(12) United States Patent
Jeon et al.

(10) Patent No.: US 11,925,115 B2
(45) Date of Patent: Mar. 5, 2024

(54) ORGANIC LIGHT-EMITTING DEVICE COMPRISING EMISSION LAYER SATISFYING SPECIFIC SINGLET EXCITATION ENERGY LEVEL CONDITIONS

(71) Applicant: Samsung Electronics Co., Ltd., Suwon-si (KR)

(72) Inventors: Soonok Jeon, Suwon-si (KR); Inkoo Kim, Suwon-si (KR); Won-Joon Son, Yongin-si (KR); Yeonsook Chung, Seoul (KR); Hyeonho Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 80 days.

(21) Appl. No.: 18/050,138

(22) Filed: Oct. 27, 2022

(65) Prior Publication Data
US 2023/0309390 A1 Sep. 28, 2023

Related U.S. Application Data

(63) Continuation of application No. 16/903,913, filed on Jun. 17, 2020, now Pat. No. 11,552,258.

(30) Foreign Application Priority Data

Aug. 30, 2019 (KR) .................. 10-2019-0107649

(51) Int. Cl.
*H10K 85/60* (2023.01)
*C07D 403/10* (2006.01)
(Continued)

(52) U.S. Cl.
CPC ....... *H10K 85/6572* (2023.02); *C07D 403/10* (2013.01); *C07D 403/14* (2013.01);
(Continued)

(58) Field of Classification Search
None
See application file for complete search history.

(56) References Cited

U.S. PATENT DOCUMENTS 10,153,438 B2 12/2018 Li et al.
10,326,093 B2 * 6/2019 Seo .................. H10K 85/654
(Continued)

FOREIGN PATENT DOCUMENTS

KR 1020160100961 A 8/2016
KR 1020180014738 A 2/2018
(Continued)

OTHER PUBLICATIONS

Dongdong Zhang, et al., Sterically Shielded Blue Thermally Activated Delayed Fluorescence Emitters with Improved Efficiency and Stability, XP055604793, Material Horizons, 2016, 3, 145-151.
(Continued)

*Primary Examiner* — Nduka E Ojeh
(74) *Attorney, Agent, or Firm* — CANTOR COLBURN LLP

(57) ABSTRACT

Disclosed is an organic light-emitting device including an emission layer that includes a compound satisfying conditions 5' and 6 below:

$0\ eV < \Delta E_{ST2} \leq 0.1\ eV$     Condition 1:

$\Delta E_{ST} > 0.2\ eV$     Condition 6:

20 Claims, 2 Drawing Sheets

(51) Int. Cl.
| | |
|---|---|
| *C07D 403/14* | (2006.01) |
| *C09K 11/06* | (2006.01) |
| *H10K 50/11* | (2023.01) |
| *H10K 50/19* | (2023.01) |
| *H10K 50/12* | (2023.01) |
| *H10K 101/10* | (2023.01) |
| *H10K 101/30* | (2023.01) |
| *H10K 101/00* | (2023.01) |

(52) U.S. Cl.
CPC ............ *C09K 11/06* (2013.01); *H10K 85/654* (2023.02); *C09K 2211/1018* (2013.01); *H10K 50/11* (2023.02); *H10K 50/121* (2023.02); *H10K 50/19* (2023.02); *H10K 2101/10* (2023.02); *H10K 2101/30* (2023.02); *H10K 2101/90* (2023.02)

(56) References Cited

U.S. PATENT DOCUMENTS

| | | | |
|---|---|---|---|
| 2016/0197282 A1* | 7/2016 | Tanimoto | H10K 85/626 |
| | | | 257/40 |
| 2018/0182980 A1 | 6/2018 | Lennartz et al. | |
| 2018/0219159 A1 | 8/2018 | Yersin et al. | |
| 2019/0081248 A1 | 3/2019 | Lin et al. | |
| 2020/0044165 A1 | 2/2020 | Lennartz et al. | |
| 2020/0136056 A1 | 4/2020 | Cui et al. | |
| 2020/0321537 A1 | 10/2020 | Jeon et al. | |

FOREIGN PATENT DOCUMENTS

| | | |
|---|---|---|
| KR | 1020180021100 A | 2/2018 |
| WO | 2015159971 A1 | 10/2015 |
| WO | 2018216820 A1 | 11/2018 |

OTHER PUBLICATIONS

Extended European search report issued by the European Patent Office on Dec. 11, 2020 in the examination of the European Patent Application No. 20185766.1, which corresponds to the U.S. Application above.

Filipp Furche, et al., TWIREs Comput Mol Sci 2014, 4:91-100. doi: 10.1002/wcms.1162.

Hartmut Yersin, et al., TADF Material Design: Photophysical Background and Case Studies Focusing on Cu(I) and Ag (I) Complexes, 2017, 60 pp.

Hiroki Uoyama, et al., Highly efficient organic light-emitting diodes from delayed fluorescence, 234, Nature, vol. 492, Dec. 13, 2012, 7 pp.

Tyun-il Seo, et al., Theoretical Study for Thermally Activated Delayed Fluorescence (TADF) Property in Organic Light-Emitting Diode (OLED) Candidates, Journal of the Korean Chemical Society 2019, vol. 63, No. 3, 9 pp.

Inkoo Kim, et al., Reverse Intersystem Crossing Rates for Thermally Activated Delayed Fluorescence: Correlation Function Approach with Spin-Vibronic Coupling, 2019, 6 pp.

Ke Liang, et al., Theoretical investigation of the singlet-triplet splittings for carbazole-based thermally activated delayed fluorescence emitters, Phys.Chem.Chem.Phys., 2016, 18, 26623-26629.

Matteo Frigo, et al., The Design and Implementation of FFTW3, Proceedings of the IEEE, vol. 93, No. 2, Feb. 2005, 216-231.

Yihan Shao, et al., Advances in molecular quantum chemistry contained in the Q-Chem 4 program package, Molecular Physics: An International Journal at the Interface Between Chemistry and Physics, DOI: 10.1080/00268976.2014.952696, 2014, 35 pp.

* cited by examiner

ORGANIC LIGHT-EMITTING DEVICE COMPRISING EMISSION LAYER SATISFYING SPECIFIC SINGLET EXCITATION ENERGY LEVEL CONDITIONS

CROSS-REFERENCE TO RELATED APPLICATION

This continuation application claims priority to U.S. application Ser. No. 16/903,913, filed on Jun. 17, 2020, which claims priority to and the benefit of Korean Patent Application No. 10-2019-0107649, filed on Aug. 30, 2019, in the Korean Intellectual Property Office, the entire contents of which are incorporated herein by reference.

BACKGROUND

1. Field

One or more embodiments relate an organic light-emitting device including an emission layer that includes a compound.

2. Description of the Related Art

Organic light-emitting devices (OLEDs) are self-emission devices that, as compared with conventional devices, have wide viewing angles, high contrast ratios, short response times, and excellent characteristics in terms of brightness, driving voltage, and response speed, and produce full-color images.

An example of the organic light-emitting devices may include an anode, a cathode, and an organic layer disposed between the anode and the cathode and including an emission layer. Such an organic light-emitting device may include a hole transport region between the anode and the emission layer, and an electron transport region between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons may transition from an excited state to a ground state, thereby generating light.

SUMMARY

One or more embodiments include an organic light-emitting device including an emission layer that includes a compound.

Additional aspects will be set forth in part in the description which follows and, in part, will be apparent from the description, or may be learned by practice of the presented embodiments.

An aspect of the present disclosure provides an organic light-emitting device including: a first electrode; a second electrode; and an organic layer disposed between the first electrode and the second electrode and including an emission layer, wherein the emission layer includes a compound satisfying Conditions 1 to 4 below:

$\Delta E_{ST} > \Delta E_{ST2} + \Delta E'_{TT}$          <Condition 1>

$0\ eV < \Delta E_{ST2} + \Delta E'_{TT} \leq 1.0\ eV$          <Condition 2>

$0\ eV < \Delta E'_{TT} \leq 0.15\ eV$          <Condition 3>

$\Delta E_{ST2} > 0\ eV.$          <Condition 4>

In Conditions 1 to 4,
- $\Delta E_{ST}$ indicates a difference between a lowest singlet excitation energy level calculated for an $S_1$ equilibrium structure of the compound and a lowest triplet excitation energy level calculated for a $T_1$ equilibrium structure of the compound;
- $\Delta E_{ST2}$ indicates the value obtained by subtracting a 2nd-lowest triplet excitation energy level calculated for the $T_2$ equilibrium structure of the compound from a lowest singlet excitation energy level calculated for an $S_1$ equilibrium structure of the compound; and
- $\Delta E'_{TT}$ indicates a difference between a 2nd-lowest singlet excitation energy level calculated for a $T_2$ equilibrium structure of the compound and a lowest triplet excitation energy level calculated for a $T_2$ equilibrium structure of the compound.

Another aspect of the present disclosure provides an organic light-emitting device including: a first electrode; a second electrode; light-emitting units in the number of m disposed between the first electrode and the second electrode and including at least one emission layer; and a charge generation layer in the number of m−1 disposed between two light-emitting units adjacent to each other among the light-units in the number of m and comprising an n-type charge generation layer and a p-type charge generation layer, wherein m is an integer of 2 or more, a maximum emission wavelength of light emitted from at least one light-emitting unit among the light-units in the number of m is different from that of light emitted from at least one light-emitting unit among the remaining light-emitting units, and the emission layer includes a compound satisfying Conditions 1 to 4 above.

Another aspect of the present disclosure provides an organic light-emitting device including: a first electrode; a second electrode; and emission layers in the number of m disposed between the first electrode and the second electrode, wherein m is an integer of 2 or more, a maximum emission wavelength of light emitted from at least one emission layer among the emission layers in the number of m is different from that of light emitted from at least one emission layer among the remaining the emission layers, and the emission layer includes a compound satisfying Conditions 1 to 4 above.

BRIEF DESCRIPTION OF THE DRAWINGS

These and/or other aspects will become apparent and more readily appreciated from the following description of the embodiments of the present disclosure, taken in conjunction with the accompanying drawings in which.

DETAILED DESCRIPTION

Figure 1:
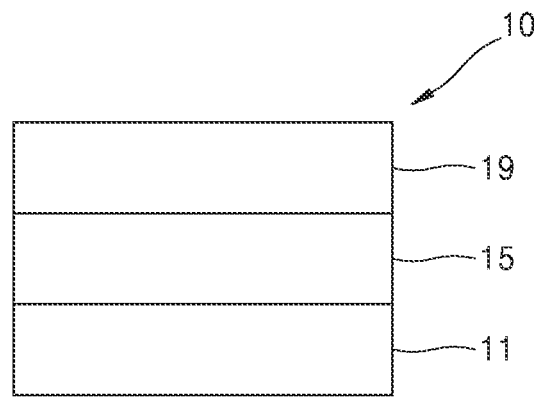
FIG. 1 is a schematic view of an organic light-emitting device 1 according to an exemplary embodiment.

Reference will now be made in detail to embodiments, examples of which are illustrated in the accompanying drawings, wherein like reference numerals refer to like elements throughout and duplicative descriptions may not be provided. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of" and "one of", when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or a group thereof.

Furthermore, relative terms, such as "lower" or "bottom" and "upper" or "top," may be used herein to describe one element's relationship to another element as illustrated in the Figures It will be understood that relative terms are intended to encompass different orientations of the device in addition to the orientation depicted in the Figures For example, if the device in one of the figures is turned over, elements described as being on the "lower" side of other elements would then be oriented on "upper" sides of the other elements The exemplary term "lower," can therefore, encompasses both an orientation of "lower" and "upper," depending on the particular orientation of the figure Similarly, if the device in one of the figures is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

Description of FIG. 1

FIG. 1 is a schematic view of an organic light-emitting device 10 according to an exemplary embodiment. Hereinafter, the structure of an organic light-emitting device according to an embodiment and a method of manufacturing an organic light-emitting device according to an embodiment will be described in connection with FIG. 1.

The organic light-emitting device 10 of FIG. 1 includes a first electrode 11, a second electrode 19 facing the first electrode 11, and an organic layer 10A disposed between the second electrode 19 and the first electrode 11.

The organic layer 10A may include an emission layer 15. A hole transport region 12 may be disposed between the first electrode 11 and the emission layer 15, and an electron transport region 17 may be disposed between the emission layer 15 and the second electrode 19.

A substrate may be additionally disposed under the first electrode 11 or above the second electrode 19. For use as the substrate, a substrate used in a typical organic light-emitting device may be used, and may be a glass substrate or a plastic substrate, each having excellent mechanical strength, thermal stability, transparency, surface smoothness, ease of handling, and water resistance.

First Electrode 11

The first electrode 11 may be formed by depositing or sputtering a material for forming the first electrode 11 on the substrate. The first electrode 11 may be an anode. The material for forming the first electrode 11 may be a material with a high work function to facilitate hole injection.

The first electrode 11 may be a reflective electrode, a semi-reflective electrode, or a transmissive electrode. When the first electrode 11 is a transmissive electrode, a material for forming a first electrode may be indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be magnesium (Mg), silver (Ag), aluminum (Al), aluminum-lithium (Al—Li), calcium (Ca), magnesium-indium (Mg—In), magnesium-silver (Mg—Ag), or any combinations thereof, but embodiments of the present disclosure are not limited thereto.

The first electrode 11 may have a single-layered structure or a multi-layered structure including two or more layers.

Emission Layer 15

The emission layer 15 may include a compound.

In one or more embodiments, the emission layer 15 may include a compound, and the compound may satisfy Conditions 1 to 4 below:

$\Delta E_{ST} > \Delta E_{ST2} + \Delta E'_{TT}$                      ⟨Condition 1⟩

$0\ eV < \Delta E_{ST2} + \Delta E'_{TT} \leq 1.0\ eV$             ⟨Condition 2⟩

$0\ eV < \Delta E'_{TT} \leq 0.15\ eV$                  ⟨Condition 3⟩

$\Delta E_{ST2} > 0\ eV$.                                        ⟨Condition 4⟩

In Conditions 1 to 4 above, $\Delta E_{ST}$ indicates a difference between a lowest singlet excitation energy level calculated for an $S_1$ equilibrium structure of the compound and a lowest triplet excitation energy level calculated for a $T_1$ equilibrium structure of the compound;

$\Delta E_{ST2}$ indicates the value obtained by subtracting a 2nd-lowest triplet excitation energy level calculated for the $T_2$ equilibrium structure of the compound from a lowest singlet excitation energy level calculated for an $S_1$ equilibrium structure of the compound; and $\Delta E'_{TT}$ indicates a difference between a 2nd-lowest singlet excitation energy level calculated for a $T_2$ equilibrium structure of the compound and a lowest triplet excitation energy level calculated for a $T_2$ equilibrium structure of the compound.

The specific calculation method is as follows.

To calculate the RISC rate between triplet-singlet states, Equation 1 below based on the Fermi Golden Rule was used:

$$k_{RISC} = \frac{1}{3} \sum_M \frac{2\pi}{\hbar} \sum_{v v'} P_v(T) |H'^M|^2 \delta(\Delta E_{ST} + E_v - E_{v'}).$$     ⟨Equation 1⟩

In Equation 1, h indicates a Plank constant, $P_v(T)$ indicates a Boltzmann distribution in a triplet oscillation state at a temperature T, $E_v$ and $E_{v'}$ indicate a triplet oscillation energy and a singlet oscillation energy, respectively, and $H'^M$ indicates perturbation Hamiltonian matrix element corresponding to the triplet magnetic quantum number (M=0, ±1). The perturbation Hamiltonian is characterized by the spin-orbit interaction of electrons and the non Born-Oppenheimer effect, and is represented by Equation 2 below:

$\hat{H}' = \hat{H}^{SO} + \hat{H}^{BO}$.                                       ⟨Equation 2⟩

A matrix element in Equation 2 may be represented by Equation 3 below when expanded to the second-order term:

$$H'^M = \langle S_1, v' | \hat{H}^{SO} | T_k^M, v \rangle + \sum_{n \neq k} \sum_{v''} \frac{\langle S_1, v' | \hat{H}^{SO} | T_n^M, v'' \rangle \langle T_n^M, v'' | \hat{H}^{BO} | T_k^M, v \rangle}{E_{T_n} - E_{T_1}}.$$     ⟨Equation 3⟩

Equation 3 assumes that all the triplet excited states (k=1, 2, . . . ) are true.

To obtain an analytical value of Equation 1, time correlation functions in a time domain were calculated by introducing Fourier transformation, and were then inverse-transformed.

In detail, a time-integrated interval of [−6553.6:6553.6] femtoseconds (fs) having a time interval of 0.1 fs was Fourier-transformed using the FFTW library as described by M. Frigo and S. G. Johnson, Proc. IEEE, 93, 216-231 (2005) and incorporated herein by reference.

The molecular structure was optimized by using the Turbomole program as described by Furche et al. WIRESs: Comput. Mol. Sci. 4, 91-100 (2014) and incorporated herein by reference.

The time-dependent density functional theory (DFT) using PBE0 functional within the Tamm-Dancoff approximation was used for structure optimization in $T_1$, $T_2$, and $S_1$ states. To obtain normal modes, frequency calculation was performed, and then, a lowest energy structure was identified. The nonadiabatic coupling between an excited triplet state and a $T_1$ state was calculated by using the Q-Chem program as described in Y. Shao et al. Mol. Phys. 113, 184-215 (2015) and incorporated herein by reference. In addition, the Q-Chem program was also used to calculate the spin-orbit coupling between TDDFT states by using a one-electron Breit-Pauli spin-orbit operator. Regarding all atoms, the def2-SVP basis set was used.

In general, only compounds with a relatively small $\Delta E_{ST}$ are known to emit thermally activated delayed fluorescence. However, according to the present disclosure, even if the compound has a relatively large $\Delta E_{ST}$, the compound satisfying Conditions 1 to 4 may emit thermally activated delayed fluorescence, thereby improving the efficiency of the organic light-emitting device including the compound.

Furthermore, when the compound is used as a sensitizer, the energy transferred to the triplet state was changed to the singlet state by reverse intersystem crossing. Then, when the singlet energy of the compound is transferred to a dopant through Förster energy transfer, the efficiency and lifespan of the organic light-emitting device may be improved simultaneously.

In detail, the compound of the organic light-emitting device may further satisfy Condition 5 below:

$\Delta E_{ST2} \leq 0.1\ eV$.                                       ⟨Condition 5⟩

In Condition 5, $\Delta E_{ST2}$ indicates the value obtained by subtracting a 2nd-lowest triplet excitation energy level calculated for the $T_2$ equilibrium structure of the compound from a lowest singlet excitation energy level calculated for an $S_1$ equilibrium structure of the compound.

In one or more embodiments, the compound of the organic light-emitting device may further satisfy Condition 6 below:

$\Delta E_{ST} > 0.2\ eV$.                                       ⟨Condition 6⟩

In Condition 6,

ΔE$_{ST}$ indicates a difference between a lowest singlet excitation energy level calculated for an S$_1$ equilibrium structure of the compound and a lowest triplet excitation energy level calculated for a T$_1$ equilibrium structure of the compound.

That is, the organic light-emitting device of the present disclosure may emit thermally activated delayed fluorescence (TADF), even when ΔE$_{ST}$ is greater than 0.2 eV.

A thickness of the emission layer may be in a range of about 100 Å to about 1000 Å, for example, about 200 Å to about 600 Å. When the thickness of the emission layer is within this range, excellent light-emission characteristics may be obtained without a substantial increase in driving voltage.

First Embodiment

In a First Embodiment, the compound may be used as a fluorescence emitter.

According to the First Embodiment, the emission layer consists of the compound only; or the emission layer may further include a host (hereinafter, referred to as 'host A', which is not identical to the compound).

Thus, according to the First Embodiment, a ratio of a light emitted by the compound to the total light emitted by the emission layer may be about 80% or more, for example, about 90% or more. For example, the ratio of a light emitted by the compound to the total light-emitted by the emission layer may be about 95% or more.

Here, the compound emits fluorescence and/or delayed fluorescence, and light emitted by the compound may be the sum of prompt emission of the compound and delayed fluorescence emission by reverse intersystem crossing. In addition, the host may not emit light.

In the First Embodiment, when the emission layer further includes, in addition to the compound, a host A, an amount of the compound may be, based on 100 parts by weight of the emission layer, about 50 parts by weight or less, for example, about 30 parts by weight or less, and an amount of host A may be, based on 100 parts by weight of the emission layer, about 50 parts by weight or more, for example, about 70 parts by weight or more, but embodiments of the present disclosure are not limited thereto.

In the First Embodiment, when the emission layer further includes host A in addition to the compound, host A and the compound may satisfy Condition A below:

$E(H_A)_{S1} > E_{S1}$. <Condition A>

In Condition A,

E(H$_A$)$_{S1}$ indicates a lowest singlet excitation energy level of host A;

E$_{S1}$ indicates a lowest singlet excitation energy level of the compound.

E(H$_A$)$_{S1}$ and E$_{S1}$ are evaluated by using a DFT method of Gaussian program that is structurally optimized at a level of B3LYP/6-31G(d,p).

When the compound satisfies Conditions 1 to 4 above, and the compound and host A satisfy Condition A above, the compound may emit fluorescence and/or delayed fluorescence. Therefore, the luminescence efficiency of the organic light-emitting device including the compound and host A may be improved.

For example, host A may be a host material described below, but embodiments of the present disclosure are not limited thereto.

Second Embodiment

In a Second Embodiment, the compound may be used as a sensitizer.

According to the Second Embodiment, the emission layer includes a host, a sensitizer, and a dopant, wherein the sensitizer may include the compound. The dopant may be, for example, a fluorescent dopant or a thermally activated, delayed fluorescence dopant.

Thus, according to the Second Embodiment, a ratio of a light emitted by the dopant to the total light emitted by the emission layer may be about 80% or more, for example, about 90% or more (In one or more embodiments, 95% or more). For example, the dopant may emit fluorescence. In addition, each of the host and the compound may not emit light.

In the Second Embodiment, the emission layer consists of the host, the dopant, and the compound. That is, the emission layer does not further include, in addition to the host, the dopant, and the compound, other materials.

In more detail, a description of the general energy transfer of the organic light-emitting device including the emission layer that consists of the host, the dopant, and the compound is as follows.

The energy of singlet excitons formed at a ratio of 25% in the host is transferred to the compound by Förster energy transfer, and the energy of triplet excitons formed at a ratio of 75% in the host is transferred to the singlet and triplet states of the compound. The energy transferred to the triplet state is changed to the singlet state by reverse intersystem crossing, and then, the singlet energy of the compound is transferred to the dopant by Förster energy transfer. Accordingly, by delivering both the singlet excitons and triplet excitons that are generated in the emission layer to the dopant, an organic light-emitting device thus obtained may have improved efficiency. Furthermore, since an organic light-emitting device in which the energy lost is significantly reduced may be obtained, such an organic light-emitting device may also have improved lifespan characteristics.

In the emission layer, an amount of the compound may be in a range of about 5 weight % to about 50 weight %, for example, about 10 weight % to about 30 weight %. When the amount is within this range, efficient energy transfer in the emission layer may be achieved, thereby implementing the organic light-emitting device having high efficiency and a long lifespan.

In the emission layer, an amount of the dopant may be in a range of about 0.01 weight % to about 15 weight %, for example, about 0.05 weight % to about 3 weight %, but embodiments of the present disclosure are not limited thereto.

For example, in the Second Embodiment, when the dopant is a fluorescent dopant (hereinafter, referred to as 'fluorescent dopant B'), each of the host (hereinafter, referred to as 'host B'), the compound, and fluorescent dopant B may satisfy Condition B below:

$E(H_B)_{S1} > E_{S1} > E(F_B)_{S1}$. <Condition B>

In Condition B,

E(H$_B$)$_{S1}$ indicates a lowest singlet excitation energy level of host B;

E$_{S1}$ indicates a lowest singlet excitation energy level of the compound; and E(F$_B$)$_{S1}$ indicates a lowest singlet excitation energy level of fluorescent dopant B.

$E(H_B)_{S1}$, $E_{S1}$, and $E(F_B)_{S1}$ are evaluated by using a DFT method of Gaussian program that is structurally optimized at a level of B3LYP/6-31G(d,p).

When host B, the compound, and fluorescent dopant B satisfy Condition B above, Forster energy transfer from the compound to fluorescent dopant B may be promoted. Therefore, the luminescence efficiency of the organic light-emitting device including host B, the compound, and fluorescent dopant B may be improved.

Each of host B and the compound may further satisfy Condition C below:

$$E(H_B)_{T1} - E_{T1} > 0.05 \text{ eV}. \qquad \text{<Condition C>}$$

In Condition C, $E(H_B)_{T1}$ indicates a lowest triplet excitation energy level of the host B; and $E_{T1}$ indicates a lowest triplet excitation energy level of the compound.

$E(H_B)_{T1}$ and $E_{T1}$ are evaluated by using a DFT method of Gaussian program that is structurally optimized at a level of B3LYP/6-31G(d,p).

In the Second Embodiment, when Condition C above (for example, $E(H_B)_{T1} - E_{T1}$ is satisfied within 0.10 eV or more and 0.65 eV or less) is satisfied, the energy of the triplet excitons generated by the sensitizer in the emission layer is not transferred to host B in the emission layer, thereby reducing the probability that the triplet excitons are lost in a path other than emission. Accordingly, an organic light-emitting device thus obtained may have high efficiency.

Each of the compound and fluorescent dopant B may further satisfy Condition D below:

$$E(F_B)_{S1} - E_{S1} < 0 \text{ eV}. \qquad \text{<Condition D>}$$

In Condition D, $E(F_B)_{S1}$ indicates a lowest singlet excitation energy level of the fluorescent dopant; and $E_{S1}$ indicates a lowest singlet excitation energy level of the compound.

$E(F_B)_{S1}$ and $E_{S1}$ are evaluated by using a DFT method of Gaussian program that is structurally optimized at a level of B3LYP/6-31G(d,p).

In the Second Embodiment, when Condition D above (for example, $E_{S1(FD)} - E_{S1(AD)}$ is satisfied within –0.4 eV or more and –0.05 eV or less) is satisfied, the energy of the singlet excitons generated by the sensitizer in the emission layer is promptly transferred to fluorescent dopant B. In this regard, substantially, in the emission layer of the organic light-emitting device, only fluroescent dopant B emits light, thereby realizing a fluorescence emission spectrum having excellent color purity based on fluorescent dopant B. In addition, fluorescence emission with a relatively short exciton lifespan may be achieved, thereby realizing an organic light-emitting device having high efficiency by suppressing low-efficiency rolling-off under high-luminance (so-called a roll-off phenomenon) that may be caused by interactions between a plurality of excitons (exciton-exciton interactions) or interactions between excitons and charges (e.g., holes or electrons) (exciton-polaron interactions), so that an organic light-emitting device having high efficiency may be implemented. Furthermore, since the sensitizer has a short exciton lifespan, the probability of chemical or physical deterioration occurring in the exciton state of the sensitizer may be reduced, and thus an organic light-emitting satisfying Condition D may have improved durability.

The host of the Second Embodiment may be a host material described below, but embodiments of the present disclosure are not limited thereto.

The dopant of the Second Embodiment may be a dopant material described below, but embodiments of the present disclosure are not limited thereto.

Host in Emission Layer 15

The host may not include a metal atom.

In one or more embodiments, the host may consist of one type of host. When the host consists of one type of host, the one type of host may be an amphiprotic host which will be described below, an electron transport host, a hole transport host, or any combination thereof.

In one or more embodiments, the host may be a mixture of two or more different hosts. For example, the host may be a mixture of an electron transport host and a hole transport host, a mixture of two different electron transport hosts, or a mixture of two different hole transport hosts. The electron transport host and the hole transport host may be understood by referring to the descriptions thereof presented herein.

In one or more embodiments, the host may include an electron transport host hat includes at least one electron transport moiety and a hole transport host that does not include an electron transport moiety.

The electron transport moiety may be a cyano group, a π electron-depleted nitrogen-containing cyclic group, a group represented by one of the following formulae, or any combination thereof:

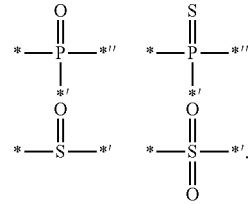

In the formulae above, *, *', and *" each indicate a binding site to a neighboring atom.

In one or more embodiments, the electron transport host in the emission layer 15 may include at least one a cyano group, a π electron-depleted nitrogen-containing cyclic group, or any combination thereof.

In one or more embodiments, the electron transport host in the emission layer 15 may include at least one cyano group.

In one or more embodiments, the electron transport host in the emission layer 15 may include at least one cyano group and at least one π electron-depleted nitrogen-containing cyclic group.

In one or more embodiments, the host may include an electron transport host and a hole transport host, wherein the electron transport host may include at least one π electron-depleted nitrogen-free cyclic group and at least one electron transport moiety, and the hole transport host may include at least one π electron-depleted nitrogen-free cyclic group and may not include an electron transport moiety.

The term "π electron-depleted nitrogen-containing cyclic group" as used herein refers to a cyclic group having at least one *—N=*' moiety, and for example, may be: an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group; or a condensed ring of two or more π electron-depleted nitrogen-containing cyclic a group.

In one or more embodiments, the π electron-depleted nitrogen-free cyclic group may be: a benzene group, a heptalene group, an indene group, a naphthalene group, an azulene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a triindolobenzene group; or a condensed ring of two or more π electron-depleted nitrogen-free cyclic a group, but embodiments of the present disclosure are not limited thereto.

In one or more embodiments, the electron transport host may include a compound represented by Formula E-1 below, and the hole transport host may include a compound represented by Formula H-1 below, but embodiments of the present disclosure are not limited thereto:

$$[Ar_{301}]_{xb11}-[(L_{301})_{xb1}-R_{301}]_{xb21} \quad \text{<Formula E-1>}$$

In Formula E-1,

Ar$_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, L$_{301}$ may be a single bond, a group represented by one of the following formulae, a substituted or unsubstituted $C_5$-$C_{60}$ carbocyclic group, a substituted or unsubstituted $C_1$-$C_{60}$ heterocyclic group, or any combination thereof:

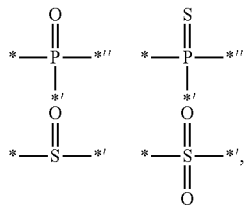

wherein *, *', and *" in the formulae above each indicate a binding site to a neighboring atom, xb1 may be an integer from 1 to 5, R$_{301}$ may be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{301}$)(Q$_{302}$)(Q$_{303}$), —N(Q$_{301}$)(Q$_{302}$), —B(Q$_{301}$)(Q$_{302}$), —C(=O)(Q$_{301}$), —S(=O)$_2$(Q$_{301}$), —S(=O)(Q$_{301}$), —P(=O)(Q$_{301}$)(Q$_{302}$), or —P(=S)(Q$_{301}$)(Q$_{302}$), xb21 may be an integer from 1 to 5, Q$_{301}$ to Q$_{303}$ may each independently be $C_1$-$C_{10}$ alkyl group, a $C_1$-$C_{10}$ alkoxy group, a phenyl group, a biphenyl group, a terphenyl group, or a naphthyl group, and the electron transport host may satisfy at least one of <Condition H-1> to <Condition H-3>:

<Condition H-1> at least one Ar$_{301}$, L$_{301}$, and R$_{301}$ in Formula E-1 may each independently include a π electron-depleted nitrogen-containing cyclic group, <Condition H-2>

L$_{301}$ in Formula E-1 may be a group represented by one of the following formulae:

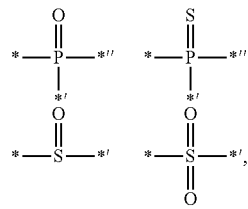

<Condition H-3>

R$_{301}$ in Formula E-1 may be a cyano group, —S(=O)$_2$(Q$_{301}$), —S(=O)(Q$_{301}$), —P(=O)(Q$_{301}$)(Q$_{302}$), or —P(=S)(Q$_{301}$)(Q$_{302}$), $$Ar_{401}-(L_{401})_{xd1}-(Ar_{402})_{xd11}, \quad \text{<Formula H-1>}$$

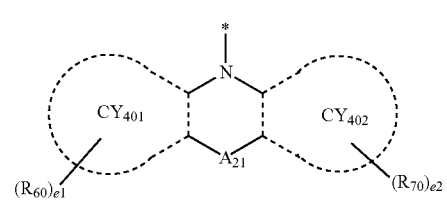

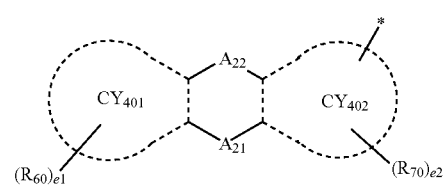

in Formulae H-1, 11, and 12, $L_{401}$ may be:

a single bond; or a benzene group, a heptalene group, an indene group, a naphthalene group, an azulene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group, each unsubstituted or substituted with at least one deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si($Q_{401}$)($Q_{402}$)($Q_{403}$), or any combination thereof, xd1 may be an integer from 1 to 10, wherein, when xd1 is 2 or more, two or more $L_{401}$(S) may be identical to or different from each other, $Ar_{401}$ may be a group represented by Formulae 11 or 12, $Ar_{402}$ may be:

a group represented by Formulae 11 and 12, a phenyl group, a naphthyl group, a fluorenyl group, a carbazolyl group, a dibenzofuranyl group, a dibenzothiophenyl group, a biphenyl group, a terphenyl group, or a triphenylenyl group; or a phenyl group, a naphthyl group, a fluorenyl group, a carbazolyl group, a dibenzofuranyl group, a dibenzothiophenyl group, a biphenyl group, a terphenyl group, or a triphenylenyl group, each substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, a terphenyl group, a triphenylenyl group, or any combination thereof, $CY_{401}$ and $CY_{402}$ may each independently be a benzene group, a naphthalene group, a fluorene group, a carbazole group, a benzocarbazole group, an indolocarbazole group, a dibenzofuran group, a dibenzothiophene group, a dibenzosilole group, a benzonaphthofuran group, a benzonaphthothiophene group, or a benzonaphthosilole group, $A_{21}$ may be a single bond, O, S, N($R_{51}$), C($R_{51}$)($R_{52}$), or Si($R_{51}$)($R_{52}$), $A_{22}$ may be a single bond, O, S, N($R_{53}$), C($R_{53}$)($R_{54}$), or Si($R_{53}$)($R_{54}$), at least one of $A_{21}$ and $A_{22}$ in Formula 12 is not a single bond, $R_{51}$ to $R_{54}$, $R_{60}$, and $R_{70}$ may each independently be:

hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, or a dibenzothiophenyl group;

a π electron-depleted nitrogen-free cyclic group (for example, a phenyl group, a naphthyl group, a fluorenyl group, a carbazolyl group, a dibenzofuranyl group, a dibenzothiophenyl group, a biphenyl group, a terphenyl group, and a triphenylenyl group);

a π electron-depleted nitrogen-free cyclic group (for example, a phenyl group, a naphthyl group, a fluorenyl group, a carbazolyl group, a dibenzofuranyl group, a dibenzothiophenyl group, a biphenyl group, a terphenyl group, and a triphenylenyl group) substituted with at least one deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or any combination thereof; or —Si($Q_{404}$)($Q_{405}$)($Q_{406}$), e1 and e2 may each independently be an integer from 0 to 10, $Q_{401}$ to $Q_{406}$ may each independently be hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, a biphenyl group, a terphenyl group, or a triphenylenyl group, and

* indicates a binding site to a neighboring atom.

In one or more embodiments, $Ar_{301}$ and $L_{301}$ in Formula E-1 may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof, at least one of $L_{301}$(s) in the number of xb1 may each independently be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyrdinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyrdazinyl group, a pyrimidinyl group, a phenylpyrimidinyl group, a diphenylpyrimidinyl group, a biphenylpyrimidinyl group, a di(biphenyl)pyrmidinyl group, a triazinyl group, a phenyltriazinyl group, a diphenyltriazinyl group, a biphenyltriazinyl group, a di(biphenyl)trazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof, $R_{301}$ may be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a tetraphenyl group, a naphthyl group, a cyano group-containing phenyl group, a cyano group-containing biphenyl group, a cyano group-containing terphenyl group, a cyano group-containing tetraphenyl group, a cyano group-containing naphthyl group, a pyridinyl group, a phenylpyridinyl group, a diphenylpyridinyl group, a biphenylpyridinyl group, a di(biphenyl)pyrdinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrmidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group, but embodiments of the present disclosure are not limited thereto.

In one or more embodiments, $Ar_{301}$ may be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, or a dibenzothiophene group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyrdinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrmidinyl group, a triazinyl group, a phenyltriazinyl group, a diphenyltriazinyl group, a biphenyltriazinyl group, a di(biphenyl)triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof; or a group represented by one of Formulae 5-1 to 5-3 and 6-1 to 6-33, and L₃₀₁ may be a group represented by Formulae 5-1 to 5-3 and 6-1 to 6-33 below:
5-1
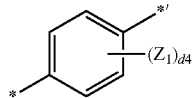
5-2
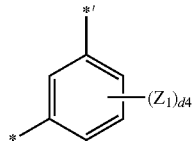
5-3
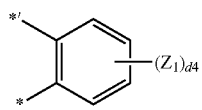
6-1
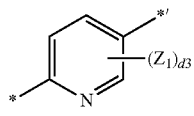
6-2
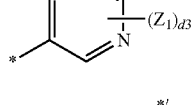
6-3
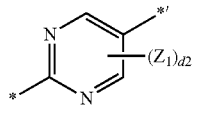
6-4
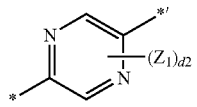
6-5
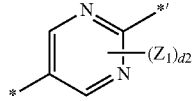
6-6
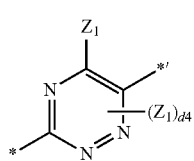
6-7
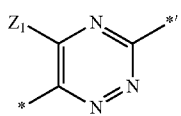
6-8
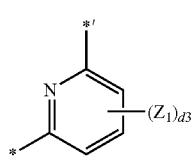
-continued
6-9
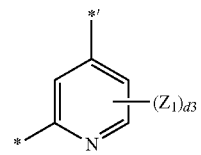
6-10
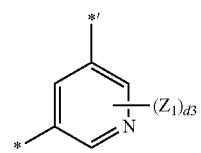
6-11
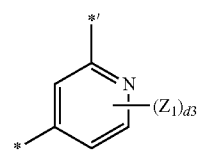
6-12
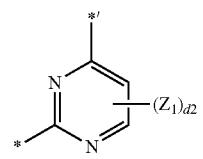
6-13
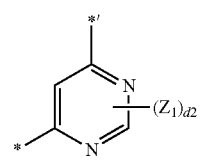
6-14
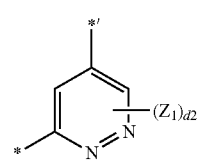
6-15
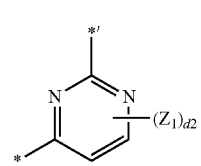
6-16
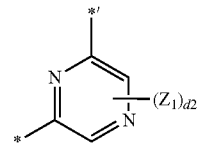
6-17
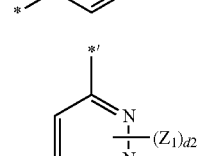
6-18
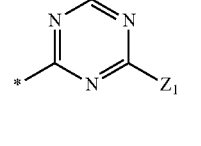

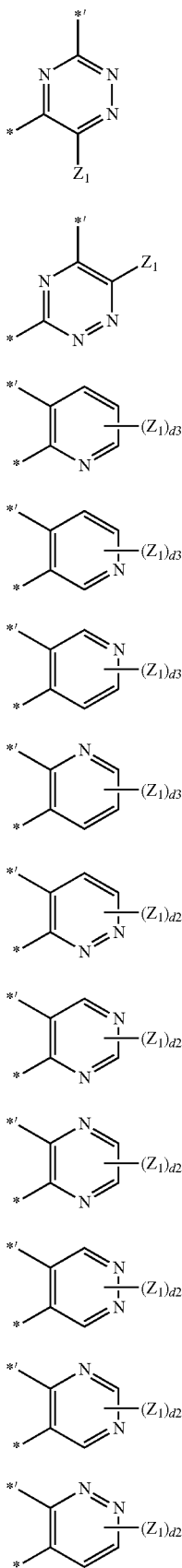
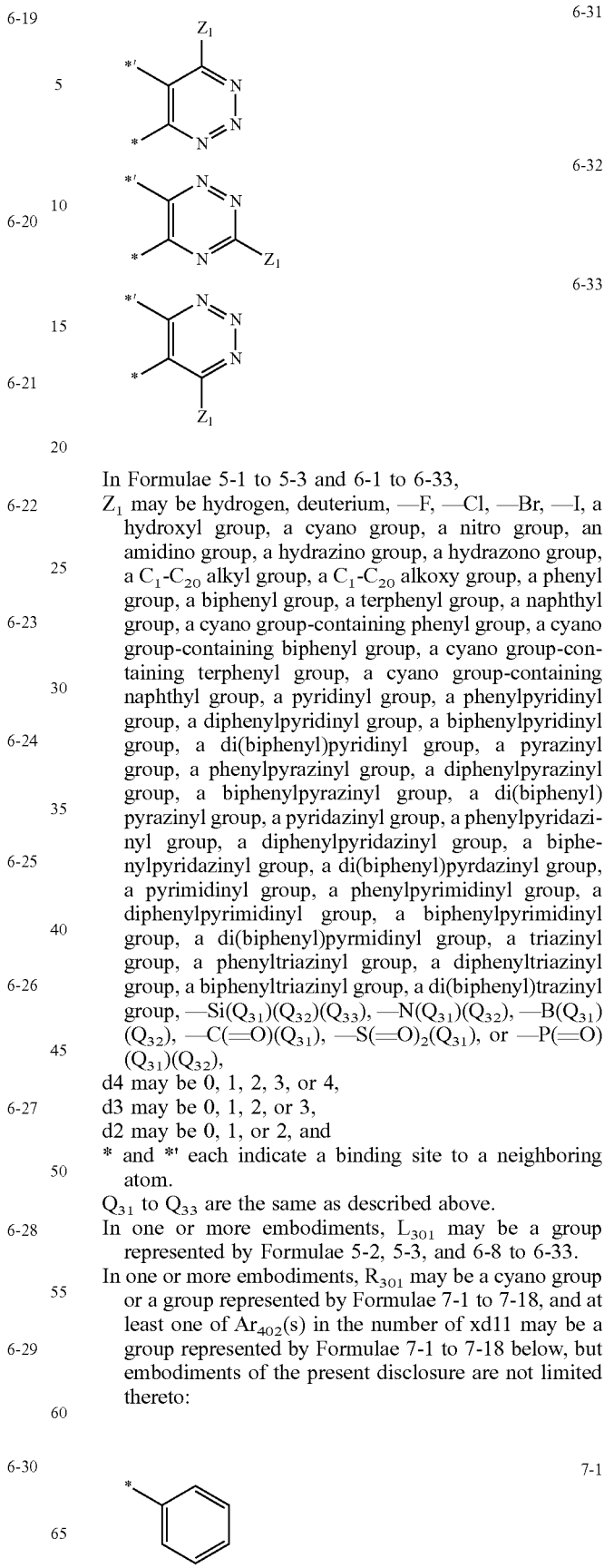

In Formulae 5-1 to 5-3 and 6-1 to 6-33, $Z_1$ may be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyrdazinyl group, a pyrimidinyl group, a phenylpyrimidinyl group, a diphenylpyrimidinyl group, a biphenylpyrimidinyl group, a di(biphenyl)pyrmidinyl group, a triazinyl group, a phenyltriazinyl group, a diphenyltriazinyl group, a biphenyltriazinyl group, a di(biphenyl)trazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), d4 may be 0, 1, 2, 3, or 4, d3 may be 0, 1, 2, or 3, d2 may be 0, 1, or 2, and

* and *' each indicate a binding site to a neighboring atom.

$Q_{31}$ to $Q_{33}$ are the same as described above.

In one or more embodiments, $L_{301}$ may be a group represented by Formulae 5-2, 5-3, and 6-8 to 6-33.

In one or more embodiments, $R_{301}$ may be a cyano group or a group represented by Formulae 7-1 to 7-18, and at least one of $Ar_{402}$(s) in the number of xd11 may be a group represented by Formulae 7-1 to 7-18 below, but embodiments of the present disclosure are not limited thereto:

7-2 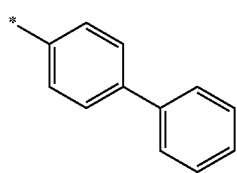
7-3 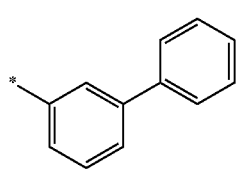
7-4 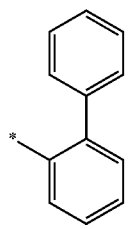
7-5 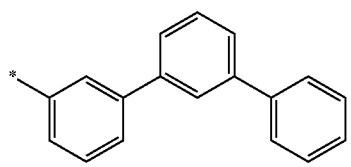
7-6 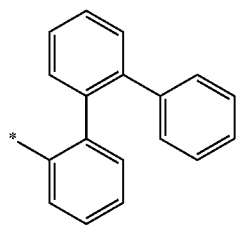
7-7 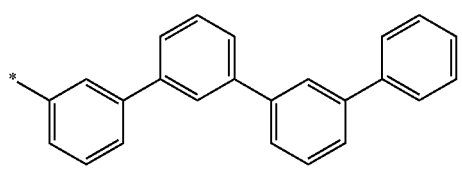
7-8 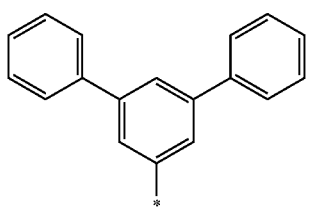
7-9 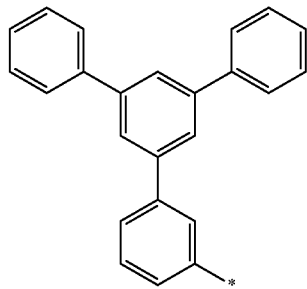
7-10 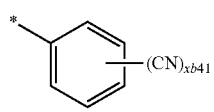
7-11 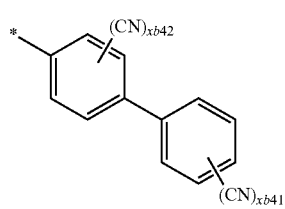
7-12 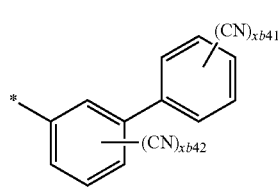
7-13 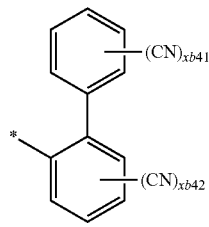
7-14 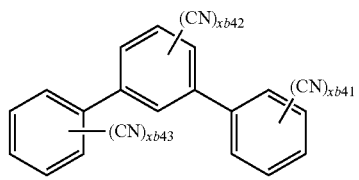
7-15 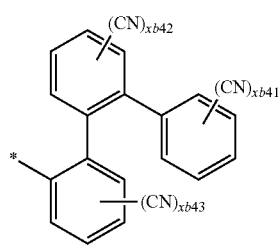

-continued 7-16
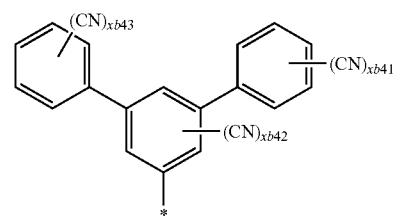

7-17
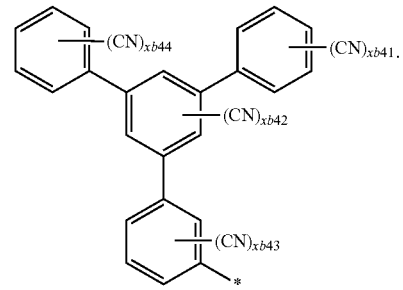

7-18
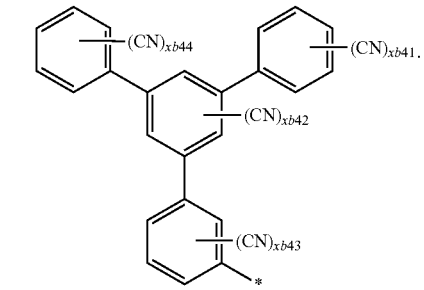

In Formulae 7-1 to 7-18, xb41 to xb44 may each independently be 0, 1, or 2, wherein xb41 in Formula 7-10 is not 0, xb41+xb42 in Formulae 7-11 to 7-13 is not 0, xb41+xb42+xb43 in Formulae 7-14 to 7-16 is not 0, xb41+xb42+xb43+xb44 in Formulae 7-17 and 7-18 is not 0, and * indicates a binding site to a neighboring atom.

In Formula E-1, two or more $A_{301}$(s) may be identical to or different from each other, and two or more $L_{301}$(s) may be identical to or different from each other. In Formula H-1, two or more $L_{401}$(s) may be identical to or different from each other, and two or more $Ar_{402}$(s) may be identical to or different from each other.

In one or more embodiments, the electron transport host may include i) at least one of a cyano group, a pyrimidine group, a pyrazine group, or a triazine group, and ii) a triphenylene group, and the hole transport host may include a carbazole group.

In one or more embodiments, the electron transport host may include at least one cyano group.

The electron transport host may be, for example, a compound belonging to <Group HE1> to <Group HE7>, but embodiments of the present disclosure are not limited thereto:

<Group HE1>

H-E1
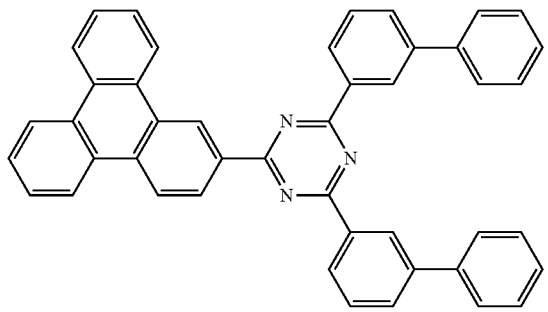

H-E2
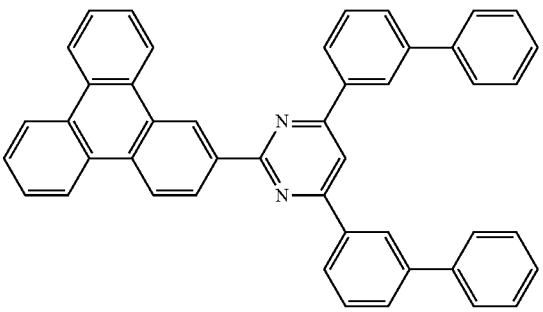

H-E3
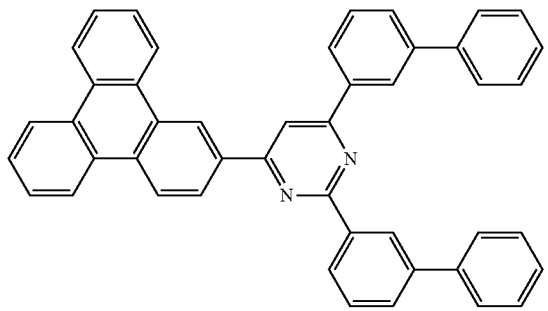

H-E4
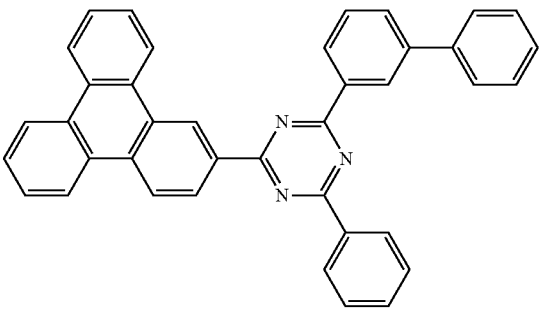

-continued
H-E5
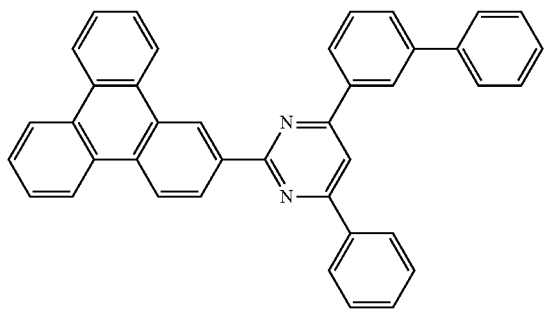
H-E6
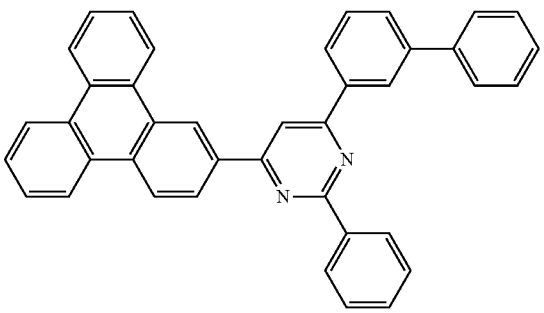
H-E7
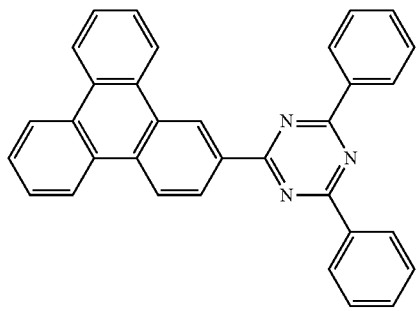
H-E8
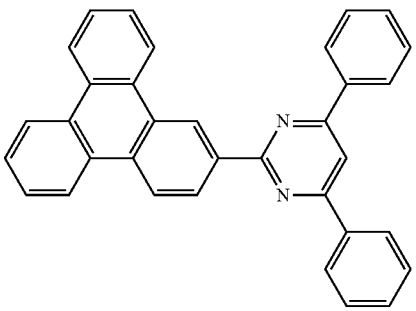
H-E9
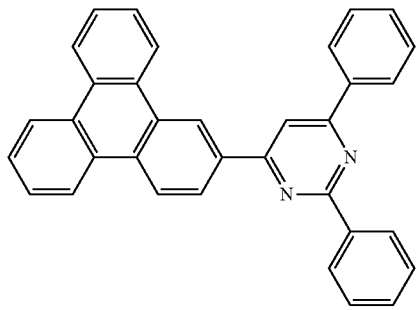
H-E10
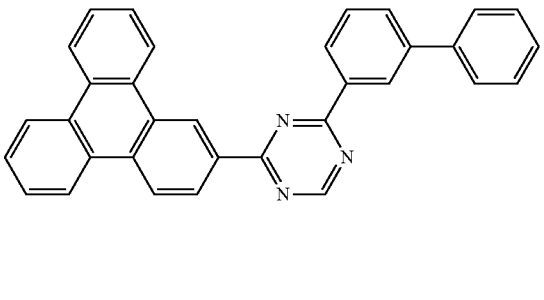
H-E11
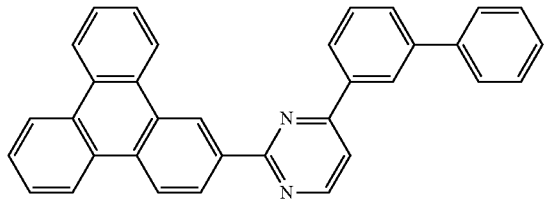
H-E12
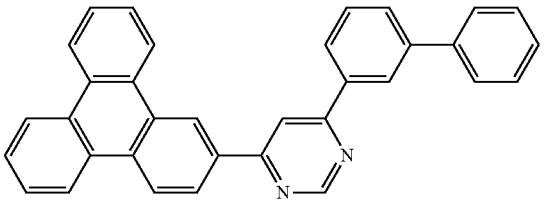
H-E13
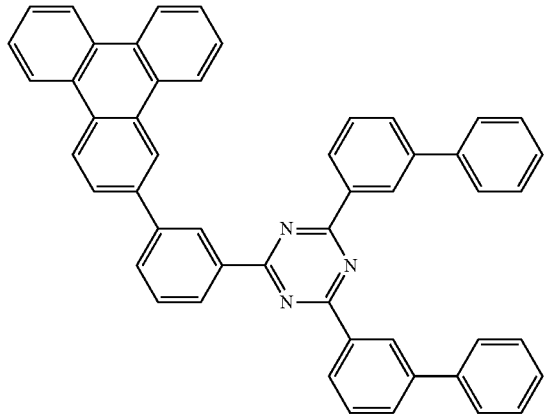
H-E14
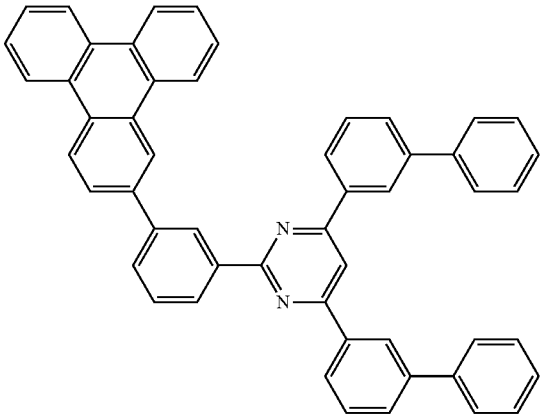

-continued
H-E15
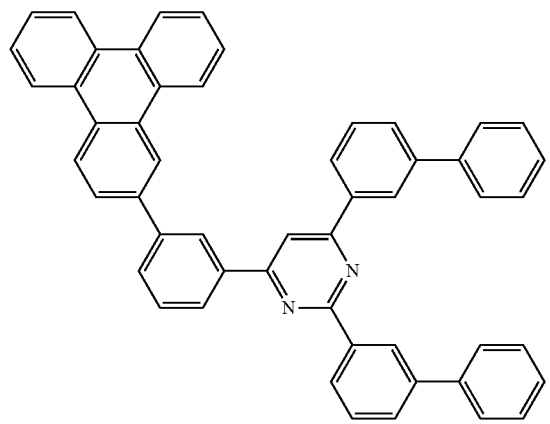
H-E16
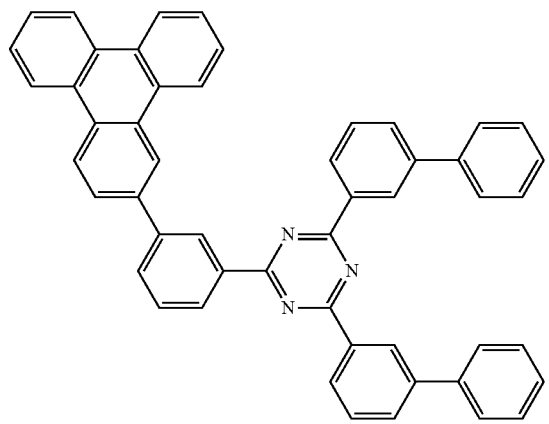
H-E17
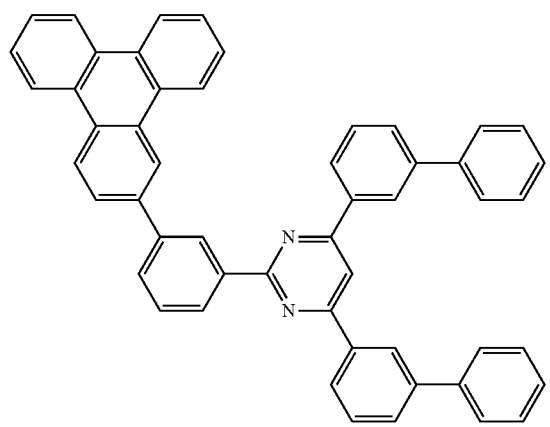
H-E18
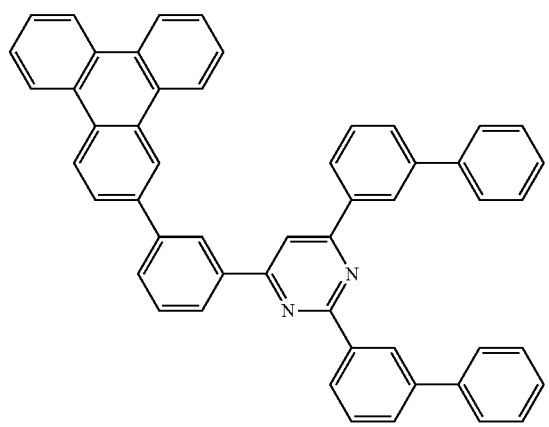
H-E19
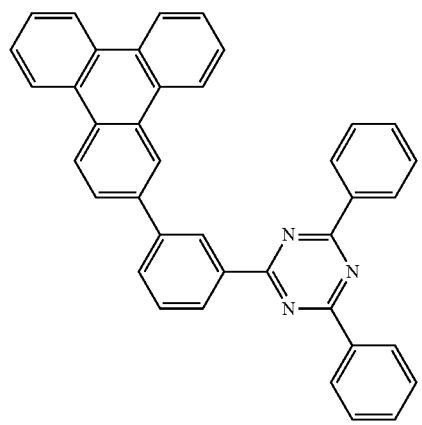
H-E20
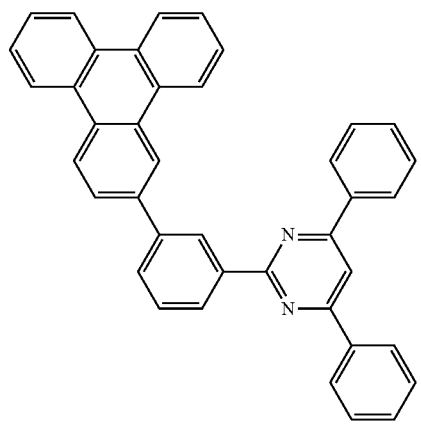

-continued
H-E21
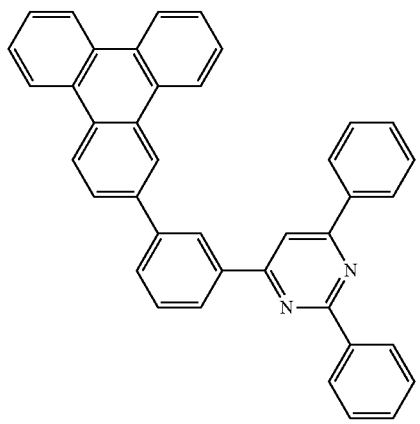
H-E22
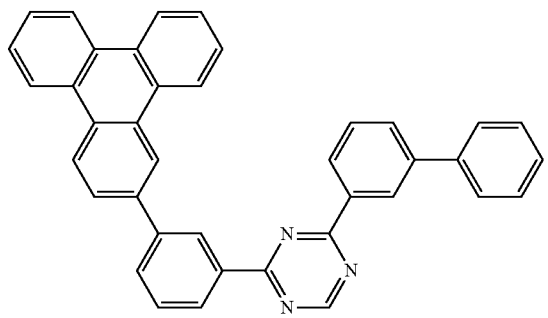
H-E23
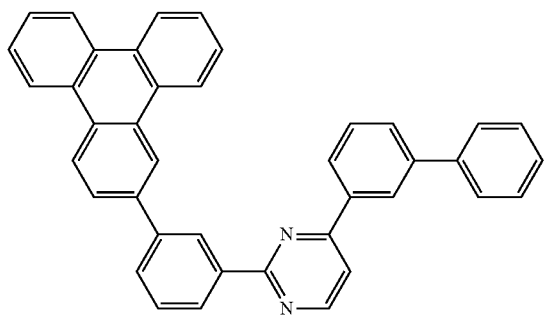
H-E24
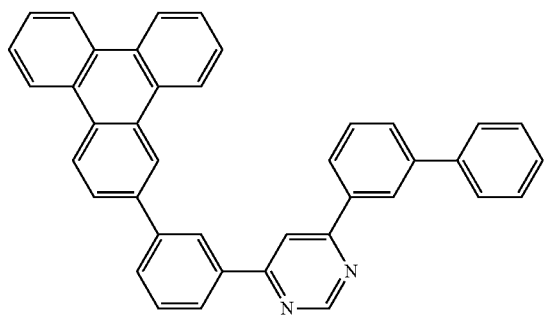
H-E25
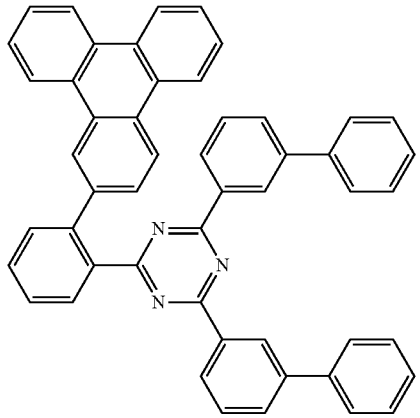
H-E26
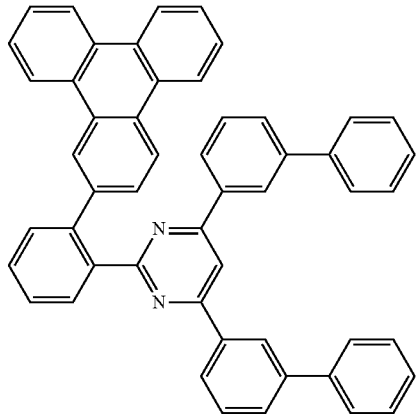
H-E27
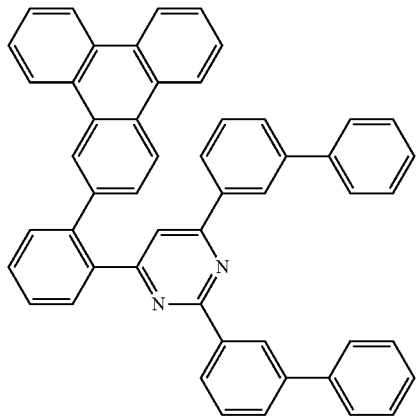
H-E28
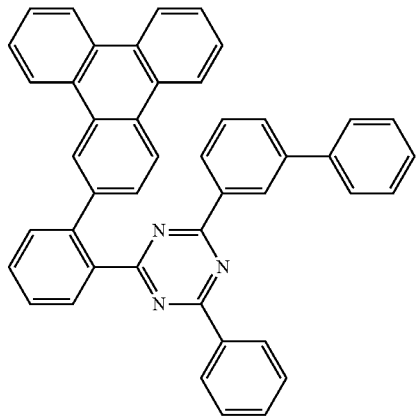

-continued
H-E29
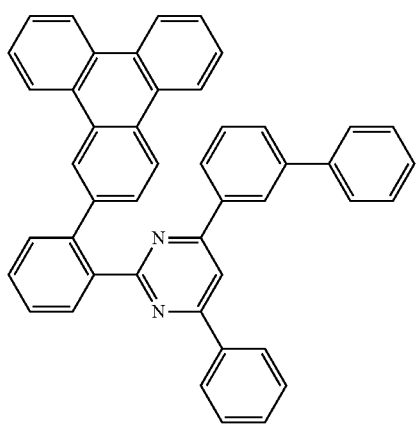
H-E30
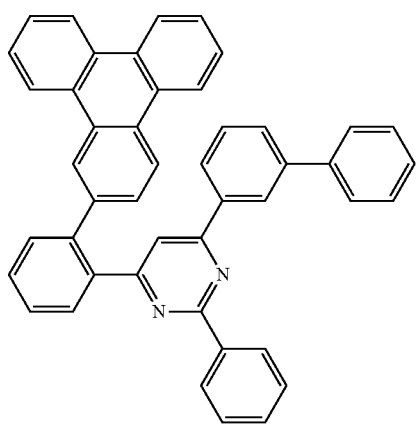
H-E31
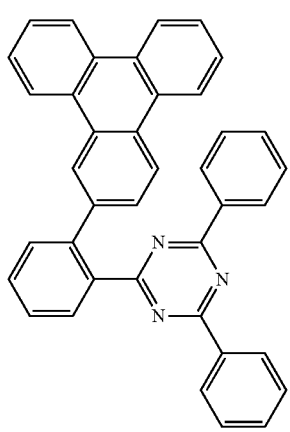
H-E32
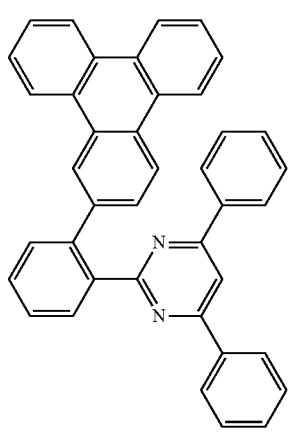
H-E33
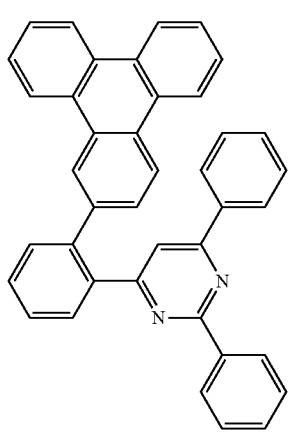
H-E34
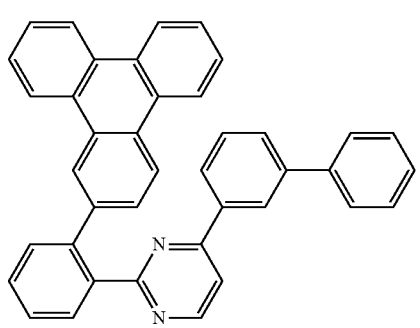
H-E35
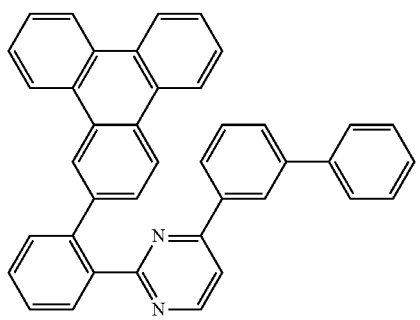
H-E36
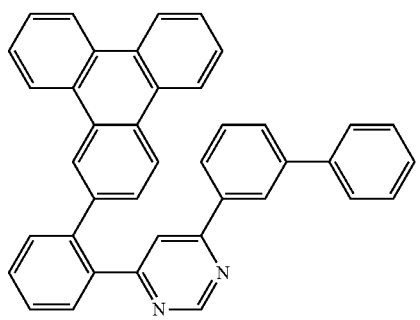

-continued
H-E37
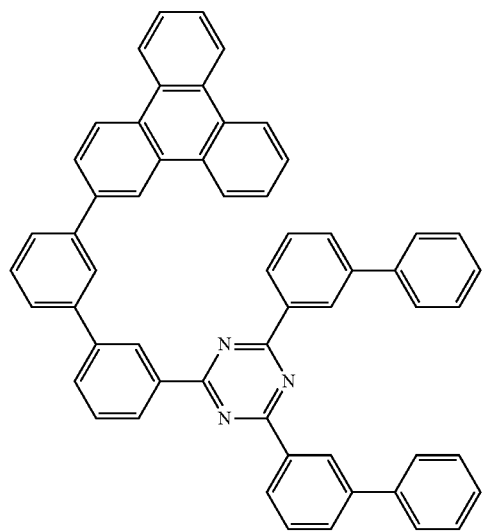
H-E38
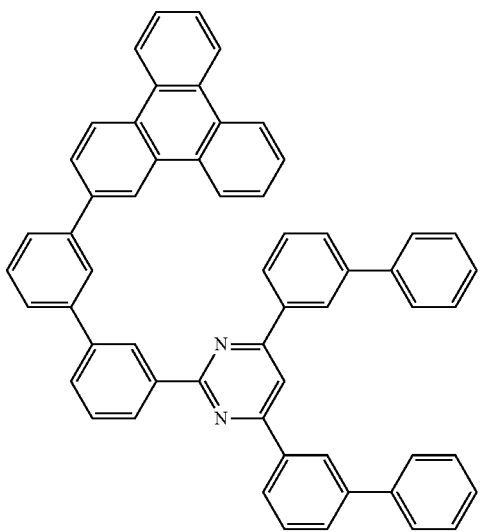
H-E39
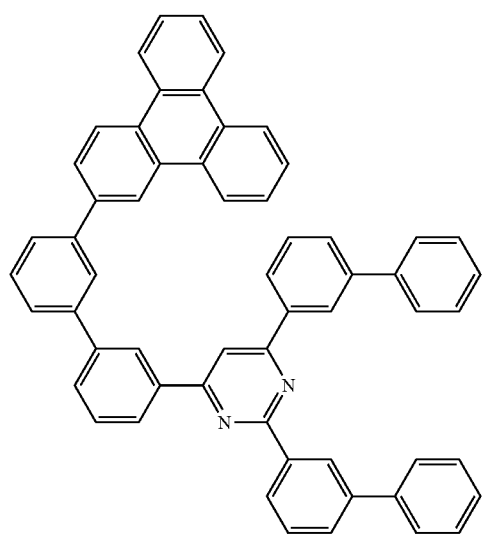
H-E40
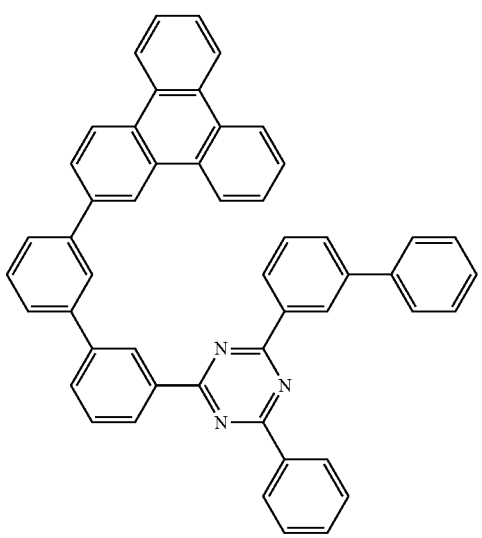
H-E41
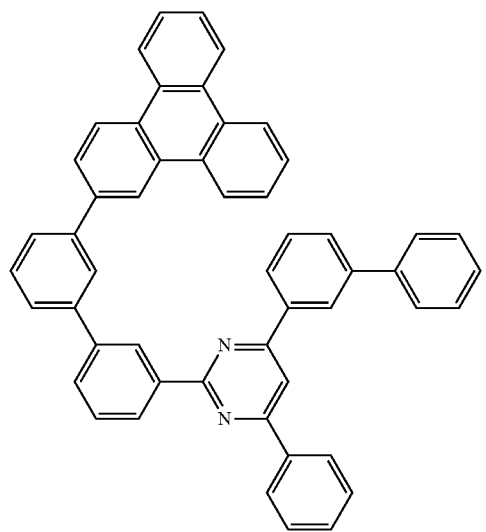
H-E42
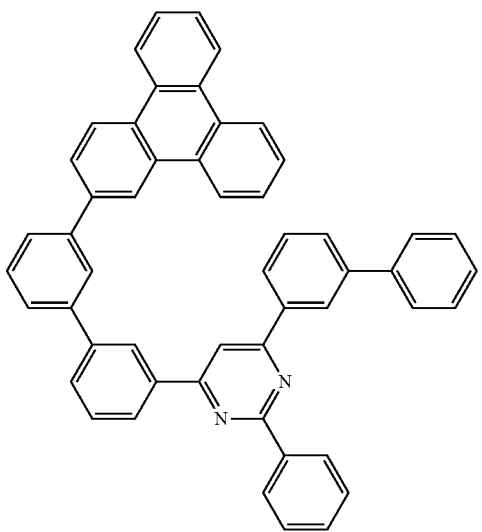

-continued
H-E43
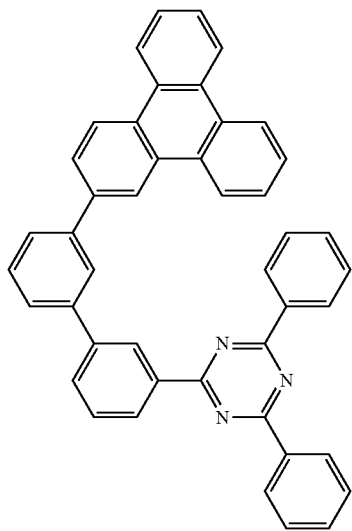
H-E44
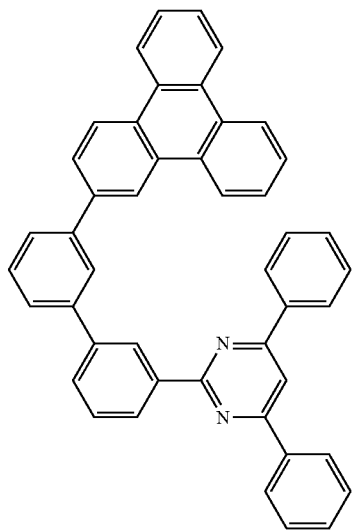
H-E45
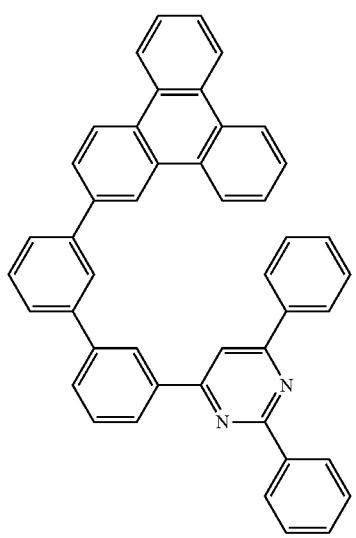
H-E46
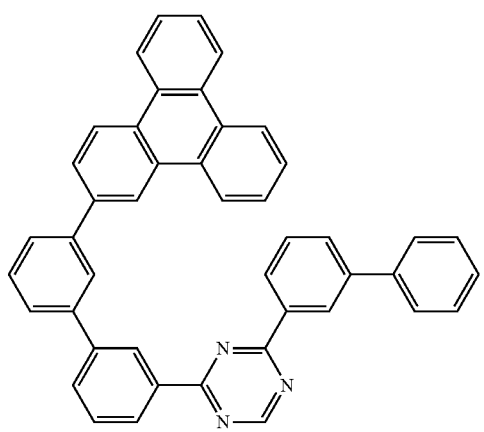
H-E47
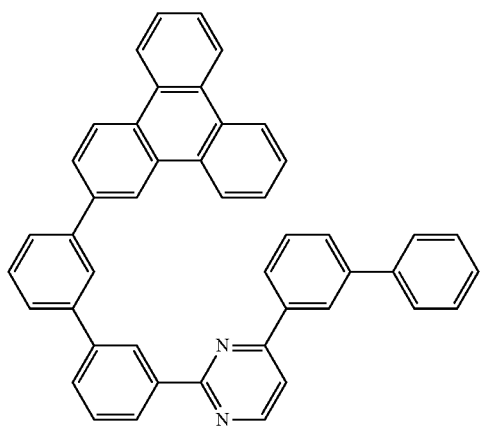
H-E48
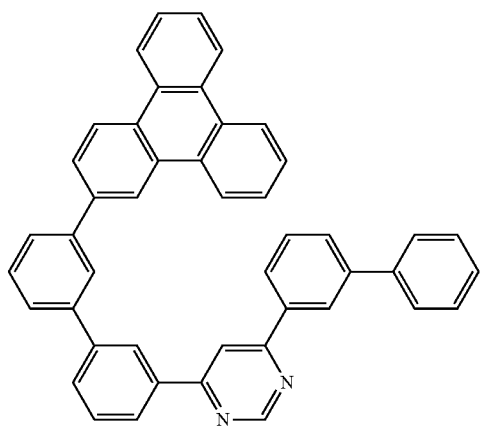

-continued
H-E49
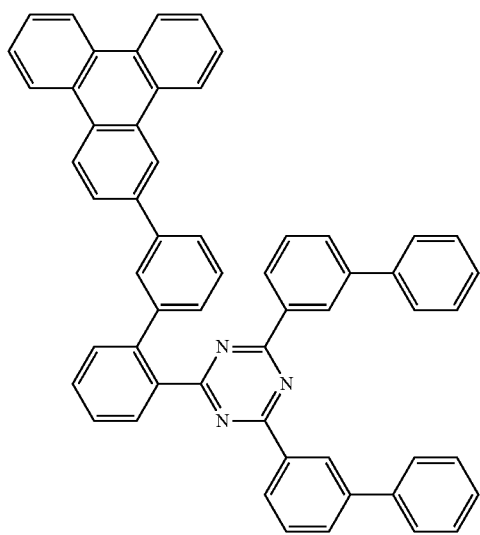
H-E50
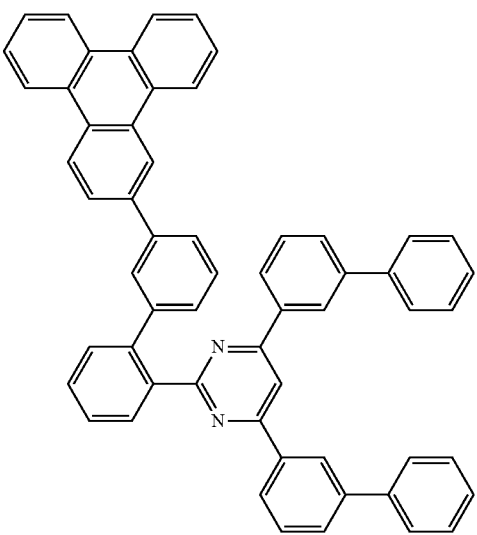
H-E51
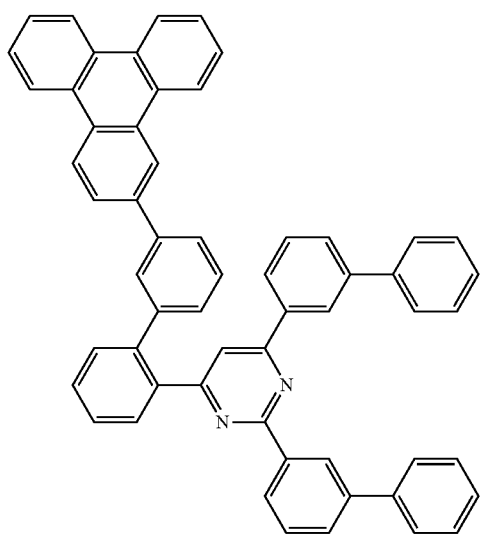
H-E52
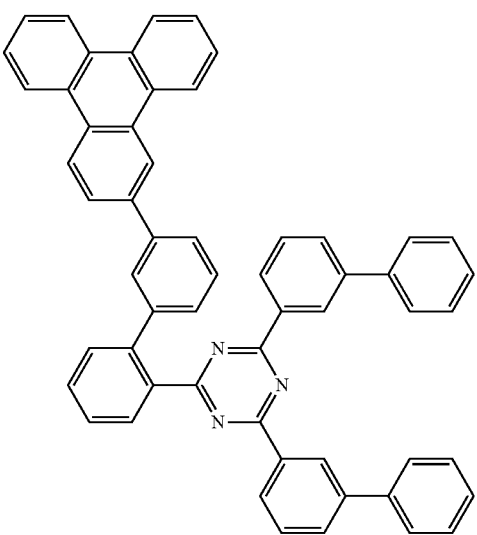
H-E53
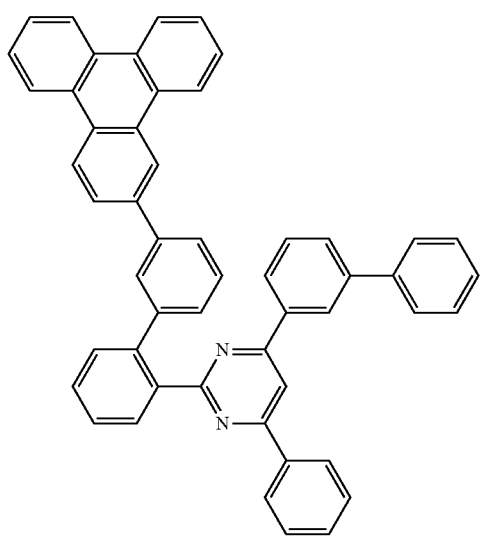
H-E54
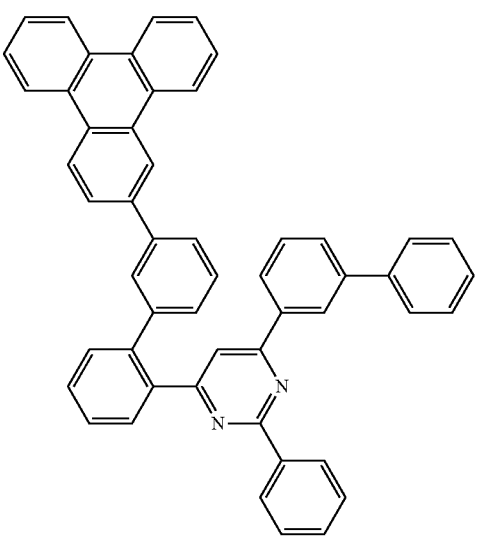

-continued
H-E55
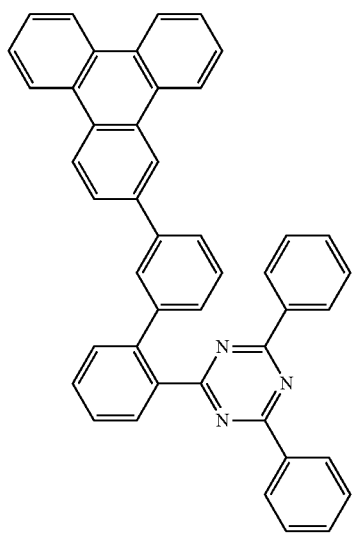
H-E56
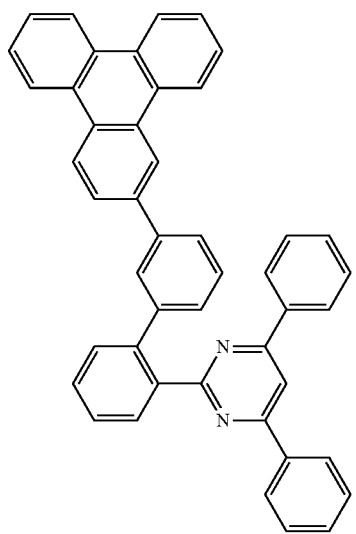
H-E57
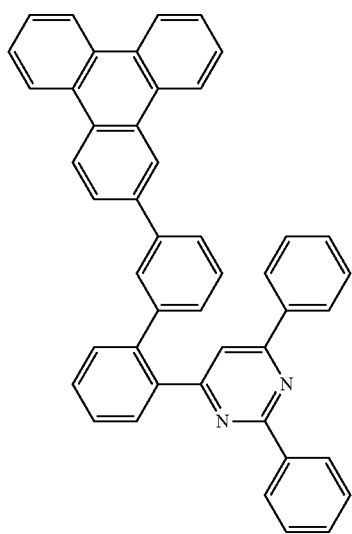
H-E58
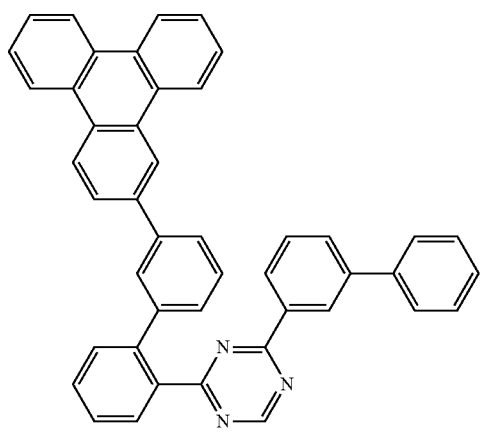
H-E59
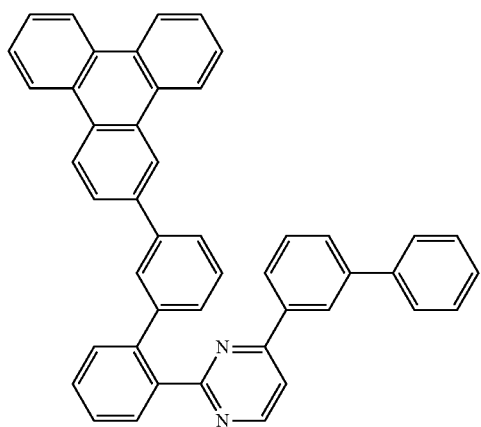
H-E60
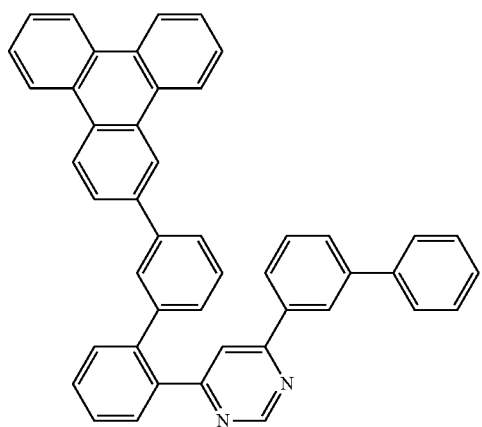

-continued
H-E61
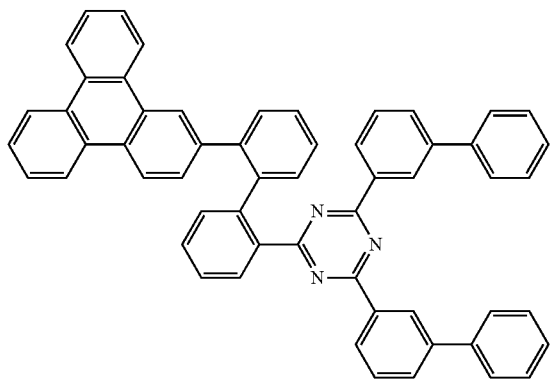
H-E62
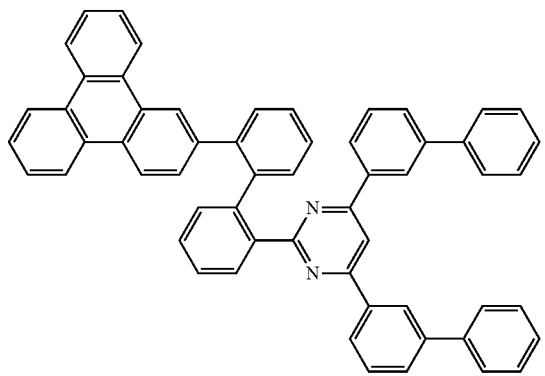
H-E63
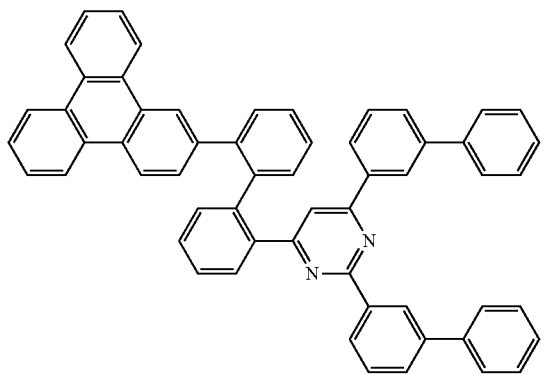
H-E64
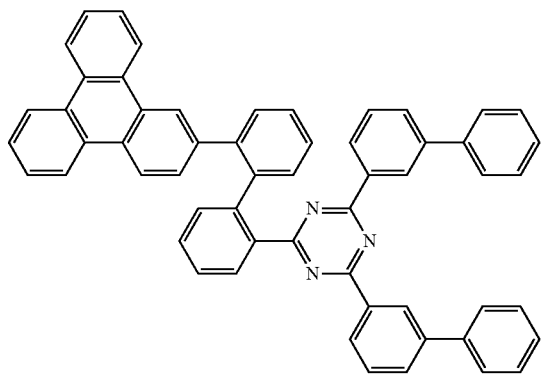
H-E65
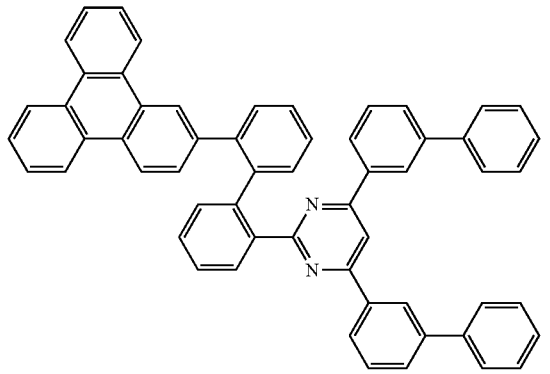
H-E66
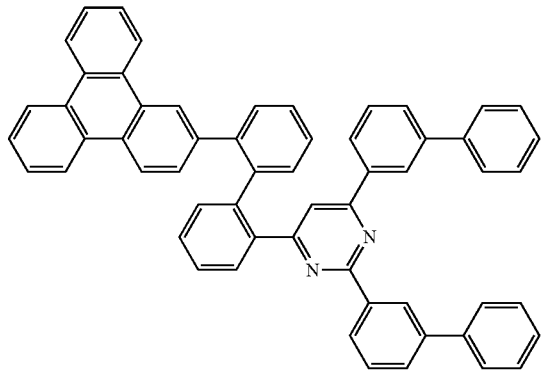
H-E67
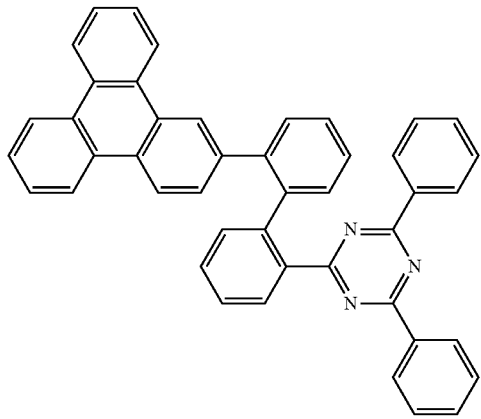
H-E68
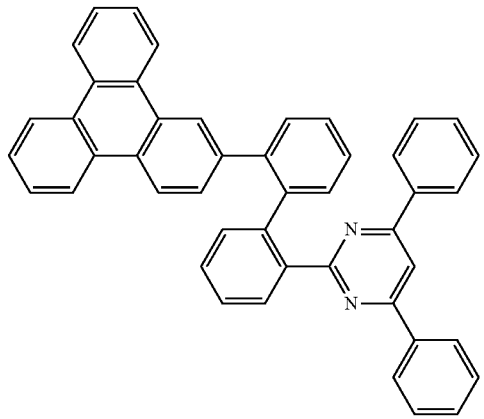

-continued
H-E69
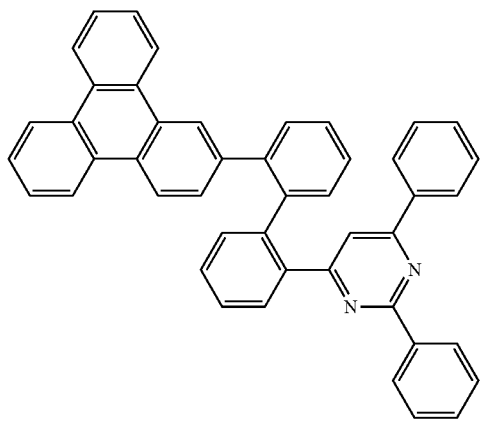
H-E70
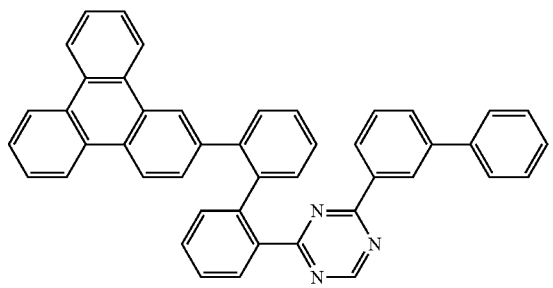
H-E71
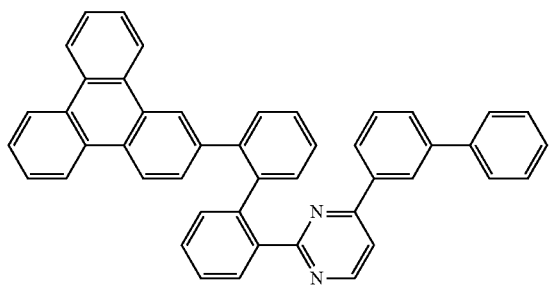
H-E72
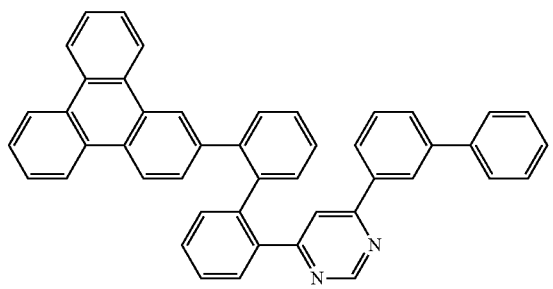
H-E73
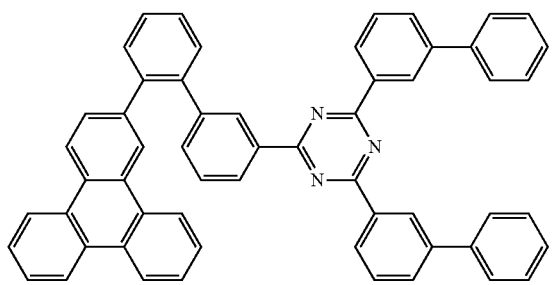
H-E74
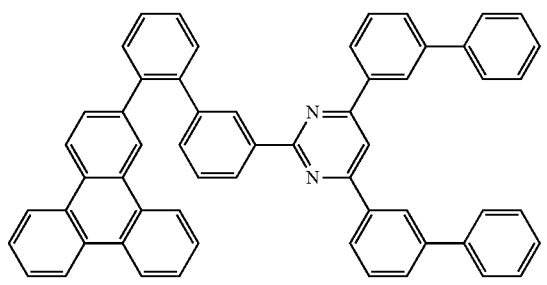
H-E75
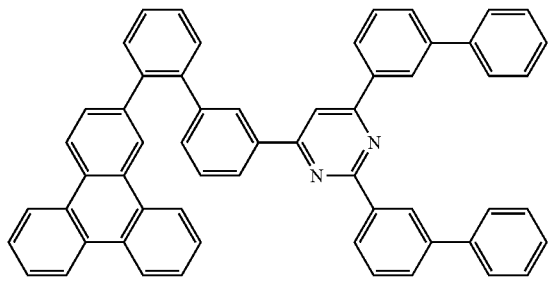
H-E76
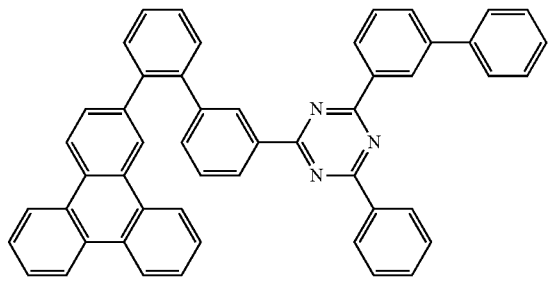

-continued
H-E77
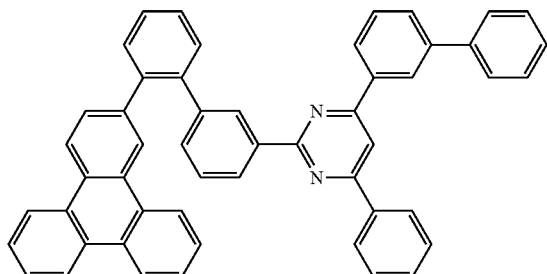
H-E78
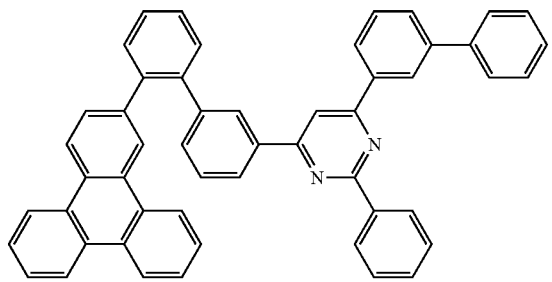
H-E79
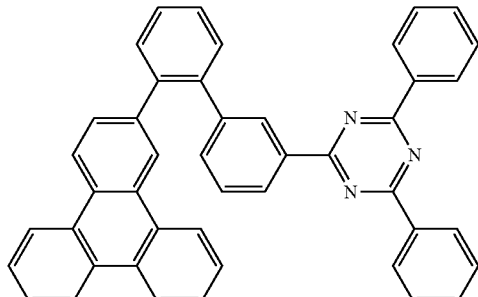
H-E80
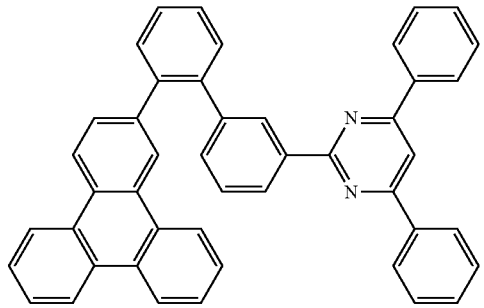
H-E81
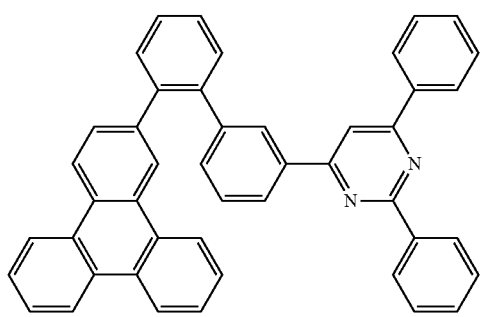
H-E82
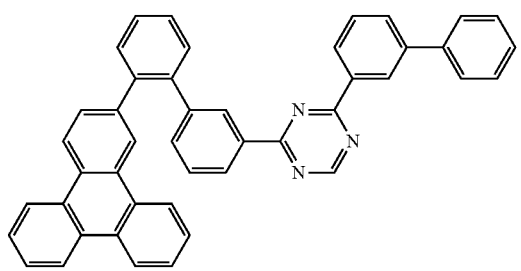
H-E83
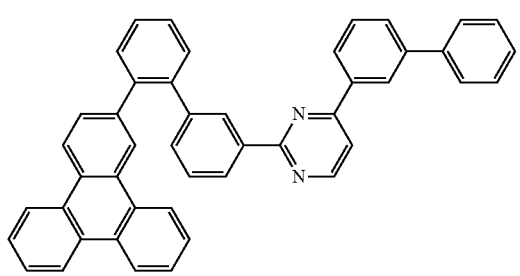
H-E84
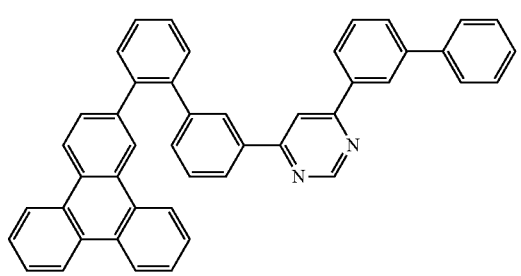
H-E(1)
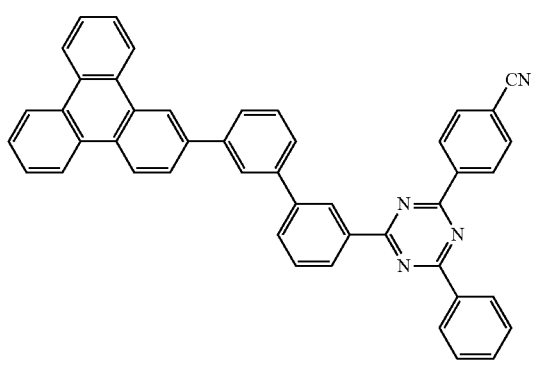
H-E(2)
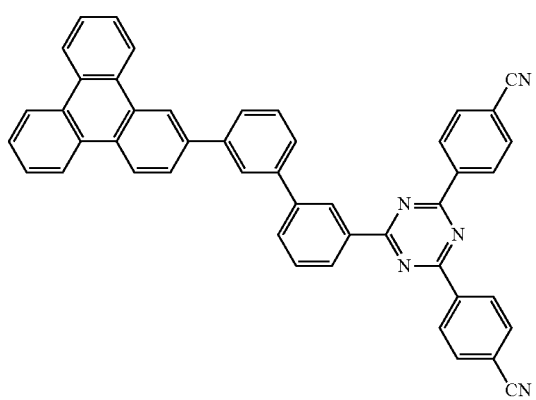

-continued
H-E(3)
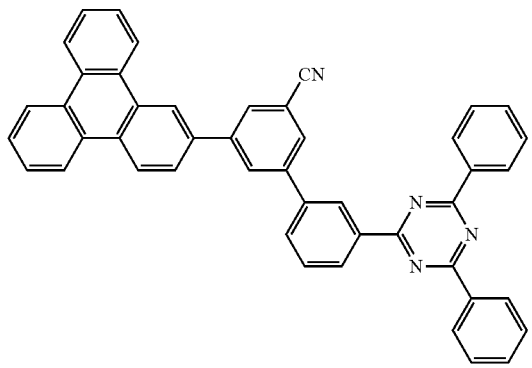
H-E(4)
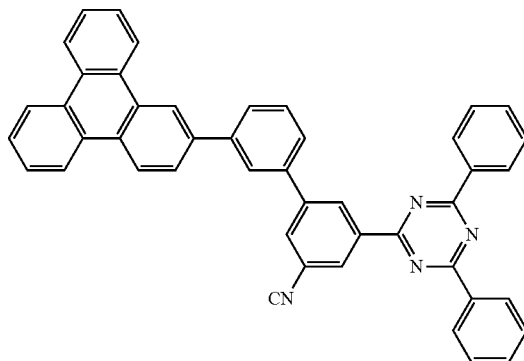
A-1
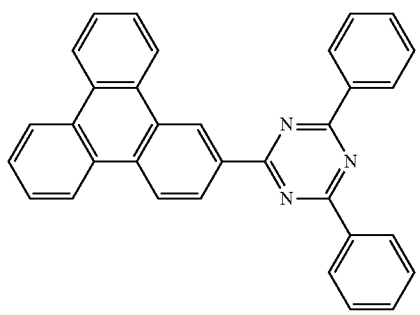
A-2
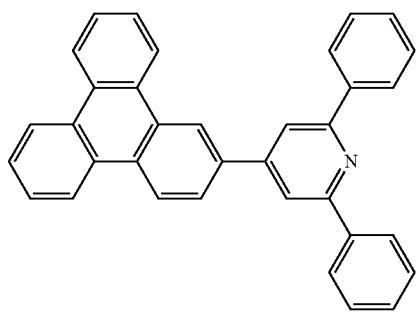
A-4
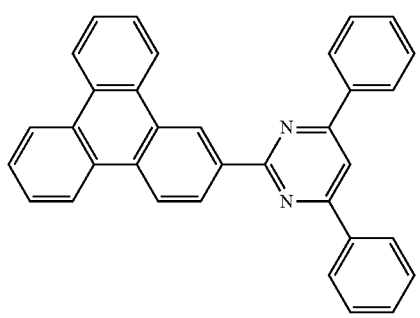
A-3
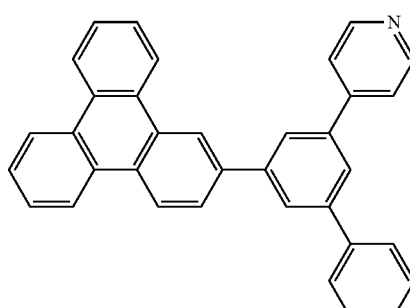
A-5
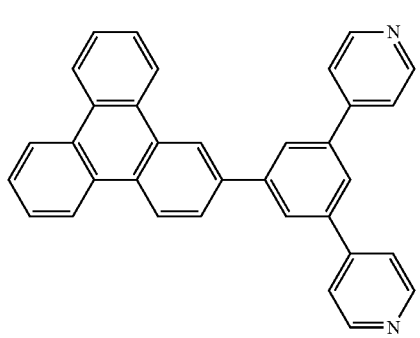
A-6
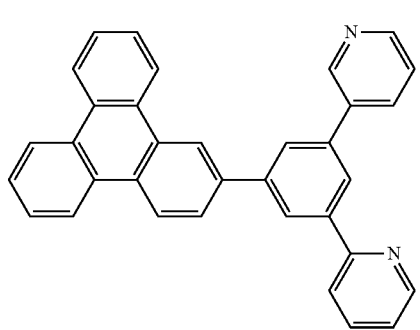

-continued
A-7
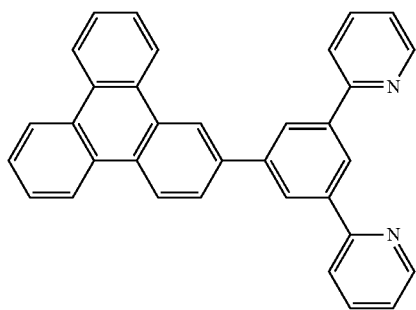
A-8
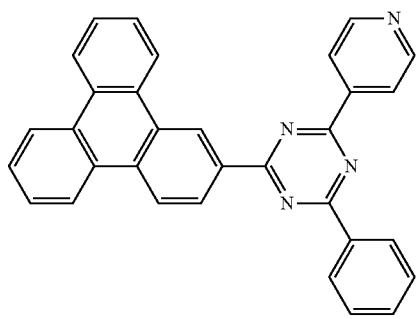
A-9
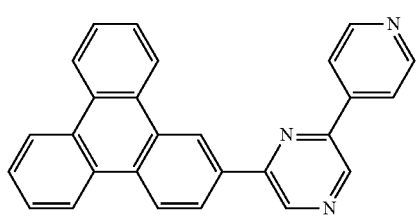
A-10
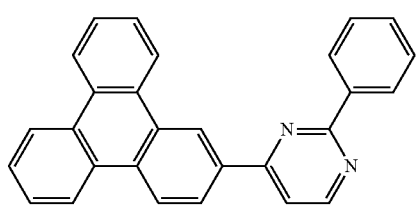
A-11
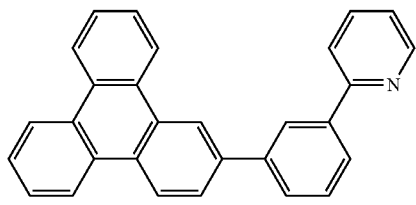
A-12
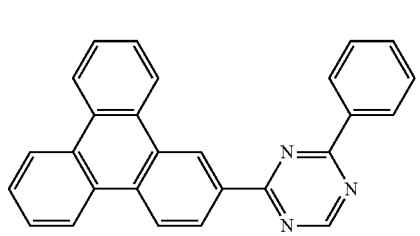
A-13
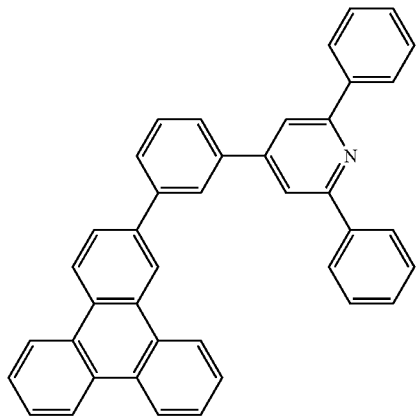
A-14
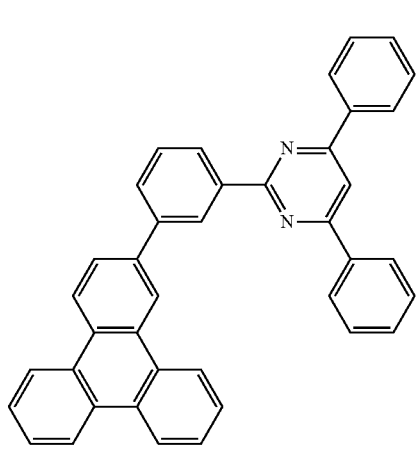
A-15
A-16
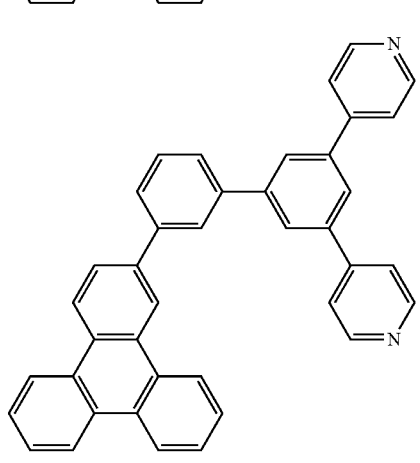

-continued

A-17

A-18

A-19

A-20

A-21

A-22

-continued
A-23
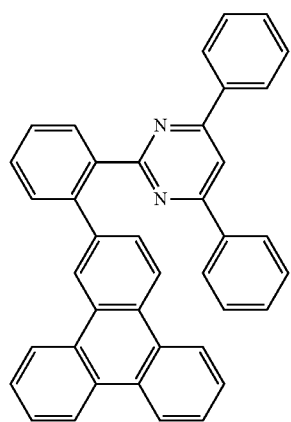
A-24
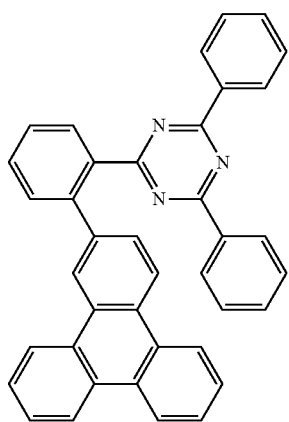
A-25
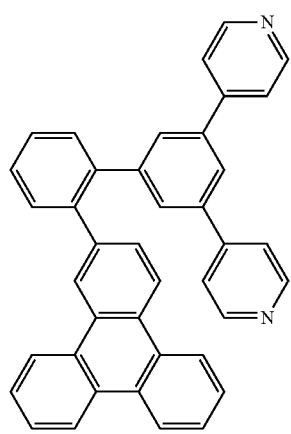
A-26
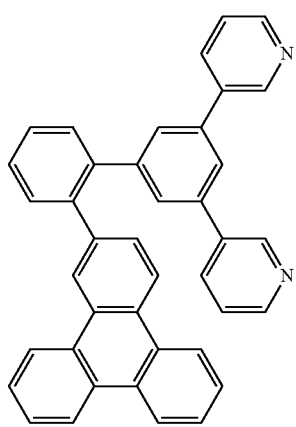
A-27
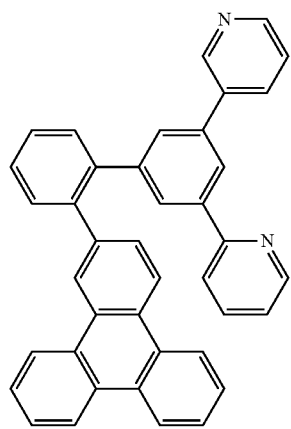
A-28
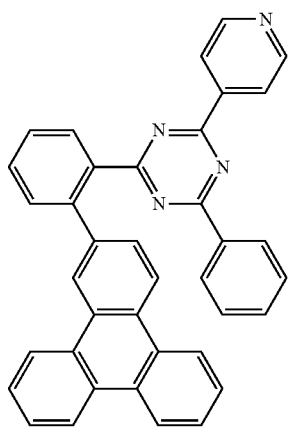

-continued
A-29
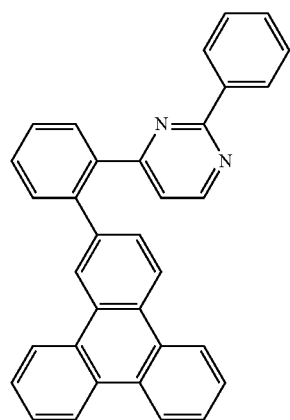
A-30
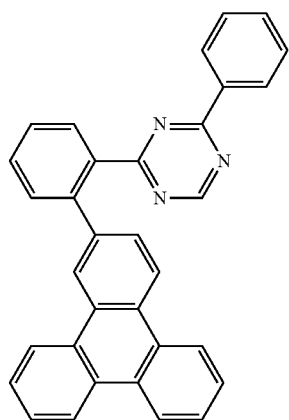
A-31
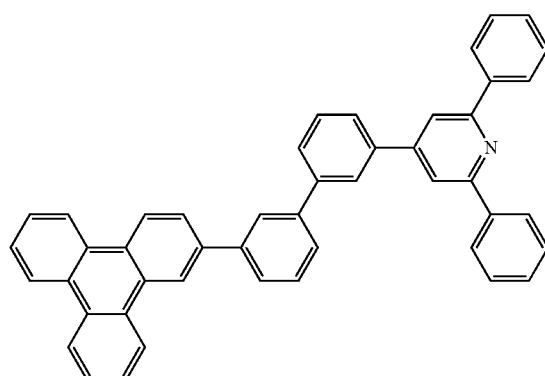
A-32
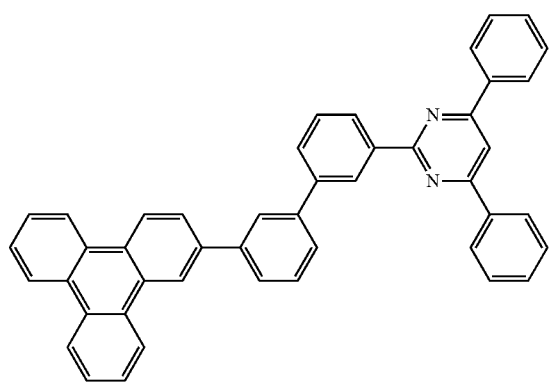
A-33
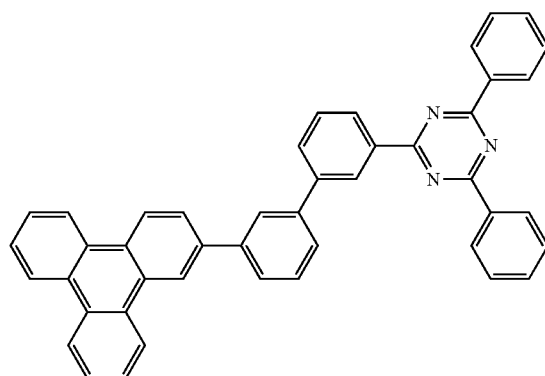
A-34
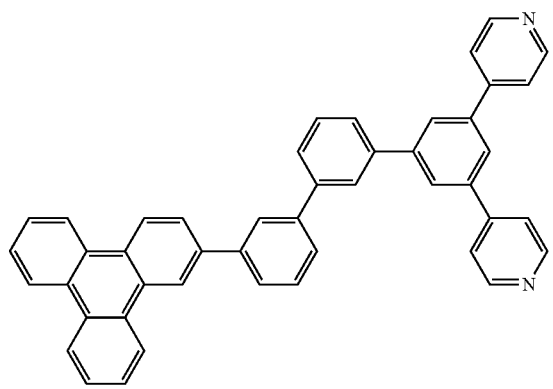
A-35
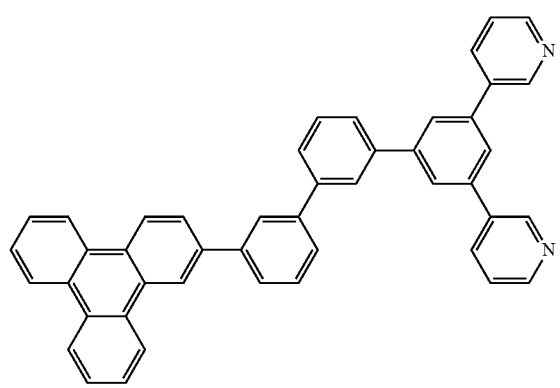
A-36
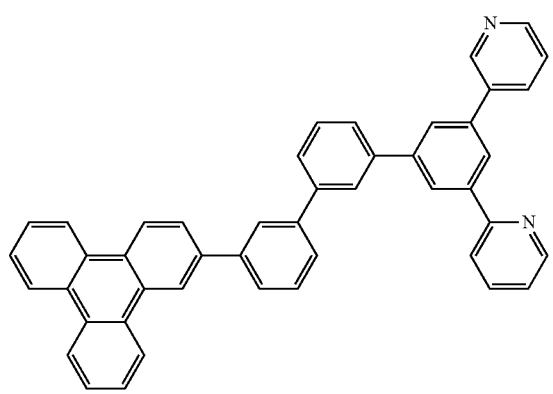

-continued
A-37
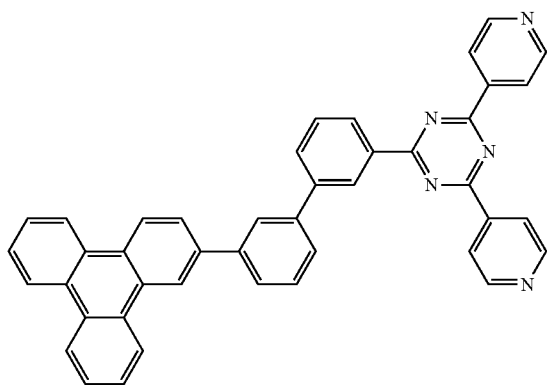
A-38
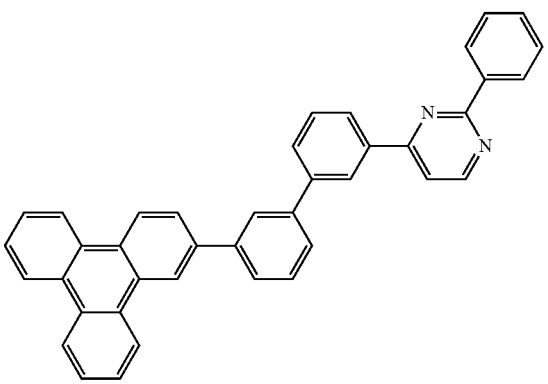
A-39
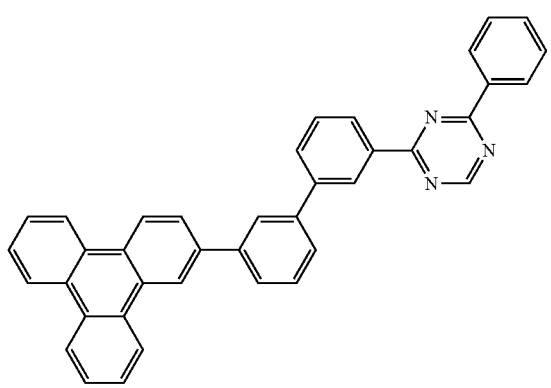
A-40
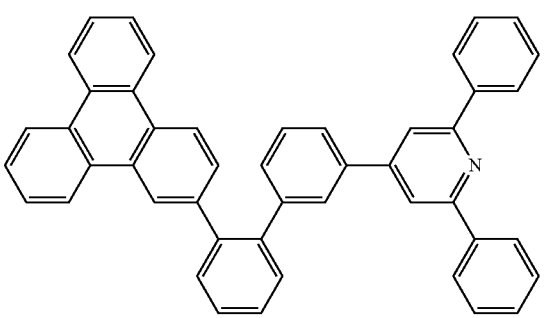
A-41
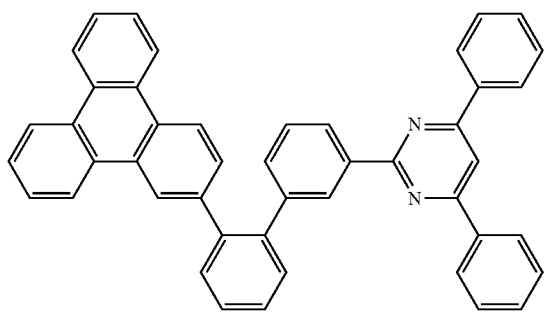
A-42
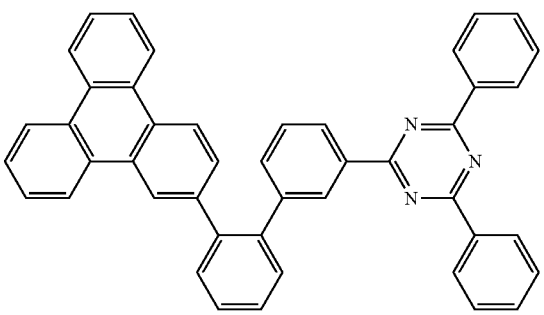
A-43
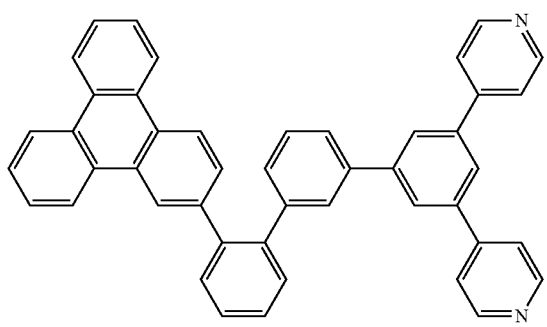
A-44
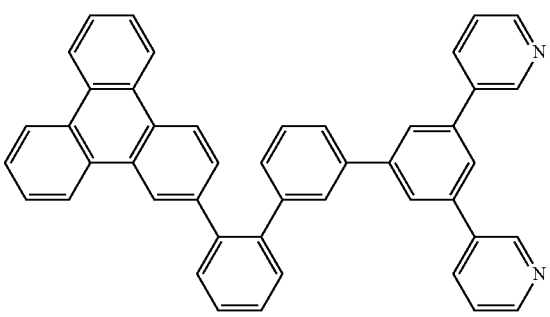

-continued
A-45
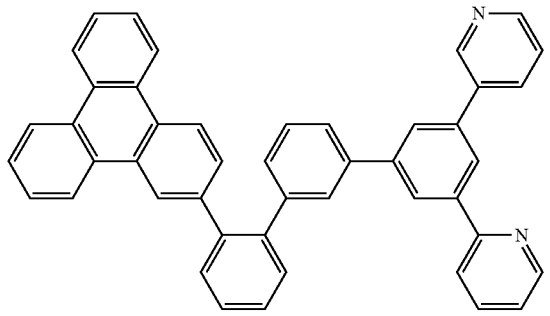
A-46
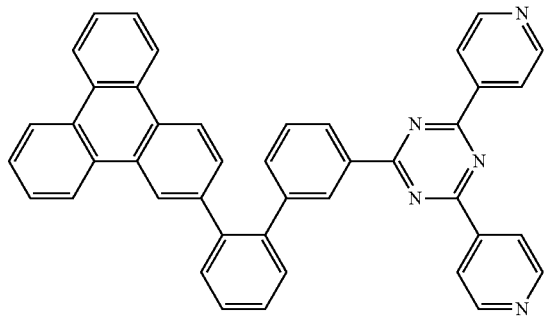
A-47
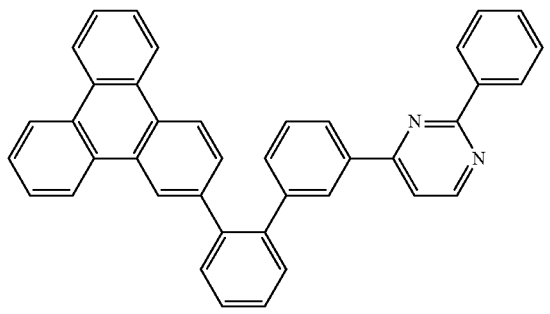
A-48
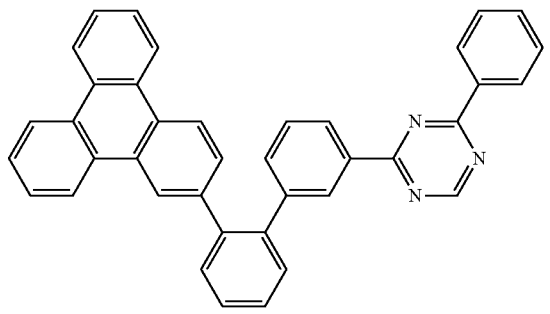
A-49
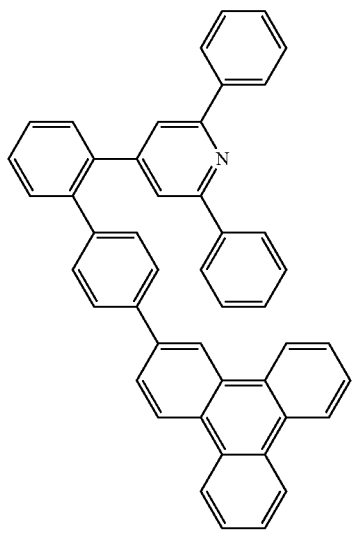
A-50
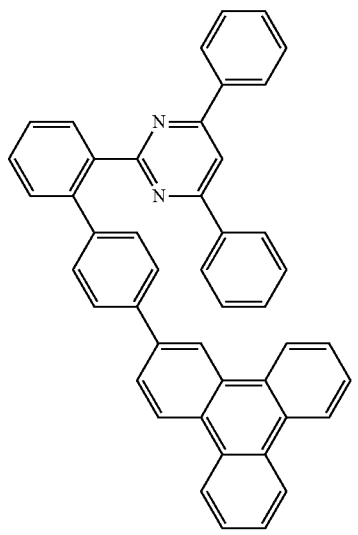

-continued
A-51
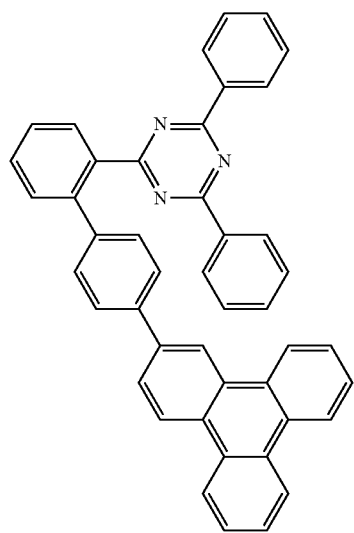
A-52
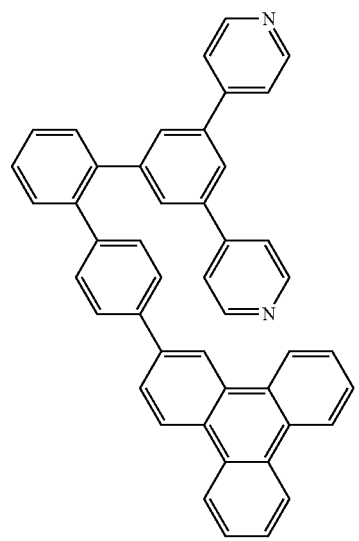
A-54
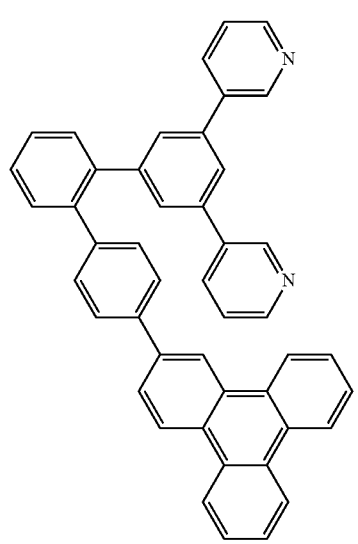
A-53
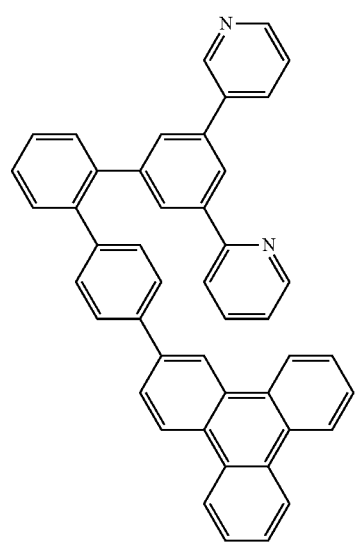
A-55
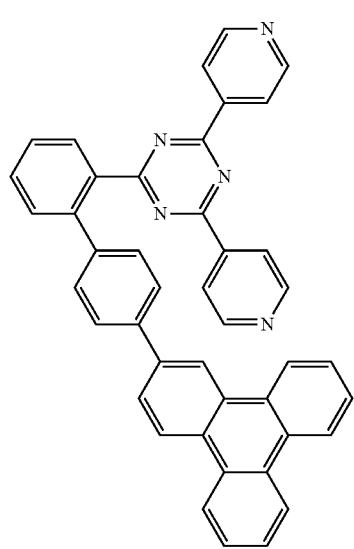
A-56
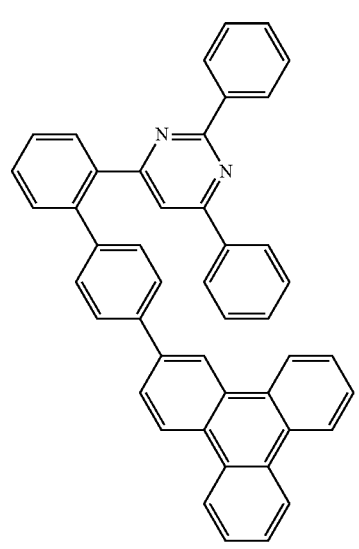

-continued

A-57

A-58

A-59

A-60

A-61

A-62

-continued
A-63
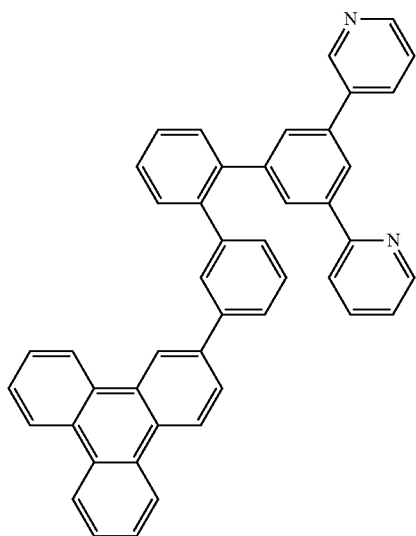
A-64
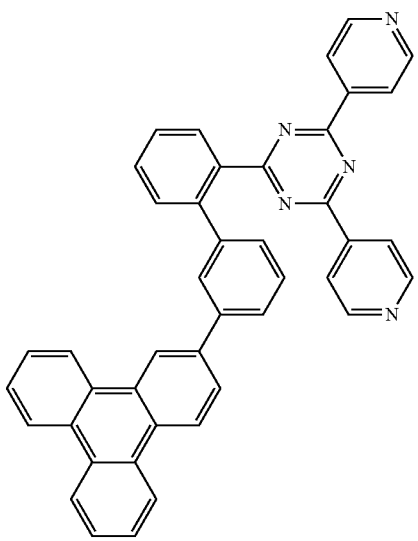
A-65
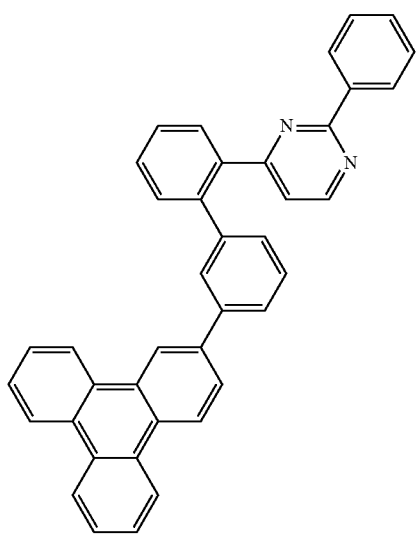
A-66
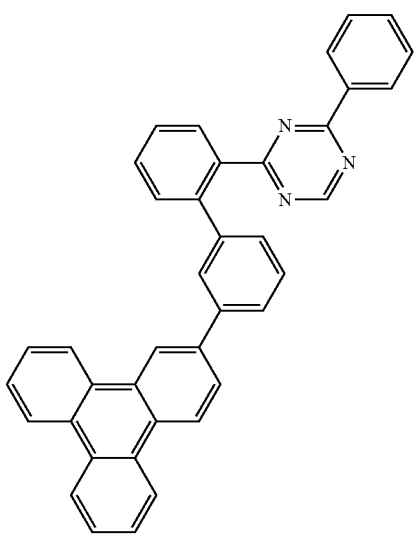
A-67
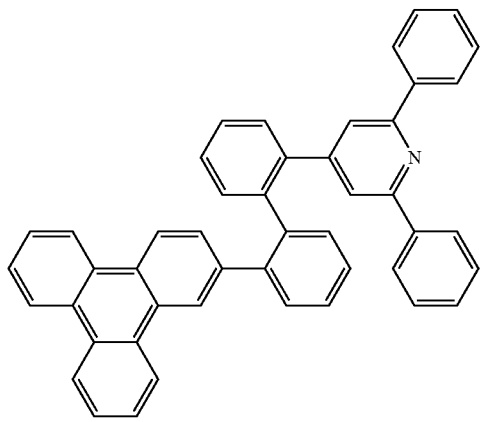
A-68
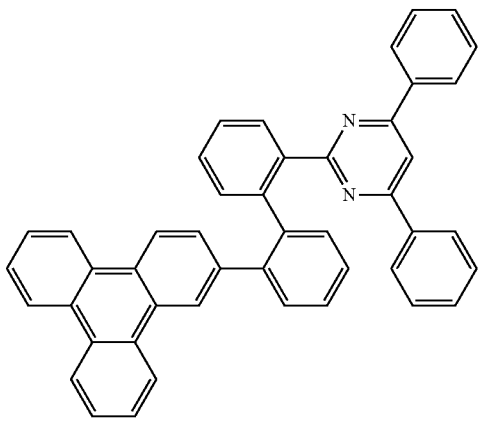

-continued
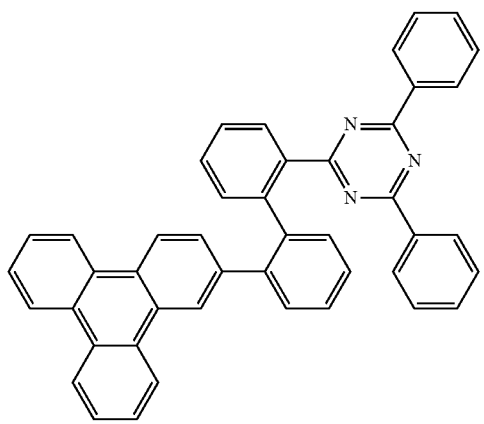
A-69
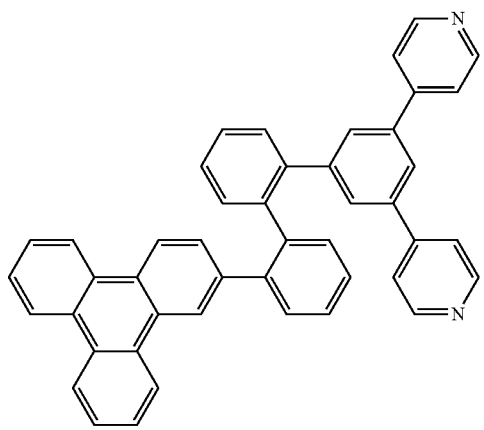
A-70
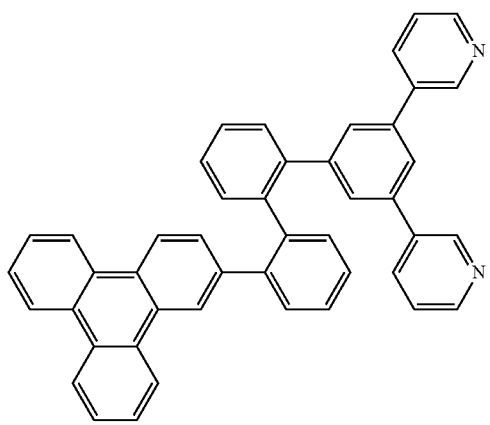
A-71
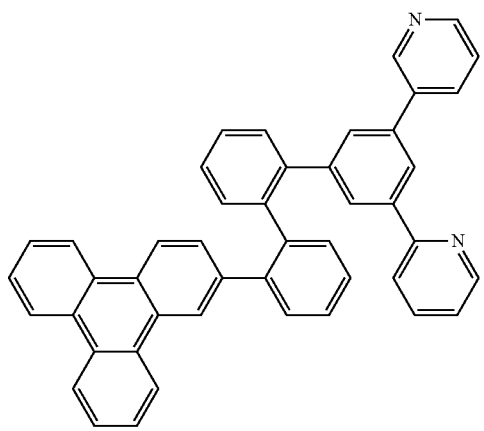
A-72
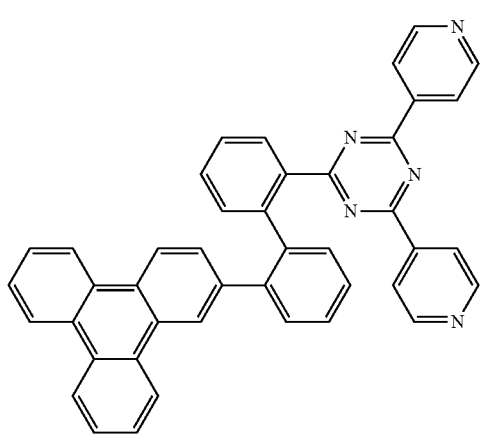
A-73
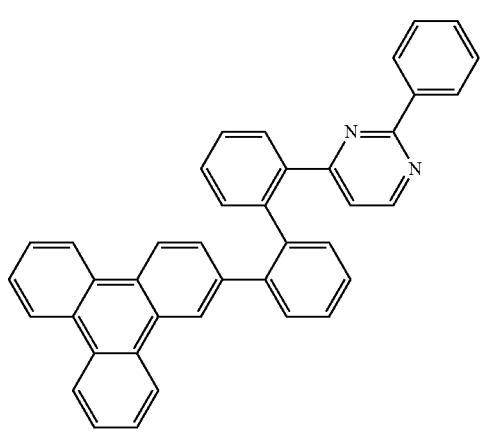
A-74

-continued
A-75
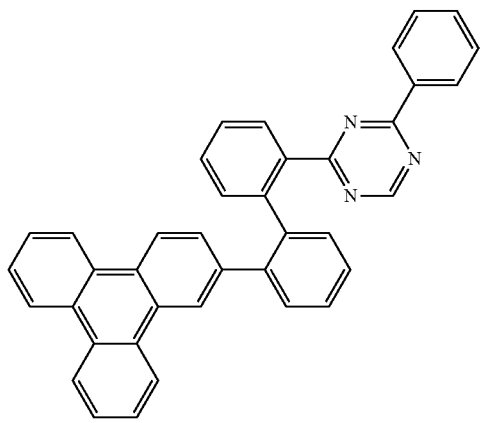
A-76
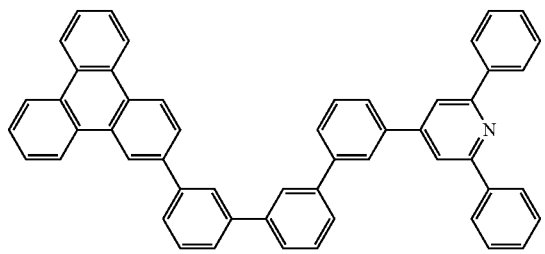
A-77
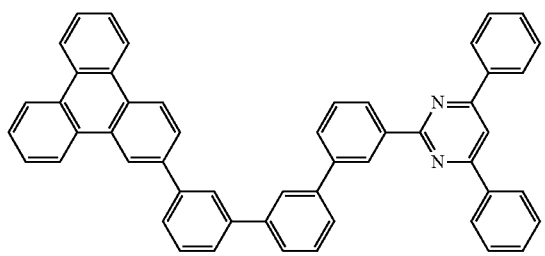
A-78
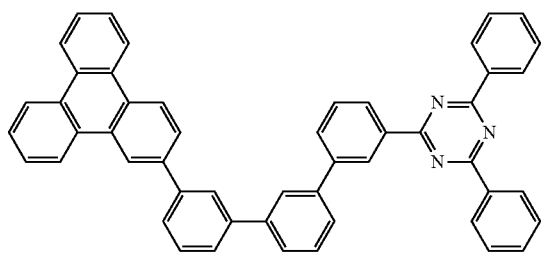
A-79
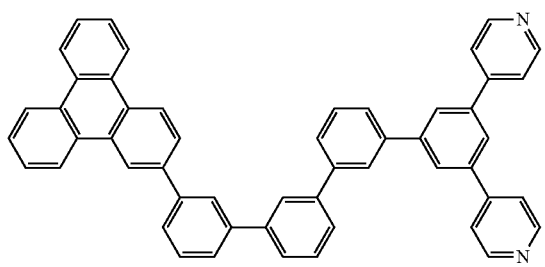
A-80
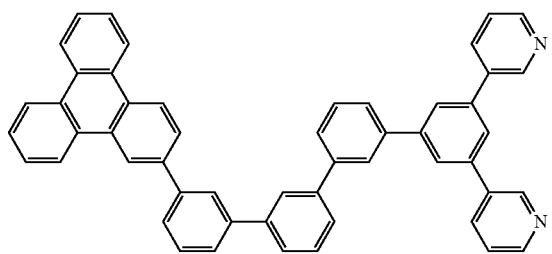
A-81
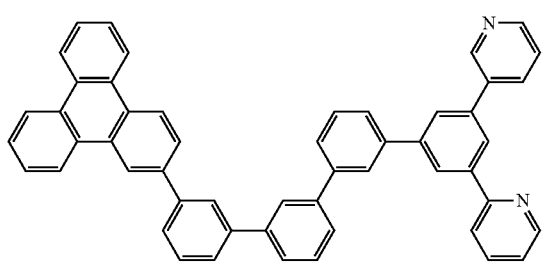
A-82
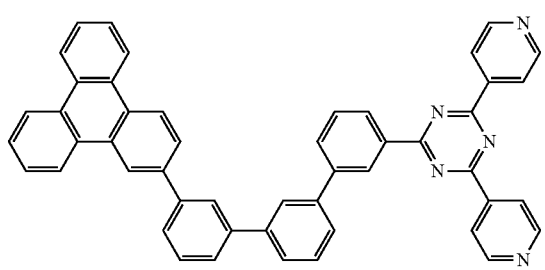
A-83
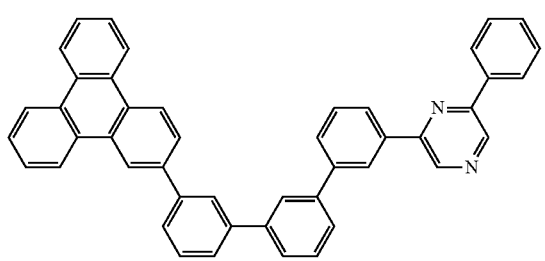
A-84
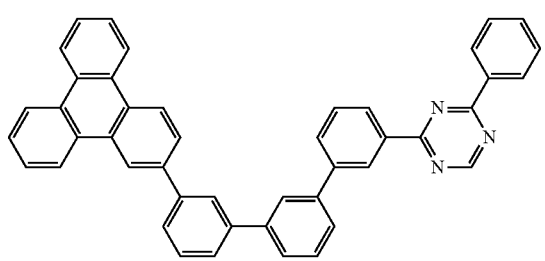

-continued
A-85
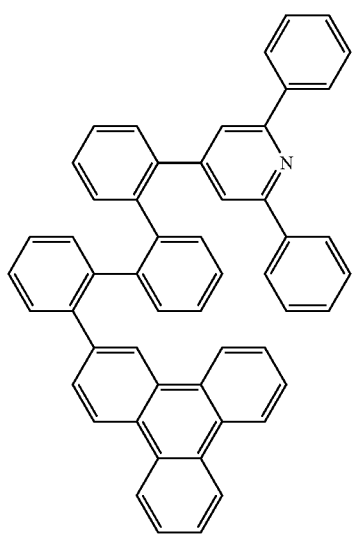
A-86
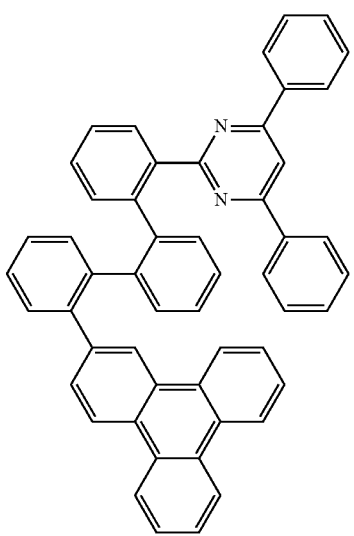
A-87
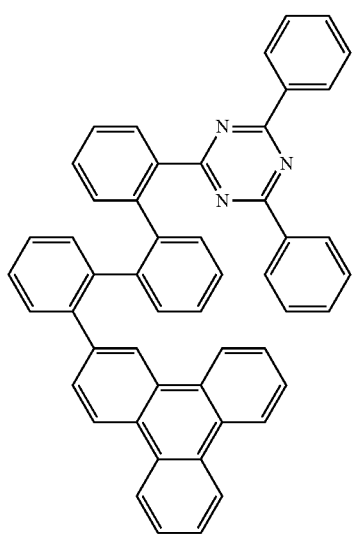
A-88
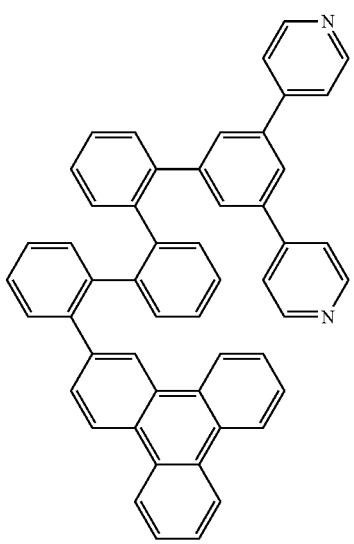
A-89
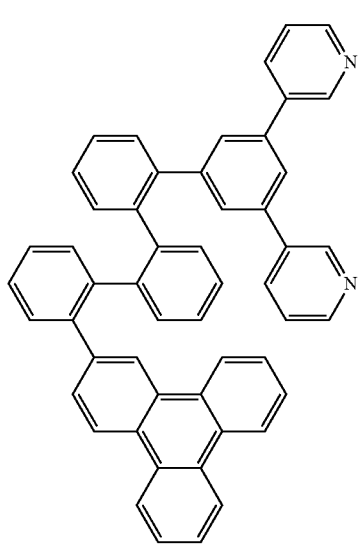
A-90
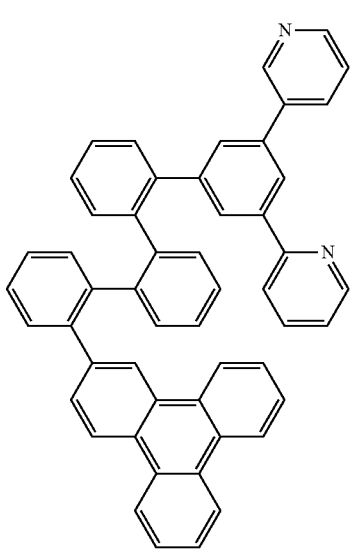

-continued
A-91
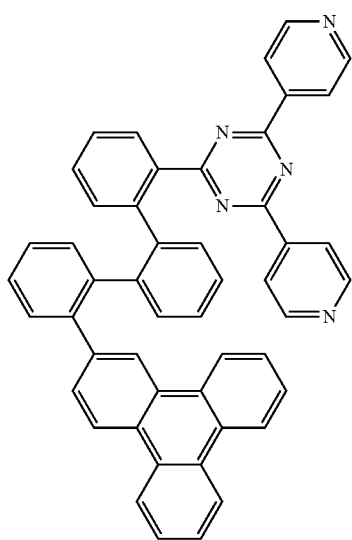
A-92
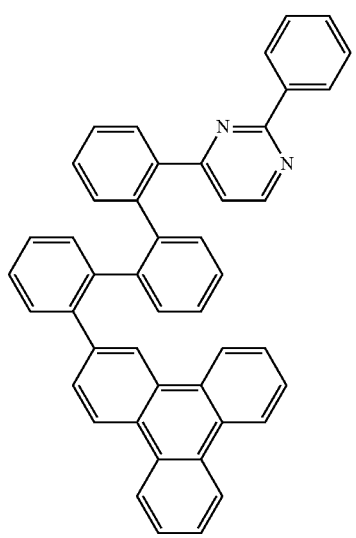
A-93
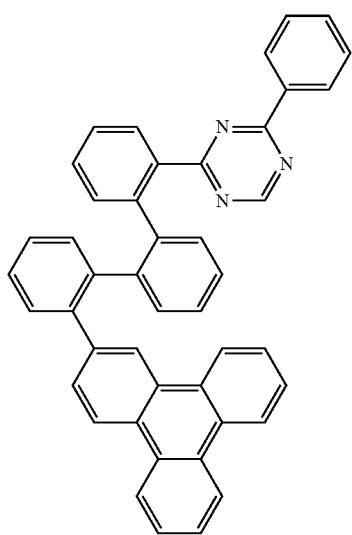
A-94
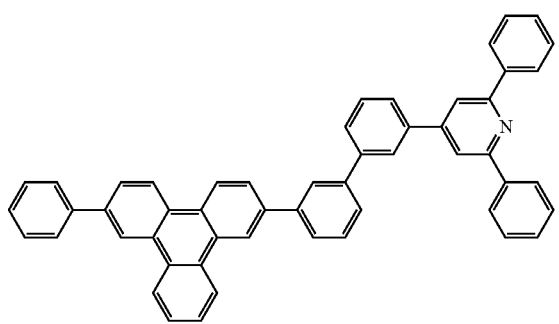
A-95
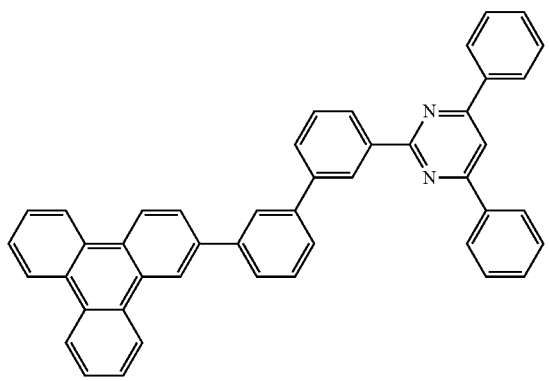
A-96
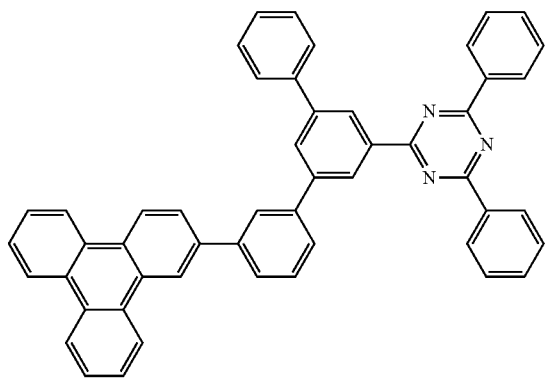

-continued
A-97
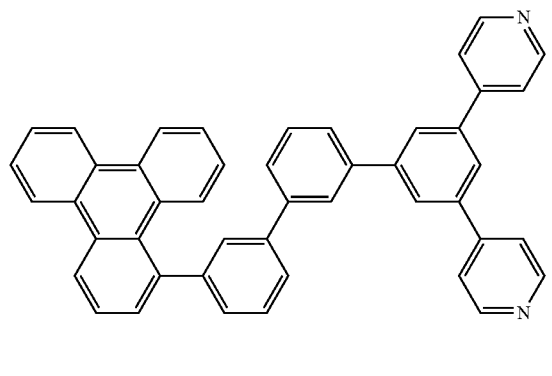
A-98
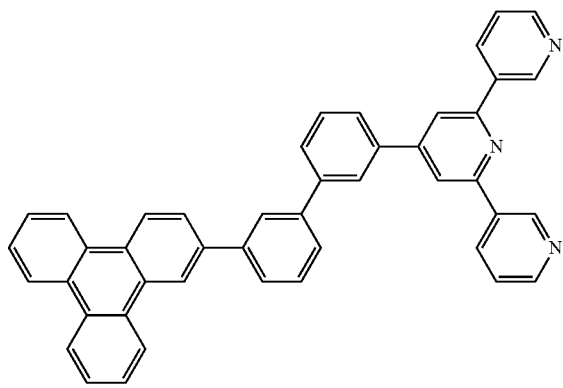
A-99
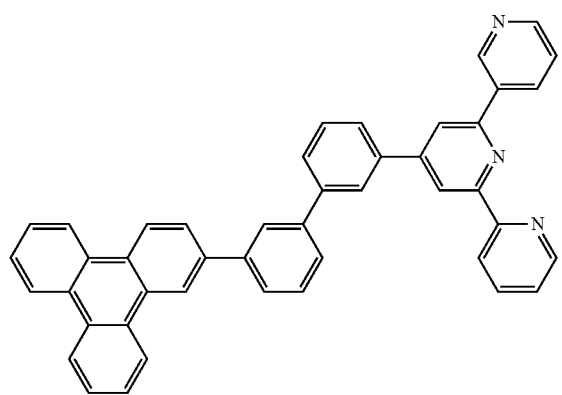
A-100
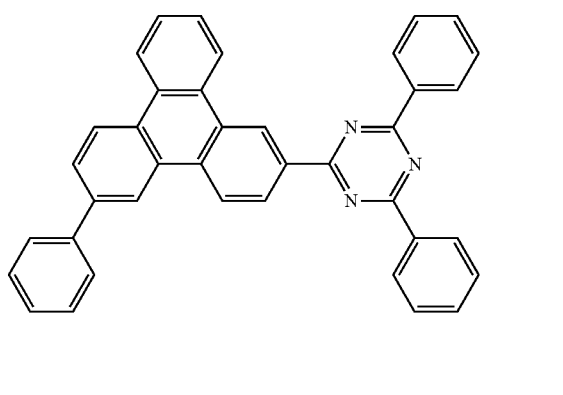
A-101
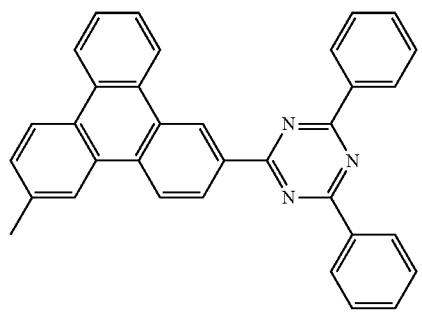
A-102
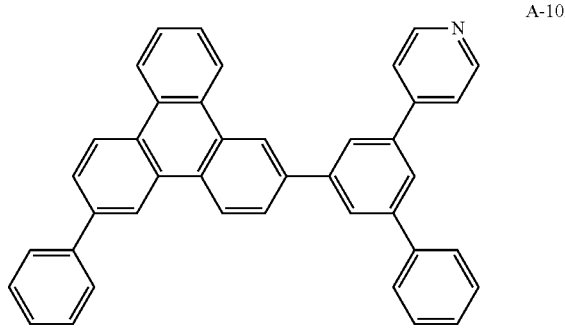
A-103
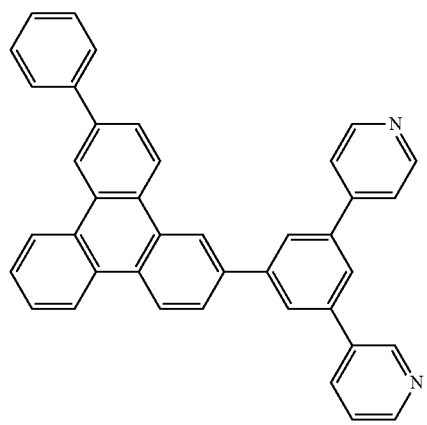
A-104
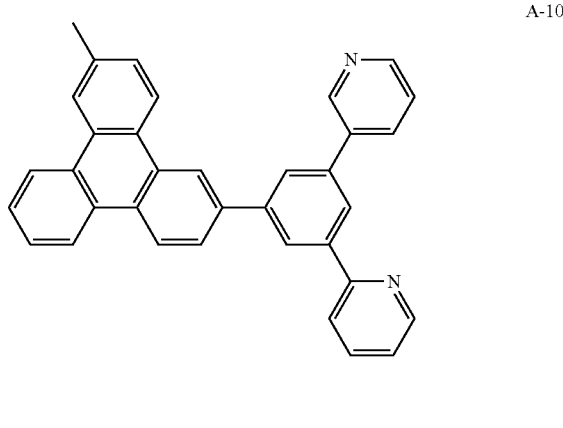

-continued
A-105
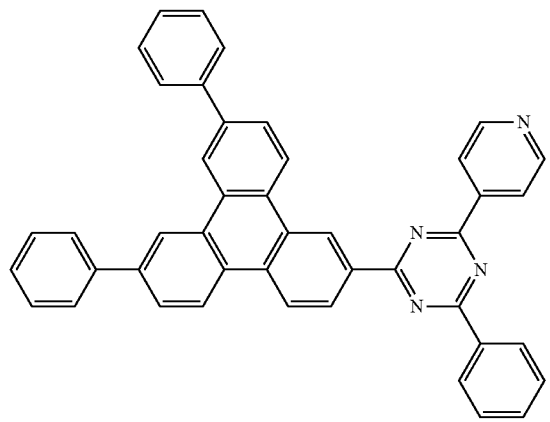
A-106
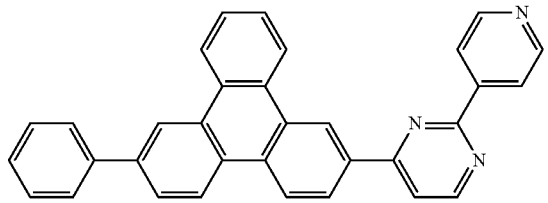
A-107
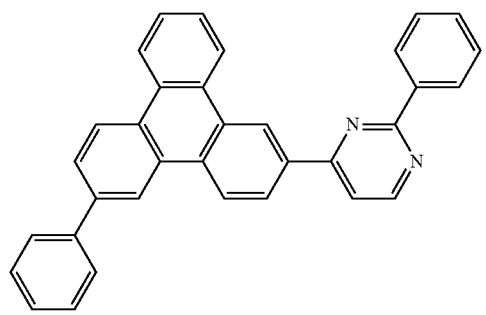
A-108
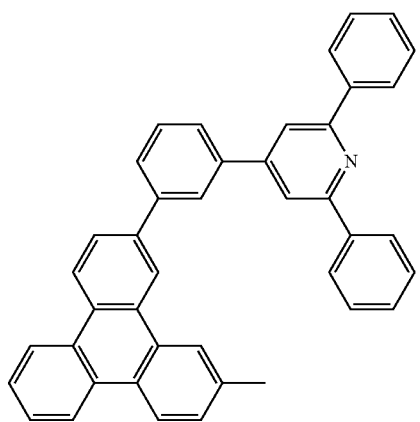
A-109
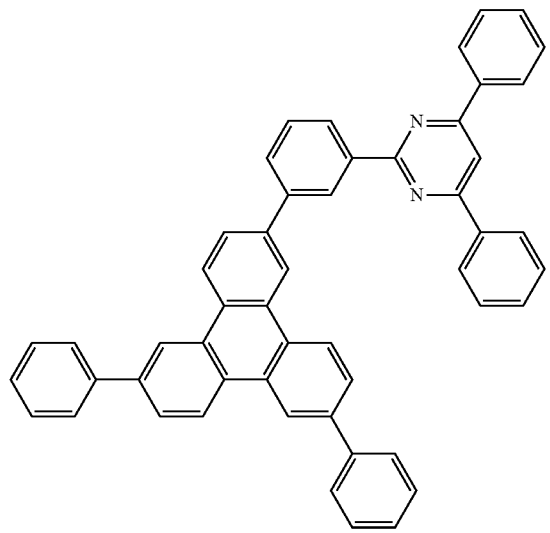
A-110
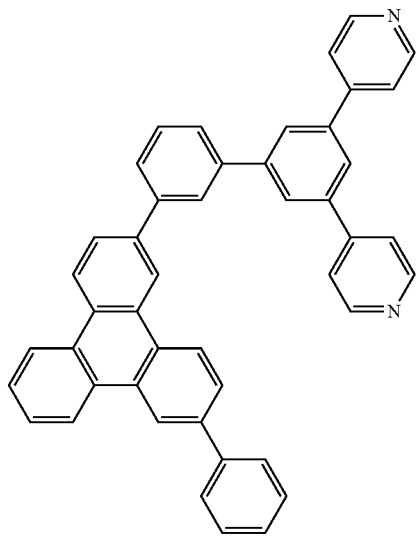

-continued
A-111
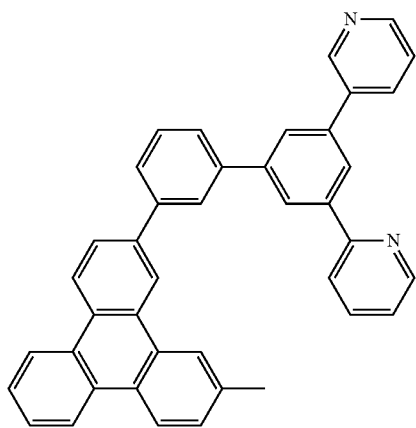
A-112
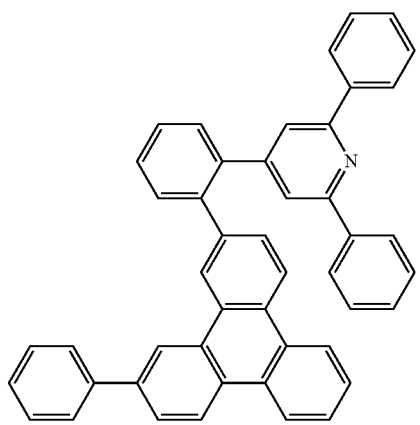
A-113
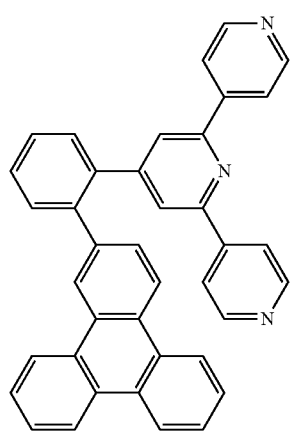
A-114
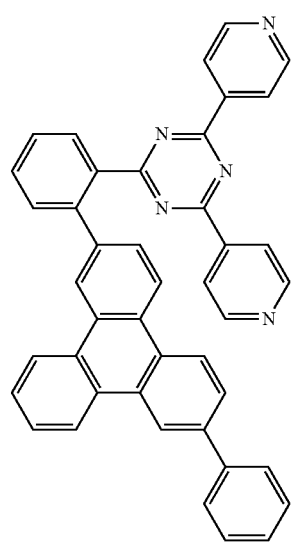
A-115
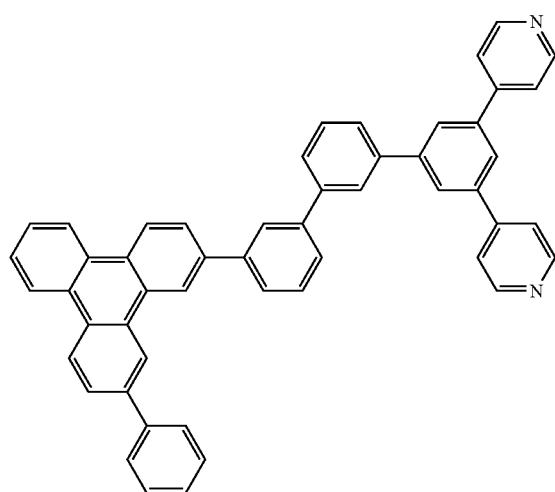
A-116
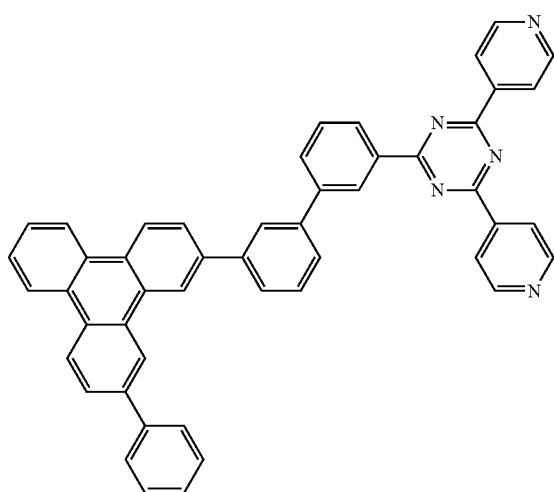

-continued
A-117
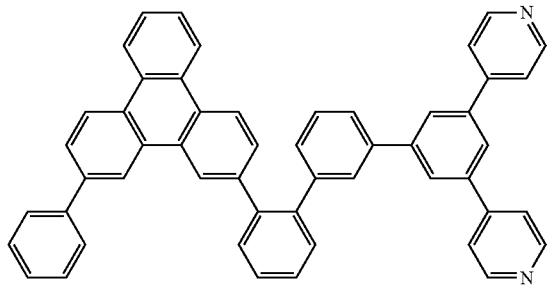
A-118
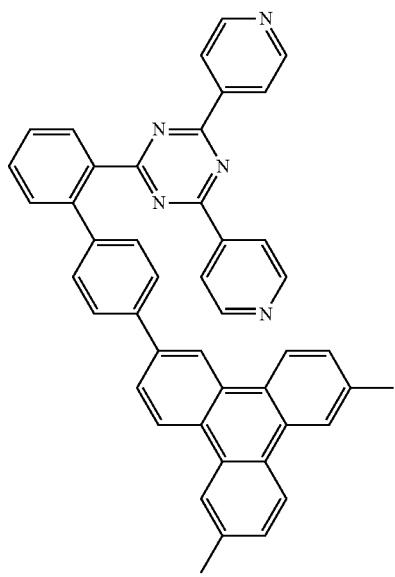
A-119
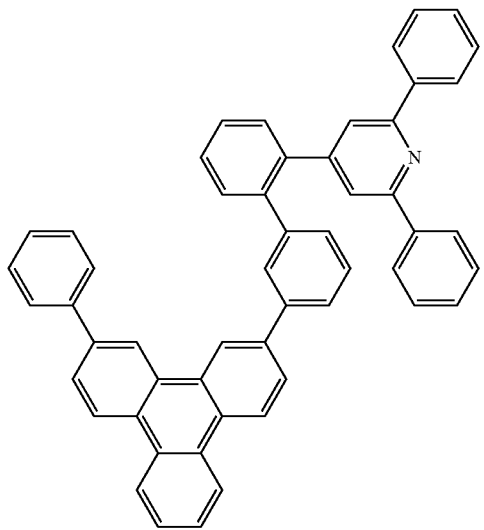
A-120
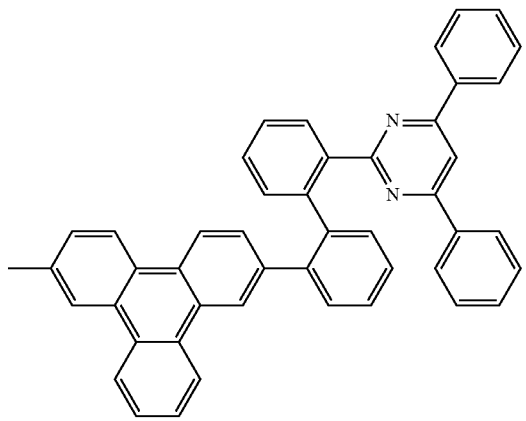

-continued
A-121
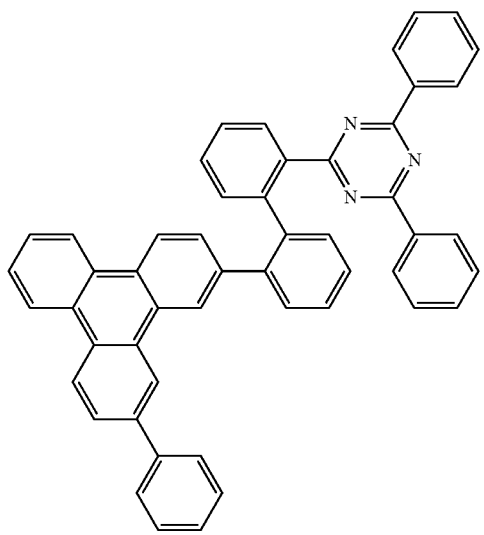
A-122
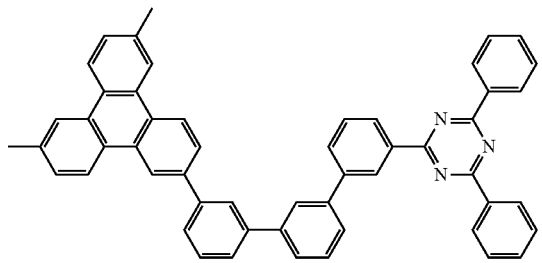
A-123
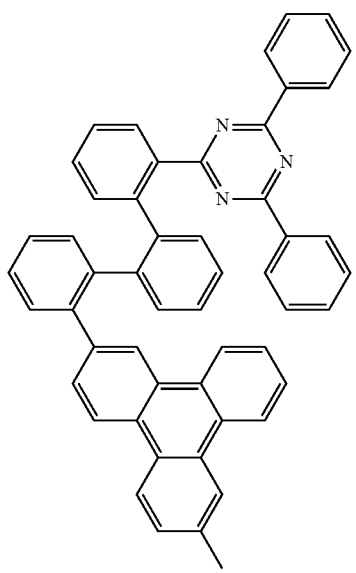
A-124
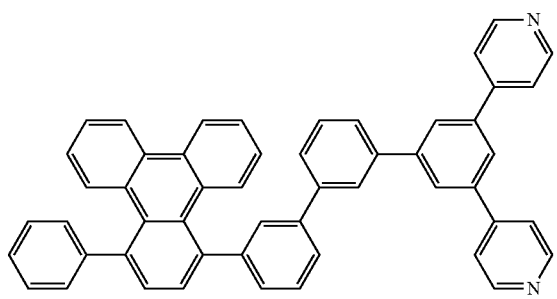
A-125 A(1)
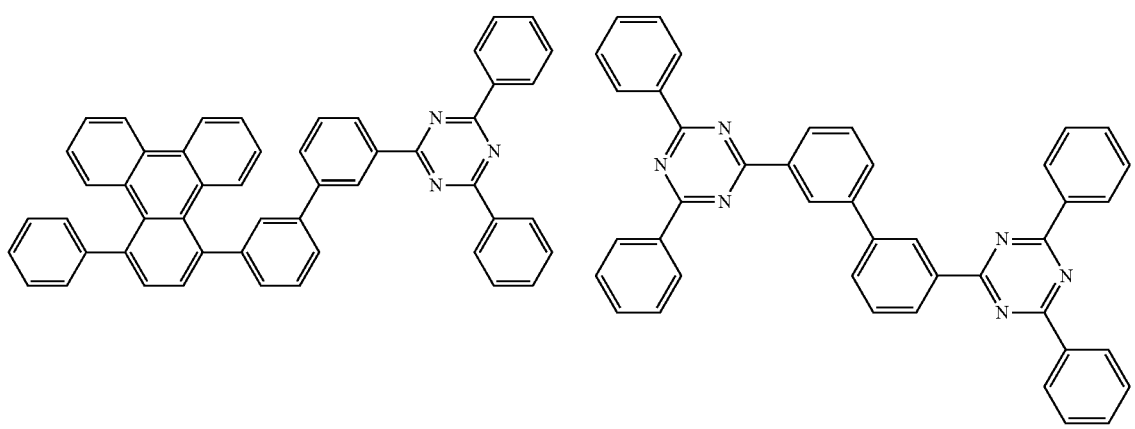

-continued
A(2)
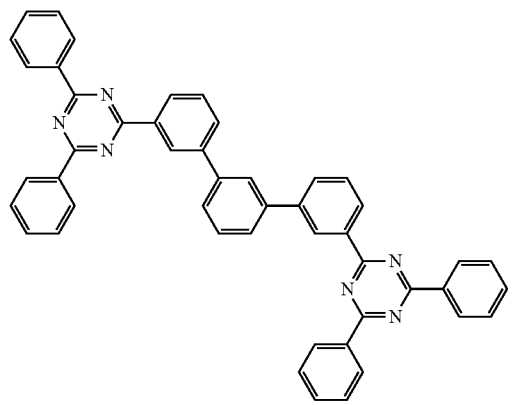
A(3)
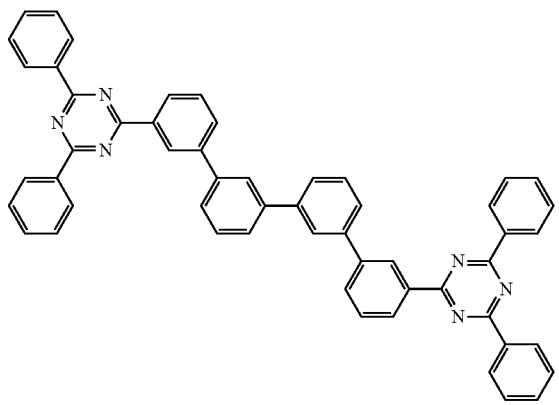
A(4)
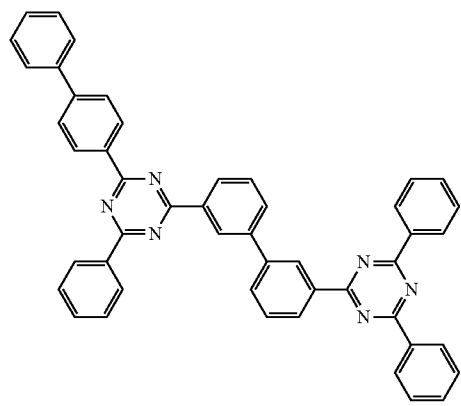
A(5)
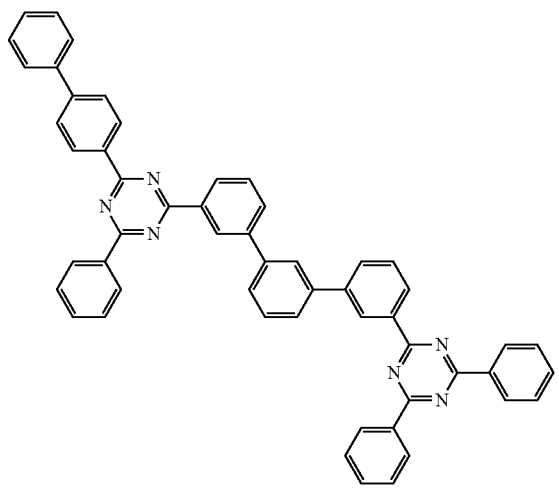
A(6)
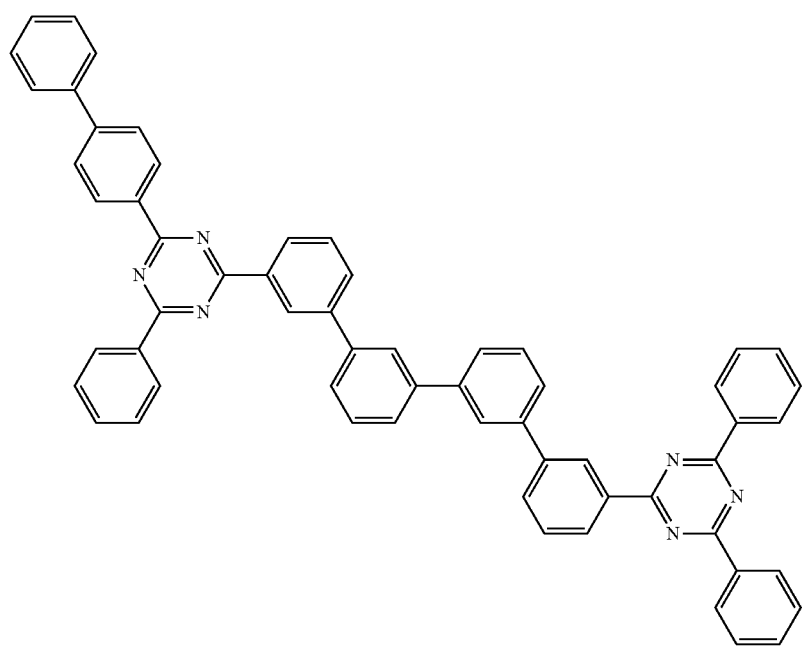

A(7)
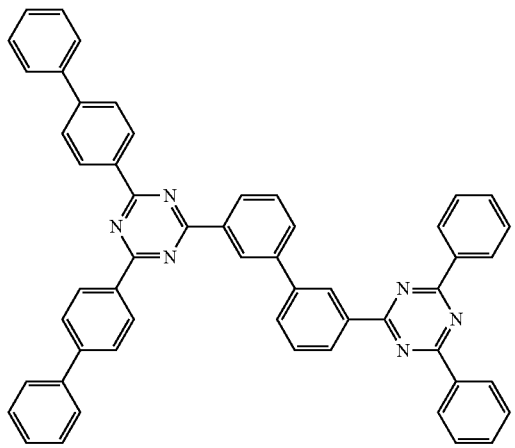
A(8)
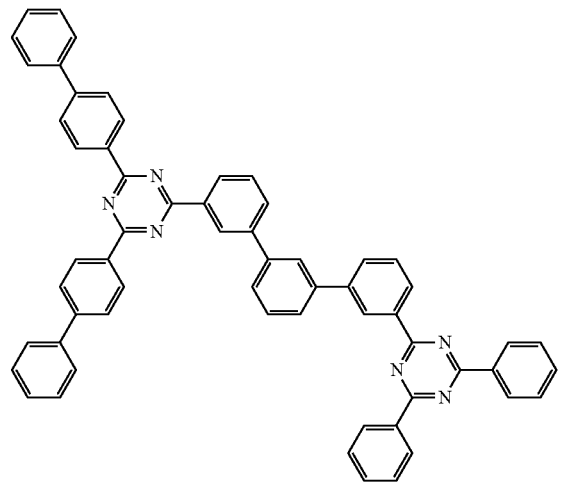
A(9)
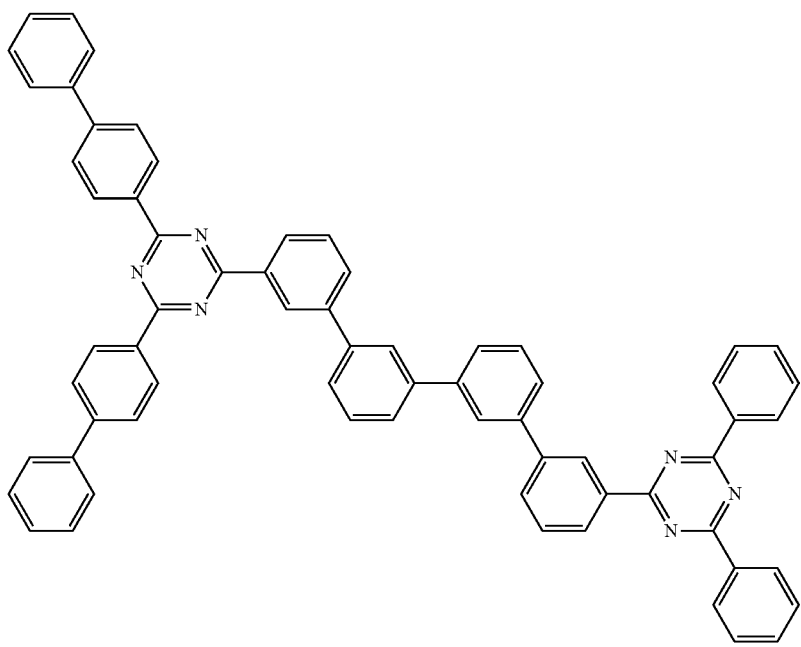

-continued
A(10)
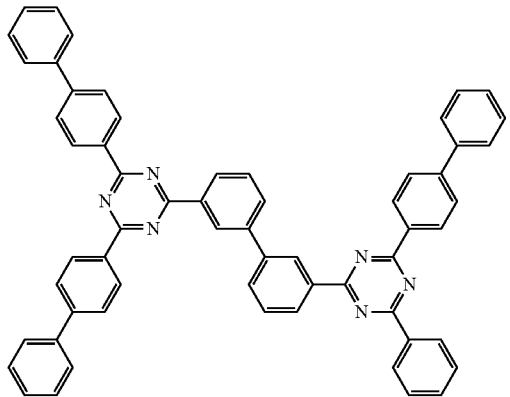
A(11)
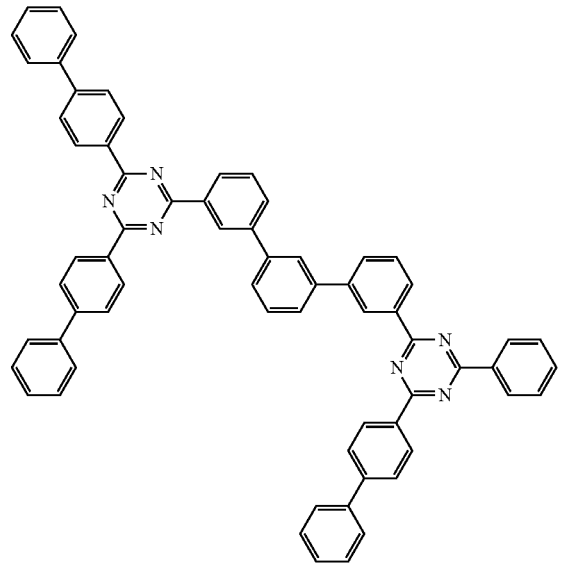
A(12)
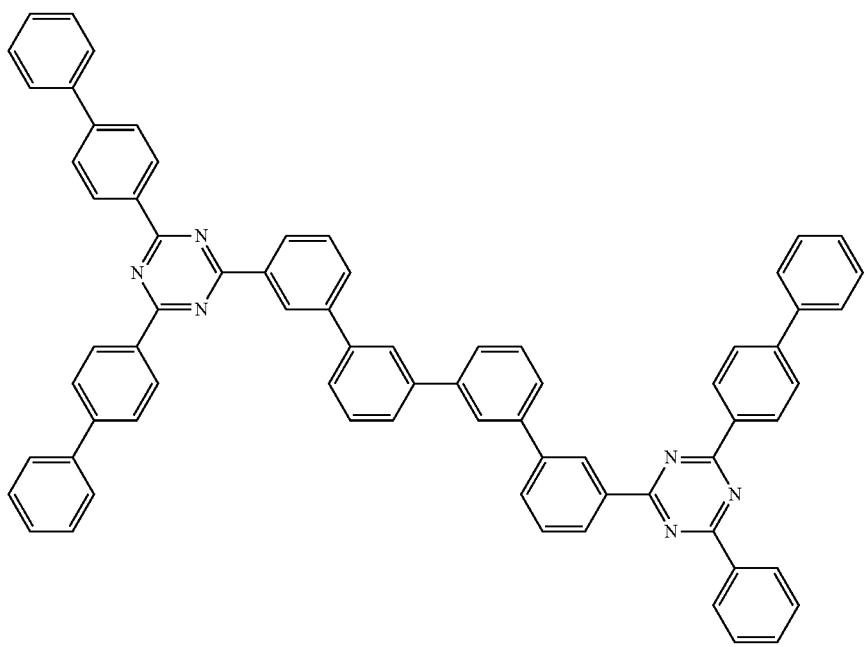

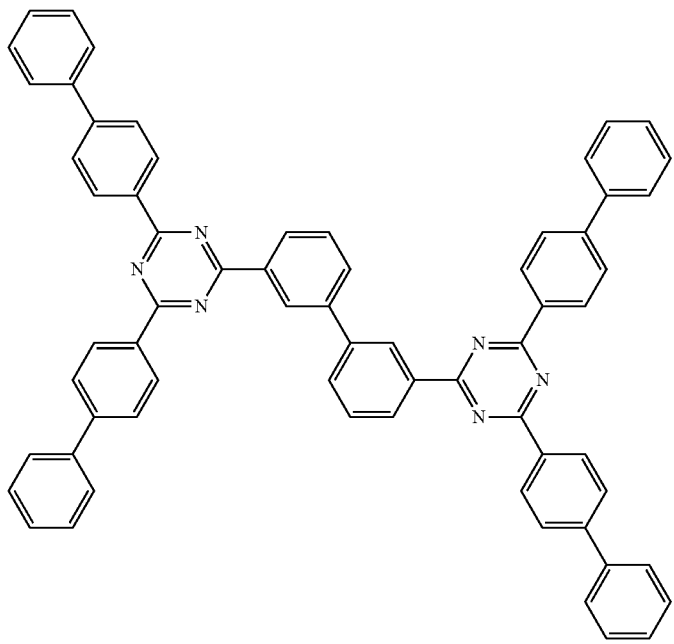
A(13)
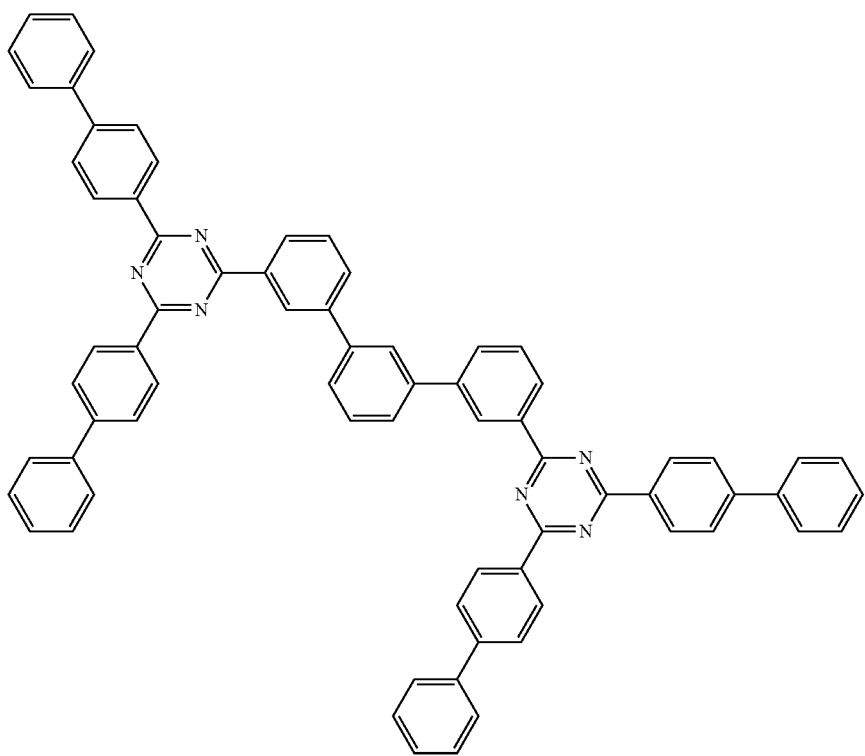
A(14)

-continued
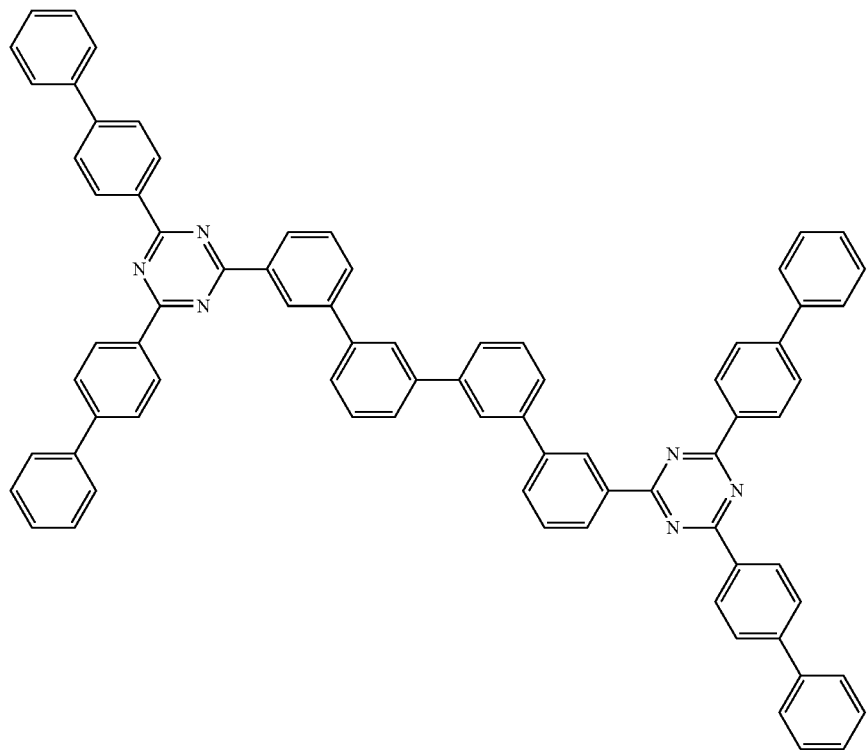
A(15)
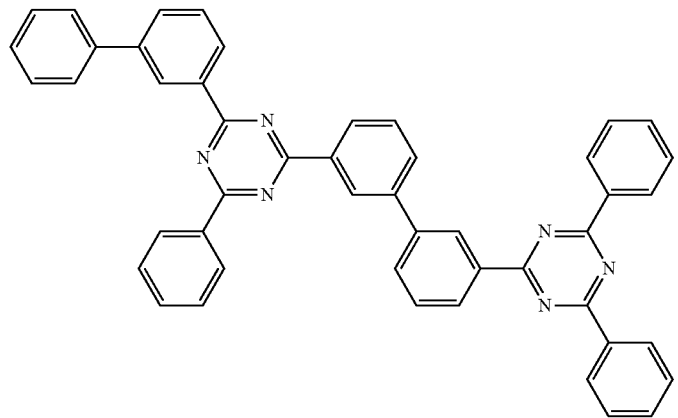
A(16)

-continued
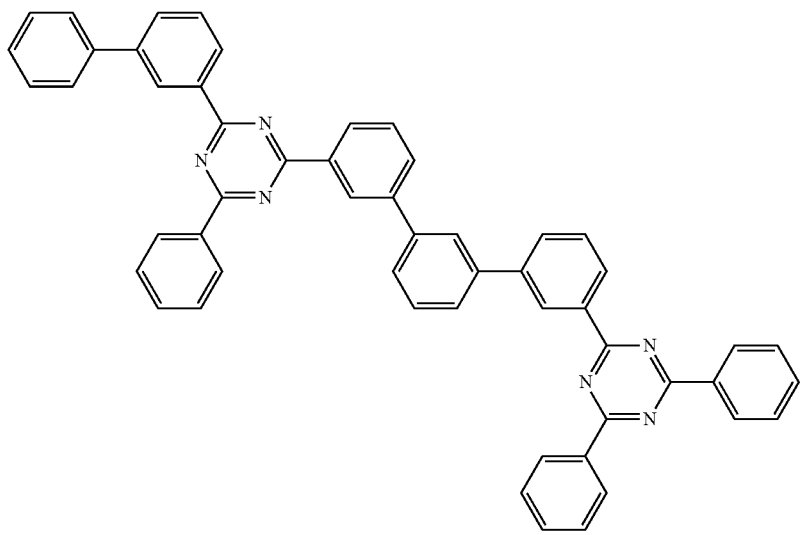
A(17)
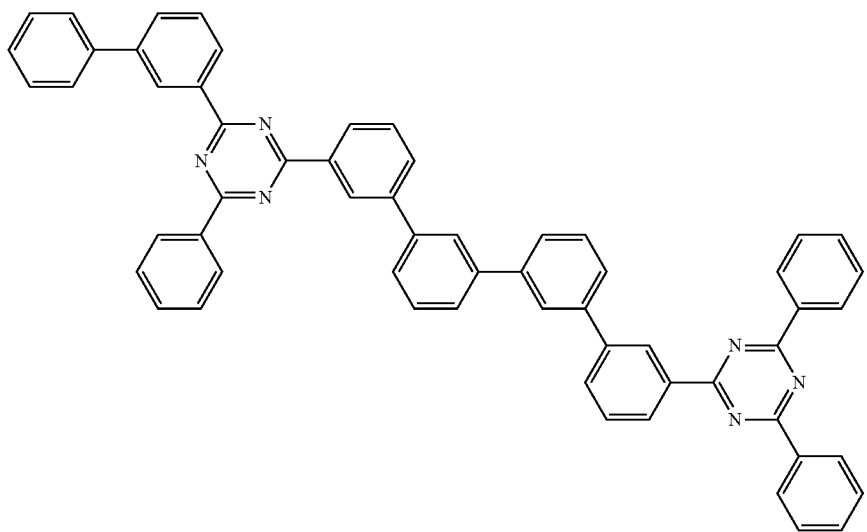
A(18)
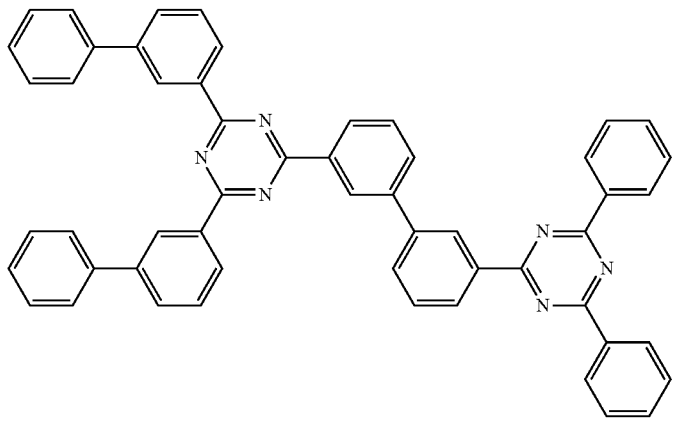
A(19)

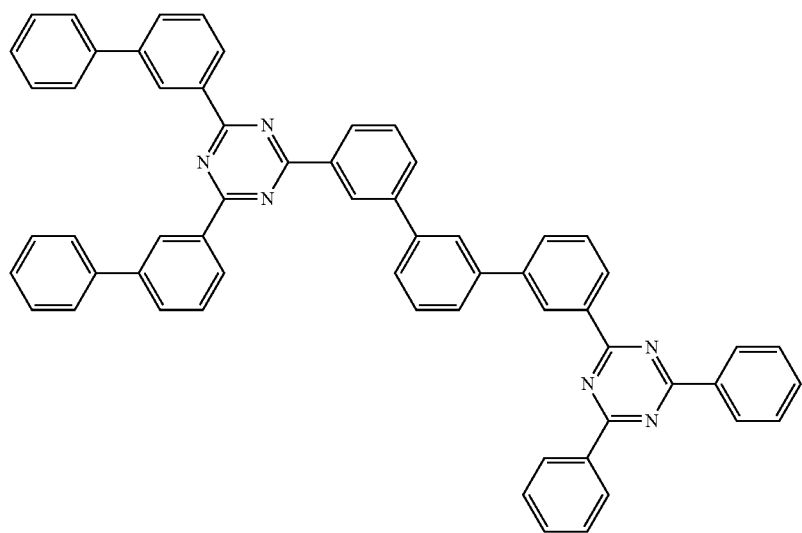
A(20)
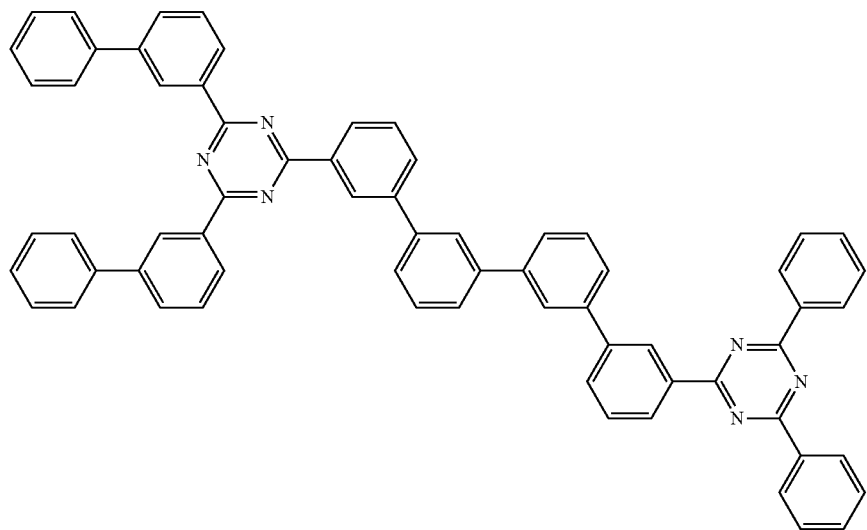
A(21)
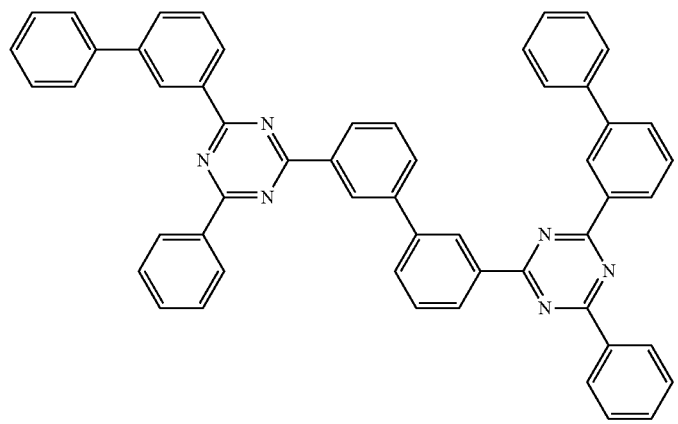
A(22)

-continued
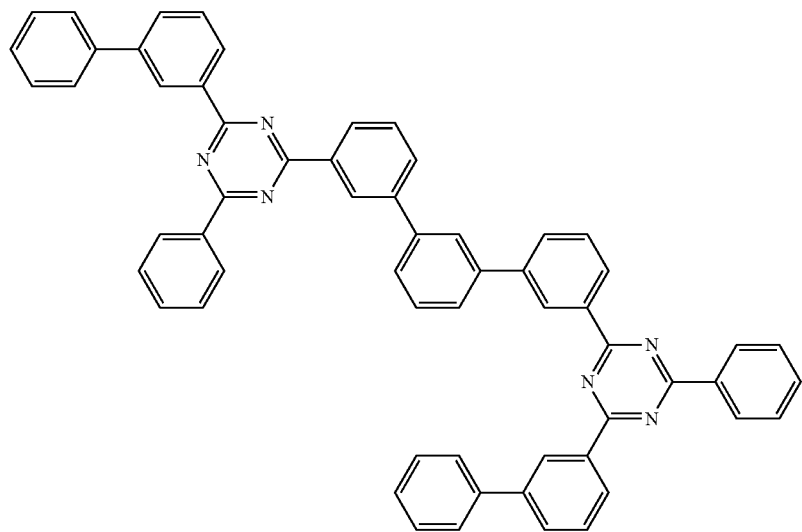
A(23)
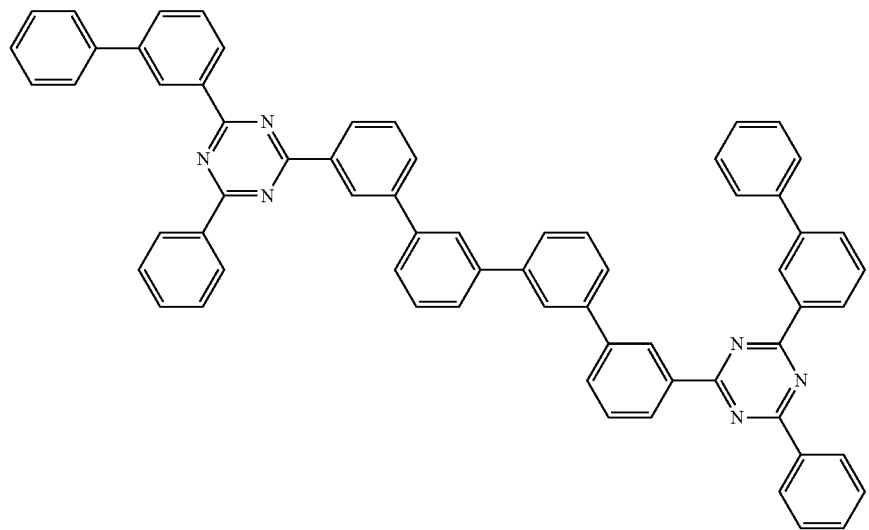
A(24)
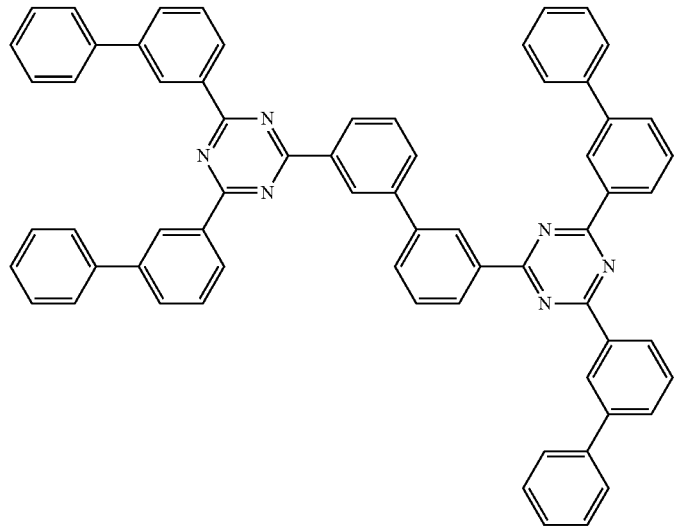
A(25)

A(26)
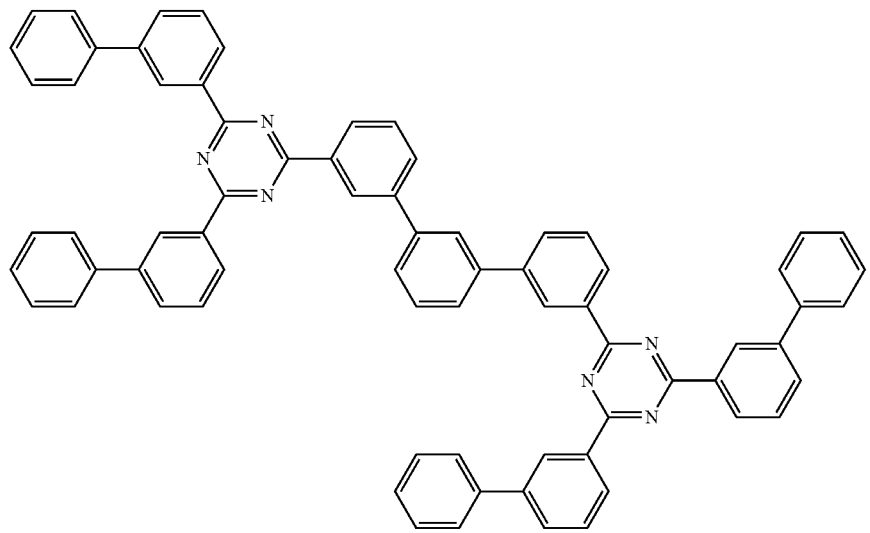
A(27)
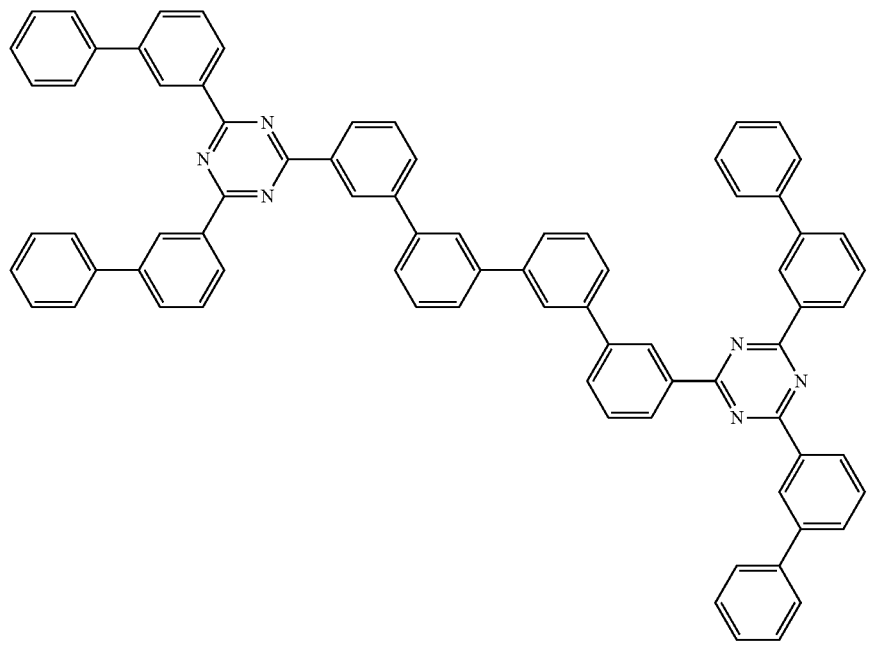
A(28) A(29)
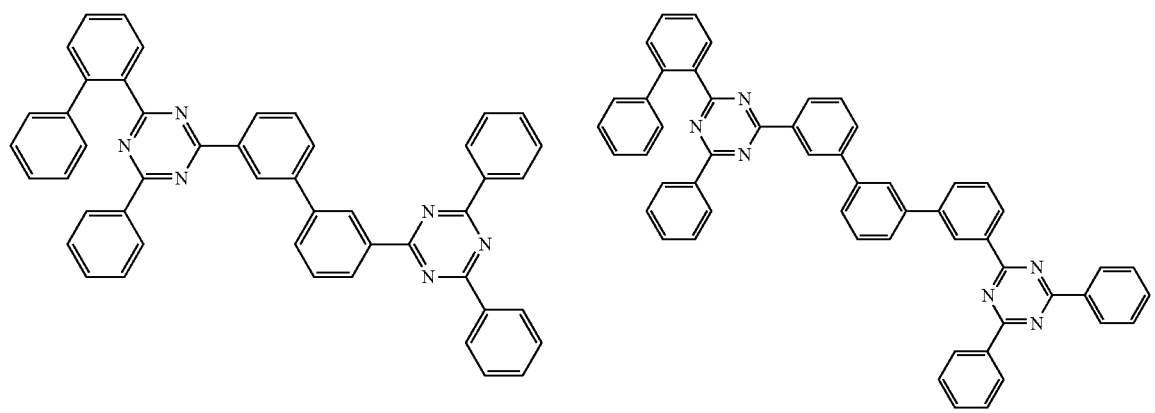

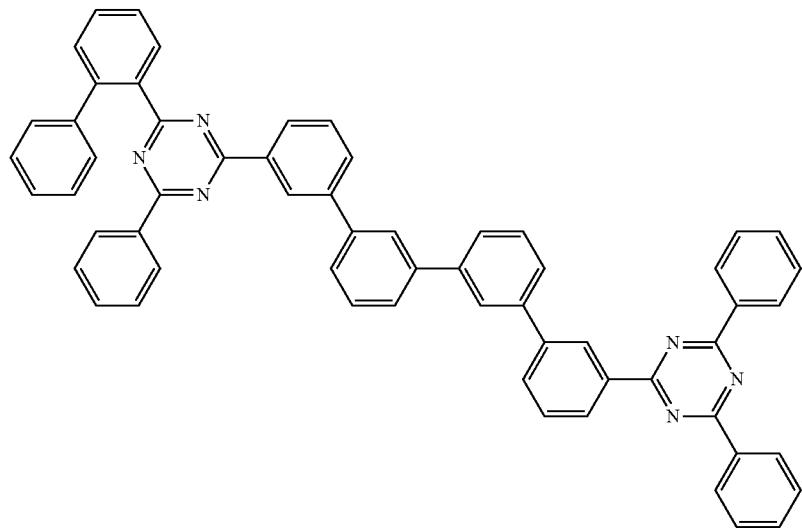
A(30)
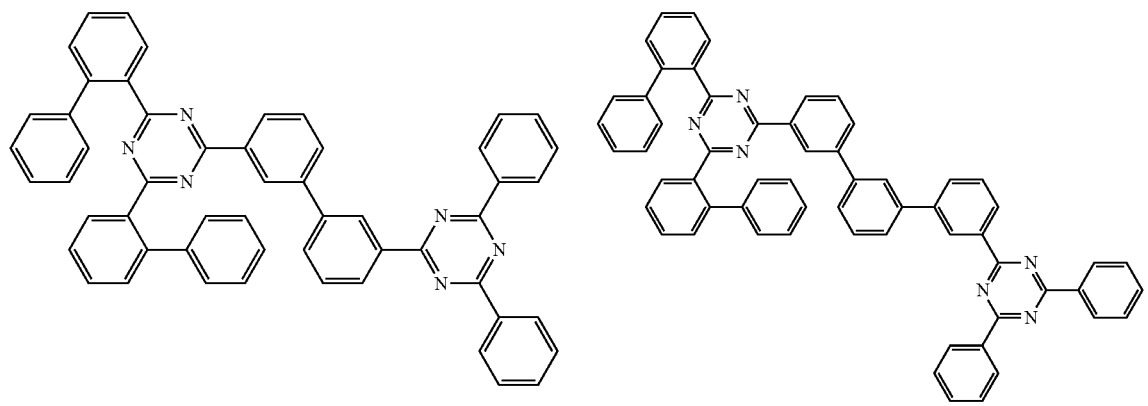
A(31)　　A(32)
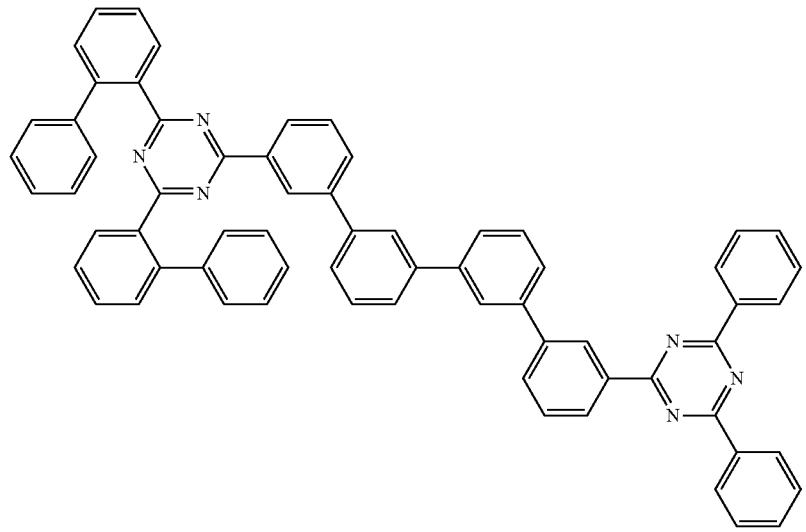
A(33)

A(34)
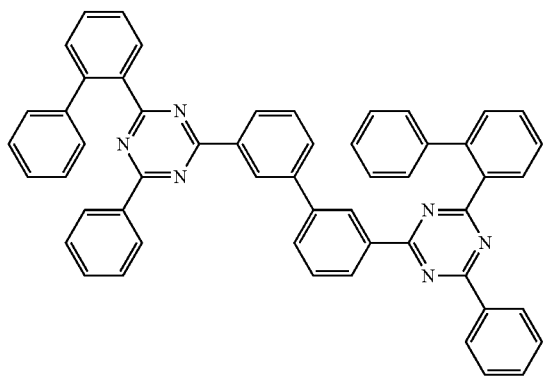
A(35)
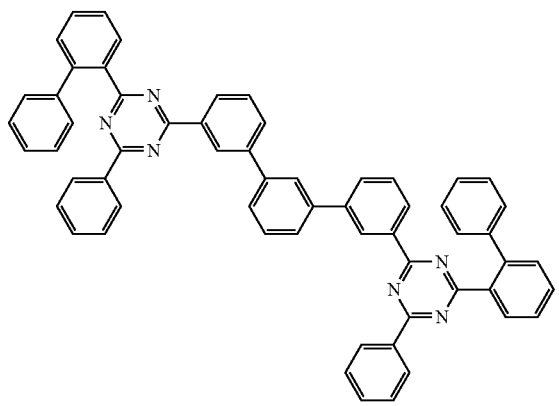
A(36)
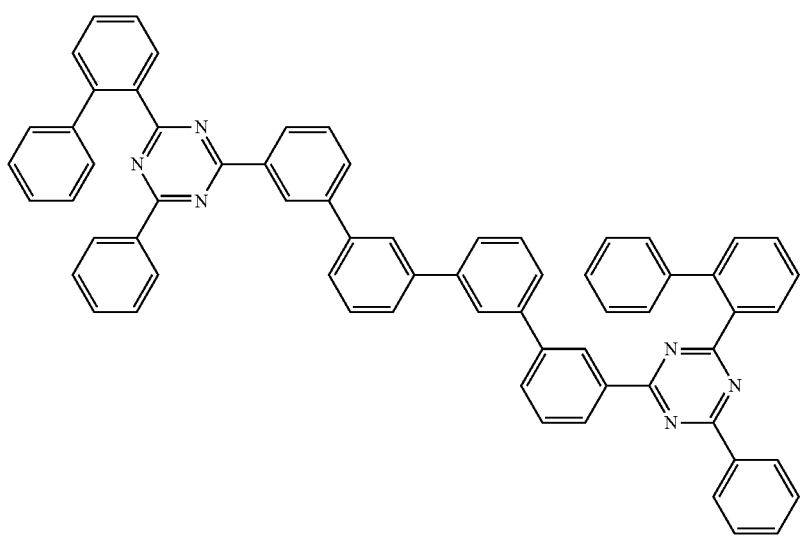
A(37)
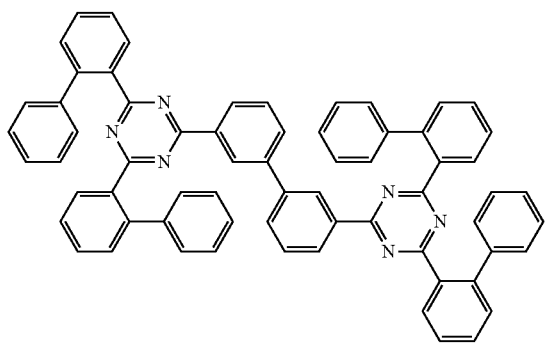
A(38)
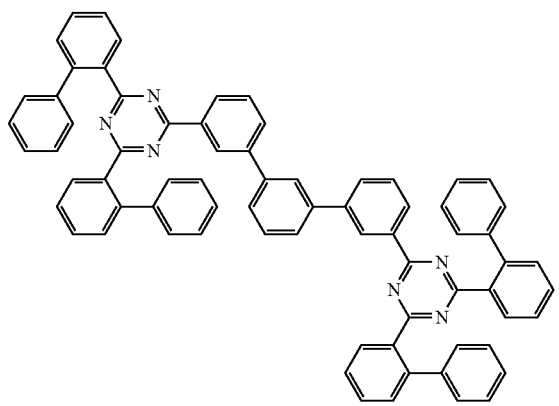

-continued
A(39)
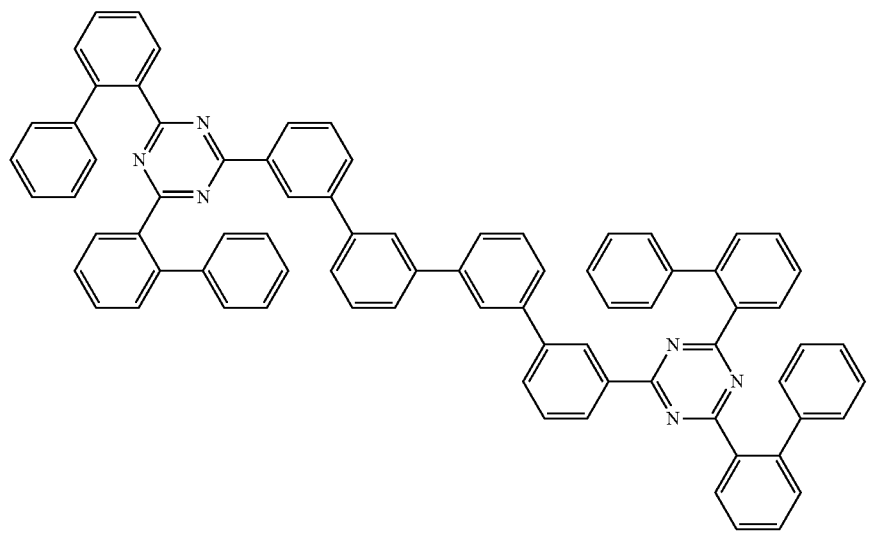
A(40)
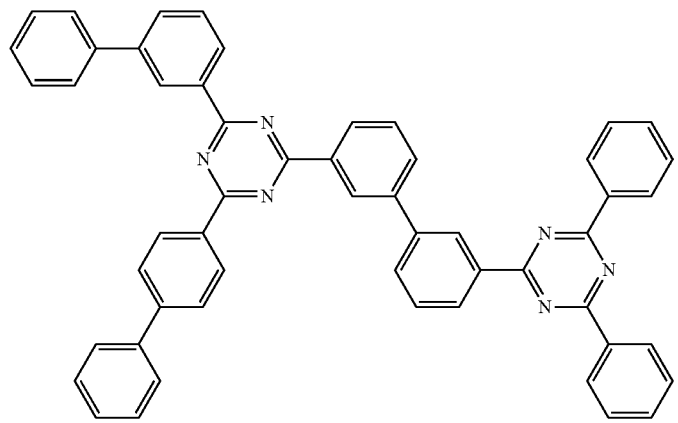
A(41)
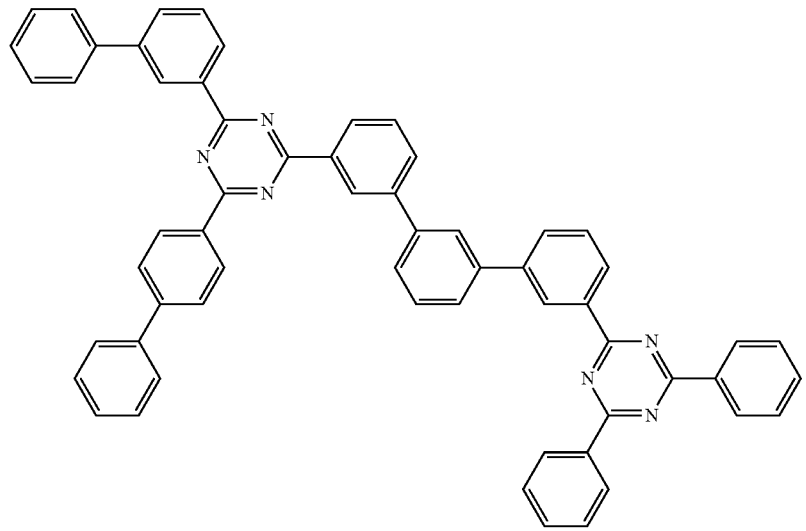

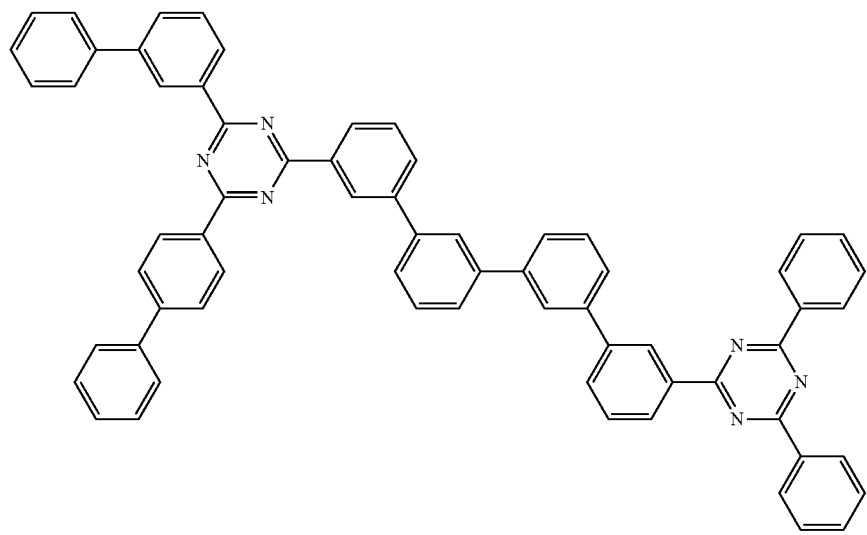
A(42)
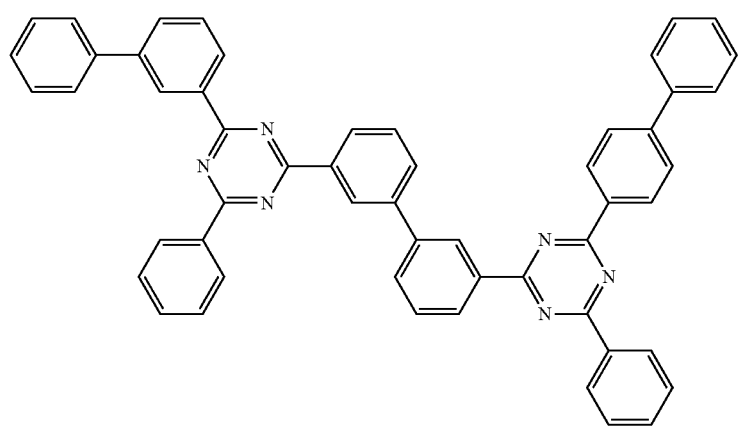
A(43)
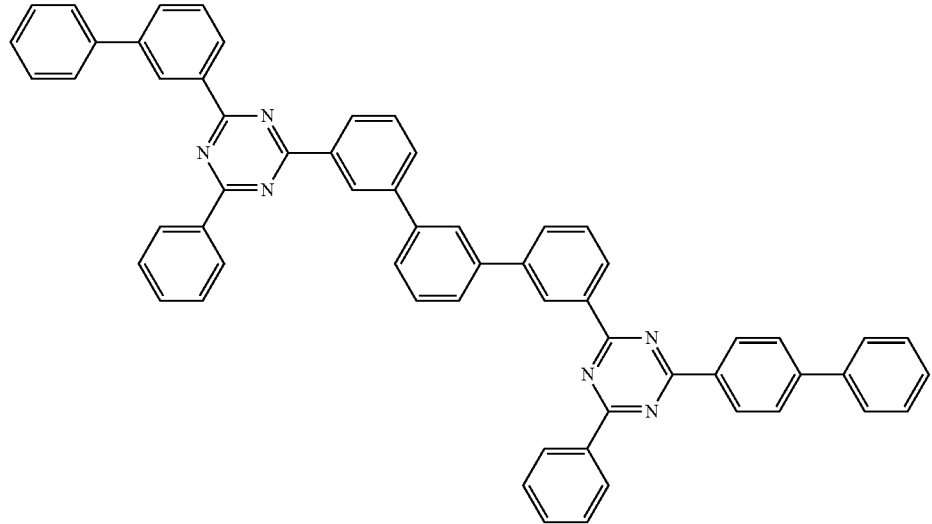
A(44)

A(45)
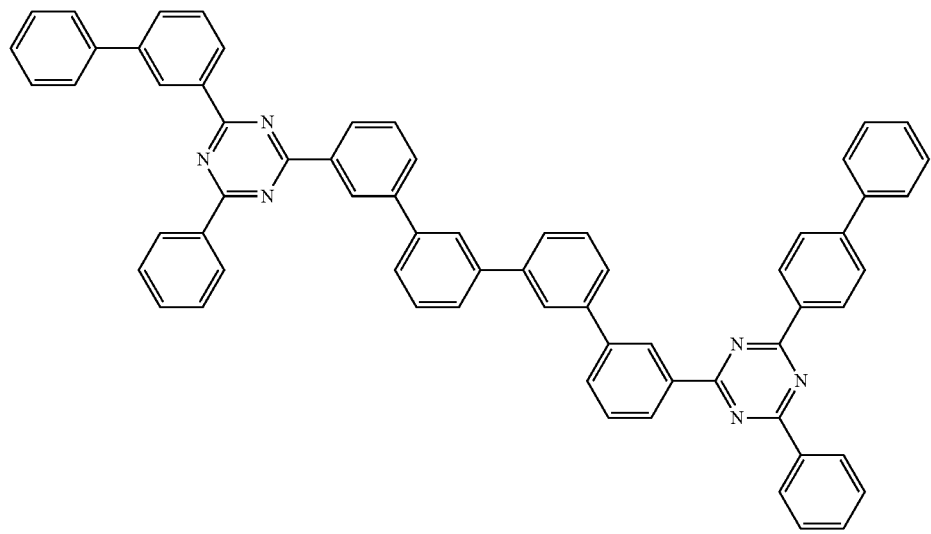
A(46)
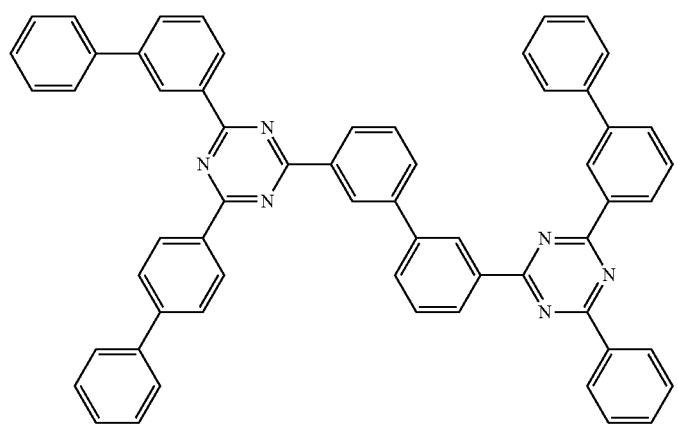
A(47)
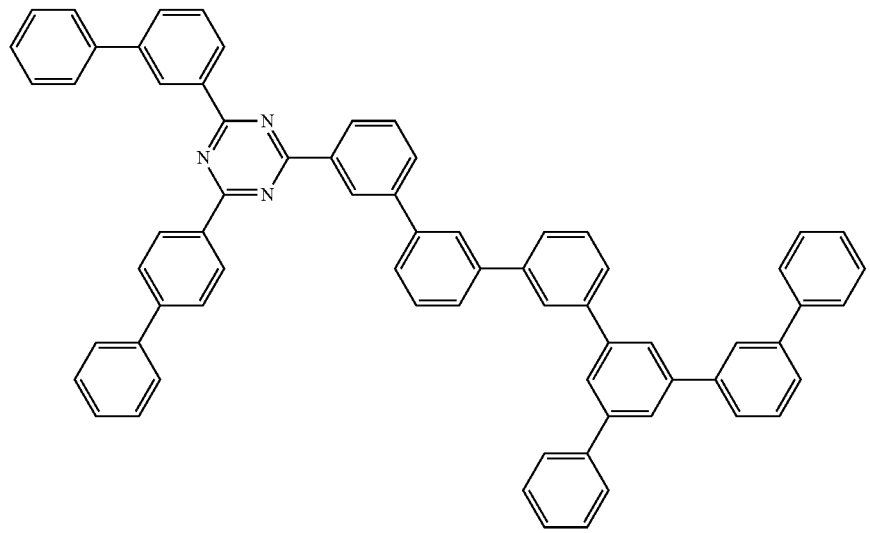

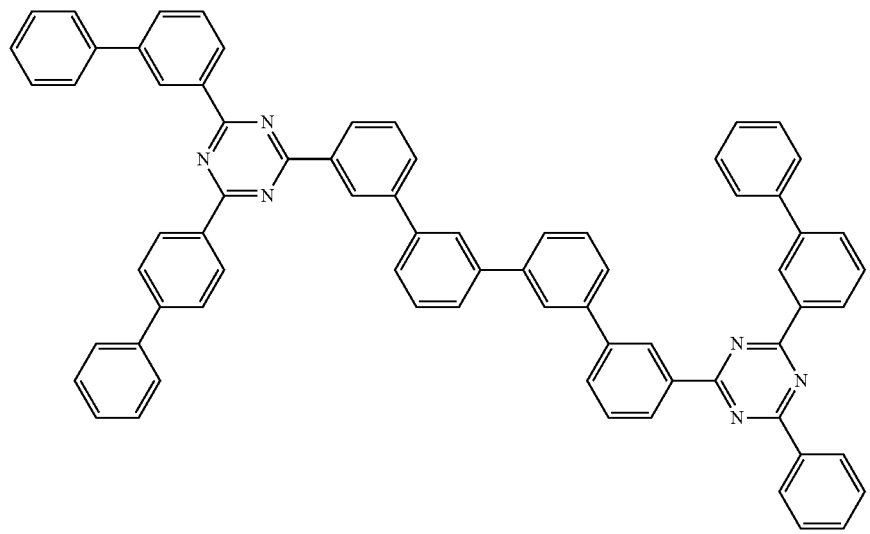
A(48)
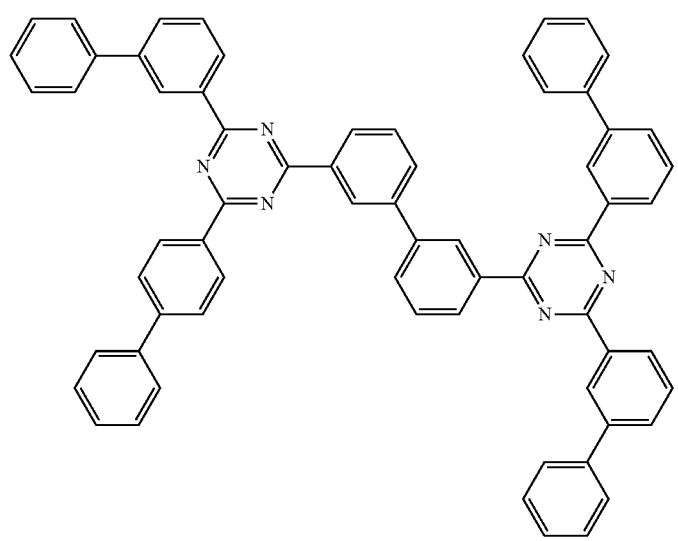
A(49)
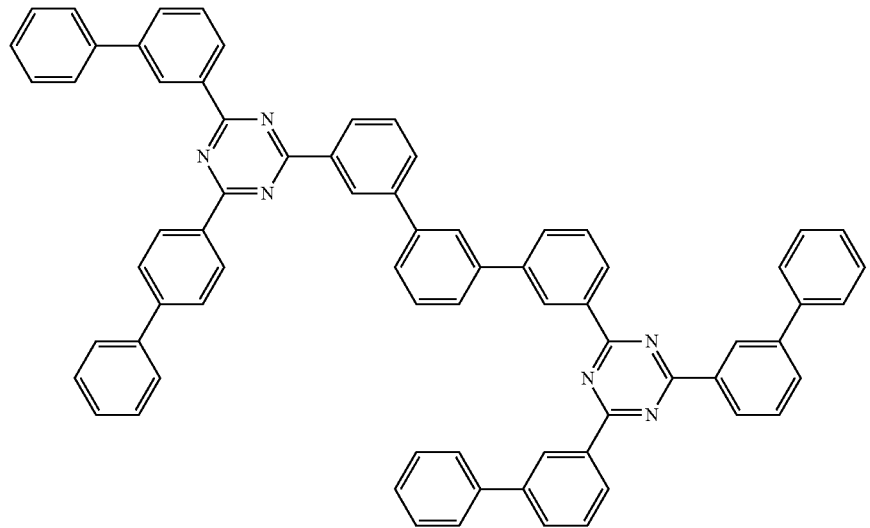
A(50)

-continued
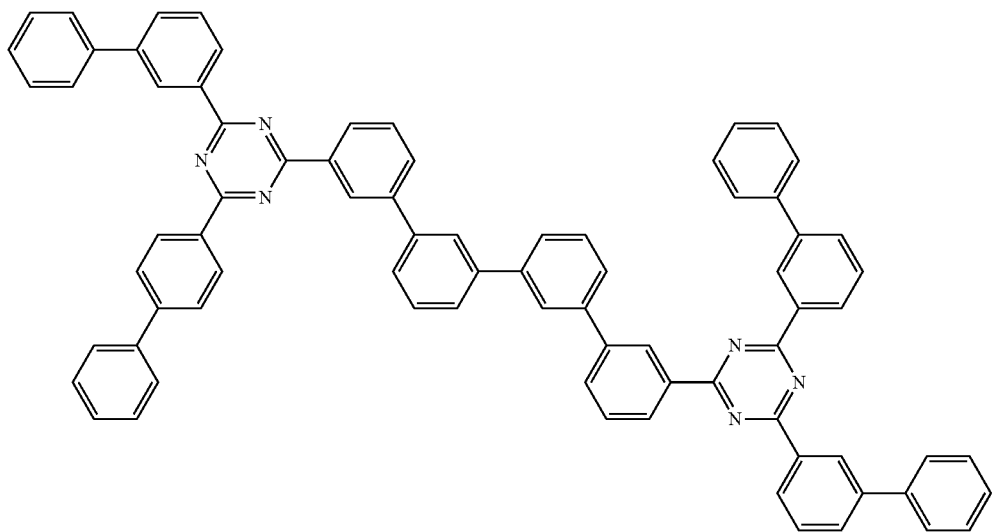
A(51)
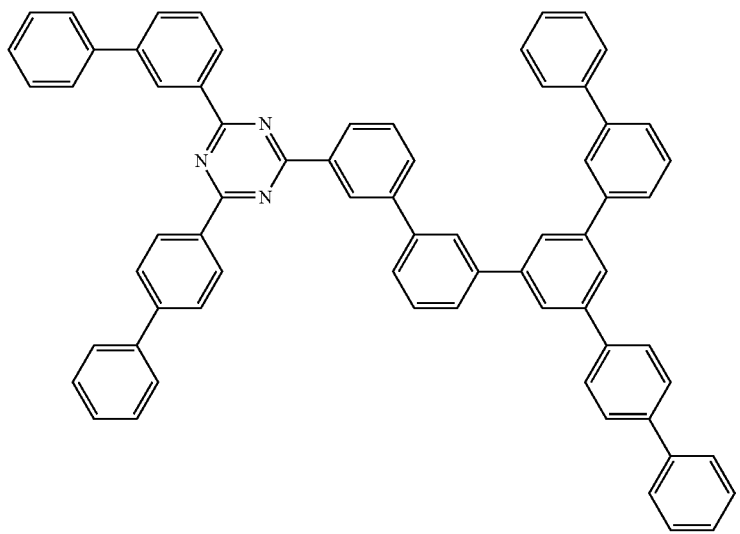
A(52)

A(53)
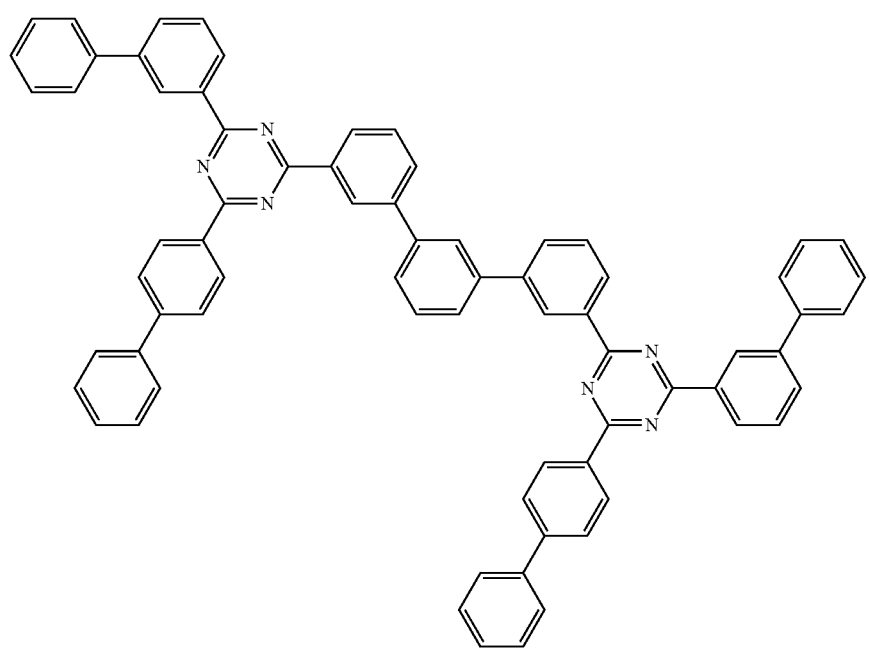
A(54)
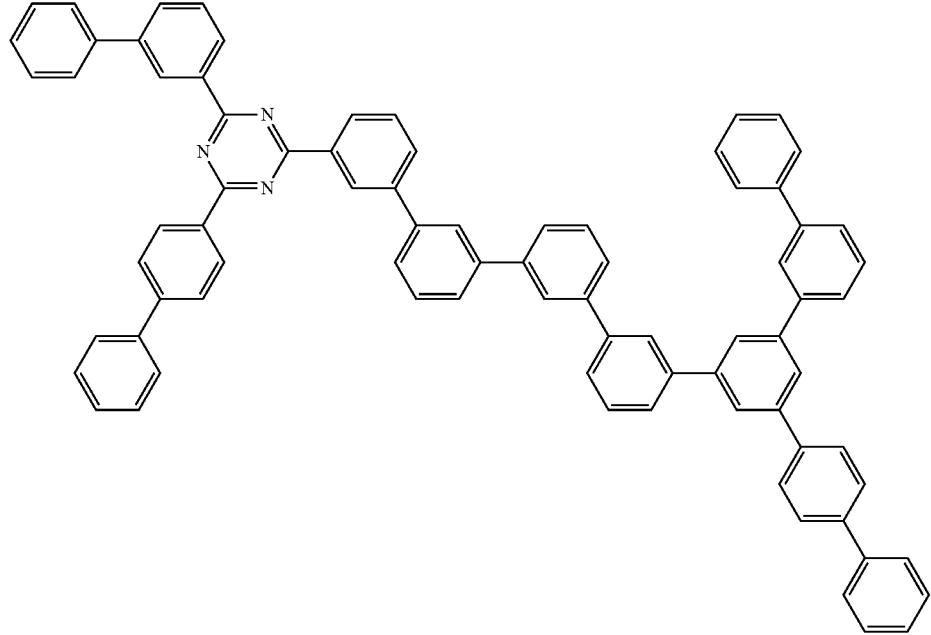

-continued
A(55)
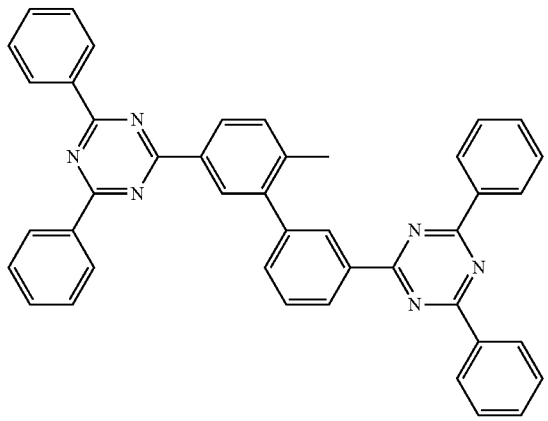
A(56)
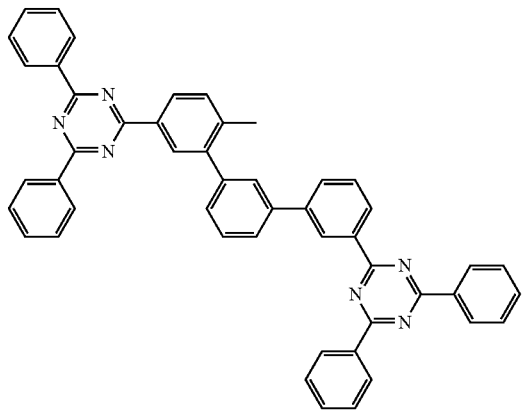
A(57)
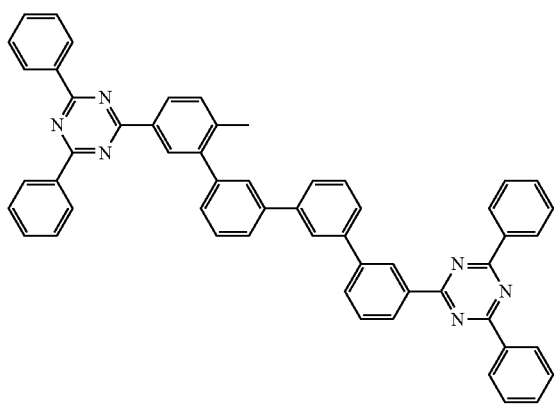
A(58)
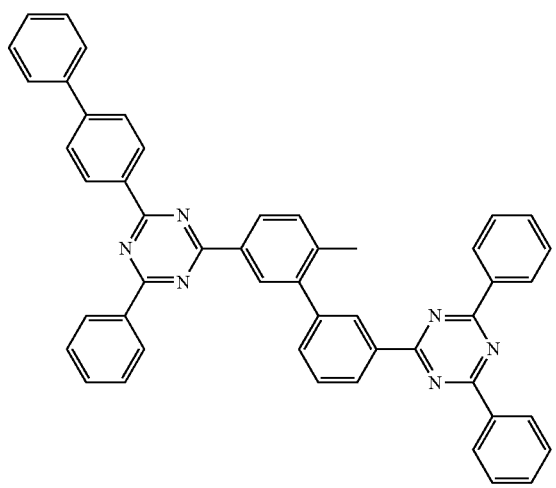
A(59)
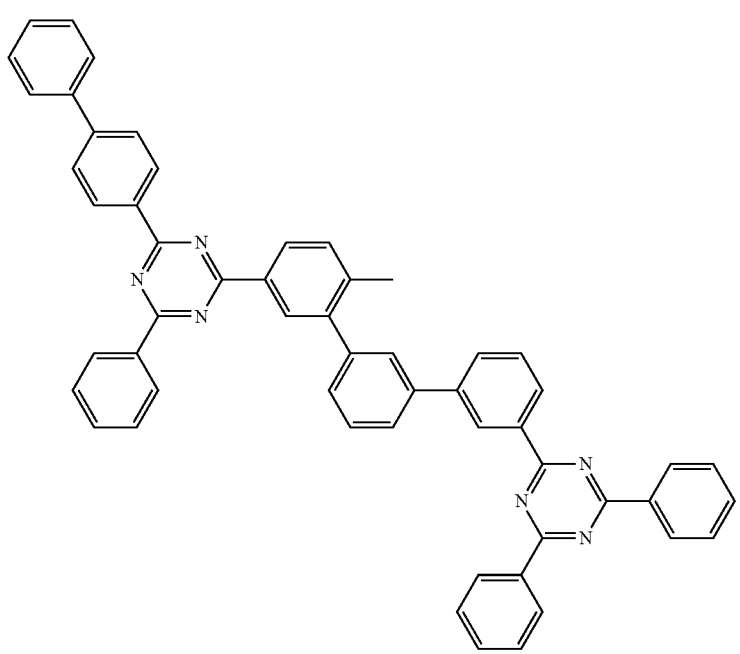

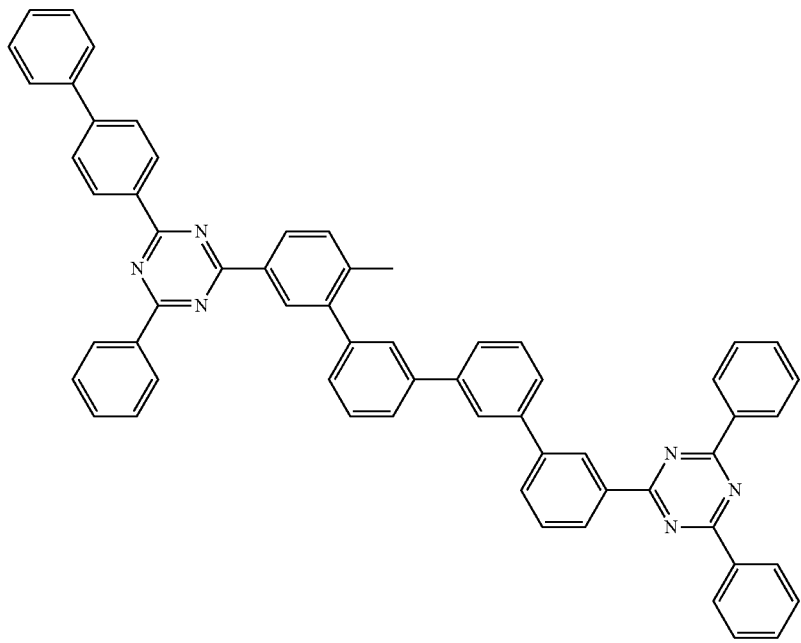
A(60)
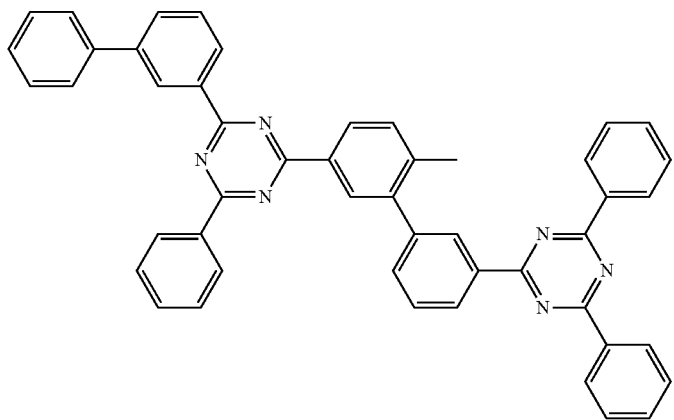
A(61)
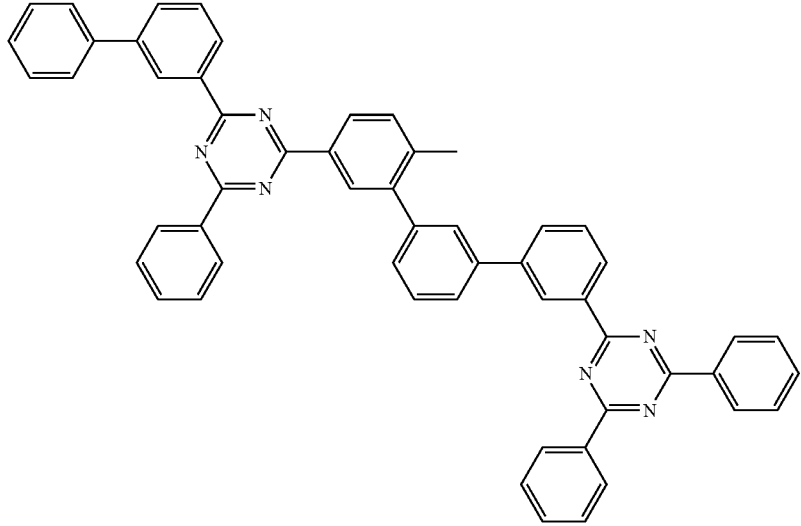
A(62)

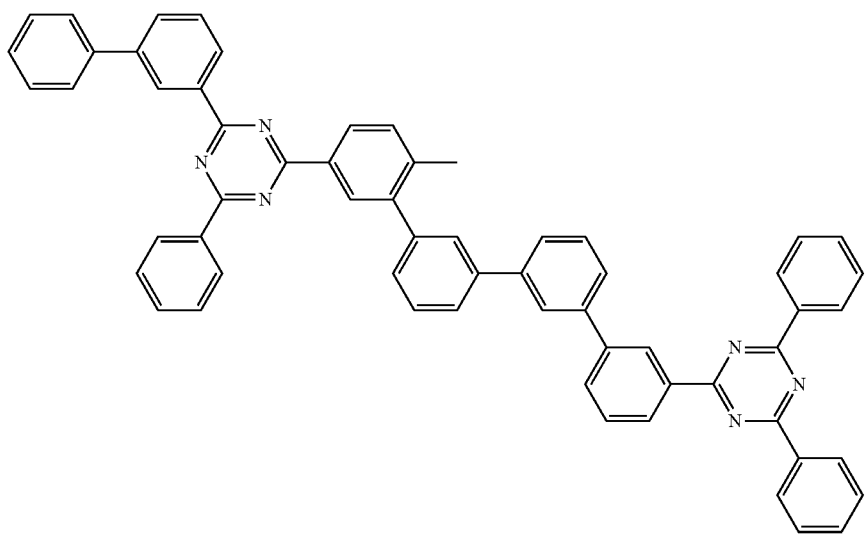
A(63)
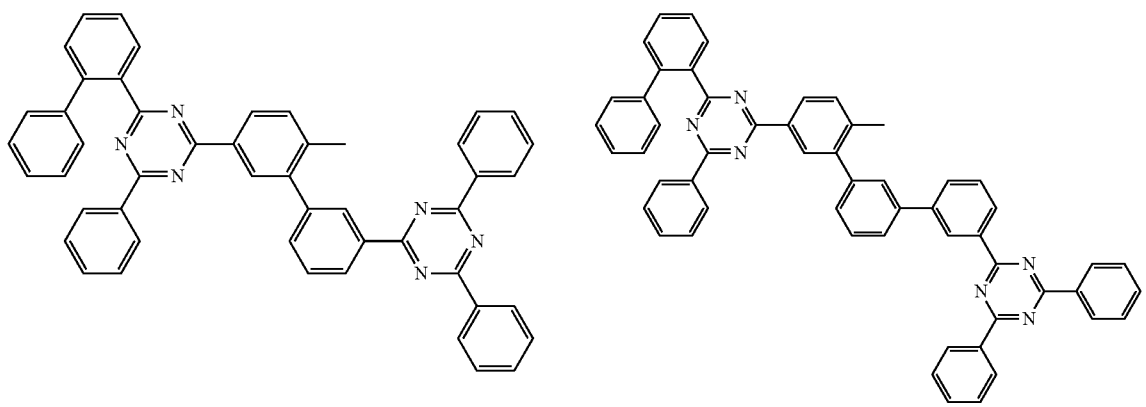
A(64)  A(65)
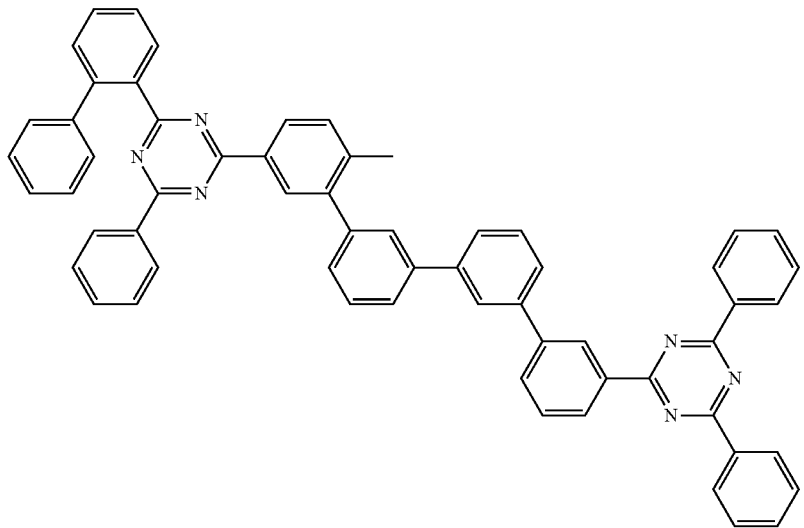
A(66)

-continued
A(67)
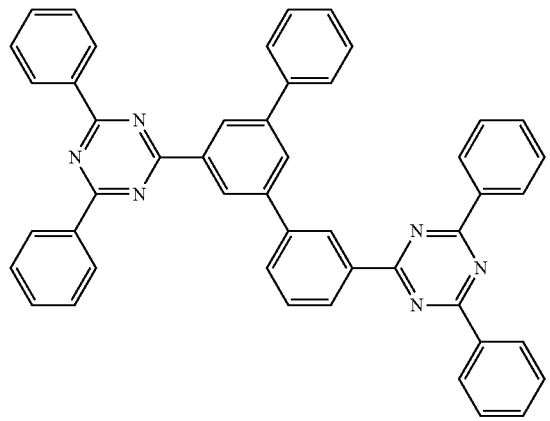
A(68)
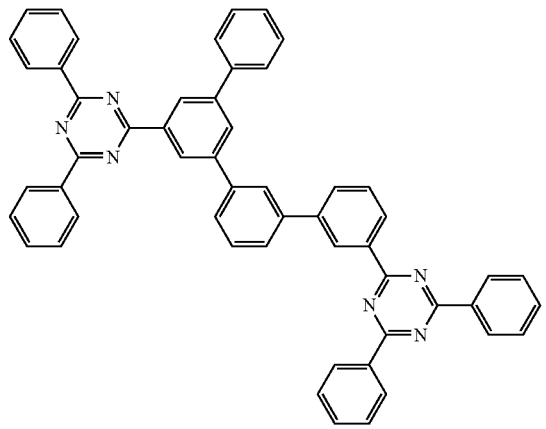
A(69)
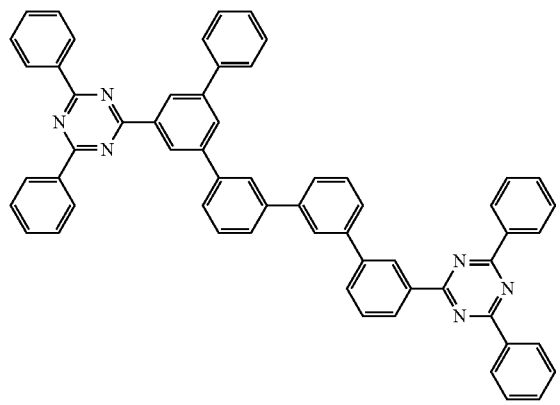
A(70)
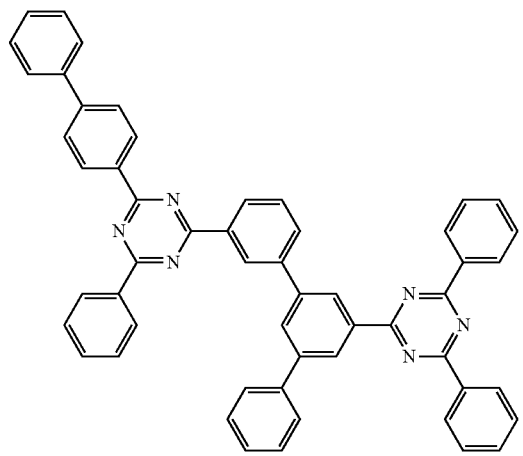
A(71)
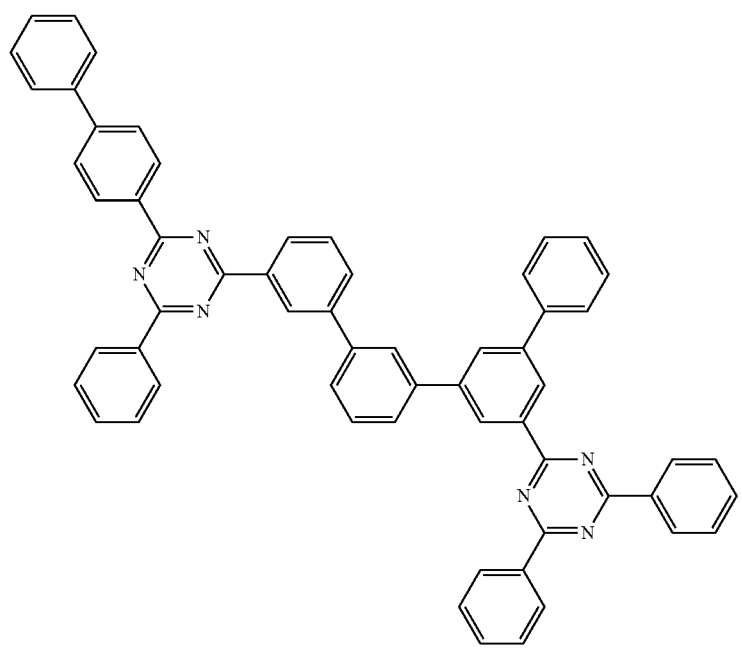

-continued
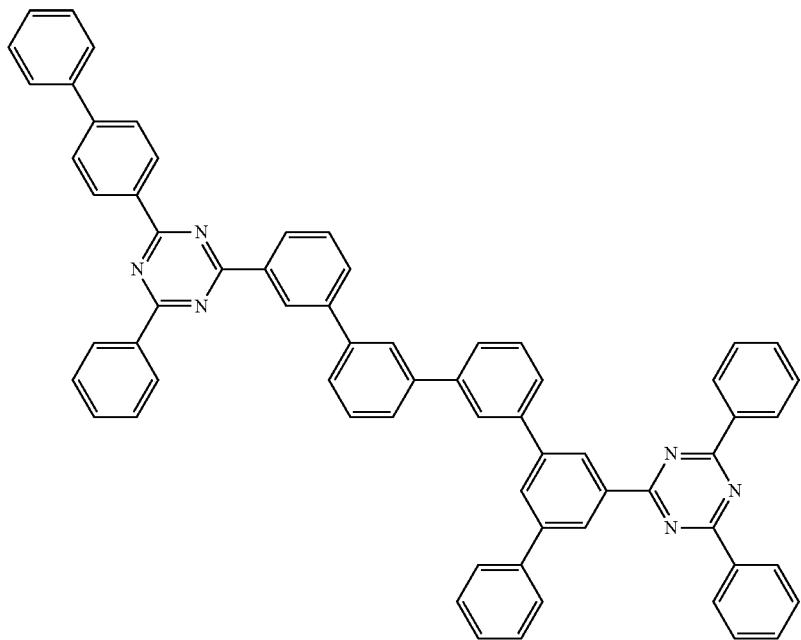
A(72)
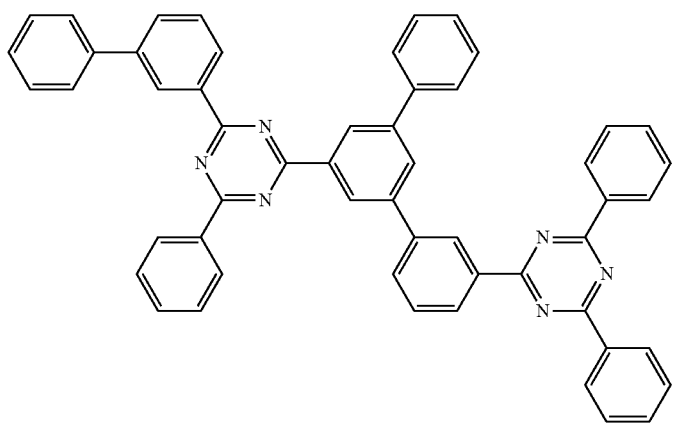
A(73)
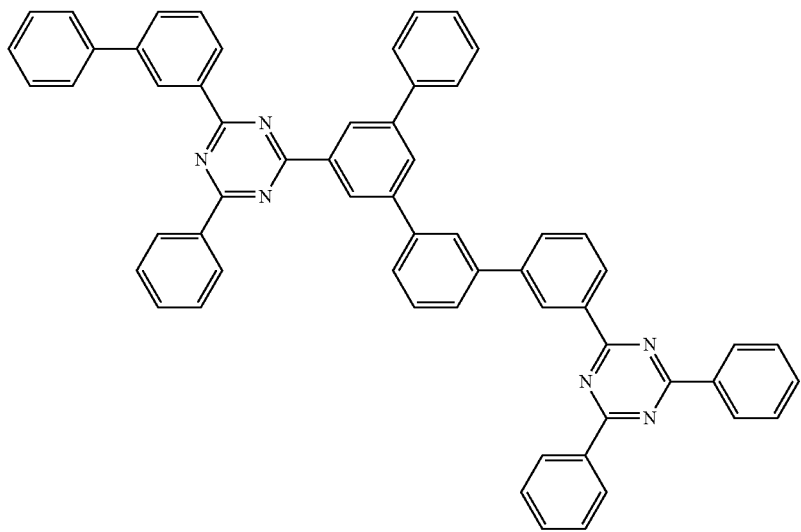
A(74)

-continued
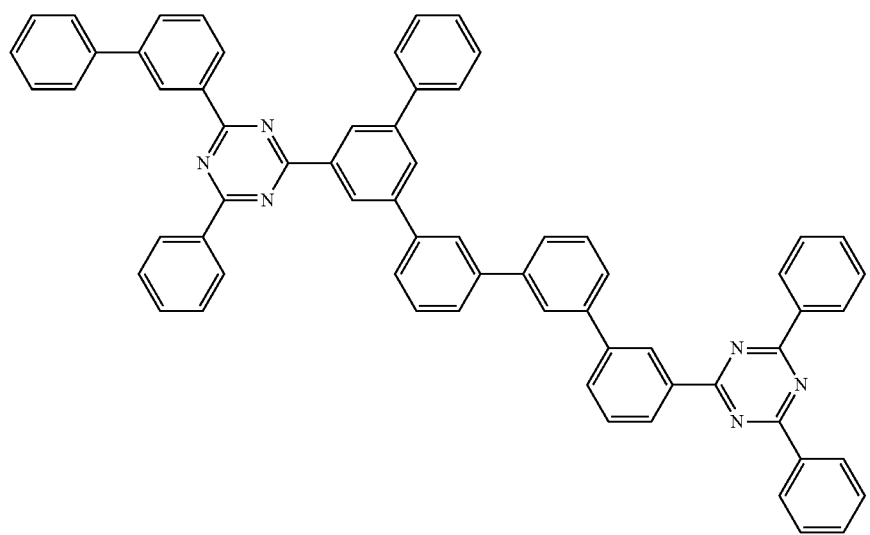
A(75)
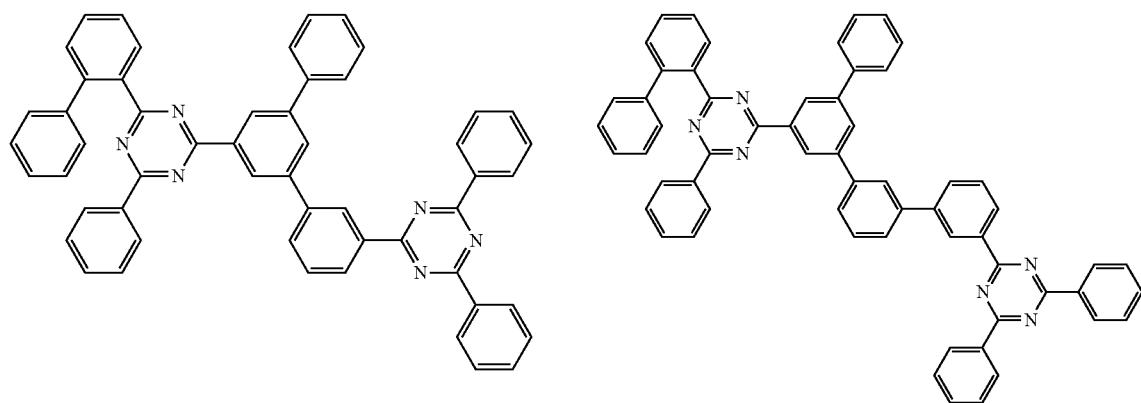
A(76)
A(77)
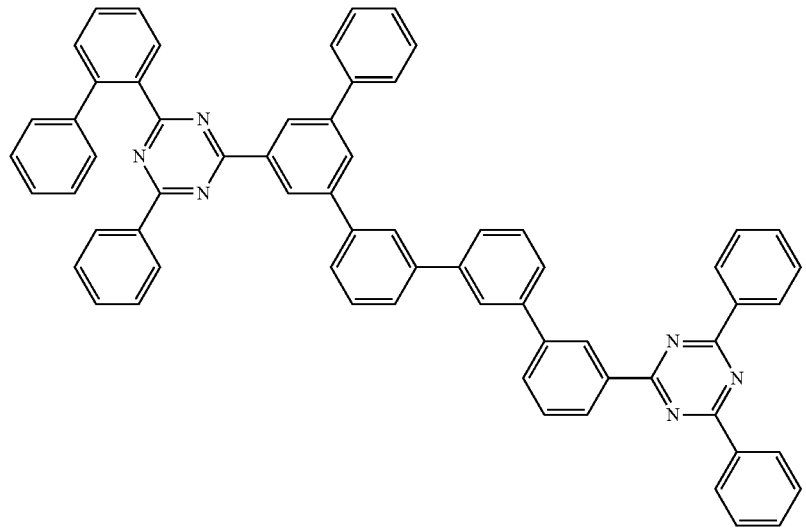
A(78)

-continued
A(79)
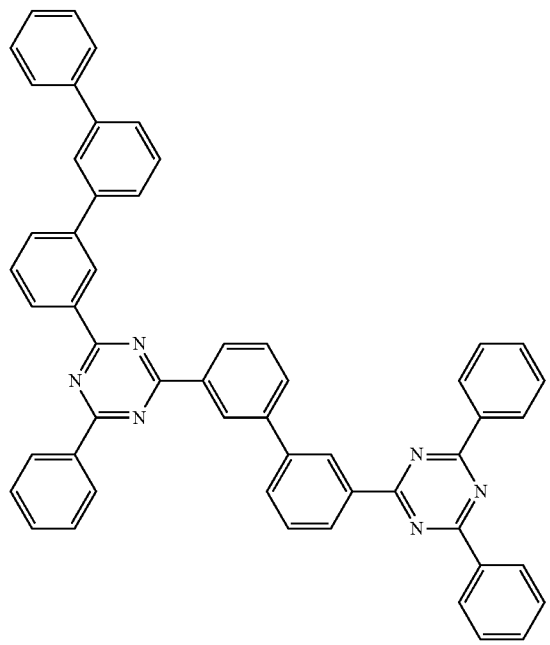
A(80)
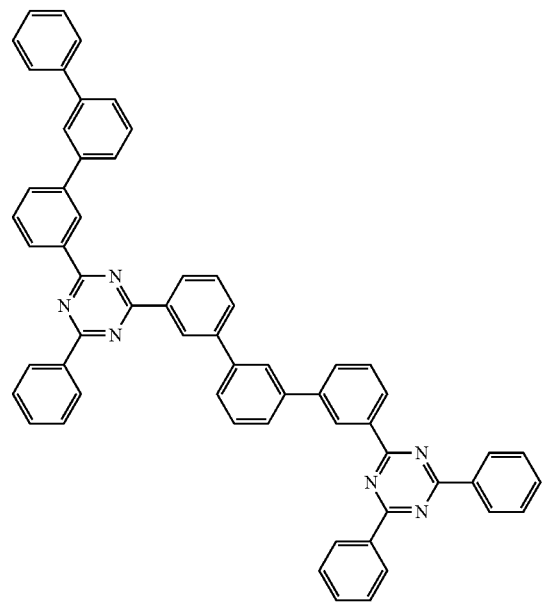
A(81)
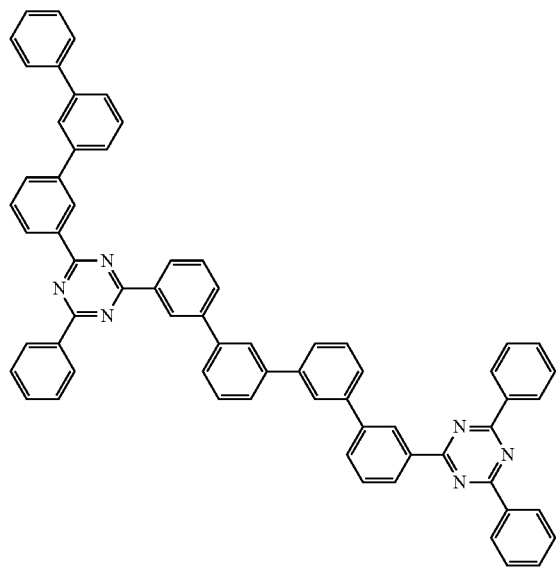
A(82)
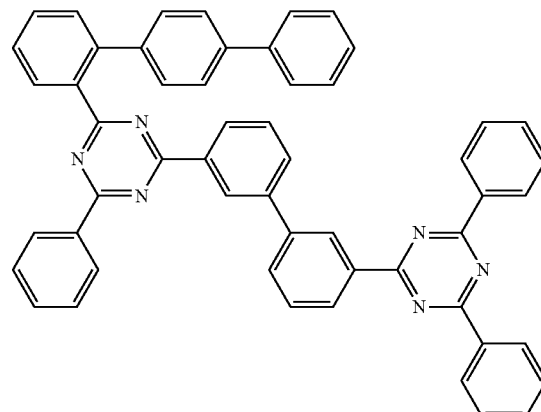

-continued
A(83)
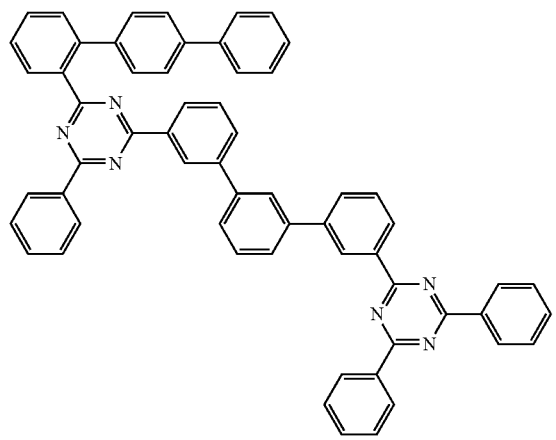
A(84)
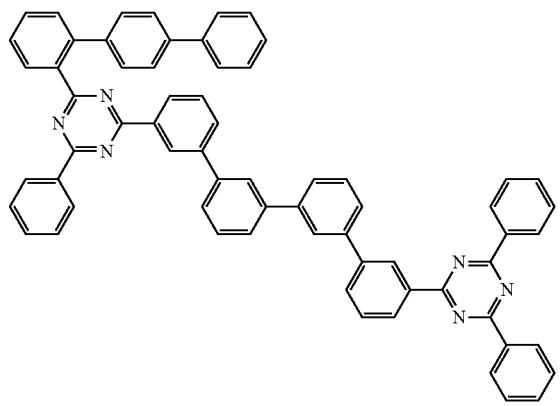
A(85)
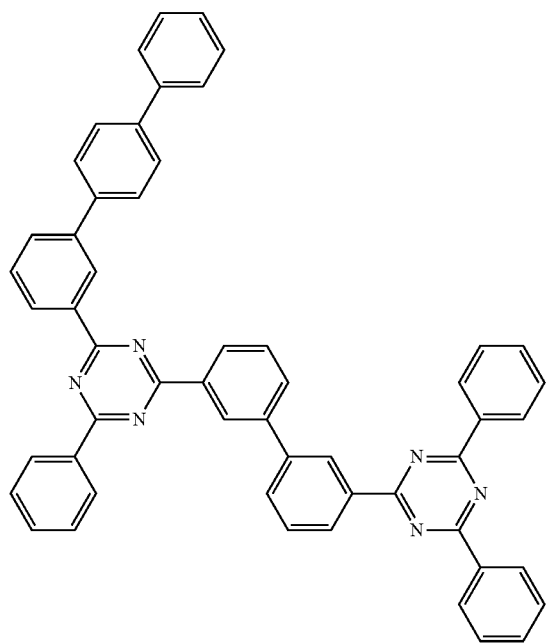
A(86)
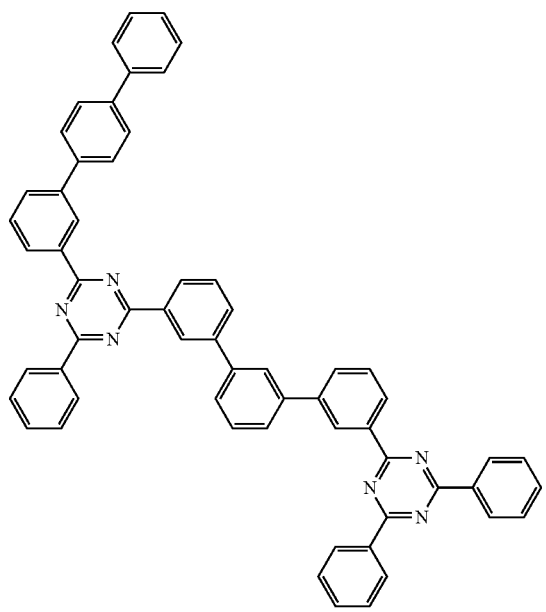

-continued
A(87)
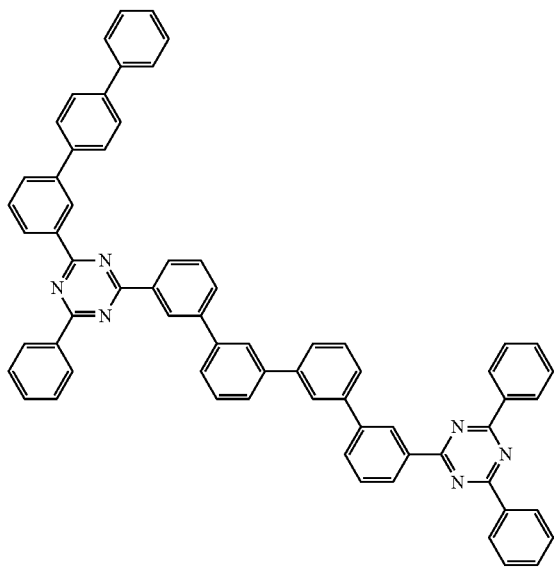
A(88)
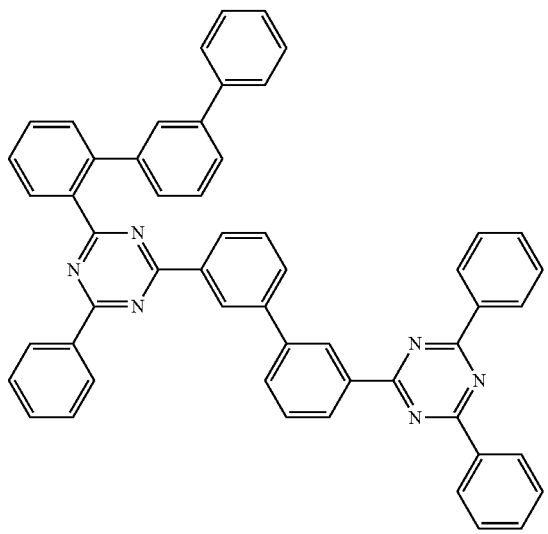
A(89)
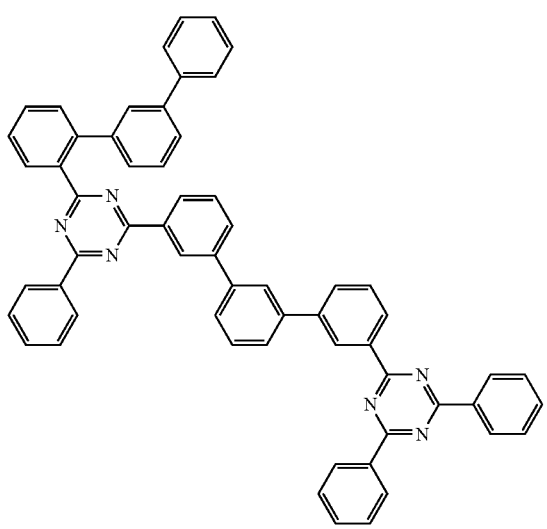
A(90)
A(91)
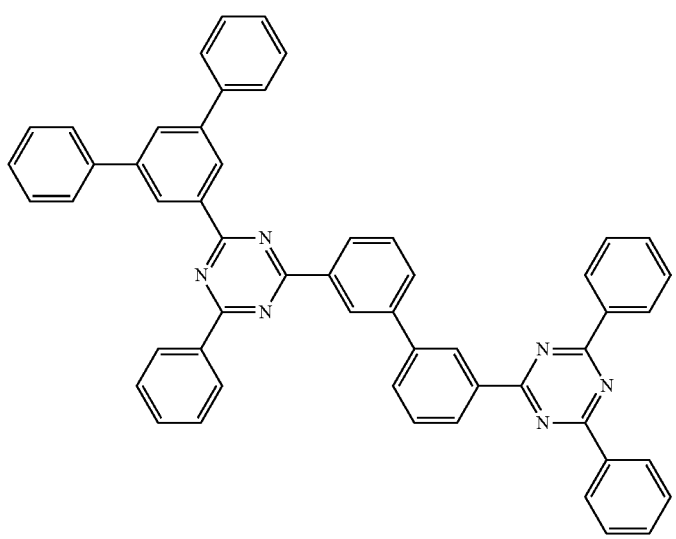

-continued
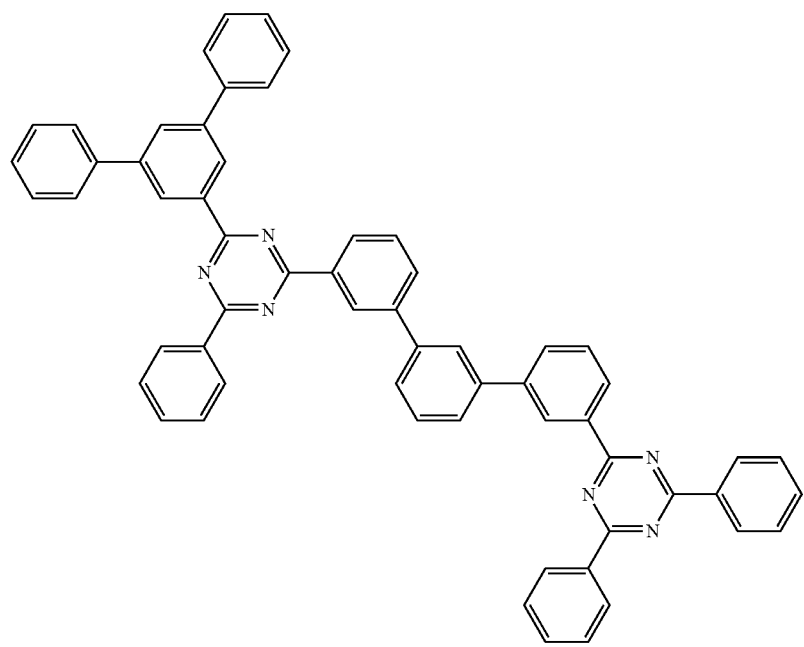
A(92)
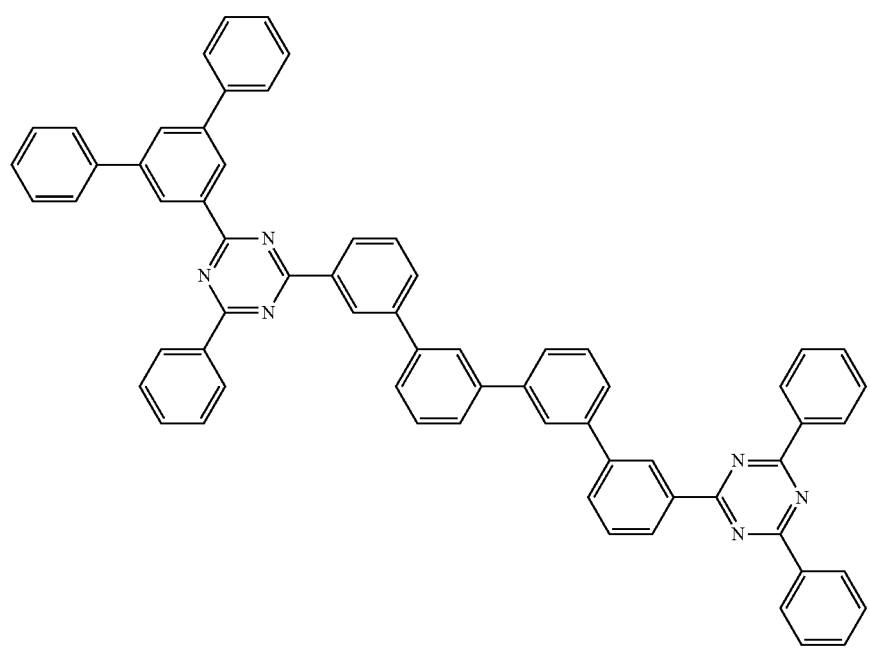
A(93)

A(94)
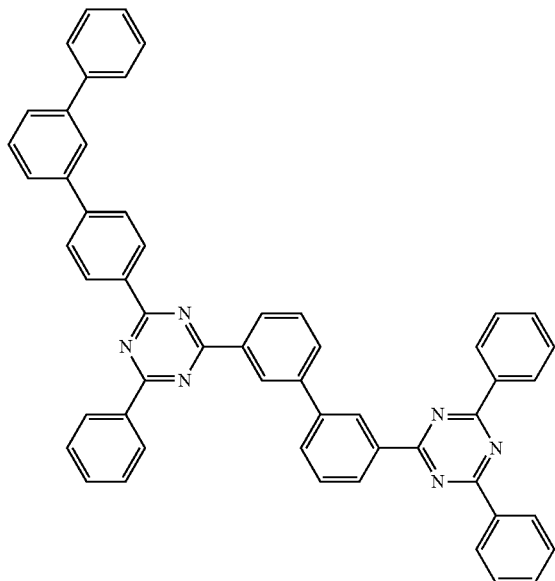
A(95)
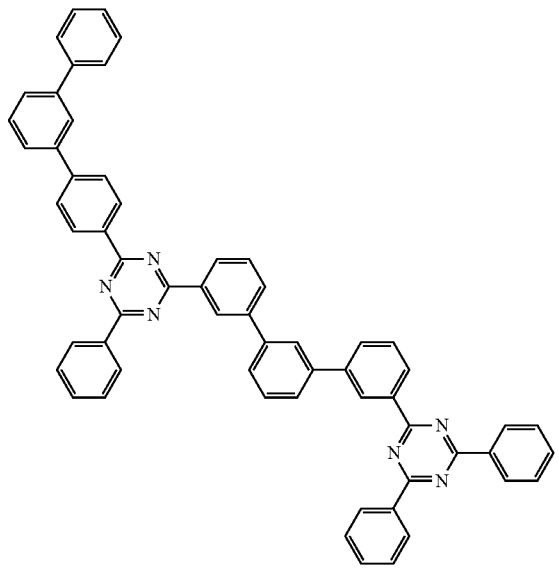
A(96)
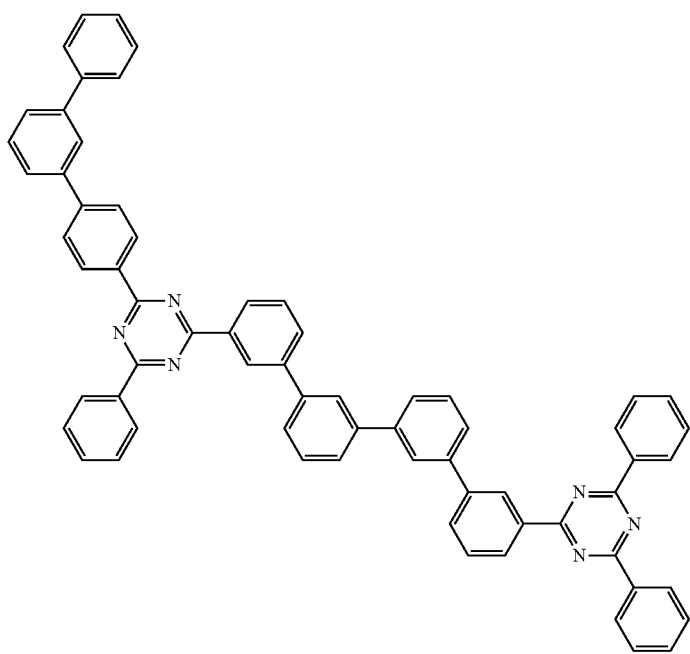

A(97)
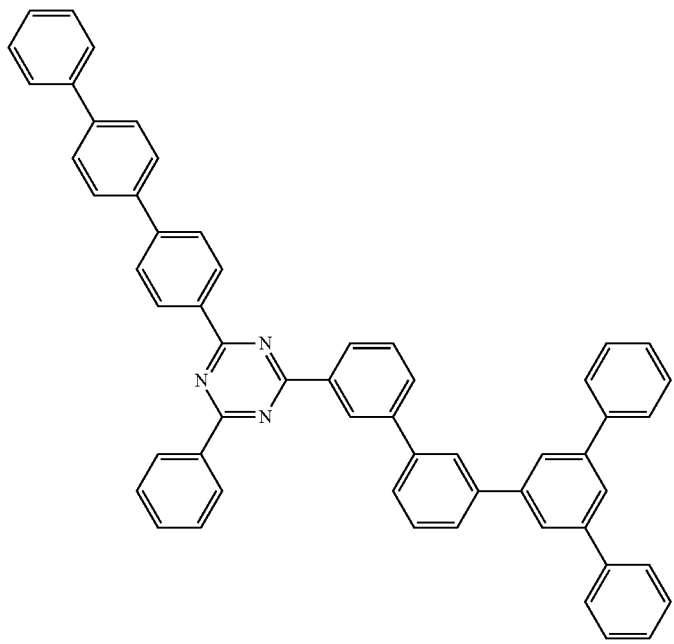
(98)
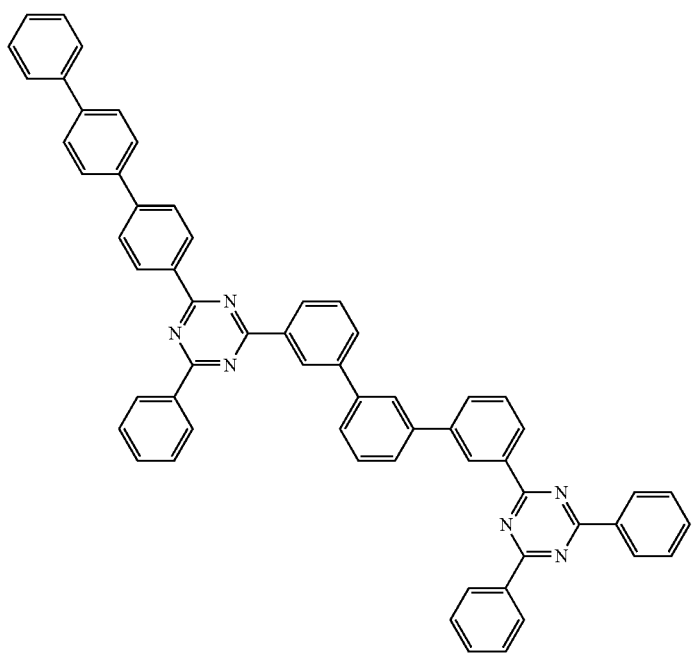

-continued
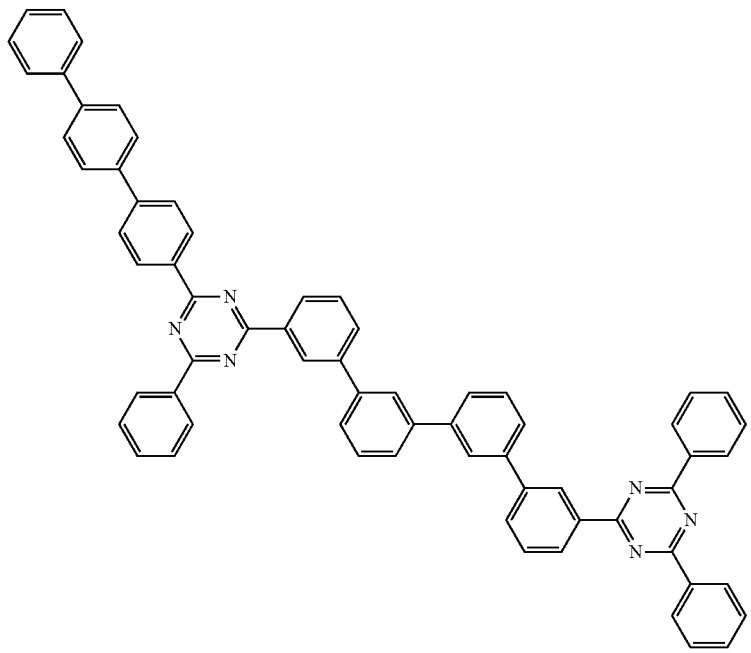
A(99)
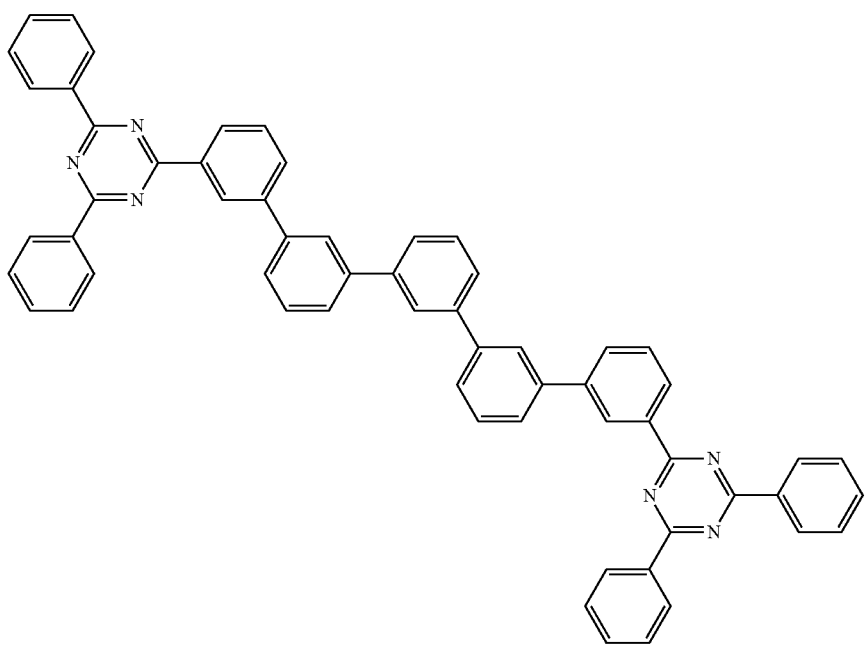
A(100)

-continued
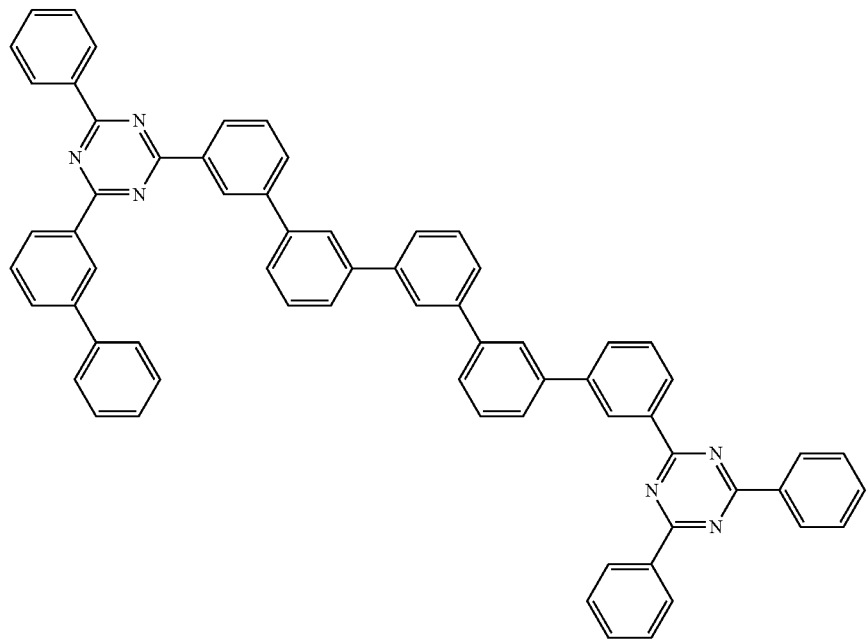
A(101)
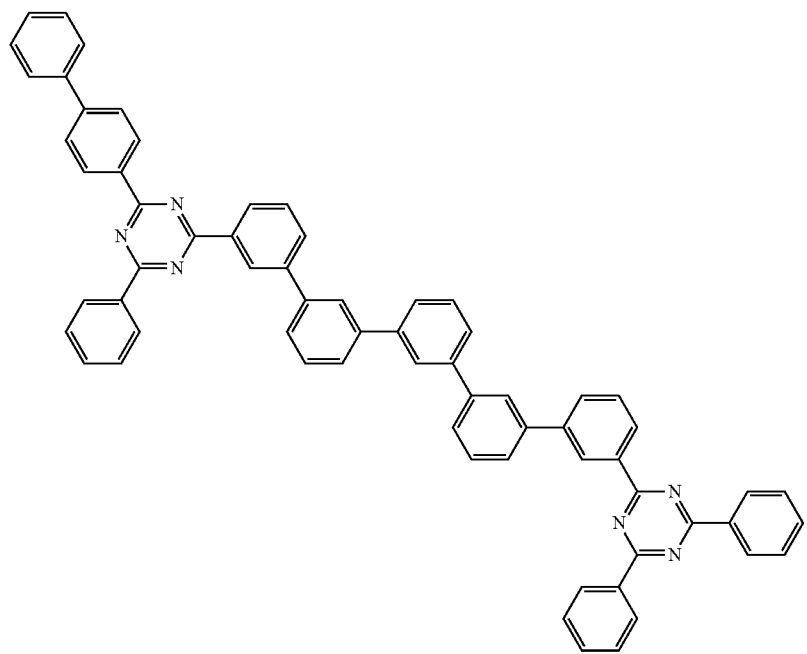
A(102)

-continued
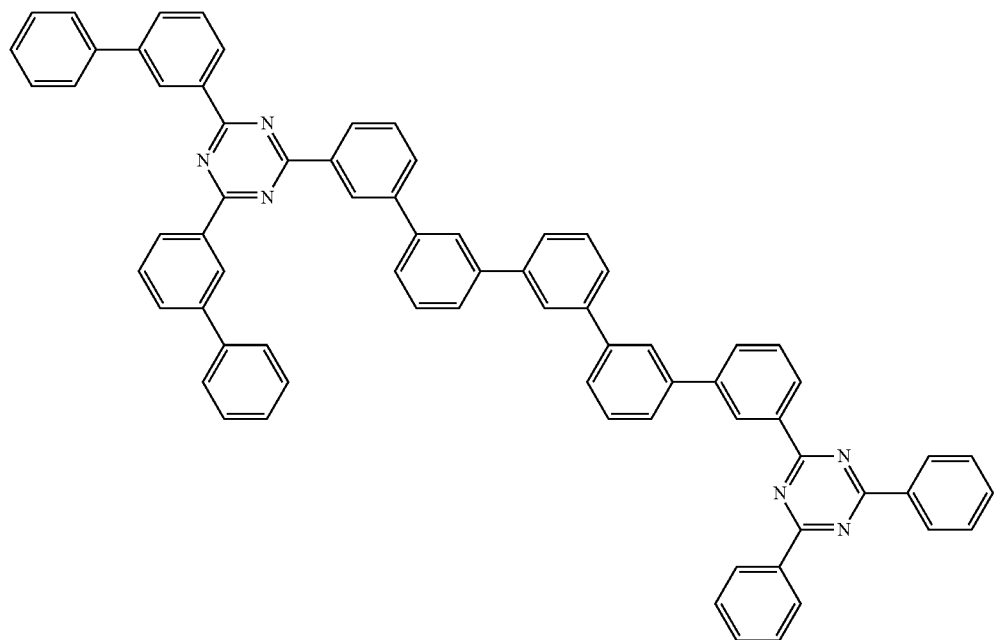
A(103)
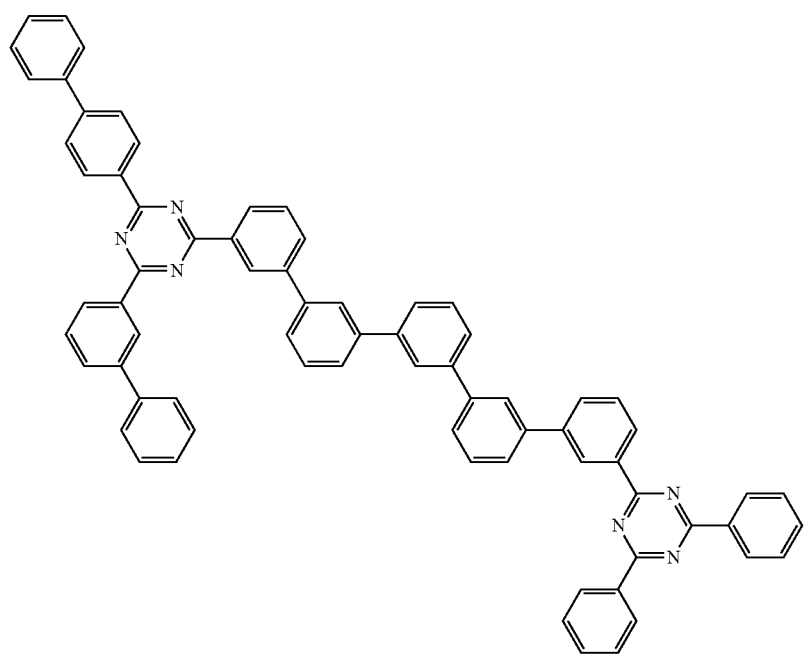
A(104)

A(105)
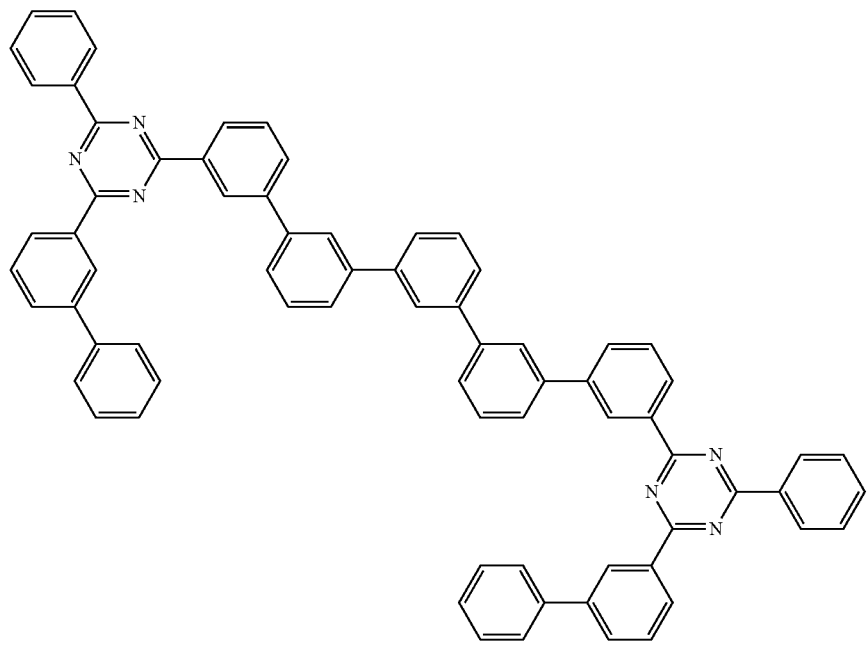
A(106)
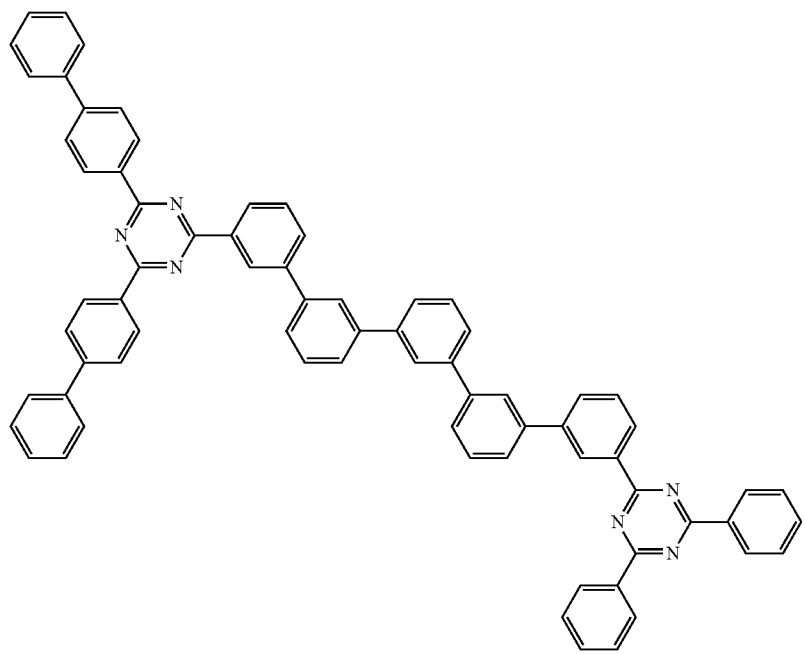

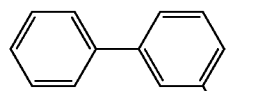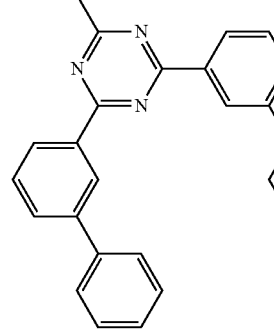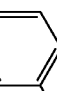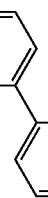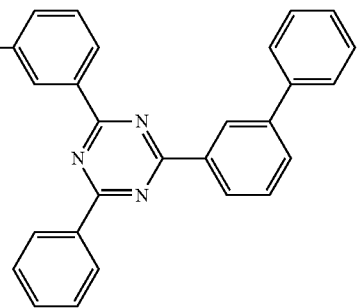
A(107)
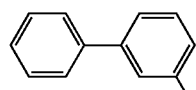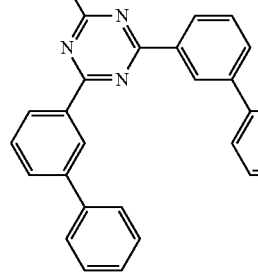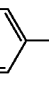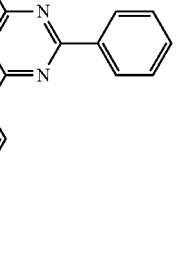
A(108)

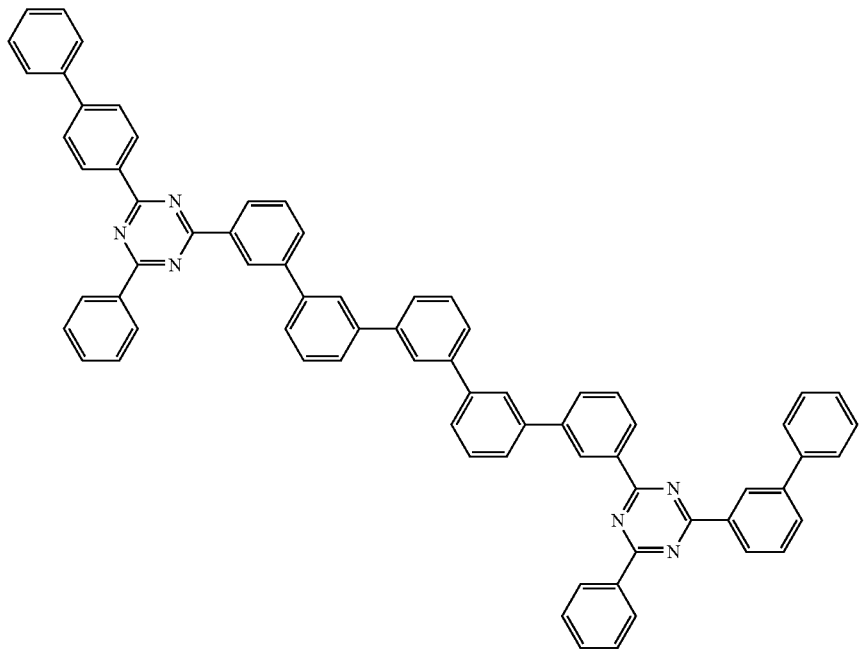
A(109)
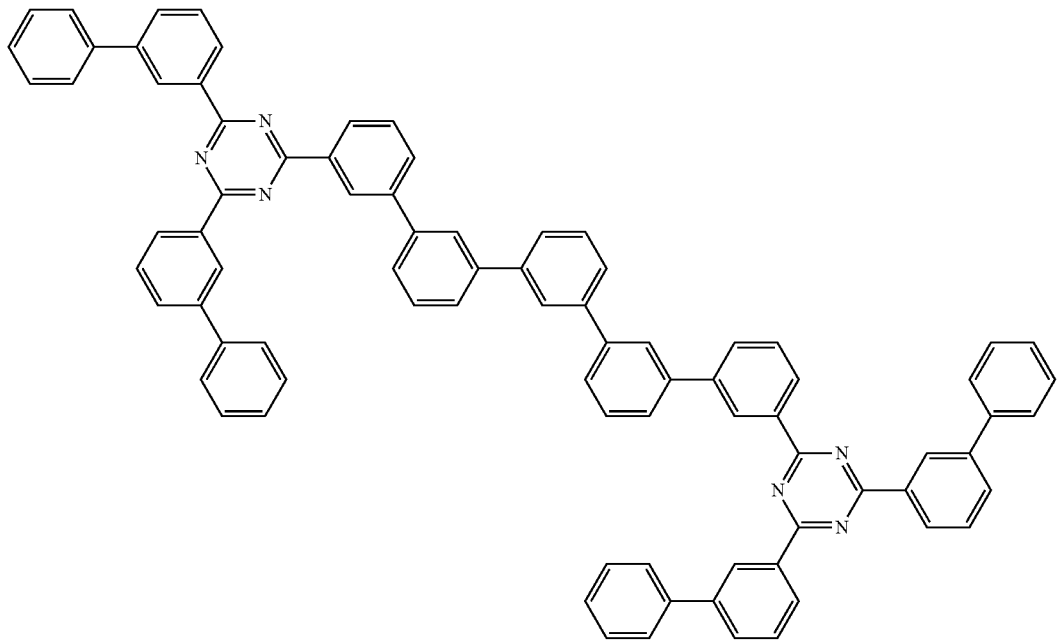
A(110)

-continued
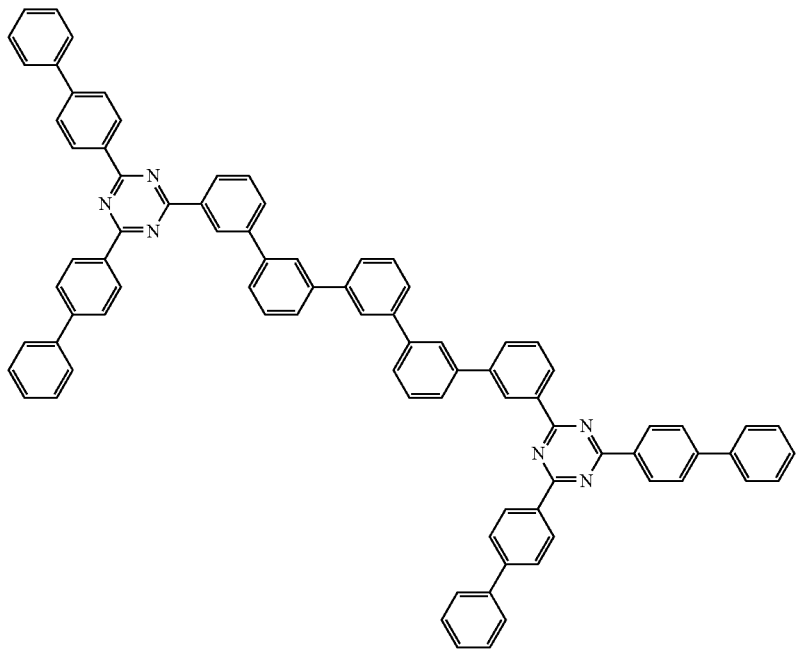
A(111)
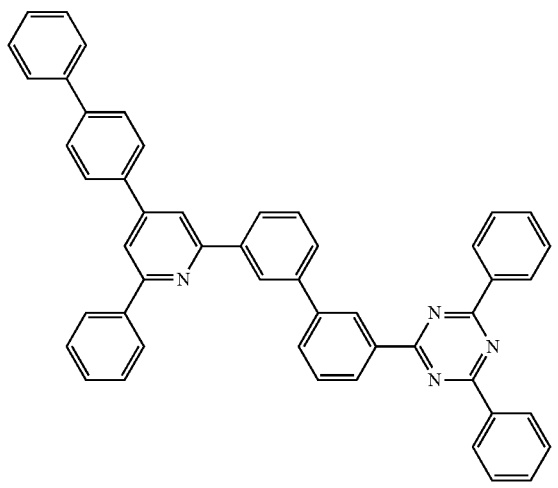
A(112)

A(113)
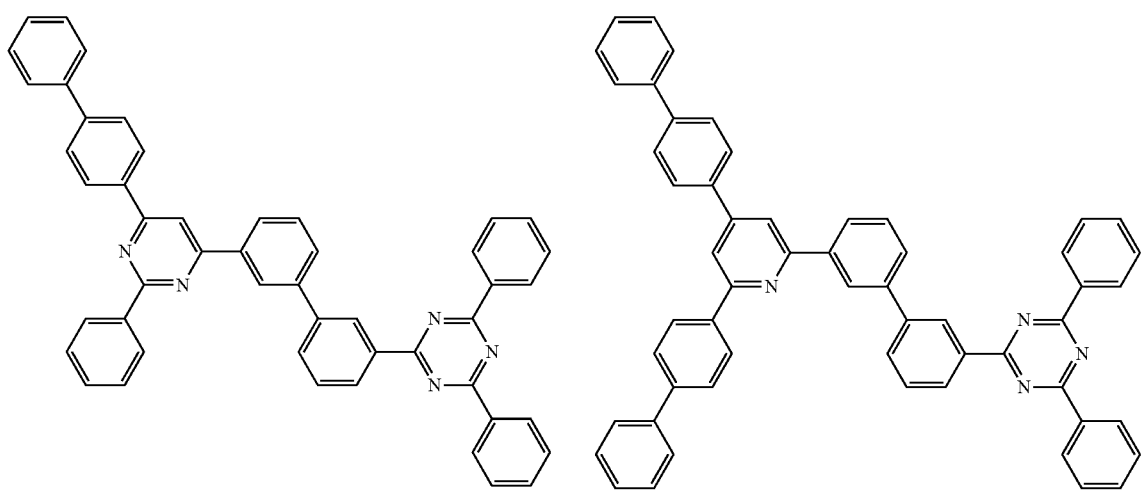
A(114)　　　　　　　　A(115)

-continued
A(116)
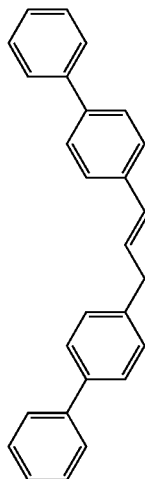
A(117)
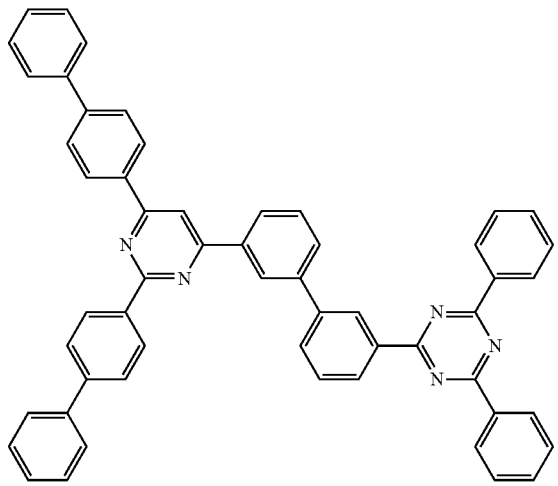
A(118)
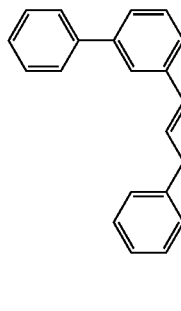
A(119)
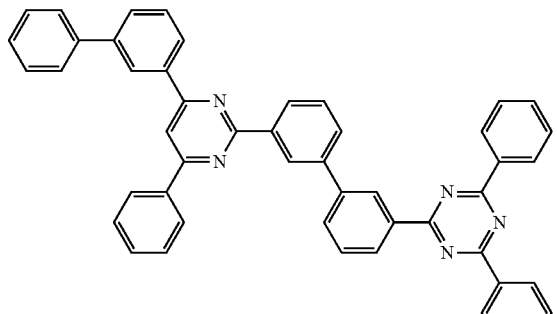
A(120)
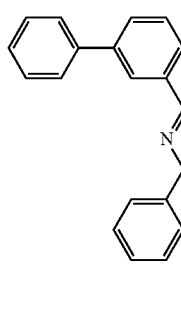
A(121)
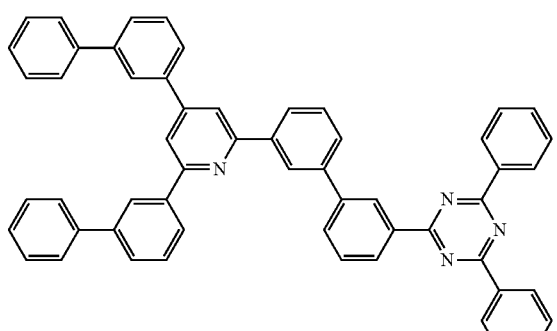
A(122)
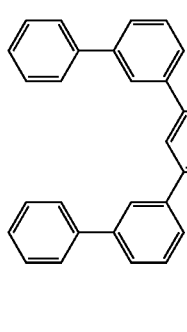
A(123)
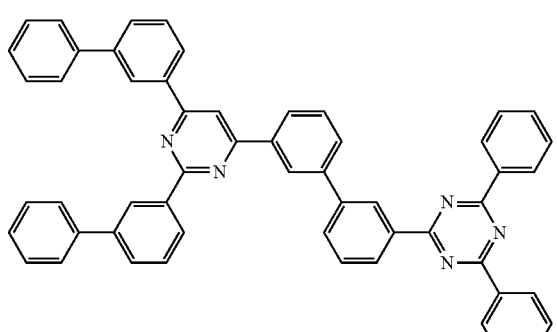

-continued
A(124)
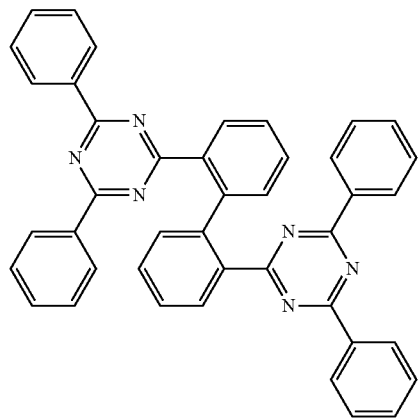
A(125)
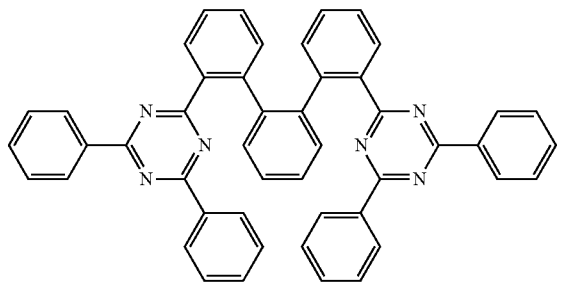
A(126)
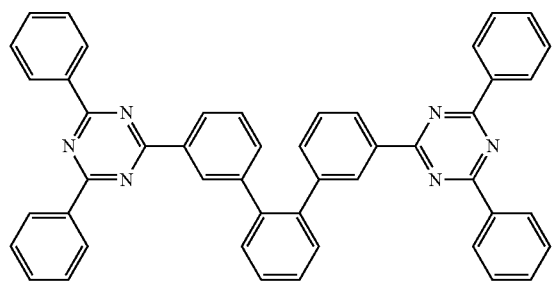
A(127)
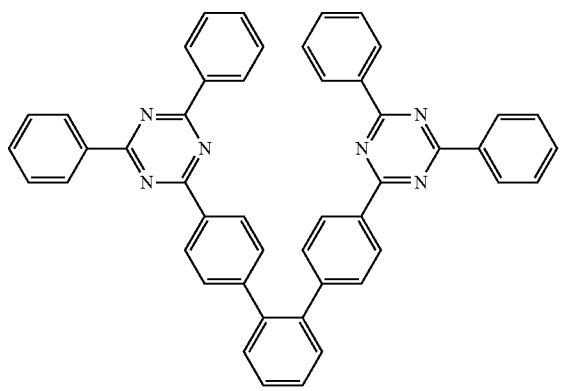
A(128)
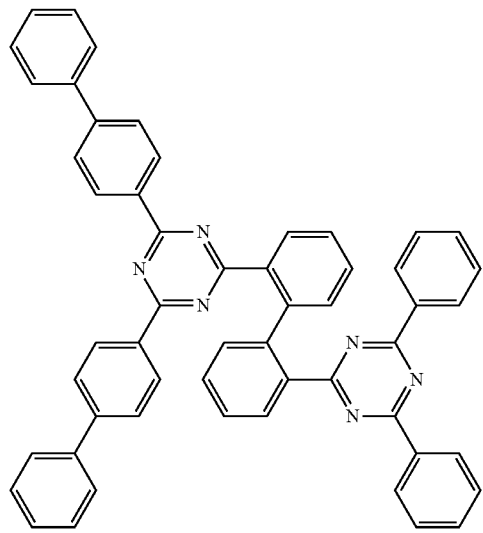
A(129)
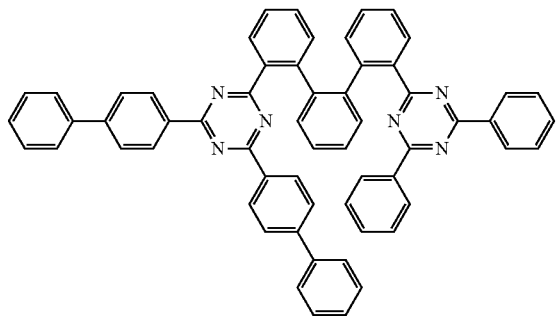

-continued
A(130) 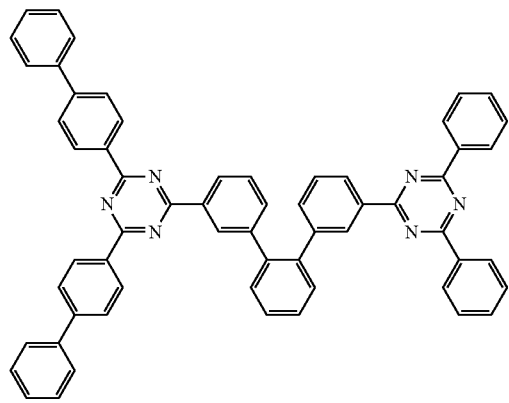
A(131) 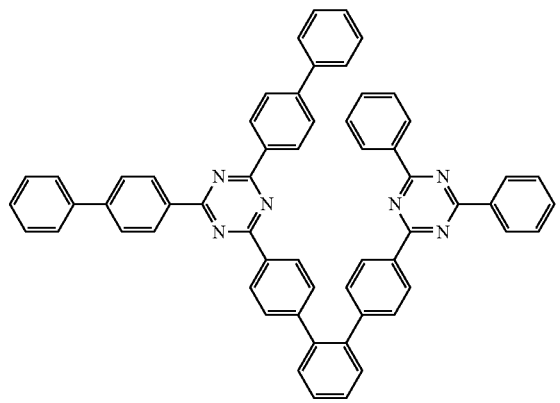
A(132) 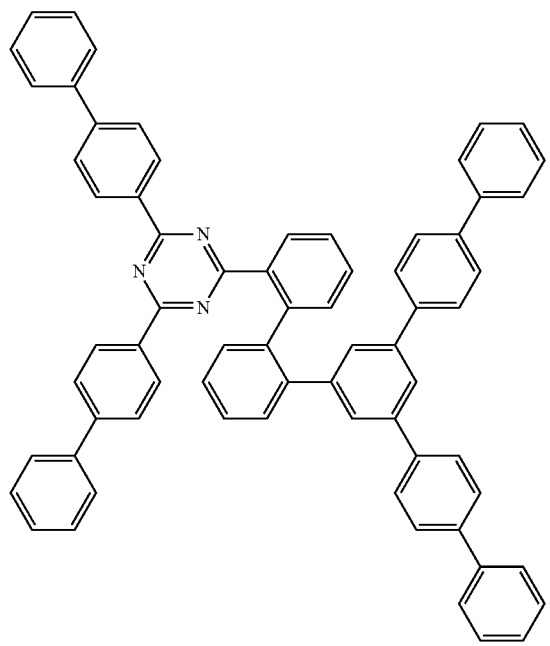
A(133) 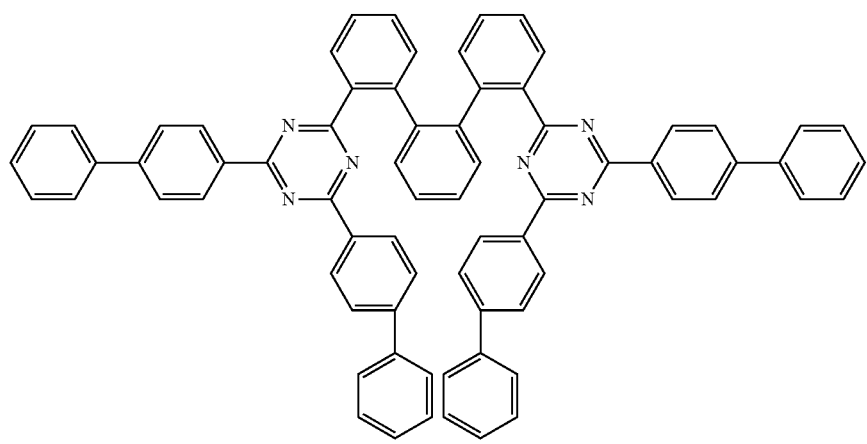

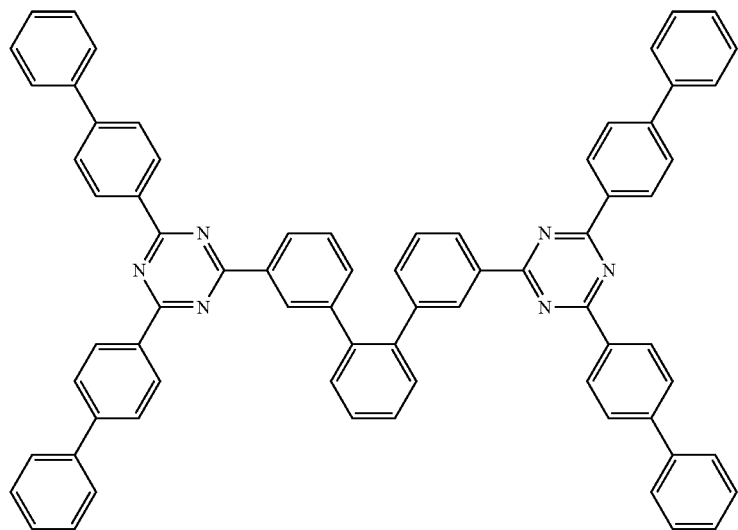
A(134)
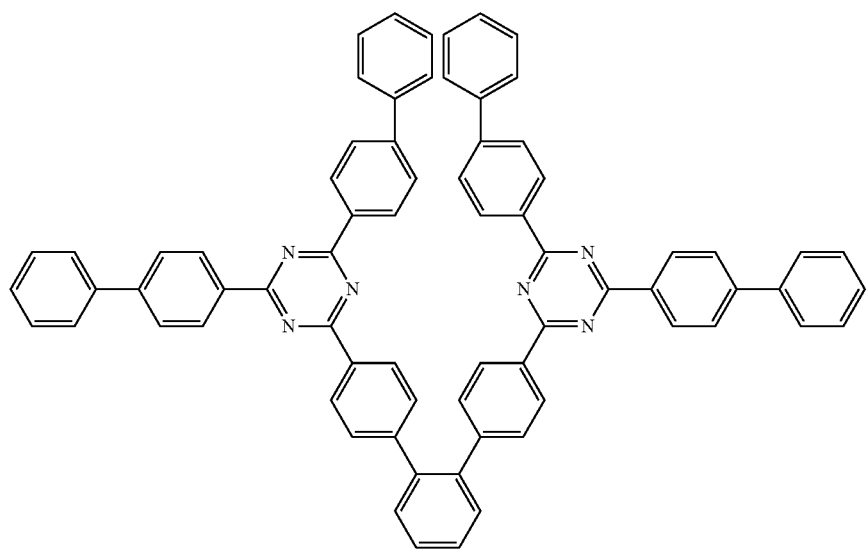
A(135)
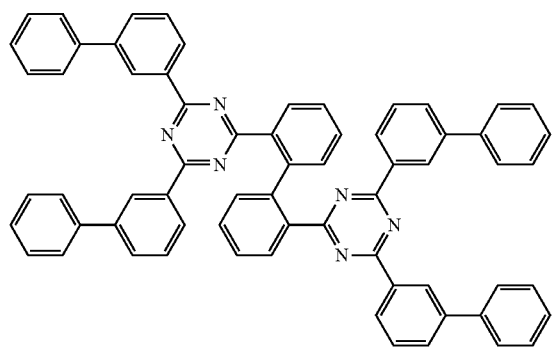
A(136)
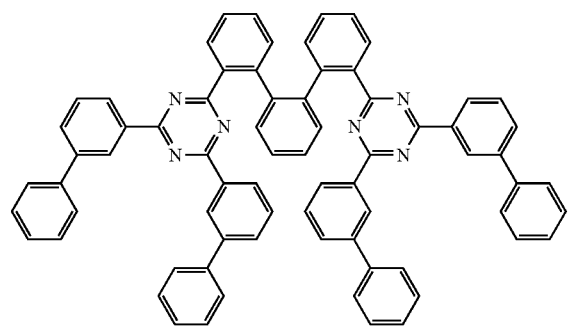
A(137)

-continued
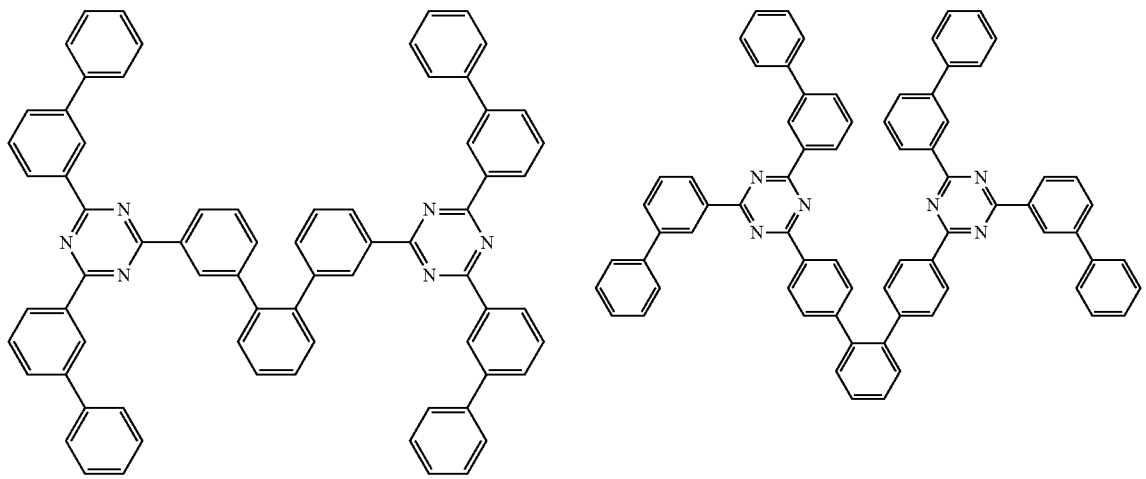
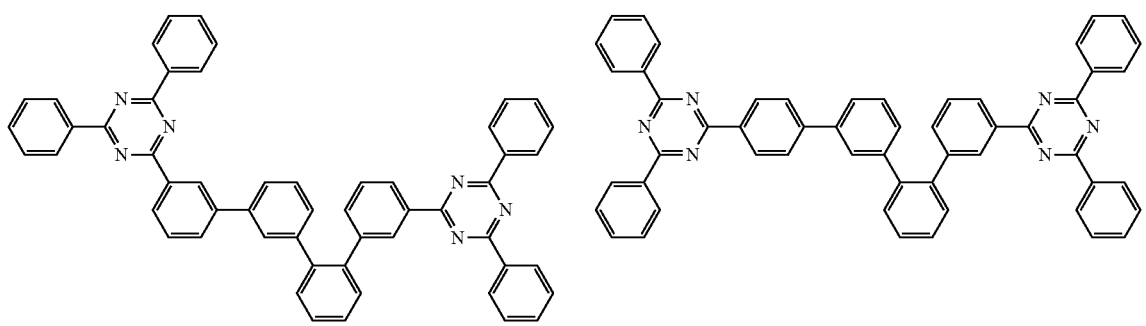
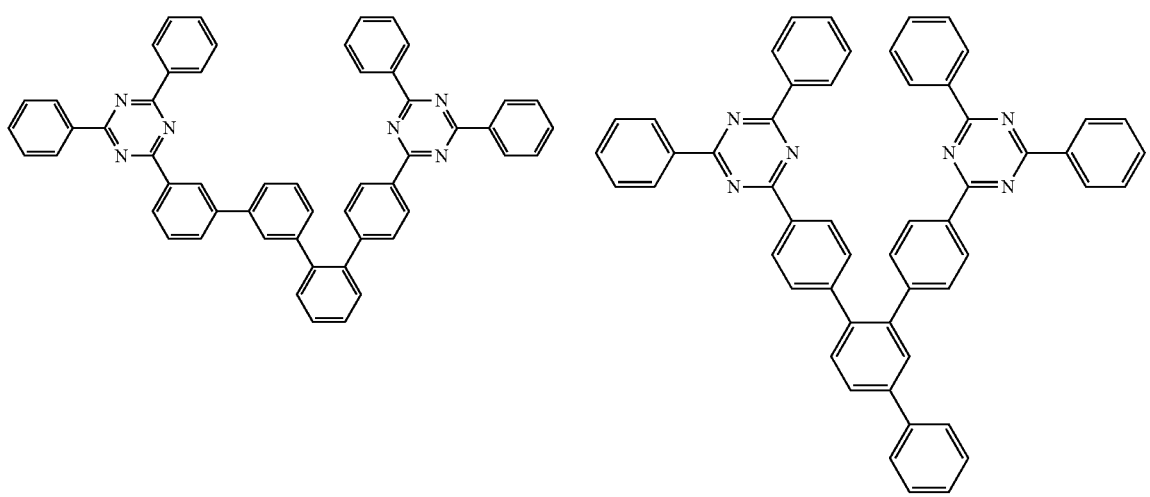

-continued
A(144)
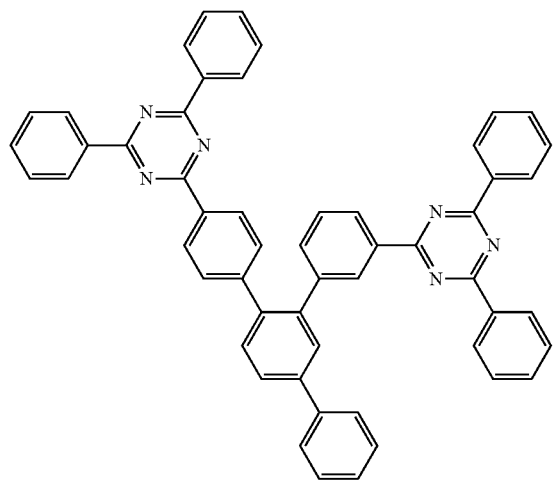
A(145)
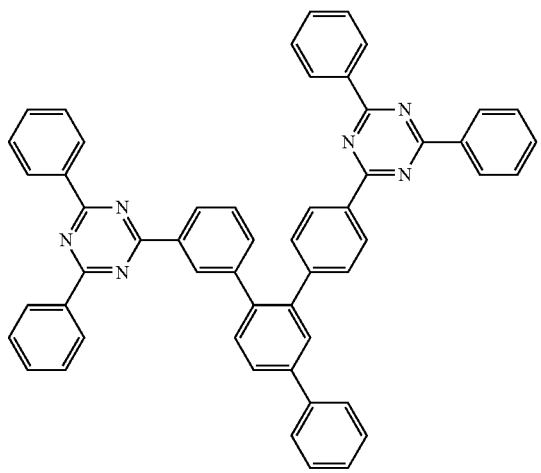
A(146)
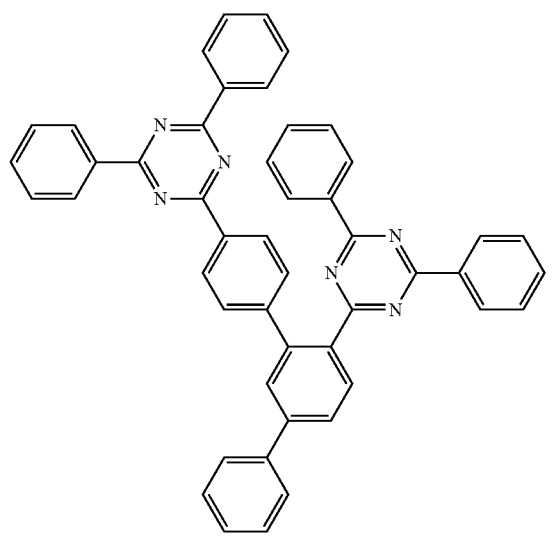
A(147)
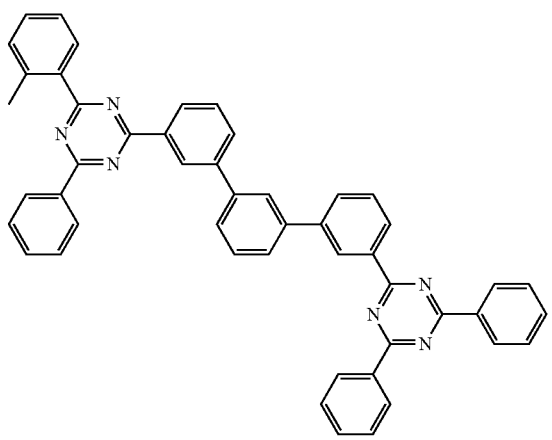
A(148)
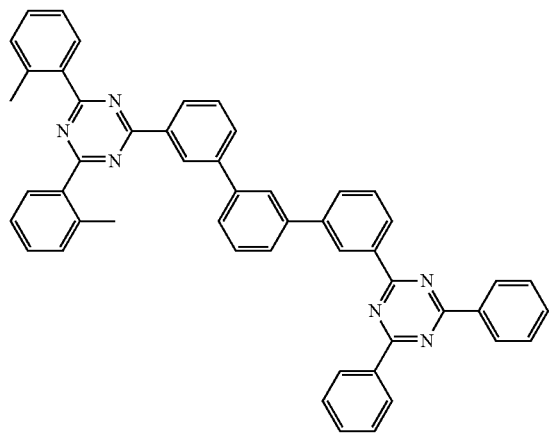
A(149)
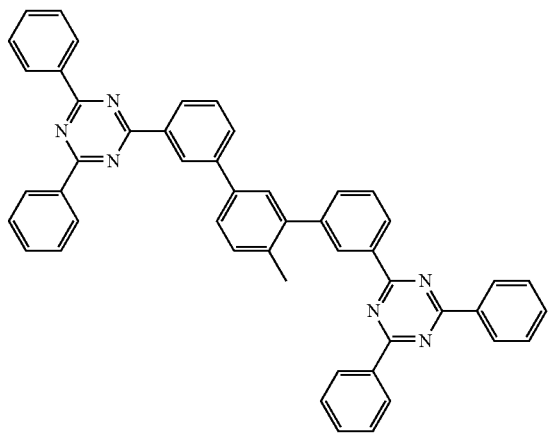

-continued
A(150)
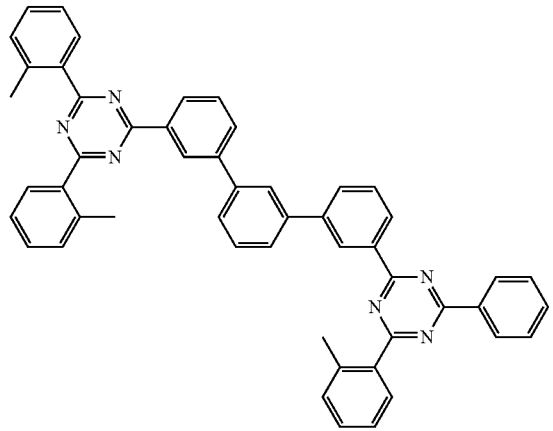
A(151)
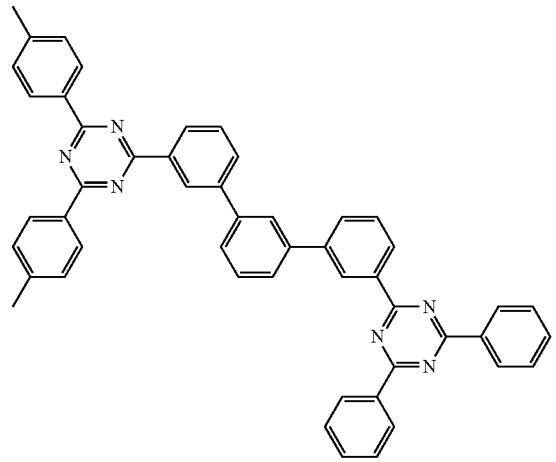
A(152)
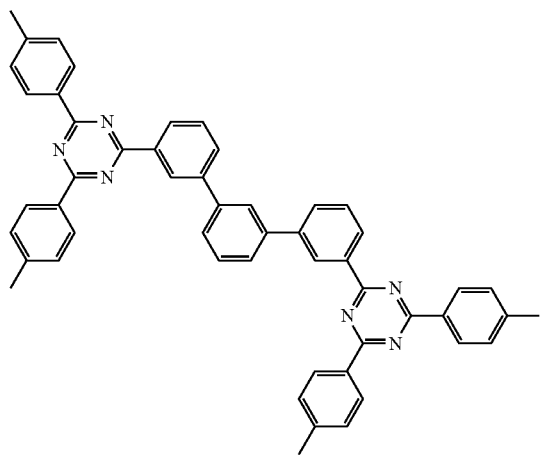
A(153)
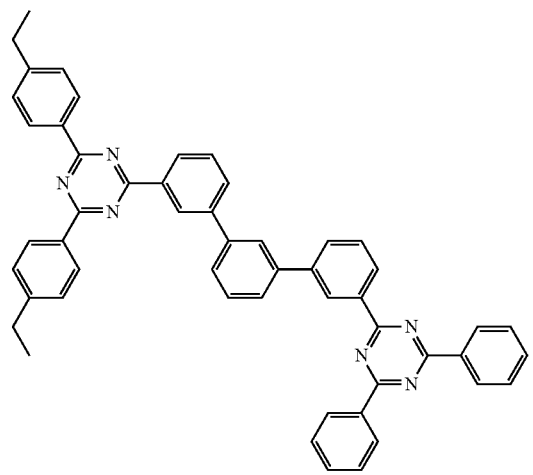
A(154)
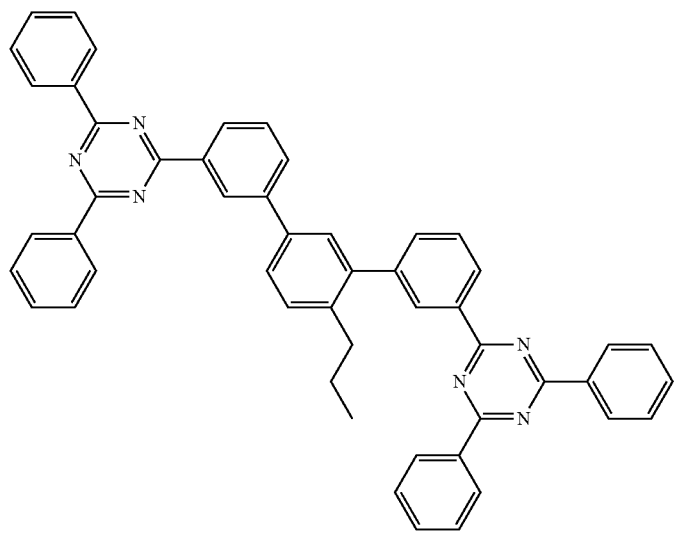

-continued
1
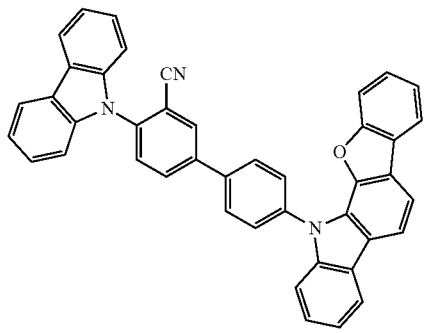
2
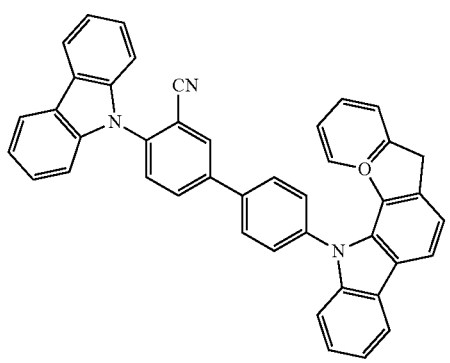
3
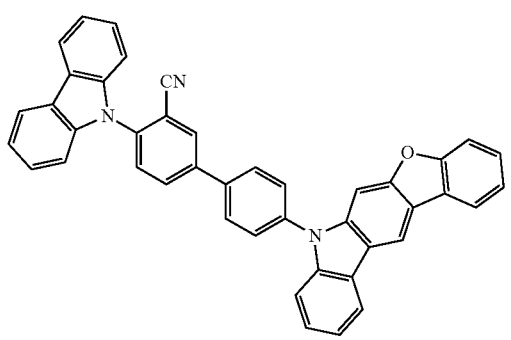
4
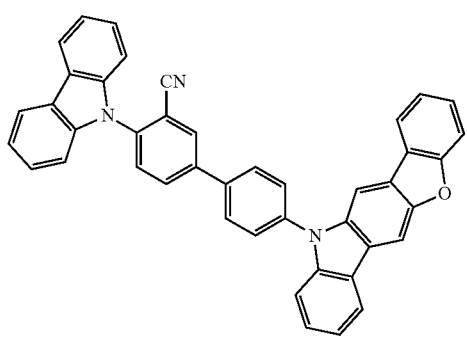
5
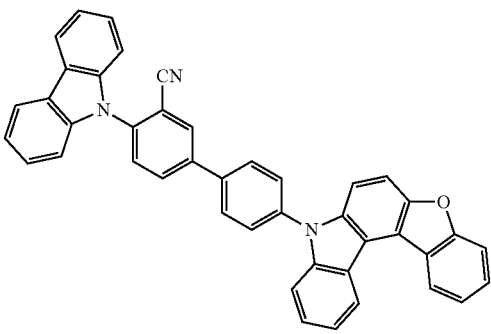
6
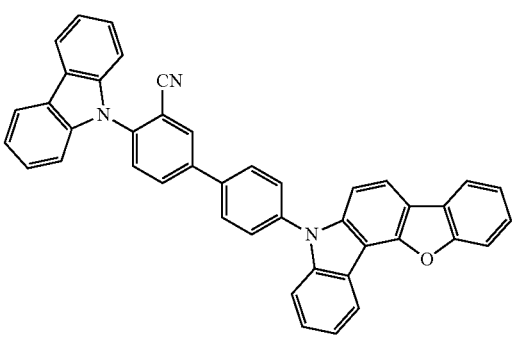
7
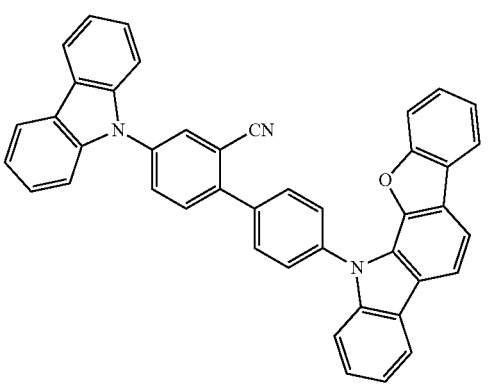
8
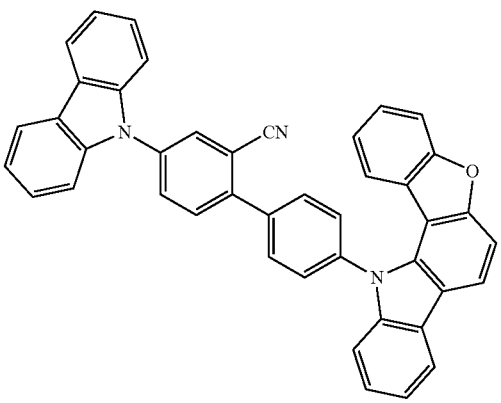

9
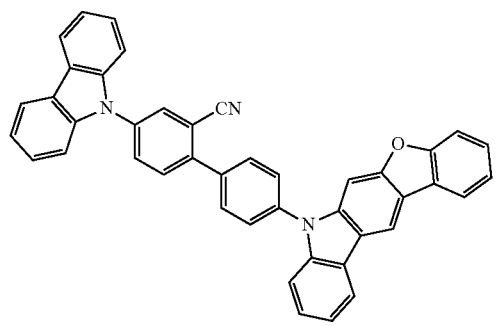
13
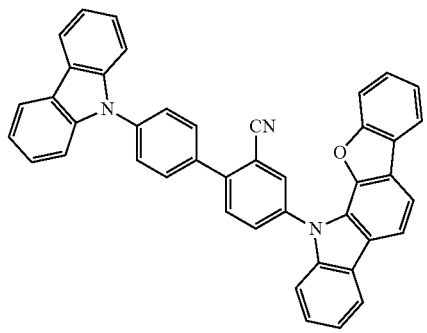
10
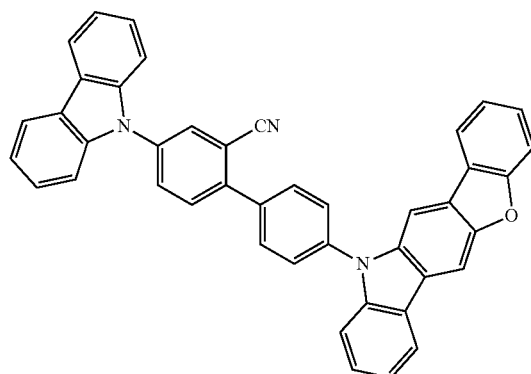
14
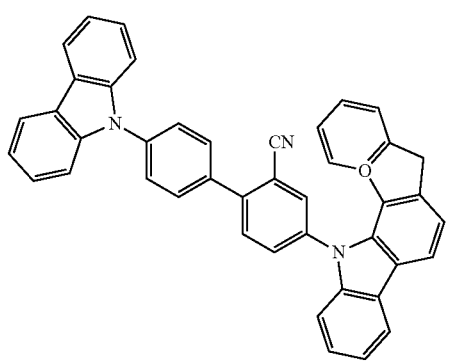
11
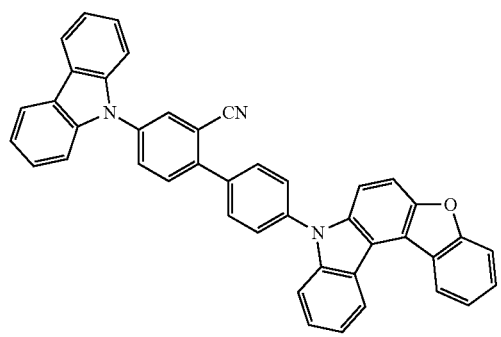
15
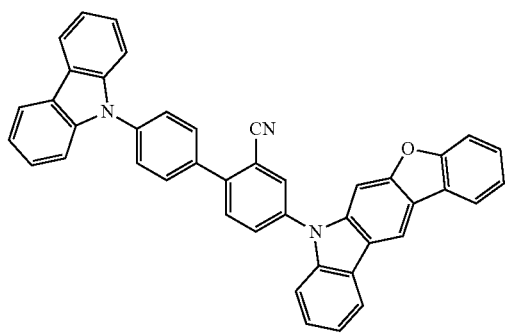
12
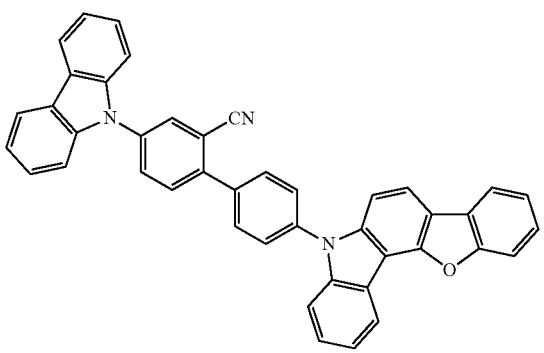
16
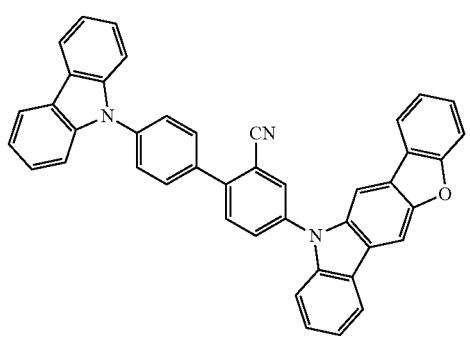

-continued

17

18

19

20

21

22

23

24

-continued
25
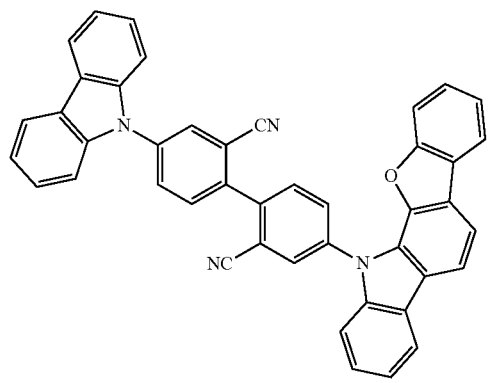
26
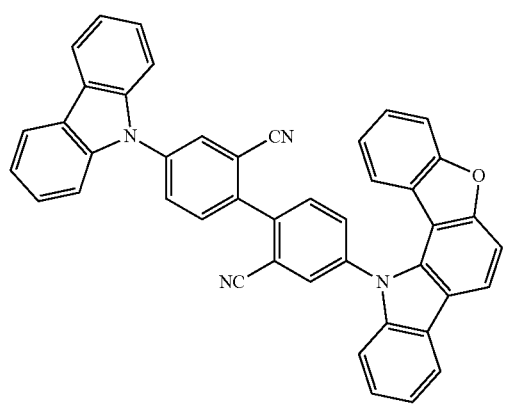
27
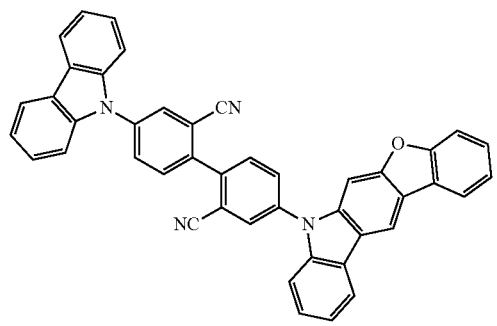
28
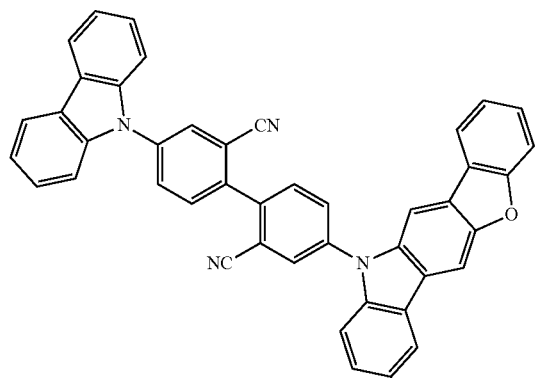
-continued
29
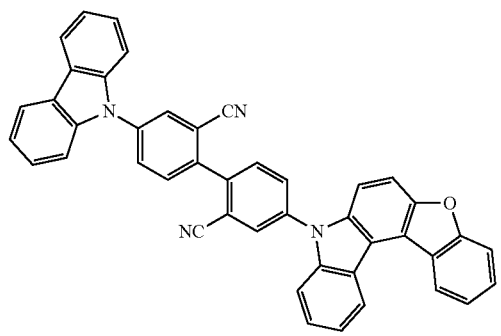
30
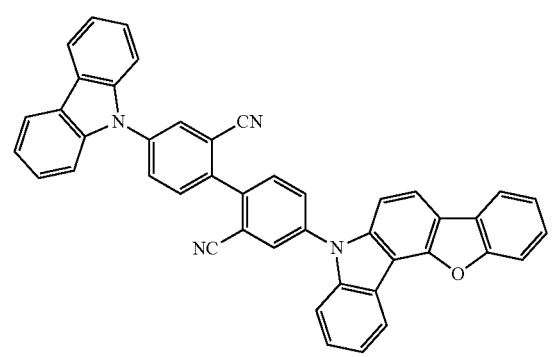
31
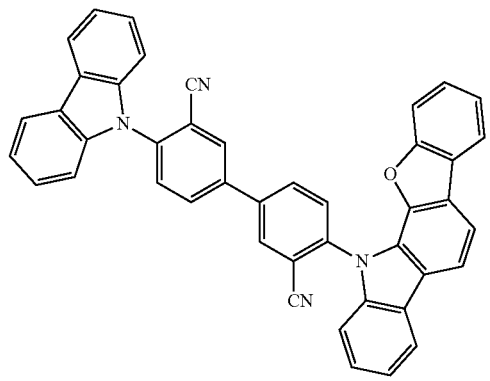
32
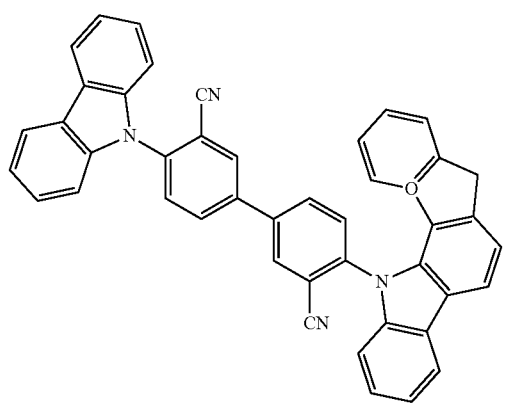

33
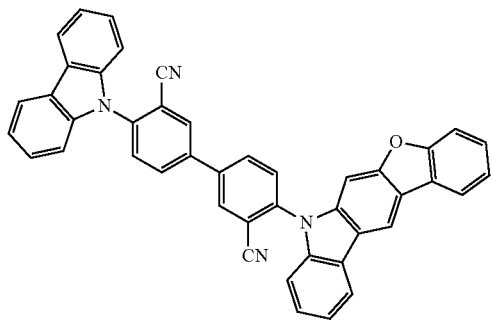
34
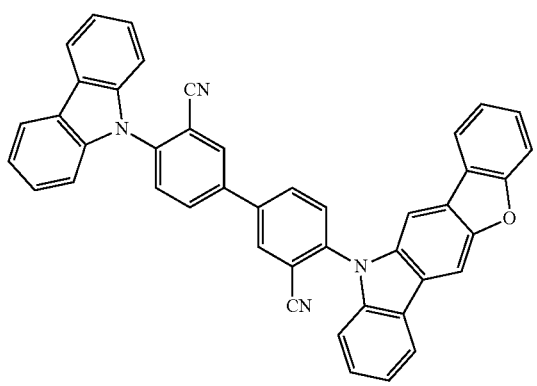
35
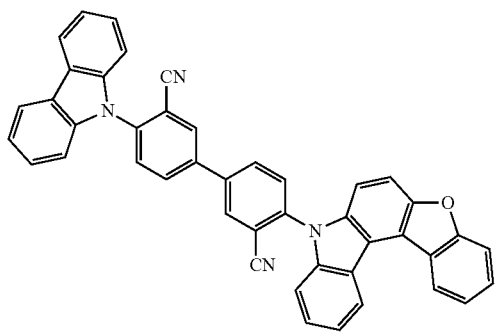
36
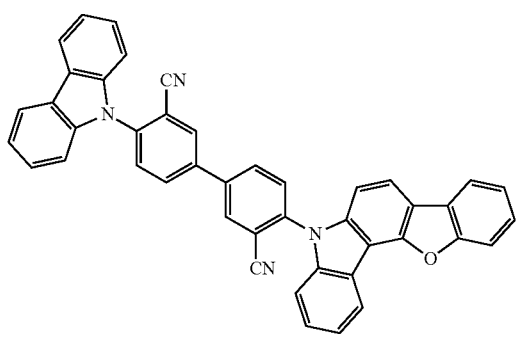
37
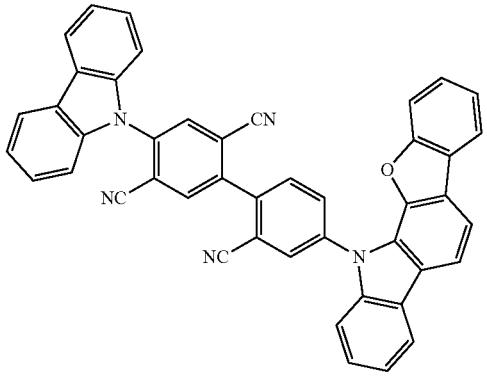
38
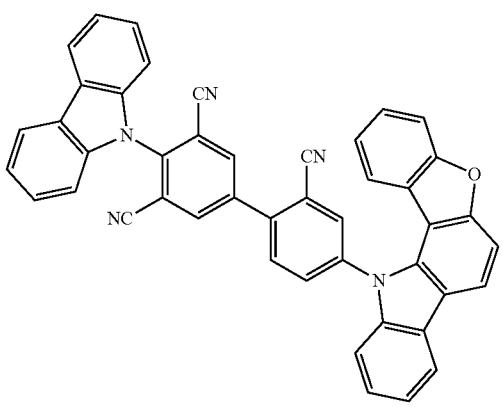
39
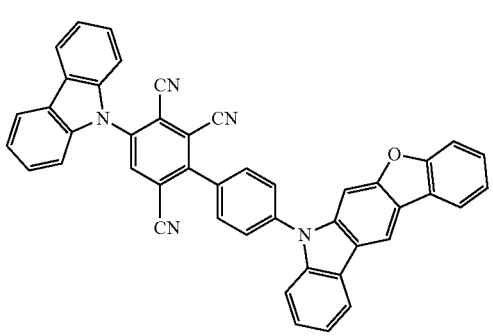
40
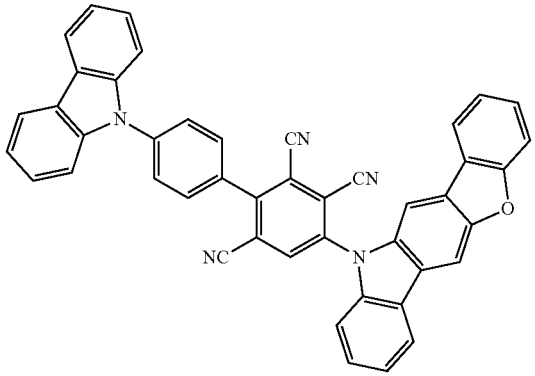

-continued
41
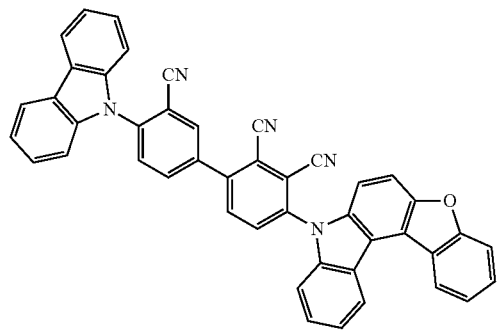
42
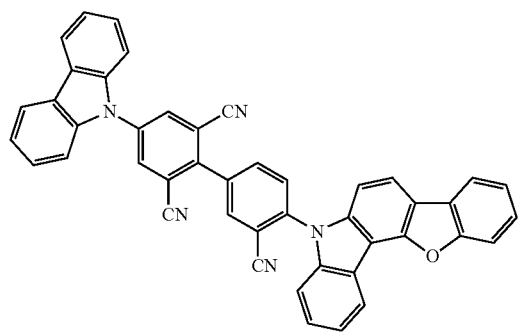
43
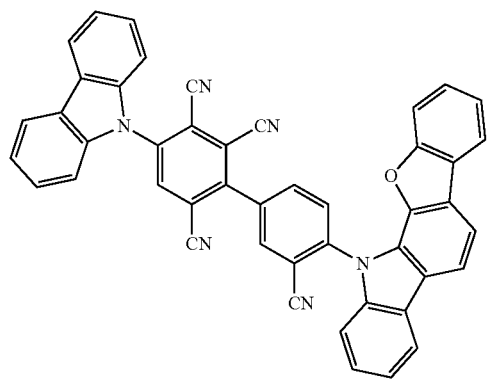
44
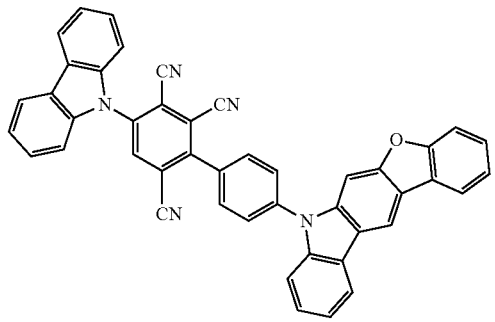
-continued
45
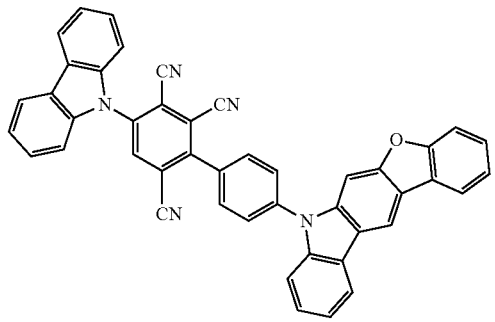
46
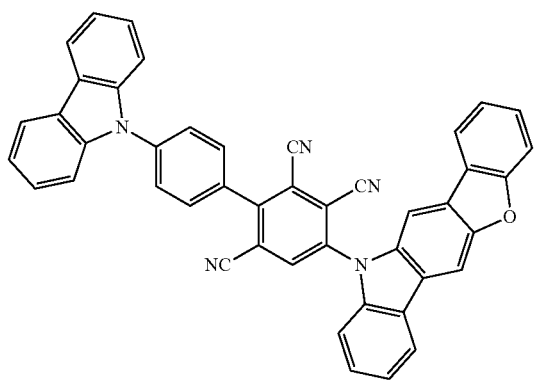
47
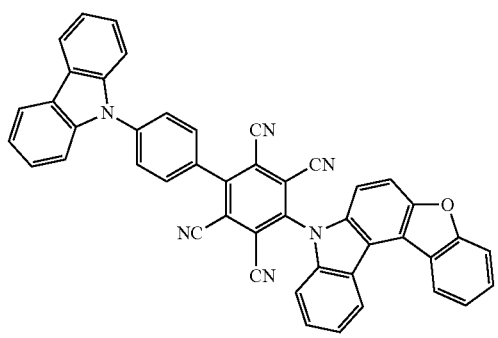
48
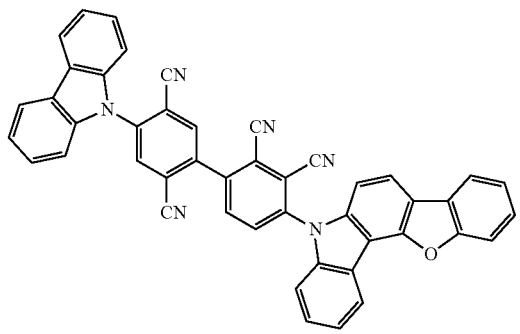

49
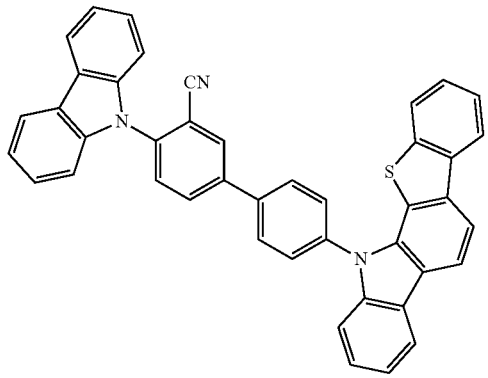
50
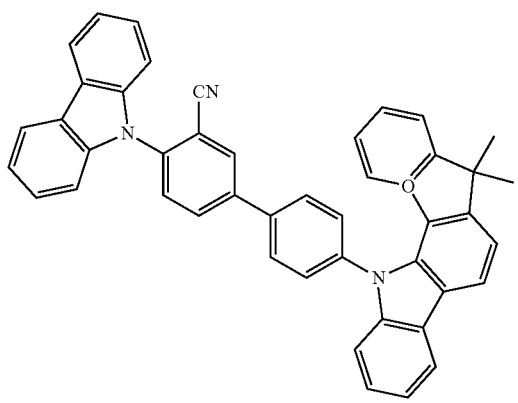
51
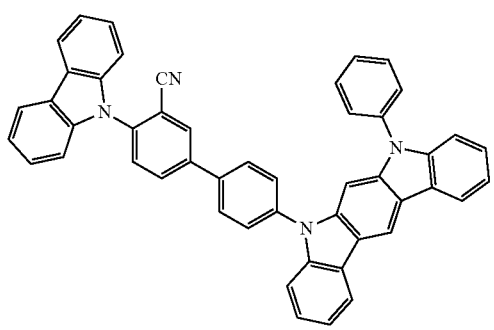
52
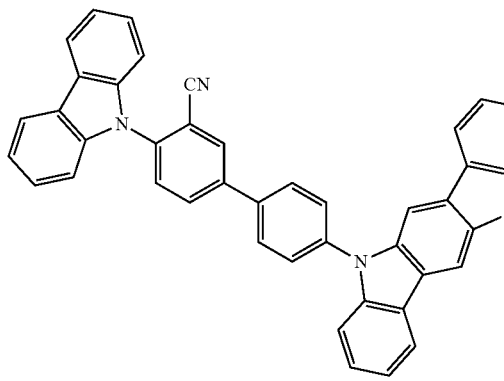
53
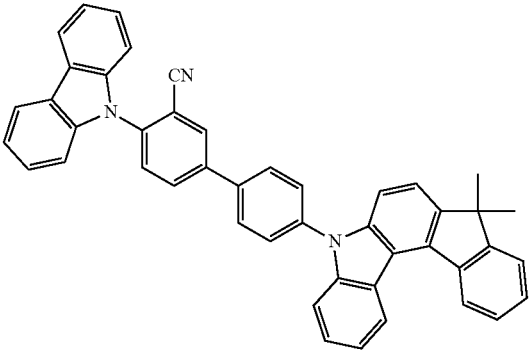
54
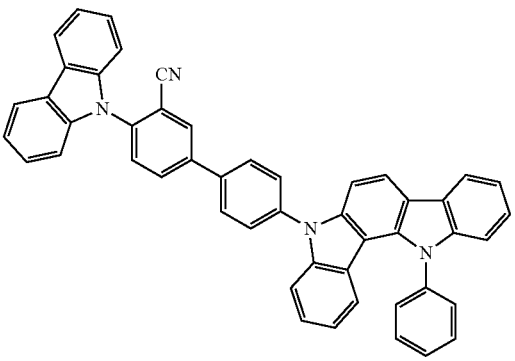
55
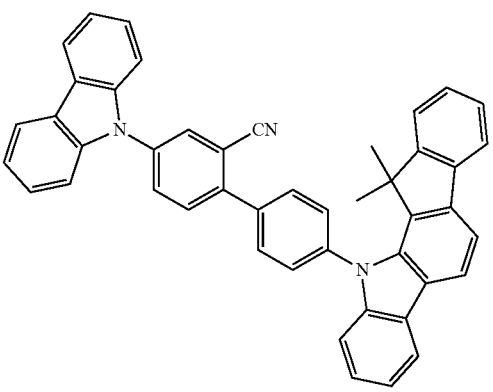
56
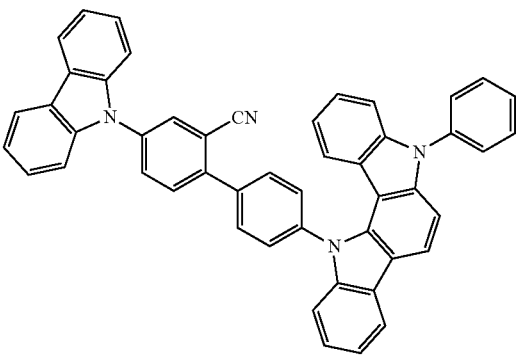

185
-continued
57
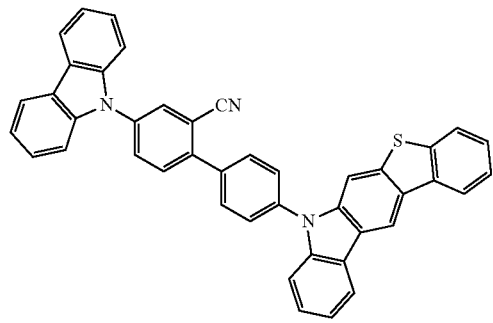
58
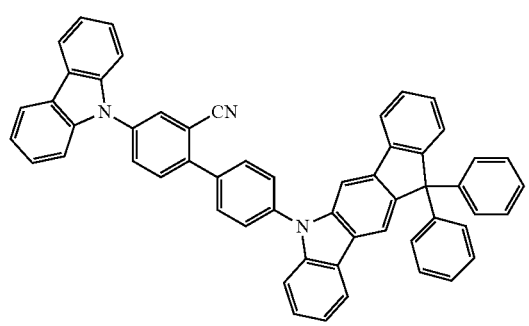
59
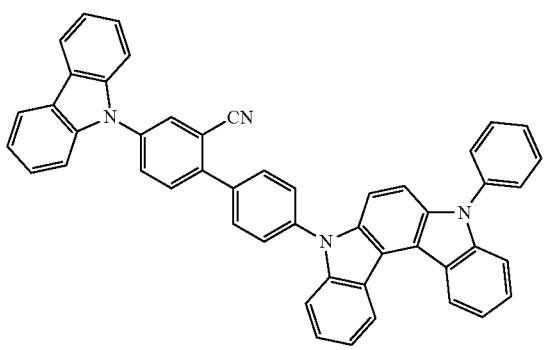
60
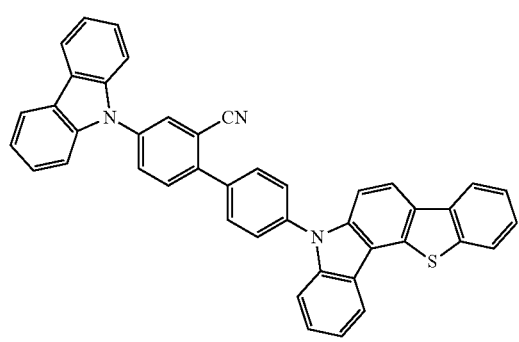
186
-continued
61
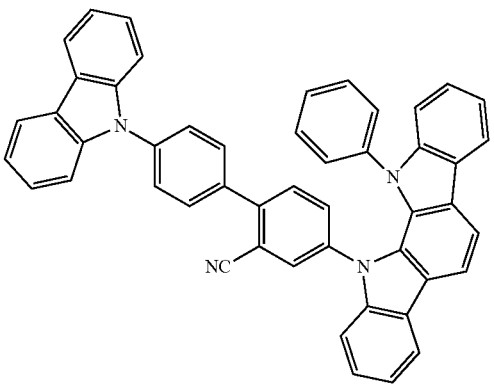
62
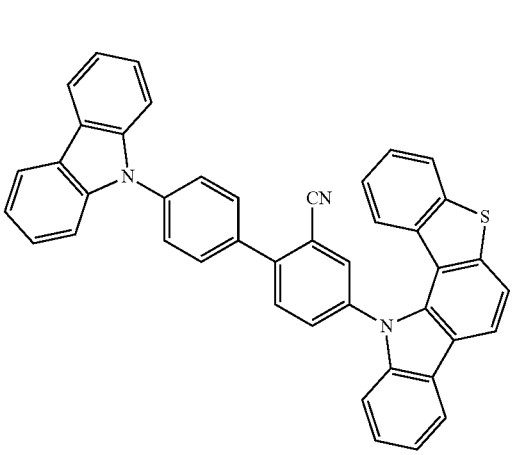
63
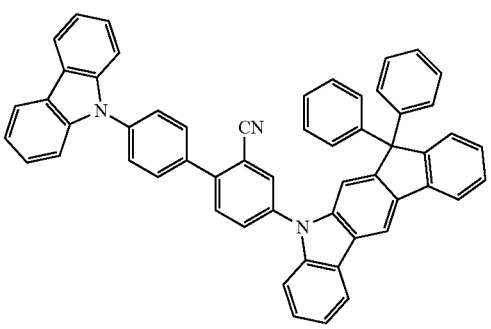
64
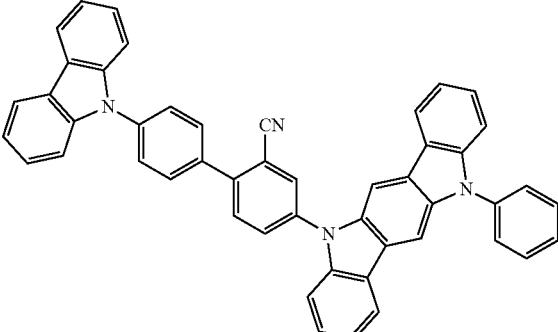

-continued
65
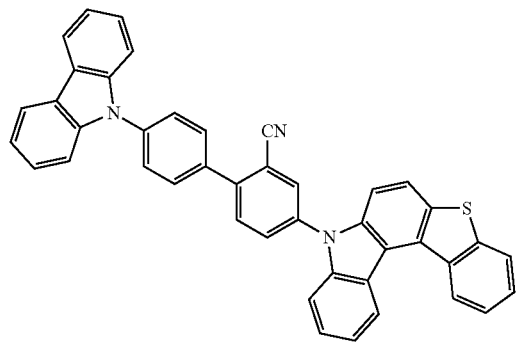
66
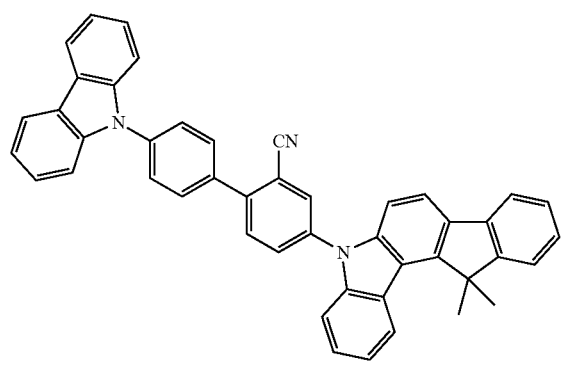
67
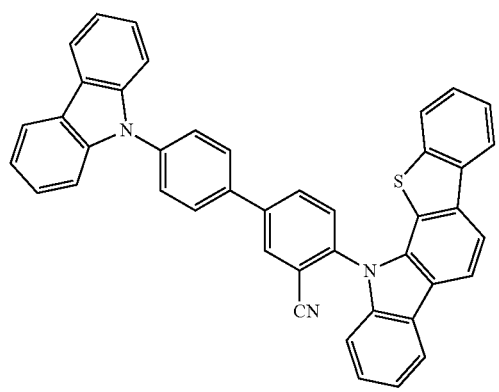
68
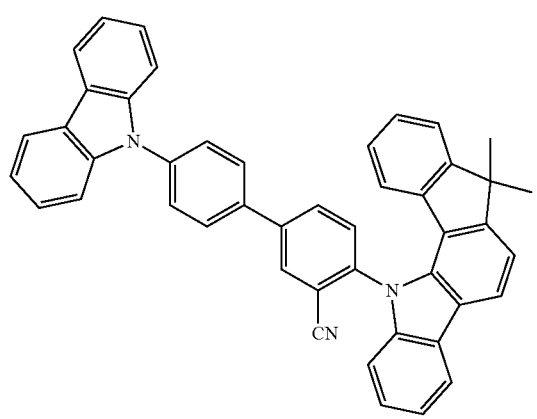
-continued
69
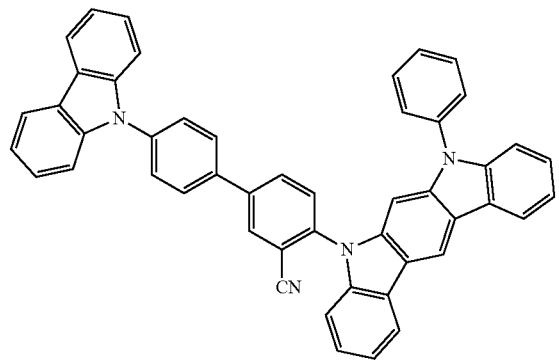
70
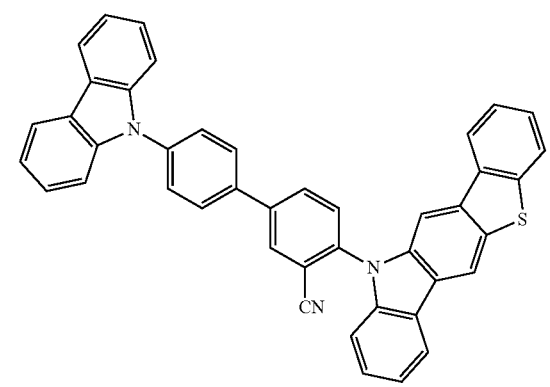
71
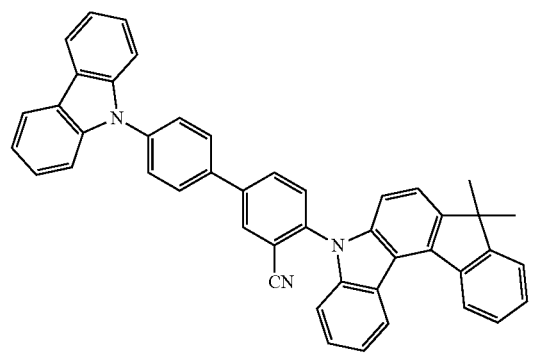
72
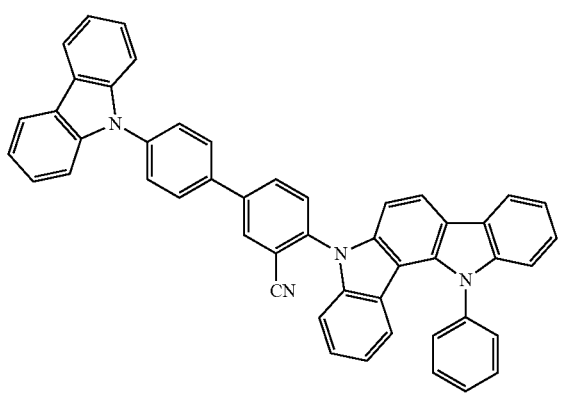

73
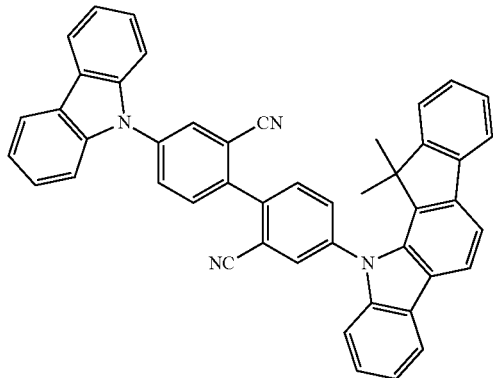
74
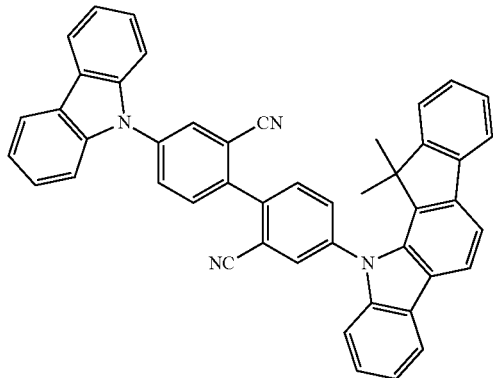
75
77
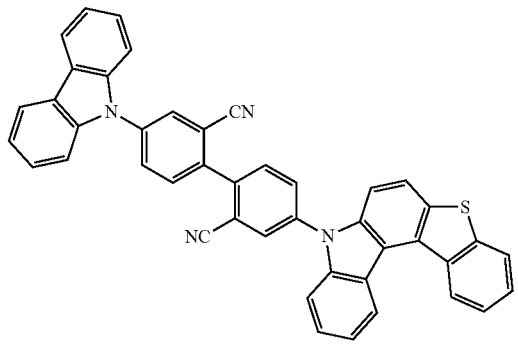
78
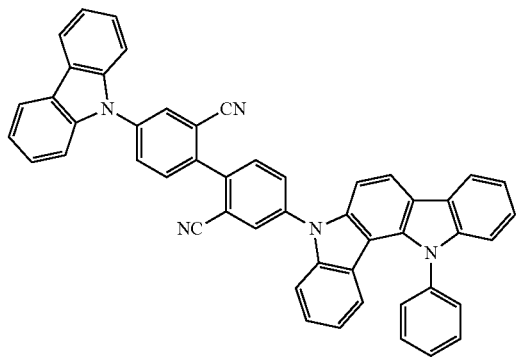
79
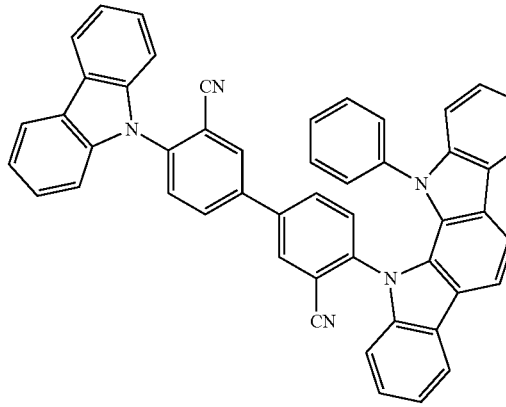
80
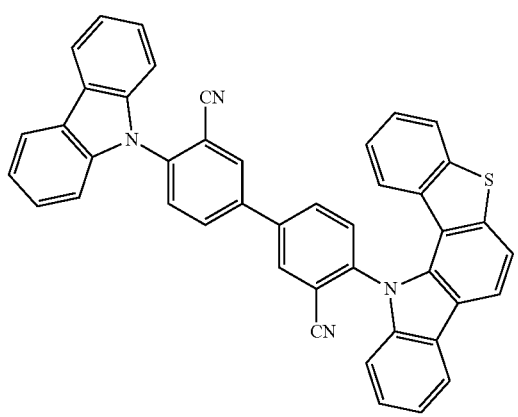
76

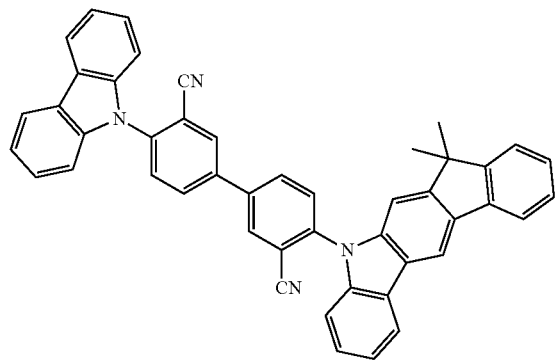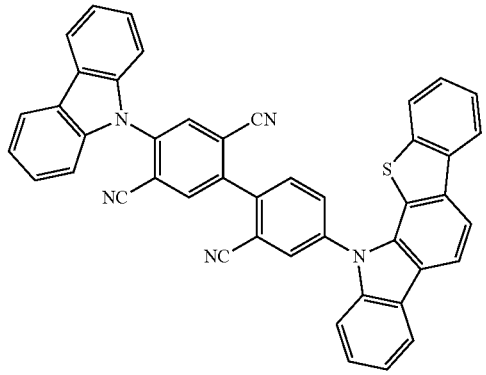

89
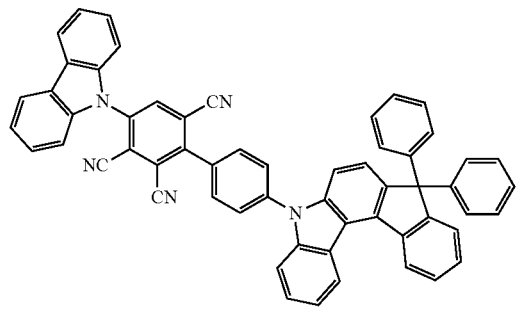
90
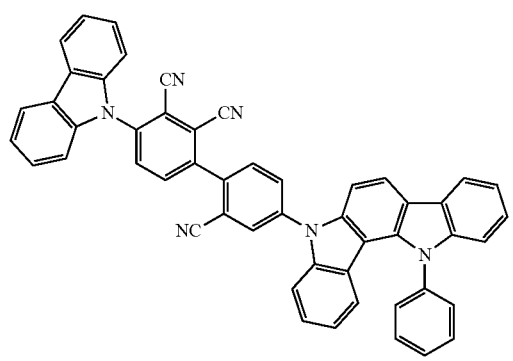
91
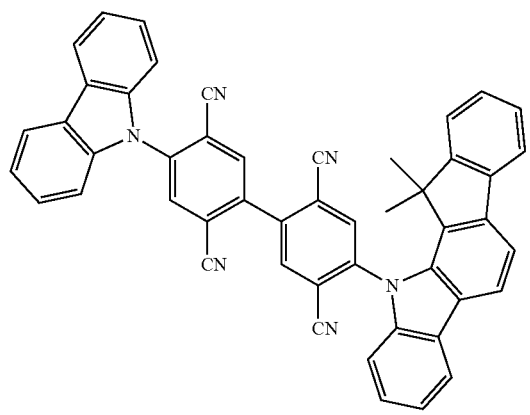
92
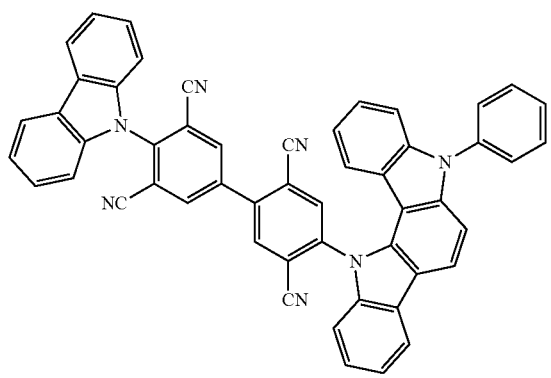
93
94
95
96
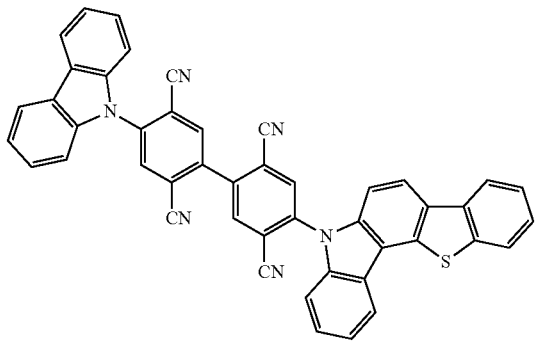

97
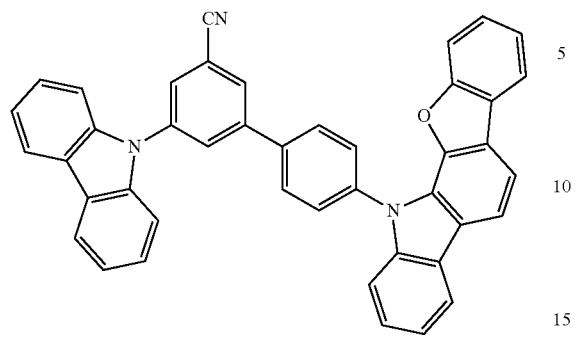
98
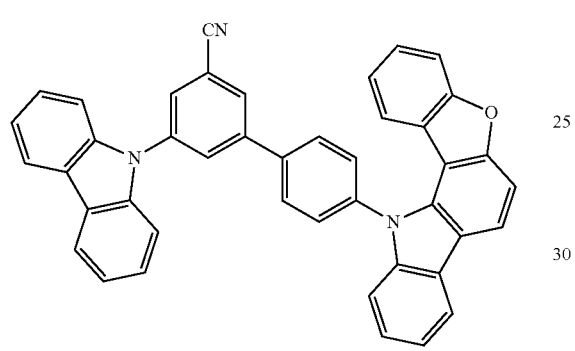
99
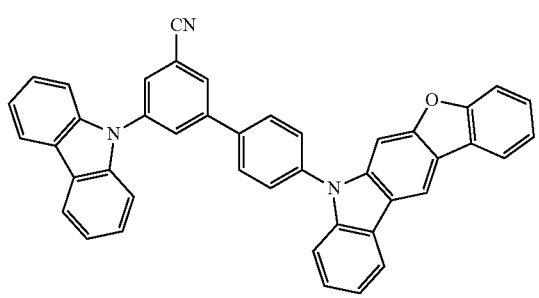
100
101
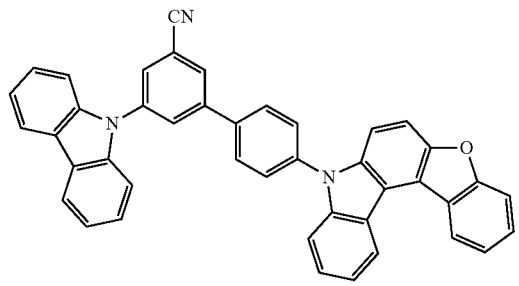
102
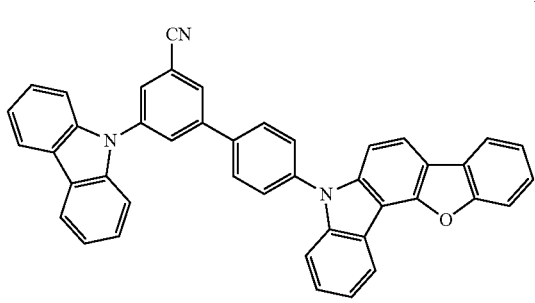
103
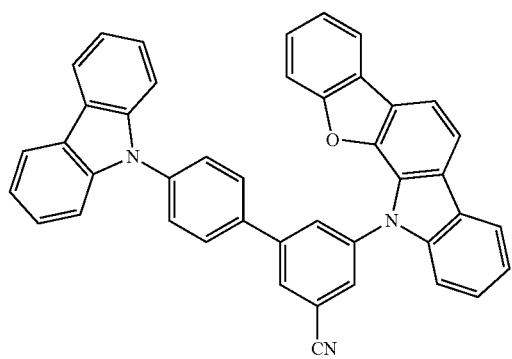
104
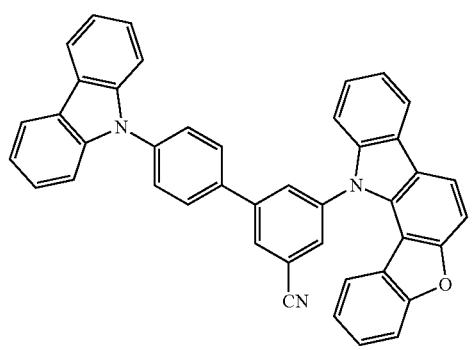

105
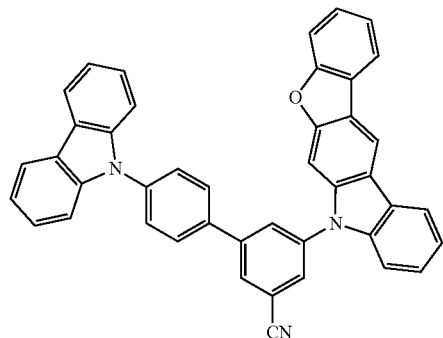
106
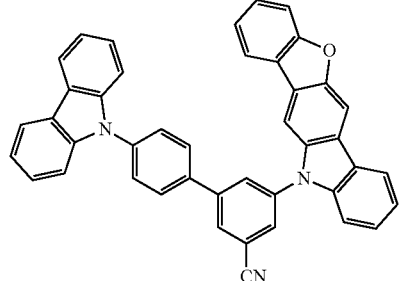
107
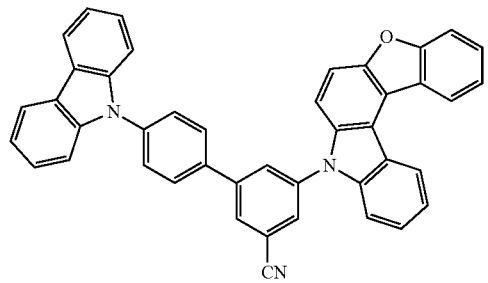
108
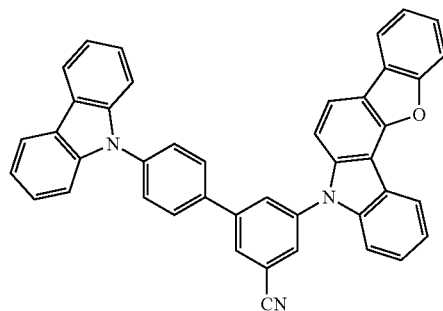
109
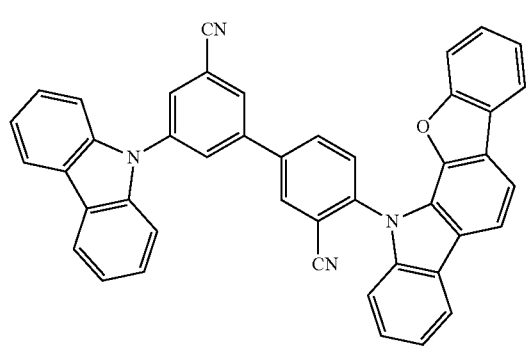
110
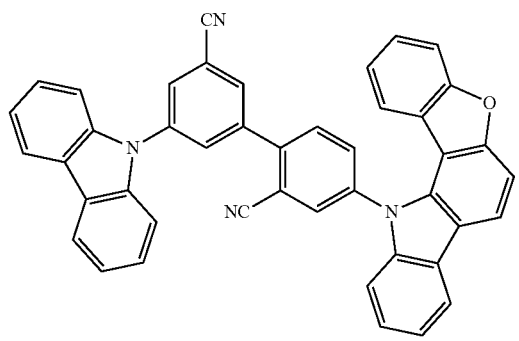
111
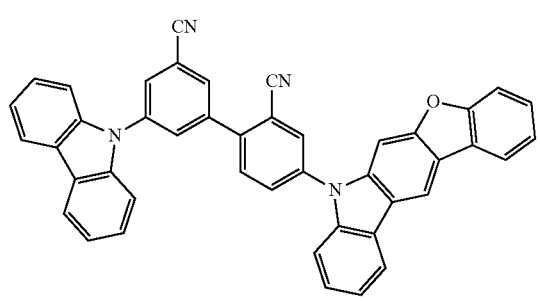
112
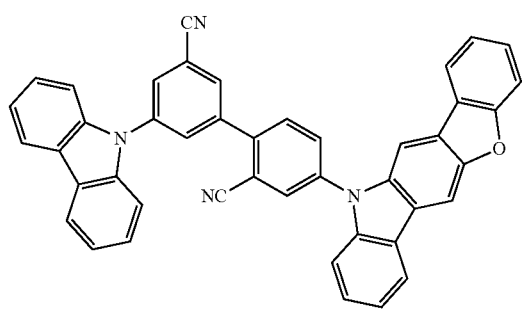
113
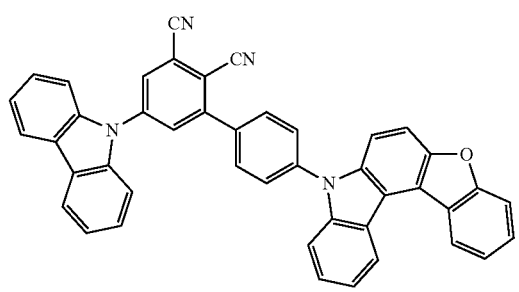
114
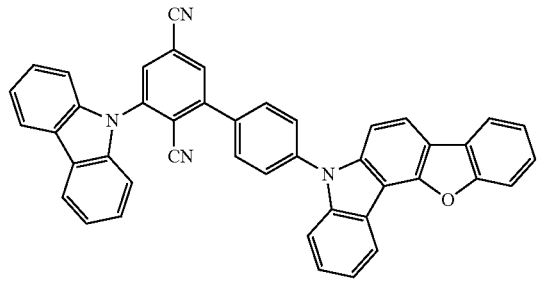

199
-continued
115
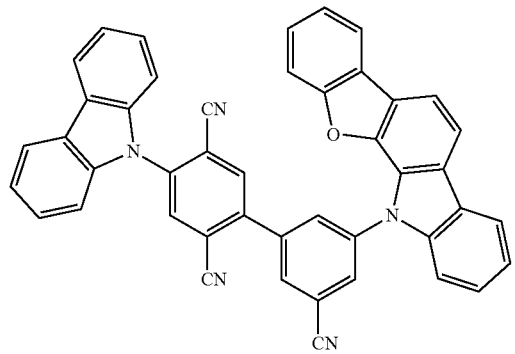
116
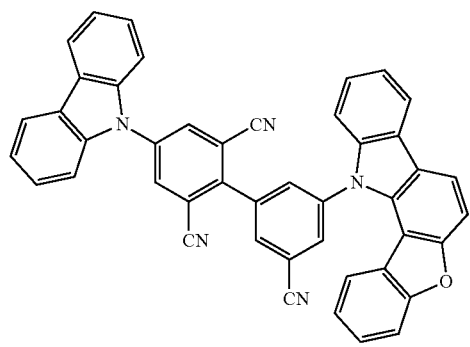
117
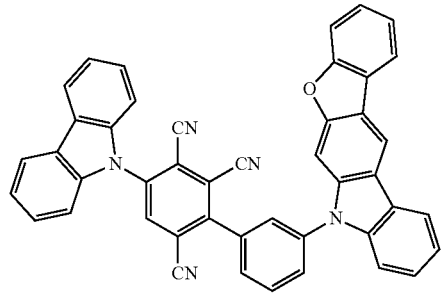
118
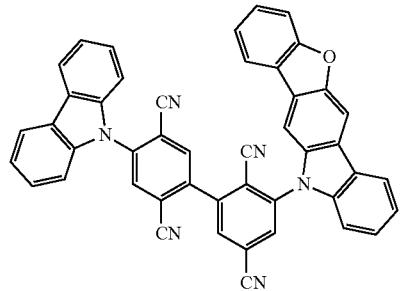
119
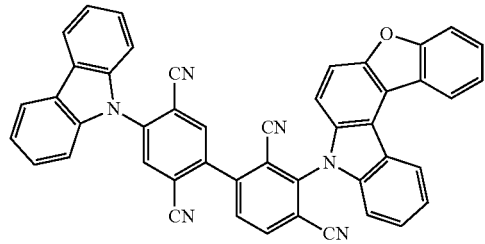
200
-continued
120
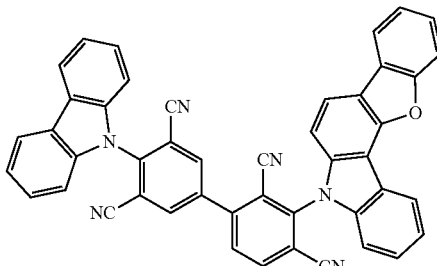
121
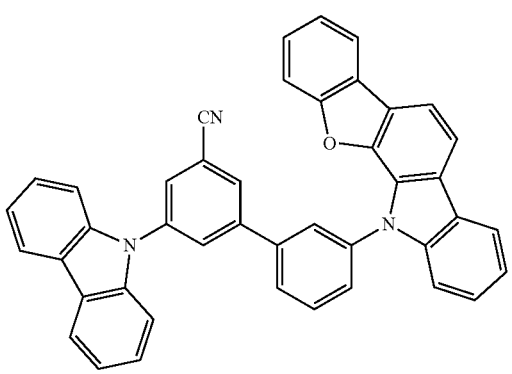
122
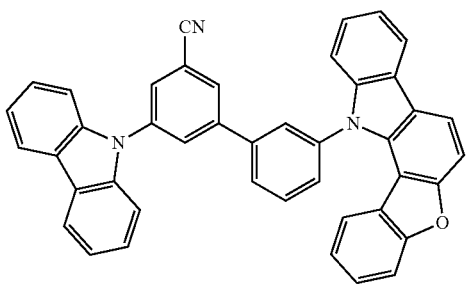
123
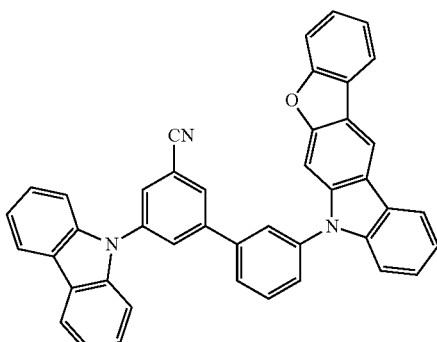
124
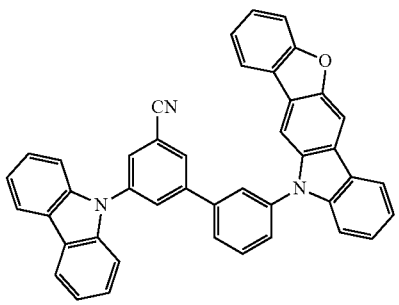

-continued
125
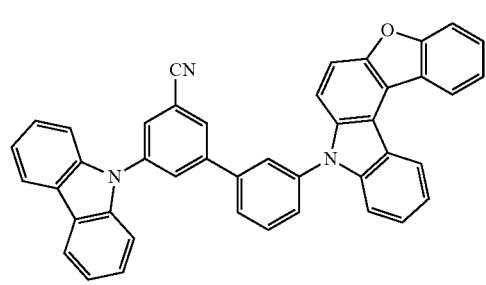
126
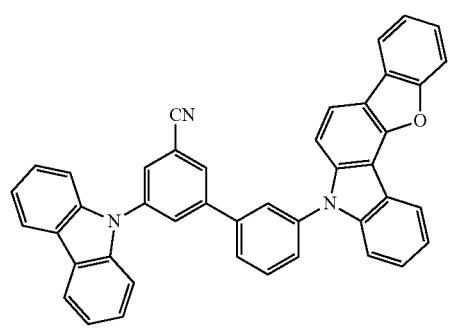
127
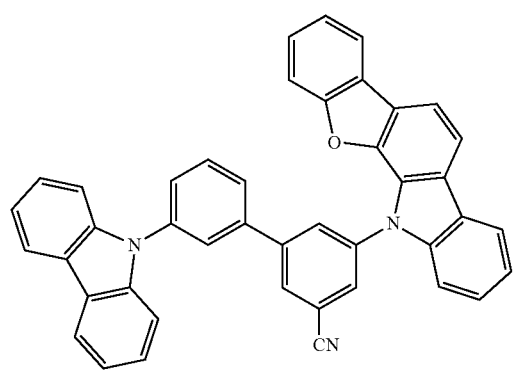
128
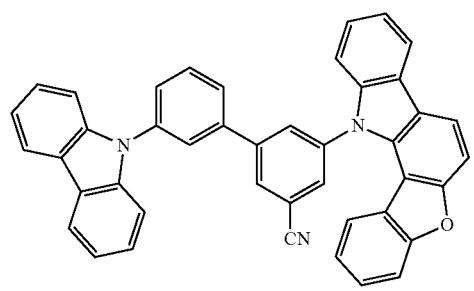
129
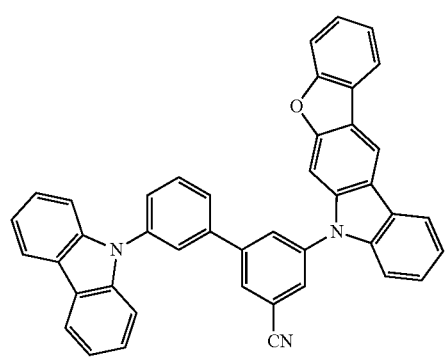
-continued
130
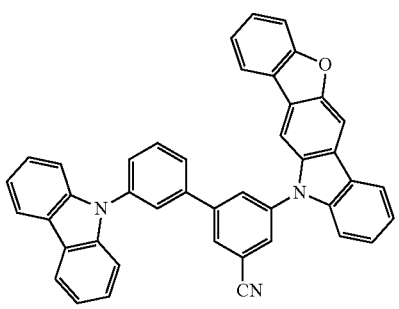
131
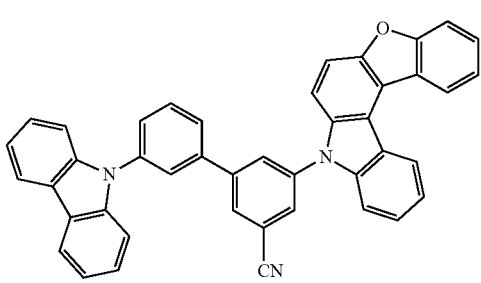
132
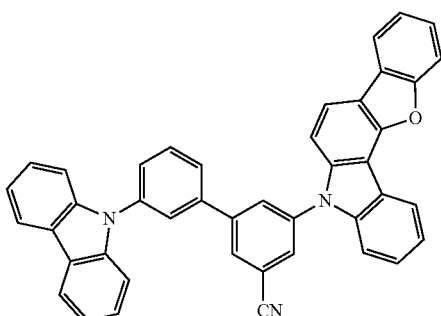
133
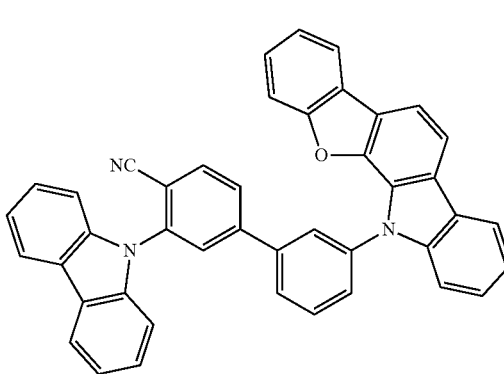
134
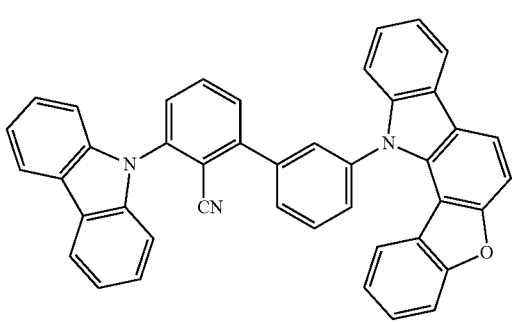

135
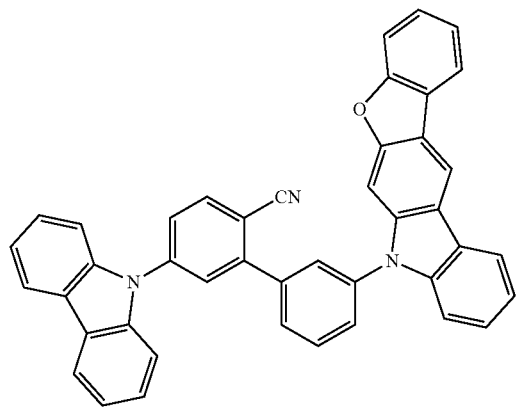
136
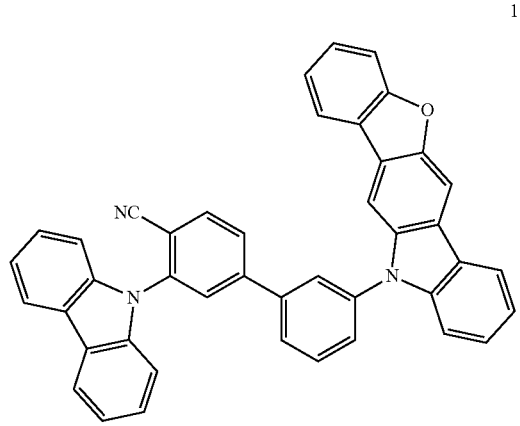
137
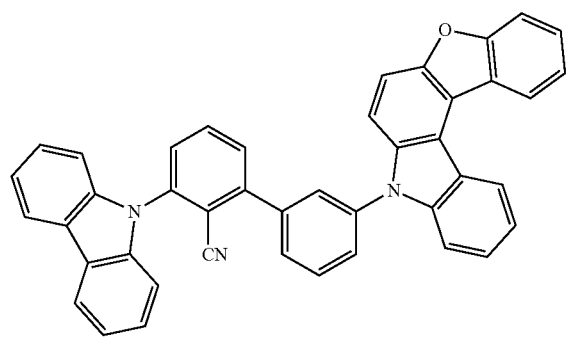
138
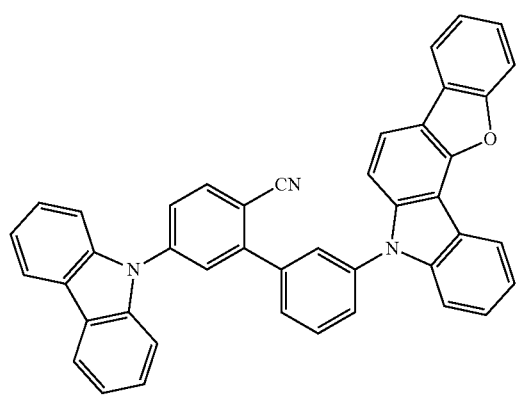
139
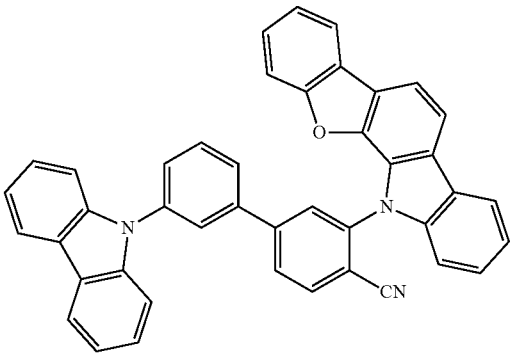
140
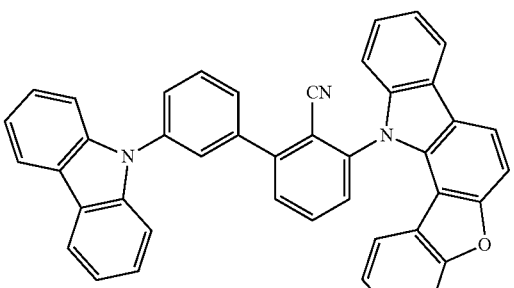
141
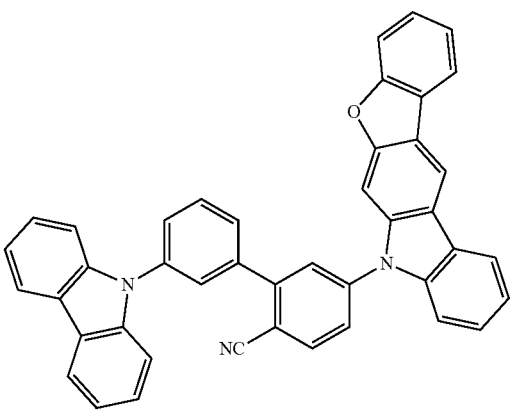
142
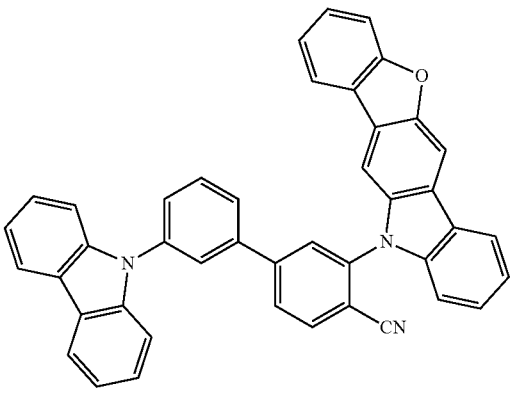

-continued
143
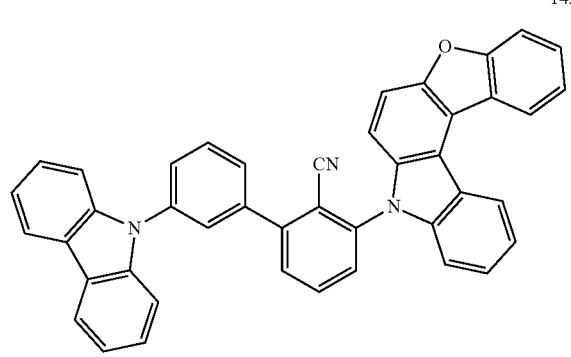
144
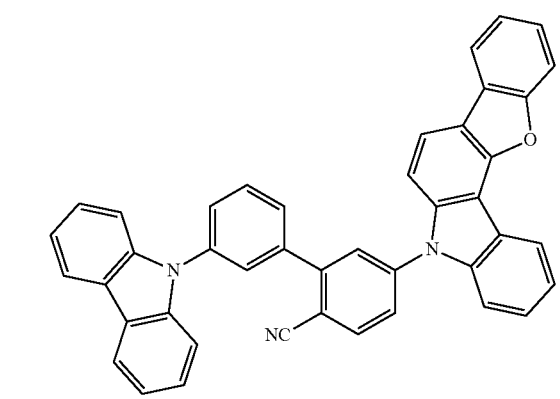
145

146

-continued
147
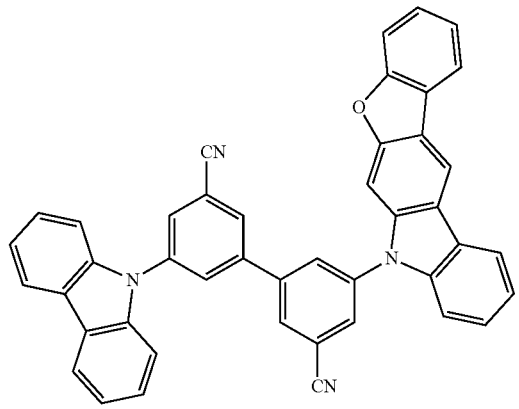
148
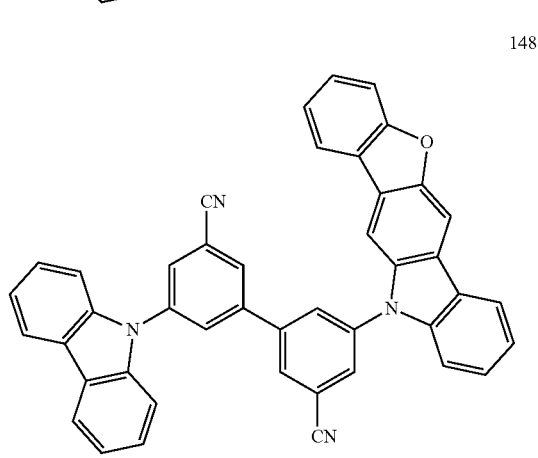
149
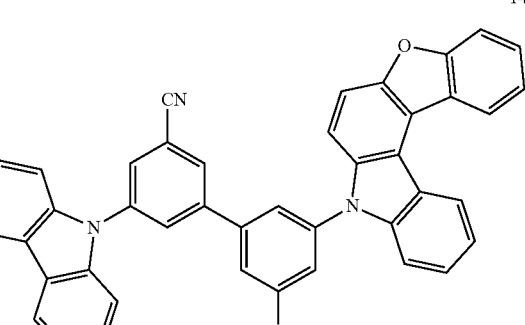
150
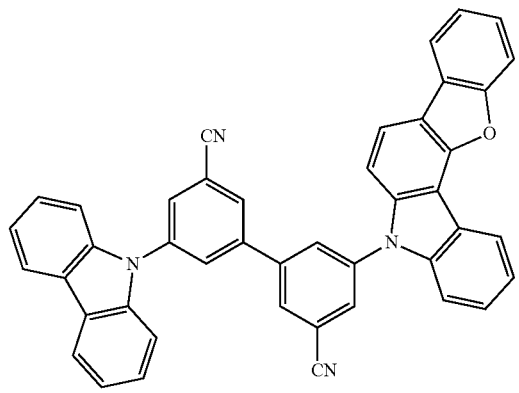

207
-continued
151
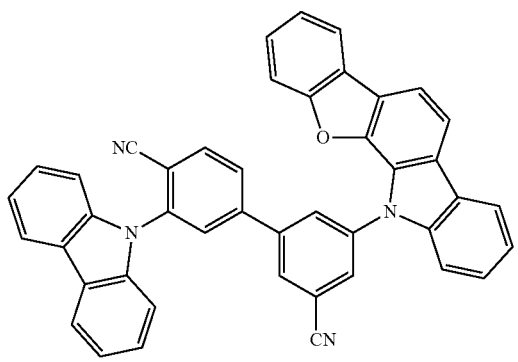
152
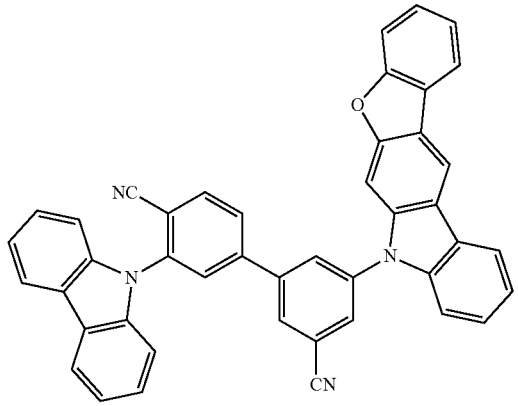
153
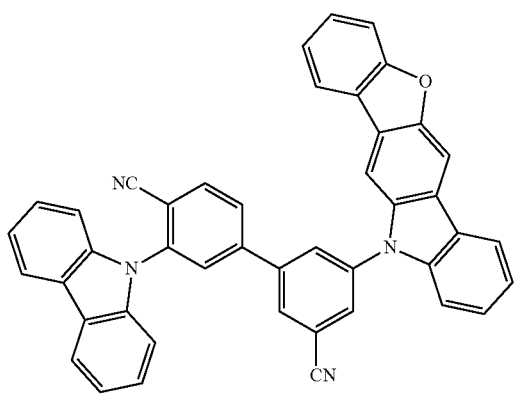
154
208
-continued
155
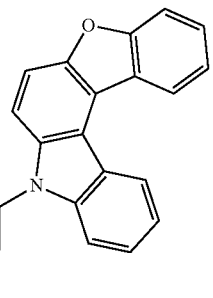
156
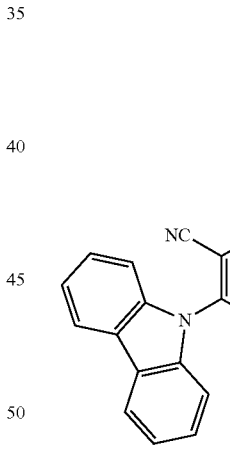
157
158
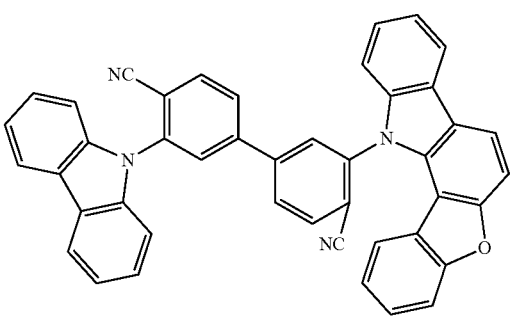

-continued
159
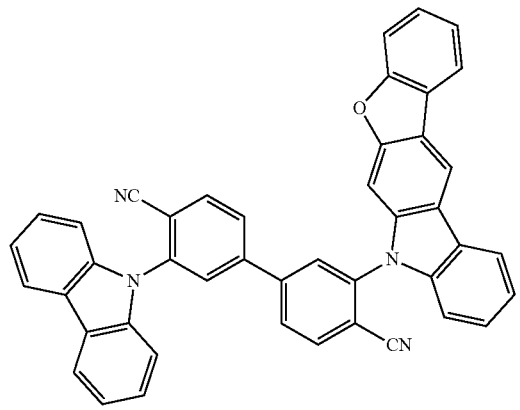
160
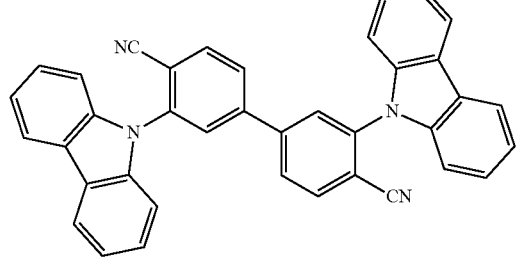
161
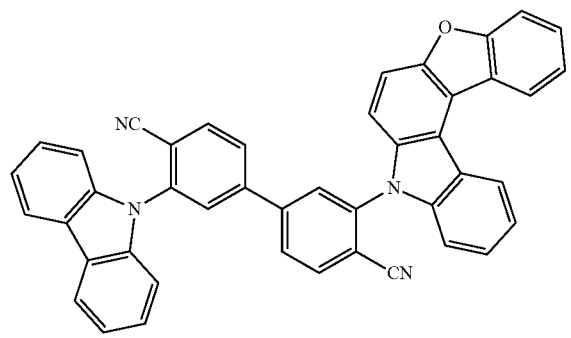
162
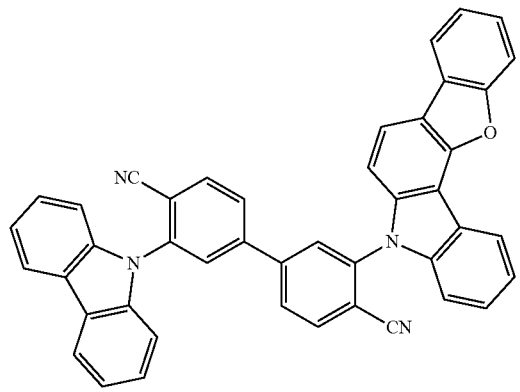
-continued
163
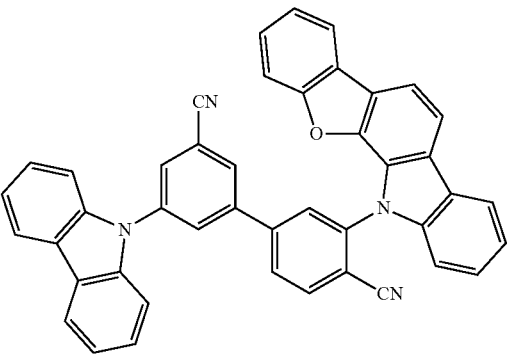
164
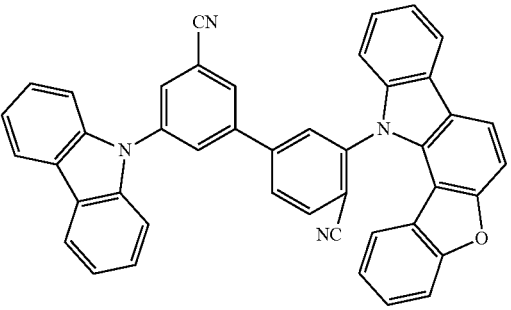
165
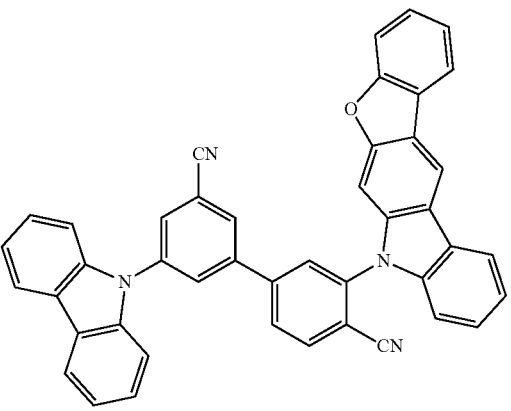
166
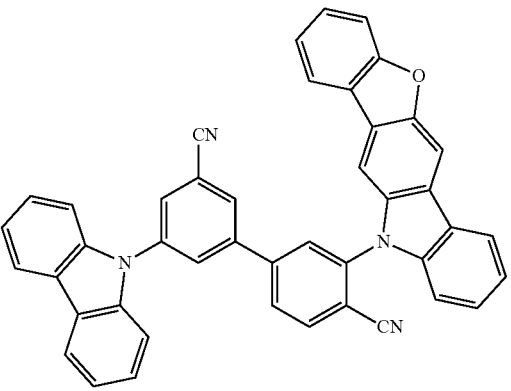

-continued
167
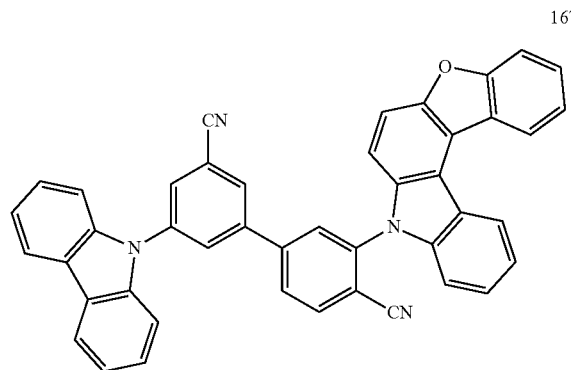
168

169

170

-continued
171

172

173
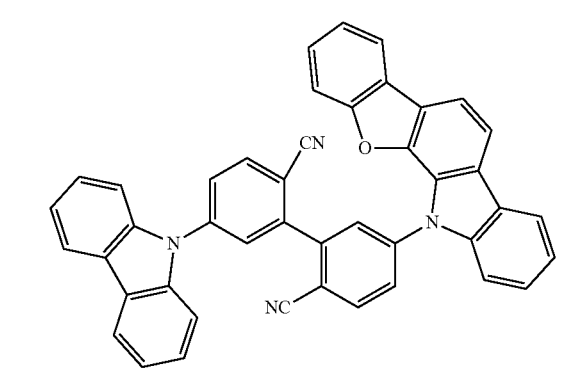
174

213
-continued
175
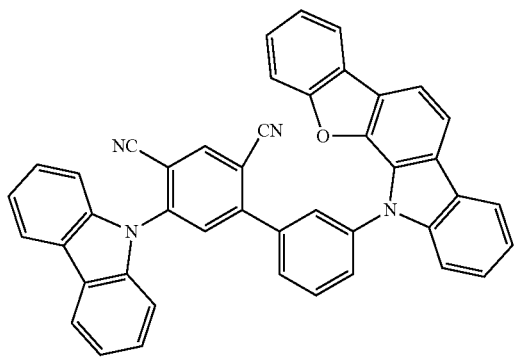
176
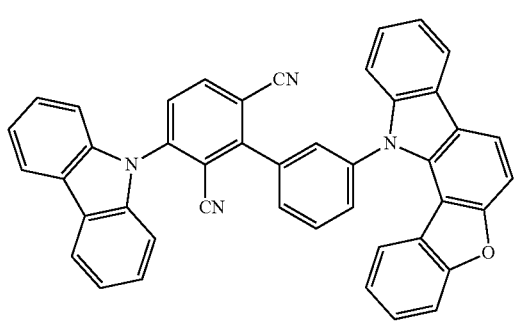
177
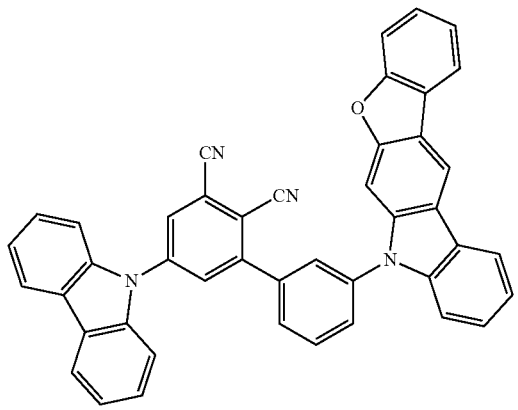
178
214
-continued
179
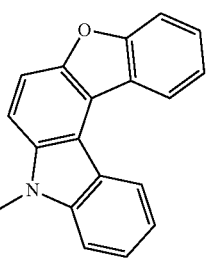
180
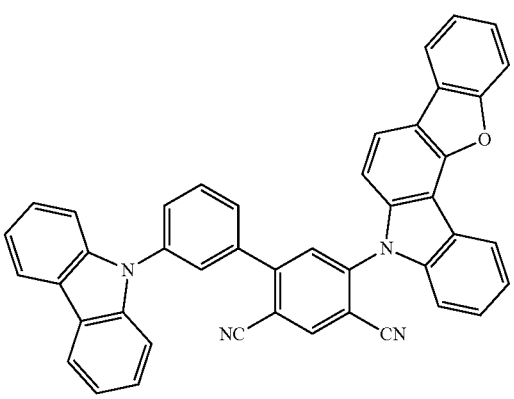
181
182
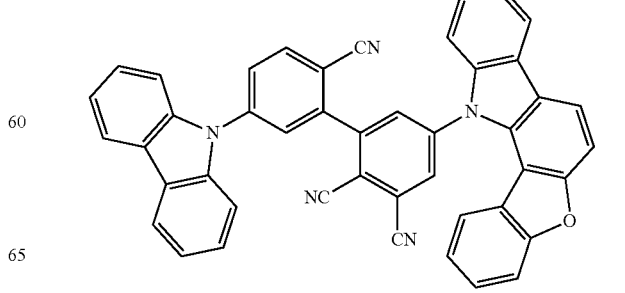

183
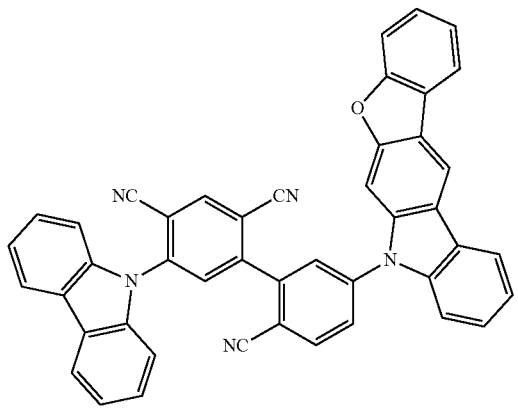
184
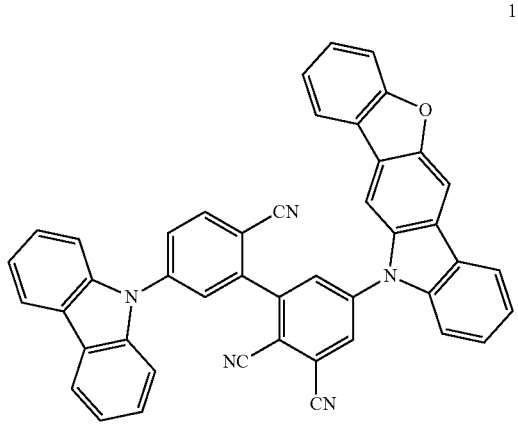
185
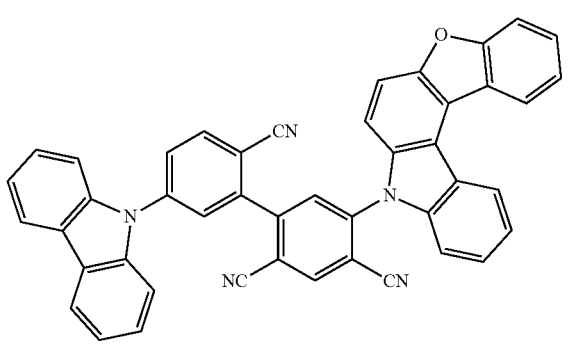
186
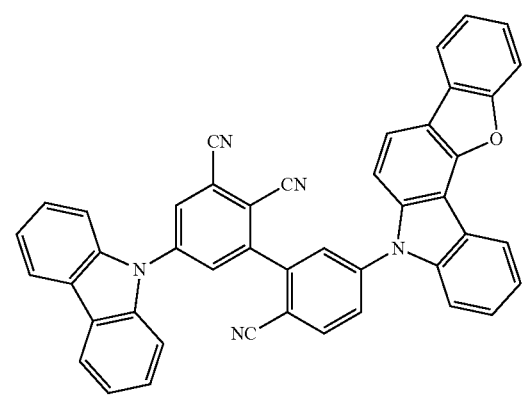
187
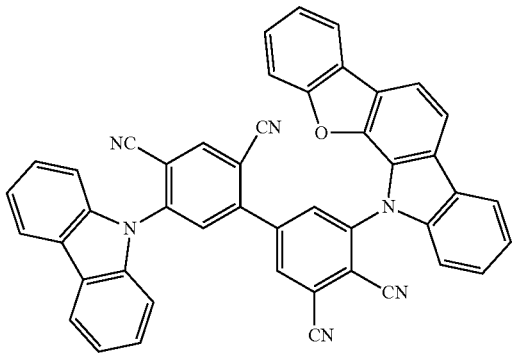
188
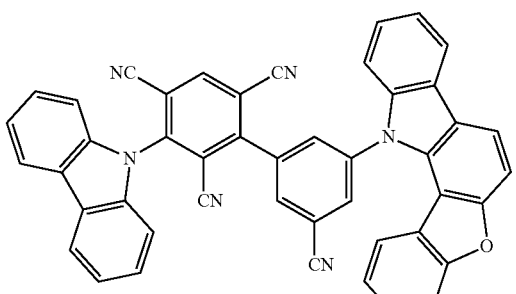
189
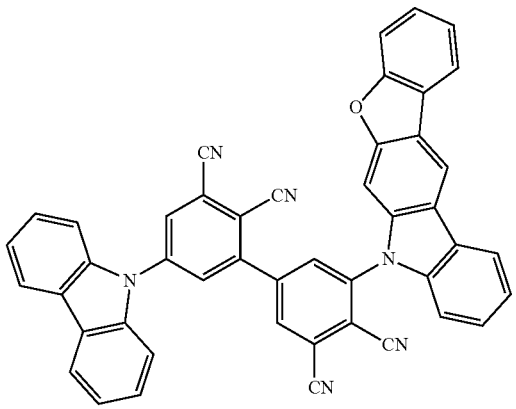
190
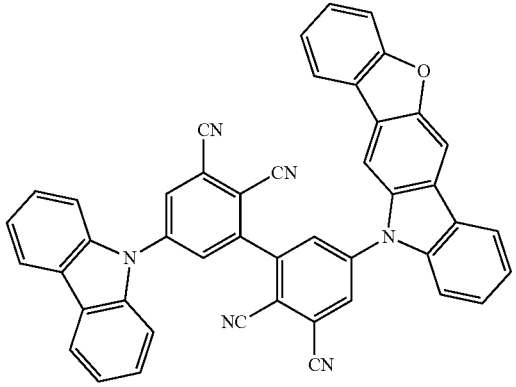

-continued
191
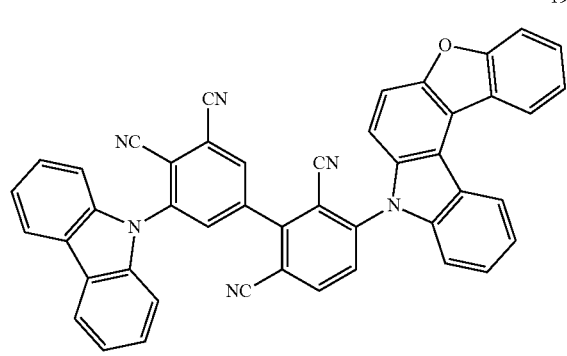
192
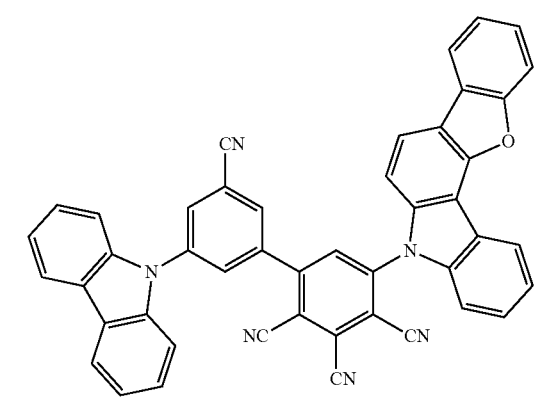
193
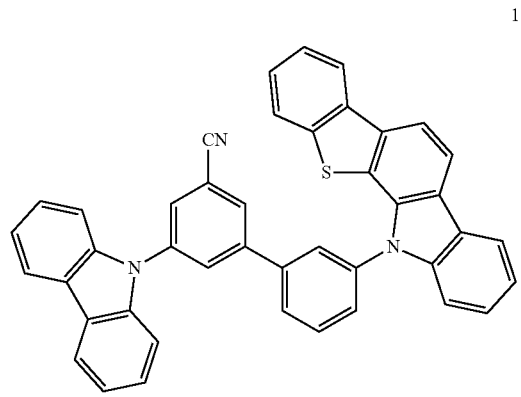
194
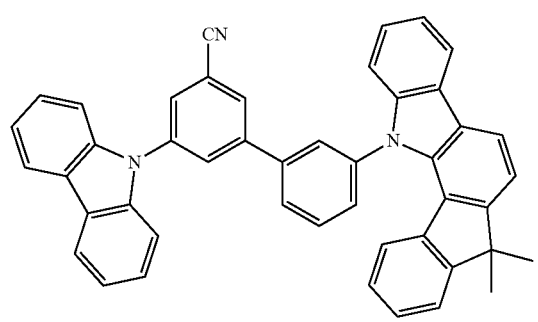
-continued
195
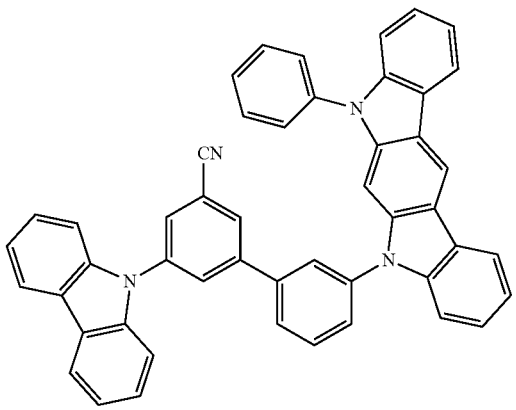
196
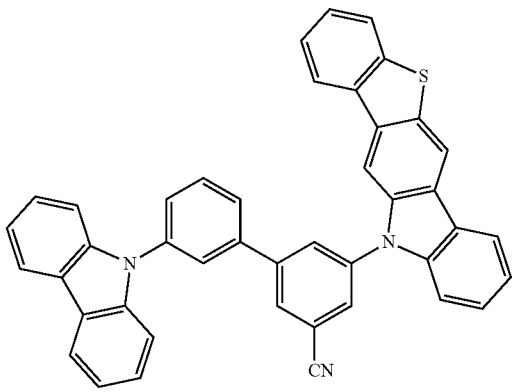
197
198
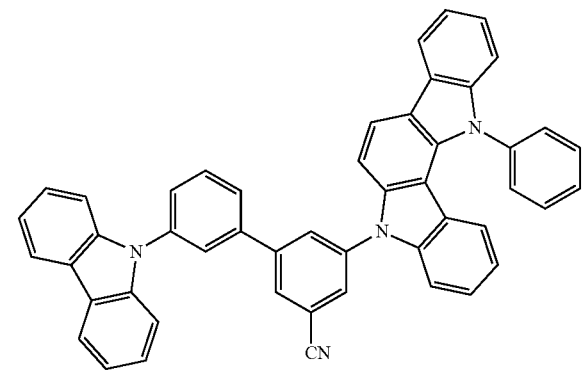

-continued
199
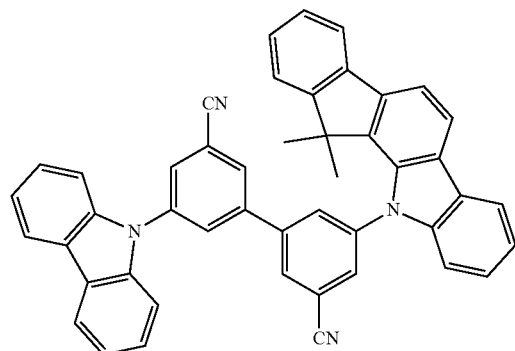
200
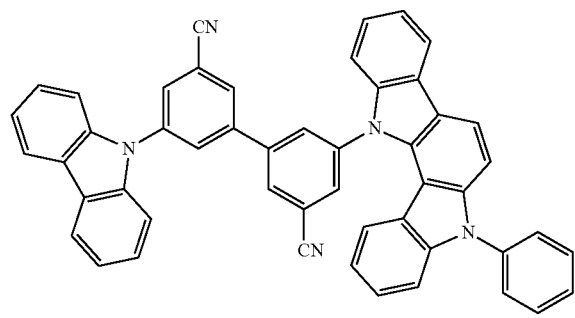
201
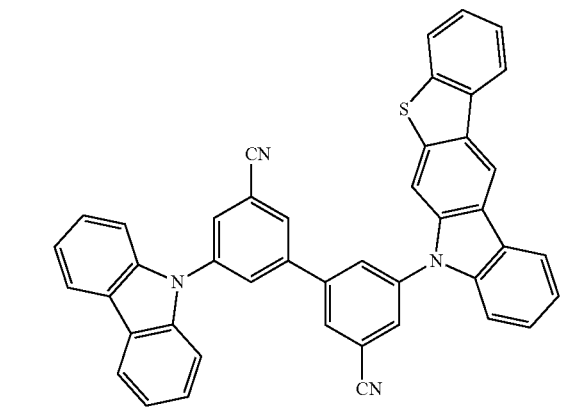
202
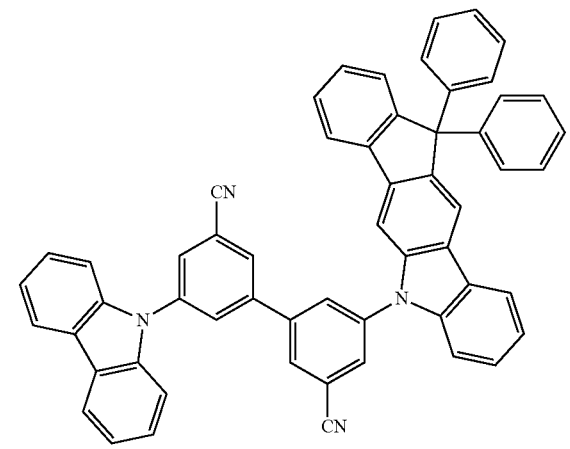
-continued
203

204

205
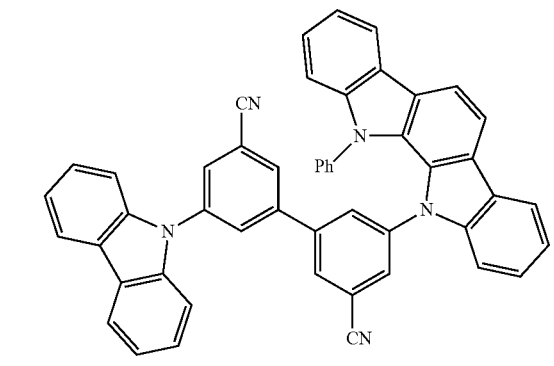
206
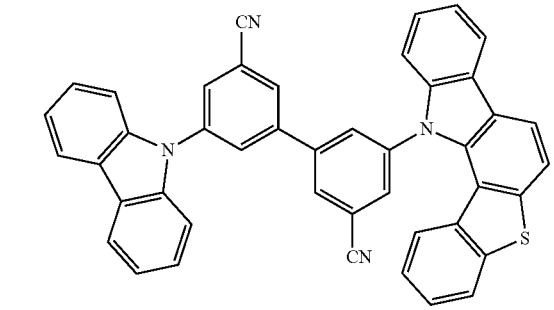

207
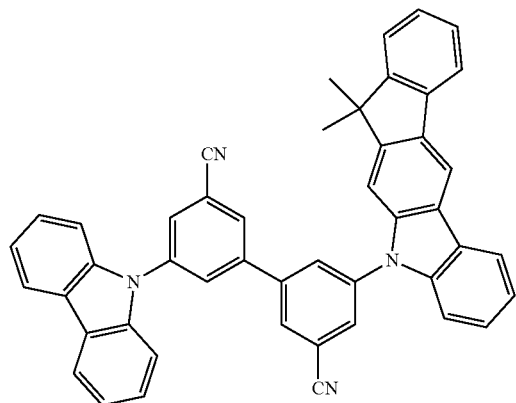
208
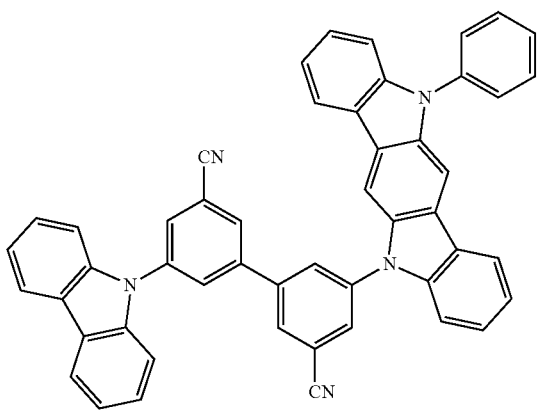
209
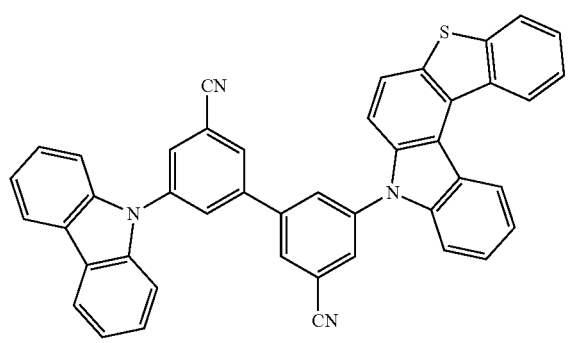
210
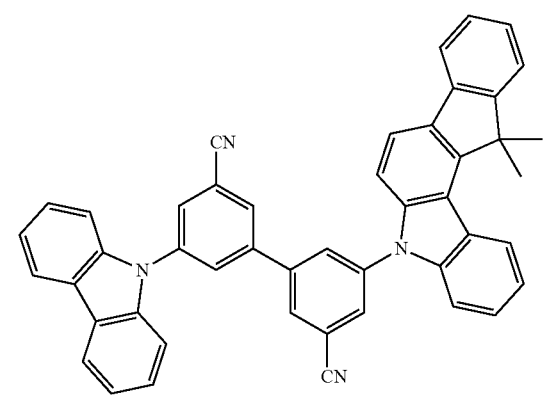
211
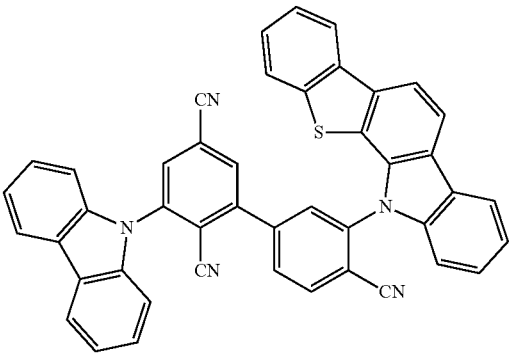
212
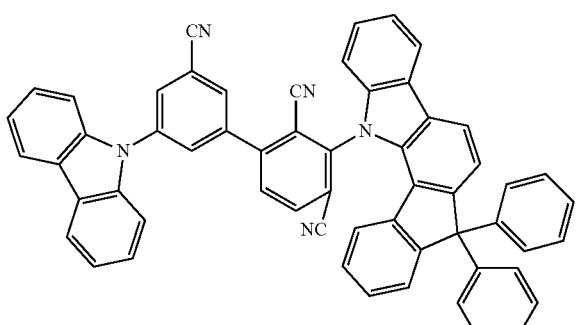
213
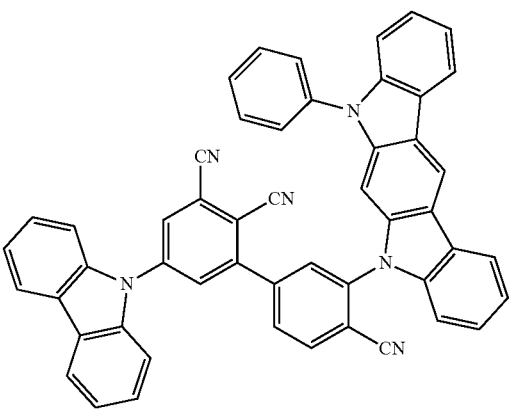
214
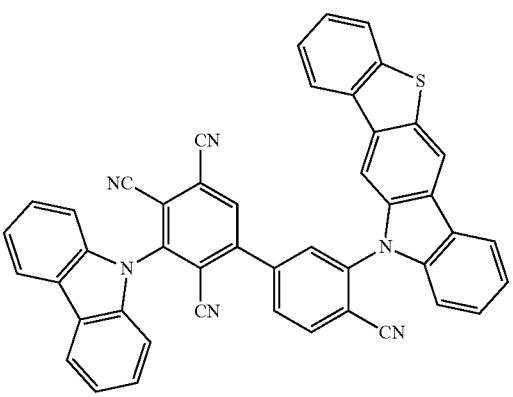

-continued
215
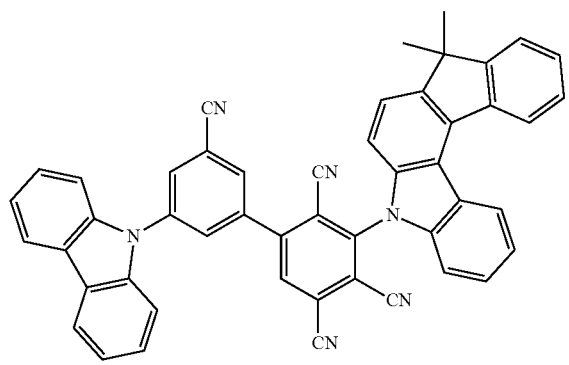
216
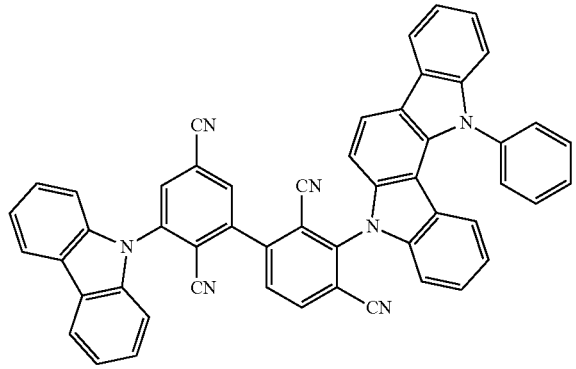
217
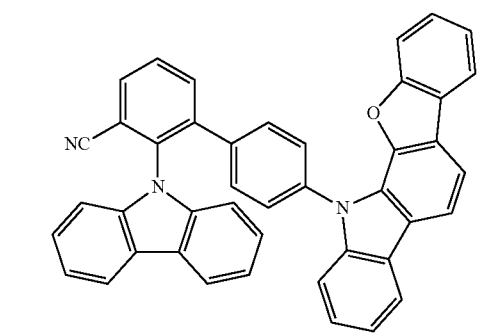
218
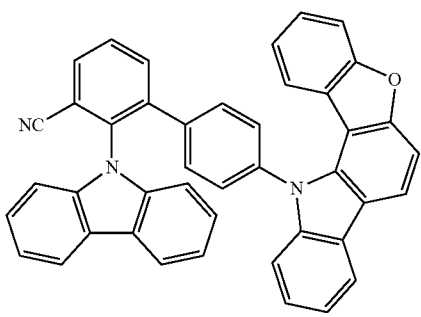
-continued
219
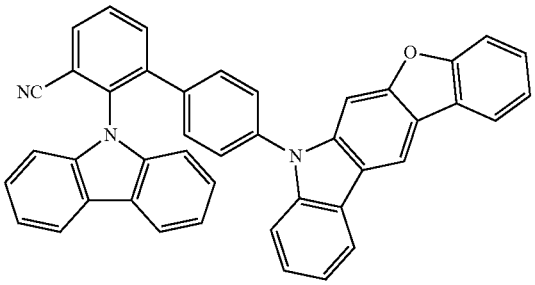
220
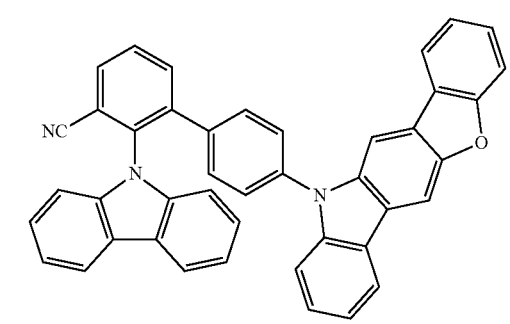
221
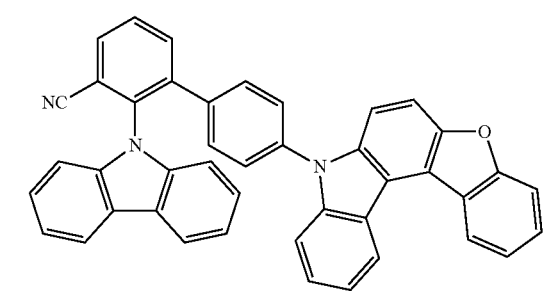
222
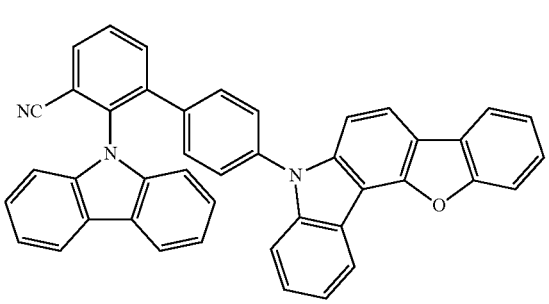
223
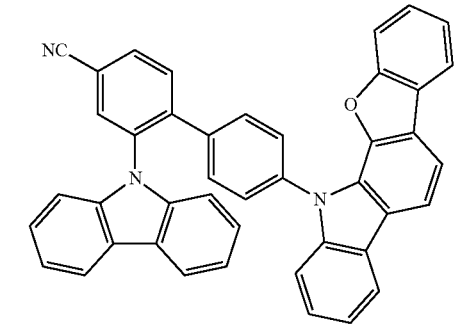

-continued
224
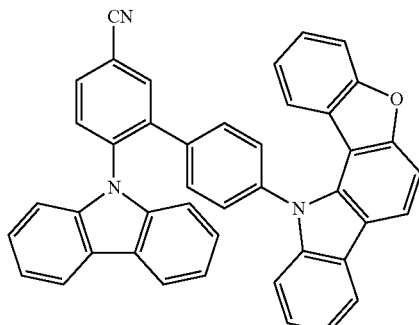
225
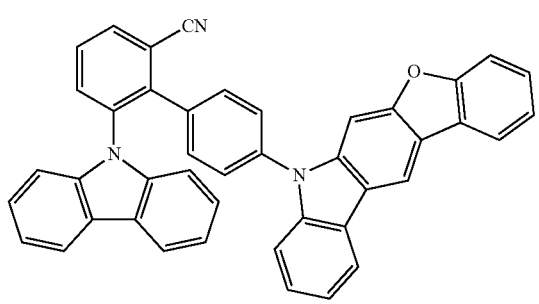
226
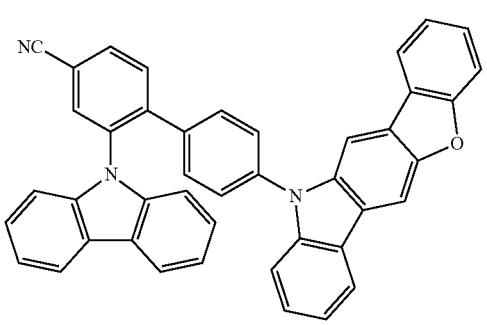
227
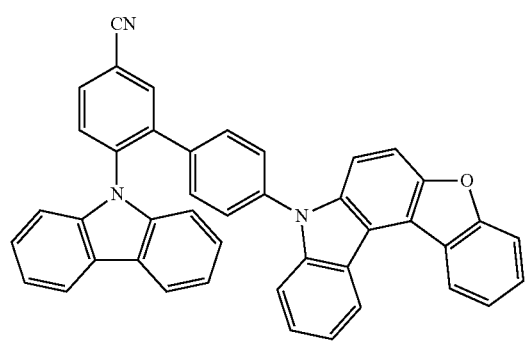
228
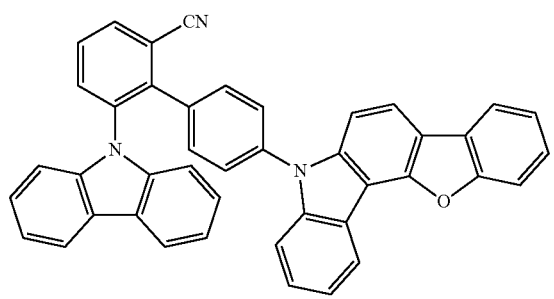
-continued
229
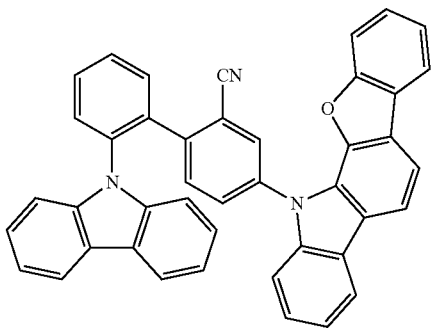
230
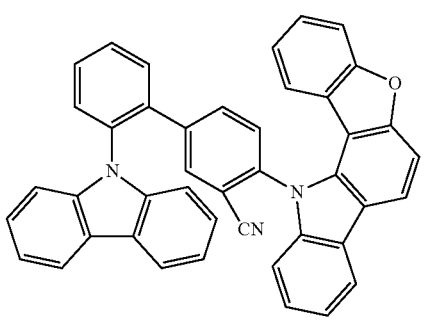
231
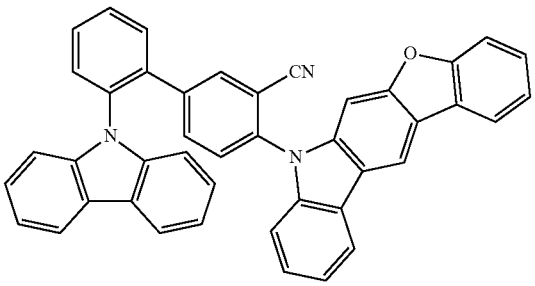
232
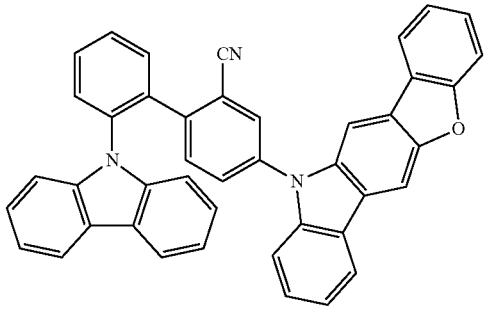
233
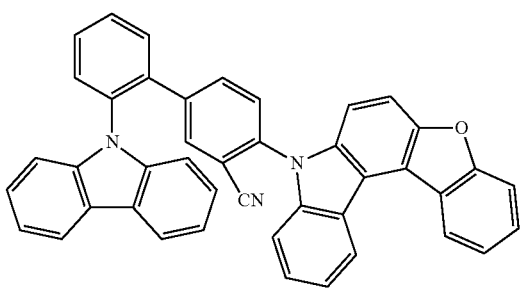

234
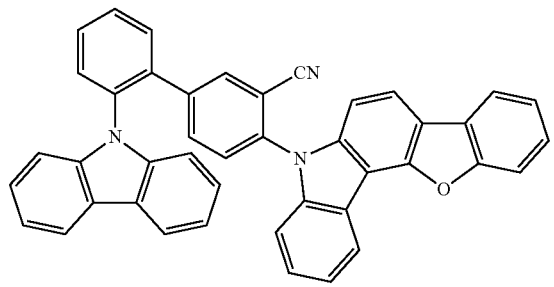
235
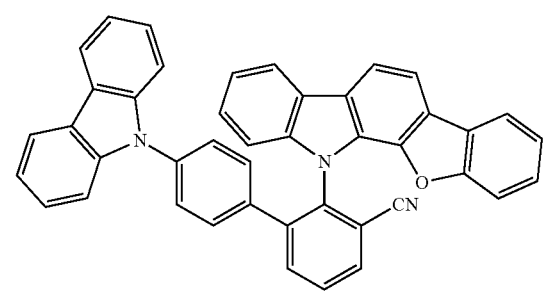
236

237
238
239
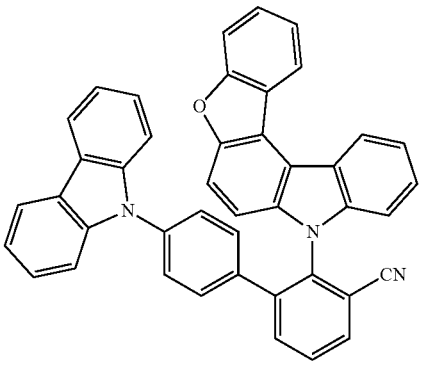
240
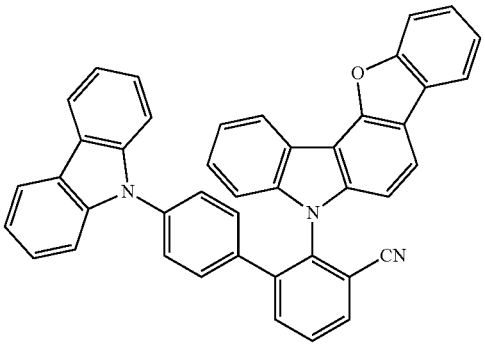
241
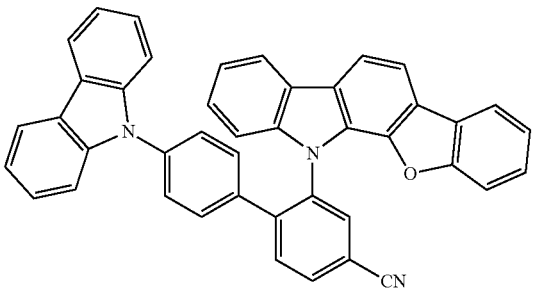
242
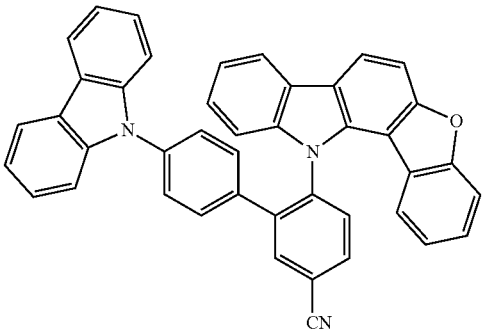

-continued
243
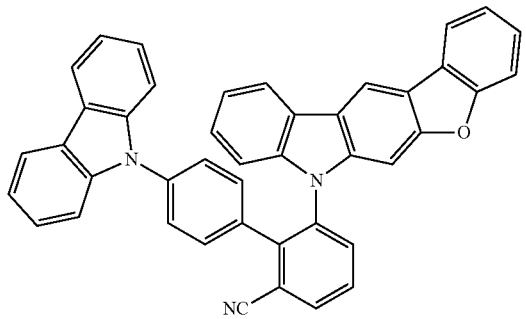
244
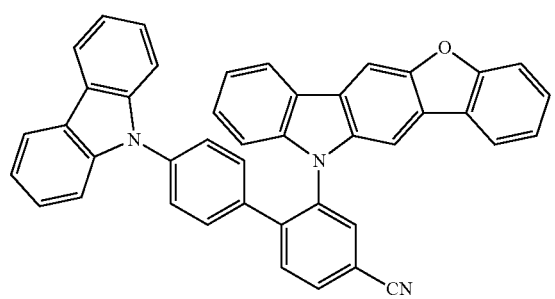
245
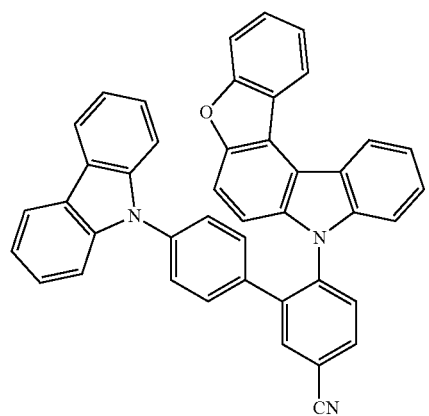
246
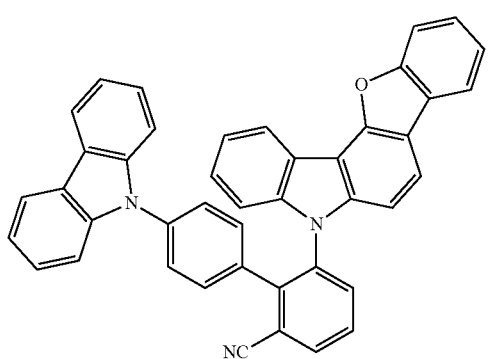
-continued
247
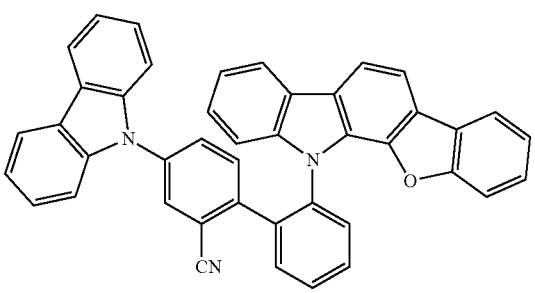
248
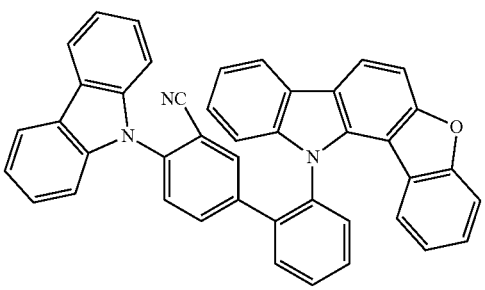
249
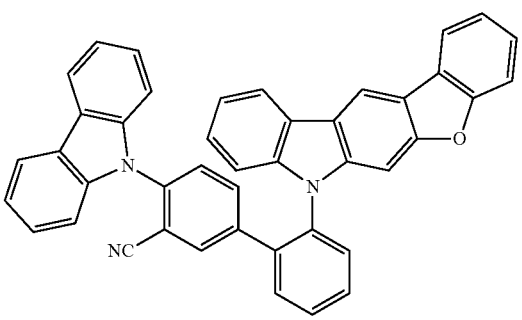
250
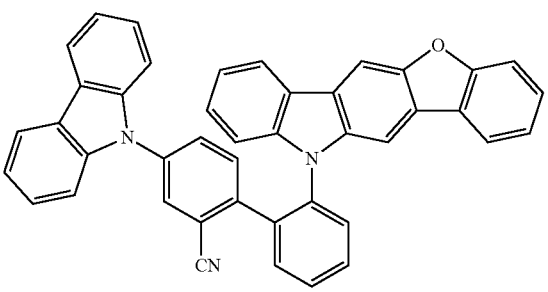
251
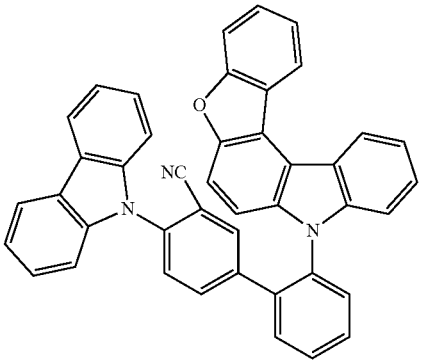

-continued
252
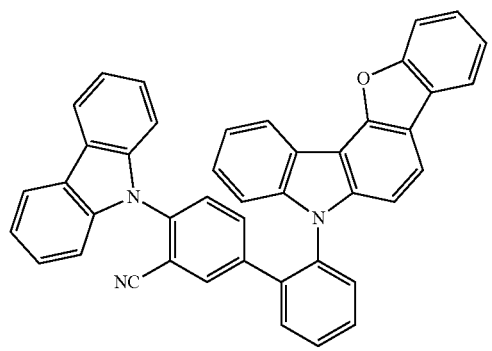
253
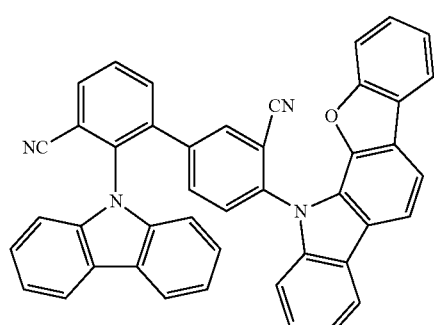
254
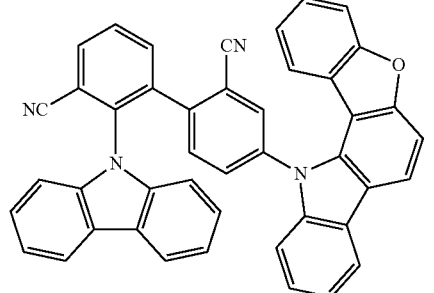
255
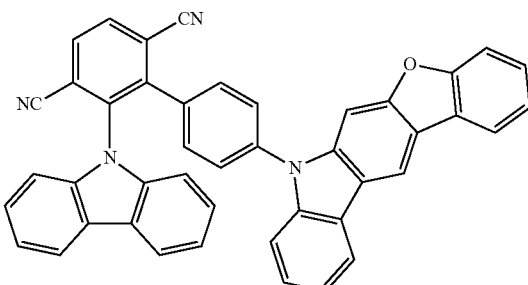
256
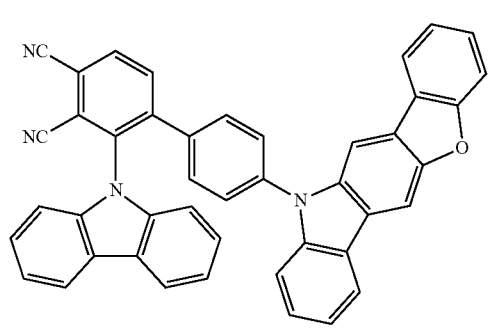
-continued
257
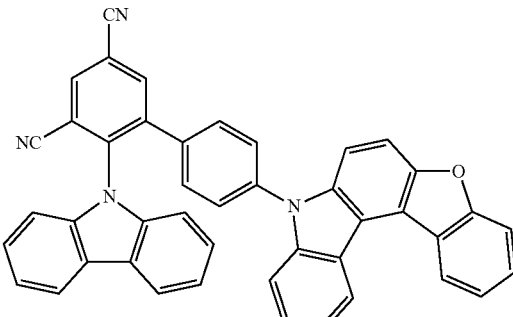
258
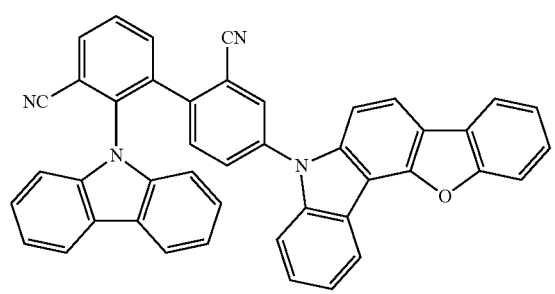
259
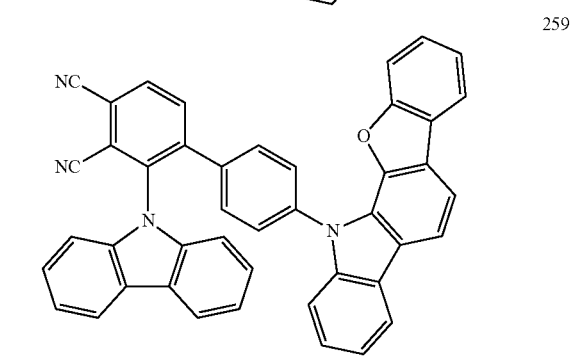
260
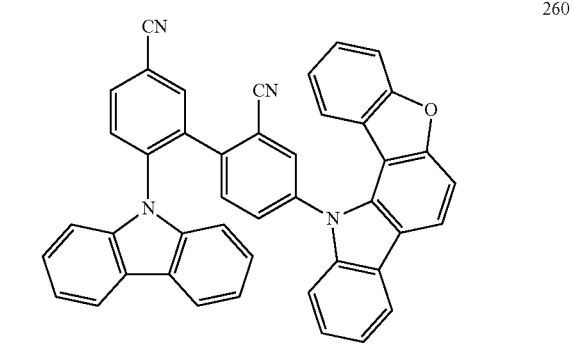
261
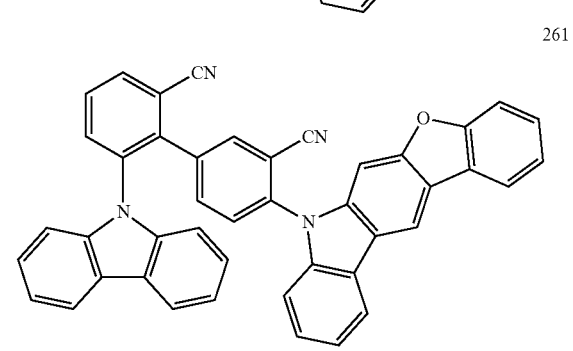

233
-continued
262
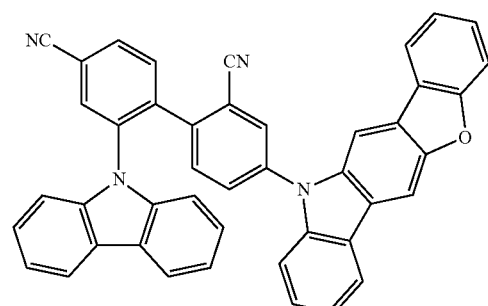
263
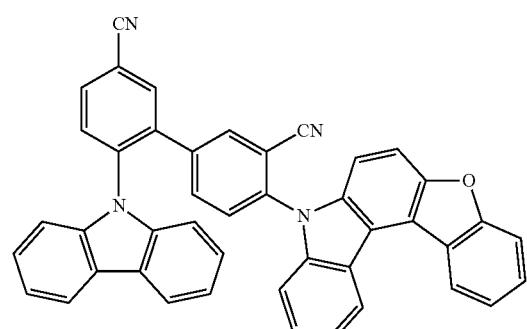
264
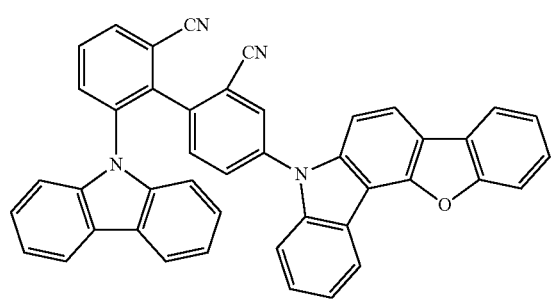
265
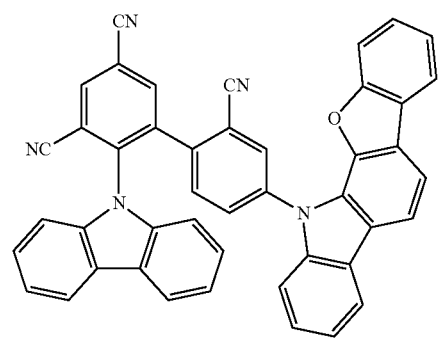
266
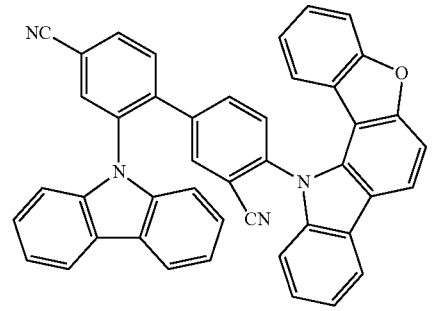
234
-continued
267
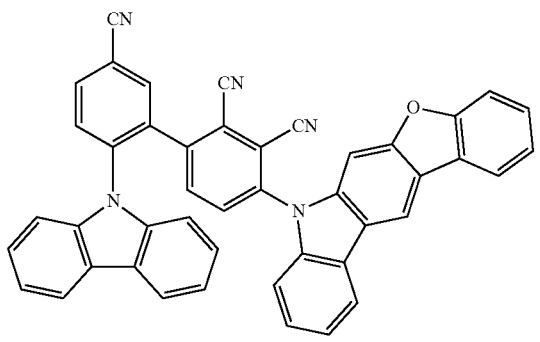
268
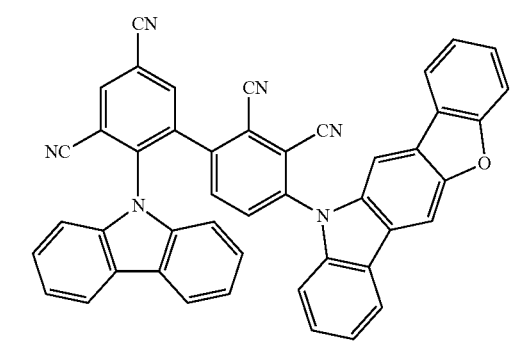
269
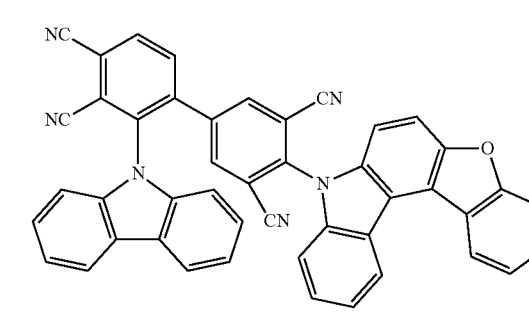
270
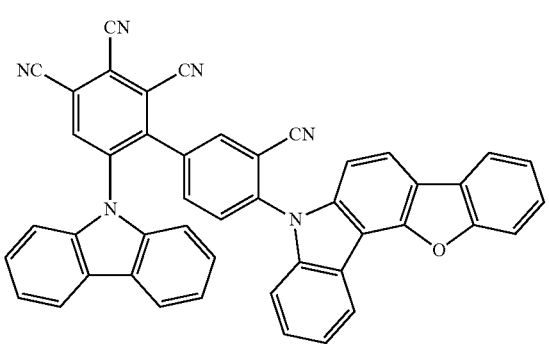

271
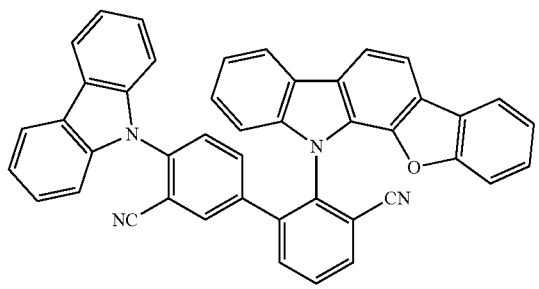
272
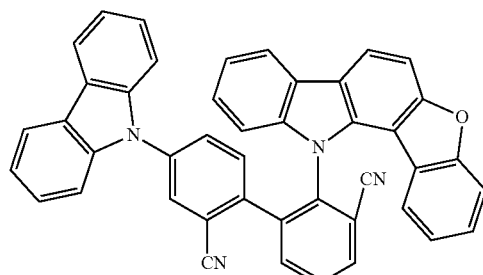
273
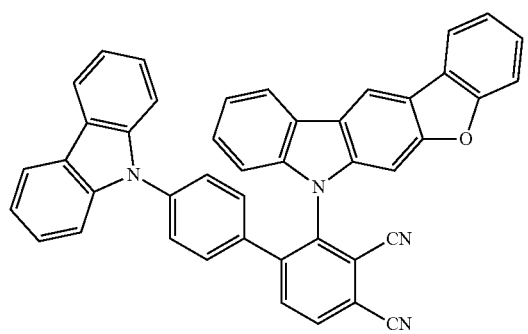
274
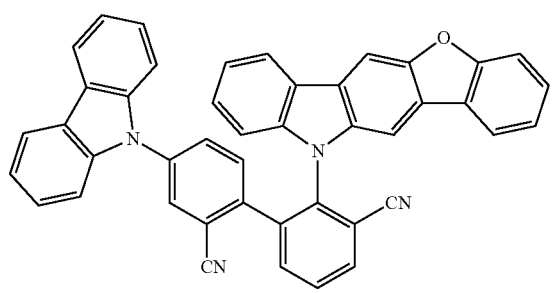
275
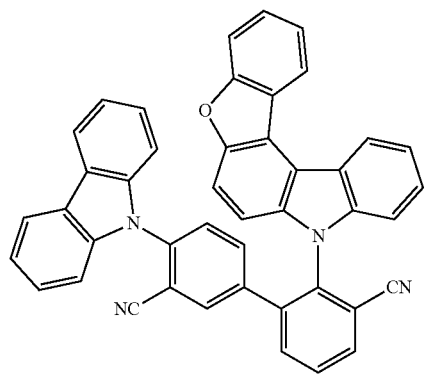
276
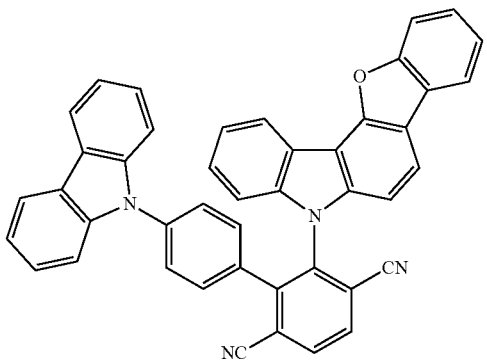
277
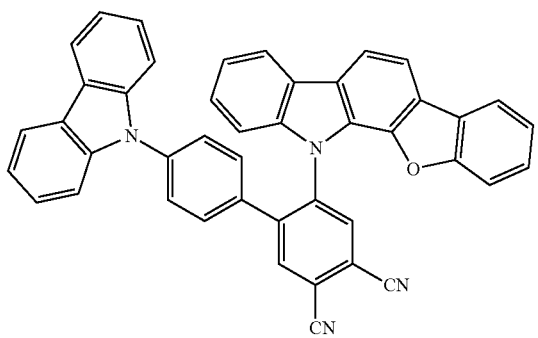
278
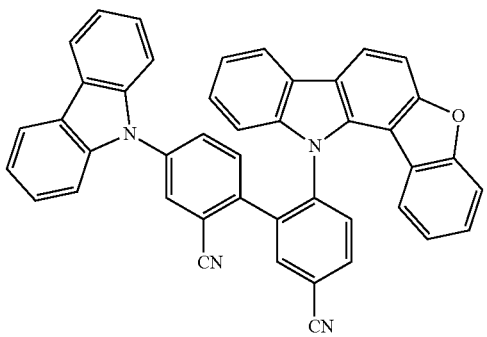
279
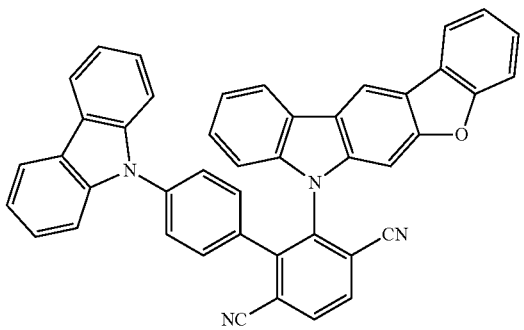

-continued
280
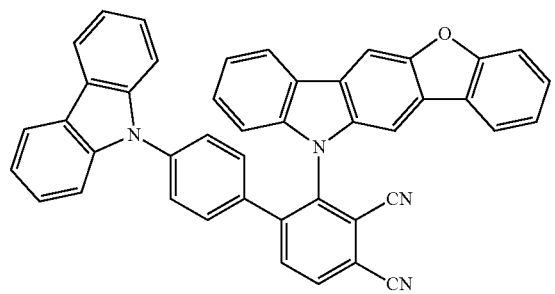
281
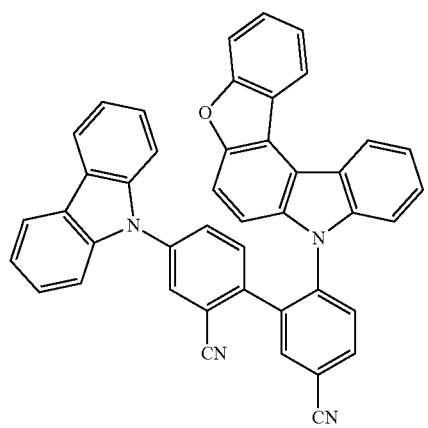
282
283
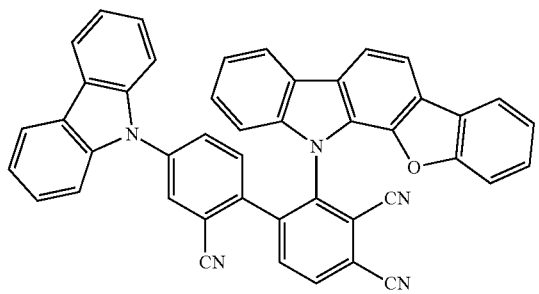
-continued
284
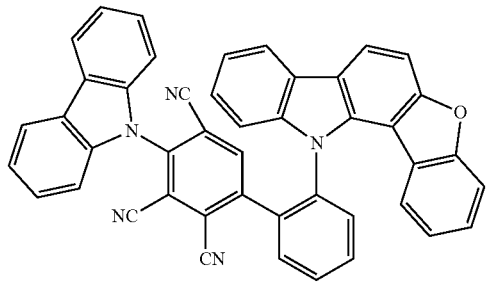
285
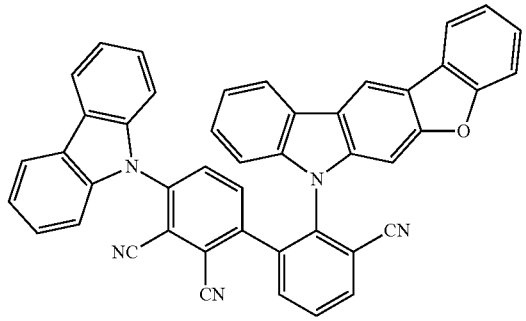
286
287
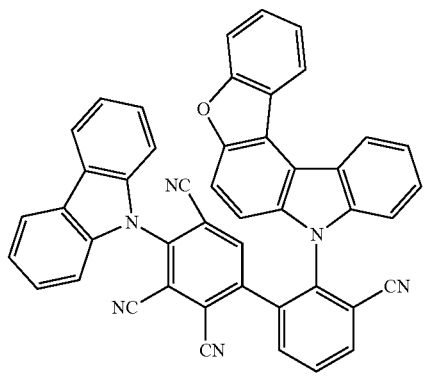

288
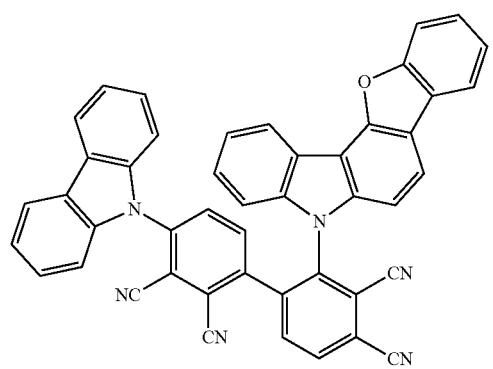
292
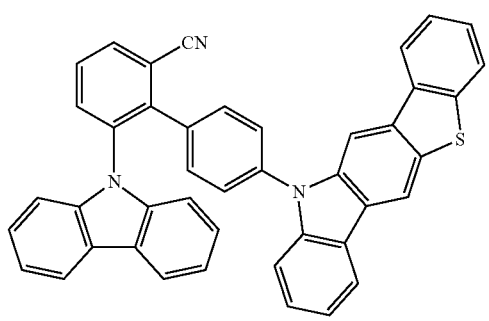
289
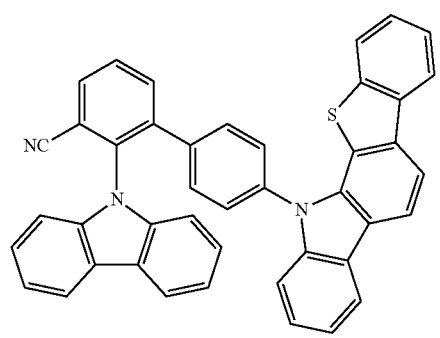
293
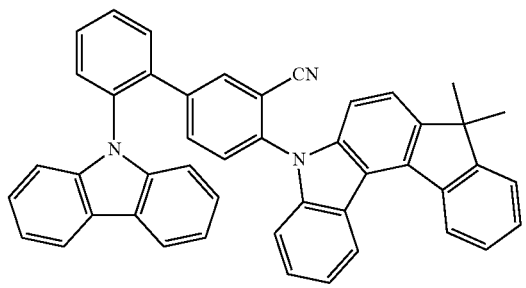
290
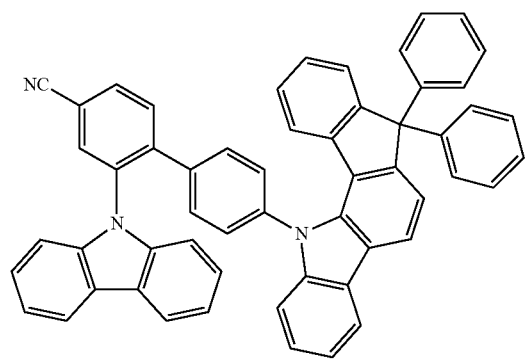
294
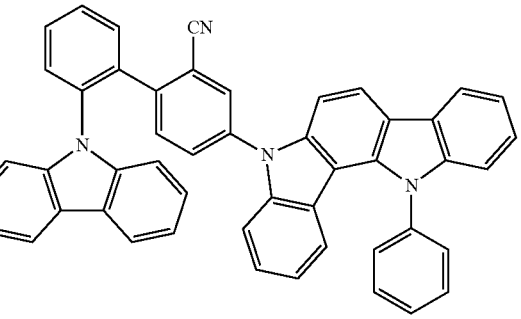
291
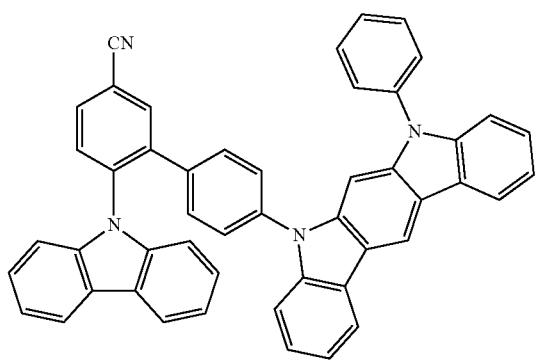
295
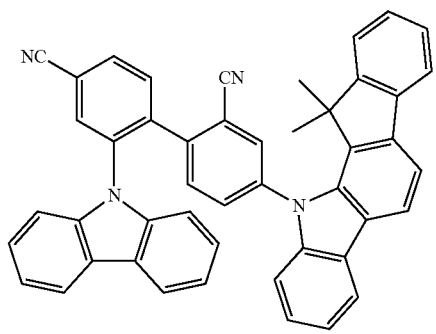

296
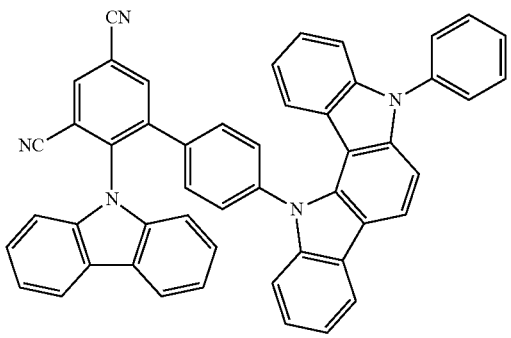
297
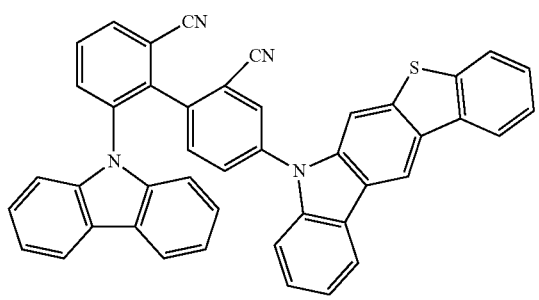
298
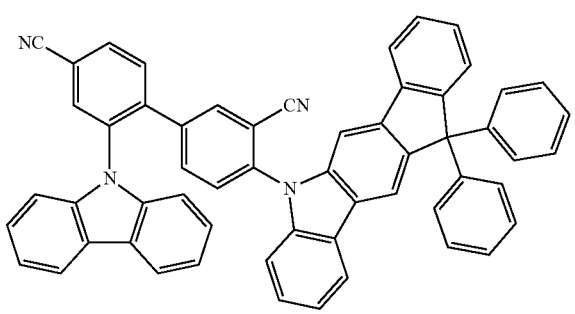
299
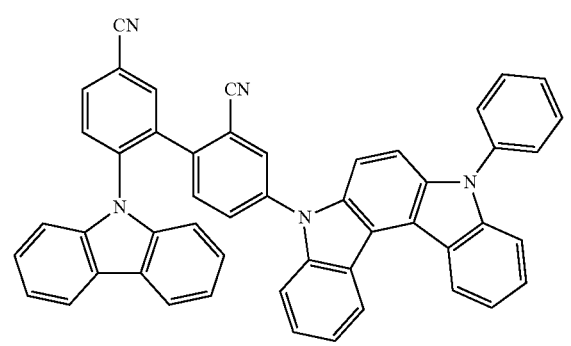
300
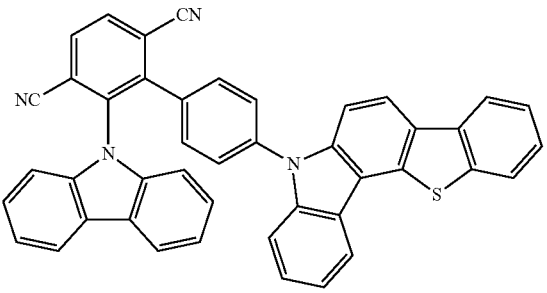
301
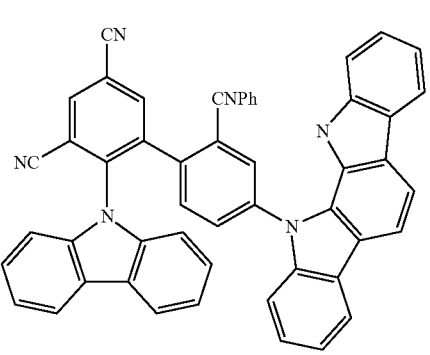
302
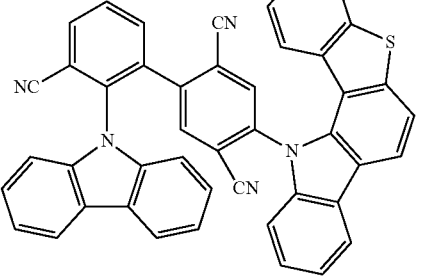
303
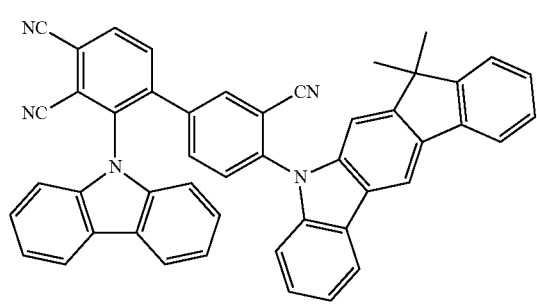
304
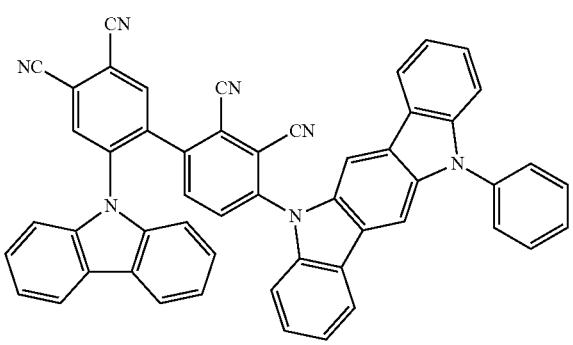

243
-continued
305
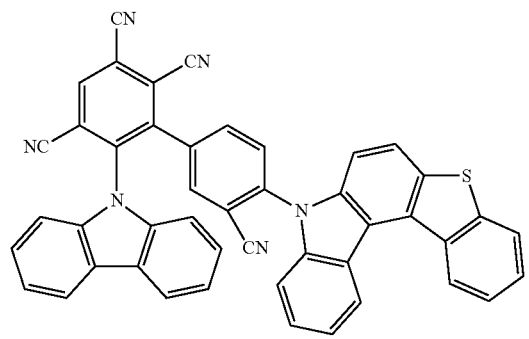
306
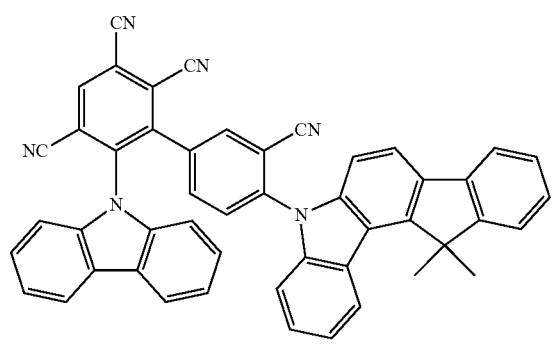
307
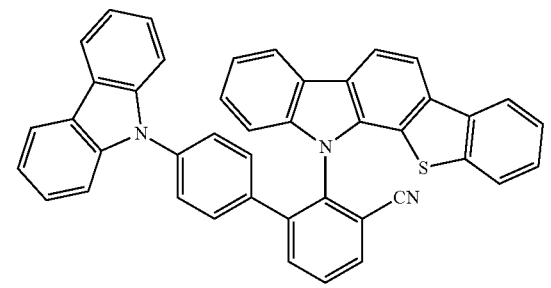
308
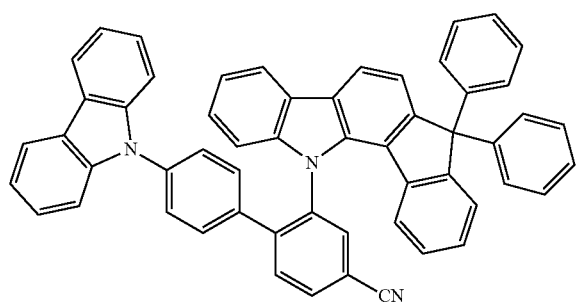
244
-continued
309
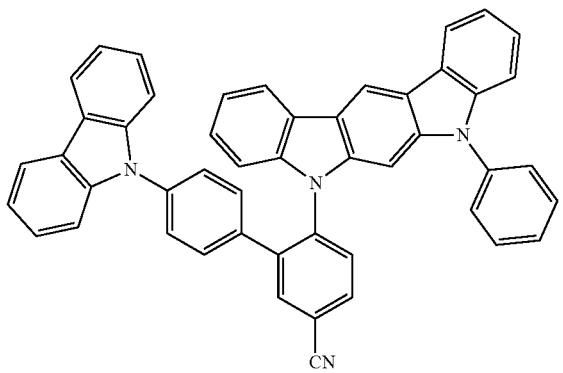
310

311
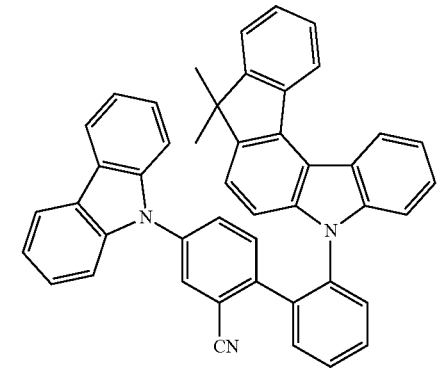
312
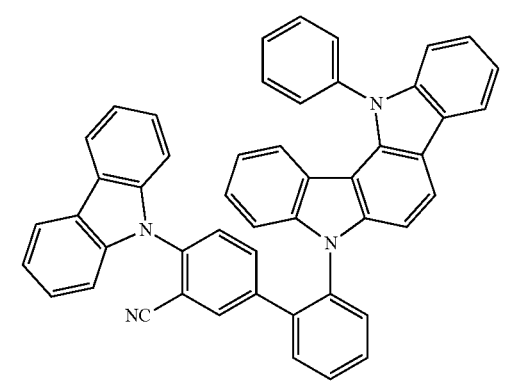

-continued
313
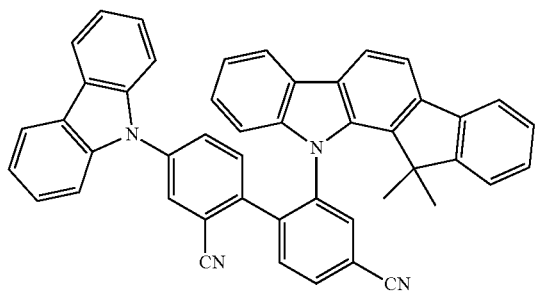
314
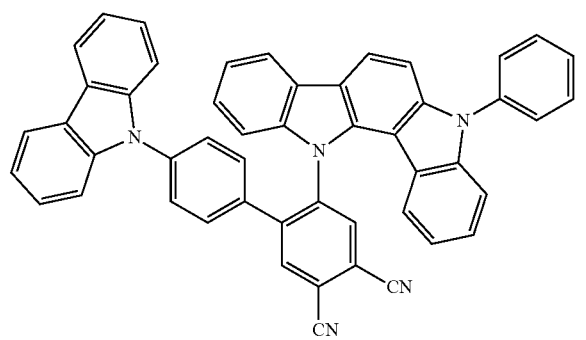
315
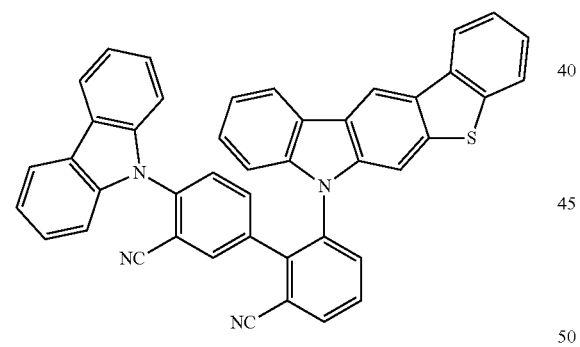
316
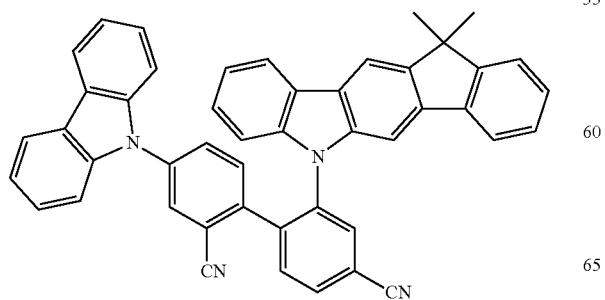
-continued
317
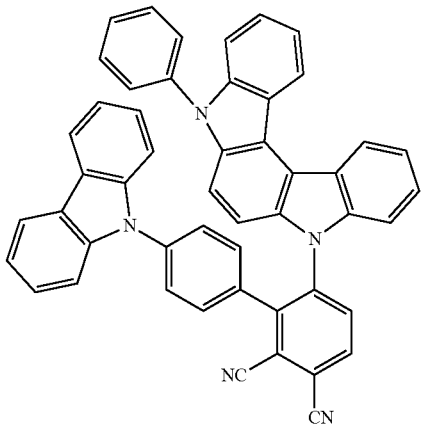
318
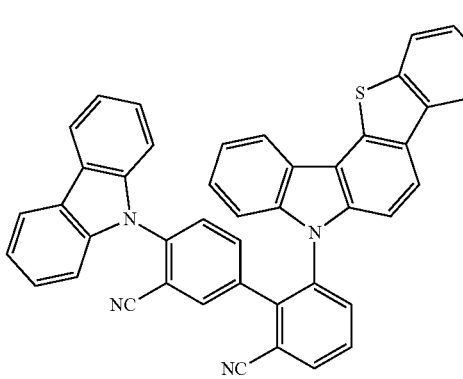
319
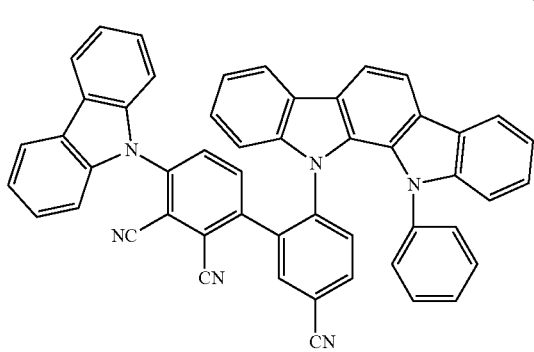
320
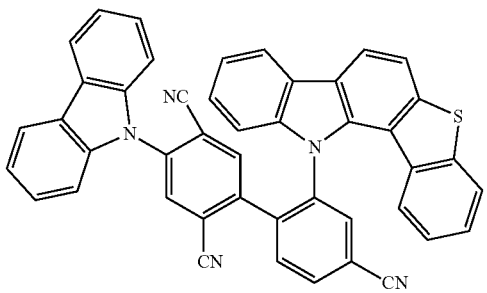

-continued
321
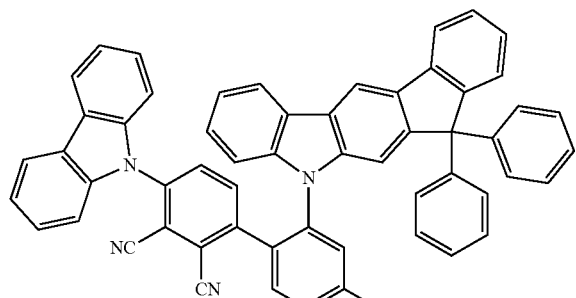
322
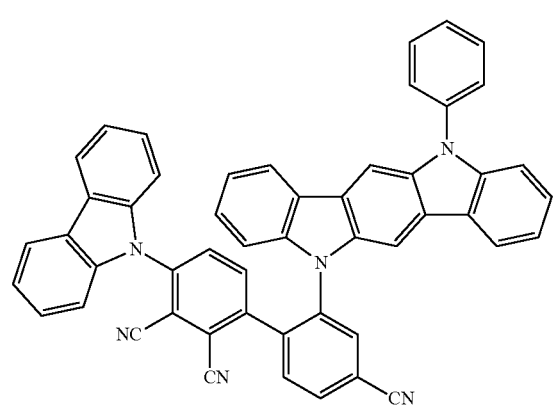
323
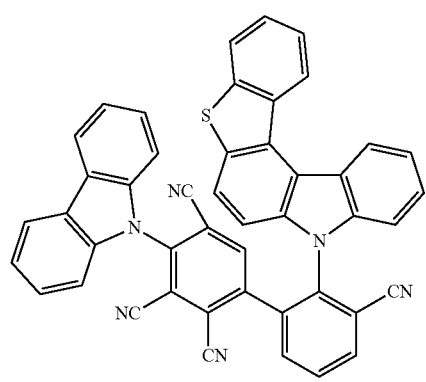
324
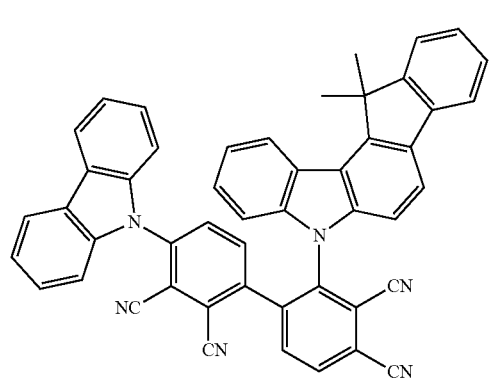
-continued
325
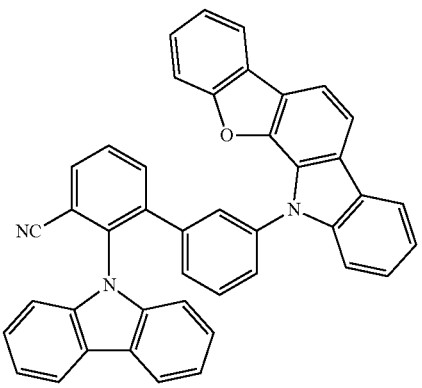
326
327
328

329
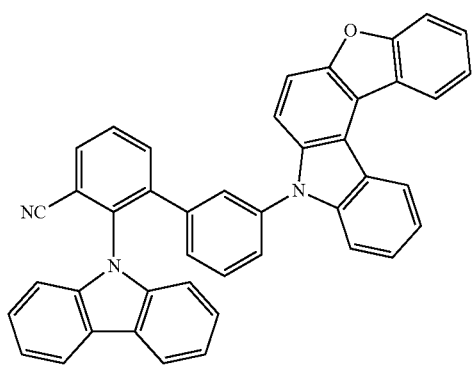
330
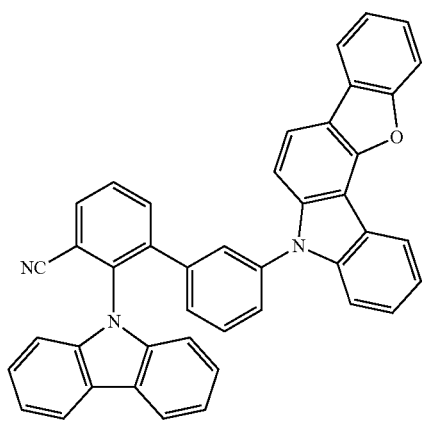
331
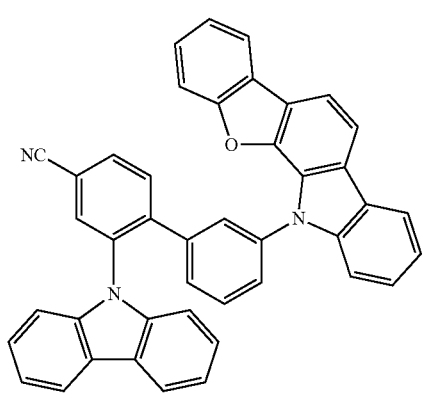
332
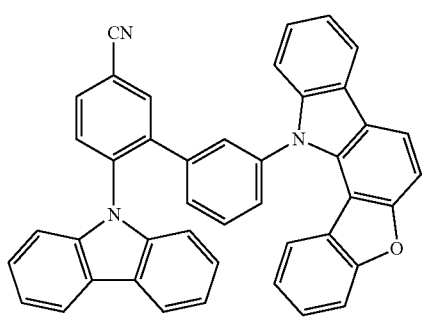
333
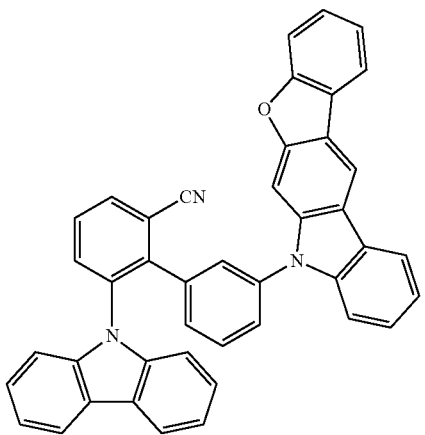
334
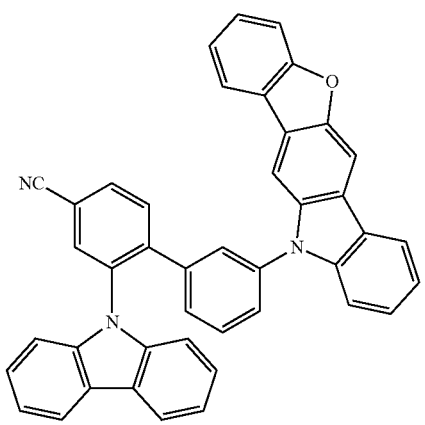
335
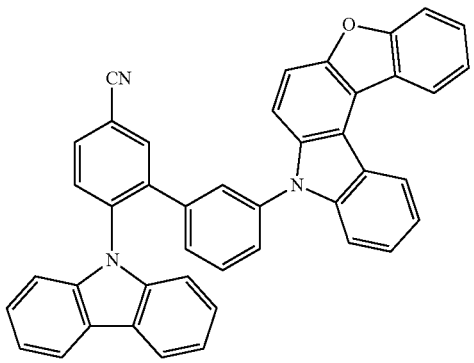
336
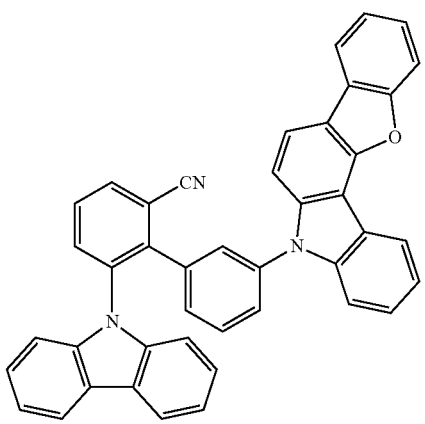

337 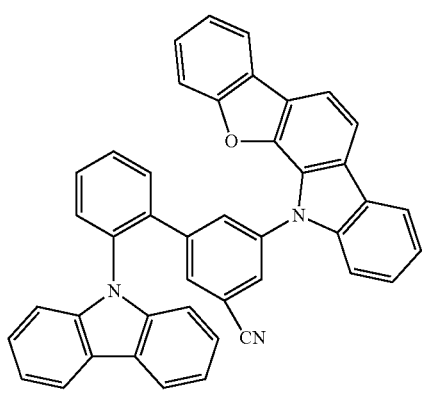
338 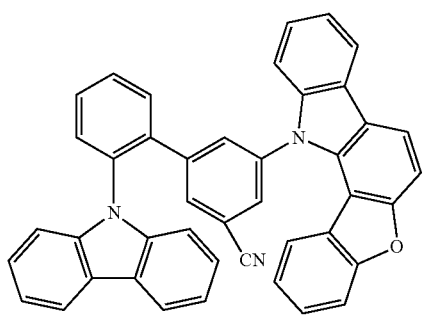
339 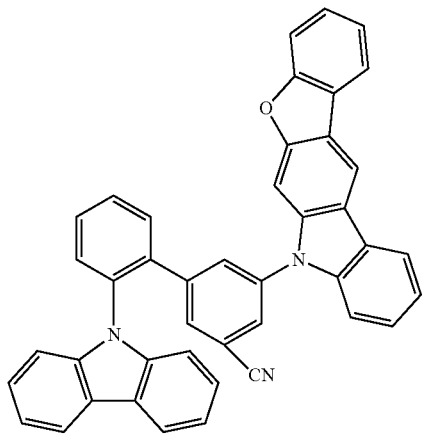
340 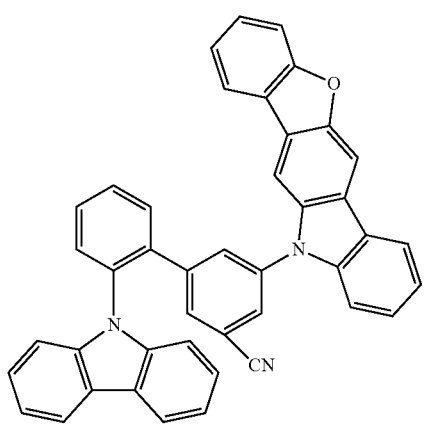
341 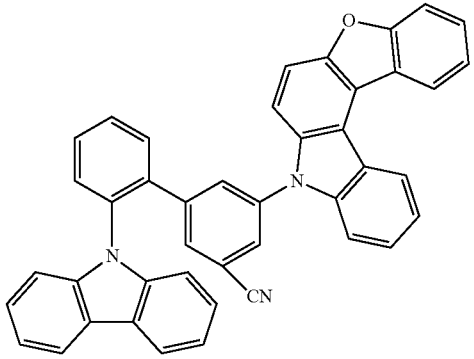
342 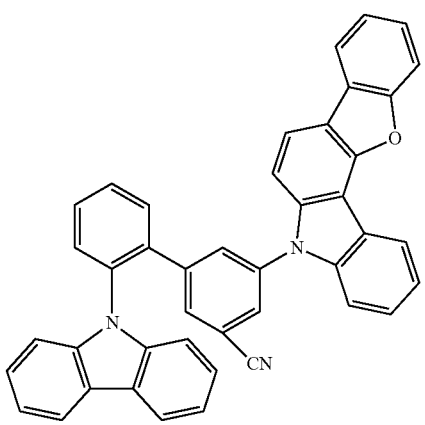
343 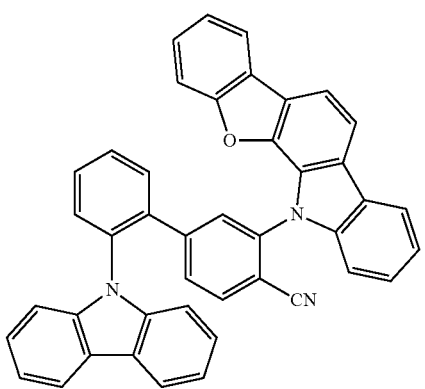
344 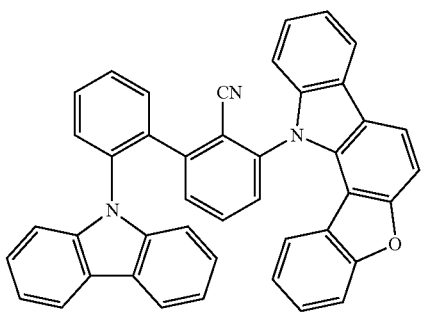

-continued
345
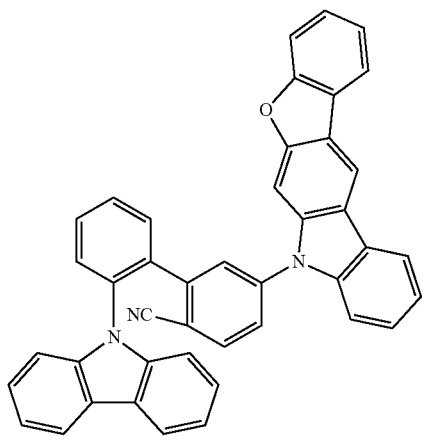
346
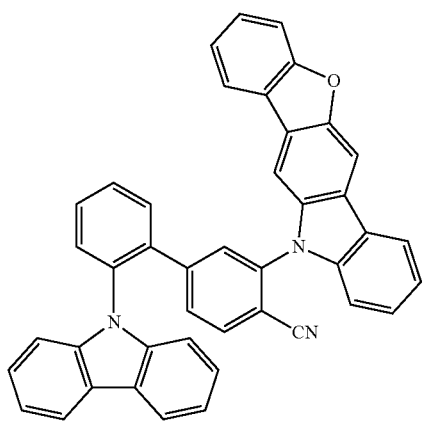
347
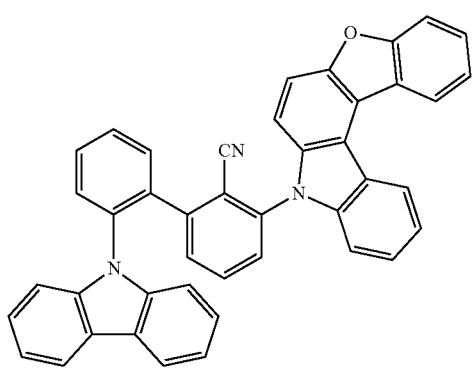
348
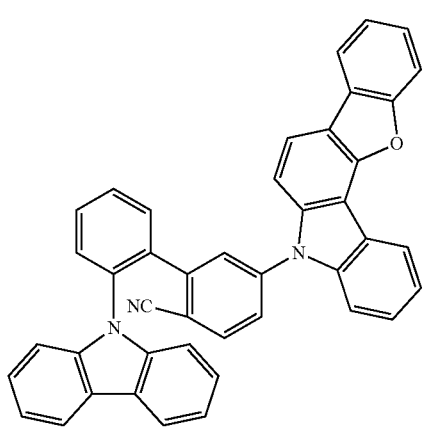
-continued
349
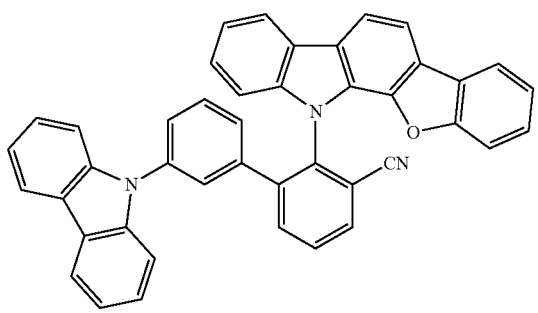
350
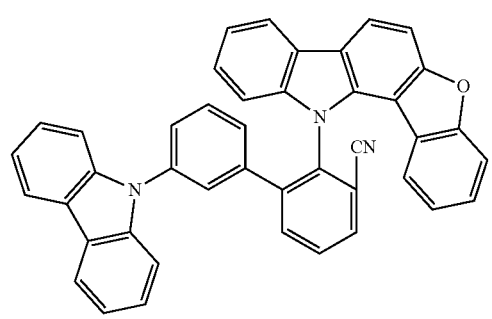
351
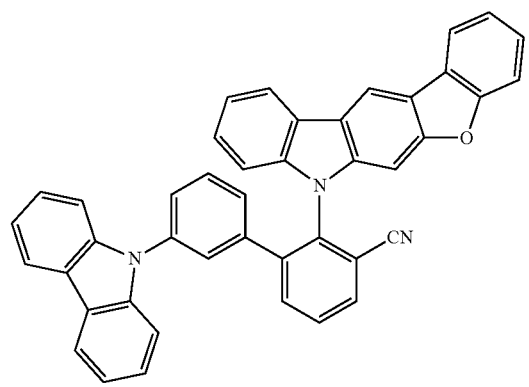
352
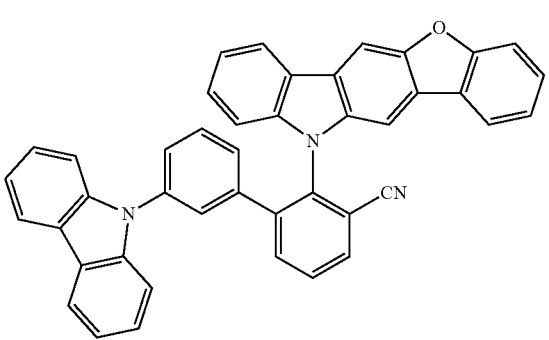

353
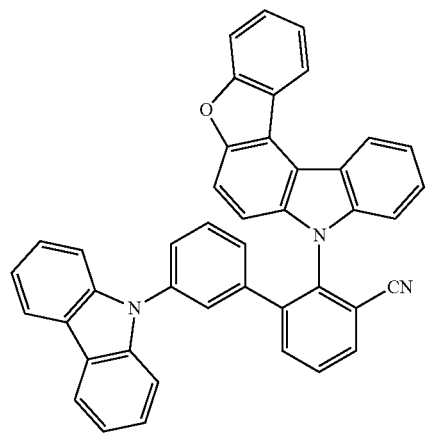
354
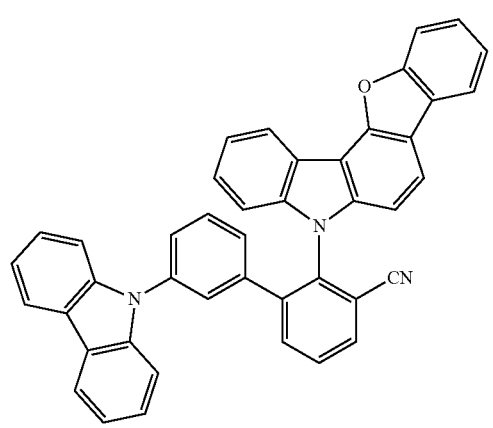
355
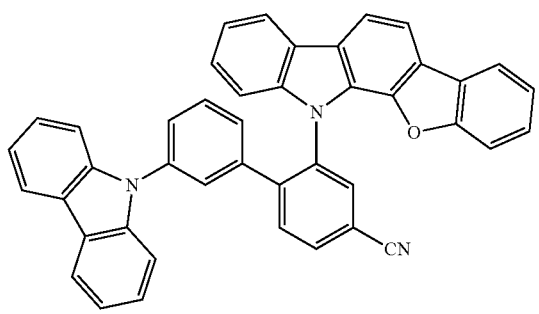
356
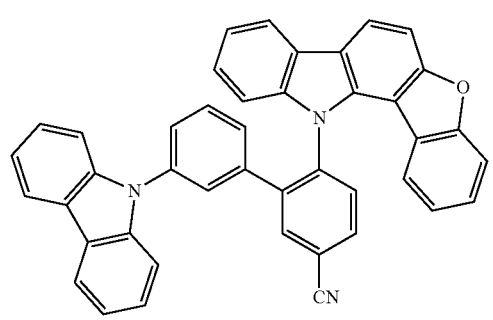
357
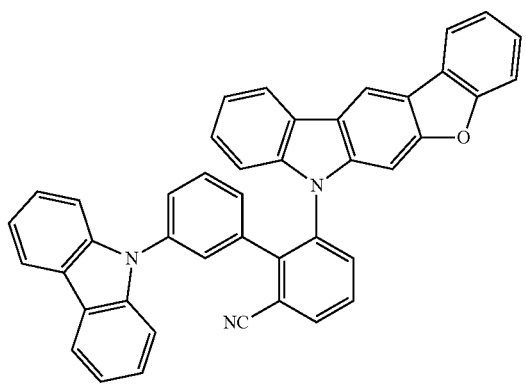
358
359
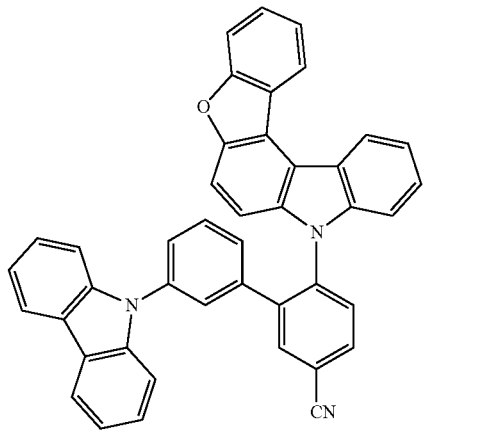
360
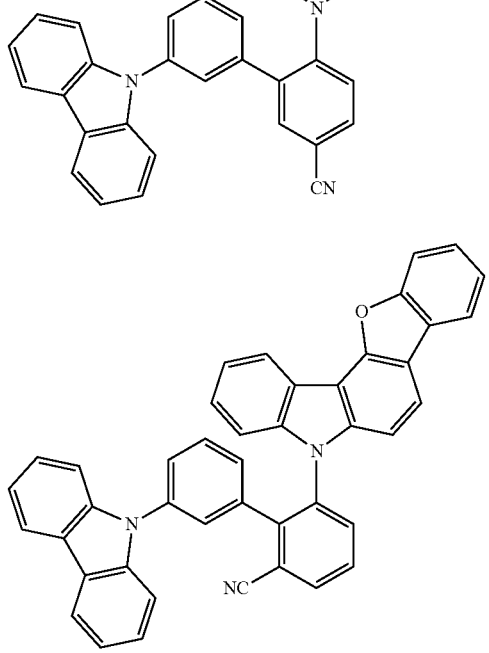

-continued
361
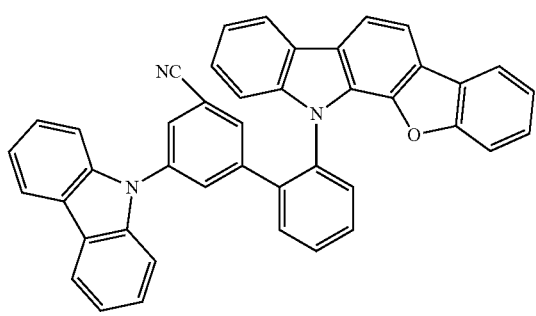
362
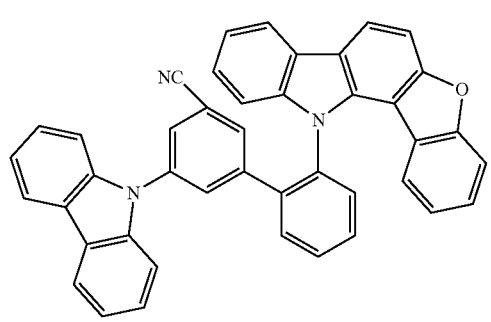
363
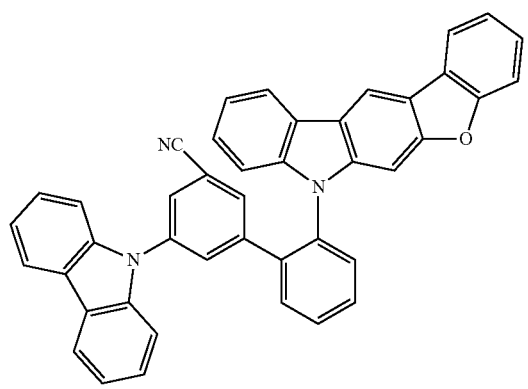
364
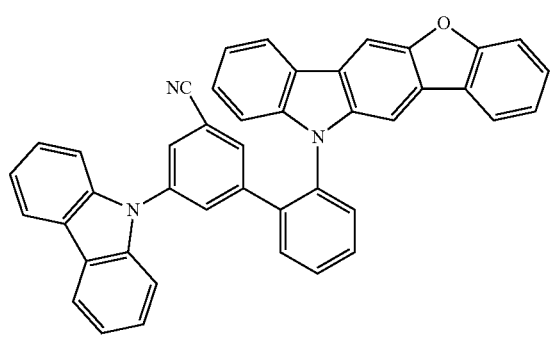
-continued
365
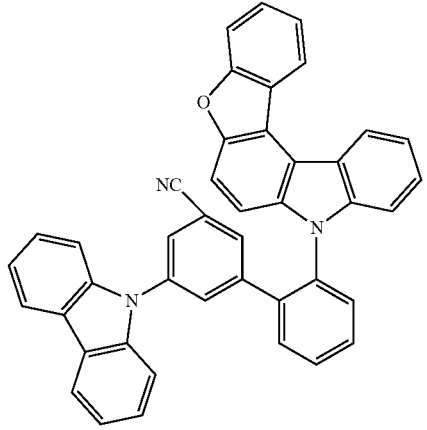
366
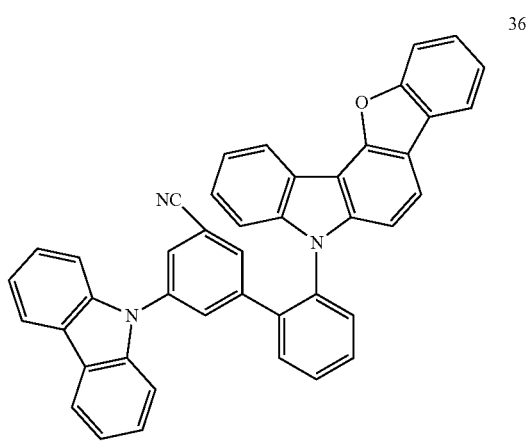
367
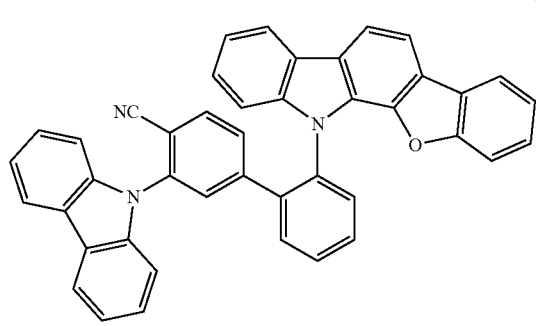
368
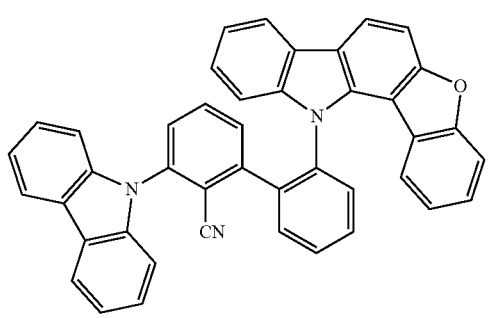

369
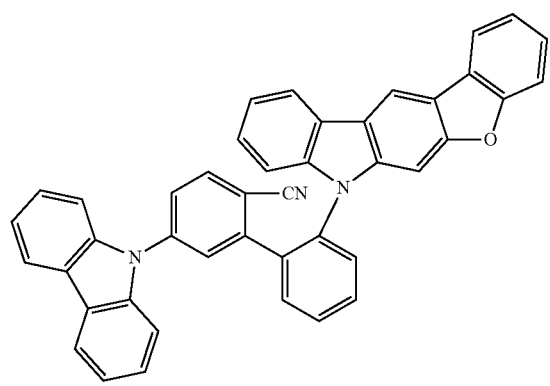
370
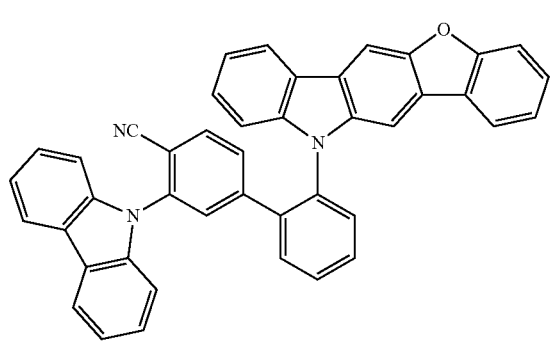
371
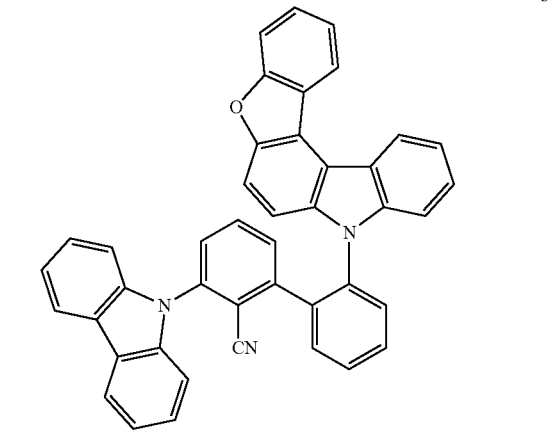
372
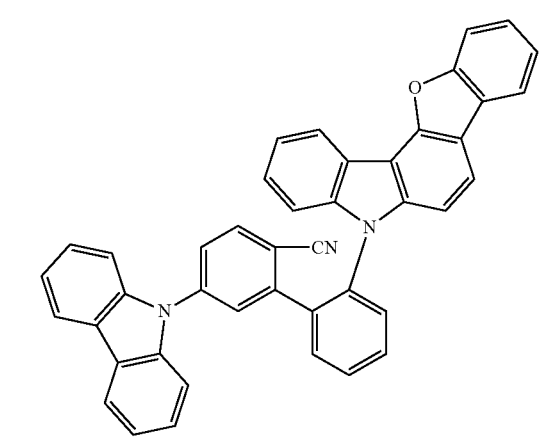
373
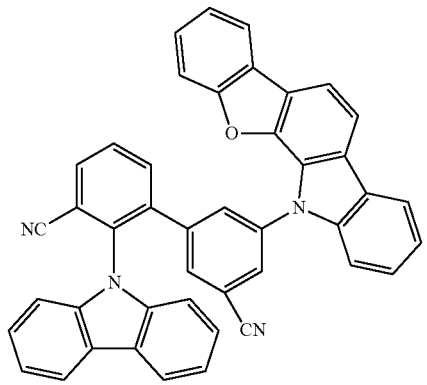
374
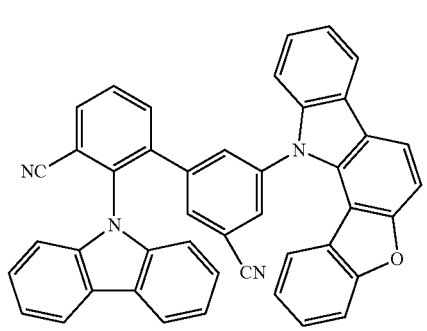
375
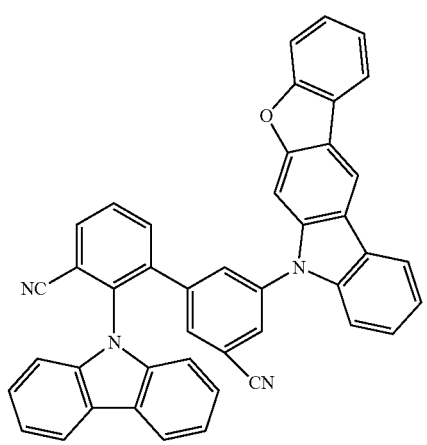
376
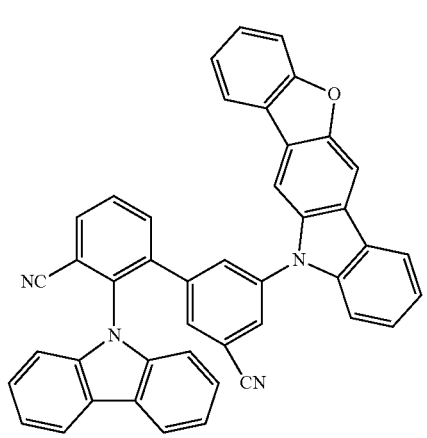

-continued
377
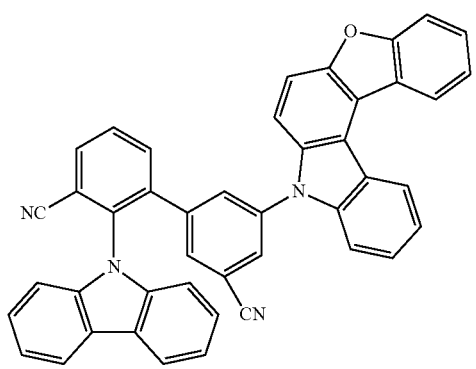
378
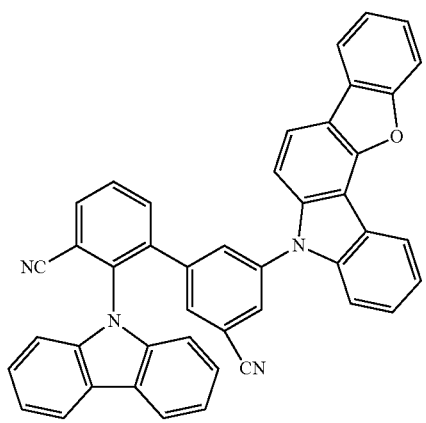
379
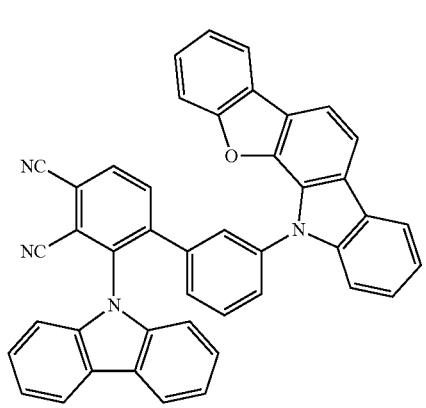
380
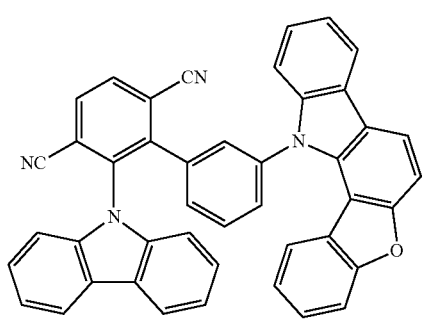
-continued
381
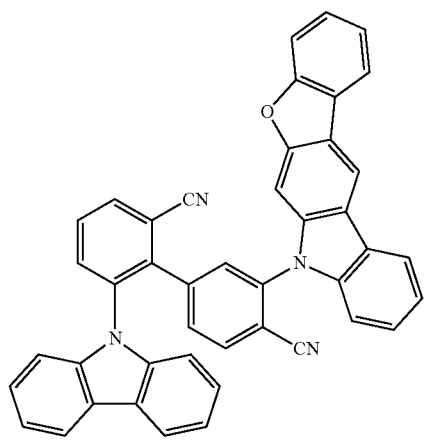
382
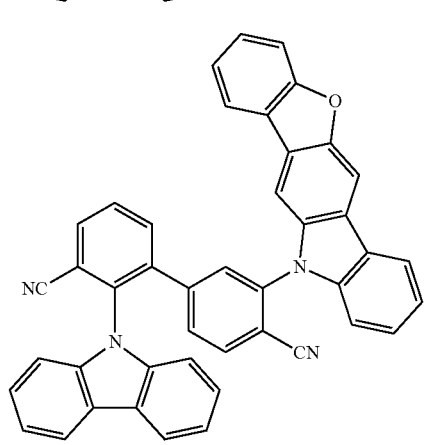
383
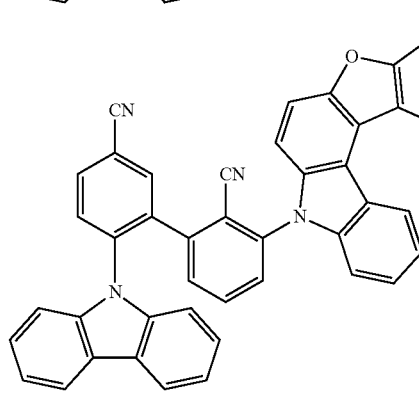
384
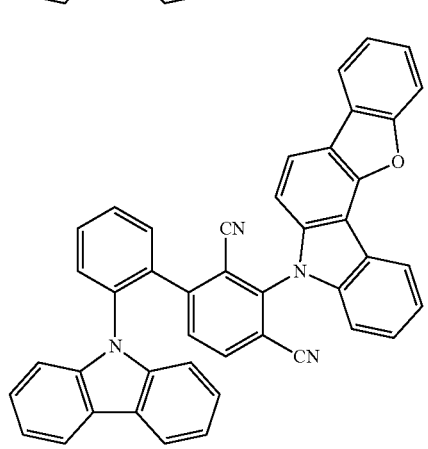

385
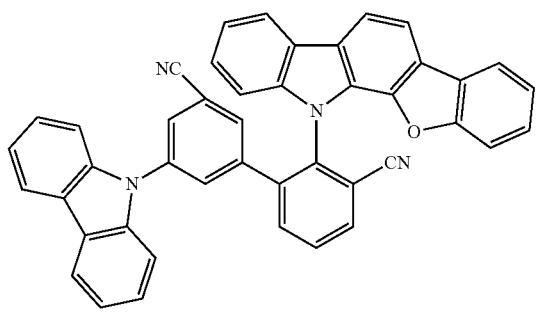
386
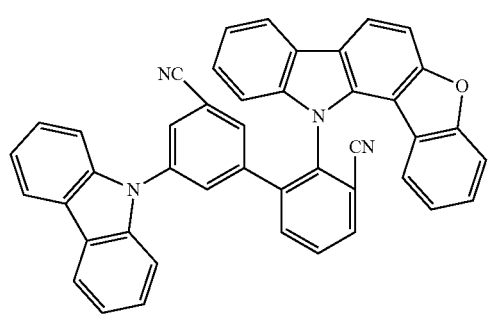
387
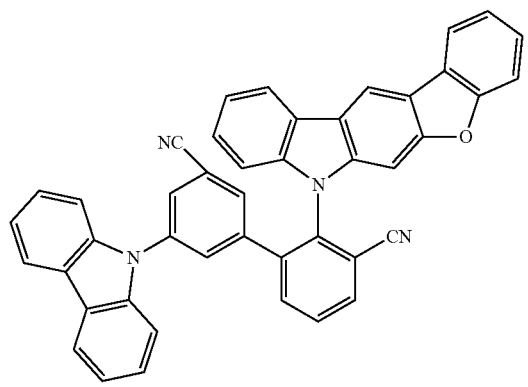
388
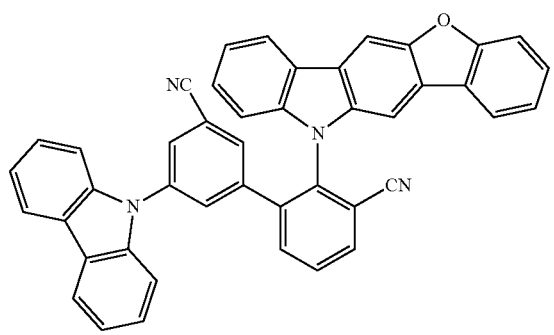
389
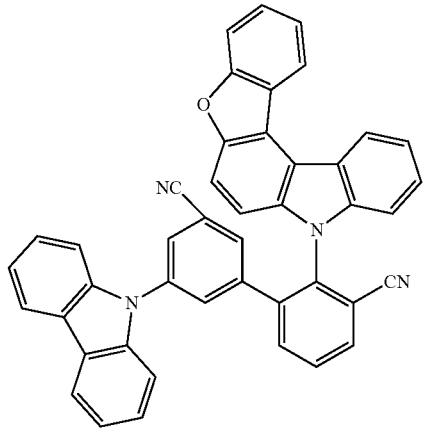
390
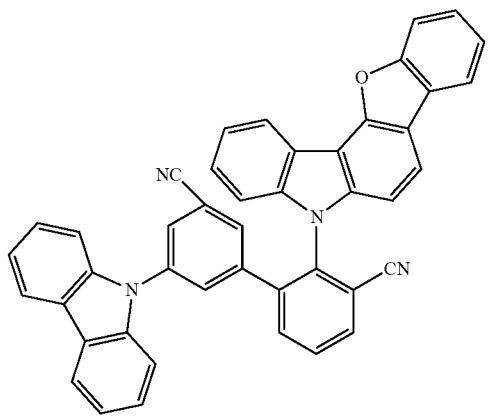
391
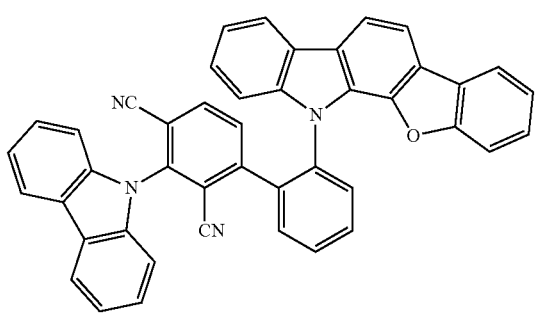
392
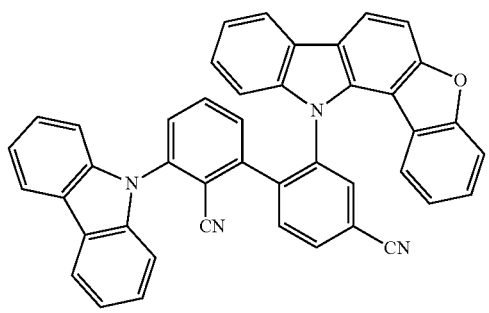

393
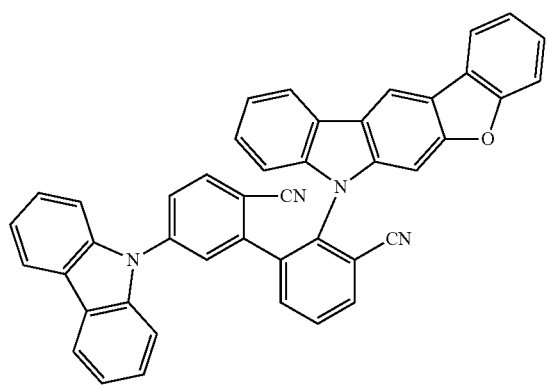
394
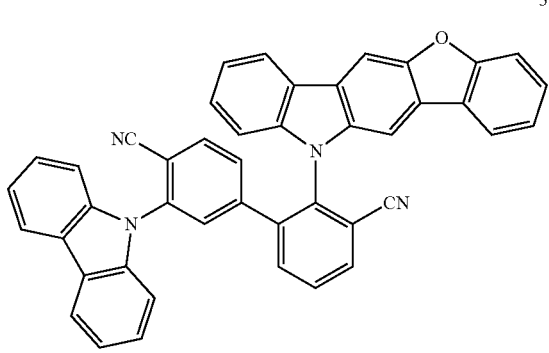
395
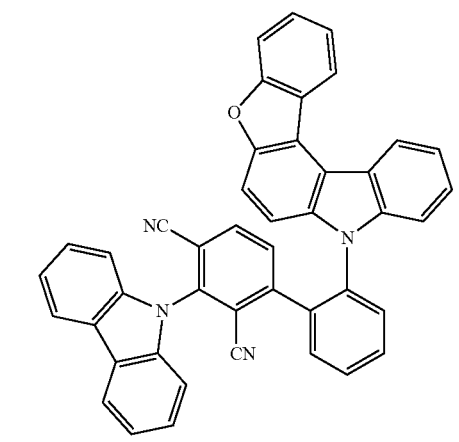
396
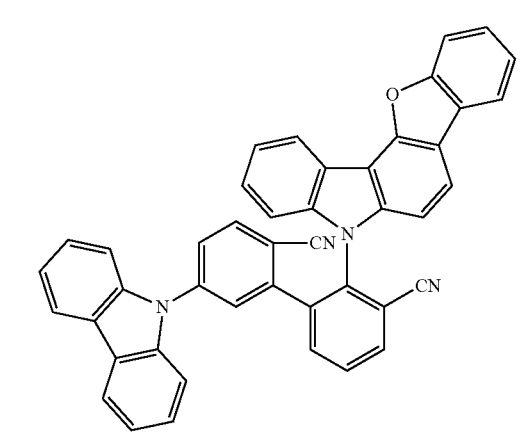
397
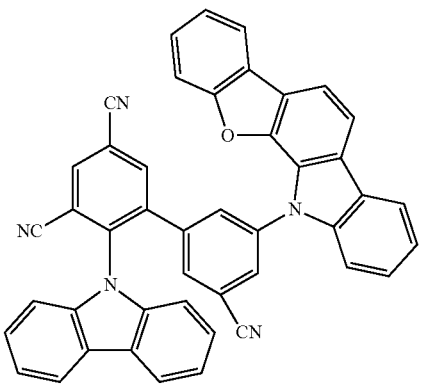
398
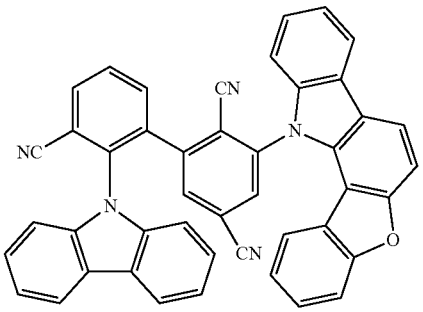
399
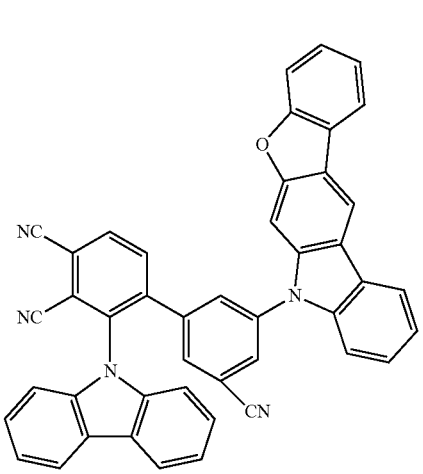
400
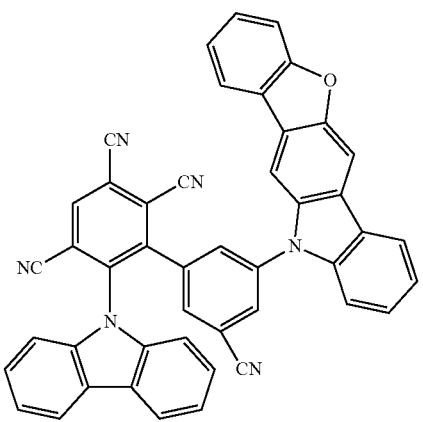

401
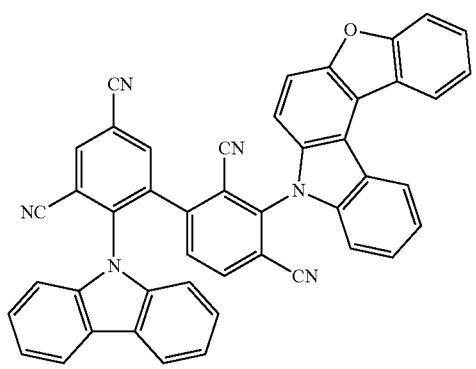
402
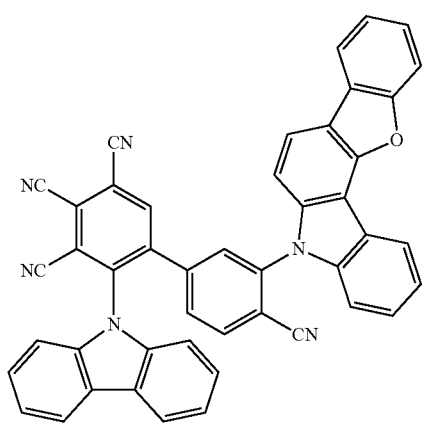
403
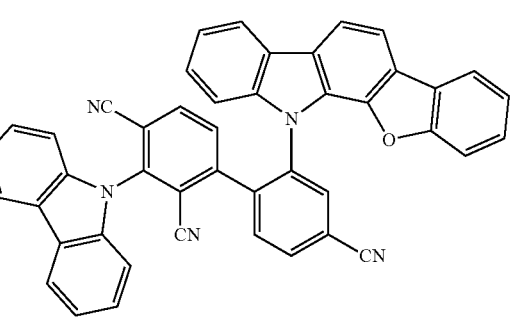
404
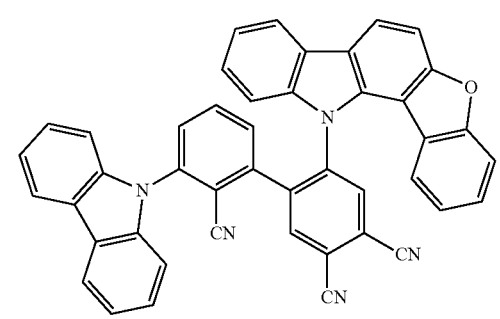
405
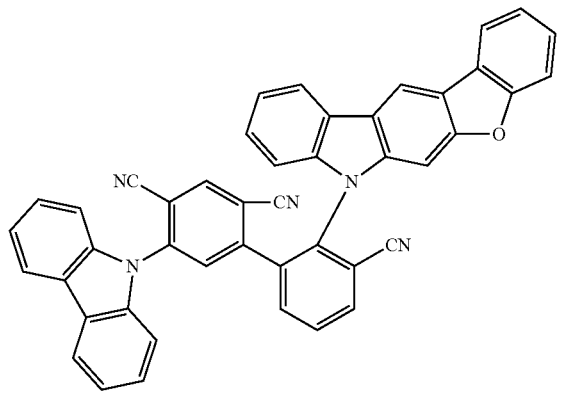
406
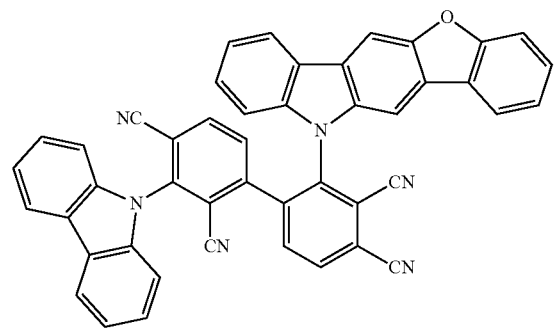
407
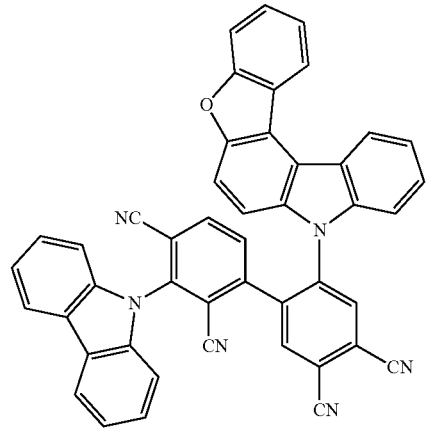
408
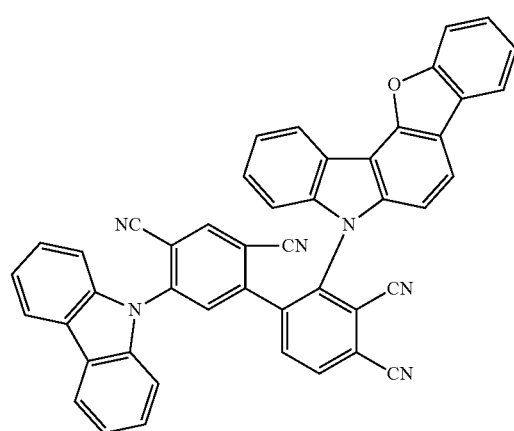

269
-continued
409
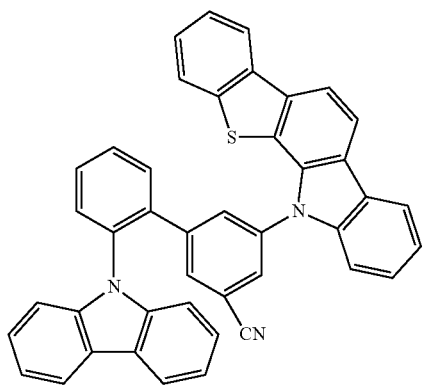
410
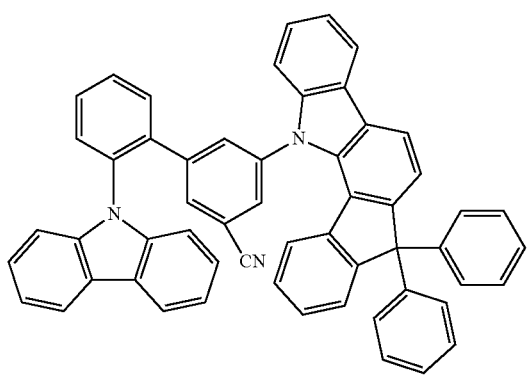
411
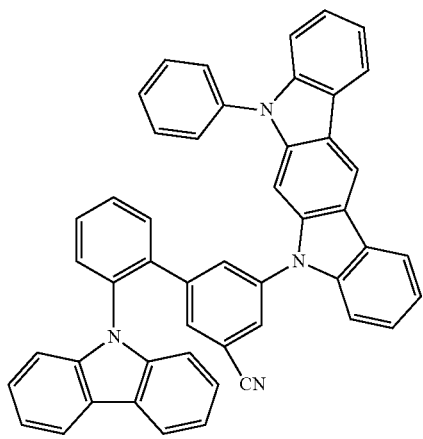
412
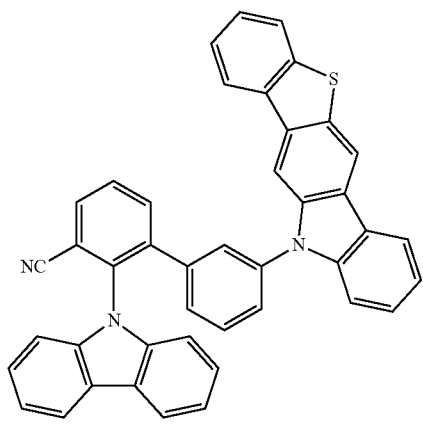
270
-continued
413
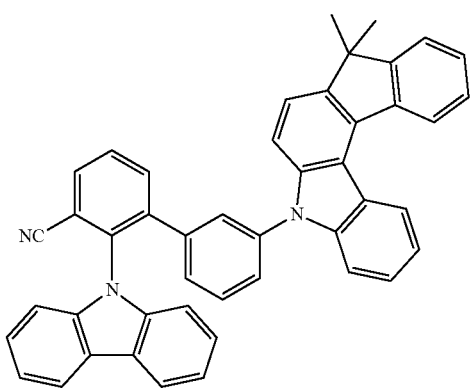
414
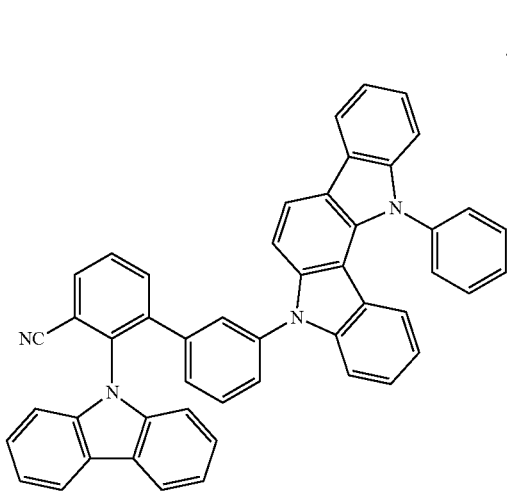
415
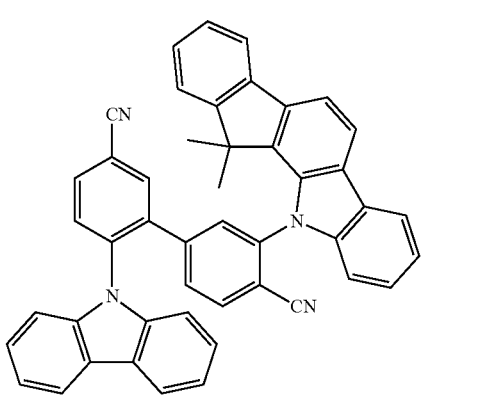
416
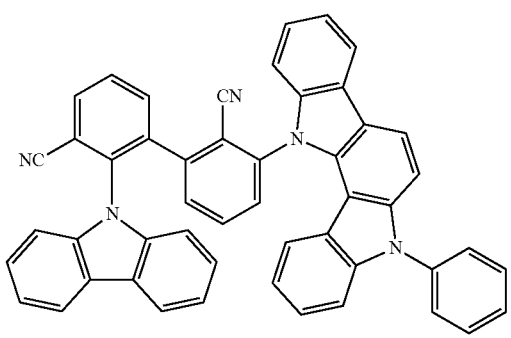

-continued
417
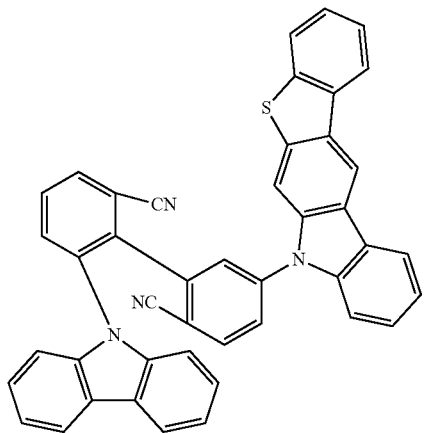
418
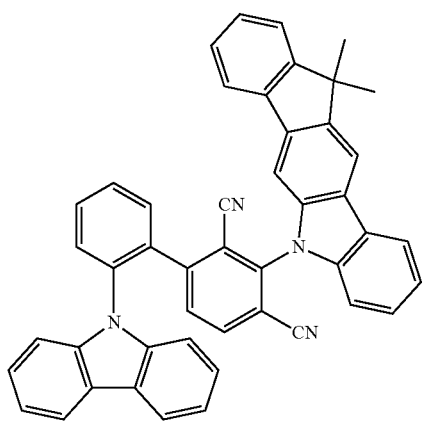
419
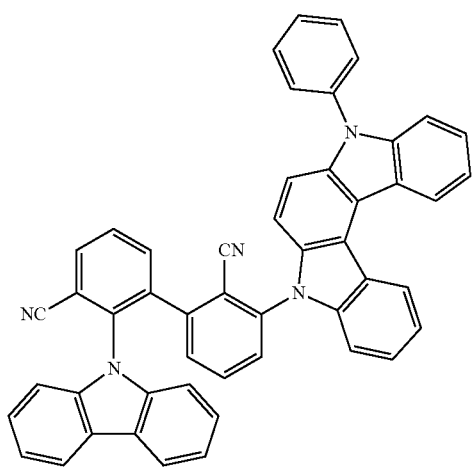
-continued
420
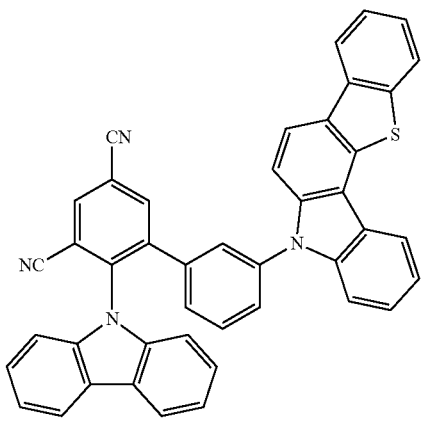
421
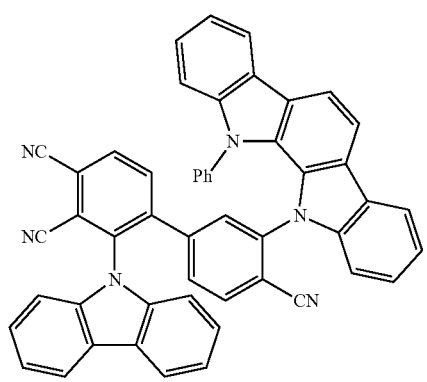
422
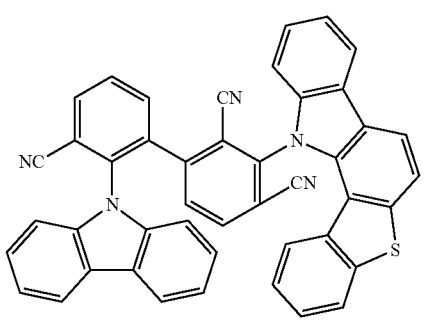
423
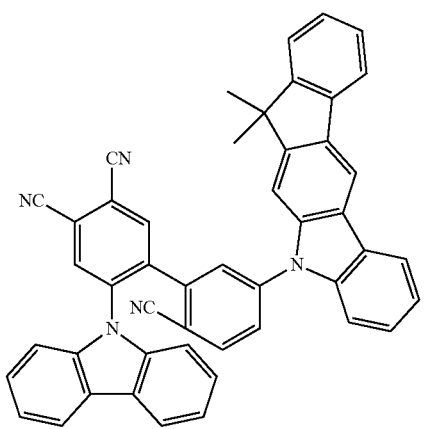

424
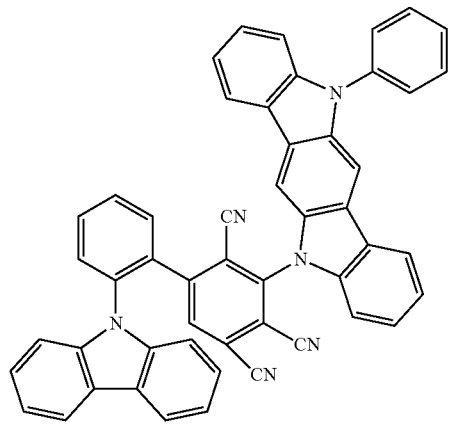
425
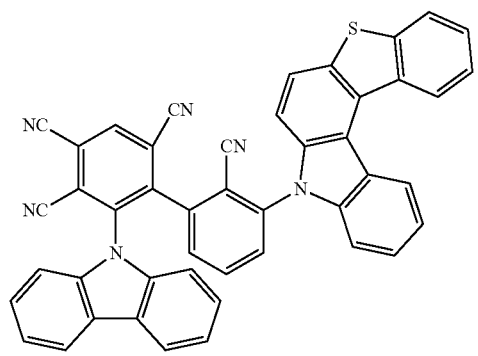
426
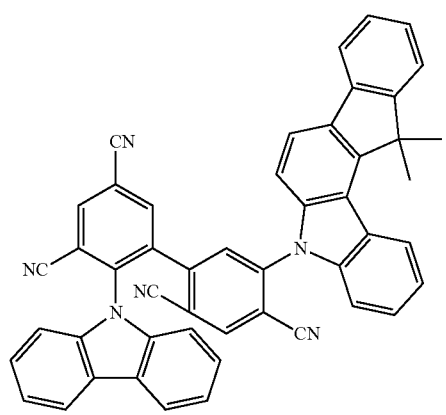
427
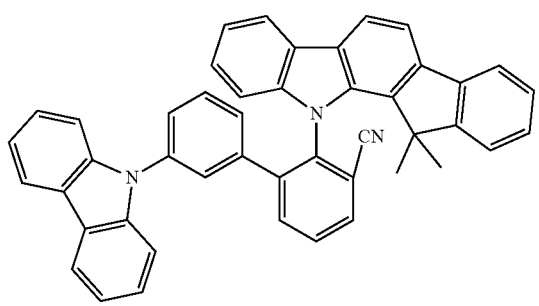
428
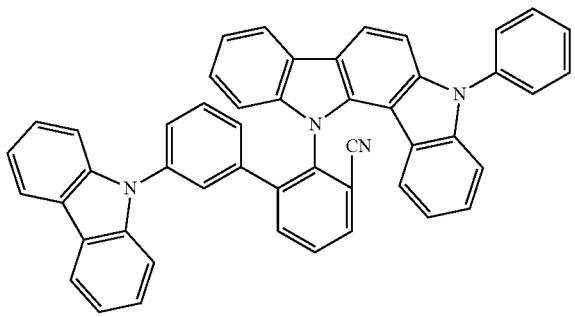
429
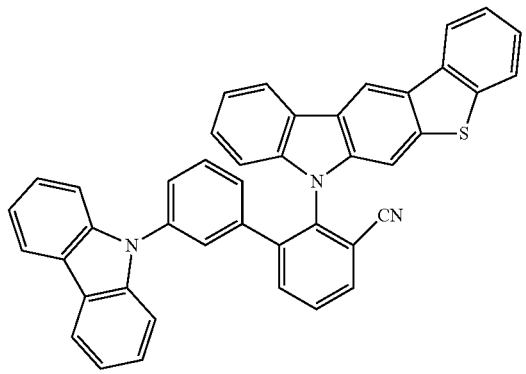
430
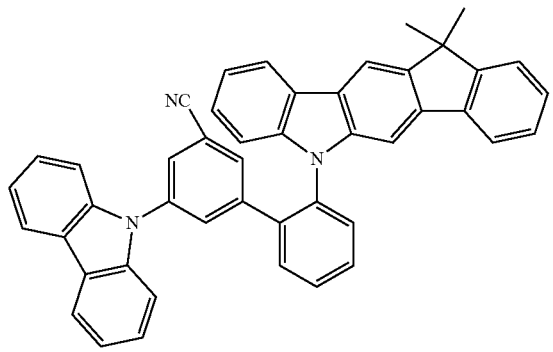
431
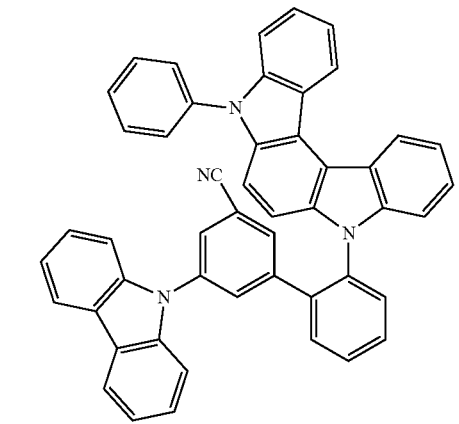

275
-continued

432

433

434

435

276
-continued

436

437

438

439

277
-continued
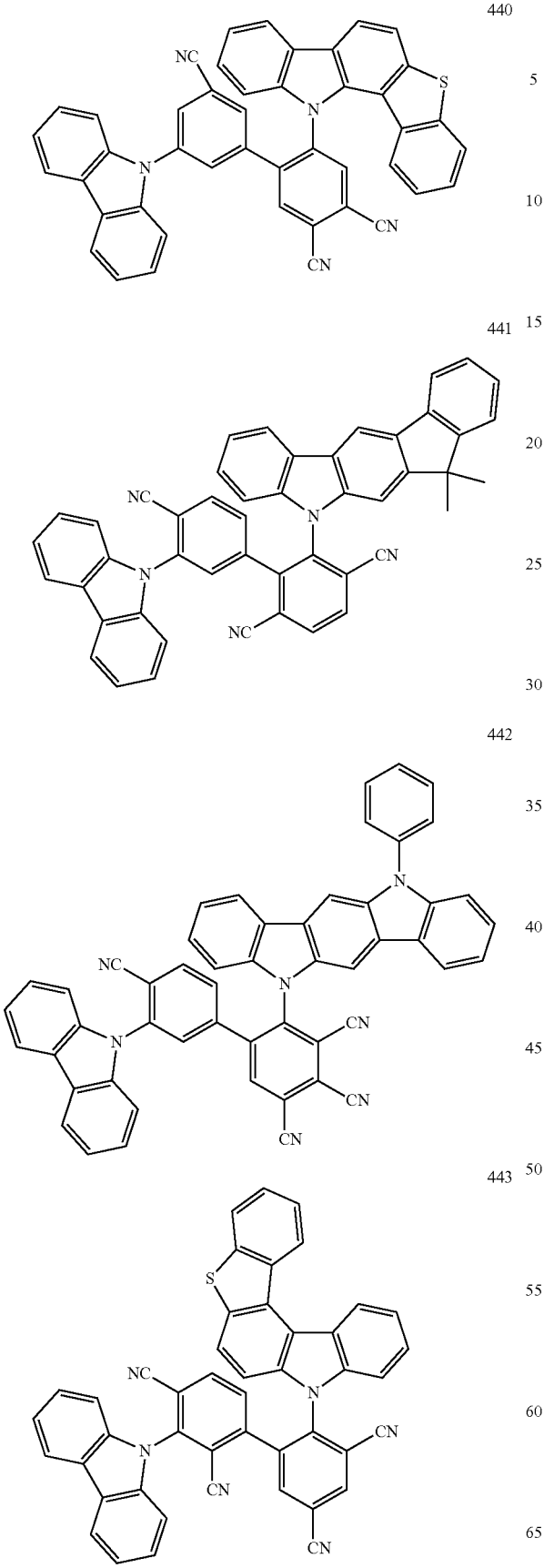
278
-continued
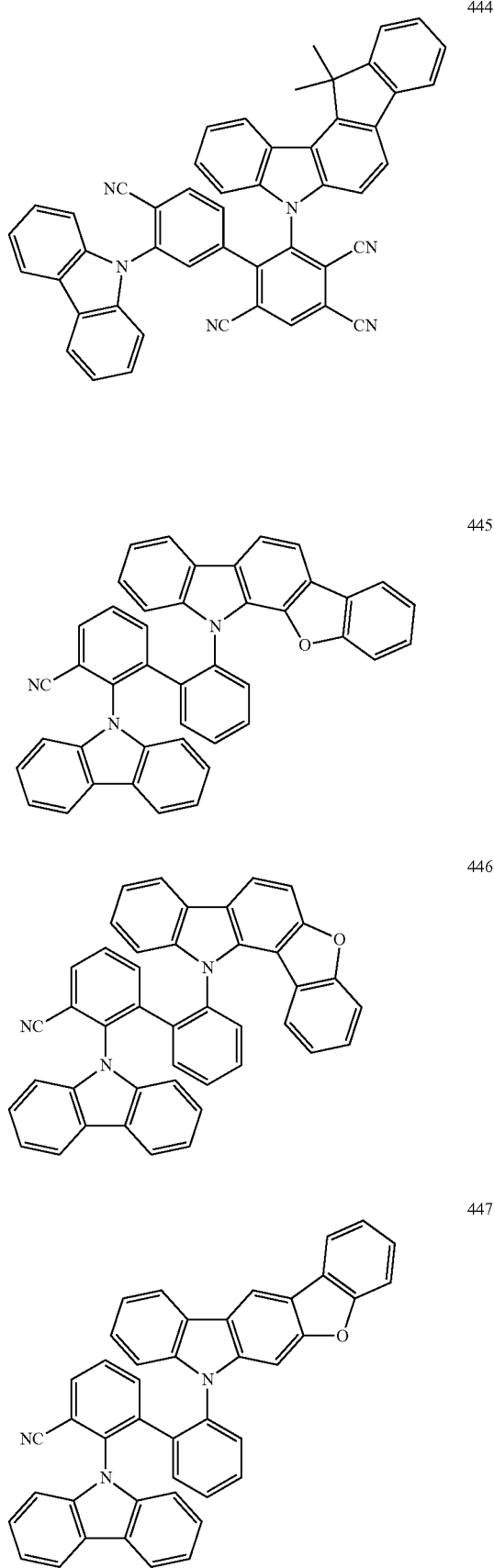

| 279 -continued | | 280 -continued | |
|---|---|---|---|
| 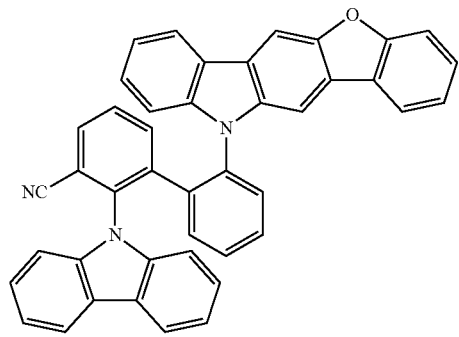 | 448 | 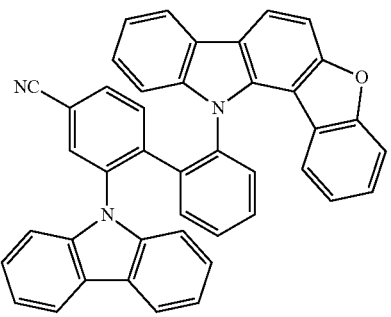 | 452 |
| 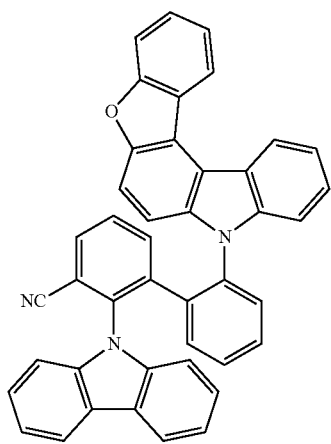 | 449 | 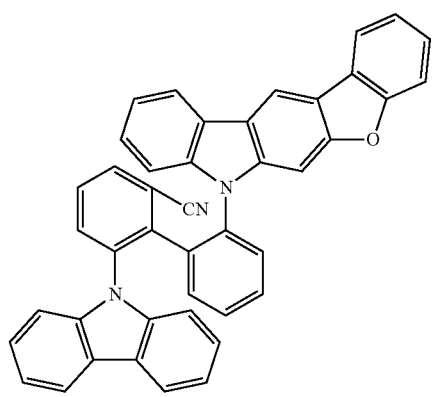 | 453 |
| 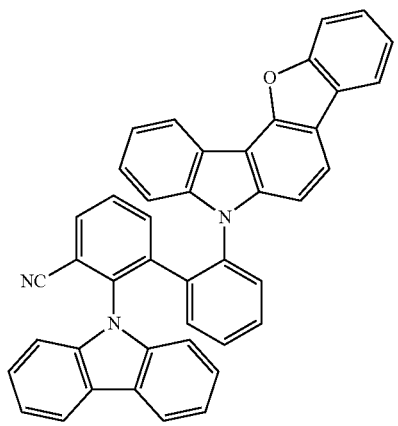 | 450 | 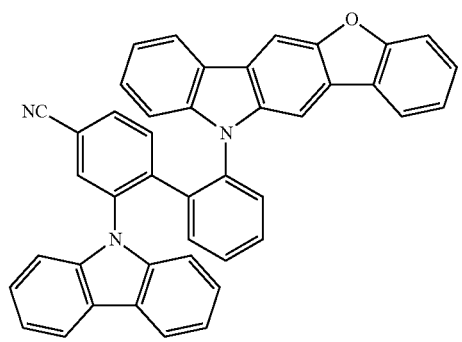 | 454 |
| 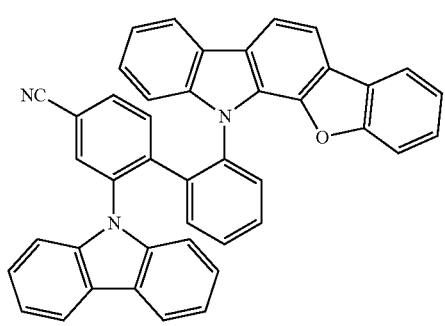 | 451 | 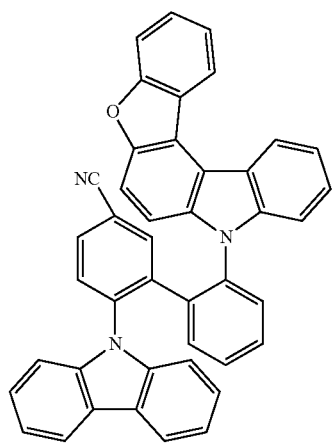 | 455 |

456
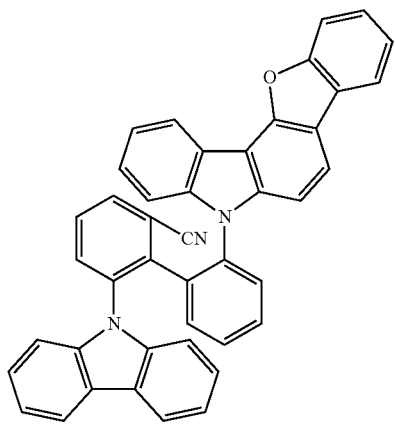
457
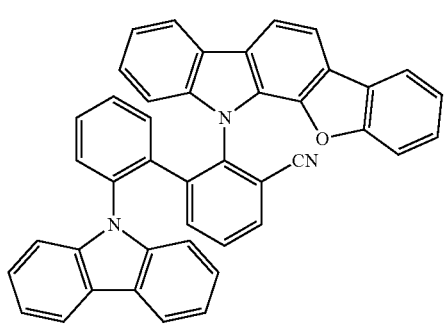
458
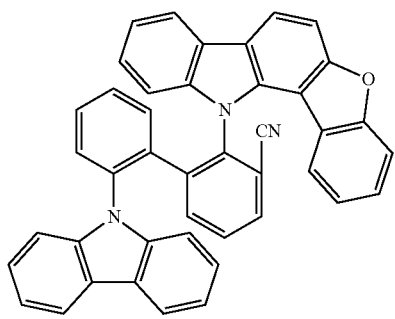
459
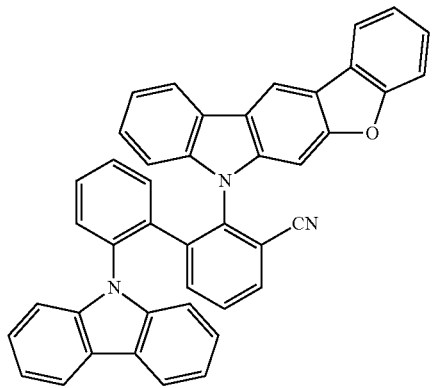
460
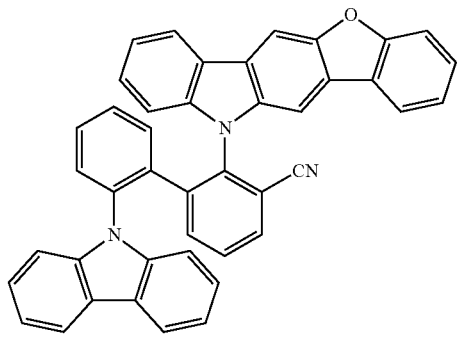
461
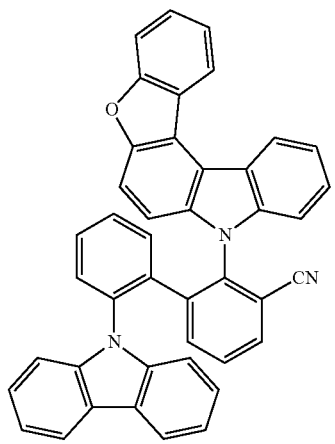
462
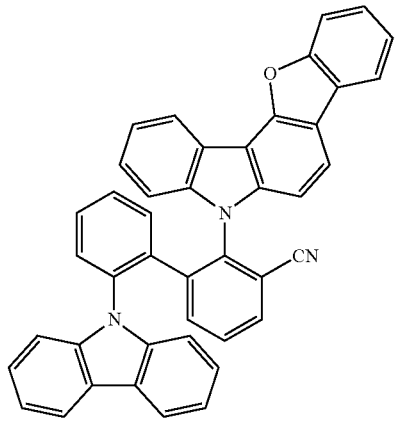
463
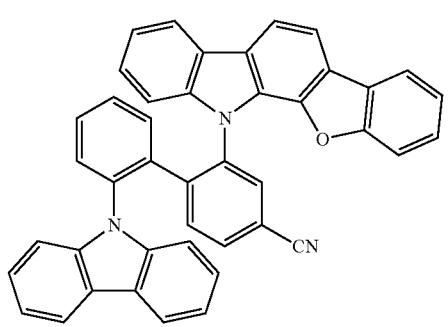

464
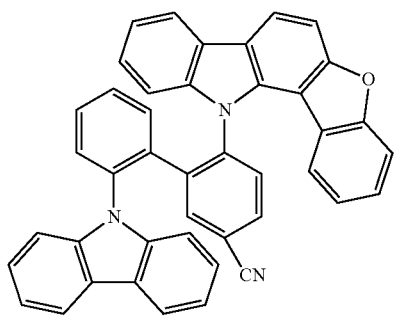
465
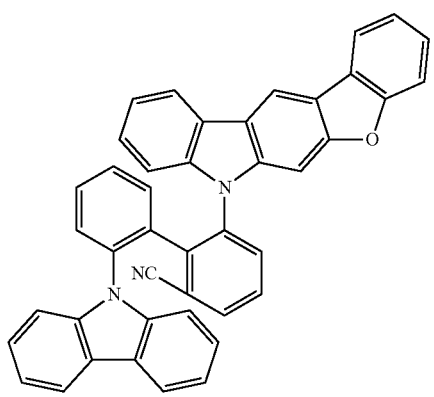
466
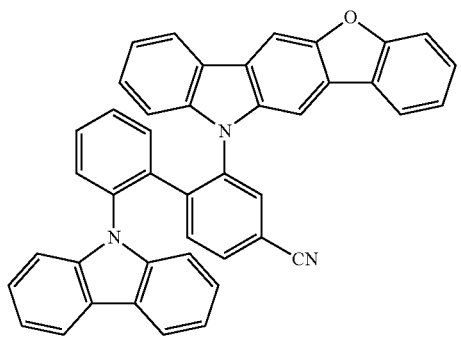
467
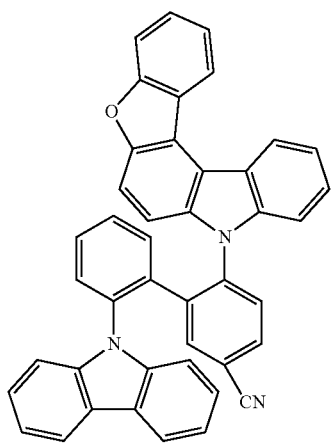
468
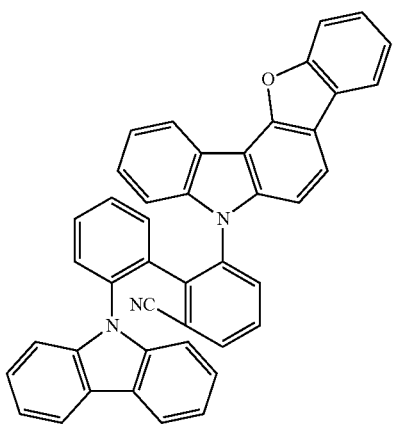
469
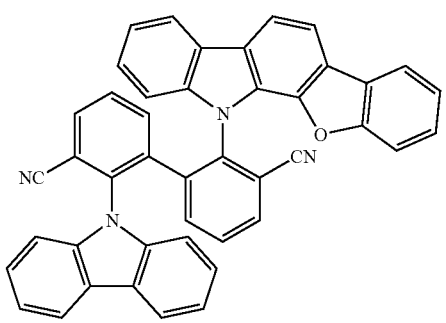
470
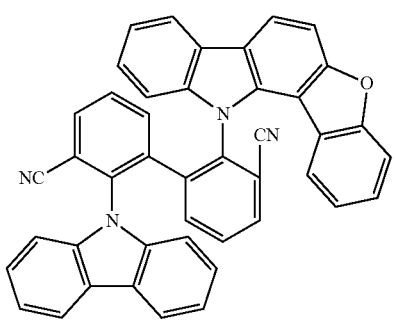
471
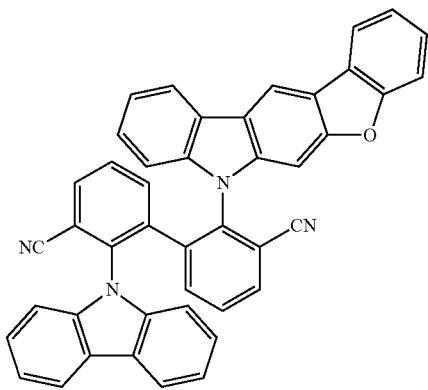

| | |
|---|---|
| 472 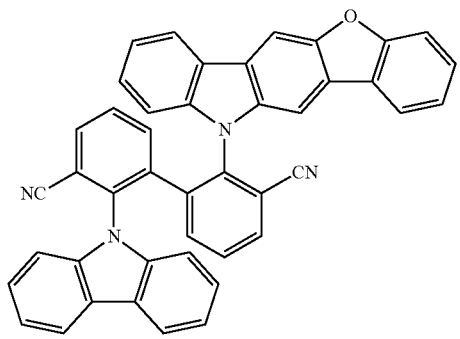 | 476 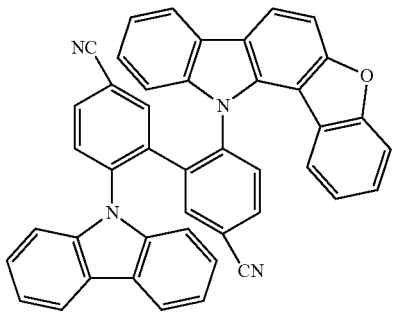 |
| 473 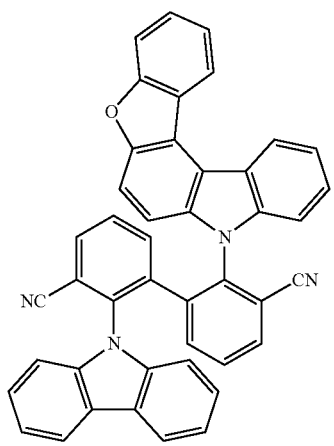 | 477 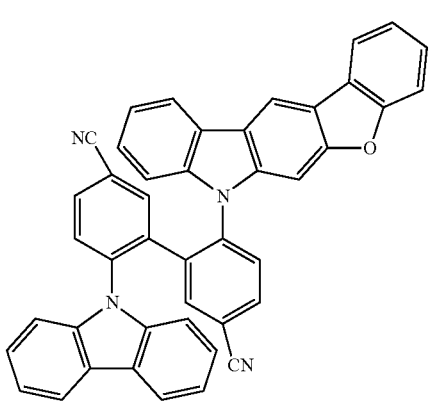 |
| 474 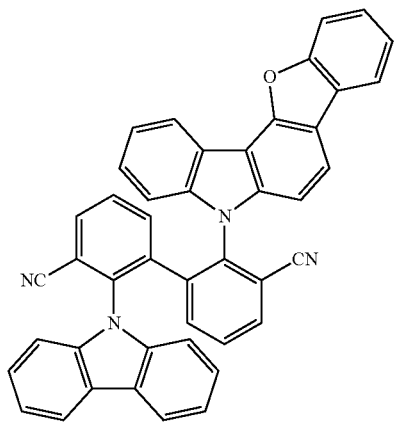 | 478 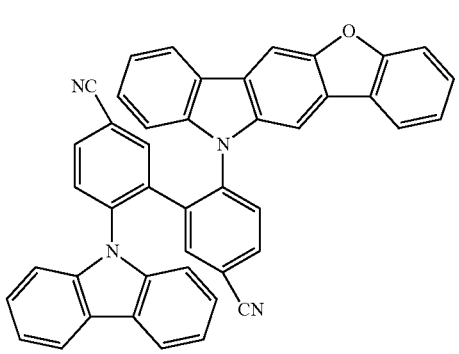 |
| 475 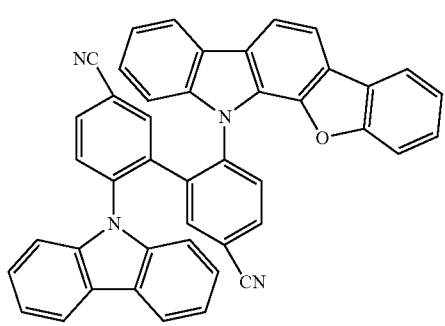 | 479 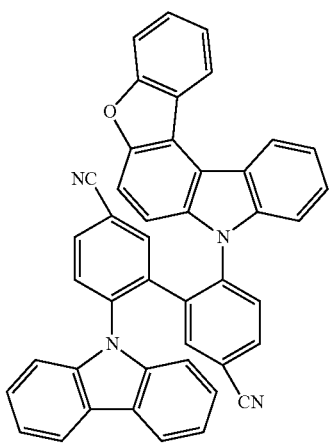 |

480
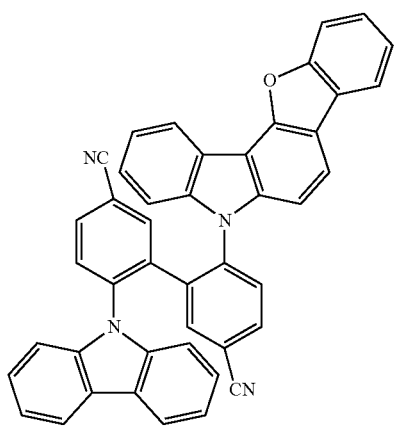
481
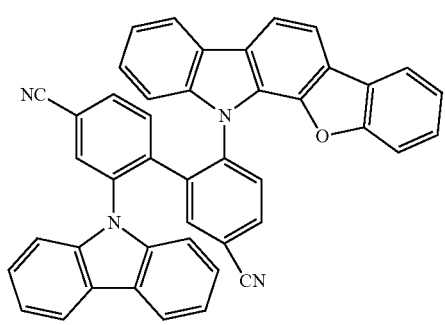
482
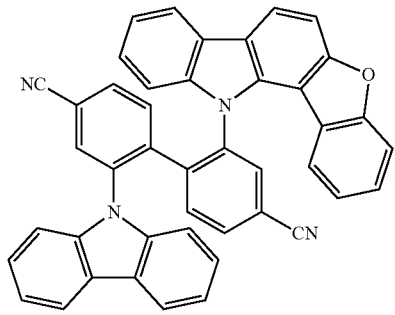
483
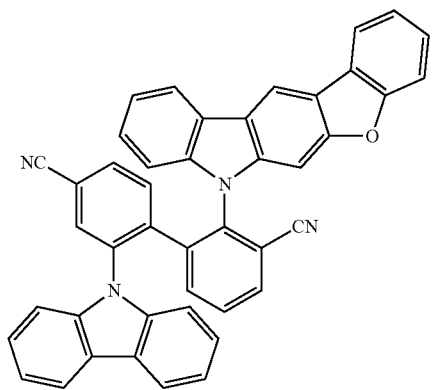
484
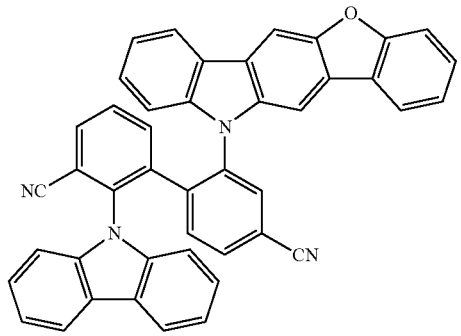
485
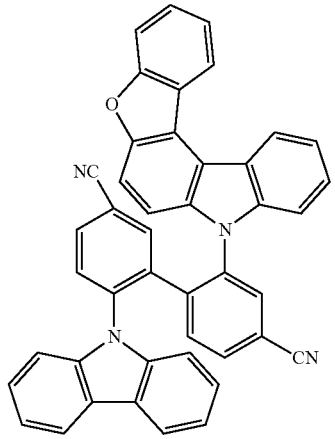
486
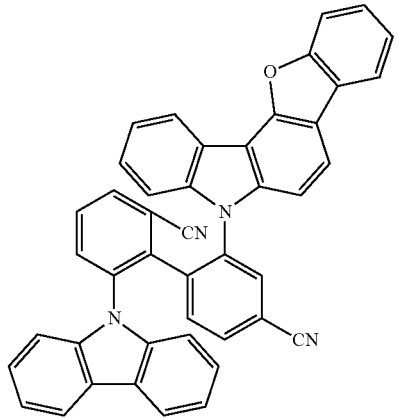
487
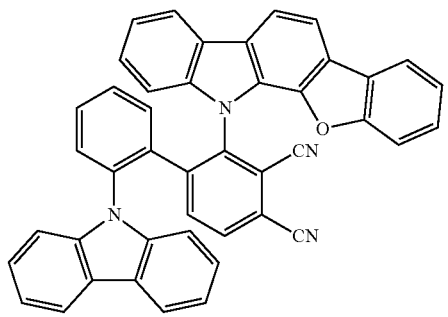

488
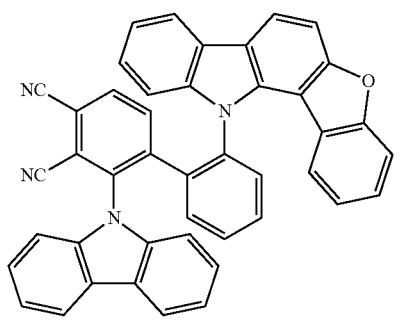
489
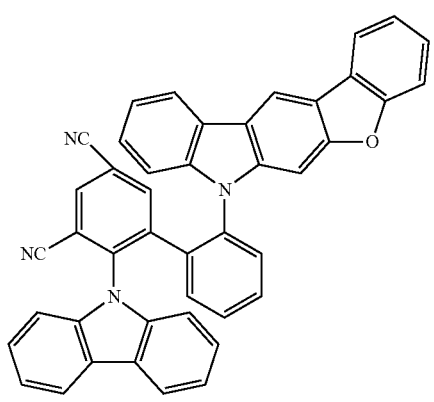
490
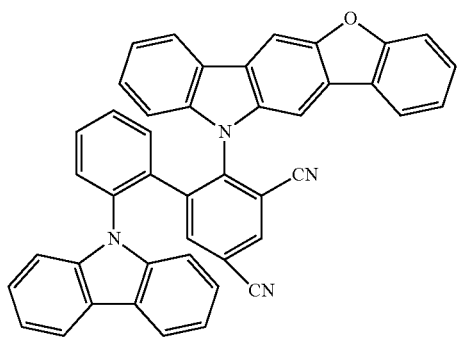
491
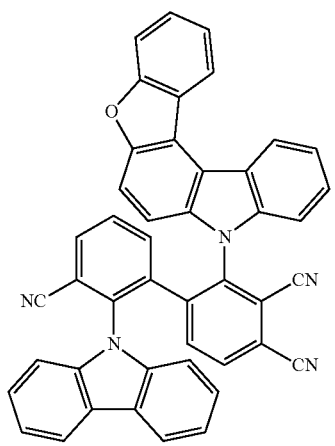
492
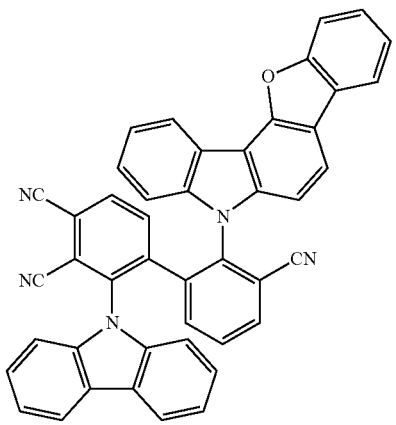
493
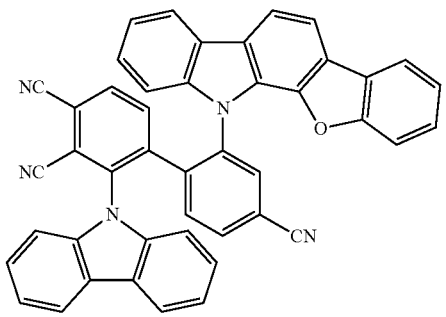
494
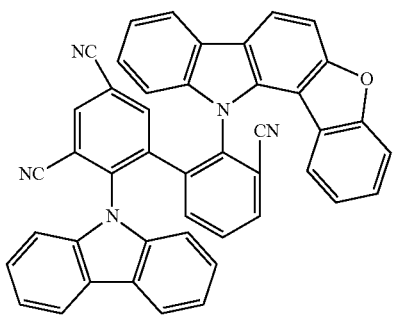
495
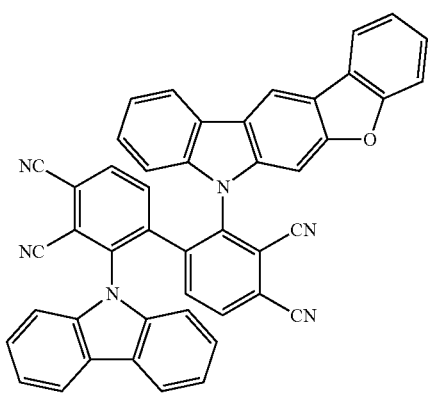

496
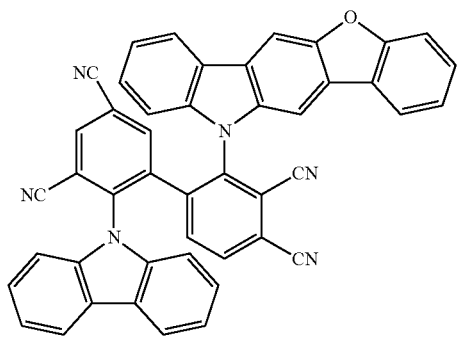
497
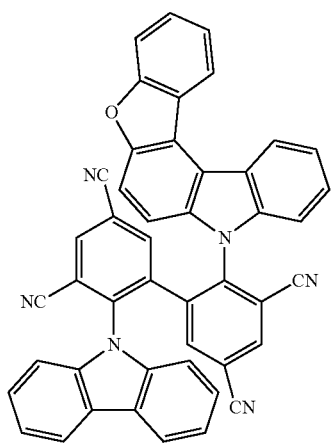
498
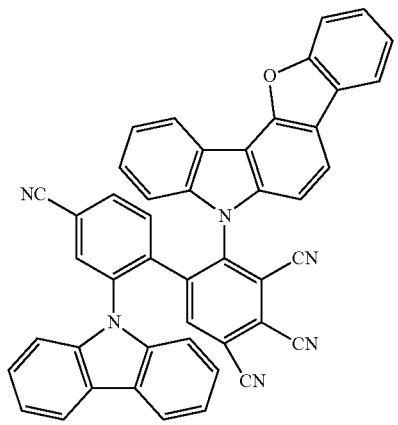
499
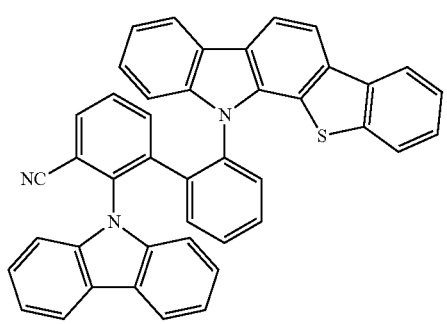
500
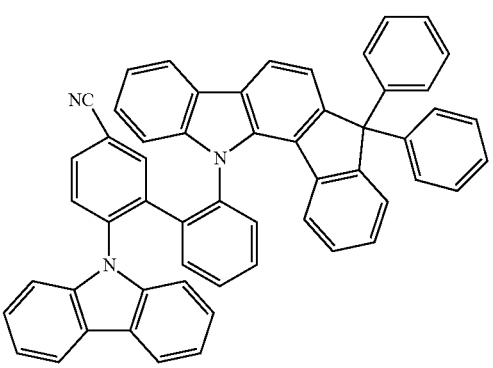
501
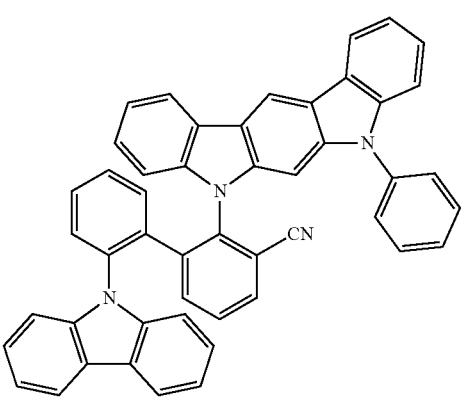
502
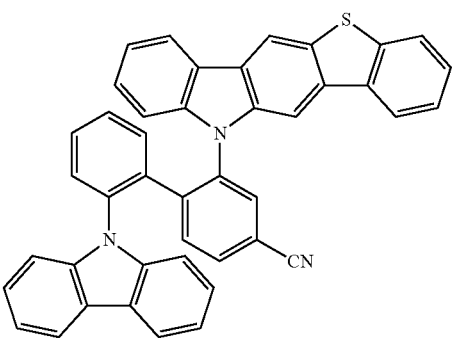
503
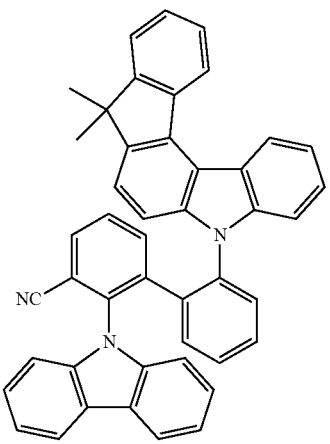

504
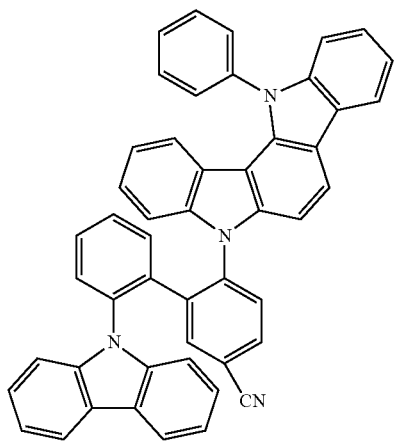
505
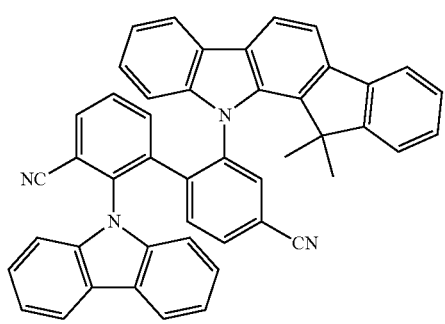
506
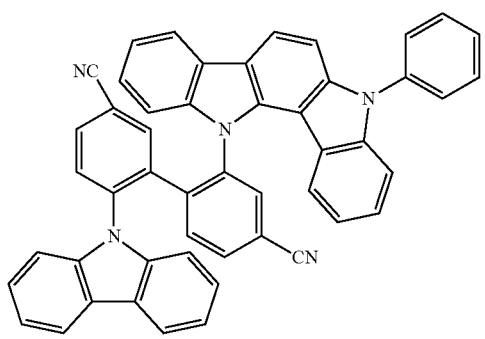
507
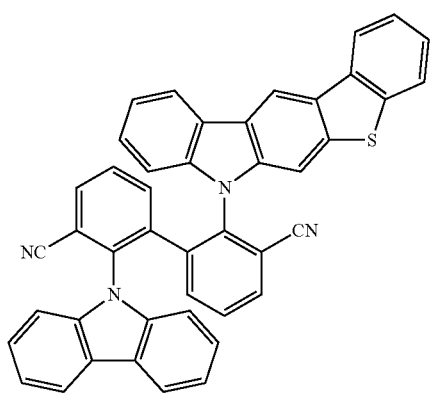
508
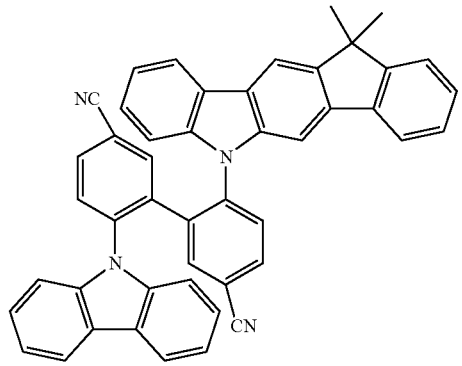
509
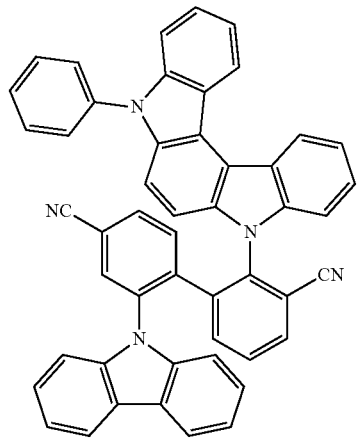
510
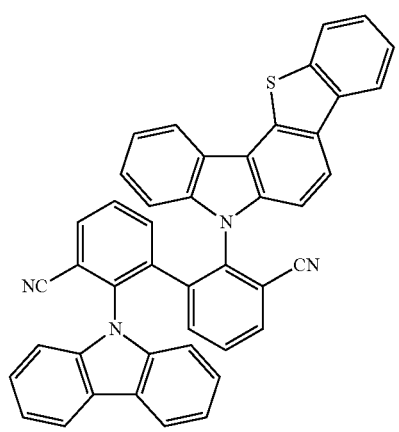
511
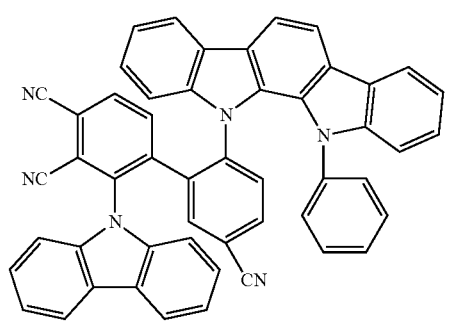

512
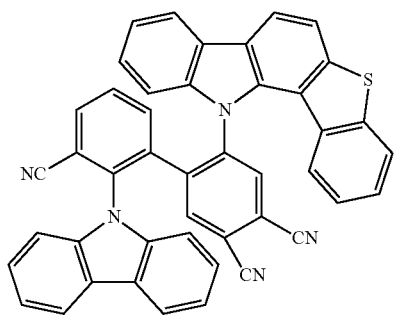
513
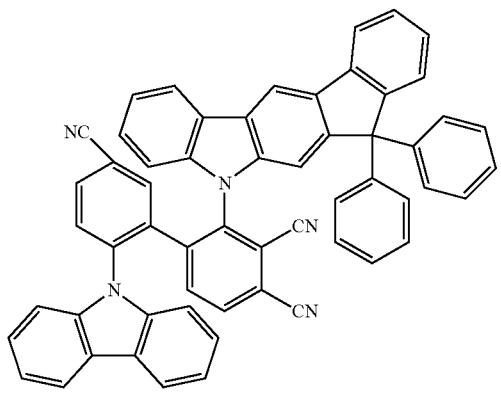
514
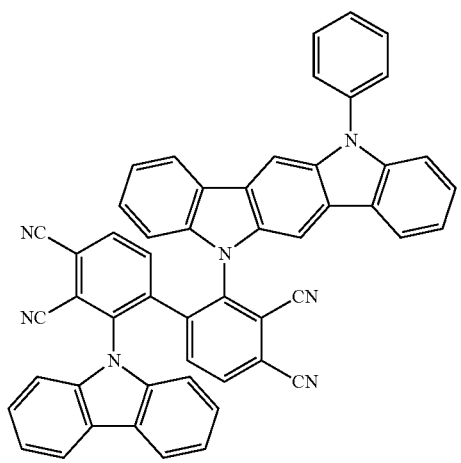
515
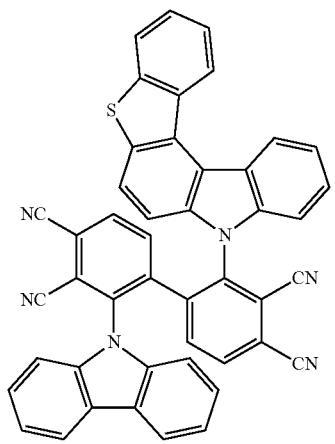
516
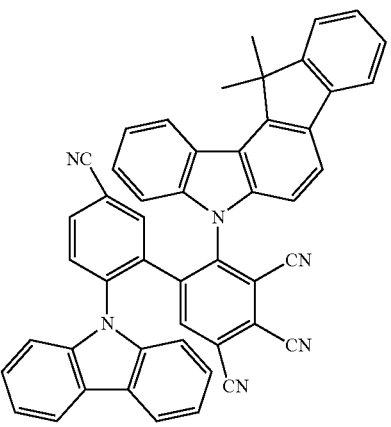
517
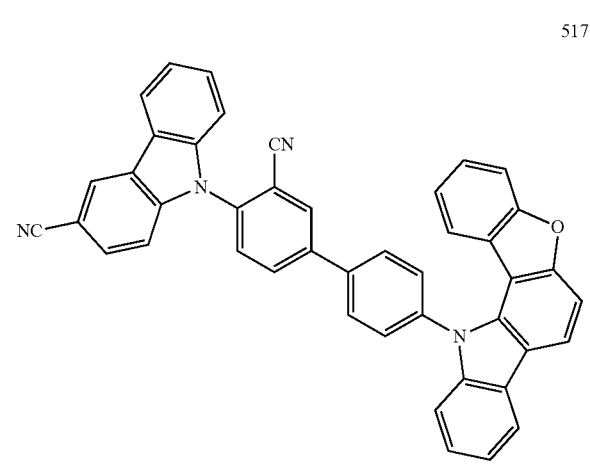
518
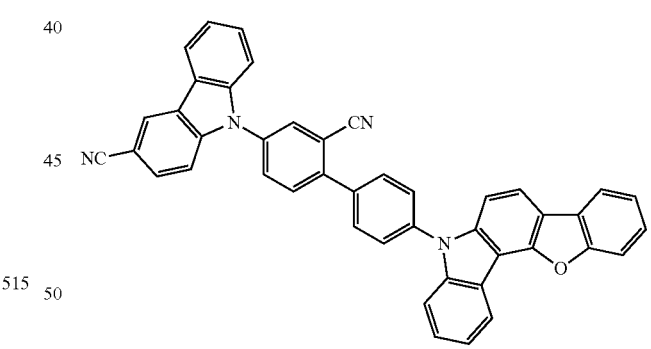
519
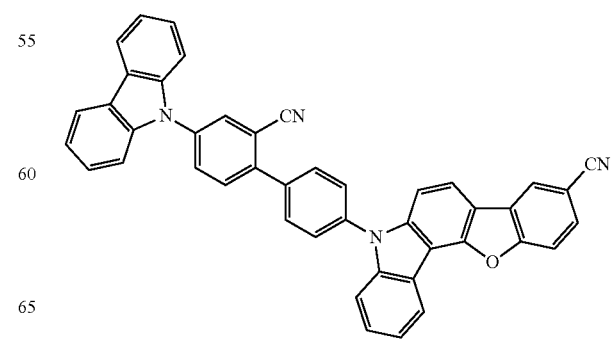

297
-continued
520
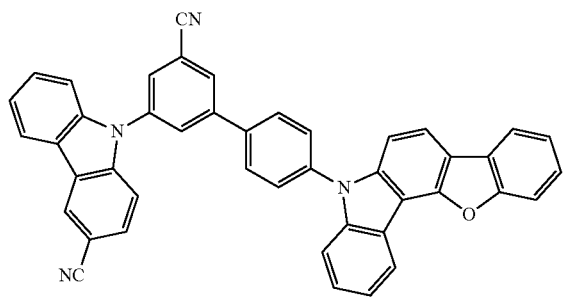
521
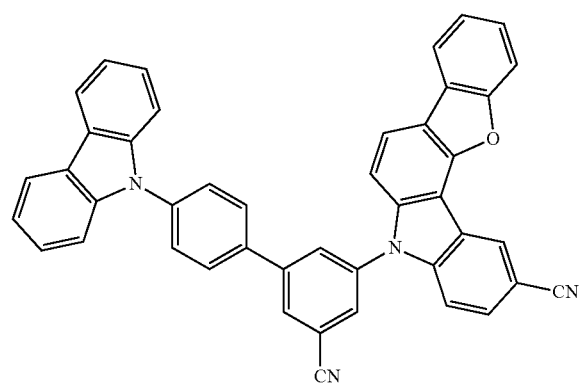
522
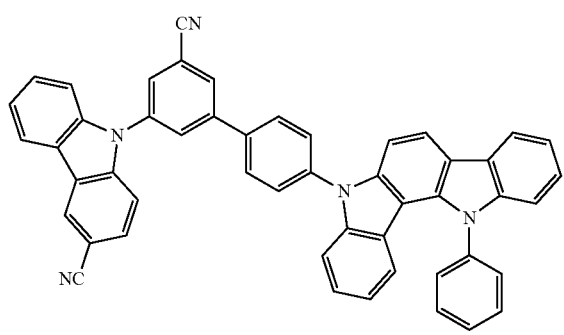
523
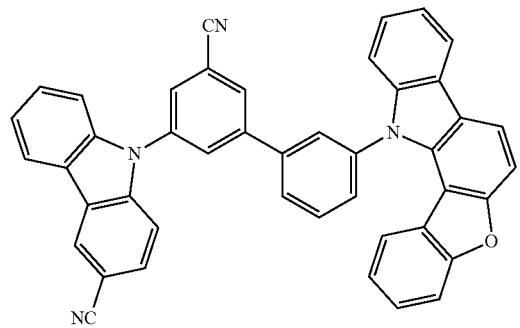
298
-continued
524
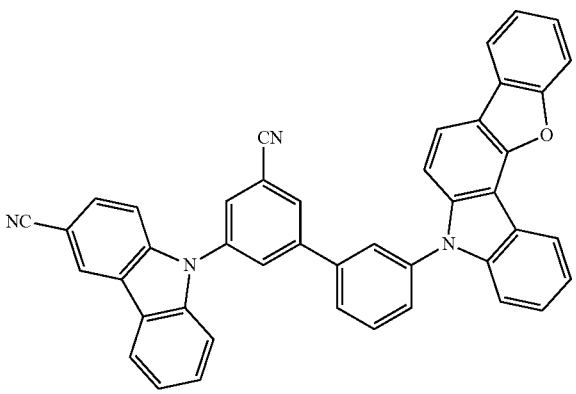
525
526
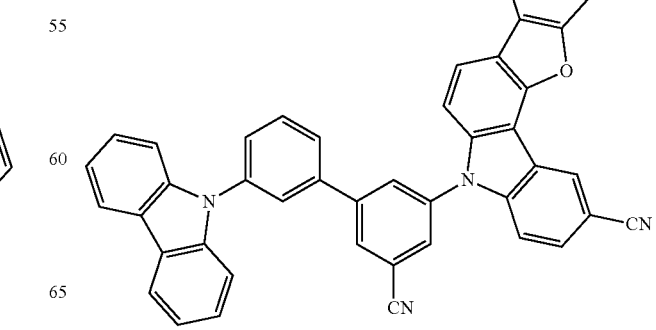

299
-continued
527
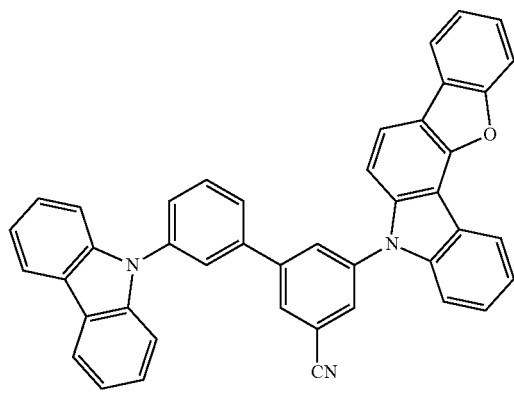
528
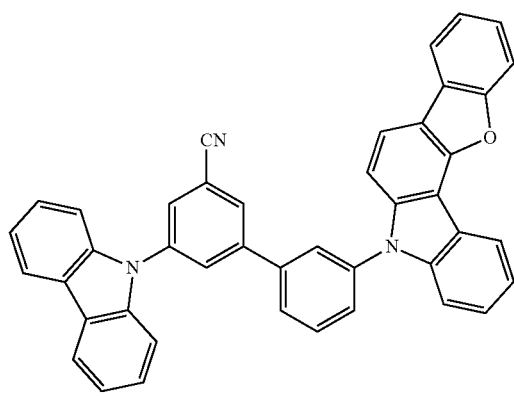
529
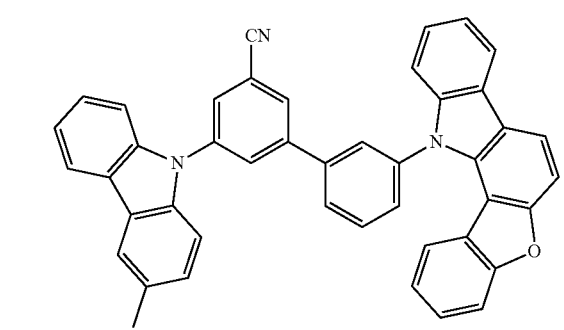
530
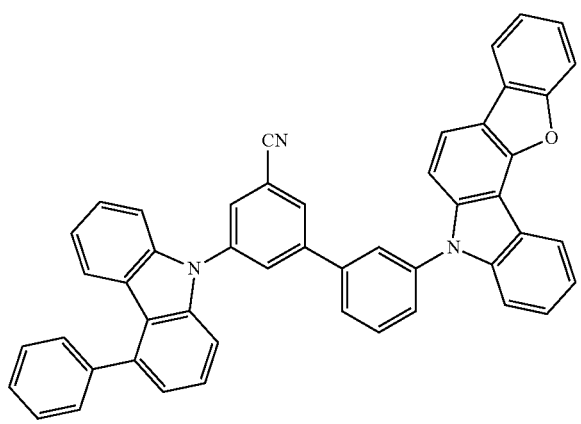
300
-continued
531
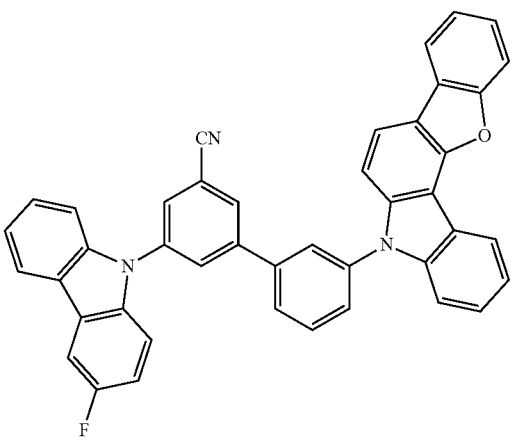
532
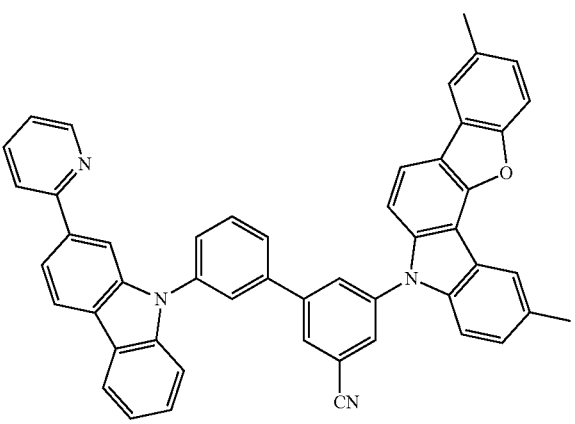
533

534
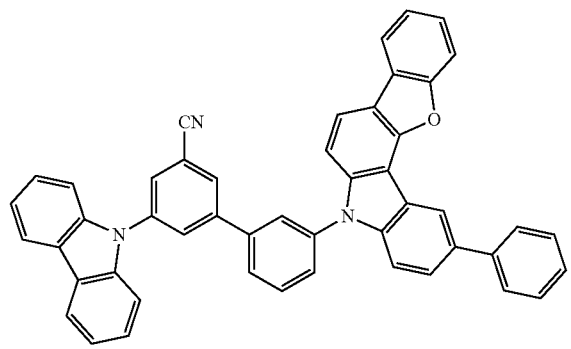
538
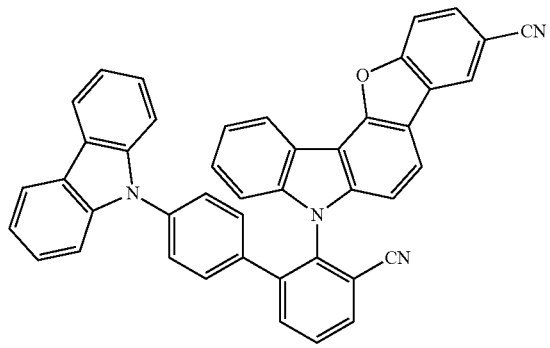
535
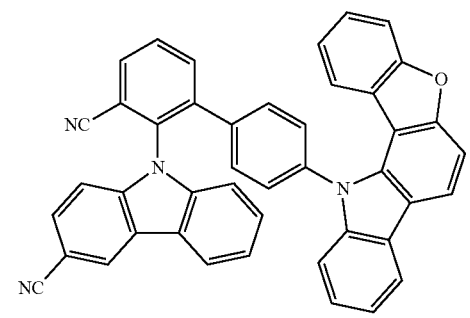
539
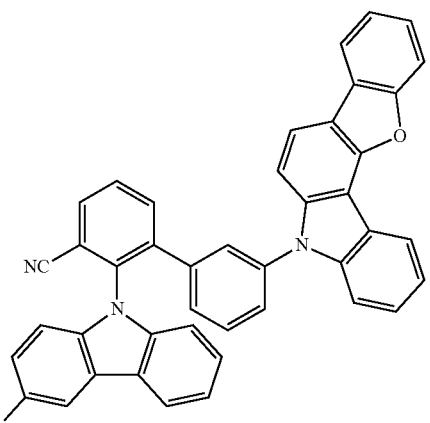
536
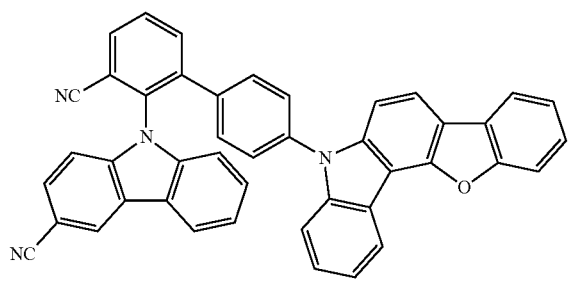
540
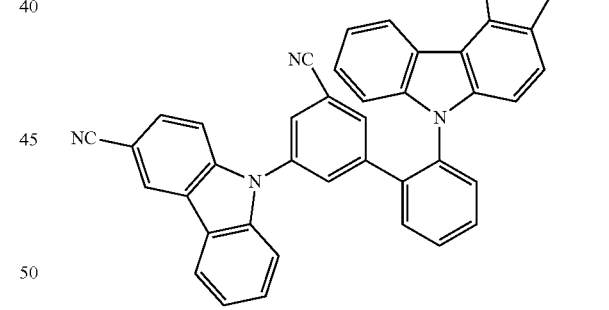
537
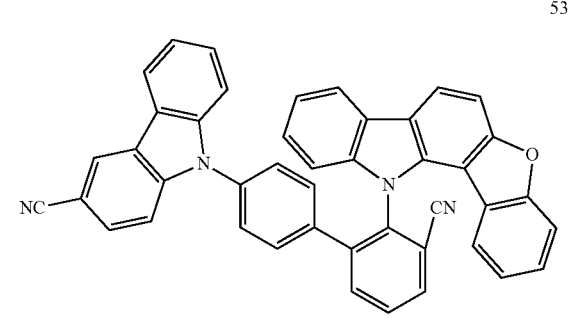
541
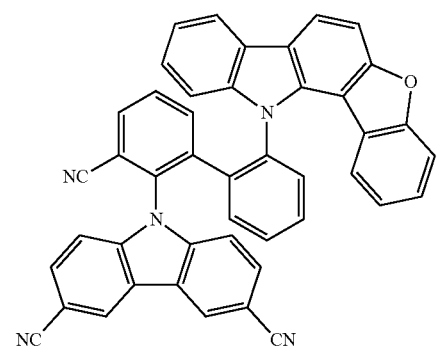

303
-continued
542
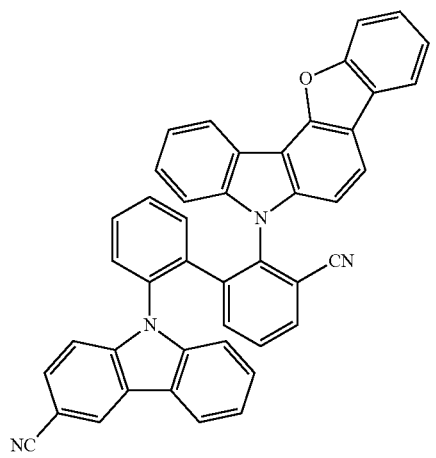
543
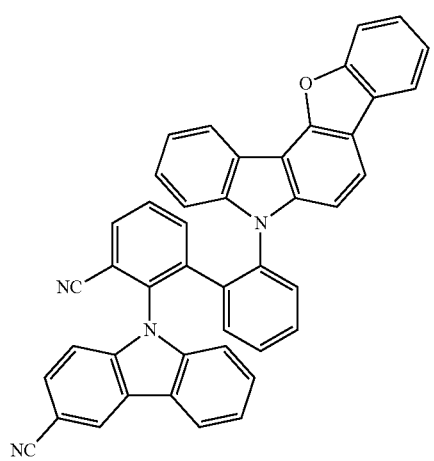
544
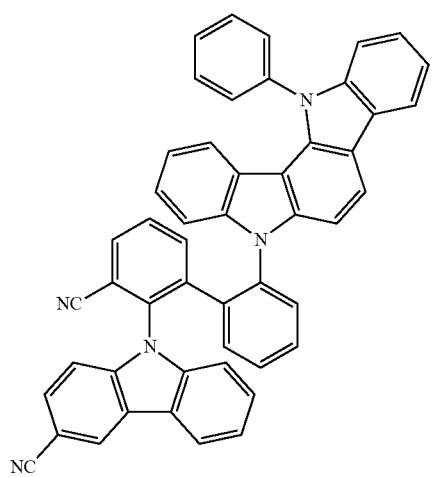
304
-continued
545
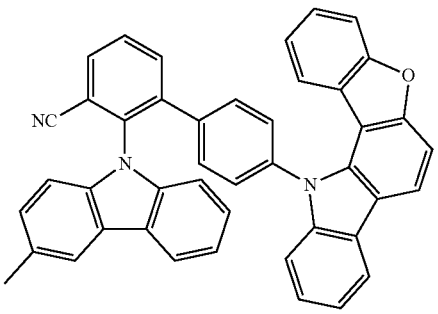
546
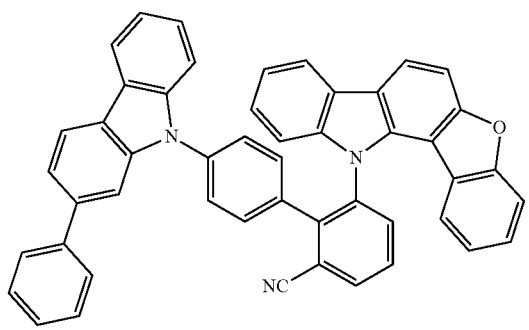
547
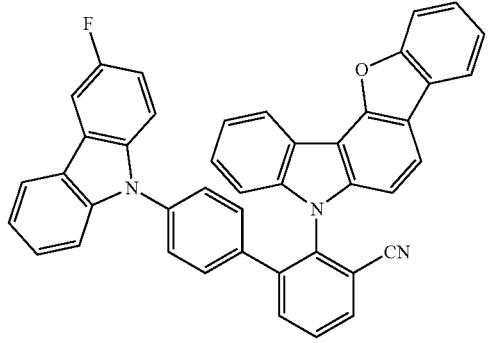
548
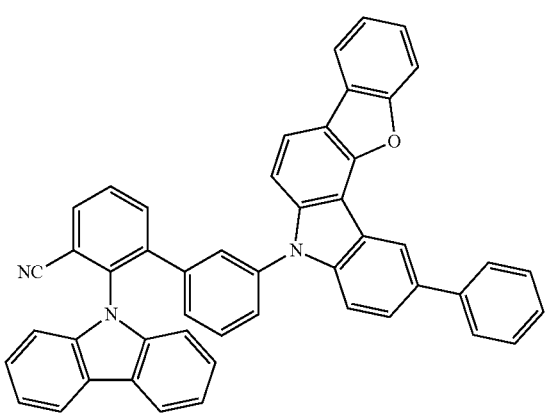

549
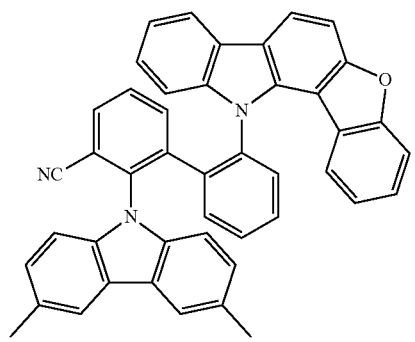
550
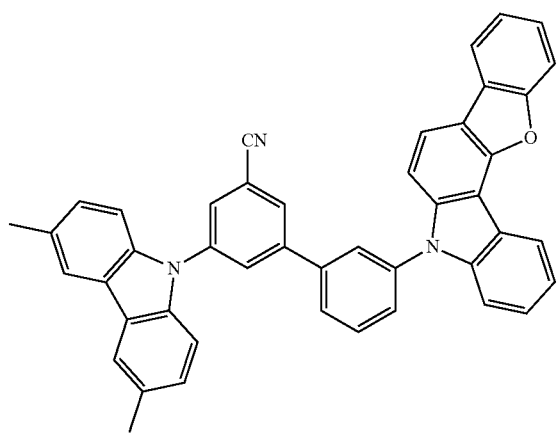
551
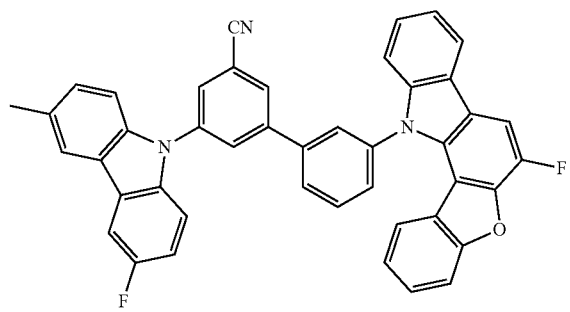
552
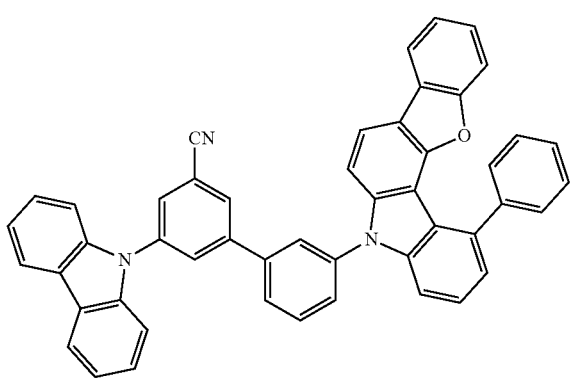
553
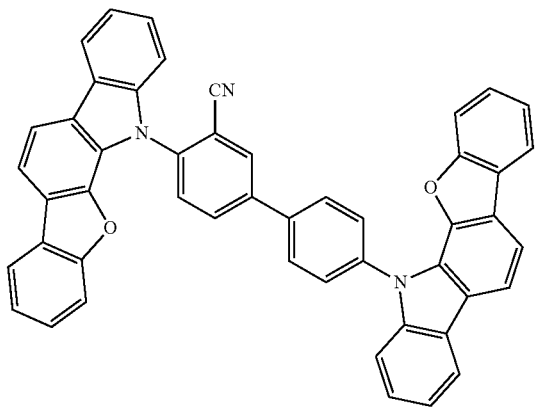
554
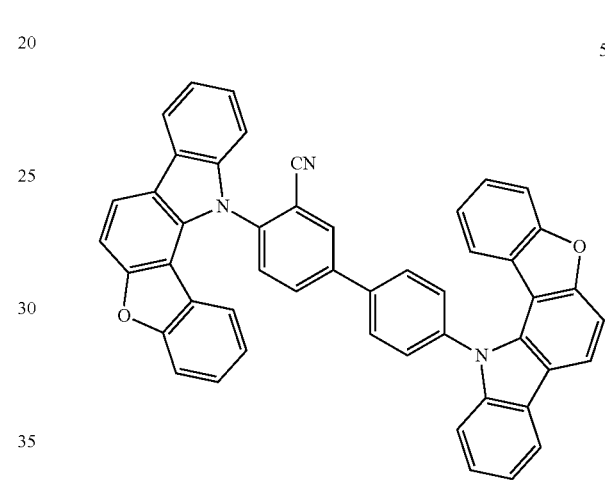
555
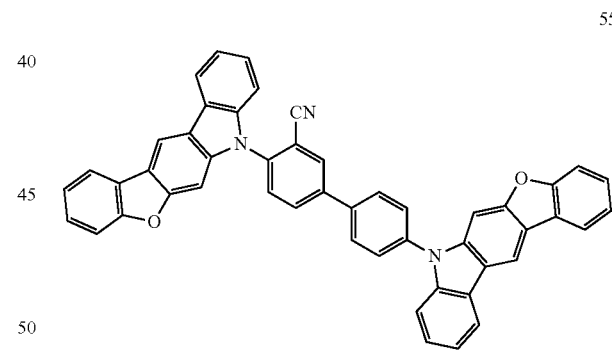
556
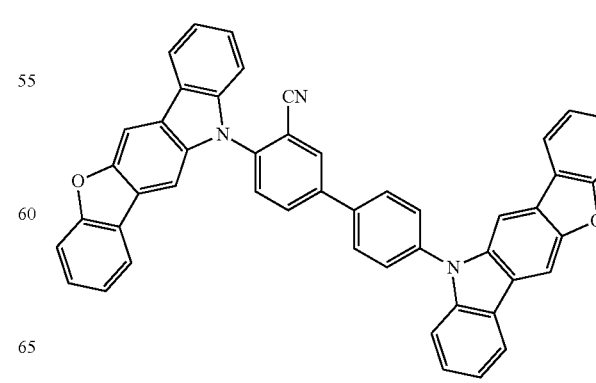

307
-continued
557
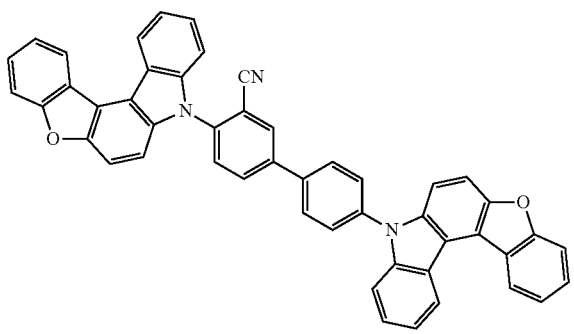
558
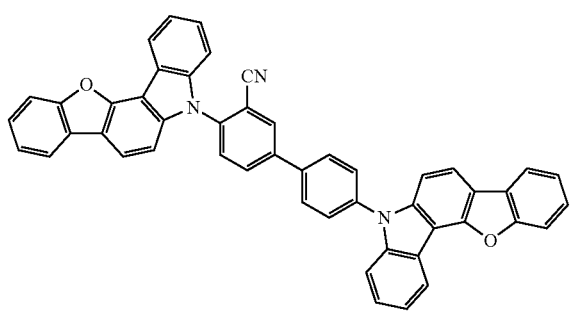
559
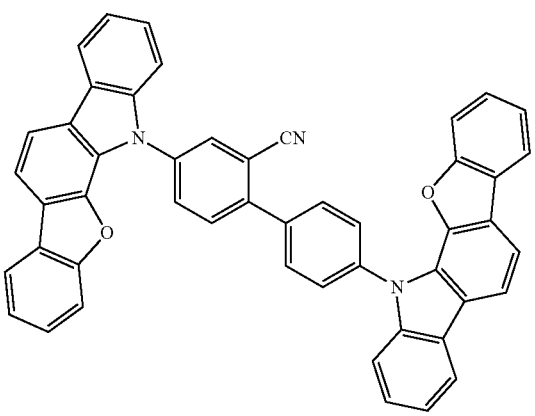
560
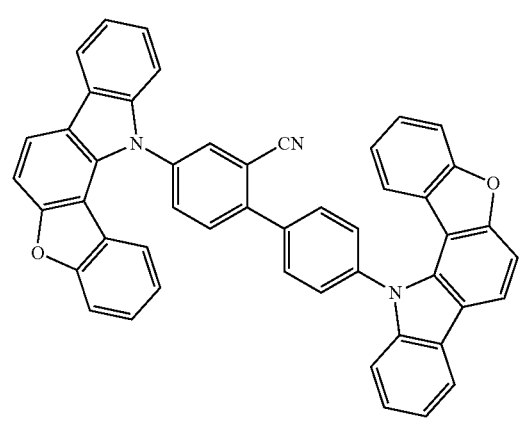
308
-continued
561
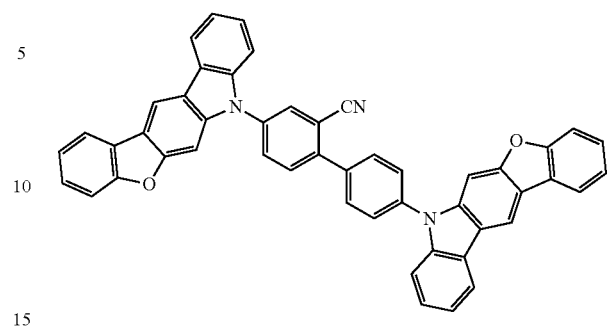
562
563
564

-continued
565
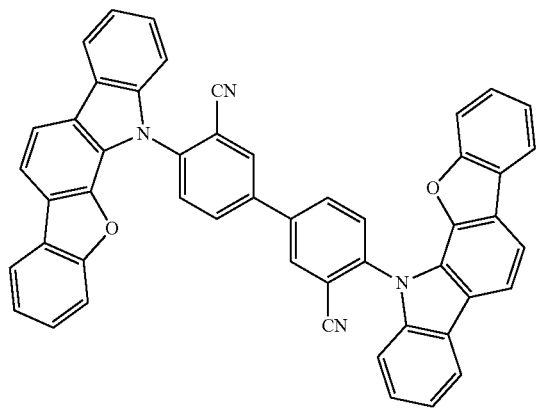
566
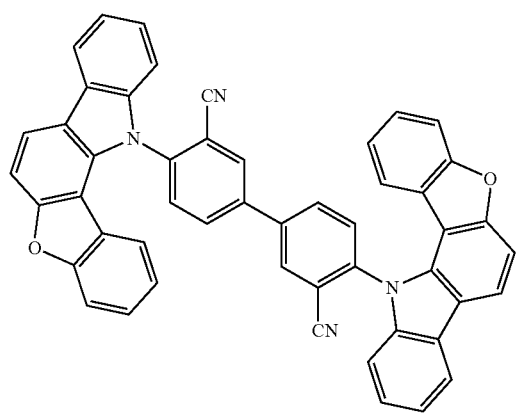
567
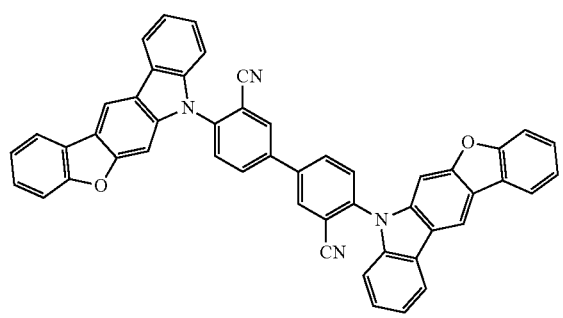
568
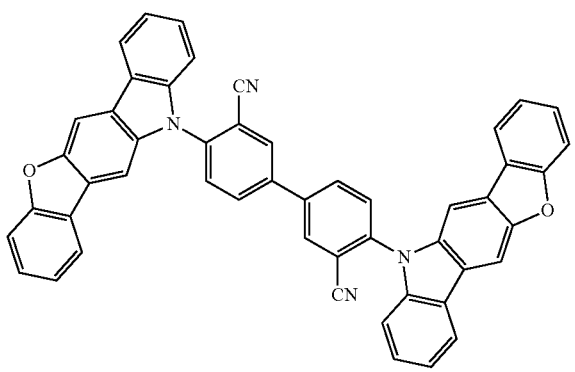
-continued
569
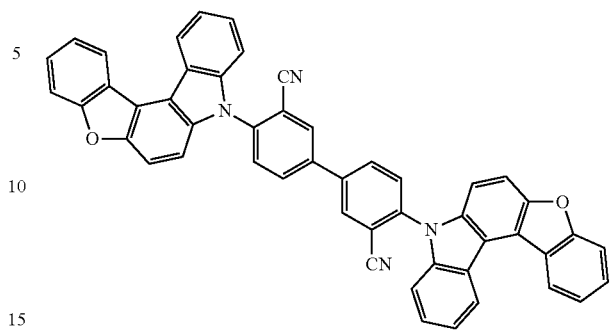
670
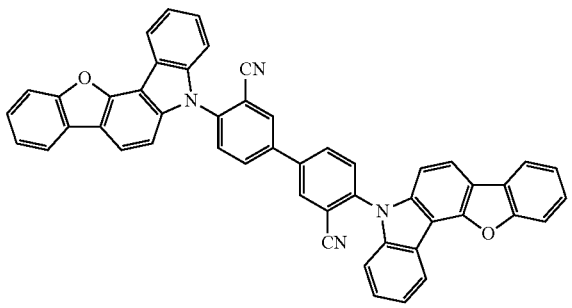
571
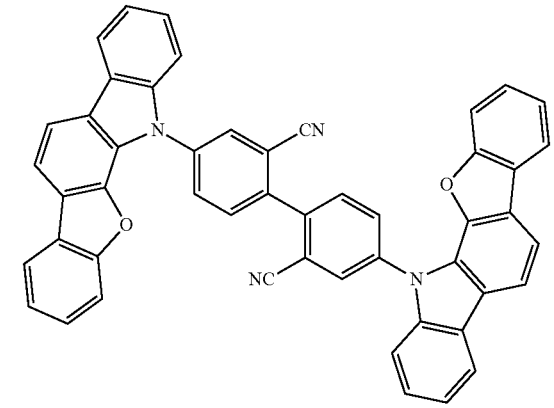
572
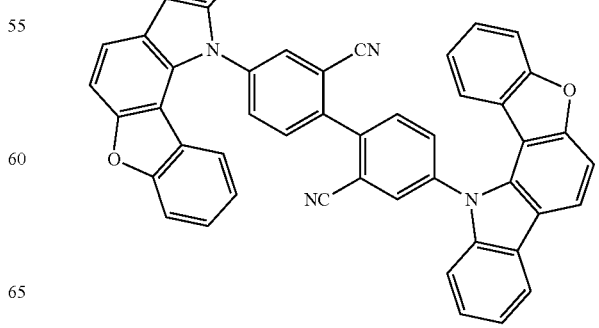

573
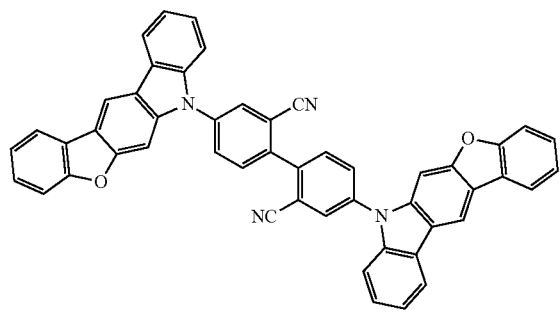
574
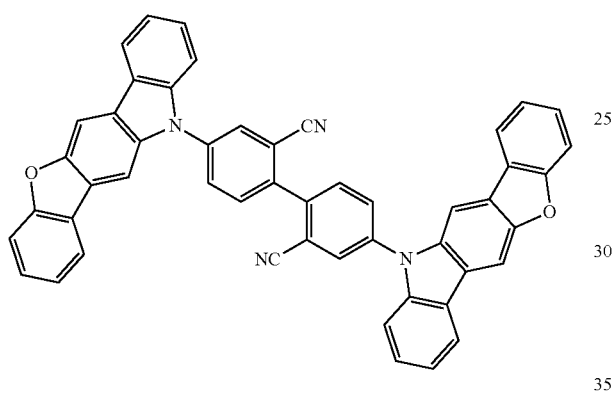
575
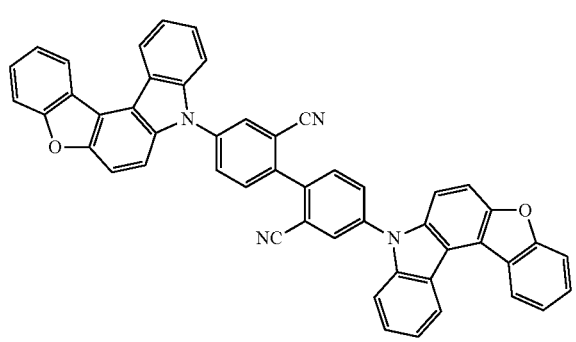
576
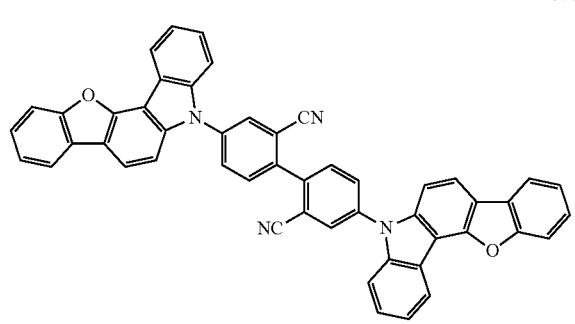
577
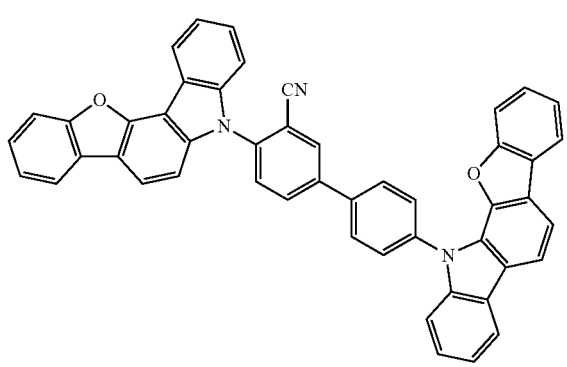
578
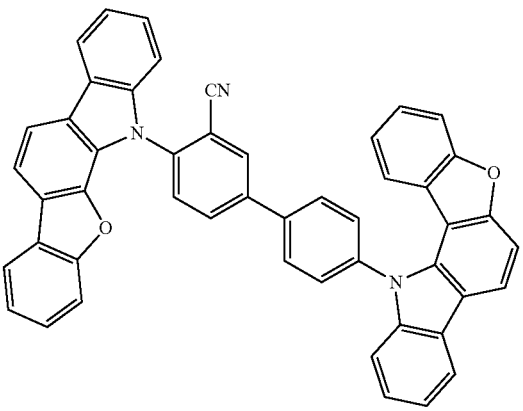
579
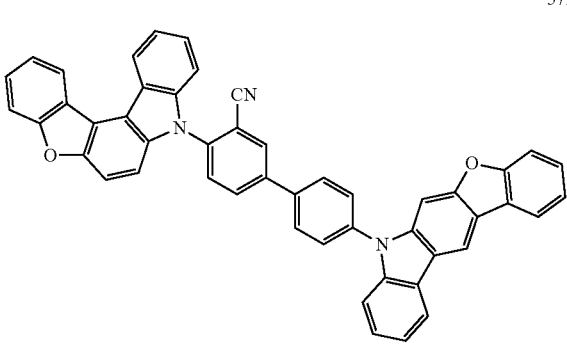
580
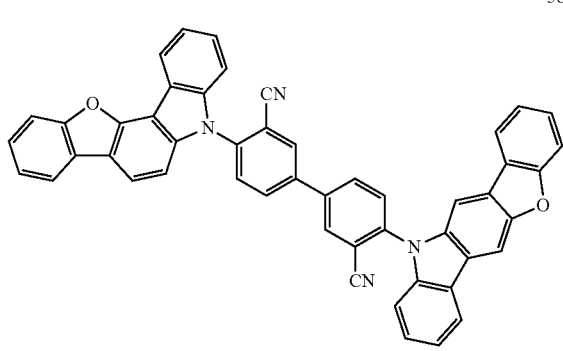

-continued
581
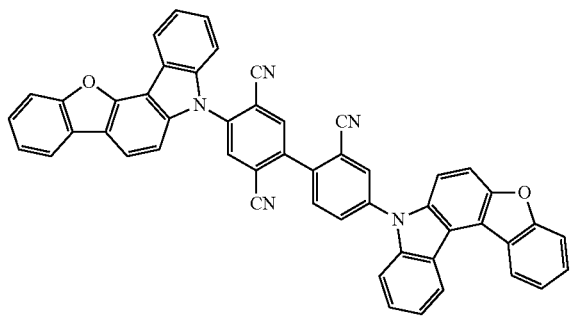
582
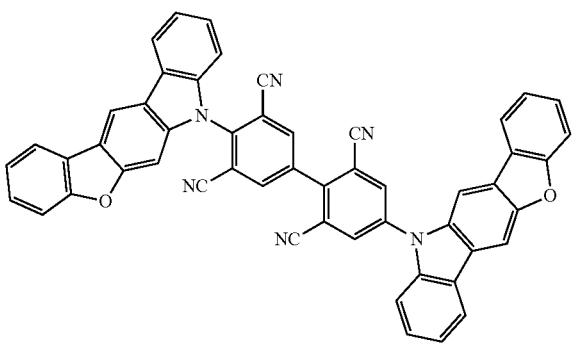
583
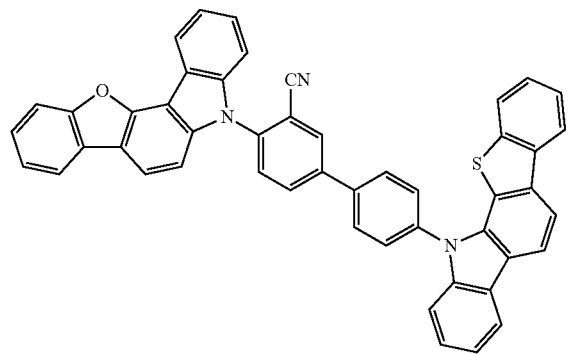
584
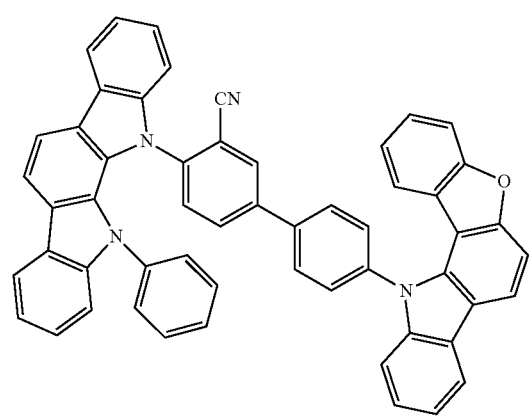
-continued
585
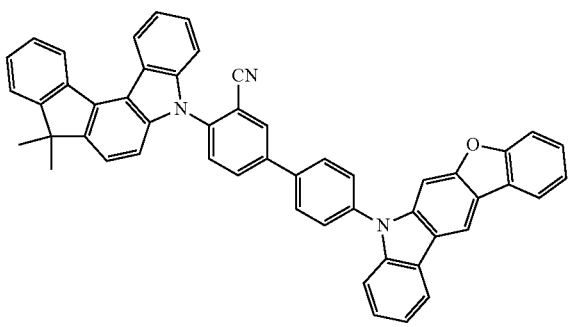
586
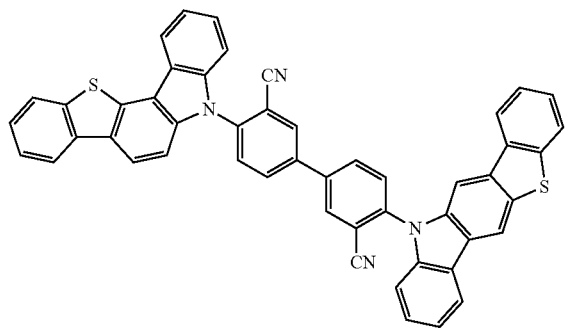
587
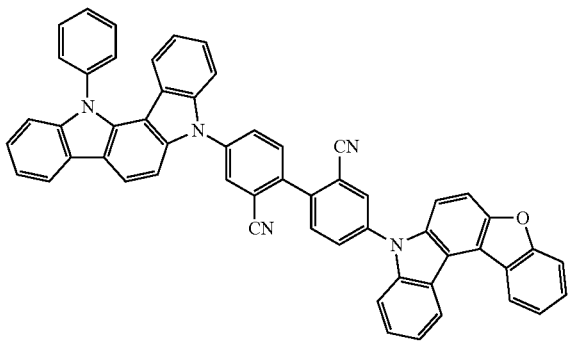
588
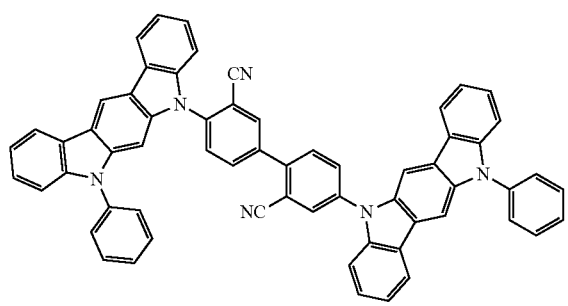

589
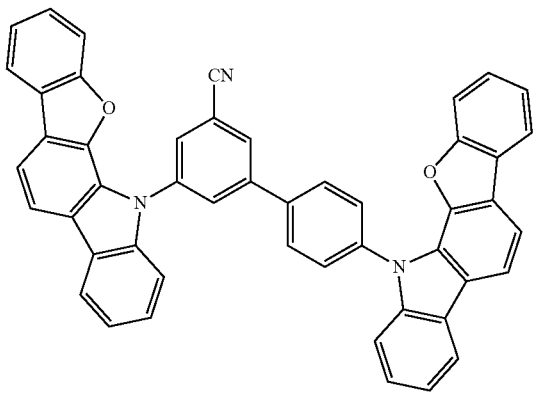
590
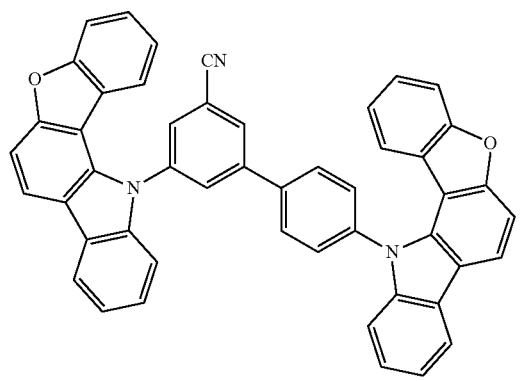
591
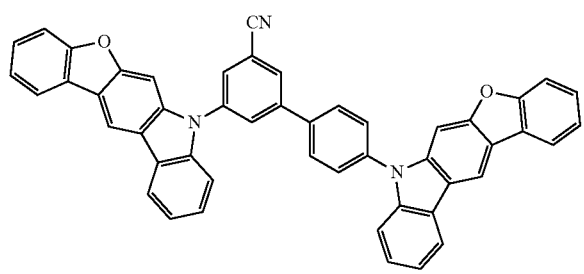
592
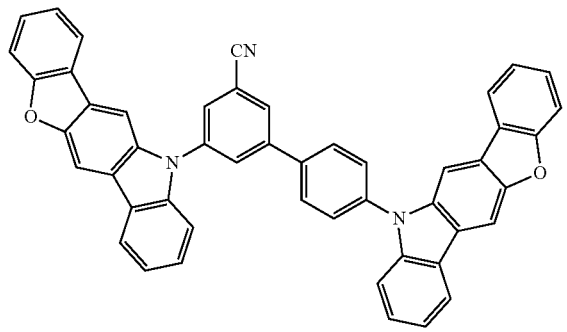
593
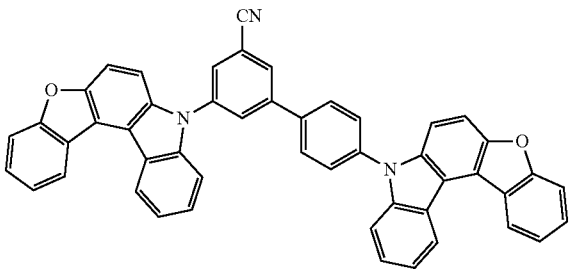
594
595
596
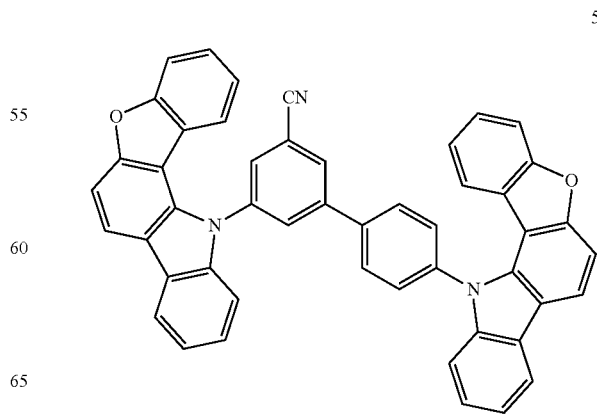

597
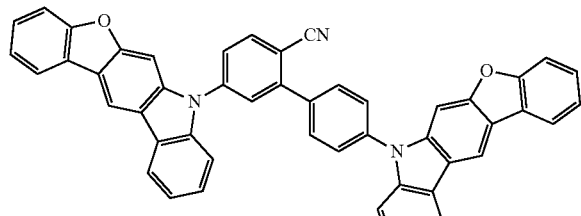
598
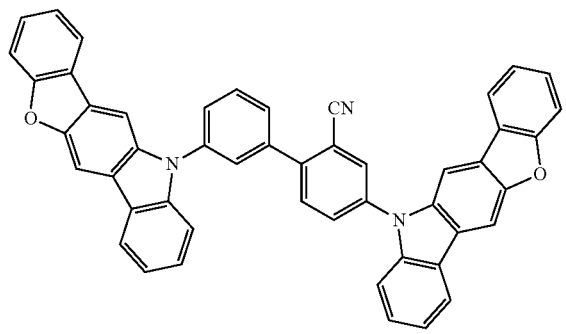
599
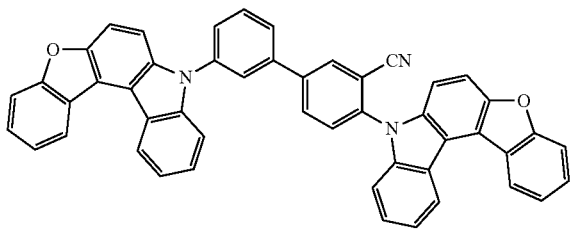
600
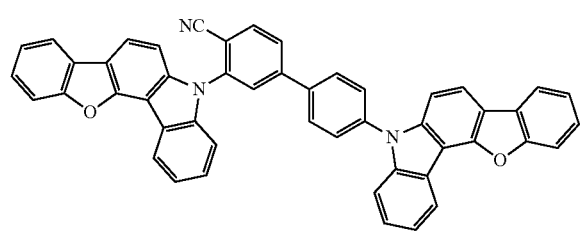
601
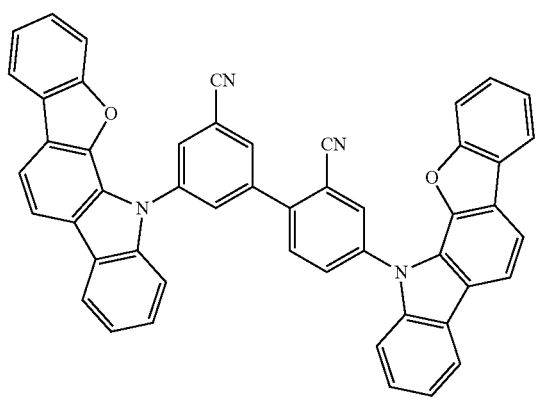
602
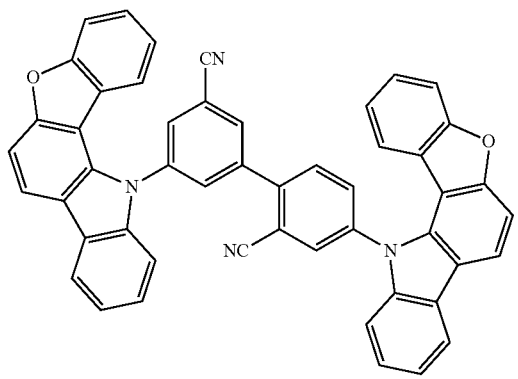
603
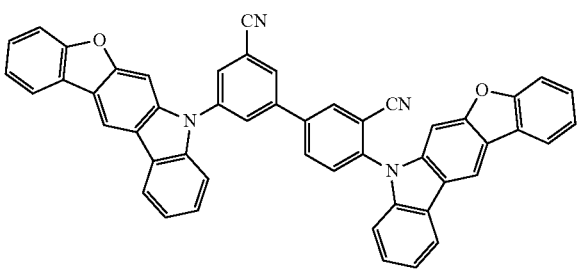
604
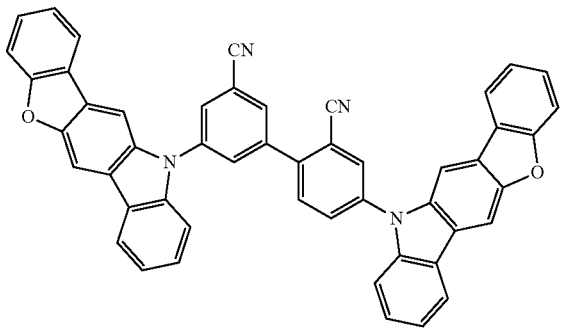
605
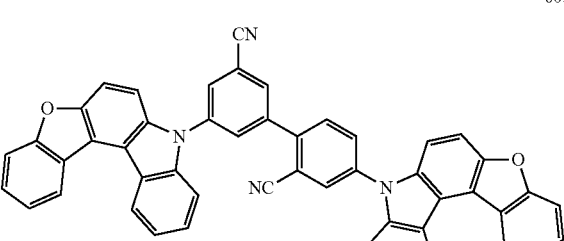
606
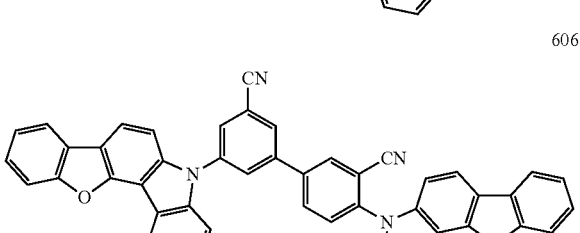

607
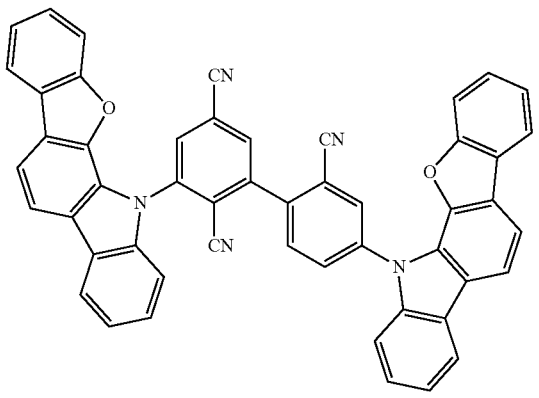
608
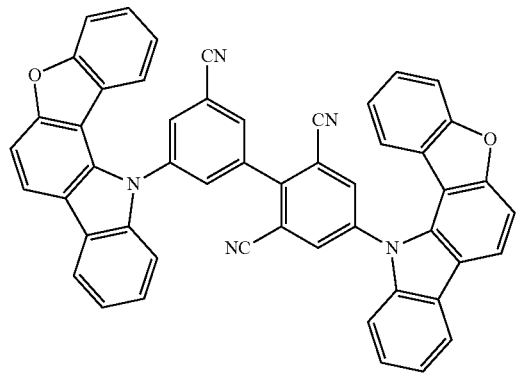
609
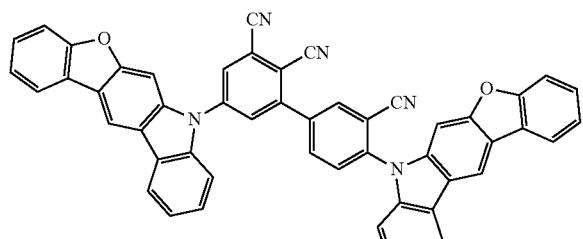
610
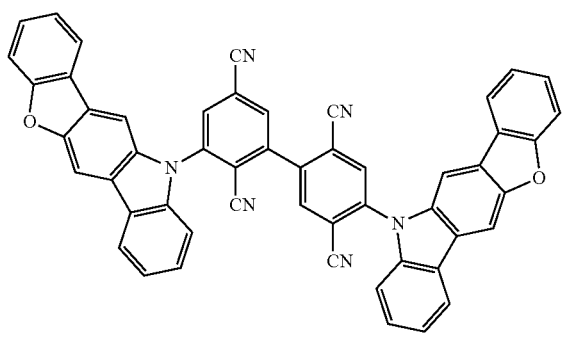
611
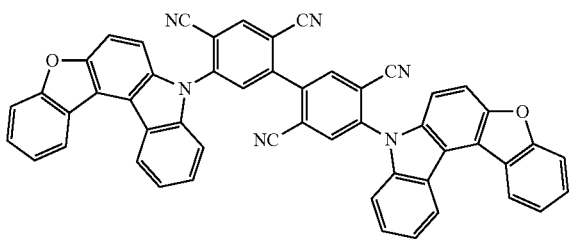
612
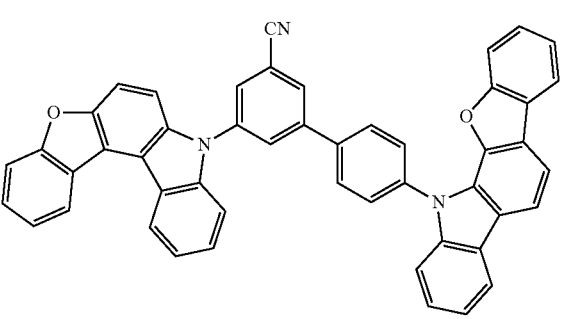
613
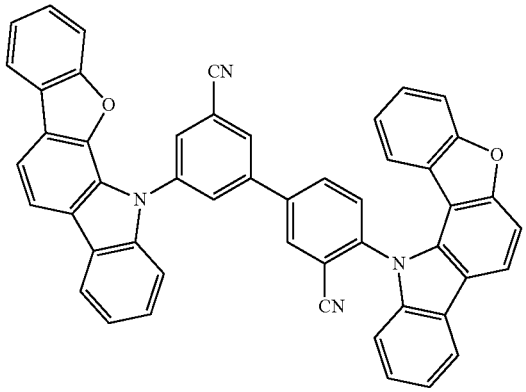
614
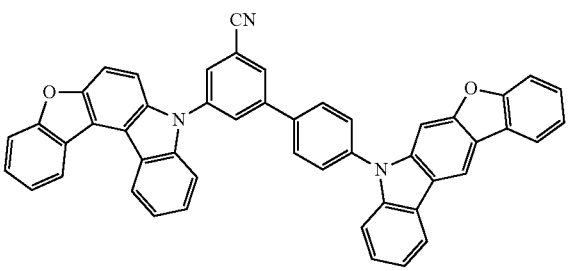
615

321
-continued
616
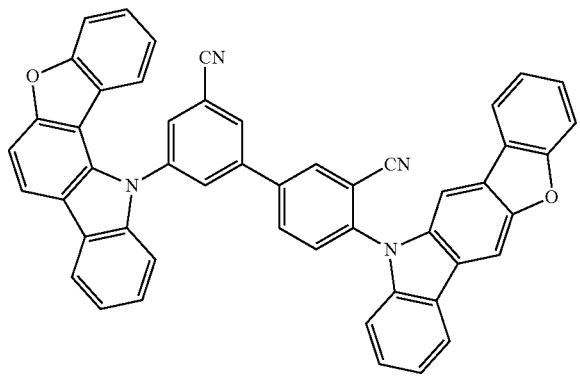
617
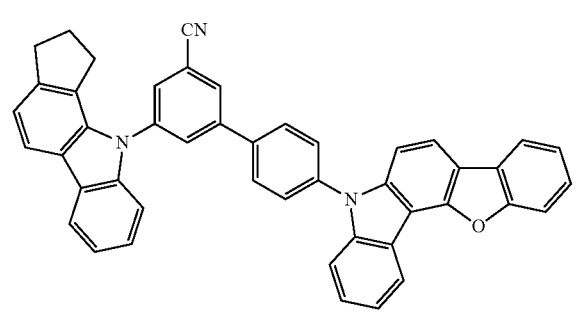
618
619
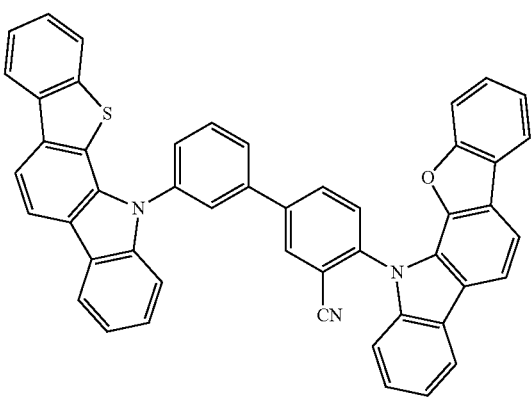
322
-continued
620
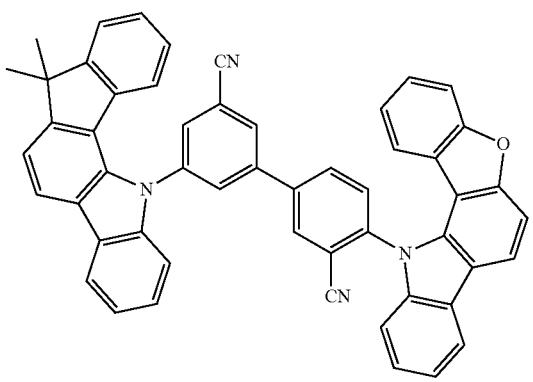
621
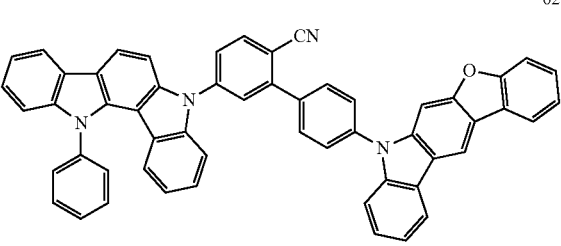
622
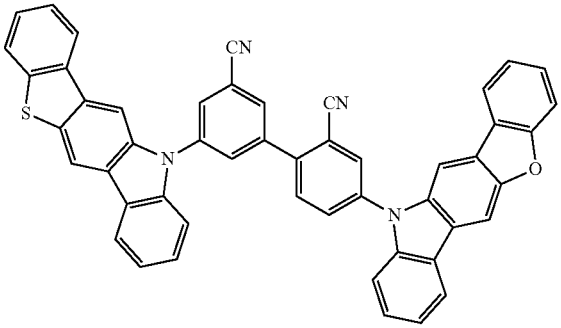
623
624
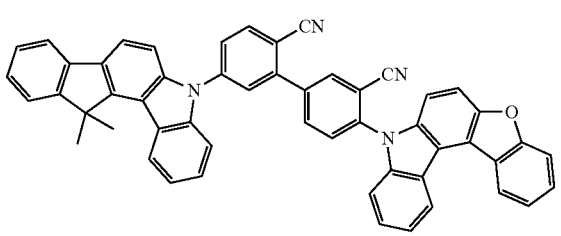

625
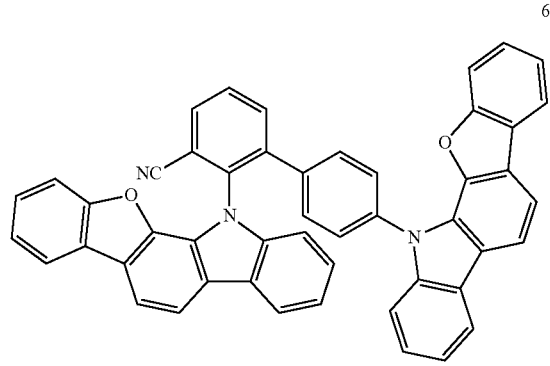
626
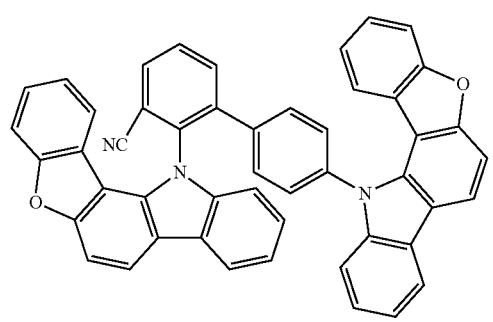
627
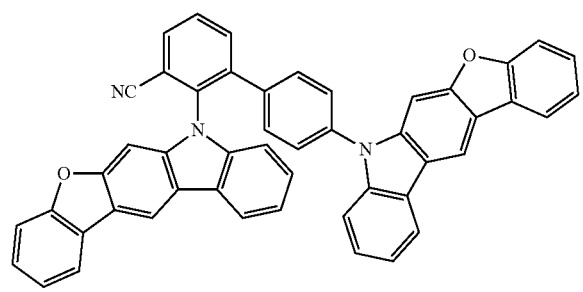
628
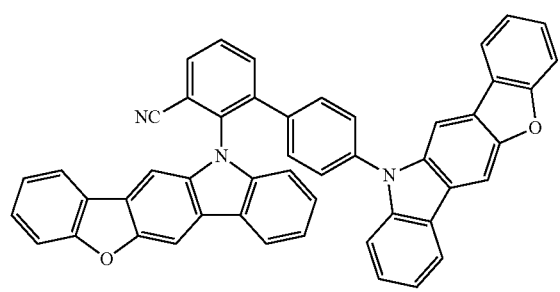
629
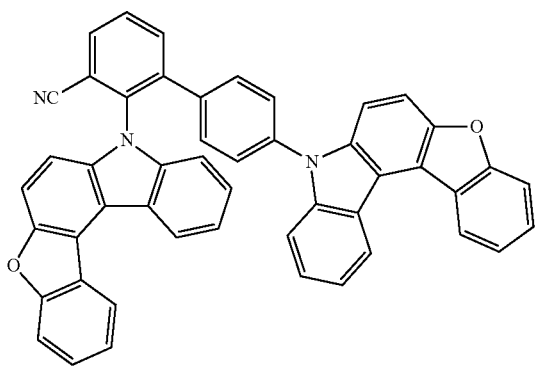
630
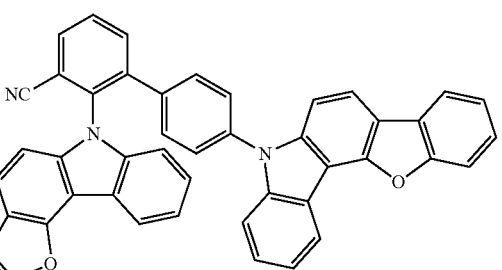
631
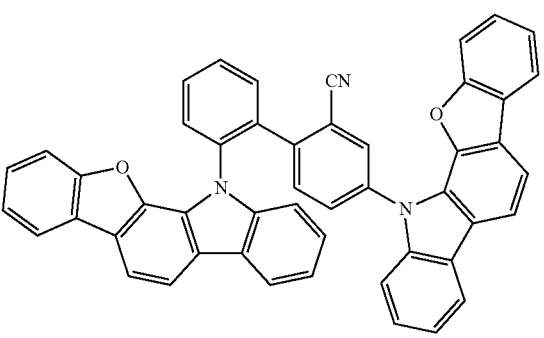
632
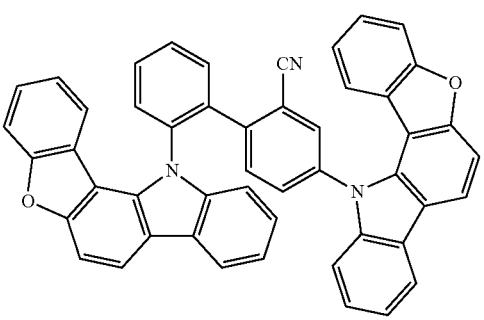

-continued
633
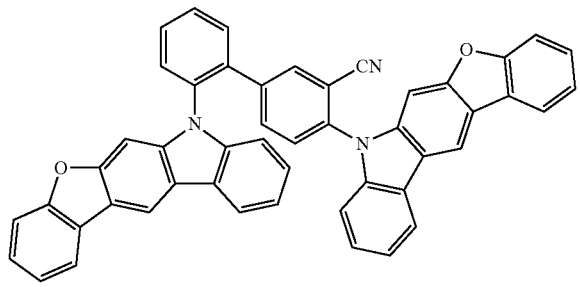
634
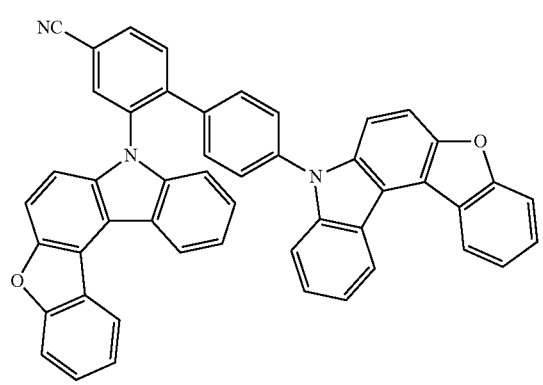
635
636
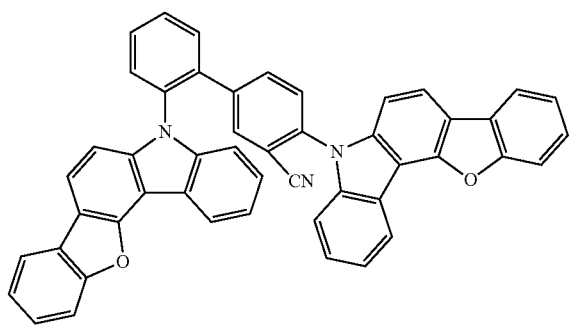
-continued
637
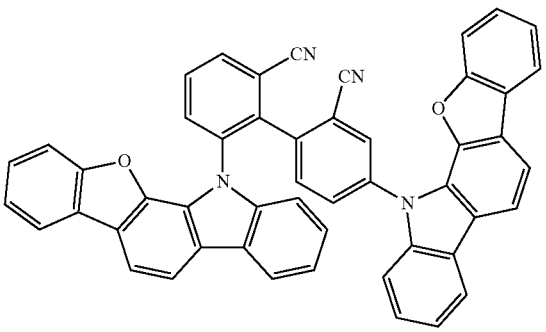
638
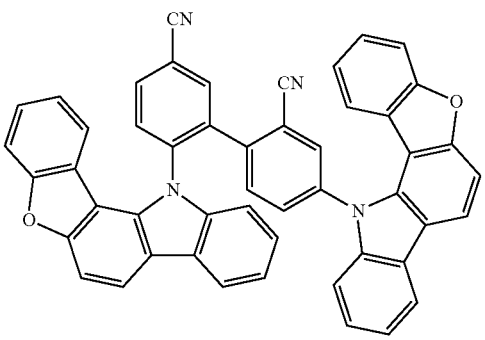
639
640
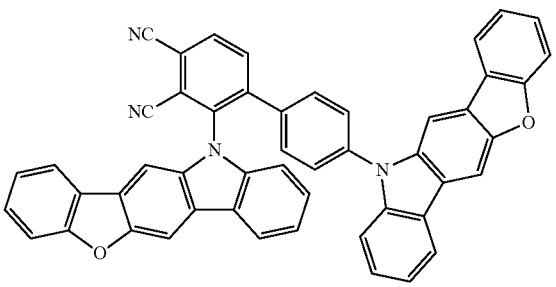

641
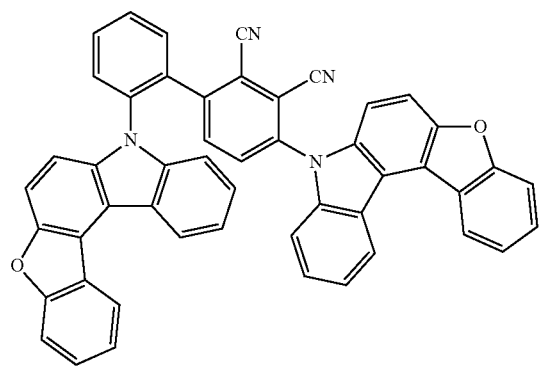
642
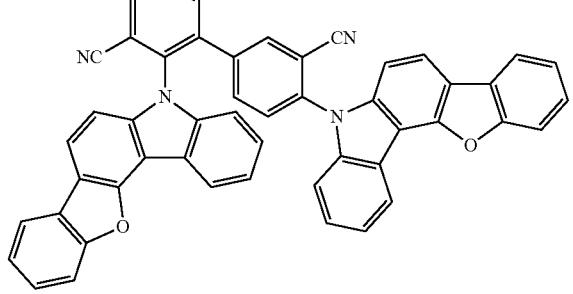
643
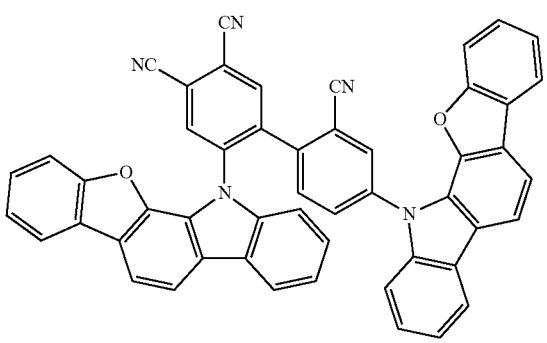
644
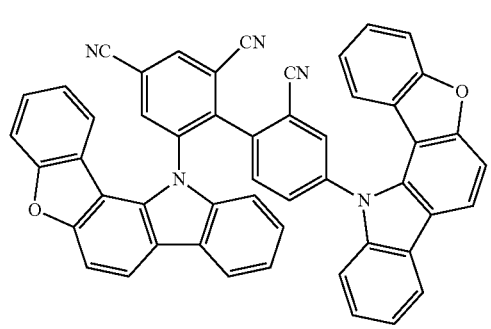
645
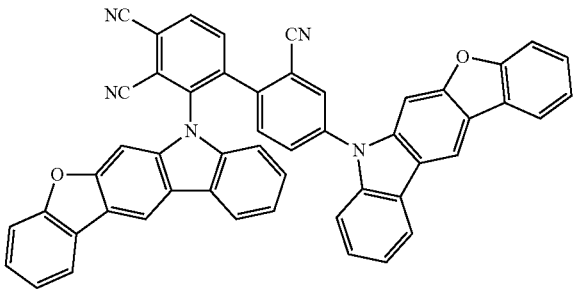
646
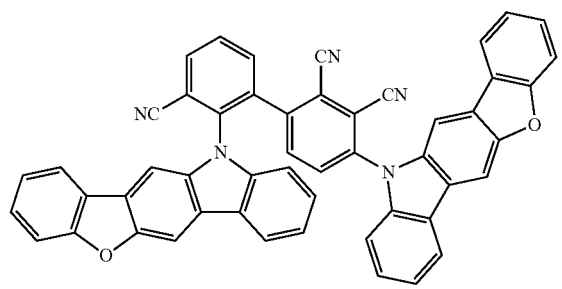
647
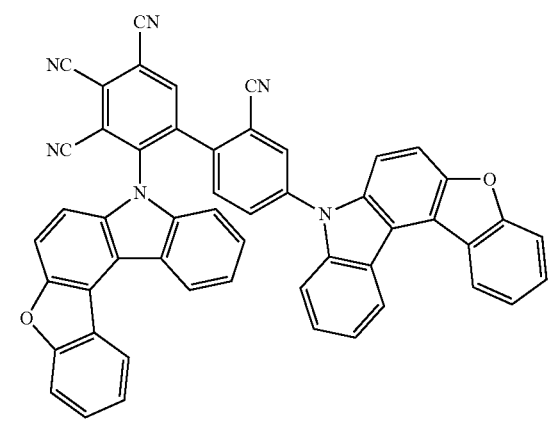
648
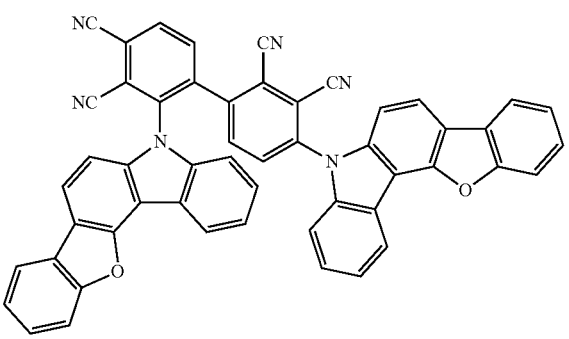

329
-continued
649
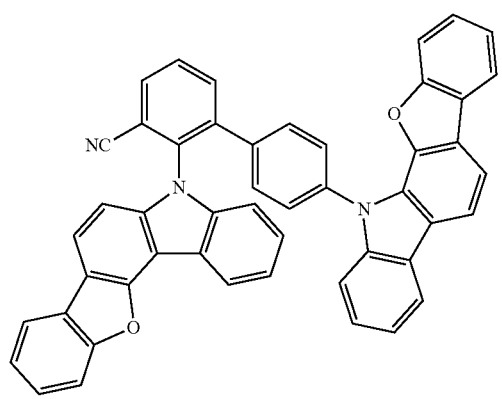
650
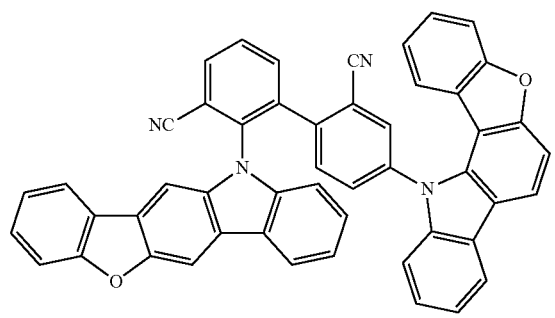
651
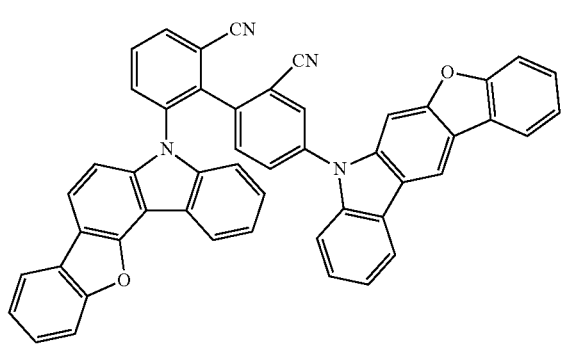
652
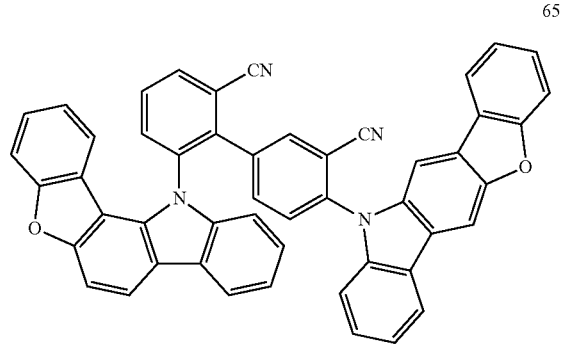
330
-continued
653
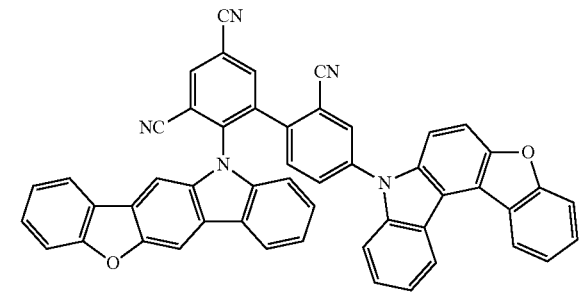
654
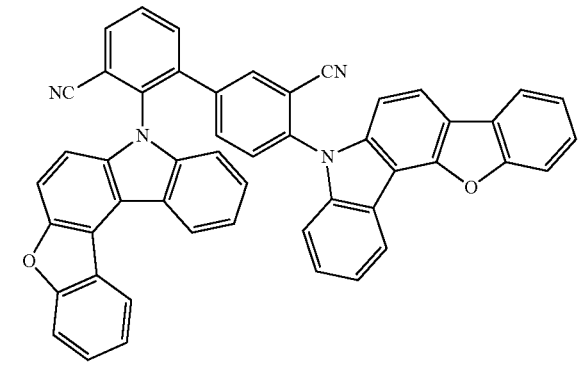
655
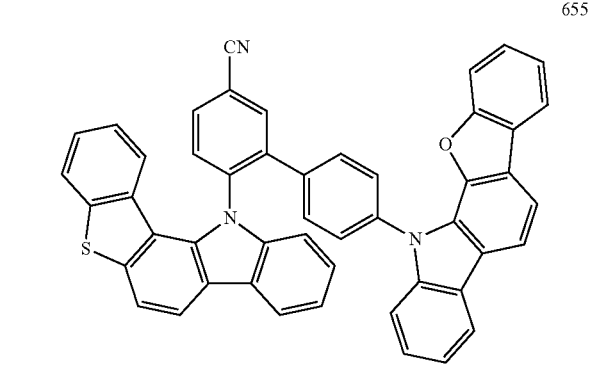
656
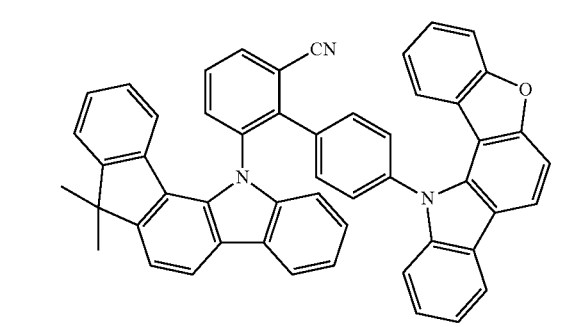

331
-continued
657
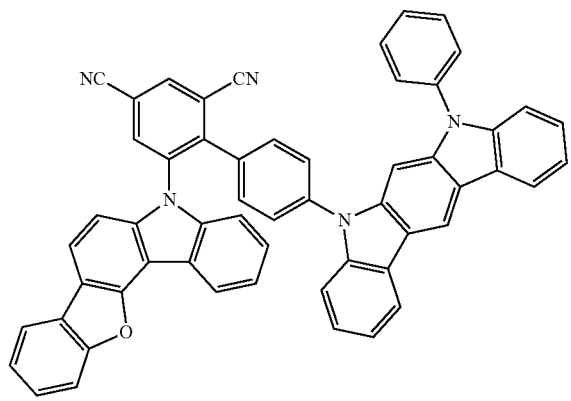
658
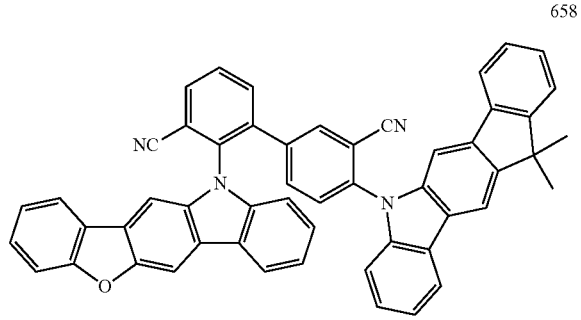
659
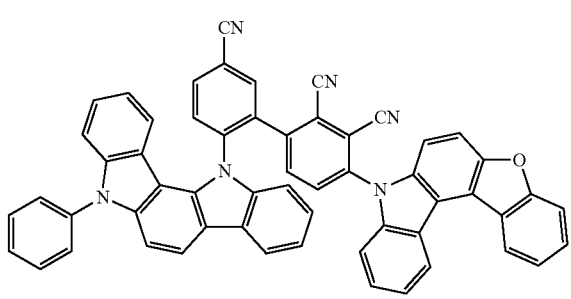
660
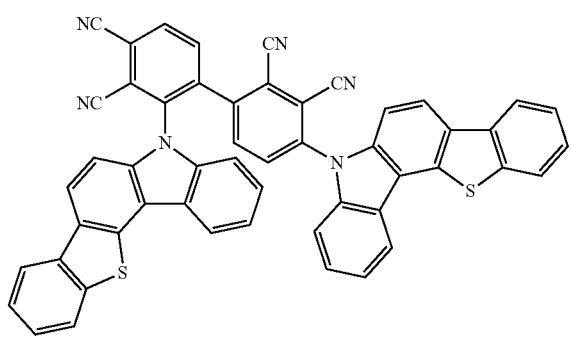
332
-continued
661
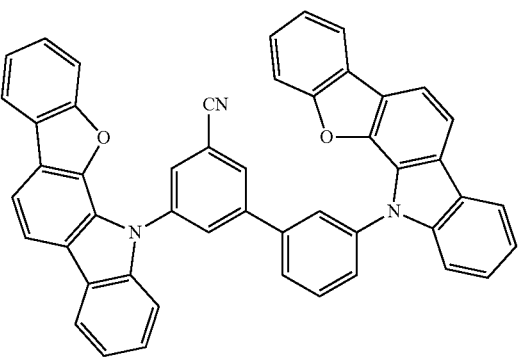
662
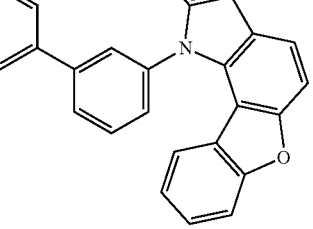
663
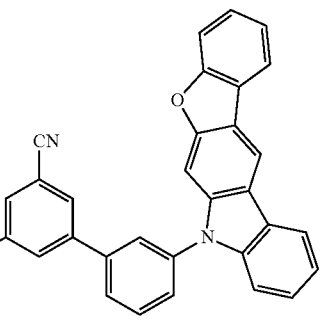
664
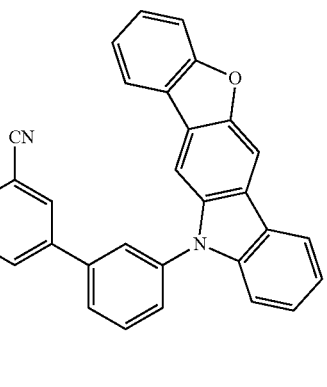

333
-continued
665
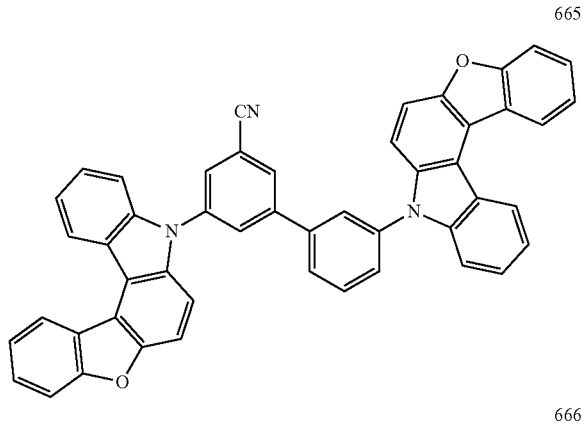
666
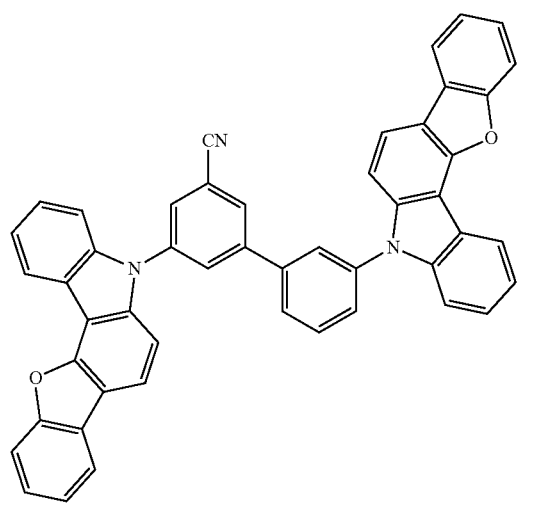
667
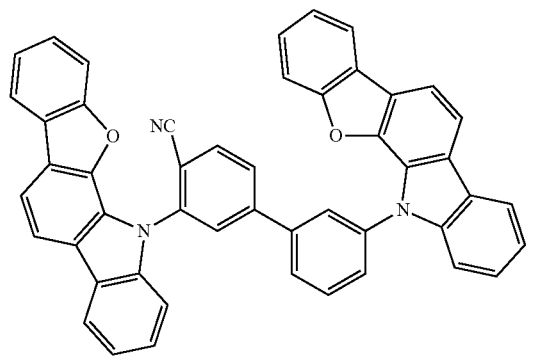
668
334
-continued
669
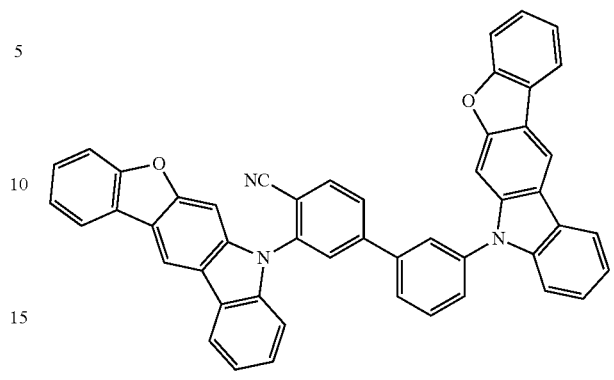
670
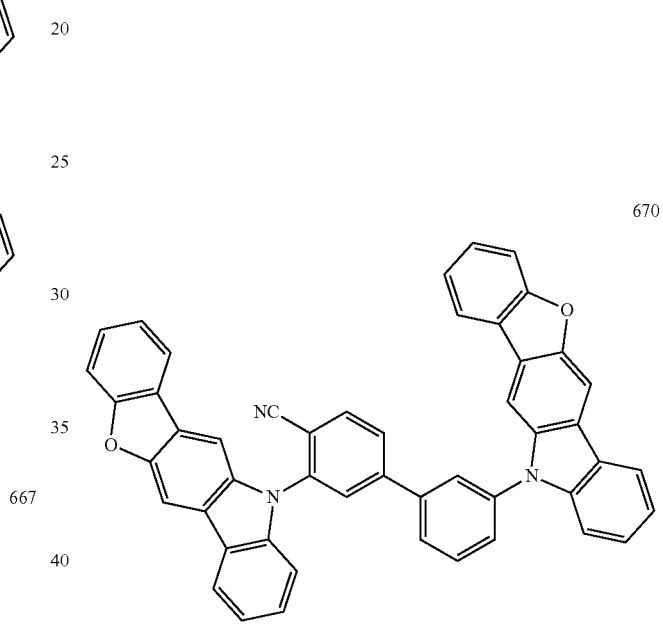
671
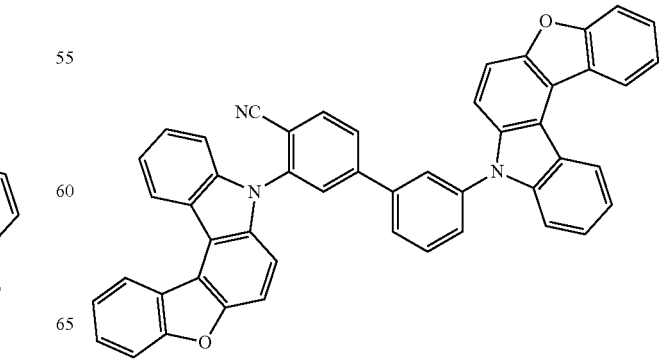

335
-continued
672
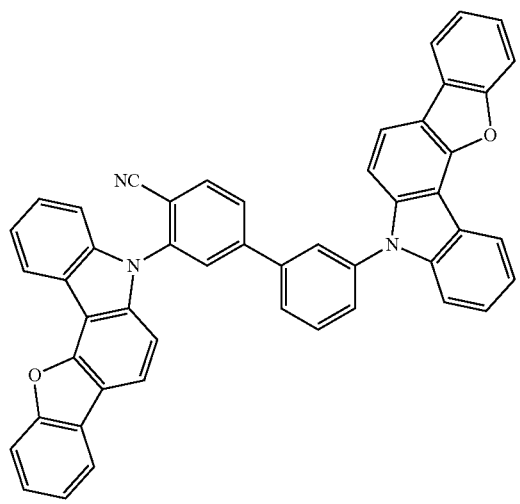
673
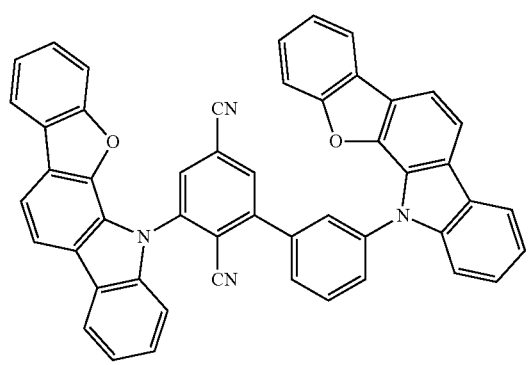
674
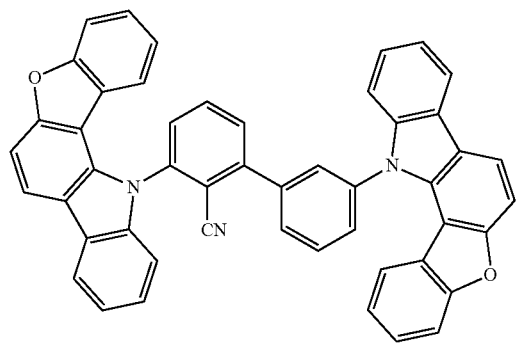
675
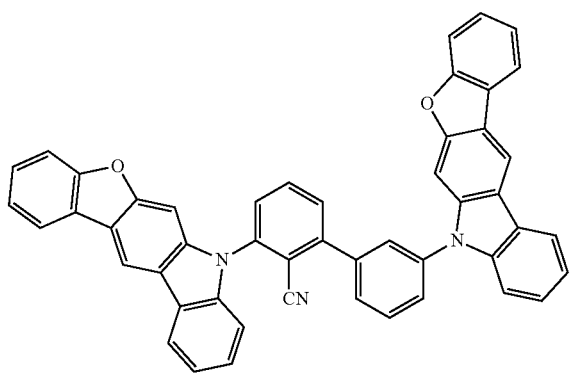
336
-continued
676
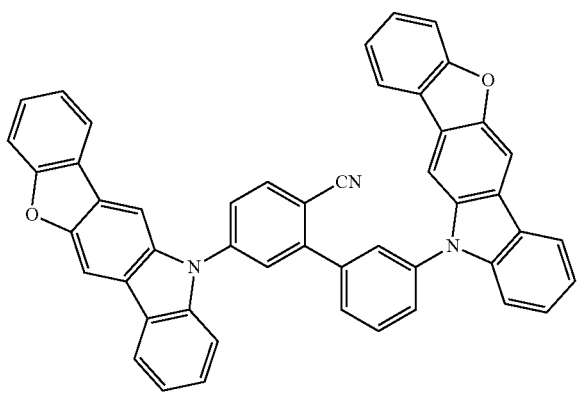
677
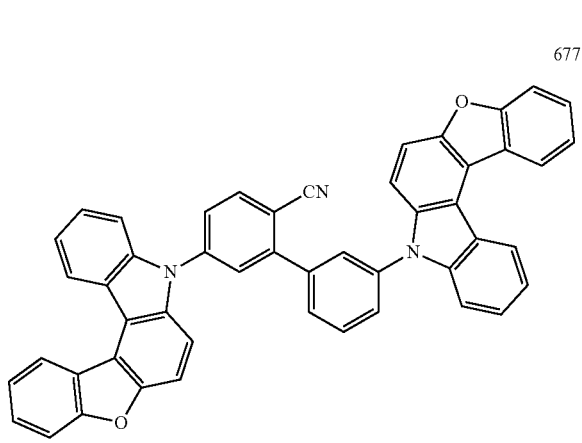
678
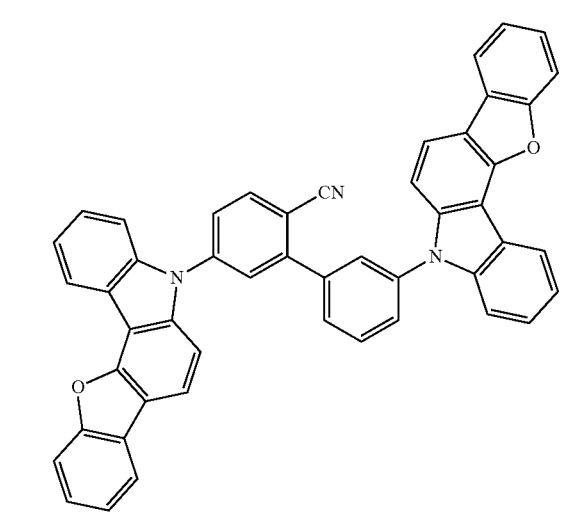

US 11,925,115 B2
337
-continued
679
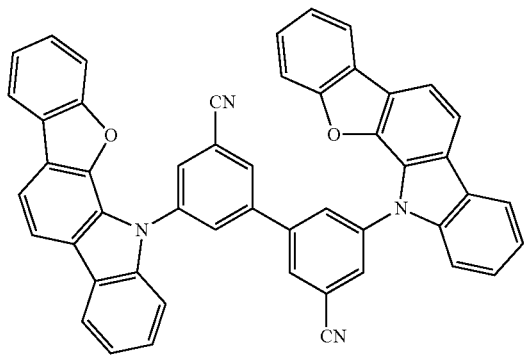
680
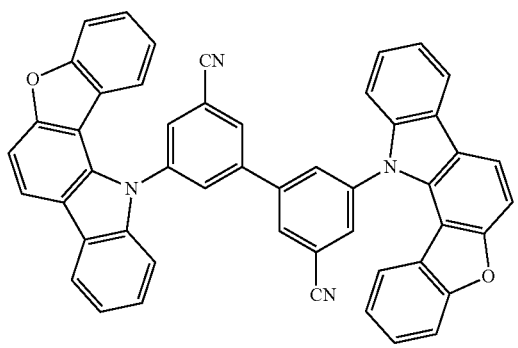
681
682
338
-continued
683
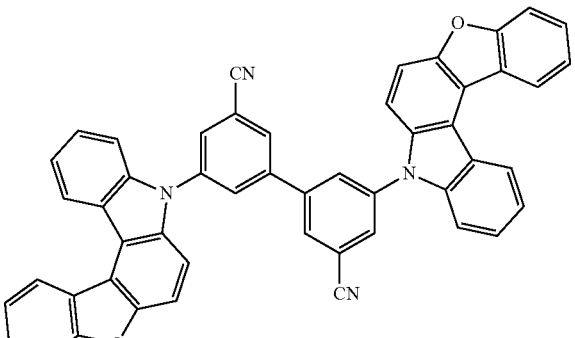
684
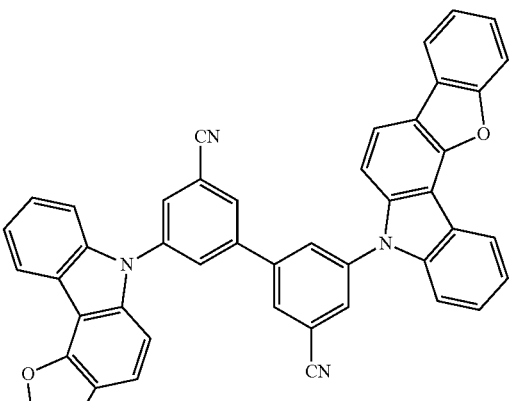
685
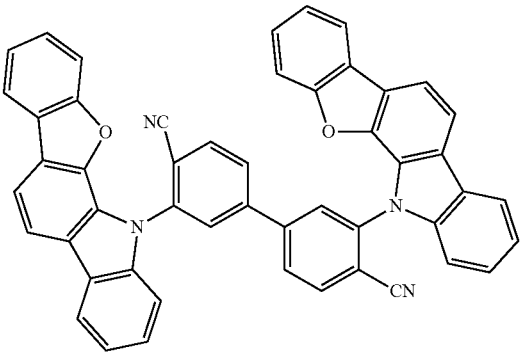
686
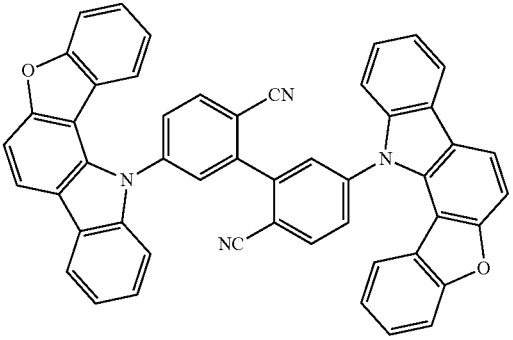

687
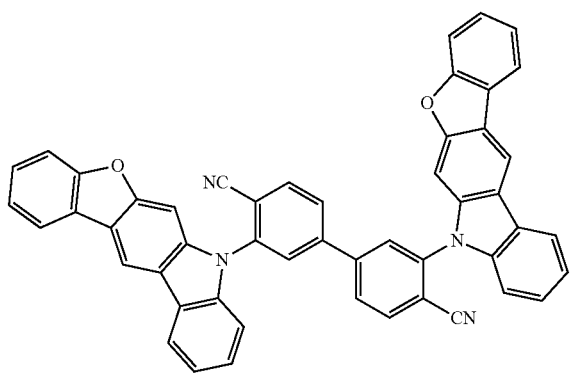
688
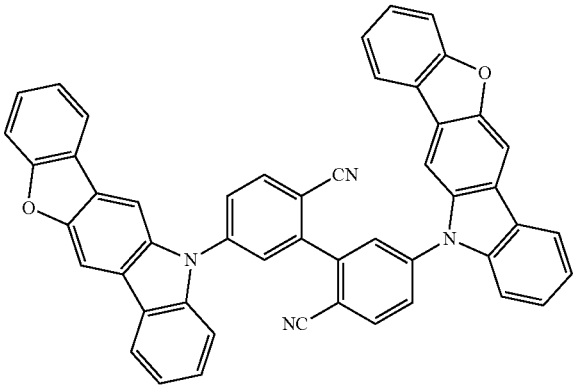
689
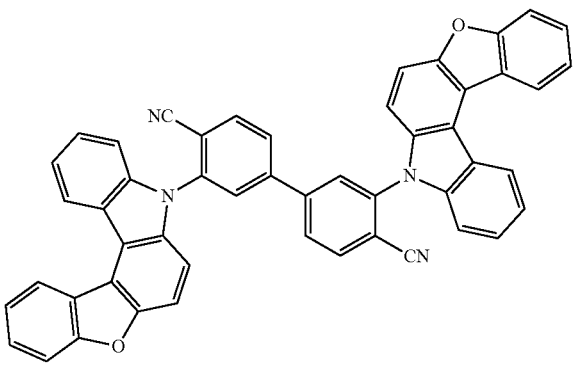
690
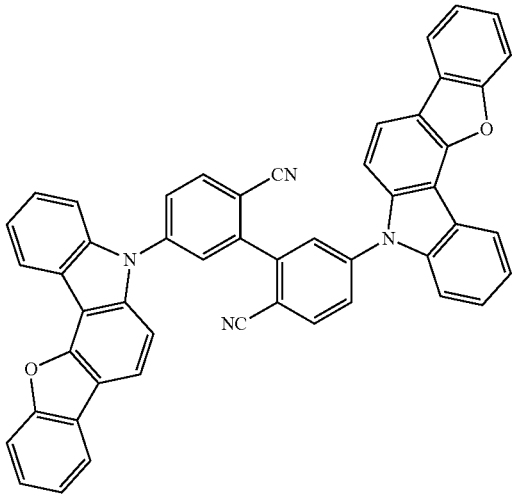
691
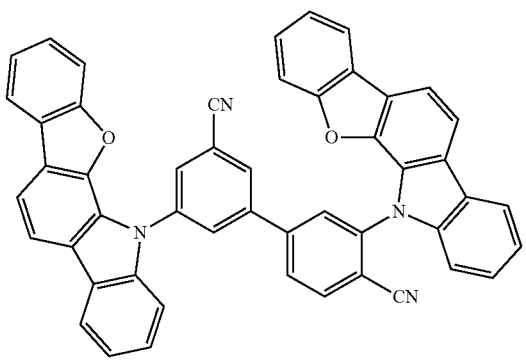
692
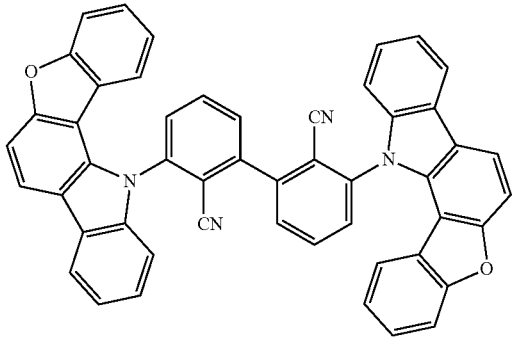
693
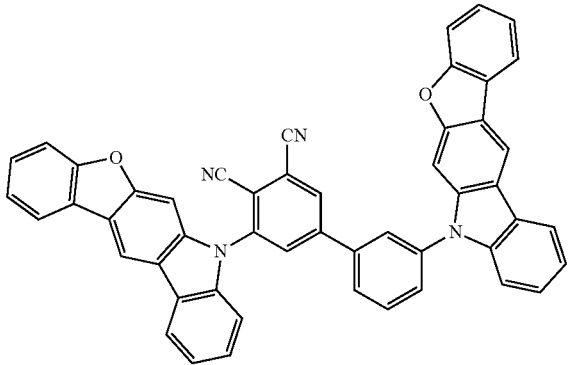

694
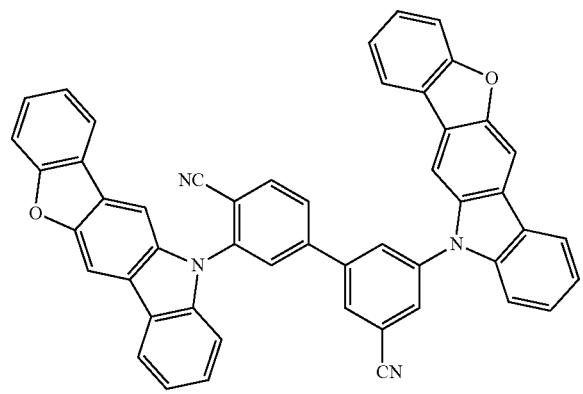
695
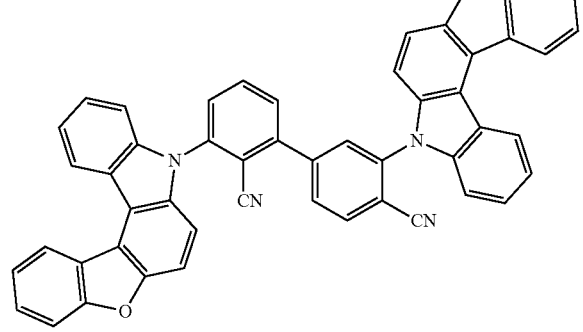
696
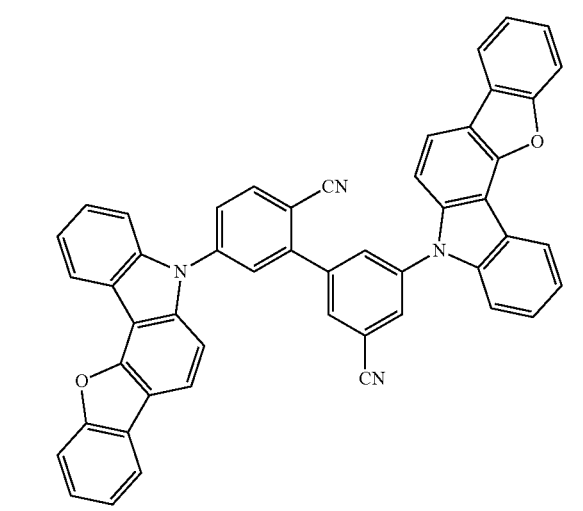
697
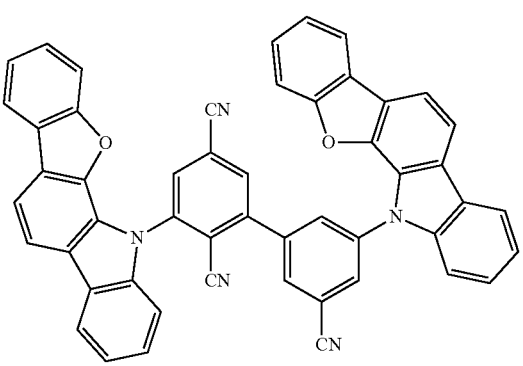
698
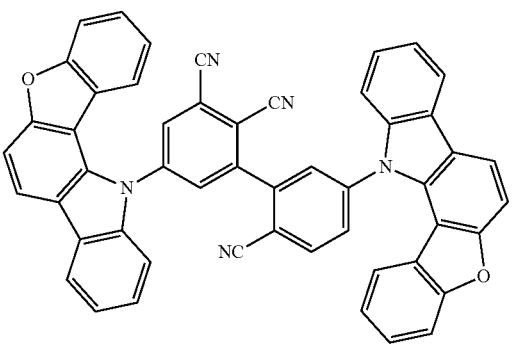
699
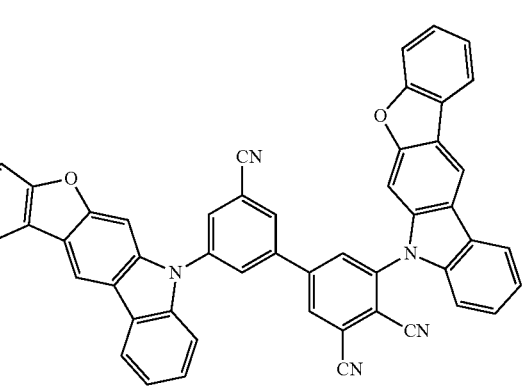
700
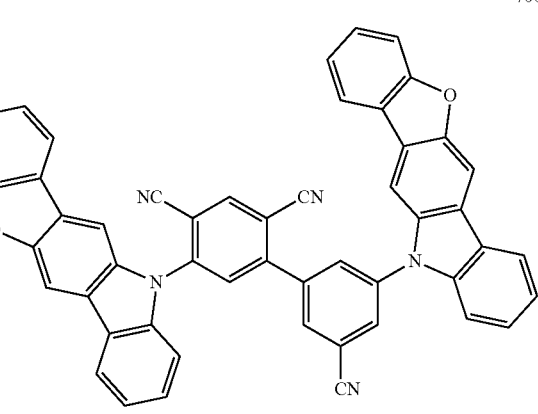

-continued
701
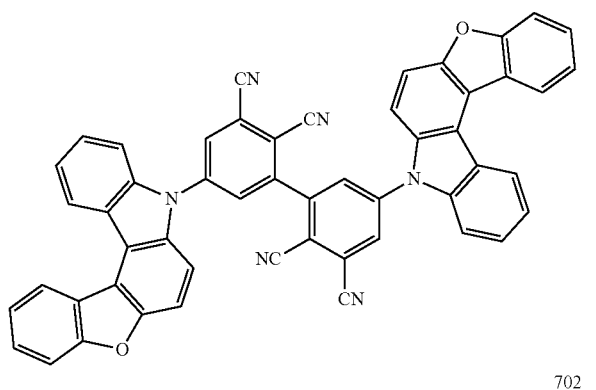
702

703
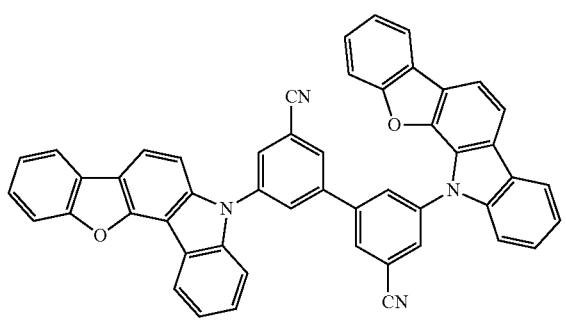
704
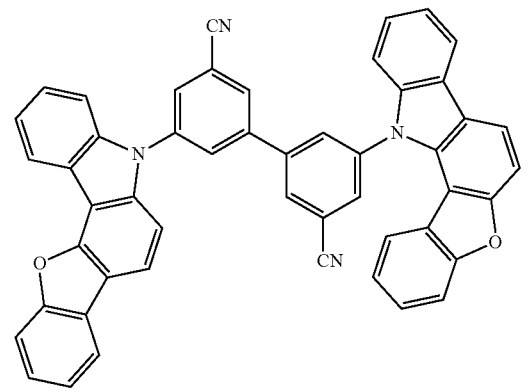
-continued
705
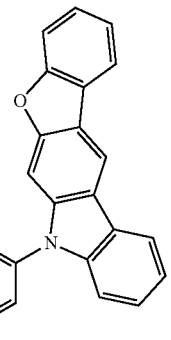
706
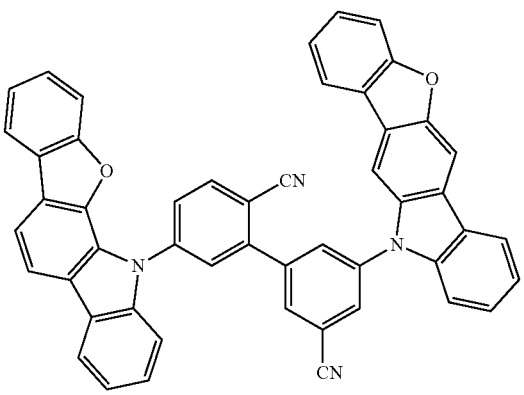
707
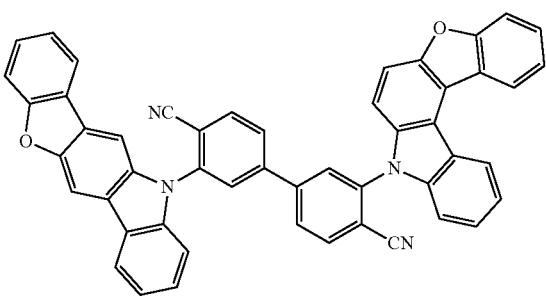
708
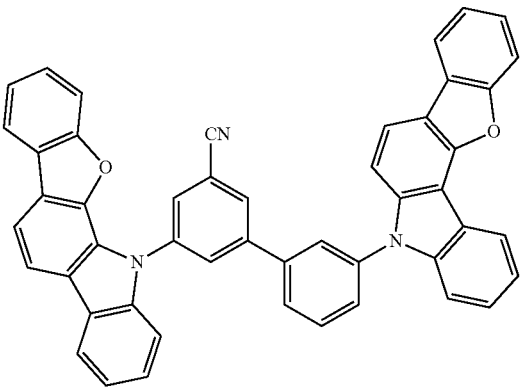

-continued
709
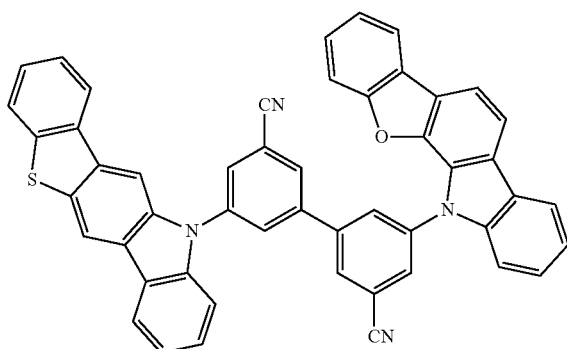
710
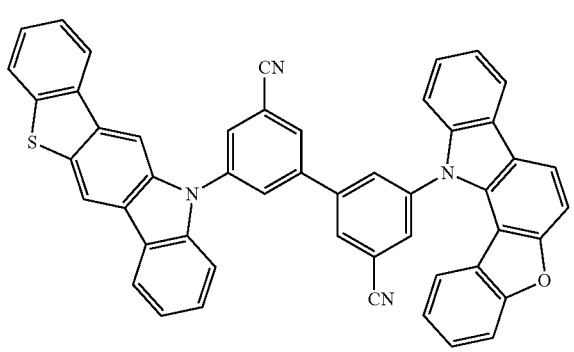
711
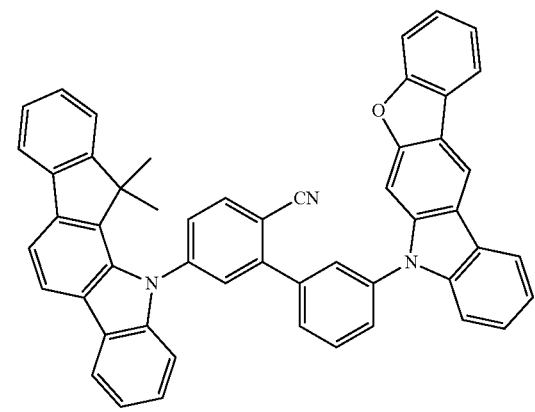
712
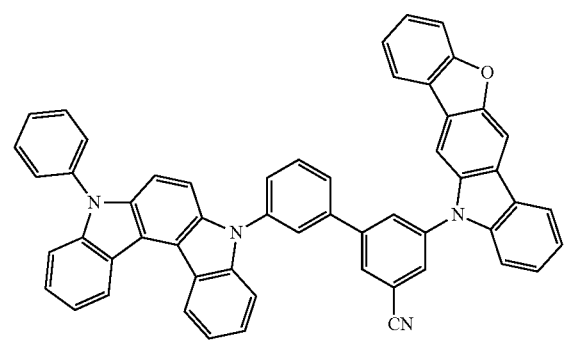
-continued
713
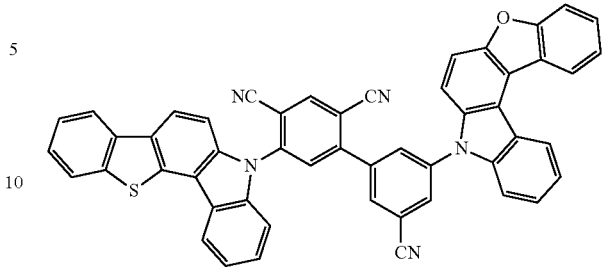
714
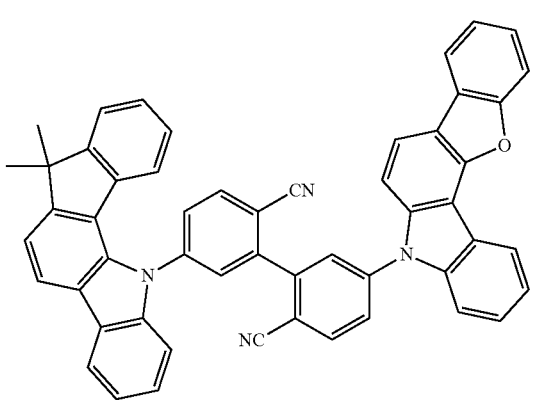
715
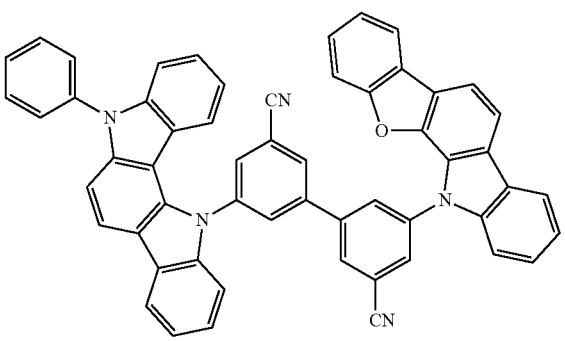
716
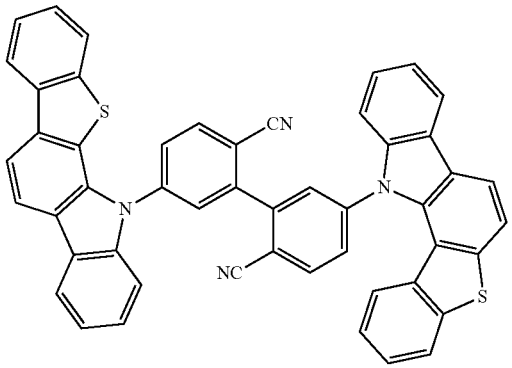

-continued
717
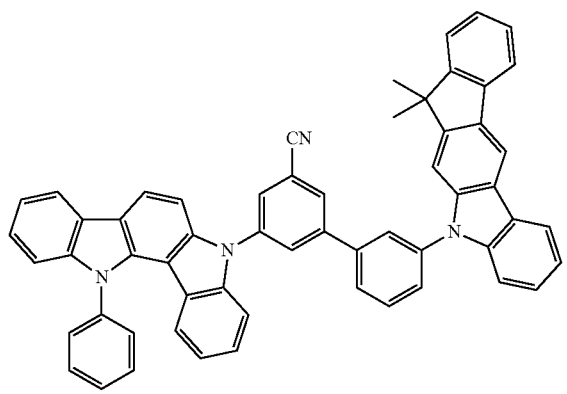
718
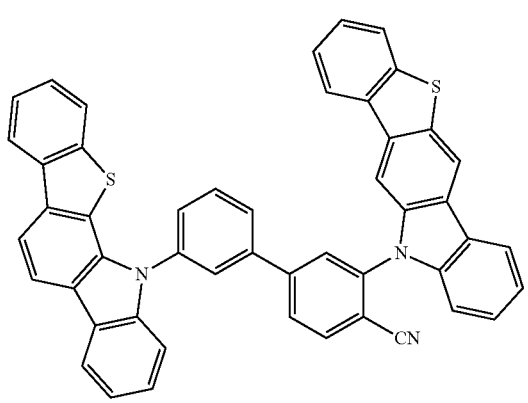
719
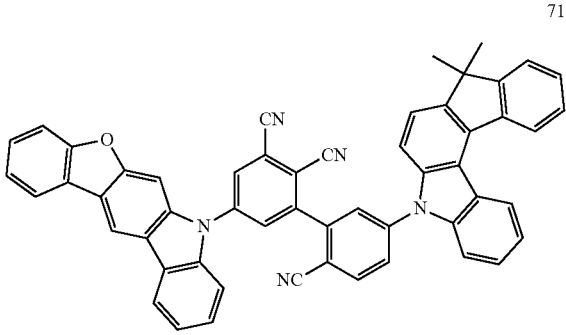
720
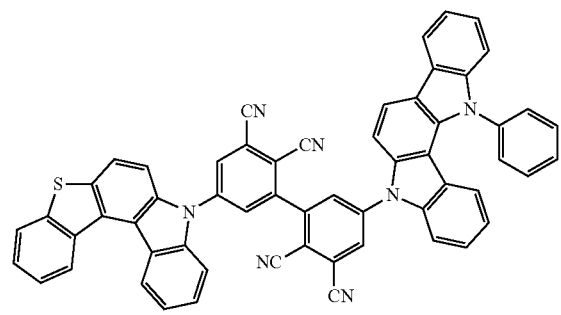
-continued
721
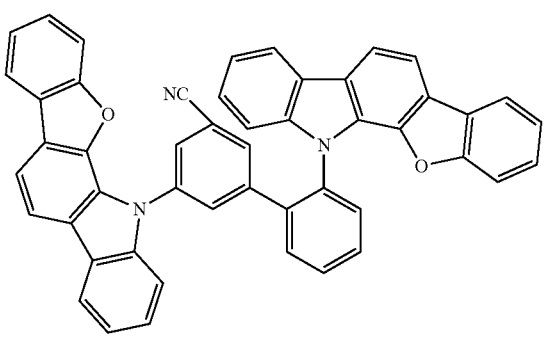
722
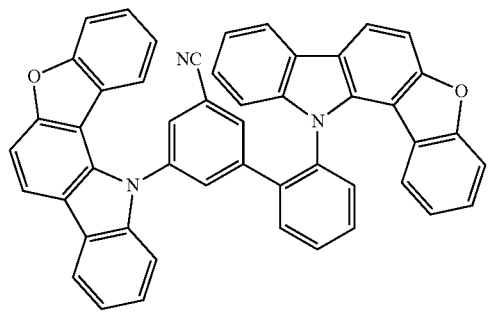
723
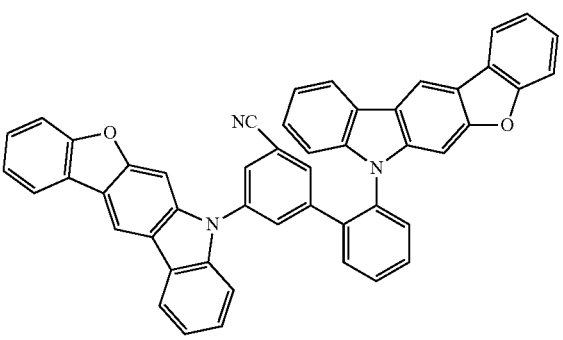
724
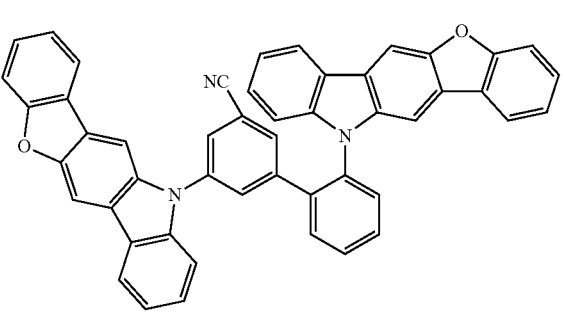

725
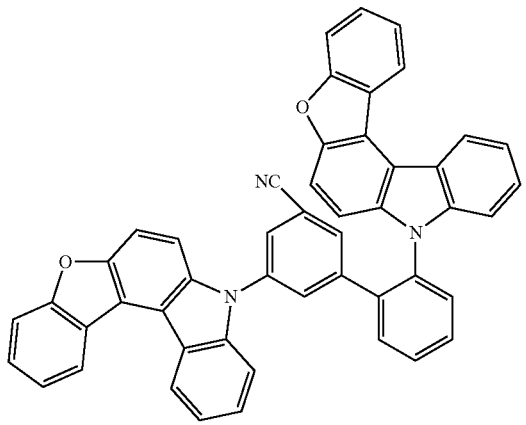
726
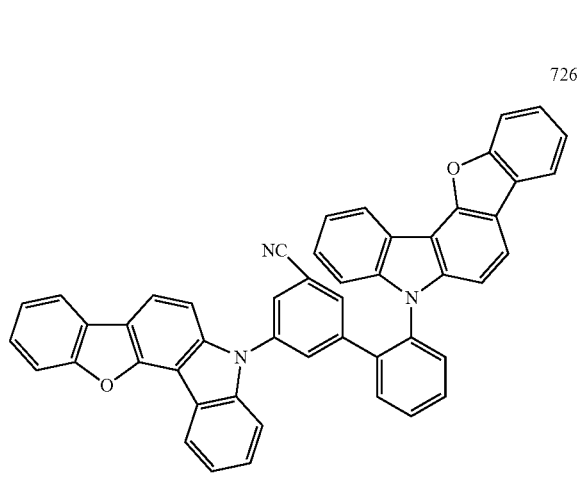
727
728
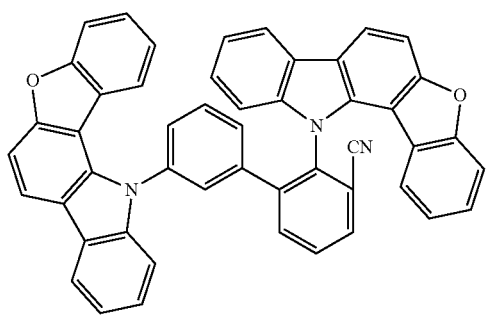
729
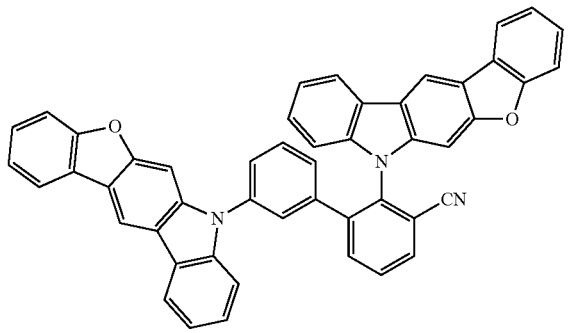
730
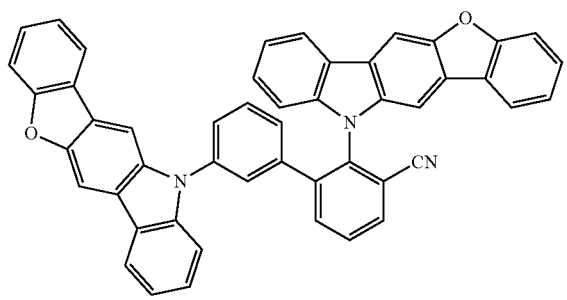
731
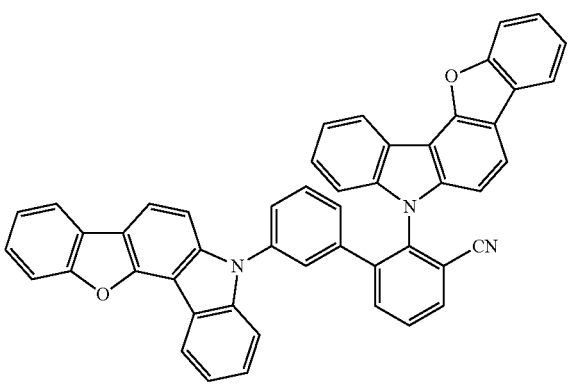
732

-continued
733
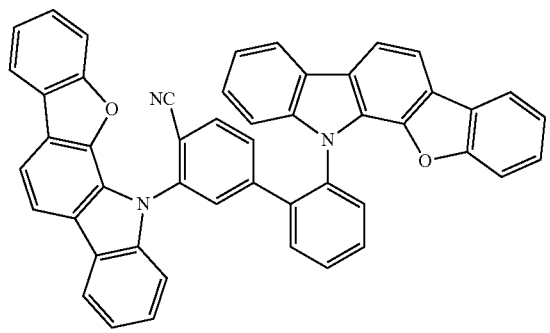
734
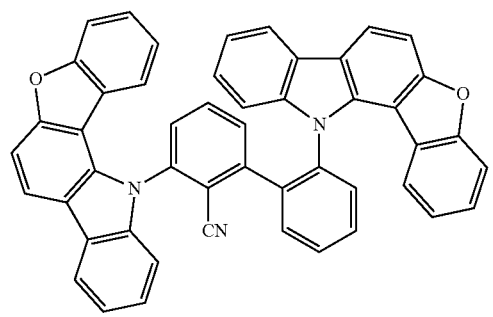
735
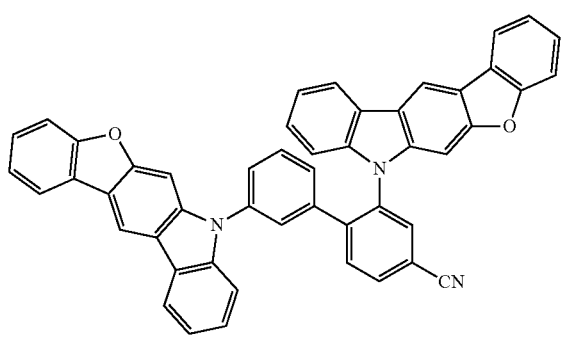
736
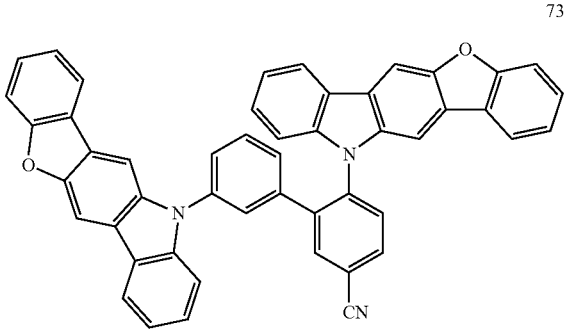
-continued
737
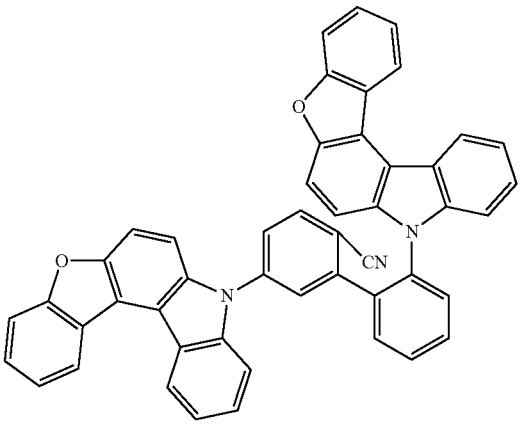
738
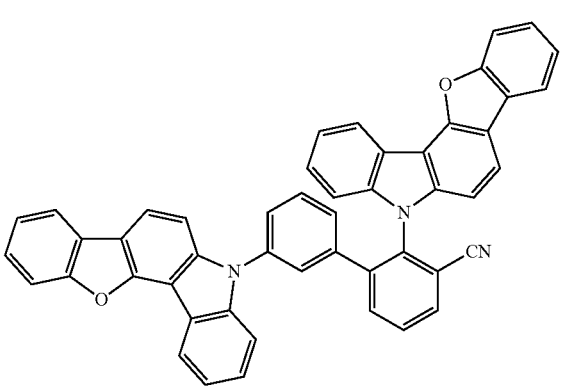
739
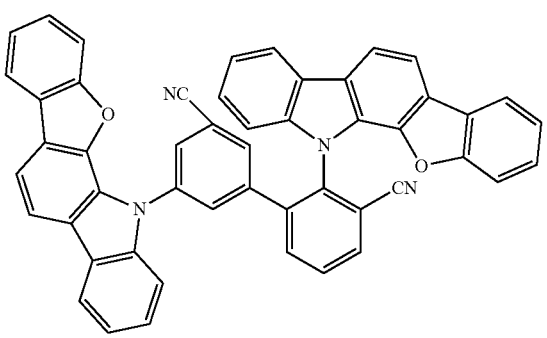
740
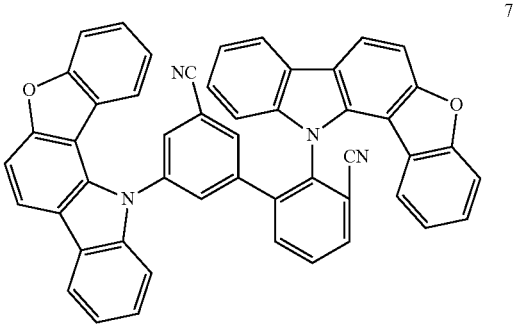

741
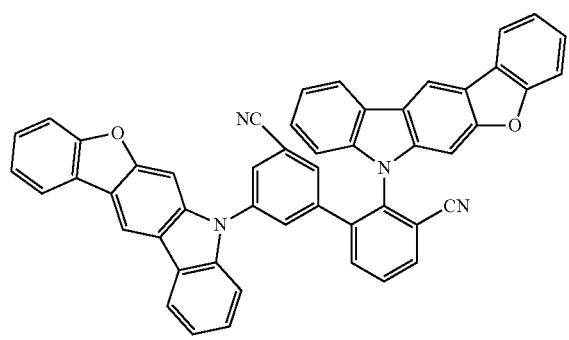
742
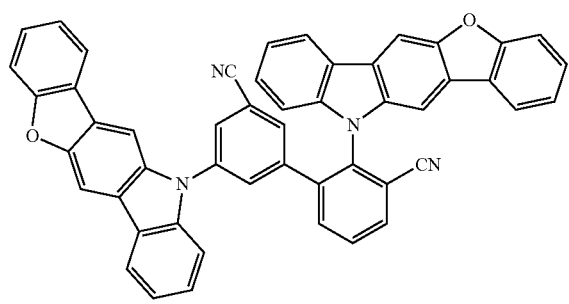
743
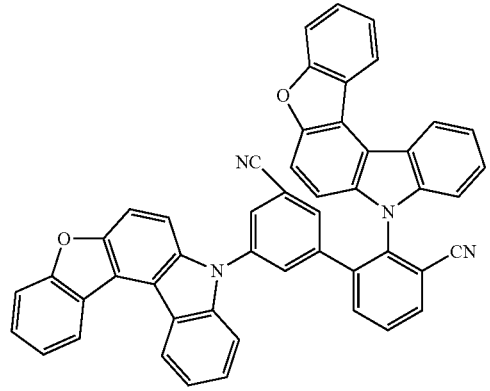
744
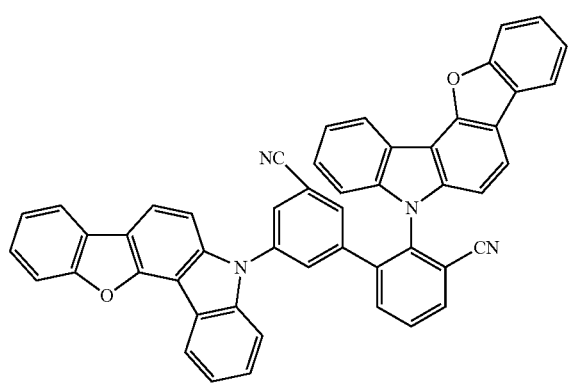
745
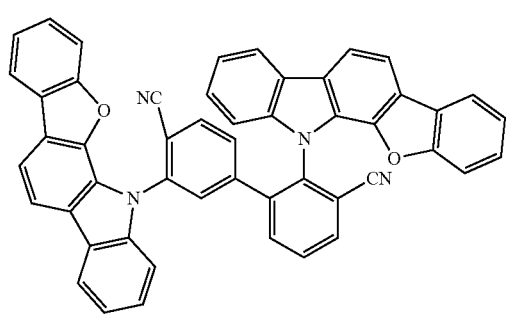
746
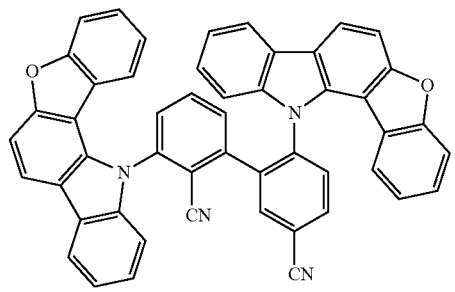
747
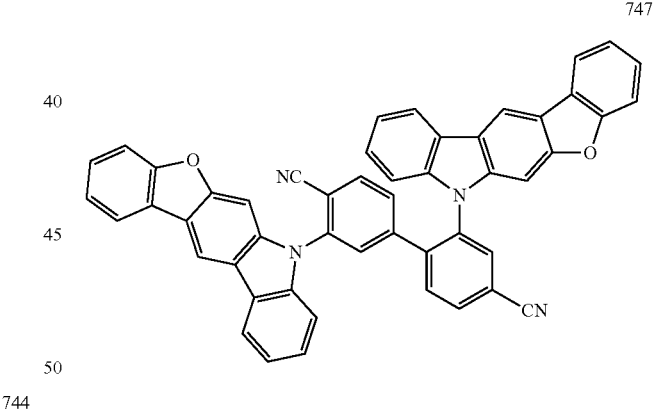
748
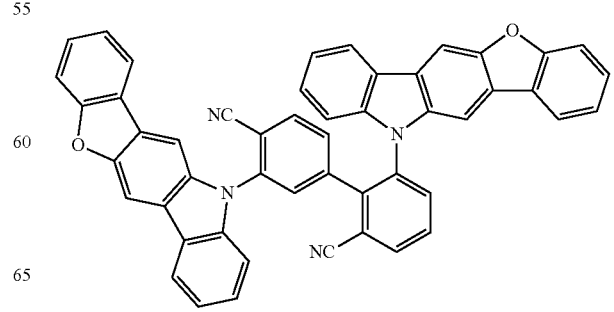

749
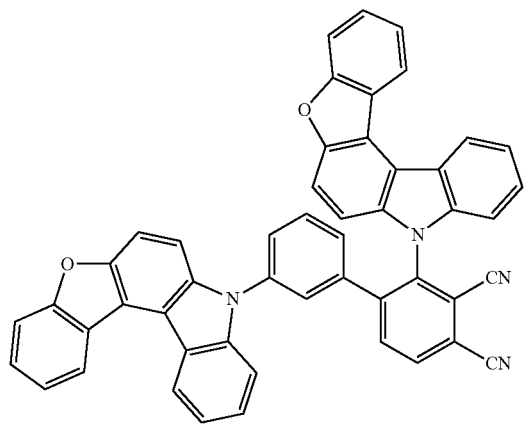
750
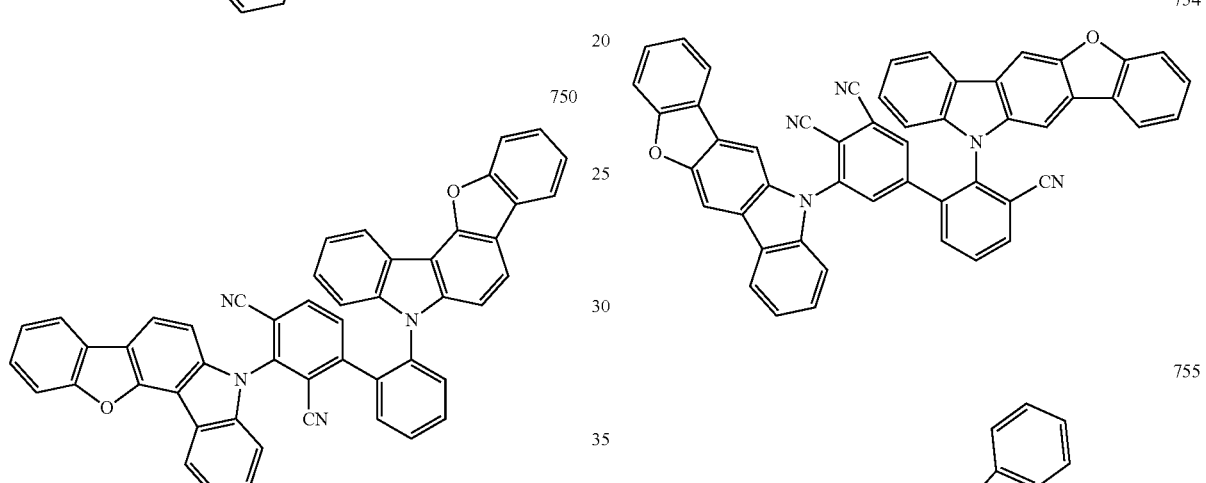
751
752
753
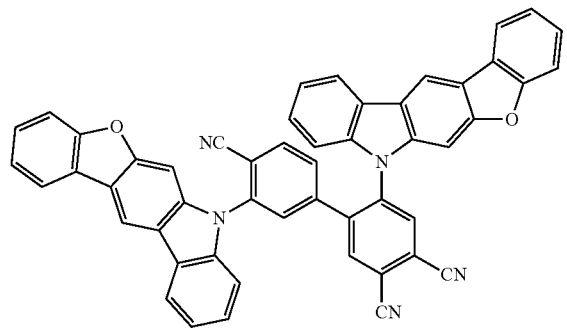
754
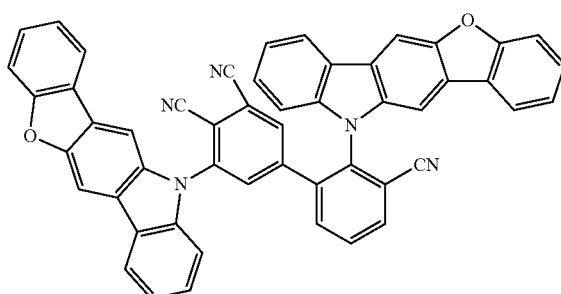
755
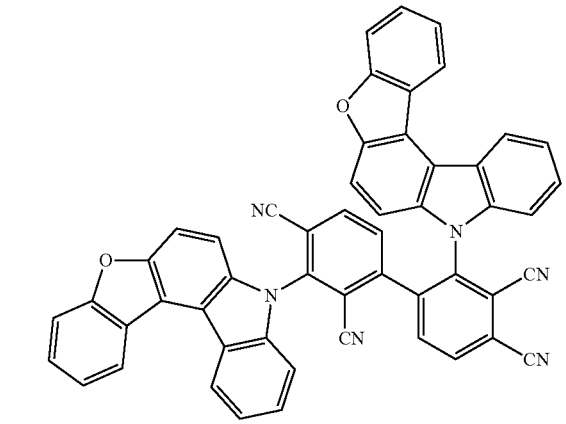
756
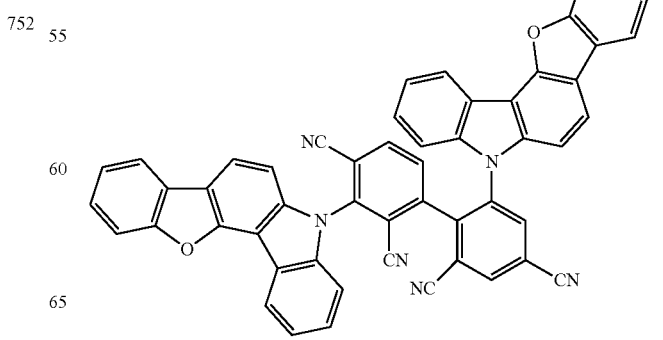

757
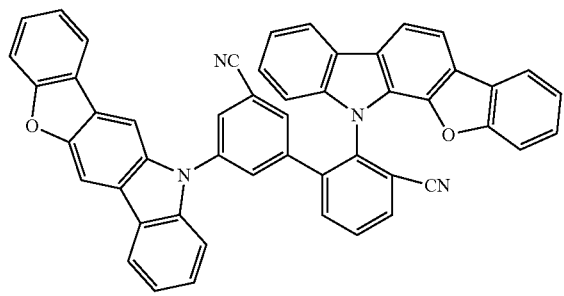
758
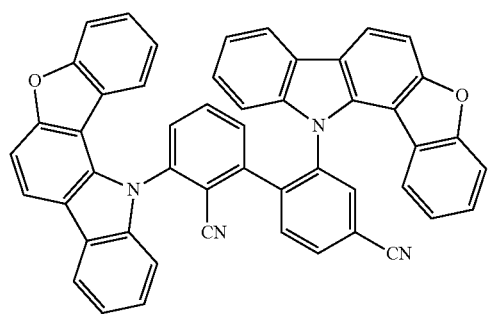
759
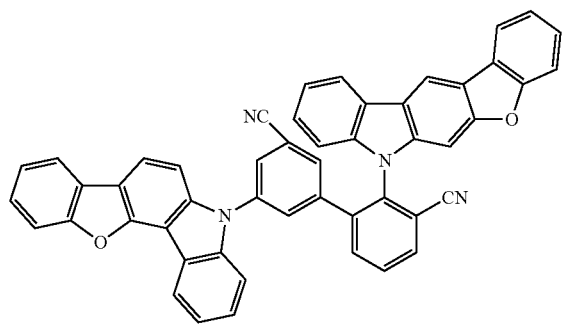
760
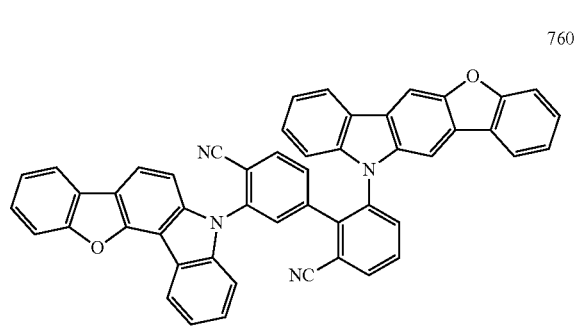
761
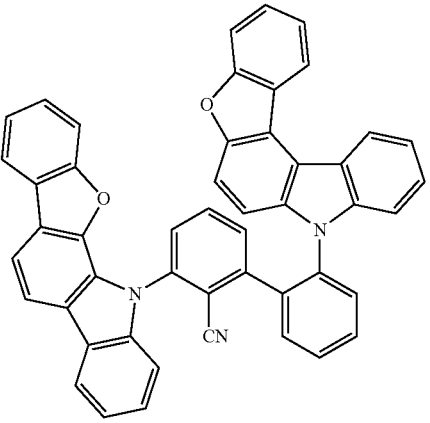
762
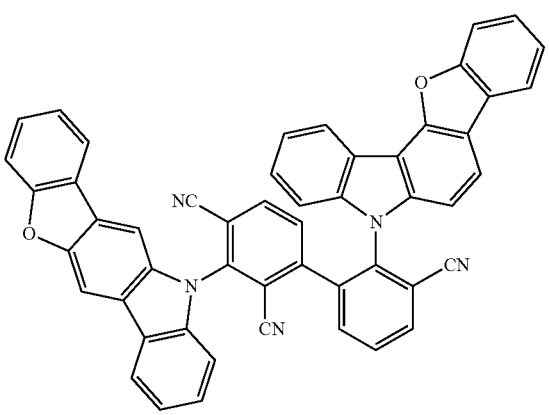
763
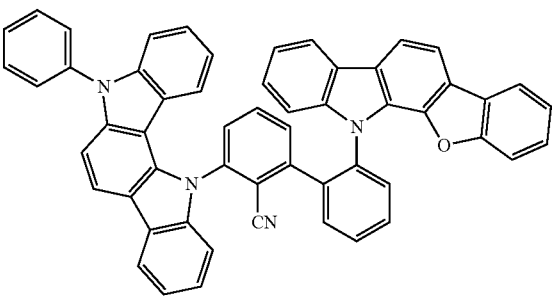
764
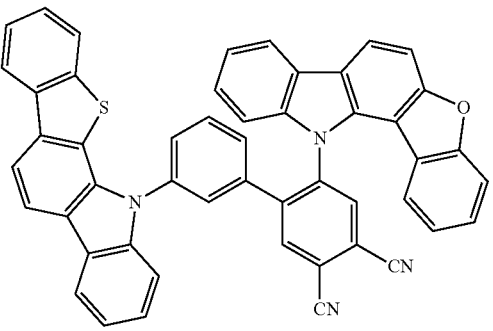

359
-continued
765
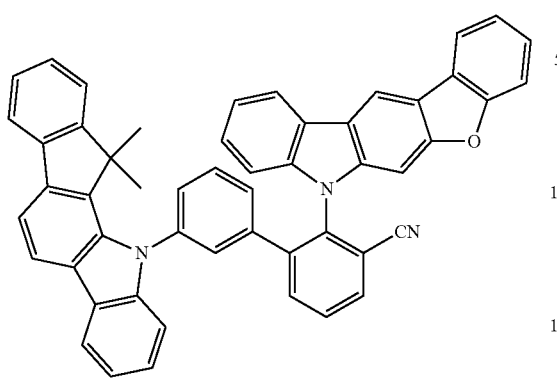
766
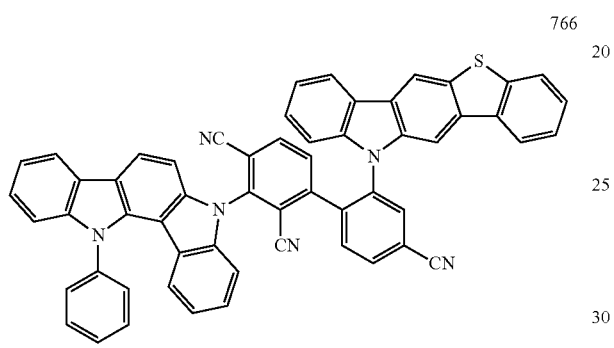
767
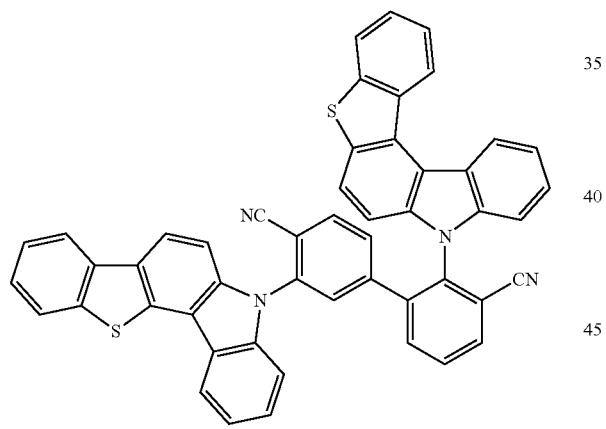
768
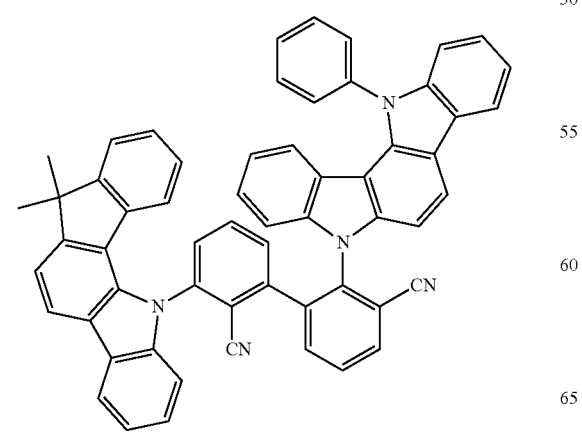
360
-continued
769
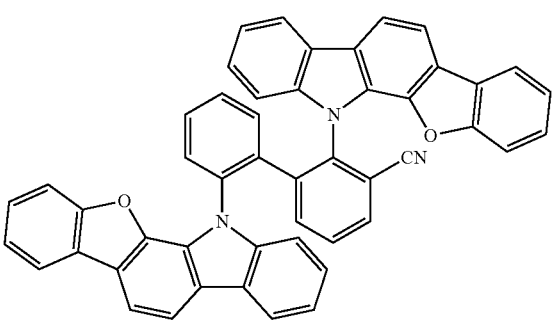
770
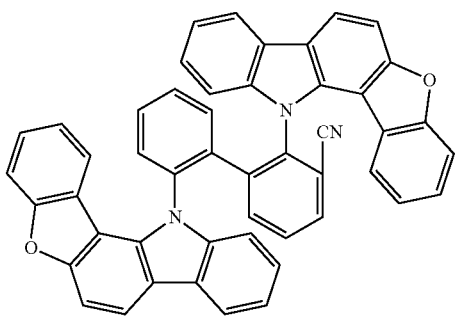
771
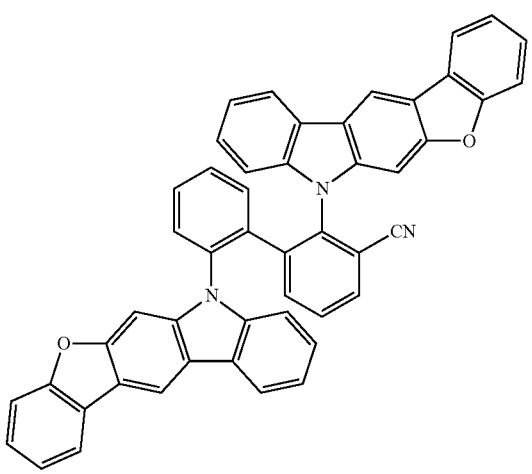
772
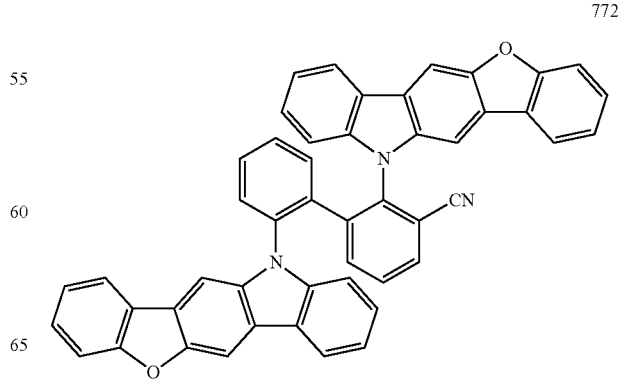

773
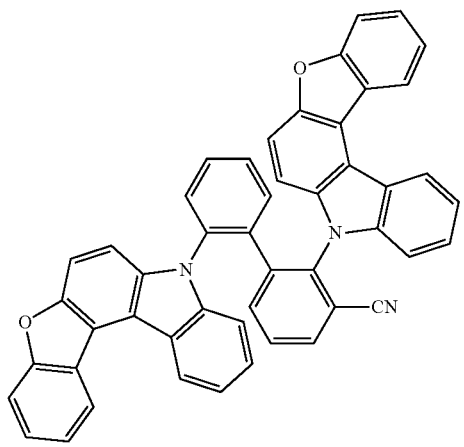
774
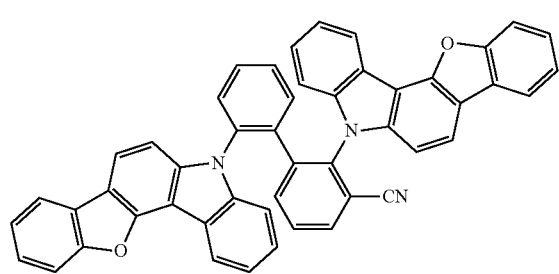
775
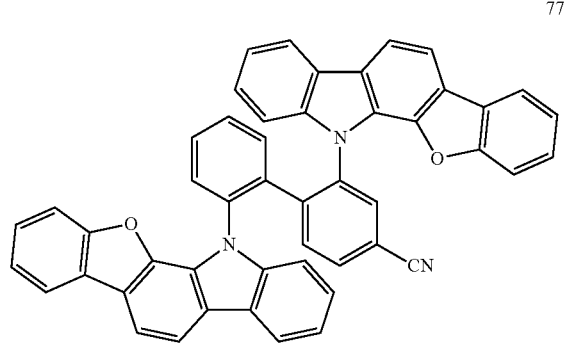
776
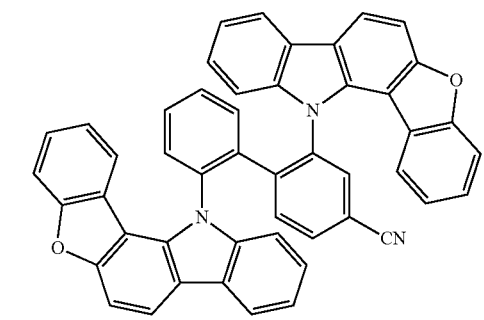
777
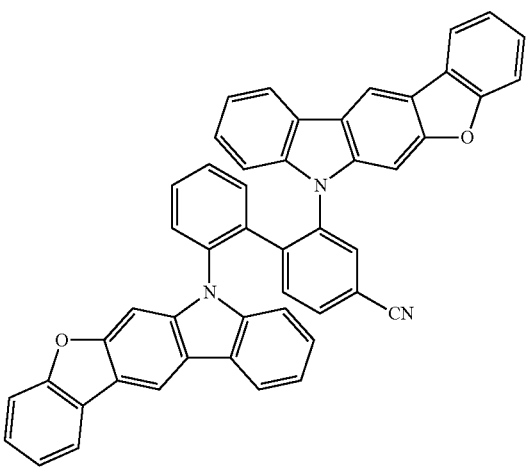
778
779
780
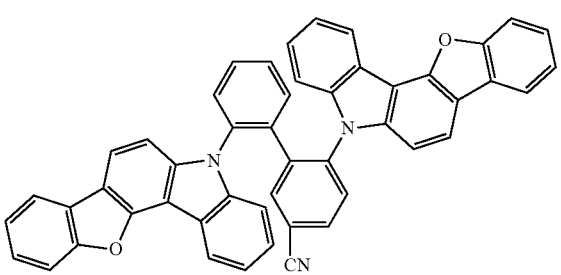

363
-continued
781
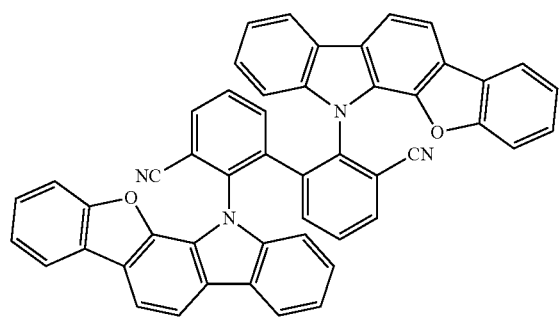
782
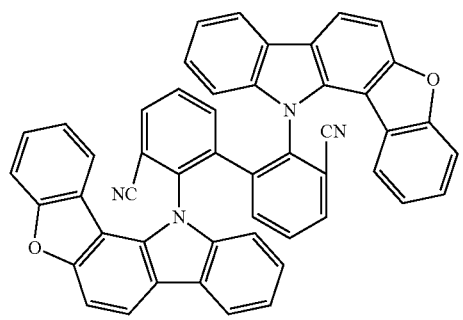
783
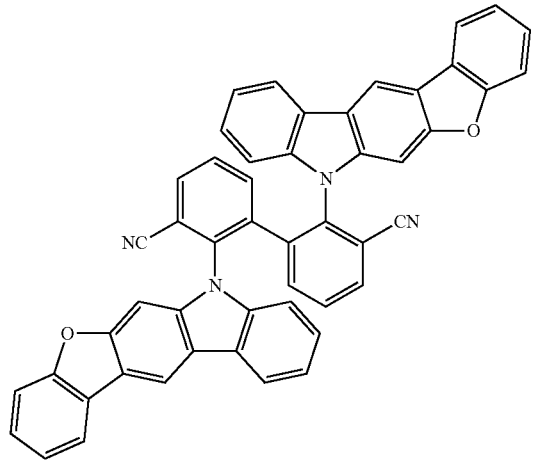
784
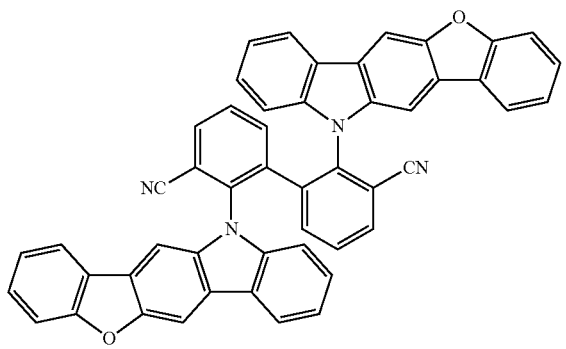
364
-continued
785
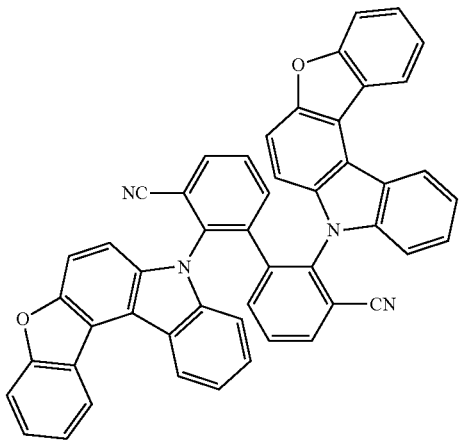
786
787
788
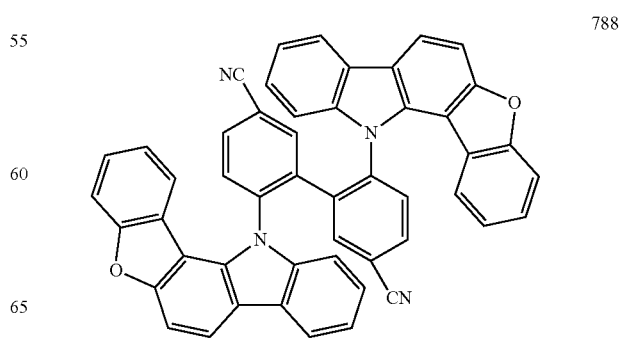

365
-continued
789
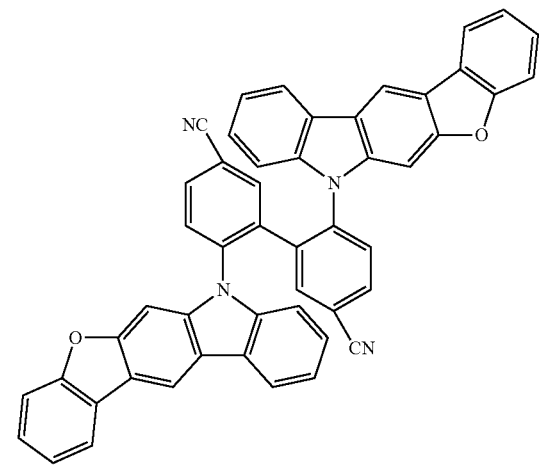
790
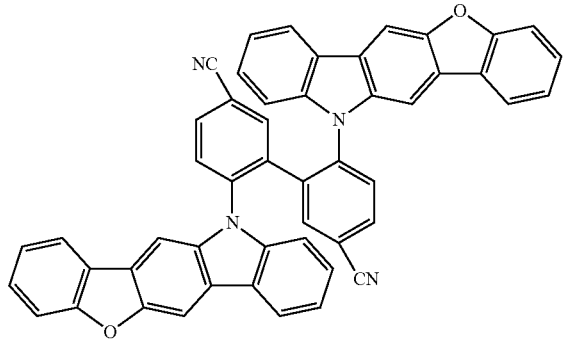
791
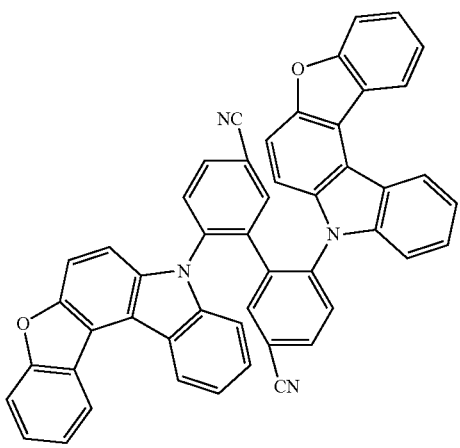
792
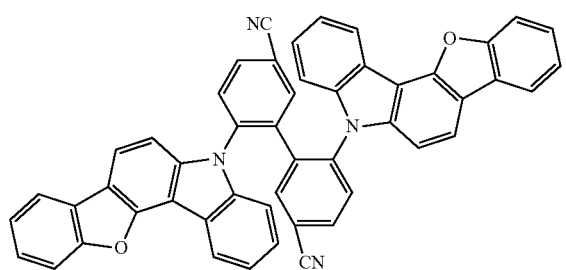
366
-continued
793
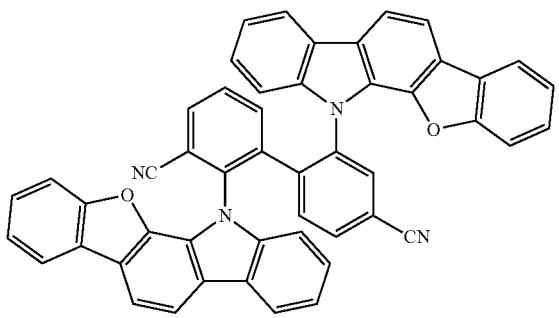
794
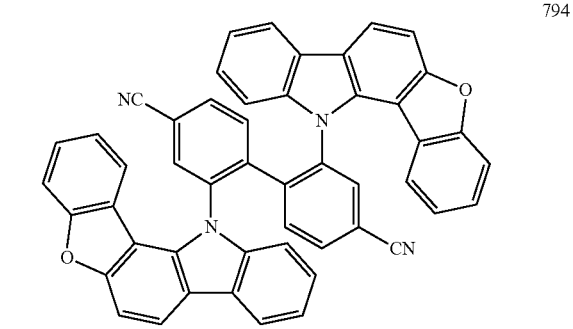
795
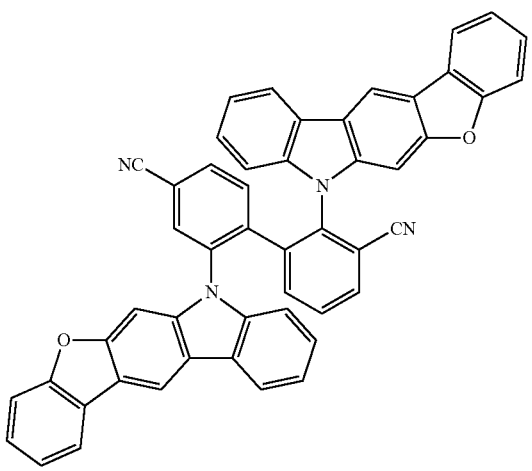
796
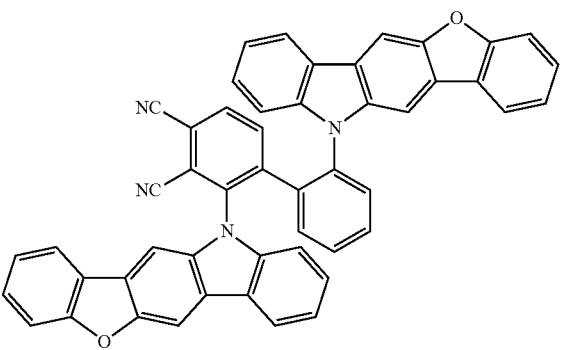

-continued
797
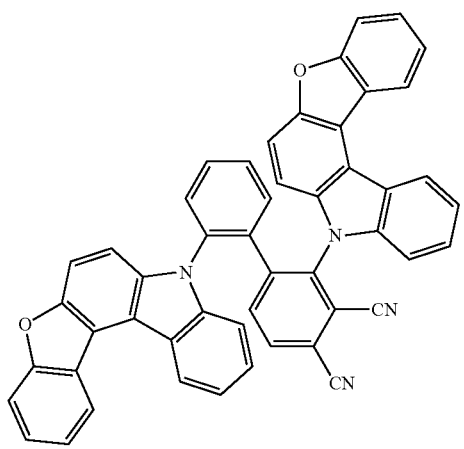
798
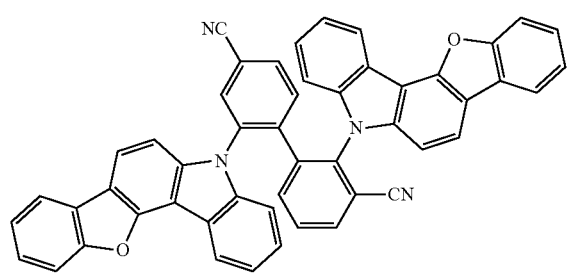
799
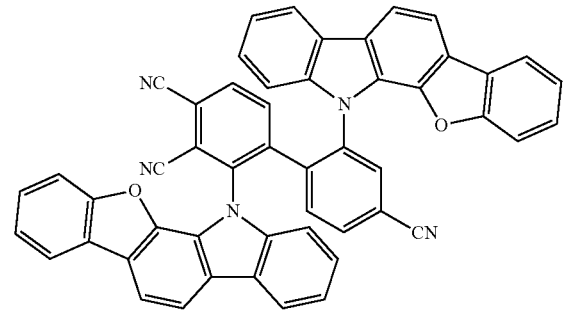
800
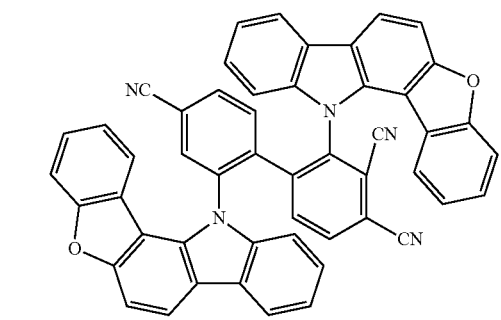
-continued
801
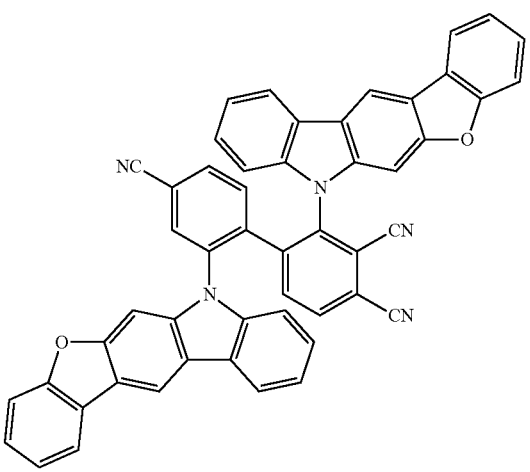
802
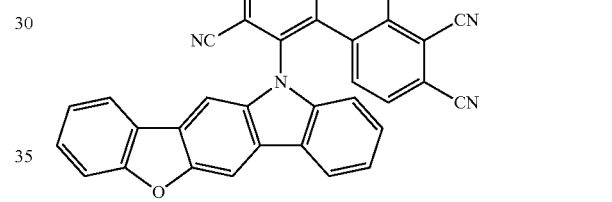
803
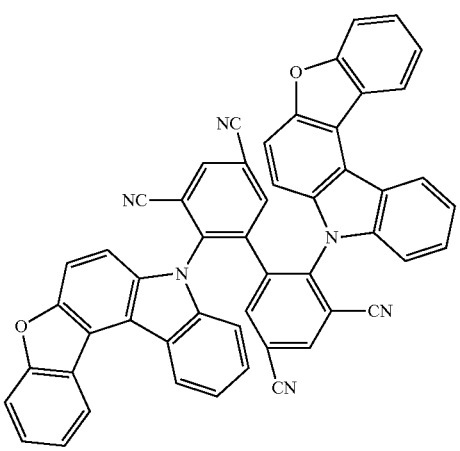
804
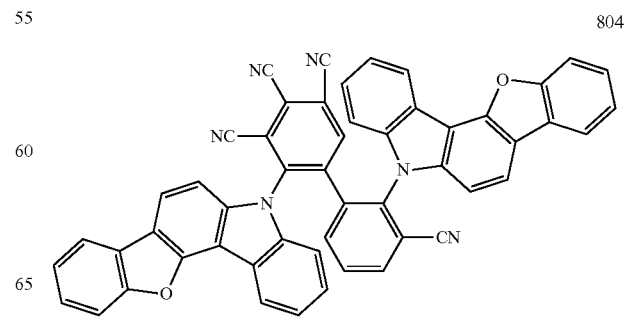

-continued
805
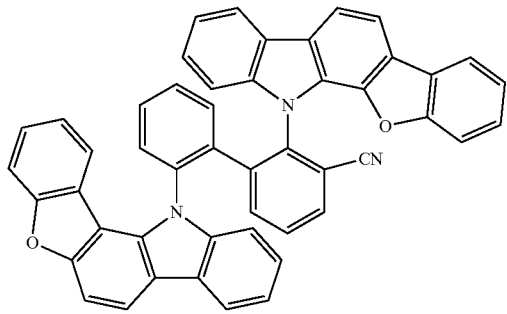
806
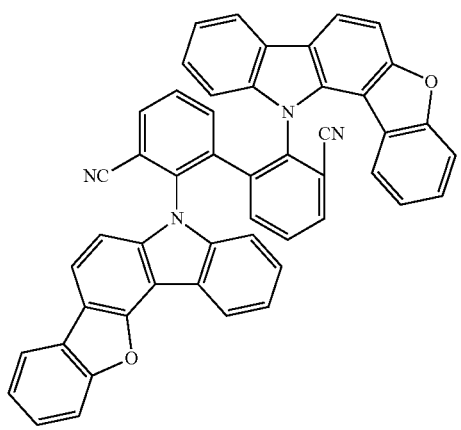
807
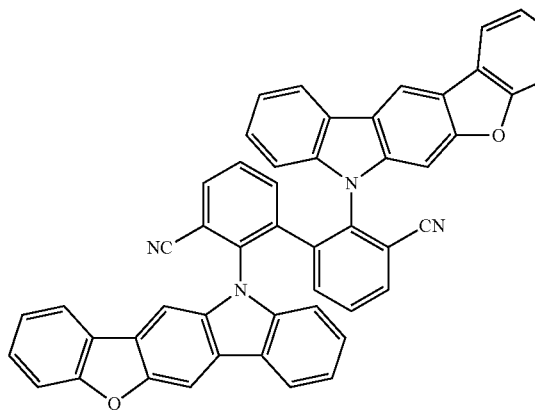
808
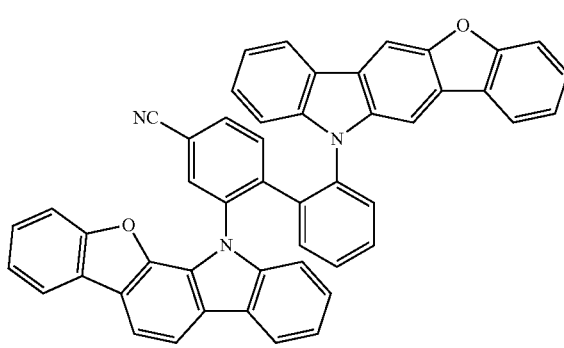
-continued
809
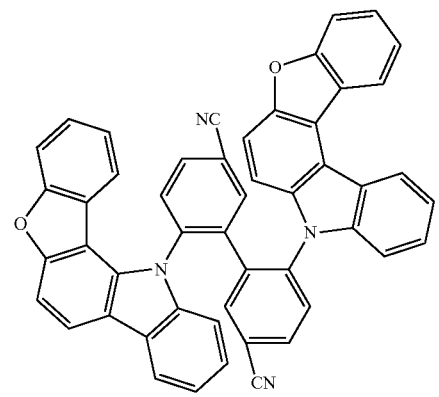
810
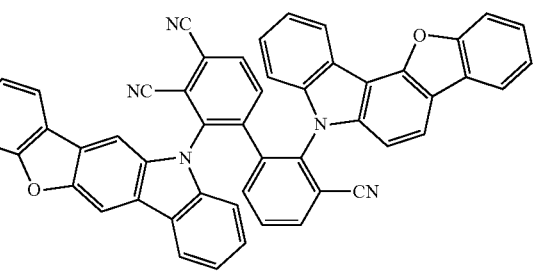
811
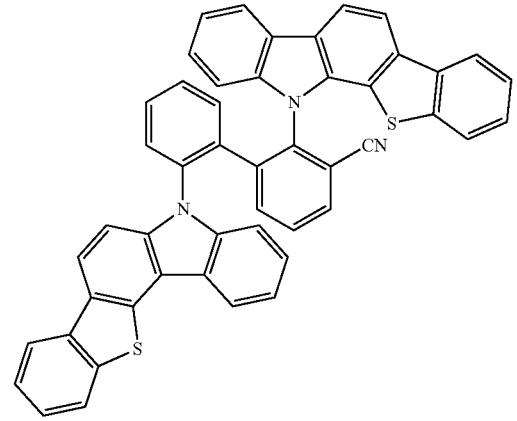
812
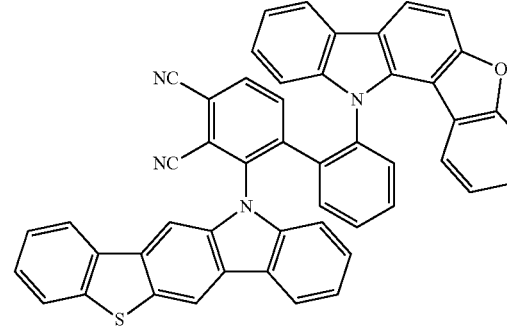

-continued
813
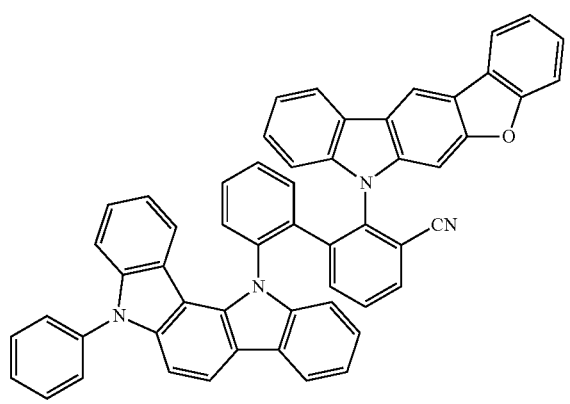
814
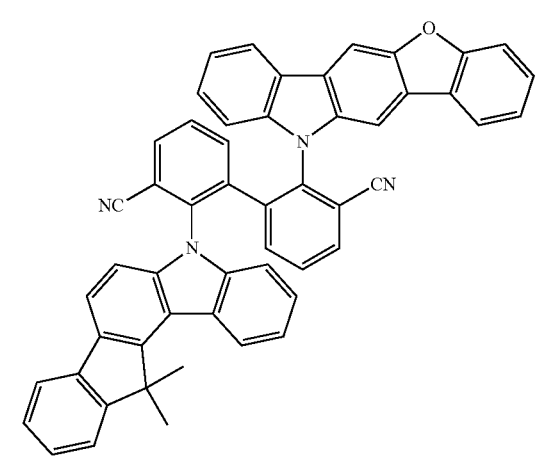
815
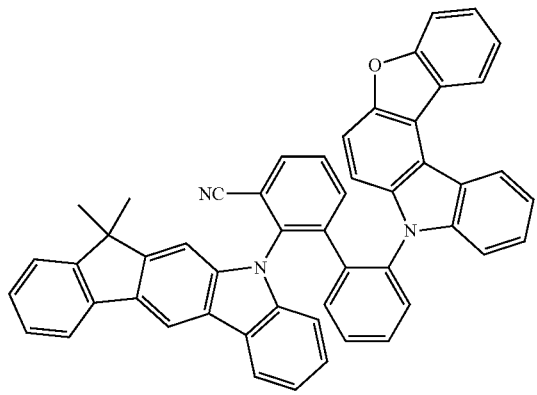
816
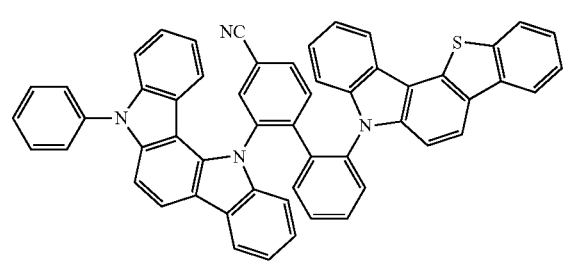
-continued
817
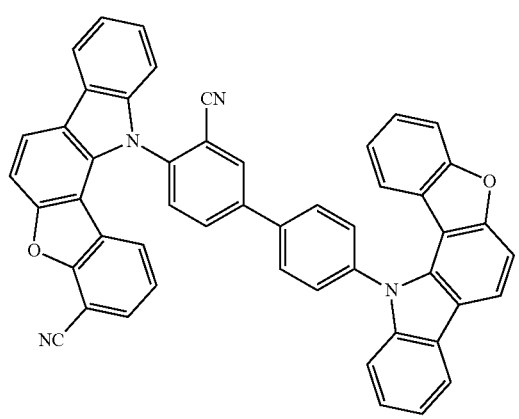
818
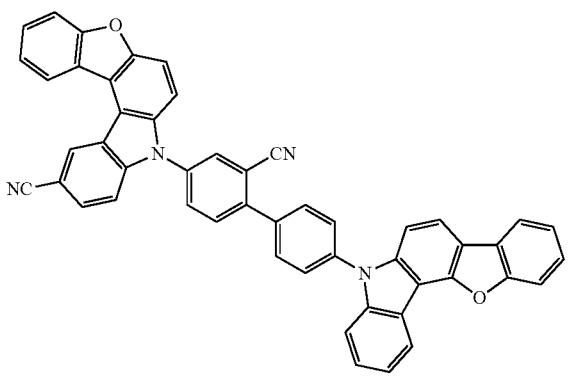
819
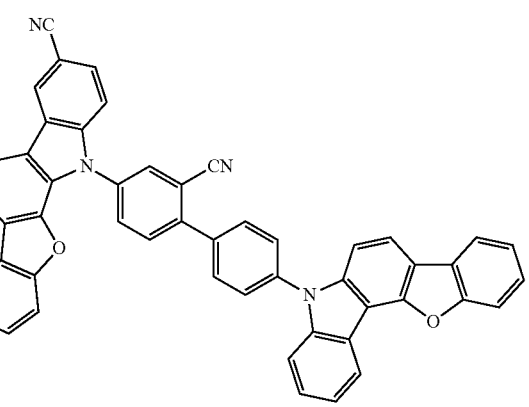
820
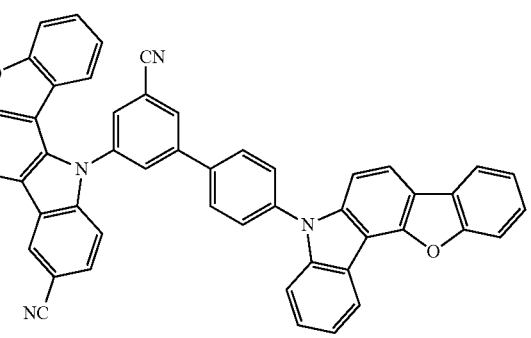

821
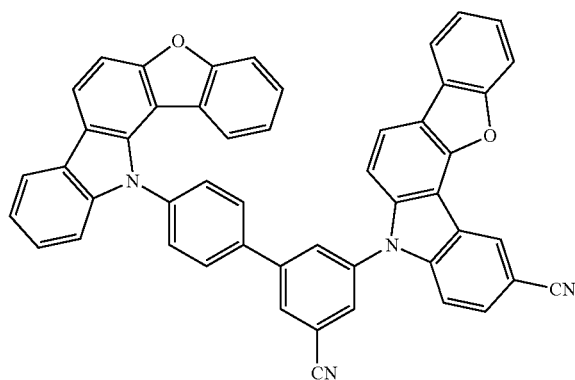
822
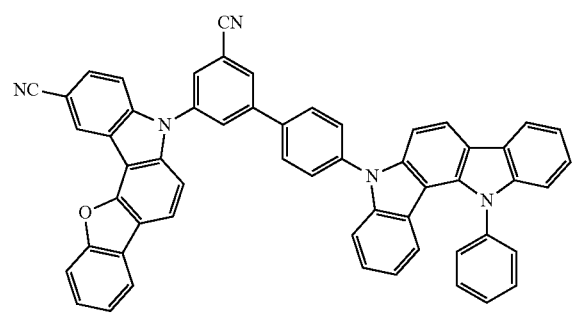
823
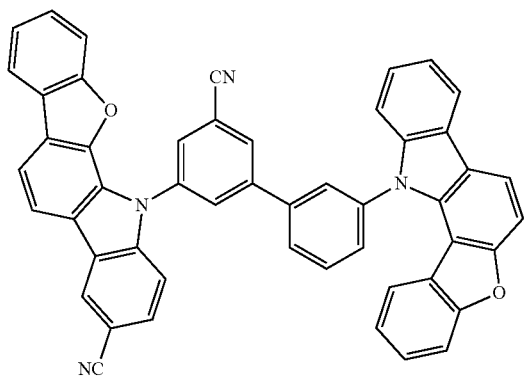
824
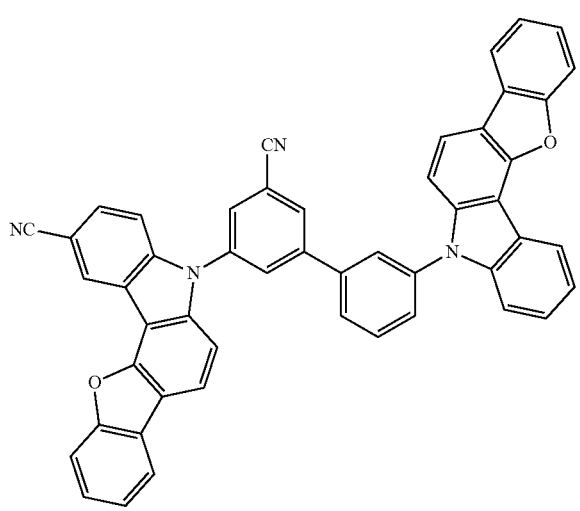
825
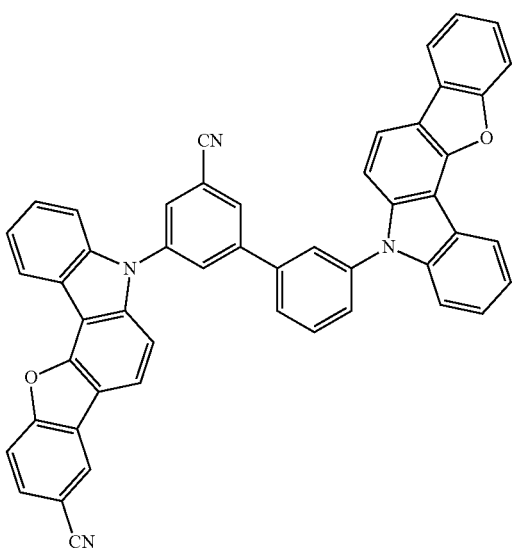
826
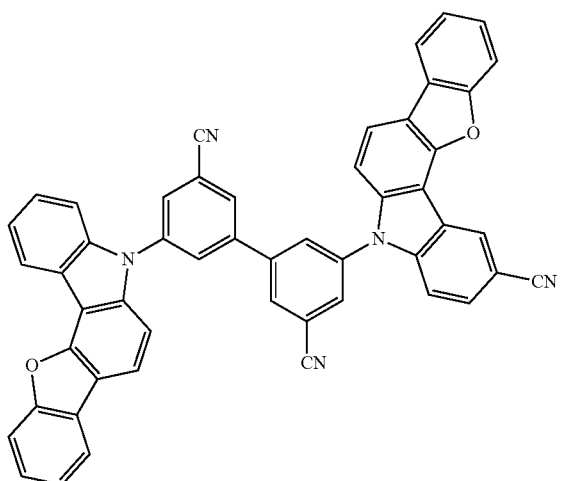
827
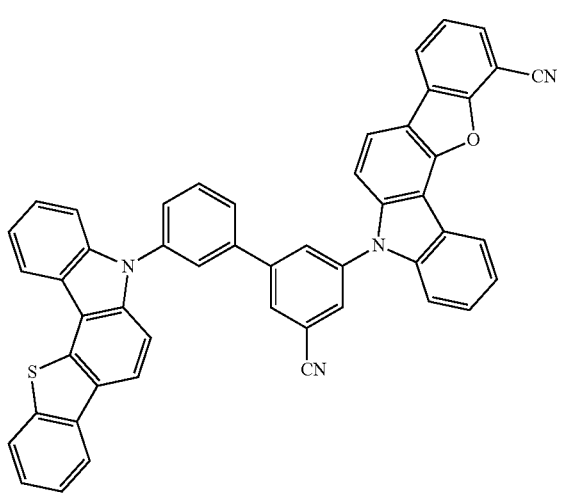

375
-continued

376
-continued

834
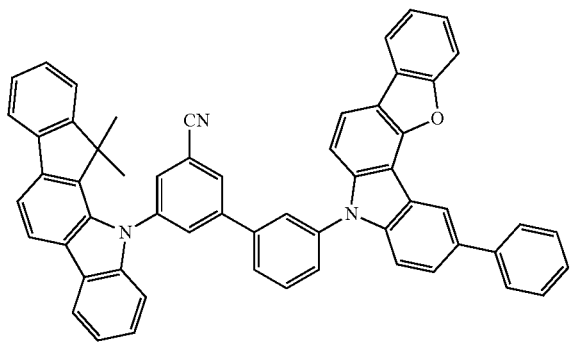
835
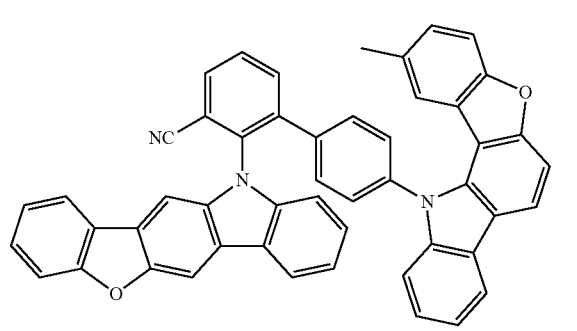
836
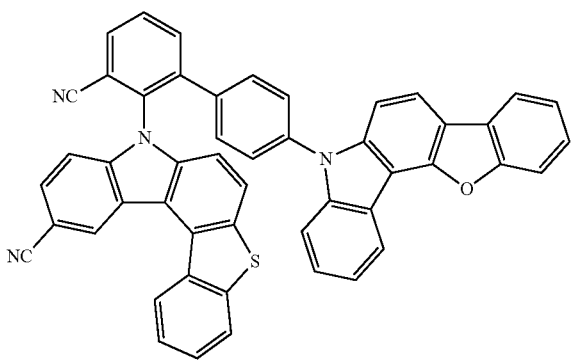
837
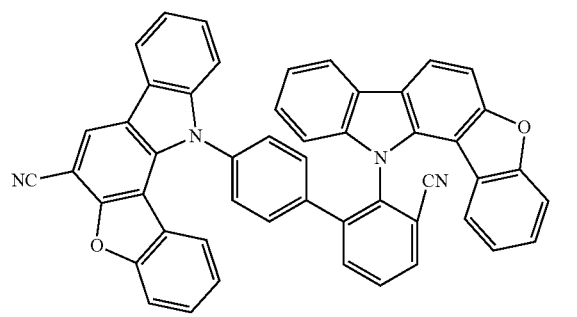
838
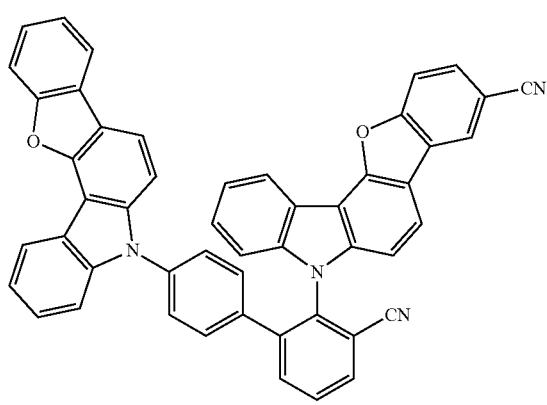
839
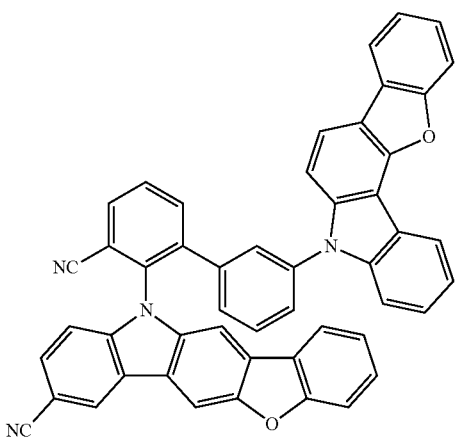
840
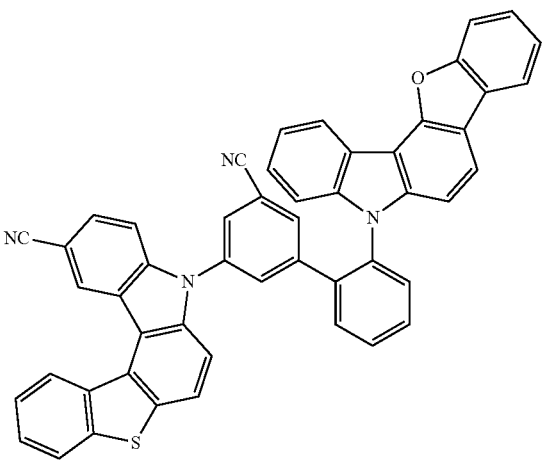

-continued
841
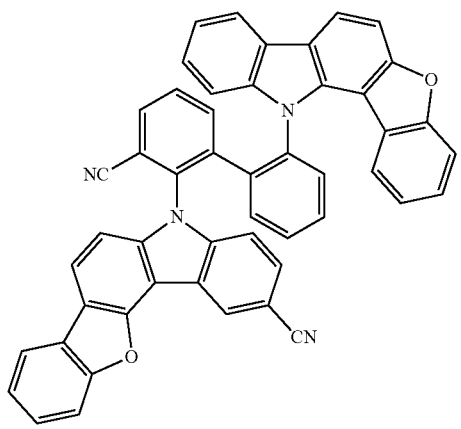
842
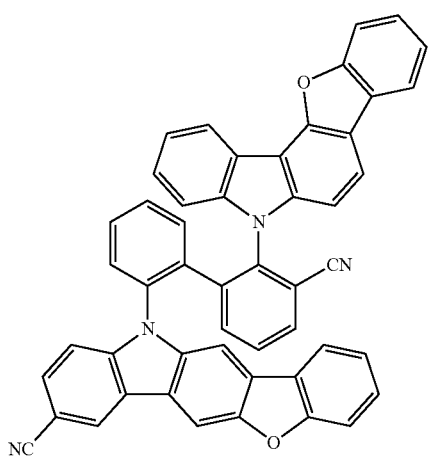
843
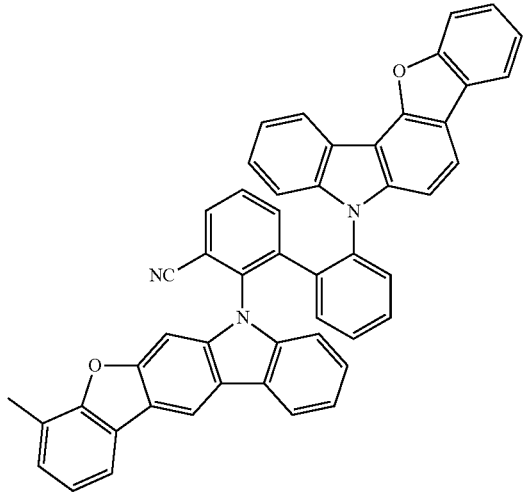
-continued
844
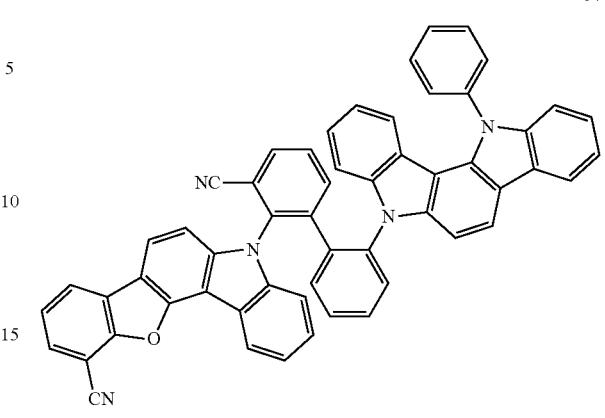
845
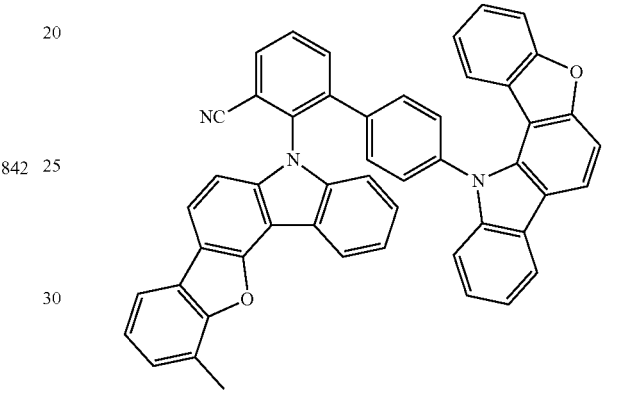
846
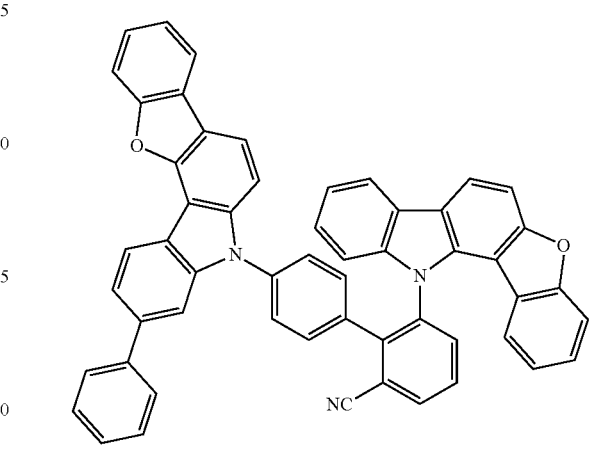
847
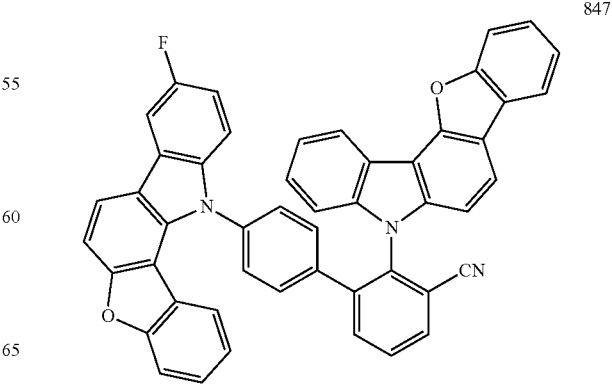

848
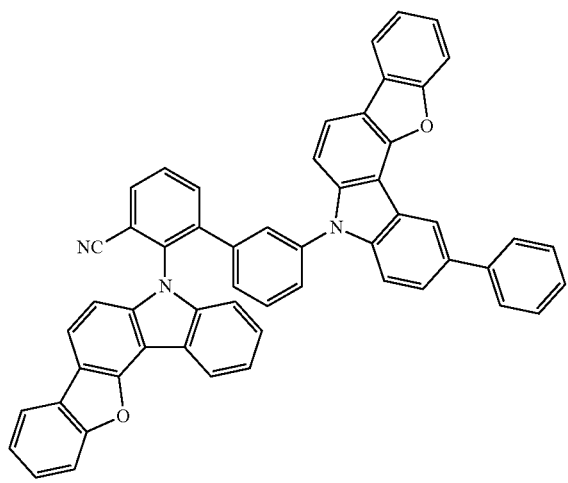
849
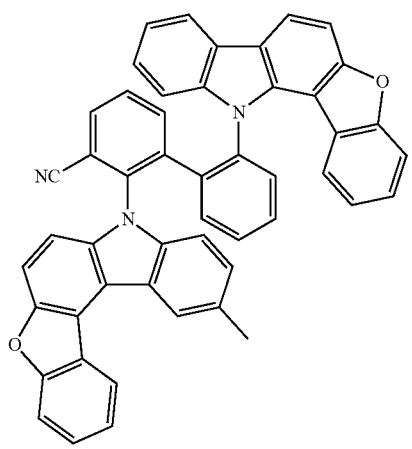
850
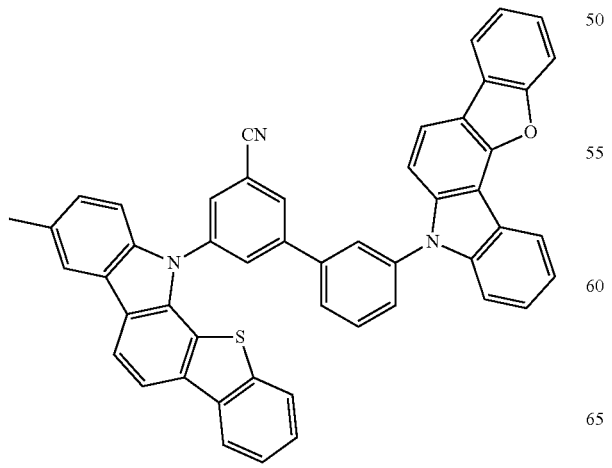
851
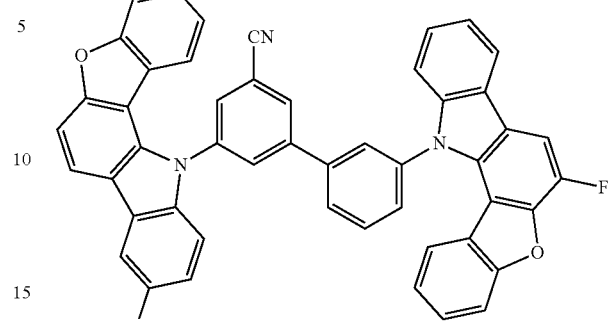
852
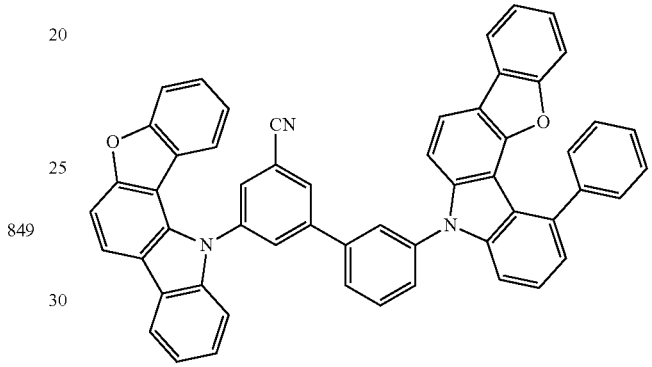
1
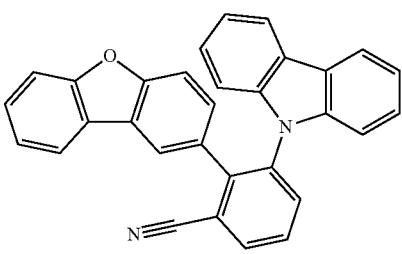
2
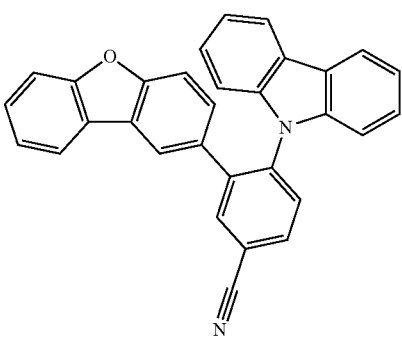

3
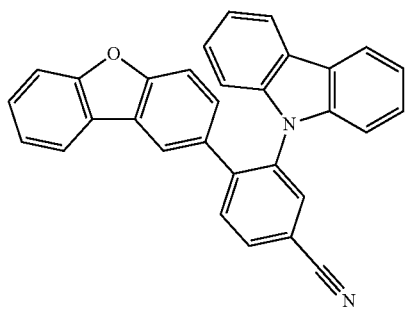
4
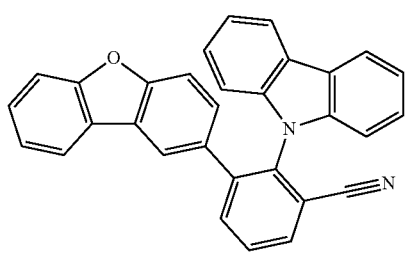
5
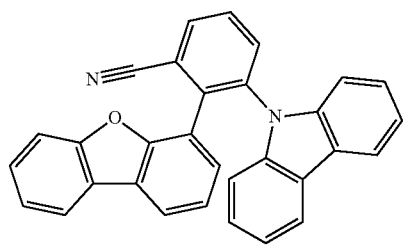
6
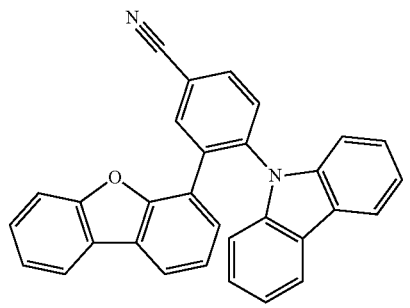
7
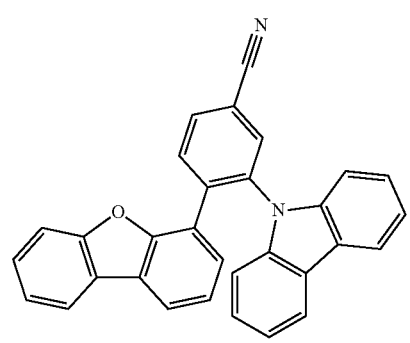
8
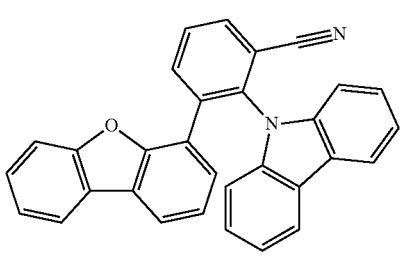
9
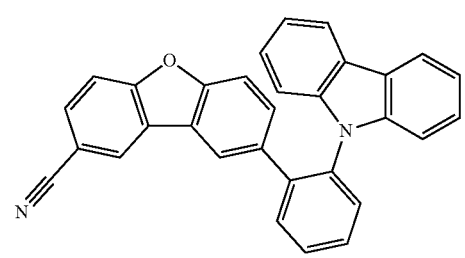
10
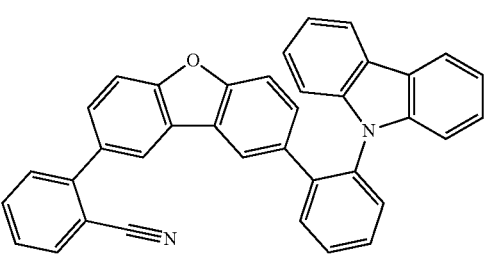
11
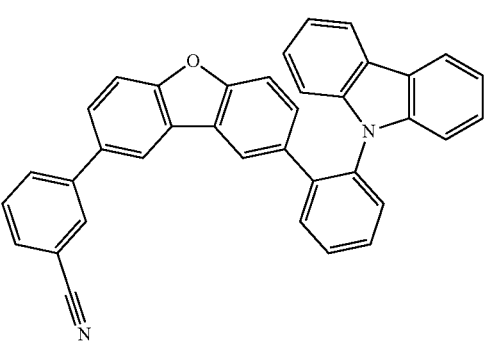
12
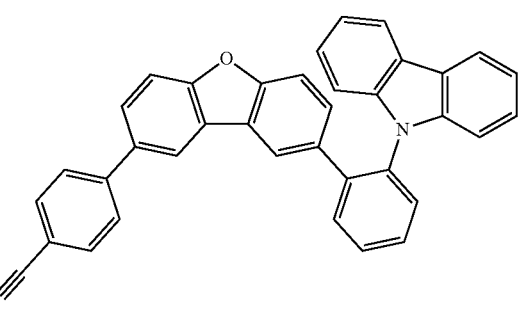

13
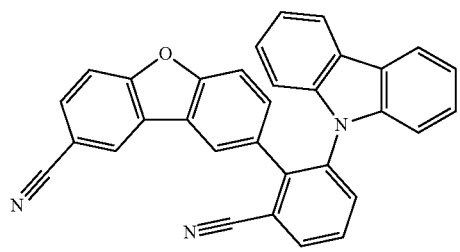
14
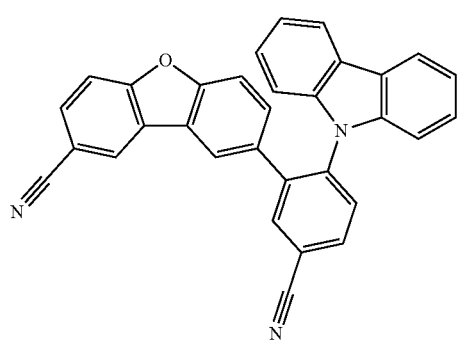
15
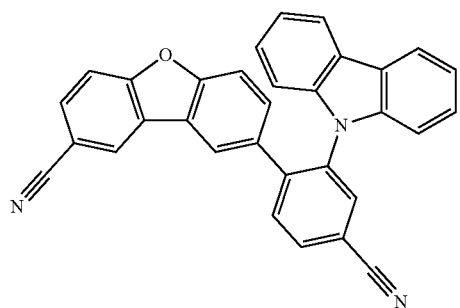
16
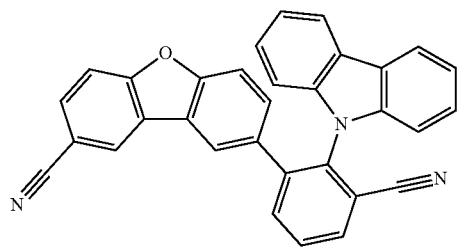
17
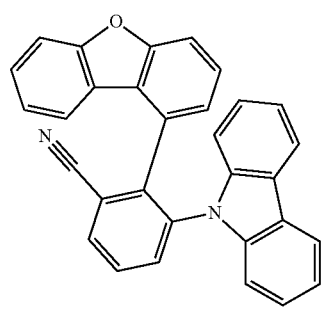
18
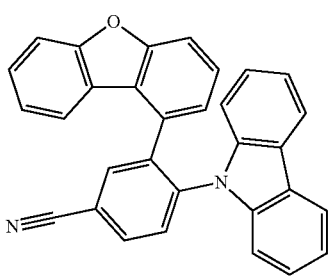
19
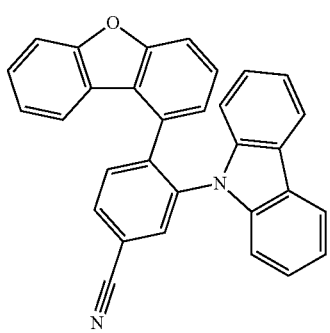
20
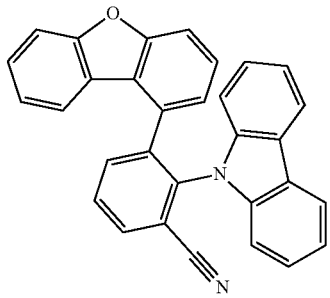
21
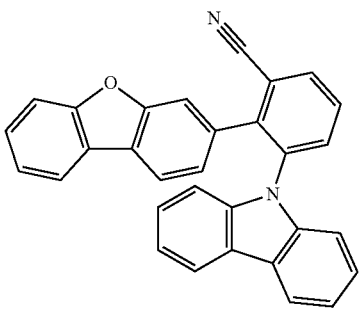
22
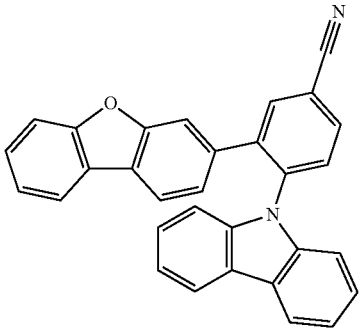

387
-continued
23
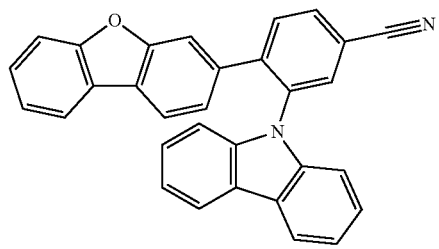
24
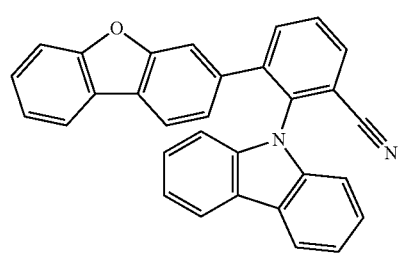
25
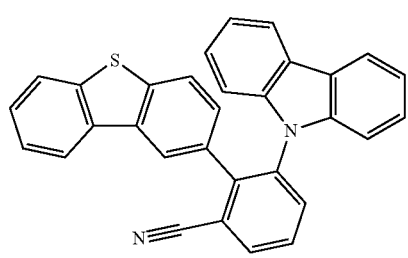
26
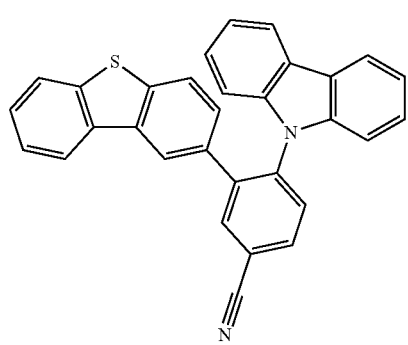
27
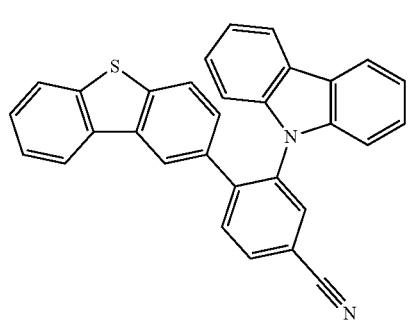
388
-continued
28
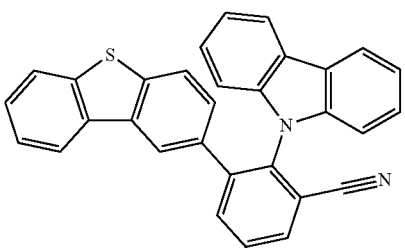
29
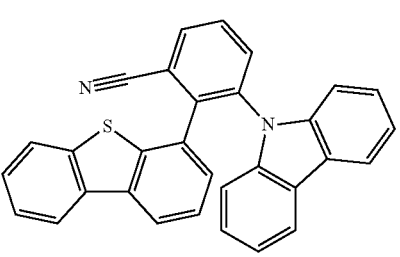
30
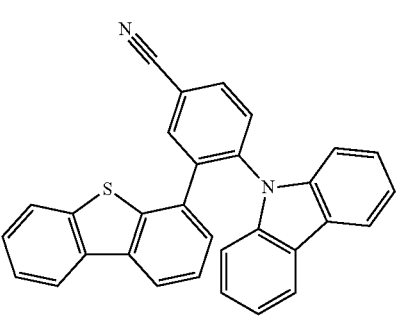
31
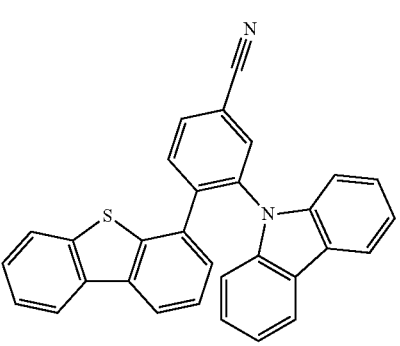
32
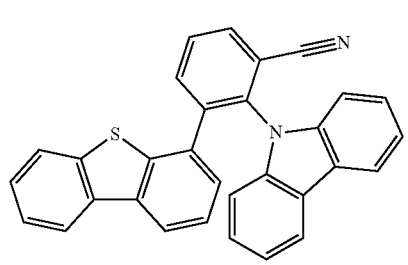

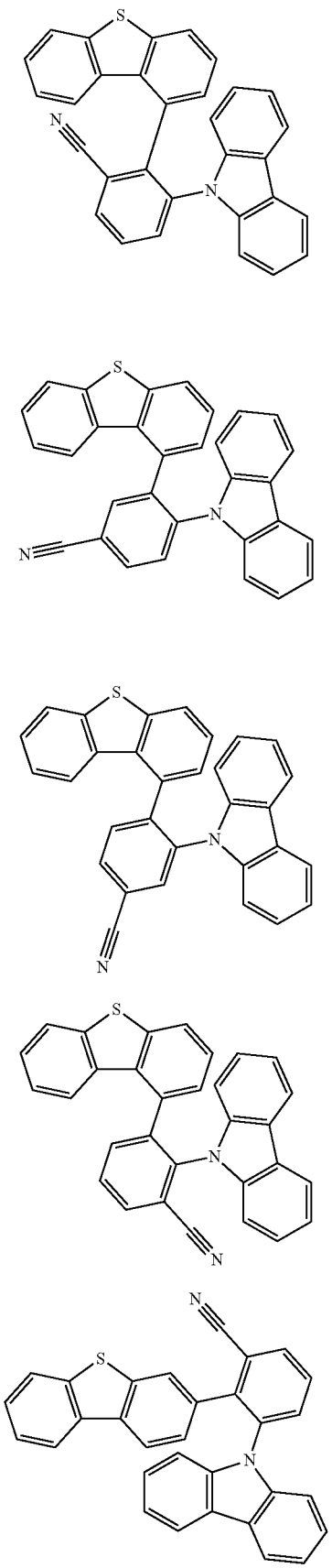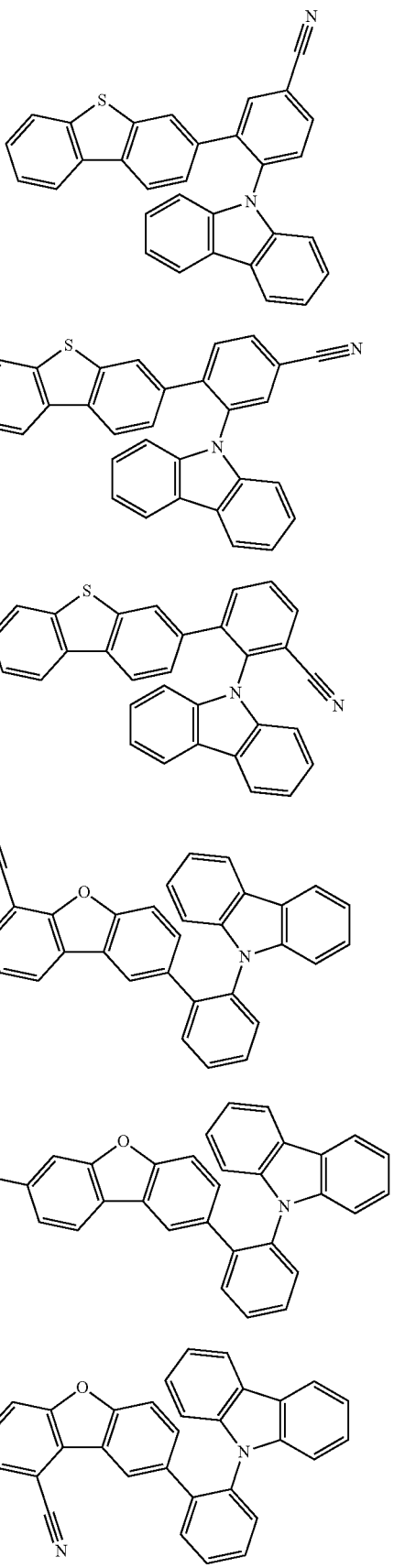

-continued
44
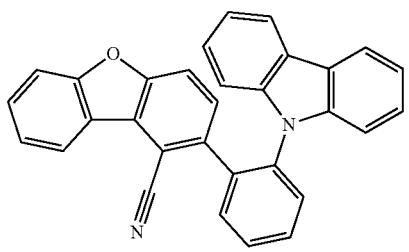
45
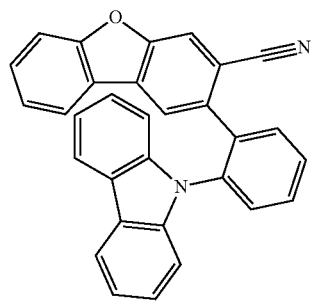
46
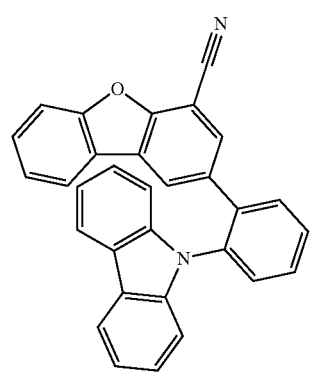
47
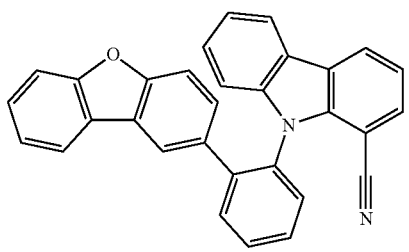
48
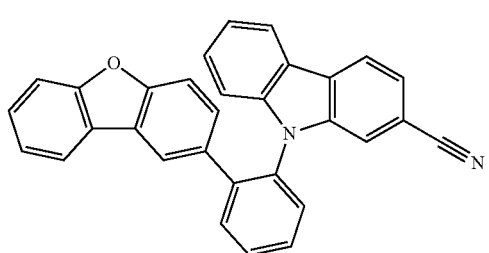
-continued
49
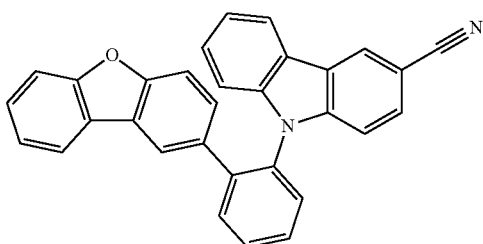
50
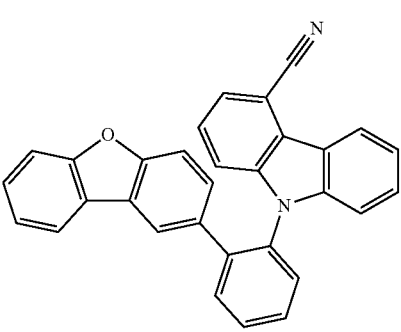
51
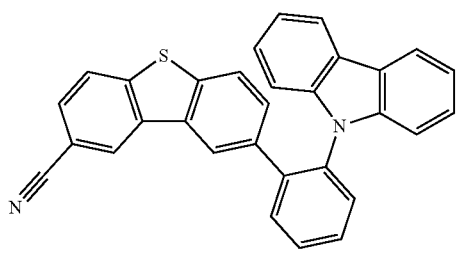
52
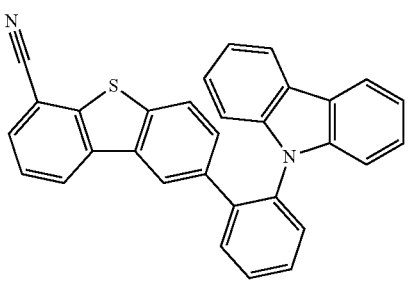
53
54
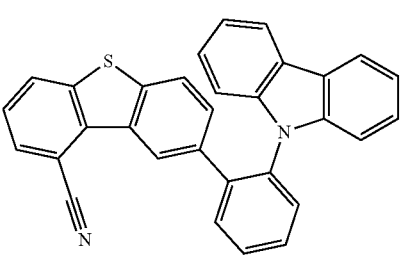

-continued
55
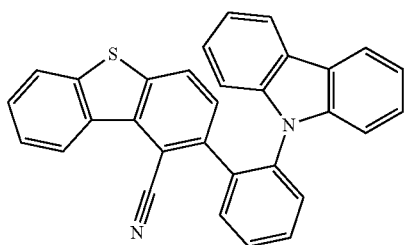
56
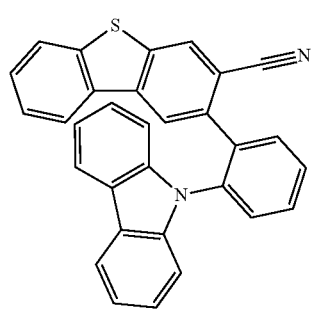
57
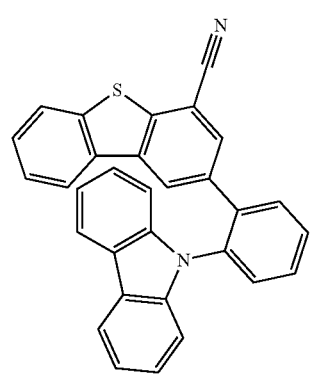
58
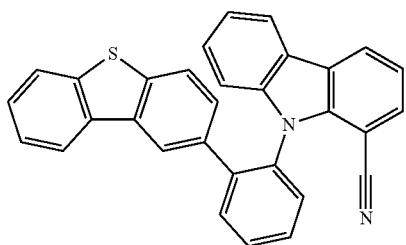
59
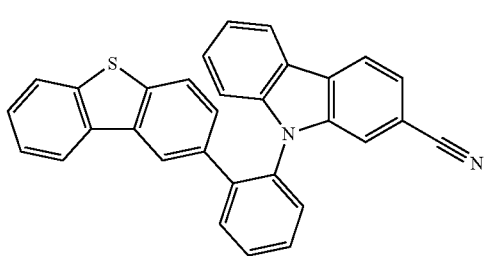
-continued
60
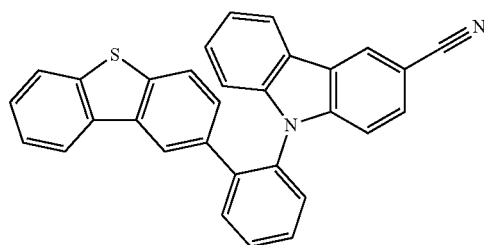
61
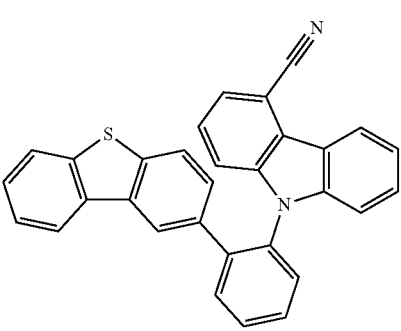
62
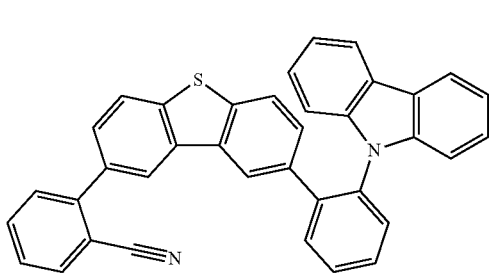
63
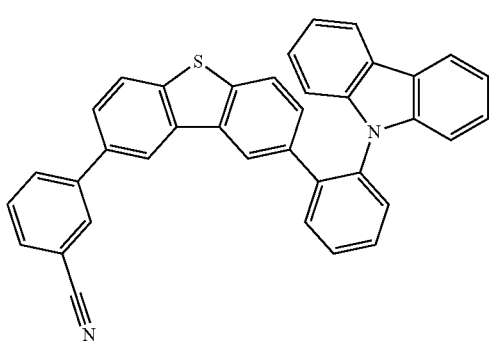
64
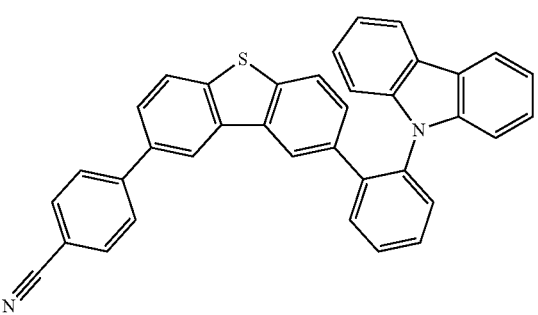

65
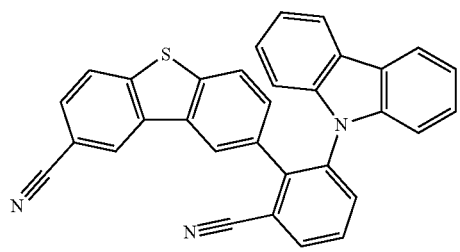
66
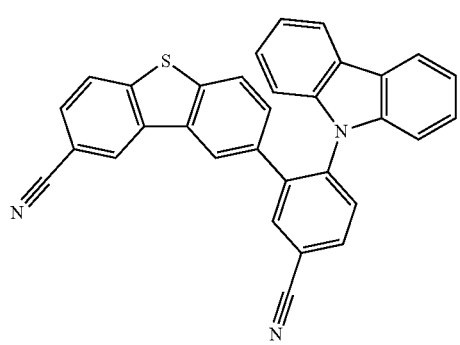
67
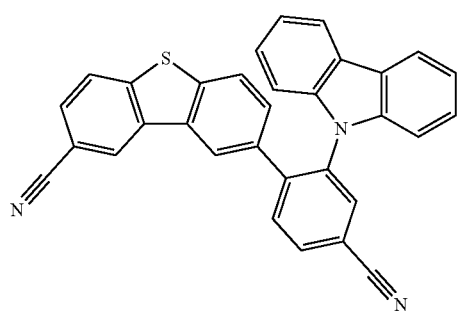
68
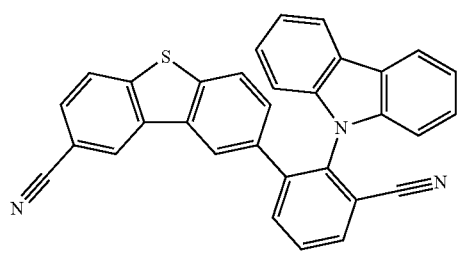
69
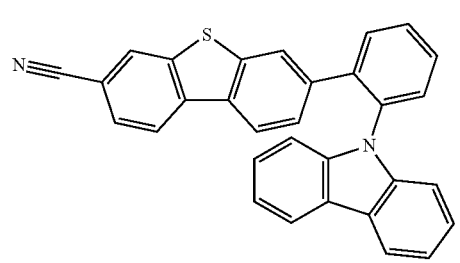
70
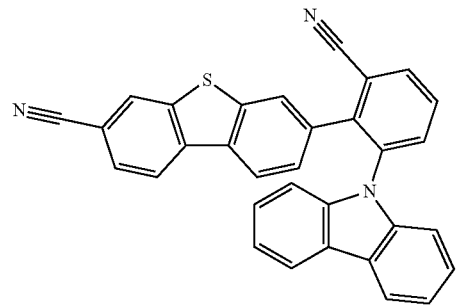
71
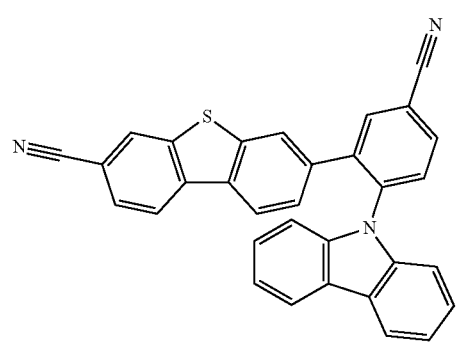
72
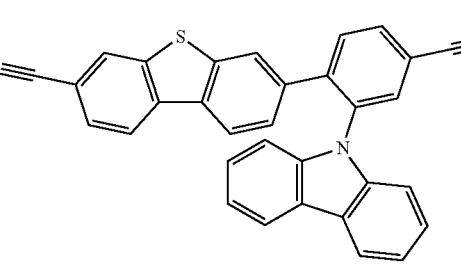
73
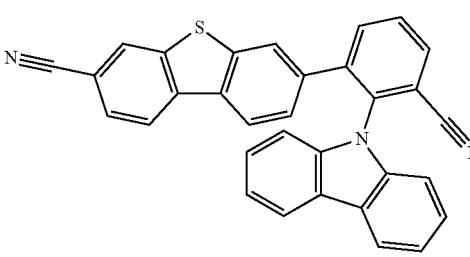
74
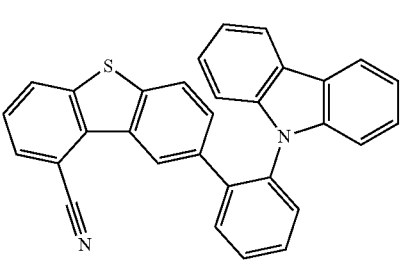

75
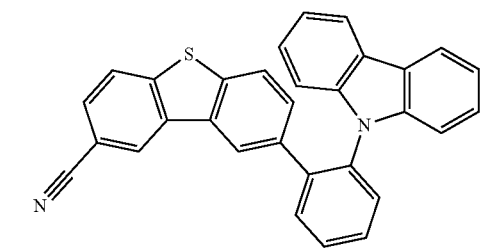
76
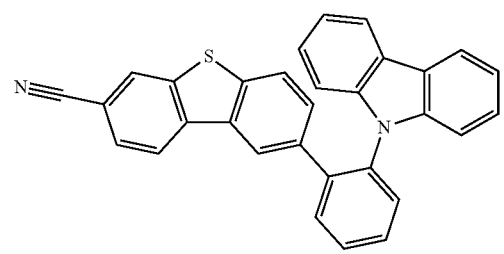
77
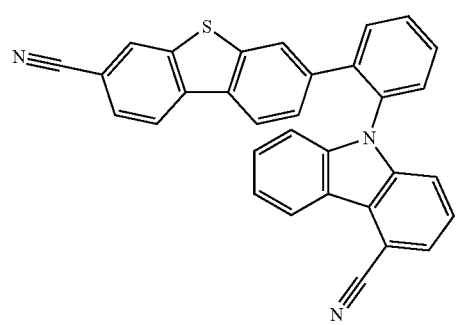
78
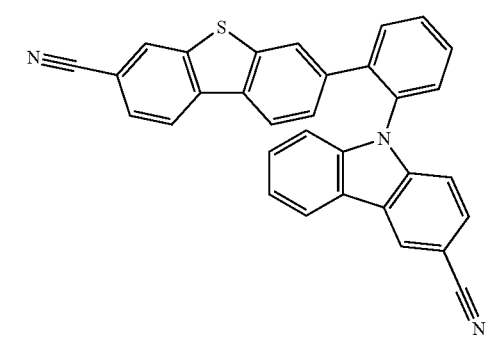
79
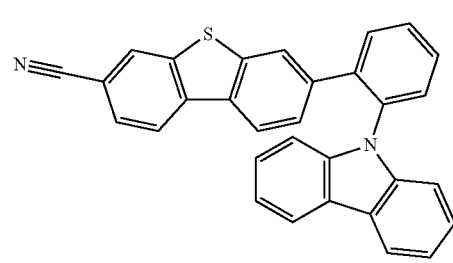
80
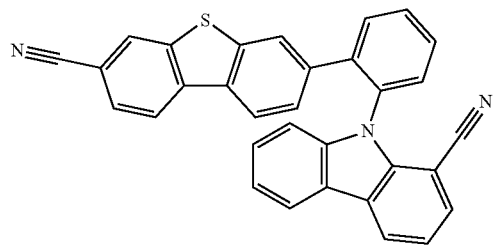
81
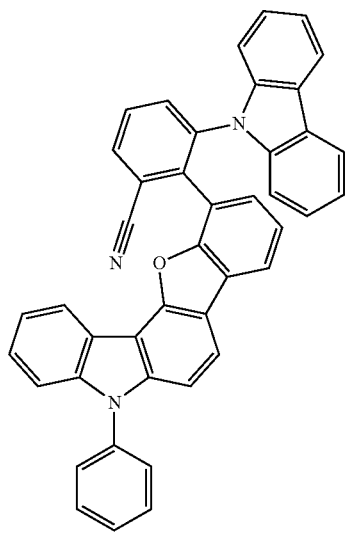
82
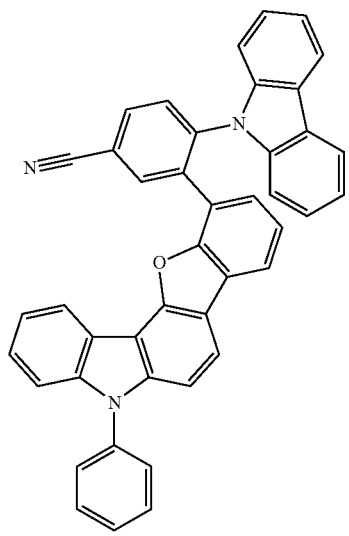

399
-continued
83
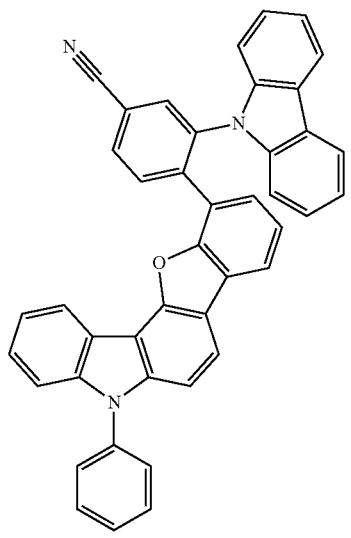
84
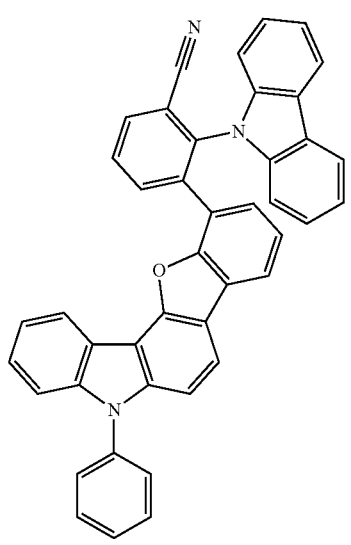
85
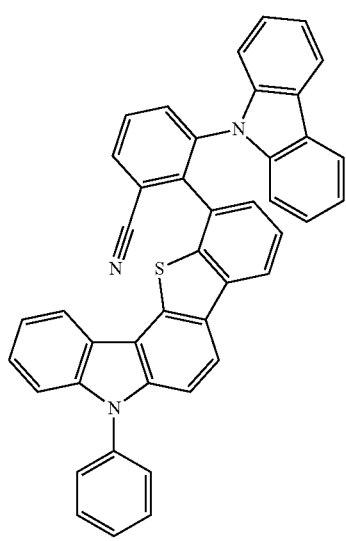
400
-continued
86
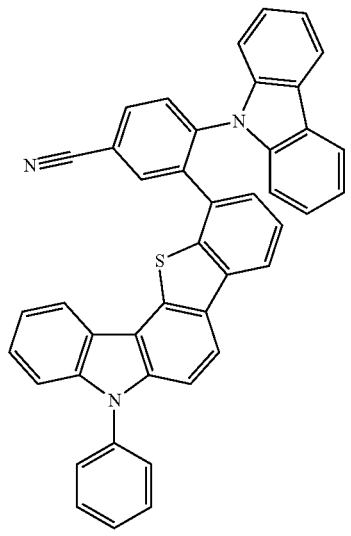
87
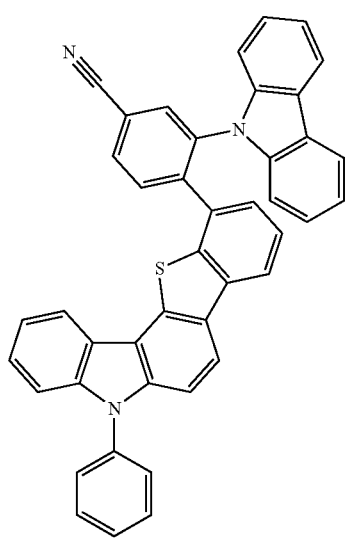
88
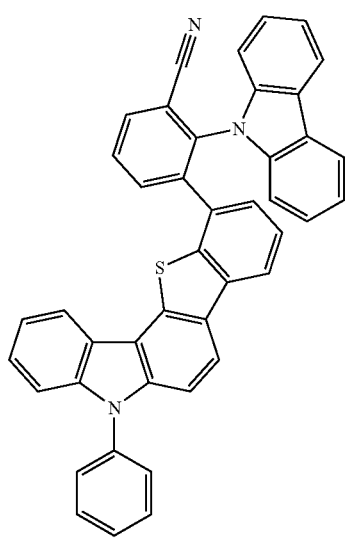

401
-continued
89
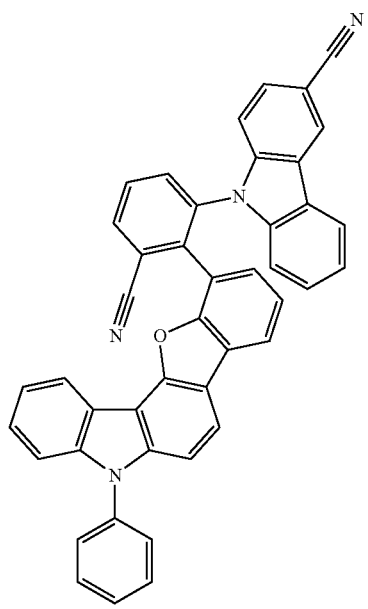
90
402
-continued
91
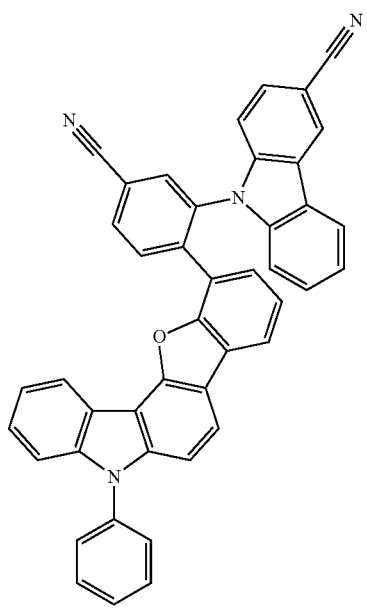
92

403
-continued
93
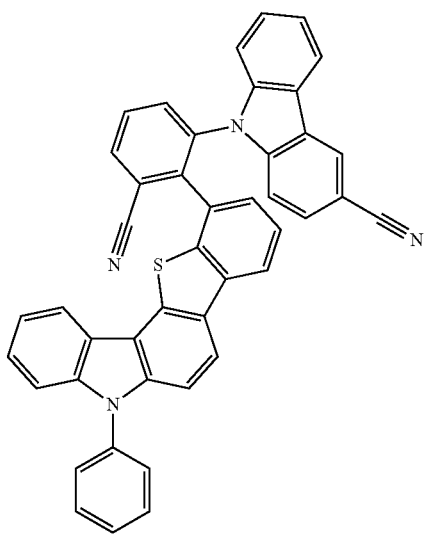
94
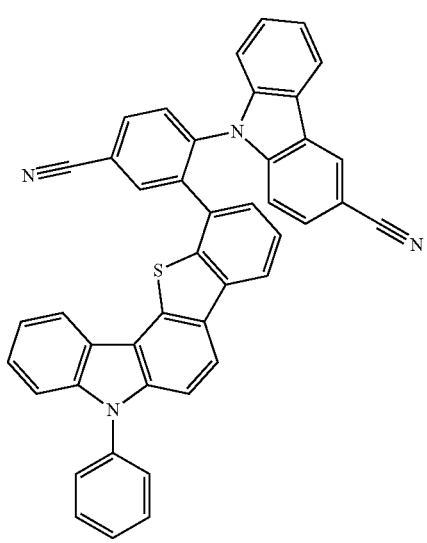
95
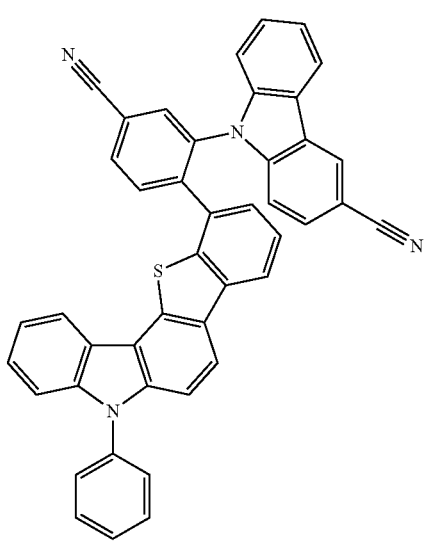
404
-continued
96
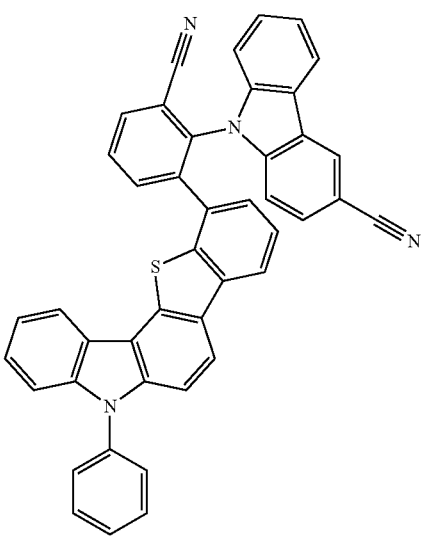
97
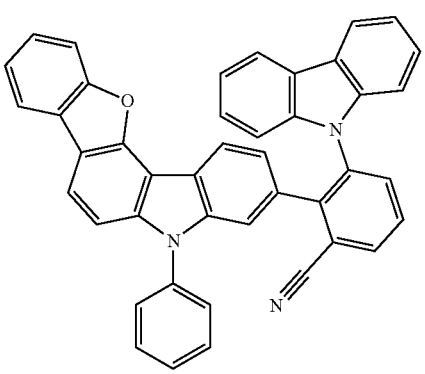
98
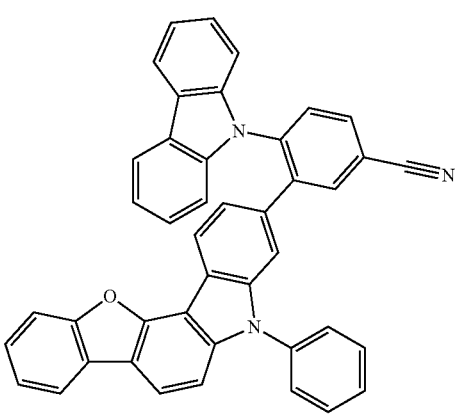

99
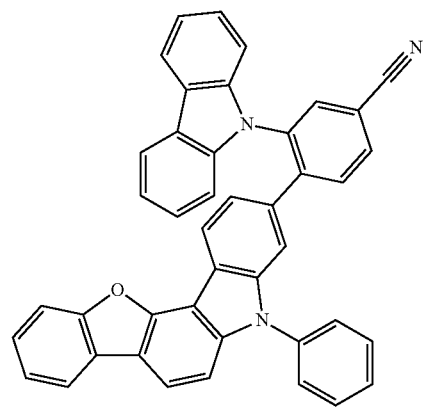
100
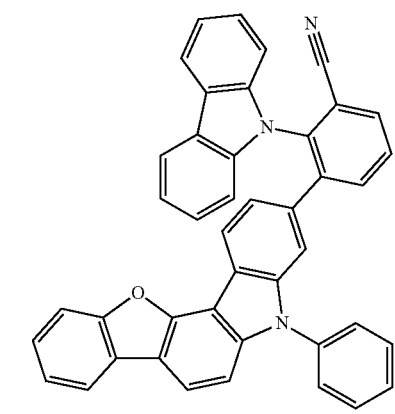
101
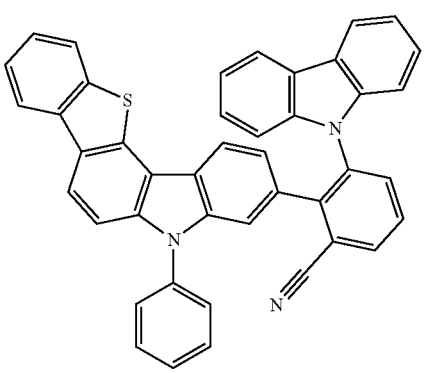
102
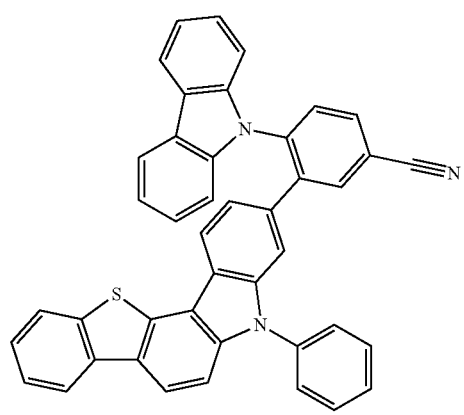
103
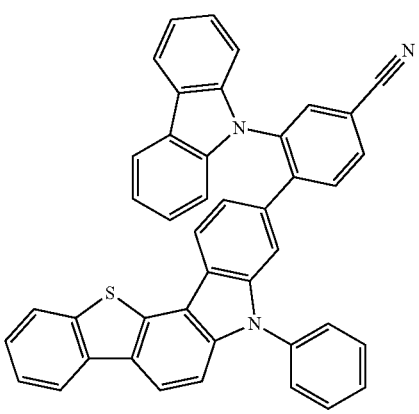
104
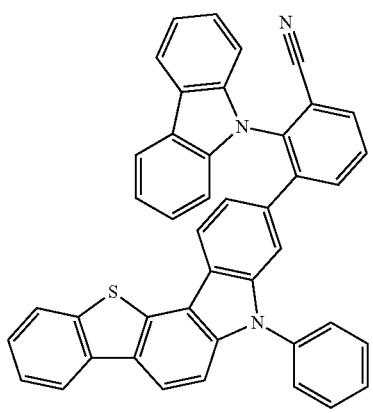
105
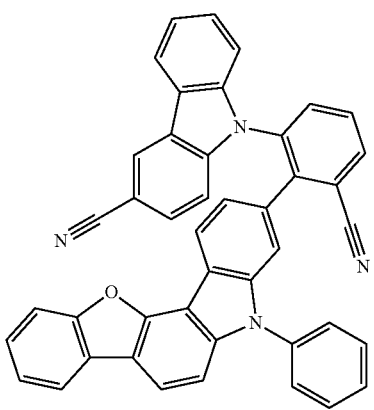
106
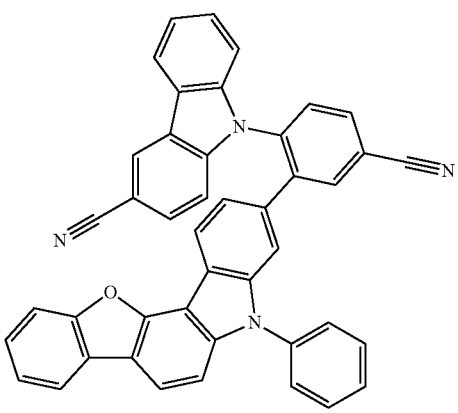

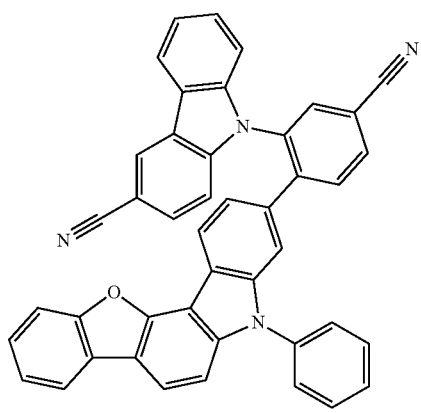
107
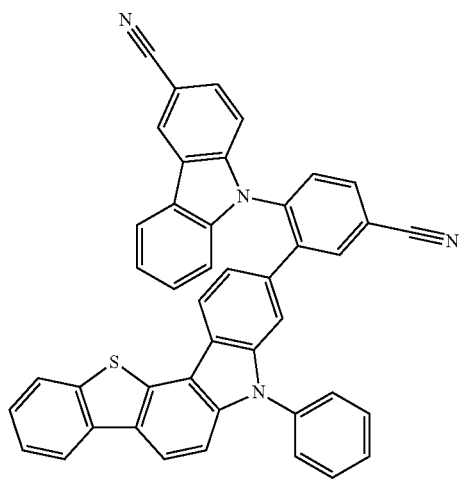
110
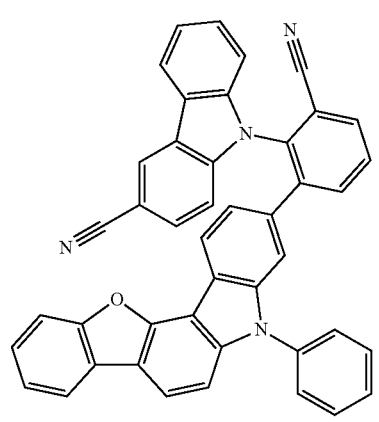
108
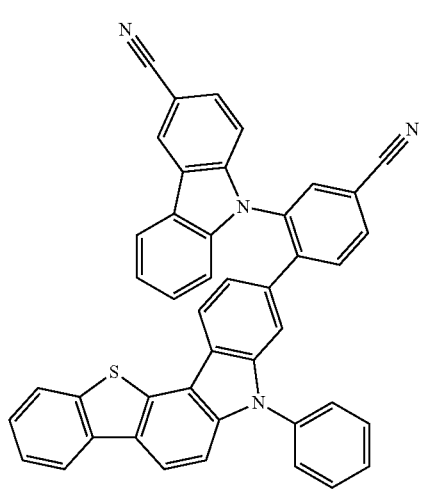
111
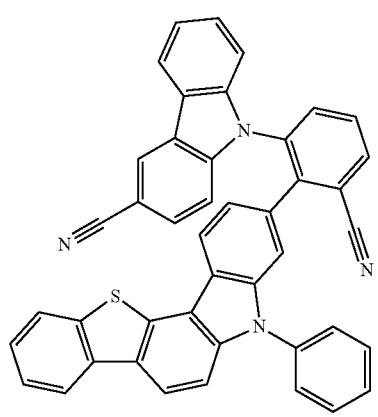
109
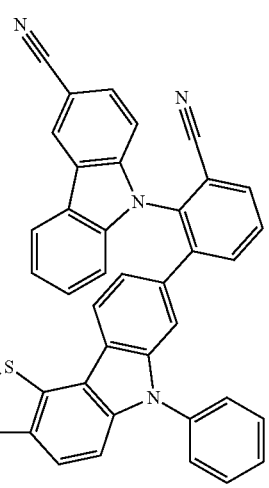
112

113
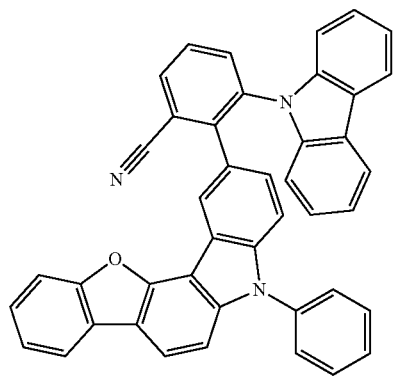
114
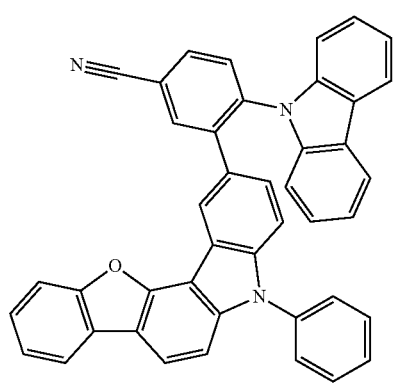
115
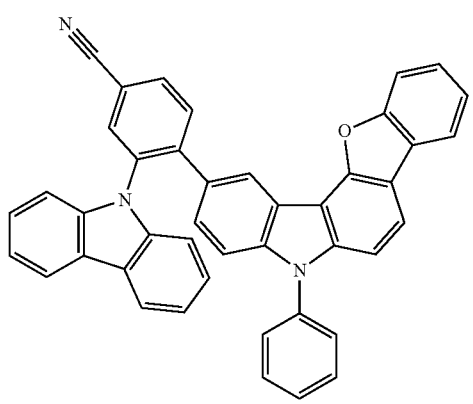
116
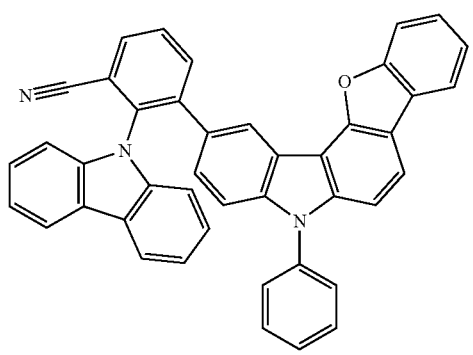
117
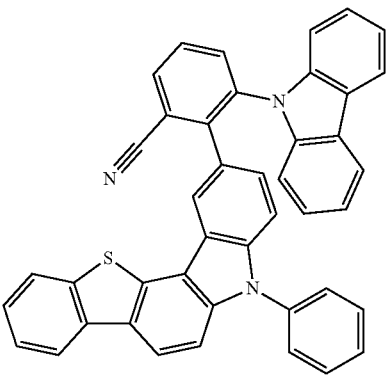
118
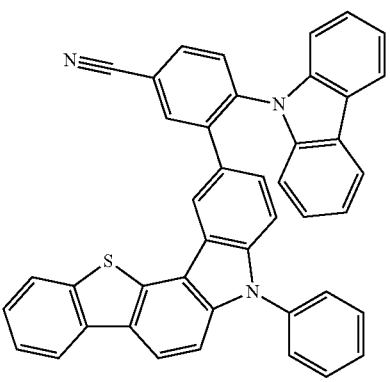
119
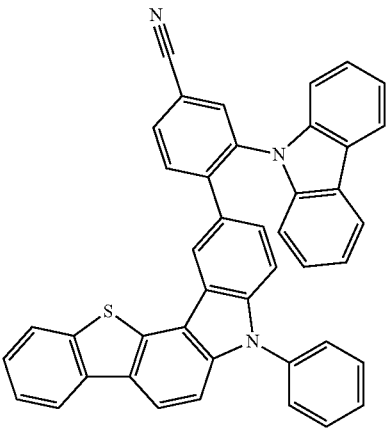
120
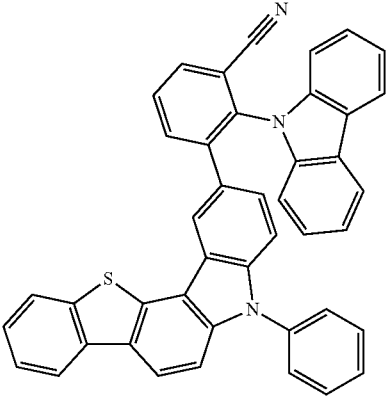

-continued
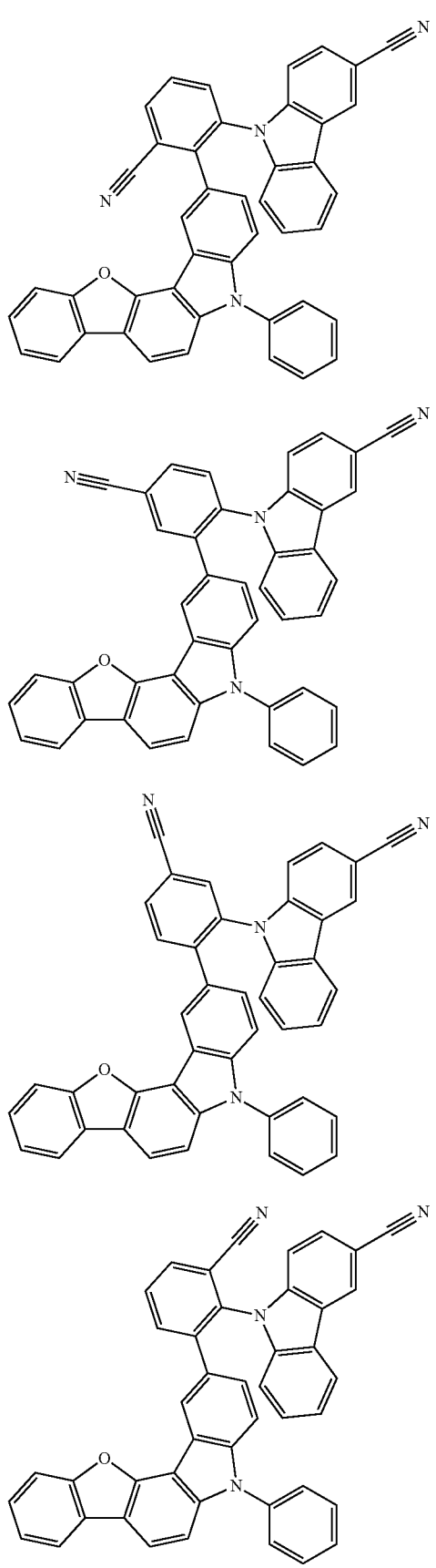
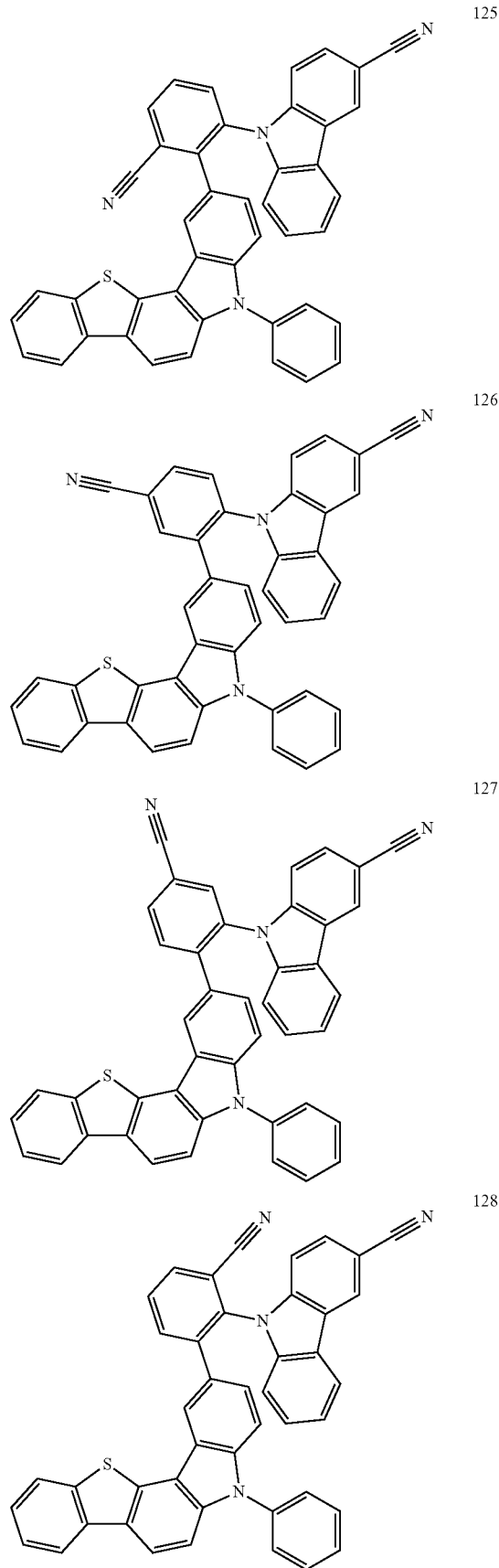

129
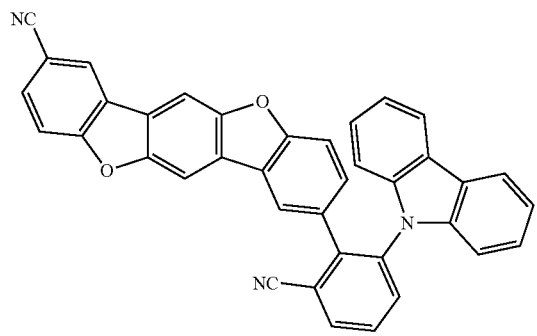
130
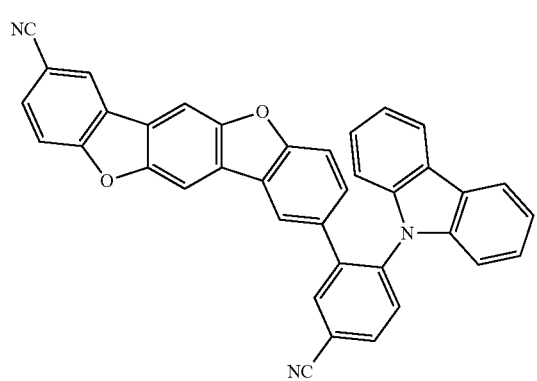
131
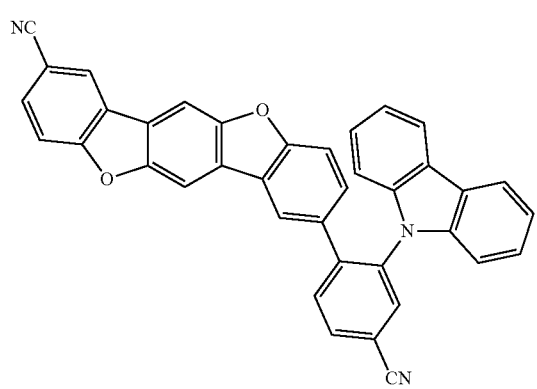
132
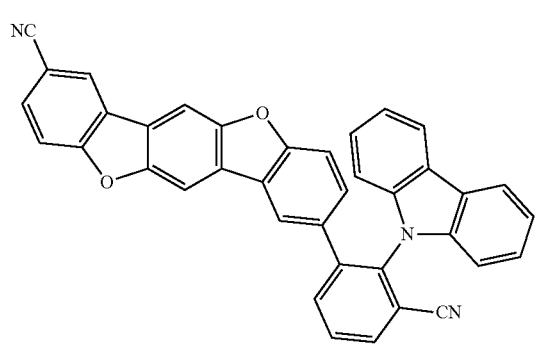
133
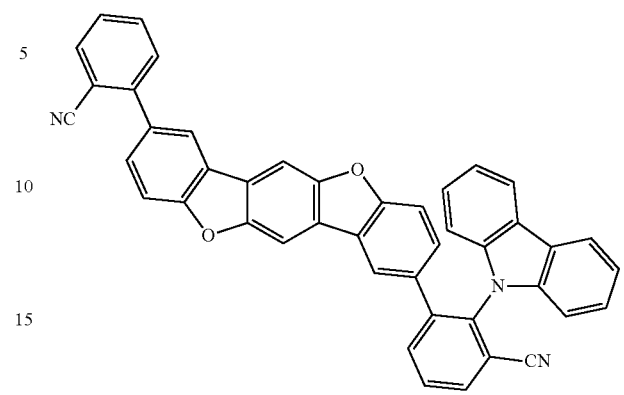
134
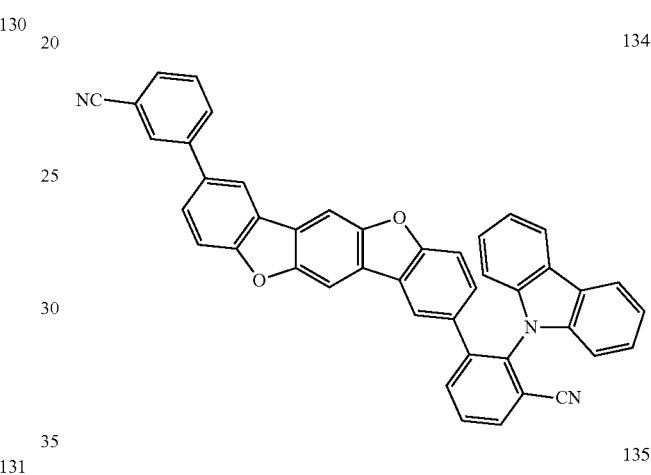
135
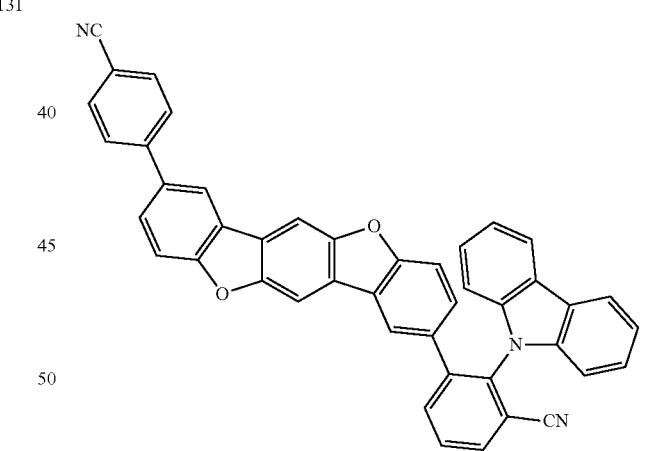
136
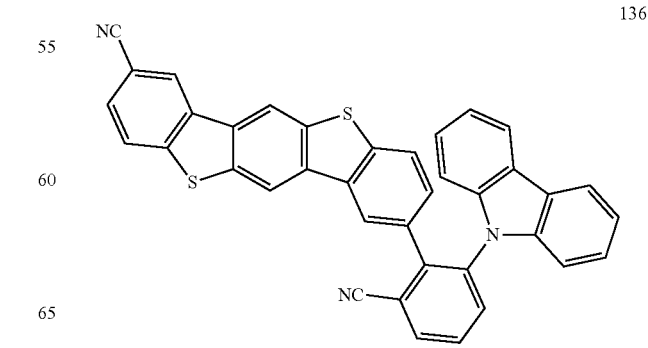

415
-continued
137
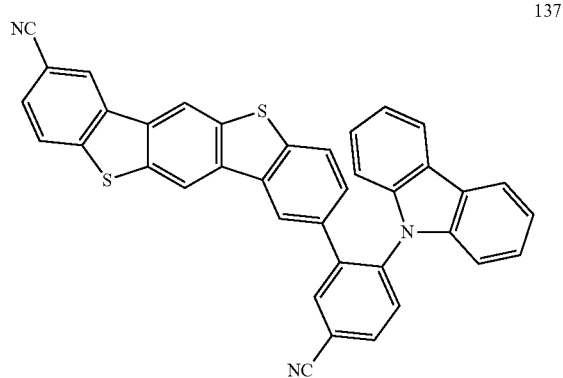
138
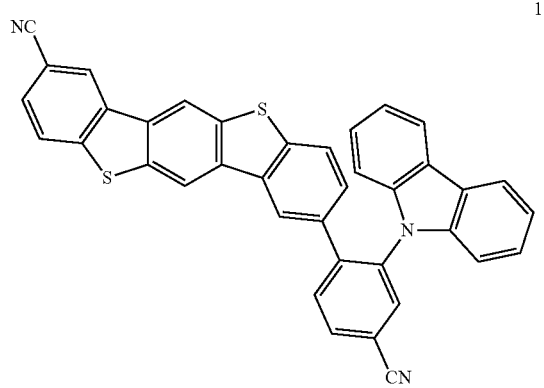
139
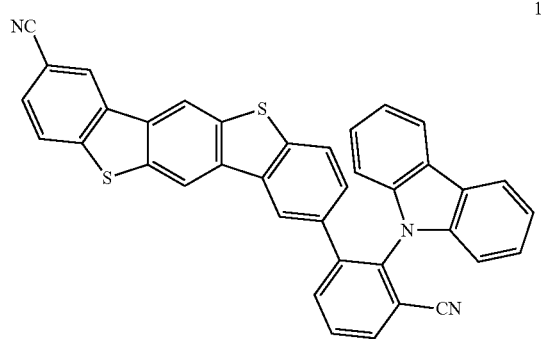
140
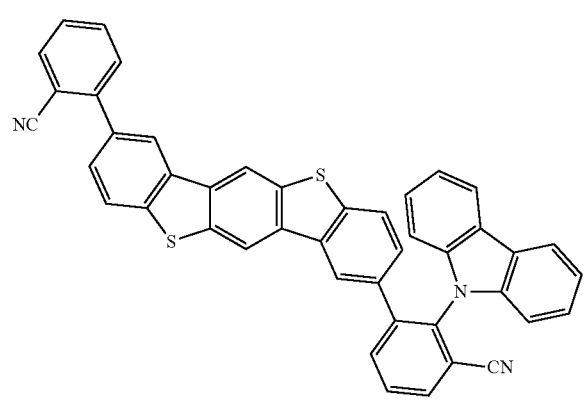
416
-continued
141
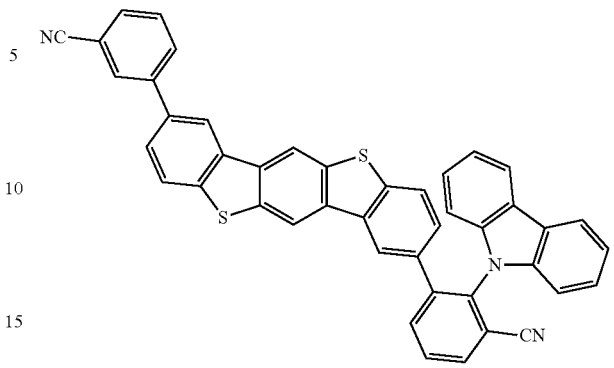
142
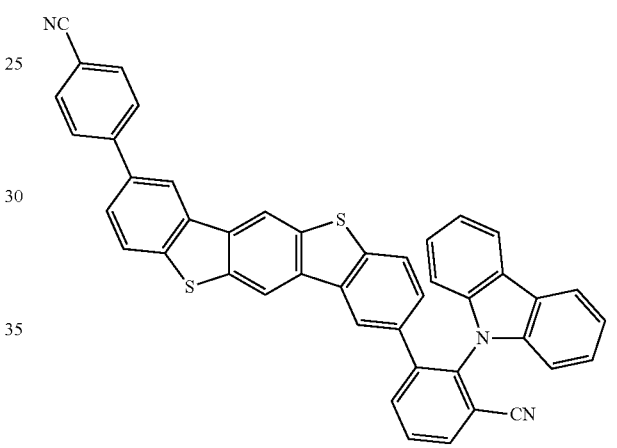
143
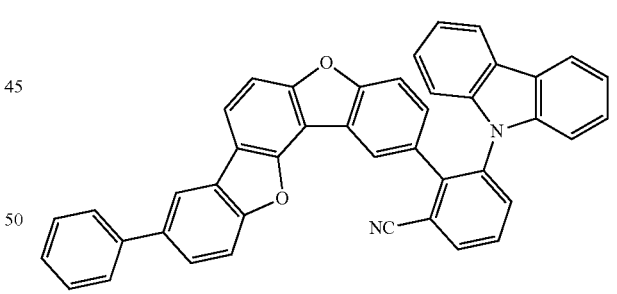
144
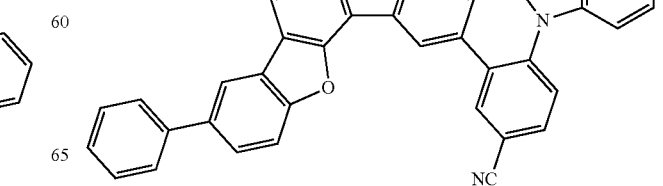

-continued
145
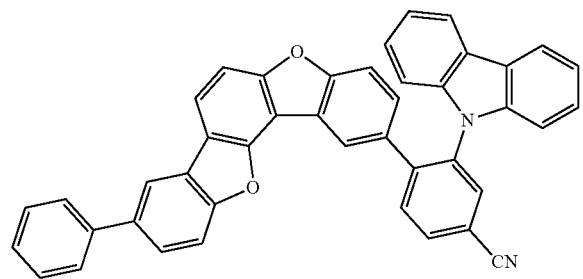
146
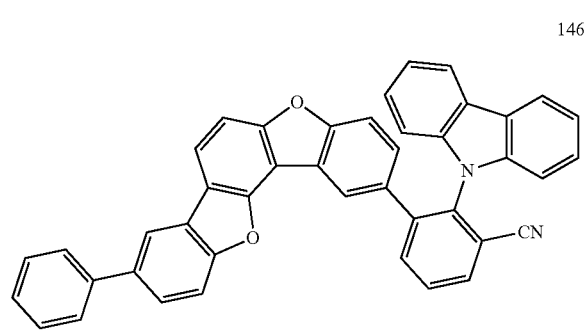
147
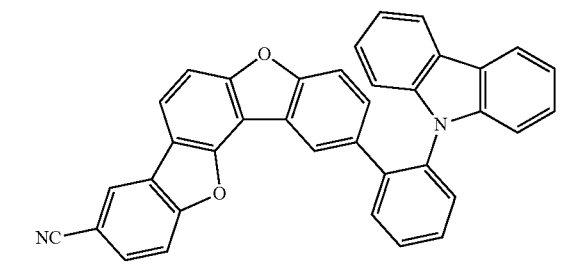
148
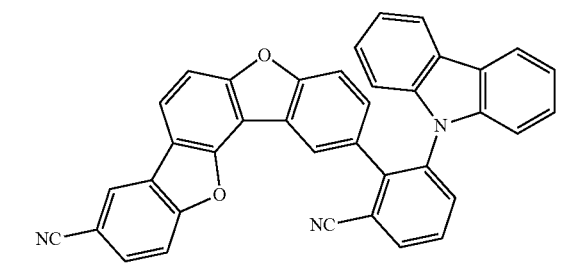
149
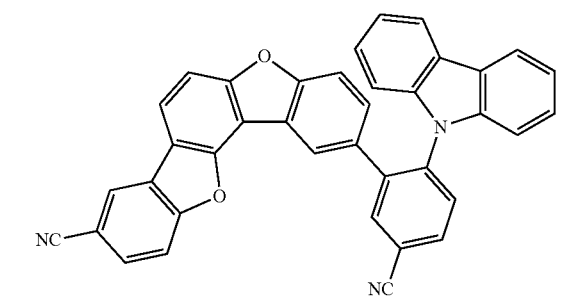
-continued
150
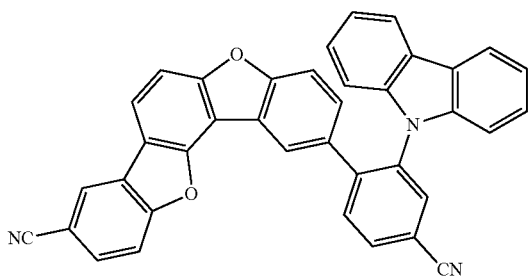
151
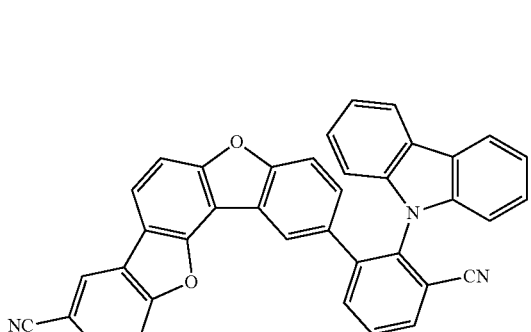
152
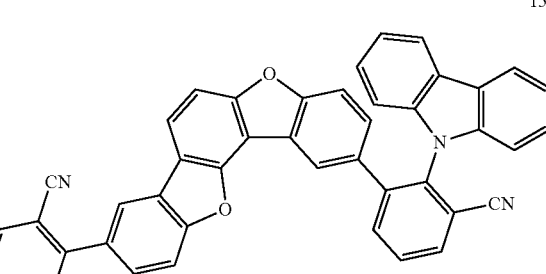
153
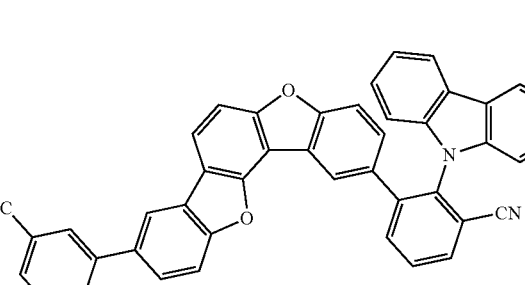
154
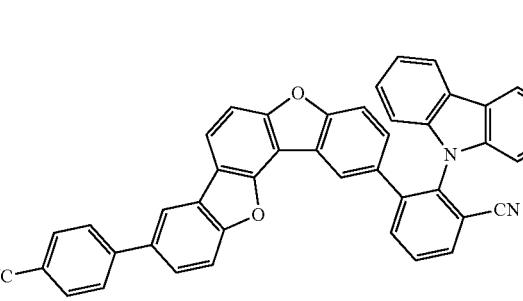

-continued
155
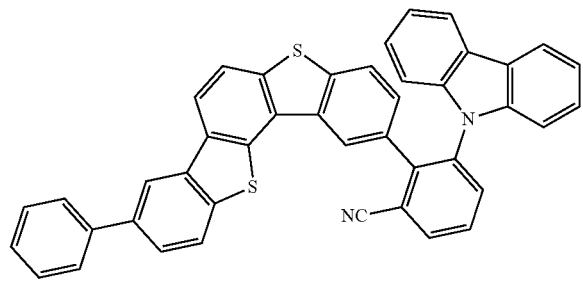
156
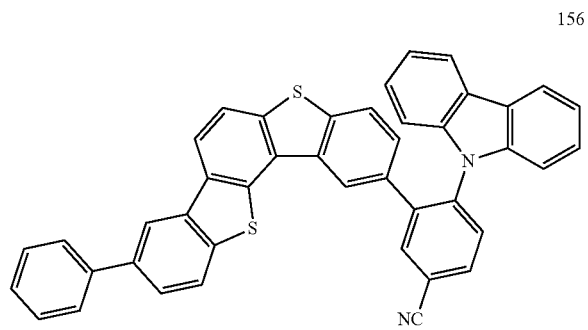
157
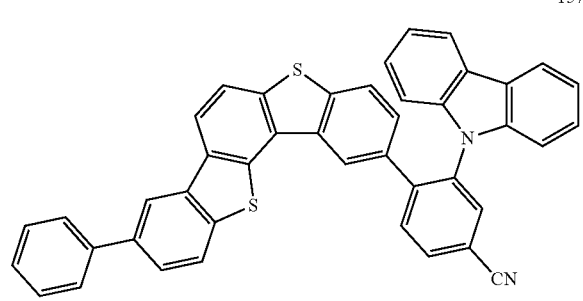
158
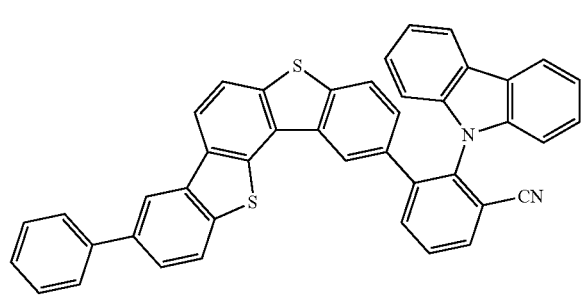
159
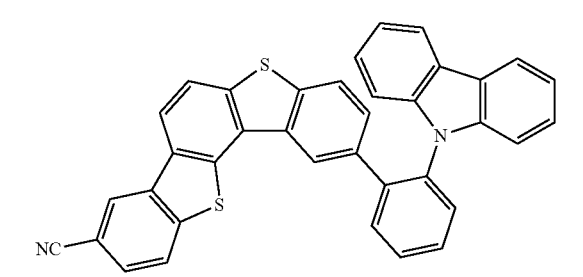
-continued
160
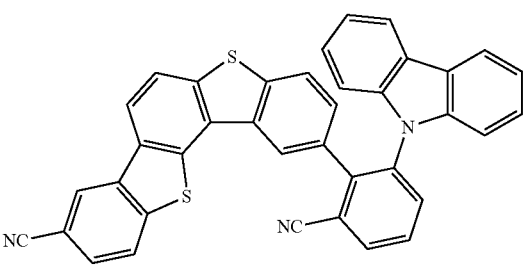
161
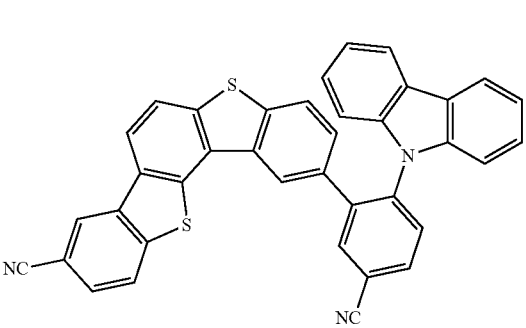
162
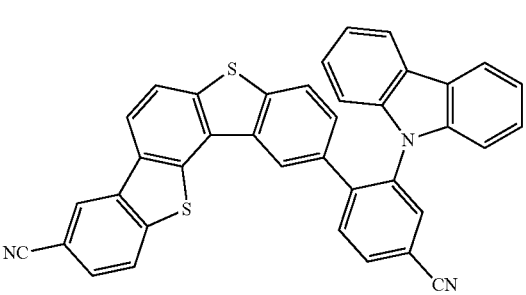
163
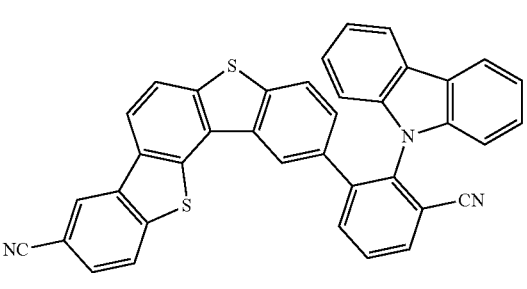
164
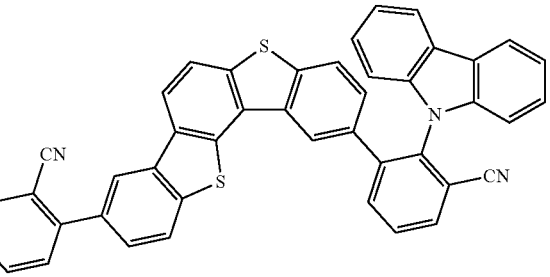

-continued
165
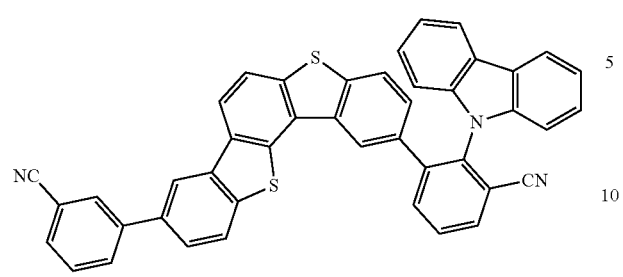
166
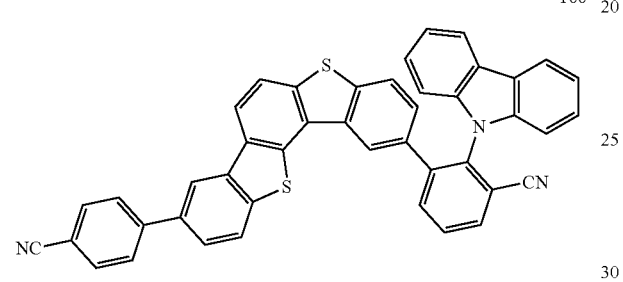
167
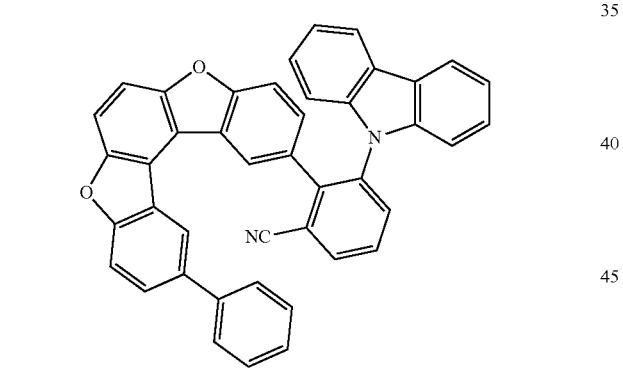
168
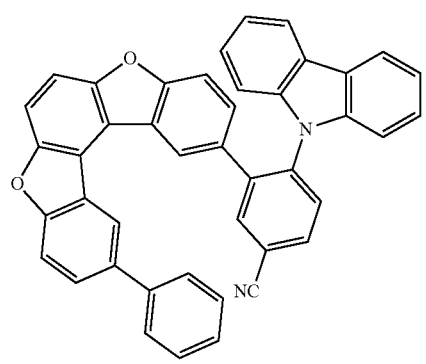
-continued
169
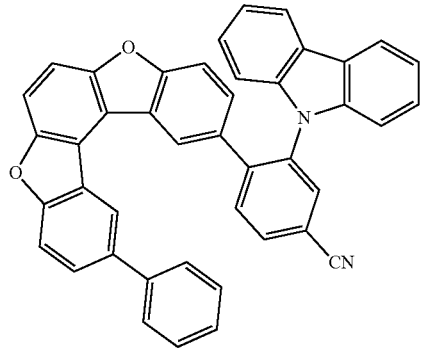
170
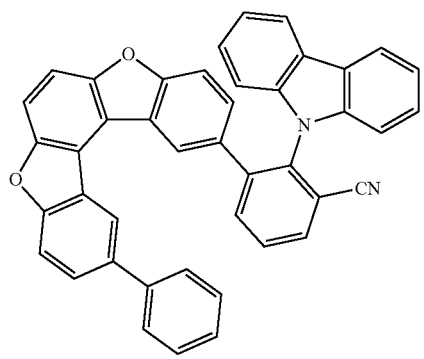
171
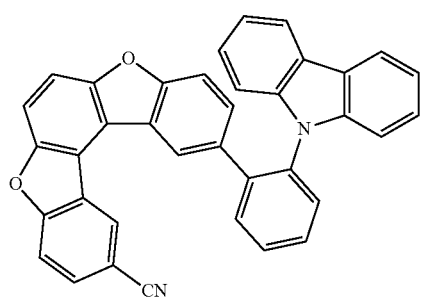
172
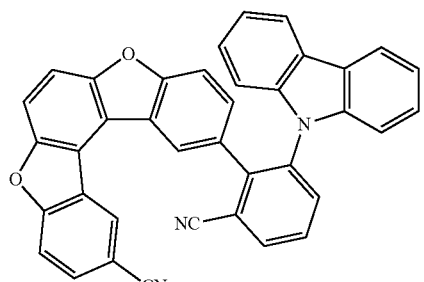
173
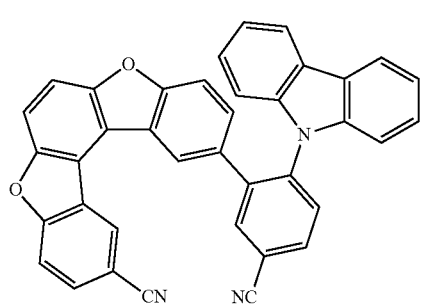

| 174 | 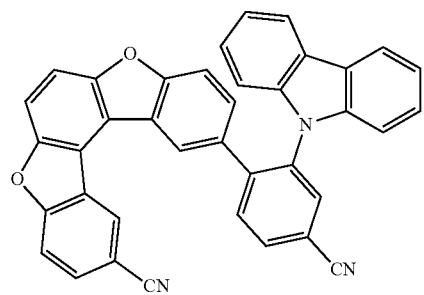 | 178 | 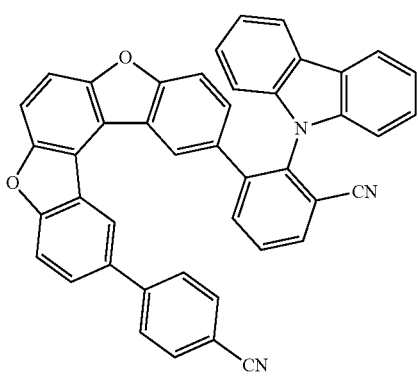 |
| 175 | 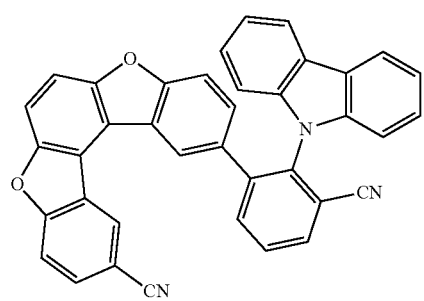 | 179 | 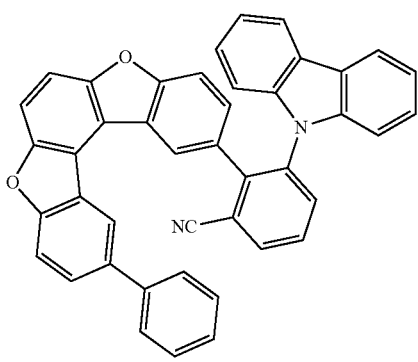 |
| 176 | 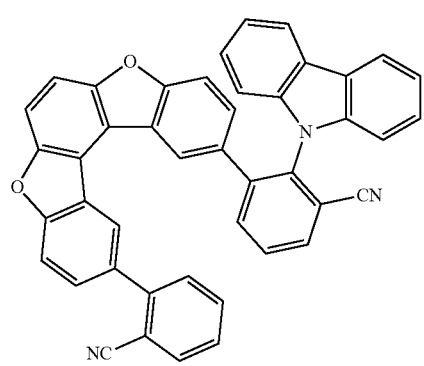 | 180 | 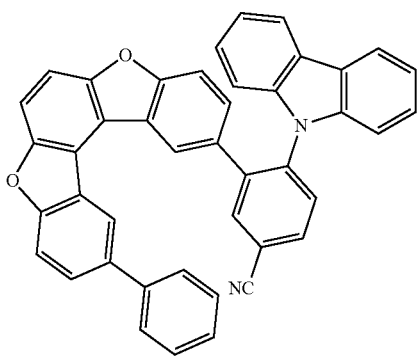 |
| 177 | 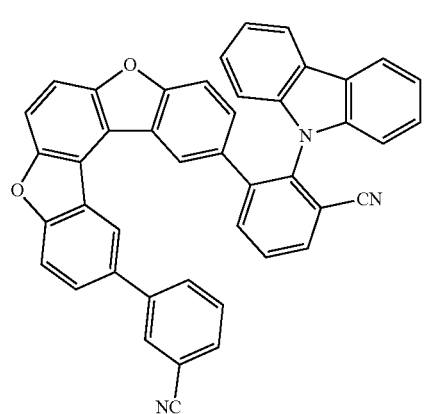 | 181 | 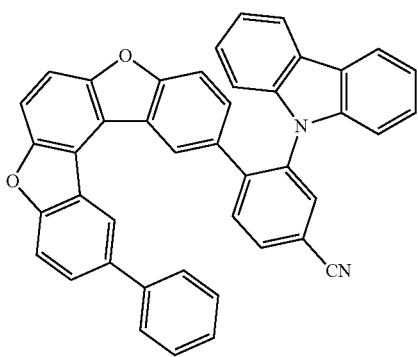 |

| 182 | 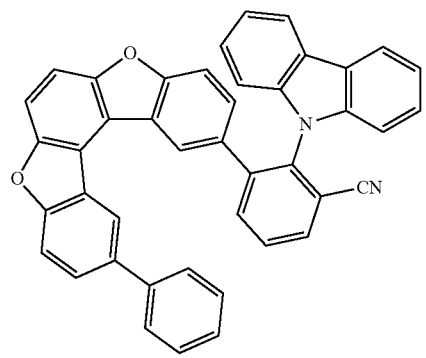 |
| --- | --- |
| 183 | 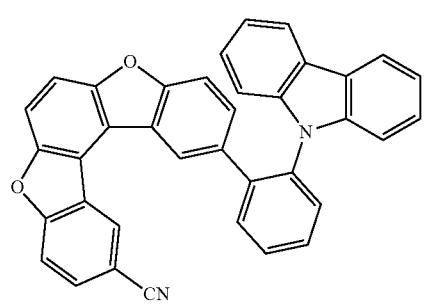 |
| 184 | 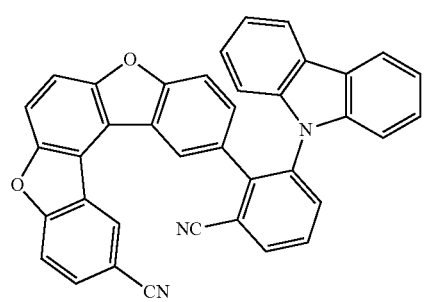 |
| 185 | 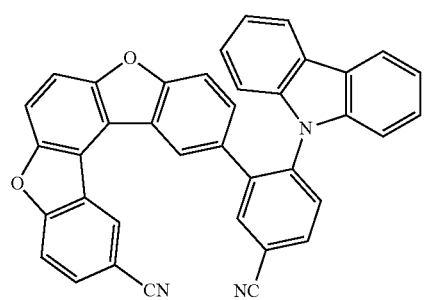 |
| 186 | 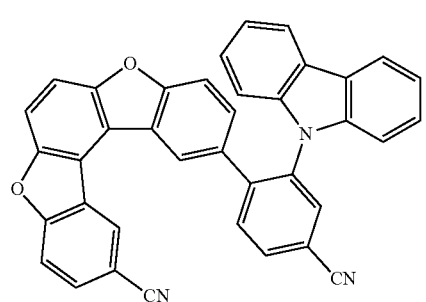 |
| 187 | 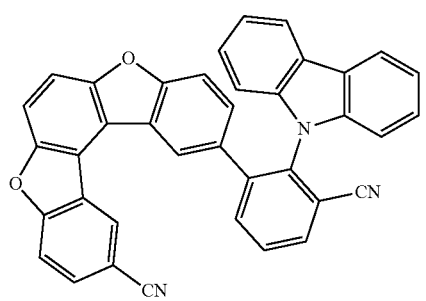 |
| 188 | 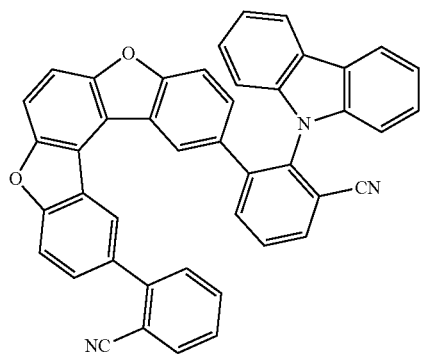 |
| 189 | 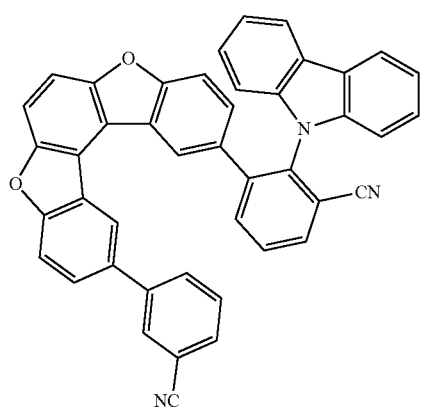 |
| 190 | 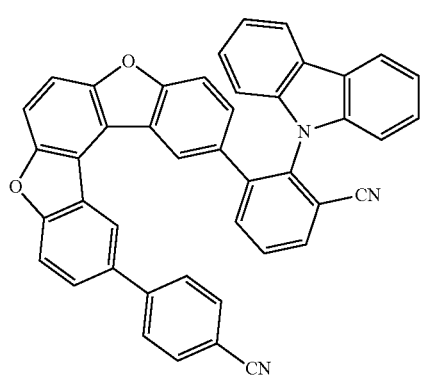 |

427
-continued
191
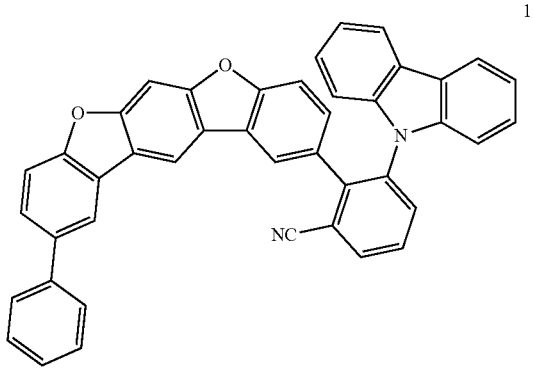
192
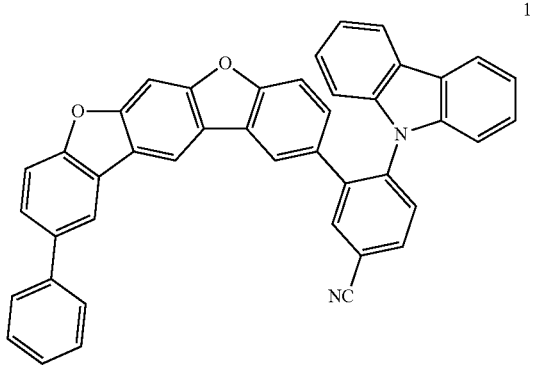
193
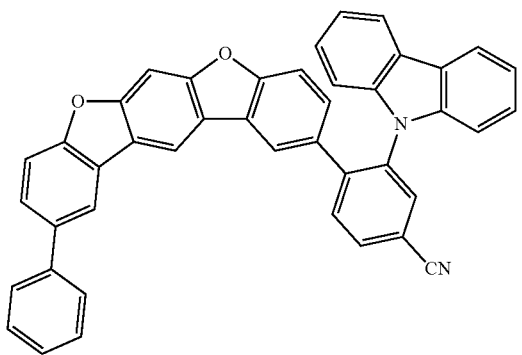
194
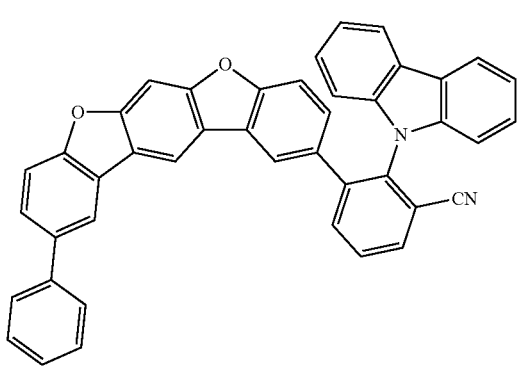
428
-continued
195
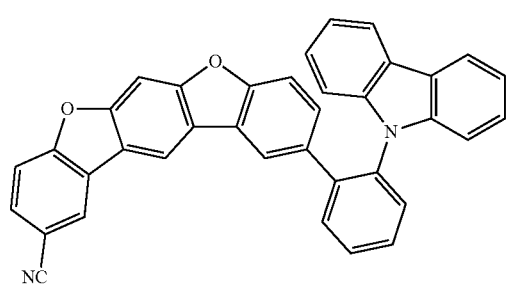
196
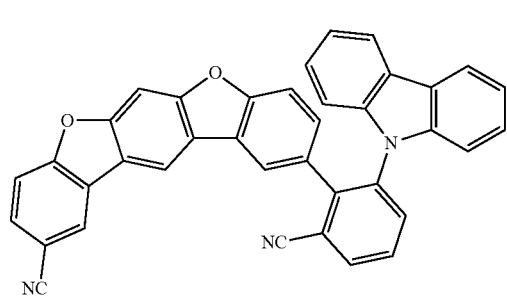
197
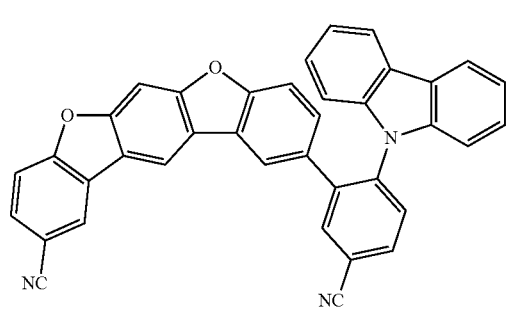
198
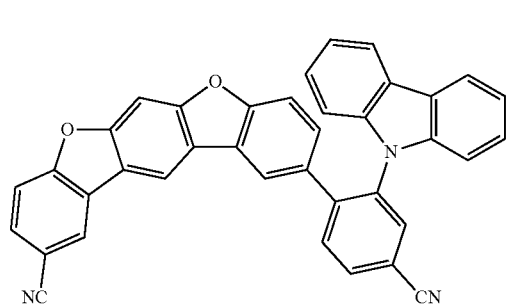
199
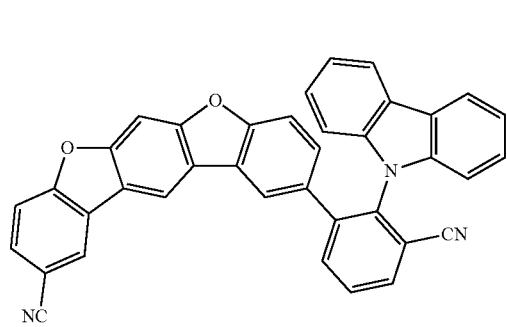

200
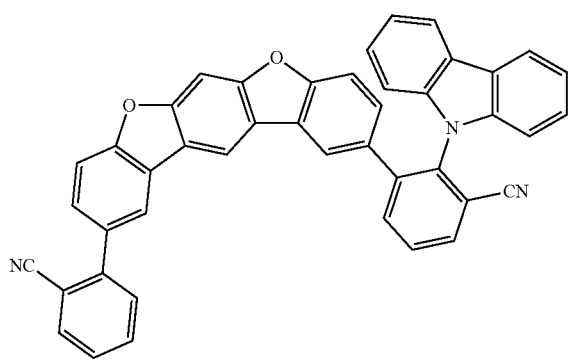
201
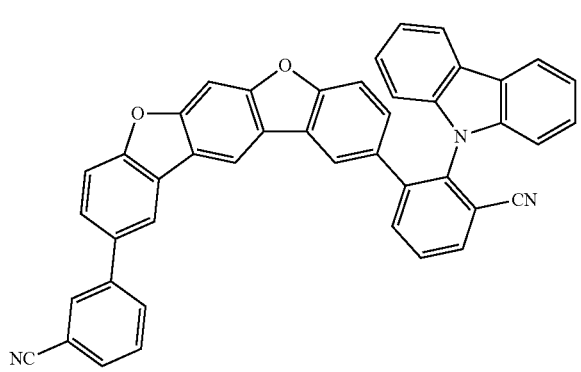
202
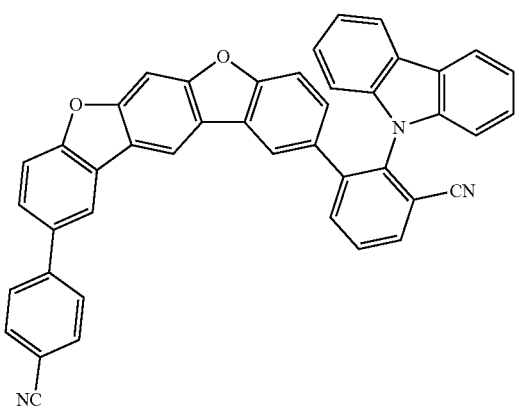
203
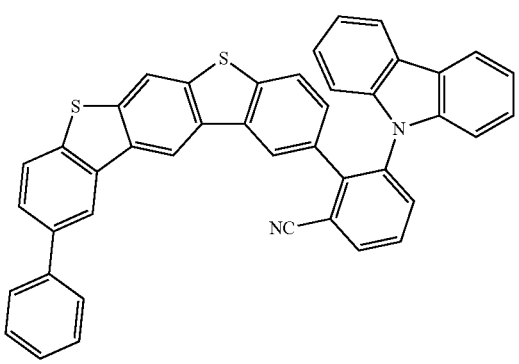
204
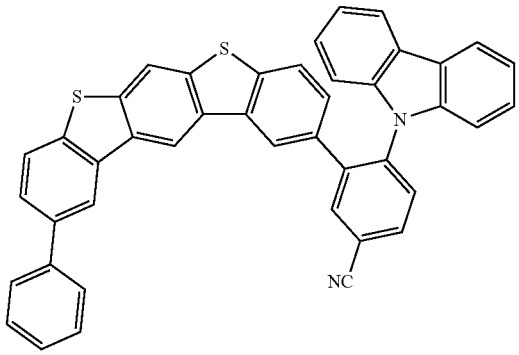
205
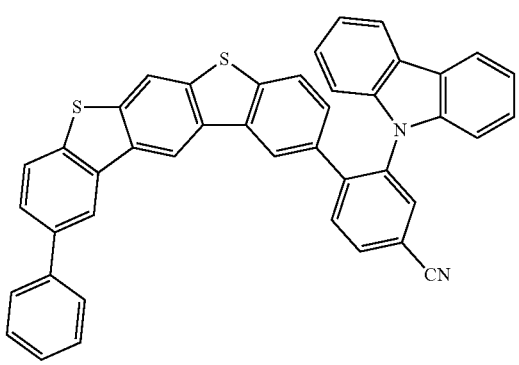
206
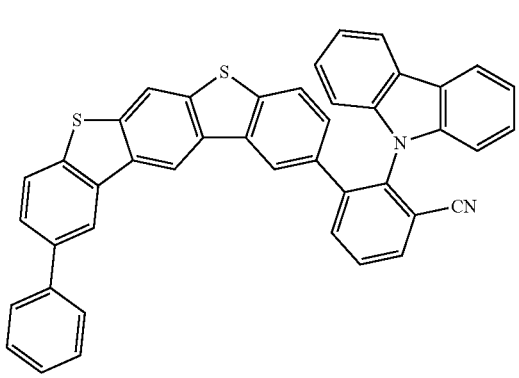
207
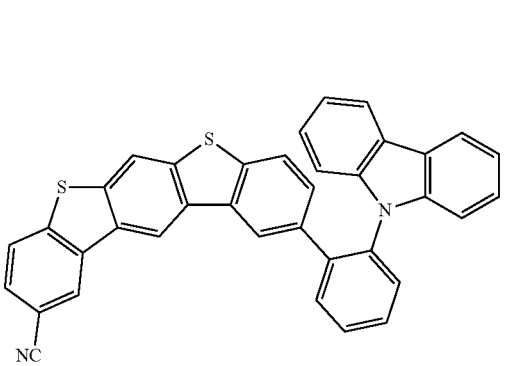

208
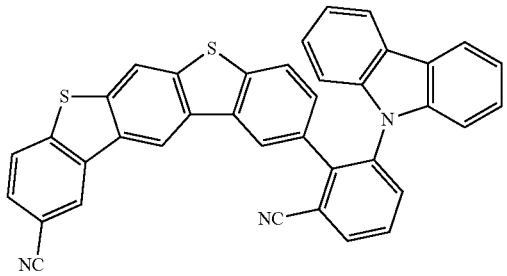
209
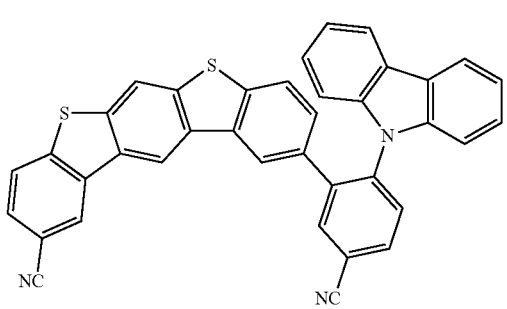
210
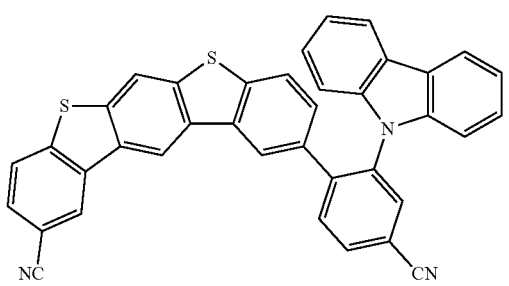
211
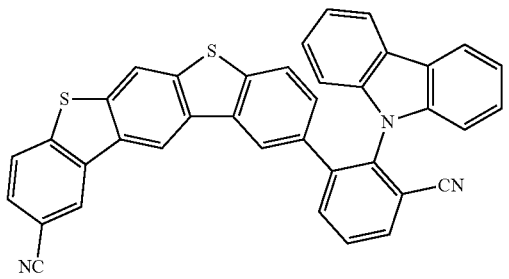
212
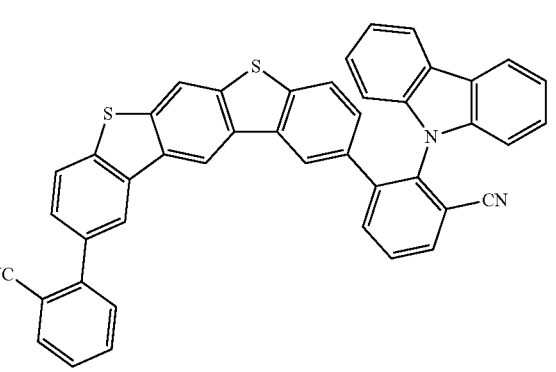
213
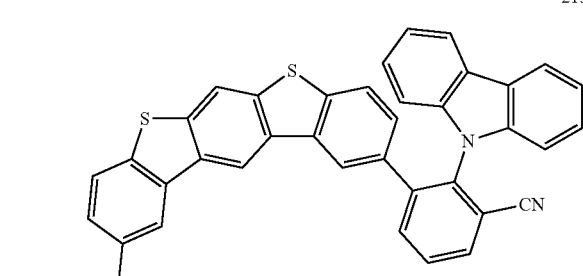
214
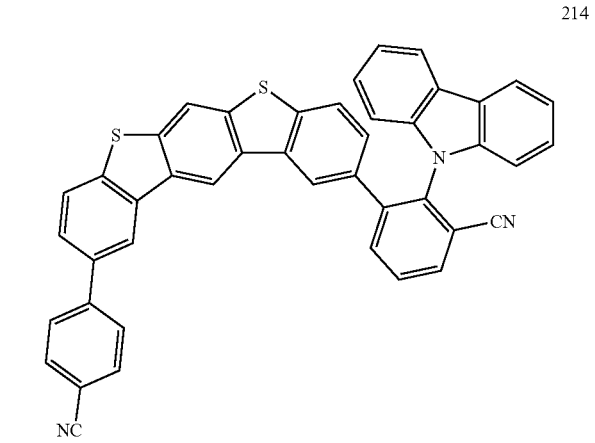
215

216
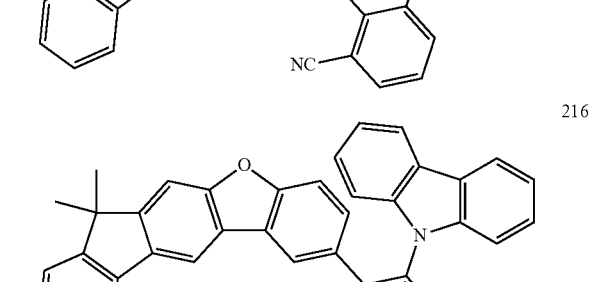
217
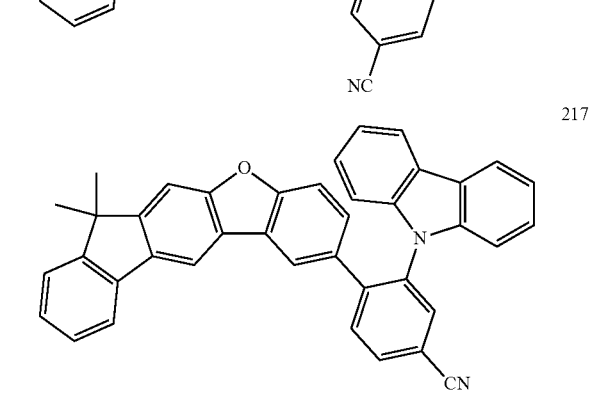

433
-continued
218
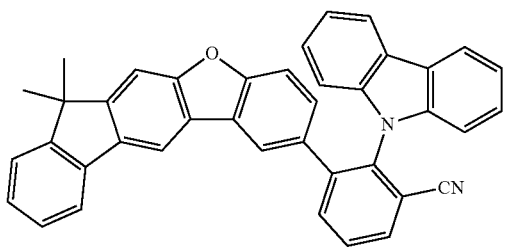
219
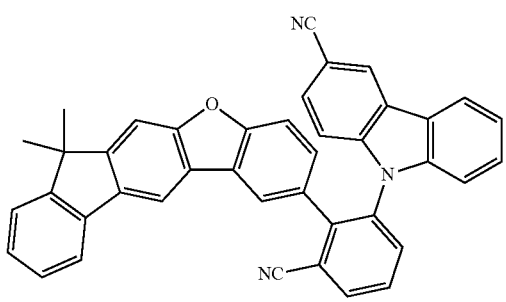
220
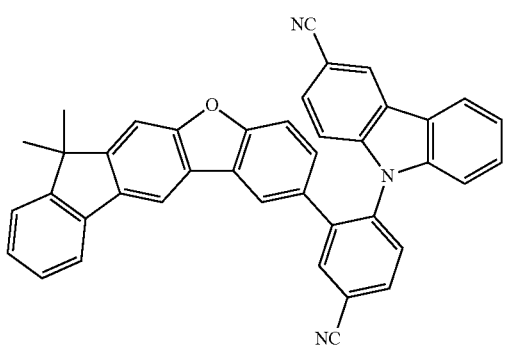
221
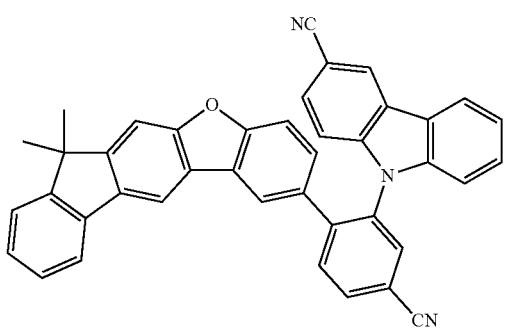
222
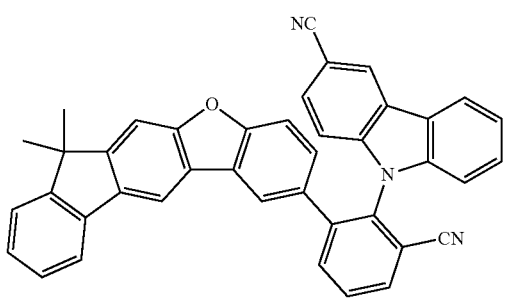
434
-continued
223
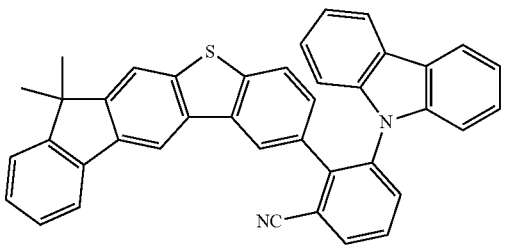
224
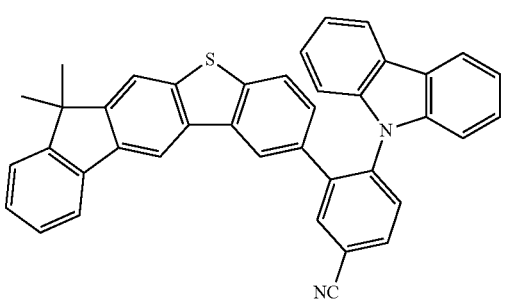
225
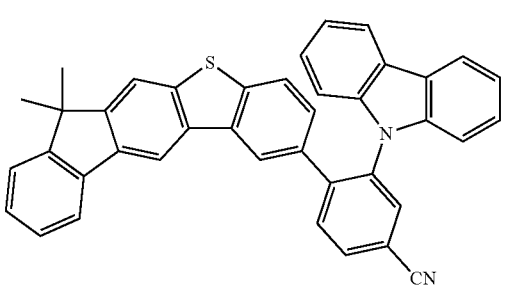
226
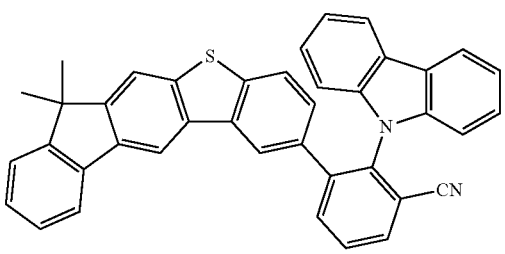
227
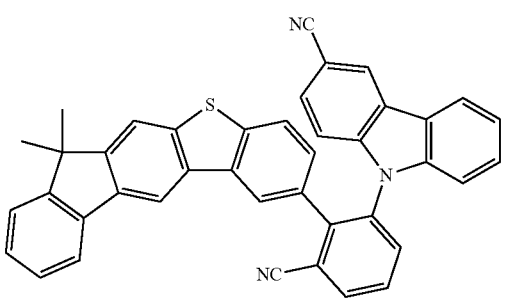

228
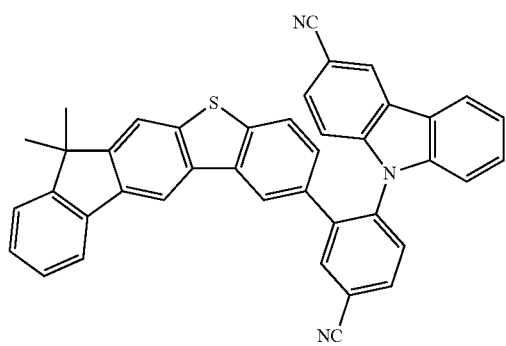
229
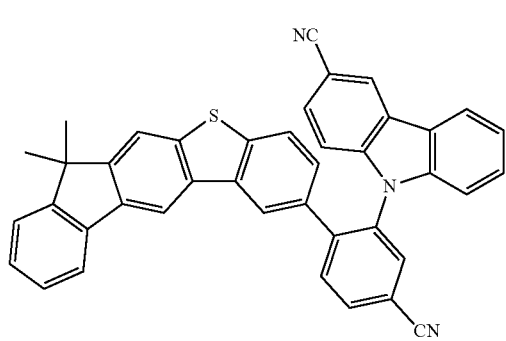
230

231

232
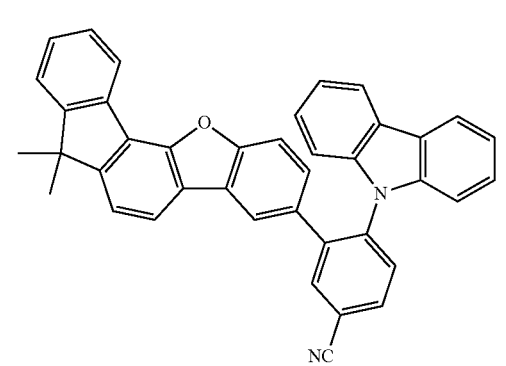
233
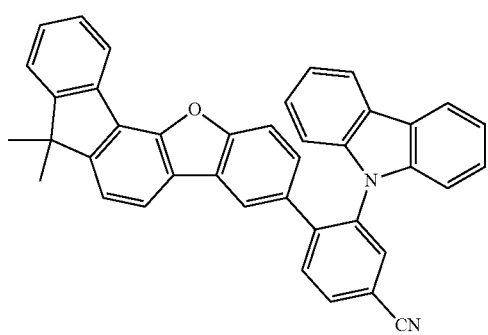
234
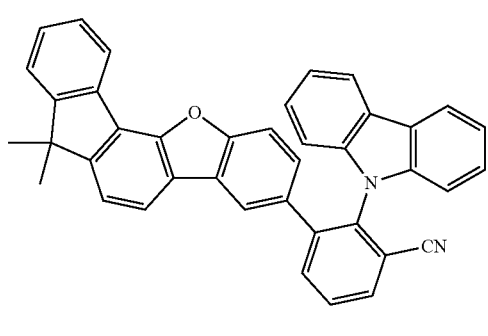
235
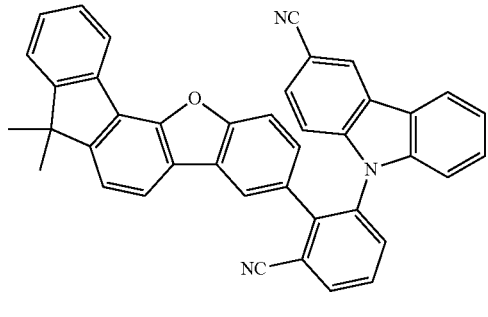
236
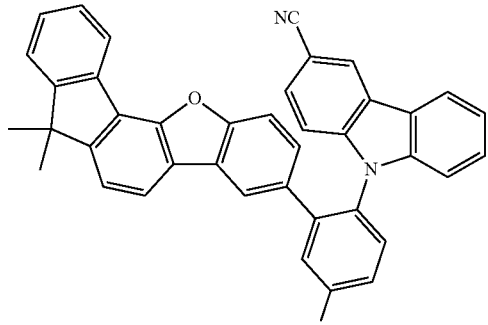
237
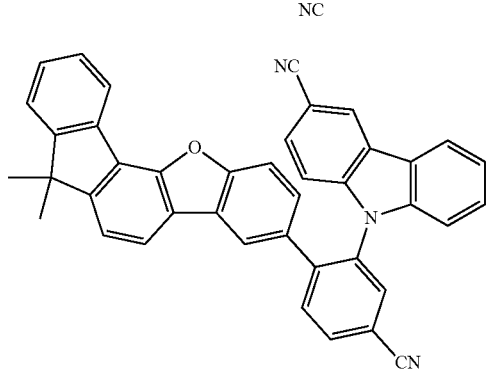

437
-continued
238
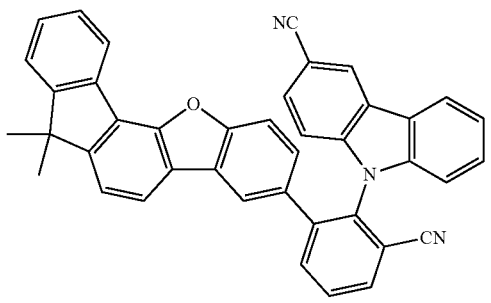
239
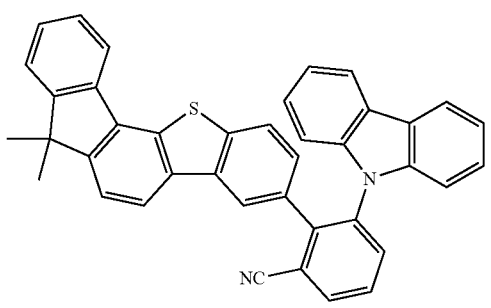
240
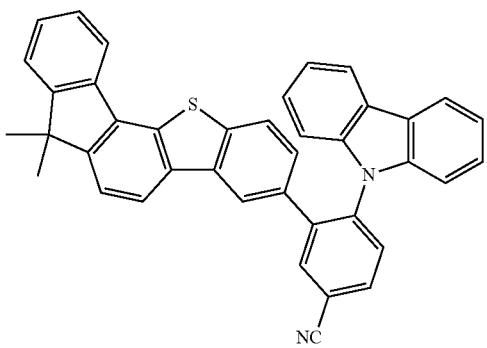
241
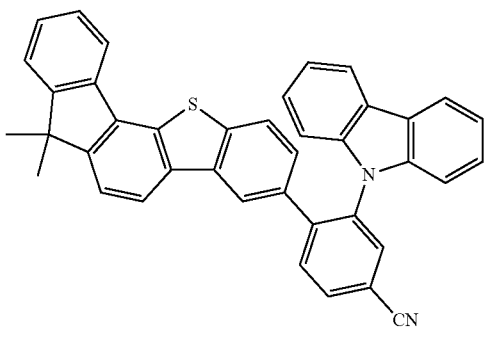
242
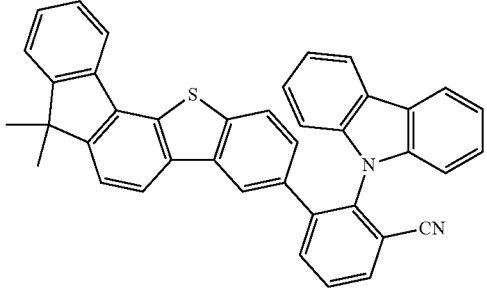
438
-continued
243
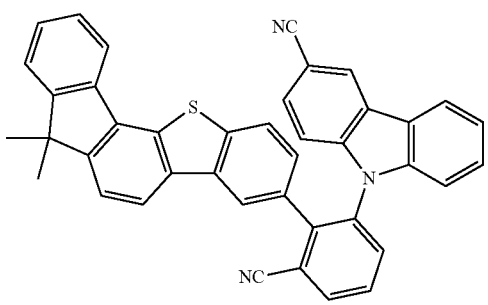
244
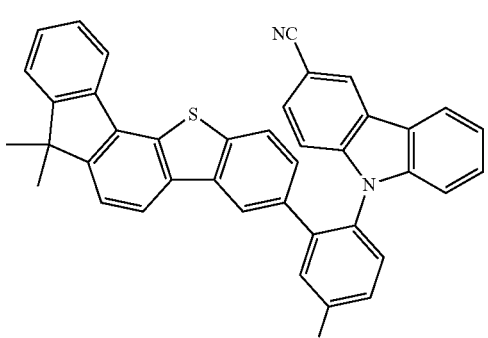
245
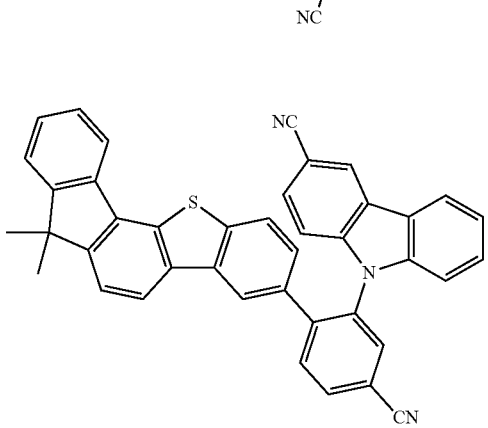
246
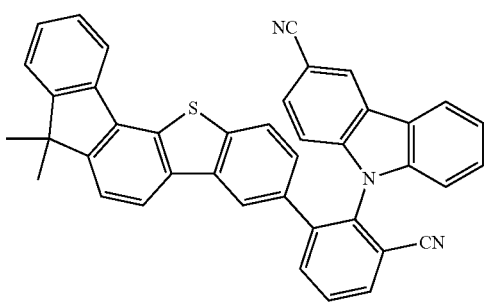
247
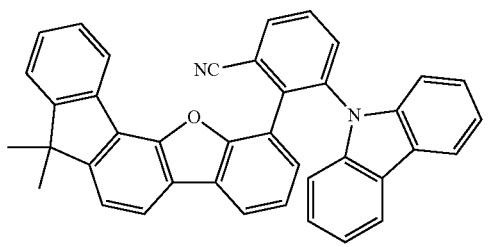

-continued
248
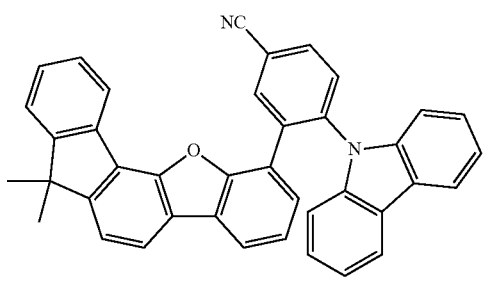
249
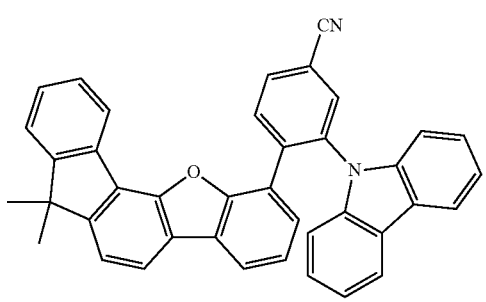
250
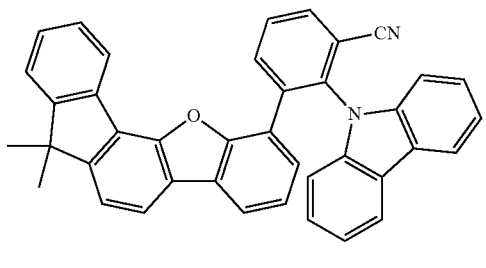
251
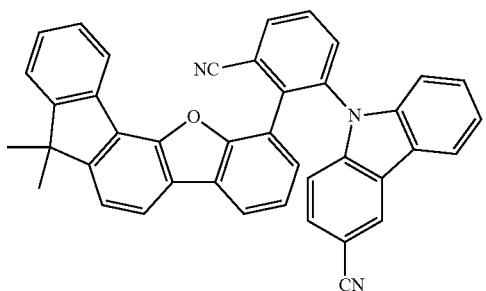
252
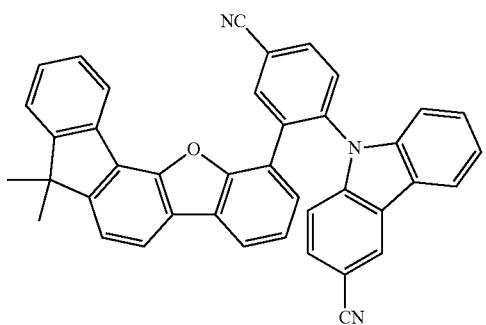
-continued
253
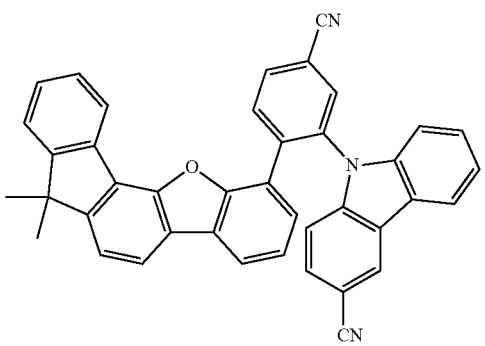
254
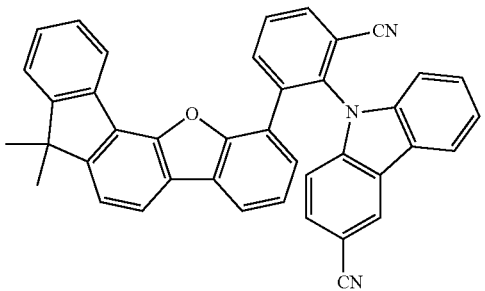
255
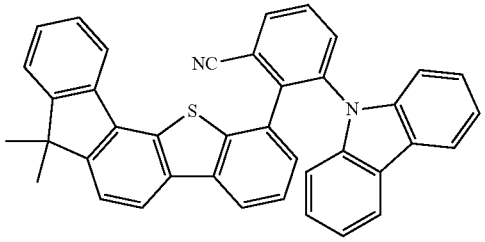
256
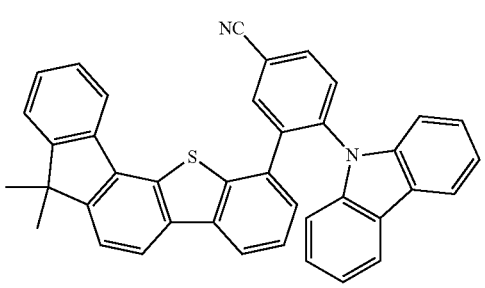
257
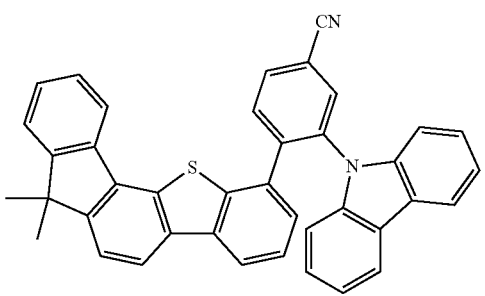

441
-continued
258
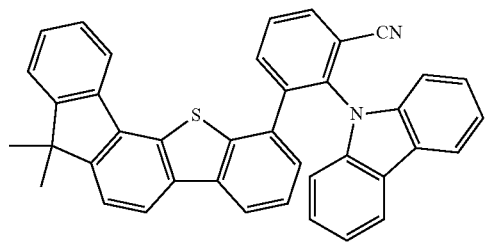
259
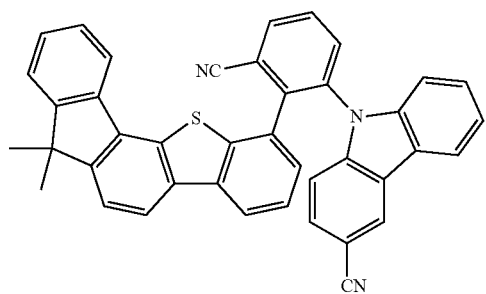
260
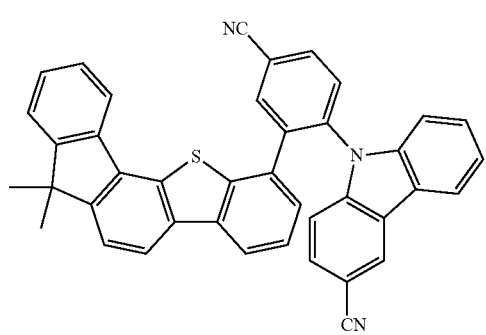
261
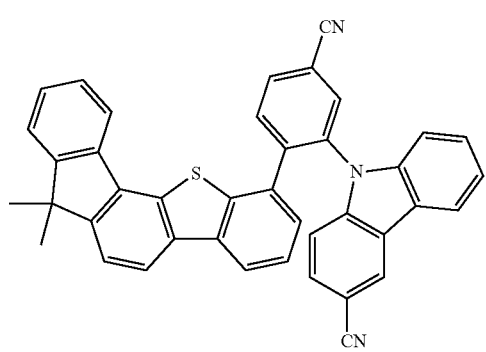
262
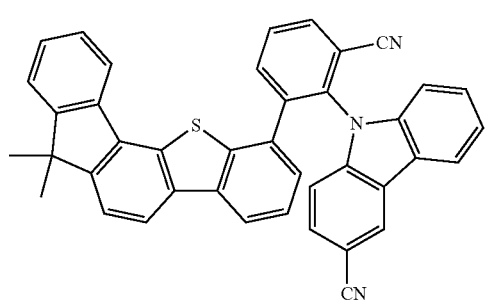
442
-continued
263
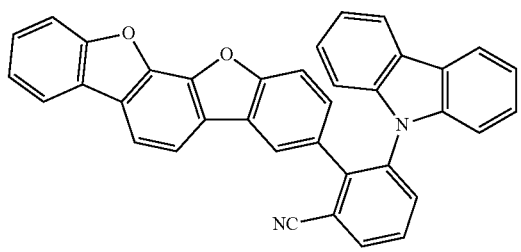
264
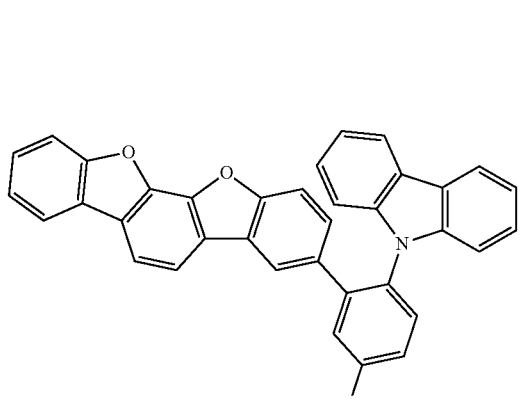
265
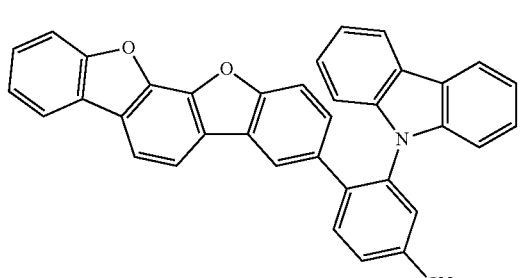
266
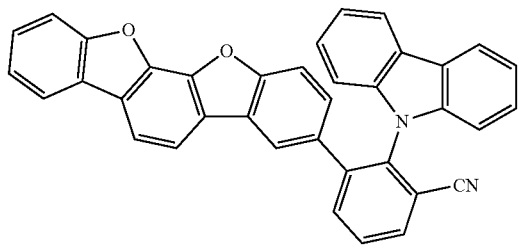
267
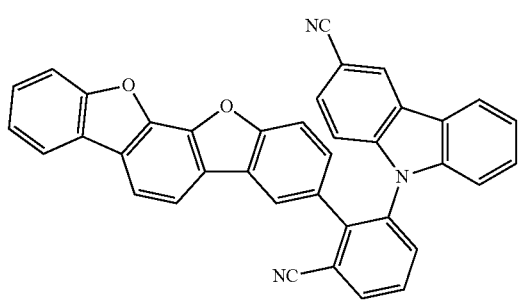

-continued
268
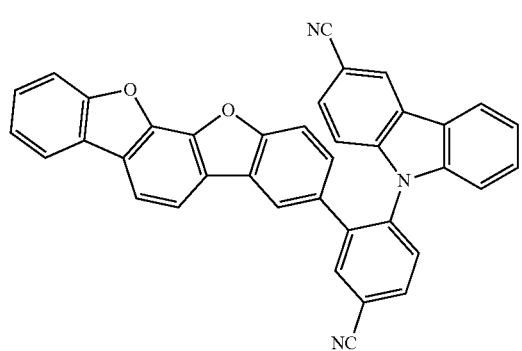
269
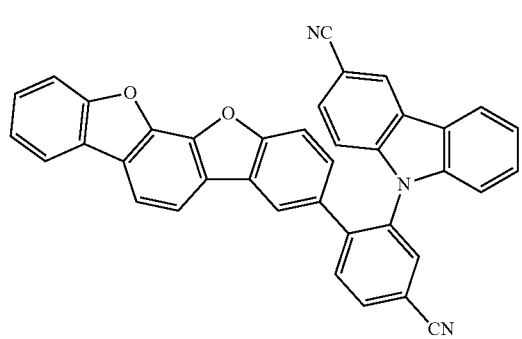
270
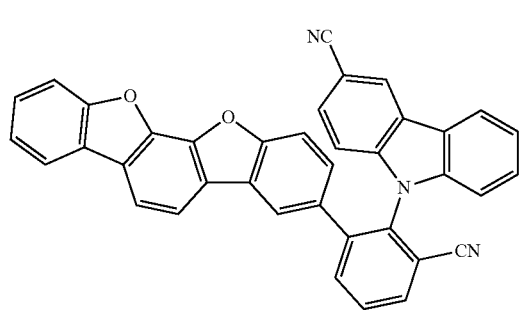
271
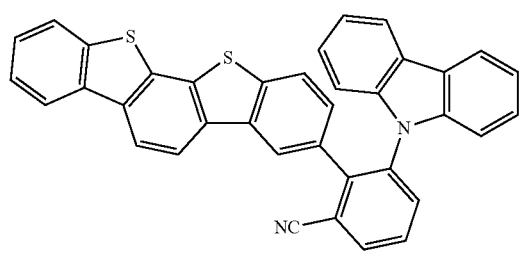
272
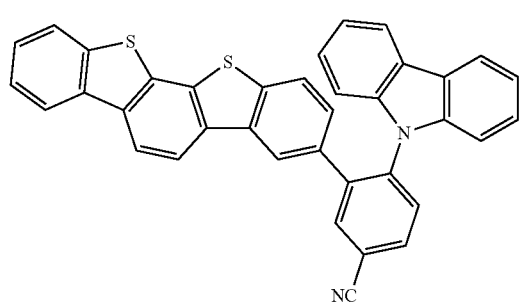
-continued
273
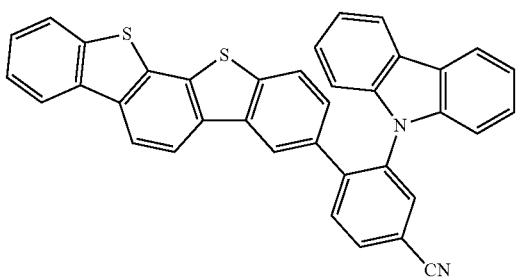
274
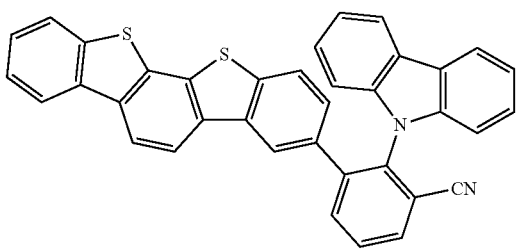
275
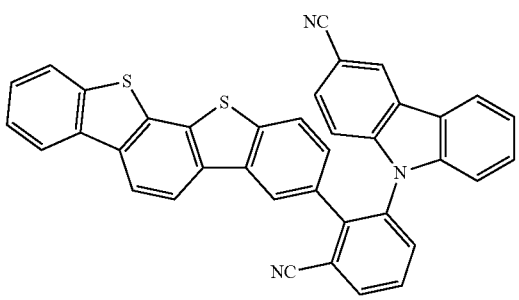
276
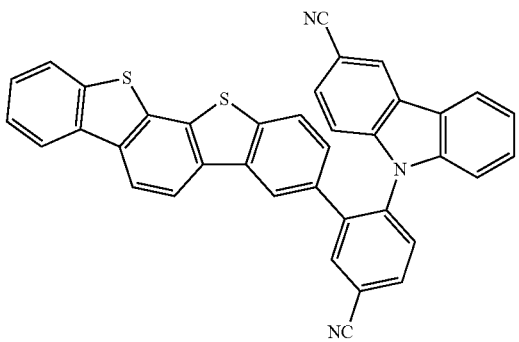
277
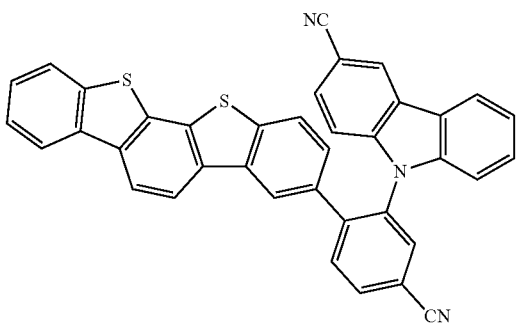

-continued
278
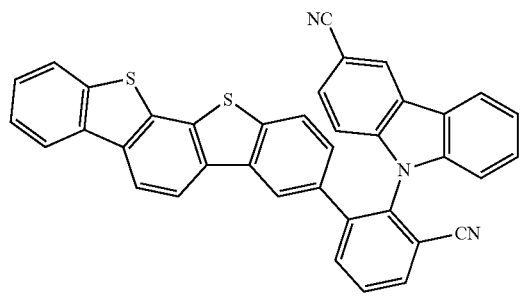
279
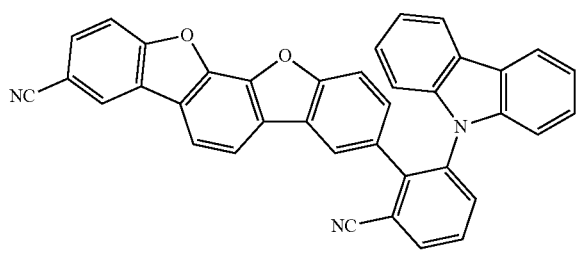
280
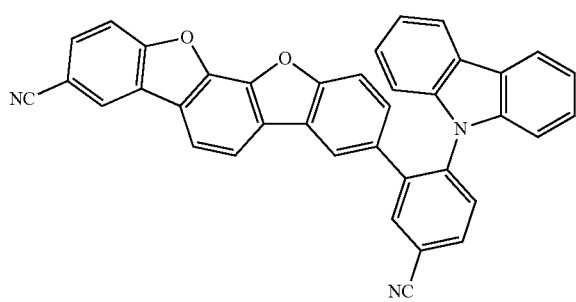
281
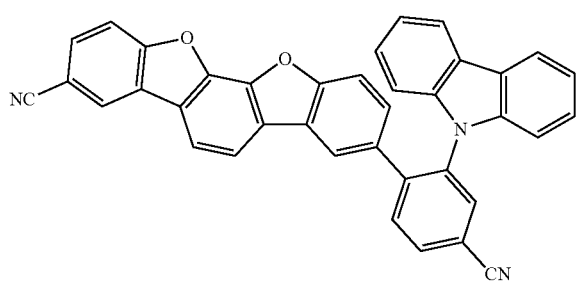
282
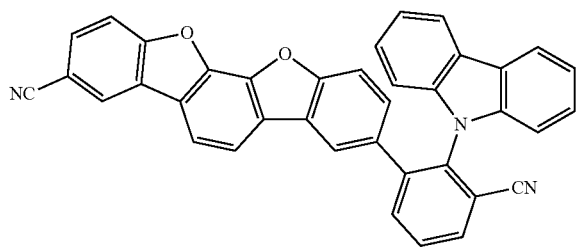
-continued
283
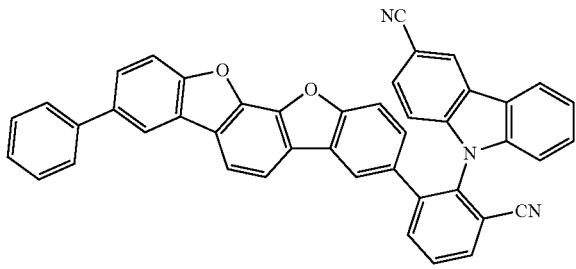
284
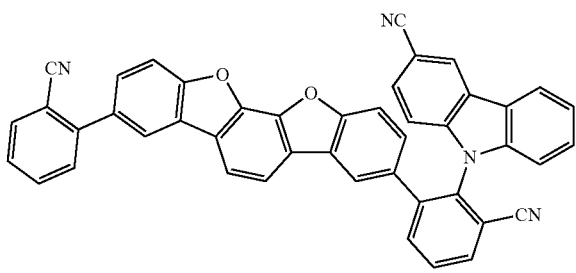
285
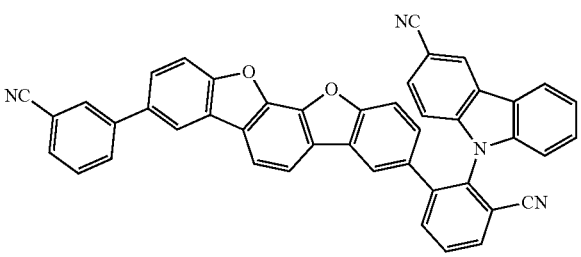
286
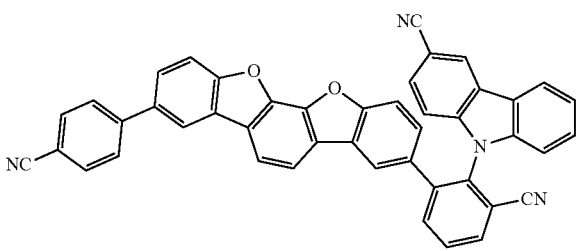
287
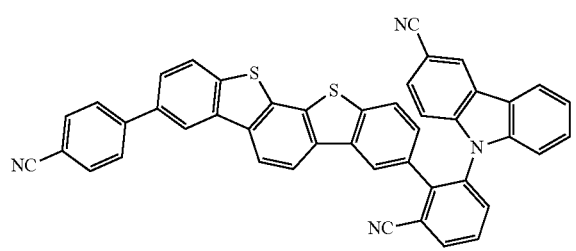

288
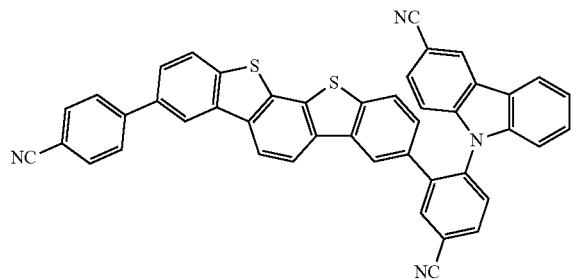
289
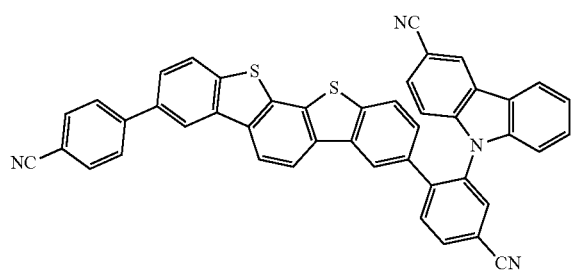
290
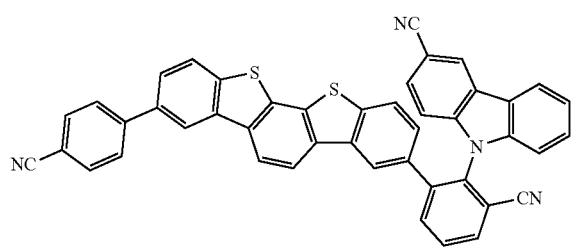
291
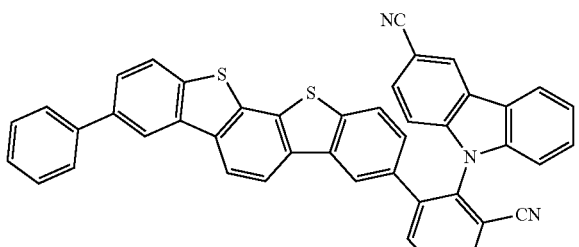
292
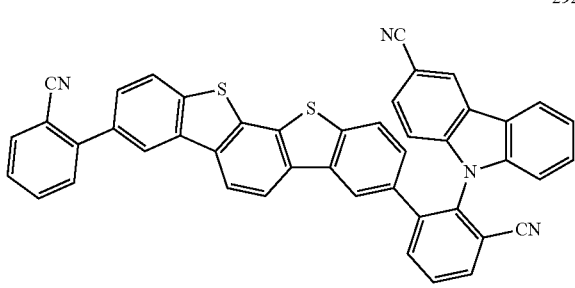
293
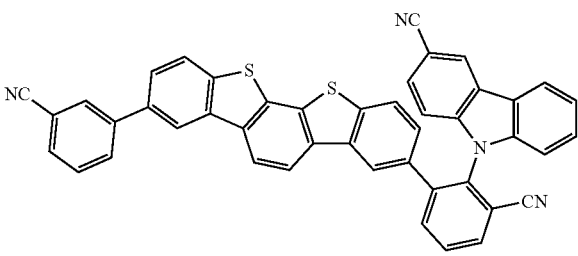
294
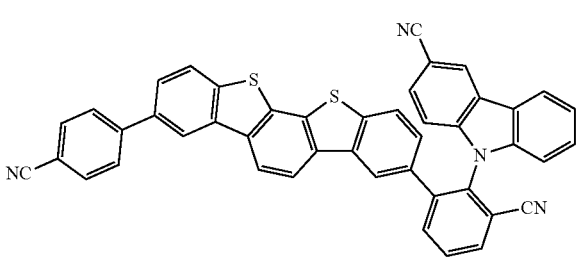
295
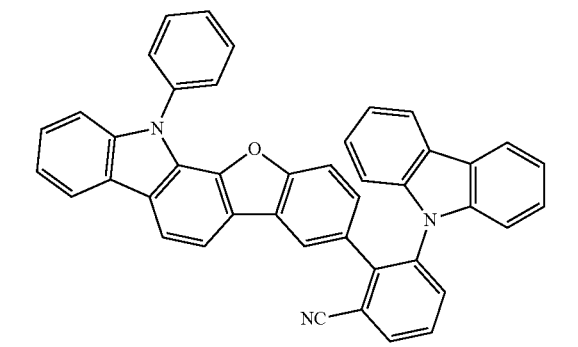
296
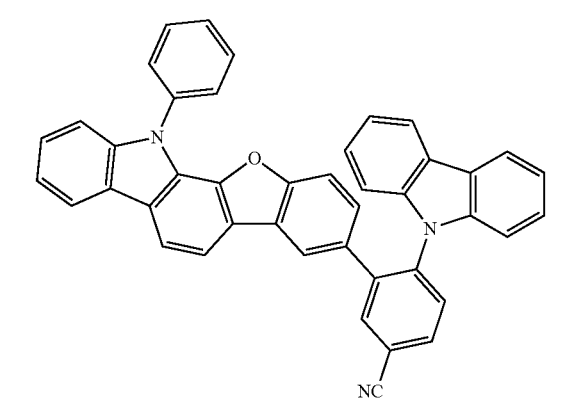

297
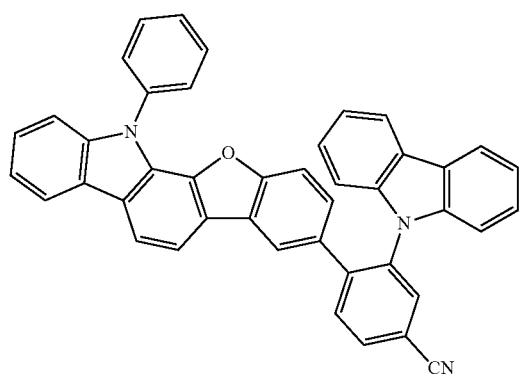
298
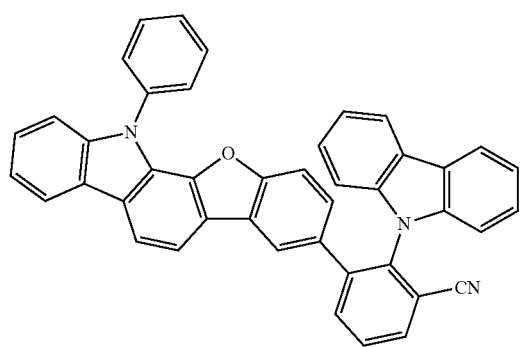
299
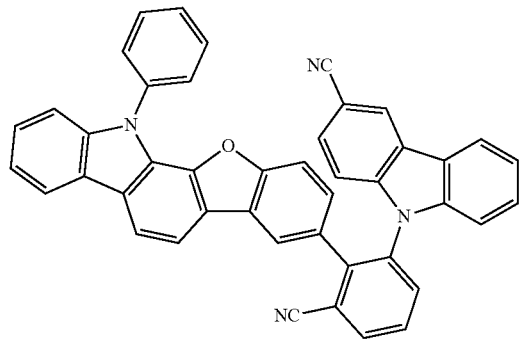
300
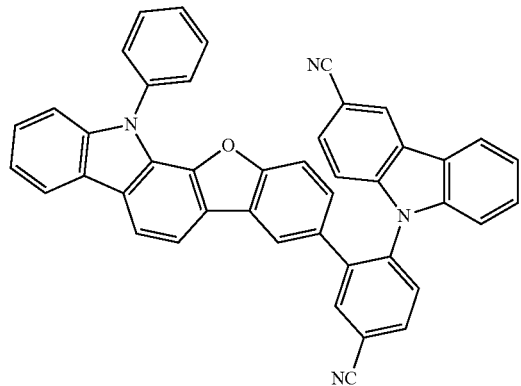
301
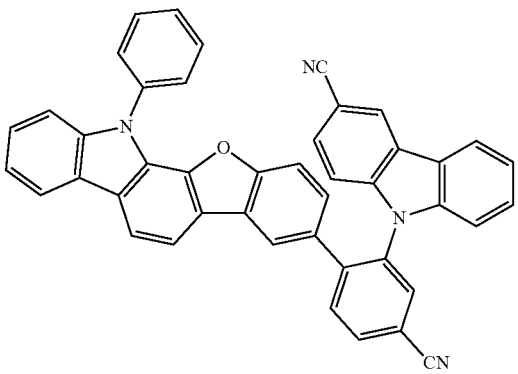
302
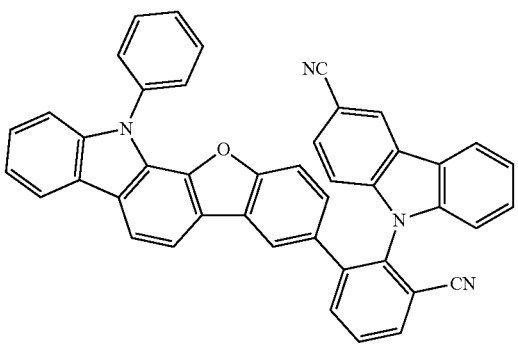
303
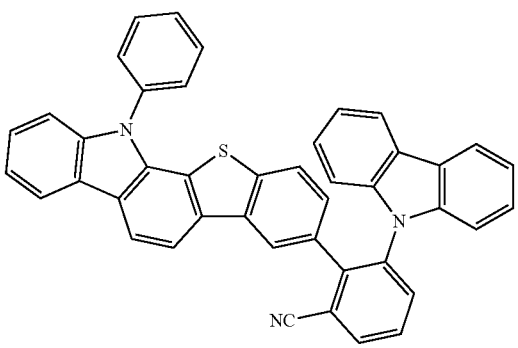
304
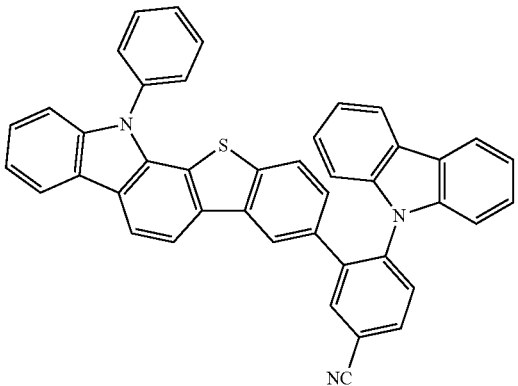

305
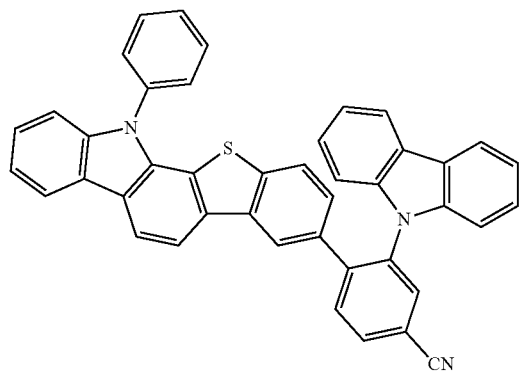
306
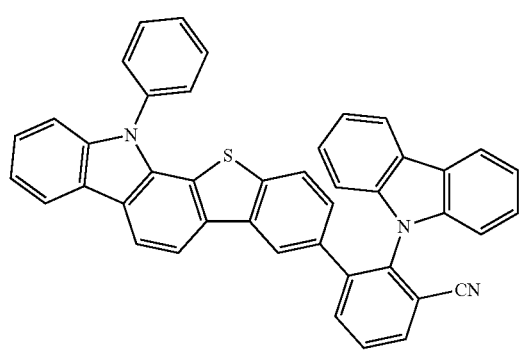
307
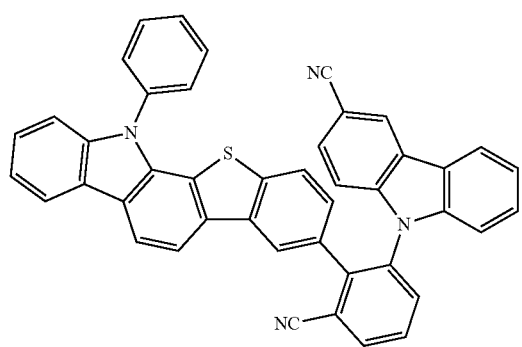
308
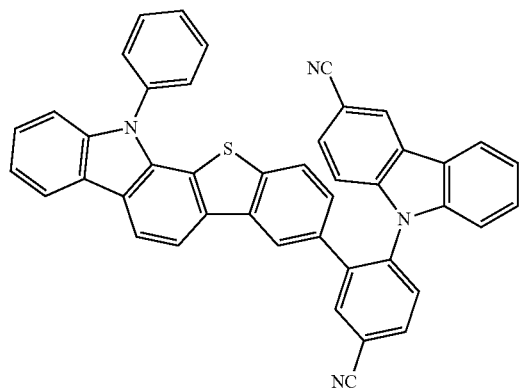
309
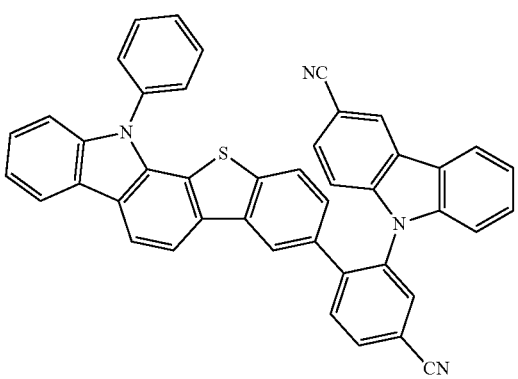
310
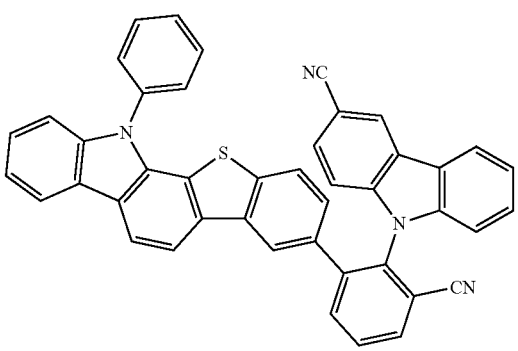
311
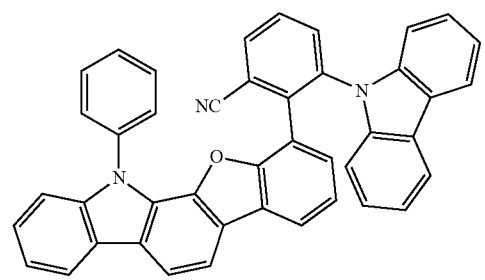
312
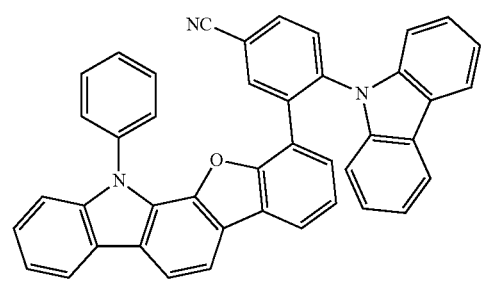
313
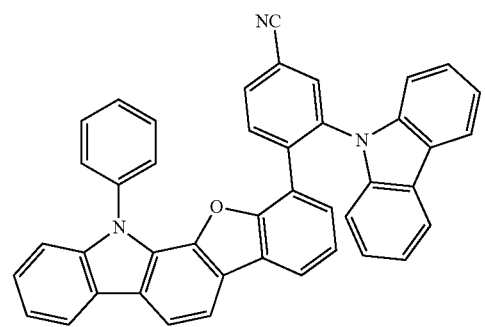

453
-continued
314
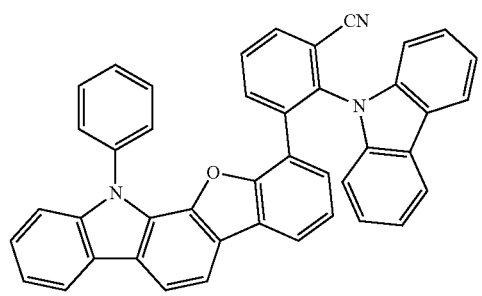
315
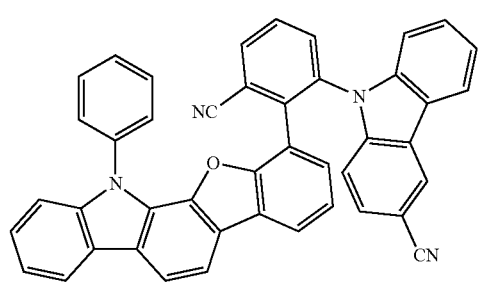
316
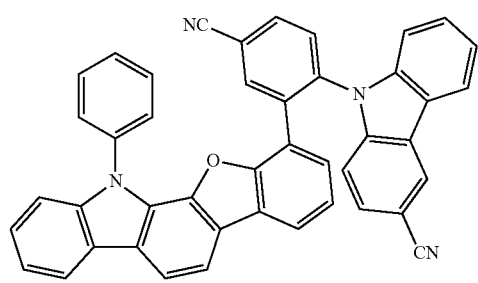
317
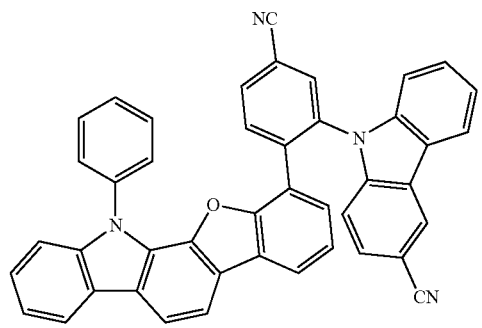
318
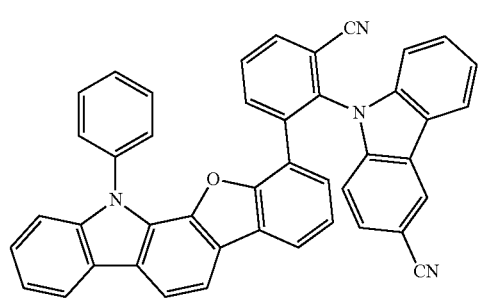
454
-continued
319
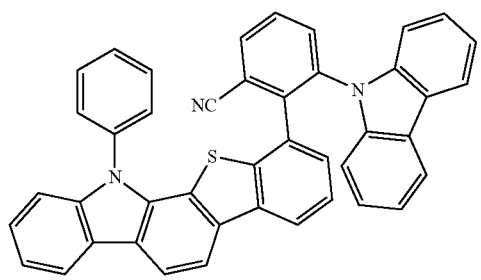
320
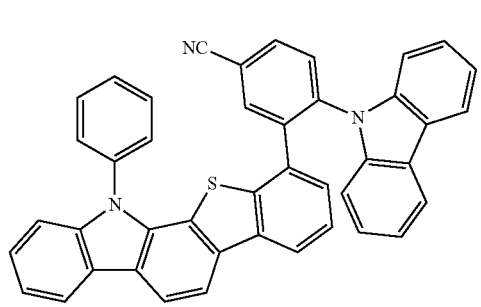
321
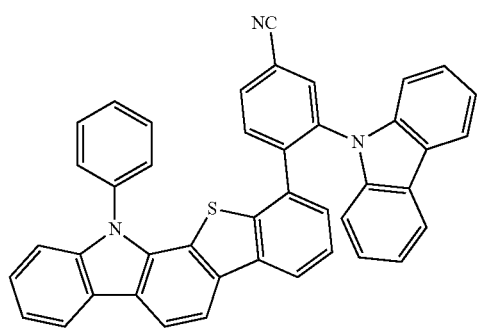
322
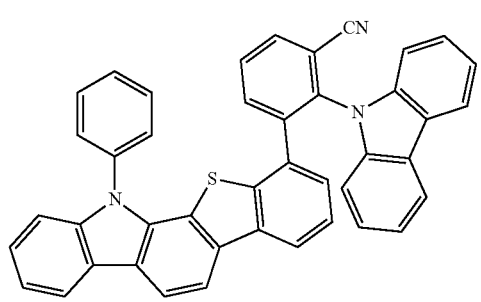
323
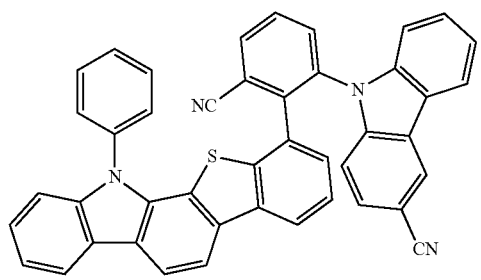

455
-continued
324
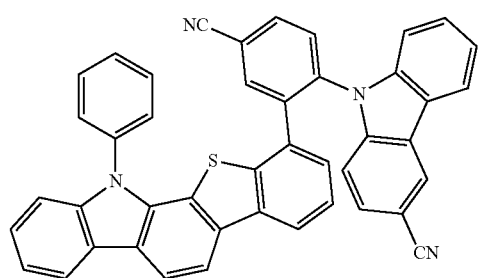
325
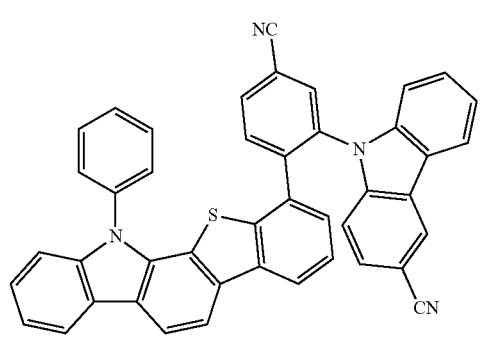
326
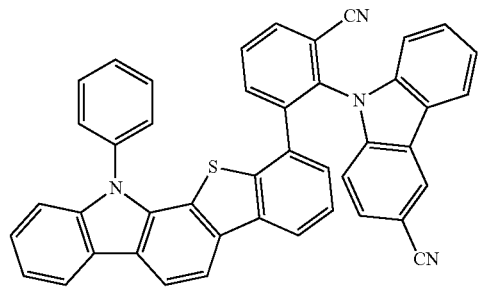
327
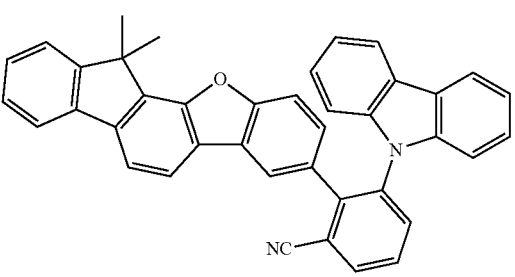
328
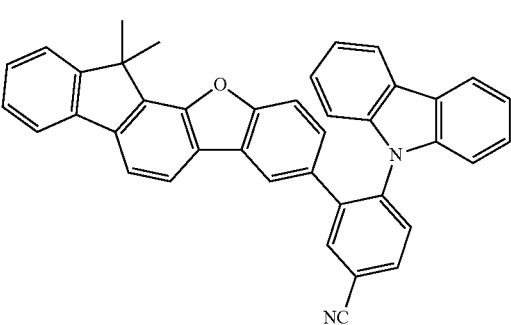
456
-continued
329
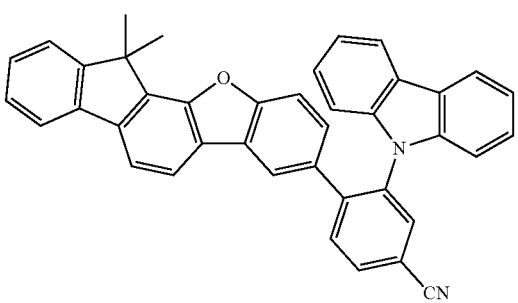
330
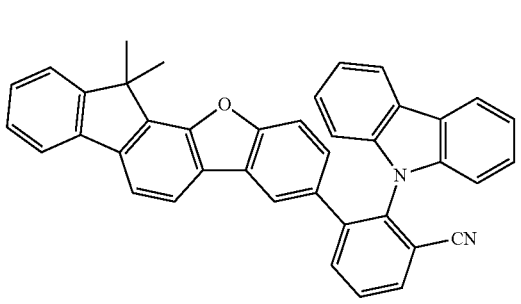
331
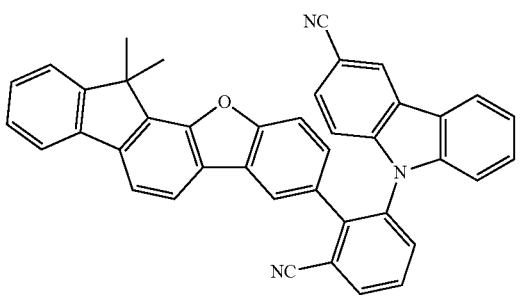
332
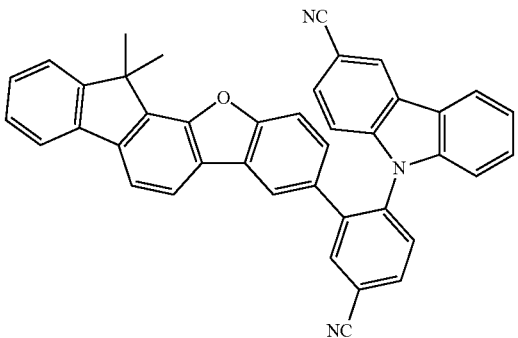
333
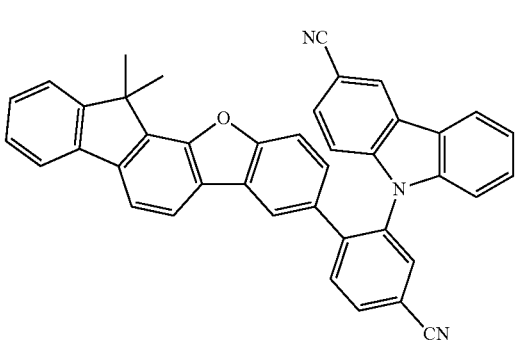

457
-continued
334
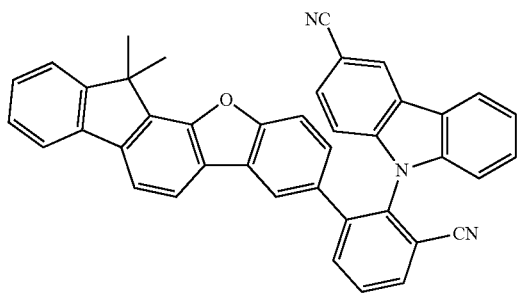
335
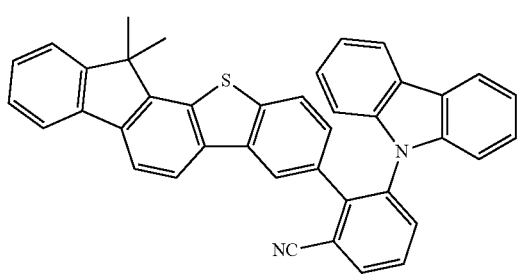
336
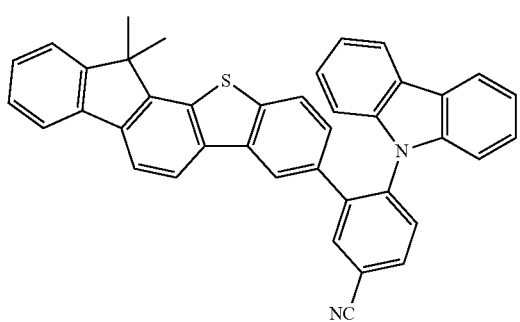
337
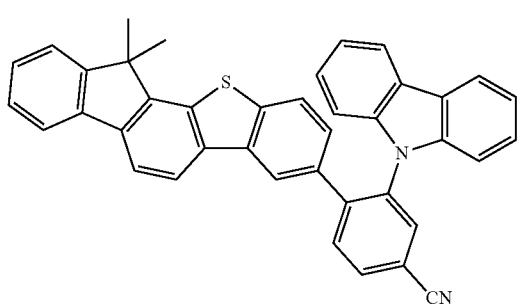
338
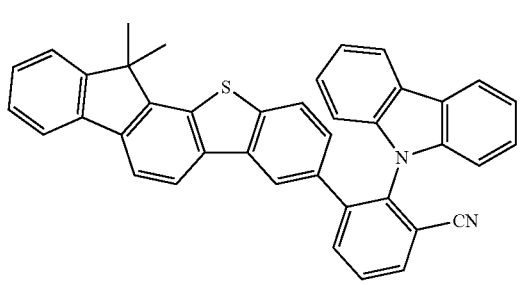
458
-continued
339
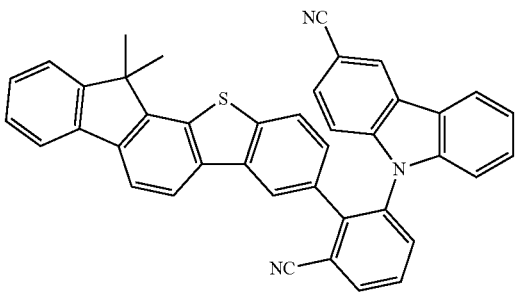
340
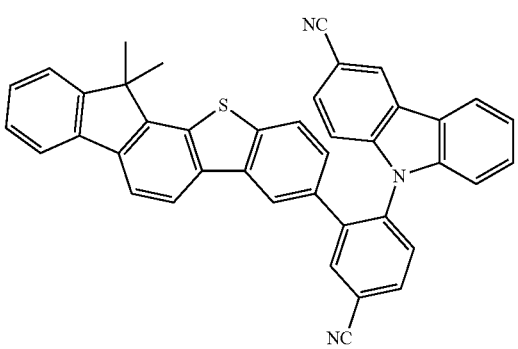
341
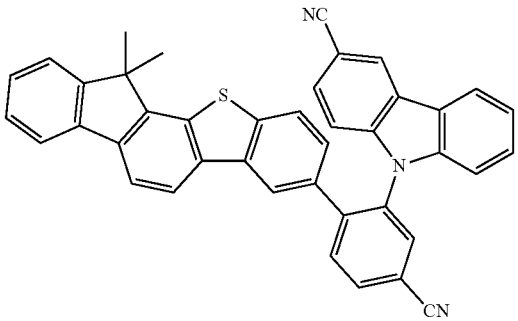
342
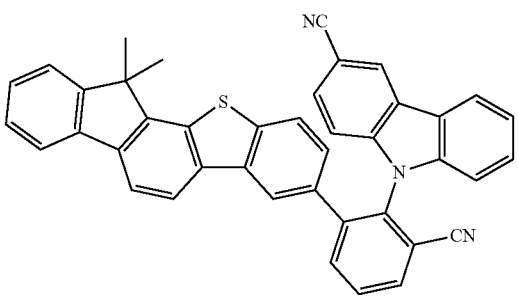
343
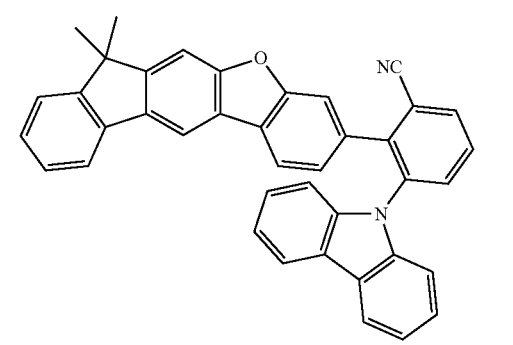

459
-continued
344
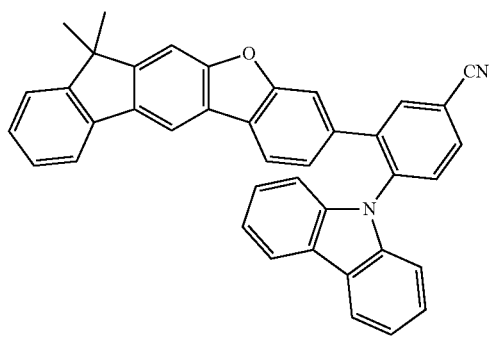
345
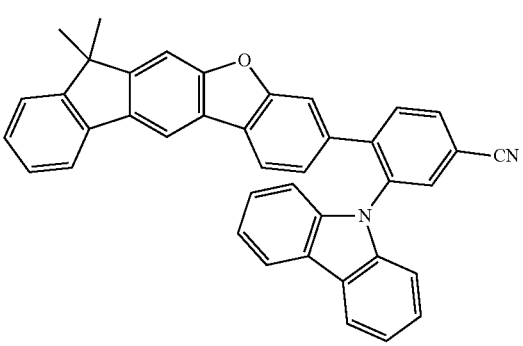
346
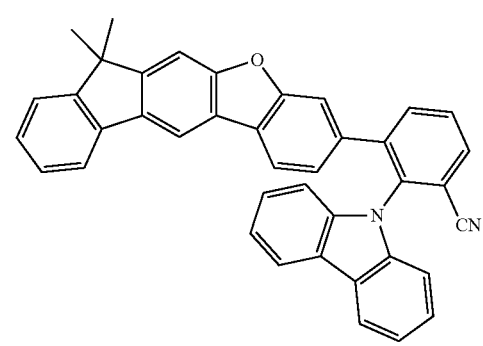
347
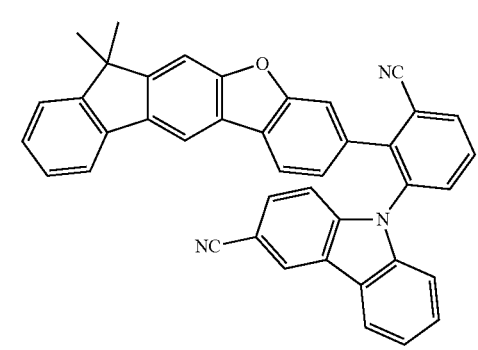
460
-continued
348
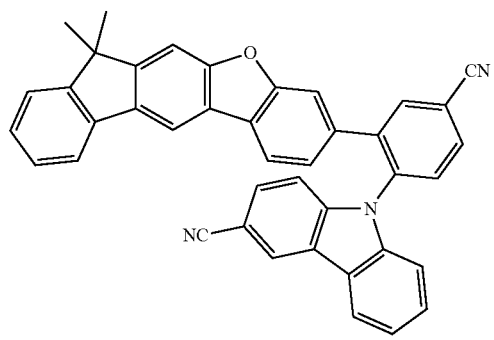
349
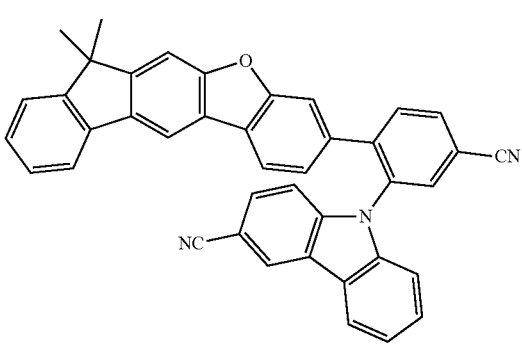
350
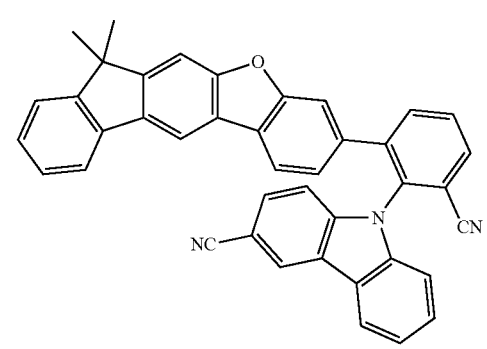
351
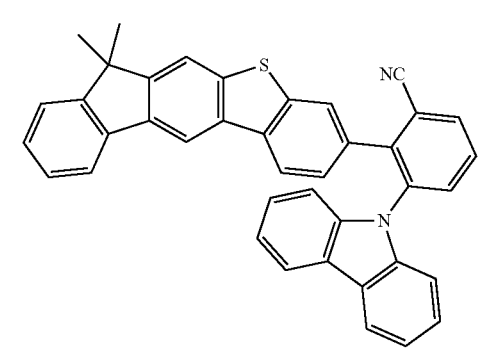

461
-continued
352
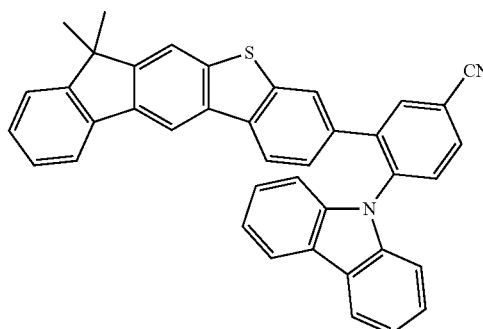
353
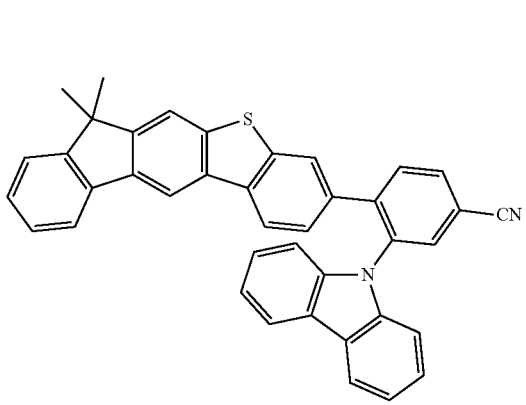
354
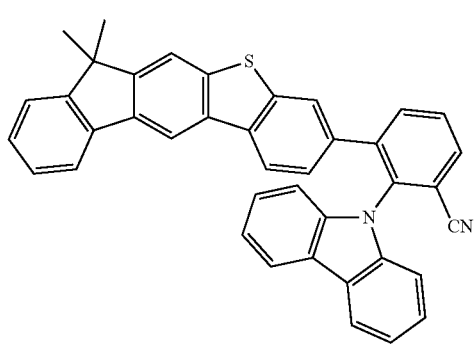
355
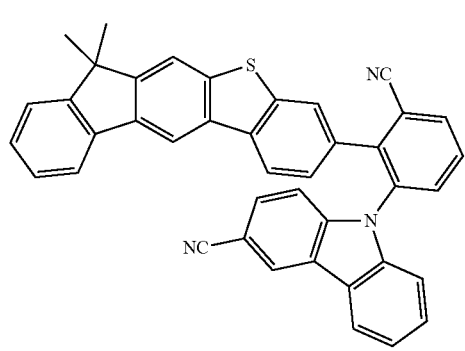
462
-continued
356
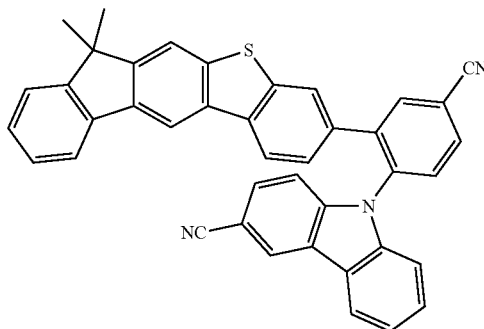
357
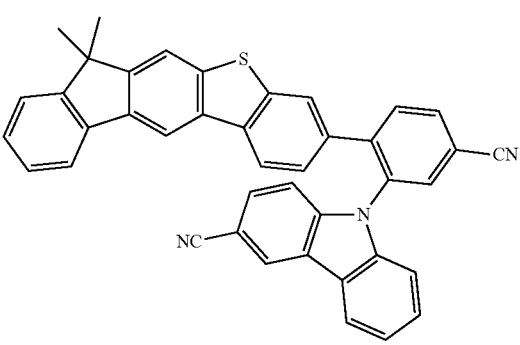
358
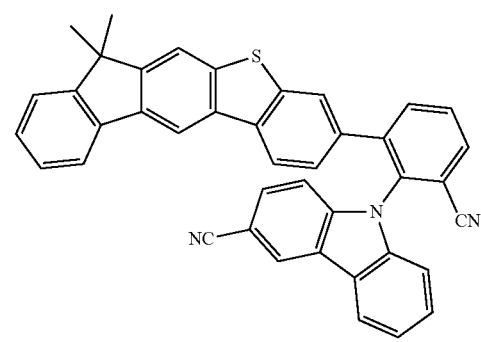
359
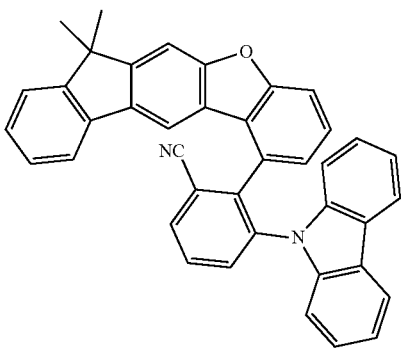

360 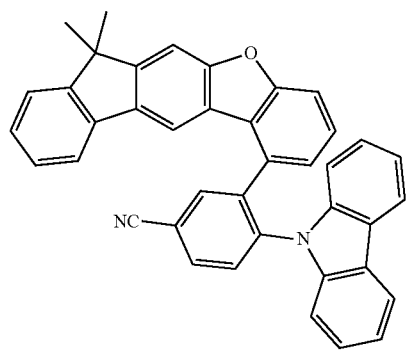
364 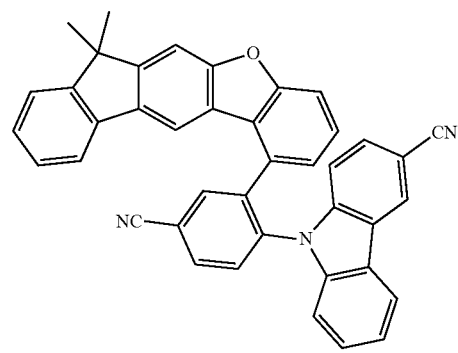
361 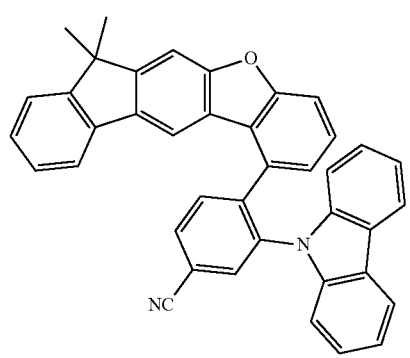
365 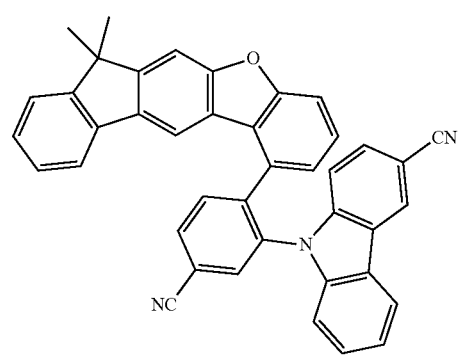
362 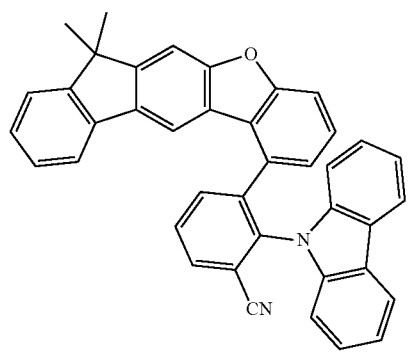
366 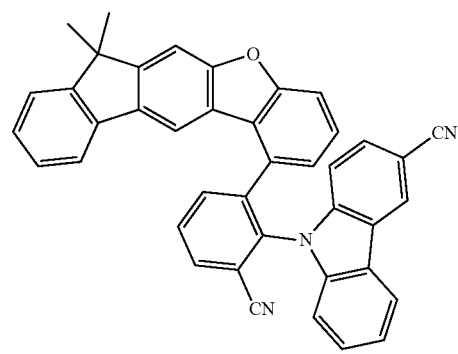
363 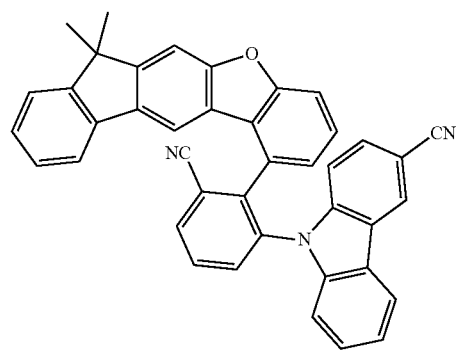
367 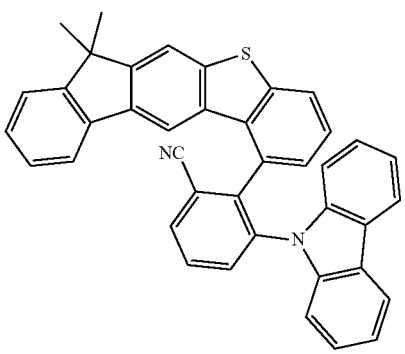

368
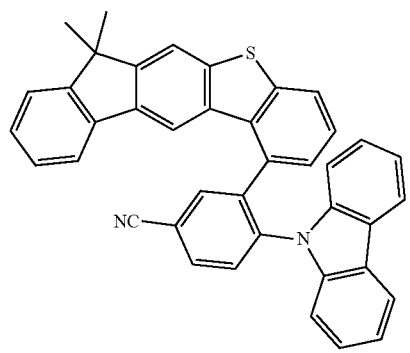
369
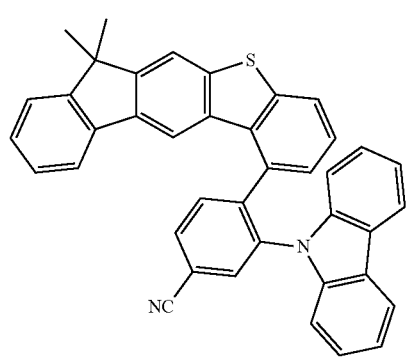
400
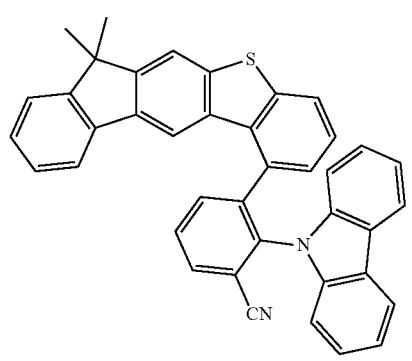
371
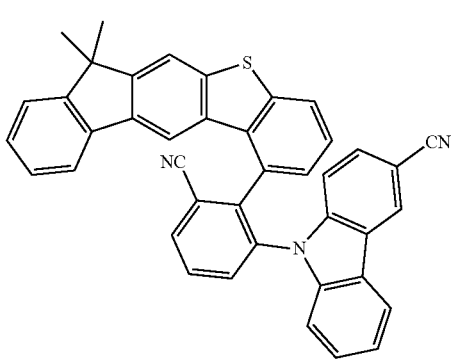
372
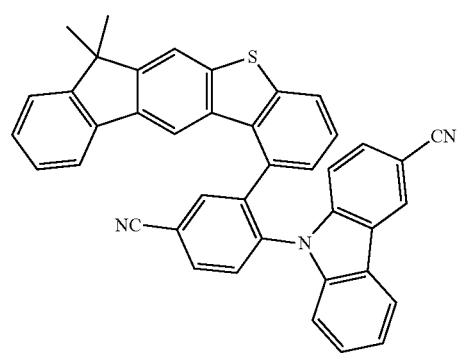
373
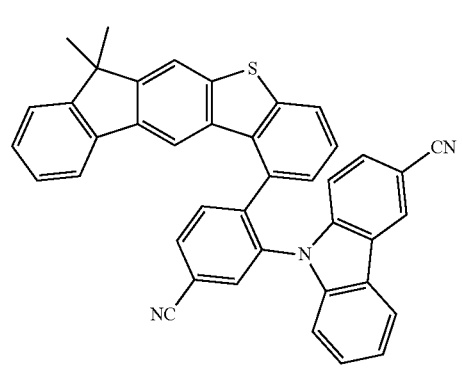
374
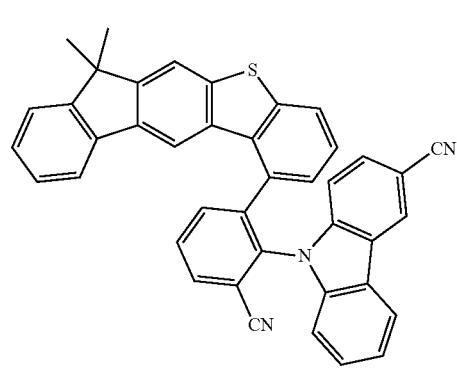
375
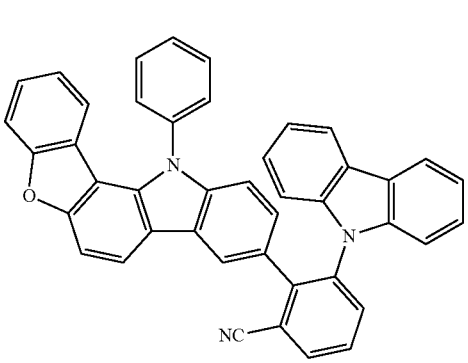

467
-continued
376
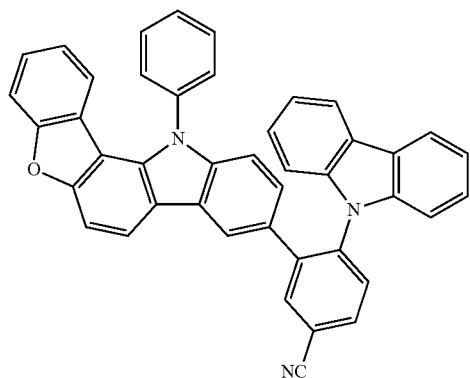
377
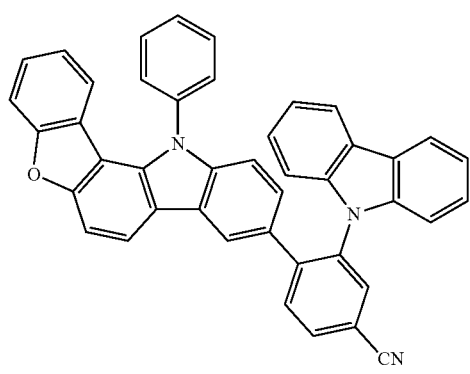
378
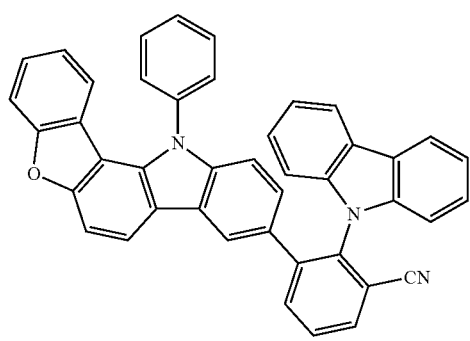
379
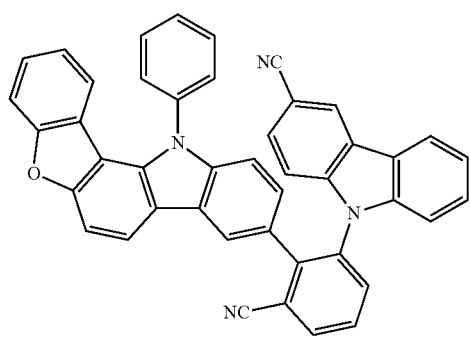
468
-continued
380
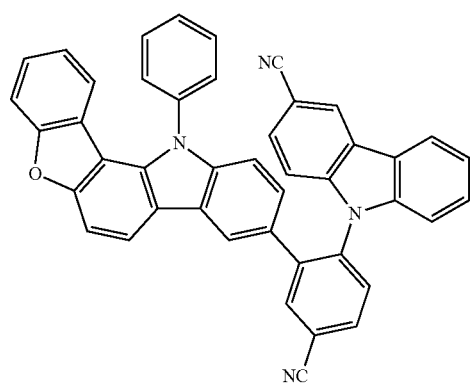
381
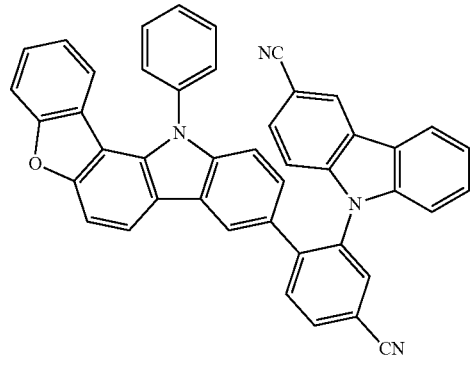
382
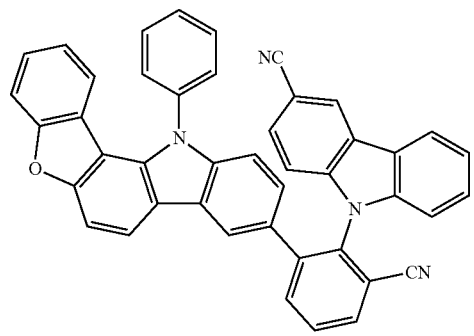
383
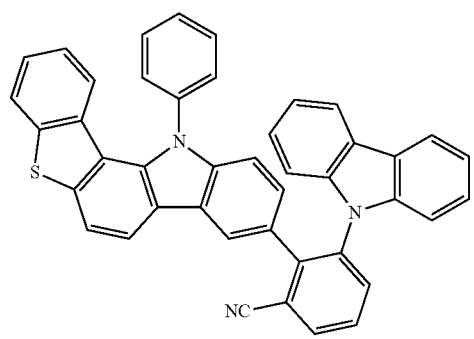

384
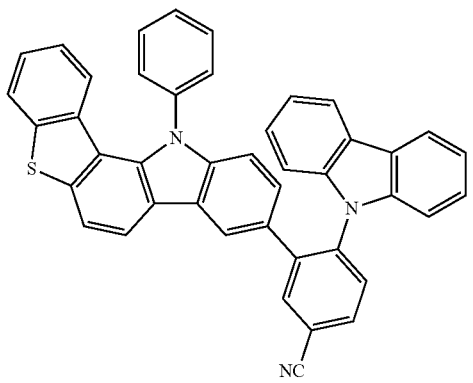
388
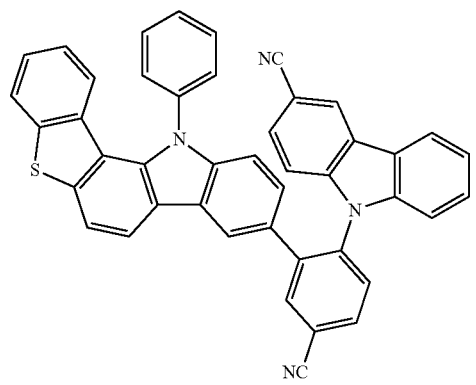
385
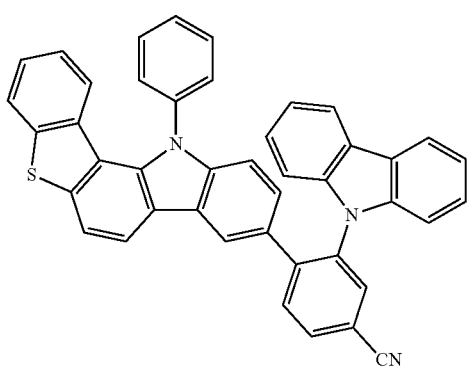
389
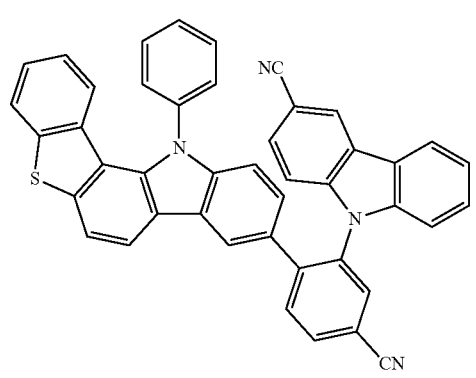
386
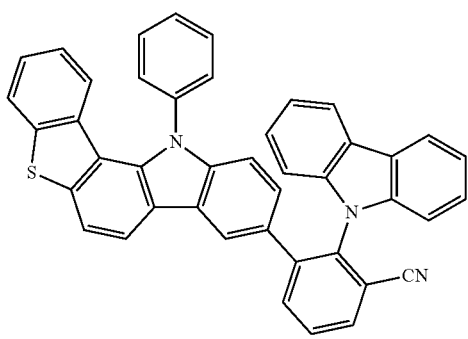
390
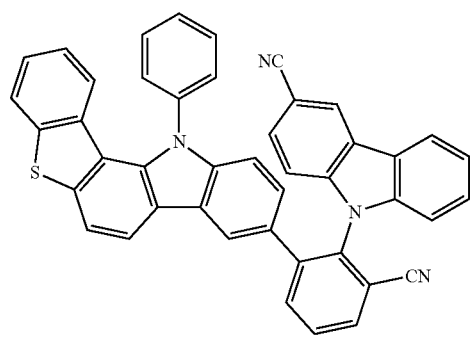
387
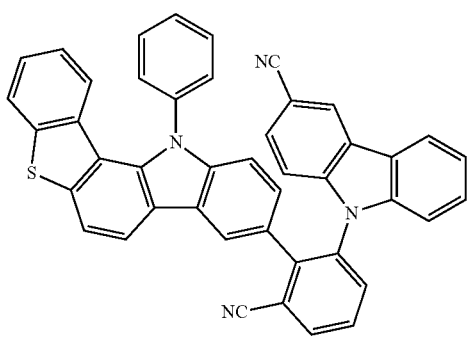
391
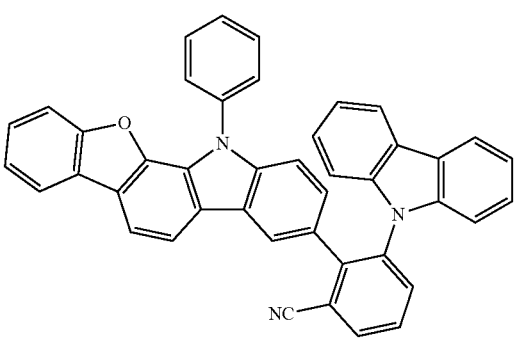

-continued
392
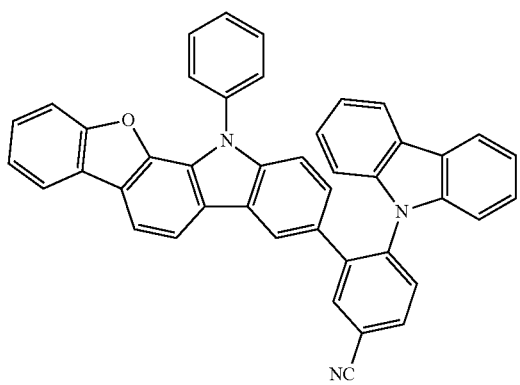
393
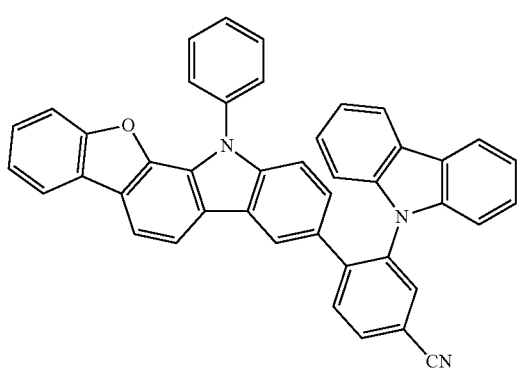
394
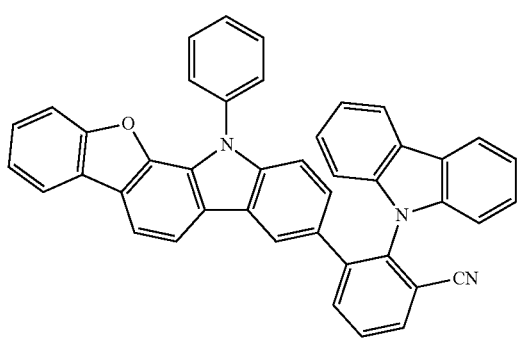
395
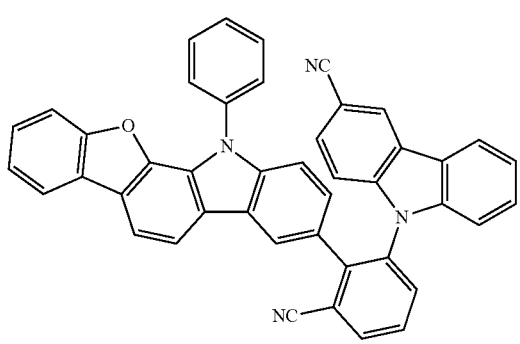
-continued
396
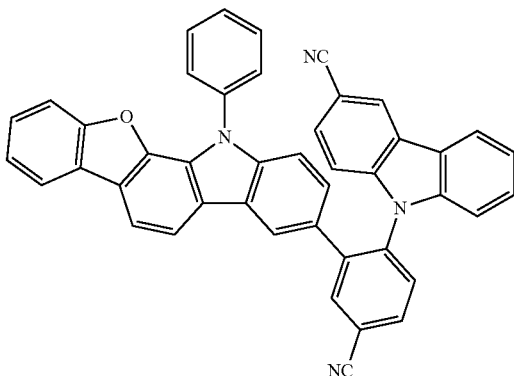
397
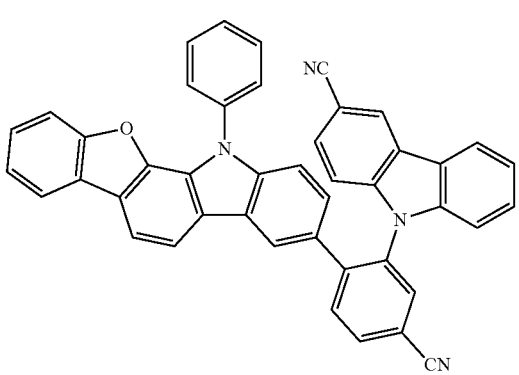
398
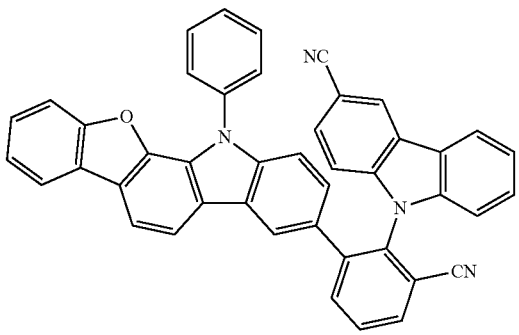
399
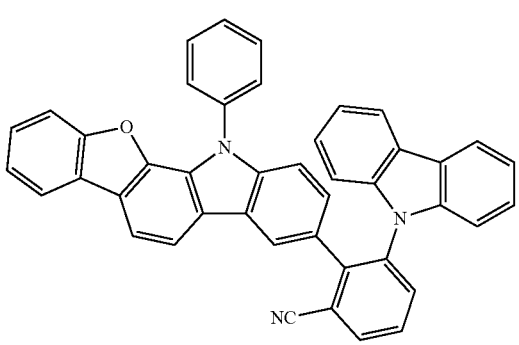

400
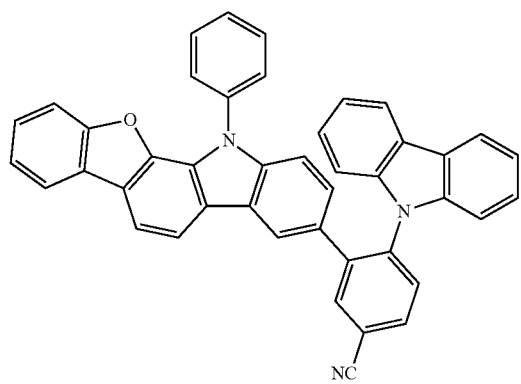
401
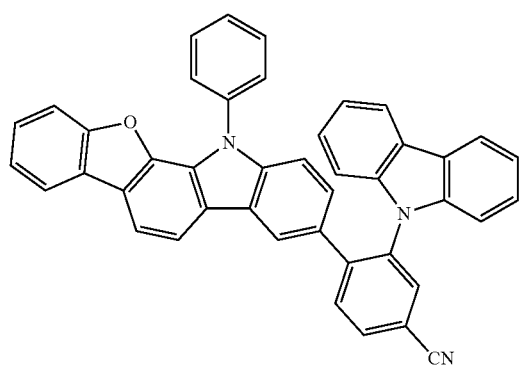
402
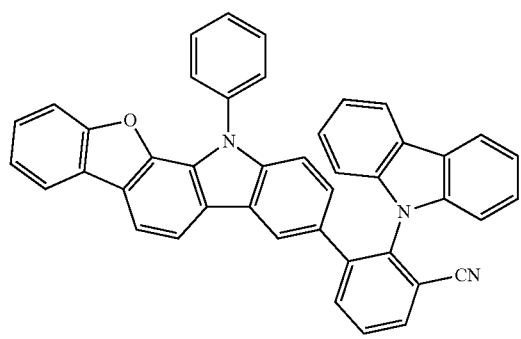
403
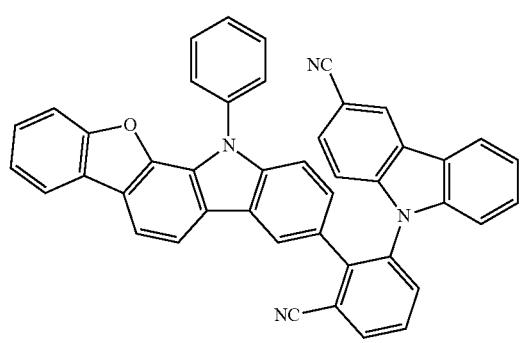
404
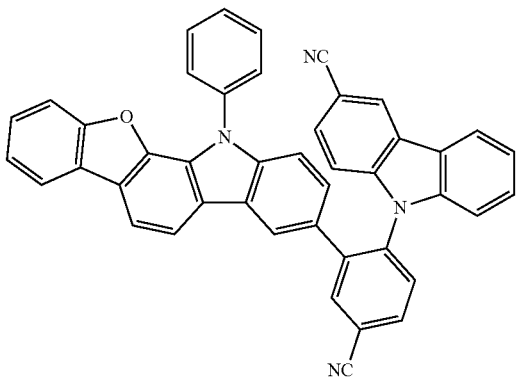
405
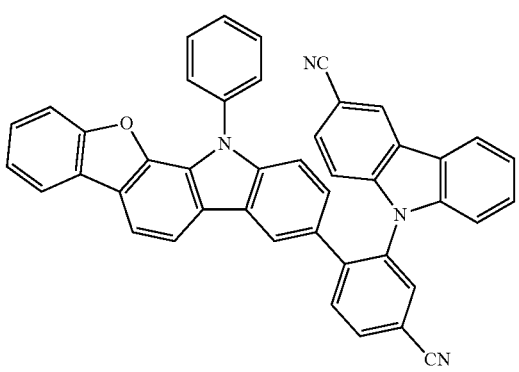
406
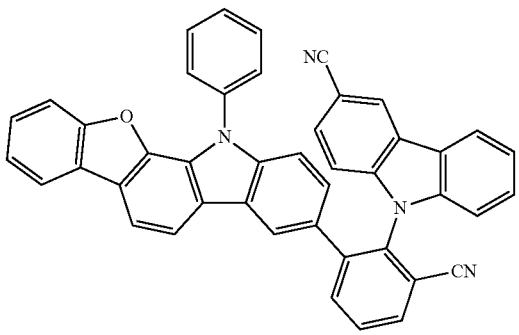
407
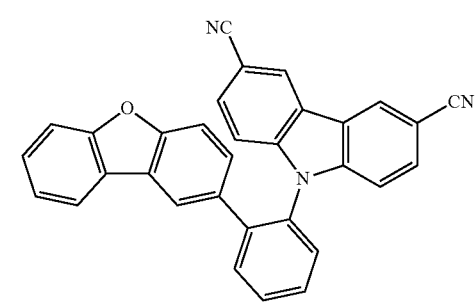

408
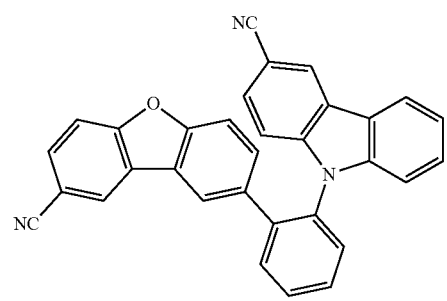
409
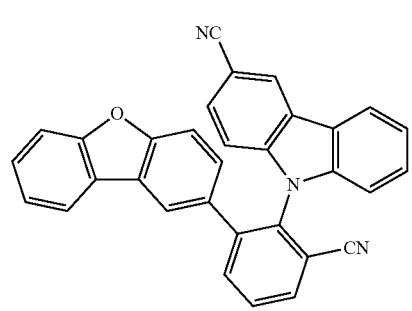
410
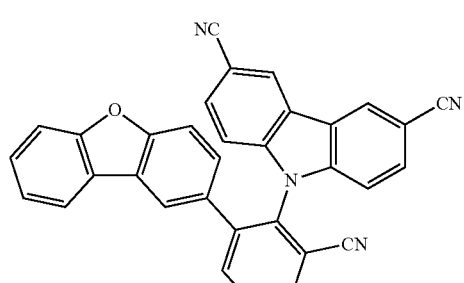
411
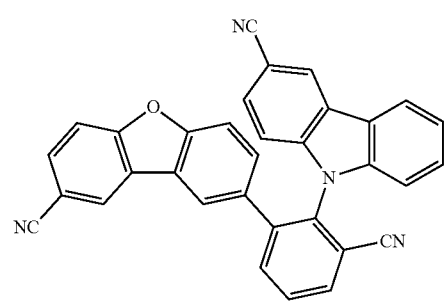
412
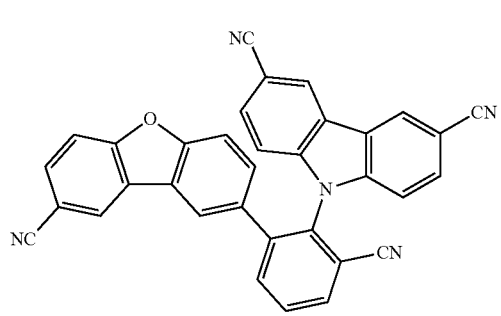
413
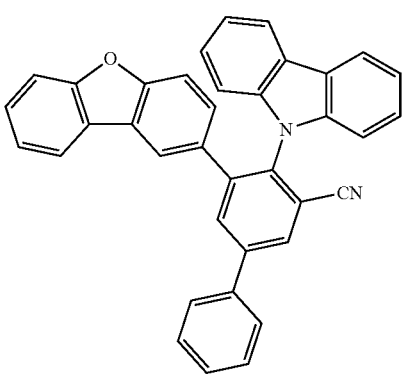
414
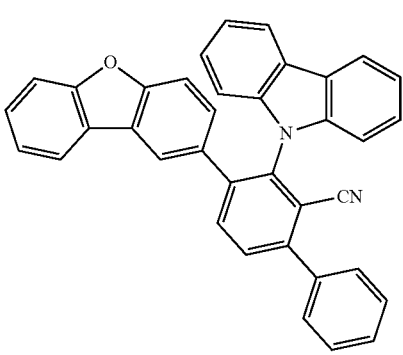
415
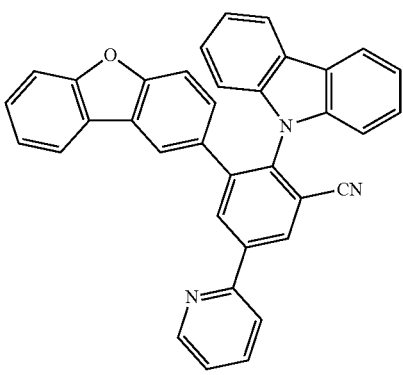
416
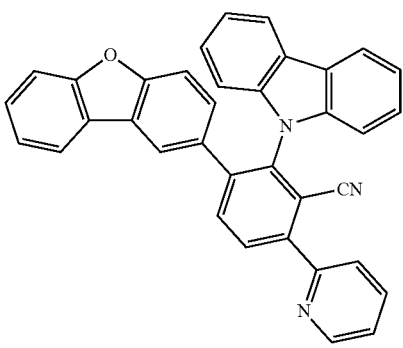

-continued
417
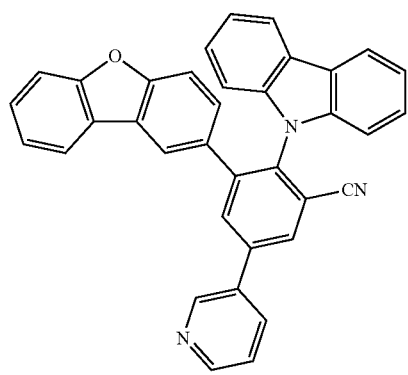
418
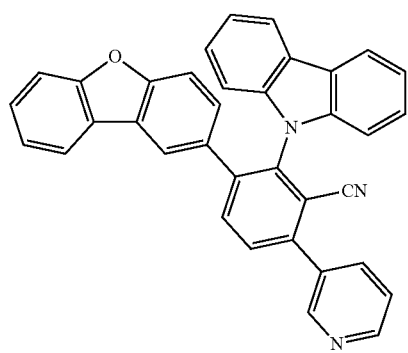
419
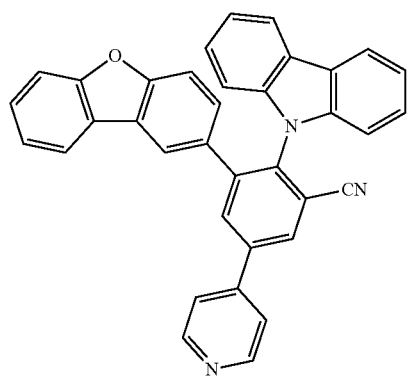
420
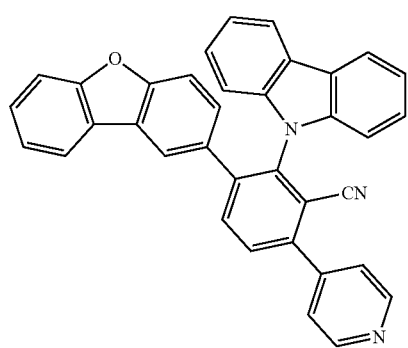
-continued
421
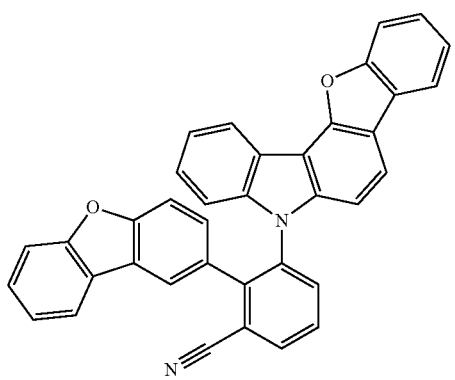
422
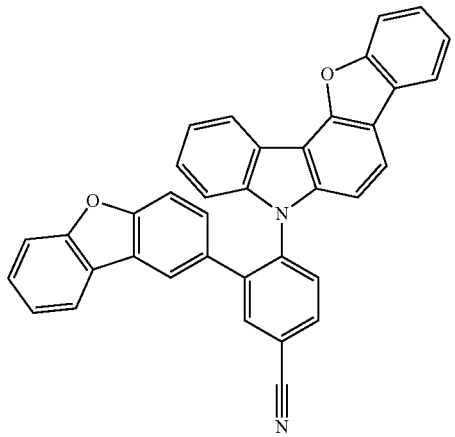
423
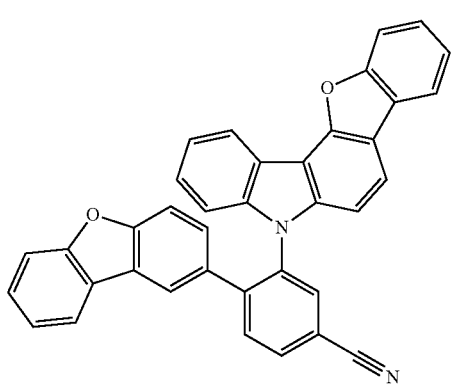
424
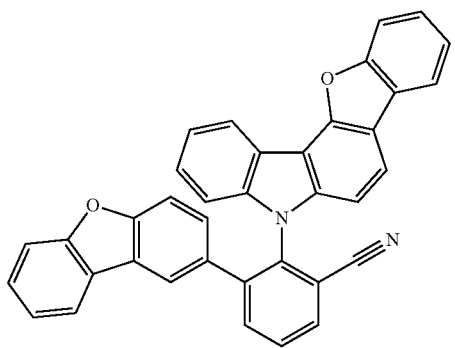

| 479 -continued | 480 -continued |
|---|---|
| 425 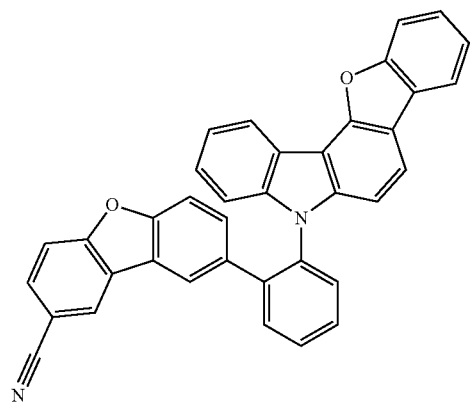 | 429 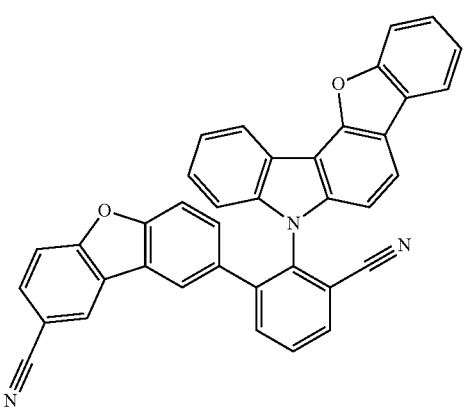 |
| 426 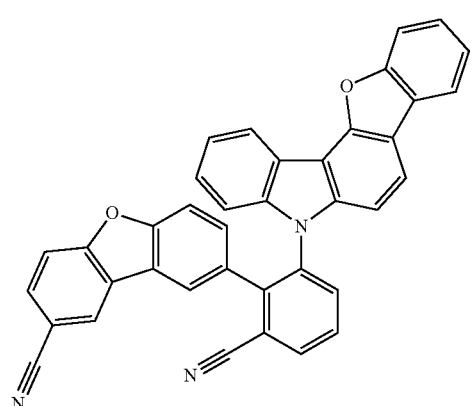 | 430 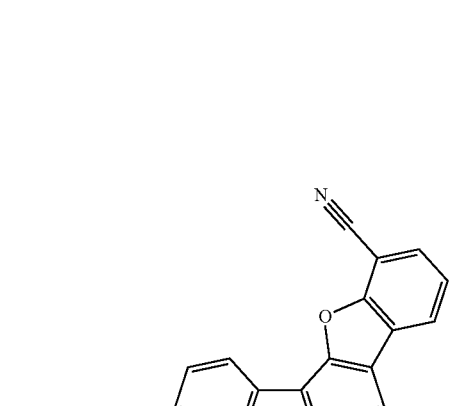 |
| 427 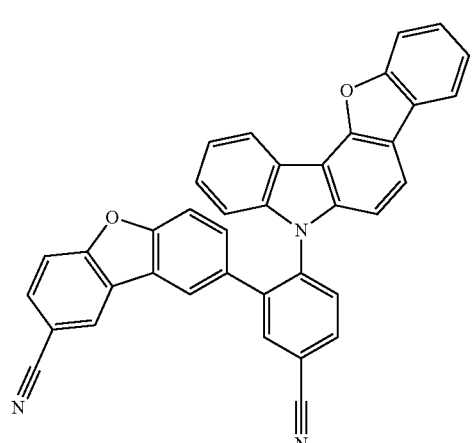 | |
| 428 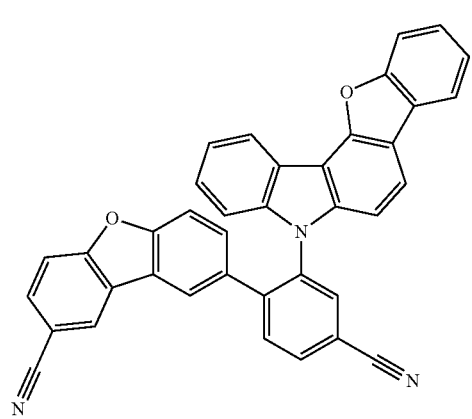 | 431 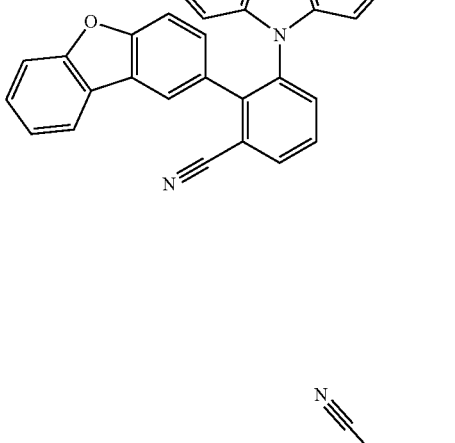 |

481
-continued
432
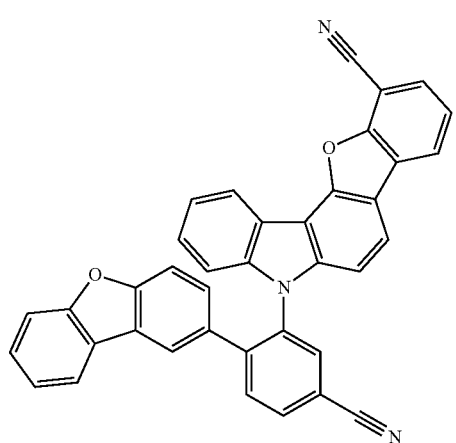
433
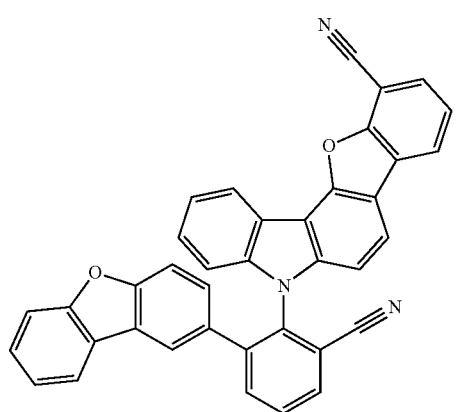
434
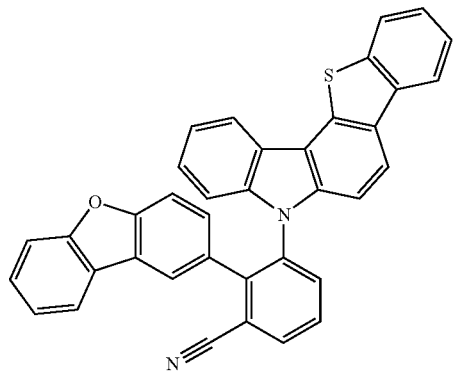
435
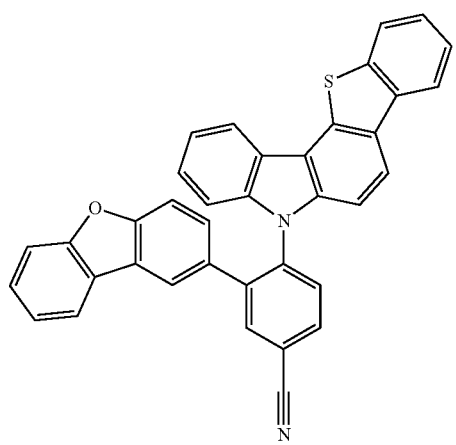
482
-continued
436
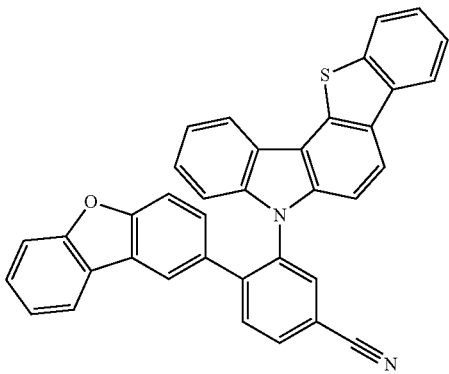
437
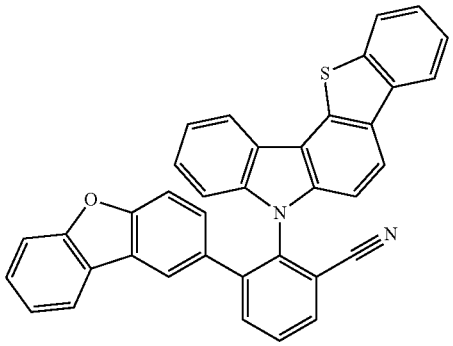
438
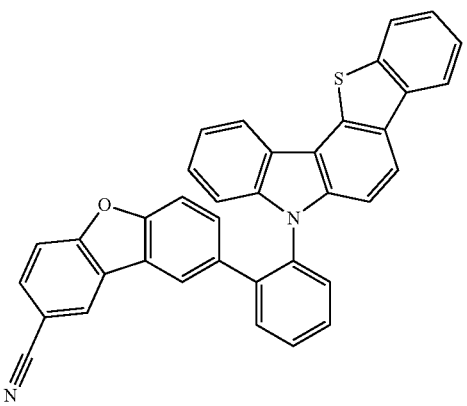
439
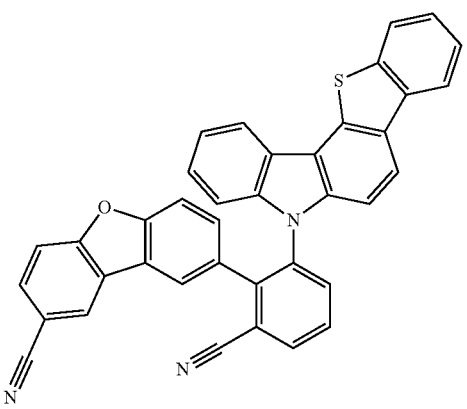

-continued
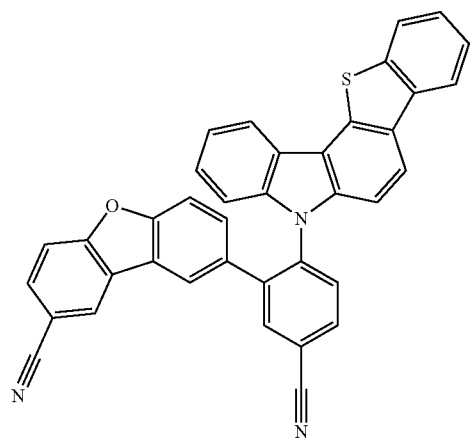
440
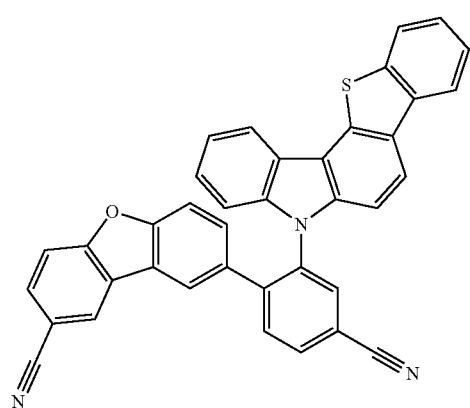
441
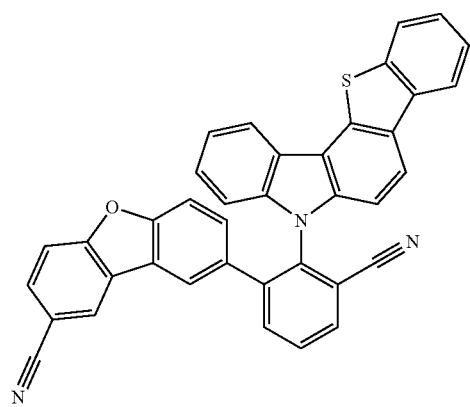
442
-continued
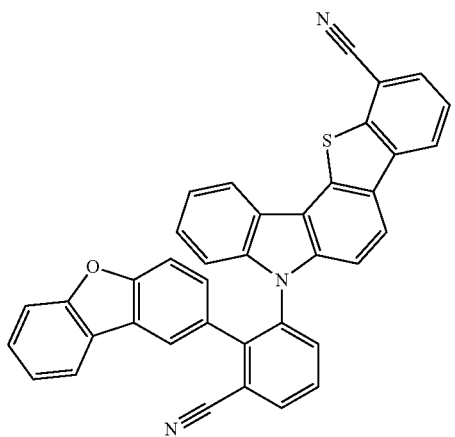
443
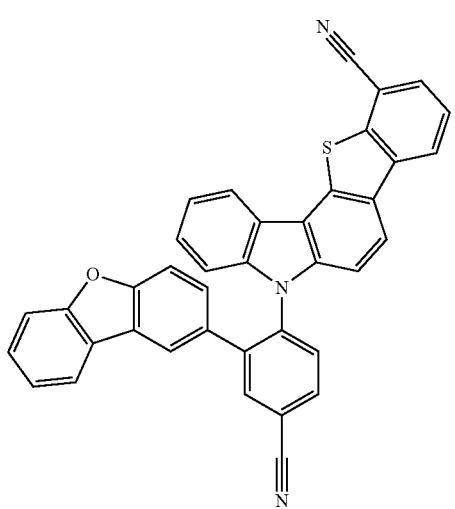
444
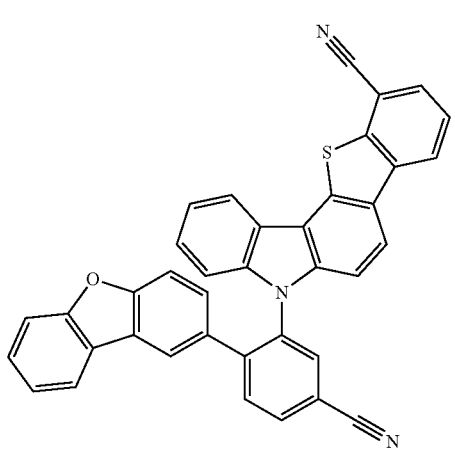
445

446
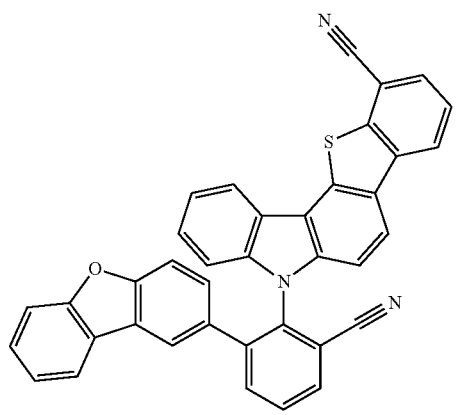
447
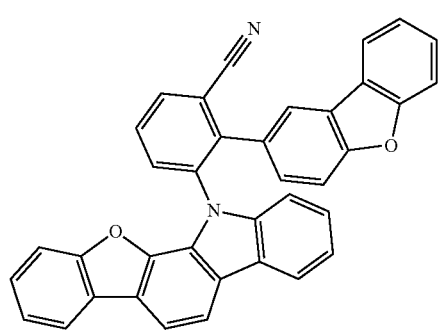
448
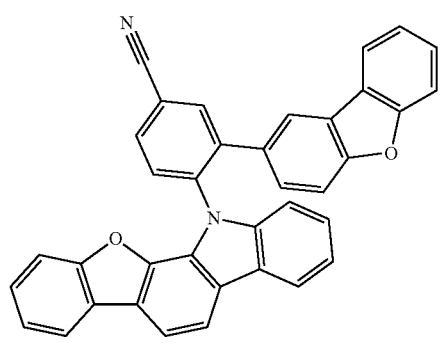
449
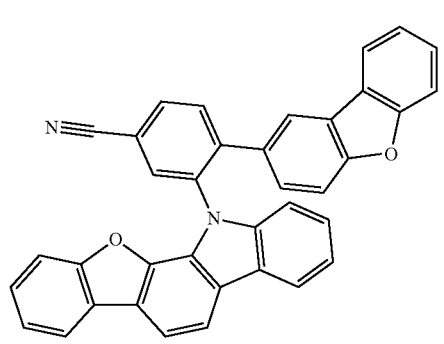
450
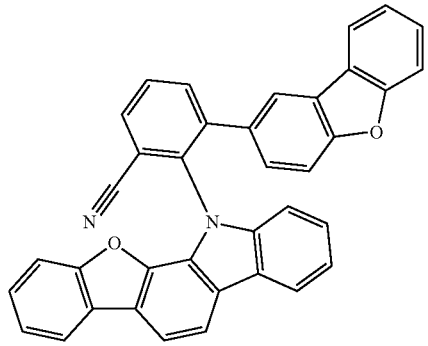
451
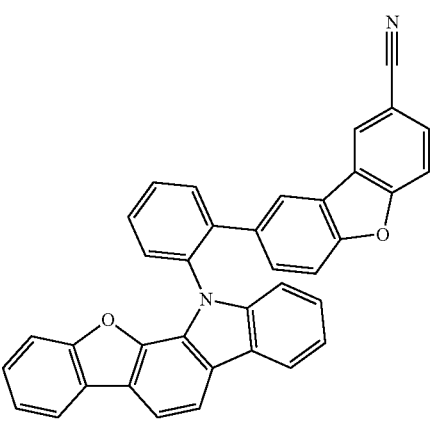
452
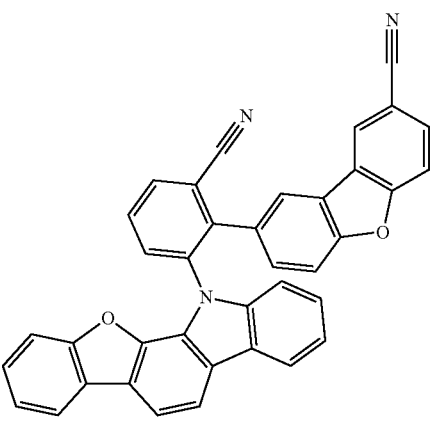
453
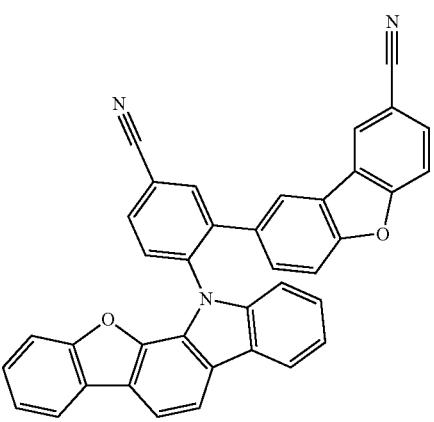

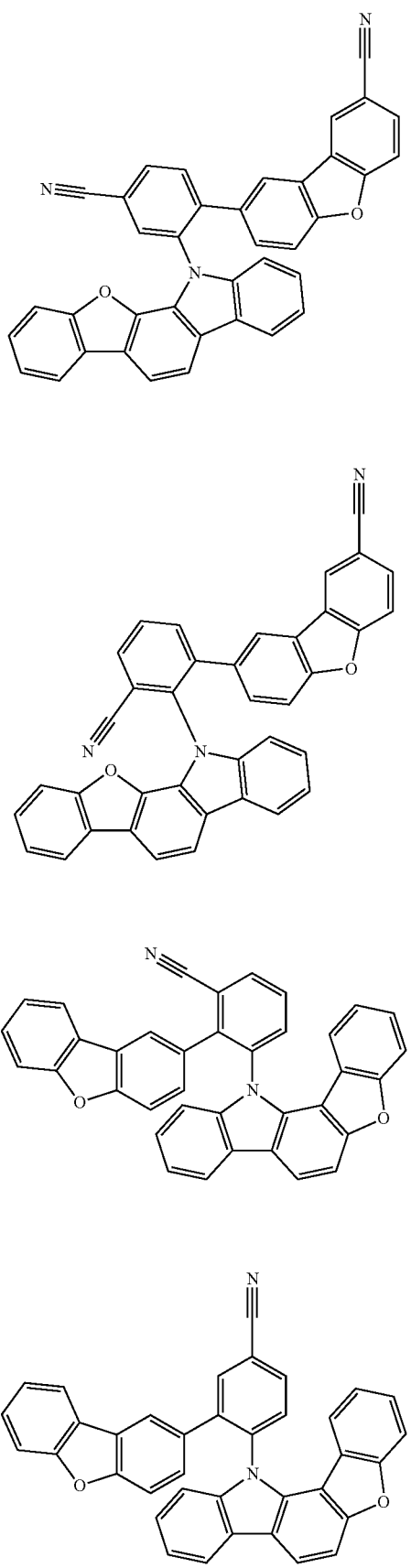
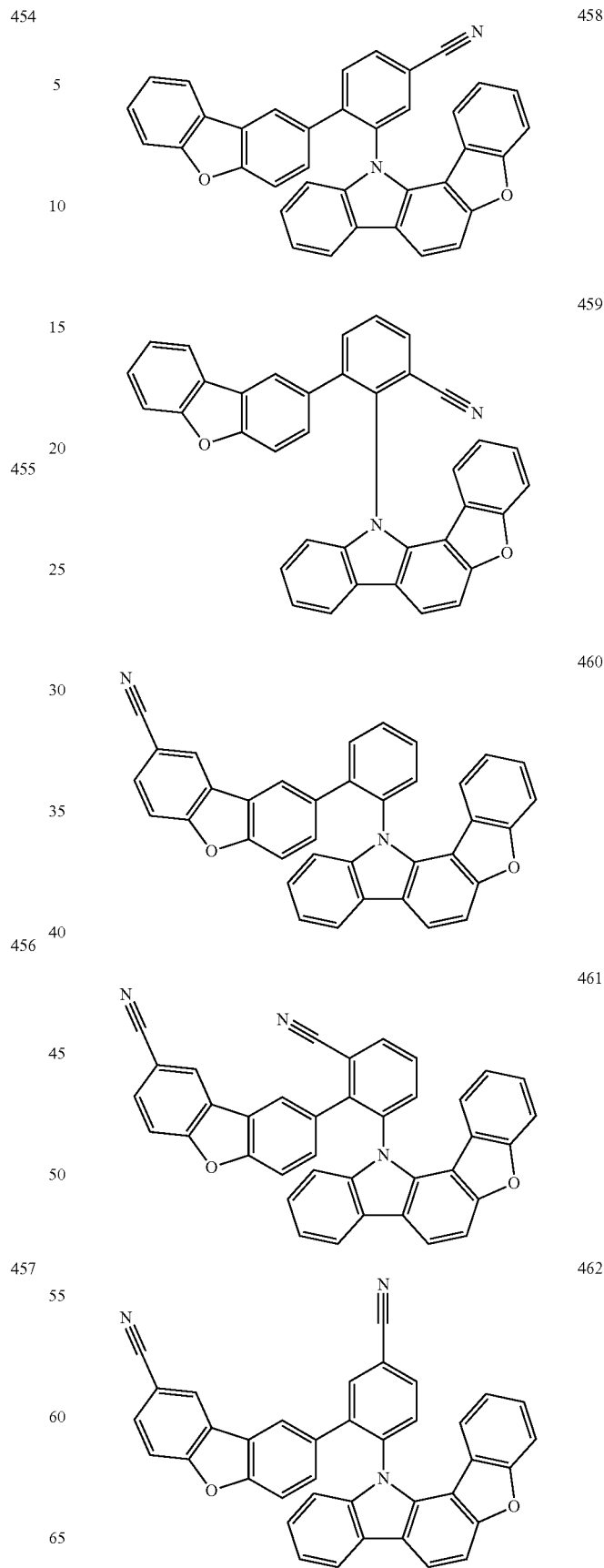

489
-continued
463
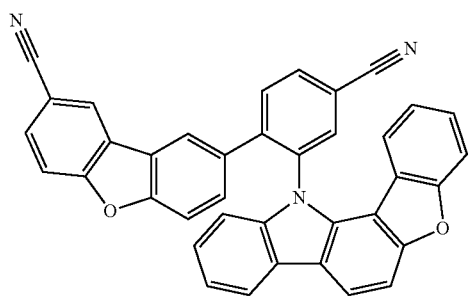
464
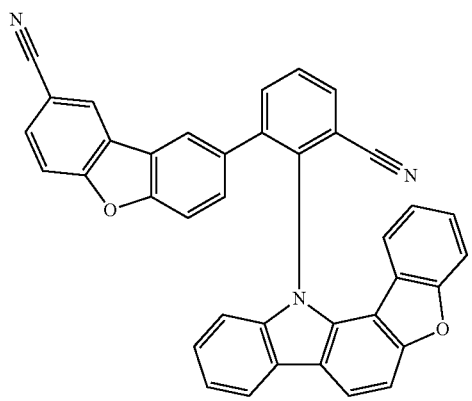
465
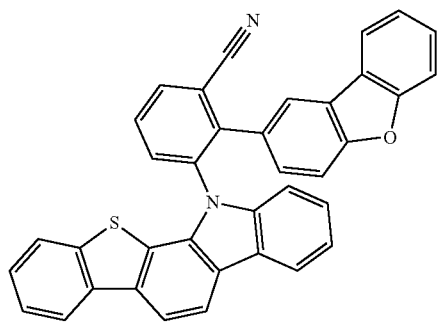
466
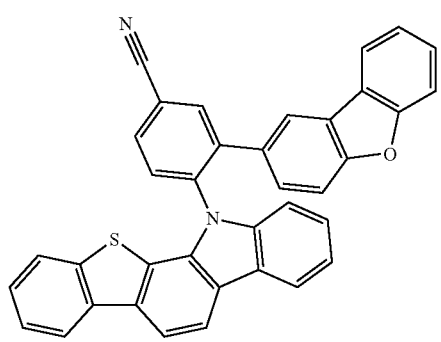
490
-continued
467
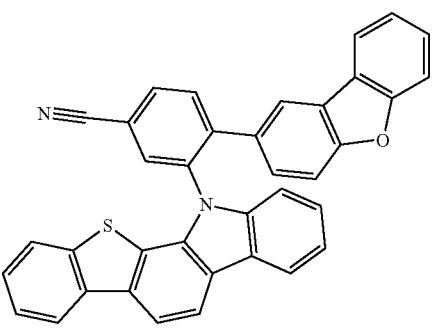
468
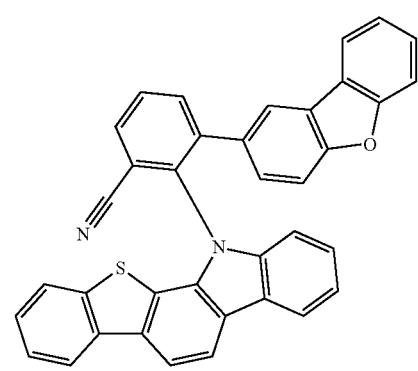
469
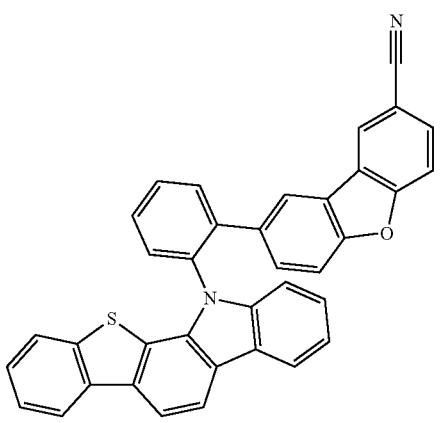
470
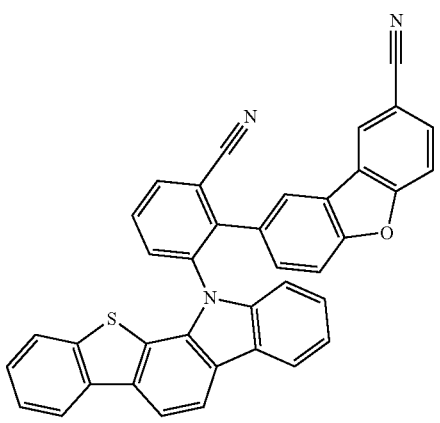

491 -continued
471
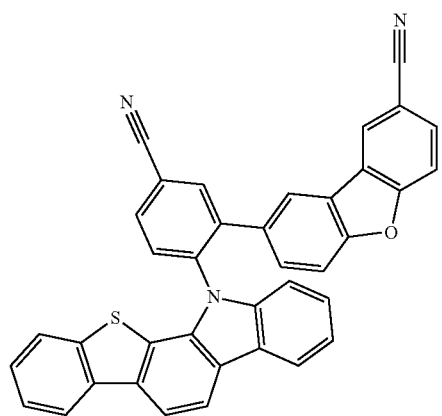
472
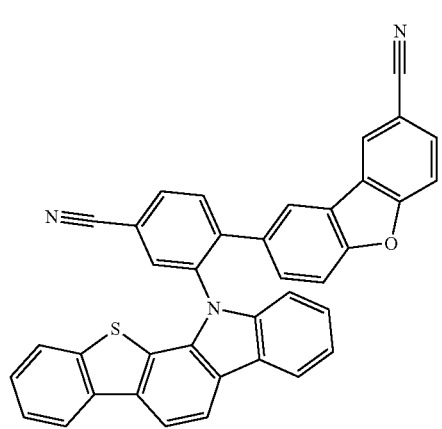
473
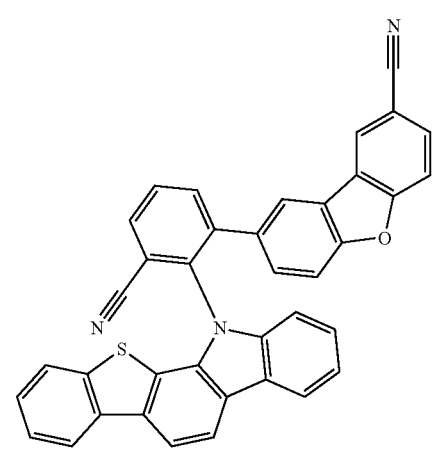
474
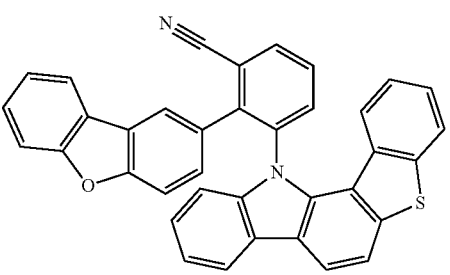
492 -continued
475
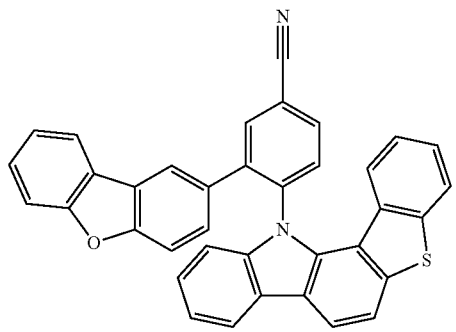
476
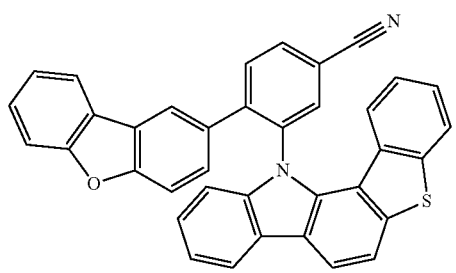
477
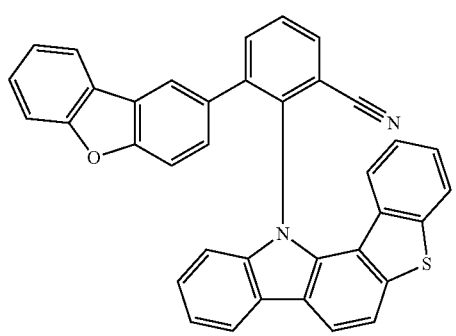
478
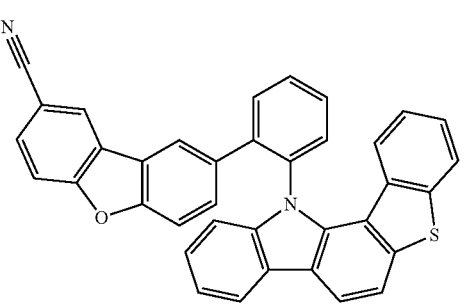
479
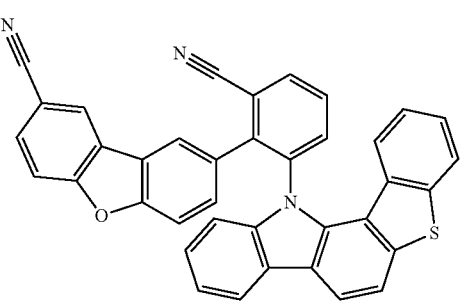

493
-continued
480
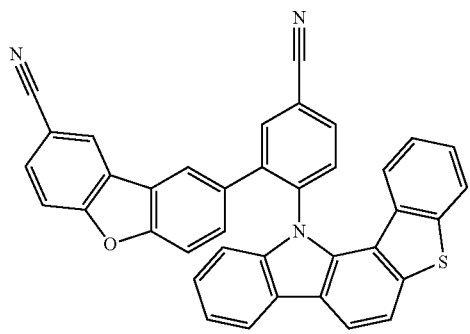
481
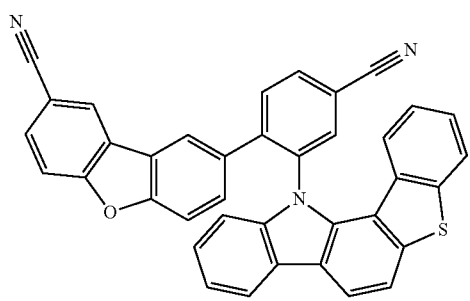
482
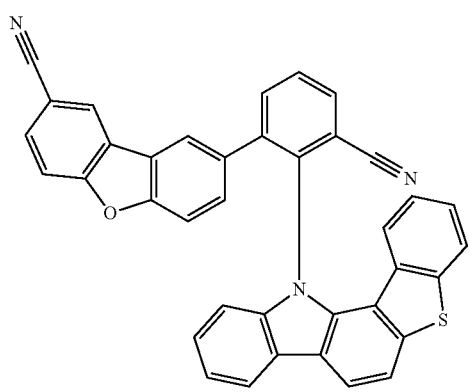
<Group HE4>
1
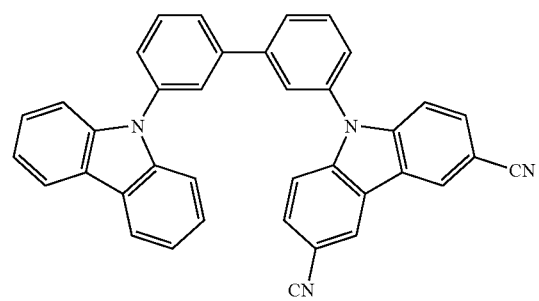
494
-continued
2
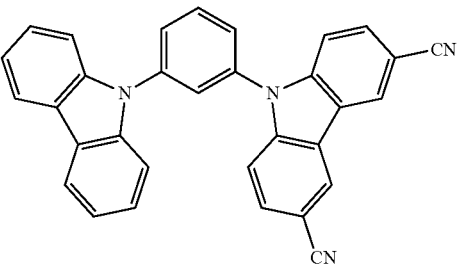
3
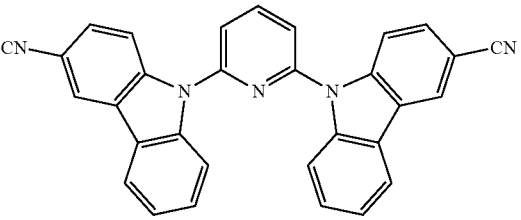
4
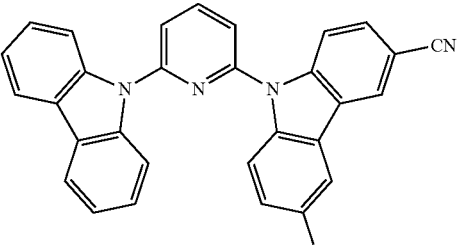
5
6
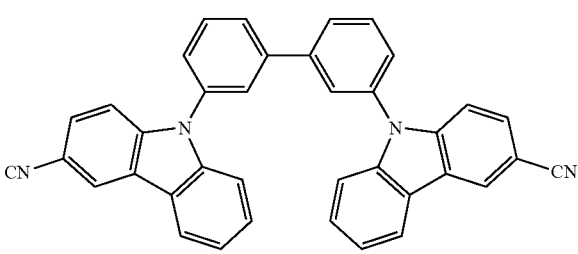

7
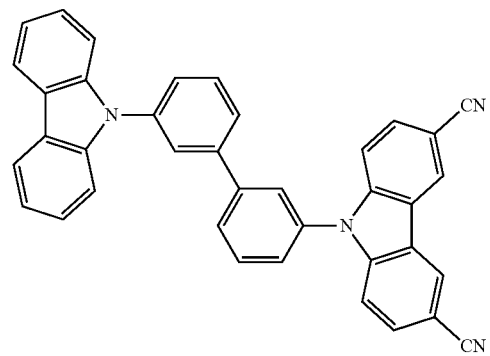
8
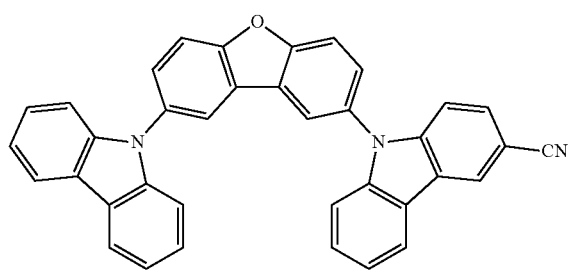
9
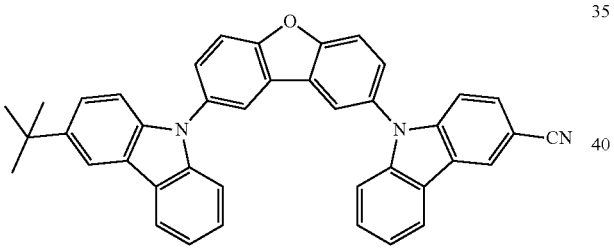
10
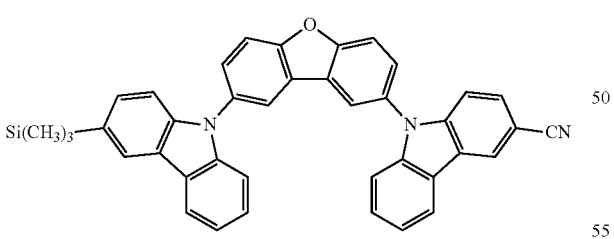
11
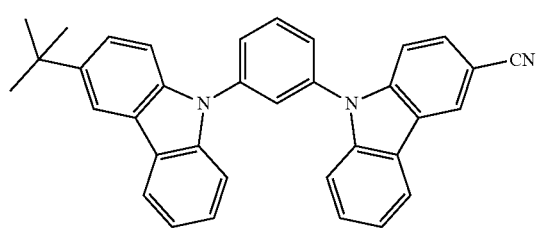
12
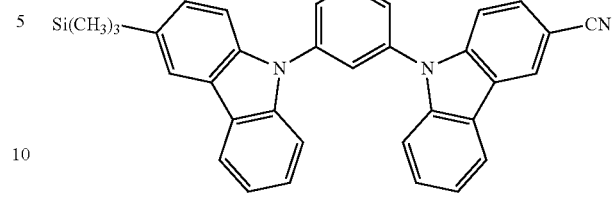
13
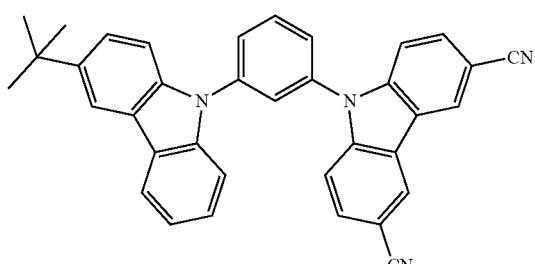
14
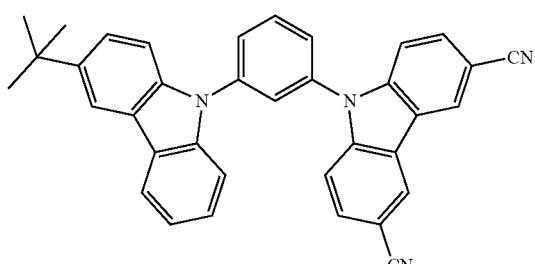
15
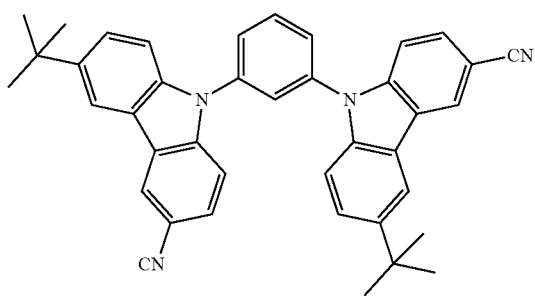
16
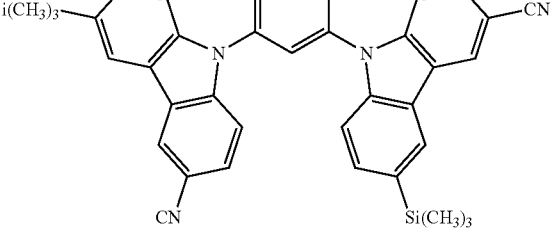

497
-continued
17
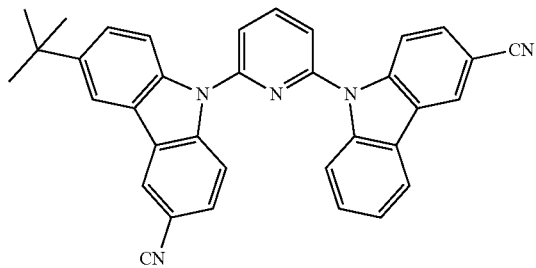
18
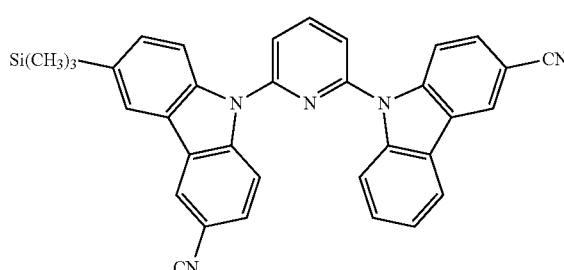
19
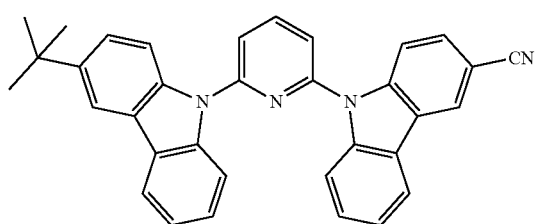
20
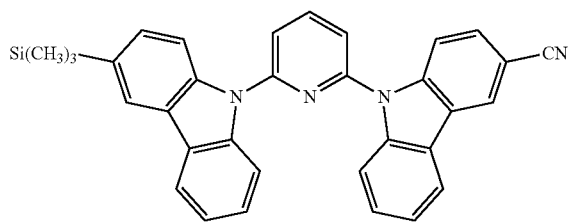
21
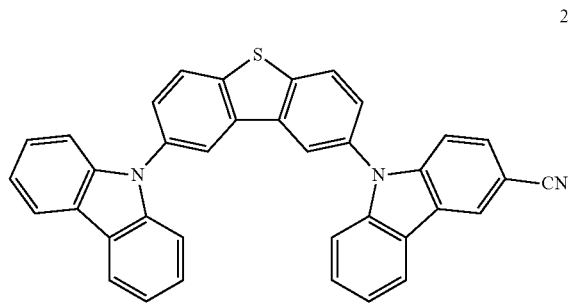
22
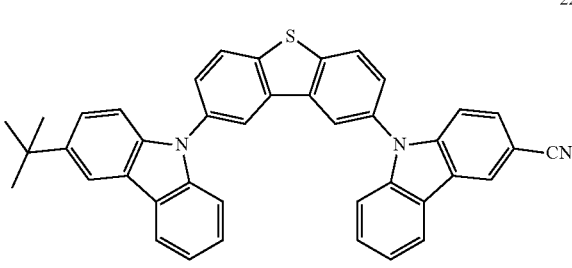
498
-continued
23
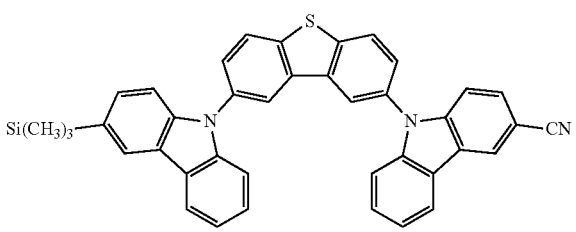
24
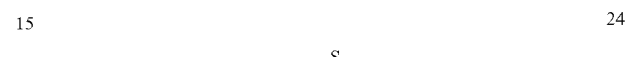
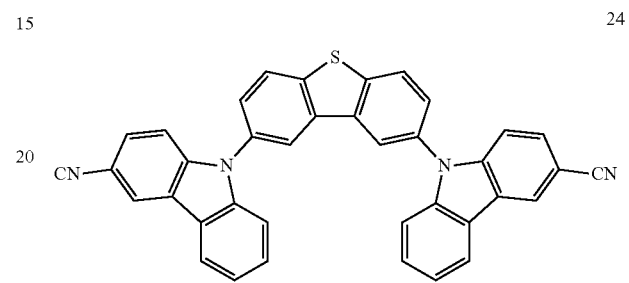
25
26
27

28
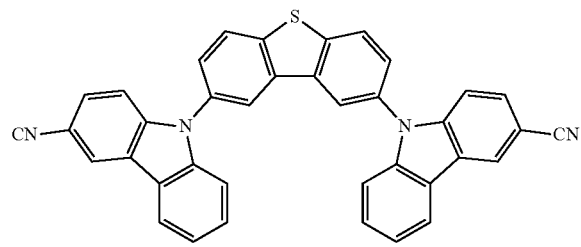
29
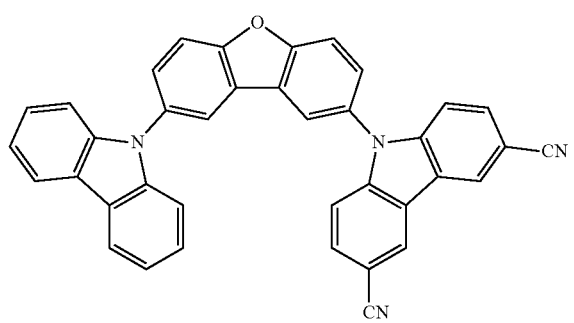
30
31
32
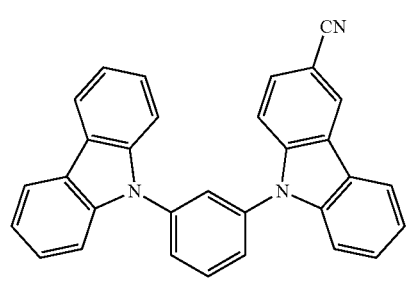
33
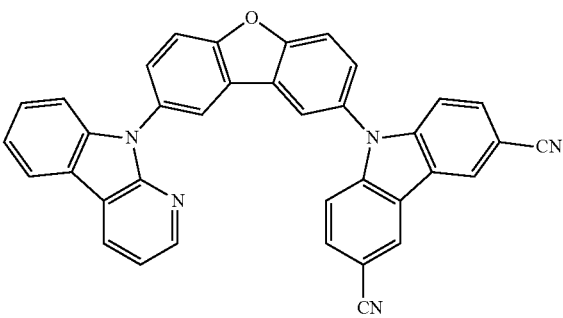
34
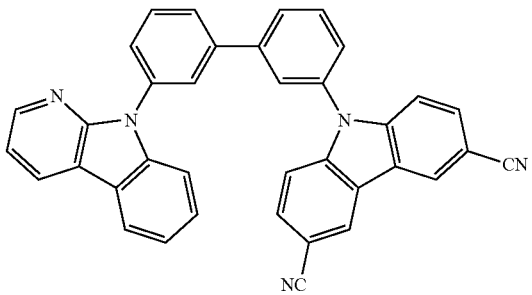
35
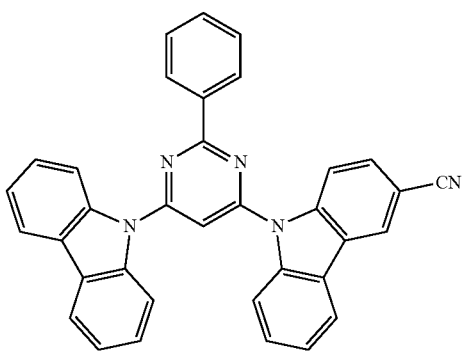
36
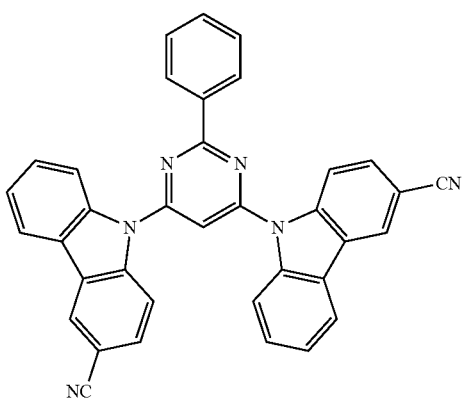

37
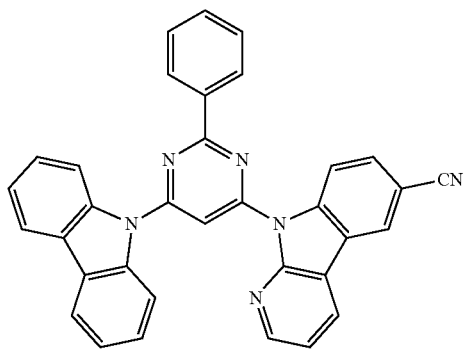
38
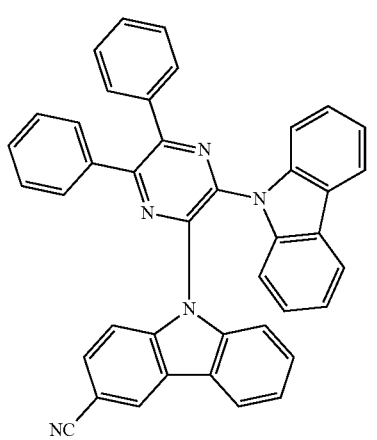
39
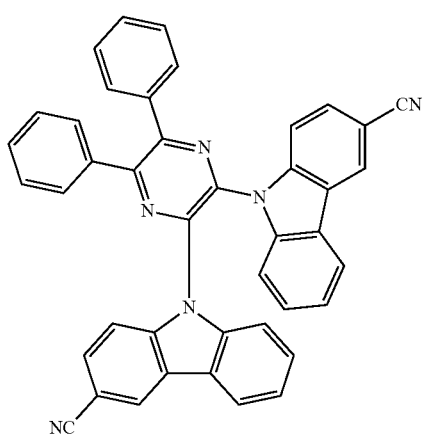
40
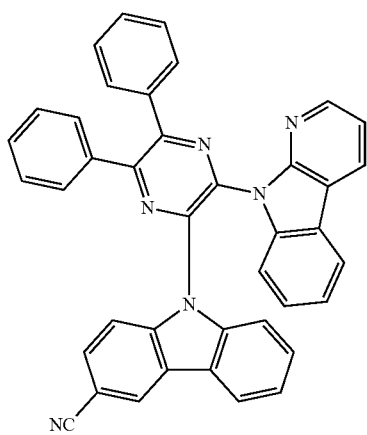
41
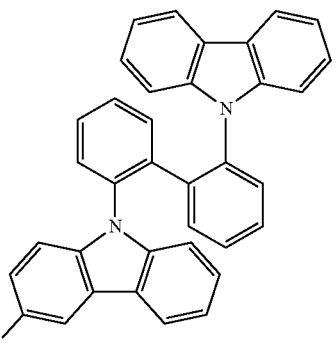
42
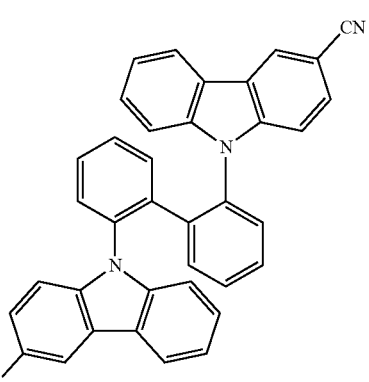
43
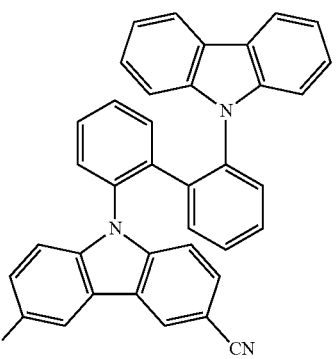
44
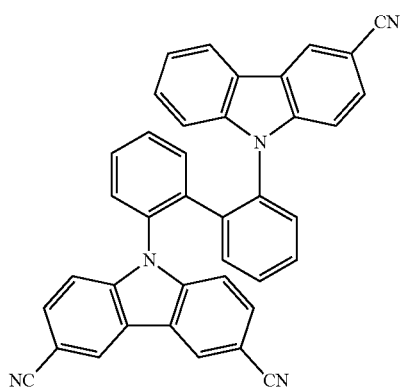

45
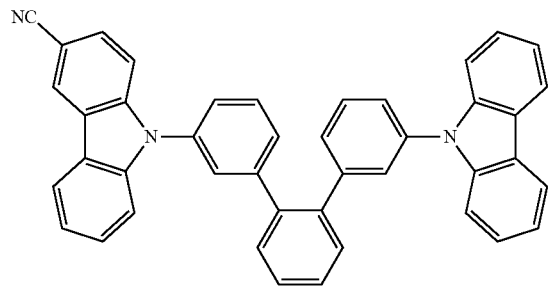
46
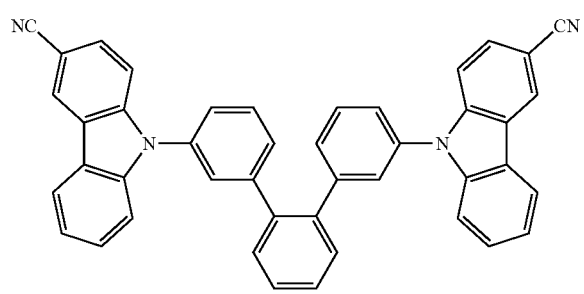
47
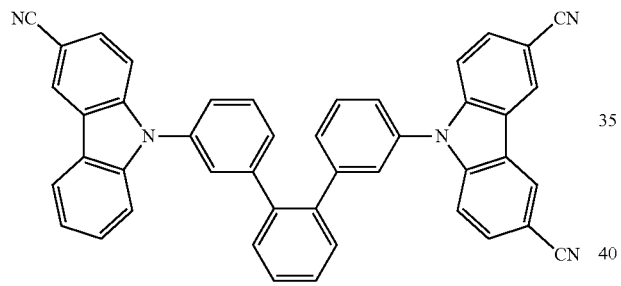
48

49

50
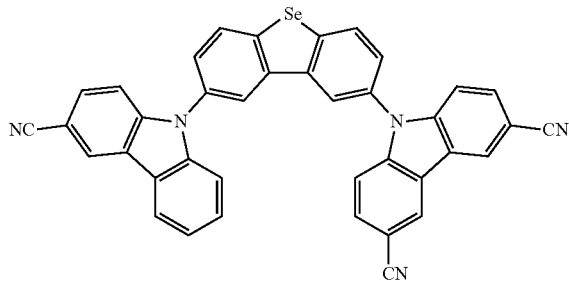
51
52
53

505
-continued
54
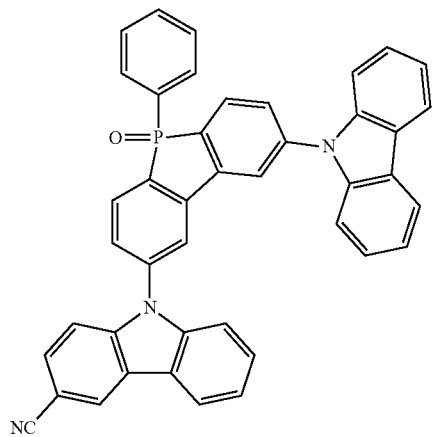
55
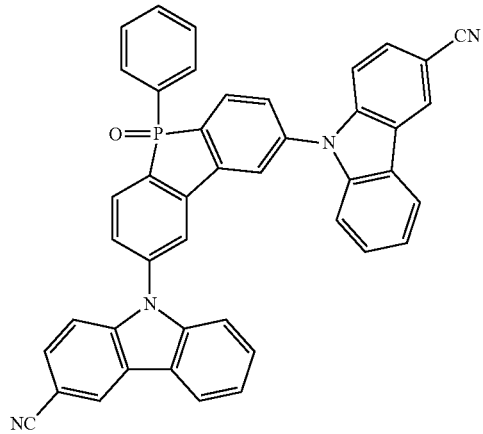
56
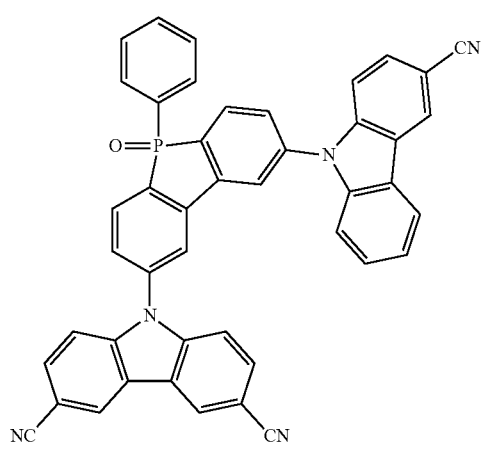
506
1
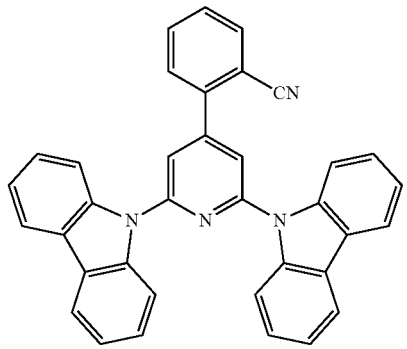
2
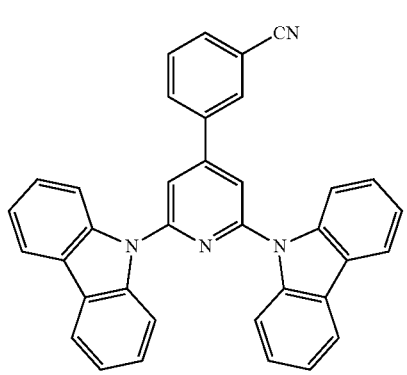
3
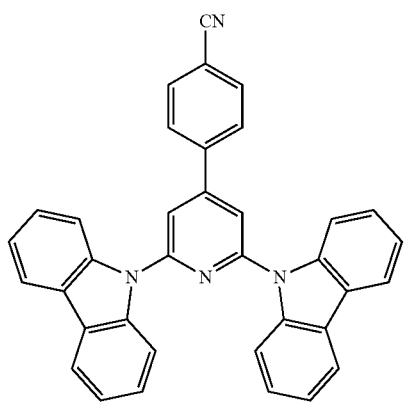
4

-continued
5
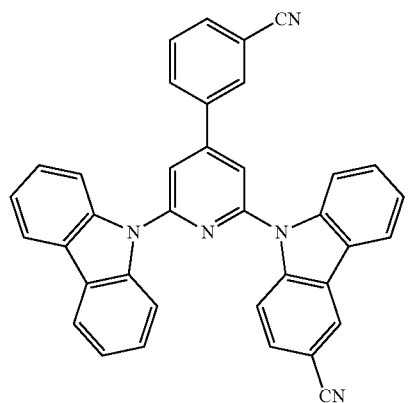
6
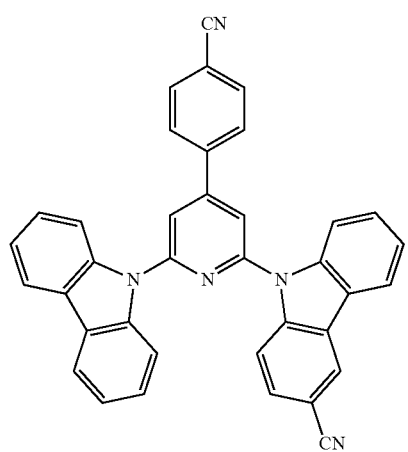
7
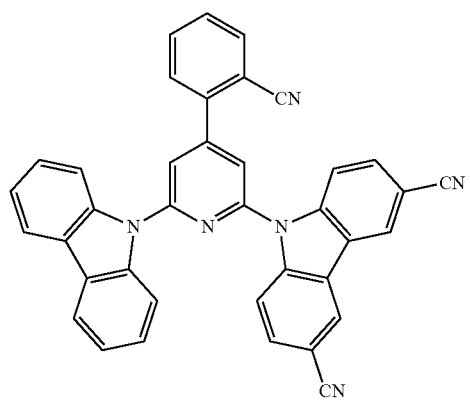
8
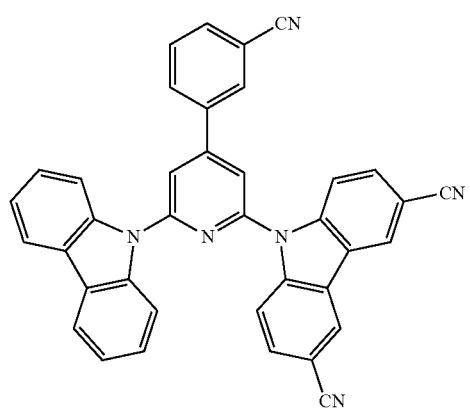
-continued
9
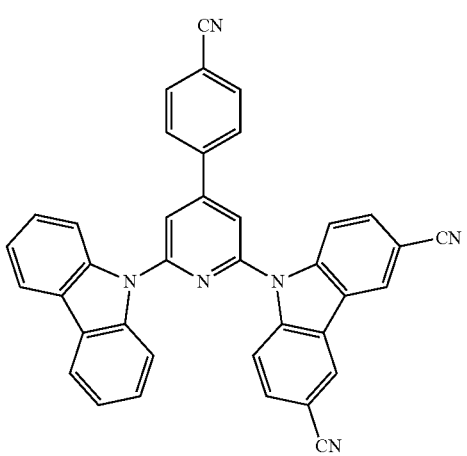
10
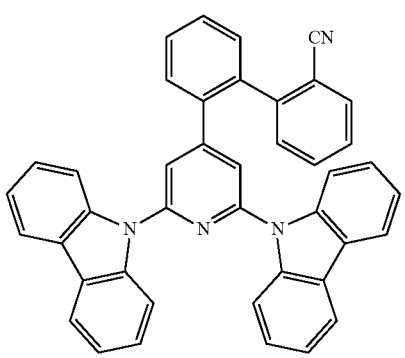
11
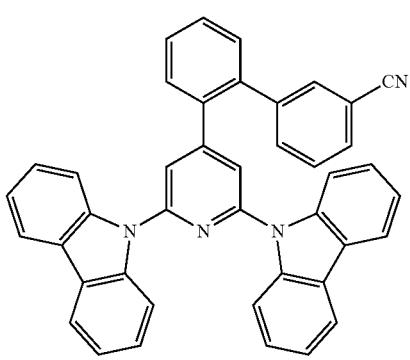
12
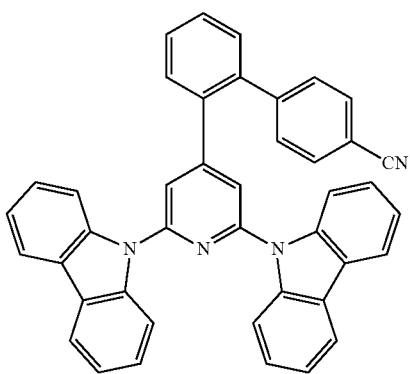

13
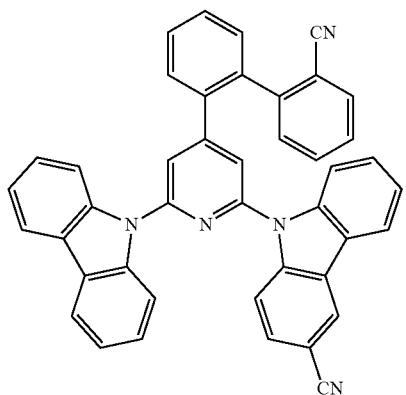
14
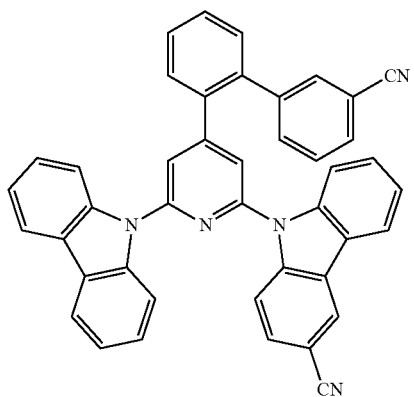
15
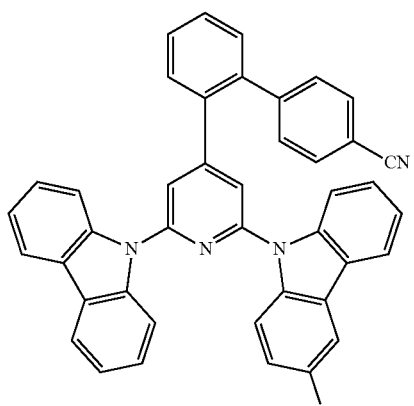
16
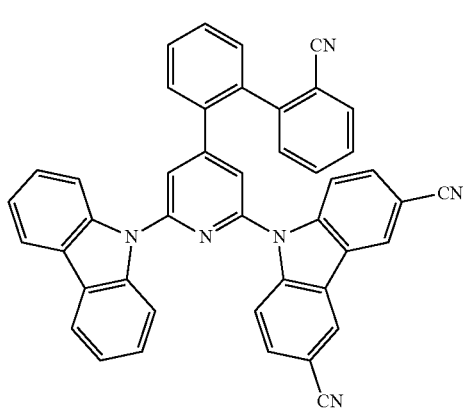
17
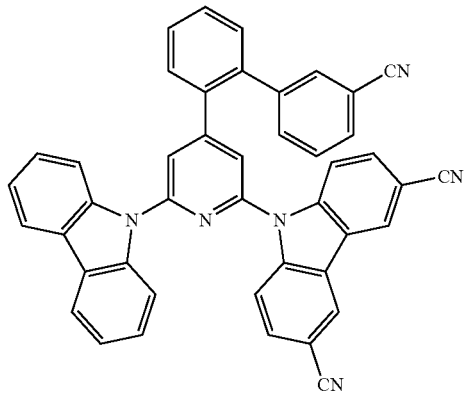
18
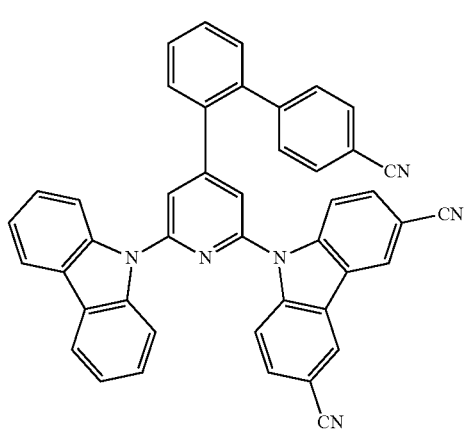
19
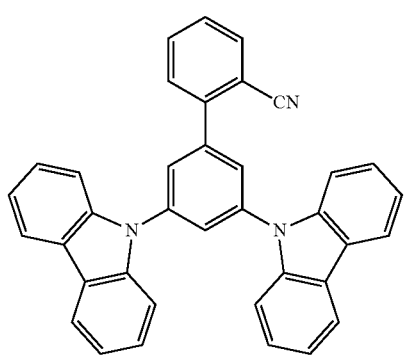
20
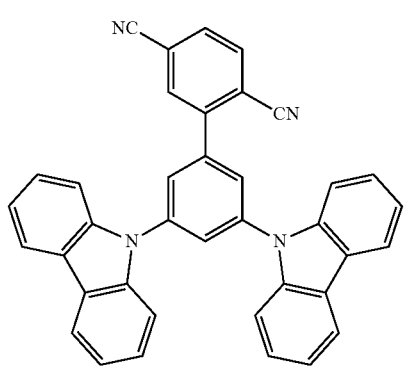

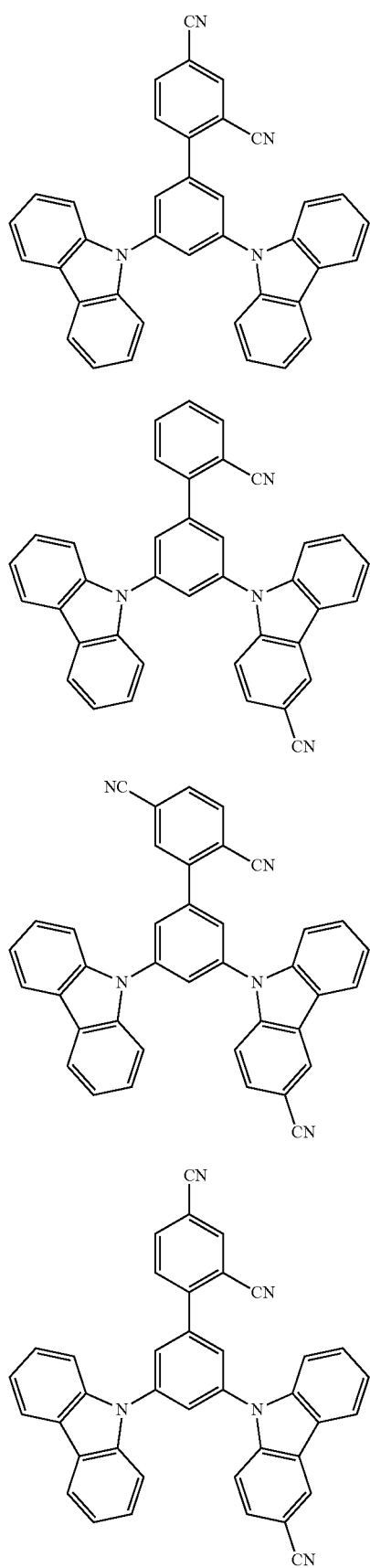
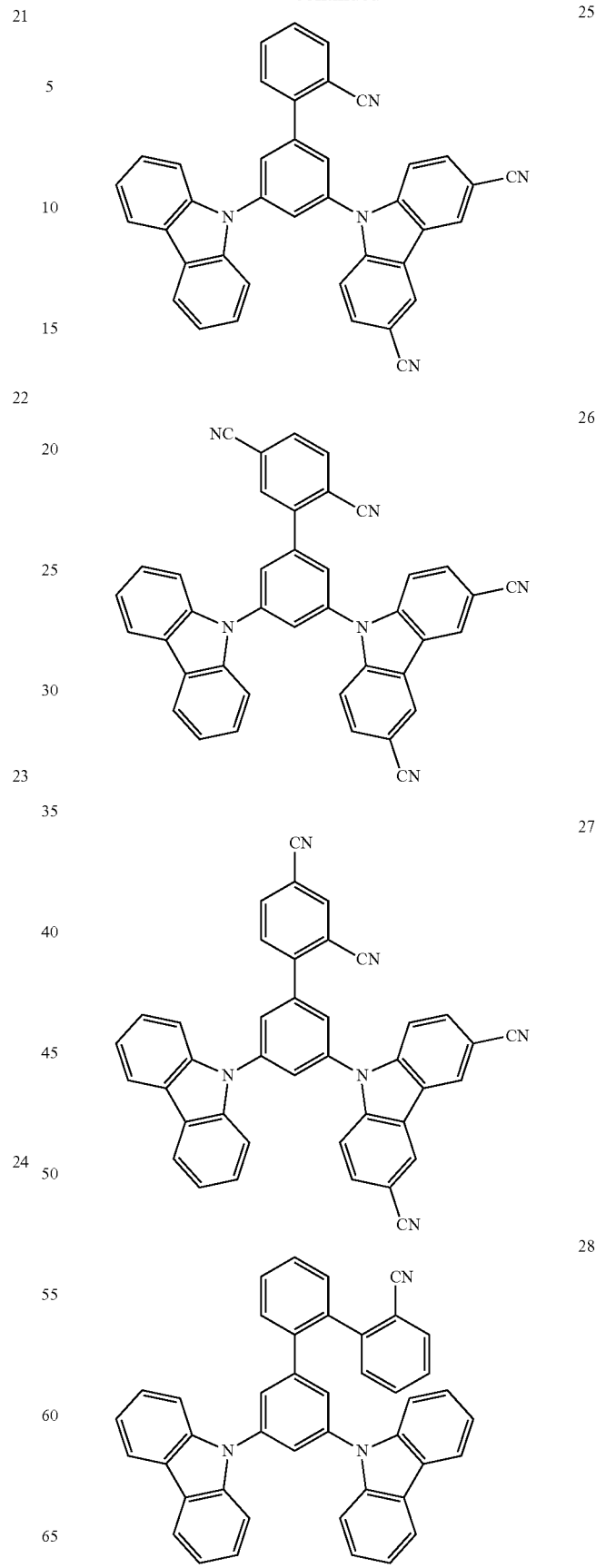

29
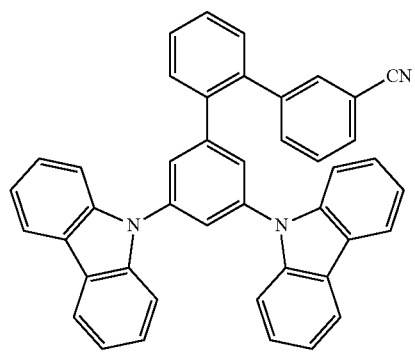
30
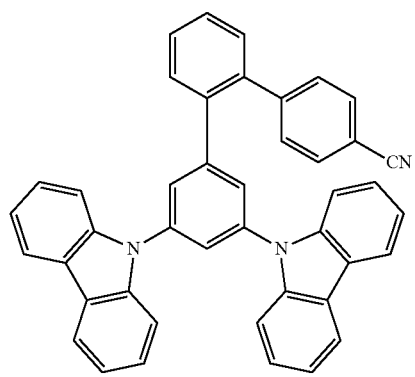
31
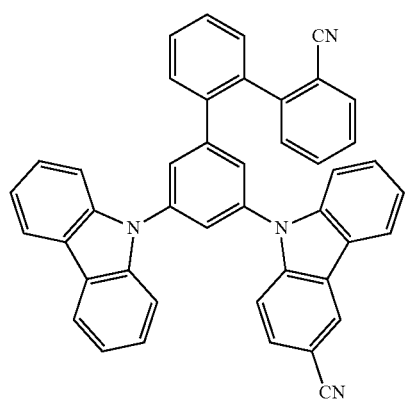
32
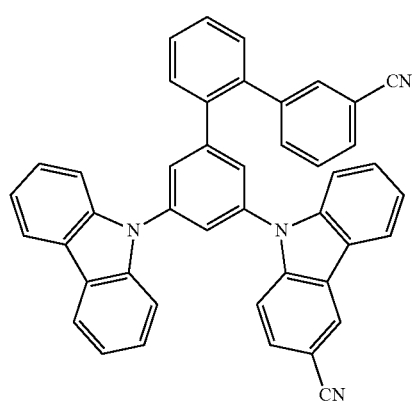
33
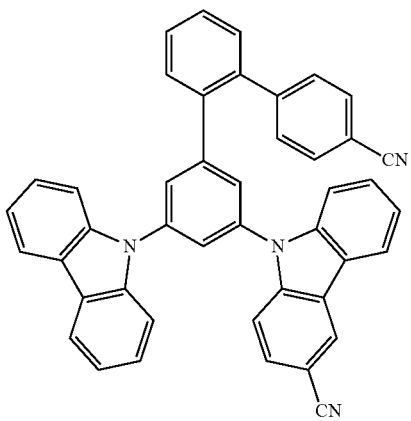
34
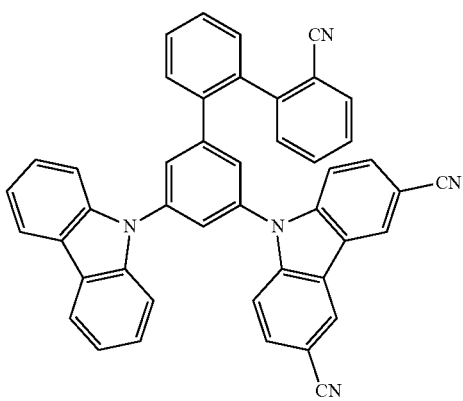
35
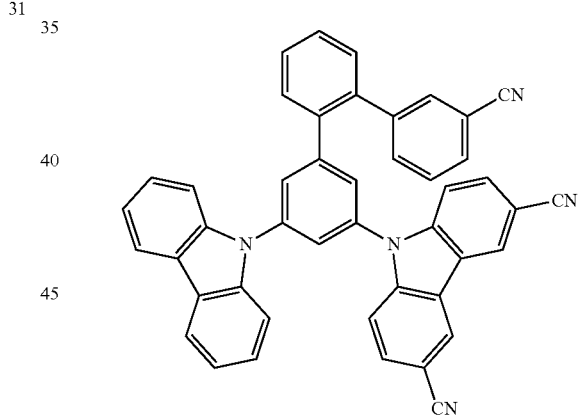
36
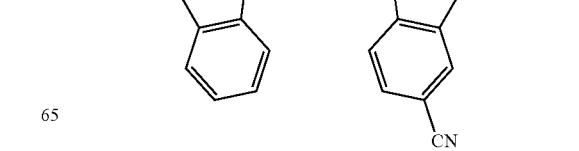

-continued
37
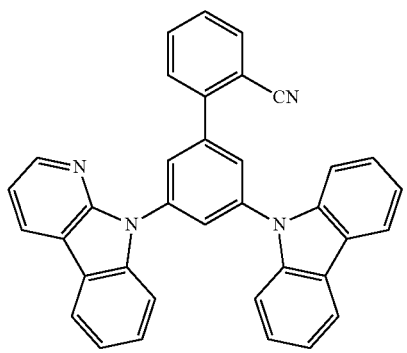
38
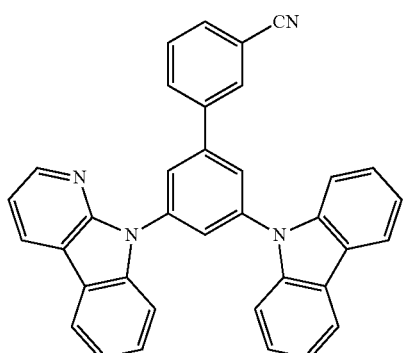
39
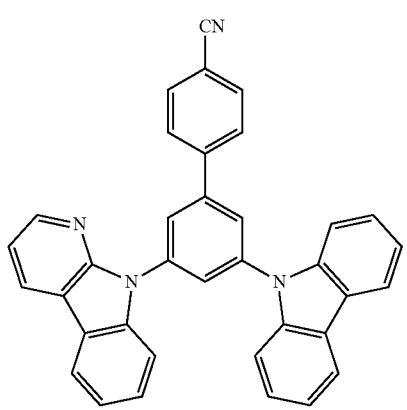
40
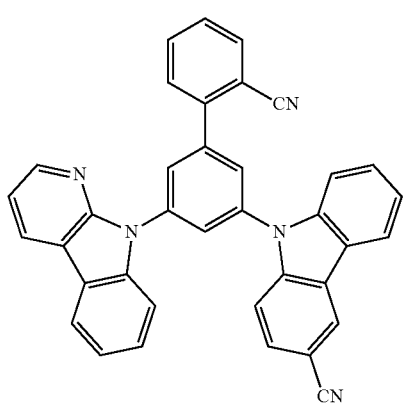
-continued
41
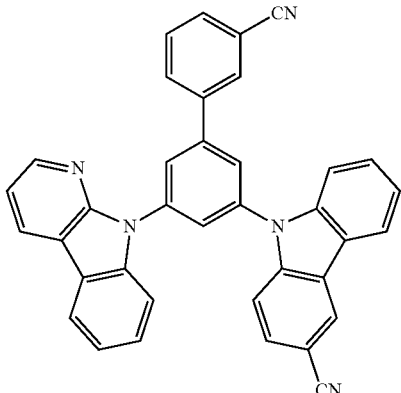
42
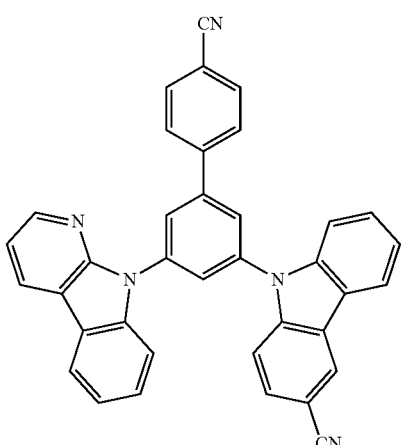
43
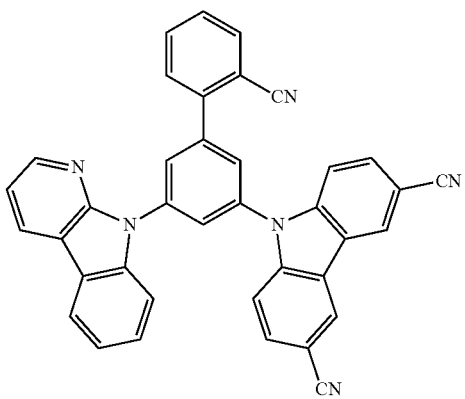
44
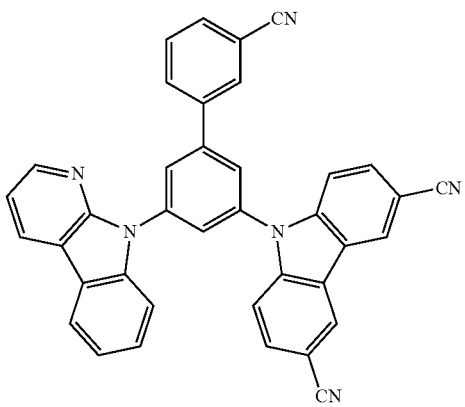

45
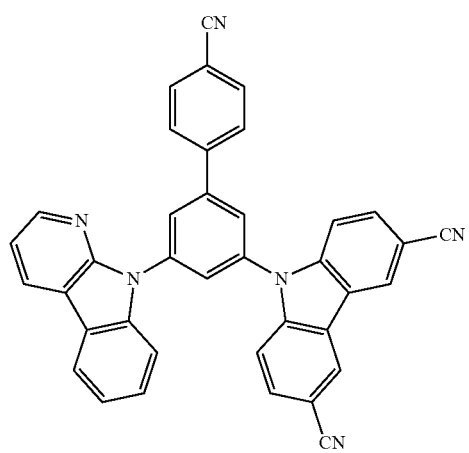
46
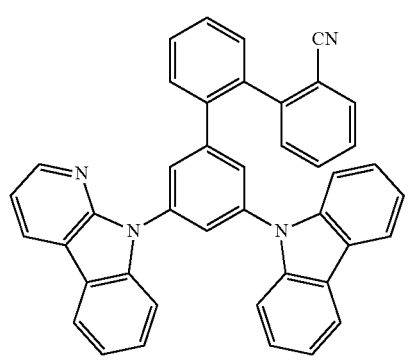
47
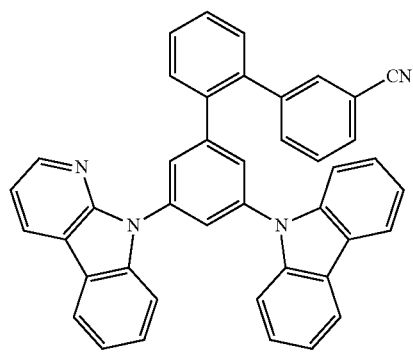
48
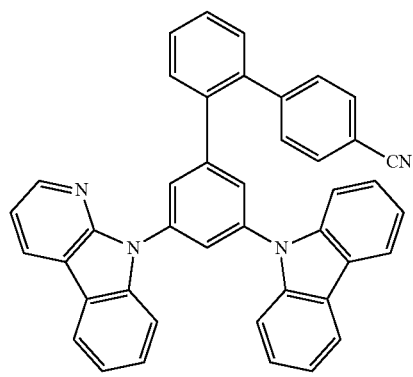
49
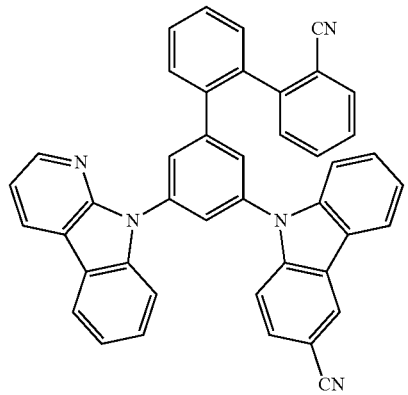
50
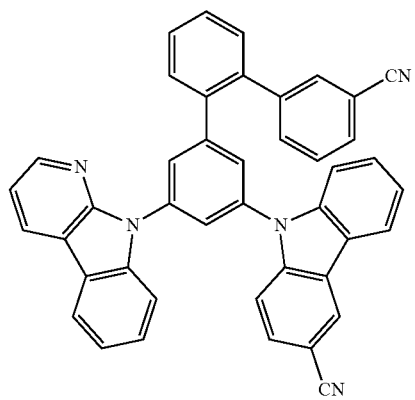
51
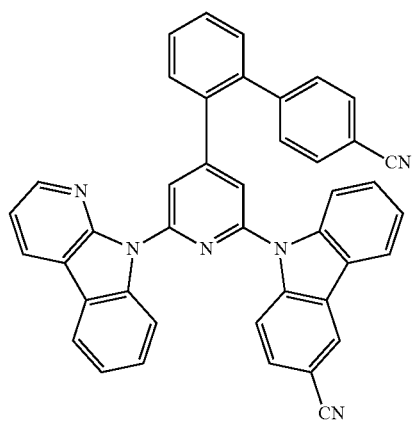
52
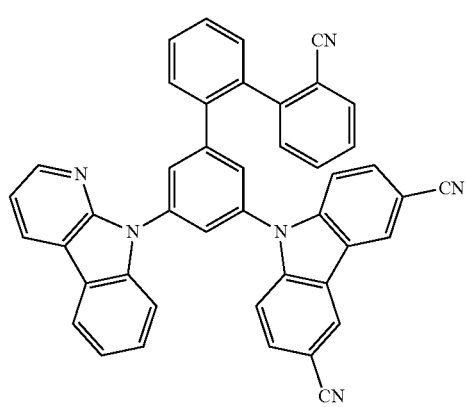

53
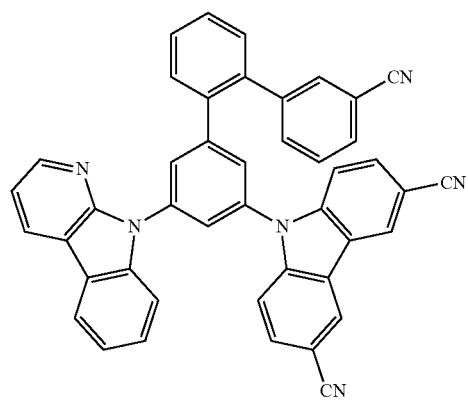
54
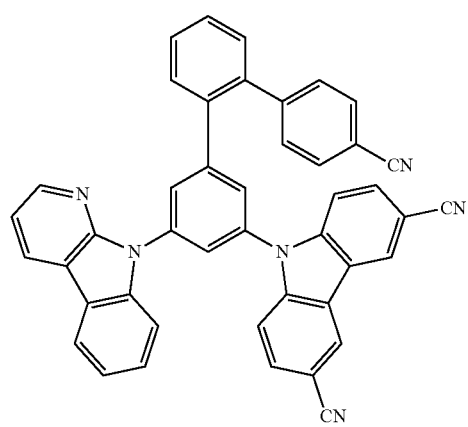
55
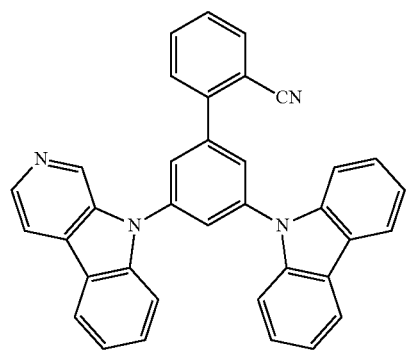
56
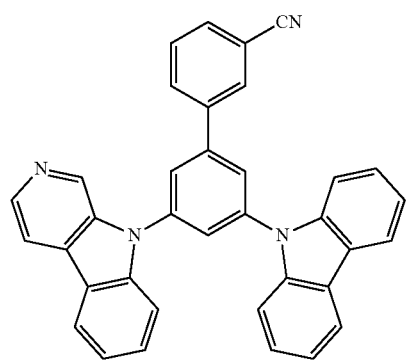
57
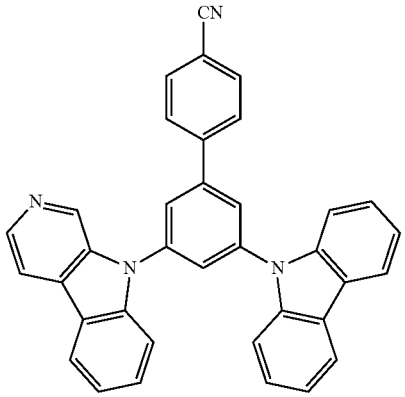
58
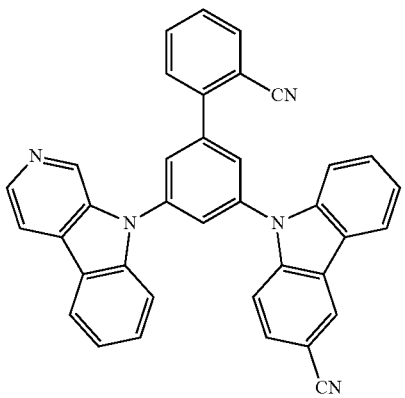
59
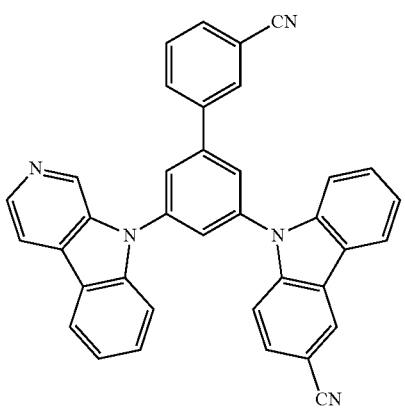
60
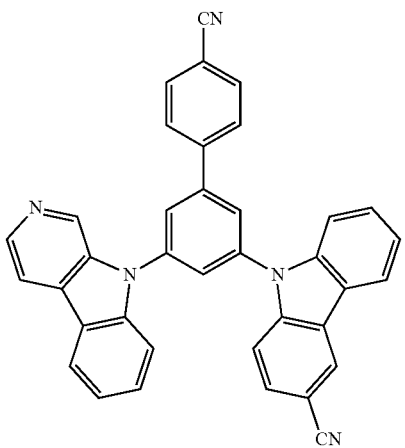

-continued
61
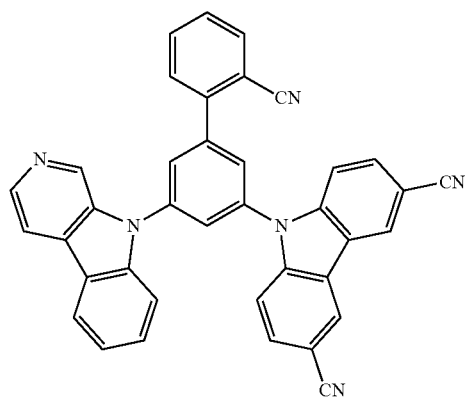
62
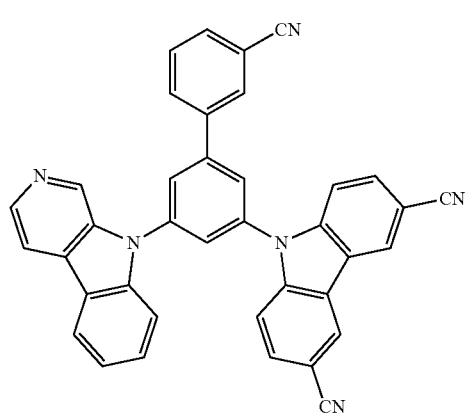
63
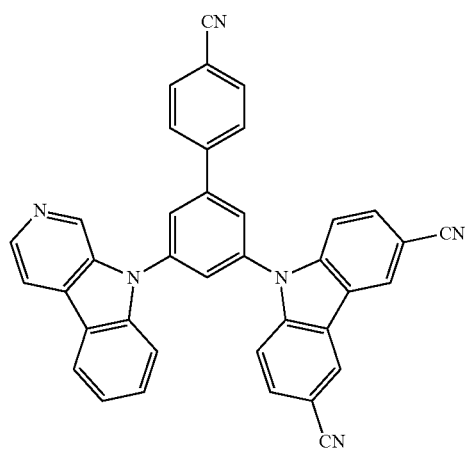
64
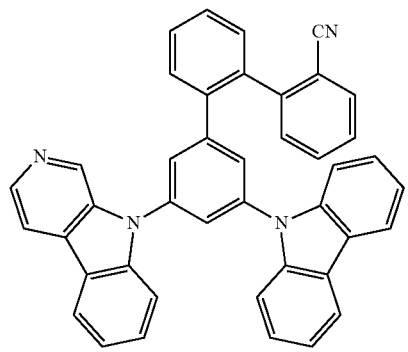
-continued
65
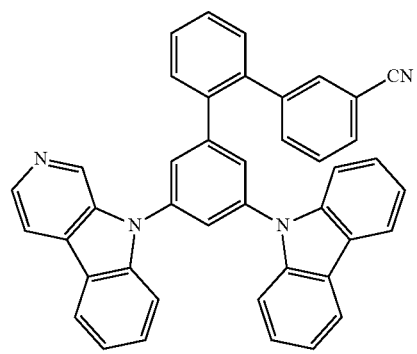
66
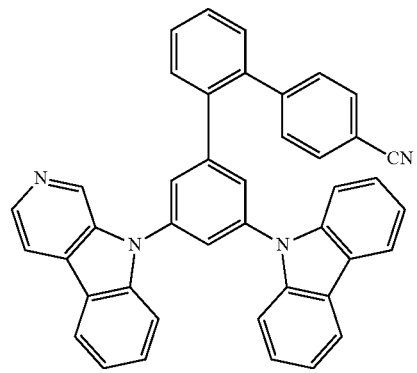
67
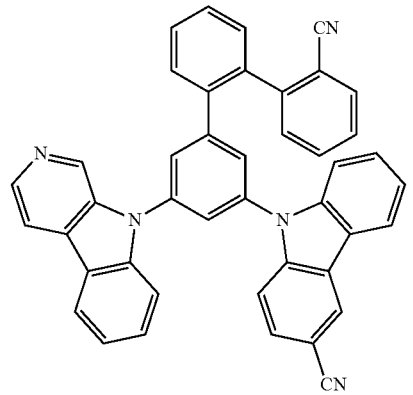
68
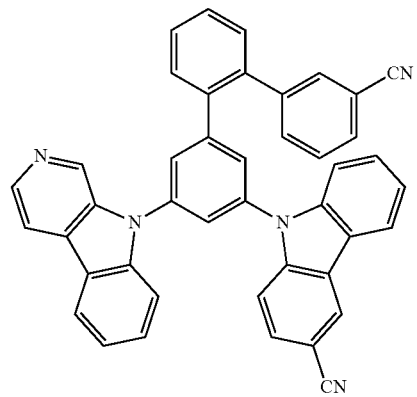

523
-continued
69
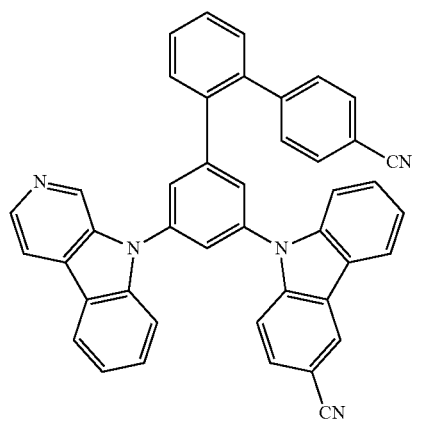
70
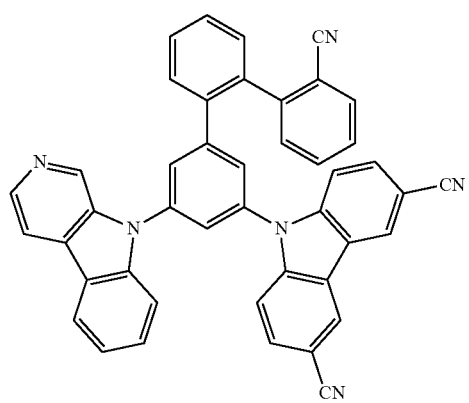
71
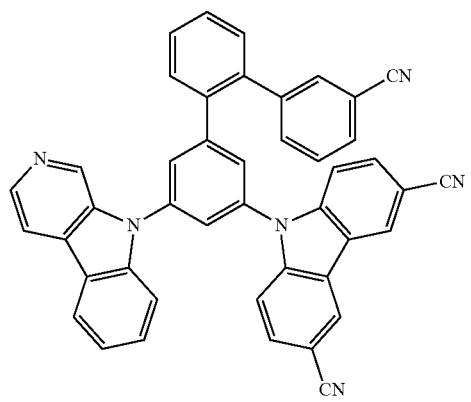
72
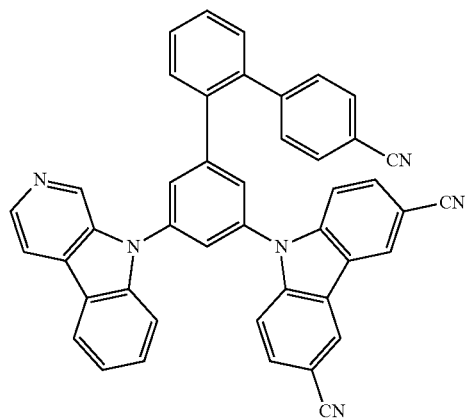
524
-continued
73
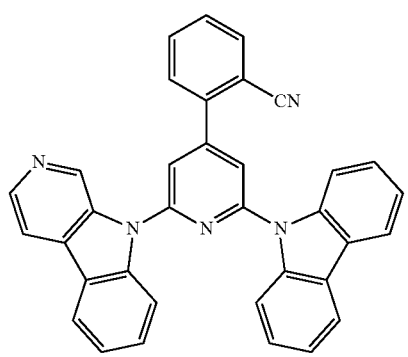
74
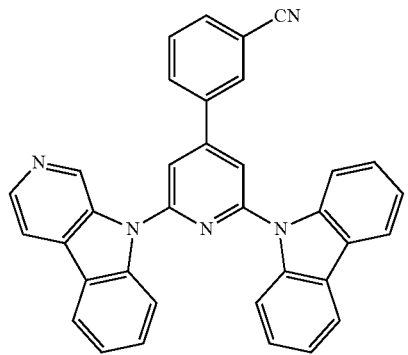
75
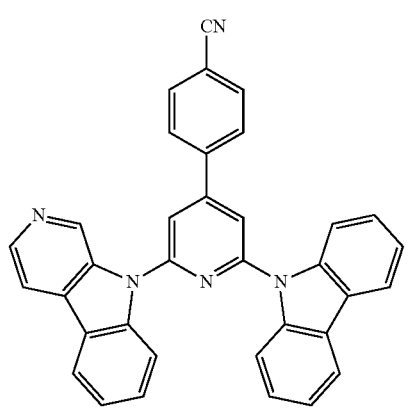
76
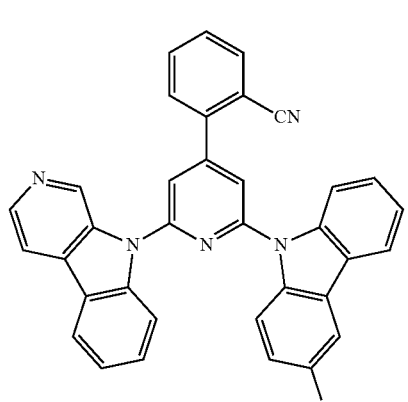

-continued
77
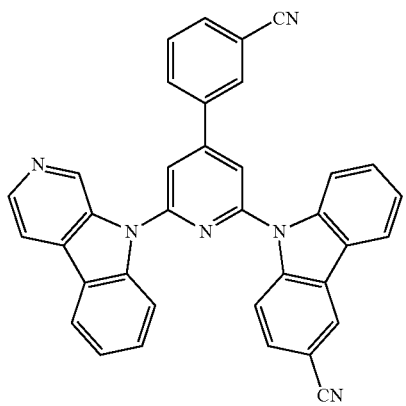
78
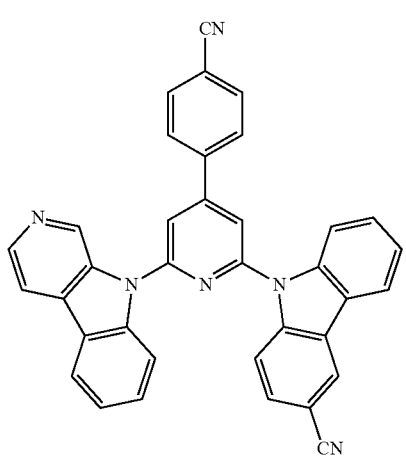
79
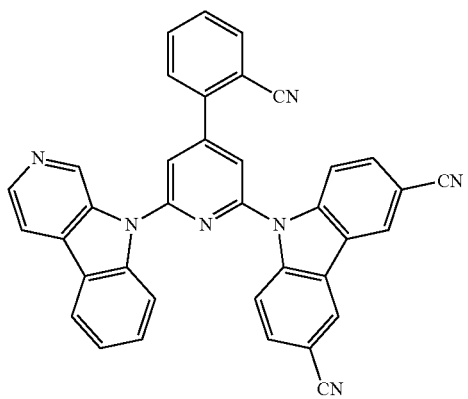
80
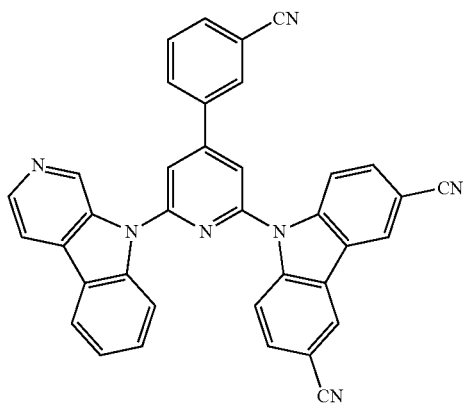
-continued
81
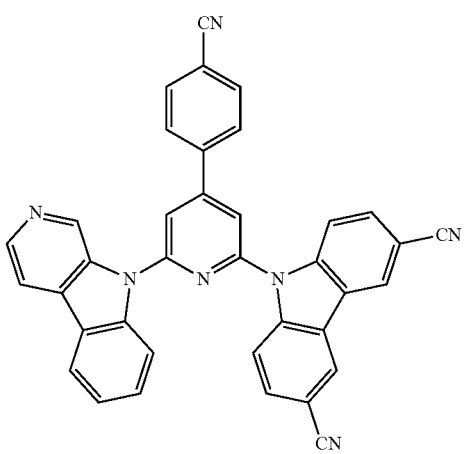
82
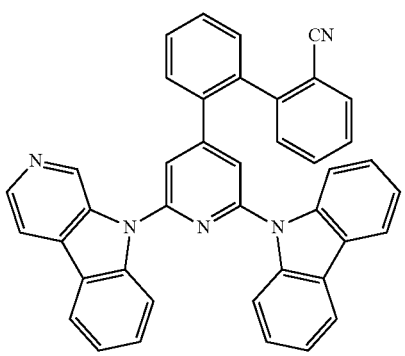
83
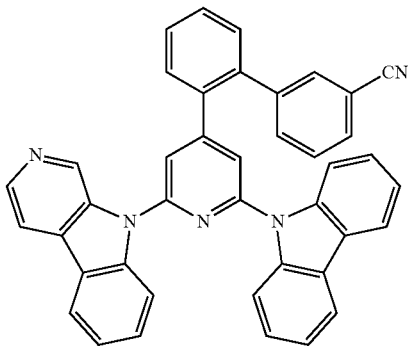
84
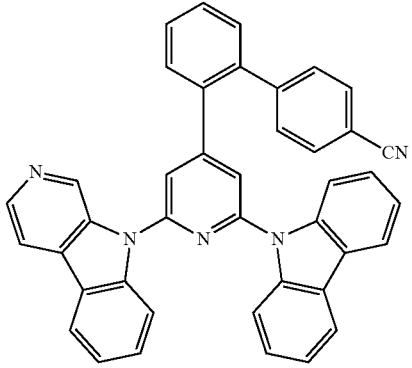

| 527 -continued | 528 -continued |
|---|---|
| 85 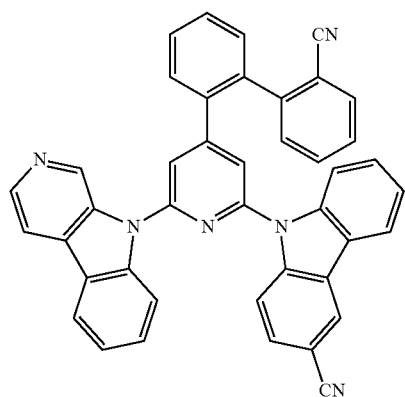 | 89 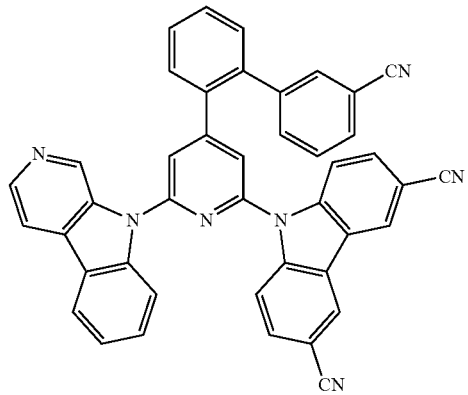 |
| 86 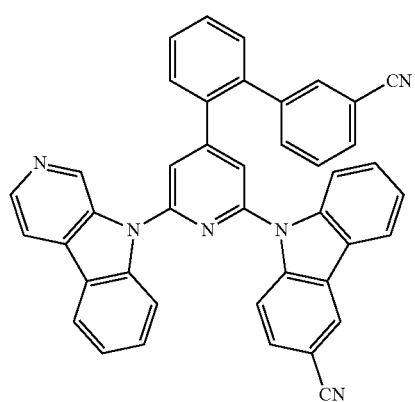 | 90 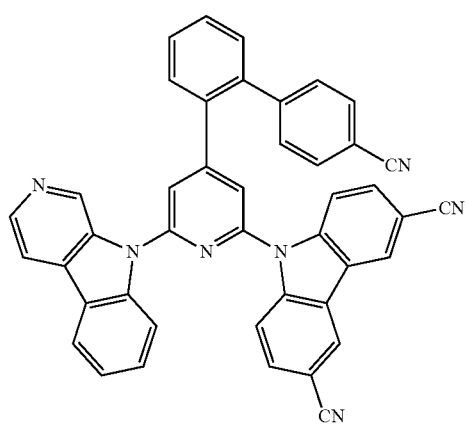 |
| 87 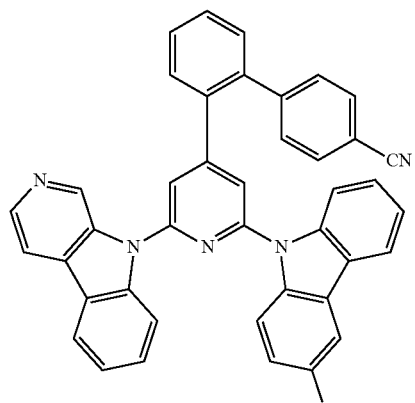 | 91 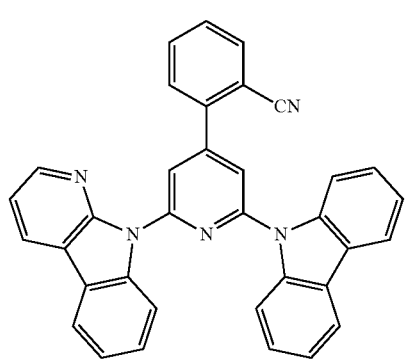 |
| 88 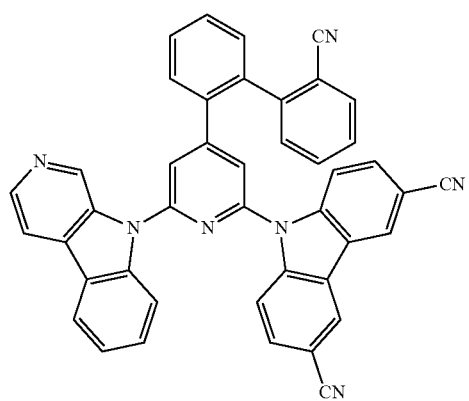 | 92 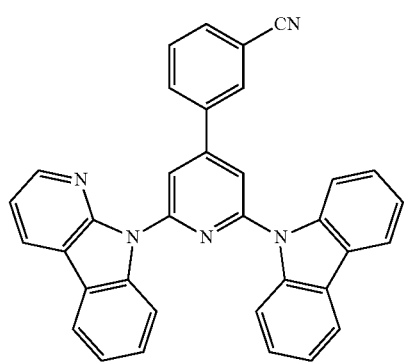 |

529
-continued
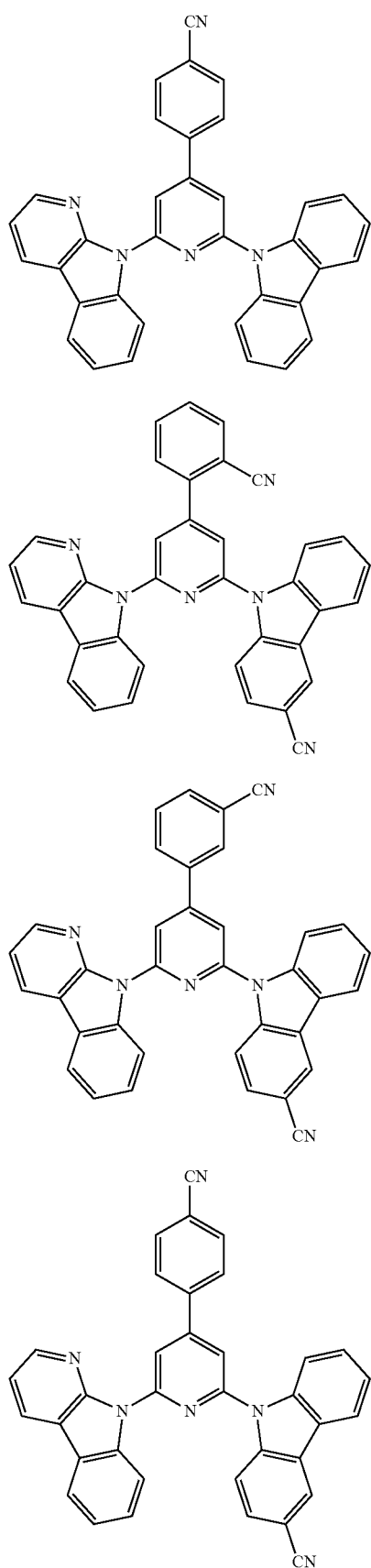
530
-continued
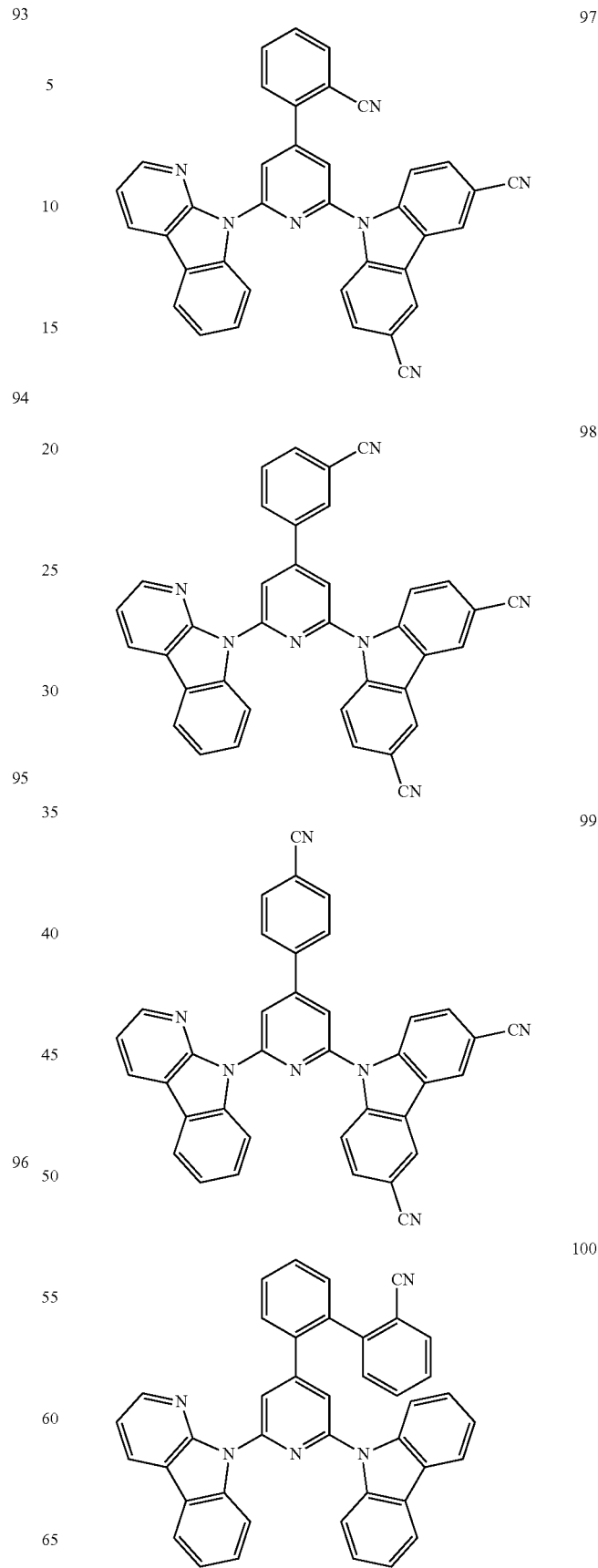

101
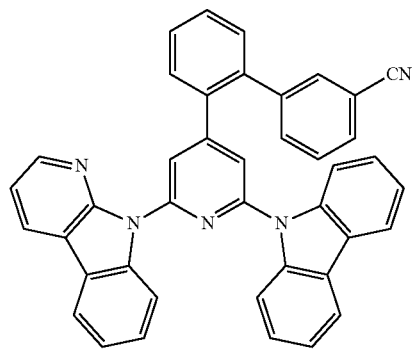
102
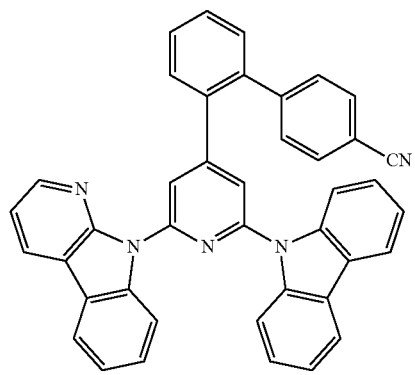
103
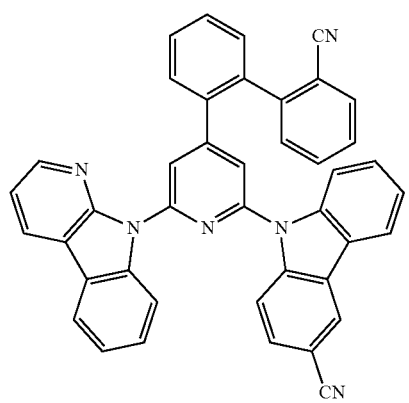
104
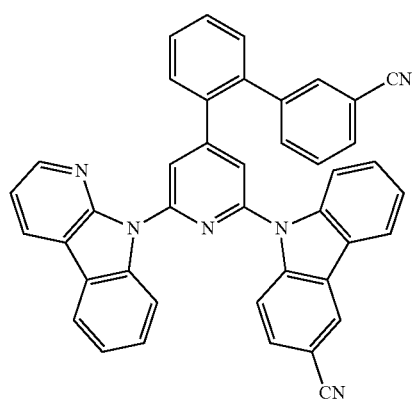
105
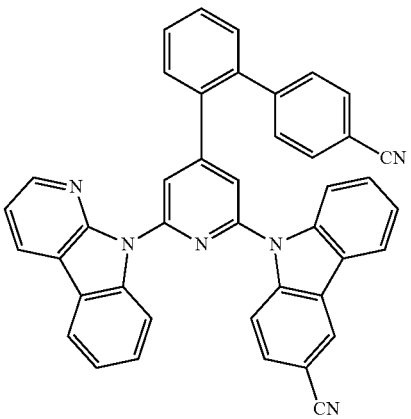
106
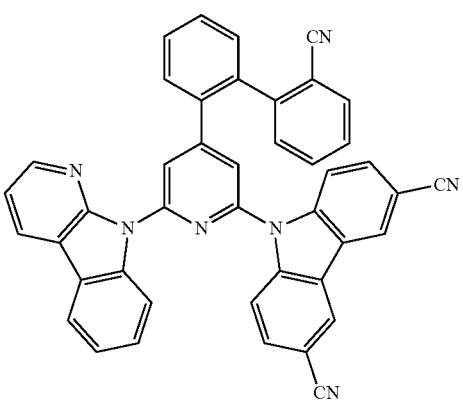
107
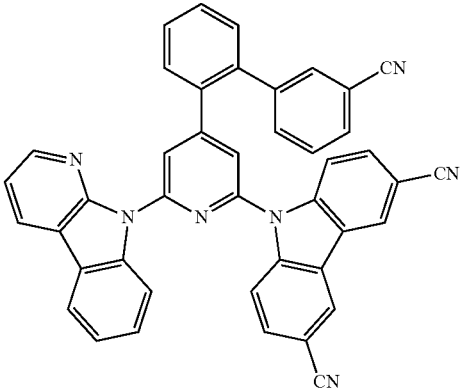
108
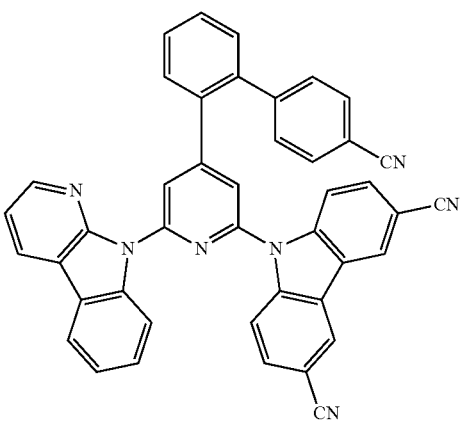

109
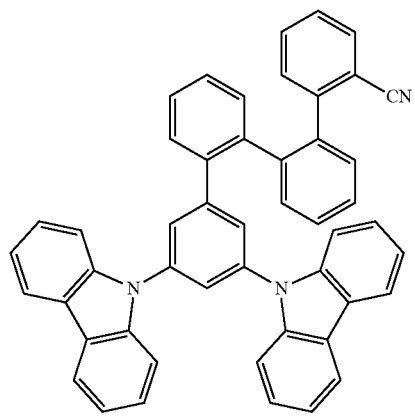
110
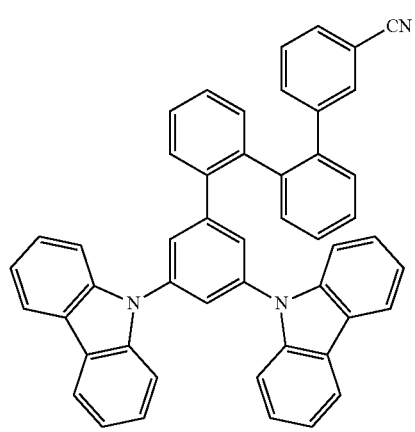
111
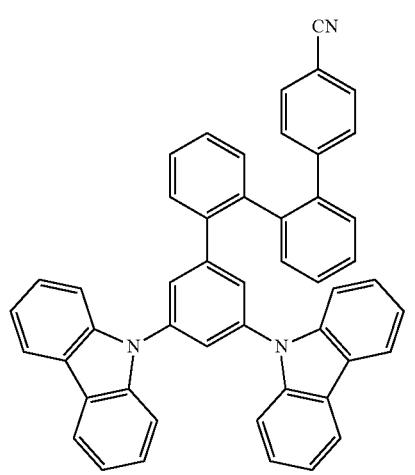
112
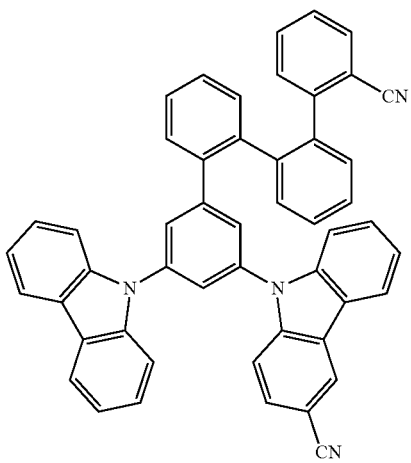
113
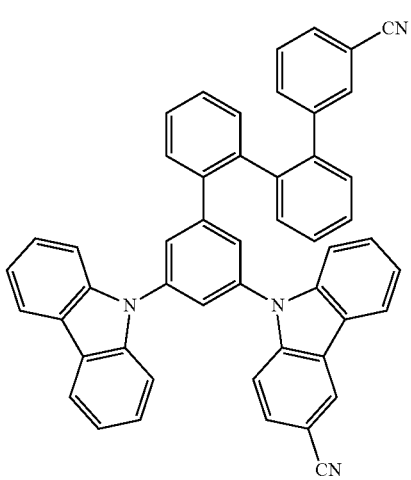
114
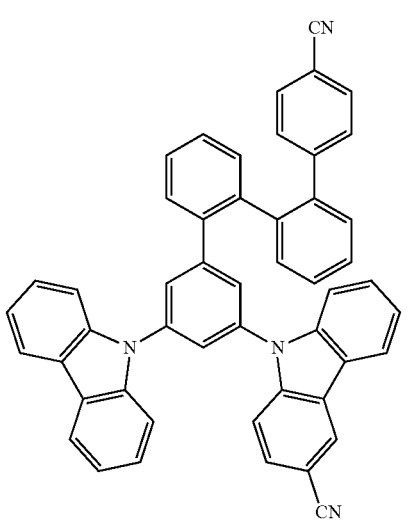

535
-continued
536
-continued
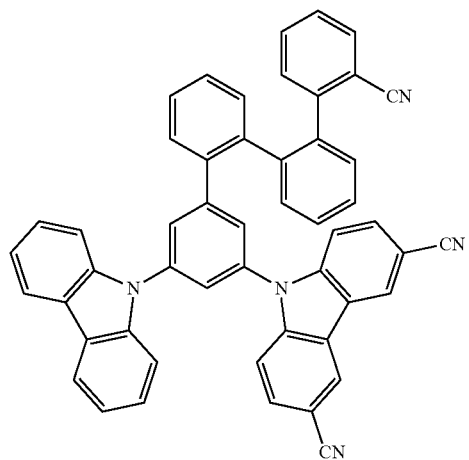
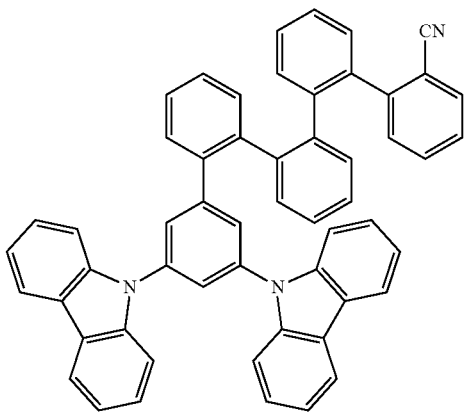

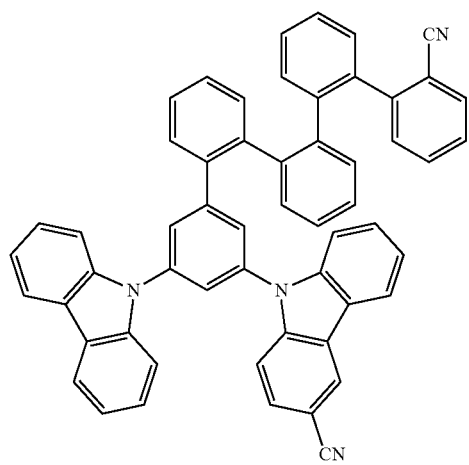
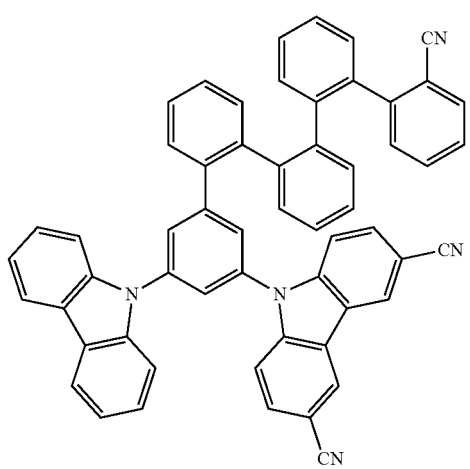

127
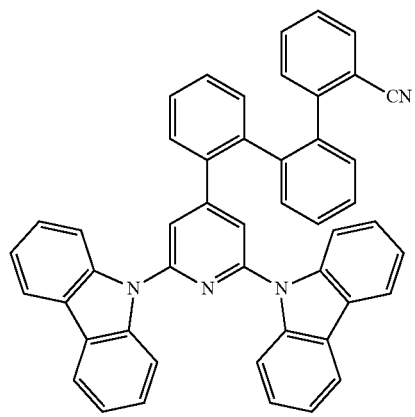
128
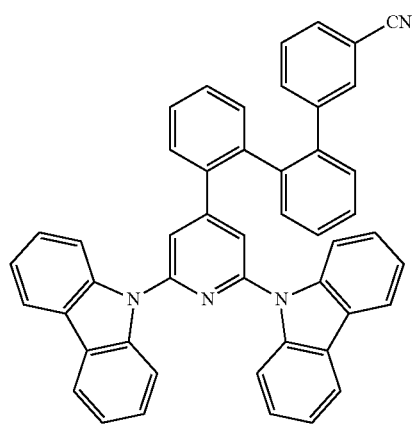
129
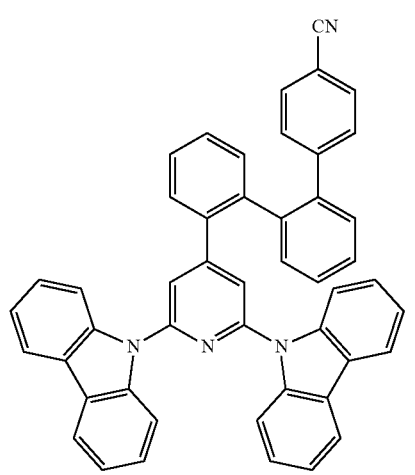
130
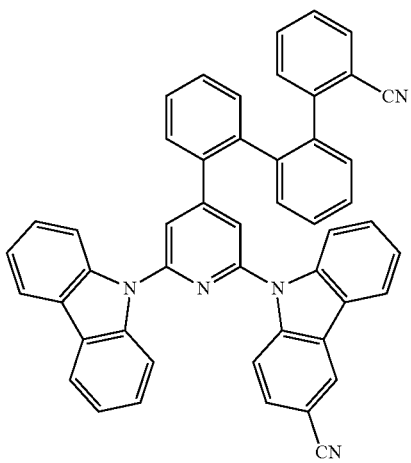
131
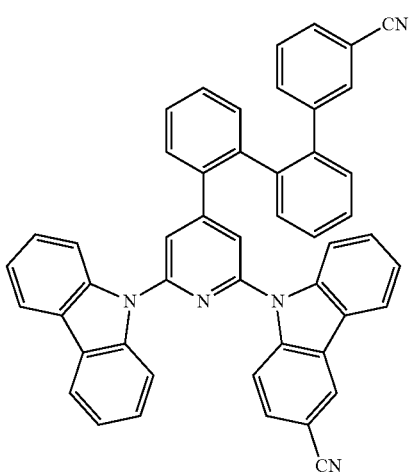
132
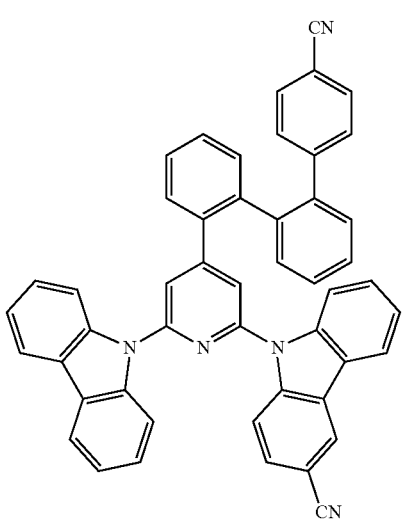

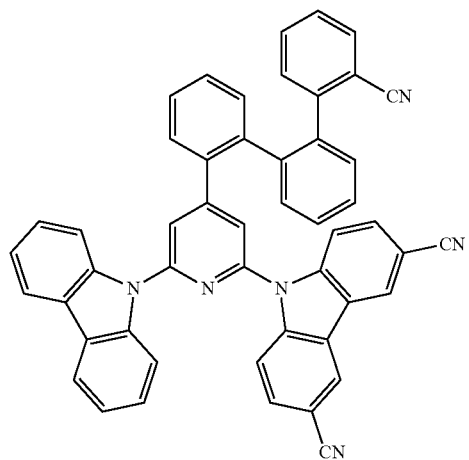
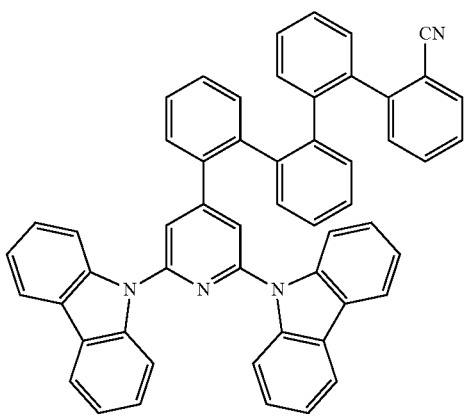

139
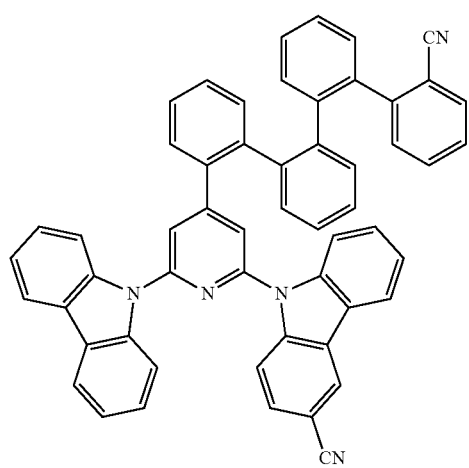
140
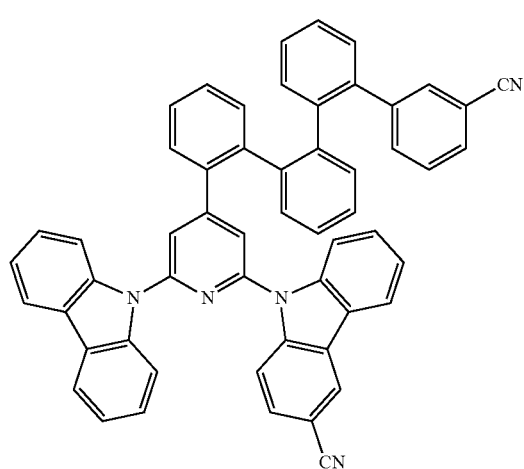
141
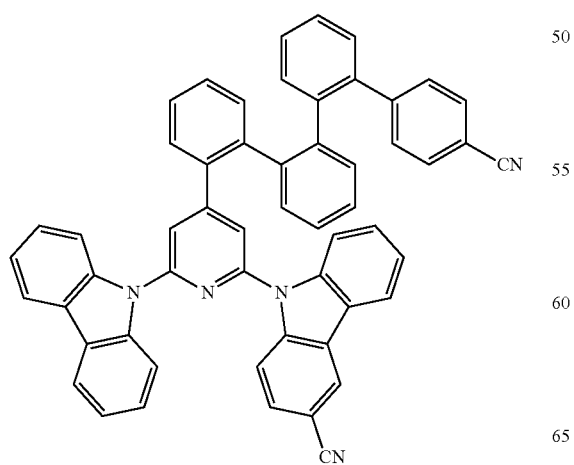
142
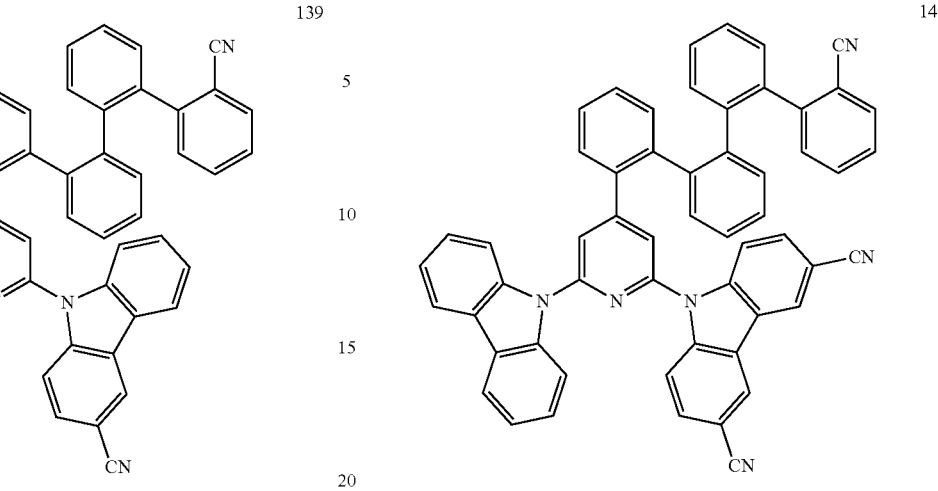
143
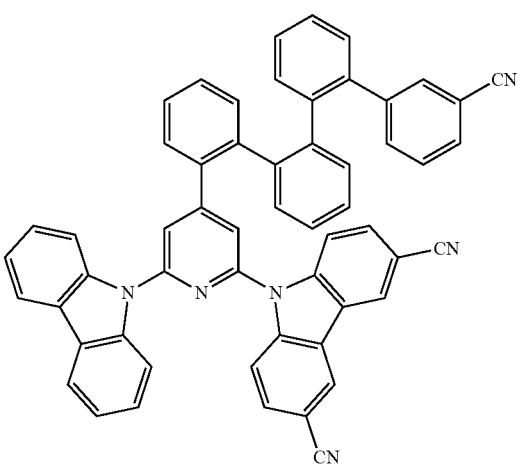
144
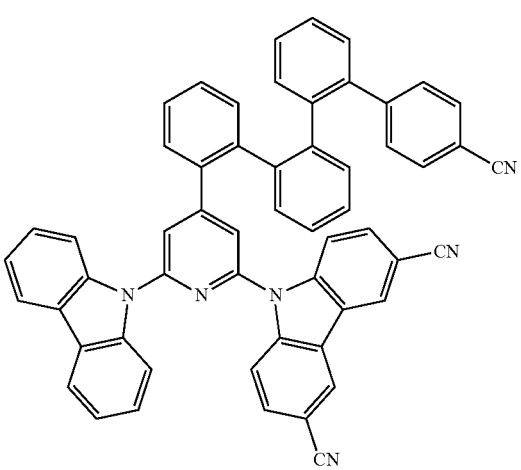

545
-continued
145
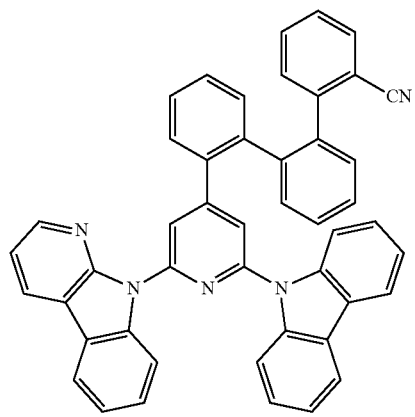
146
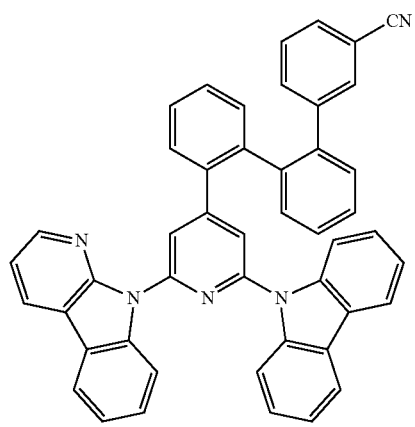
147
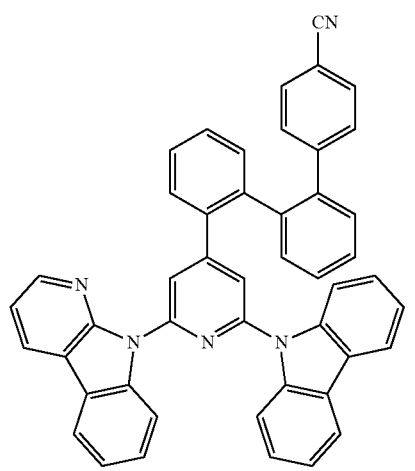
546
-continued
148
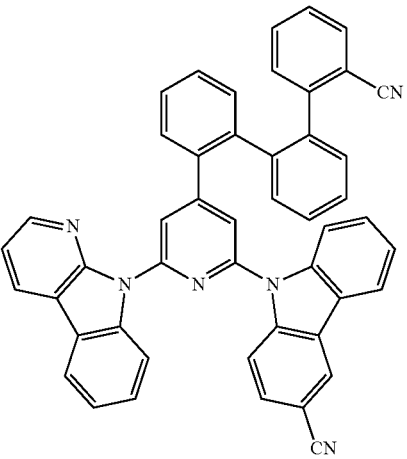
149
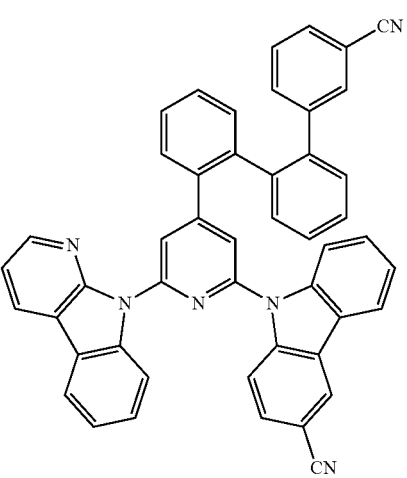
150
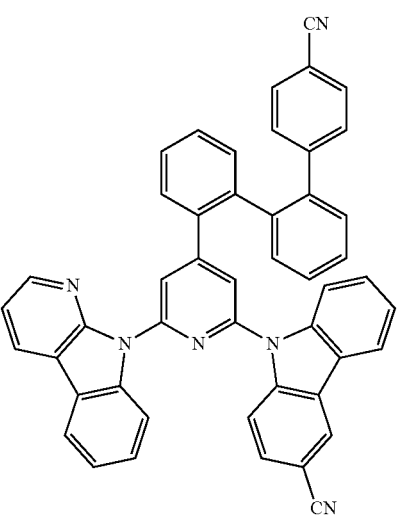

151
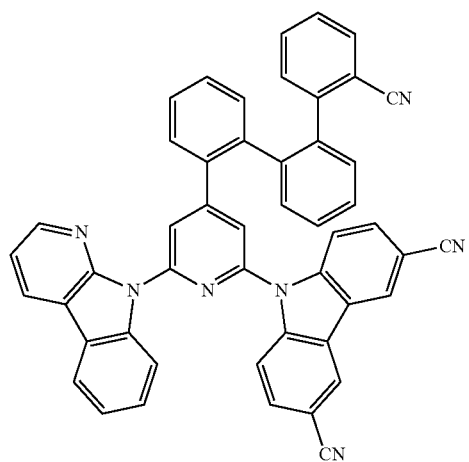
152
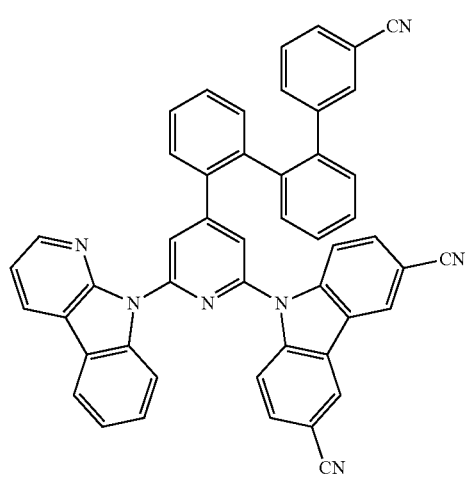
153
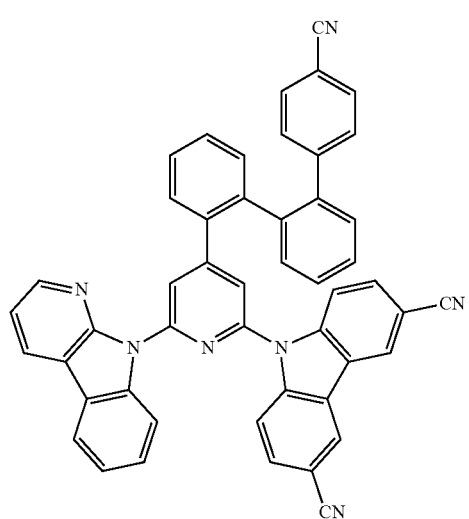
154
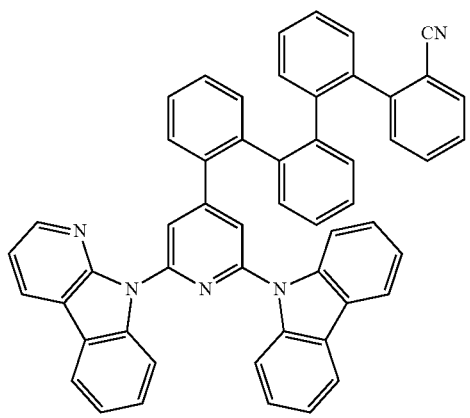
155
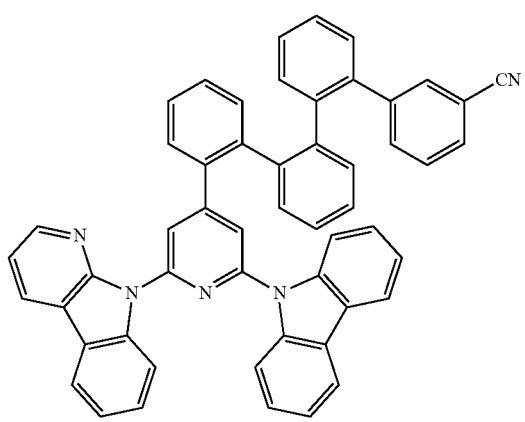
156
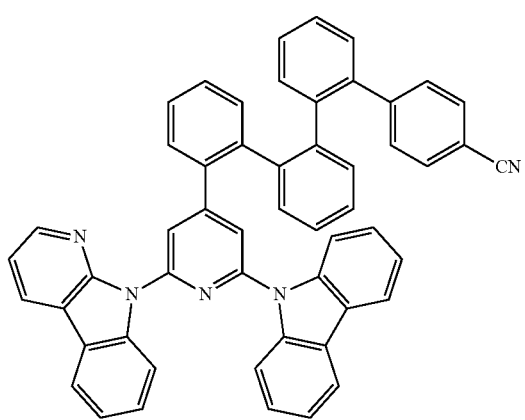

549
-continued
157
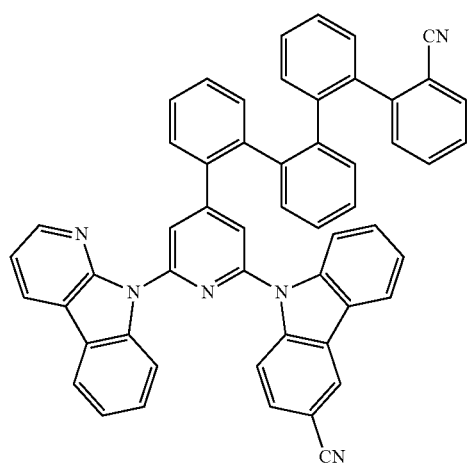
158
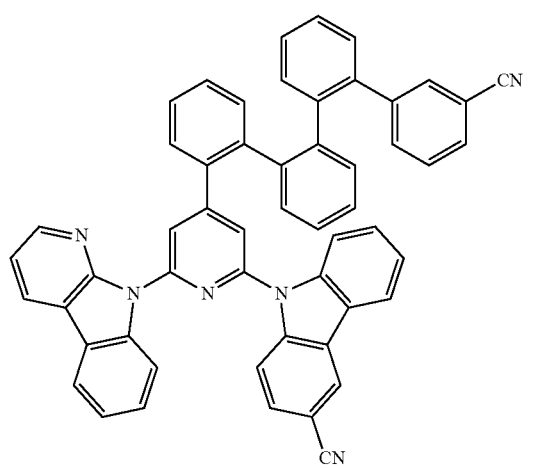
159
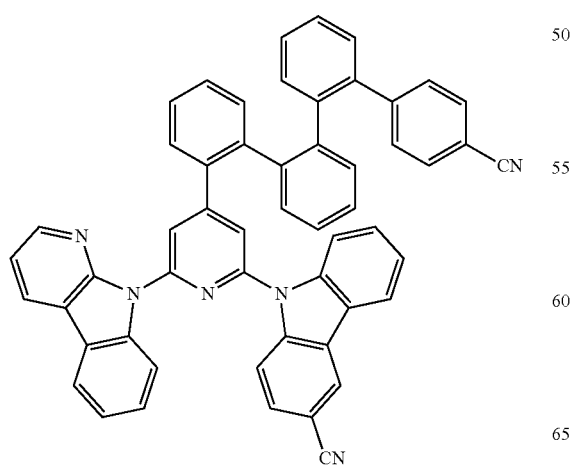
550
-continued
160
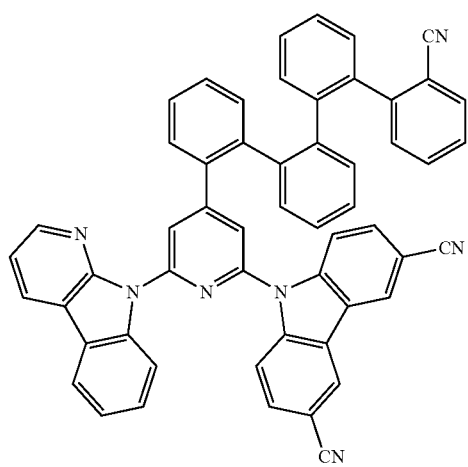
161
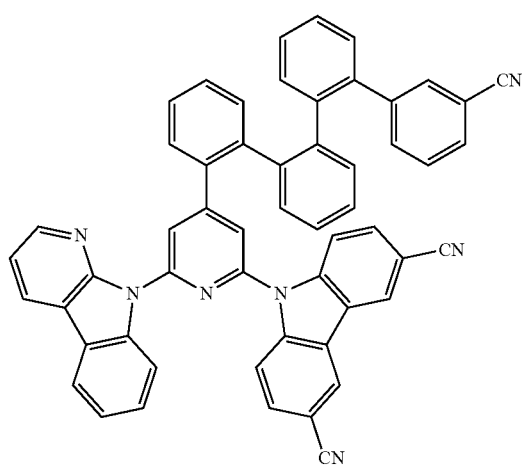
162
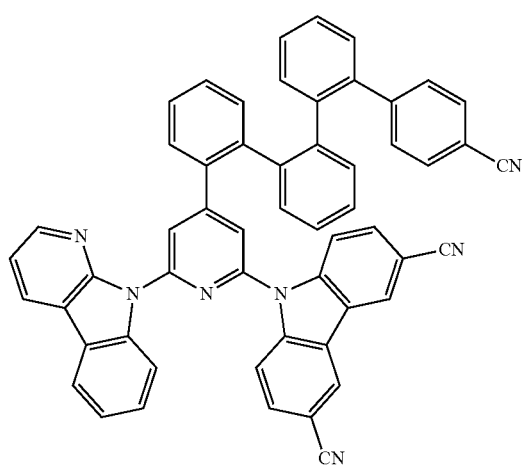

-continued
163
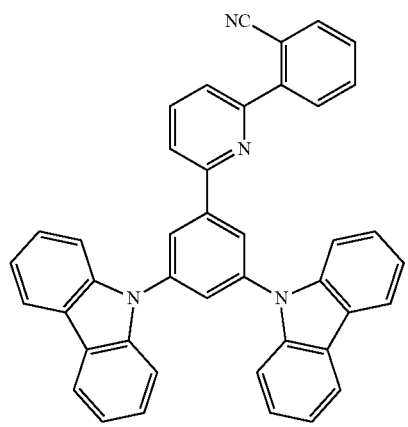
164
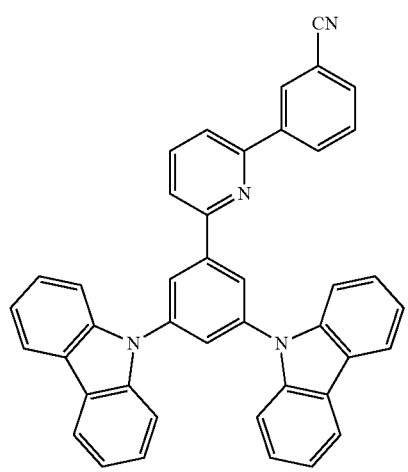
165
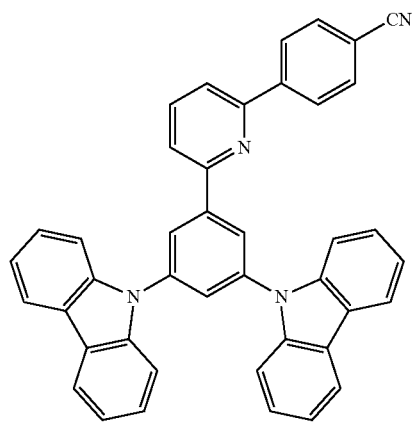
-continued
166
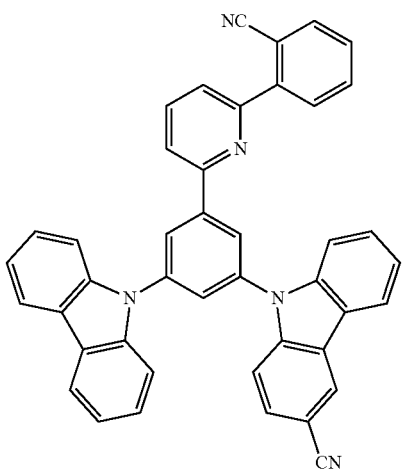
167
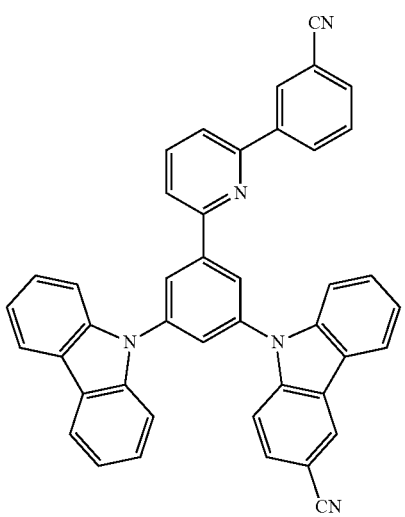
168
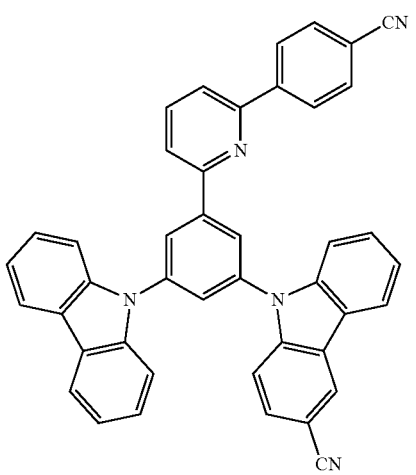

553
-continued
169
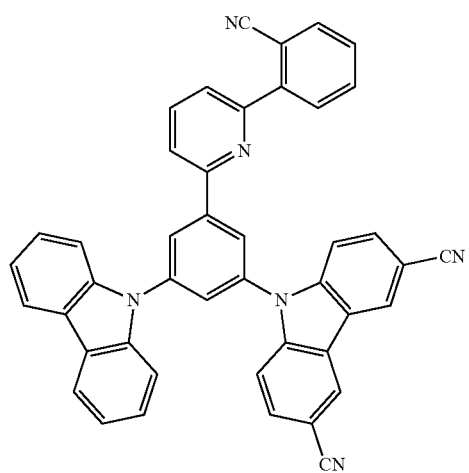
170
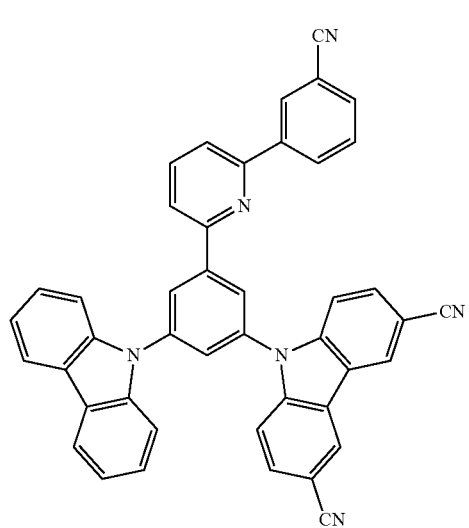
171
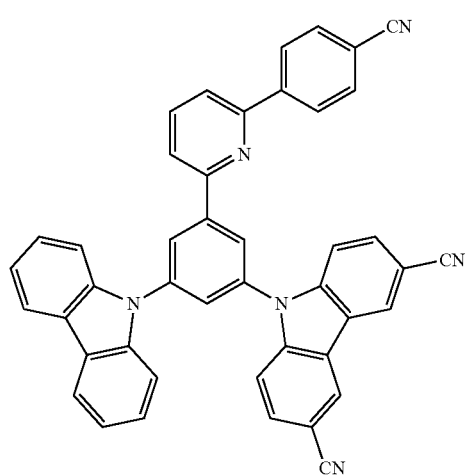
554
-continued
172
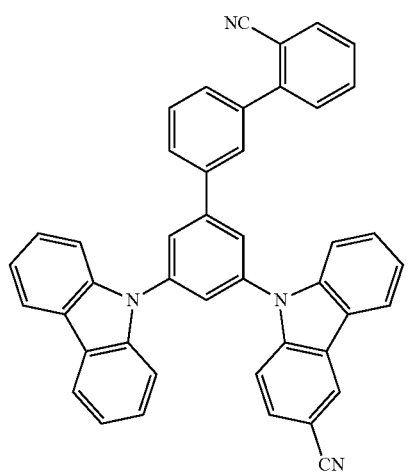
173
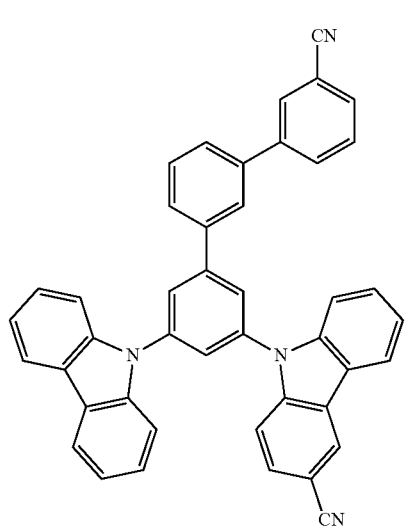
174
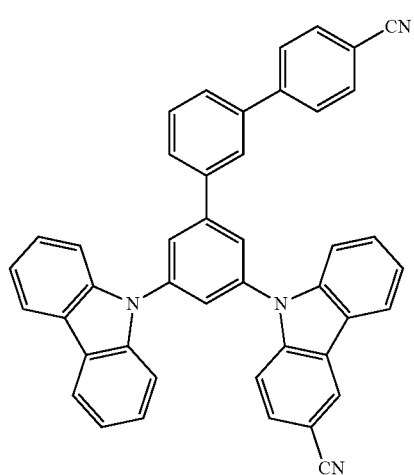

175
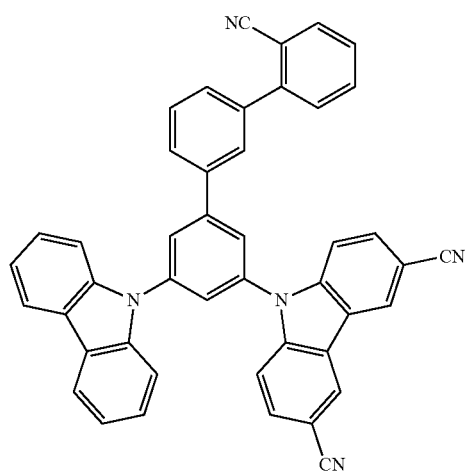
176
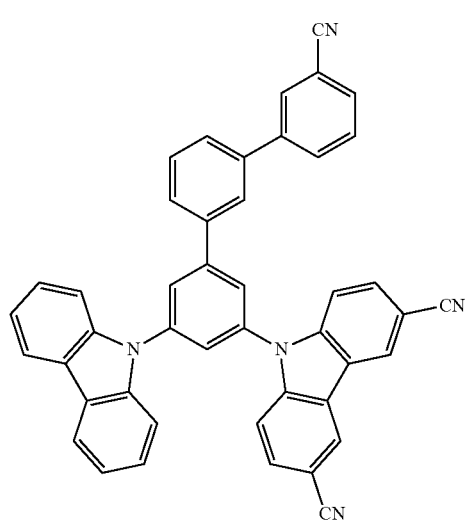
177
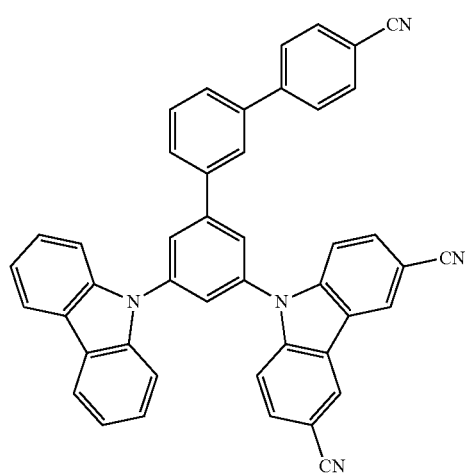
178
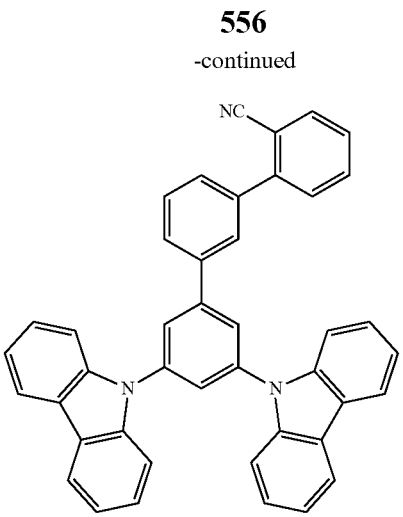
179
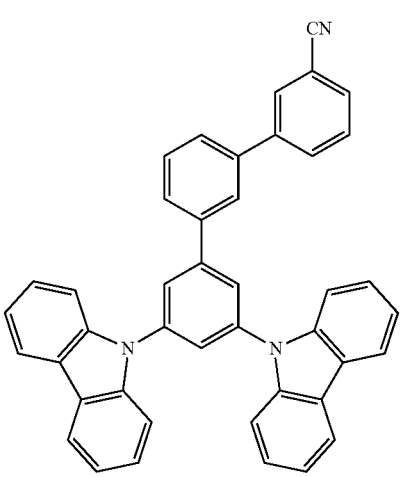
180

181 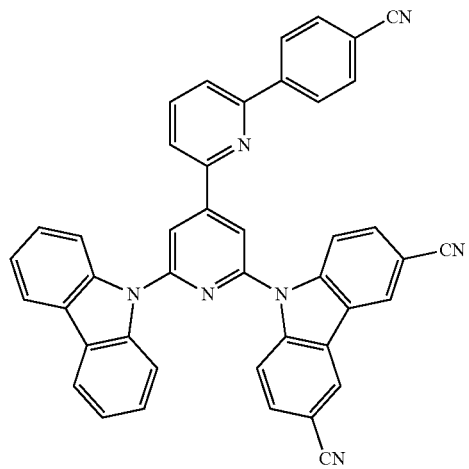
184 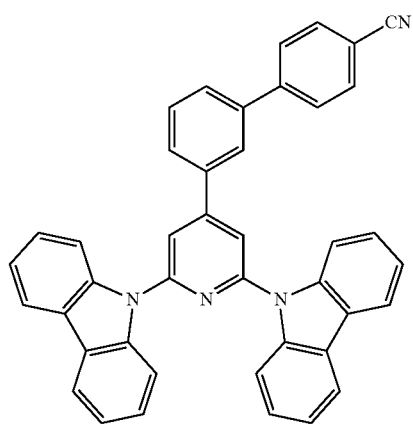
182 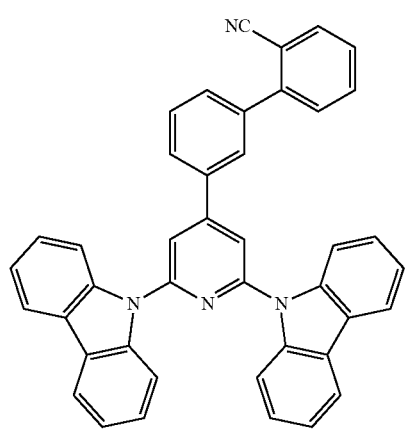
185 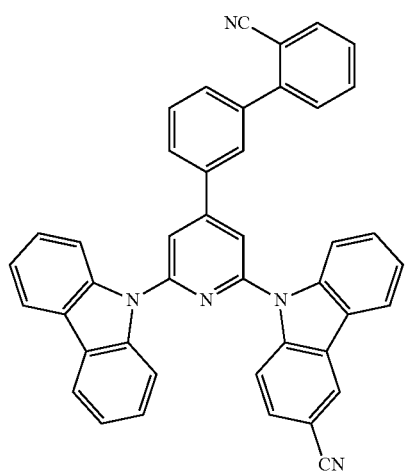
183 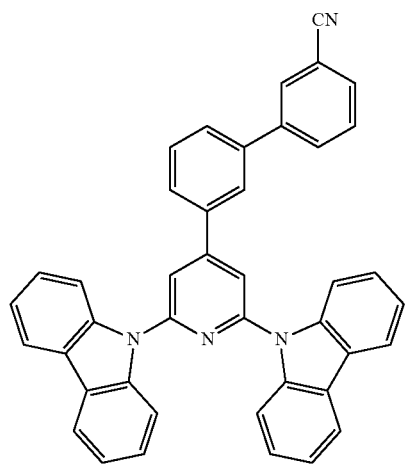
186 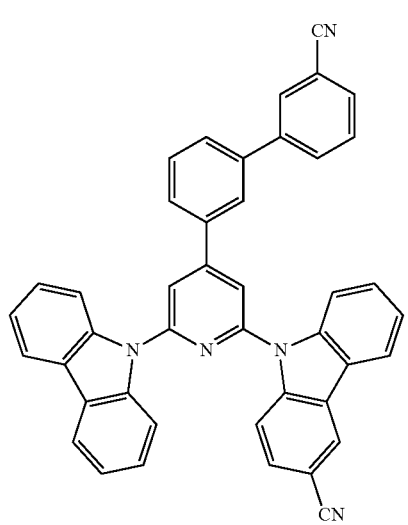

559
-continued
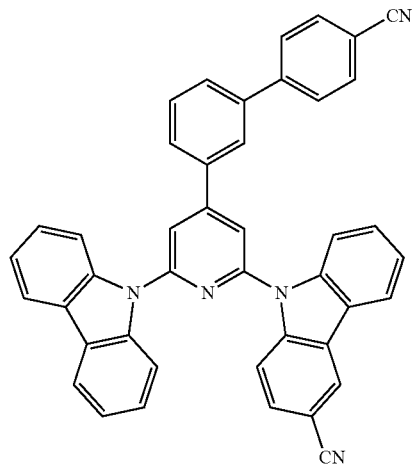187
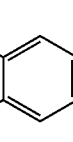188
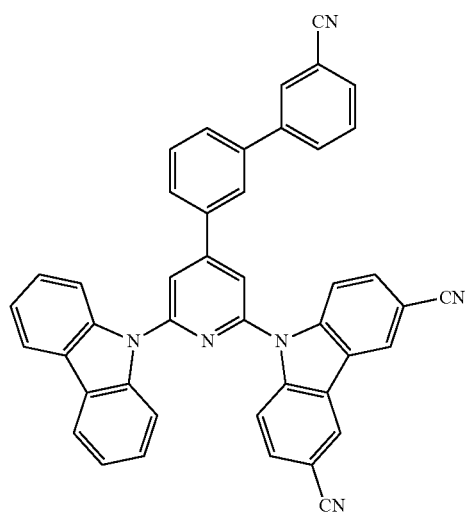189
560
-continued
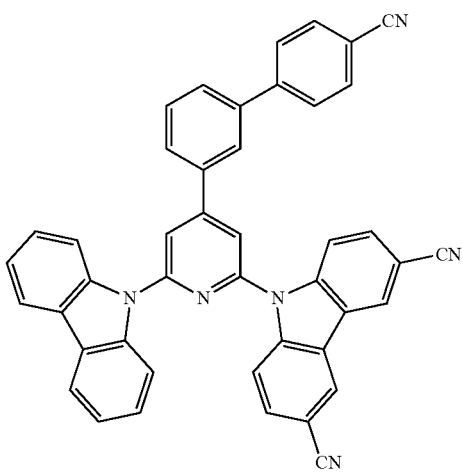190
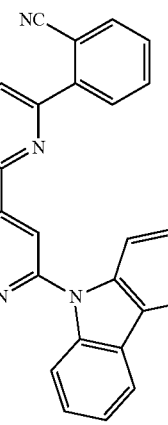191
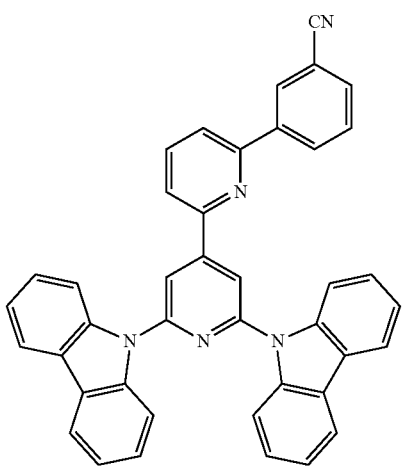192

-continued
193
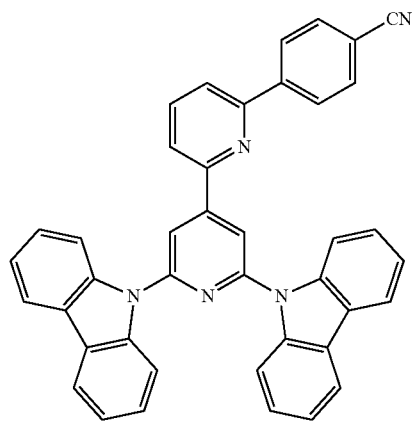
194
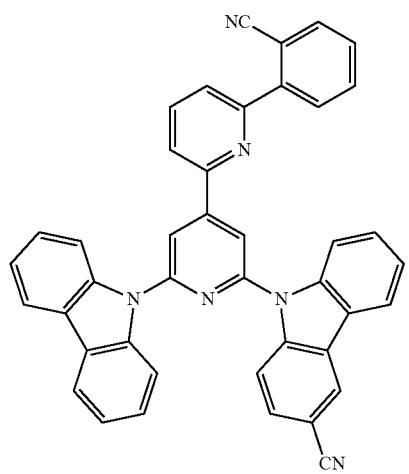
195
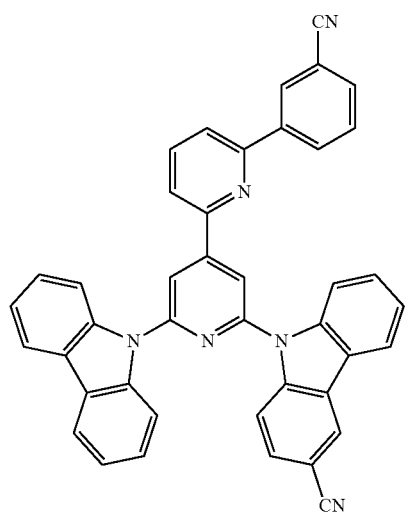
-continued
196
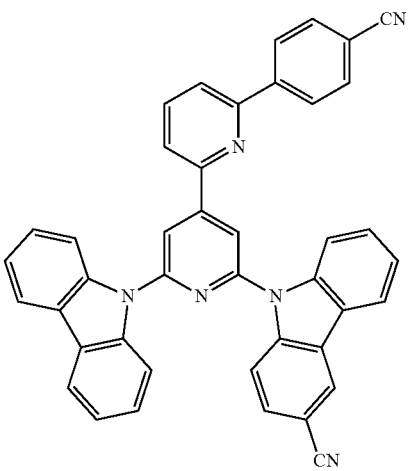
197
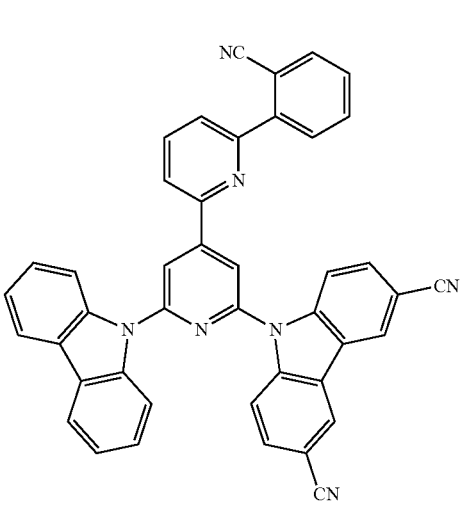
198
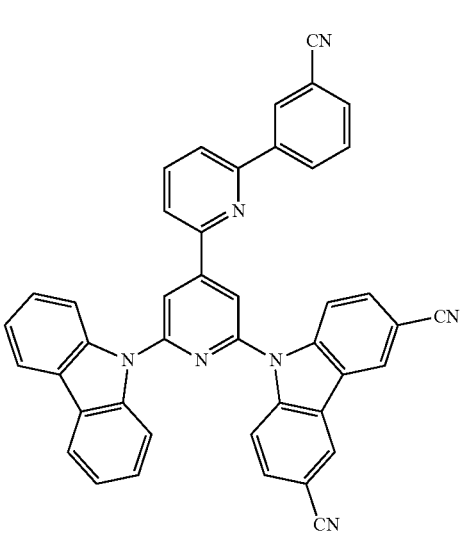

<Group HE6>
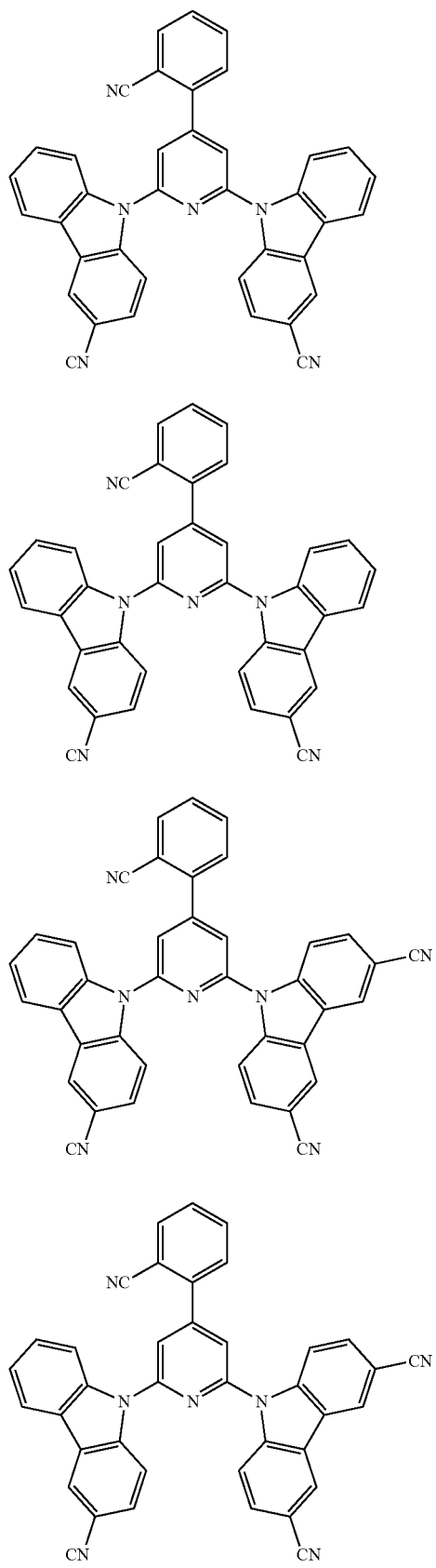
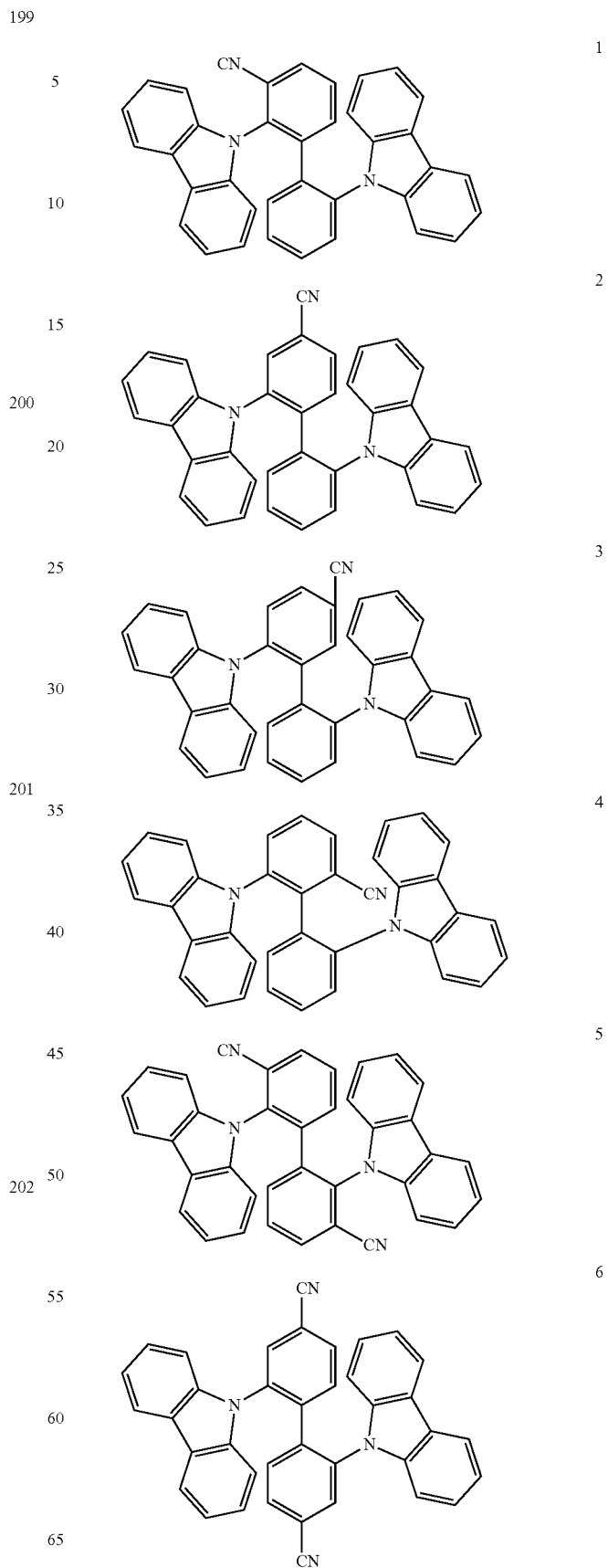

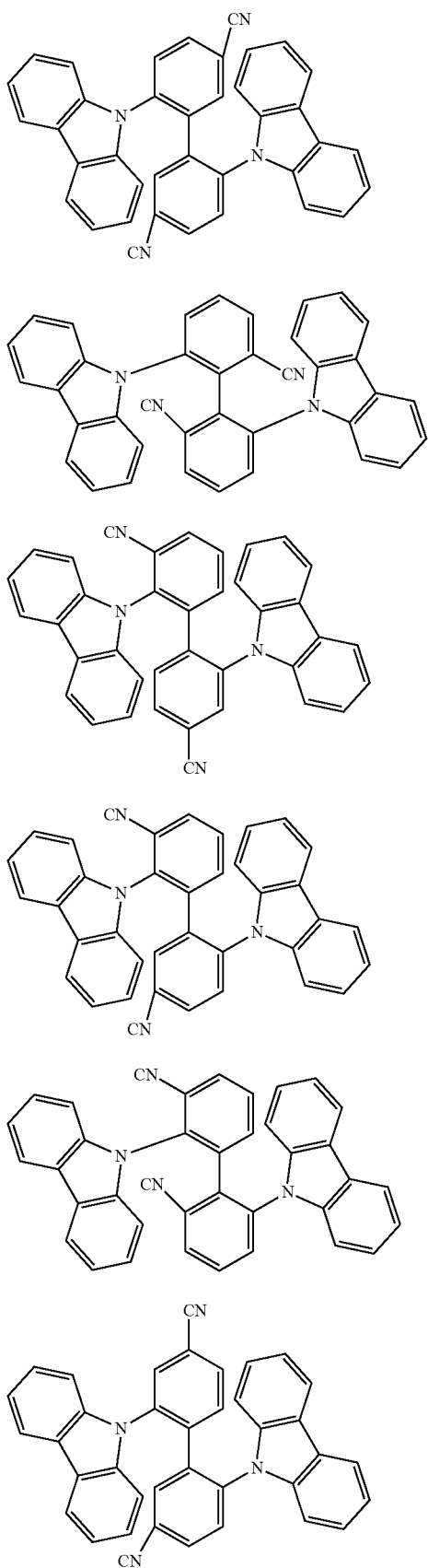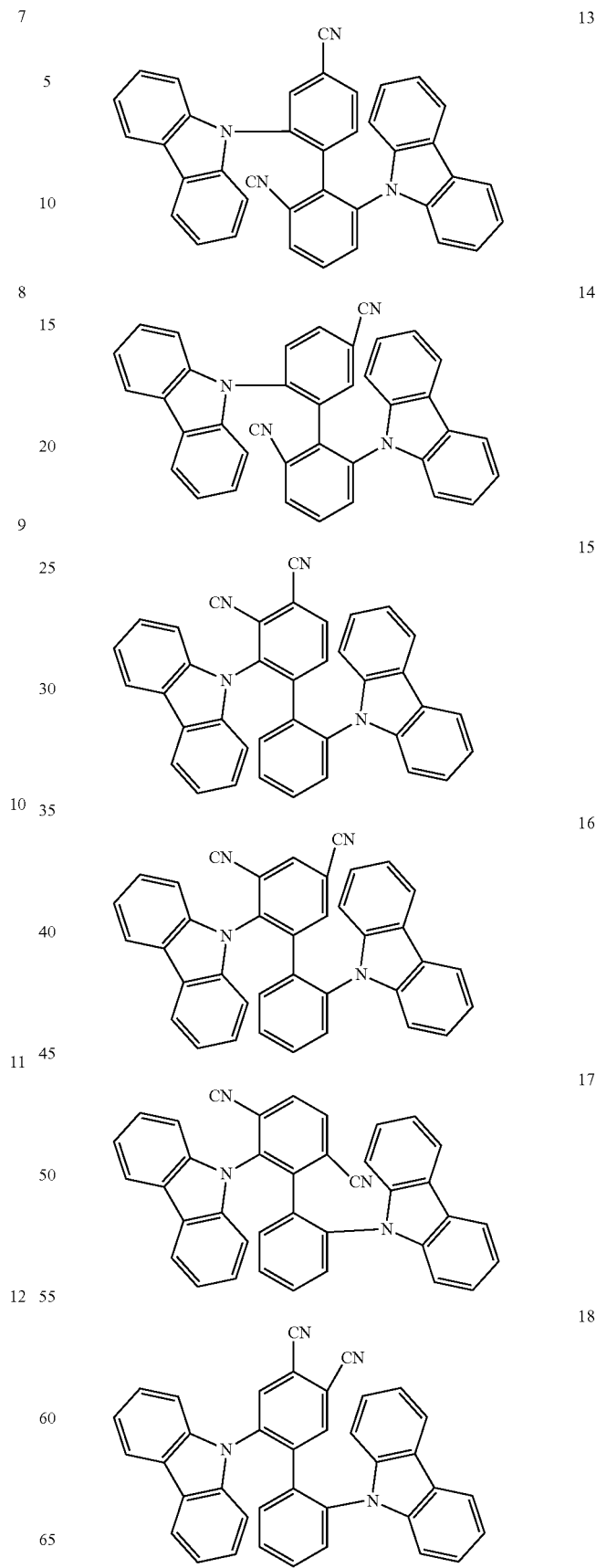

-continued
19
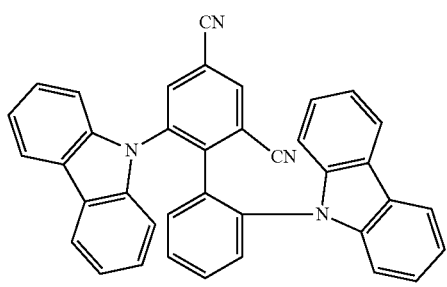
20
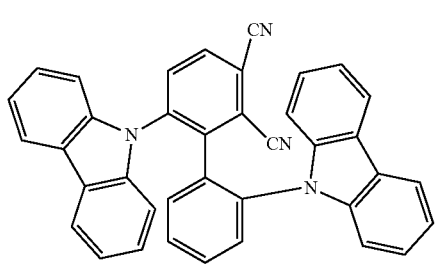
21
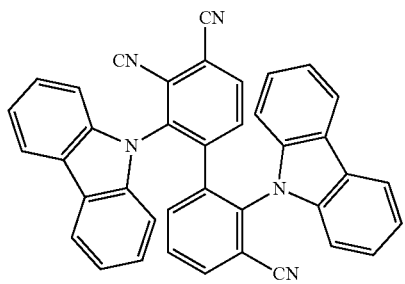
22
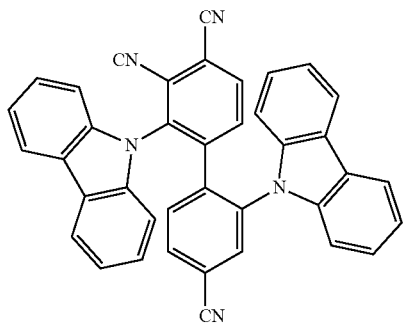
23
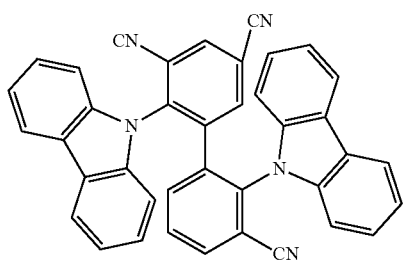
-continued
24
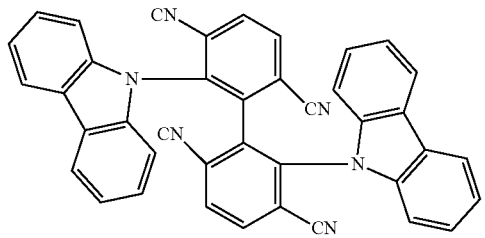
25

26
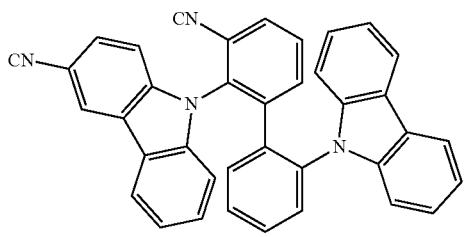
27
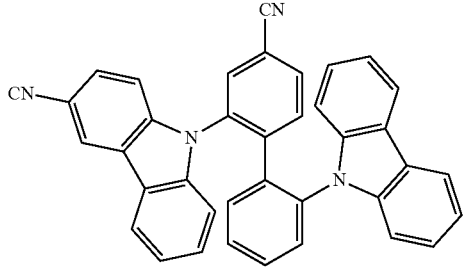
28
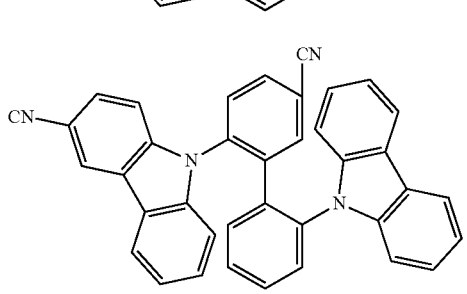
29
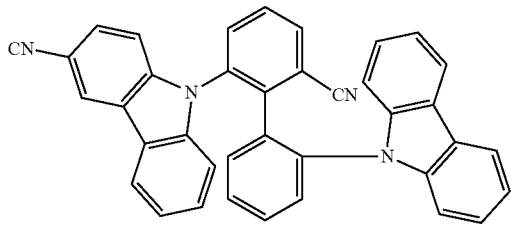

569
-continued
30
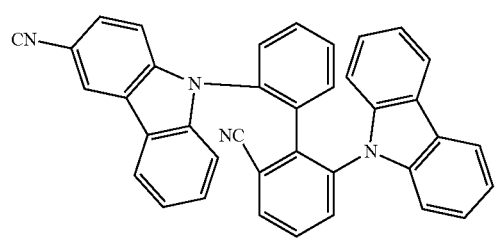
31
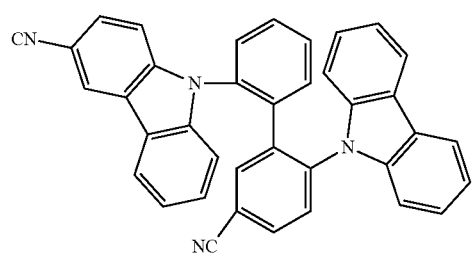
32
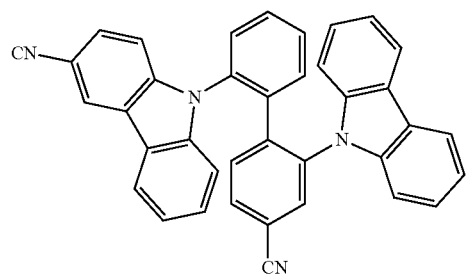
33
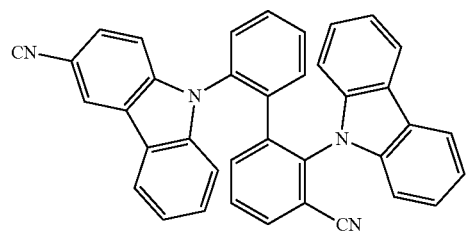
34
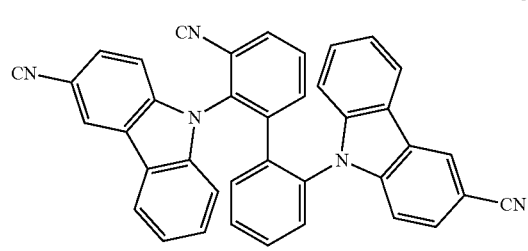
35
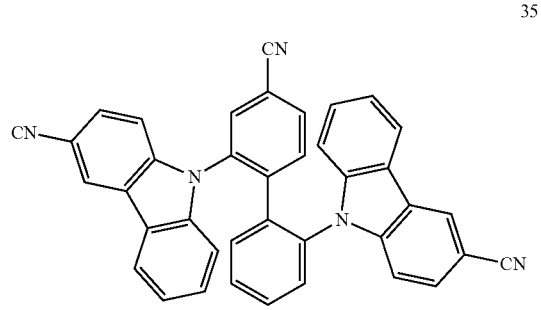
570
-continued
36
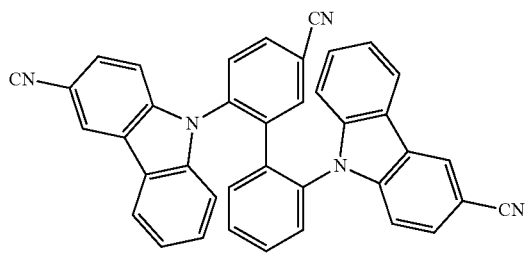
37
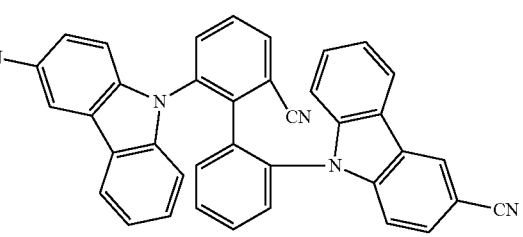
38
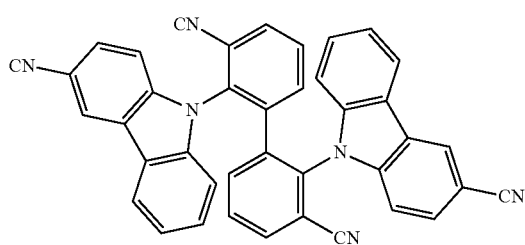
39
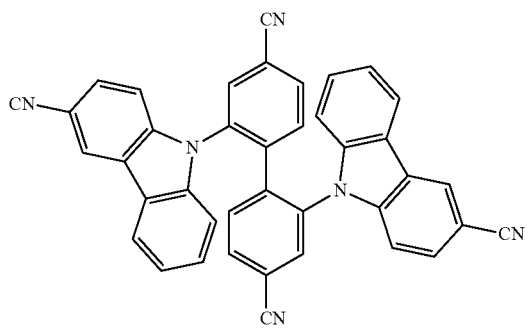
40
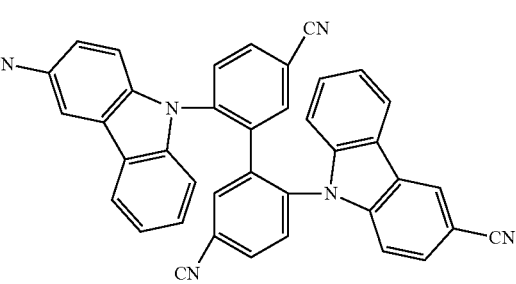

-continued
41
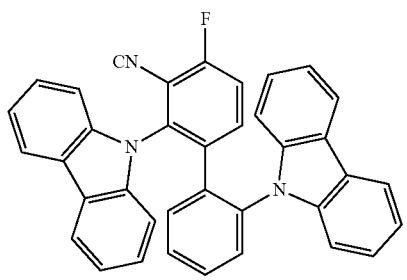
42
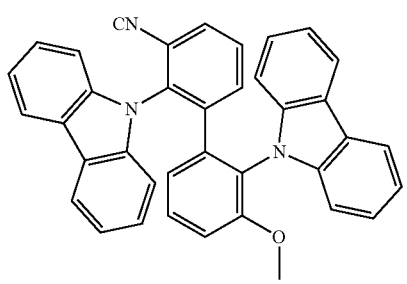
43
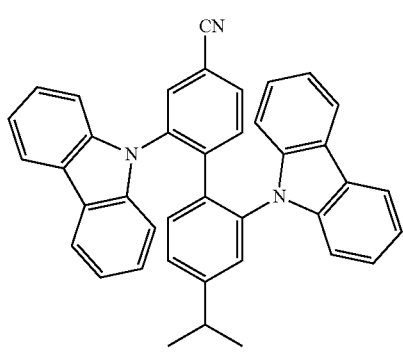
44
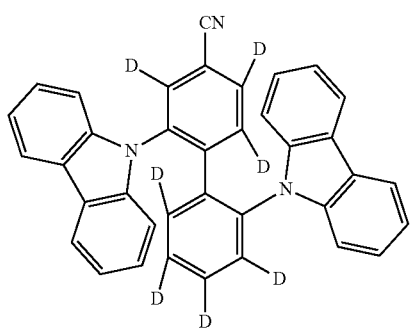
45
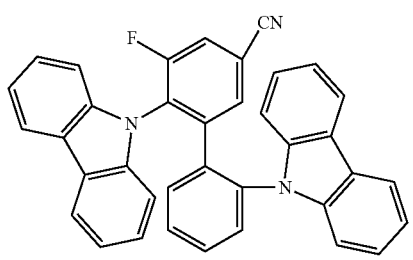
-continued
46
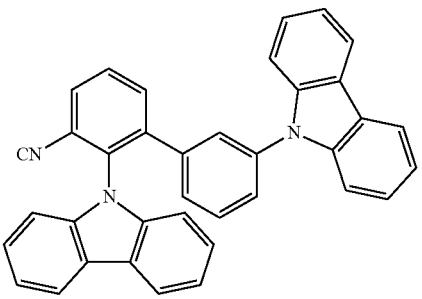
47
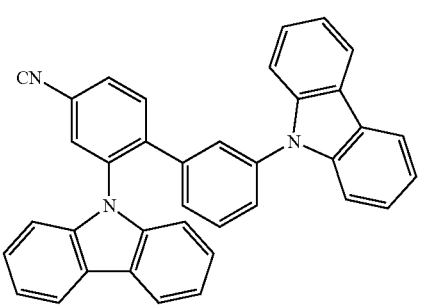
48
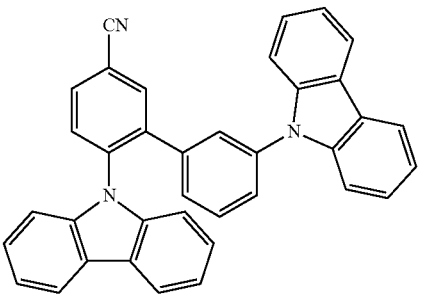
49
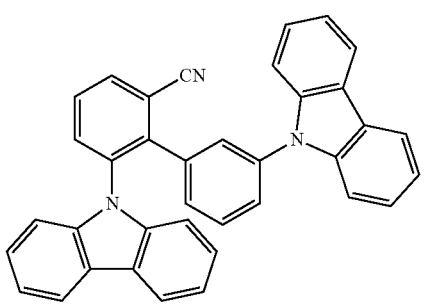
50
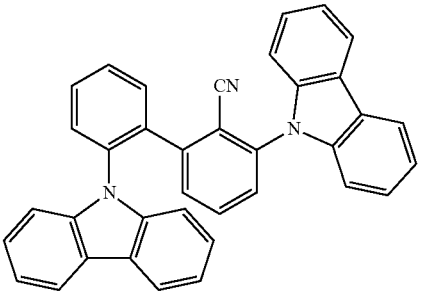

51
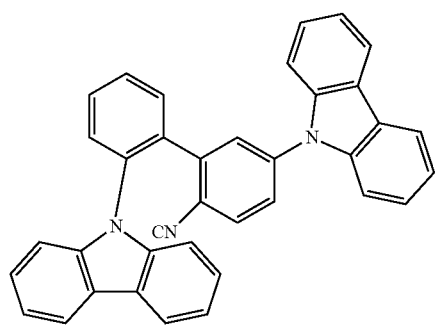
52
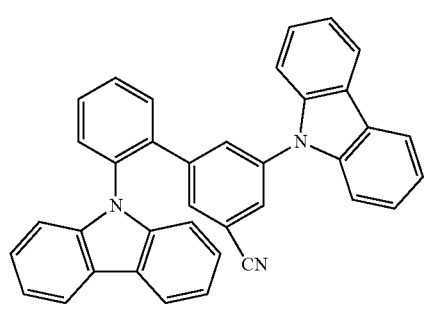
53
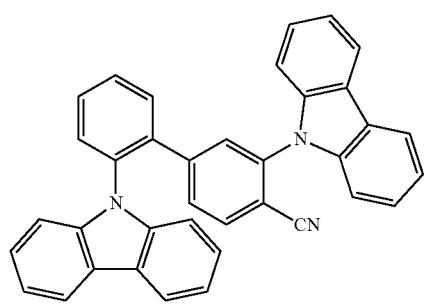
54
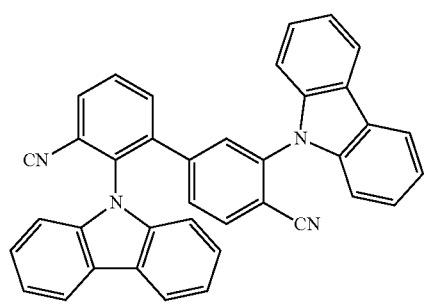
55
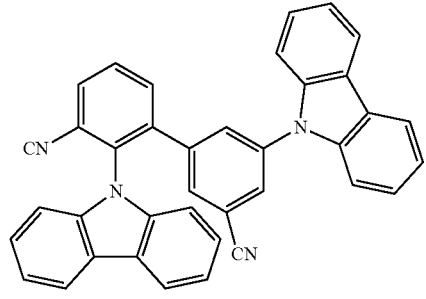
56
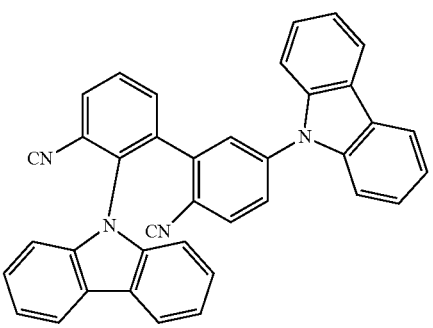
57
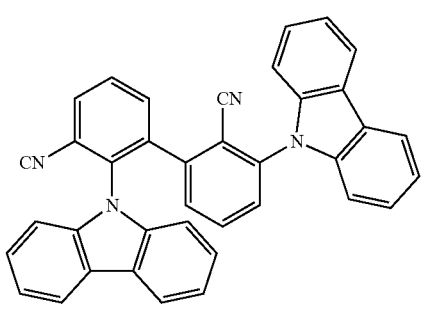
58
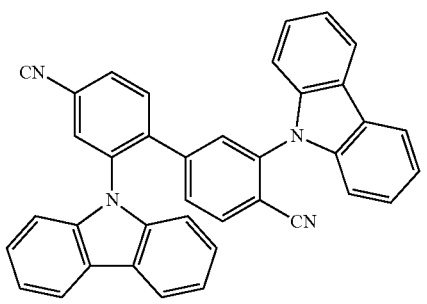
59
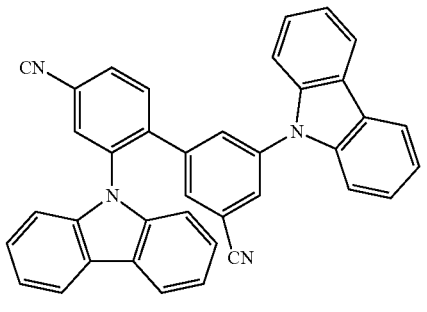
60
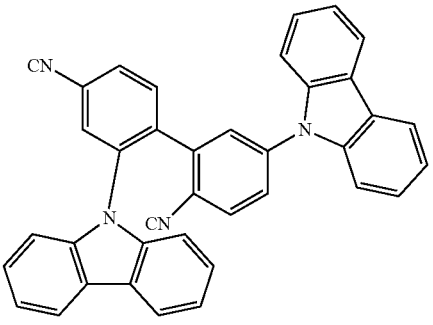

| 61 | 66 |
|---|---|
| 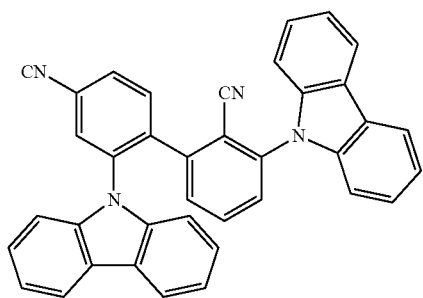 | 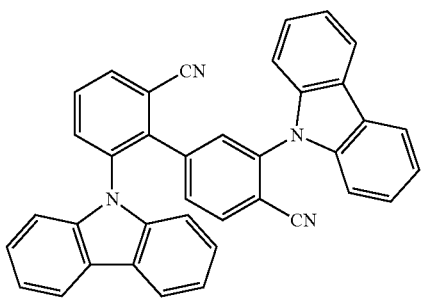 |
| 62 | 67 |
| 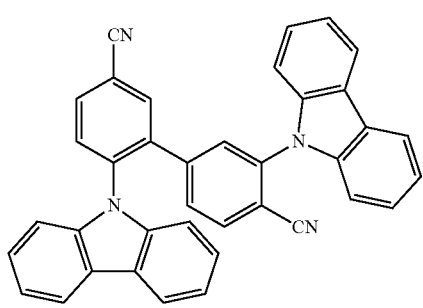 | 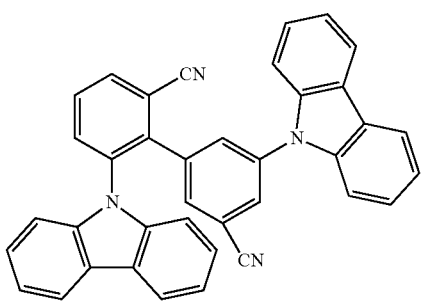 |
| 63 | 68 |
| 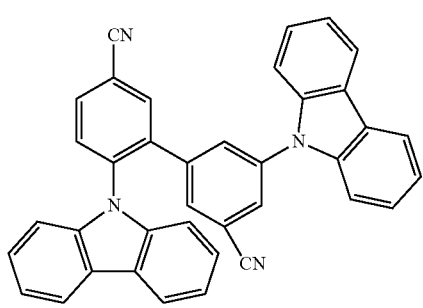 | 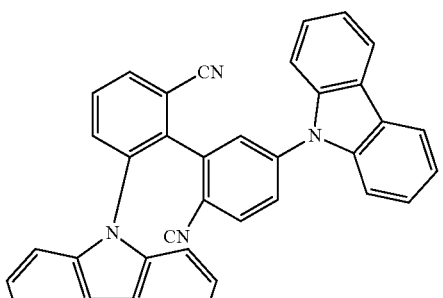 |
| 64 | 69 |
| 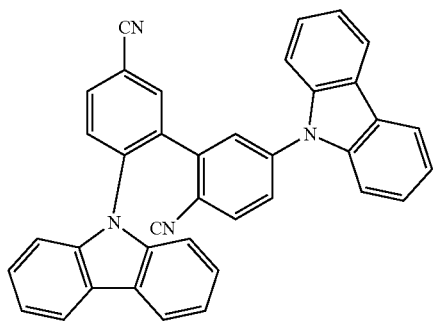 | 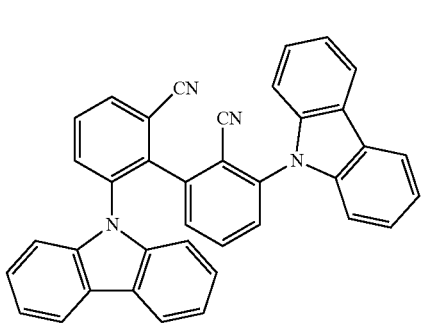 |
| 65 | 70 |
| 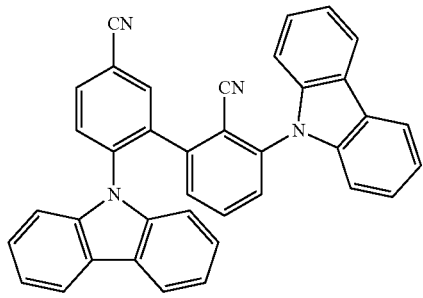 | 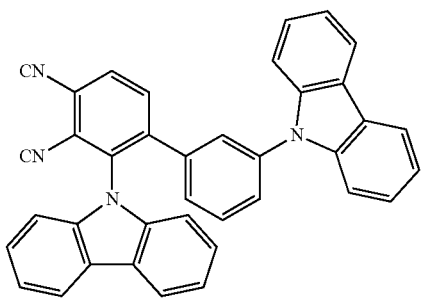 |

-continued
71
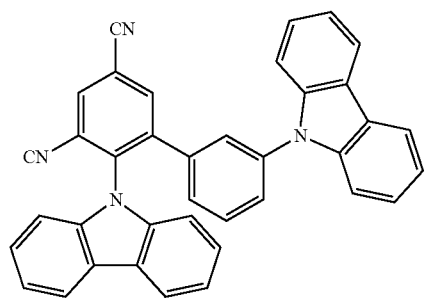
72
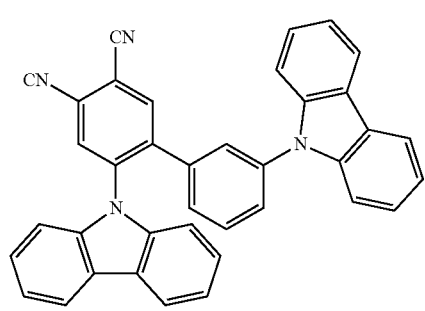
73
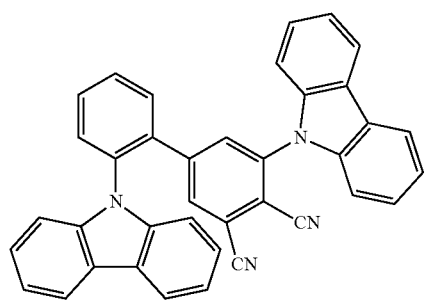
74
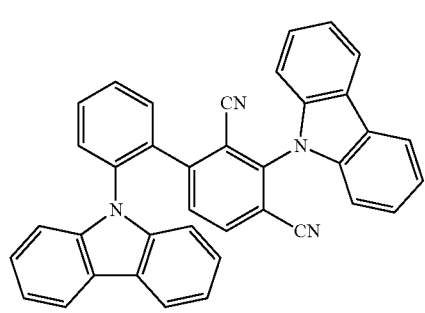
75
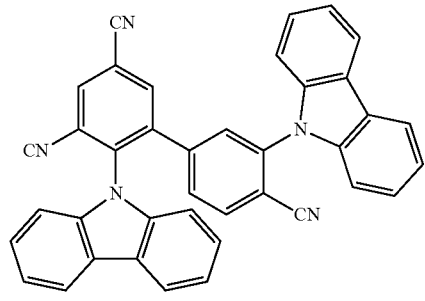
-continued
76
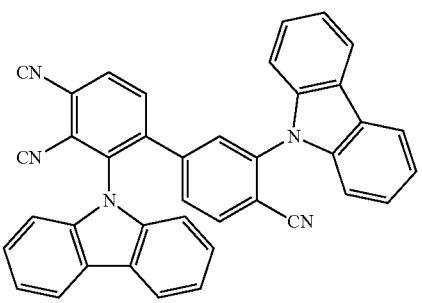
77
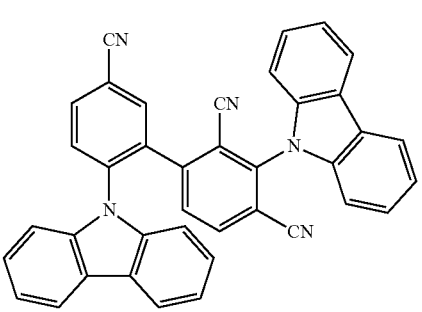
78
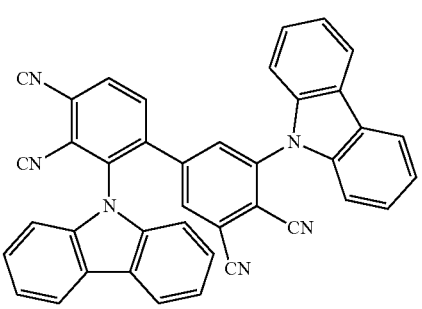
79
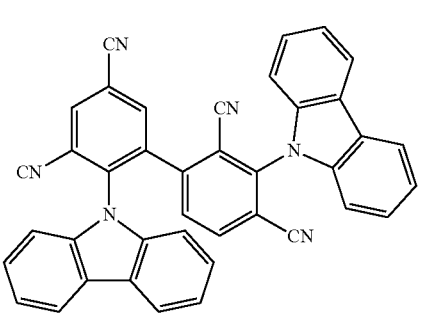
80
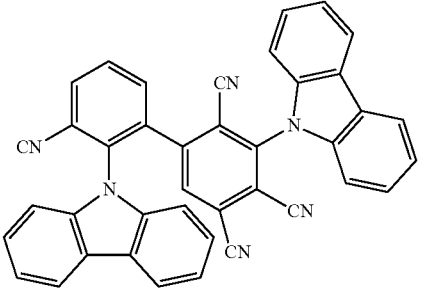

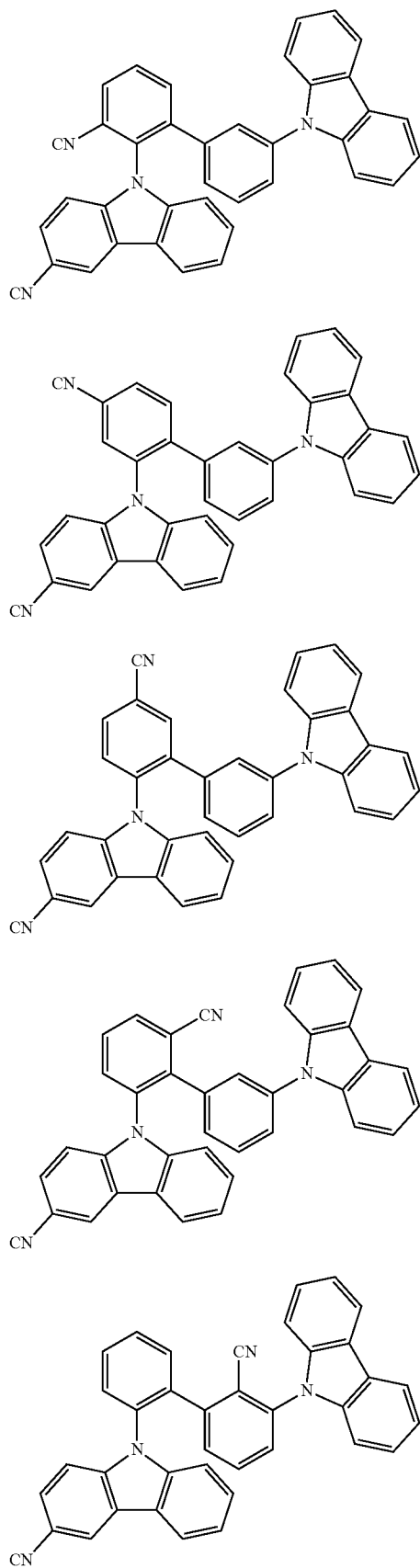
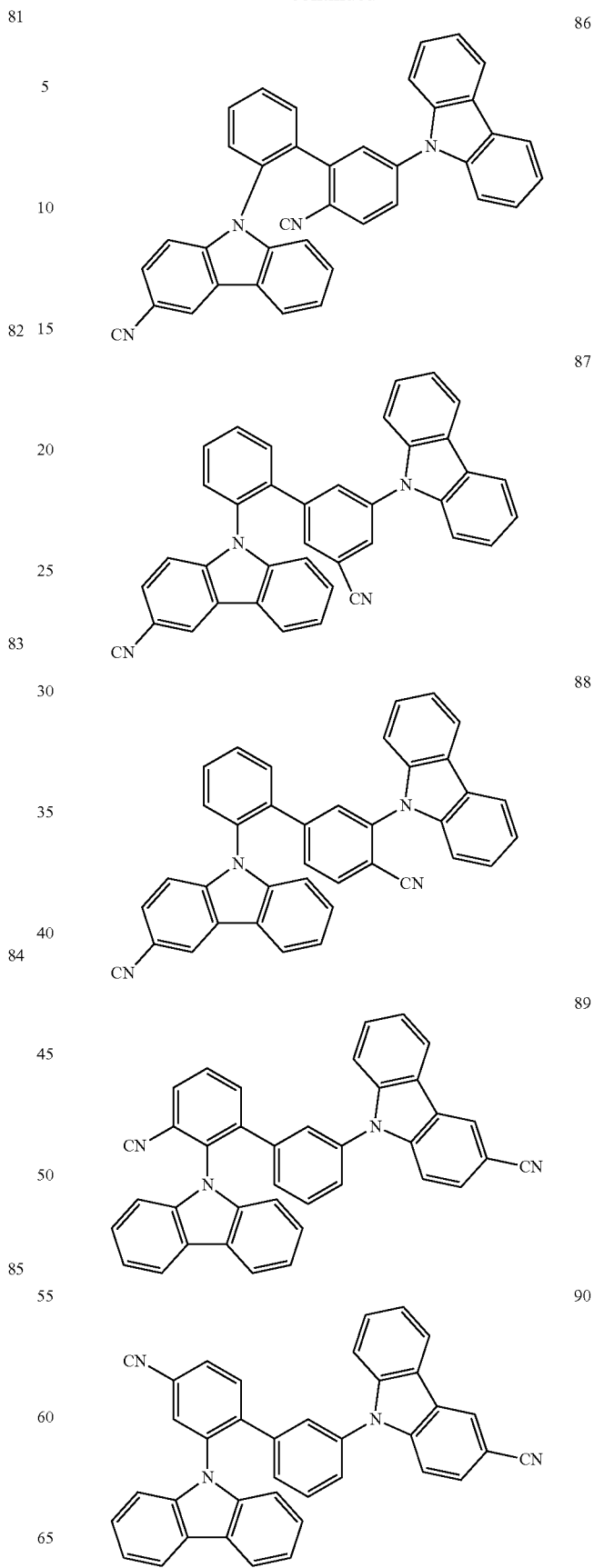

-continued
91
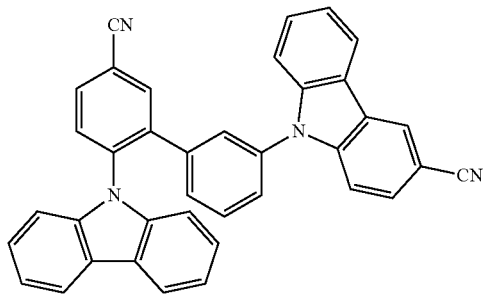
92
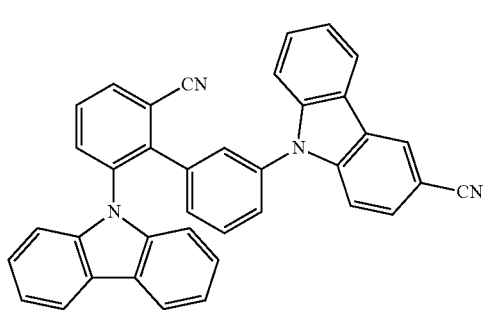
93
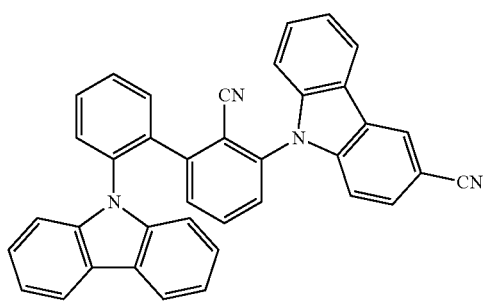
94
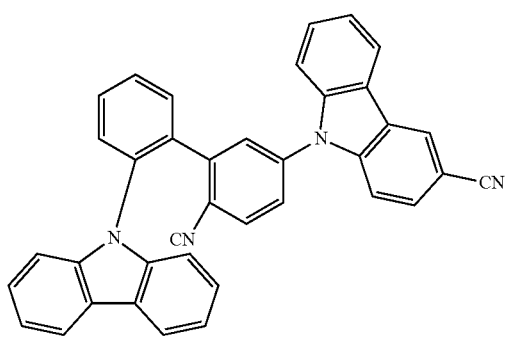
95
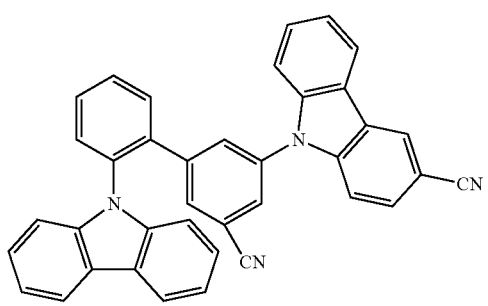
-continued
96
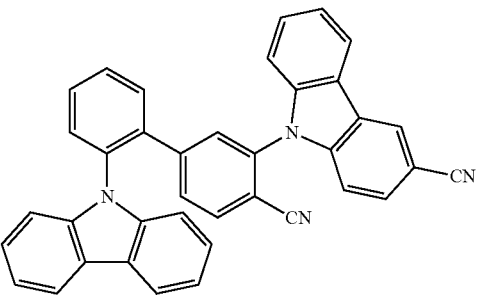
97
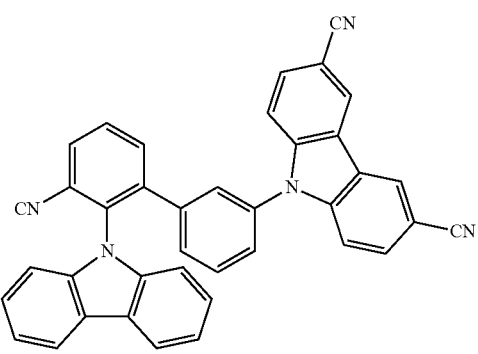
98
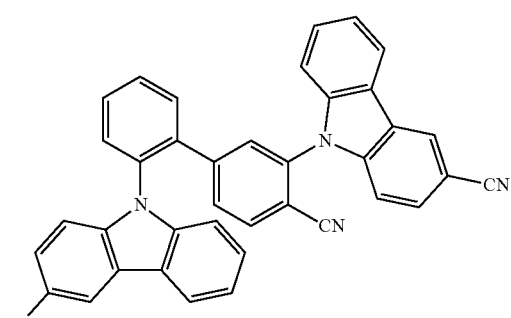
99
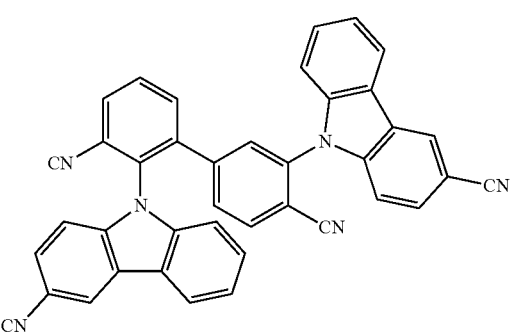

100 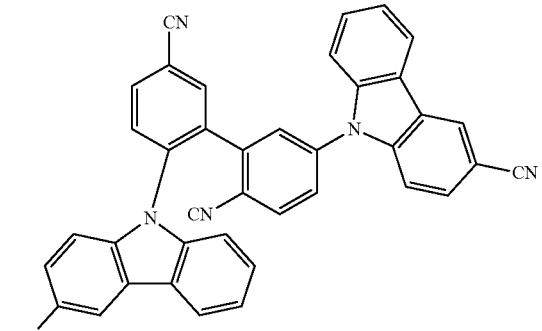
101 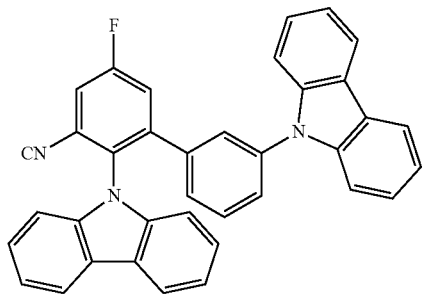
102 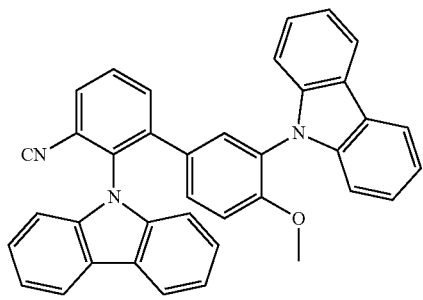
103 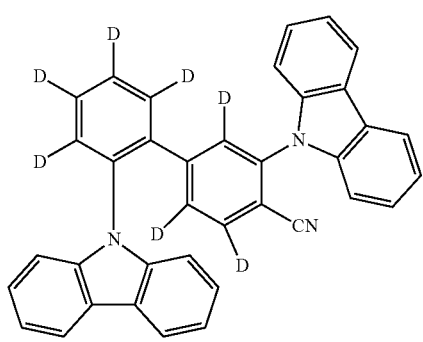
104 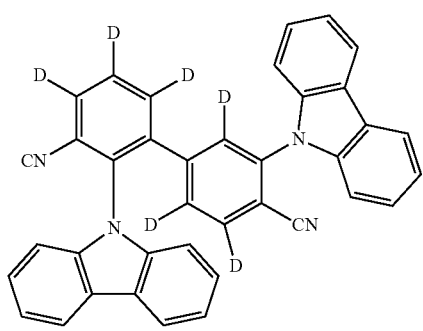
105 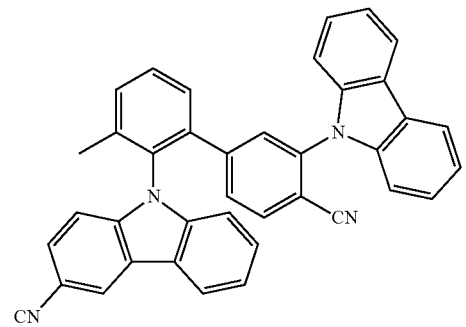
106 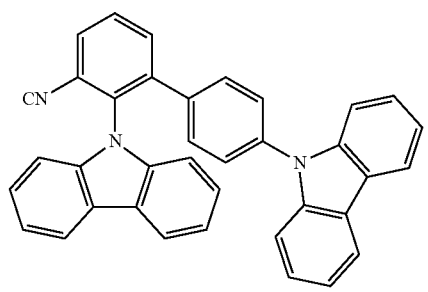
107 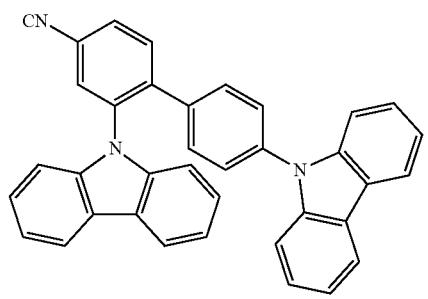
108 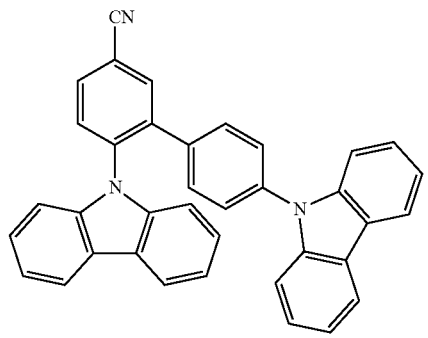
109 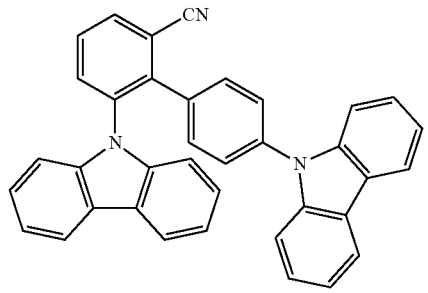

110
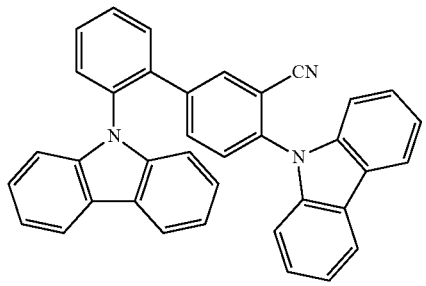
111
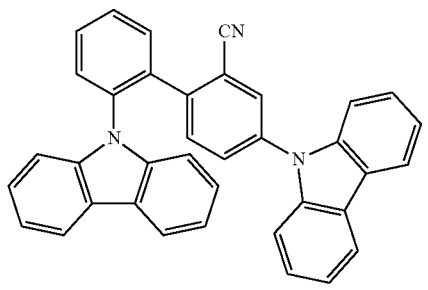
112
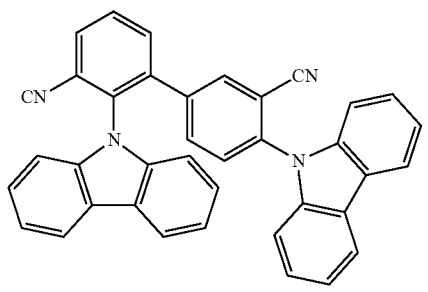
113
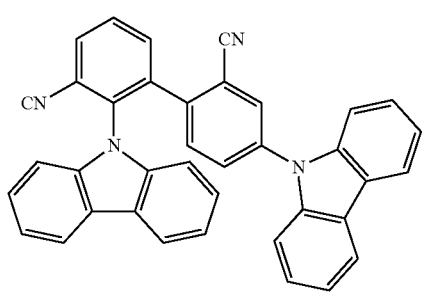
114
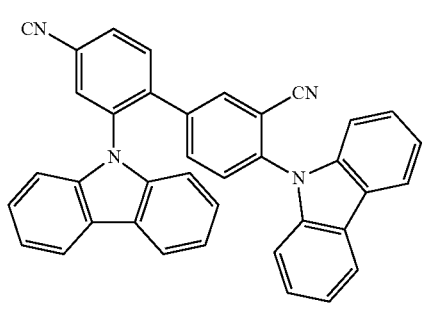
115
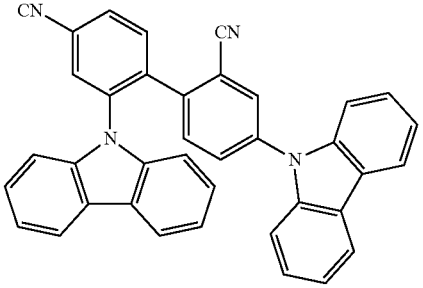
116
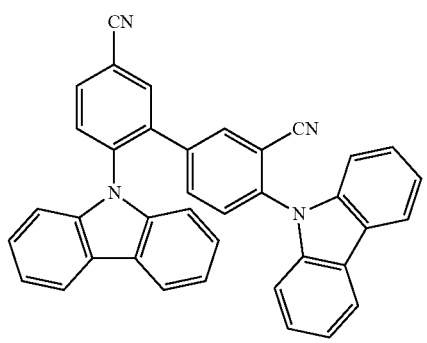
117
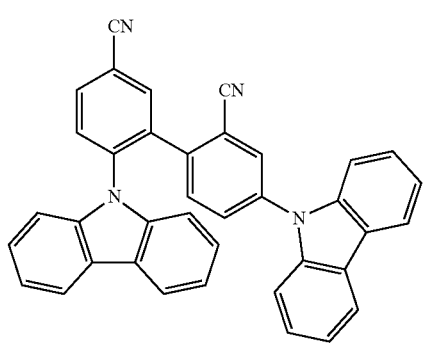
118
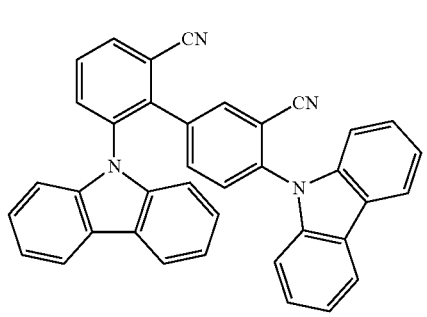
119
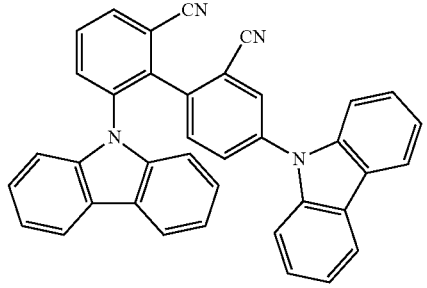

120
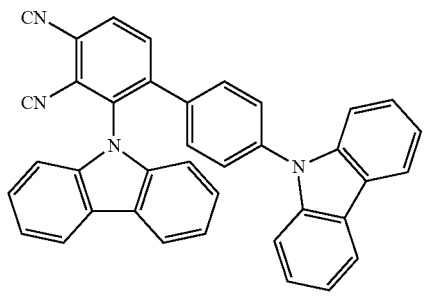
121
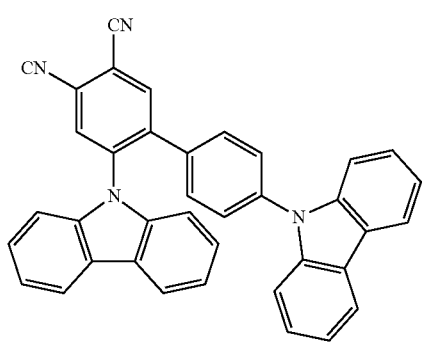
122
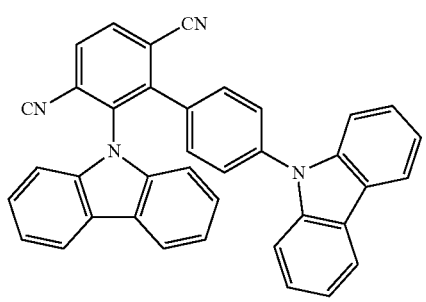
123
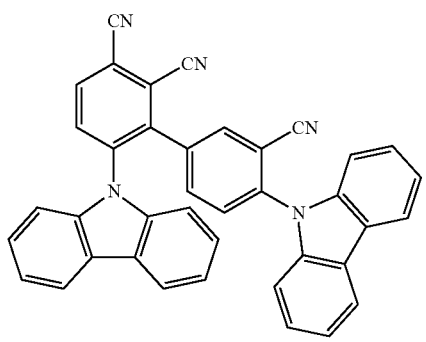
124
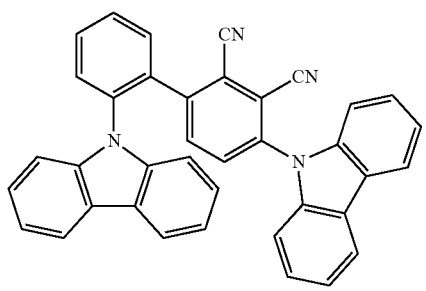
125
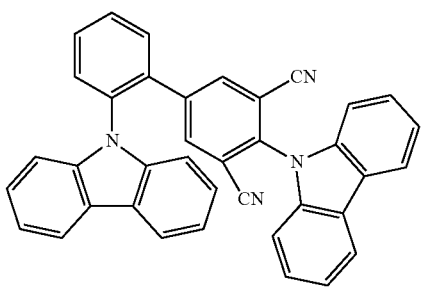
126
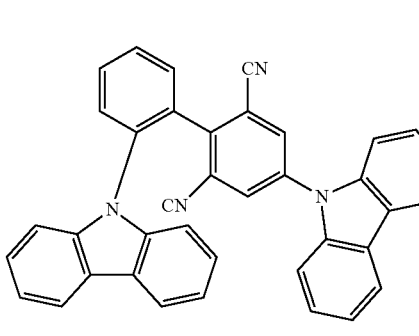
127
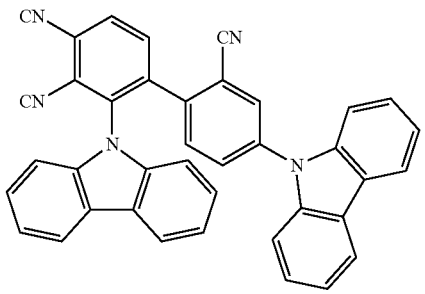
128
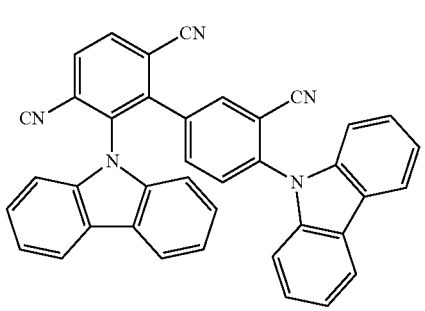
129
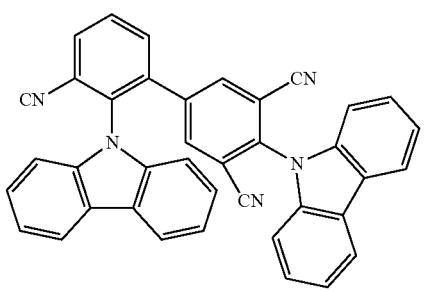

-continued
130
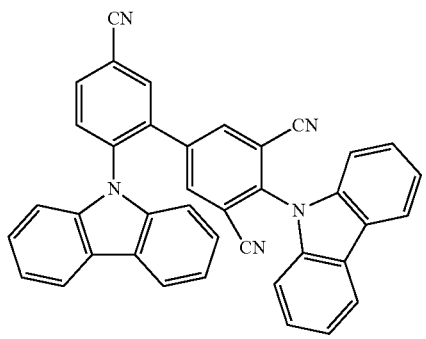
131
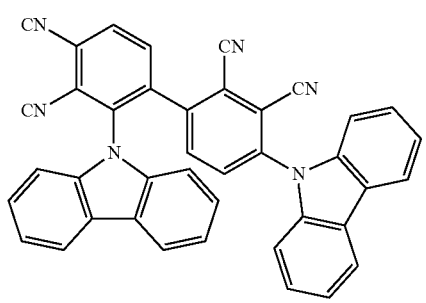
132
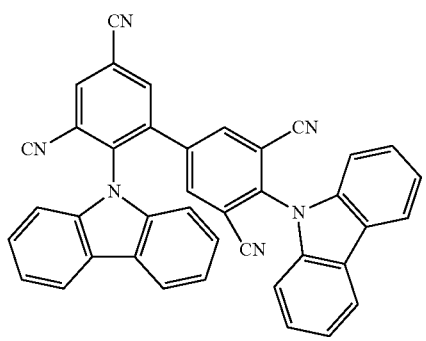
133
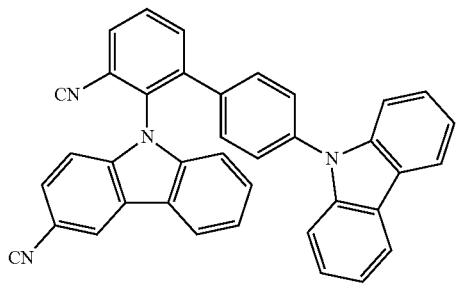
134
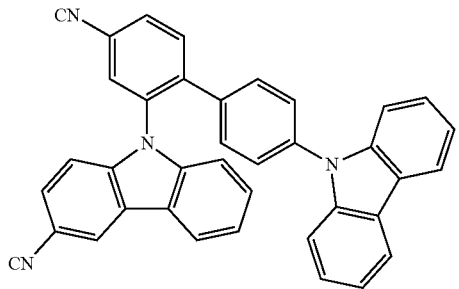
-continued
135
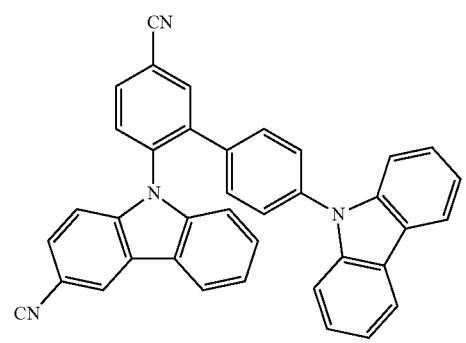
136
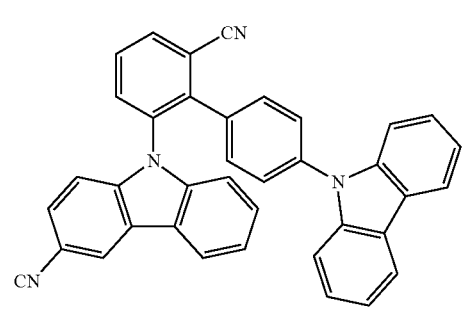
137
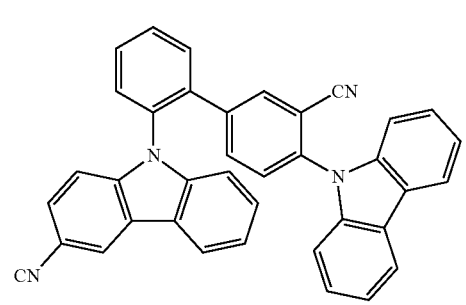
138
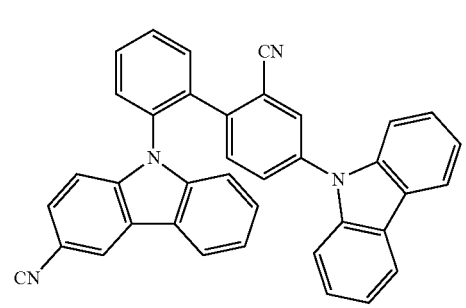
139
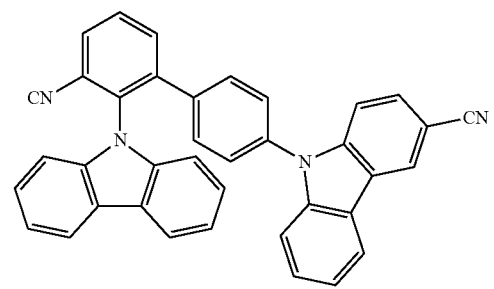

-continued
140
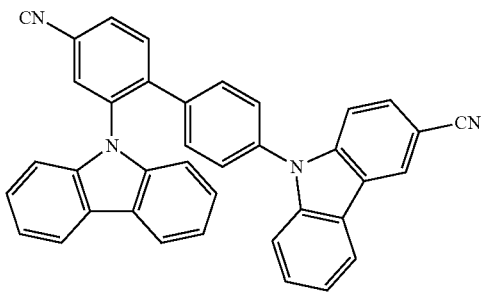
141
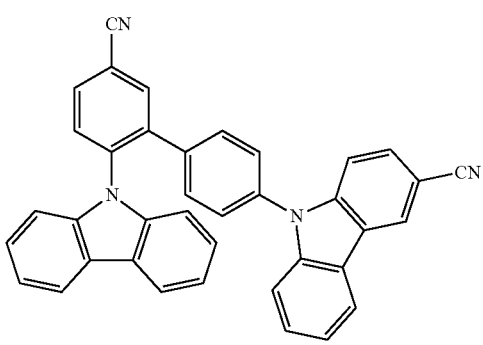
142
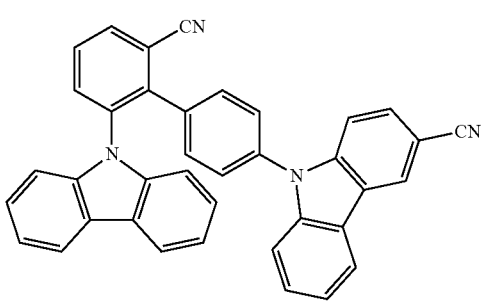
143
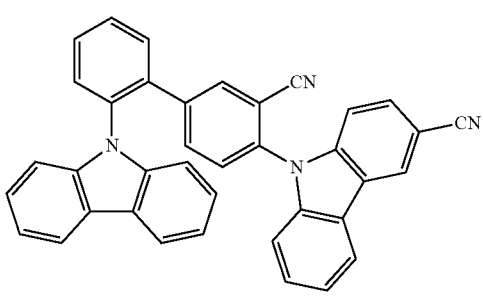
144
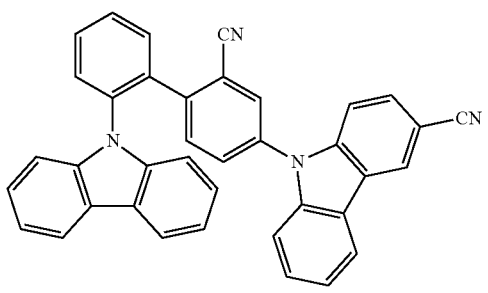
-continued
145
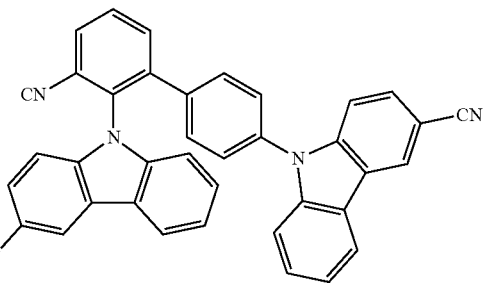
146
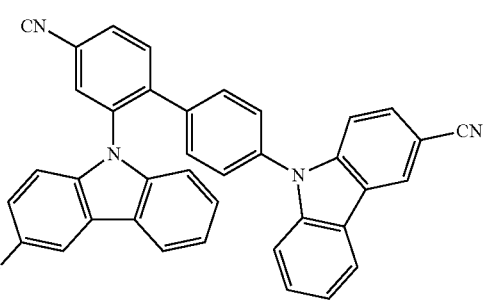
147
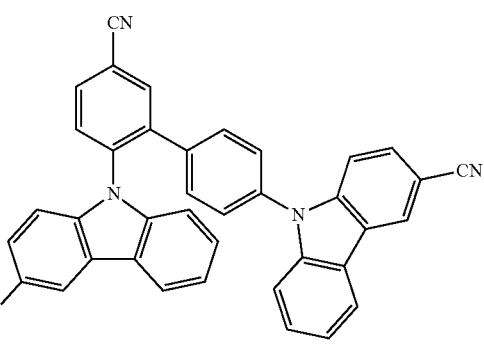
148
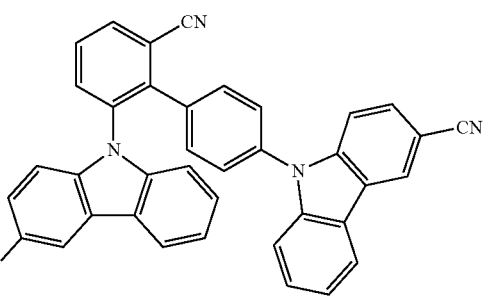
149
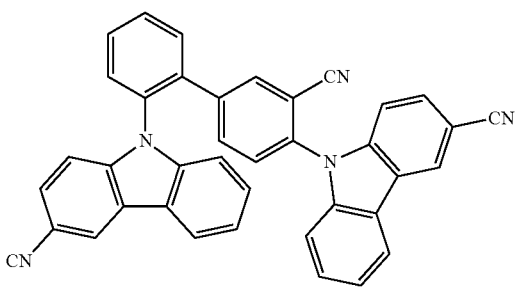

150
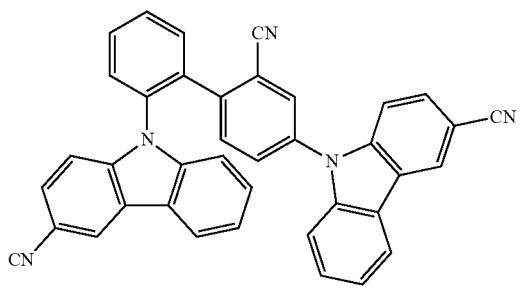
151
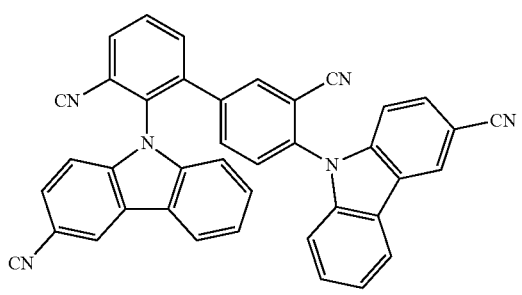
152
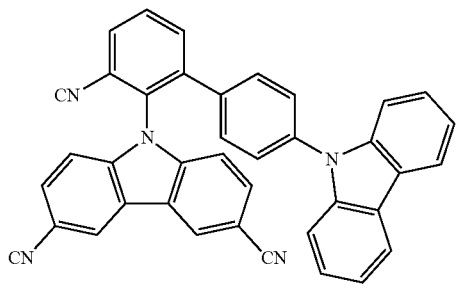
153
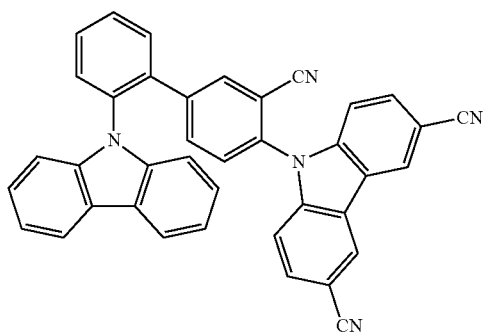
154
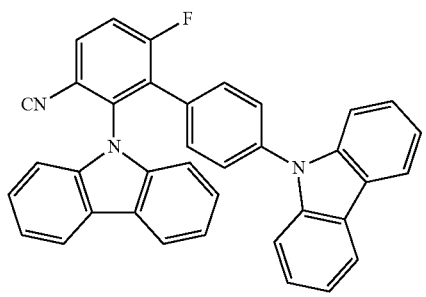
155
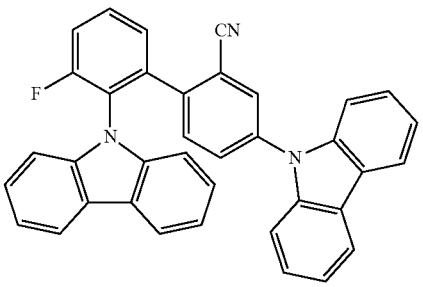
156
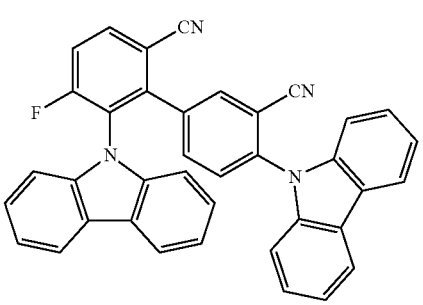
157
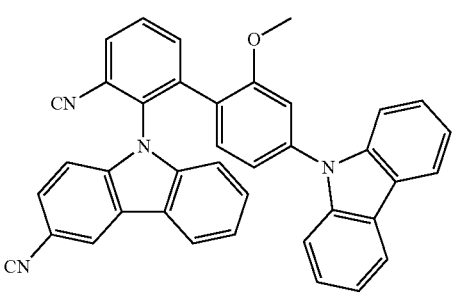
158
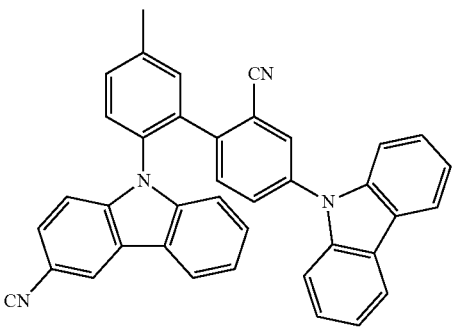
159
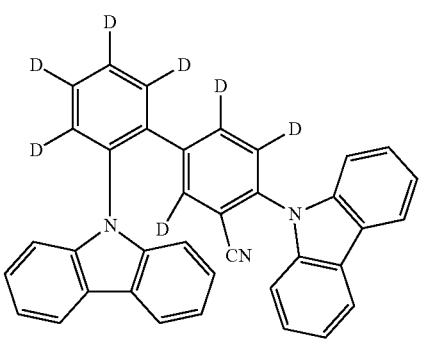

160
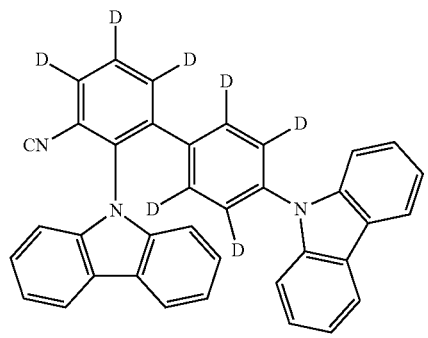
161
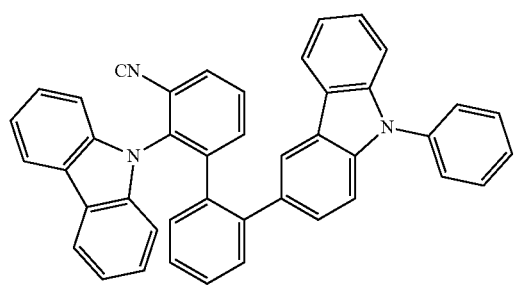
162
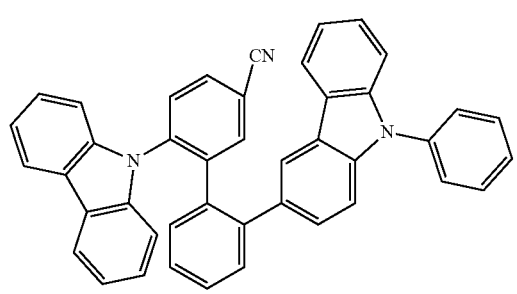
163
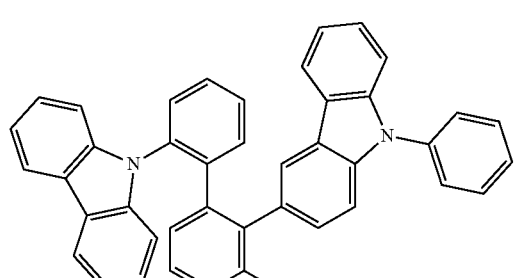
164
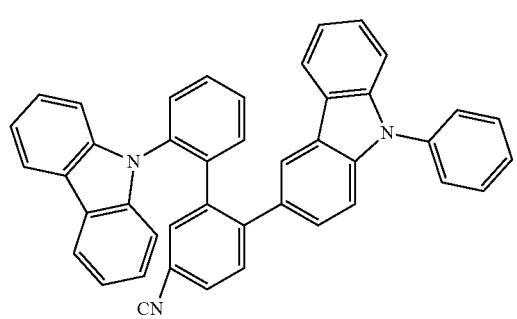
165
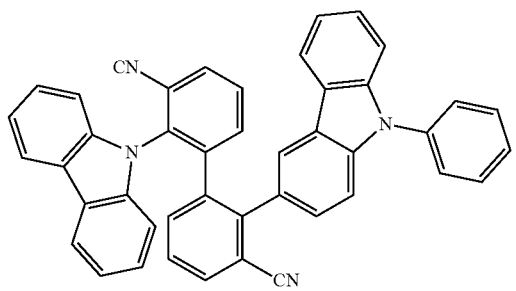
166
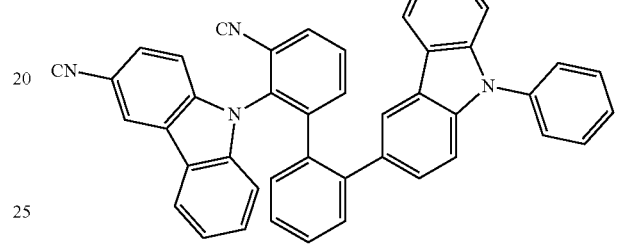
167
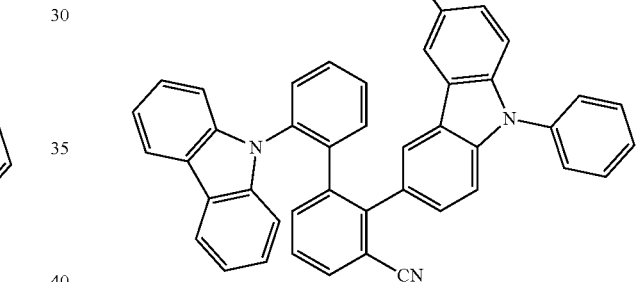
168
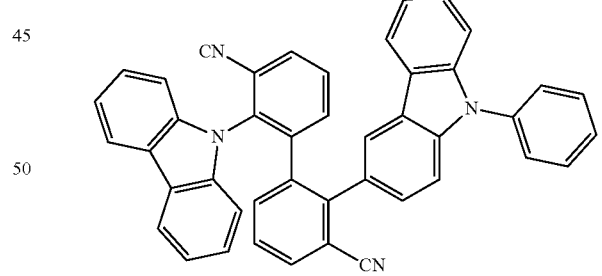
169
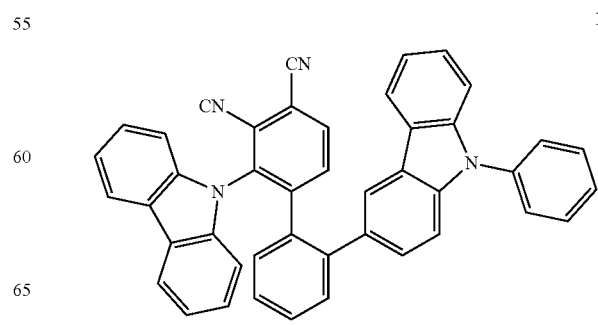

-continued
170
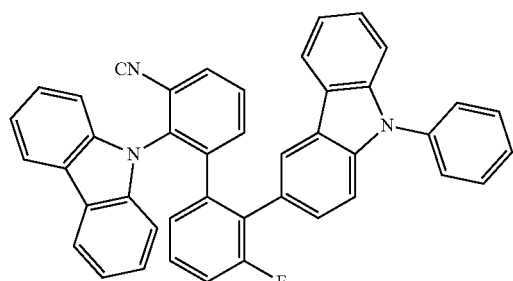
171
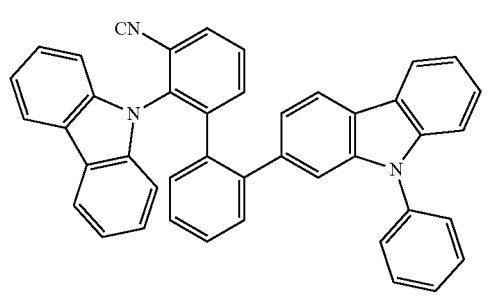
172
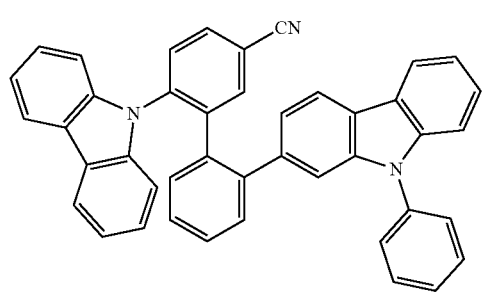
173
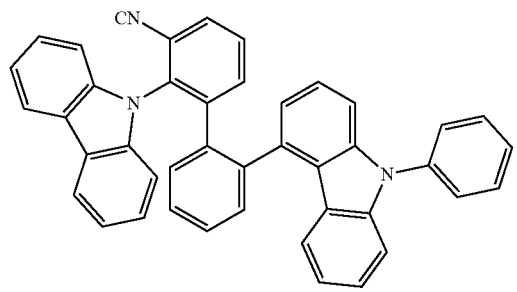
174
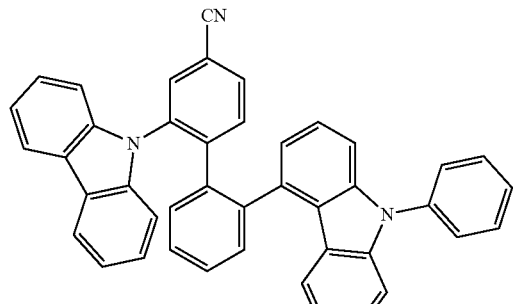
-continued
175
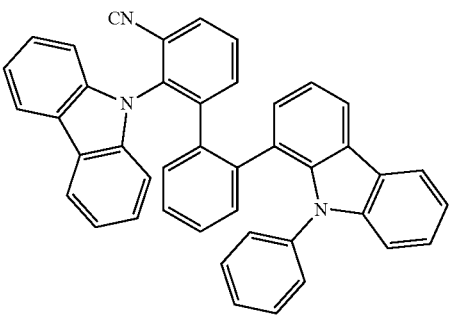
176
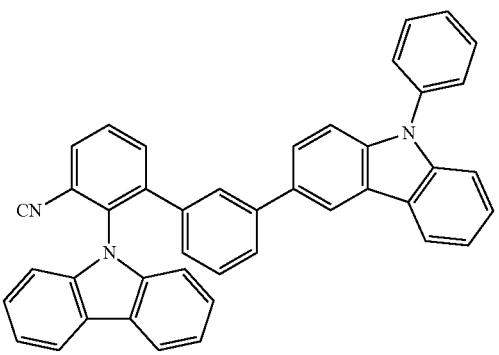
177
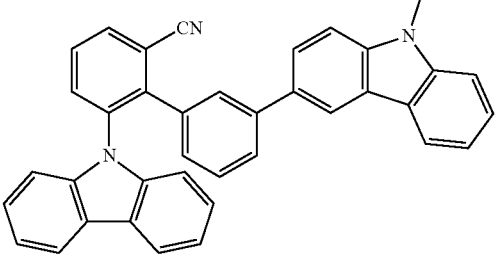
178
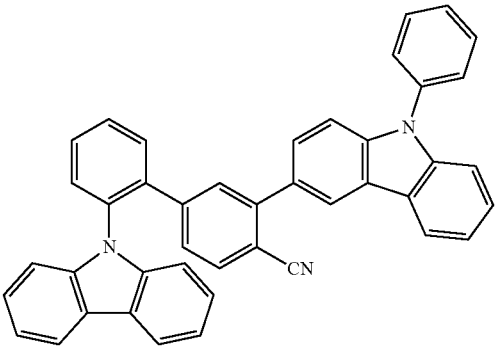

| 599 -continued | 600 -continued |
|---|---|
| 179 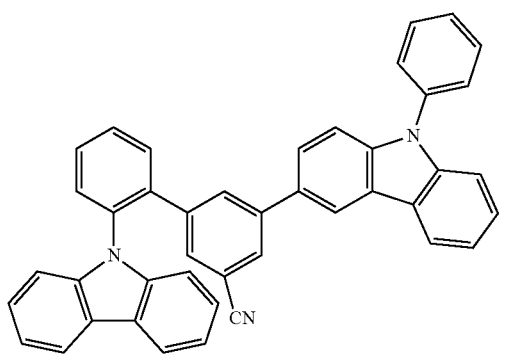 | 183 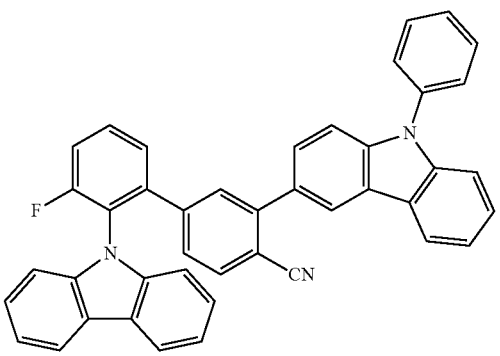 |
| 180 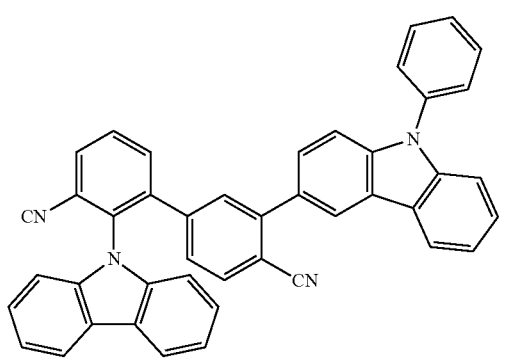 | 184 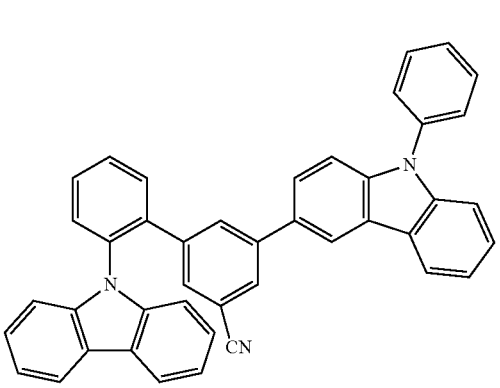 |
| 181 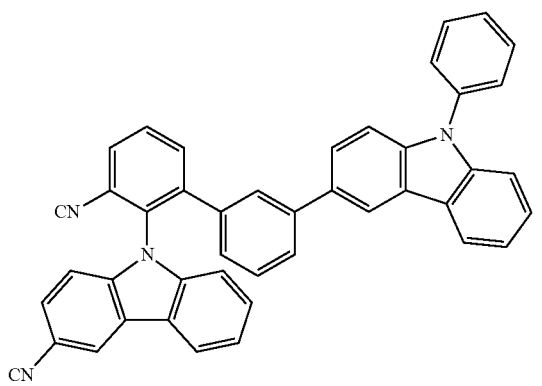 | 185 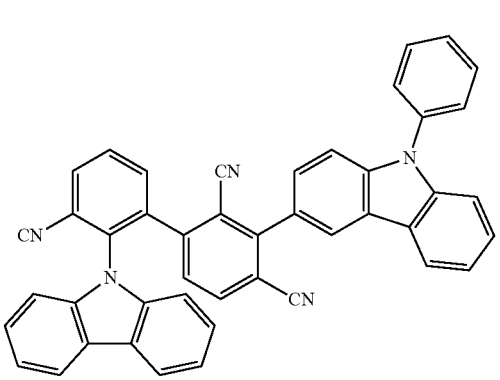 |
| 182 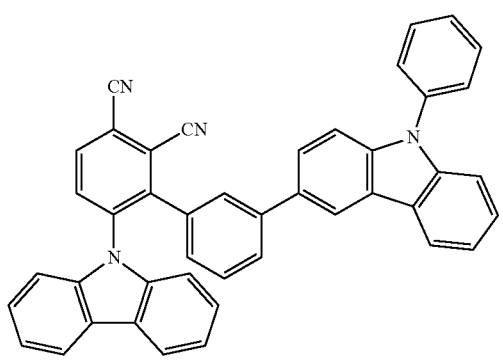 | 186 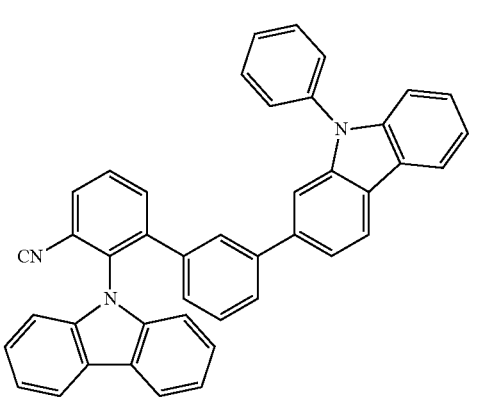 |

| 601 -continued | 602 -continued |
|---|---|
| 187 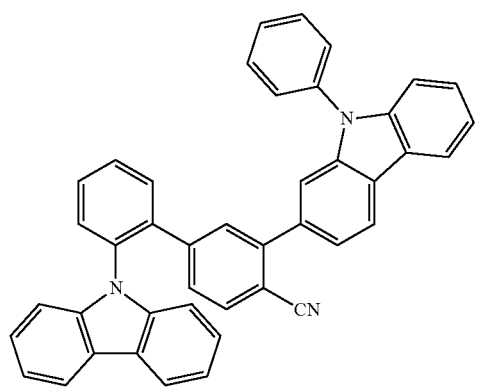 | 192 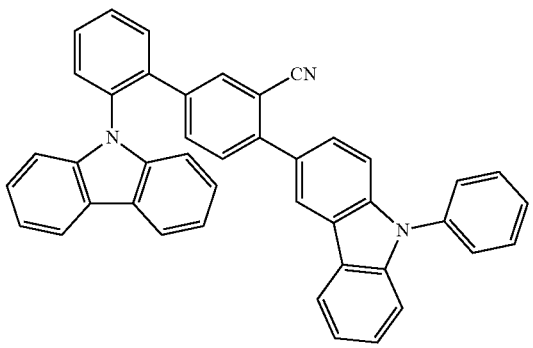 |
| 188 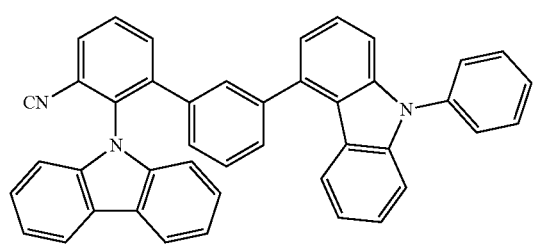 | 193 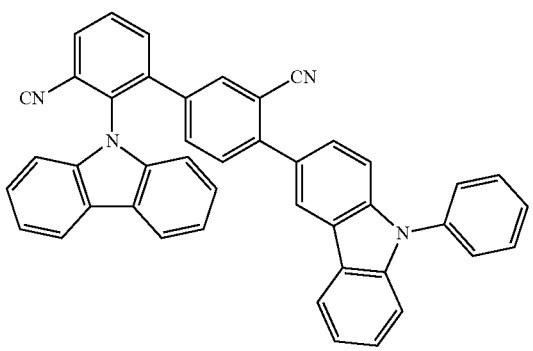 |
| 189 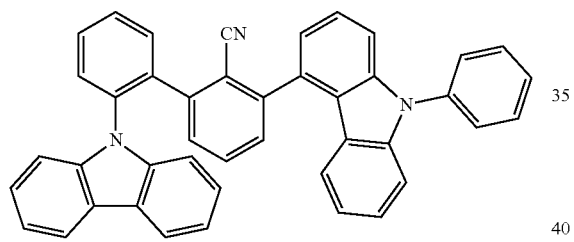 | 194 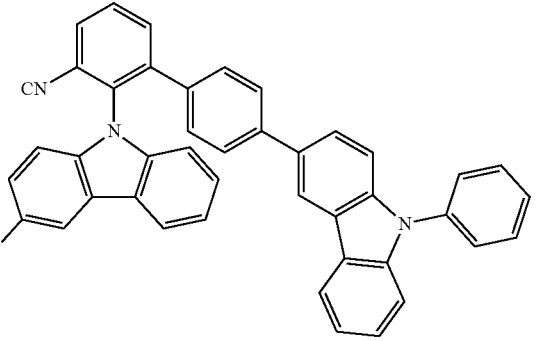 |
| 190 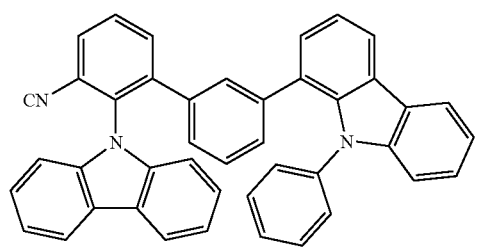 | |
| 191 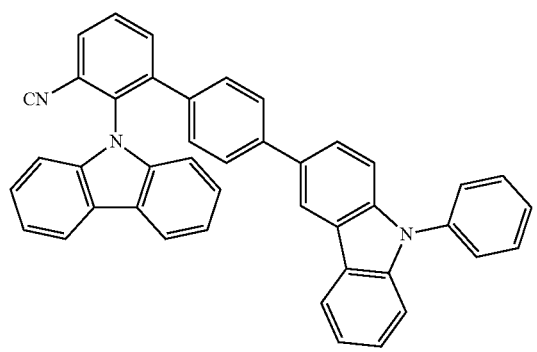 | 195 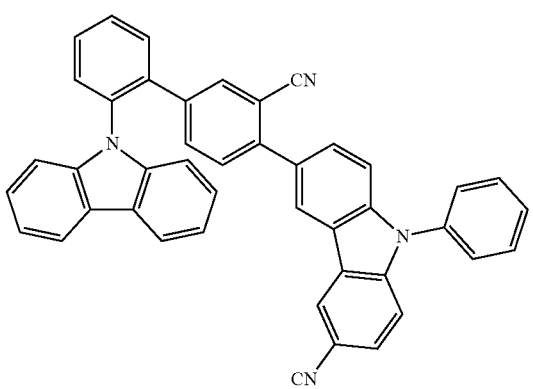 |

603
-continued
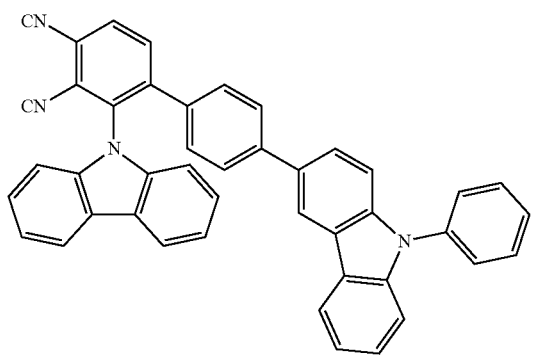
604
-continued
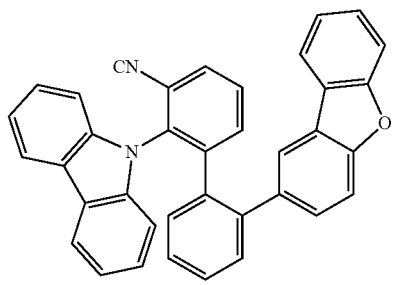
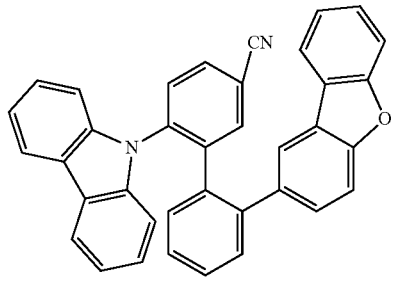
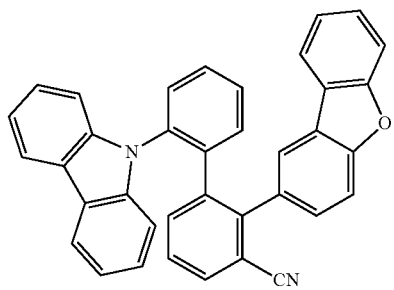
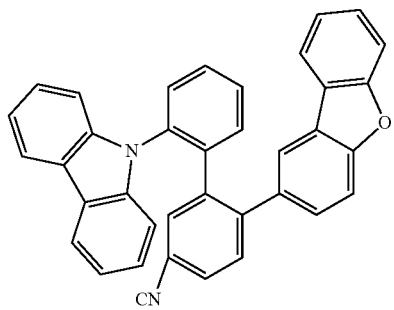
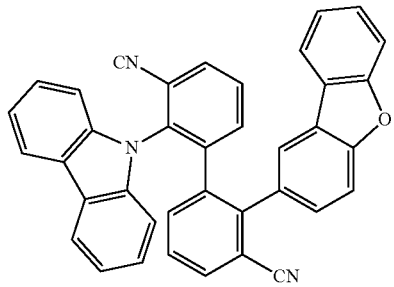

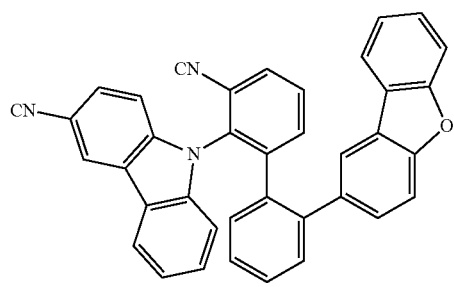
206
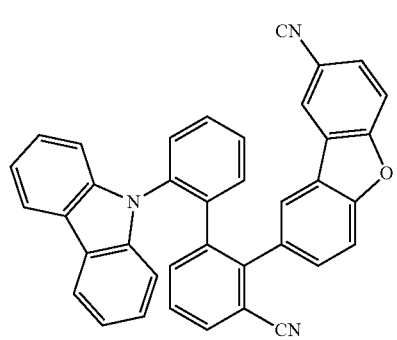
207
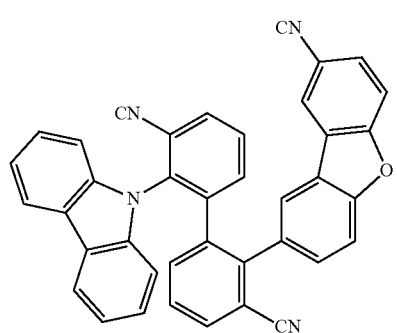
208
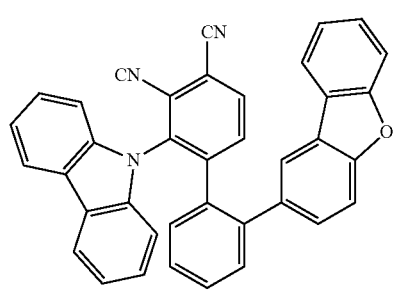
209
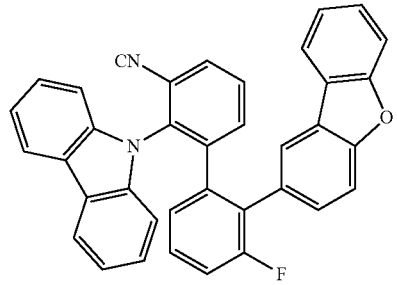
210
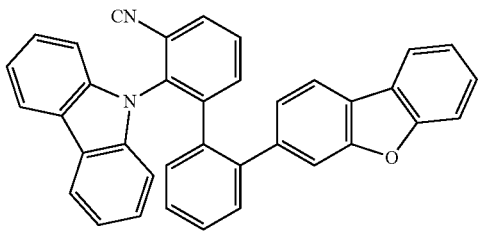
211
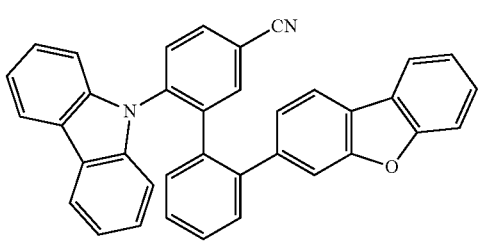
212
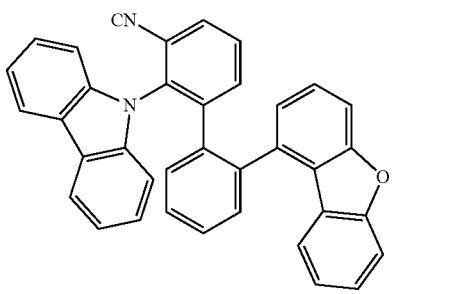
213
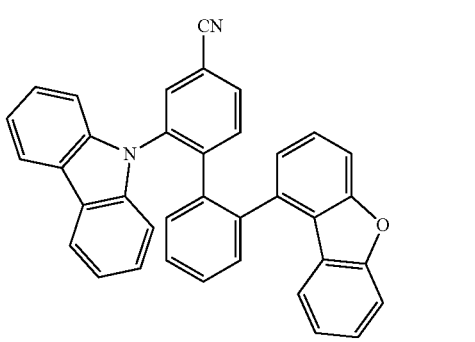
214
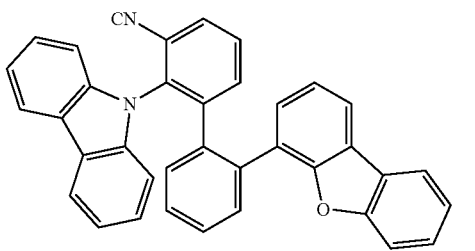
215
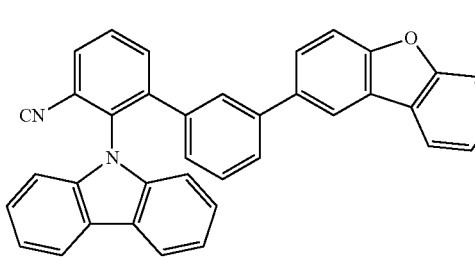
216

| 607 | 608 |
|---|---|
| -continued | -continued |
217
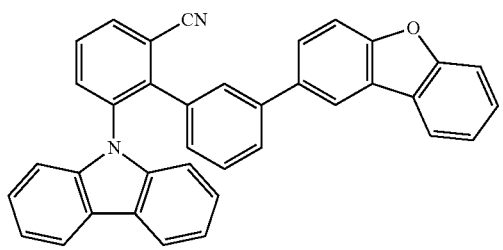
222
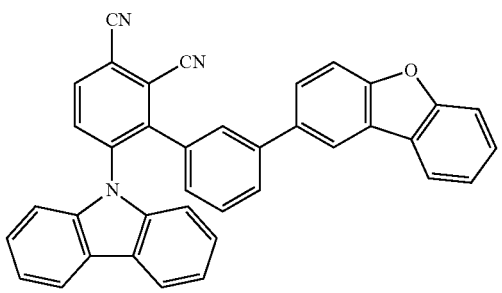
218
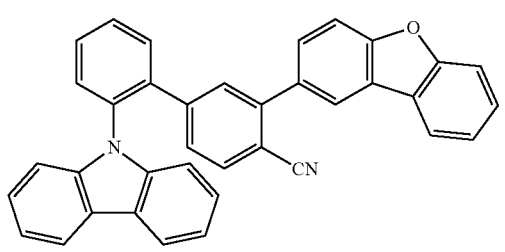
223
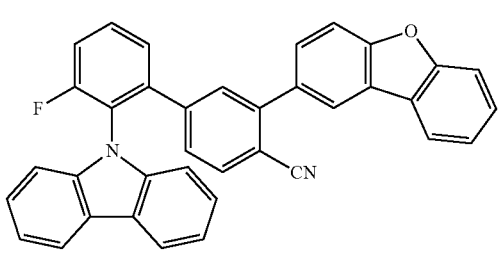
219
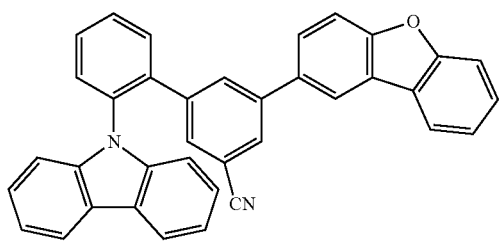
224
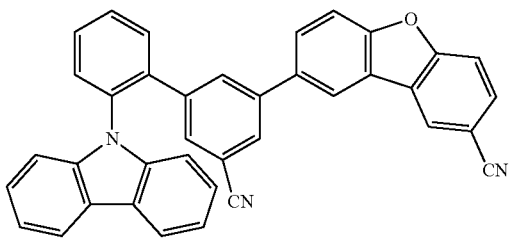
220
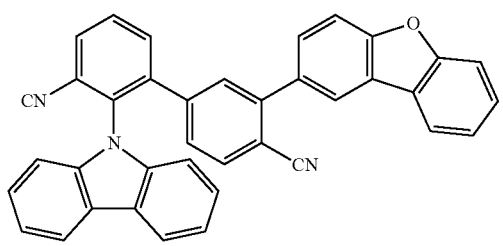
225
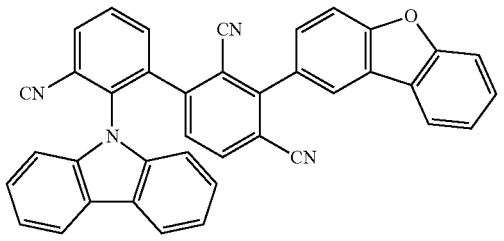
221
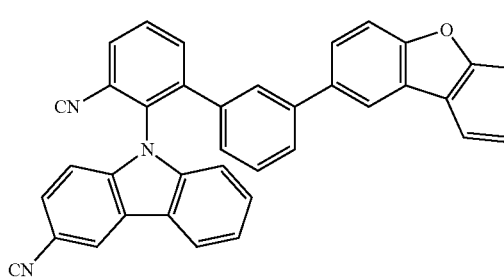
226
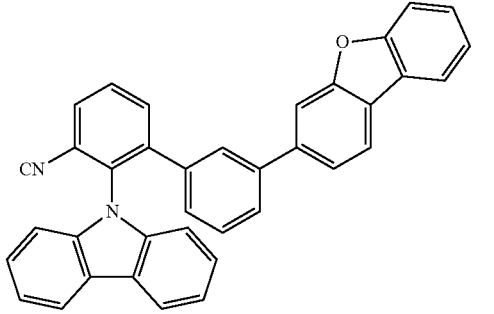

609
-continued
227
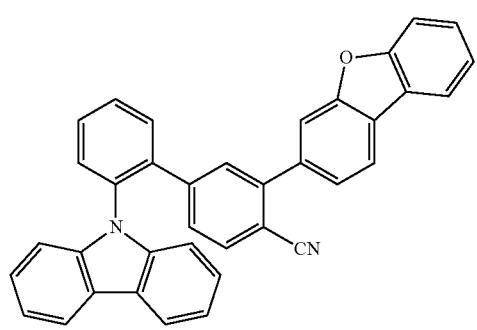
228
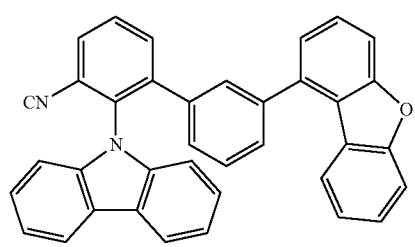
229
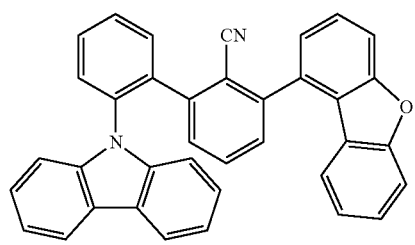
230
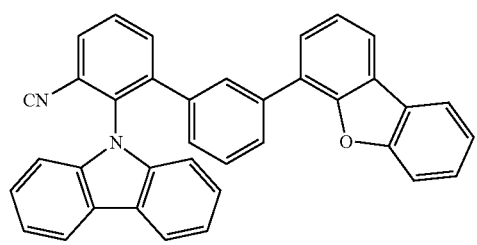
231
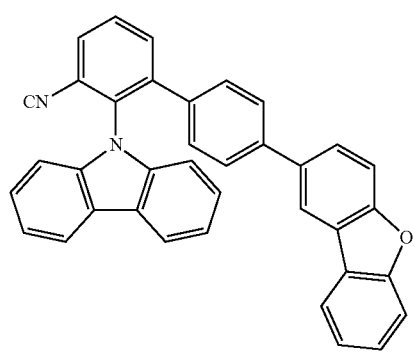
610
-continued
232
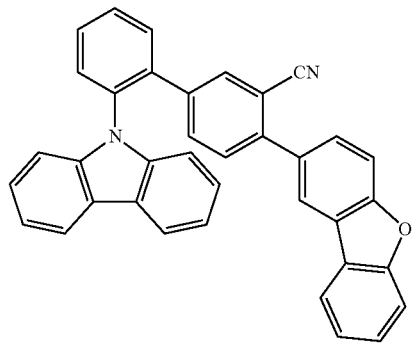
233
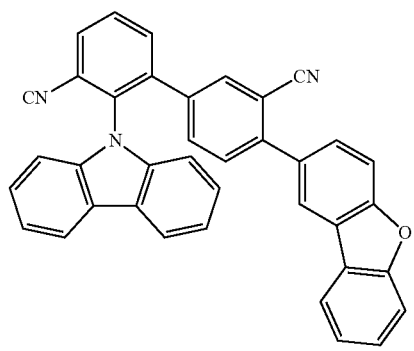
234
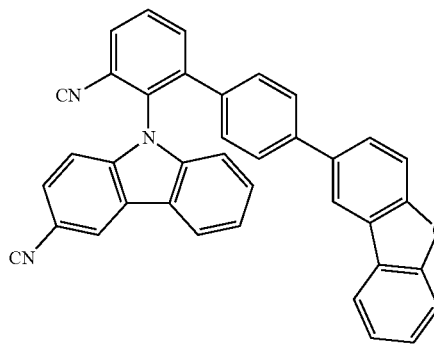
235
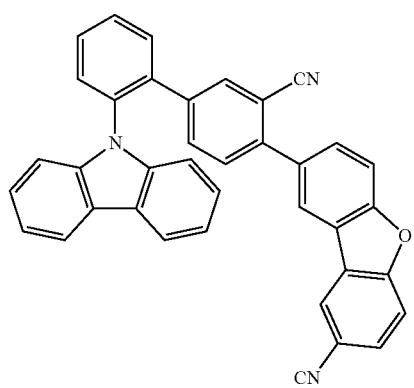

236
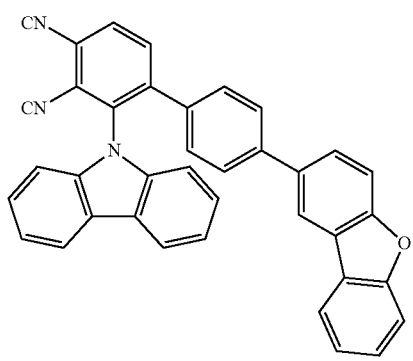
237
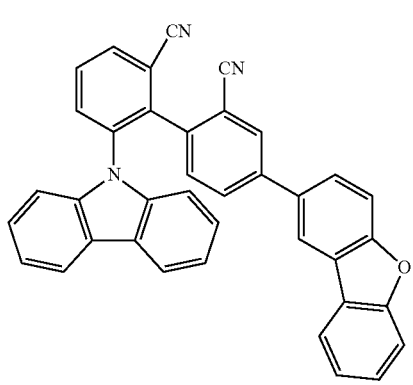
238
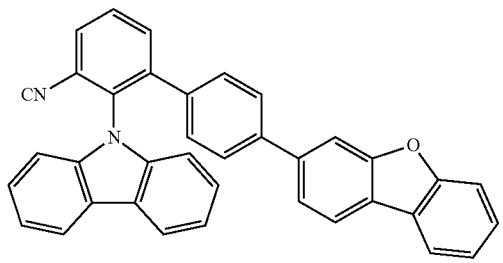
239
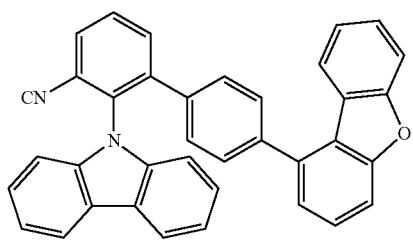
240
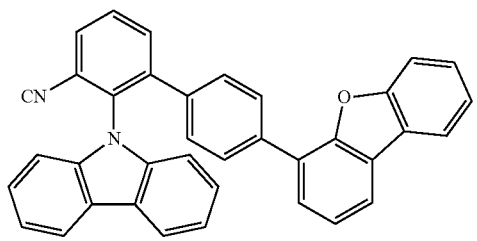
241
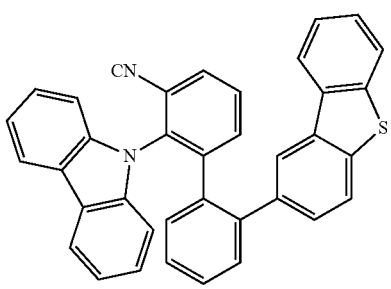
242
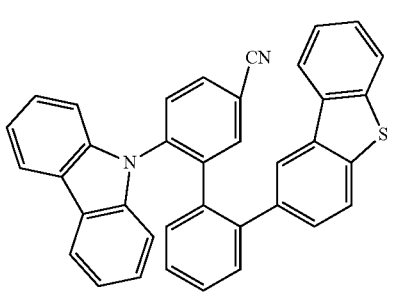
243
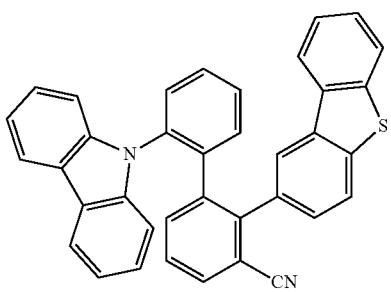
244
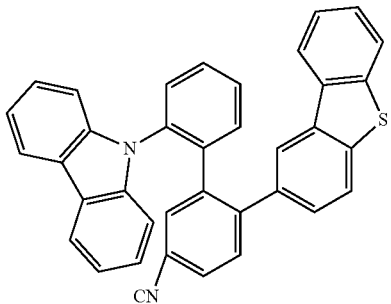
245
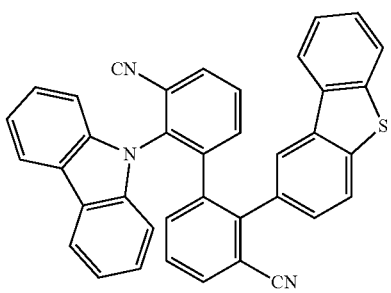

246
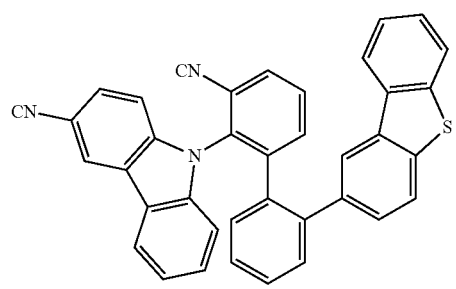
247
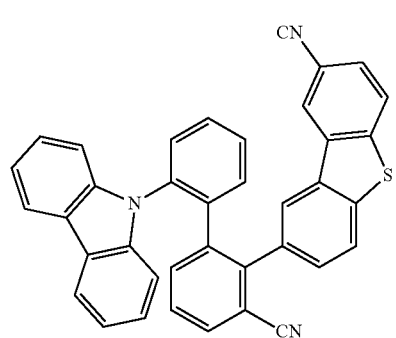
248
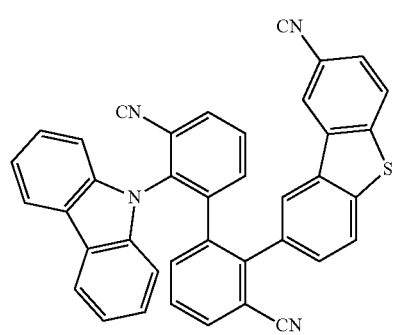
249
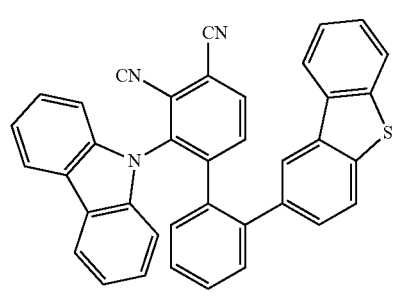
250
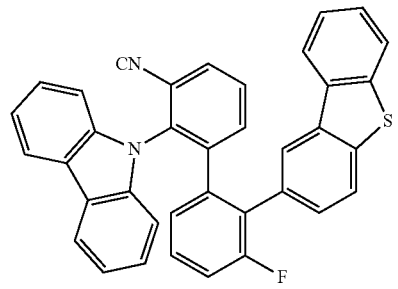
251
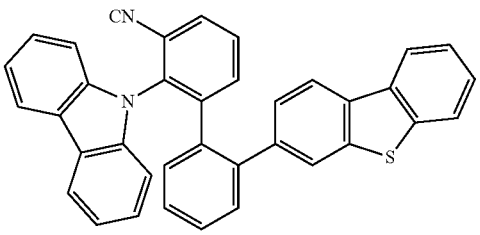
252
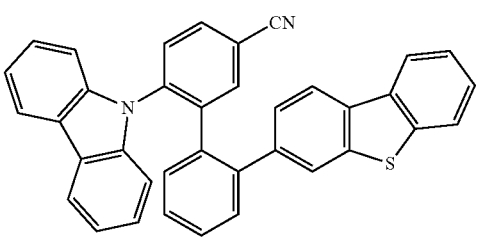
253
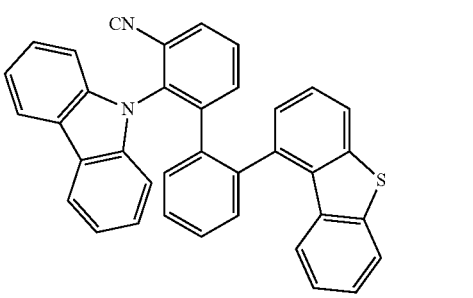
254
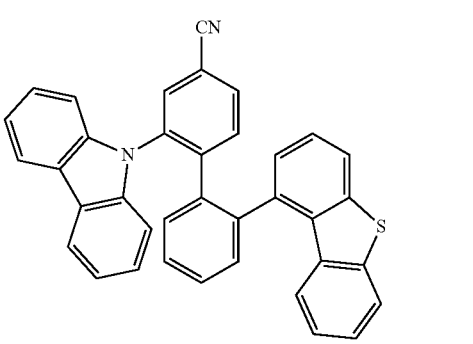
255
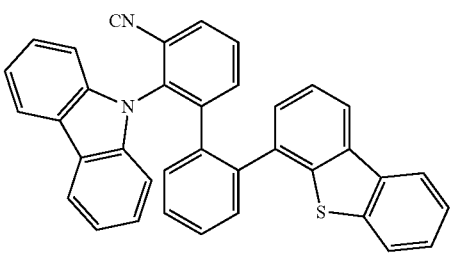
256
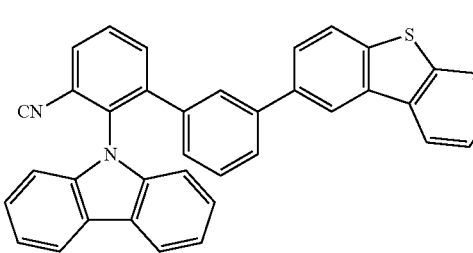

257 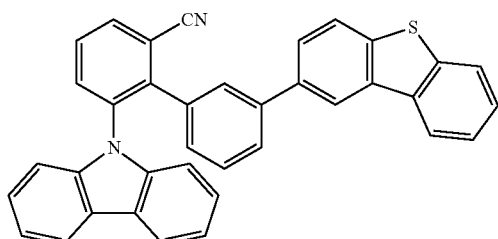
262 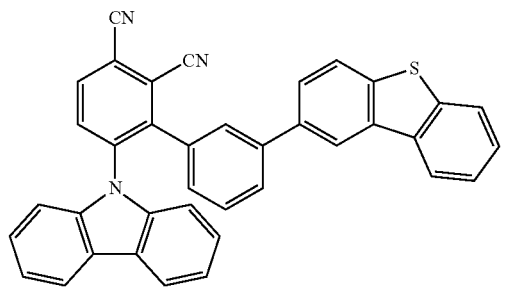
258 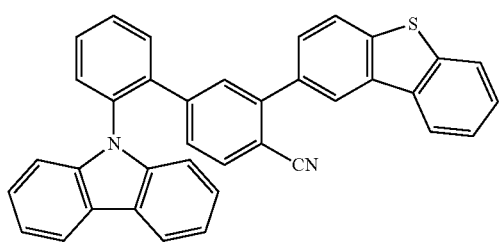
263 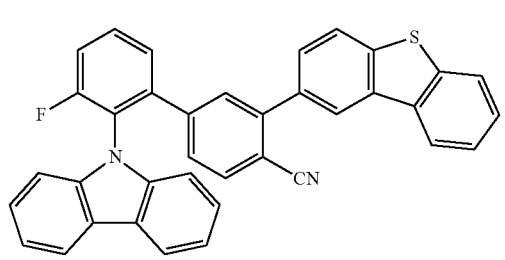
259 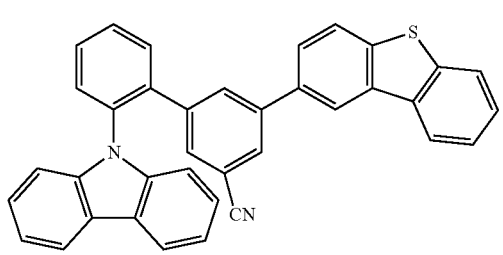
264 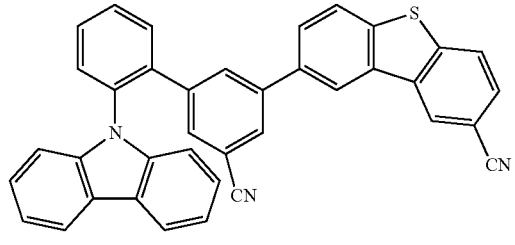
260 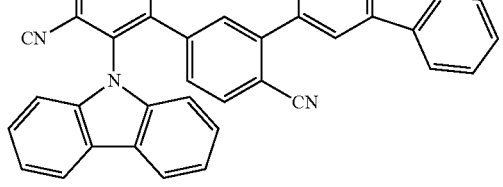
265 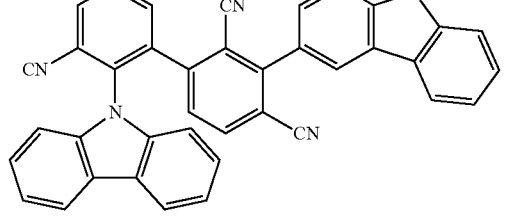
261 
266 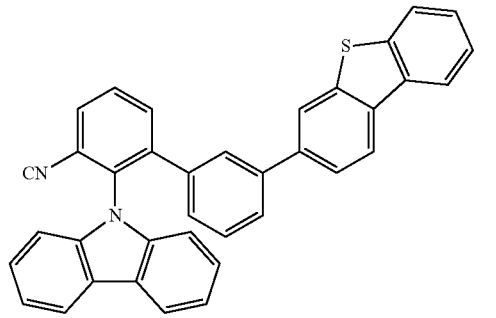

-continued
267
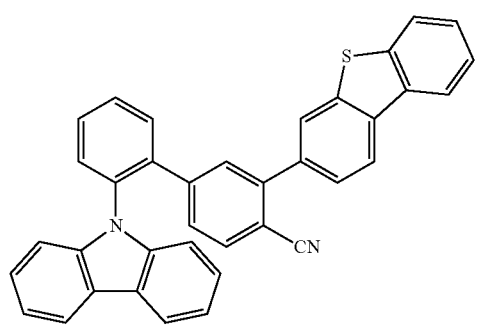
268
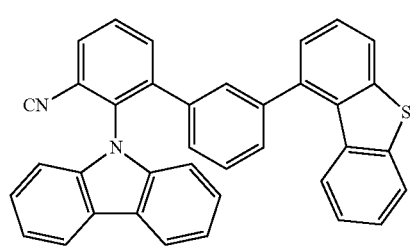
269
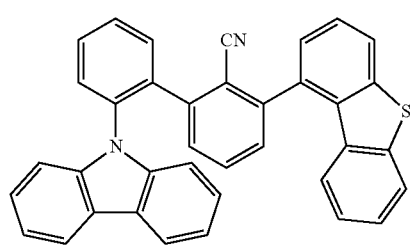
270
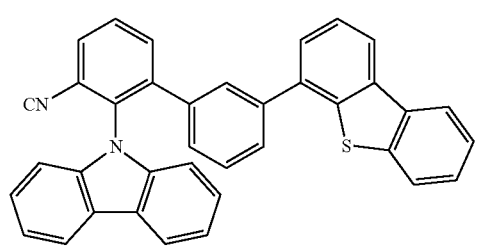
271
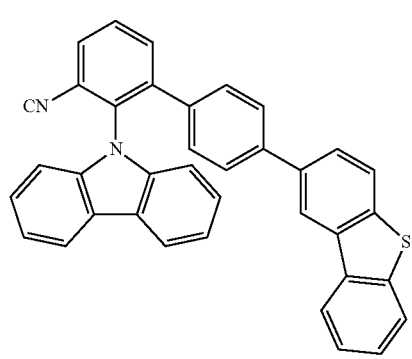
-continued
272
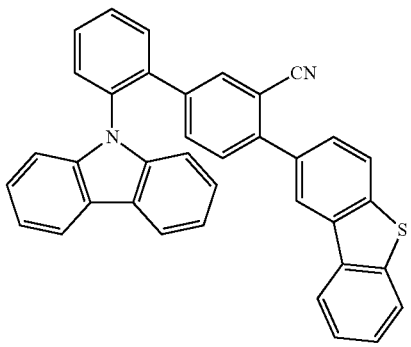
273
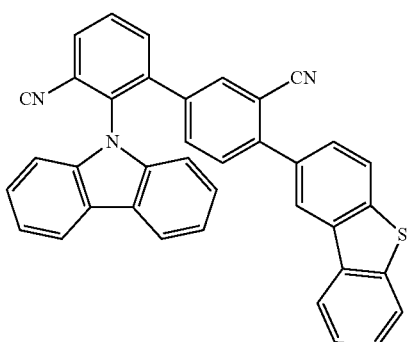
274
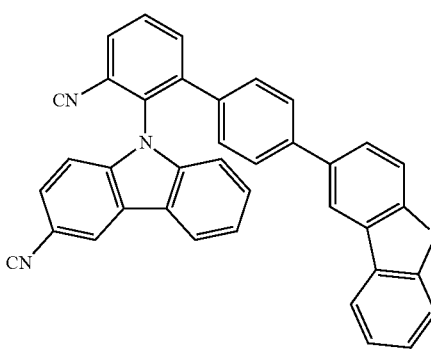
275
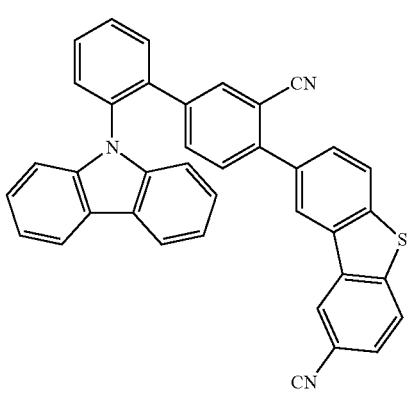

619 -continued
276
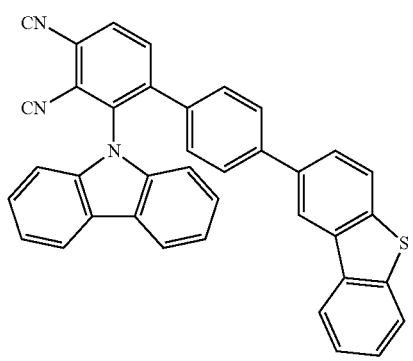
277
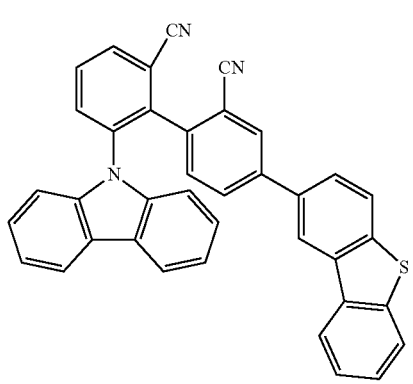
278
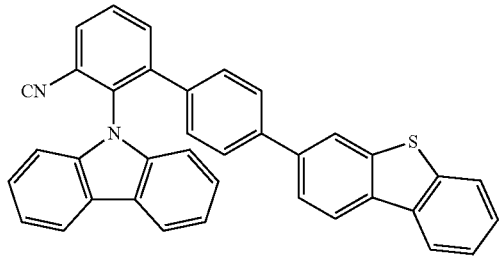
279
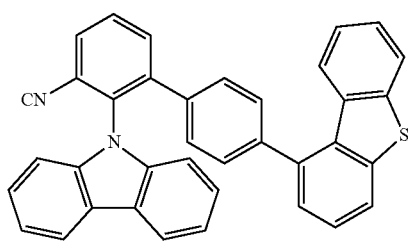
280
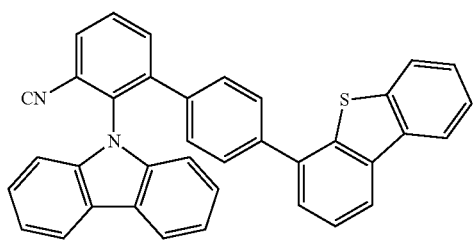
620 -continued
281
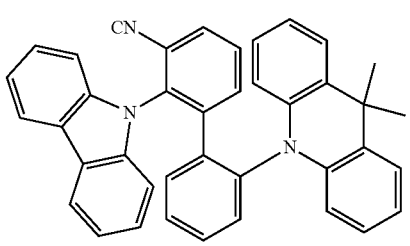
282
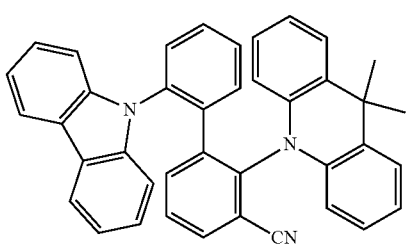
283
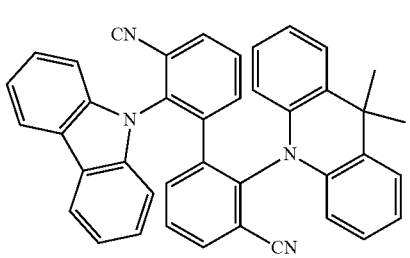
284
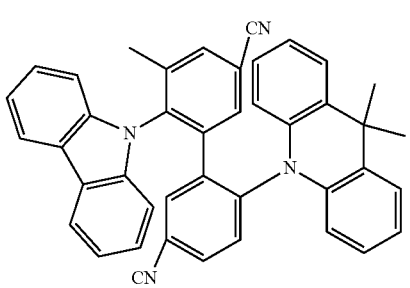
285
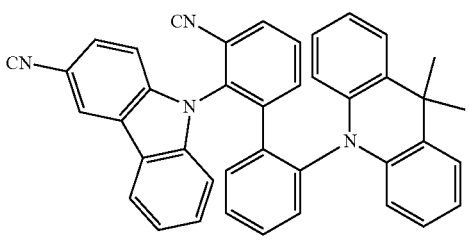
286
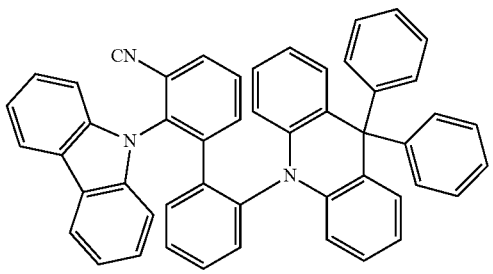

287
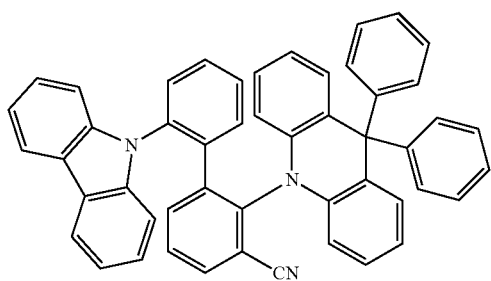
288
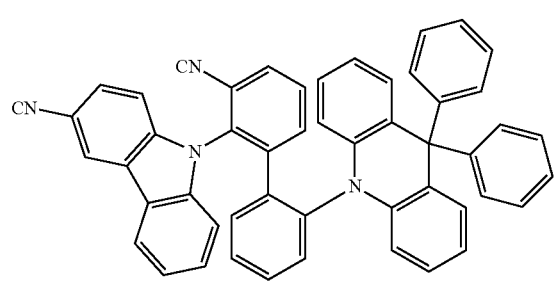
289
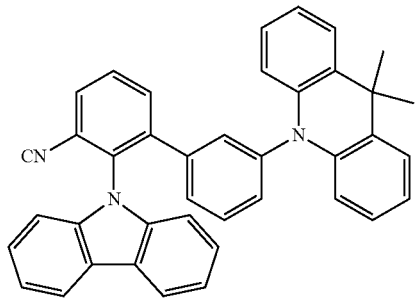
290
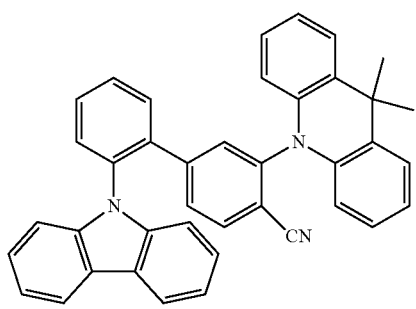
291
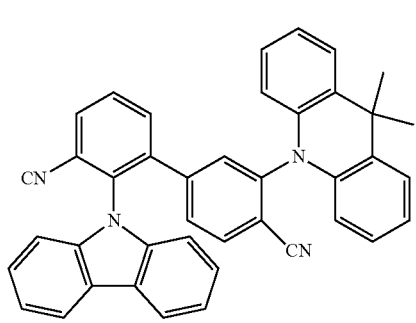
292
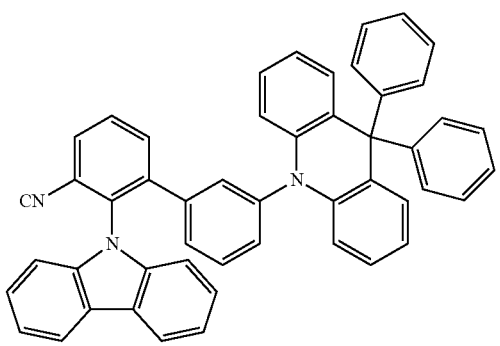
293
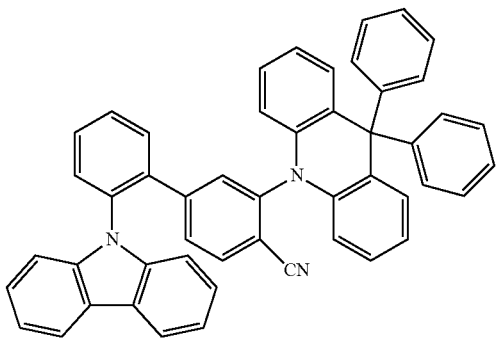
294
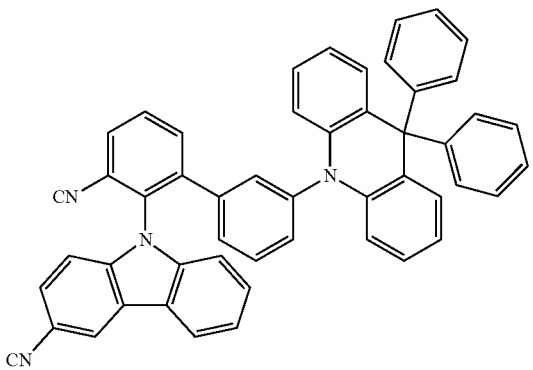
295

296
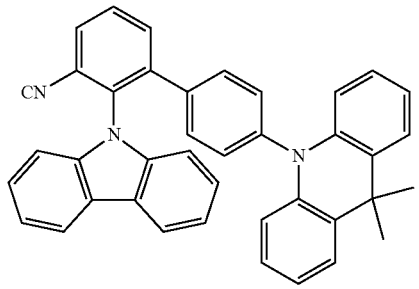
297
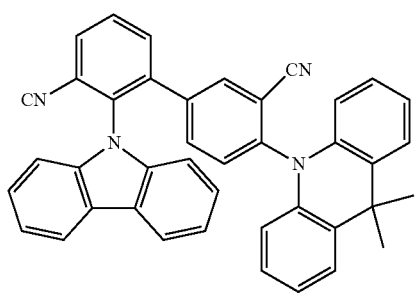
298
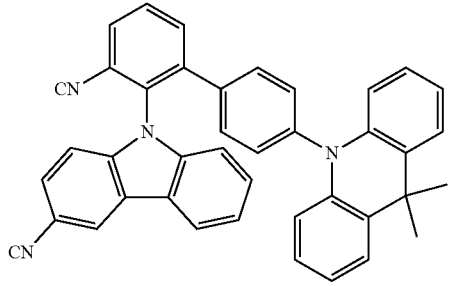
299
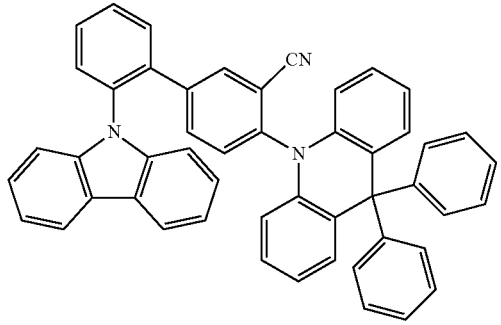
300
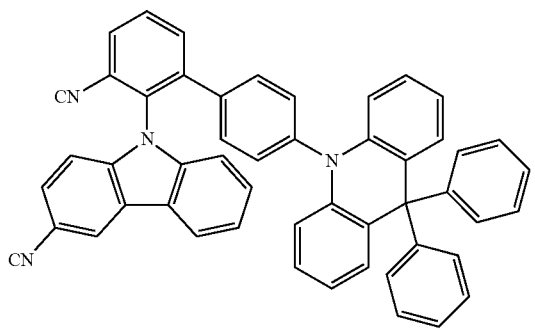
301
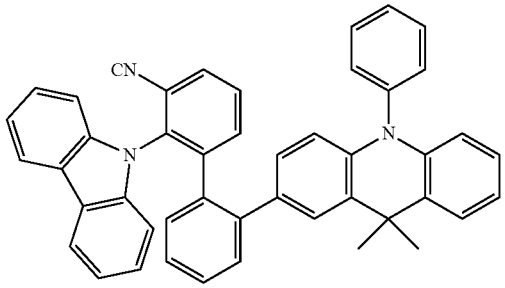
302
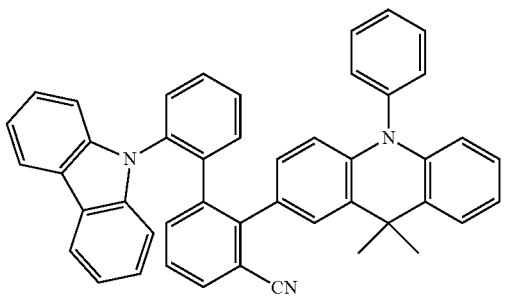
303
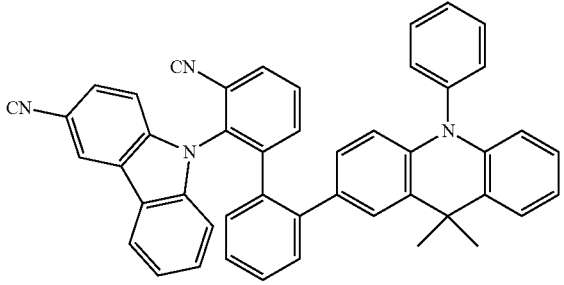
304
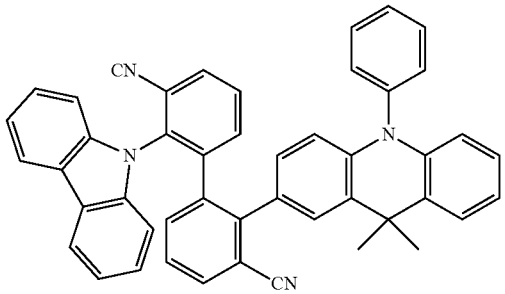
305
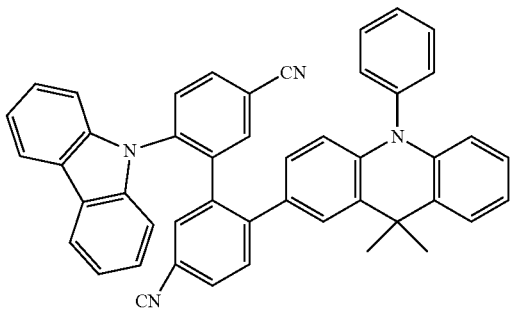

625
-continued
306
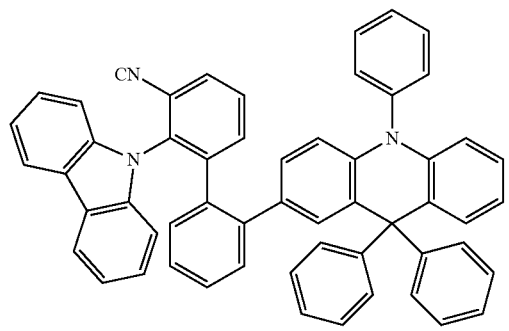
307
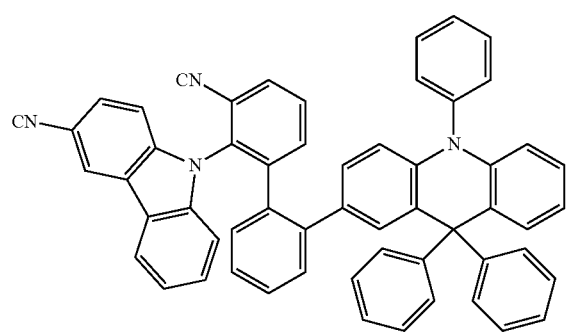
308
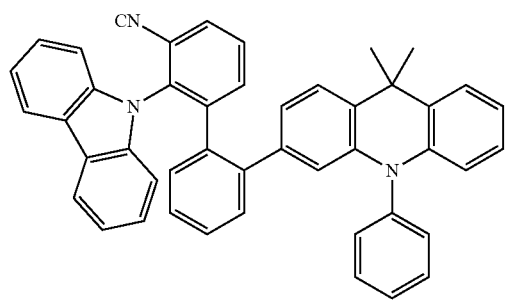
309
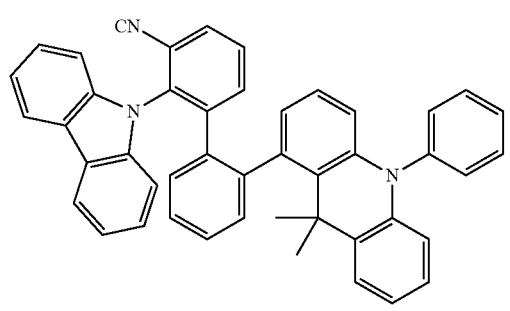
310
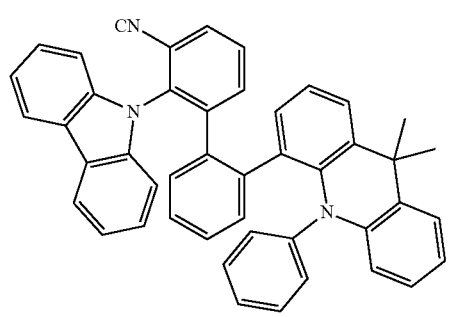
626
-continued
311
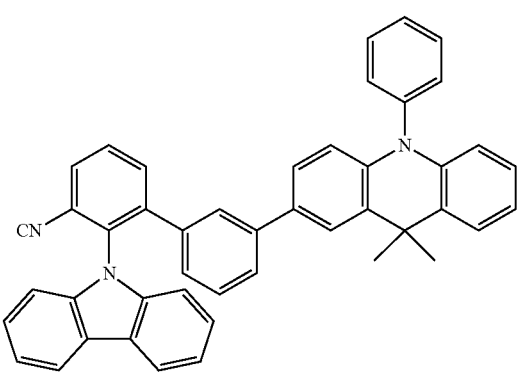
312
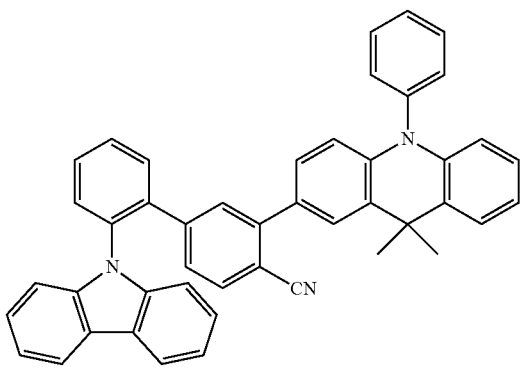
313
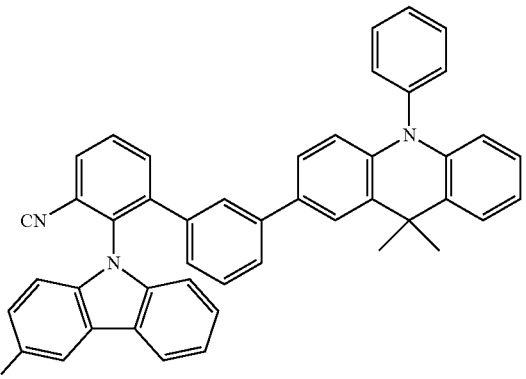
314
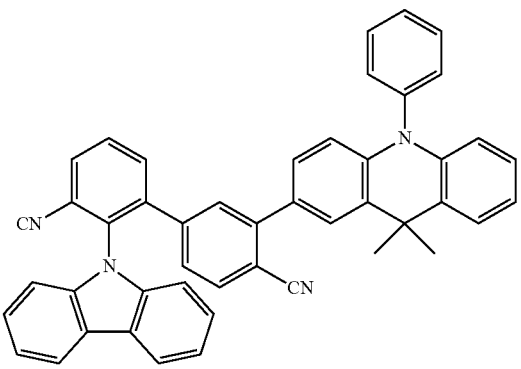

627
-continued
315
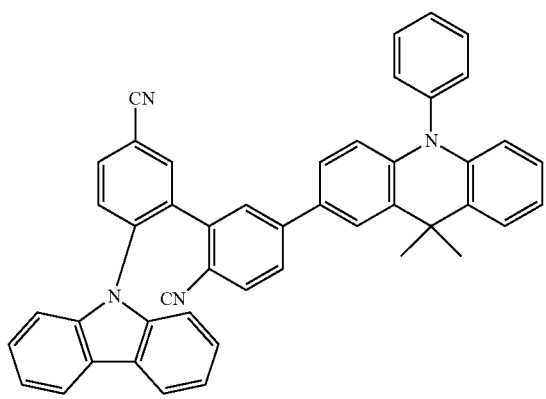
316
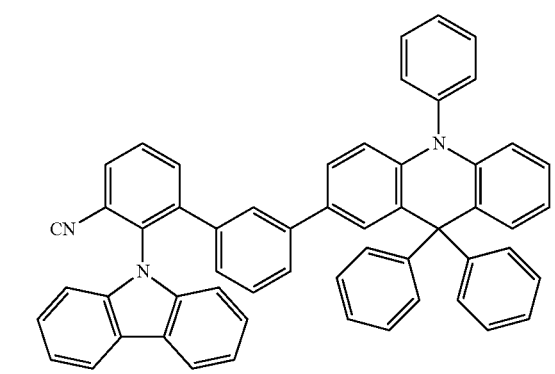
317
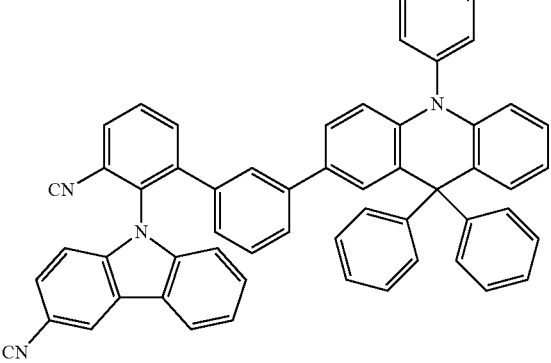
628
-continued
319
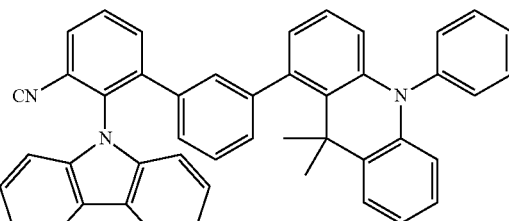
320
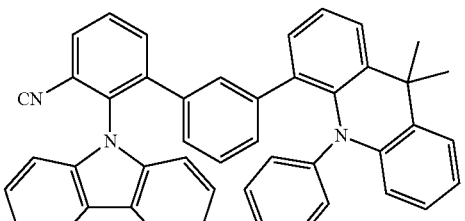
321
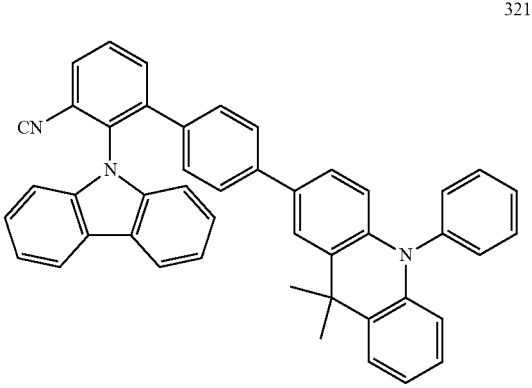
322
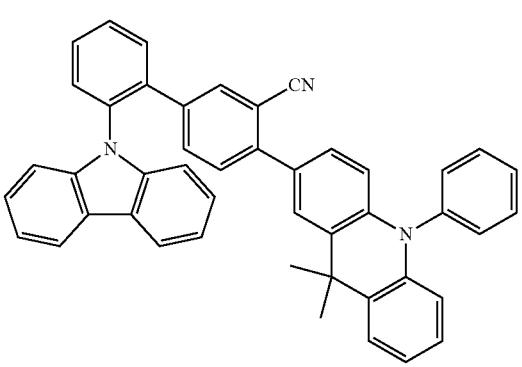
318
323
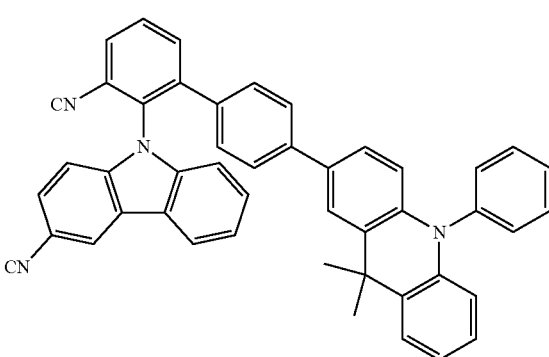

-continued
324
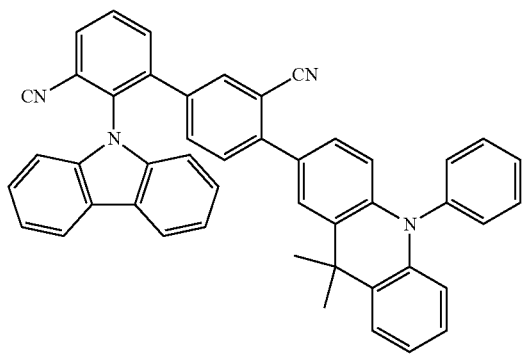
325
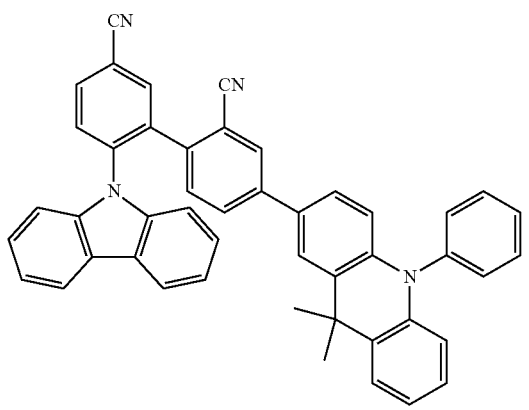
326
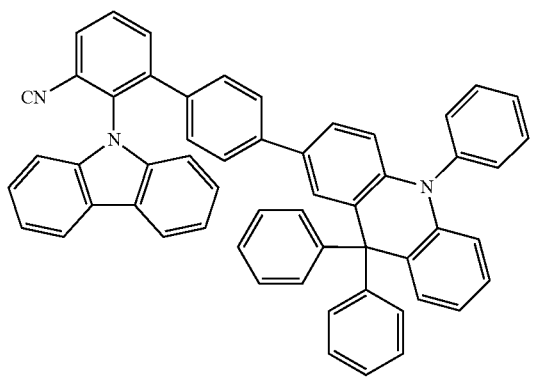
327
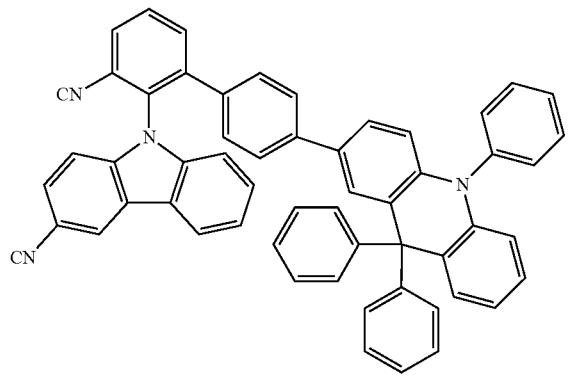
-continued
328
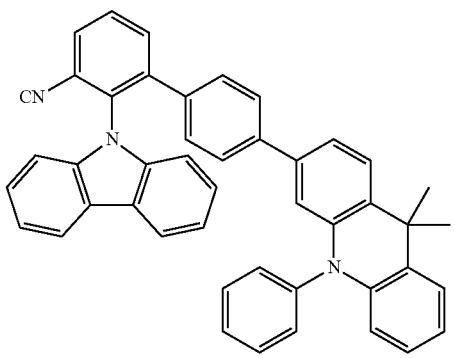
329
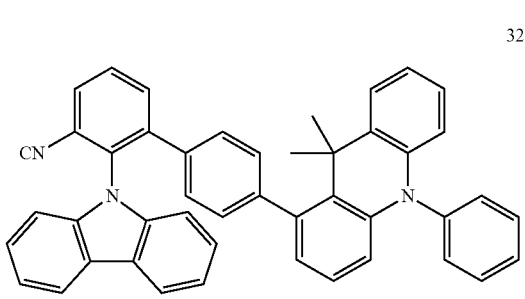
330
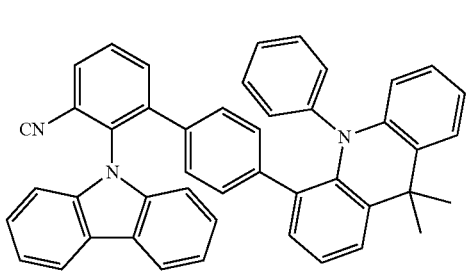
<Group HE7>
1
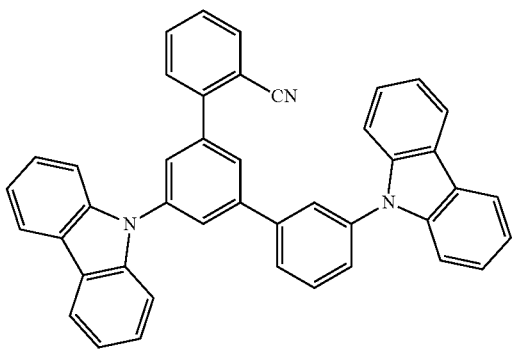

631
-continued
2
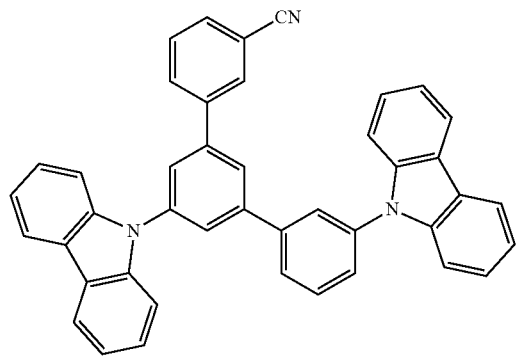
3
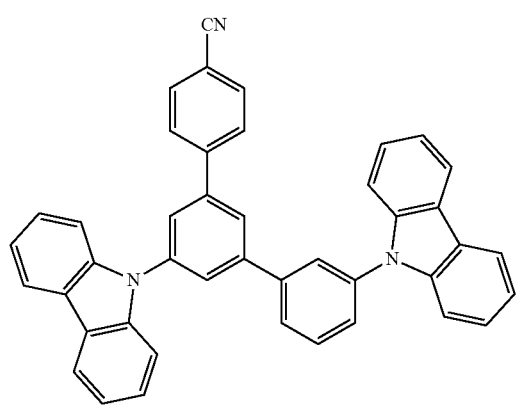
4
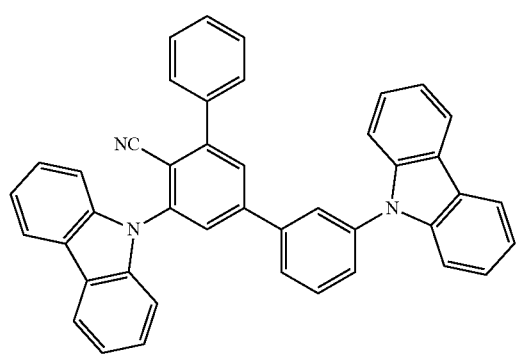
5
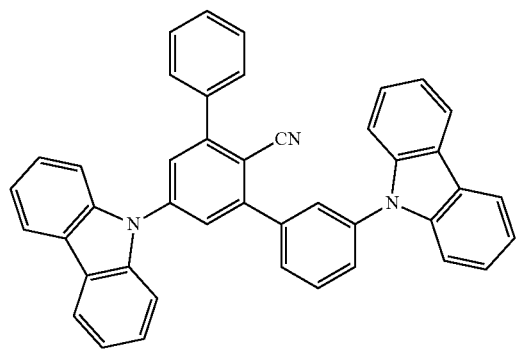
632
-continued
6
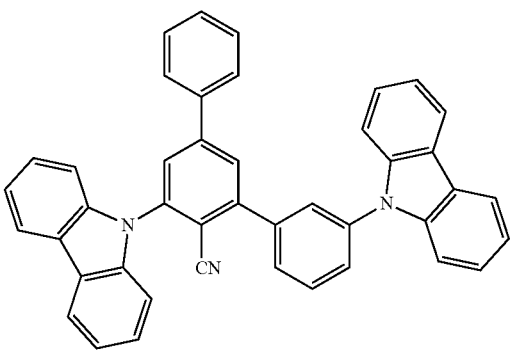
7
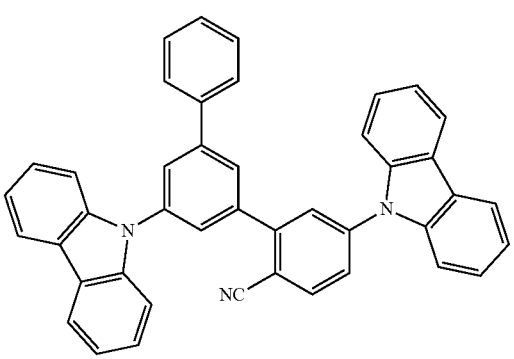
8
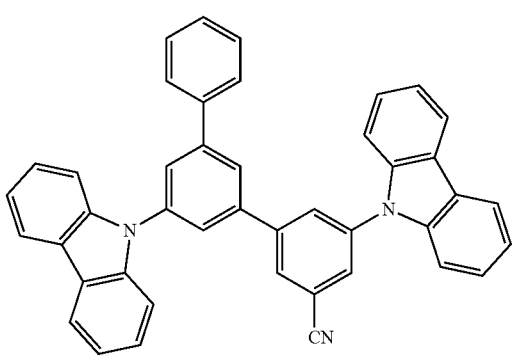
9
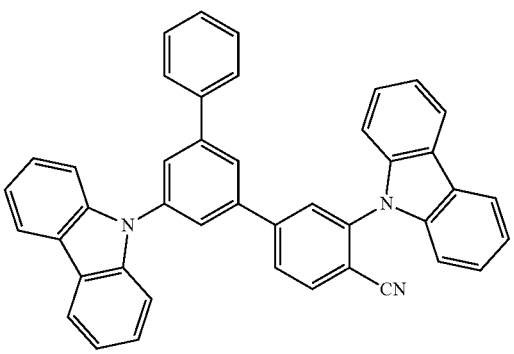

10
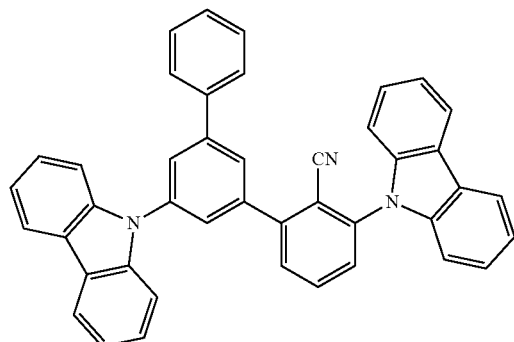
11
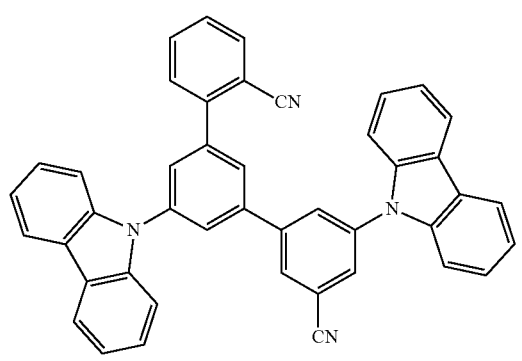
12
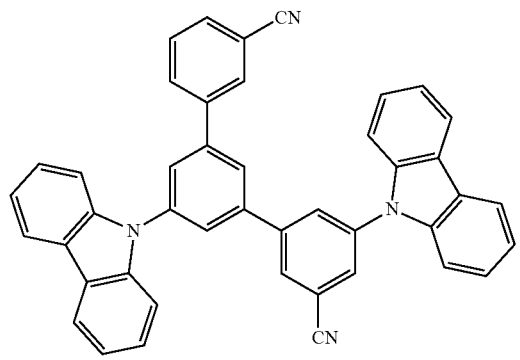
13
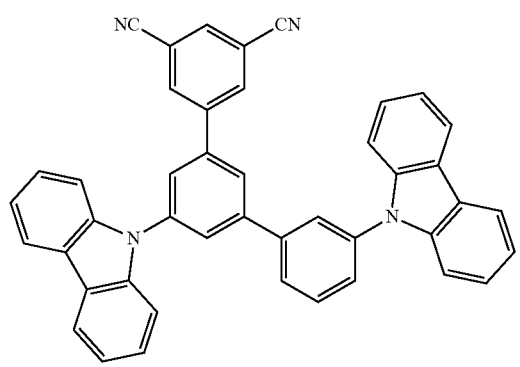
14
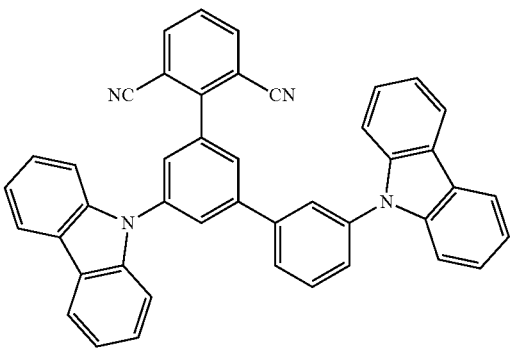
15
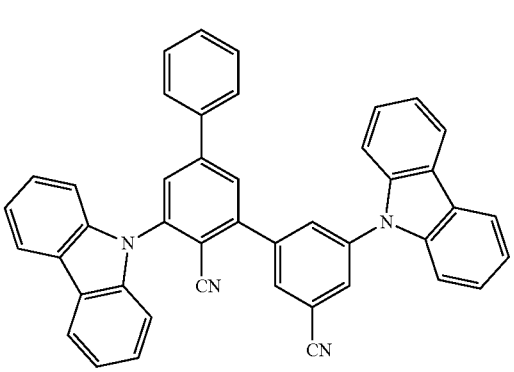
16
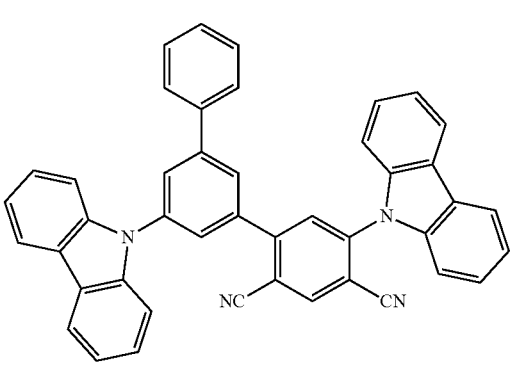
17
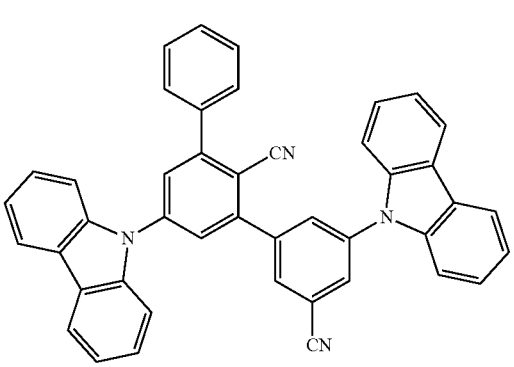

635
-continued
18
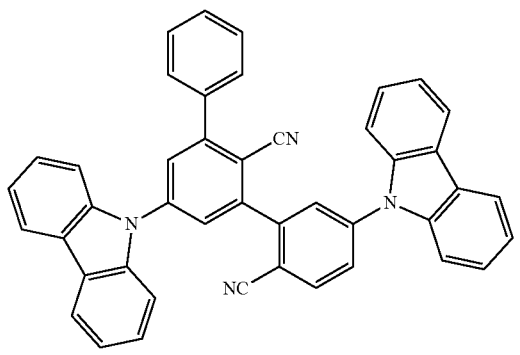
19
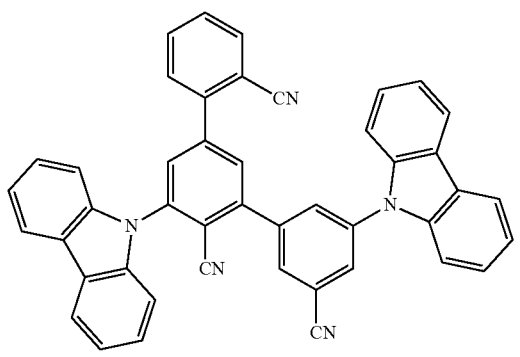
20
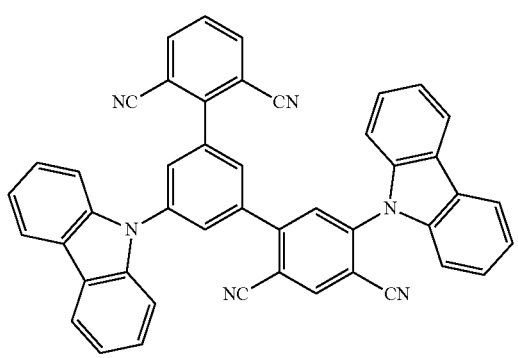
21
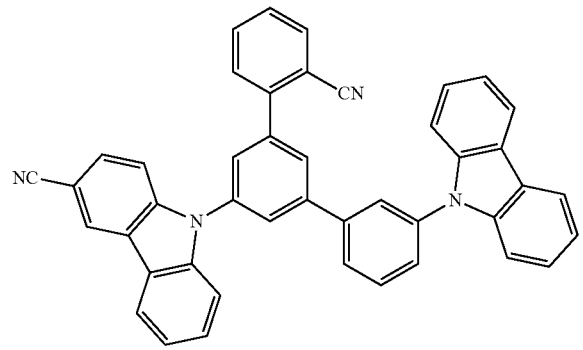
636
-continued
22
23
24
25
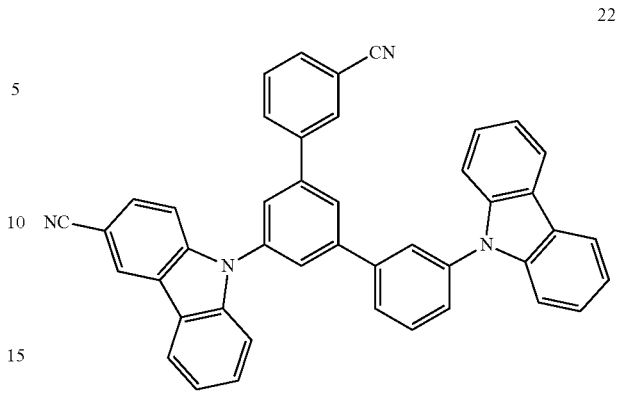
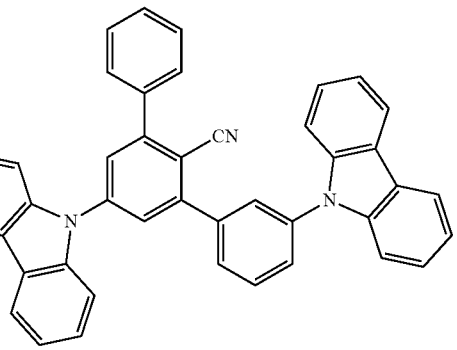

26
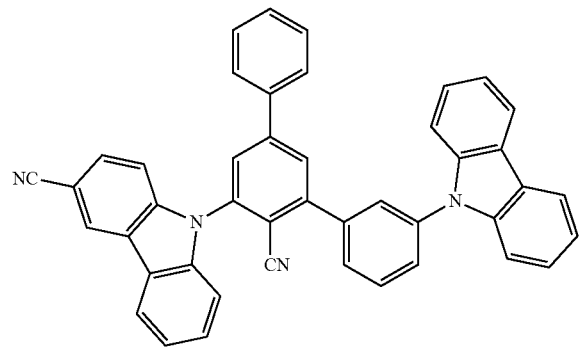
27
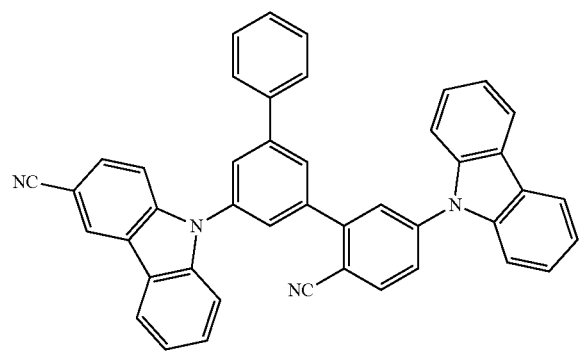
28
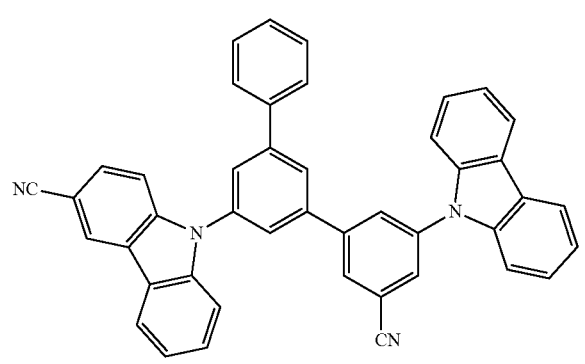
29
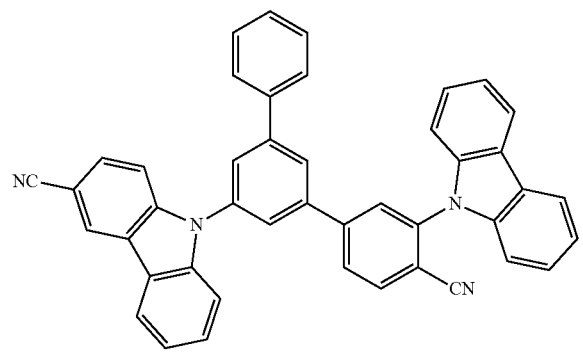
30
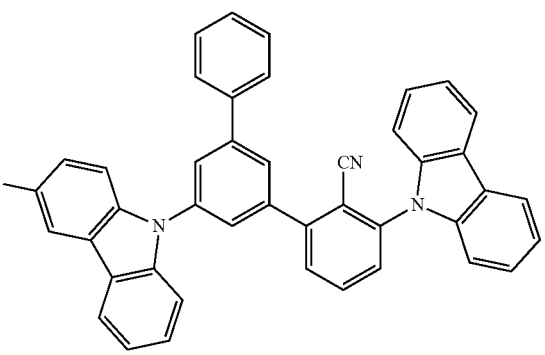
31
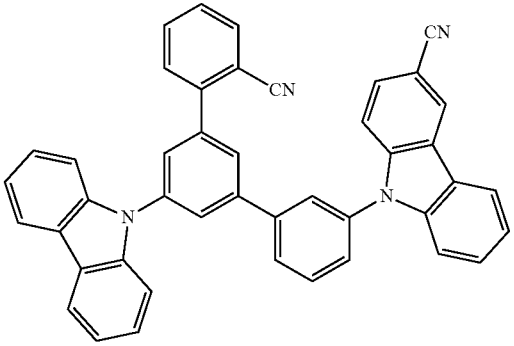
32
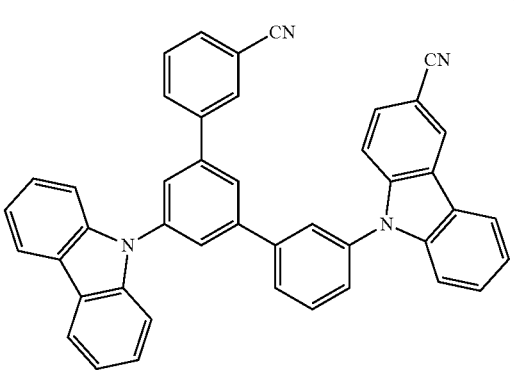
33
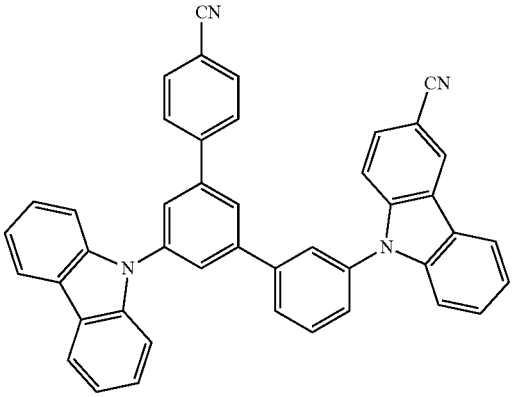

-continued
34
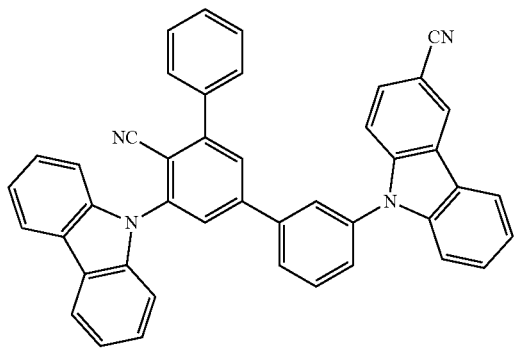
35
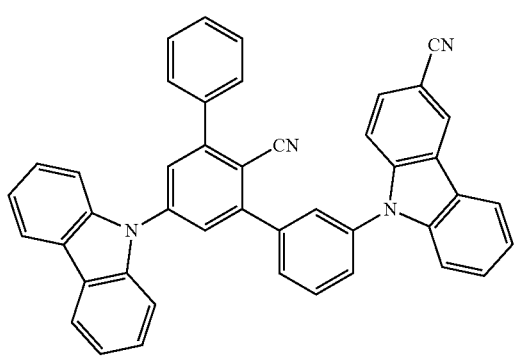
36
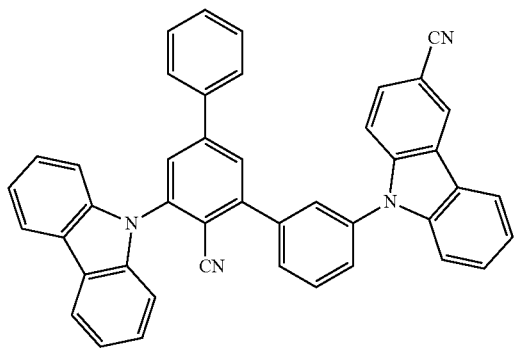
37
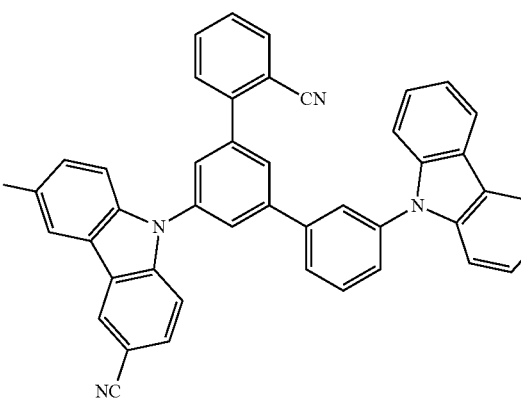
-continued
38
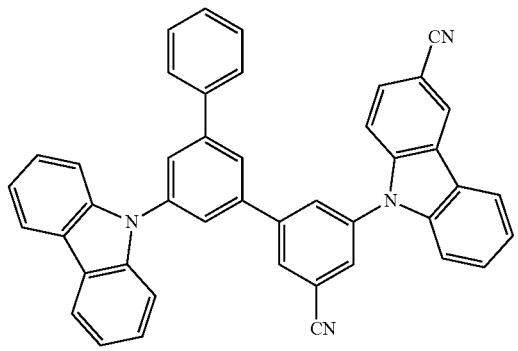
39
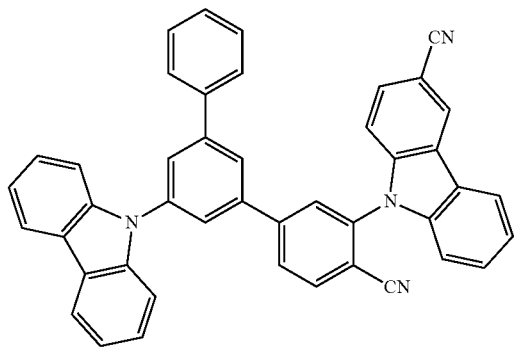
40
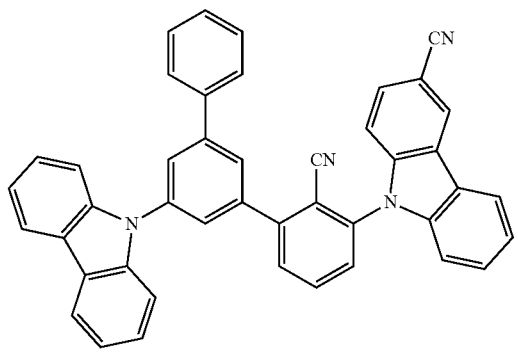
41

641
-continued
42
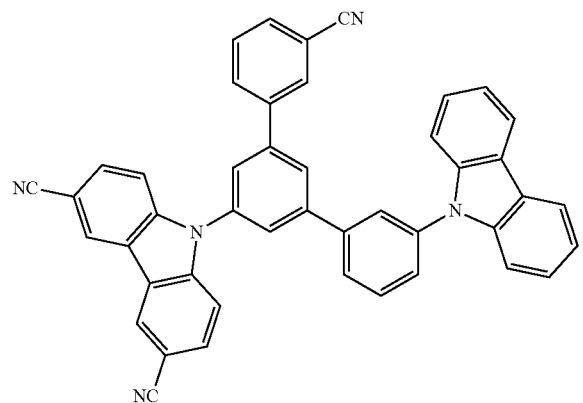
43
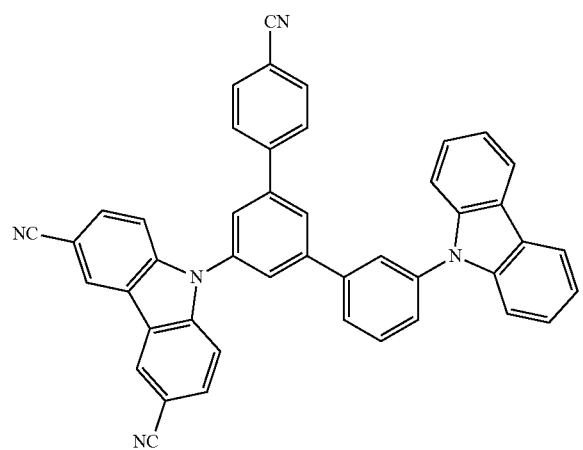
44
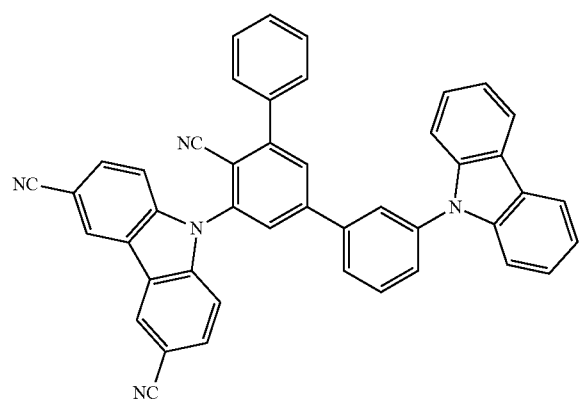
642
-continued
45
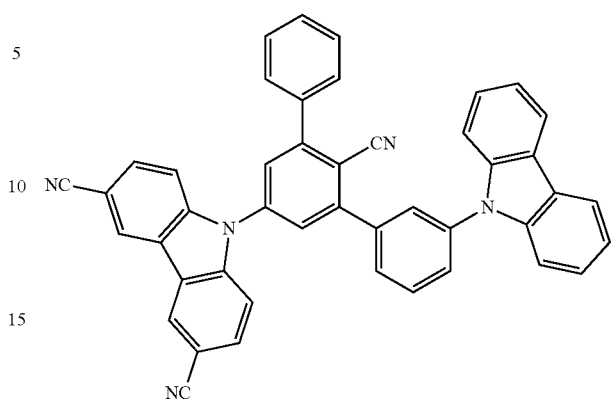
46
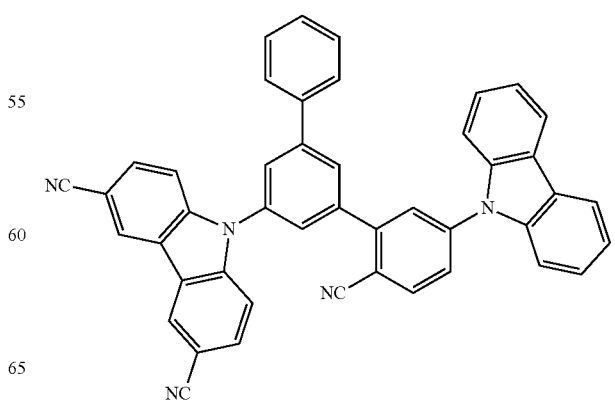
47

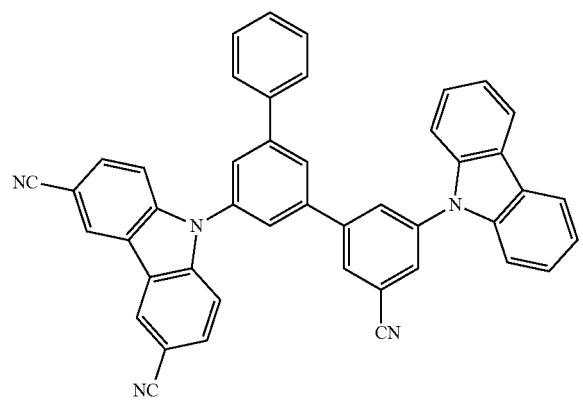
48
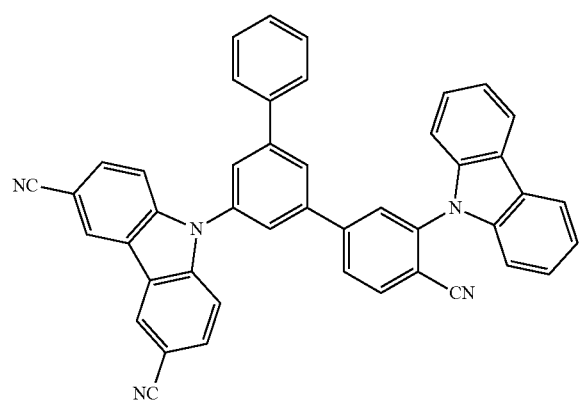
49
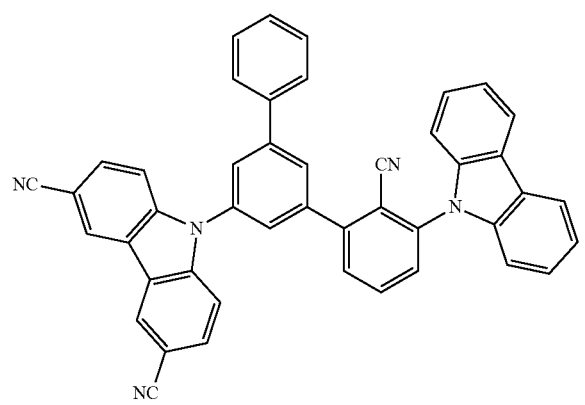
50
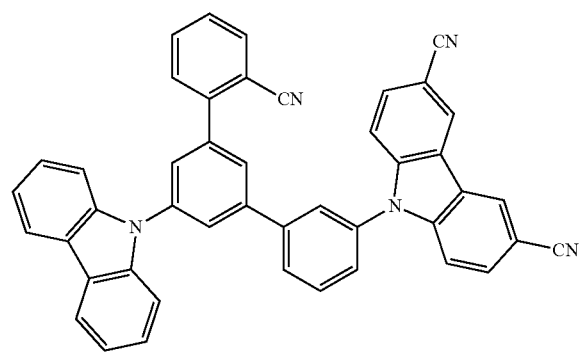
51
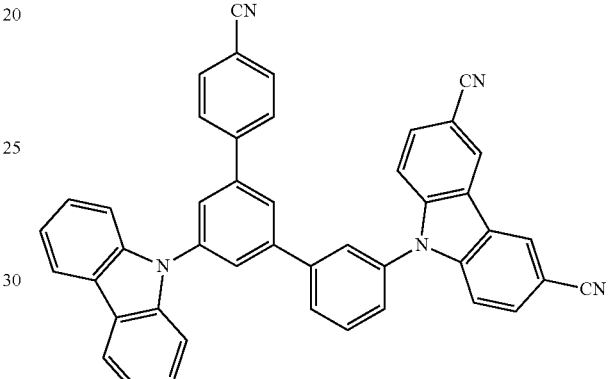
52
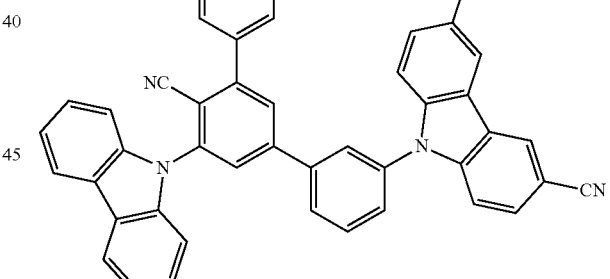
53
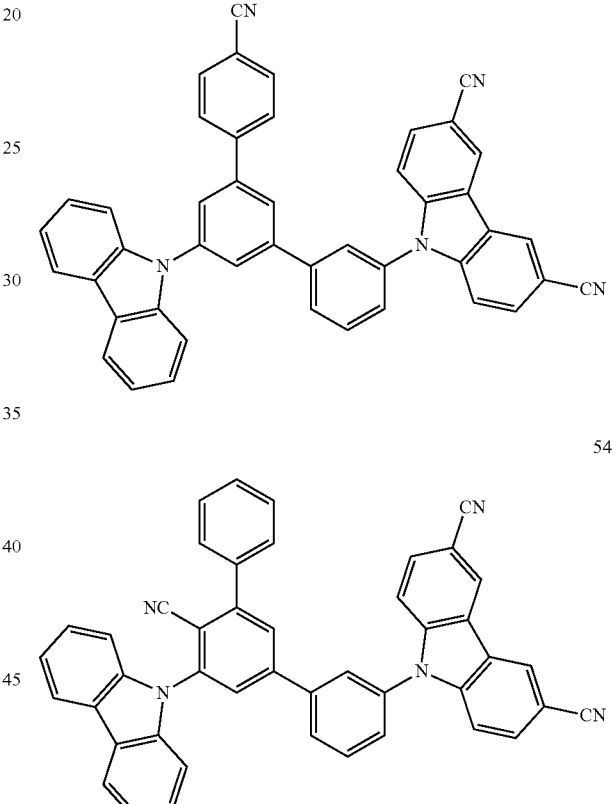
54
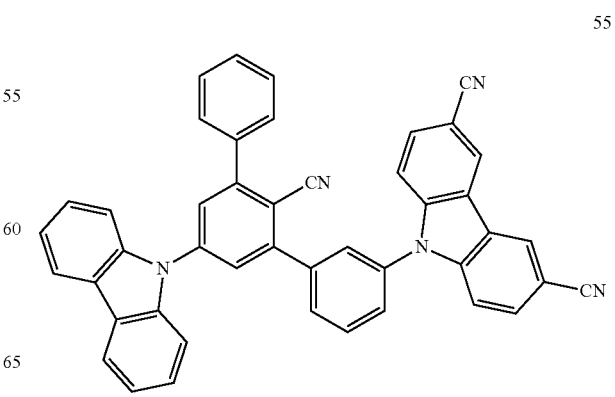
55

-continued
56
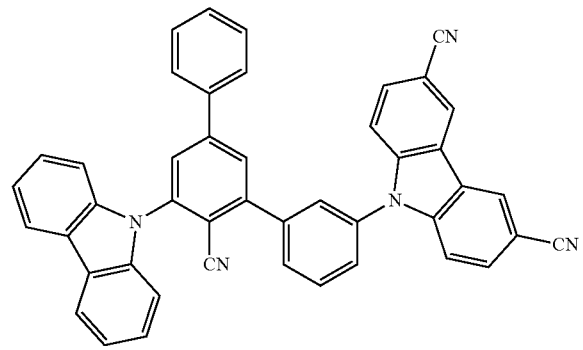
57
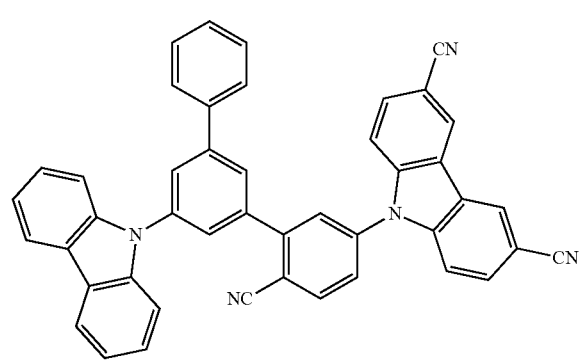
58
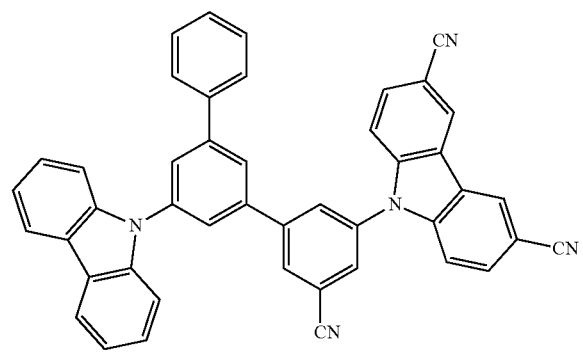
59
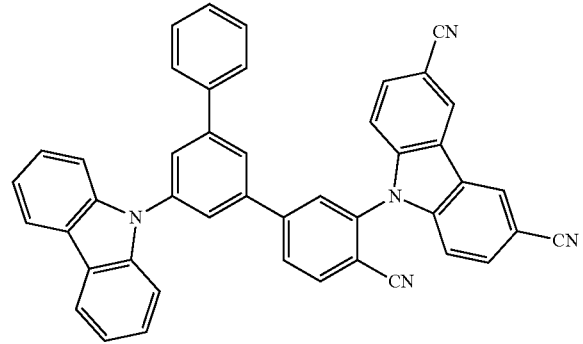
-continued
60
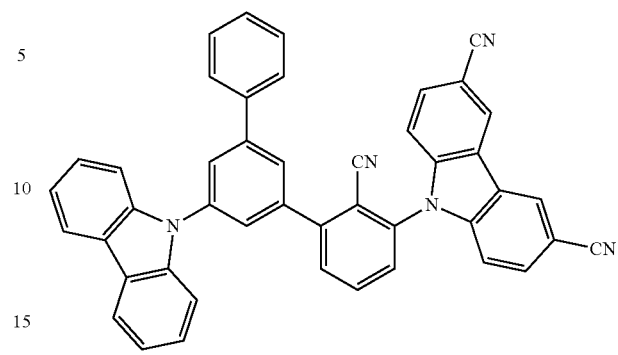
61
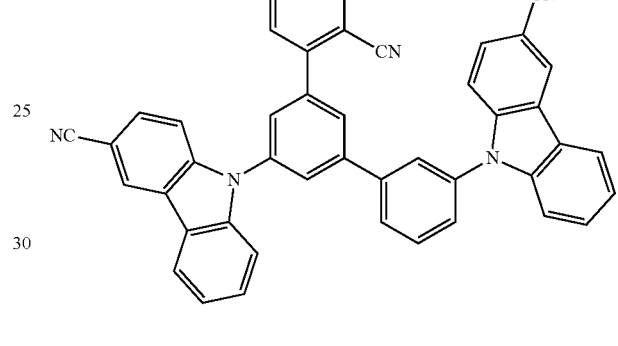
62
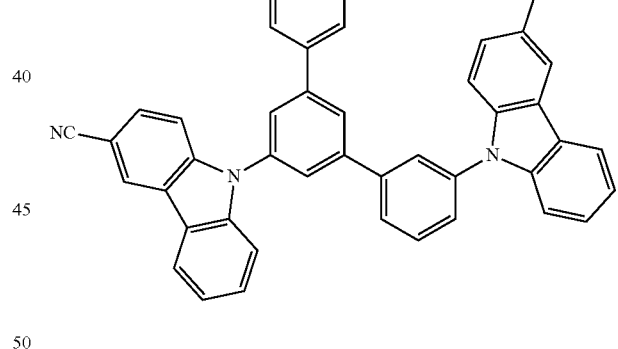
63
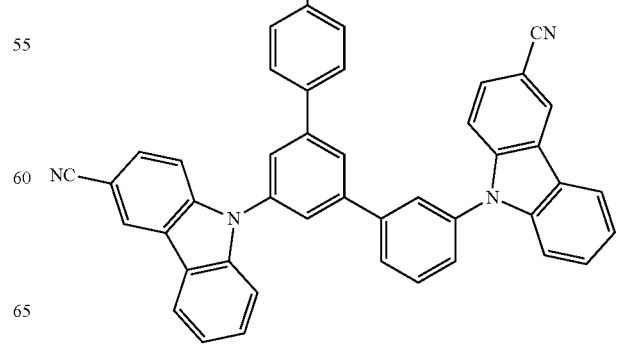

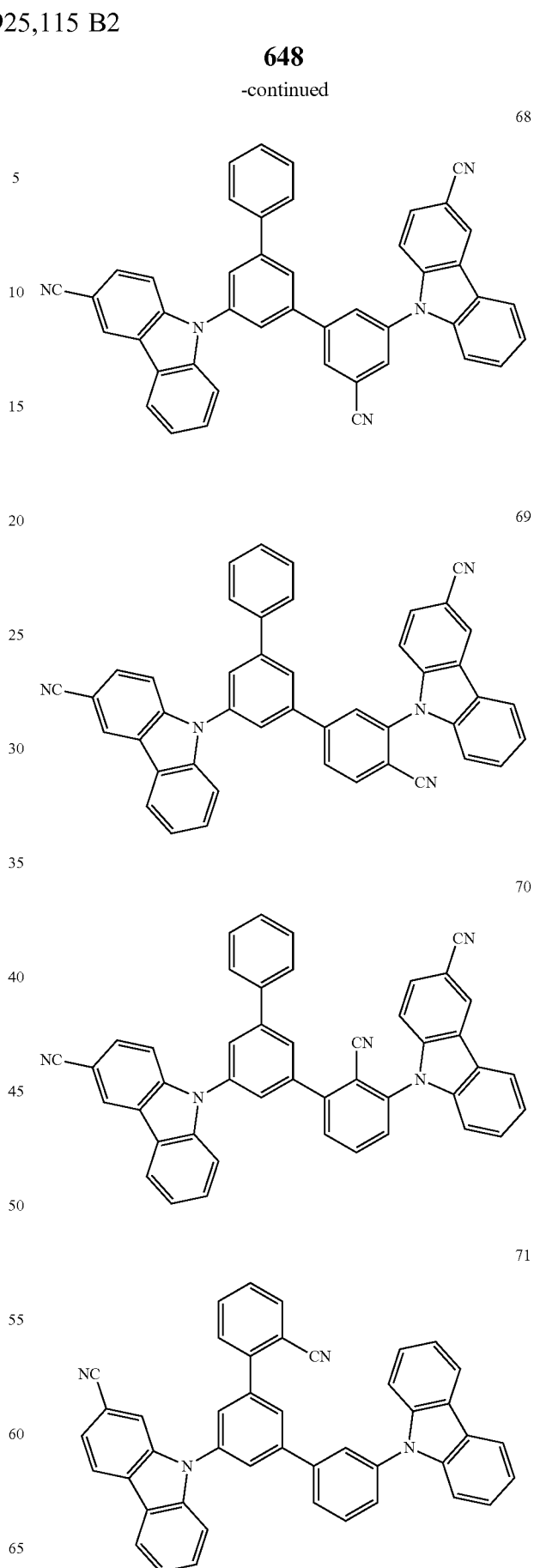

-continued
72
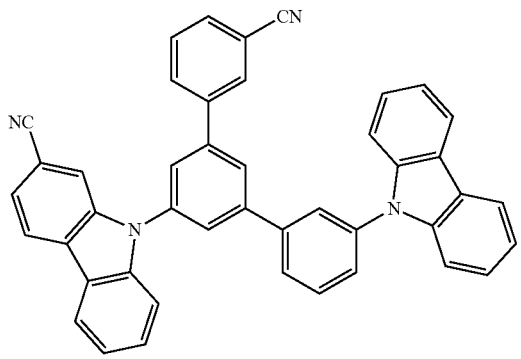
73
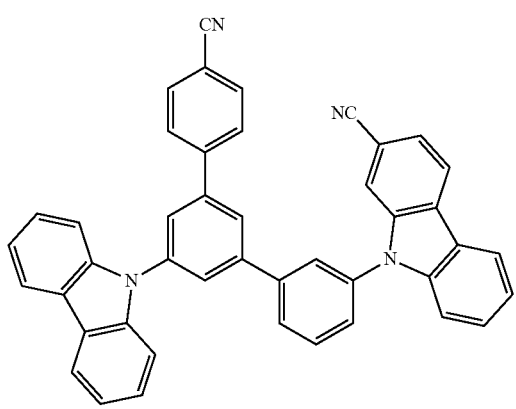
74
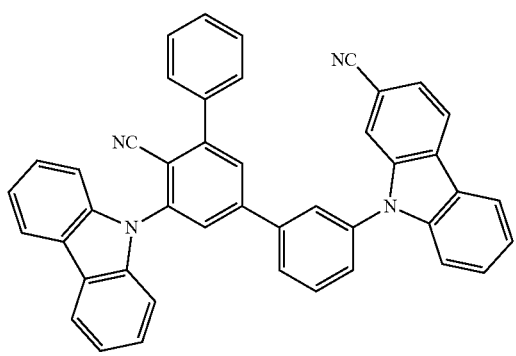
75
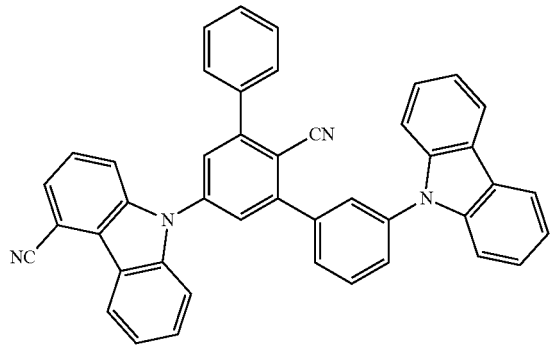
-continued
76
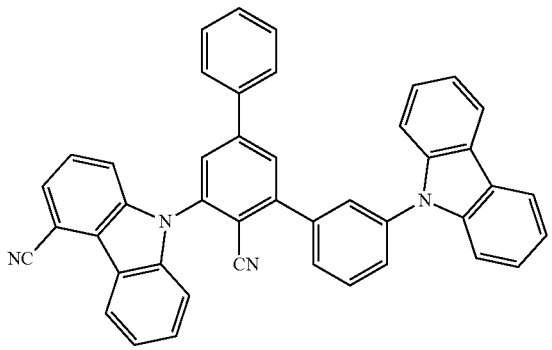
77
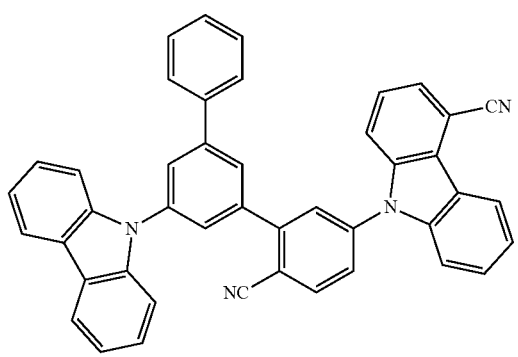
78
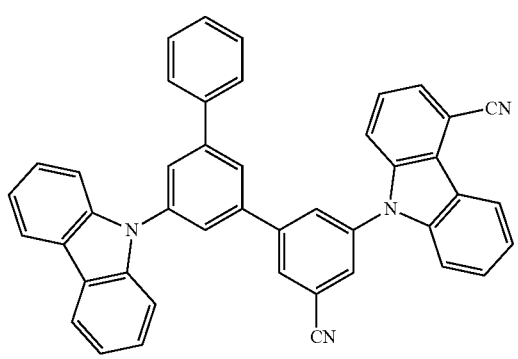
79
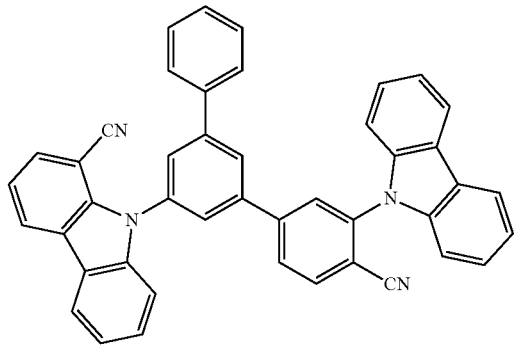

80
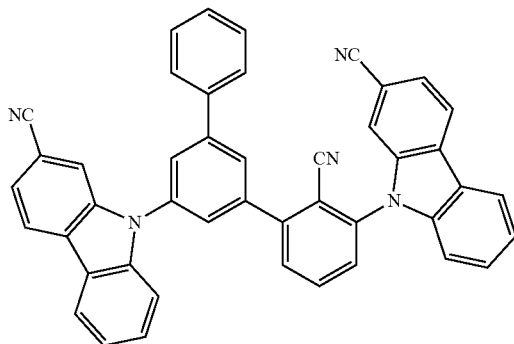
84
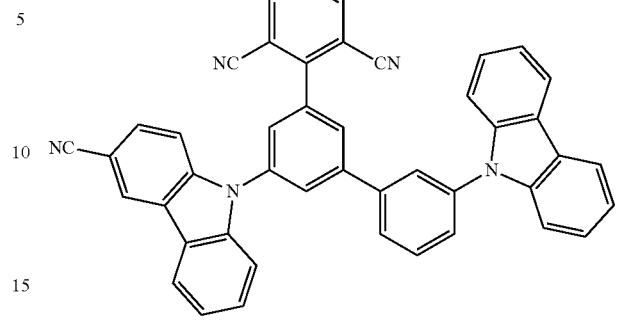
81
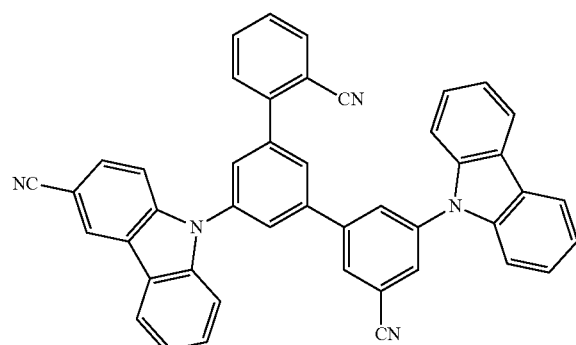
85
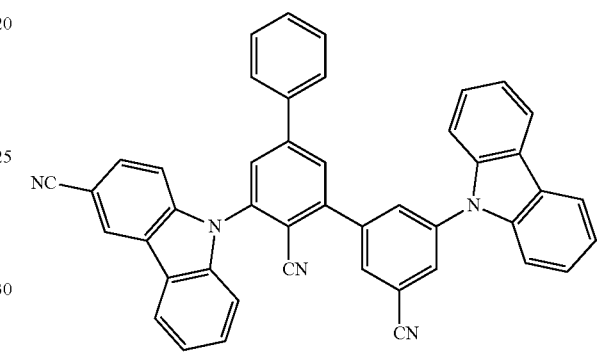
82
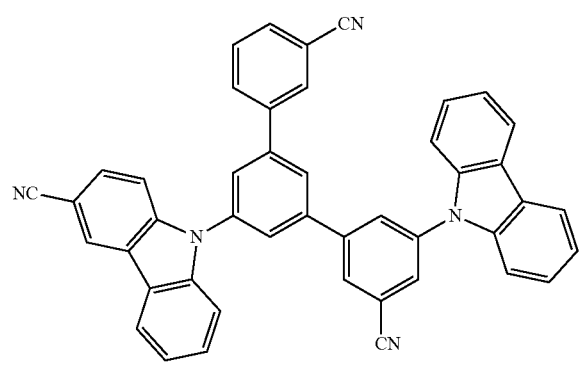
86
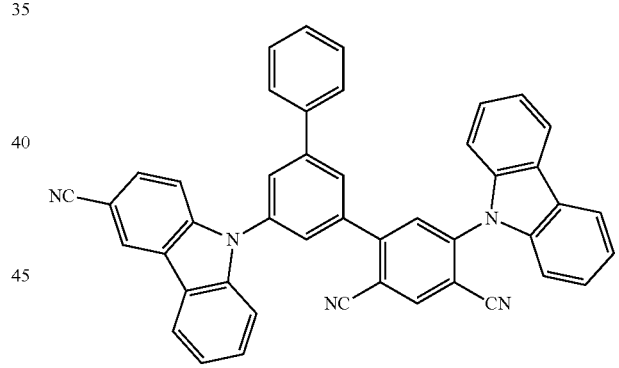
83
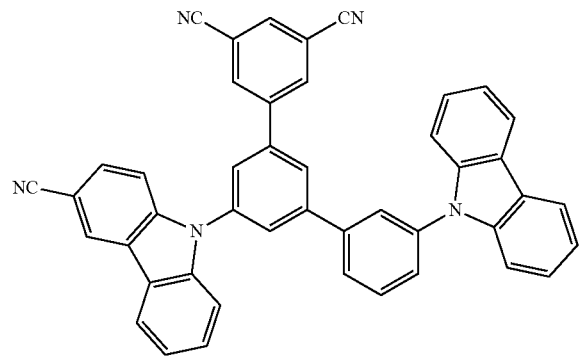
87
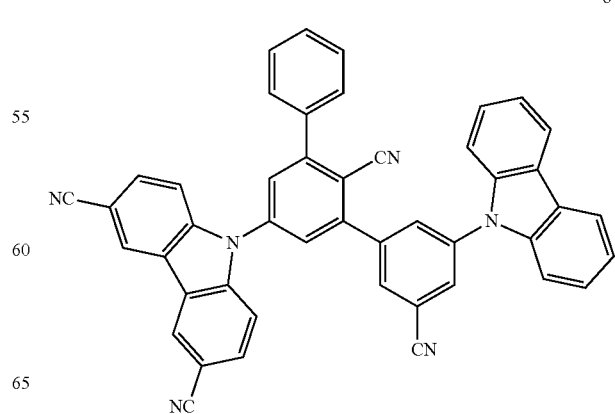

88
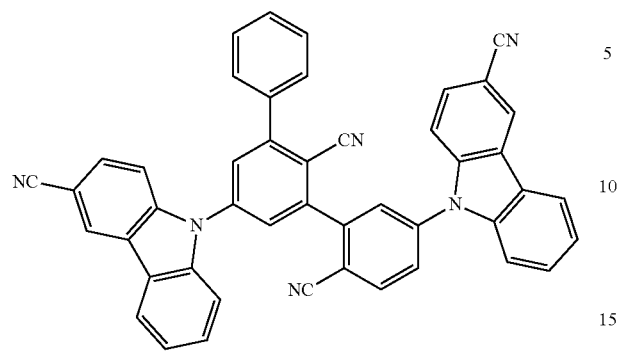
92
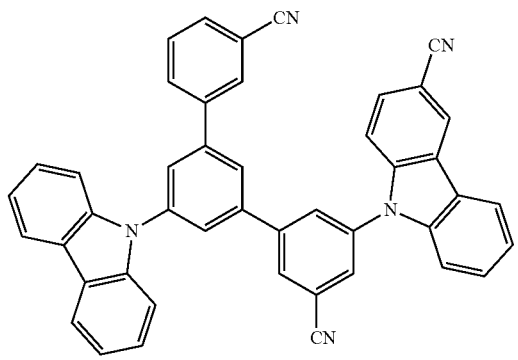
89
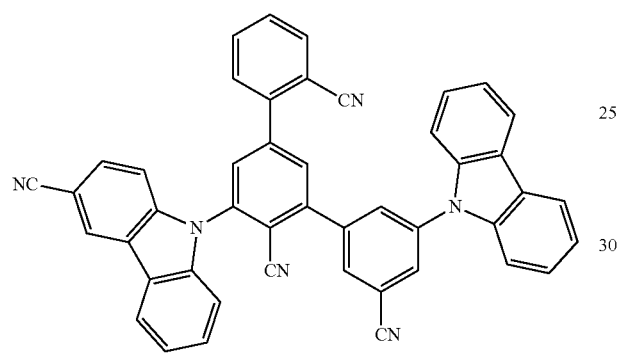
93
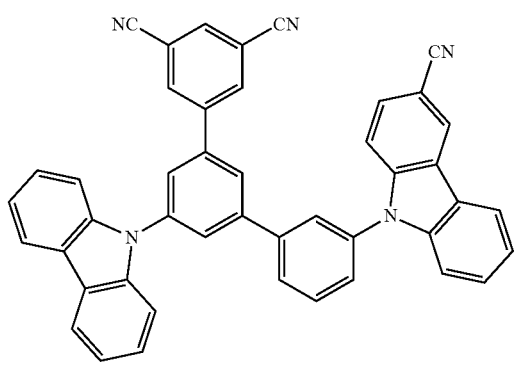
90
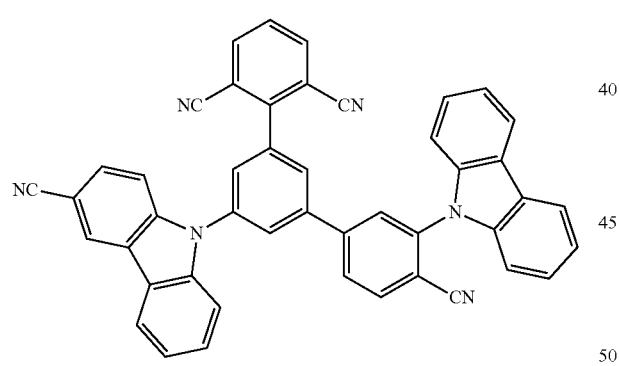
94
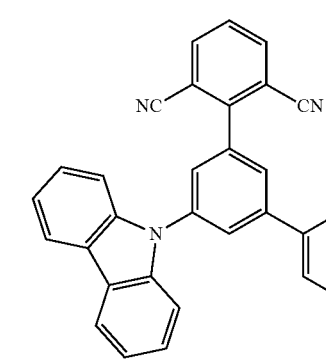
91
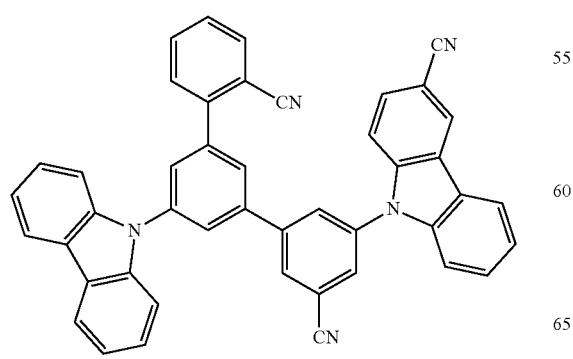
95
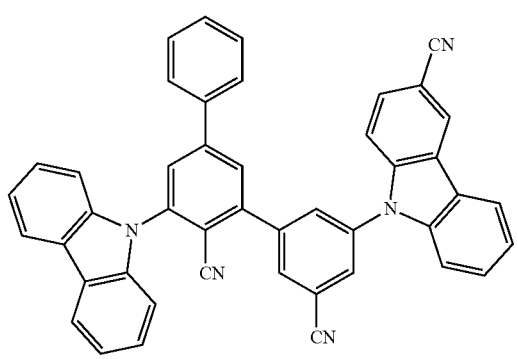

655
-continued
96
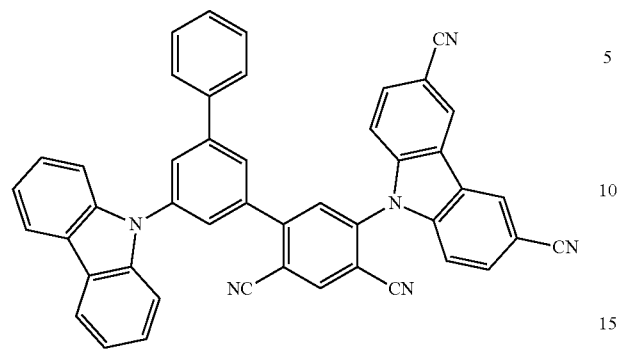
97
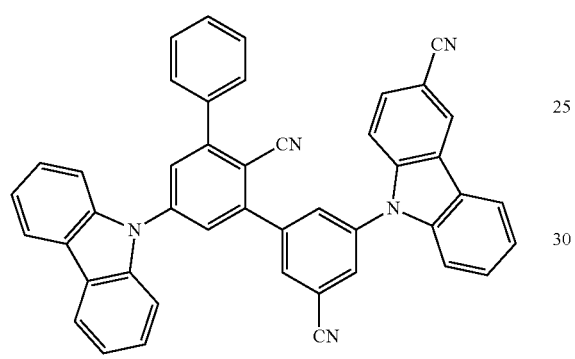
98
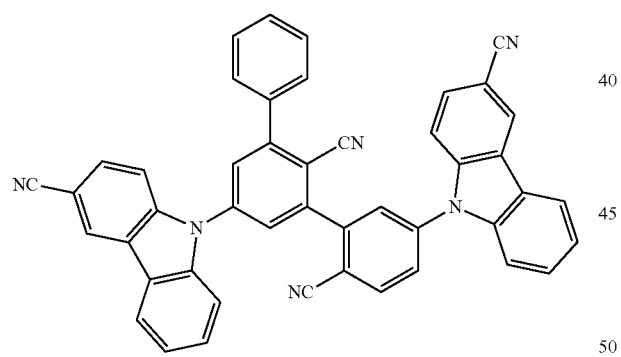
99
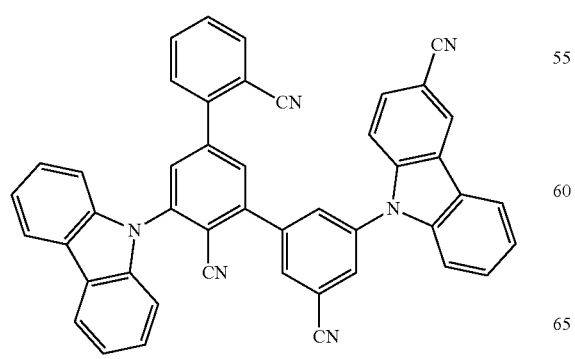
656
-continued
100
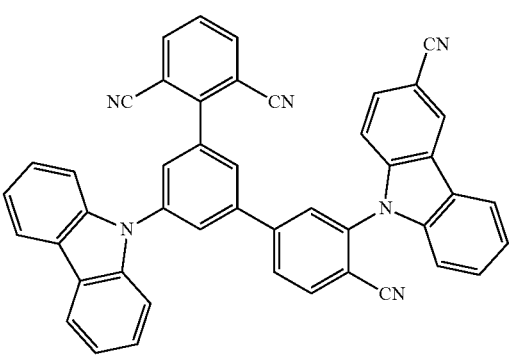
101
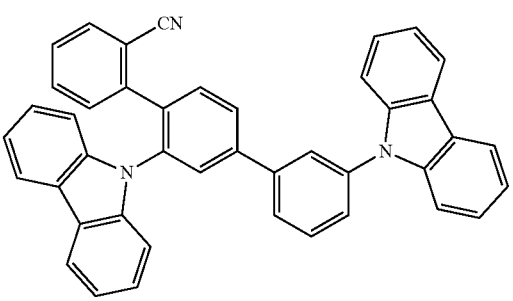
102
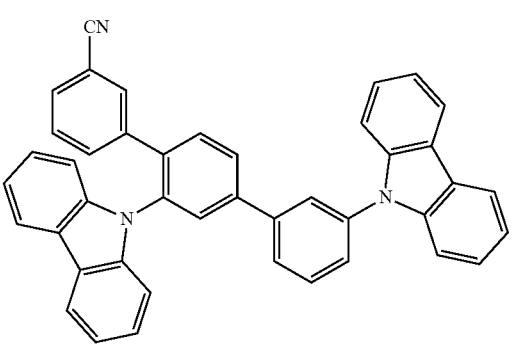
103
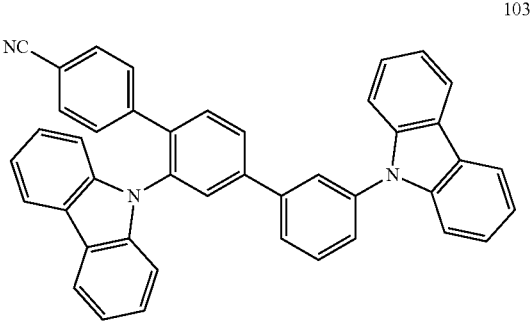

104
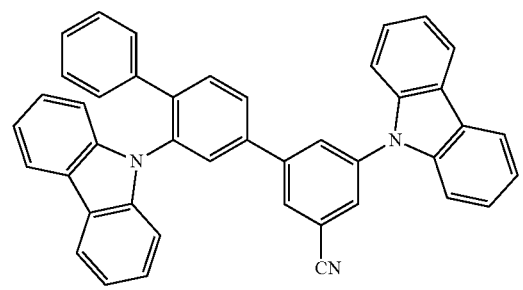
105
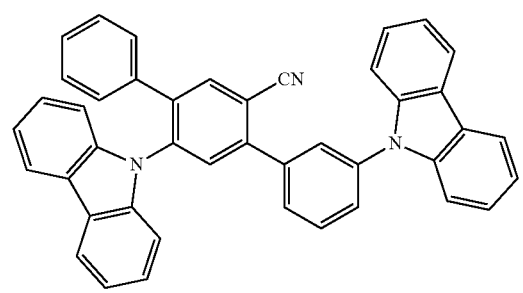
106
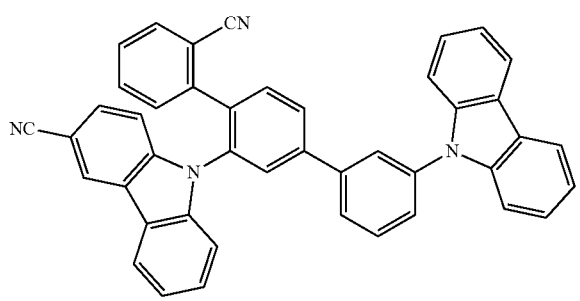
107
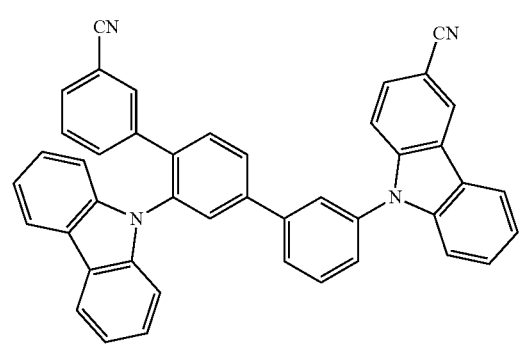
108
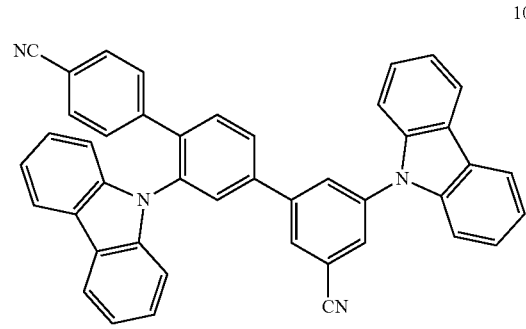
109
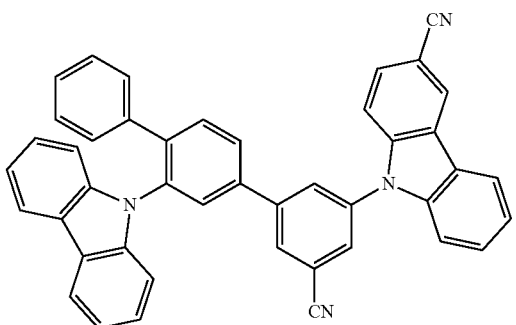
110
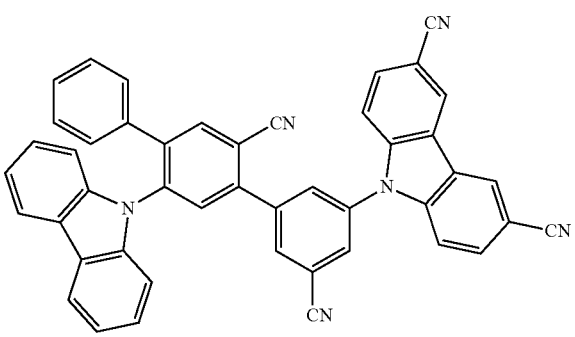
111
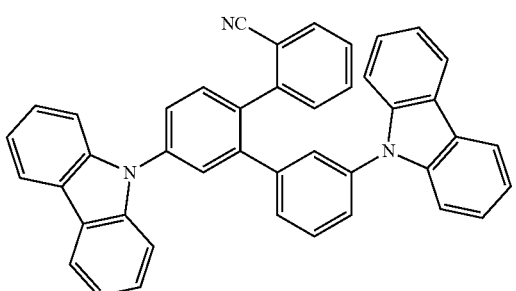
112
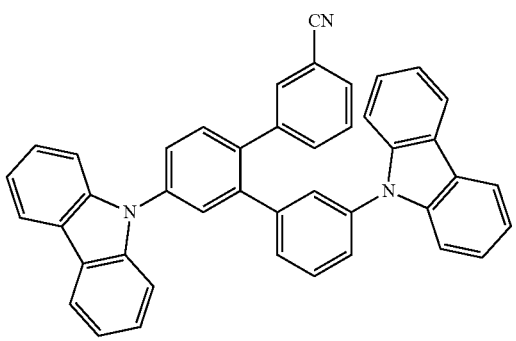

-continued
113
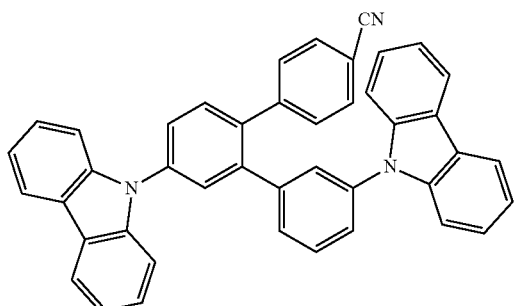
114
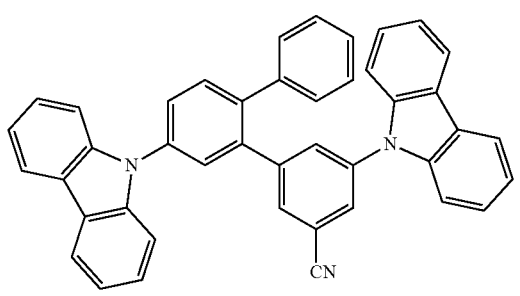
115
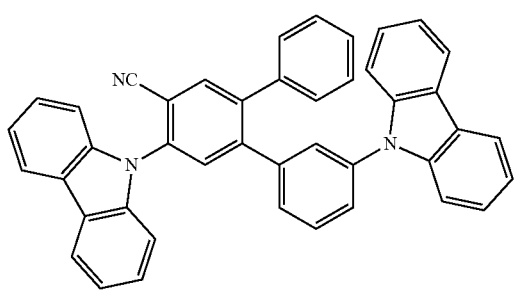
116
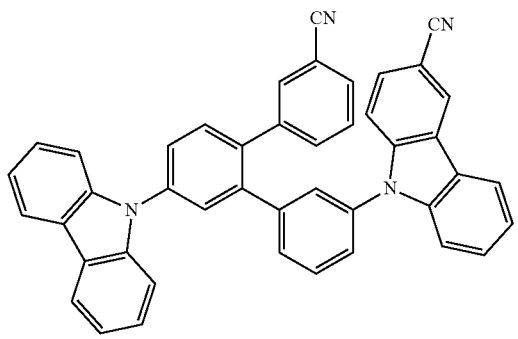
117
-continued
118
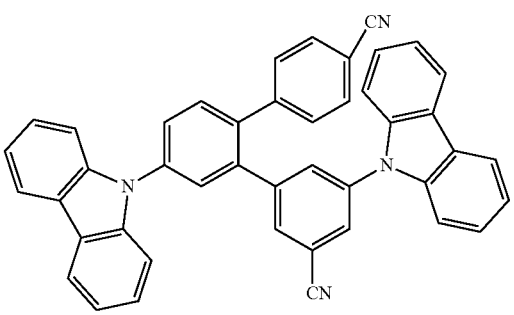
119
120
121
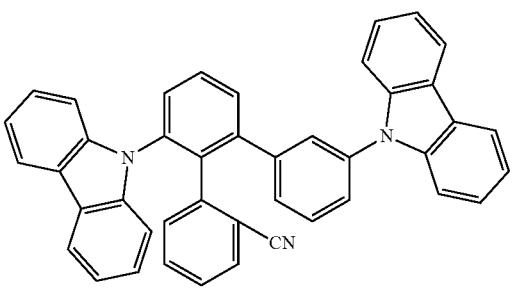

122
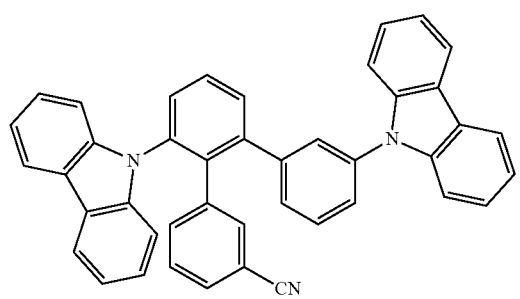
123
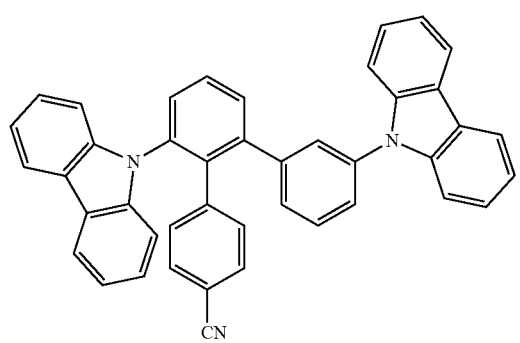
124
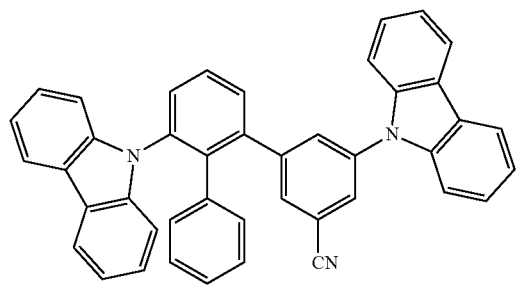
125
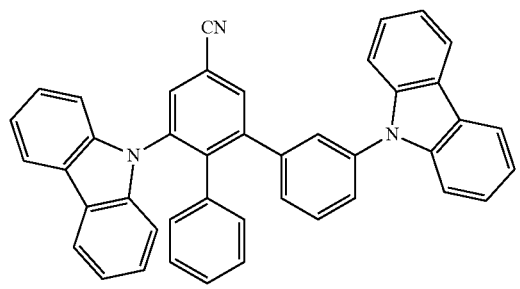
126
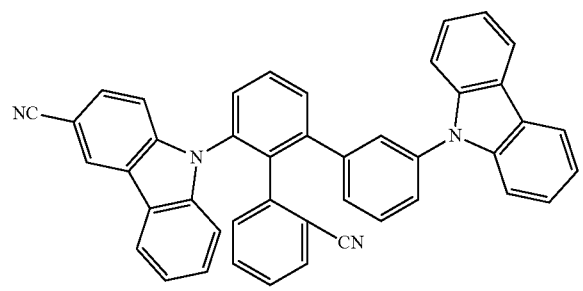
127
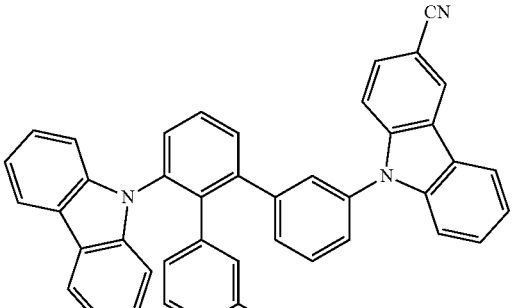
128
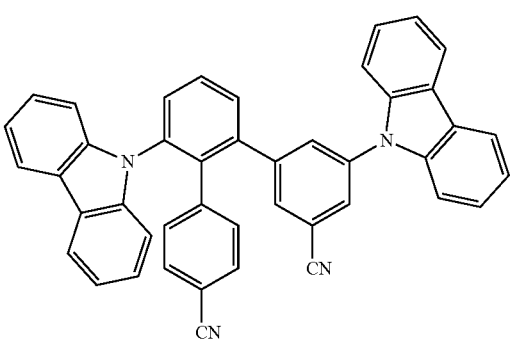
129
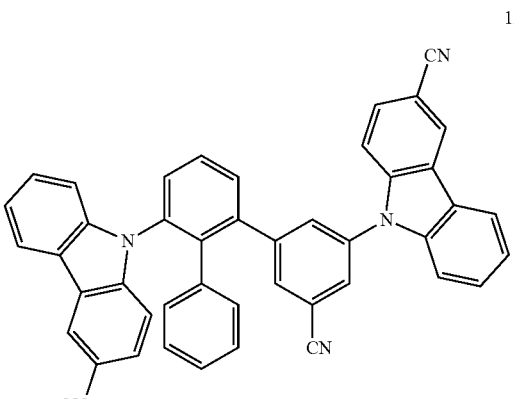
130
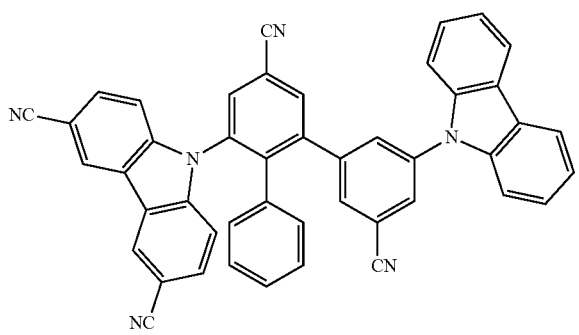

131
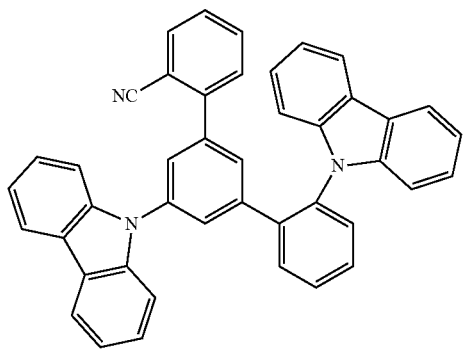
132
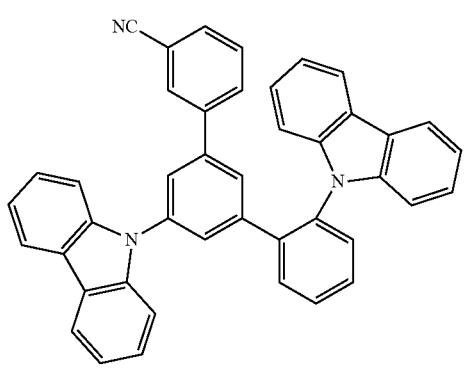
133
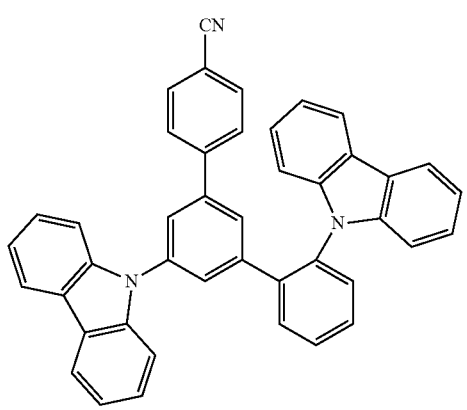
134
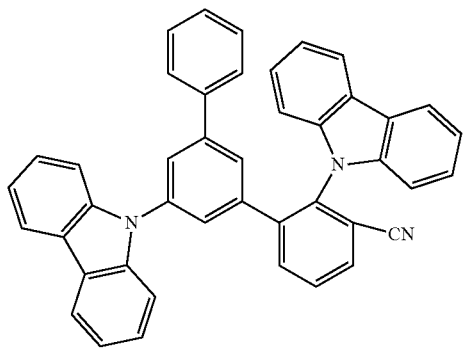
135
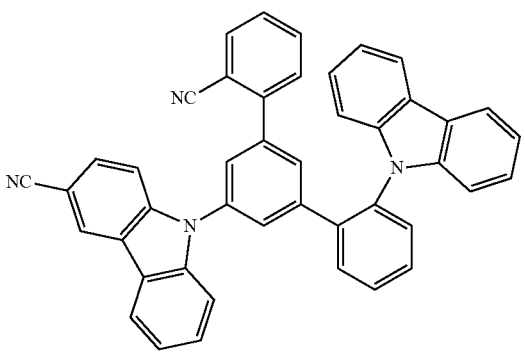
136
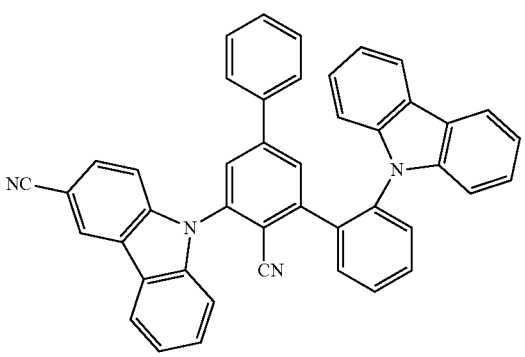
137
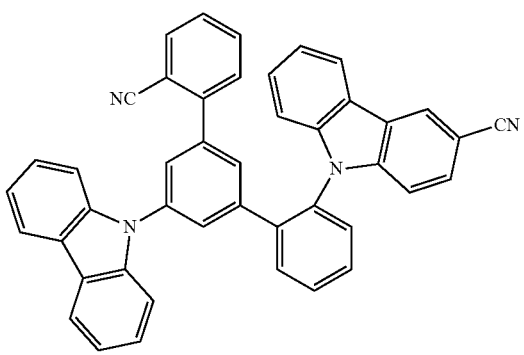
138
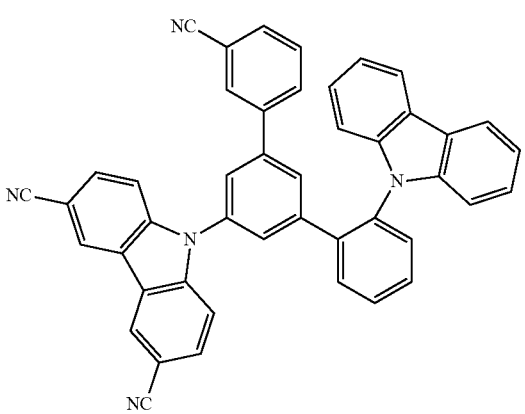

139
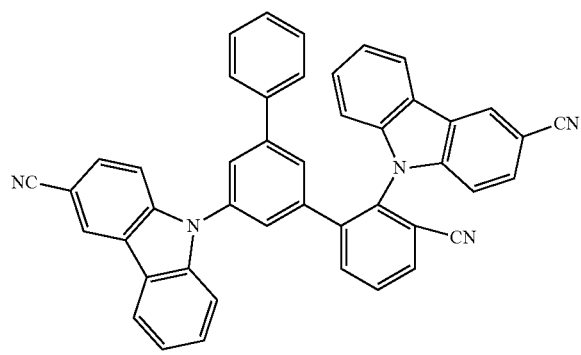
143
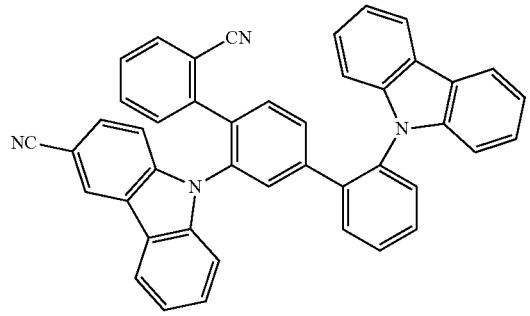
140
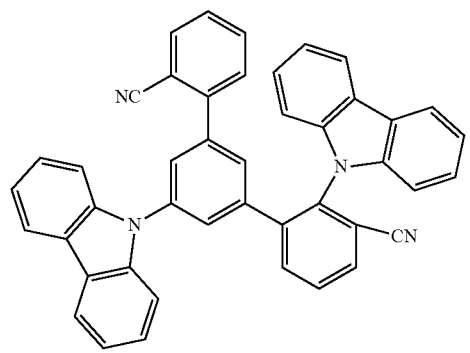
144
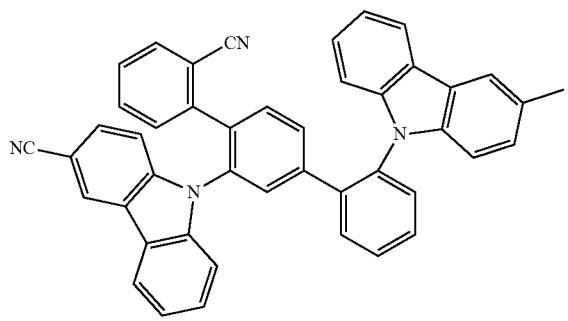
141
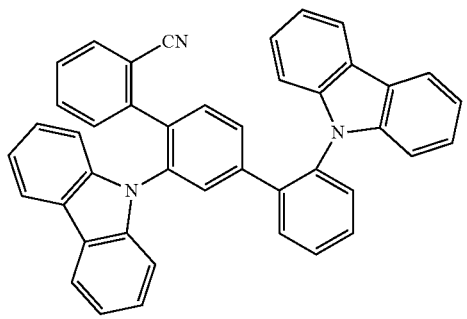
145
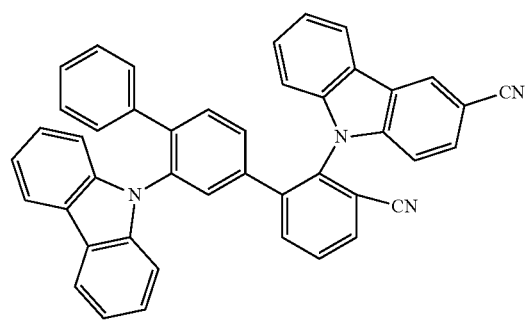
142
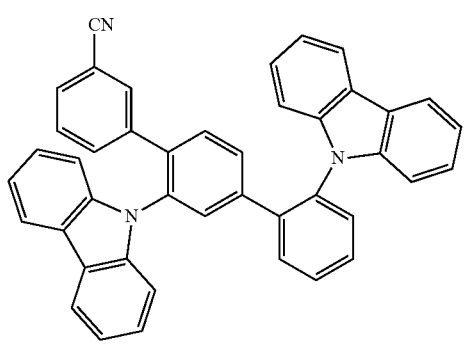
146
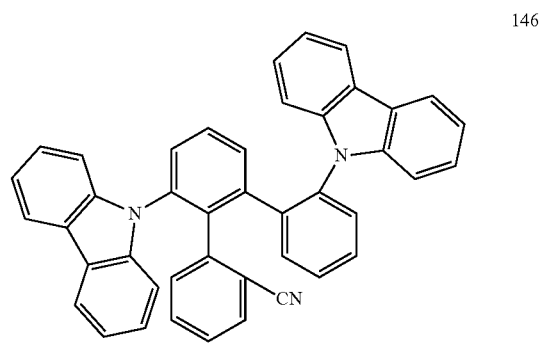

147
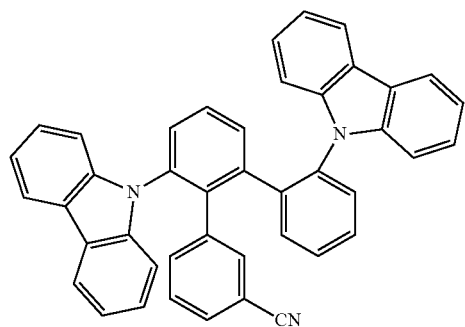
148
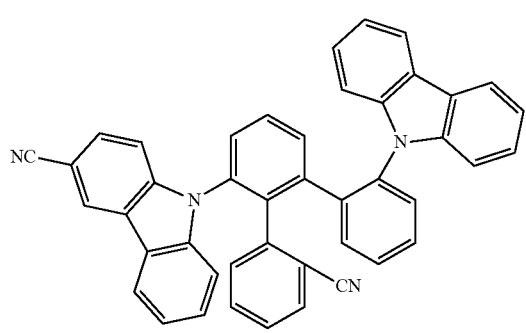
149
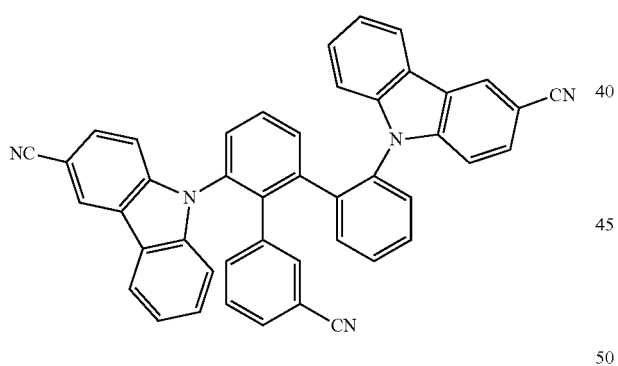
150
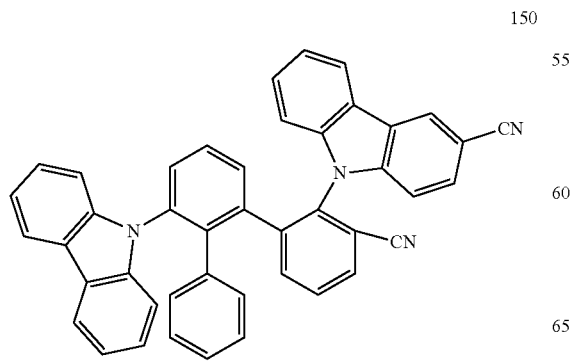
151
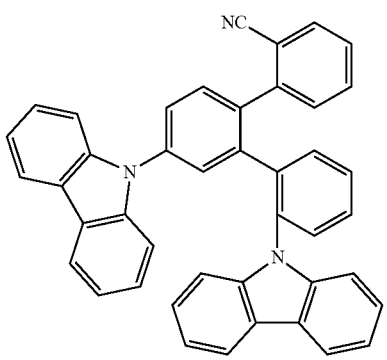
152
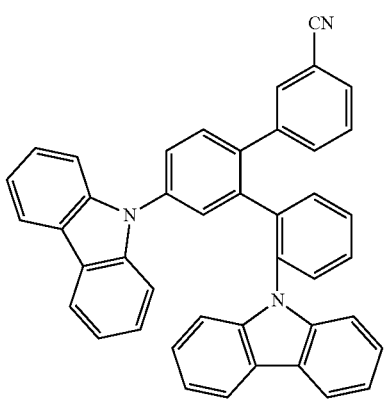
153
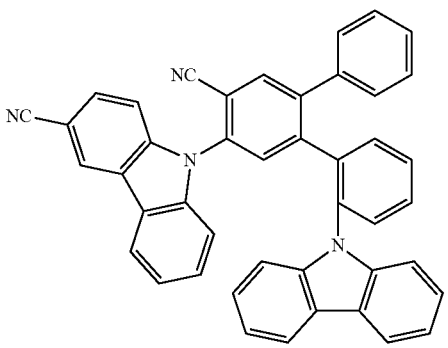
154
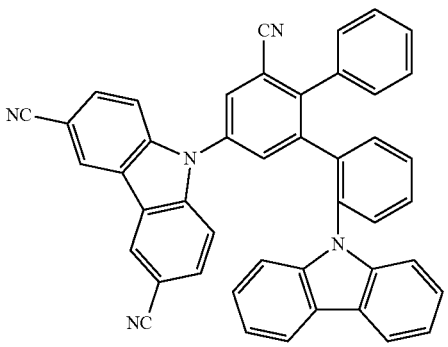

669
-continued
155
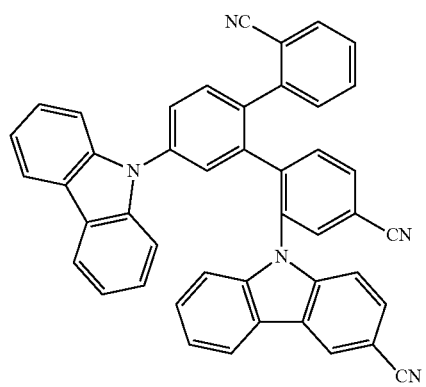
156
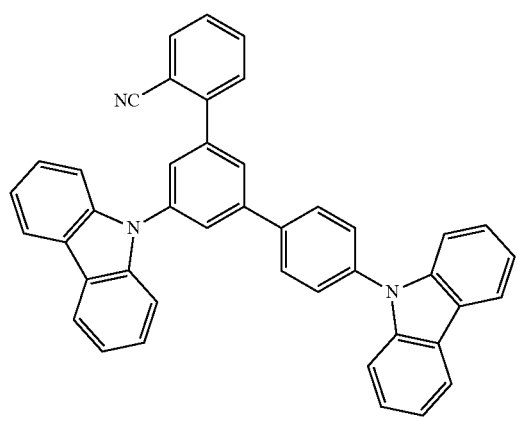
157
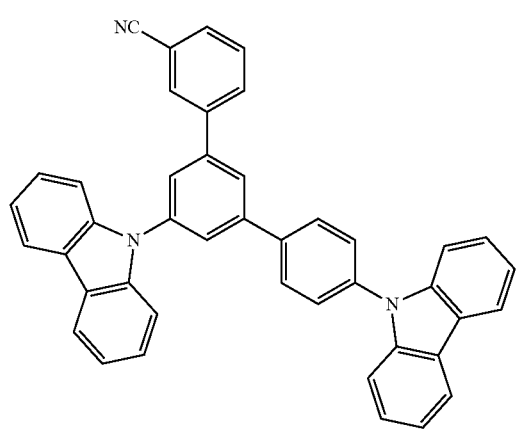
670
-continued
158
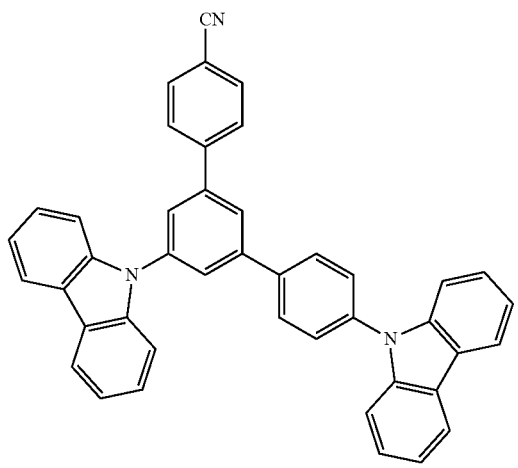
159
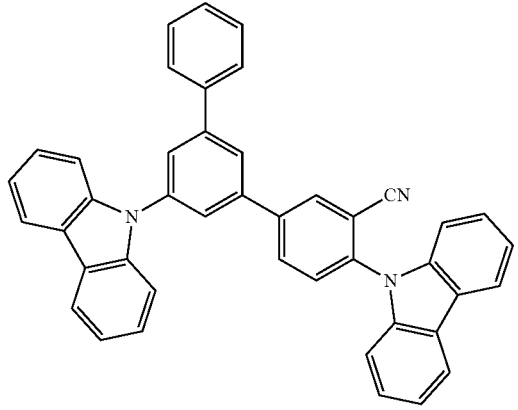
160
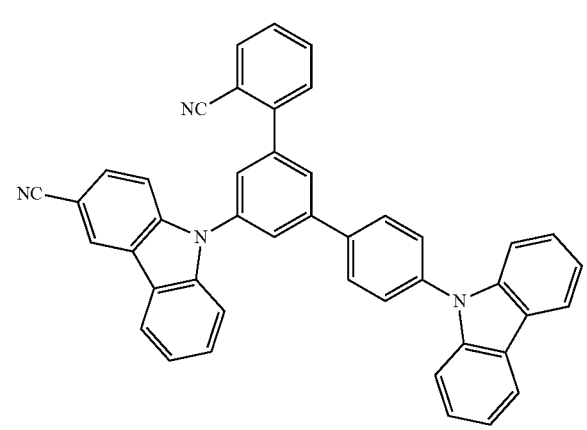

161
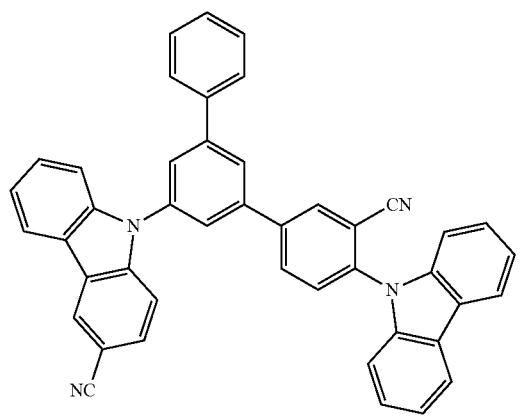
162
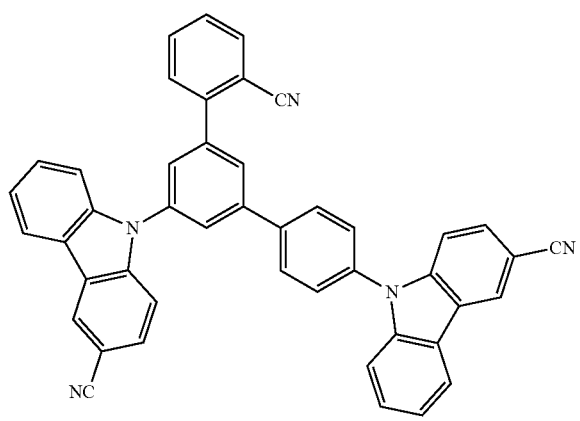
163
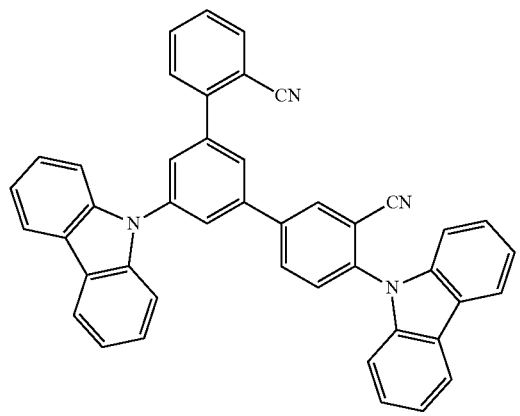
164
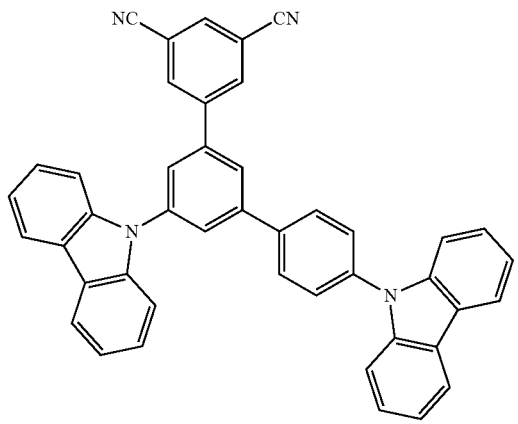
165
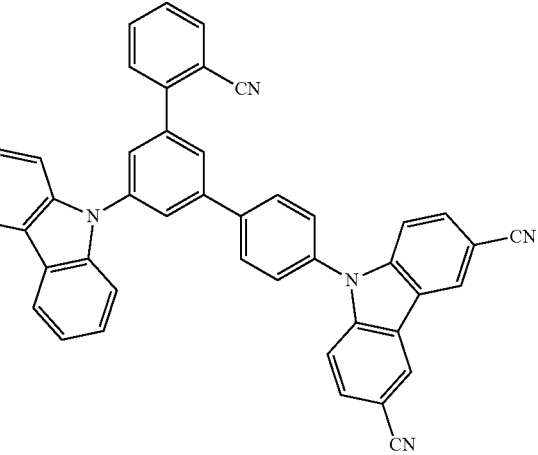
166
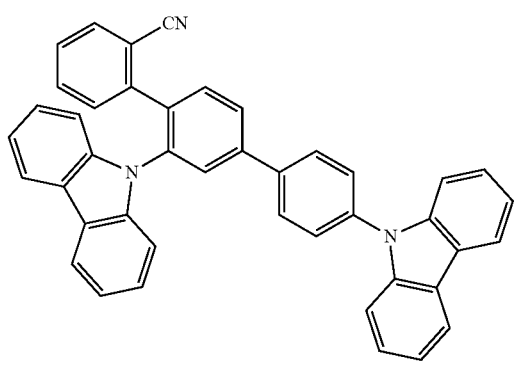

167
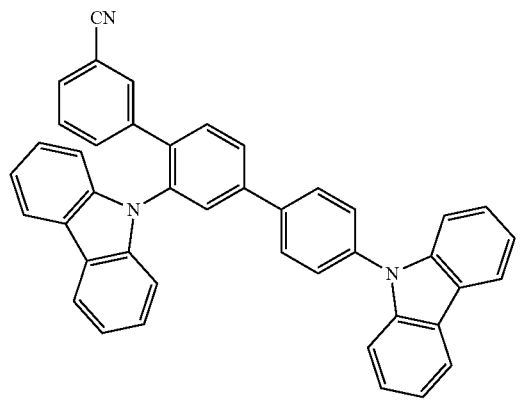
168
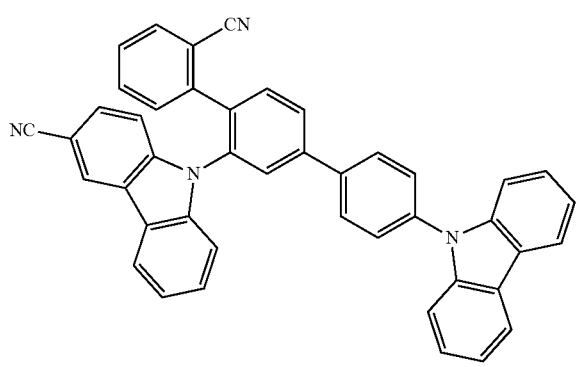
169
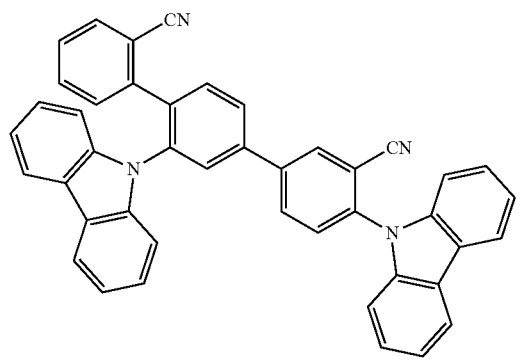
170
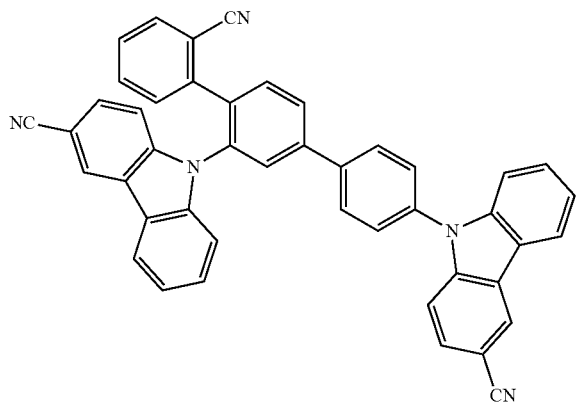
171
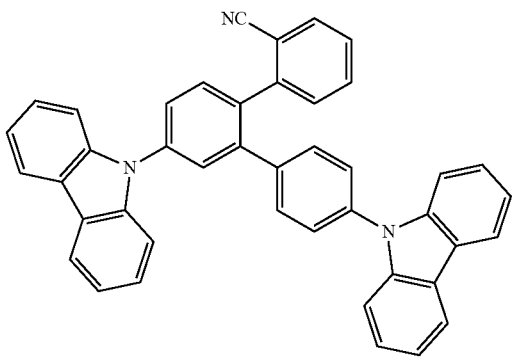
172
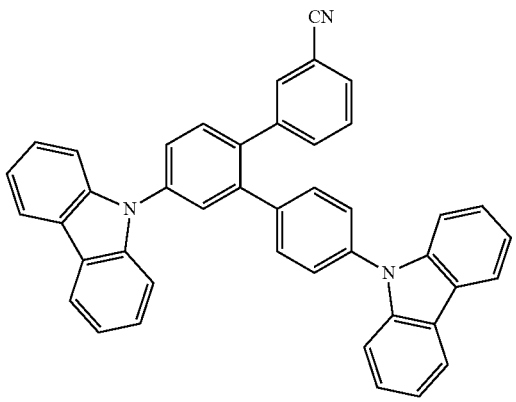
173
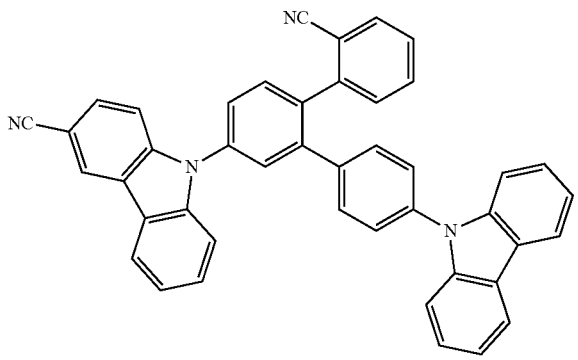
174
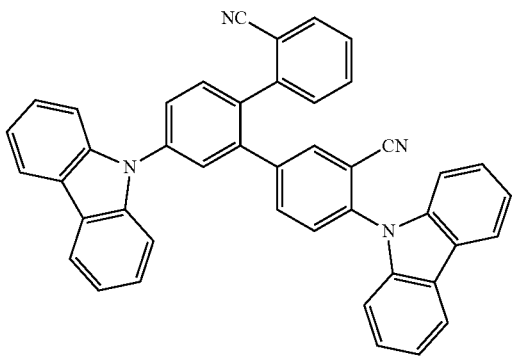

175
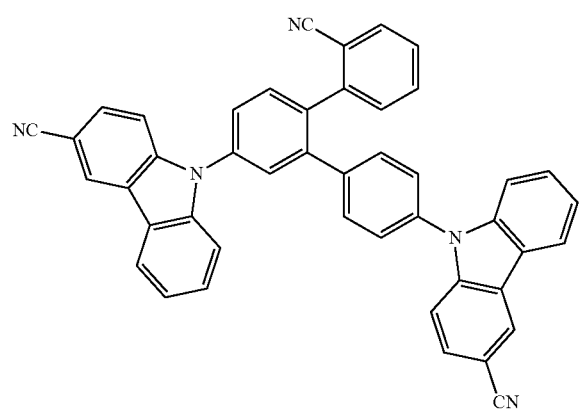
176
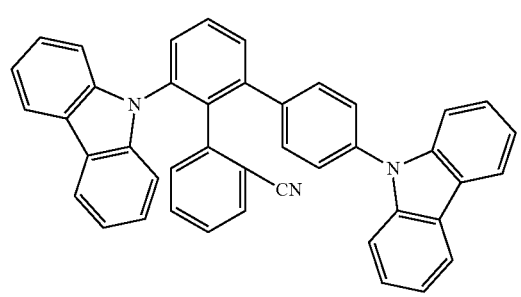
177
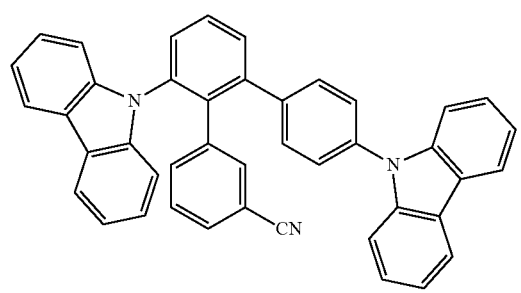
178
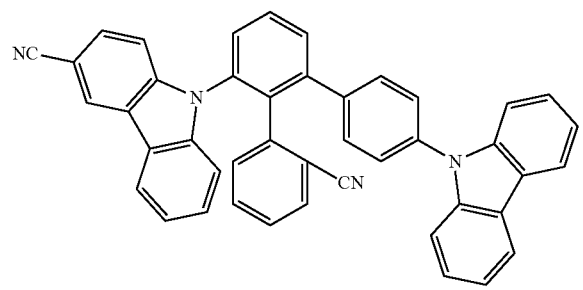
179
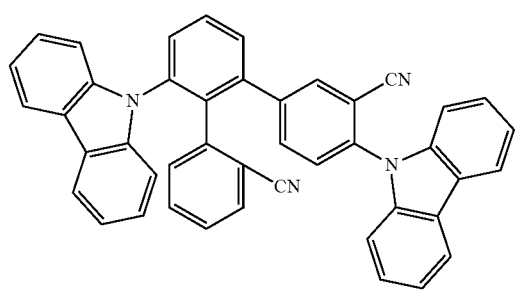
180
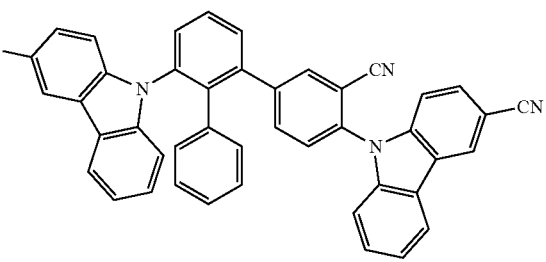
181
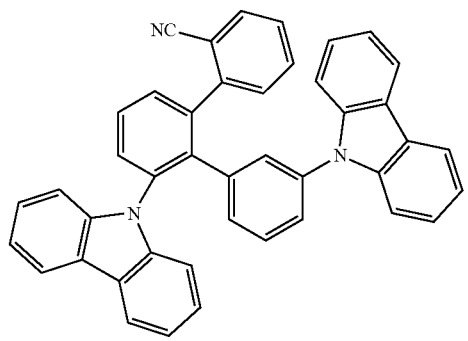
182
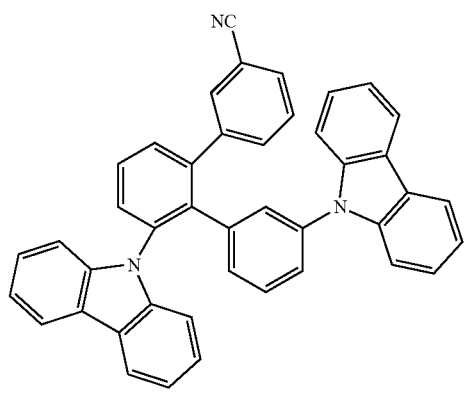

183
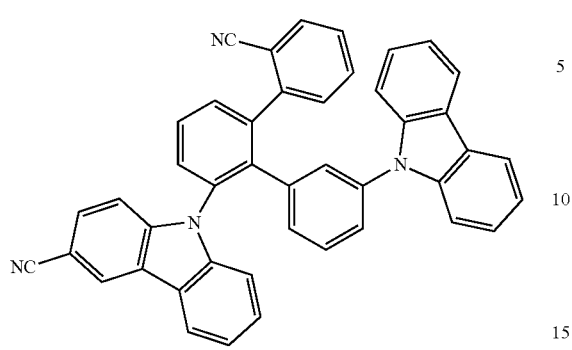
184
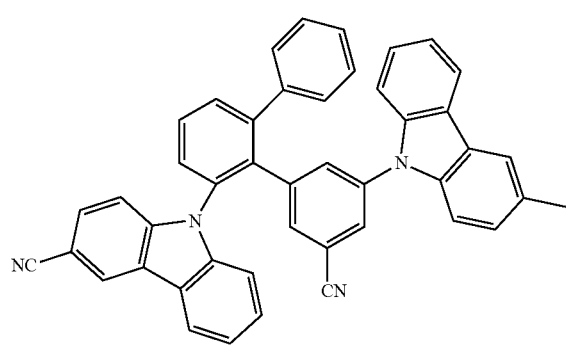
185
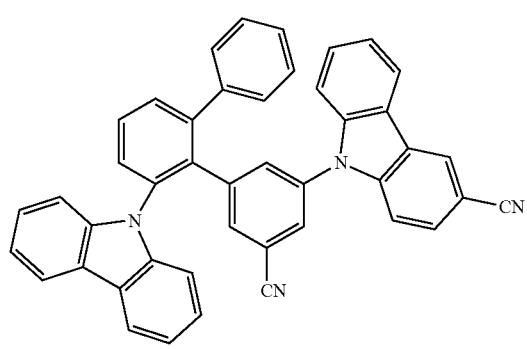
186
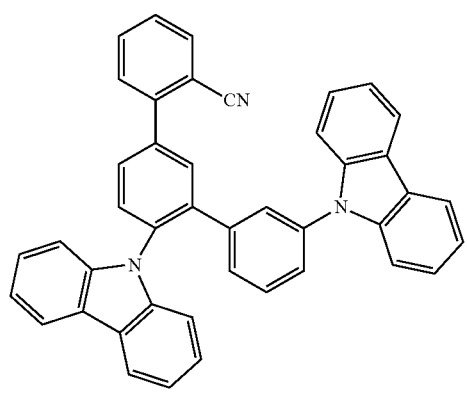
187
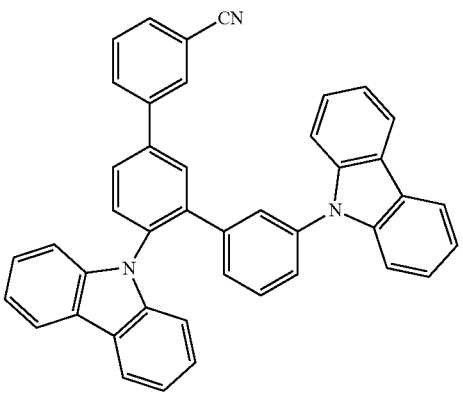
188
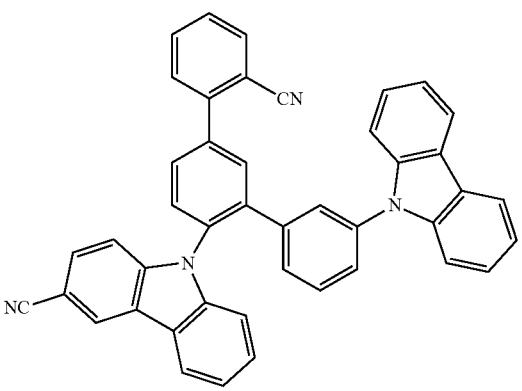
189
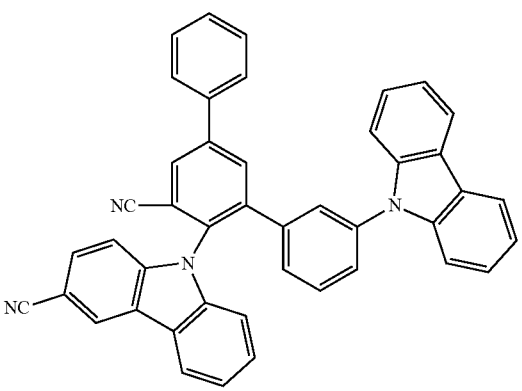
190
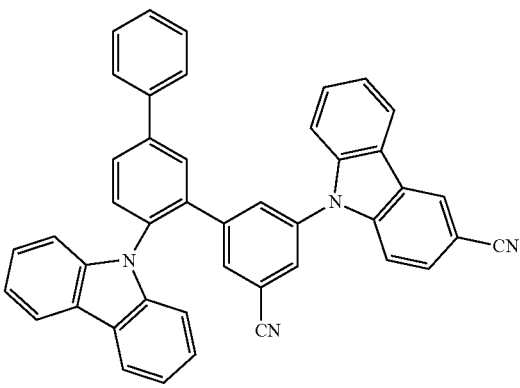

| 191 | 195 |
|---|---|
| 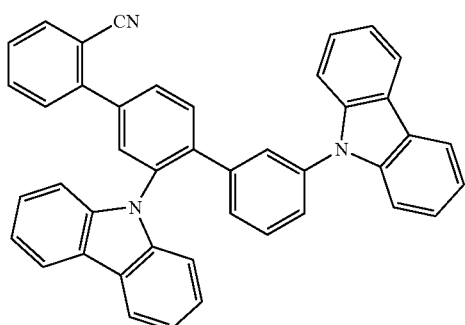 | 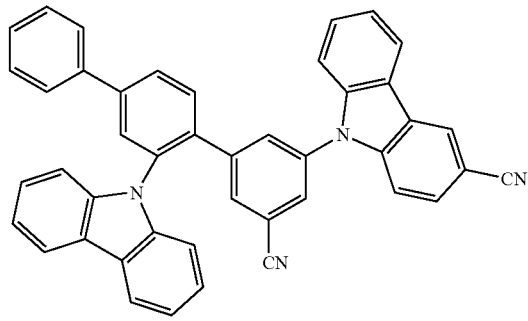 |
| 192 | 196 |
| 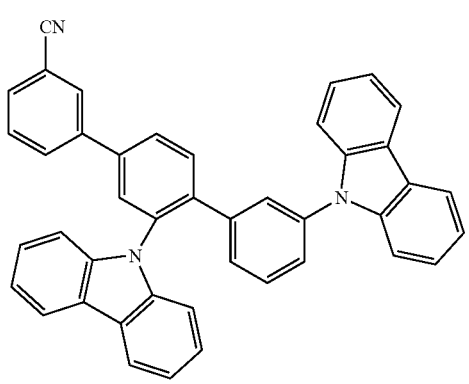 | 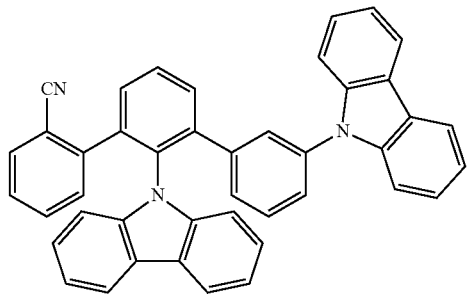 |
| 193 | 197 |
| 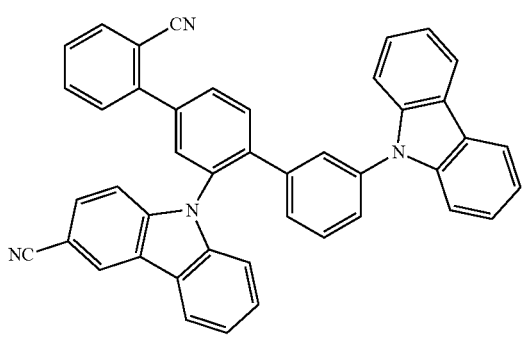 | 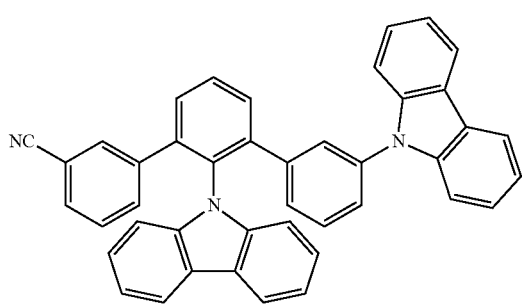 |
|  | 198 |
|  | 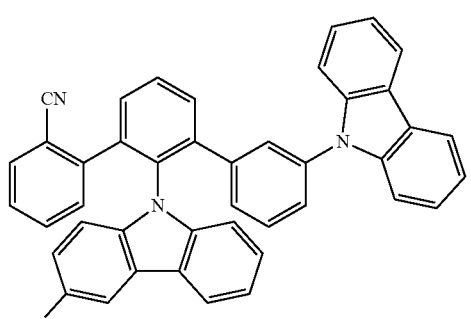 |
| 194 | 199 |
| 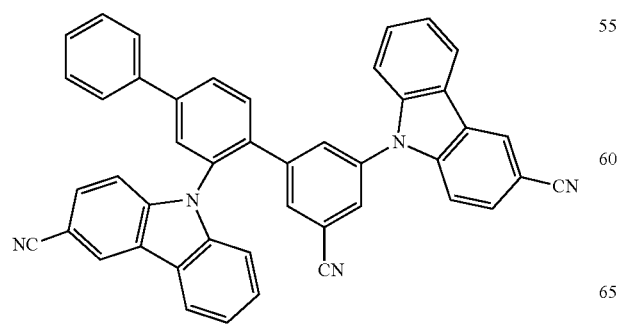 | 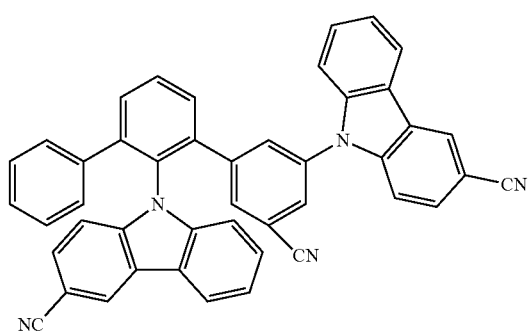 |

-continued
200
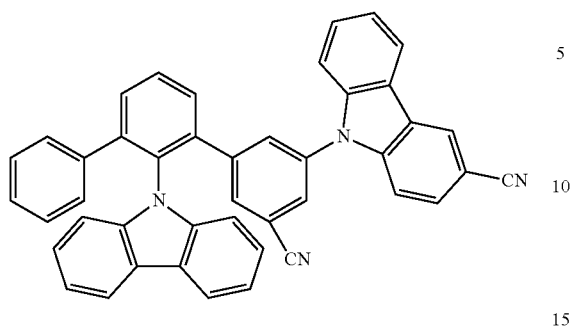
201
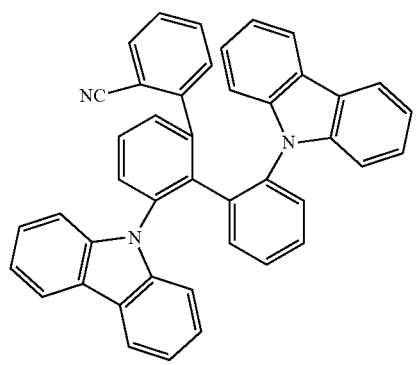
202
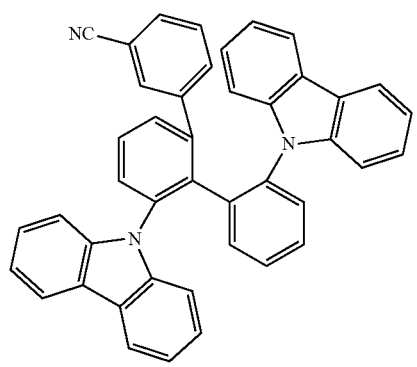
203
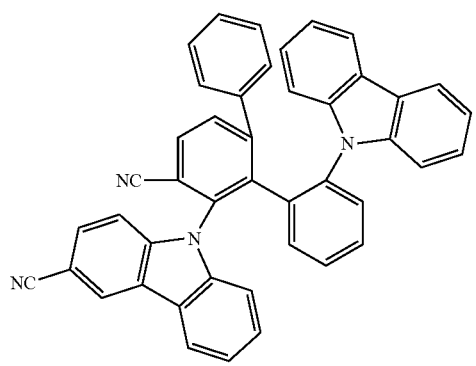
-continued
204
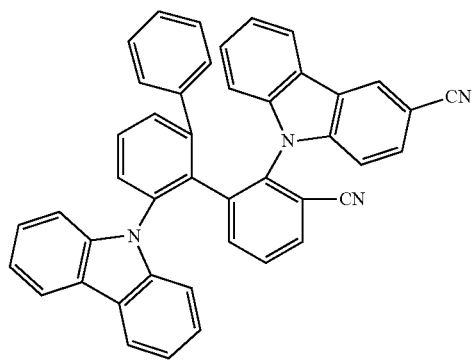
205
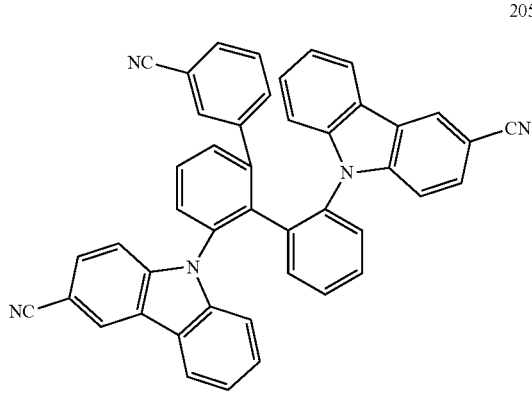
206
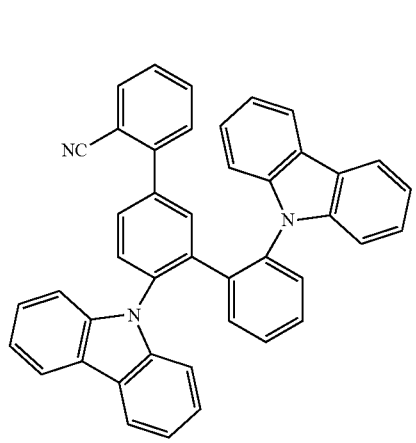
207

208
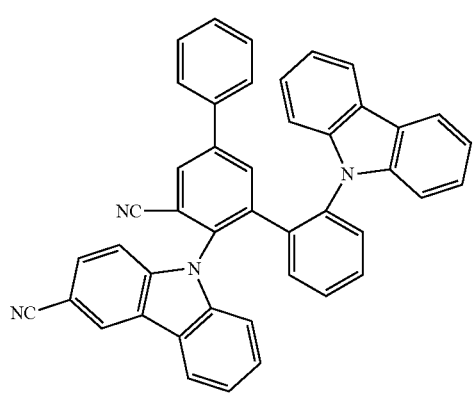
209
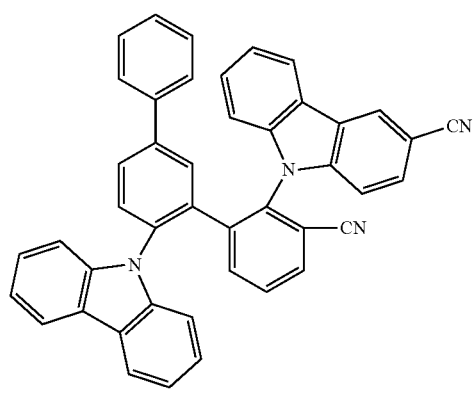
210
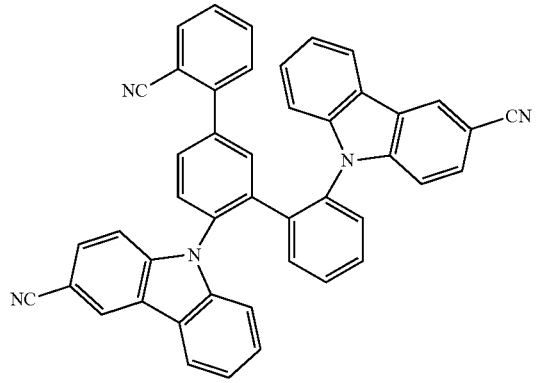
211
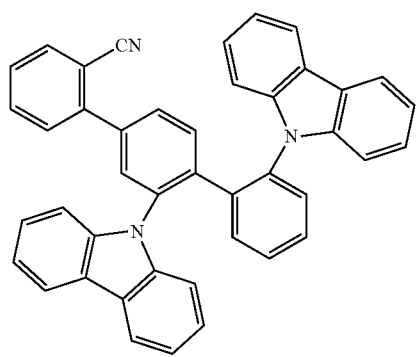
212
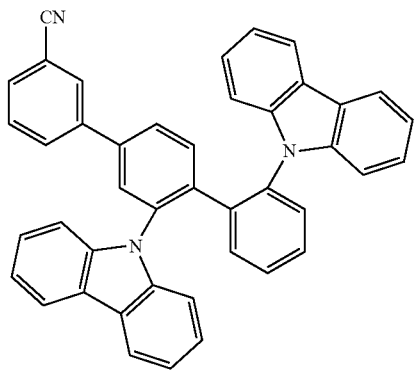
213
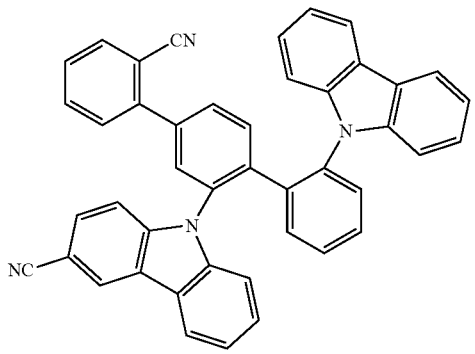
214
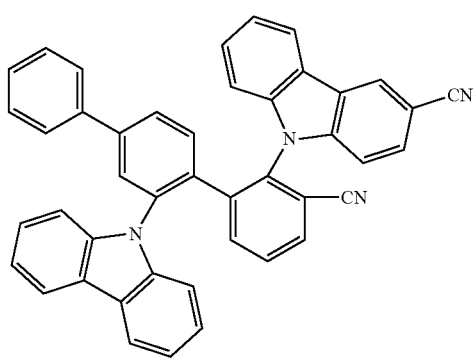
215
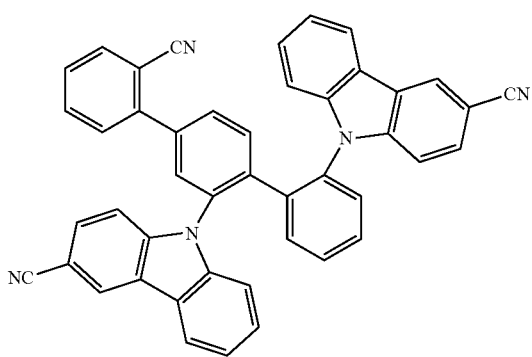

-continued
216
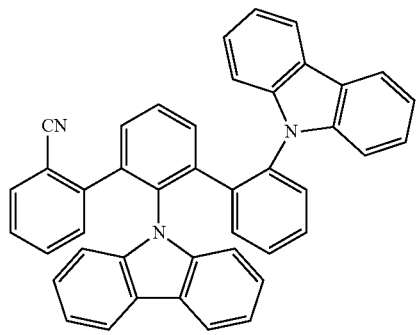
217
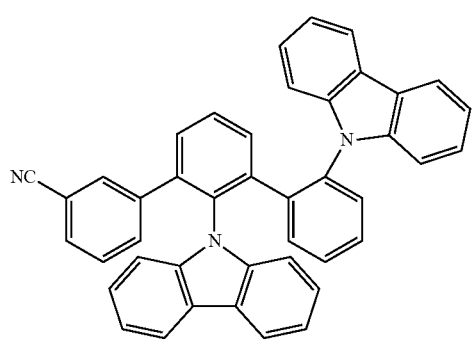
218
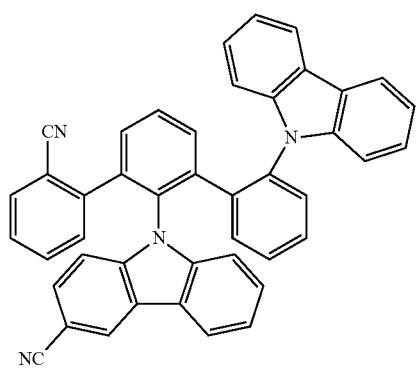
219
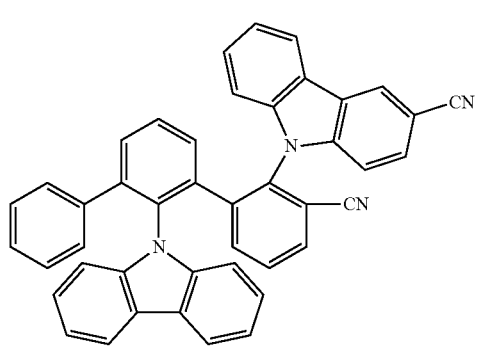
-continued
220
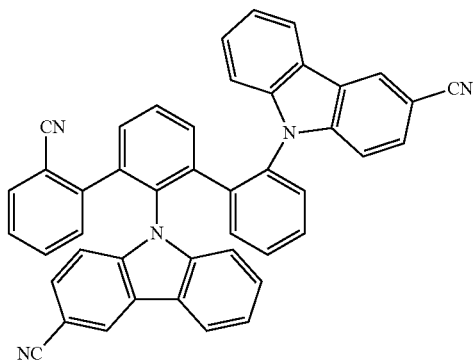
221
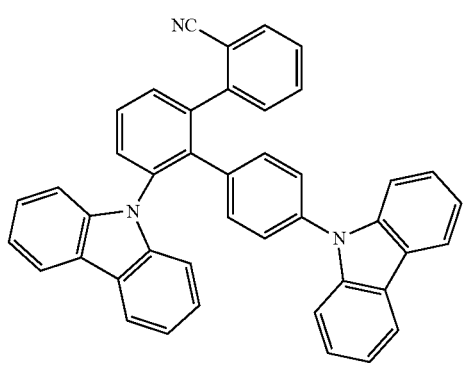
222
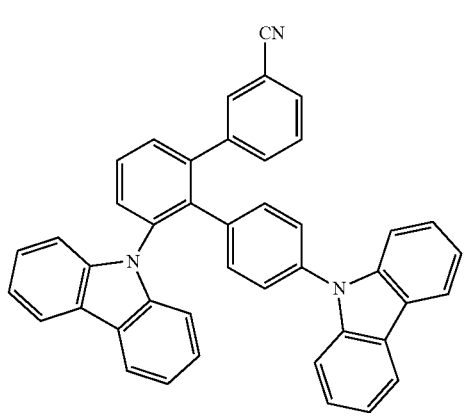
223
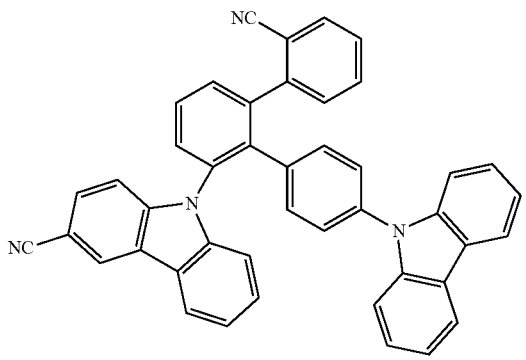

224
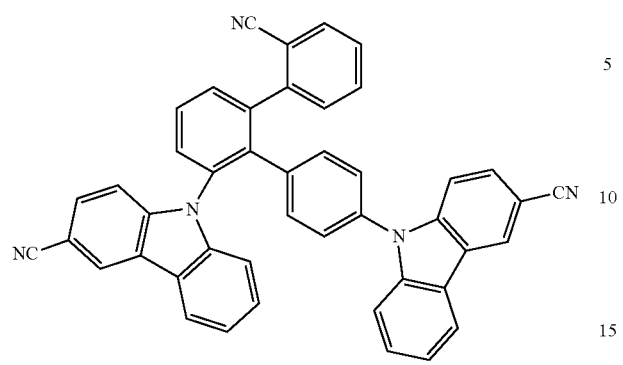
225
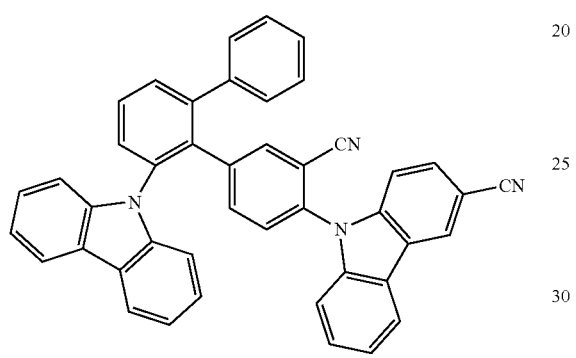
226
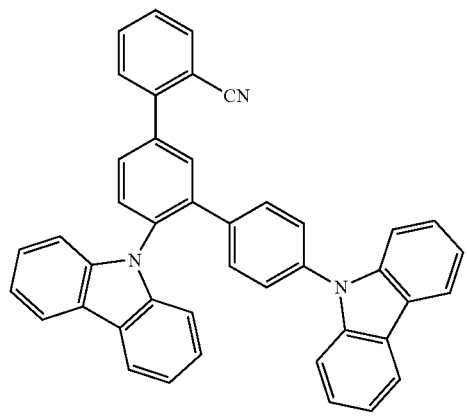
227
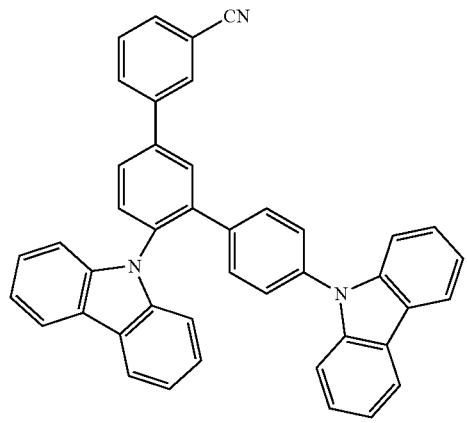
228
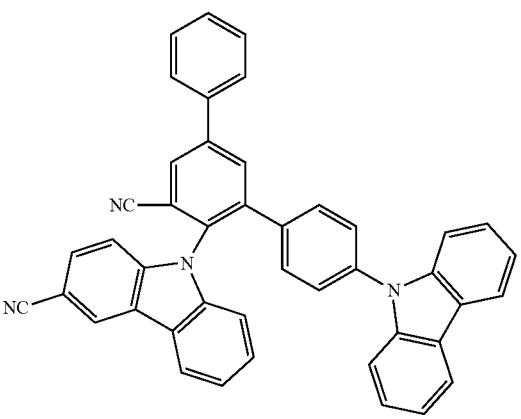
229
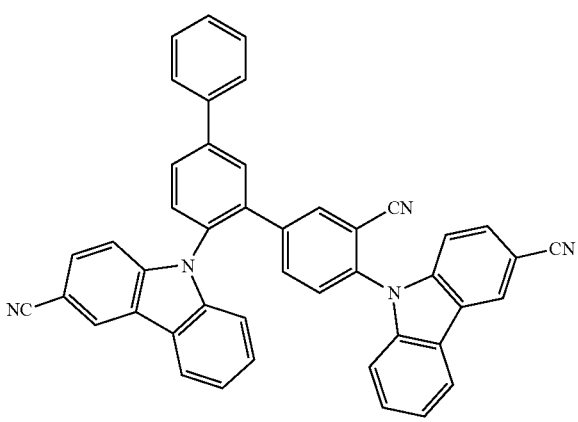
230
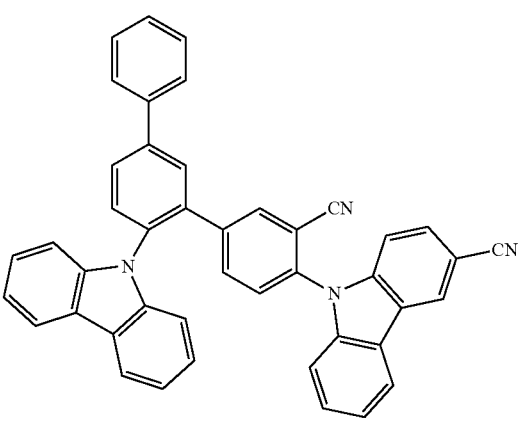

231
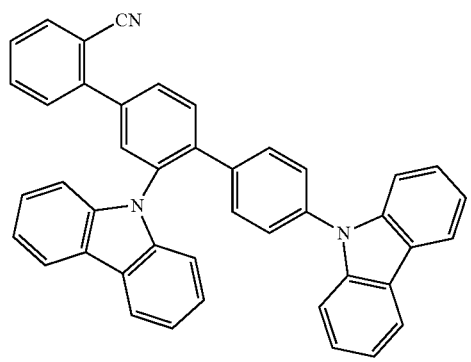
232
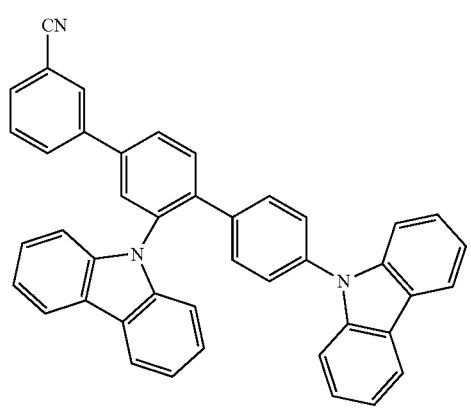
233
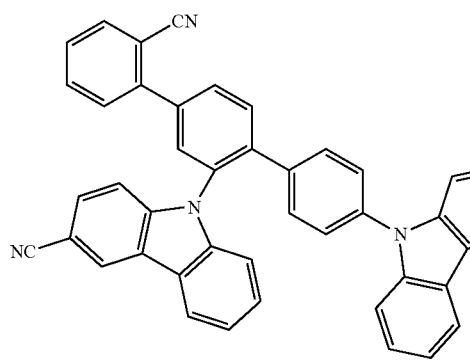
234
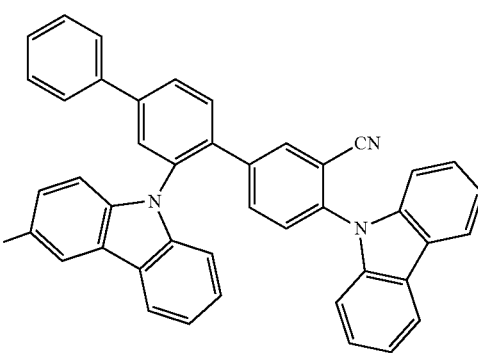
235
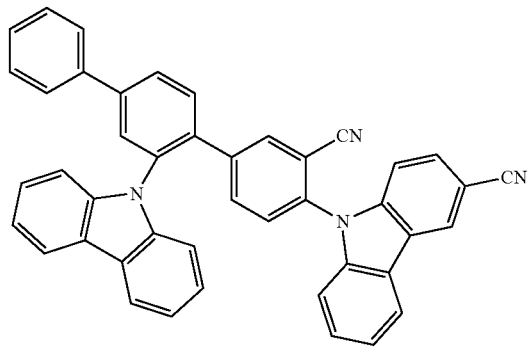
236
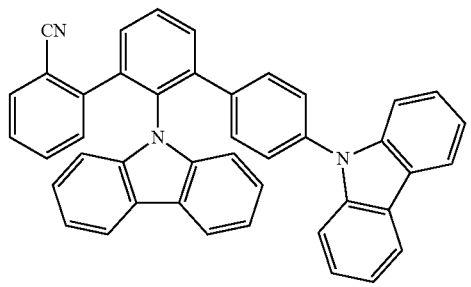
237
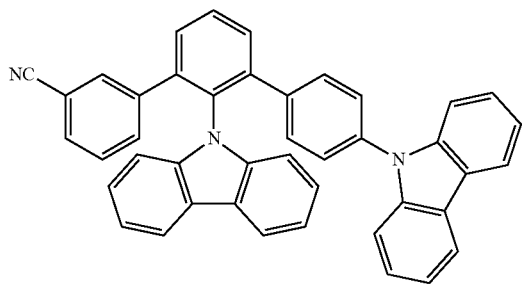
238
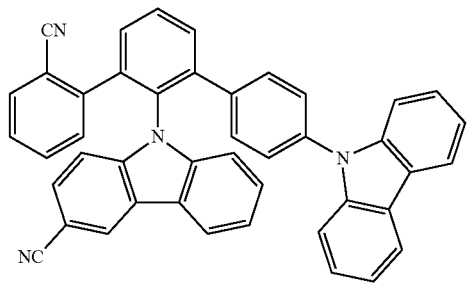
239
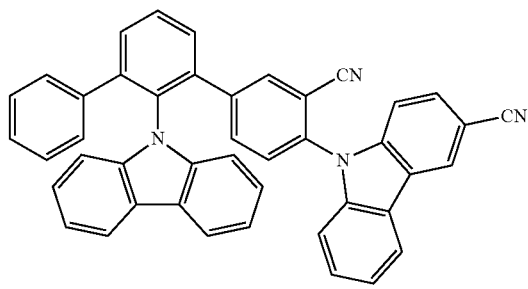

240
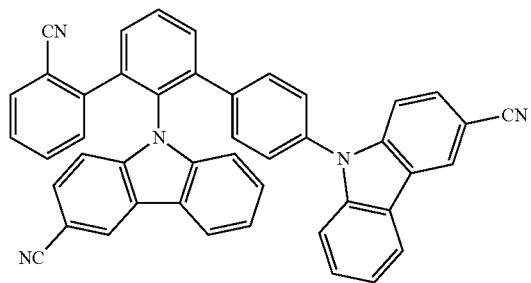
241
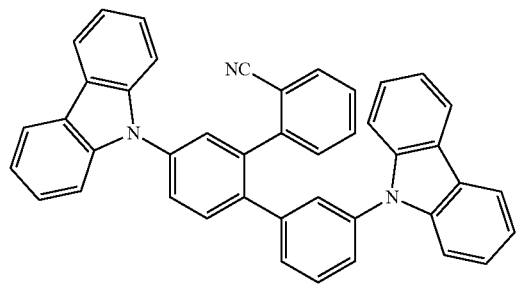
242
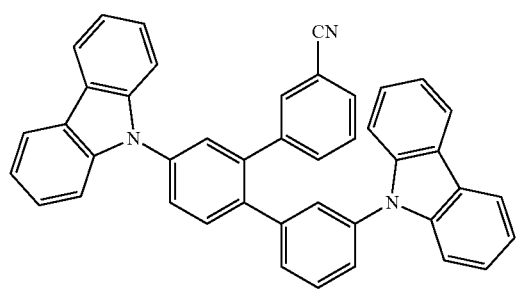
243
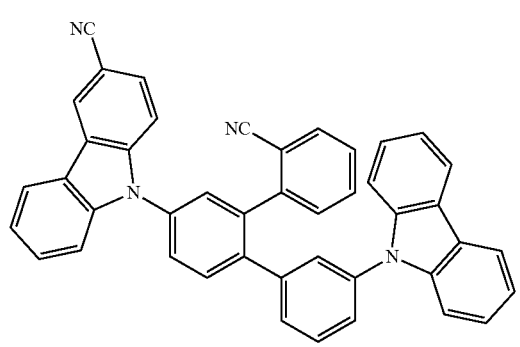
244
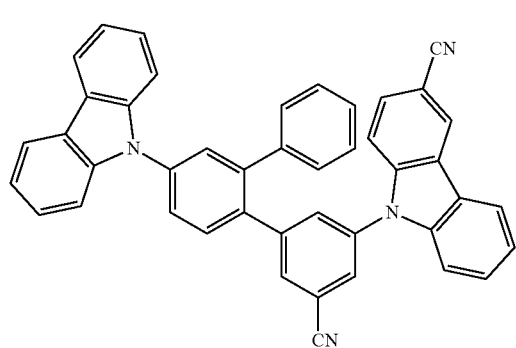
245
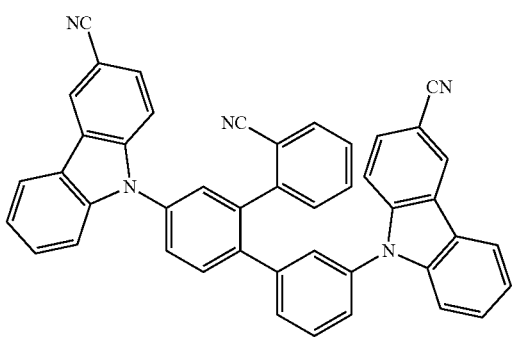
246
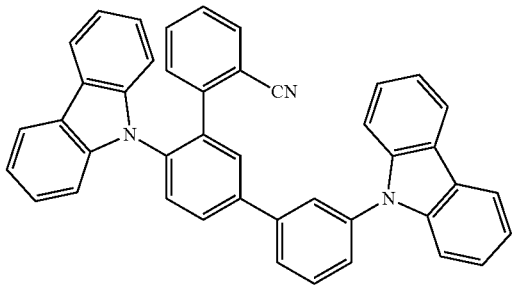
247
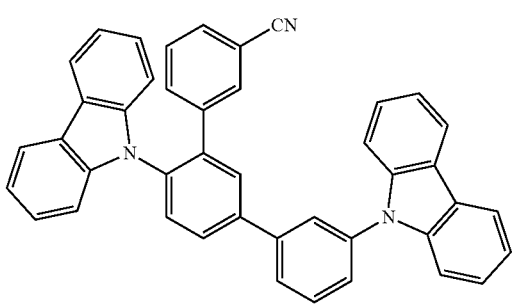
248
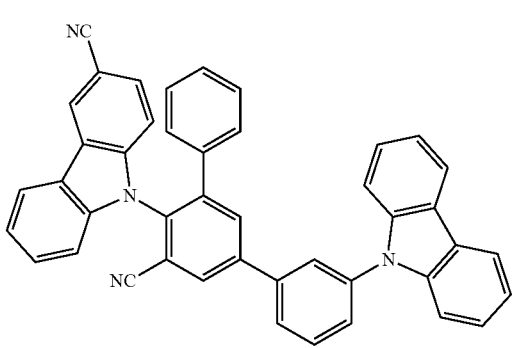

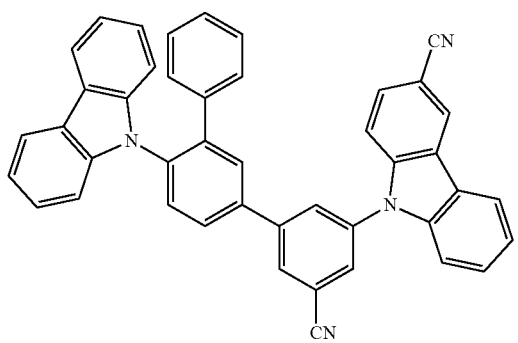
249
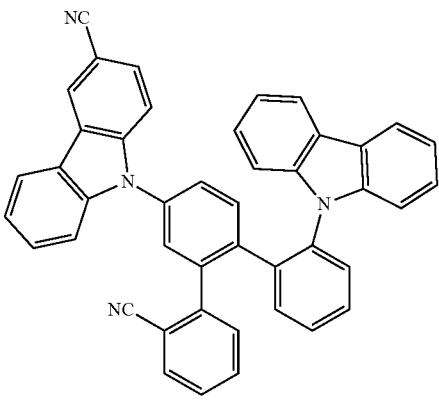
253
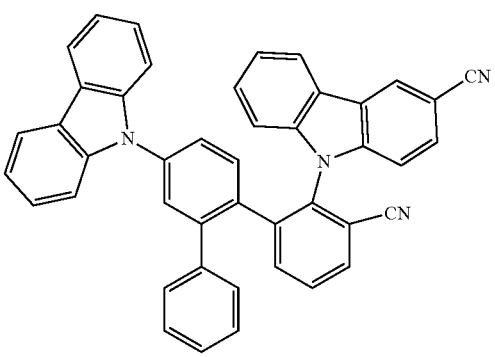
254
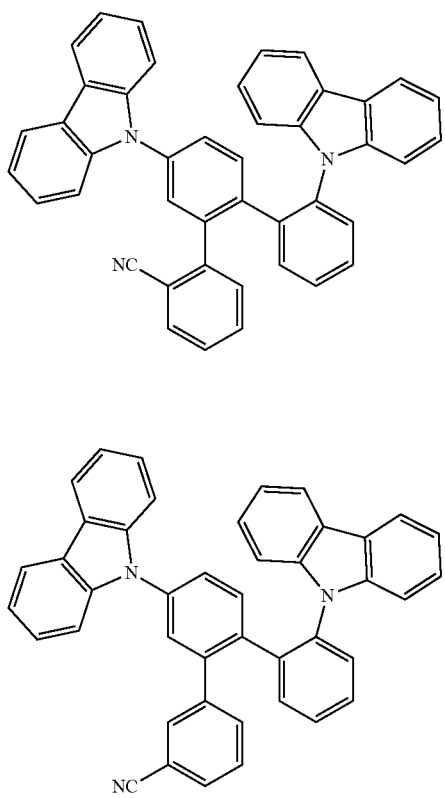
250
251
252
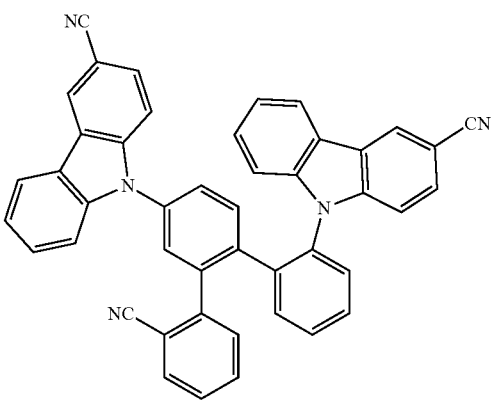
255
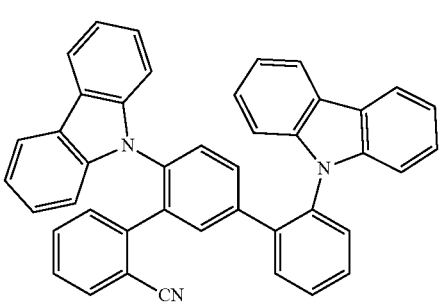
256

-continued
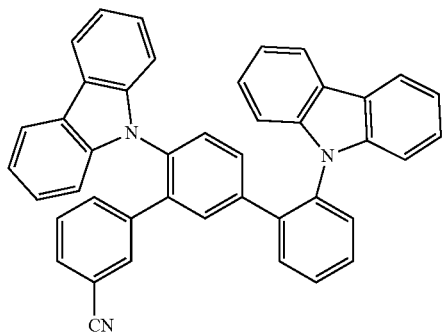
257
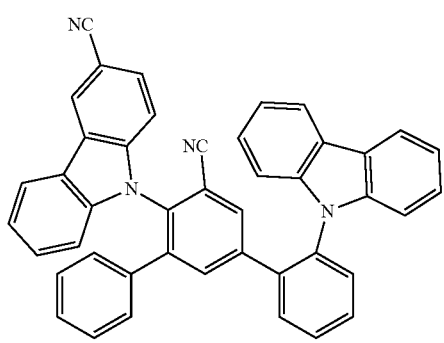
258
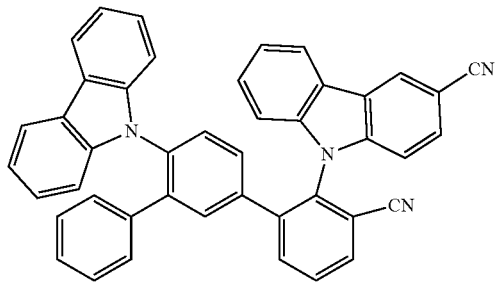
259
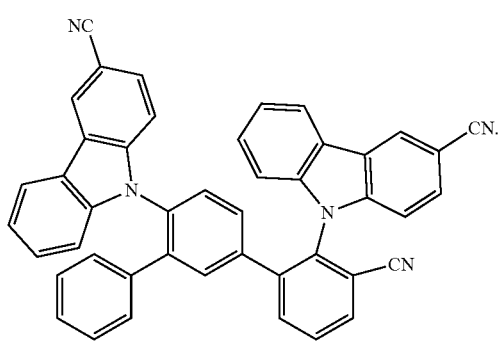
260
In one or more embodiments, the electron transport host may include DPEPO:
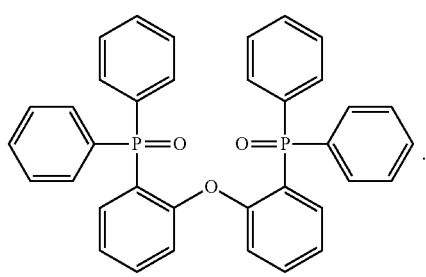 [SMILES: O=P(c1ccccc1)(c1ccccc1)c1ccccc1Oc1ccccc1P(=O)(c1ccccc1)c1ccccc1]
In one or more embodiments, the hole transport host may be one of Compounds H-H1 to H-H103, but embodiments of the present disclosure are not limited thereto:
H-H1
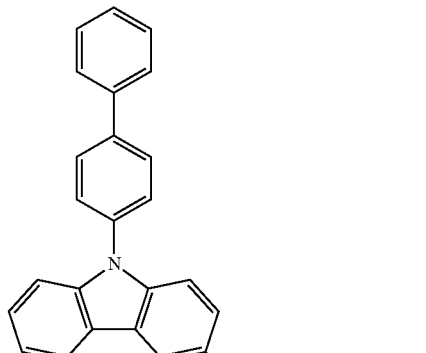

H-H2
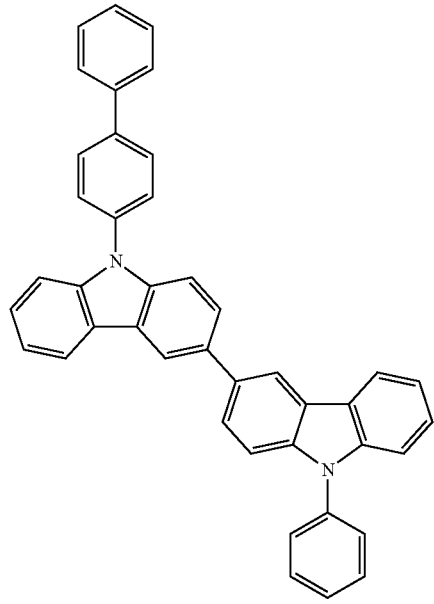
H-H5
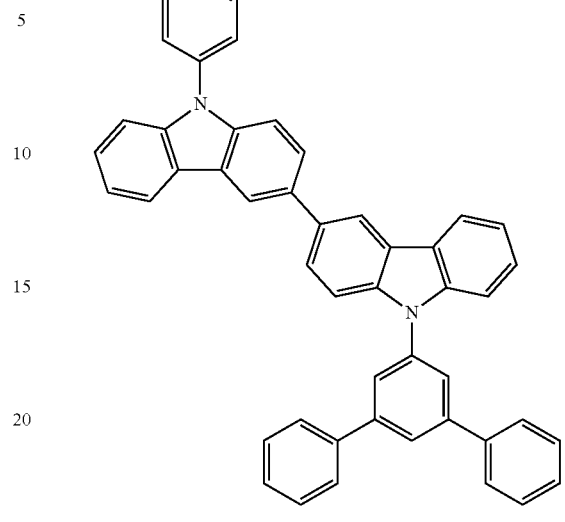
H-H3
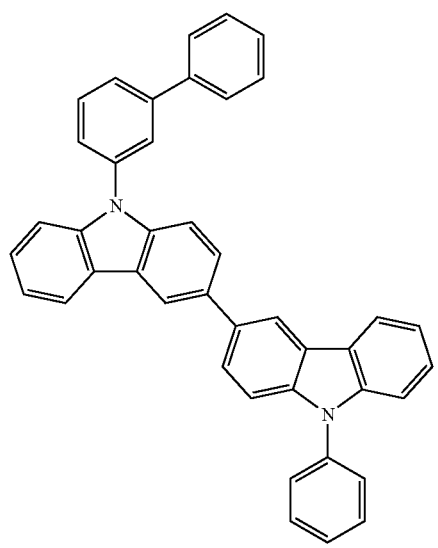
H-H4
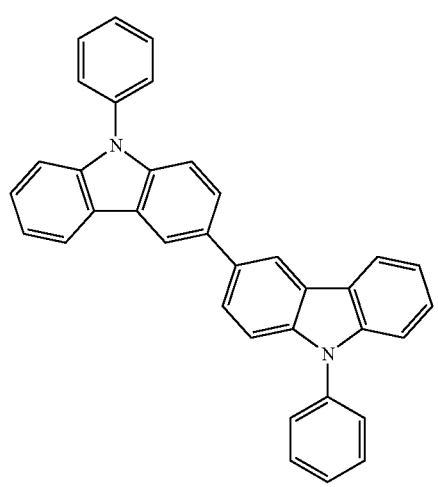
H-H6
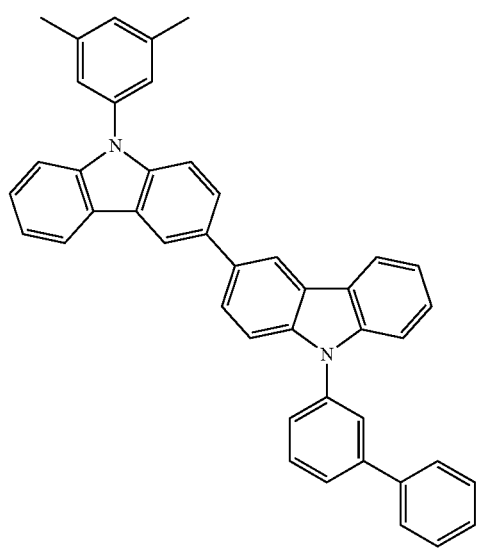

H-H7
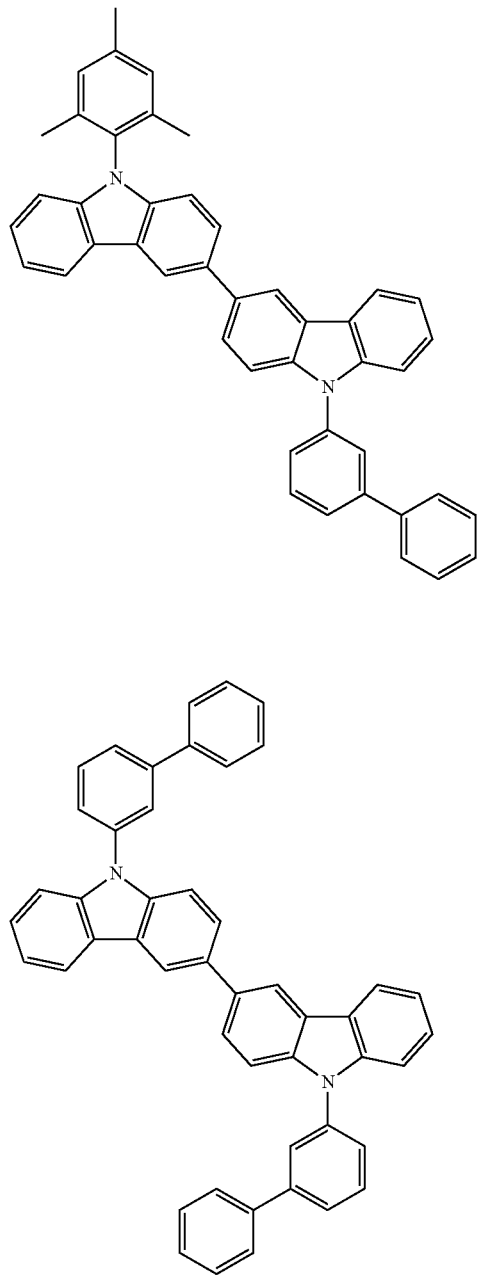
H-H8
H-H9
H-H10
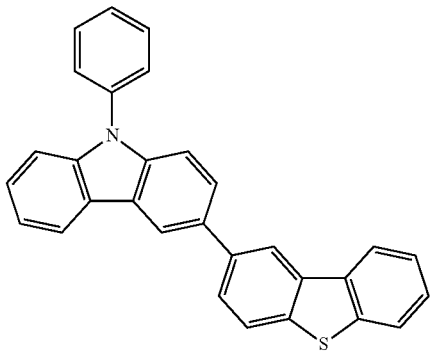
H-H11
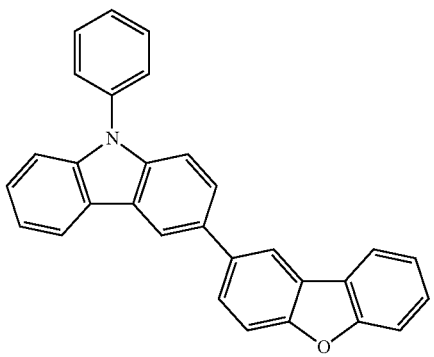
H-H12
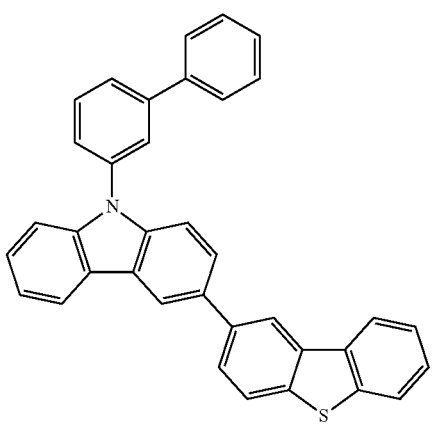
H-H13
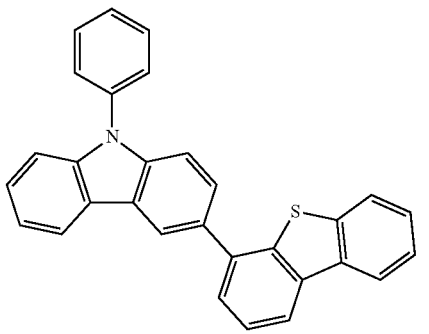

H-H14
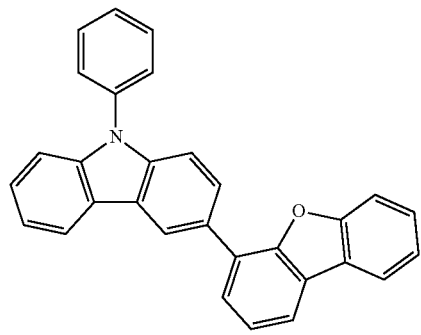
H-H15
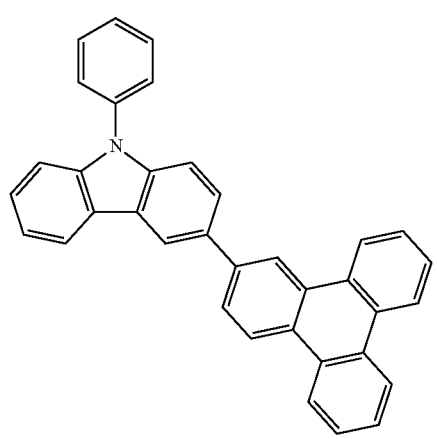
H-H16
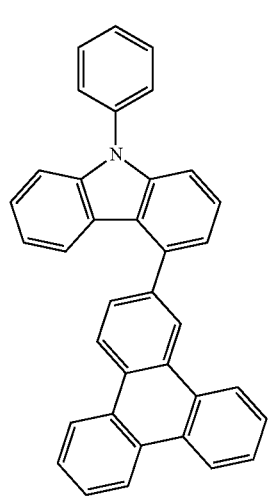
H-H17
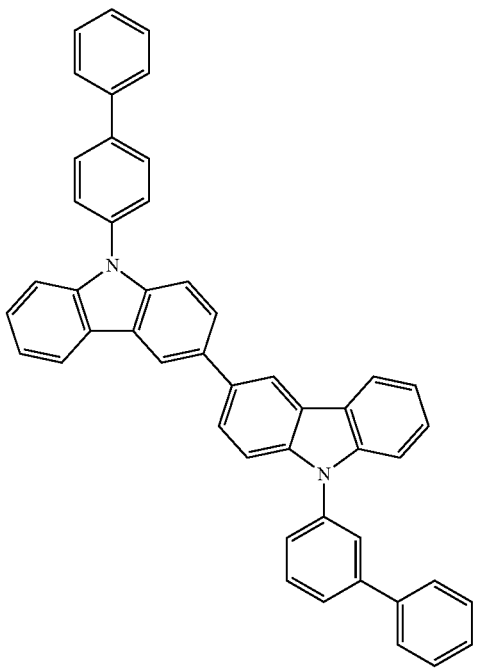
H-H18
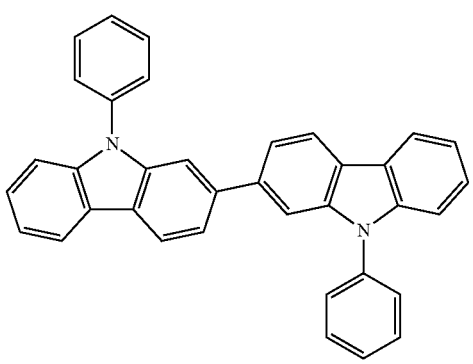
H-H19
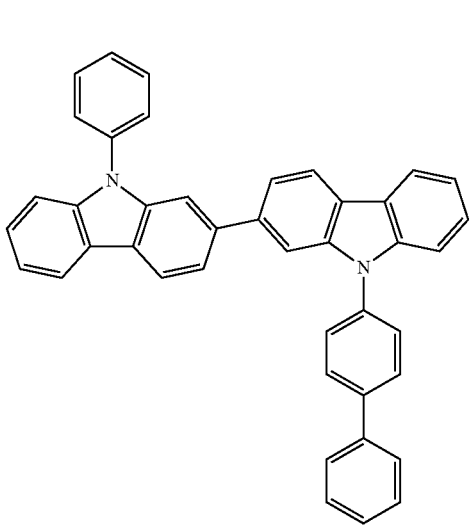

-continued
H-H20
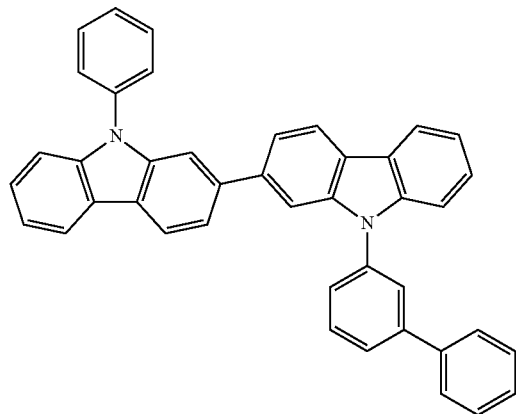
H-H21
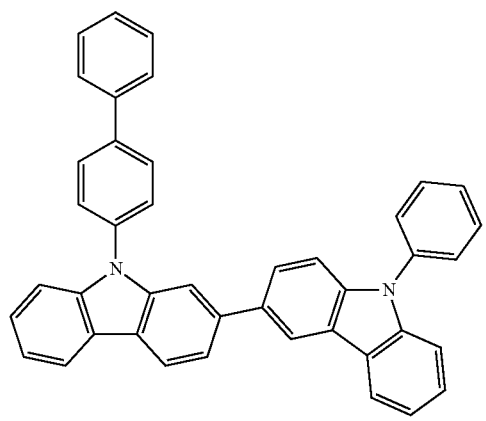
H-H22
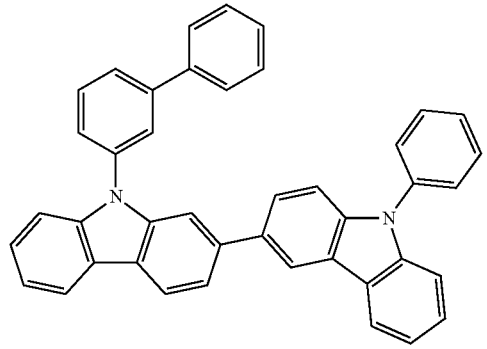
H-H23
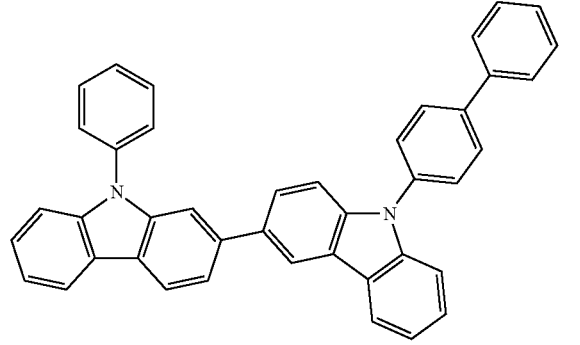
-continued
H-H24
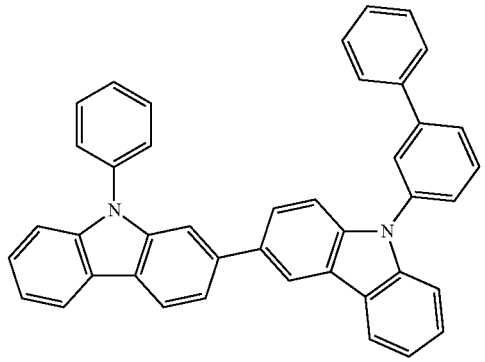
H-H25
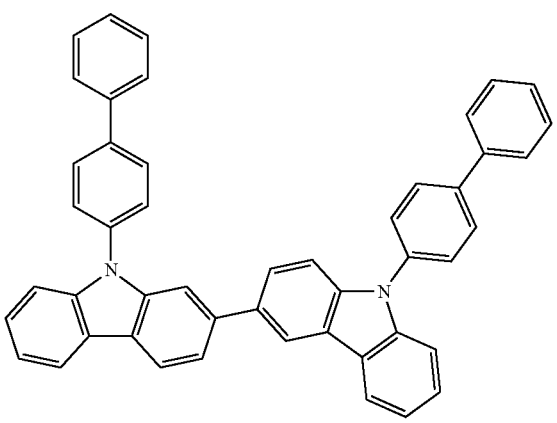
H-H26
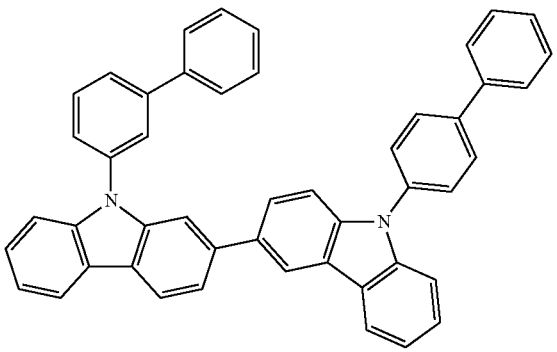
H-H27
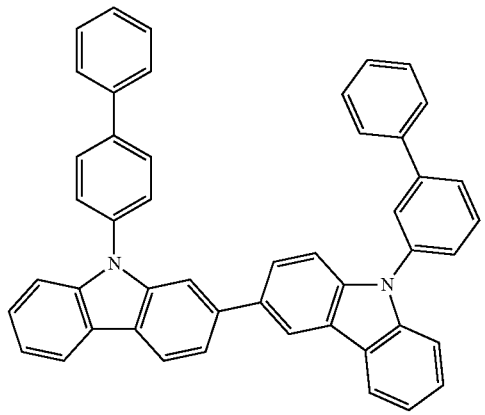

H-H28
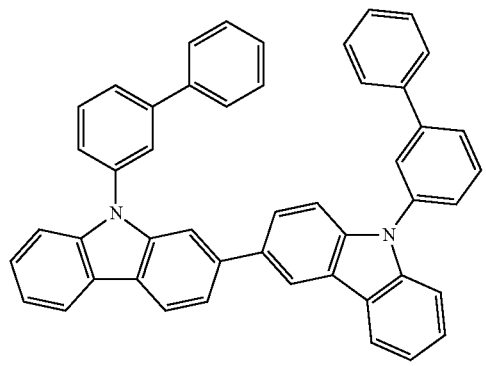
H-H29
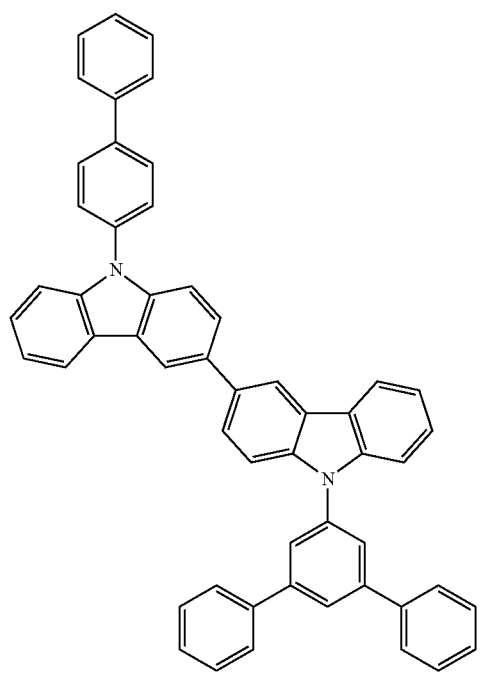
H-H30
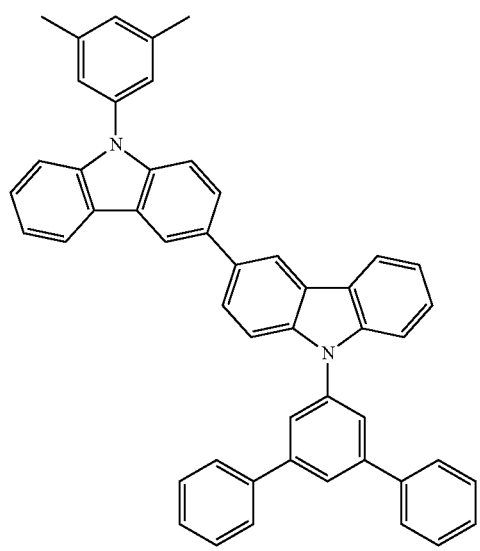
H-H31
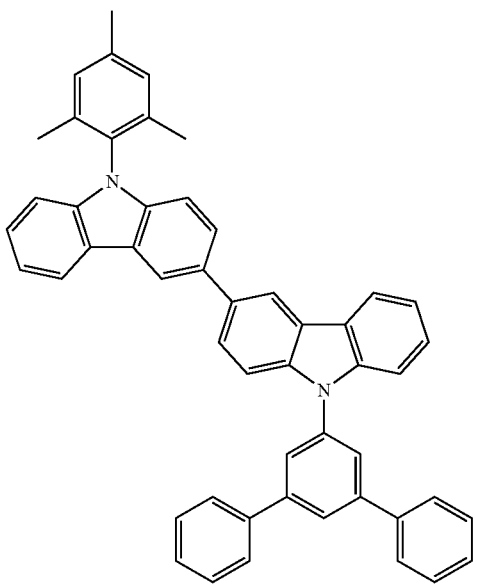
H-H32
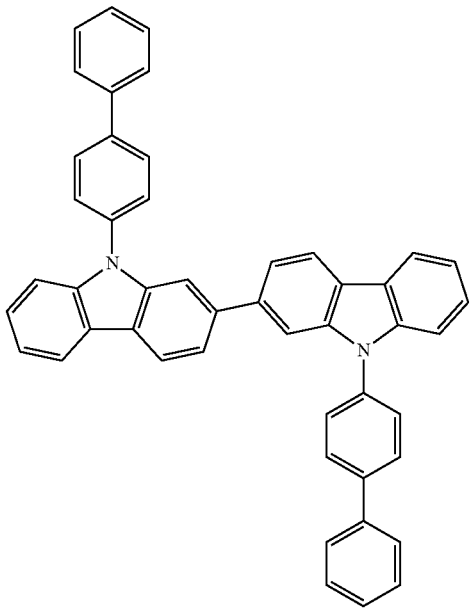

H-H33
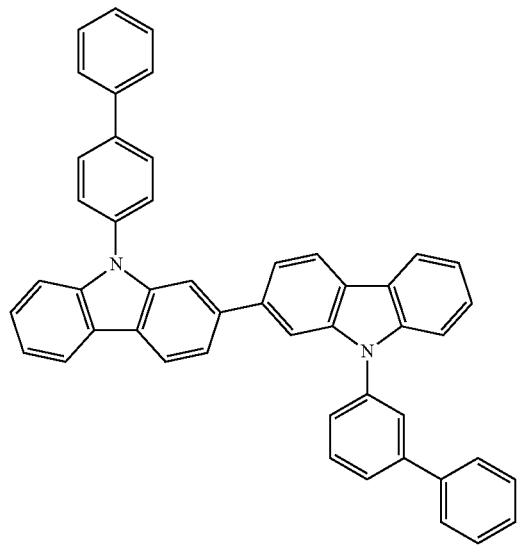
H-H34
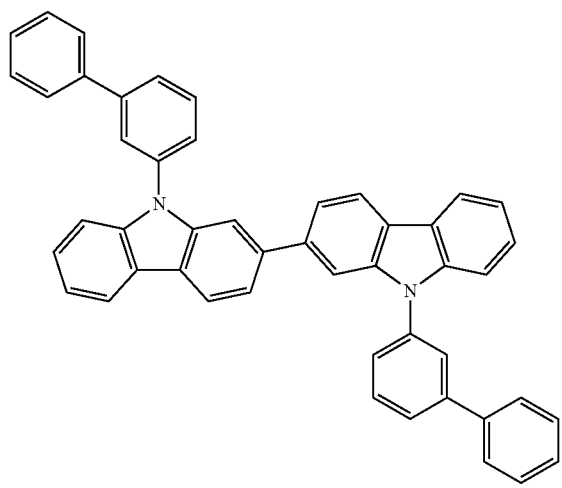
H-H35
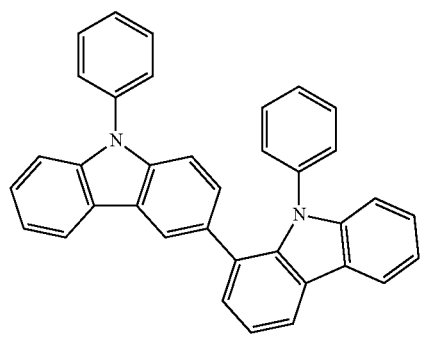
H-H36
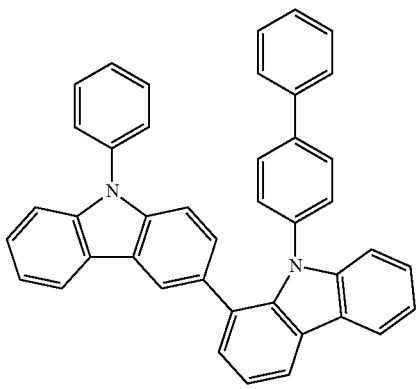
H-H37
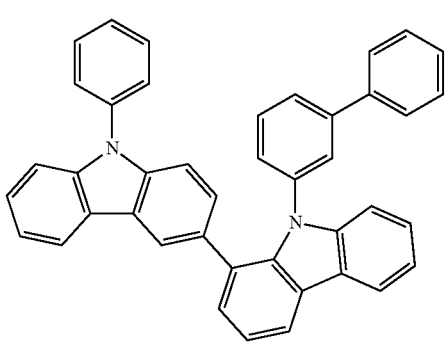
H-H38
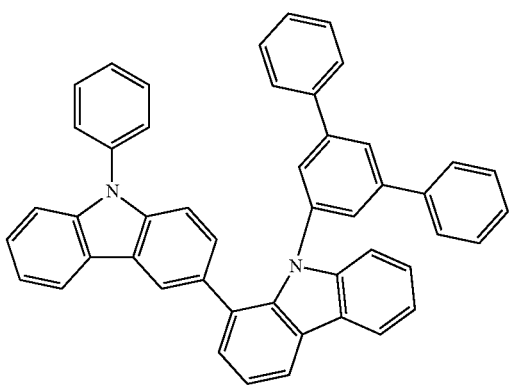
H-H39
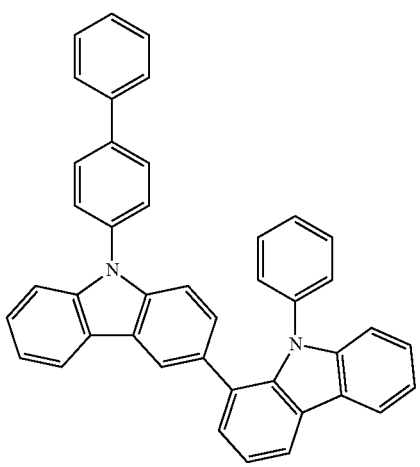

| 709 -continued | 710 -continued |
|---|---|
| H-H40 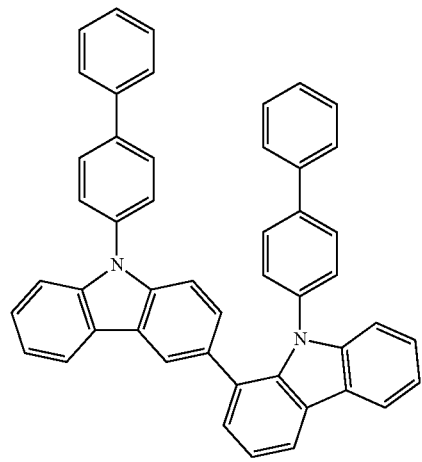 | H-H43 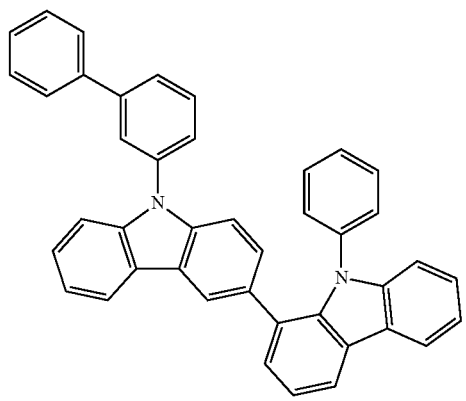 |
| H-H41 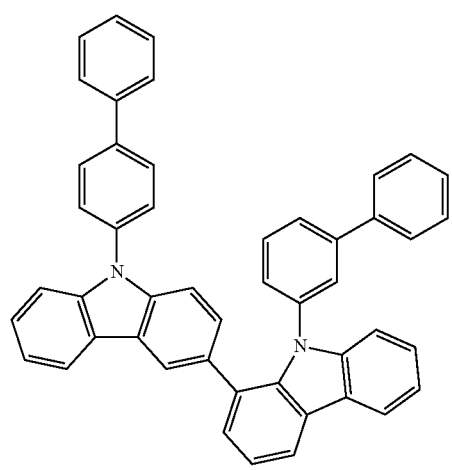 | H-H44 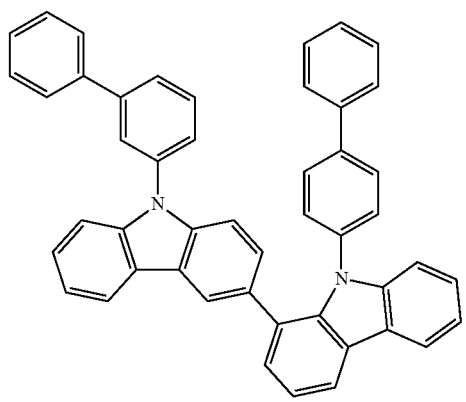 |
| H-H42 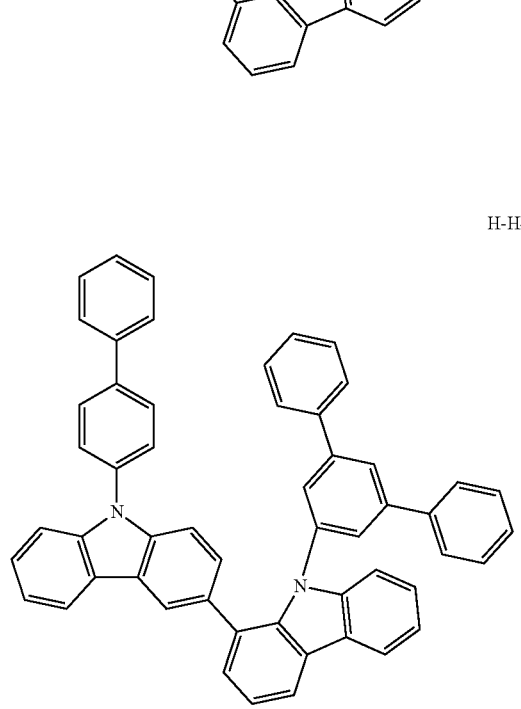 | H-H45 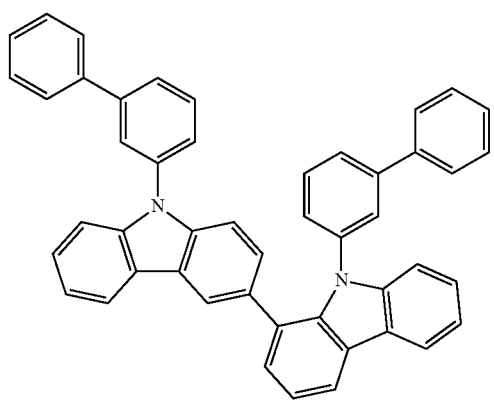 |
| | H-H46 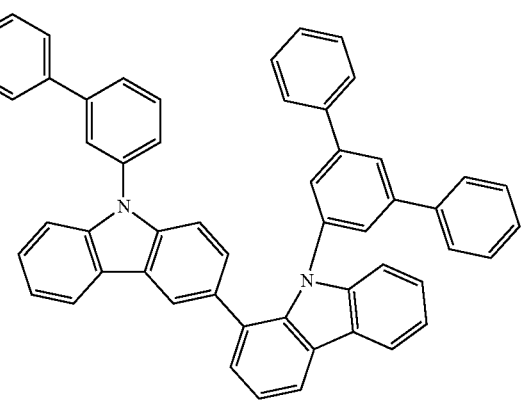 |

| 711 -continued | 712 -continued |
|---|---|
| H-H47 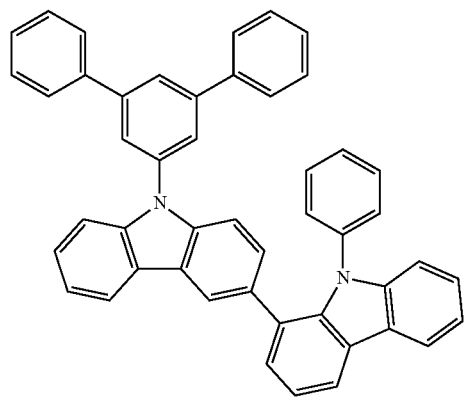 | H-H50 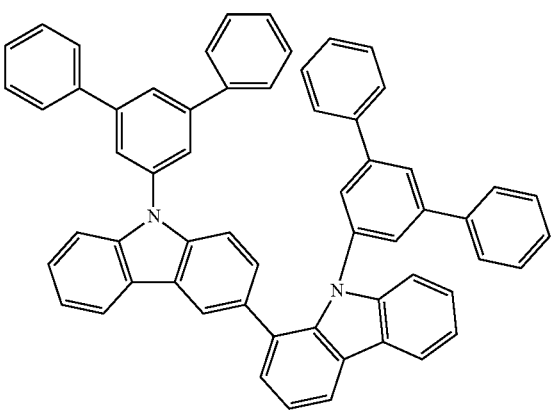 |
| H-H48 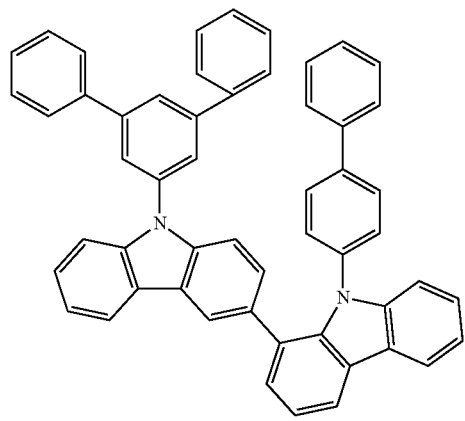 | H-H51 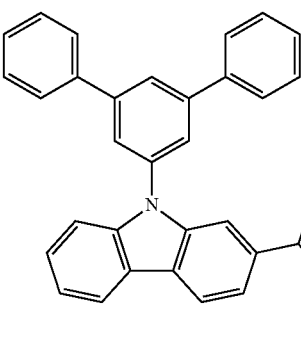 |
|  | H-H52 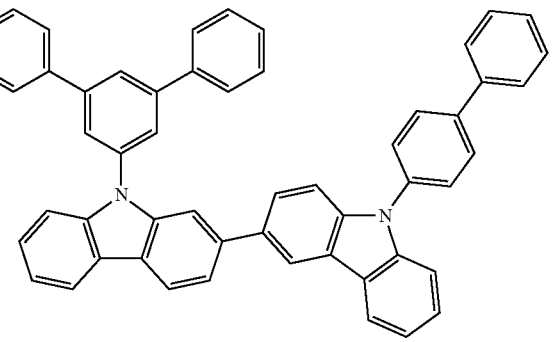 |
| H-H49 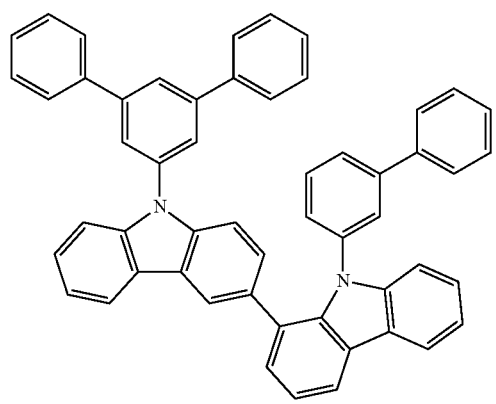 | H-H53 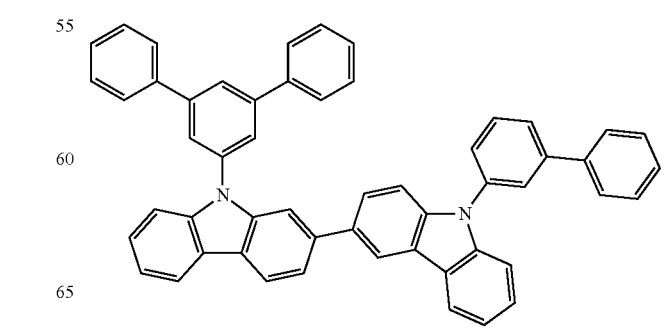 |

H-H54
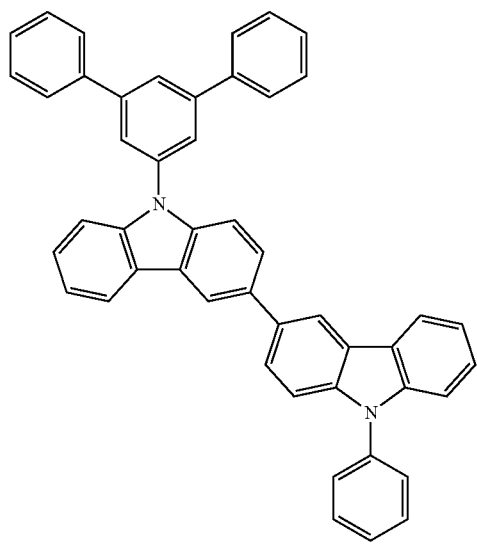
H-H55
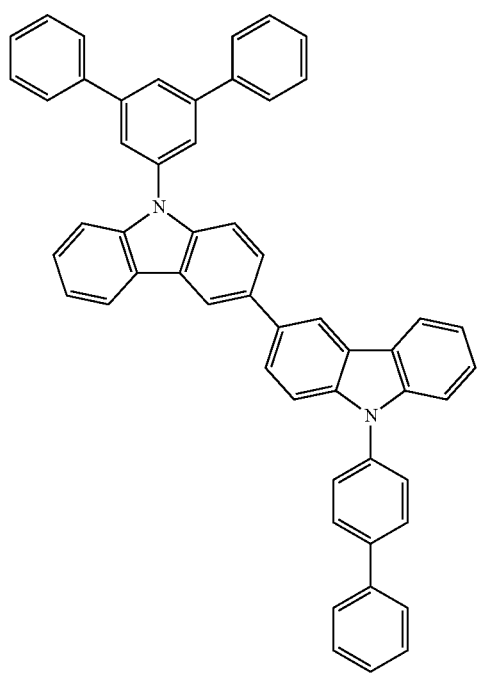
H-H56
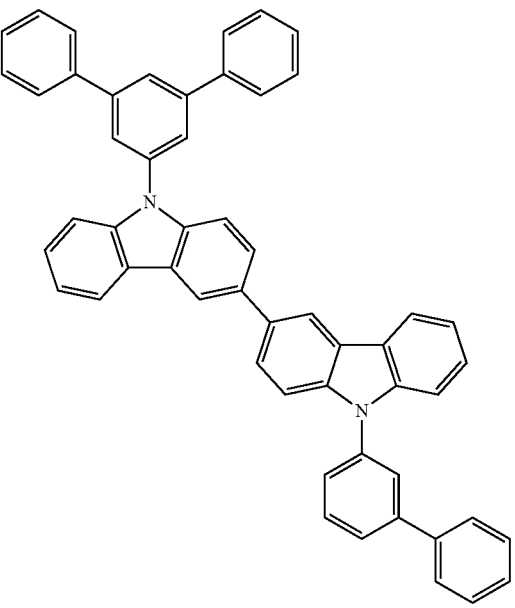
H-H57
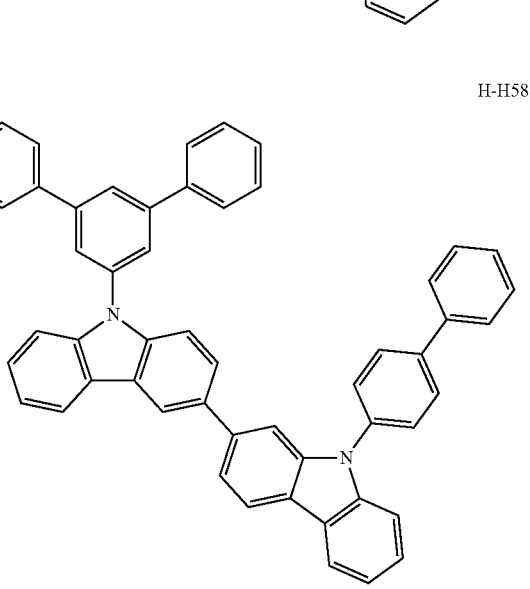
H-H58

H-H59
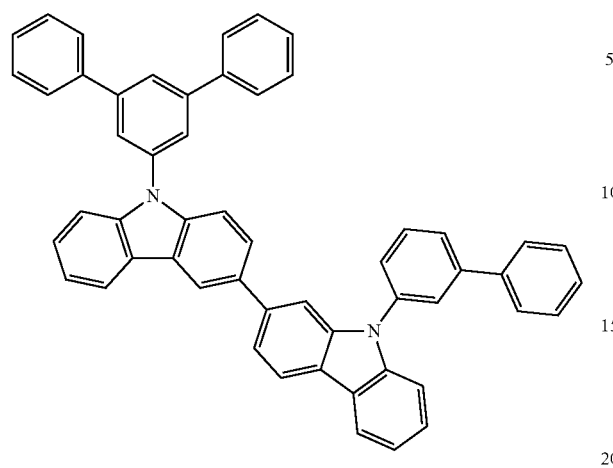
H-H60
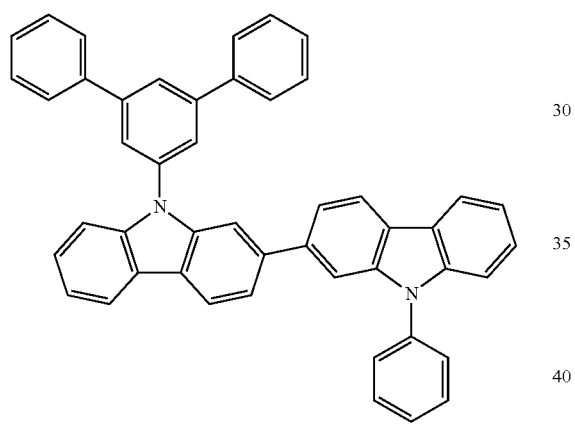
H-H61
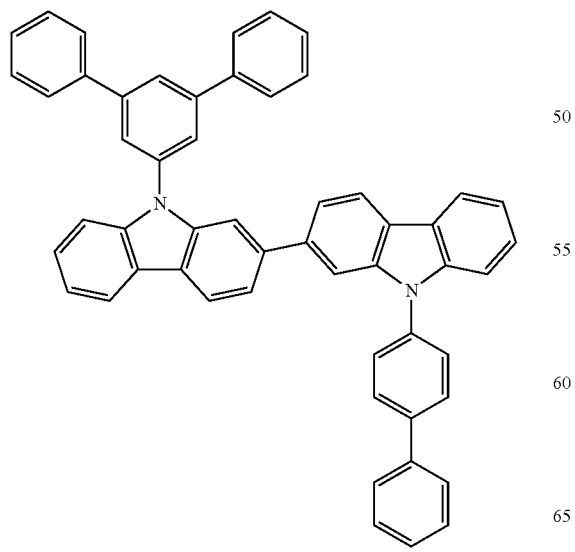
H-H62
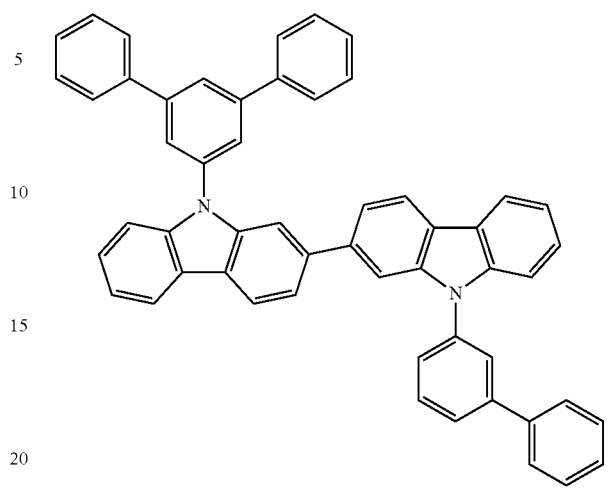
H-H63
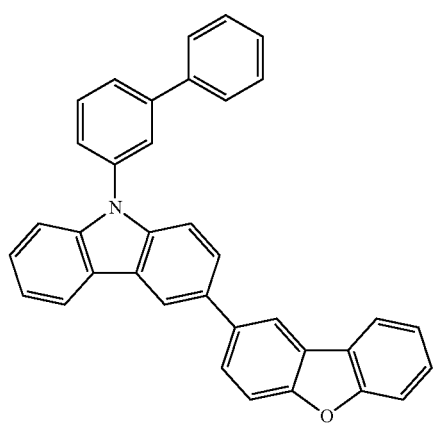
H-H64
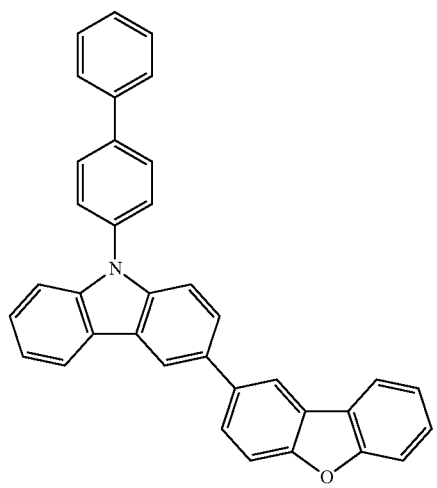

H-H65
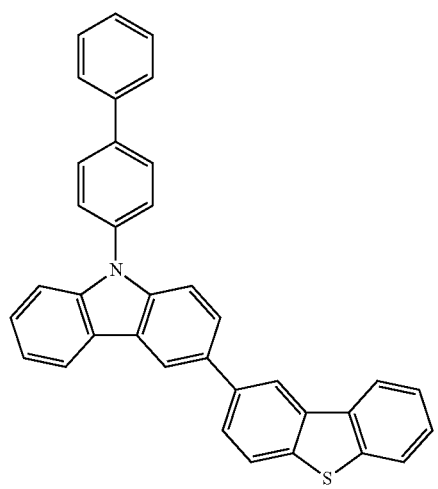
H-H66
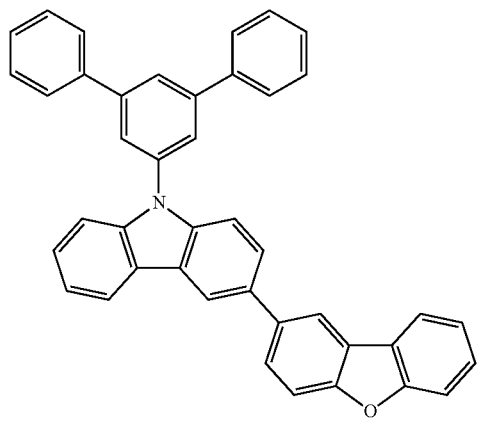
H-H67
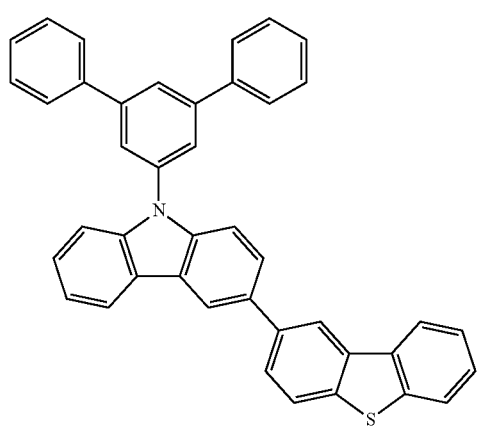
H-H68
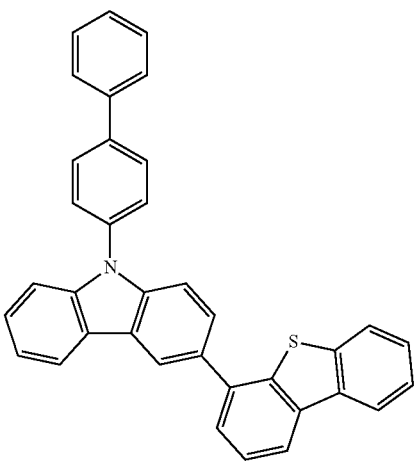
H-H69
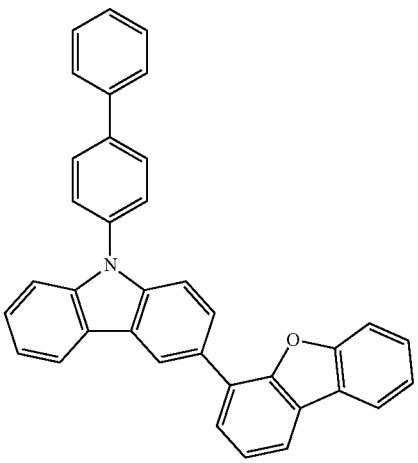
H-H70
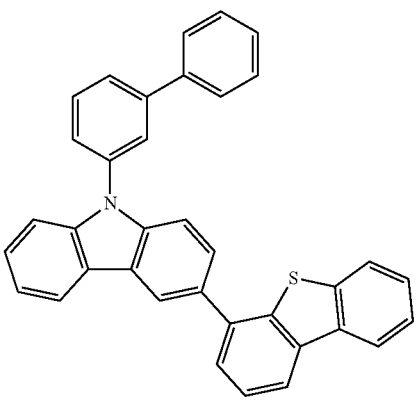

719
-continued
H-H71
H-H72
H-H73
H-H74
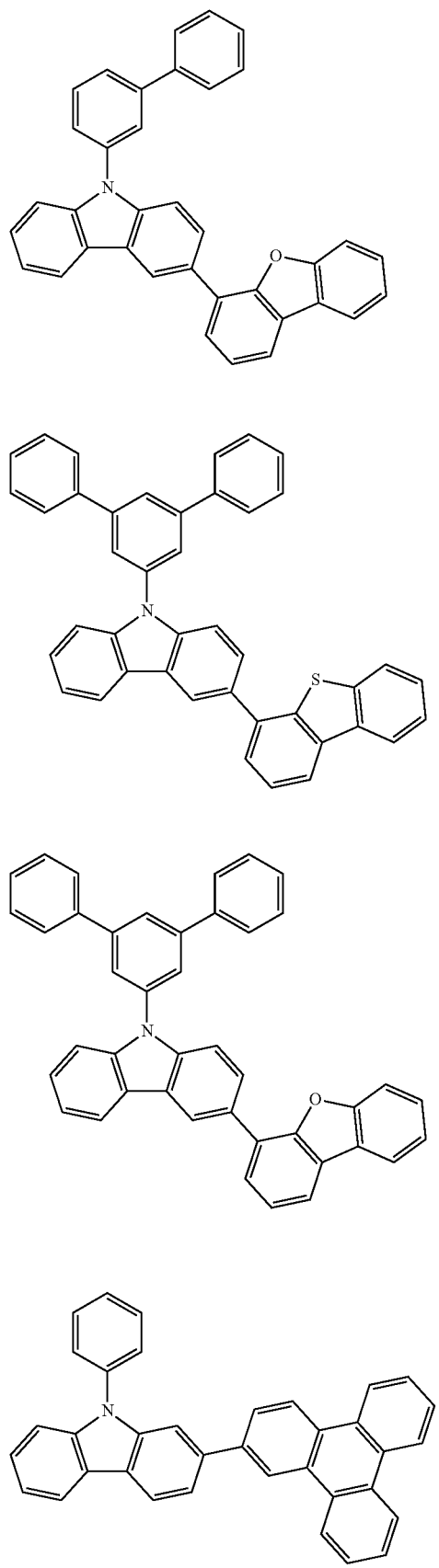
720
-continued
H-H75
H-H76
H-H77
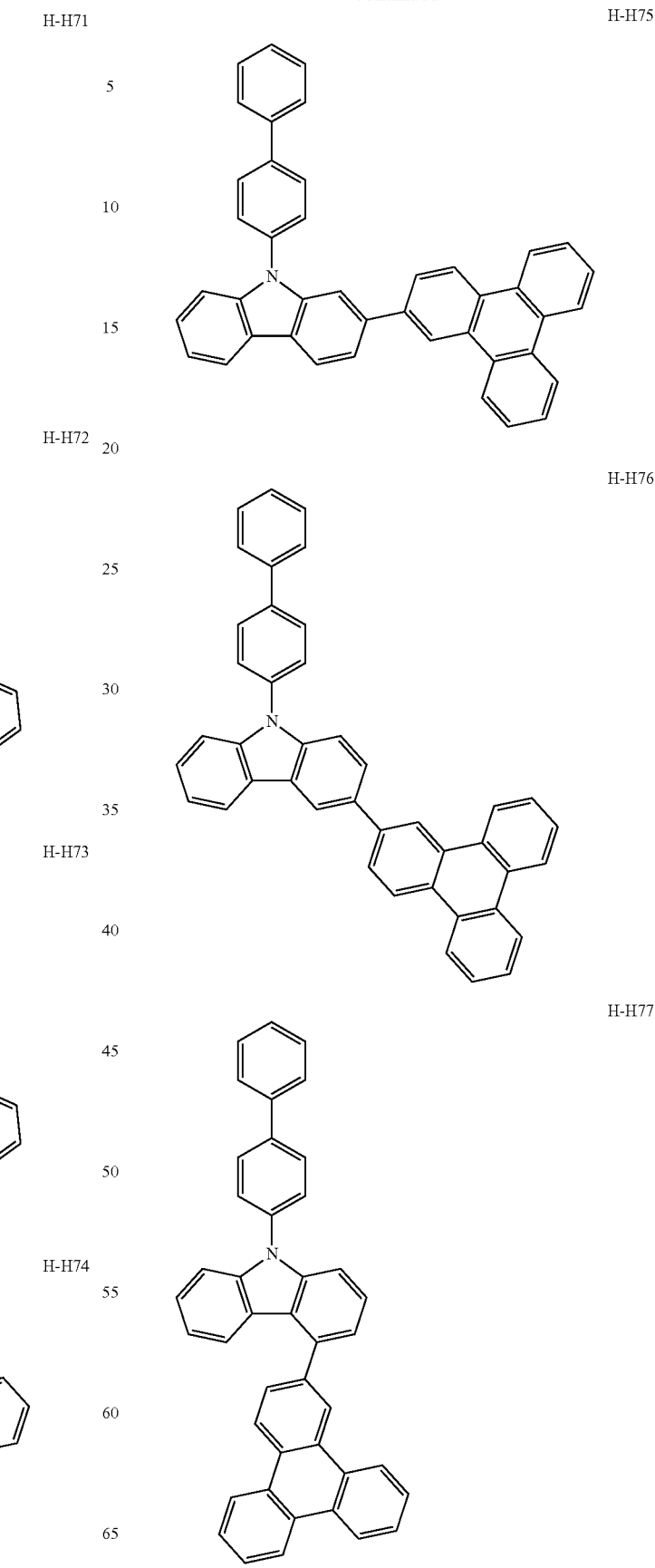

H-H78
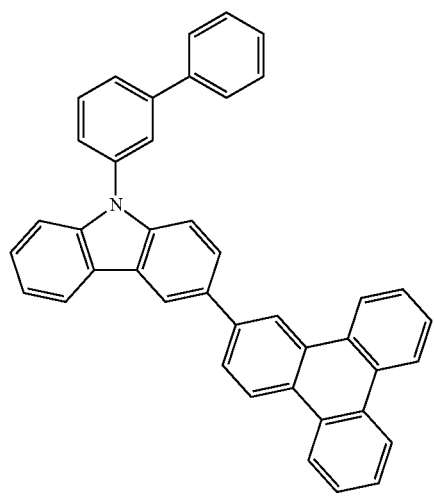
H-H79
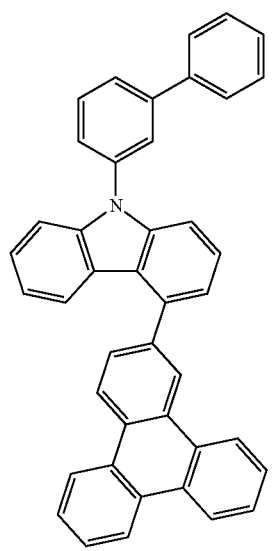
H-H80
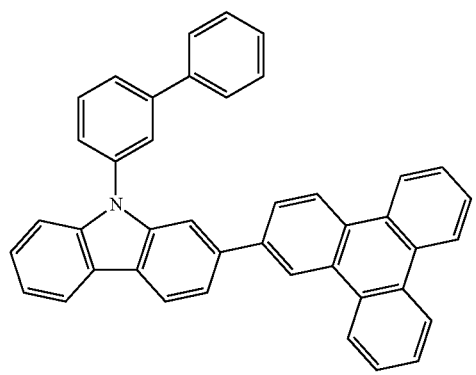
H-H81
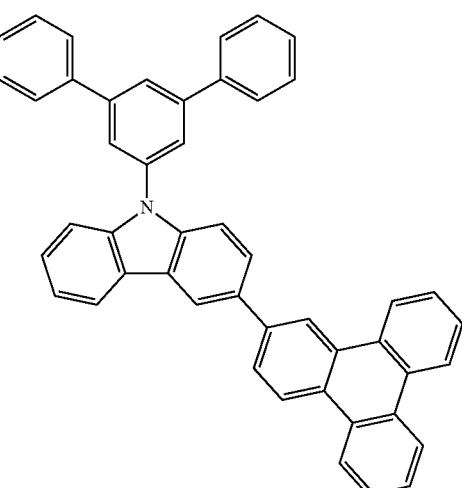
H-H82
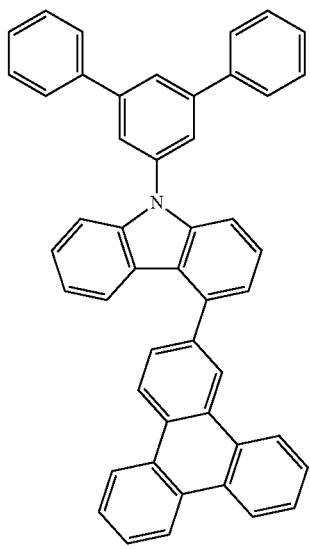
H-H83
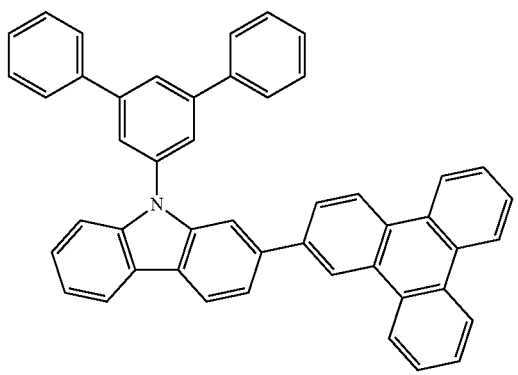

-continued
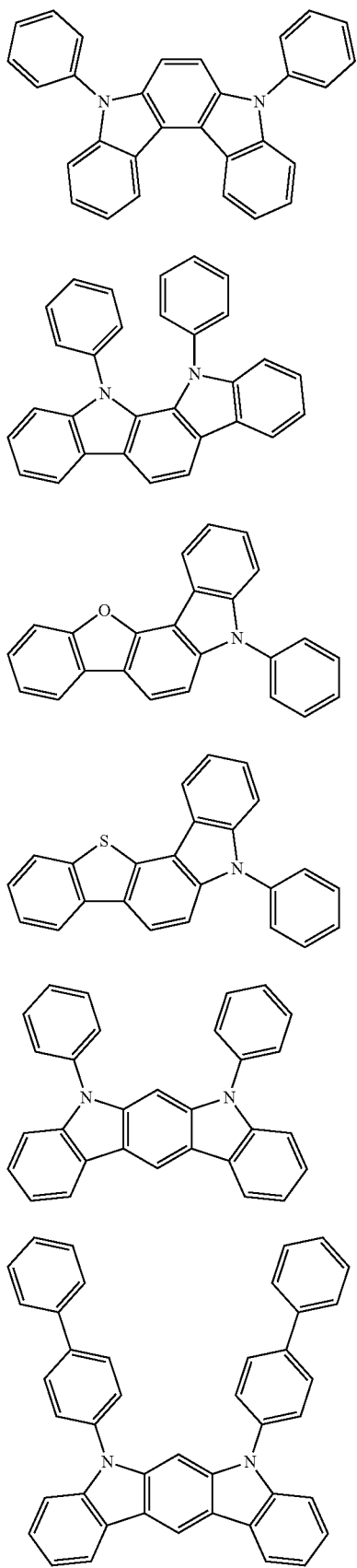
H-H84
H-H85
H-H86
H-H87
H-H88
H-H89
-continued
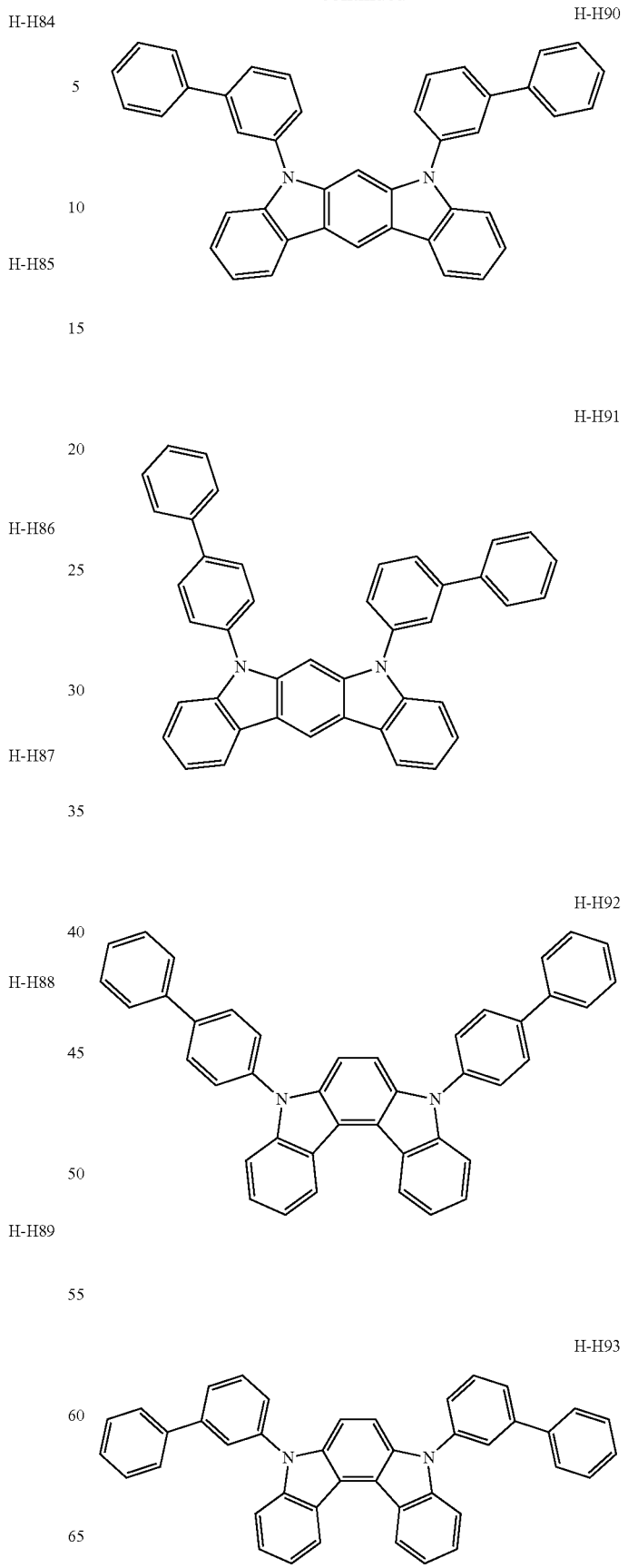
H-H90
H-H91
H-H92
H-H93

H-H94
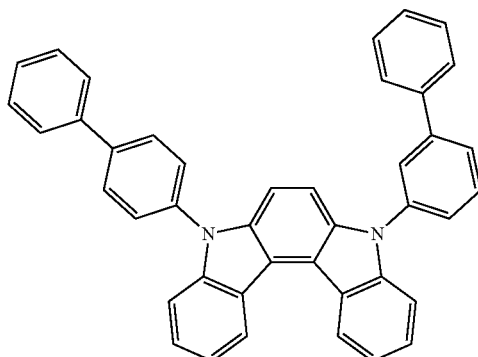
H-H95
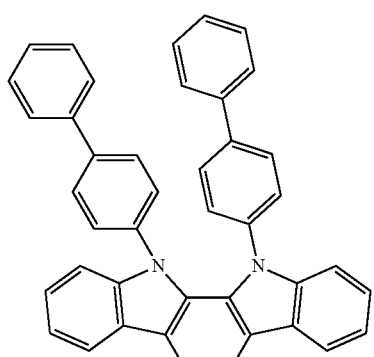
H-H96
H-H97
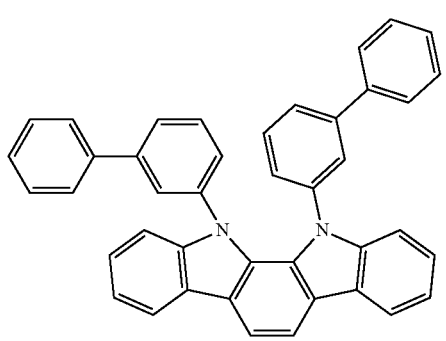
H-H98
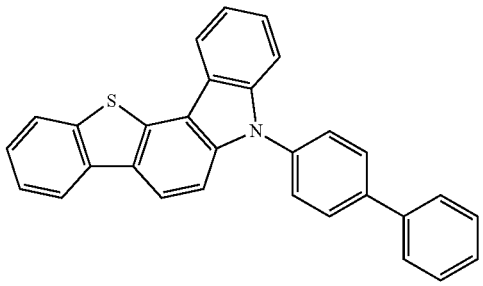
H-H99
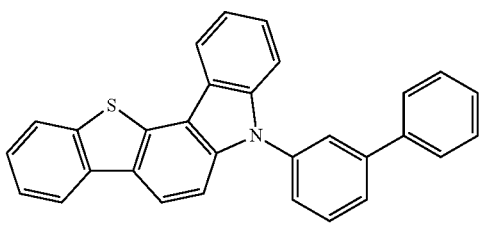
H-H100
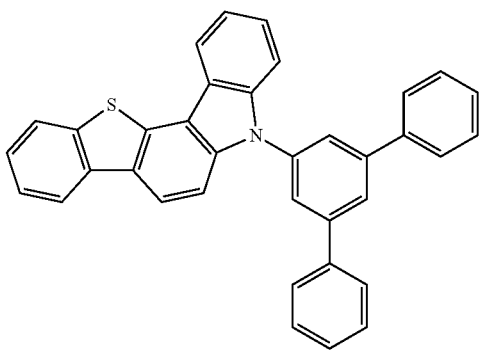
H-H101
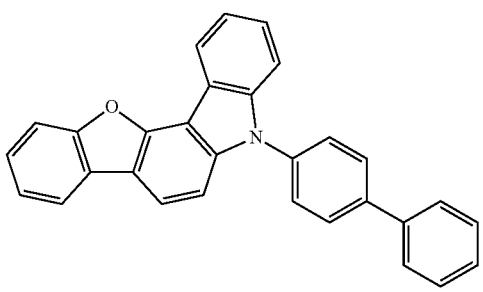
H-H102
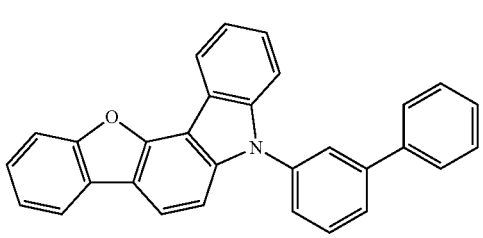

H-H103
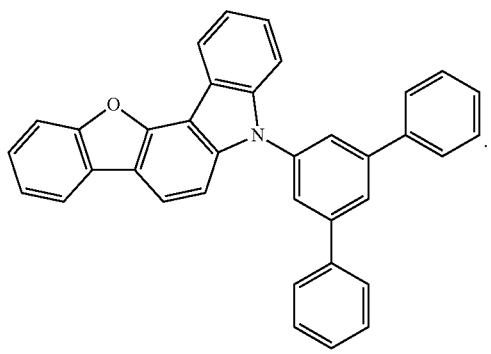
In one or more embodiments, the amphiprotic host may be compounds belonging to <Group HEH1>, but embodiments of the present disclosure are not limited thereto:
<Group HEH1>
1
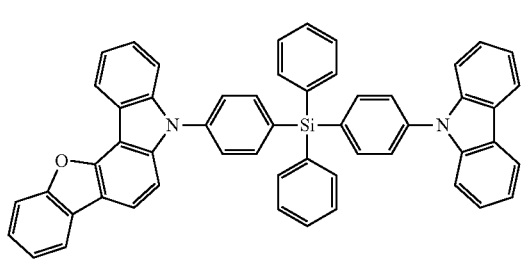
2
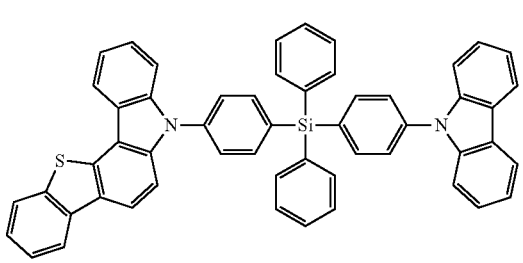
3
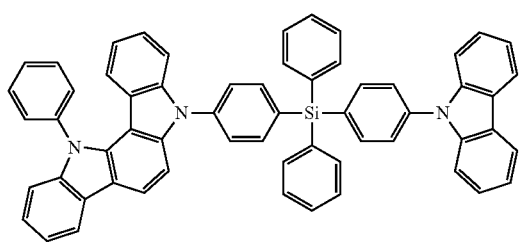
4
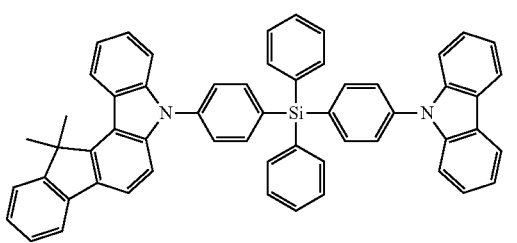
5
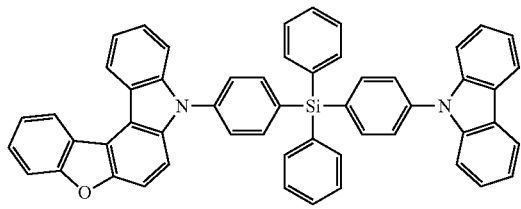
6
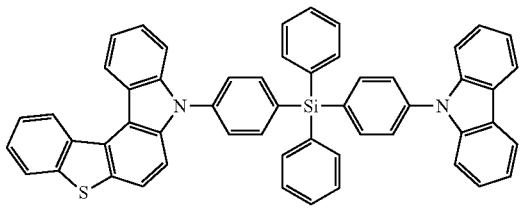
7
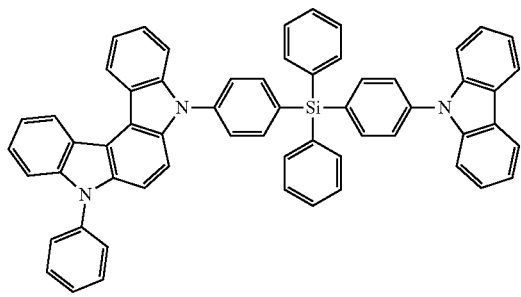
8
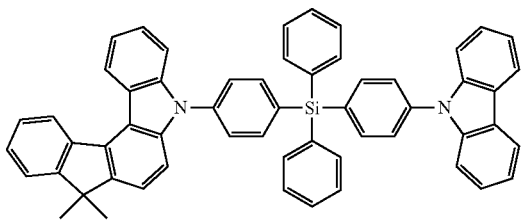

-continued
9
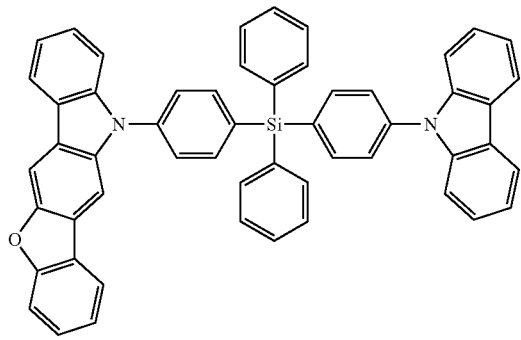
10
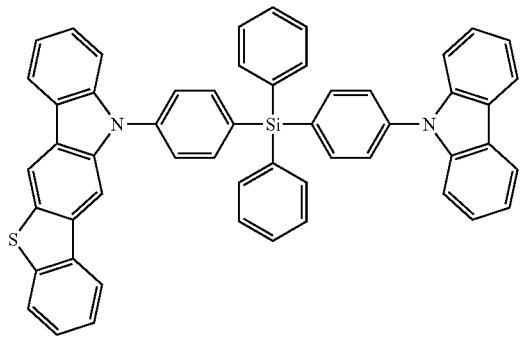
11
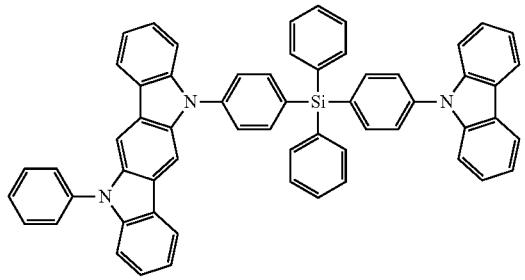
12
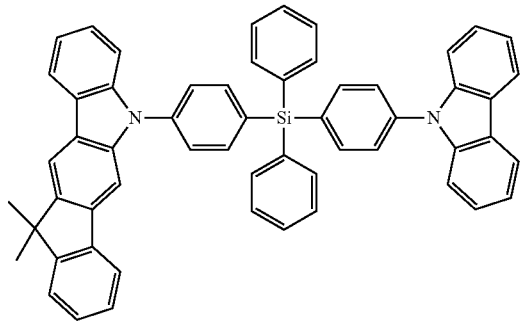
13
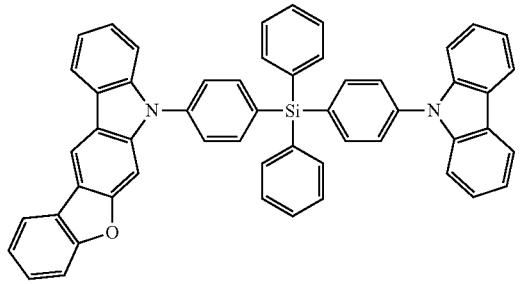
14
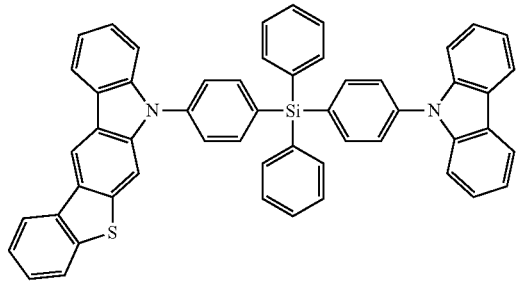
15
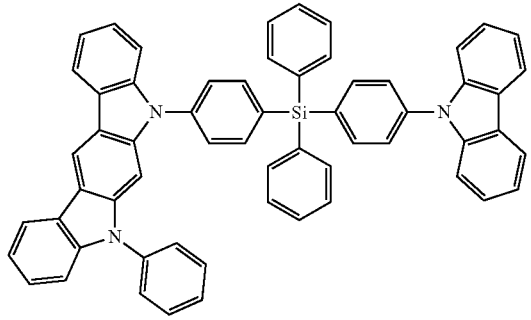
16
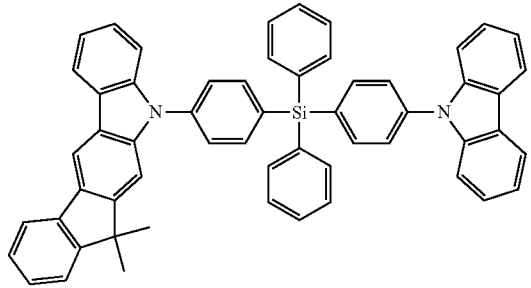
17
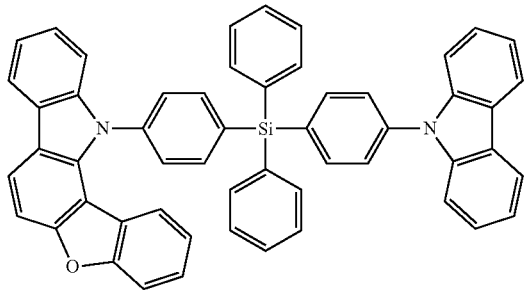
18
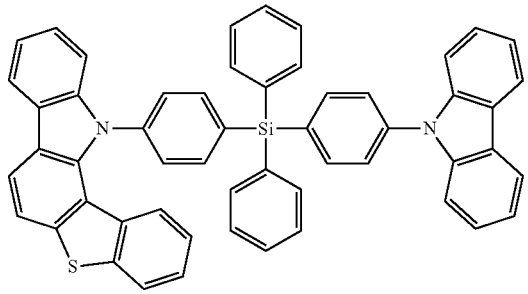

-continued
| 19 | 20 |
|---|---|
| 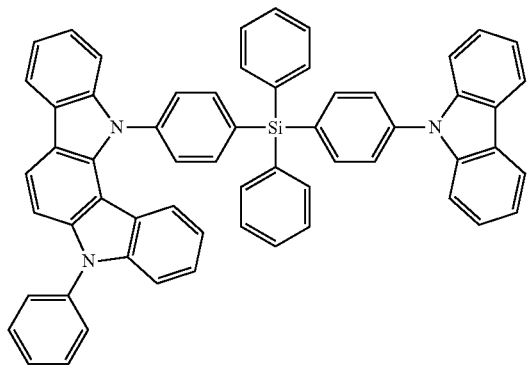 | 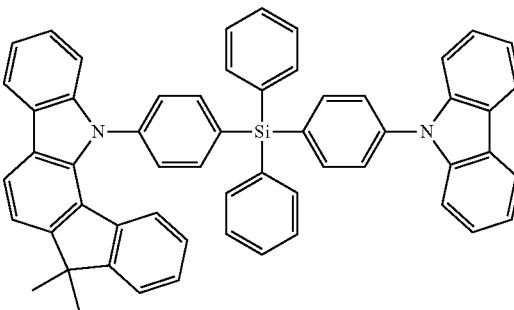 |
| 21 | 22 |
| 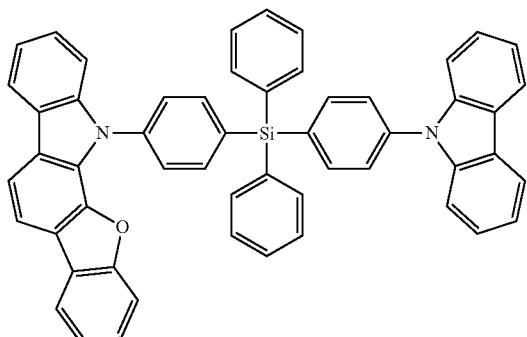 | 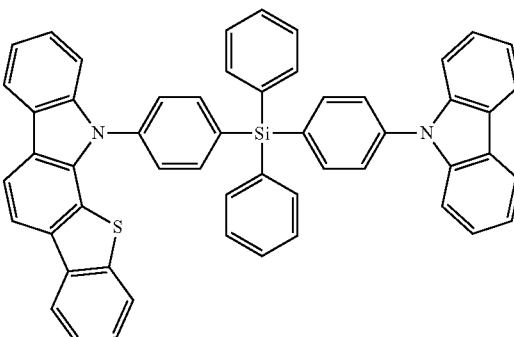 |
| 23 | 24 |
| 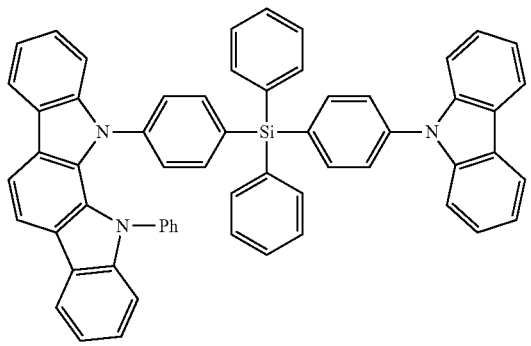 | 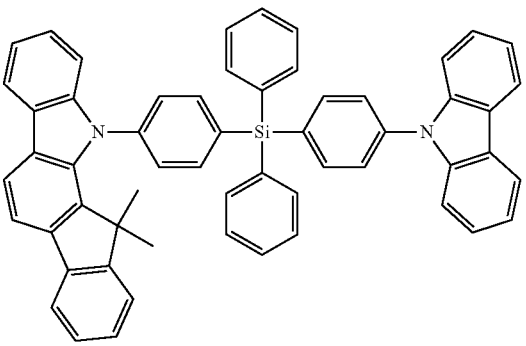 |
| 25 | 26 |
| 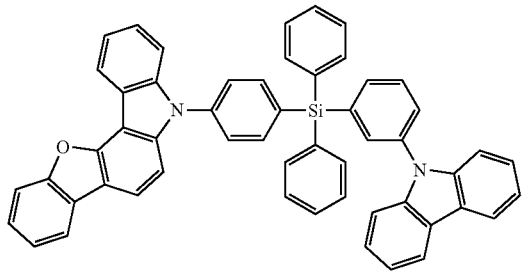 | 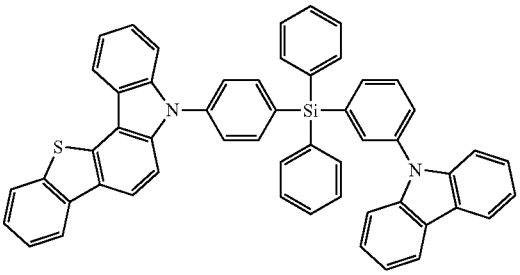 |
| 27 | 28 |
| 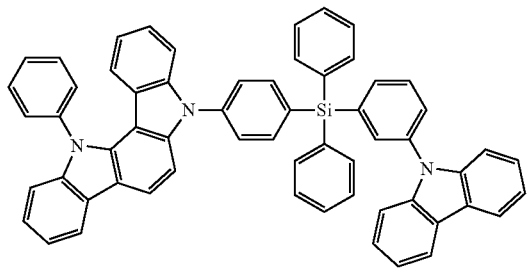 | 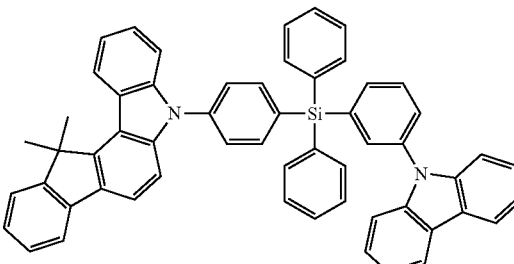 |

-continued
| 733 | 734 |
|---|---|
| 29 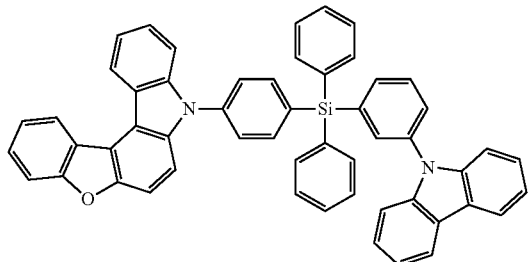 | 30 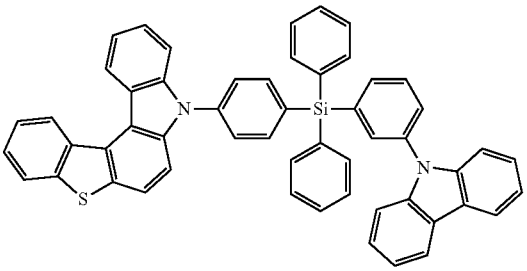 |
| 31 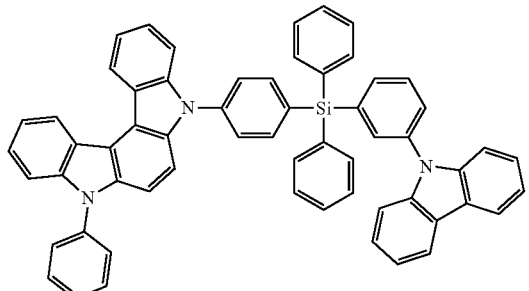 | 32 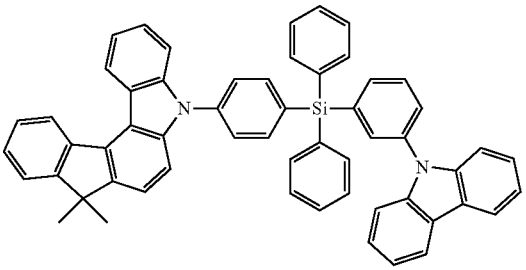 |
| 33 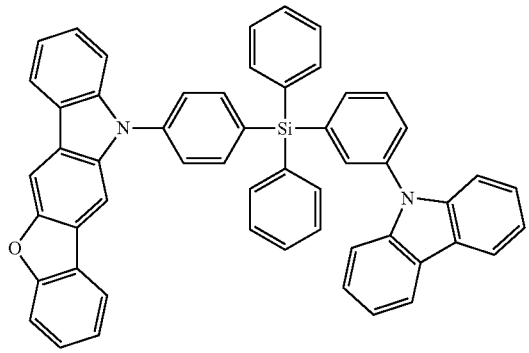 | 34 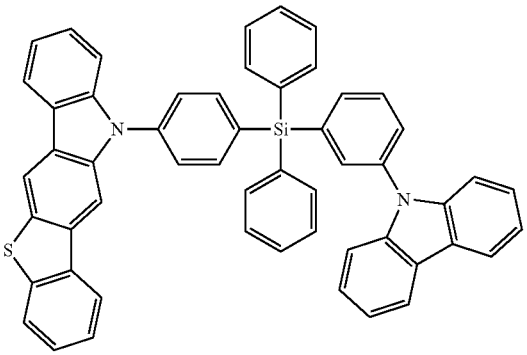 |
| 35 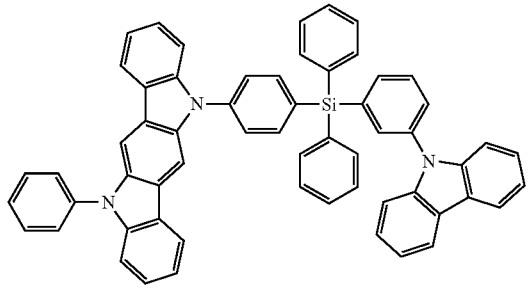 | 36 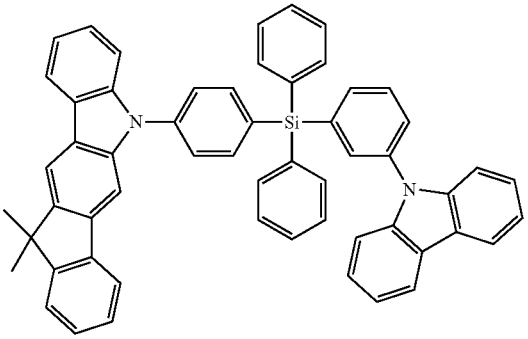 |
| 37 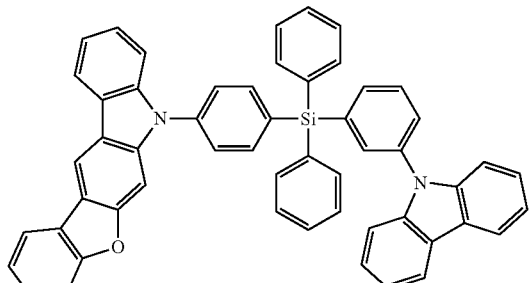 | 38 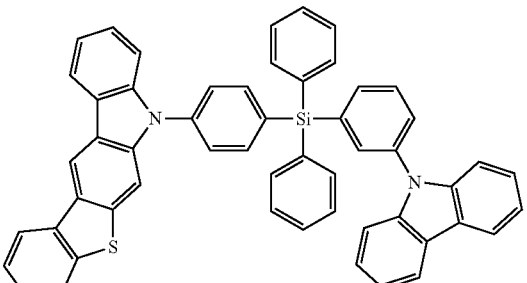 |

-continued
| 39 | 40 |
|---|---|
| 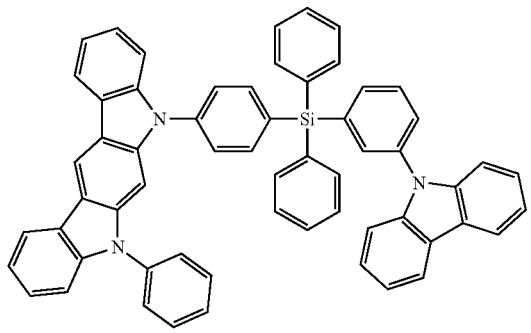 | 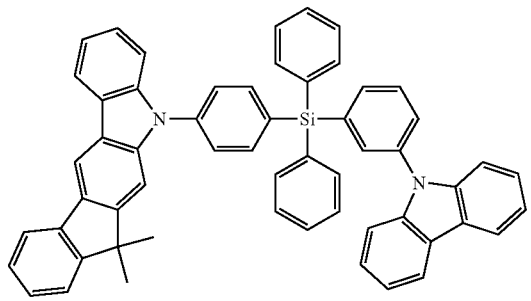 |
| 41 | 42 |
| 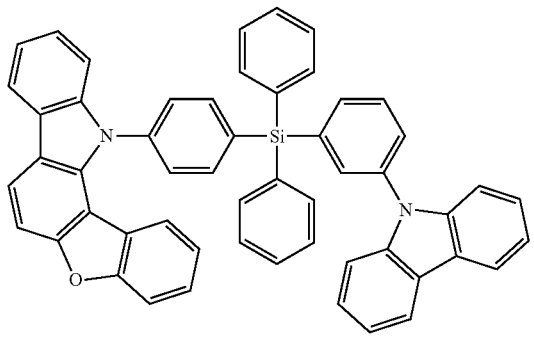 | 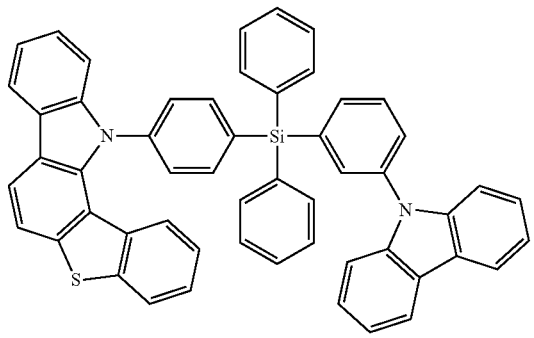 |
| 43 | 44 |
| 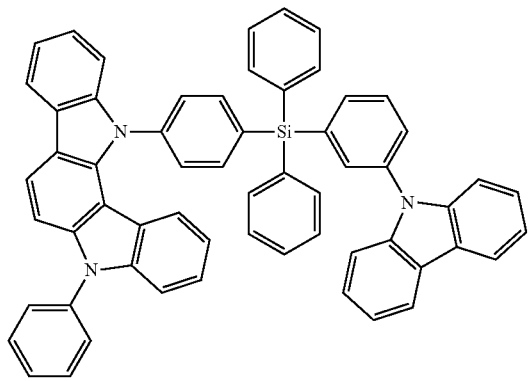 | 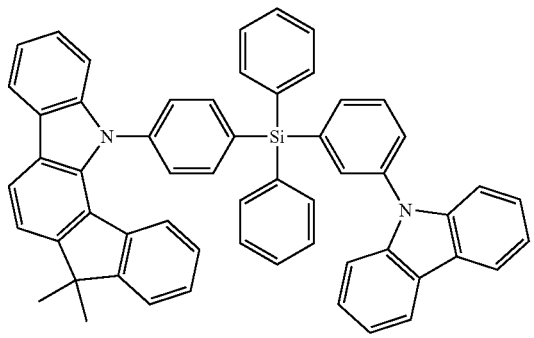 |
| 45 | 46 |
| 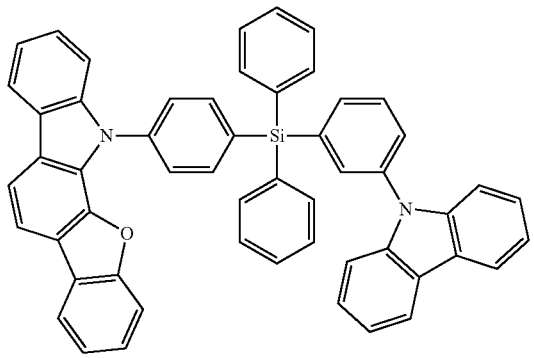 | 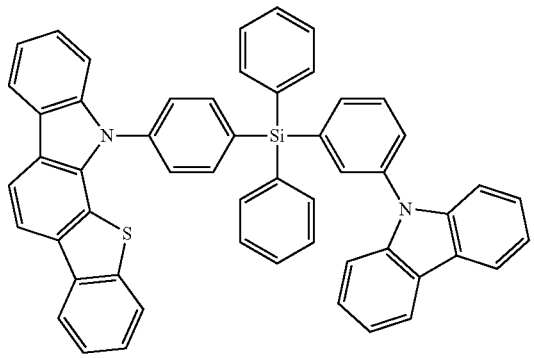 |

-continued
47
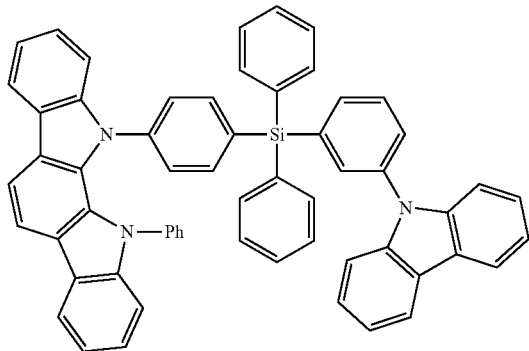
48
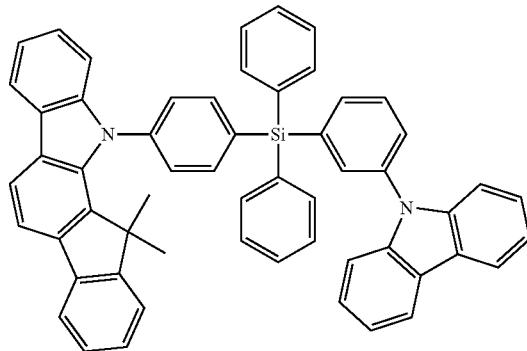
49
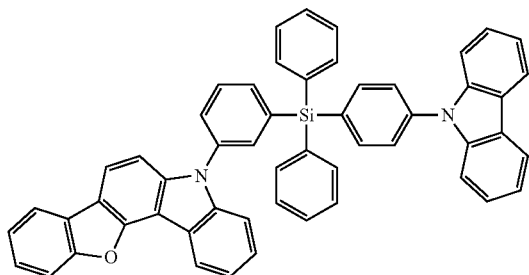
50
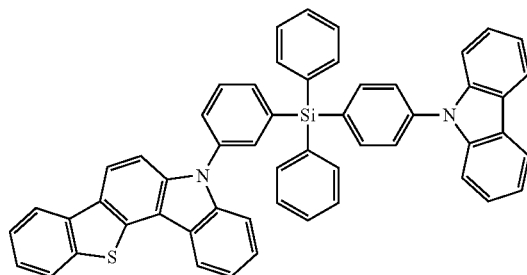
51
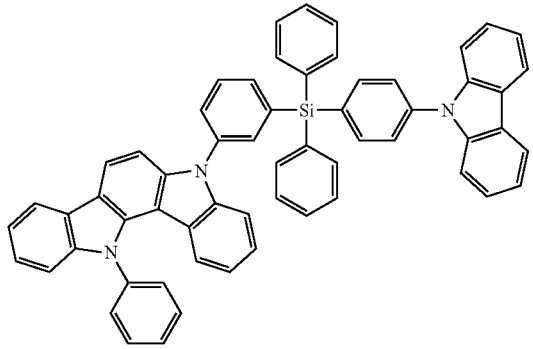
52
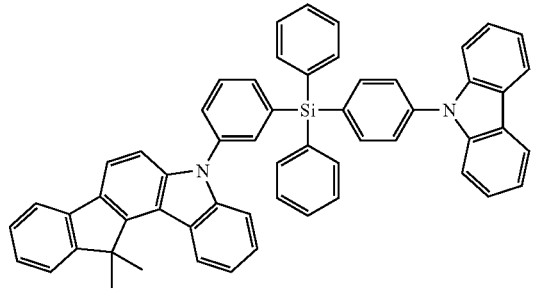
53
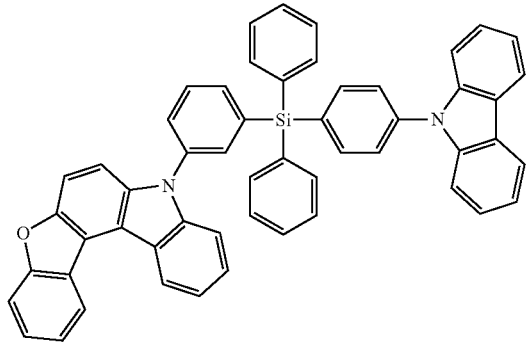
54
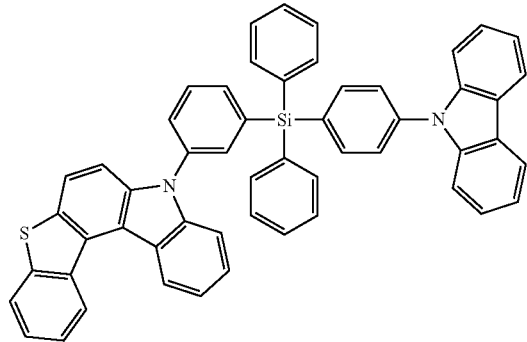

55
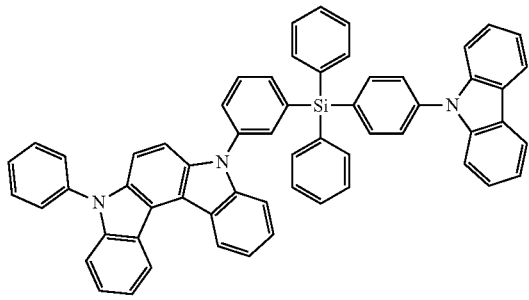
56
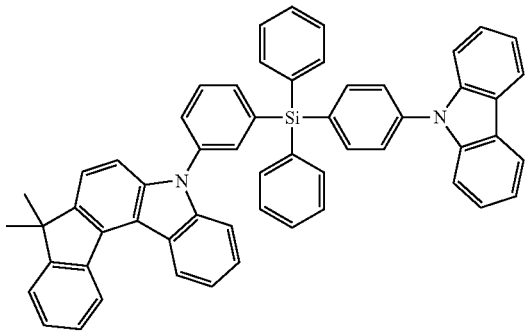
57
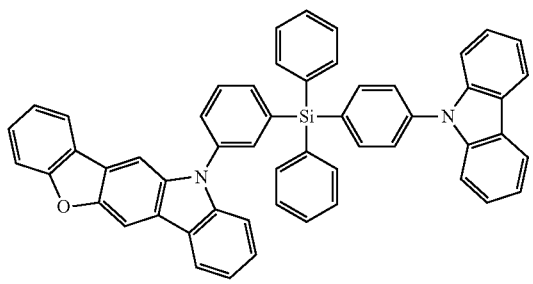
56
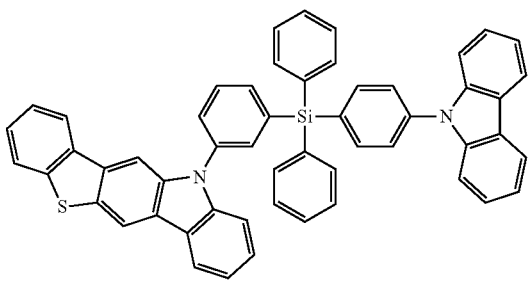
59
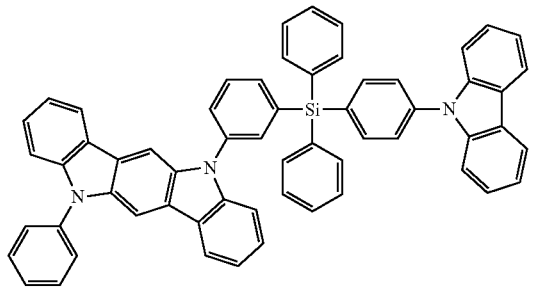
60
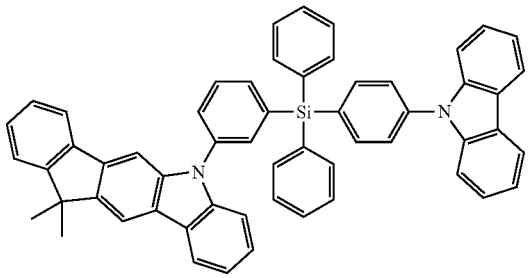
61
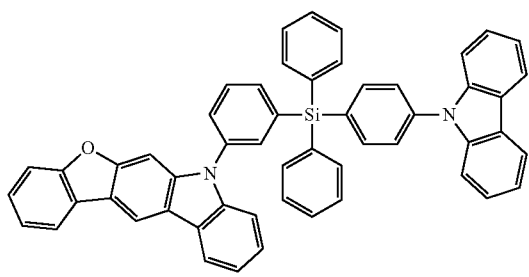
62
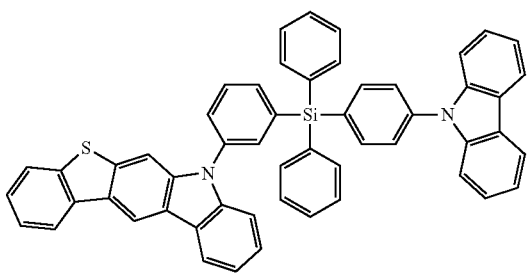
63
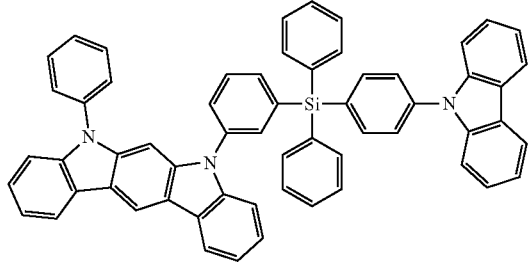
64
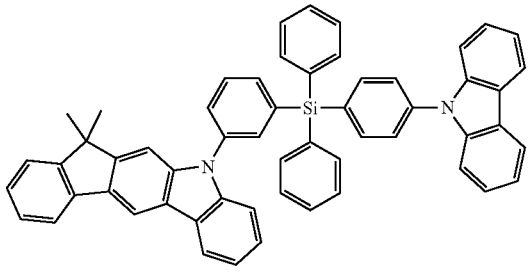

-continued
741
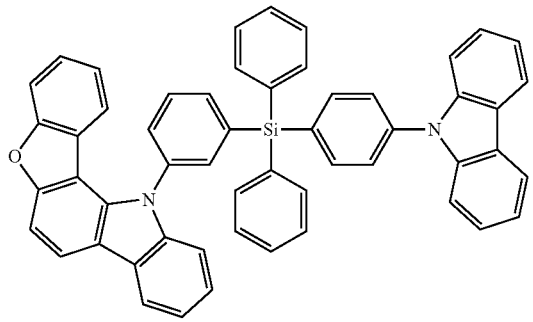
65
742
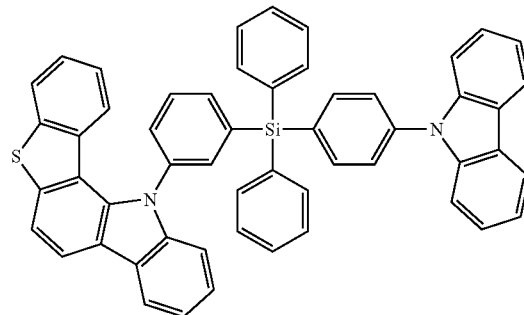
66
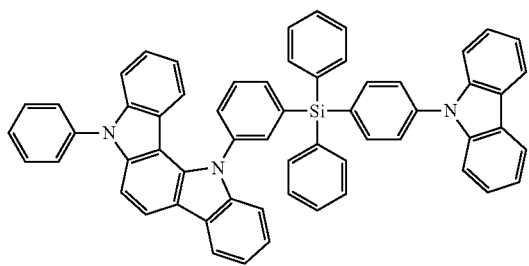
67
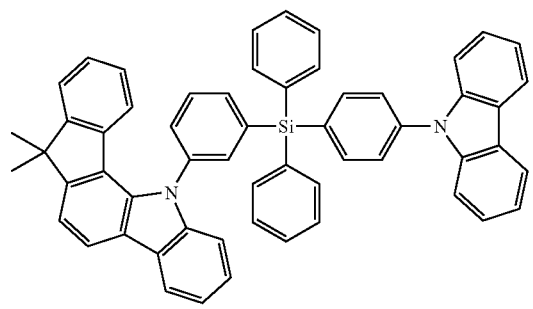
68
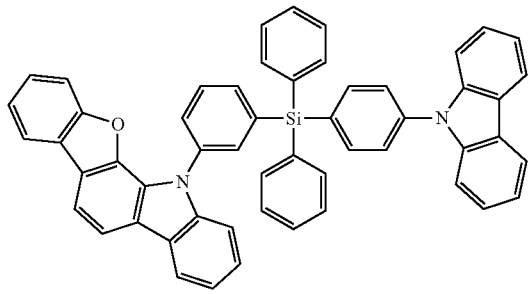
69
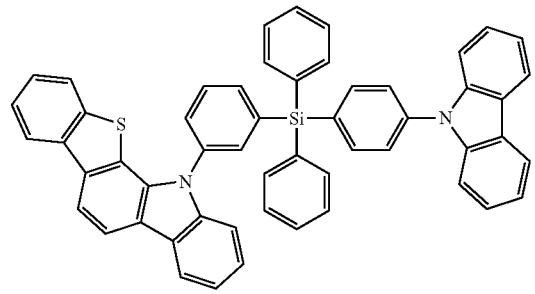
70
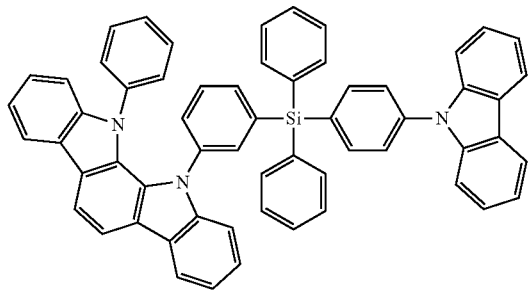
71
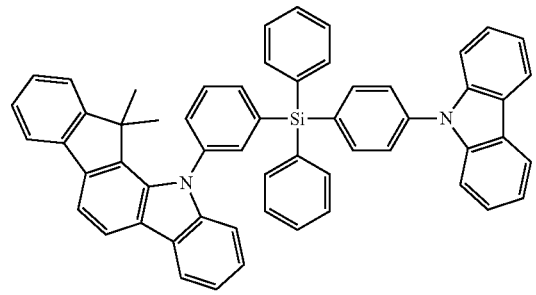
72
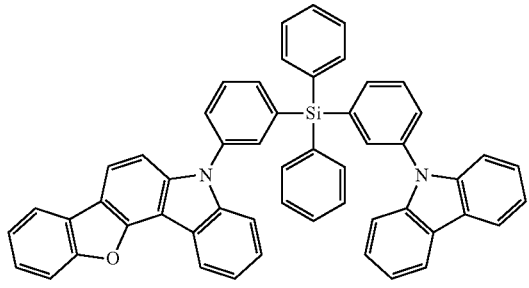
73
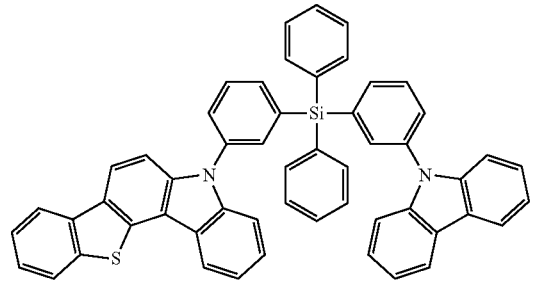
74

-continued
75
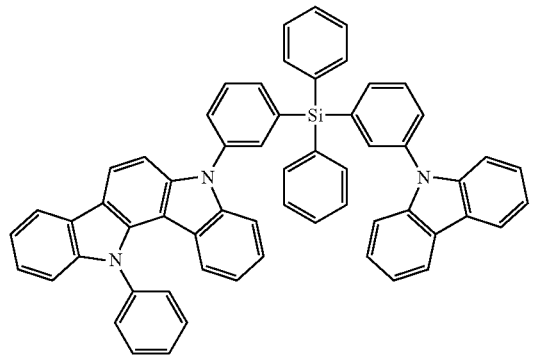
76
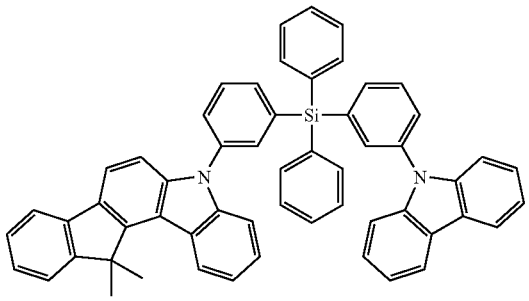
77
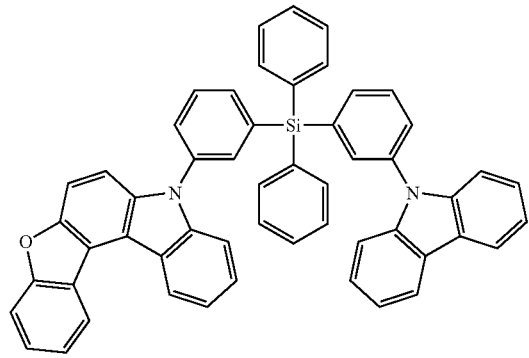
78
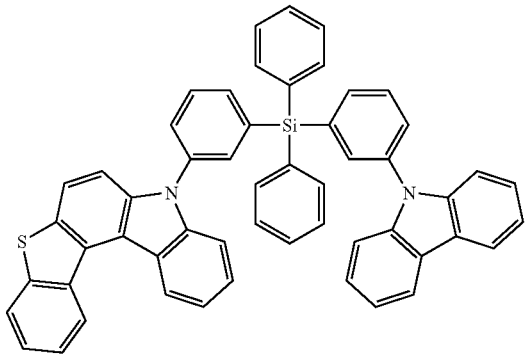
79
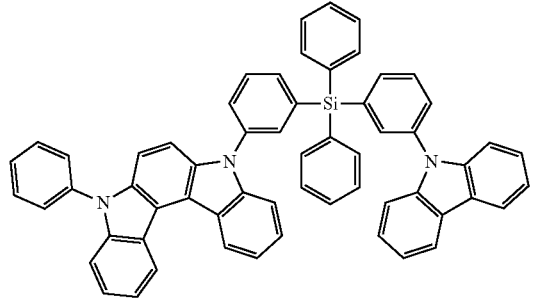
80
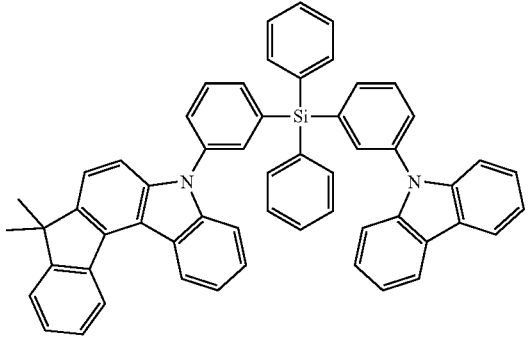
81
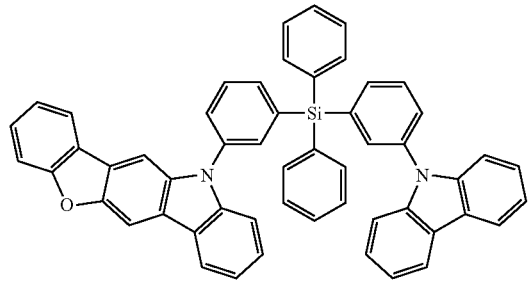
82
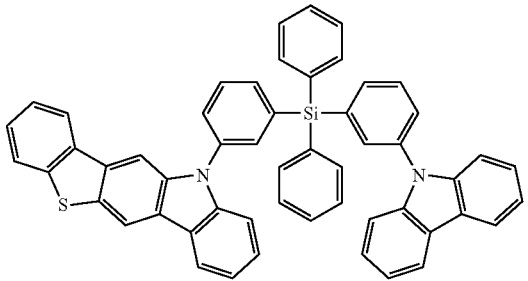

-continued
83
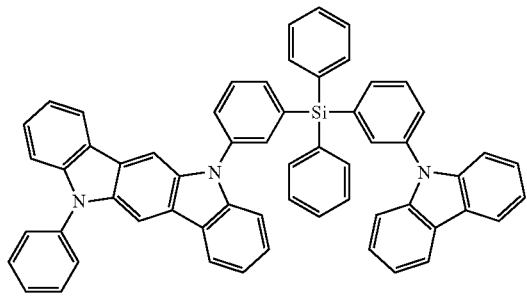
84
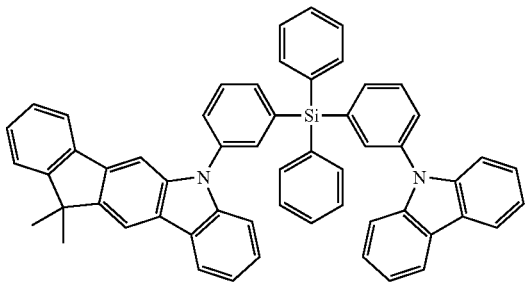
85
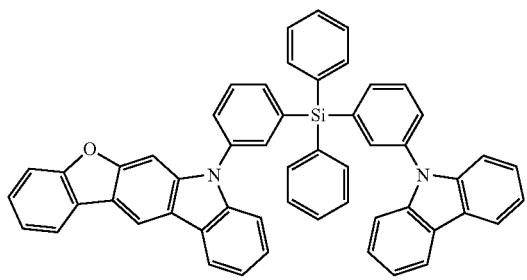
86
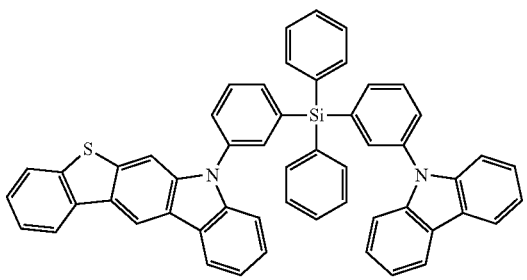
87
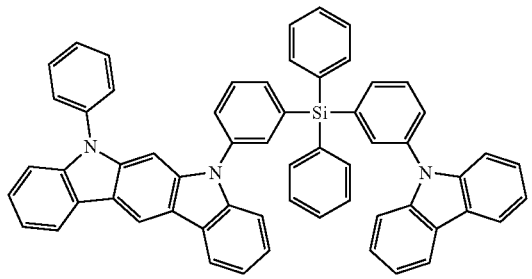
88
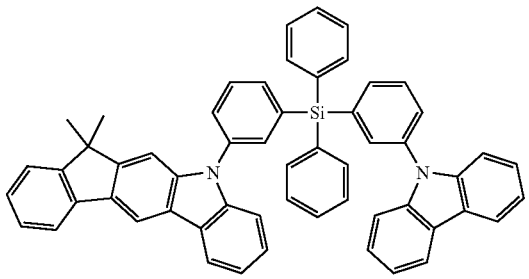
89
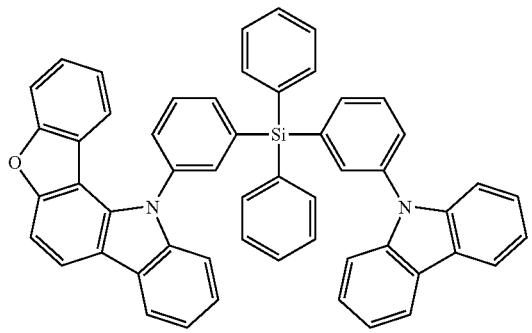
90
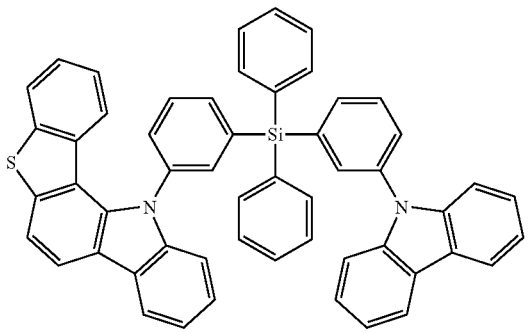
91
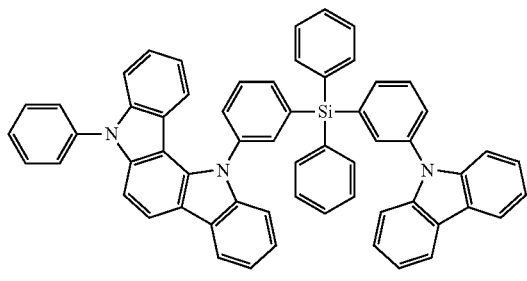
92
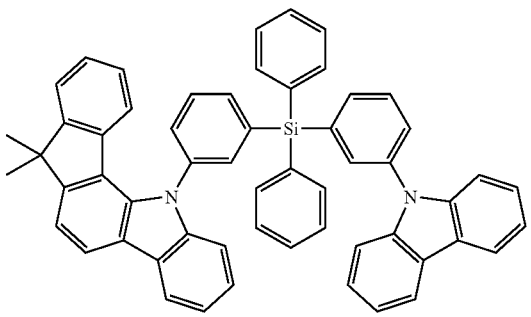

-continued
93
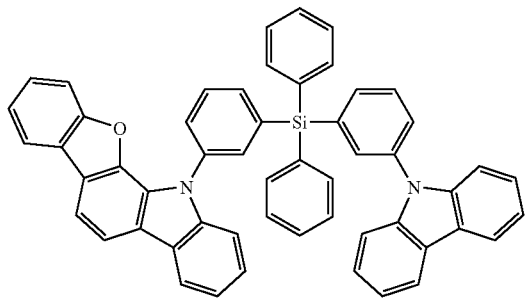
94
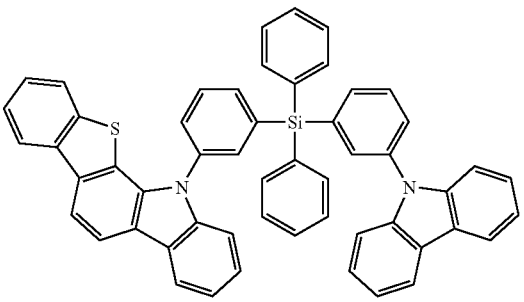
95
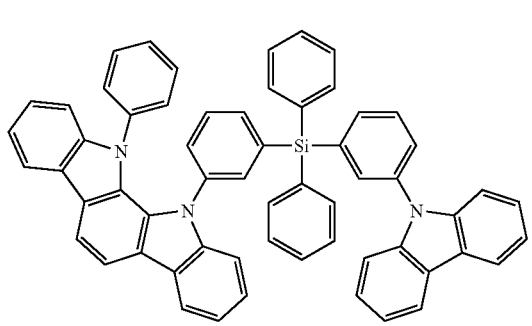
96
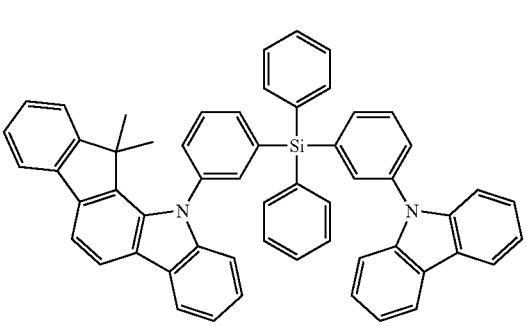
97
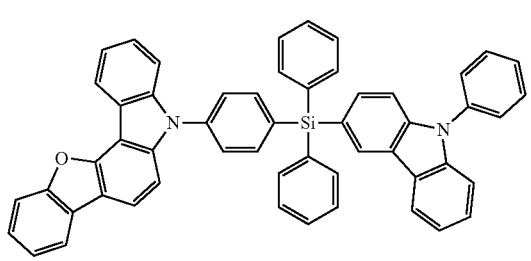
98
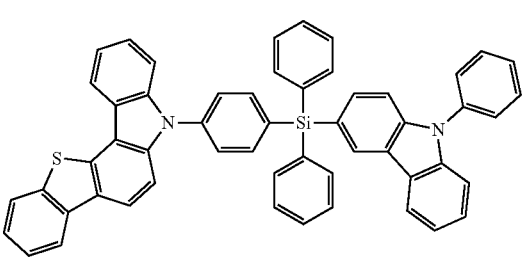
99
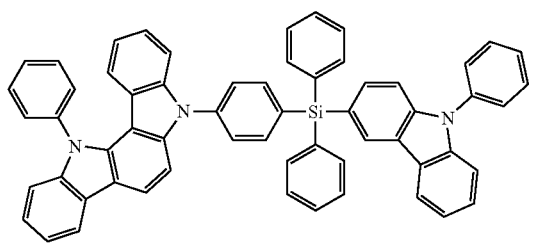
100
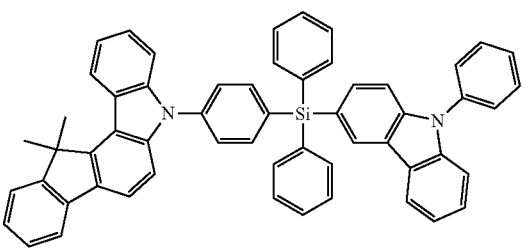
101
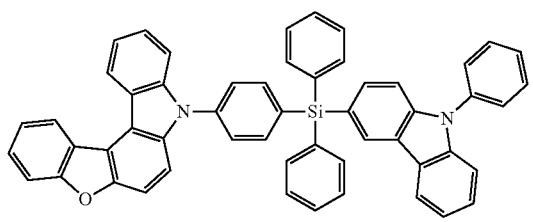
102
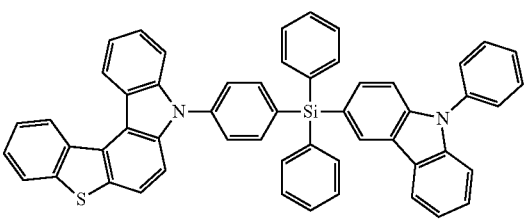

-continued
| 103 | 104 |
|---|---|
| 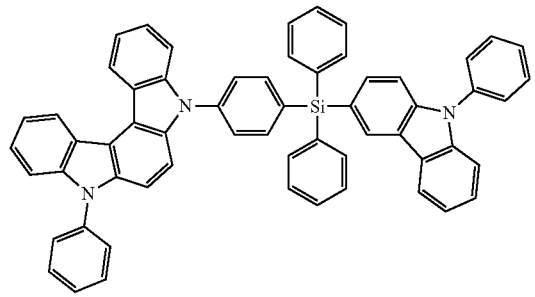 | 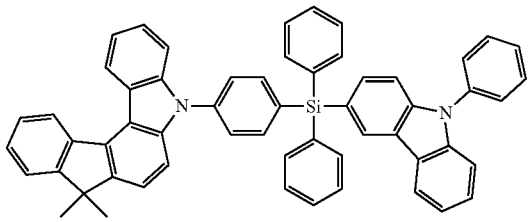 |
| 105 | 106 |
| 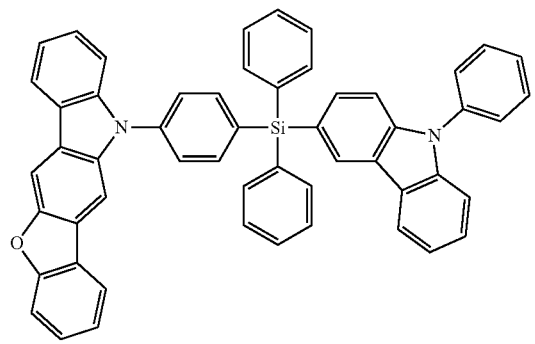 | 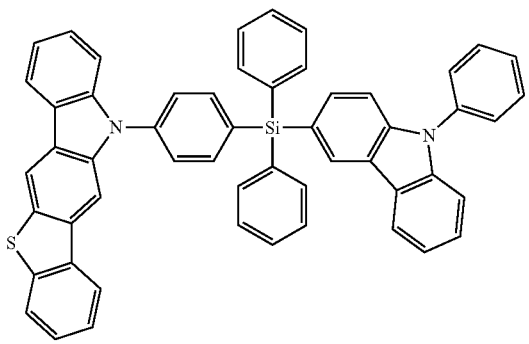 |
| 107 | 108 |
| 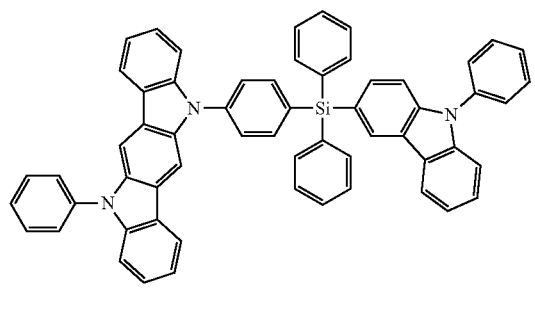 | 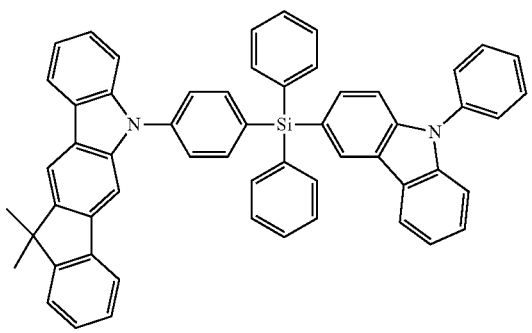 |
| 109 | 110 |
| 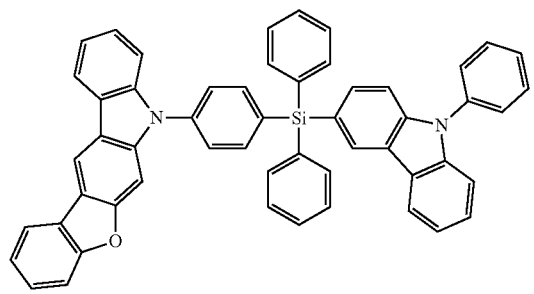 | 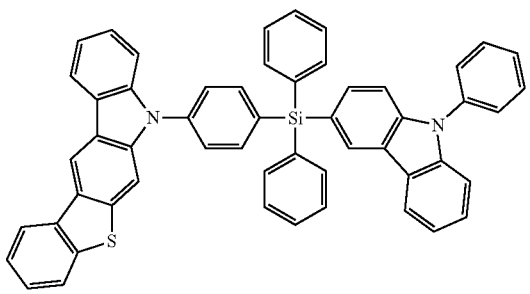 |

-continued
111
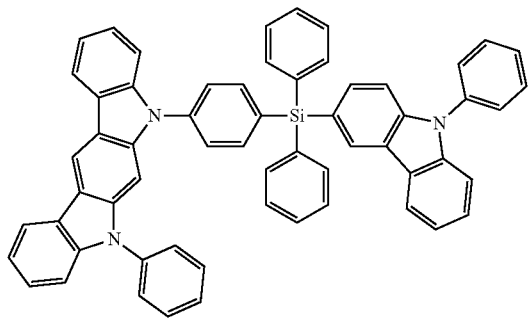
112
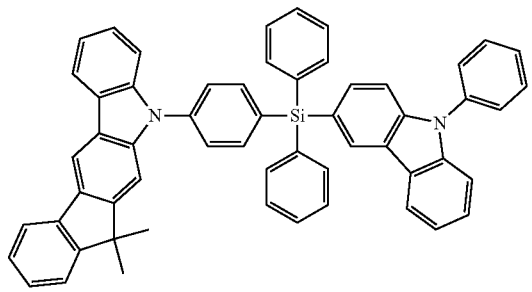
113
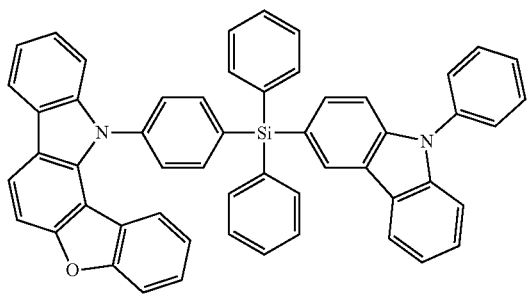
114
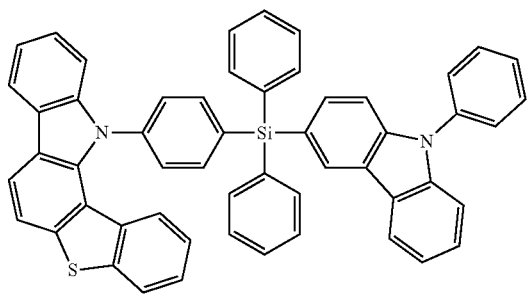
115
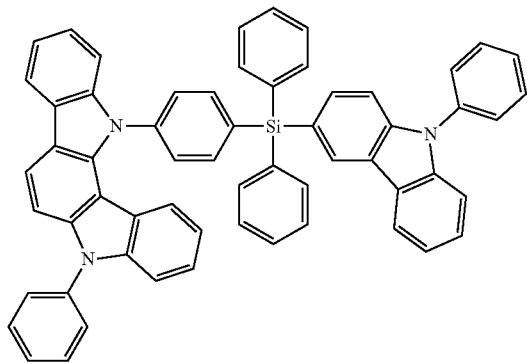
116
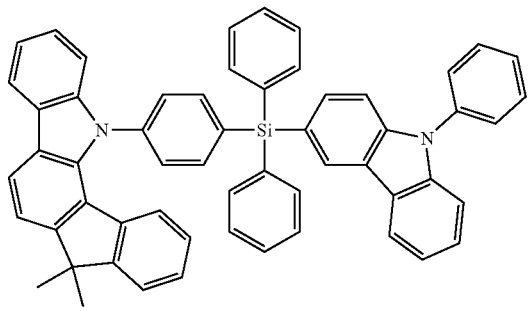
117
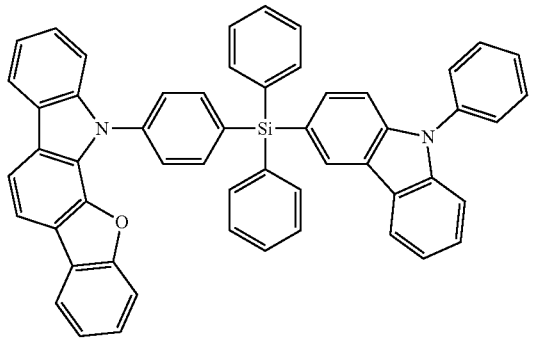
118
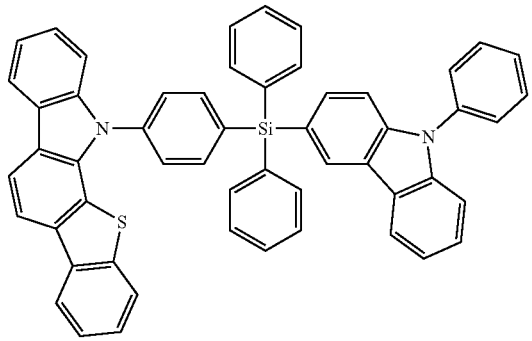

-continued
119
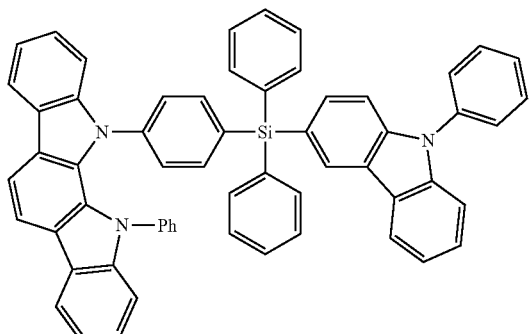
120
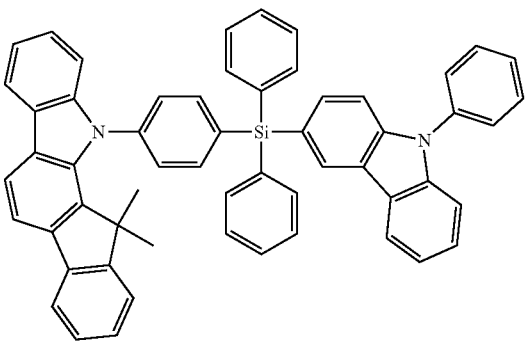
121
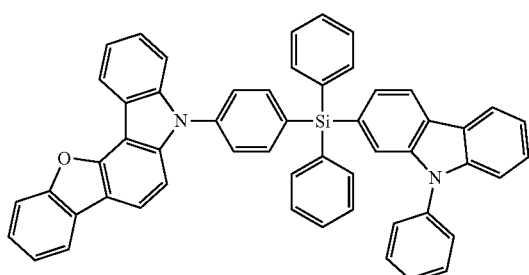
122
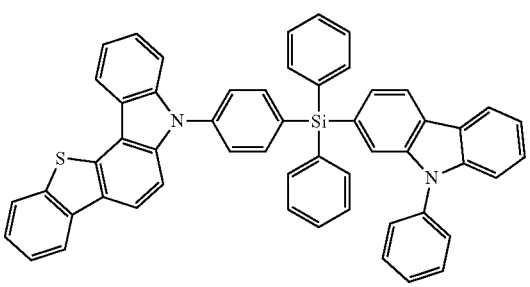
123
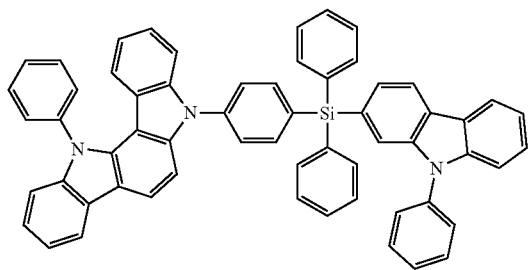
124
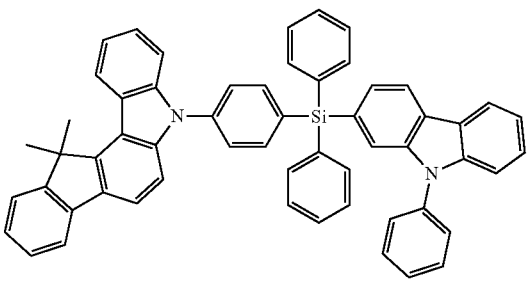
125
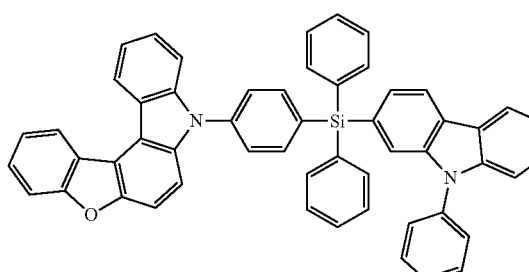
126
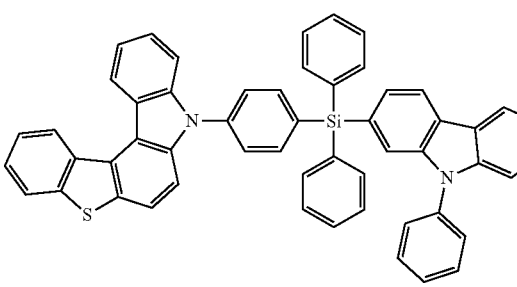
127
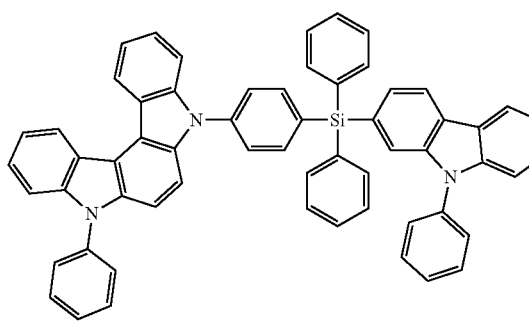
128
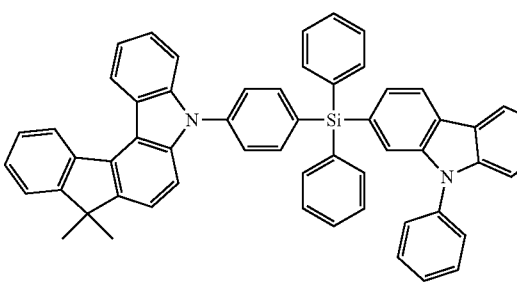

-continued
129
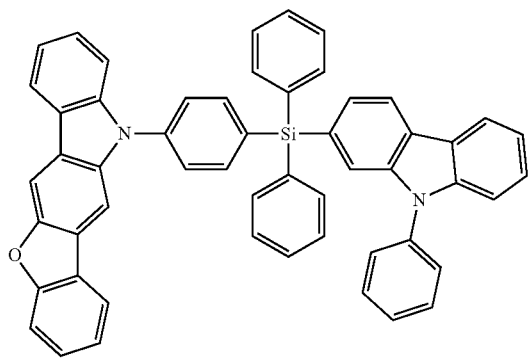
130
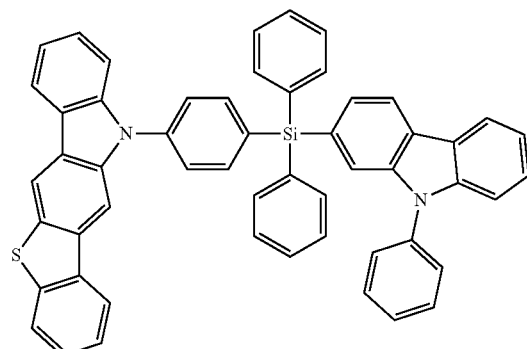
131
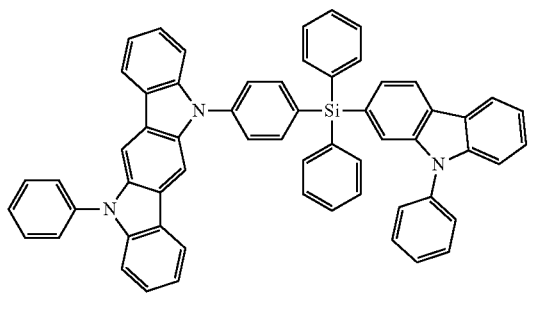
132
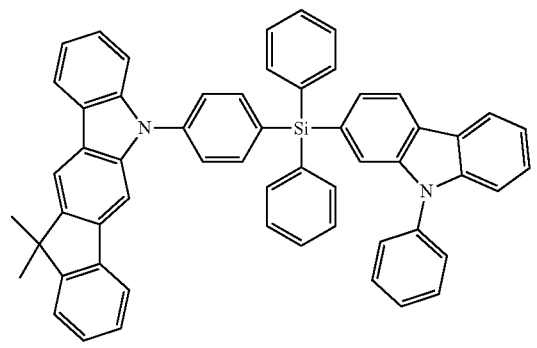
133
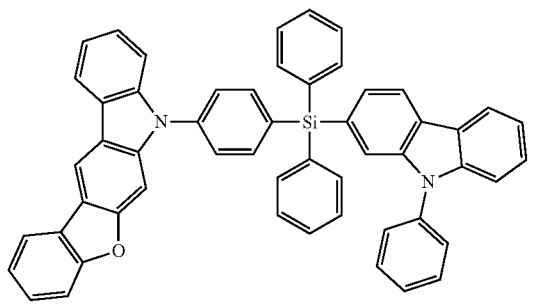
134
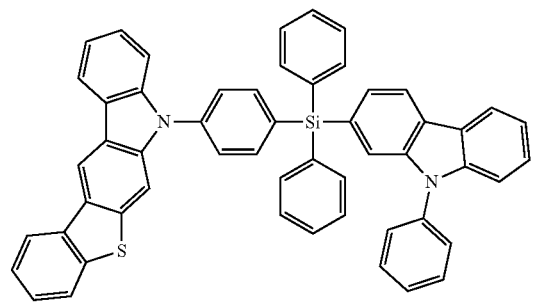
135
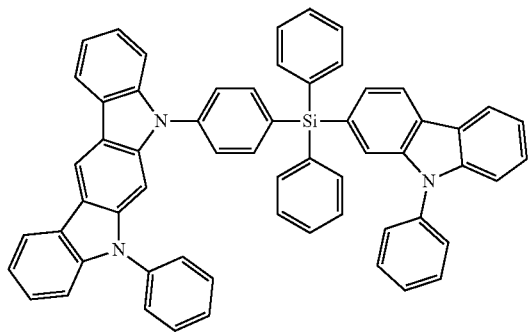
136
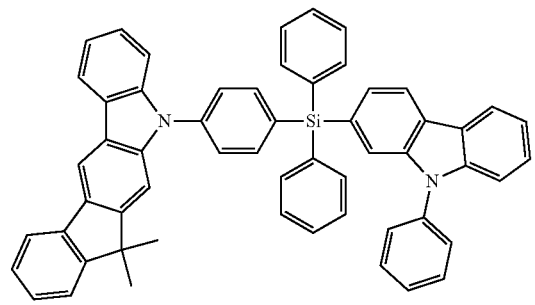

-continued
137
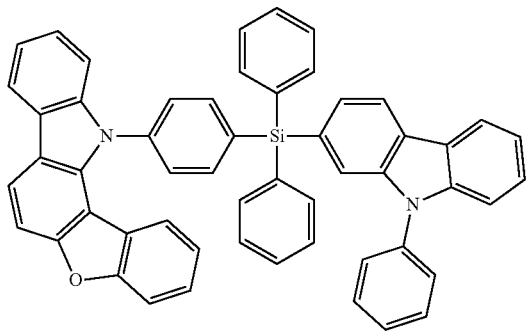
138
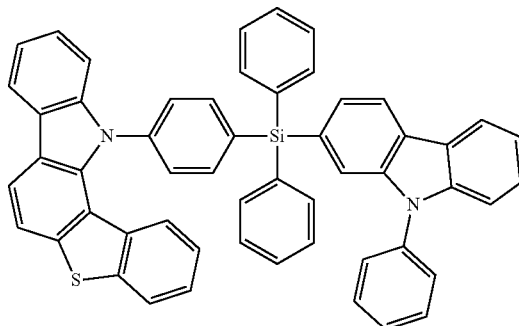
139
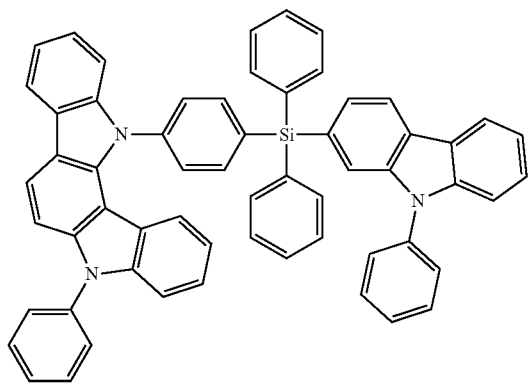
140
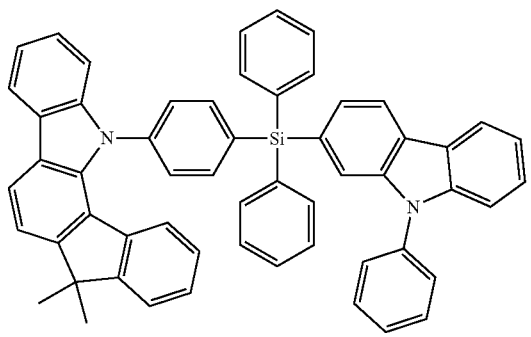
141
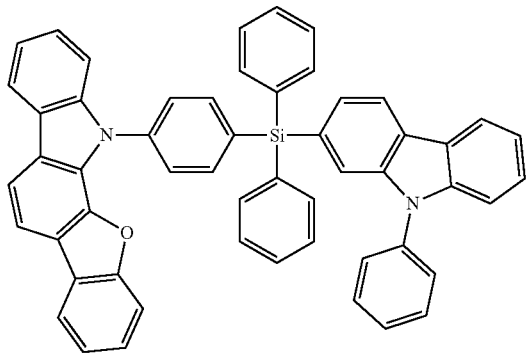
142
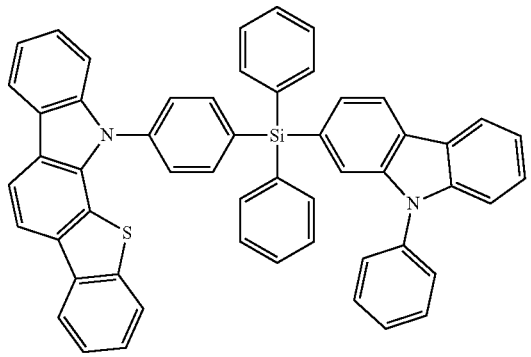
143
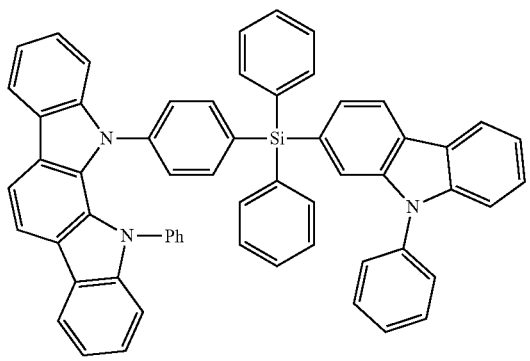
144
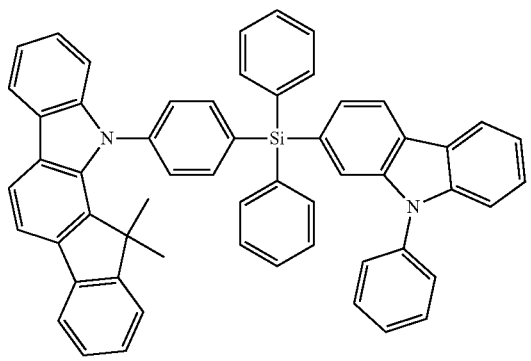

-continued
145
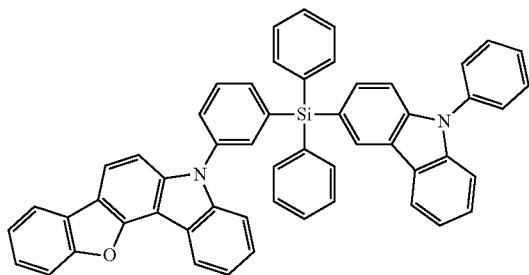
146
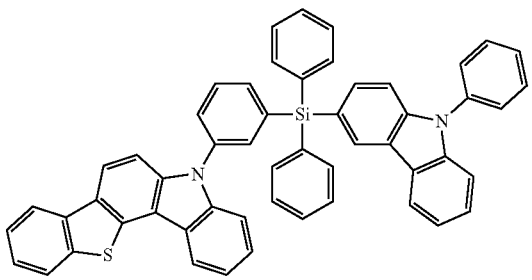
147
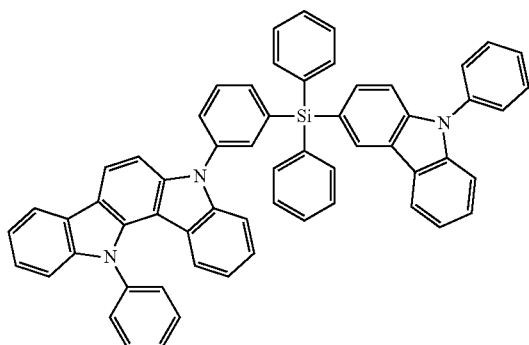
148
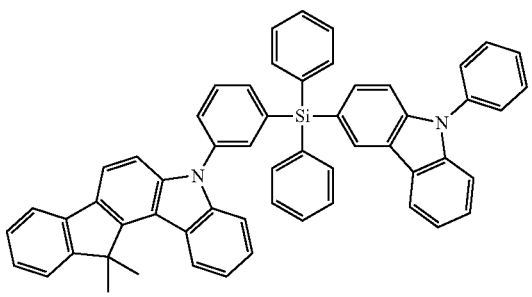
149
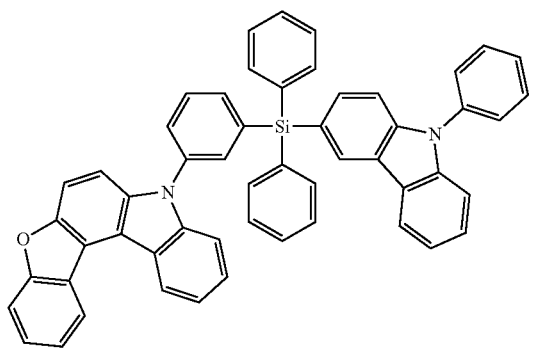
150
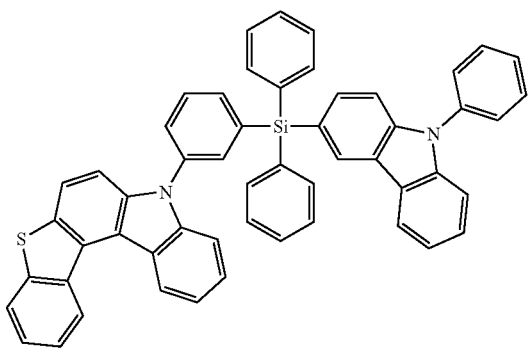
151
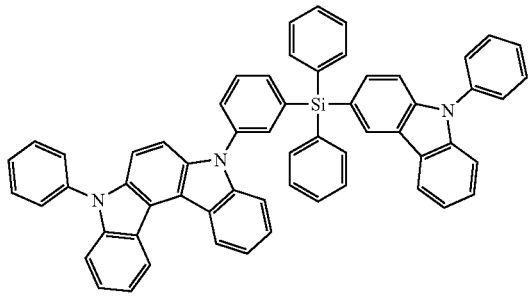
152
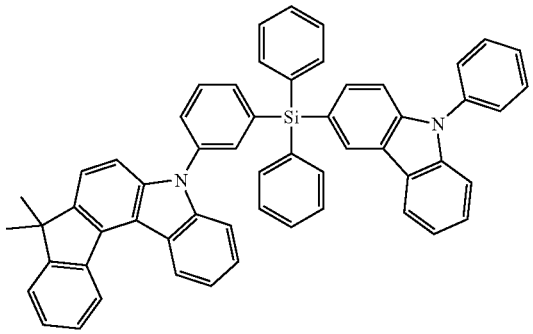

-continued
153
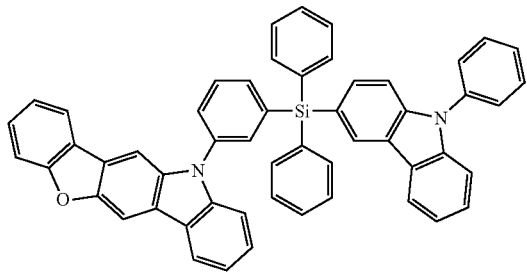
154
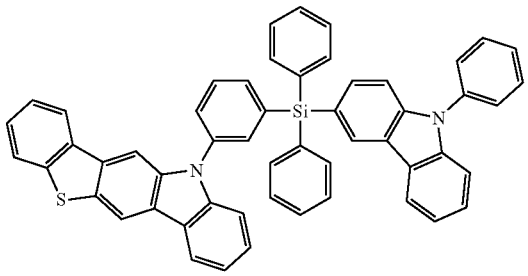
155
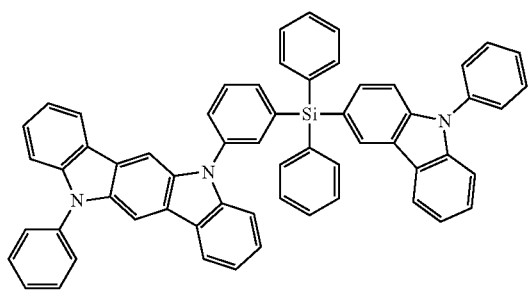
156
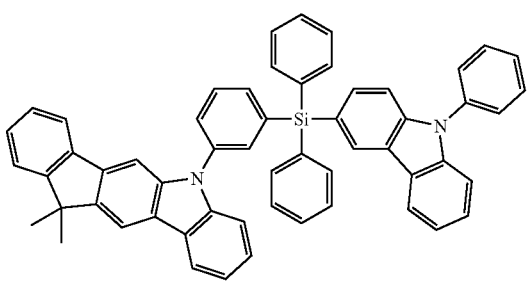
157
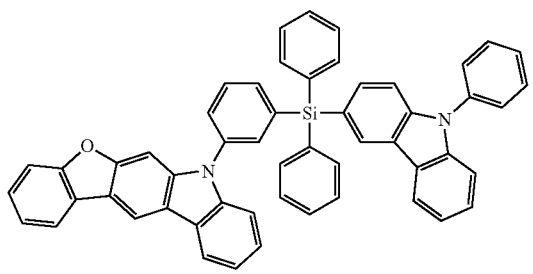
158
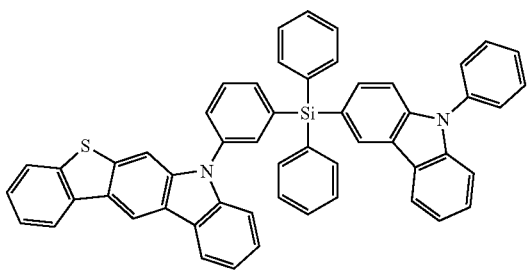
159
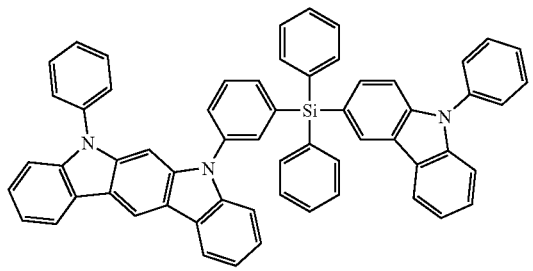
160
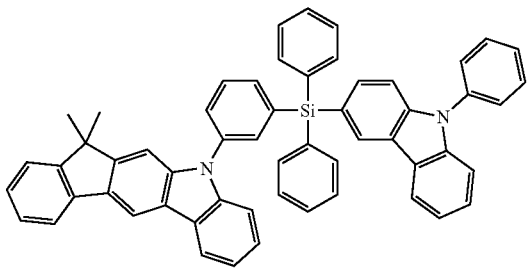
161
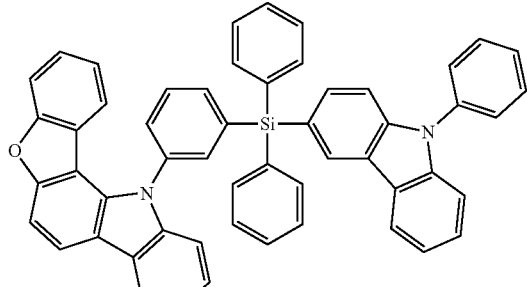
162
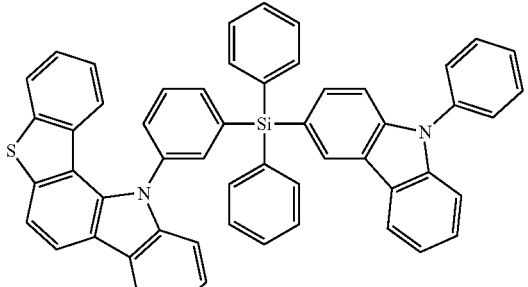

163
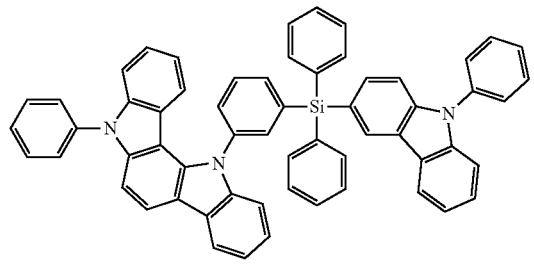
164
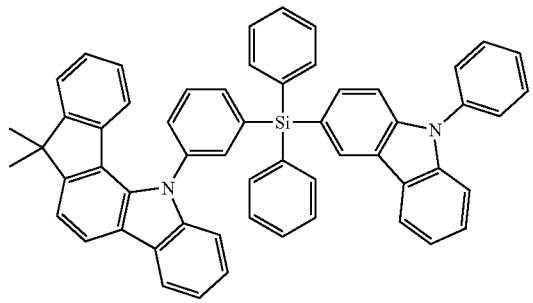
165
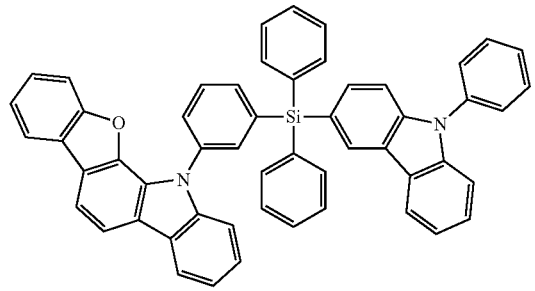
166
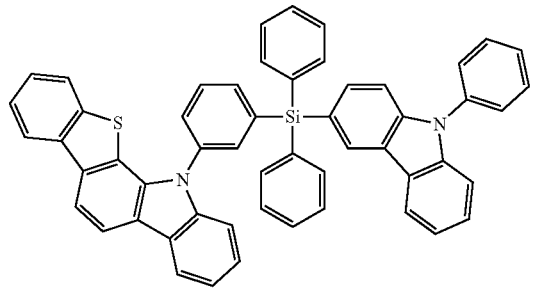
167
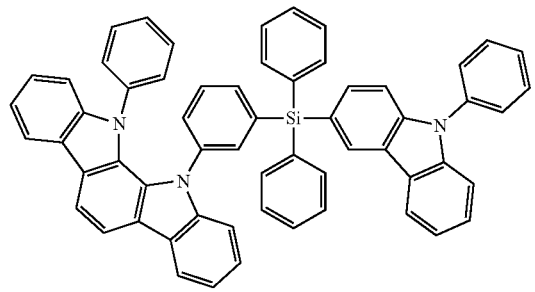
168
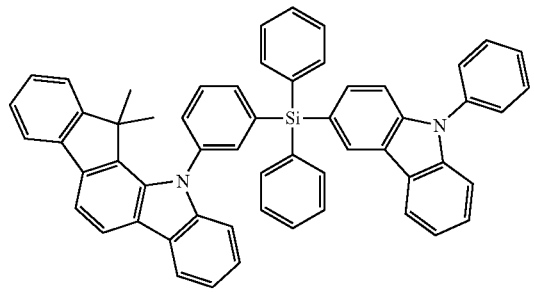
169
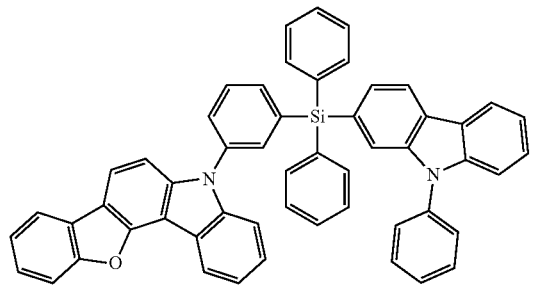
170
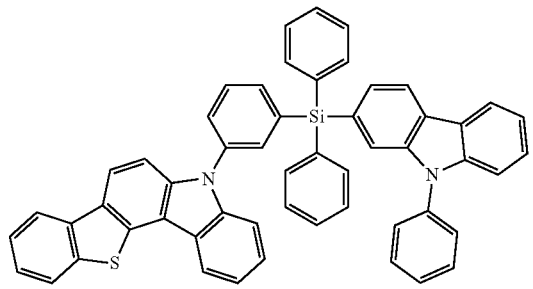

-continued
171
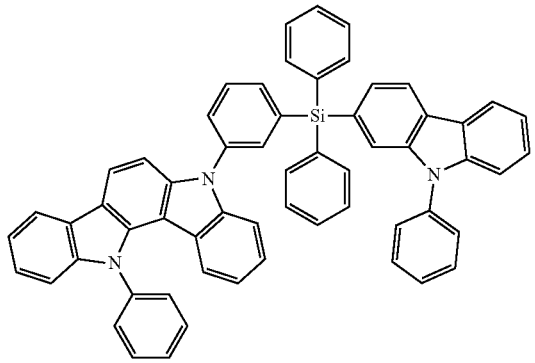
172
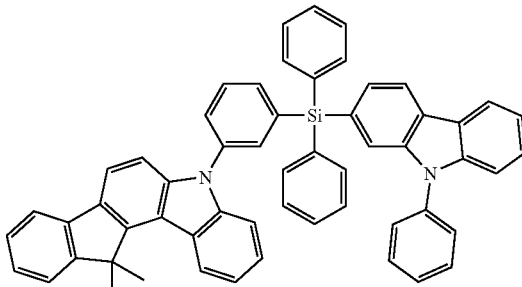
173
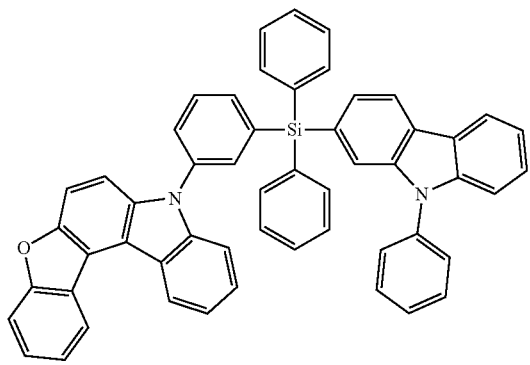
174
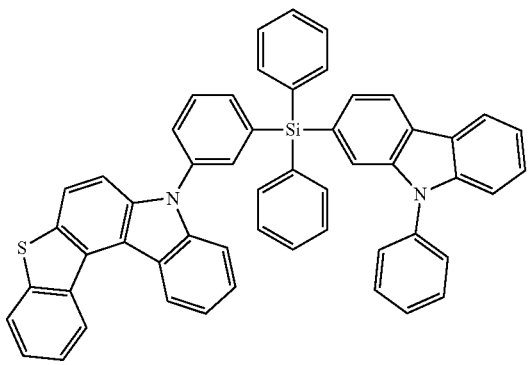
175
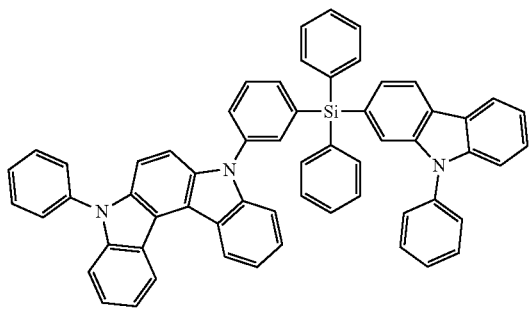
176
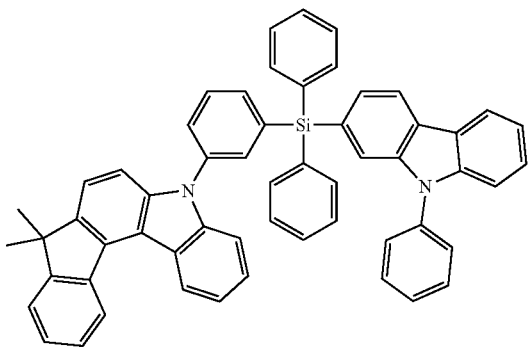
177
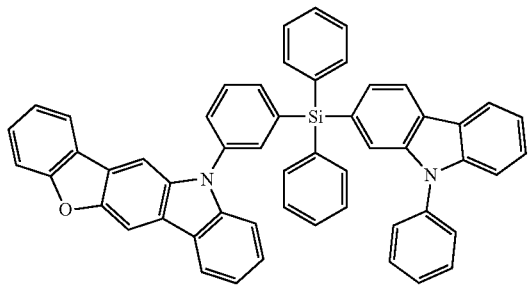
178
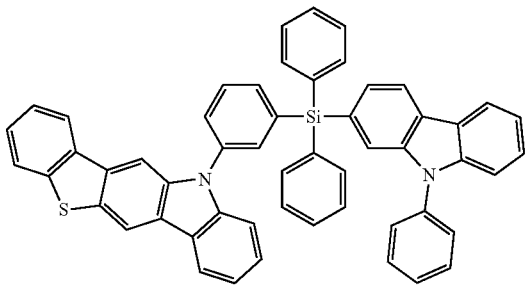

-continued
179
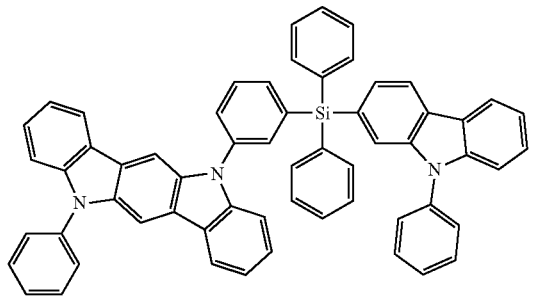
180
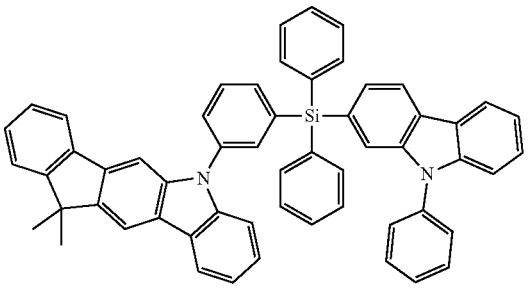
181
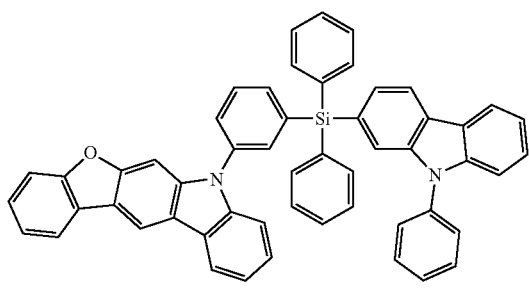
182
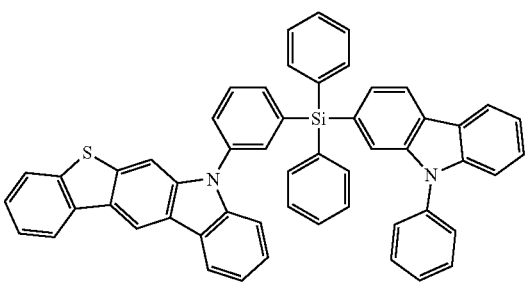
183
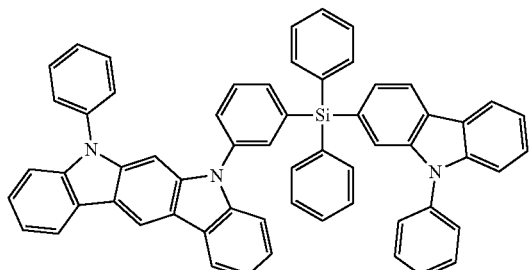
184
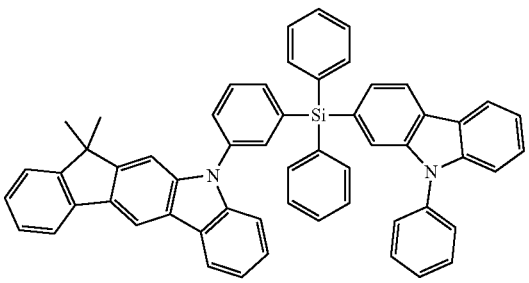
185
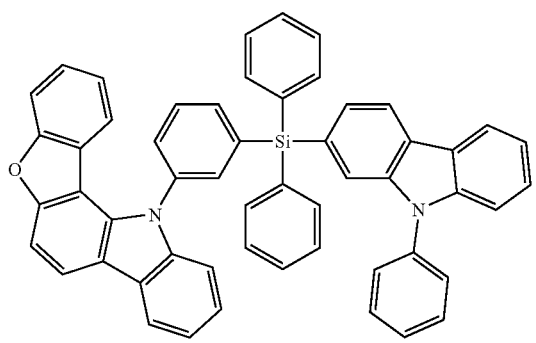
186
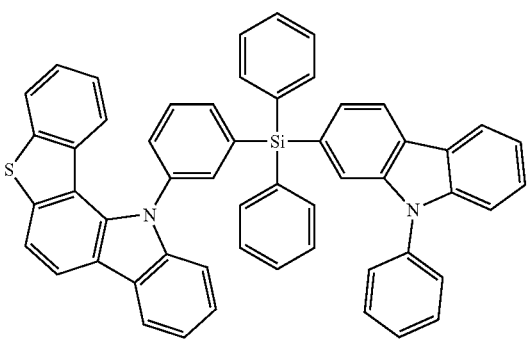
187
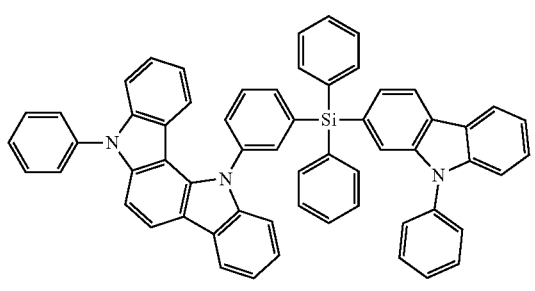
188
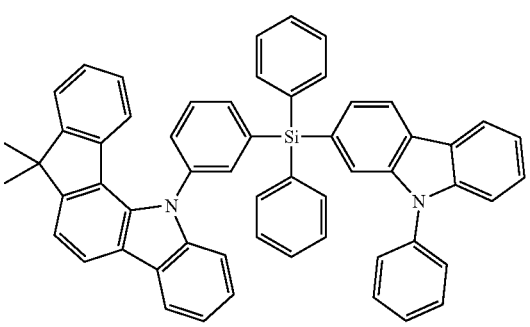

-continued
| 769 | 770 |
|---|---|
| 189 | 190 |
| 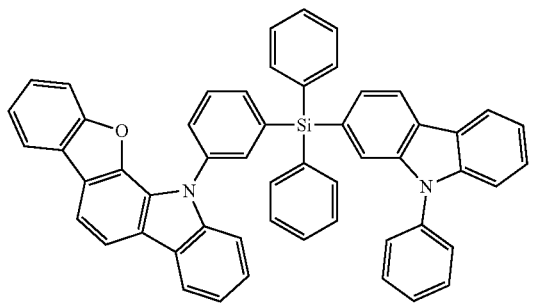 | 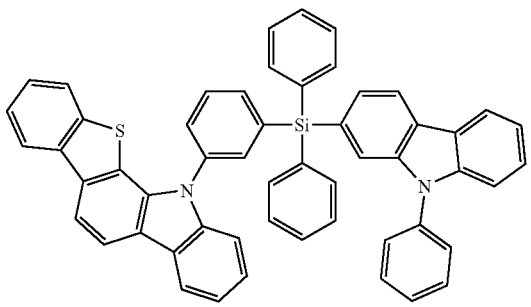 |
| 191 | 192 |
| 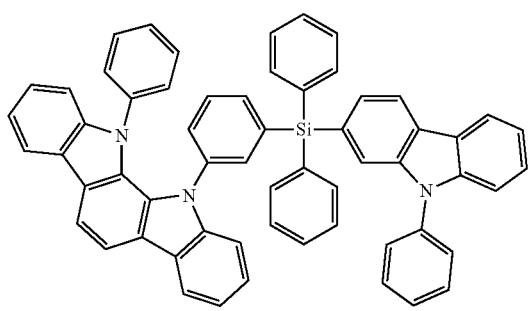 | 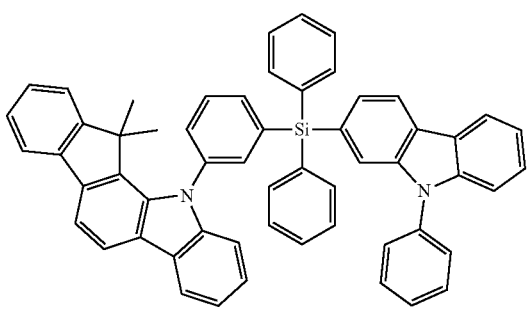 |
| 193 | 194 |
| 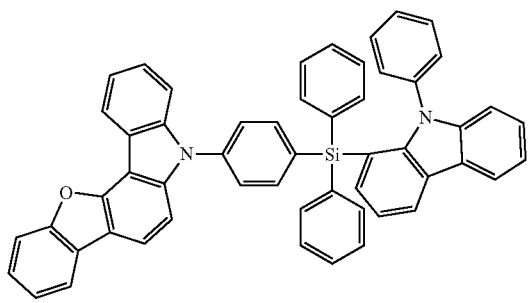 | 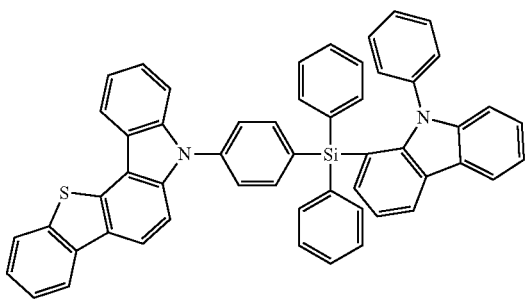 |
| 195 | 196 |
| 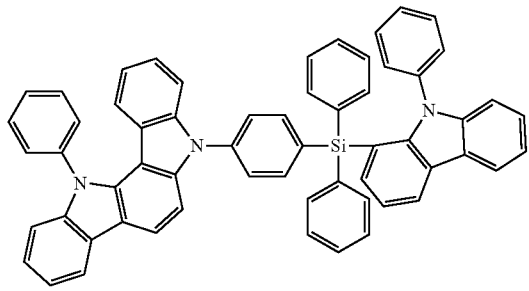 | 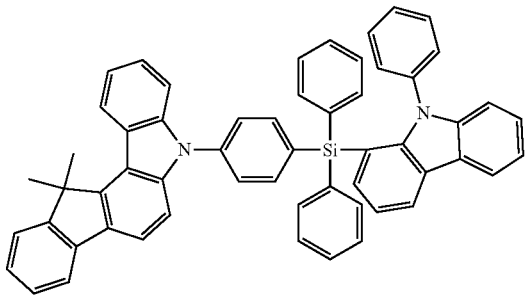 |
| 197 | 198 |
| 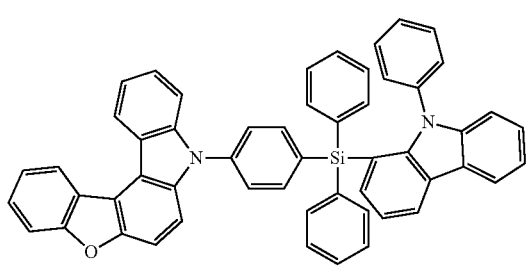 | 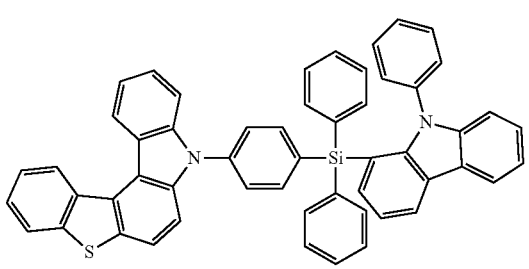 |

-continued
199
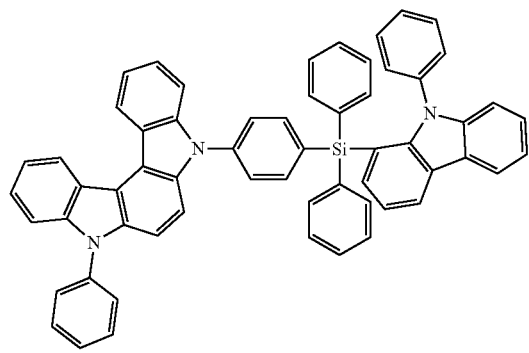
200
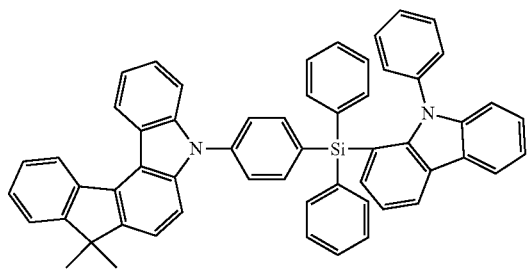
201
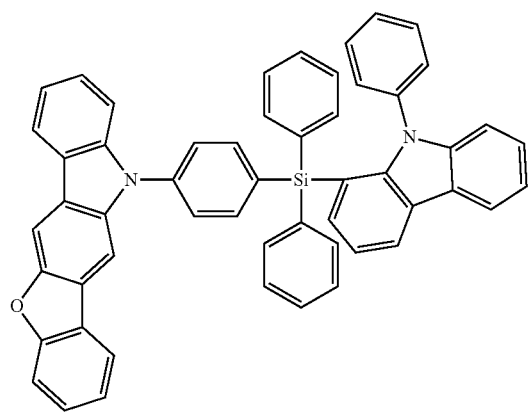
202
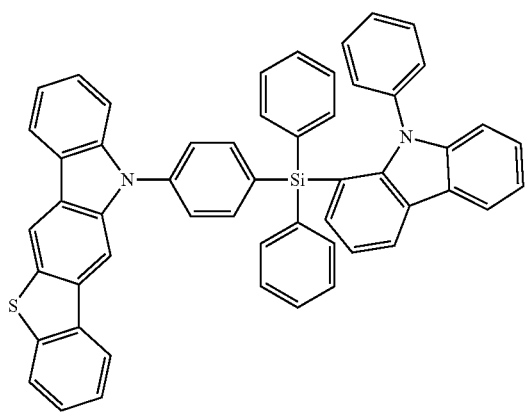
203
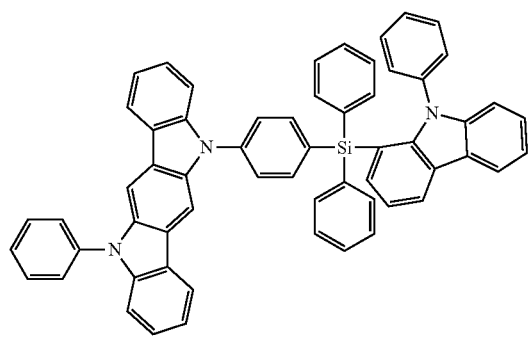
204
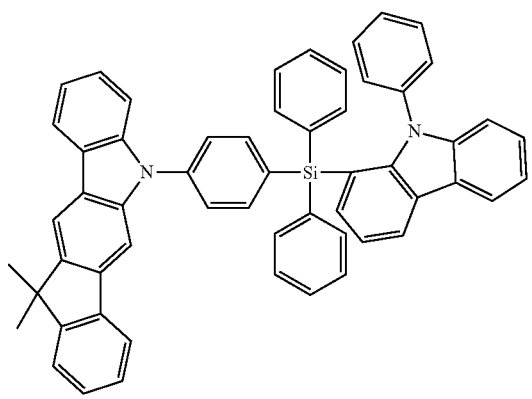
205
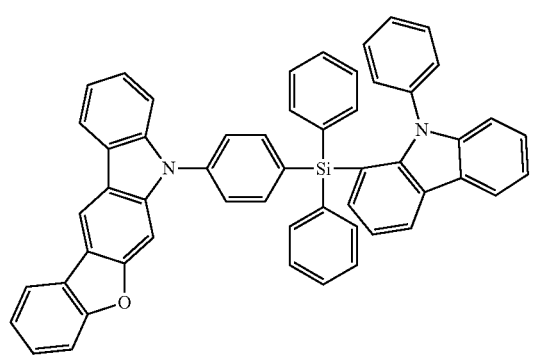
206
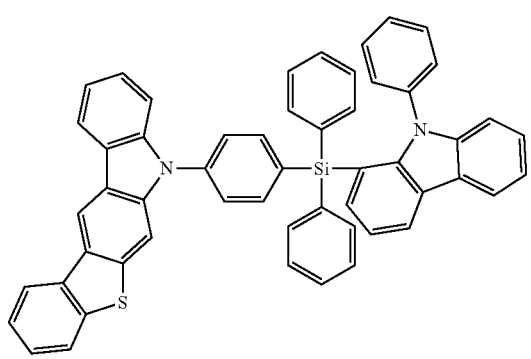

-continued
207
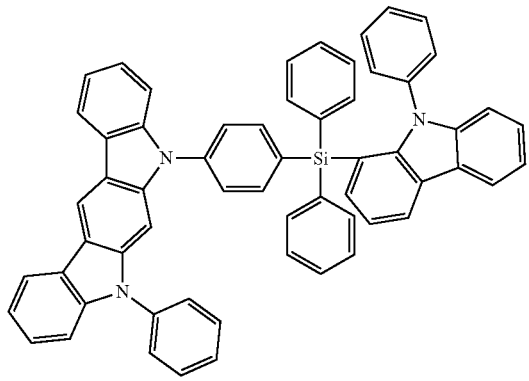
208
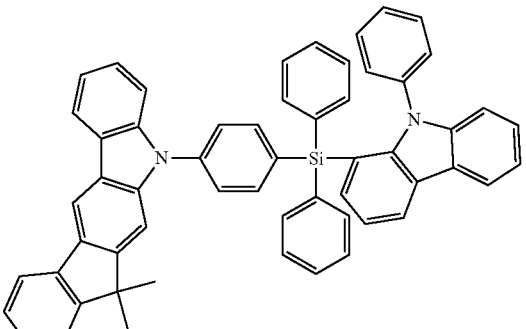
209
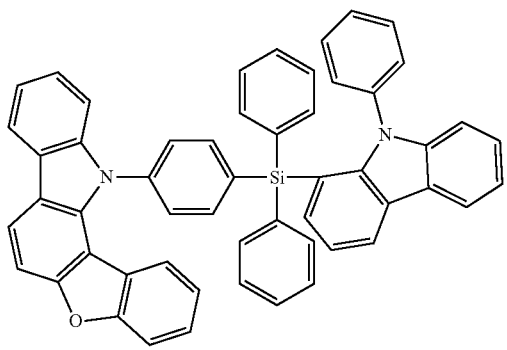
210
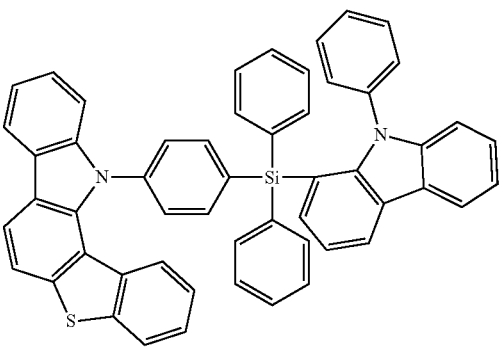
211
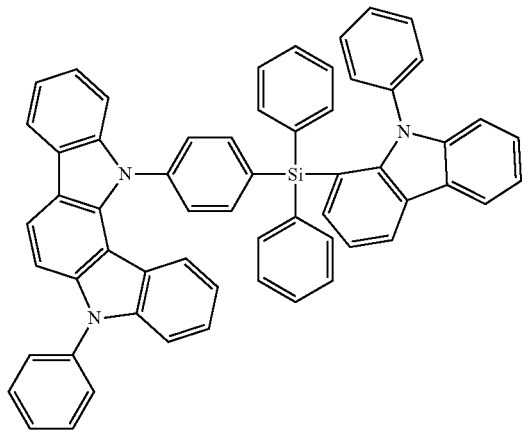
212
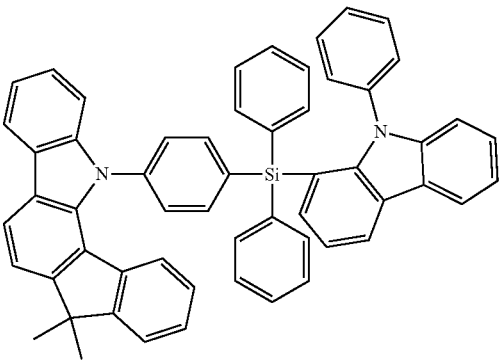
213
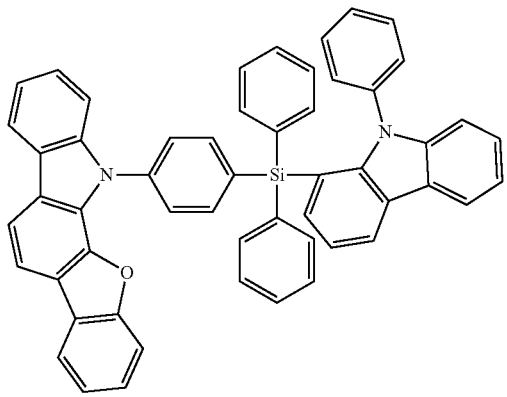
214
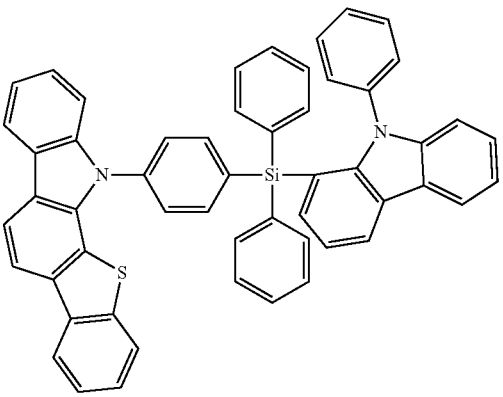

-continued
215
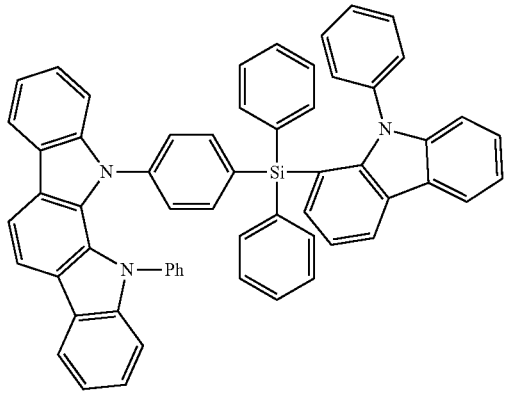
216
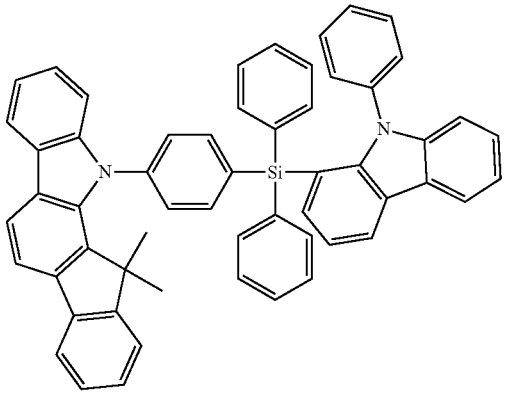
217
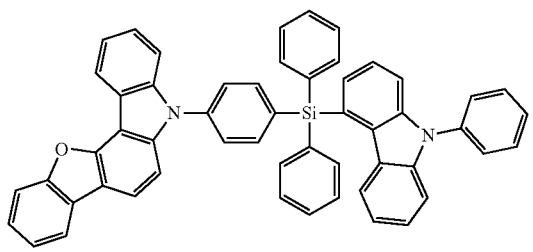
218
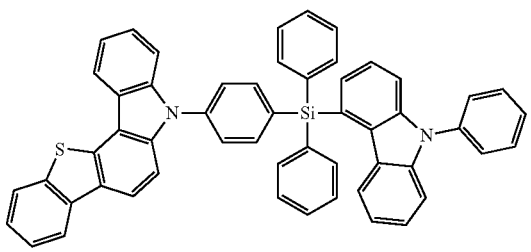
219
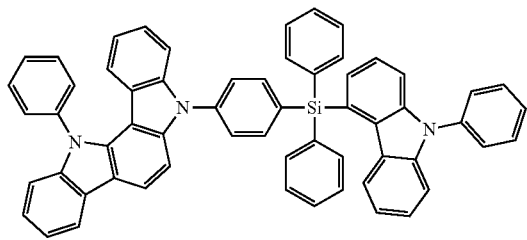
220
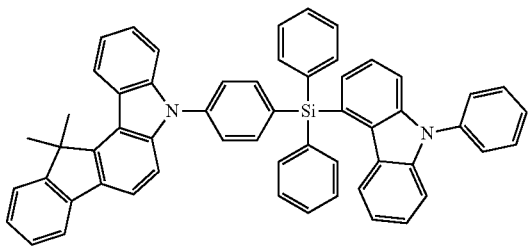
221
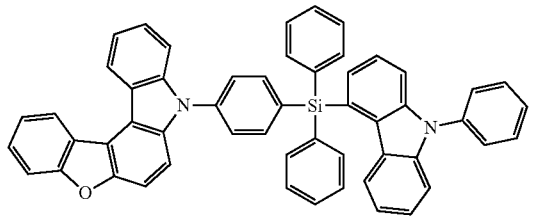
222
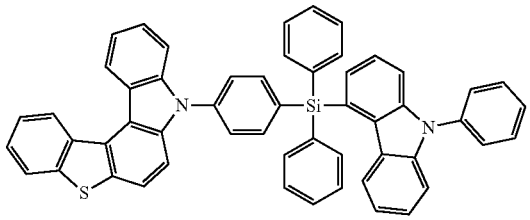
223
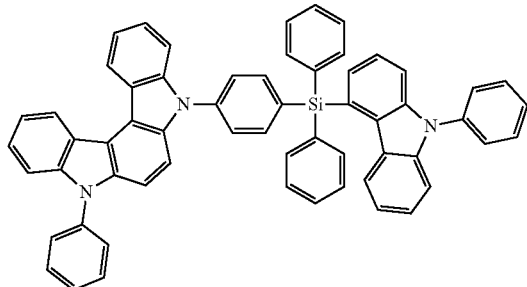
224
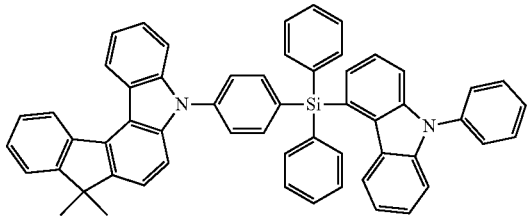

225
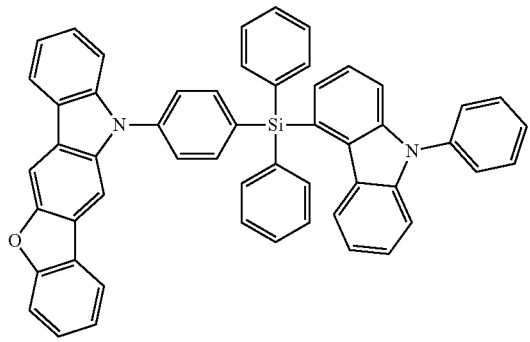
226
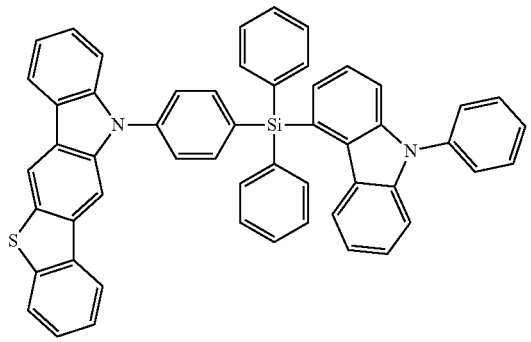
227
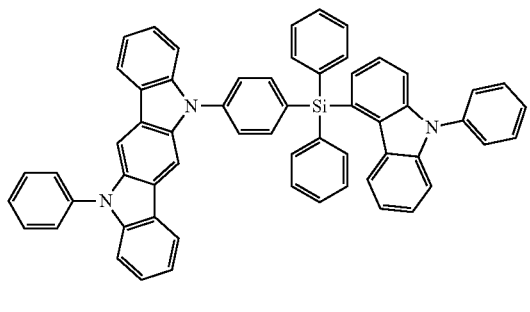
228
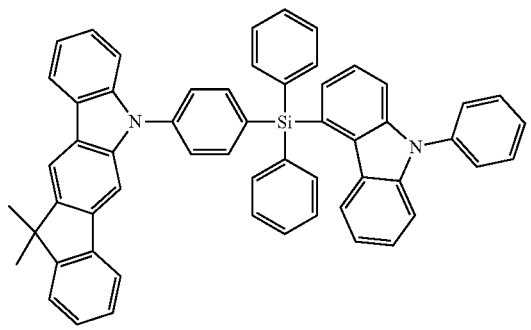
229
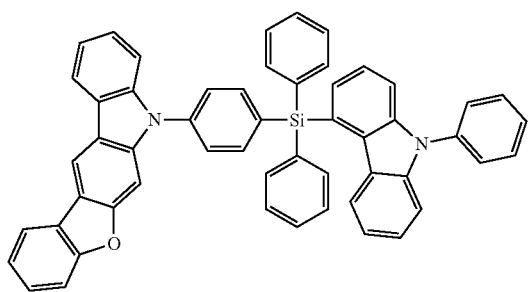
230
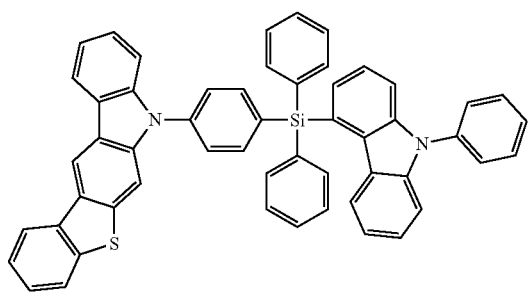
231
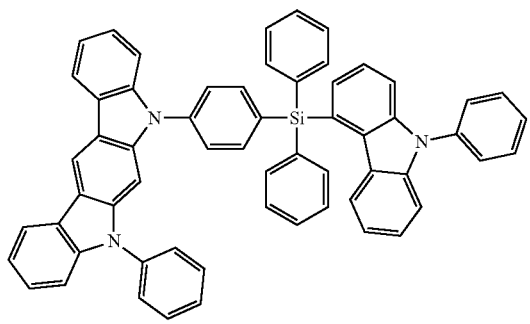
232
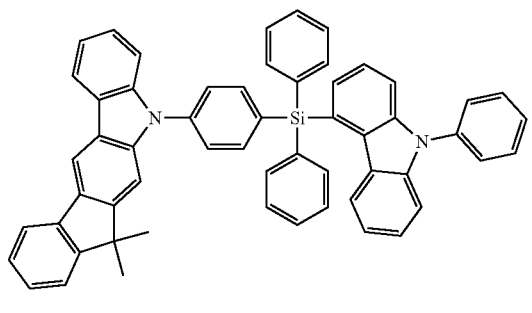

-continued
233
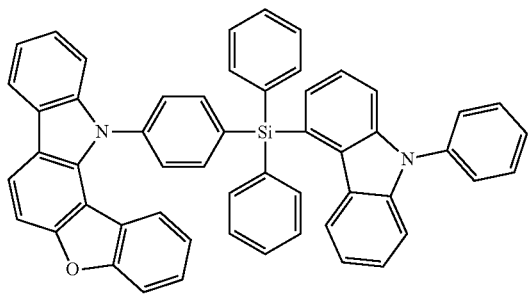
234
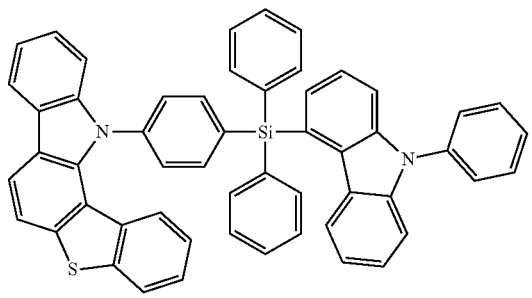
235
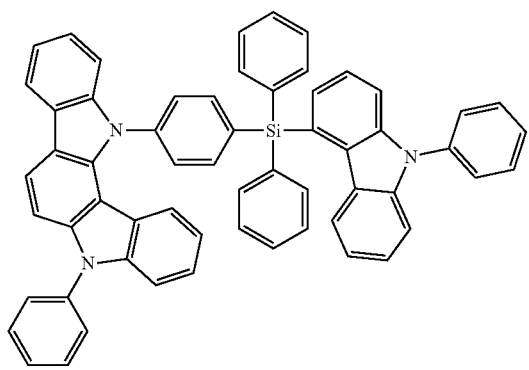
236
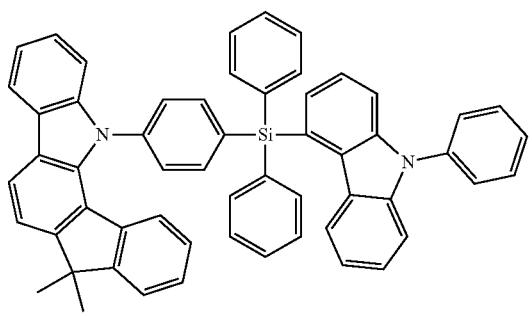
237
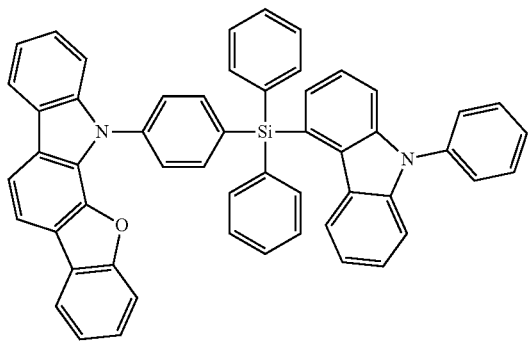
238
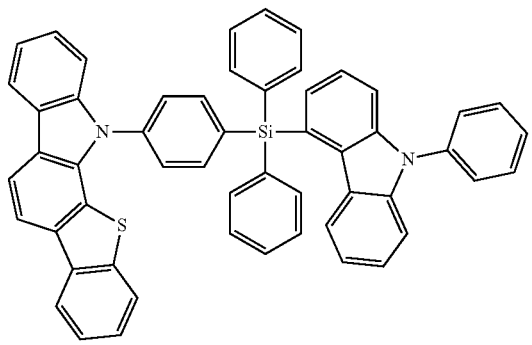
239
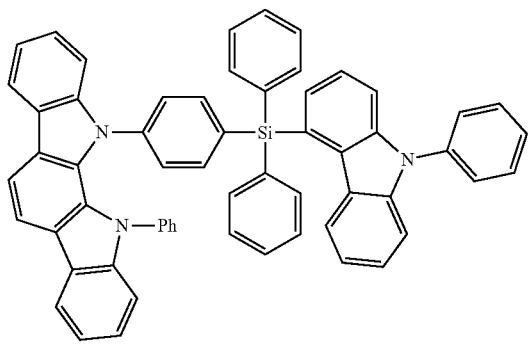
240
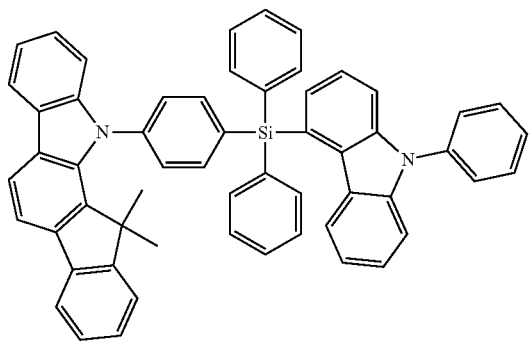

-continued
| 241 | 242 |
|---|---|
| 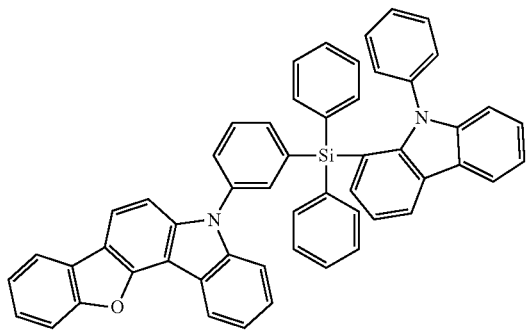 | 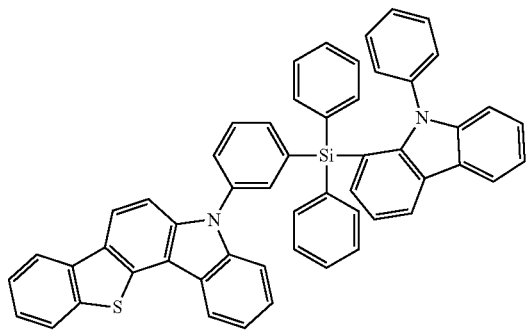 |
| 243 | 244 |
| 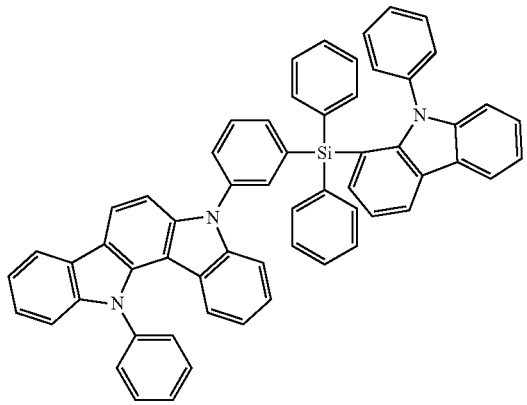 | 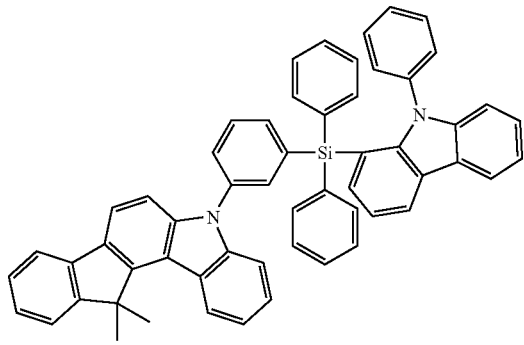 |
| 245 | 246 |
| 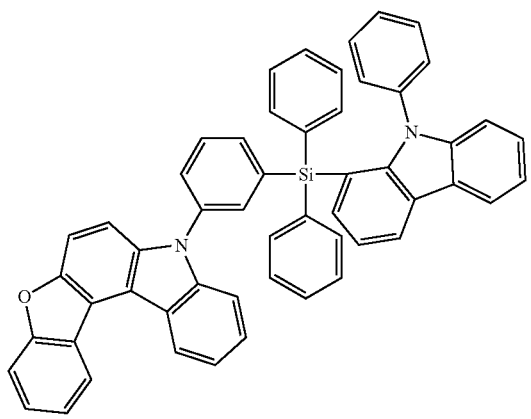 | 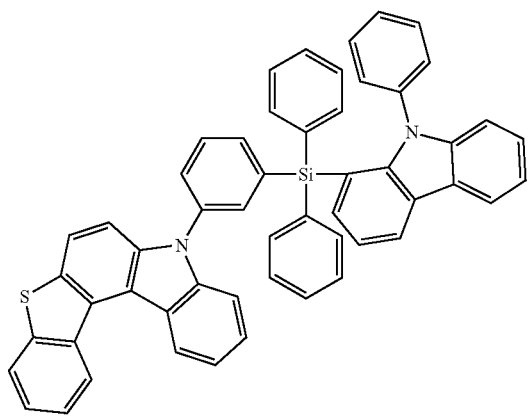 |
| 247 | 248 |
| 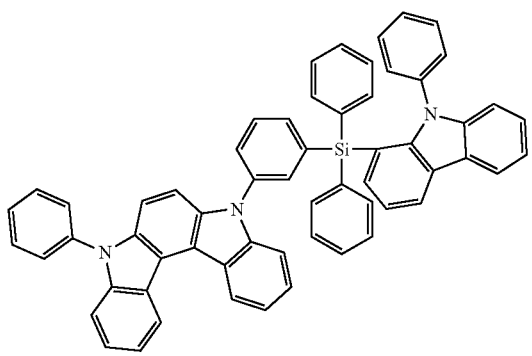 | 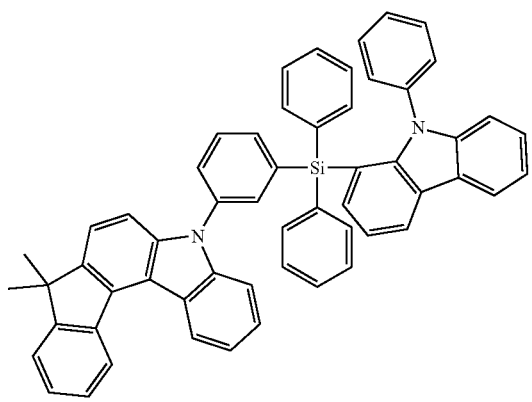 |

-continued
| 249 | 250 |
|---|---|
| 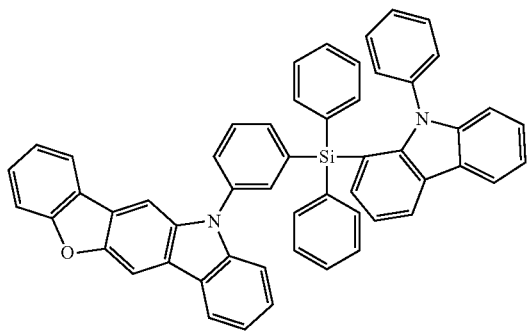 | 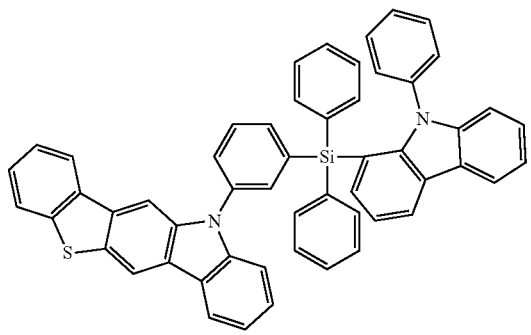 |
| 251 | 252 |
| 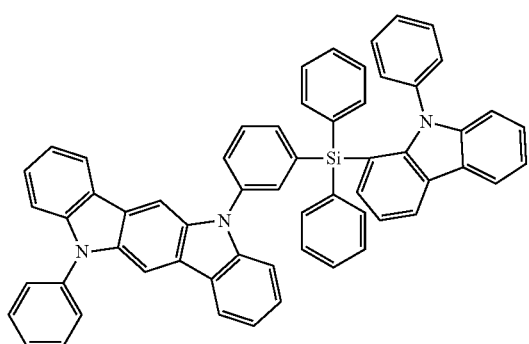 | 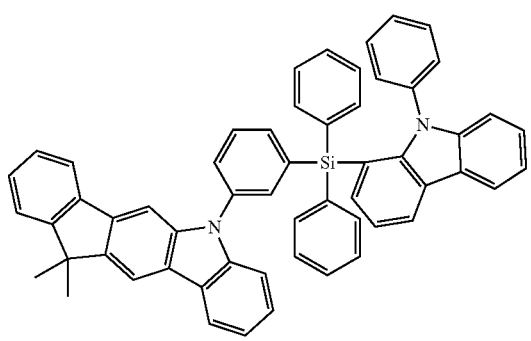 |
| 253 | 254 |
| 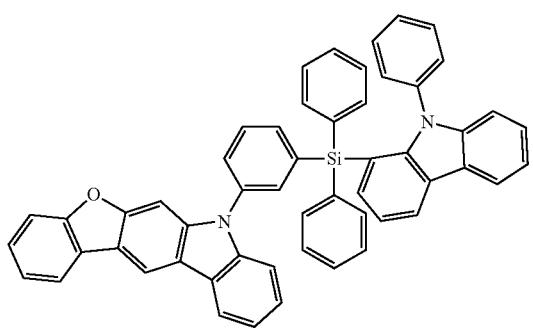 | 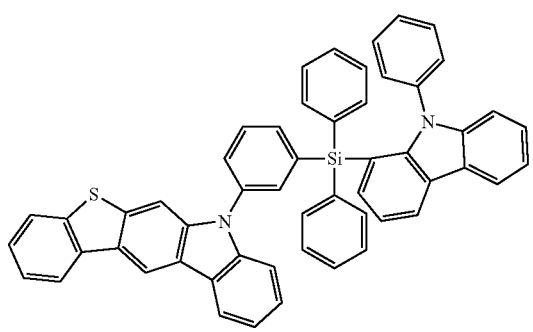 |
| 255 | 356 |
| 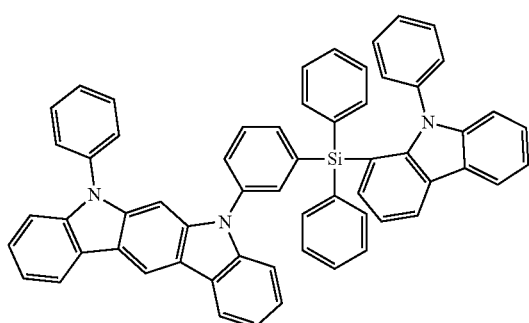 | 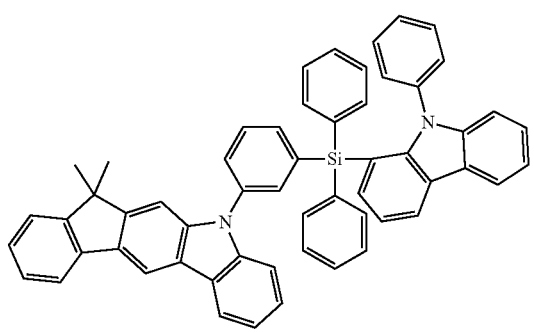 |

257
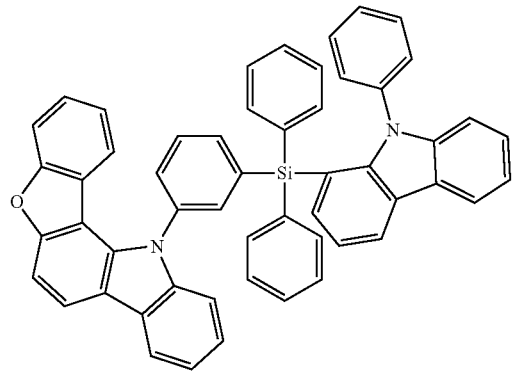
258
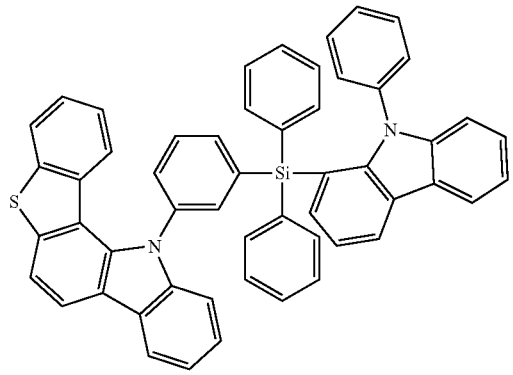
259
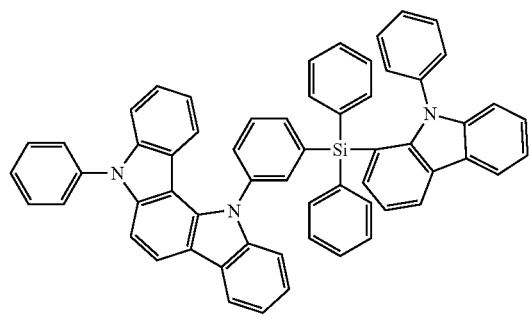
260
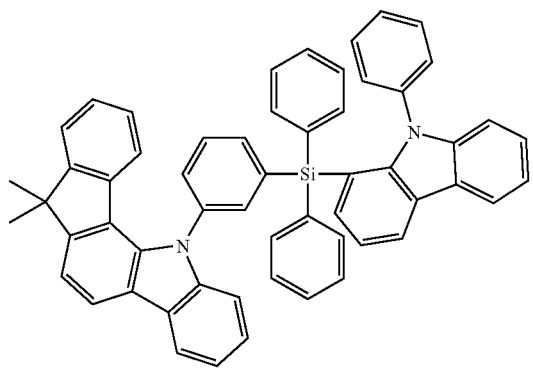
261
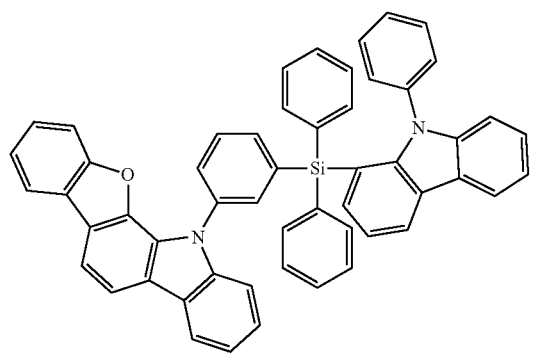
262
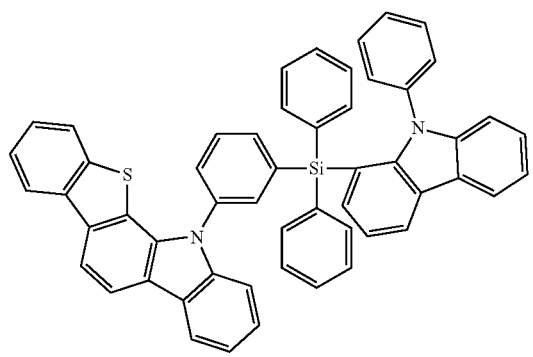
263
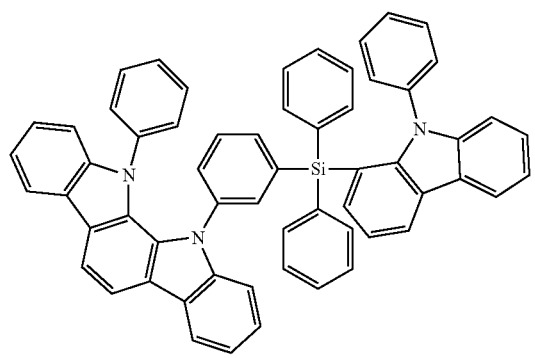
264
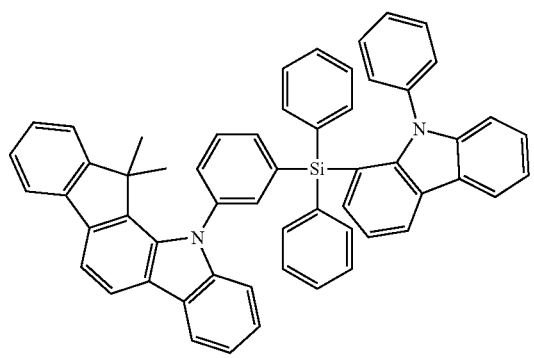

-continued
265
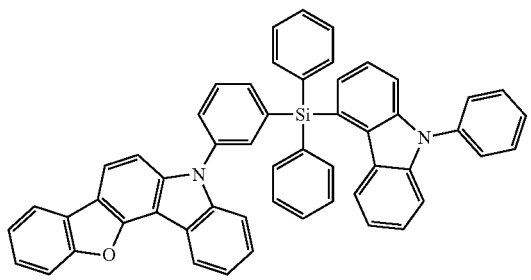
266
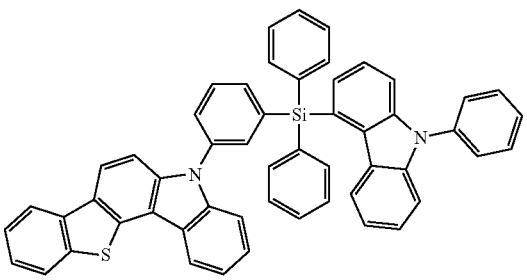
267
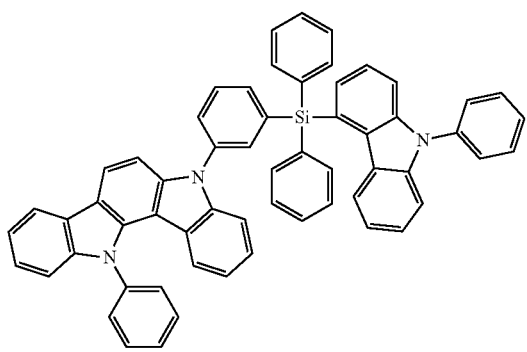
268
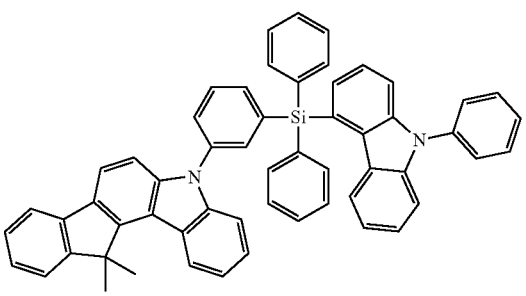
269
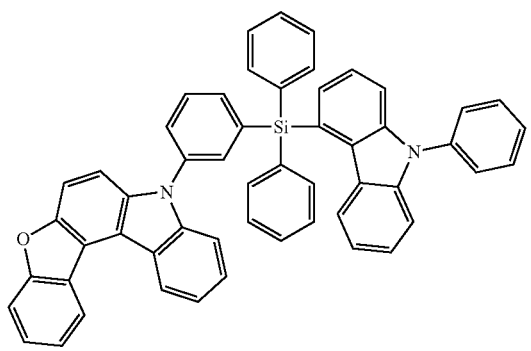
270
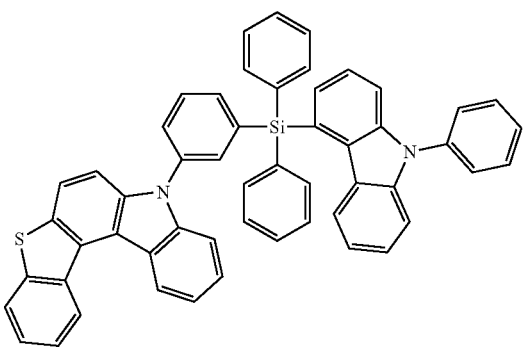
271
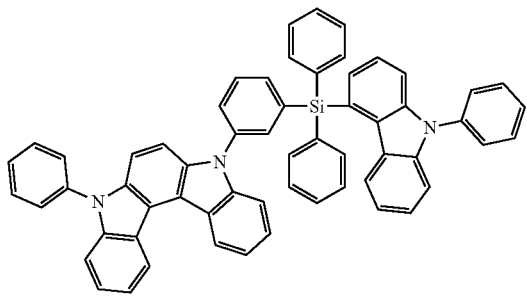
272
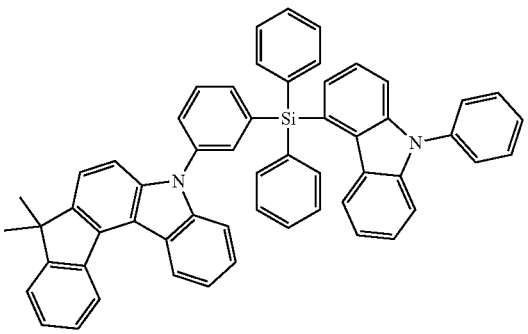

-continued
273
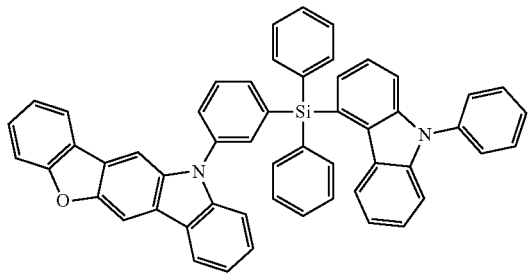
274
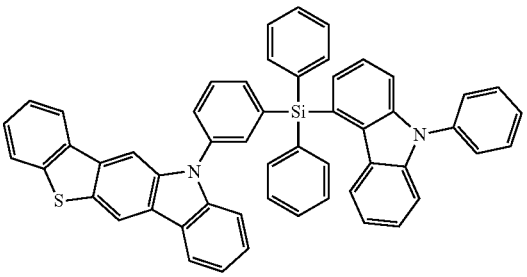
275
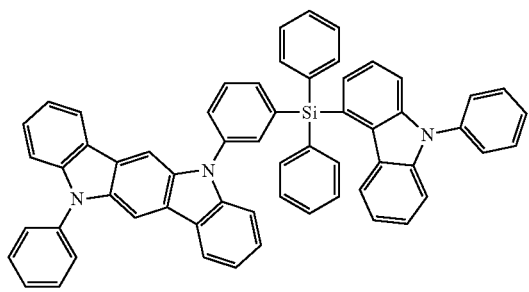
276
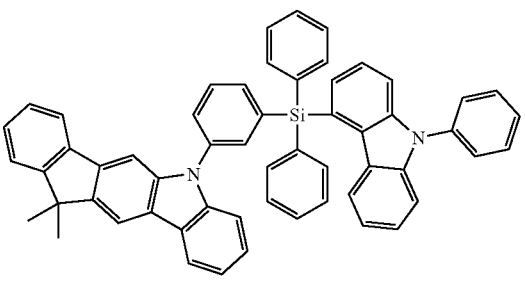
277
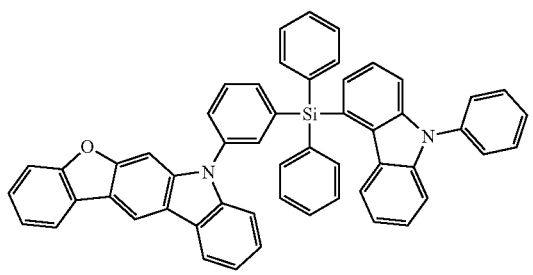
278
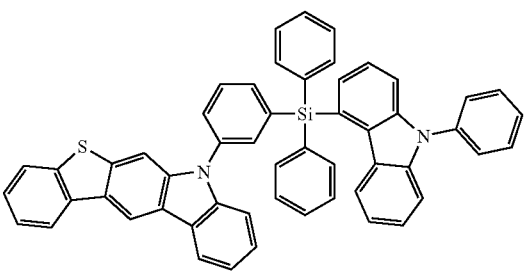
279
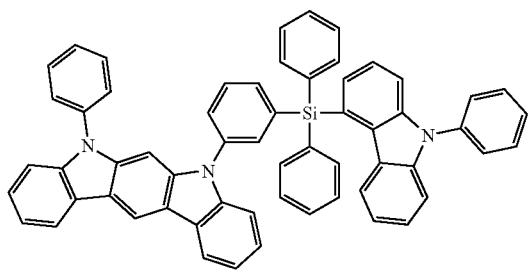
280
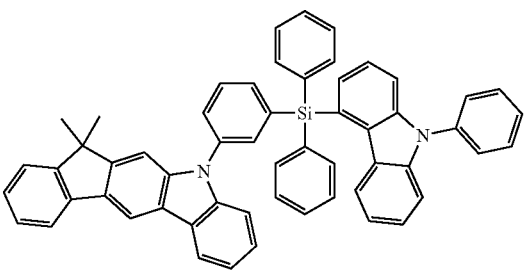
281
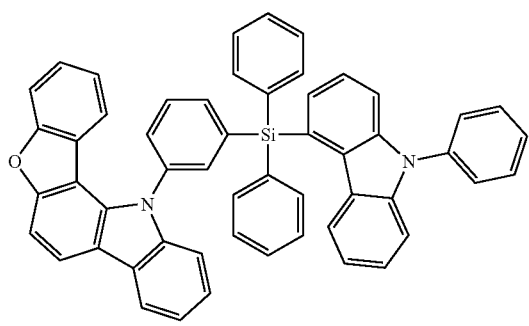
282
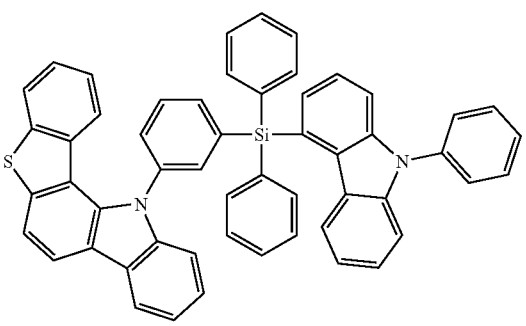

-continued
283
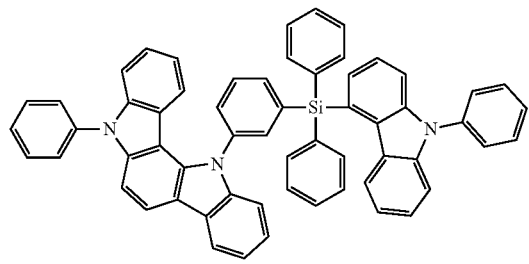
284
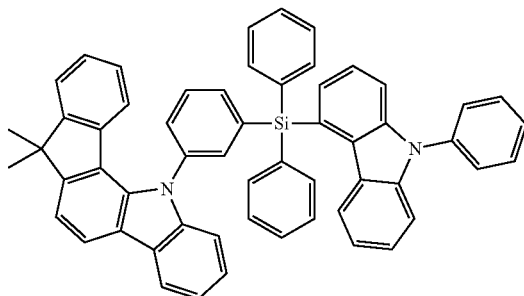
285
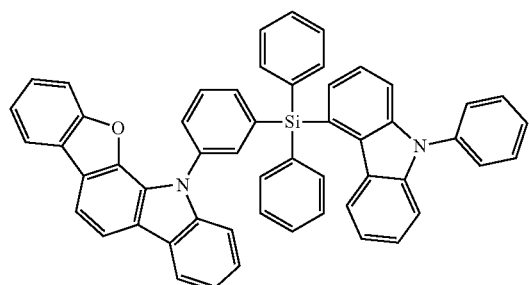
286
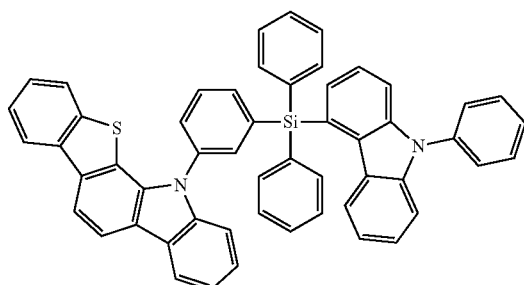
287
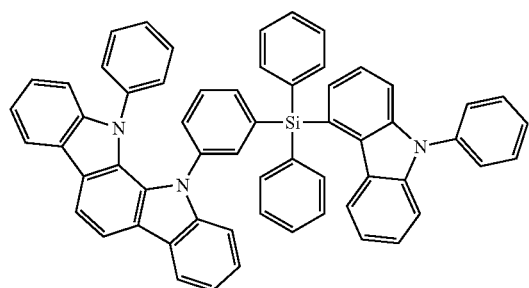
288
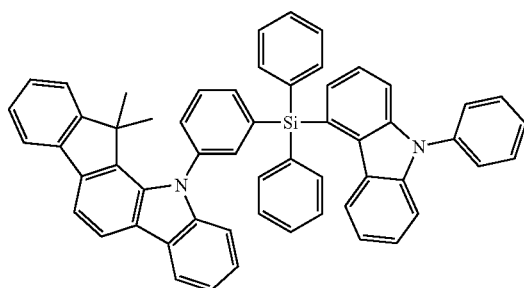
289
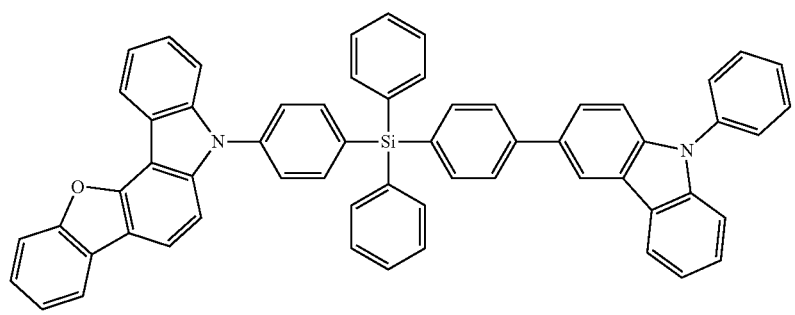
290
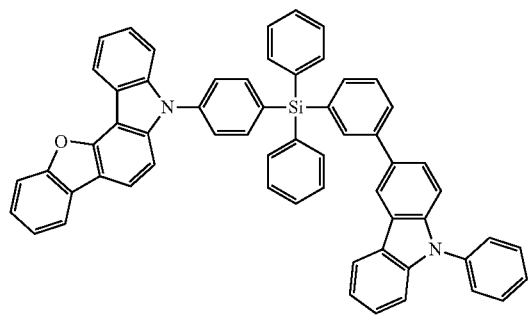

291
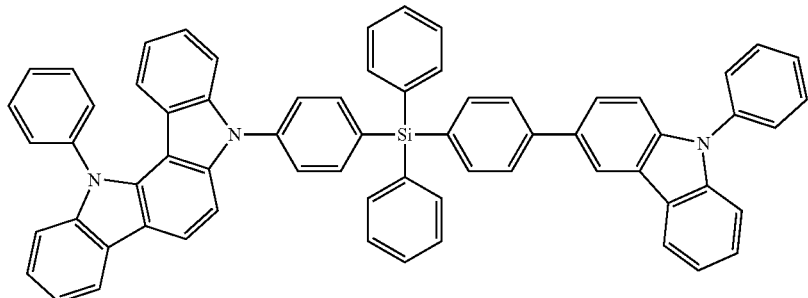
292
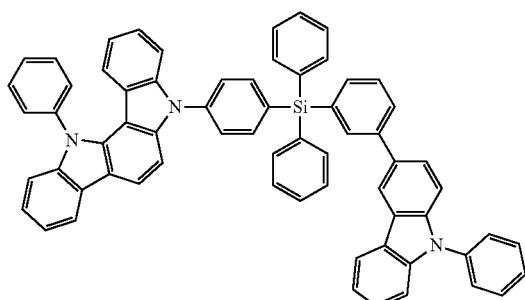
293
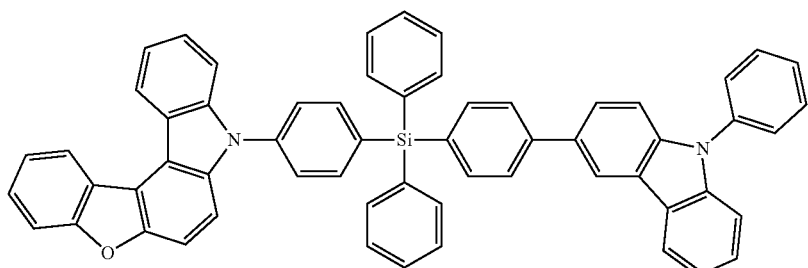
294
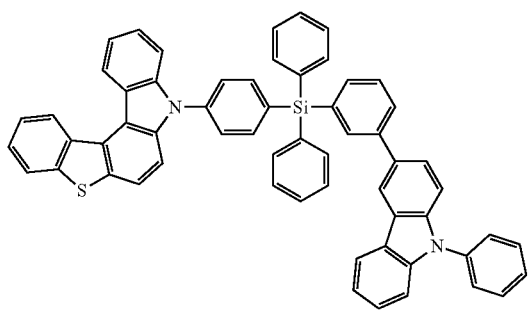
295
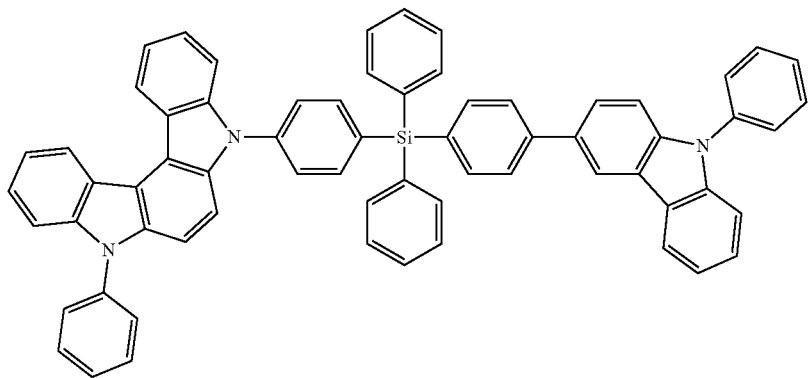

-continued
296
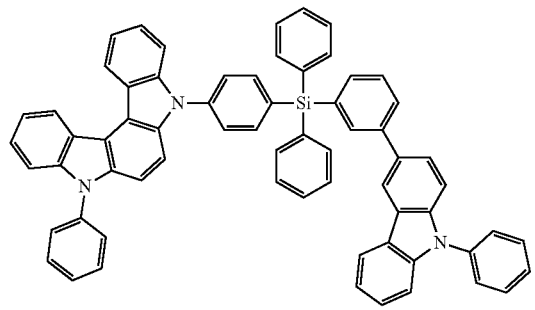
297
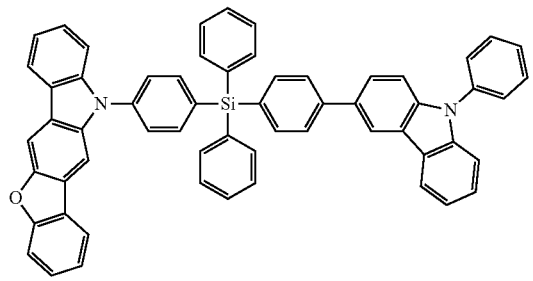
298
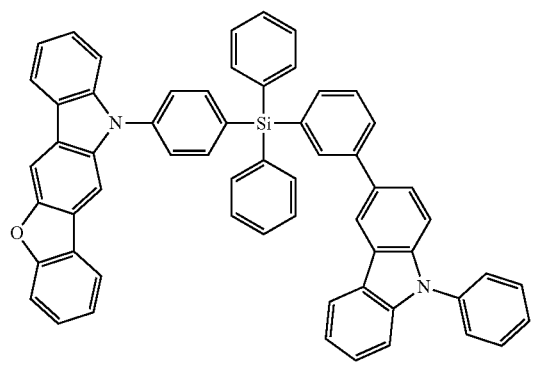
299
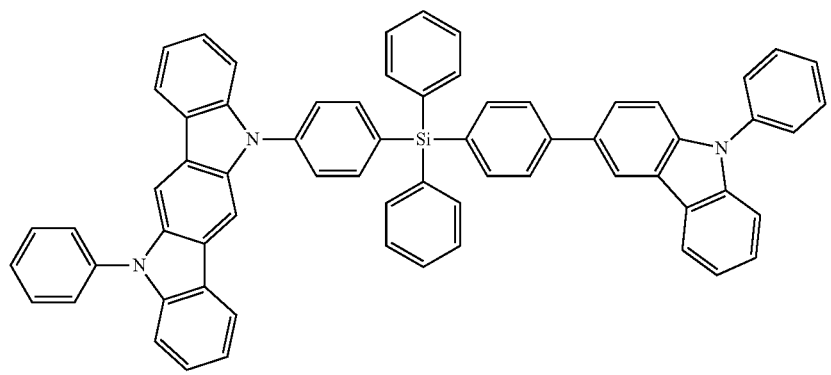
300
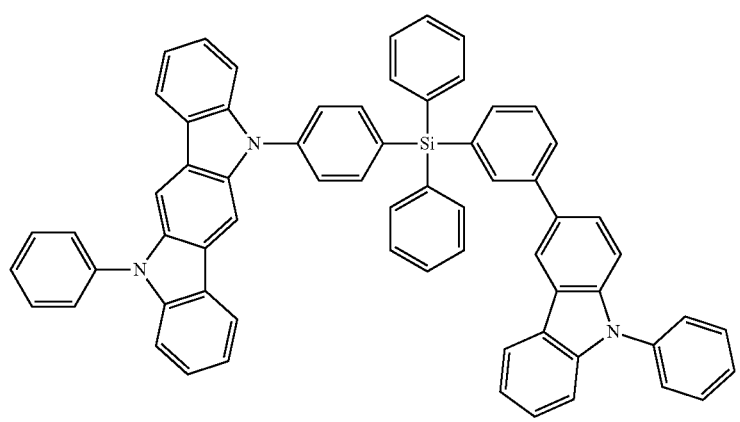

301
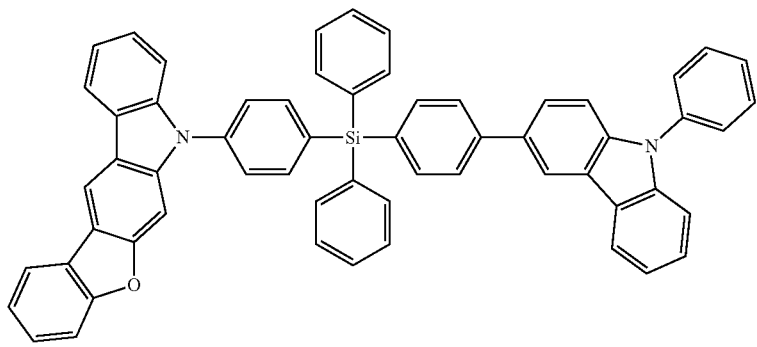
302
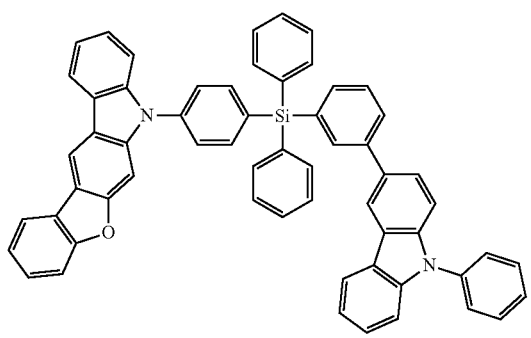
303
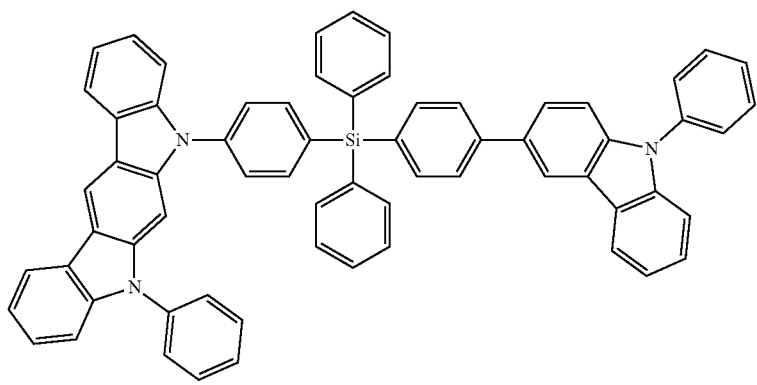
304
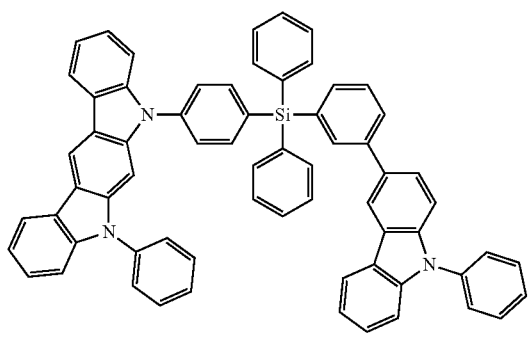
305
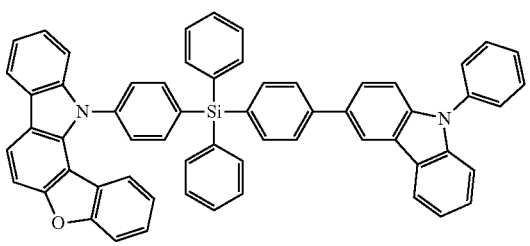

-continued
306
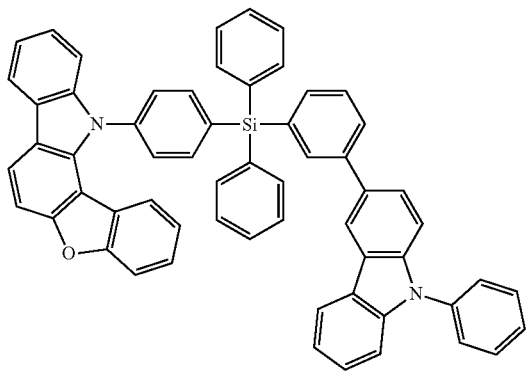
307
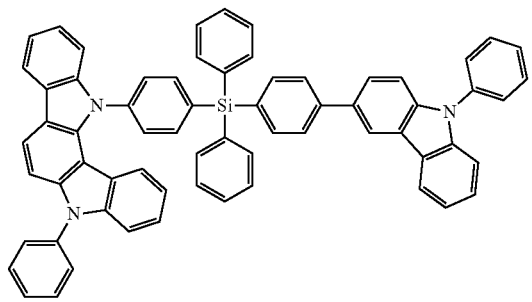
308
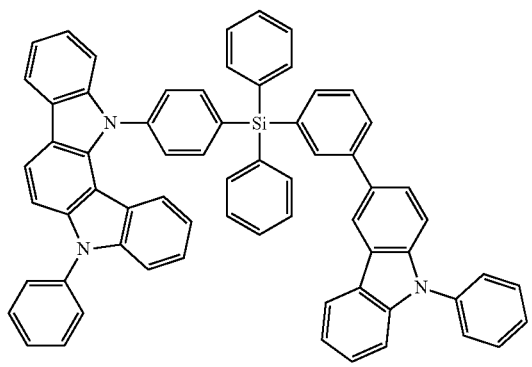
309
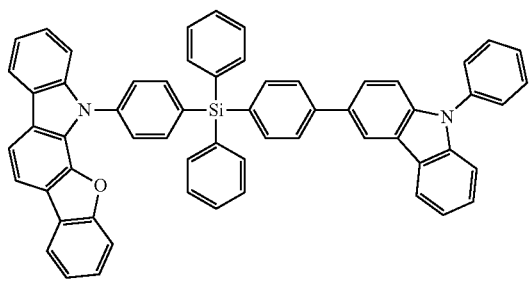
310
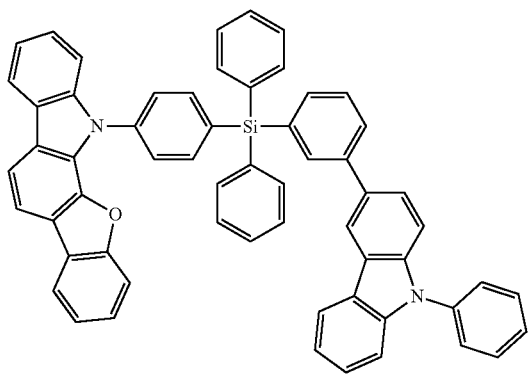
311
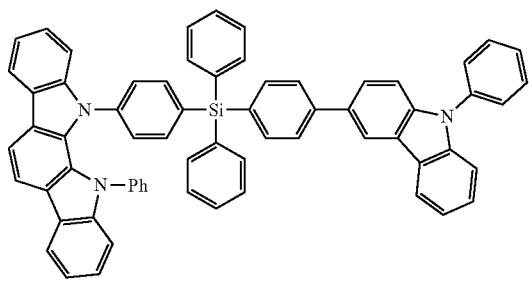
312
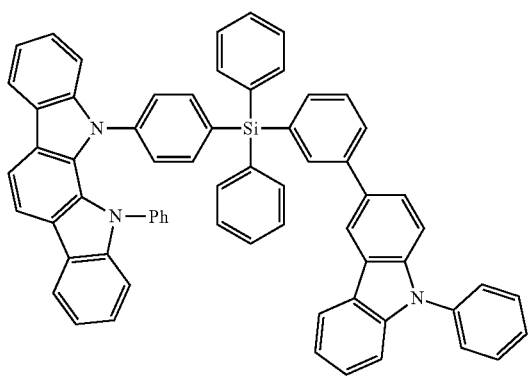

-continued
313
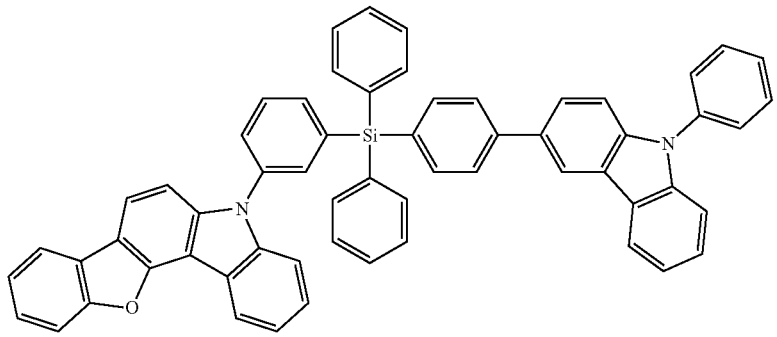
314
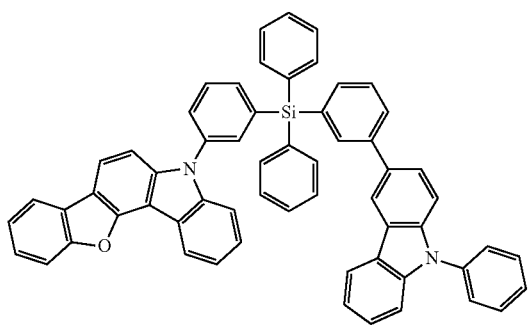
315
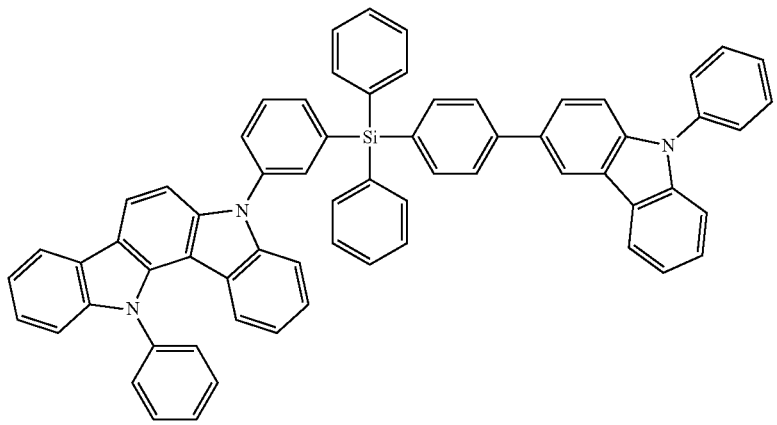
316
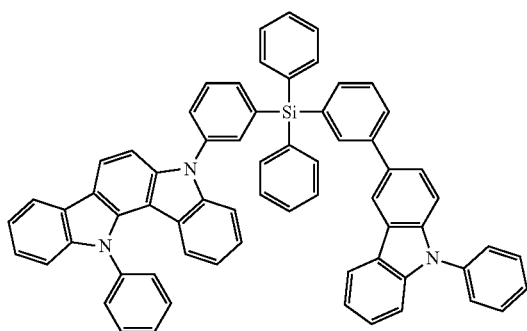
317
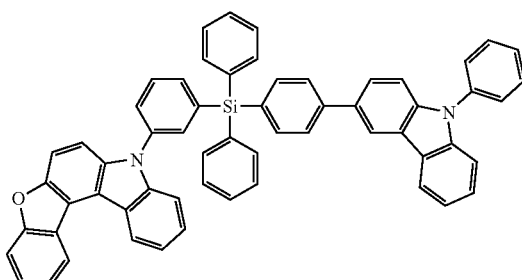

-continued
318
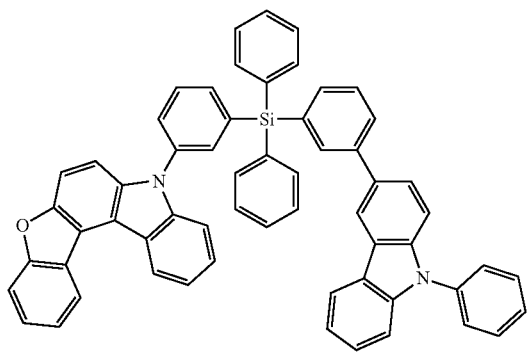
319
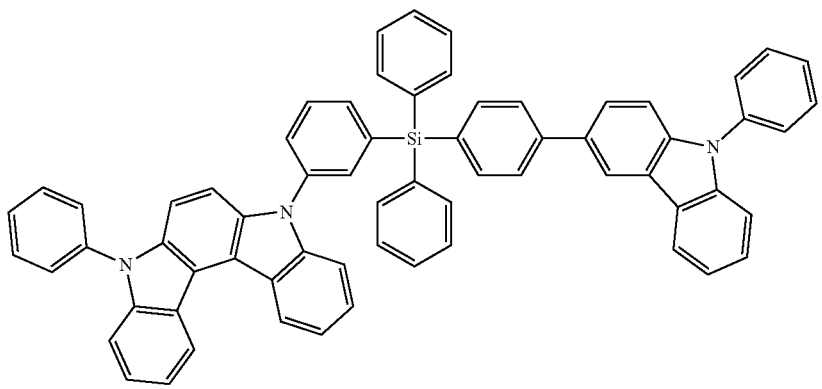
320
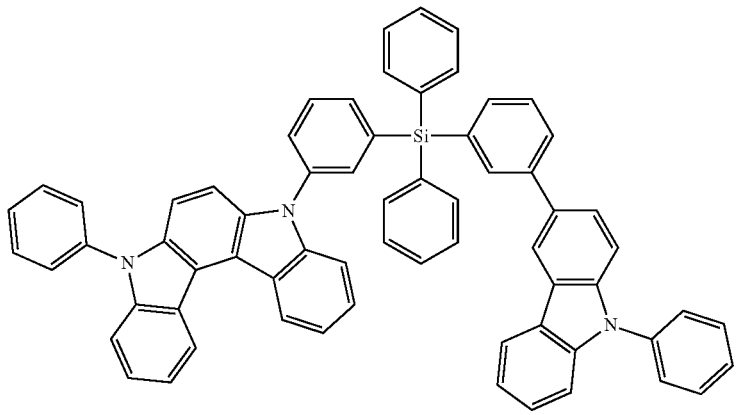
321
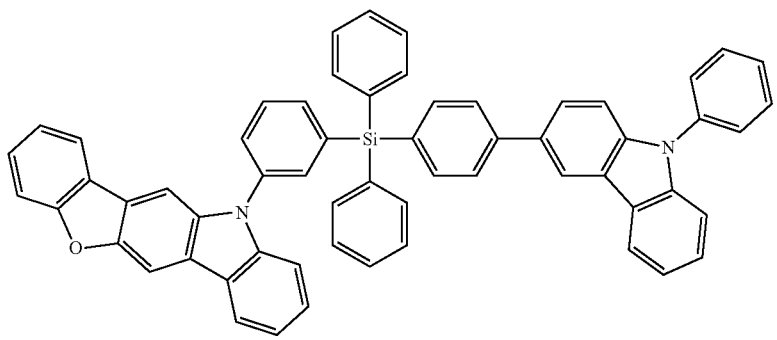

-continued
322
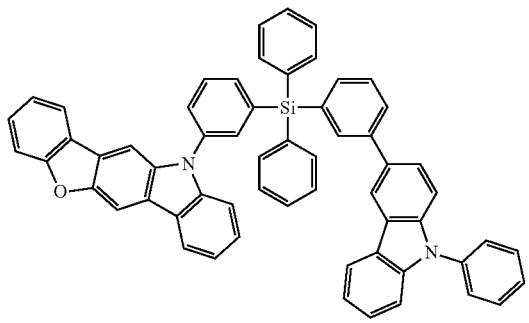
323
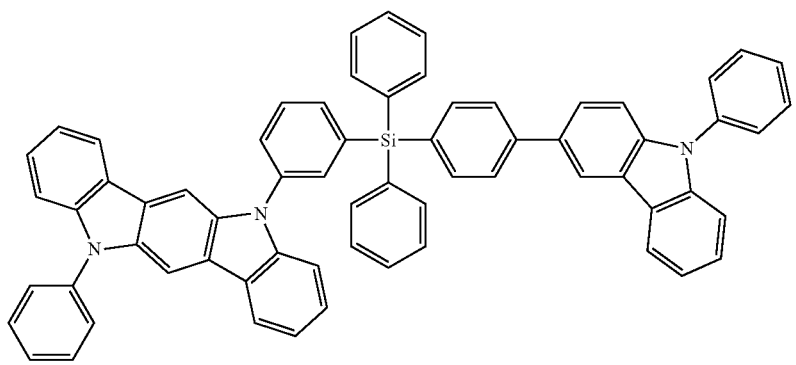
324
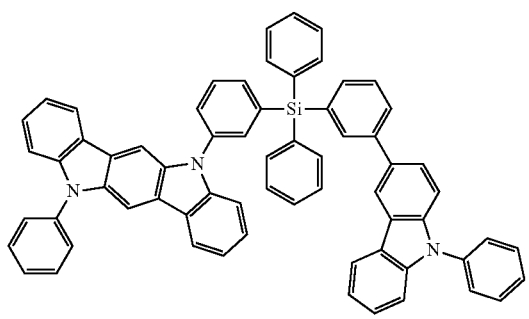
325
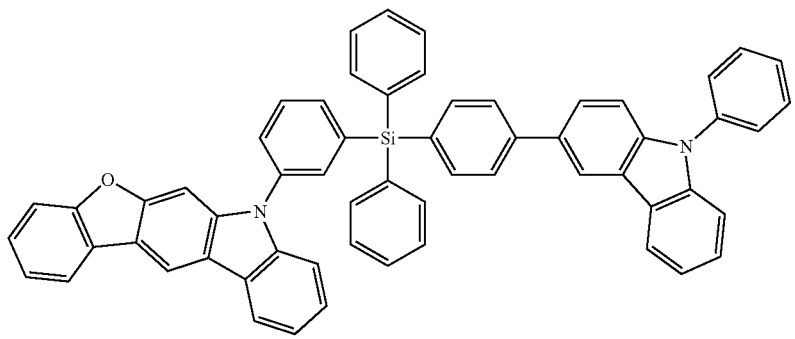

326
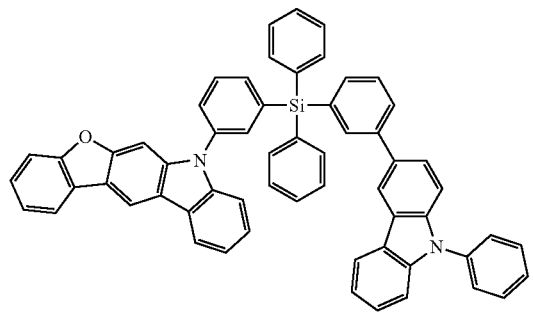
327
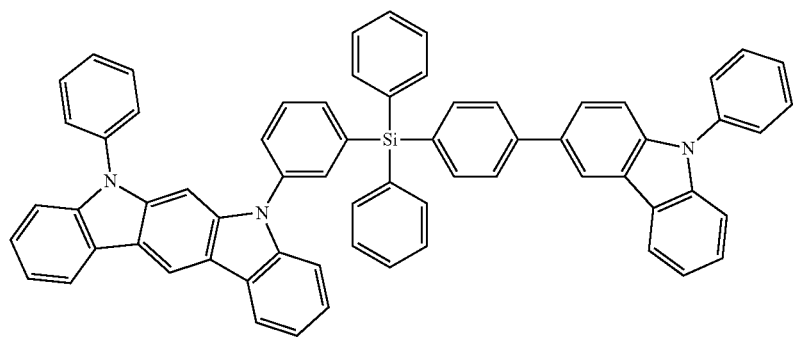
328
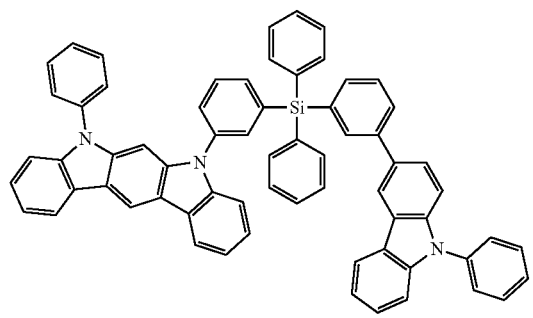
329
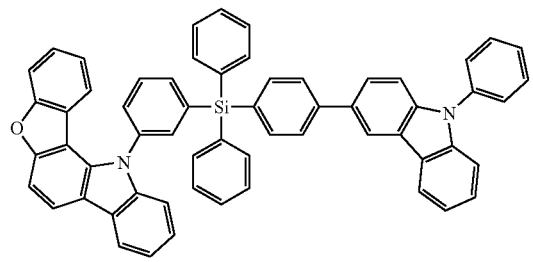
330
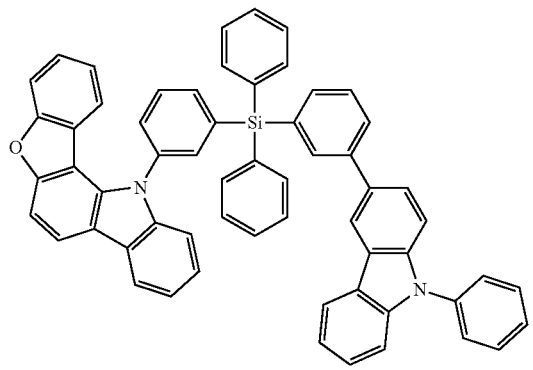

331
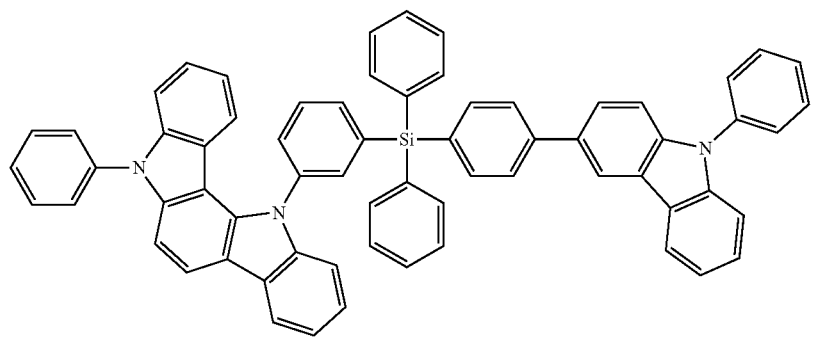
332
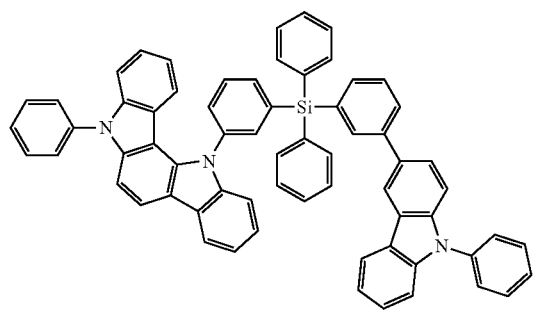
333
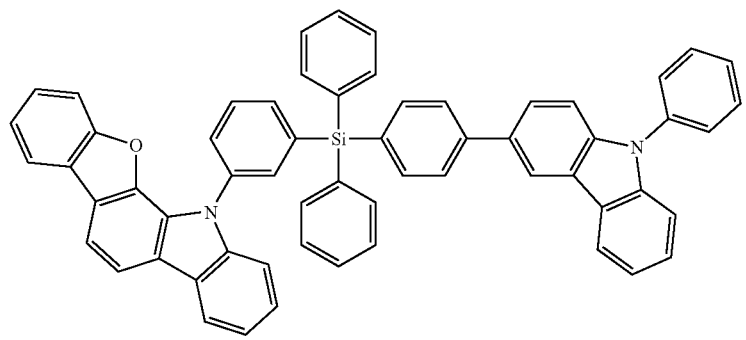
334
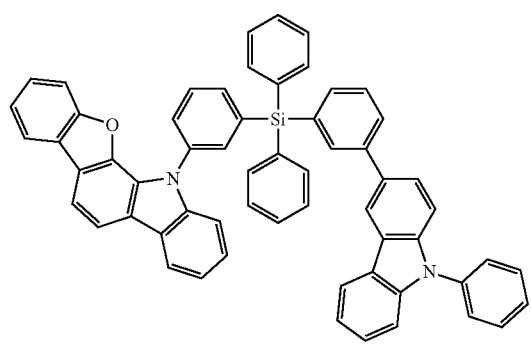

-continued
335
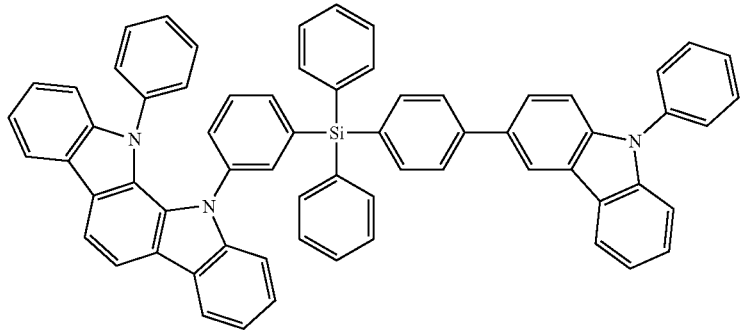
336
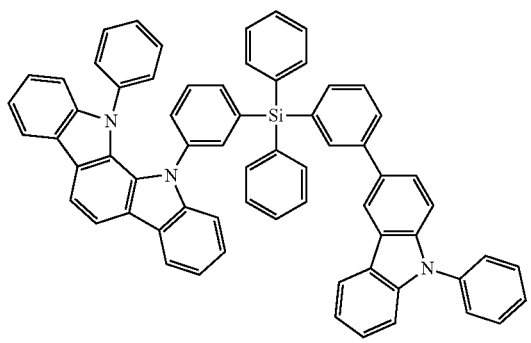
337
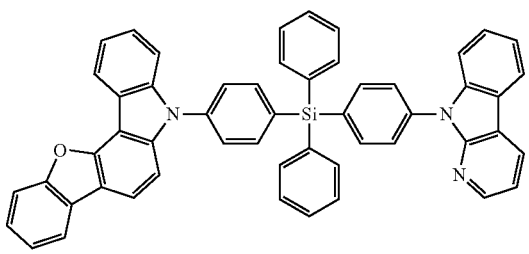
338
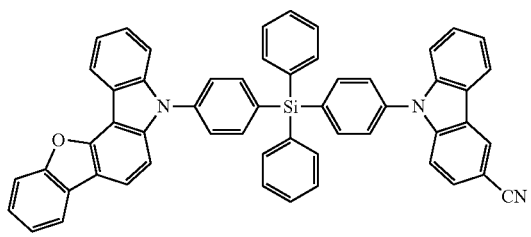
339
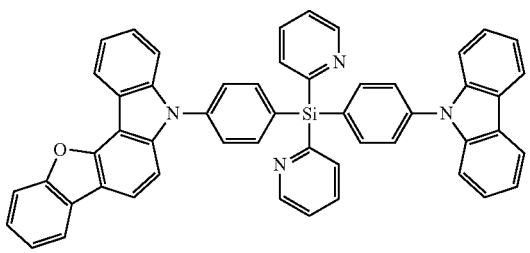
340
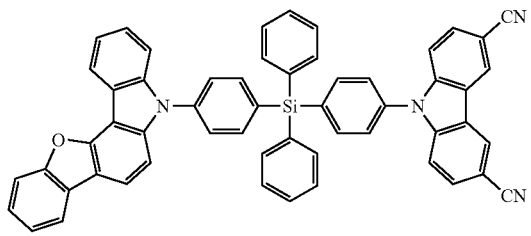
341
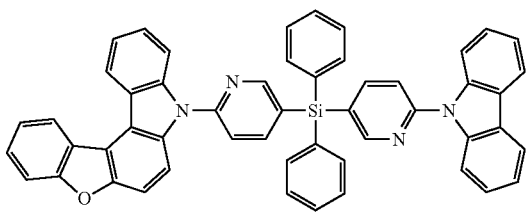
342
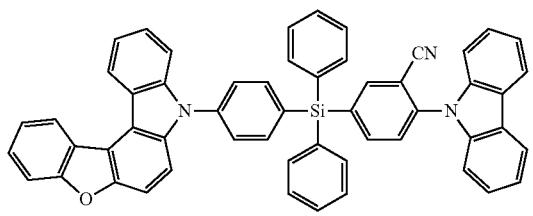
343
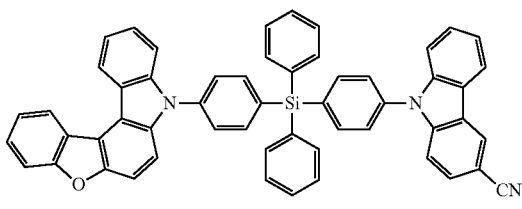

-continued
344
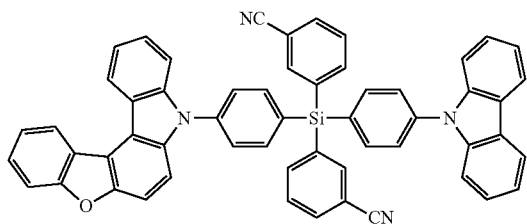
345
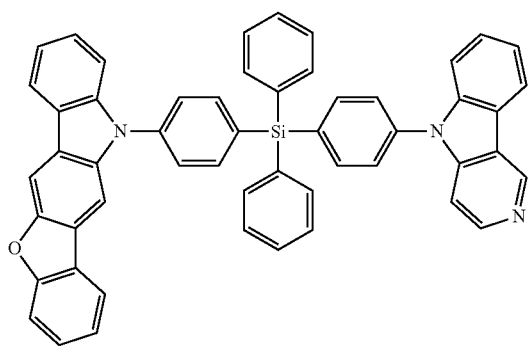
346
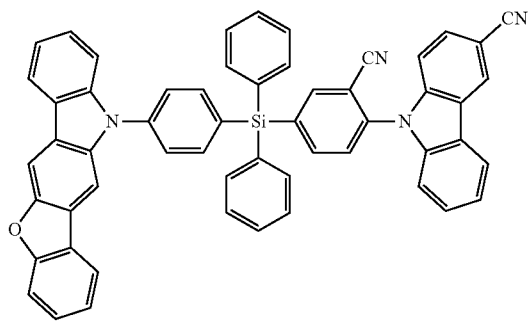
347
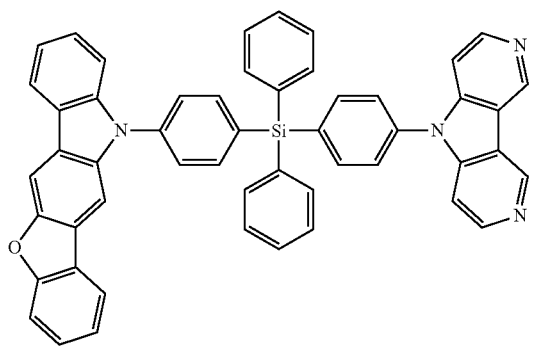
348
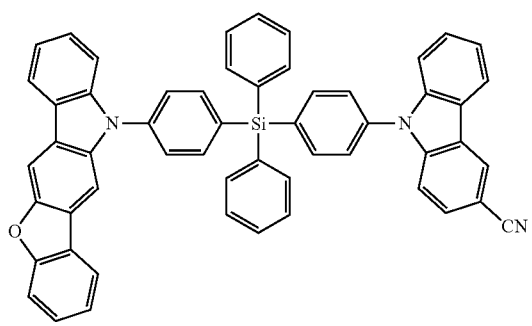
349
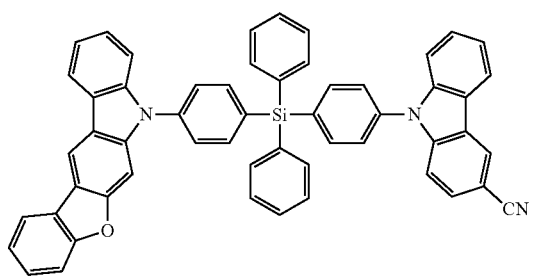
350
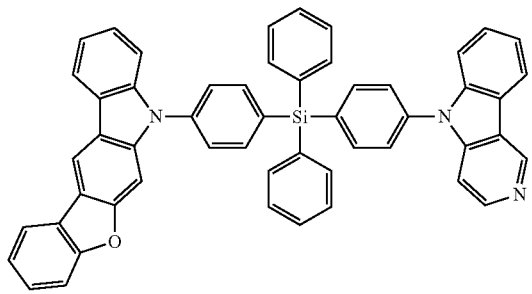
351
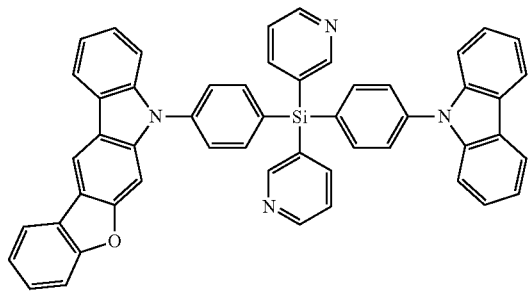

-continued
352
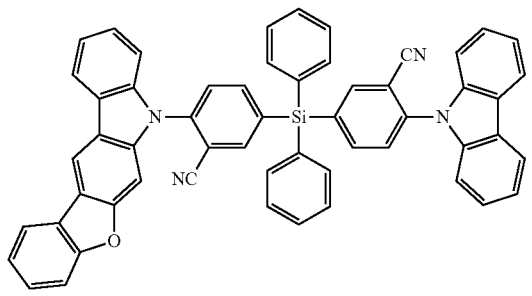
353
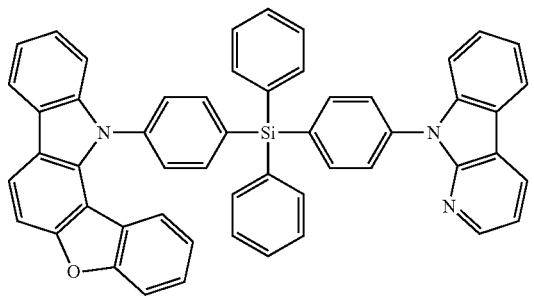
354
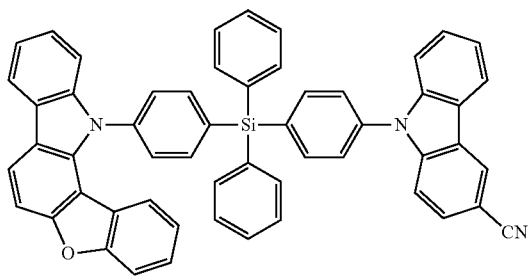
355
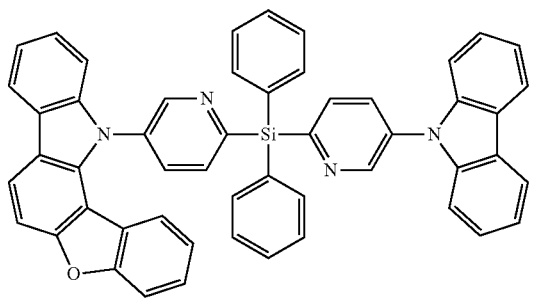
356
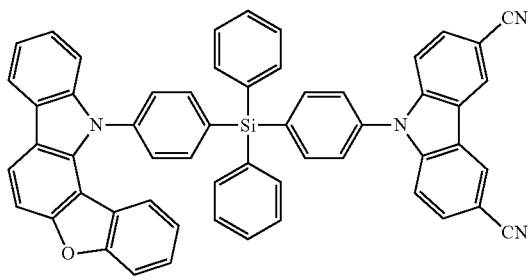
357
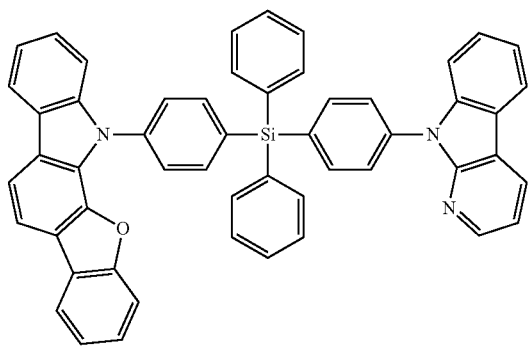
358
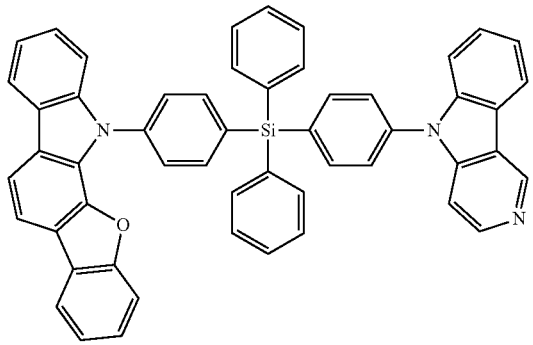
359
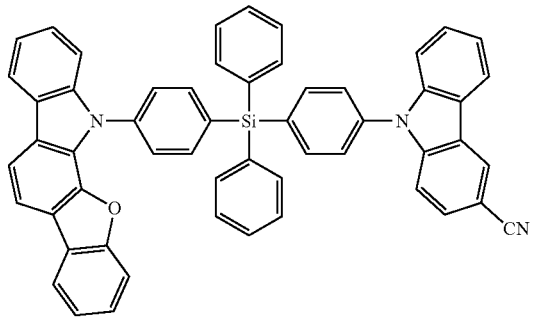

-continued
360
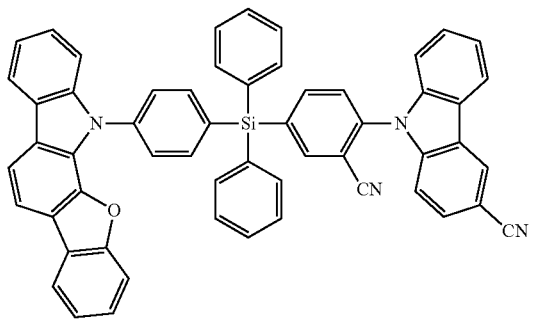
361
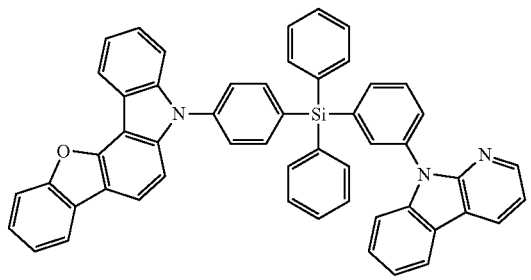
362
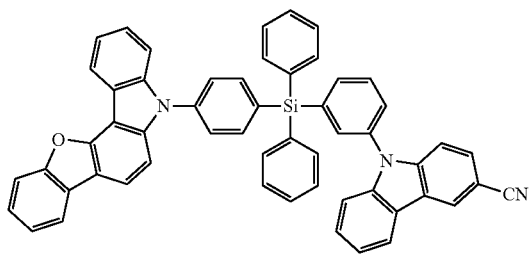
363
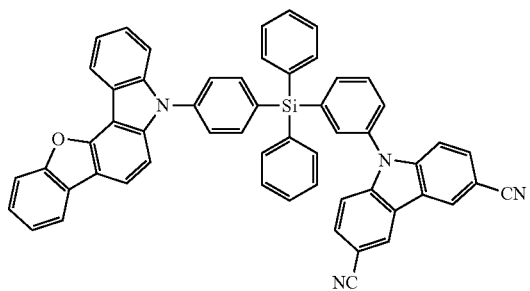
364
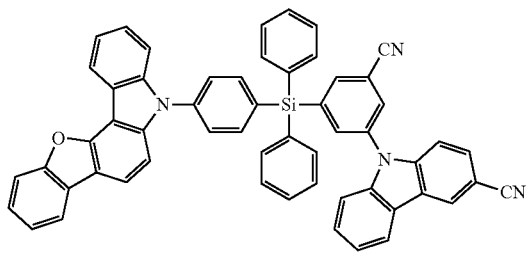
365
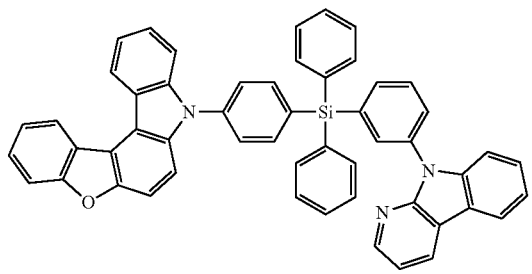
366
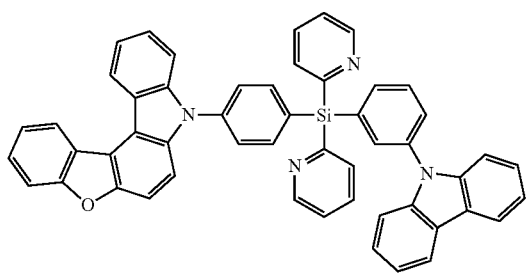
367
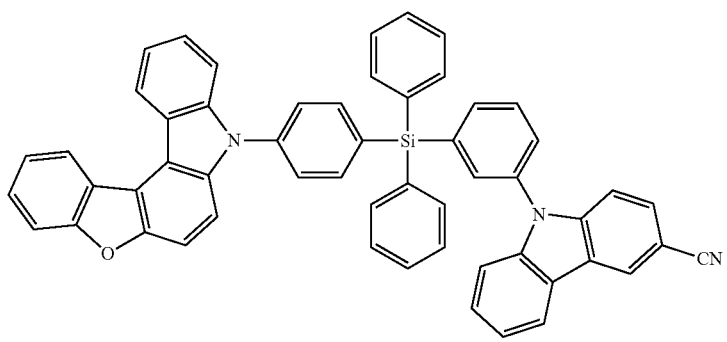

-continued
368
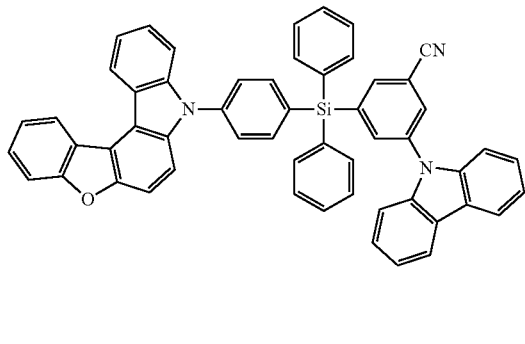
369
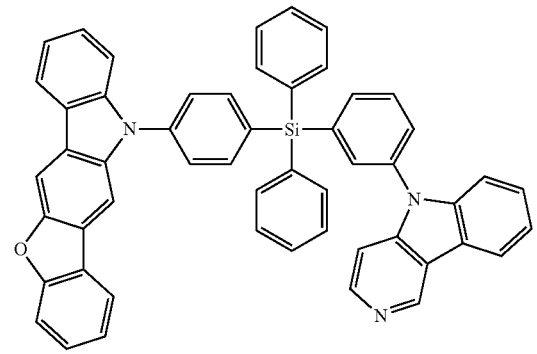
370
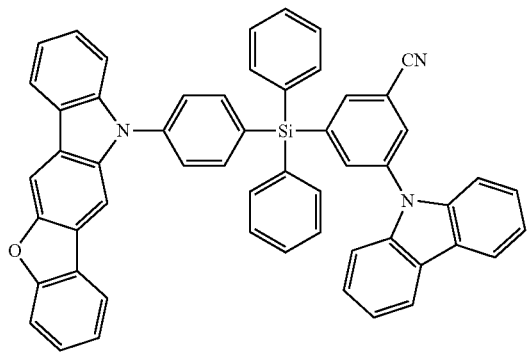
371
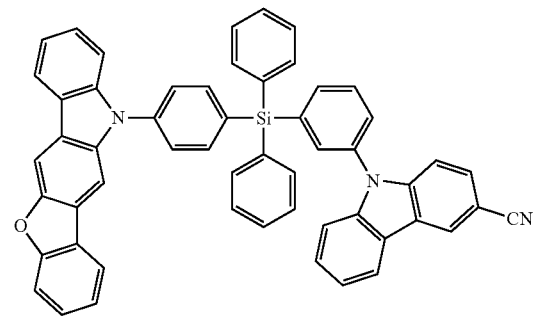
372
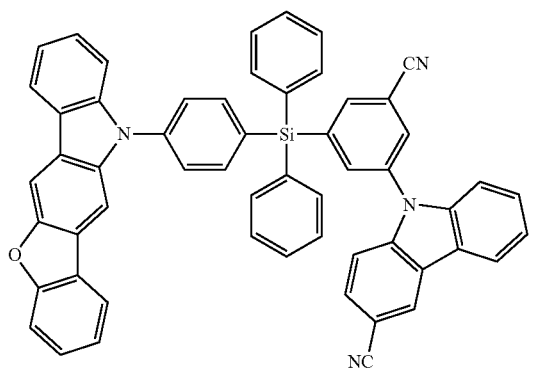
373
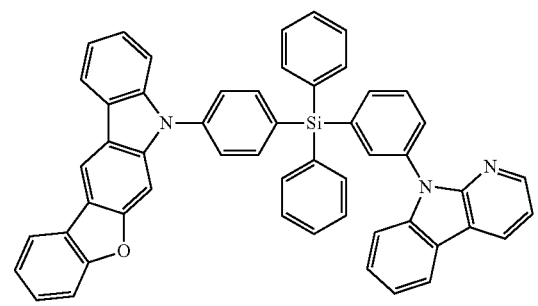
374
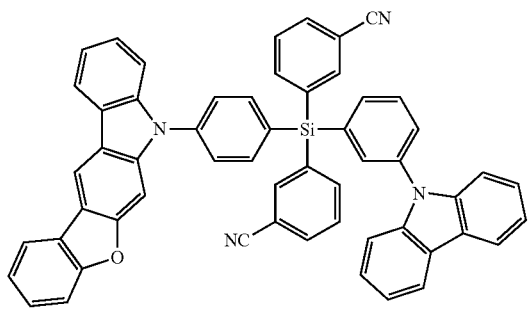
375
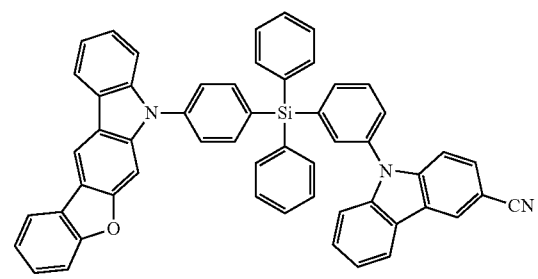

-continued
376
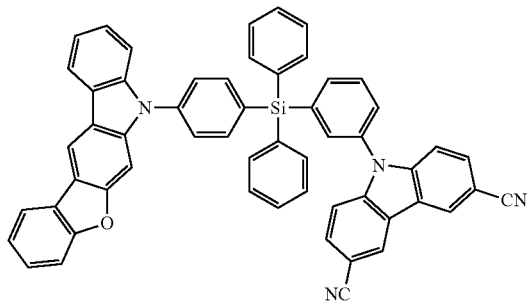
377
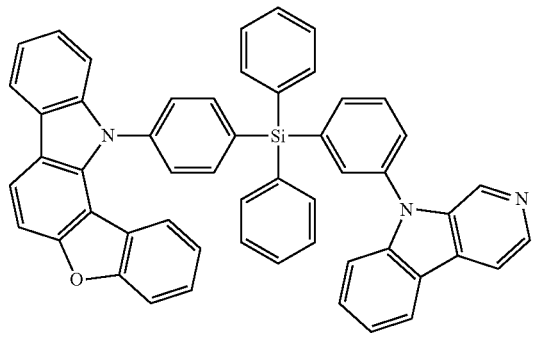
378
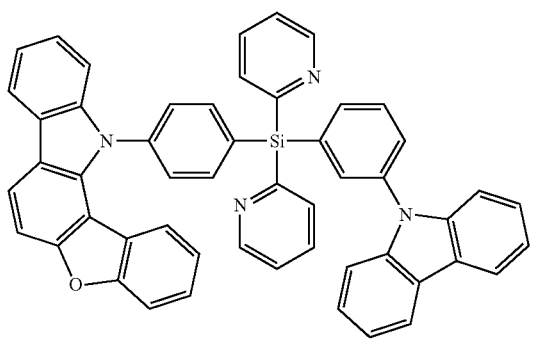
379
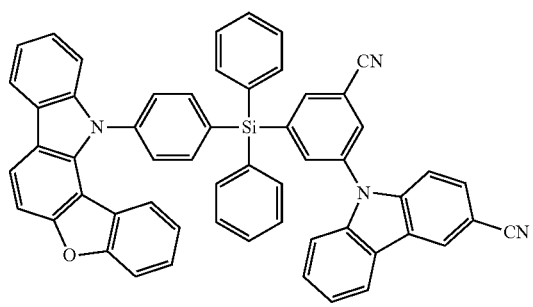
380
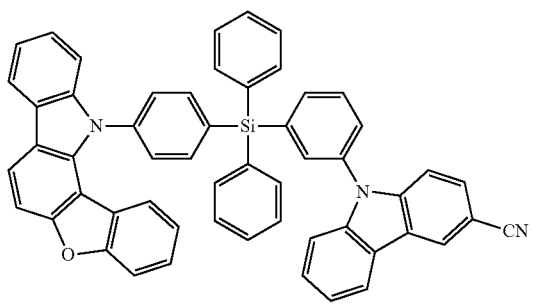
381
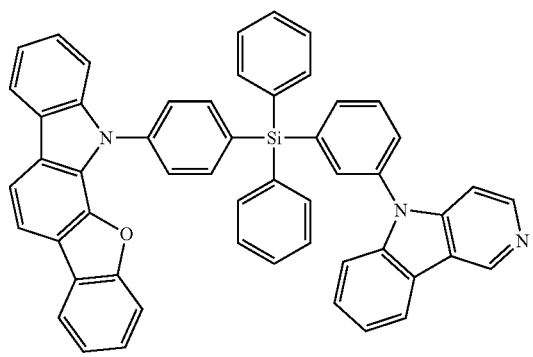
382
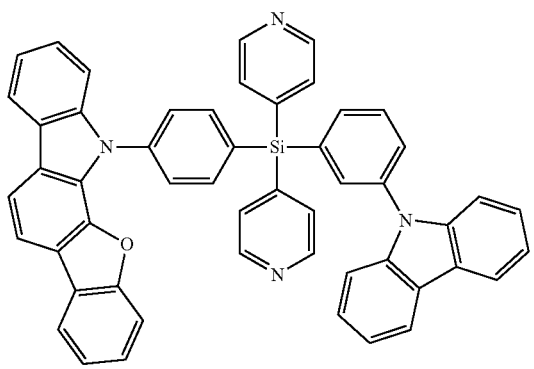
383
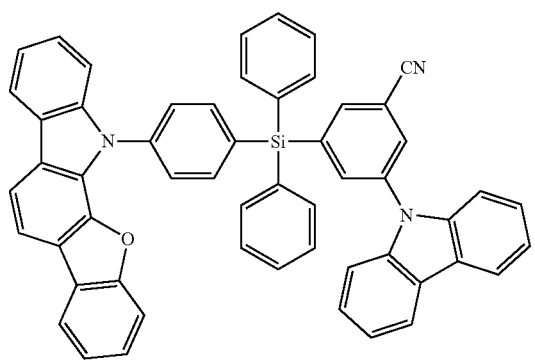

-continued
384
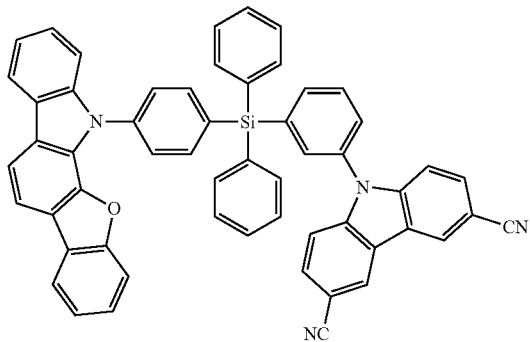
385
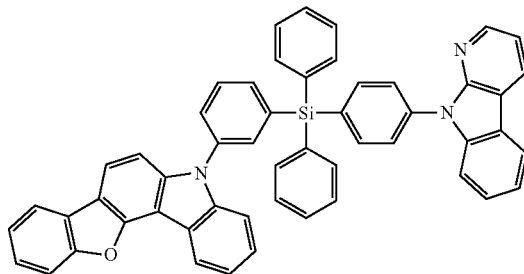
386
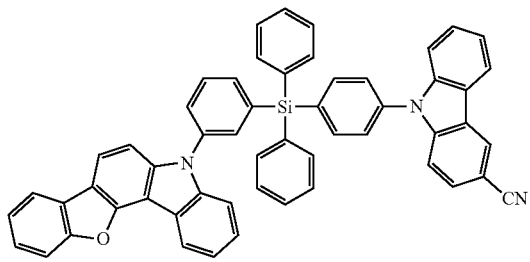
387
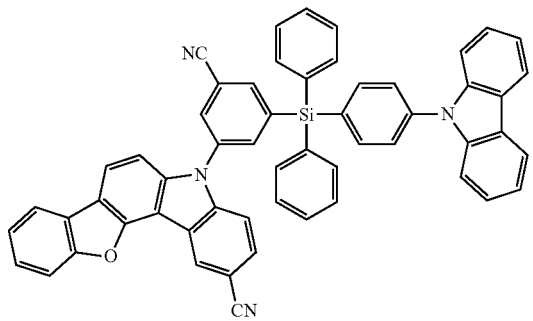
388
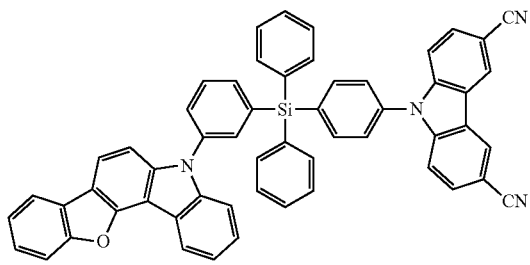
389
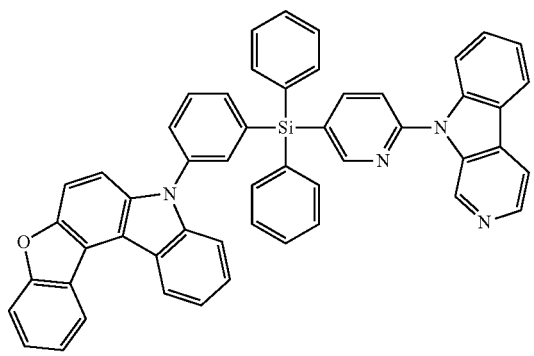
390
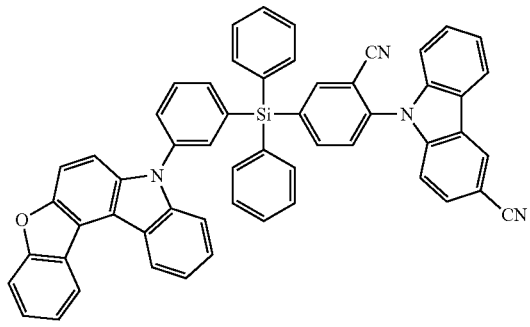
391
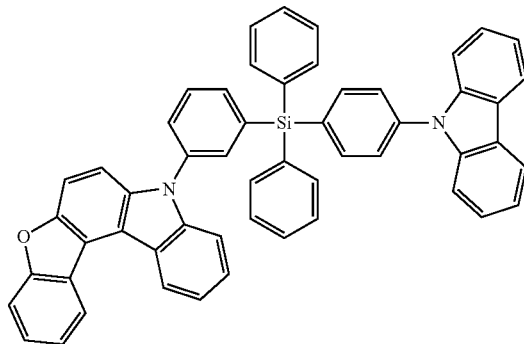

-continued
392
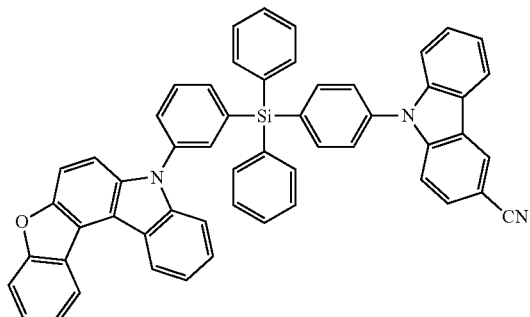
393
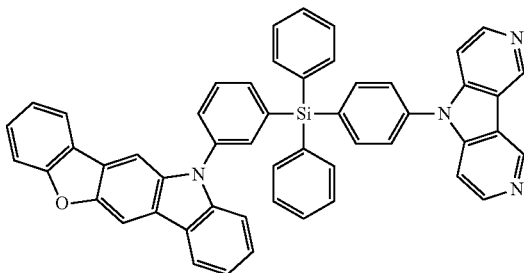
395
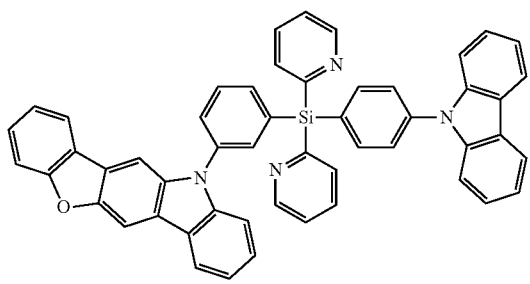
394
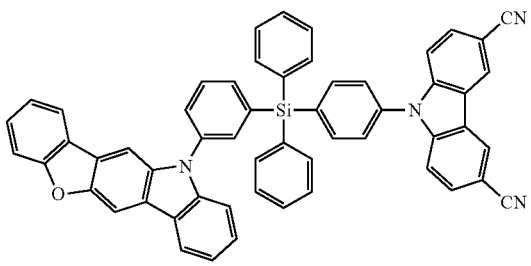
396
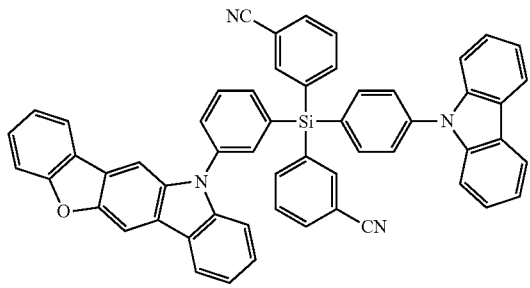
397
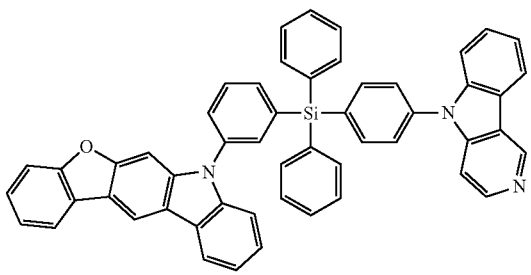
398
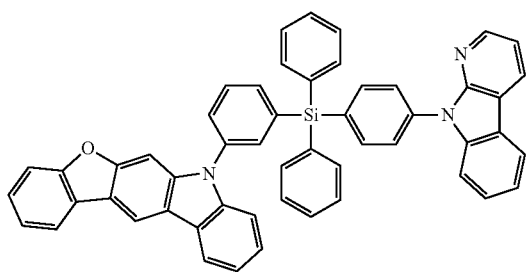
399
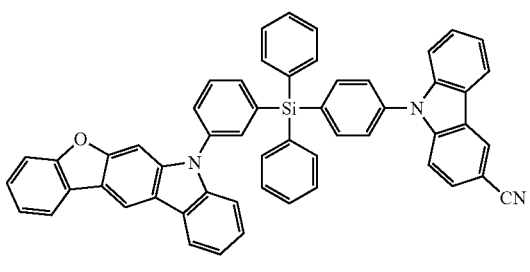
400
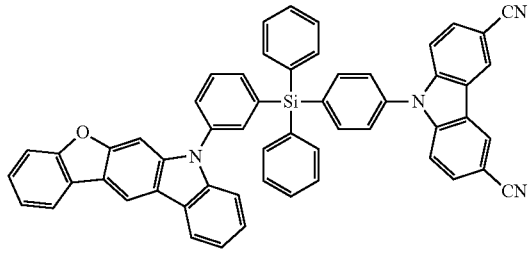
401
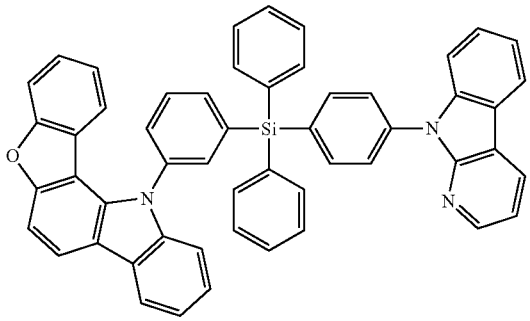

-continued
402
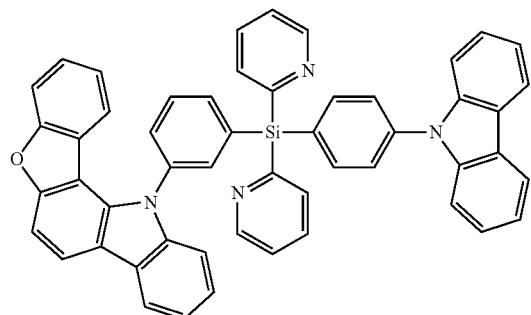
403
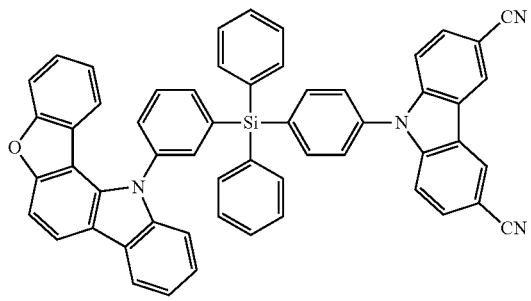
404
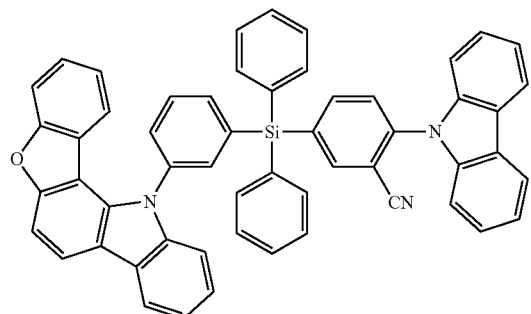
405
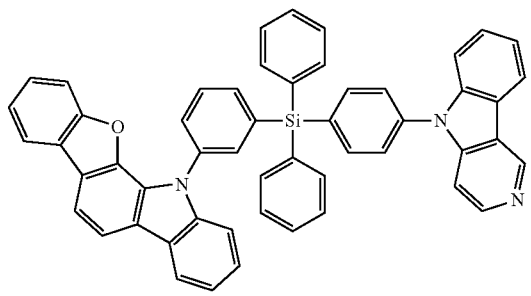
406
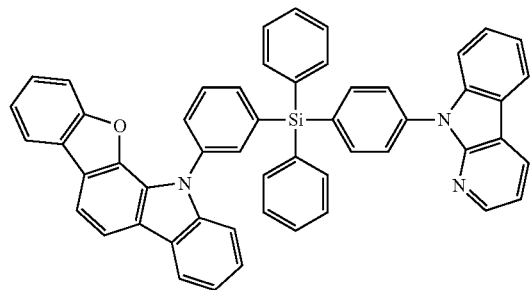
407
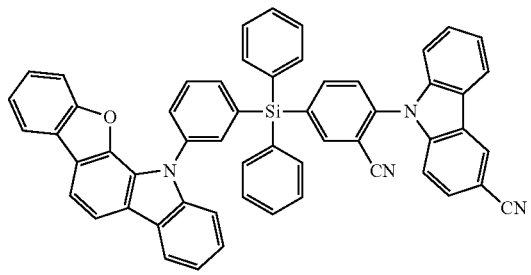
408
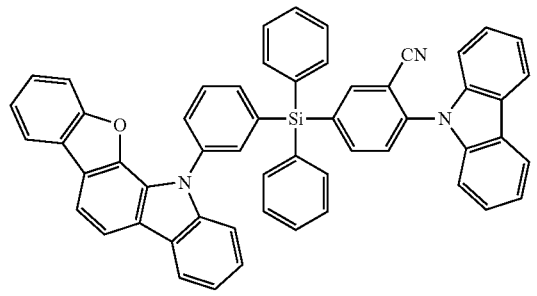
409
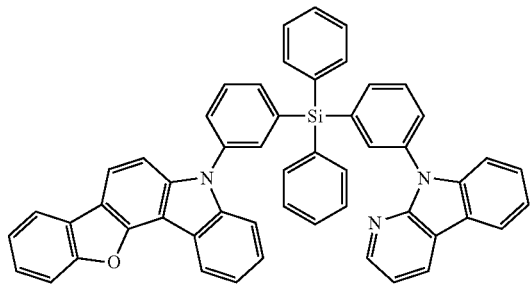
410
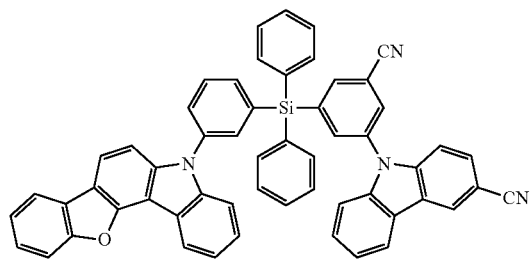
411
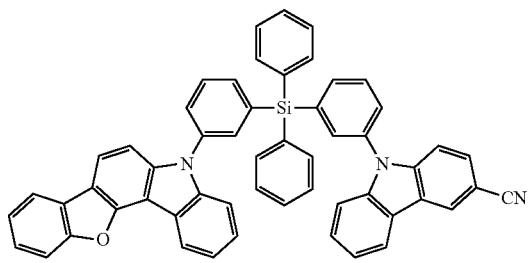

-continued
412
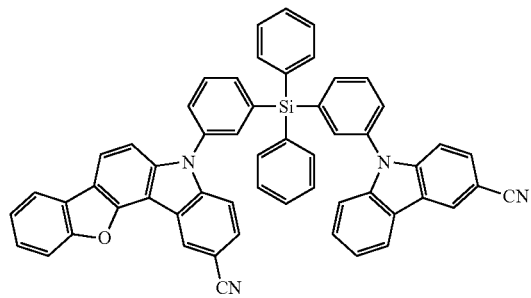
413
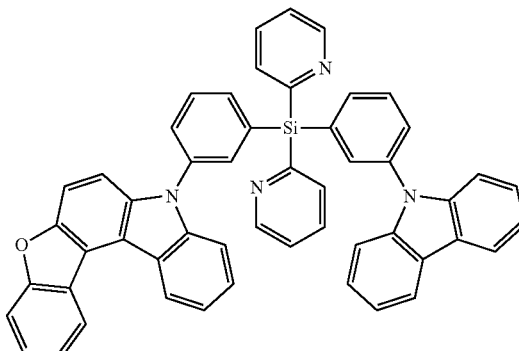
414
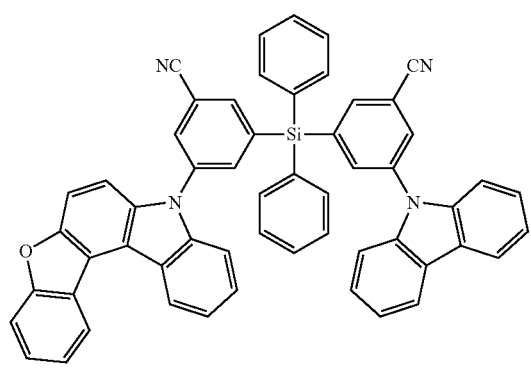
415
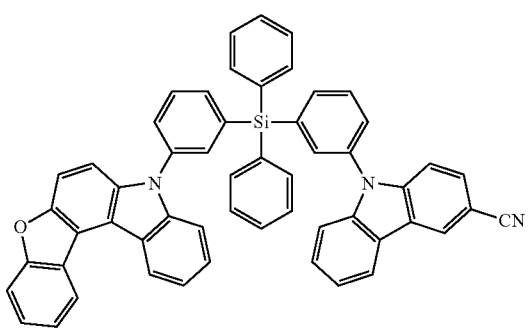
416
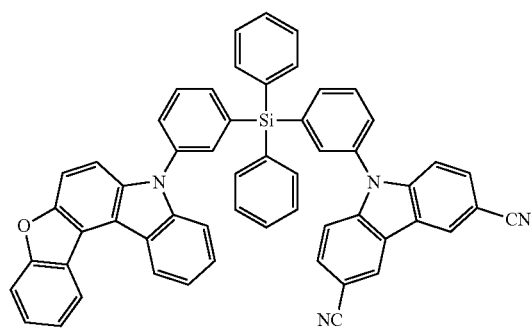
417
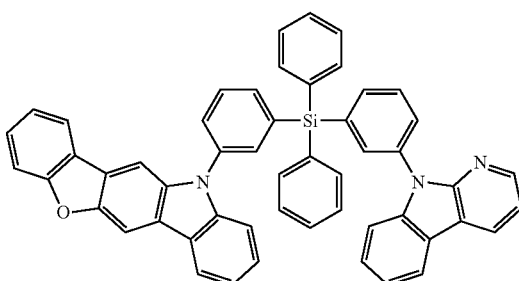
418
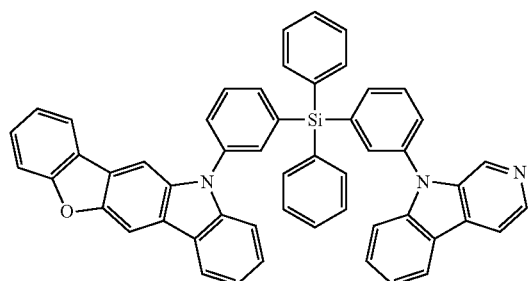
419
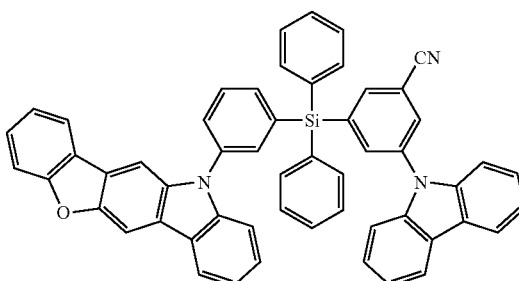

831 832
-continued
420
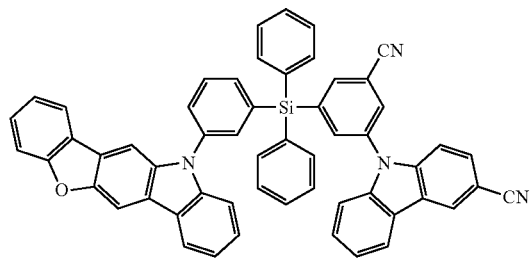
421
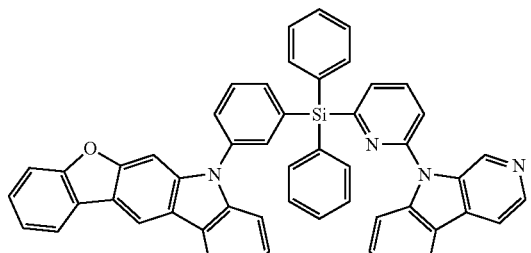
422
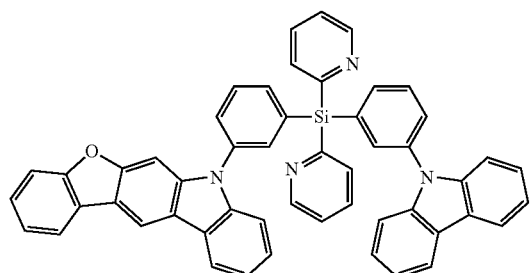
423
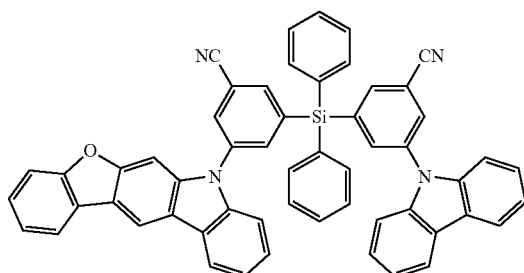
424
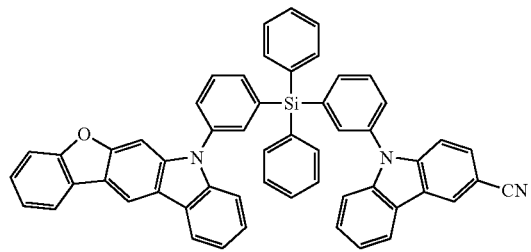
425
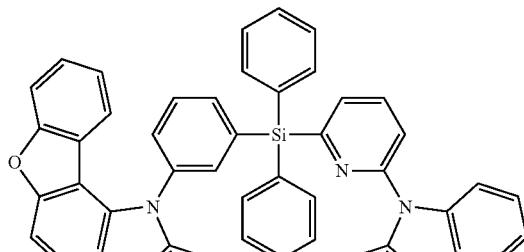
426
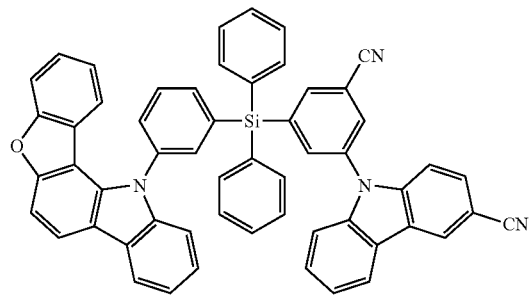
427
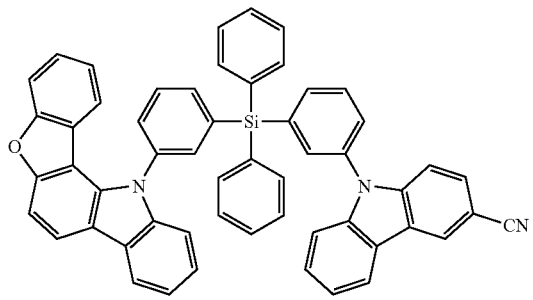
428
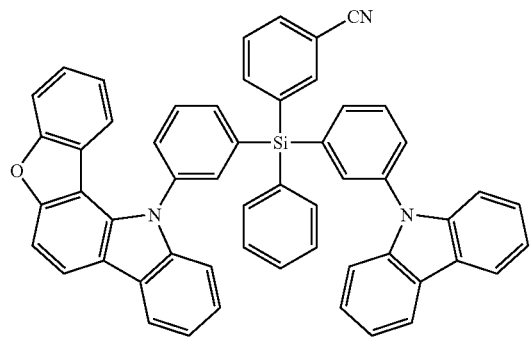
429
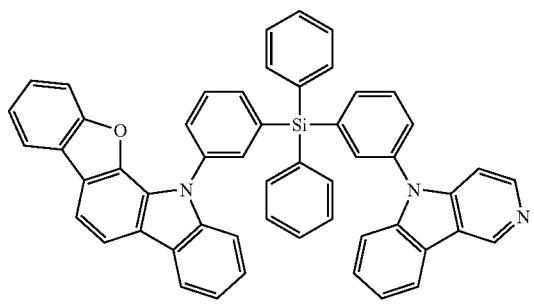

430
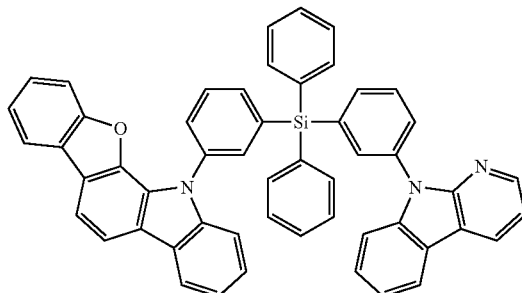

431
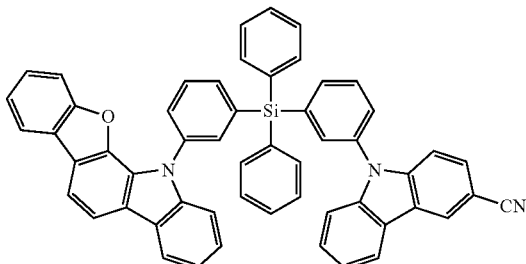

432
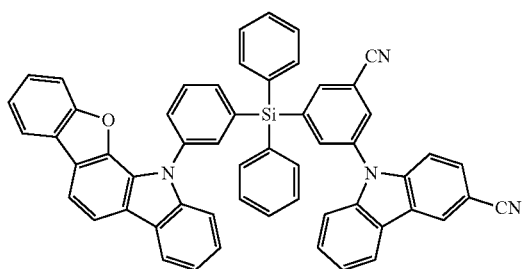

In Compounds 1 to 432,
Ph indicates a phenyl group.
In one or more embodiments, the hole transport host may include o-CBP:

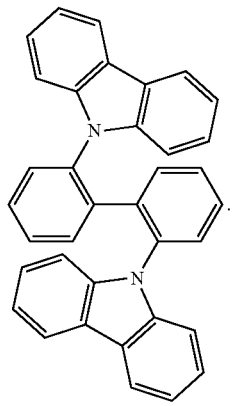 [SMILES: c1ccc(-n2c3ccccc3c3ccccc32)c(-c2ccccc2-n2c3ccccc3c3ccccc32)c1]

When the host is a mixture of the electron transport host and the hole transport host, a weight ratio of the electron transport host to the hole transport host may be 1:9 to 9:1, for example, 2:8 to 8:2, and In one or more embodiments, may be 4:6 to 6:4, and in one or more embodiments, may be 5:5. When the weight ratio of the electron transport host to the hole transport host is within the ranges above, a balance of hole and electron transport into the emission layer 15 may be achieved.

Dopant in Emission Layer 15

Since the dopant emits fluorescence, the organic light-emitting device according to the present disclosure is clearly distinguished from an organic light-emitting device including a compound emitting phosphorescence.

A maximum emission wavelength of the emission spectrum of the dopant may be 400 nm or more and 550 nm or less. For example, the maximum emission wavelength of the emission spectrum of the dopant may be 400 nm or more and 495 nm or less, or 450 nm or more and 495 nm or less. However, embodiments of the present disclosure are not limited thereto. That is, the dopant may emit blue light. The term "maximum emission wavlength" as used herein refers to a maimum wavelength of the emission intensity, and is also referred to as "peak emission wavelength".

In one or more embodiments, the dopant may not include a metal atom.

In one or more embodiments, the dopant may be a condensed polycyclic compound, a styryl-based compound, or any combination thereof.

For example, the dopant may be a naphthalene-containing core, a fluorene-containing core, a spiro-bifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, and cores represented by Formulae 501-1 to 501-18, but embodiments of the present disclosure are not limited thereto:

501-1
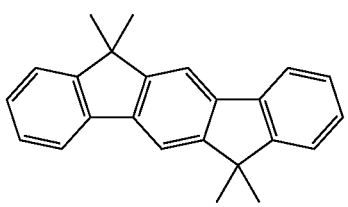

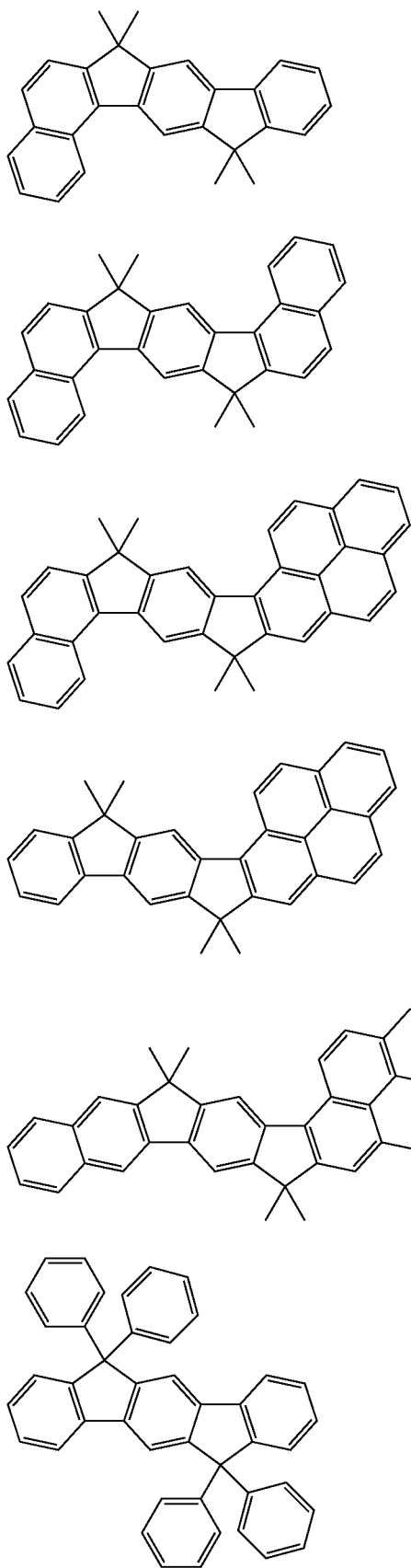
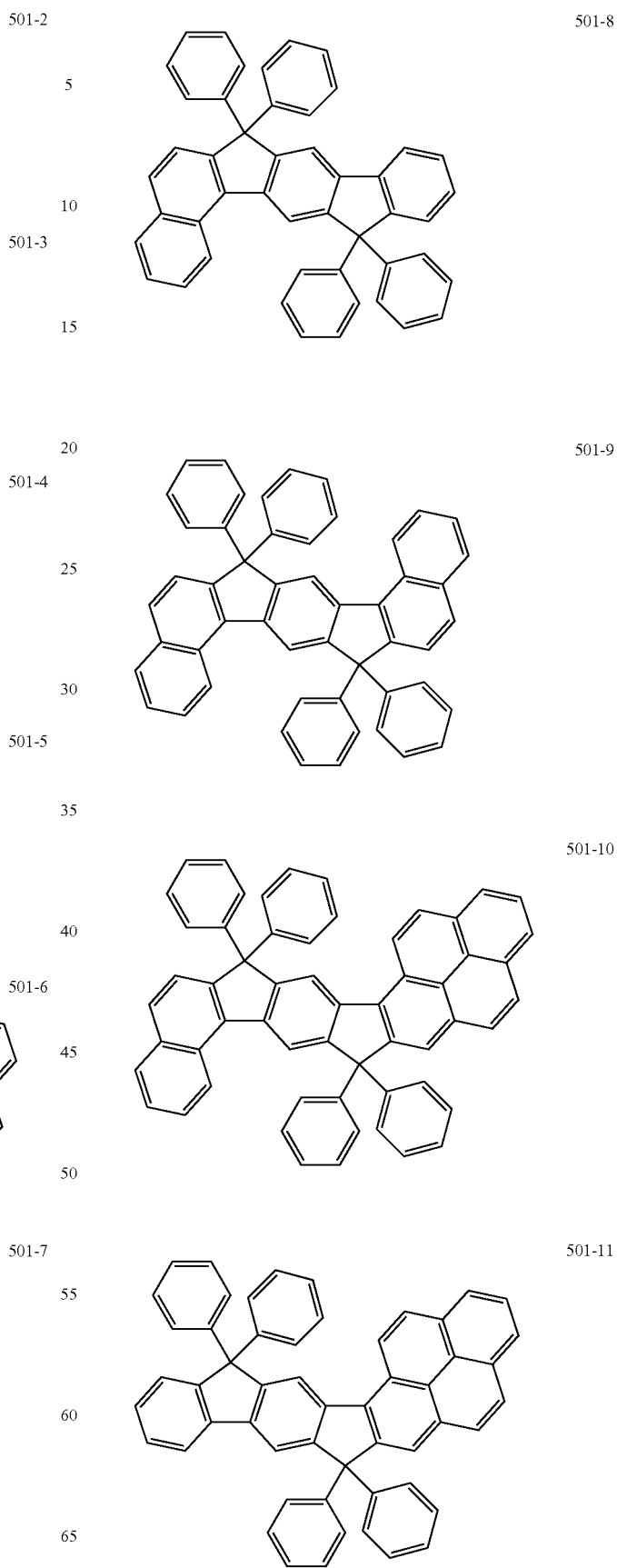

501-12

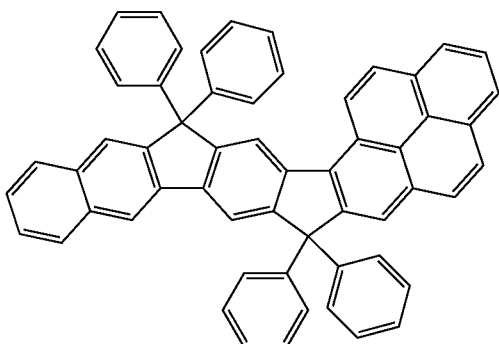

501-13

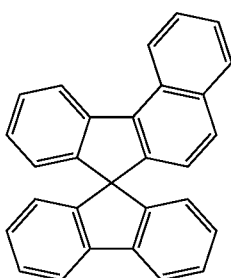

501-14

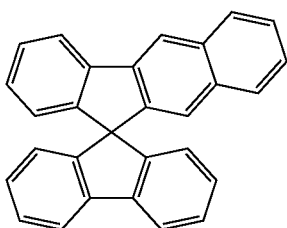

501-15

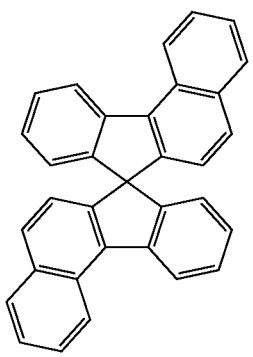

501-16

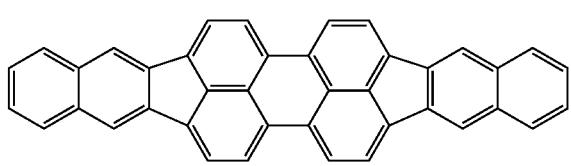

501-17

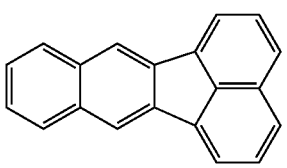

501-18

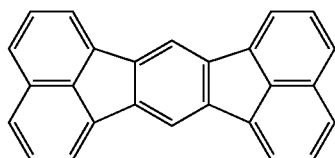

In one or more embodiments, the dopant may be a styryl-amine-based compound, a styryl-carbazole-based compound, or any combination thereof, but embodiments of the present disclosure are not limited thereto.

In one or more embodiments, the dopant may be a compound represented by Formula 501:

<Formula 501>

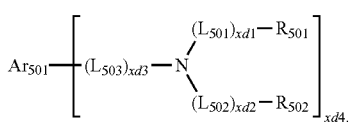

In Formula 501,
Ar$_{501}$ may be:
a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene, an indenoanthracene, a tetracene, a bisanthracene, or a group represented by Formulae 501-1 to 501-18; or
a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene an indenoanthracene, a tetracene, a bisanthracene, or a group represented by Formulae 501-1 to 501-18, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{10}$ heteroaryl group, a monovalent non-aromatic condensed polycyclic group, a monovalent non-aromatic condensed heteropolycyclic group, and —Si(Q$_{501}$)(Q$_{502}$)(Q$_{503}$) (wherein Q$_{501}$ to Q$_{503}$ may each independently be hydrogen, a C$_1$-C$_{10}$ alkyl group, a C$_1$-C$_{10}$ alkoxy group, a C$_6$-C$_{60}$ aryl group, a C$_1$-C$_{10}$ heteroaryl group, a monovalent non-aromatic condensed polycyclic group, a monovalent non-aromatic condensed heteropolycyclic group, or any combination thereof, L$_{501}$ to L$_{503}$ may each independently be a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, or a substituted or unsubstituted divalent non-aromatic condensed heteropolycyclic group, $R_{501}$ and $R_{502}$ may each independently be:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof, xd1 to xd3 may each independently be 0, 1, 2, or 3, and xd4 may be 0, 1, 2, 3, 4, 5, or 6.

For example, in Formula 501, $Ar_{501}$ may be:

a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene, an indenoanthracene, a tetracene, a bisanthracene, or a group represented by Formulae 501-1 to 501-18; or a naphthalene, a fluorene, a spiro-bifluorene, a benzofluorene, a dibenzofluorene, a phenanthrene, an anthracene, a fluoranthene, a triphenylene, a pyrene, a chrysene, a naphthacene, a picene, a perylene, a pentaphene, an indenoanthracene, a tetracene, a bisanthracene, or a group represented by Formulae 501-1 to 501-18, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, —Si($Q_{501}$)($Q_{502}$)($Q_{503}$) (wherein $Q_{501}$ to $Q_{503}$ may each independently be hydrogen, a $C_1$-$C_{20}$ alkyl group, a $C_1$-$C_{20}$ alkoxy group, a phenyl group, a biphenyl group, a terphenyl group, or a naphthyl group) or any combination thereof, $L_{501}$ to $L_{503}$ may each be understood by referring to the description presented in connection with $L_{21}$, xd1 to xd3 may each independently be 0, 1, or 2, and xd4 may be 0, 1, 2, or 3, but embodiments of the present disclosure are not limited thereto.

In one or more embodiments, the dopant may include a compound represented by one of Formulae 502-1 to 502-5:

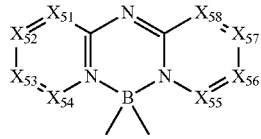

<Formula 502-1>

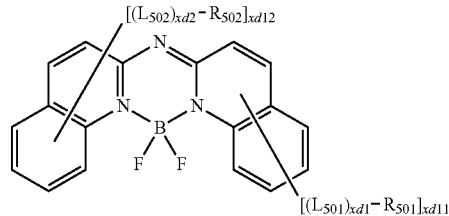

<Formula 502-2>

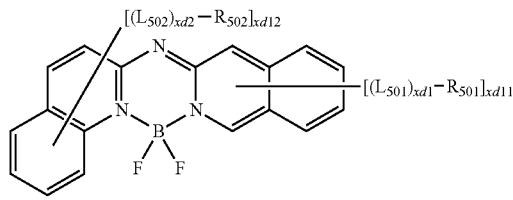

<Formula 502-3>

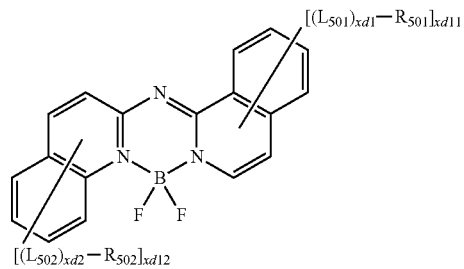

<Formula 502-4>

<Formula 502-5>

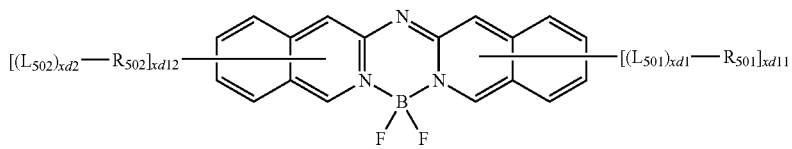

In Formulae 502-1 to 502-5, $X_{51}$ may be N or C-[$(L_{501})_{xd1}$-$R_{501}$], $X_{52}$ may be N or C-[$(L_{502})_{xd2}$-$R_{502}$], $X_{53}$ may be N or C-[$(L_{503})_{xd3}$-$R_{503}$], $X_{54}$ may be N or C-[$(L_{504})_{xd4}$-$R_{504}$], $X_{55}$ may be N or C-[$(L_{505})_{xd5}$-$R_{505}$], $X_{56}$ may be N or C-[$(L_{506})_{xd6}$-$R_{506}$], $X_{57}$ may be N or C-[$(L_{507})_{xd7}$-$R_{507}$], and $X_{58}$ may be N or C-[$(L_{508})_{xd8}$-$R_{506}$], $L_{501}$ to $L_{508}$ may each be understood by referring to the description presented in connection with $L_{501}$ in Formula 501, xd1 to xd8 may each be understood by referring to the description presented in connection with xd1 in Formula 501, $R_{501}$ to $R_{508}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof, xd11 and xd12 may each independently be an integer from 0 to 5, two substituents of $R_{501}$ to $R_{504}$ may optionally be linked to form a saturated or unsaturated ring, and two substituents of $R_{505}$ to $R_{506}$ may optionally be linked to form a saturated or unsaturated ring.

In one or more embodiments, the dopant may include a compound represented by Formula 503-1:

<Formula 503>

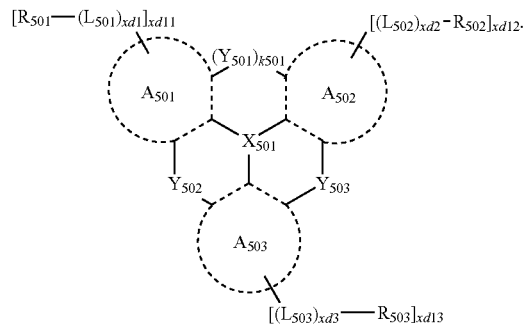

In Formula 503, $X_{501}$ may be N, B, P(=)($R_{504}$), or P(=S)($R_{504}$), $Y_{501}$ to $Y_{502}$ may each independently be O, S, N($R_{505}$), B($R_{505}$), C($R_{505}$)($R_{506}$), or Si($R_{505}$)($R_{506}$), k501 may be 0 or 1, wherein m when k501 is 0, —($Y_{501}$)$_{k501}$— does not exist, $A_{501}$ to $A_{503}$ may each independently be a $C_5$-$C_{30}$ carbocyclic group or a $C_1$-$C_{30}$ heterocyclic group, $L_{501}$ to $L_{503}$ may be understood by referring to the description presented in connection with $L_{501}$ in formula 501, xd1 to xd3 may be understood by referring to the description presented in connection with xl in Formula 501, $R_{501}$ to $R_{506}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{60}$ alkenyl group, a substituted or unsubstituted $C_2$-$C_0$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(Q$_1$)(Q$_2$)(Q$_3$), —Si(Q$_1$)(Q$_2$)(Q$_3$), —B(Q$_1$)(Q$_2$), —N(Q$_1$)(Q$_2$), —P(Q$_1$)(Q$_2$), —C(=O)(Q$_1$), —S(=O)(Q$_1$), —S(=O)$_2$(Q$_1$), —P(=O)(Q$_1$)(Q$_2$), or —P(=S)(Q$_1$)(Q$_2$), wherein R$_{501}$ to R$_{506}$ may optionally be linked to form a substituted or unsubstituted C$_5$-C$_{30}$ carbocyclic group a substituted or unsubstituted a C$_1$-C$_{30}$ heterocyclic group, xd11 and xd12 may each independently be an integer from 0 to 5, Q$_1$ to Q$_3$, Q$_{21}$ to Q$_{23}$, and Q$_{31}$ to Q$_{33}$ may each independently be hydrogen, deuterium, —F, —Cl, —Br, —I, a hydroxyl group, a cyano group, a nitro group, an amidino group, a hydrazino group, a hydrazono group, a C$_1$-C$_{10}$ alkyl group, a C$_2$-C$_{60}$ alkenyl group, a C$_2$-C$_{60}$ alkynyl group, a C$_1$-C$_{10}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a C$_1$-C$_{60}$ heteroaryloxy group, a C$_1$-C$_{60}$ heteroarylthio group, a monovalent non-aromatic condensed polycyclic group, a monovalent non-aromatic condensed heteropolycyclic group, a biphenyl group, or a terphenyl group, and Q$_1$ to Q$_3$, Q$_{21}$ to Q$_{23}$, and Q$_{31}$ to Q$_{33}$ may each independently be hydrogen, deuterium, —F, —Cl, —Br, —I, a hydroxyl group, a cyano group, a nitro group, an amidino group, a hydrazino group, a hydrazono group, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a C$_1$-C$_{60}$ heteroaryloxy group, a C$_1$-C$_{60}$ heteroarylthio group, a monovalent non-aromatic condensed polycyclic group, a monovalent non-aromatic condensed heteropolycyclic group, a biphenyl group, or a terphenyl group.

The dopant may include, for example, at least one of Compounds FD(1) to FD(16) and FD1 to FD18:

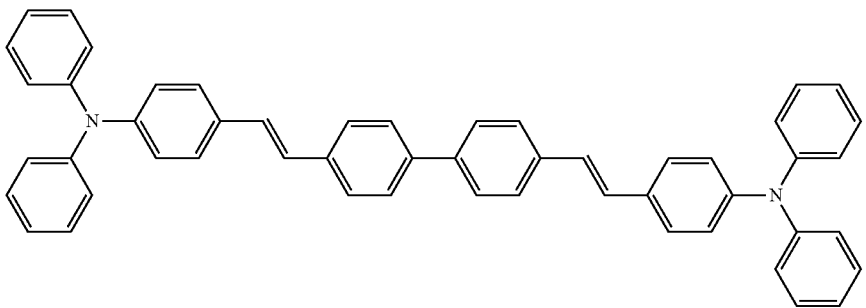

FD(1)

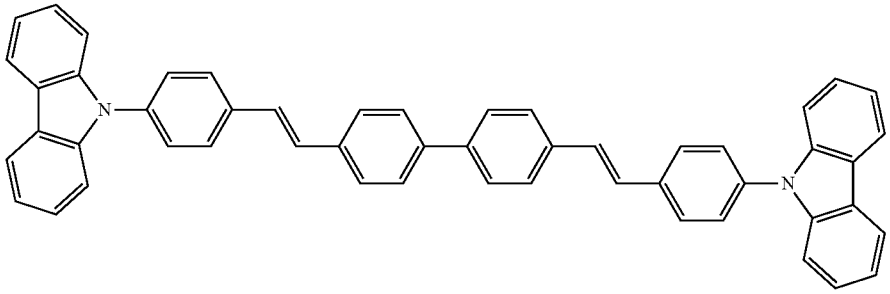

FD(2)

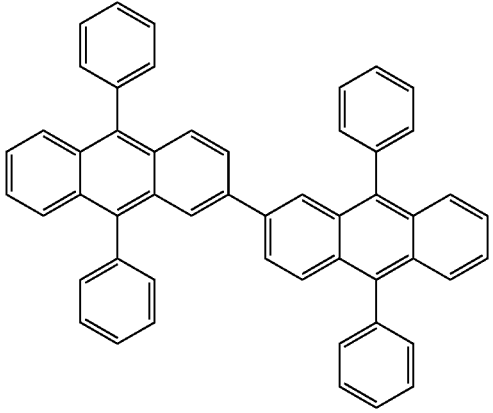

FD(3)

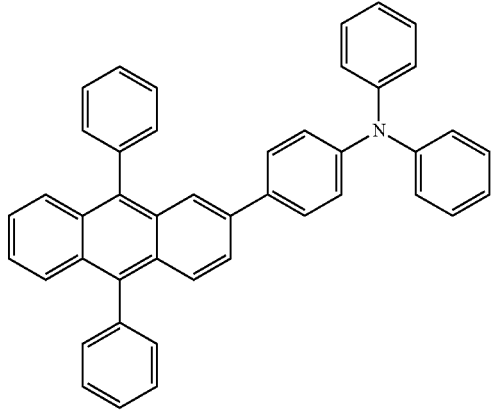

FD(4)

-continued
FD(5)
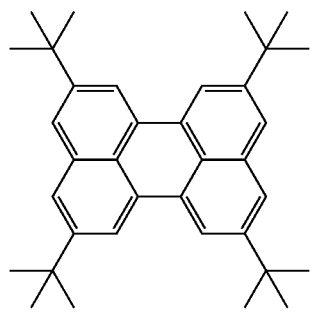
FD(6)
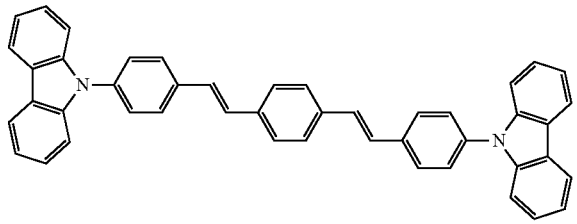
FD(7)
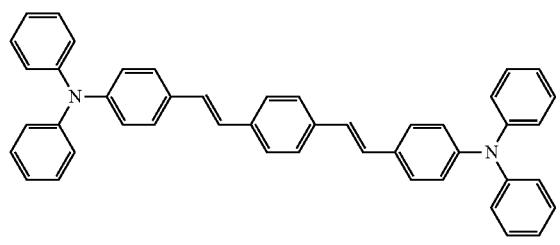
FD(8)
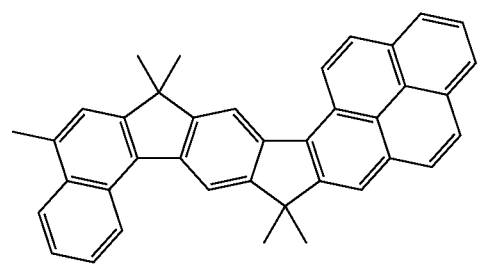
FD(9)
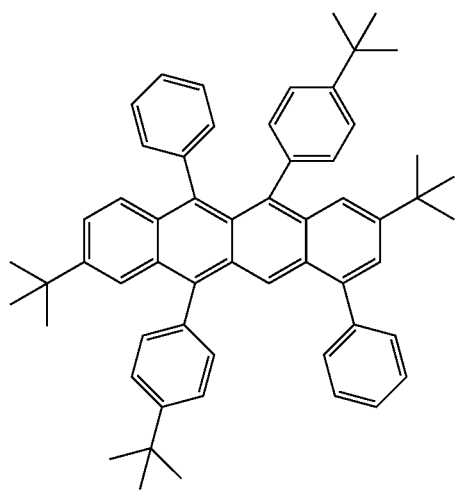
FD(10)
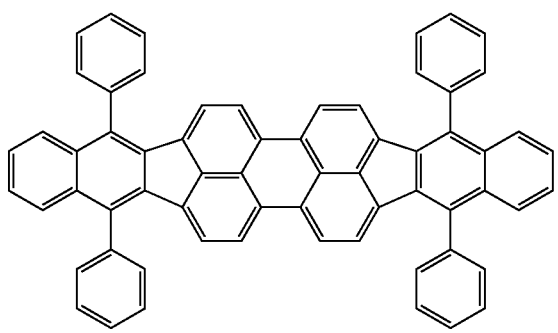
FD(11)
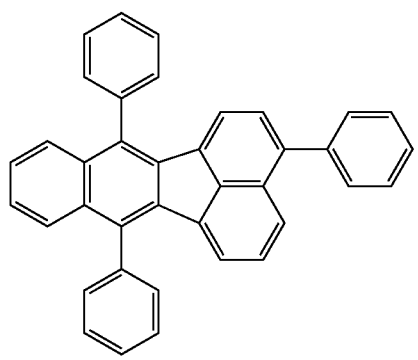
FD(12)
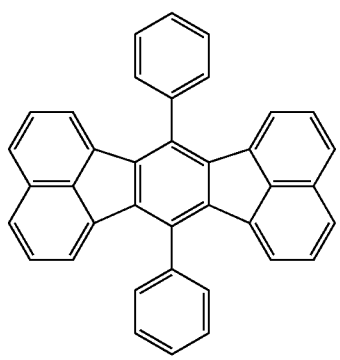

-continued
FD(13)
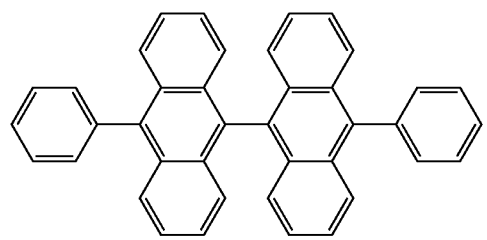
FD(14)
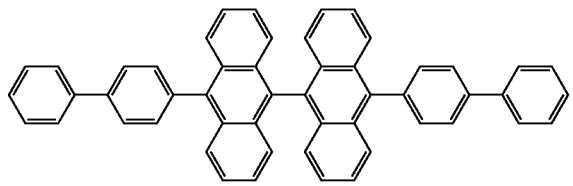
FD(15)
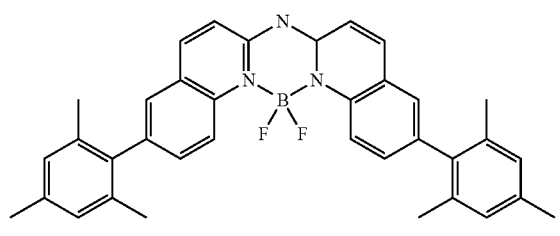
FD(16)
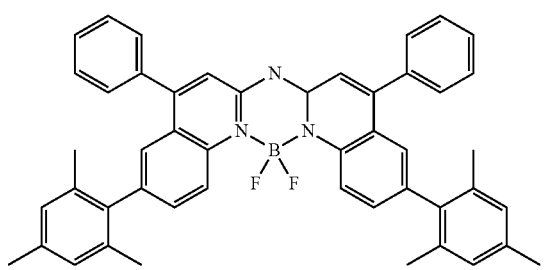
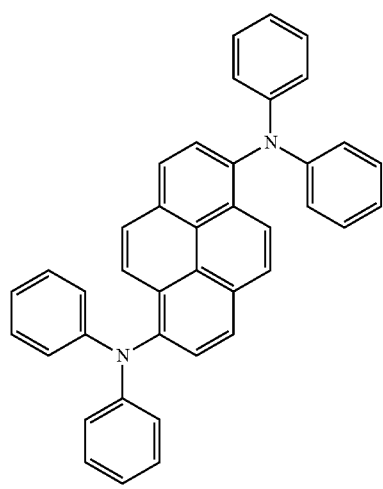
FD1
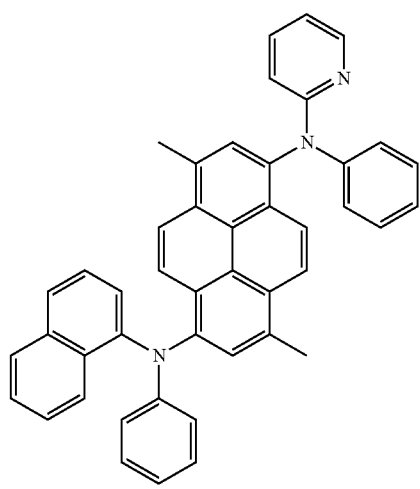

-continued
FD3
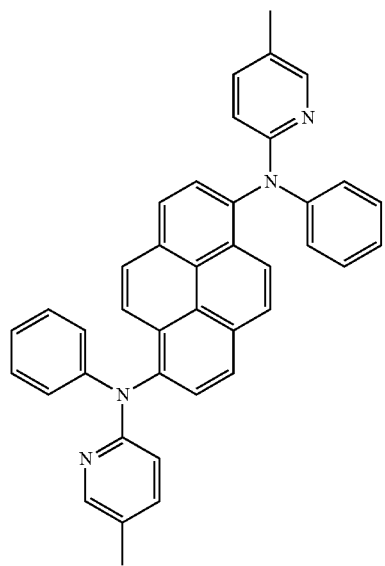
FD4
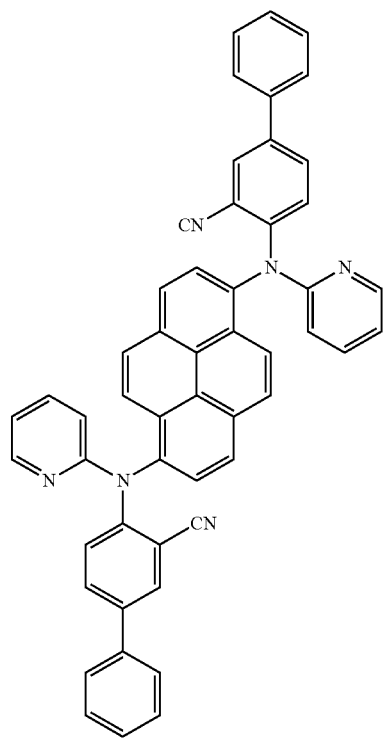
FD5
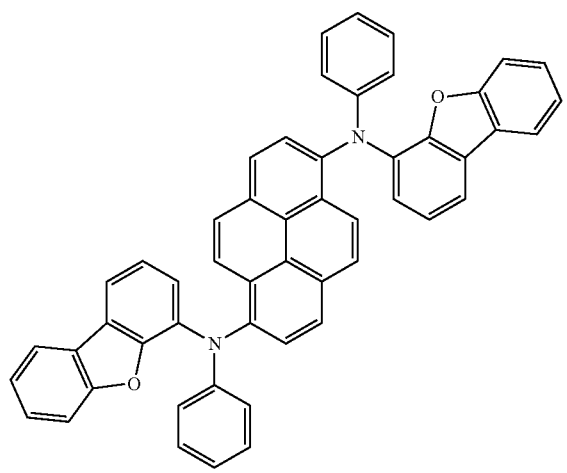
FD6
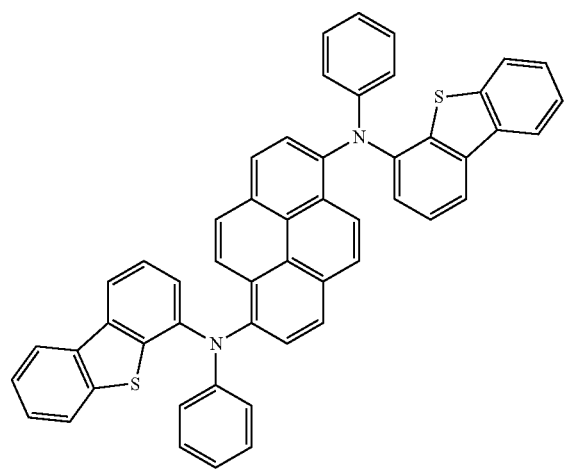
FD7
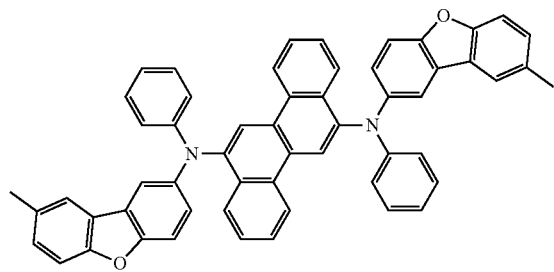
FD8
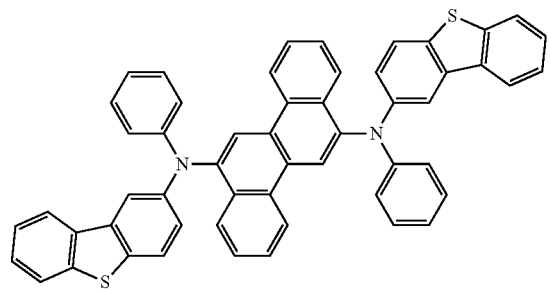

-continued
FD9
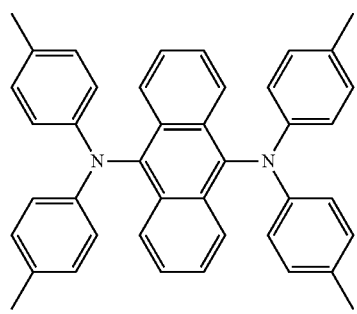
FD10
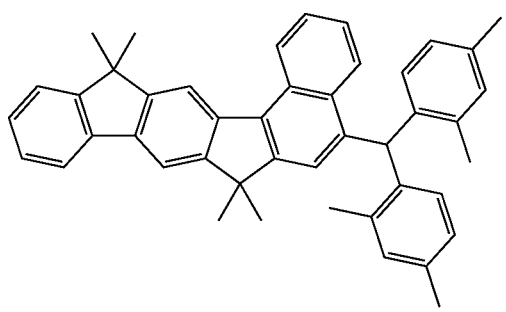
FD11
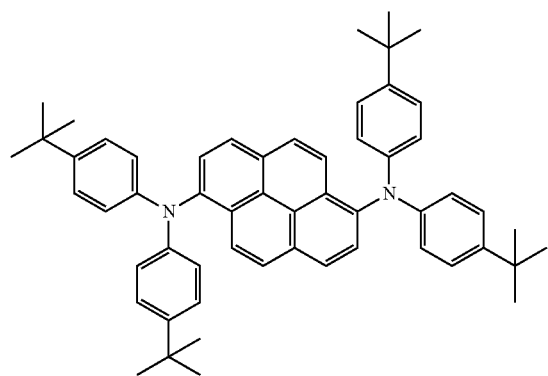
FD12
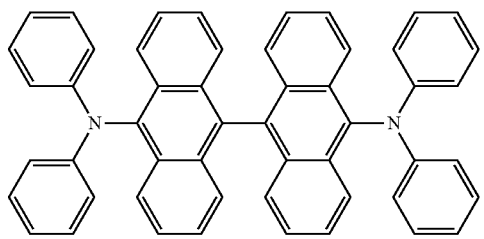
FD13
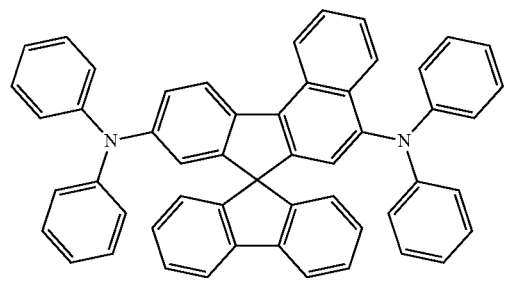
FD14
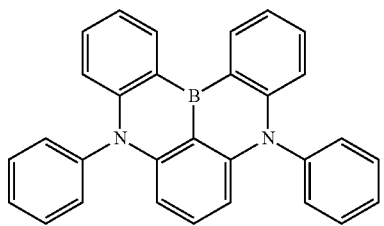
FD15
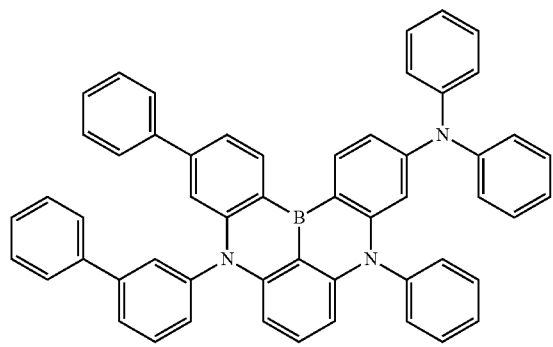
FD16
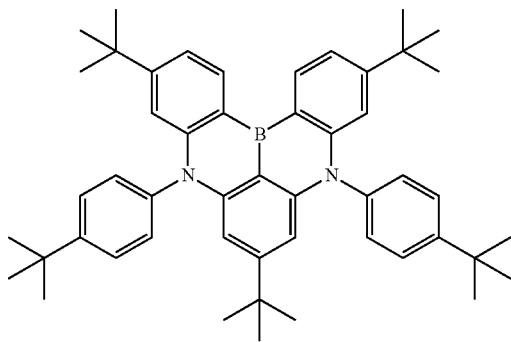

FD17

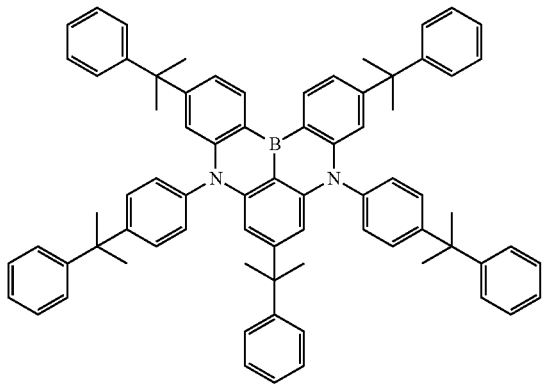

FD18

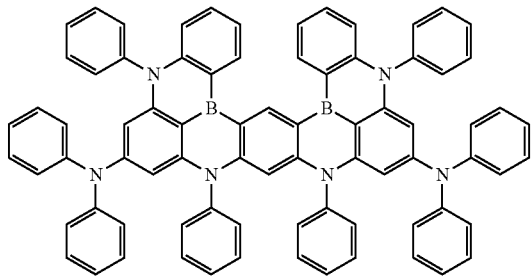

Compound in Emission Layer 15

In one or more embodiments, the compound may be represented by Formula 101 or 102:

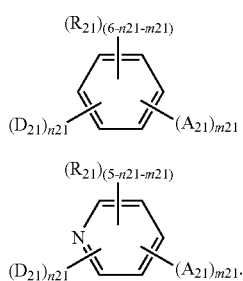

<Formula 101>

<Formula 102>

In Formulae 101 and 102, $A_{21}$ may be an acceptor group, $D_{21}$ may be a donor group, m21 may be 1, 2, or 3, n21 may be 1, 2, or 3, the sum of n21 and m21 Formula 101 may be 6 or less, and the sum of n21 and m21 in Formula 102 may be 5 or less, $R_{21}$ may be hydrogen, deuterium, —F, —Cl, —Br, —I, —$SF_5$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkyl aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and a plurality of $R_{21}$(s) may optionally be linked to form a substituted or unsubstituted $C_5$-$C_{30}$ carbocyclic group or a substituted or unsubstituted $C_1$-$C_{30}$ heterocyclic group, $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{10}$ alkyl group substituted with at least oen deuterium, —F, a cyano group, a $C_1$-$C_{10}$ alkyl group, a $C_6$-$C_{60}$ aryl group, or any combination thereof, or a $C_6$-$C_{60}$ aryl group substituted with at least one deuterium, —F, a cyano group, a $C_1$-$C_{10}$ alkyl group, a $C_6$-$C_{60}$ aryl group, or any combination thereof.

For example, $A_{21}$ in Formulae 101 and 102 may be a substituted or unsubstituted π electron-depleted nitrogen-free cyclic group.

In detail, the electron-depleted nitrogen-free cyclic group may be:

a benzene group, a heptalene group, an indene group, a naphthalene group, an azulene group, an indacene group, acenaphthylene group, a fluorene group, a spirobifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group; or a condensed ring in which two or more π electron-depleted nitrogen-free cyclic groups are condensed with each other, but embodiments of the present discourse are not limited thereto.

For example, $D_{21}$ in Formulae 101 and 102 may be:

—F, a cyano group, or a π electron-depleted nitrogen-containing cyclic group;

a $C_1$-$C_{60}$ alkyl group, a π electron-depleted nitrogen-containing cyclic group, or a u electron-depleted nitrogen-free cyclic group, each substituted with at least one —F, a cyano group, or any combination thereof; or a π electron-depleted nitrogen-containing cyclic group substituted with at least one deuterium, a $C_1$-$C_{60}$ alkyl group, a π electron-depleted nitrogen-containing cyclic group, a π electron-depleted nitrogen-free cyclic group, or any combination thereof.

In detail, the π electron-depleted nitrogen-free cyclic group may be understood by referring to the description thereof presented herein.

In detail, the π electron-depleted nitrogen-containing cyclic group may be a cyclic group having at least one *—N=* moiety, and examples thereof include an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, and a benzimidazolobenzimidazole; and a condensed cyclic ring in which two or more u electron-depleted nitrogen-containing cyclic a group are condensed with each other.

In one or more embodiments, the compound may be a compounds belonging to A group VII to XII, but embodiments of the present disclosure are not limited thereto:

<Group VII>

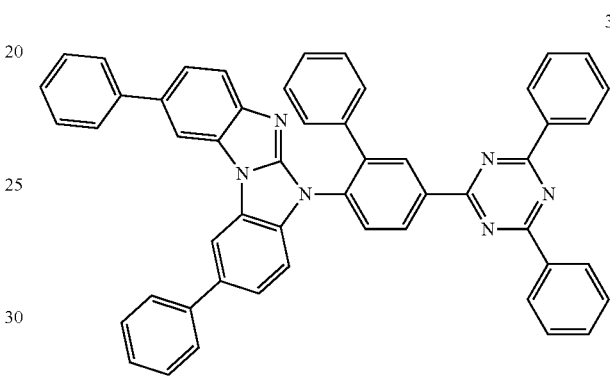

2

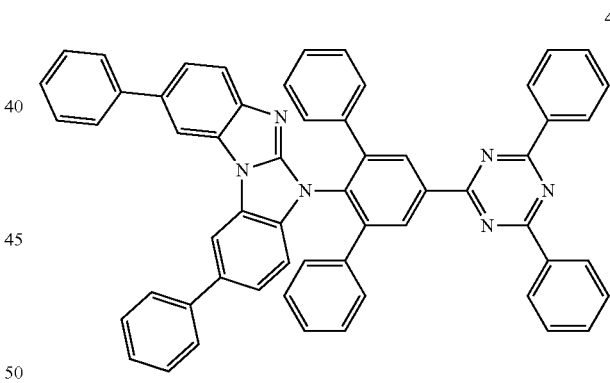

3

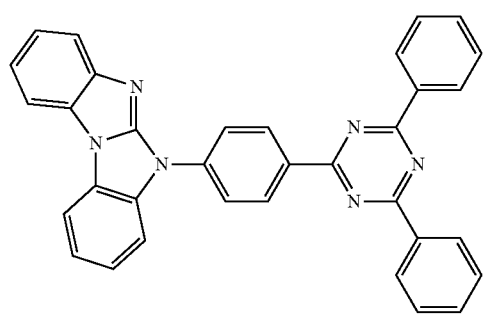

4

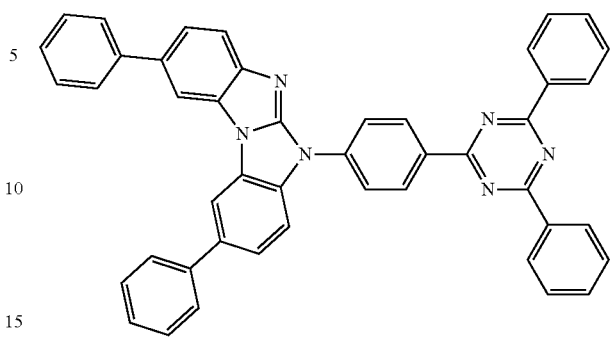

1

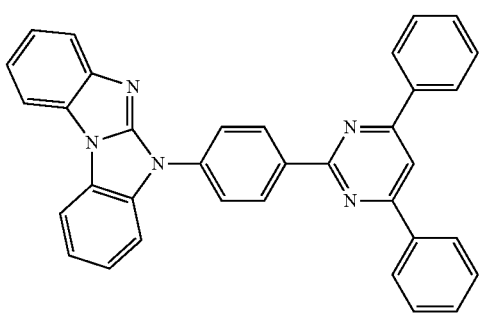

5

6
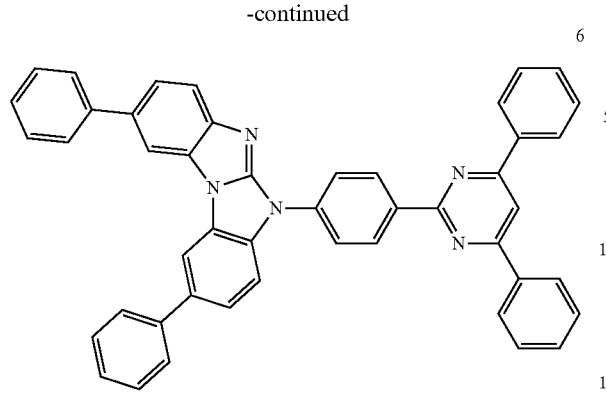
10
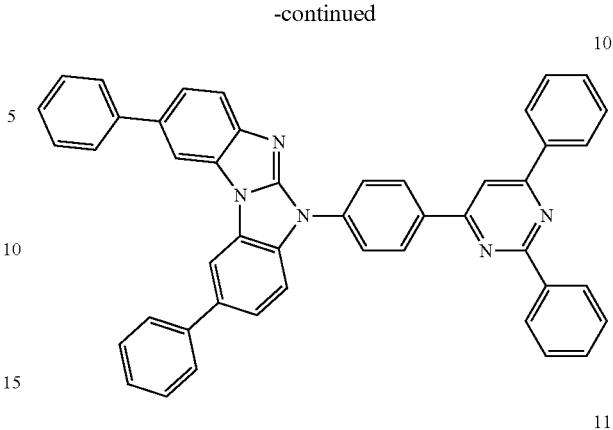
7
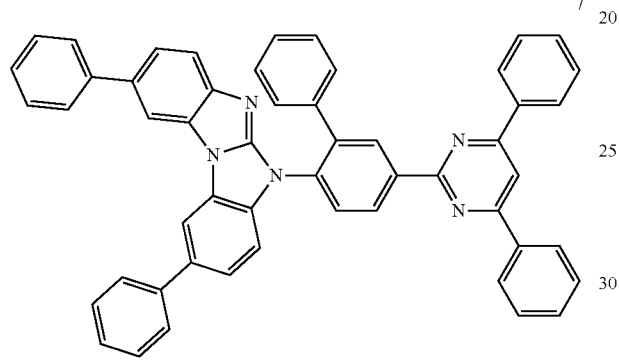
11
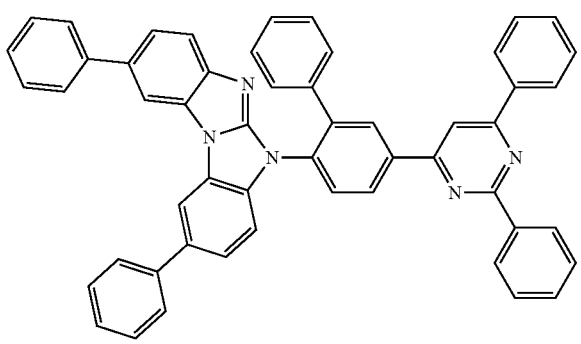
8
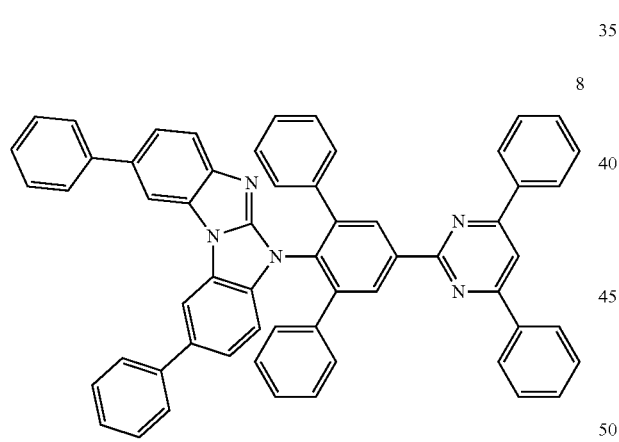
12
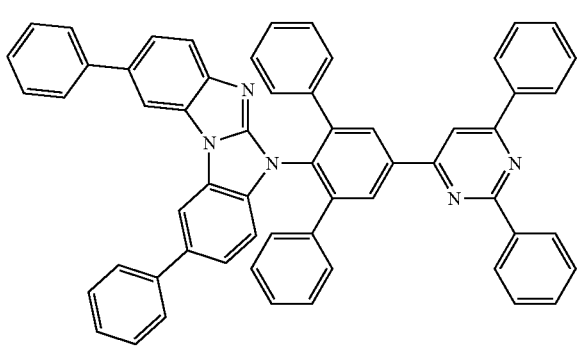
9
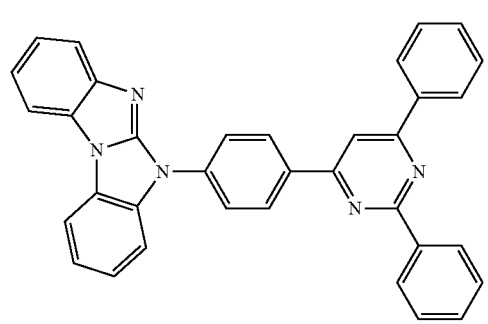
13
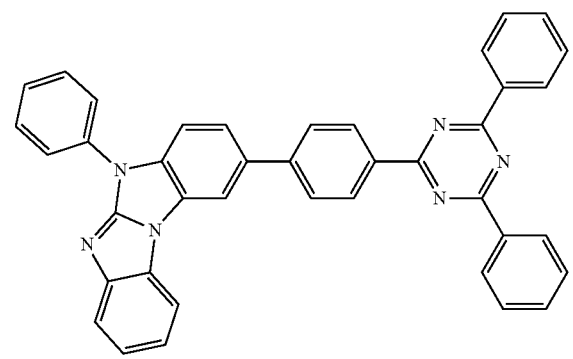

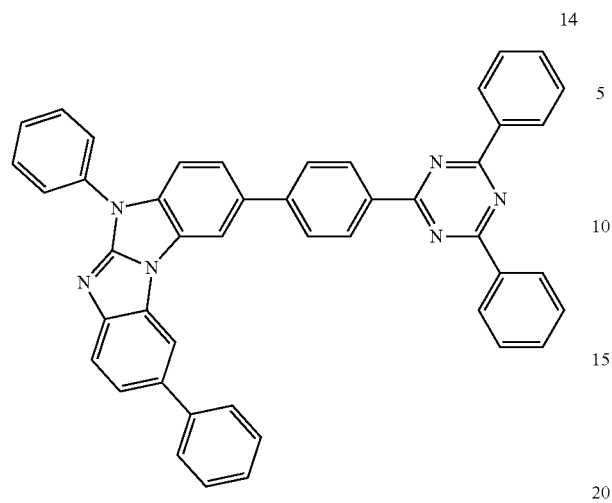
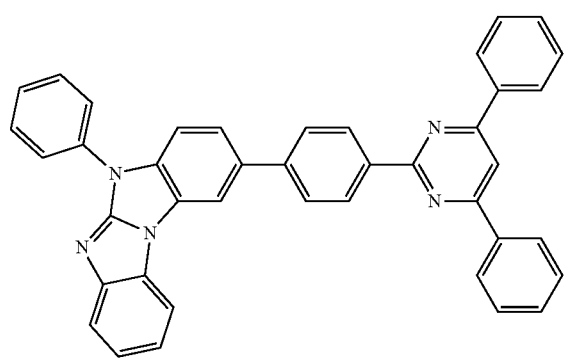
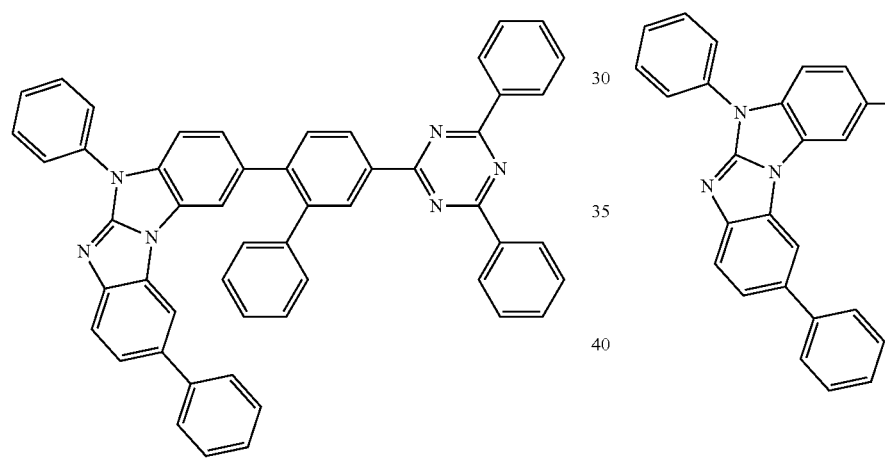

861
-continued
862
-continued
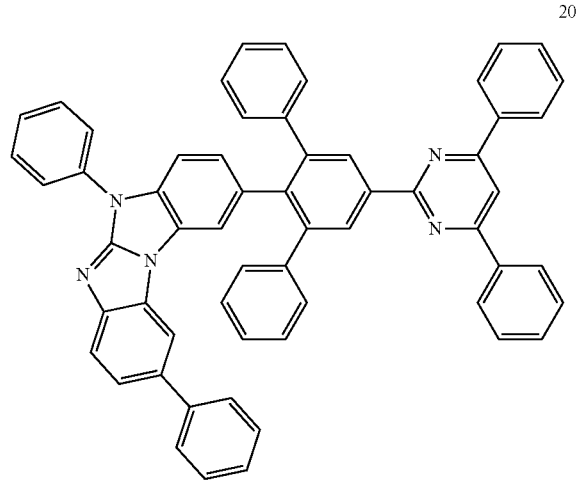
20
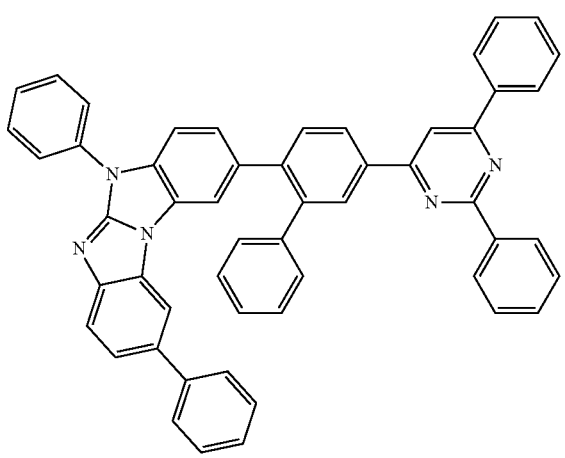
23
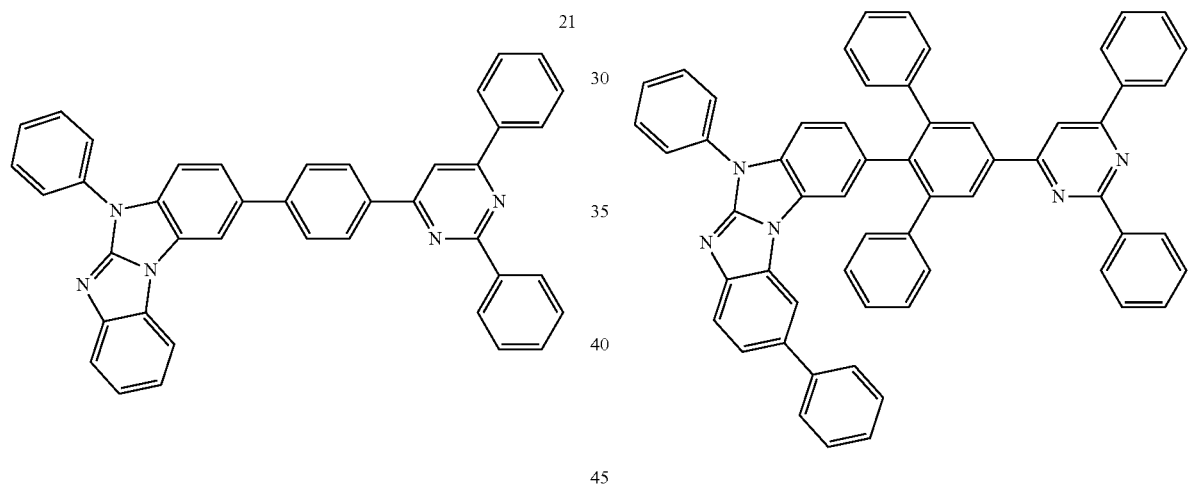
21
22
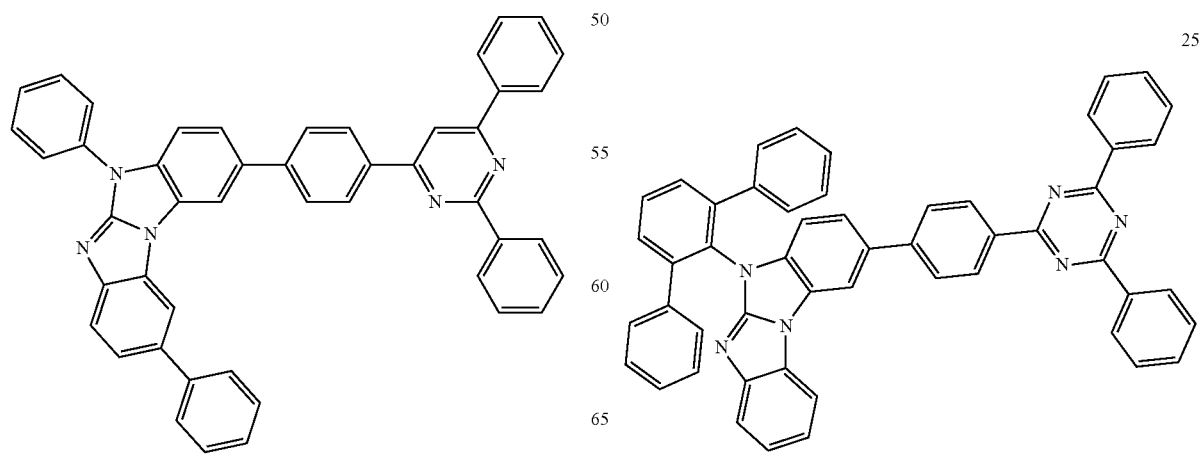
24
25

26
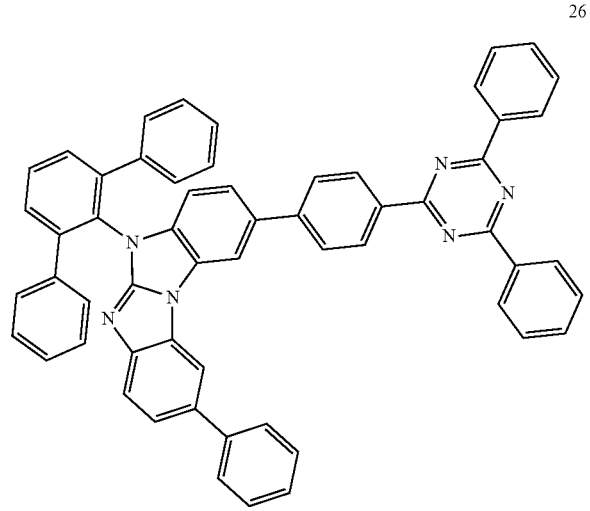
27
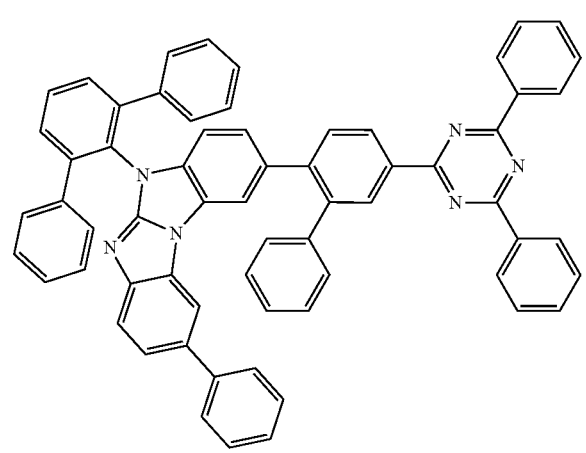
28
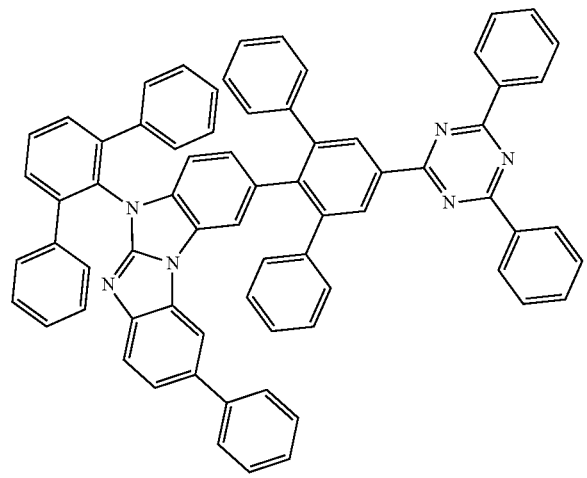
29
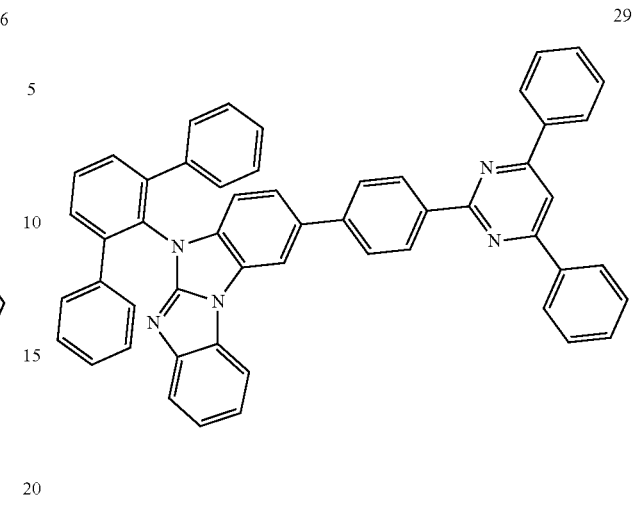
30
31
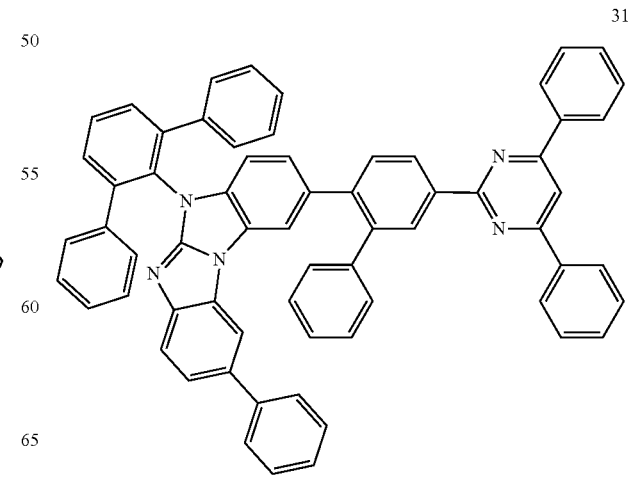

32
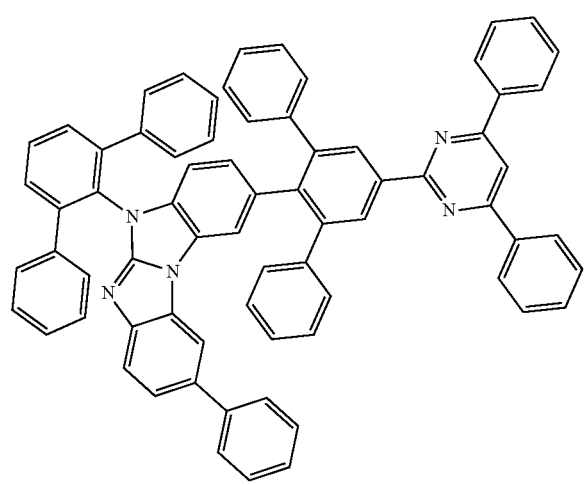
33
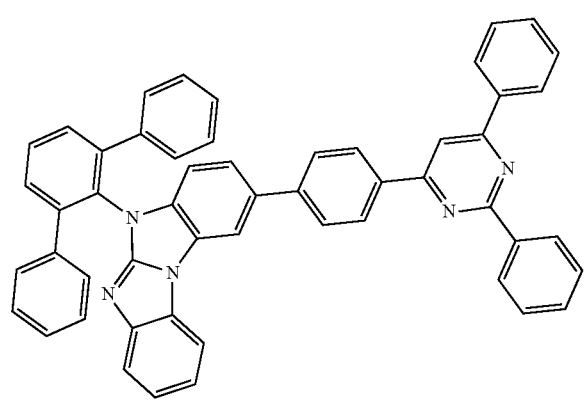
34
35
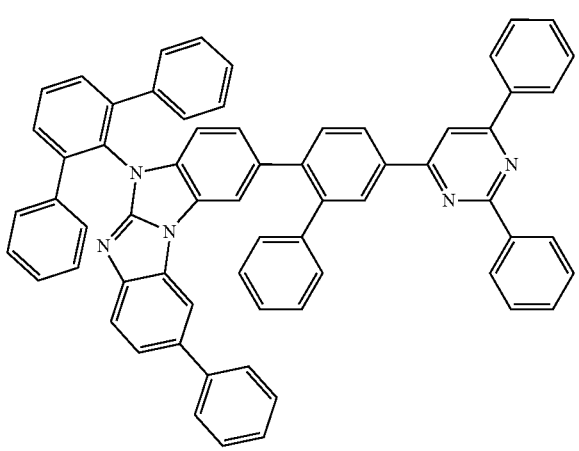
36
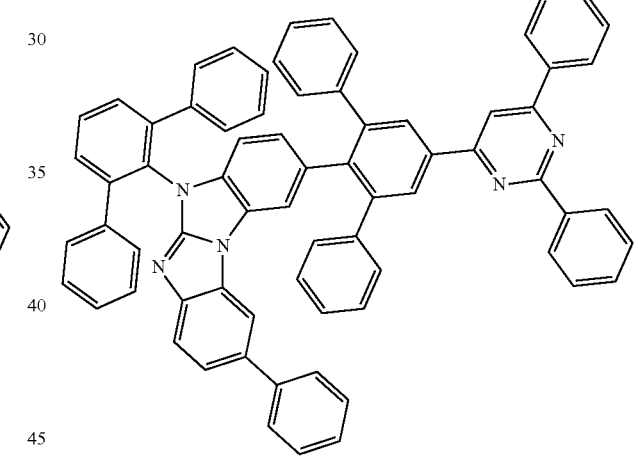
37
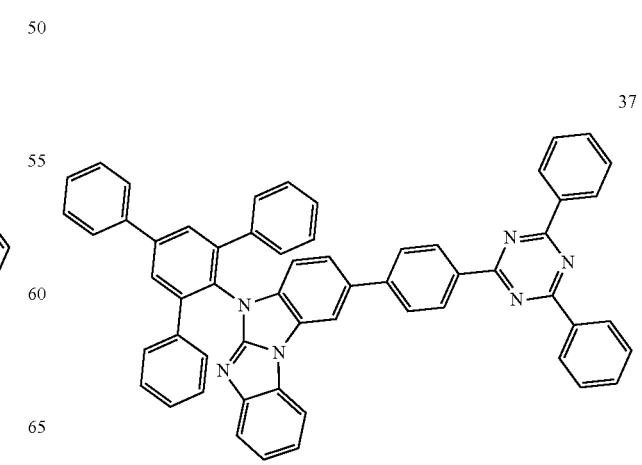

38
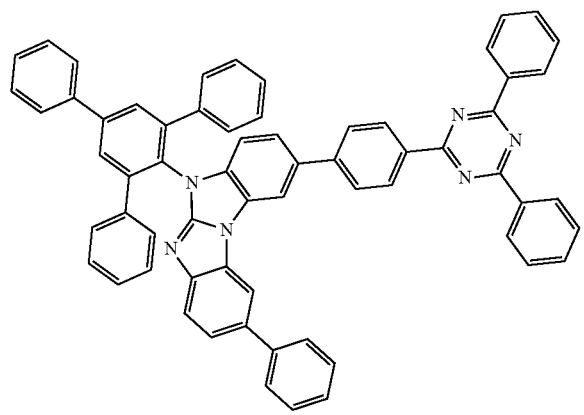
39
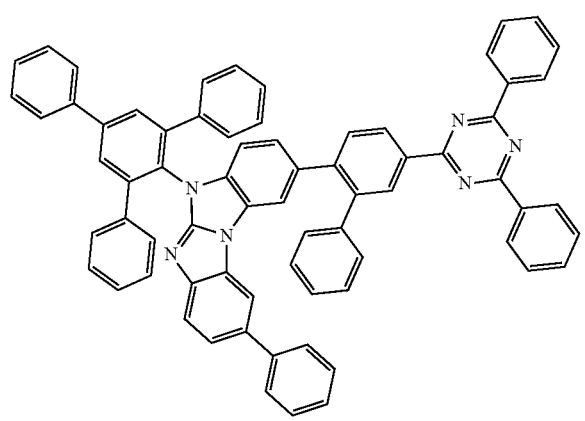
40
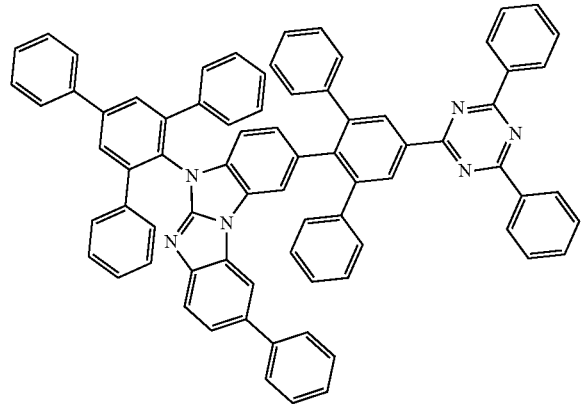
41
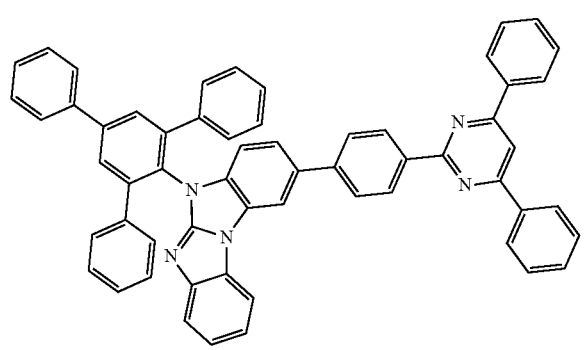
42
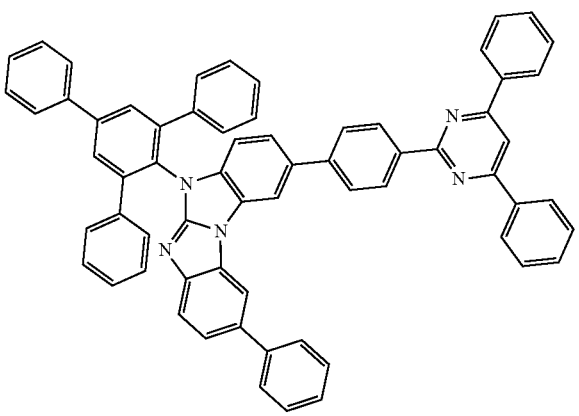
43
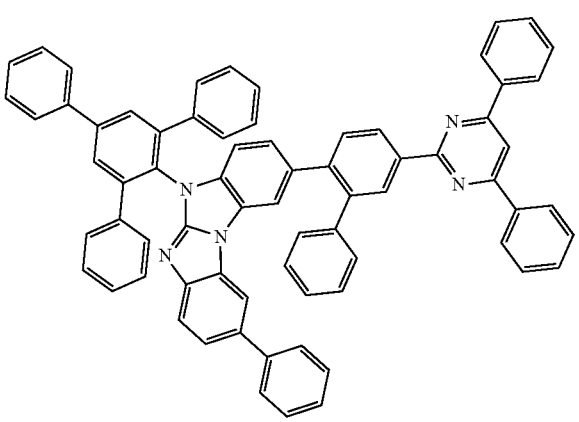
44
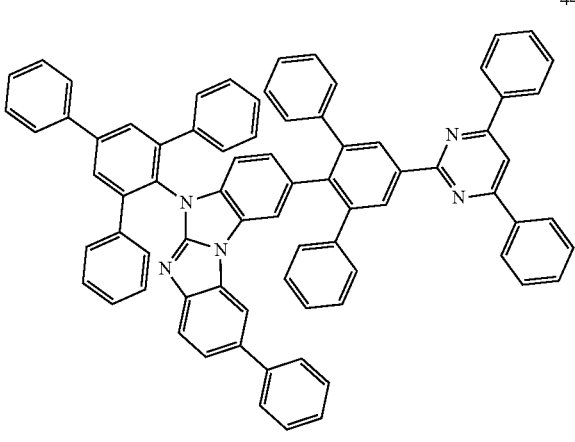
45
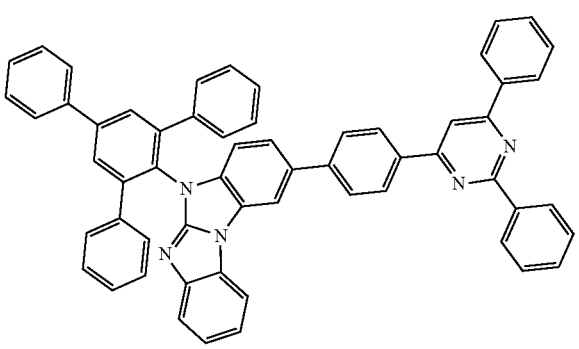

46
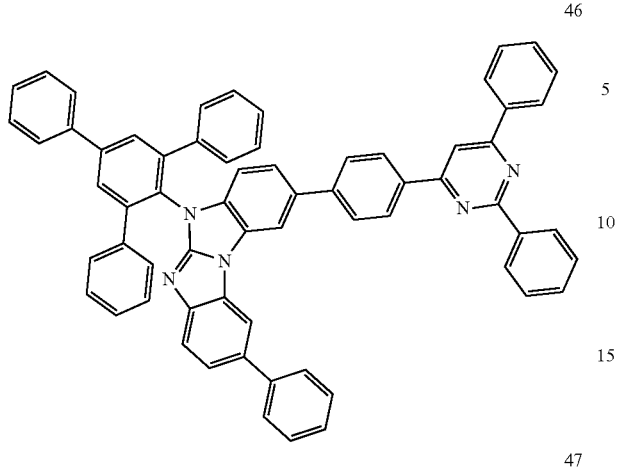
47
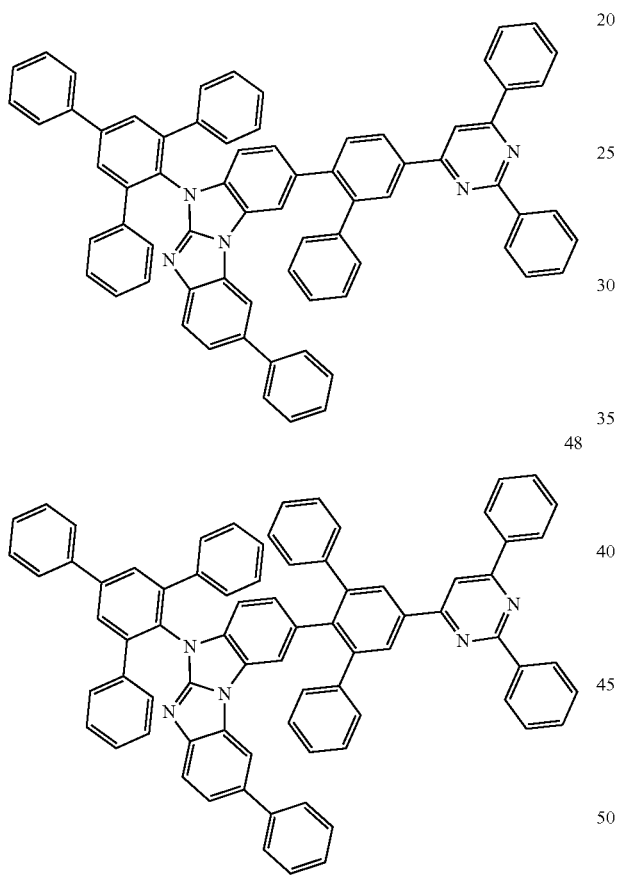
48
49
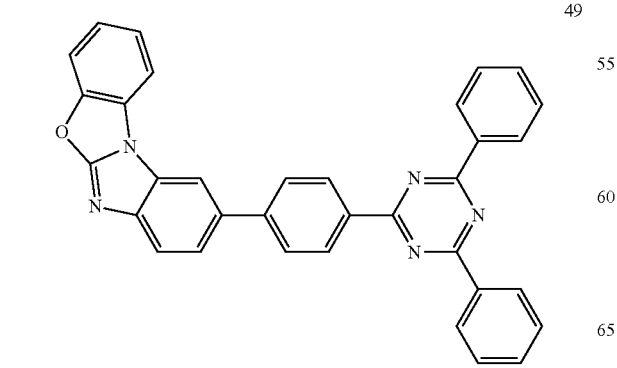
50
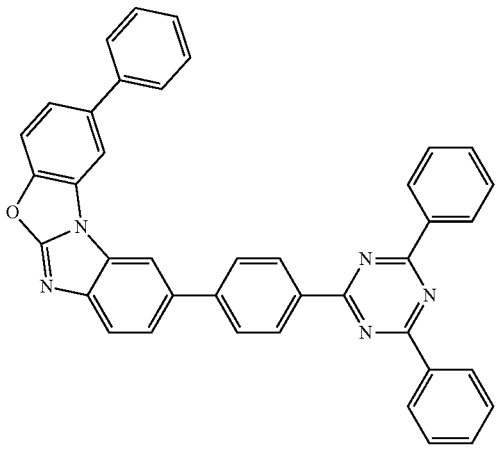
51
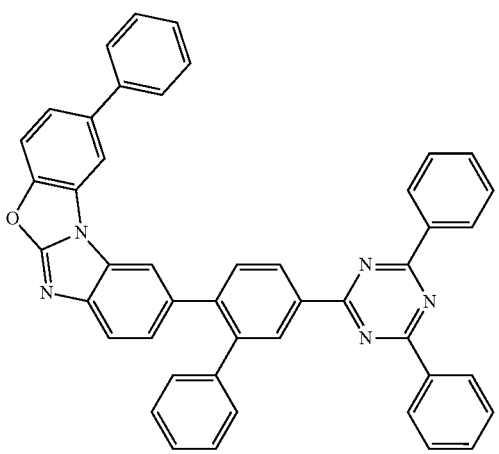
52
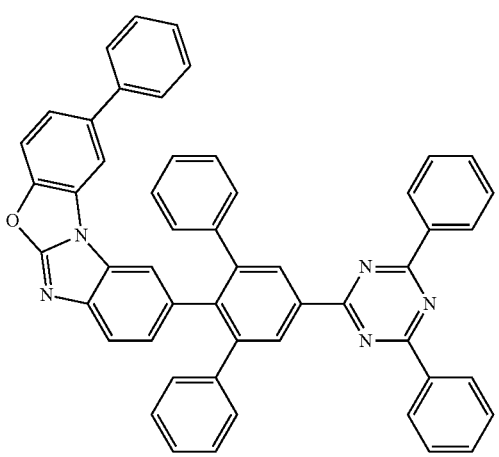

53
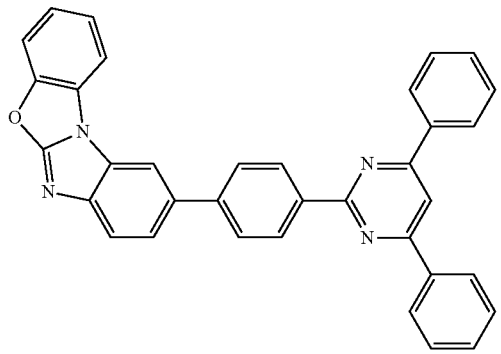
54
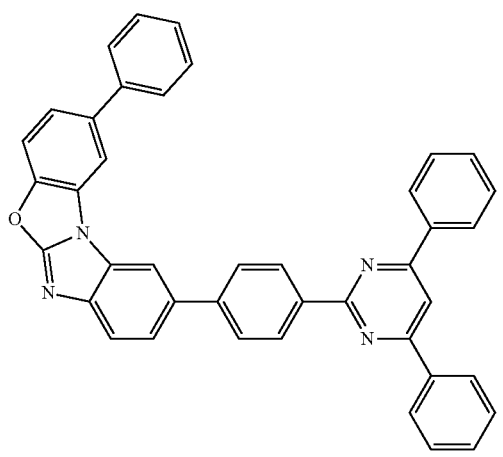
55
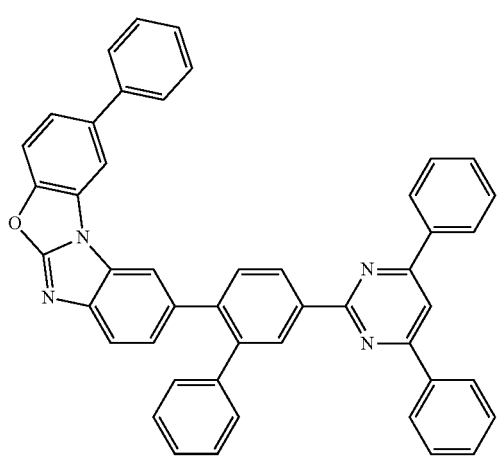
56
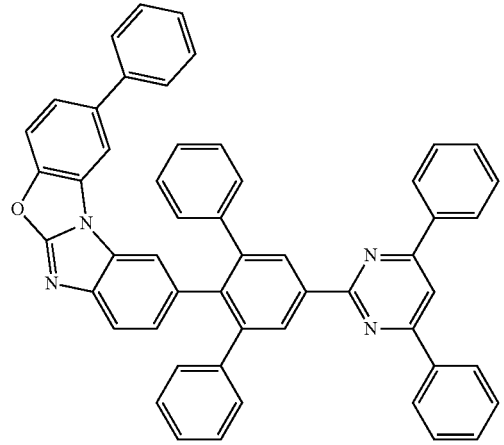
57
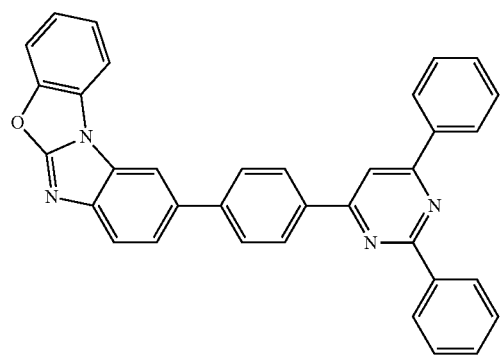
58
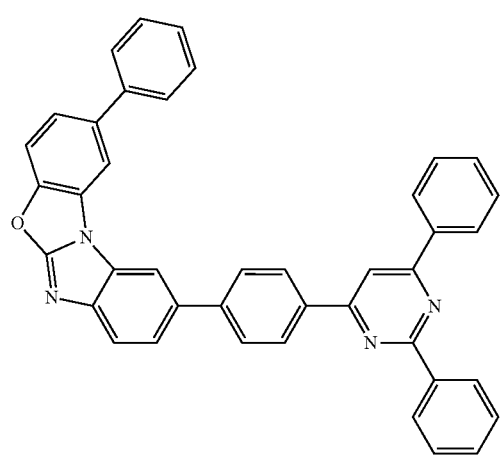

873
-continued
59
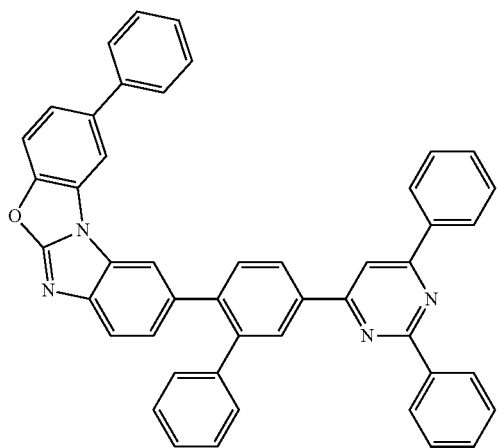
60
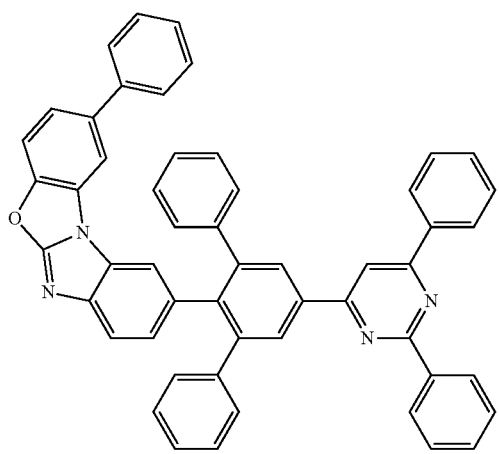
61
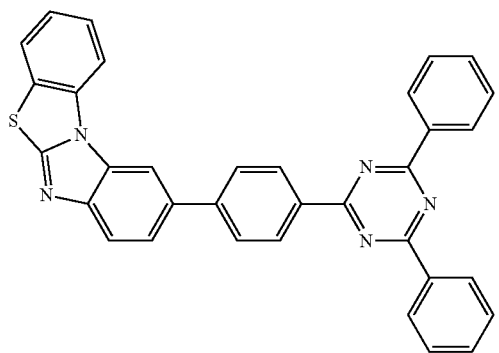
874
-continued
62
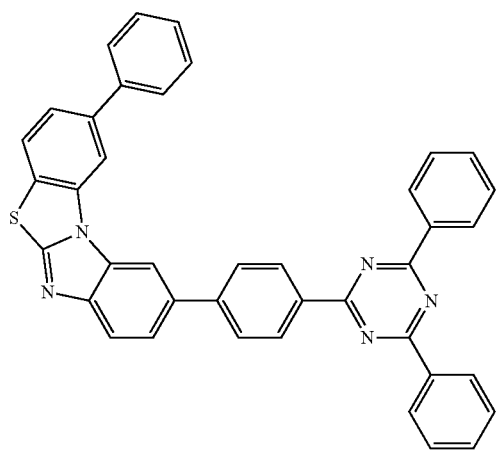
63
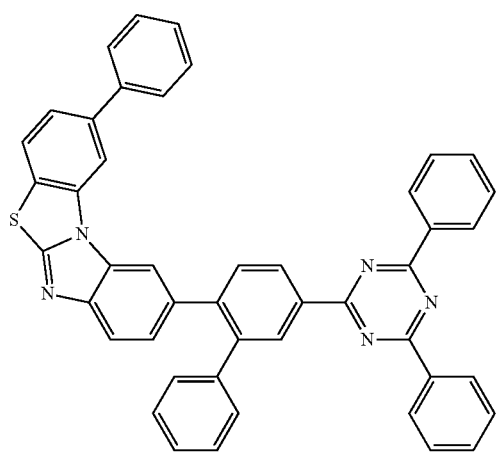
64
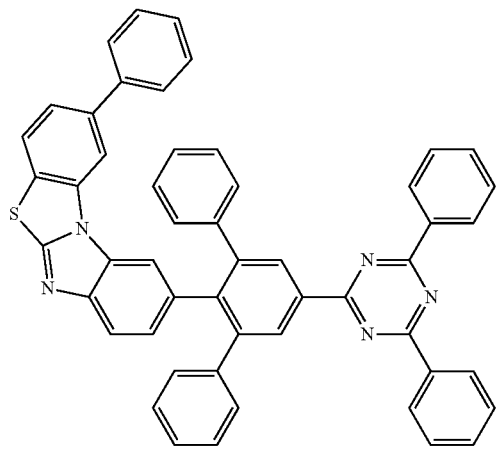

875
-continued
65
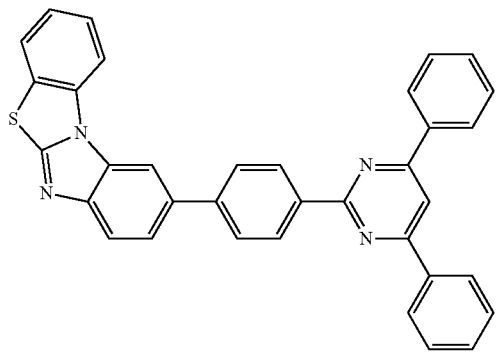
66
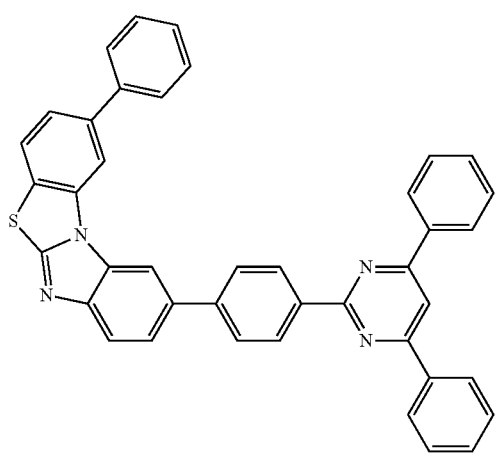
67
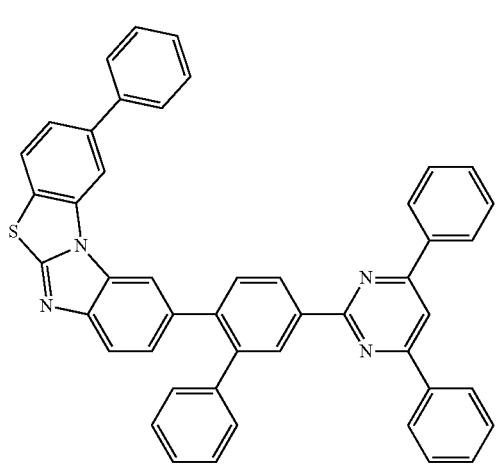
876
-continued
68
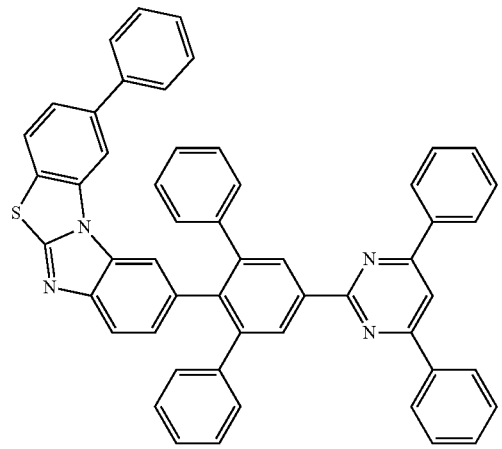
69
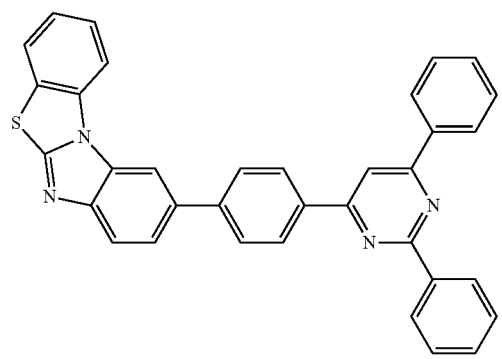
70
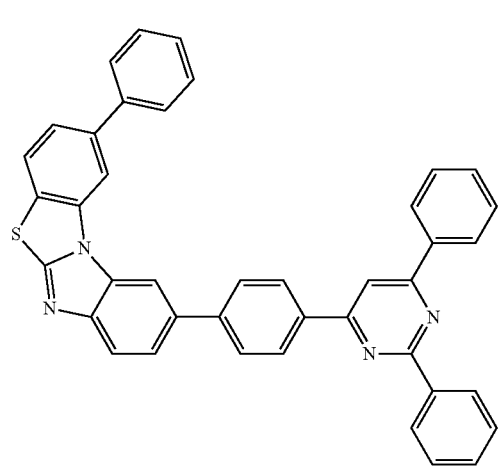

877
71
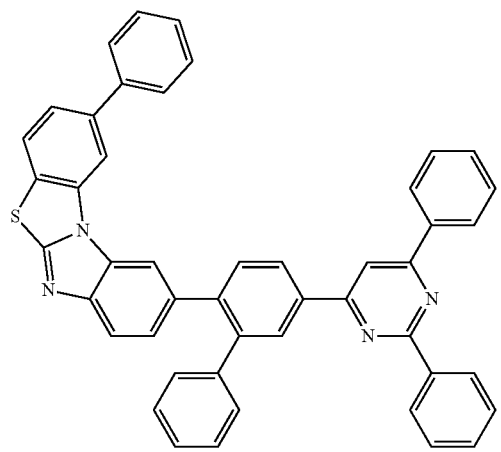
72
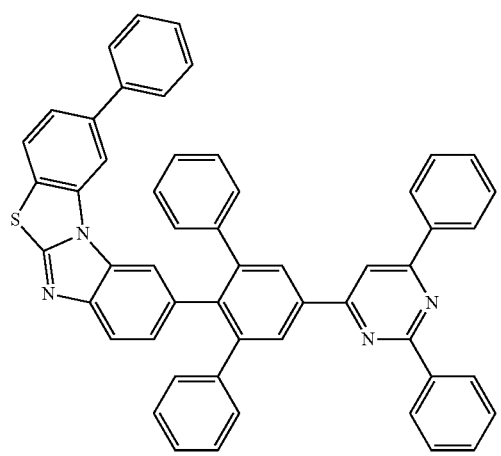
73
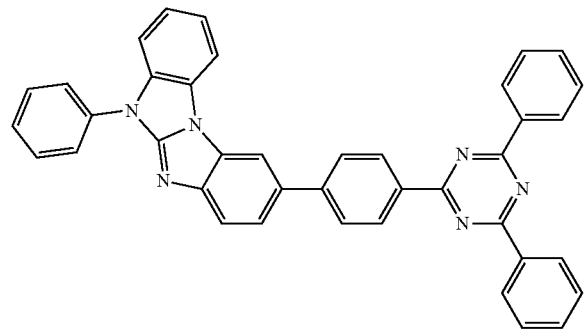
878
74
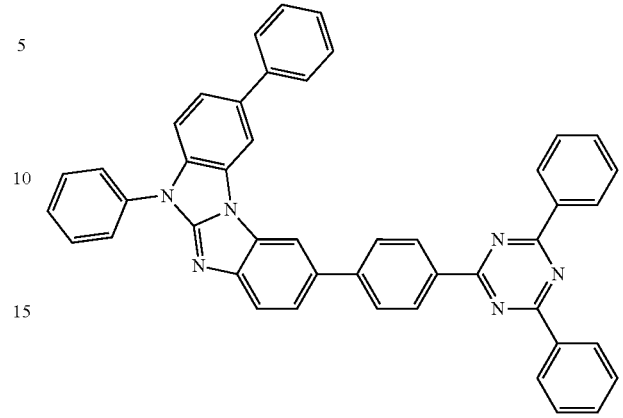
75
76
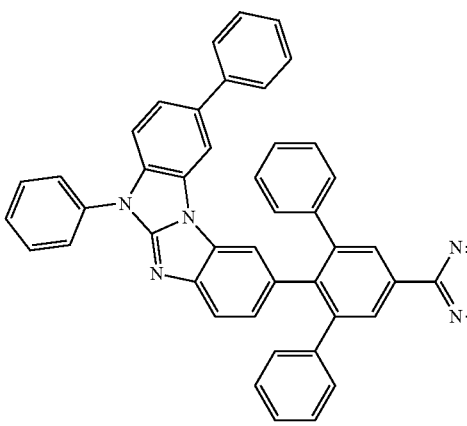

879
-continued
77
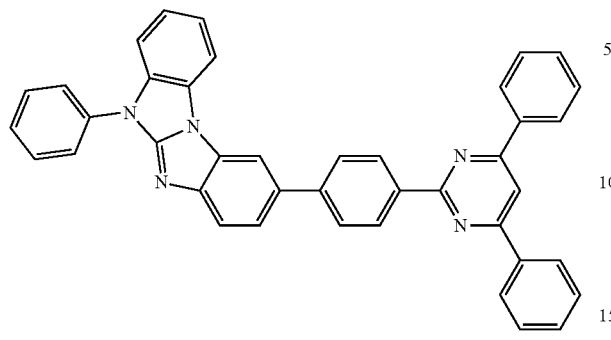
78

79
880
-continued
80
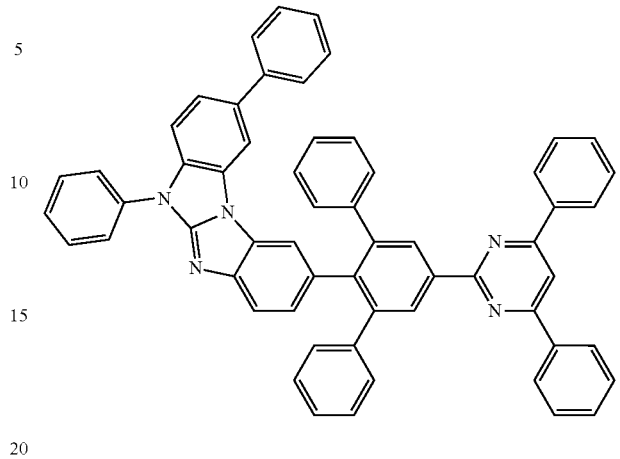
81
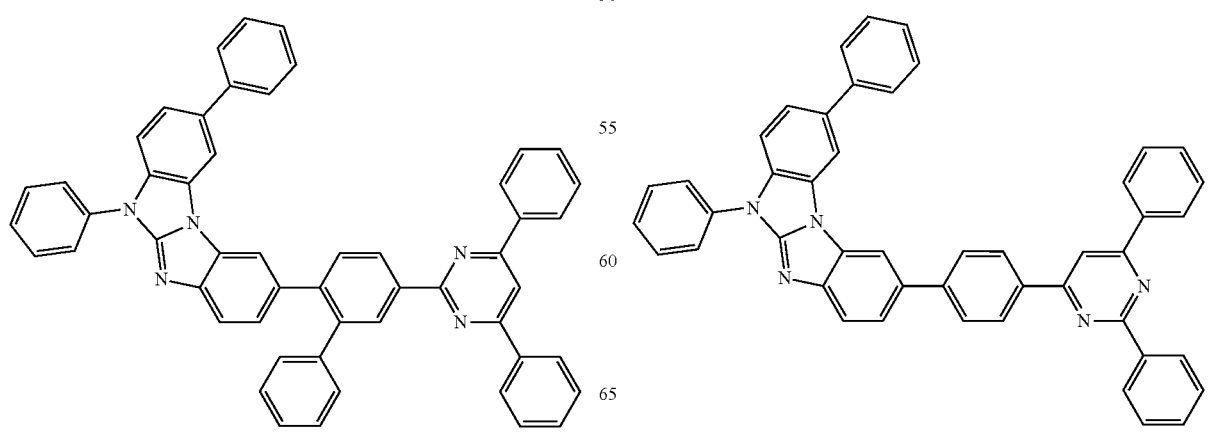
82

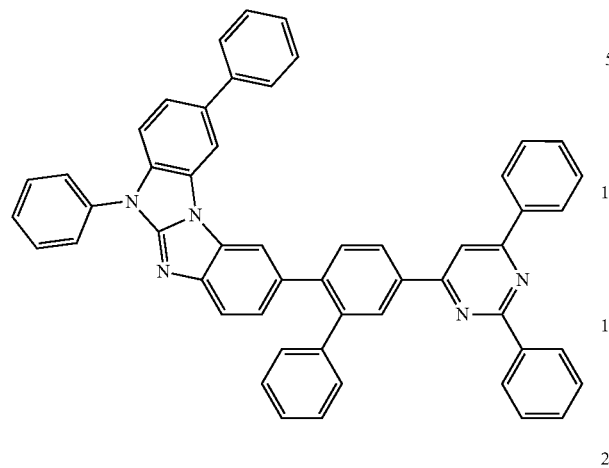
83
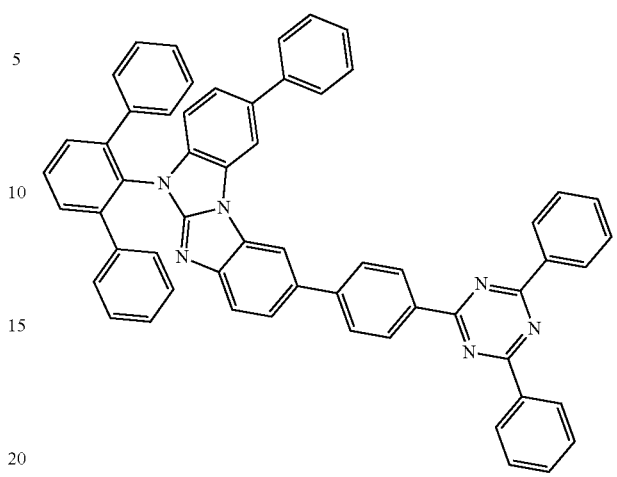
86
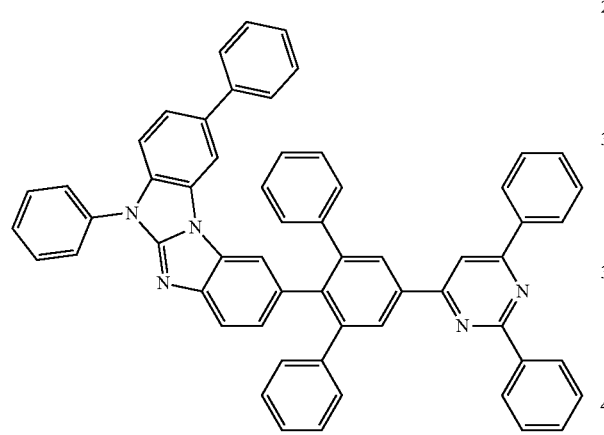
84
87
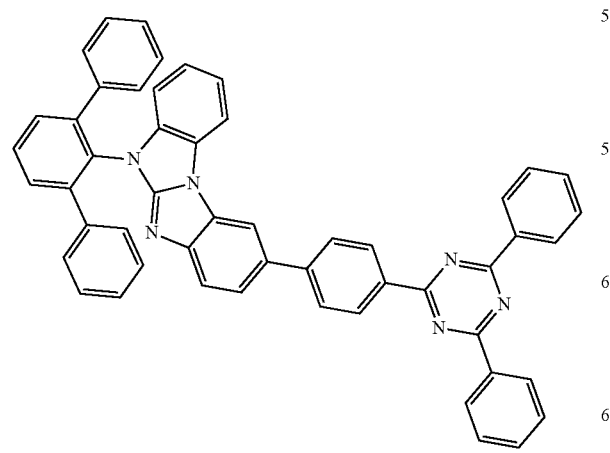
85
88

89
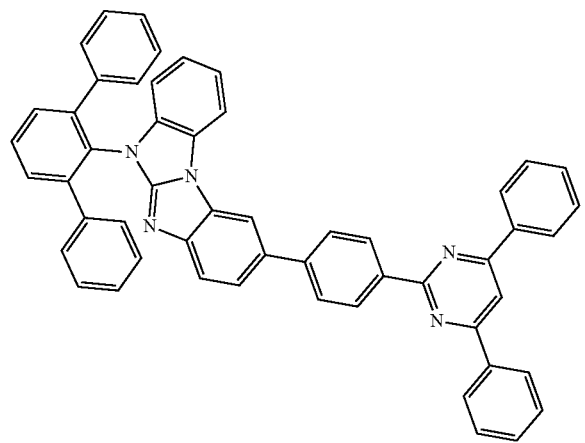
90
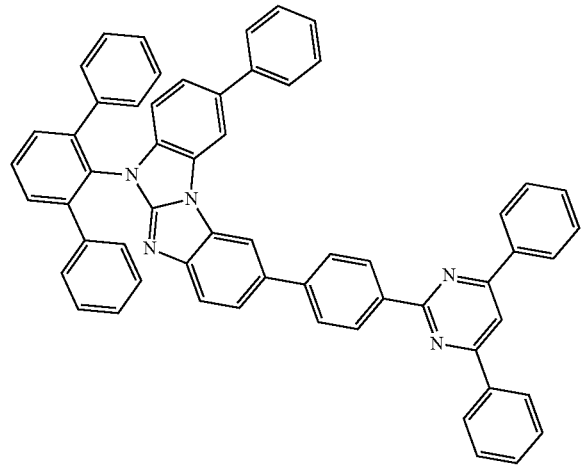
91
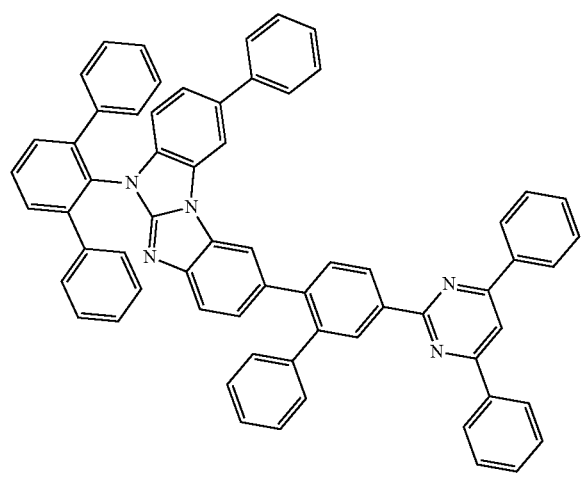
92
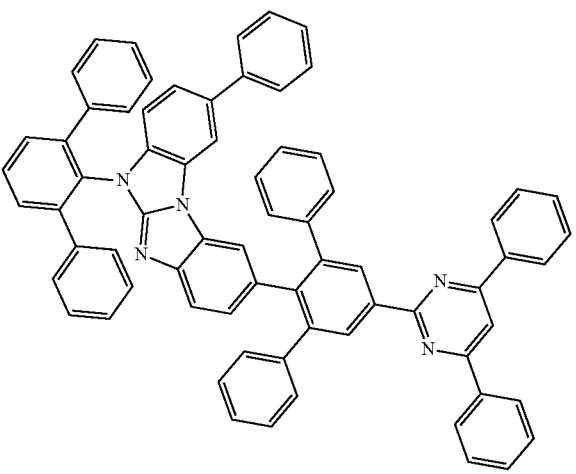
93
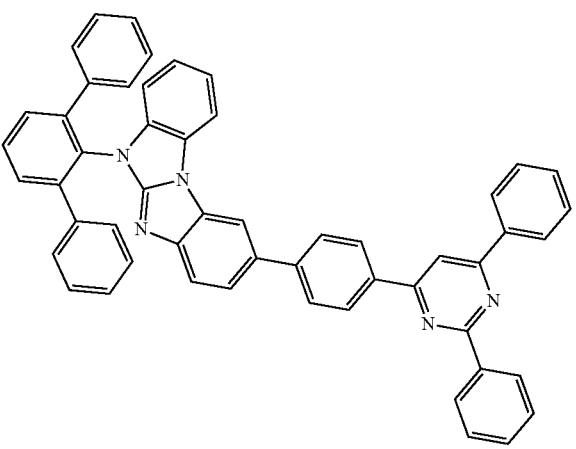
94
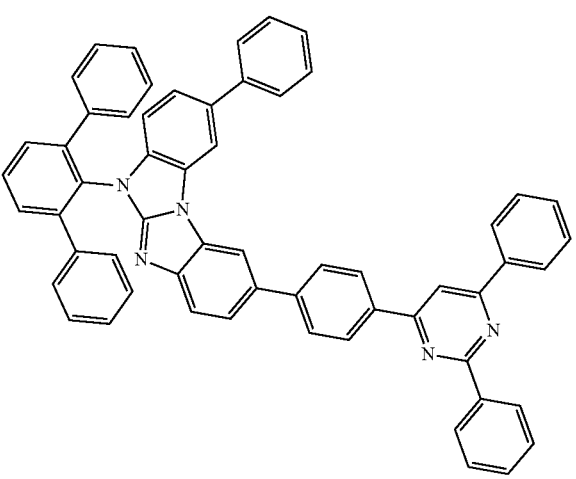

885
-continued
95
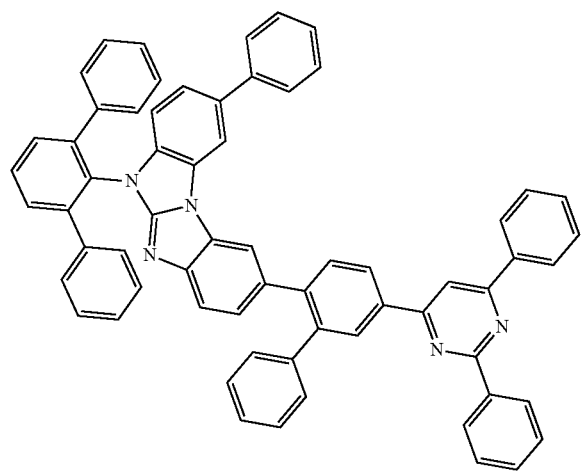
96
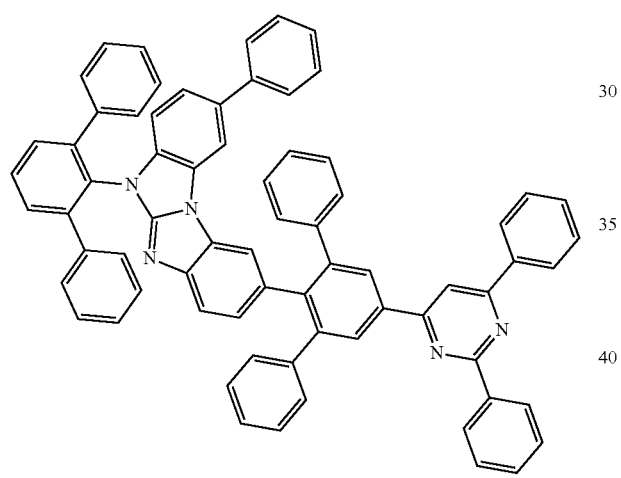
97
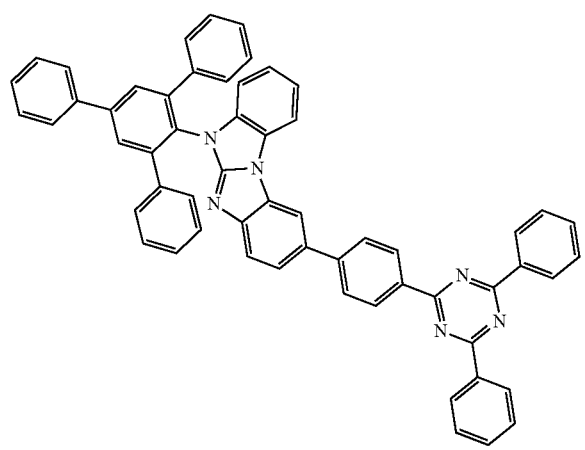
886
-continued
98
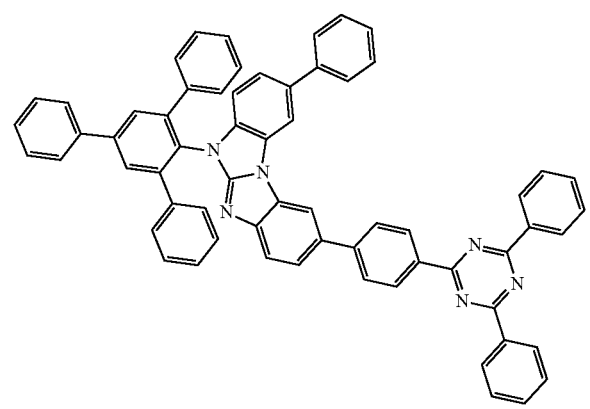
99
100
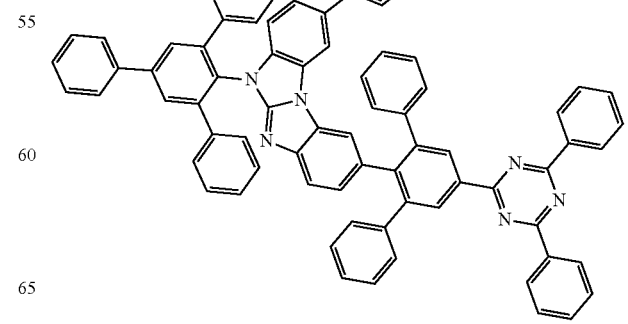

101
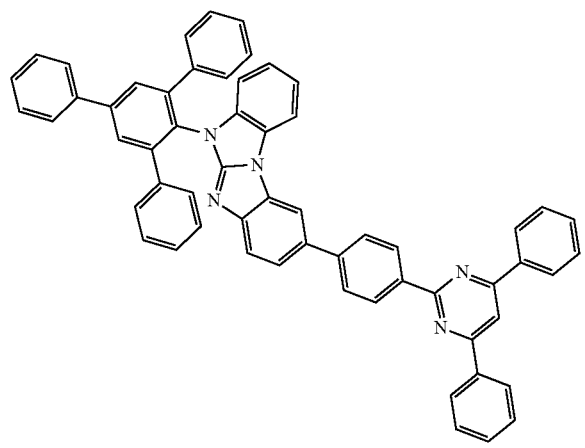
102
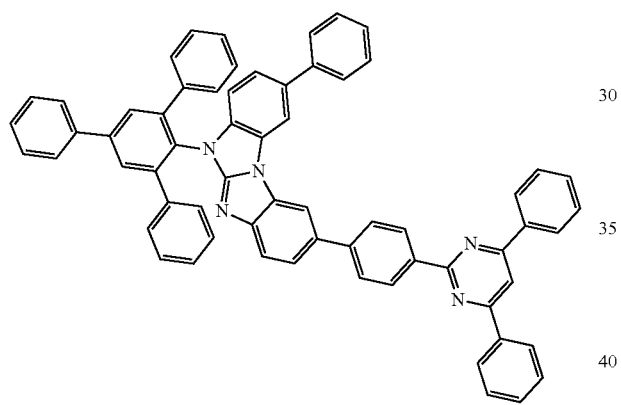
103
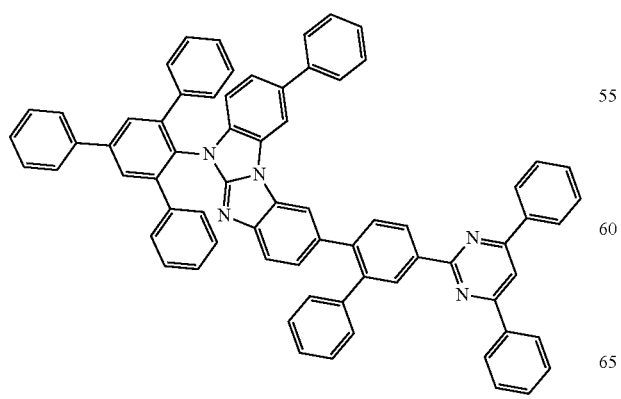
104
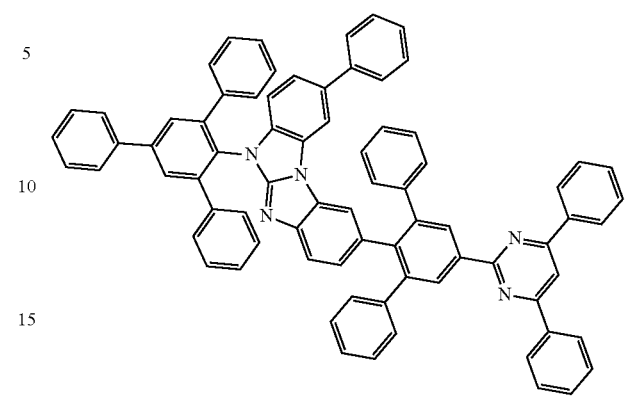
105
106

107
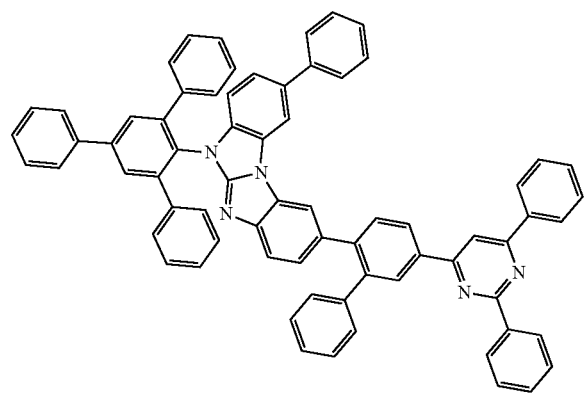
108
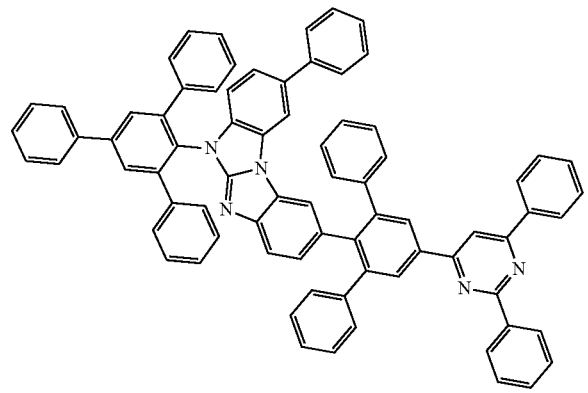
109
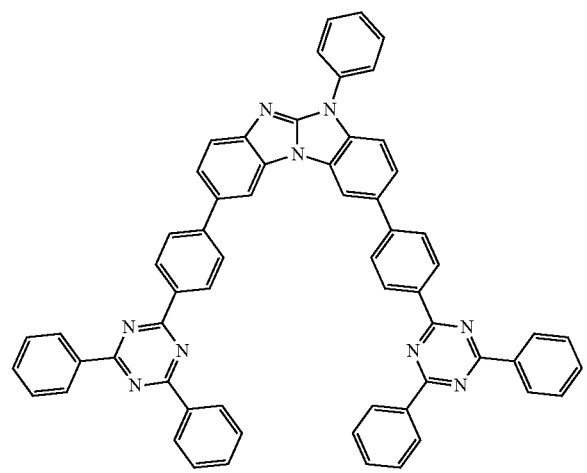
110
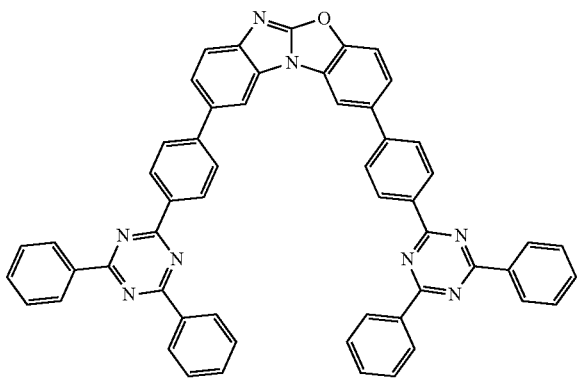

891
-continued
113
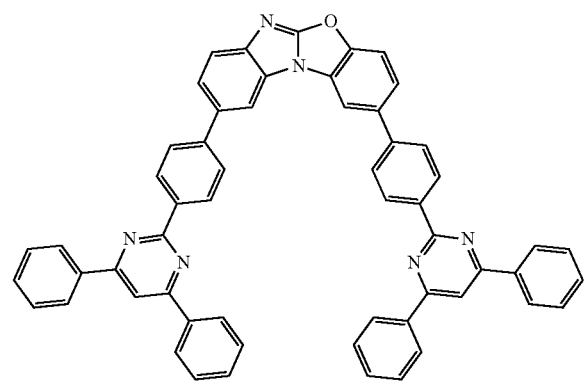
114
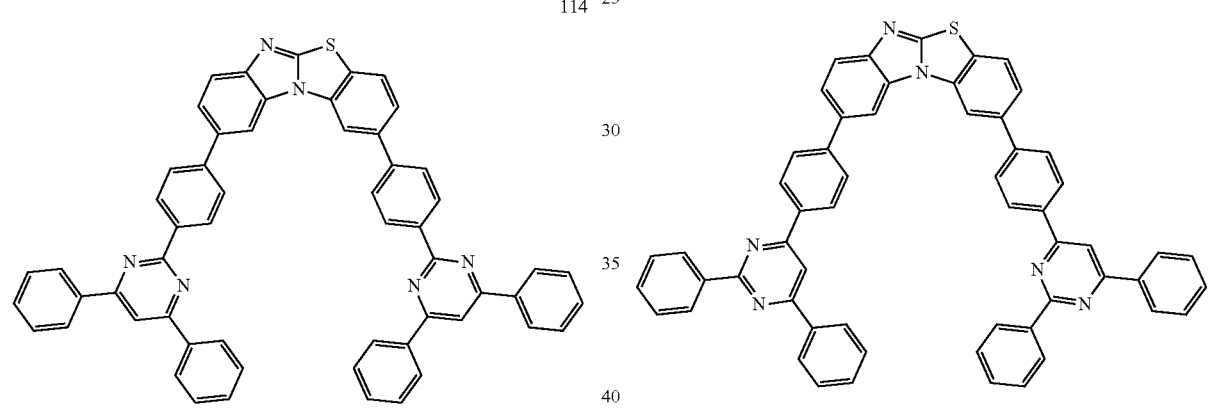
115
892
-continued
116
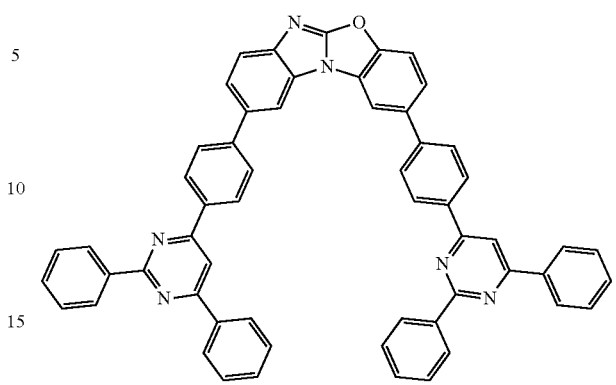
117
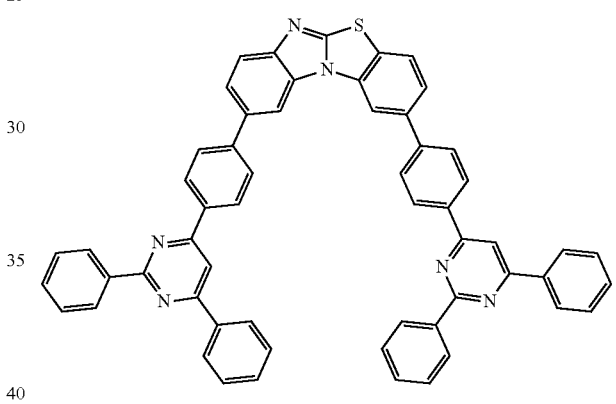
<Group VIII>
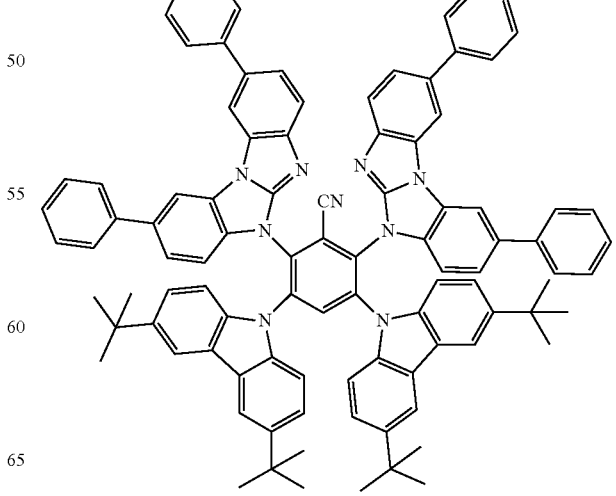

893
-continued
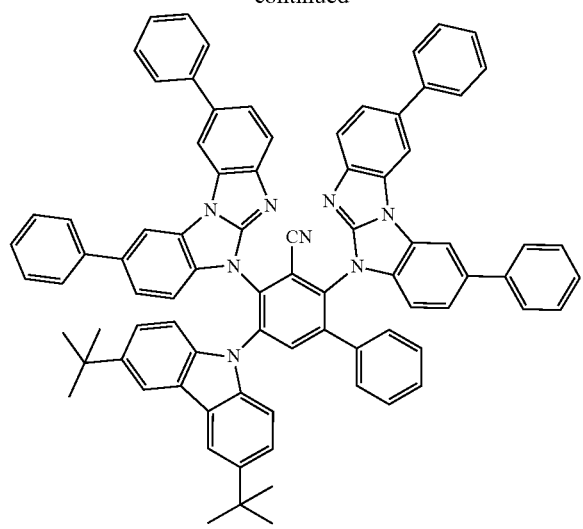
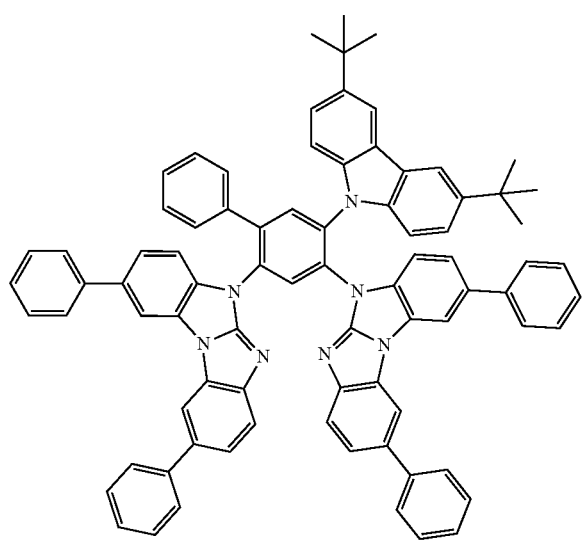
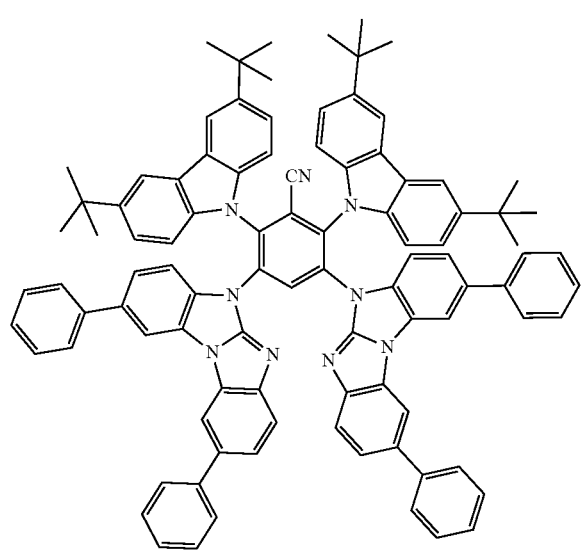
894
-continued
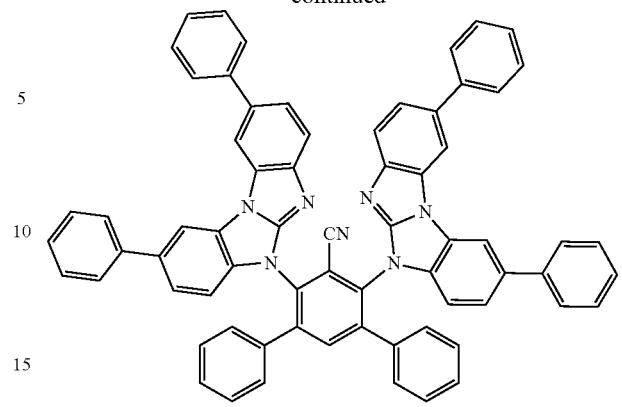
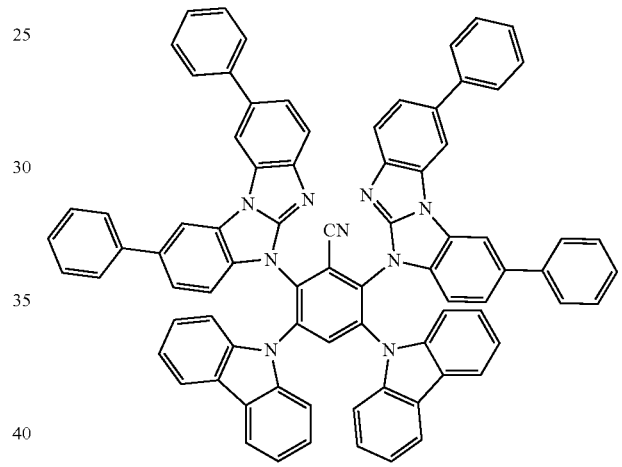
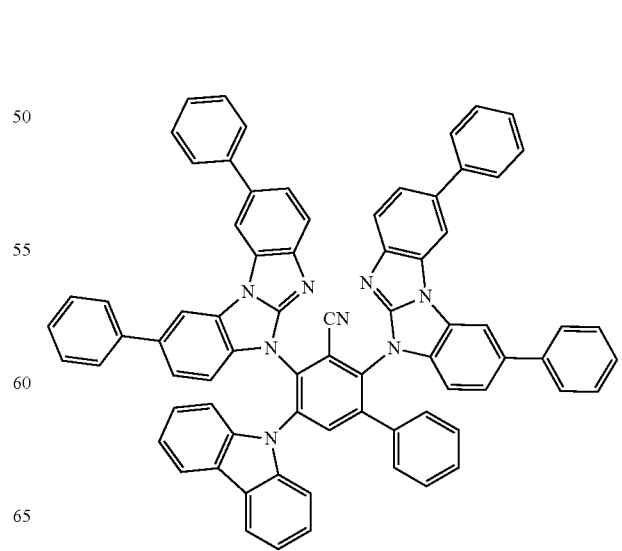

895
-continued
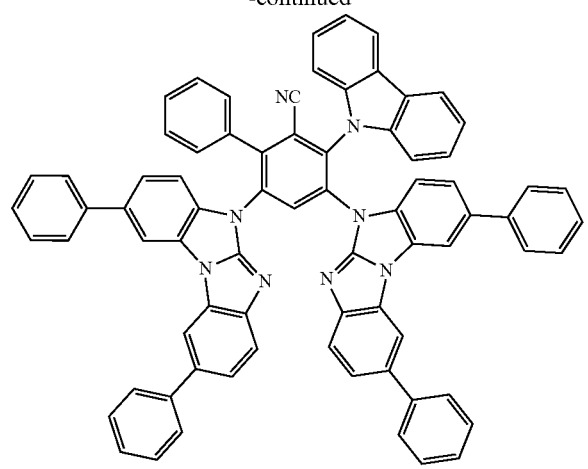
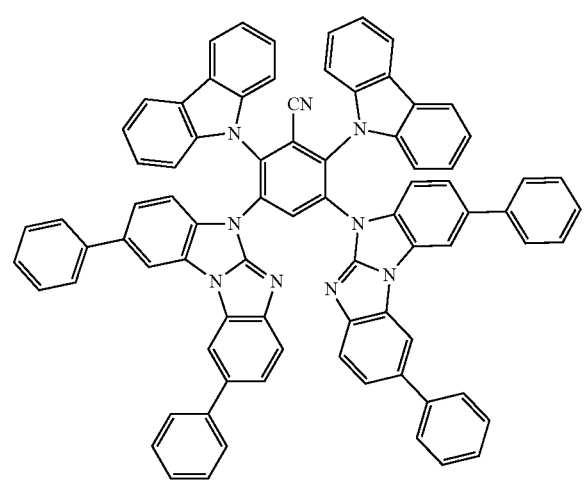
896
-continued
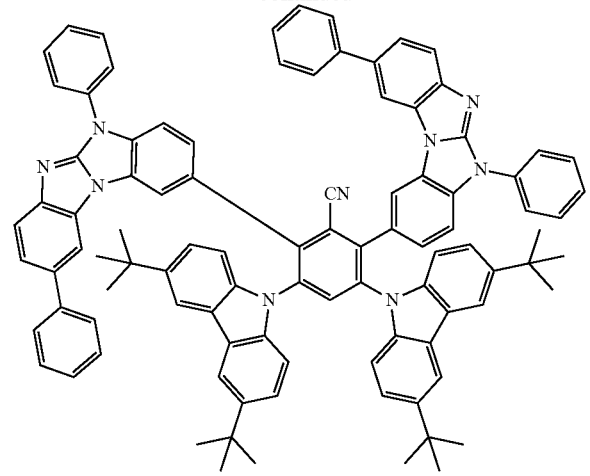
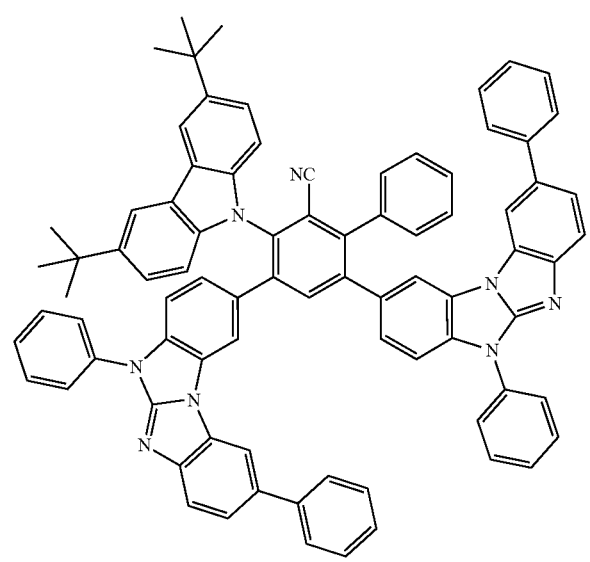

897
-continued
898
-continued
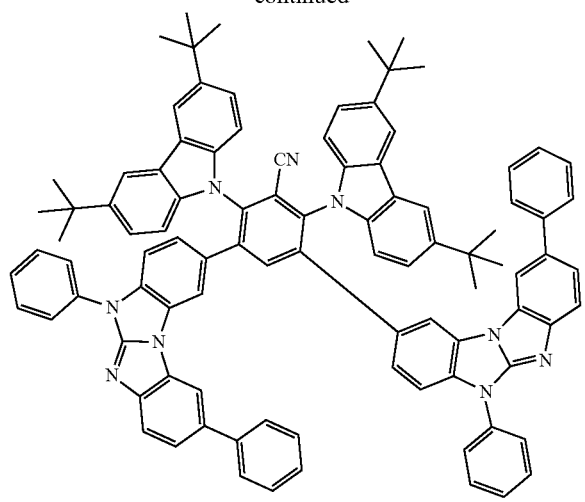
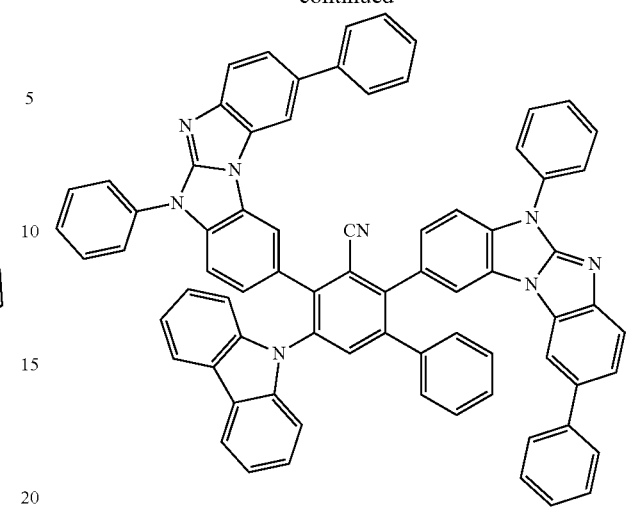
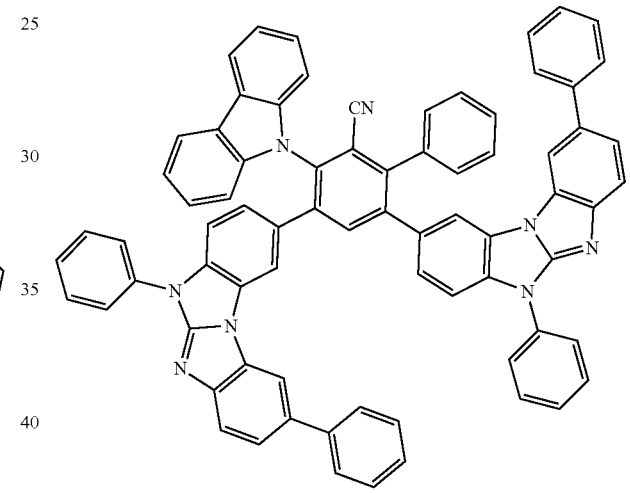
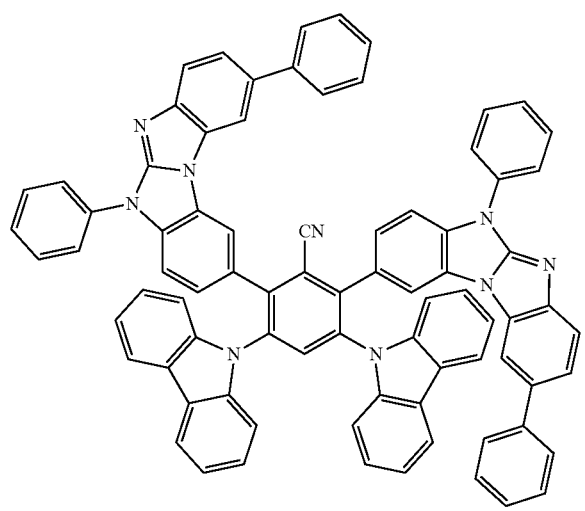
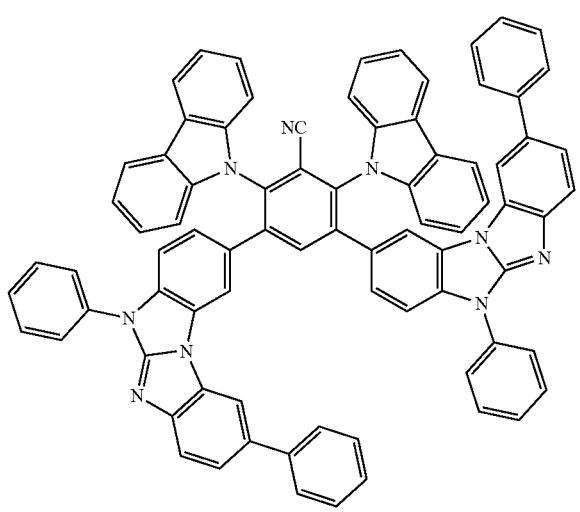

899
-continued
900
-continued
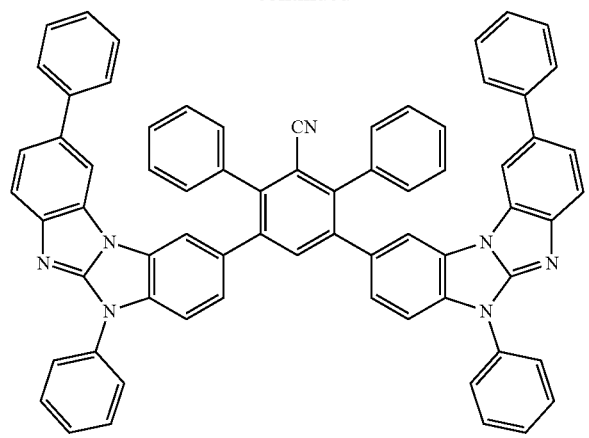
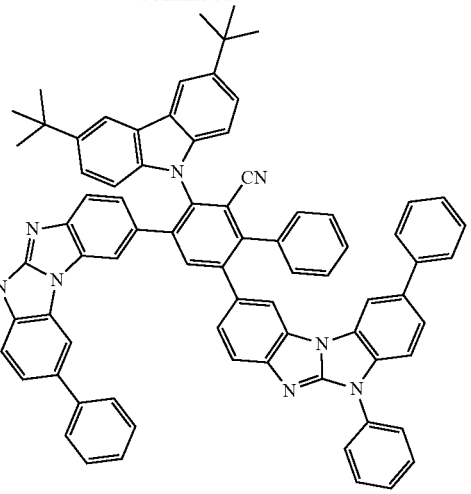
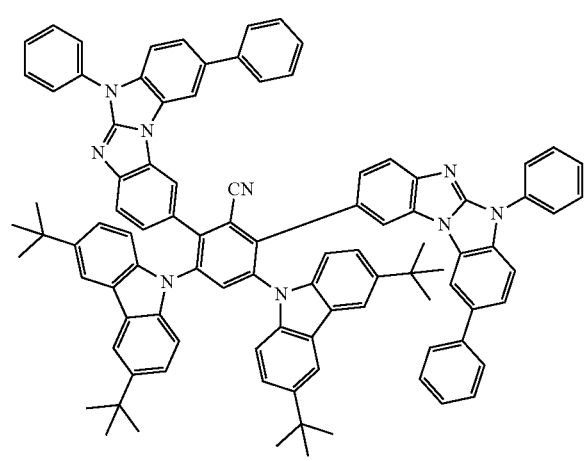
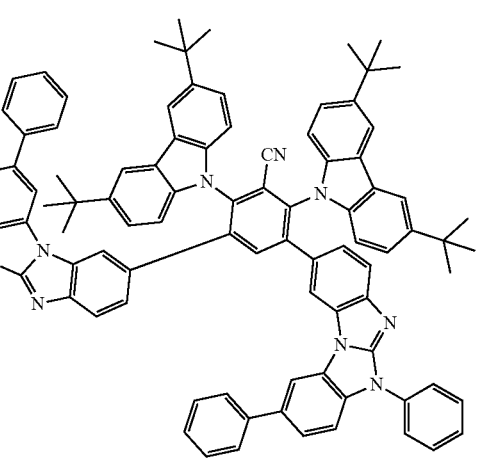
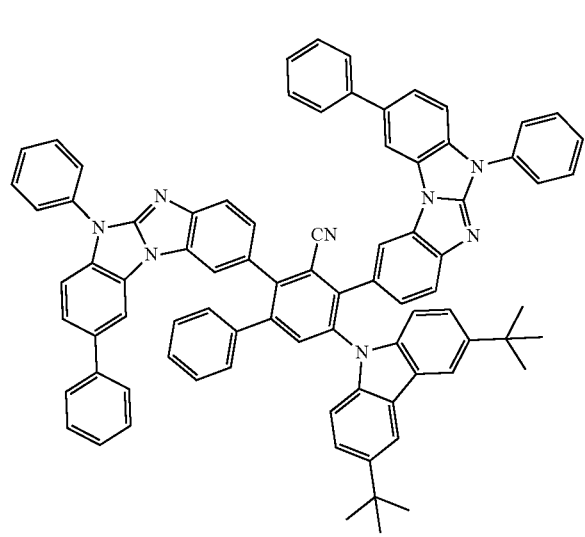
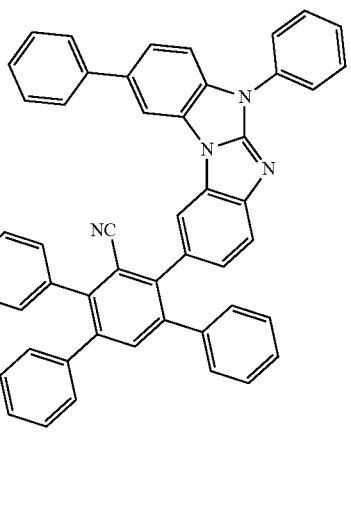

901
-continued
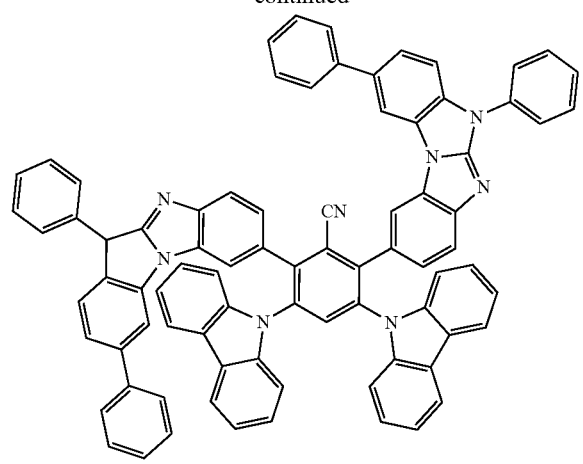
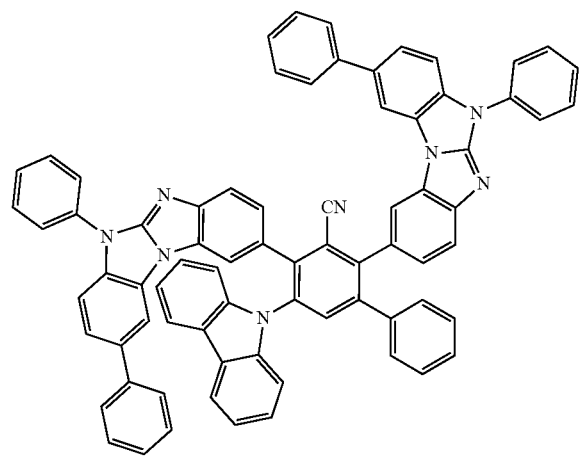
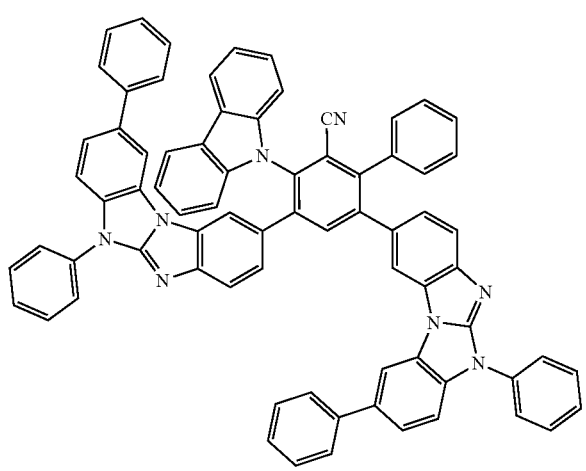
902
-continued
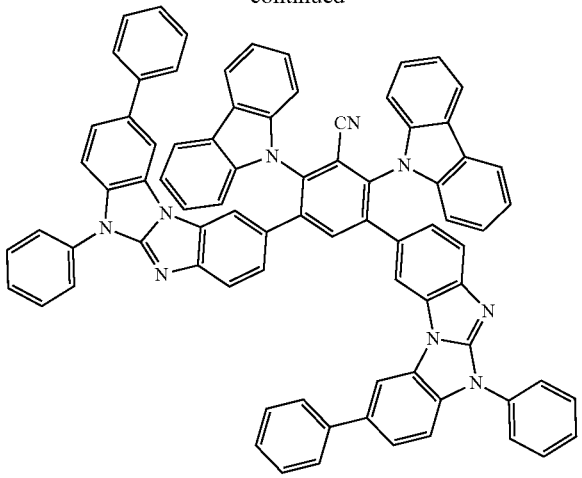
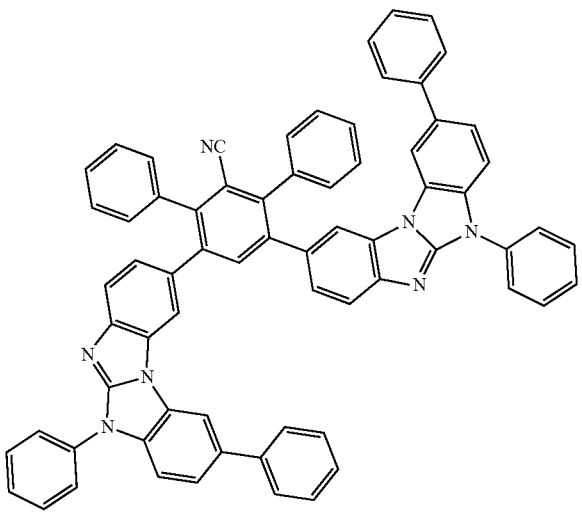
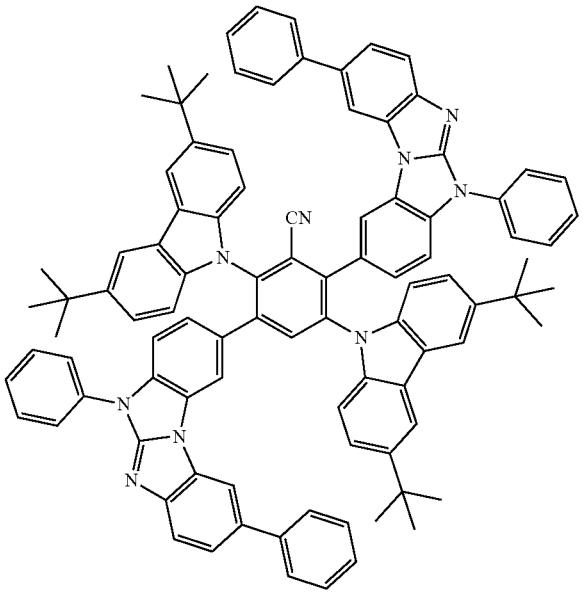

903
-continued
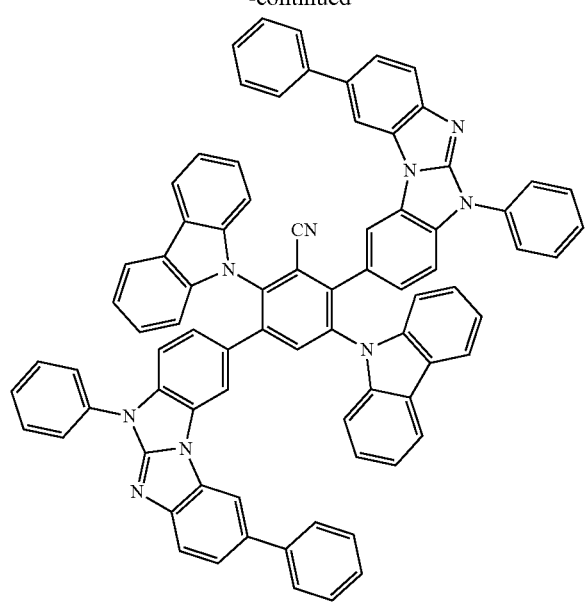
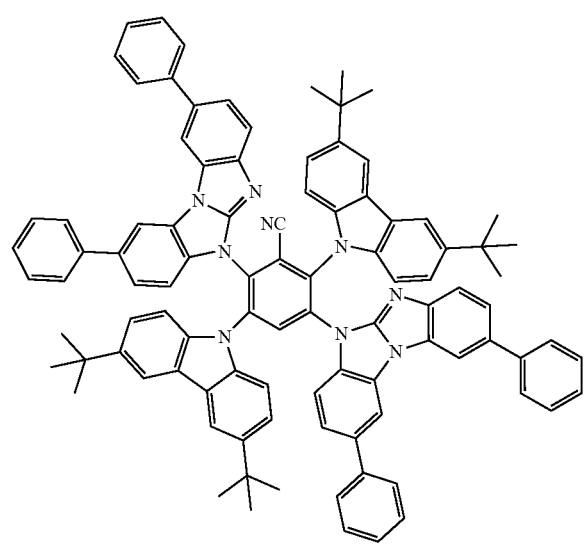
904
-continued
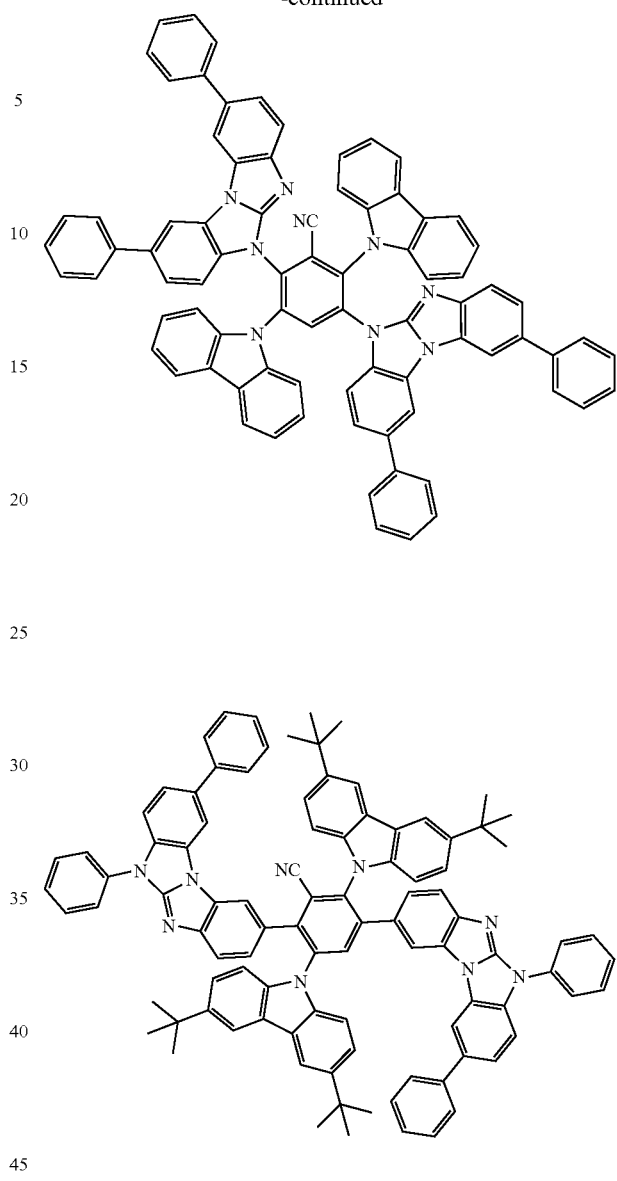
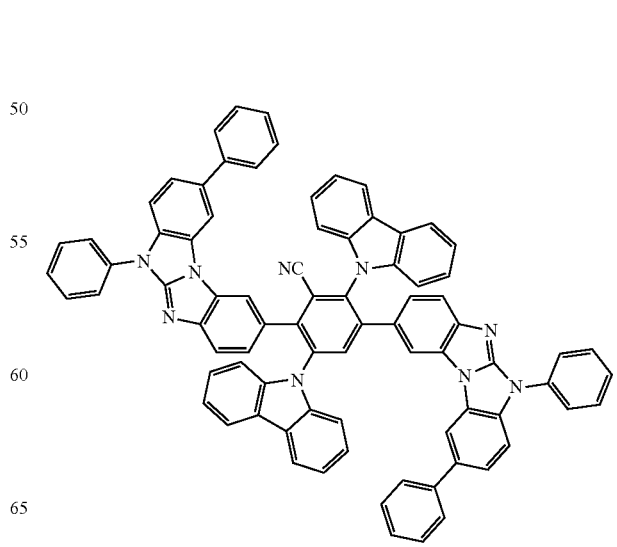

905
-continued
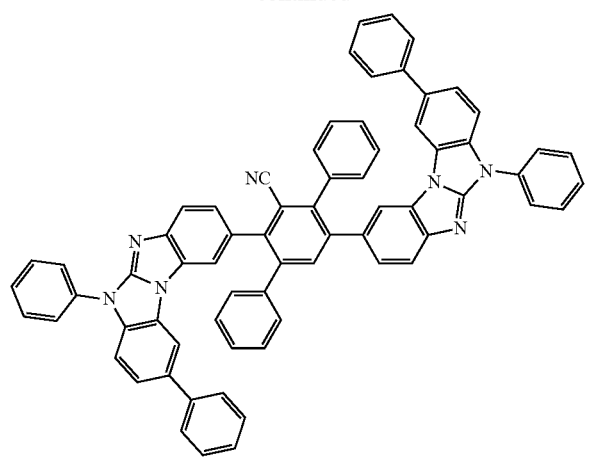
906
-continued
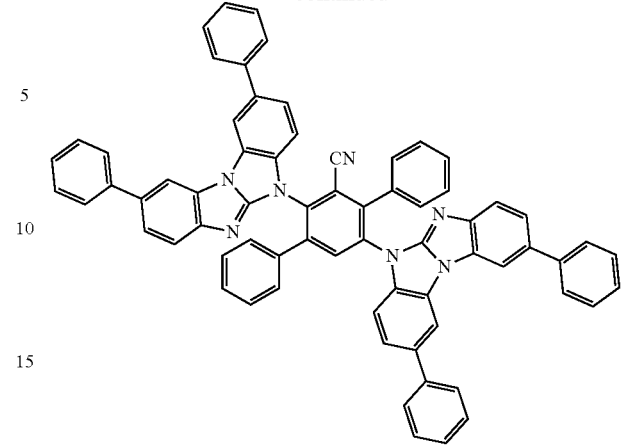
<Group IX>
1
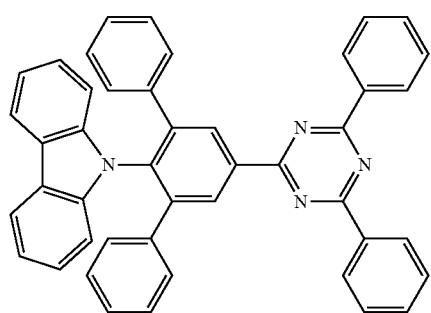
2
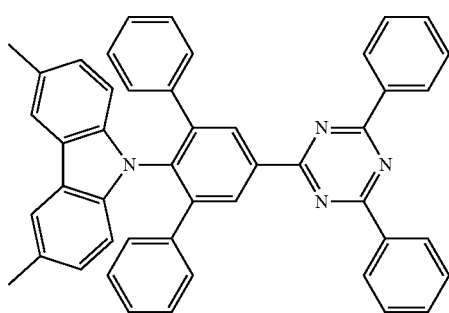
3
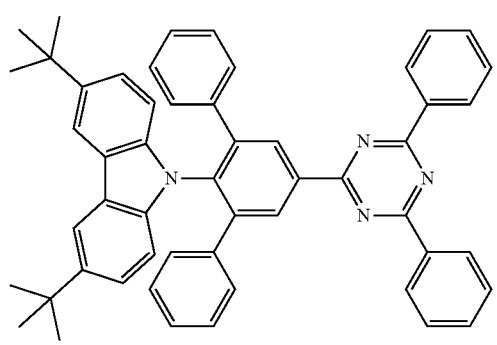
4
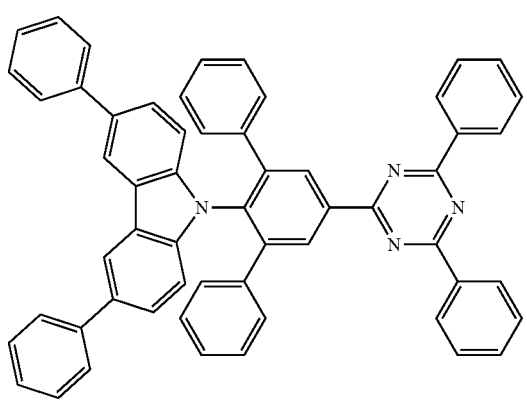

-continued
907
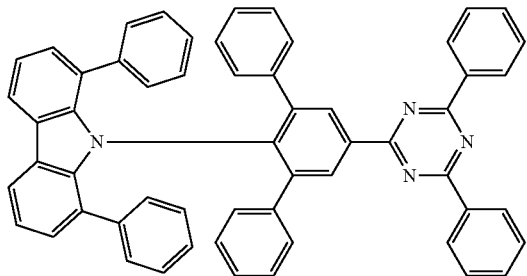
5
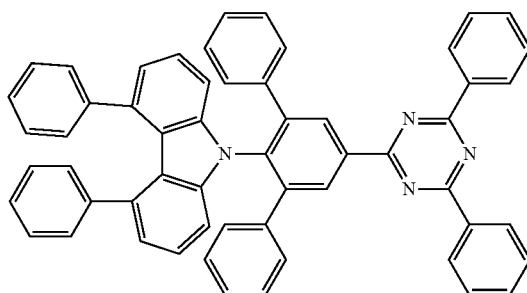
7
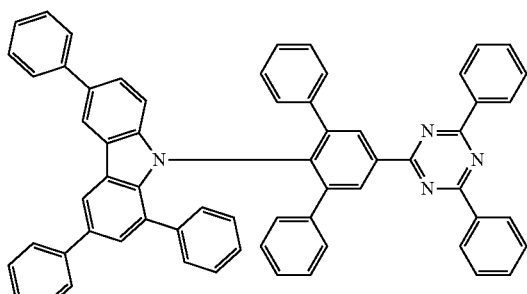
9
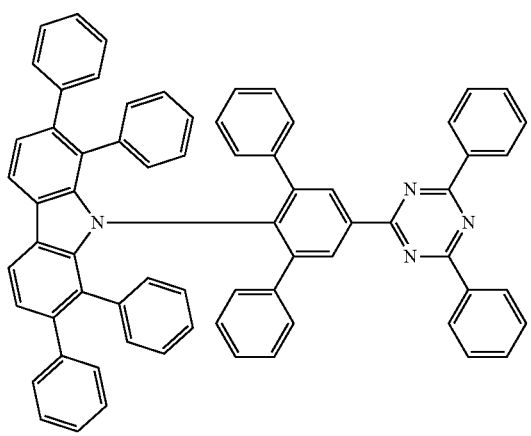
11
908
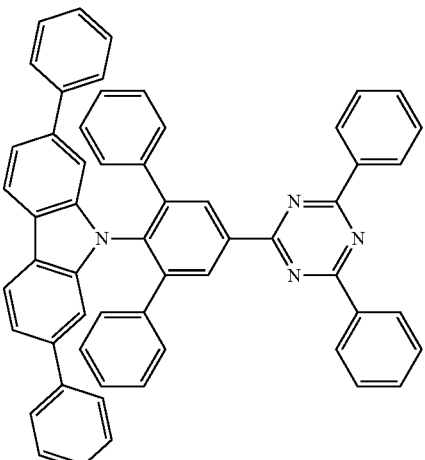
6
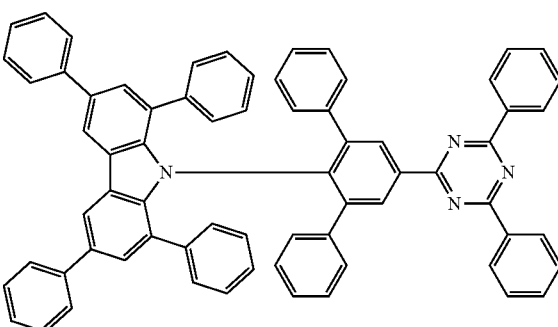
8
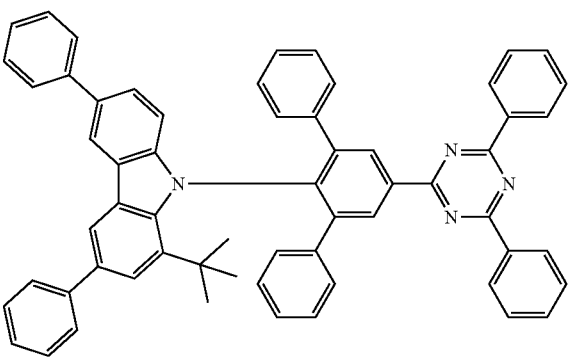
10
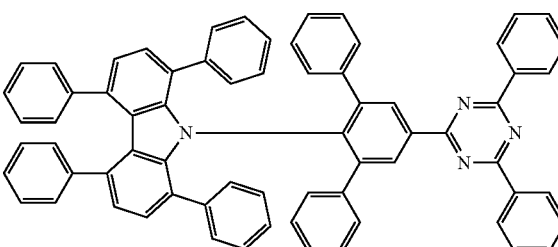
12

-continued
13
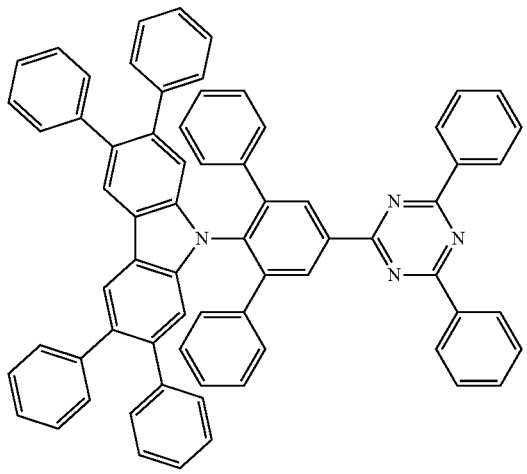
14
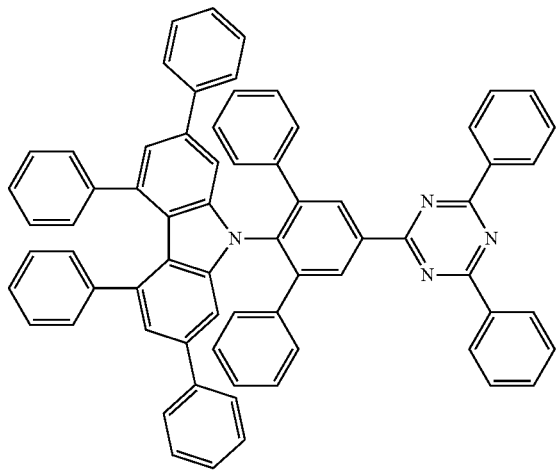
15
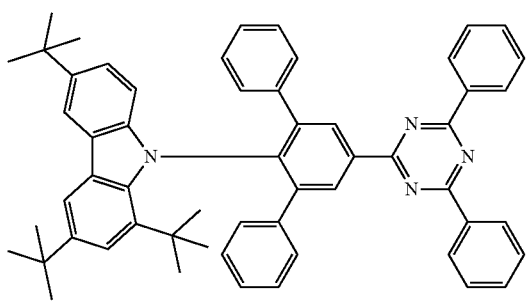
16
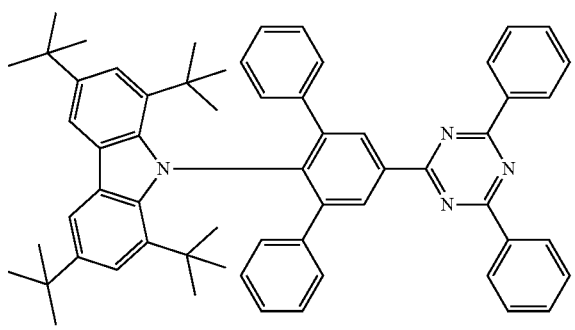
17
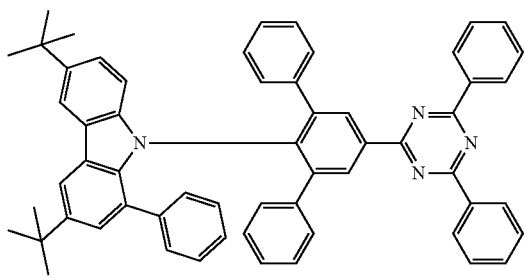
18
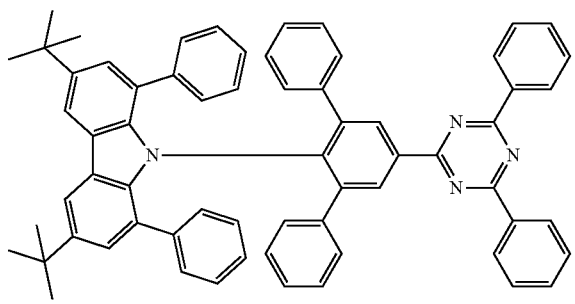
19
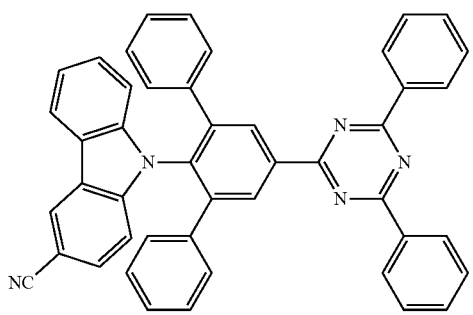
20
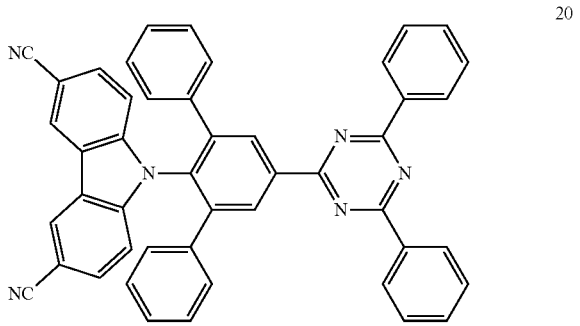

-continued
911 912
21
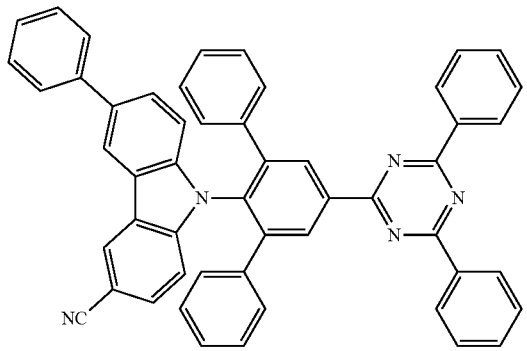
22
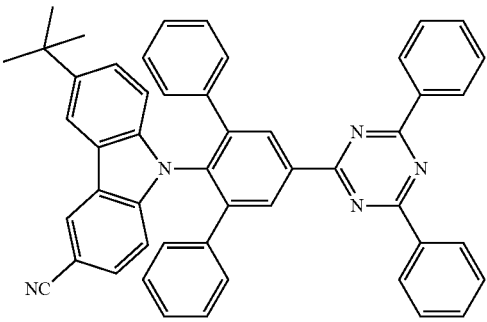
23
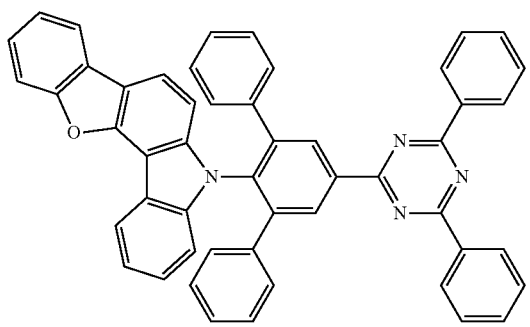
24
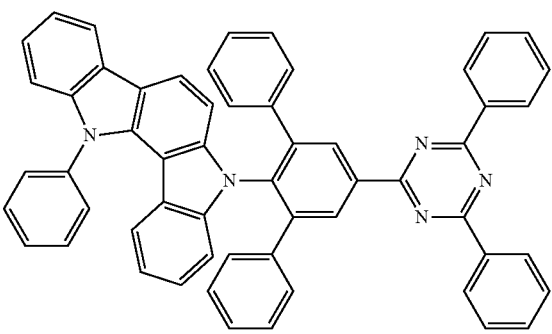
25
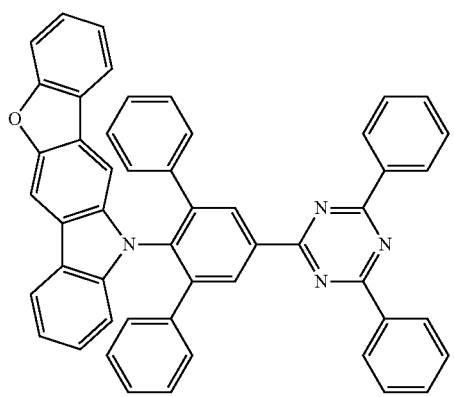
26
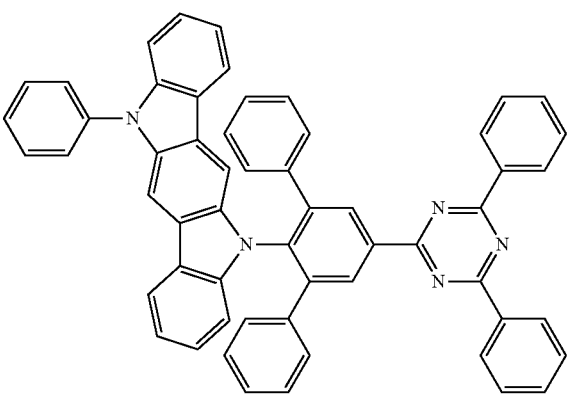
27
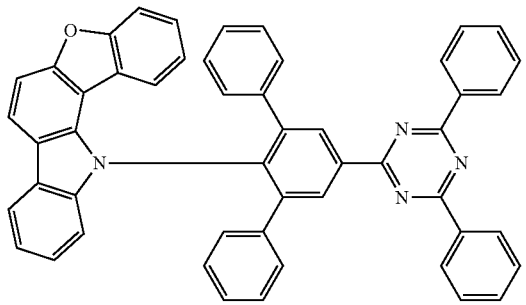
28
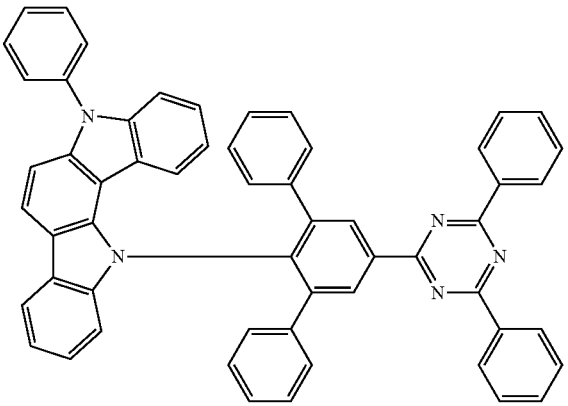

913 914
29
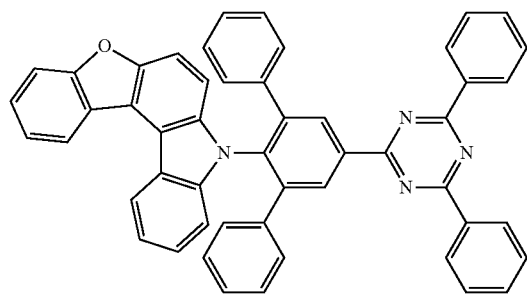
30
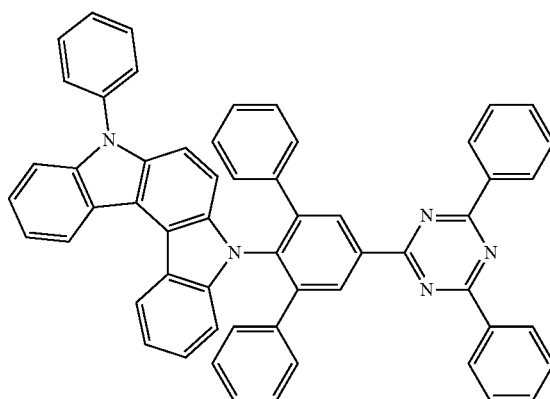
31
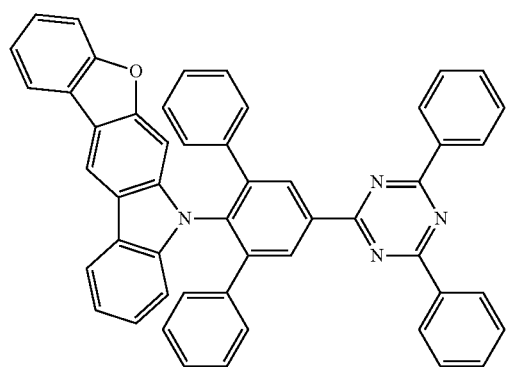
32
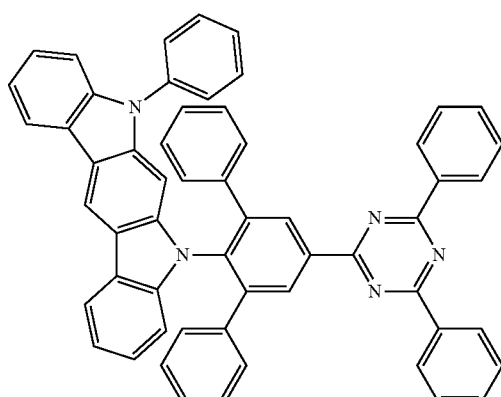
33
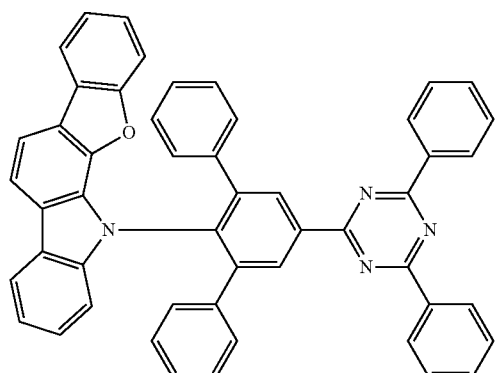
34
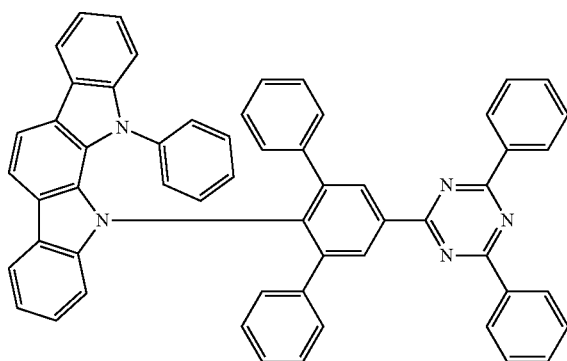
35
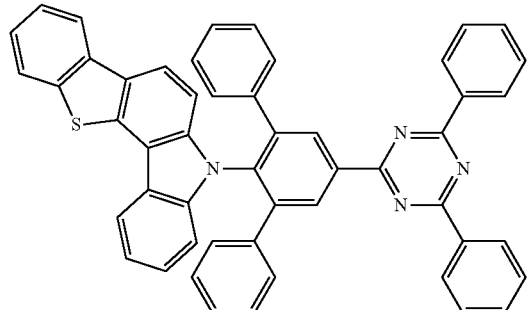
36
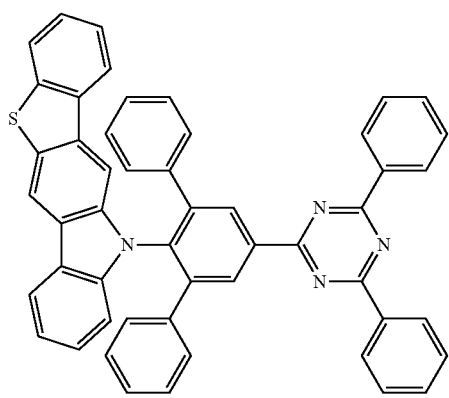

-continued
37
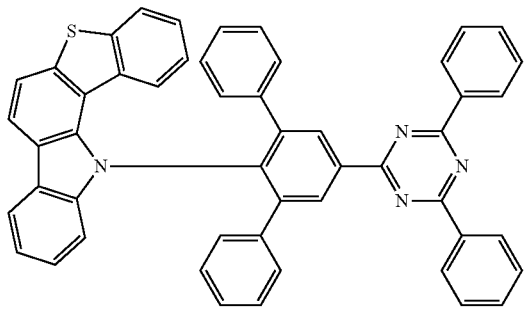
38
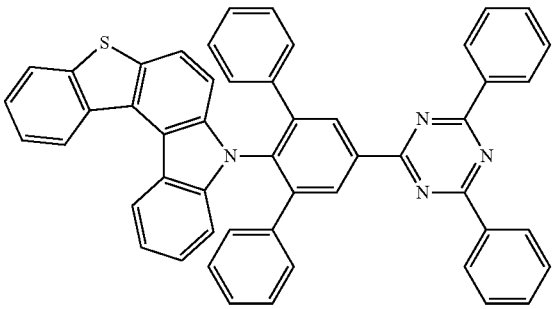
39
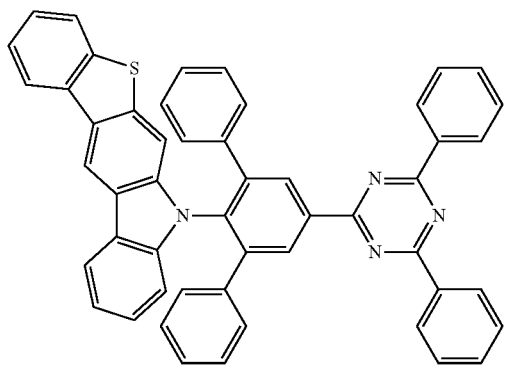
40
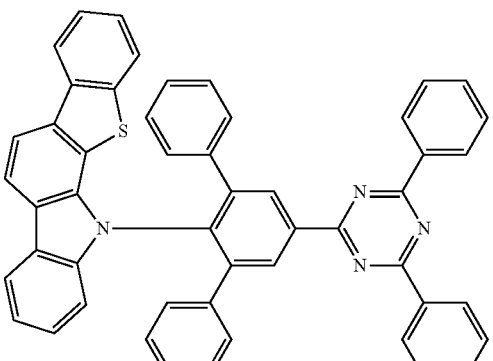
41
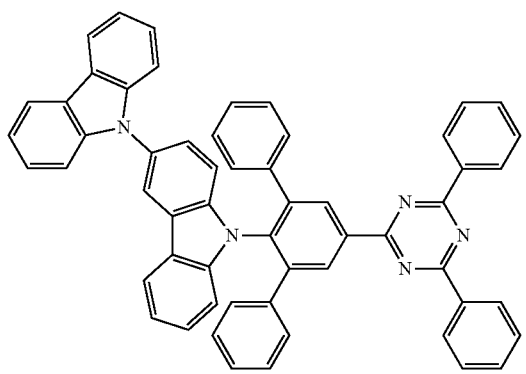
42
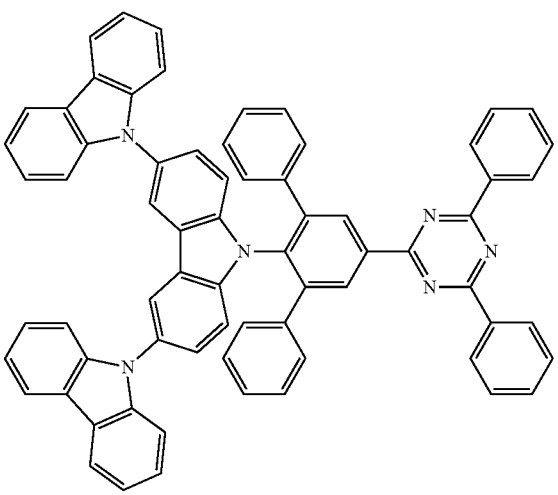
43
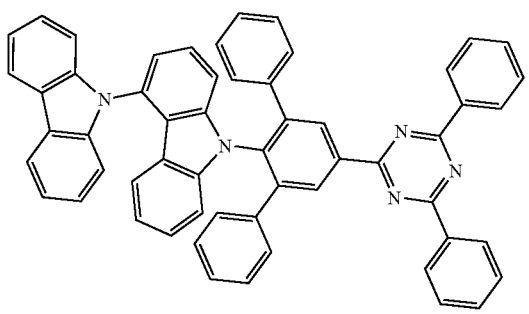
44
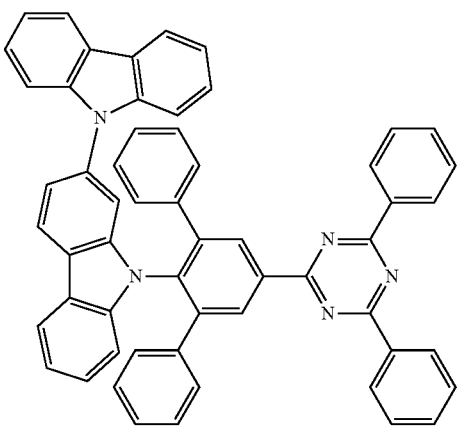

917 918
| | |
|---|---|
| 45 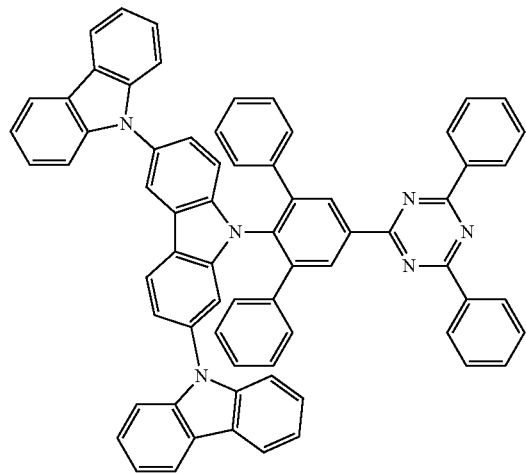 | 46 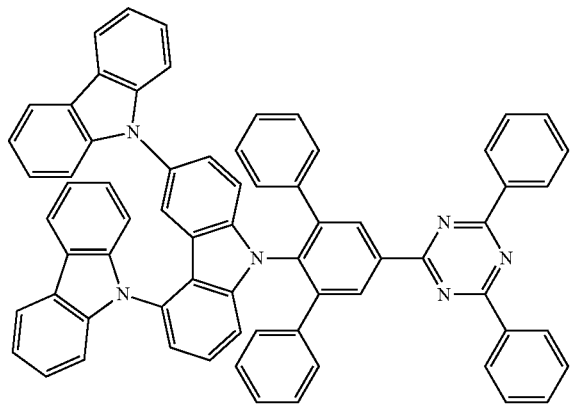 |
| 47 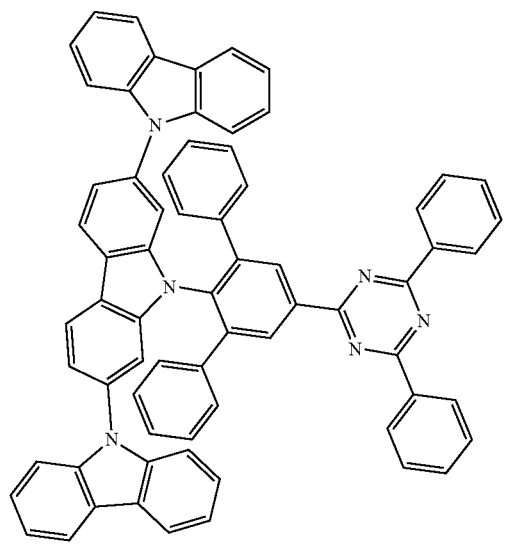 | 48 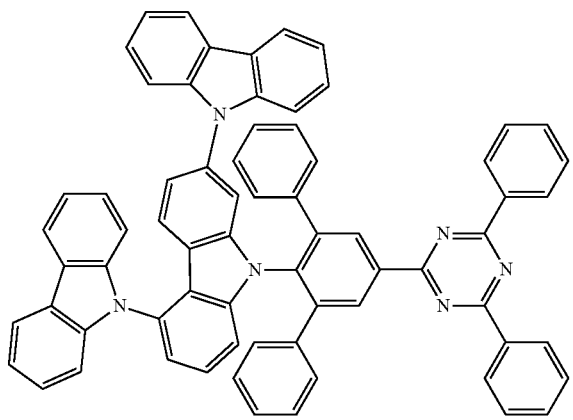 |
| 49 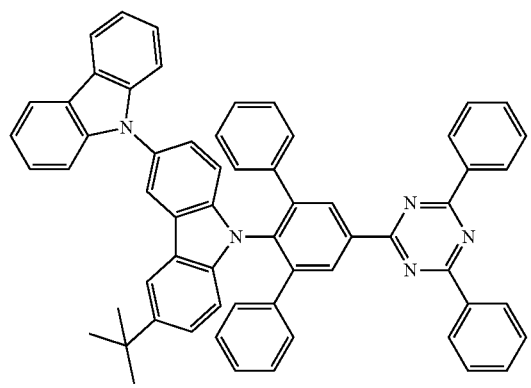 | 50 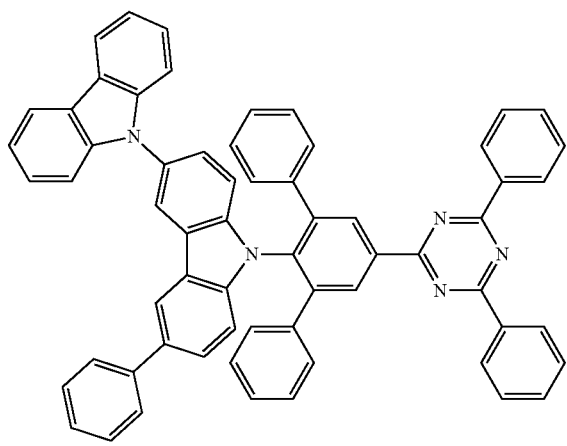 |

-continued
51
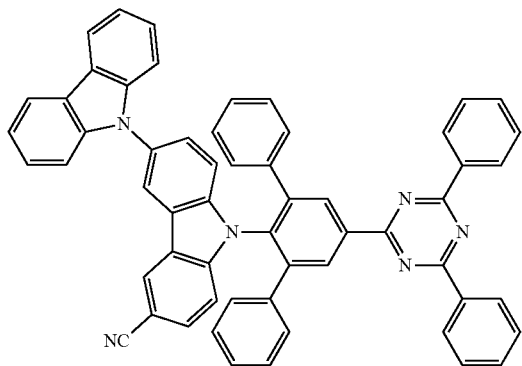
52
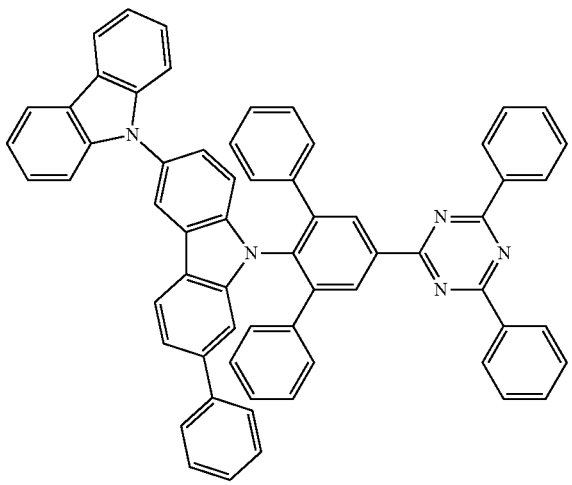
53
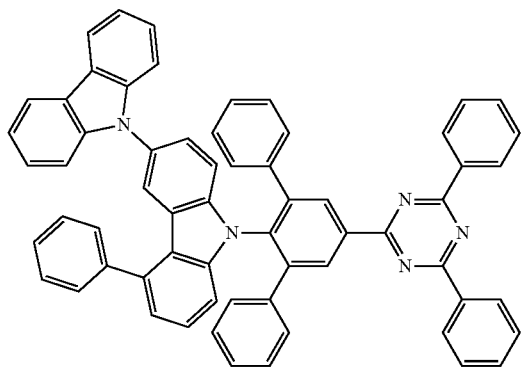
54
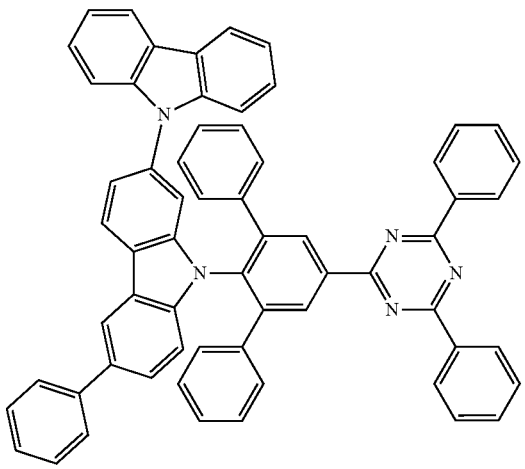
55
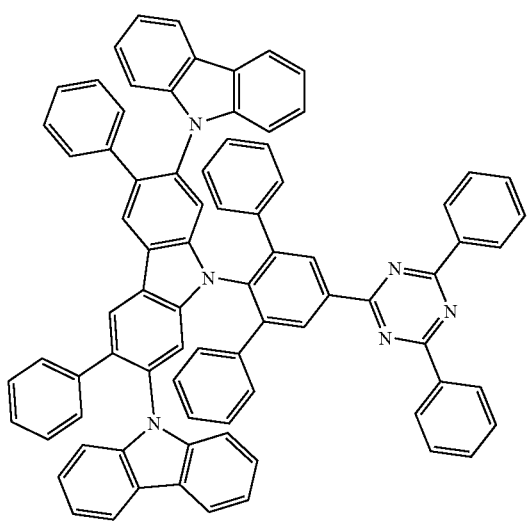
56
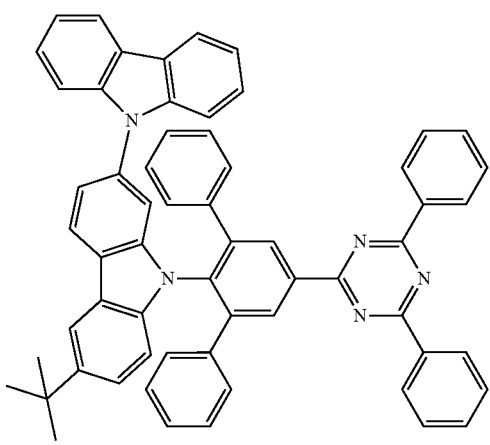

-continued
57
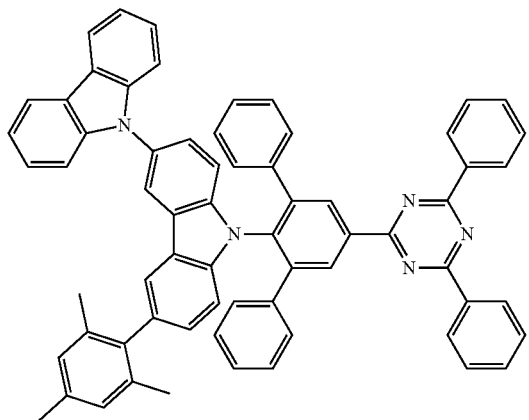
58
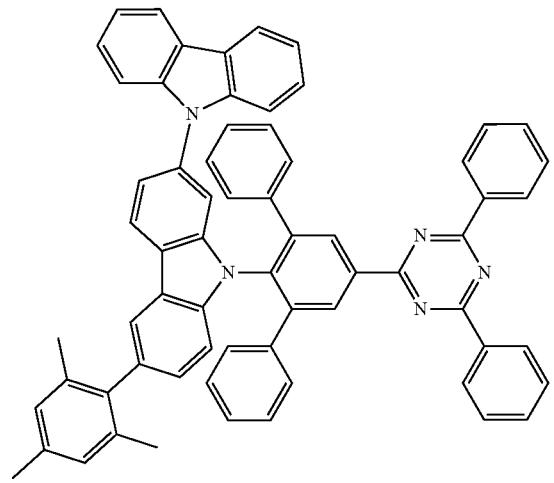
59
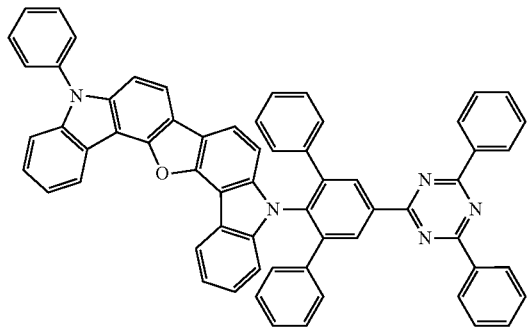
60
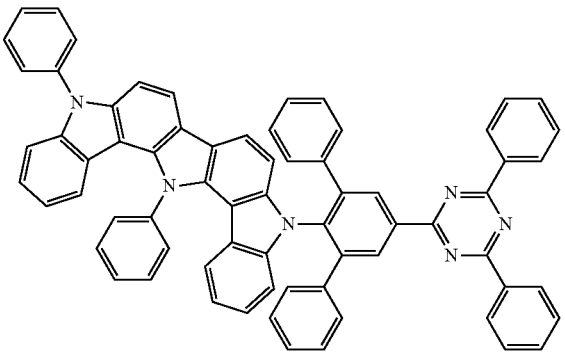
61
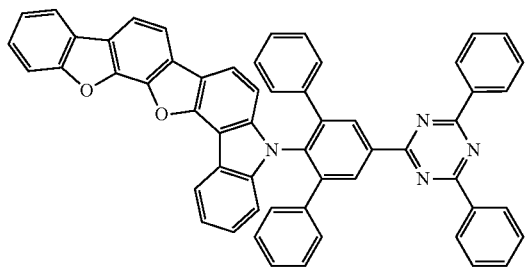
62
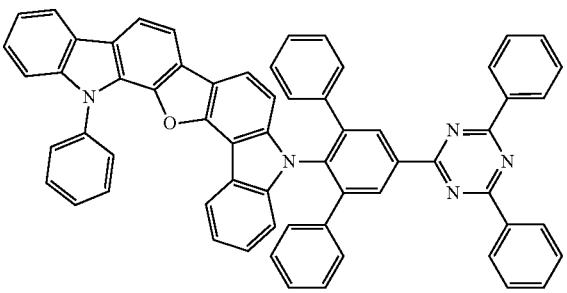
63
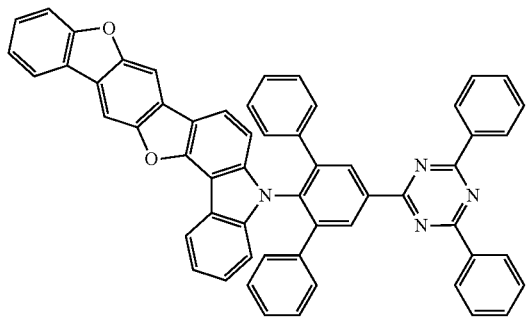
64
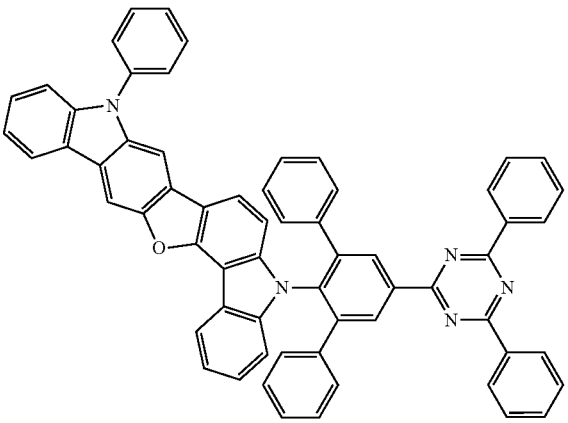

-continued
65
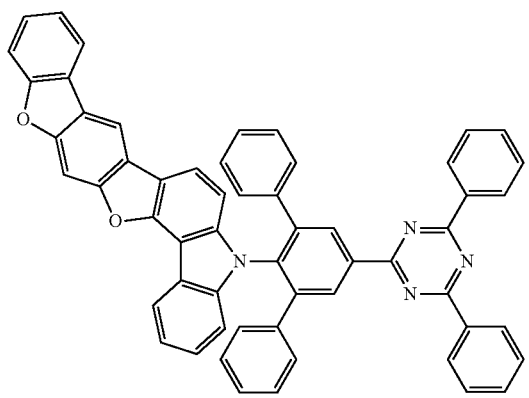
66
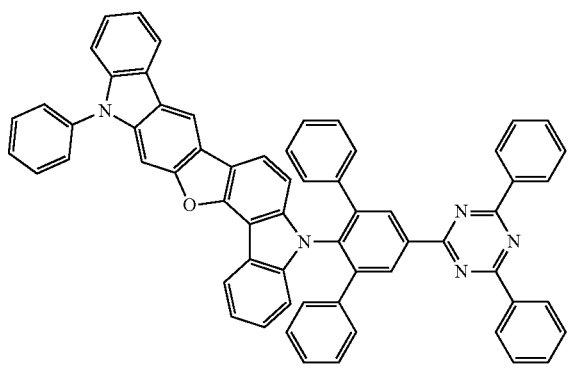
67
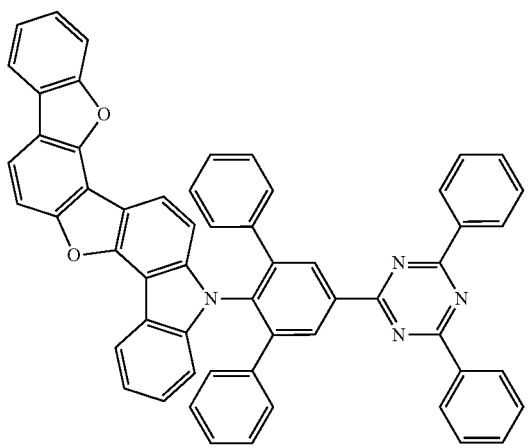
68
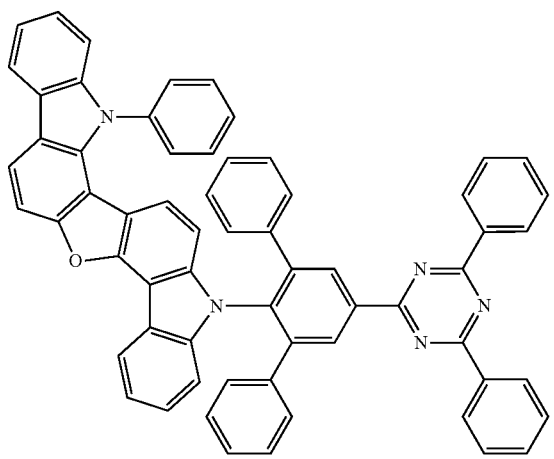
69
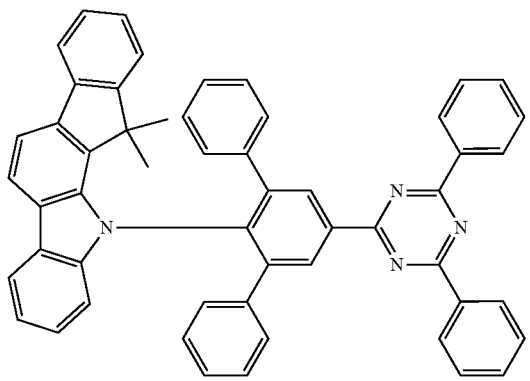
70
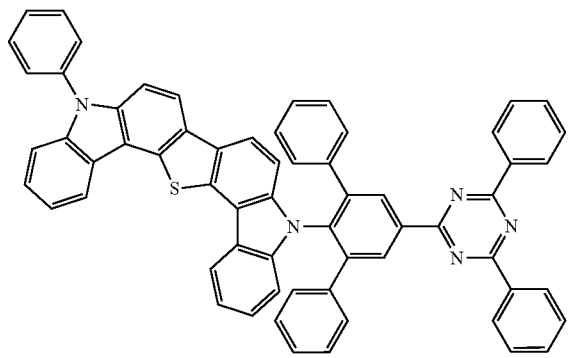
71
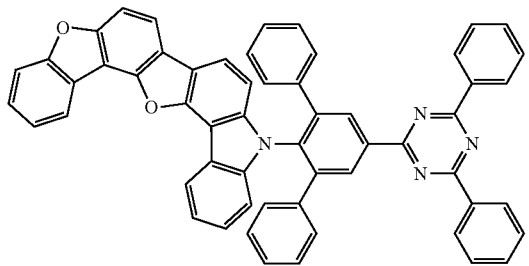
72
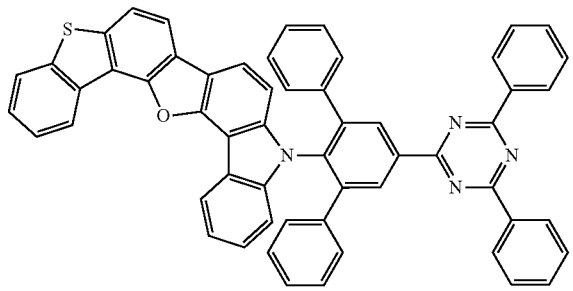

-continued
73
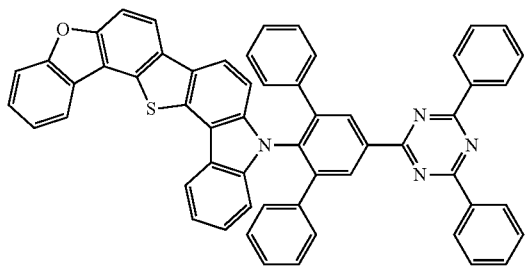
74
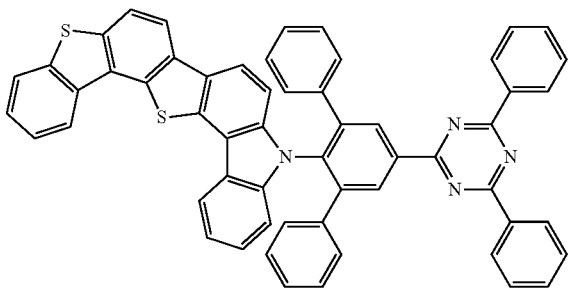
75
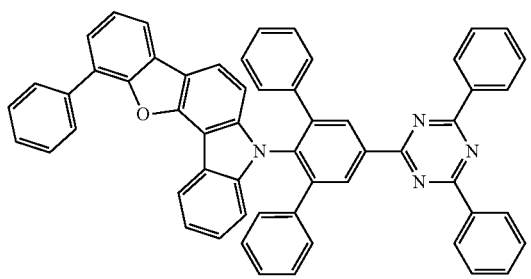
76
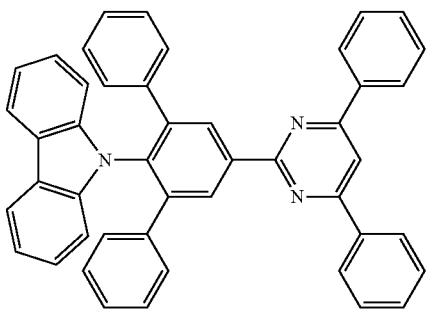
77
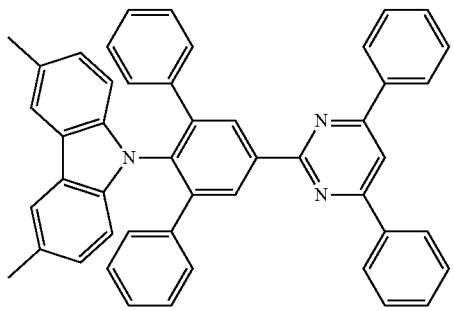
78
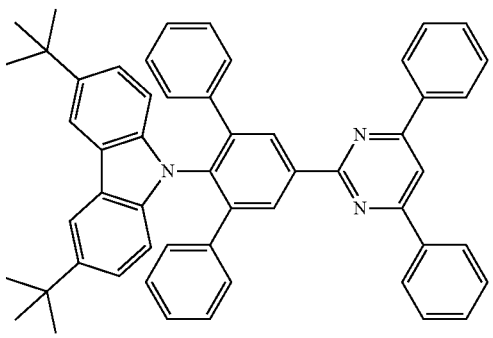
79
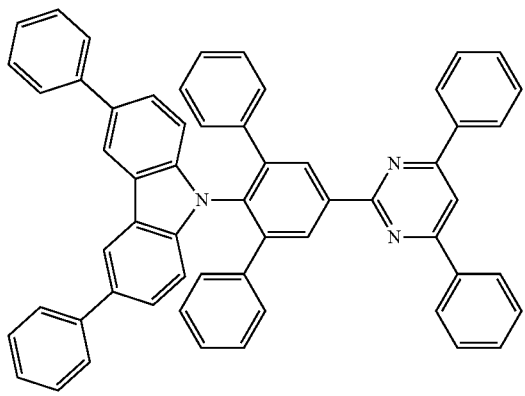
80
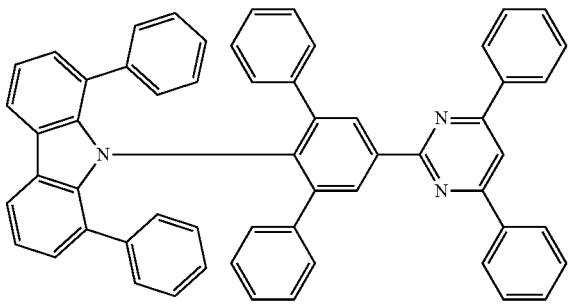

-continued
| 81 | 82 |
|---|---|
| 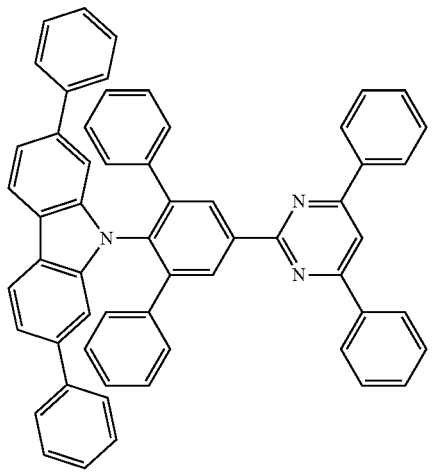 927 | 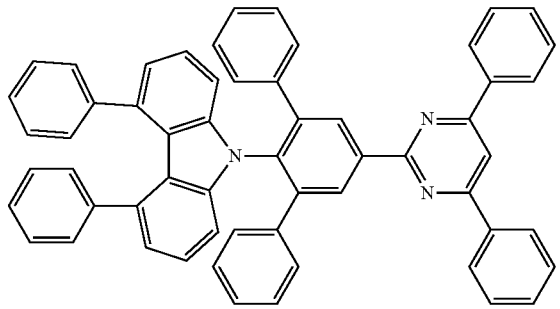 928 |
| 83 | 84 |
|---|---|
| 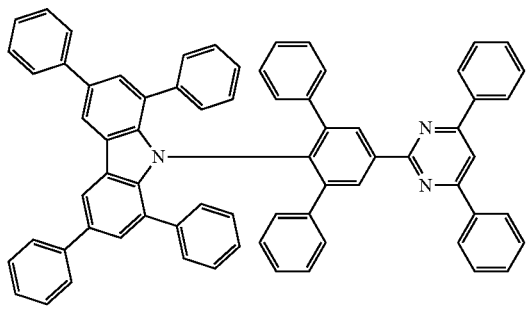 | 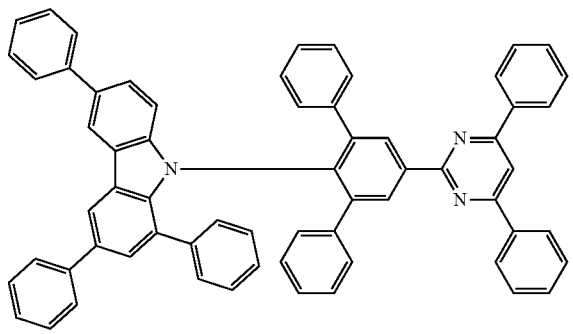 |
| 85 | 86 |
|---|---|
| 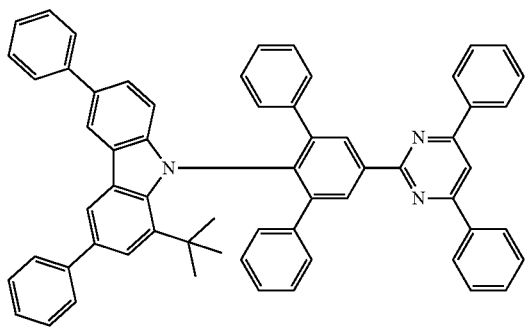 | 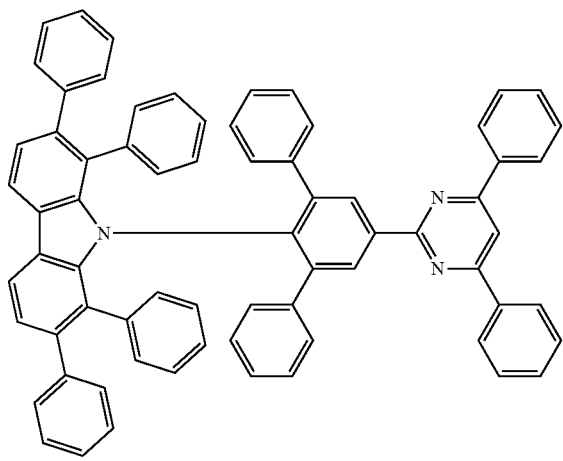 |

-continued
87
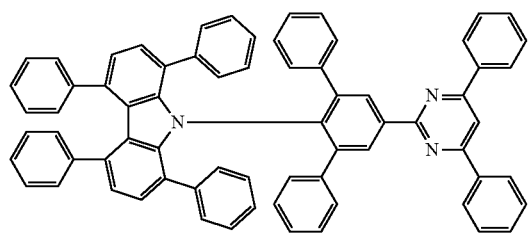
88
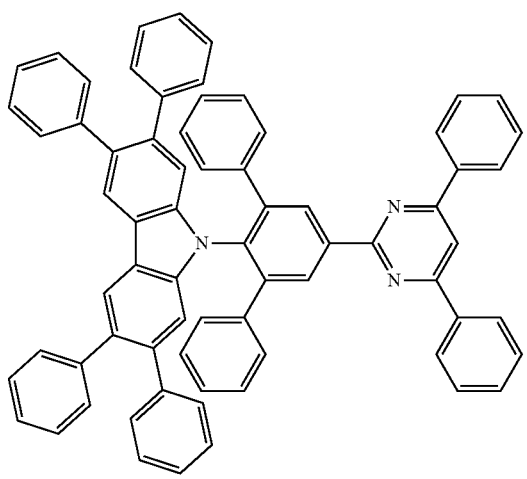
89
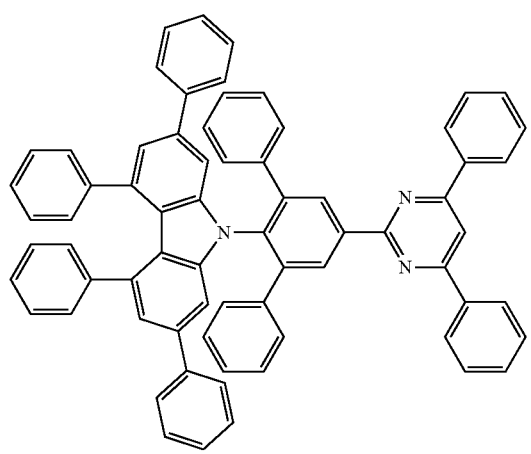
90
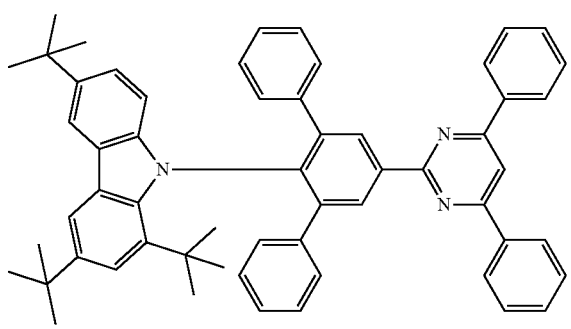
91
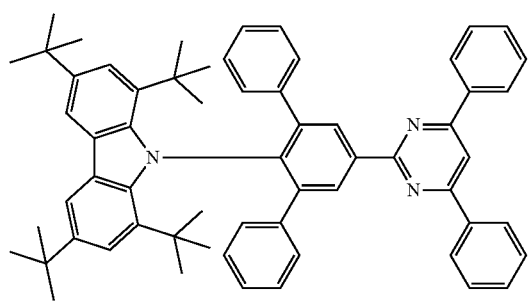
92
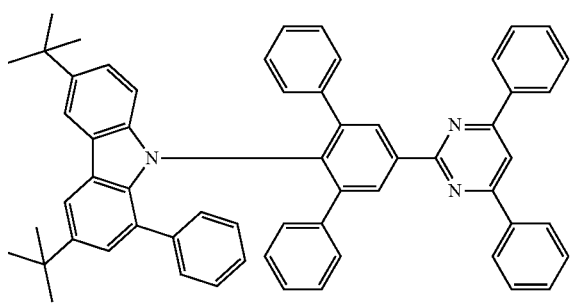
93
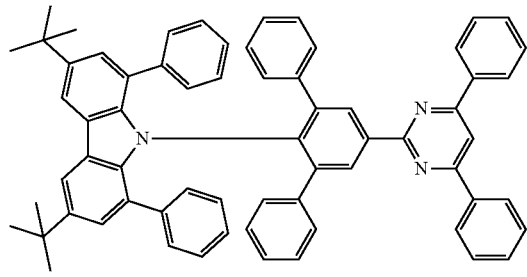
94
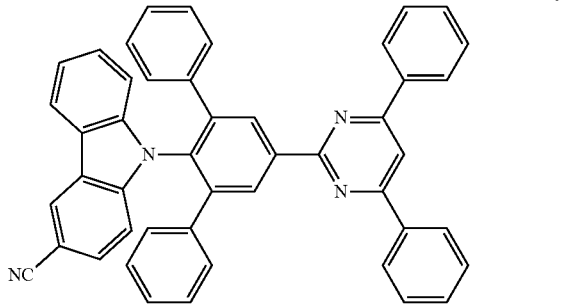

-continued
95
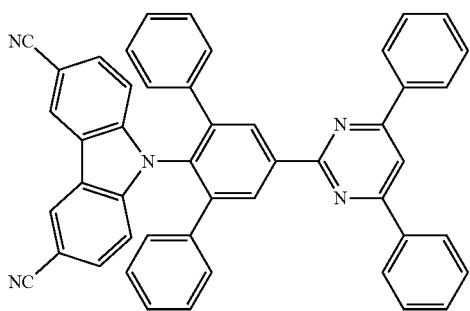
96
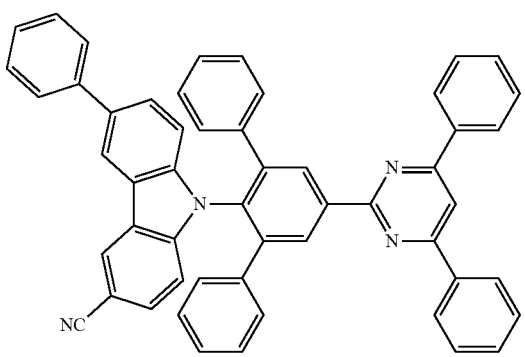
97
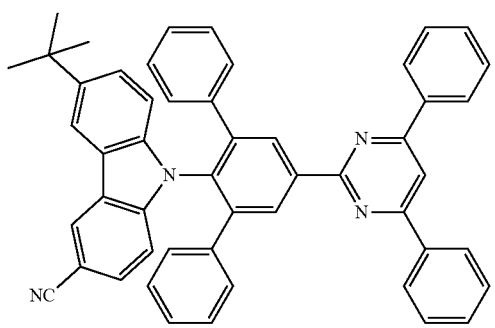
98
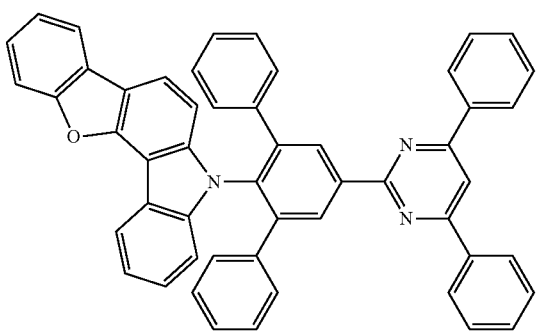
99
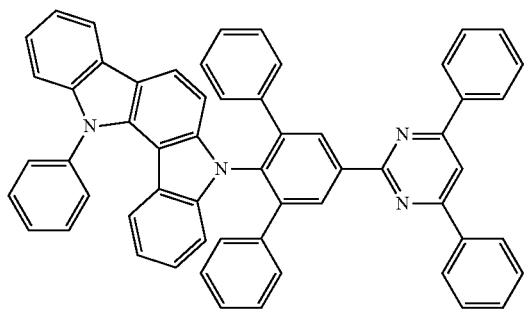
100
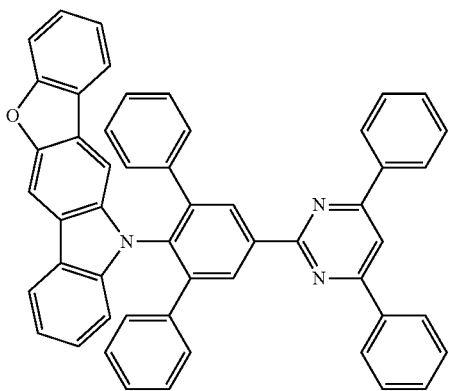
101
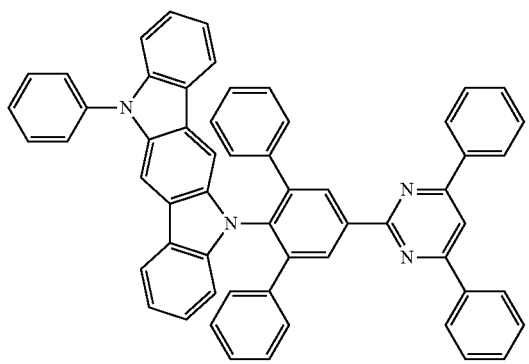
102
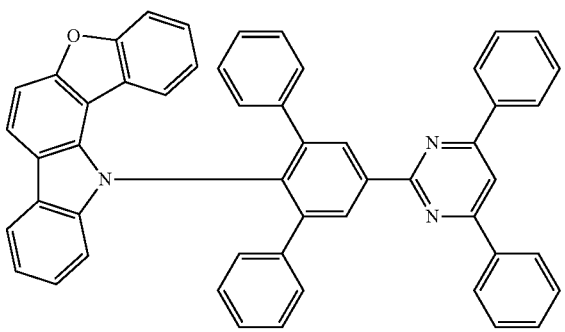

103 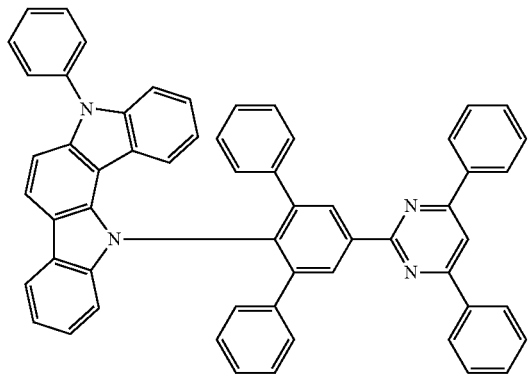
104 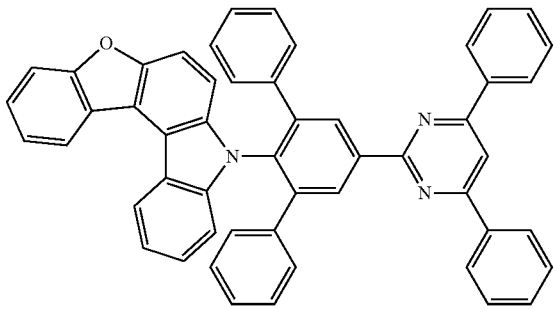
105 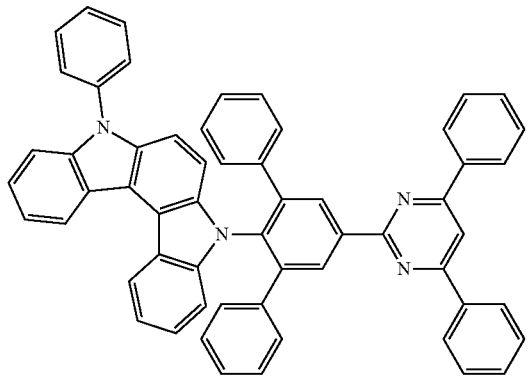
106 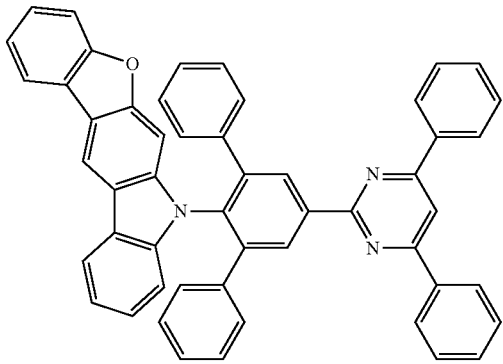
107 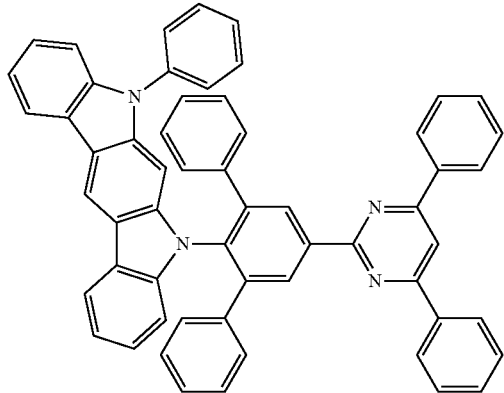
108 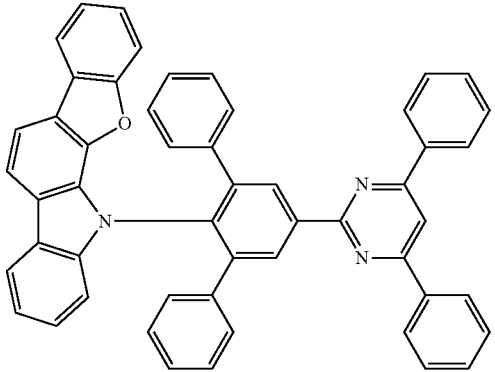
109 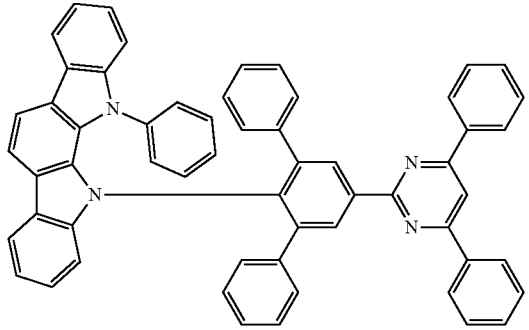
110 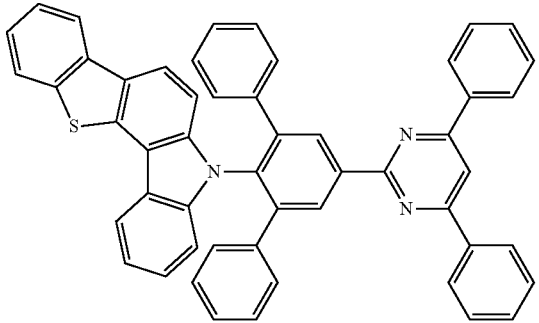

-continued
111
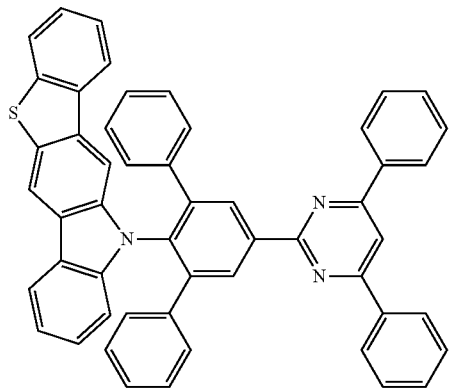
112
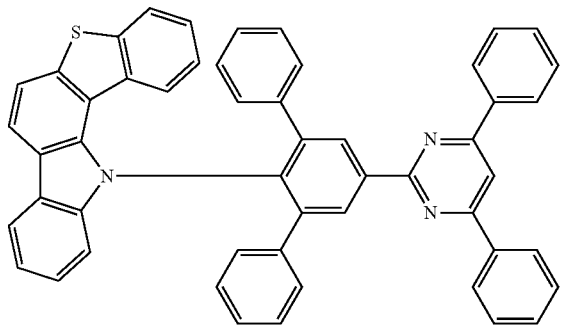
113
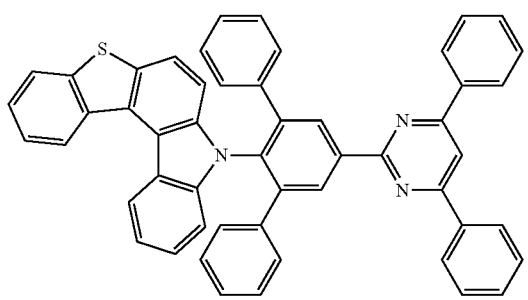
114
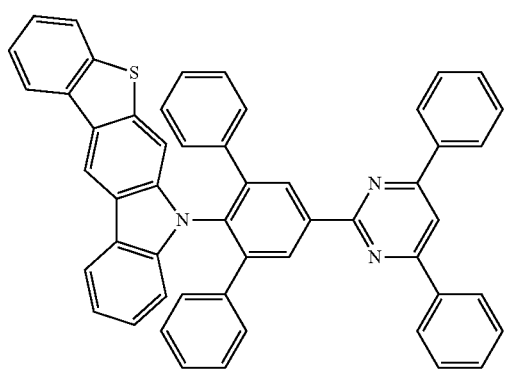
115
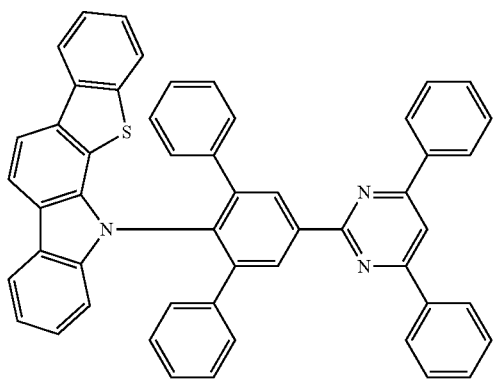
116
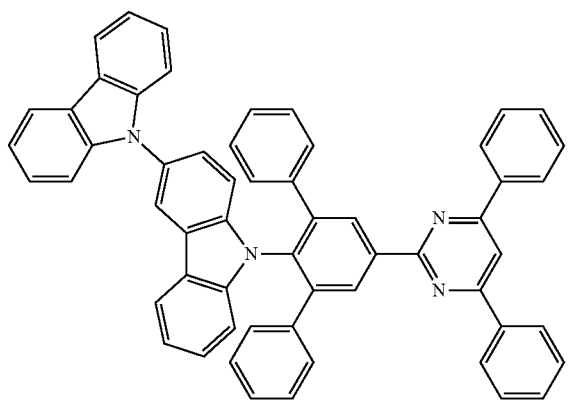

937
938
-continued
117
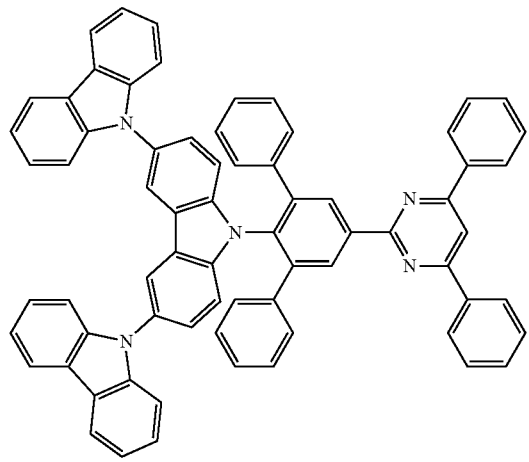
118
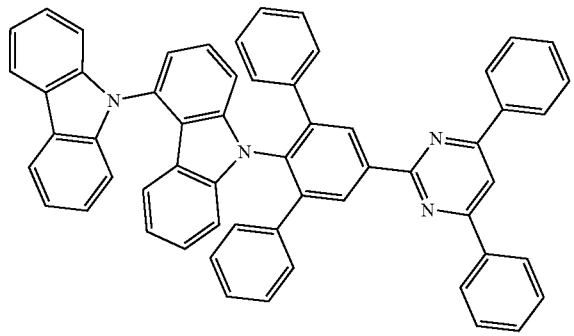
119
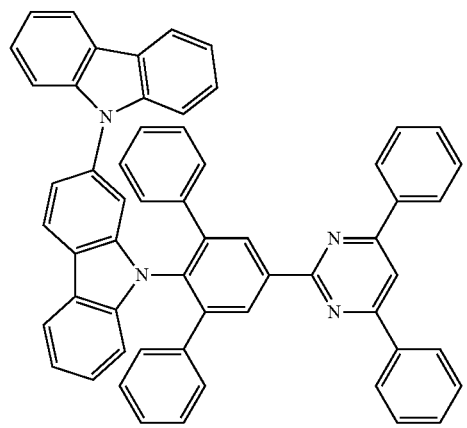
120
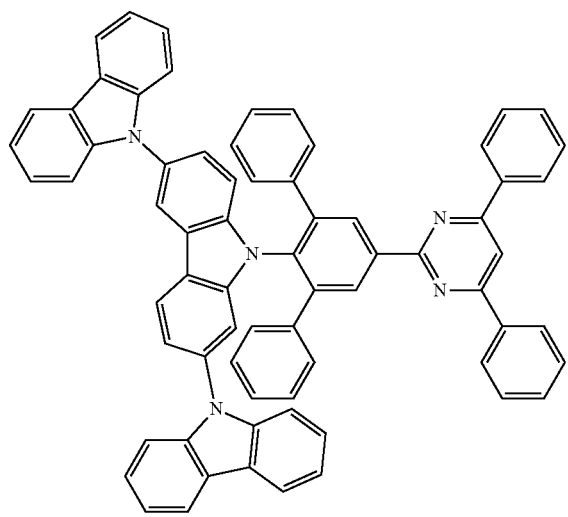
121
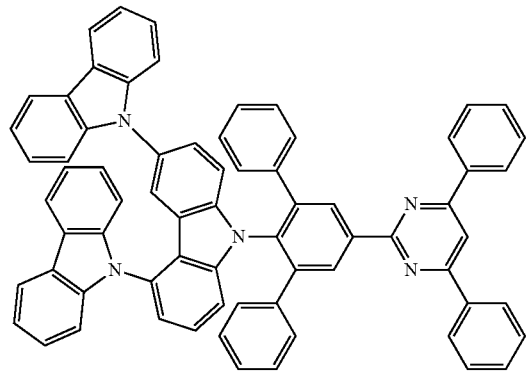
122
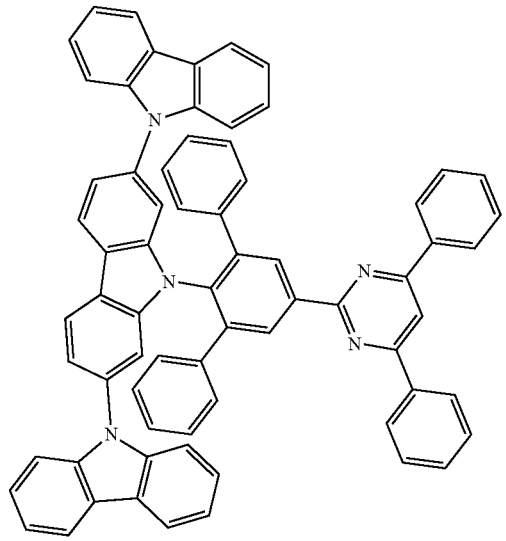

123
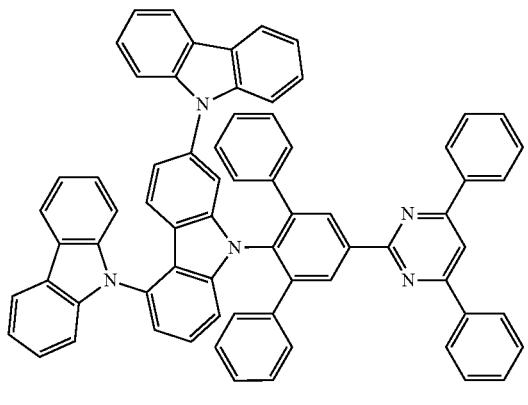
124
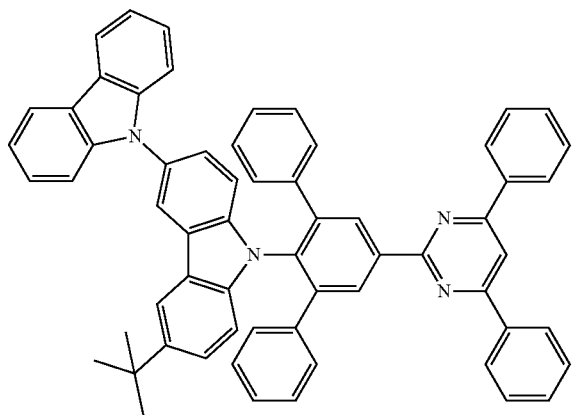
125
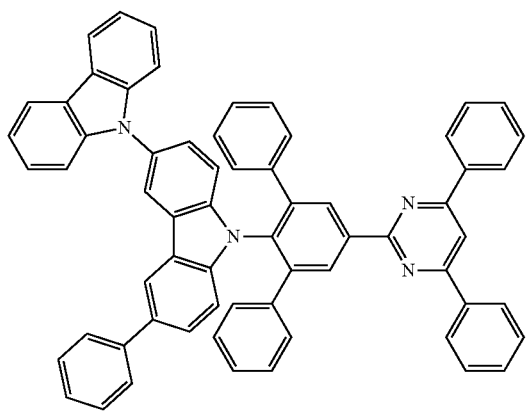
126
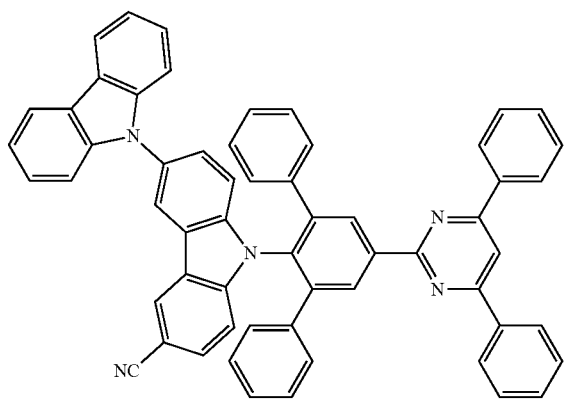
127
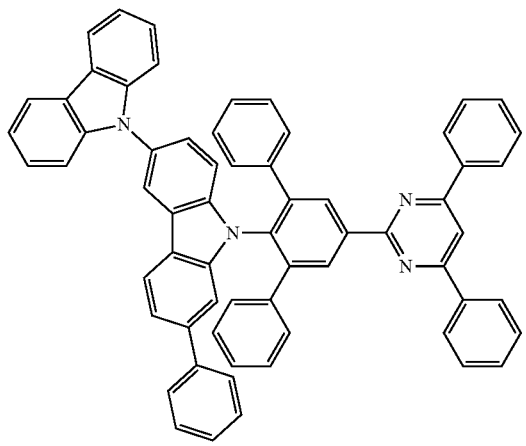
128
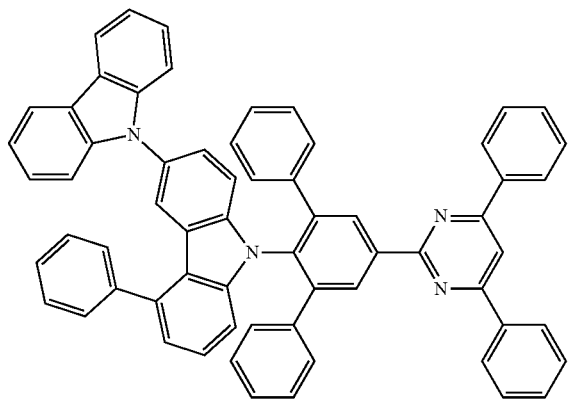

941 942
-continued
129
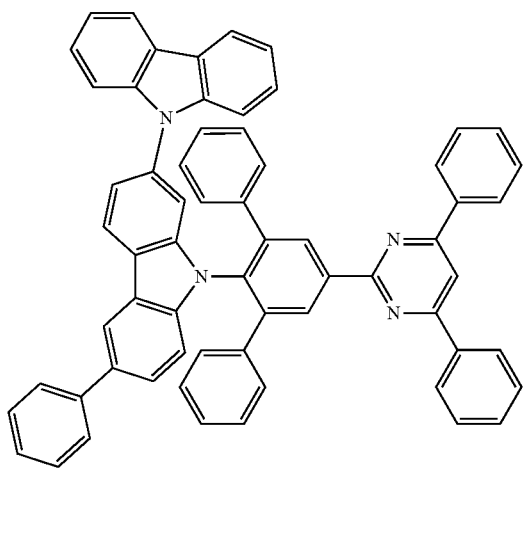
130
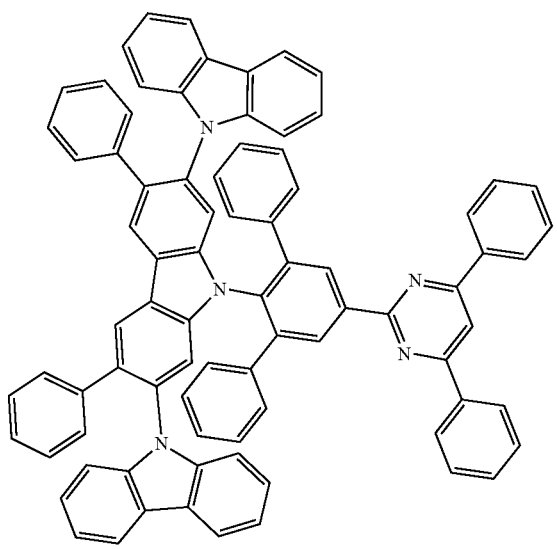
131
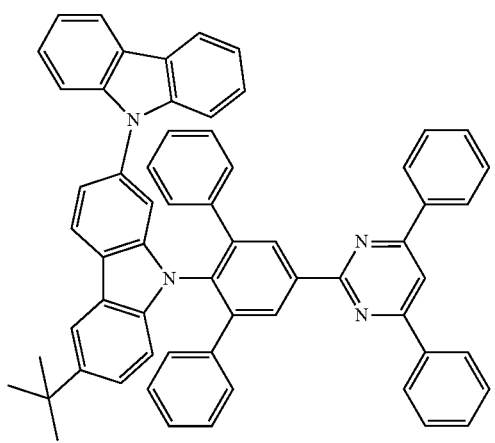
132
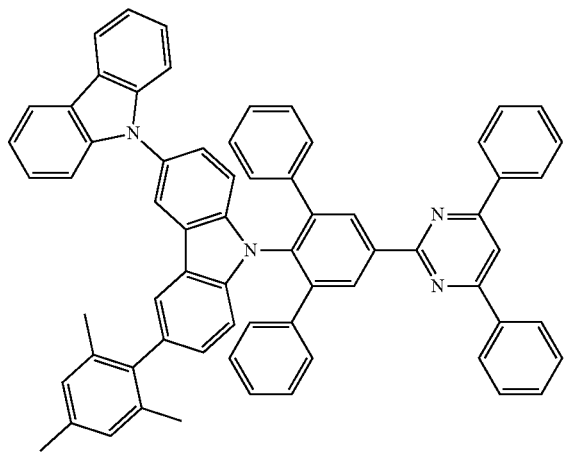
133
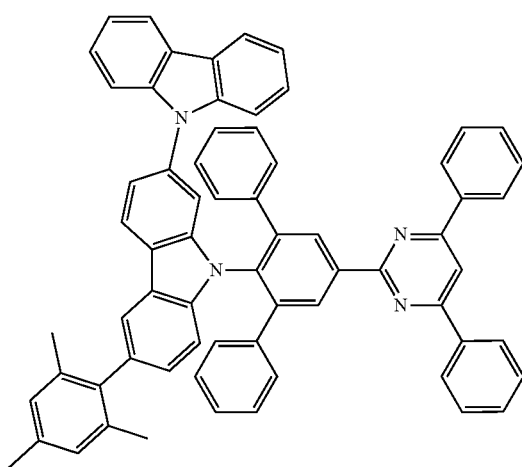
134
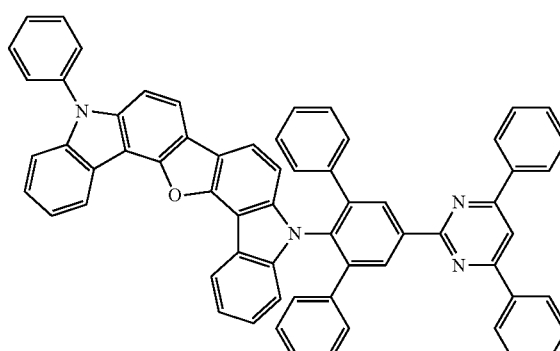

-continued
135
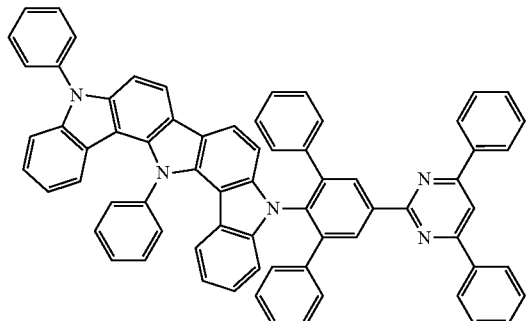
136
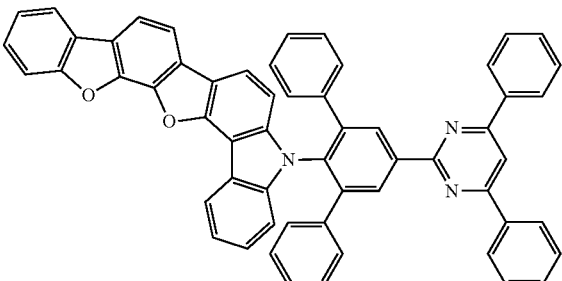
137
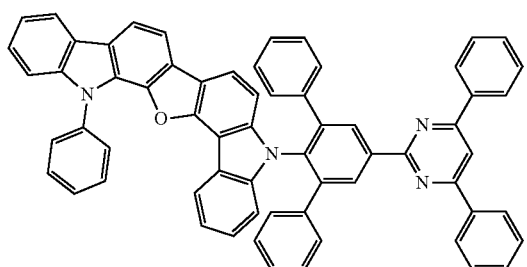
138
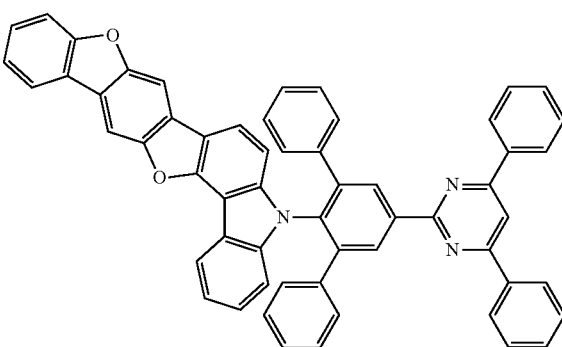
139
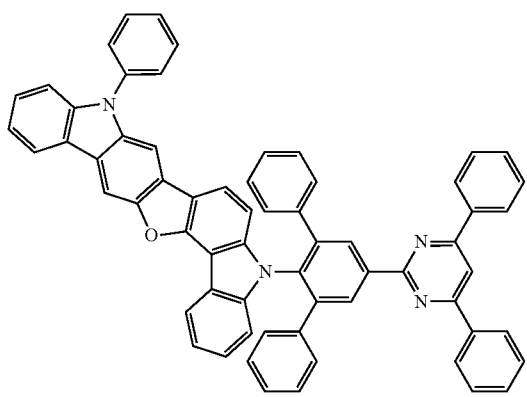
140
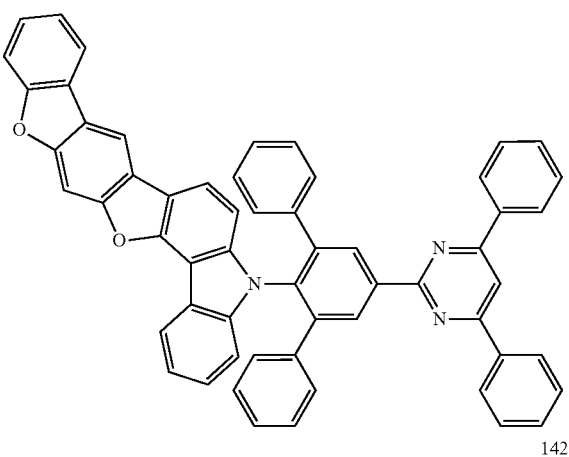
141
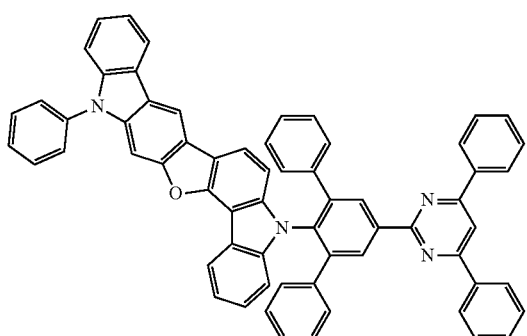
142
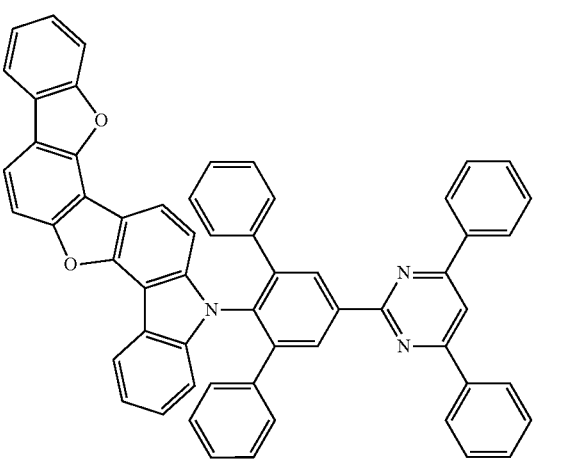

-continued
143
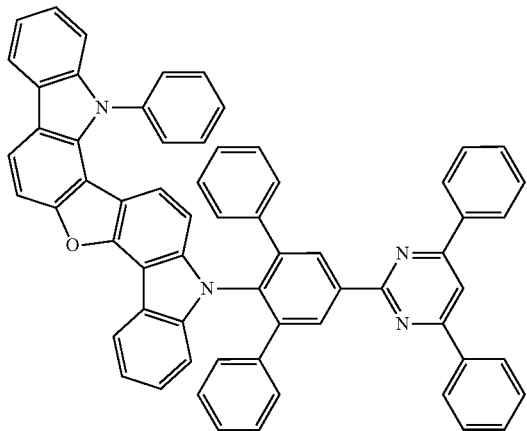
144
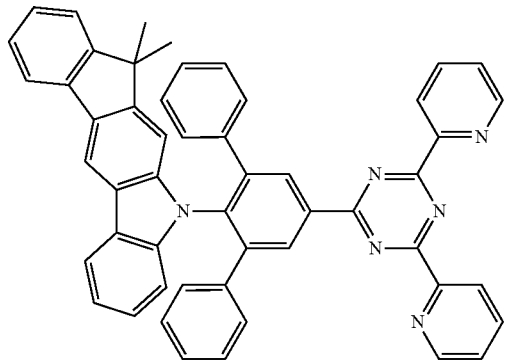
145
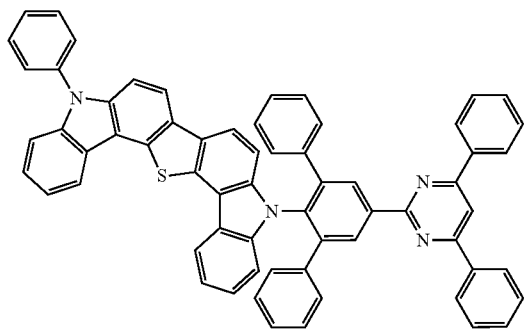
146
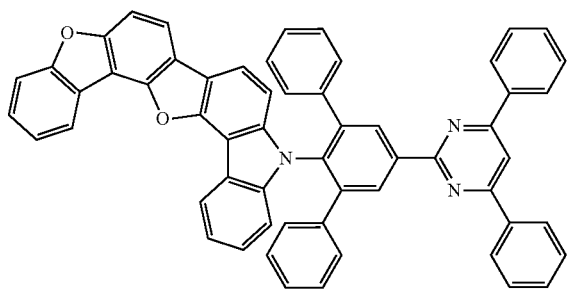
147
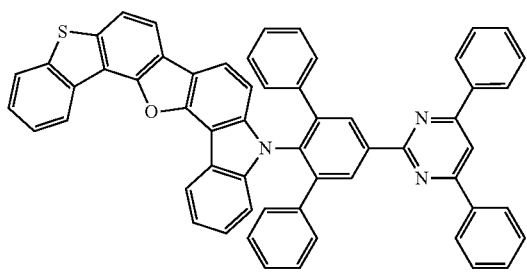
148
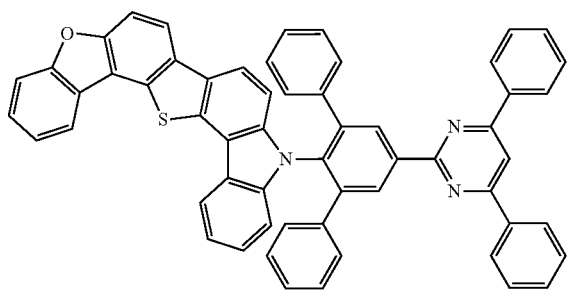
149
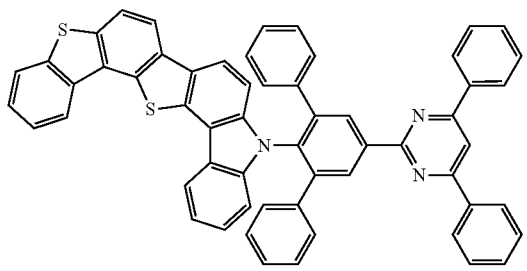
150
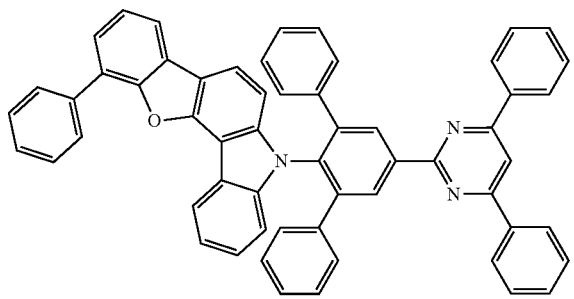

-continued
| 151 | 152 |
|---|---|
| 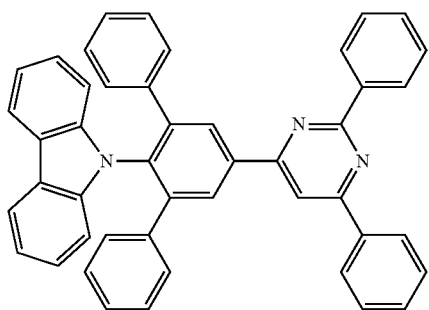 | 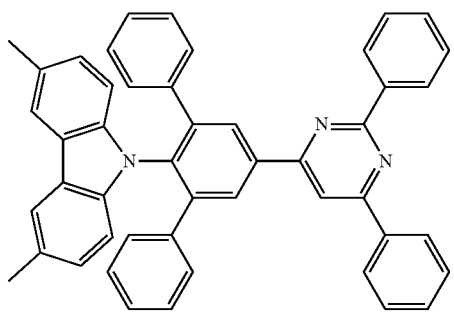 |
| 153 | 154 |
| 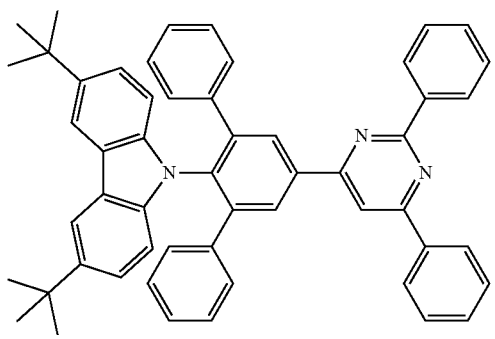 | 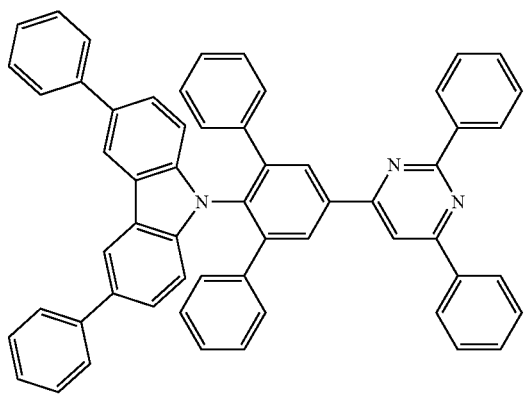 |
| 155 | 156 |
| 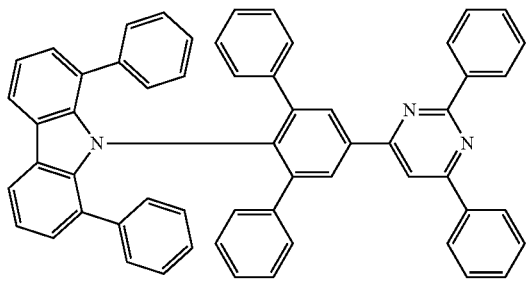 | 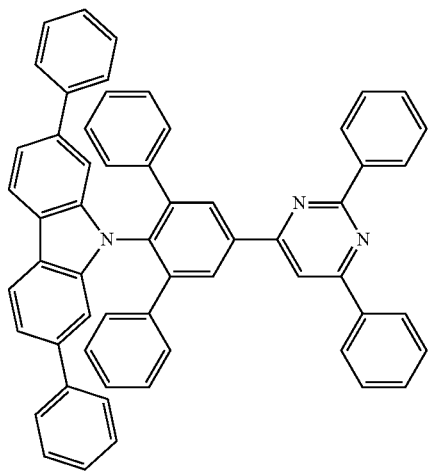 |
| 157 | 158 |
| 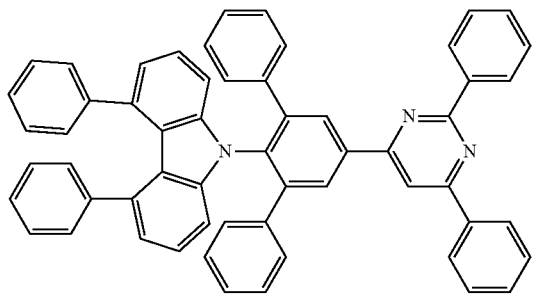 | 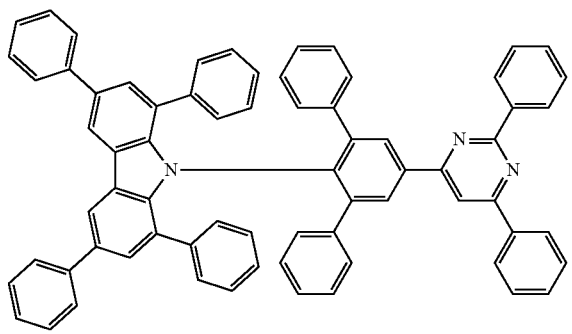 |

159 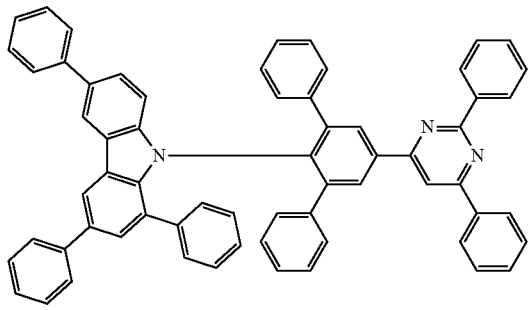
160 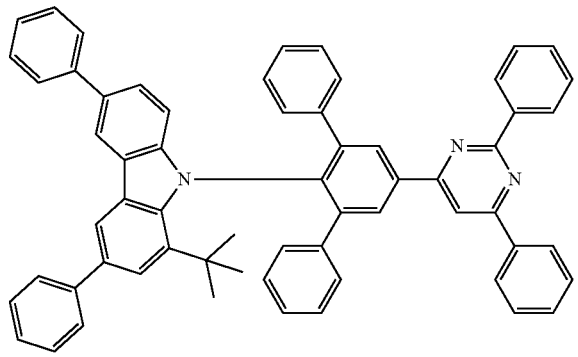
161 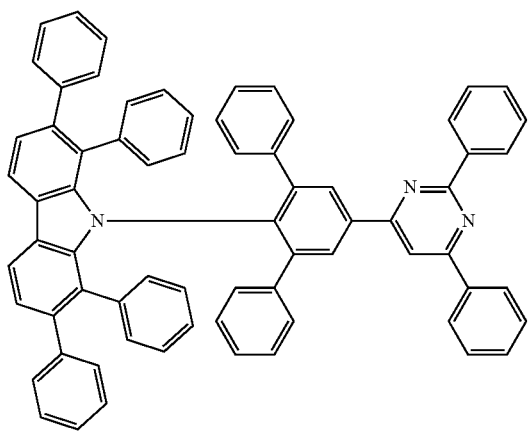
162 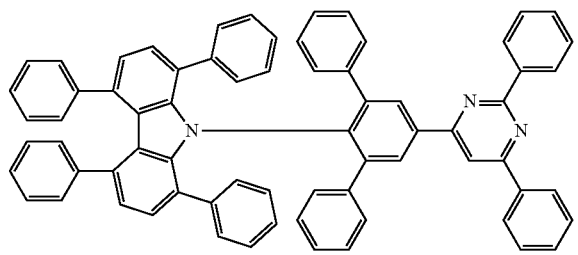
163 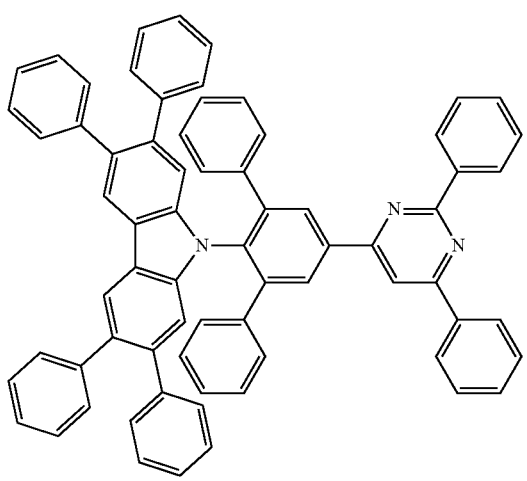
164 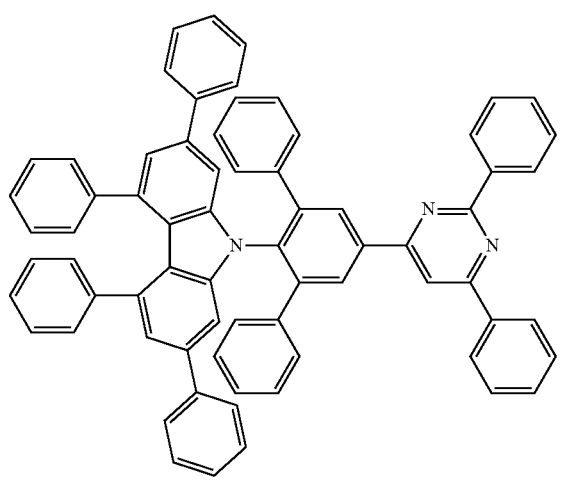

-continued
165
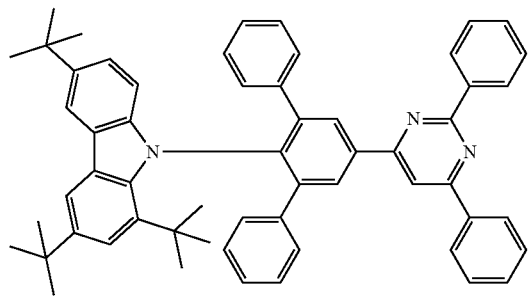
166
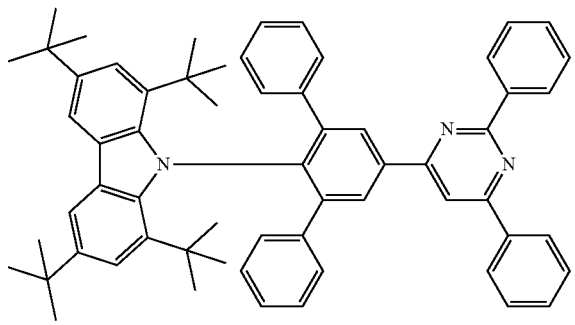
167
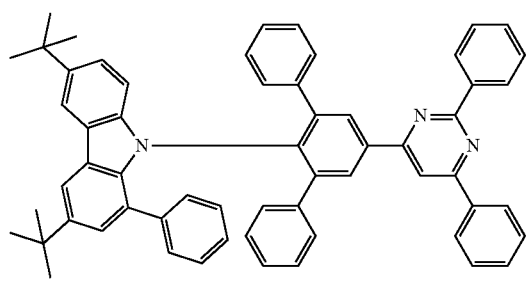
168
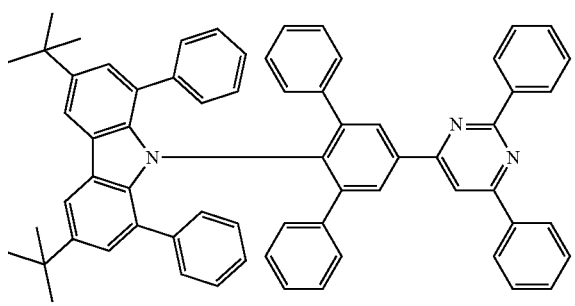
169
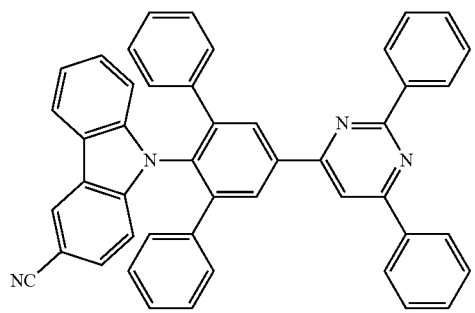
170
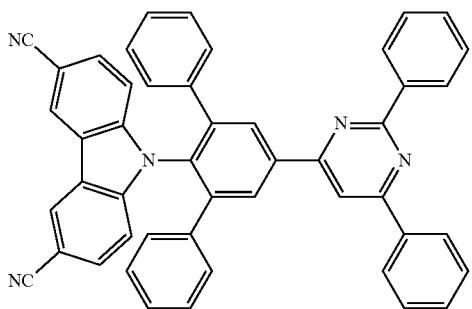
171
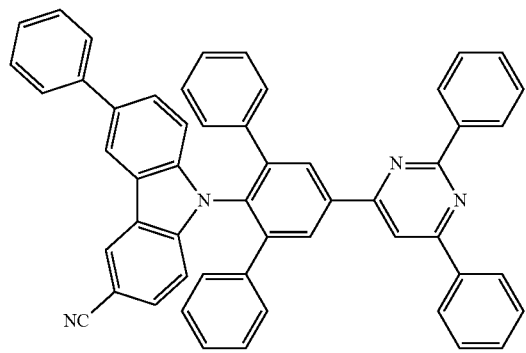
172
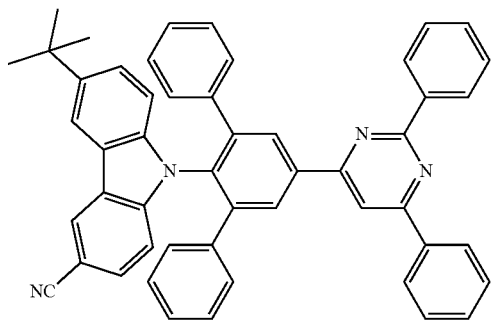

173
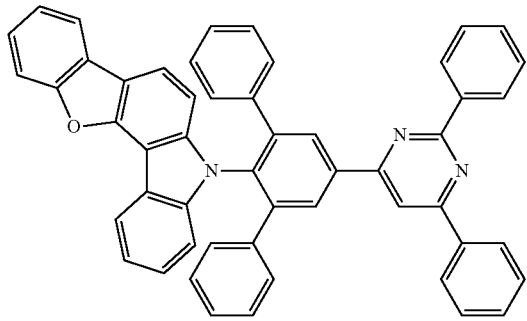
174
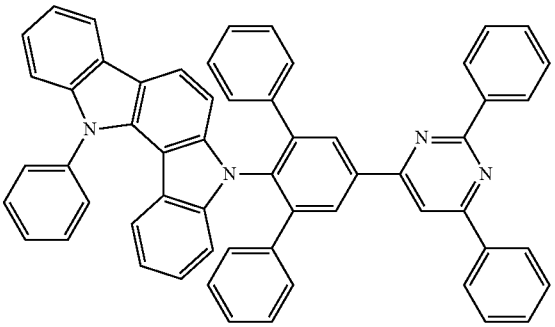
175
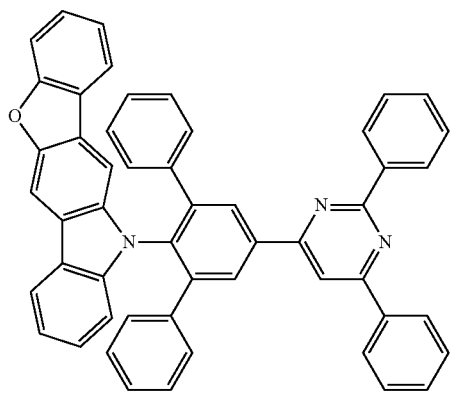
176
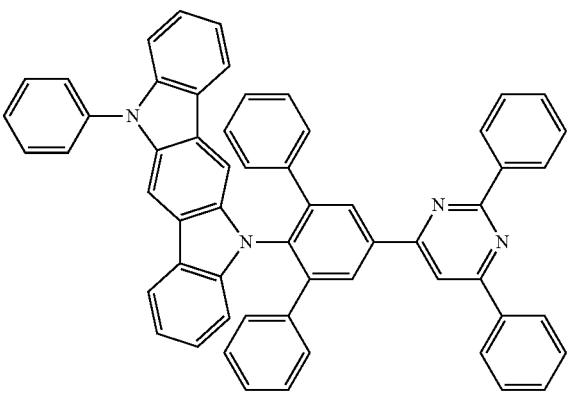
177
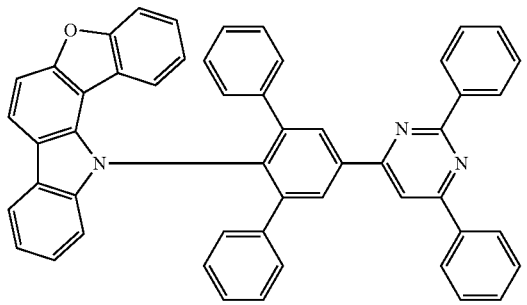
178
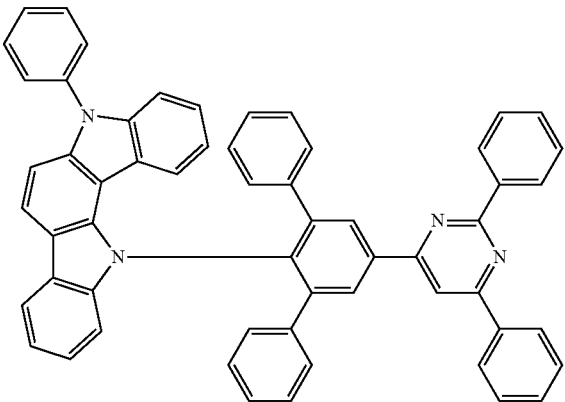
179
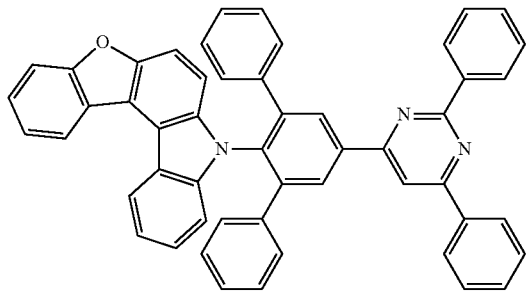
180
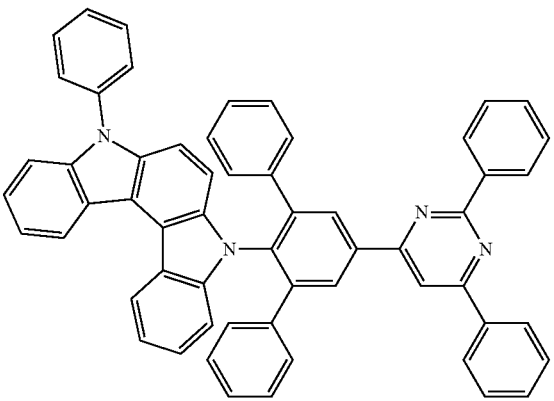

-continued
181
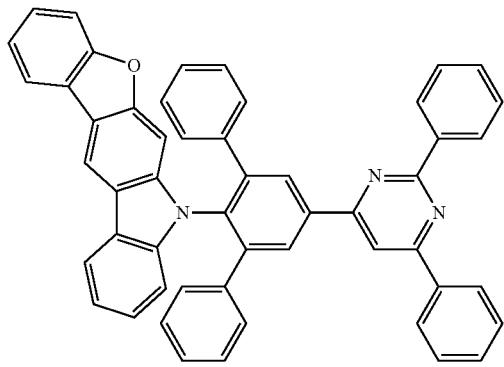
182
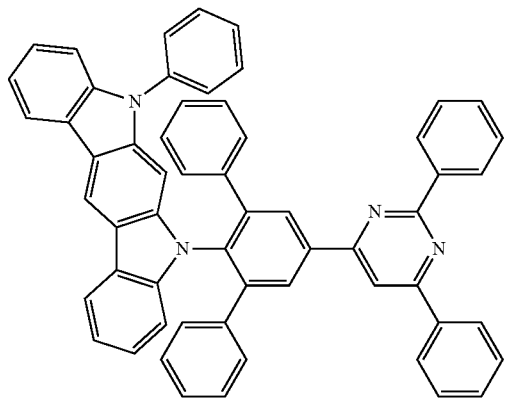
183
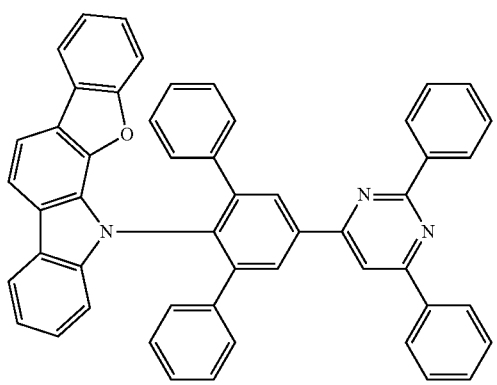
184
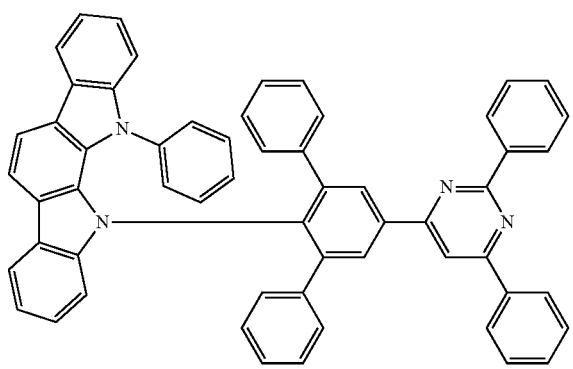
185
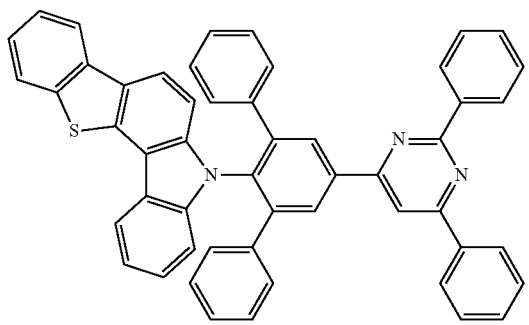
186
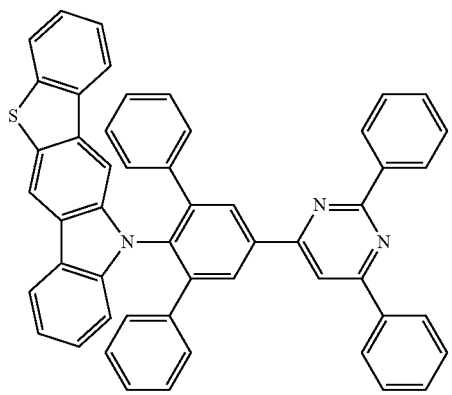
187
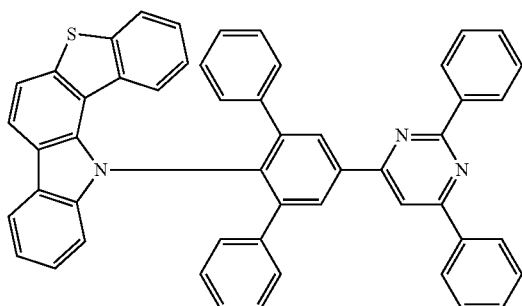
188
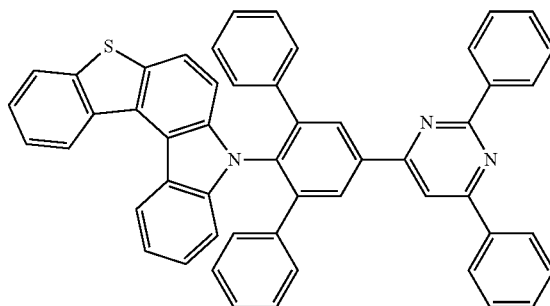

-continued
189
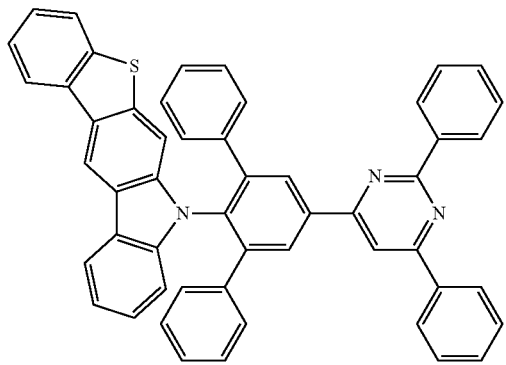
190
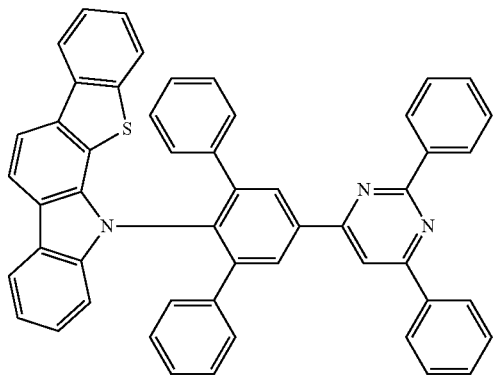
191
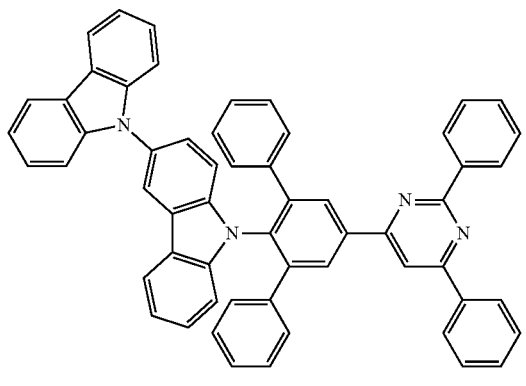
192
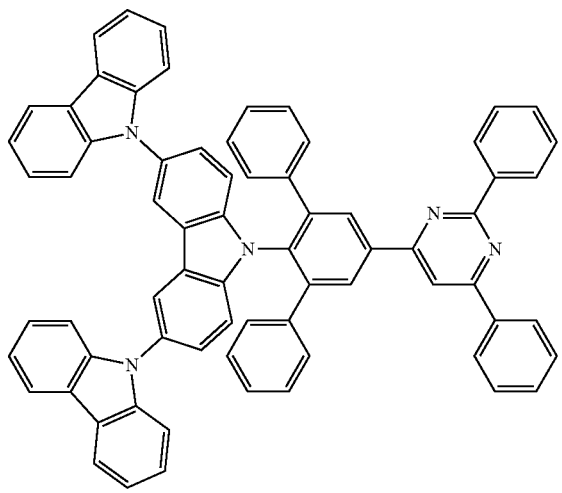
193
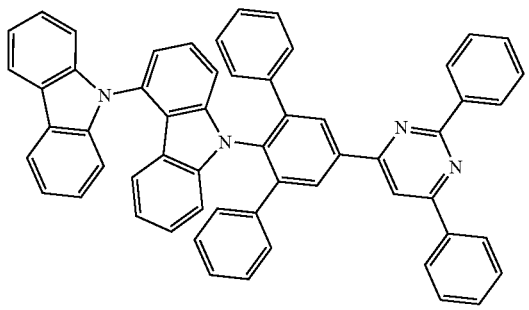
194
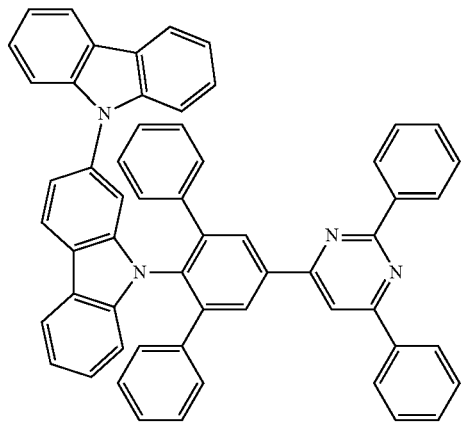

-continued
195
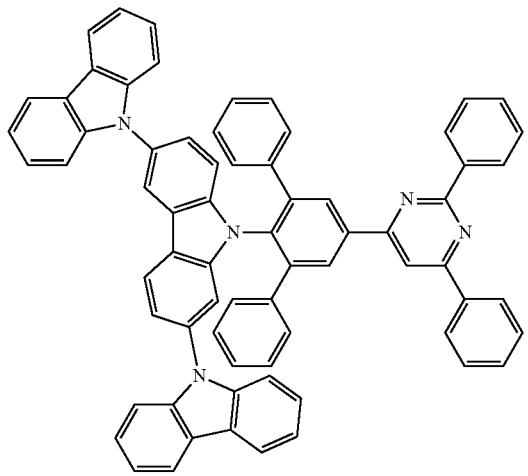
196
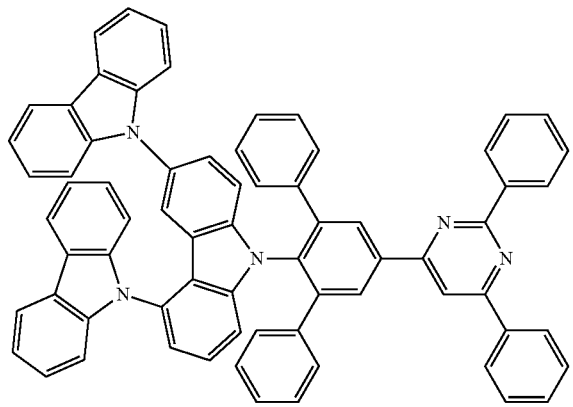
197
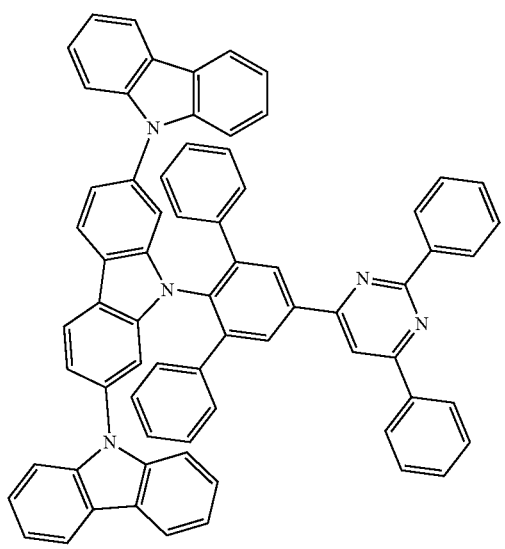
198
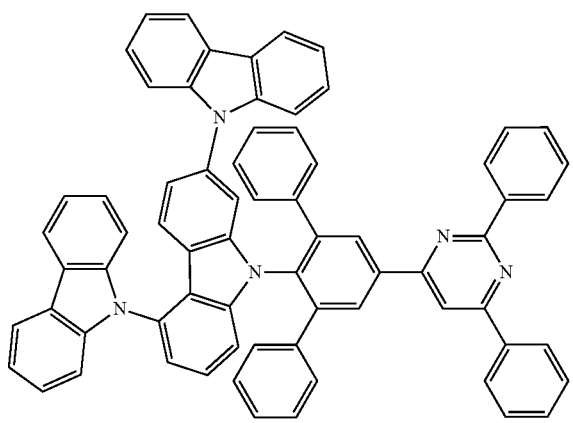
199
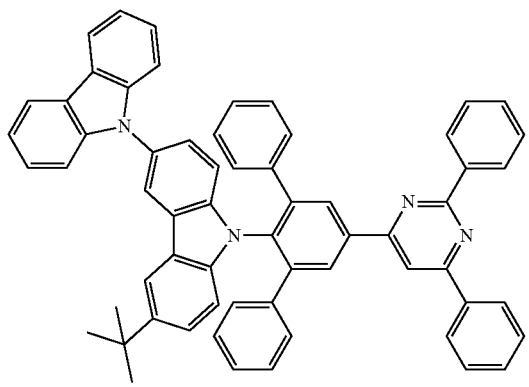
200
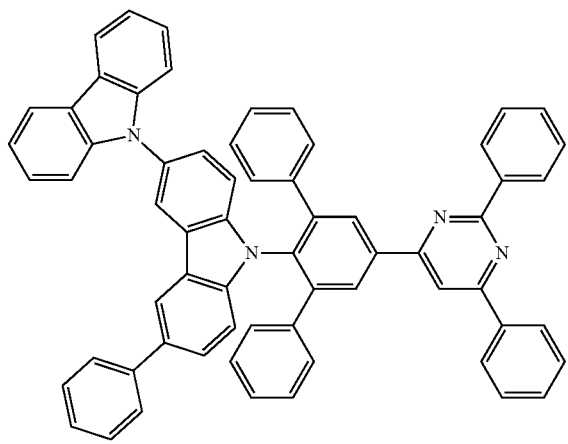

-continued
201
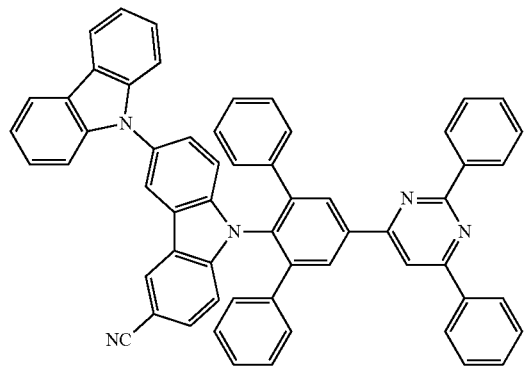
202
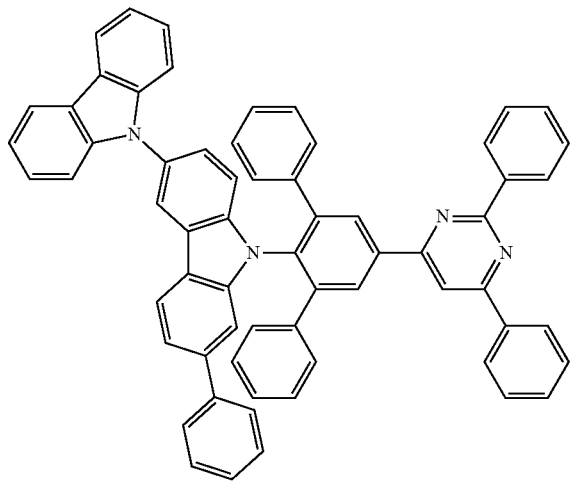
203
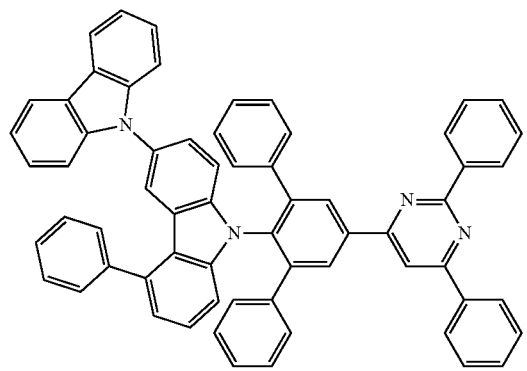
204
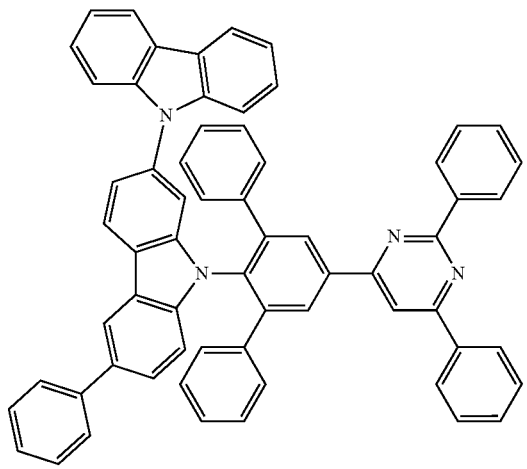
205
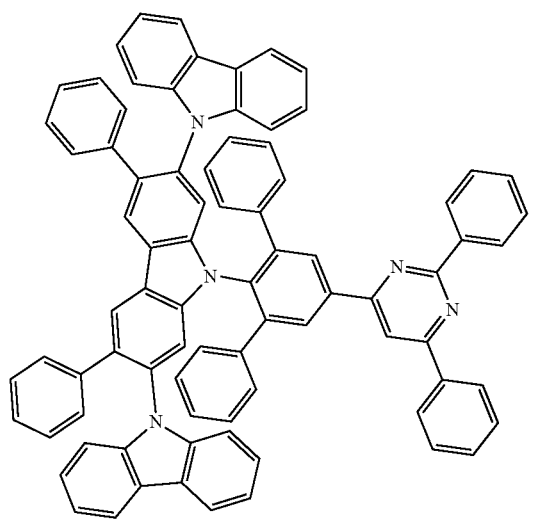
206
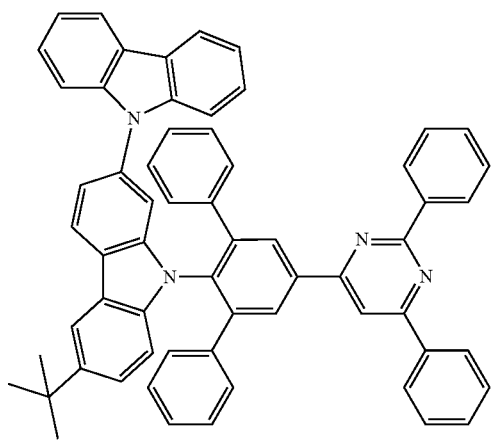

207
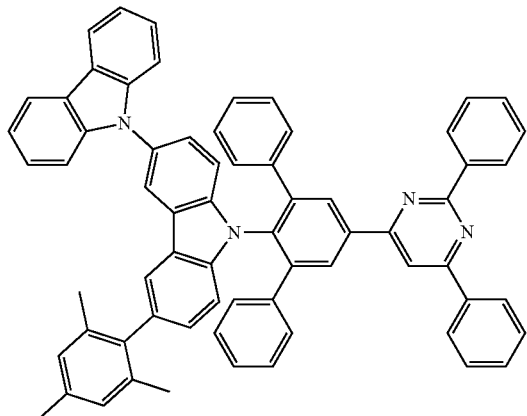
208
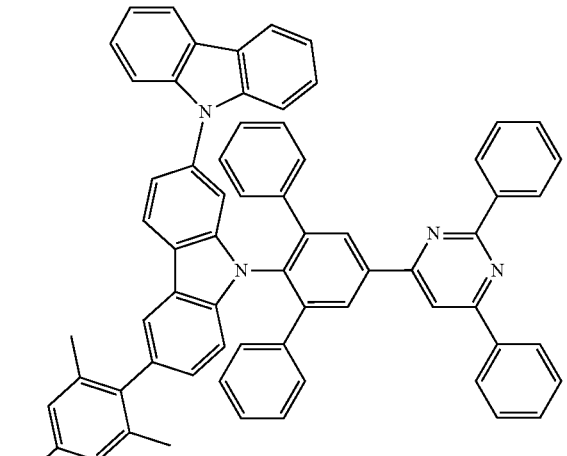
209
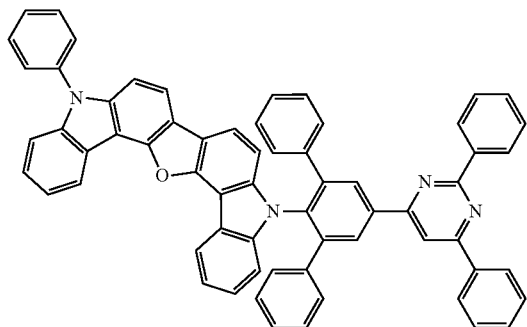
210
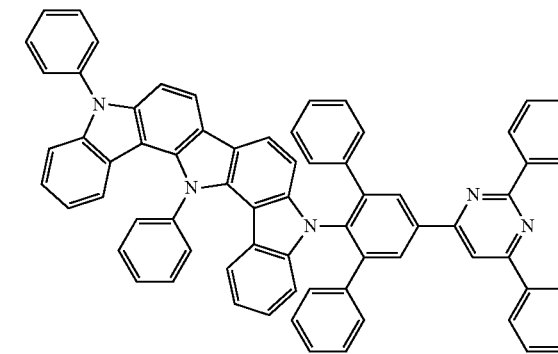
211
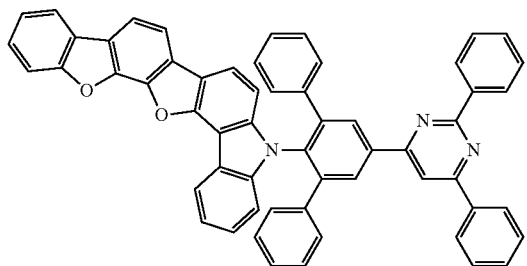
212
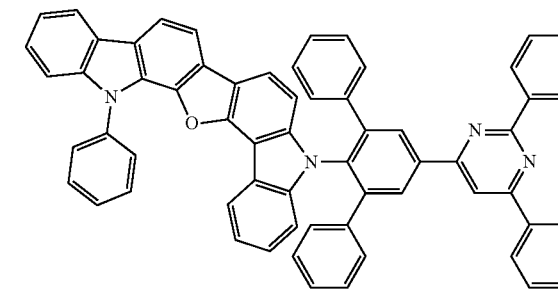
213
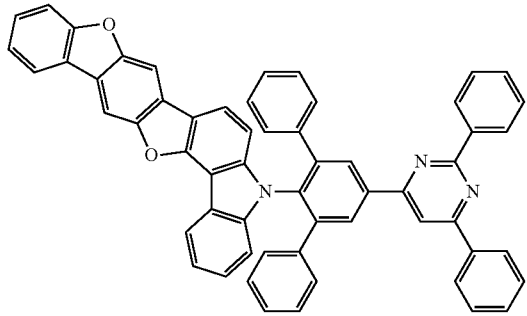
214
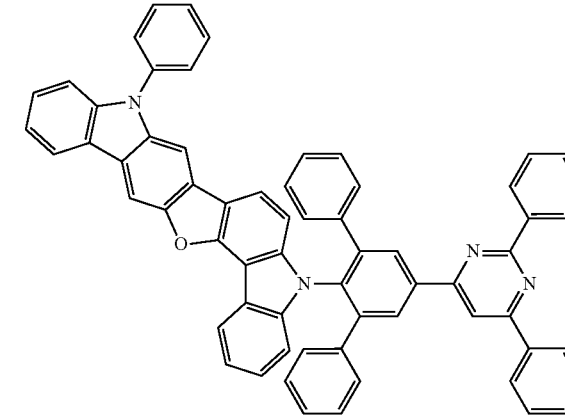

-continued
215
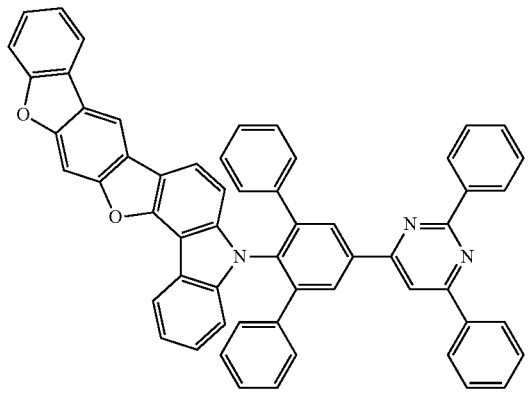
216
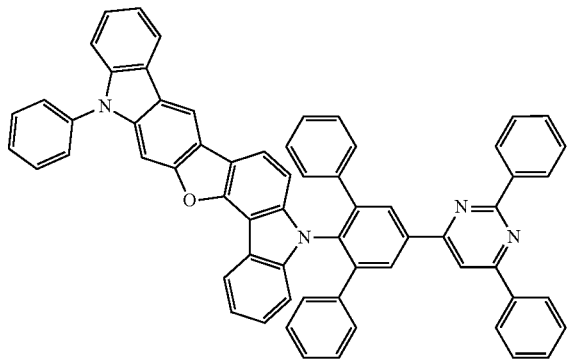
217
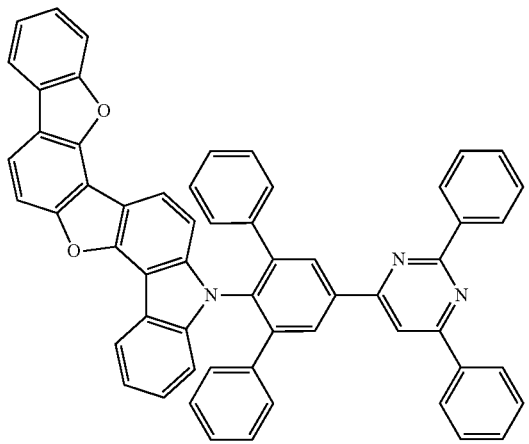
218
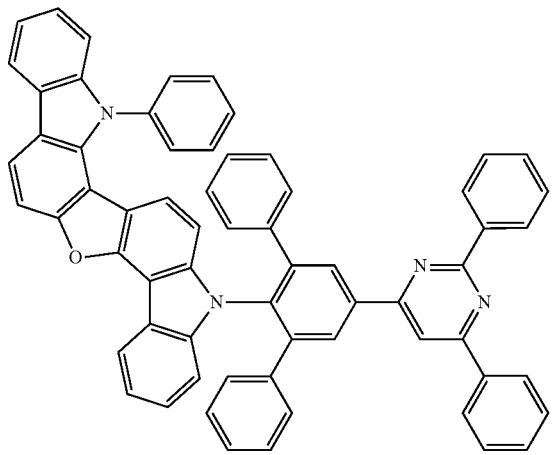
219
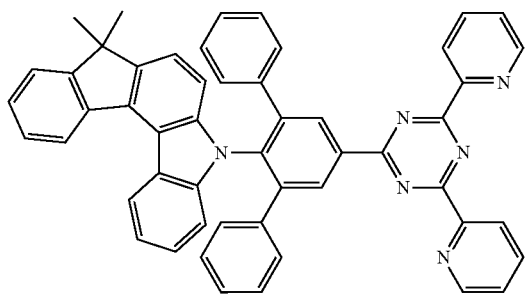
220
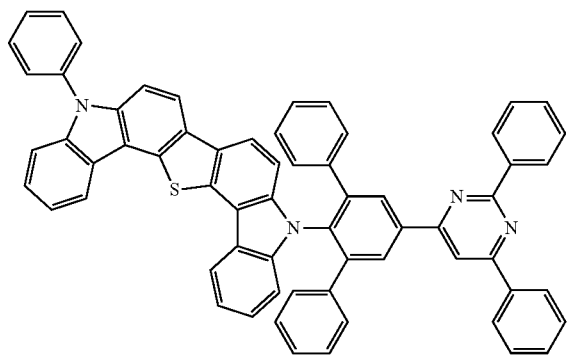
221
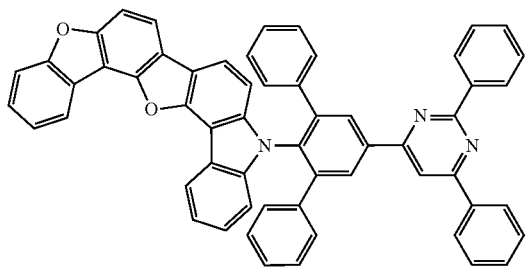
222
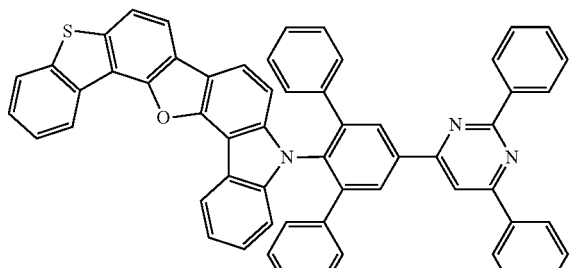

-continued
223
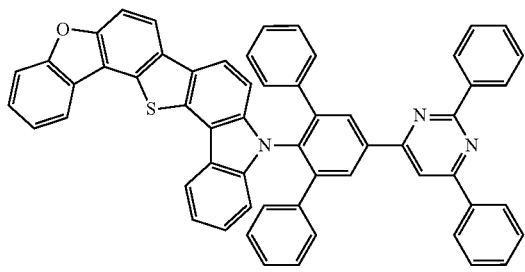
224
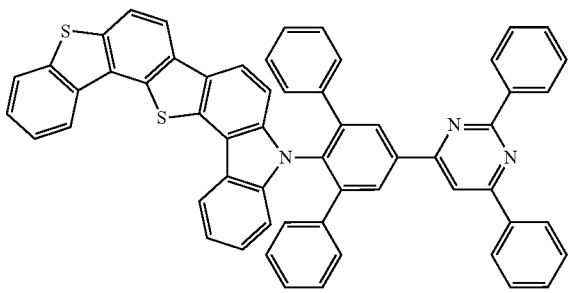
225
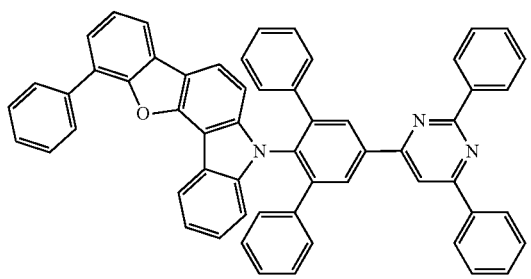
226
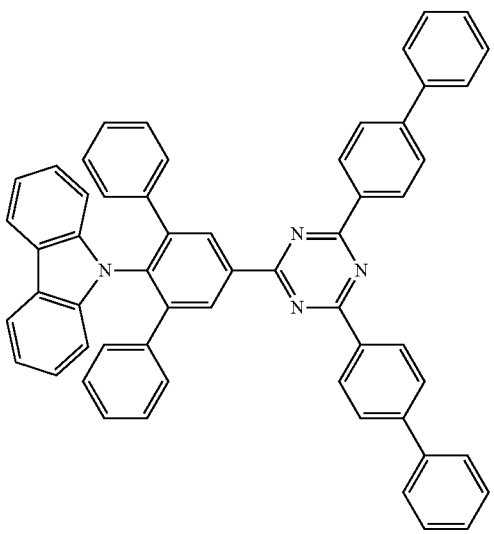
227
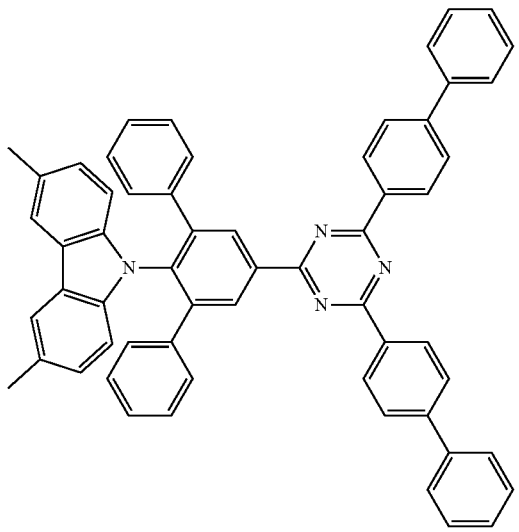
228
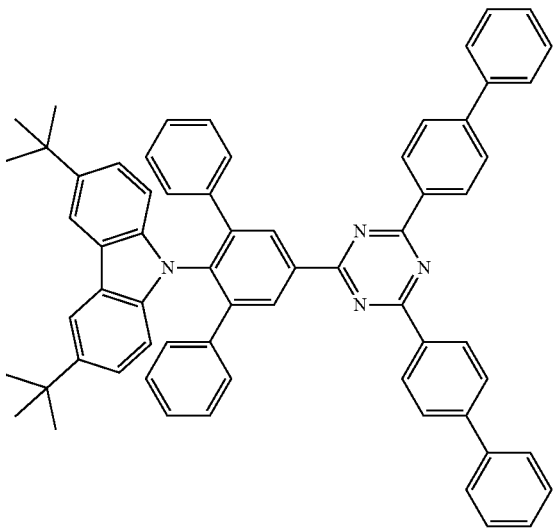

-continued
229
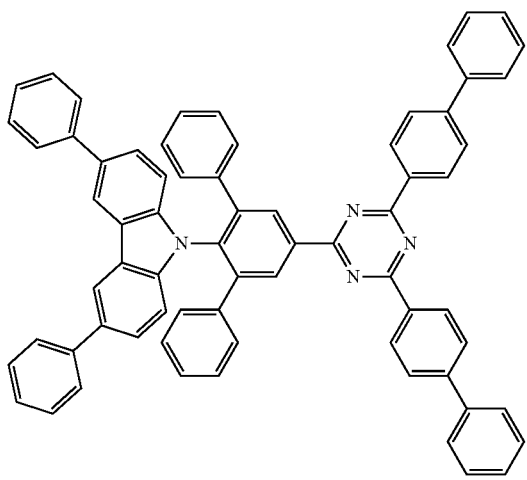
230
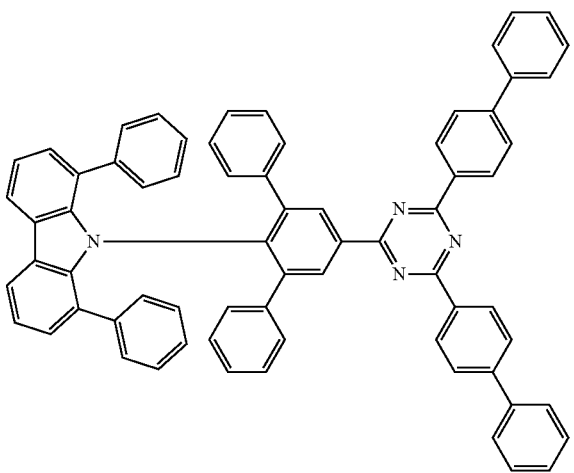
231
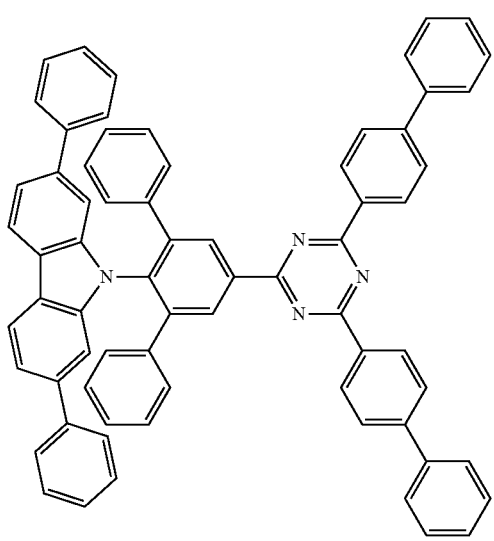
232
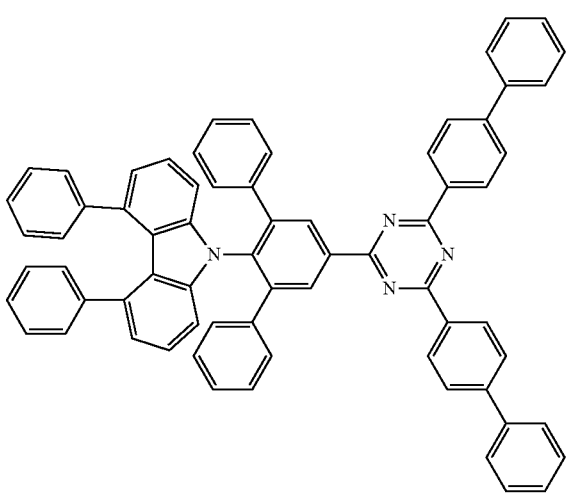
233
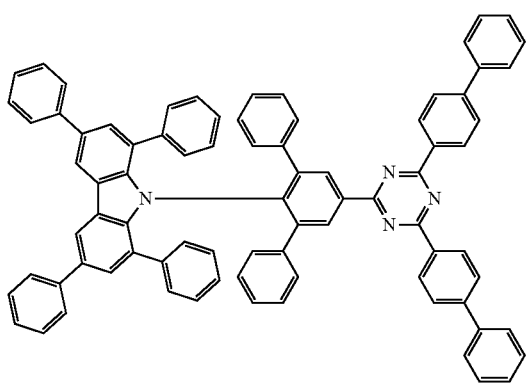
234
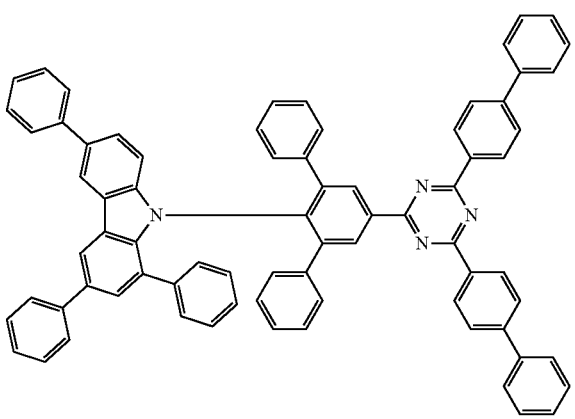

-continued
235
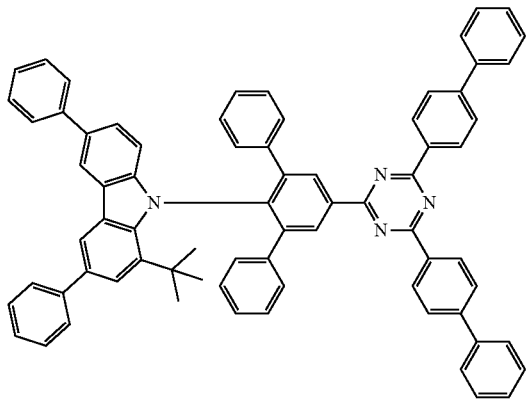
236
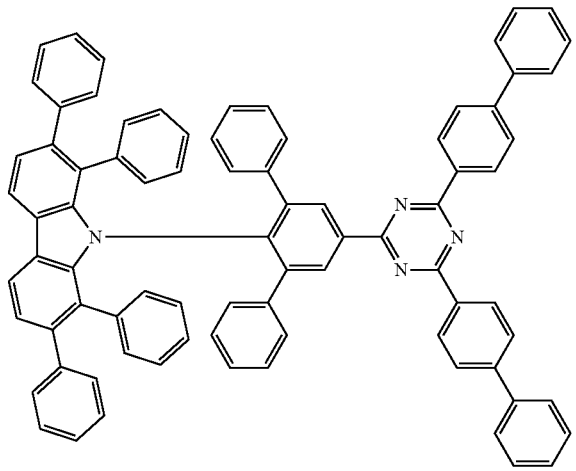
237
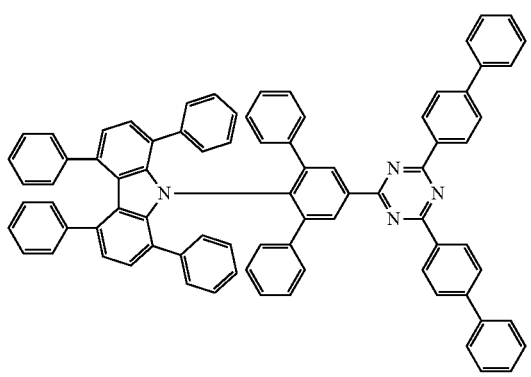
238
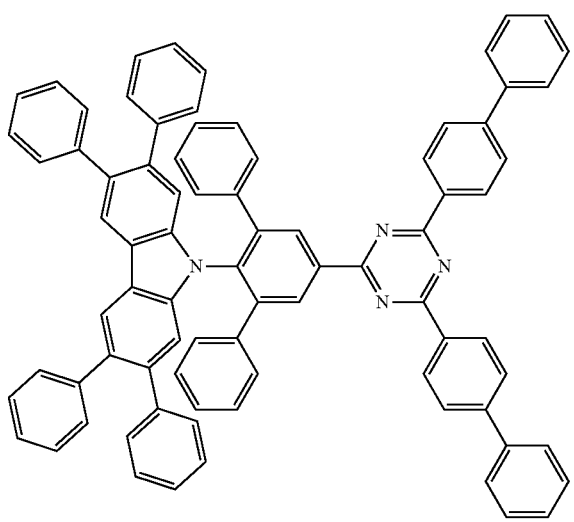
239
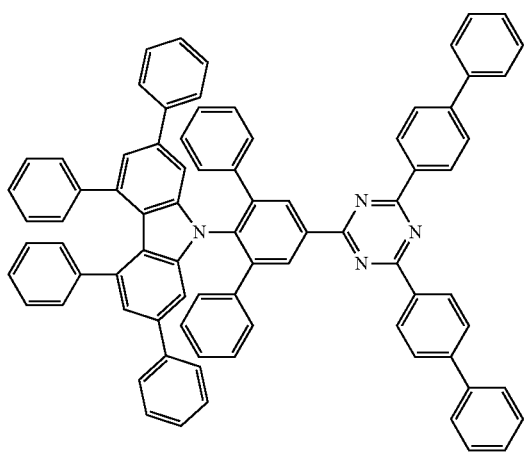
240
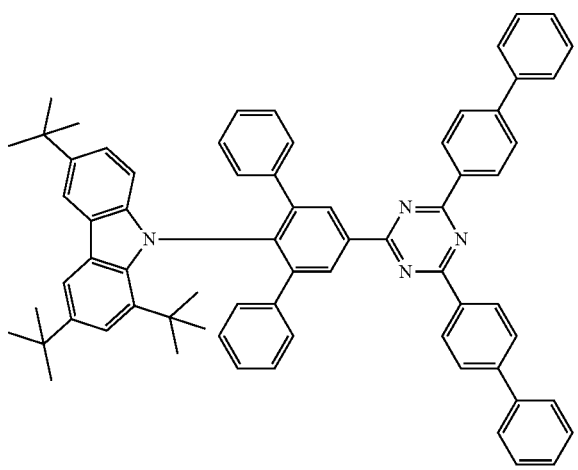

-continued
241
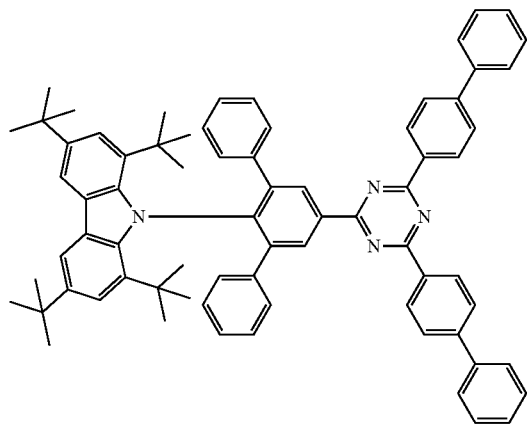
242
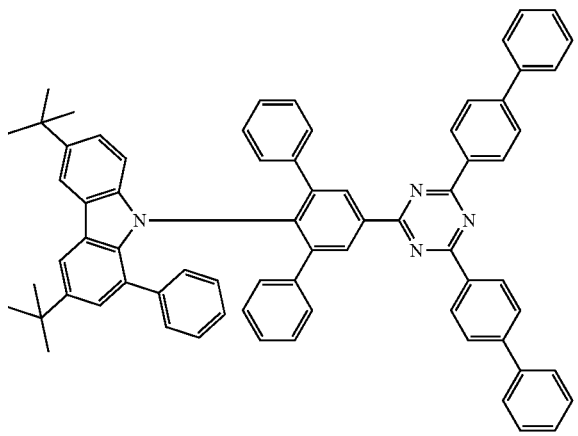
243
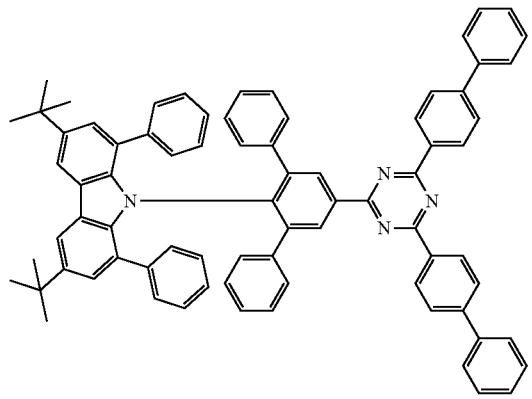
244
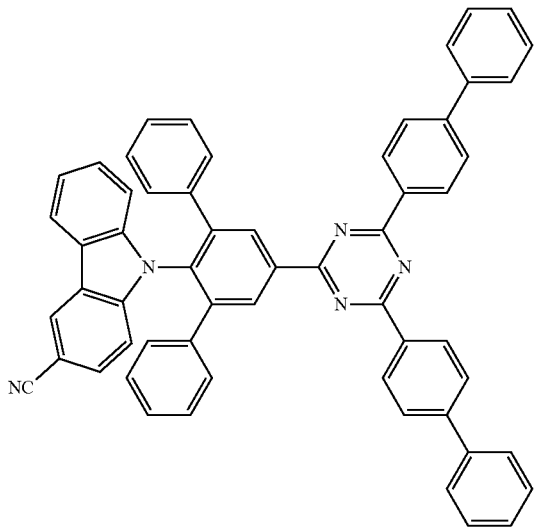
245
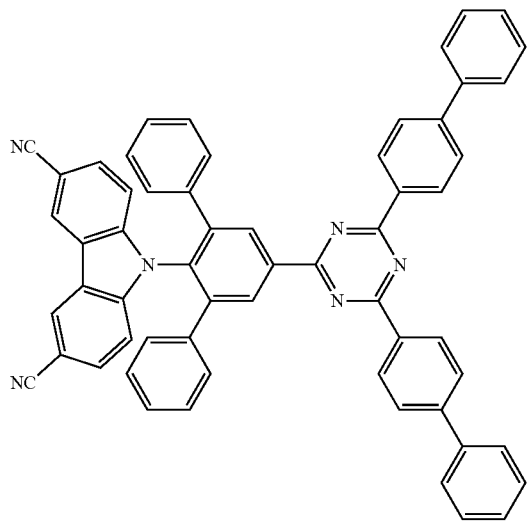
246
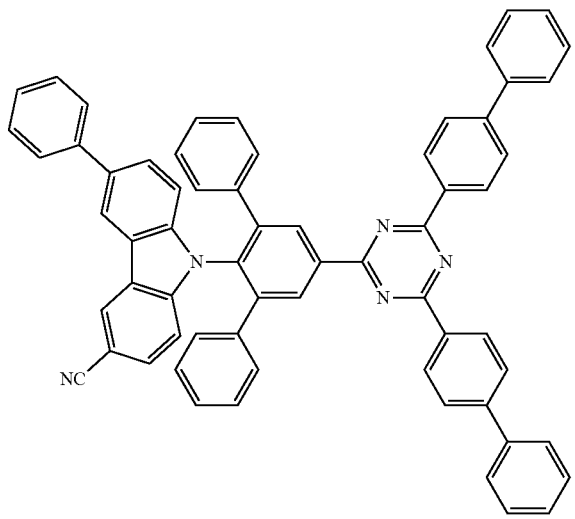

-continued
247
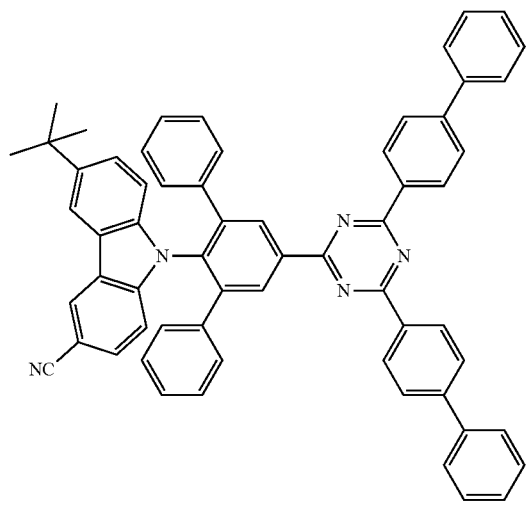
248
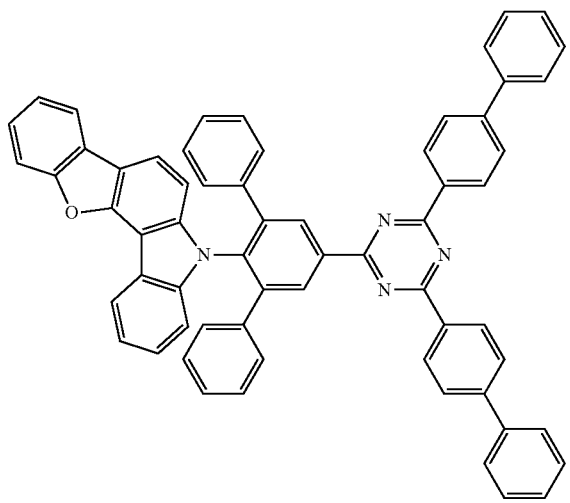
249
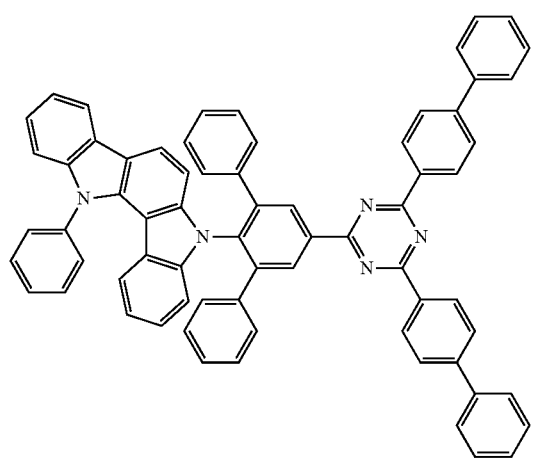
250
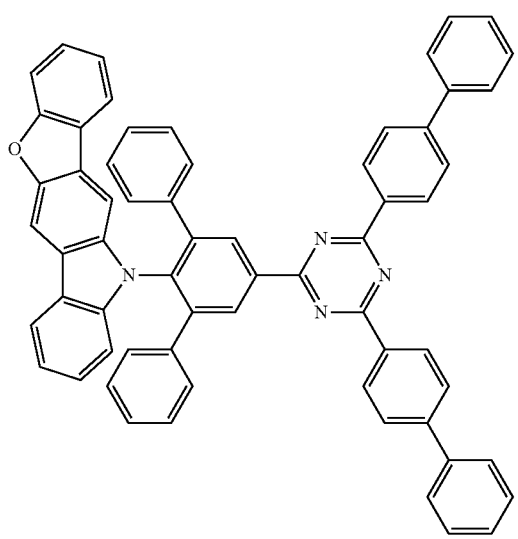
251
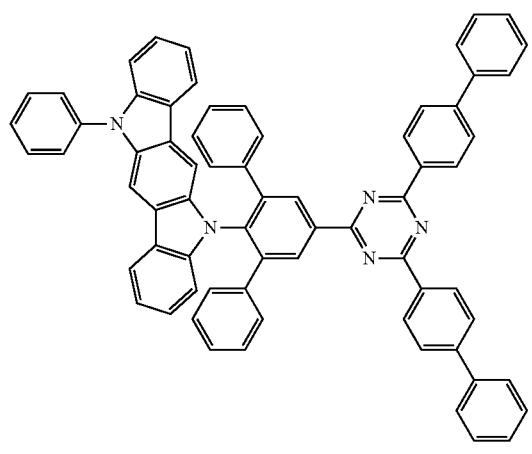
252
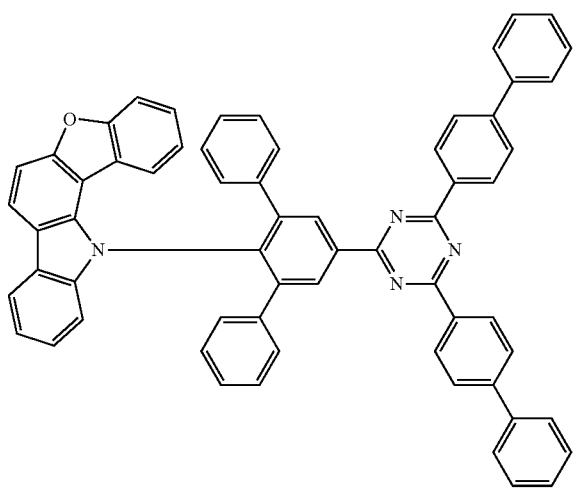

-continued
253
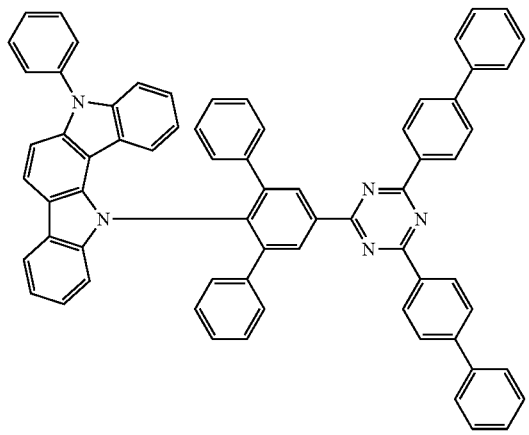
254
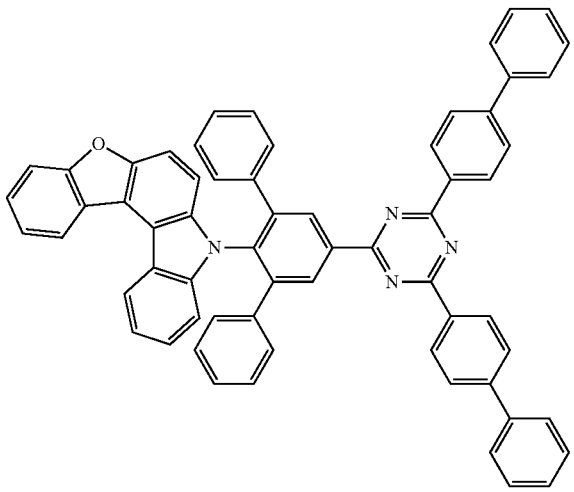
255
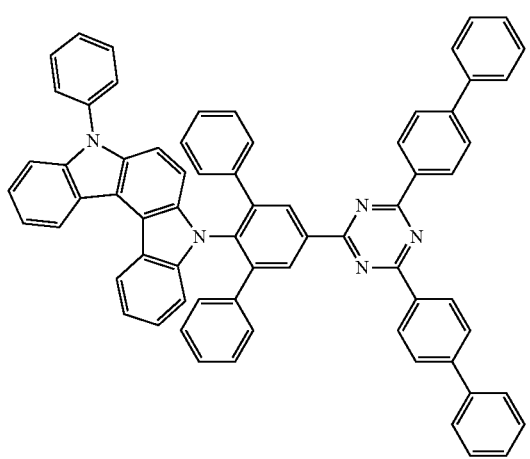
256
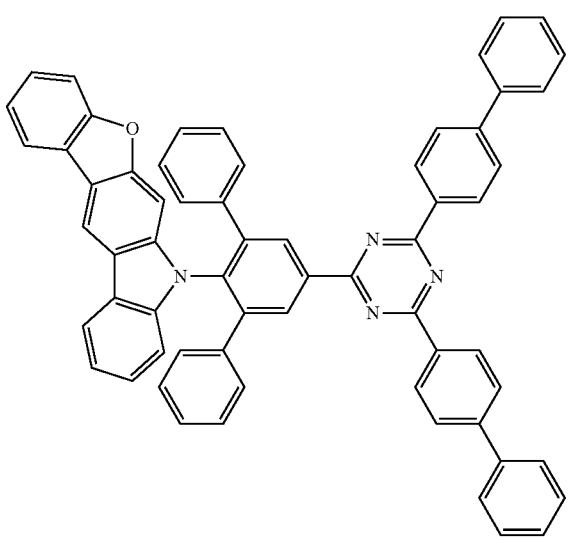
257
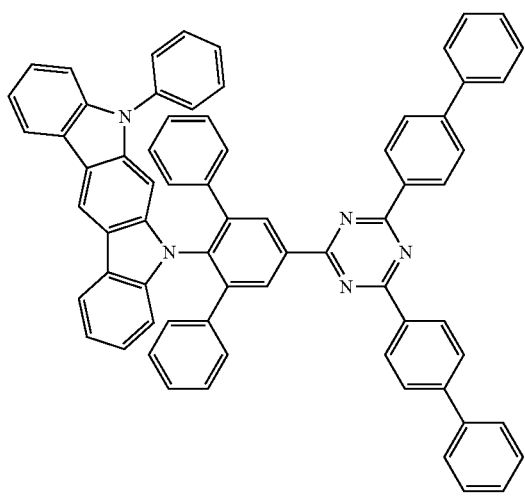
258
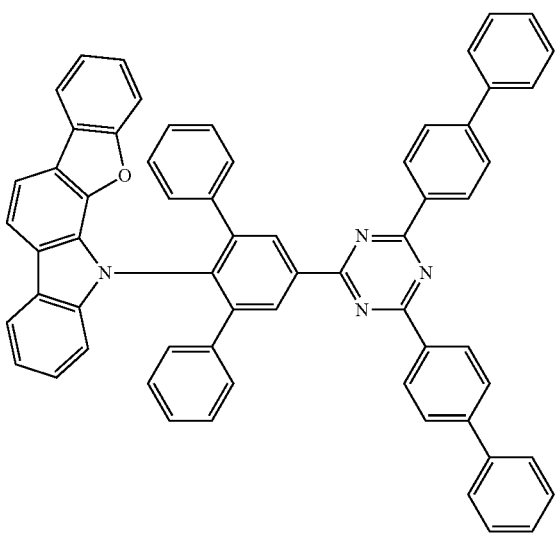

-continued
259
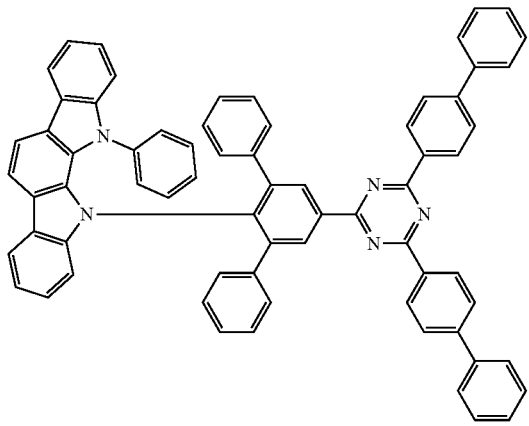
260
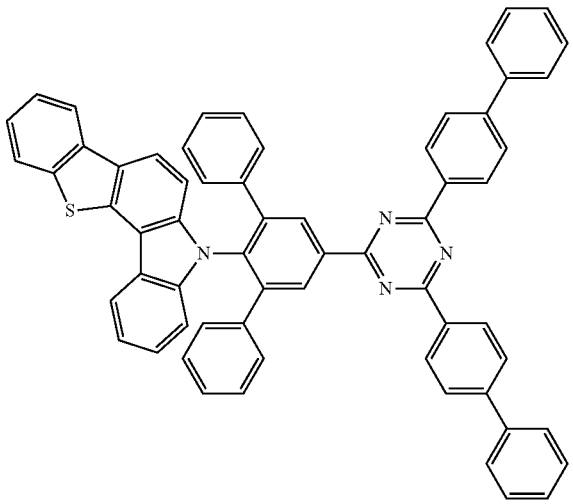
261
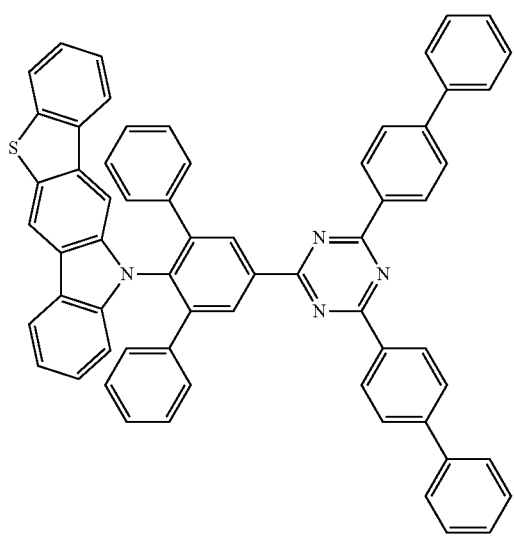
262
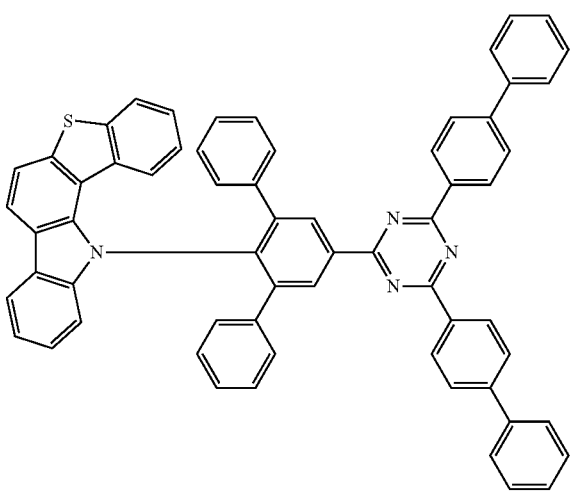
263
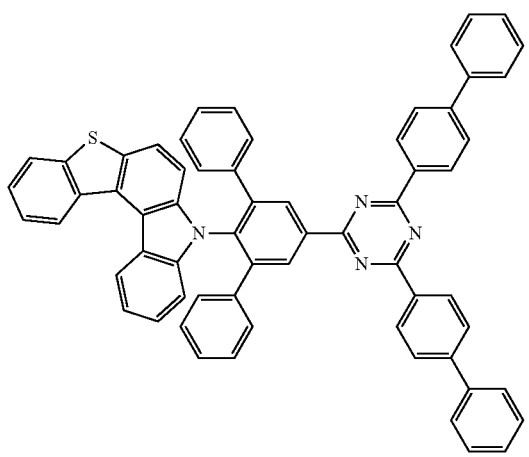
264
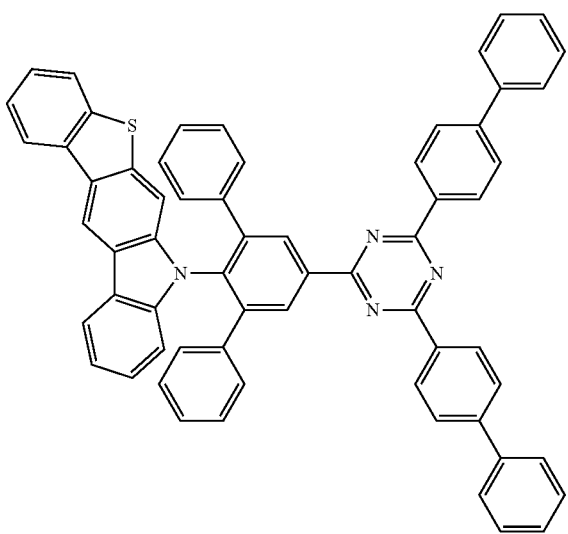

-continued
265
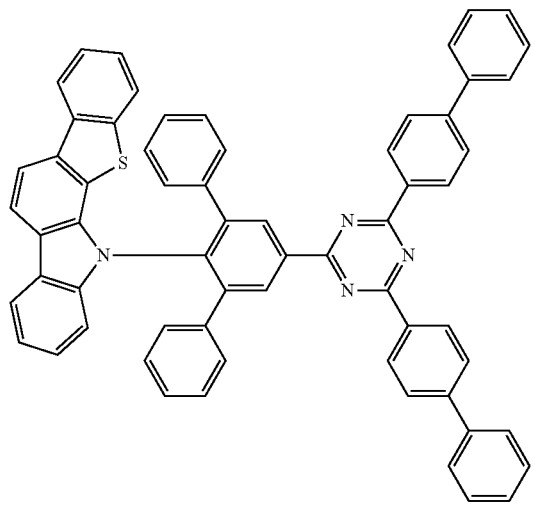
266
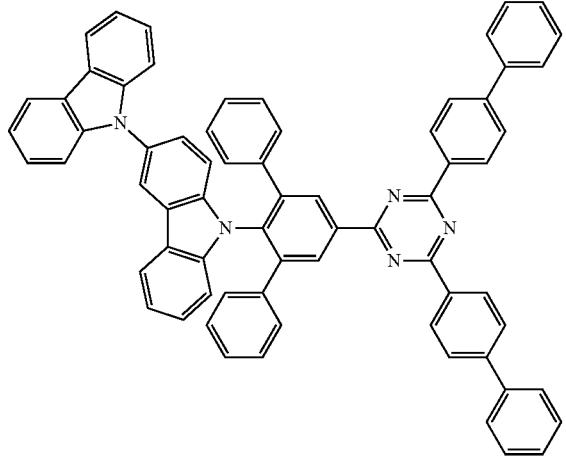
267
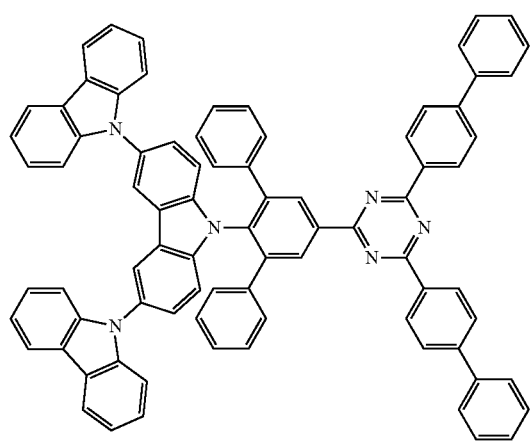
268
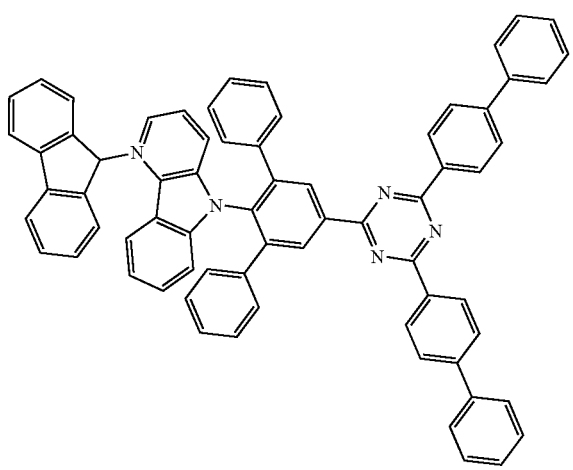
269
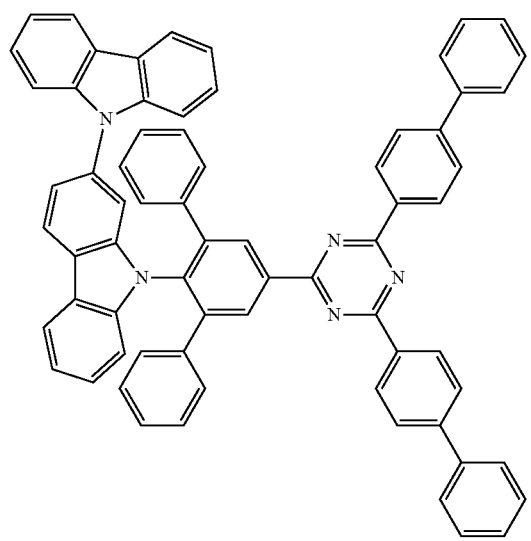
270
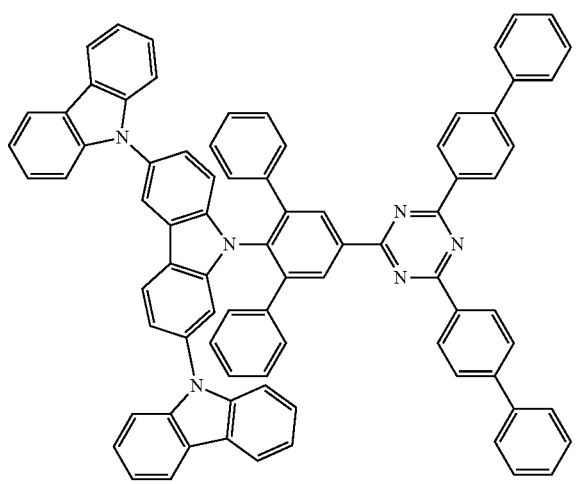

-continued
271
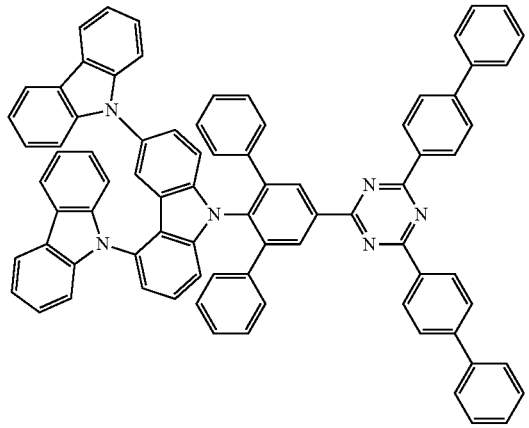
272
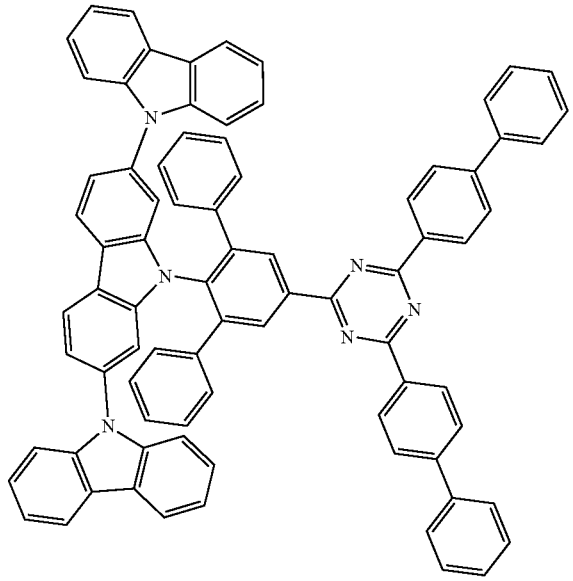
273
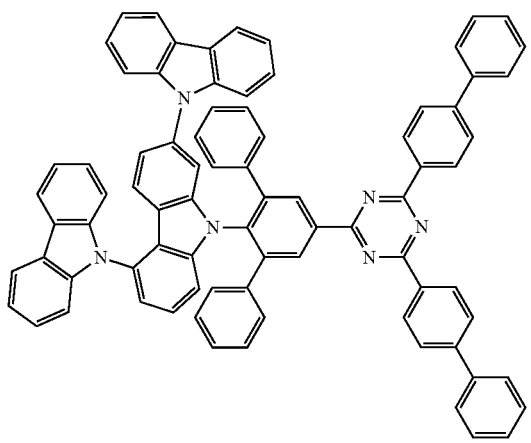
274
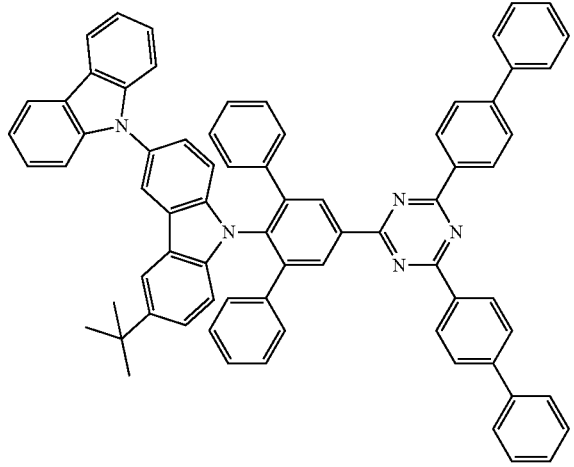
275
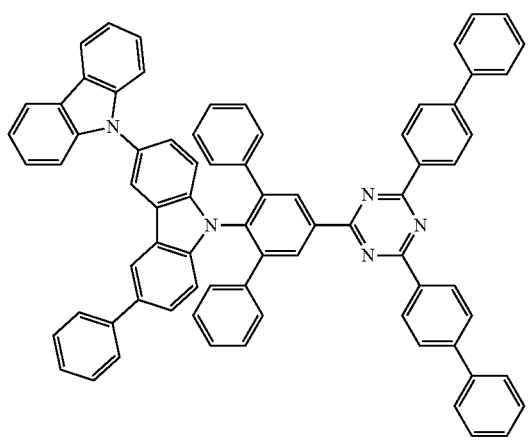
276
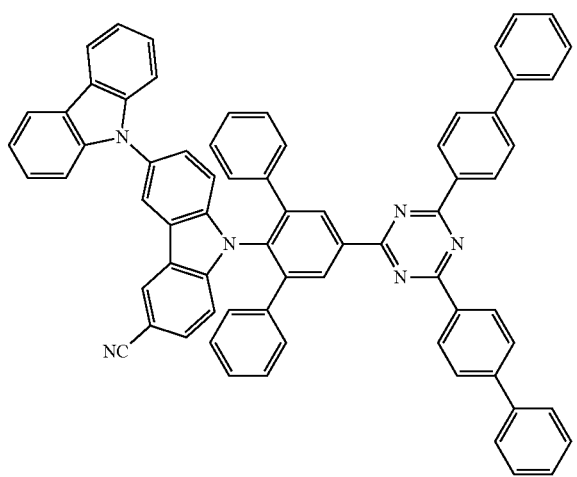

277
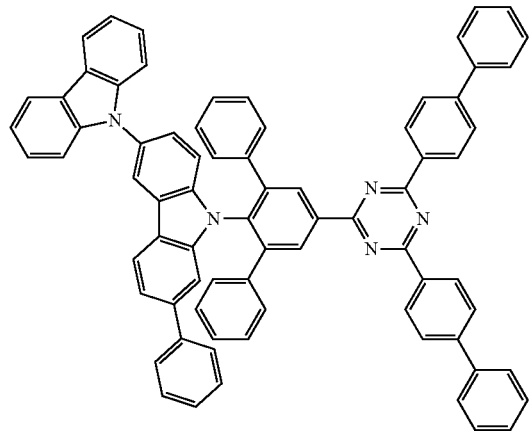
278
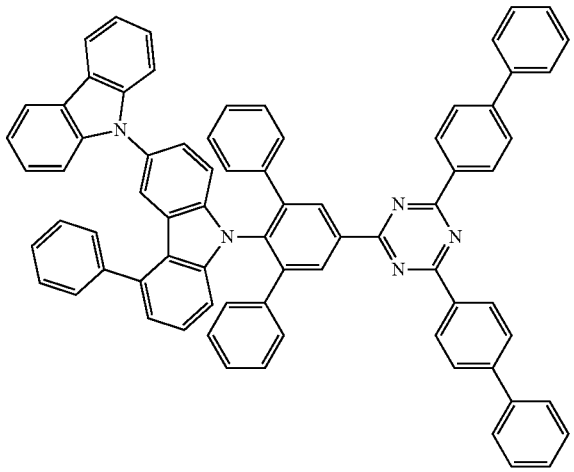
279
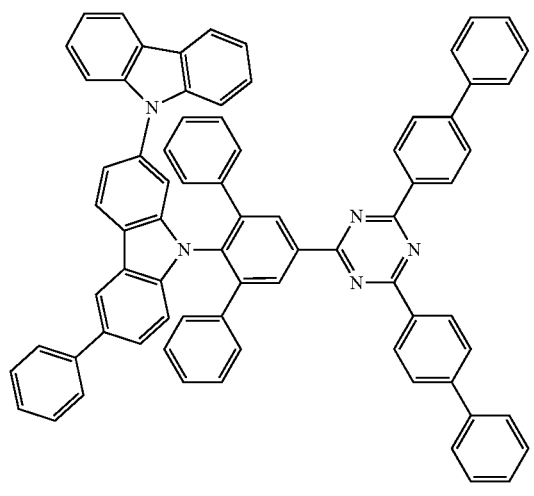
280
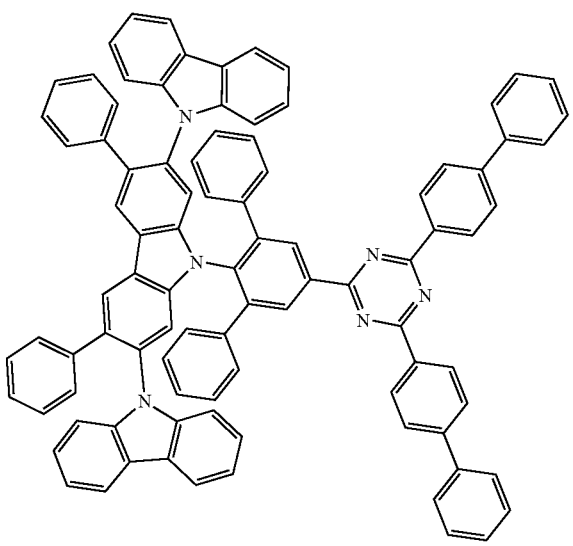
281
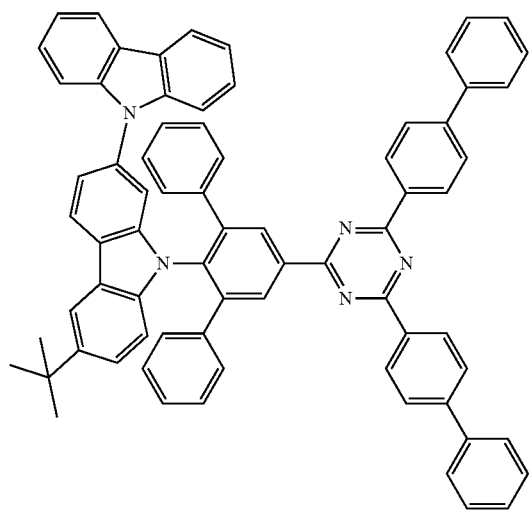
282
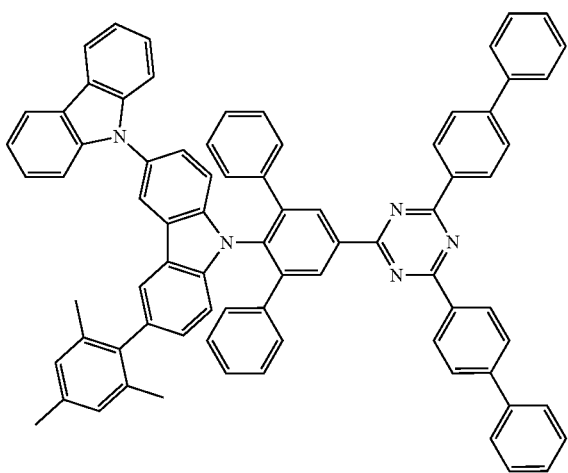

-continued
283
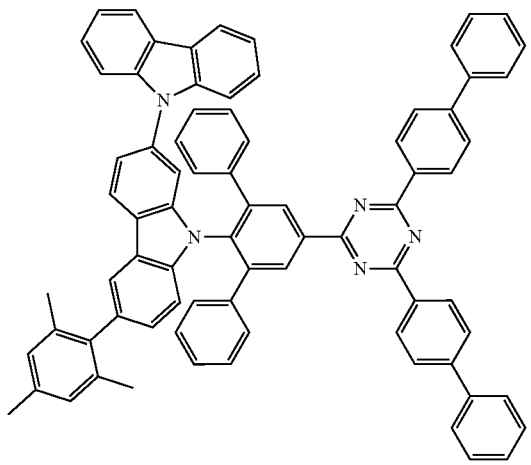
284
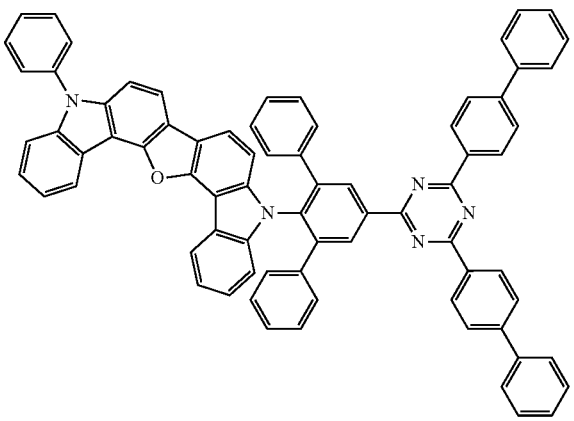
285
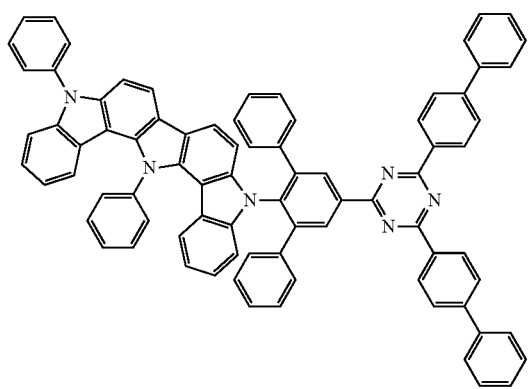
286
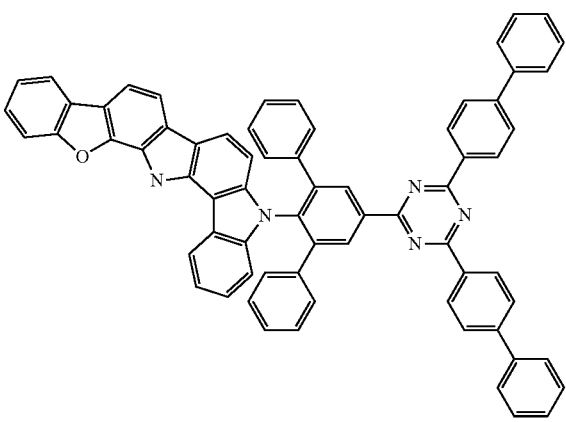
287
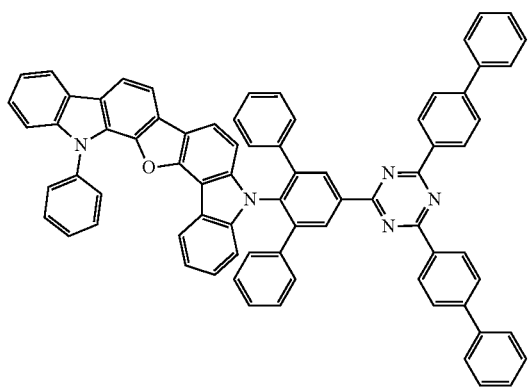
288
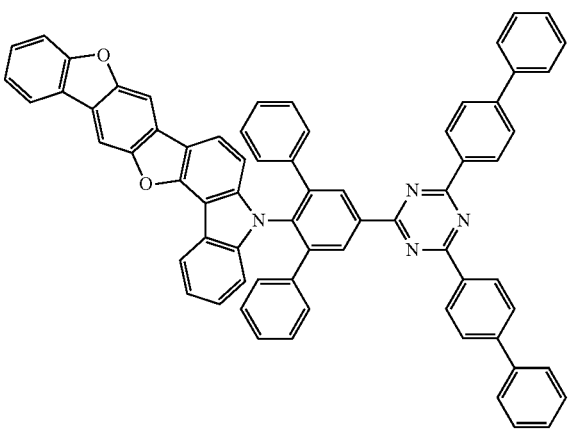

-continued
289
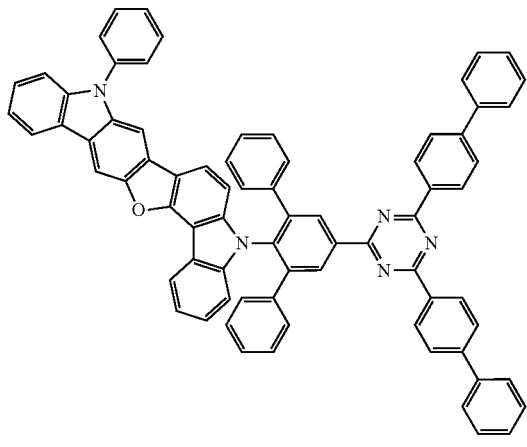
290
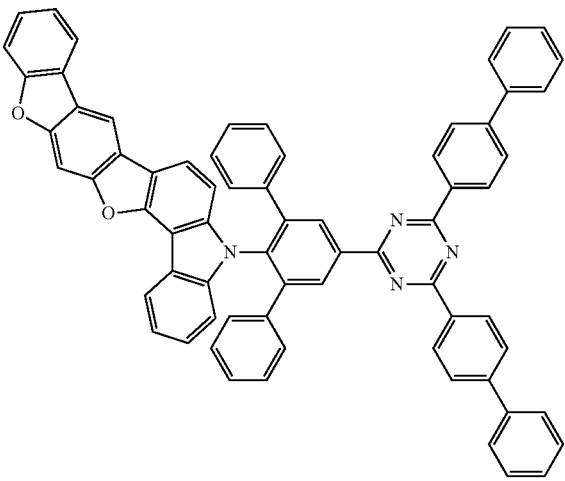
291
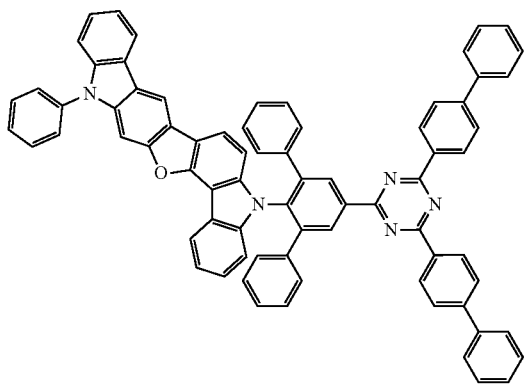
292
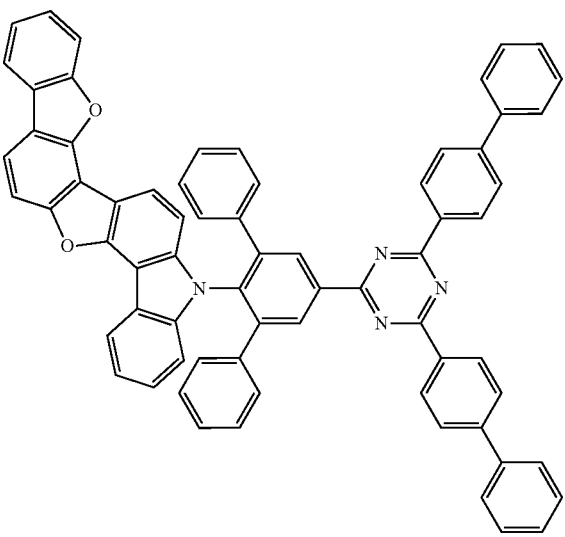
293
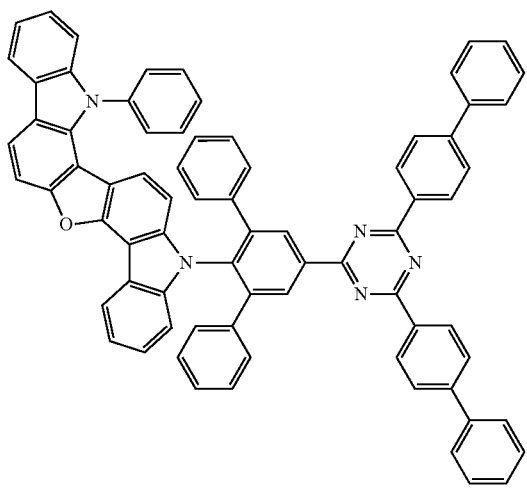
294
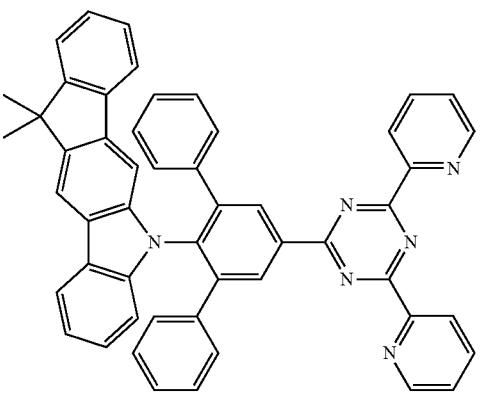

-continued
| 991 | 992 |
|---|---|
| 295 | 296 |
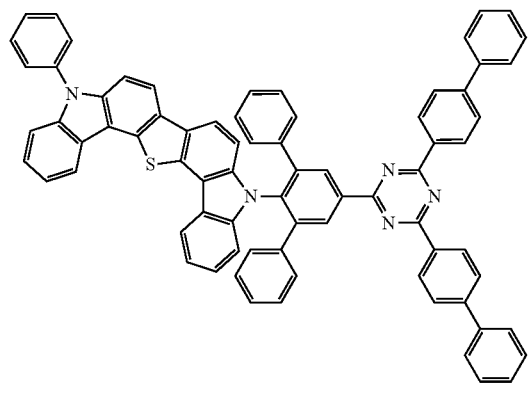
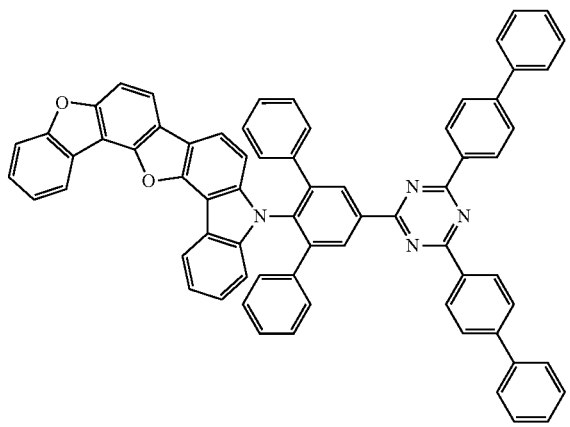
| 297 | 298 |
|---|---|
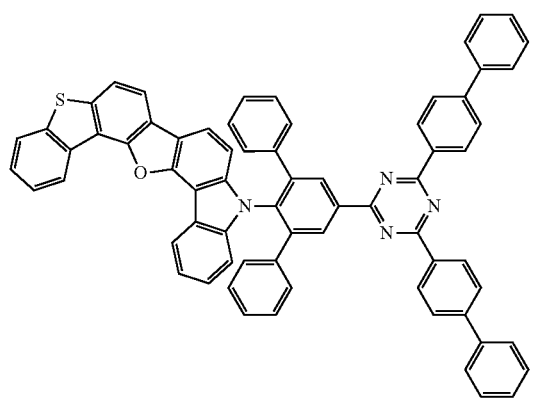
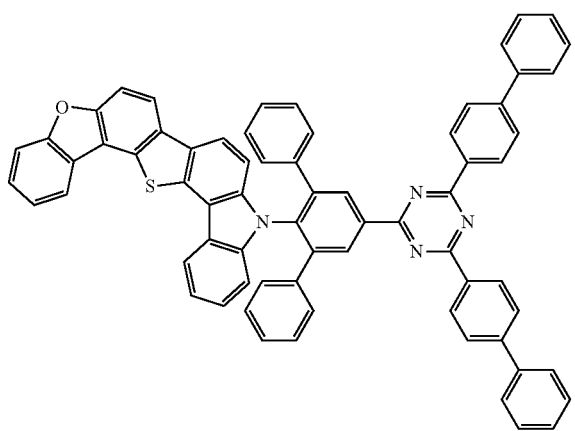
| 299 | 300 |
|---|---|
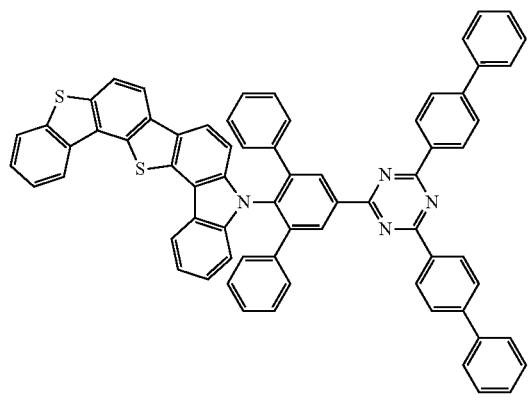
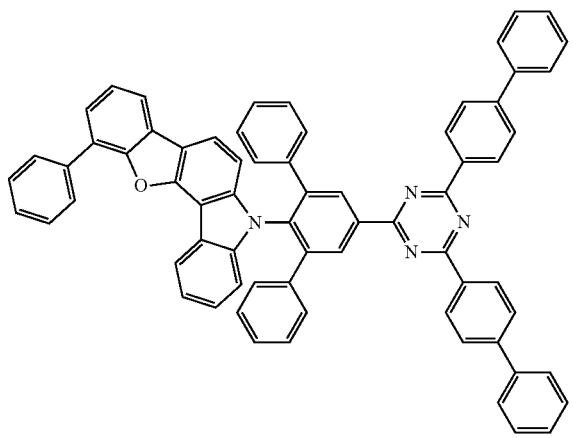

993 994
-continued
301 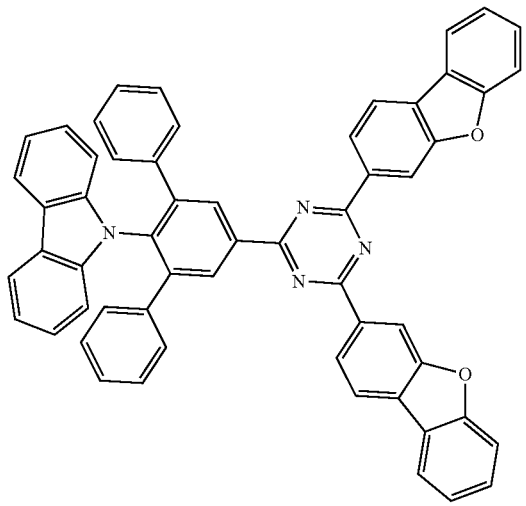 302 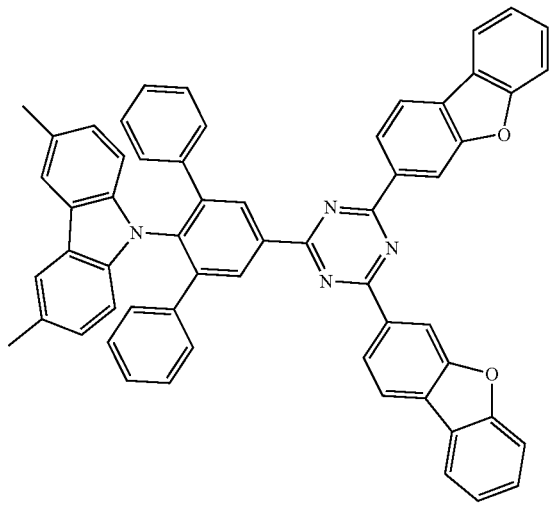
303 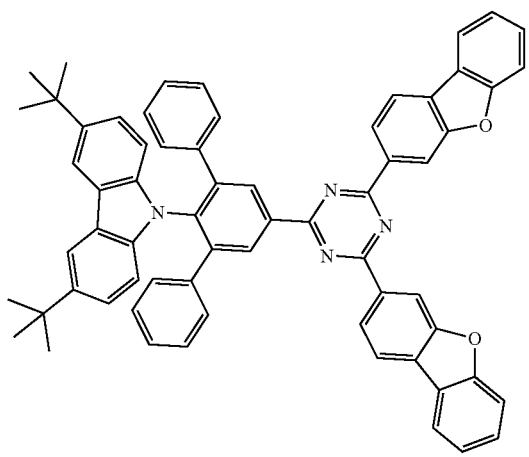 304 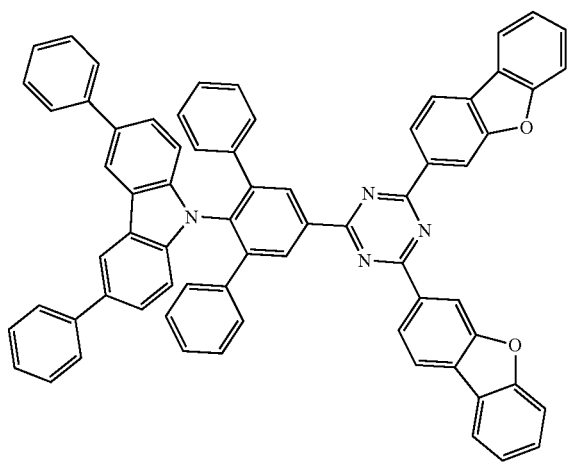
305 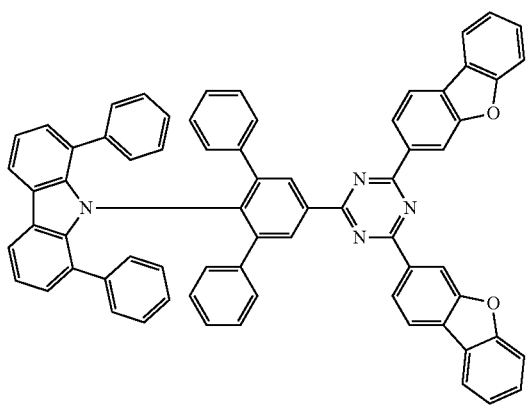 306 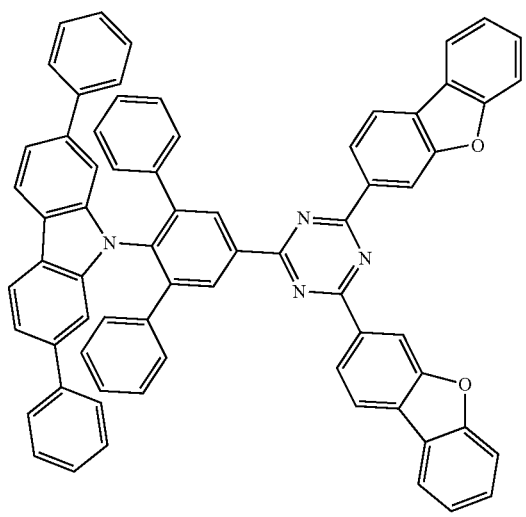

-continued
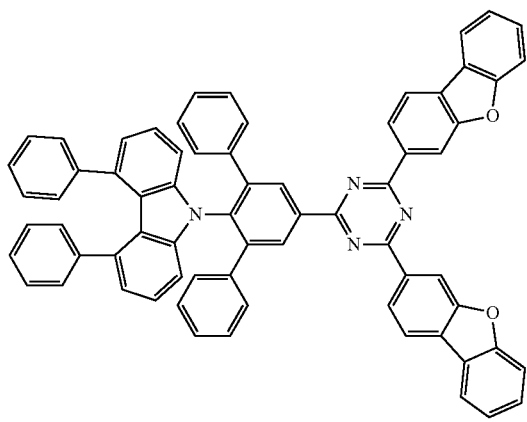
307
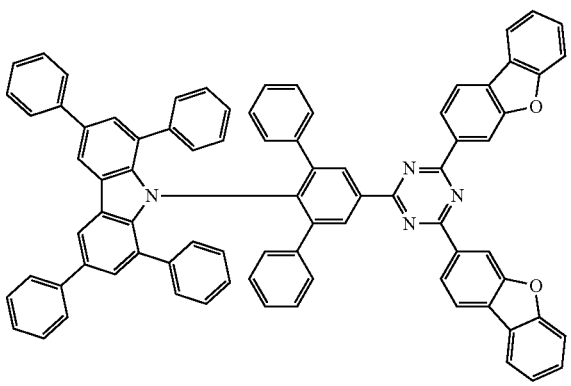
308
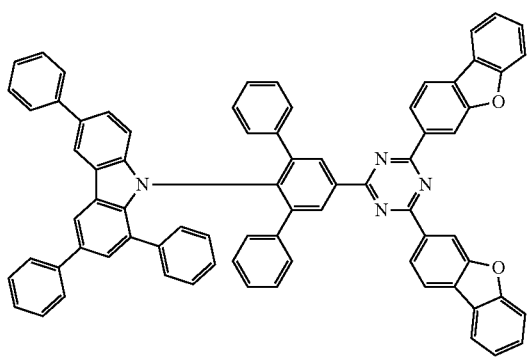
309
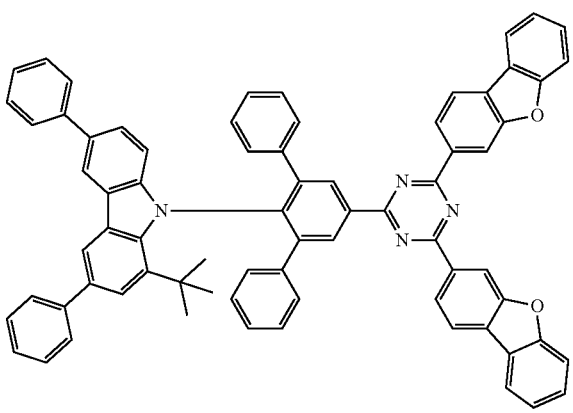
310
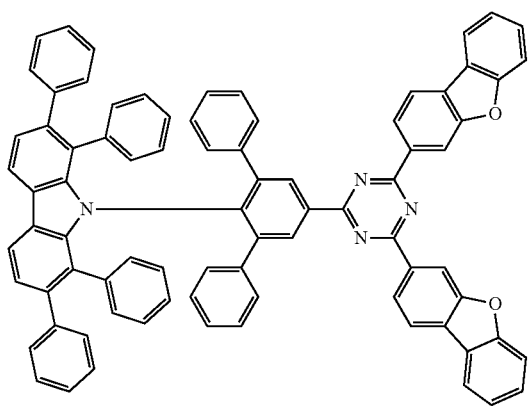
311

-continued
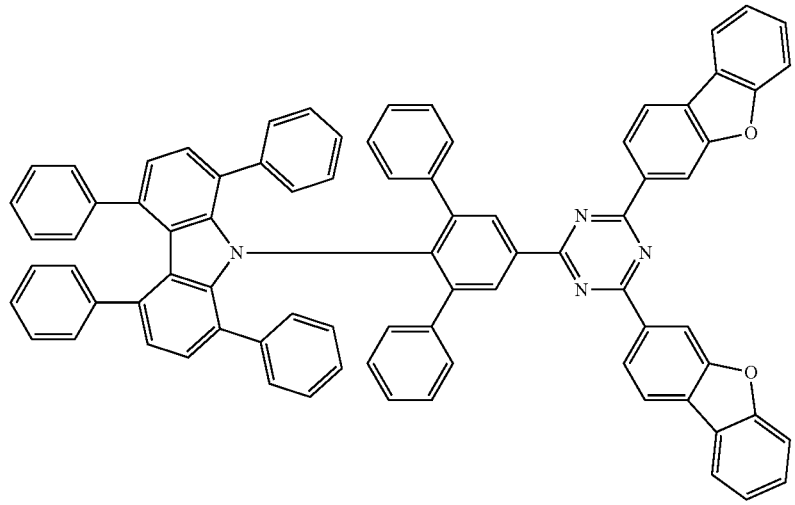
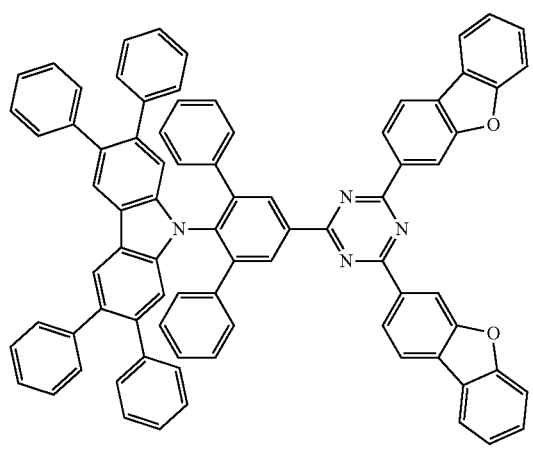
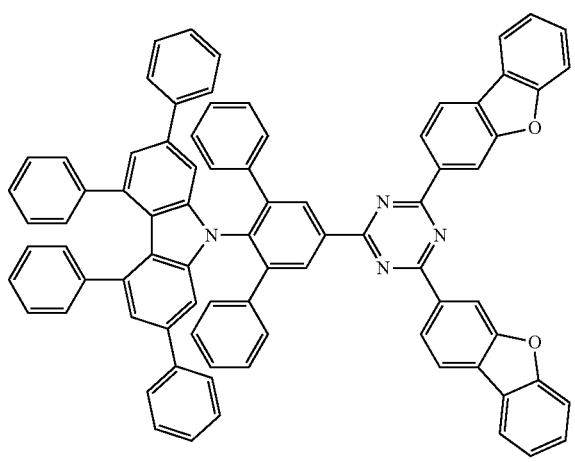
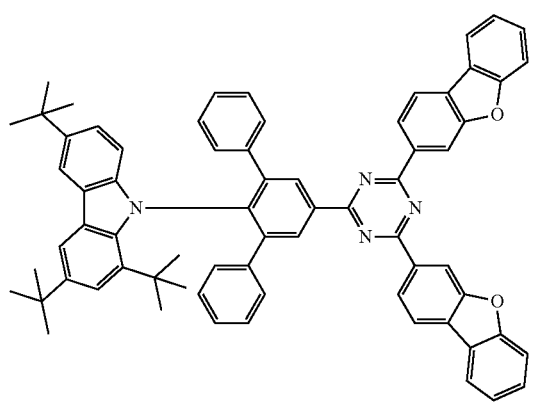
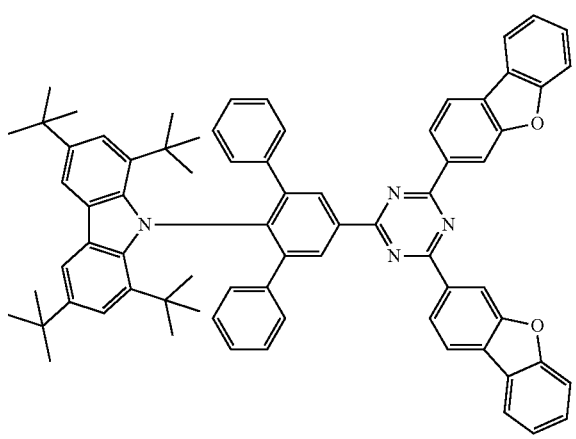

317
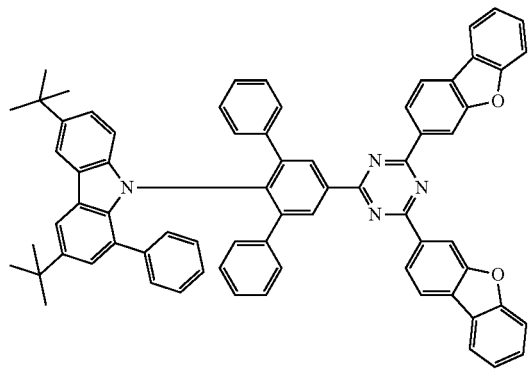
318
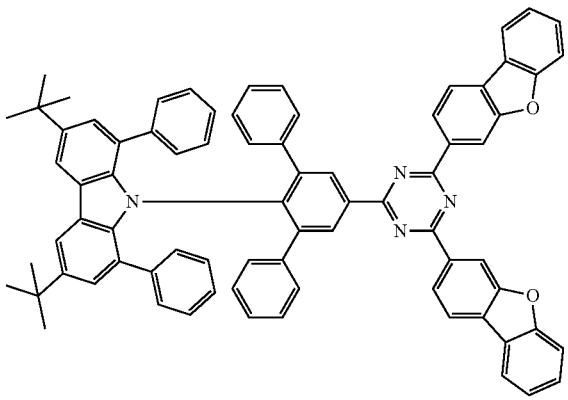
319
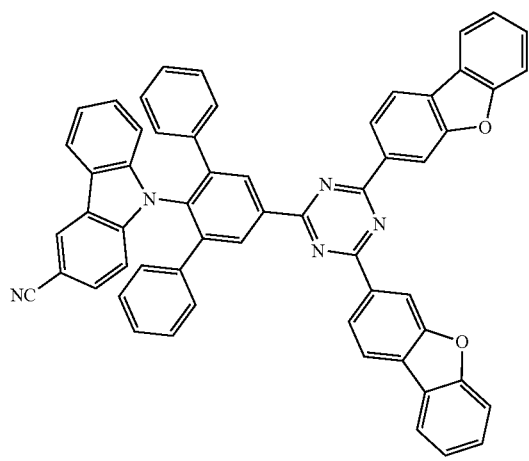
320
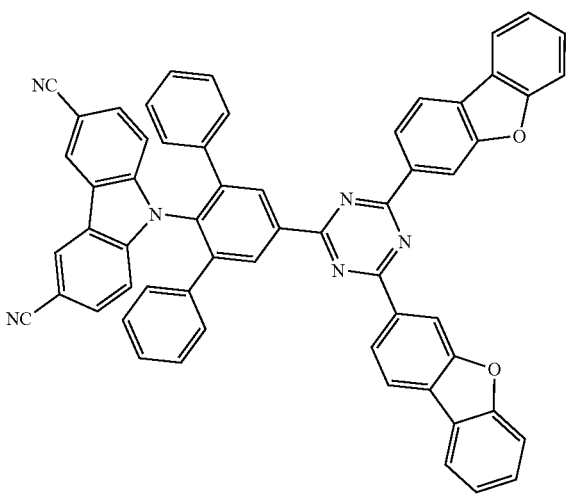
321
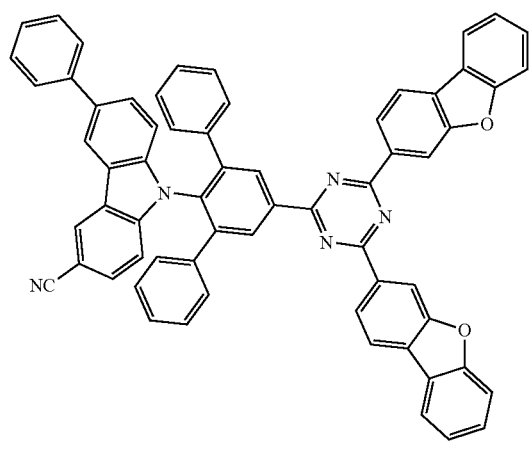
322
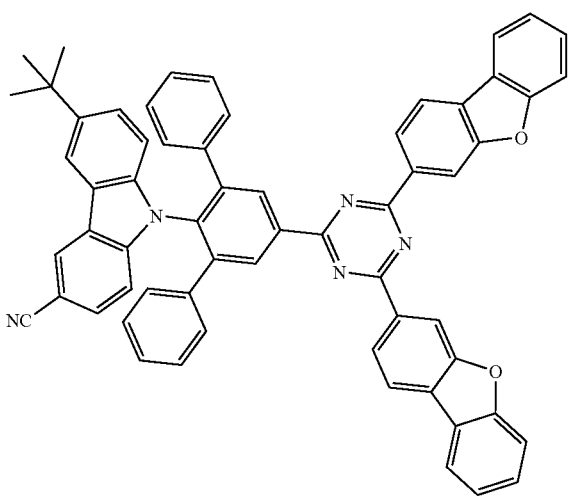

-continued
323
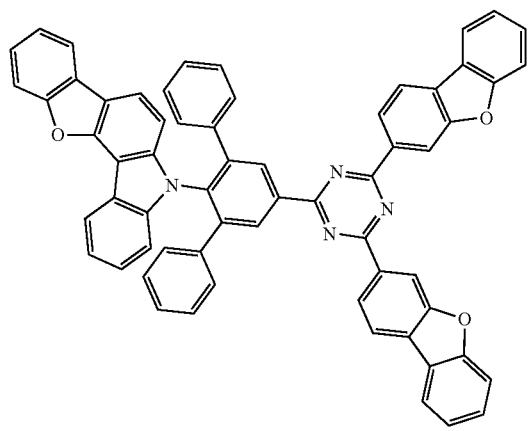
324
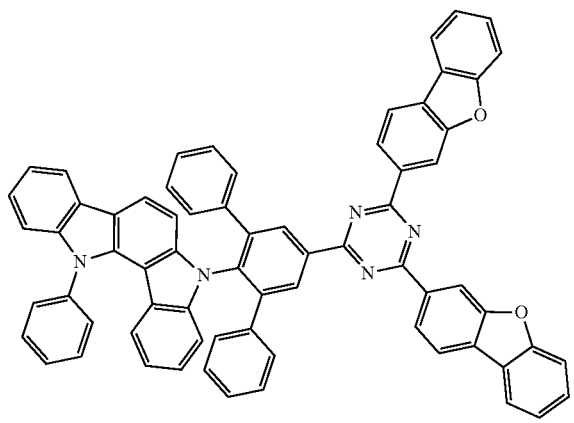
325
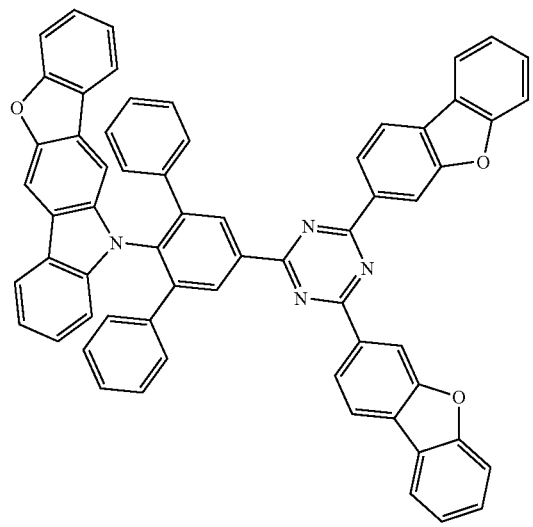
326
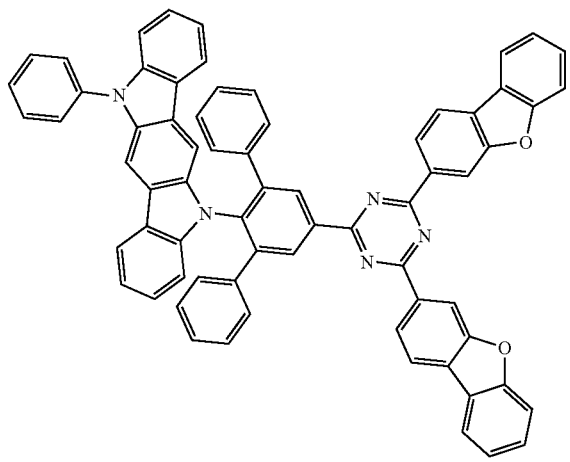
327
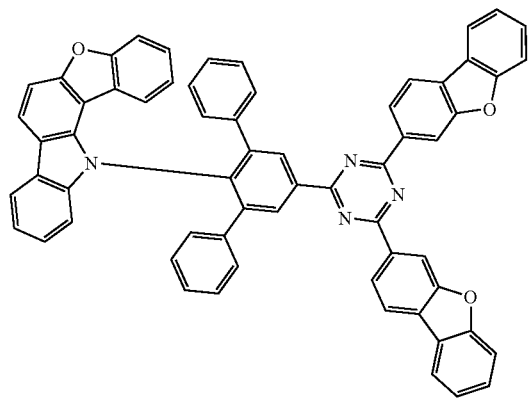
328
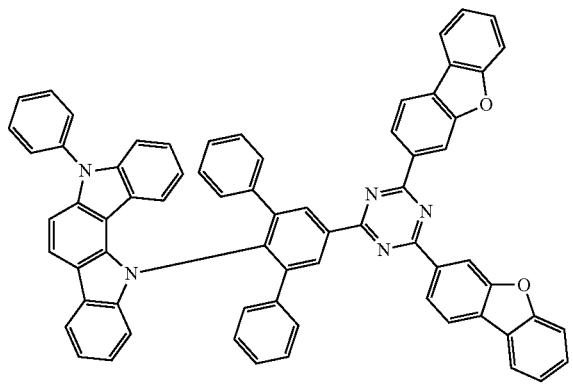

-continued
1003
329
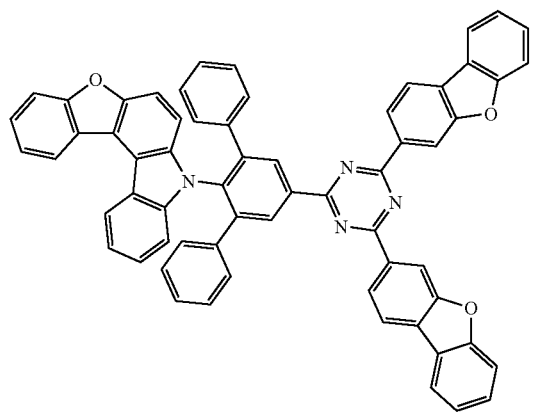
331
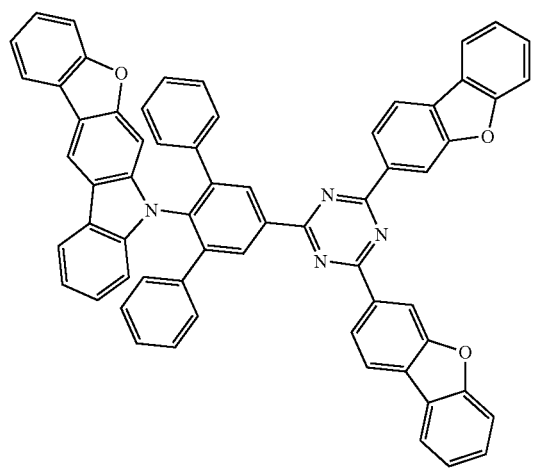
333
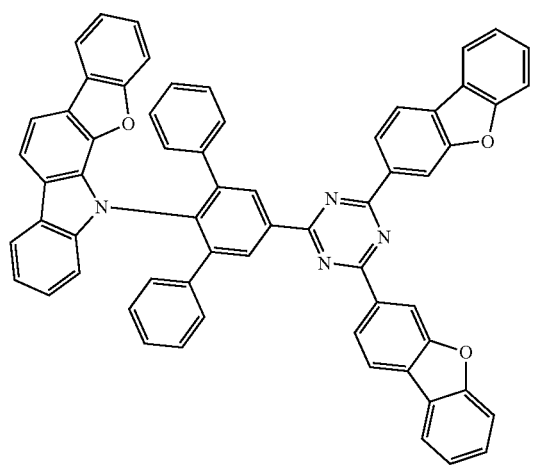
1004
330
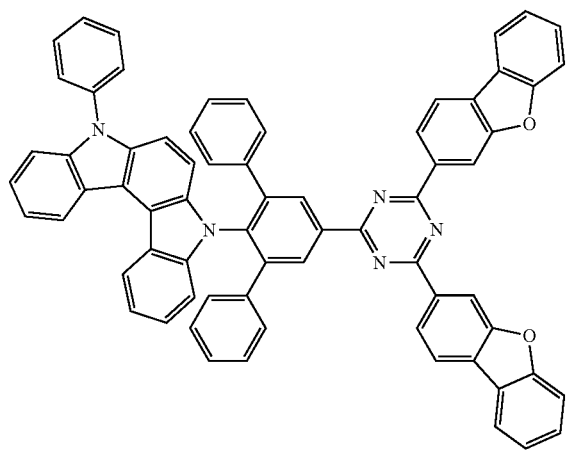
332
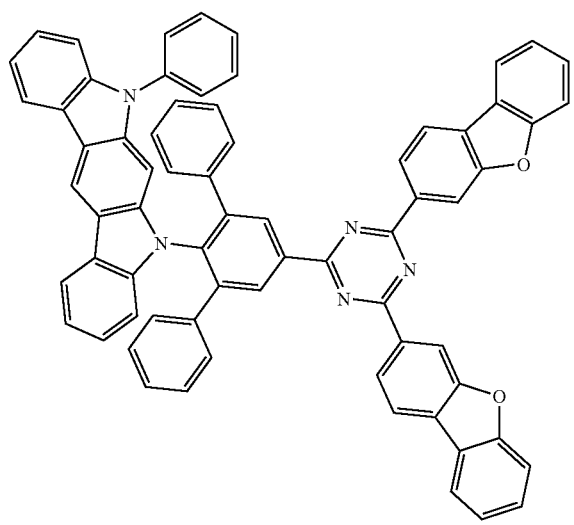
334
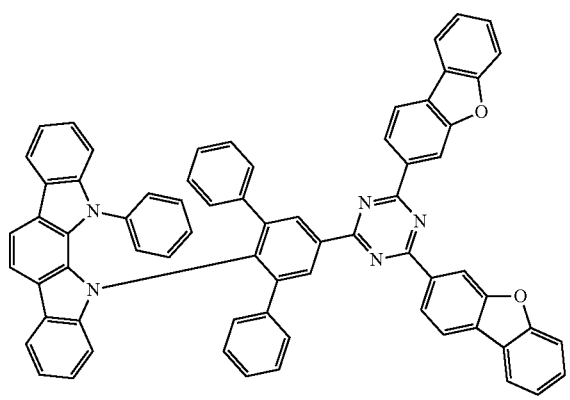

-continued
1005
335
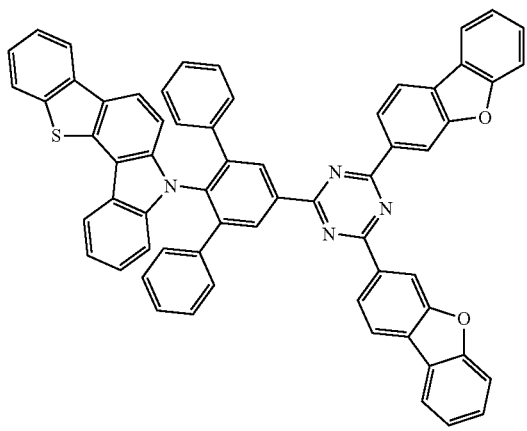
1006
336
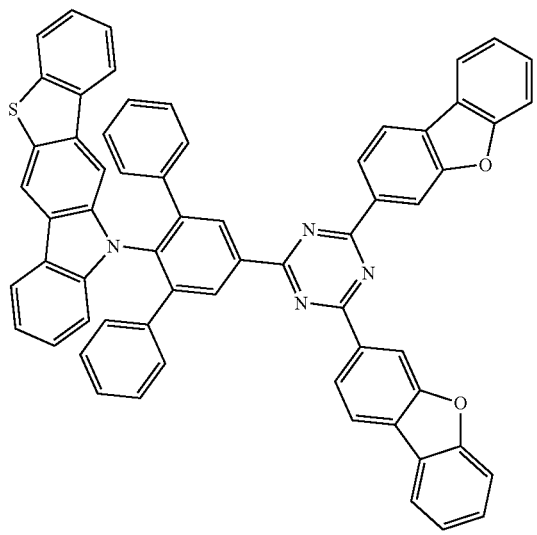
337
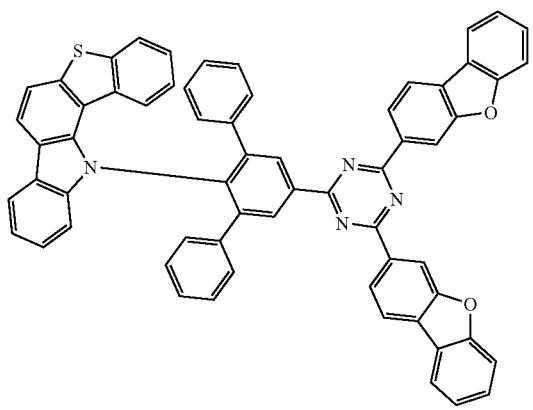
338
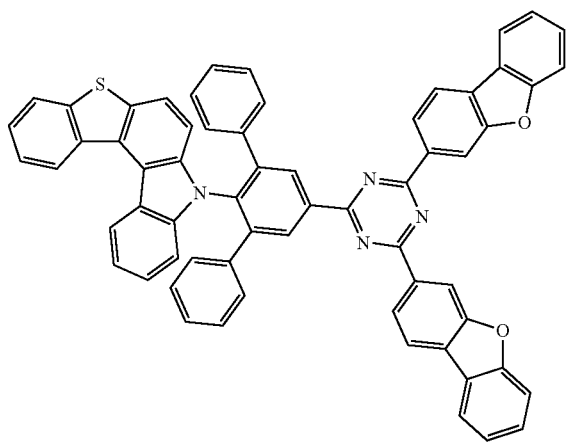
339
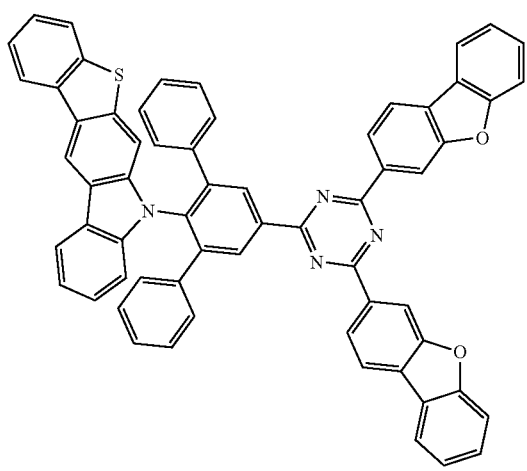
340
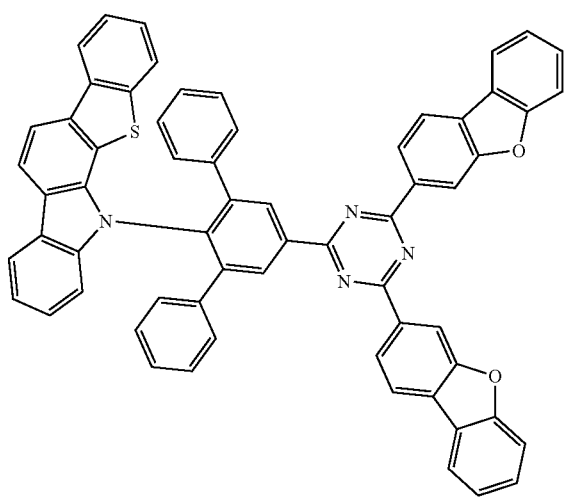

-continued
341
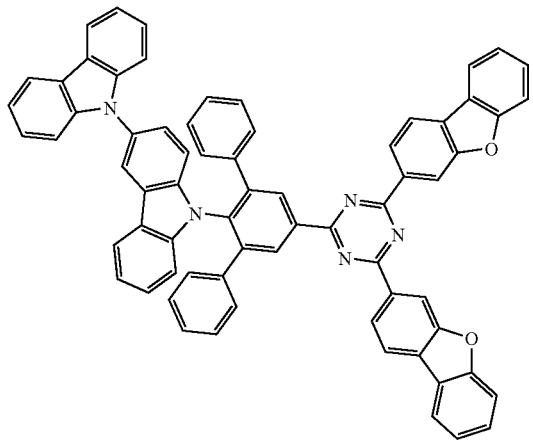
342
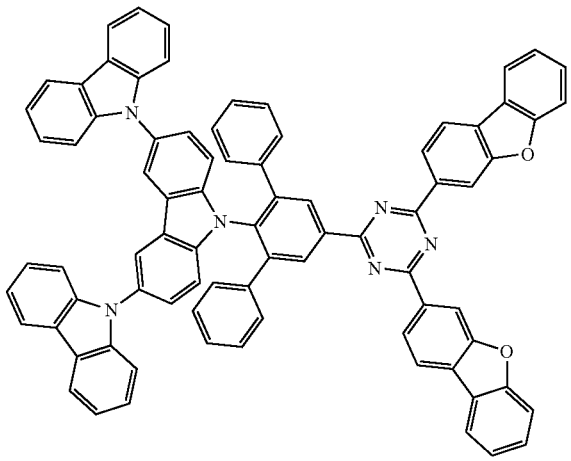
343
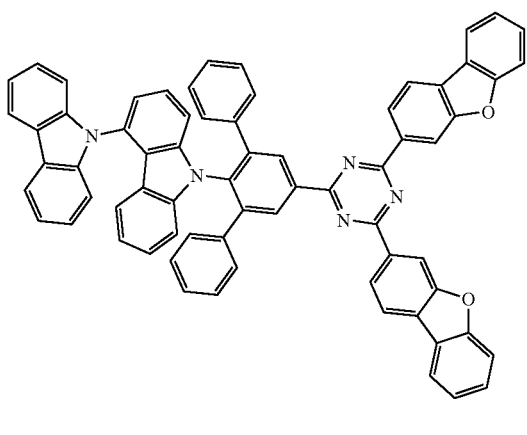
344
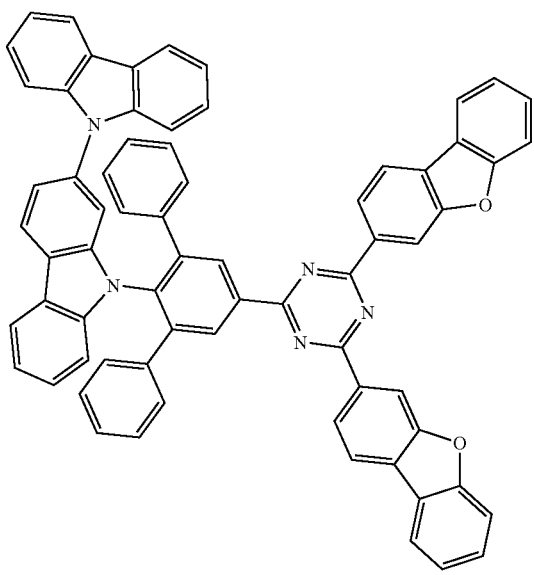
345
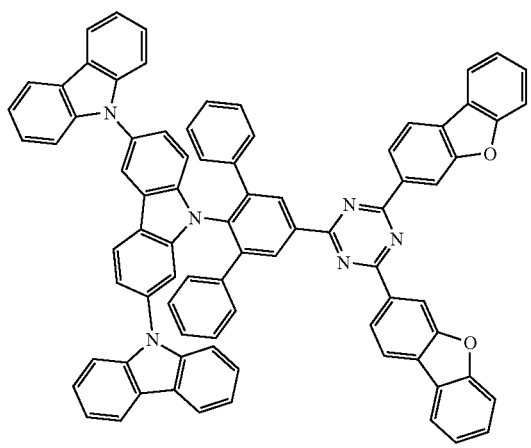
346
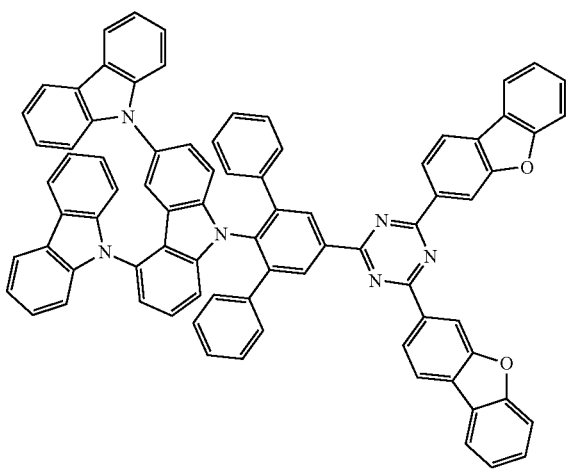

-continued
1009
347
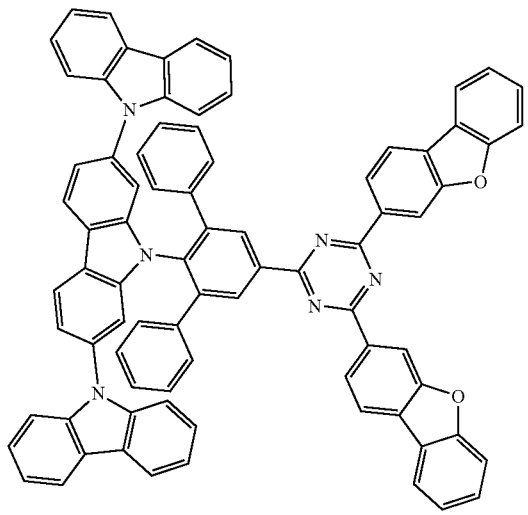
348
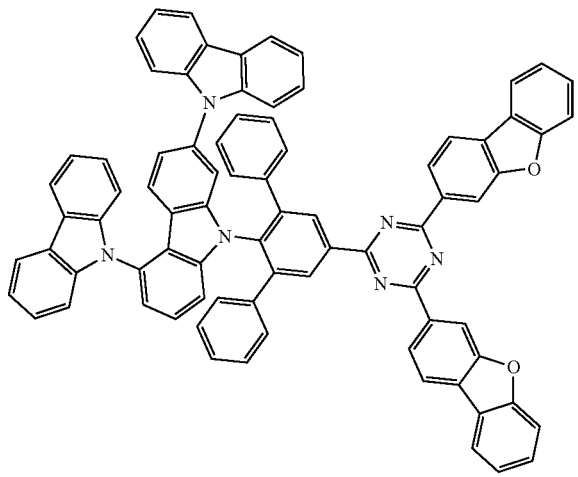
1010
349
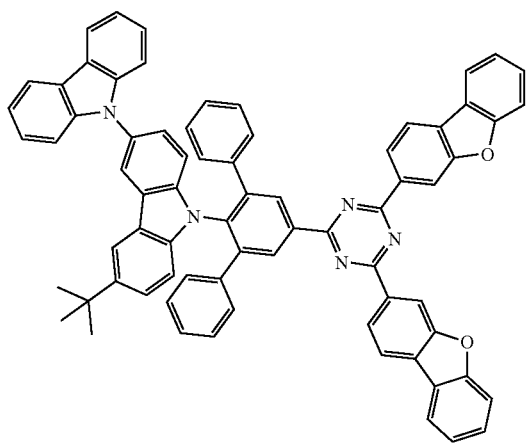
350
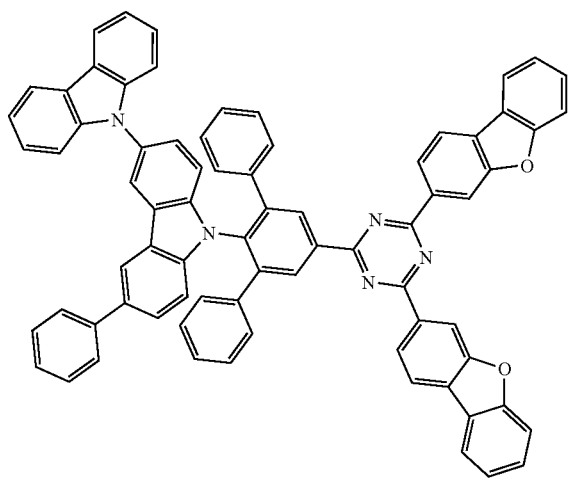
351
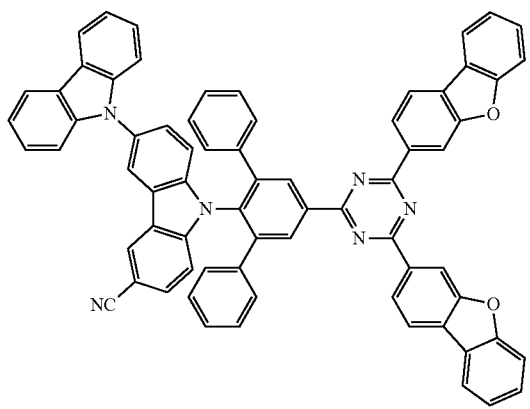
352
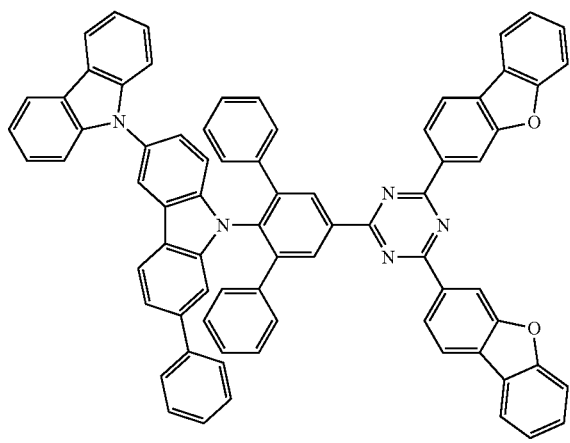

-continued
353
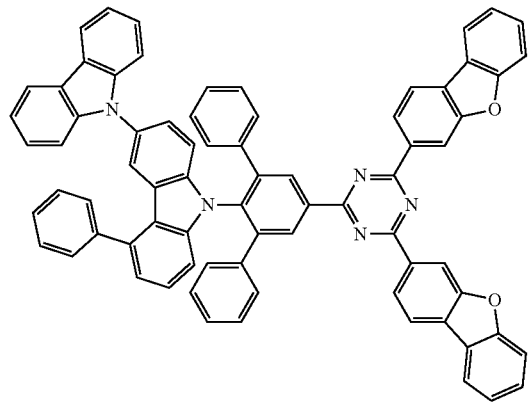
354
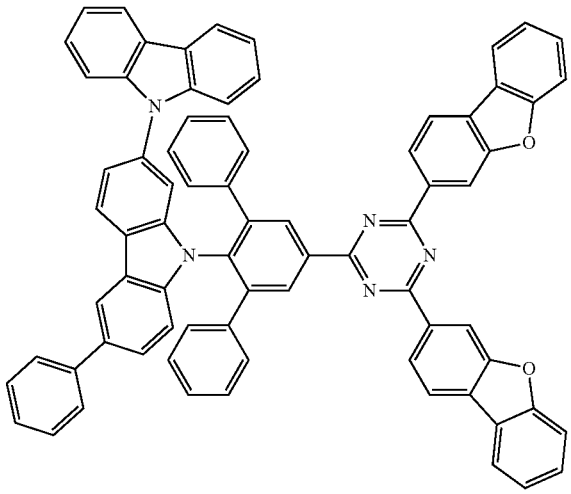
355
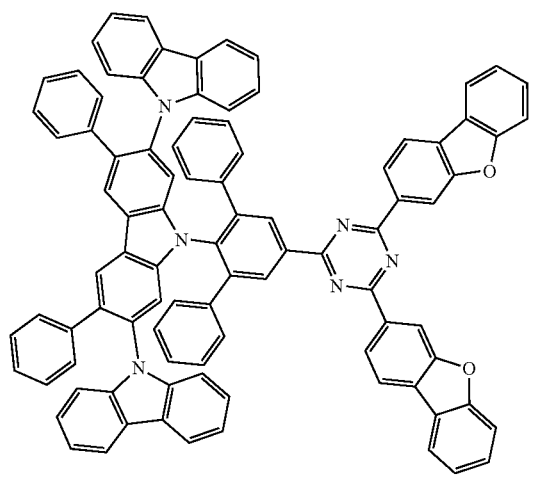
356
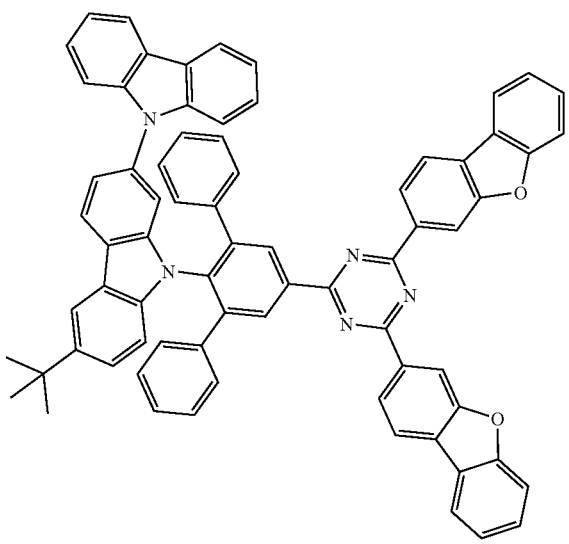
357
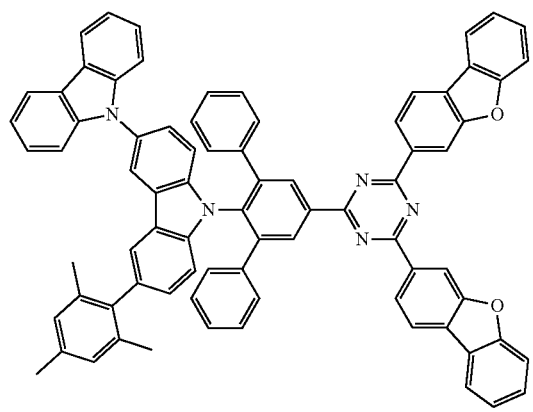
358
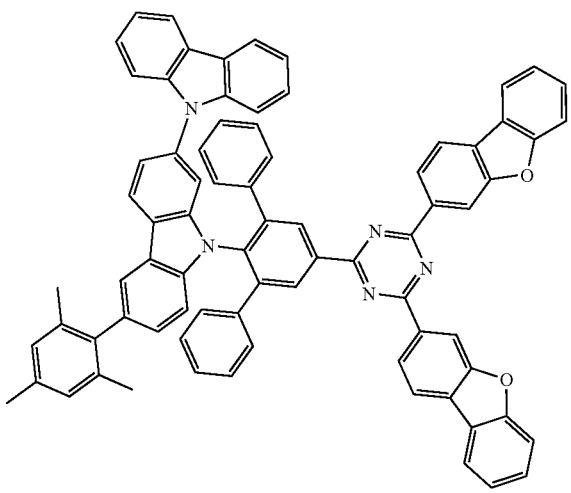

1013
1014
-continued
359
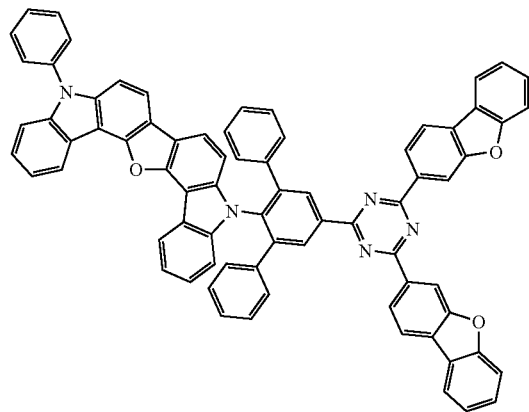
360
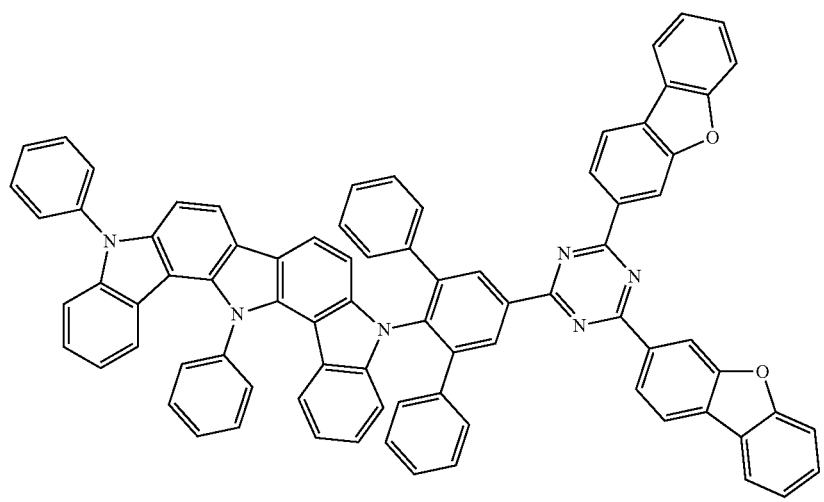
361
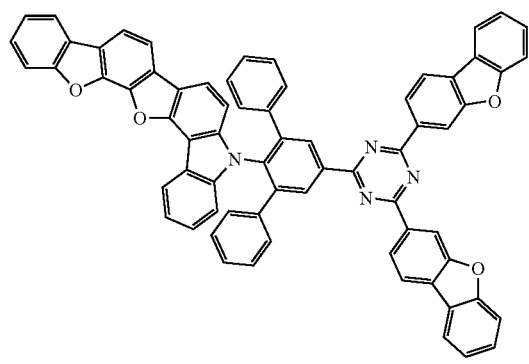
362
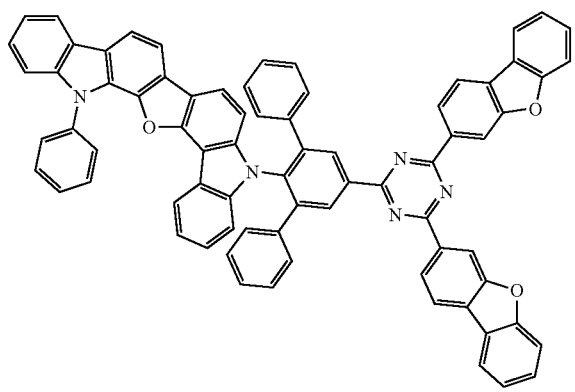

1015 1016
-continued
363
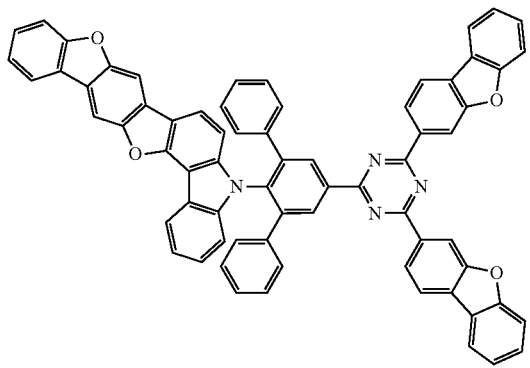
364
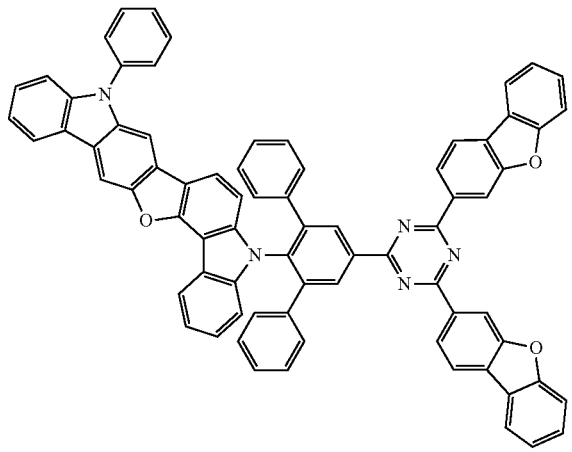
365
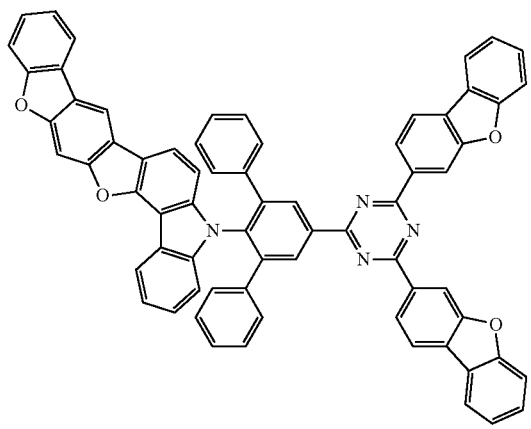
366
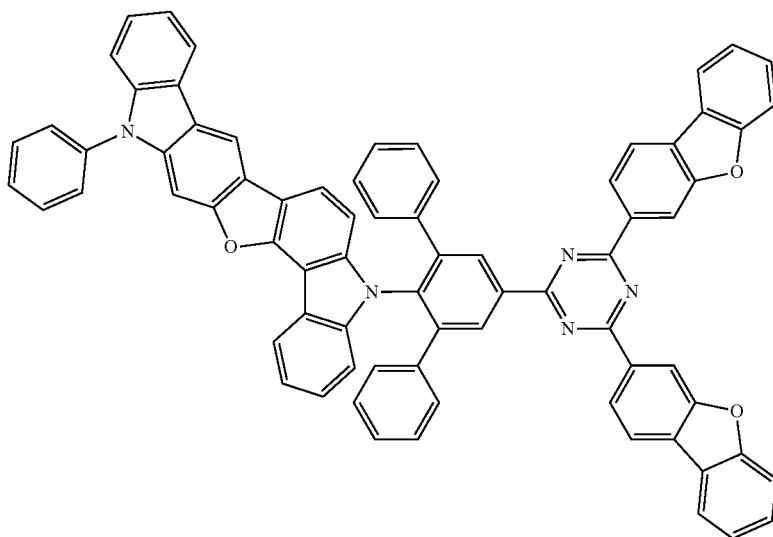

367
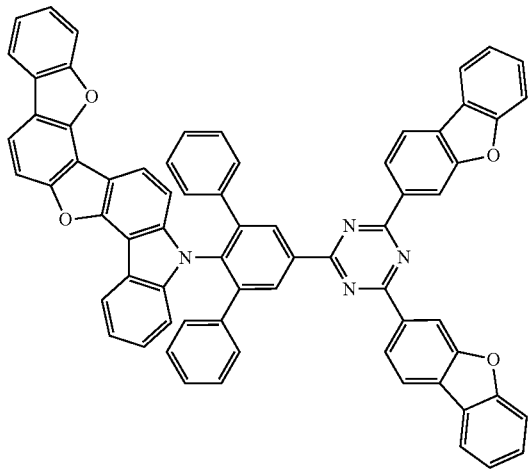
368
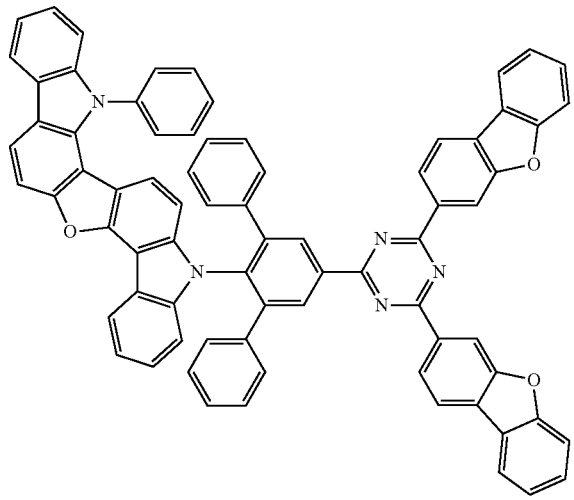
369
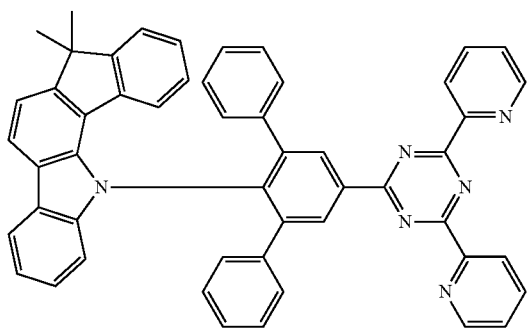
370
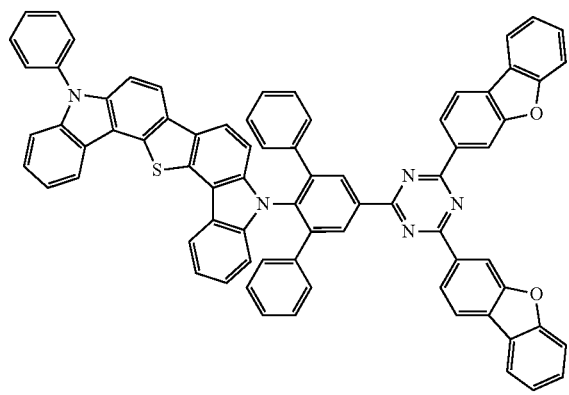
371
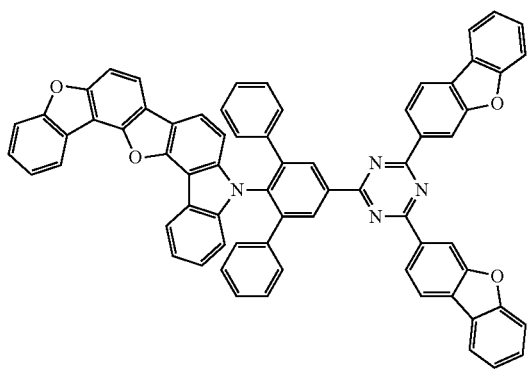
372
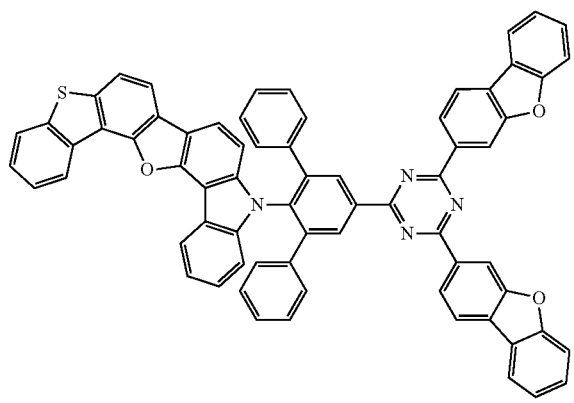

-continued
1019
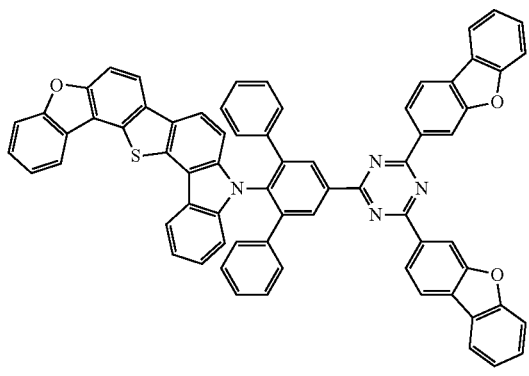
373
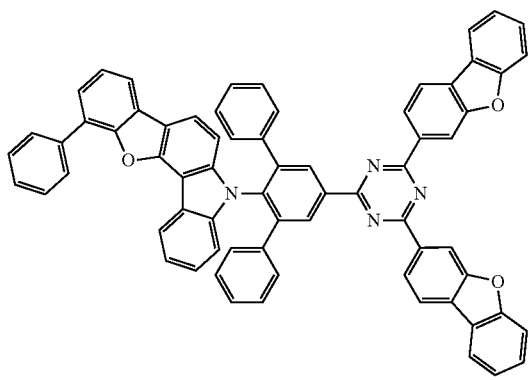
375
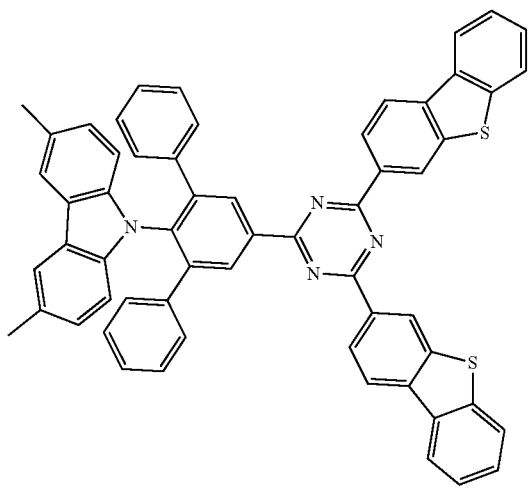
377
1020
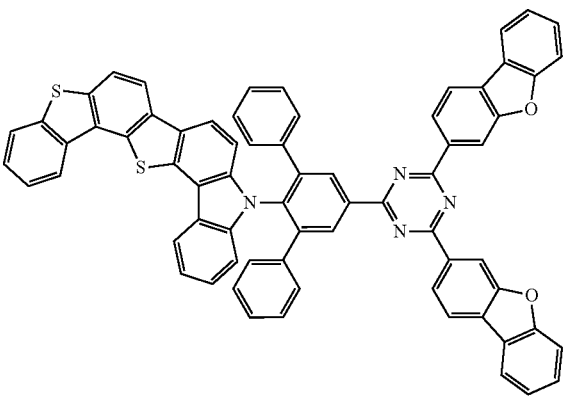
374
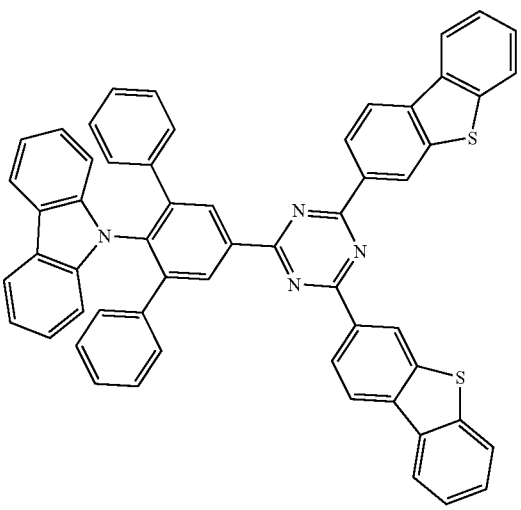
376
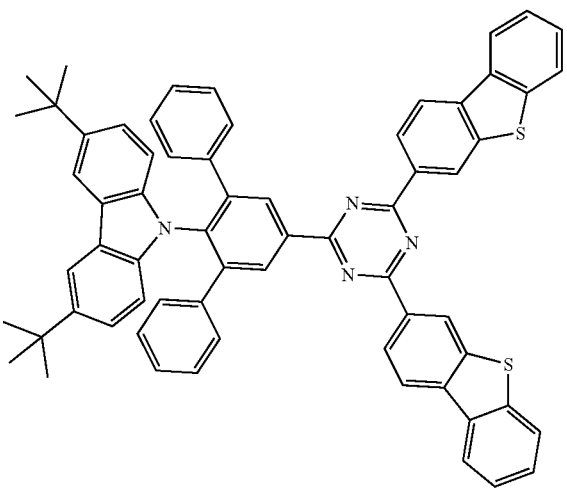
378

-continued
379
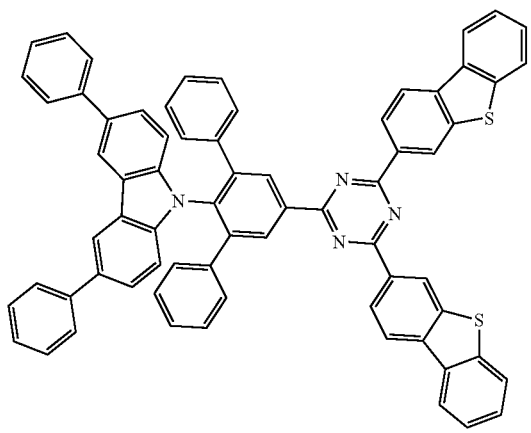
380
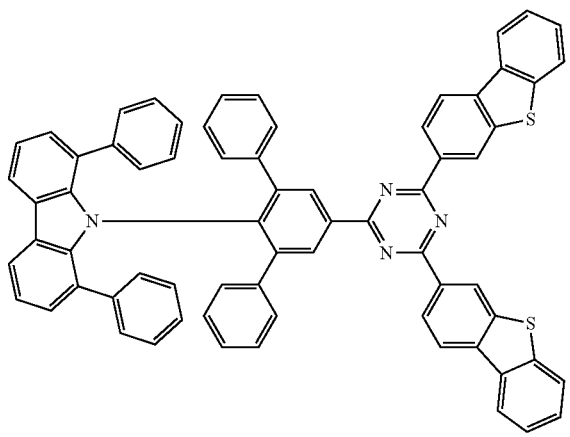
381
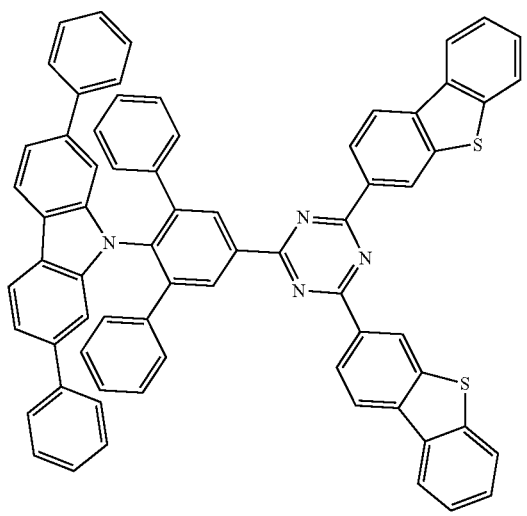
382
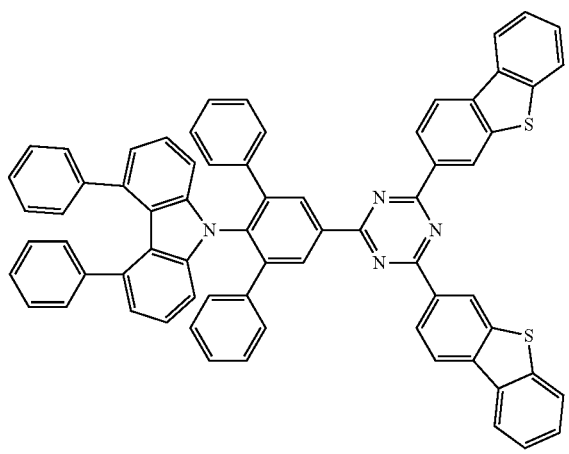
383
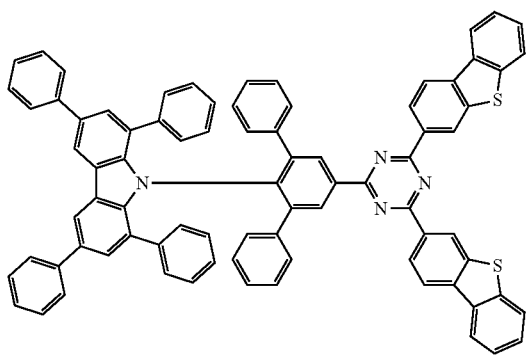
384
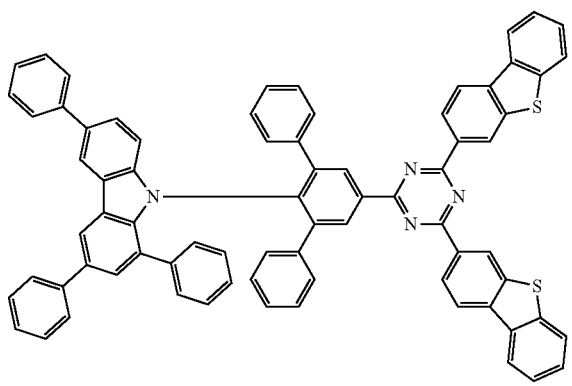

1023 1024
-continued
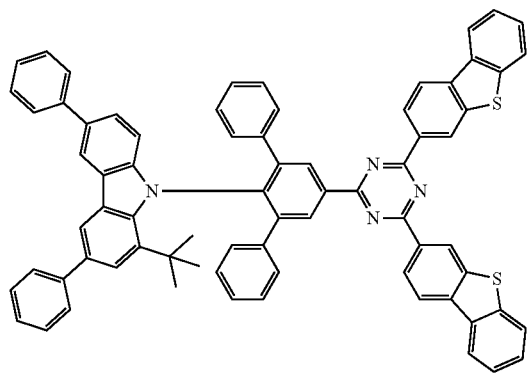
385
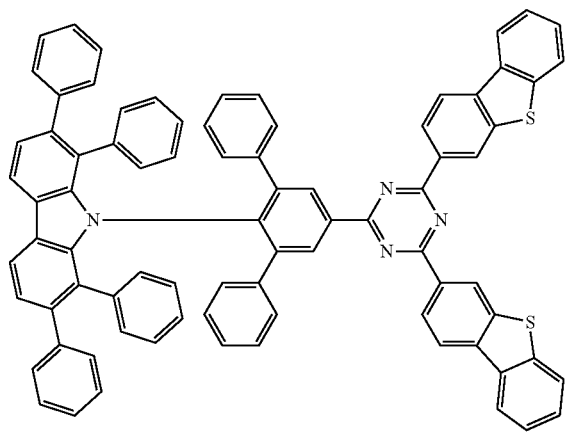
386
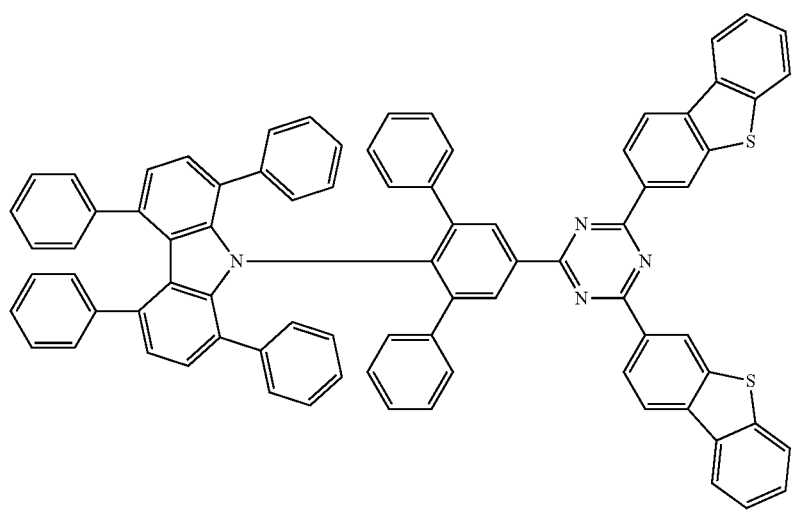
387
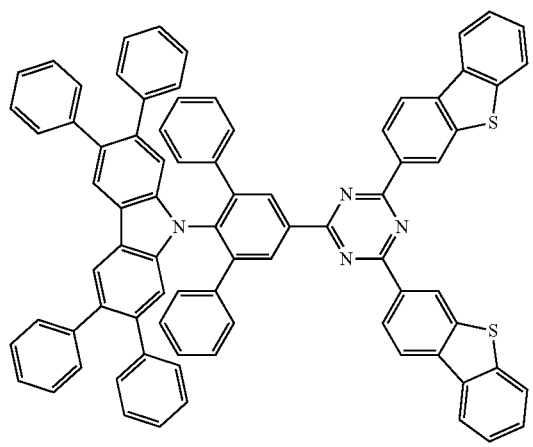
388
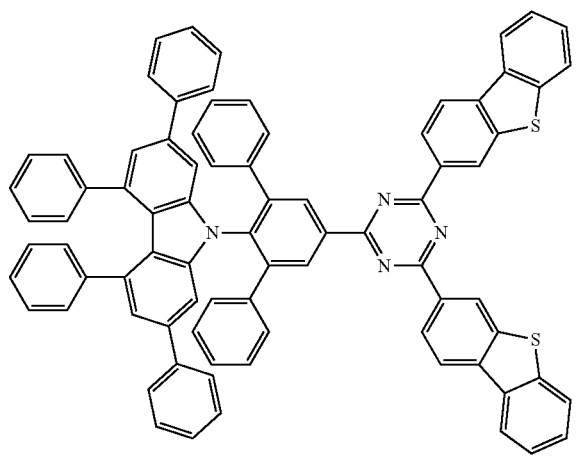
389

1025  1026
390
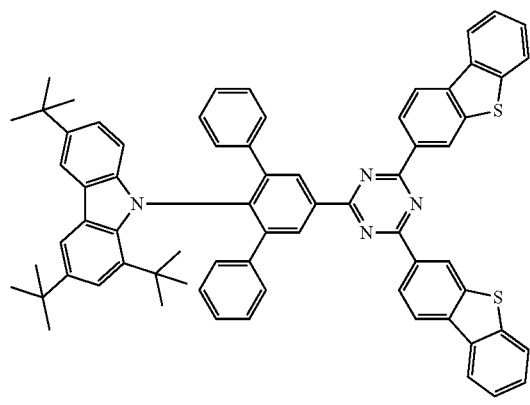
391
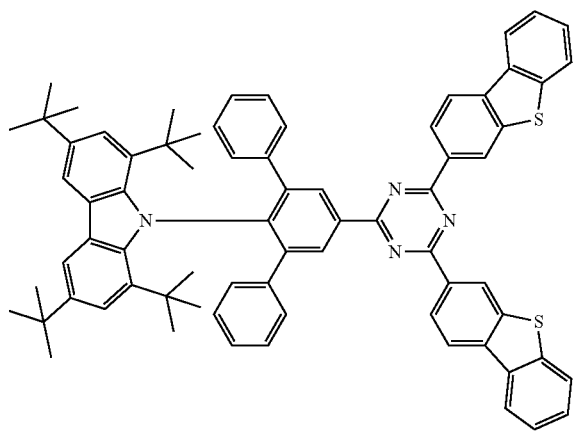
392
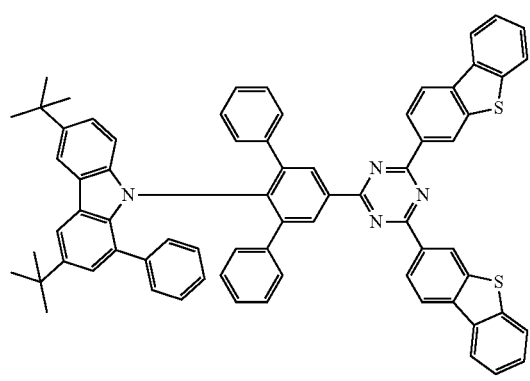
393
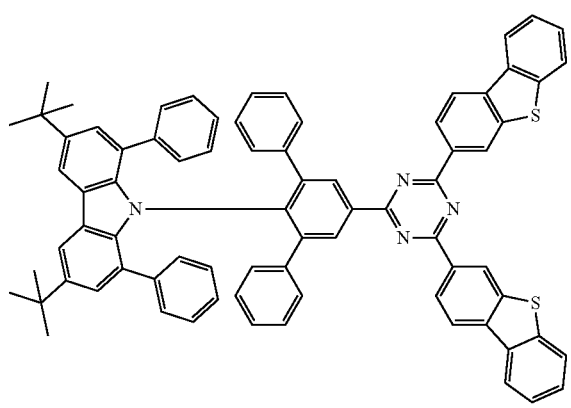
394
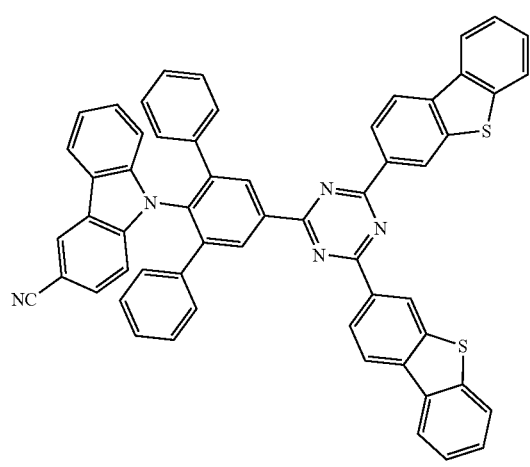
395
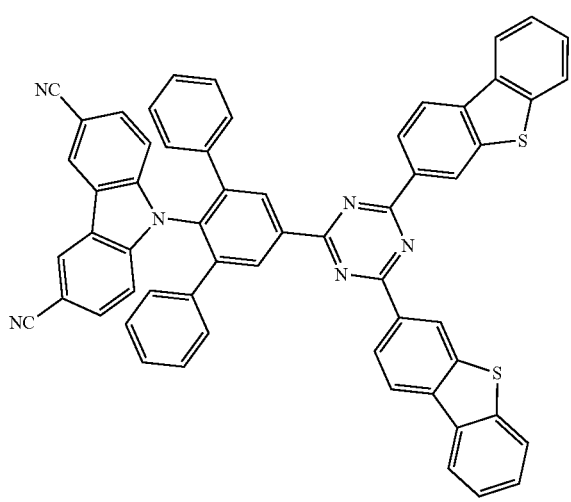

-continued
396
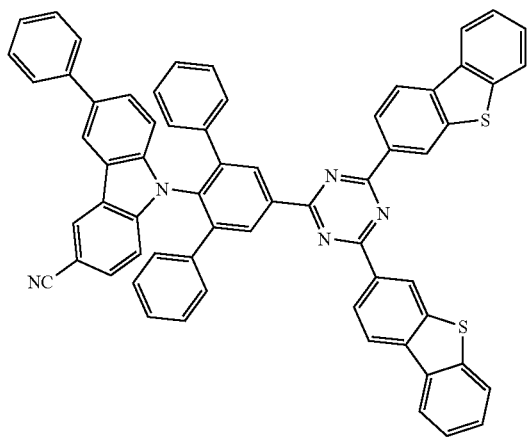
397
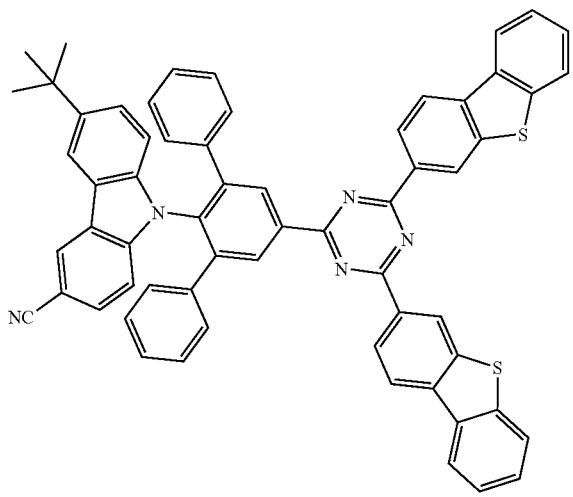
398
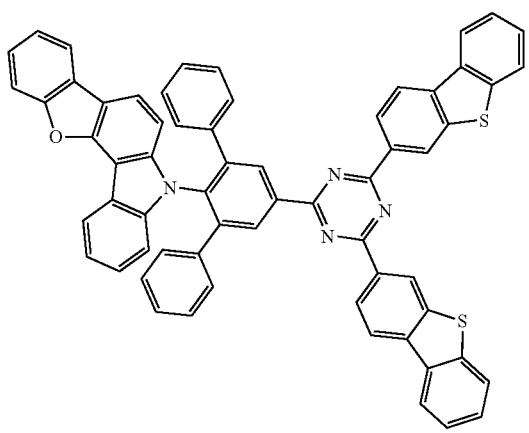
399
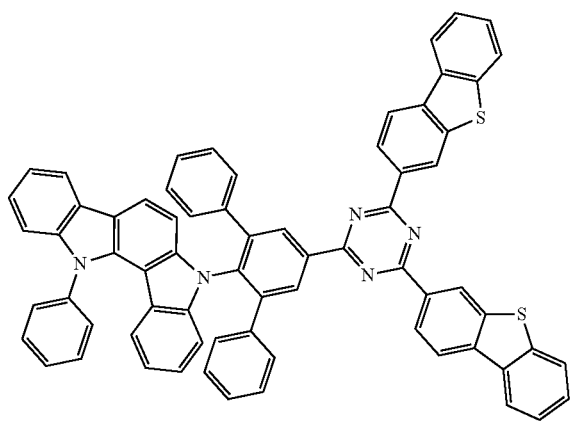
400
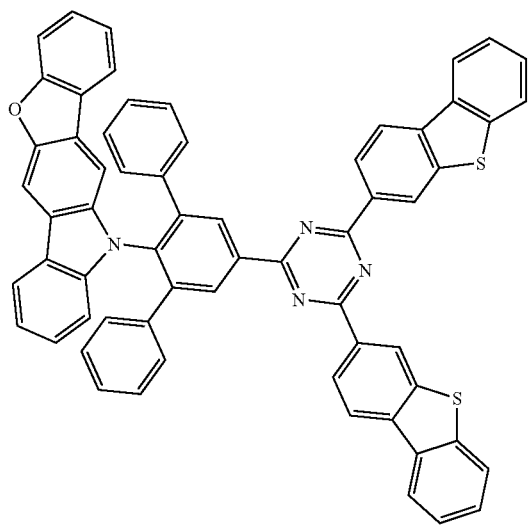
401
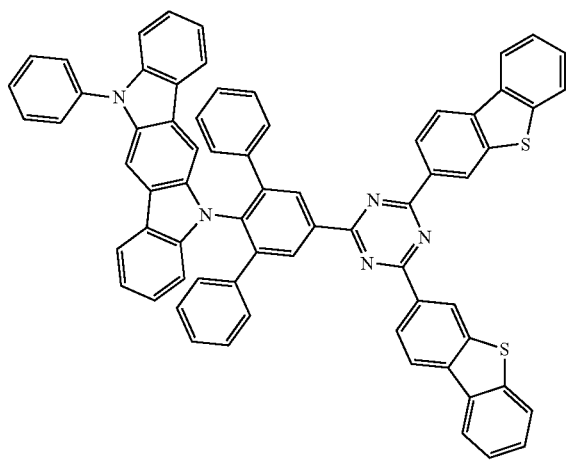

1029 1030
-continued
402
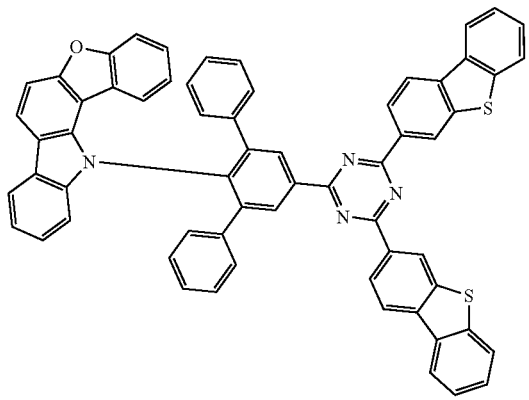
403
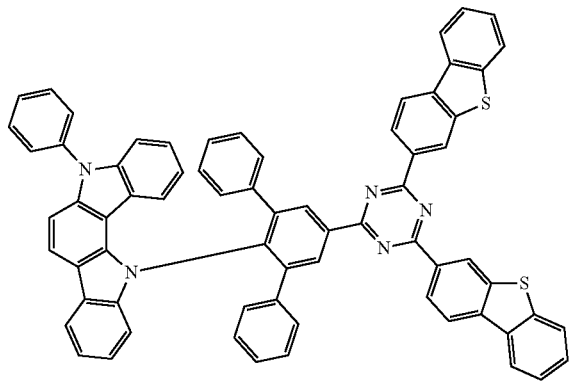
404
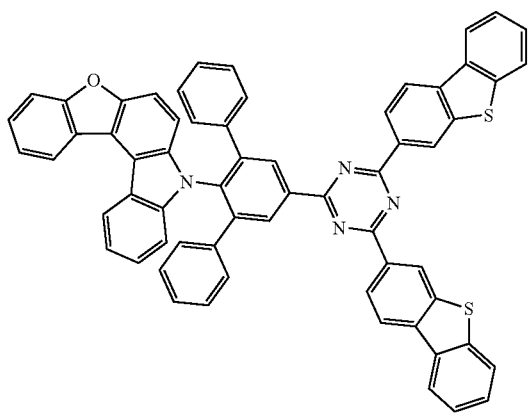
405
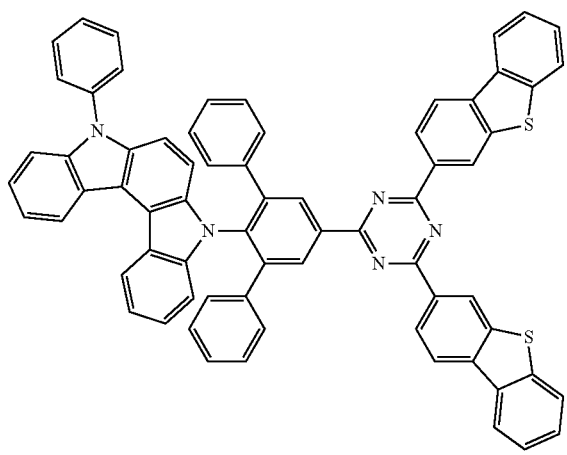
406
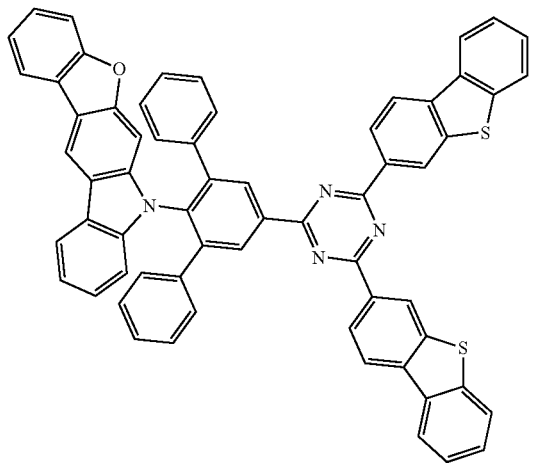
407
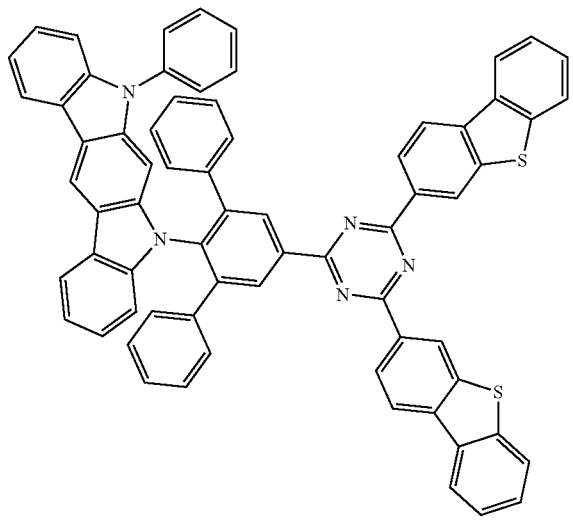

-continued
408
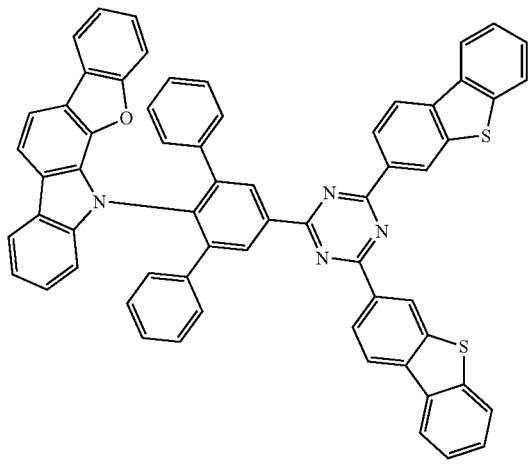
409
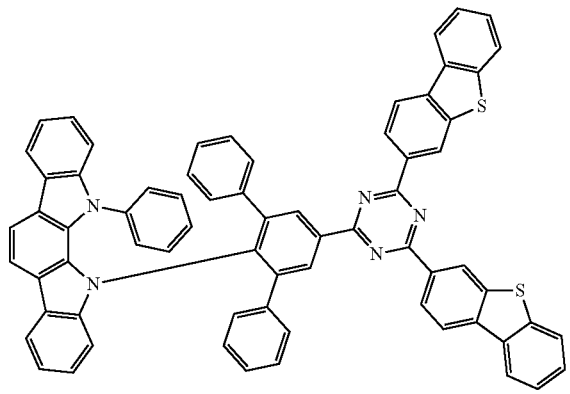
410
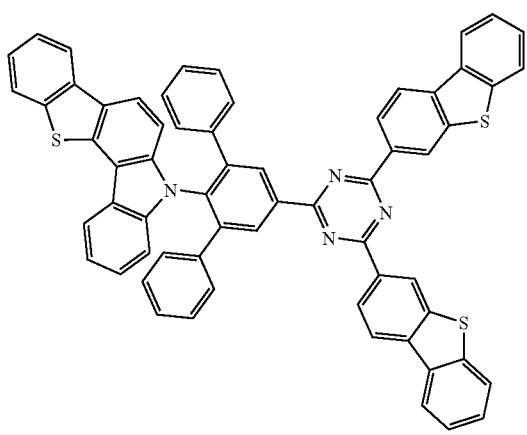
411
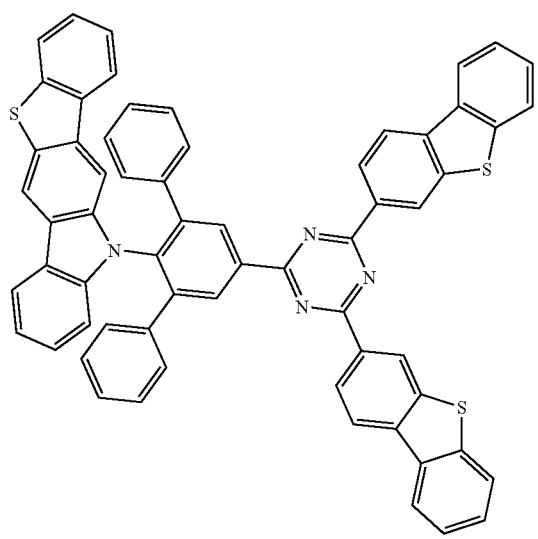
412
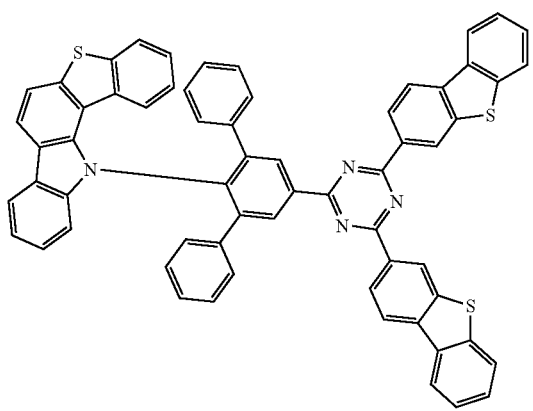
413
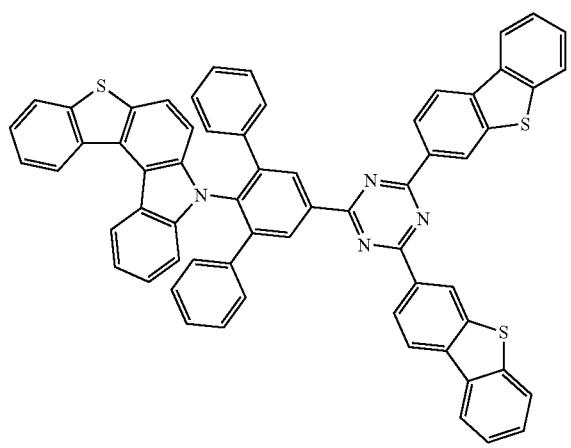

-continued
414
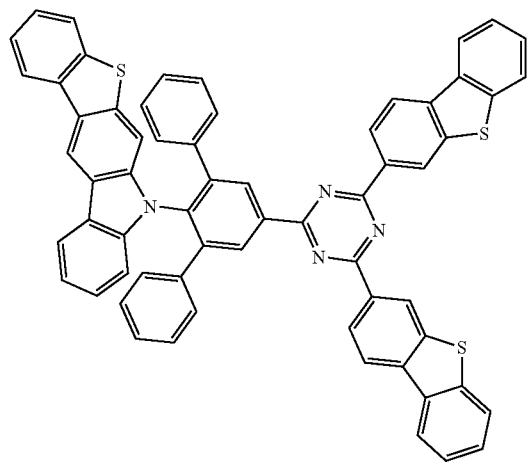
415
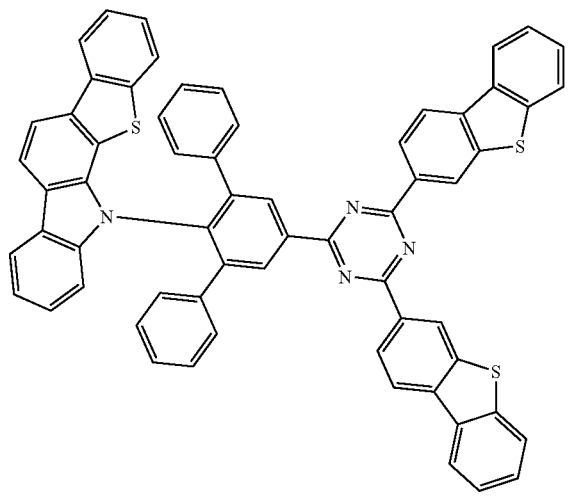
416
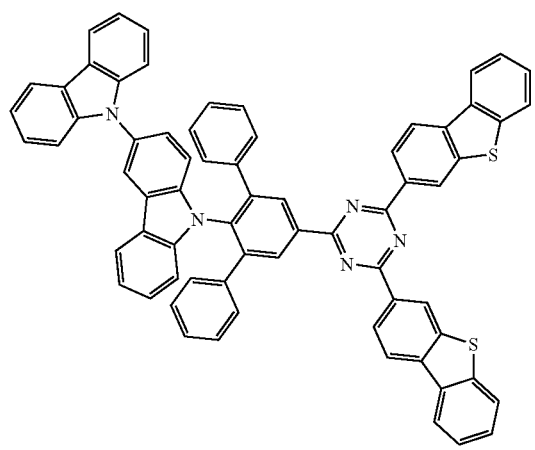
417
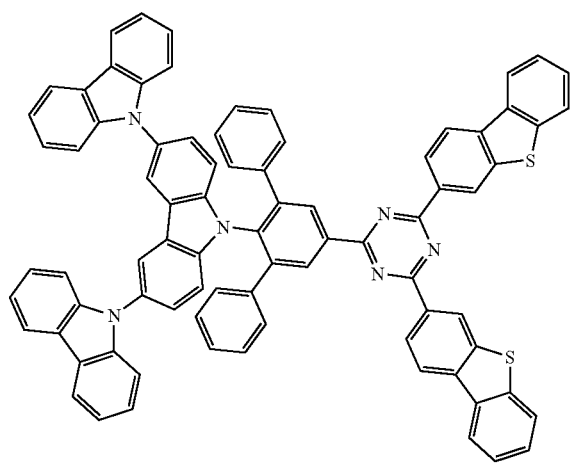
418
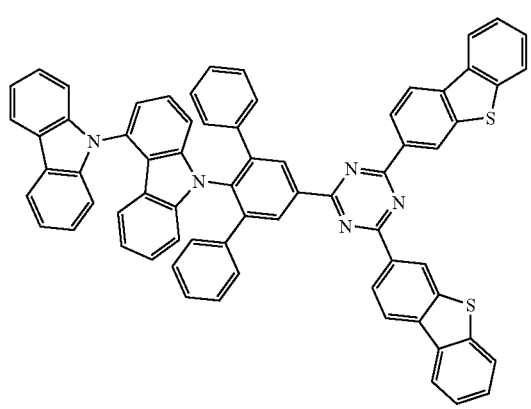
419
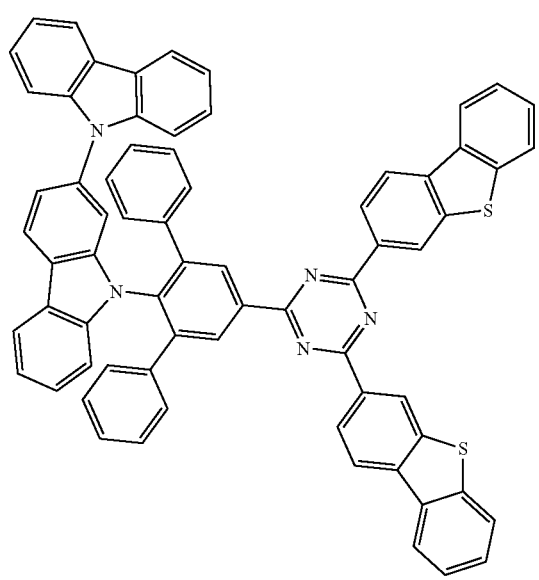

-continued
420
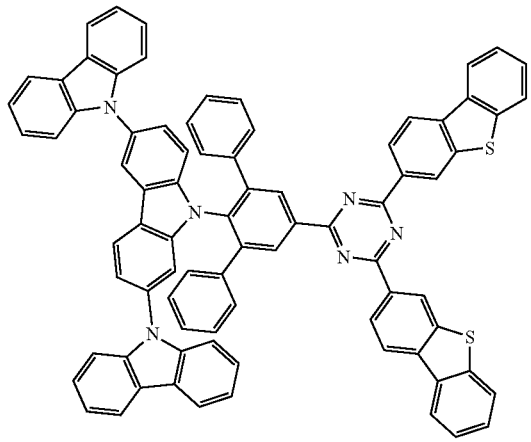
421
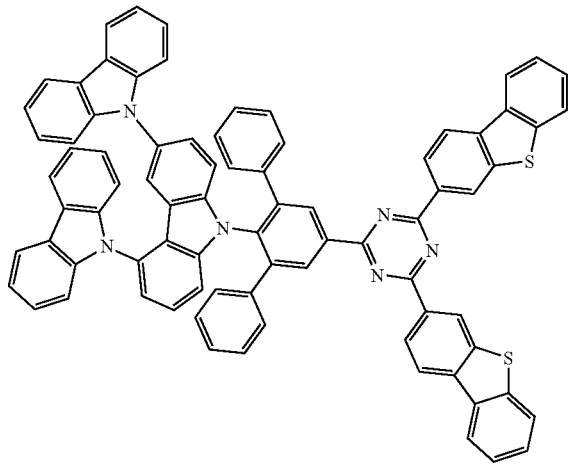
422
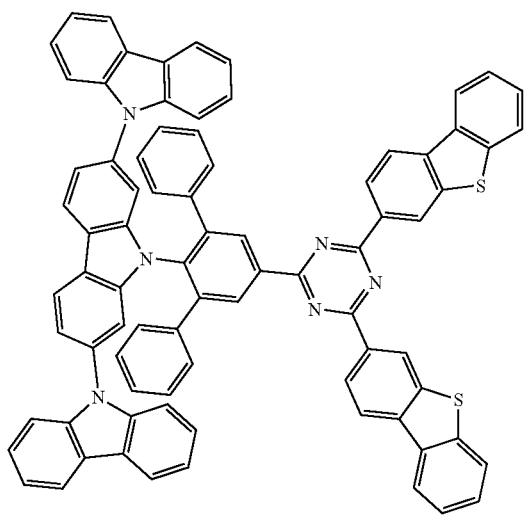
423
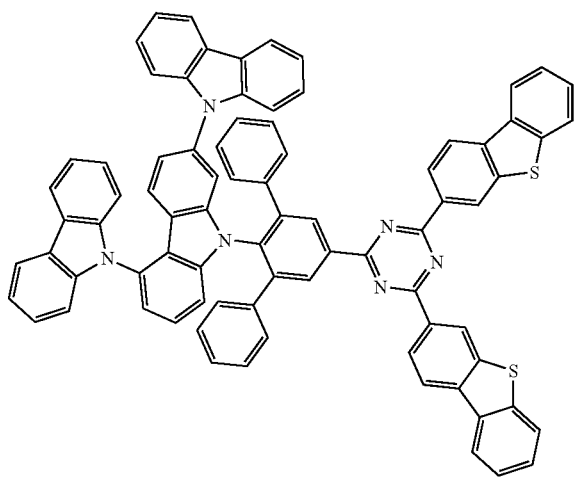
424
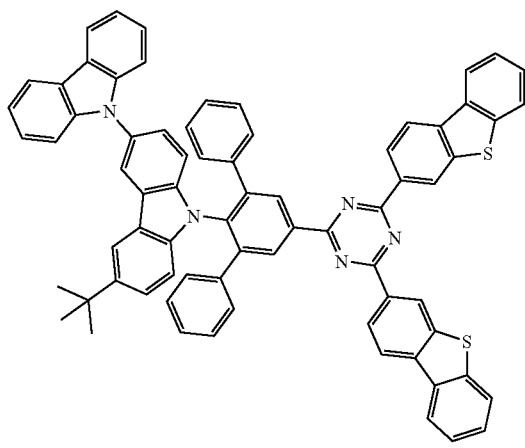
425
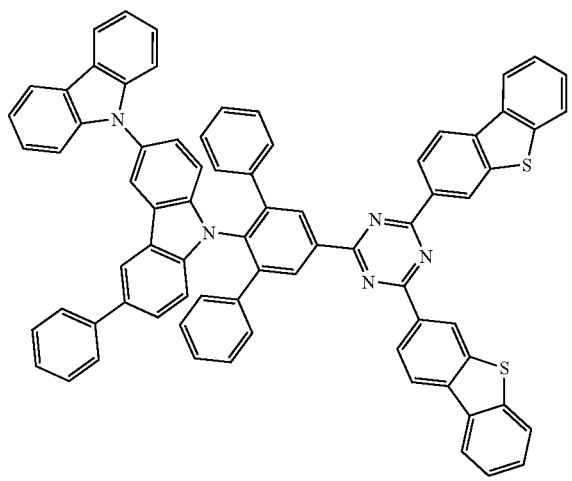

-continued
1037
426
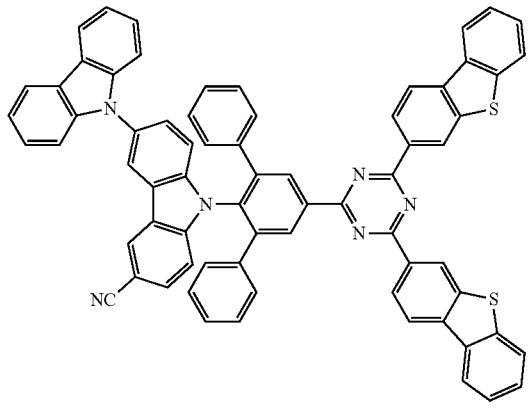
1038
427
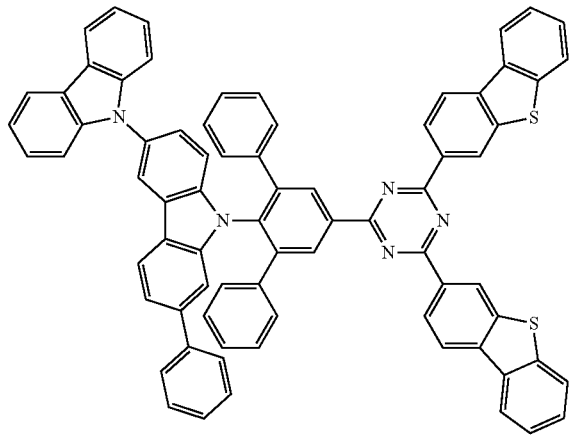
428
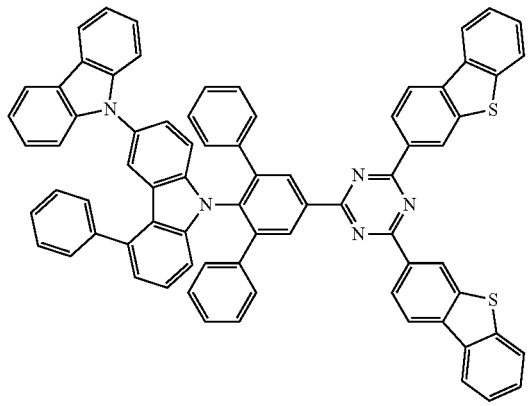
429
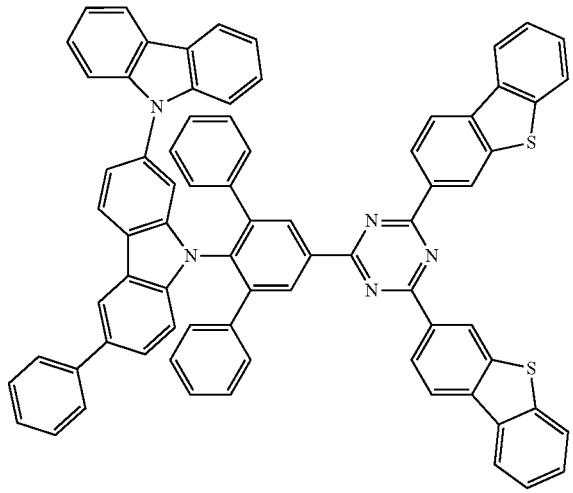
430
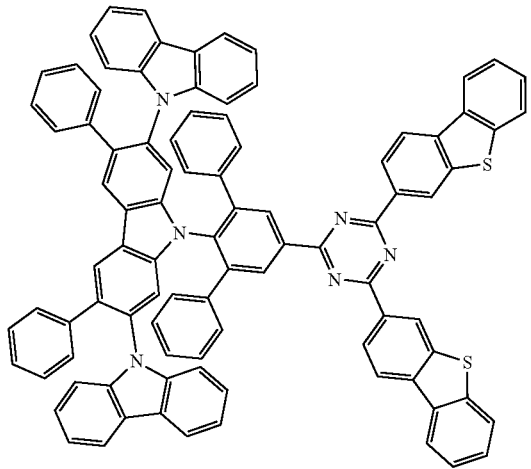
431
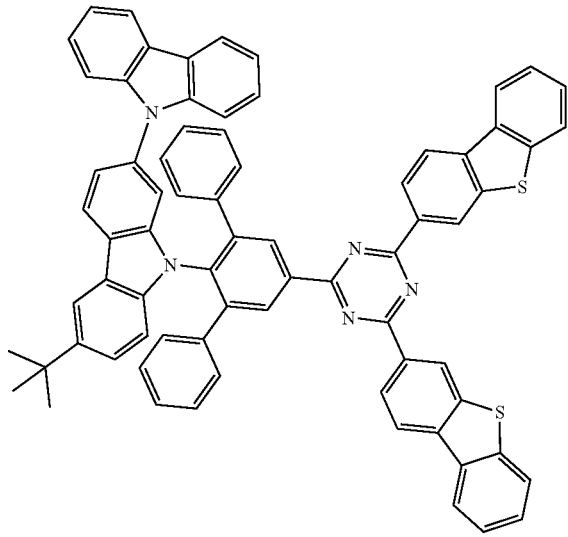

-continued
1039
432
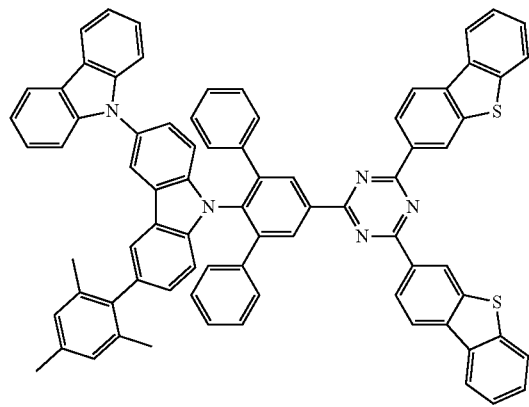
1040
433
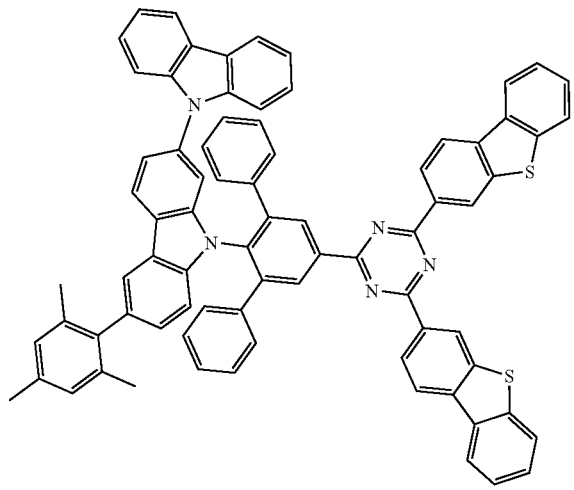
434
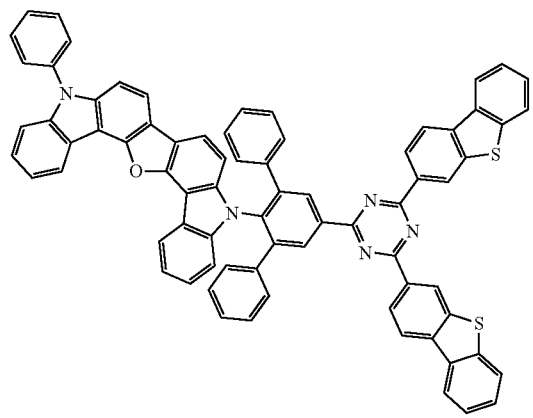
435
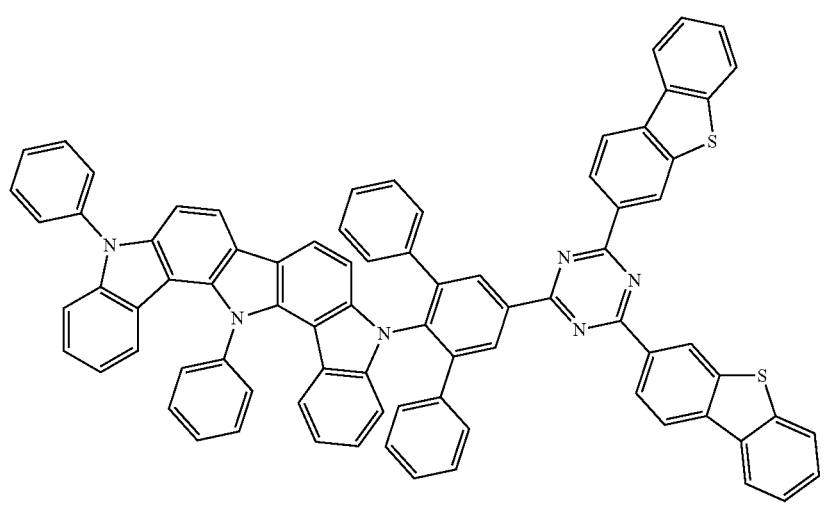

-continued
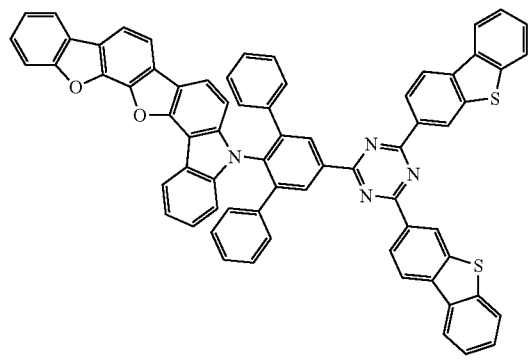
436
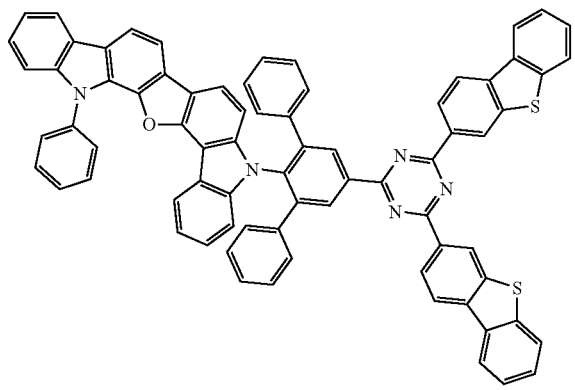
437
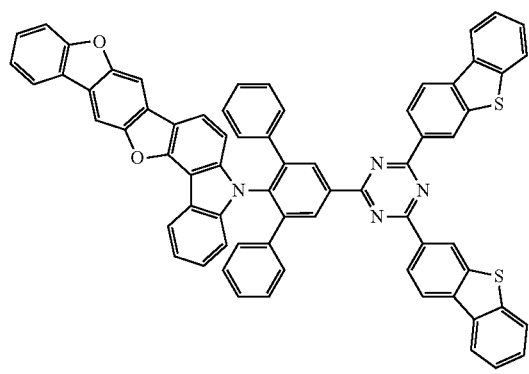
438
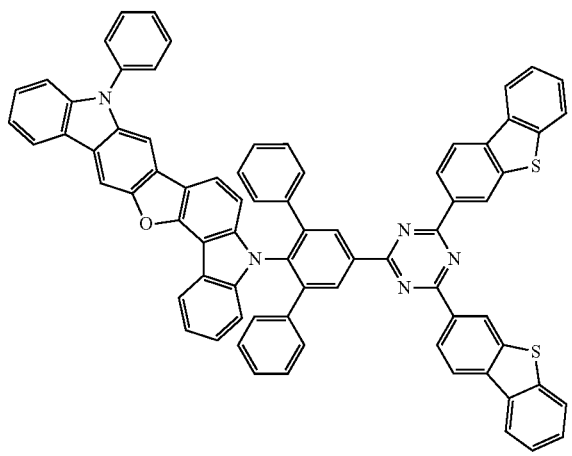
439
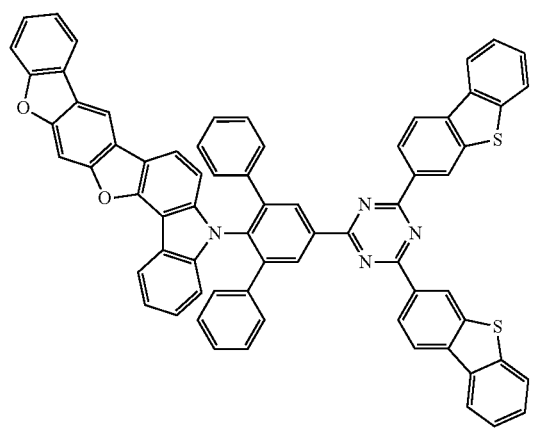
440

1043 1044
-continued
441
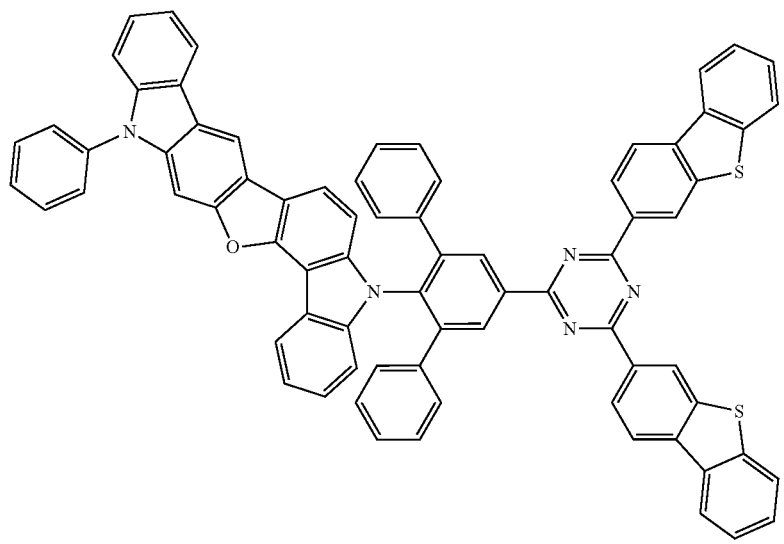
442 443
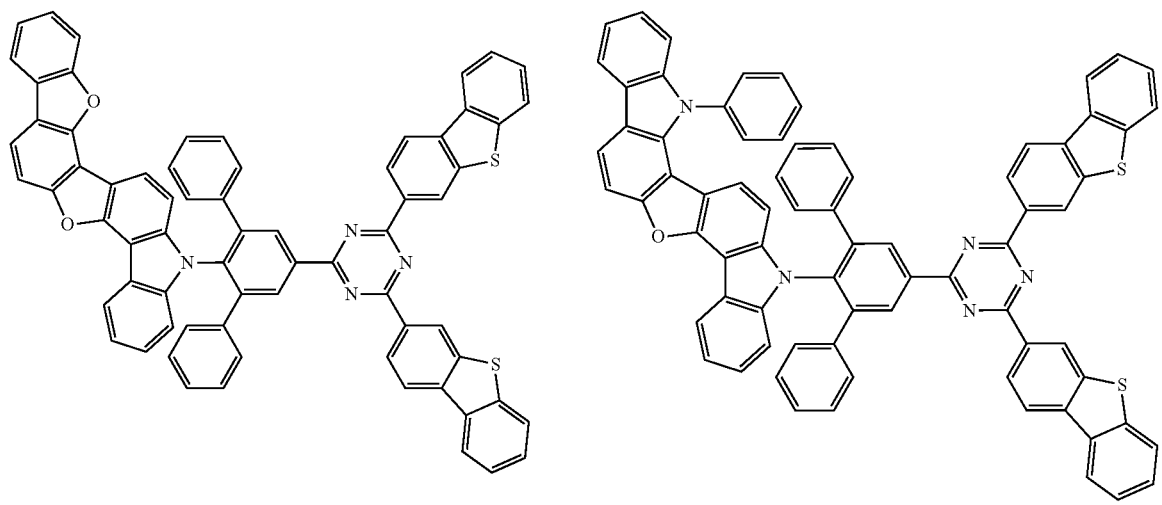
444 445
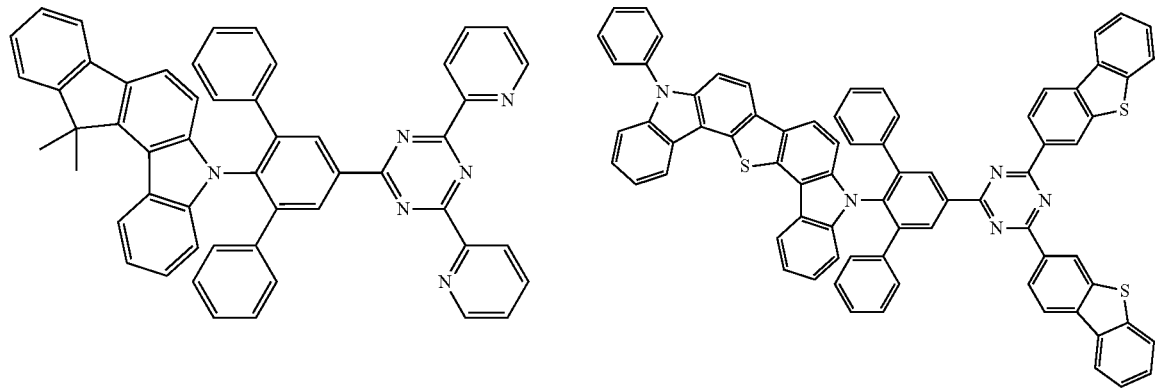

446
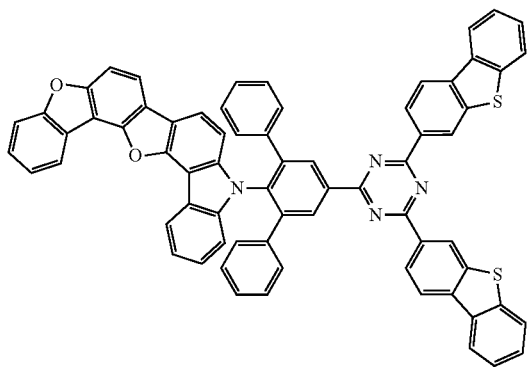
447
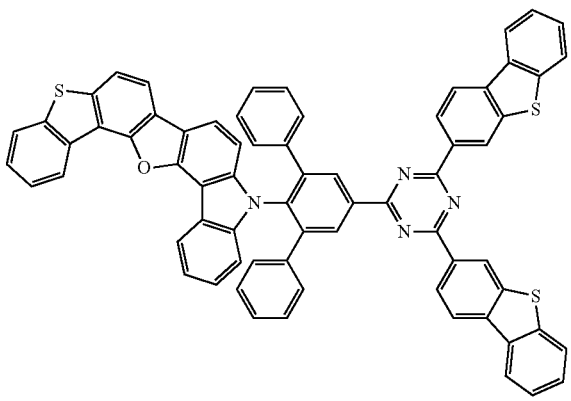
448
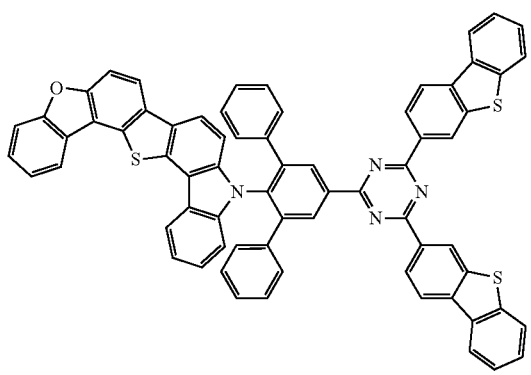
449
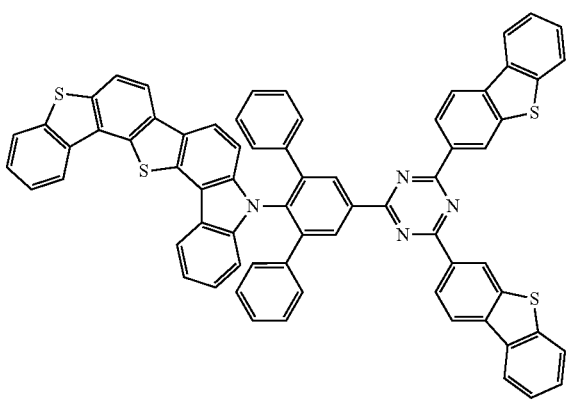
450
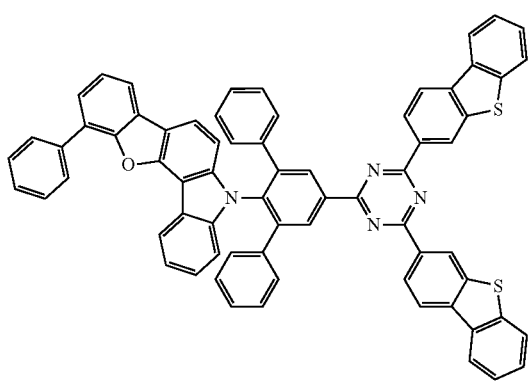
451
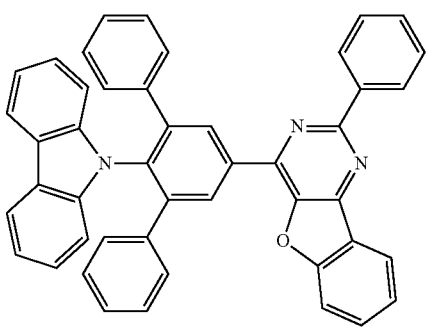
452
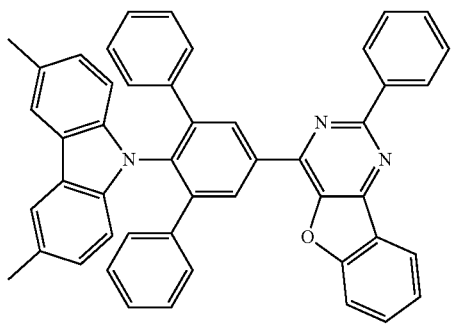
453
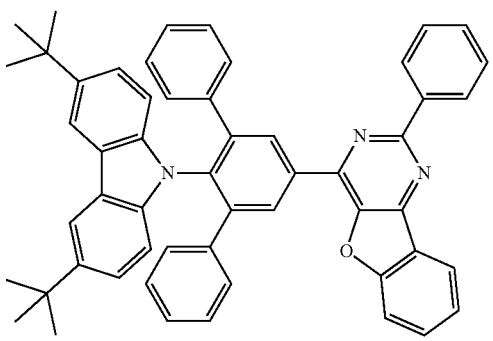

-continued
454
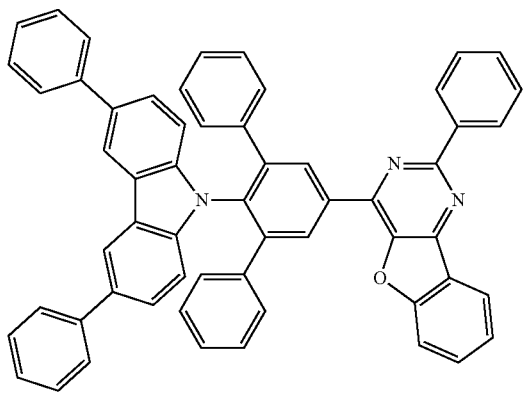
455
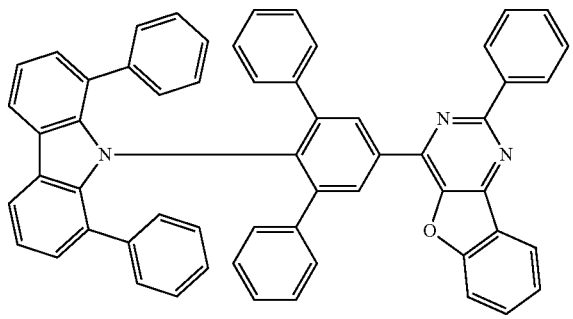
456
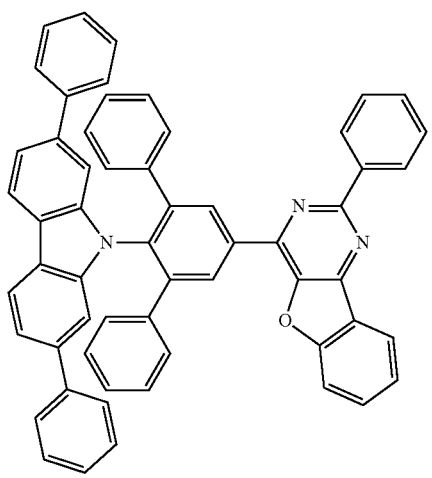
457
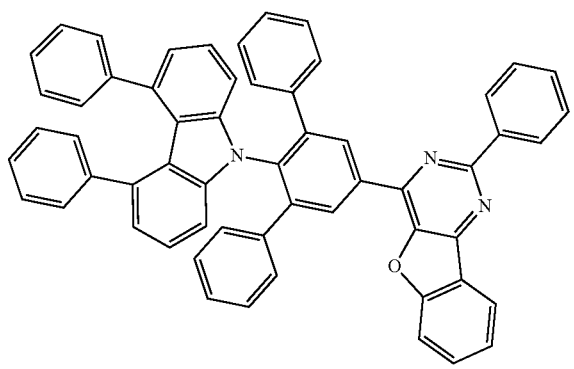
458
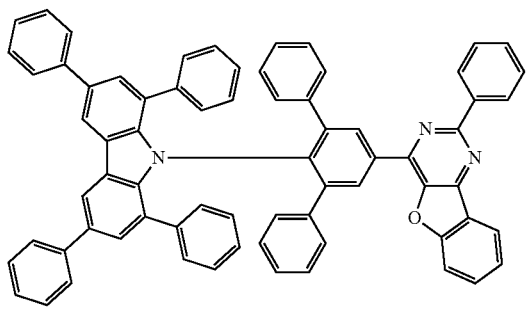
459
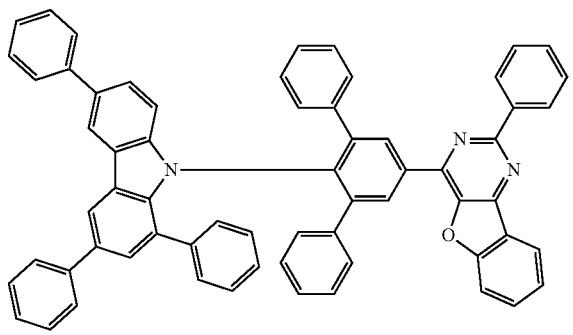

-continued
1049
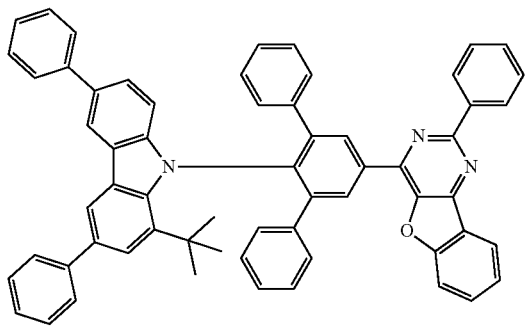
460
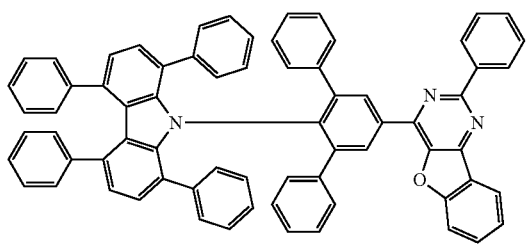
462
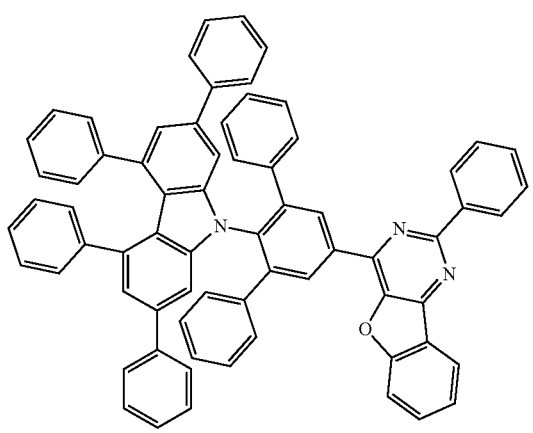
464
1050
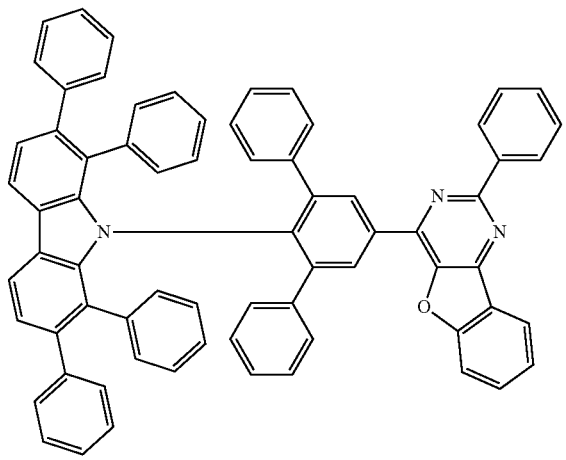
461
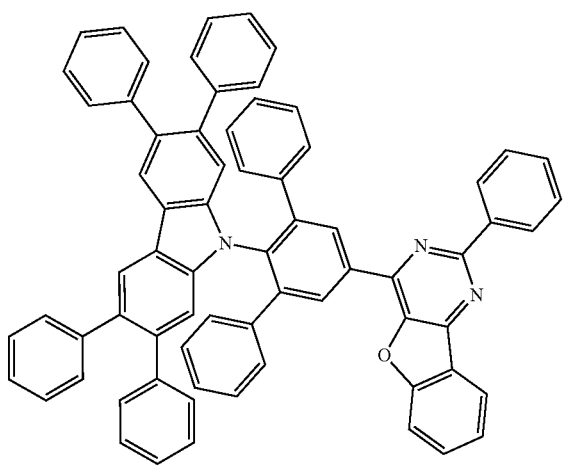
463
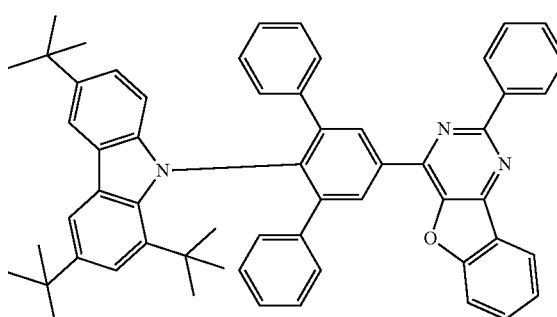
465

-continued
| 1051 | 1052 |
|---|---|
| 466 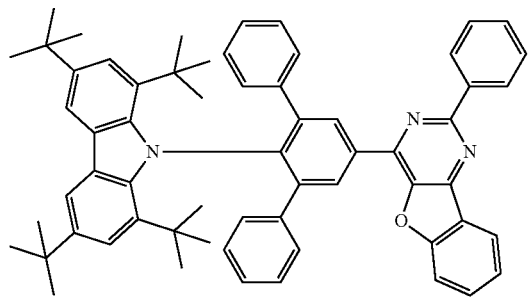 | 467 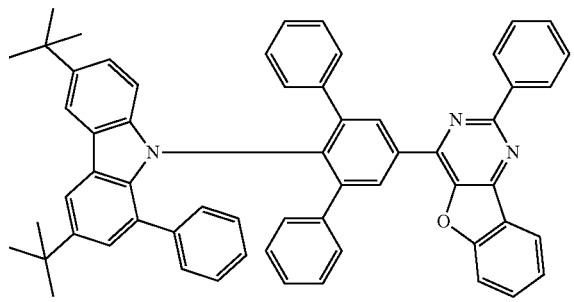 |
| 468 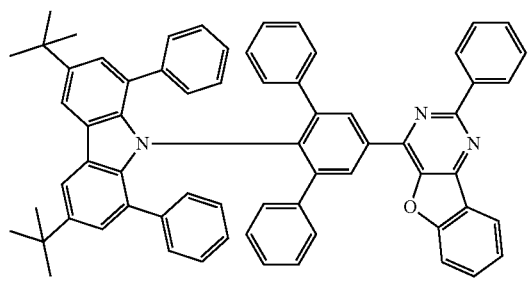 | 469 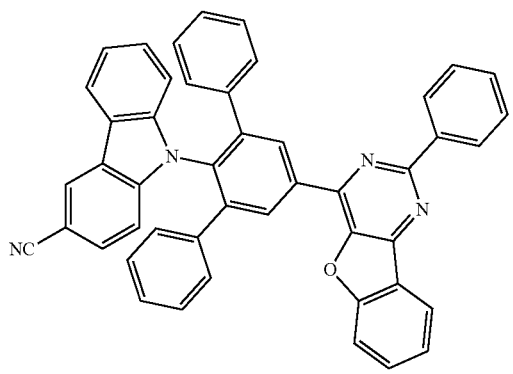 |
| 470 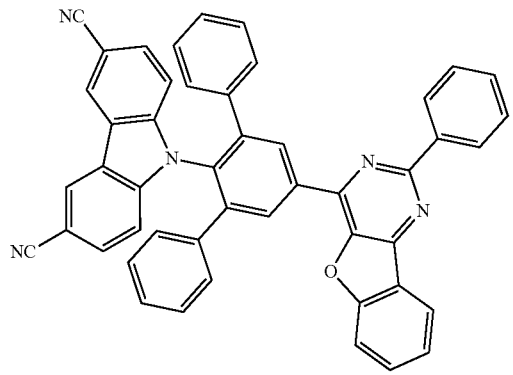 | 471 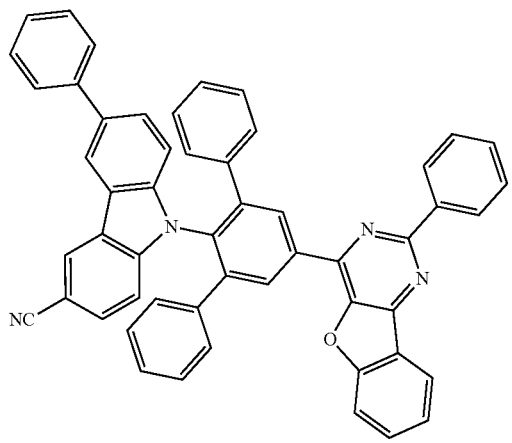 |
| 472 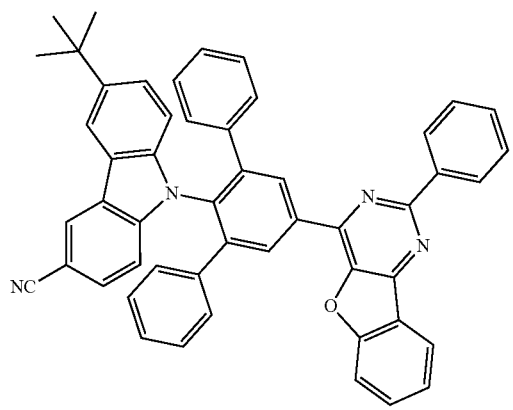 | 473 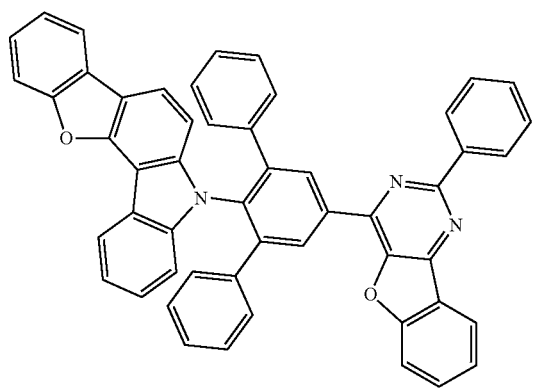 |

474
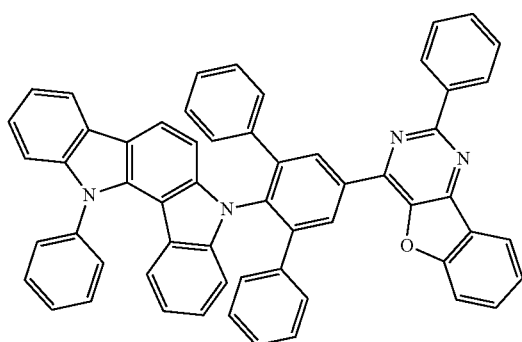
475
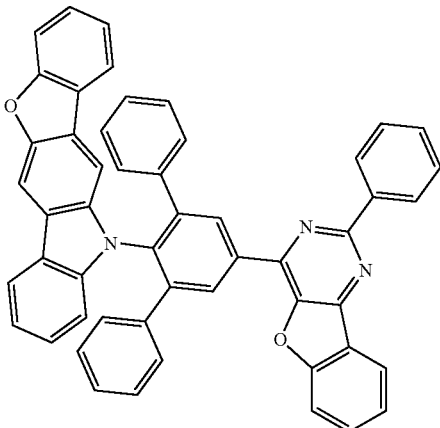
476
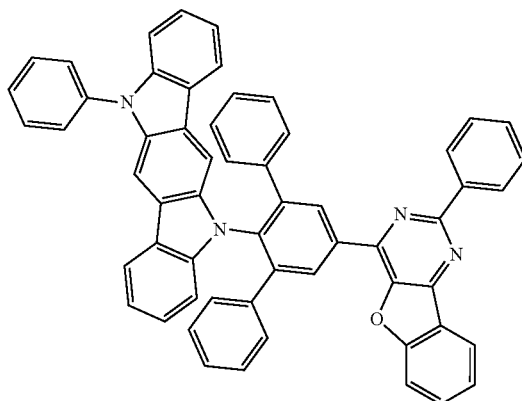
477
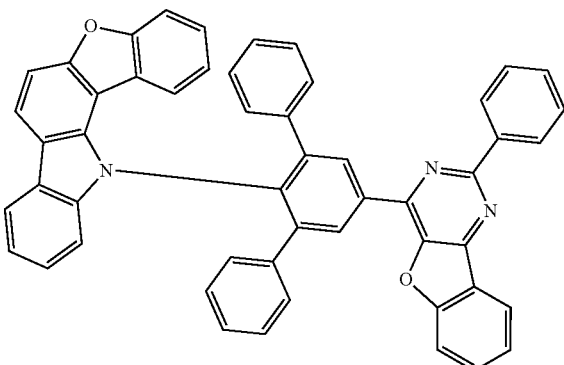
478
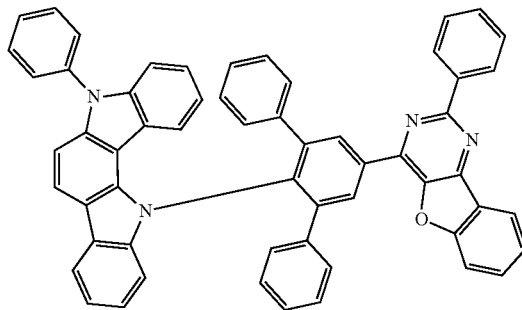
479
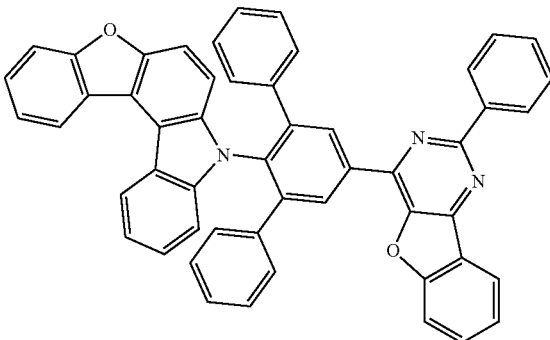
480
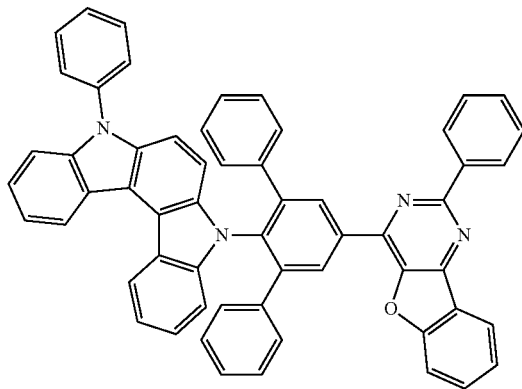
481
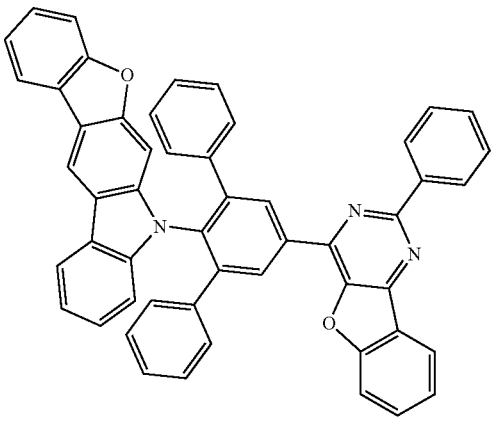

1055 1056
-continued
482
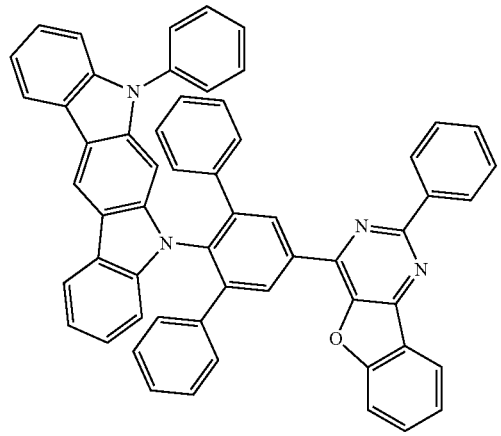
483
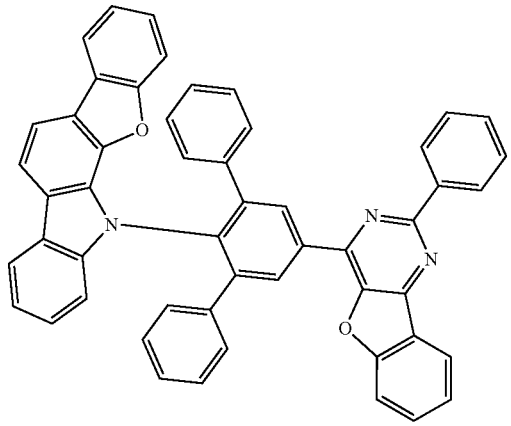
484
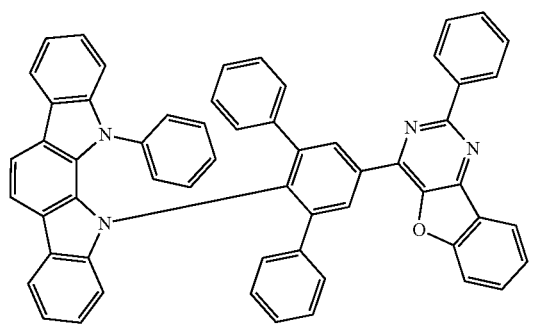
485
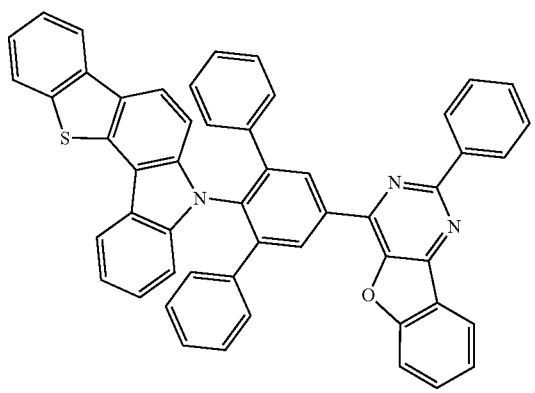
486
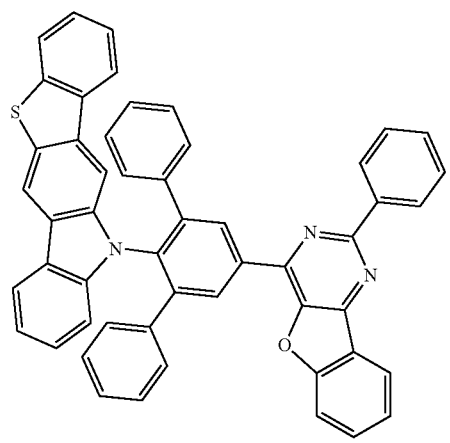
487
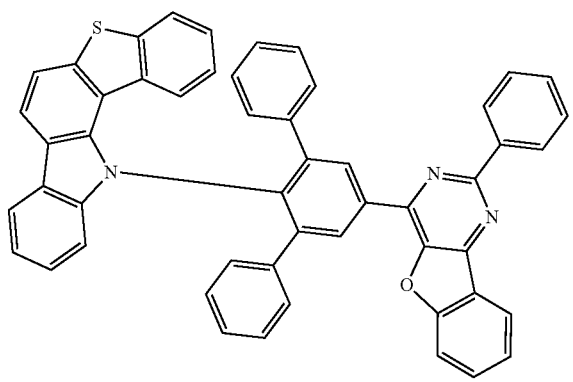

1057 1058
-continued
488
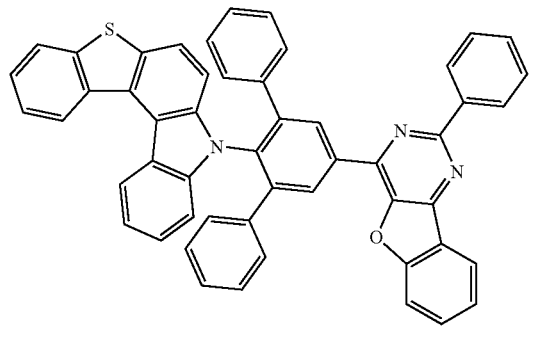
489
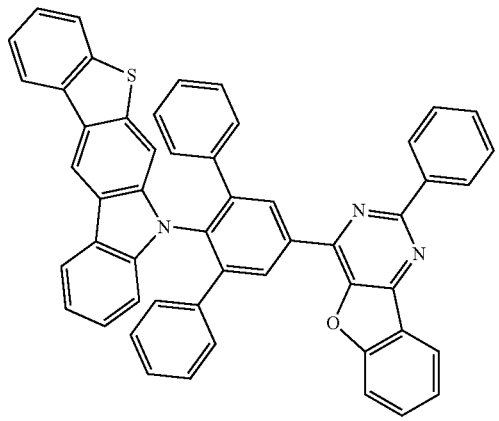
490
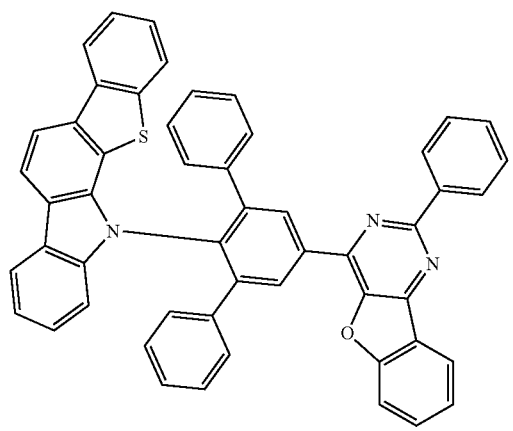
491
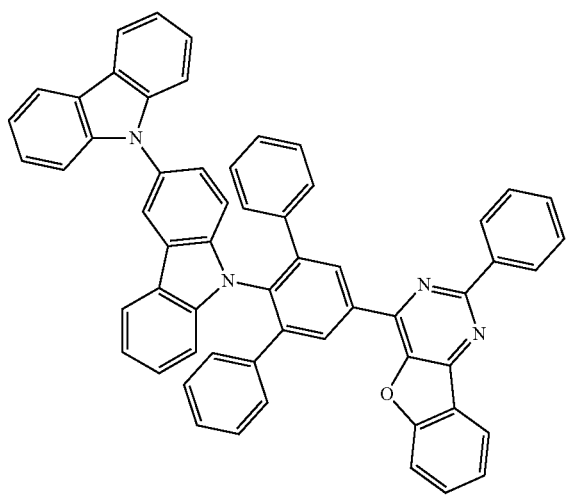
492
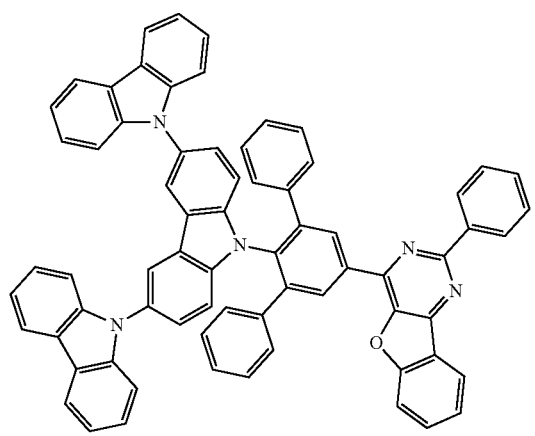
493
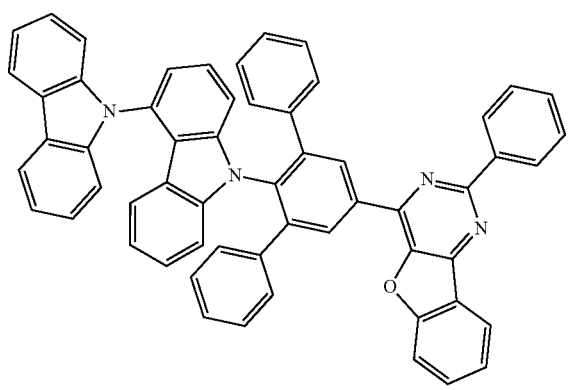

-continued
494
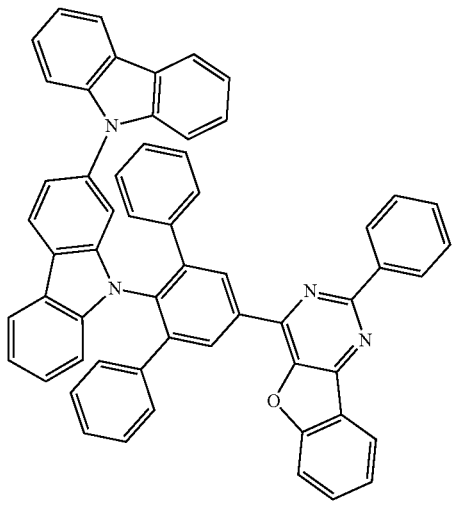
495
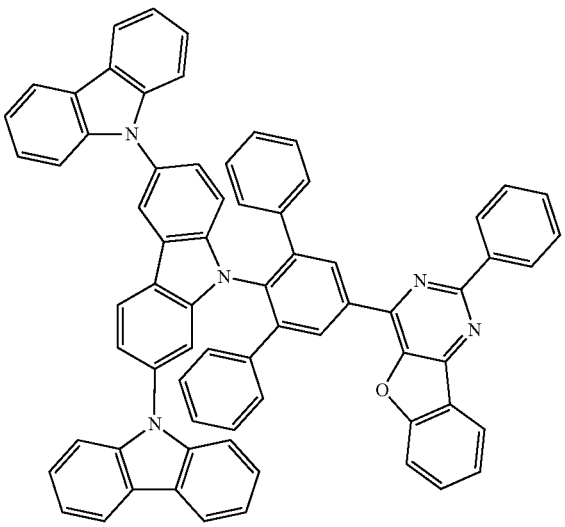
496
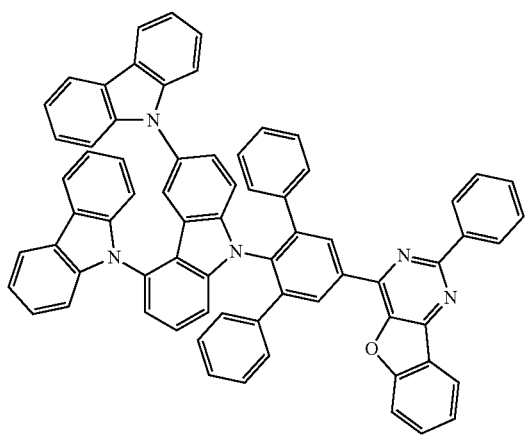
497
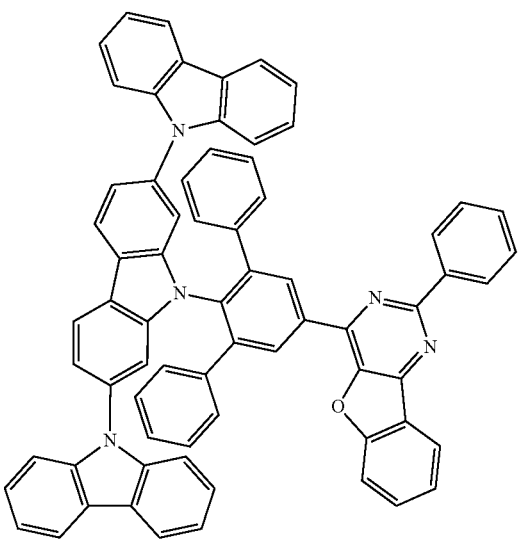
498
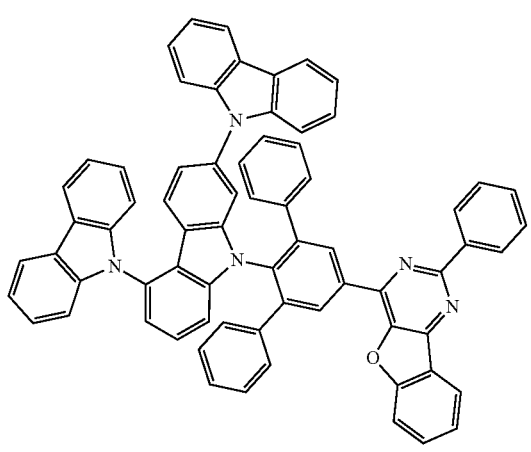
499
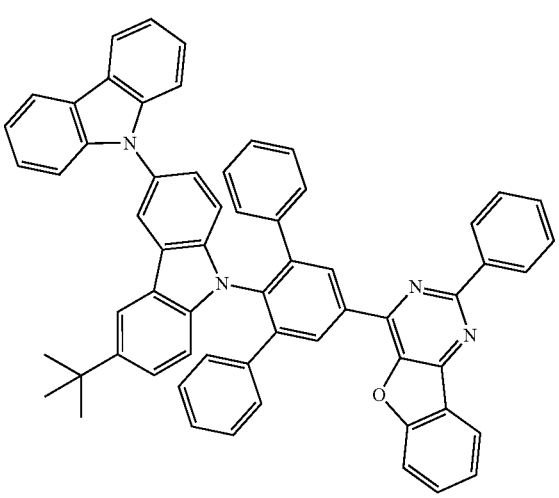

-continued
500
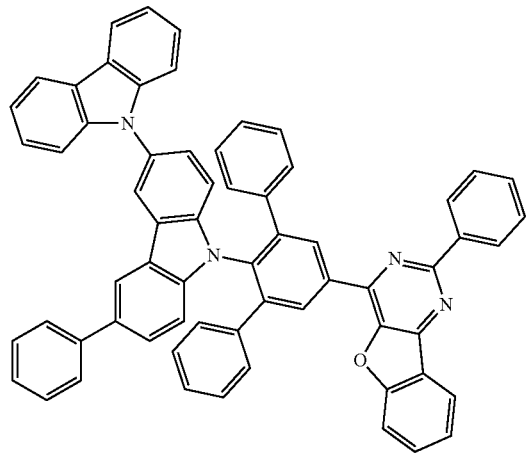
501
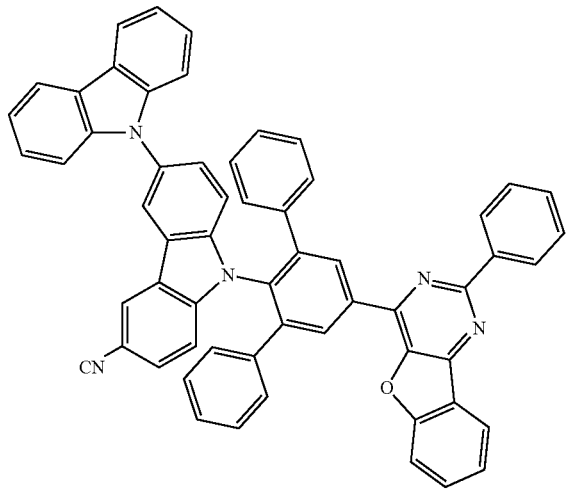
502
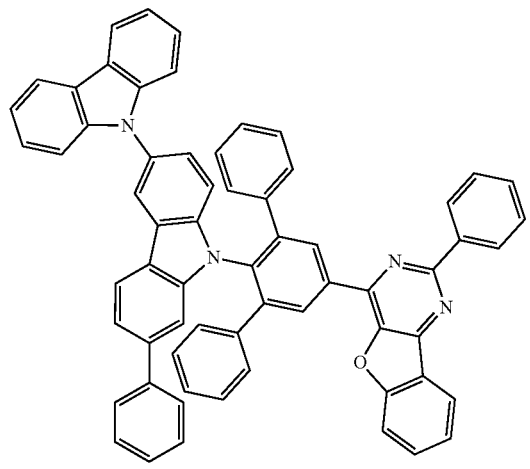
503
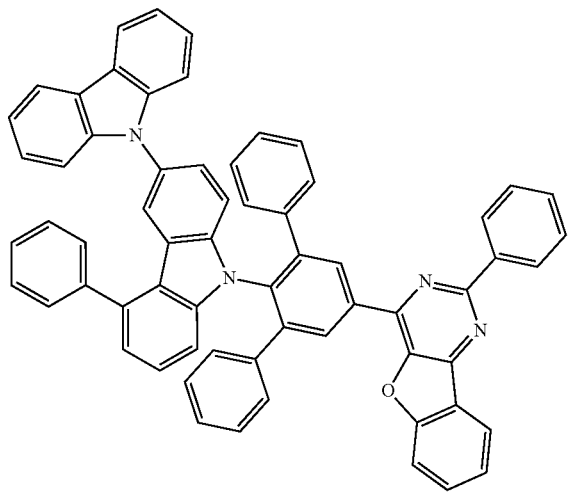
504
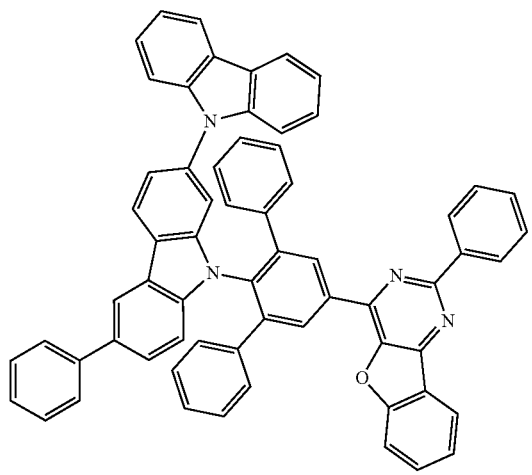
505
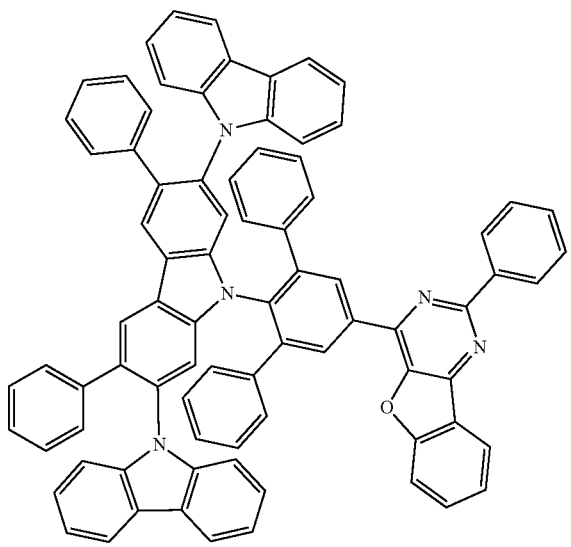

-continued
506
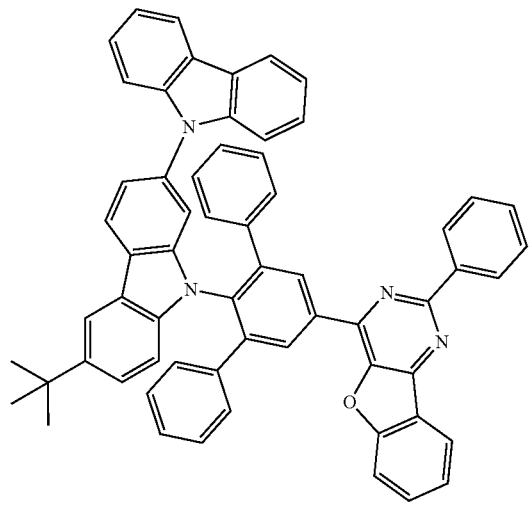
507
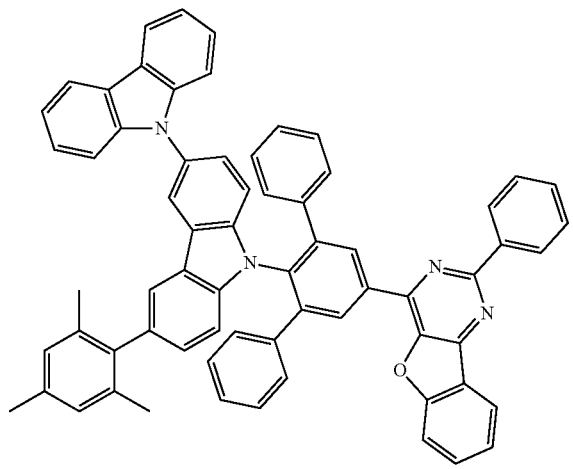
508
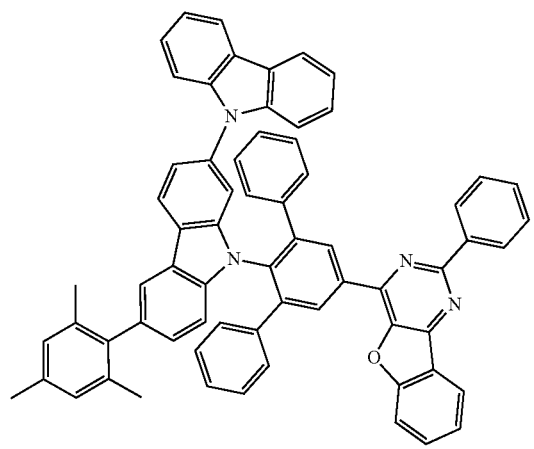
509
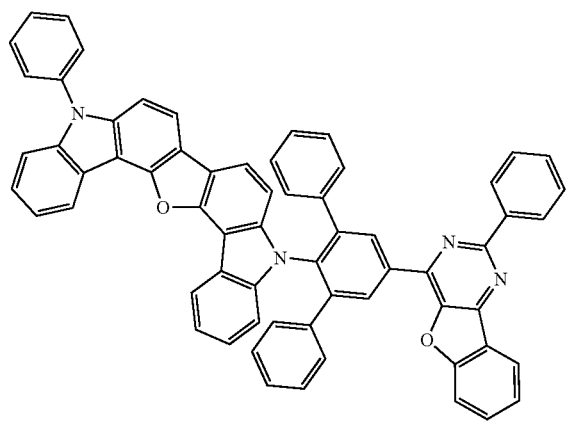
510
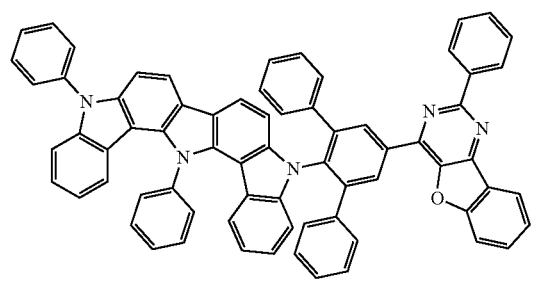
511
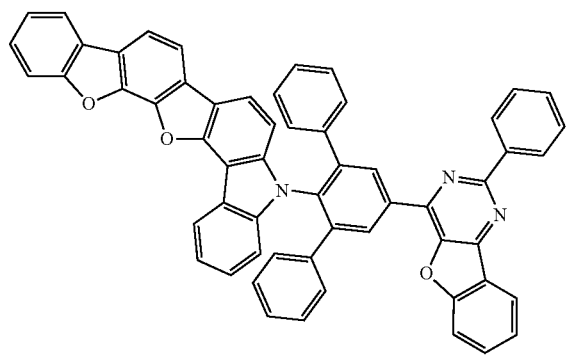

1065 1066
-continued
512
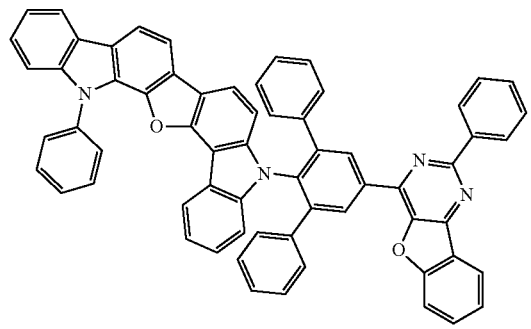
513
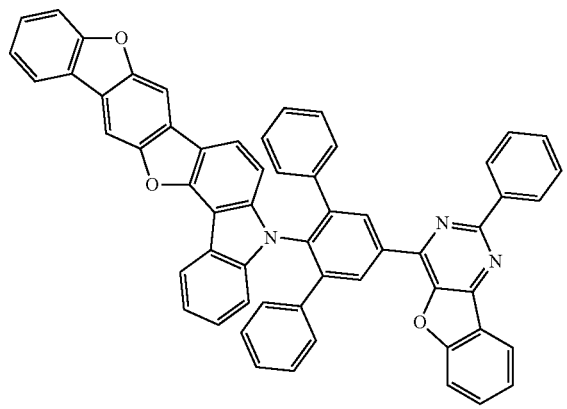
514
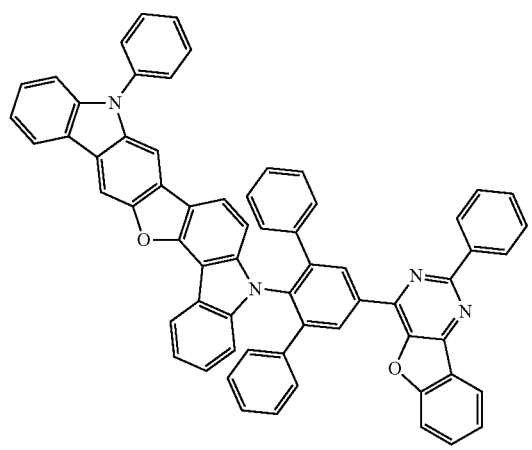
515
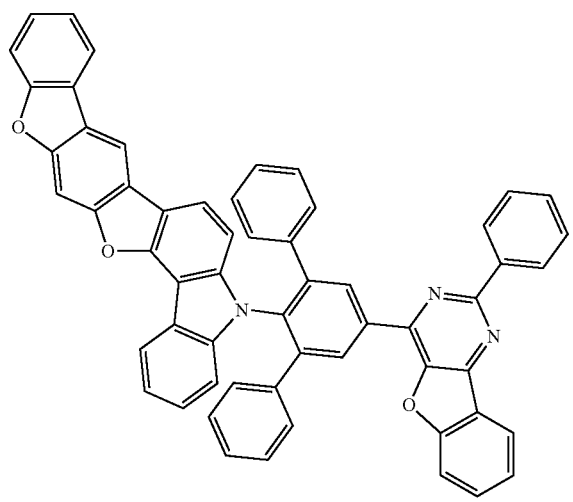
516
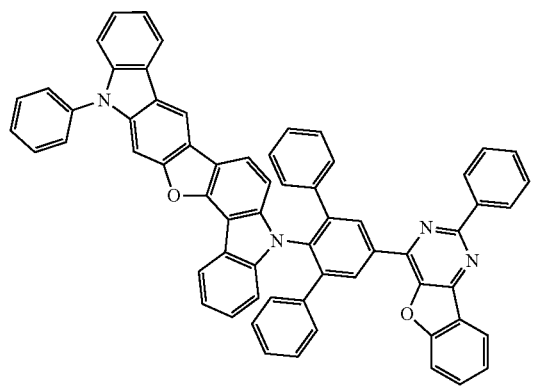
517
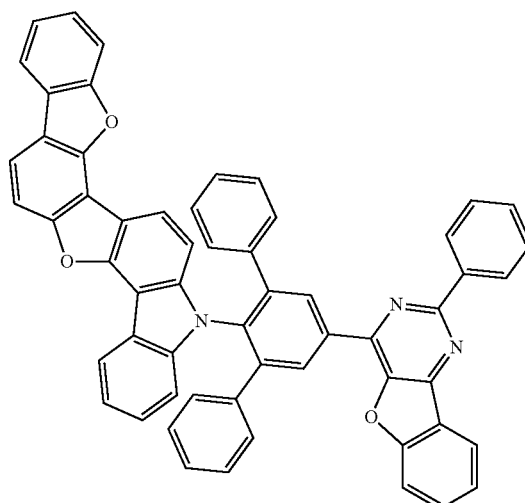

518
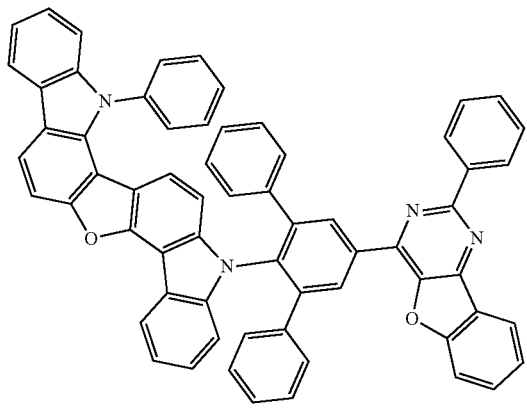
519
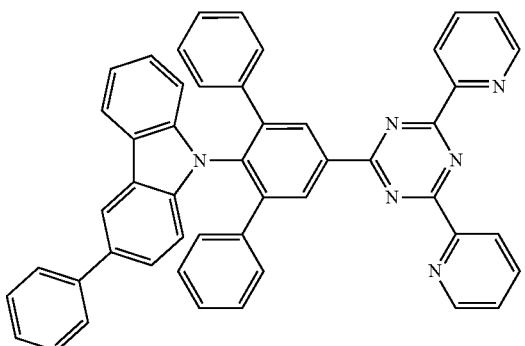
520
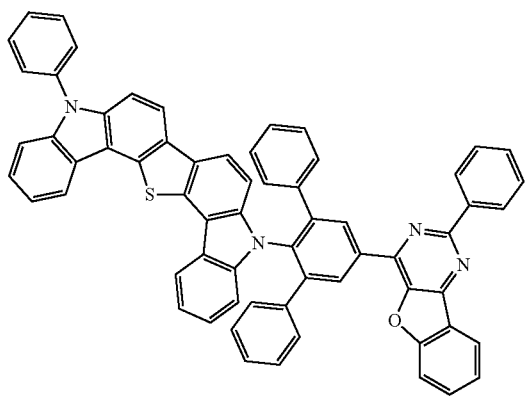
521
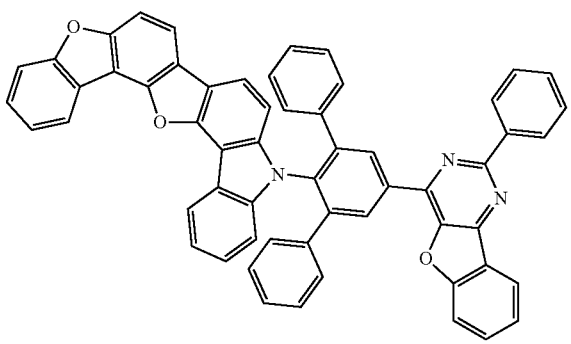
522
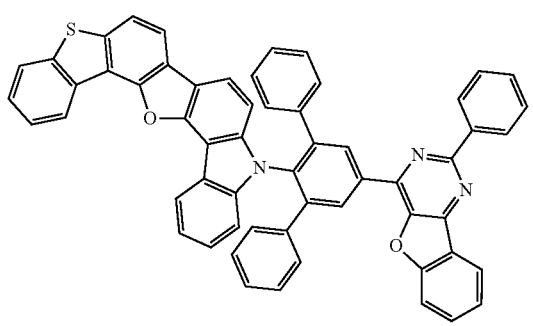
523
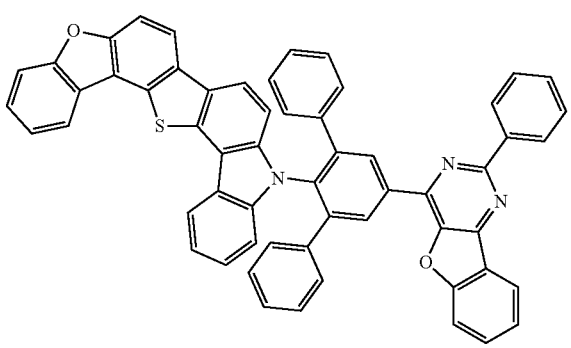
524
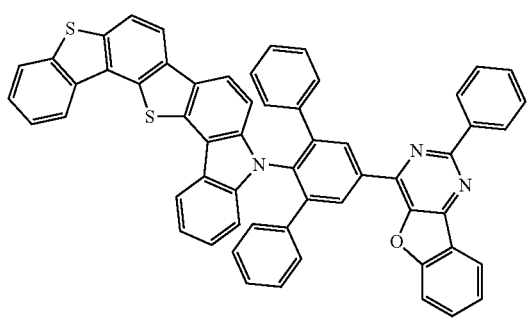
525
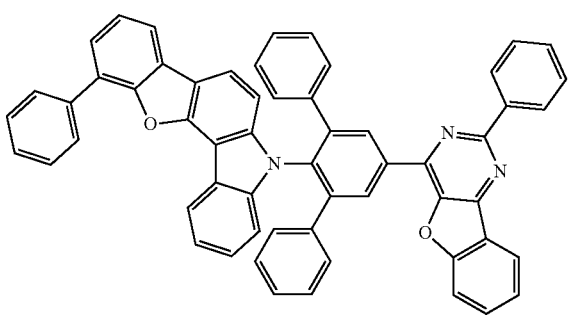

-continued
| 526 | 527 |
|---|---|
| 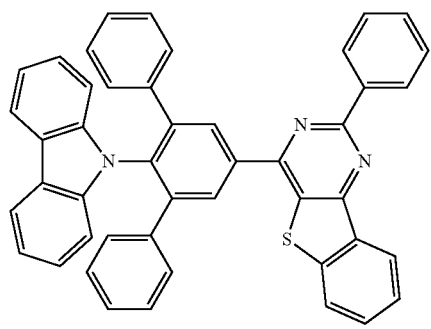 | 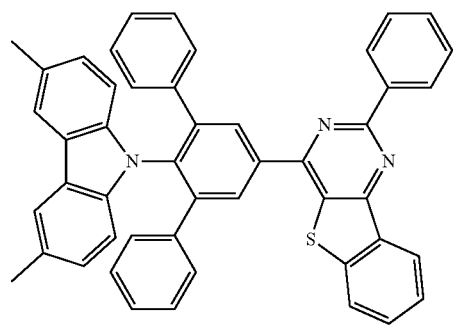 |
| 528 | 529 |
| 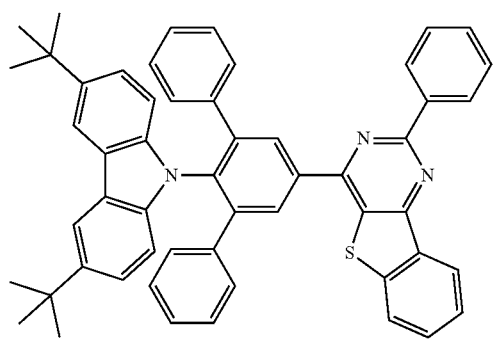 | 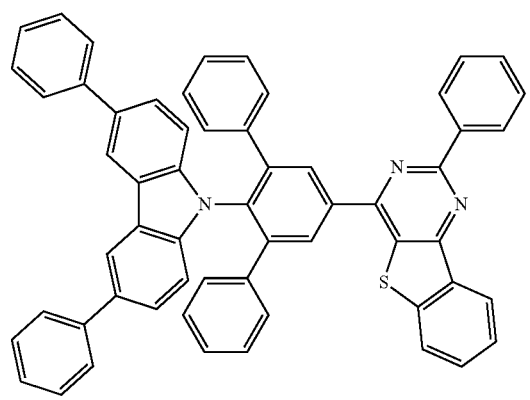 |
| 530 | 531 |
| 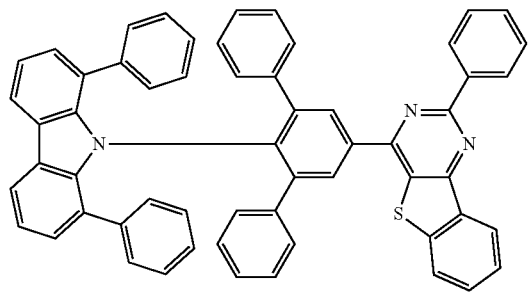 | 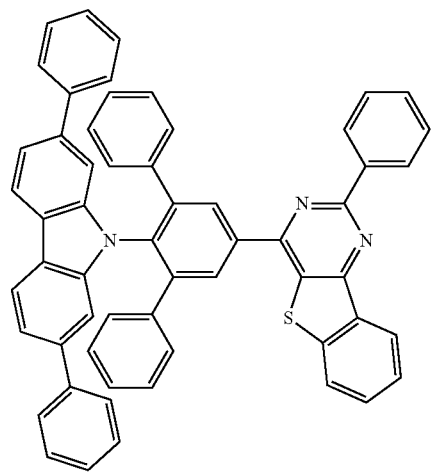 |
| 532 | 533 |
| 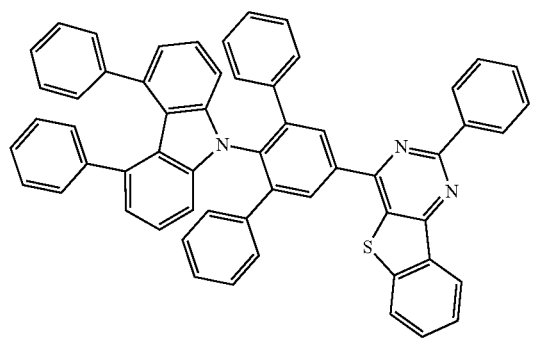 | 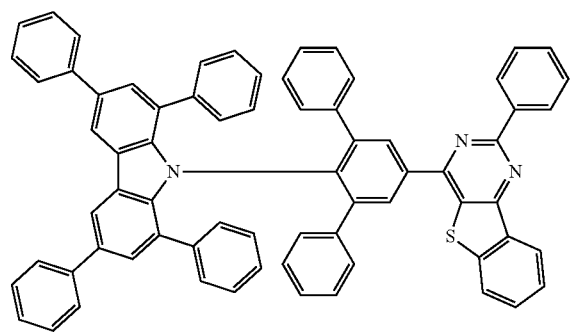 |

-continued
1071
534
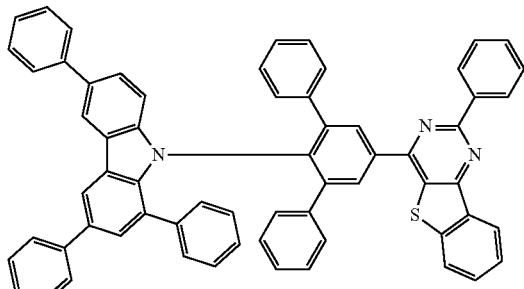
536
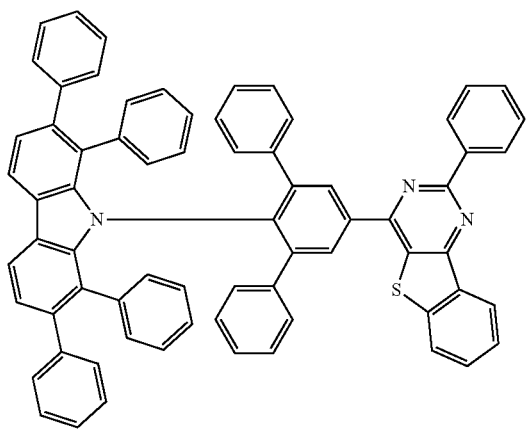
538
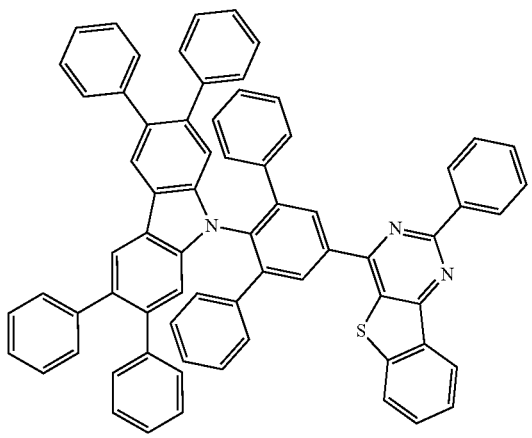
540
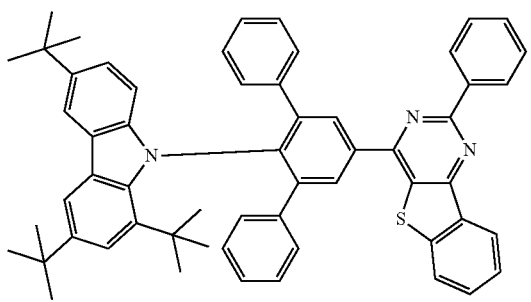
1072
535
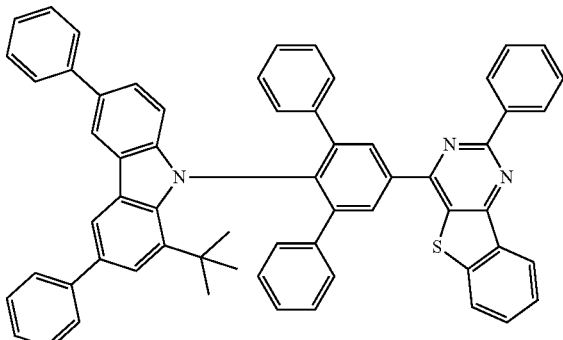
537
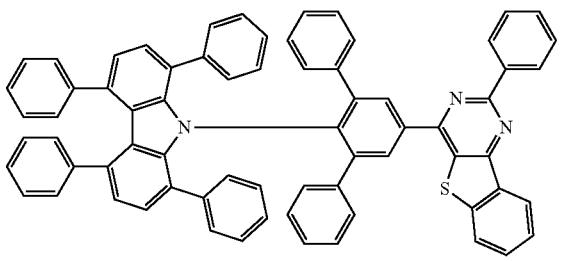
539
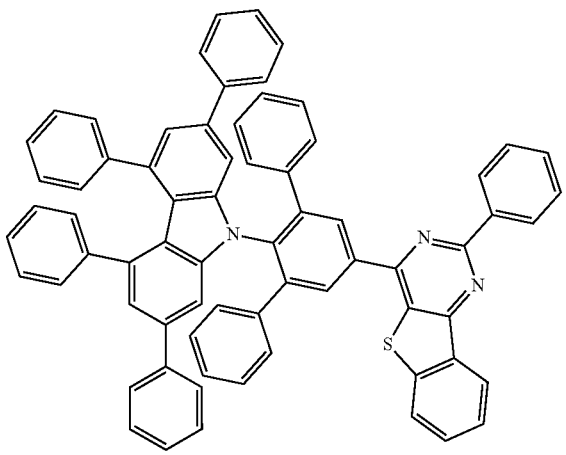
541
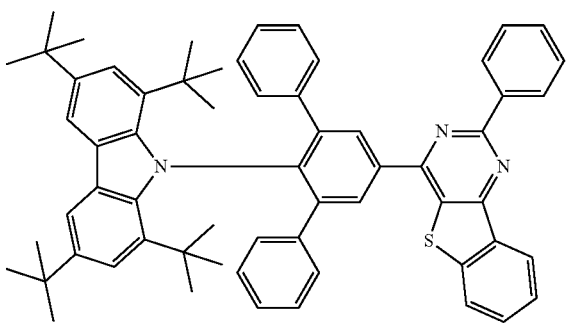

-continued
542
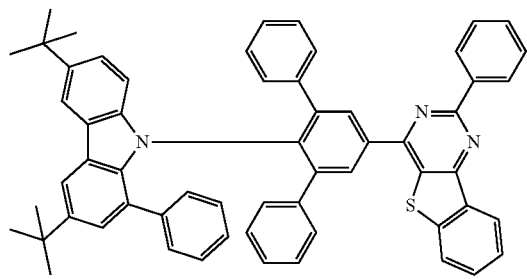
543
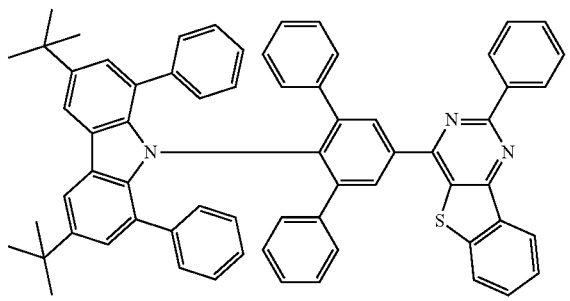
544
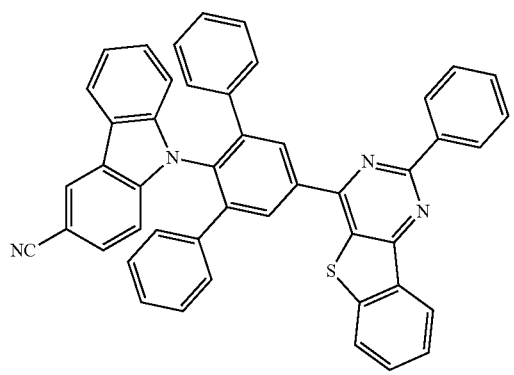
545
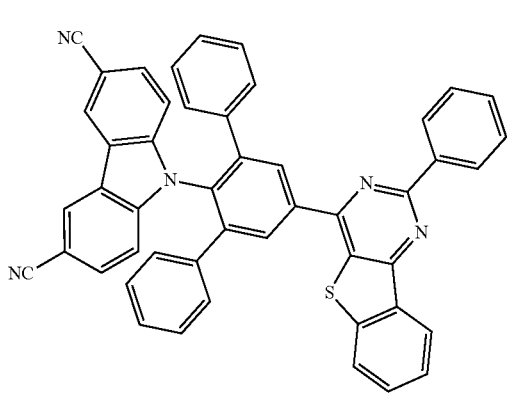
546
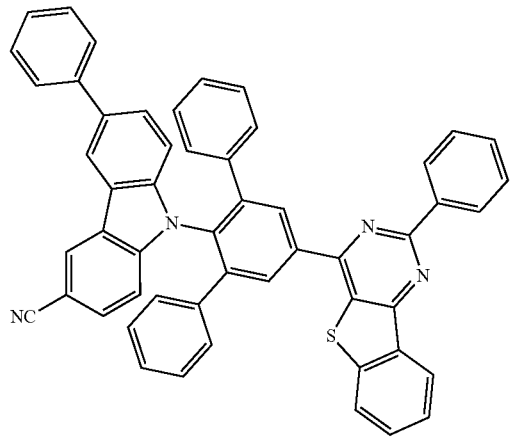
547
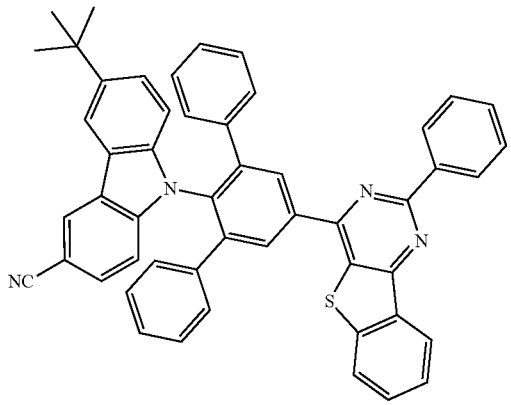
548
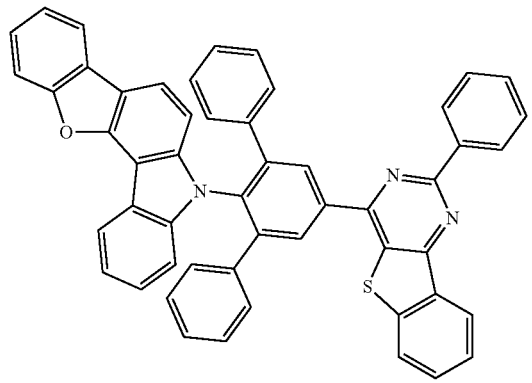
549
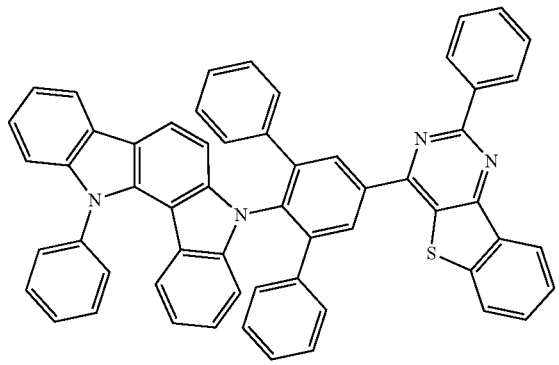

-continued
1075
550
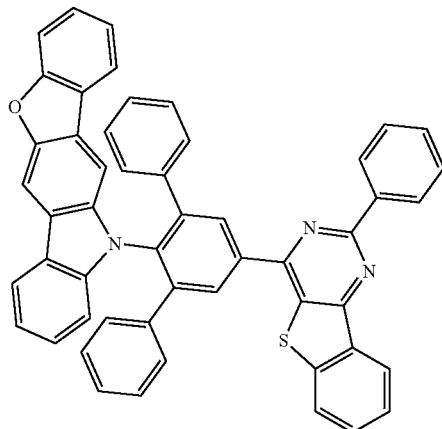
552
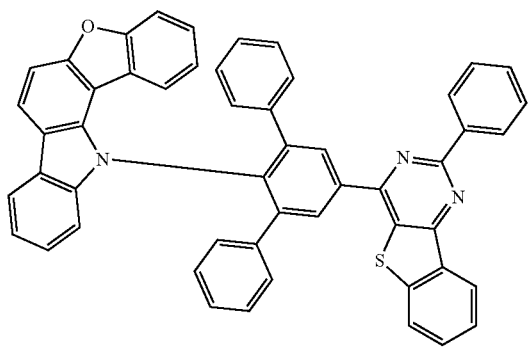
554
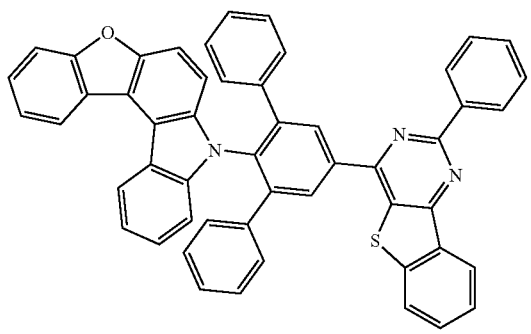
1076
551
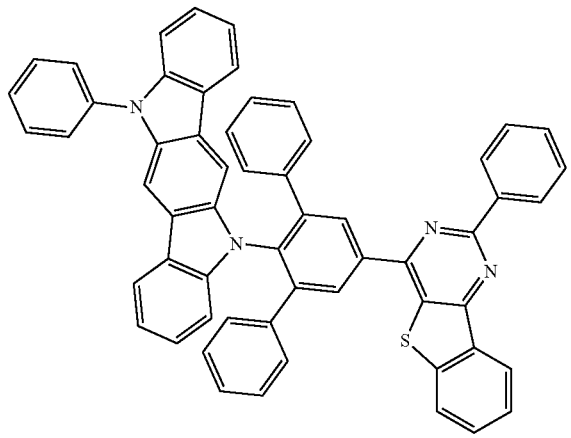
553
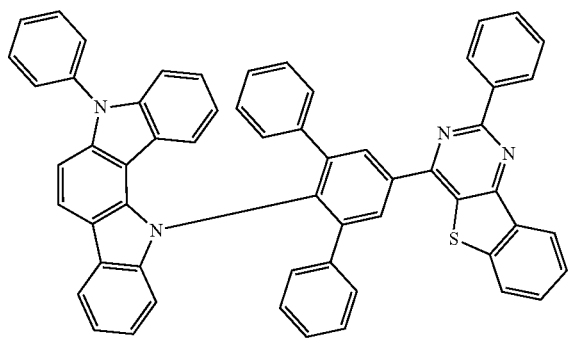
555
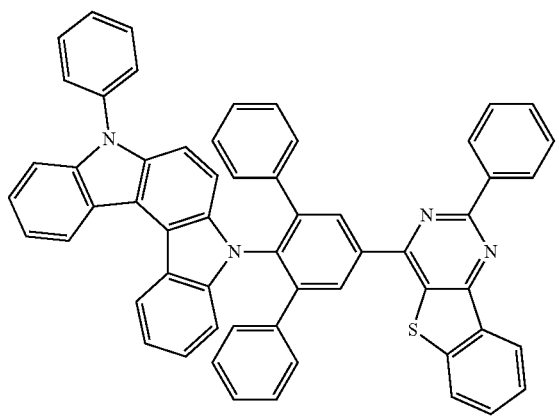

-continued
556
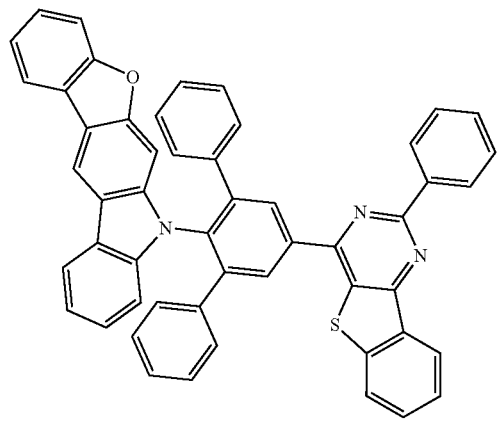
557
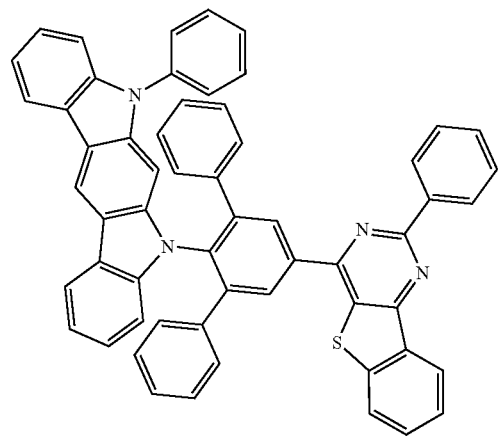
558
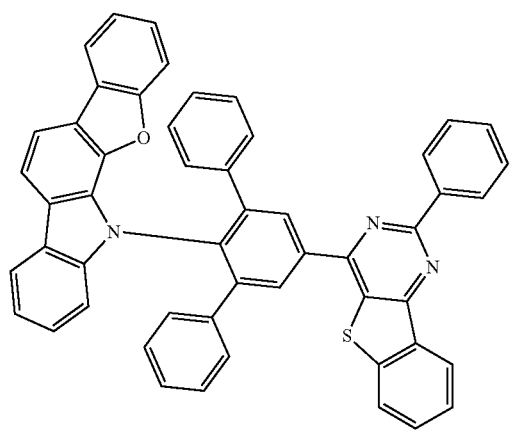
559
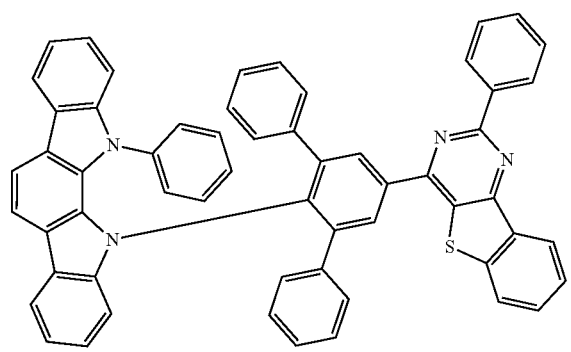
560
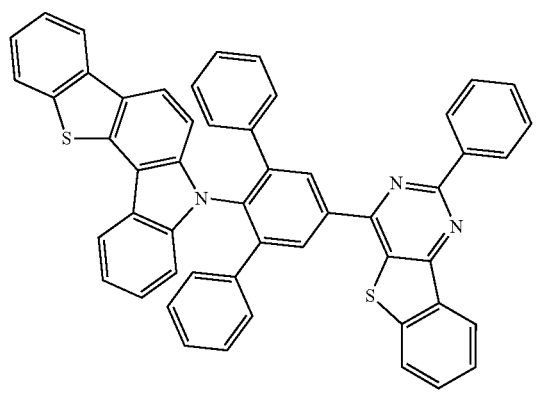
561
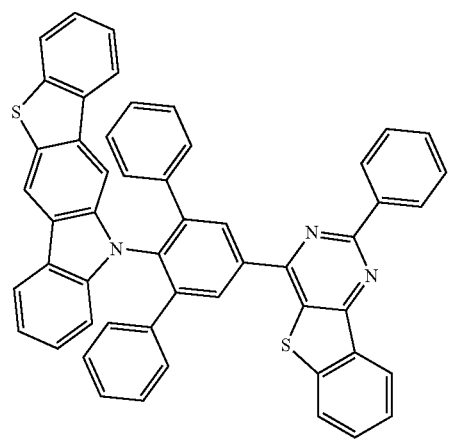

562
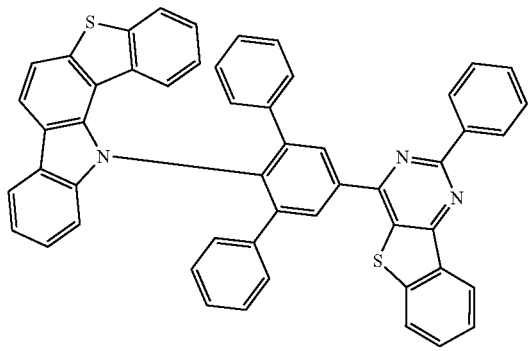
563
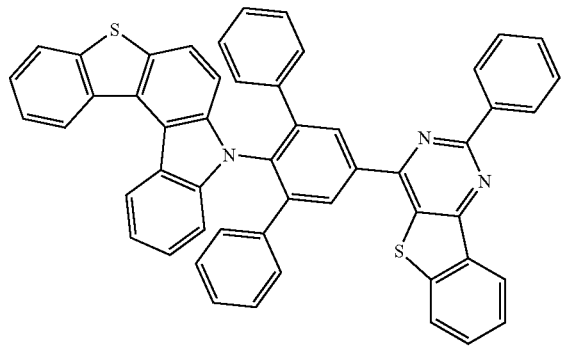
564
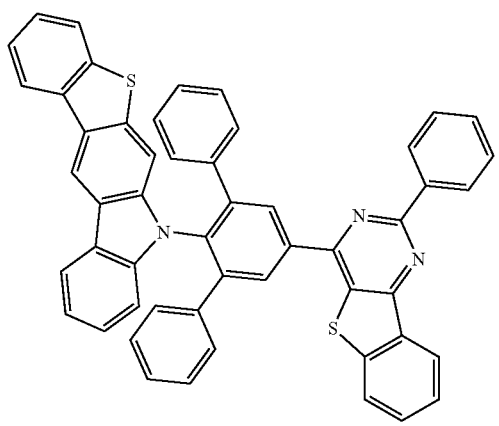
565
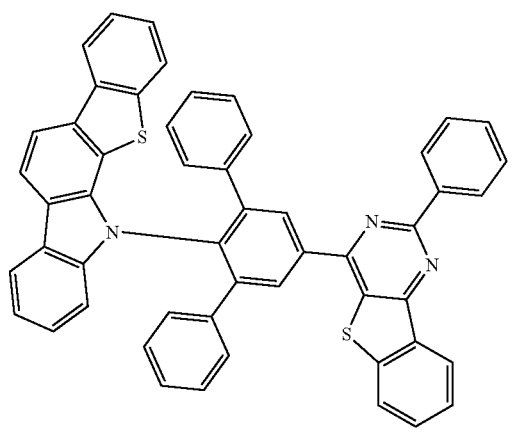
566
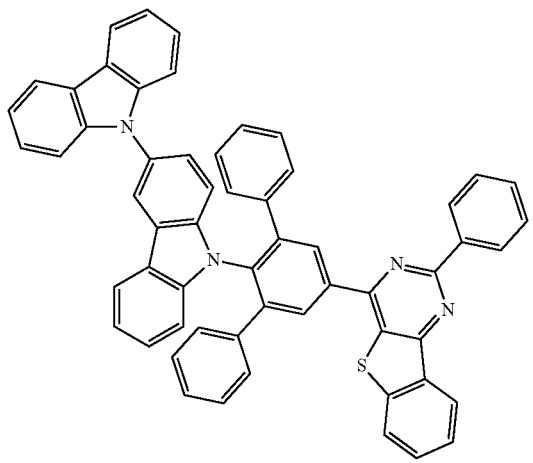
567
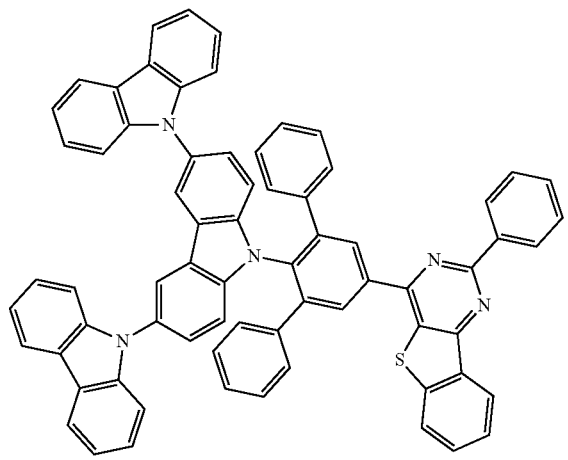

568
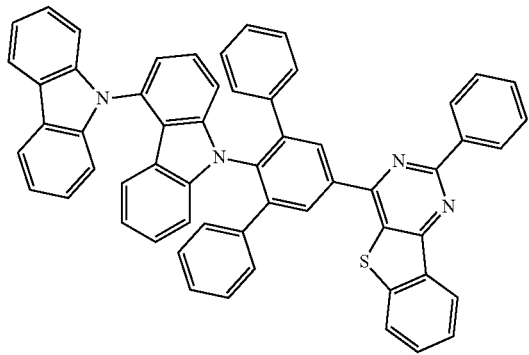
569
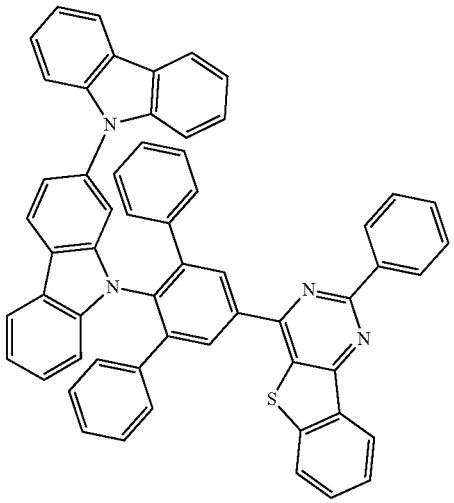
570
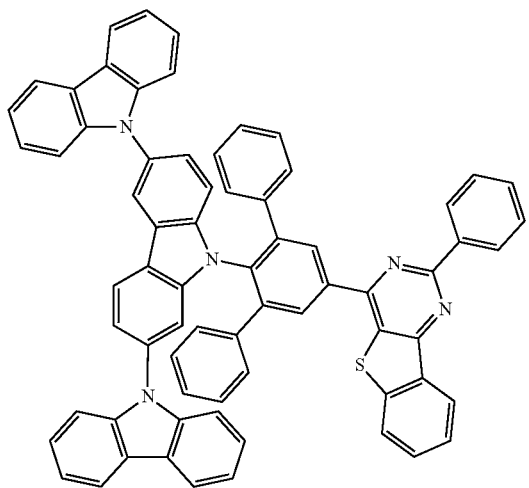
571
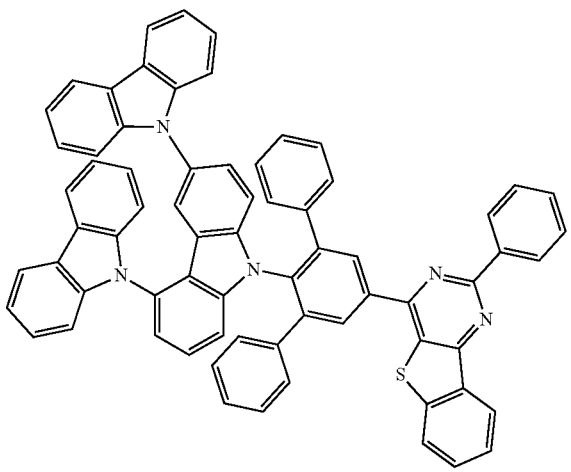
572
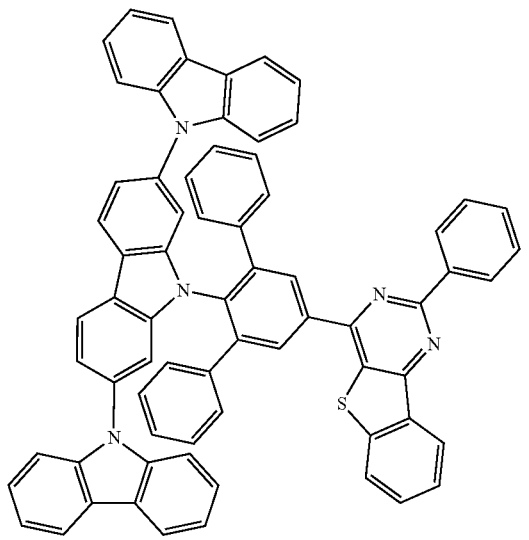
573
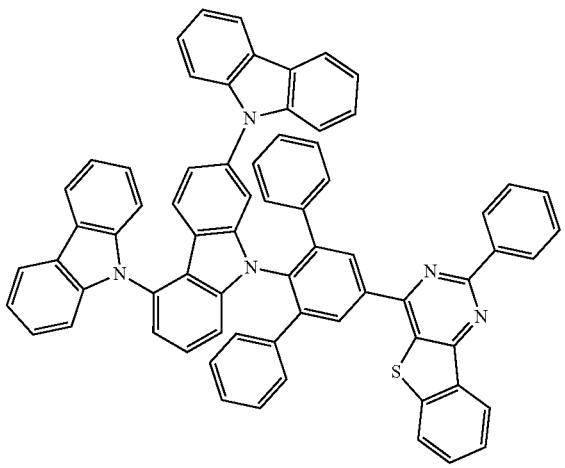

-continued
574
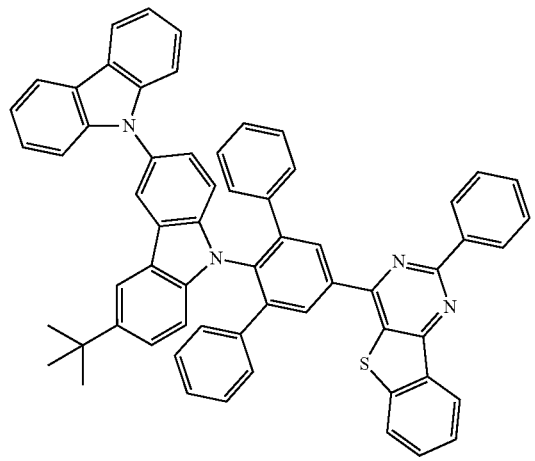
575
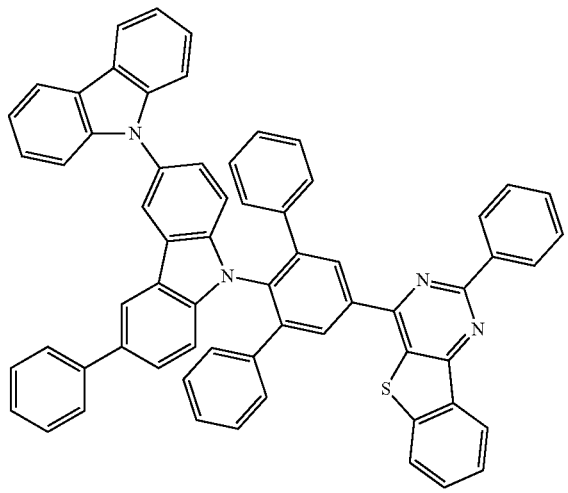
576
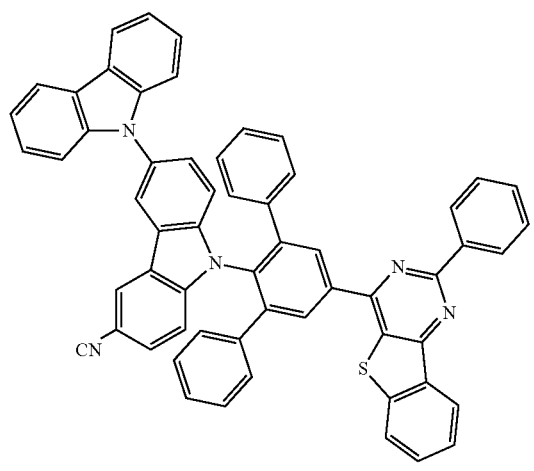
577
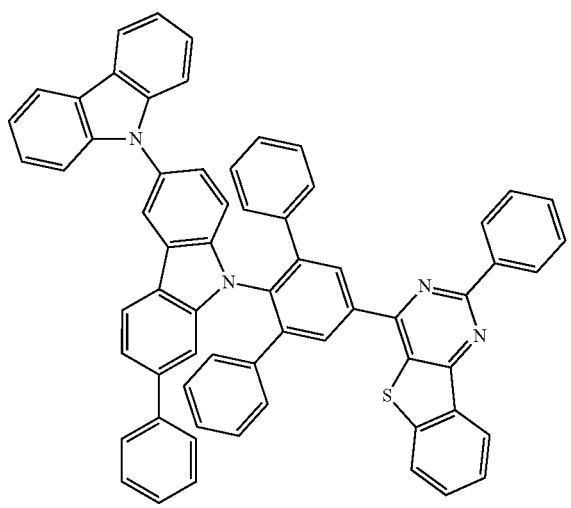
578
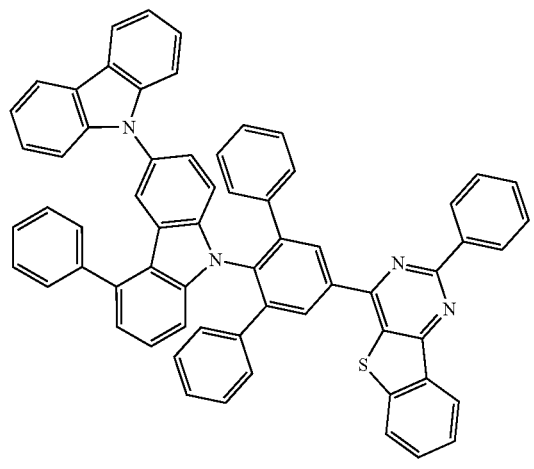
579
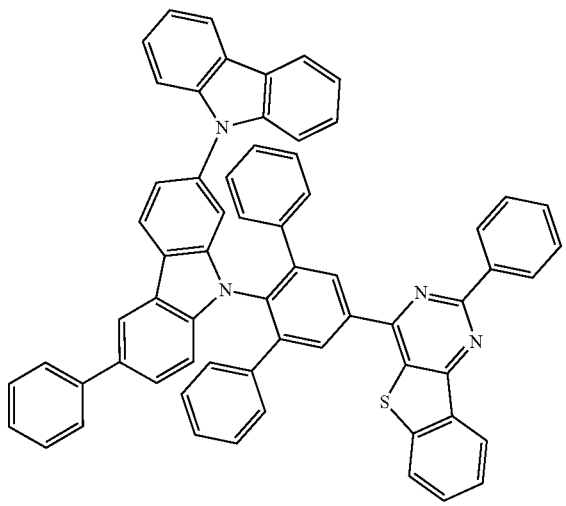

1085 1086
580
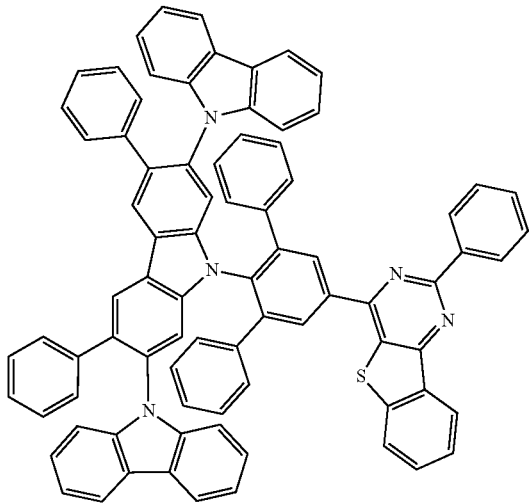
581
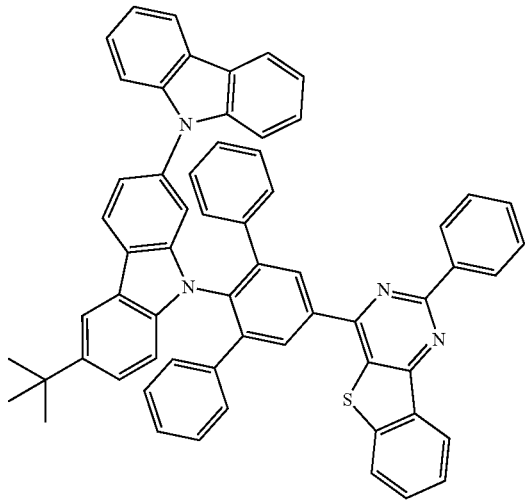
582
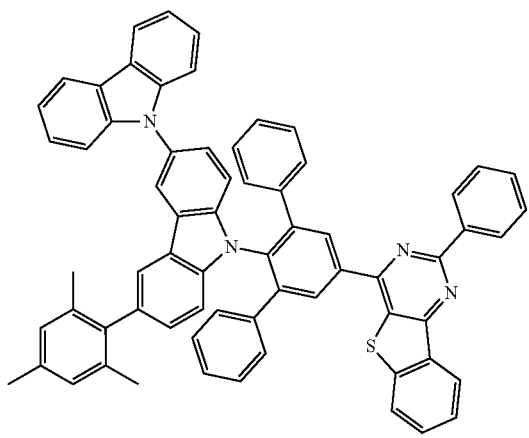
583
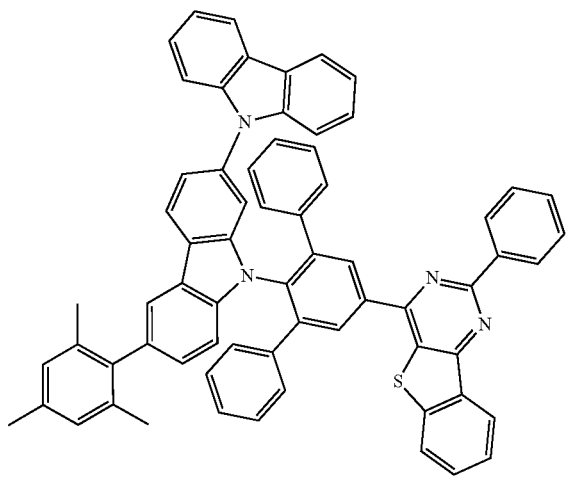
584
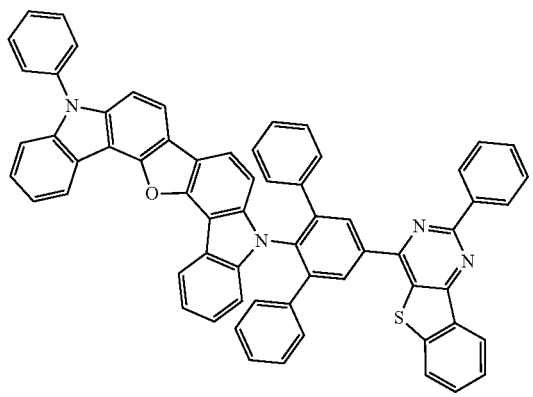
585
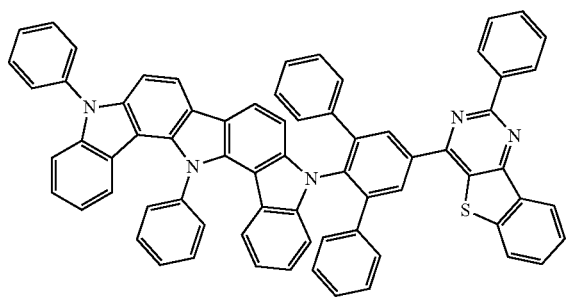

1087                                                  1088
586                                                   587
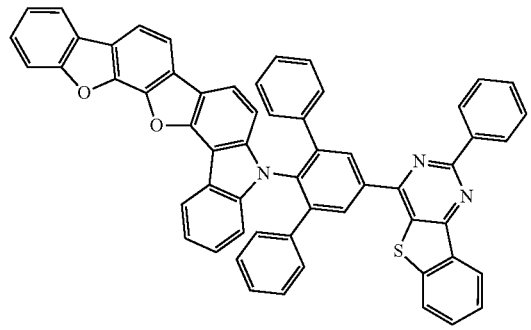   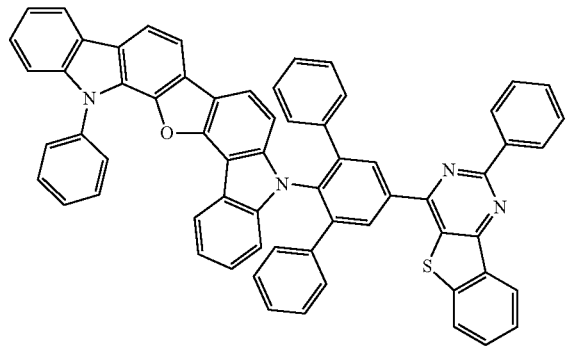
588                                                   589
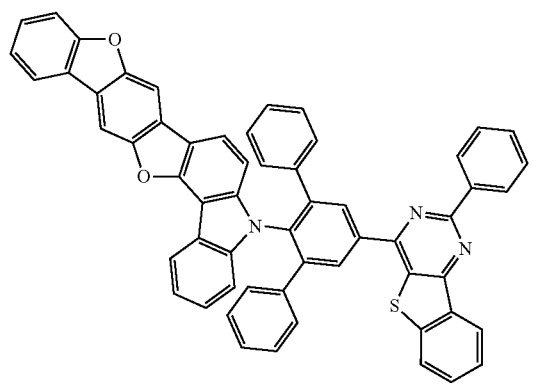   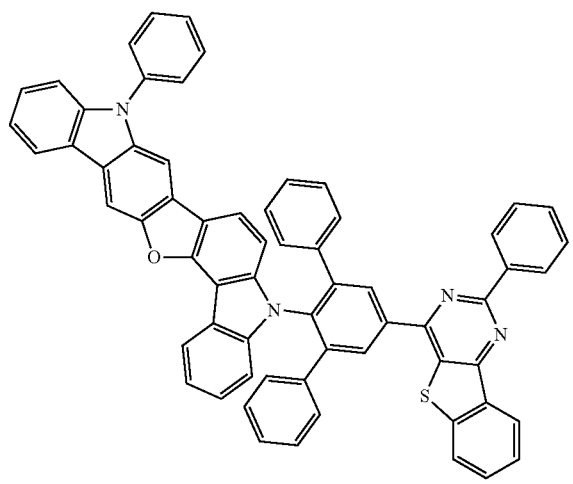
590                                                   591
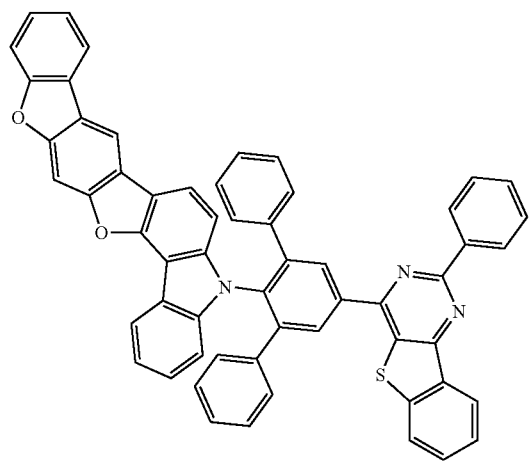   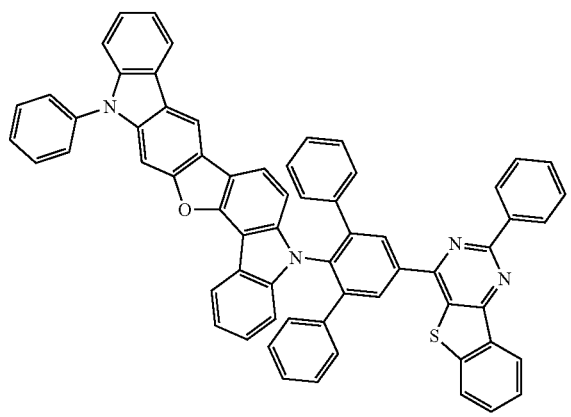

-continued
592
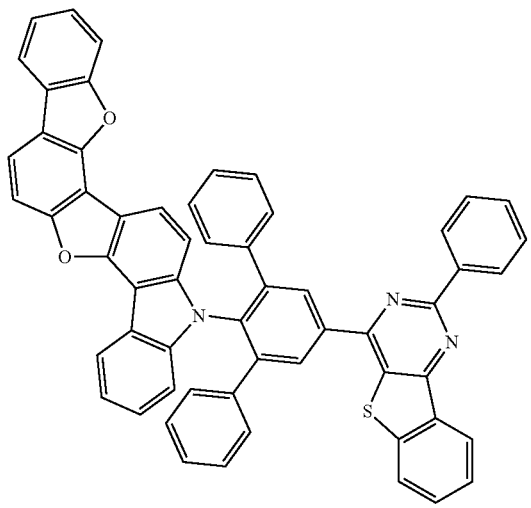
593
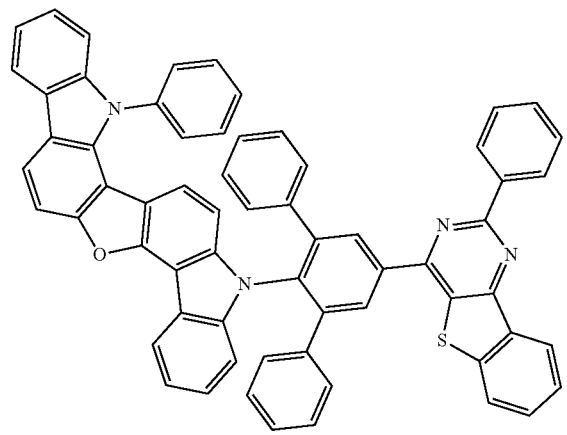
594
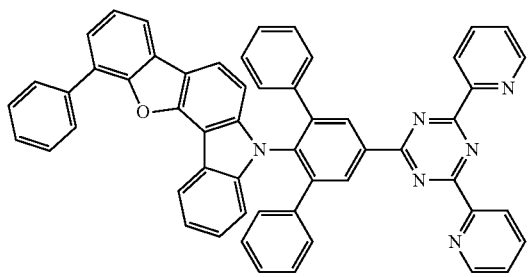
595
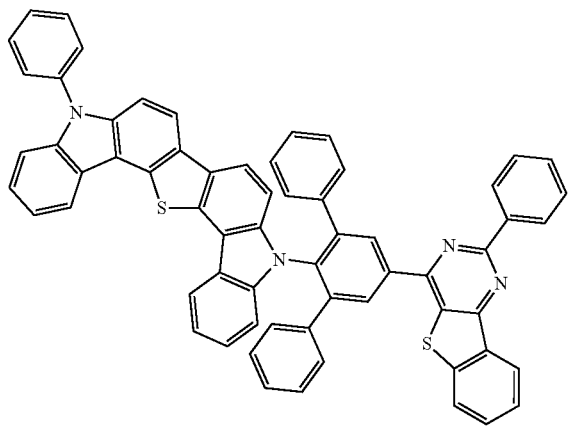
596
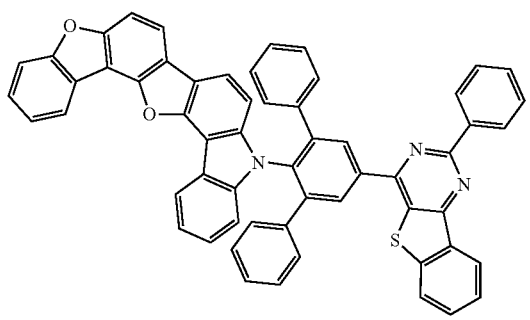
597
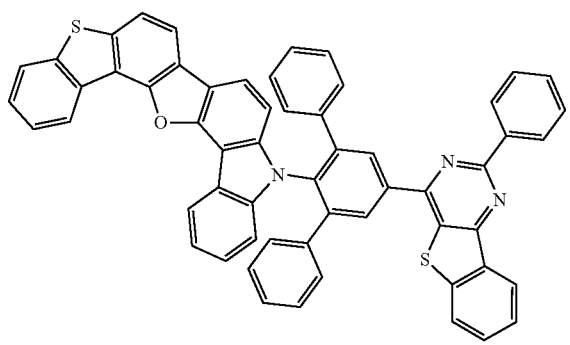

-continued
598
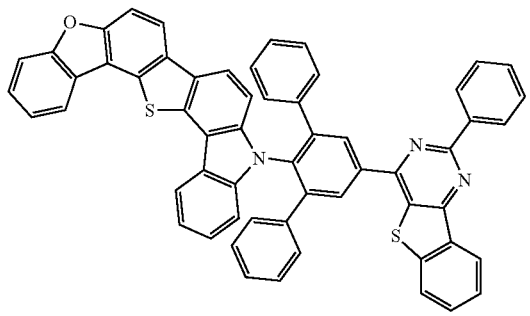
599
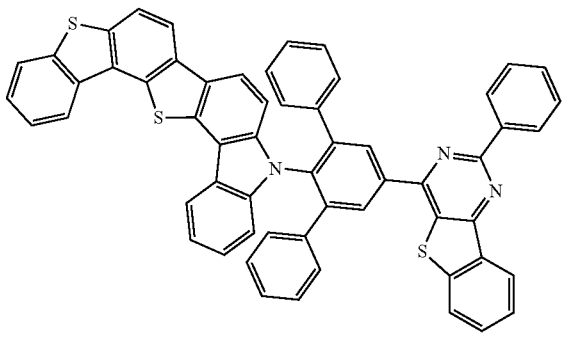
600
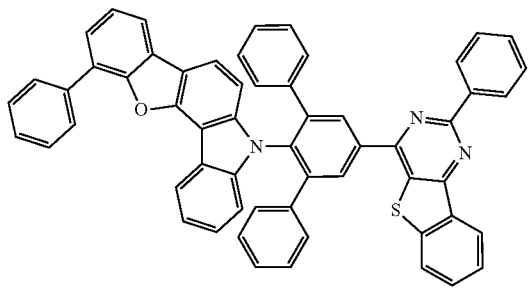
601
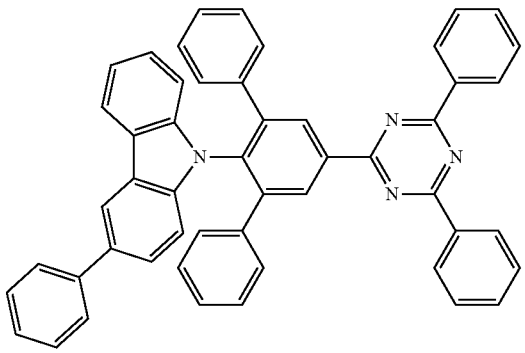
602
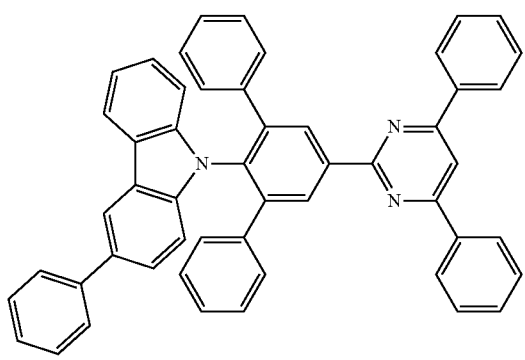
603
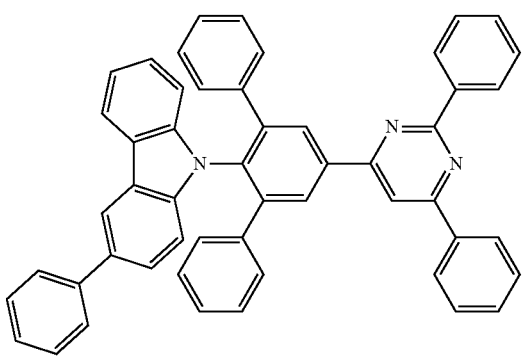
604
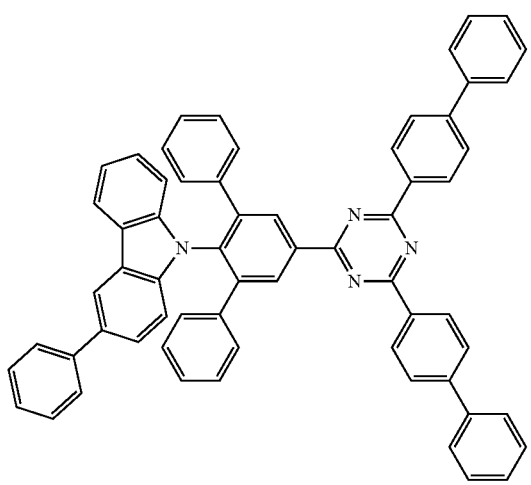
605
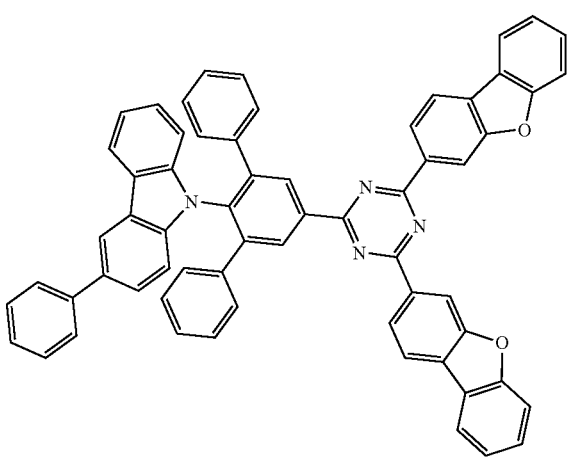

-continued
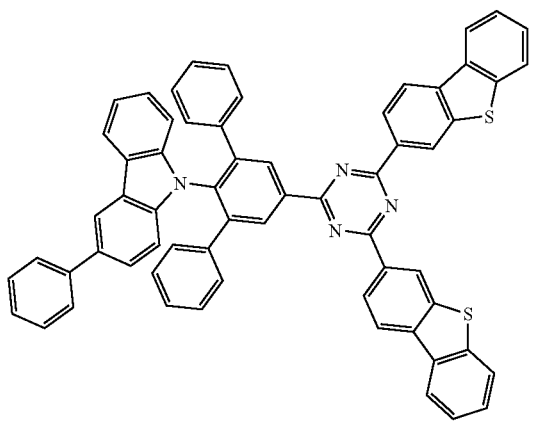
606
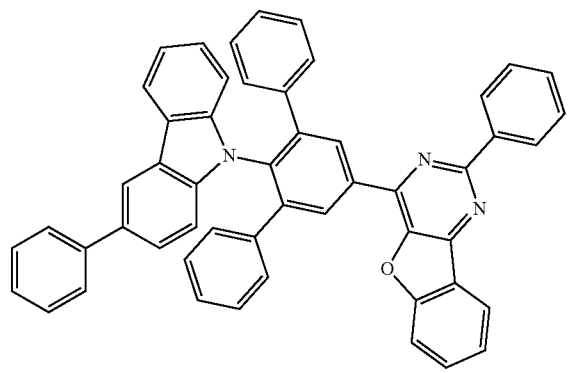
607
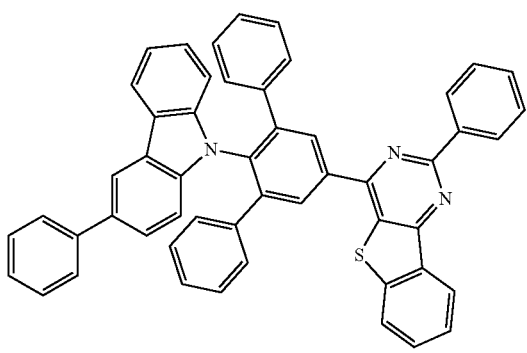
608
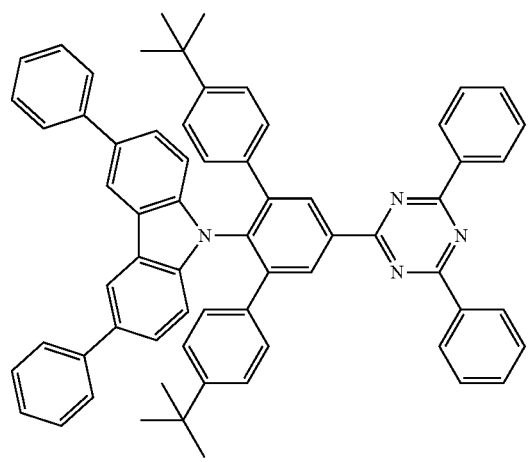
609
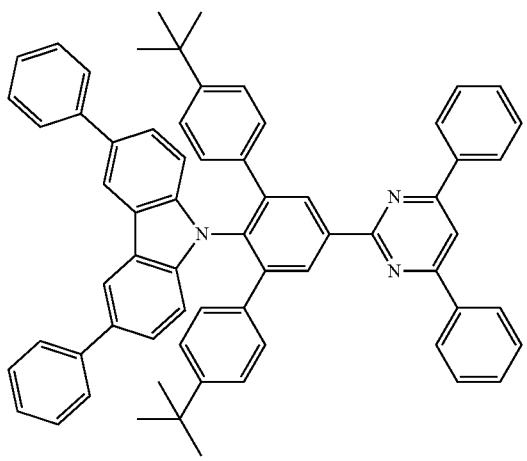
610
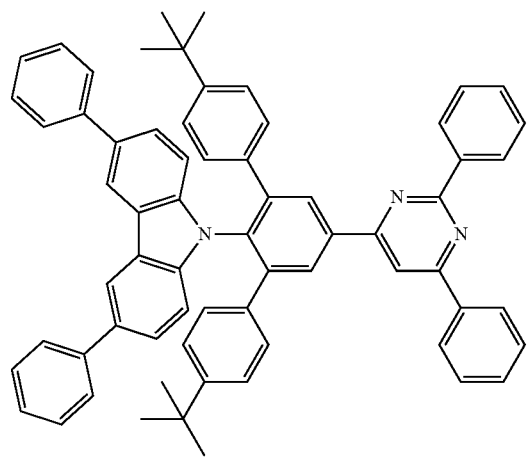
611

-continued
612
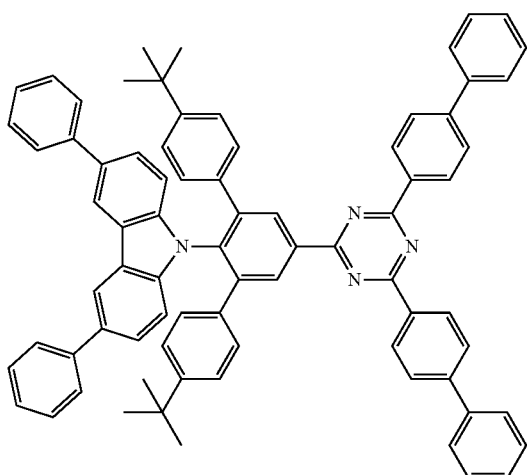
613
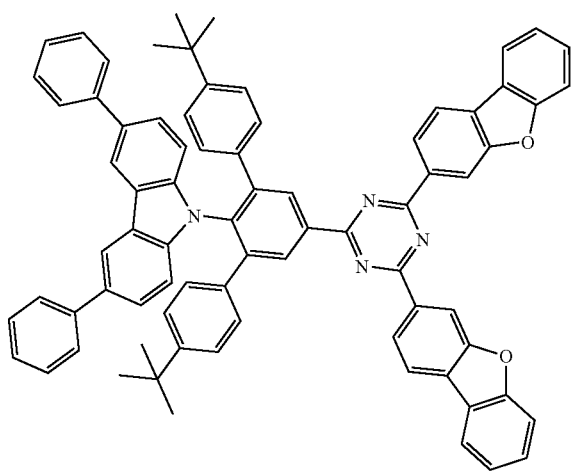
614
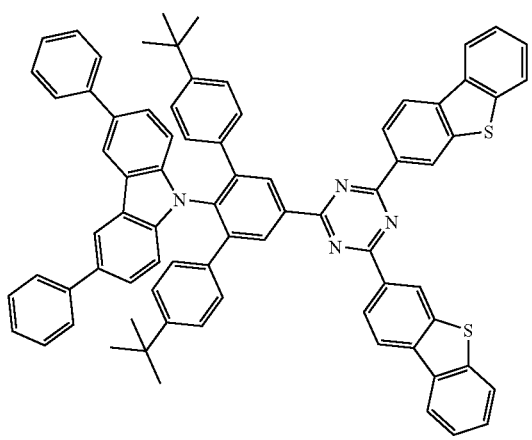
615
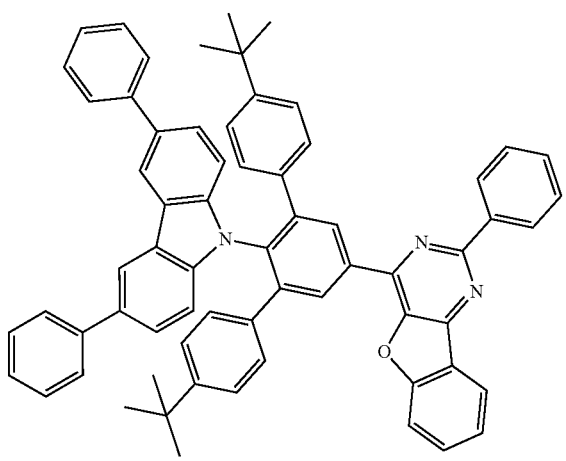
616
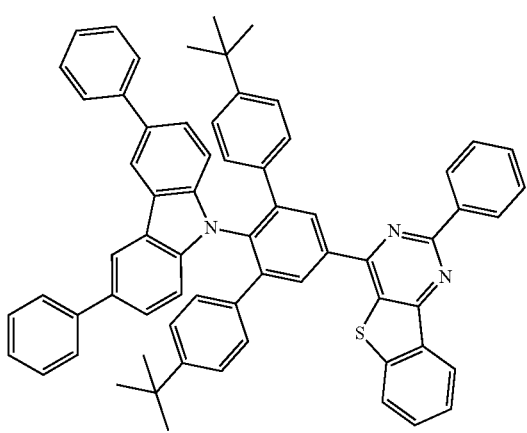
617
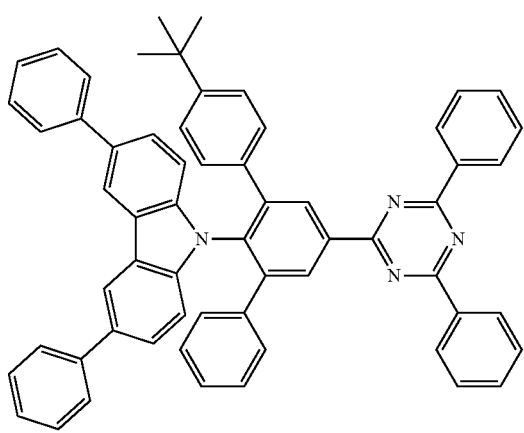

1097
1098
-continued
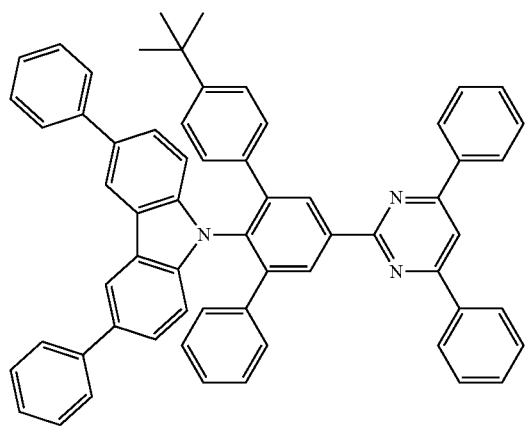
618
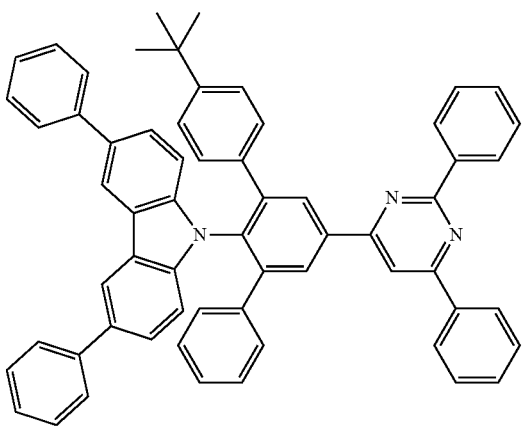
619
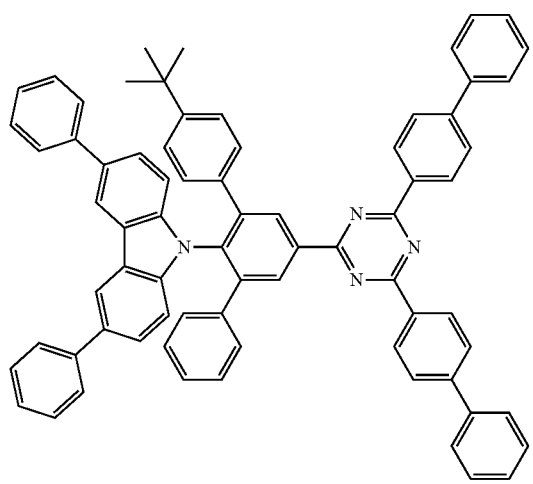
620
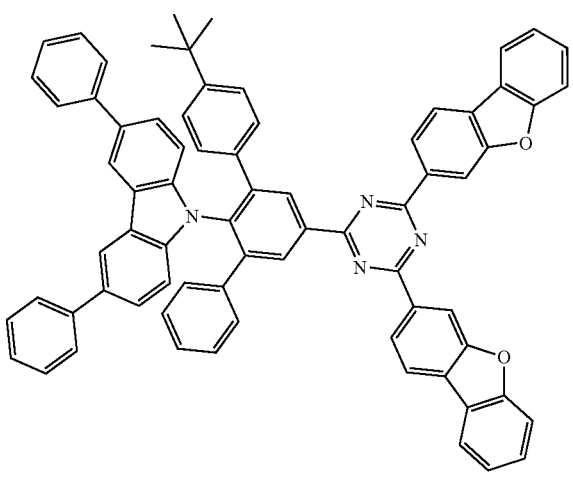
621
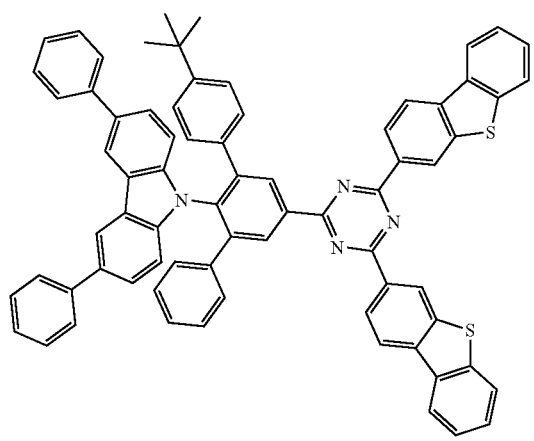
622
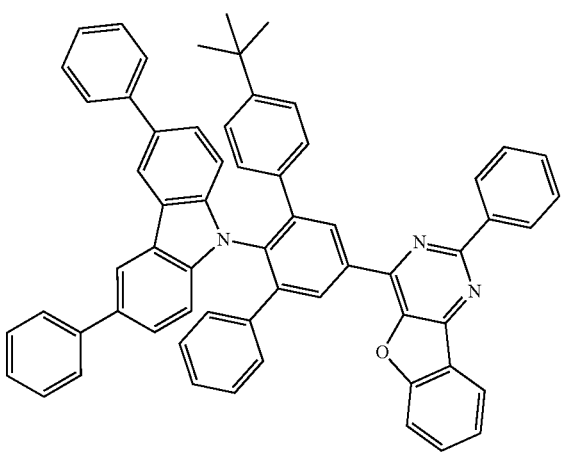
623

-continued
| 1099 | 1100 |
|---|---|
| 624 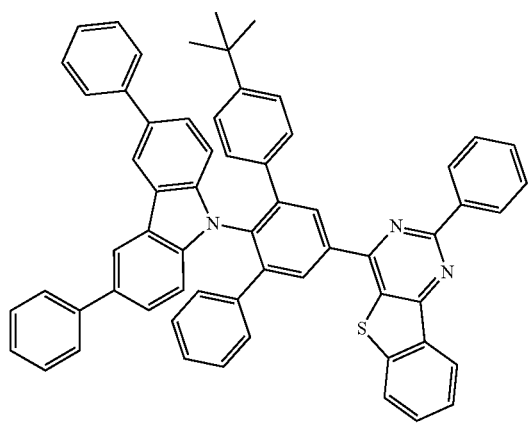 | 625 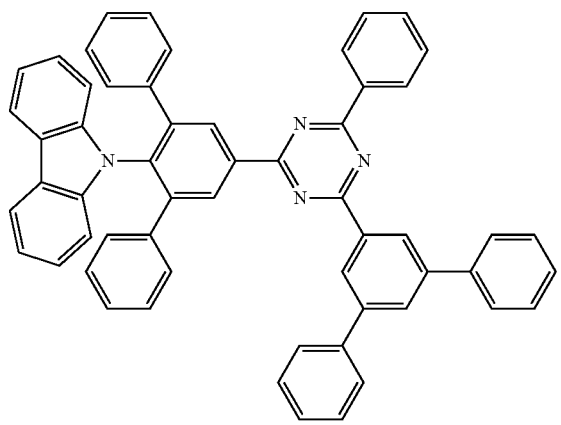 |
| 626 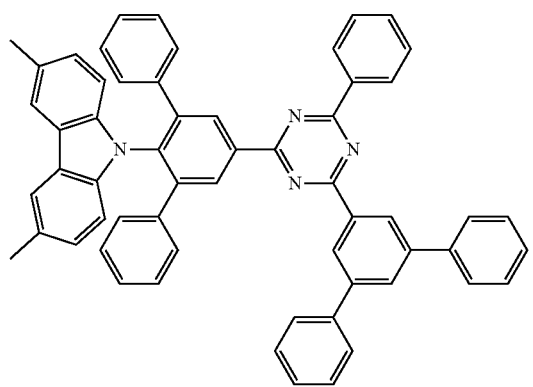 | 627 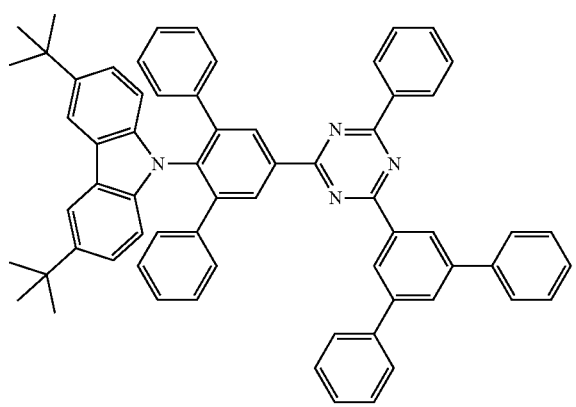 |
| 628 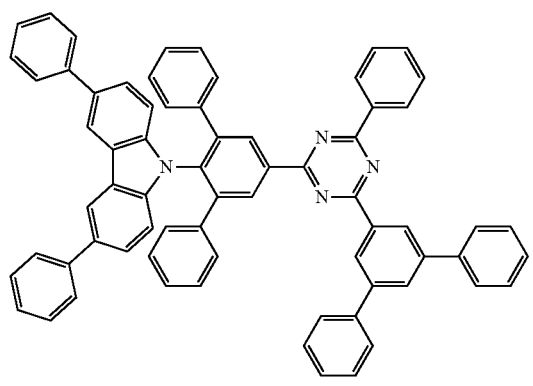 | 629 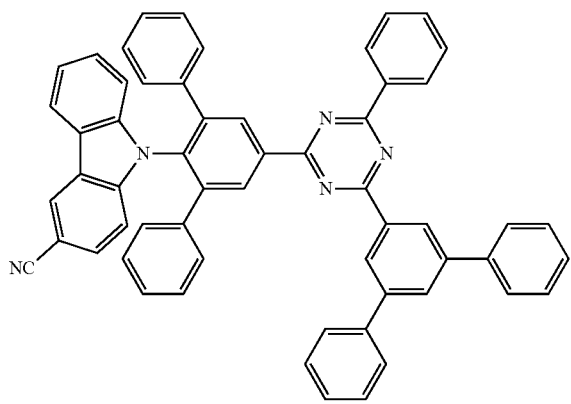 |

-continued
630
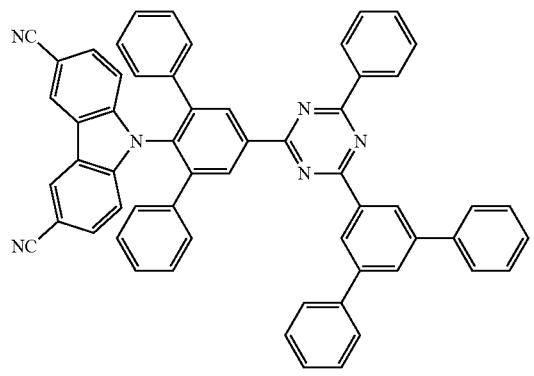
631
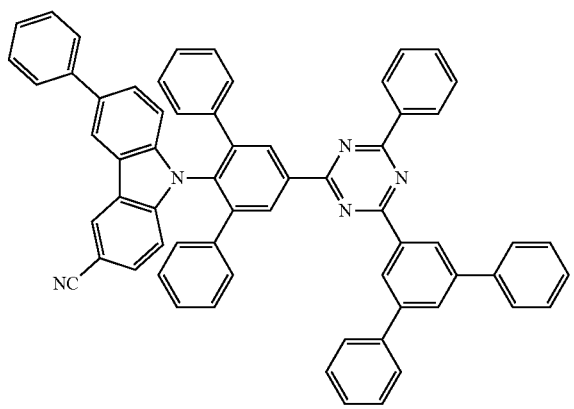
632
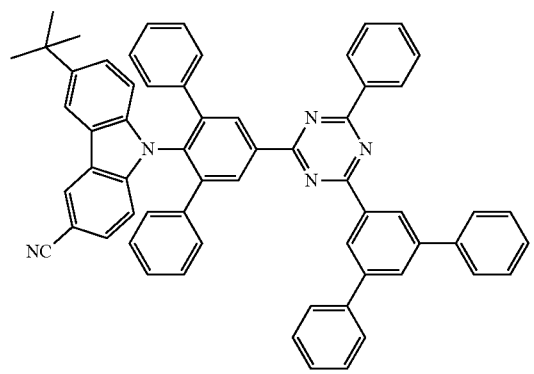
633
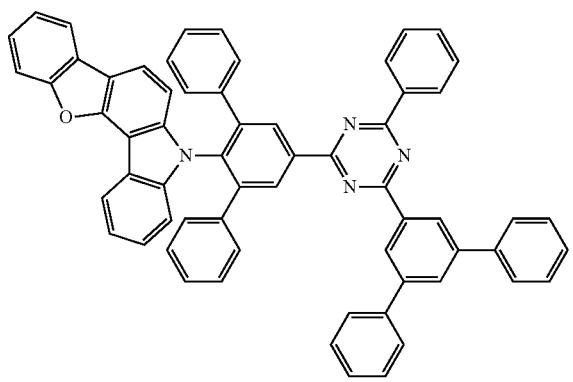
634
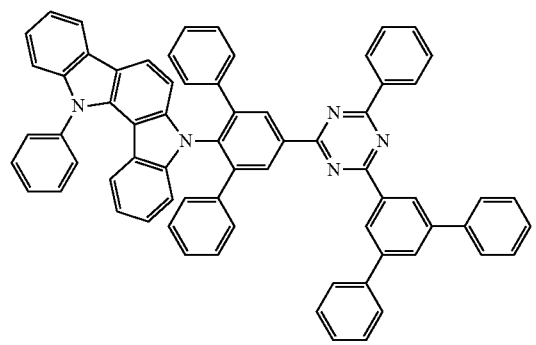
635
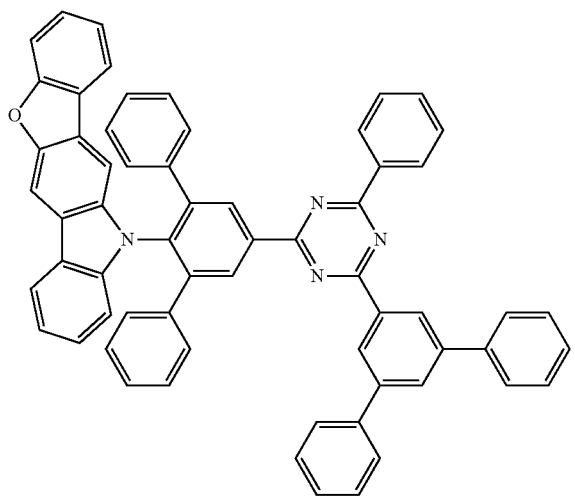

-continued
636
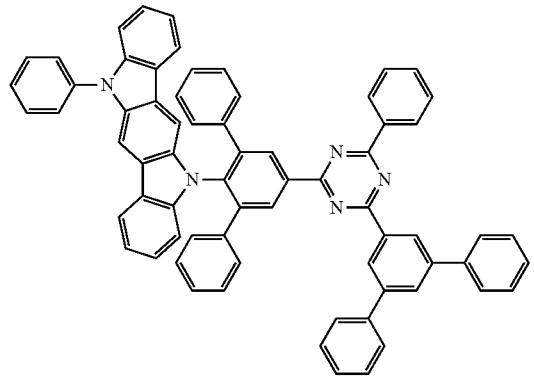
637
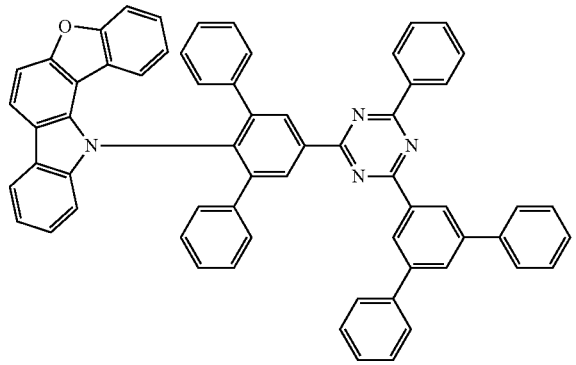
638
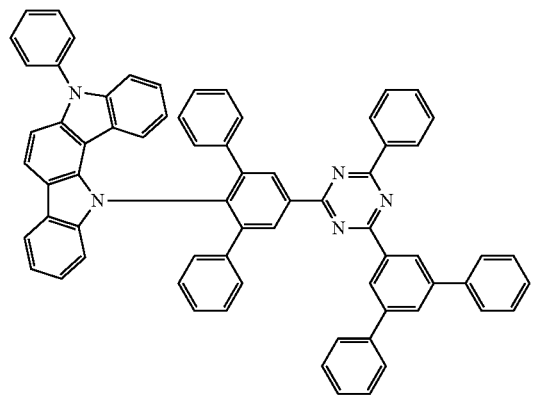
639
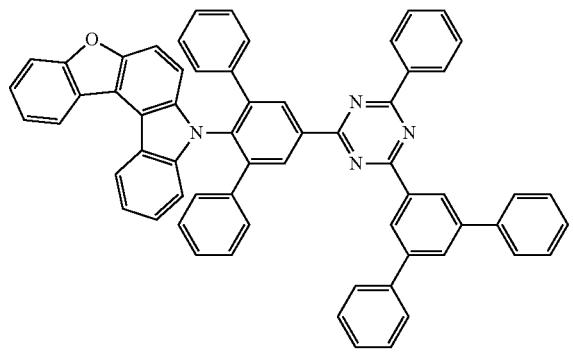
640
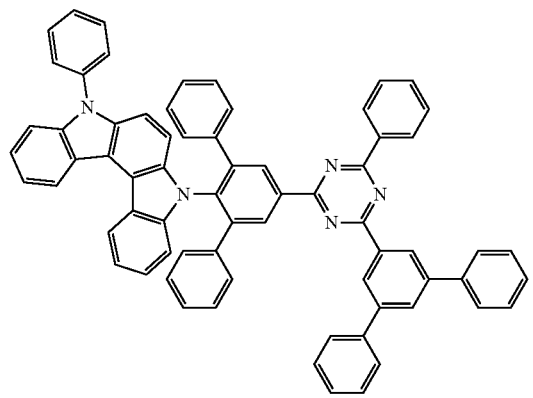
641
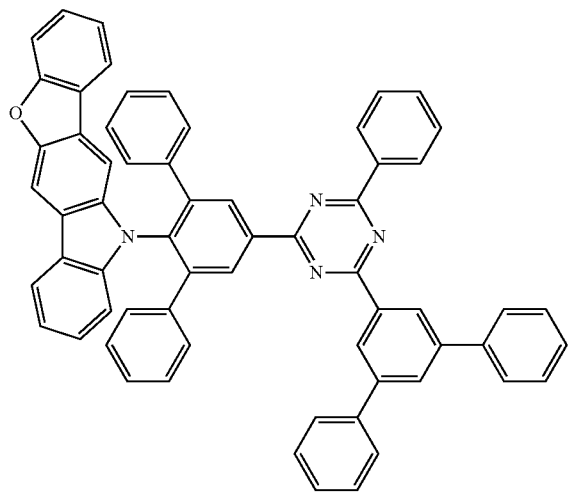

-continued
642
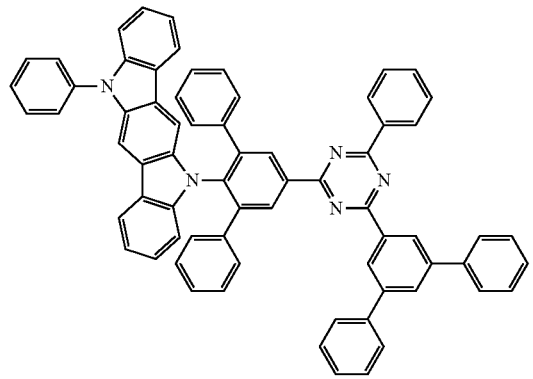
643
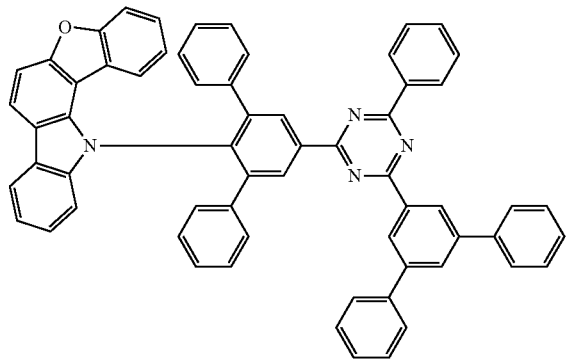
644
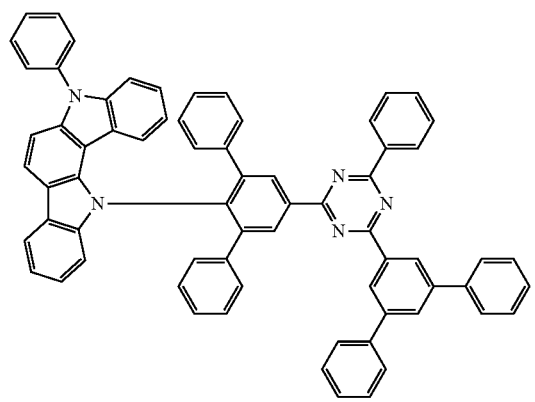
645
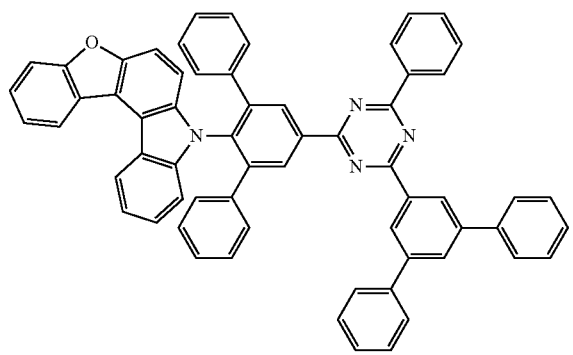
646
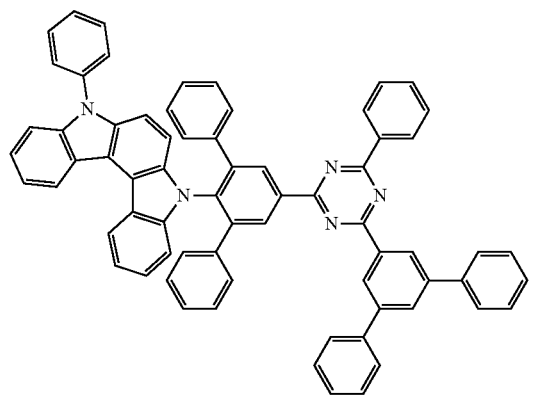
647
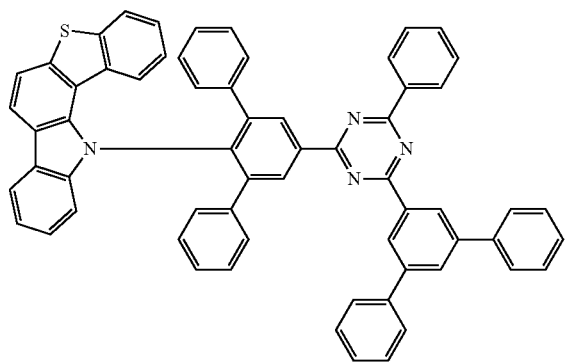

1107 1108
-continued
648
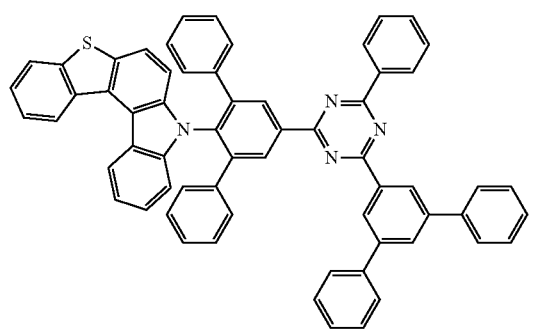
649
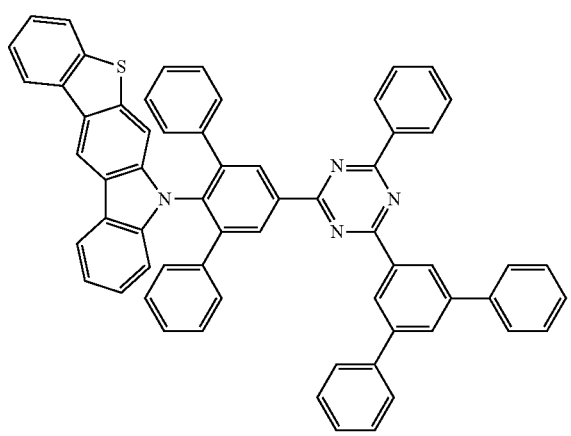
650
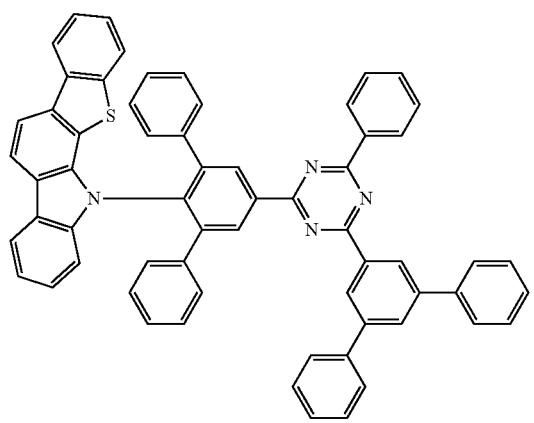
651
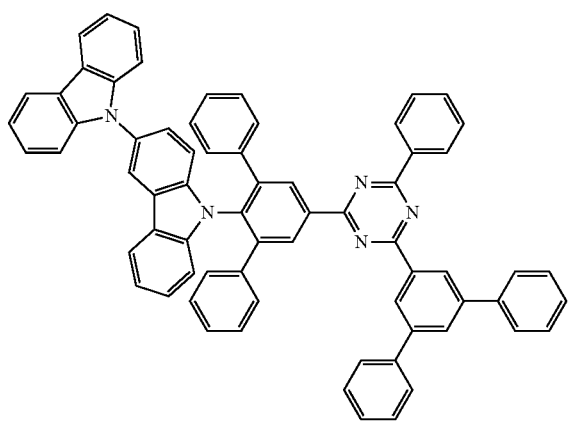
652
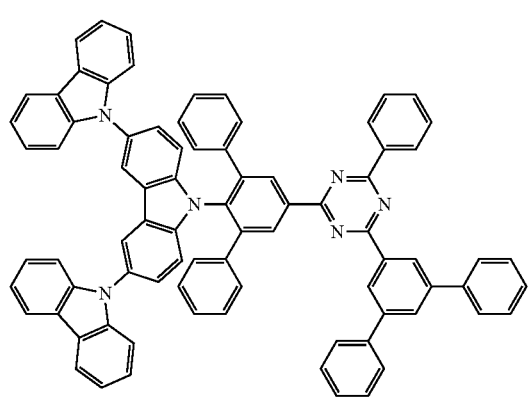

653
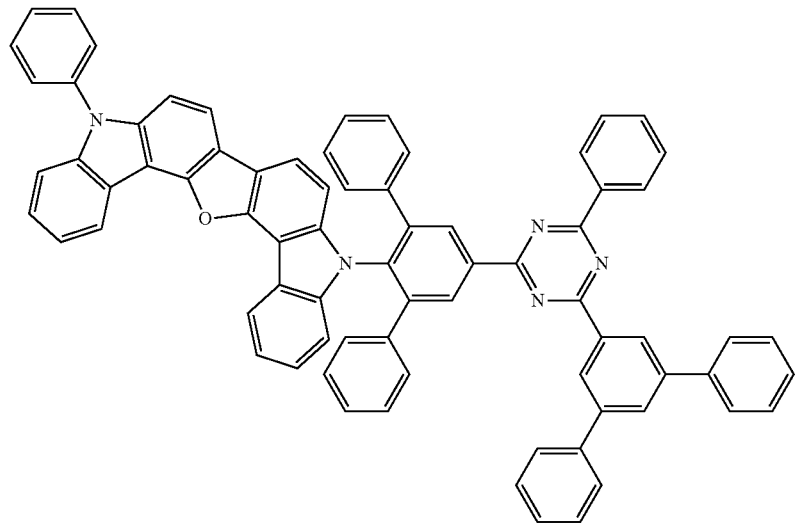
654
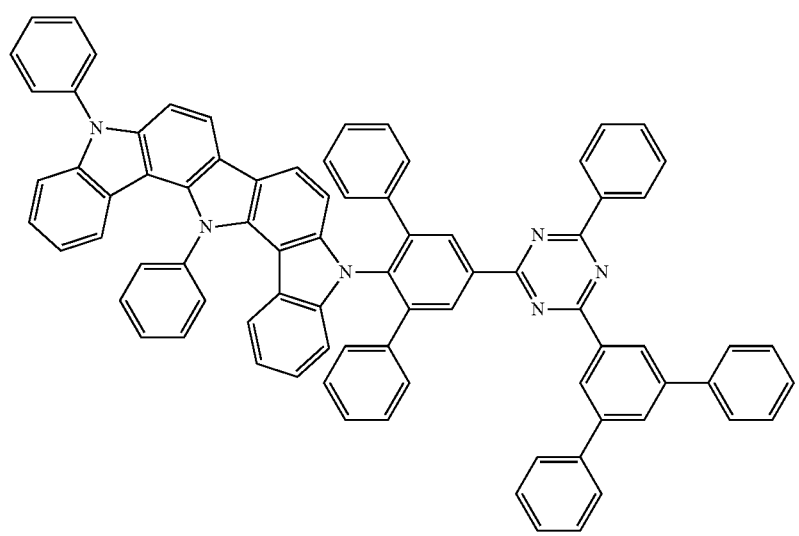
655
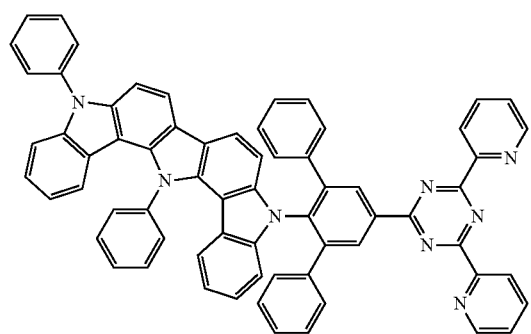

1111 1112
-continued
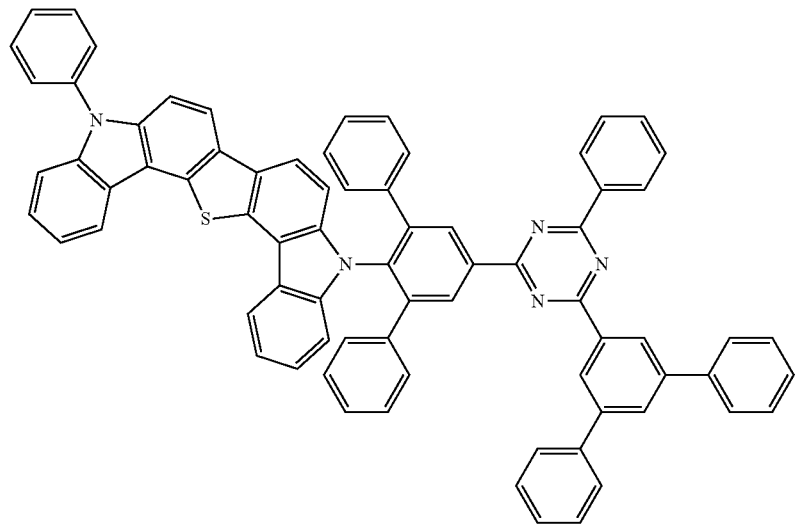
656
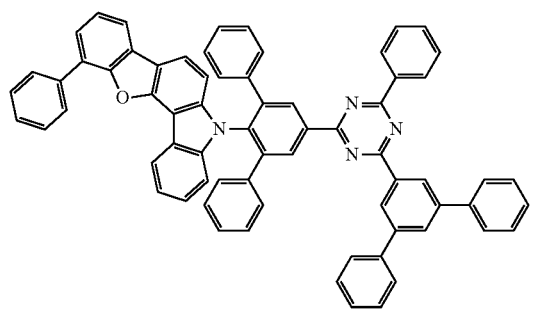
657
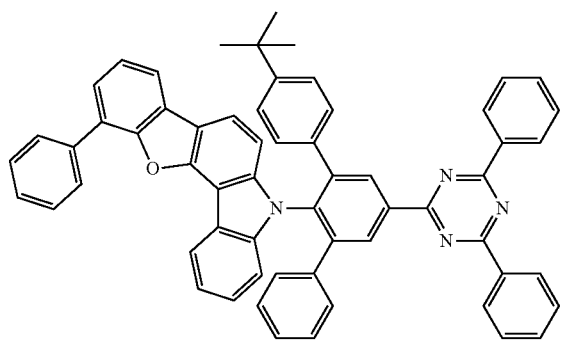
658
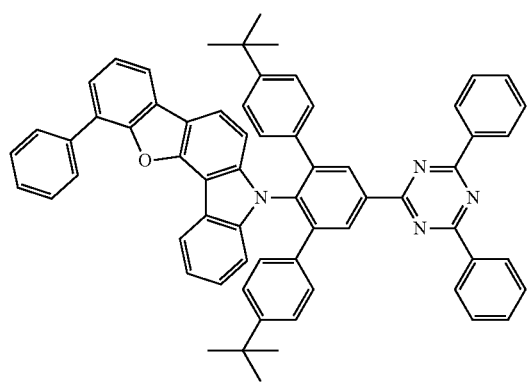
659
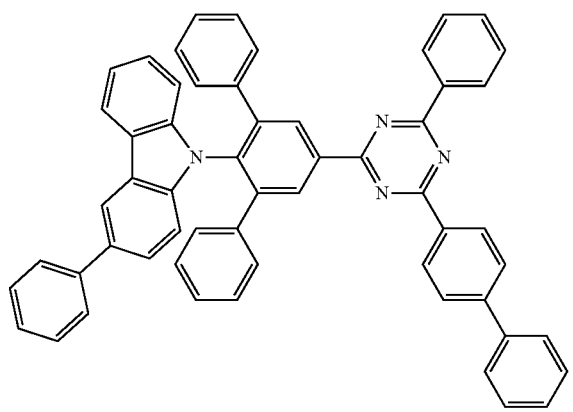
660

-continued
661
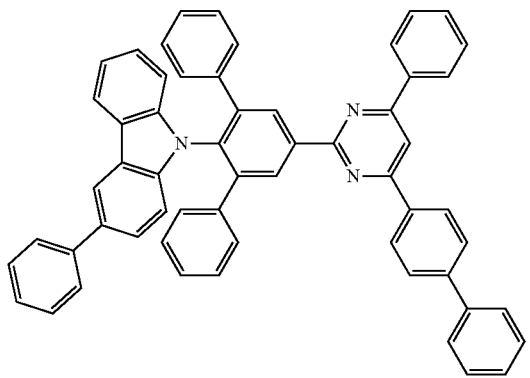
662
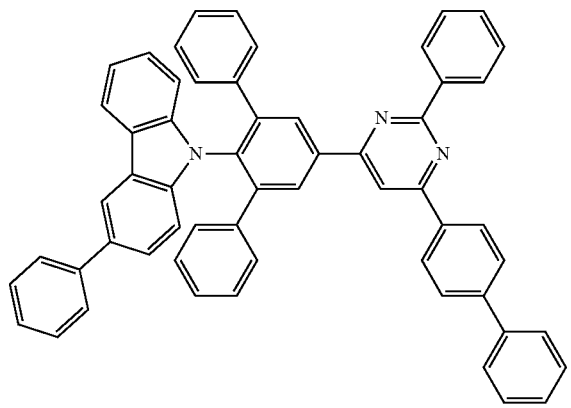
663
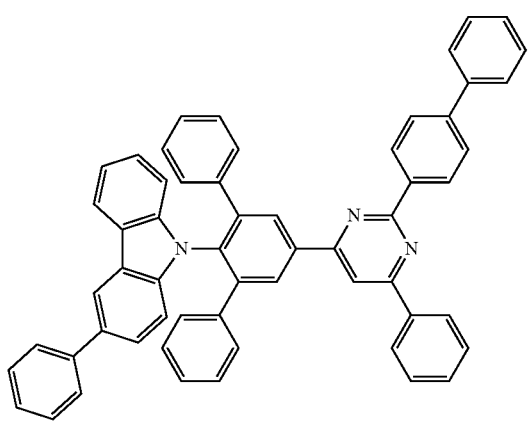
664
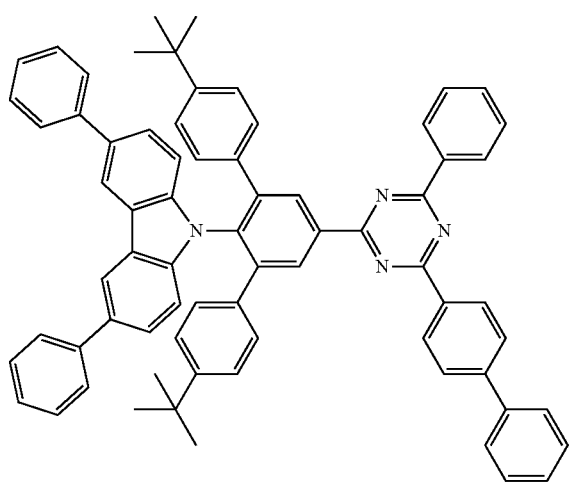
665
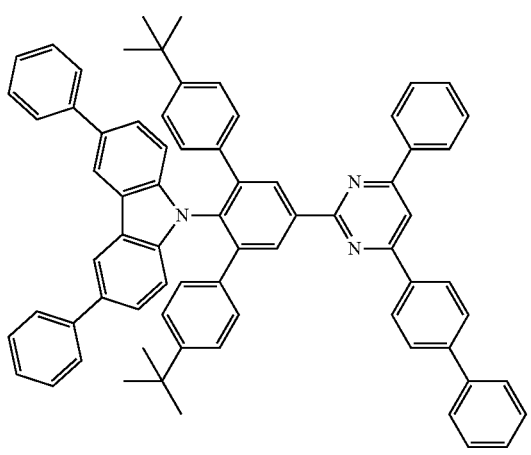
666
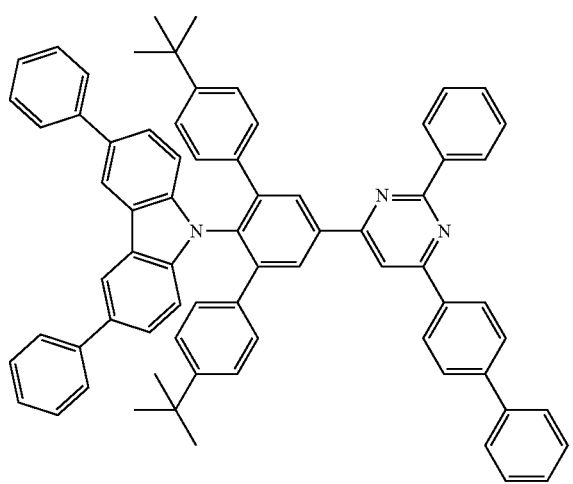

1115
1116
-continued
667
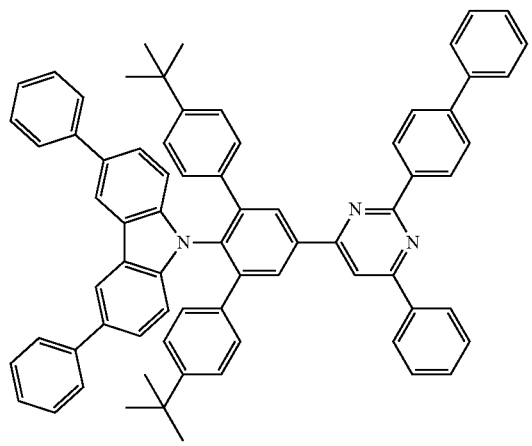
668
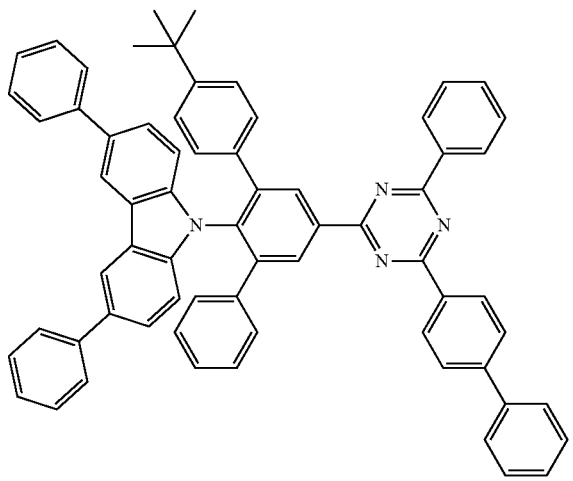
669
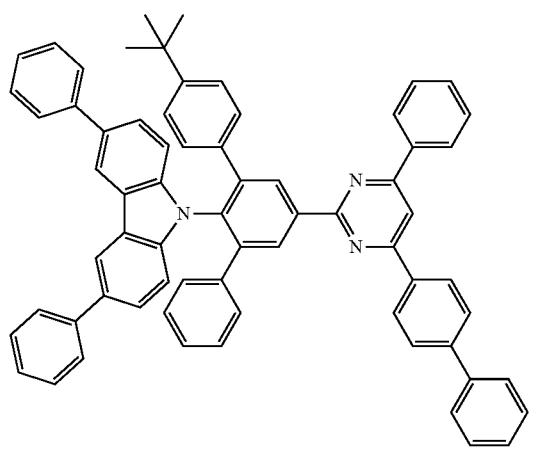
670
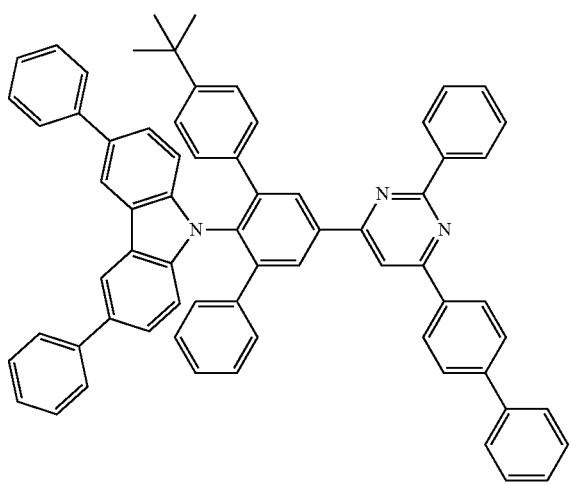
671
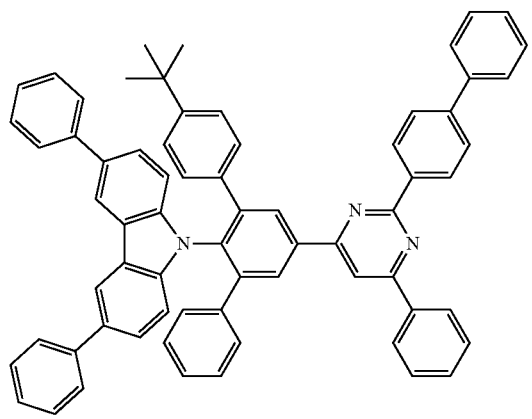
672
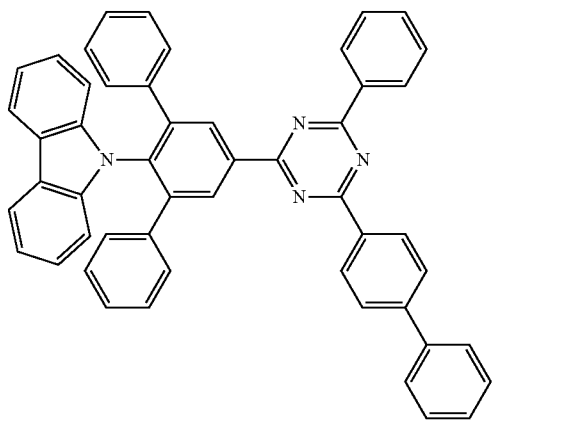

-continued
673
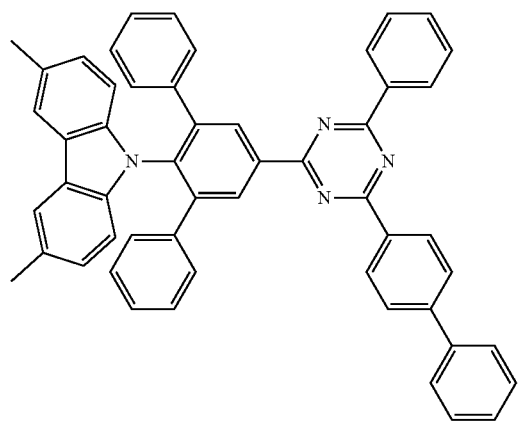
674
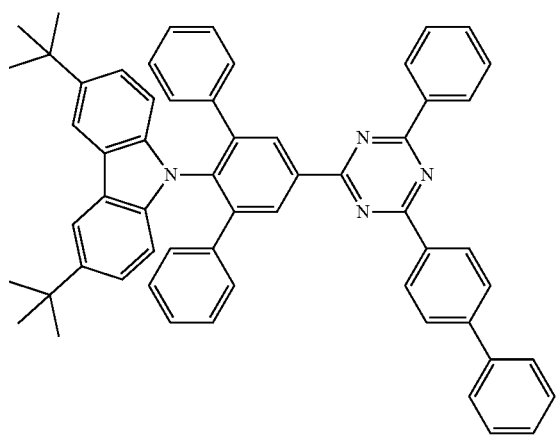
675
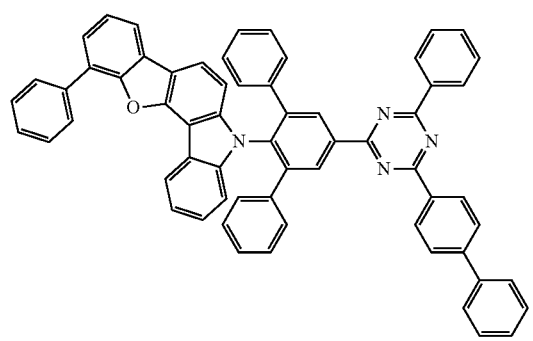
676
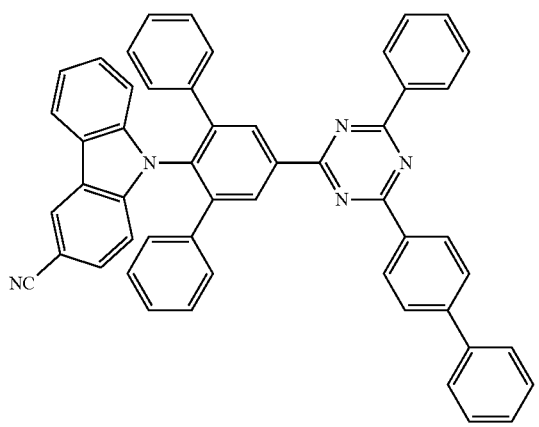
677
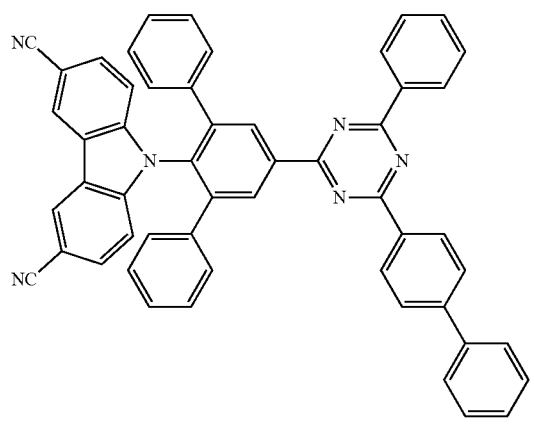
678
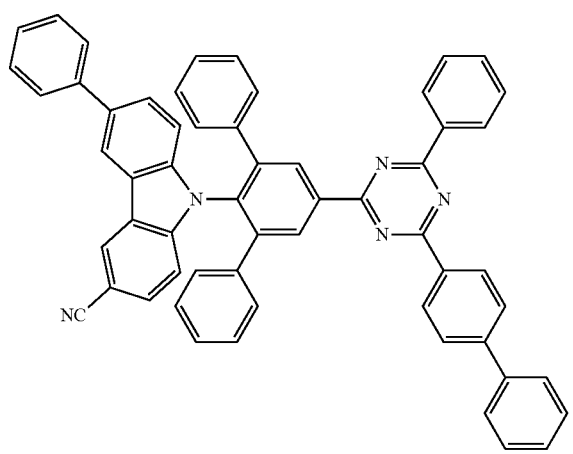

679
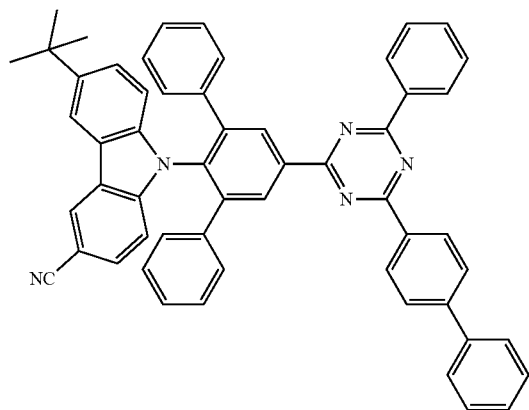
680
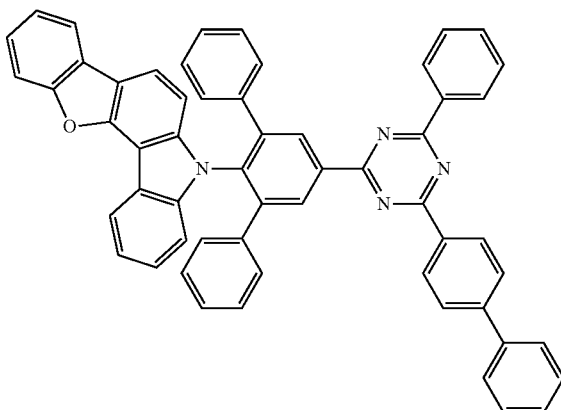
681
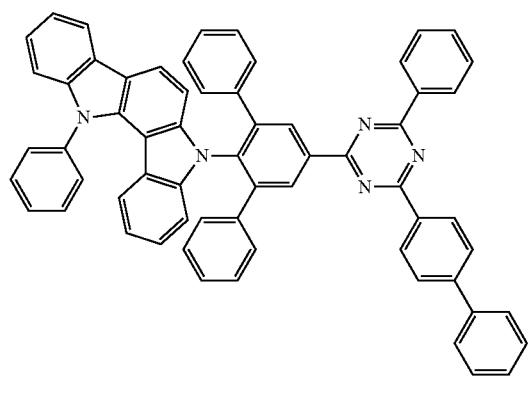
682
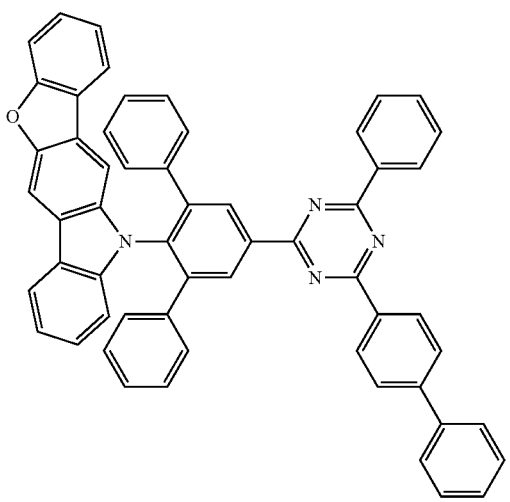
683
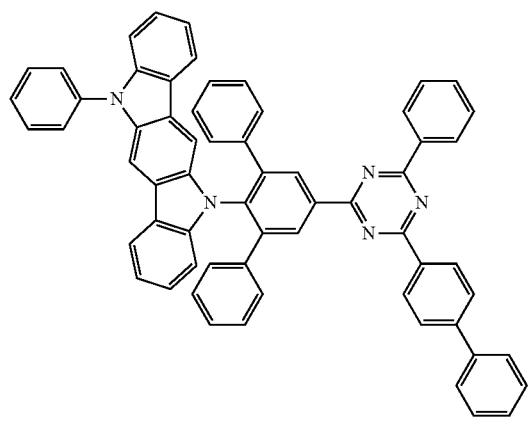
684
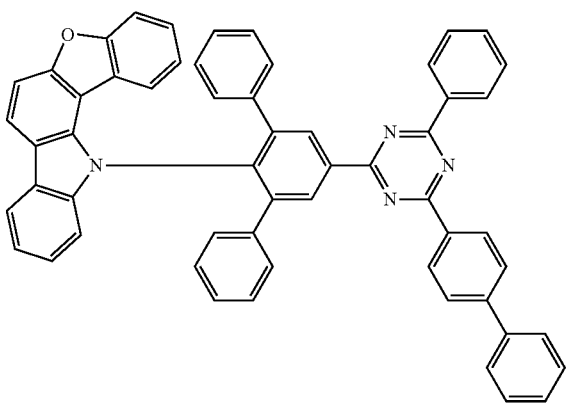

1121
-continued
685
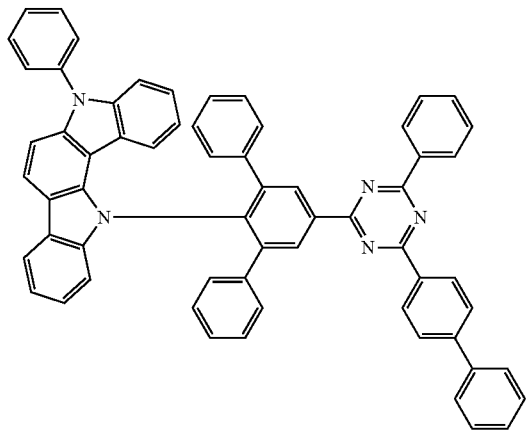
686
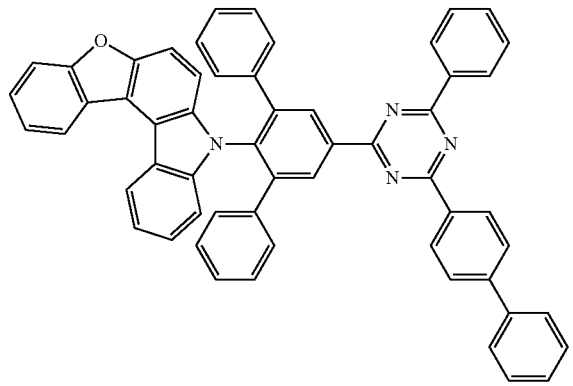
687
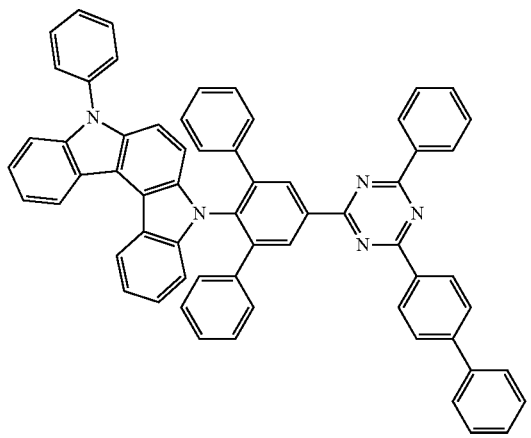
688
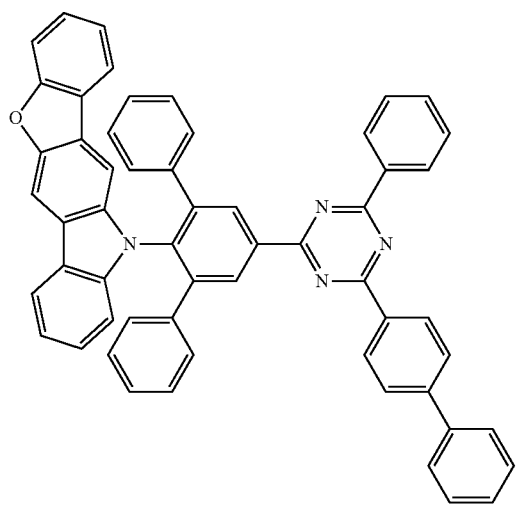
689
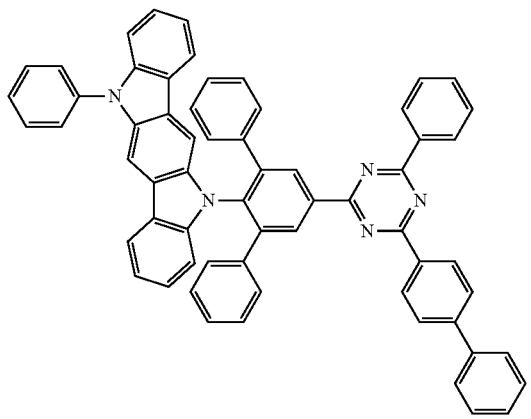
690
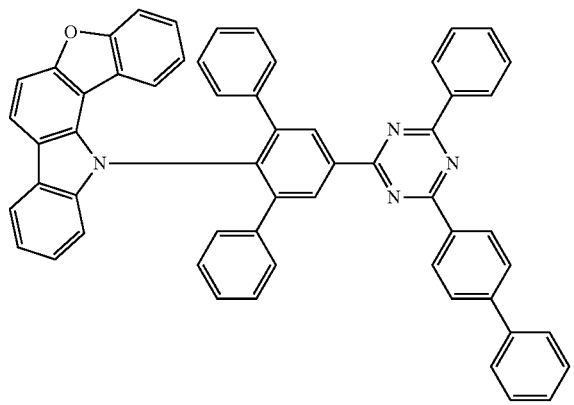

-continued
691
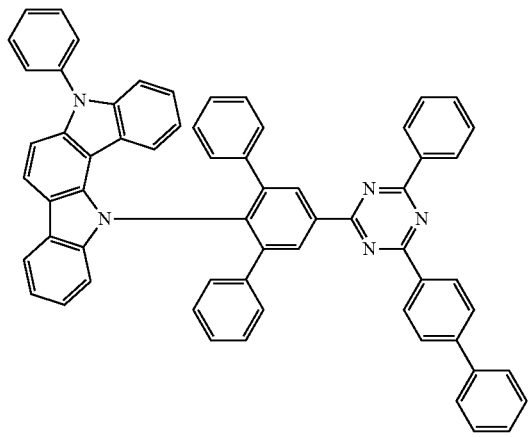
692
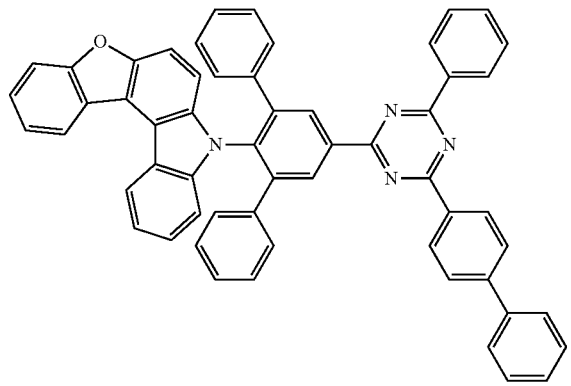
693
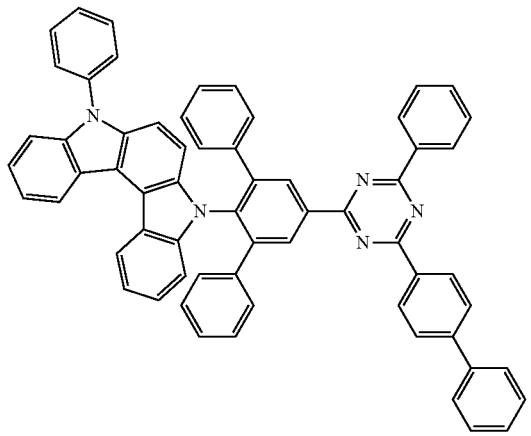
694
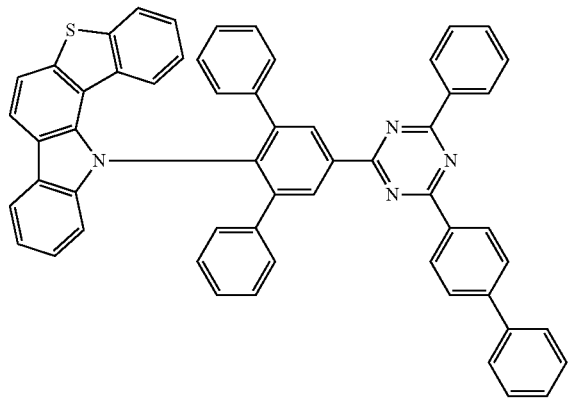
695
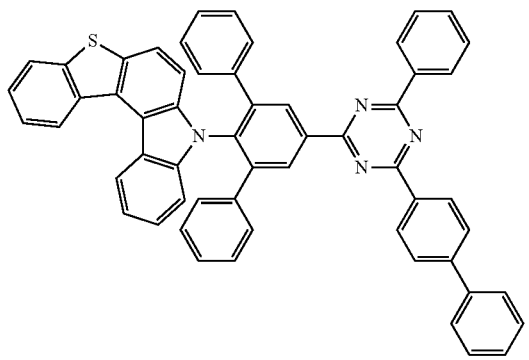
696
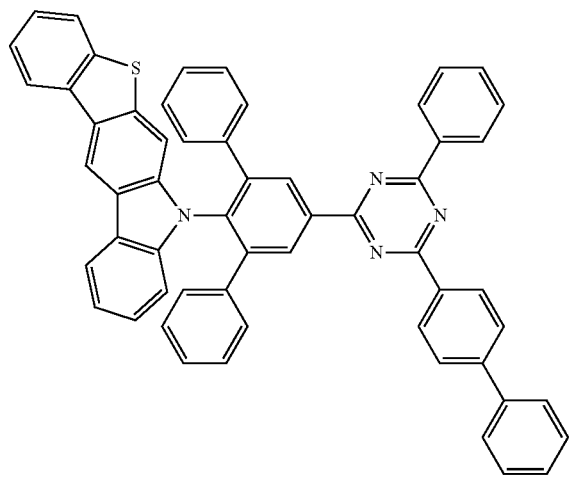

-continued
697
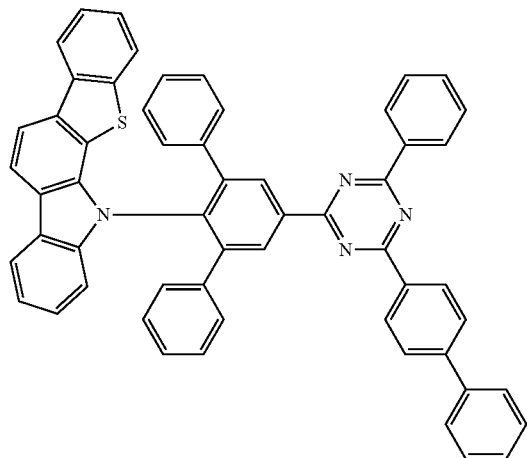
698
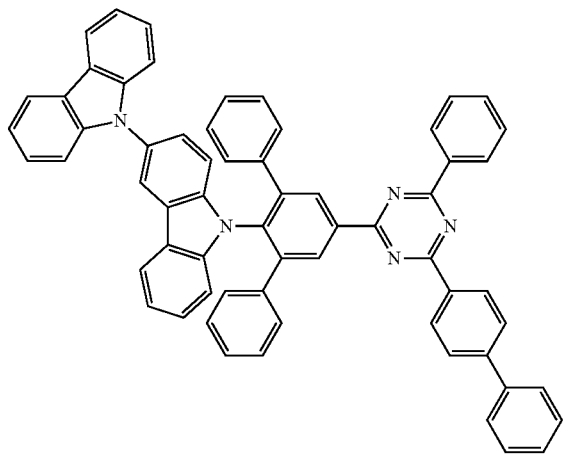
699
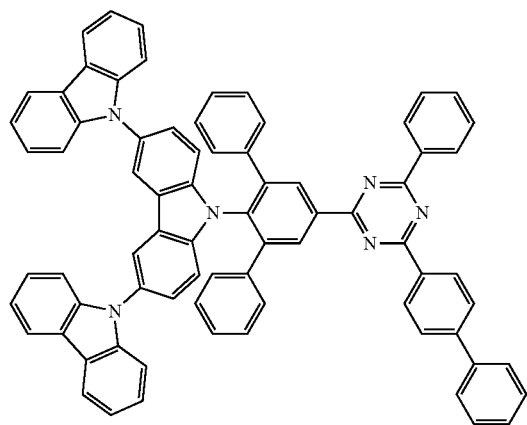
700
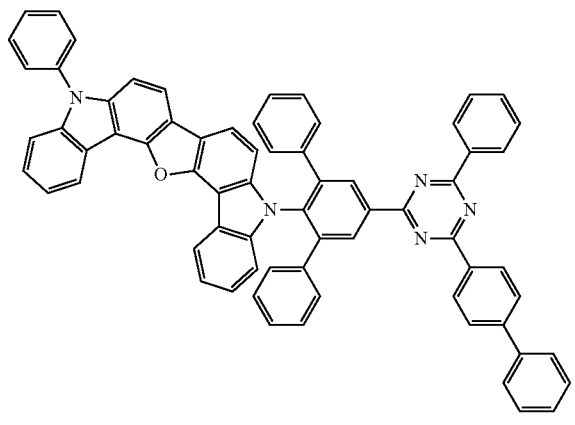
701
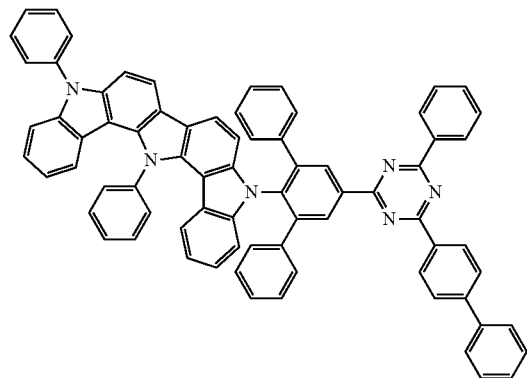
702
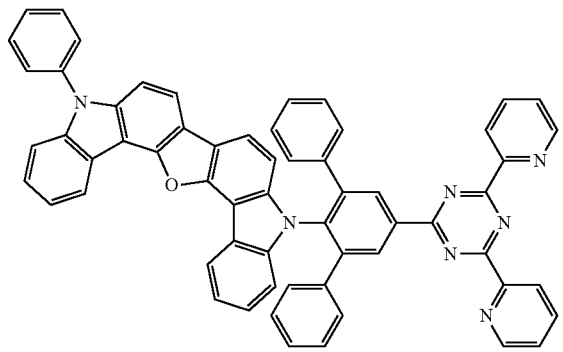

-continued
703
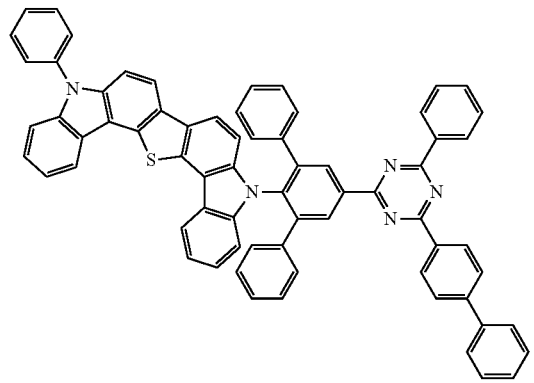
704
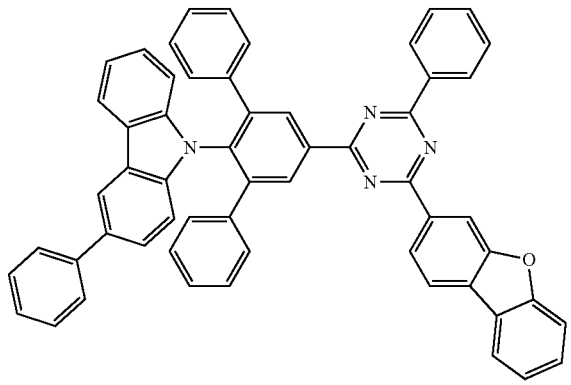
705
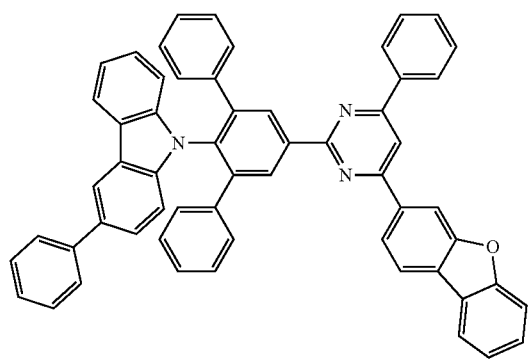
706
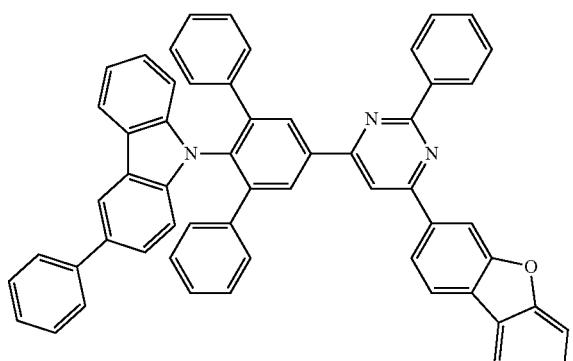
707
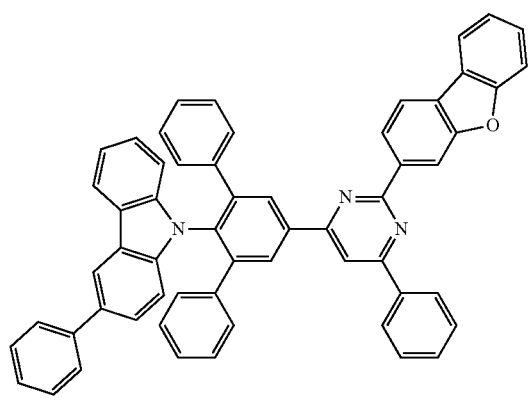
708
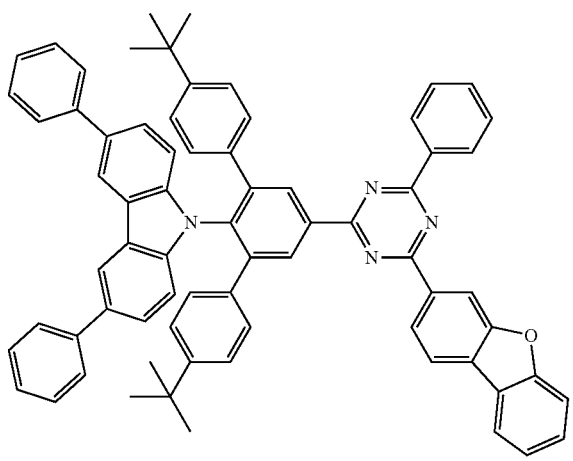

1129 1130
709
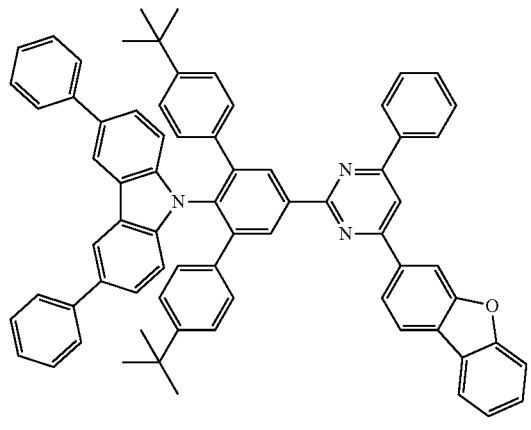
710
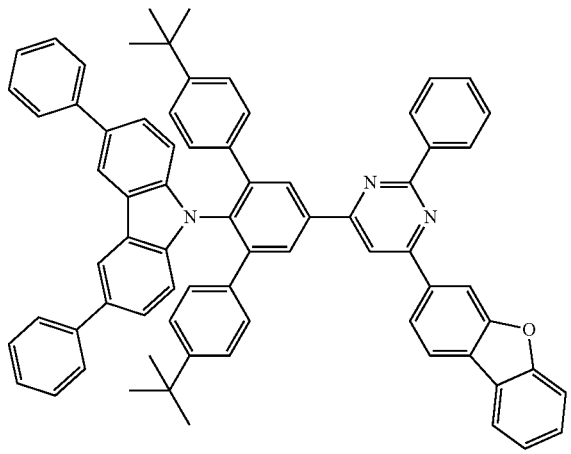
711
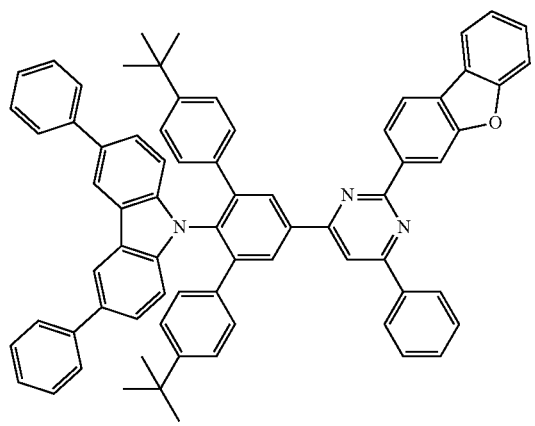
712
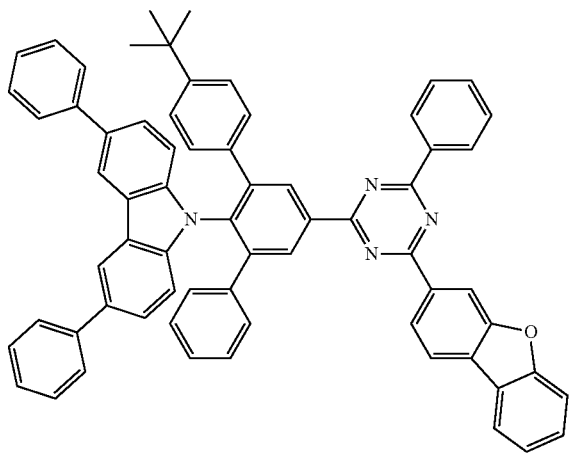
713
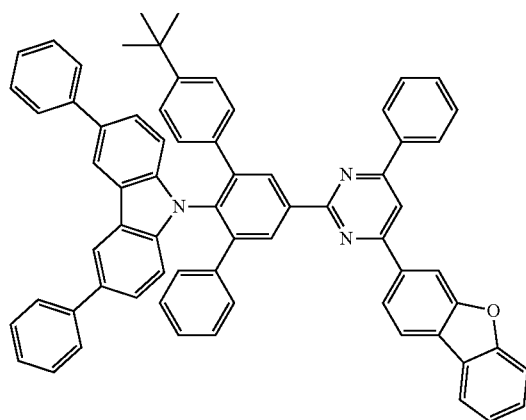
714
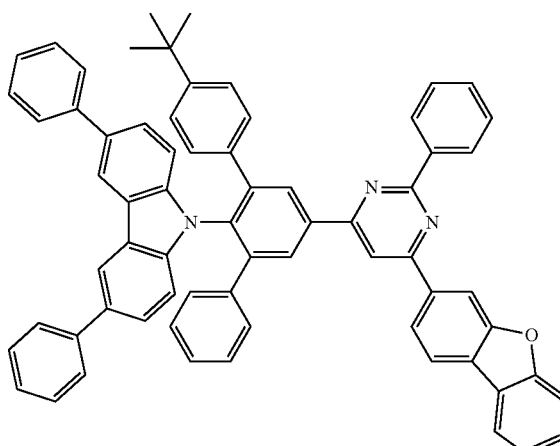

-continued
1131
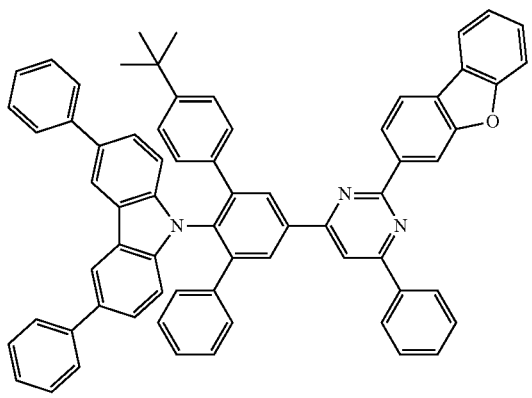
715
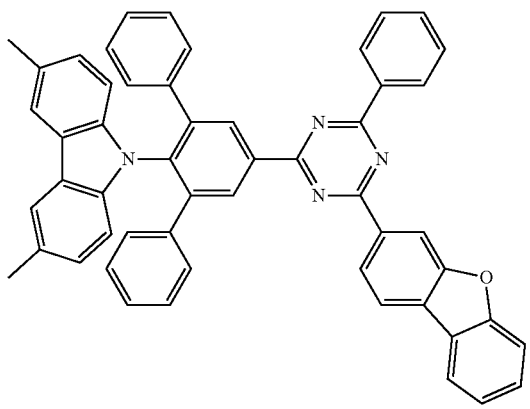
717
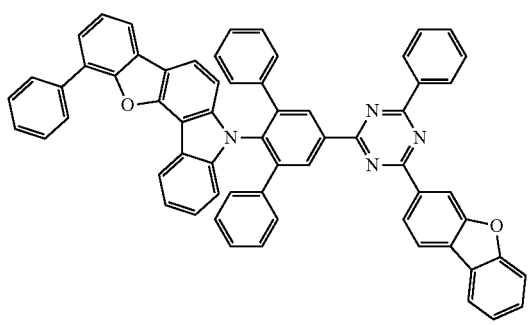
719
1132
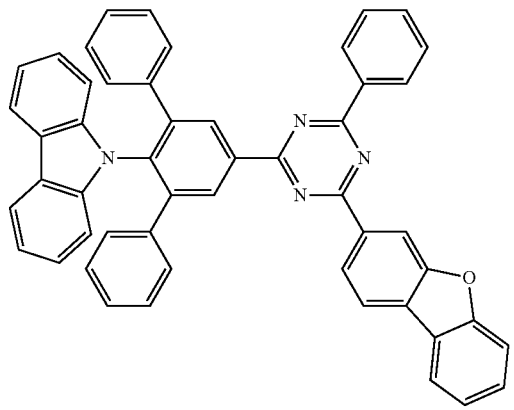
716
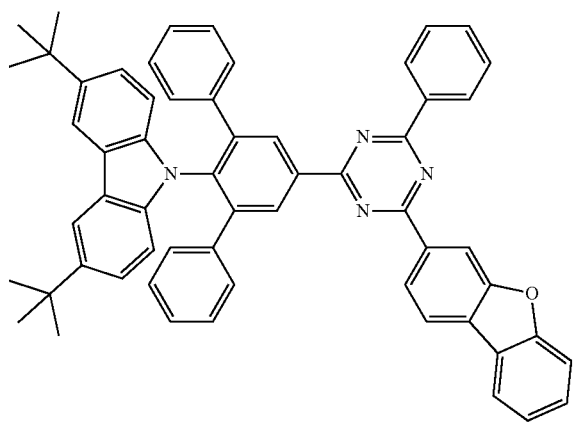
718
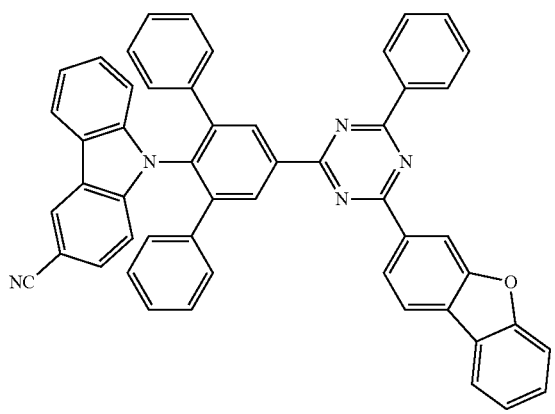
720

-continued
1133     1134
721
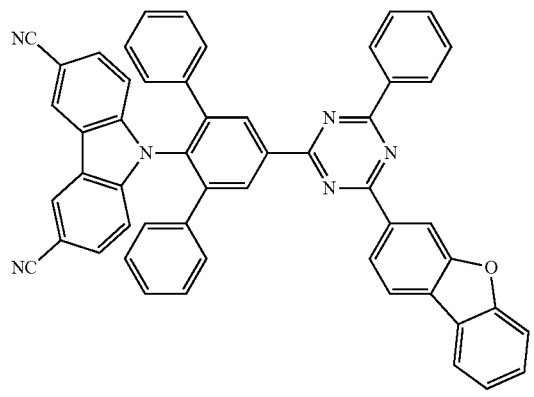
722
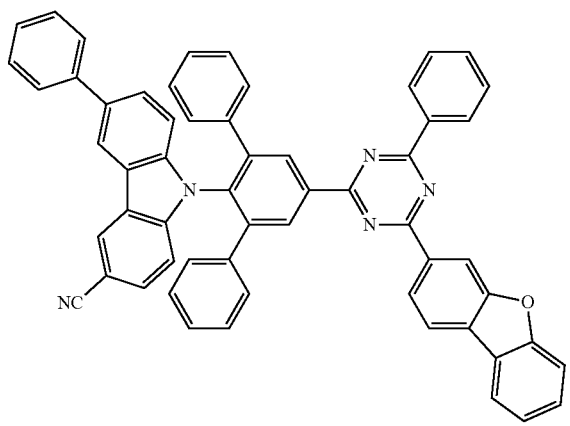
723
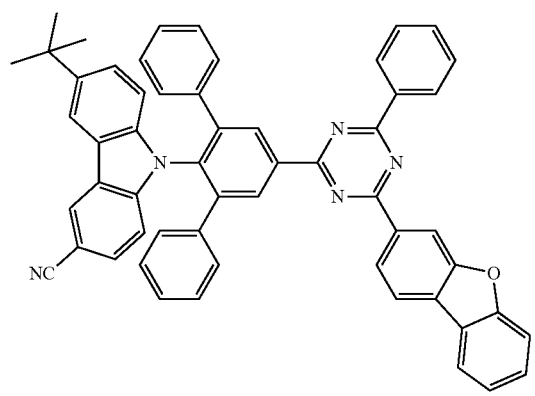
724
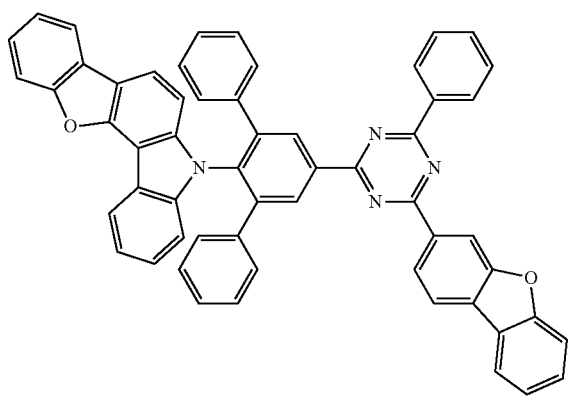
725
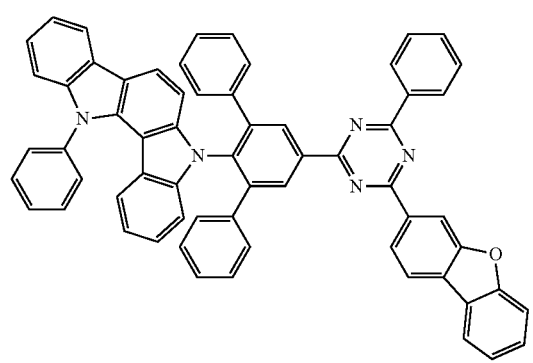
726
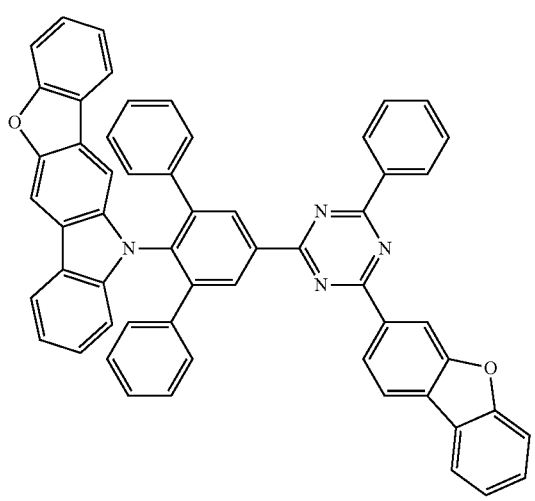

-continued
1135
727
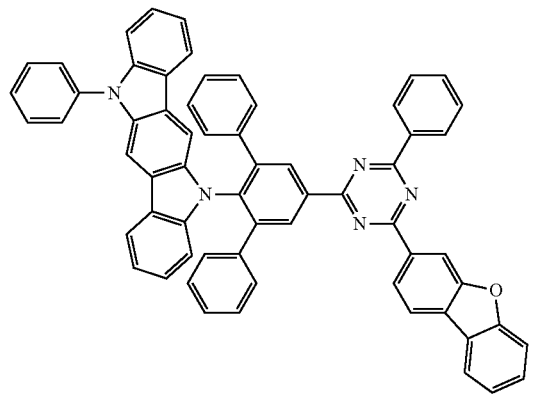
1136
728
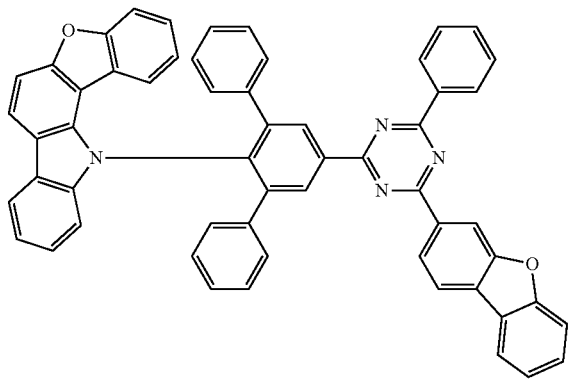
729
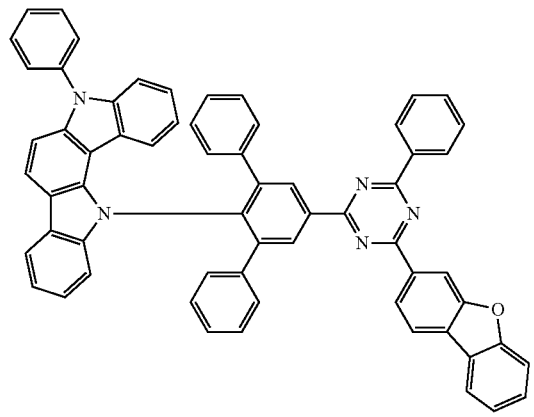
730
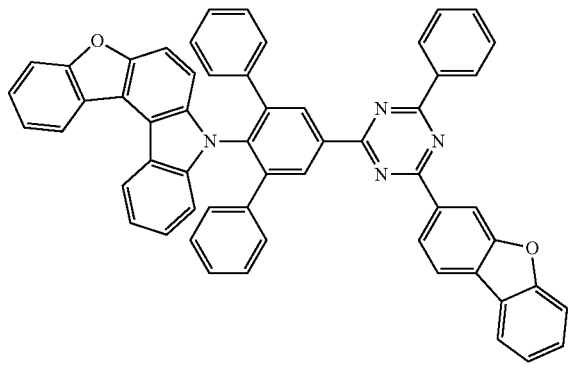
731
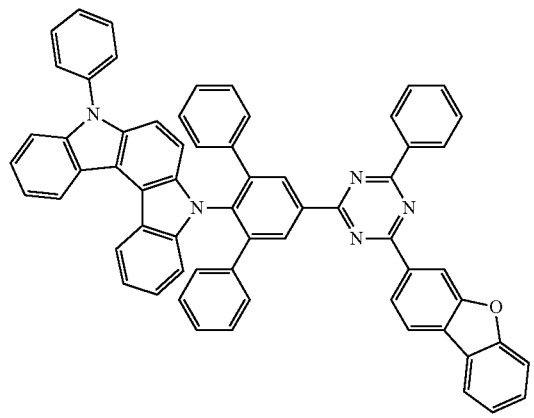
732
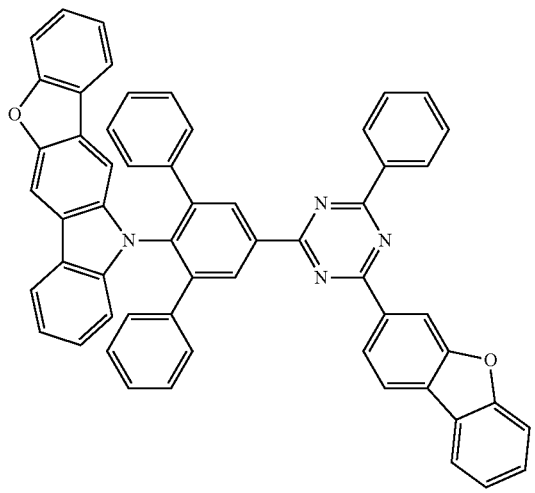

1137
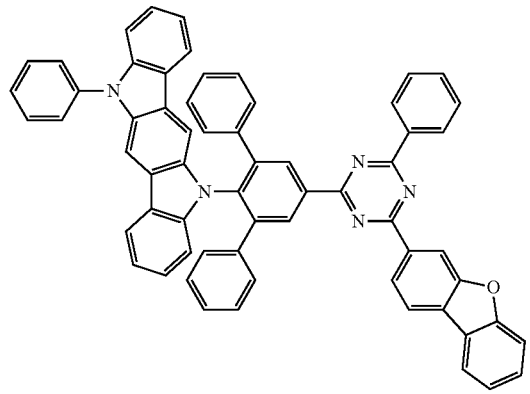
733
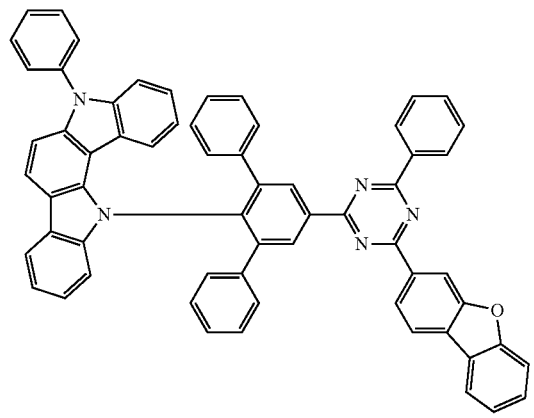
735
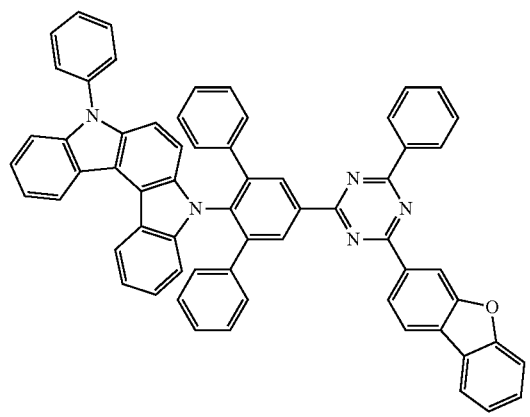
737
1138
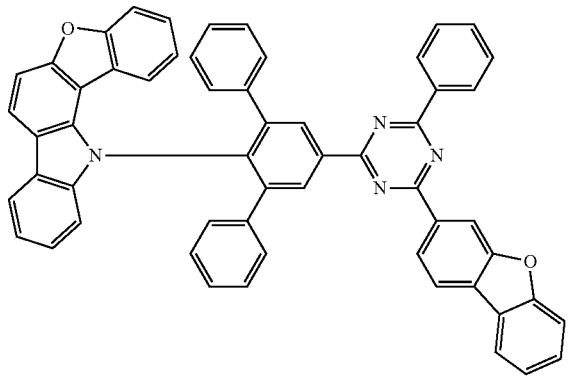
734
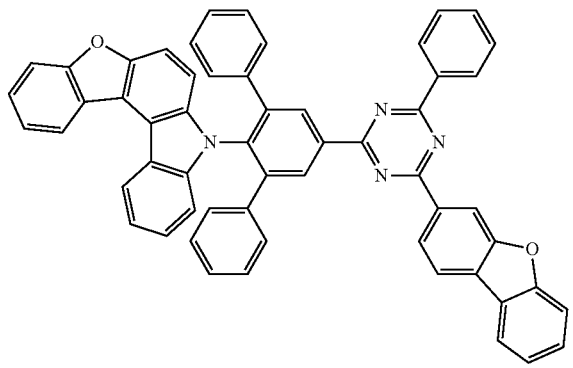
736
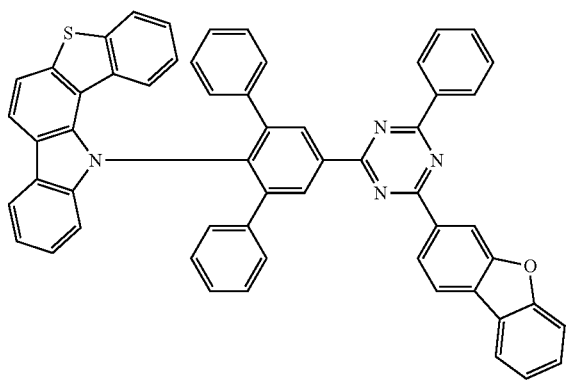
738

1139
-continued
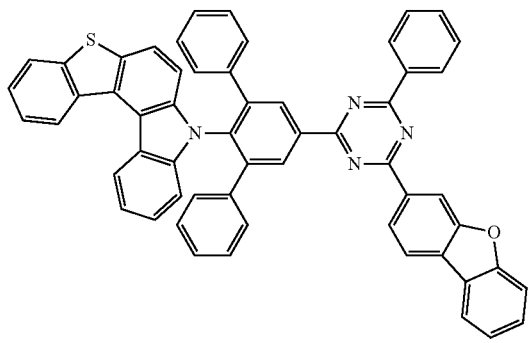
739
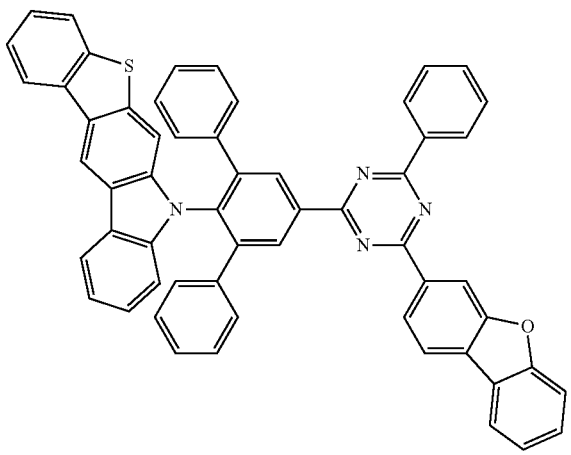
740
1140
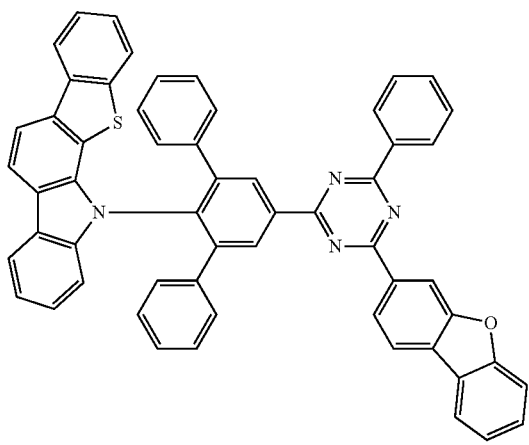
741
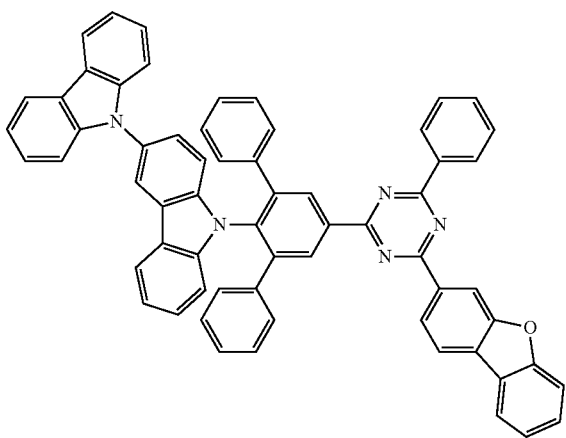
742
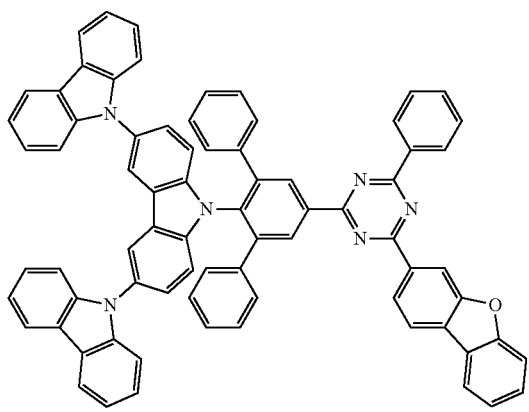
743
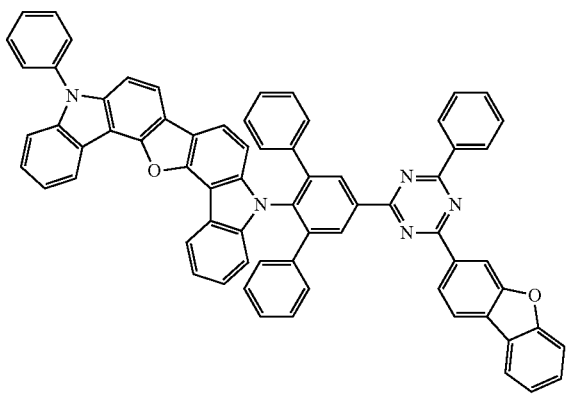
744

-continued
745
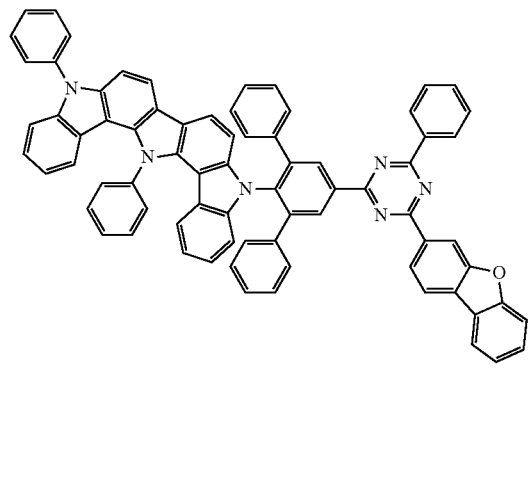
746
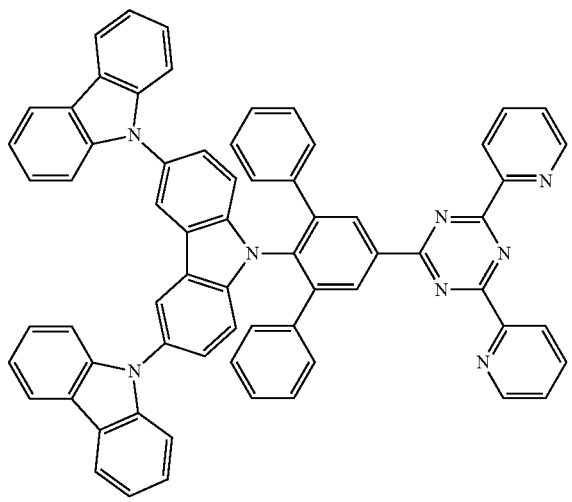
747
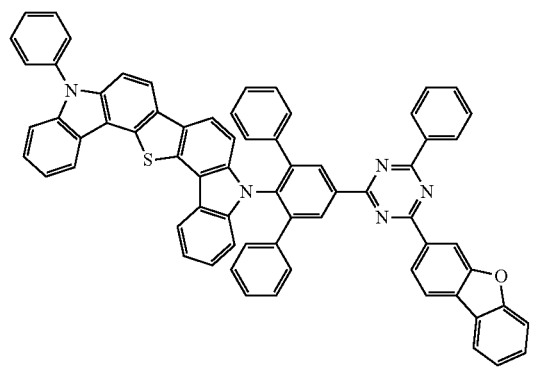
748
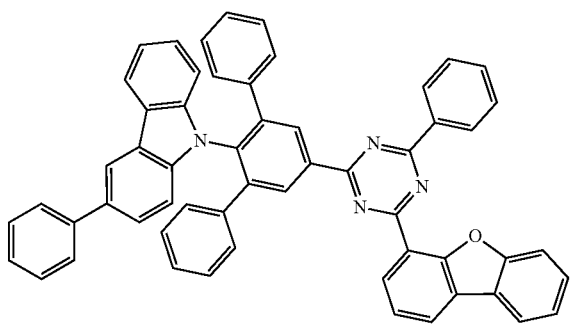
749
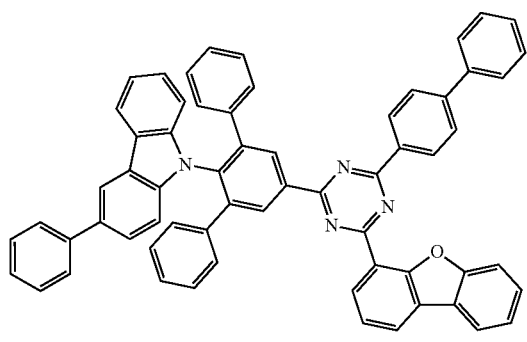
750
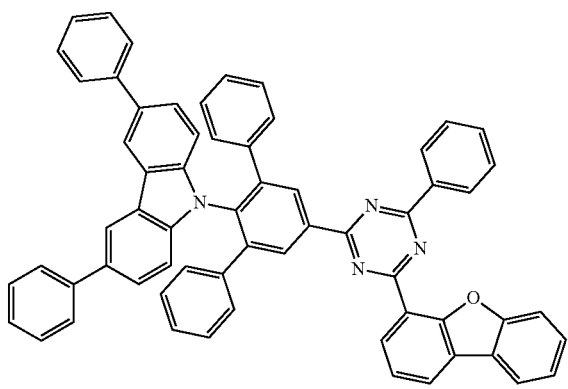

1143  1144
-continued
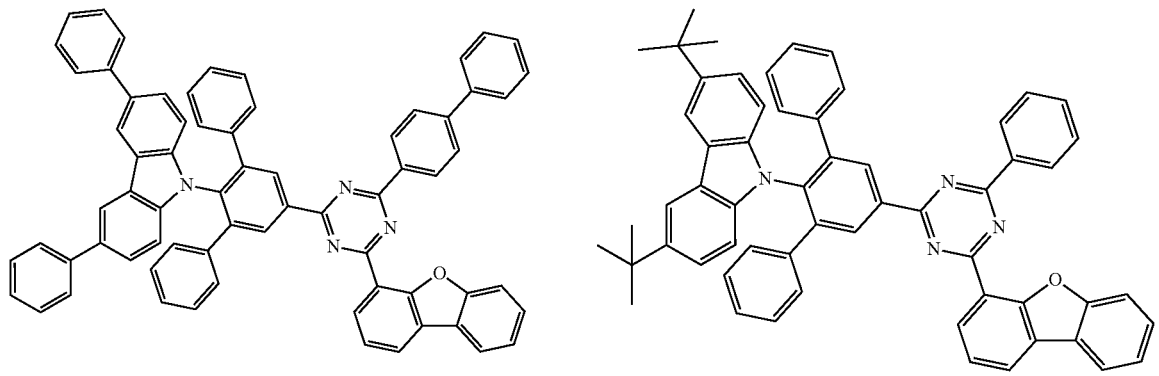
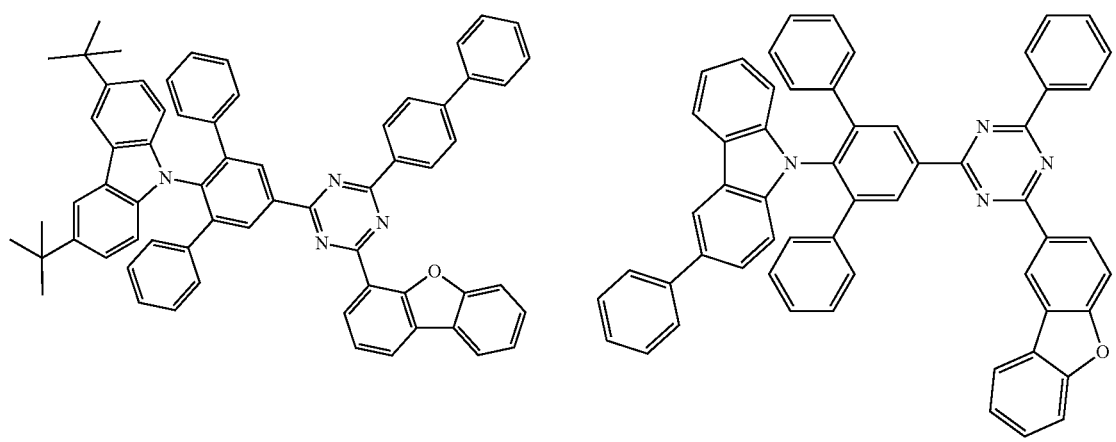
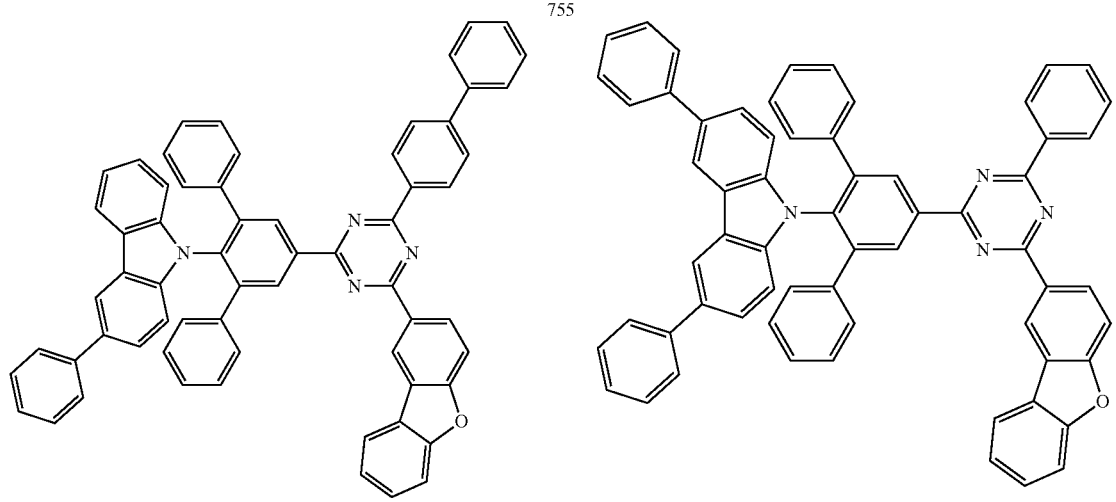

-continued
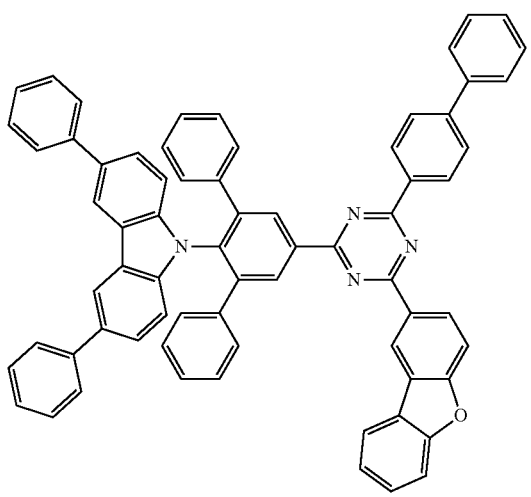
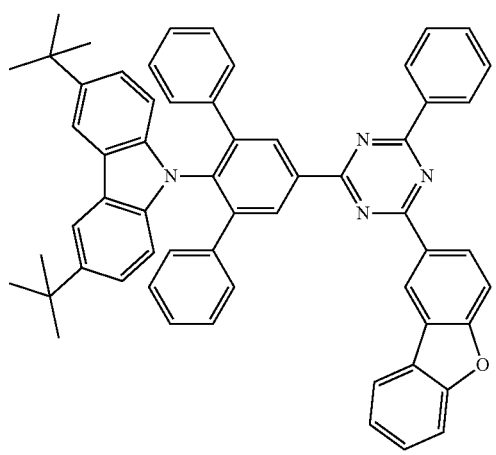
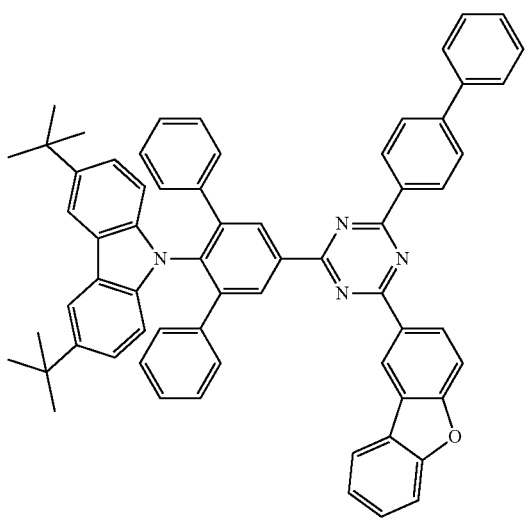
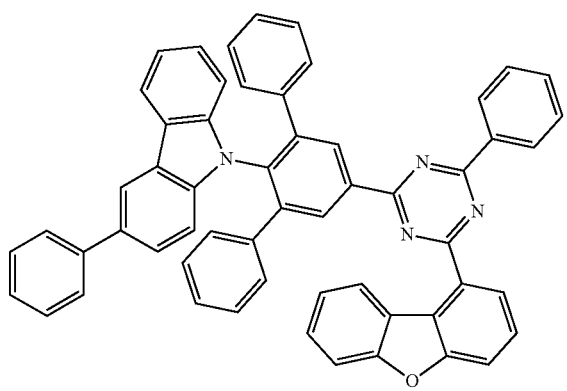
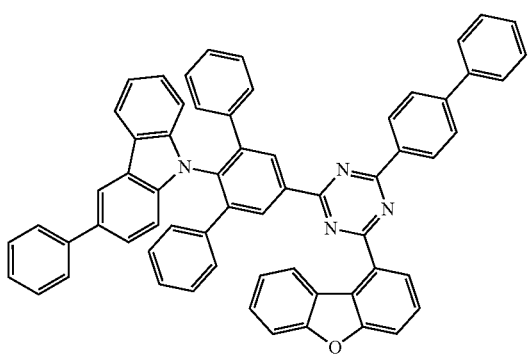
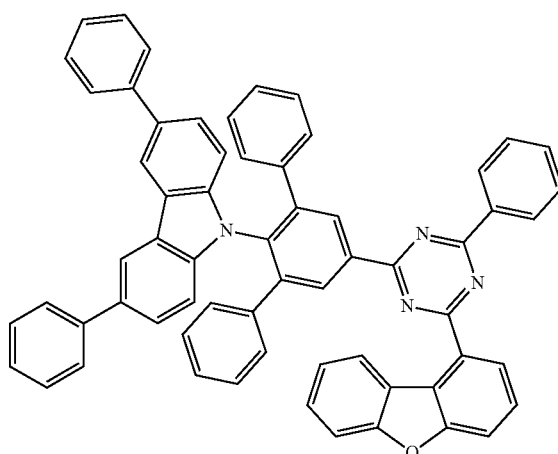

-continued
1147
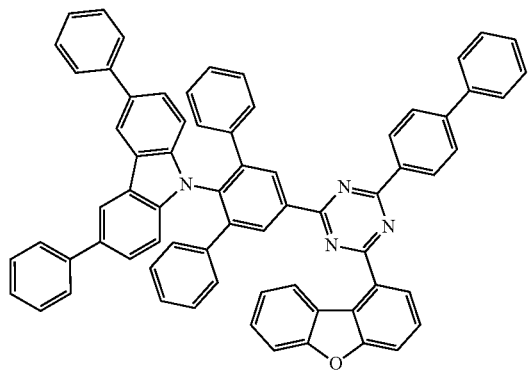
1148
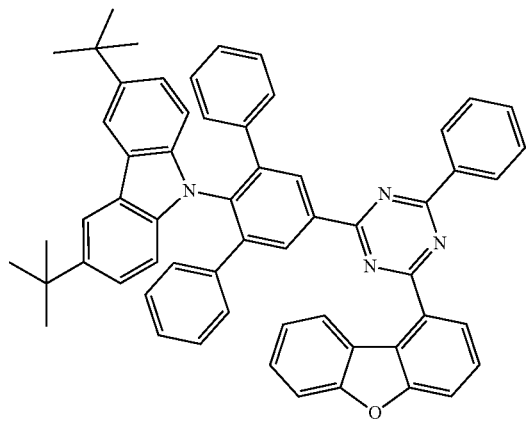
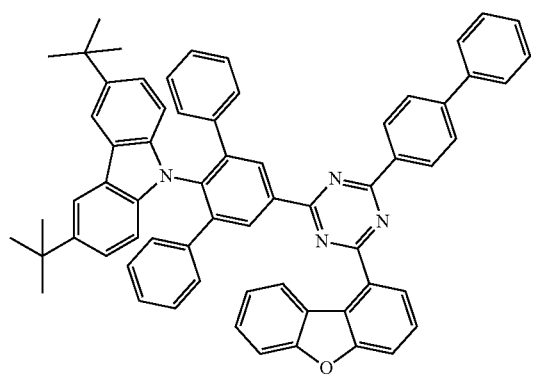
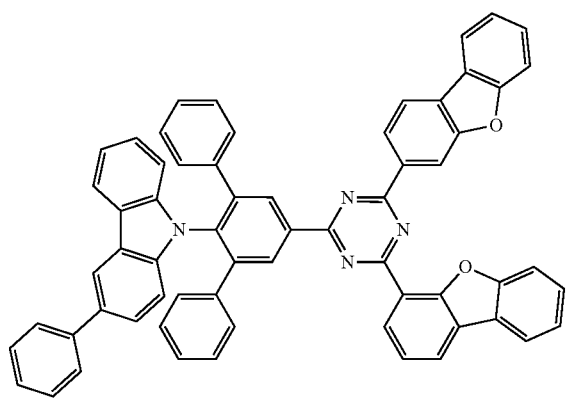
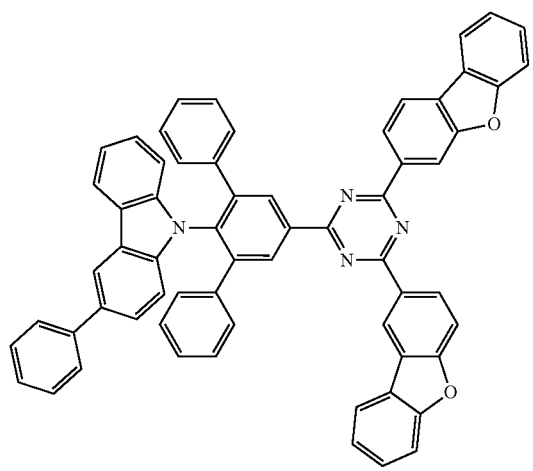
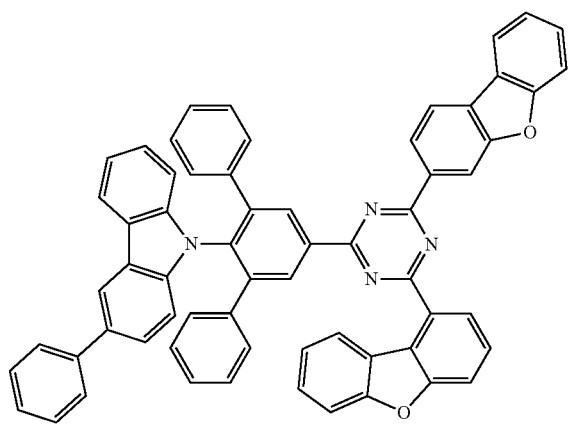

-continued
769
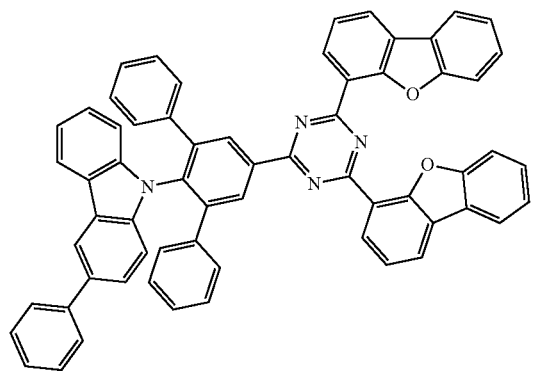
770
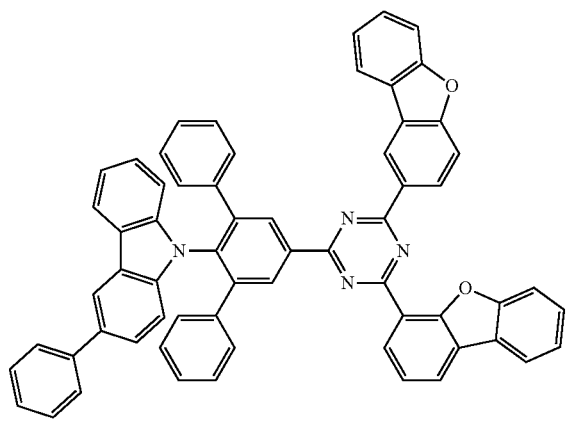
771
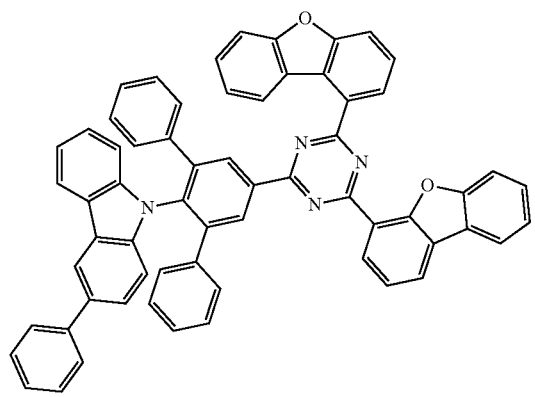
772
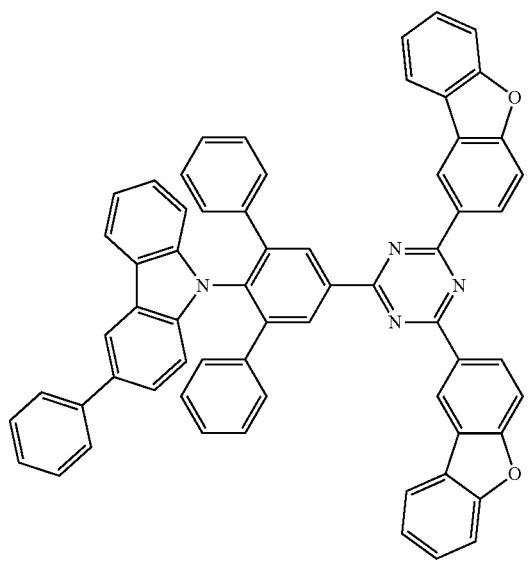
773
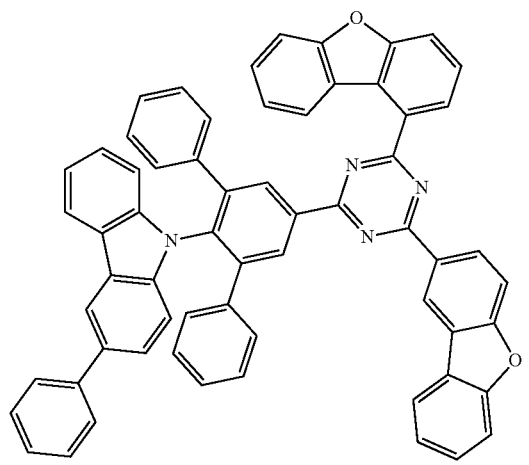
774
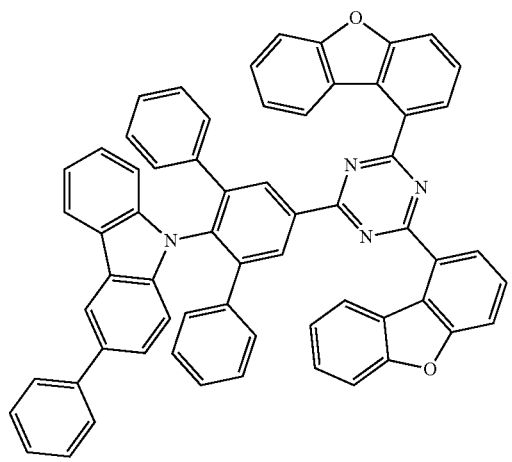

-continued
775
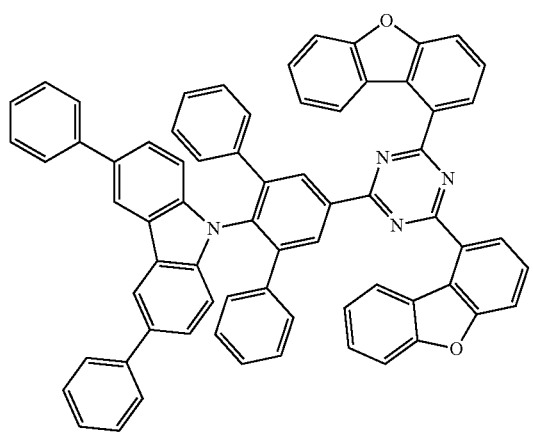
776
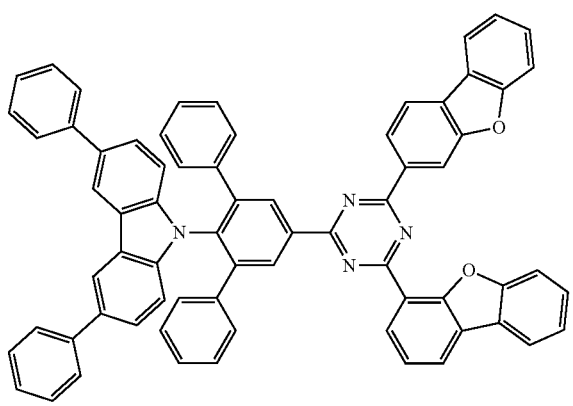
777
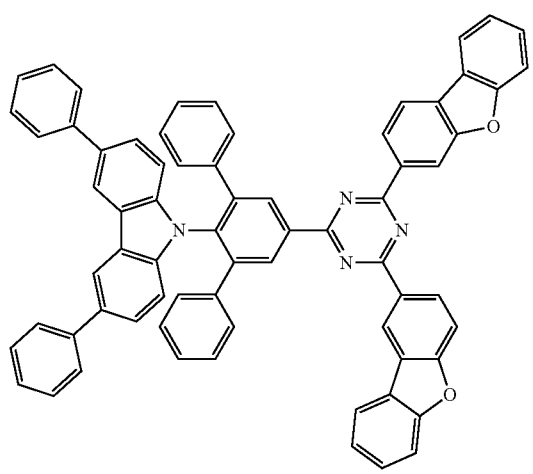
778
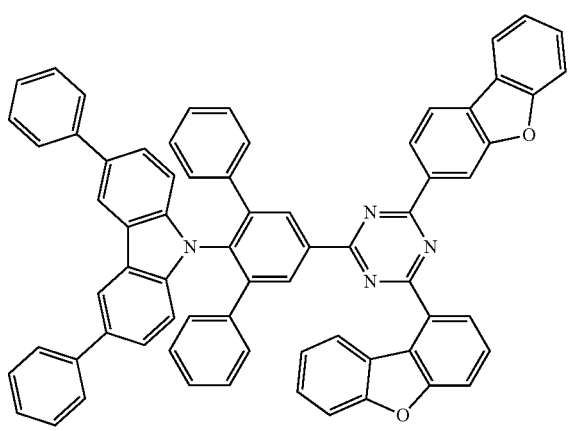
779
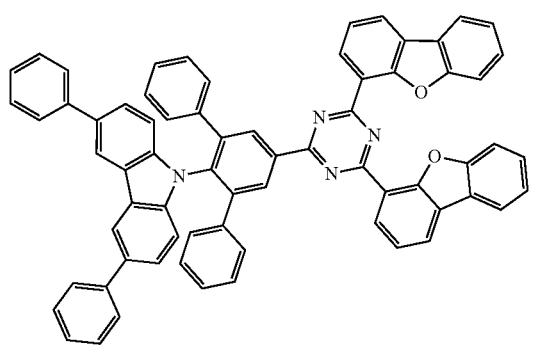
780
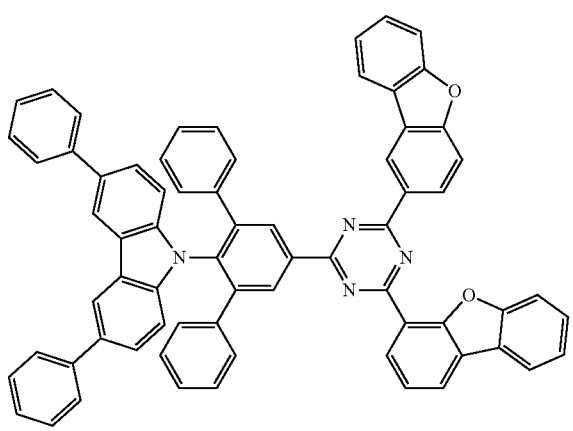

1153 1154
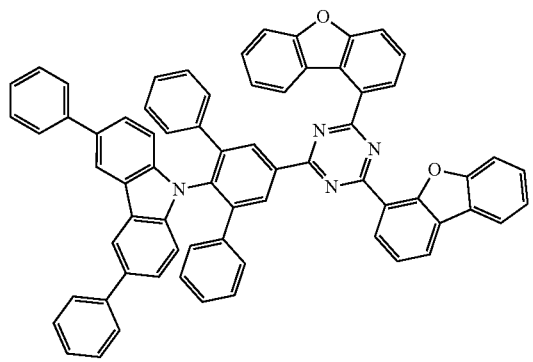
781
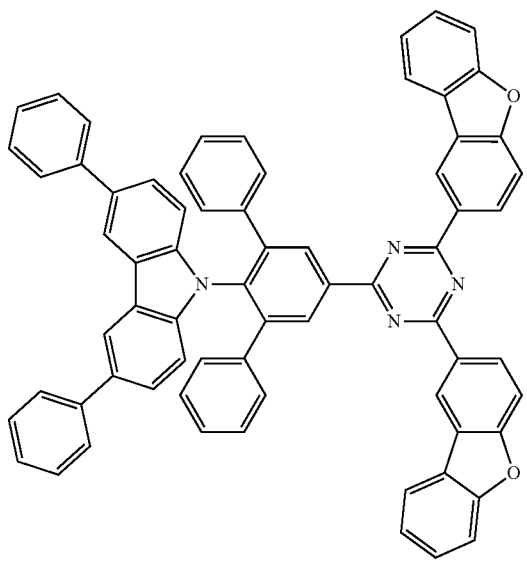
782
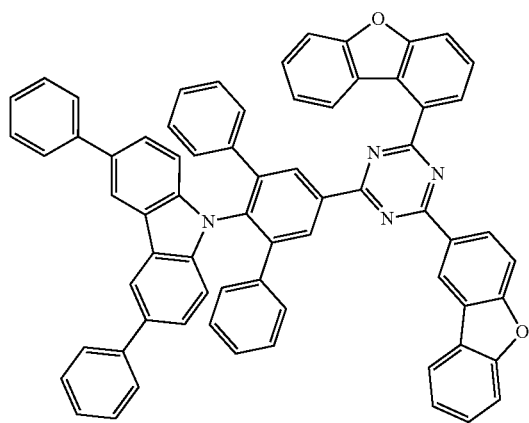
783
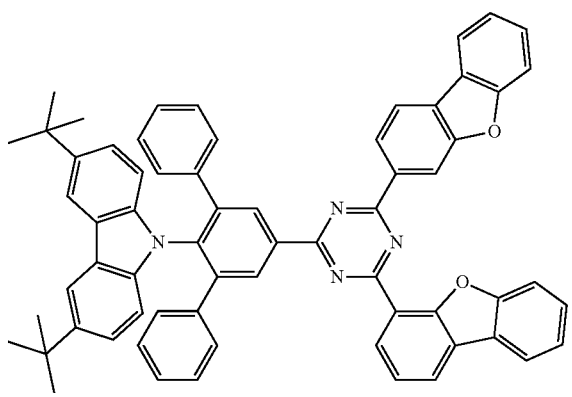
784
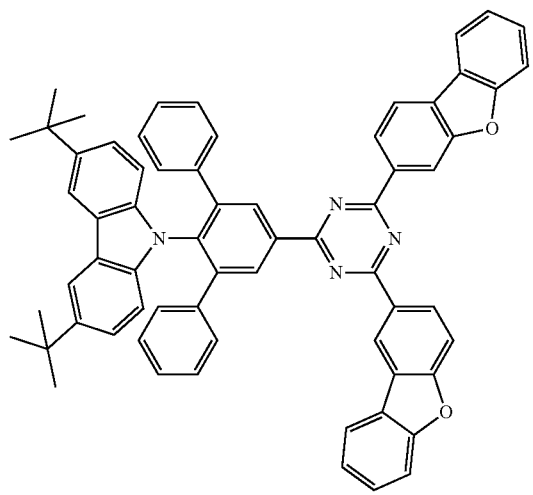
785
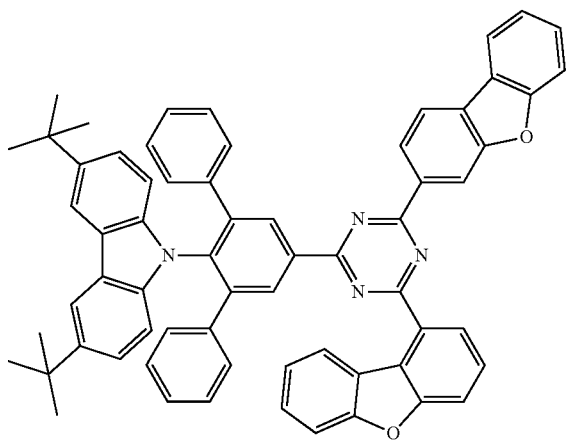
786

-continued
1155
787
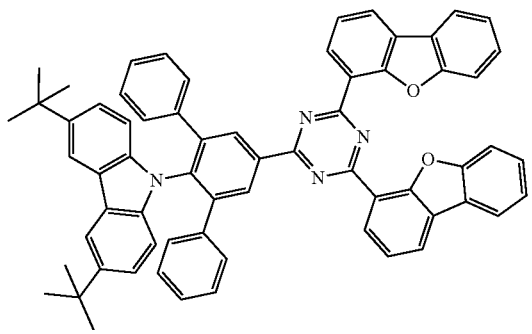
789
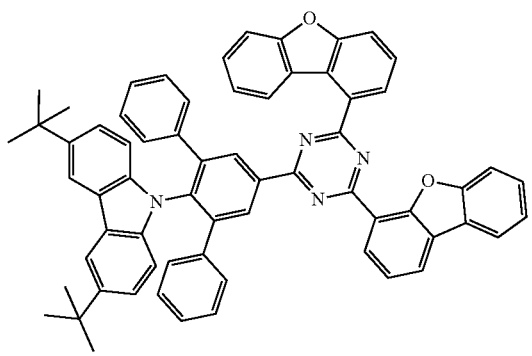
791
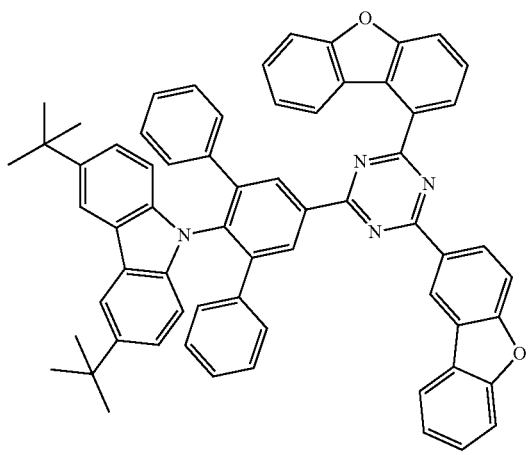
1156
788
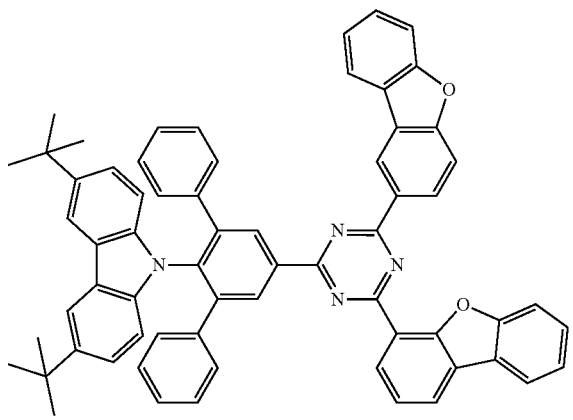
790
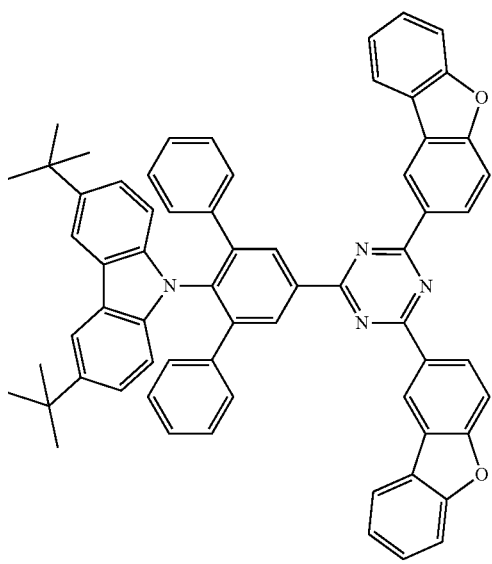
792
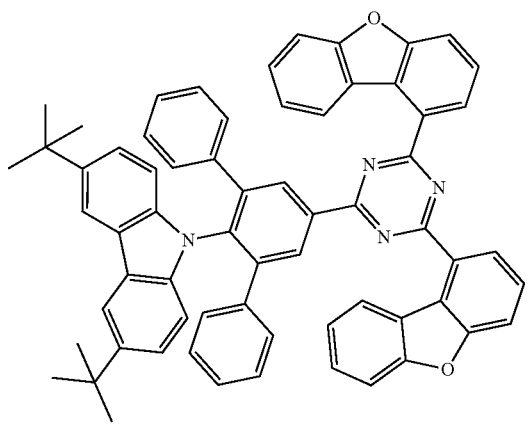

-continued
793
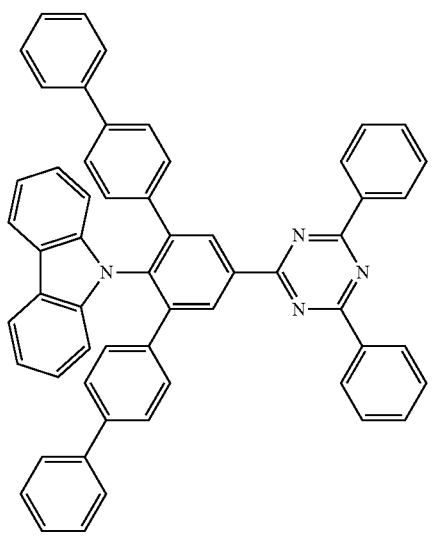
794
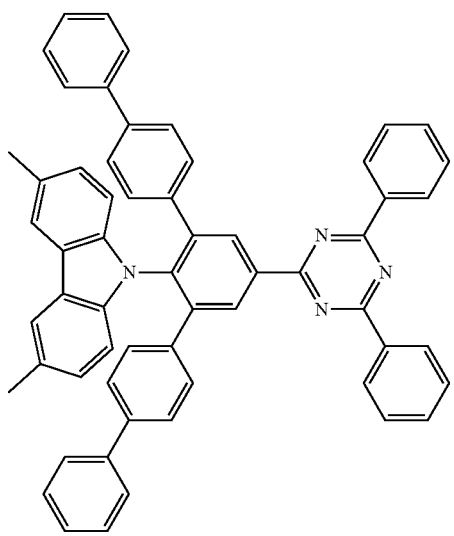
795
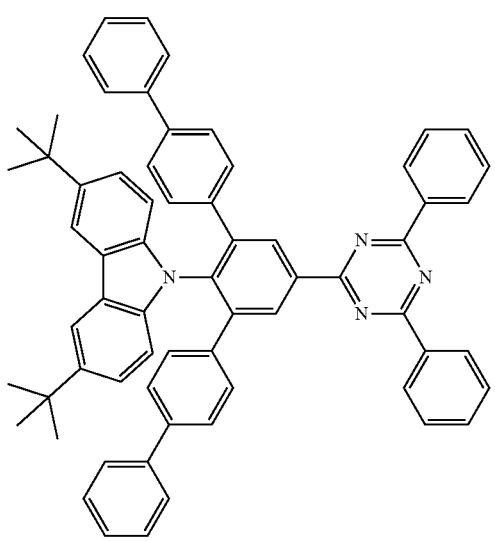
796
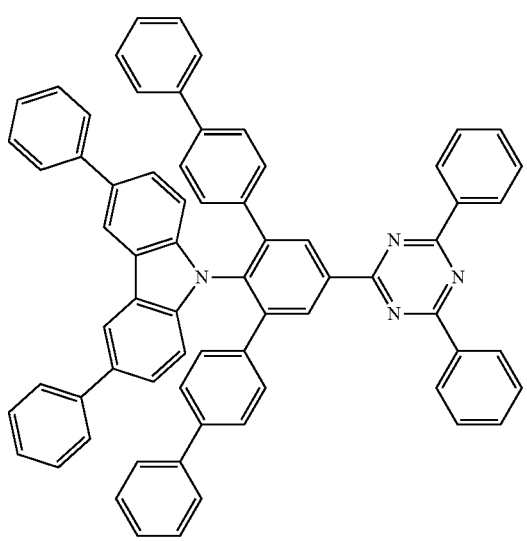
797
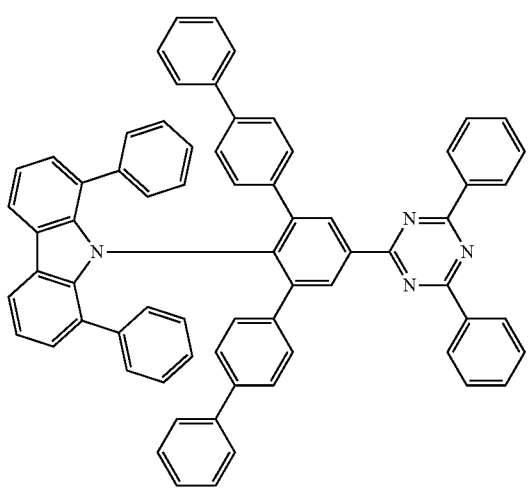
798
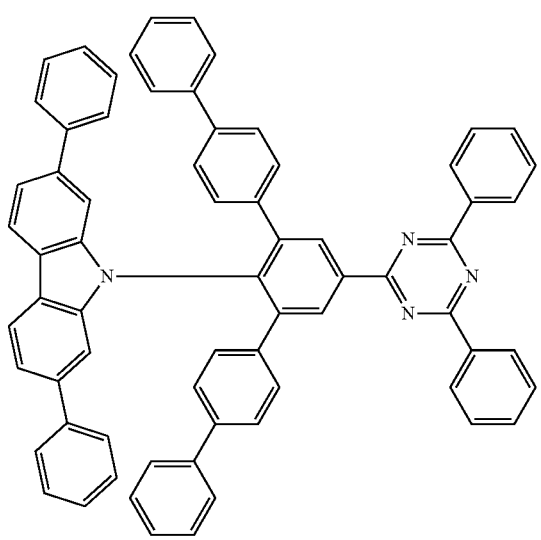

-continued
1159
799
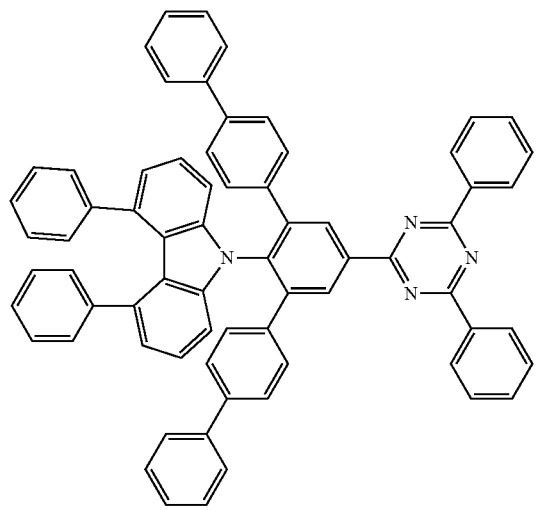
800
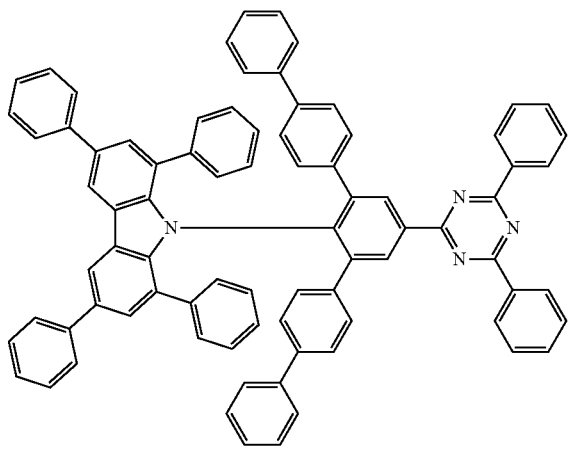
801
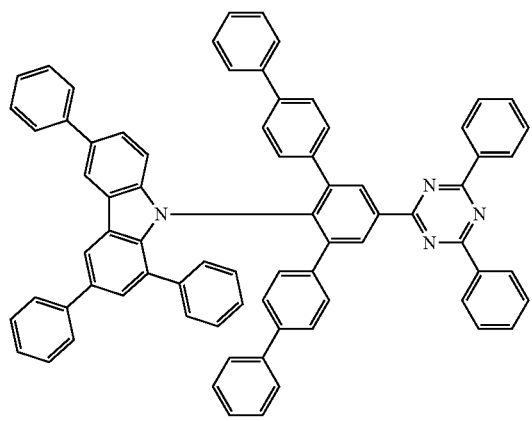
1160
802
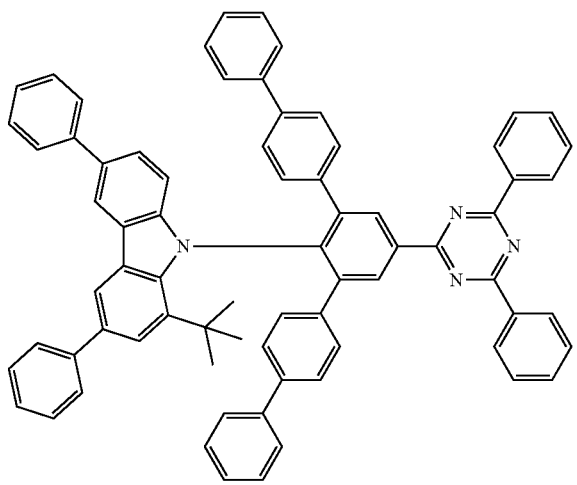
803
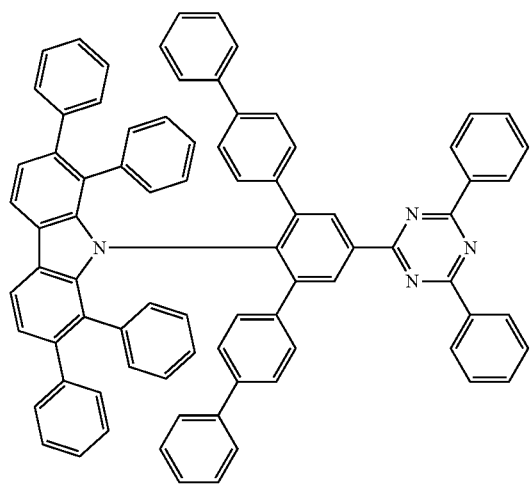
804
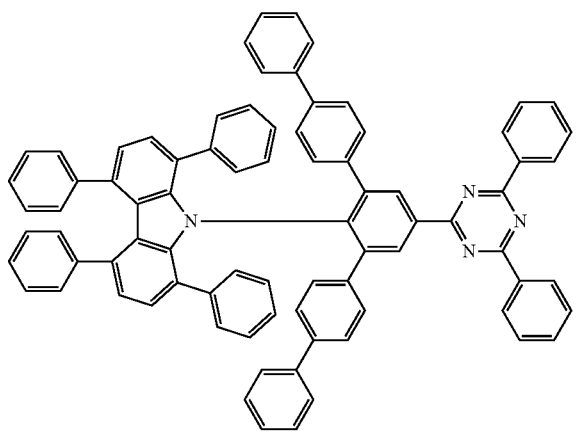

-continued
805
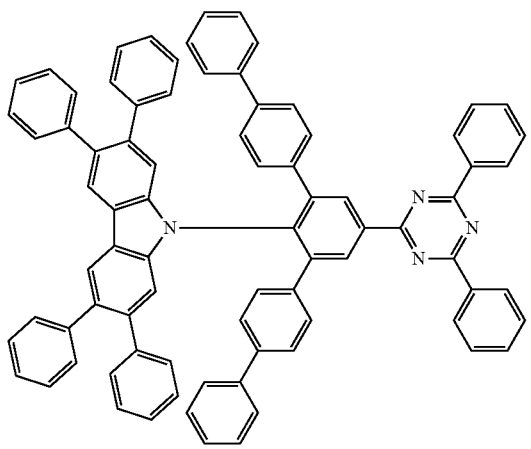
806
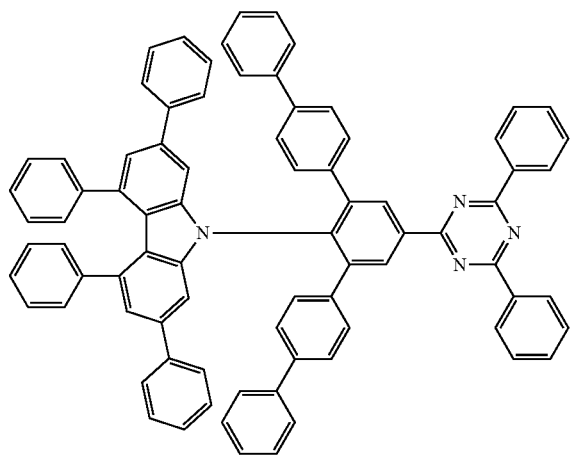
807
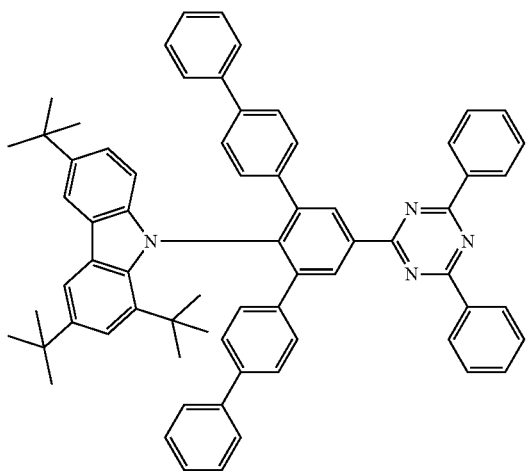
808
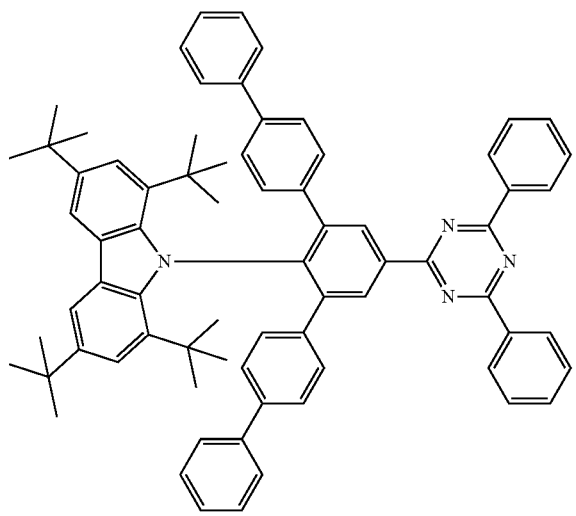
809
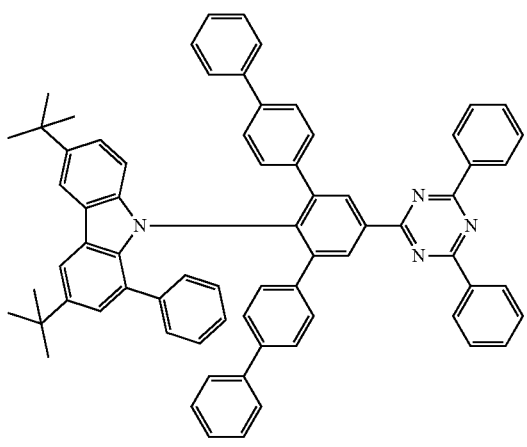
810
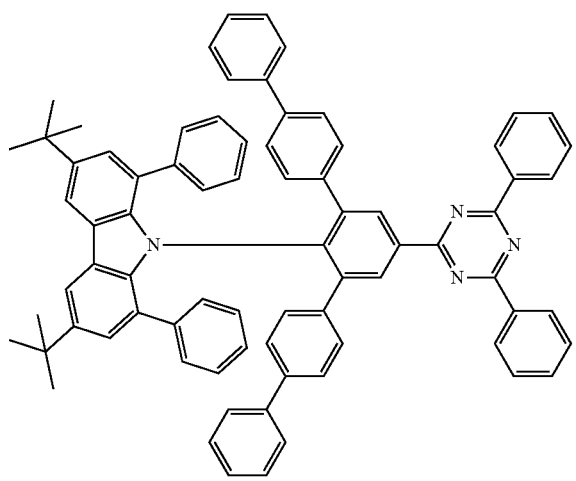

-continued
1163
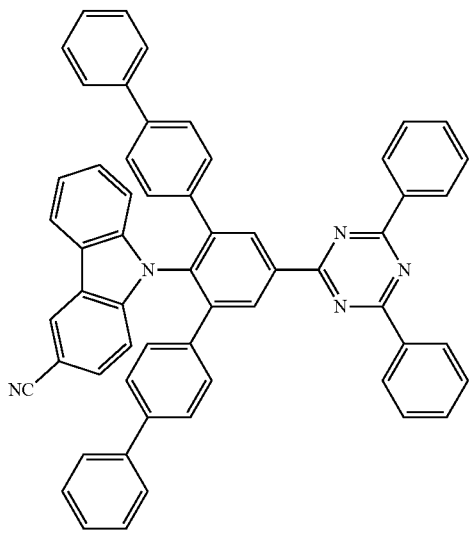
811
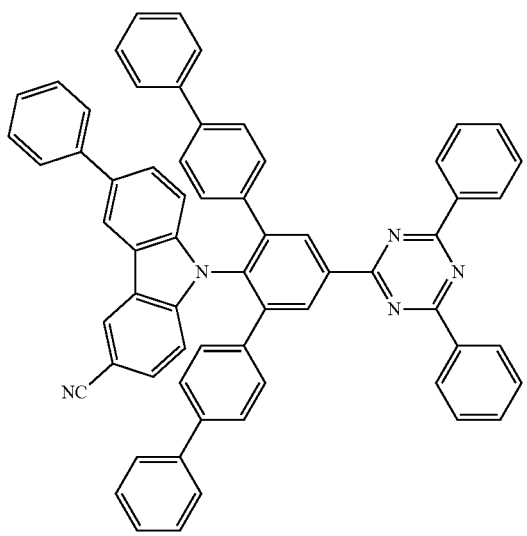
813
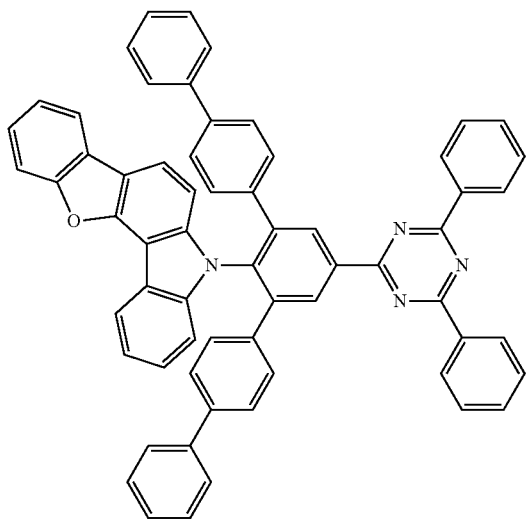
815
1164
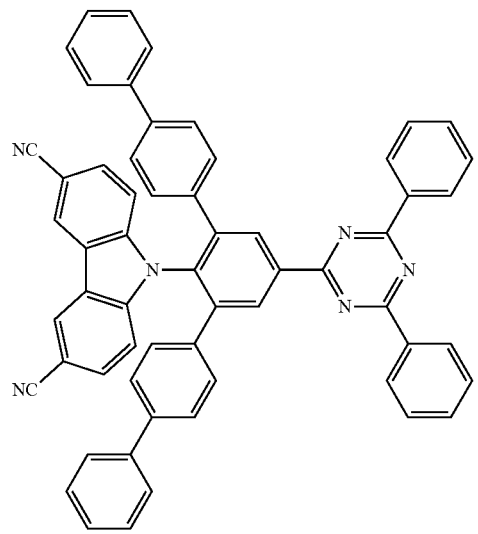
812
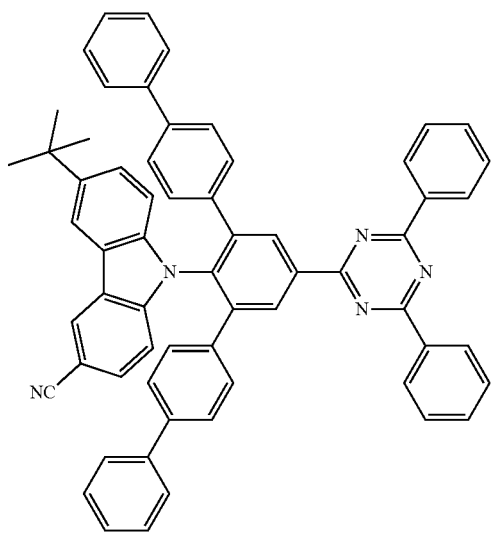
814
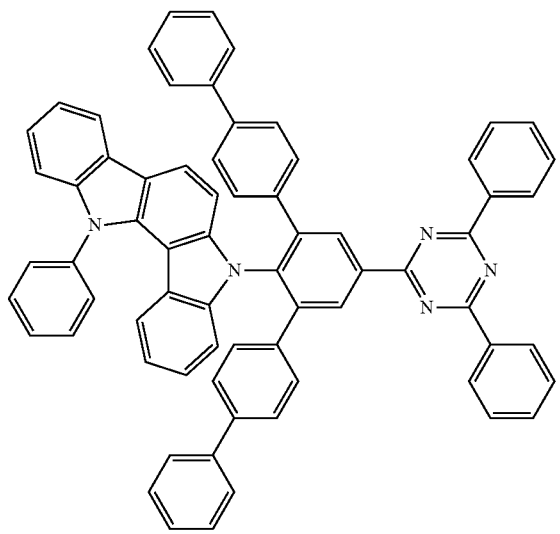
816

1165
817
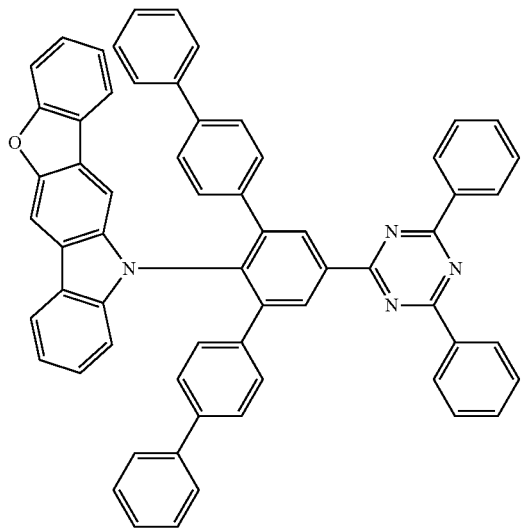
818
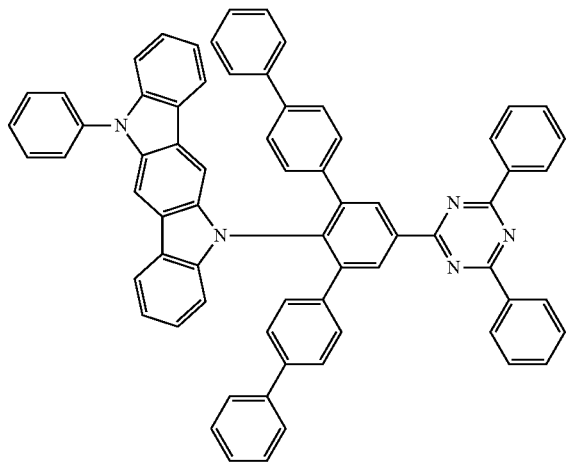
1166
819
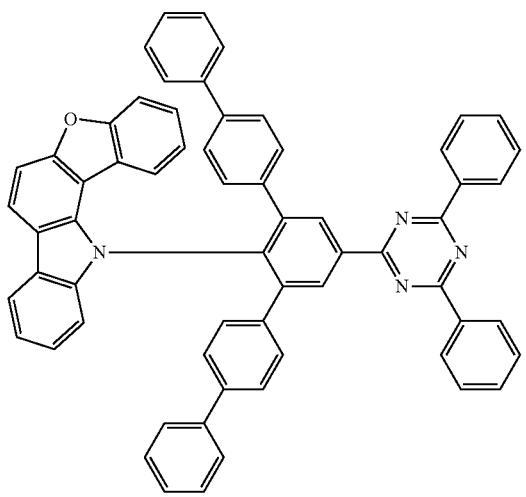
820
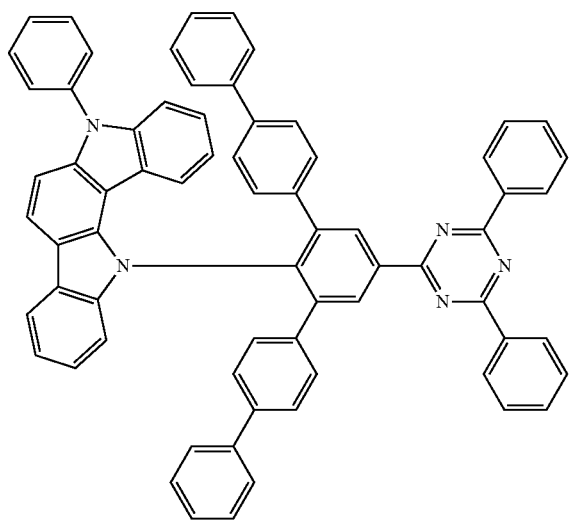
821
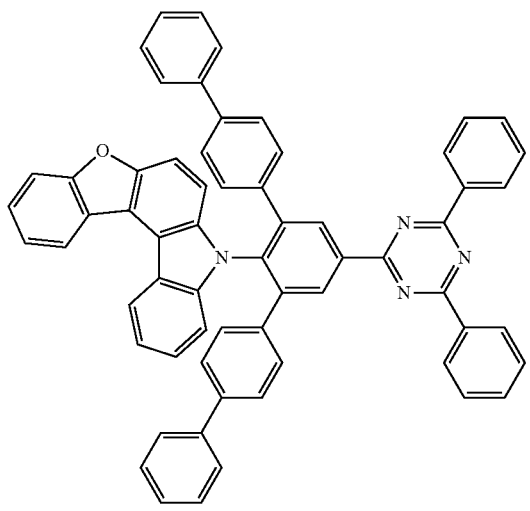
822
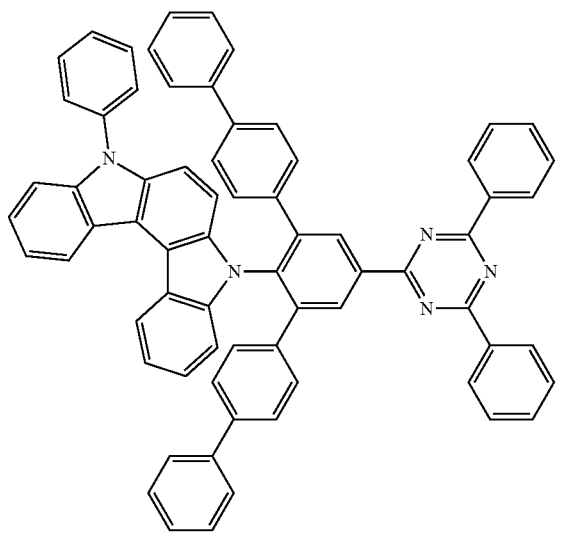

-continued
823
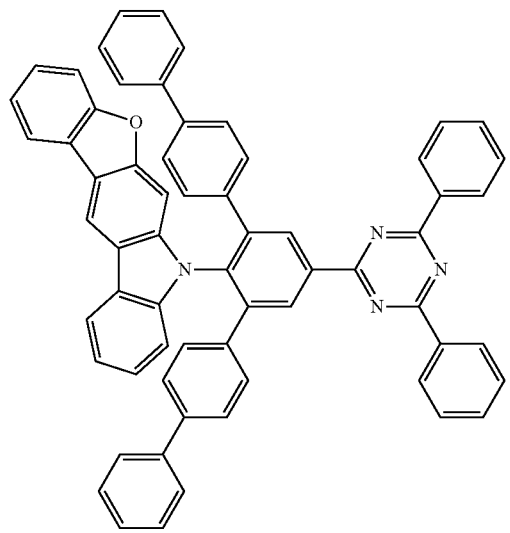
824
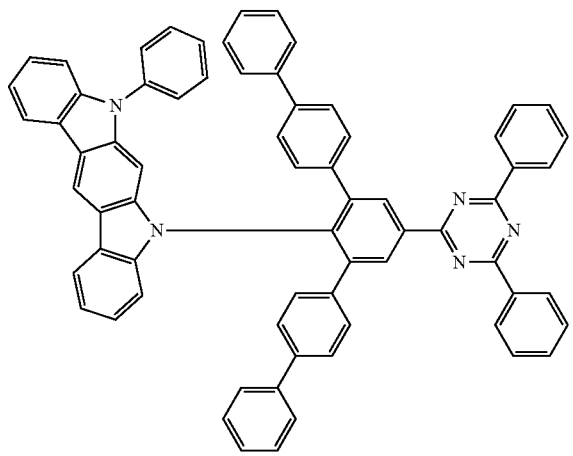
825
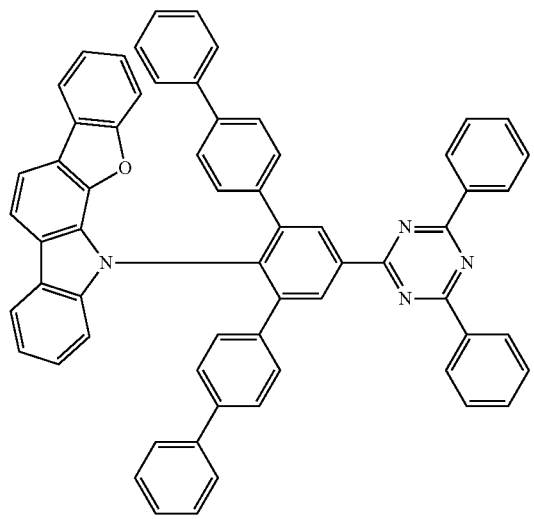
826
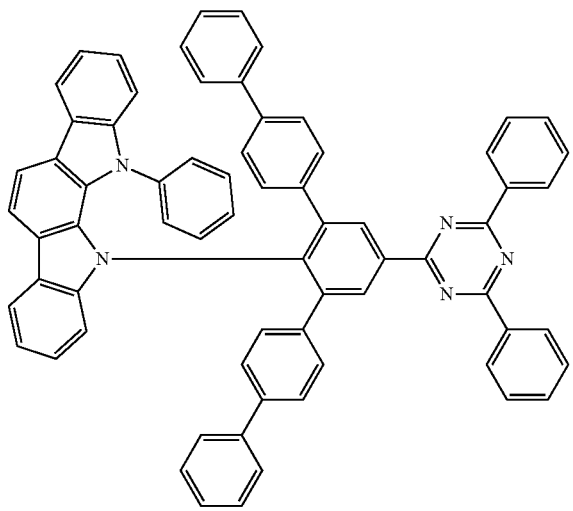
827
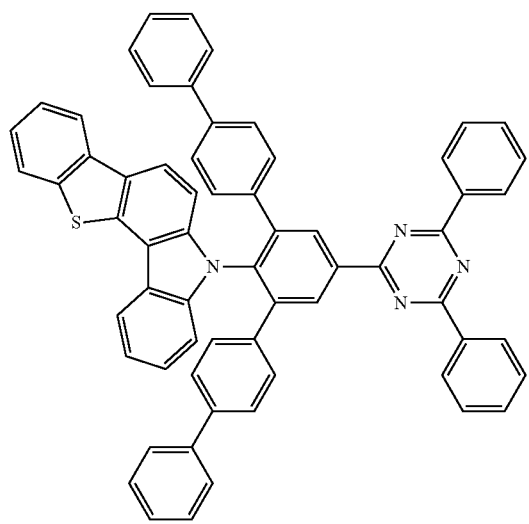
828
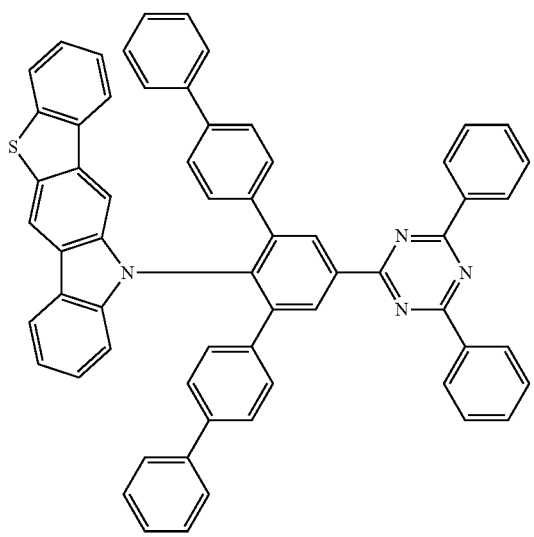

-continued
829
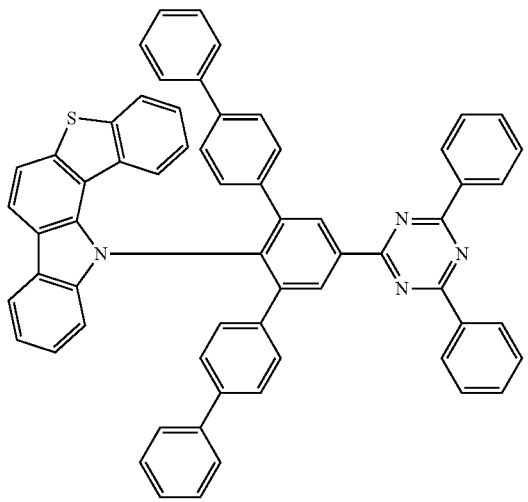
830
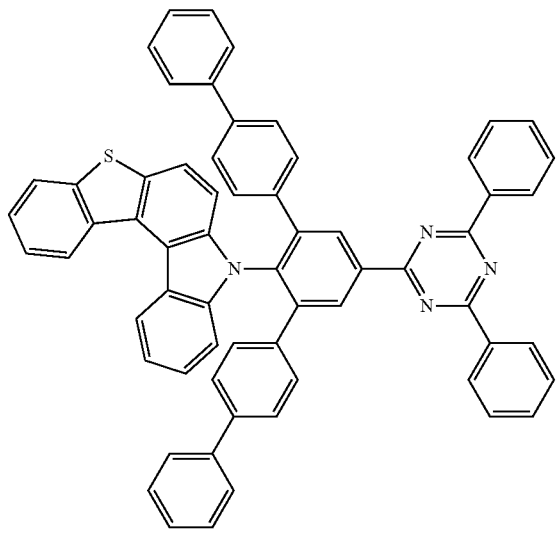
831
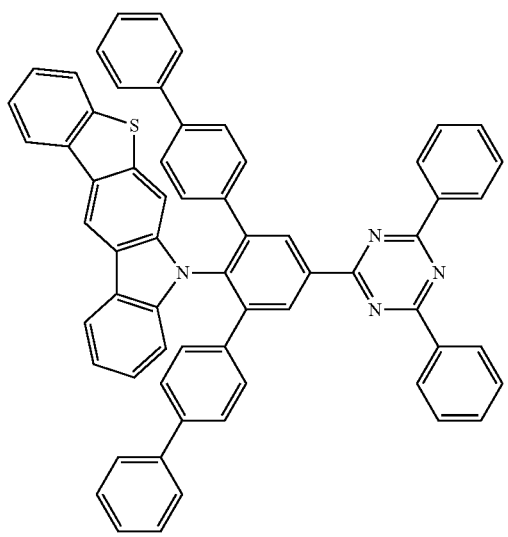
832
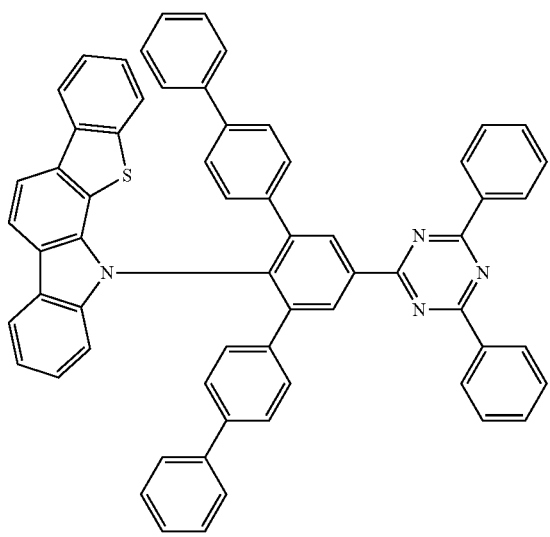
833
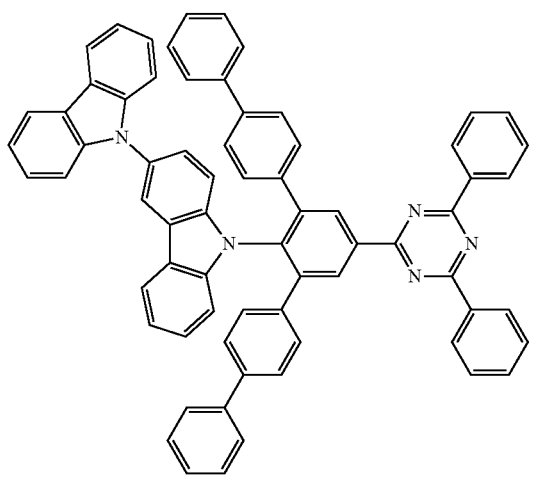
834
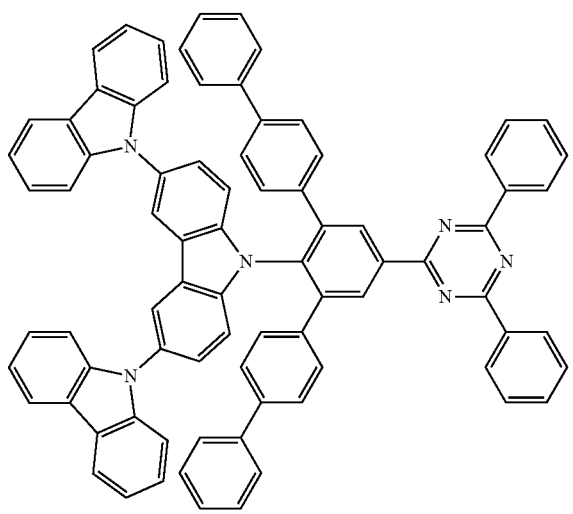

-continued
835
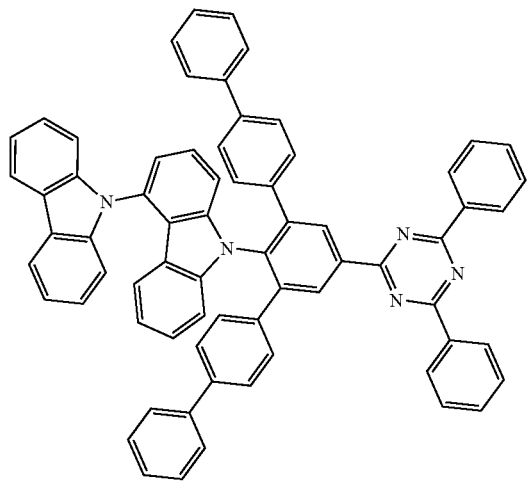
836
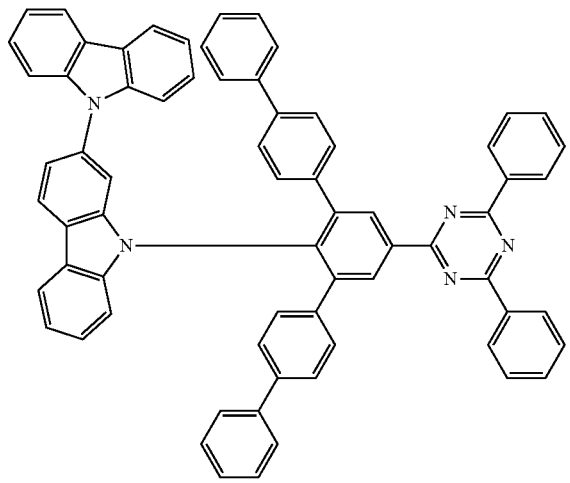
837
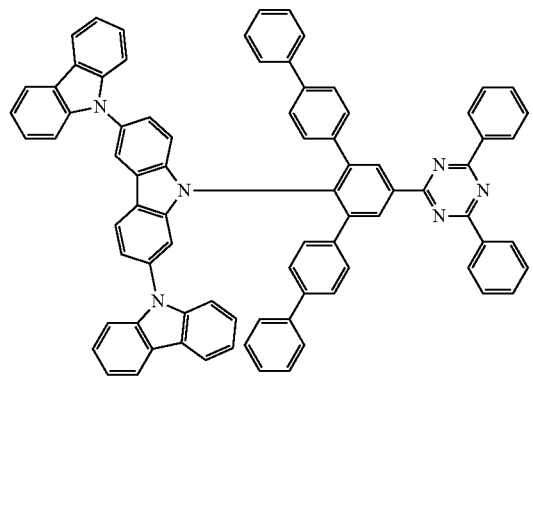
838
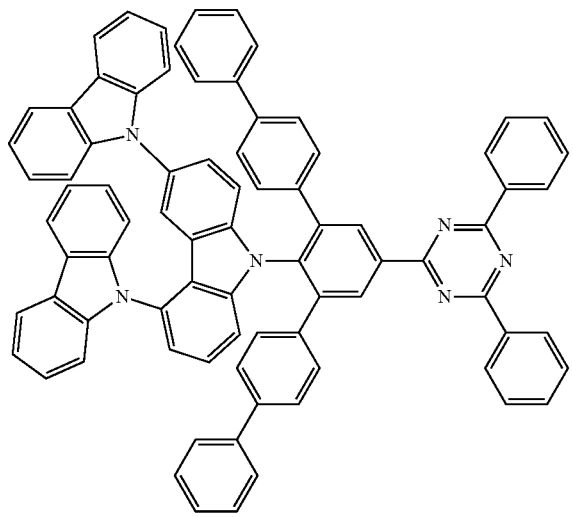
839
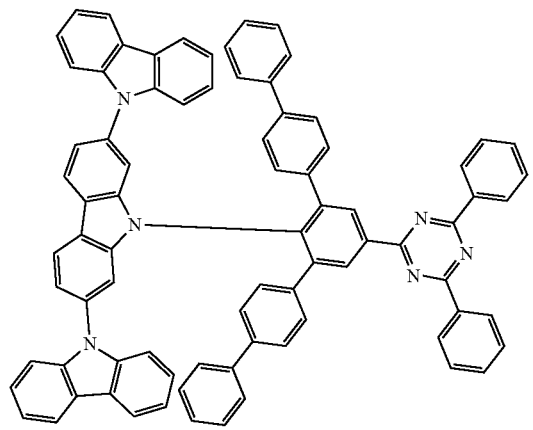
840
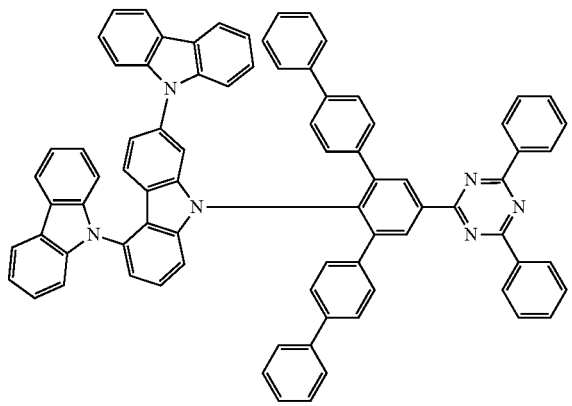

1173
1174
-continued
841
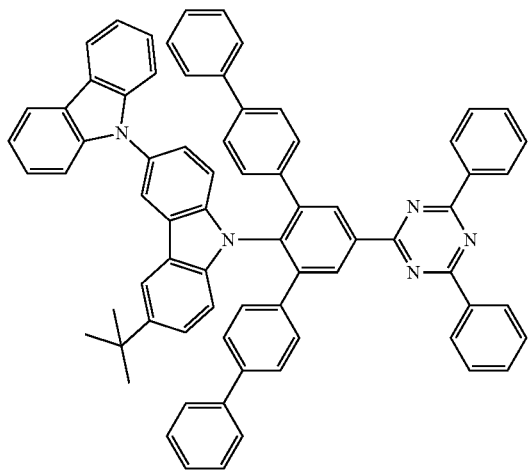
842
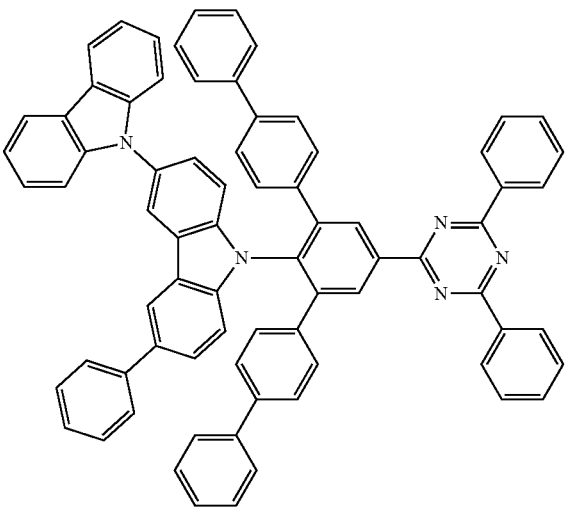
843
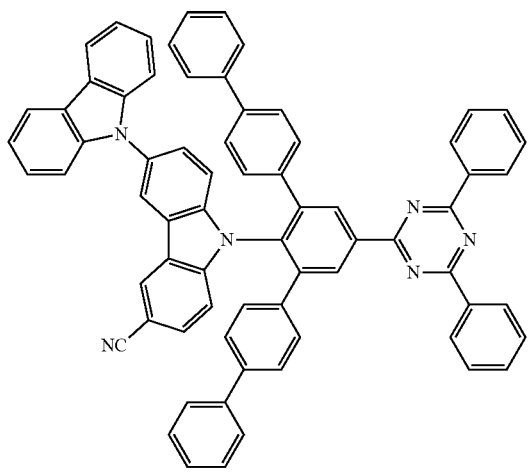
844
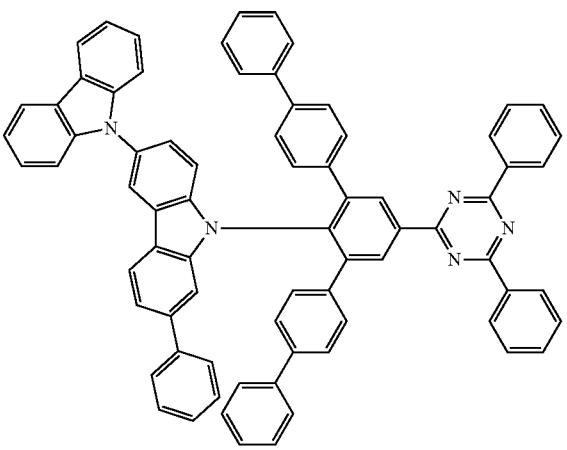
845
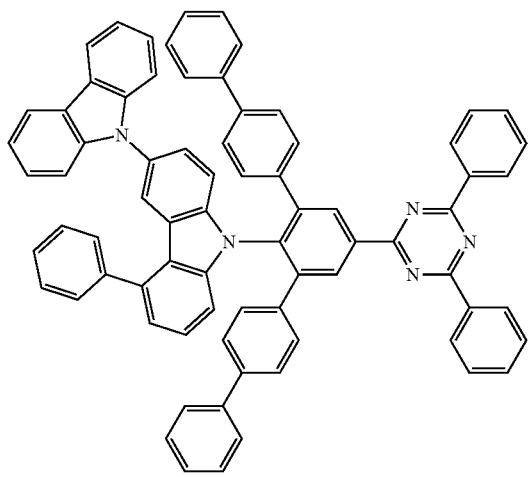
846
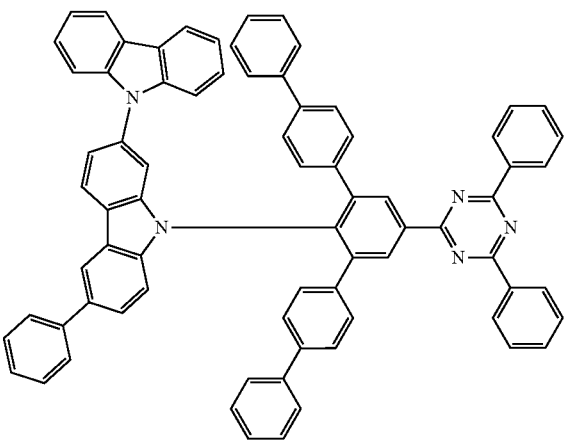

-continued
847
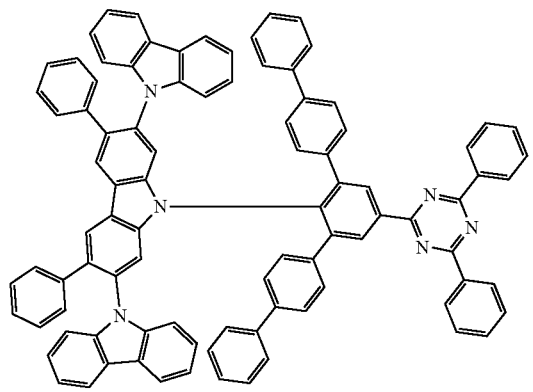
848
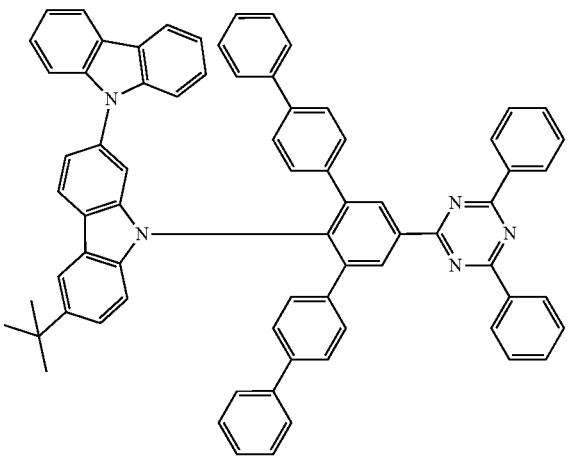
849
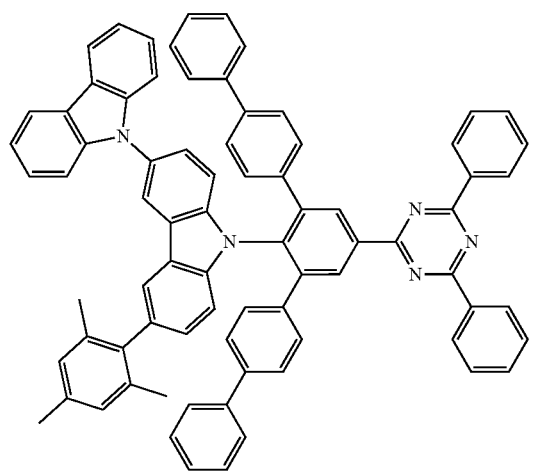
850
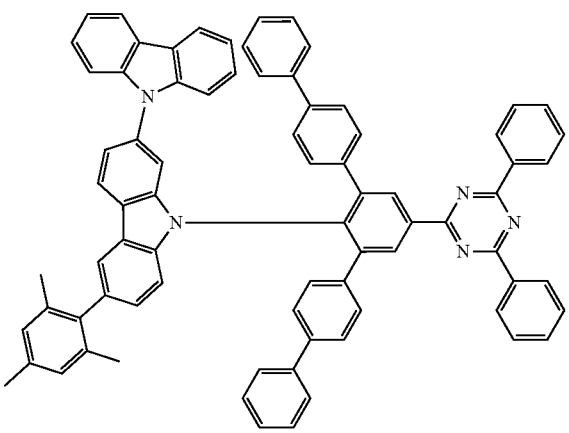
851
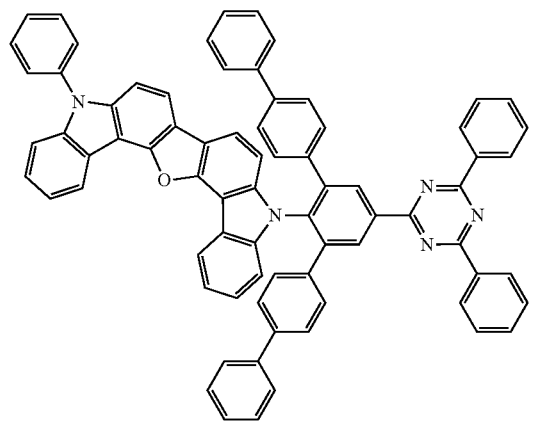
852
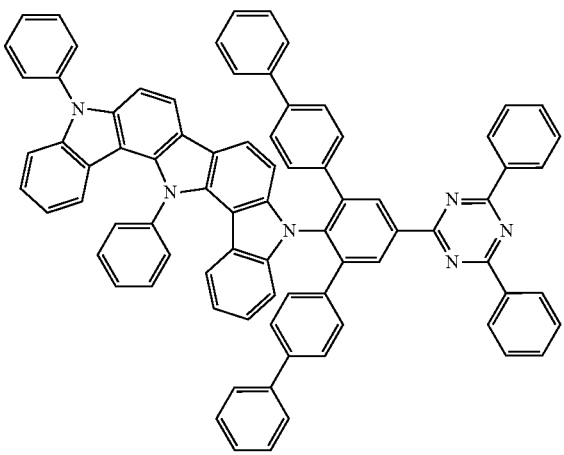

1177 -continued 1178
853
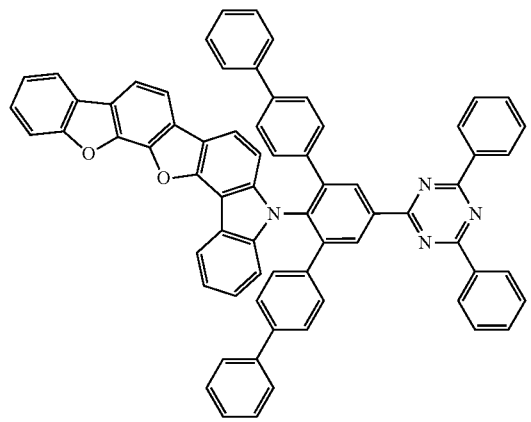
854
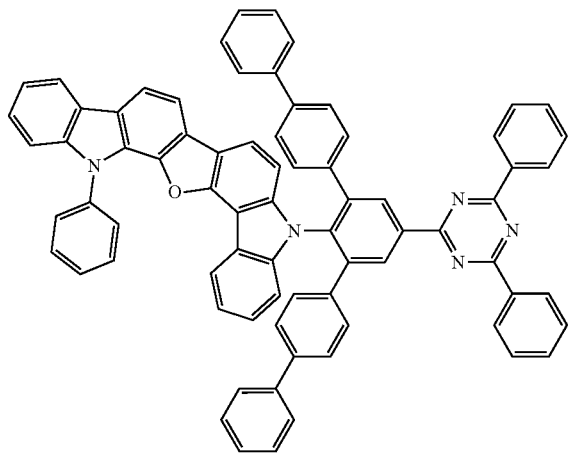
855
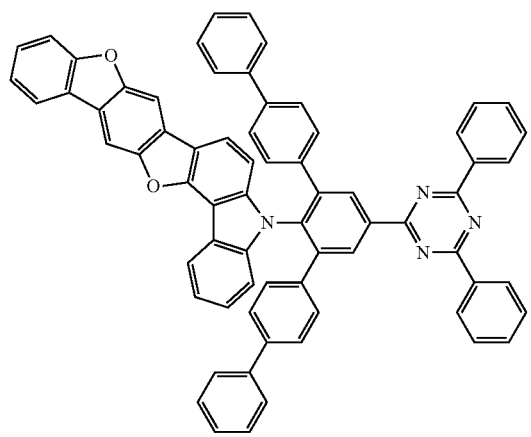
856
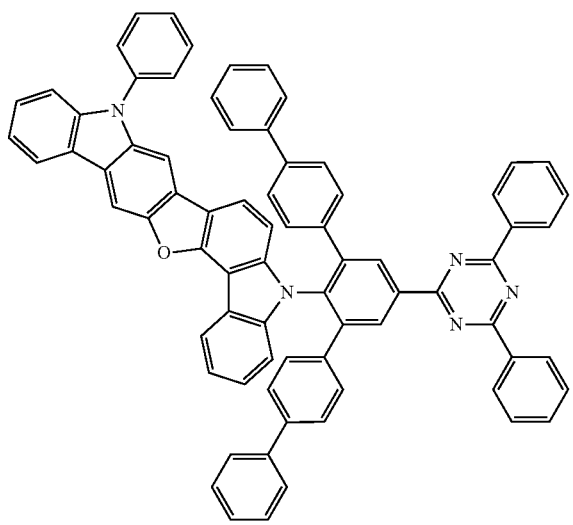
857
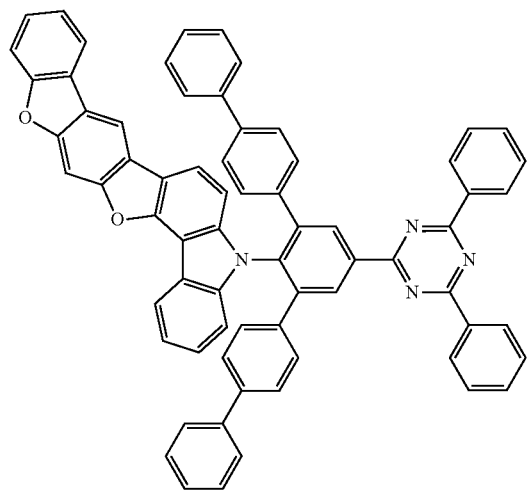
858
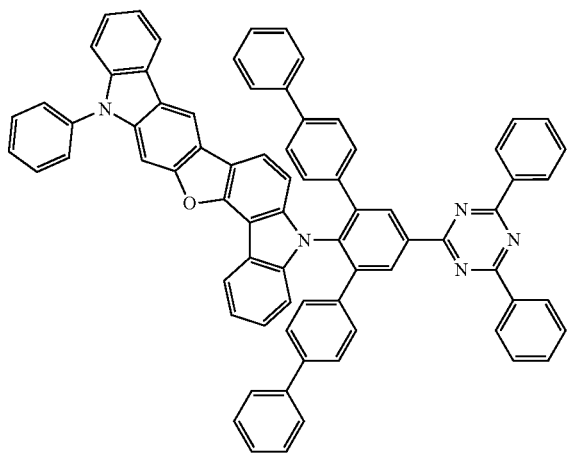

-continued
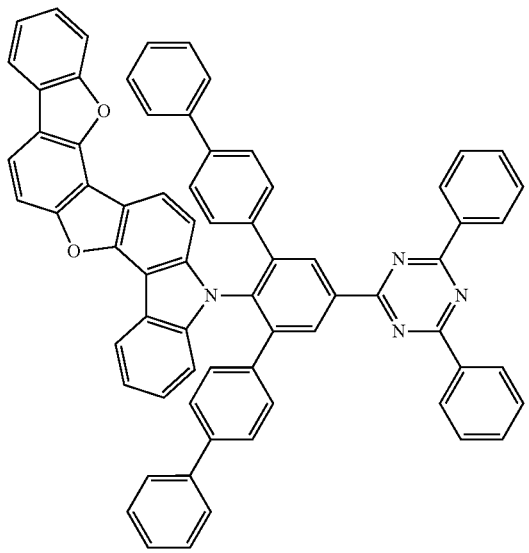
859
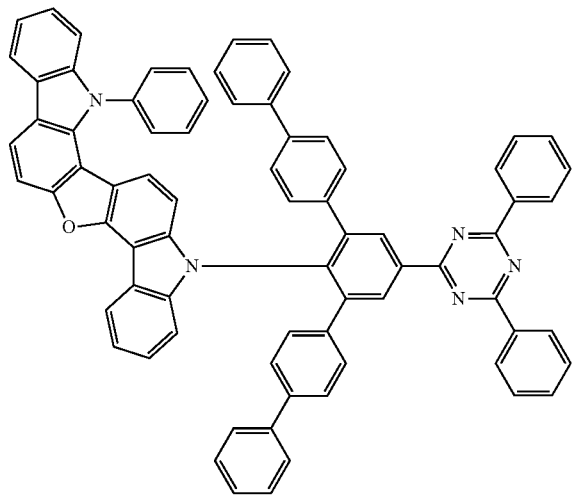
860
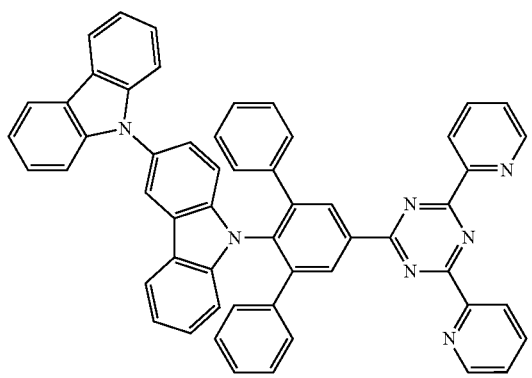
861
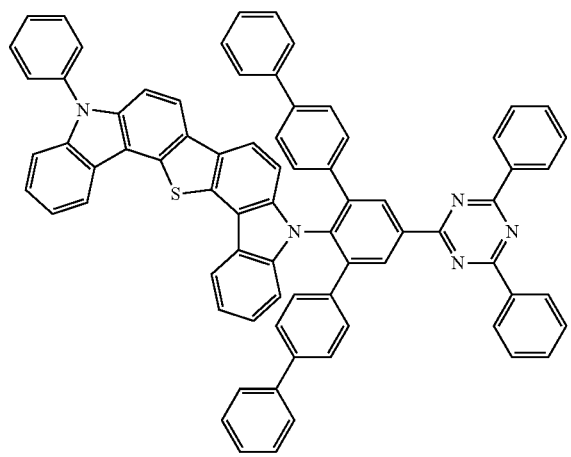
862
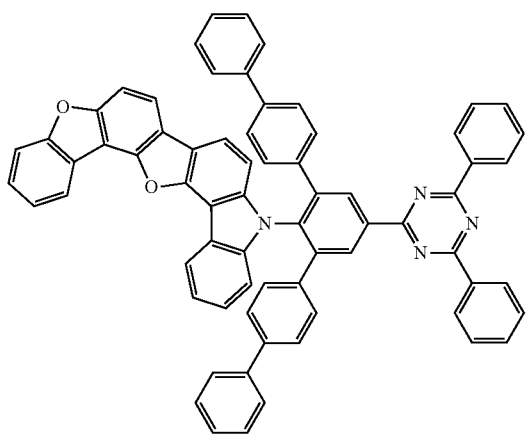
863
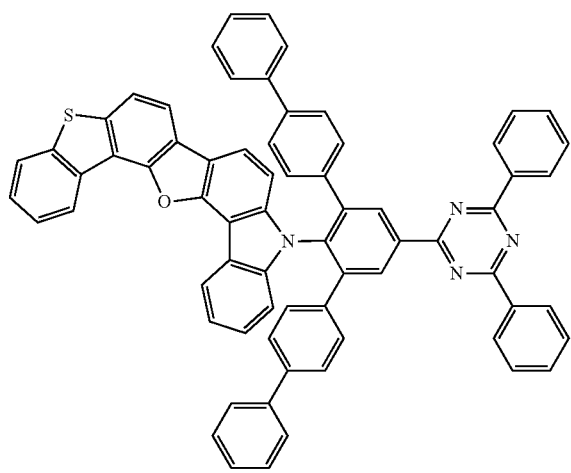
864

865
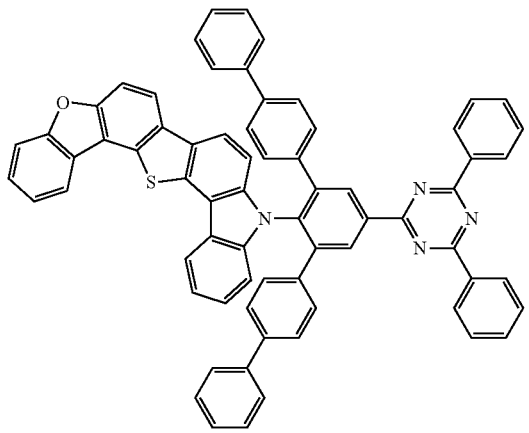
866
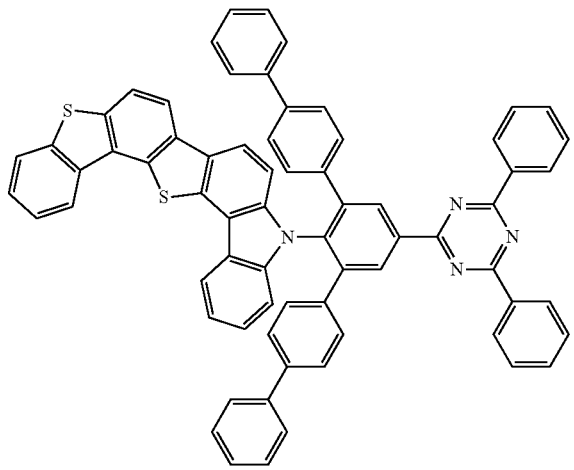
867
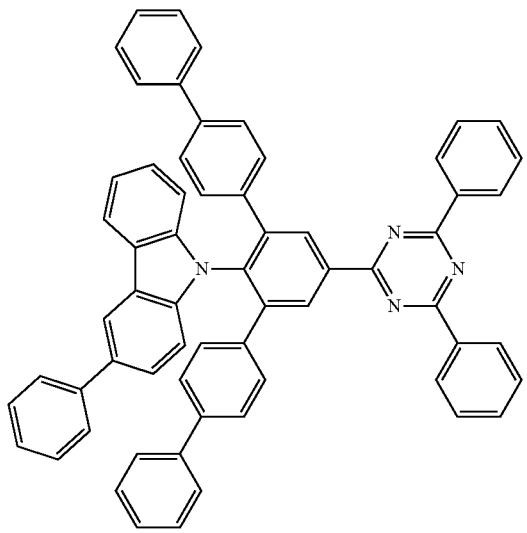
868
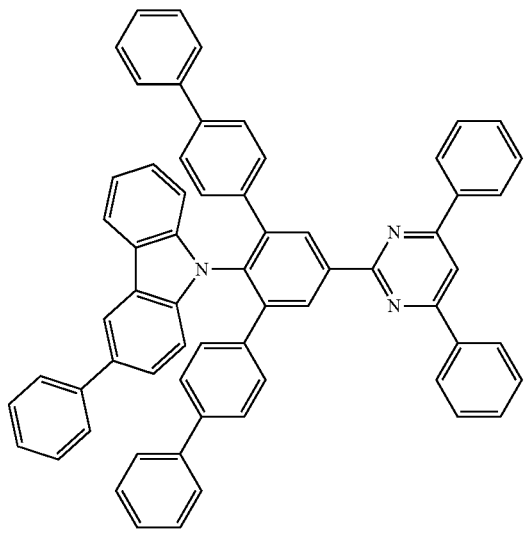
869
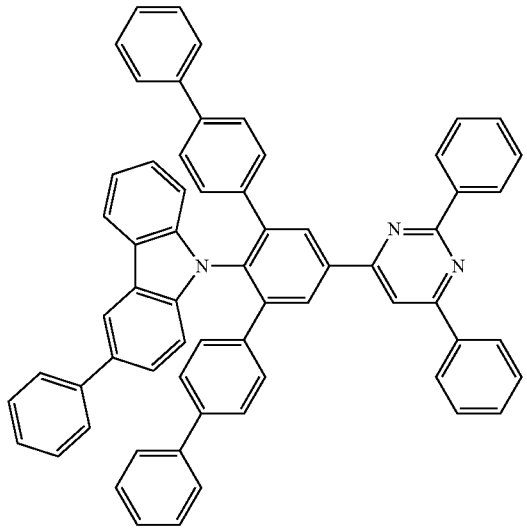
870
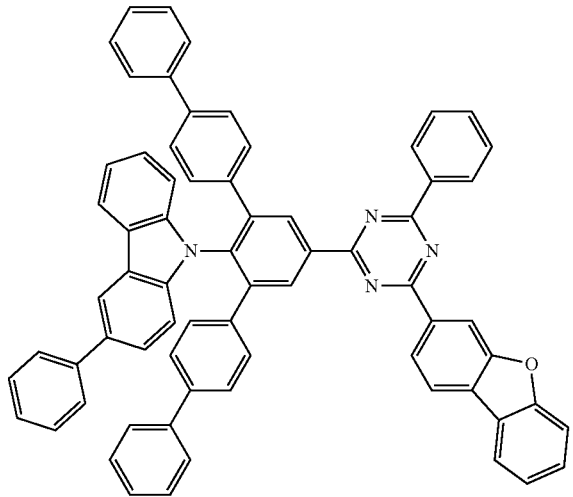

1183 1184
-continued
871
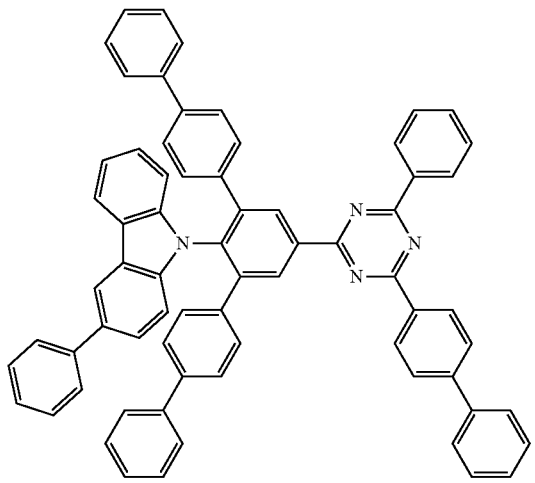
872
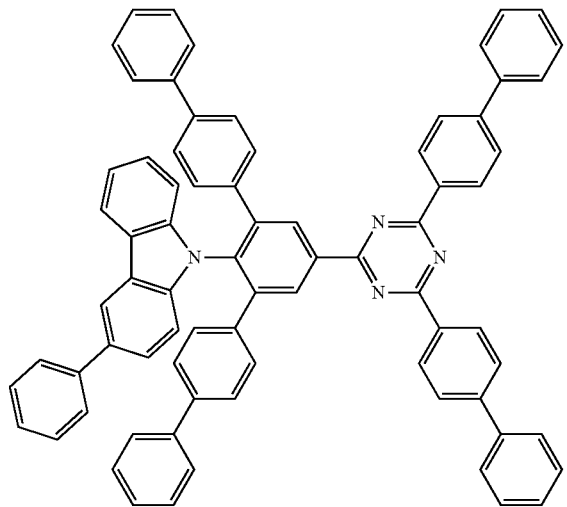
873
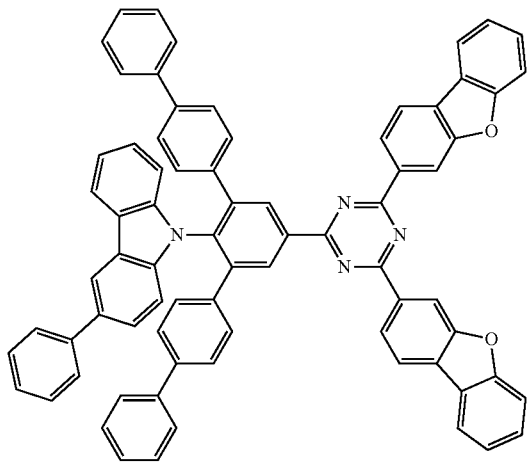
874
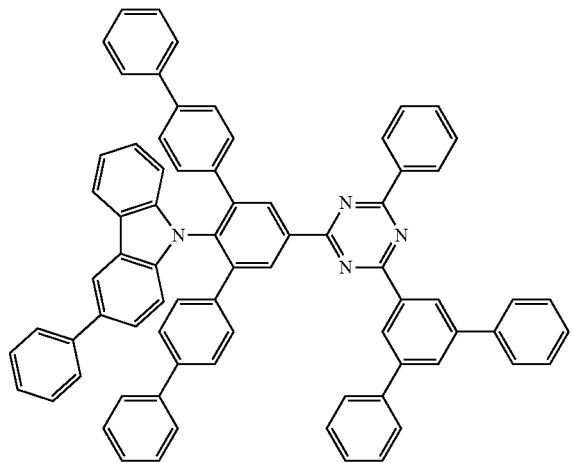
875
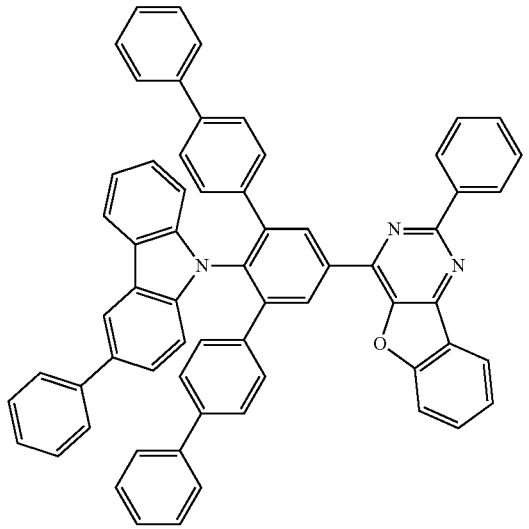
876
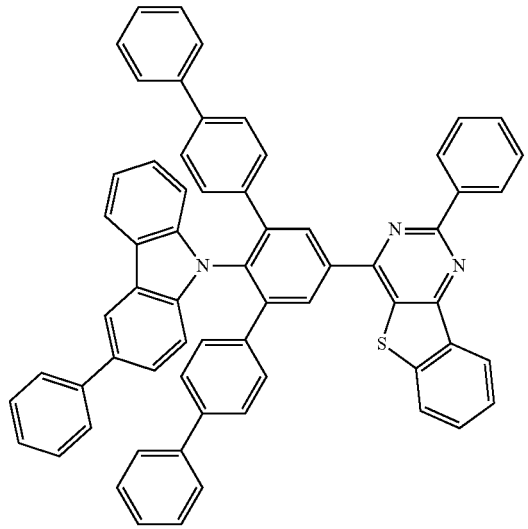

877
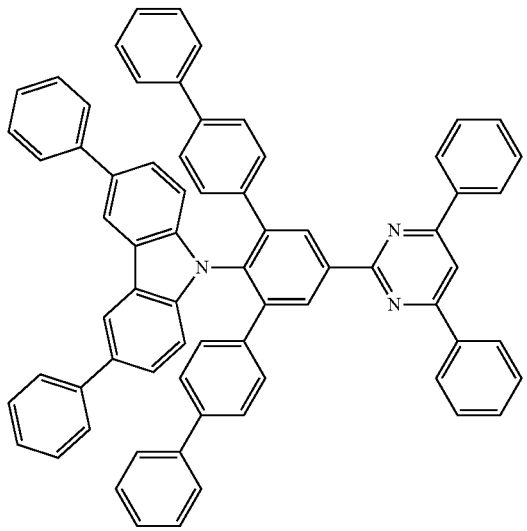
878
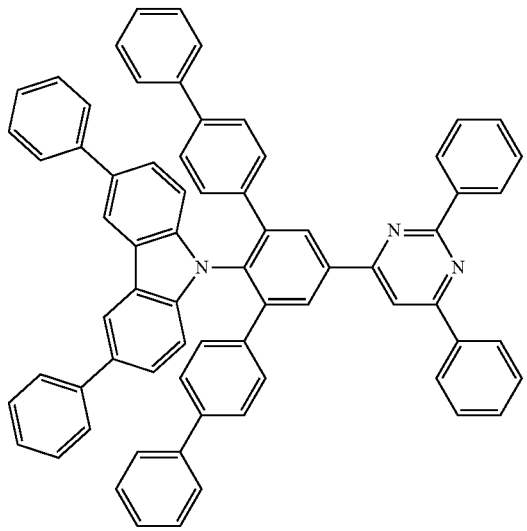
879
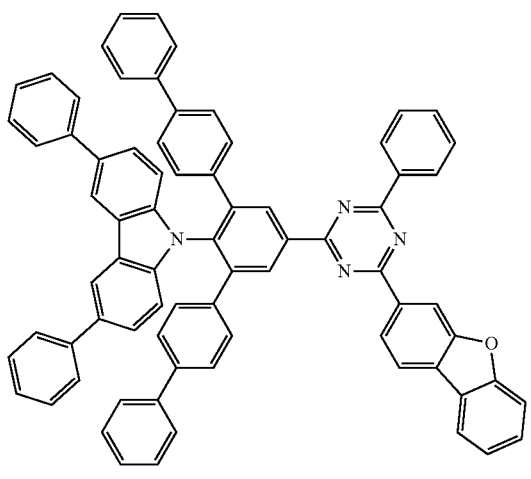
880
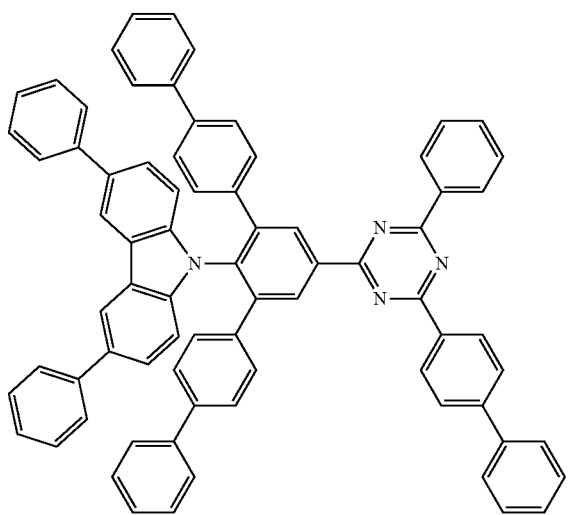
881
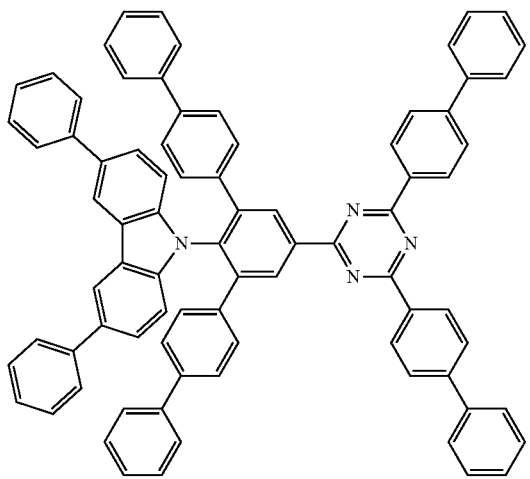
882
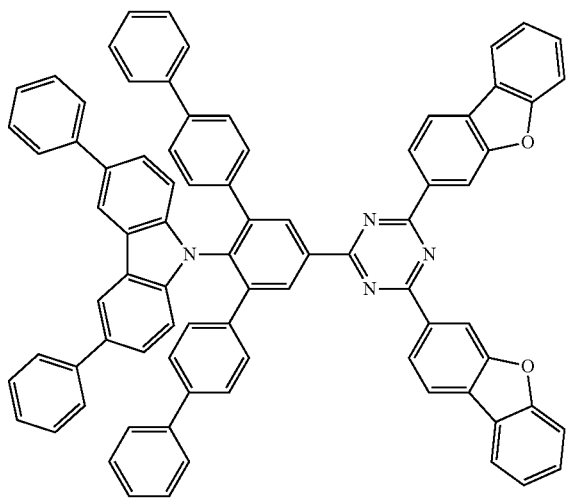

-continued
883
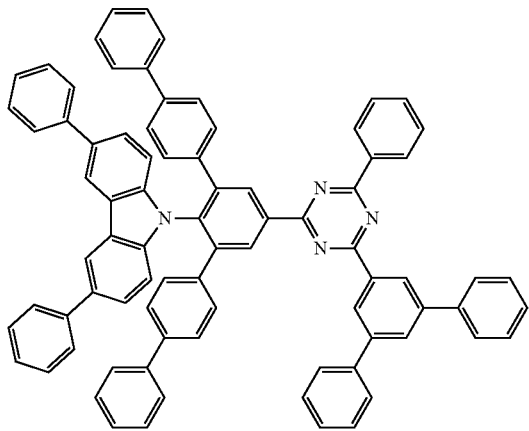
884
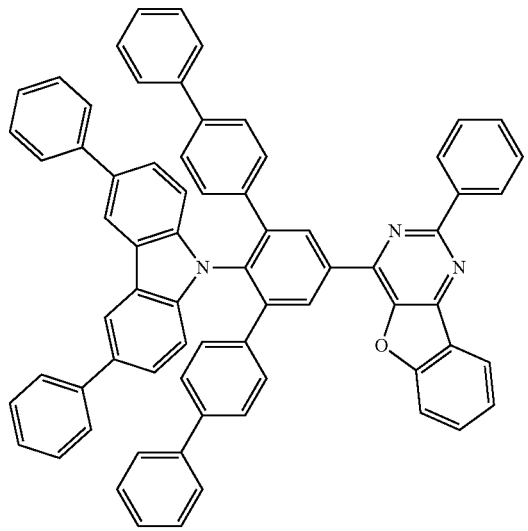
885
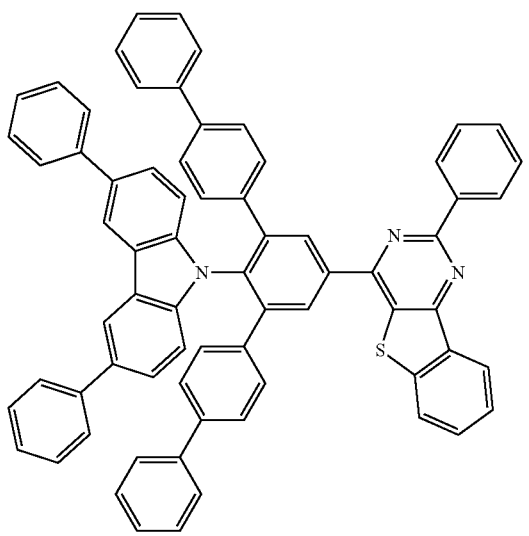
886
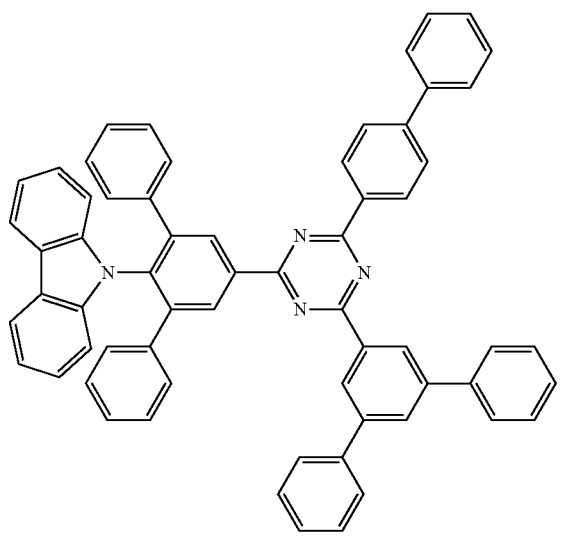
887
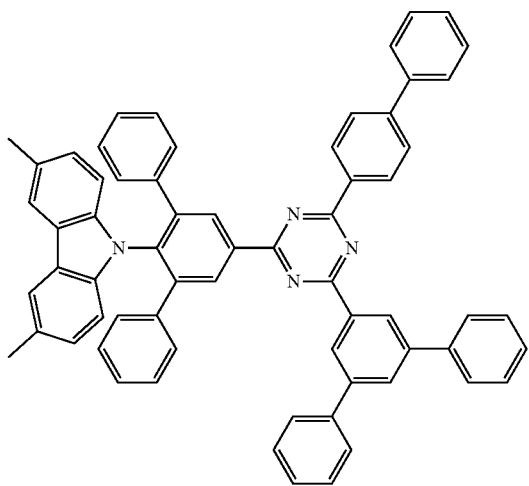
888
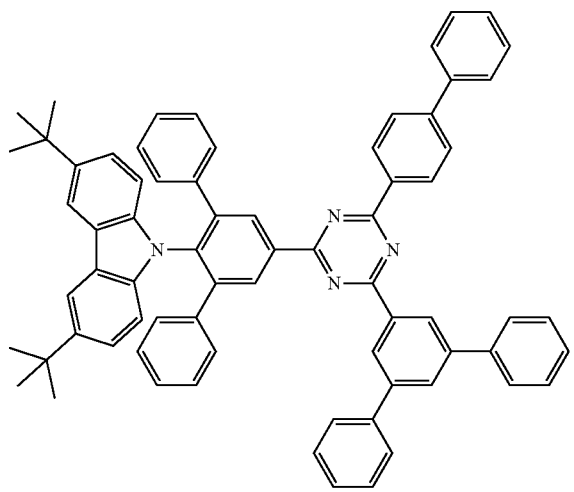

889
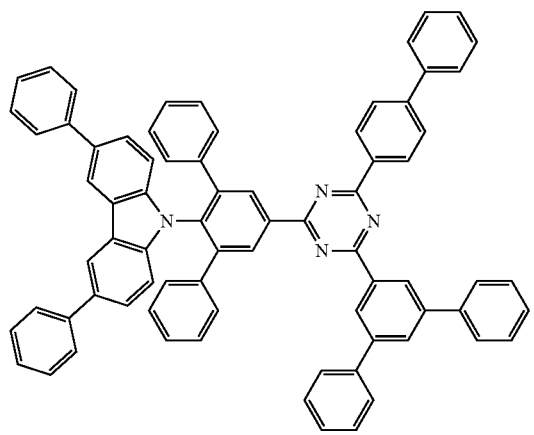
890
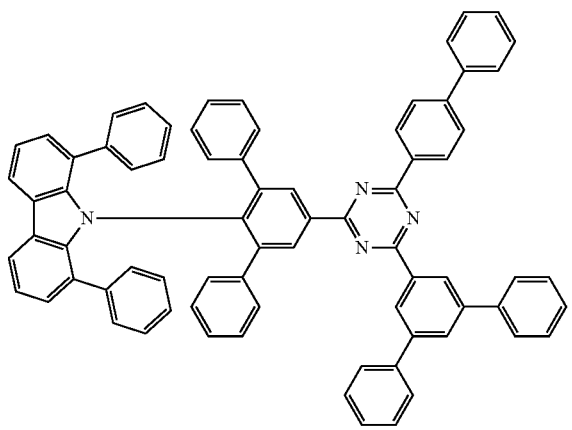
891
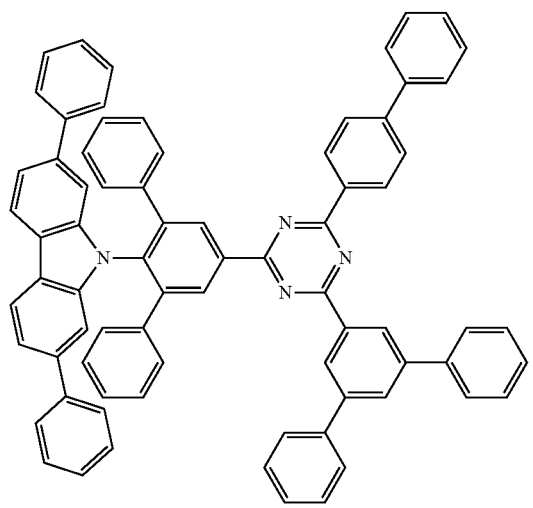
892
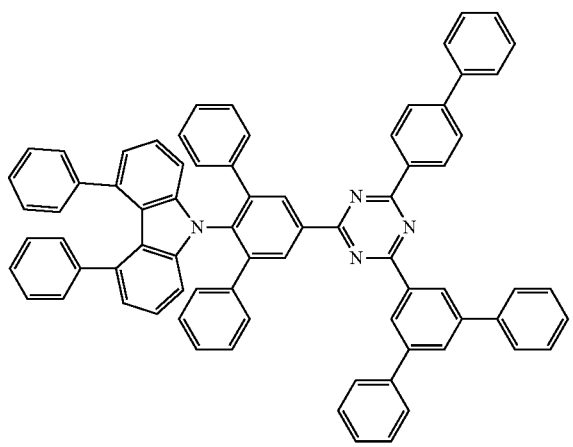
893
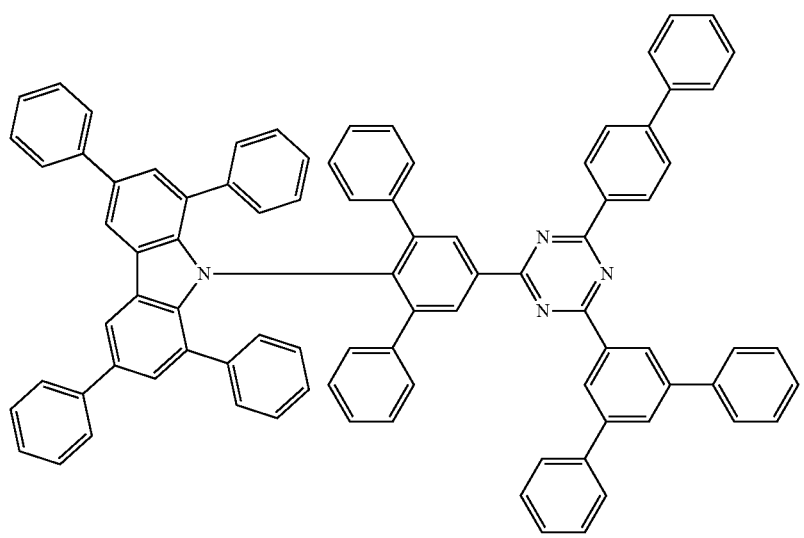

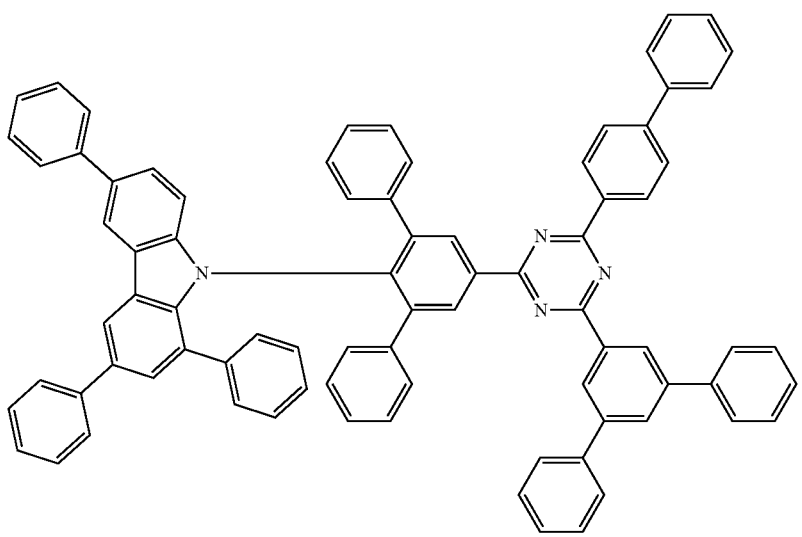
894
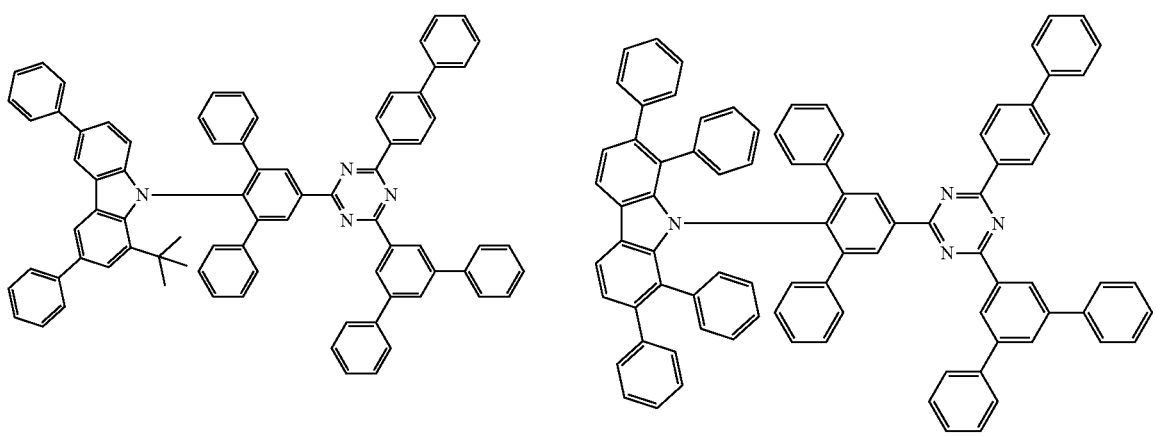
895 896
897
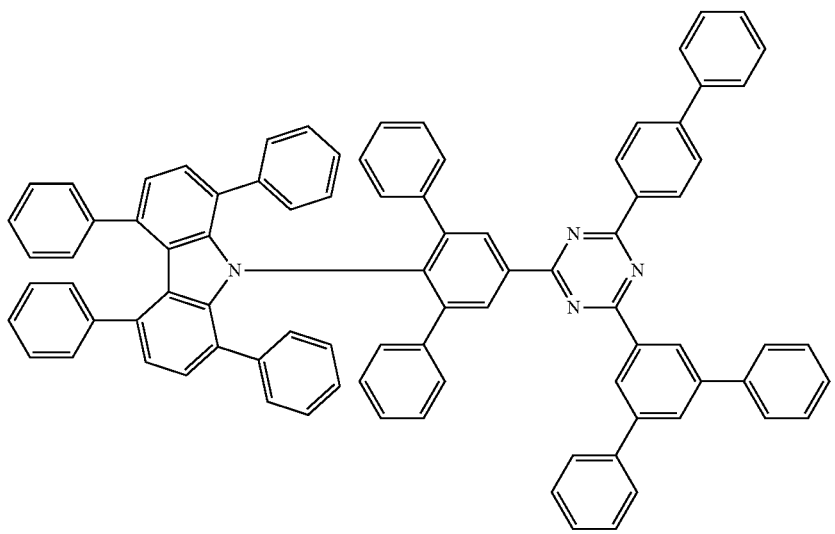

-continued
| 1193 | 1194 |
|---|---|
| 898 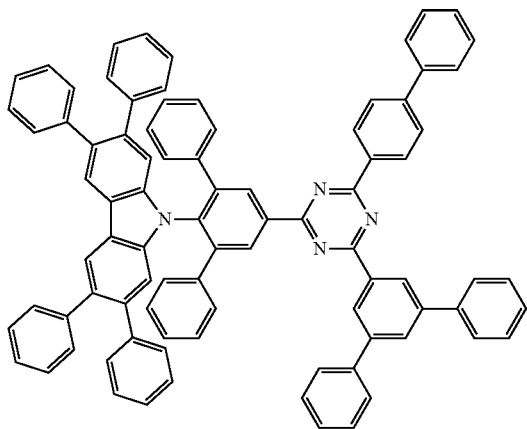 | 899 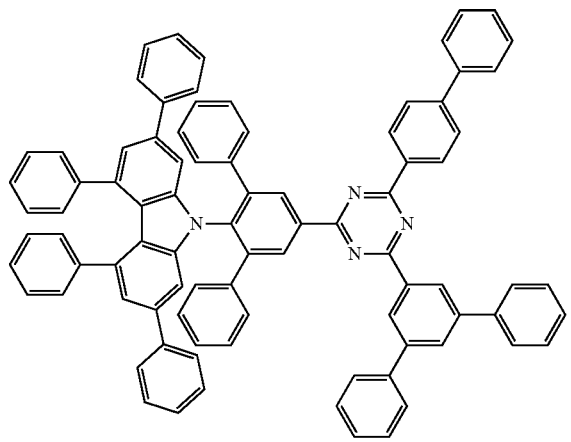 |
| 900 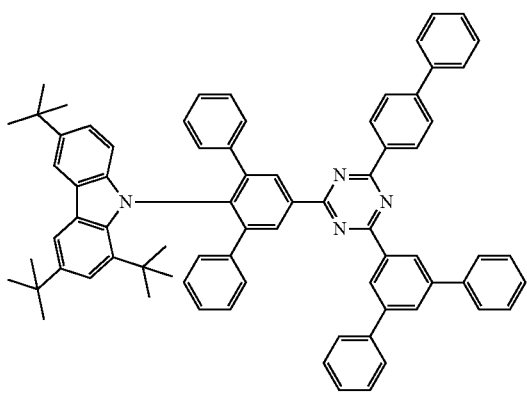 | 901 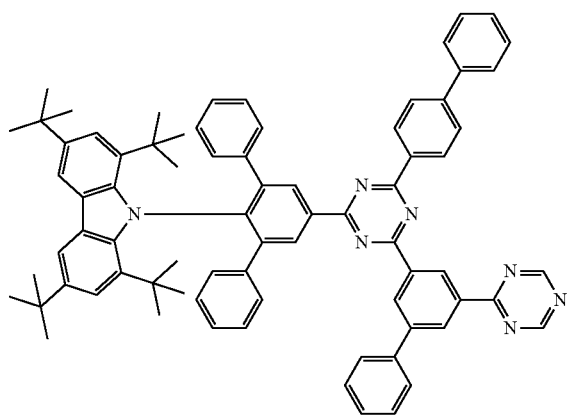 |
| 902 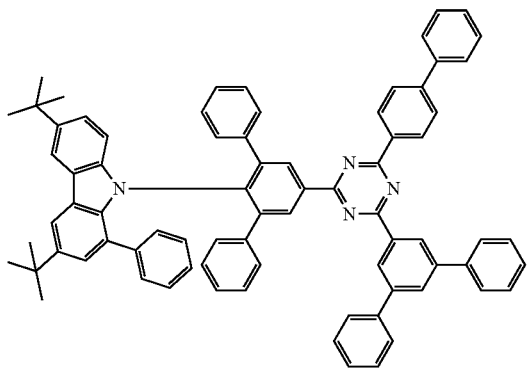 | 903 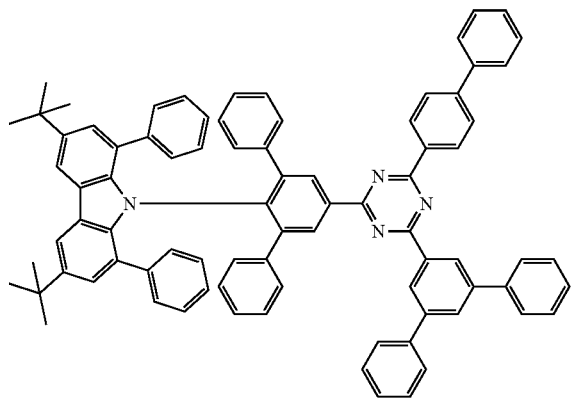 |

-continued
904
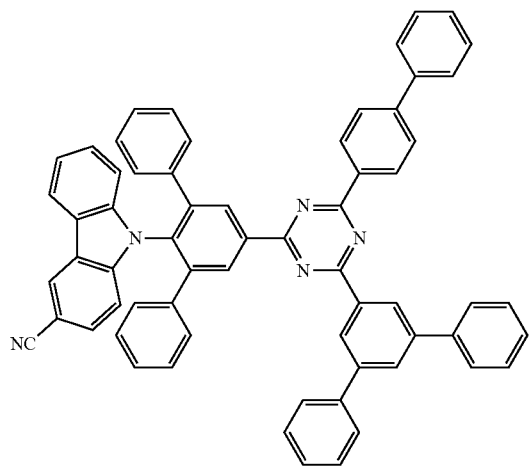
905
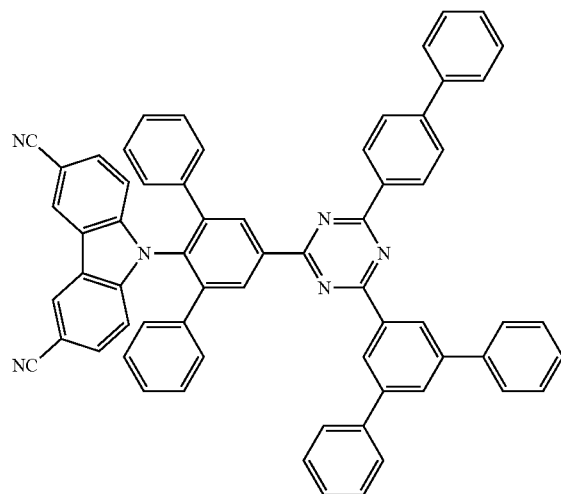
906
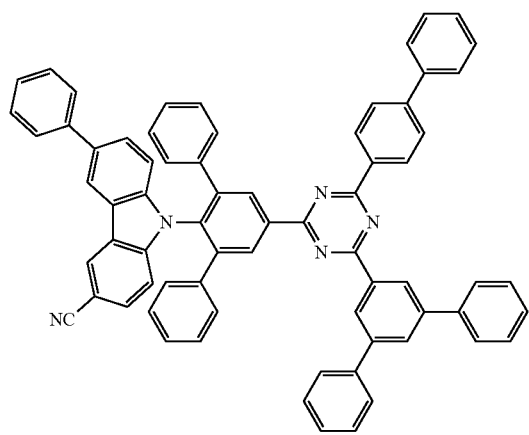
907
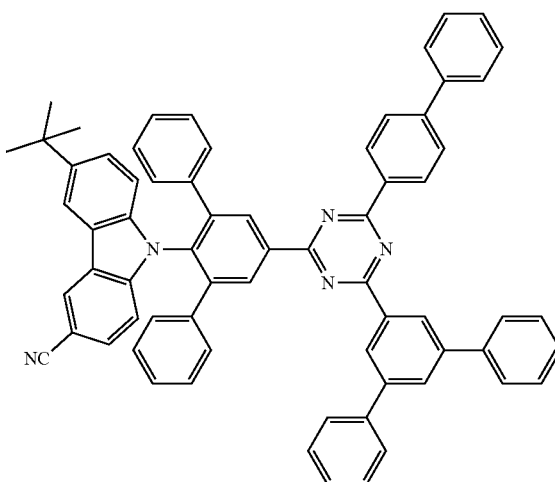
908
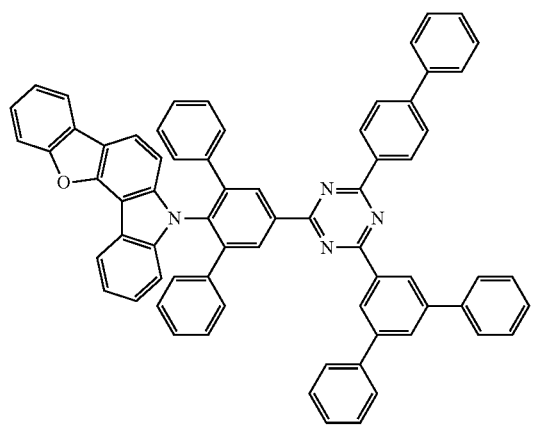
909
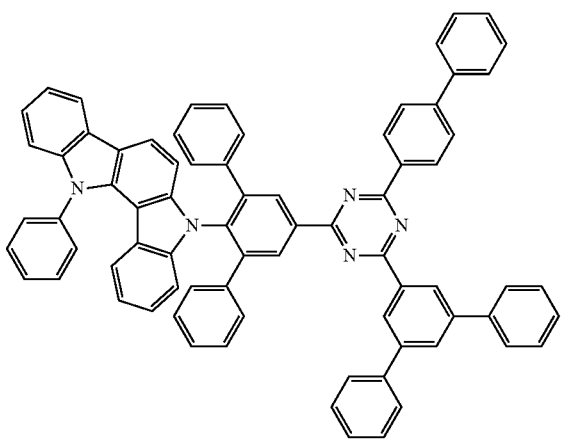

1197
910
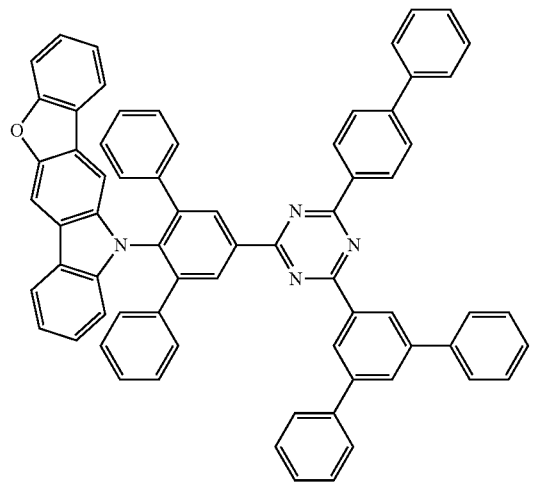
1198
911
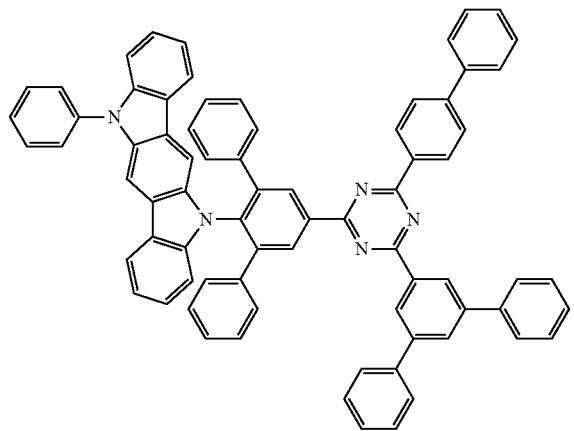
912
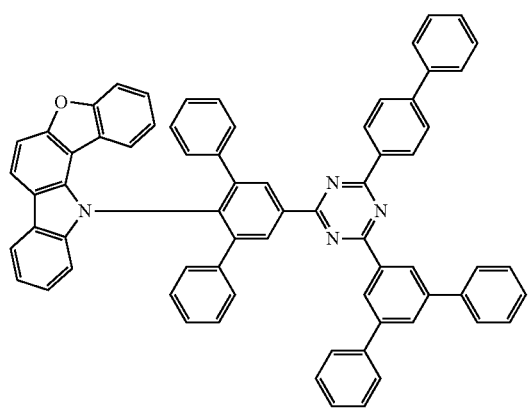
913
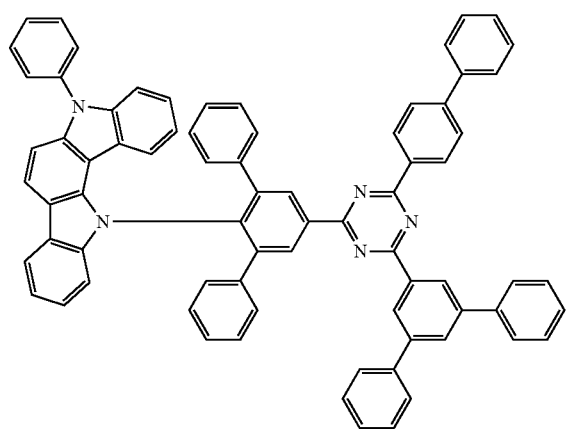
914
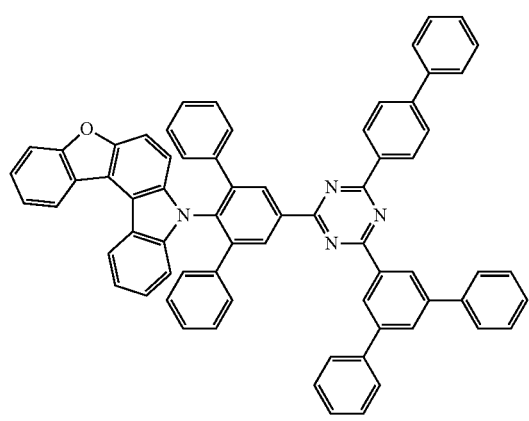
915
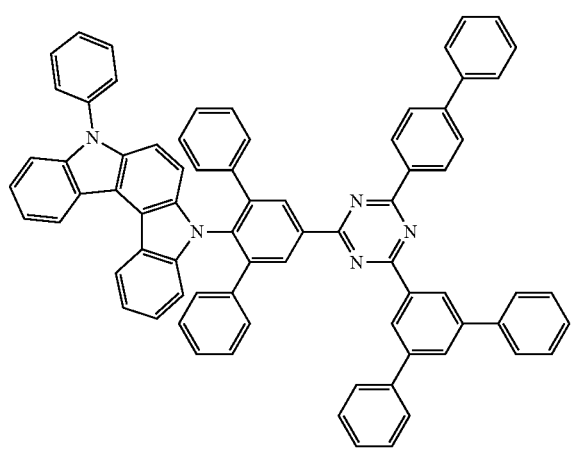

-continued
916
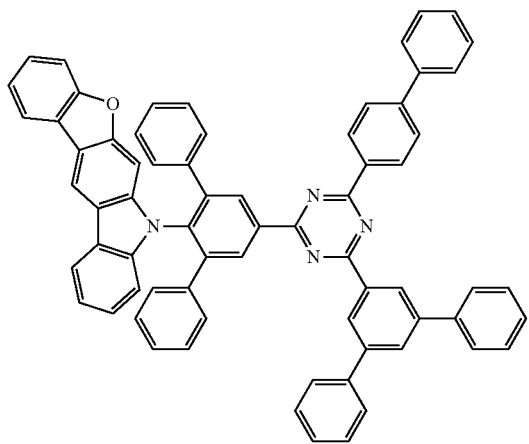
917
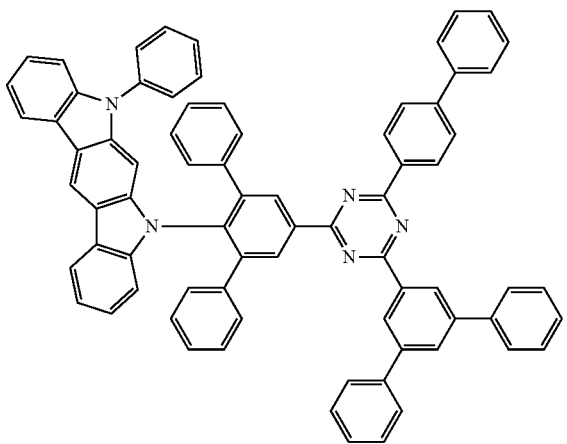
918
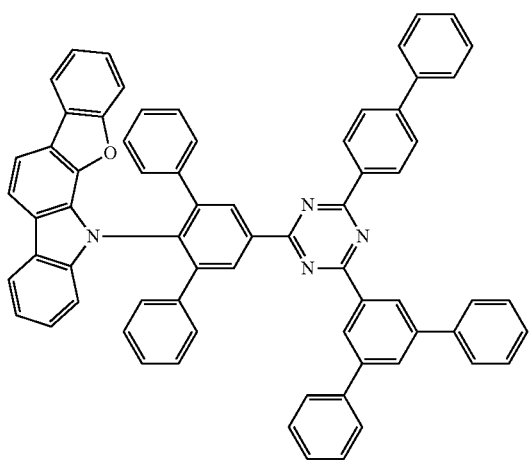
919
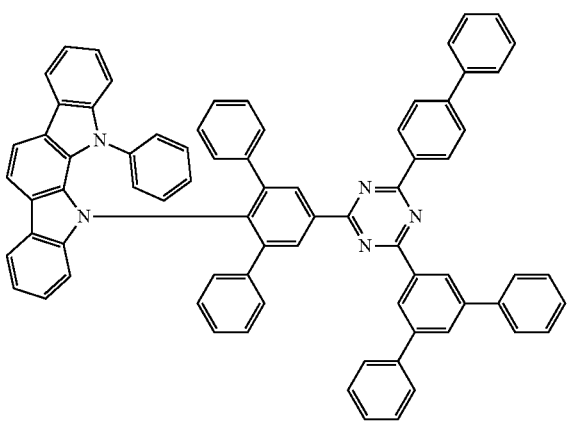
920
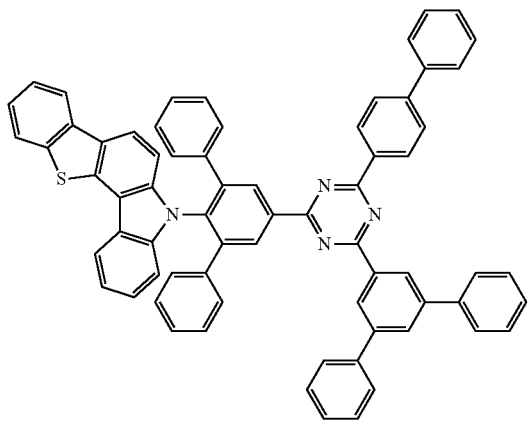
921
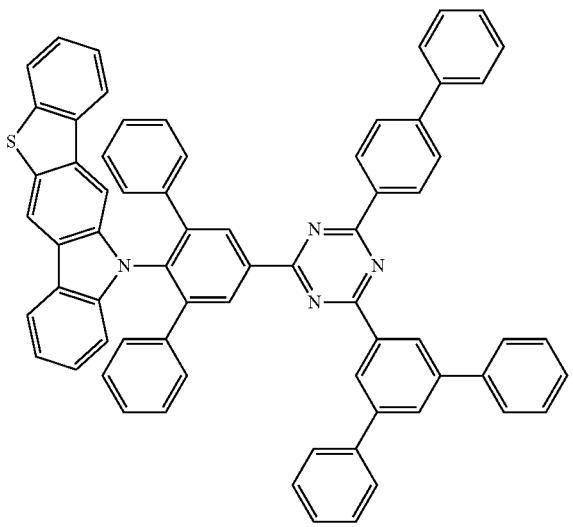

-continued
922
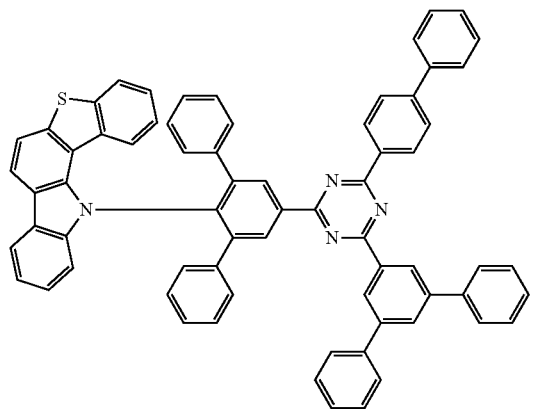
923
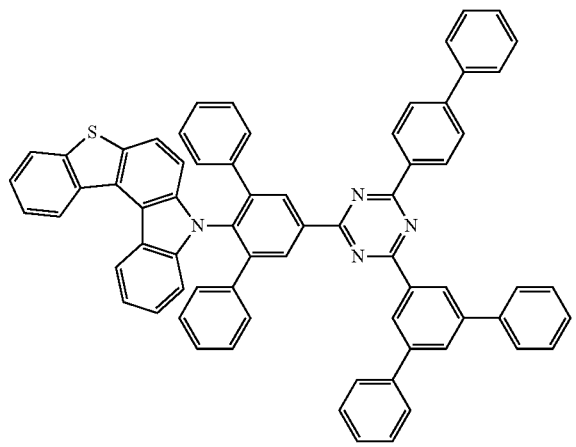
924
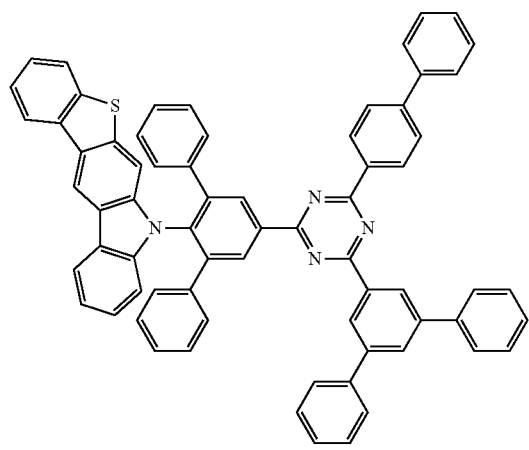
925
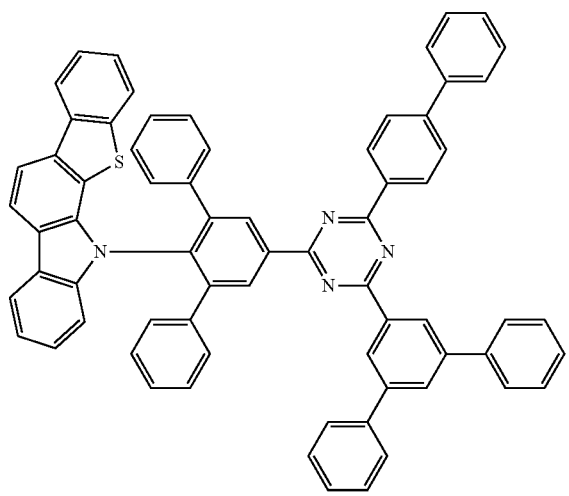
926
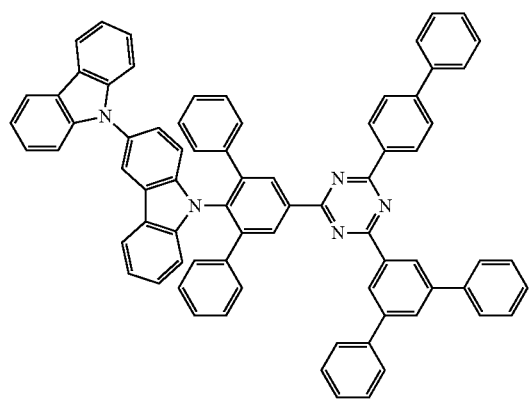
927
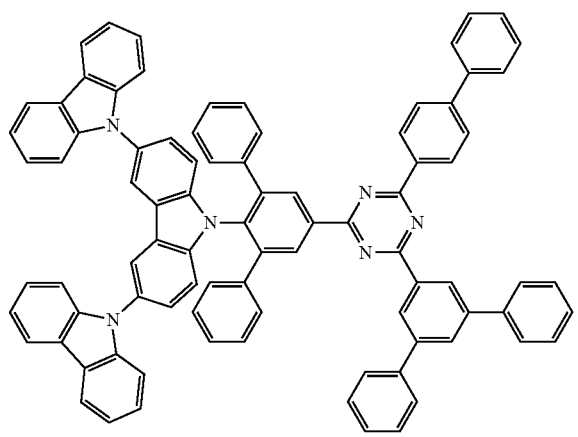

-continued
928
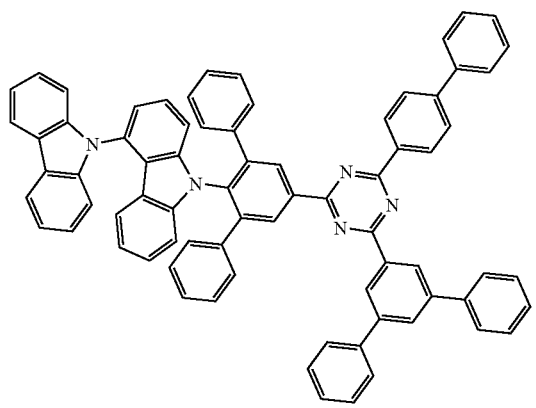
929
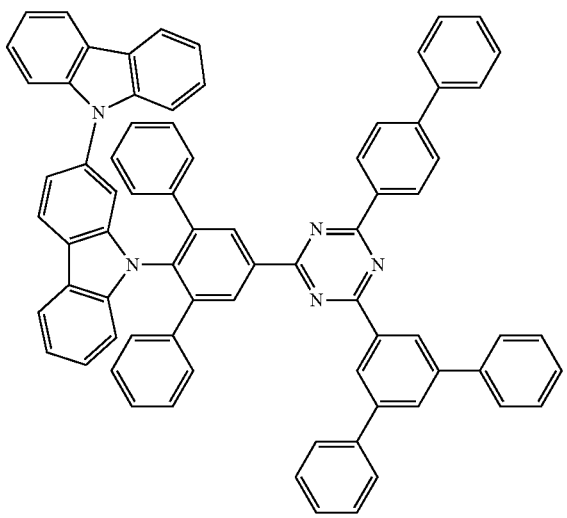
930
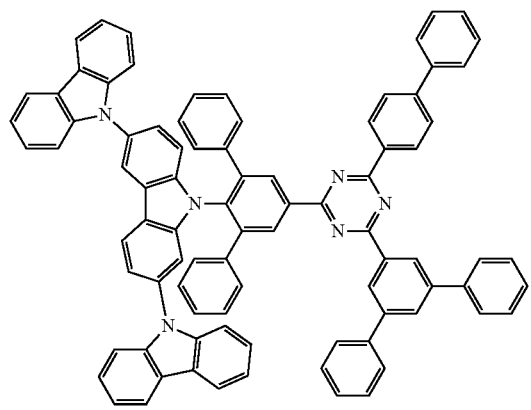
931
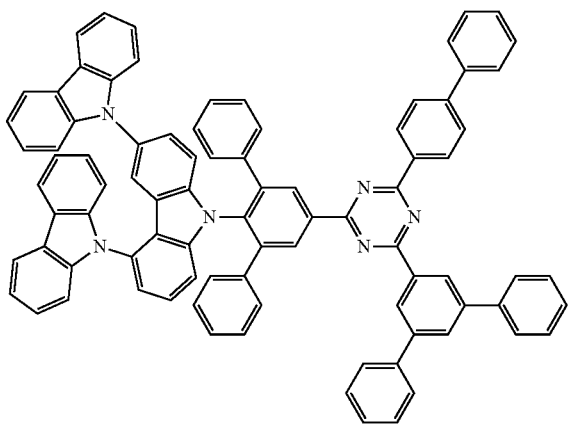
932
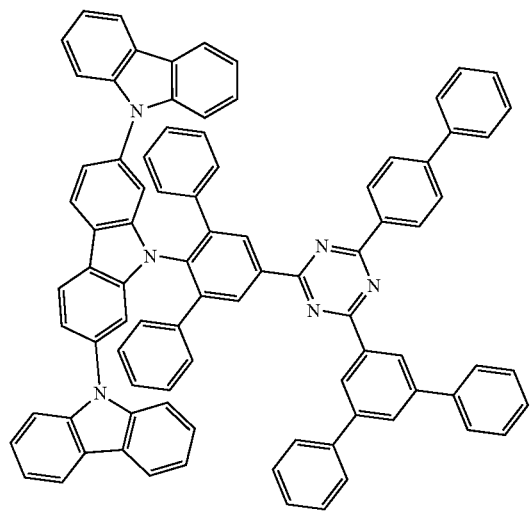
933
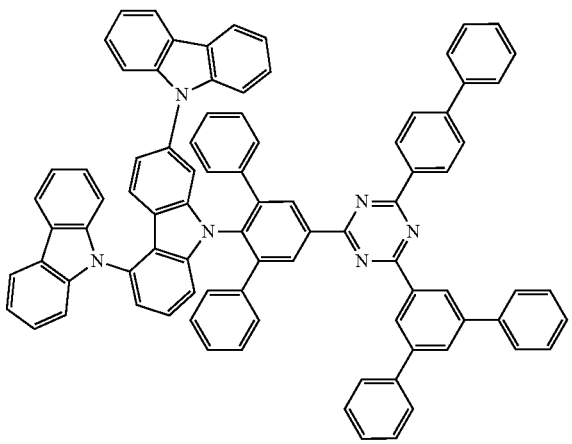

-continued
934
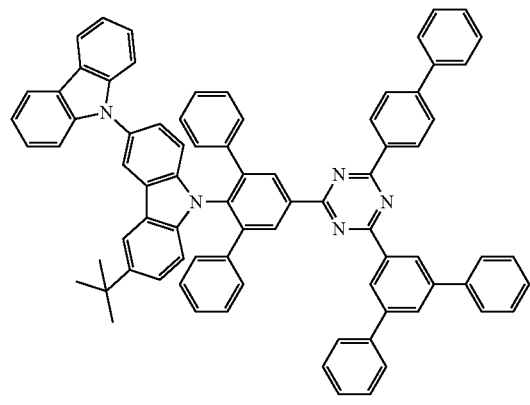
935
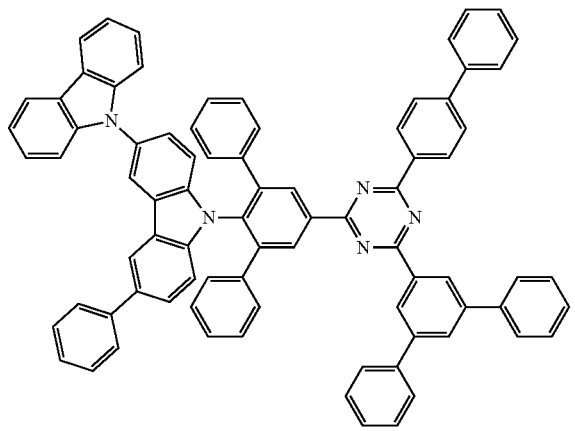
936
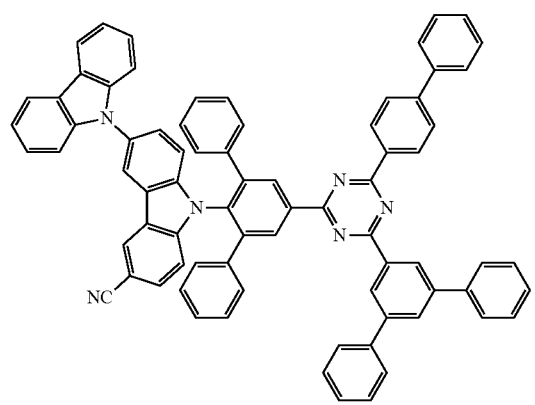
937
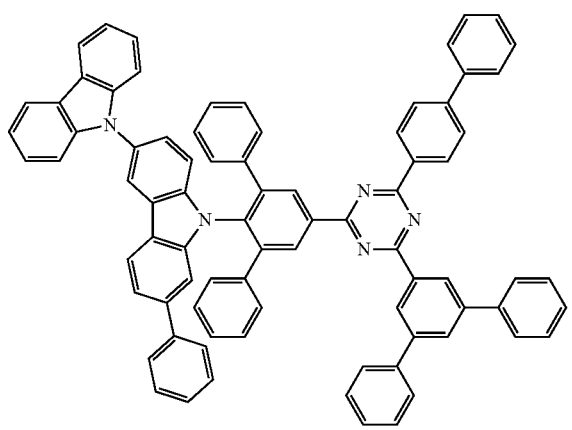
938
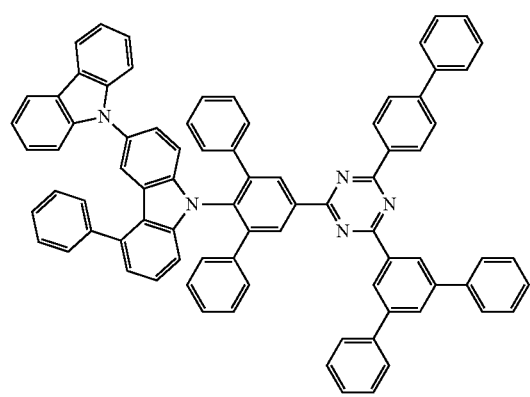
939
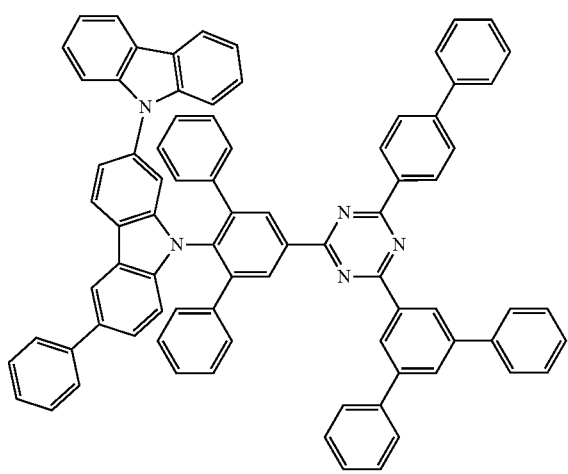

-continued
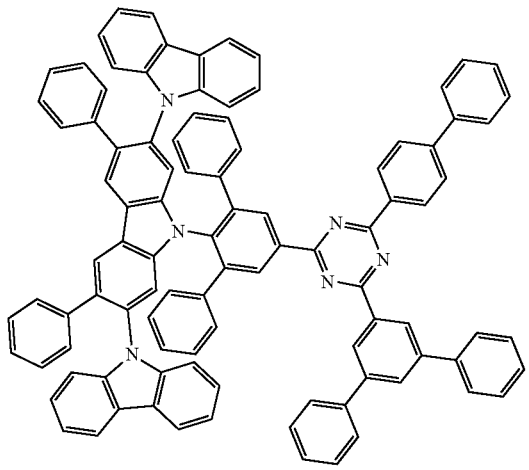
940
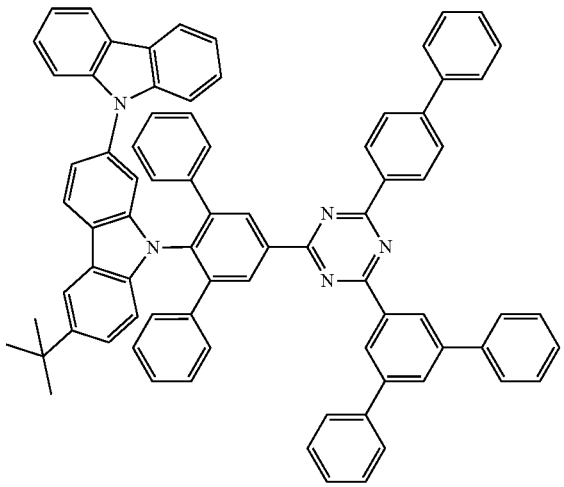
941
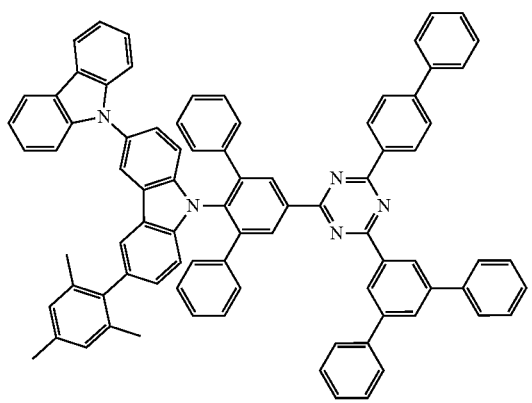
942
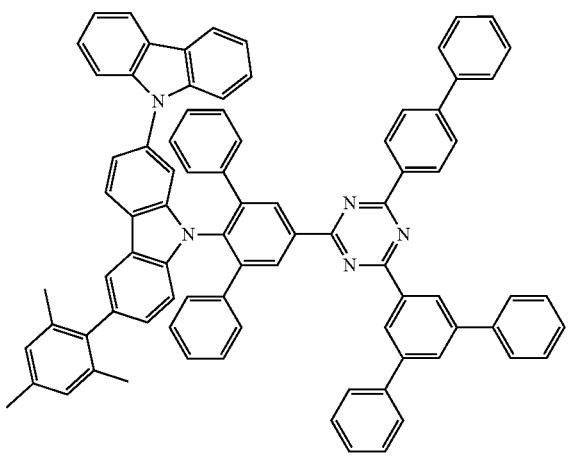
943
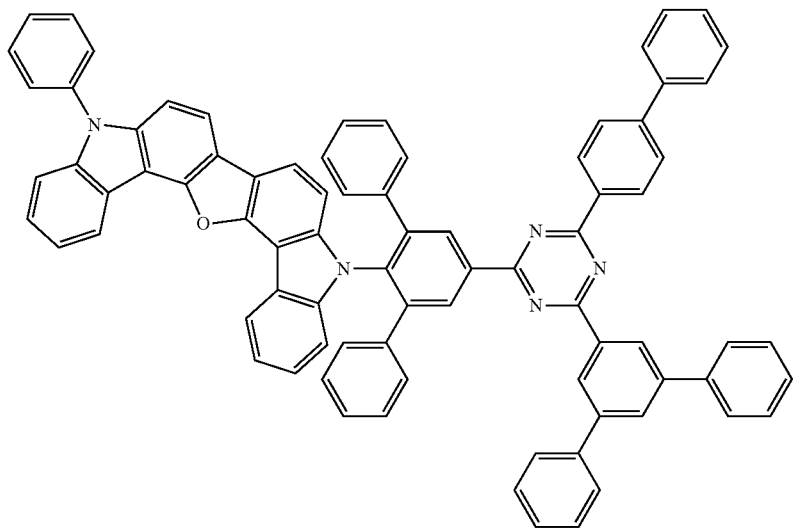
944

945
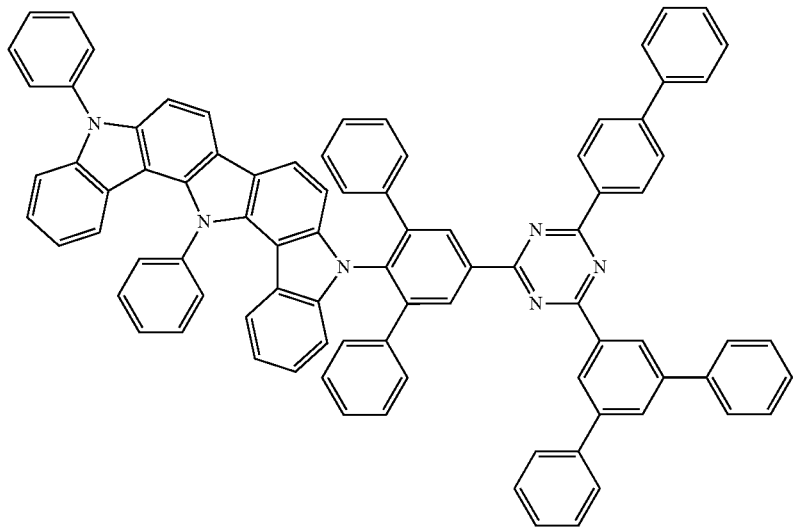
946
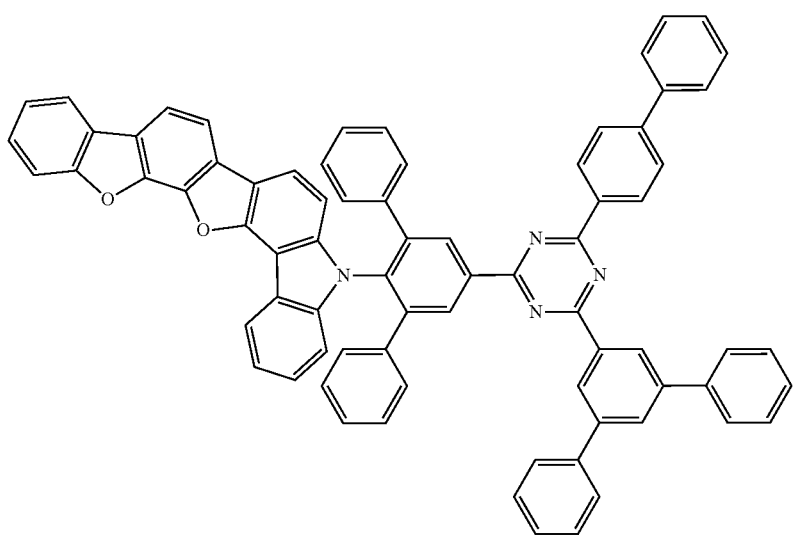
947
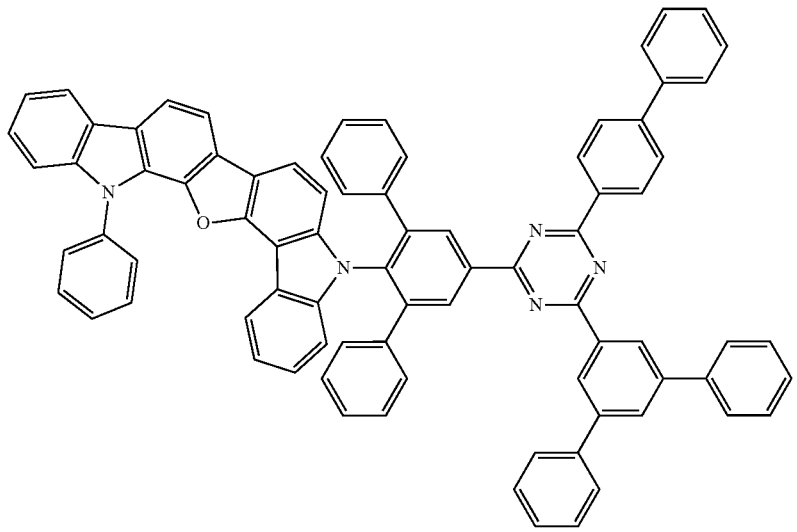

-continued
948
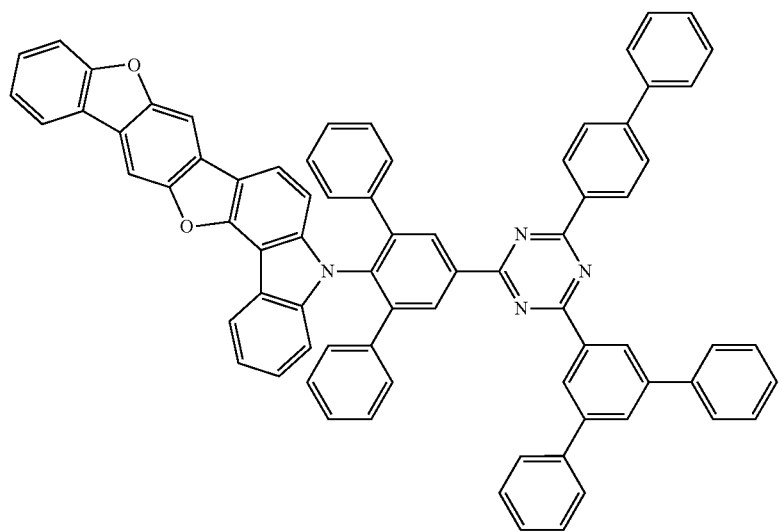
949
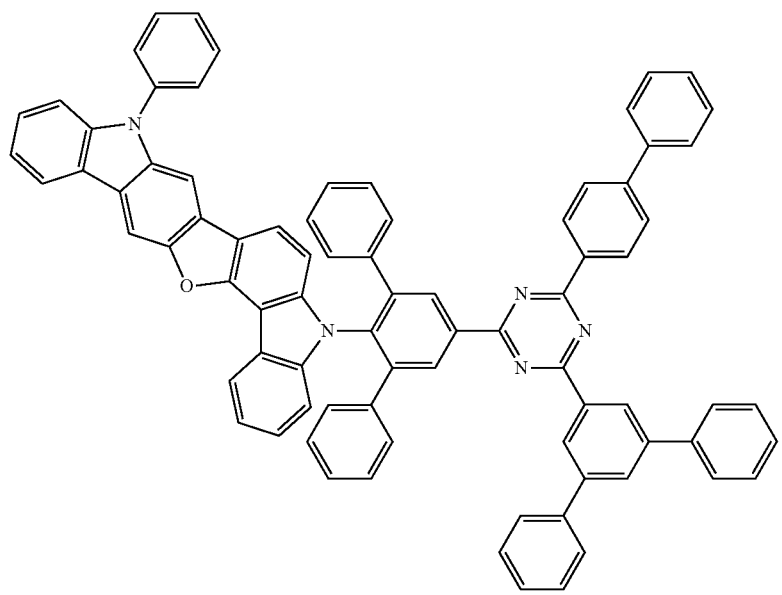
950
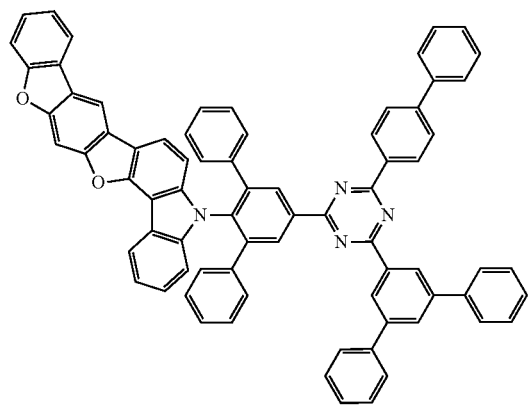

1213
-continued
1214
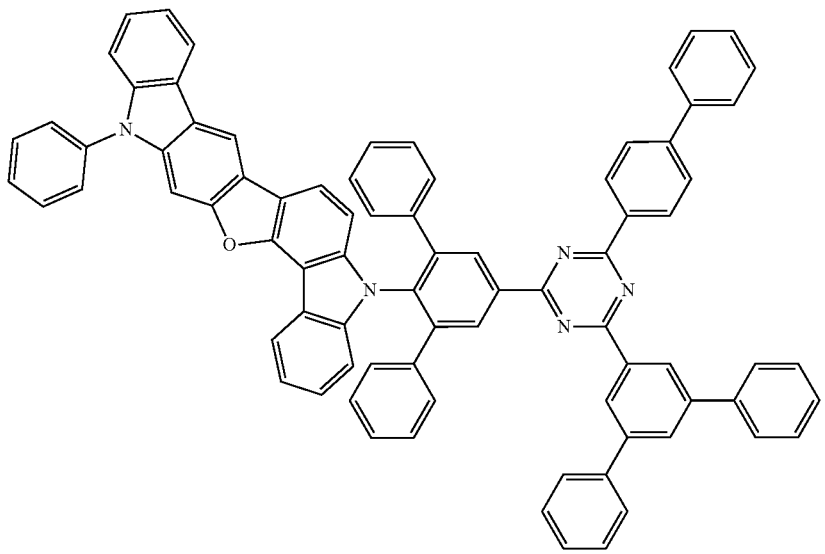
951
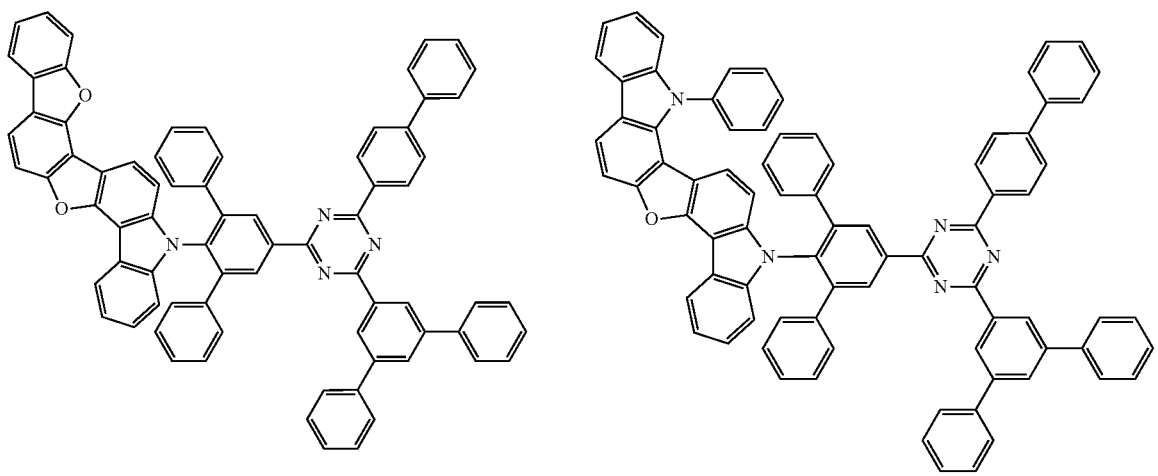
952    953
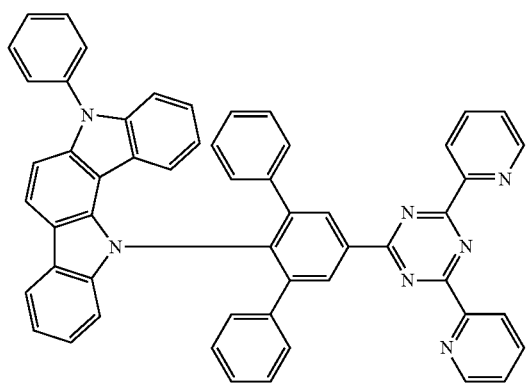
954

955
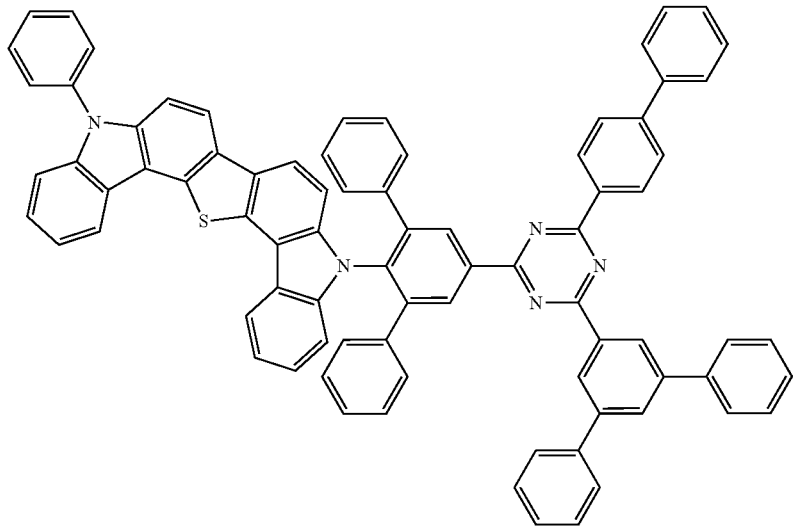
956
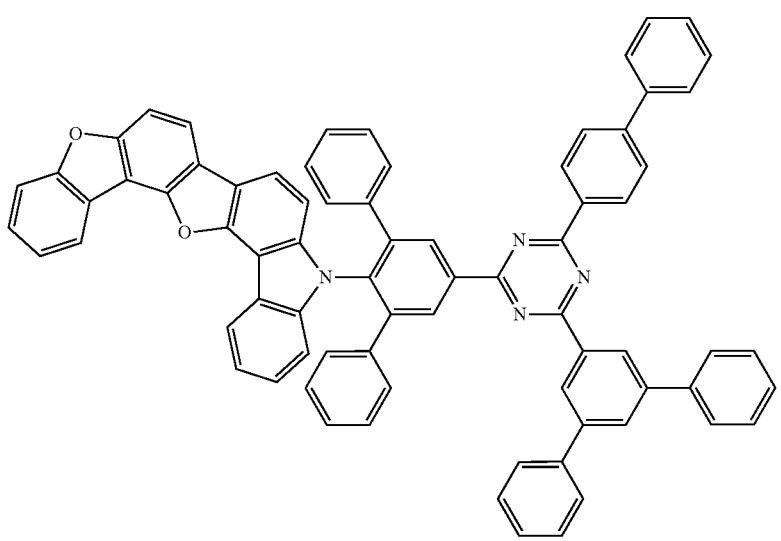
957
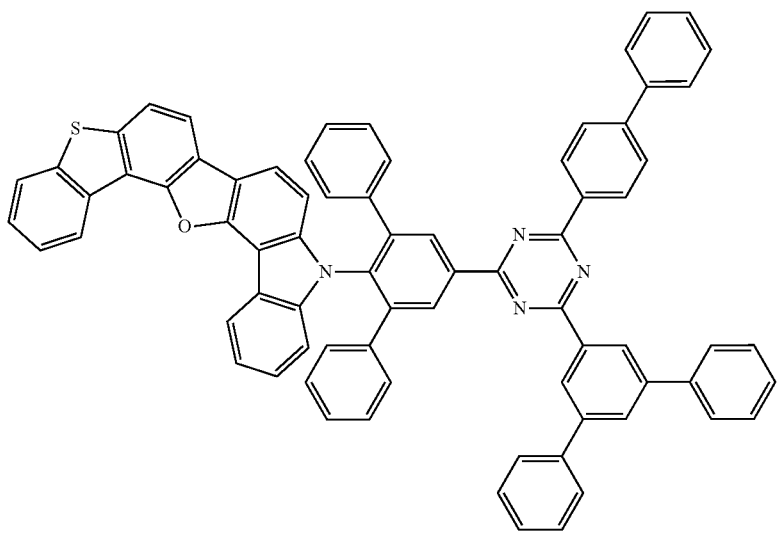

958
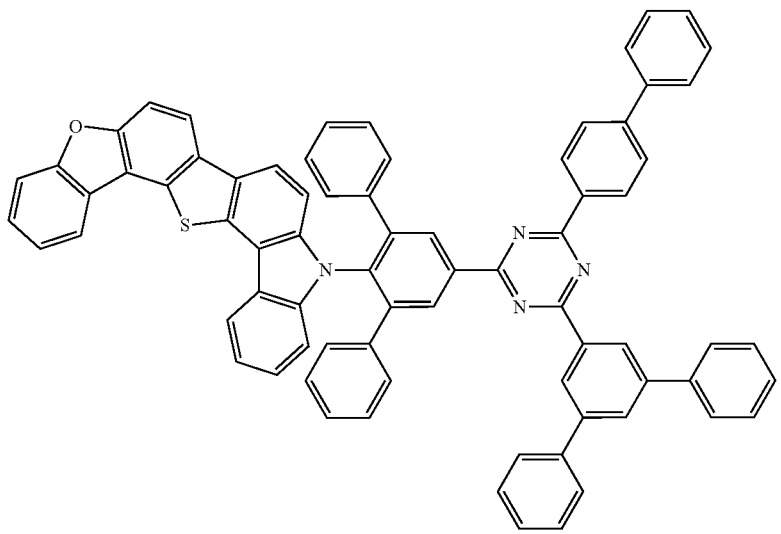
959
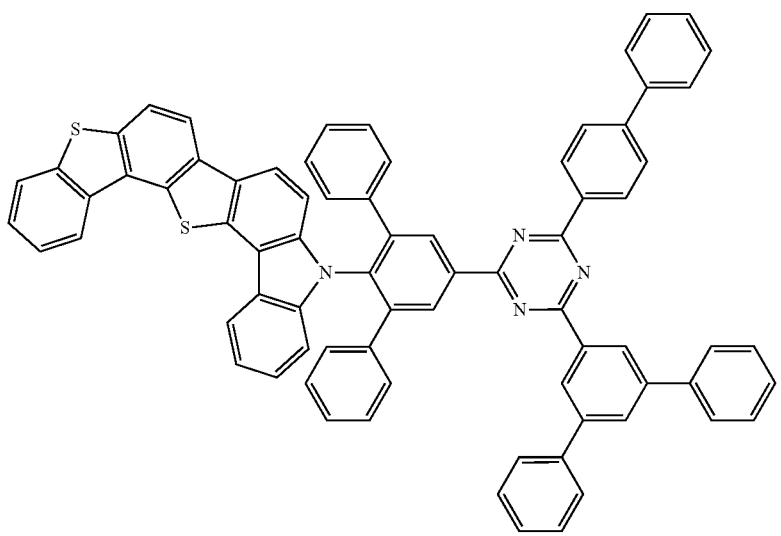
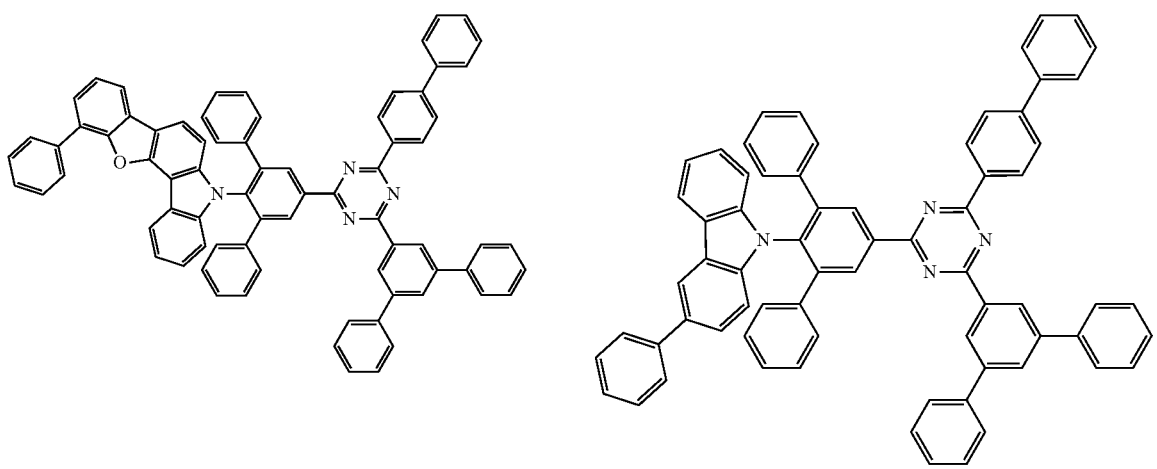
960 961

-continued
1219
962
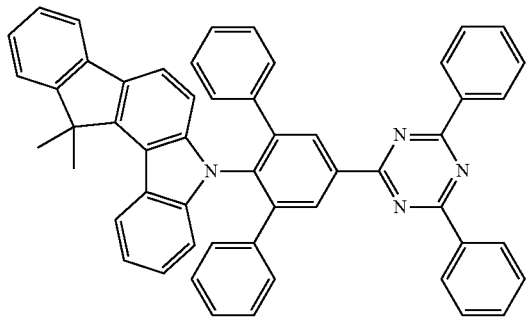
964
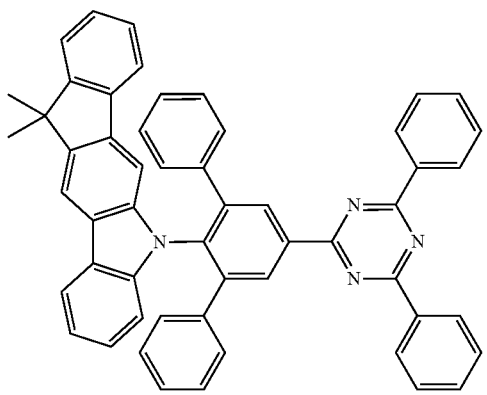
966
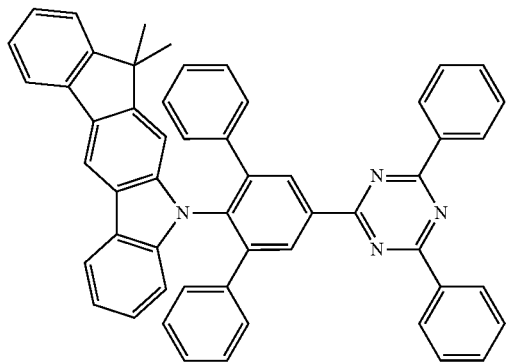
968
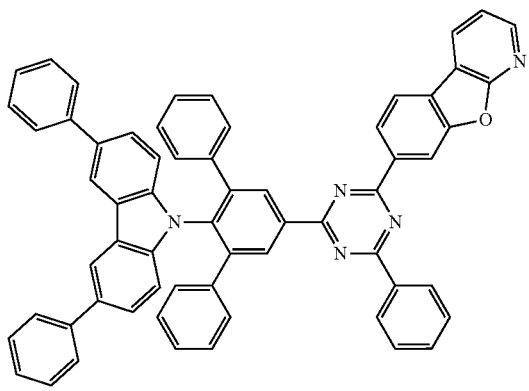
1220
963
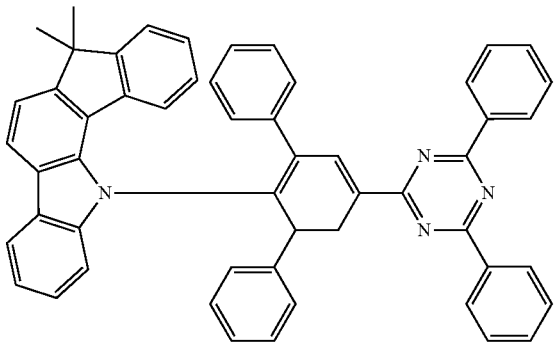
965
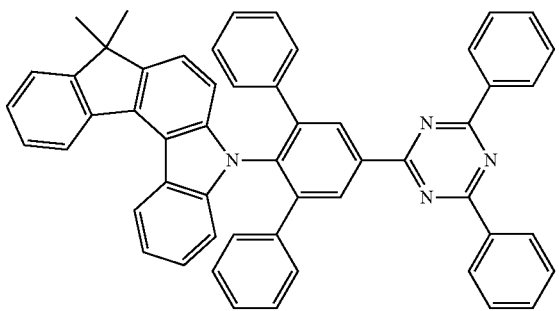
967
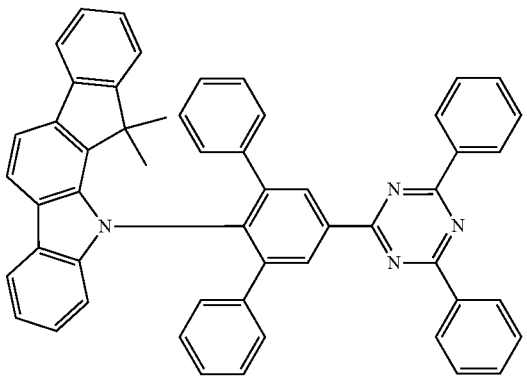
969
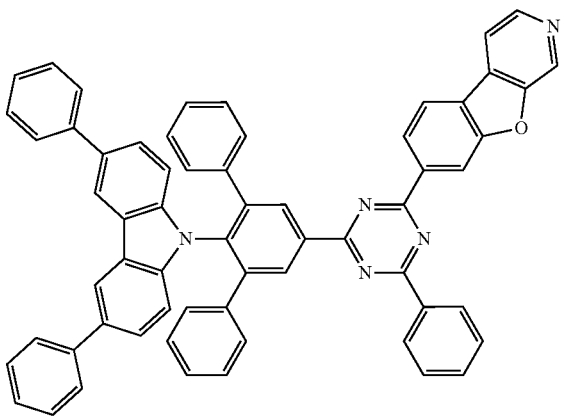

970
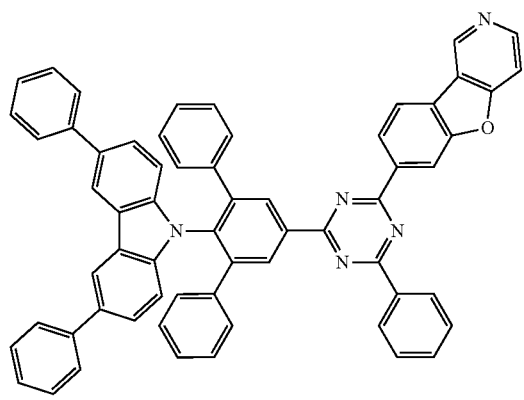
971
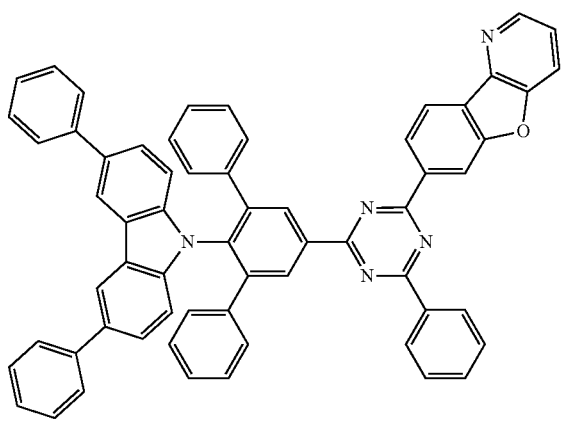
972
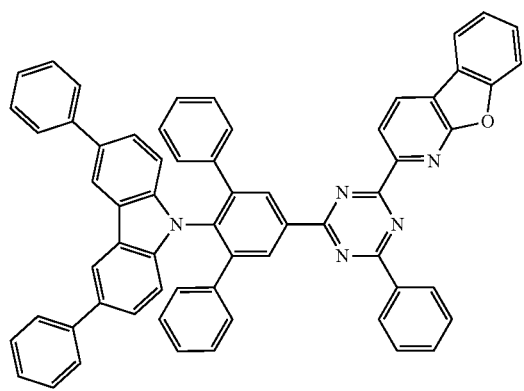
973
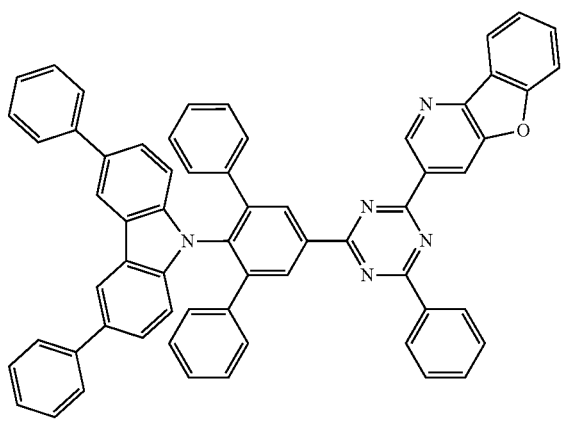
974
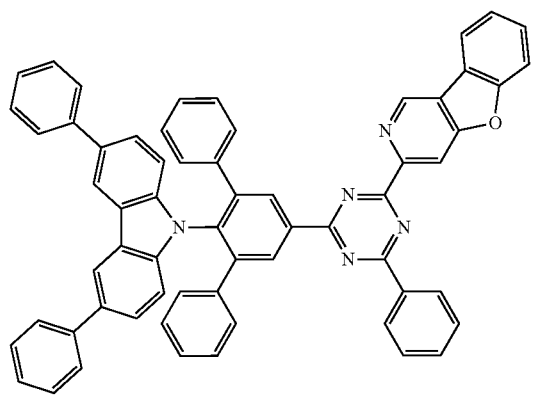
975
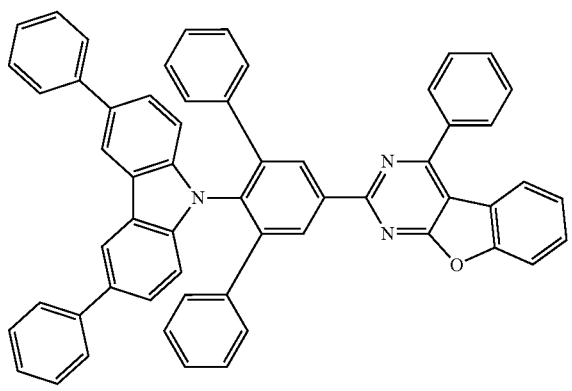

1223 1224
976
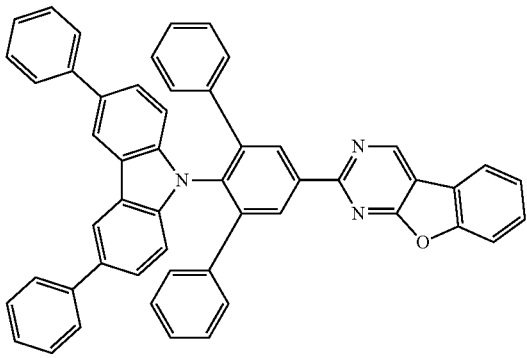
977
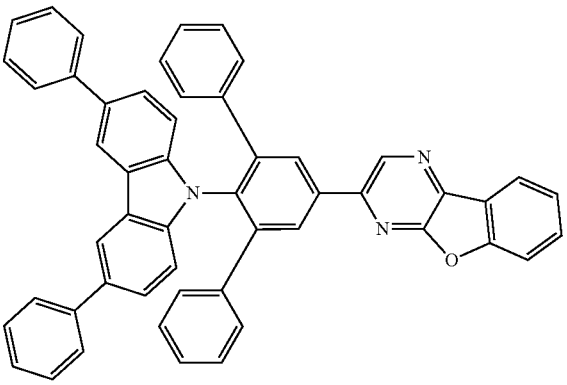
978
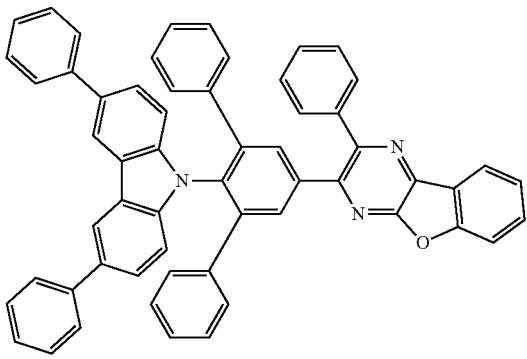
979
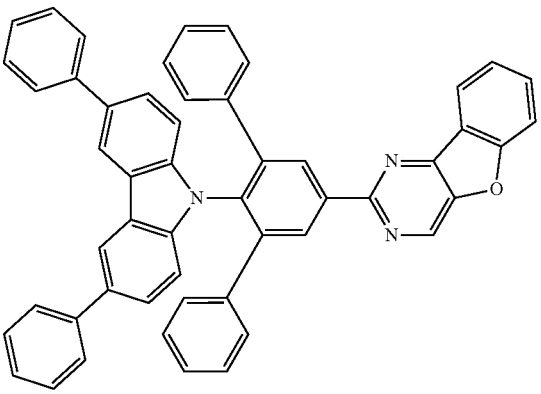
980
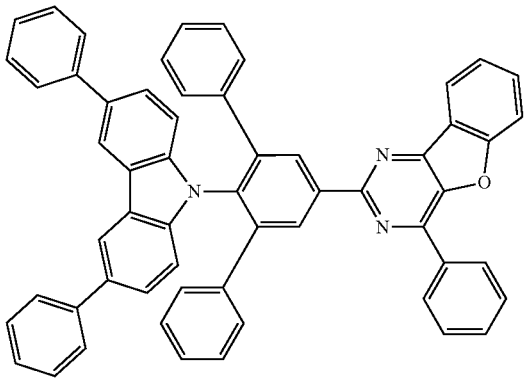
981
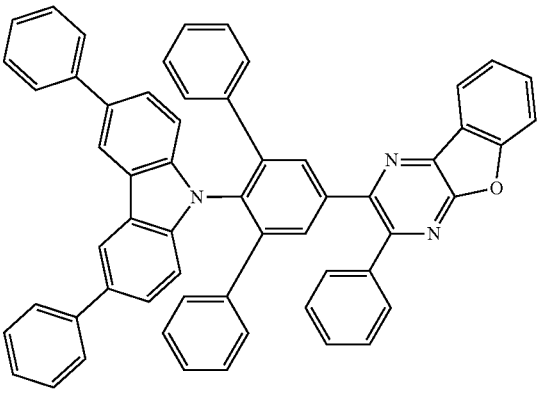
982
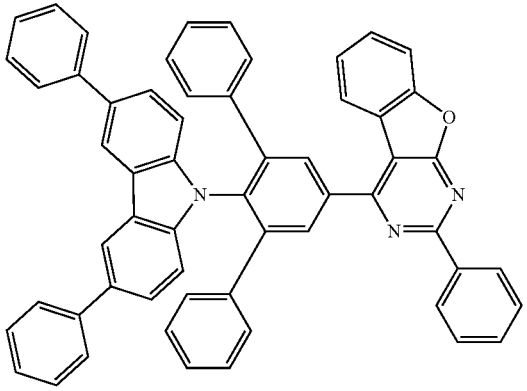
983
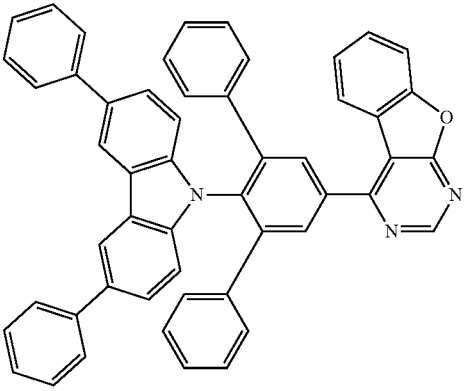

-continued
1225
984
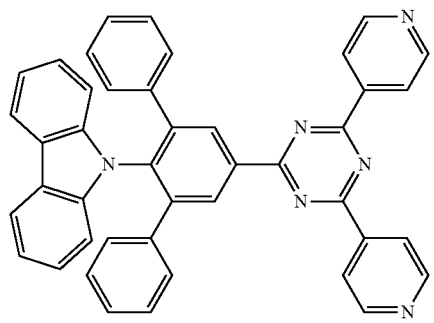
1226
985
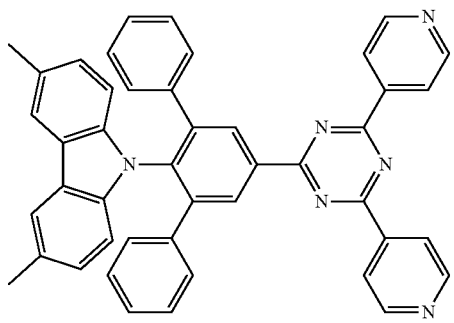
986
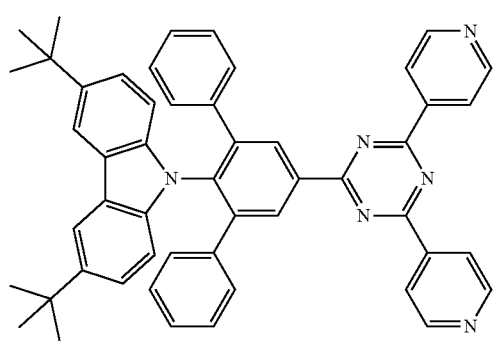
987
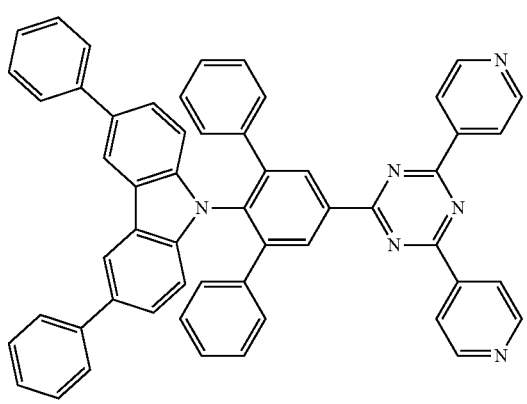
988
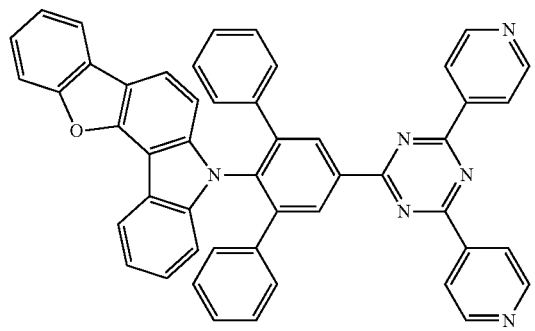
989
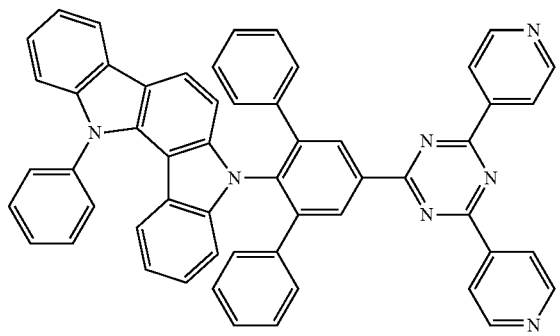
990
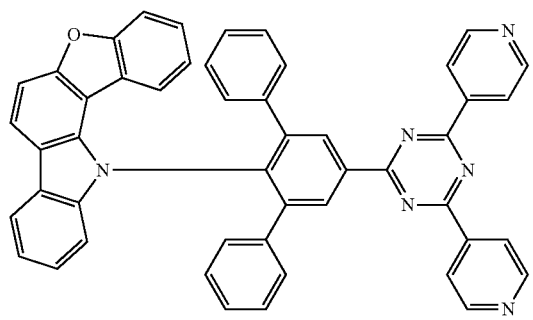
991
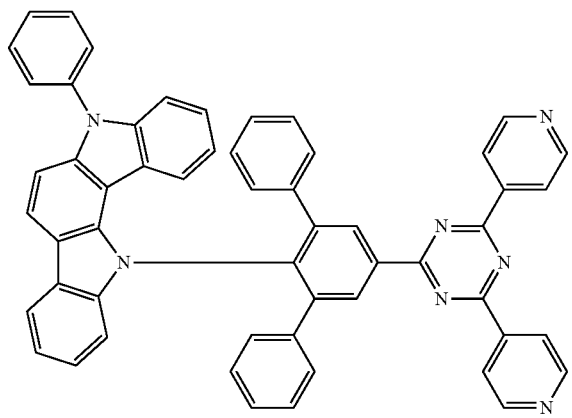

-continued
992
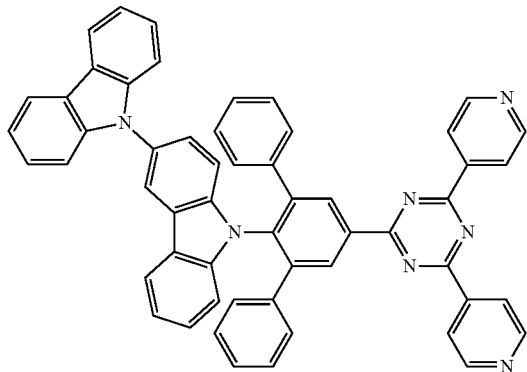
993
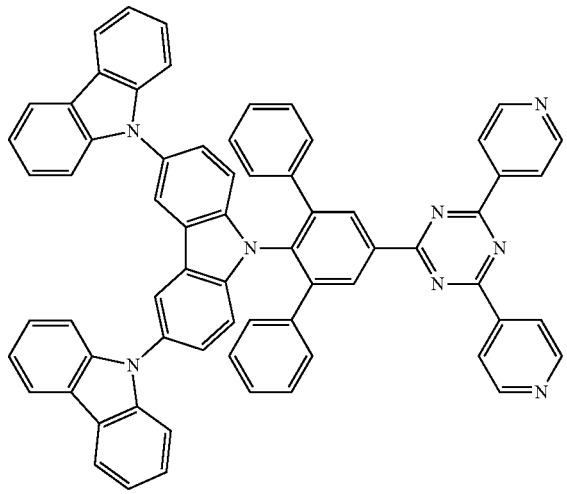
994
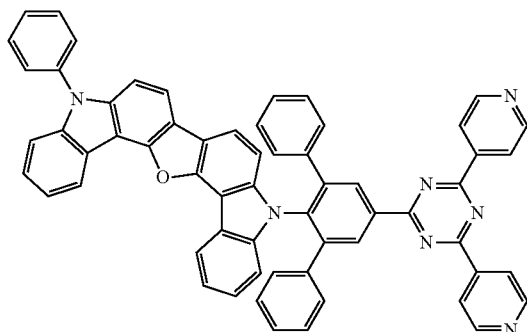
995
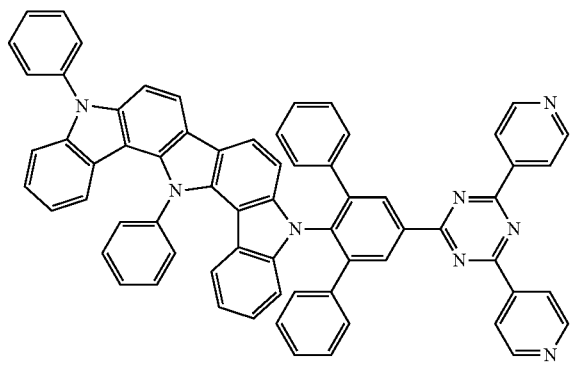
996
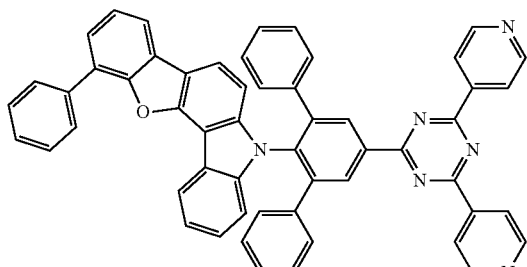
997
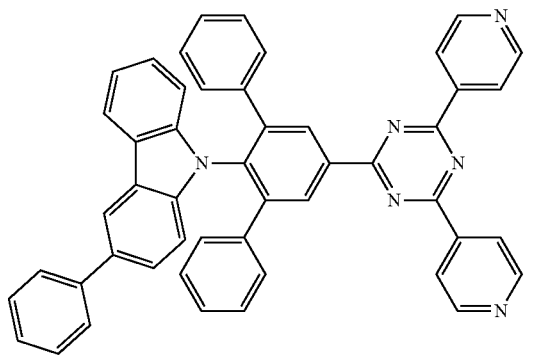
998
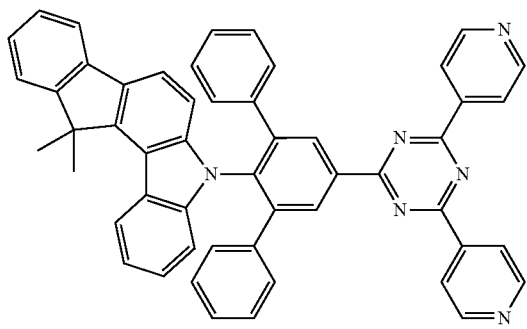
999
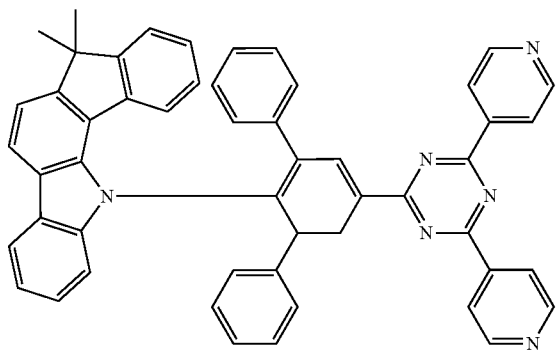

-continued
1000
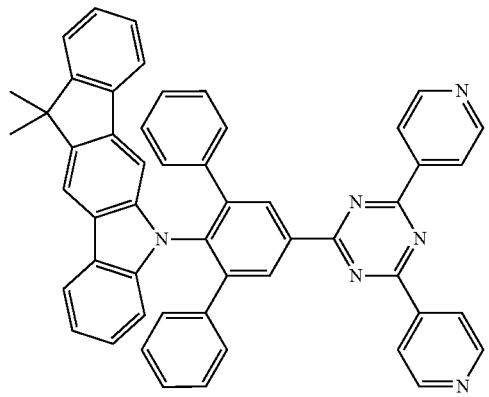
1001
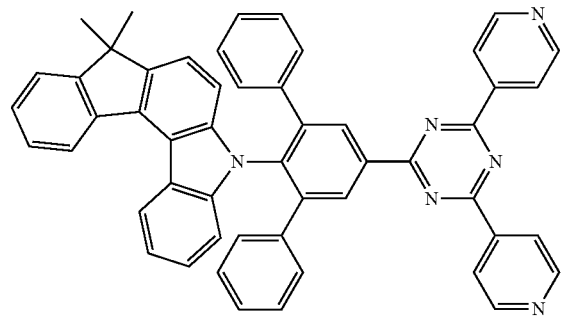
1002
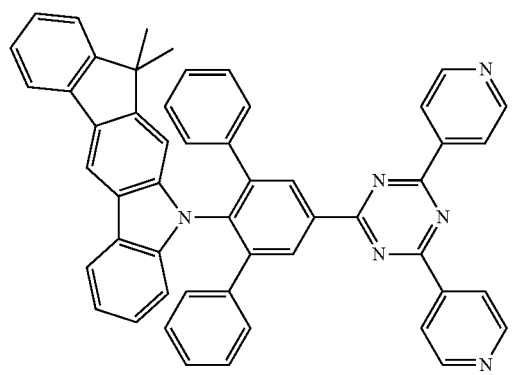
1003
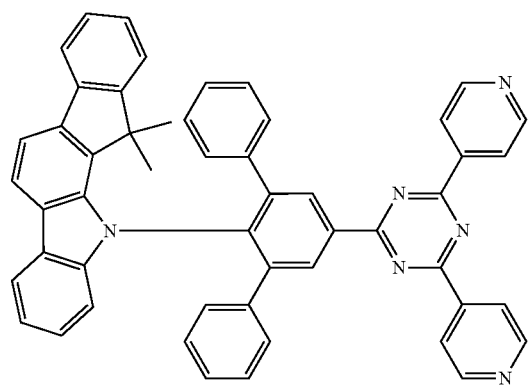
1004
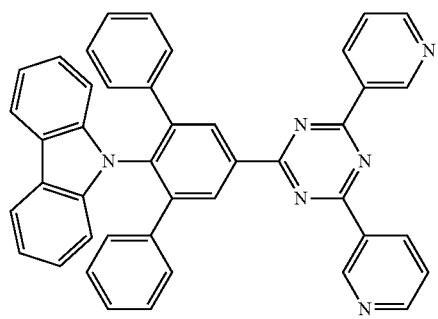
1005
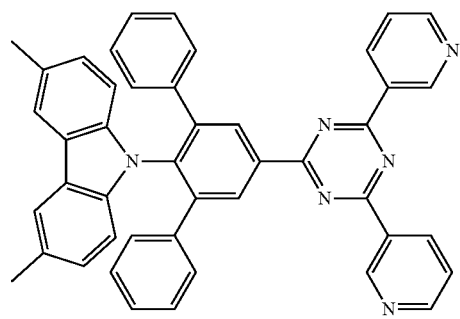
1006
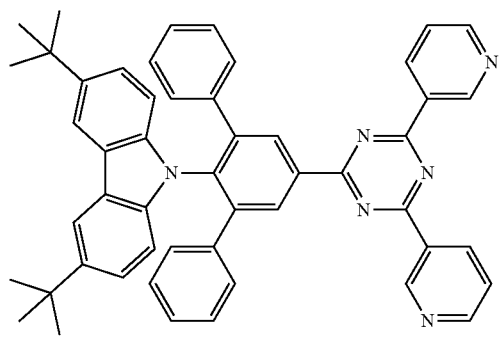
1007
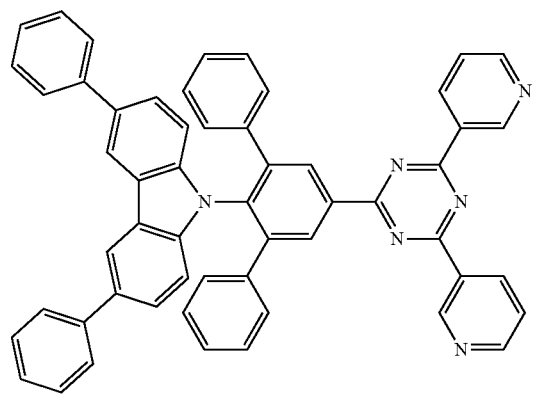

-continued
1008
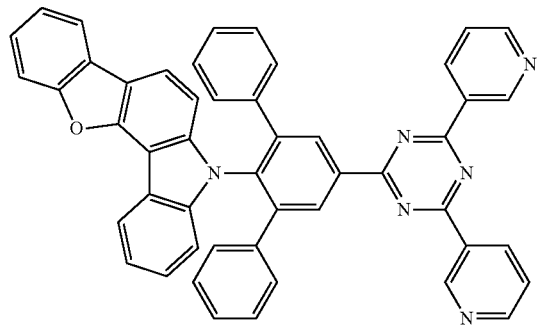
1009
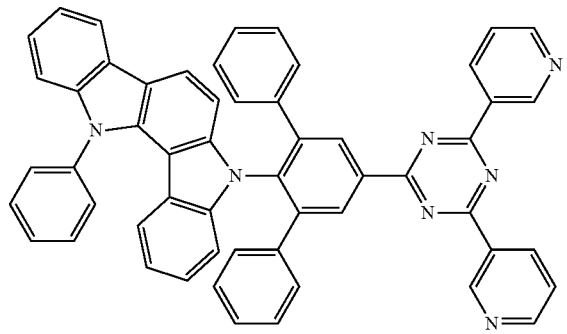
1010
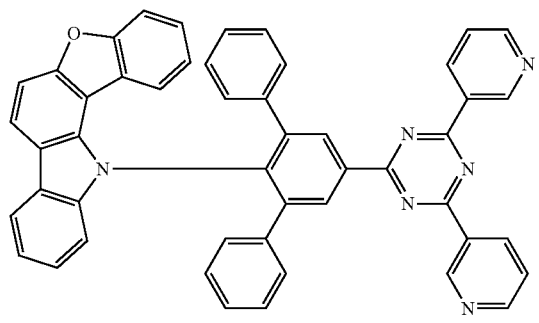
1011
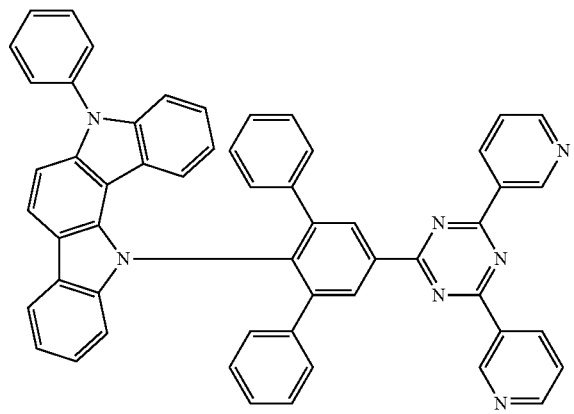
1012
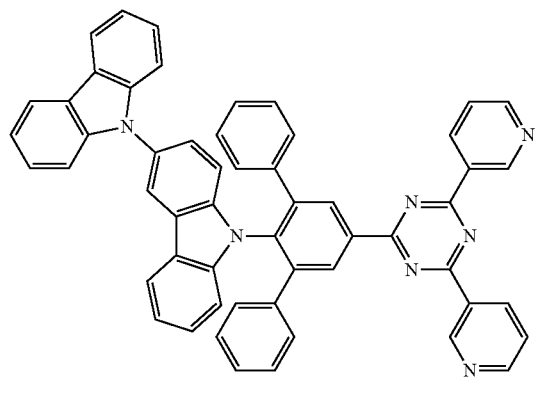
1013
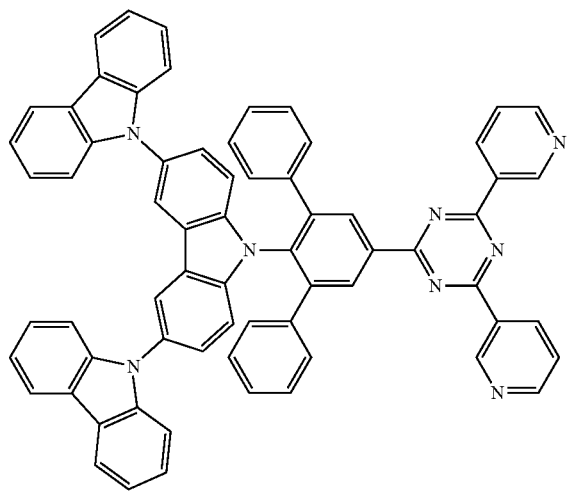

-continued
1014
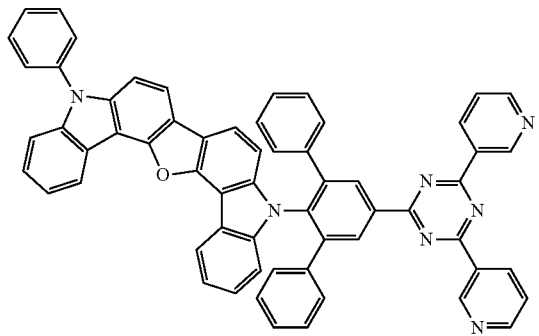
1015
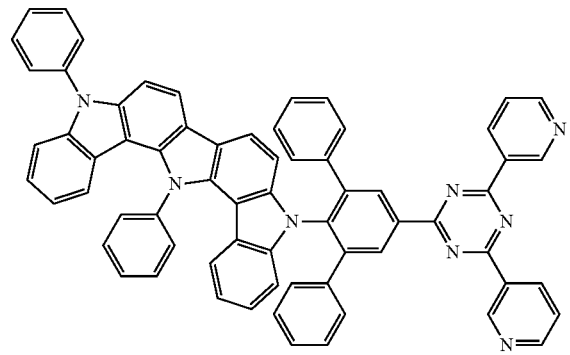
1016
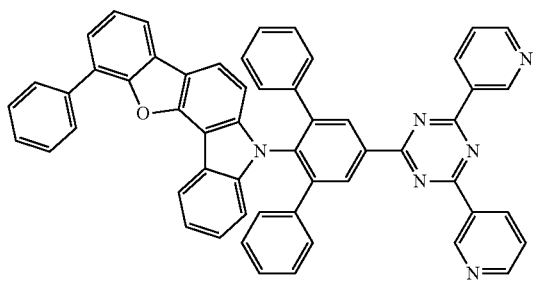
1017
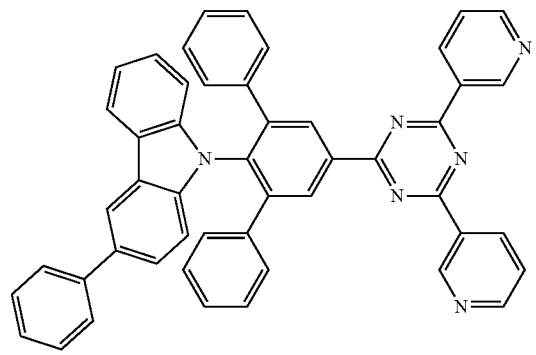
1018
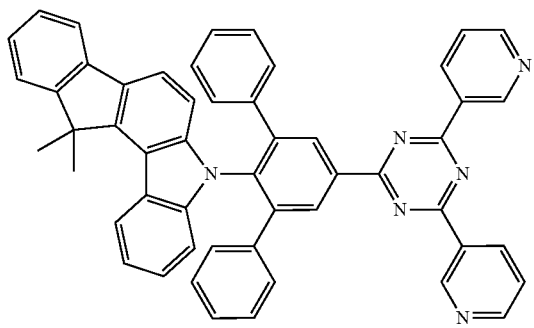
1019
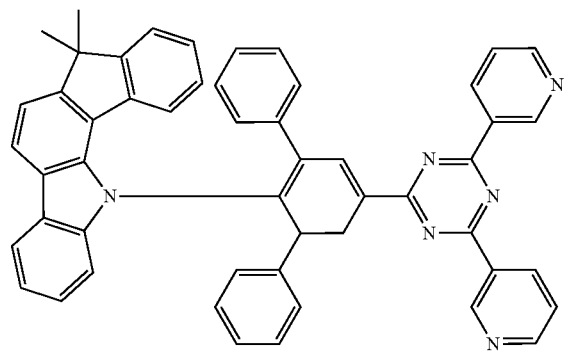
1020
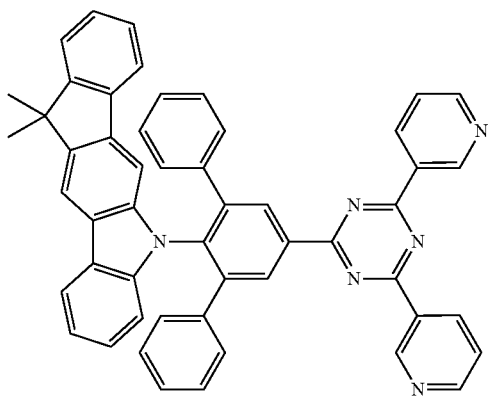
1021
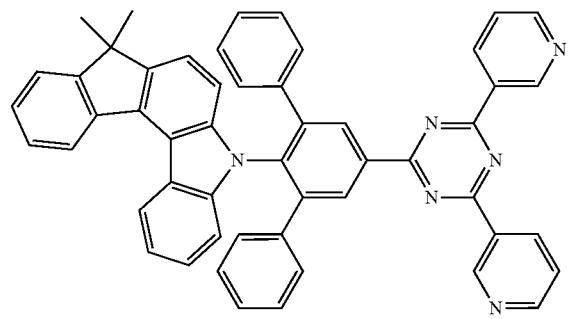

1235 1236
-continued
1022 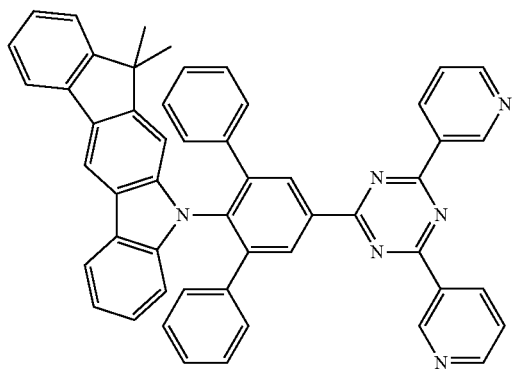 1023 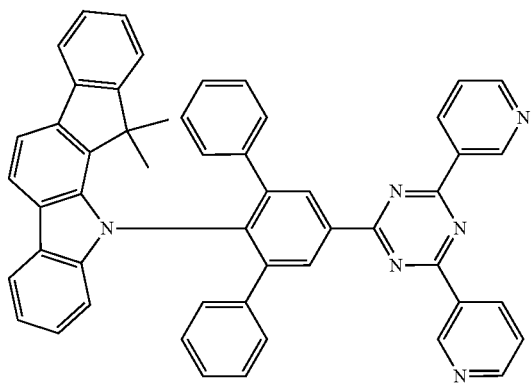
1024 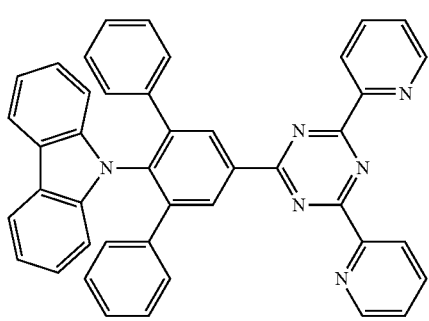 1025 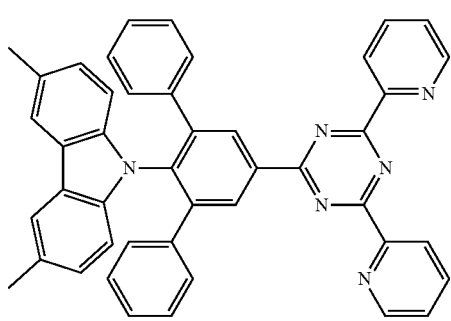
1026 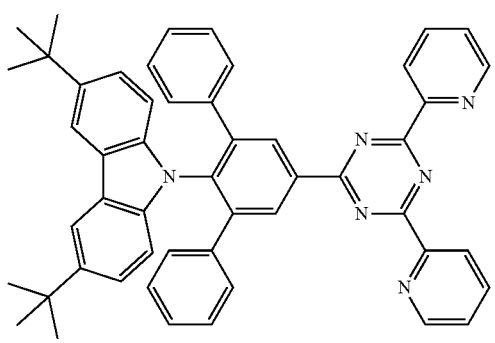 1027 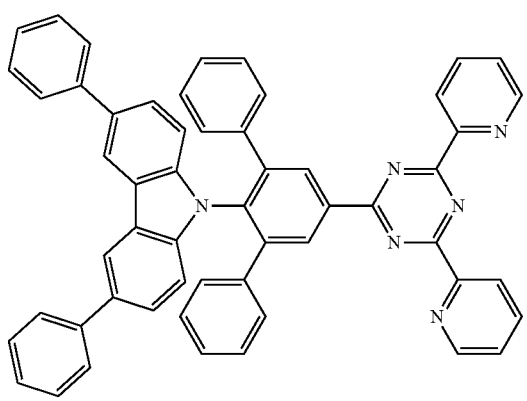
1028 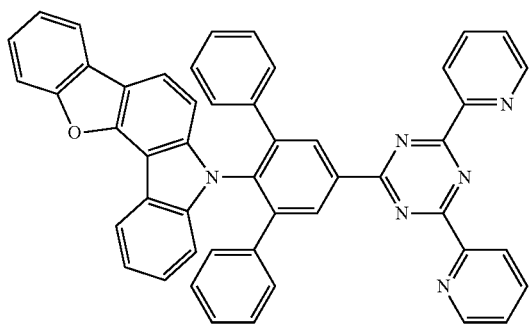 1029 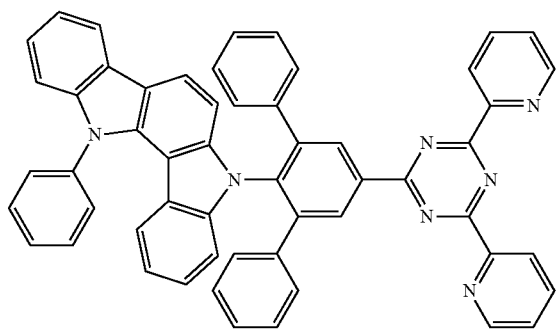

1237
-continued
1030
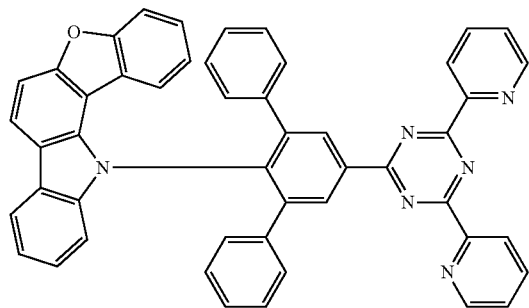
<Group X>
1
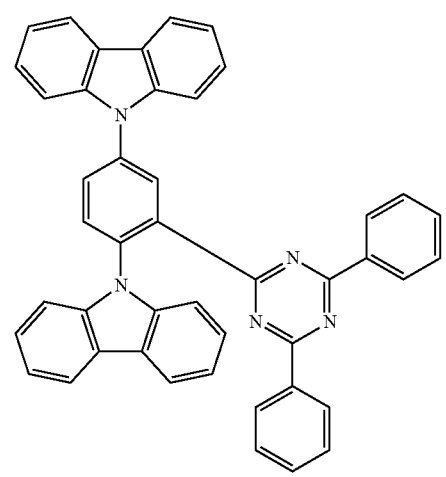
2
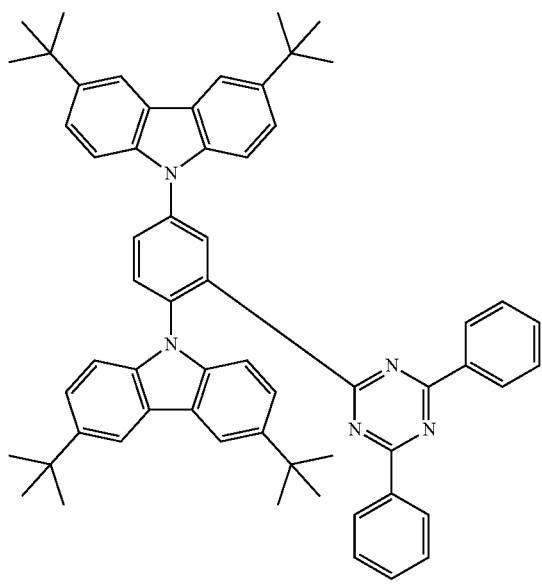
1238
-continued
3
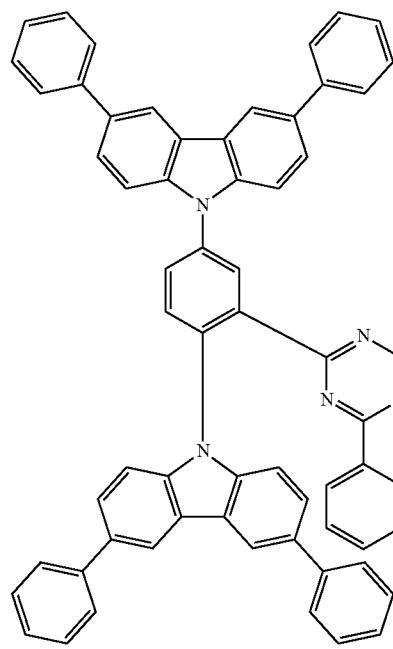
4
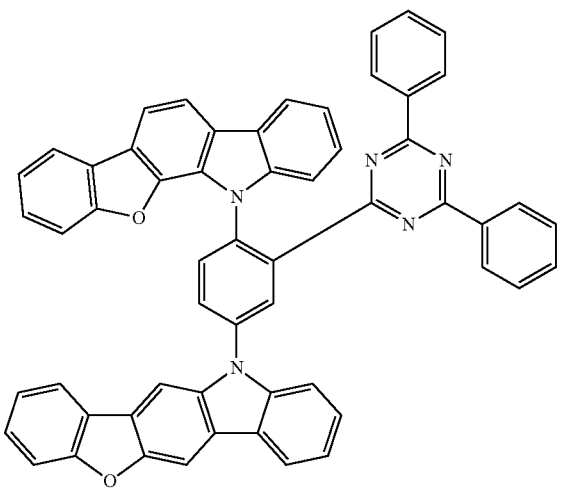

1239
-continued
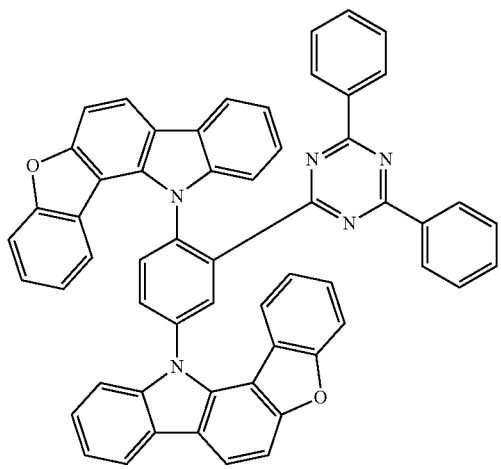
5
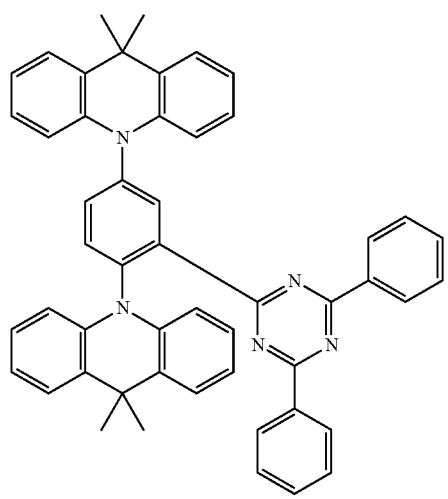
6
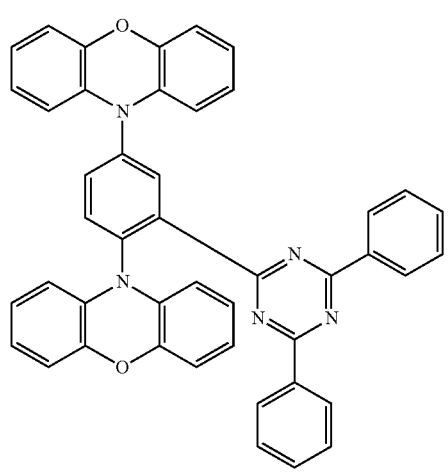
7
1240
-continued
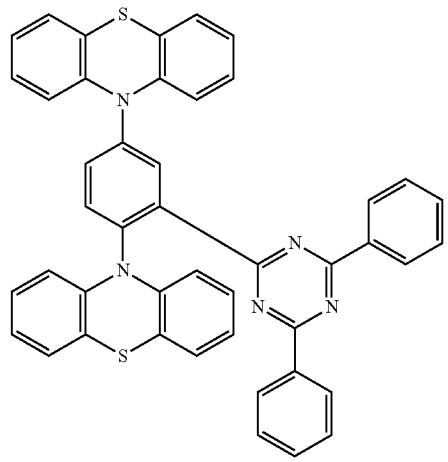
8
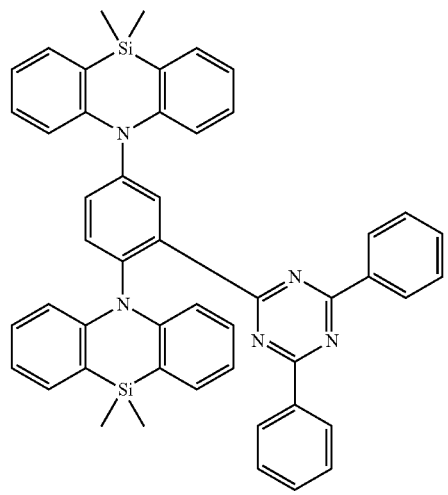
9
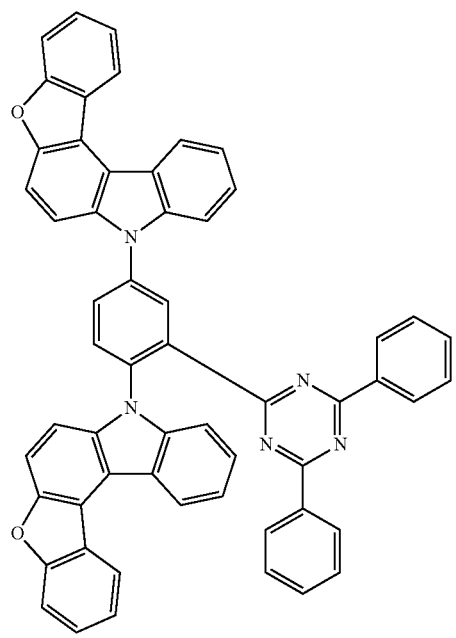
10

1241
-continued
11
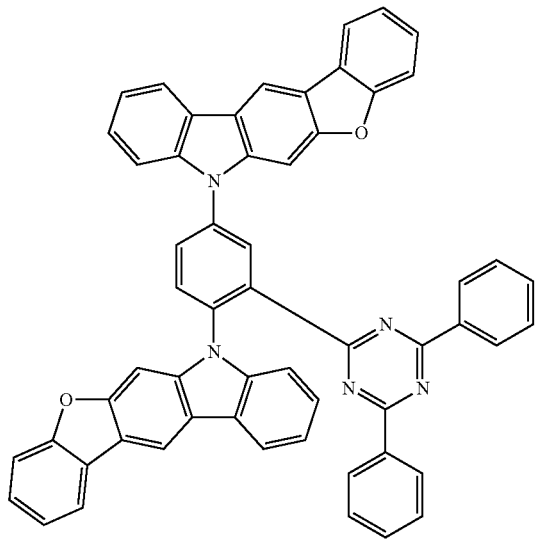
12
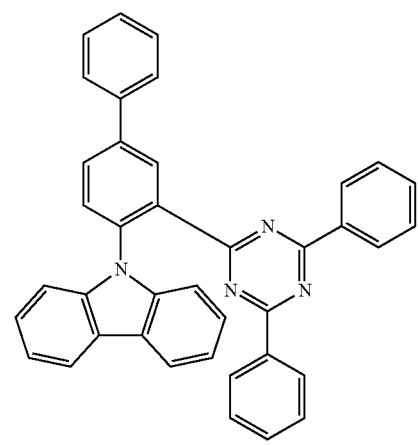
13
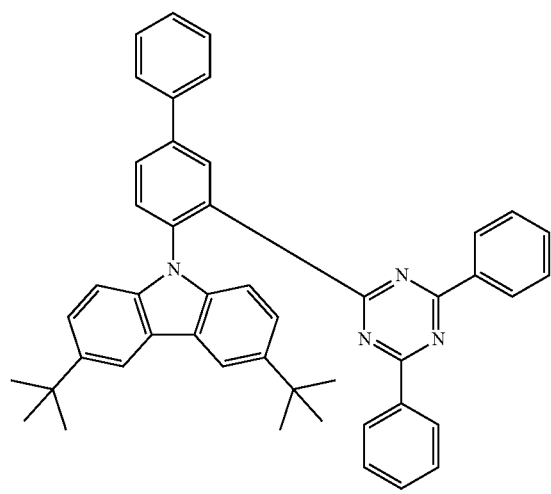
1242
-continued
14
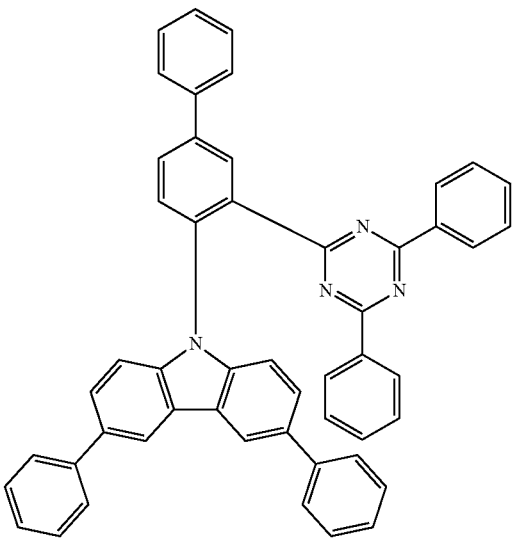
15
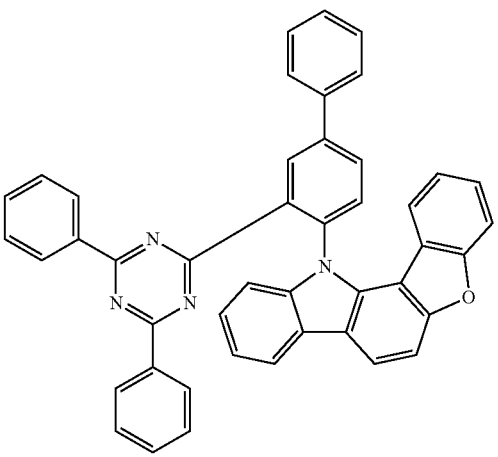
16

17
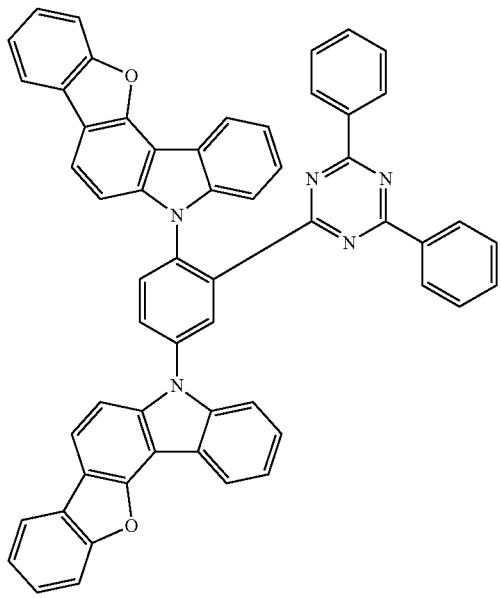
18
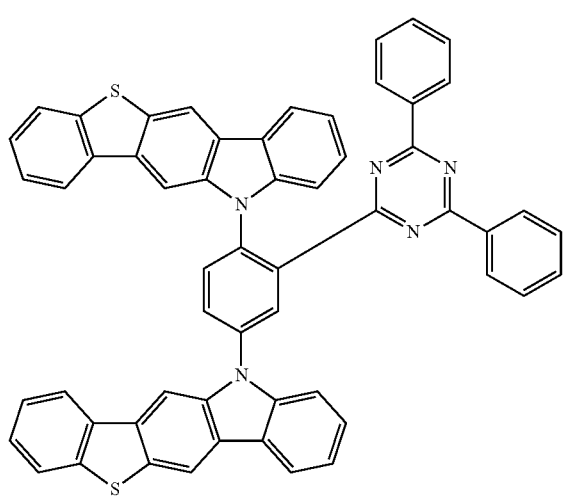
19
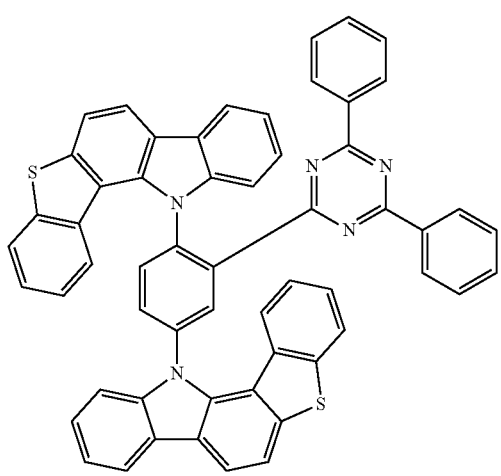
20
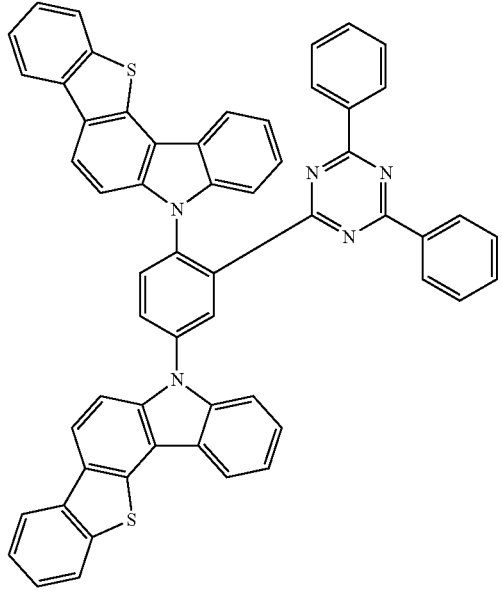
21
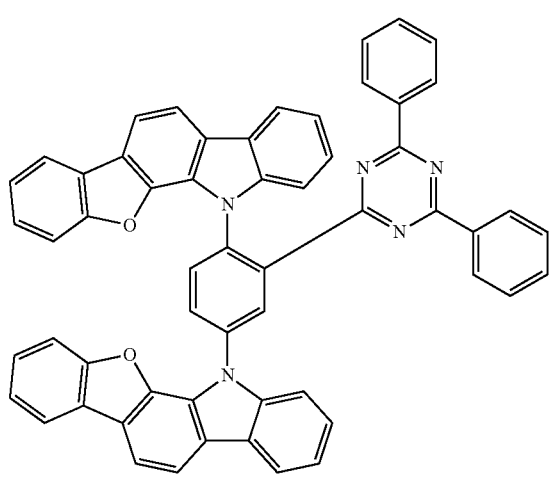

1245
-continued
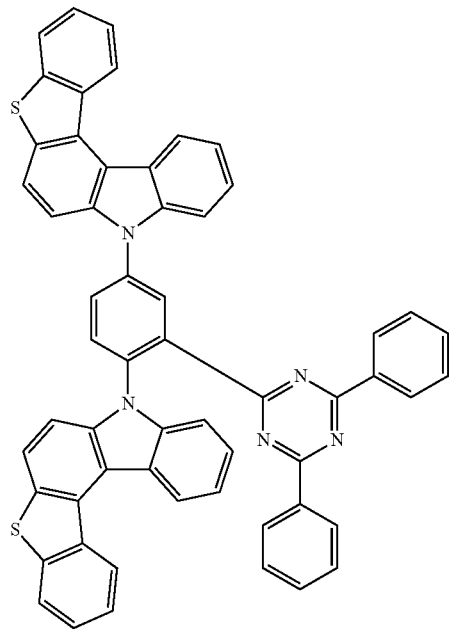
22
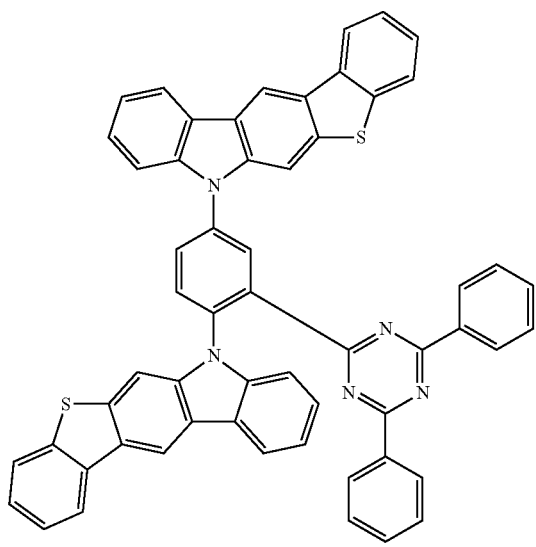
23
1246
-continued
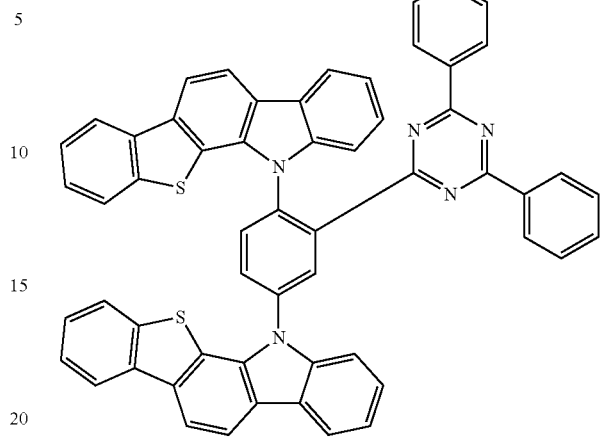
24
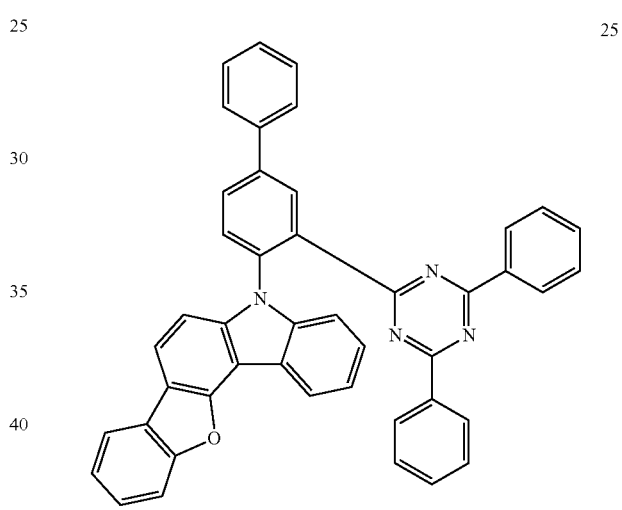
25
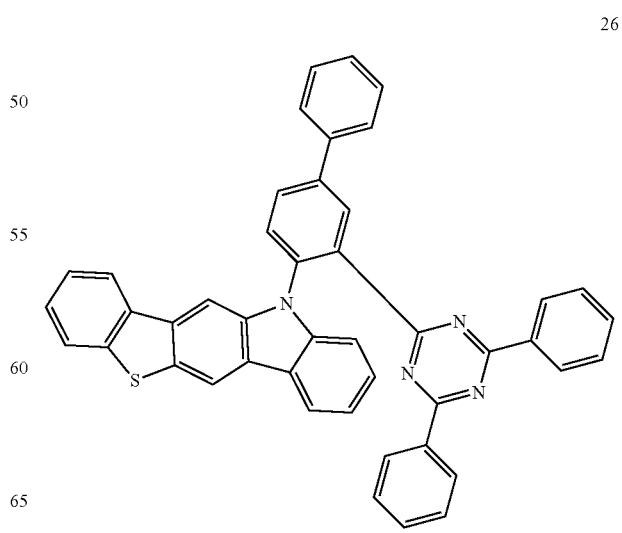
26

1247
27
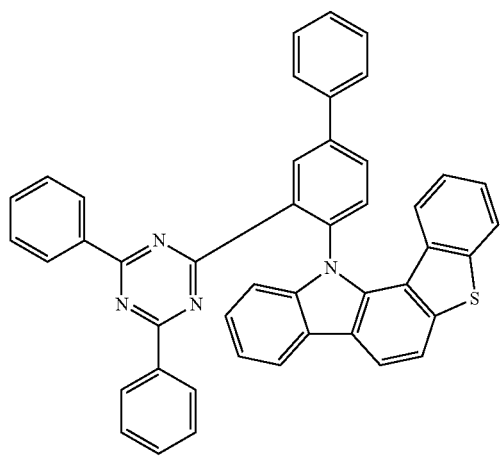
28
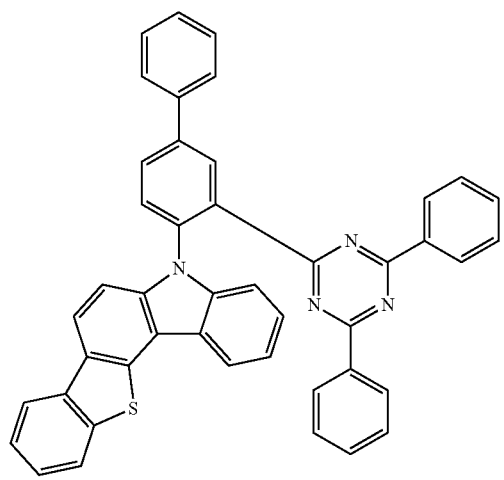
29
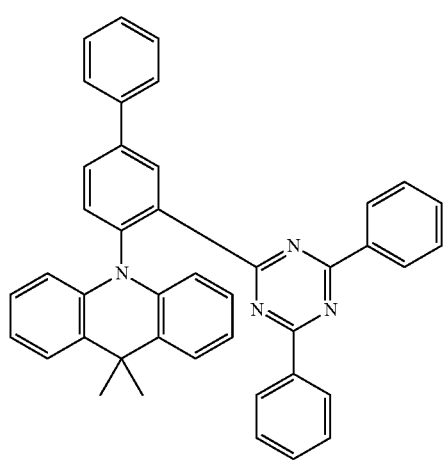
1248
30
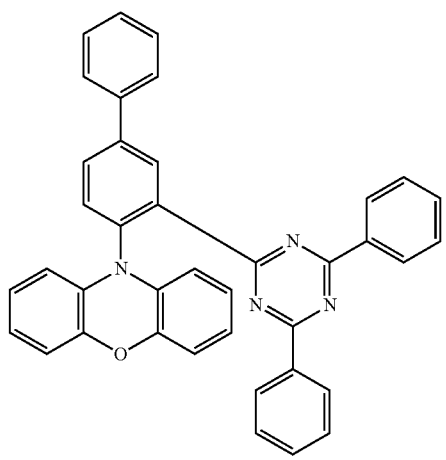
31
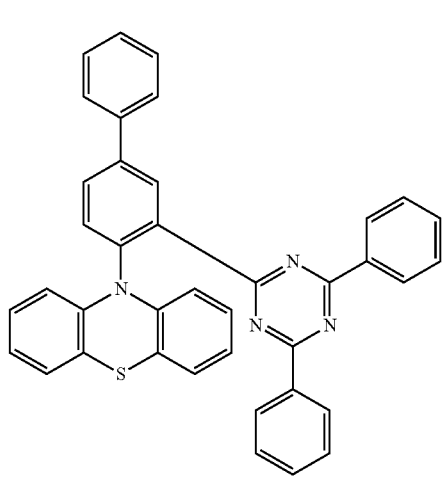
32
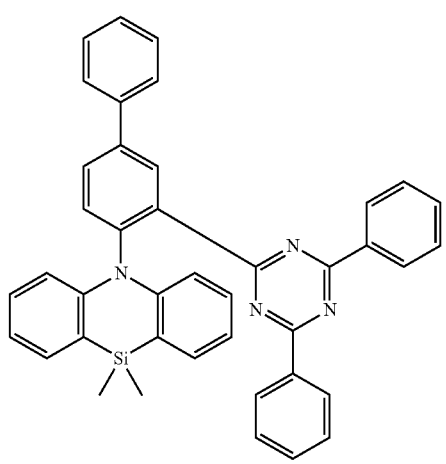

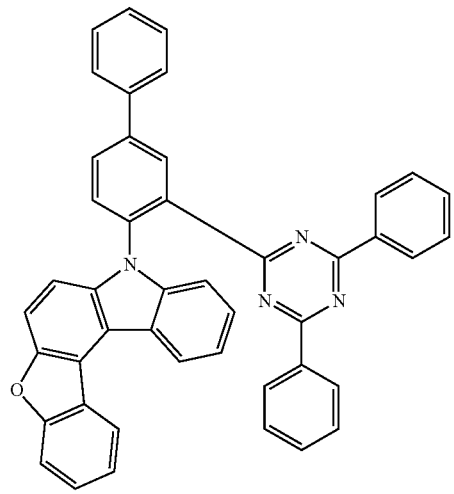
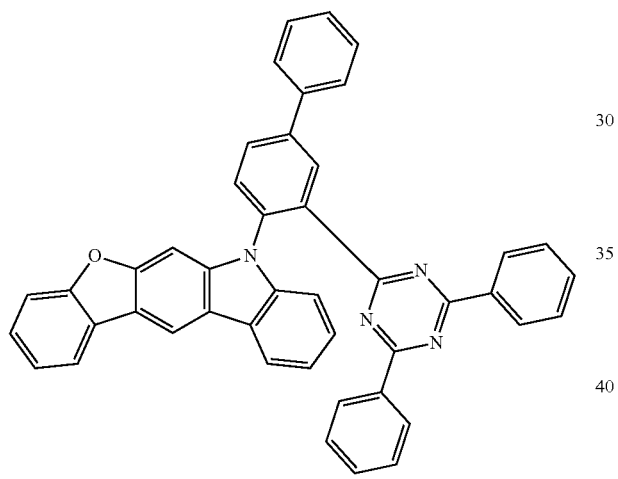
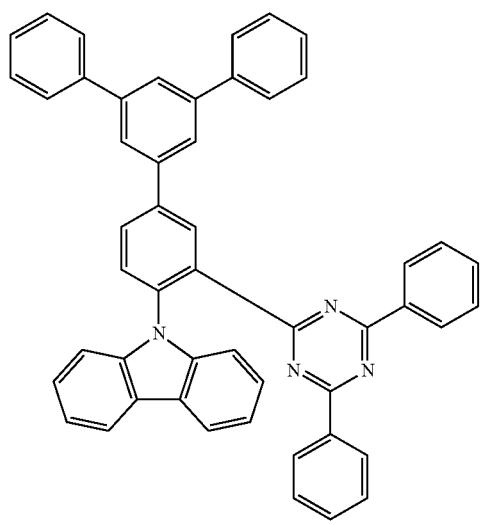
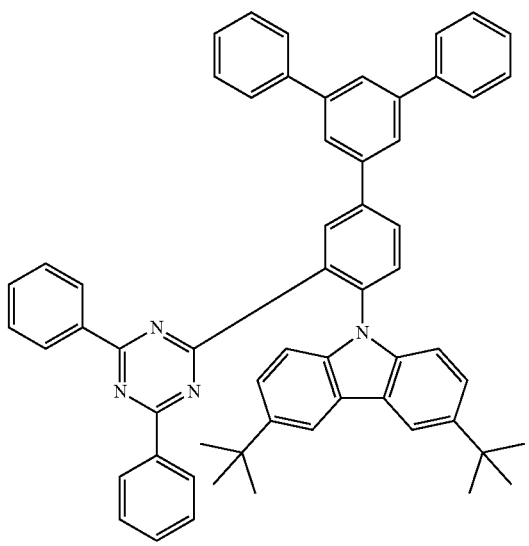
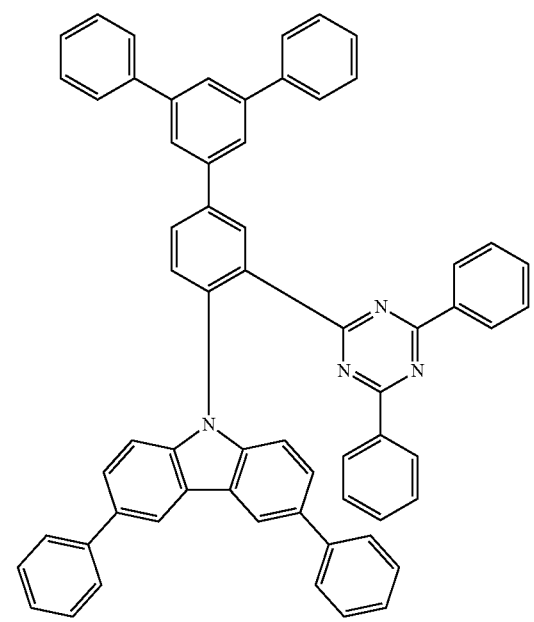

1251
-continued
38
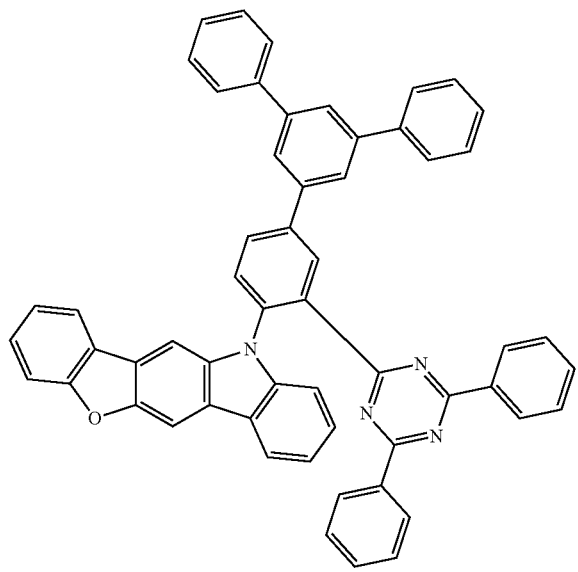
39
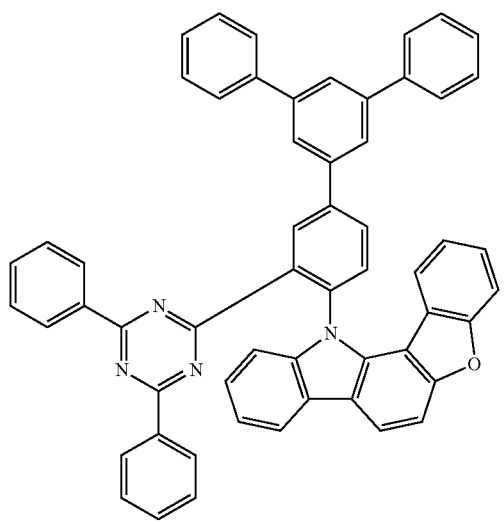
40
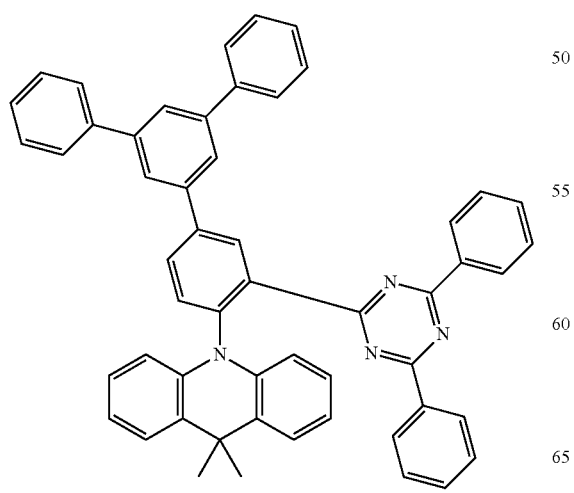
1252
-continued
41
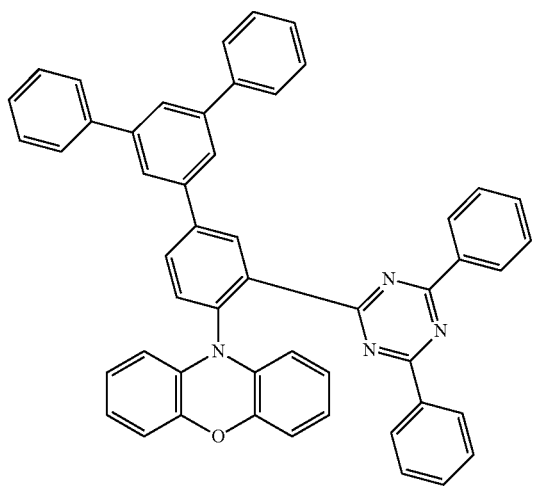
42
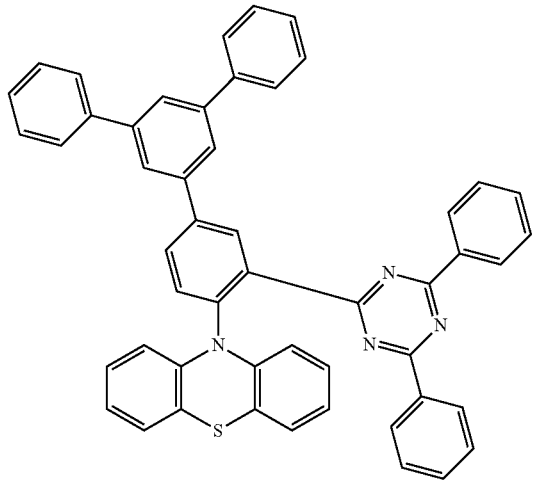
43
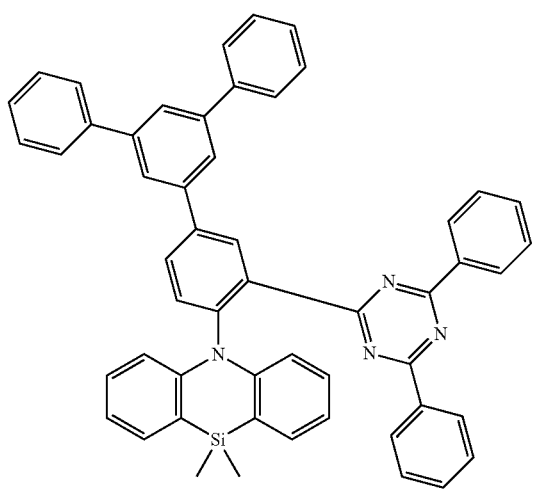

44
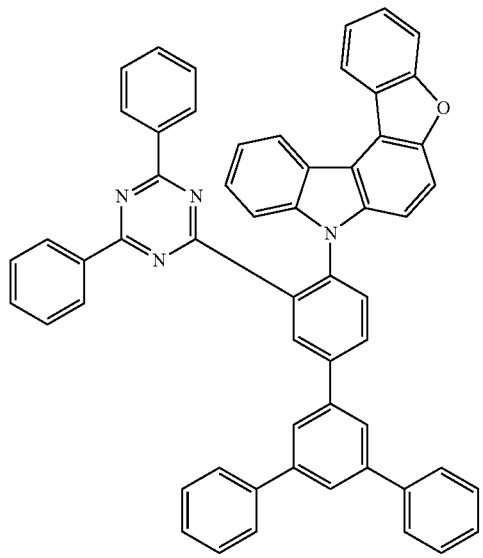
45
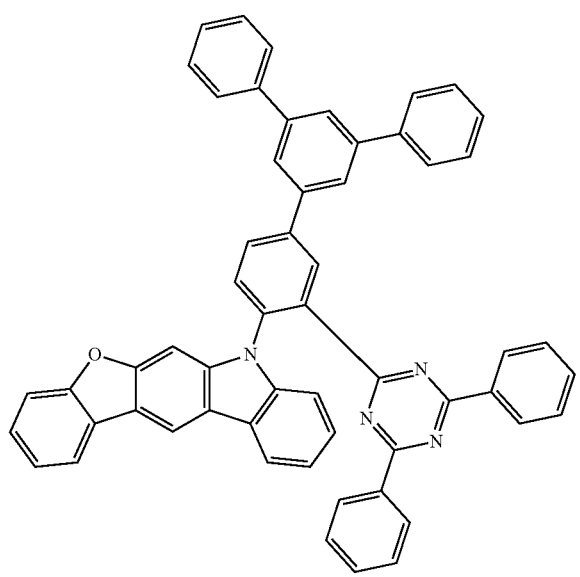
46
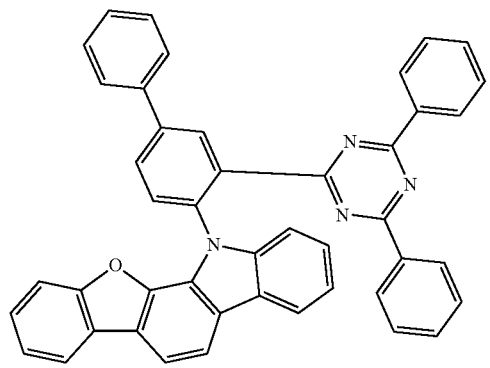
47
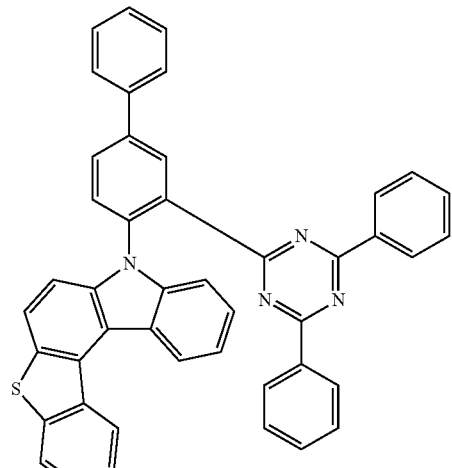
48
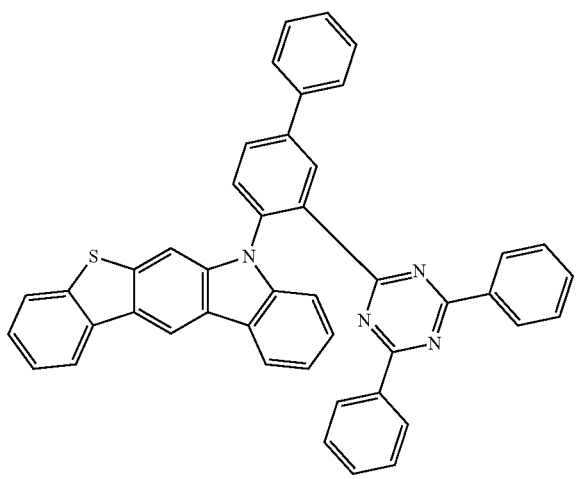
49
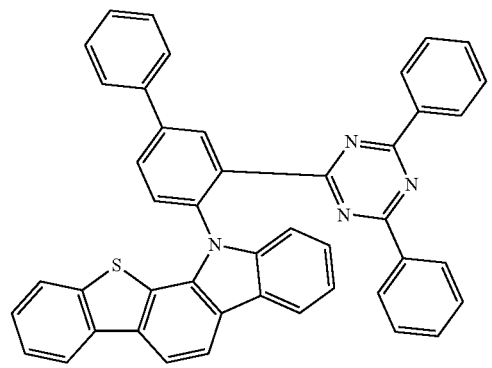

1255
-continued
50    1256
-continued
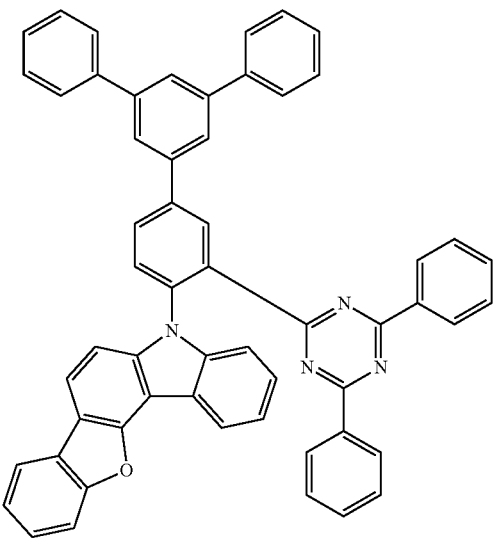
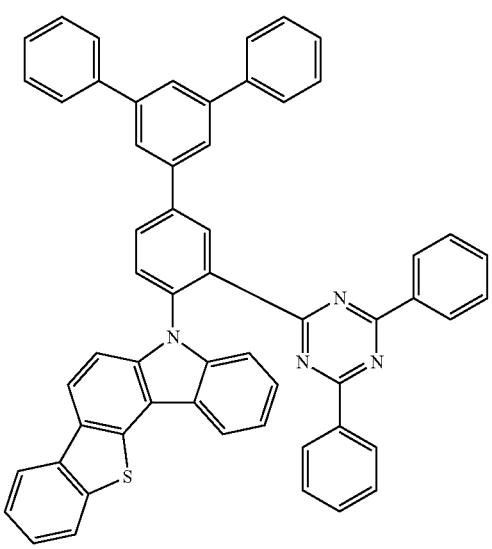
51
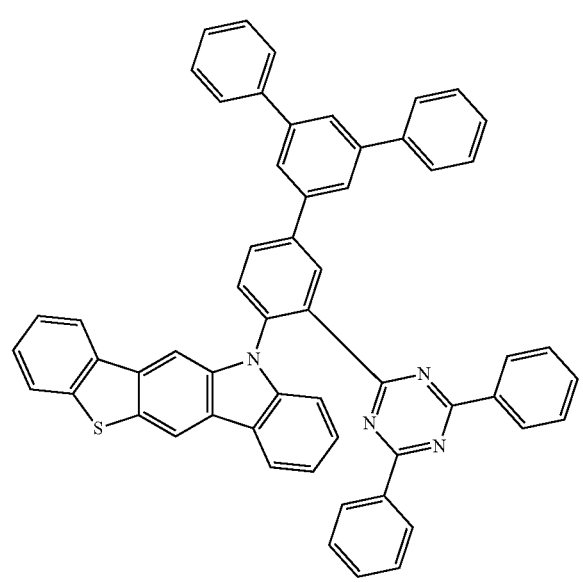
54
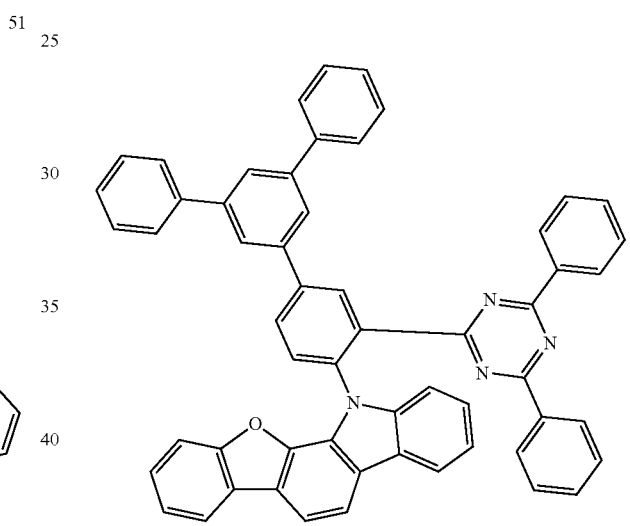
52
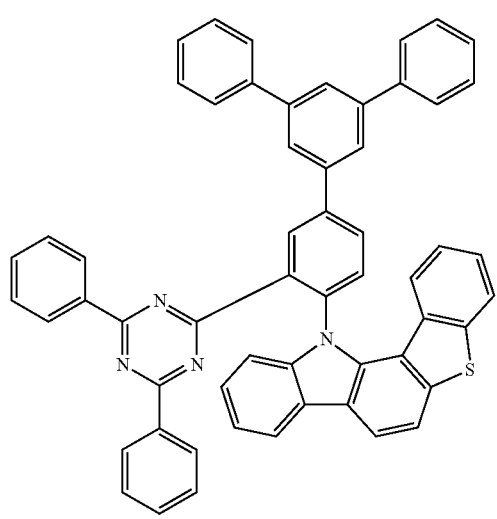
55
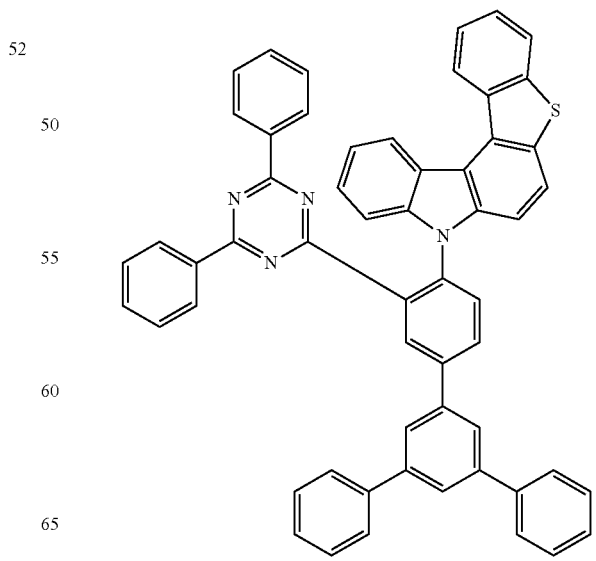

1257
-continued
56
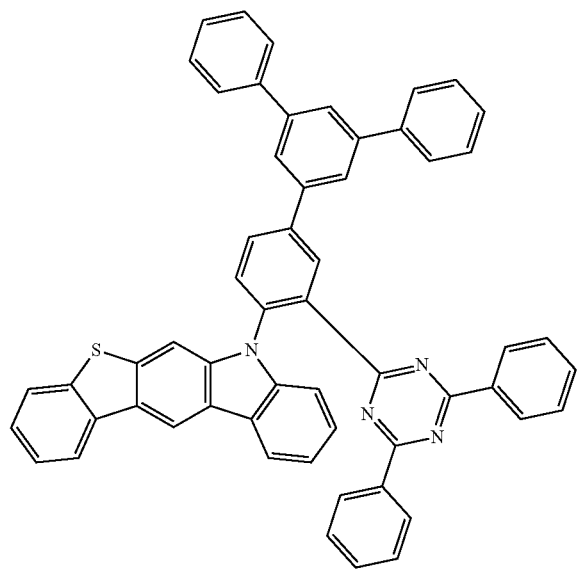
57
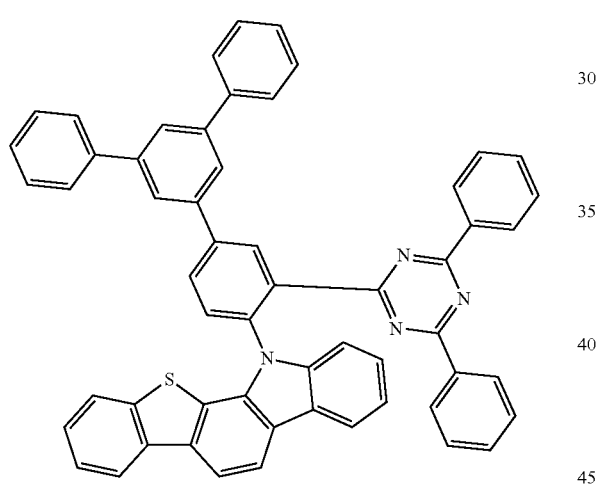
58
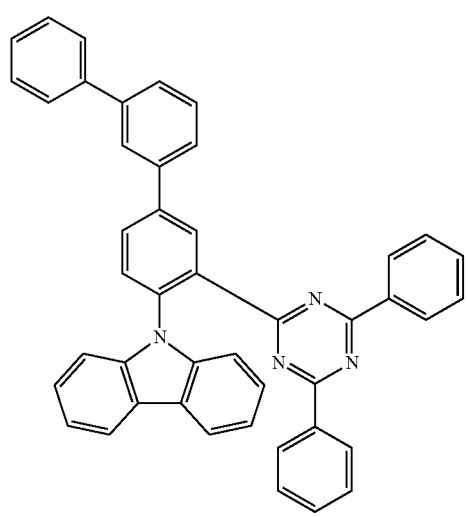
1258
-continued
59
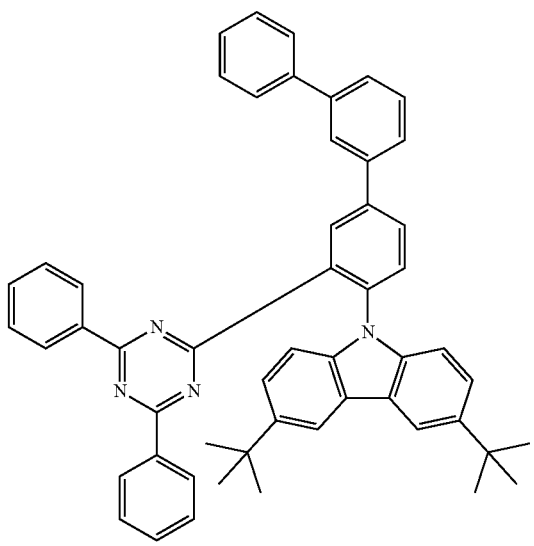
60
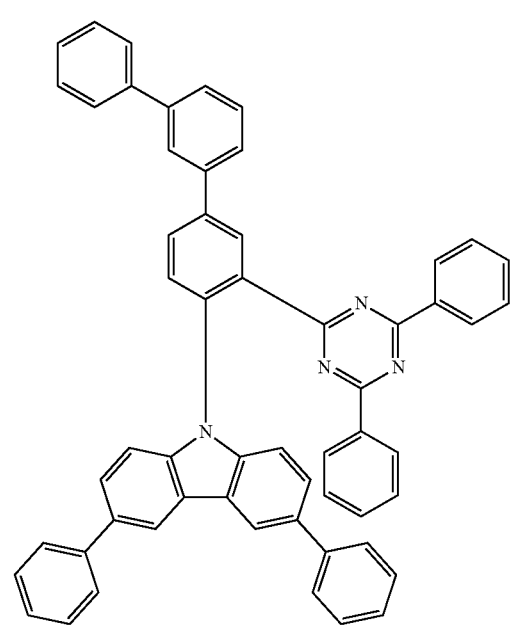

1259
-continued
61
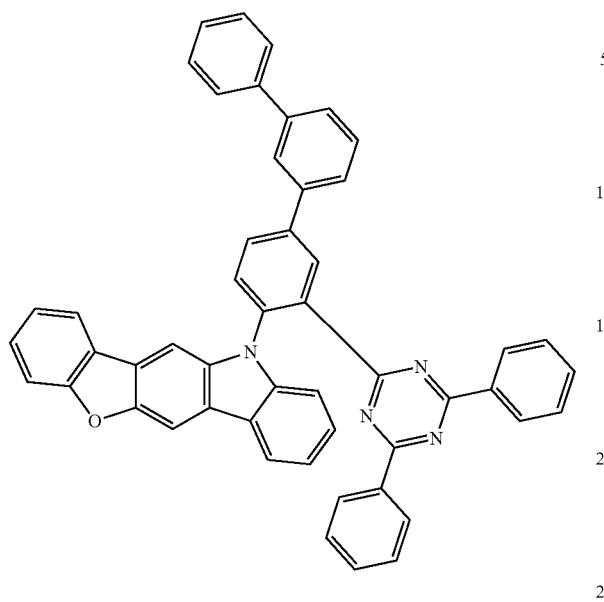
62
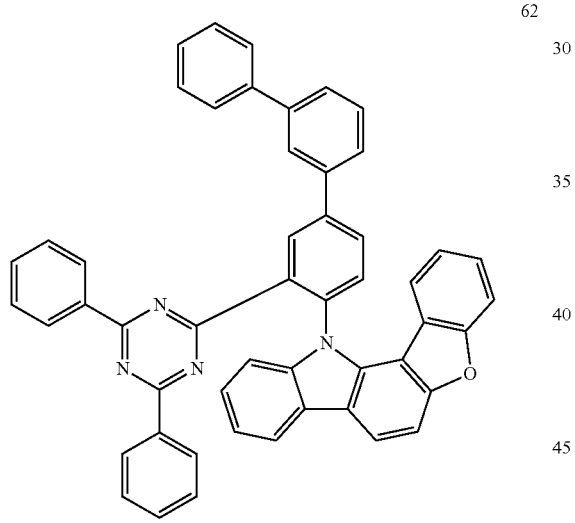
63
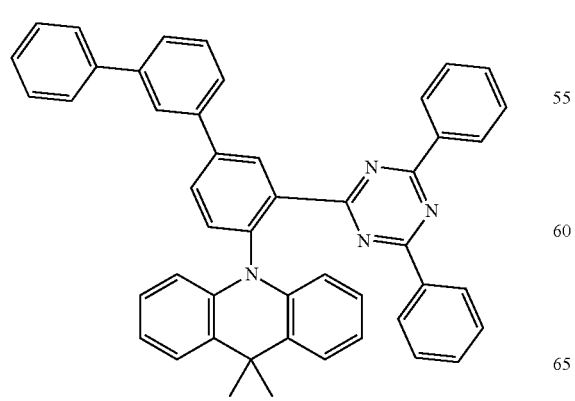
1260
-continued
64
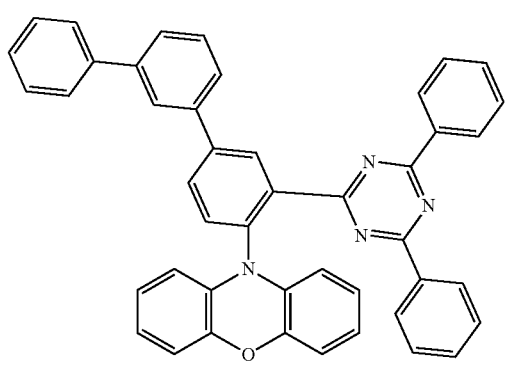
65
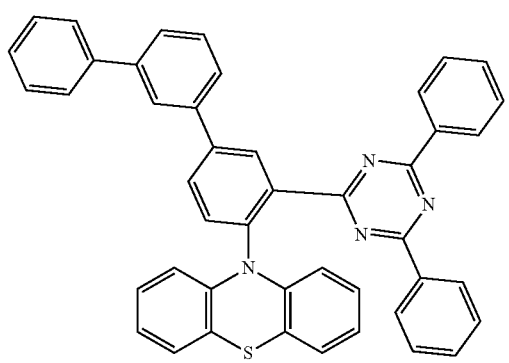
66
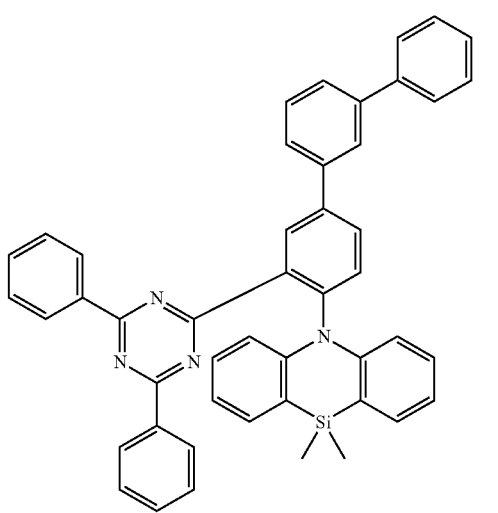

1261
-continued
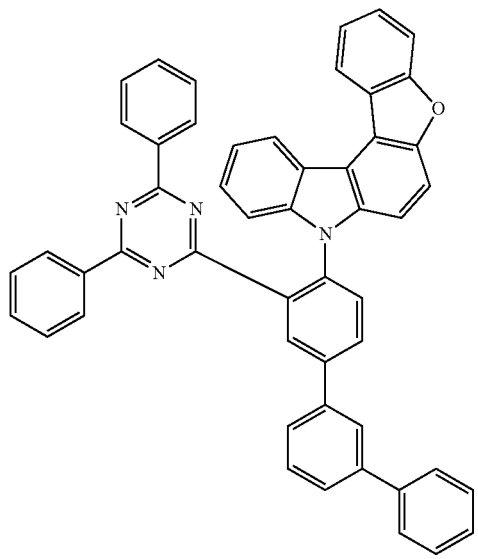
67
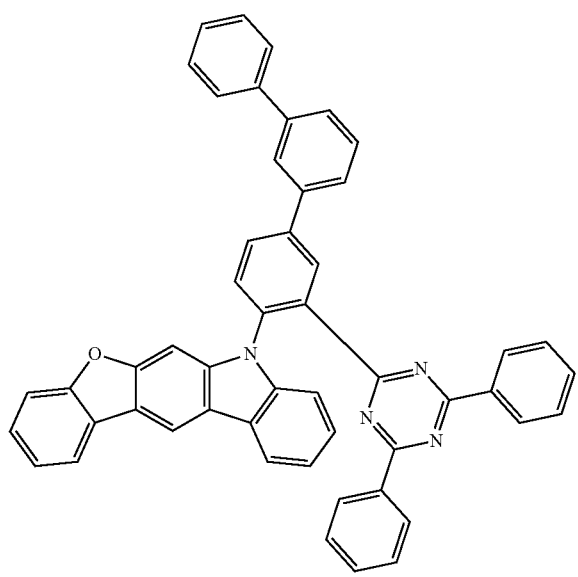
68
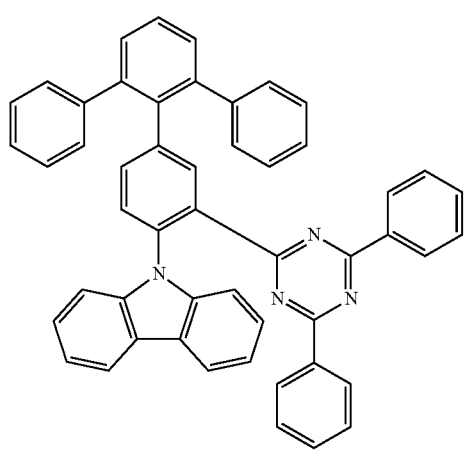
69
1262
-continued
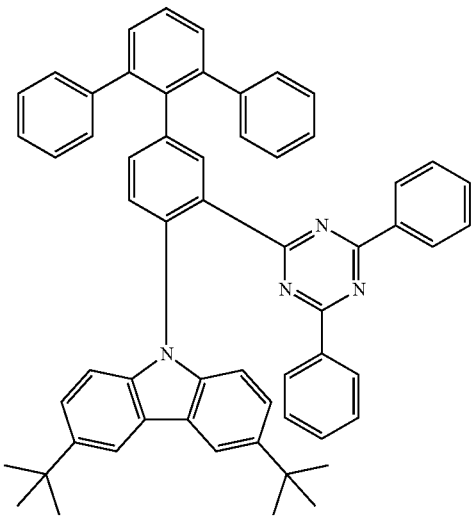
70
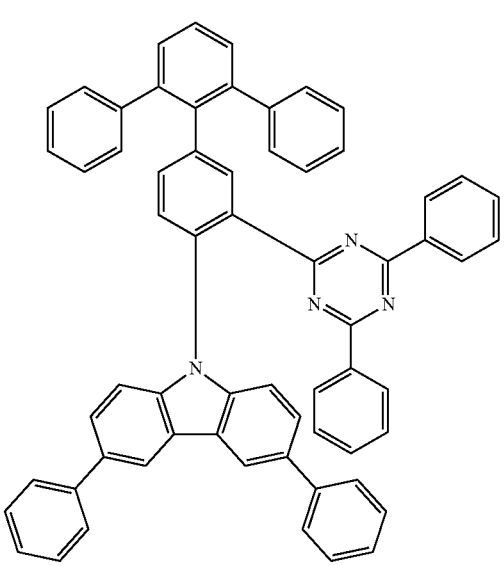
71
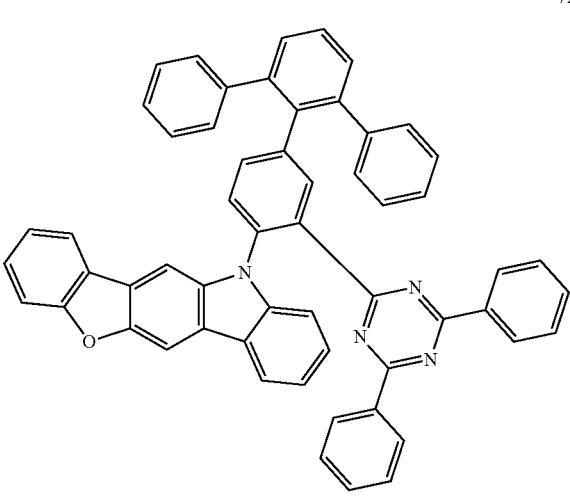
72

1263
-continued
73
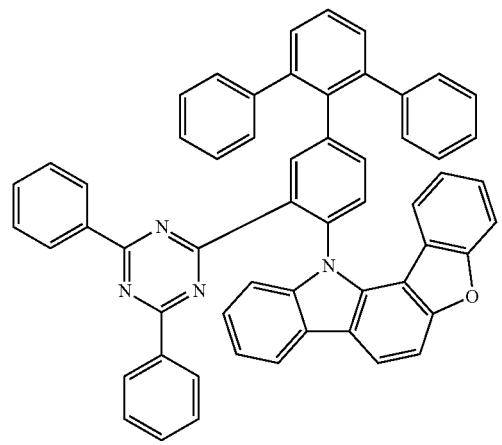
74
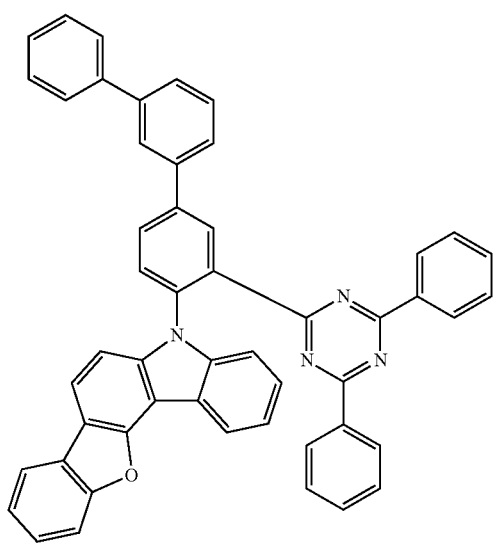
75
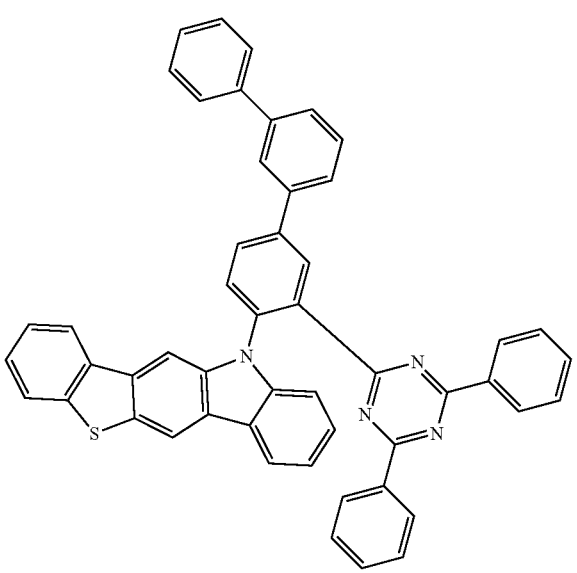
1264
-continued
76
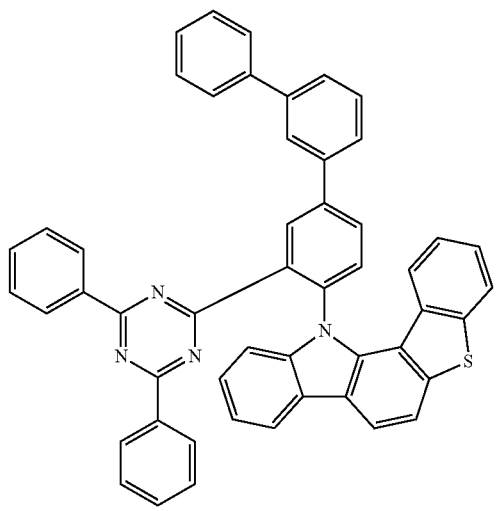
77
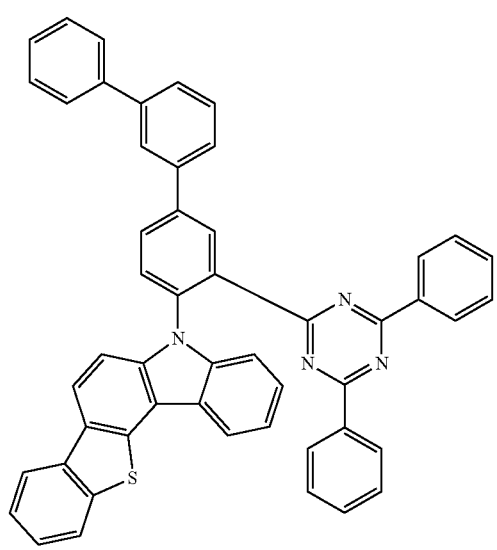
78
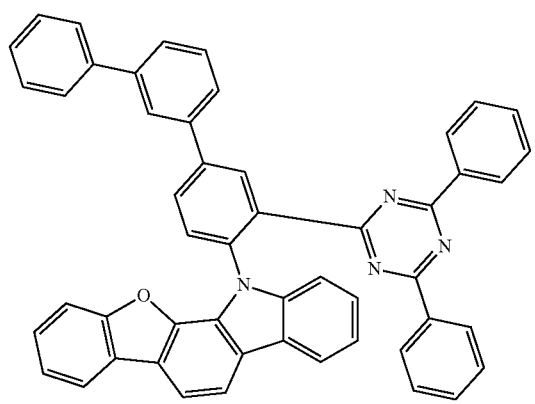

1265
-continued
79
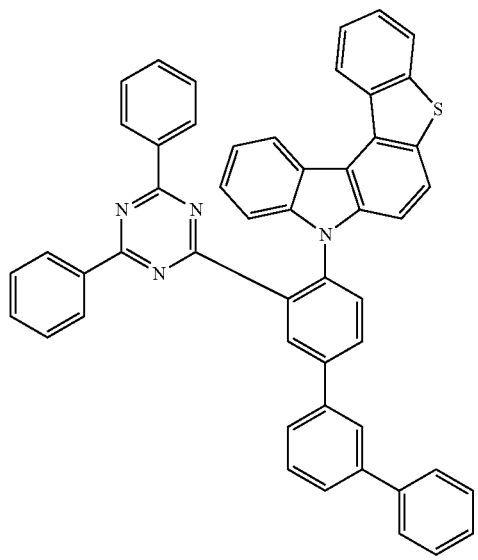
80
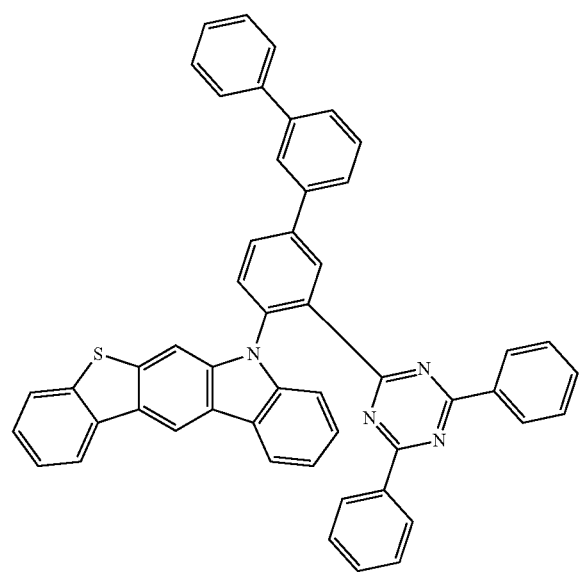
81
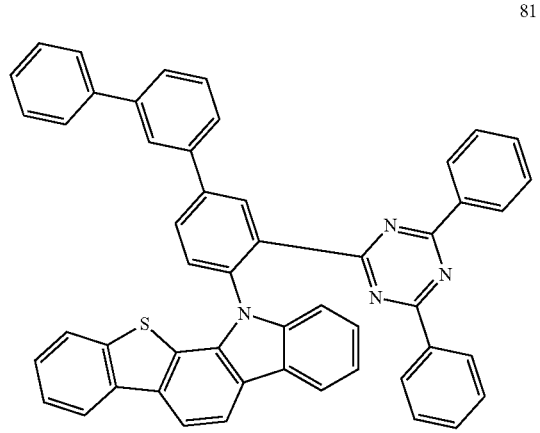
1266
-continued
82
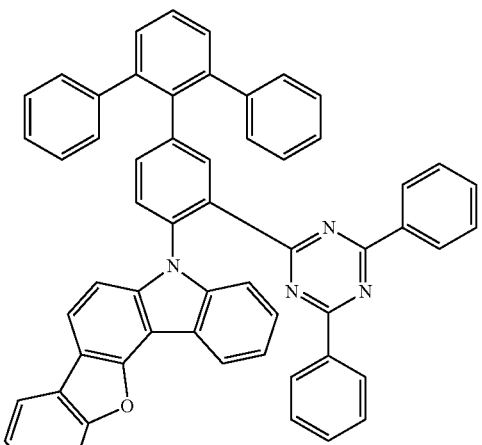
83
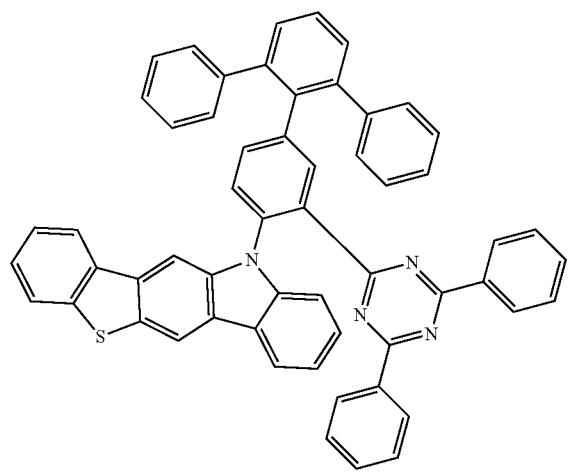
84
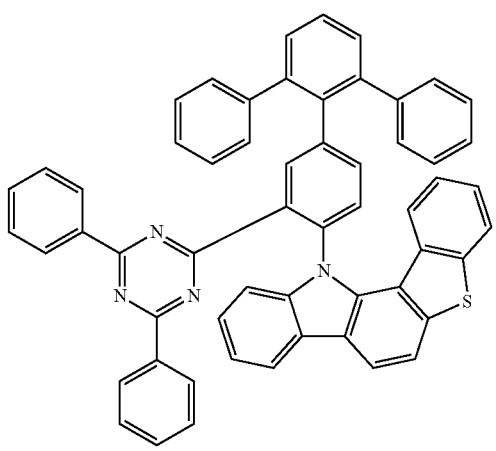

1267
-continued
85
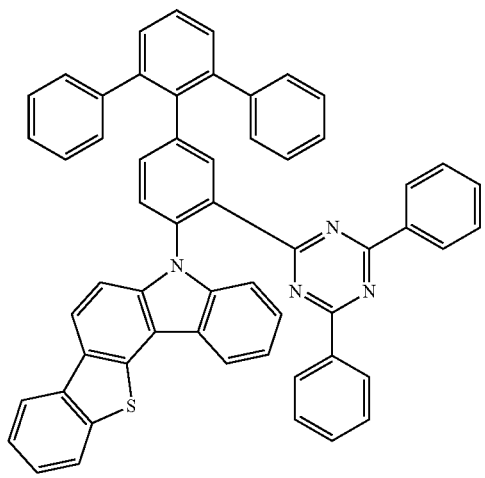
86
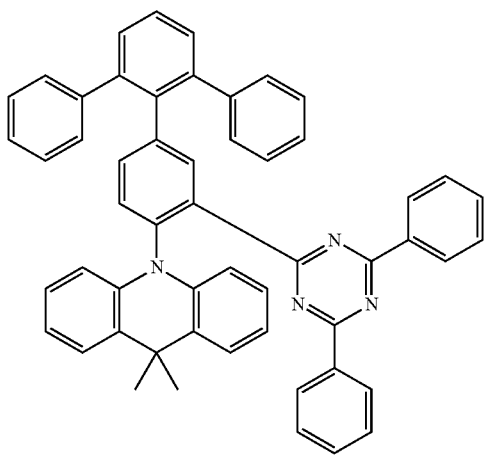
87
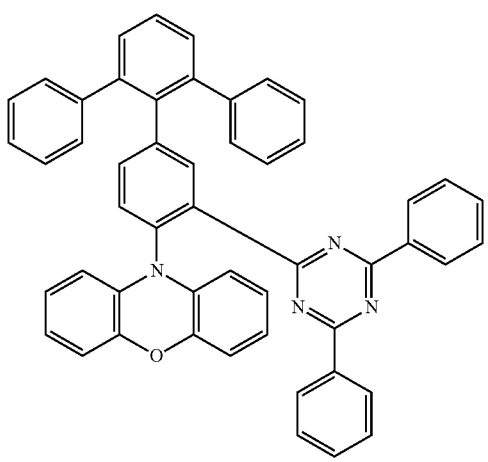
1268
-continued
88
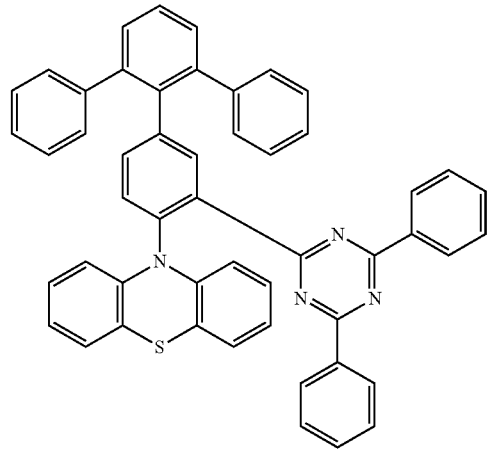
89
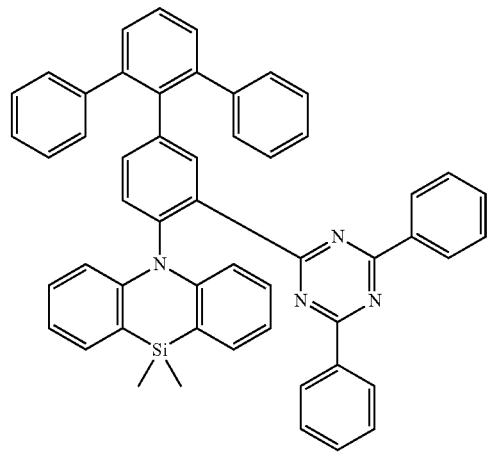
90
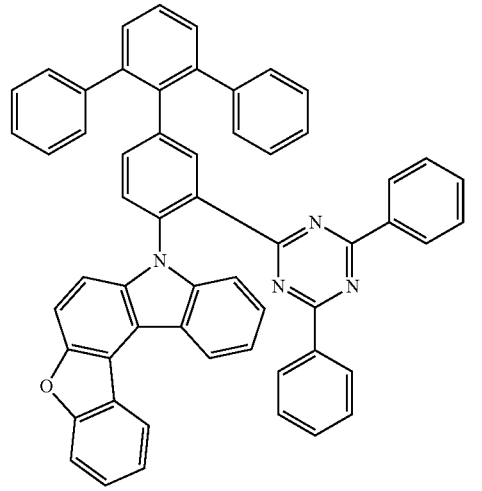

1269
-continued
91
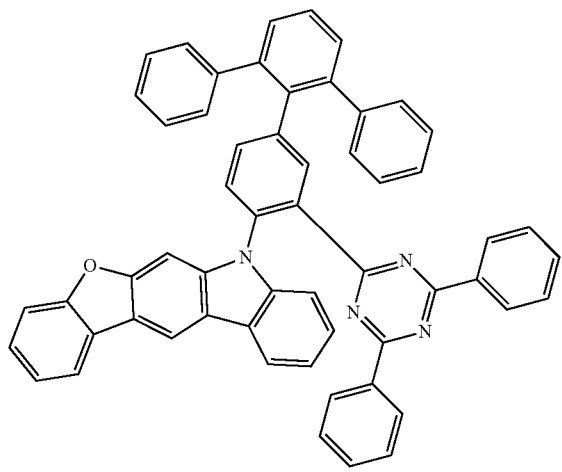
92
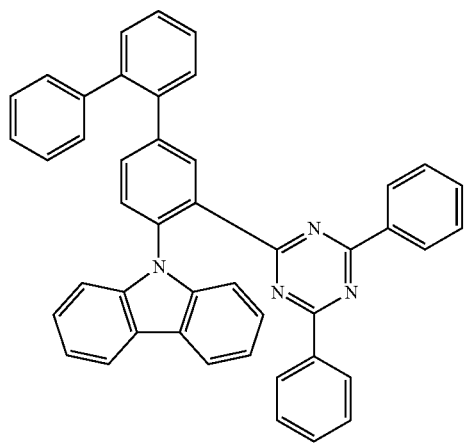
93
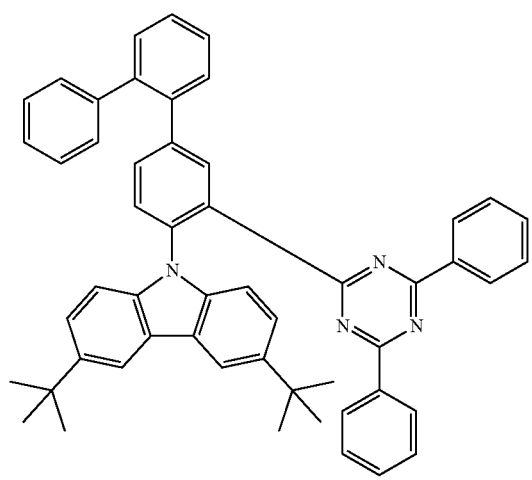
1270
-continued
94
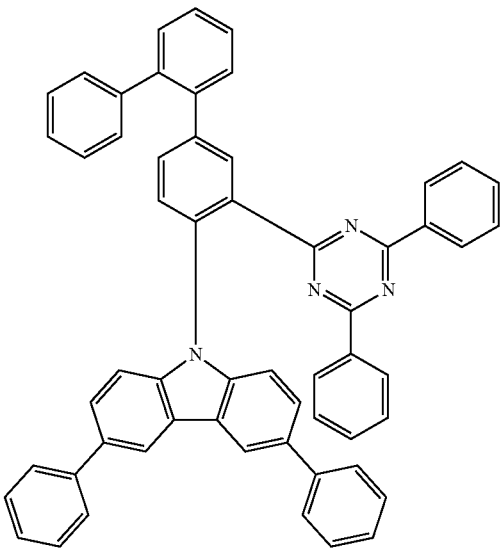
95
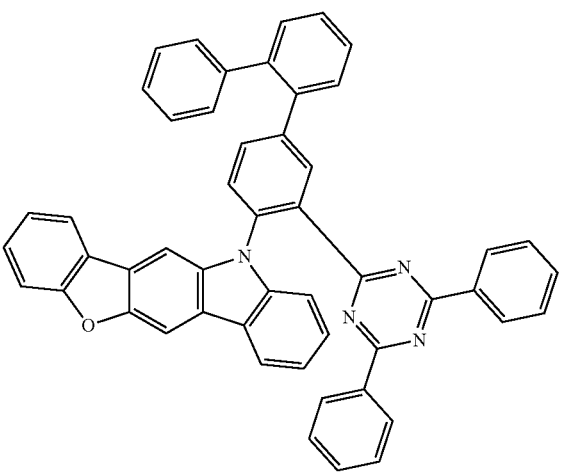
96
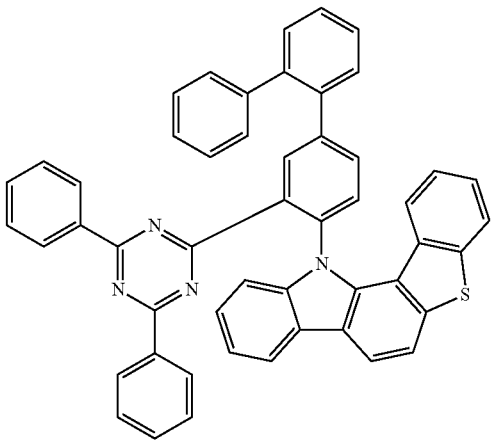

1271
-continued
97
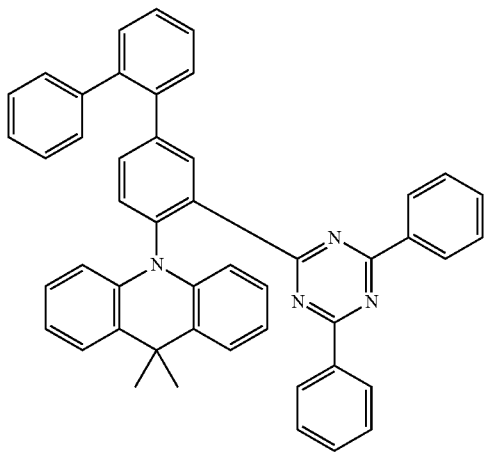
98
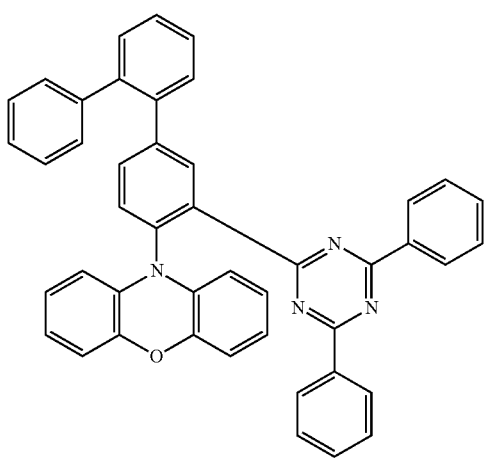
99
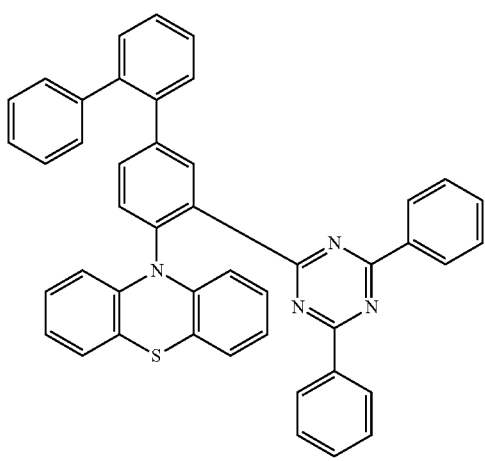
1272
-continued
100
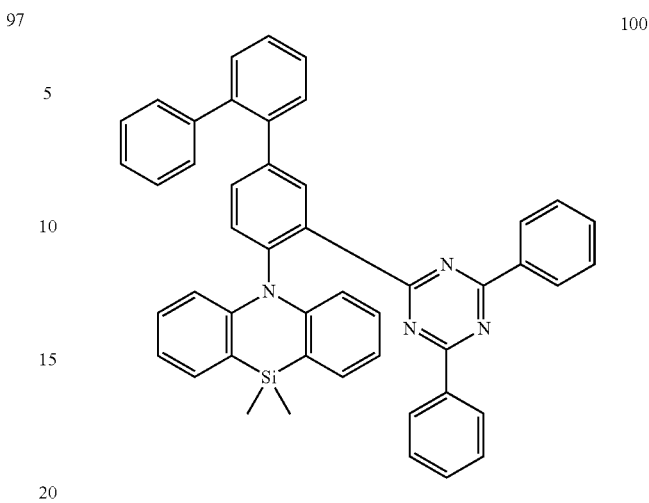
101
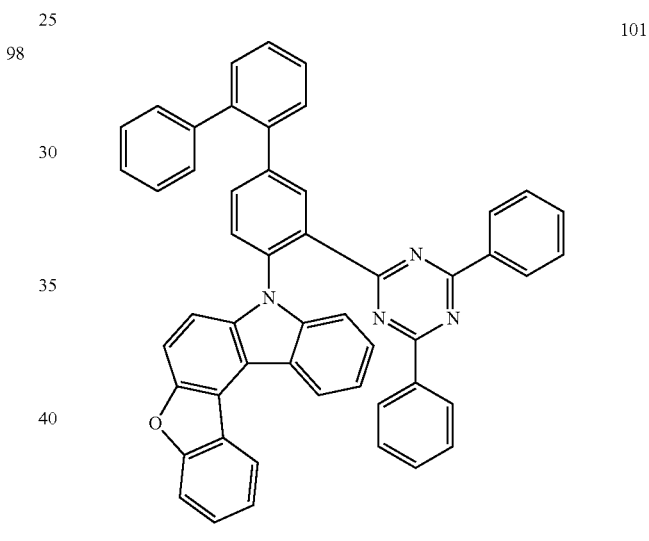
102
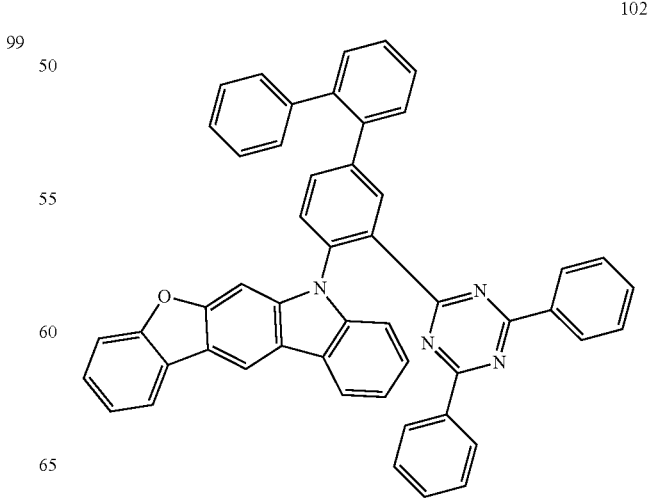

103
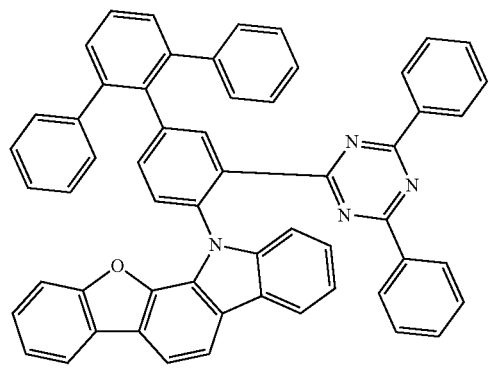
104
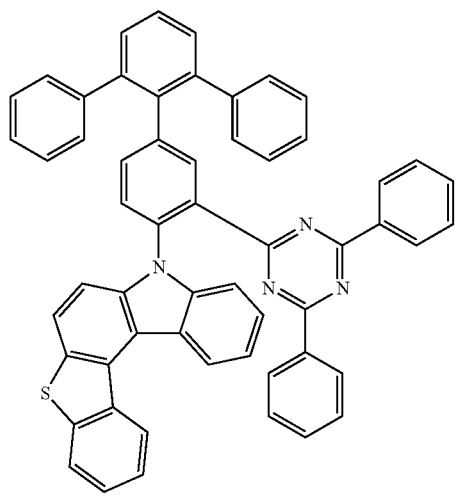
105
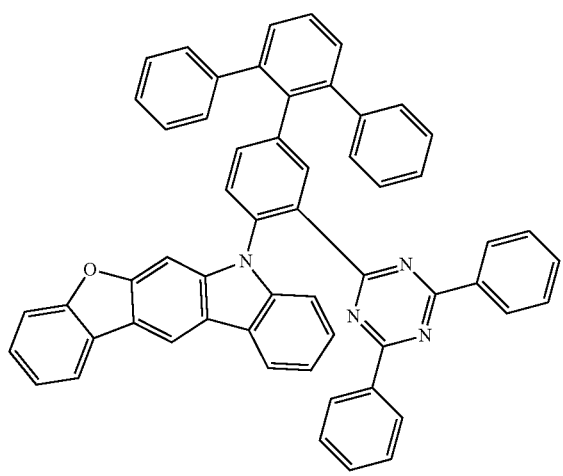
106
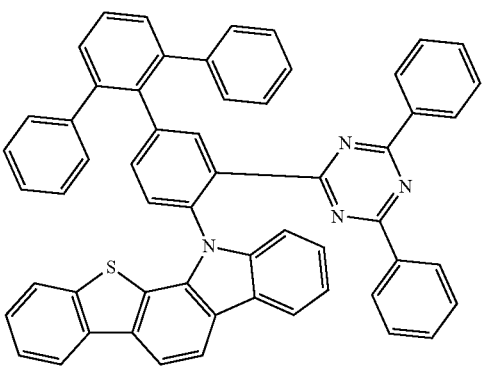
107
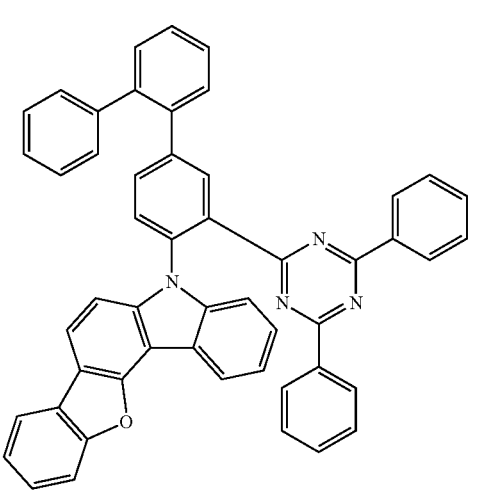
108
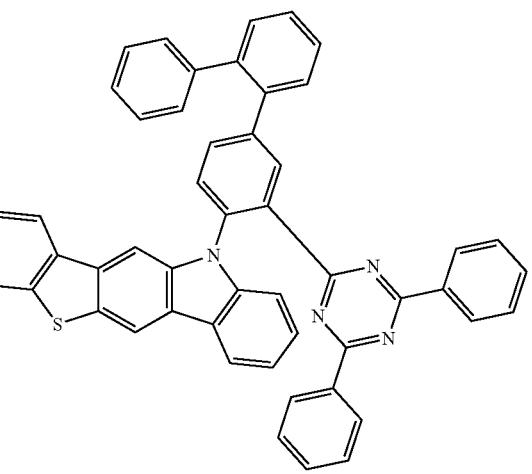

1275
-continued
109
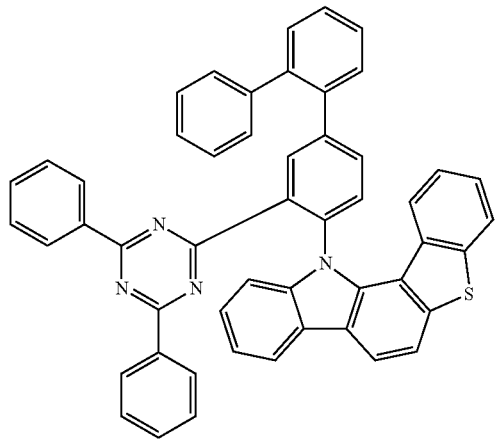
110
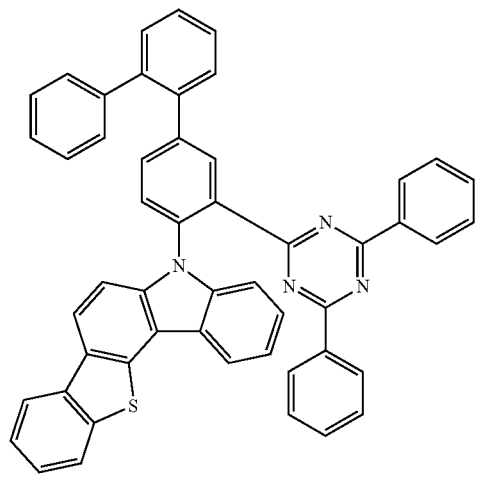
111
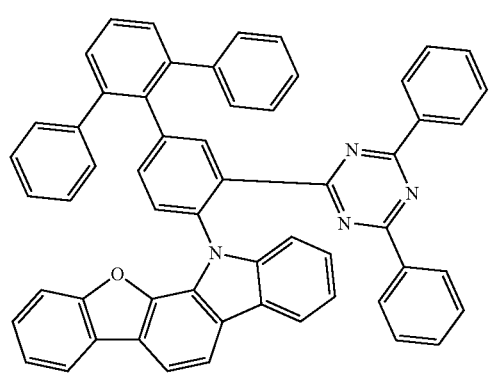
1276
-continued
112
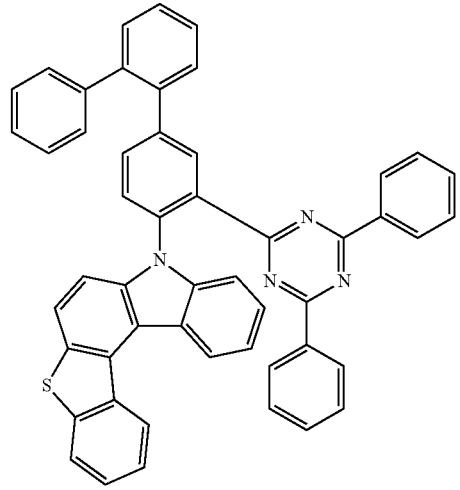
113
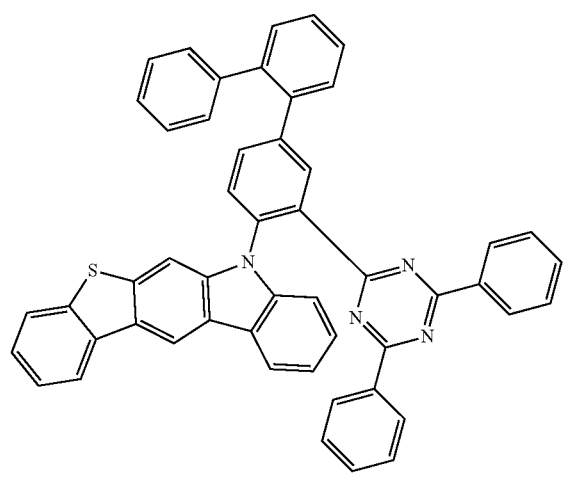
114
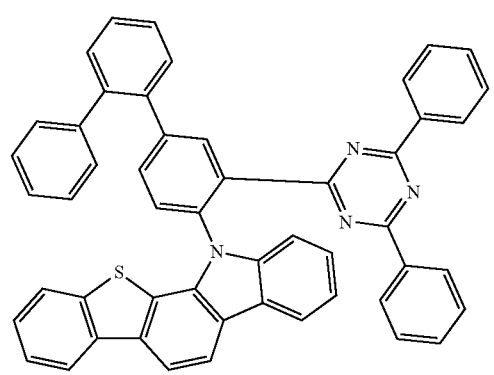

1277
-continued
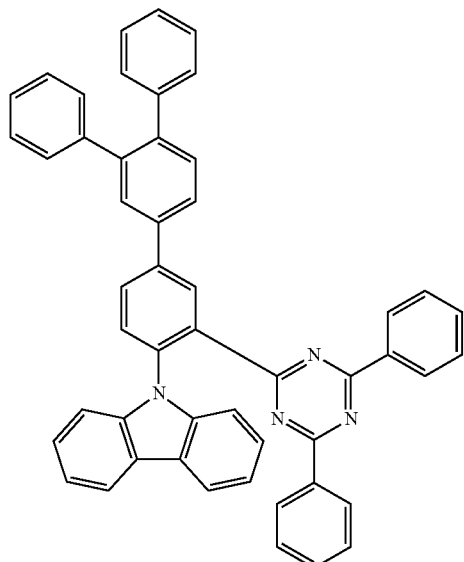
1278
-continued
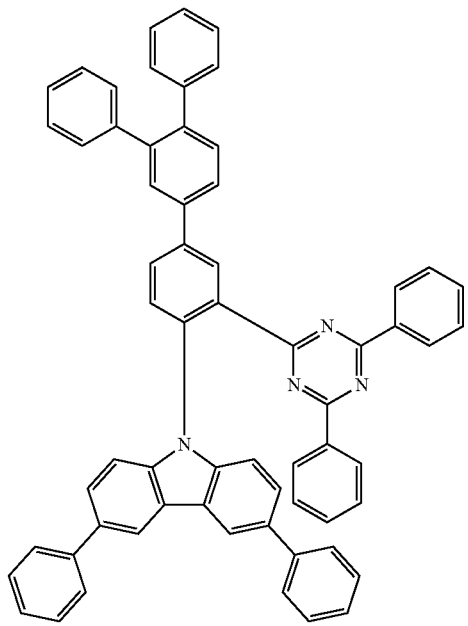
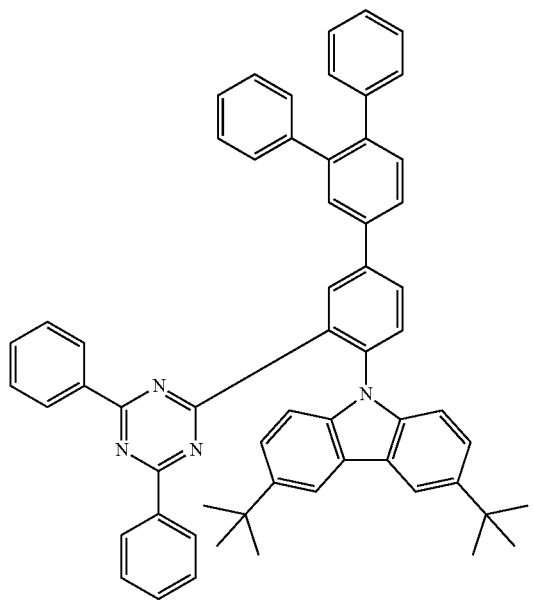
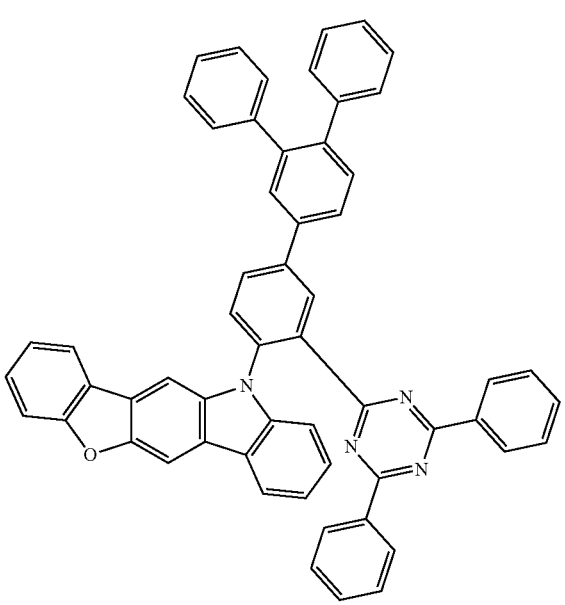

1279
-continued
119
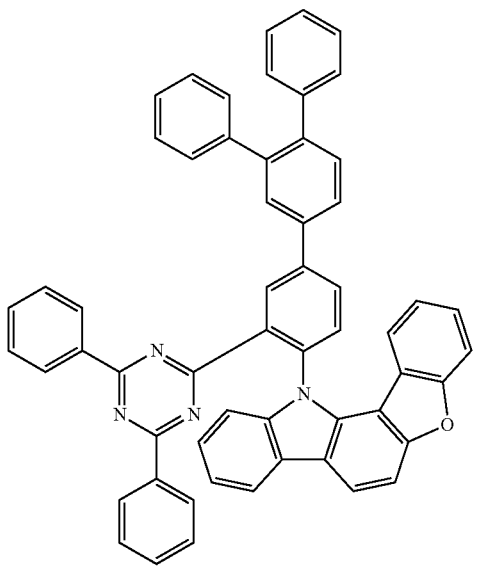
120
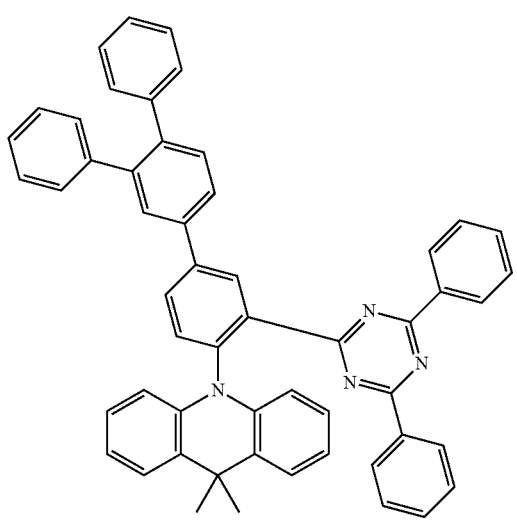
121
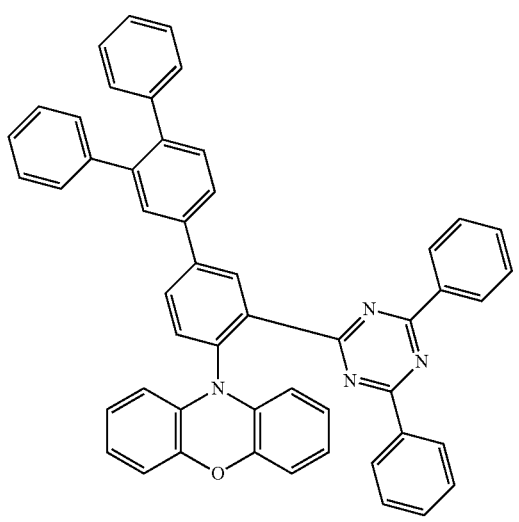
1280
-continued
122
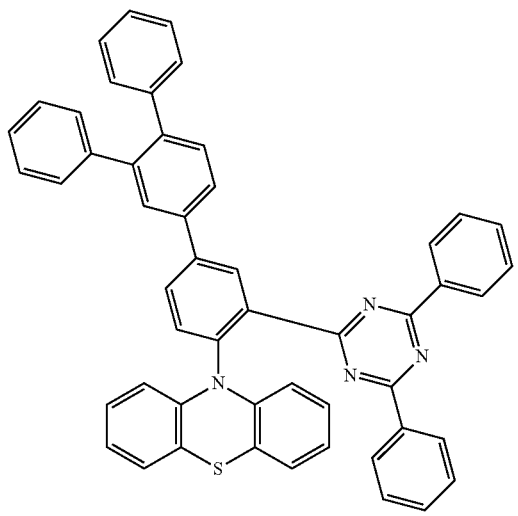
123
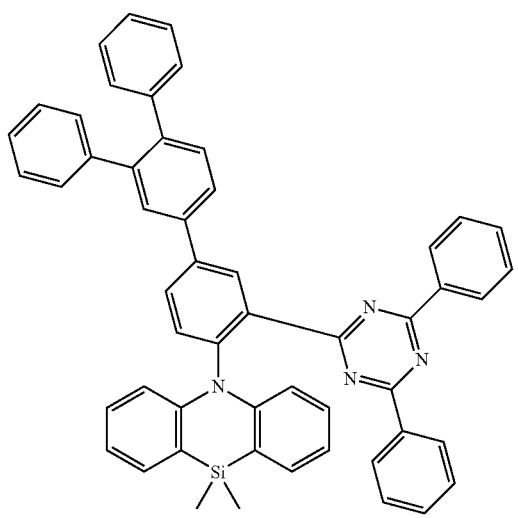

1281
-continued
124
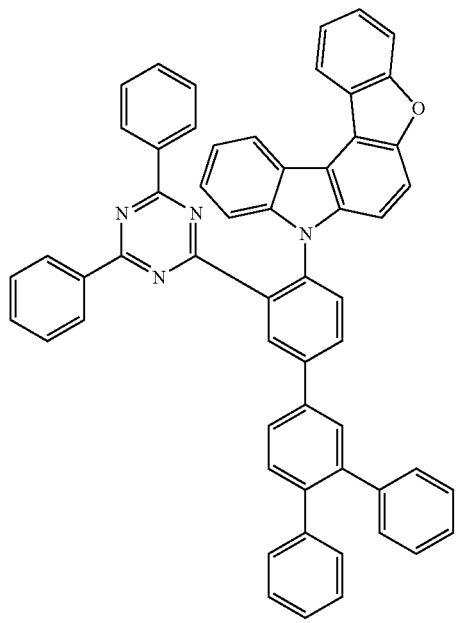
125
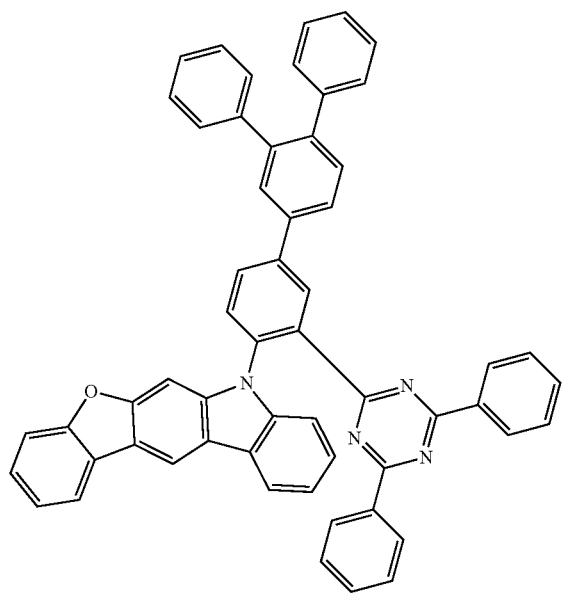
1282
-continued
126
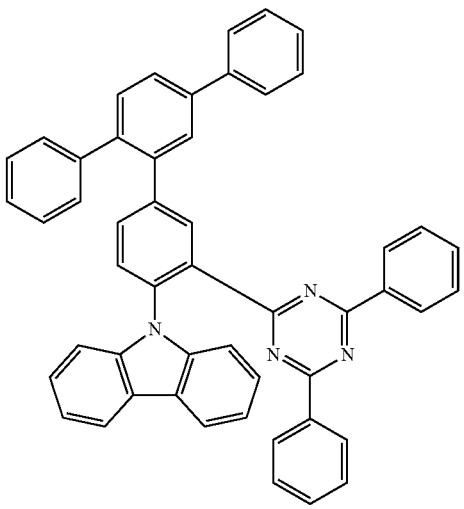
127
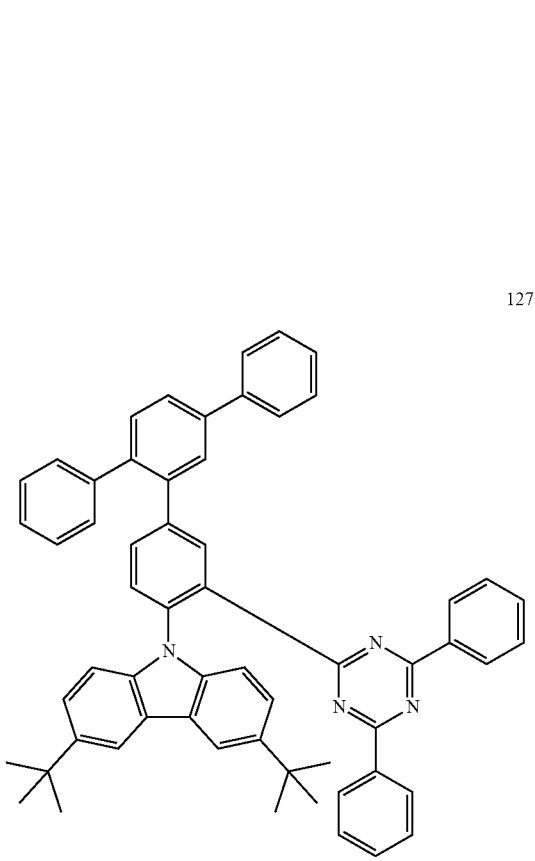

1283
-continued
128
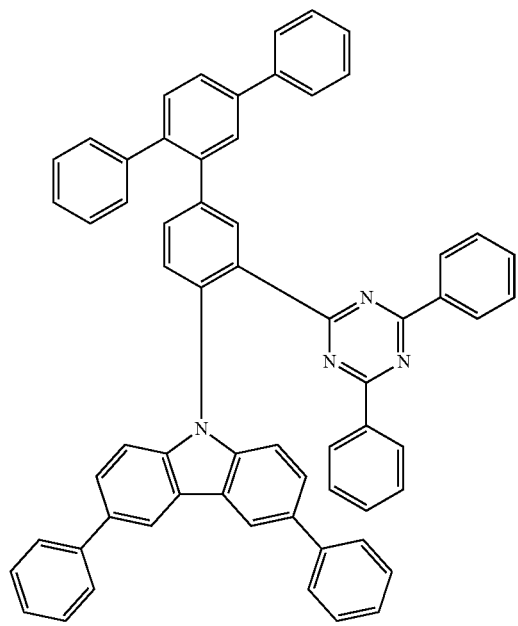
1284
-continued
130
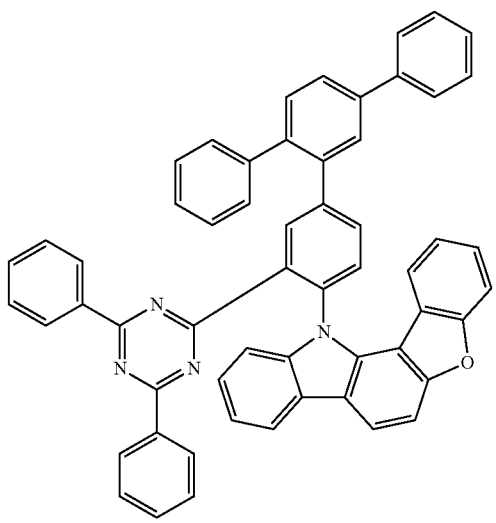
129
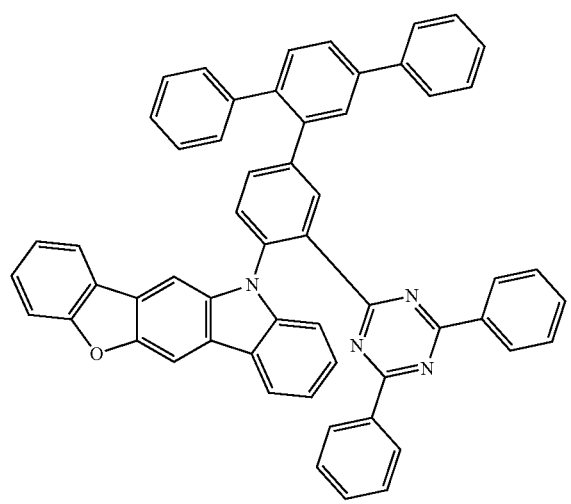
131
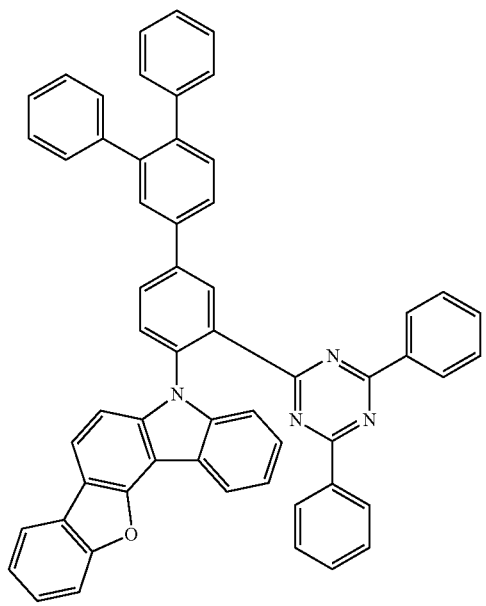

132
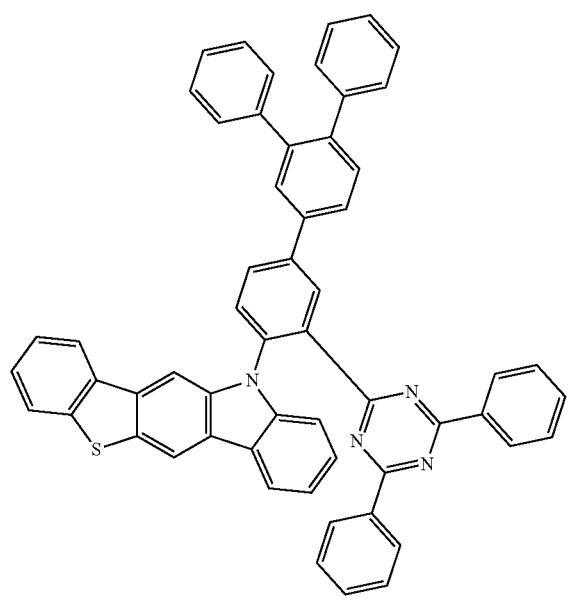
133
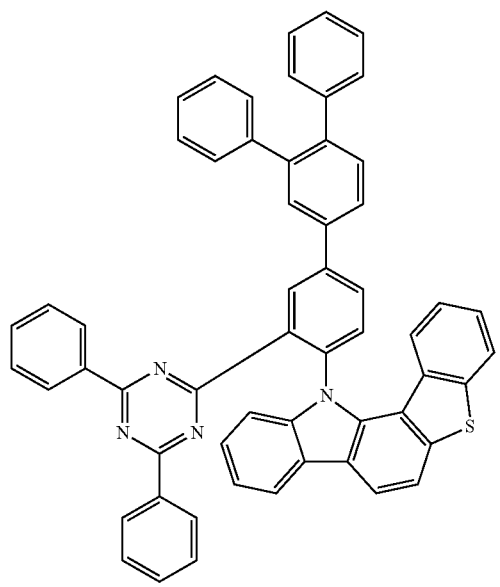
134
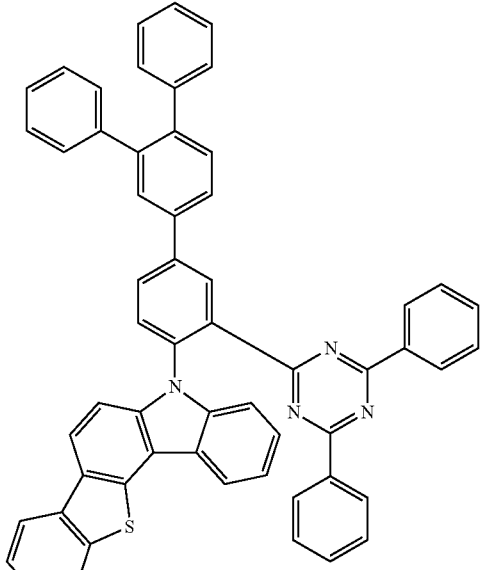
135
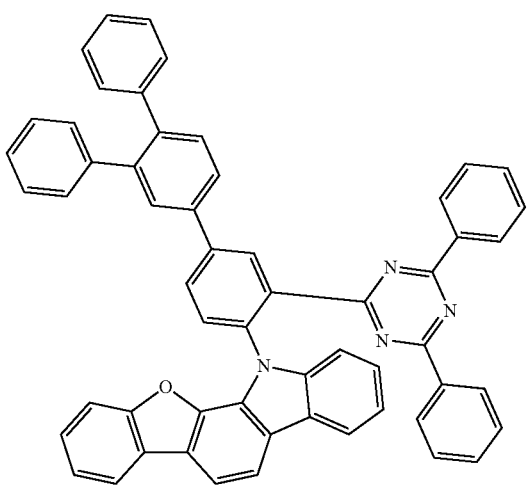

1287
-continued
136
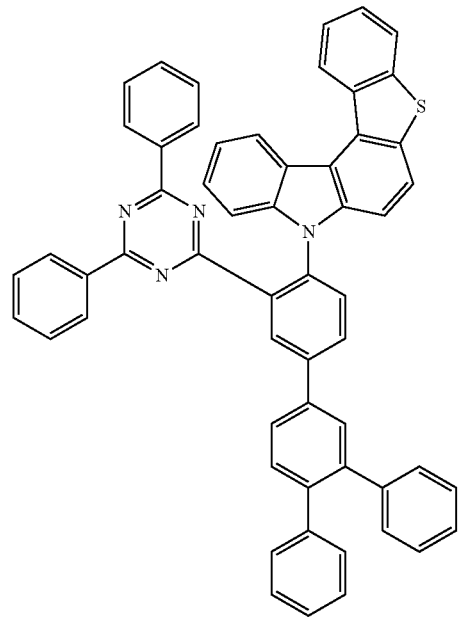
1288
-continued
138
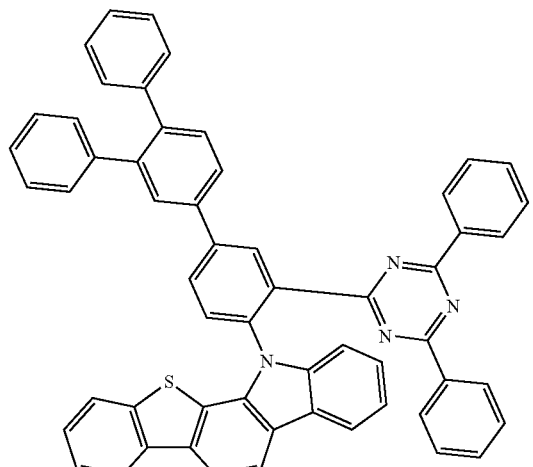
139
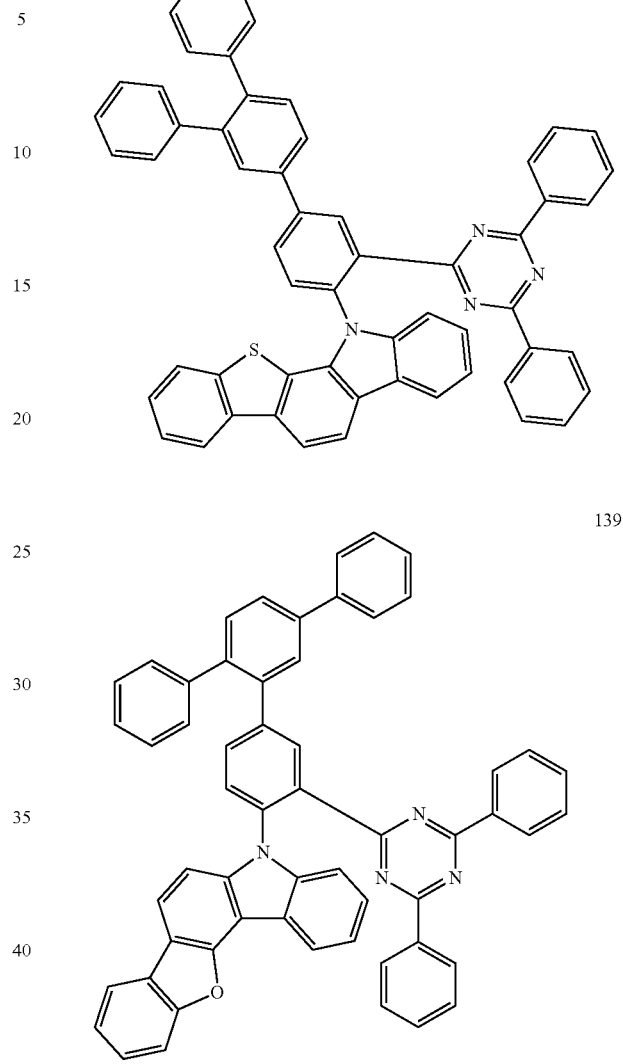
137
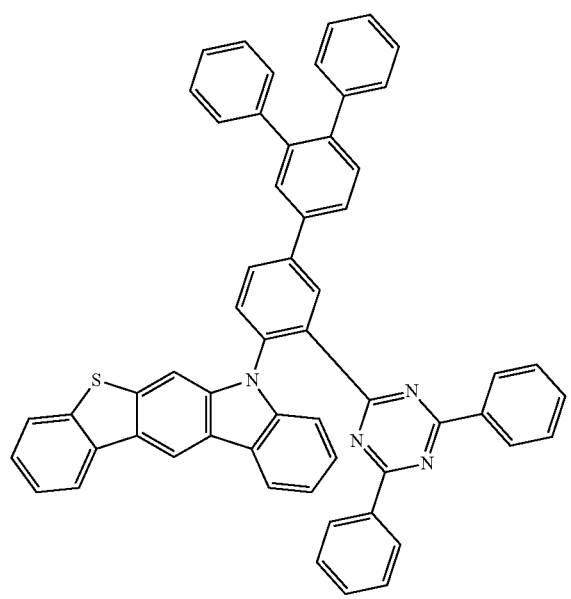
140
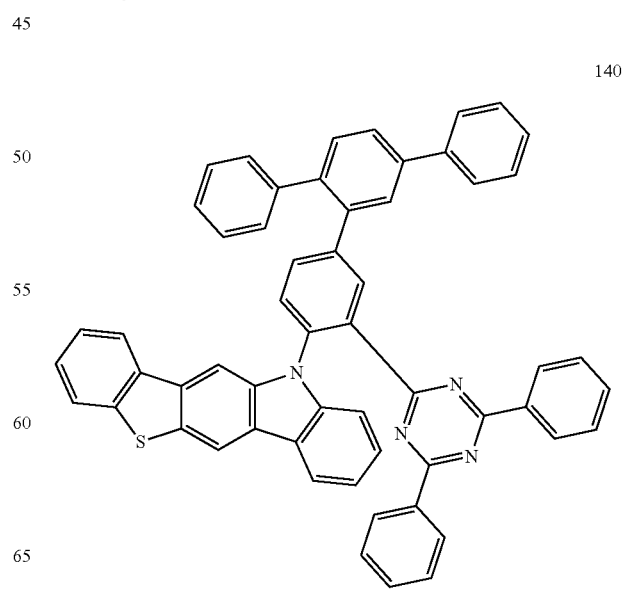

141
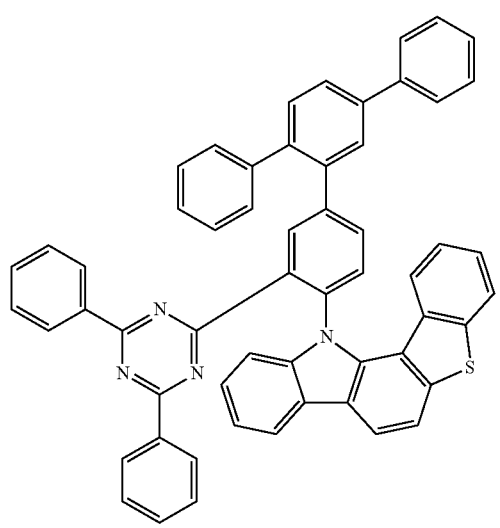
142
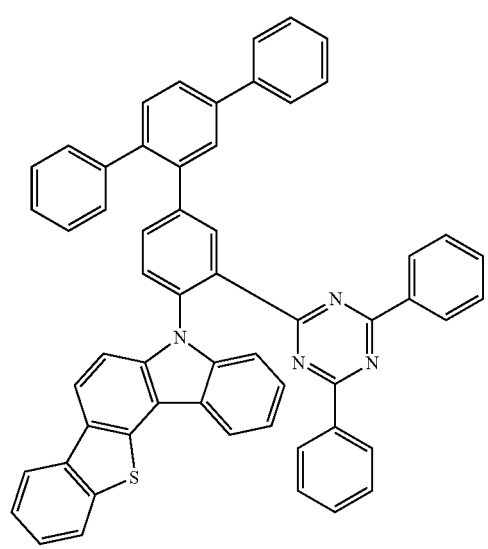
143
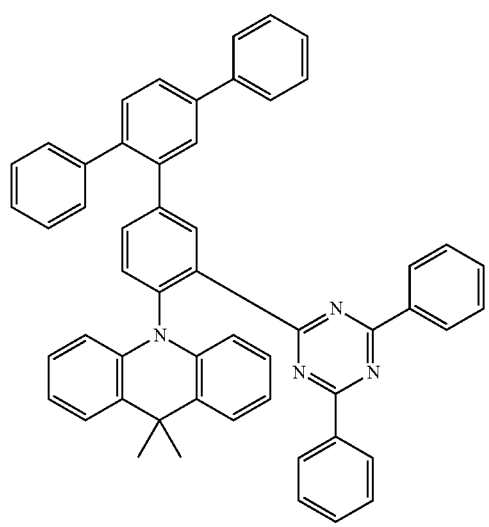
144
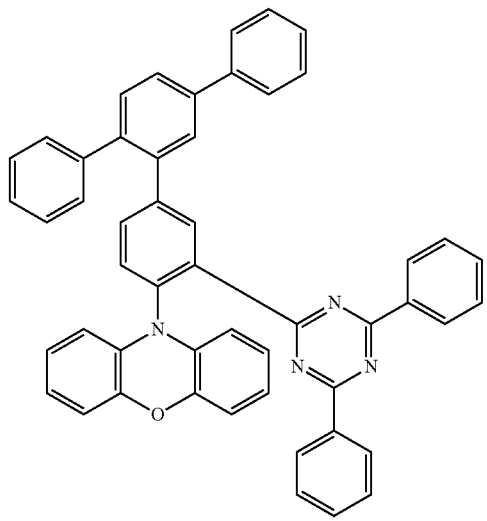
145
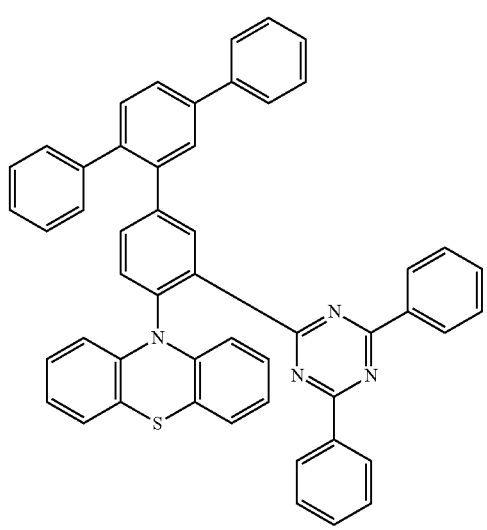
146
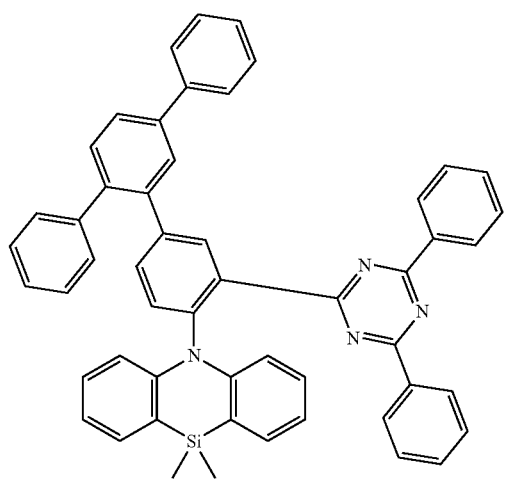

1291
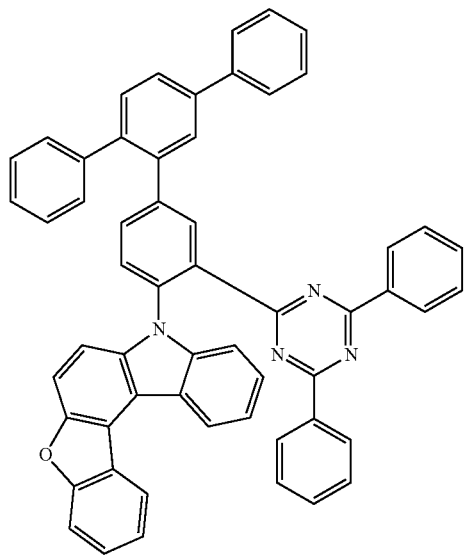
147
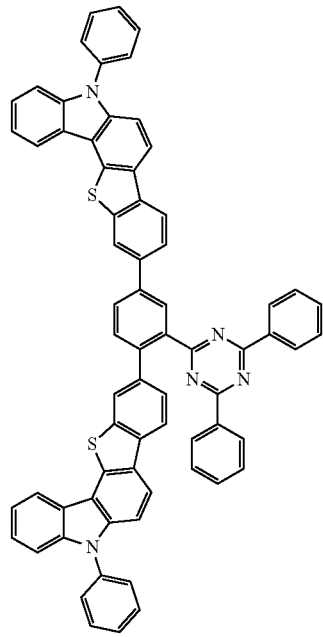
149
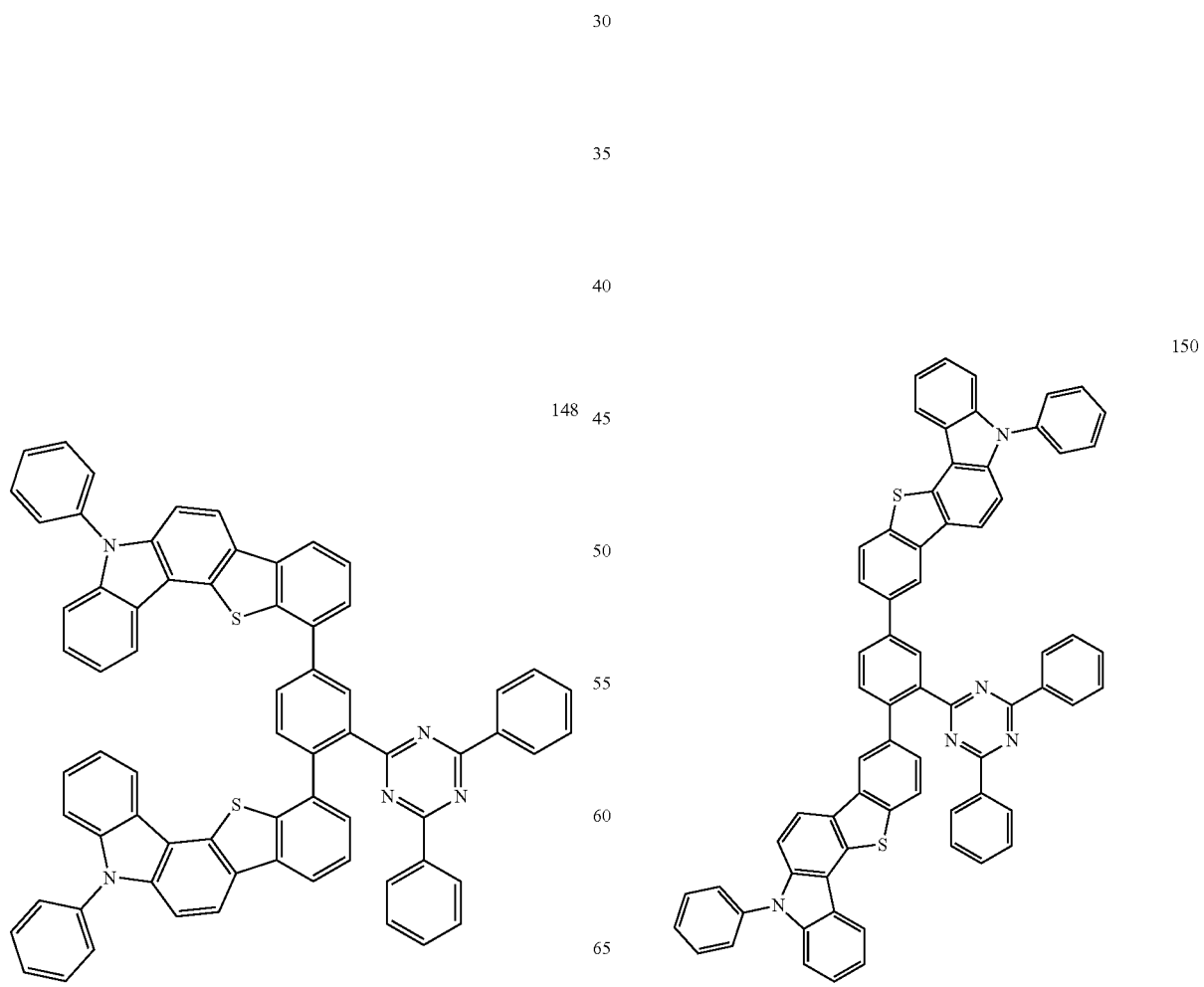
1292

1293
-continued
151
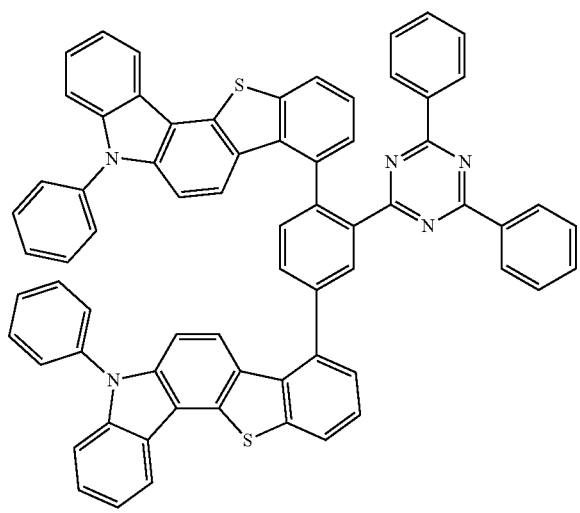
152
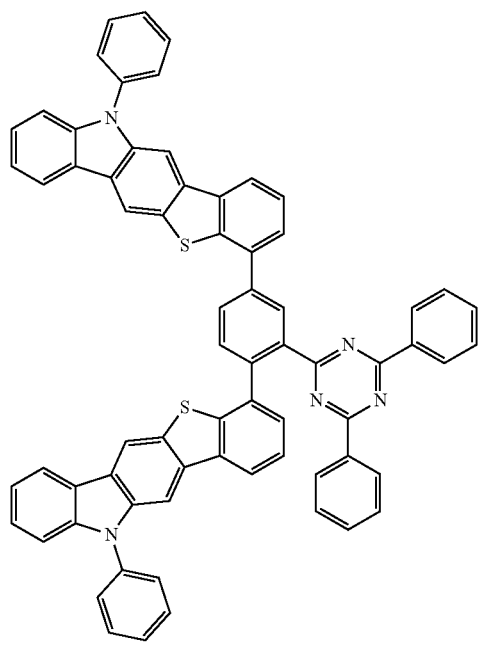
1294
-continued
153
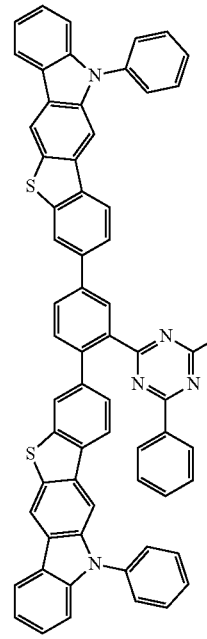
154
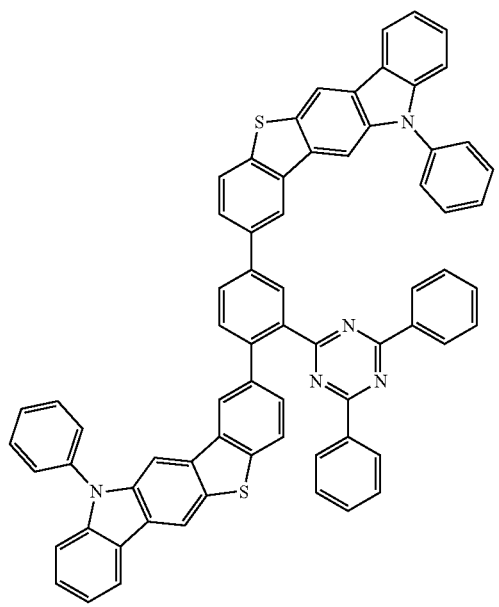

1295
-continued
155
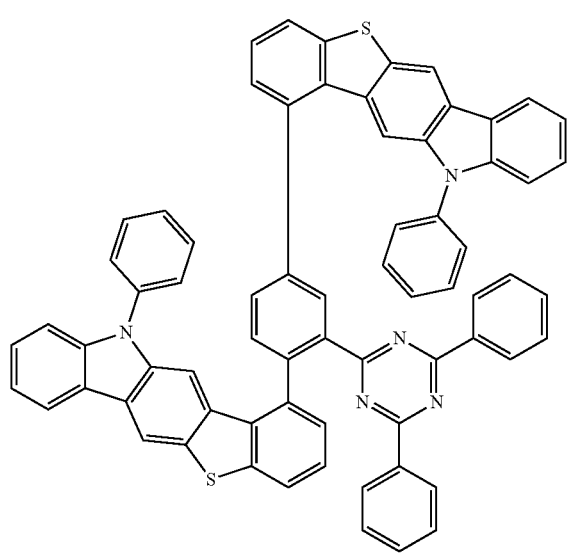
156
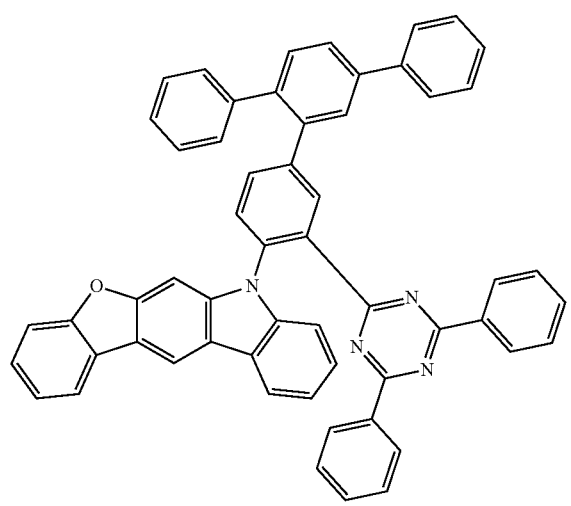
157
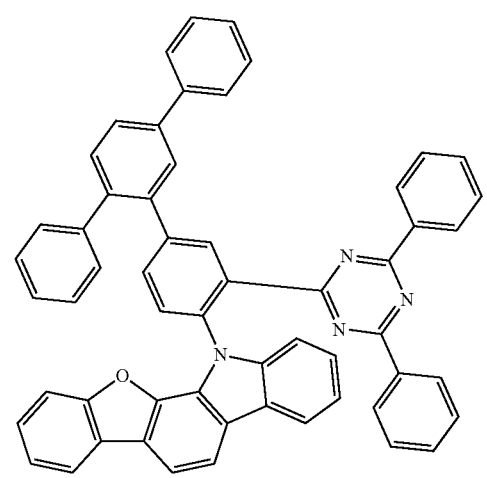
1296
-continued
158
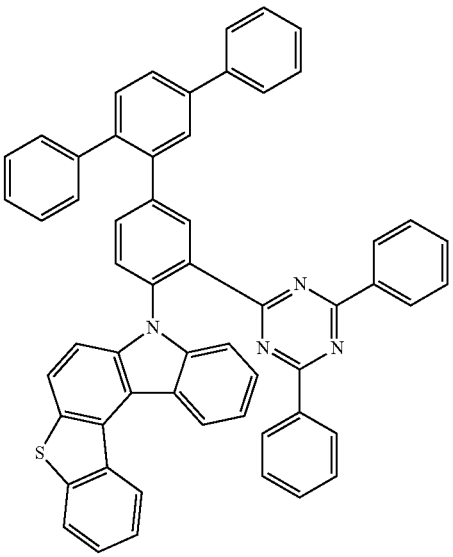
159
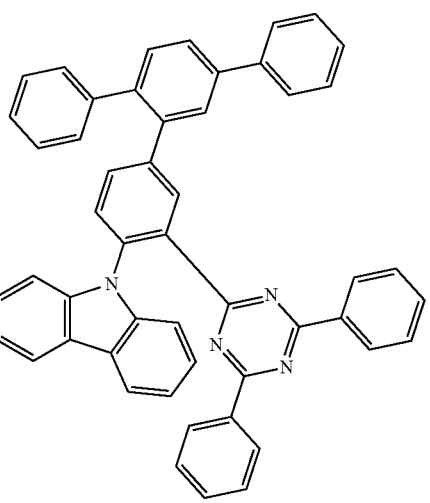
160
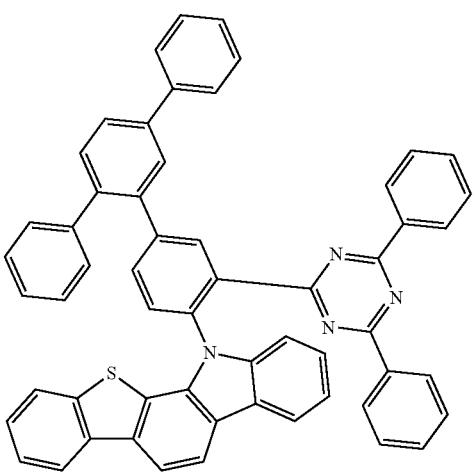

1297
-continued
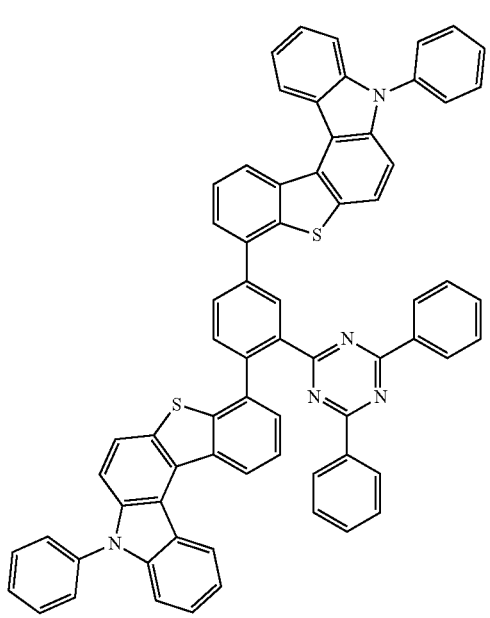
161
1298
-continued
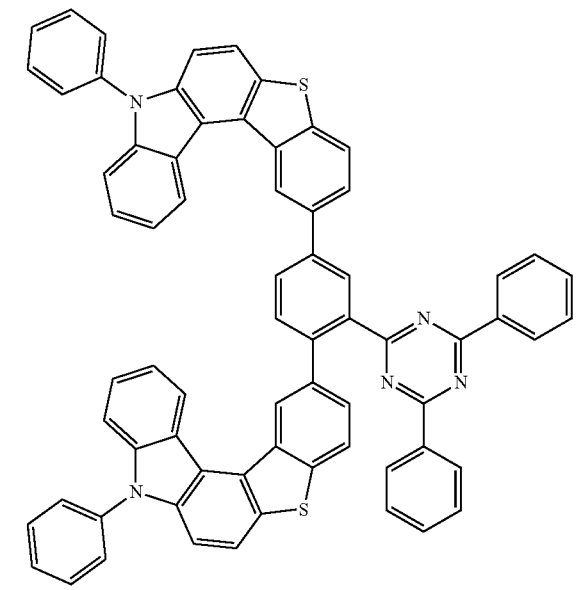
163
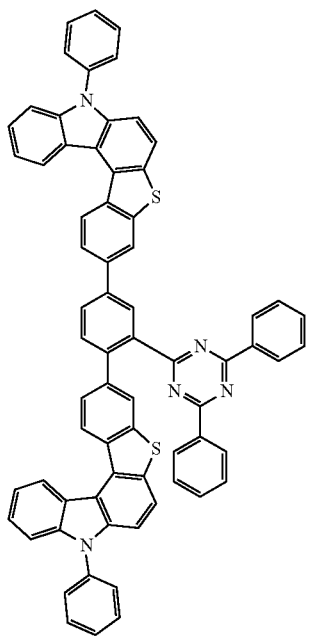
162
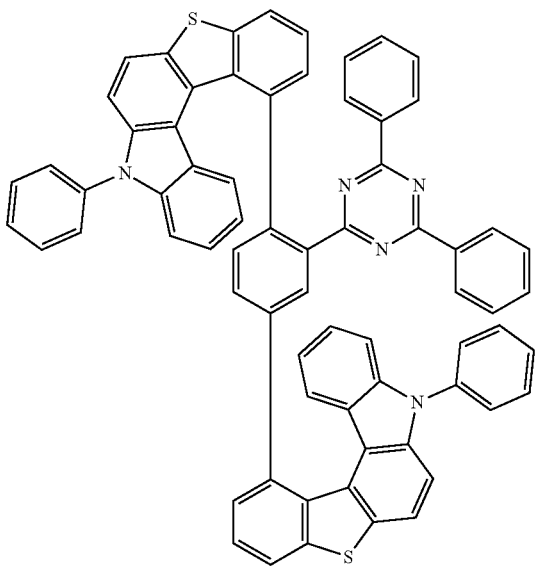
164

1299
-continued
165
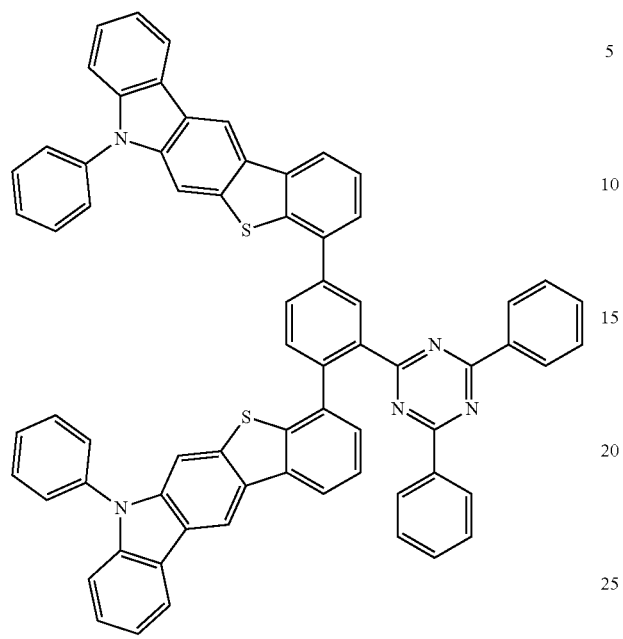
166
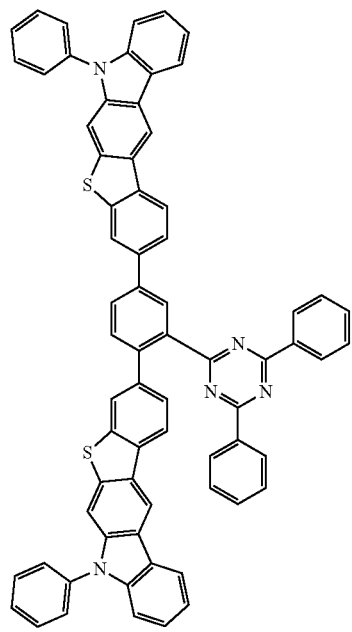
1300
-continued
167
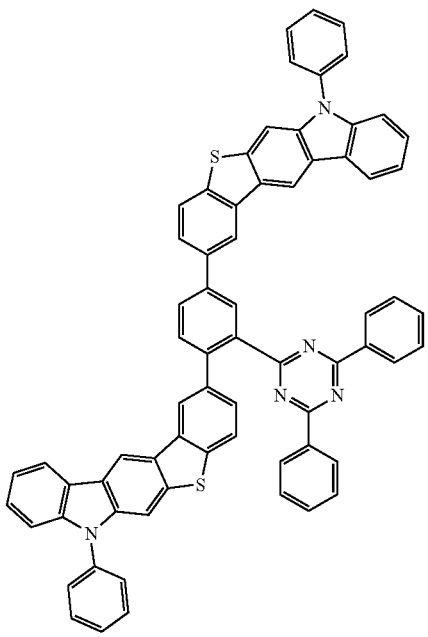
168
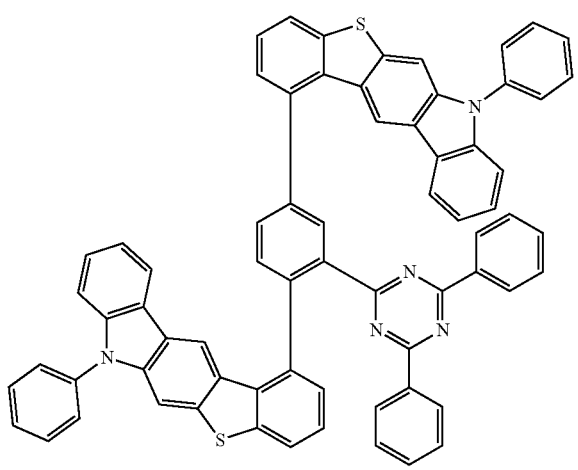

1301
-continued
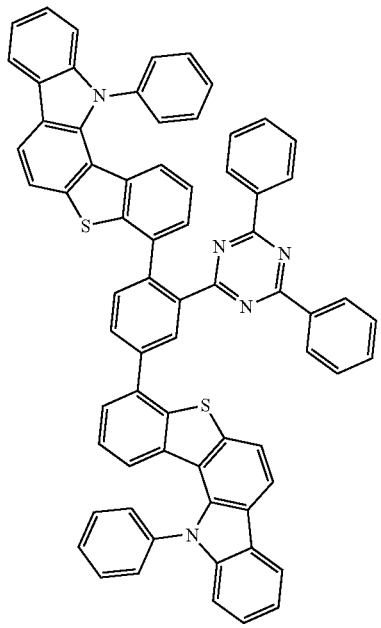
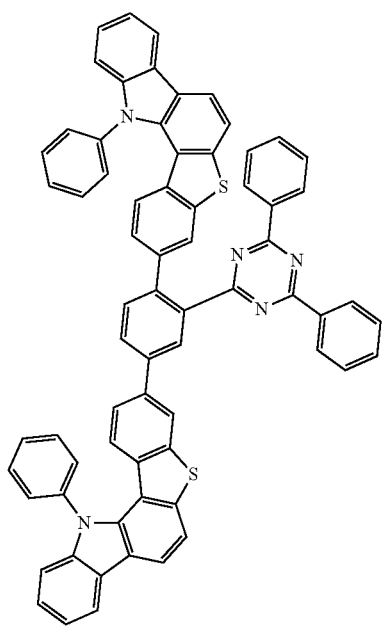
1302
-continued
169
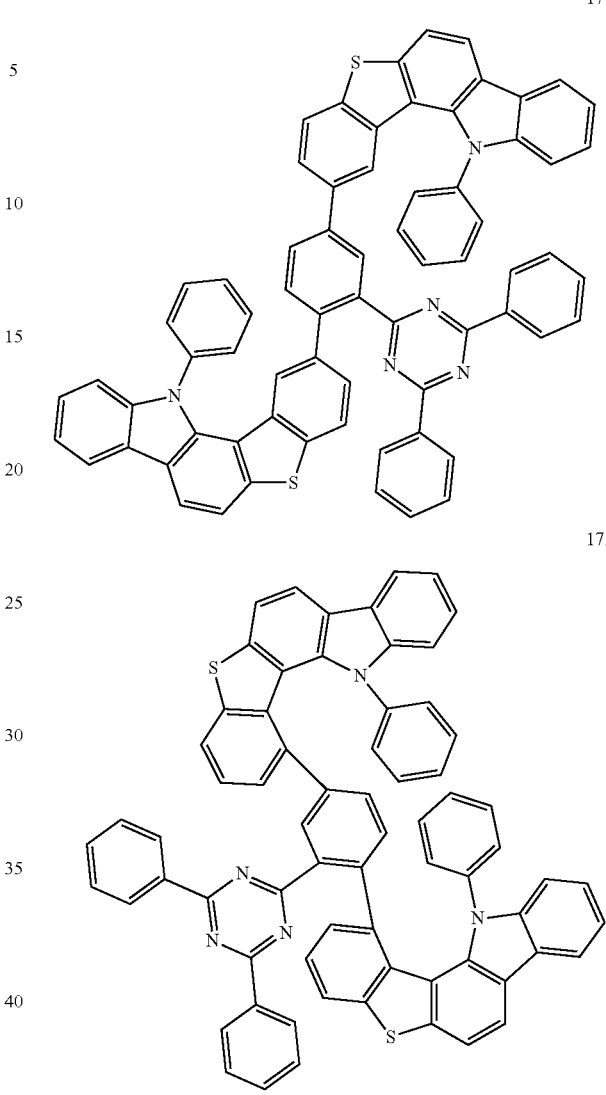
171
172
170
173
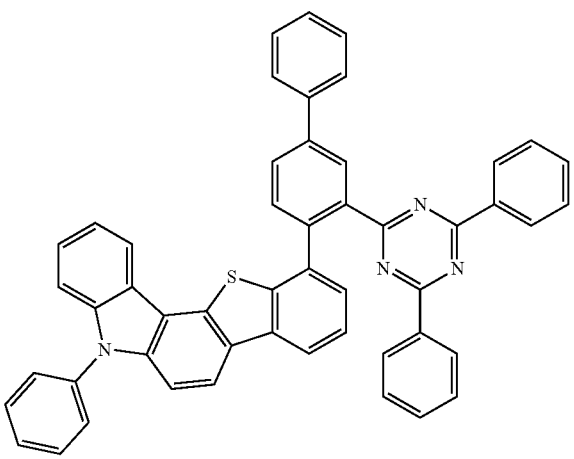

1303
-continued
174
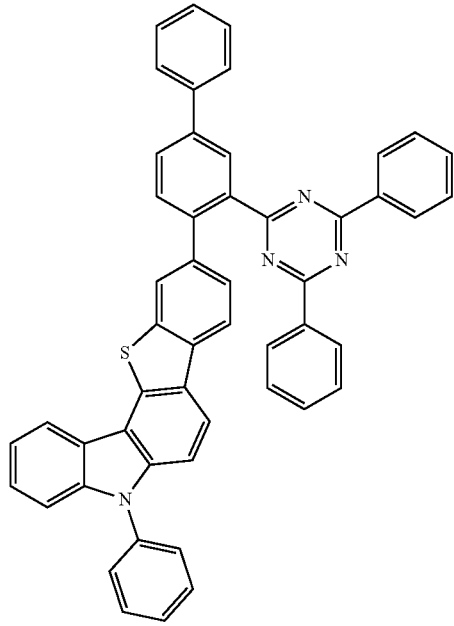
175
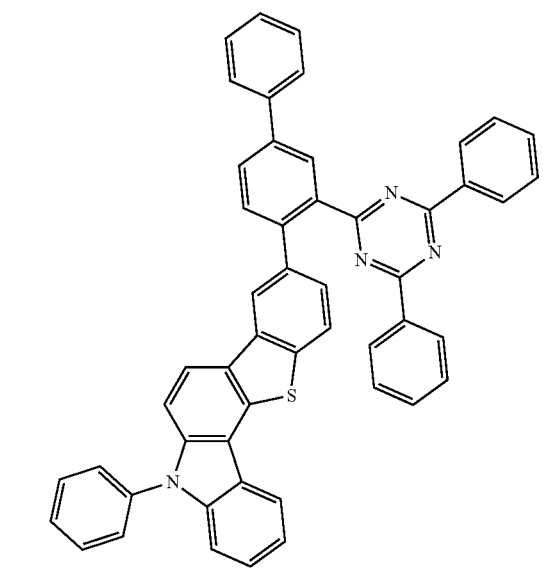
176
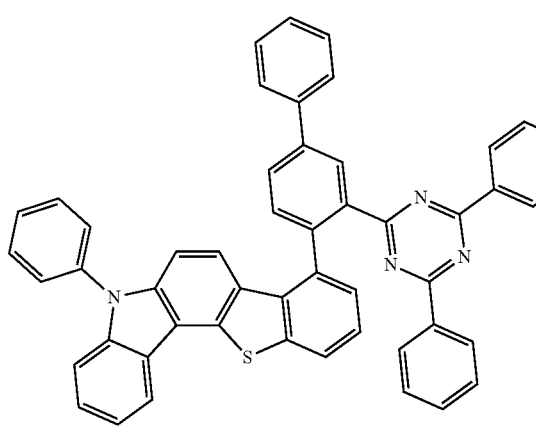
1304
-continued
177
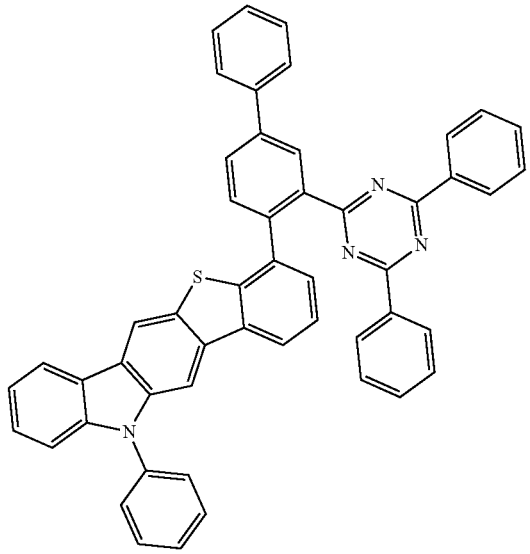
178
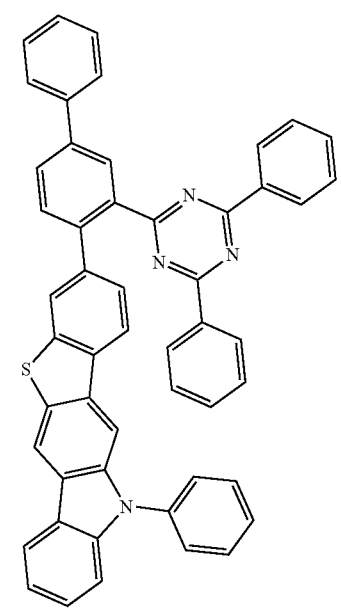

1305
-continued
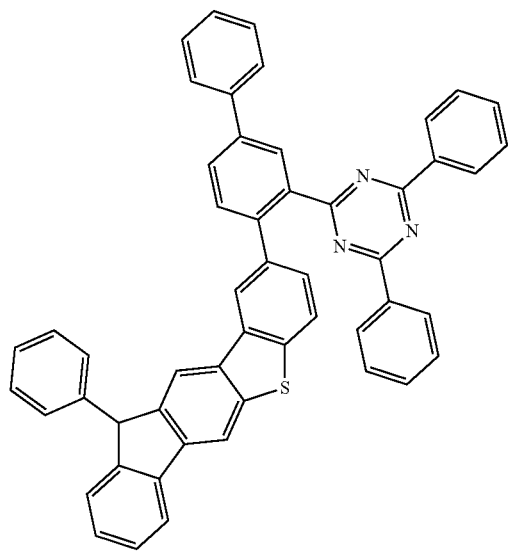
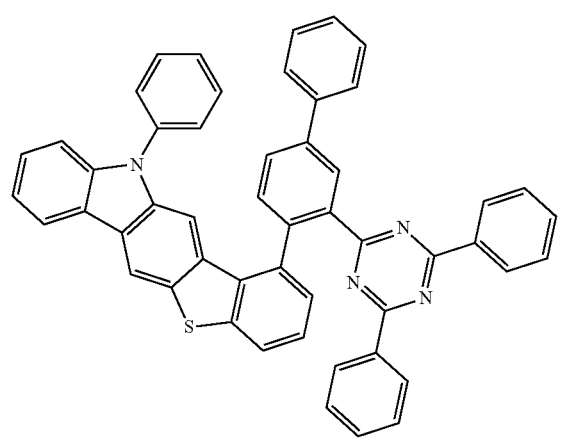
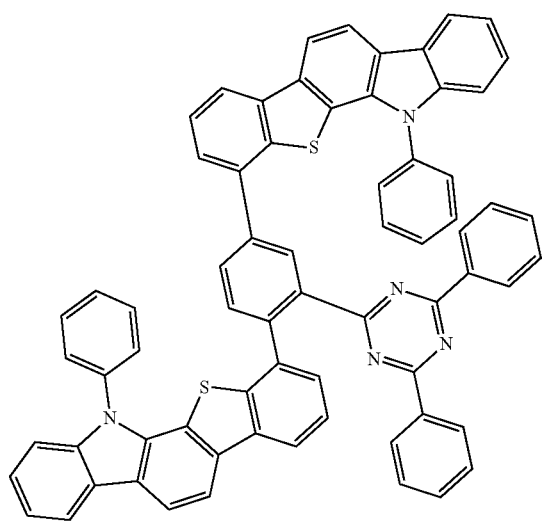
1306
-continued
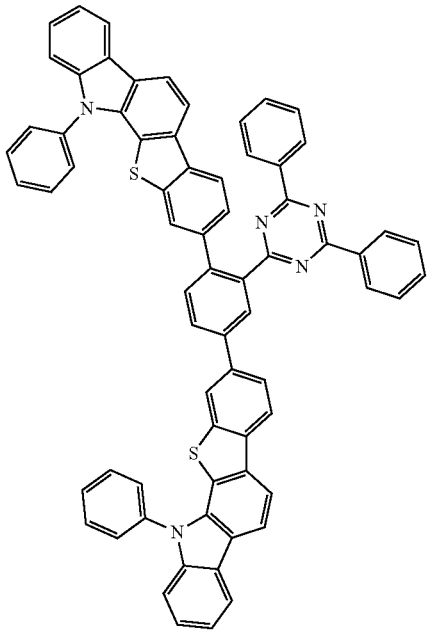
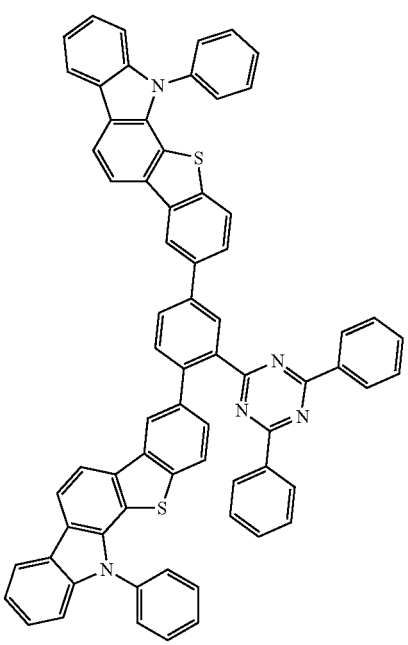

1307
-continued
1308
-continued
184
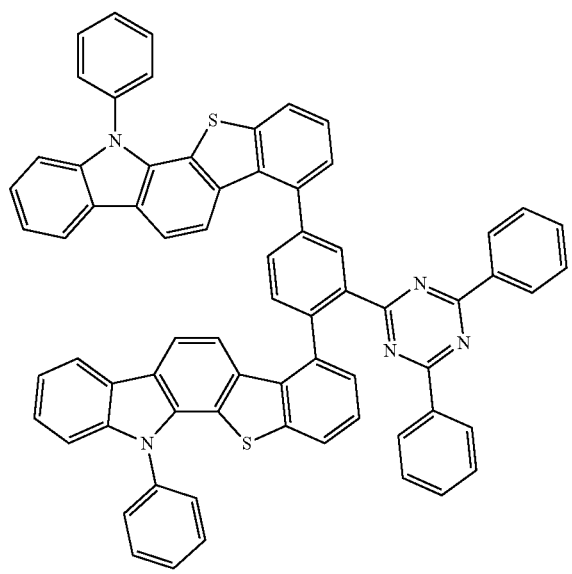
186
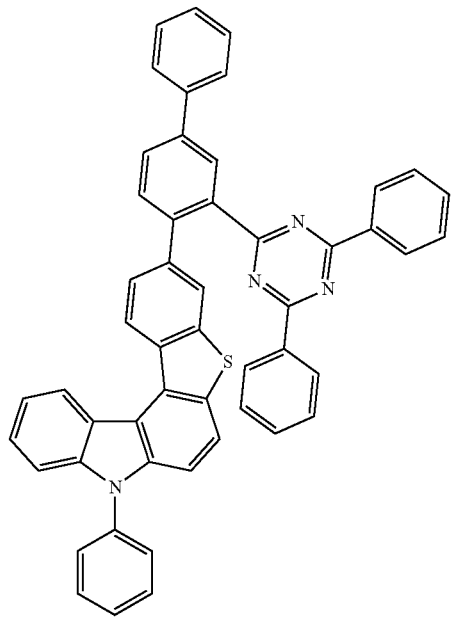
187
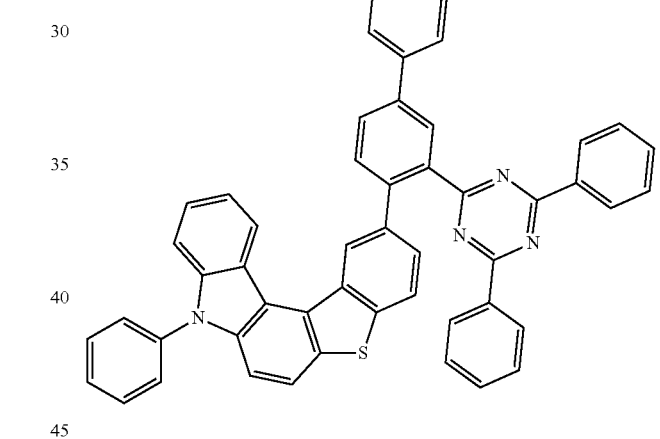
185
188
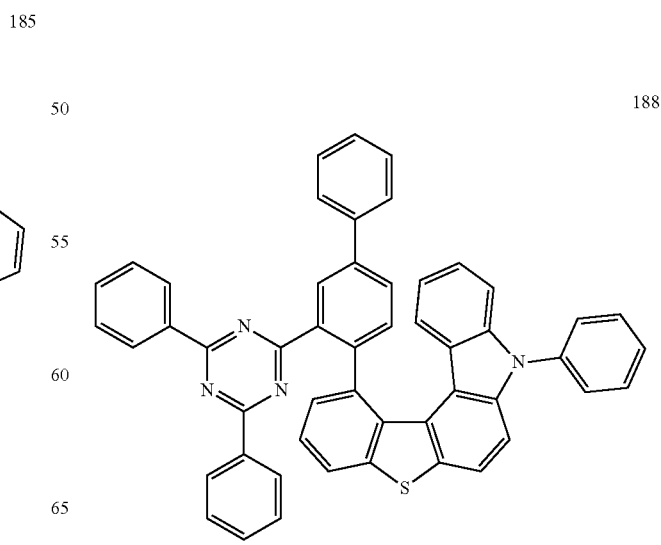

1309
-continued
189
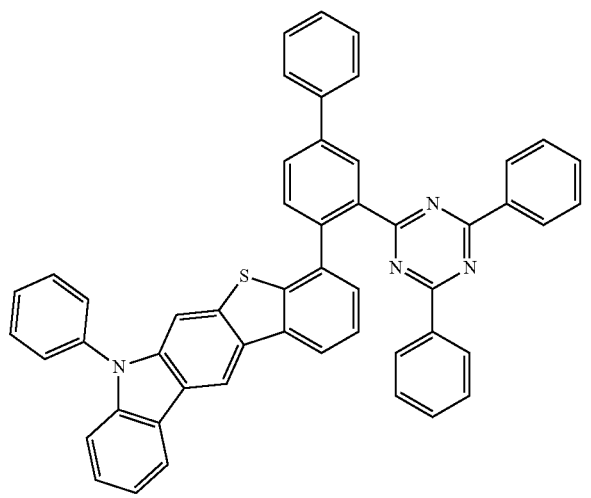
190
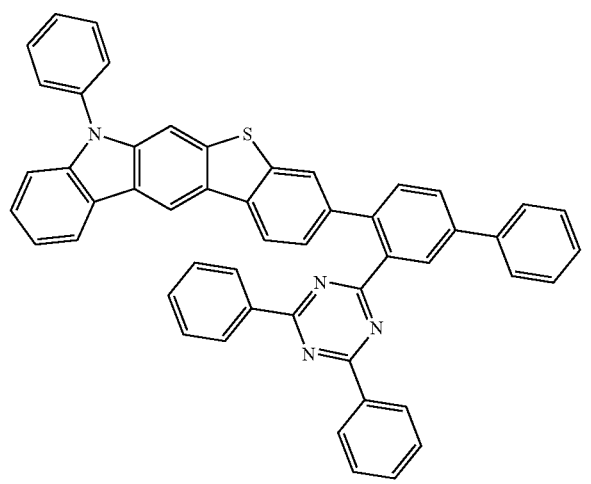
191
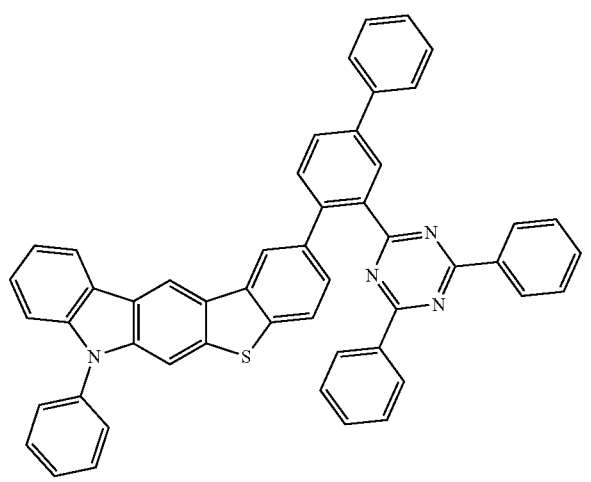
1310
-continued
192
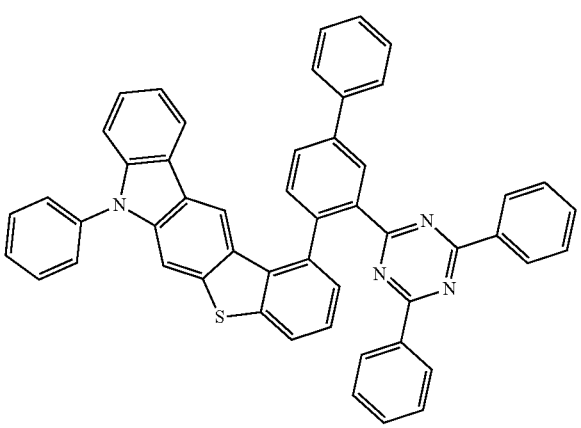
193
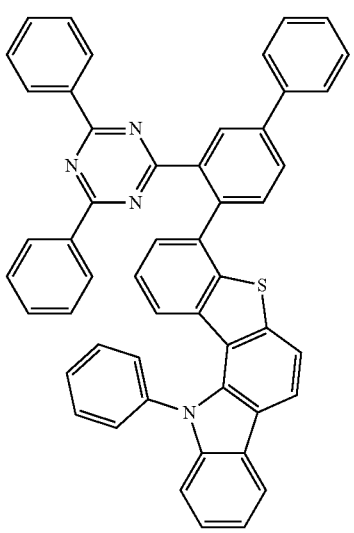
194
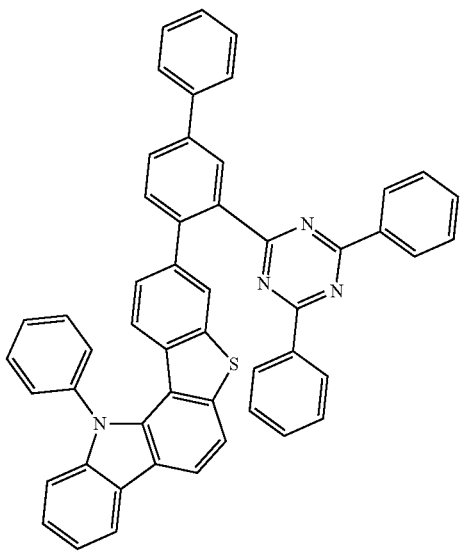

1311
-continued
195
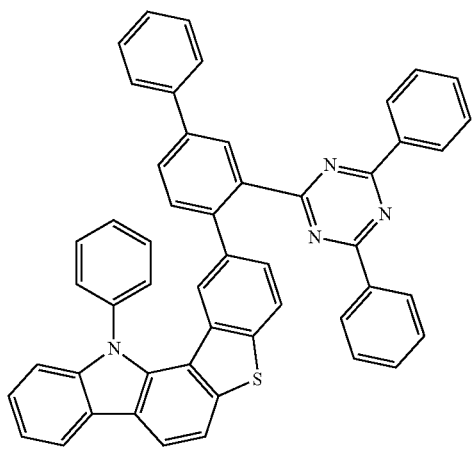
196
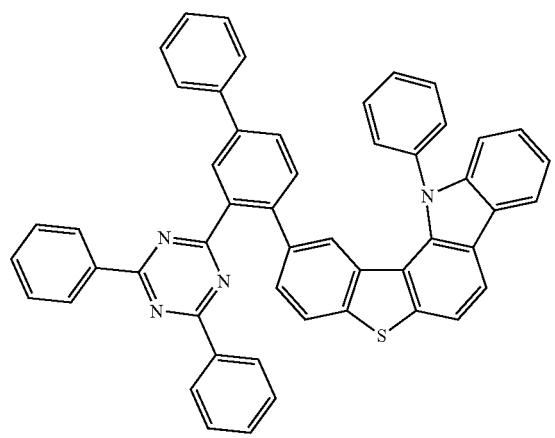
197
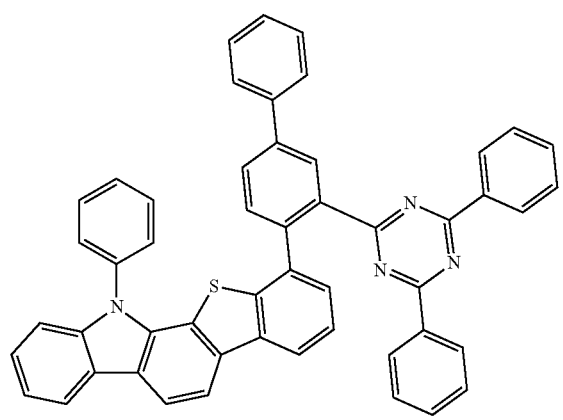
1312
-continued
198
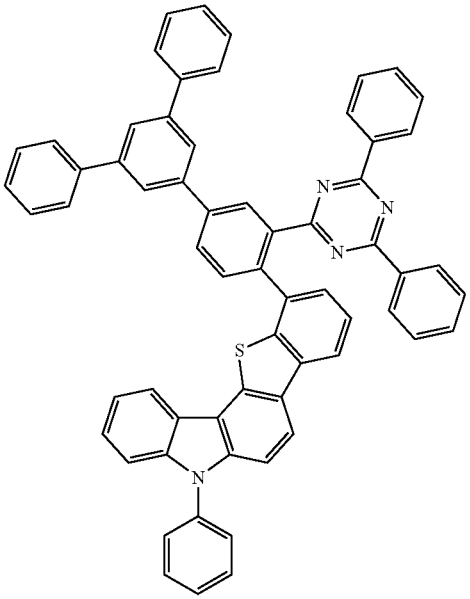
199
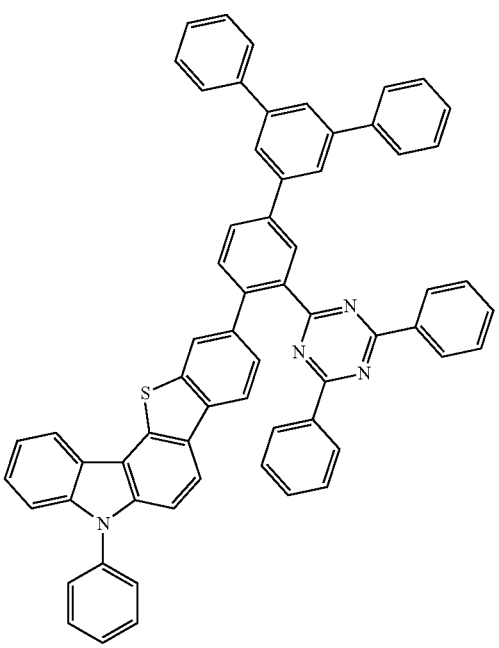

1313
-continued
1314
-continued
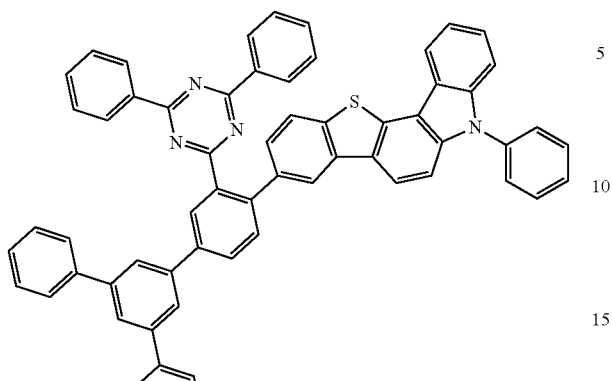
200
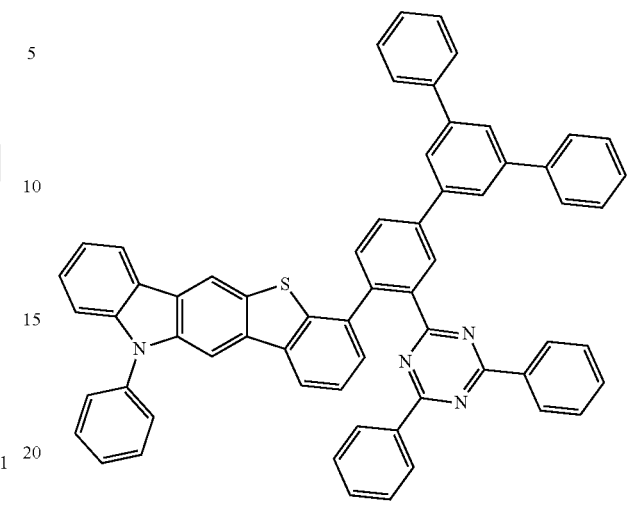
203
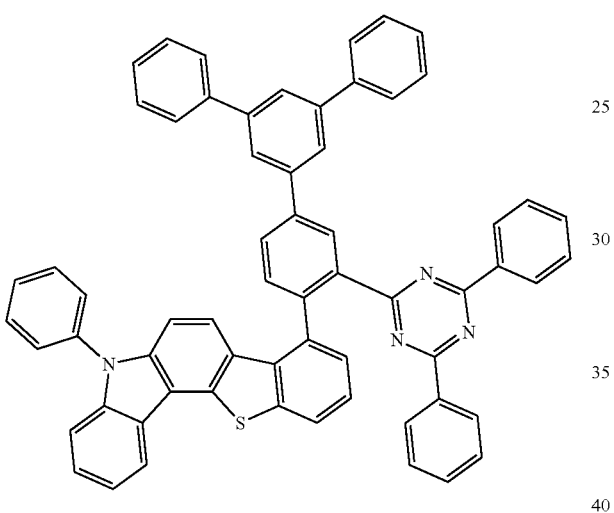
201
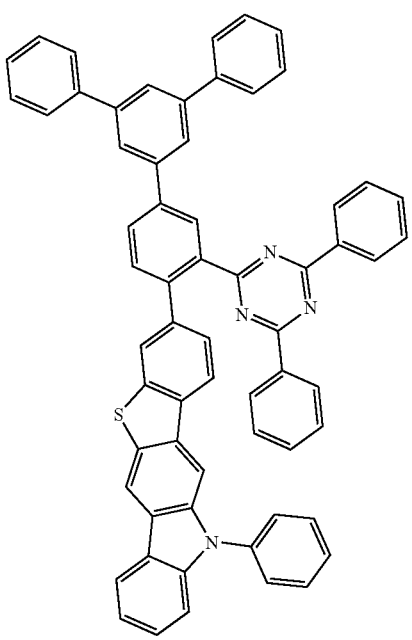
204
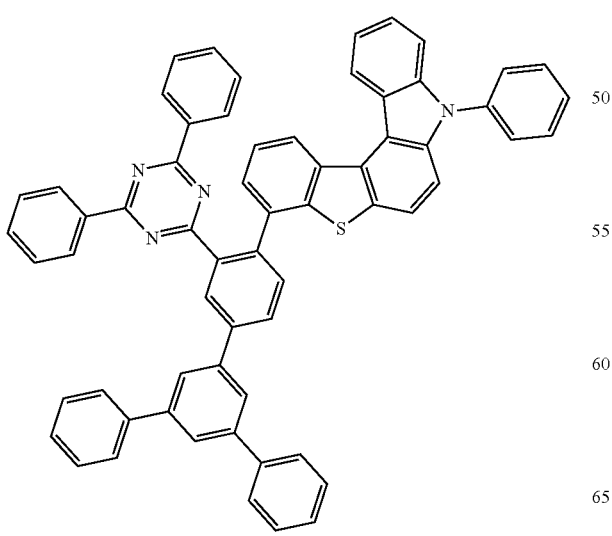
202

-continued
205
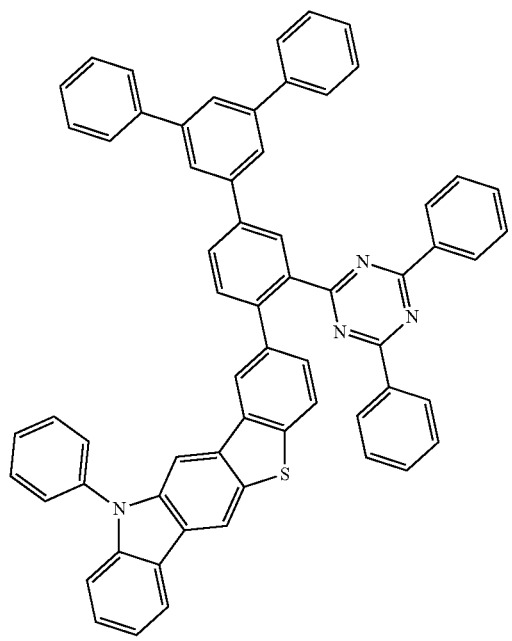
206
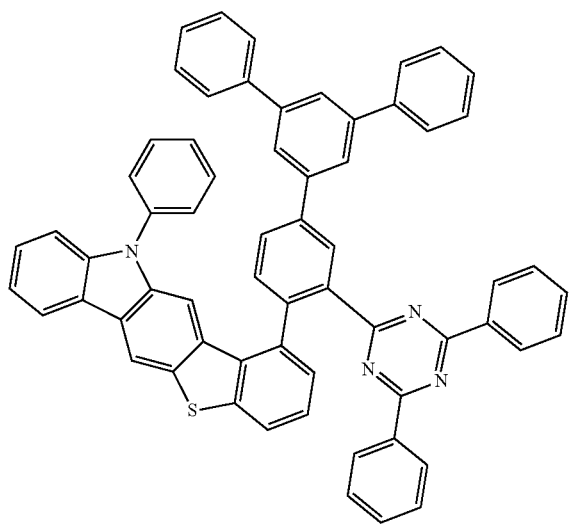
-continued
207
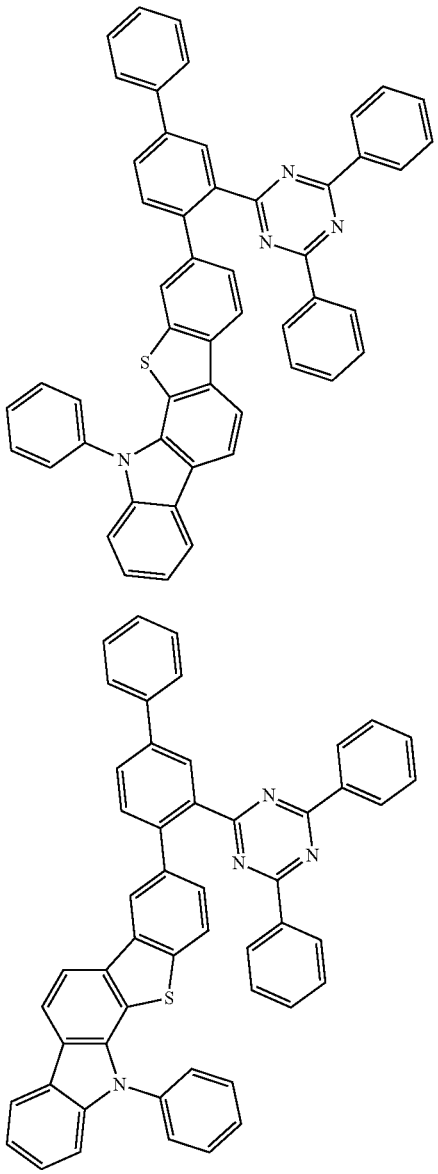
208
209
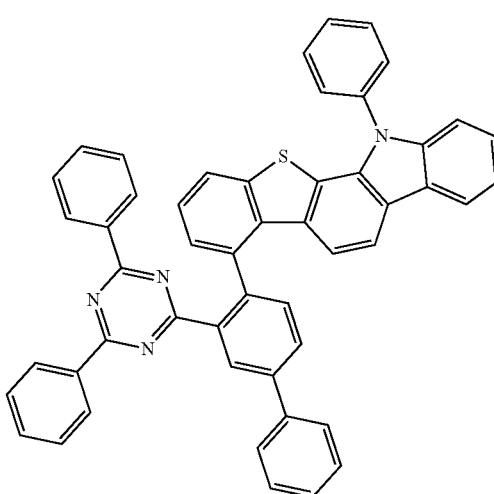

1317
-continued
210
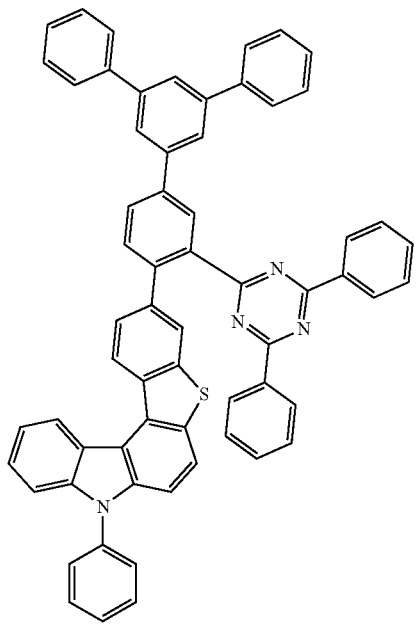
211
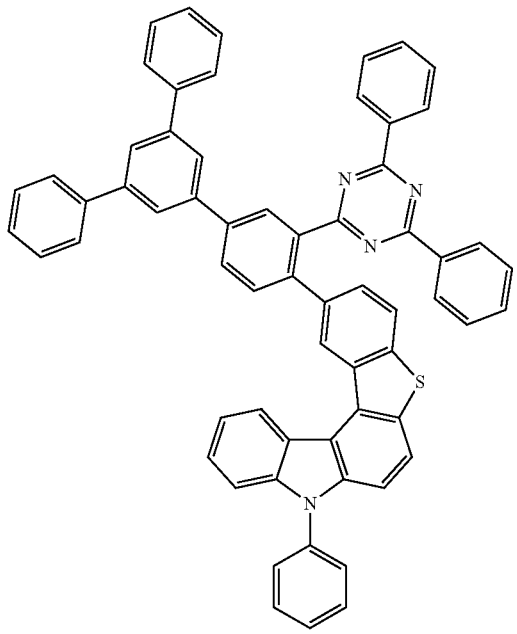
1318
-continued
212
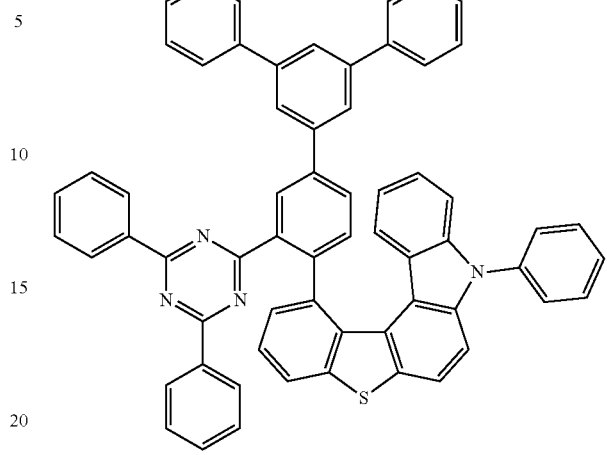
213
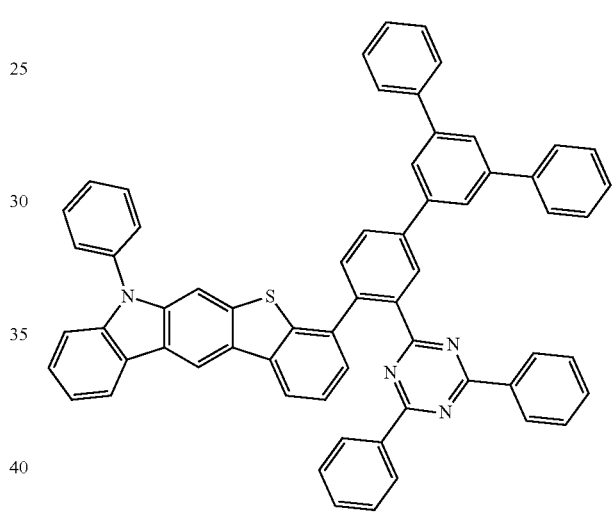
213
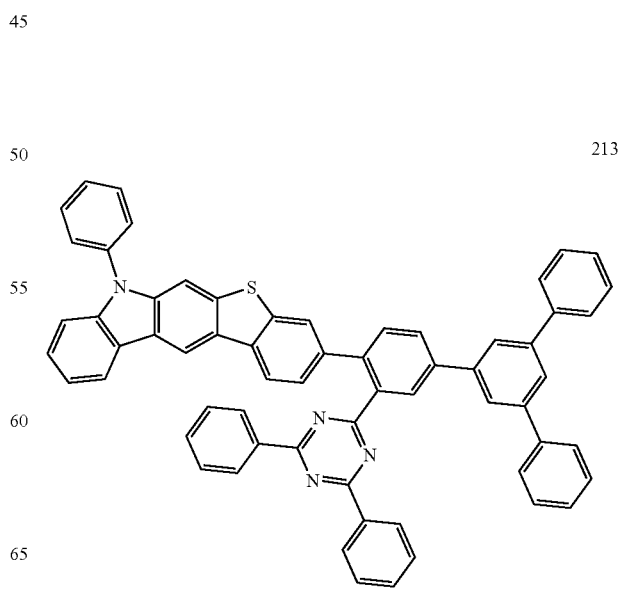

1319
-continued
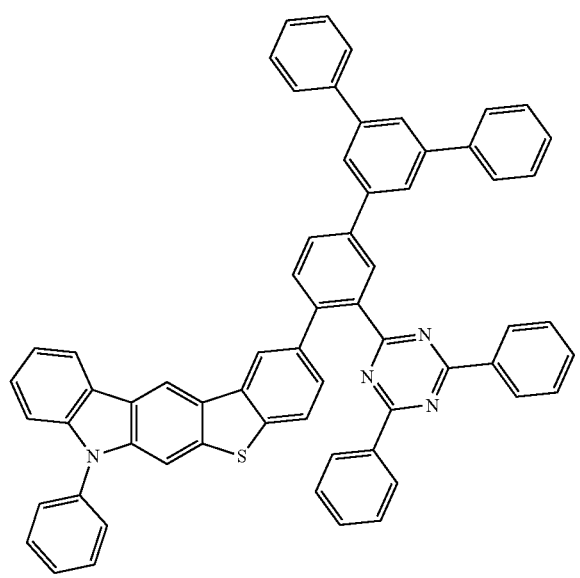
215
1320
-continued
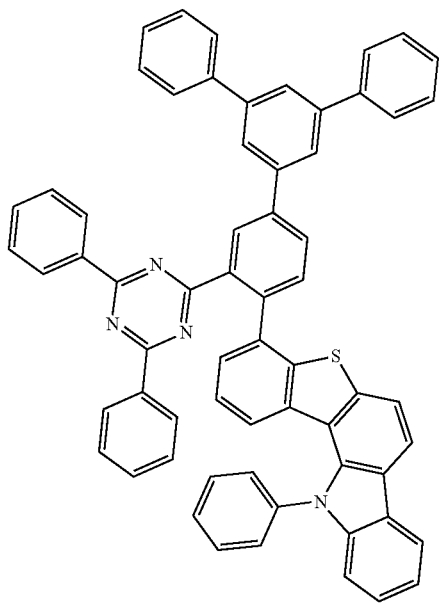
217
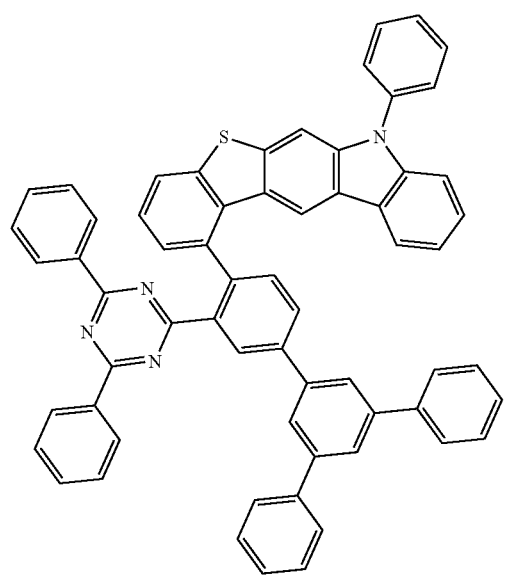
216
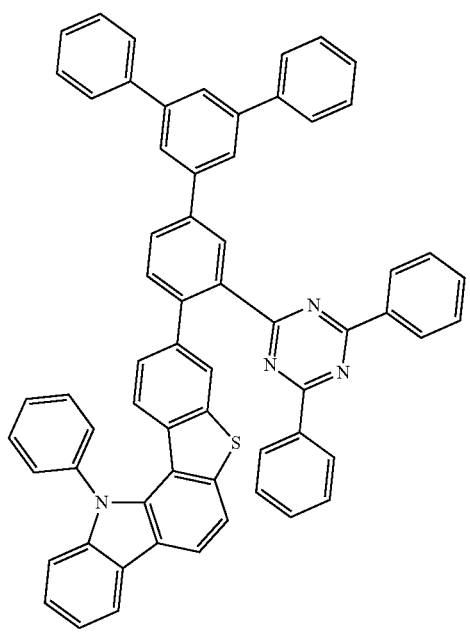
218

1321
-continued
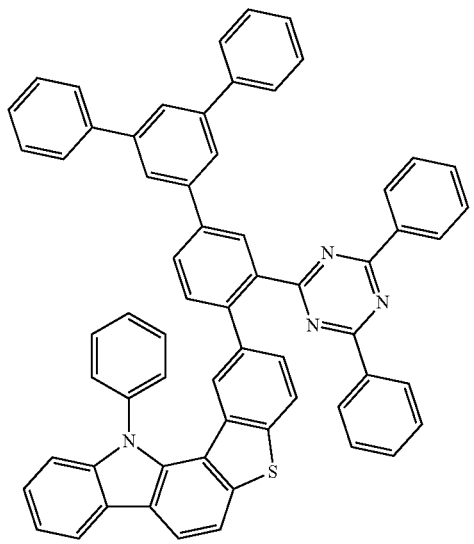
219
1322
-continued
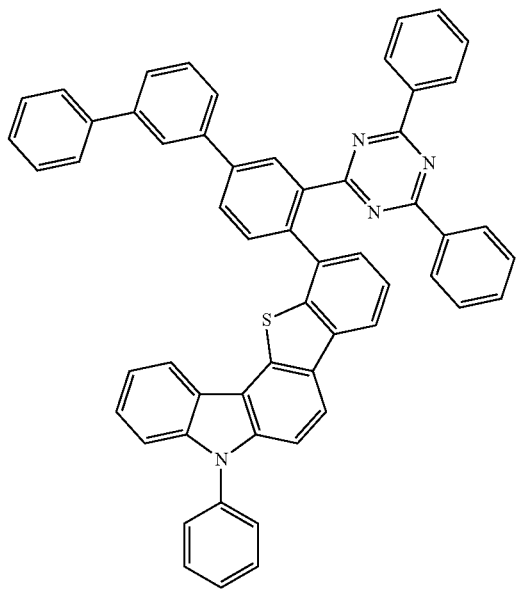
221
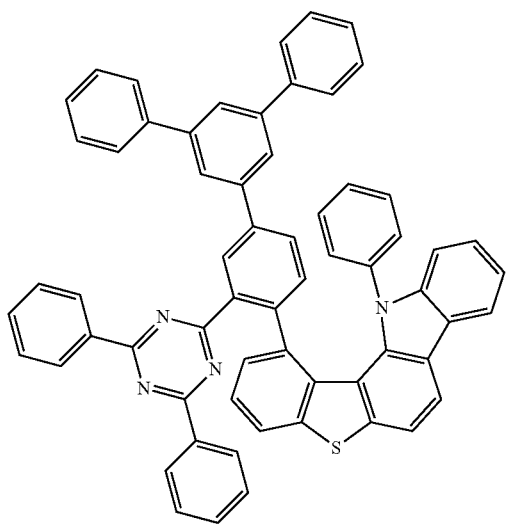
220
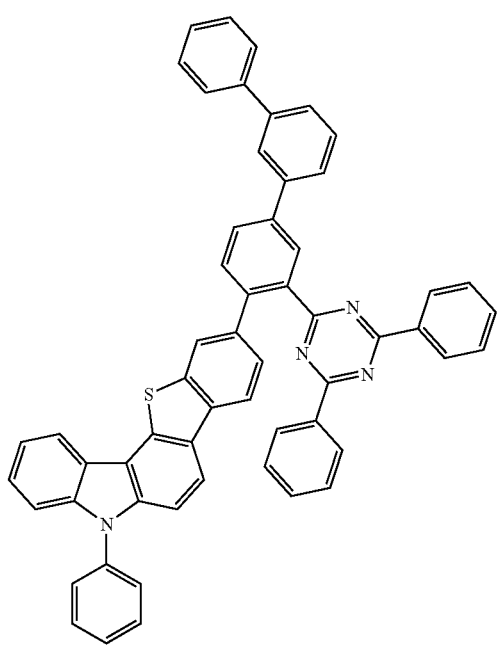
222

1323
-continued
223
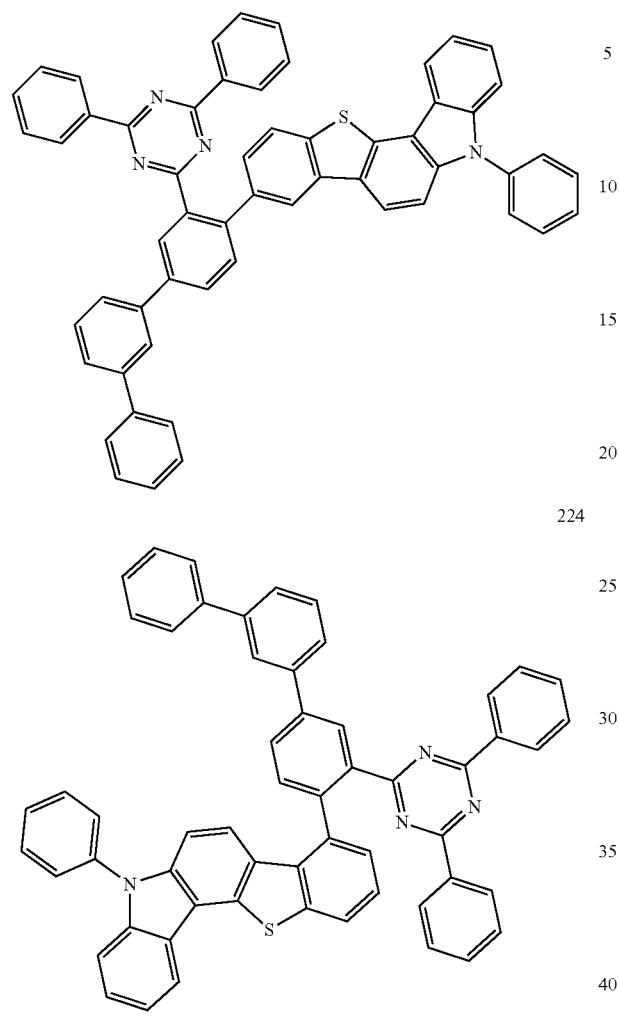
224
225
1324
-continued
226
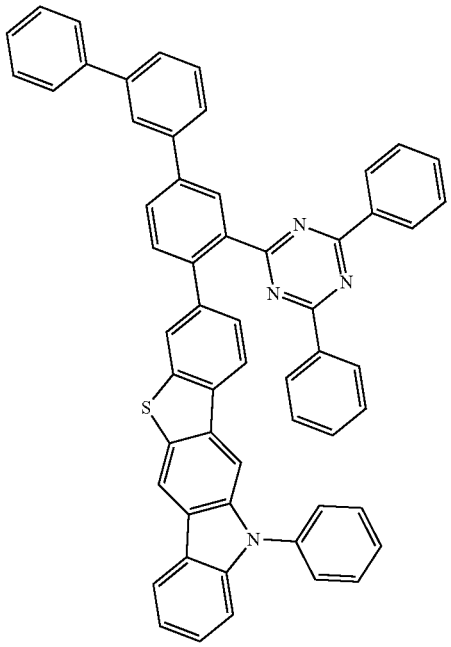
227
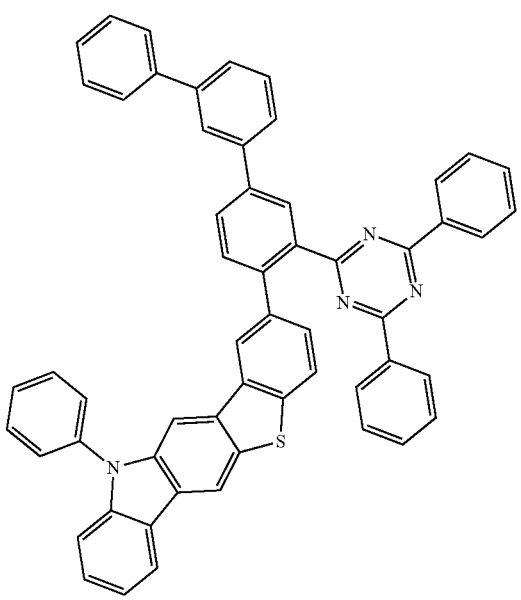
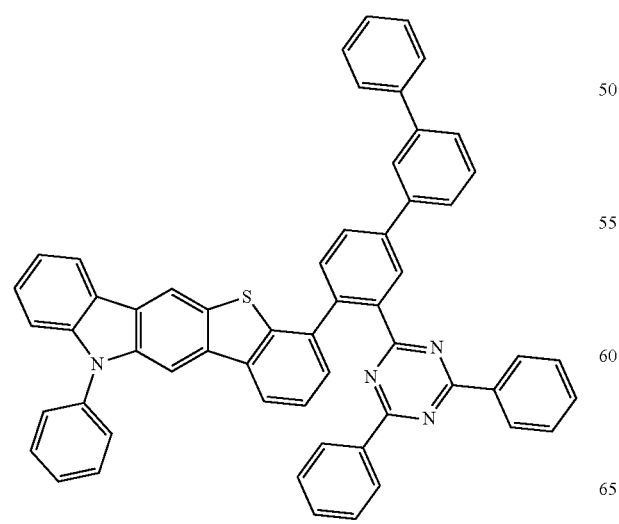

228
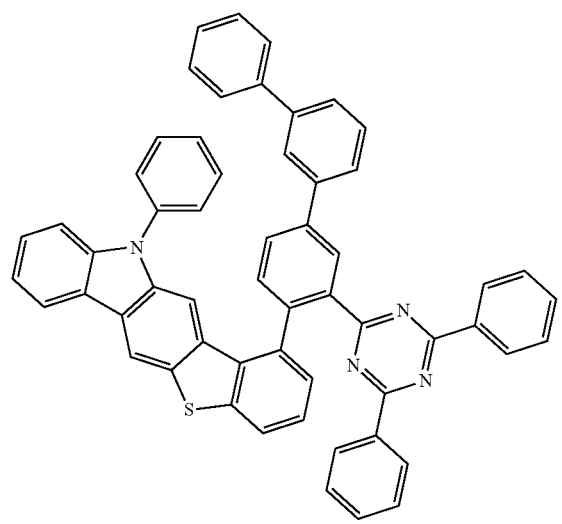
229
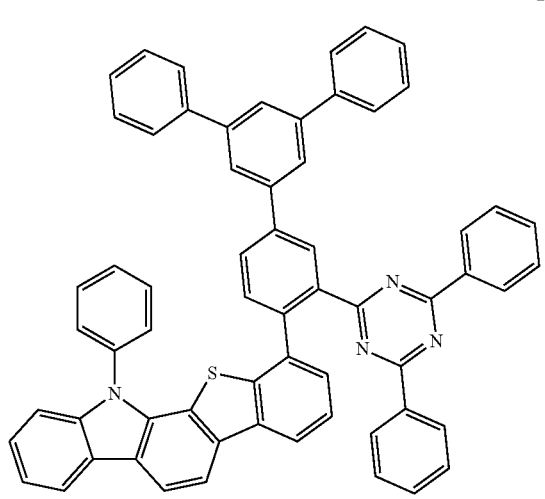
230
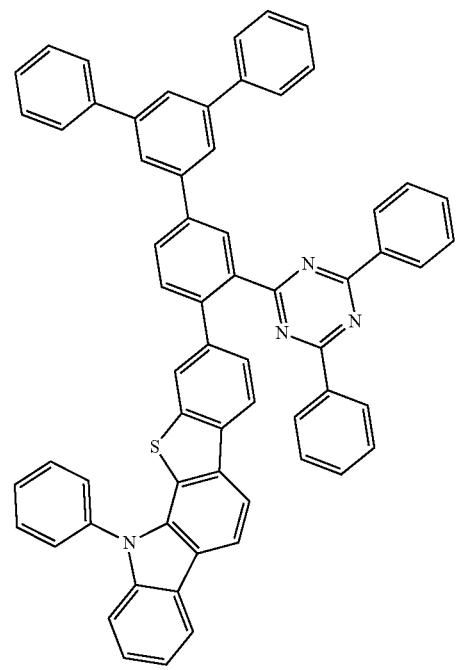
231
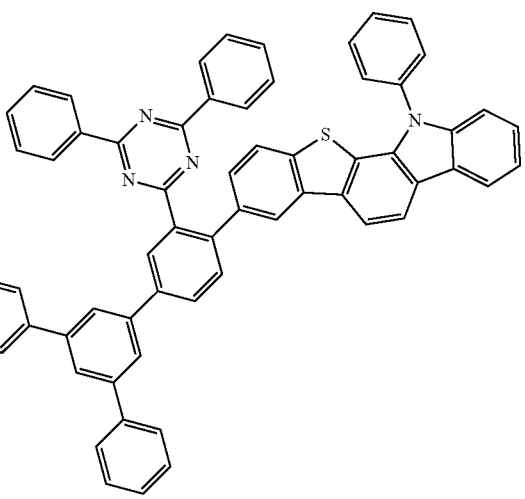

232
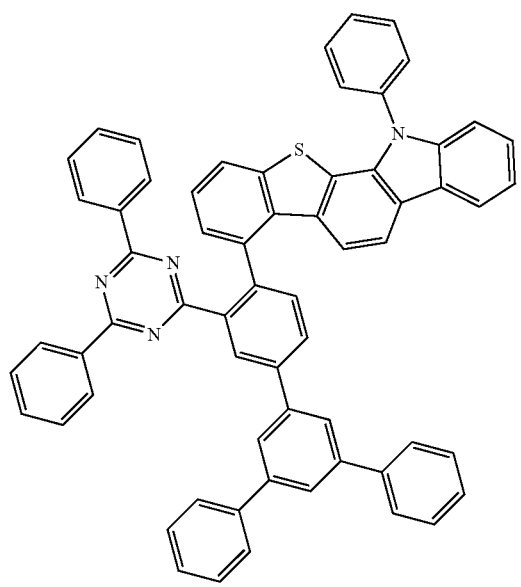
234
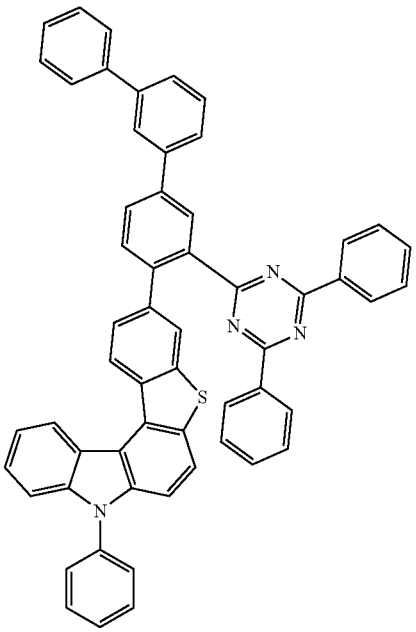
233
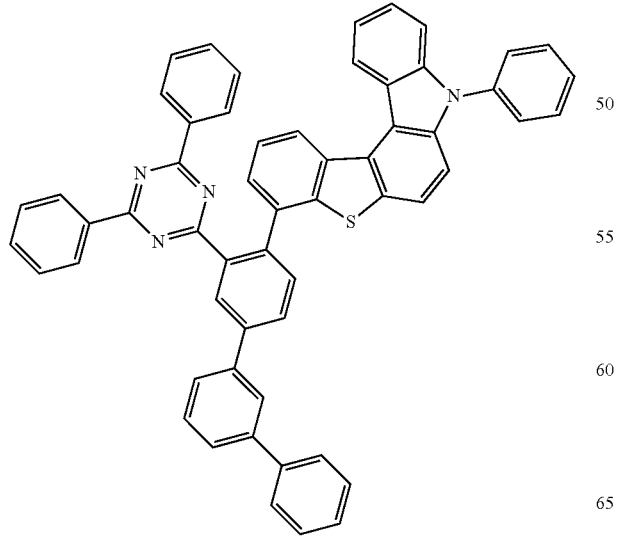
235
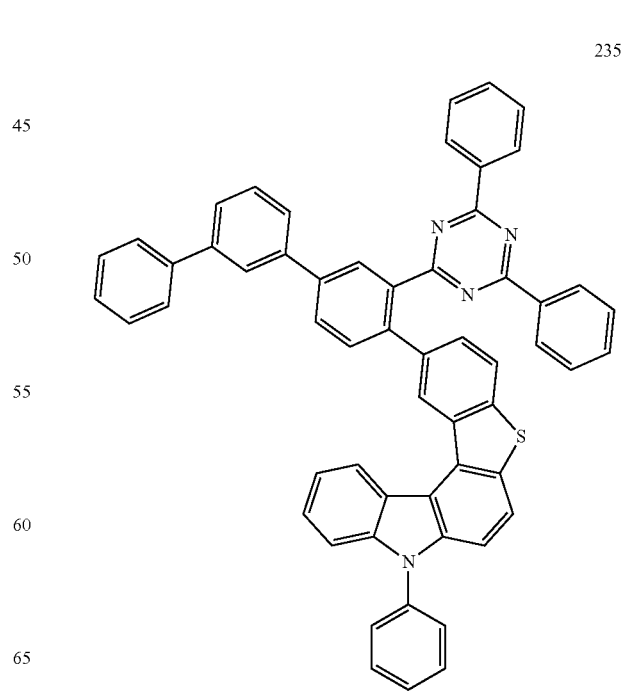

236
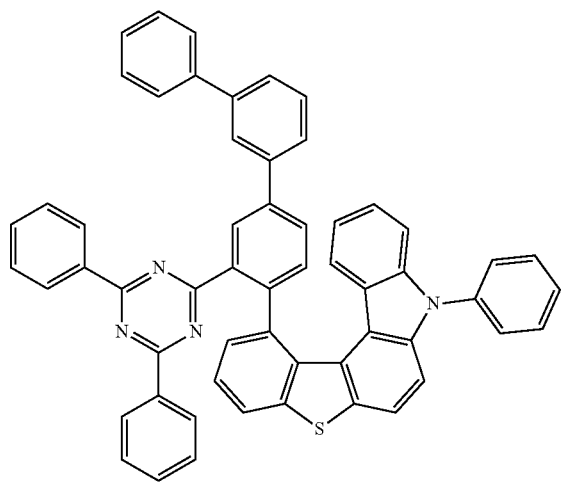
237
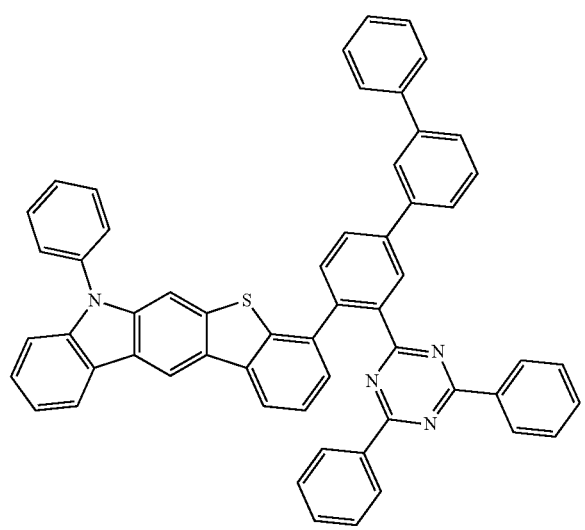
238
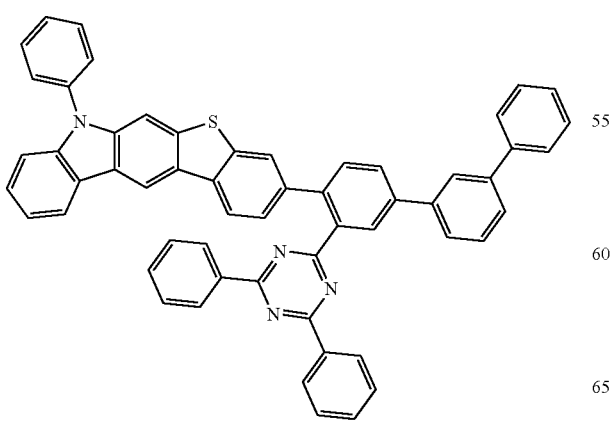
239
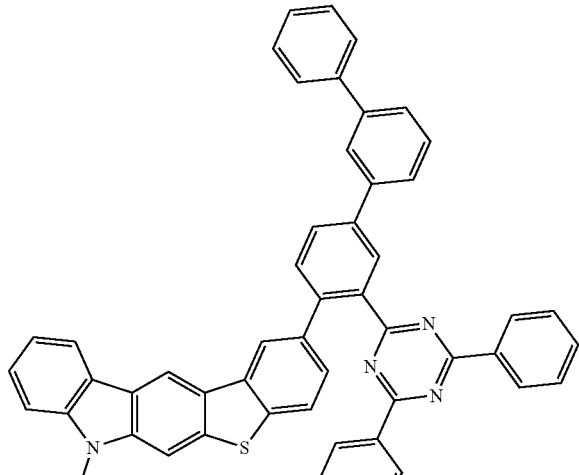
240
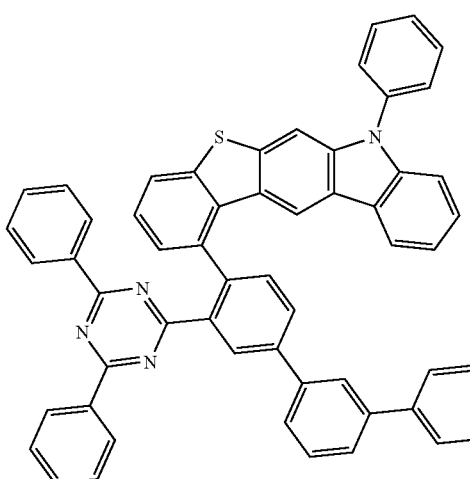
241
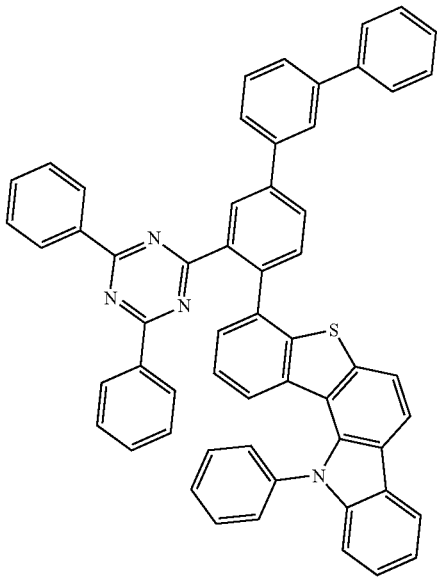

1331
-continued
242
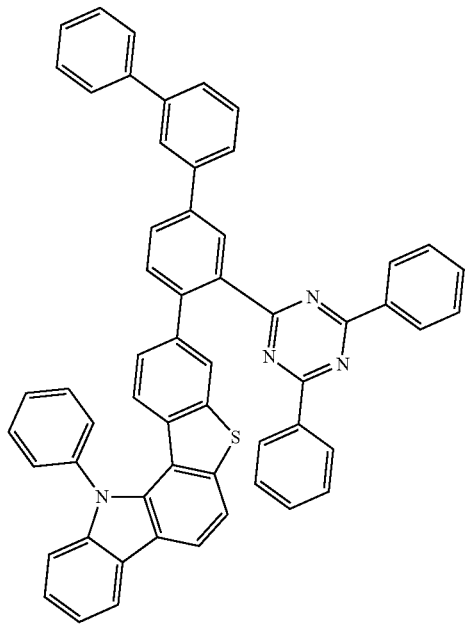
243
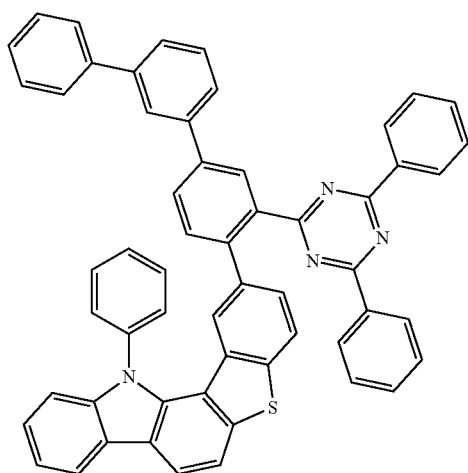
244
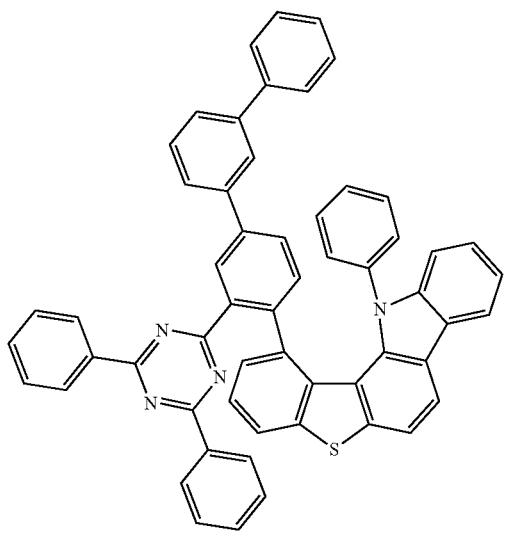
1332
-continued
245
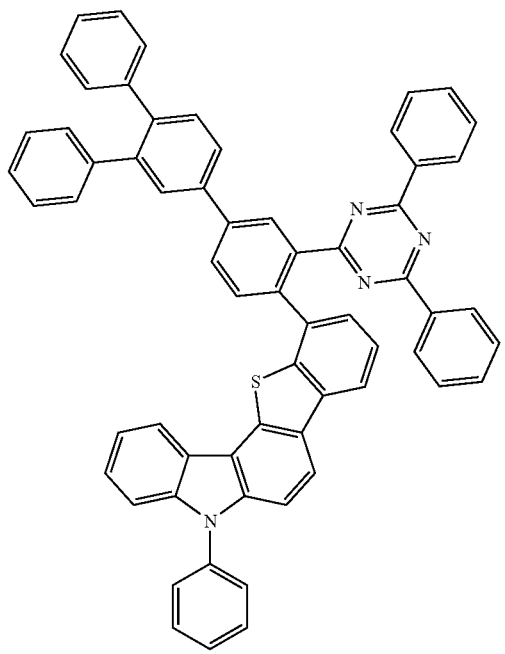
246
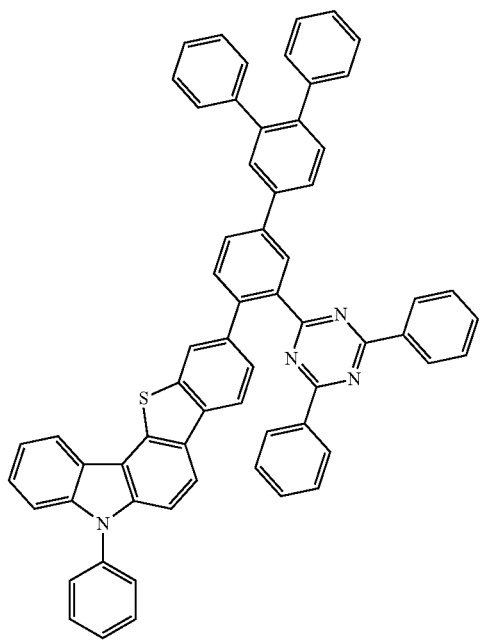

1333
-continued
247
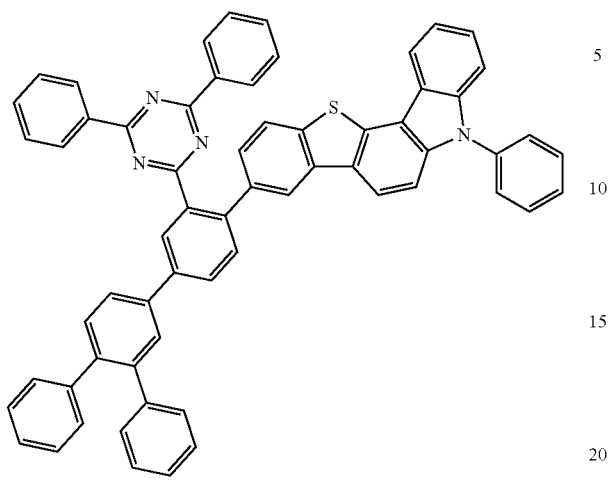
248
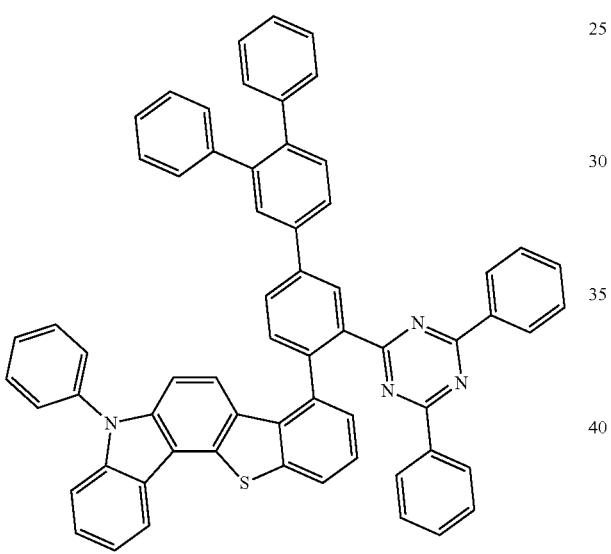
1334
-continued
250
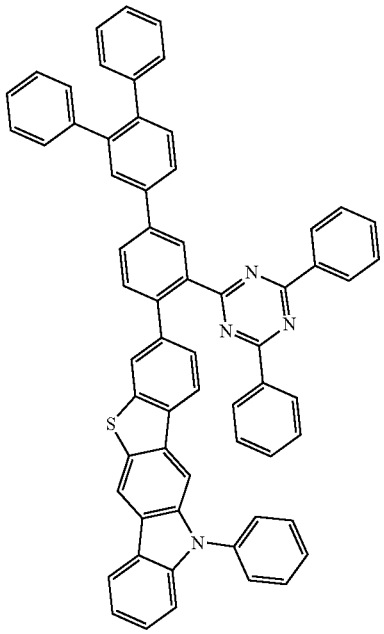
249
251
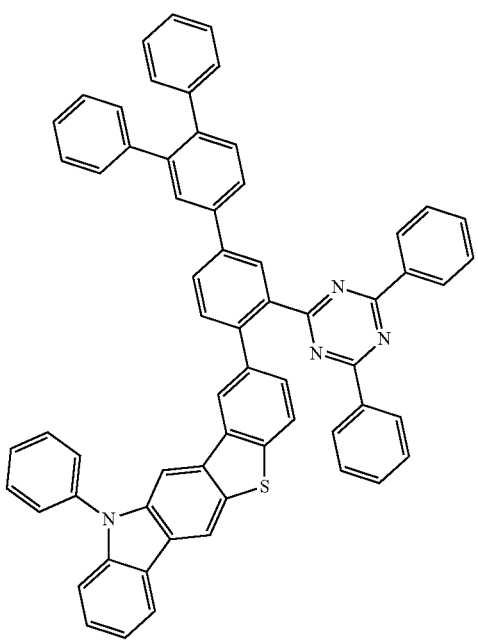

1335 -continued
252
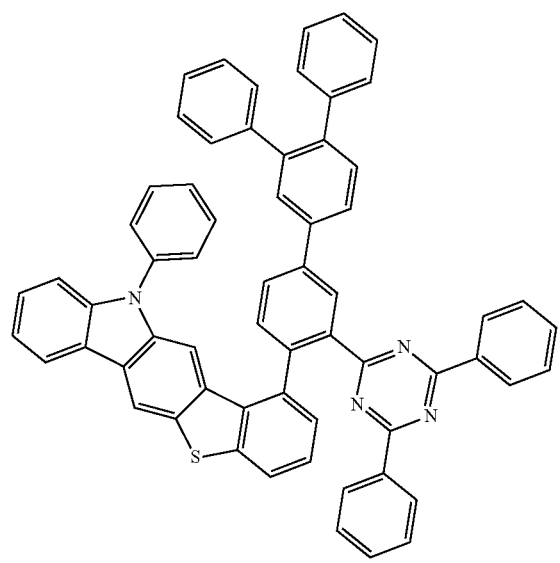
253
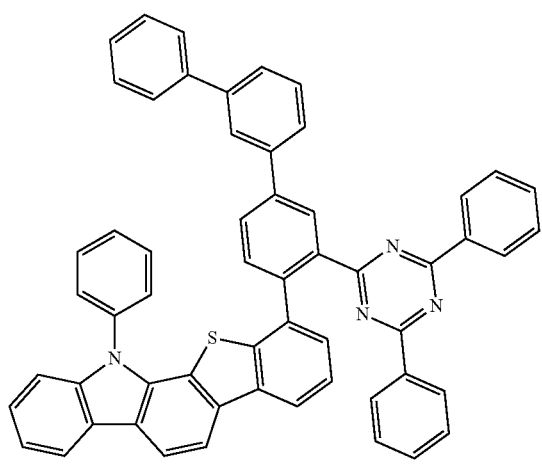
1336 -continued
254
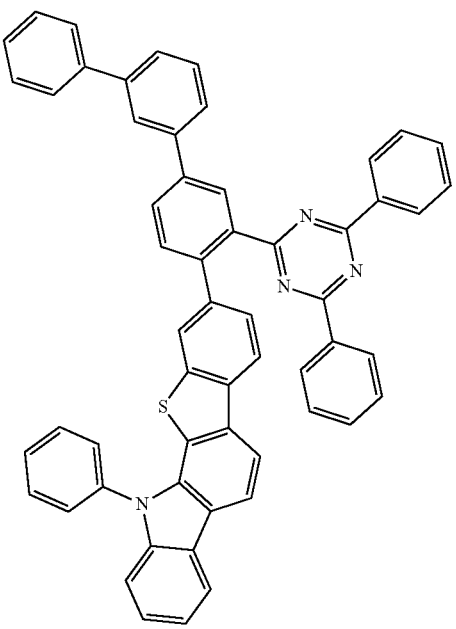
255
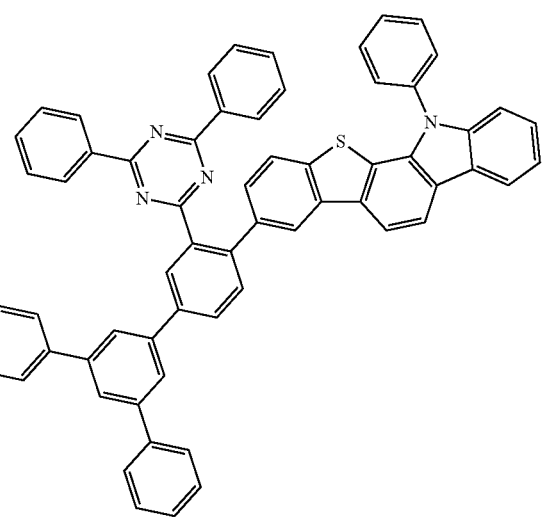

256
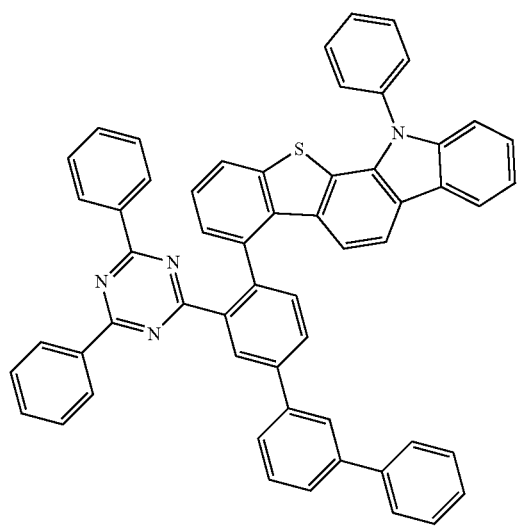
258
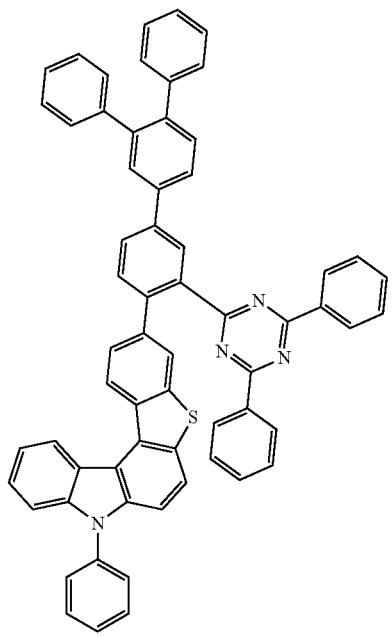
257
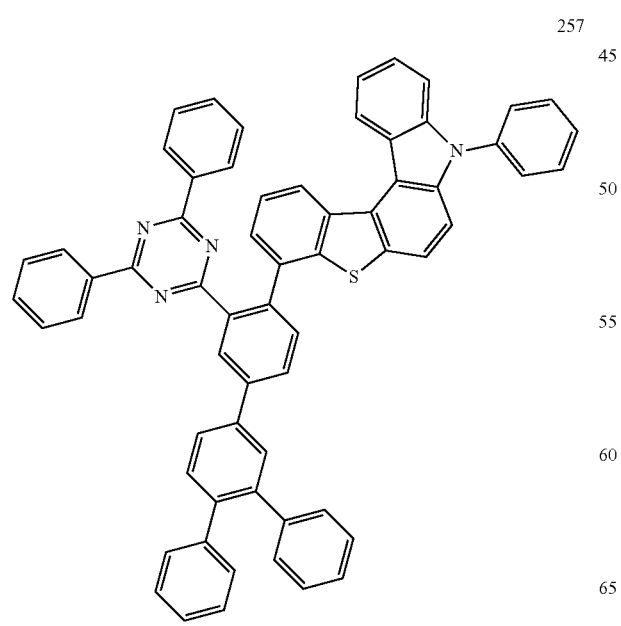
259
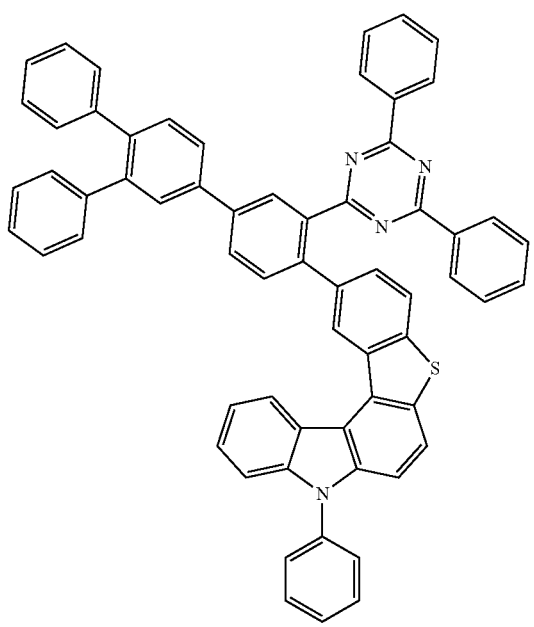

1339
-continued
260
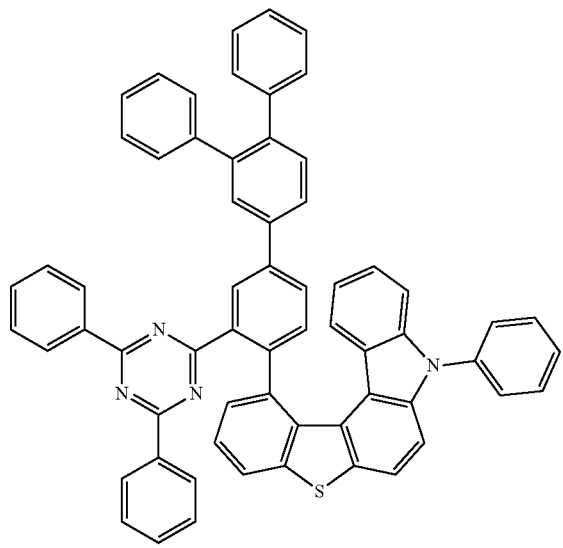
261
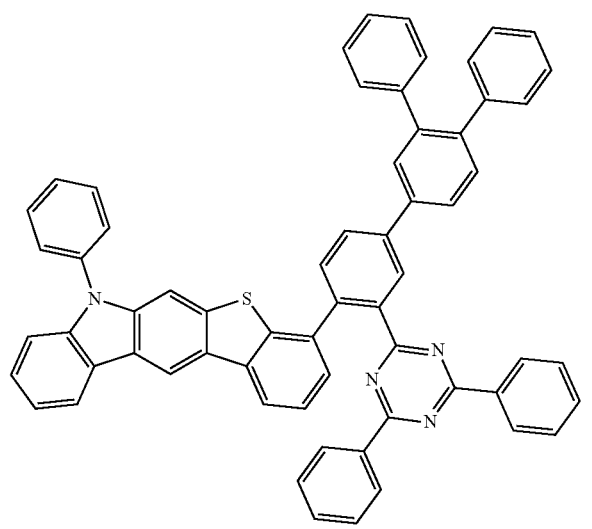
262
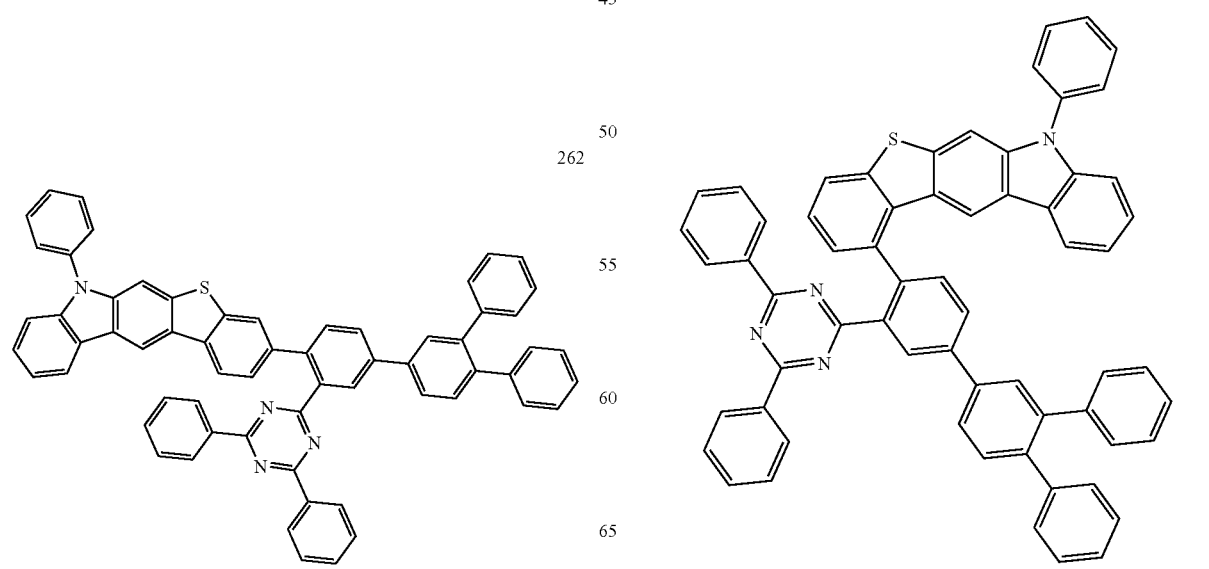
1340
-continued
263
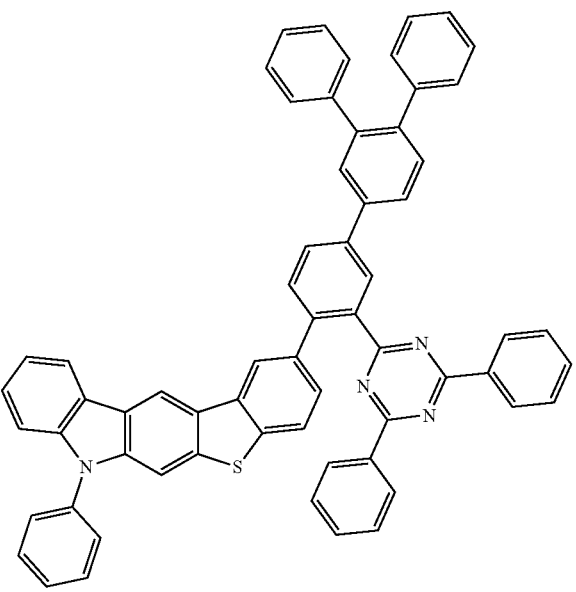
264
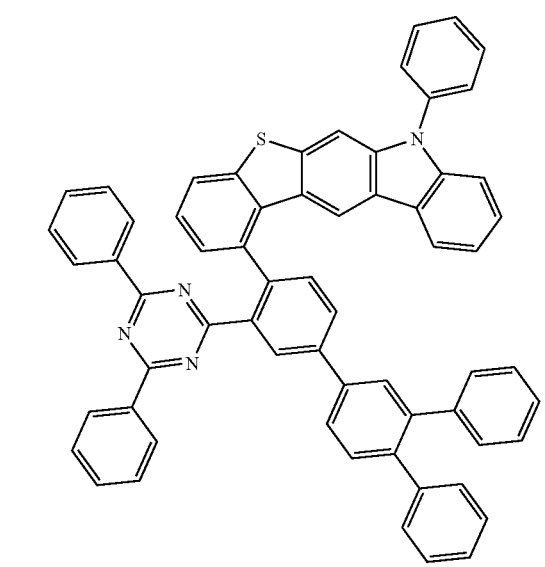

1341
-continued
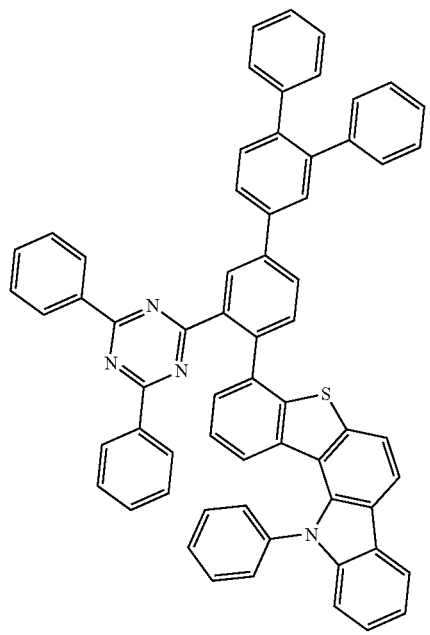
265
1342
-continued
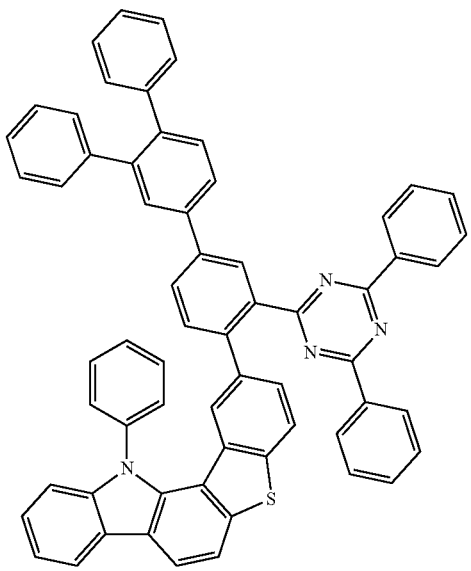
267
266
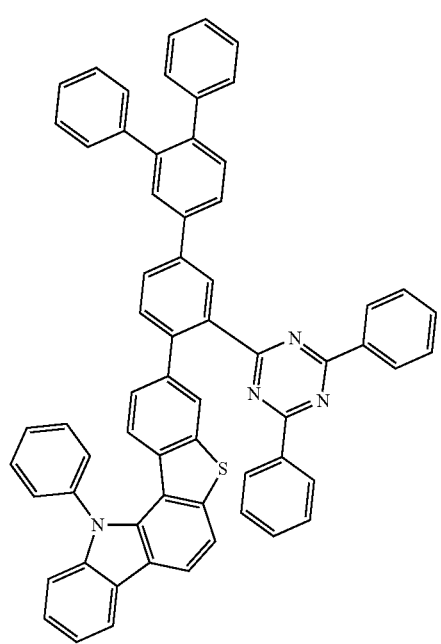
268
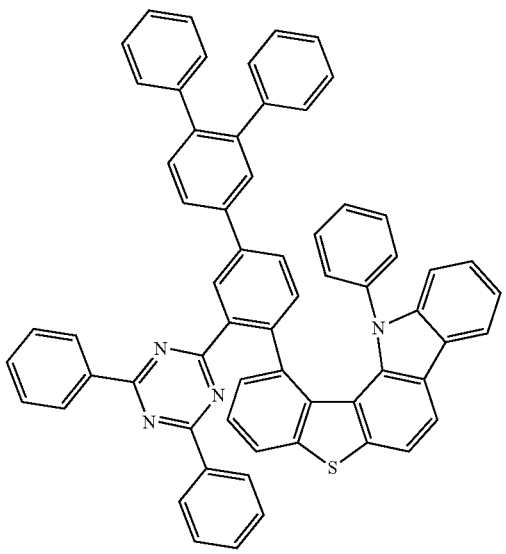

1343
-continued
269
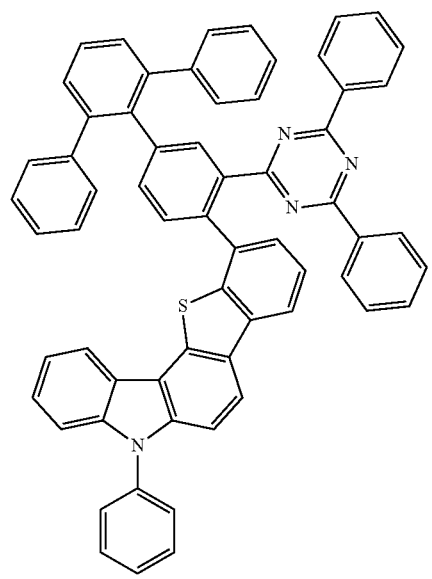
270
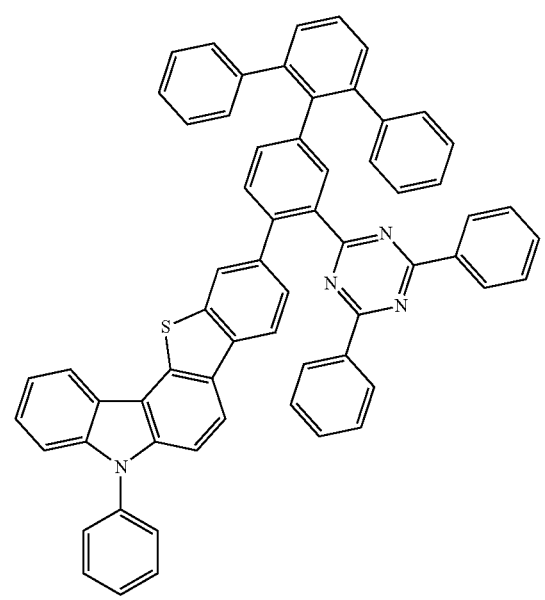
271
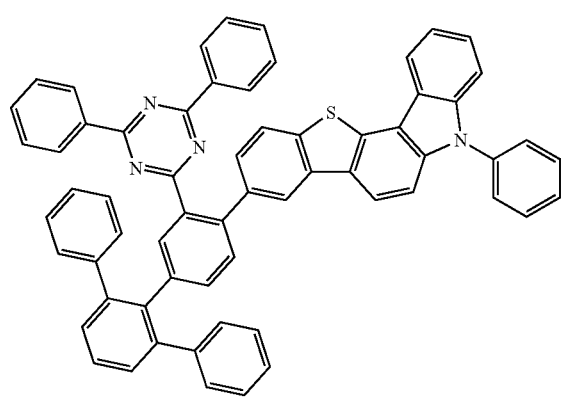
1344
-continued
272
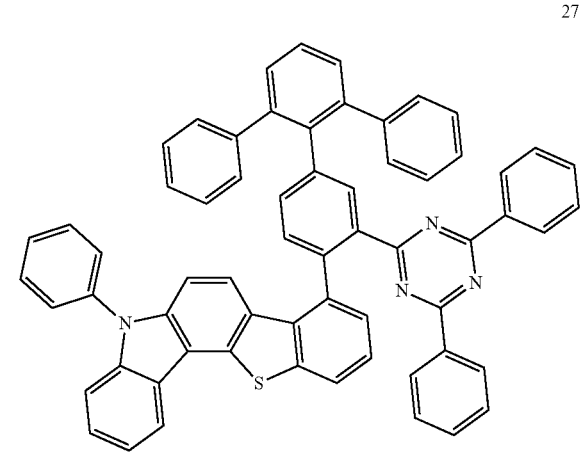
273
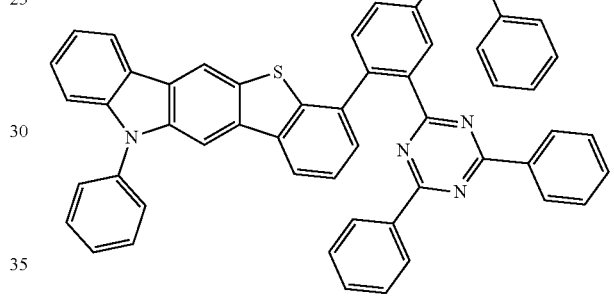
274
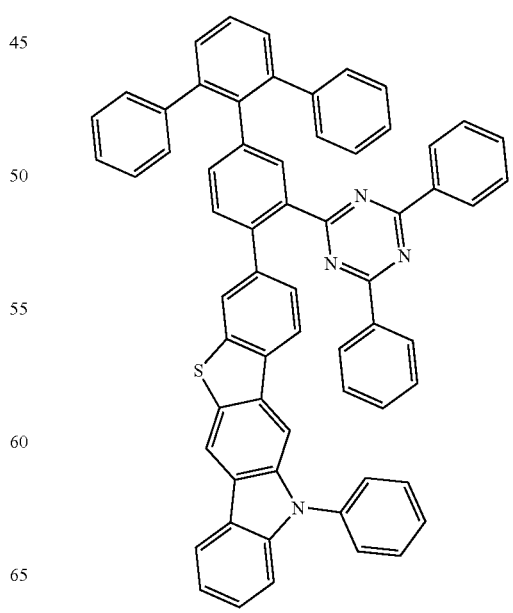

275
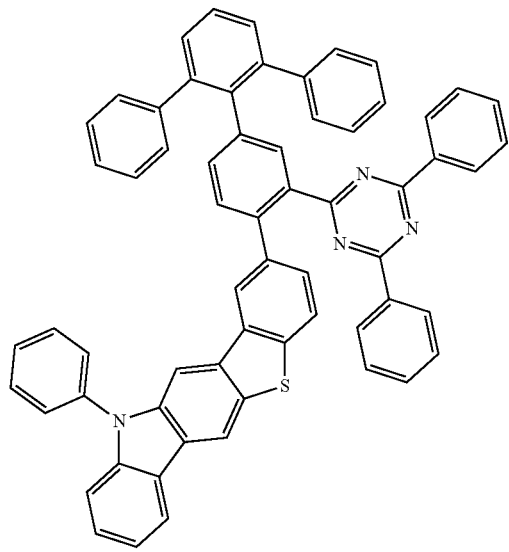
276
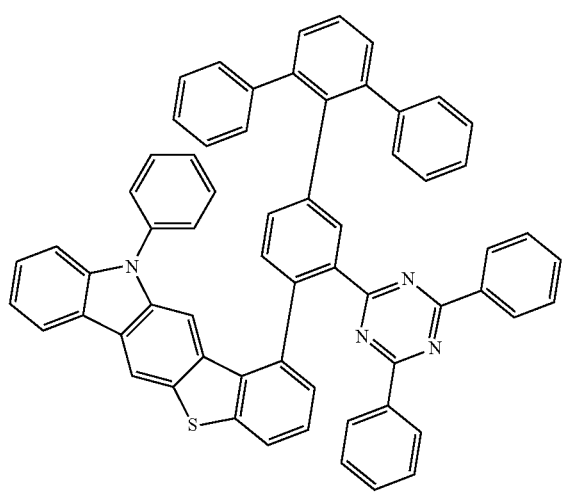
277
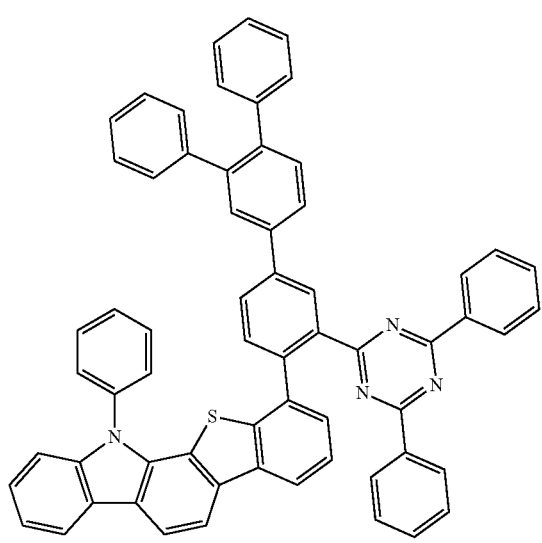
278
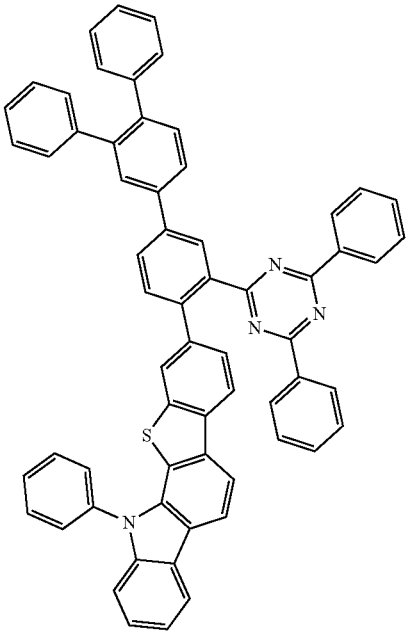
279
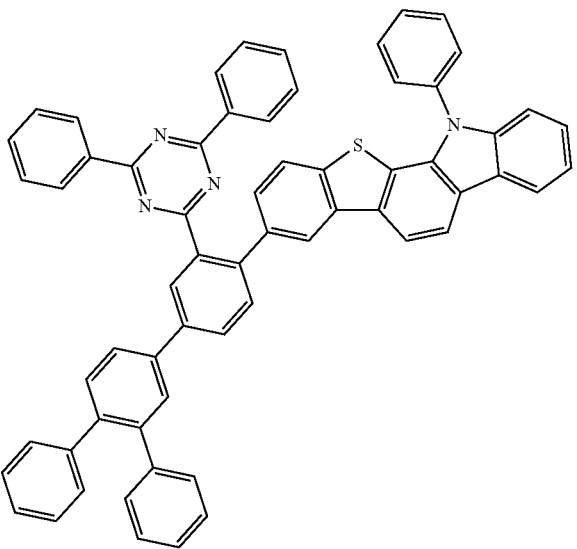

1347
-continued
280
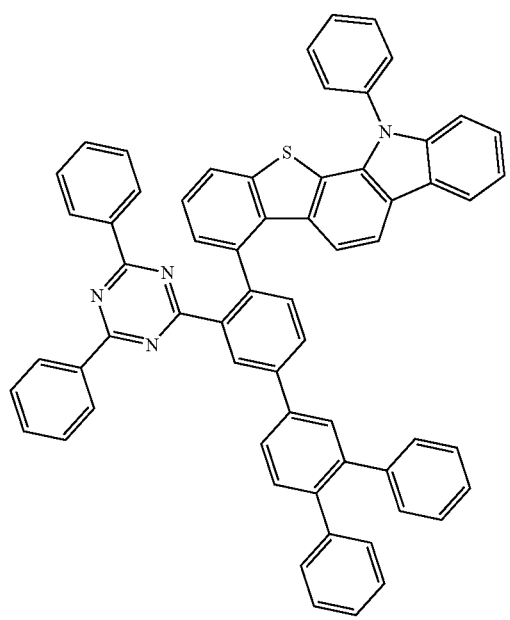
281
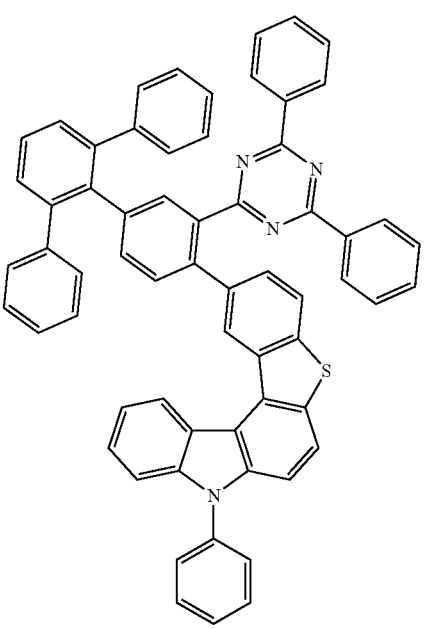
1348
-continued
282
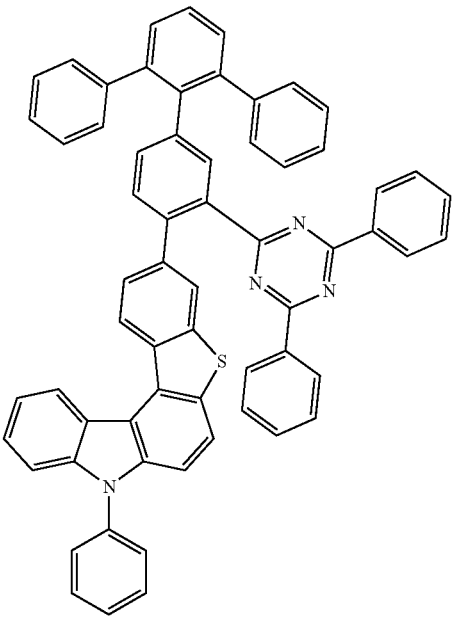
283

-continued
284
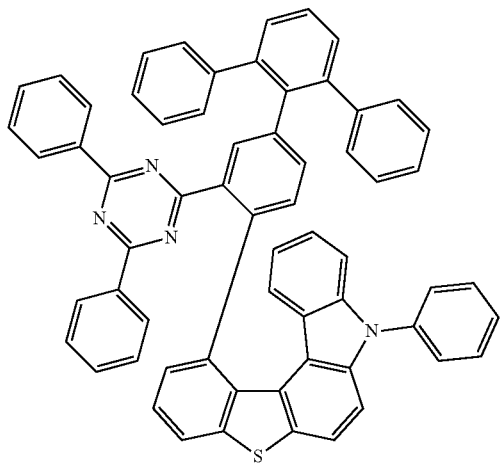
285
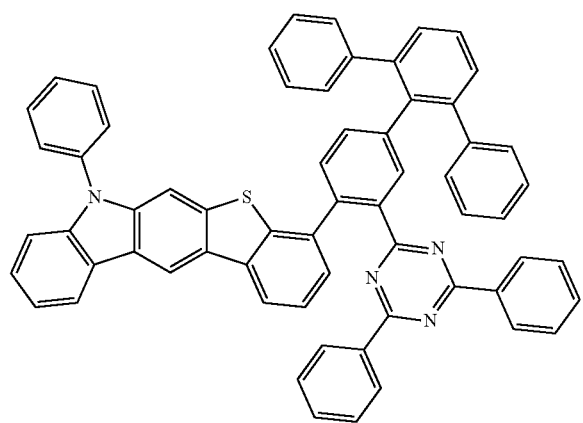
286
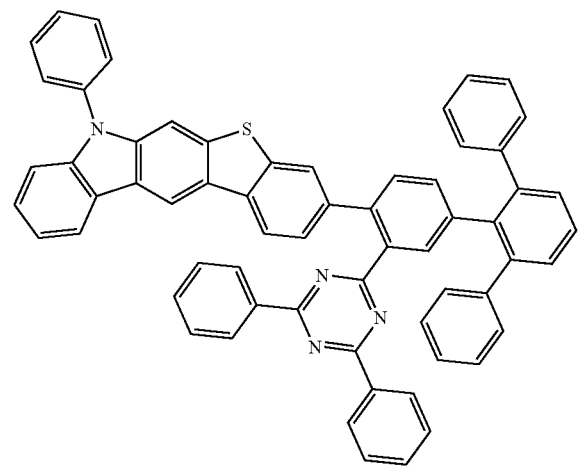
-continued
287
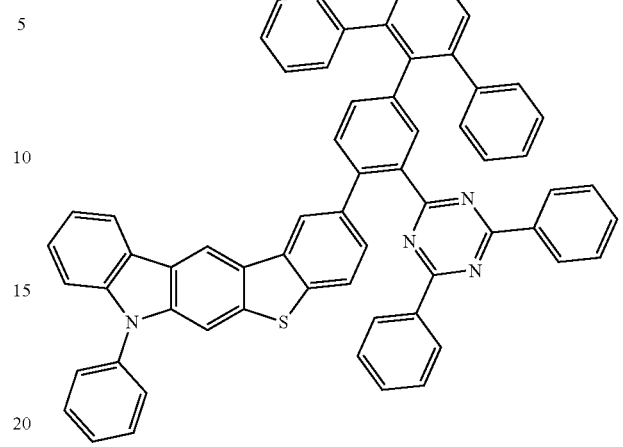
288
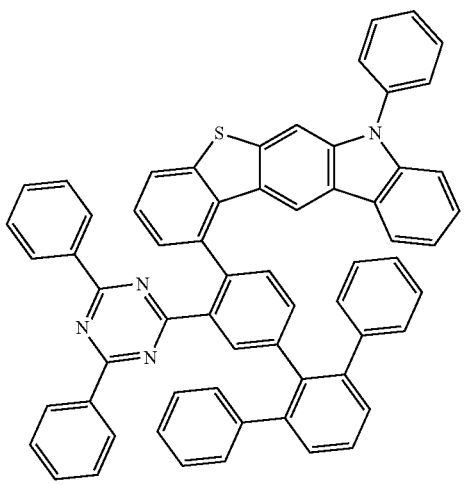
289
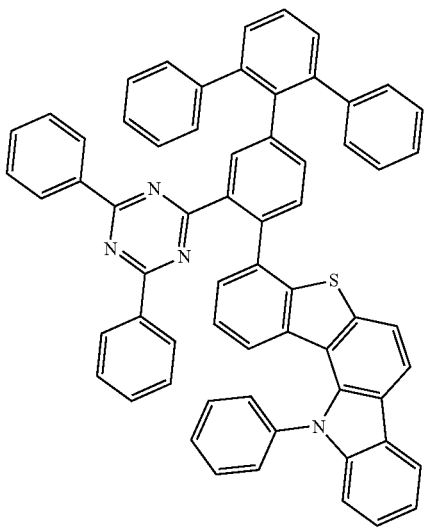

290
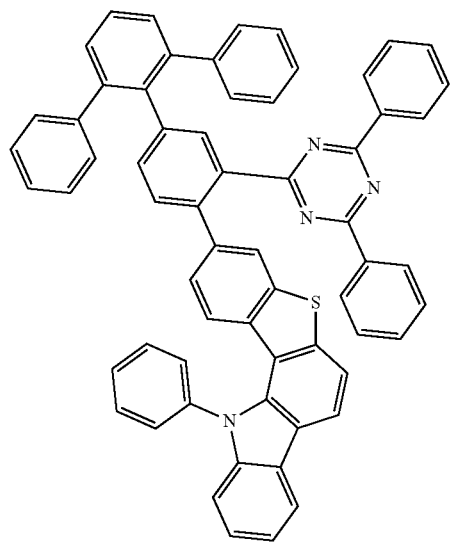
293
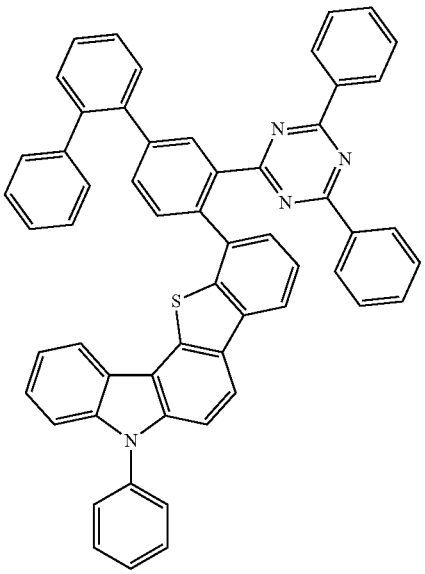
291
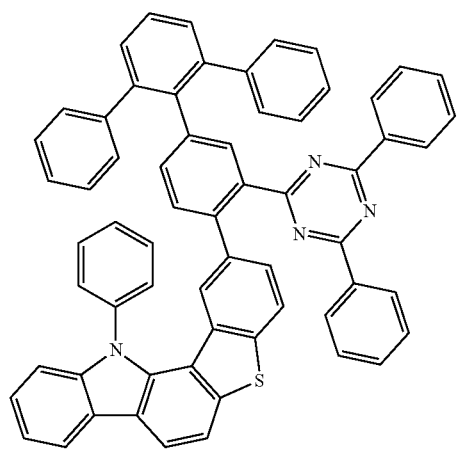
294
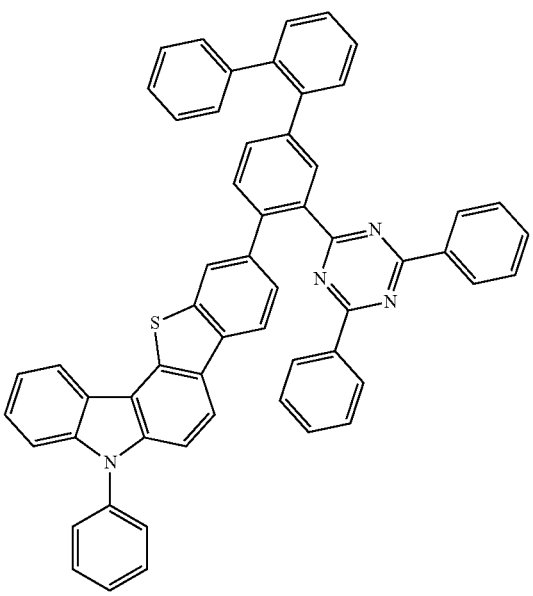
292
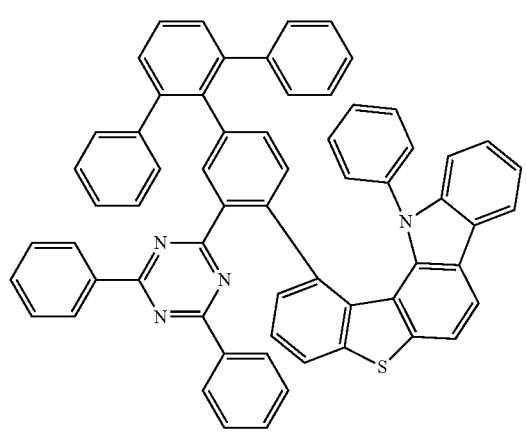
295
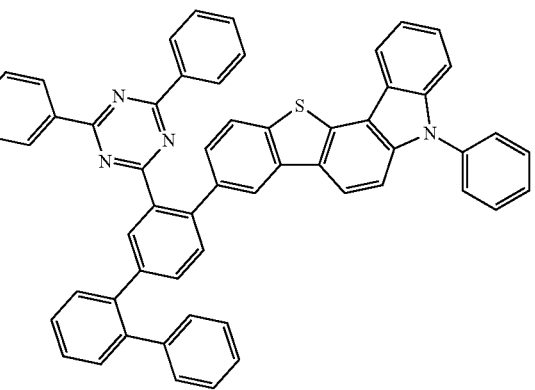

296
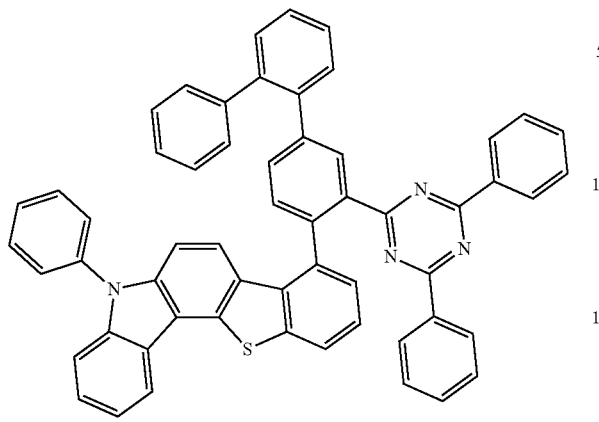
297
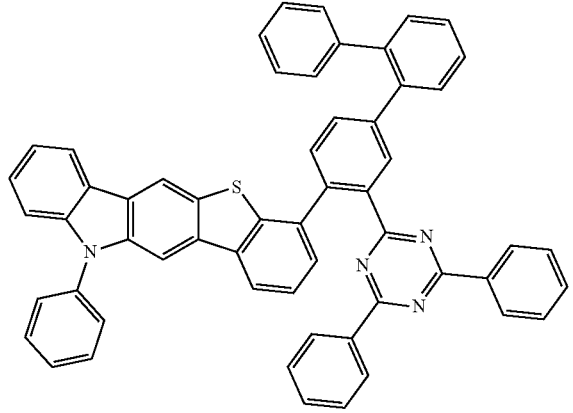
298
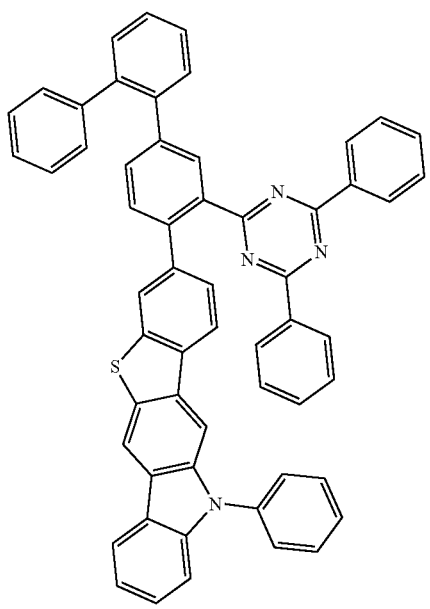
299
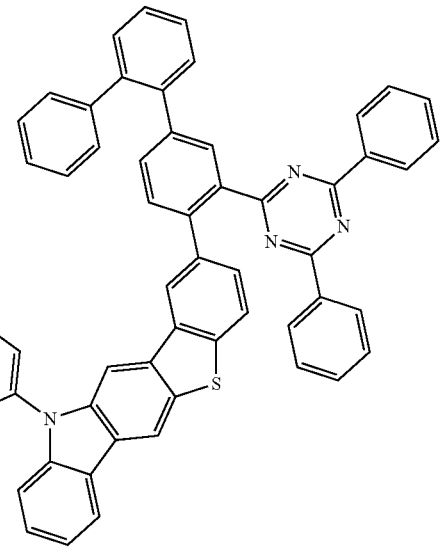
300
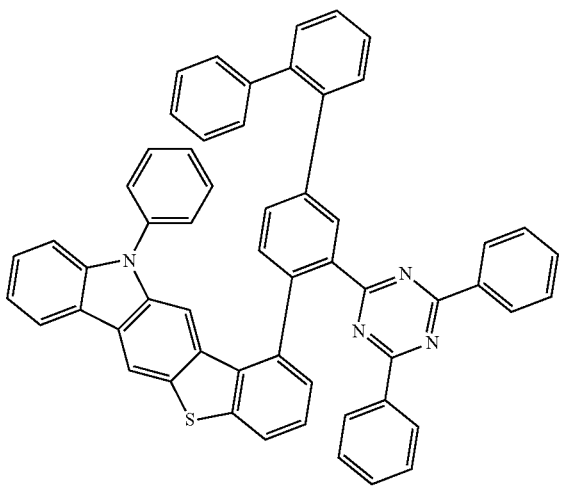
301
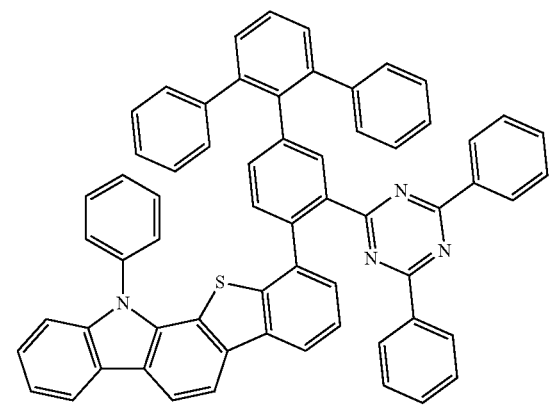

1355
-continued
302
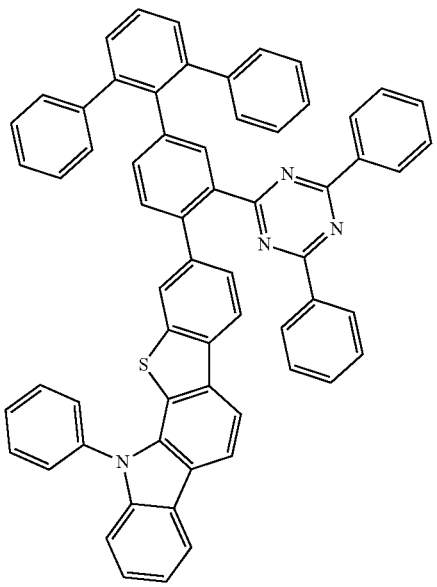
303
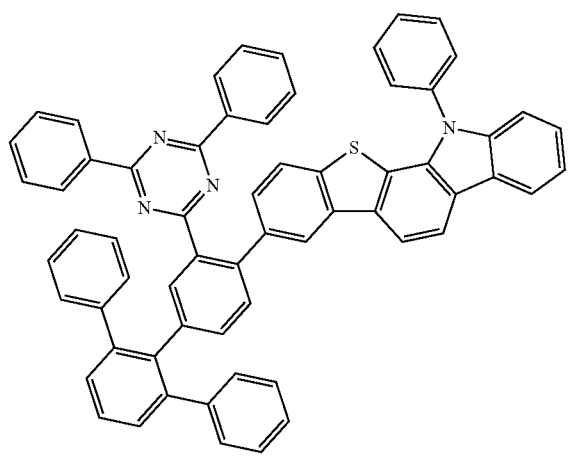
304
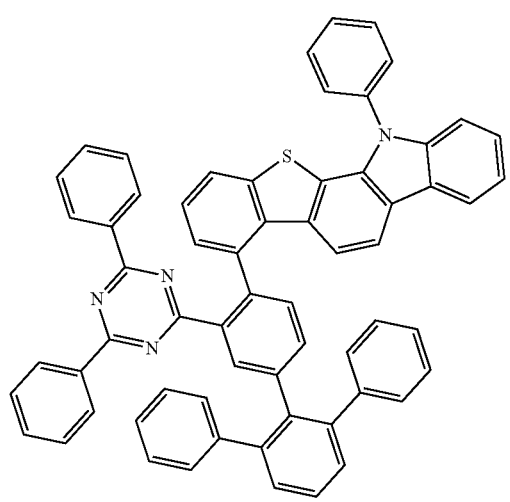
1356
-continued
305
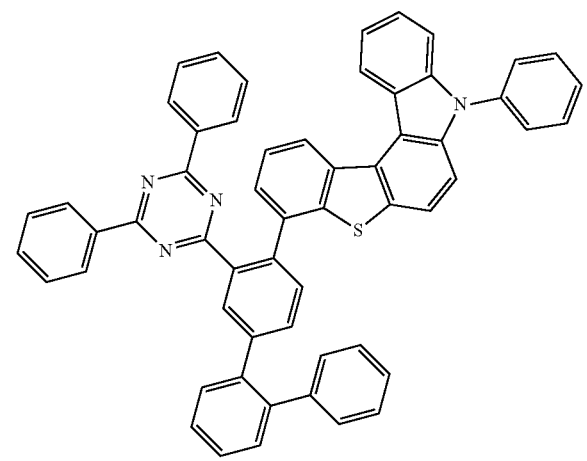
306
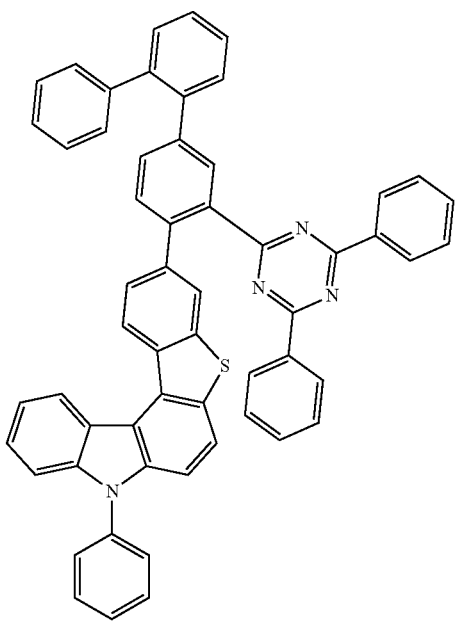

307
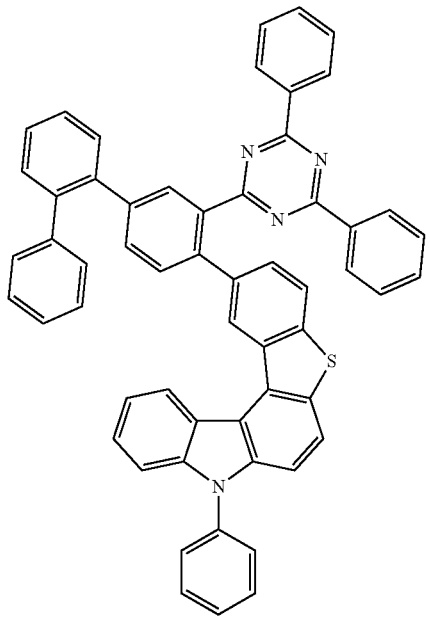
308
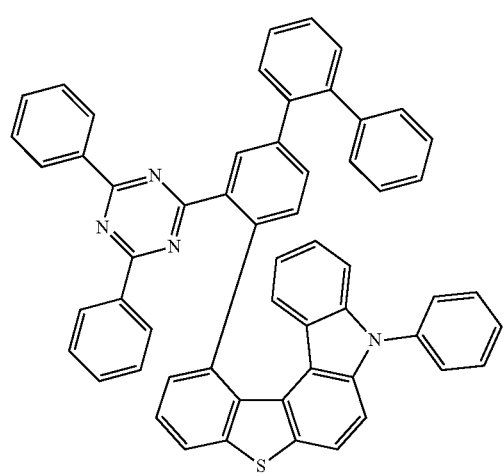
309
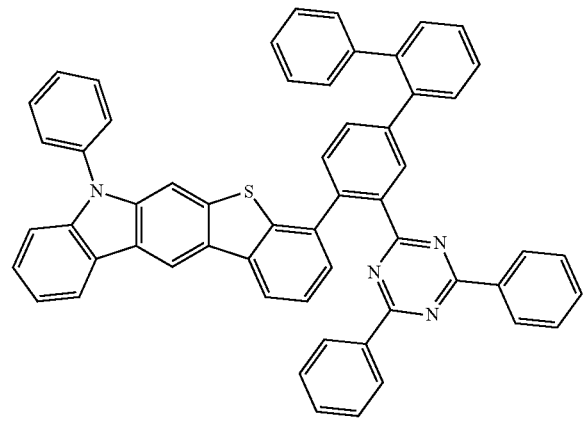
310
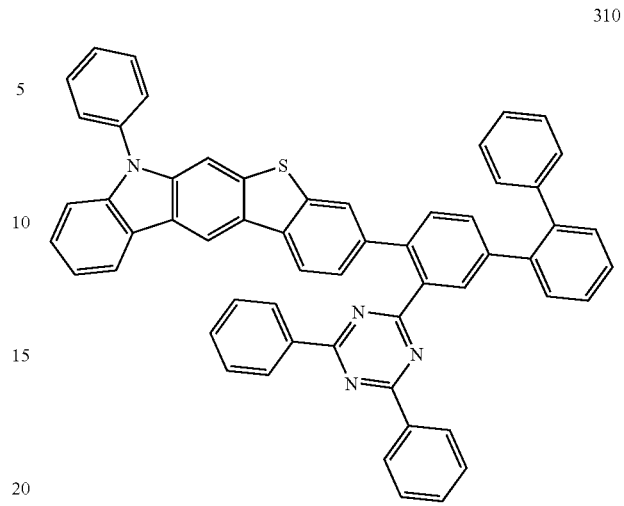
311
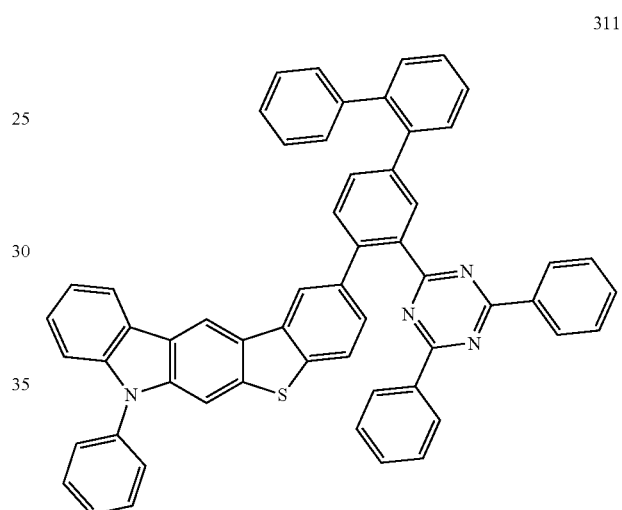
312
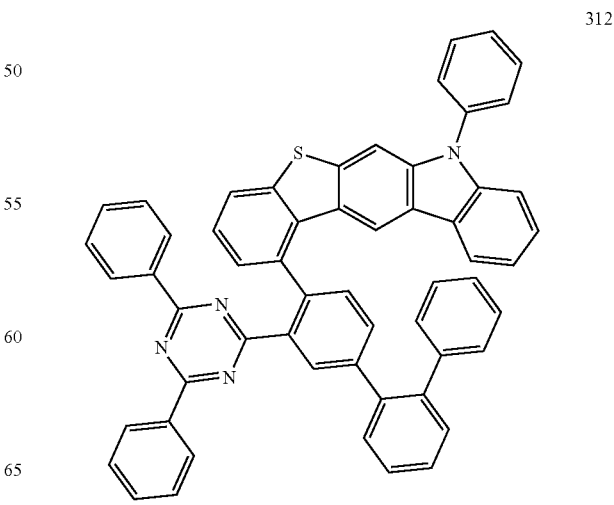

1359
-continued
313
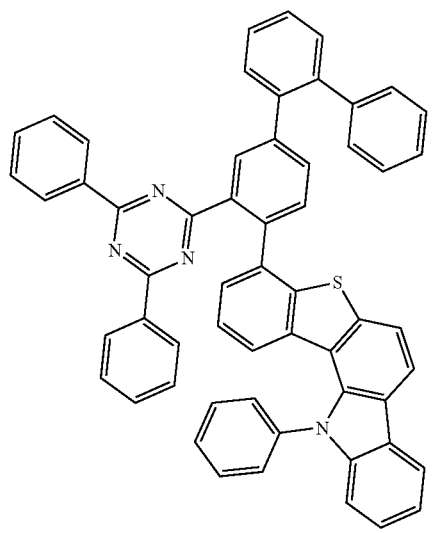
314
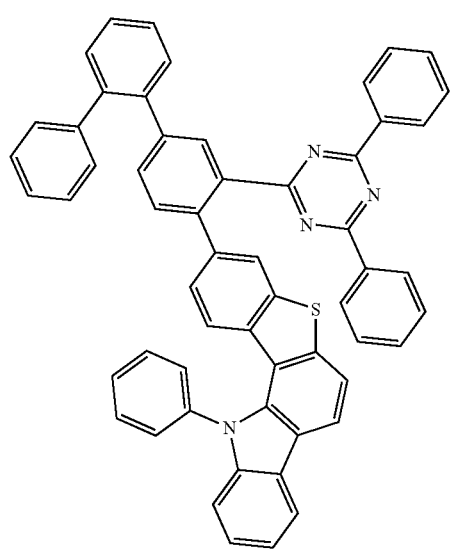
315
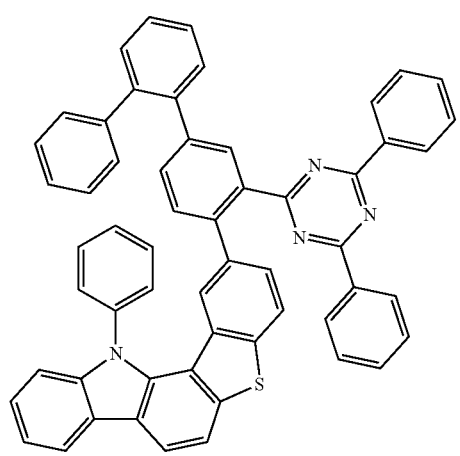
1360
-continued
316
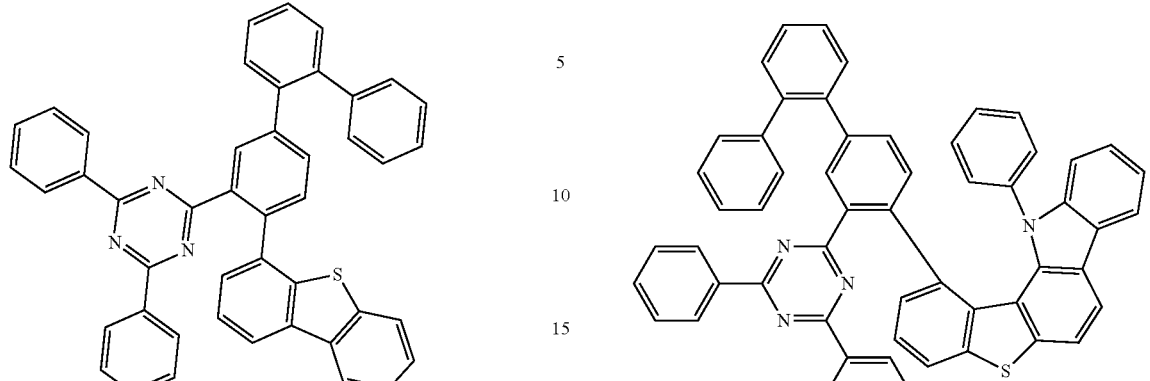
317
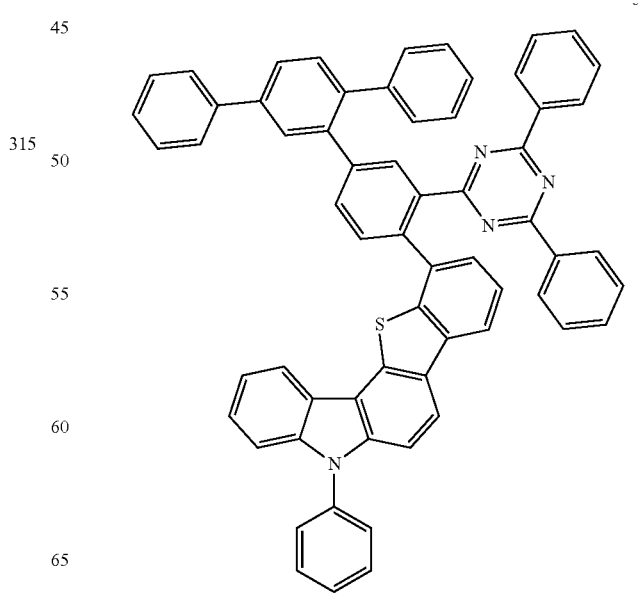

1361
-continued
318
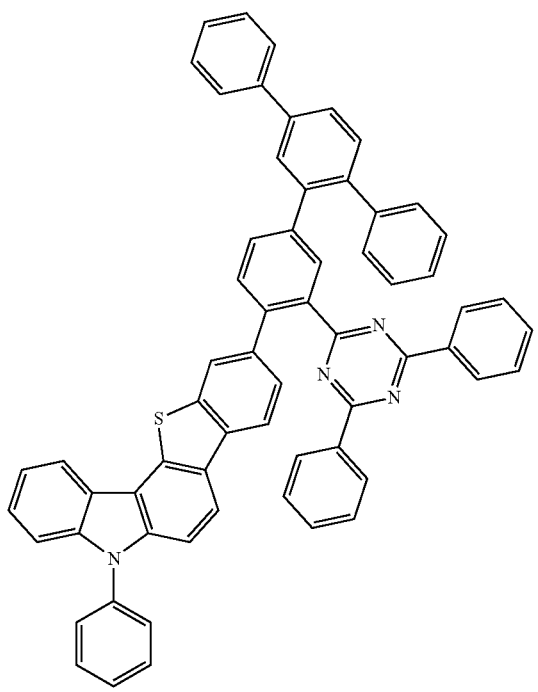
319
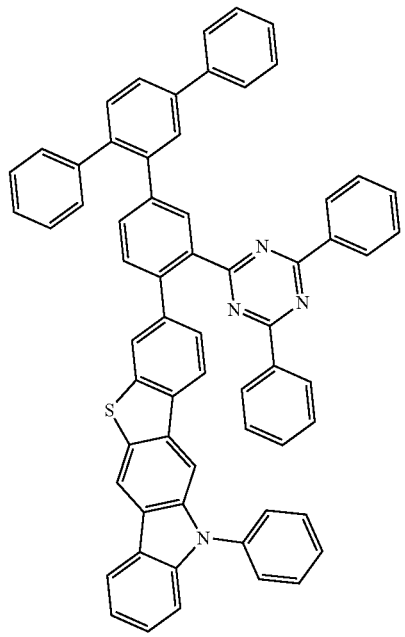
1362
-continued
320
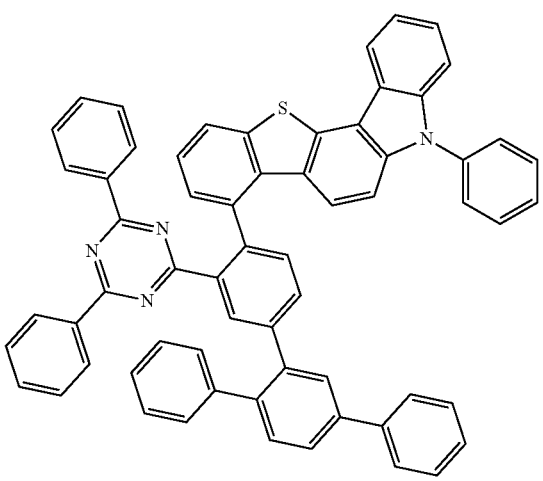
321
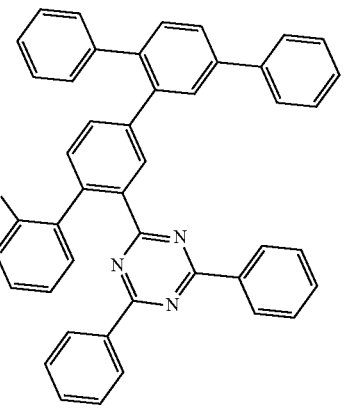
322

323
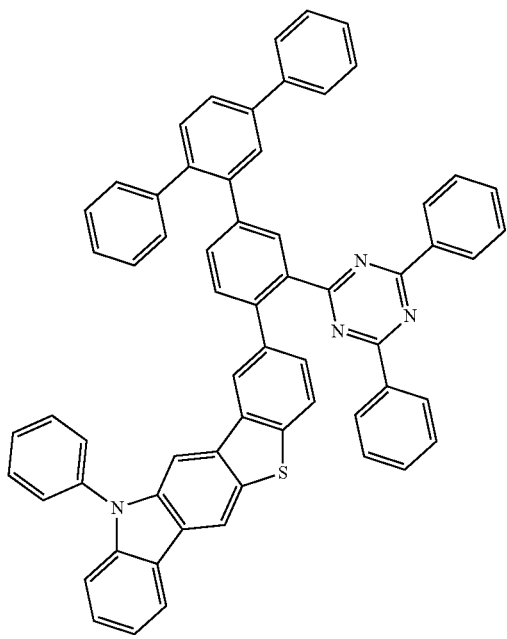
324
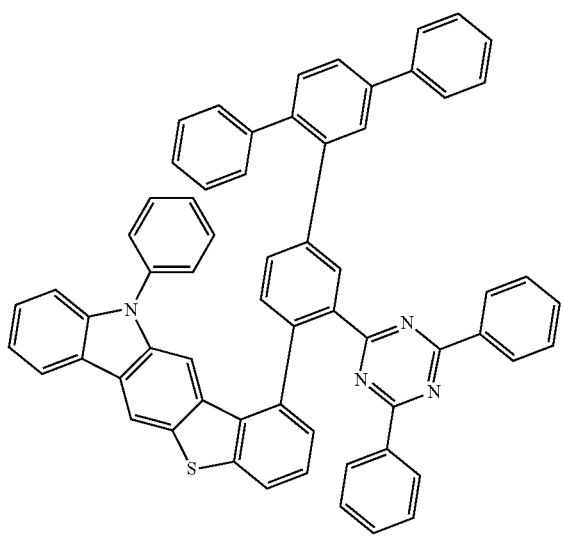
325
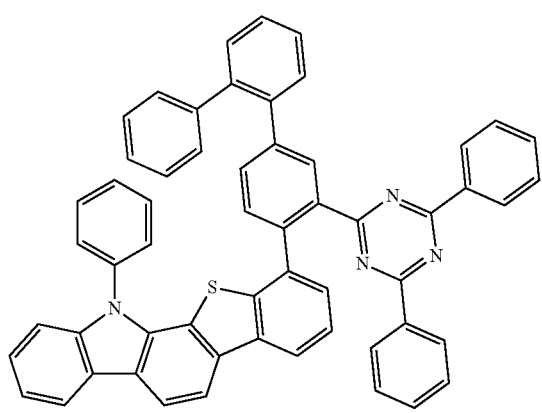
326
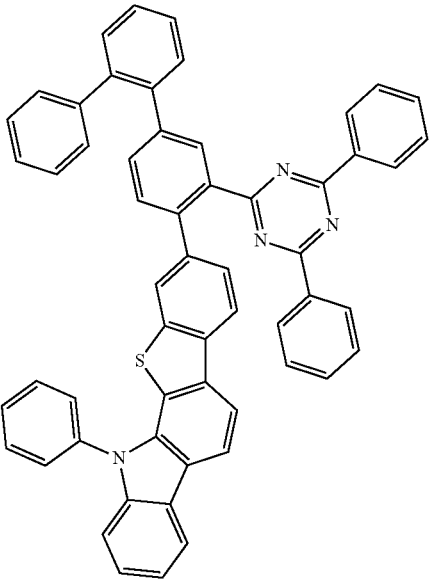
327
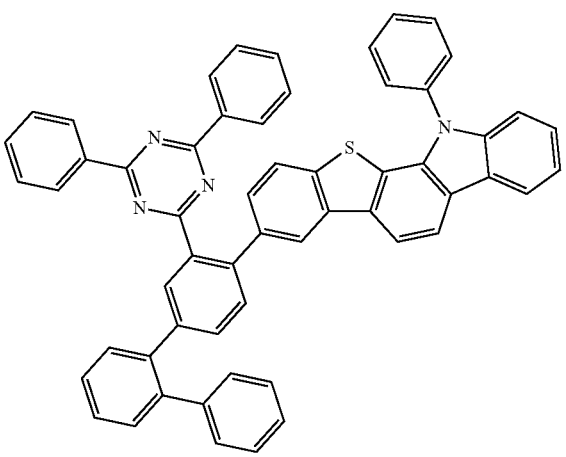
328
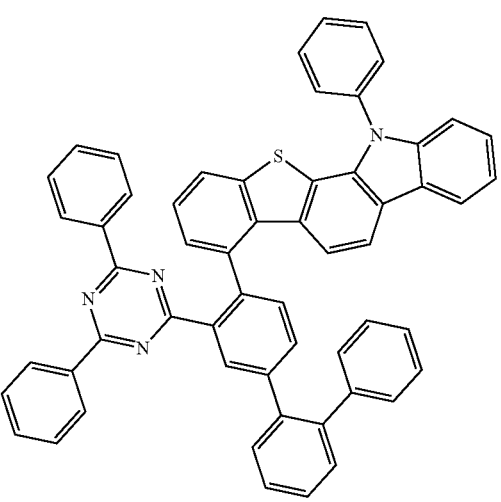

1365
-continued
329
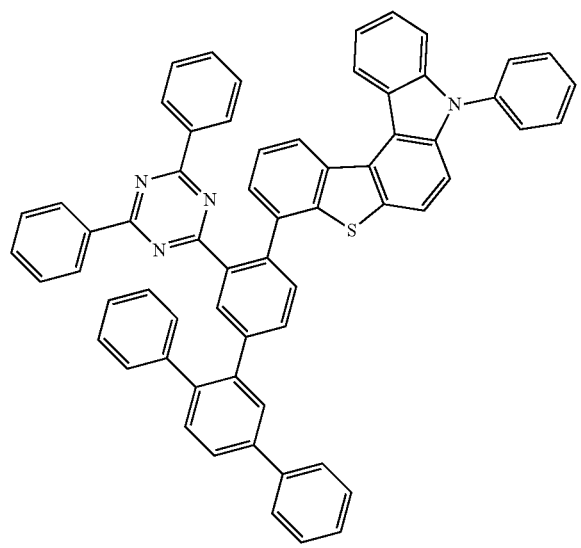
330
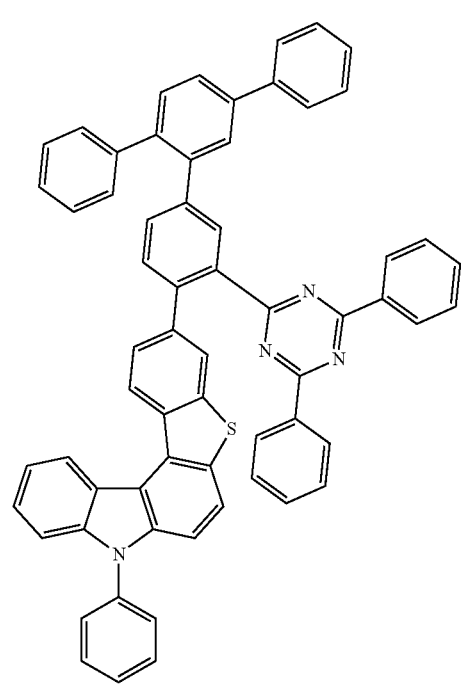
1366
-continued
331
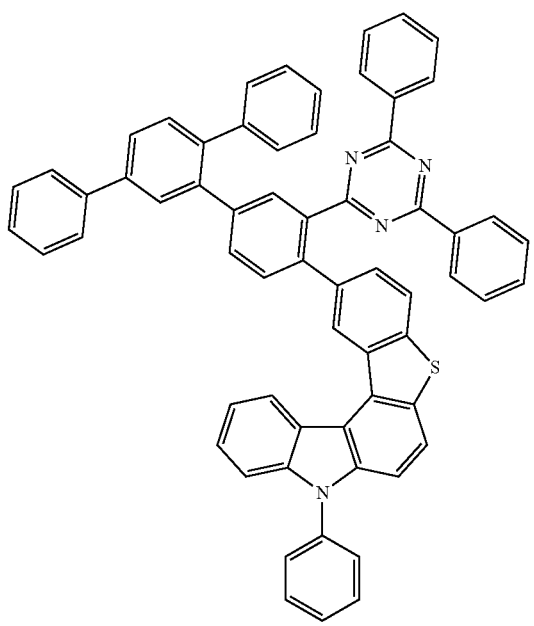
332
333
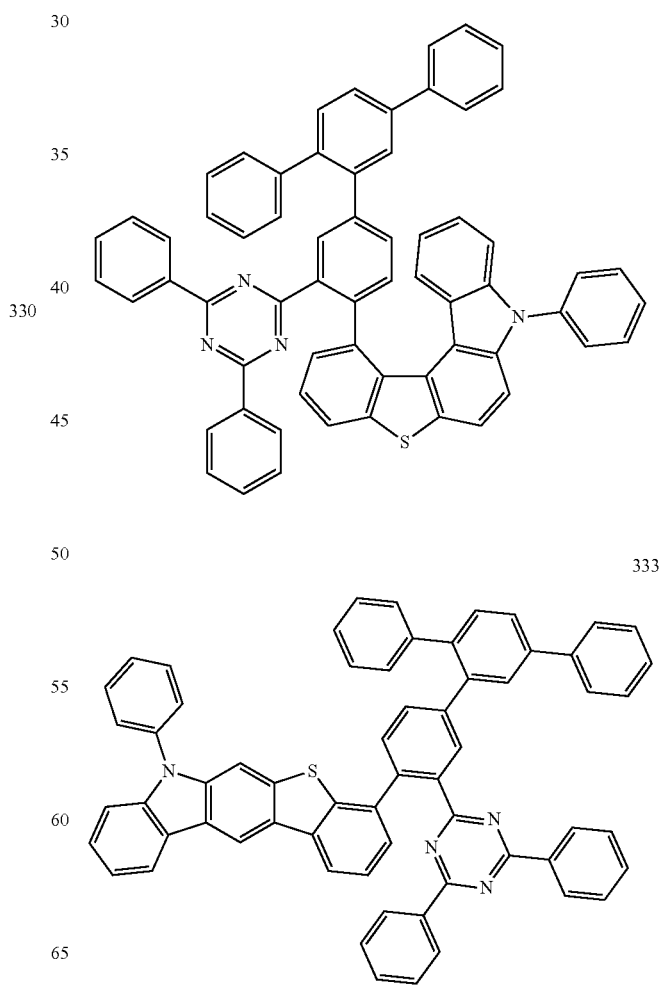

1367
-continued
334
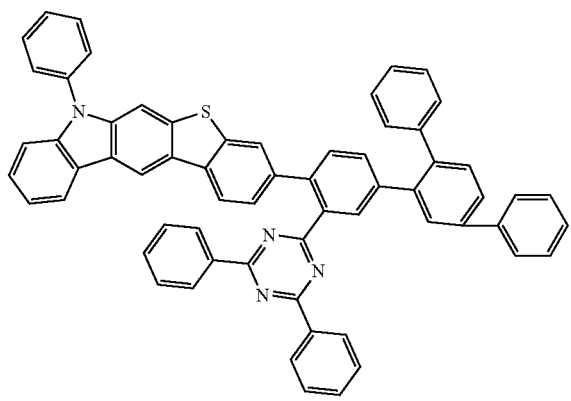
335
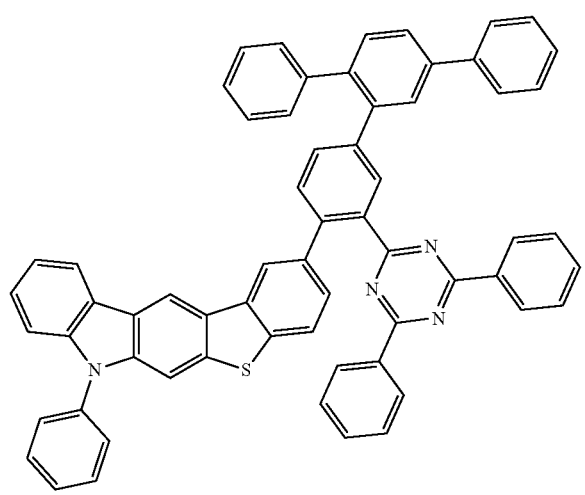
1368
-continued
337
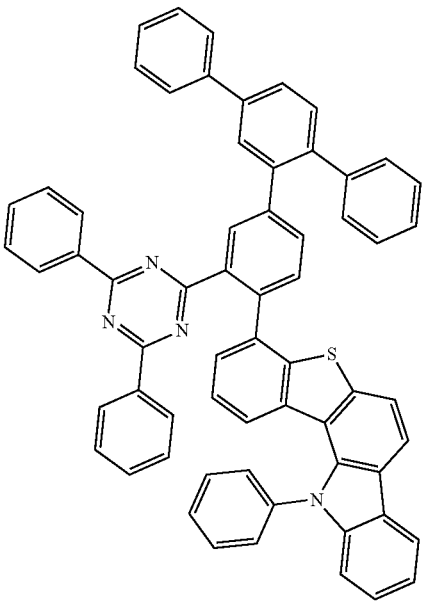
336
338
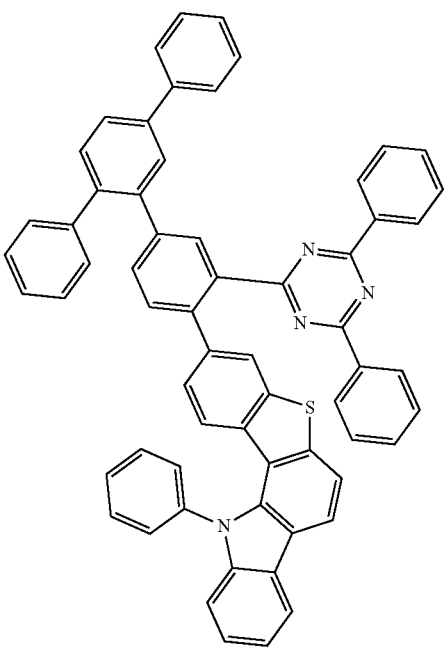

1369
-continued
339
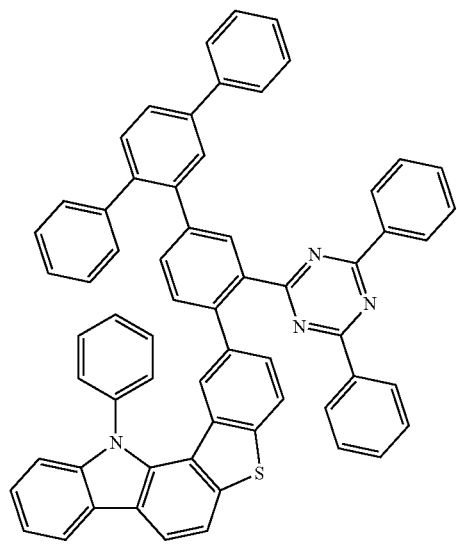
340
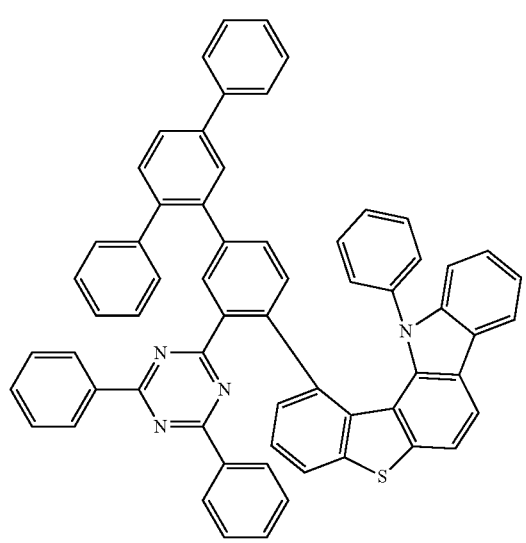
341
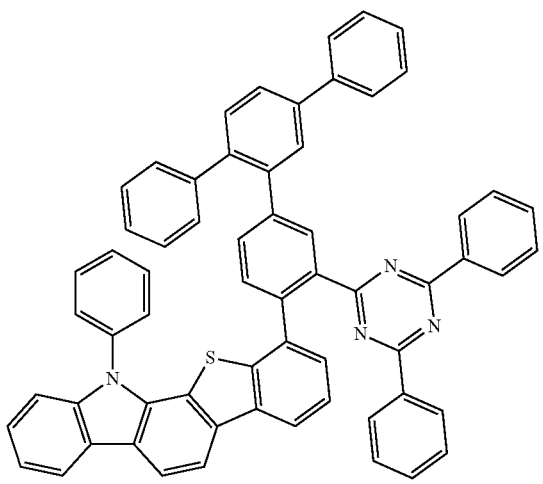
1370
-continued
342
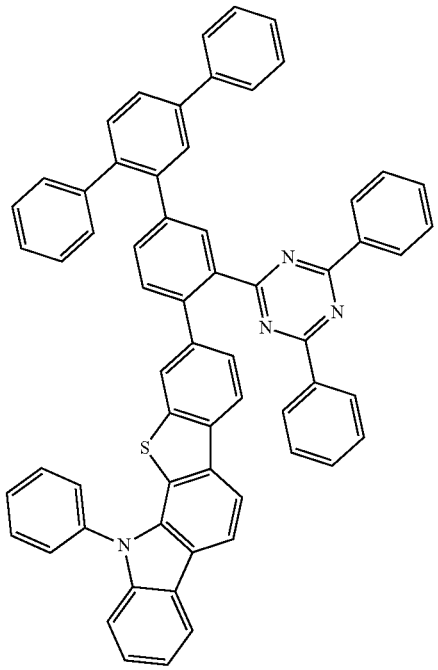
343
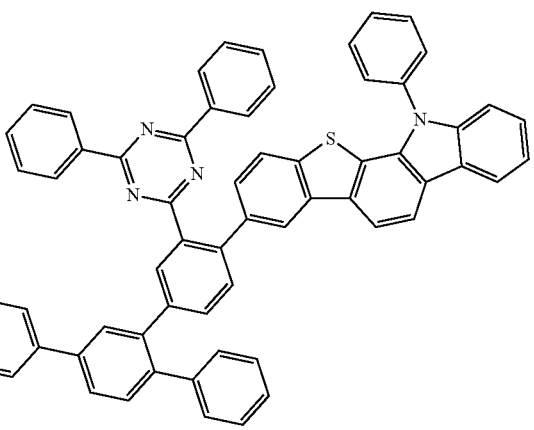

1371
-continued
344
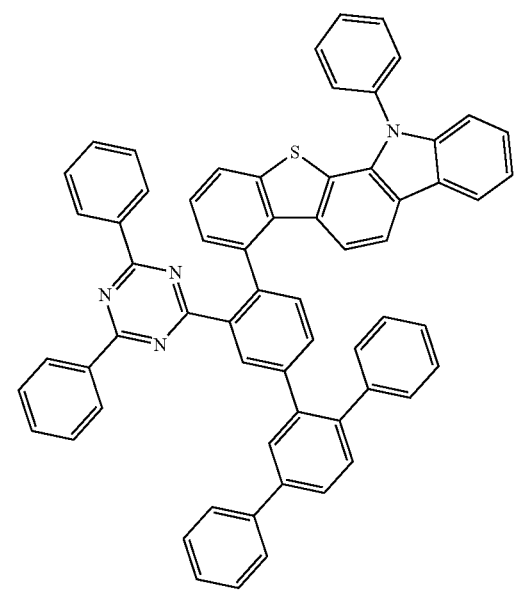
345
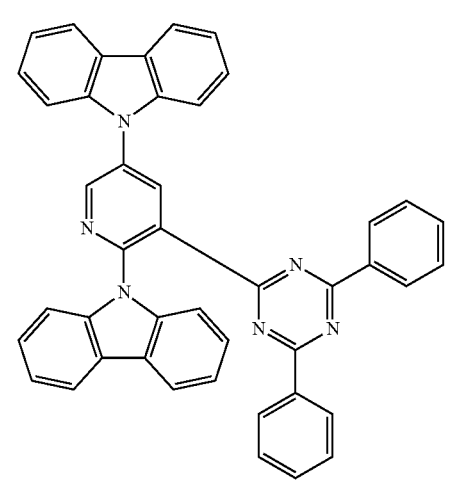
346
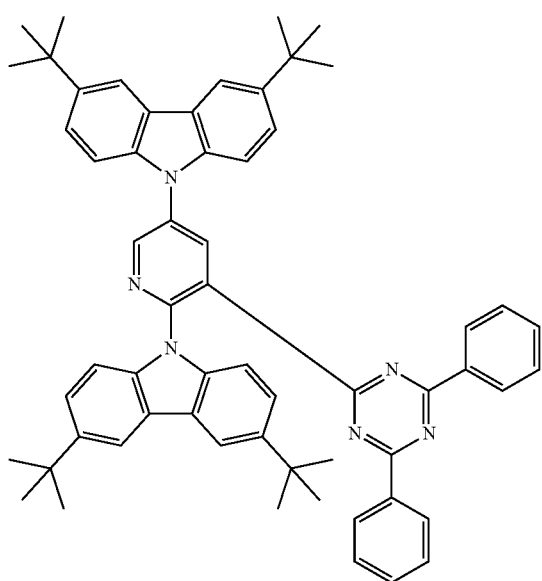
1372
-continued
347
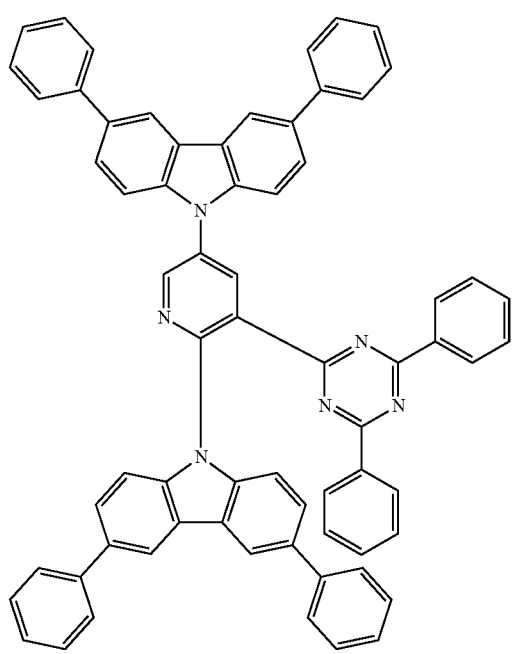
348
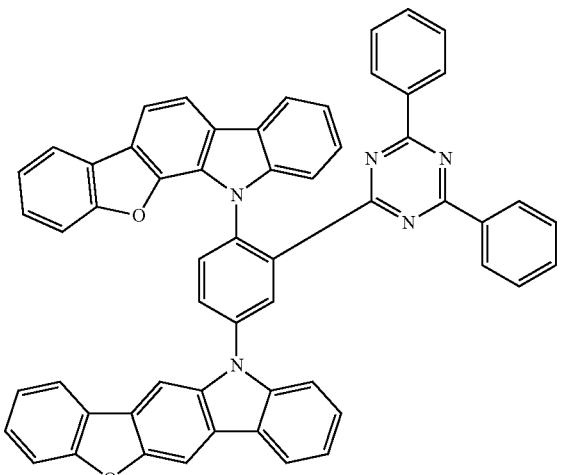
349
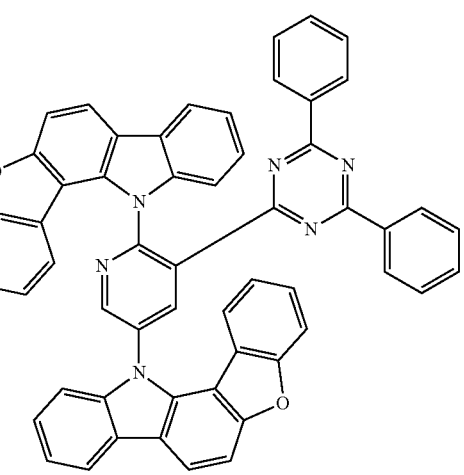

350
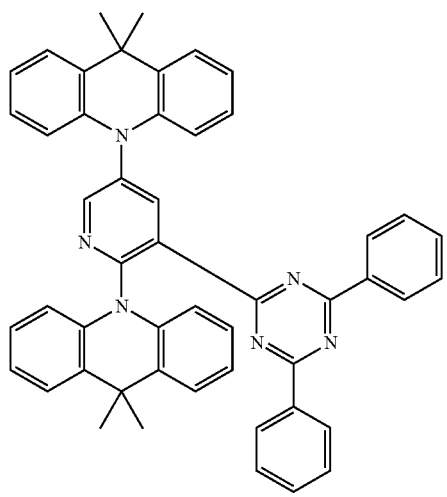
351
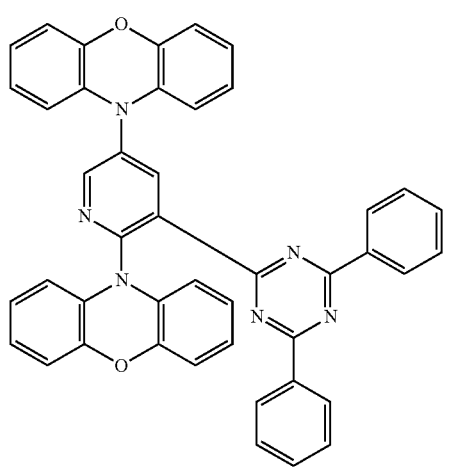
352
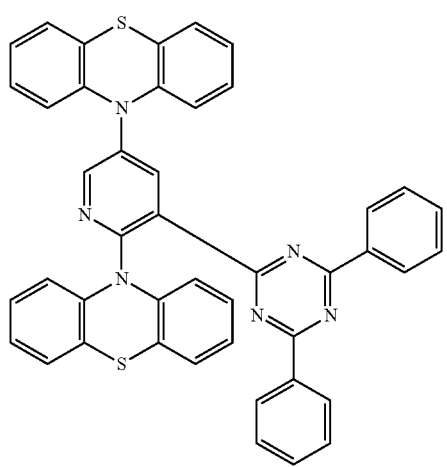
353
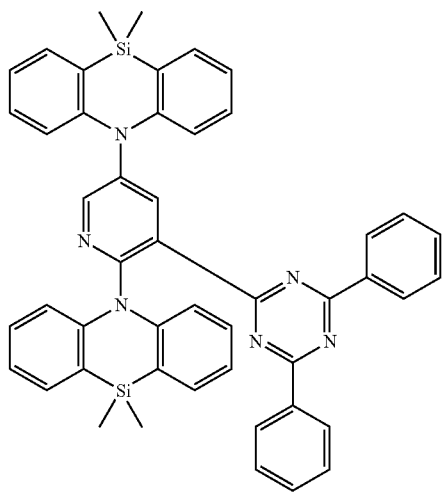
354
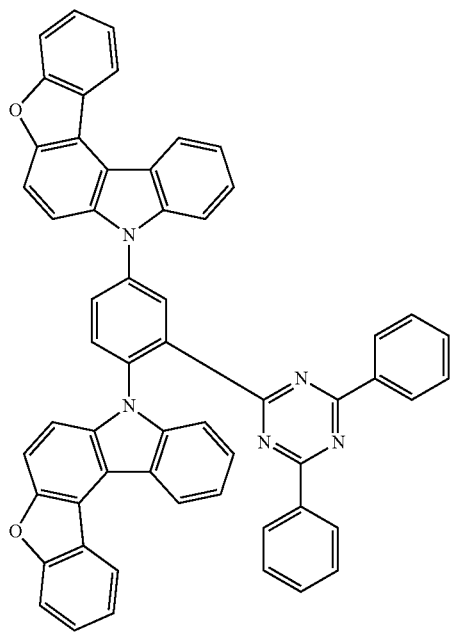

355
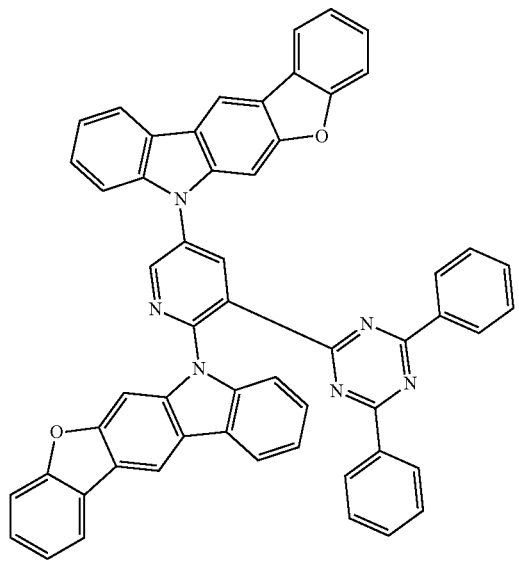
356
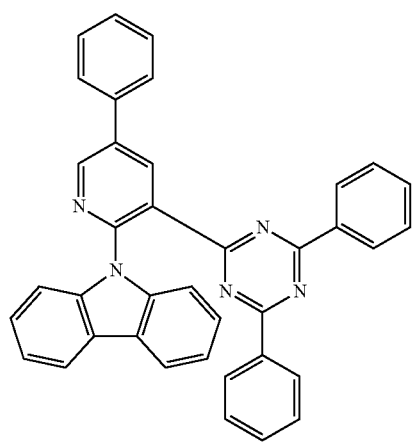
357
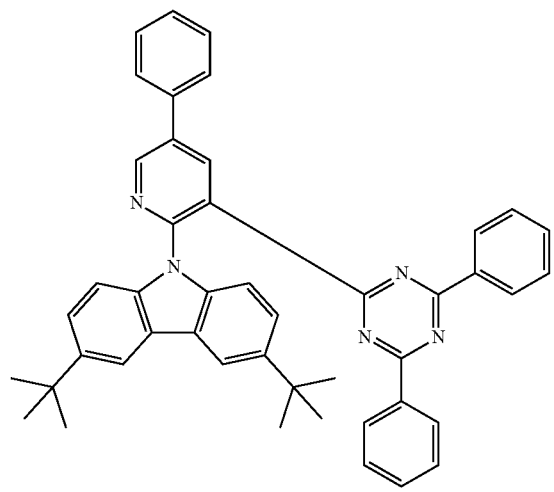
358
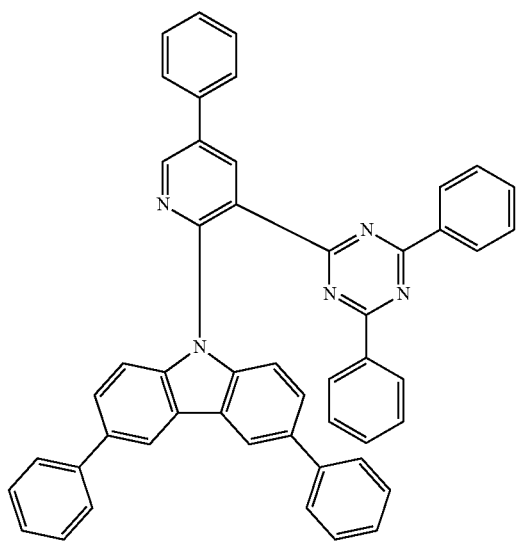
359
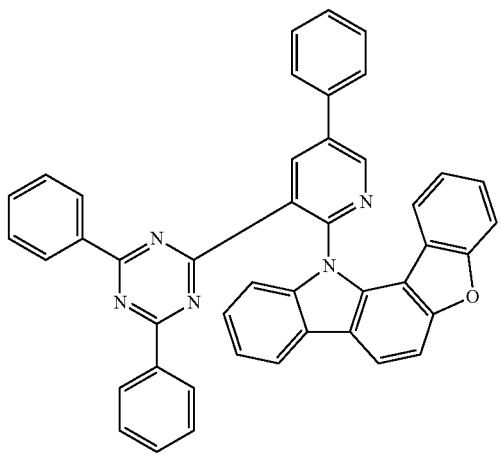
360

1377
-continued
361
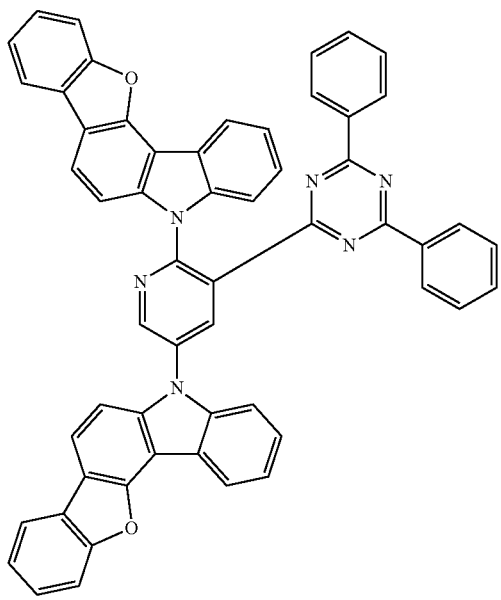
362
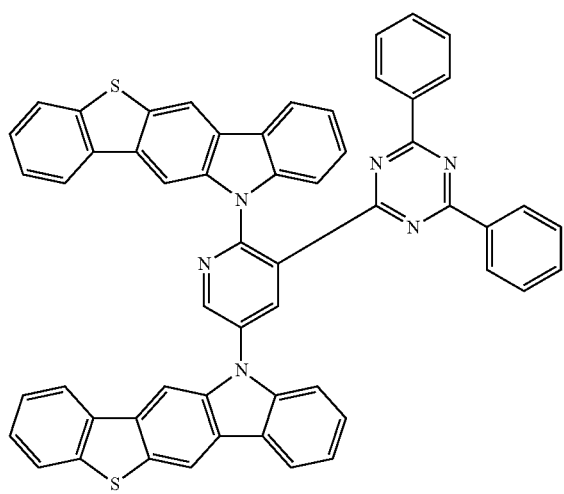
363
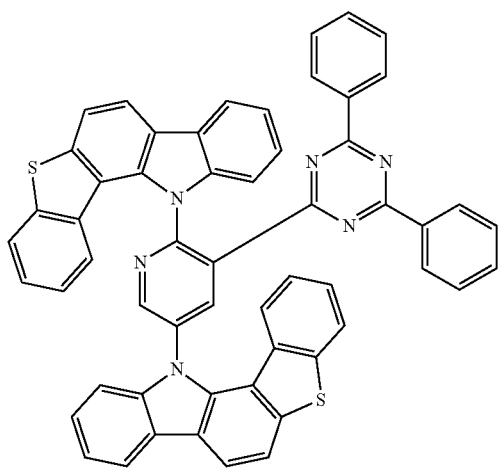
1378
-continued
364
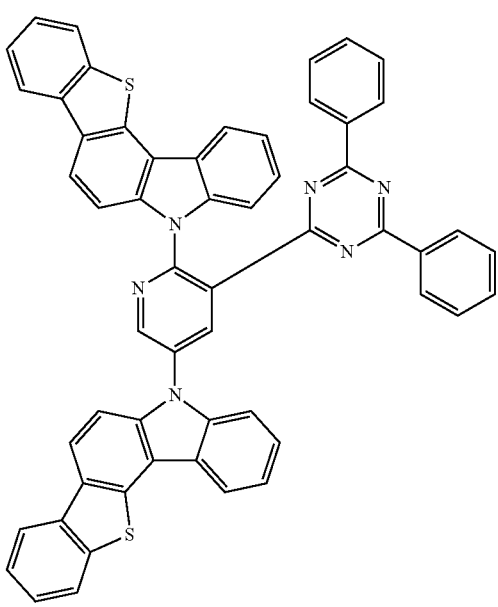
365
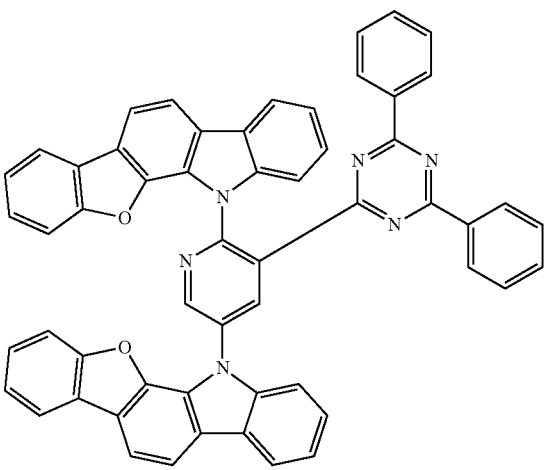

1379
-continued
366
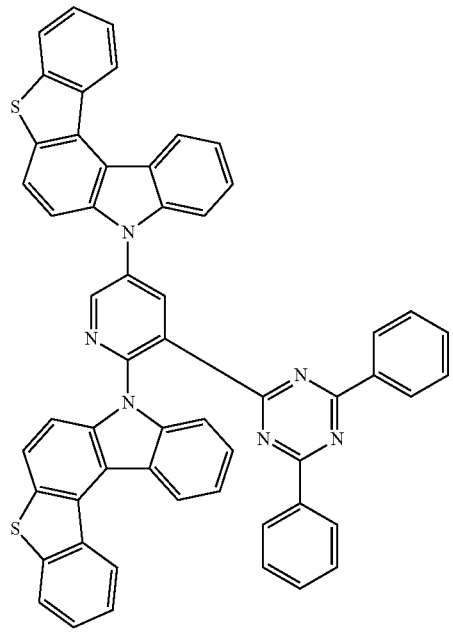
367
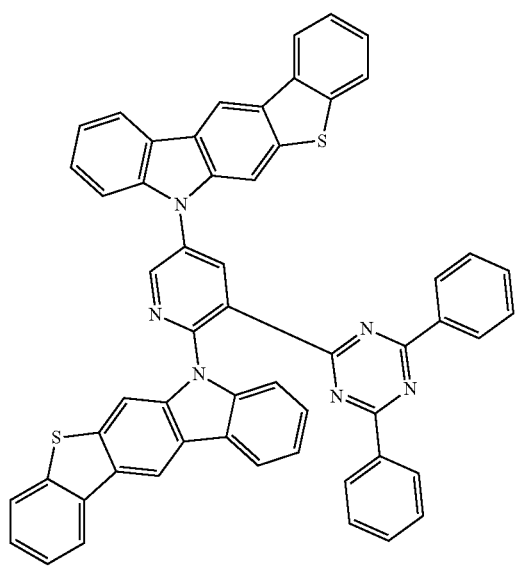
1380
-continued
368
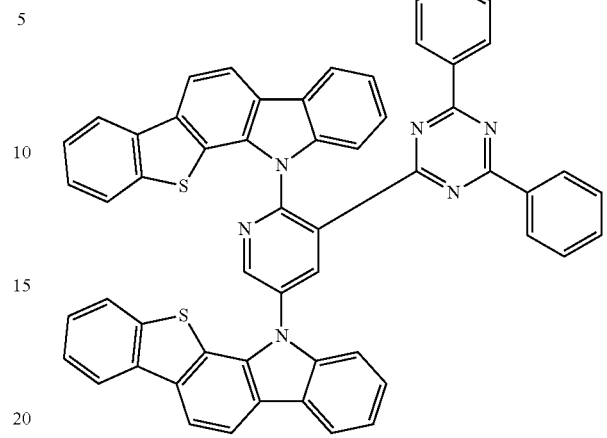
369
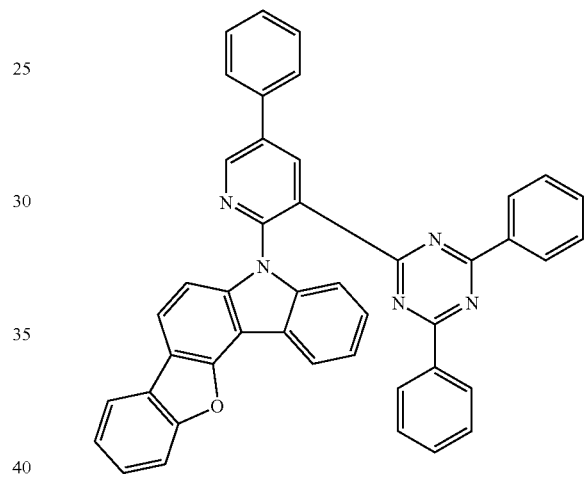
370
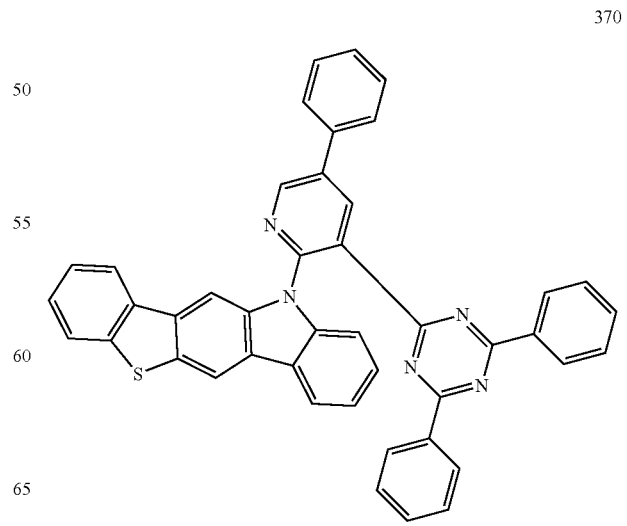

1381
-continued
371
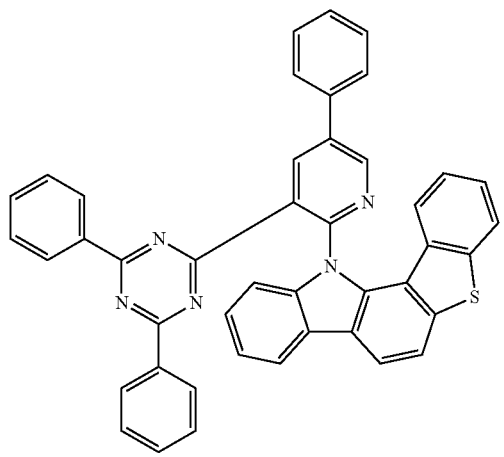
372
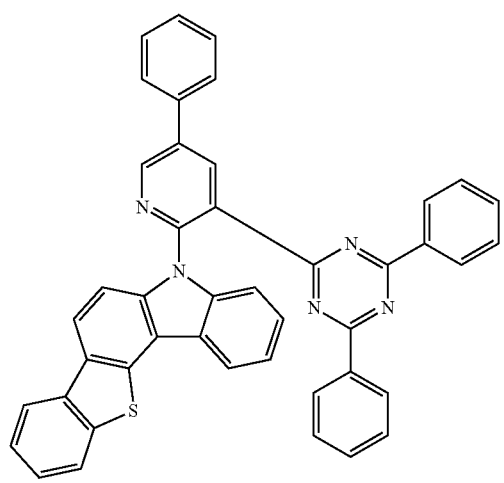
373
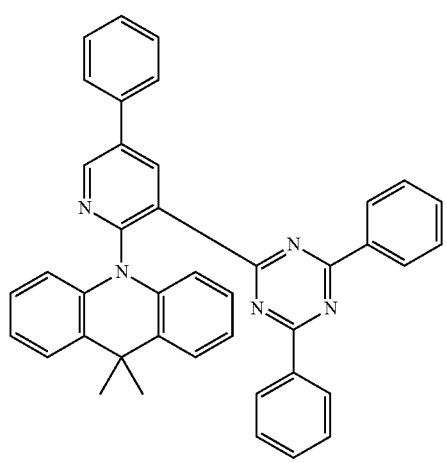
1382
-continued
374
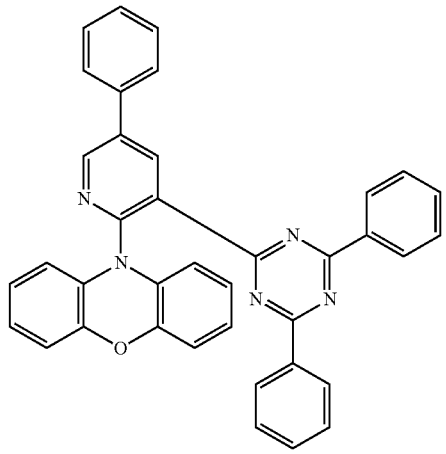
375
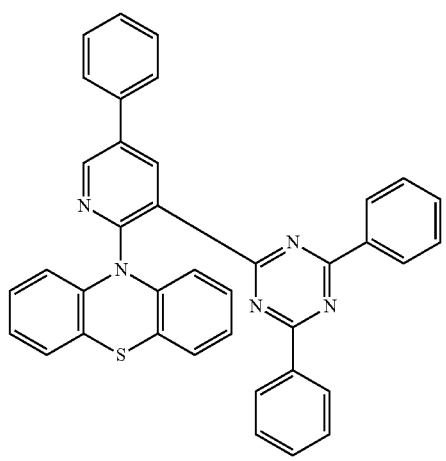
376
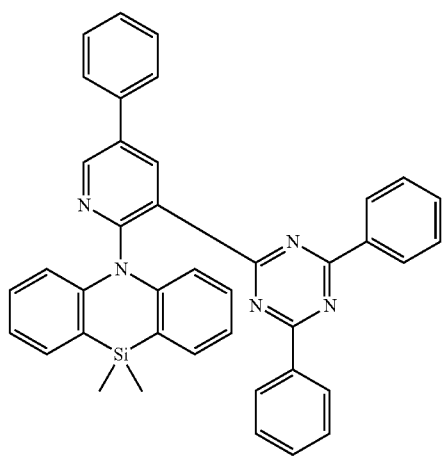

1383
-continued
377
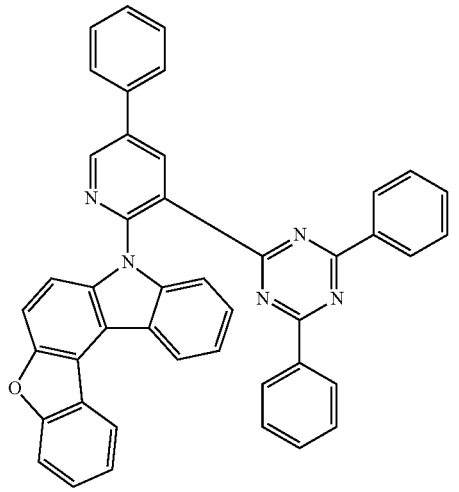
378
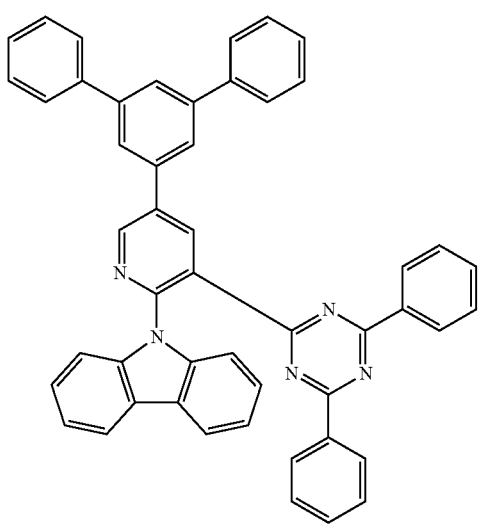
379
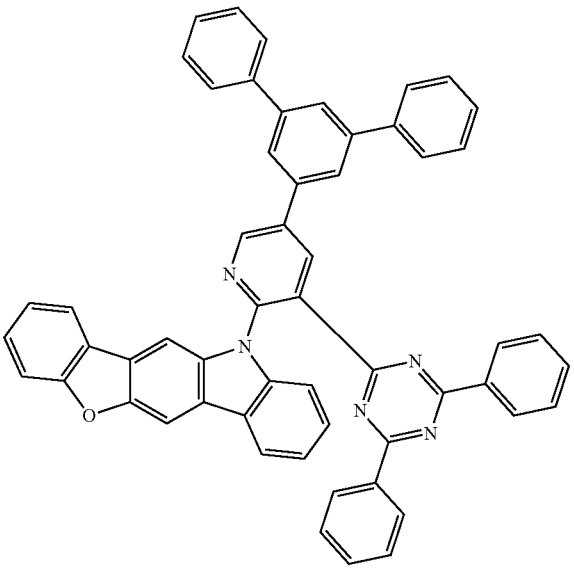
1384
-continued
380
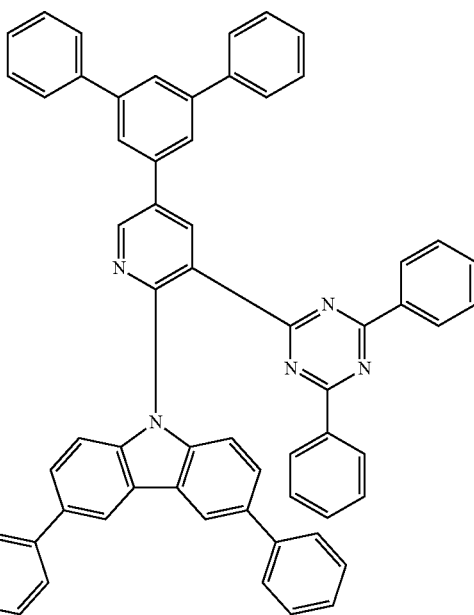
381

382
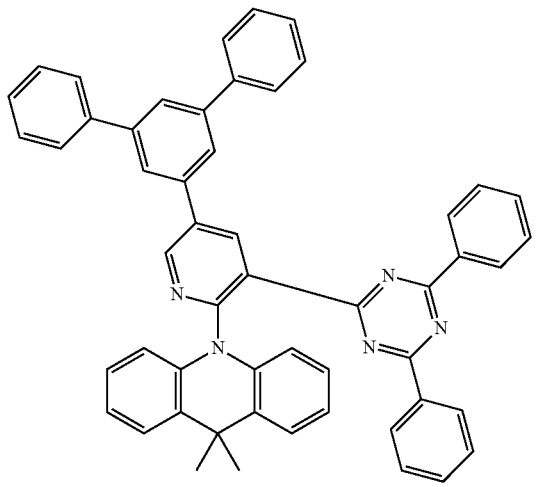
385
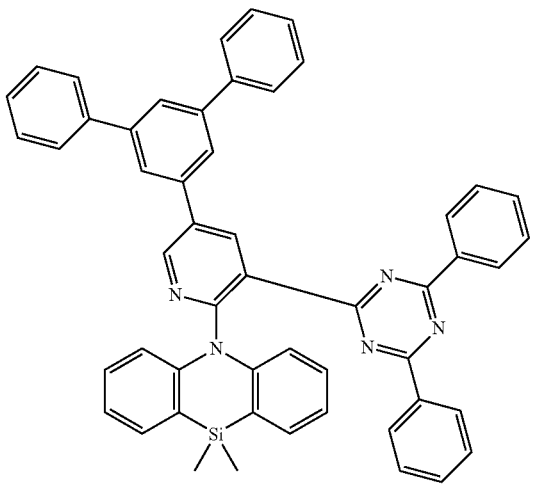
383
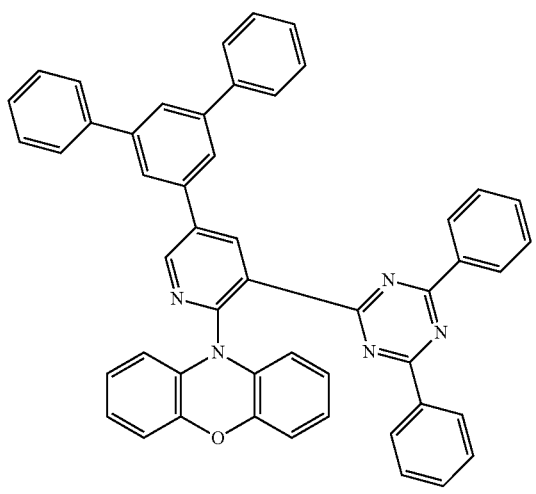
386
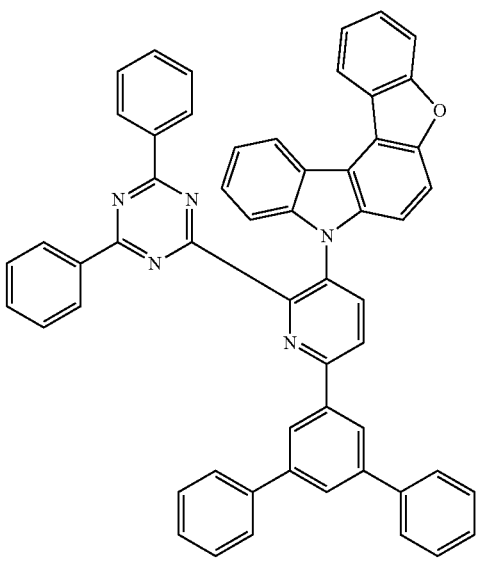
384
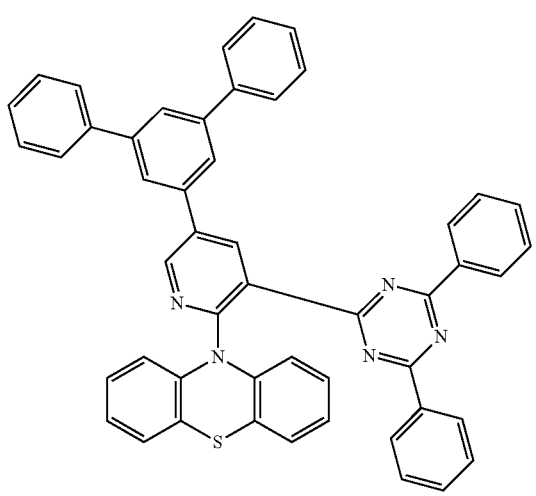
387
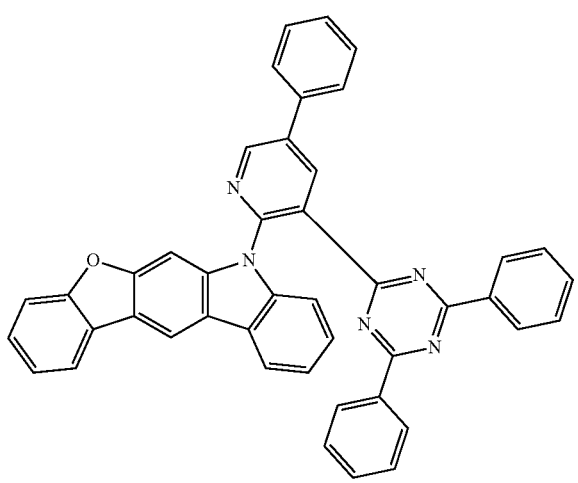

1387 -continued
388
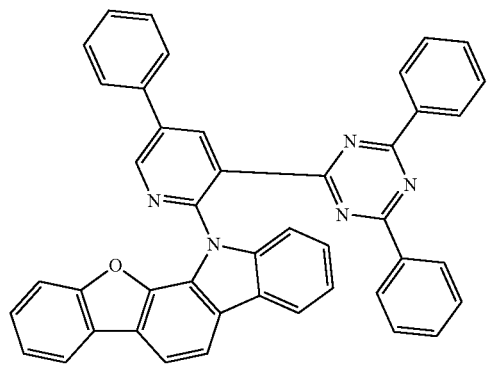
389
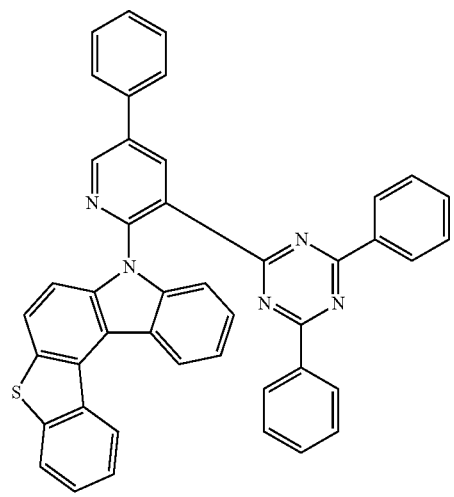
390
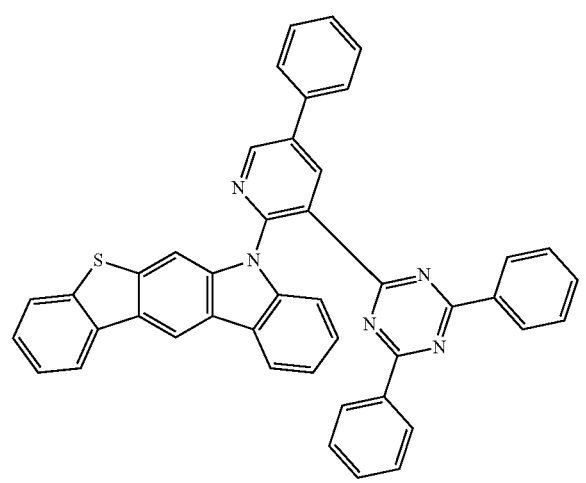
1388 -continued
391
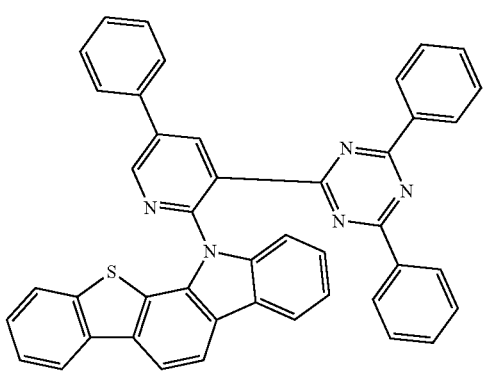
392
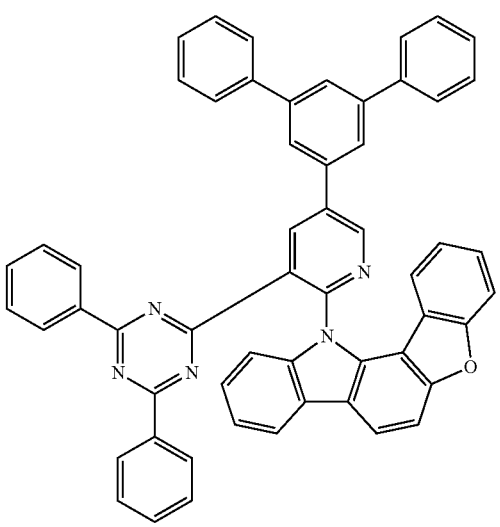
393
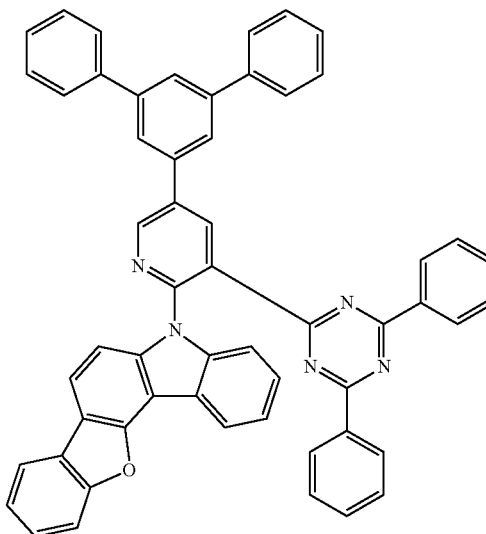

1389
-continued
394
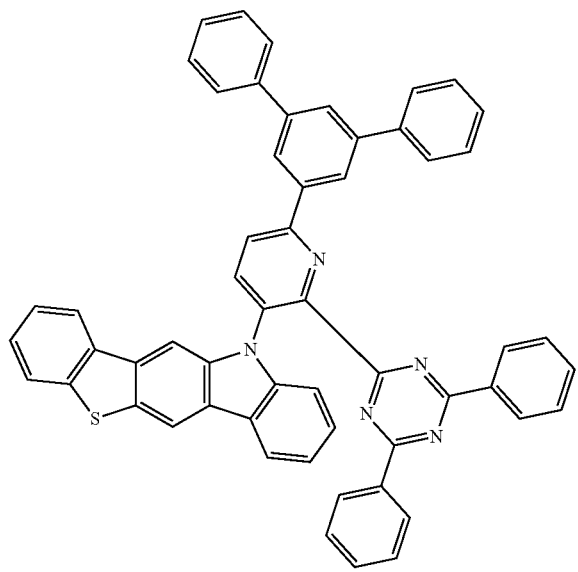
395
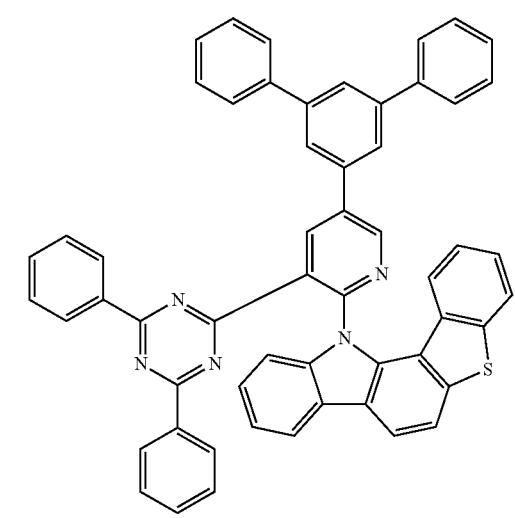
396
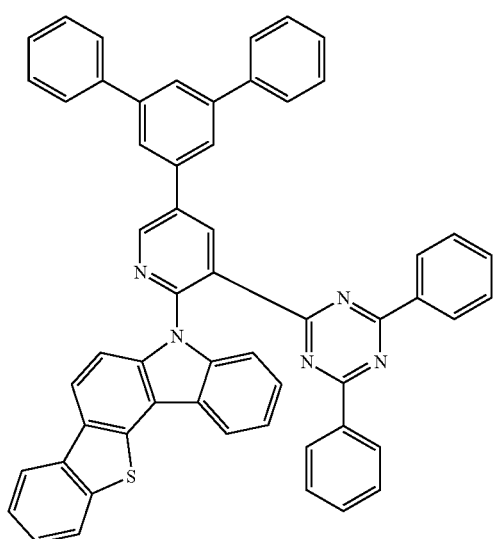
1390
-continued
397
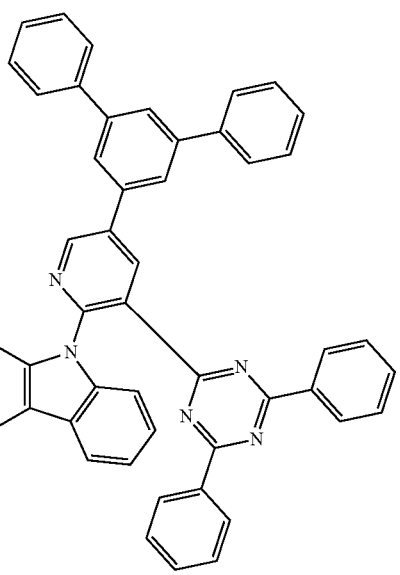
398
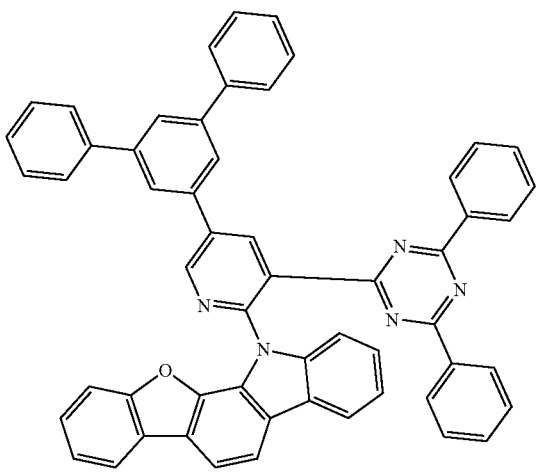
399
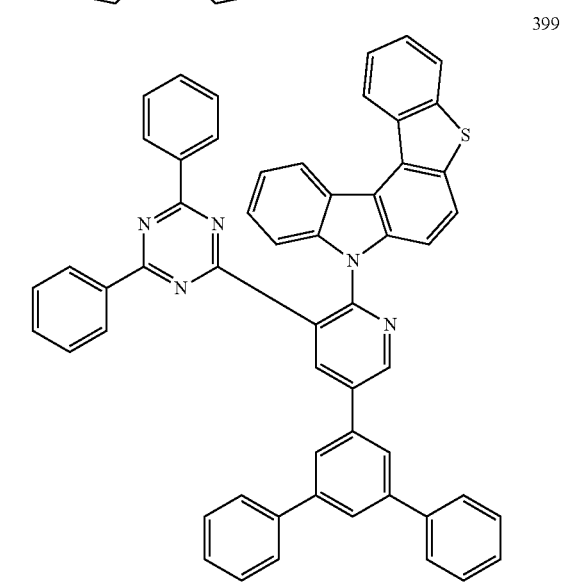

1391
-continued
400
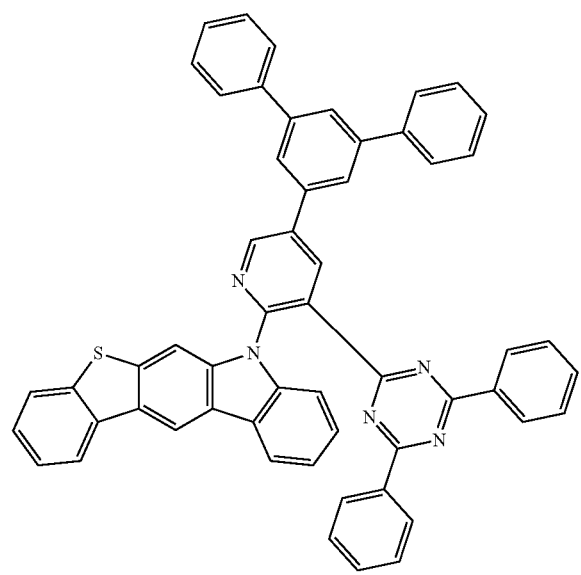
401
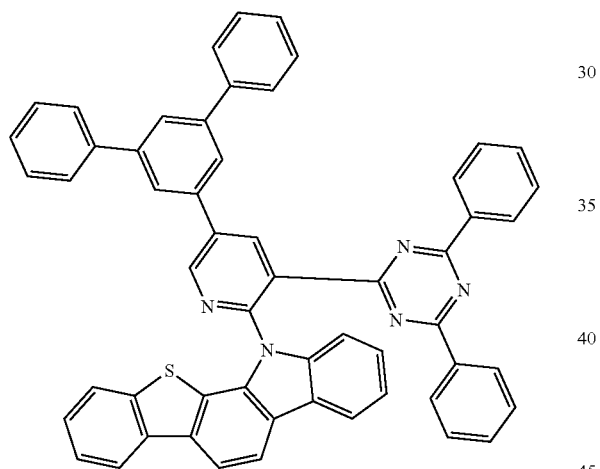
402
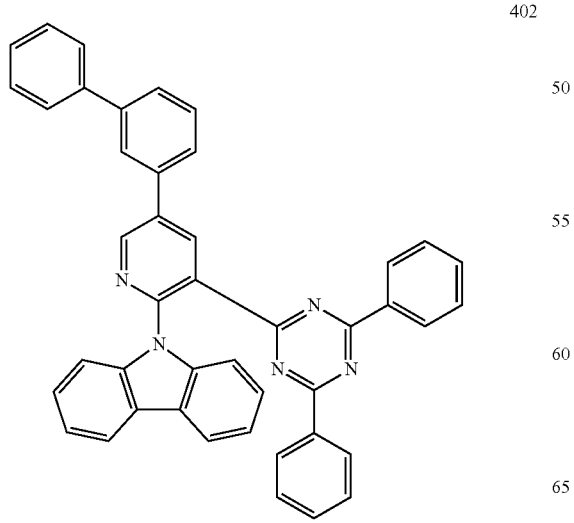
1392
-continued
403
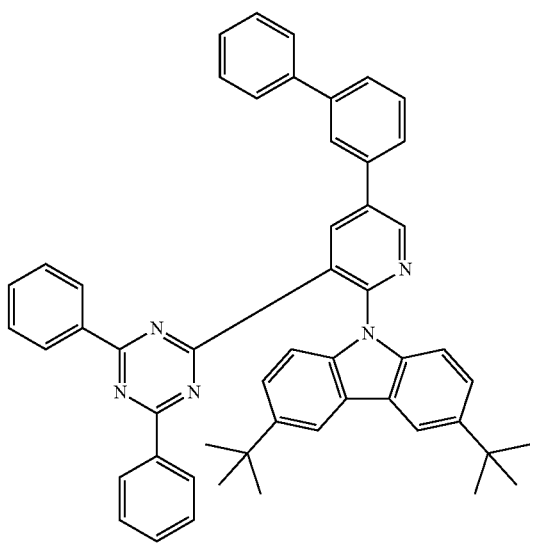
404
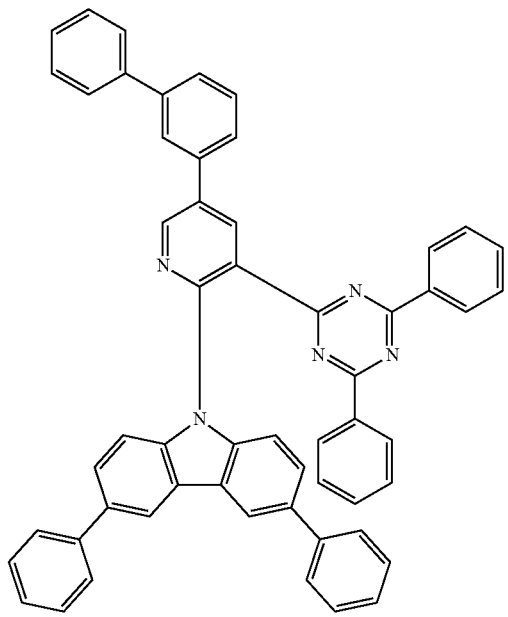

405
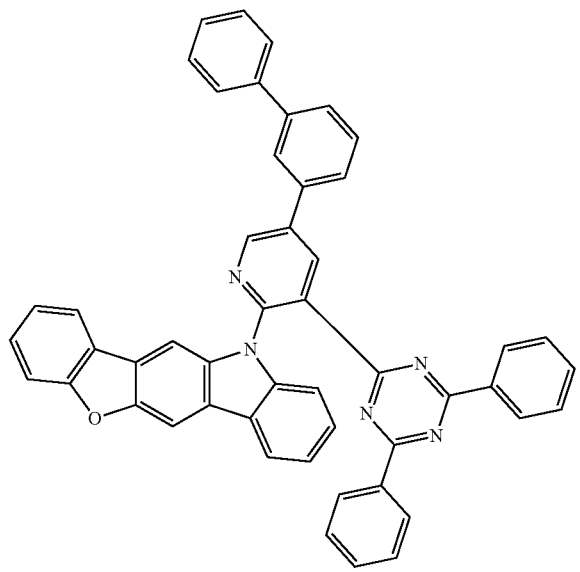
406
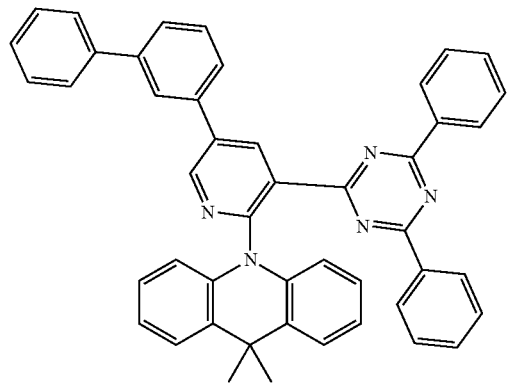
407
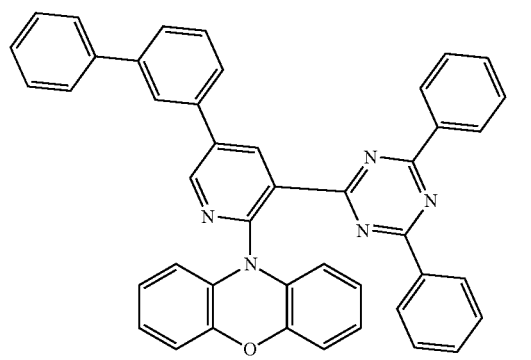
408
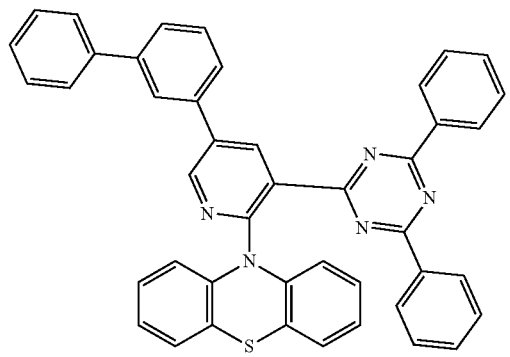
409
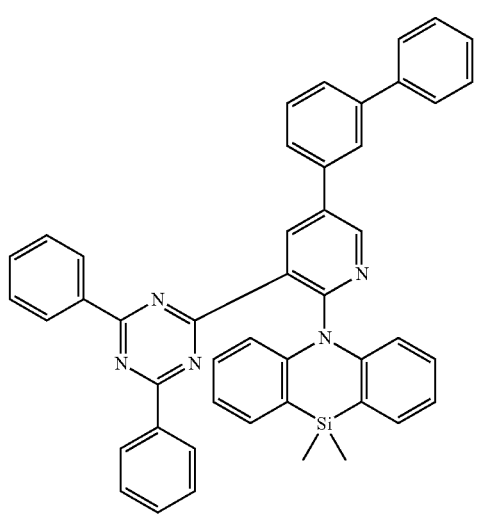
410
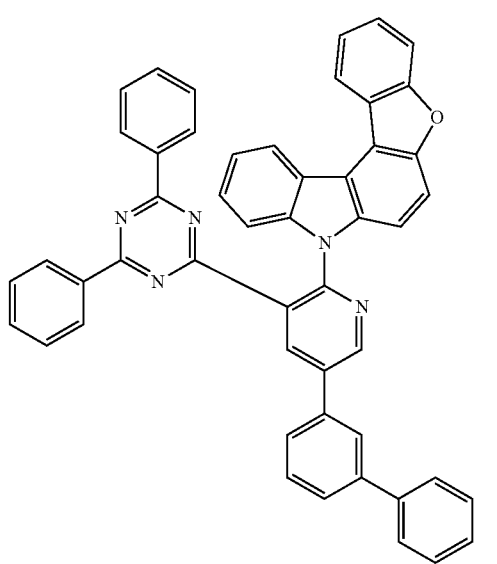

1395
-continued
411
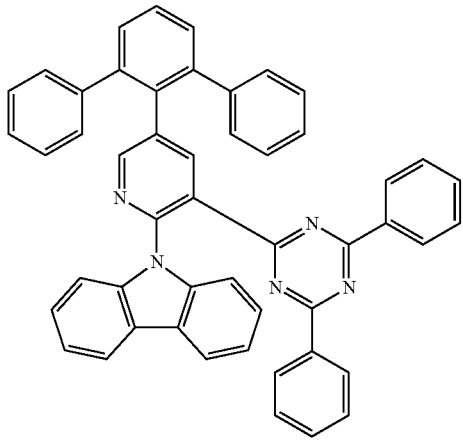
412
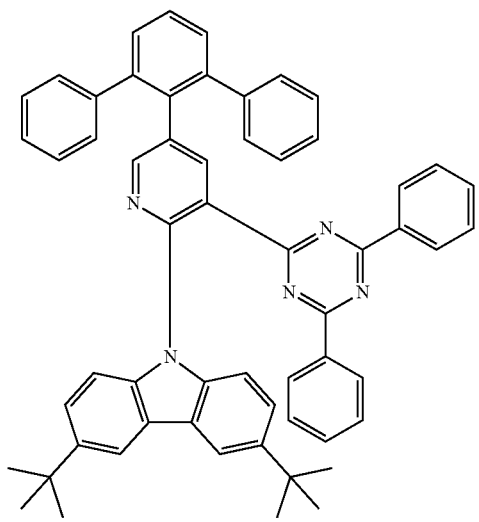
413
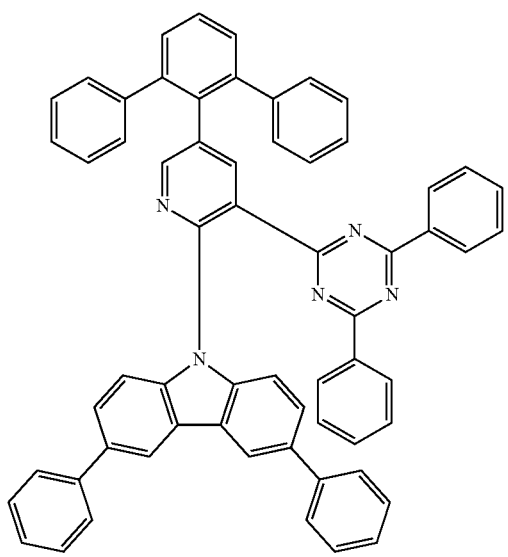
1396
-continued
414
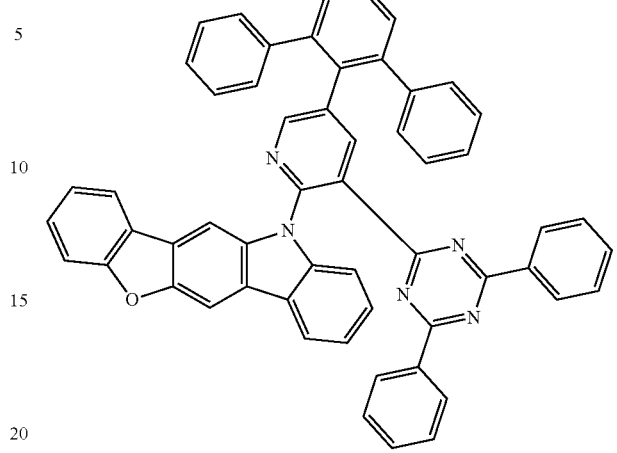
416
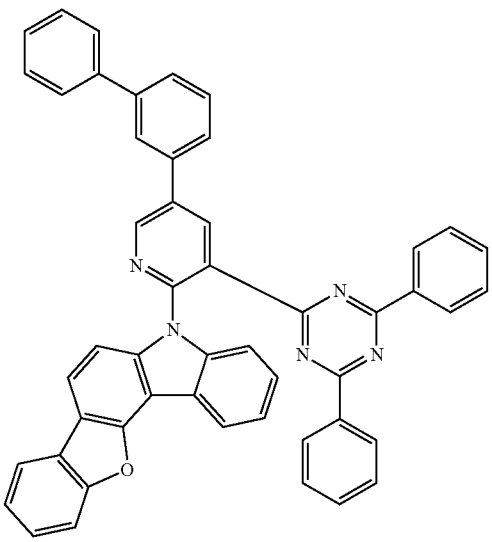
417
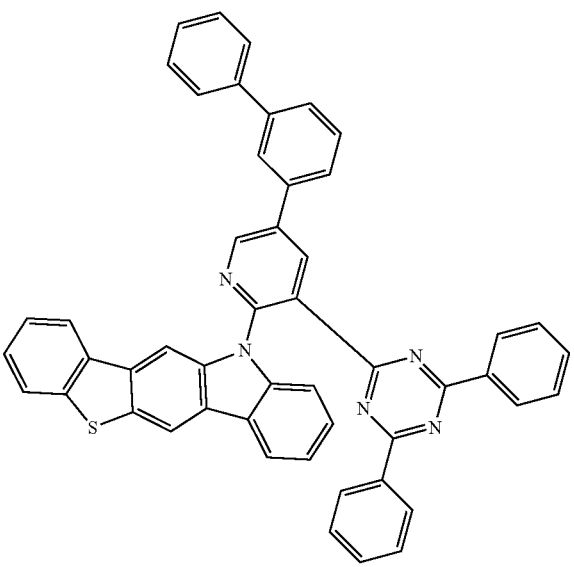

1397
-continued
418
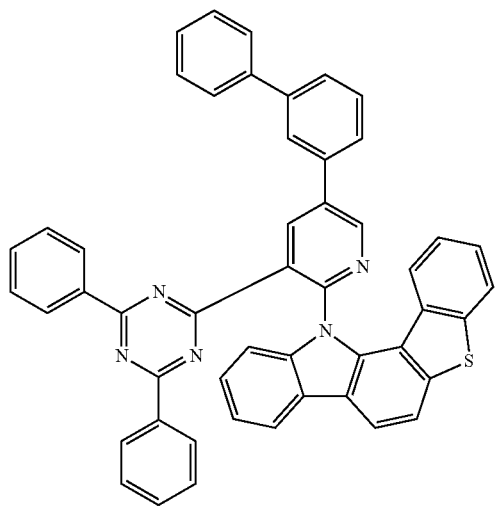
419
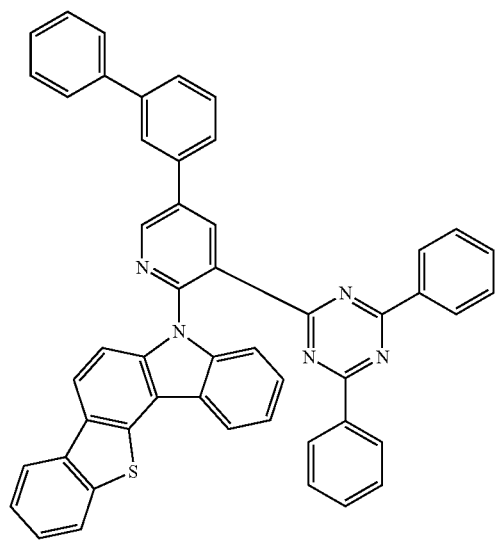
420
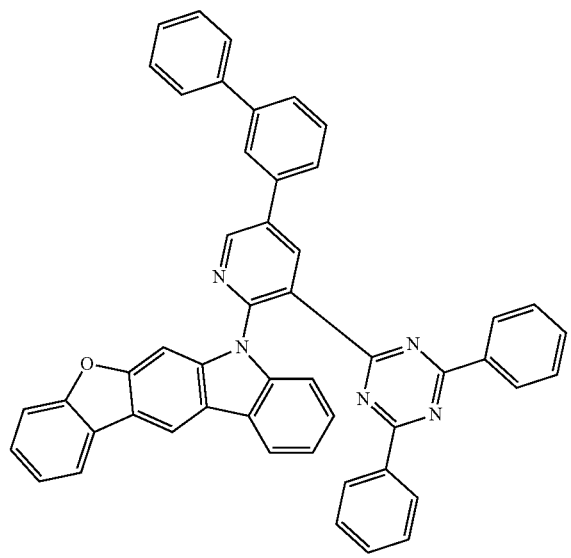
1398
-continued
421
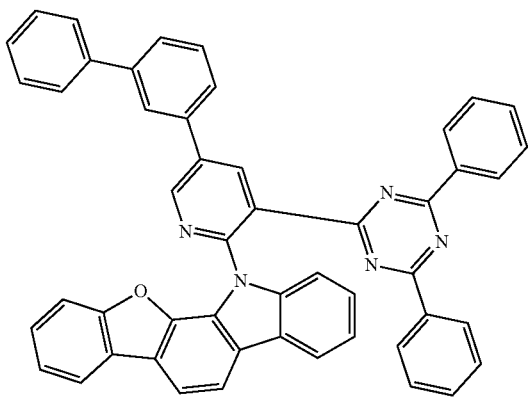
423
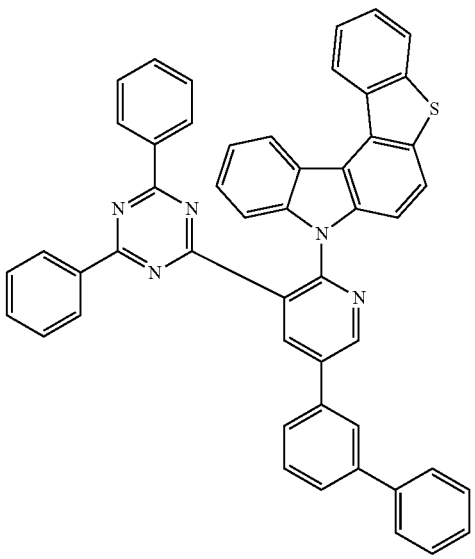
424
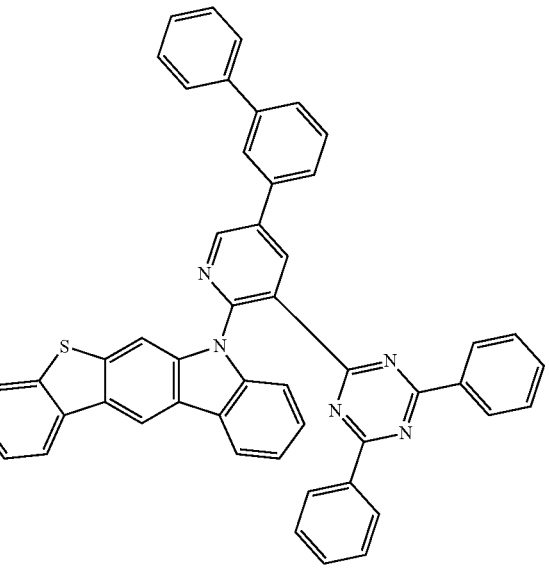

1399
-continued
425
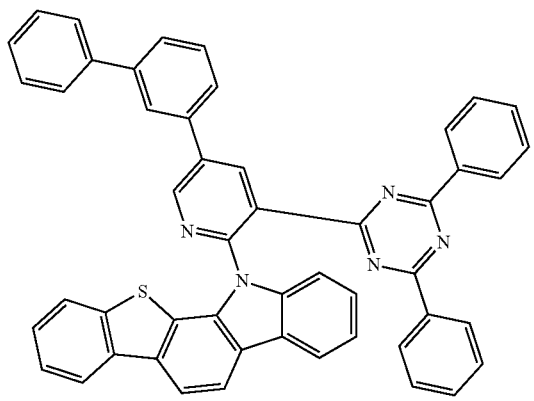
426
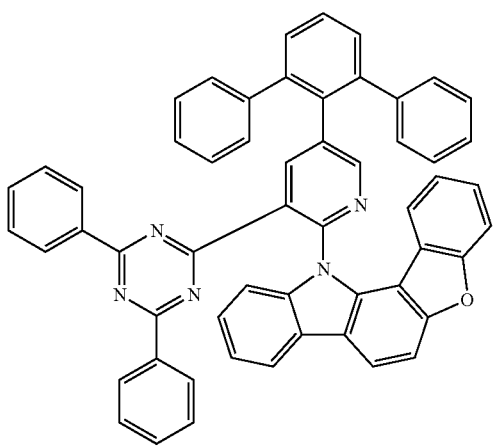
427
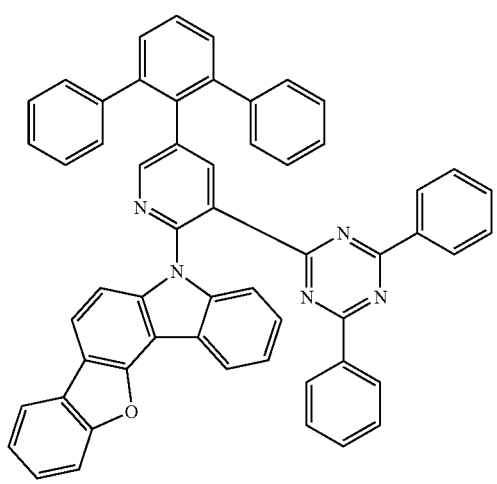
1400
-continued
428
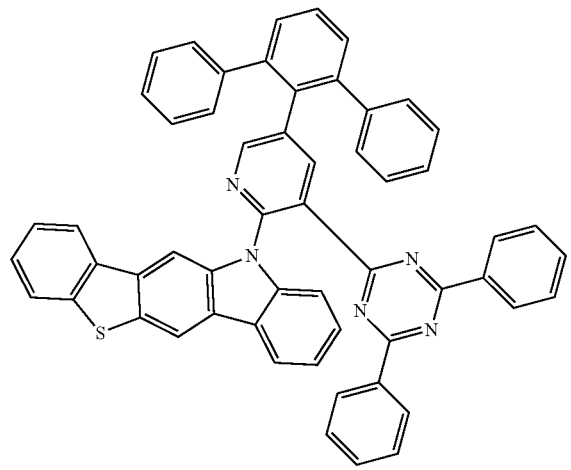
429
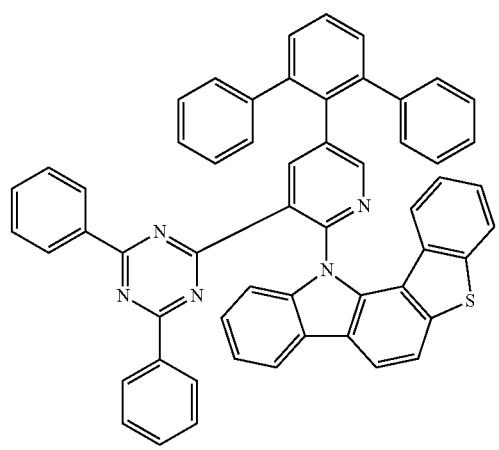
430
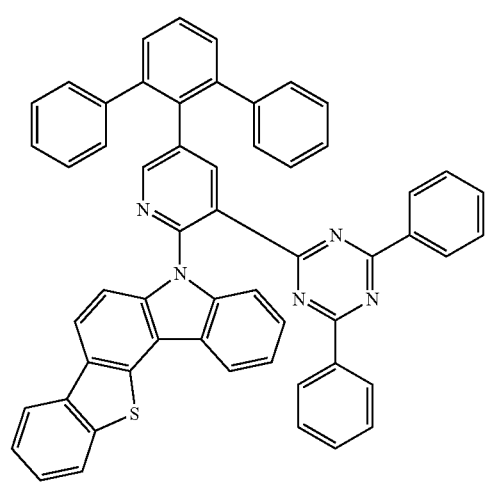

1401
-continued
431
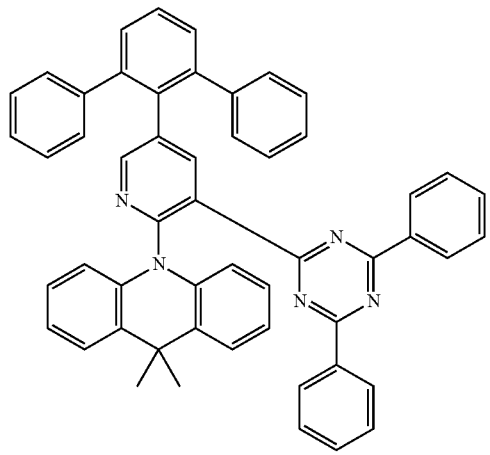
432
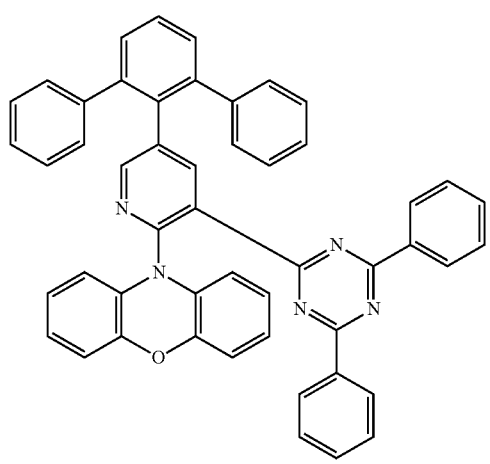
433
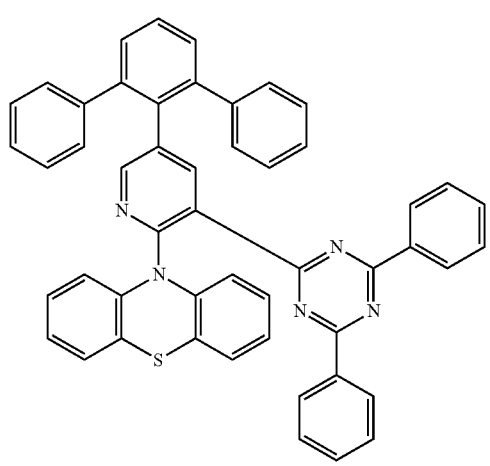
1402
-continued
434
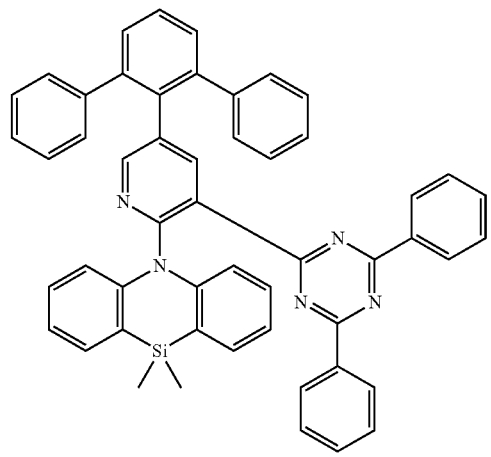
435
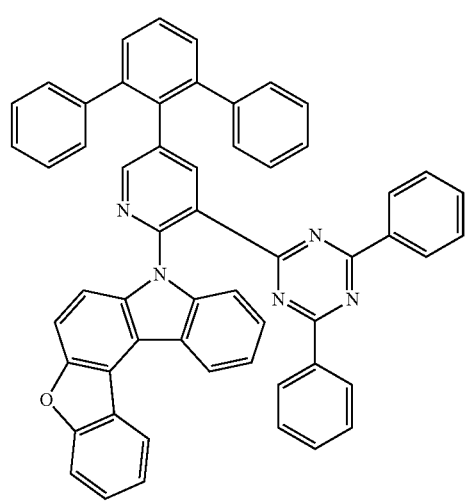
436
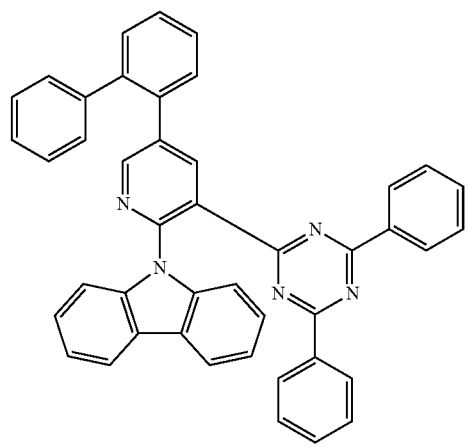

1403
-continued
437
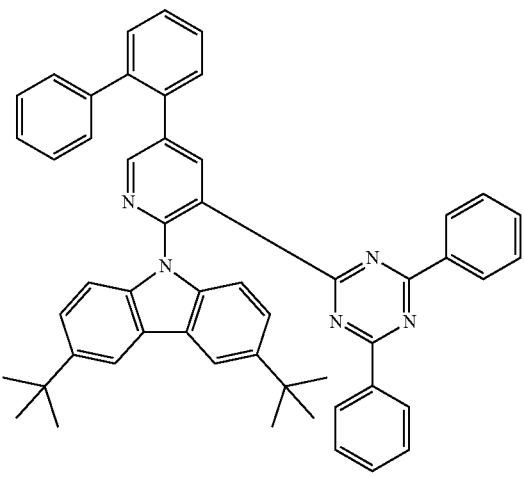
438
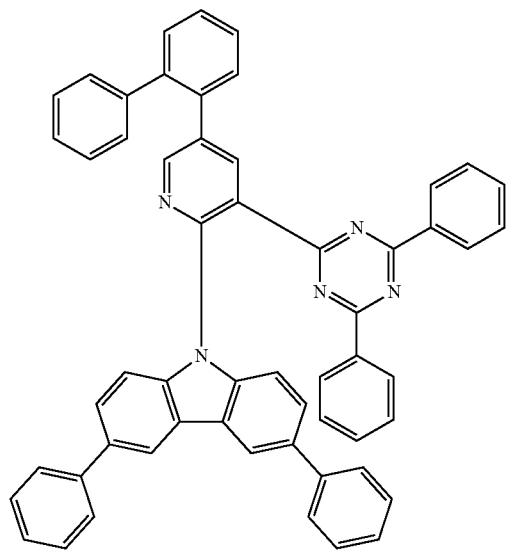
439
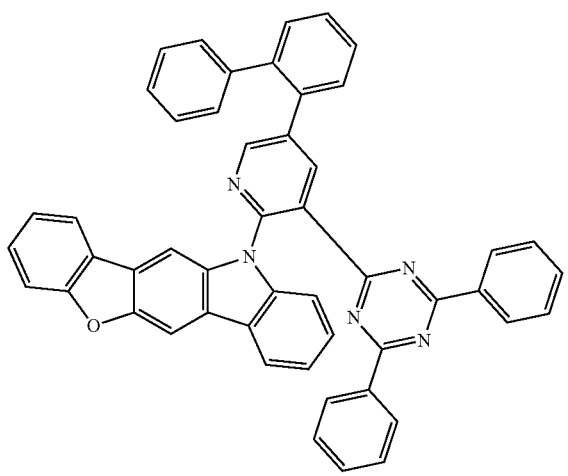
1404
-continued
440
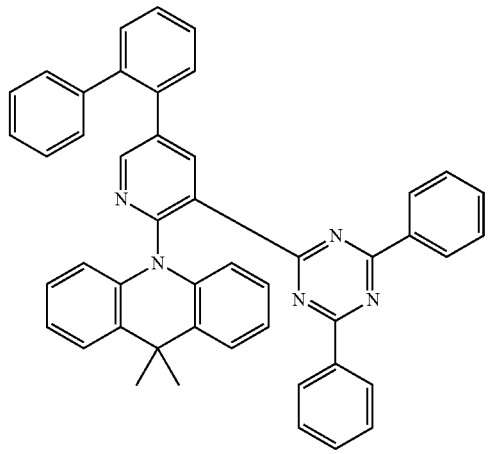
441
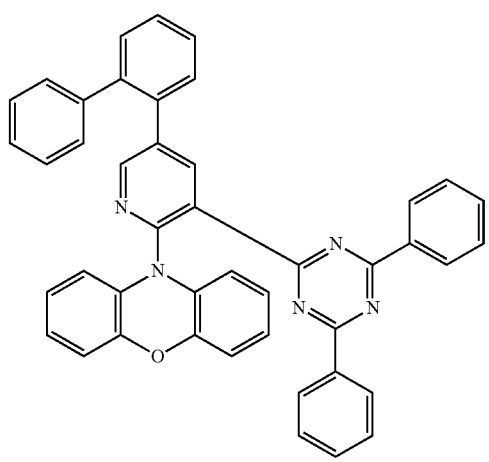
442
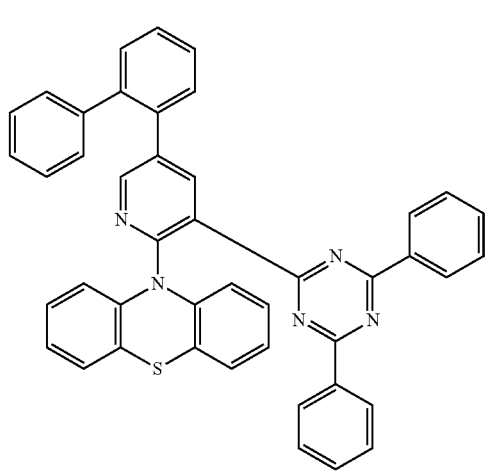

1405
-continued
443
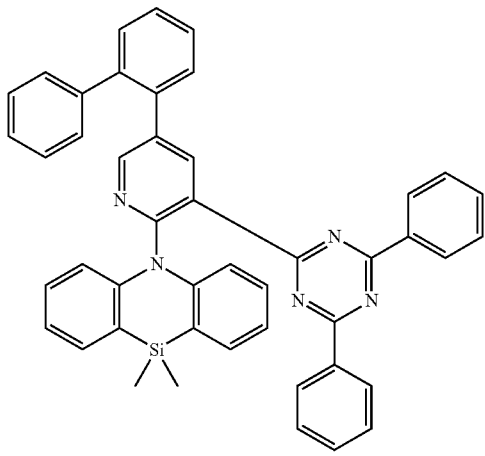
444
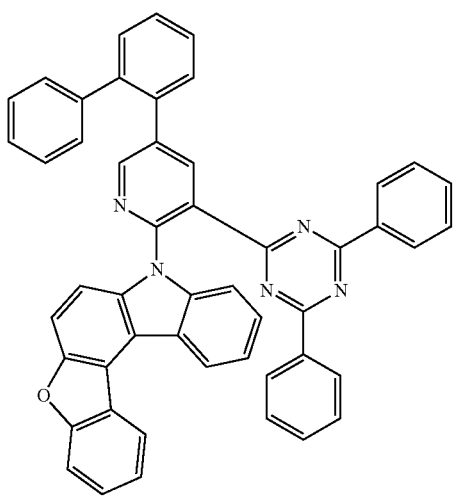
445
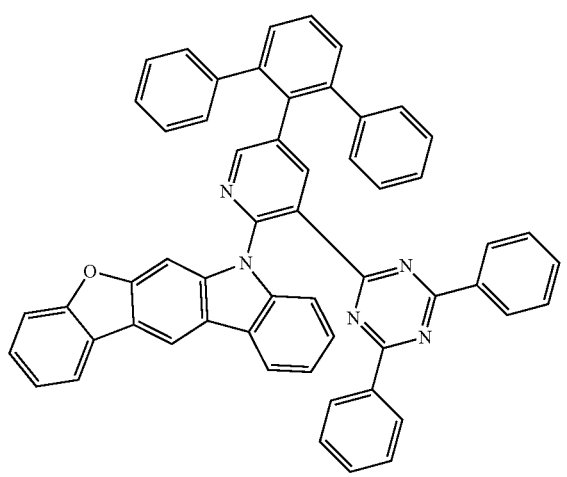
1406
-continued
446
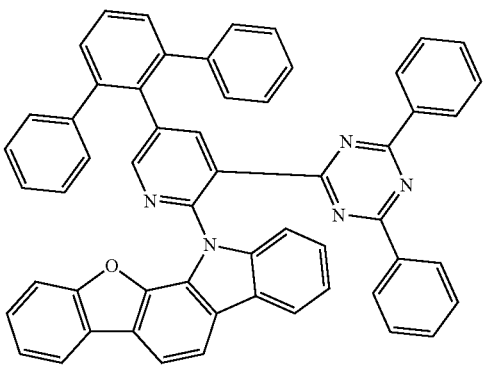
447
448
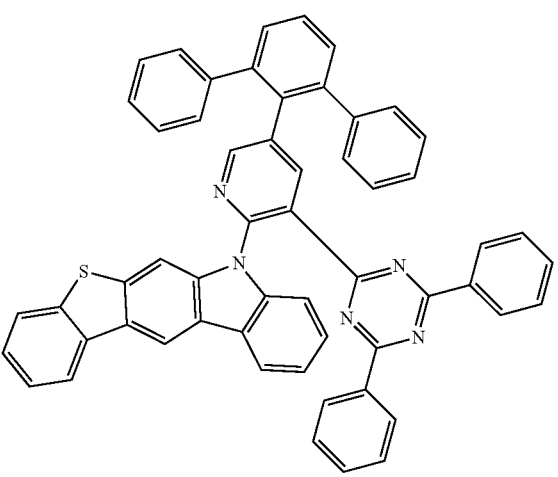

1407
-continued
449
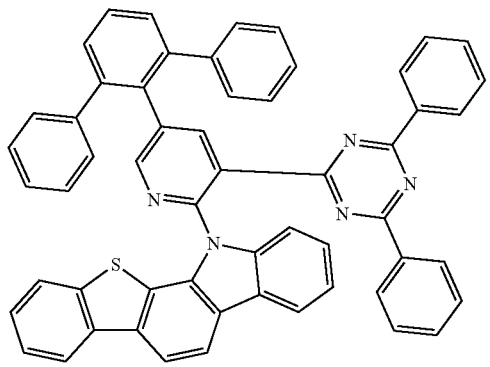
450
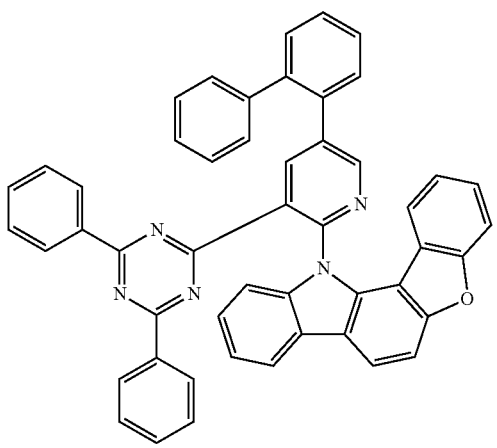
451
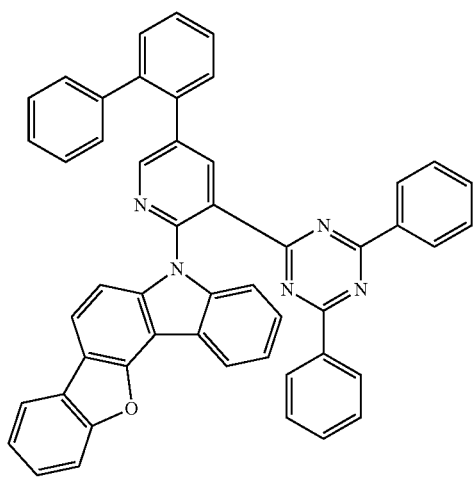
1408
-continued
452
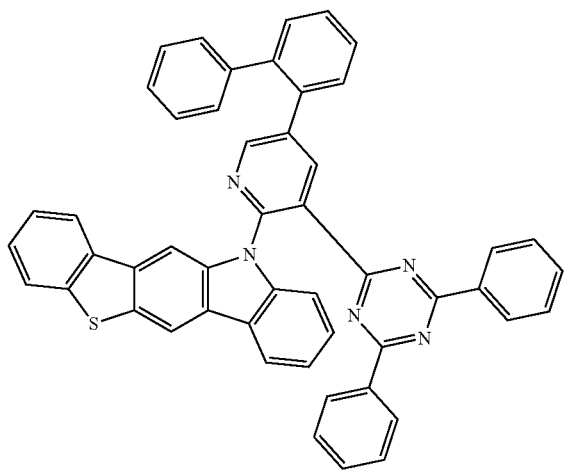
453
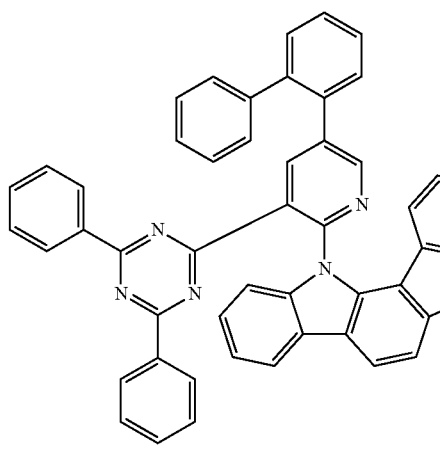
454
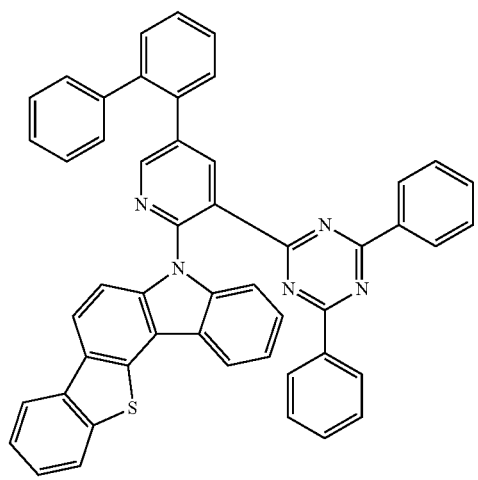

1409
-continued
455
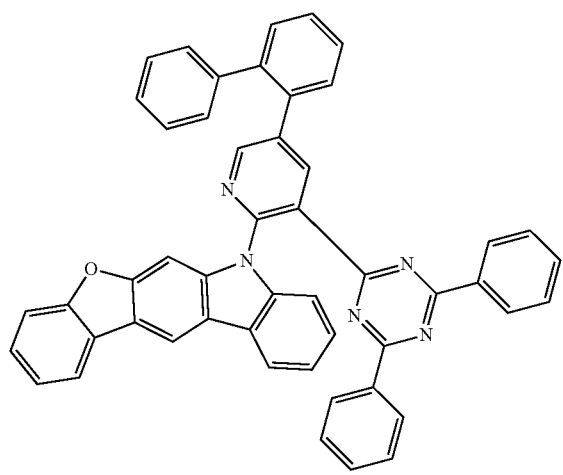
456
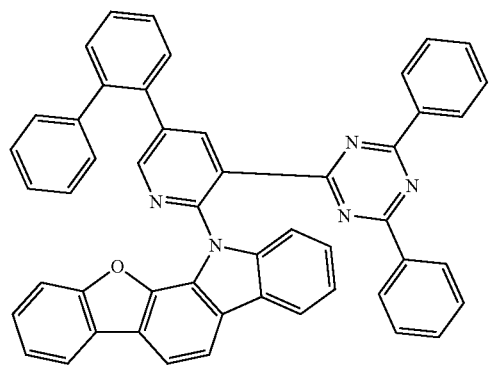
457
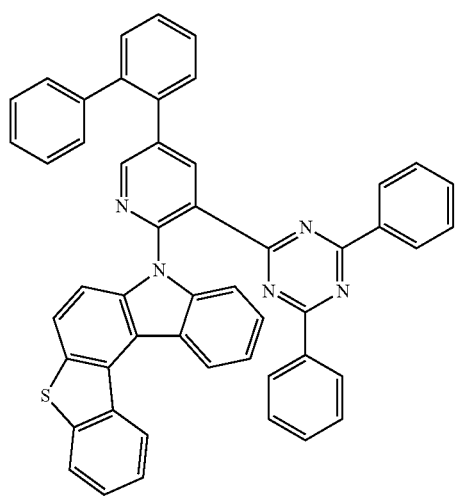
1410
-continued
458
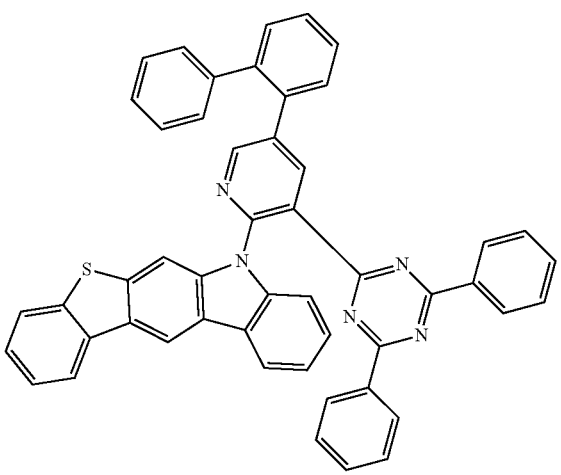
459
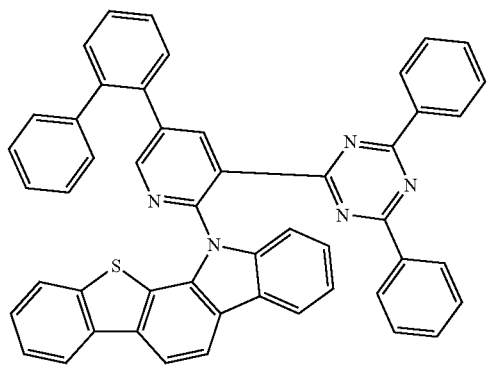
460
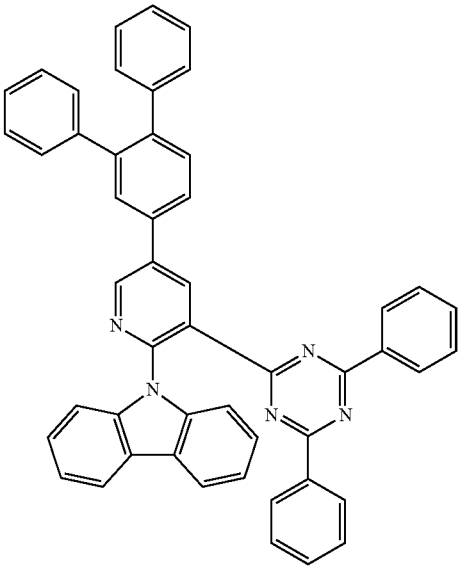

1411
-continued
461
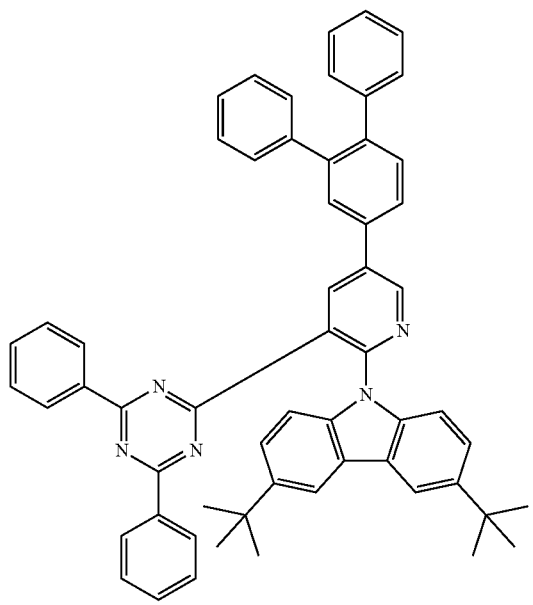
462
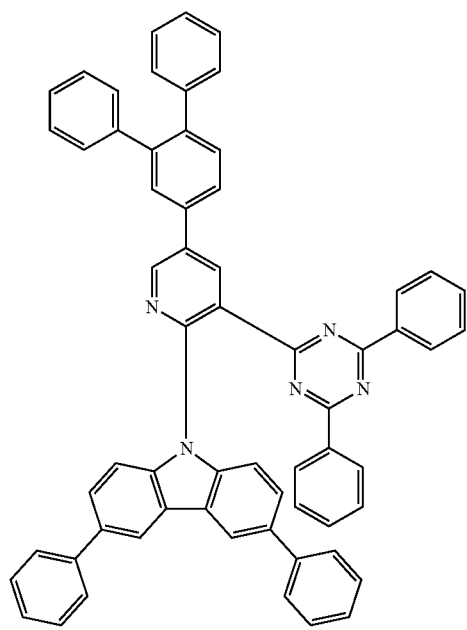
1412
-continued
463
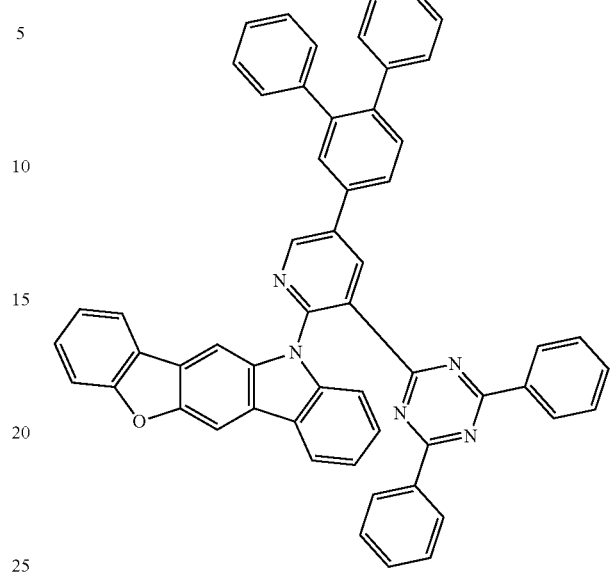
464
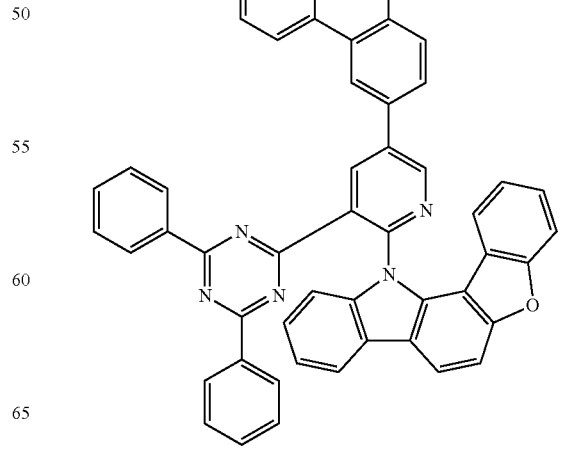

1413
-continued
465
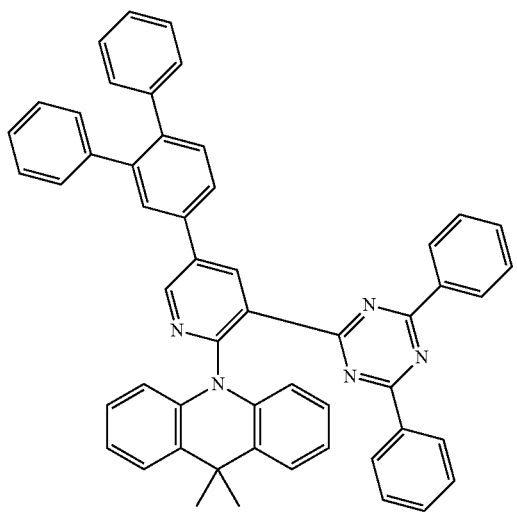
466
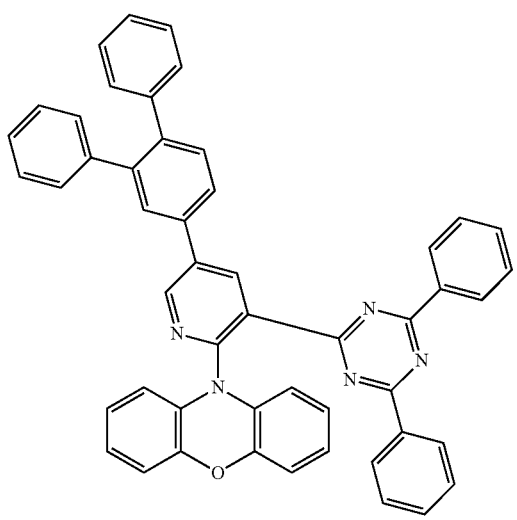
467
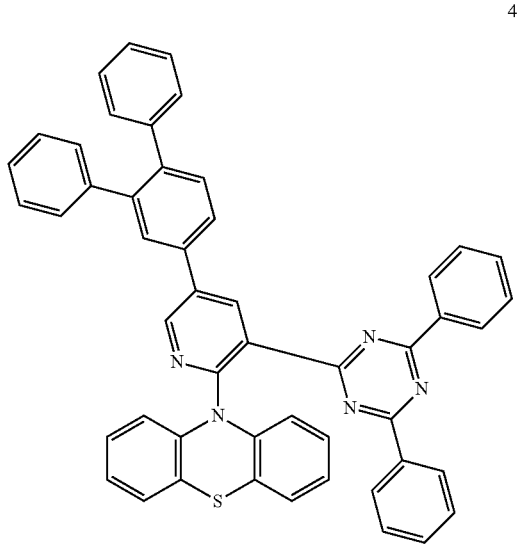
1414
-continued
468
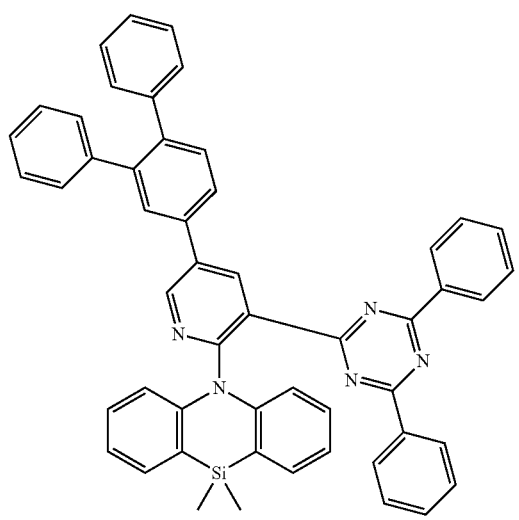
469
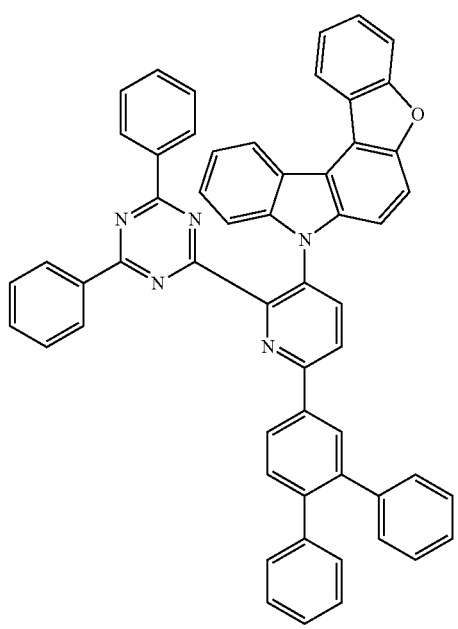

1415
-continued
470
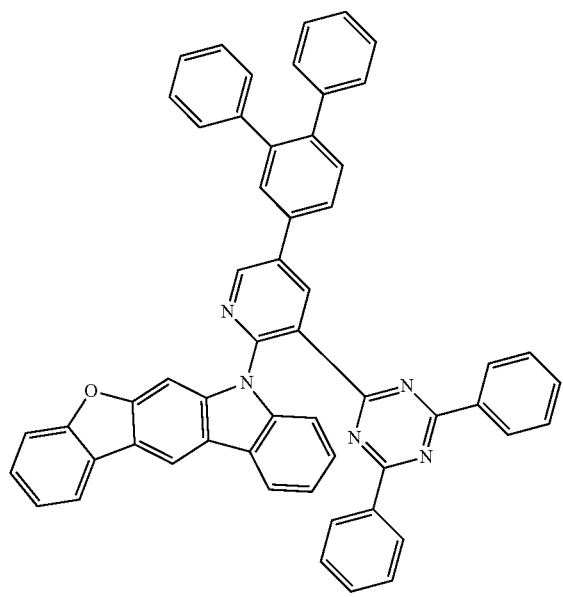
471
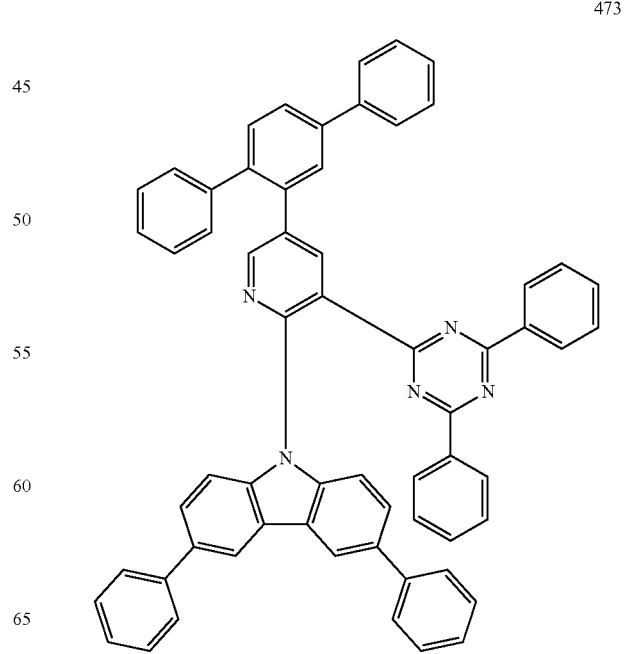
1416
-continued
472
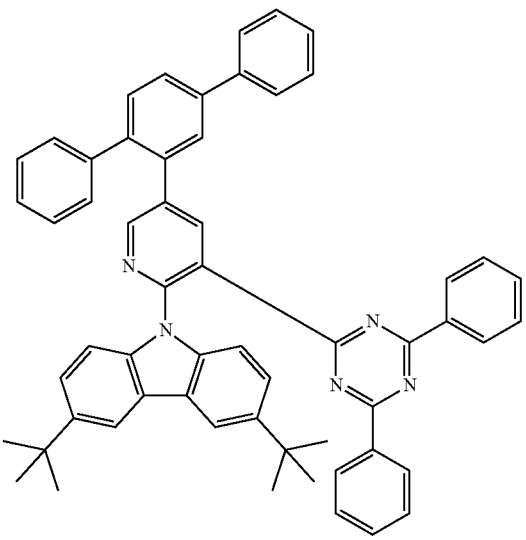
473
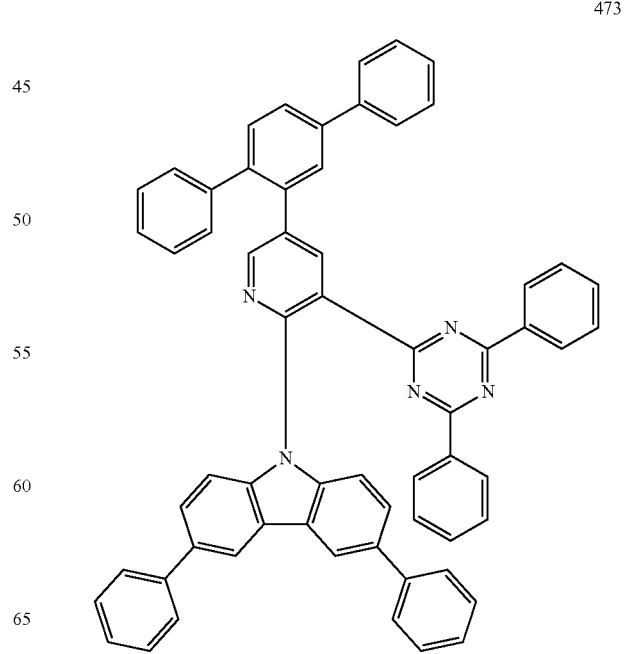

1417
-continued
474
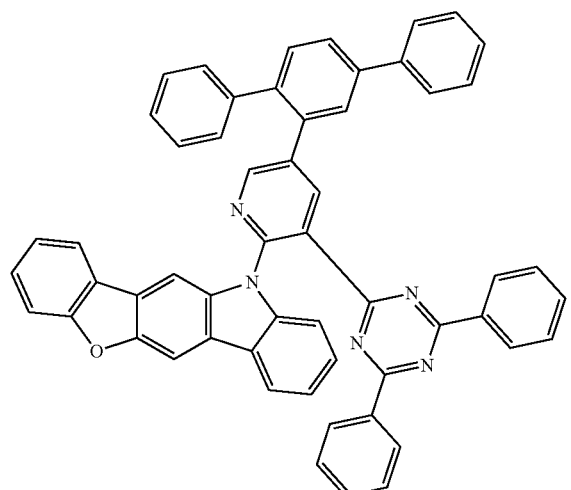
475
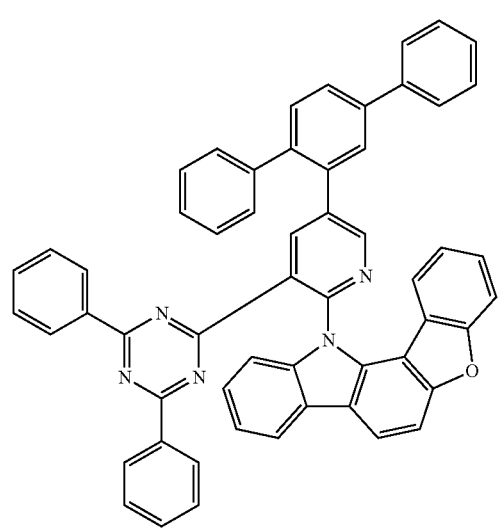
476
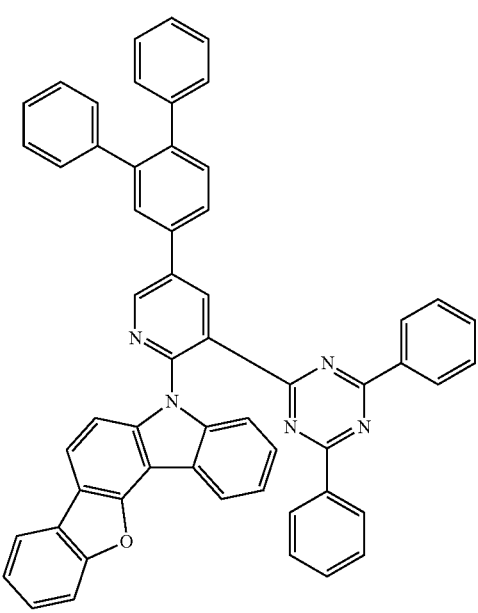
1418
-continued
477
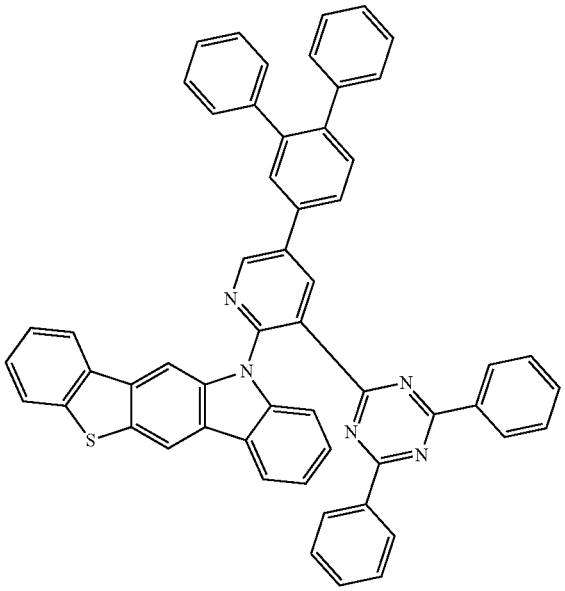
478
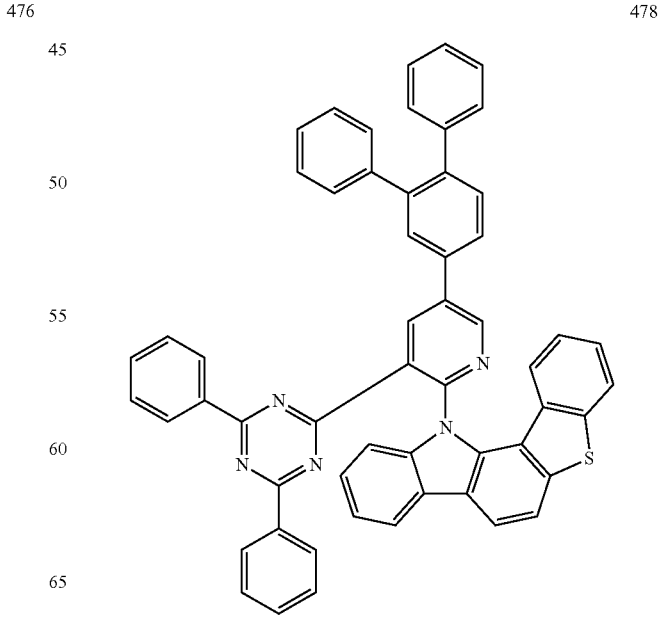

1419
-continued
479
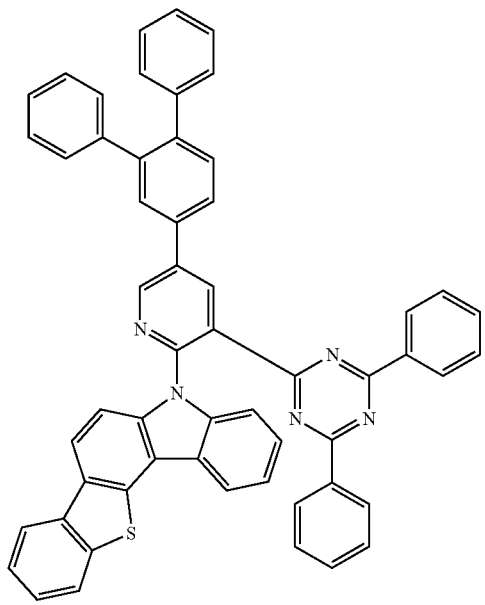
1420
-continued
481
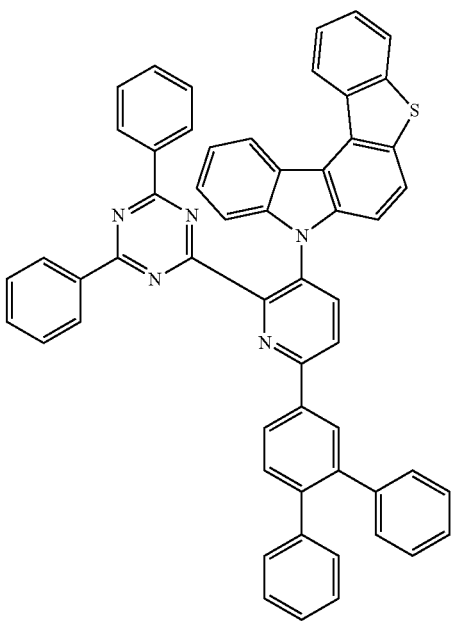
480
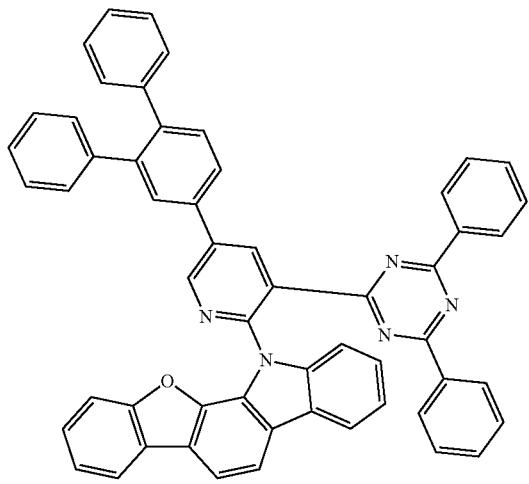
482
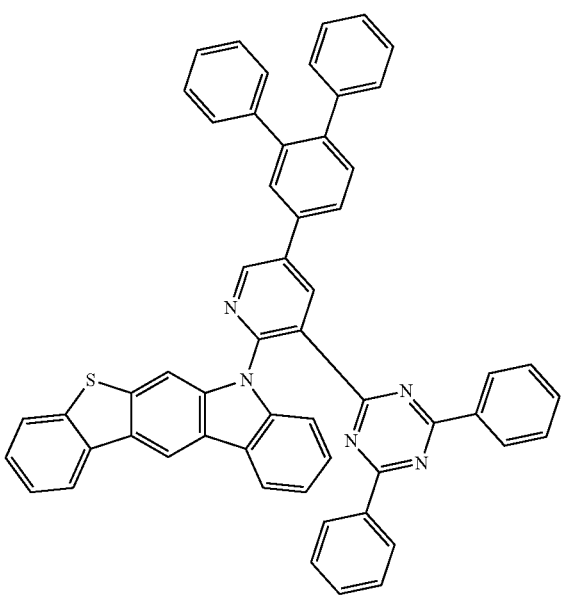

1421 -continued
483
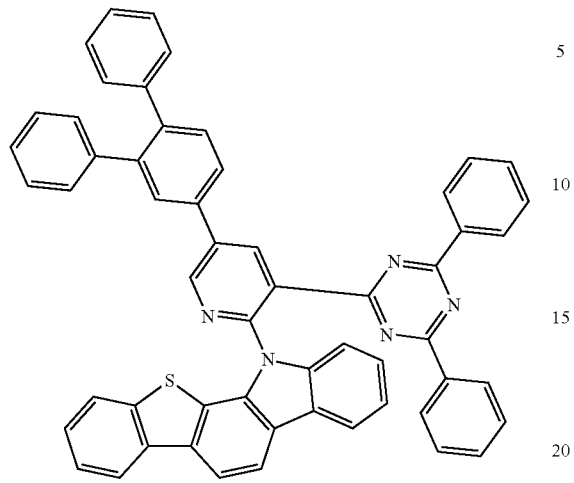
484
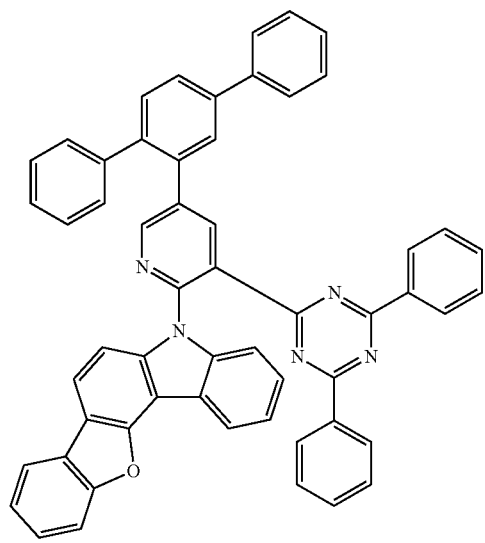
485
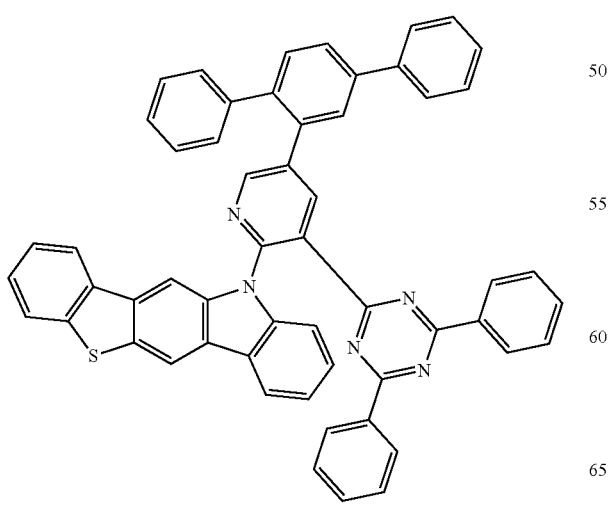
1422 -continued
486
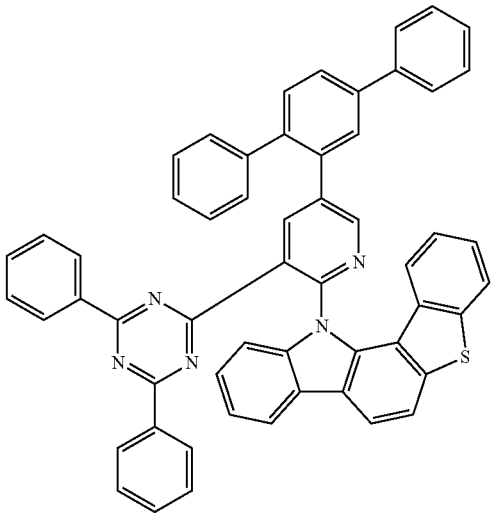
487
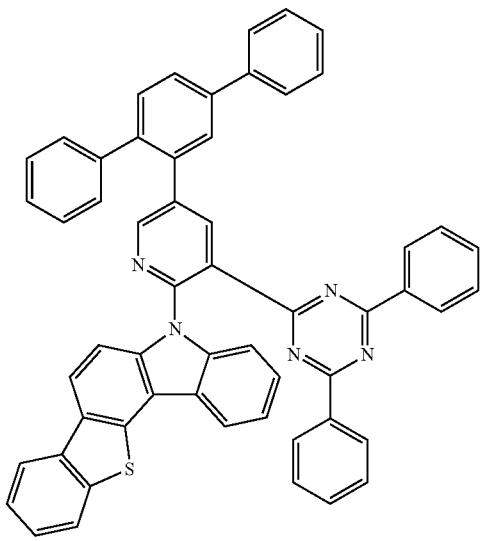
488
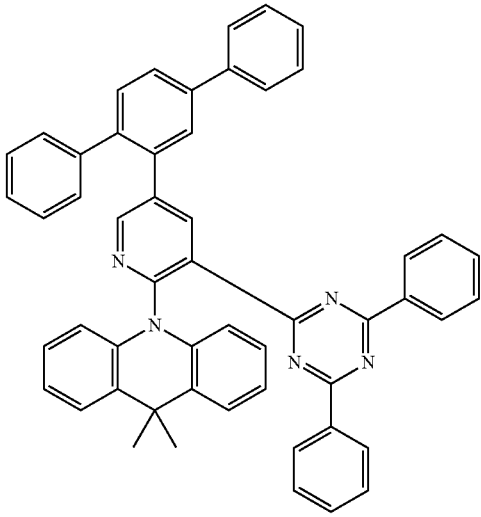

1423
-continued
489
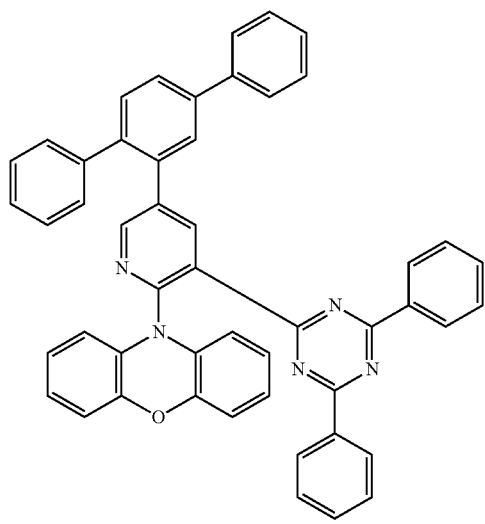
490
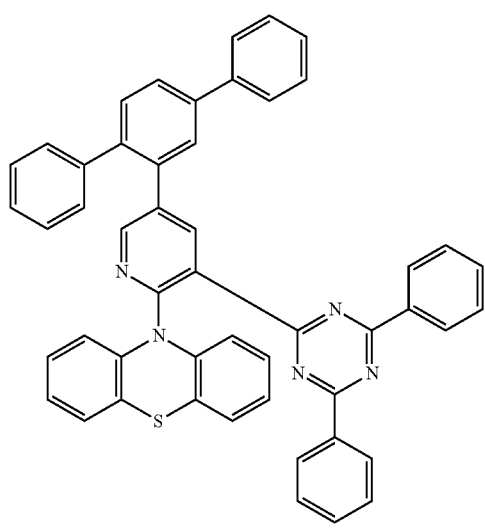
491
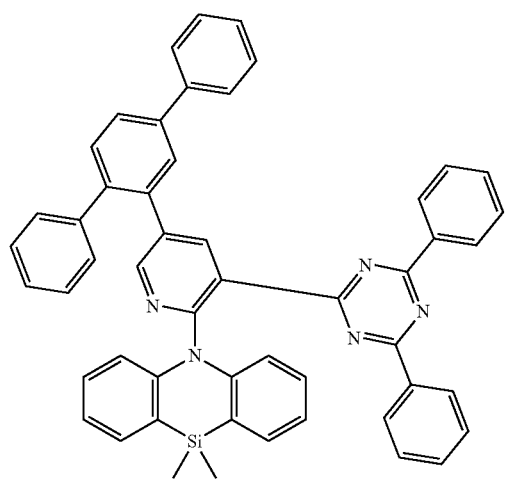
1424
-continued
492
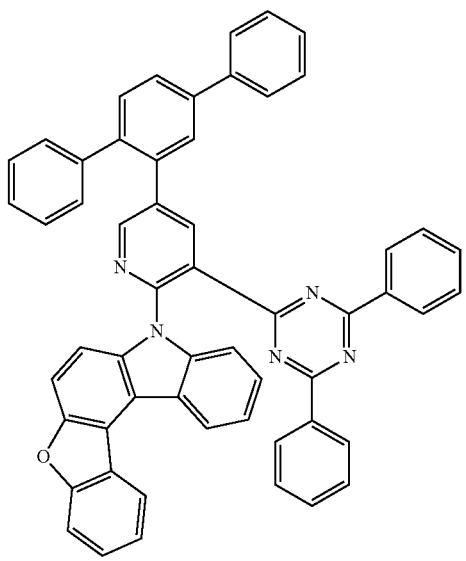
493
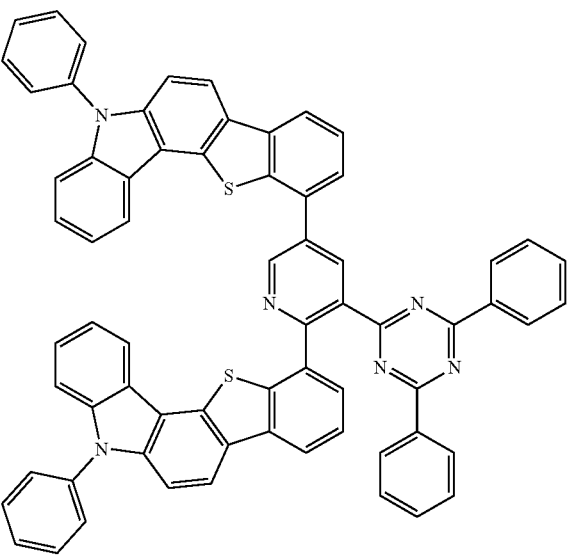

1425
-continued
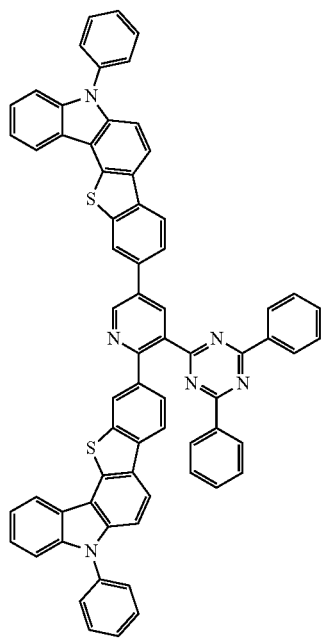
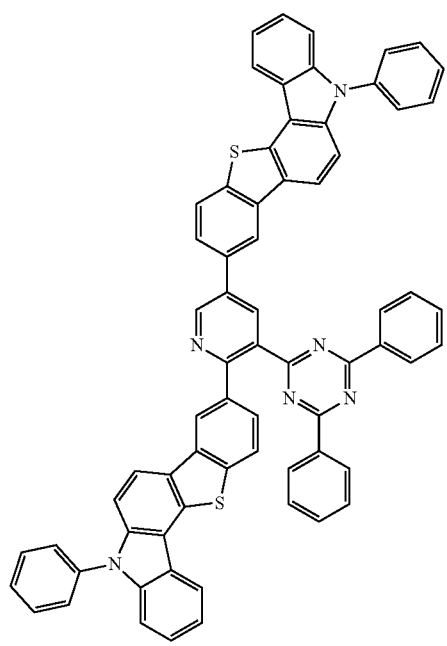
1426
-continued
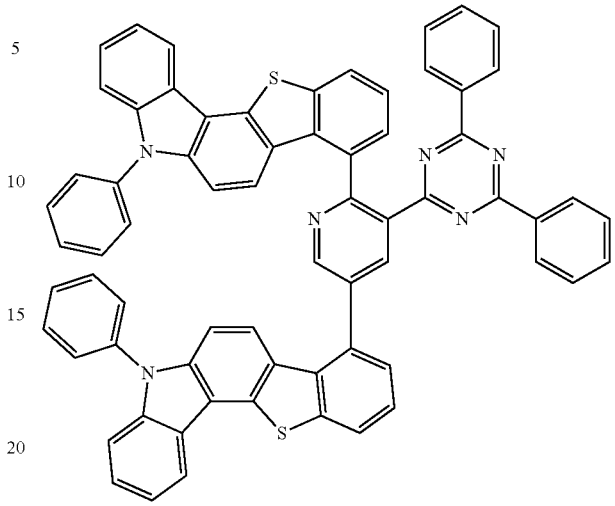
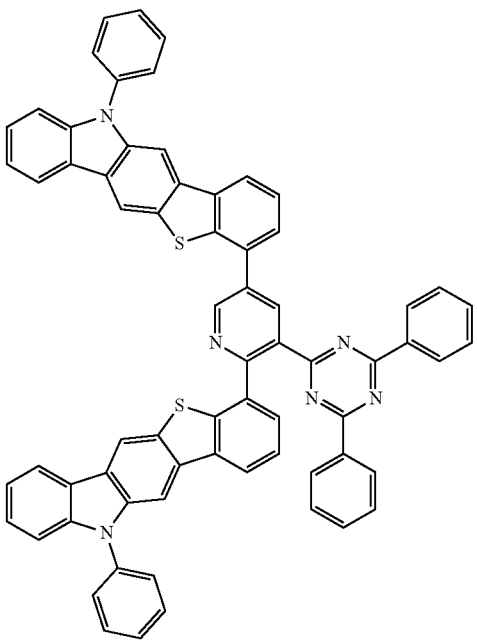

1427
-continued
498
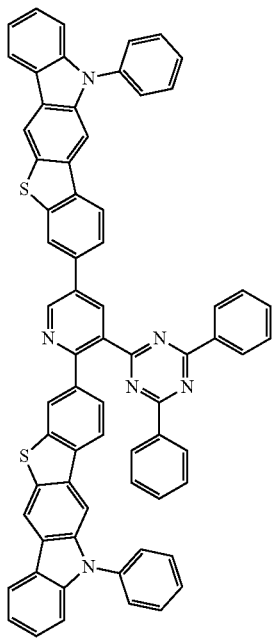
1428
-continued
500
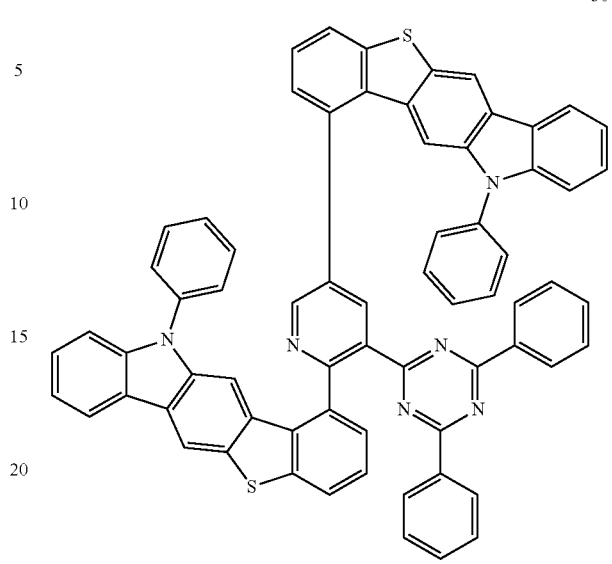
501
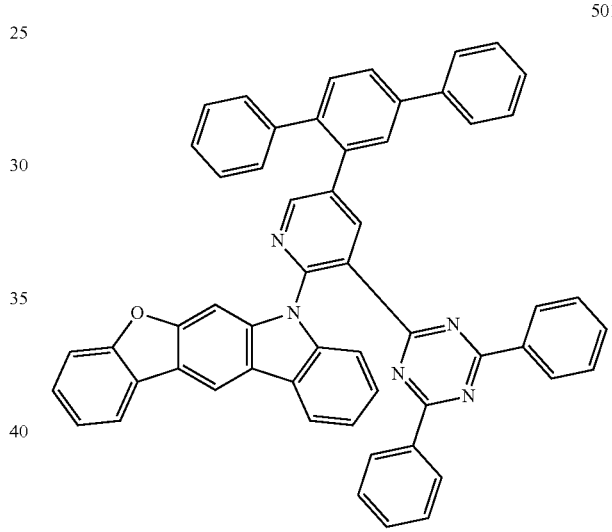
499
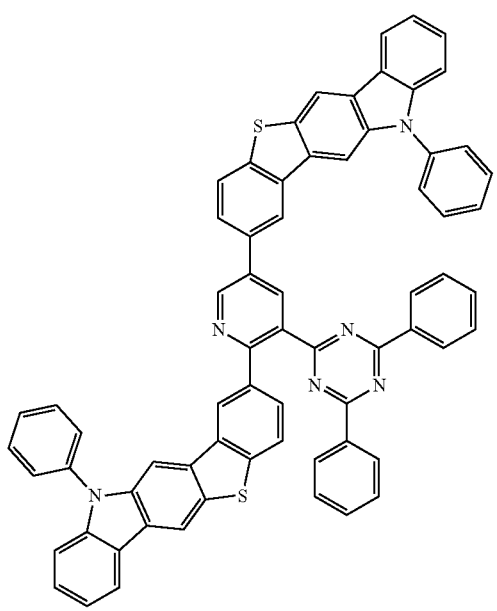
502
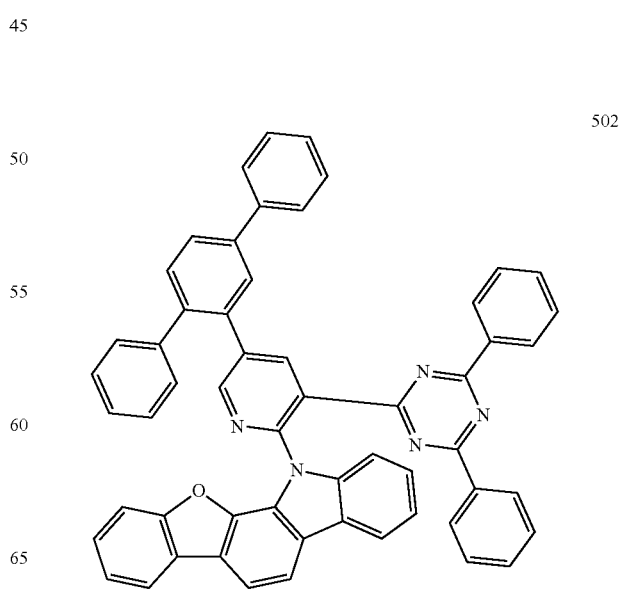

1429
-continued
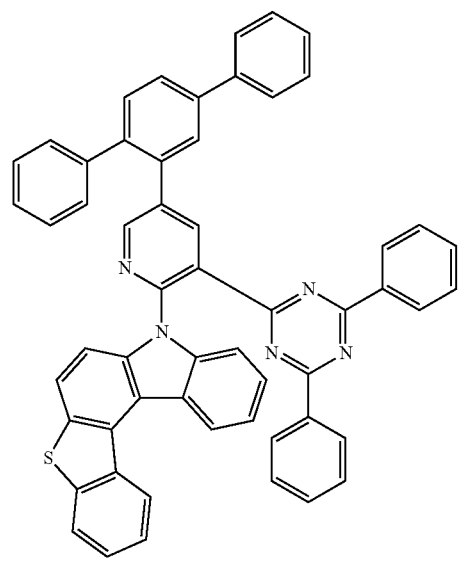
503
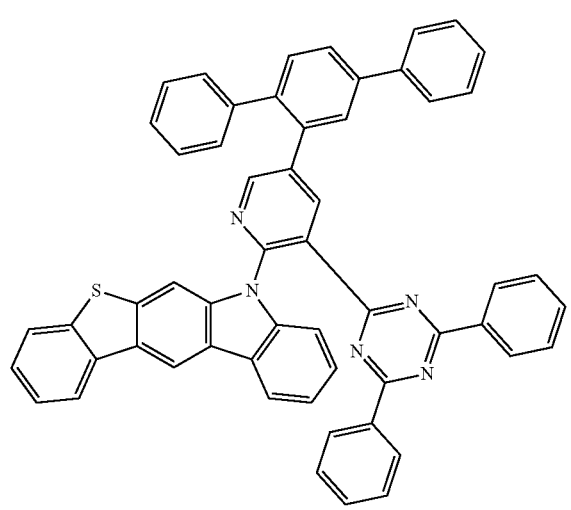
504
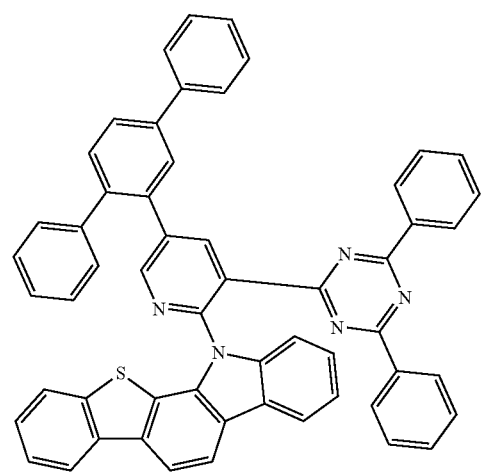
505
1430
-continued
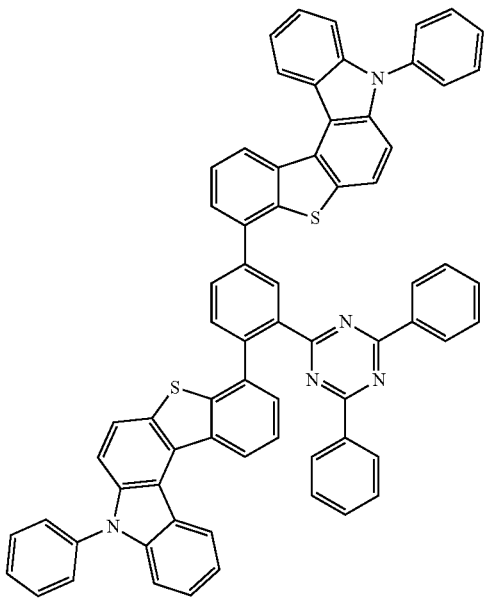
506
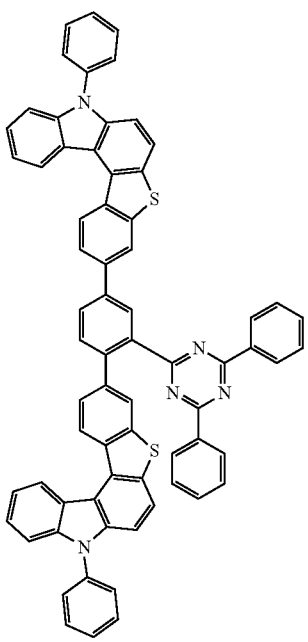
507

508
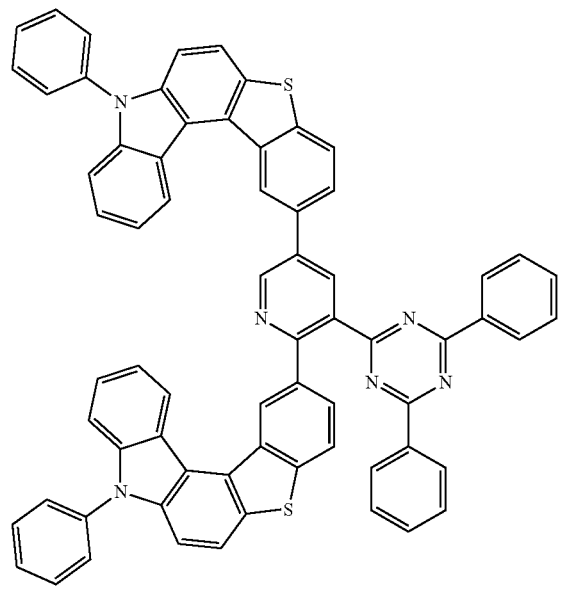
510
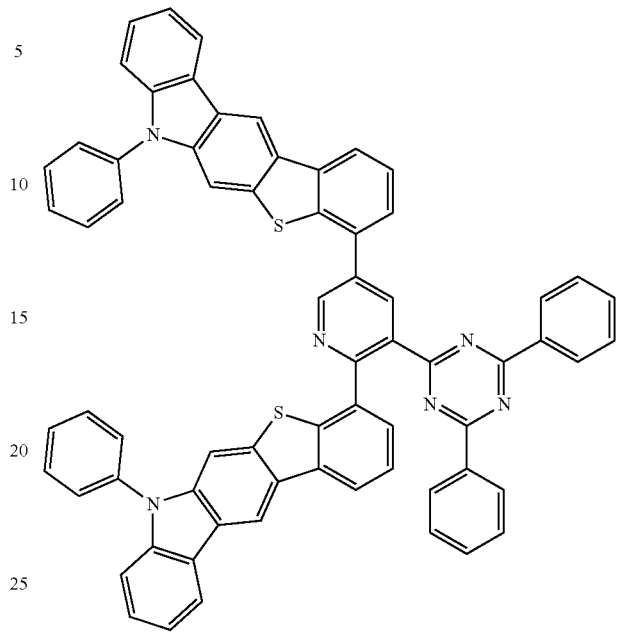
509
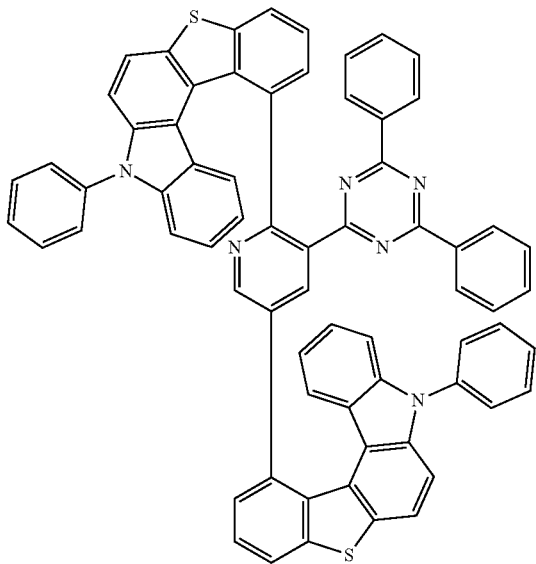
511
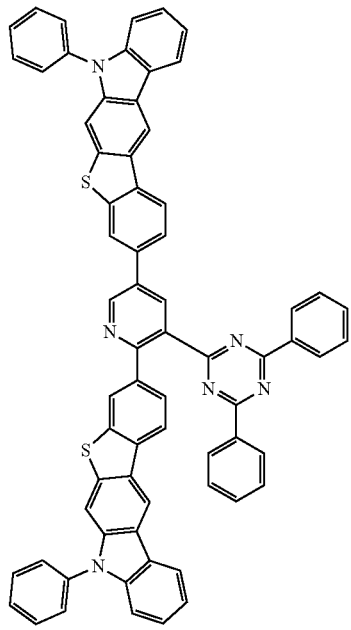

1433
-continued
512
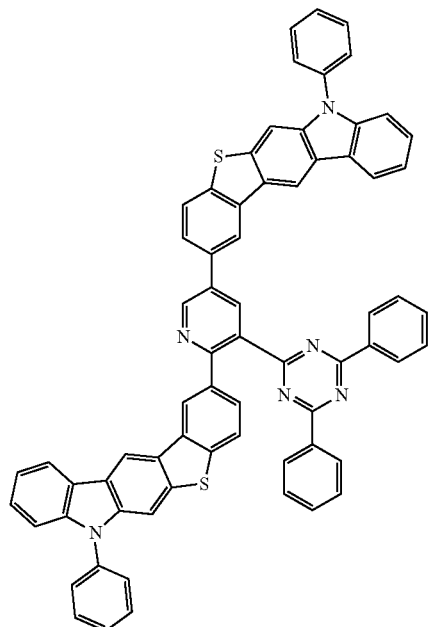
1434
-continued
514
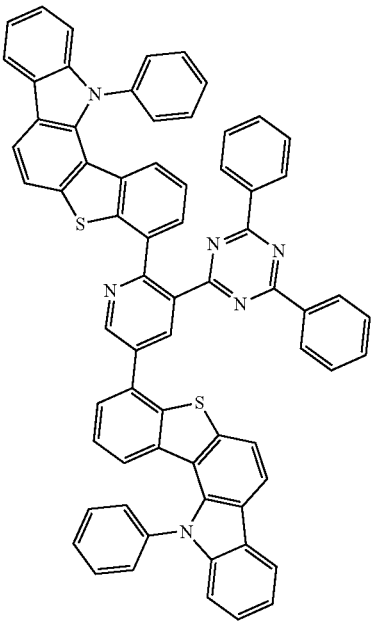
513
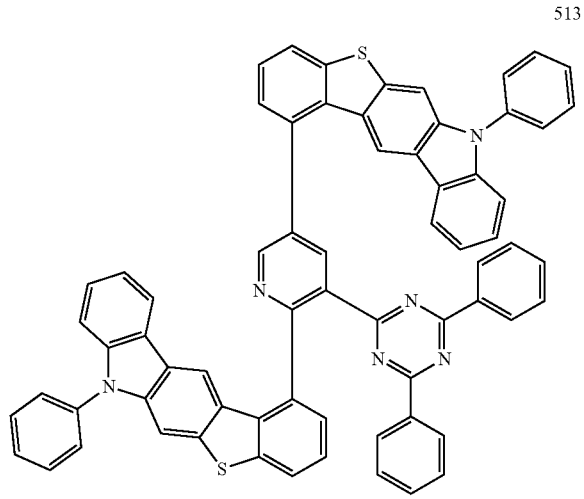
515
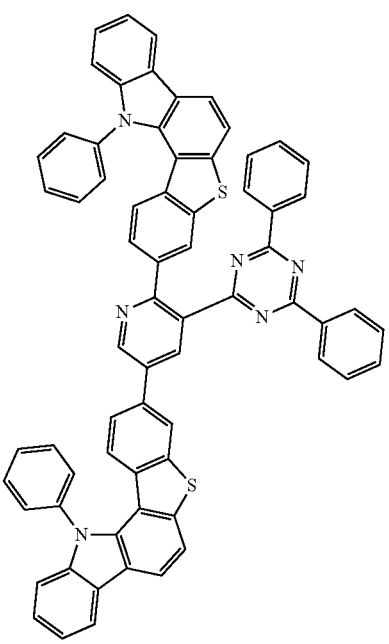

516
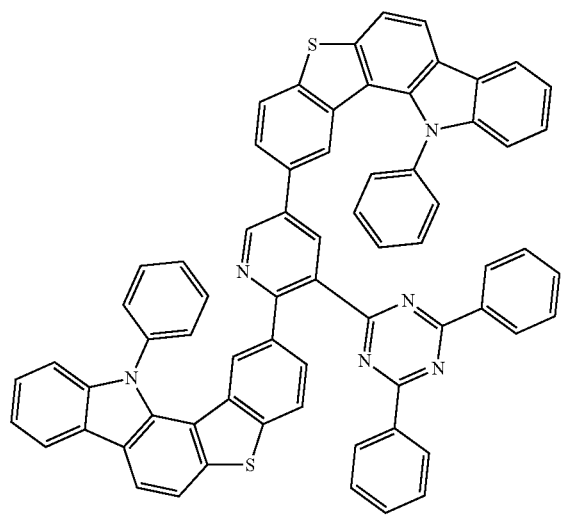
517
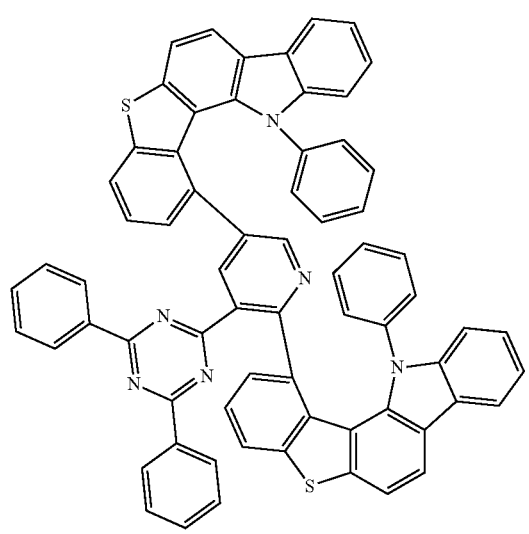
518
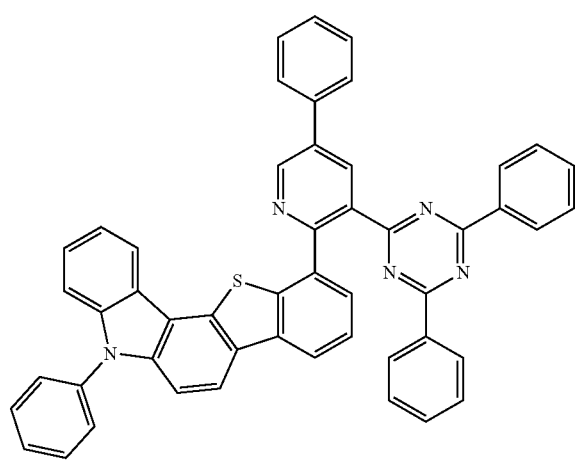
519
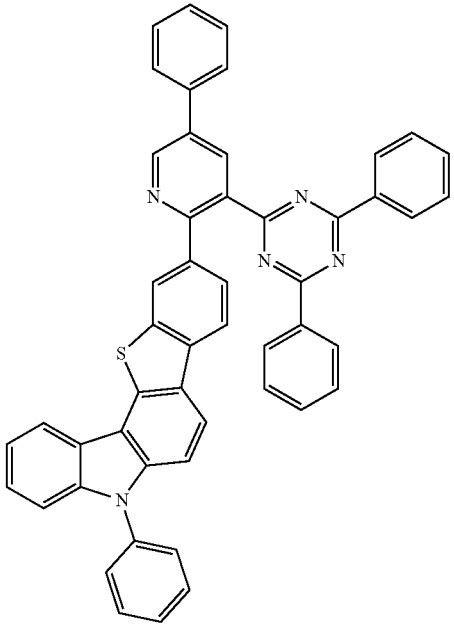
520
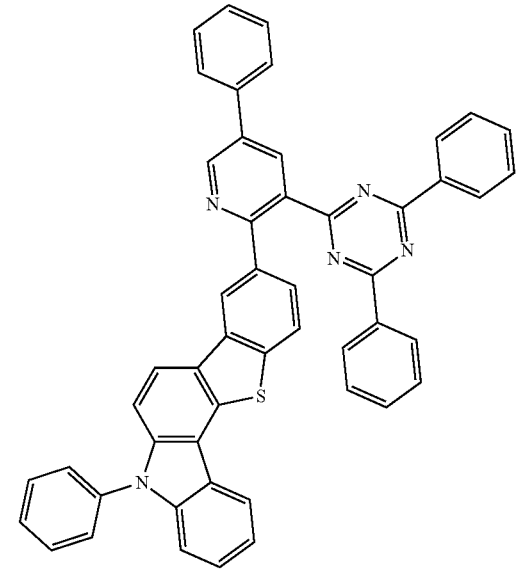
521
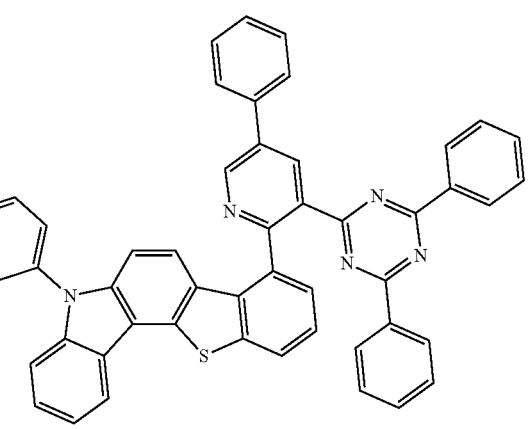

1437
-continued
522
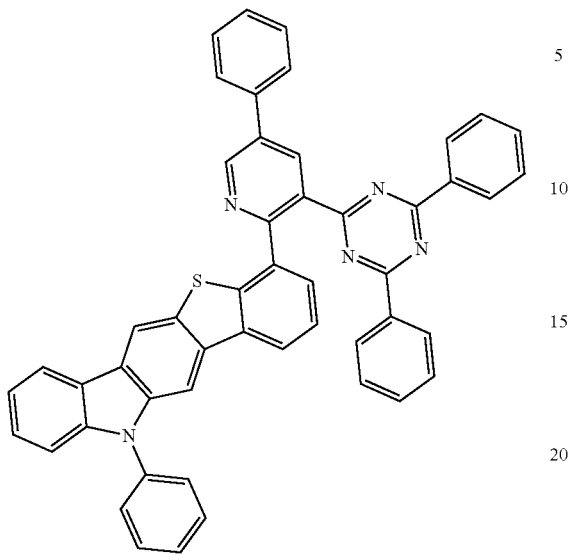
523
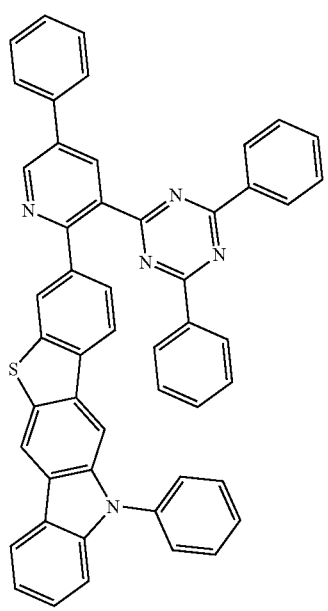
1438
-continued
524
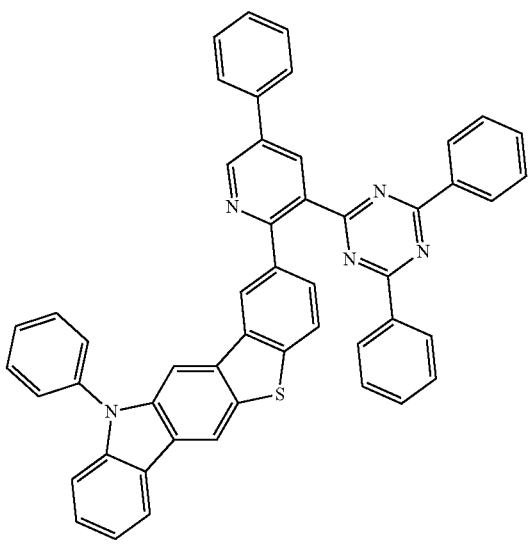
525
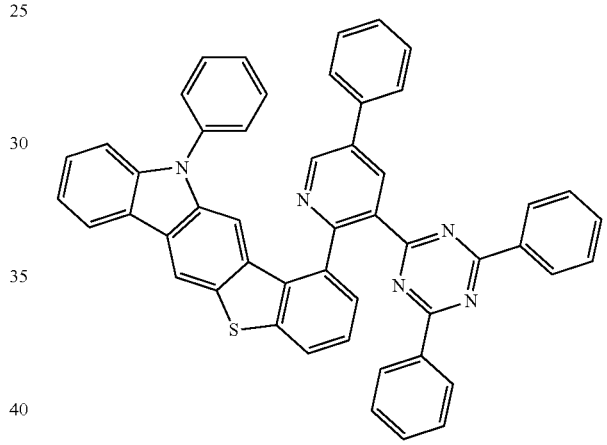
526
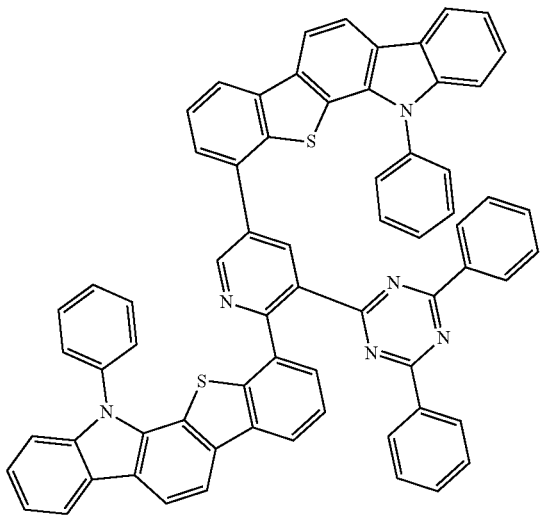

1439-continued
527
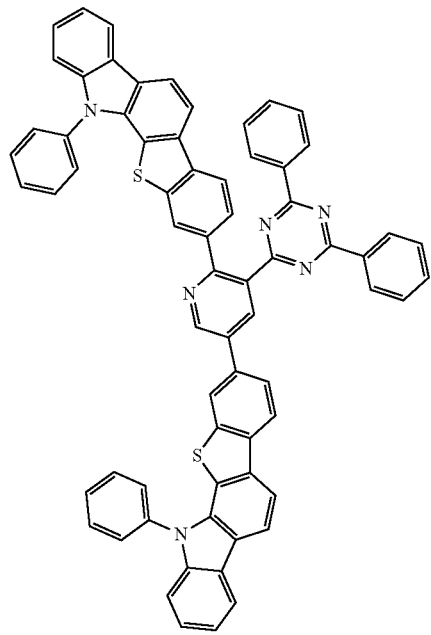
529
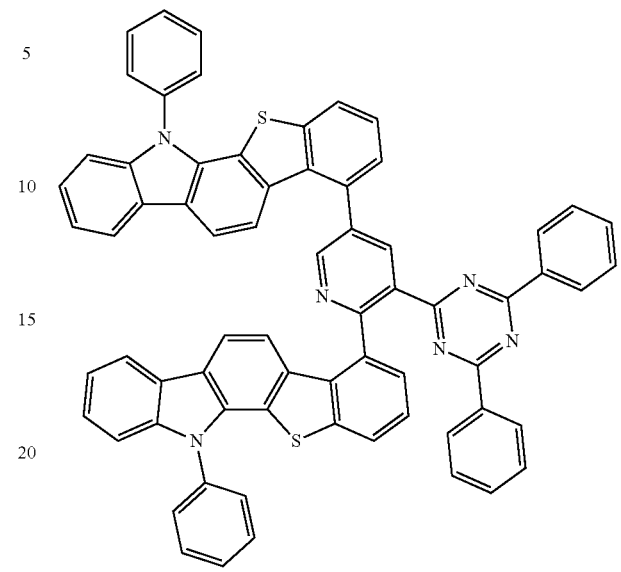
258
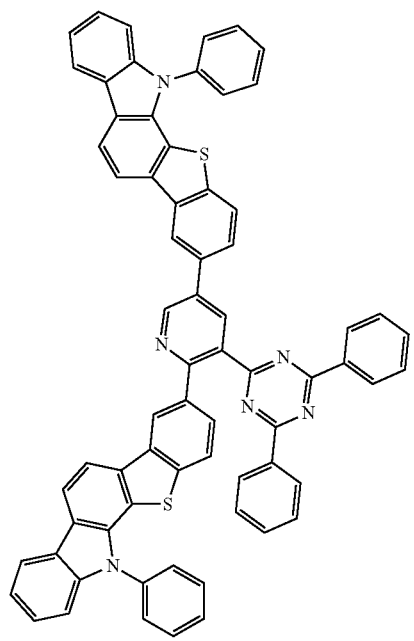
1440-continued
185
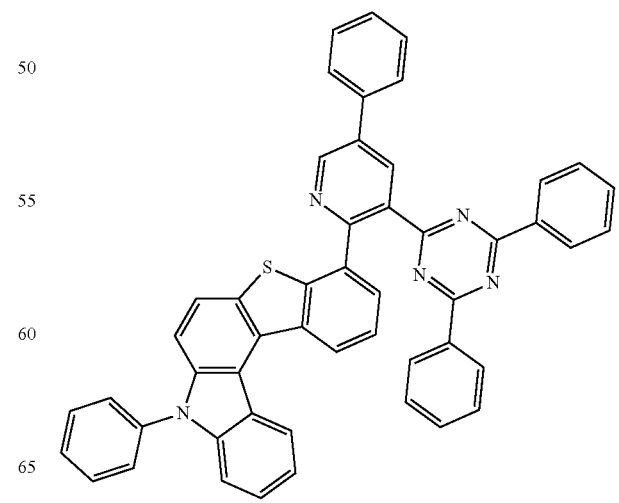

1441
-continued
531
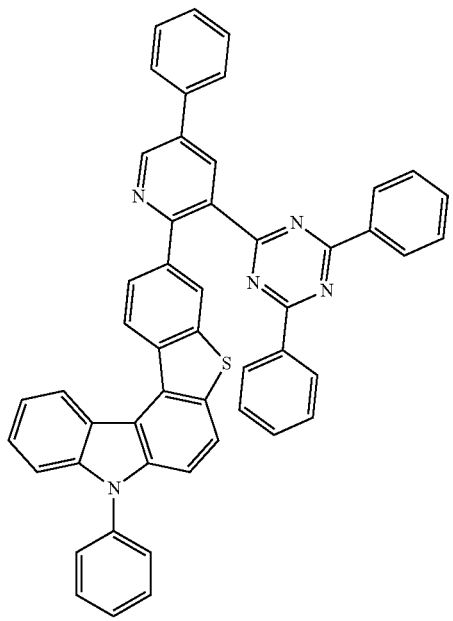
532
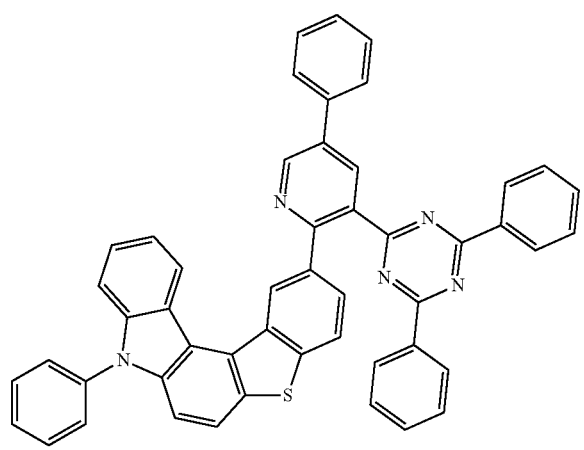
533
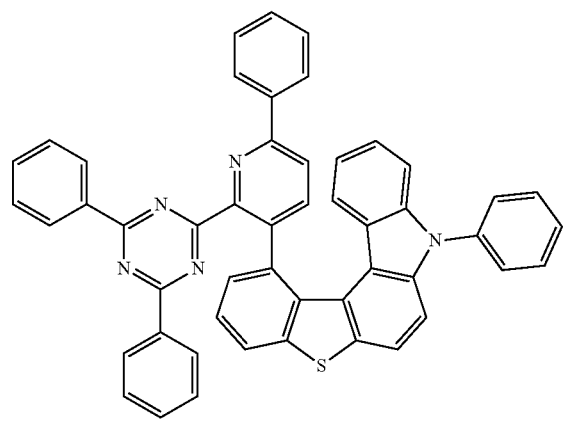
1442
-continued
534
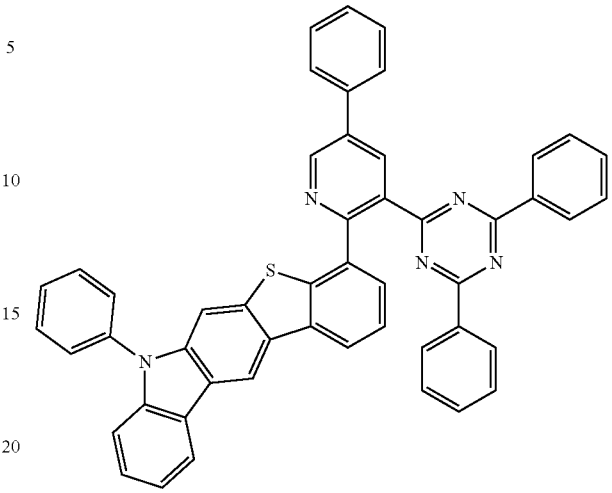
535
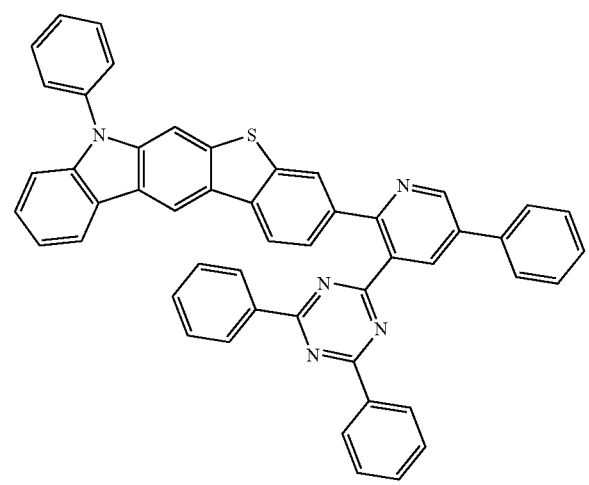
536
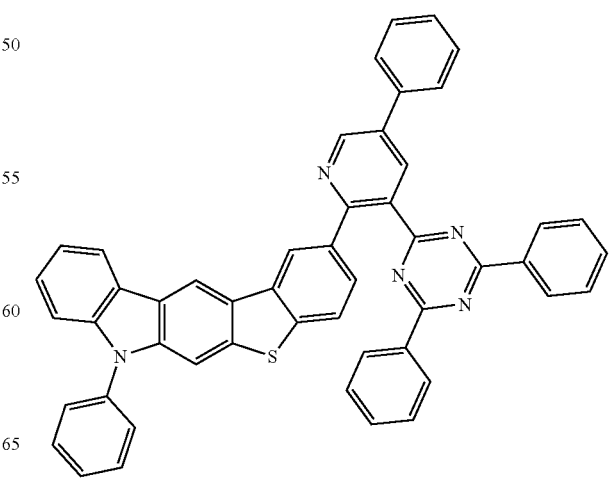

-continued
537
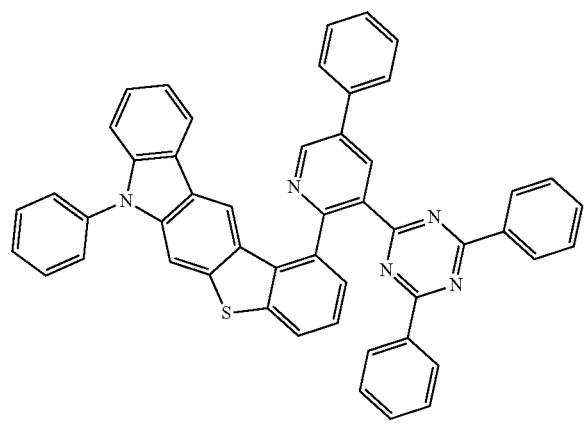
538
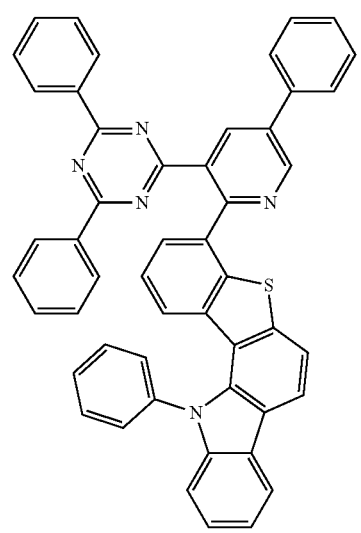
539
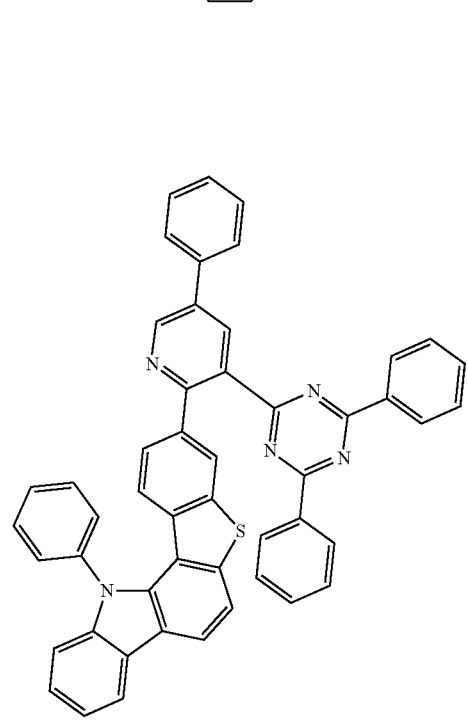
-continued
540
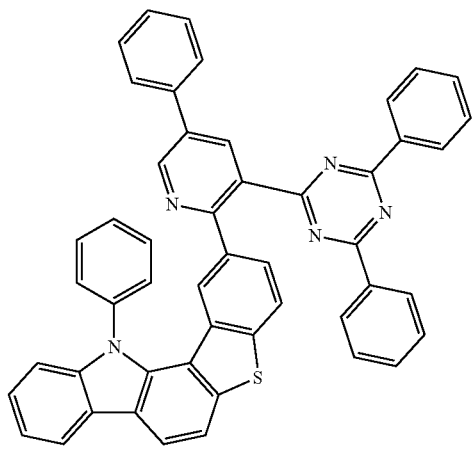
541
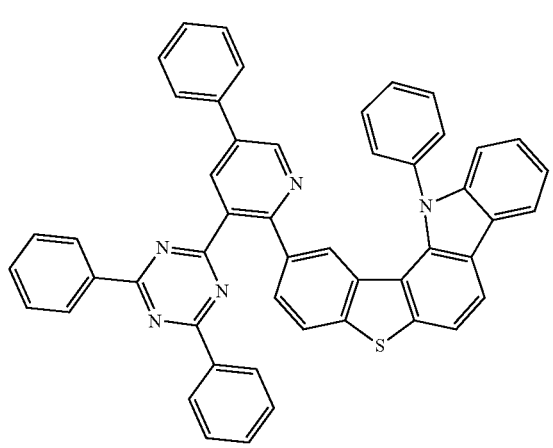
542
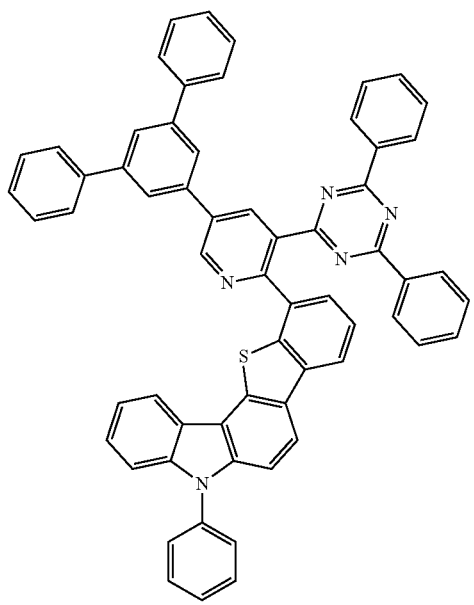

1445
-continued
543
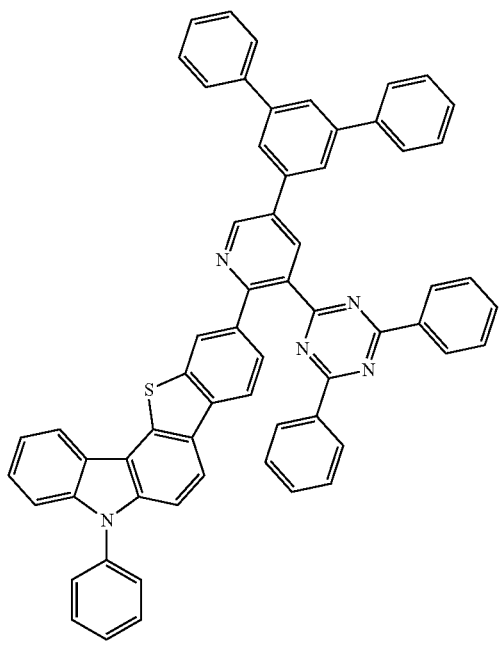
544
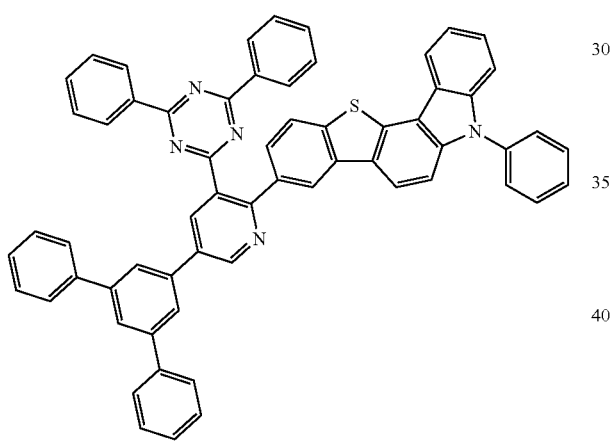
545
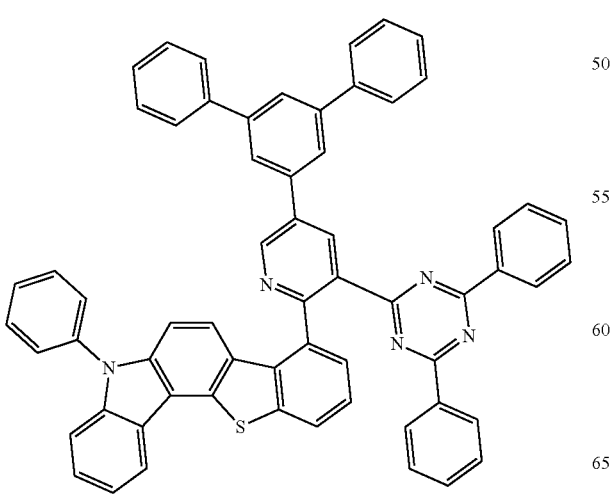
1446
-continued
546
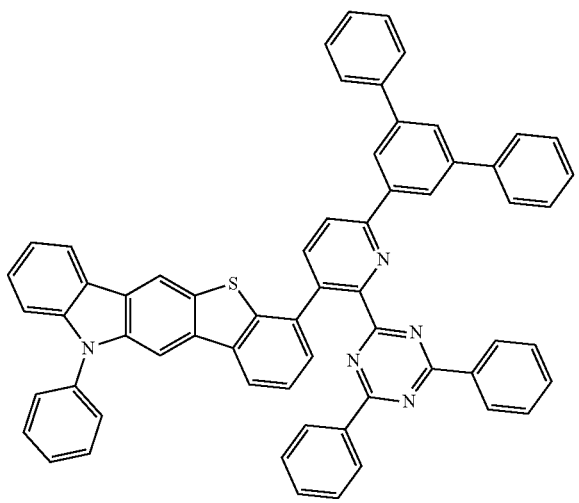
547
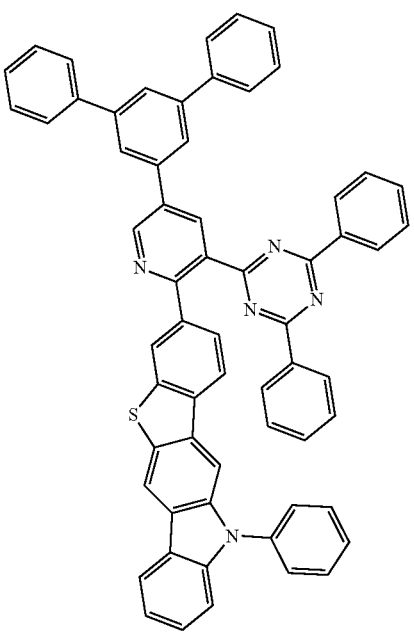

-continued
548
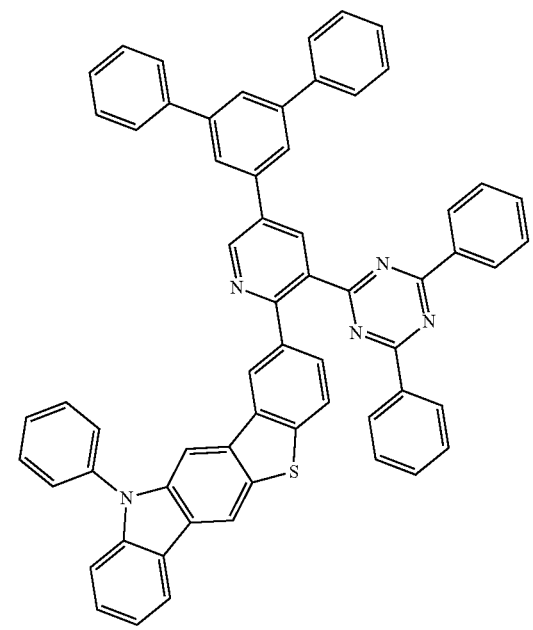
549
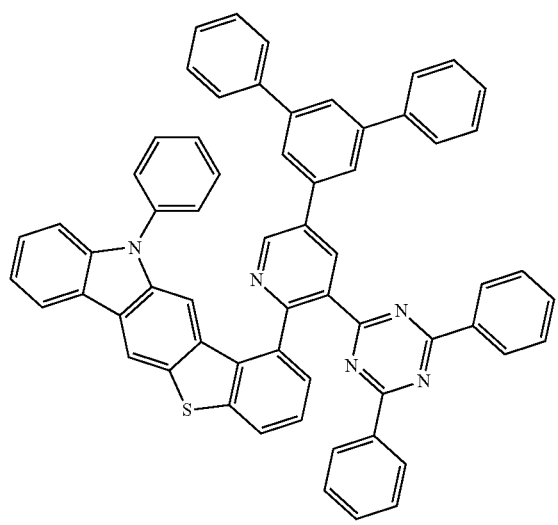
550
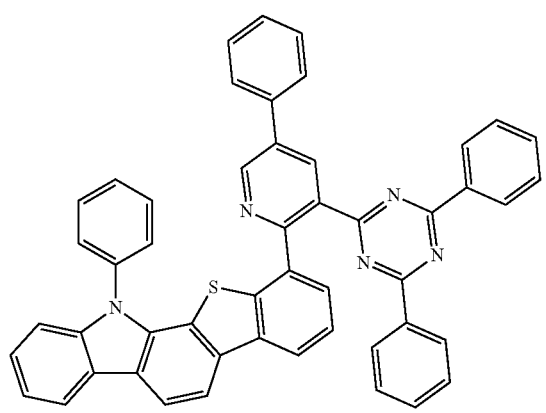
-continued
551
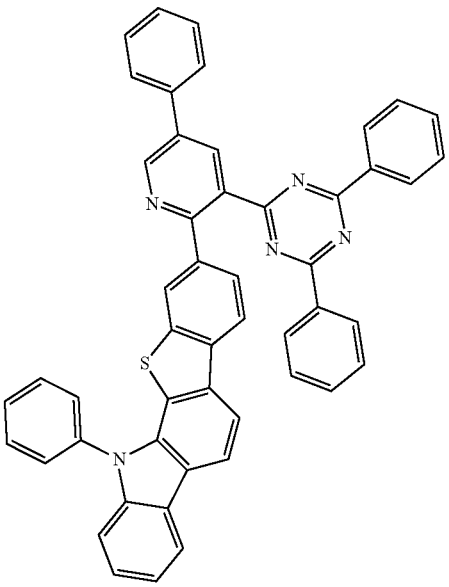
552
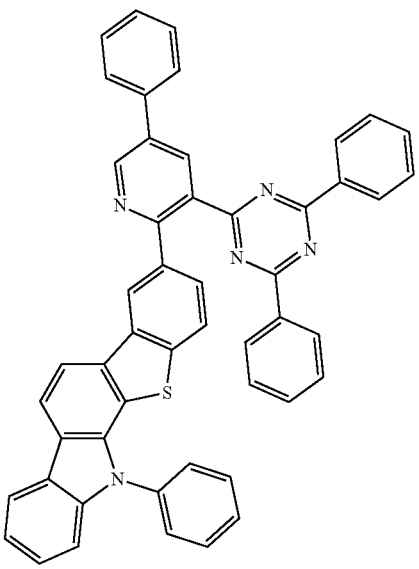
553
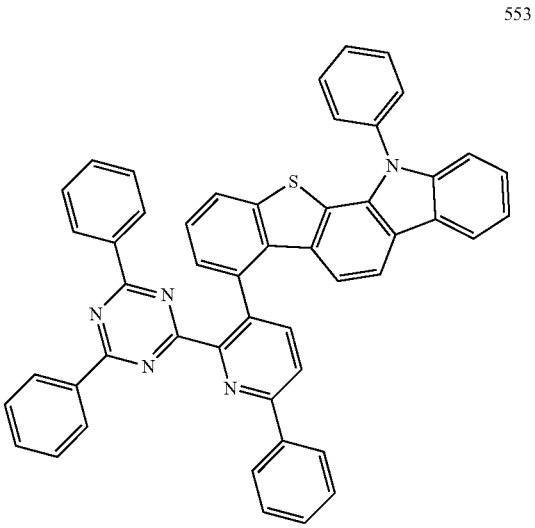

554
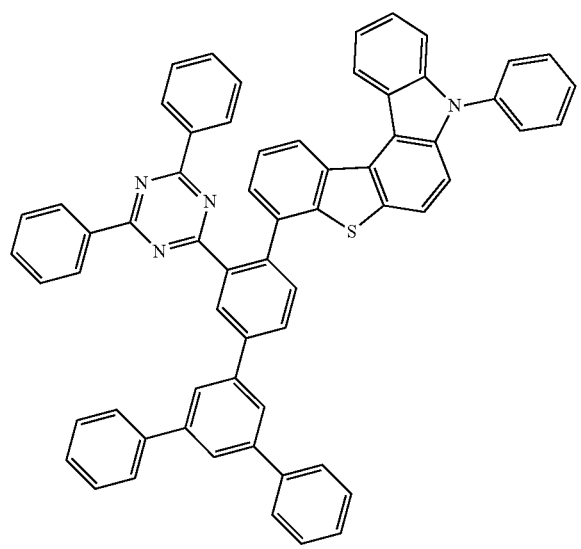
555
556
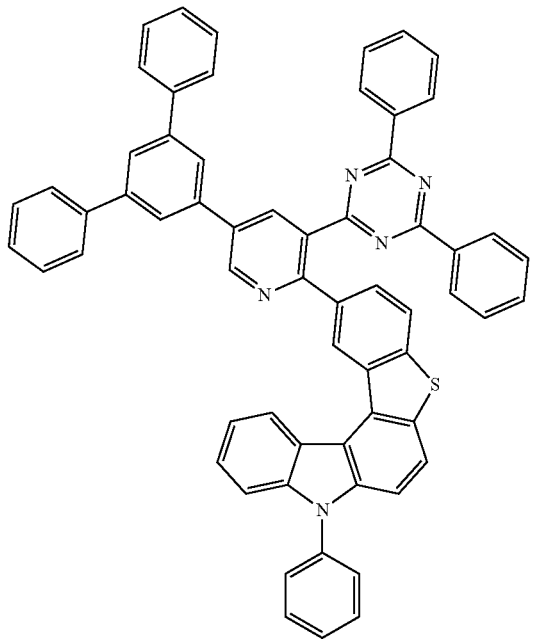
557
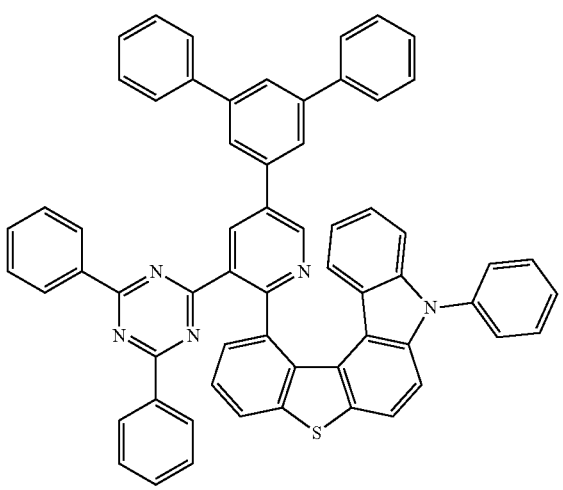

558
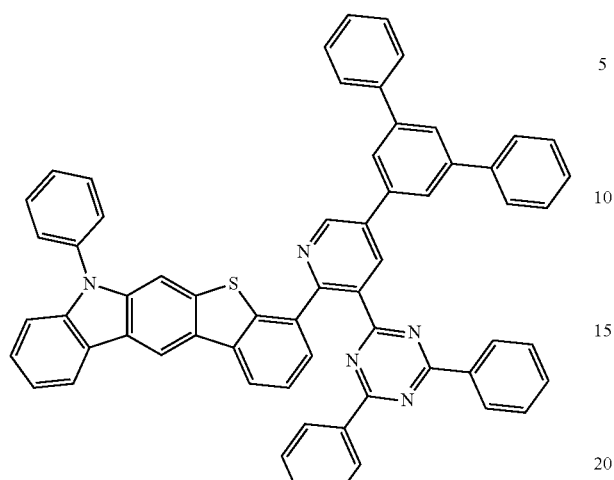
559
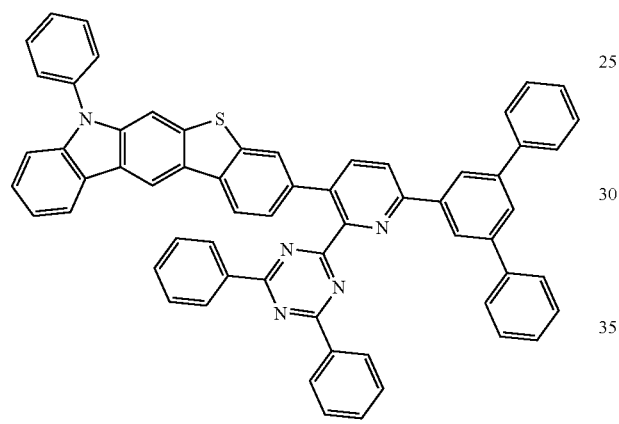
560
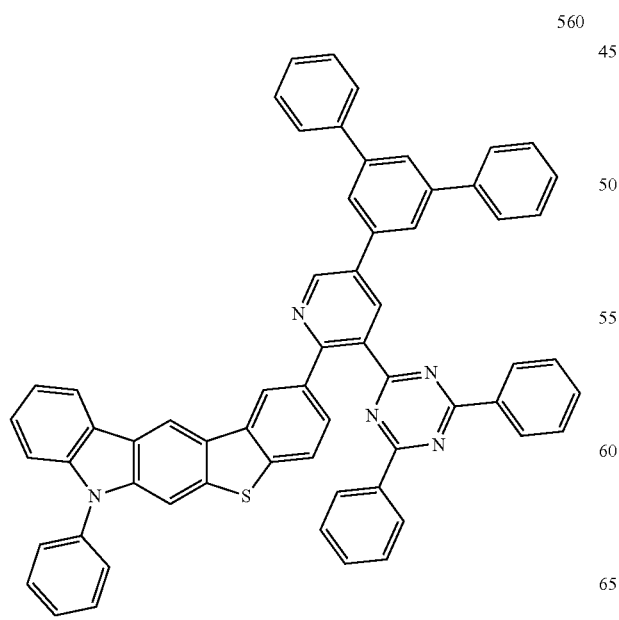
561
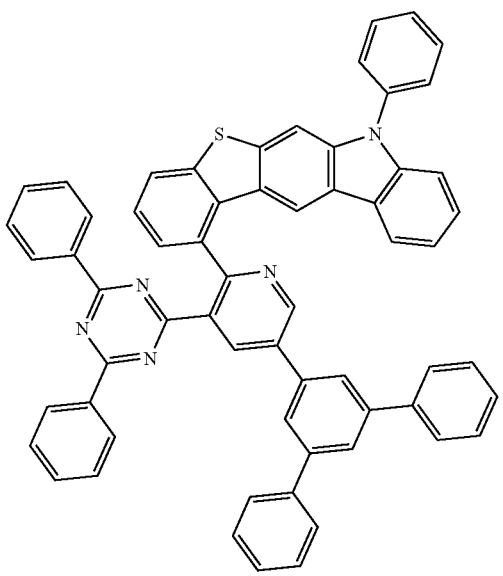
562
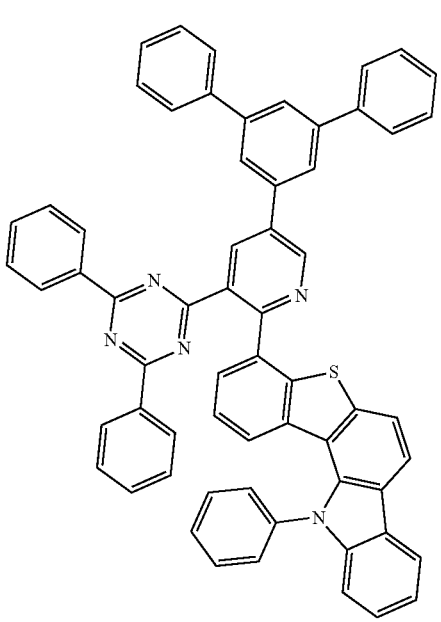

1453
-continued
563
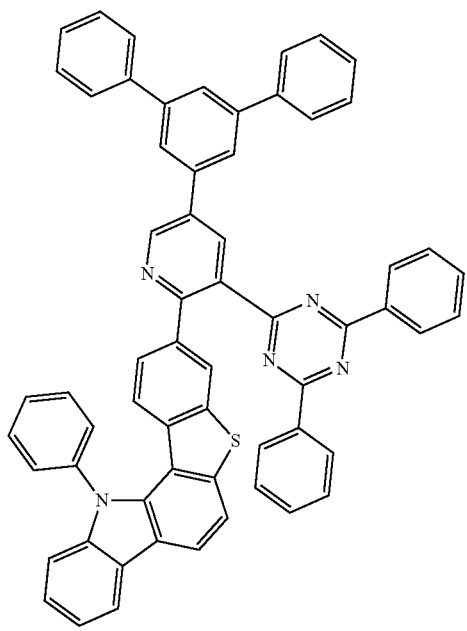
1454
-continued
565
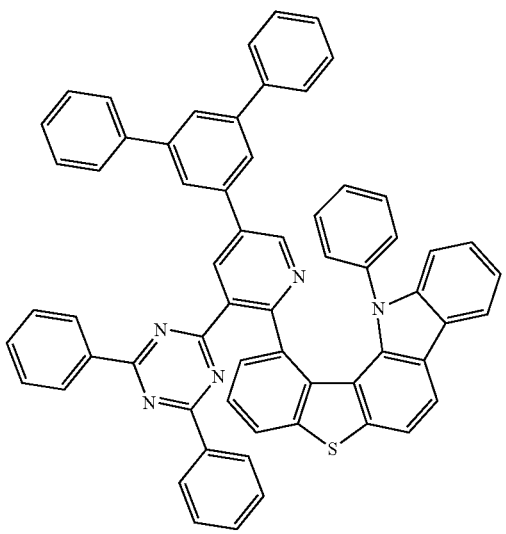
564
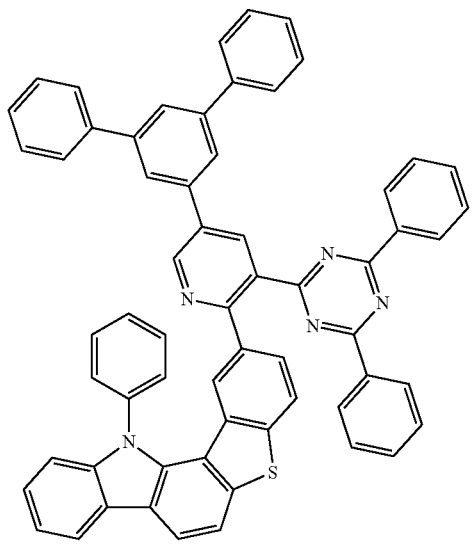
566
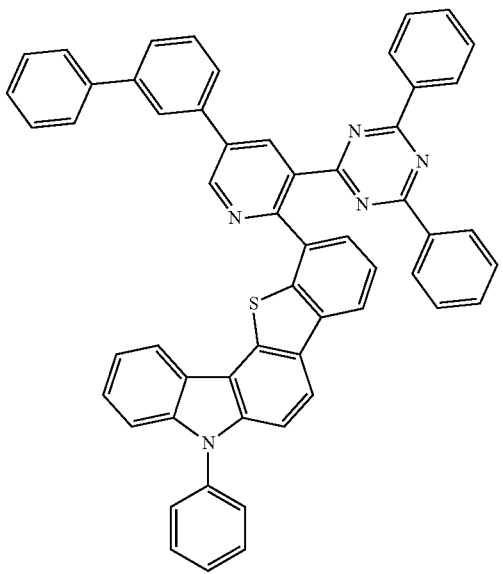

1455
-continued
1456
-continued
567
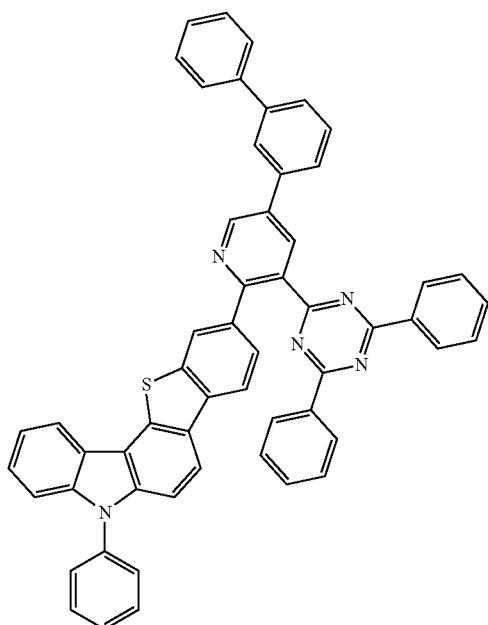
570
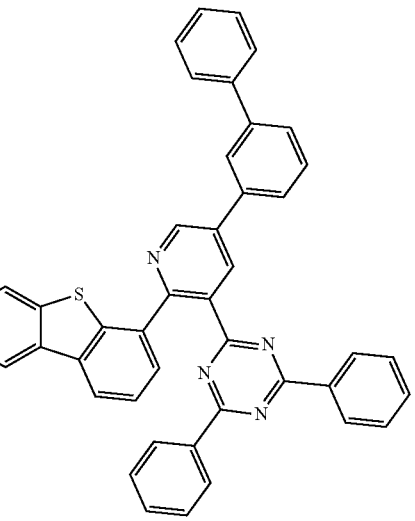
568
571
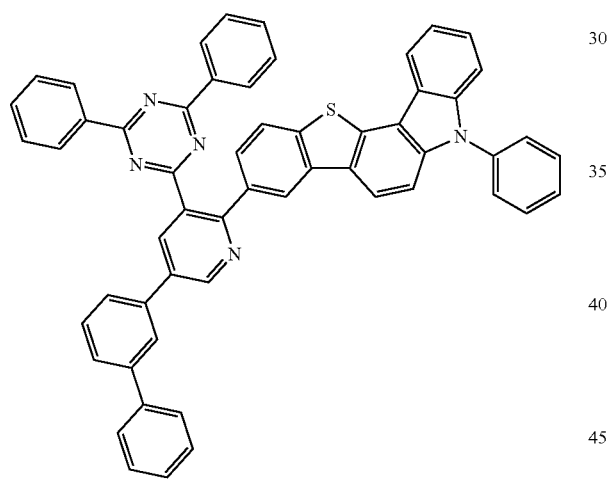
569

1457
-continued
572
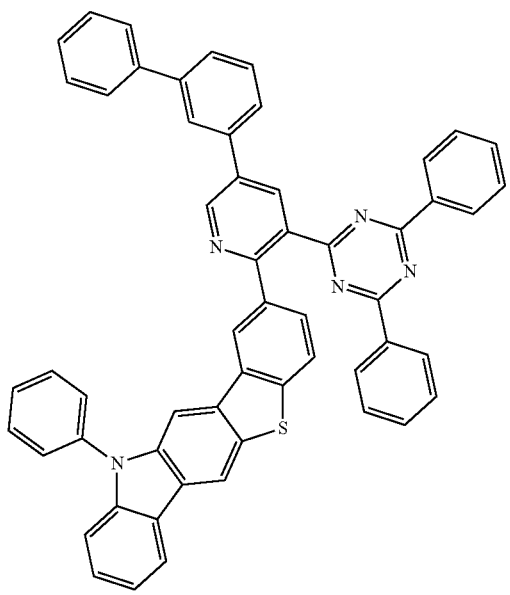
573
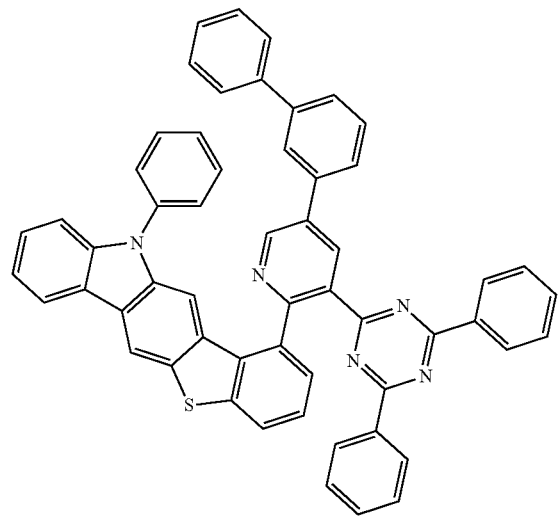
574
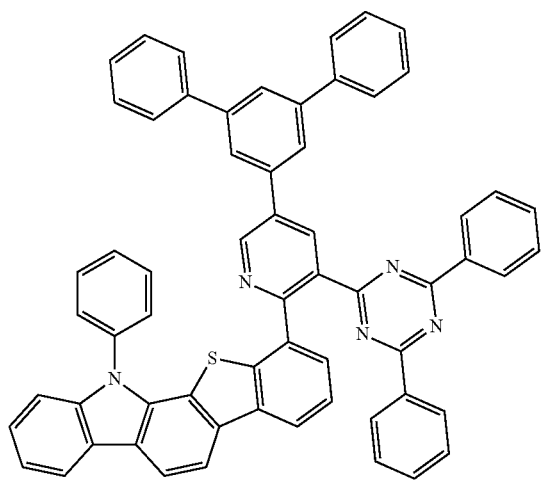
1458
-continued
575
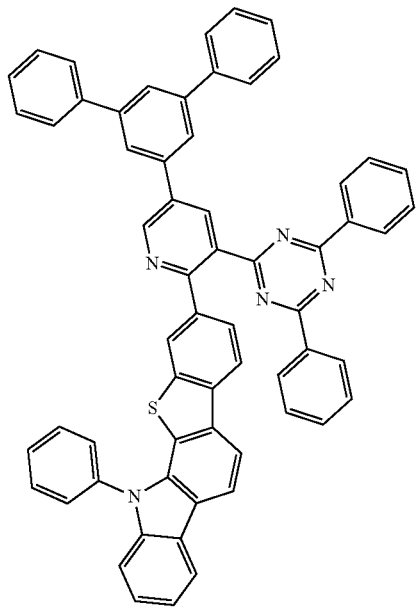
576
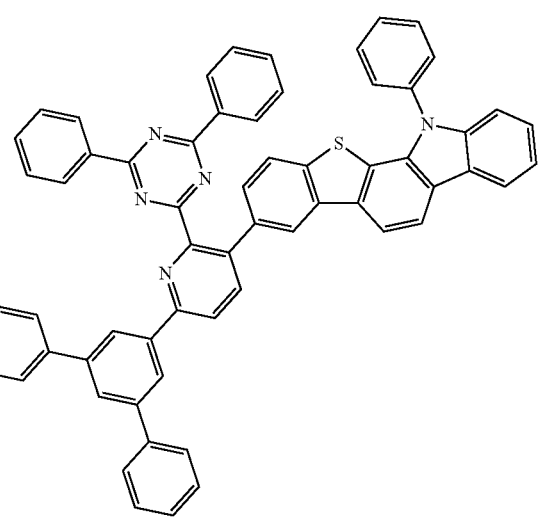

1459
-continued
577
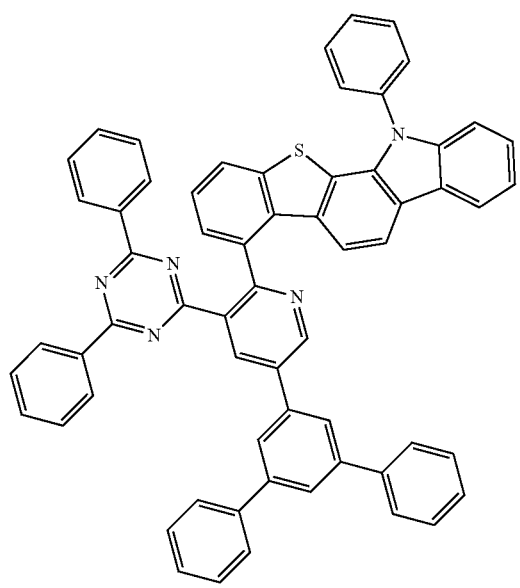
578
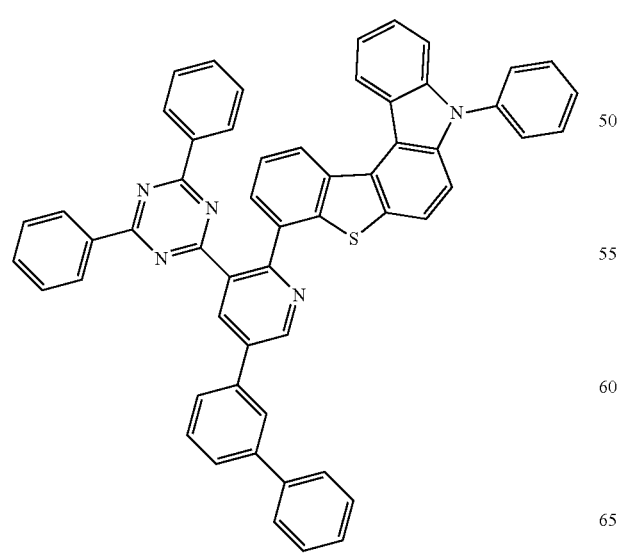
1460
-continued
579
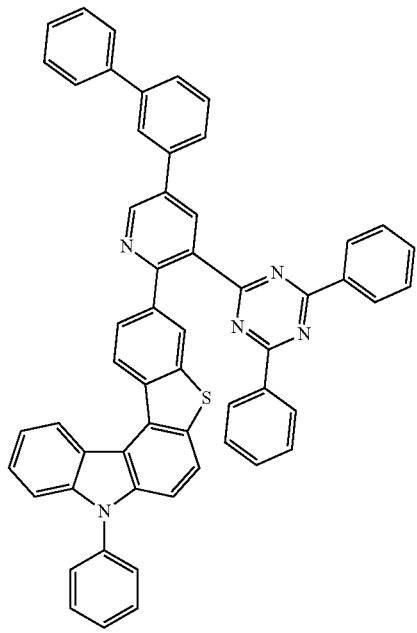
580
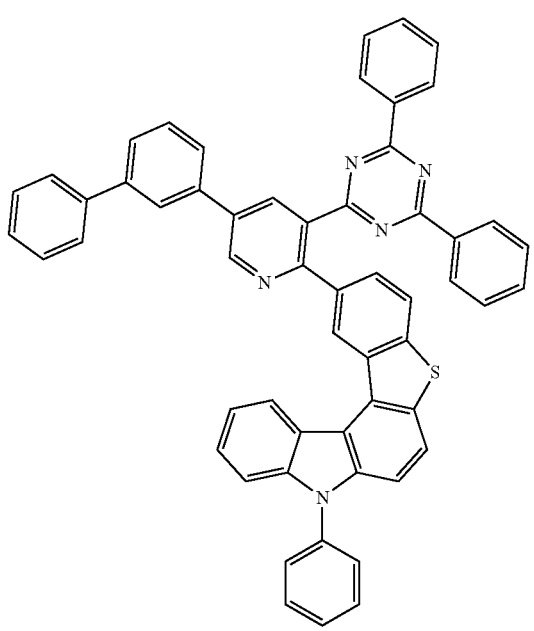

1461
-continued
584
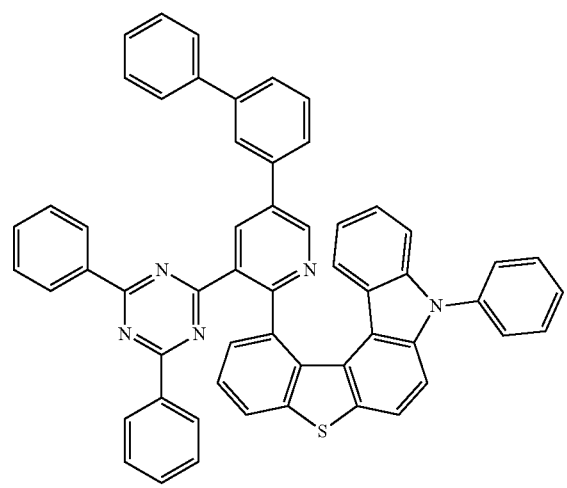
581
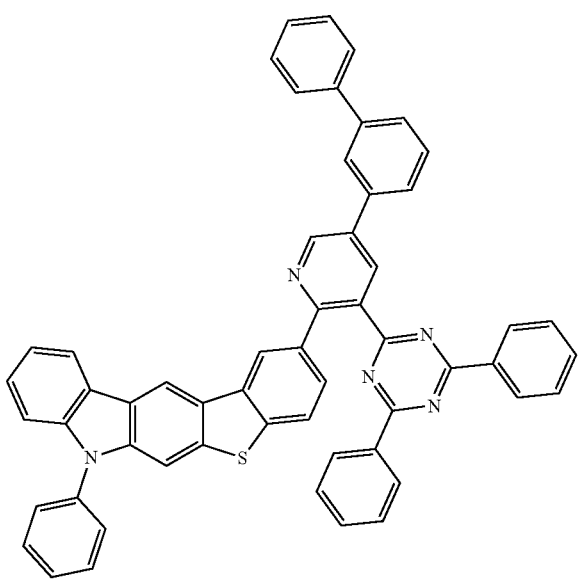
584
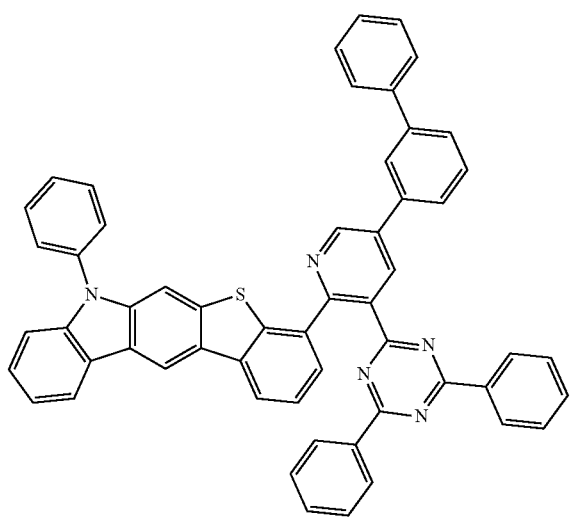
582
1462
-continued
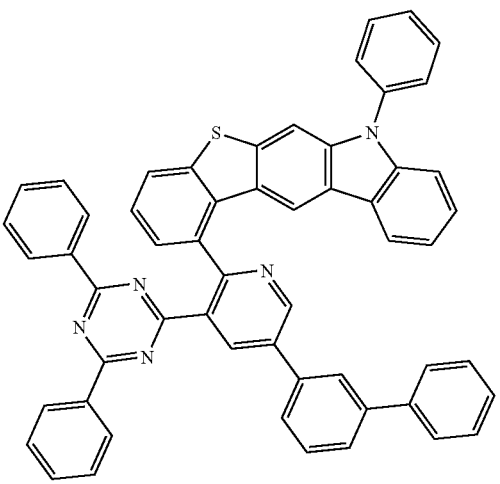
585
583

-continued
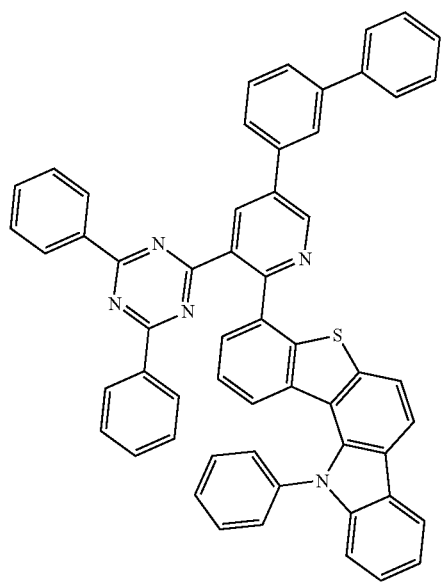
586
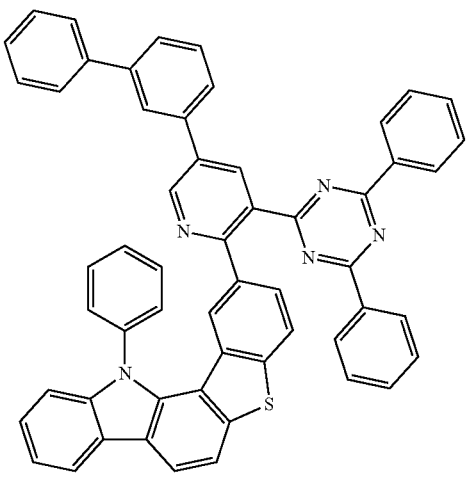
588
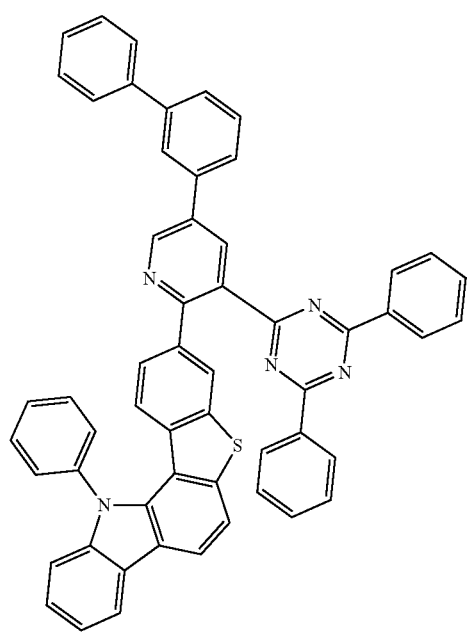
587
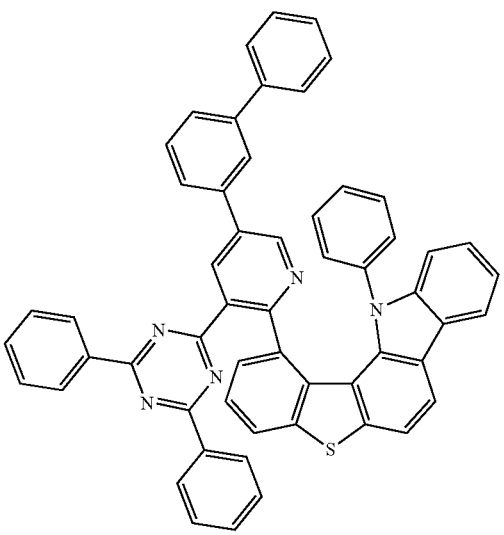
589

1465
-continued
590
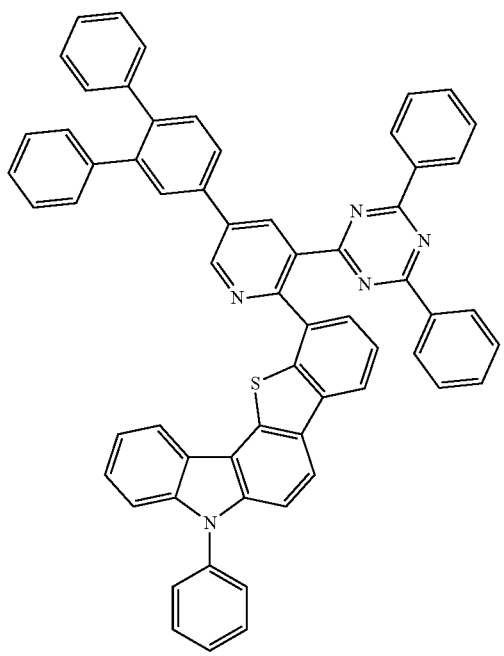
591
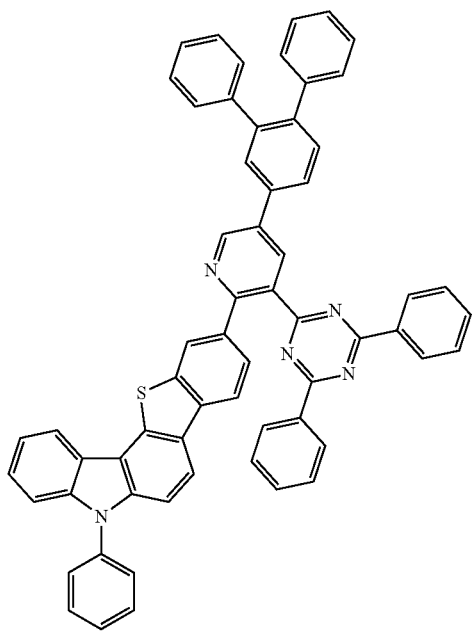
1466
-continued
592
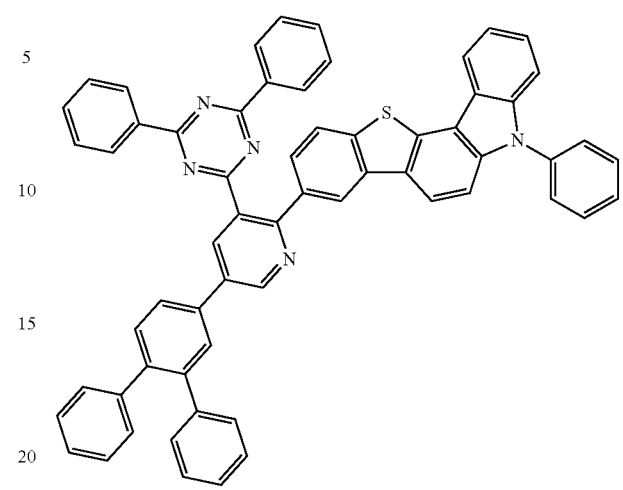
593
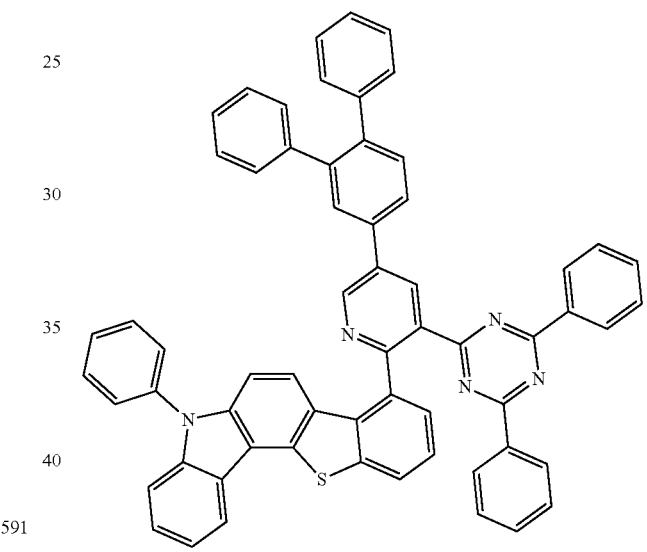
594
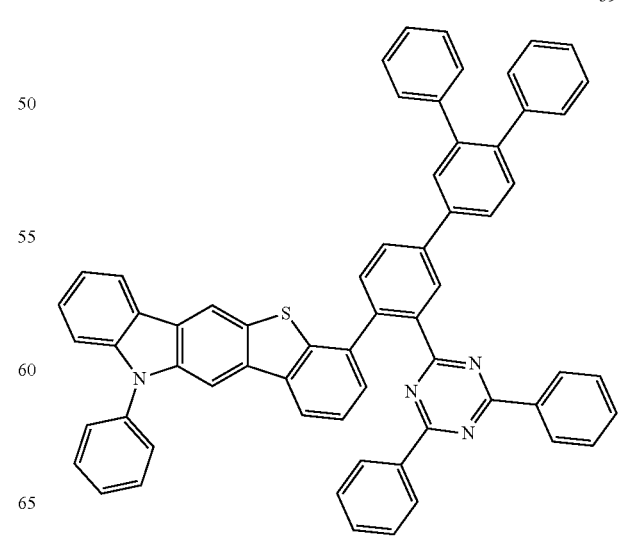

1467
-continued
595
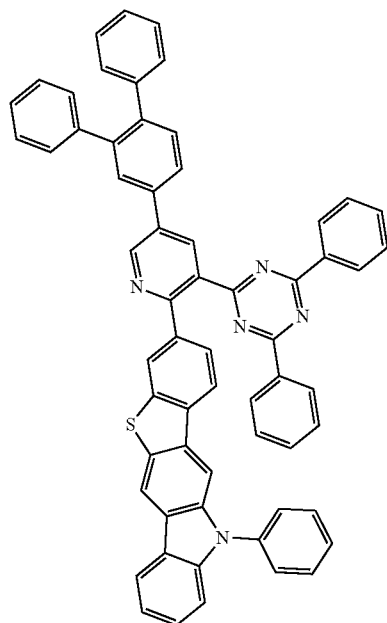
596
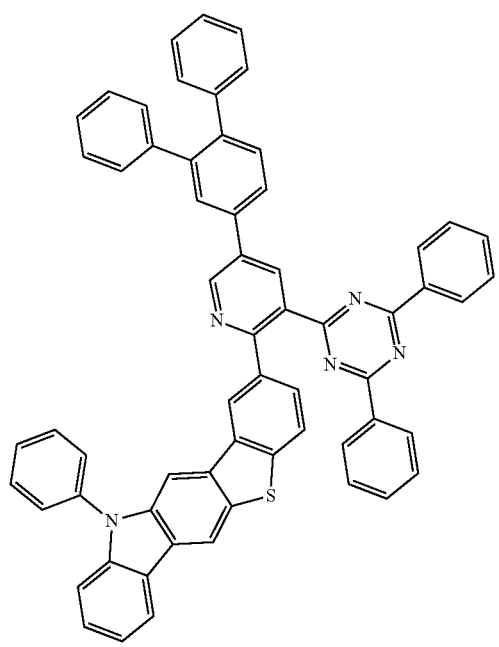
1468
-continued
597
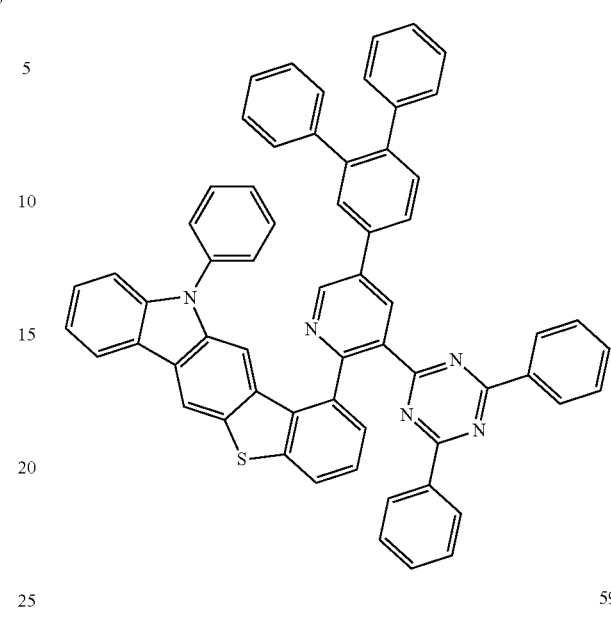
598
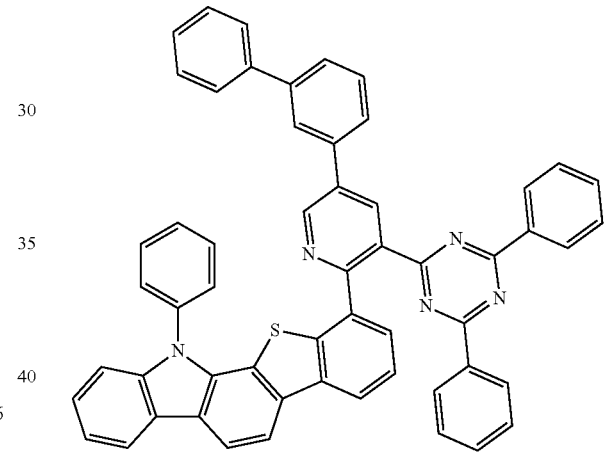
599
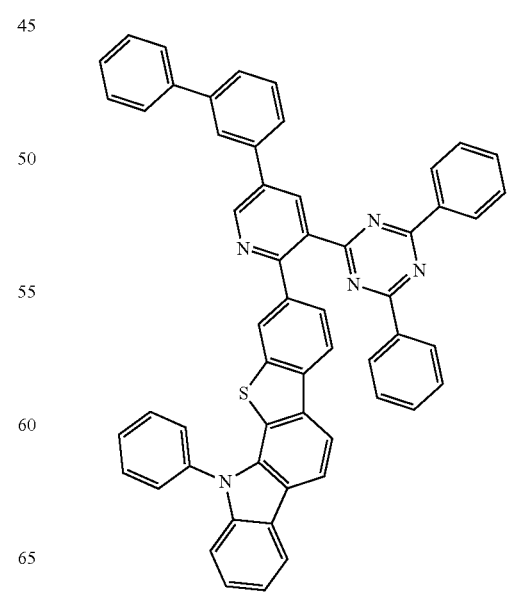

1469
-continued
1470
-continued
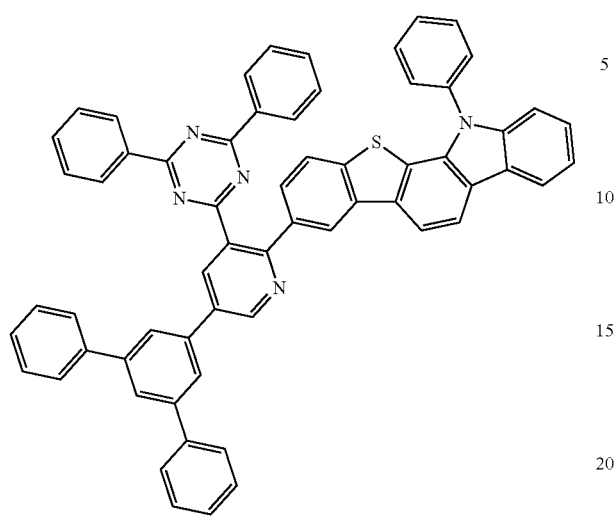
600
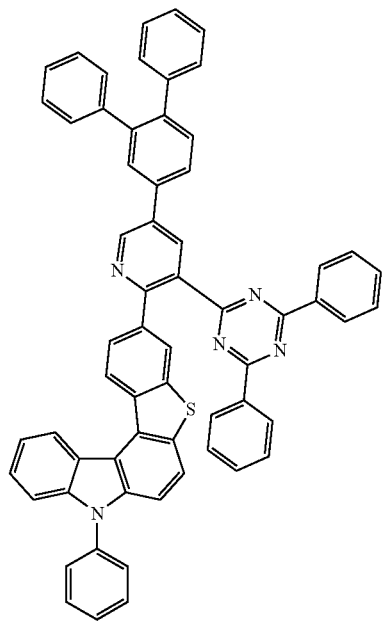
603
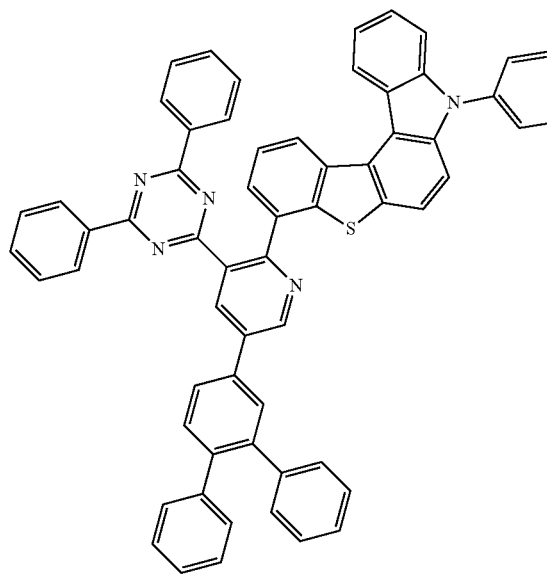
601
602
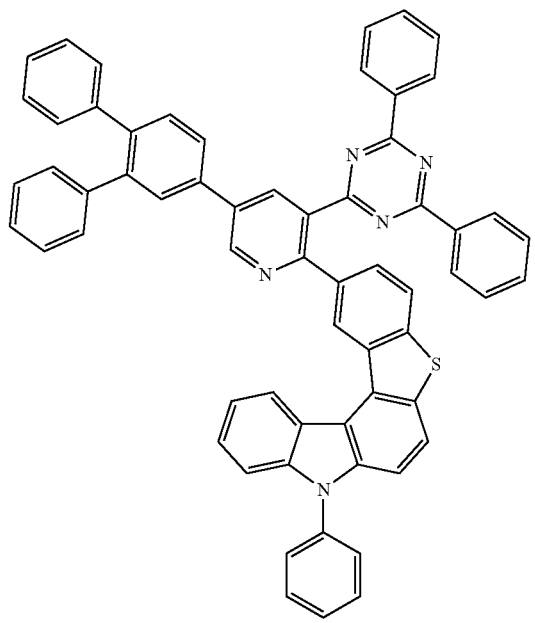
604

1471
-continued
1472
-continued
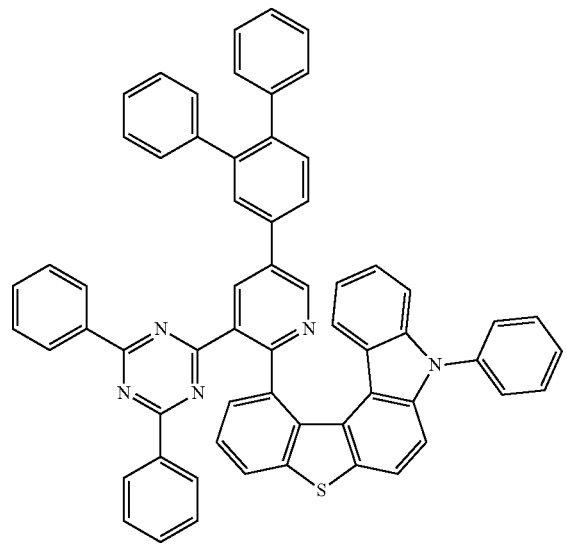
605
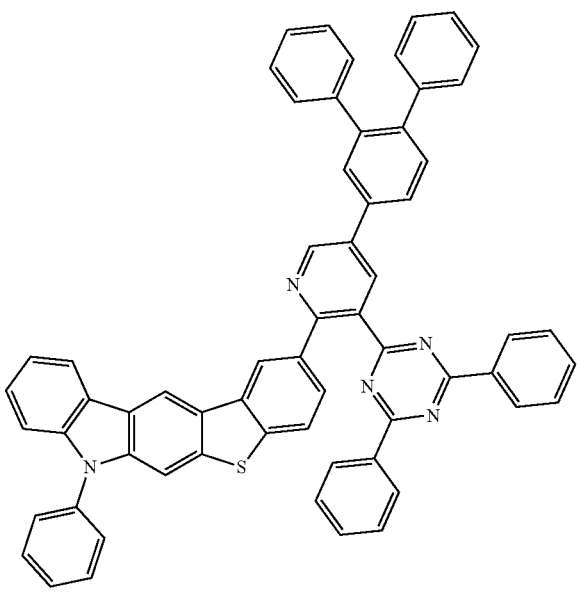
608
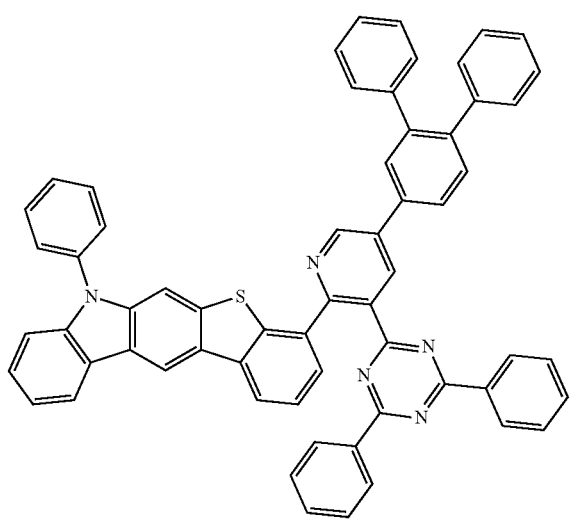
606
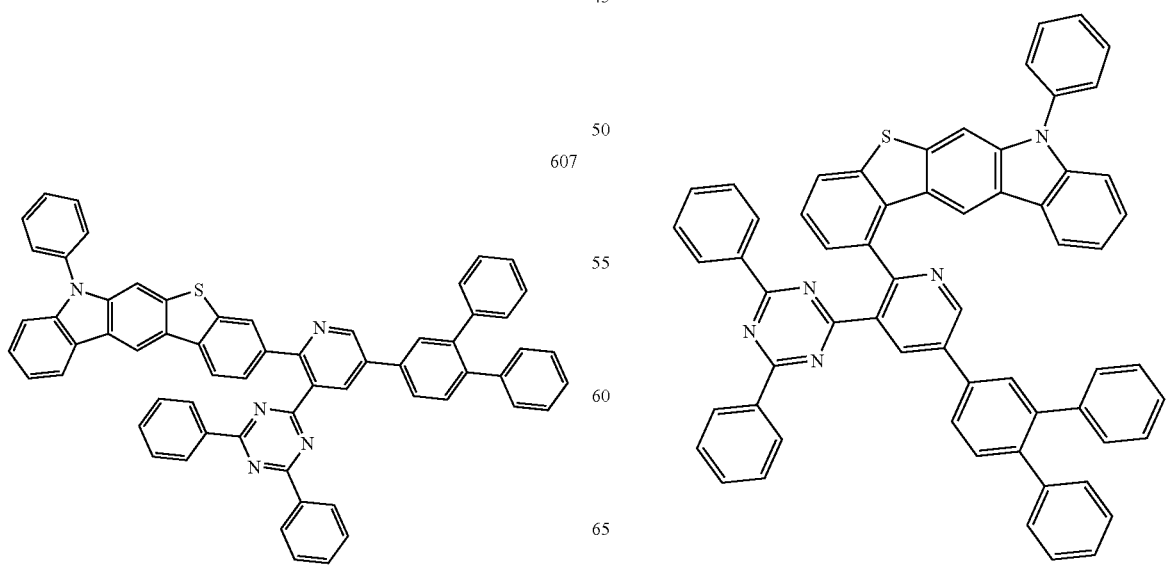
607
609

610
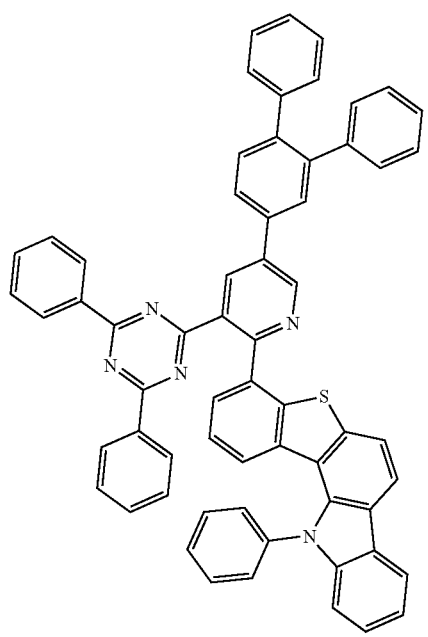
612
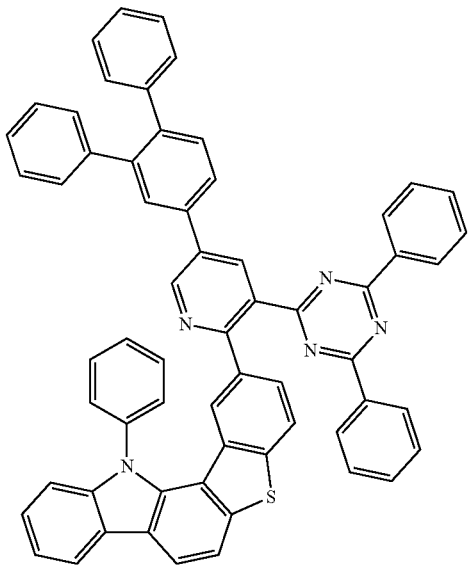
611
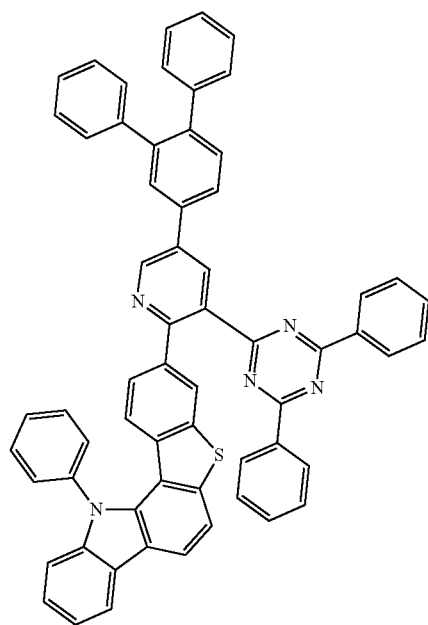
613
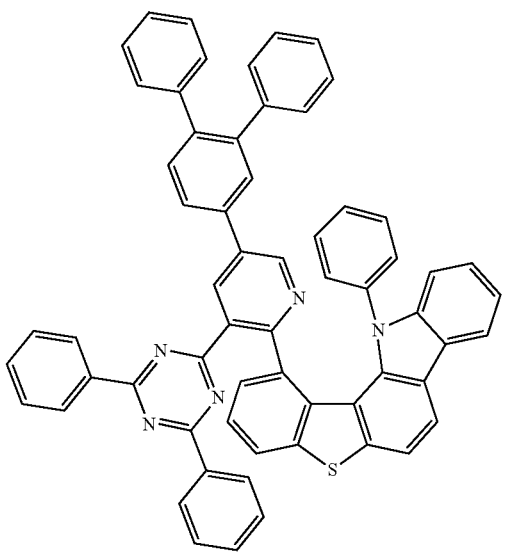

1475
-continued
614
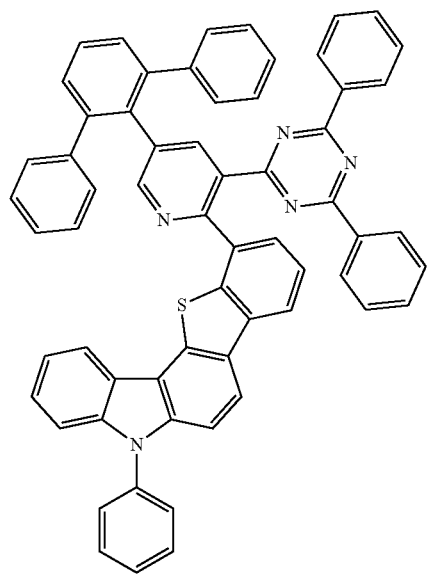
615
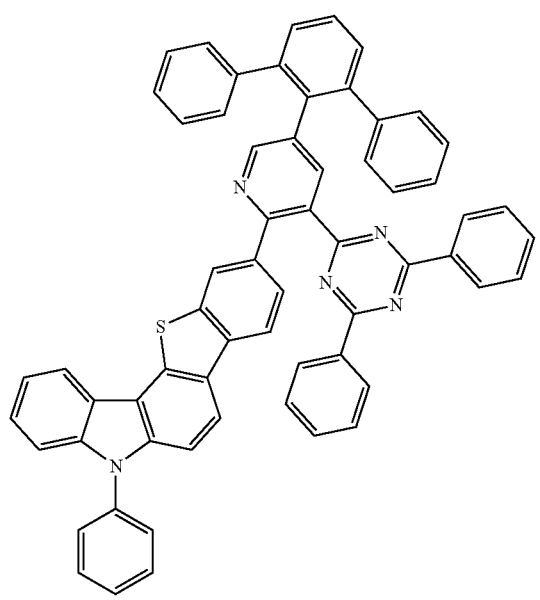
616
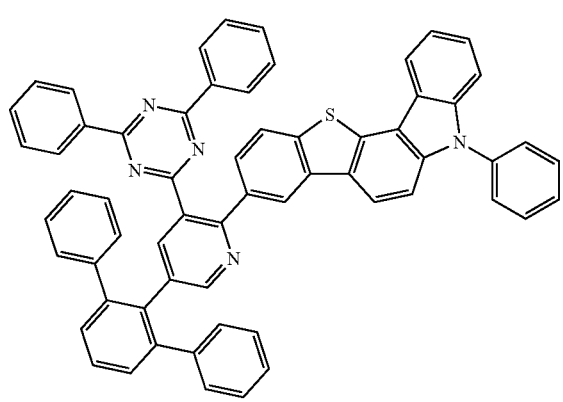
1476
-continued
617
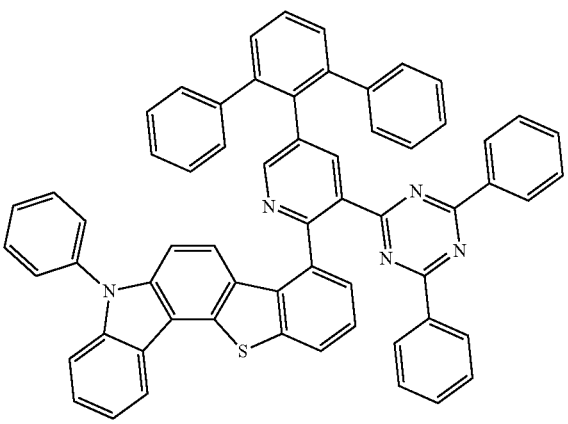
618
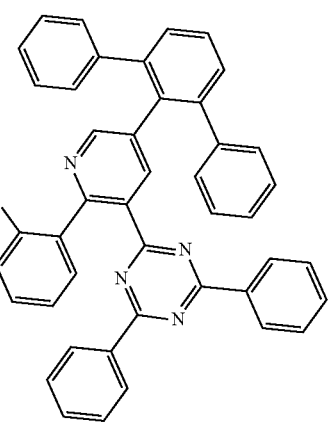
619
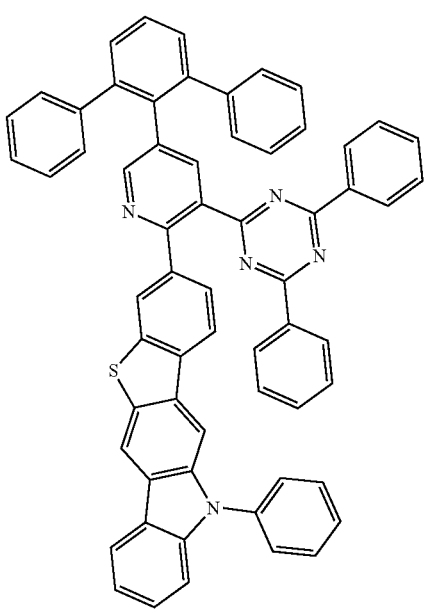

1477
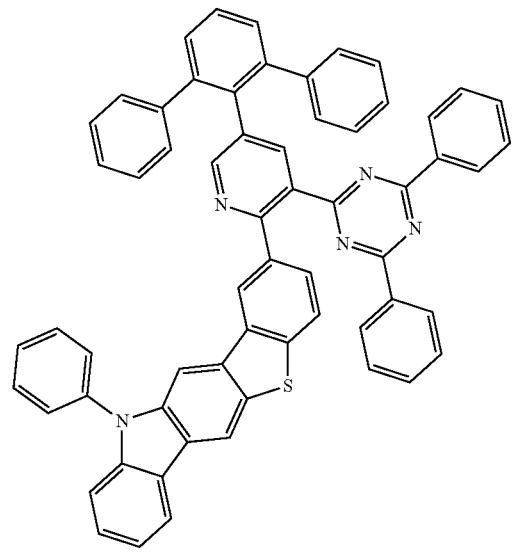
620
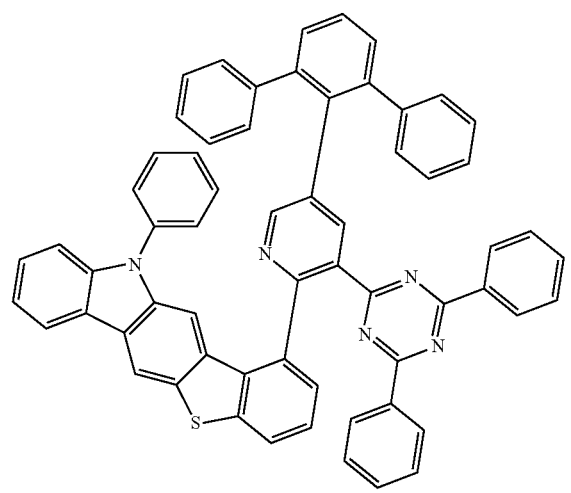
621
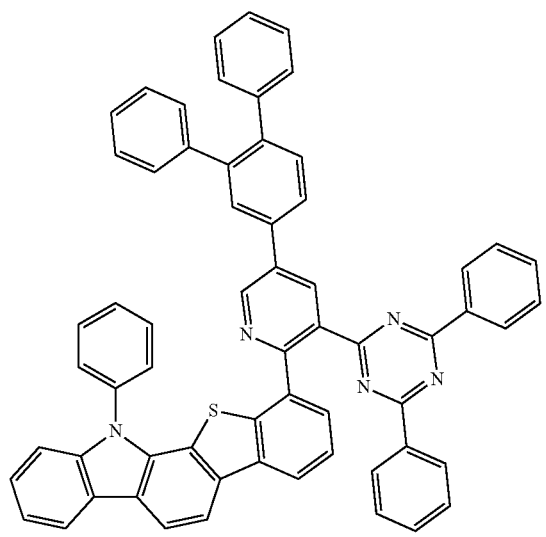
622
1478
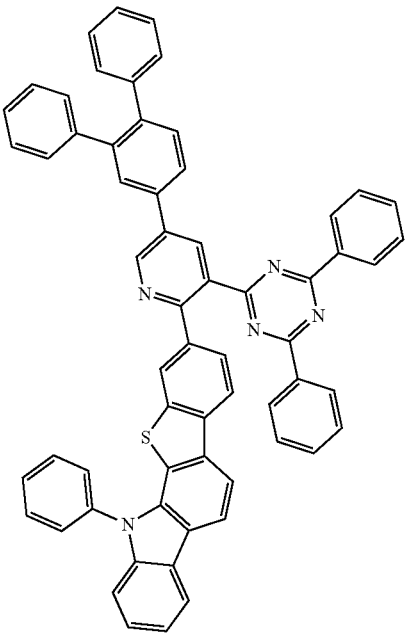
623
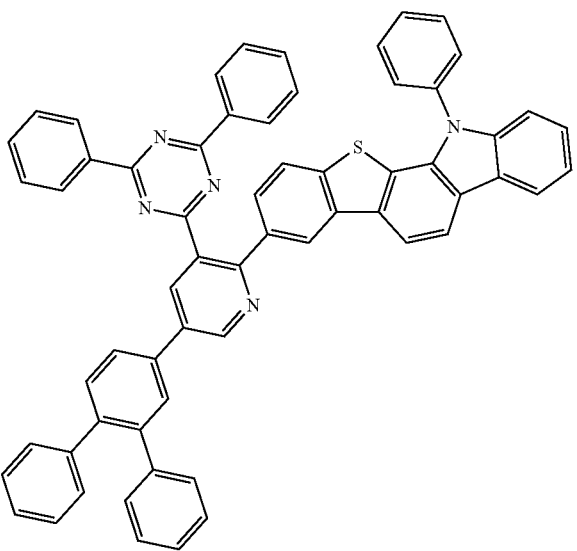
624

1479
-continued
625
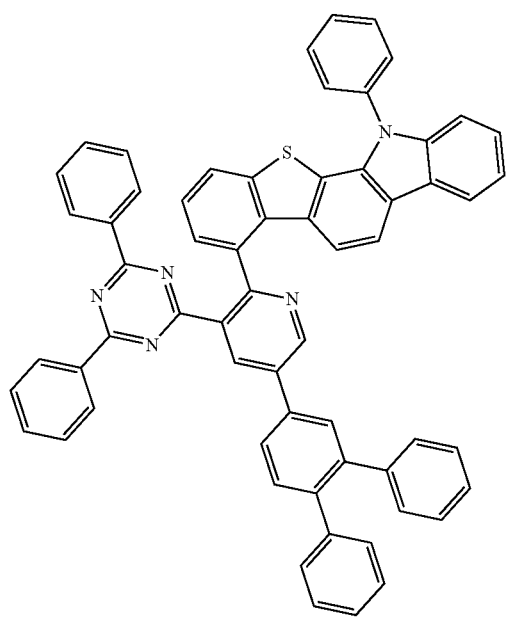
626
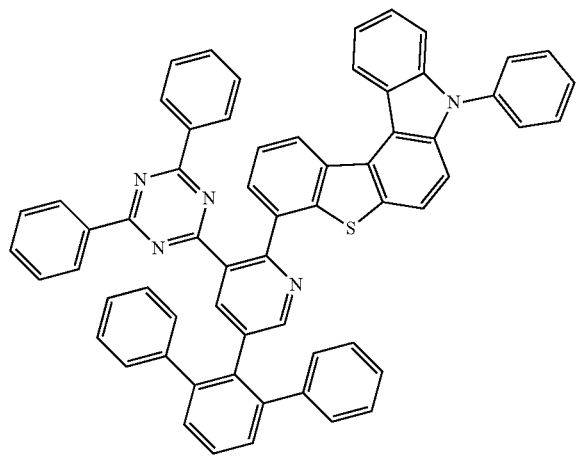
1480
-continued
627
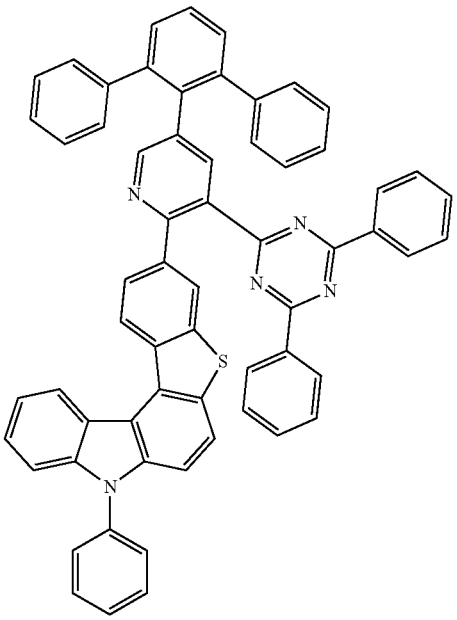
628
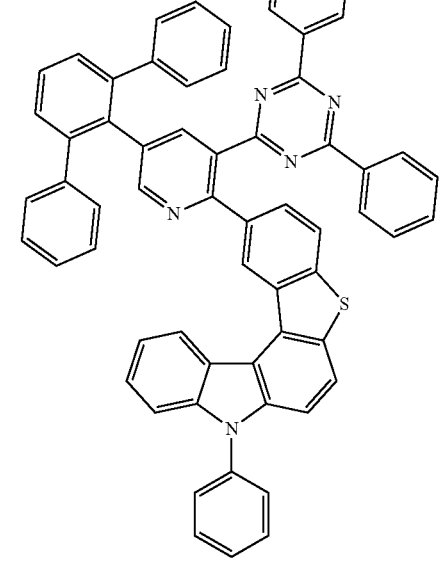

1481
-continued
629
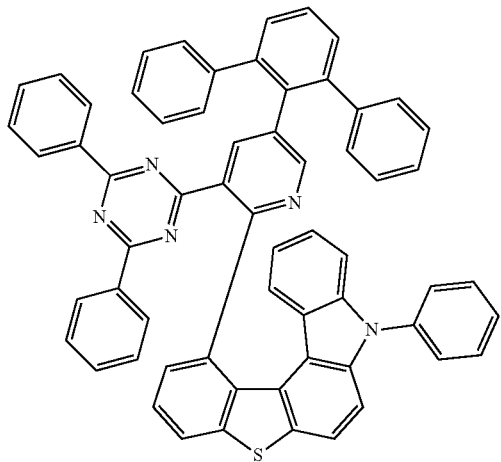
630
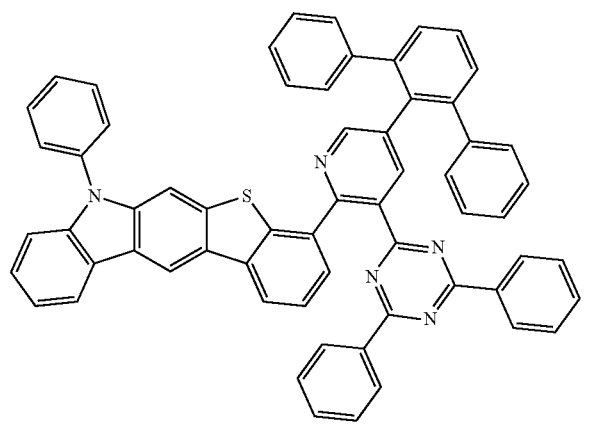
631
1482
-continued
632
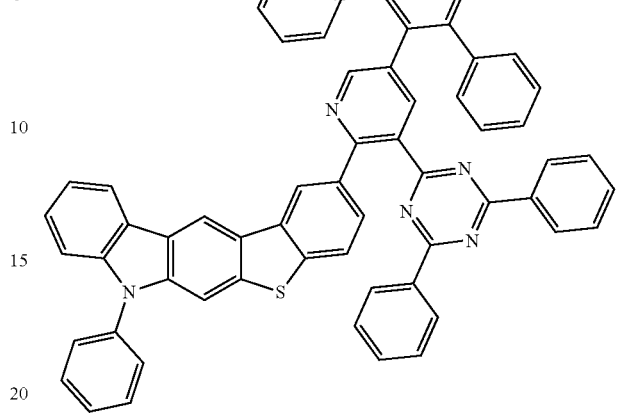
633
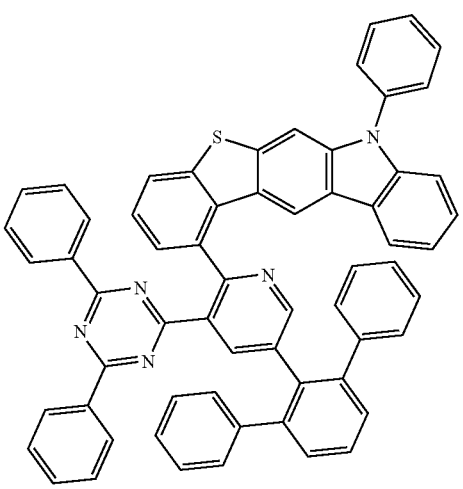
634
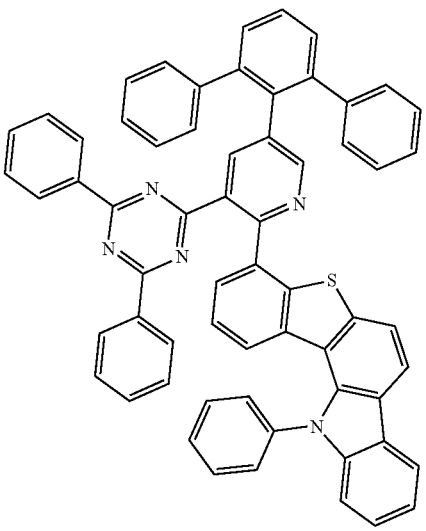

1483
-continued
635
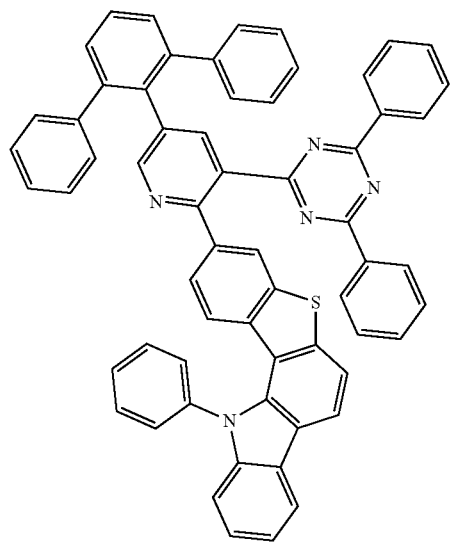
636
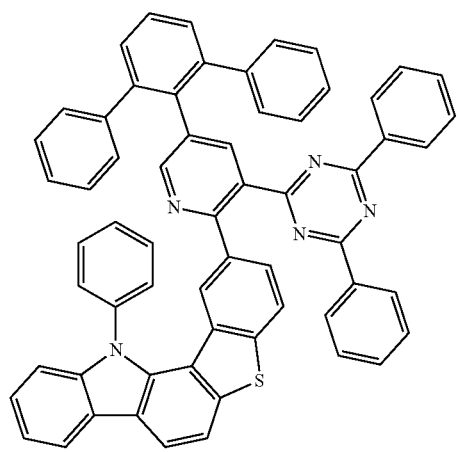
637
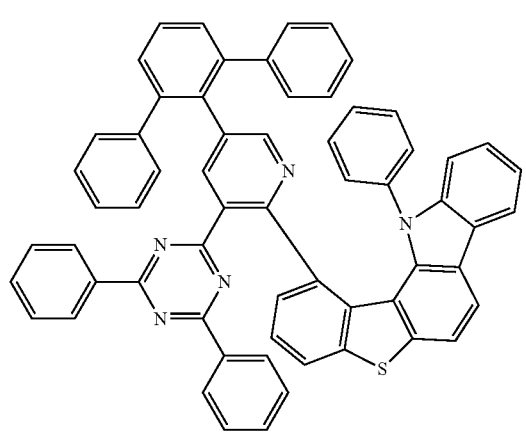
1484
-continued
638
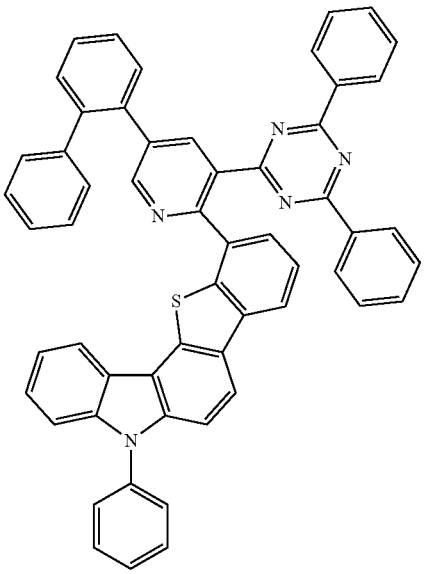
639
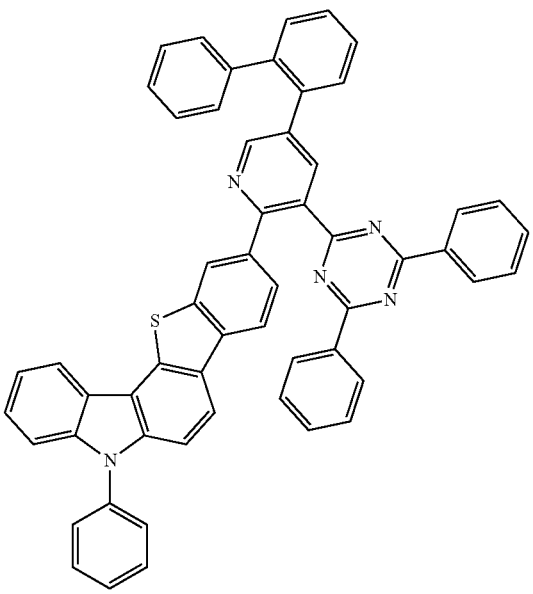
640
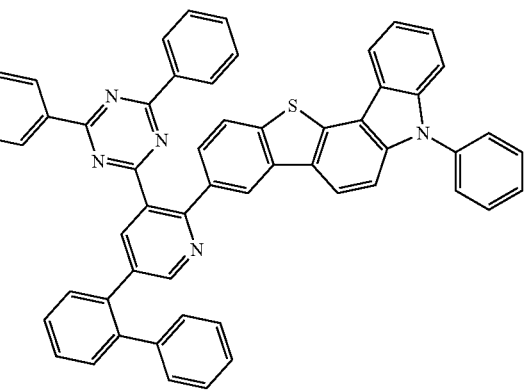

1485
-continued
1486
-continued
641
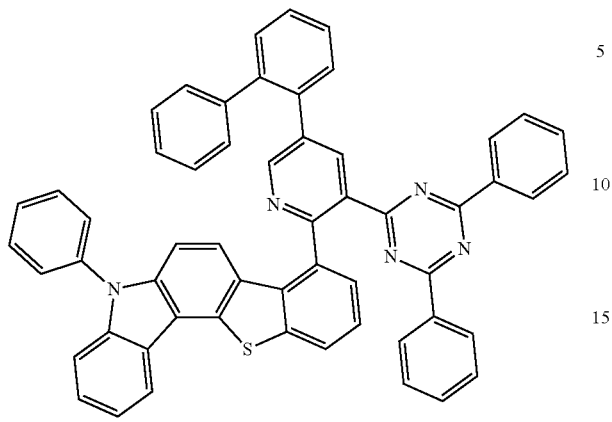
644
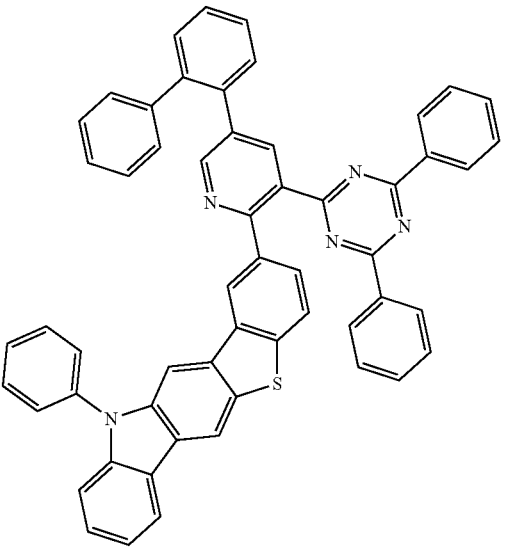
642
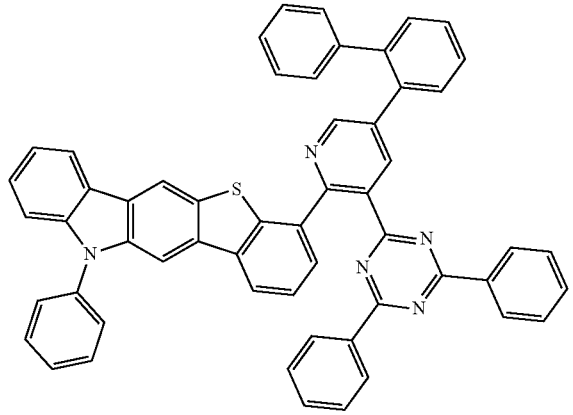
645
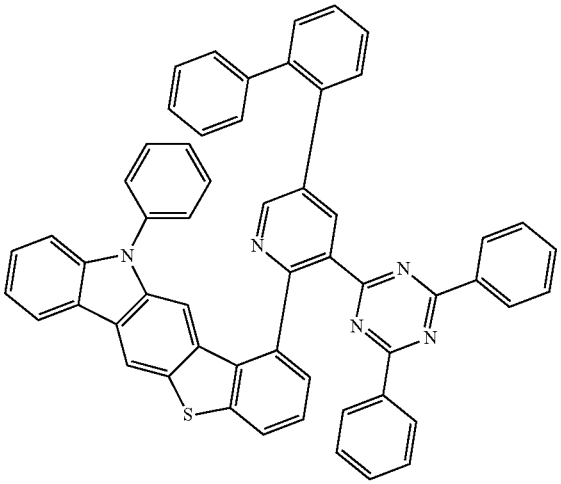
643
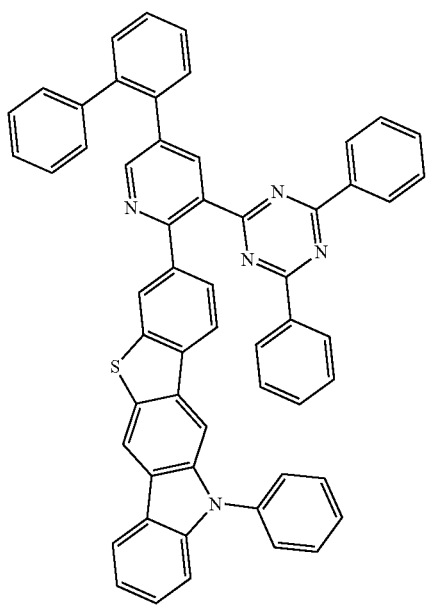
646

1487
-continued
647
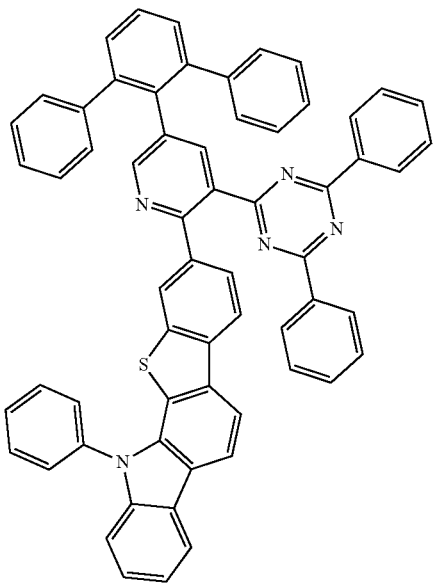
648
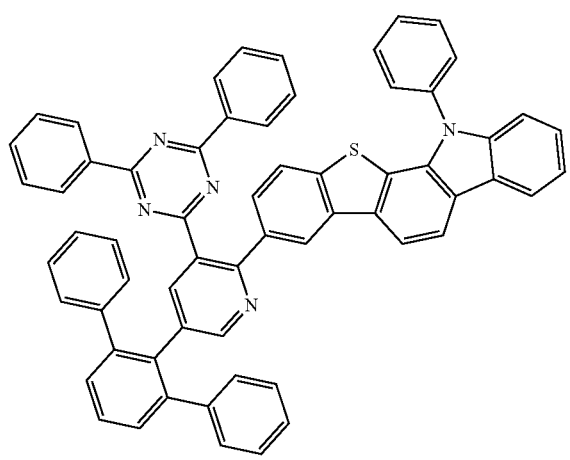
649
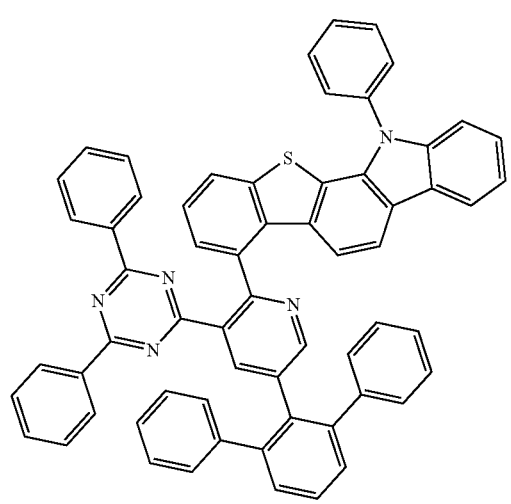
1488
-continued
650
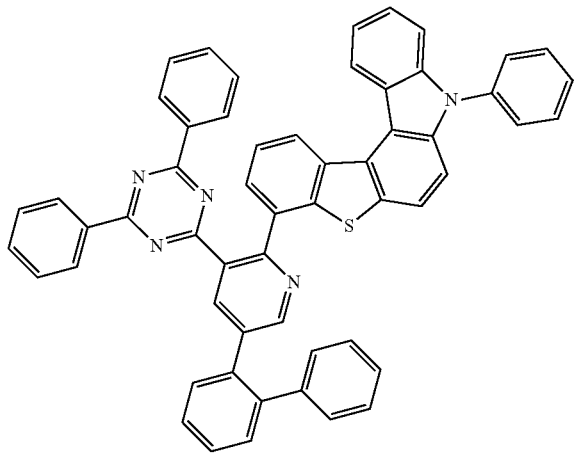
651
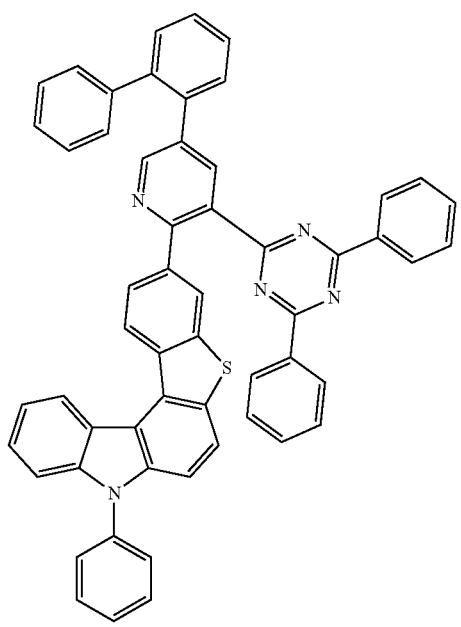

1489
-continued
652
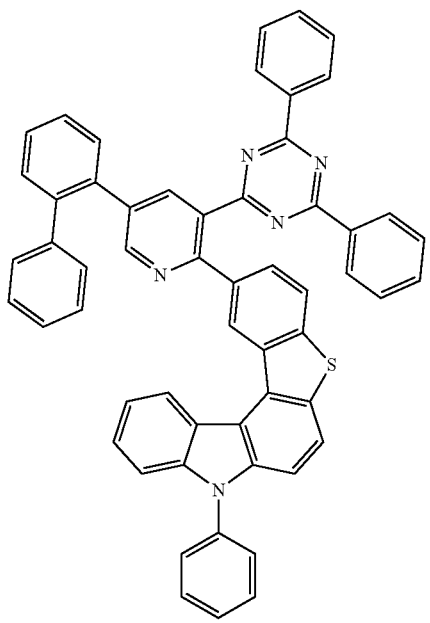
653
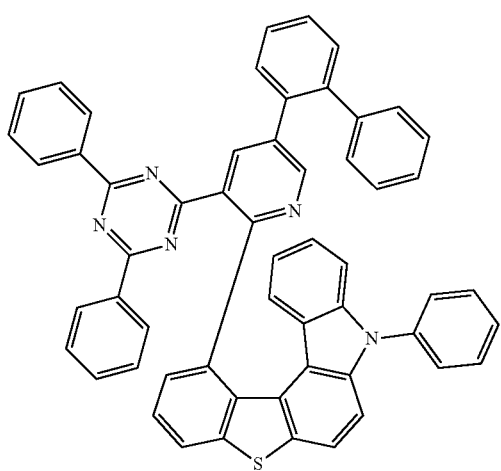
654
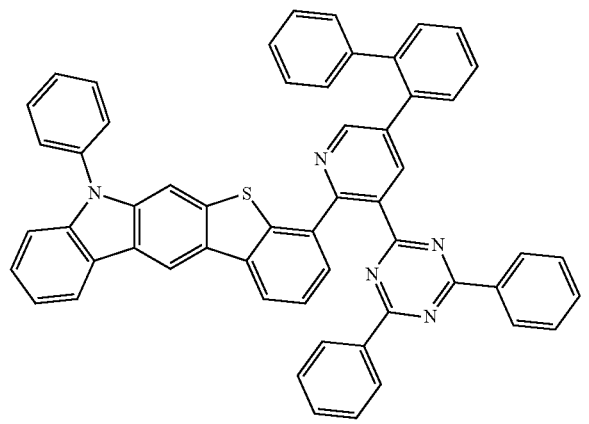
1490
-continued
655
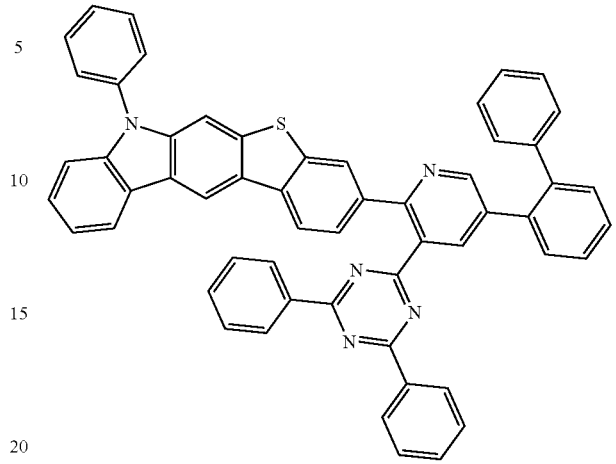
656
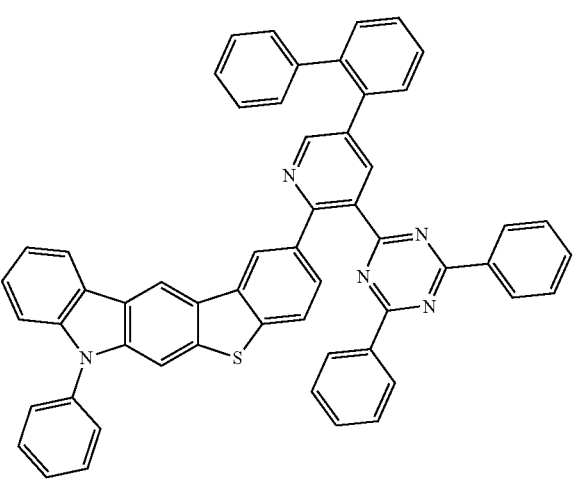
657
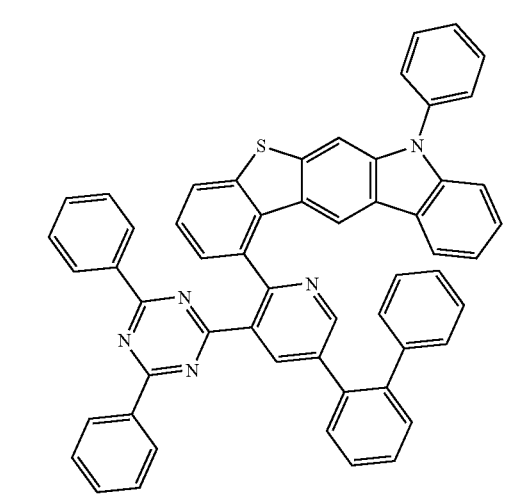

1491
-continued
658
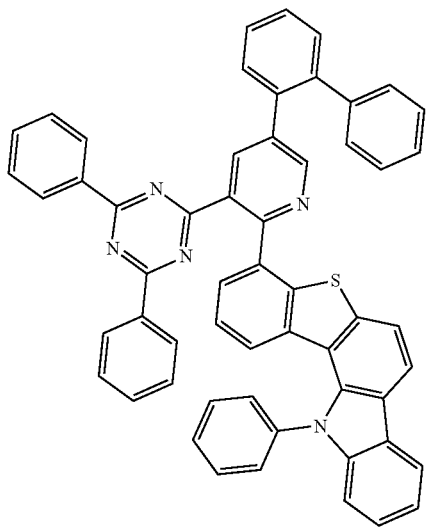
659
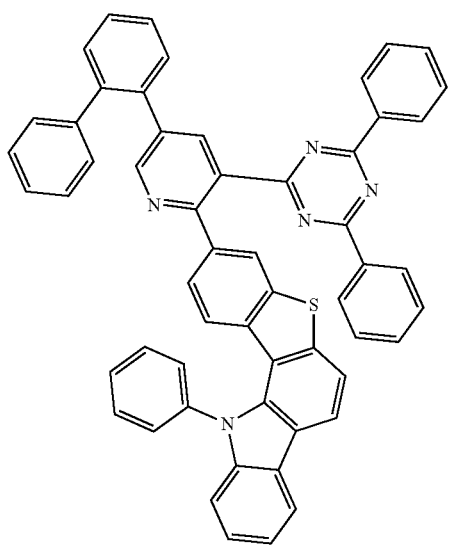
660
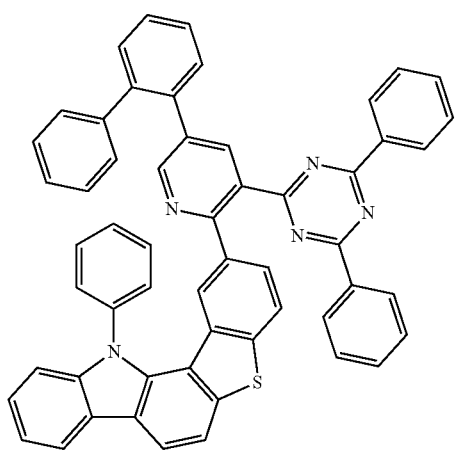
1492
-continued
661
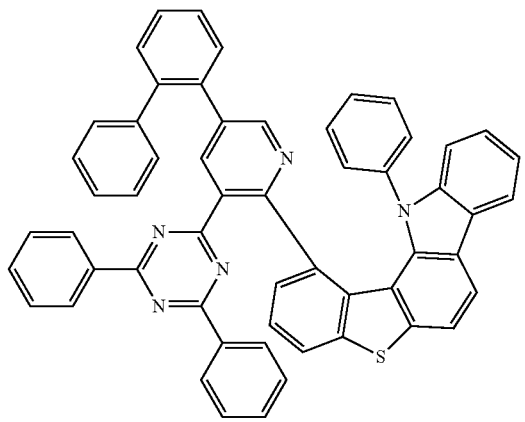
662
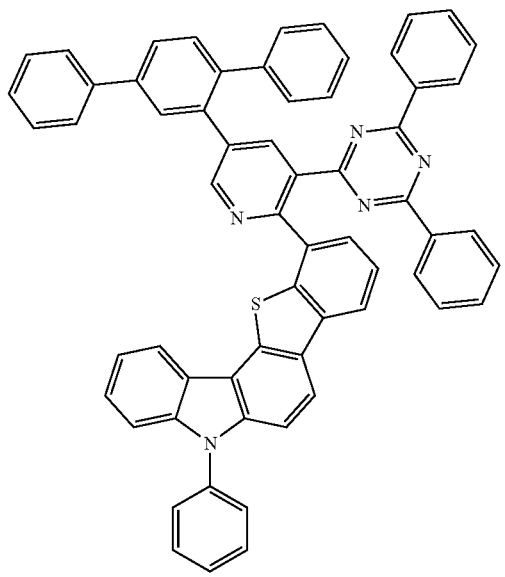

1493
-continued
663
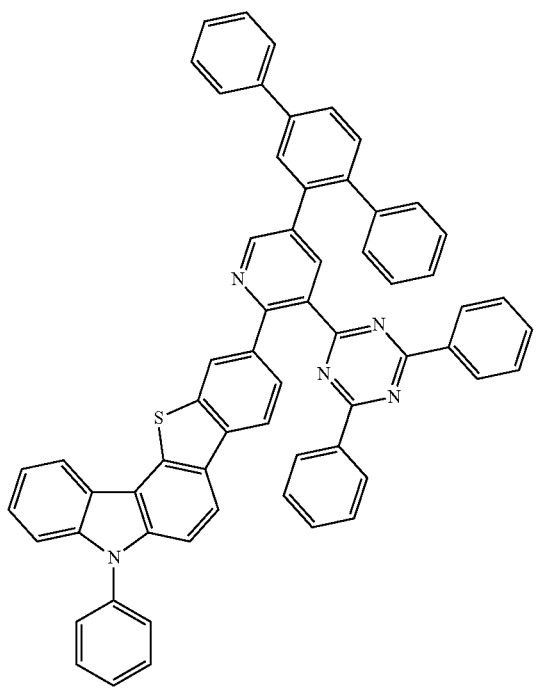
664
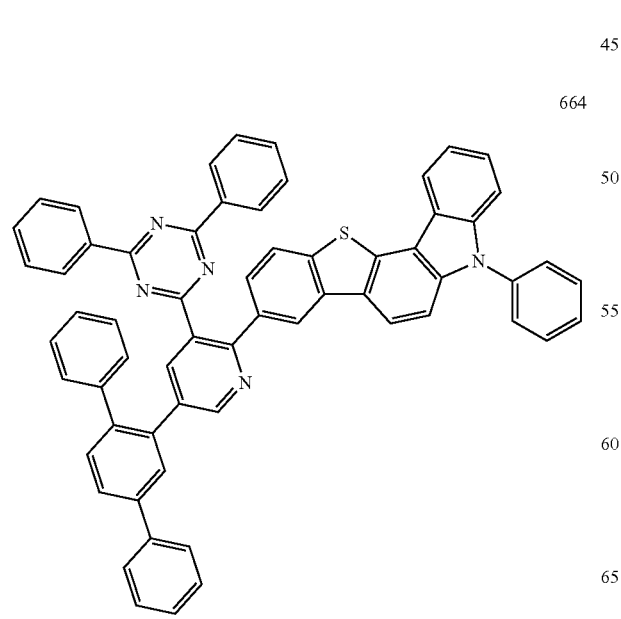
1494
-continued
665
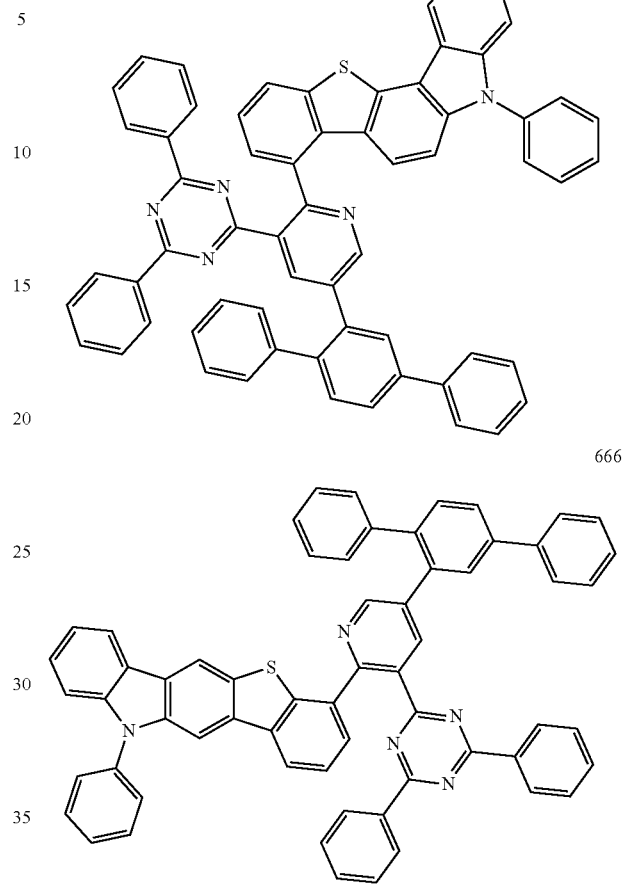
666
667
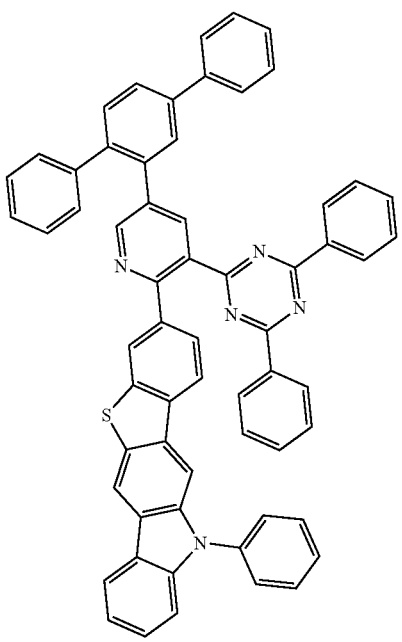

1495
-continued
668
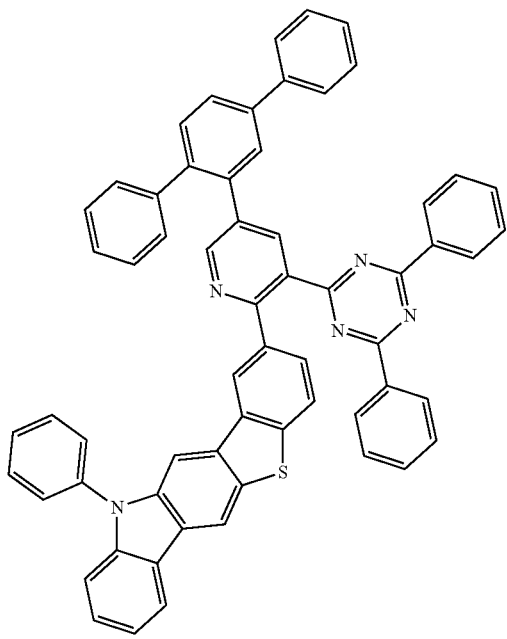
669
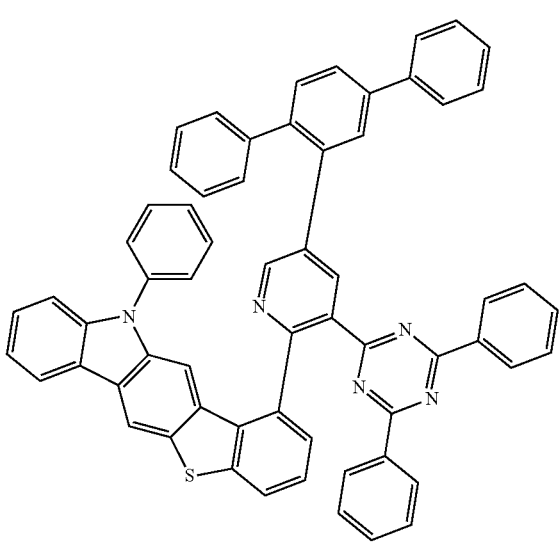
670
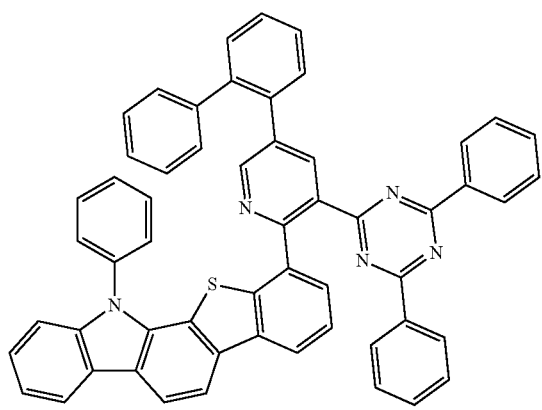
1496
-continued
671
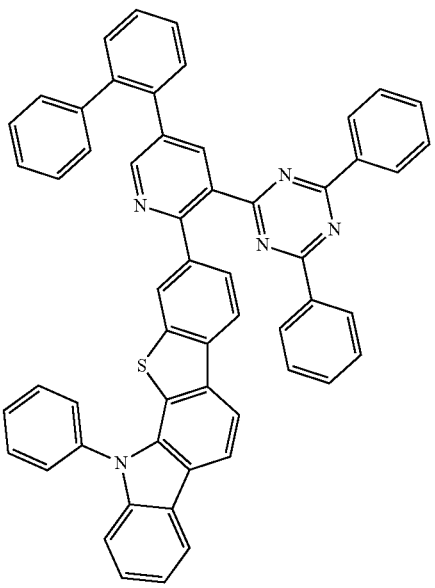
672
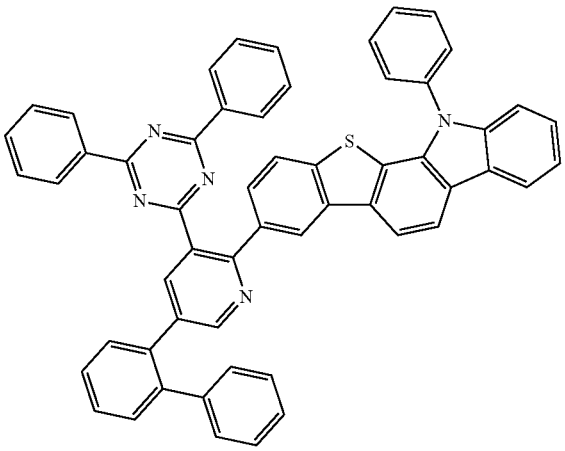
673
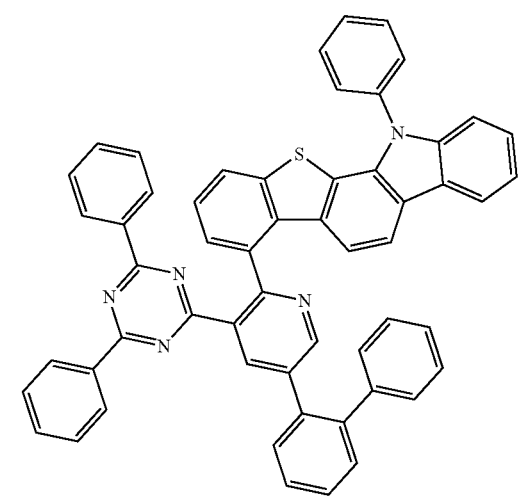

1497 -continued
674
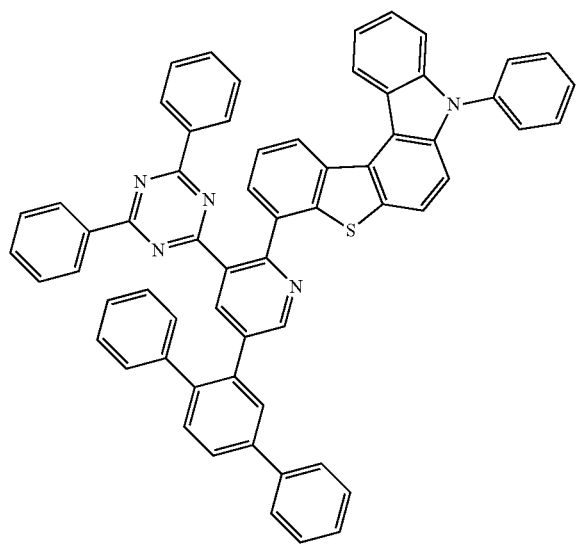
675
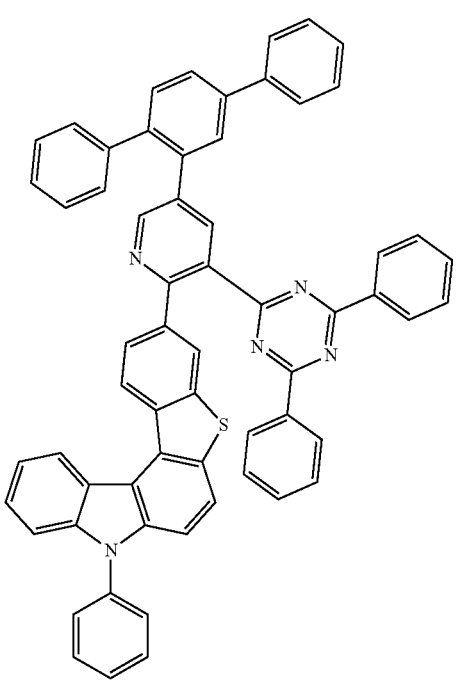
1498 -continued
676
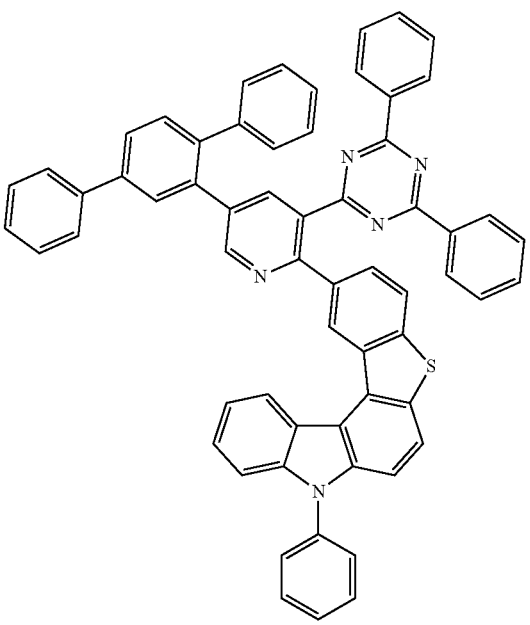
677
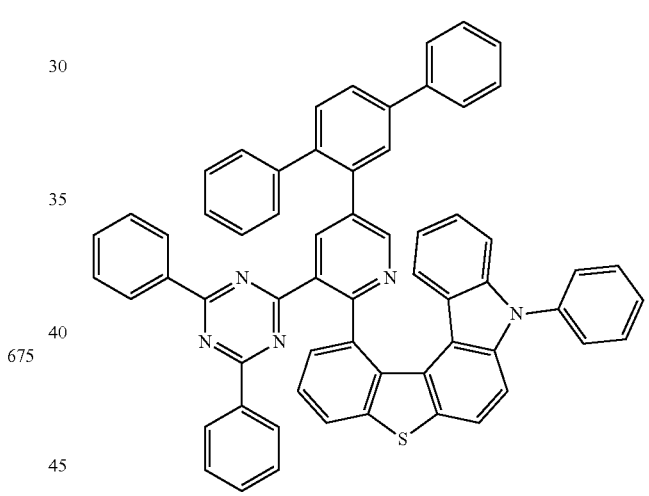
678
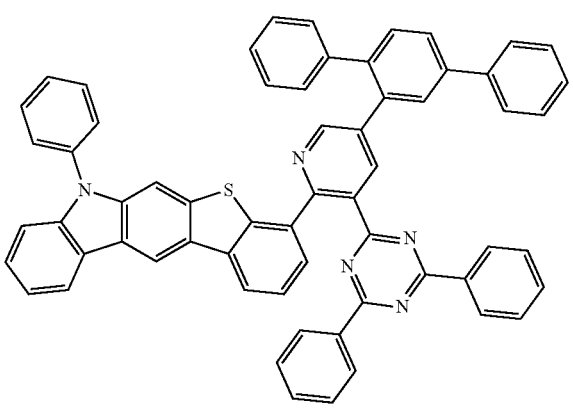

1499
-continued
679
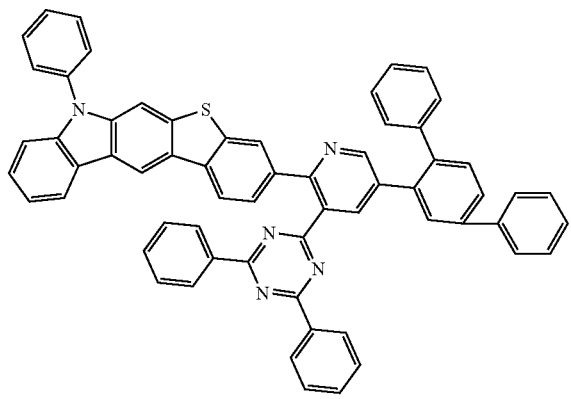
680
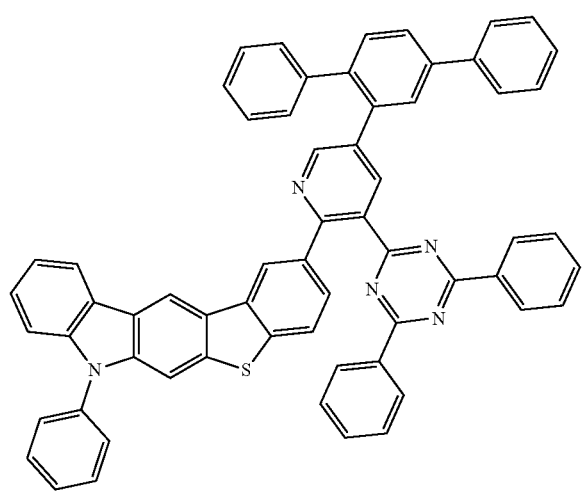
681
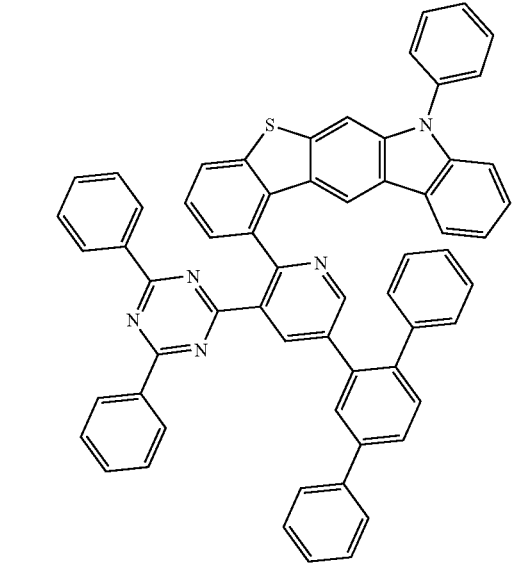
1500
-continued
682
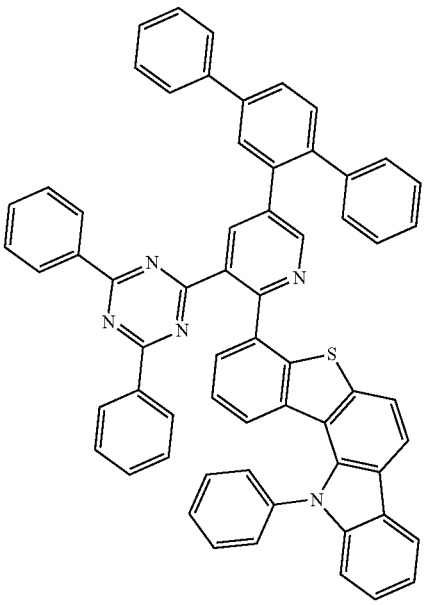
683
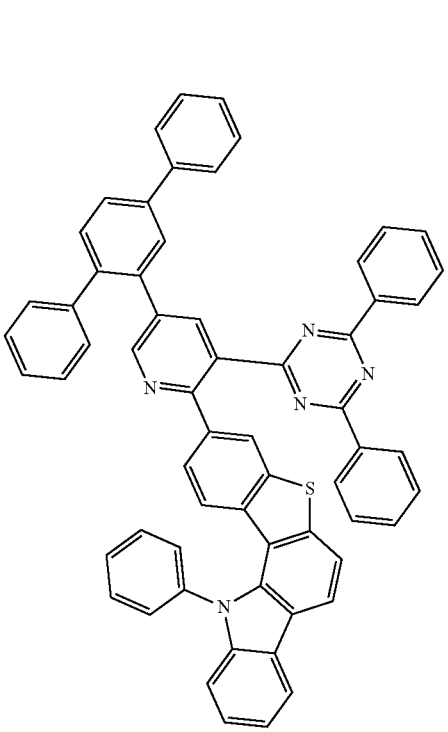

1501
-continued
684
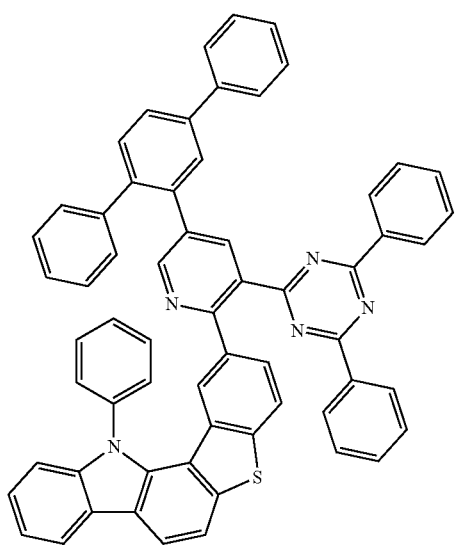
685
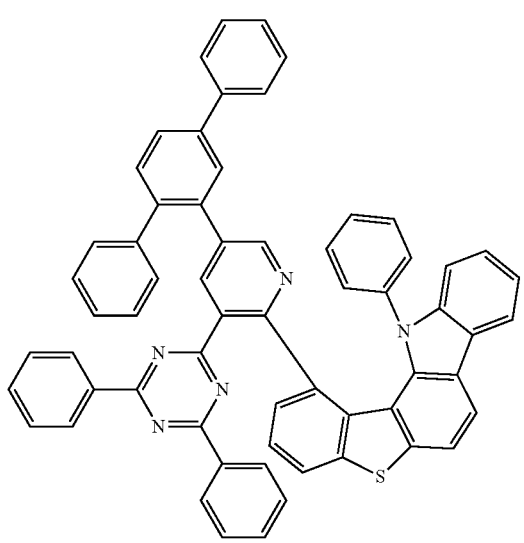
686
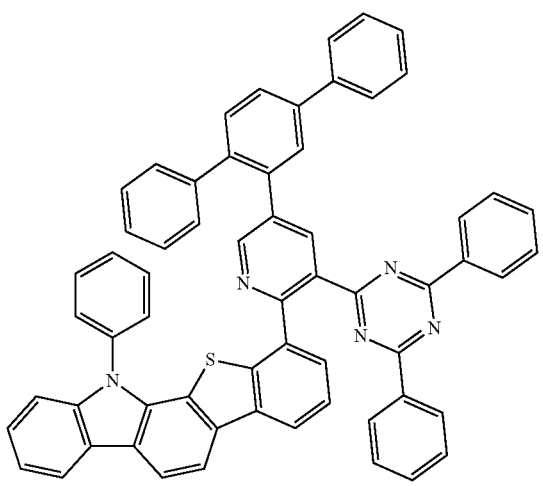
1502
-continued
687
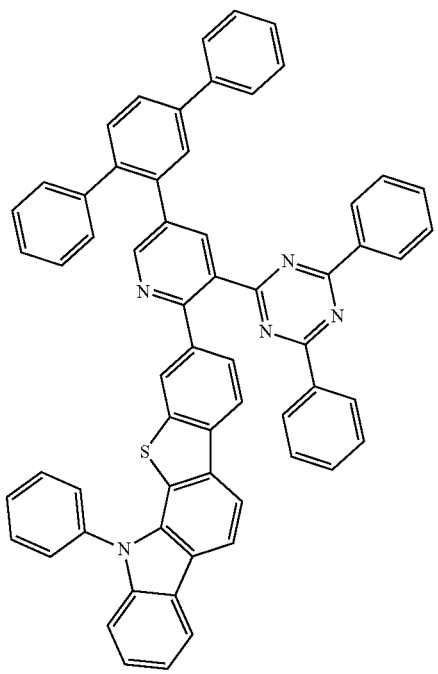
688
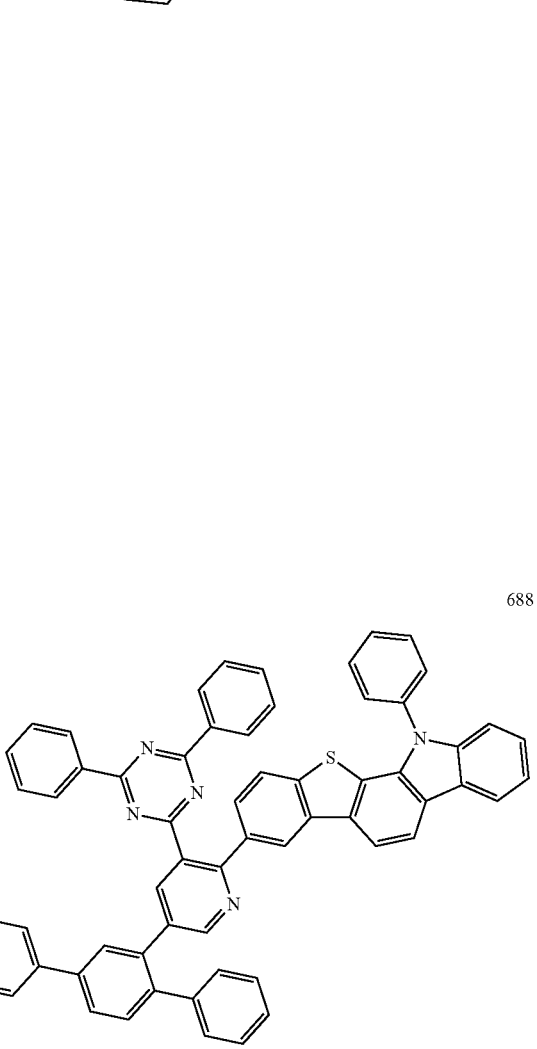

1503
-continued
689
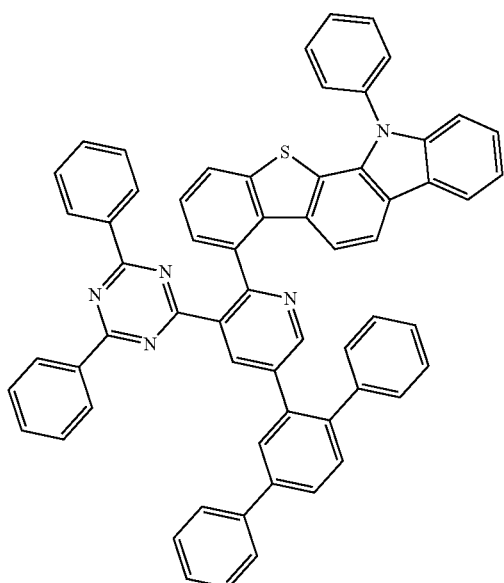
1504
-continued
691
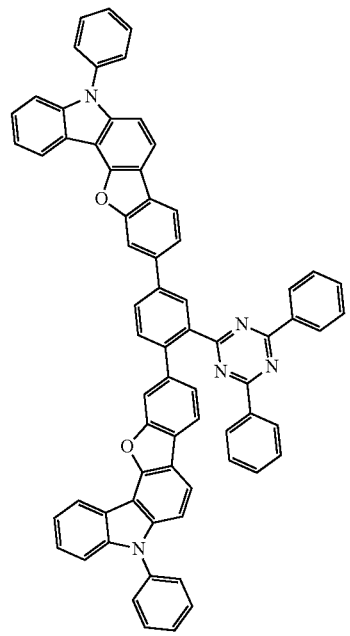
690
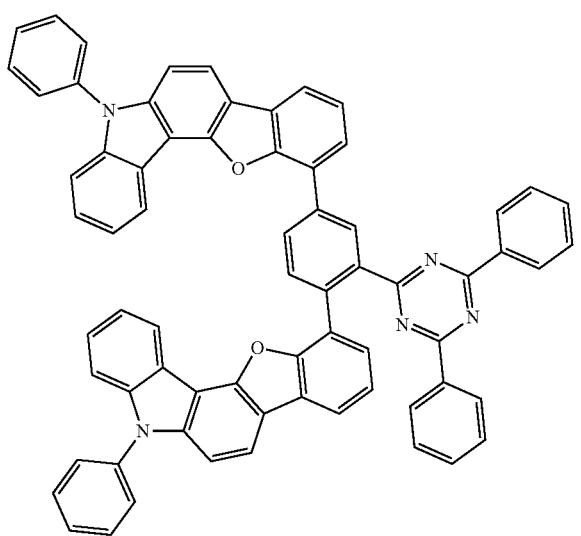
692
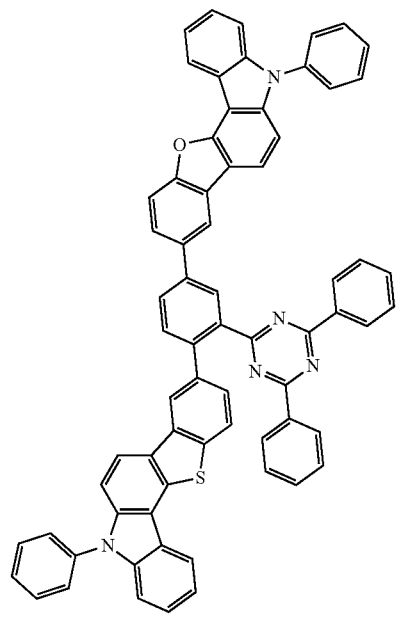

1505
-continued
693
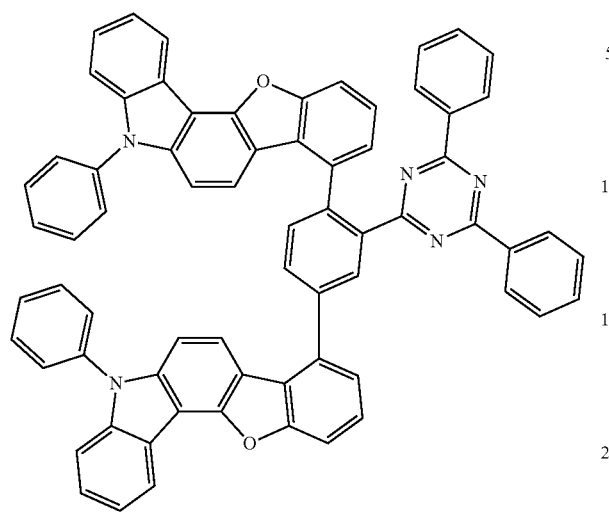
694
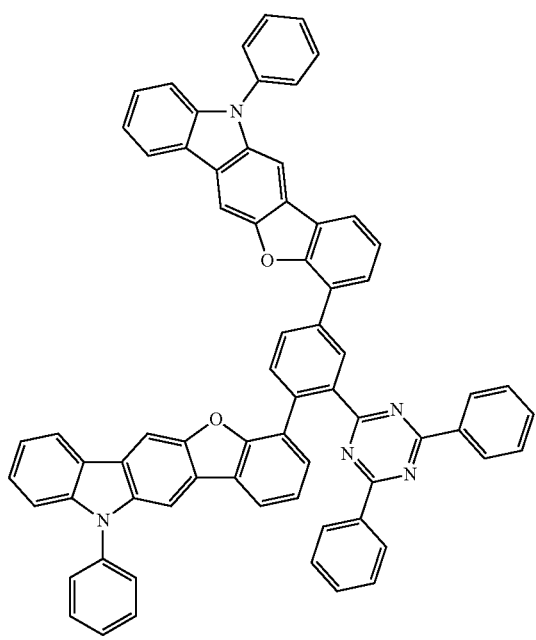
1506
-continued
695
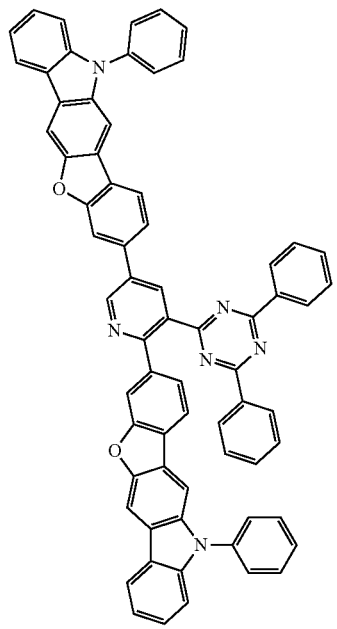
696
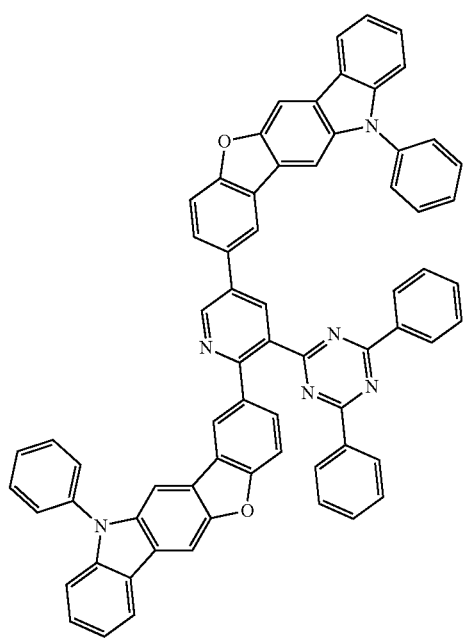

1507
-continued
697
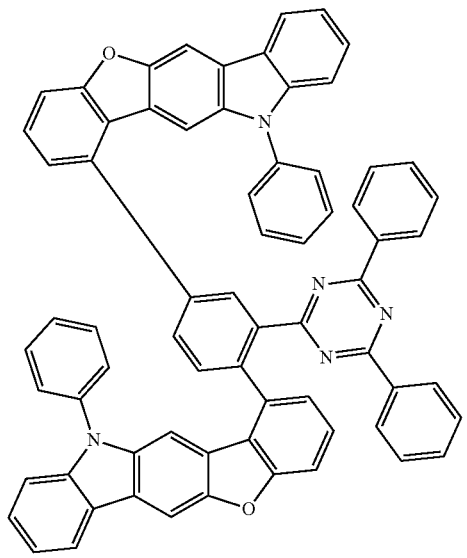
1508
-continued
699
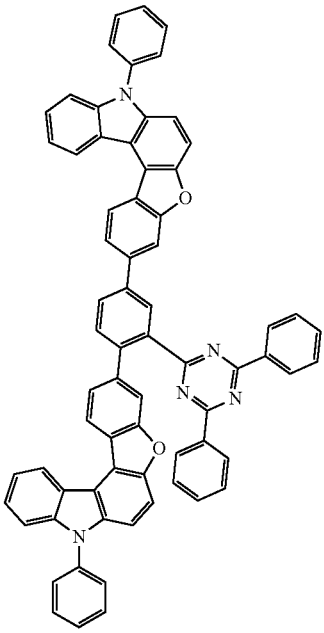
698
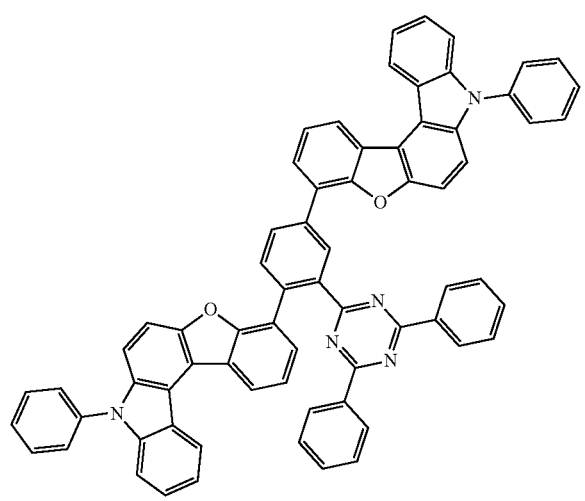
700
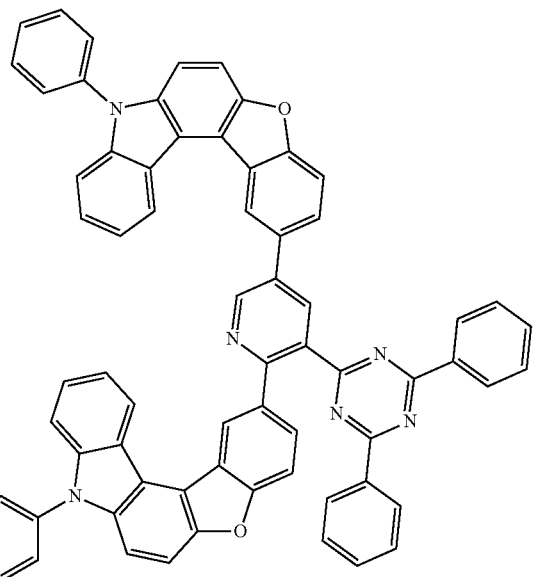

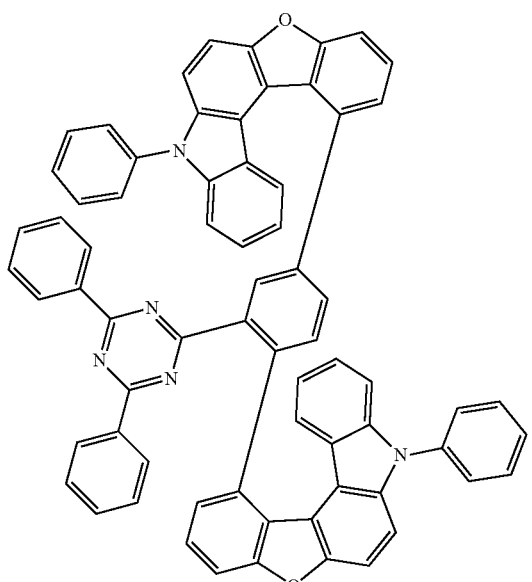
701
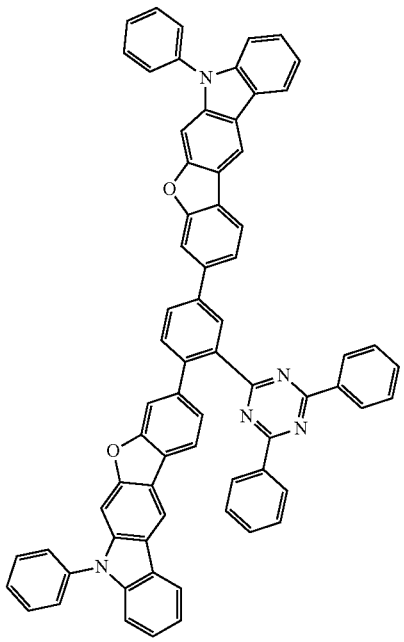
703
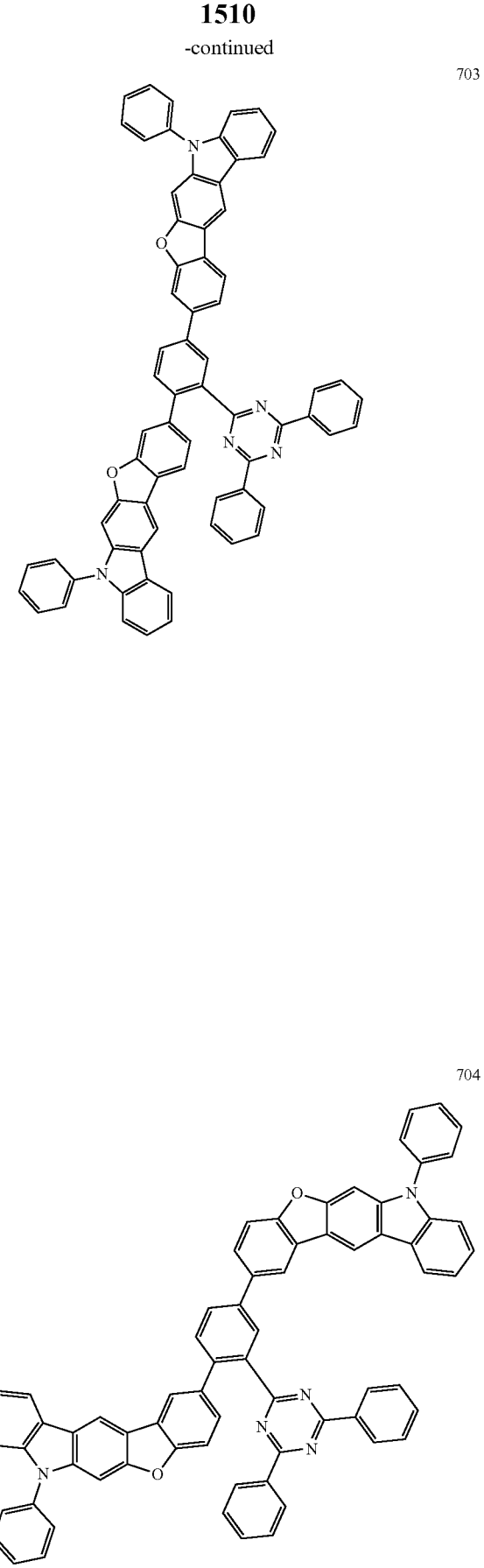
702
704

1511
-continued
705
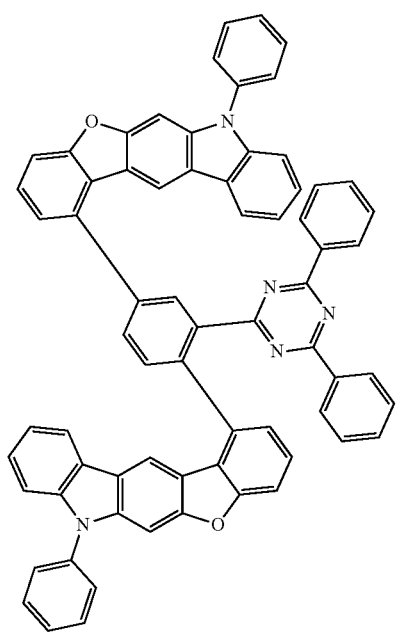
1512
-continued
707
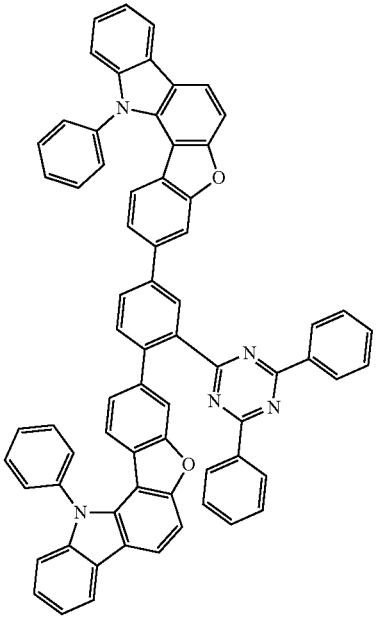
708
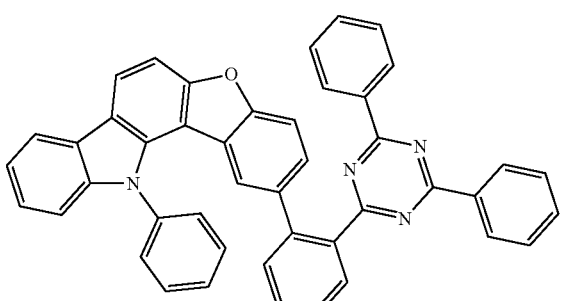
706
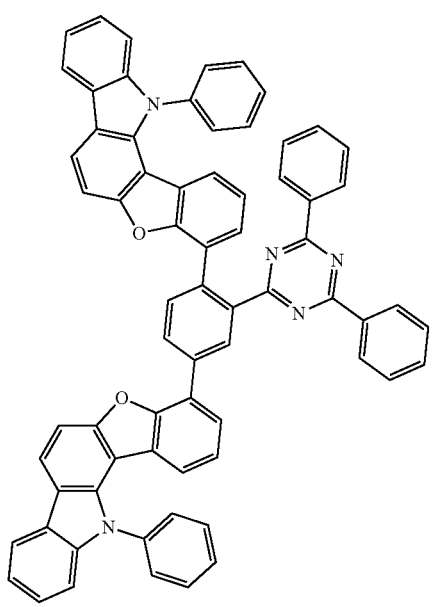
709
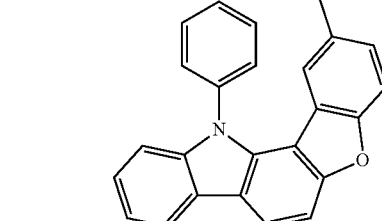
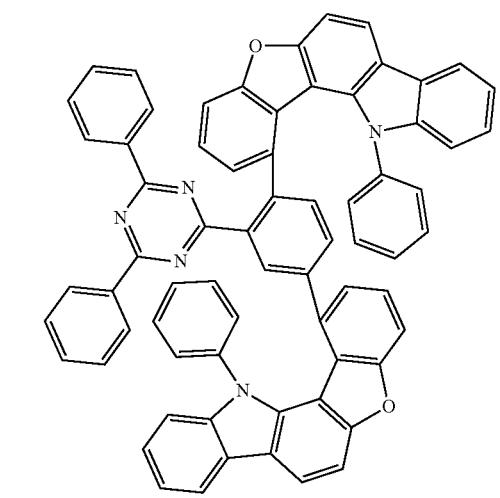

1513
-continued
710
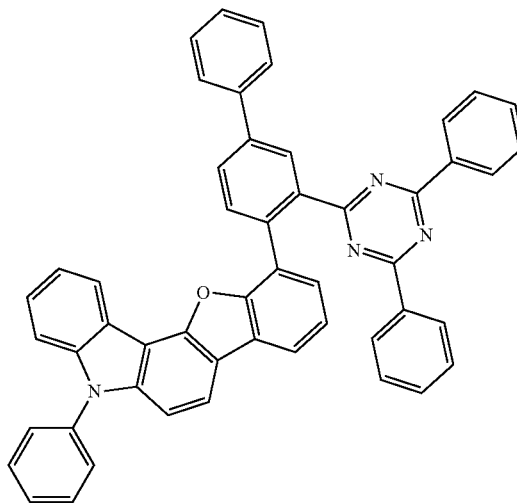
711
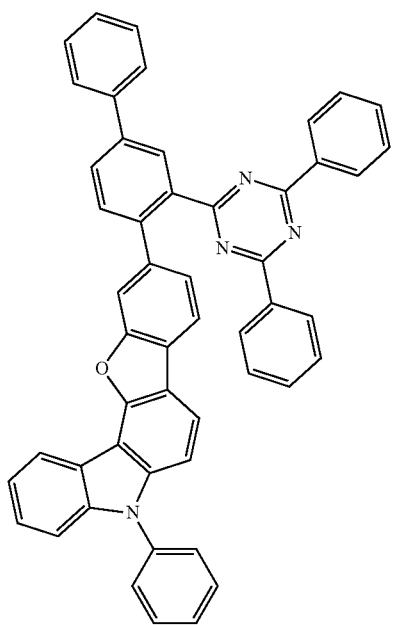
1514
-continued
712
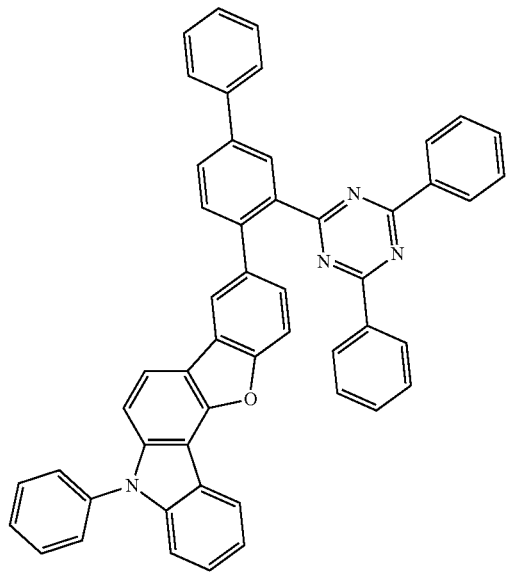
713
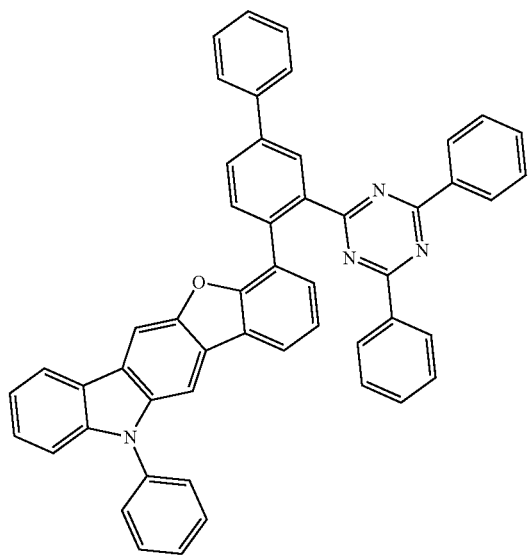
714

1515
-continued
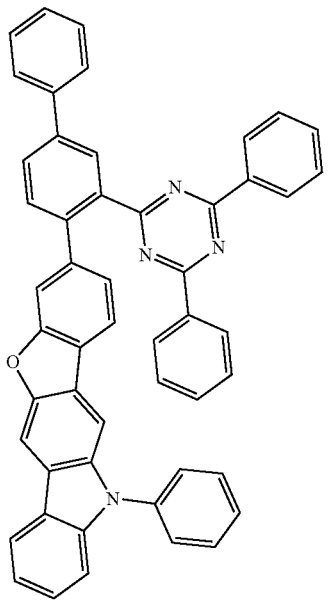
1516
-continued
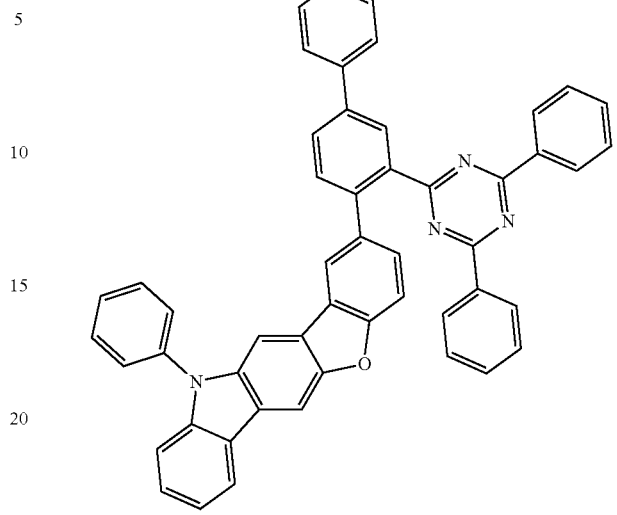
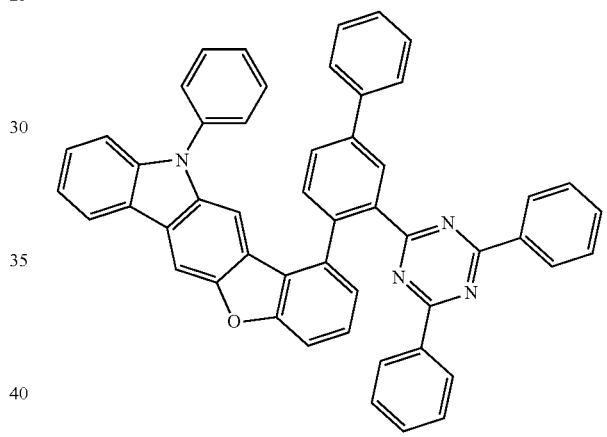
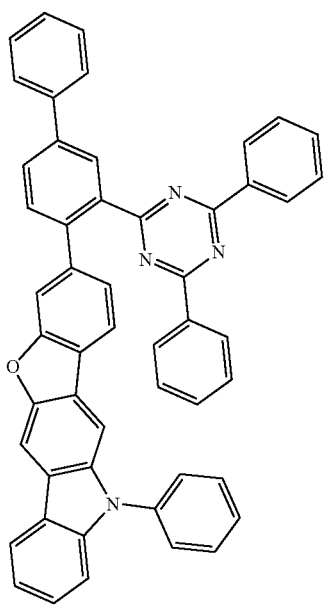
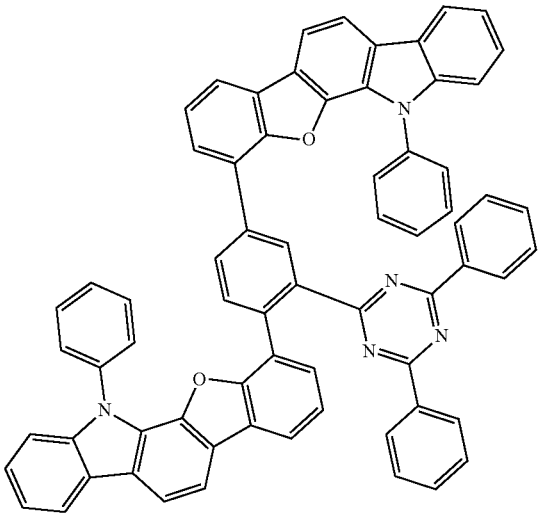

1517
-continued
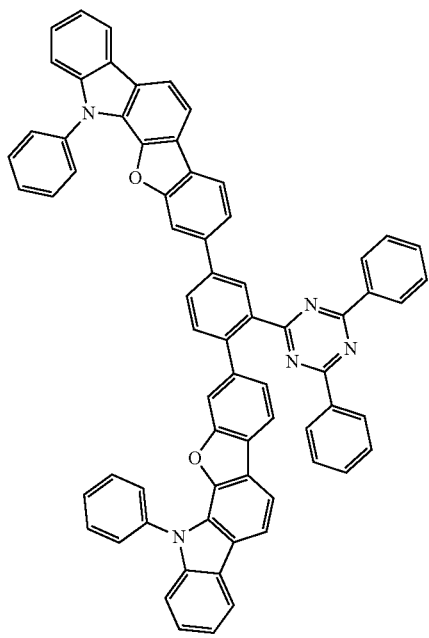
1518
-continued
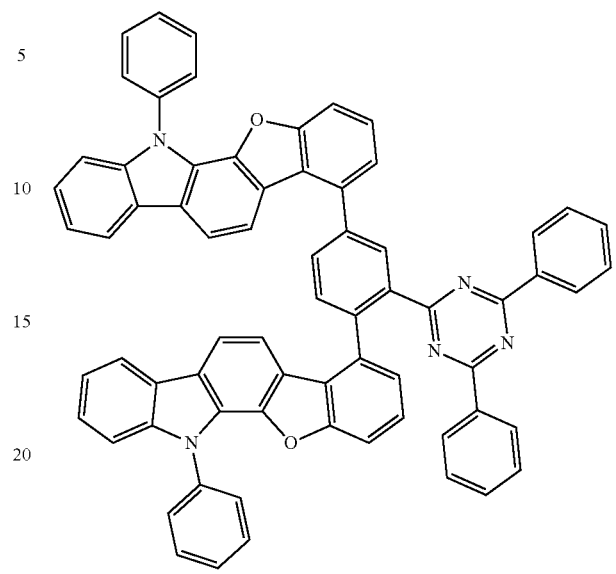
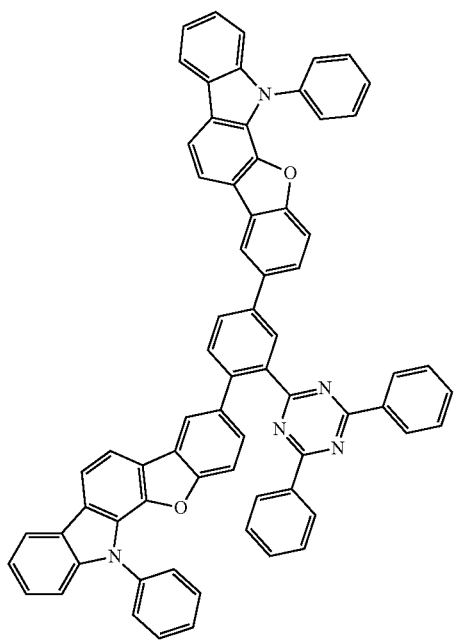
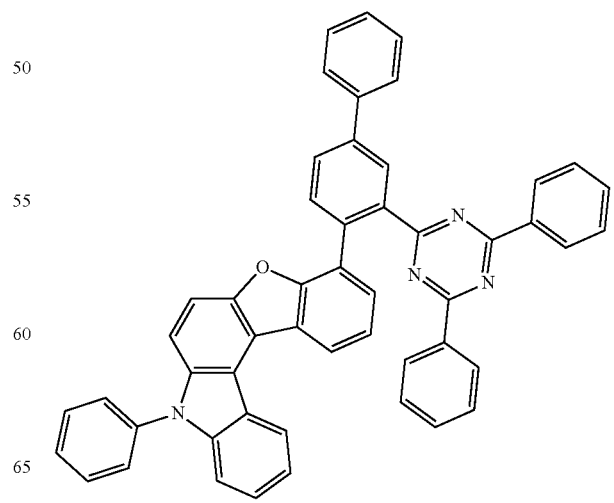

1519 1520
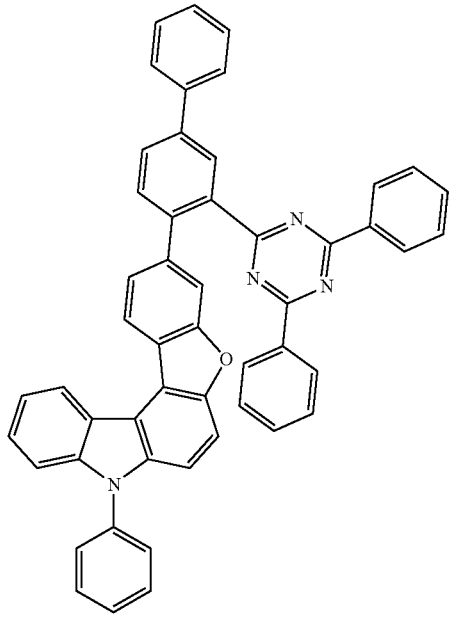
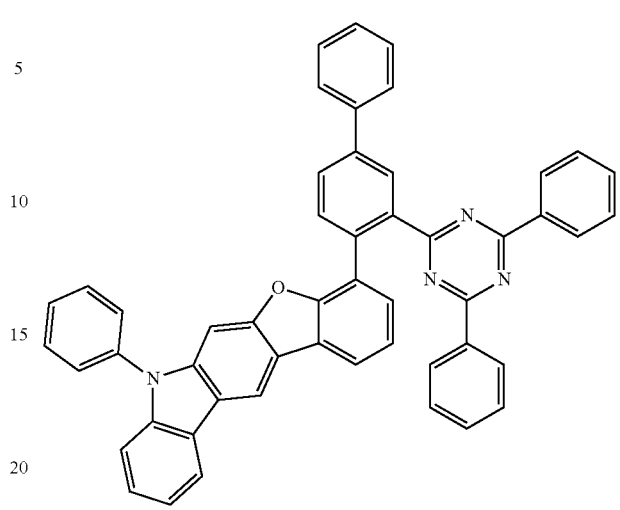
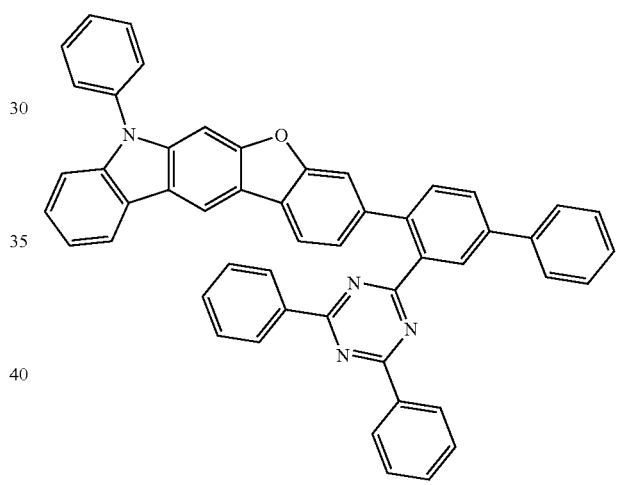
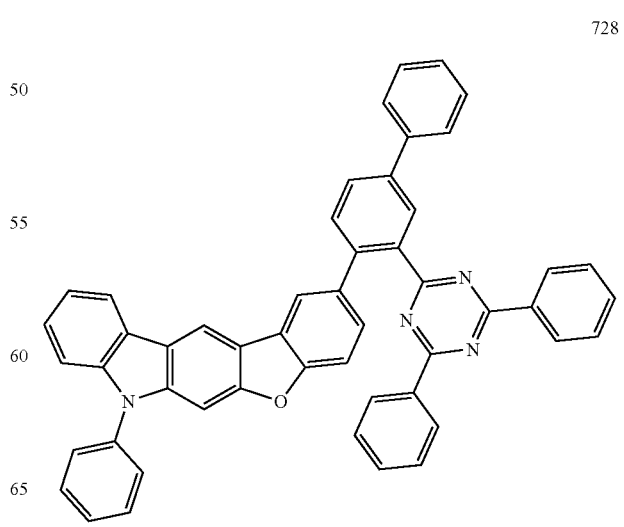

-continued
729
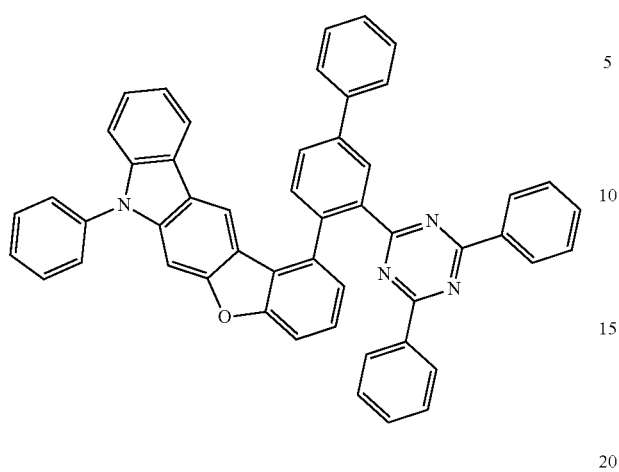
730
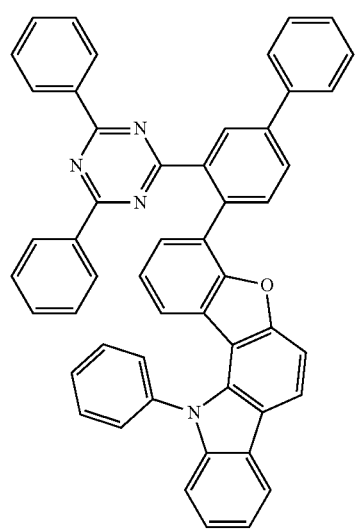
731
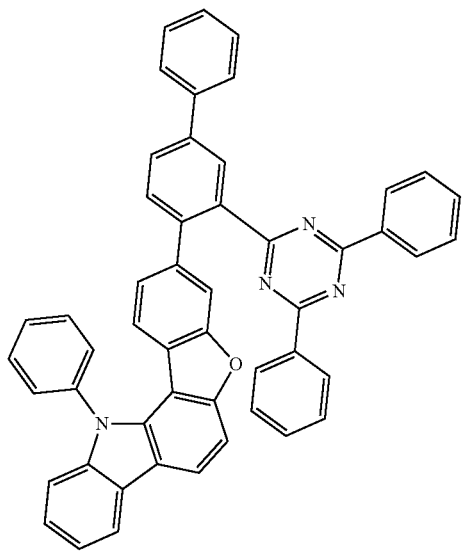
-continued
732
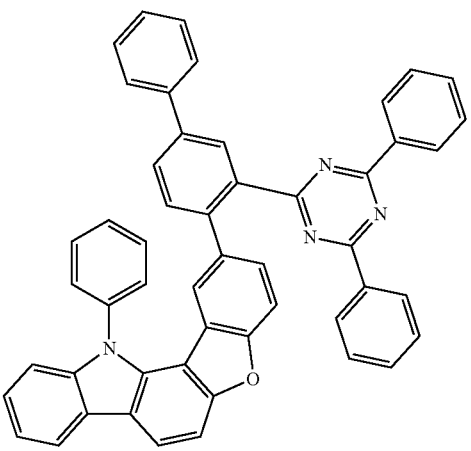
733
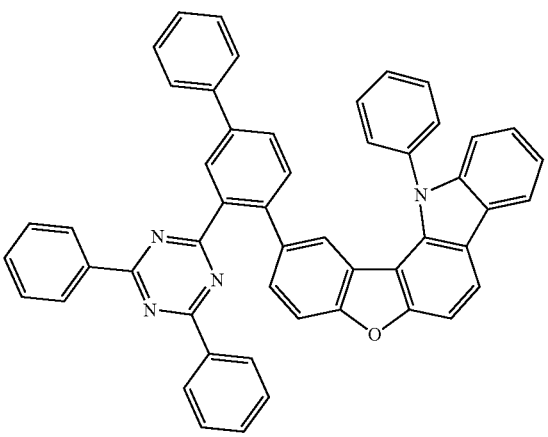
734
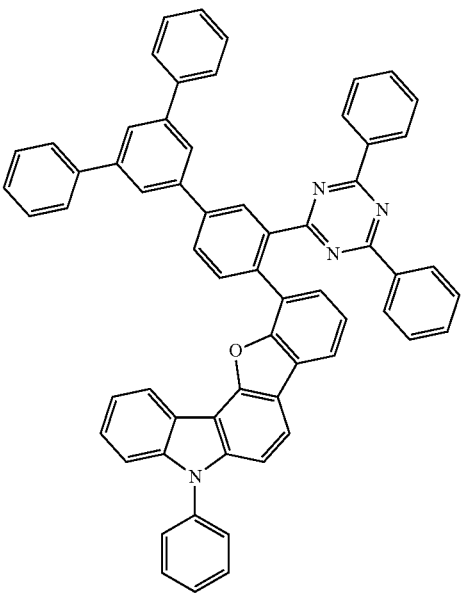

1523
-continued
1524
-continued
735
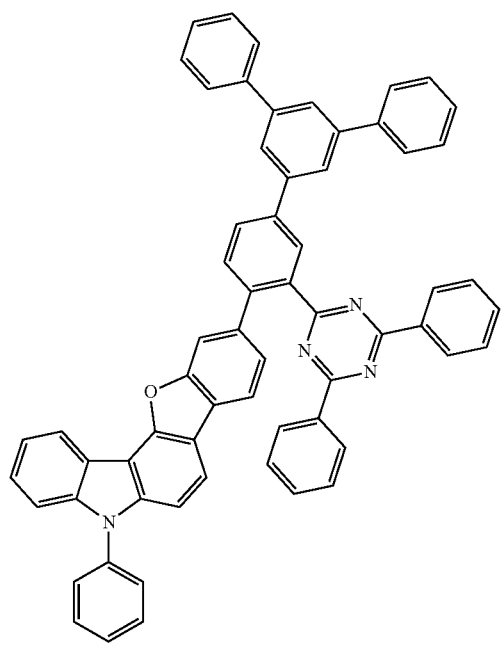
738
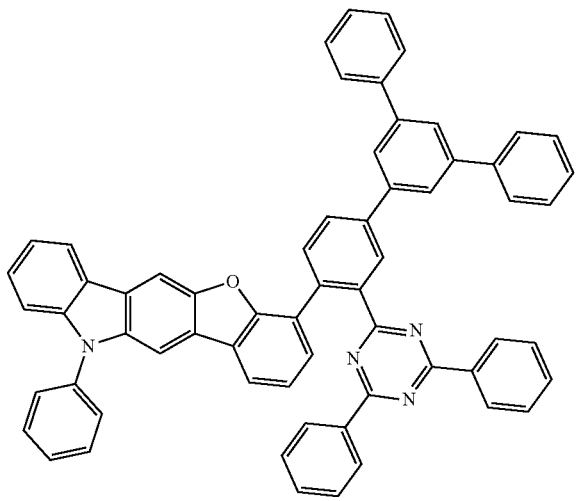
736
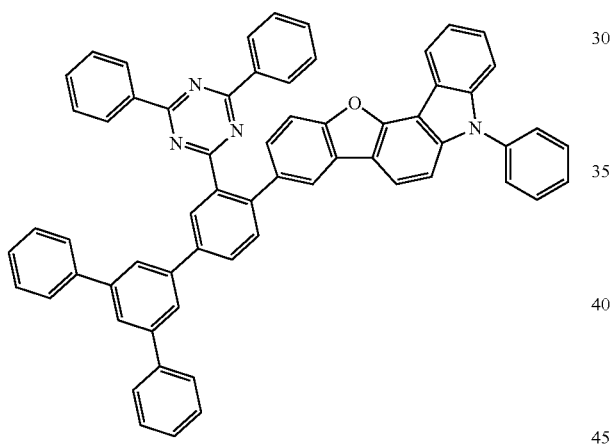
737
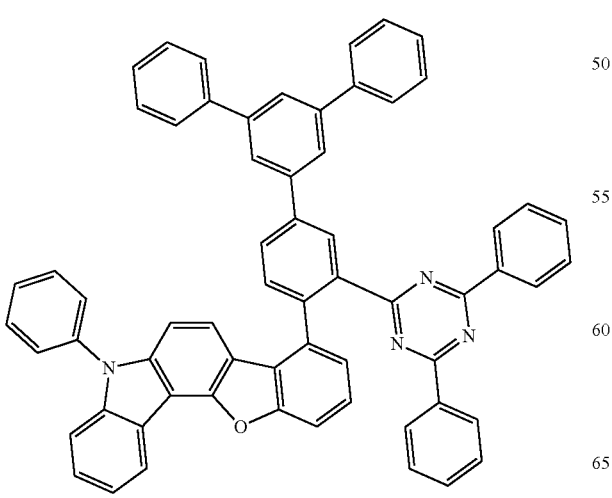
739
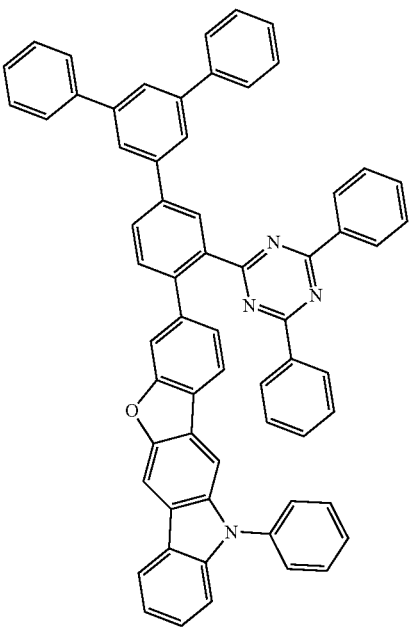

1525
-continued
740
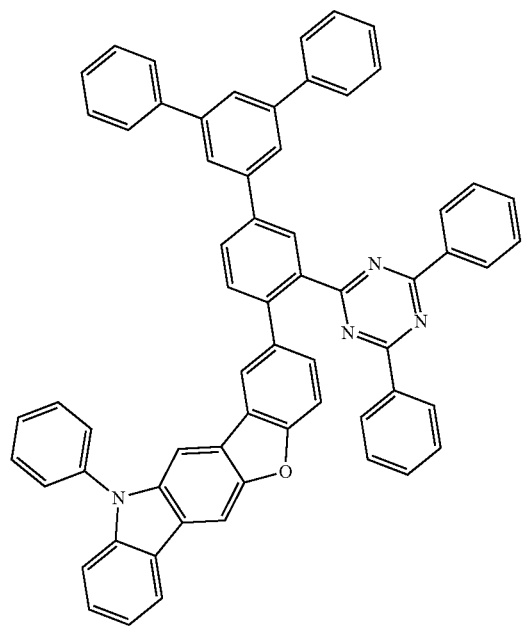
741
742
1526
-continued
743
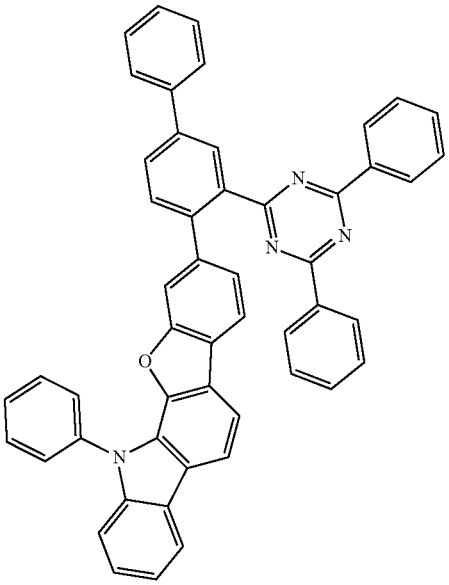
744
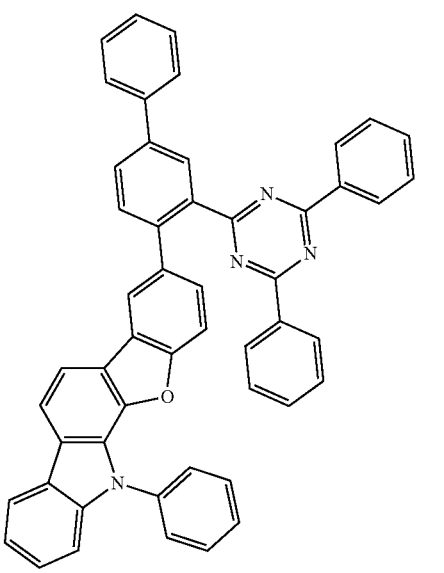
745
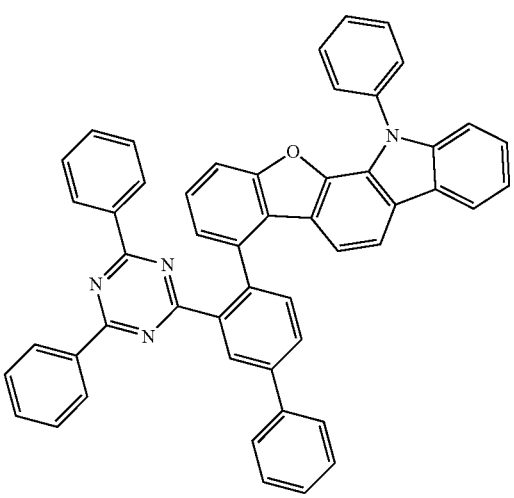

1527
-continued
746
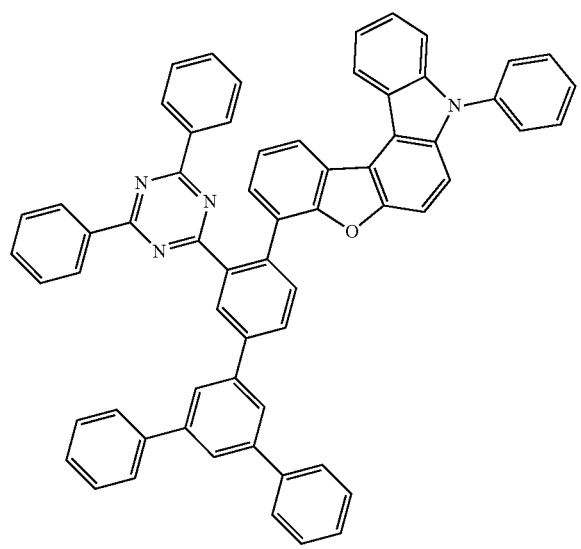
747
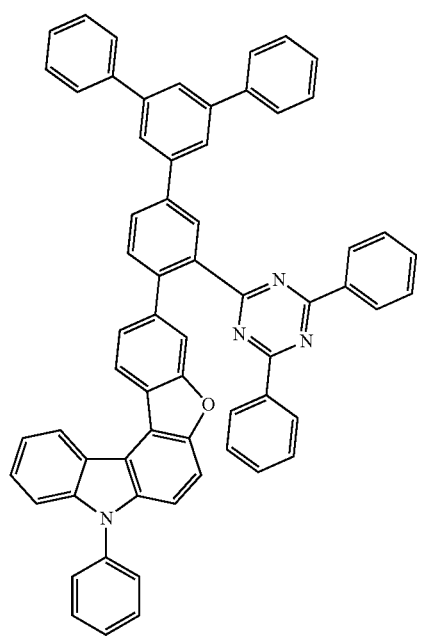
1528
-continued
748
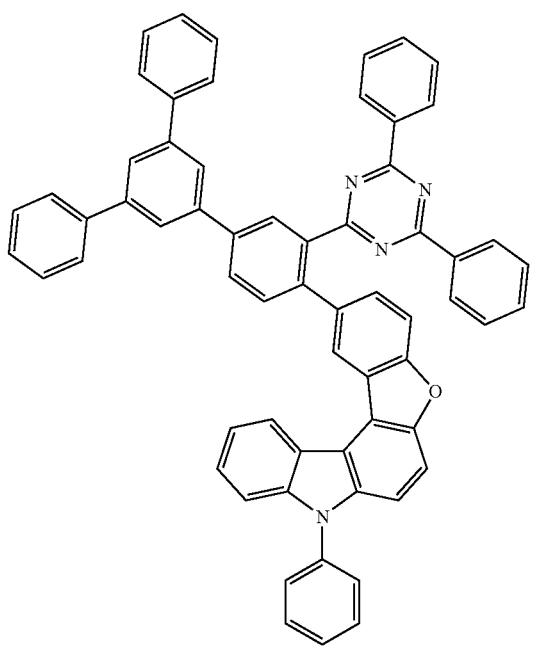
749
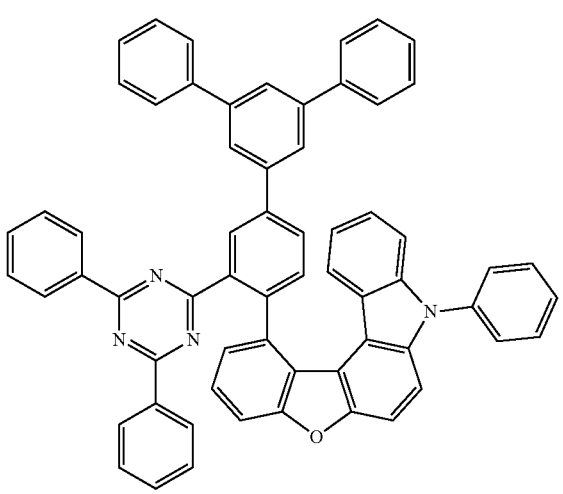

1529
-continued
750
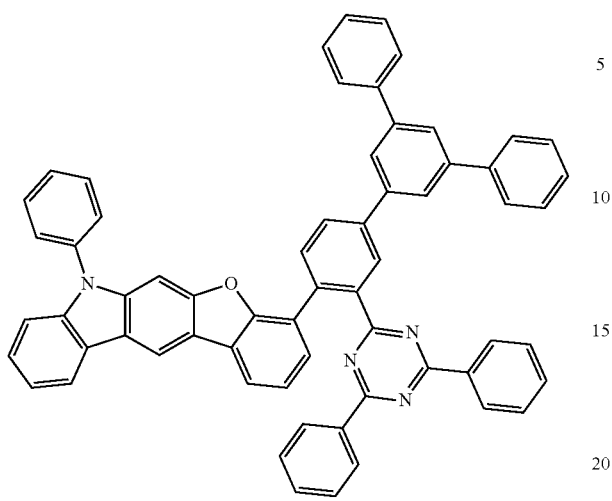
751
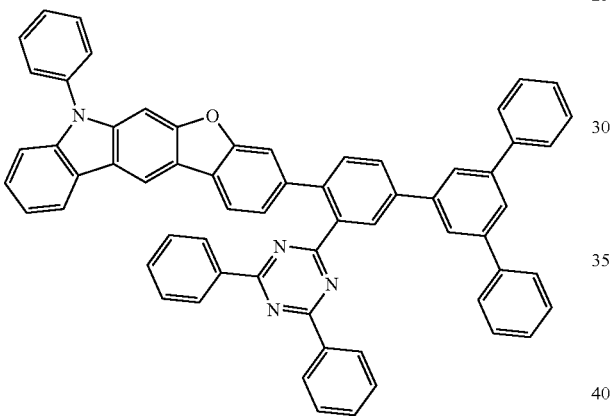
752
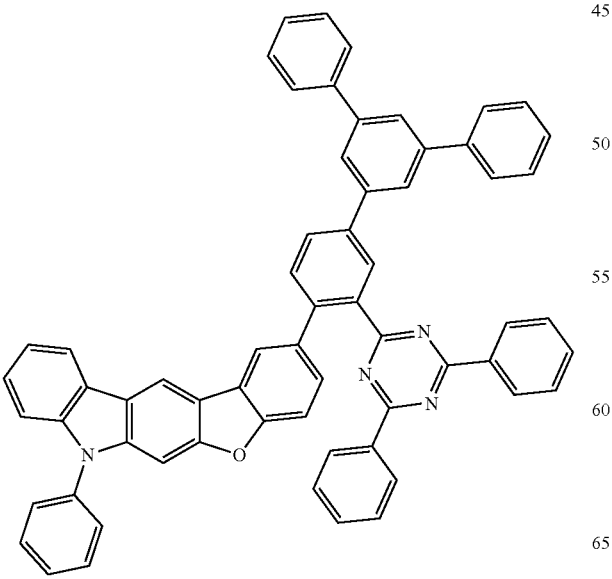
1530
-continued
753
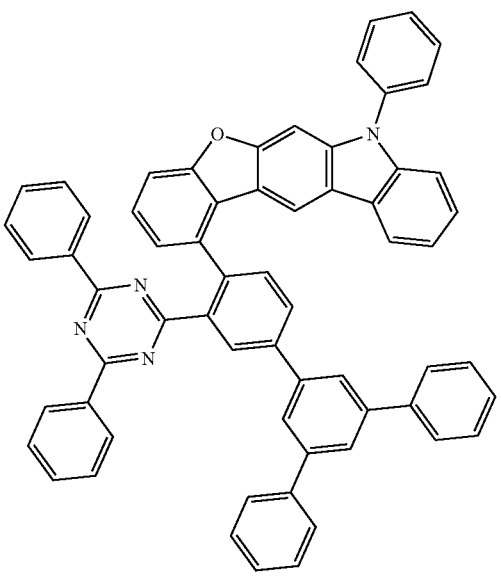
764
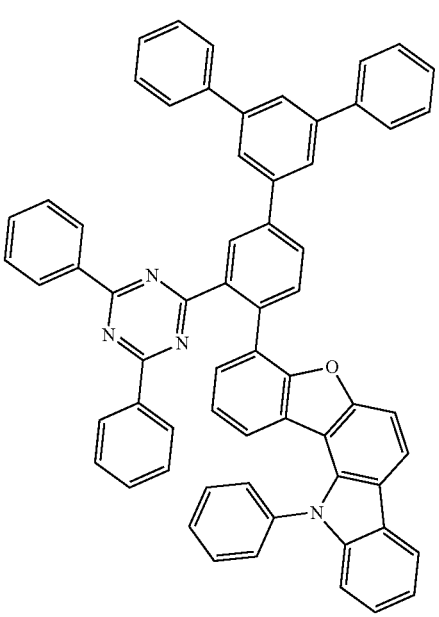

1531
-continued
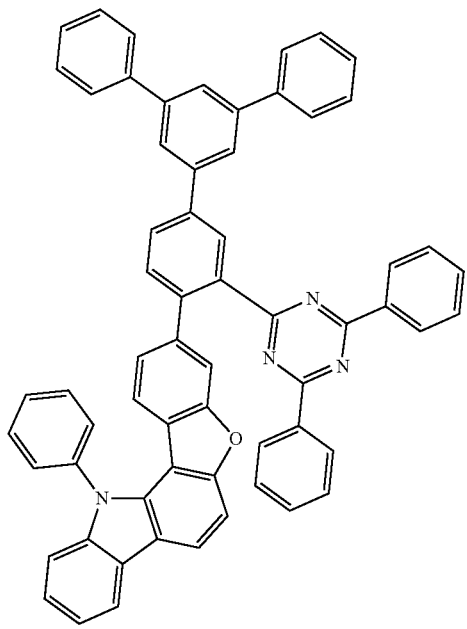
755
1532
-continued
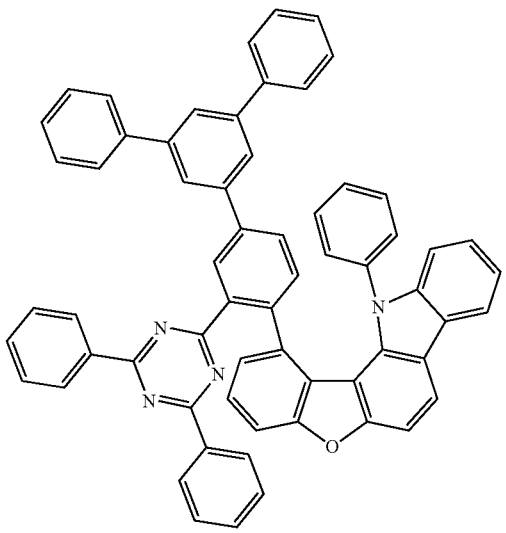
757
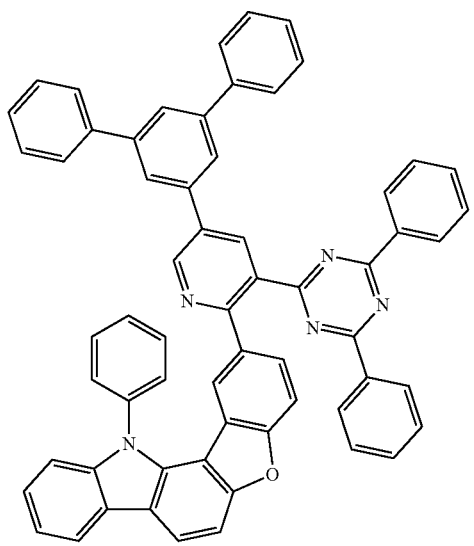
756
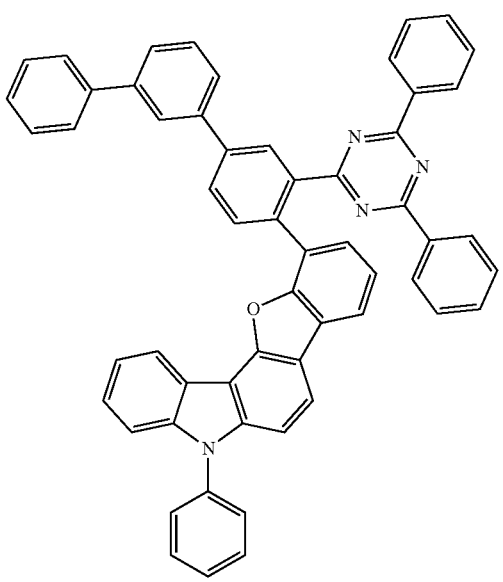
758

1533
-continued
759
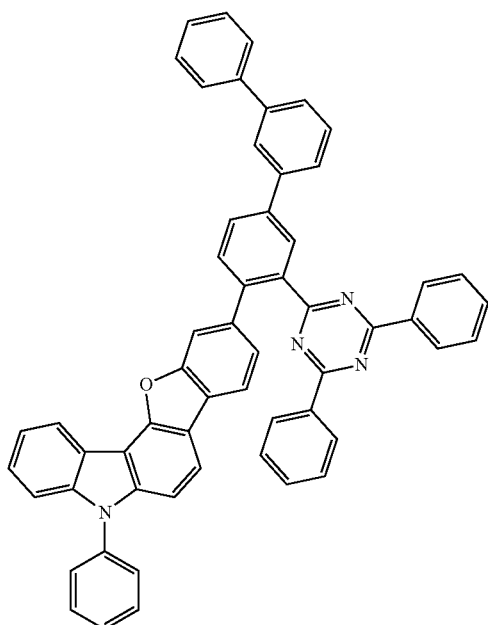
760
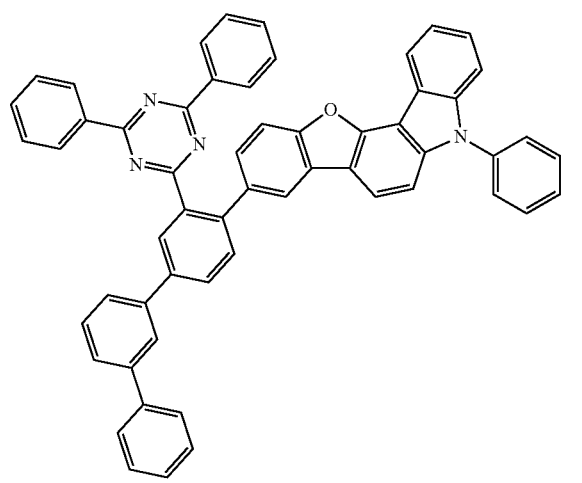
761
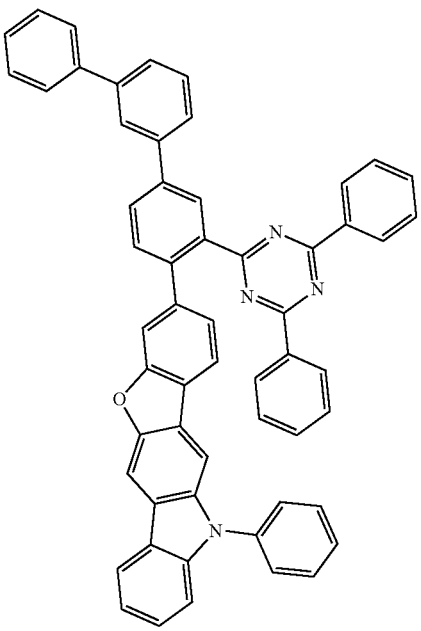
1534
-continued
762
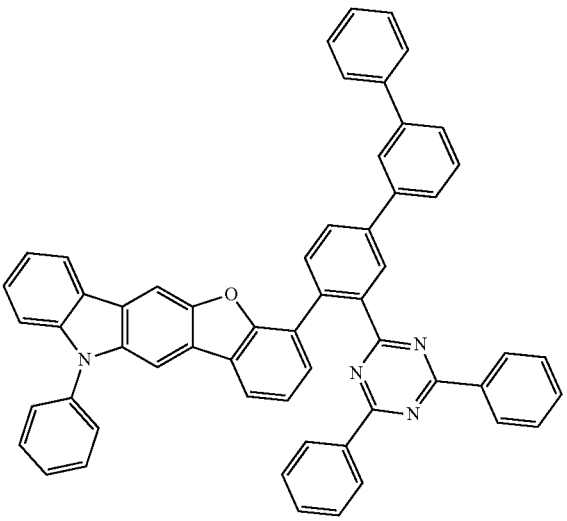
763
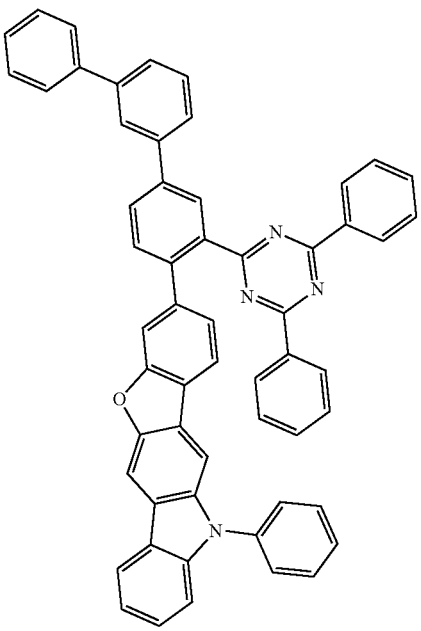

1535
-continued
764
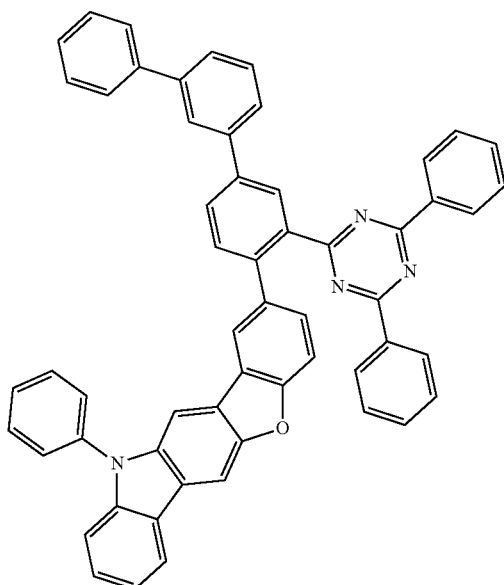
765
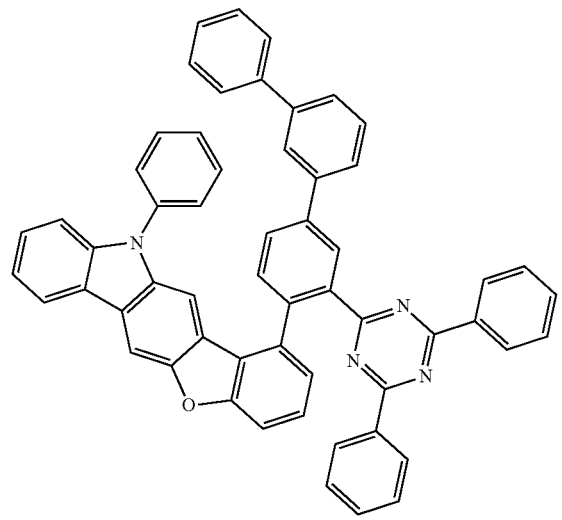
766
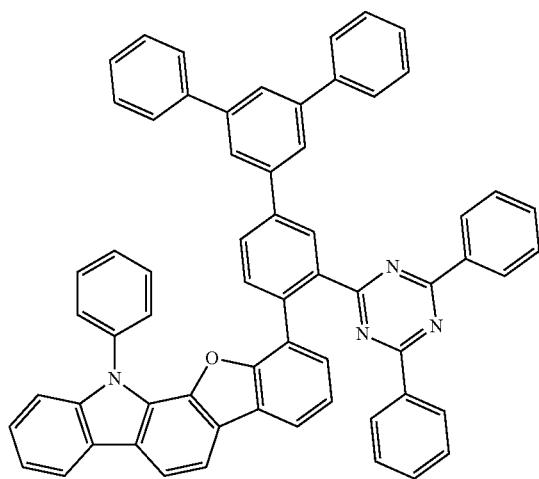
1536
-continued
767
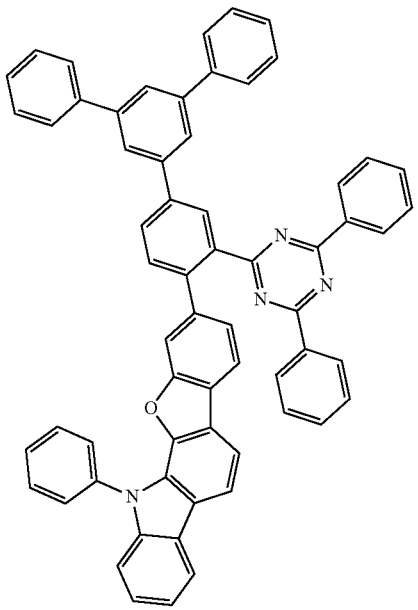
768
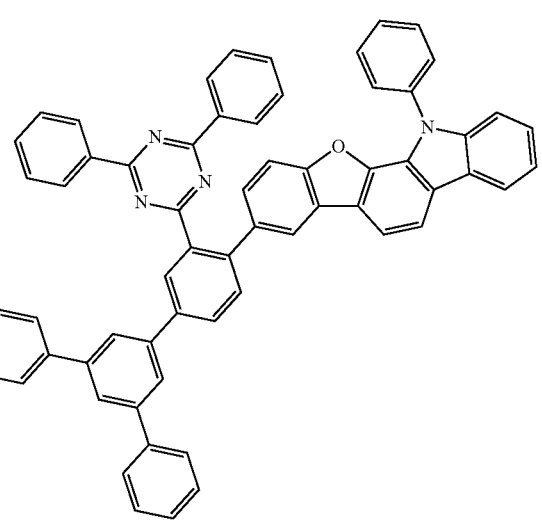

1537
-continued
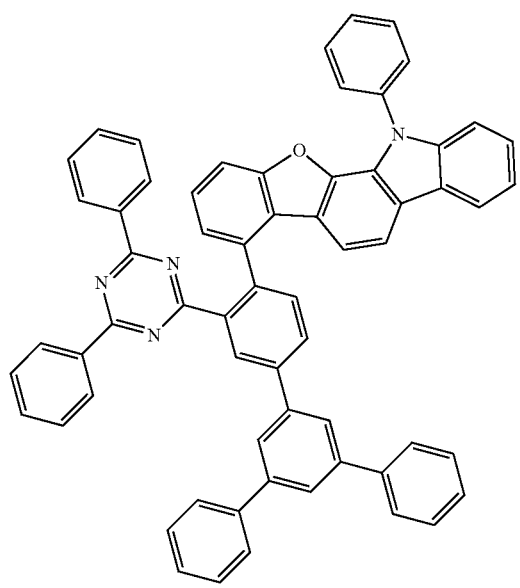
769
1538
-continued
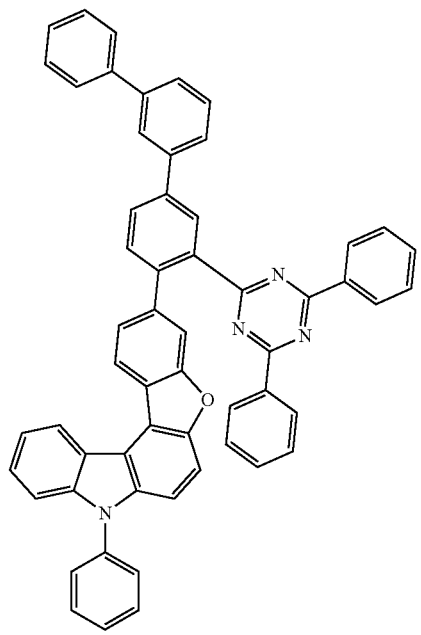
771
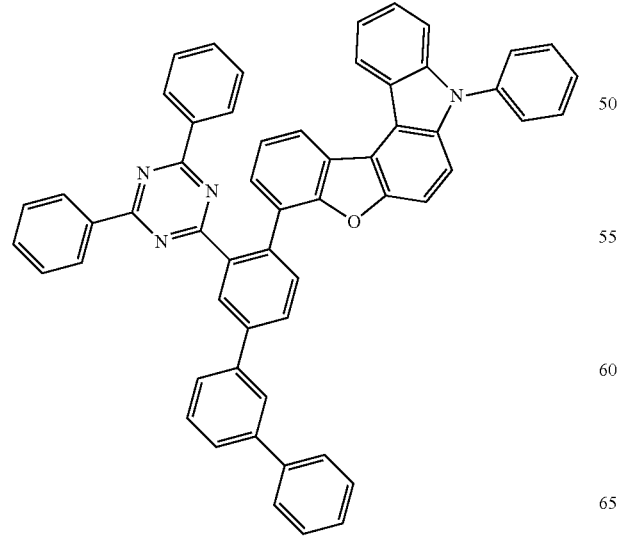
770
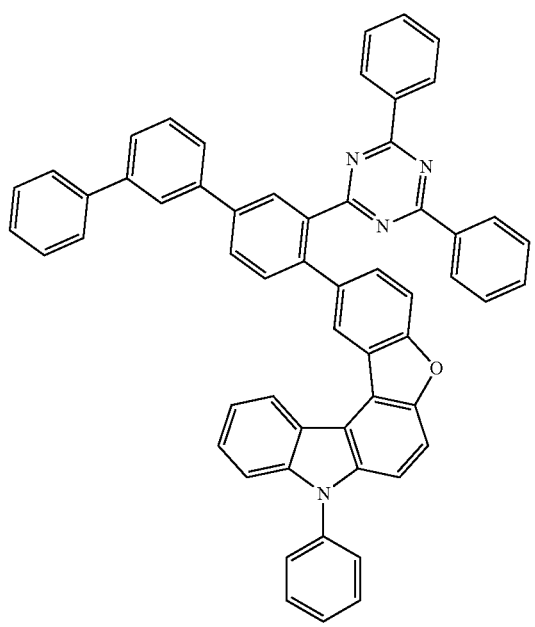
772

1539
-continued
773
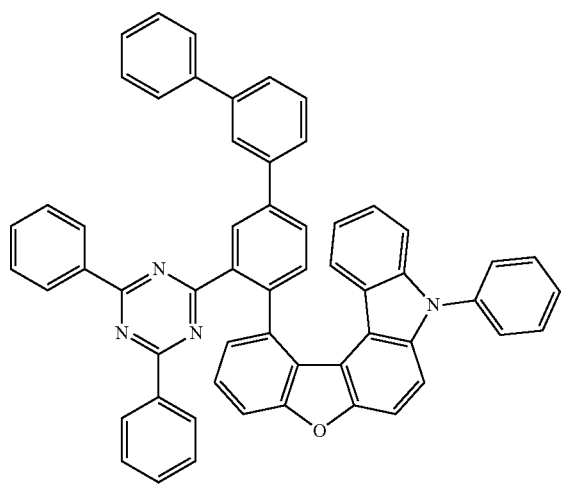
774
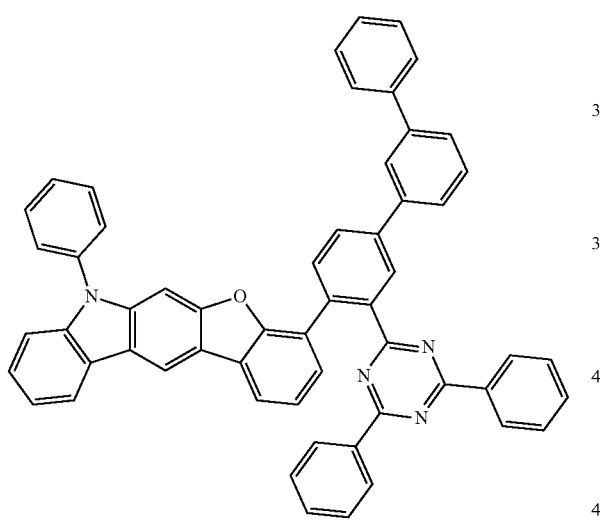
775
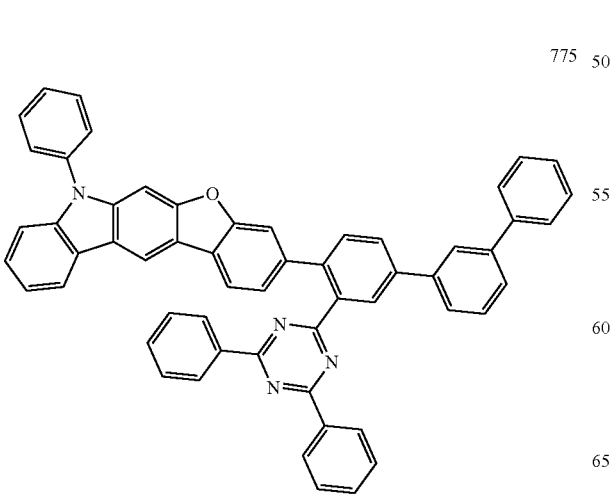
1540
-continued
776
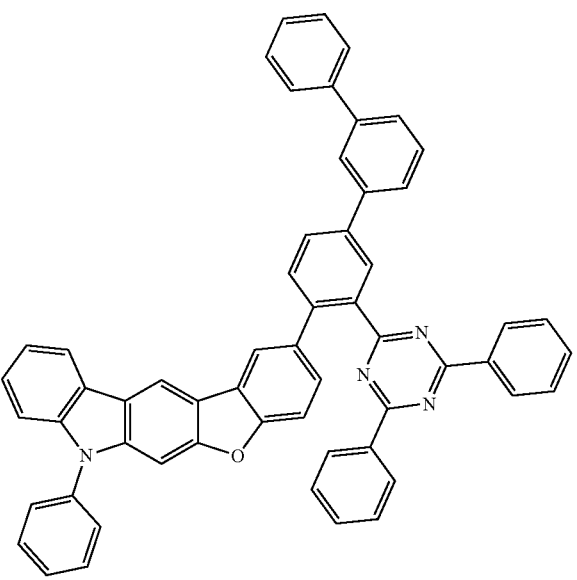
777
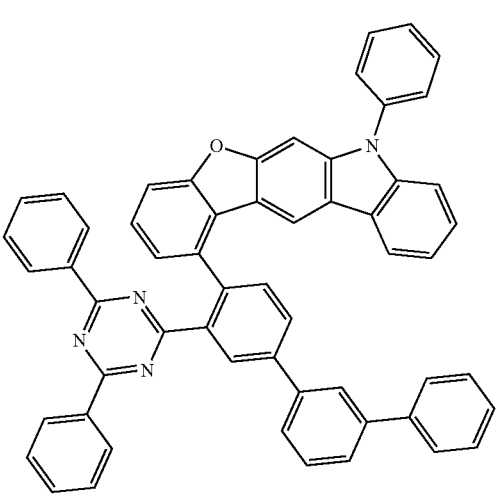

1541
-continued
778
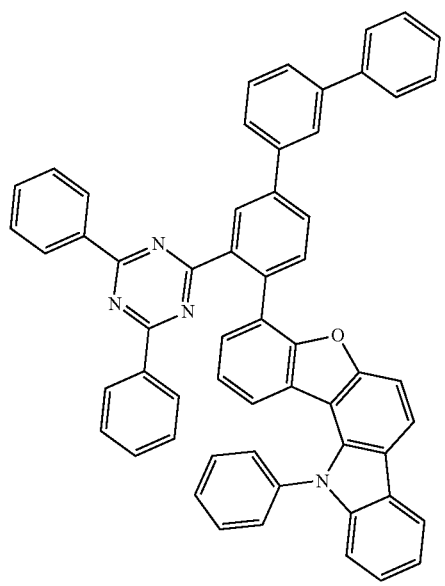
1542
-continued
780
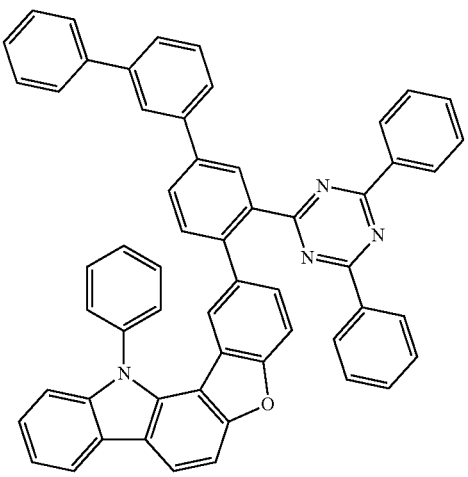
779
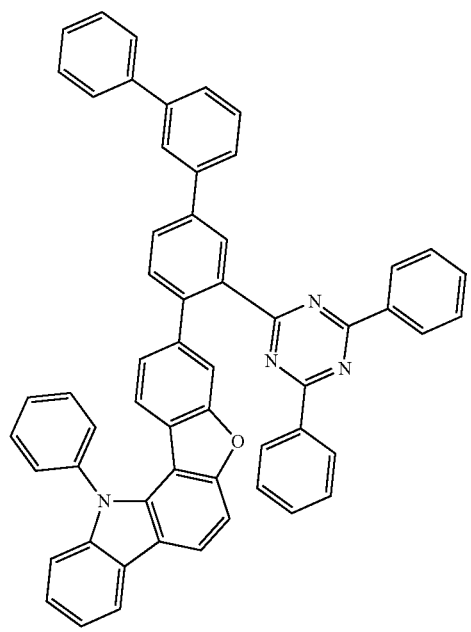
781
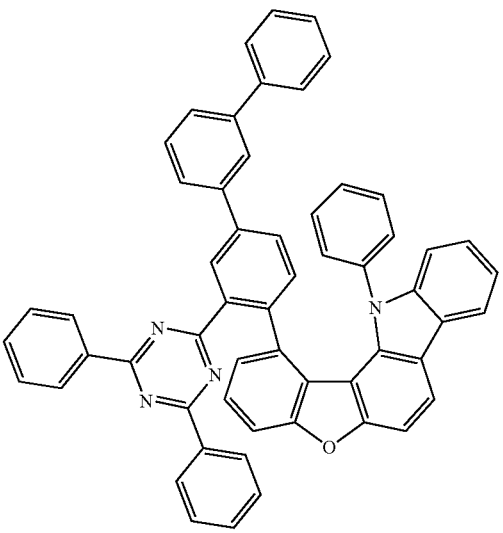

1543
-continued
1544
-continued
782
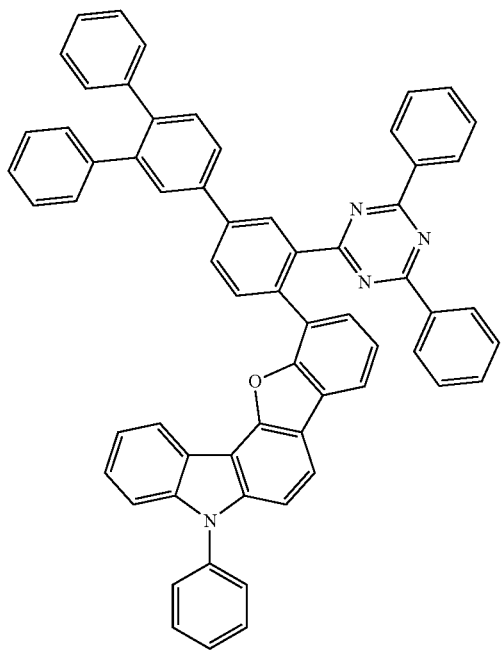
784
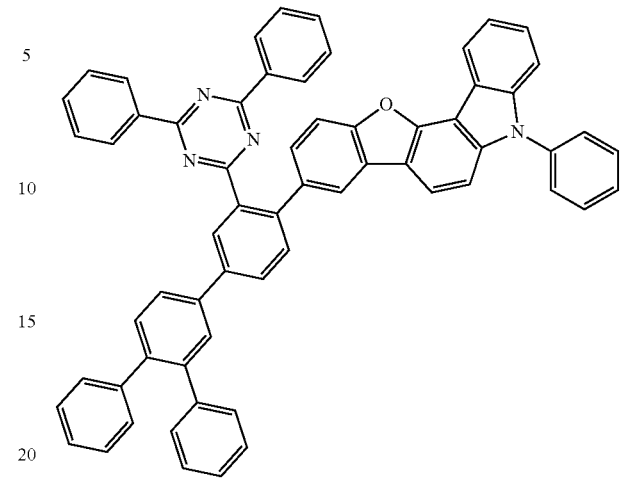
785
783
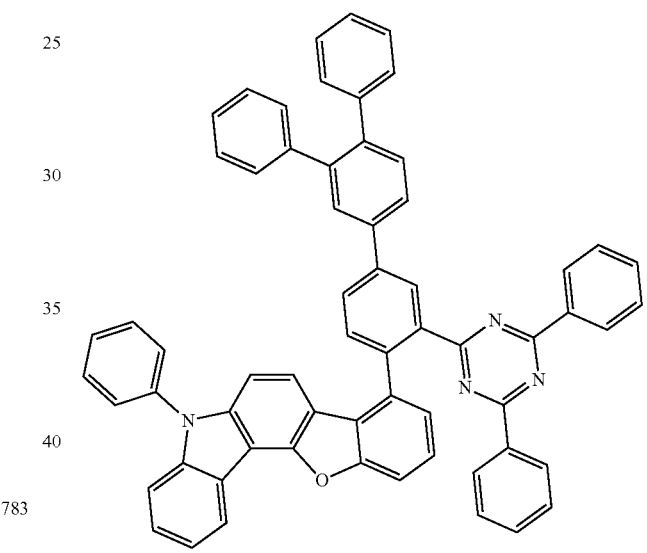
786
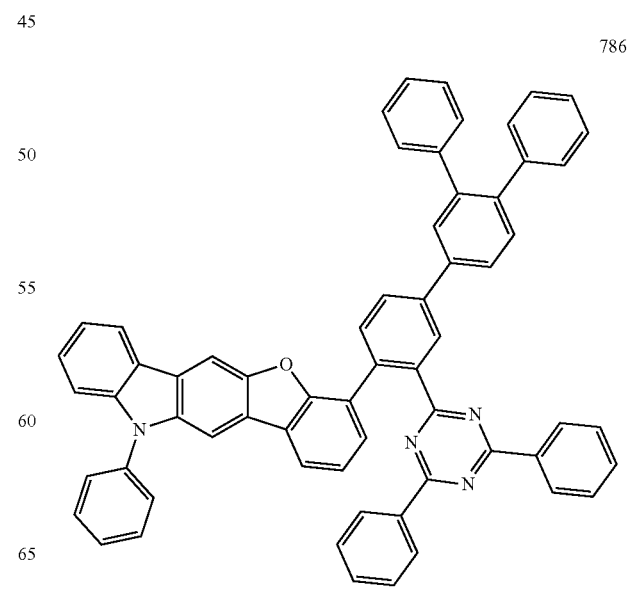

1545
-continued
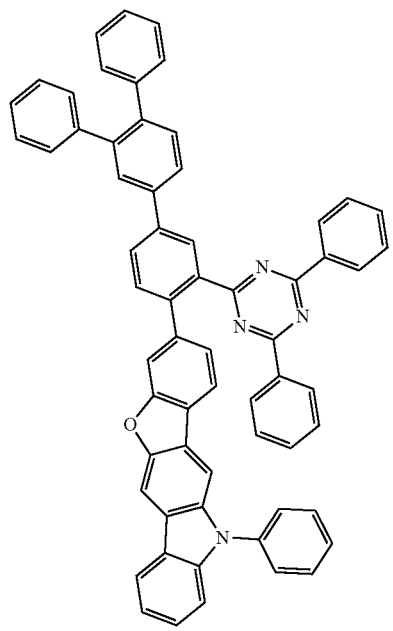
1546
-continued
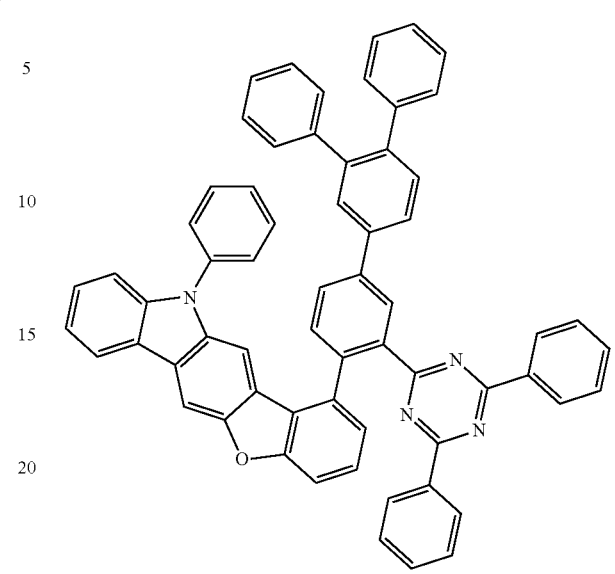
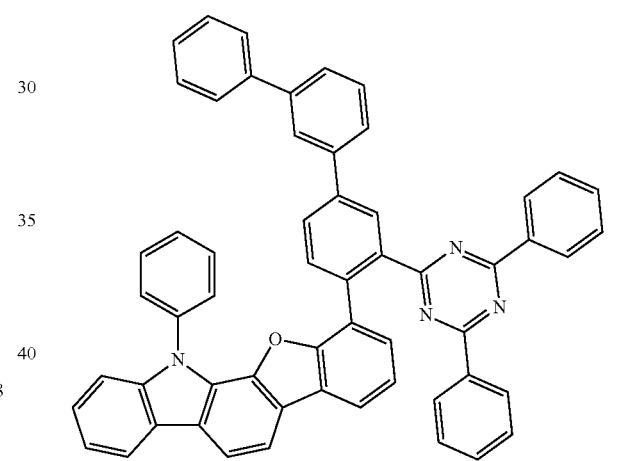
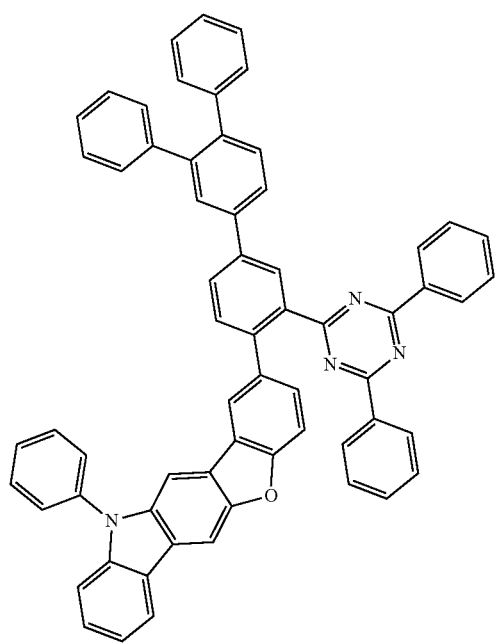
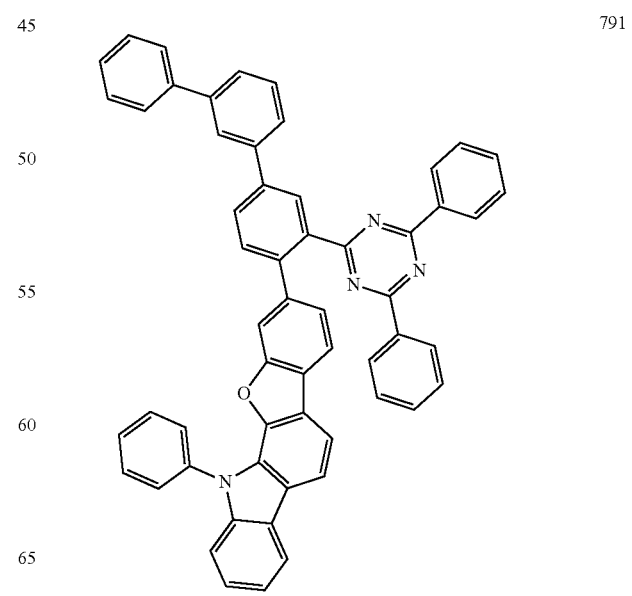

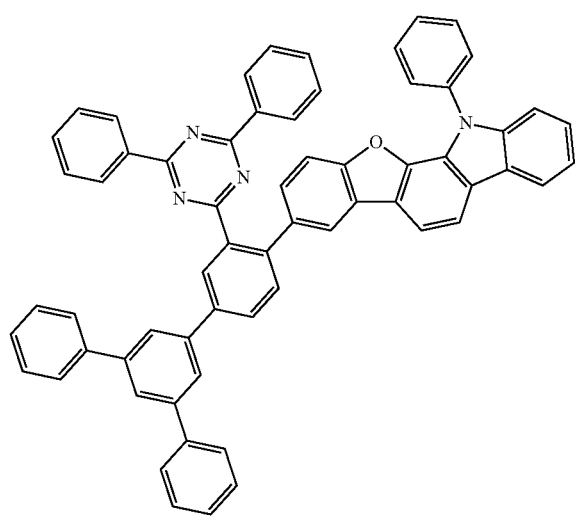
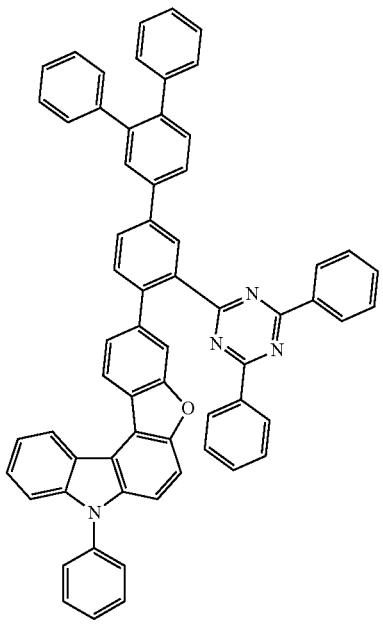
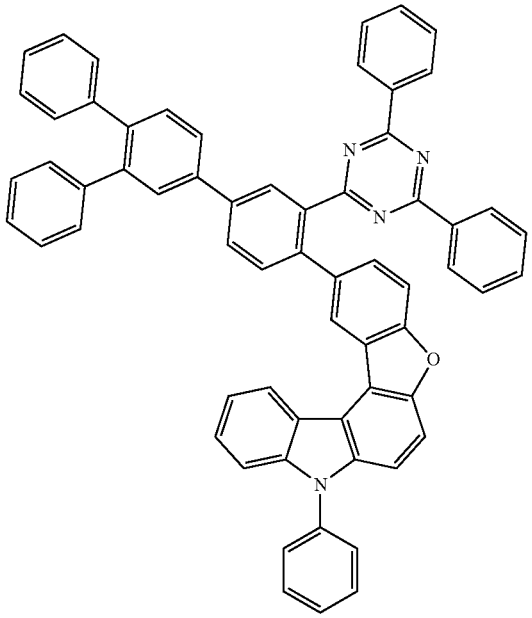

1549
-continued
797
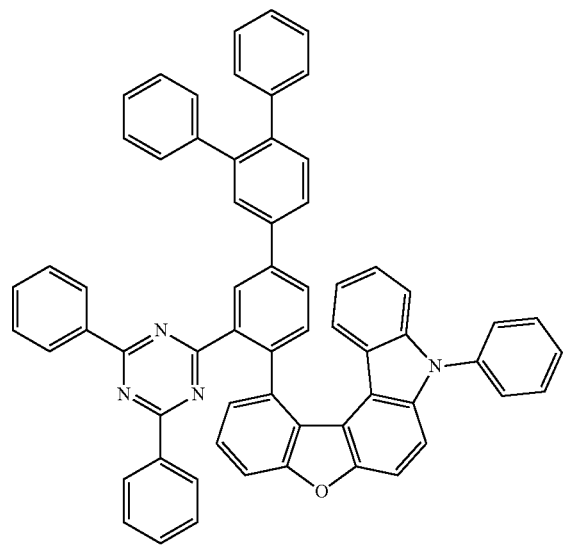
798
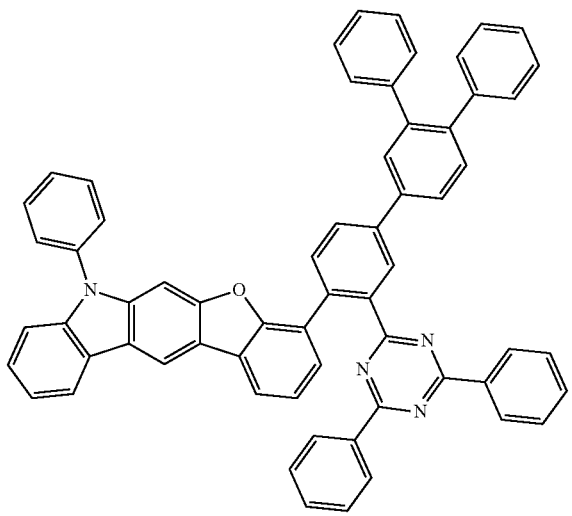
799
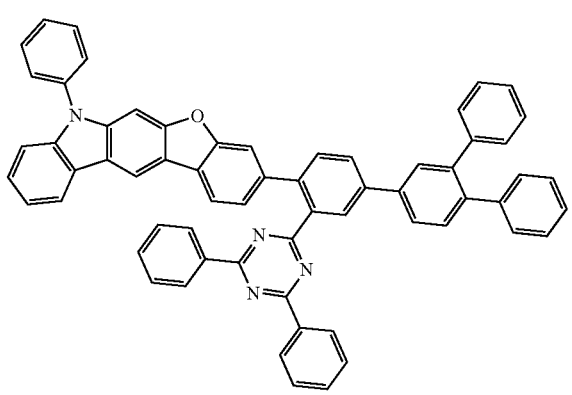
1550
-continued
800
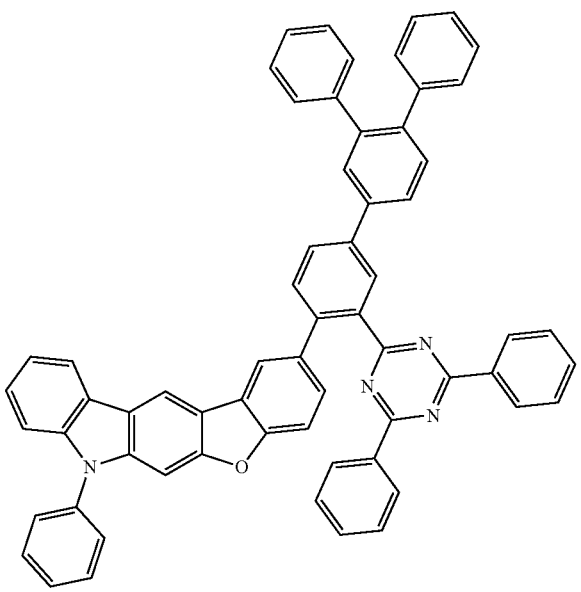
801
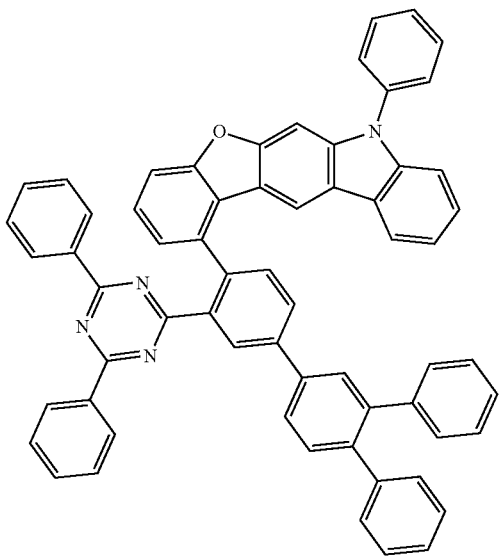

1551
-continued
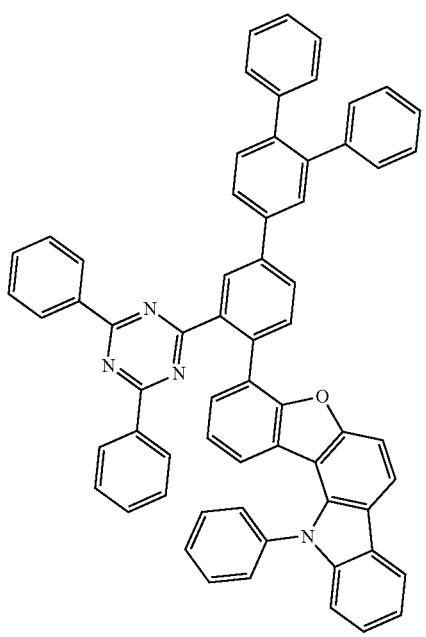
802
1552
-continued
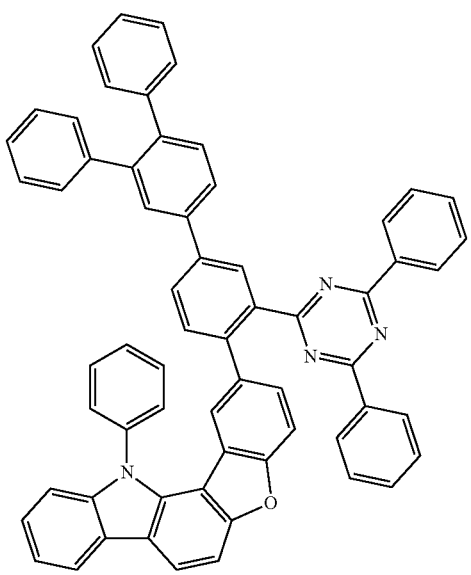
804
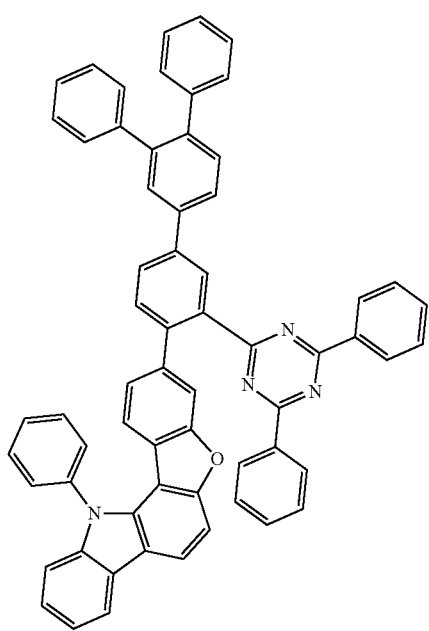
803
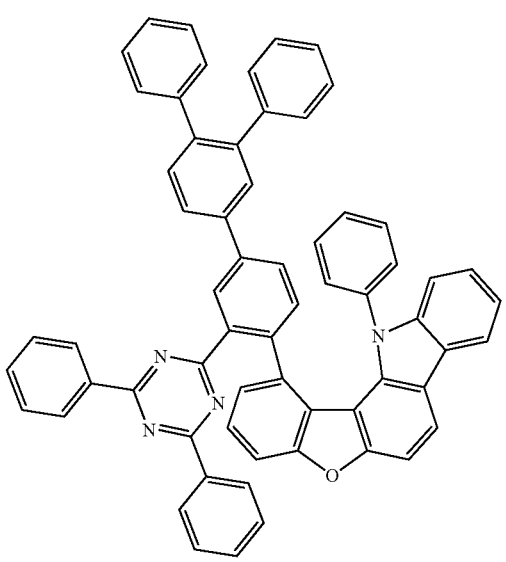
805

1553
-continued
806
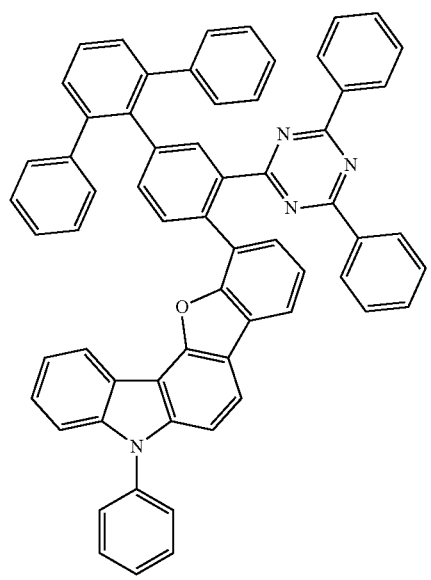
807
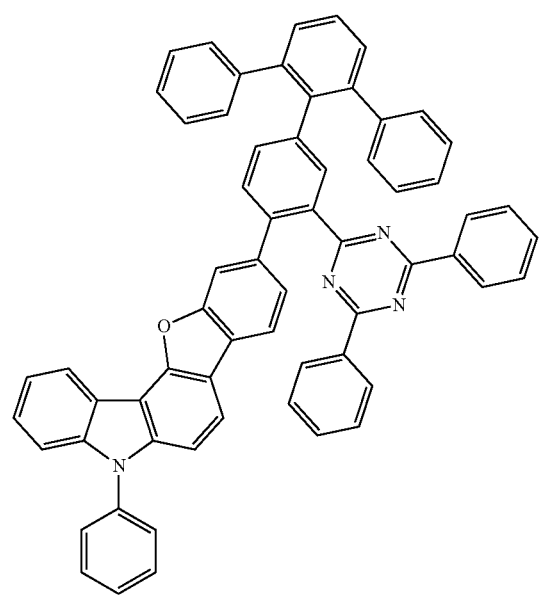
808
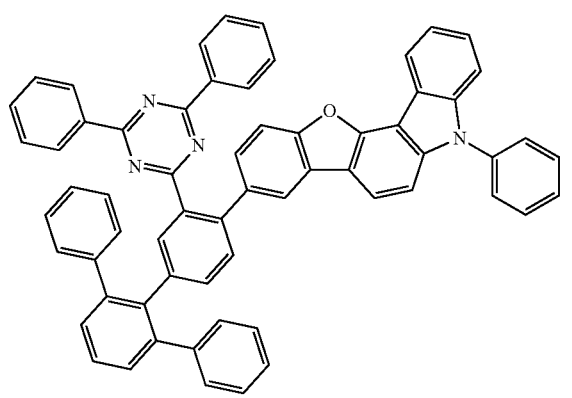
1554
-continued
809
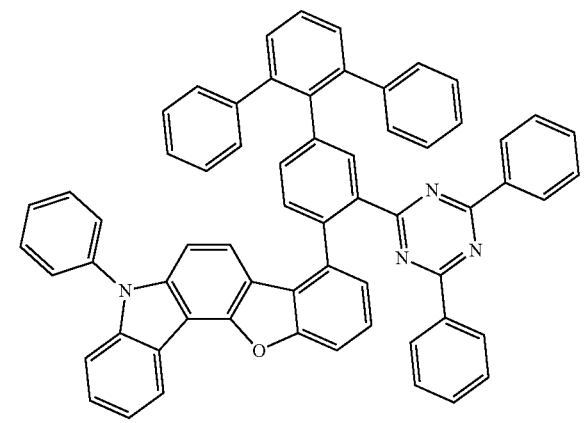
810
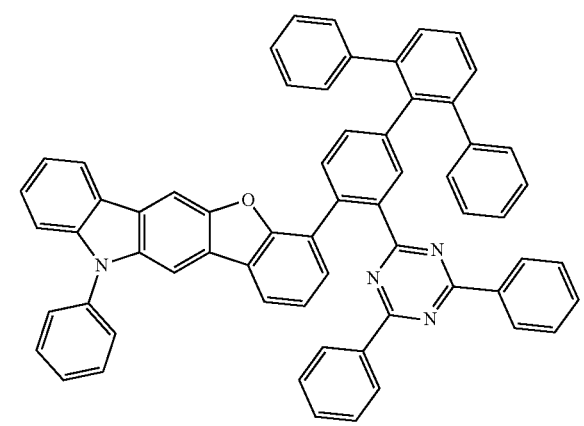
811
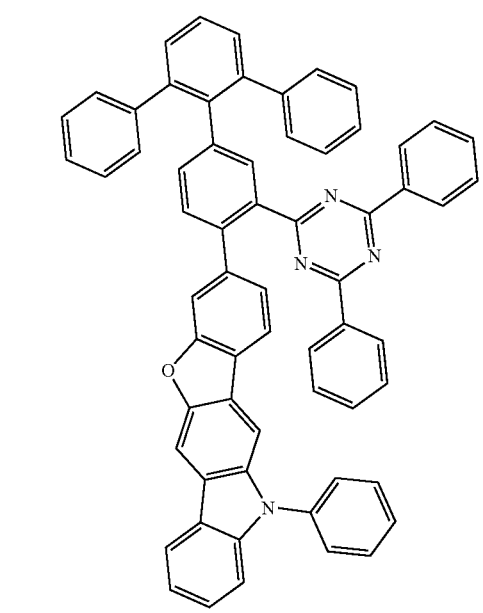

-continued
812
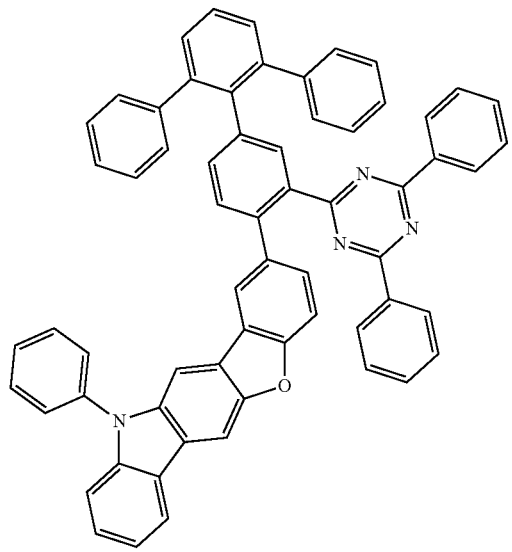
813
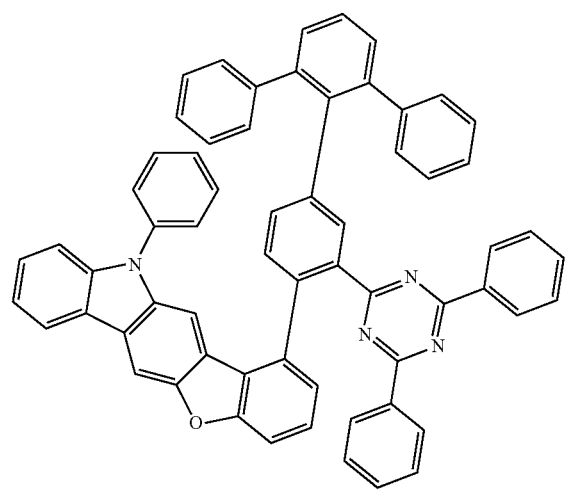
814
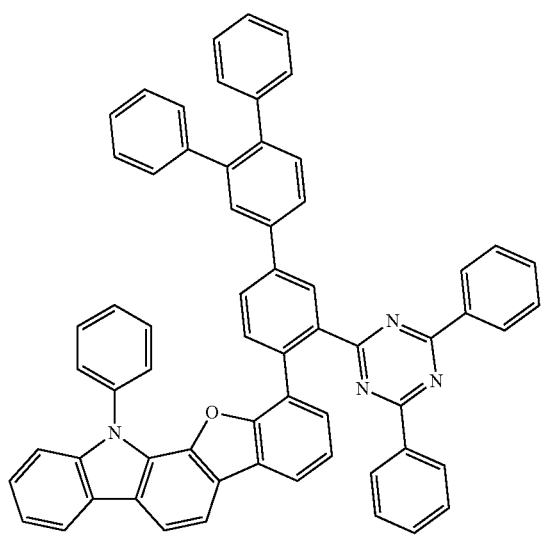
-continued
815
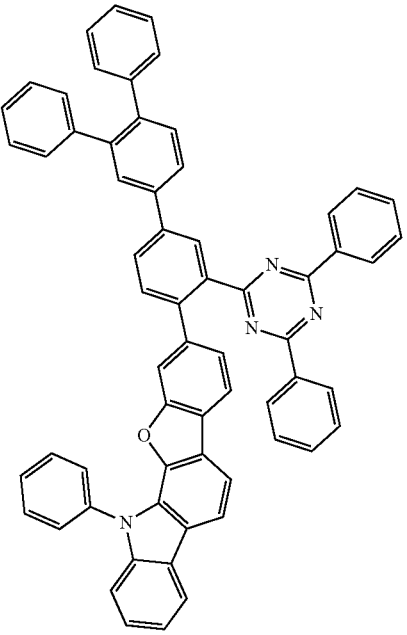
816
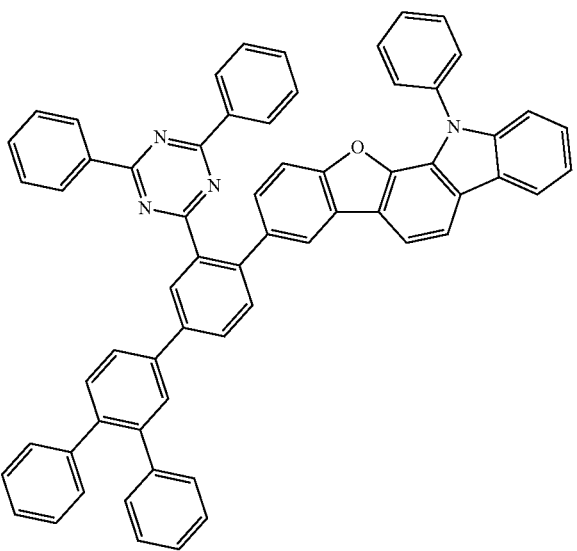

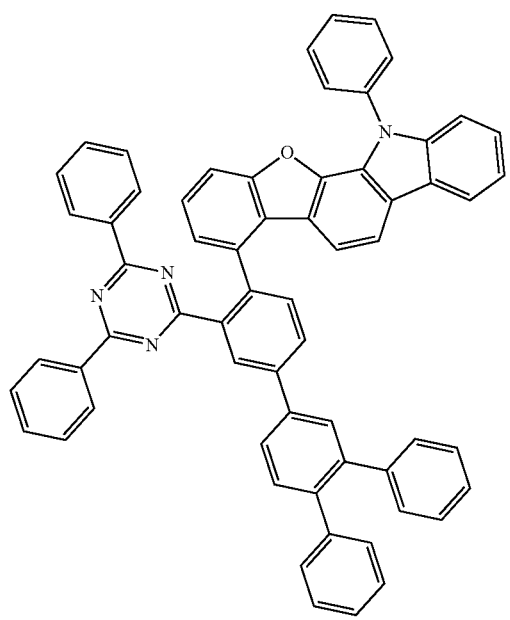
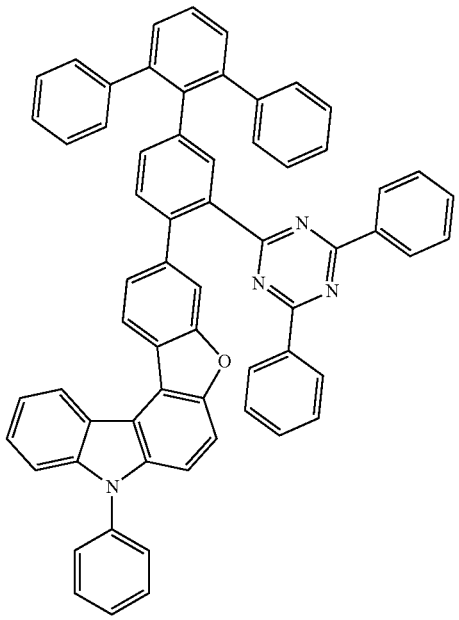
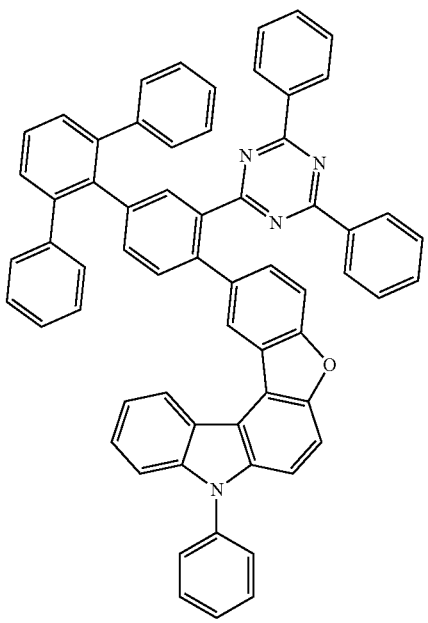

1559
-continued
821
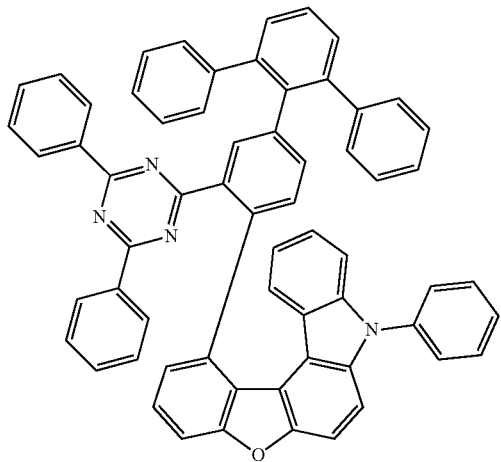
822
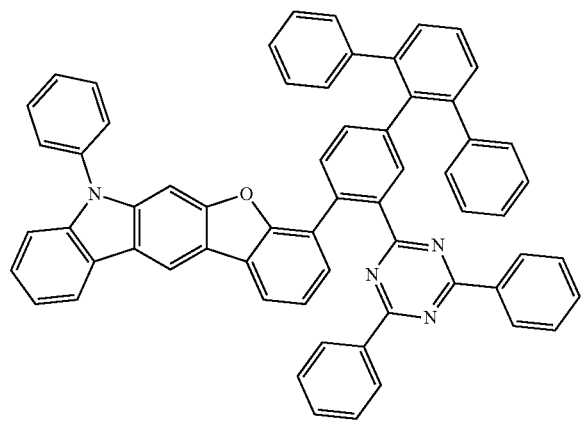
823
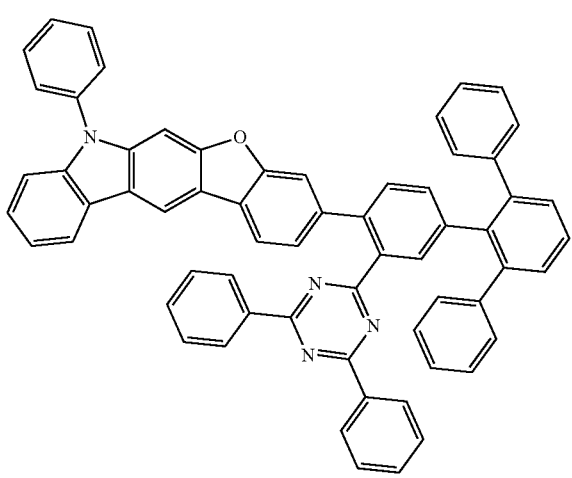
1560
-continued
824
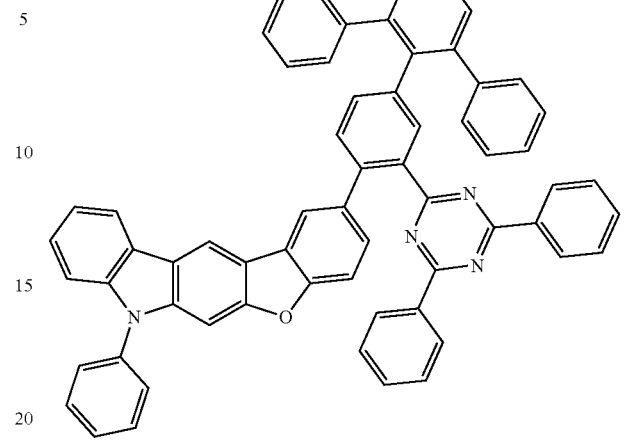
825
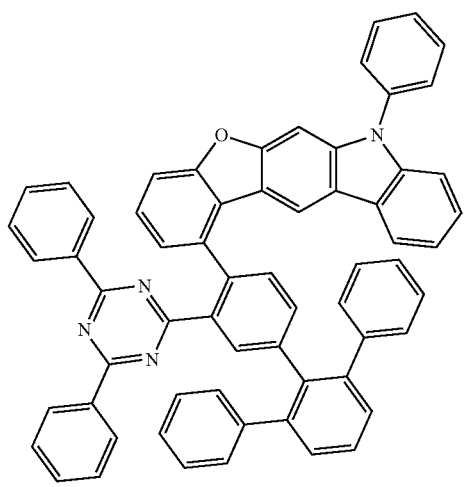
826
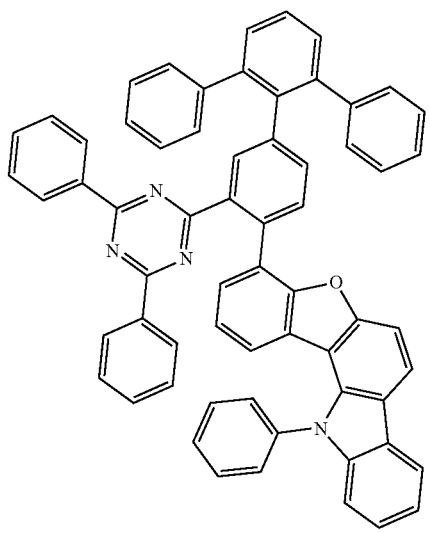

| 1561 -continued | 1562 -continued |
|---|---|
| 827 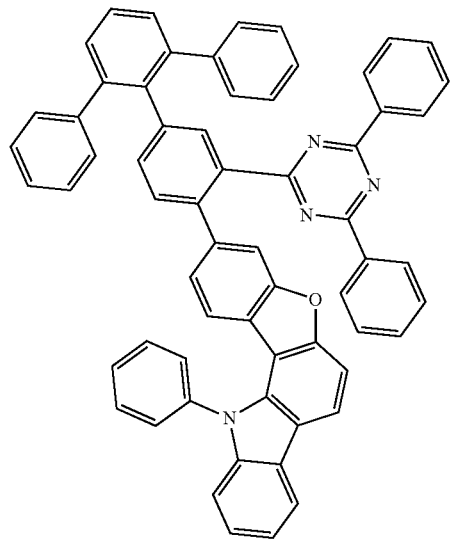 | 830 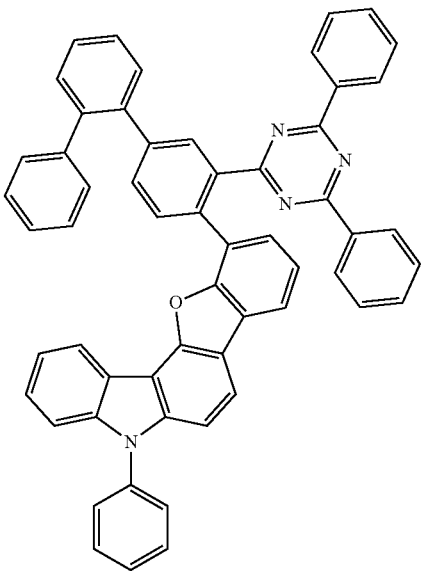 |
| 828 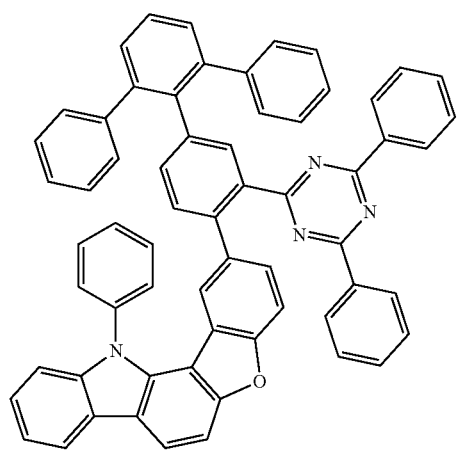 | 831 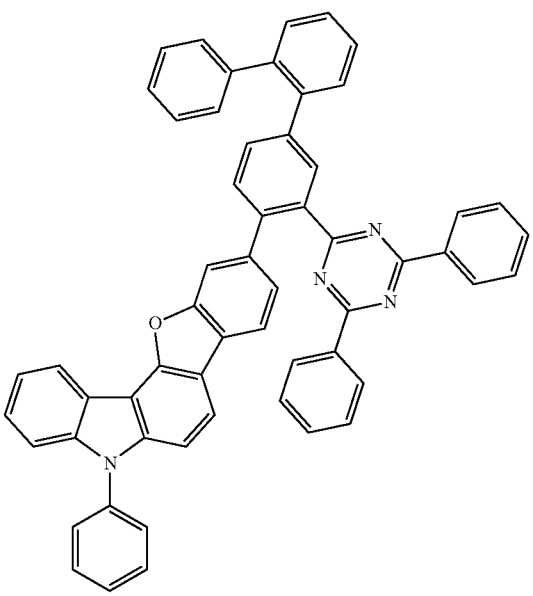 |
| 829 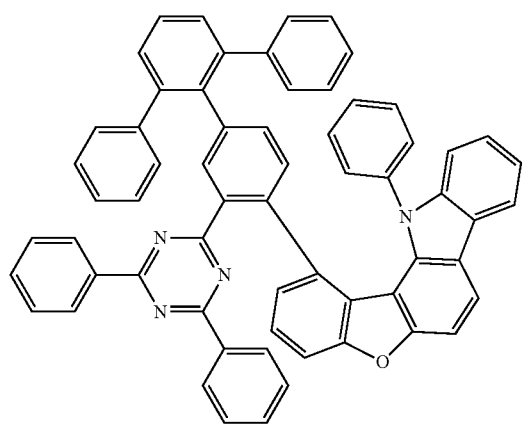 | 832 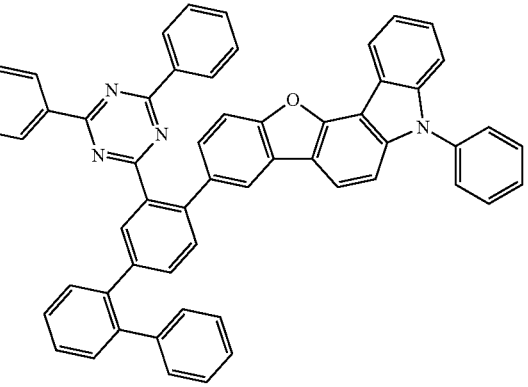 |

1563 -continued
833
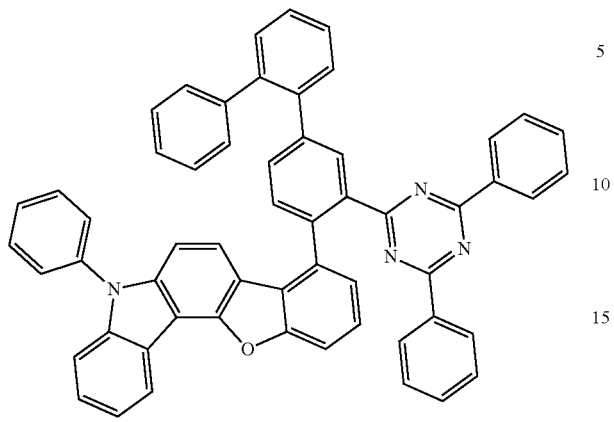
834
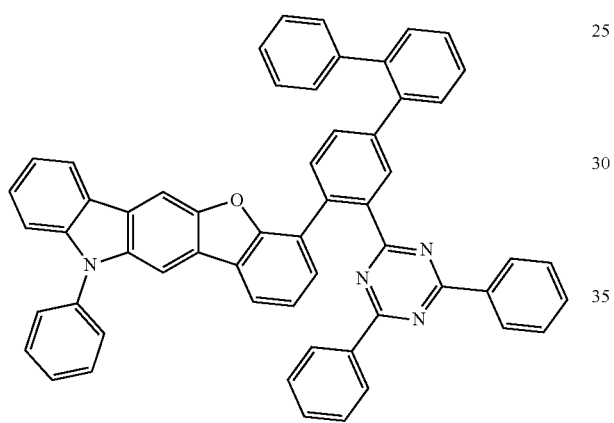
835
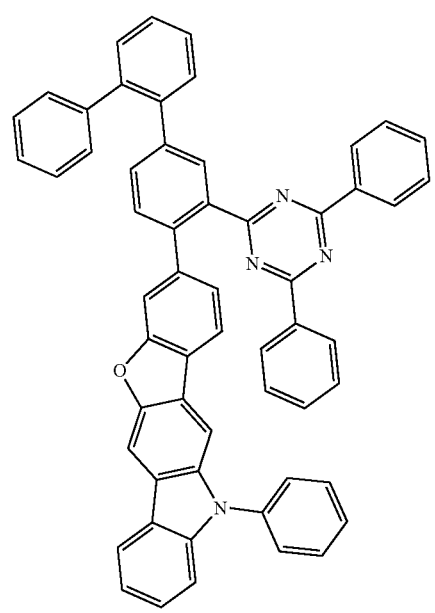
1564 -continued
836
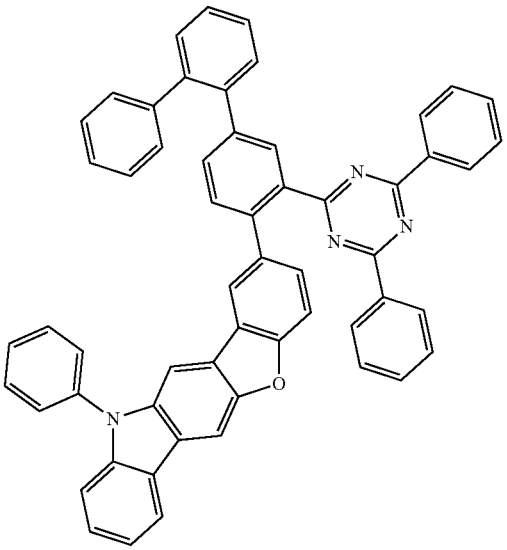
837
838
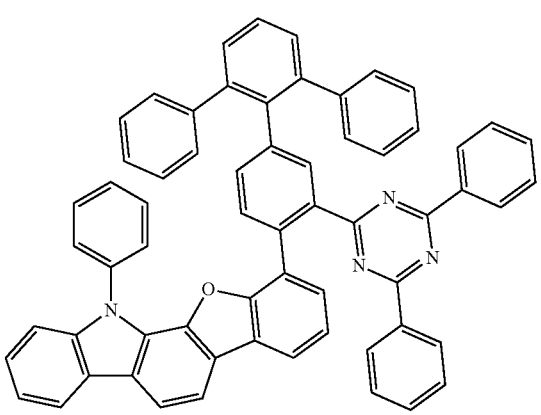

1565
-continued
839
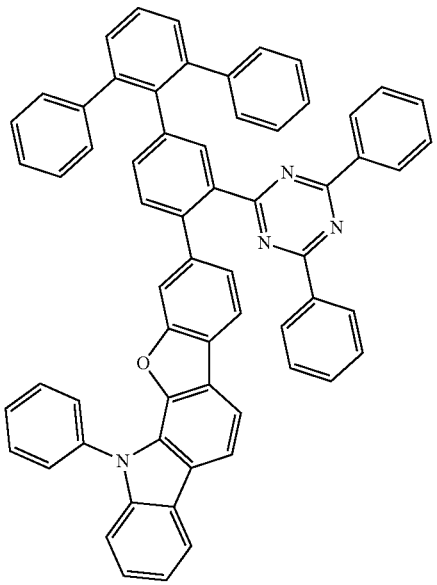
840
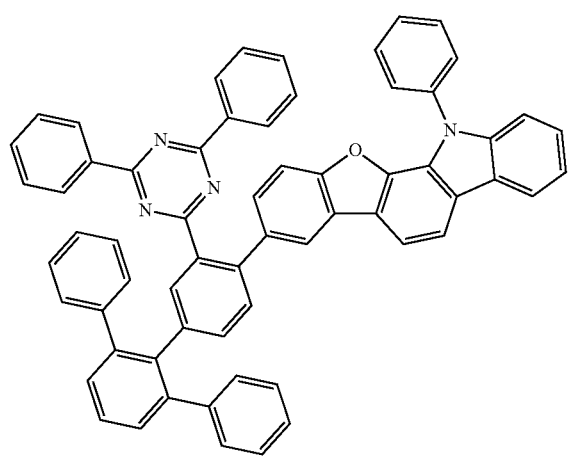
841
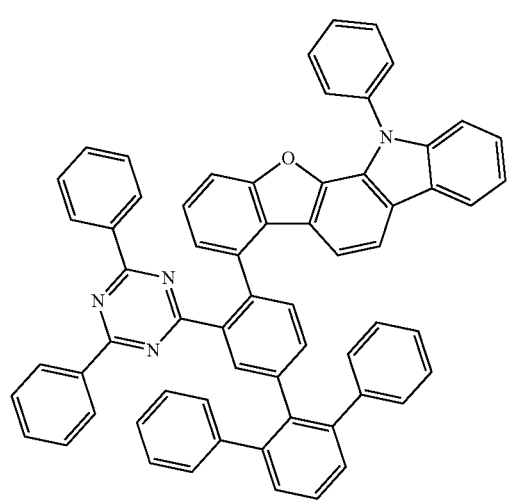
1566
-continued
842
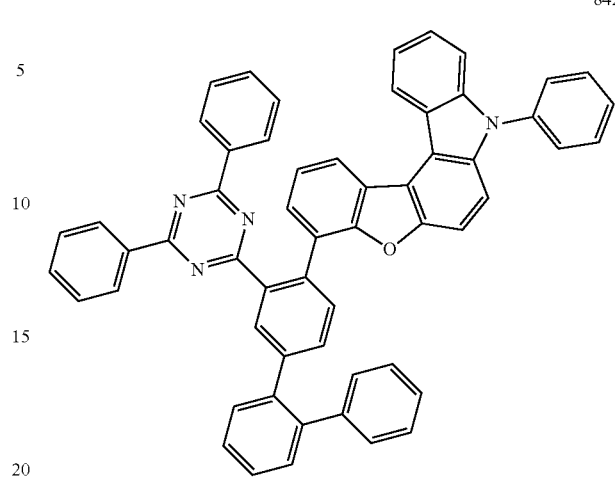
843
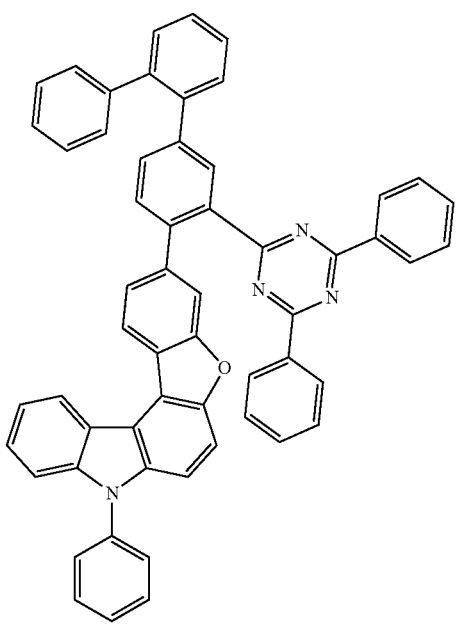

844
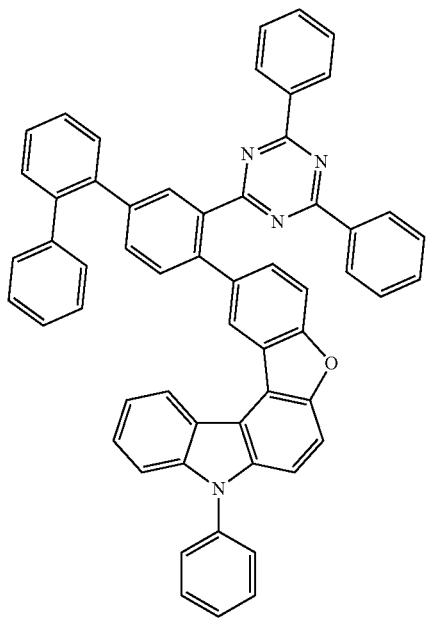
845
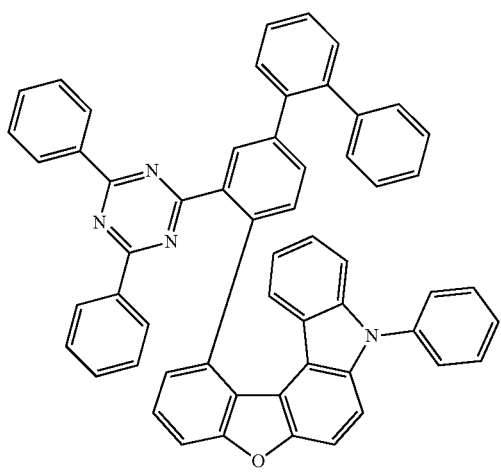
846
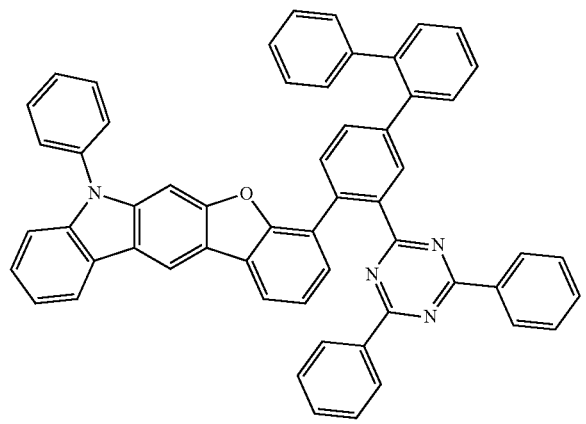
847
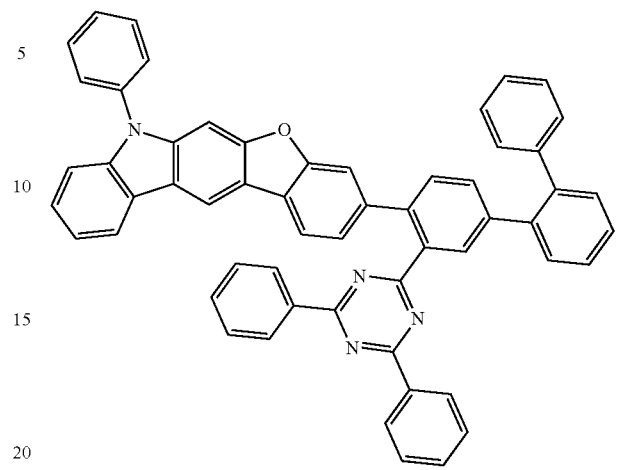
848
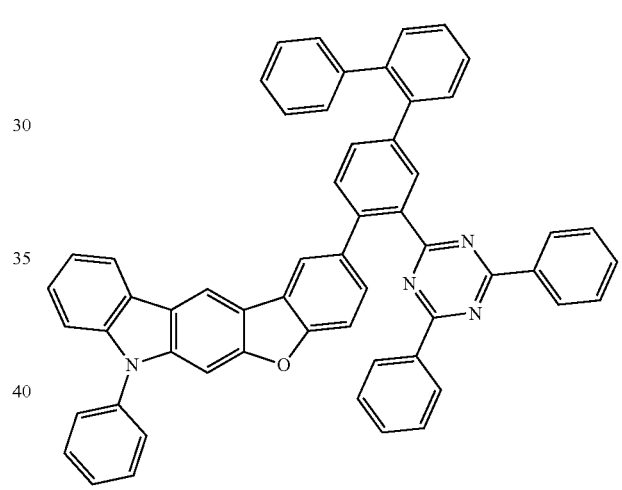
849
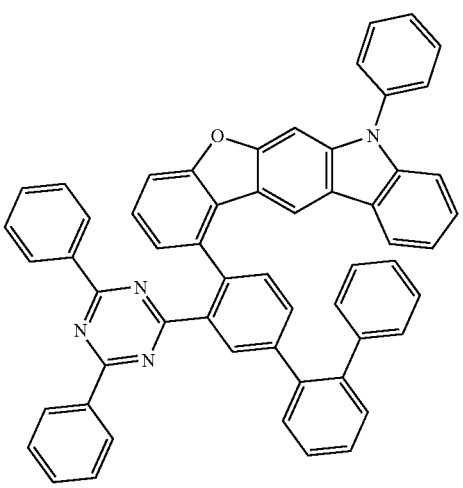

1569
-continued
850
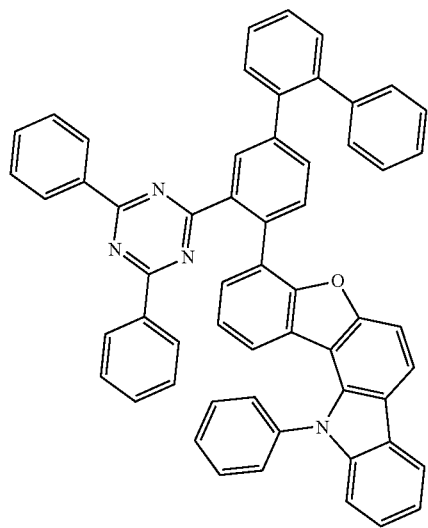
851
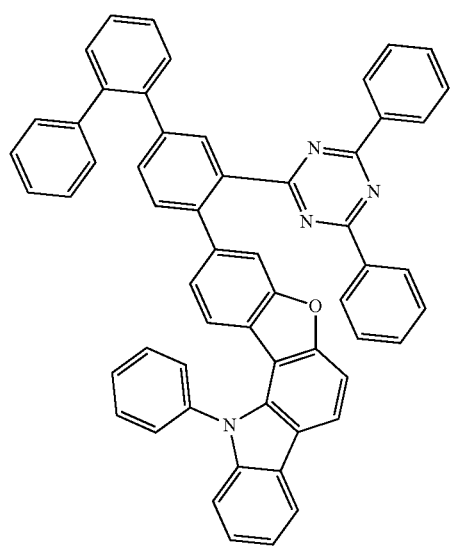
852
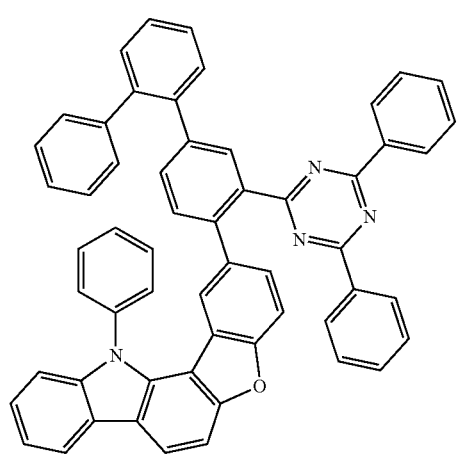
1570
-continued
853
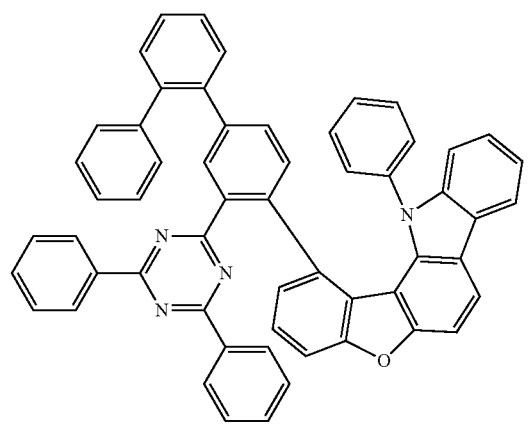
854
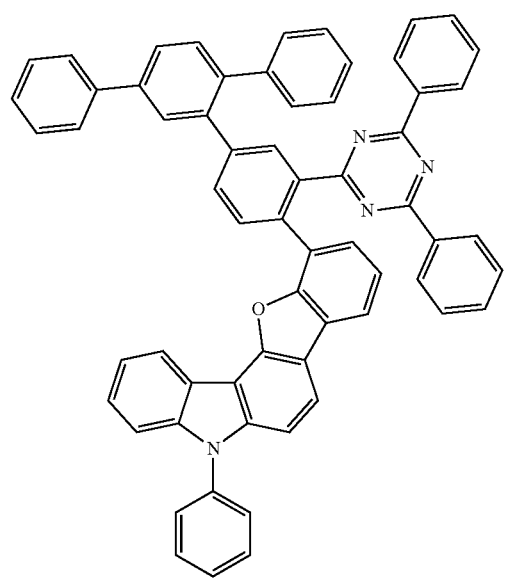

1571
-continued
855
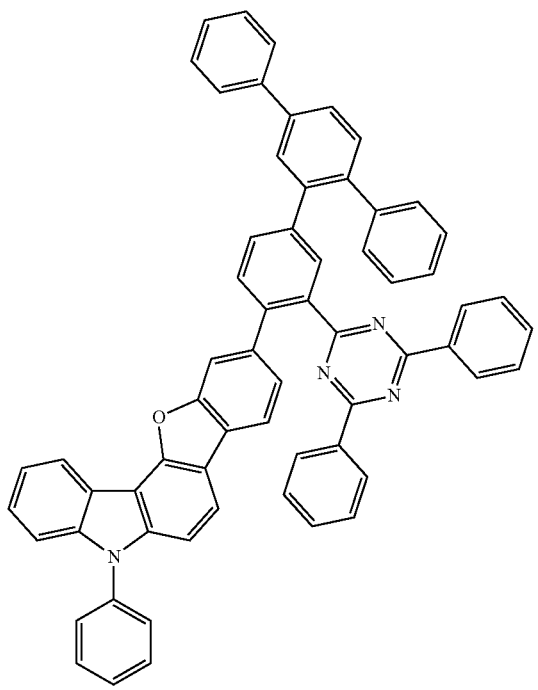
856
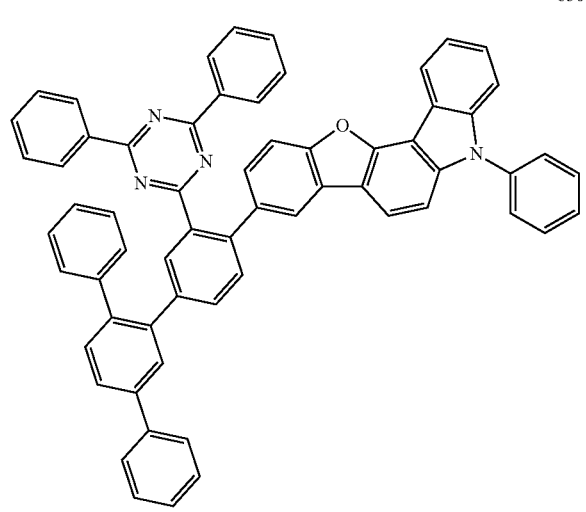
1572
-continued
857
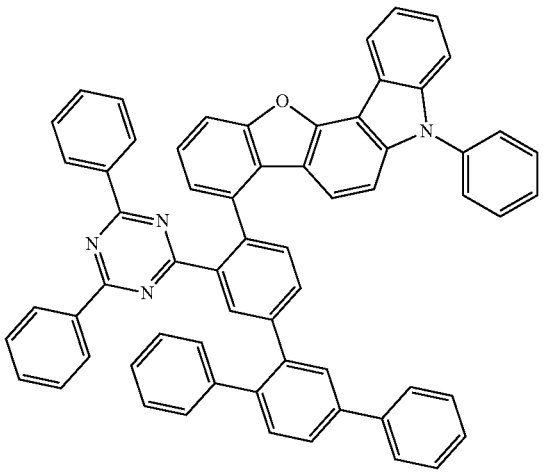
858
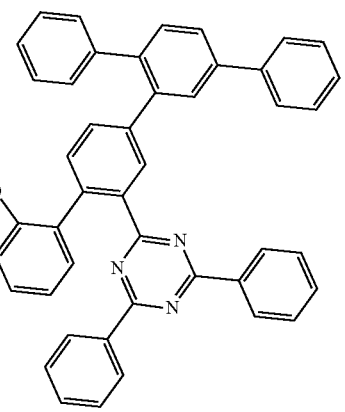
859
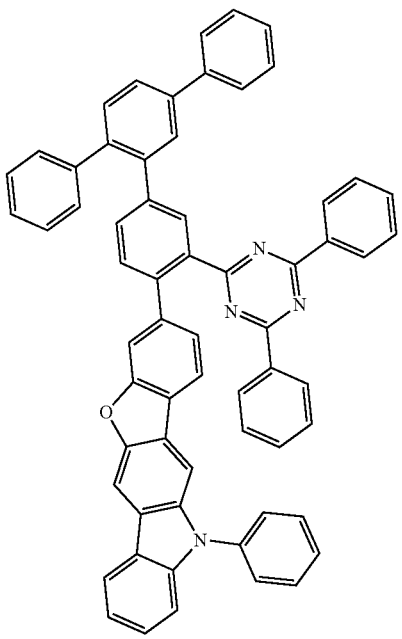

1573
-continued
860
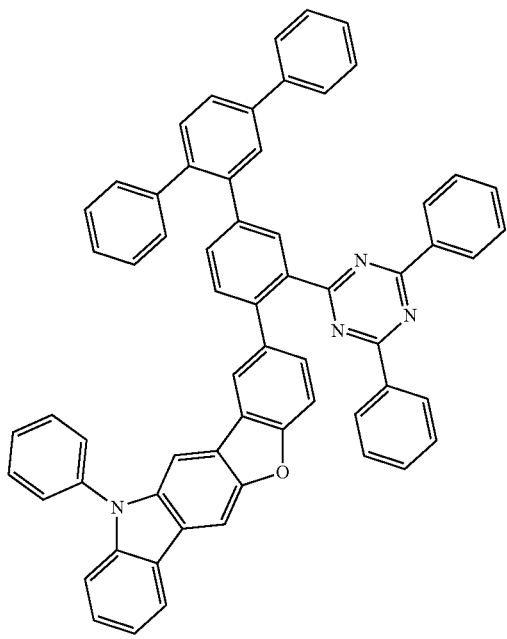
861
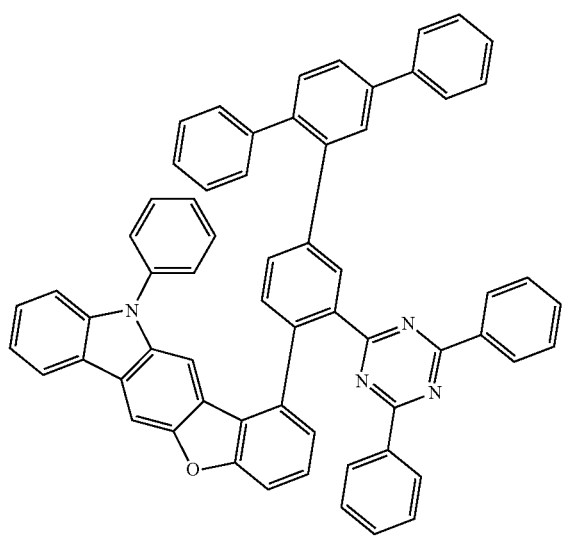
862
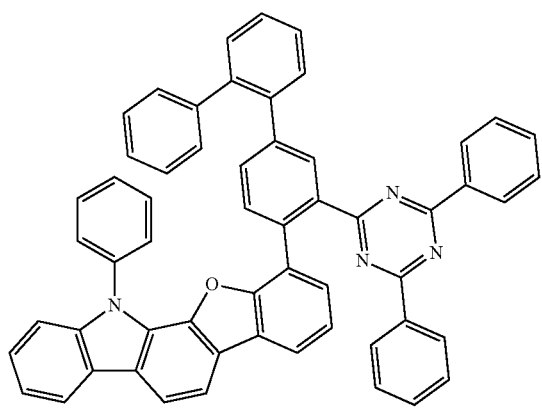
1574
-continued
863
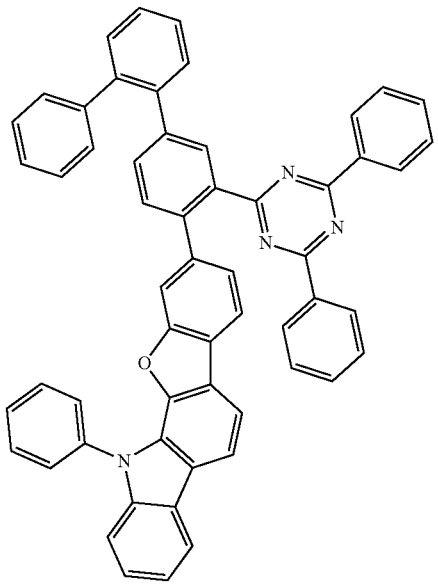
864
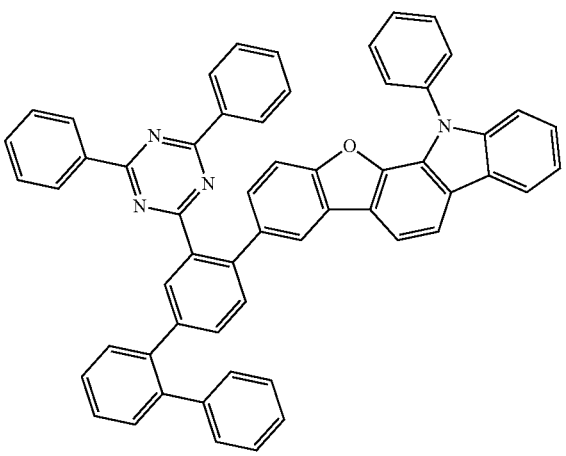
865
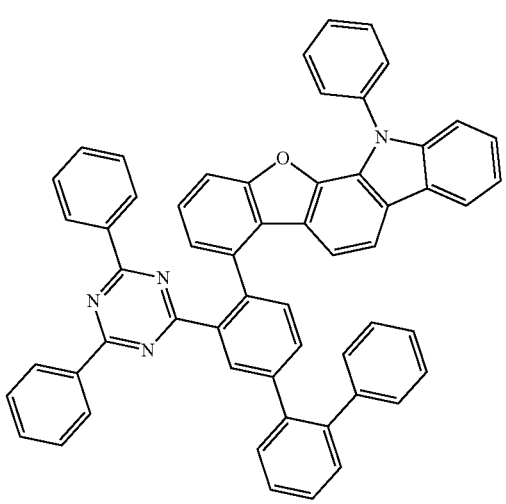

866
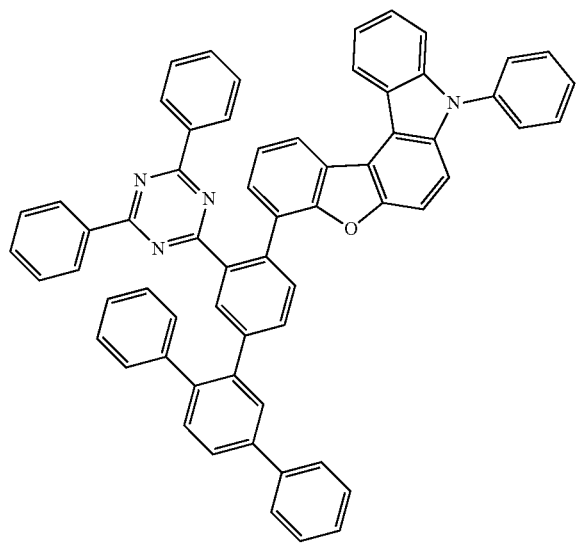
867
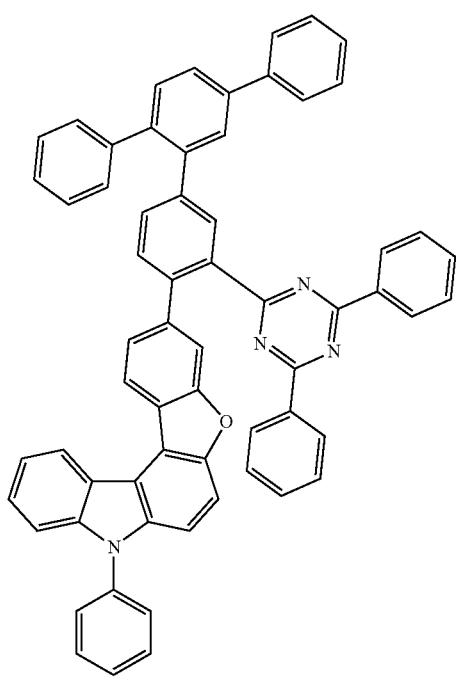
868
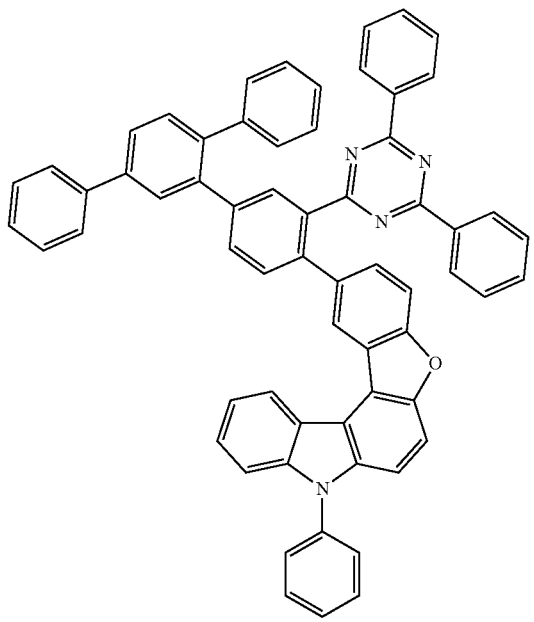
869
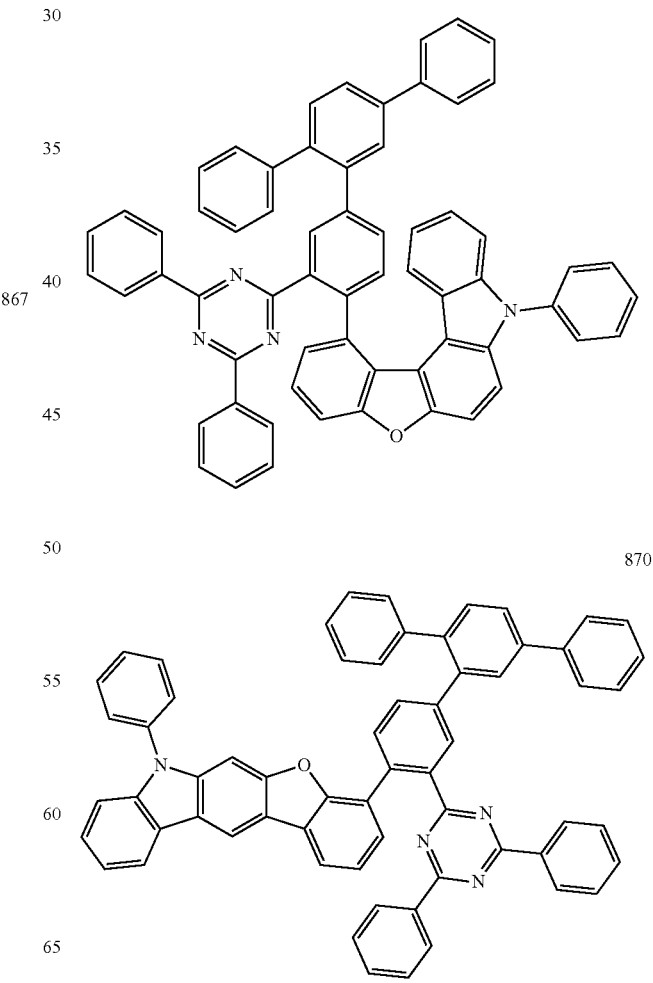
870

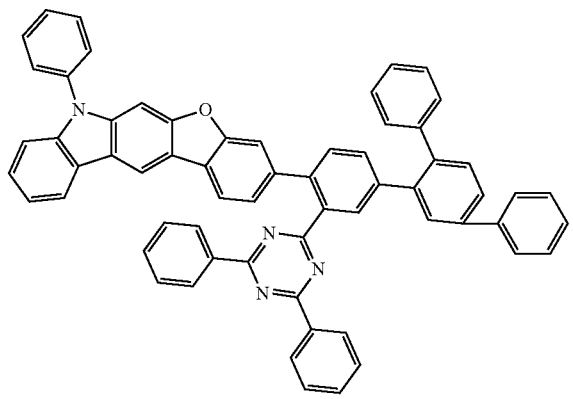
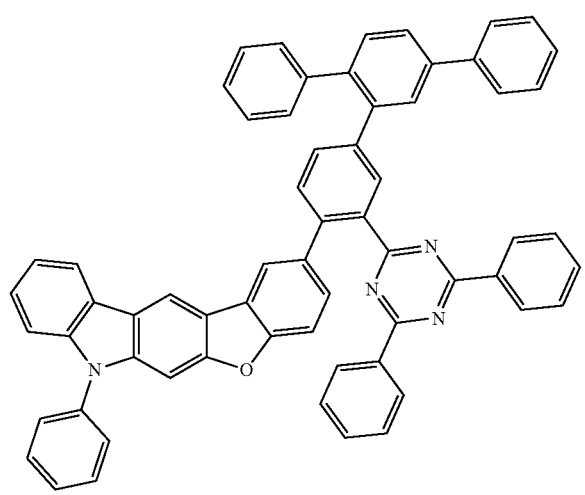
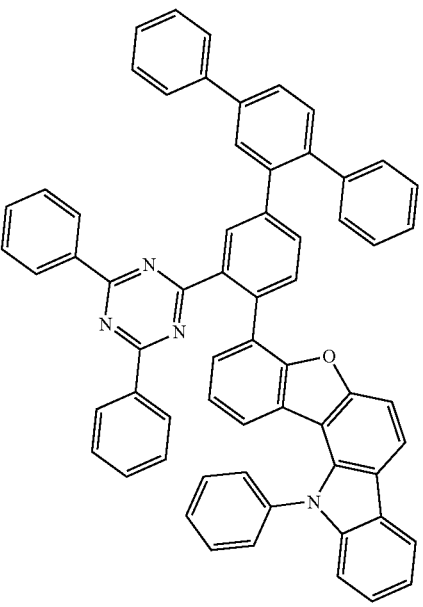
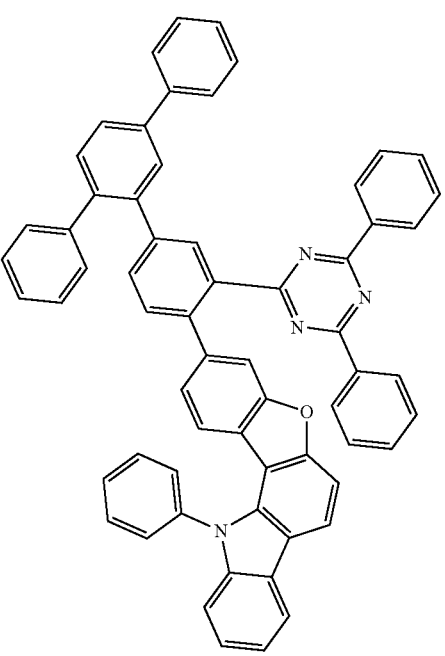

876 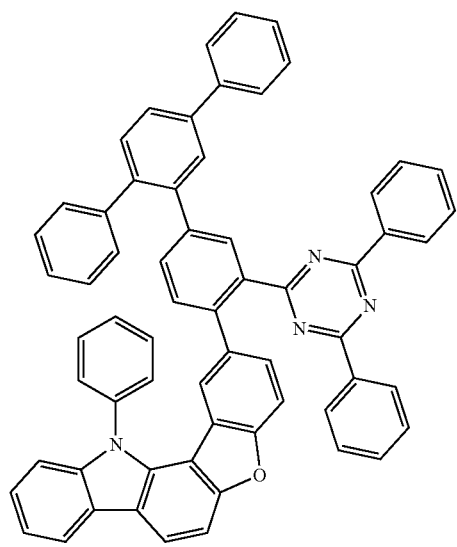
877 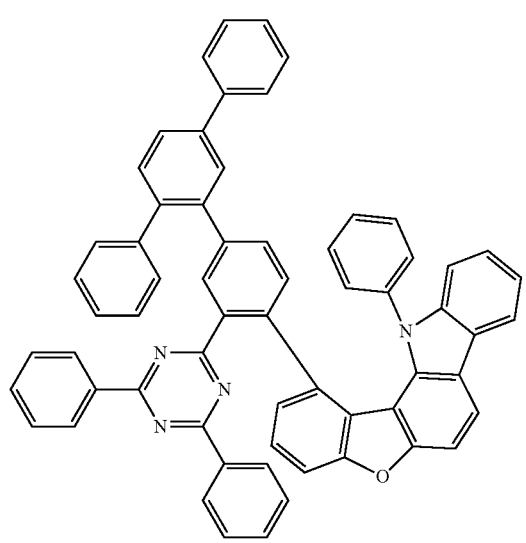
878 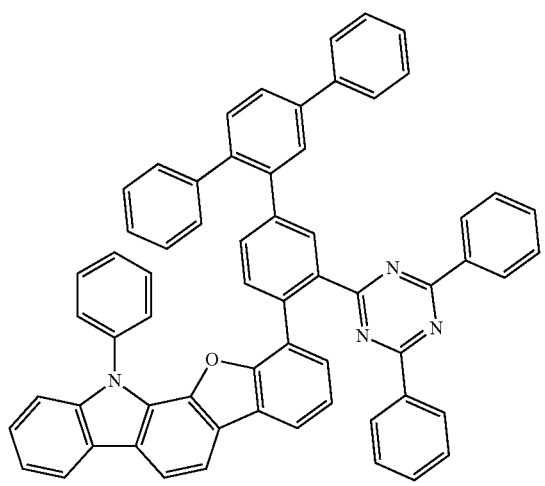
879 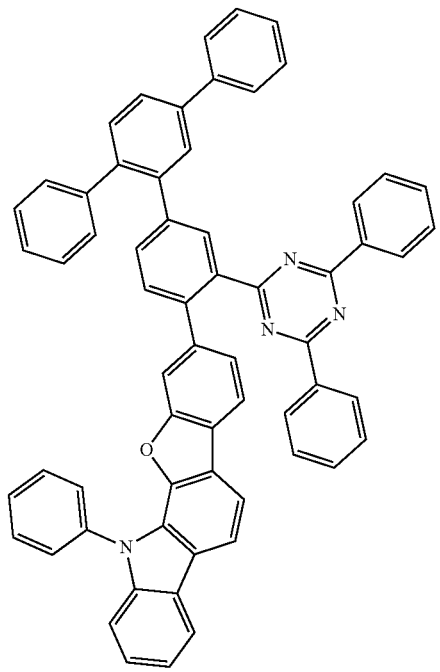
880 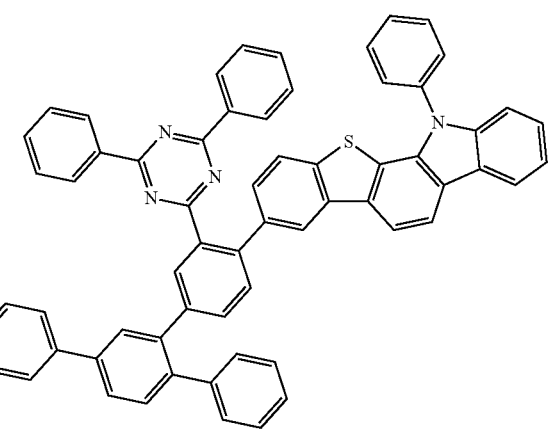

1581
-continued
881
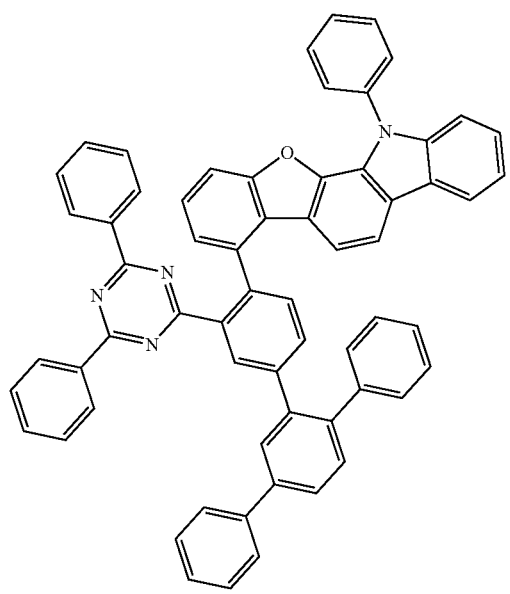
882
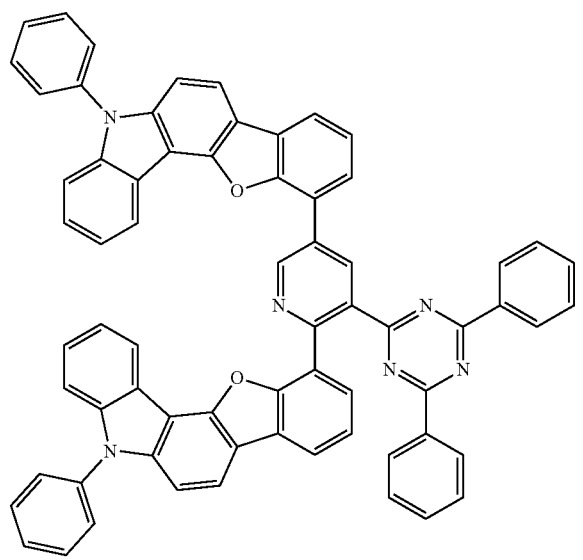
1582
-continued
883
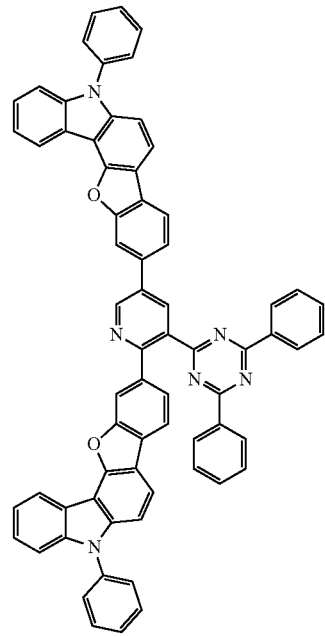
884
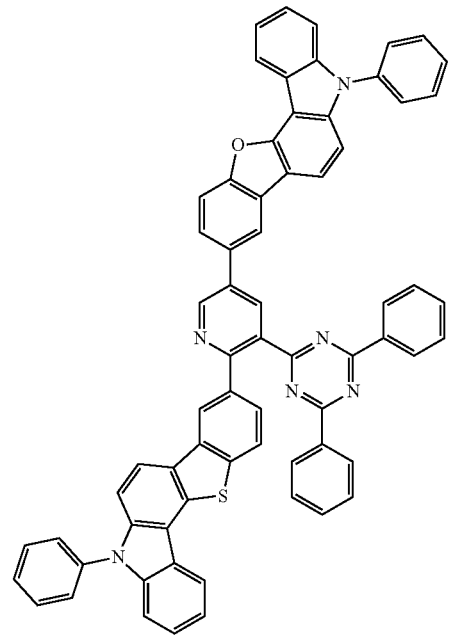

1583
-continued
885
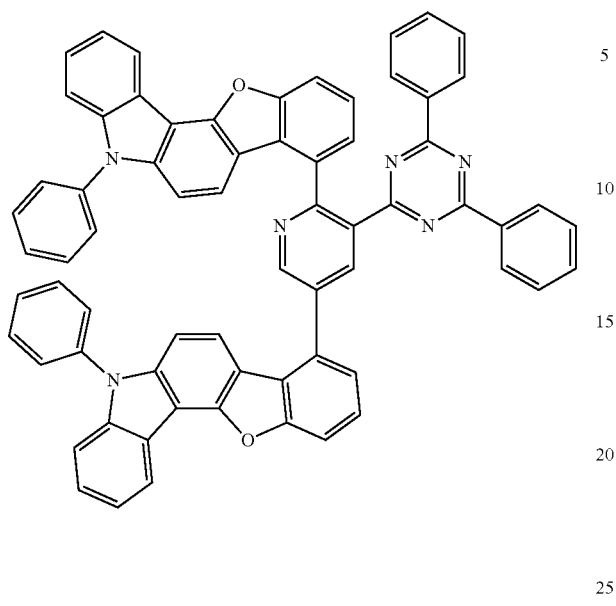
886
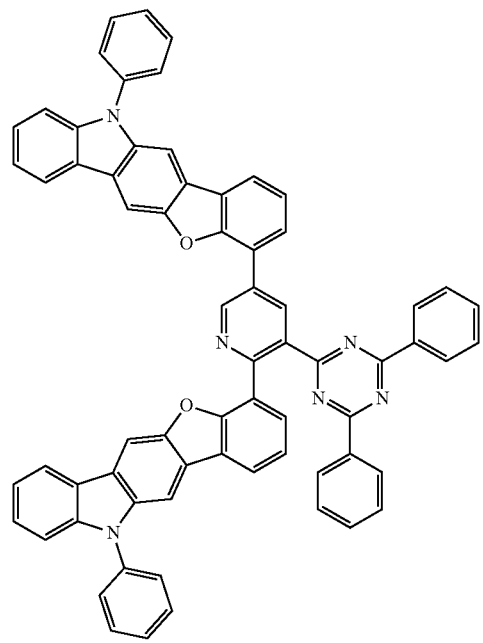
1584
-continued
887
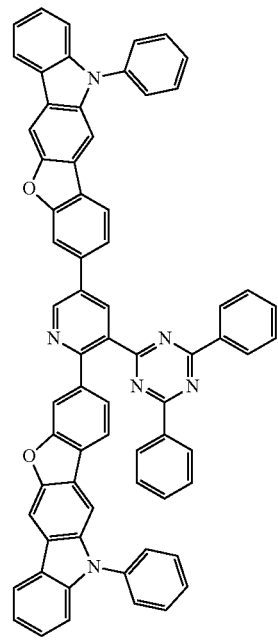
888
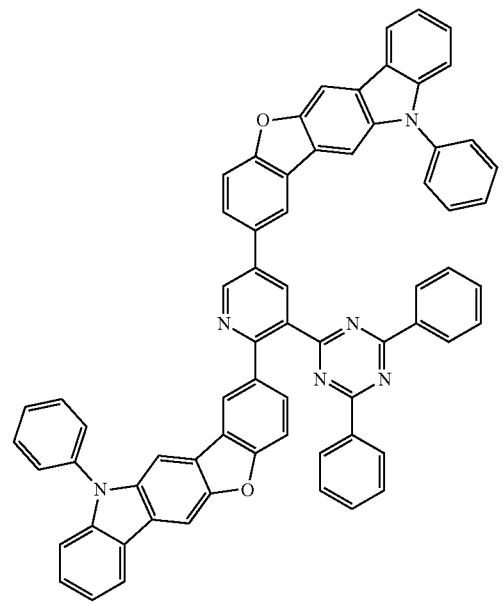

889
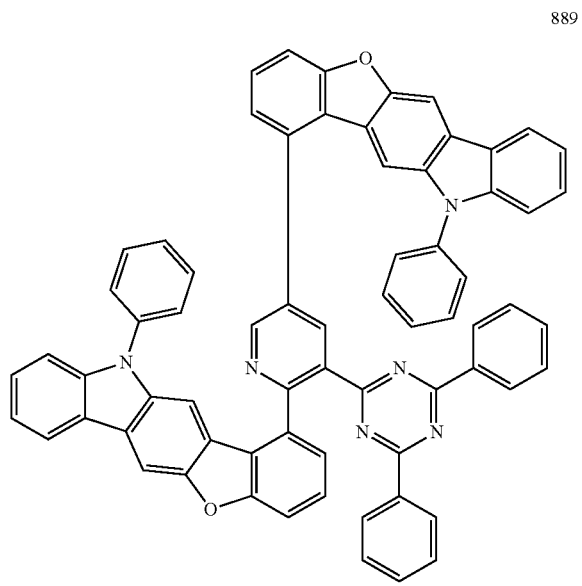
890
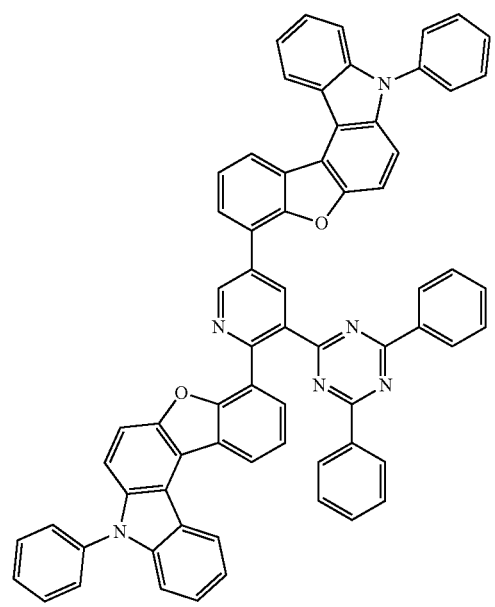
891
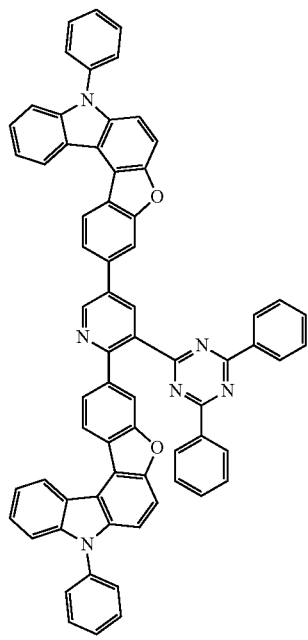
892
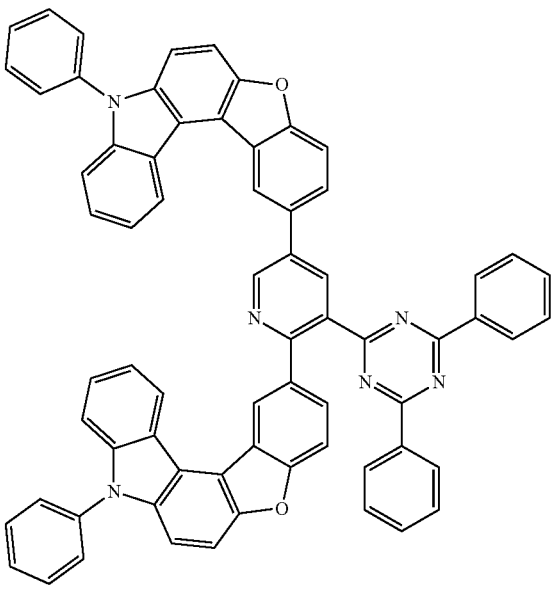

1587
-continued
893
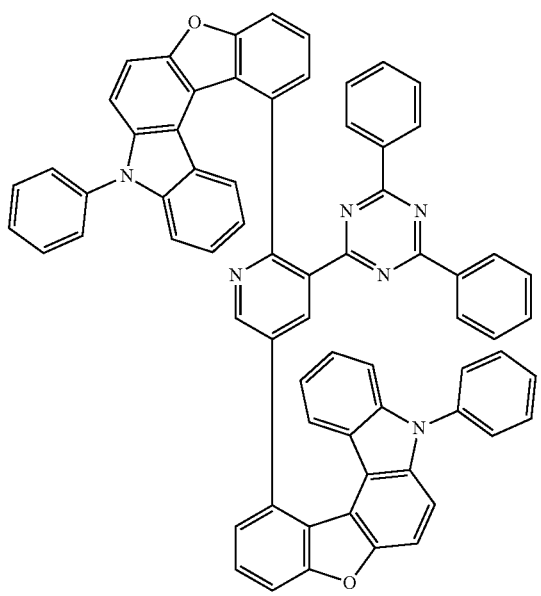
1588
-continued
895
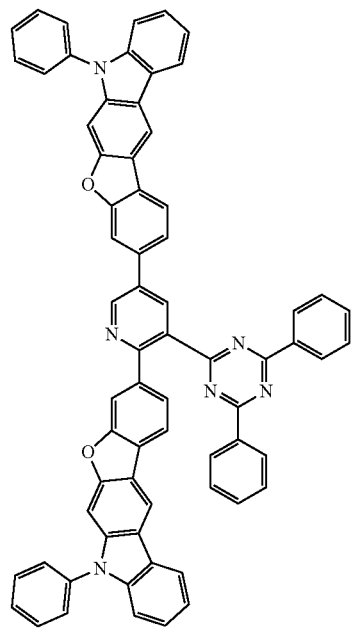
894
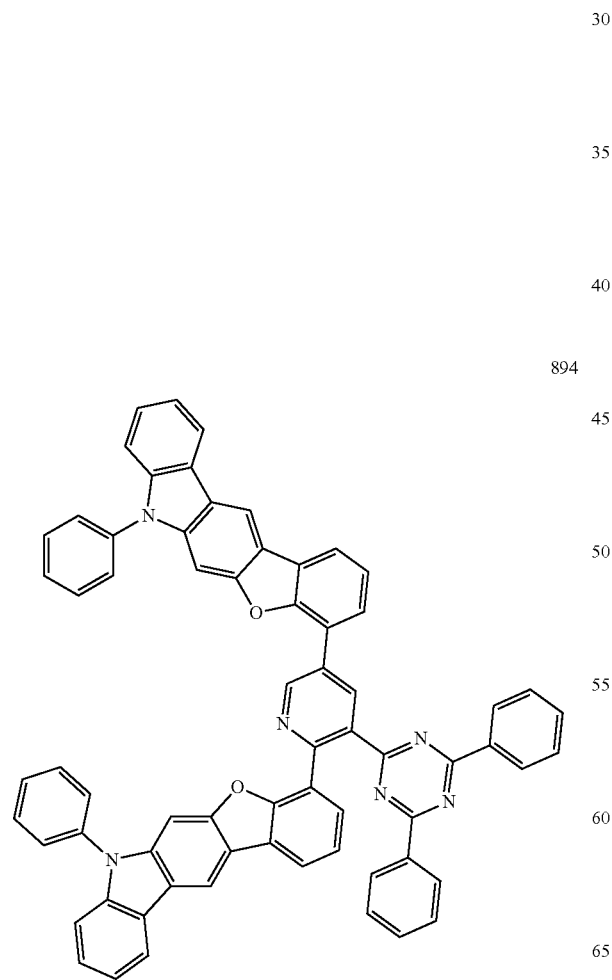
896
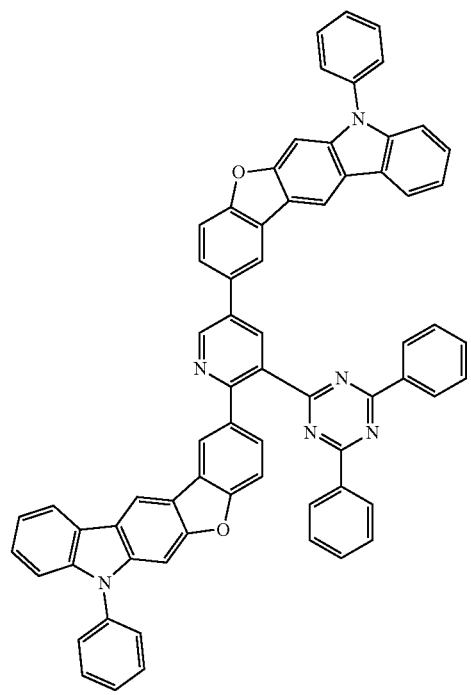

1589
-continued
1590
-continued
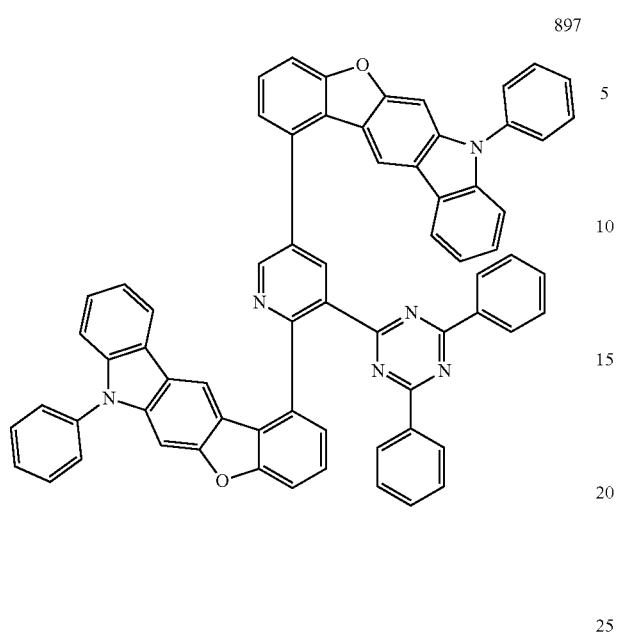
897
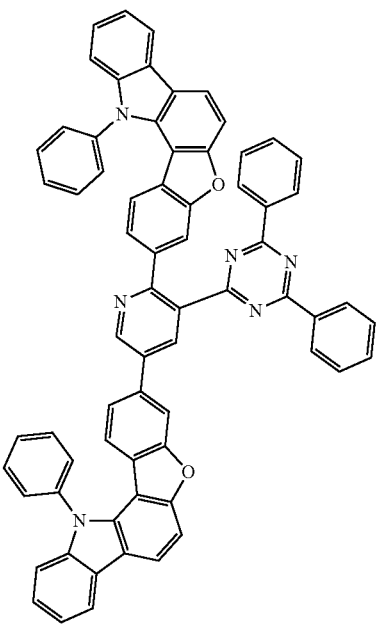
899
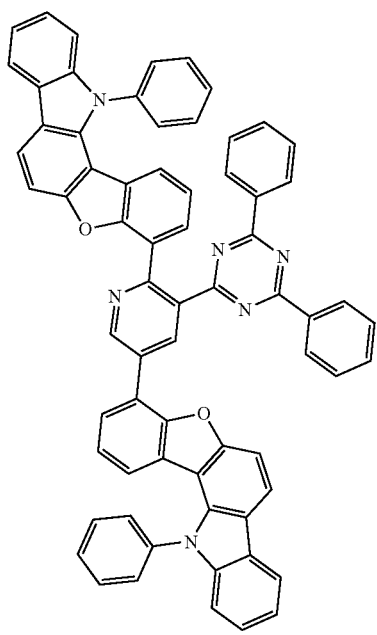
898
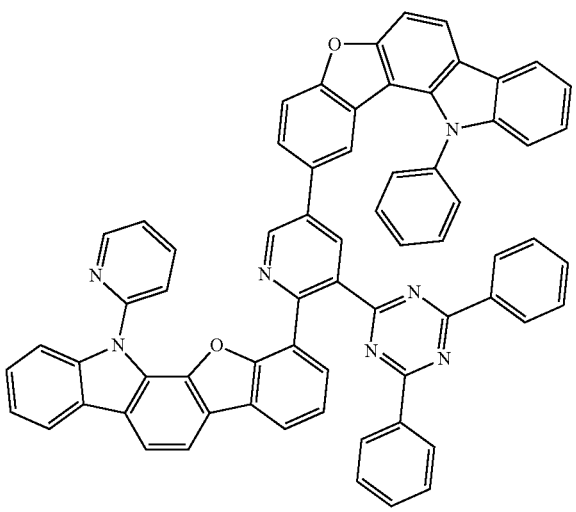
900

-continued
901
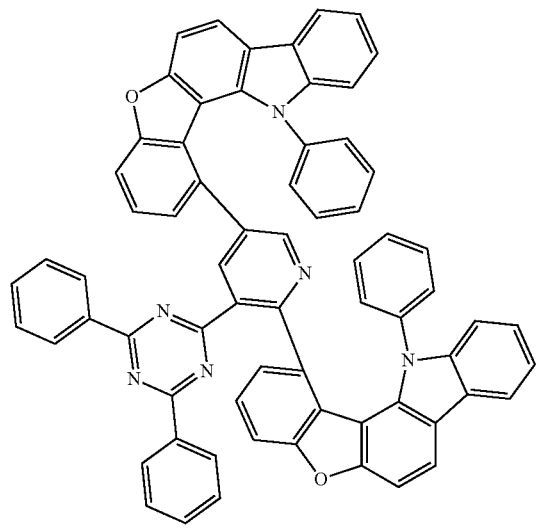
902
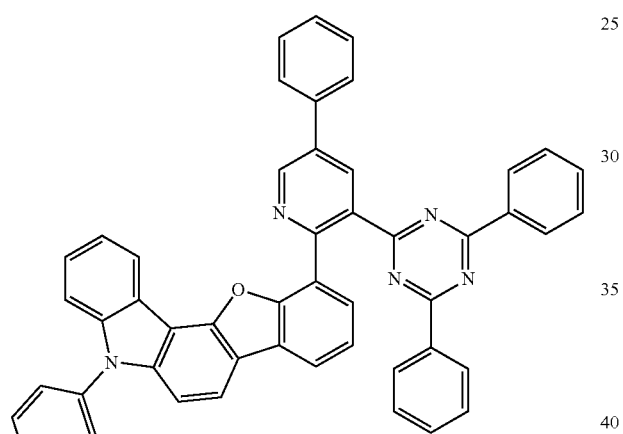
903
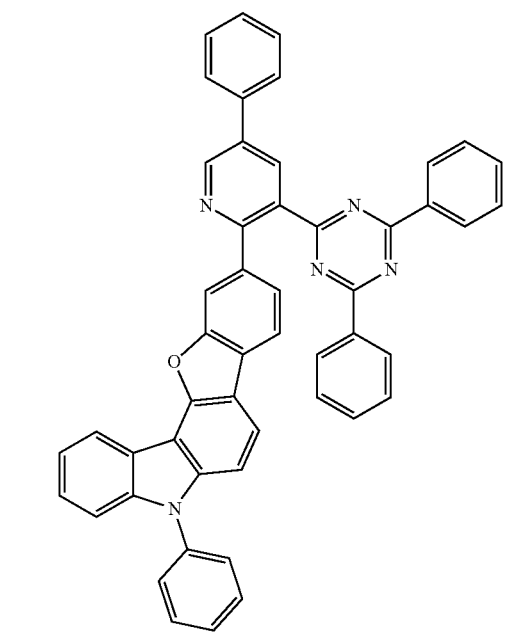
-continued
904
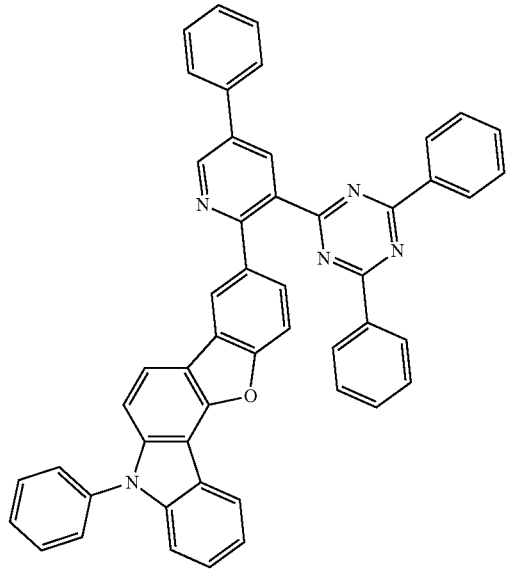
905
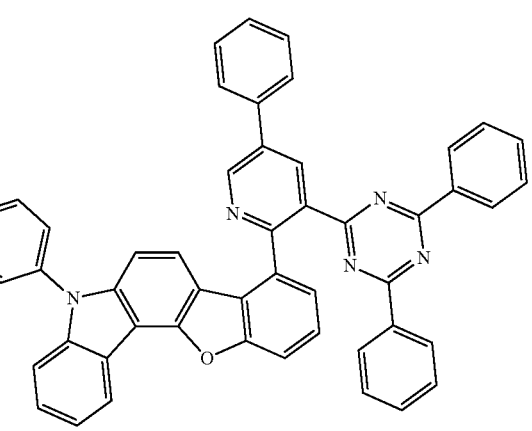
906
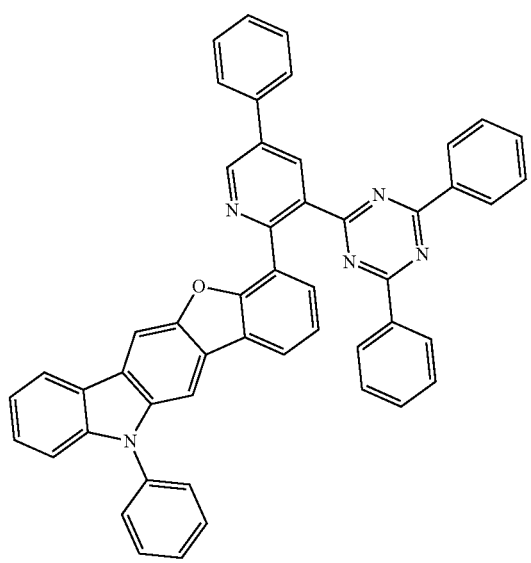

1593
-continued
907
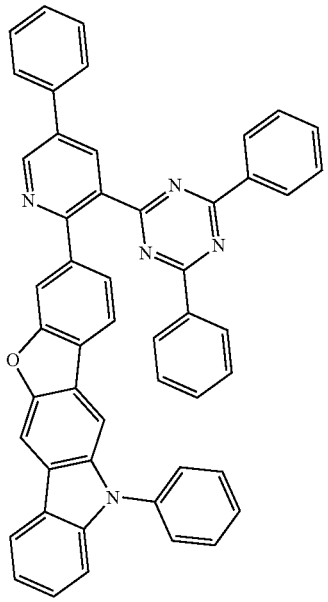
908
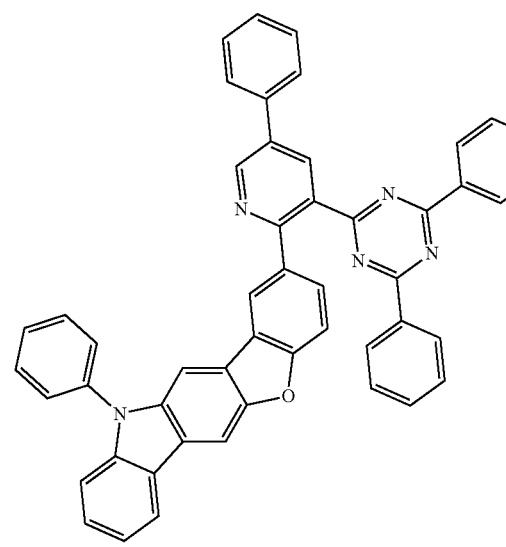
909
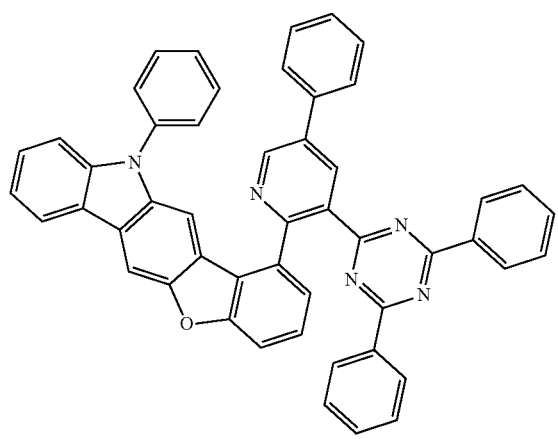
1594
-continued
910
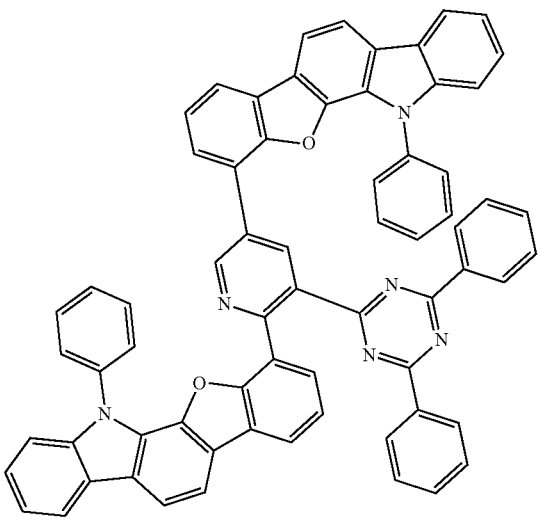
911
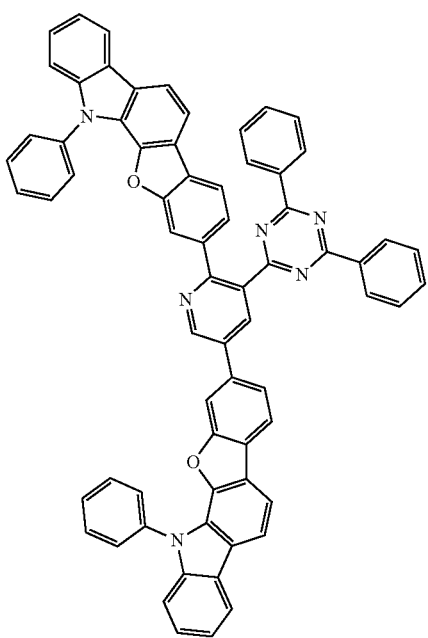

1595
-continued
912
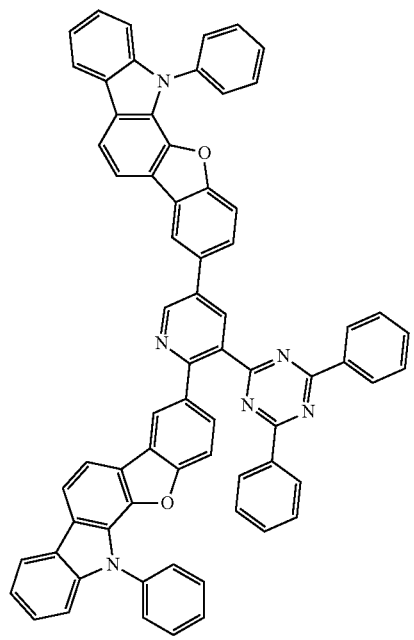
913
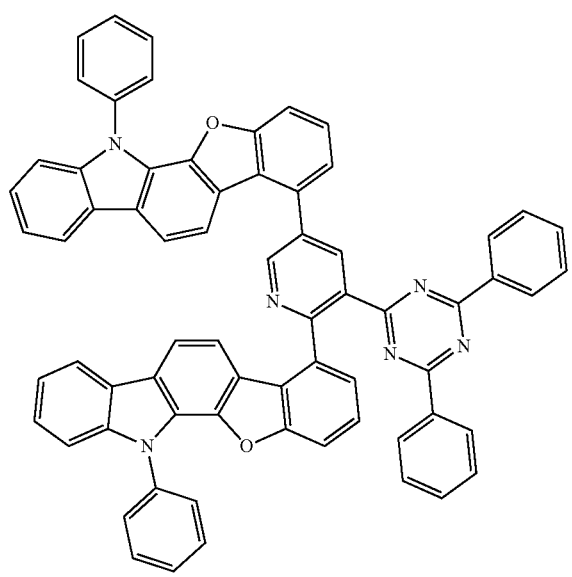
1596
-continued
914
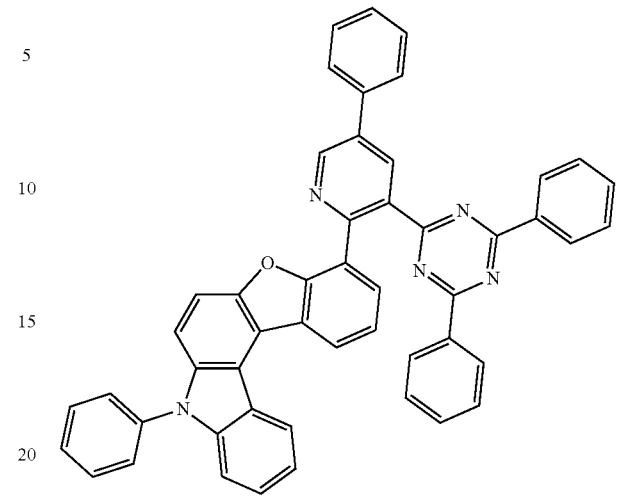
915
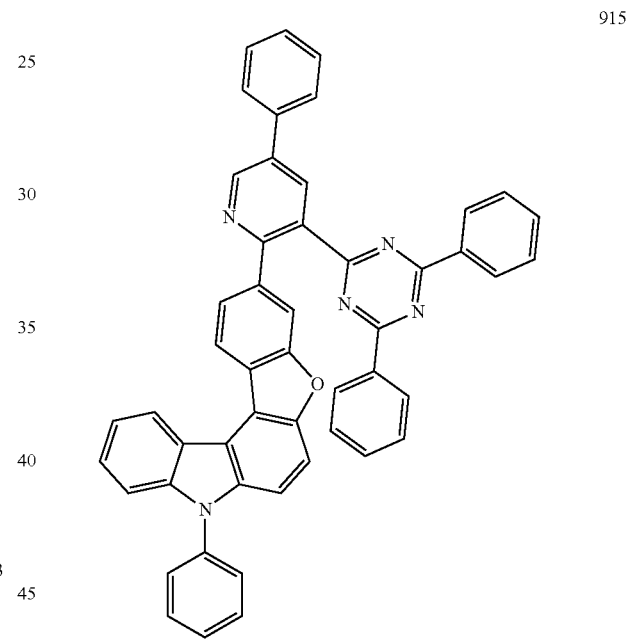
916
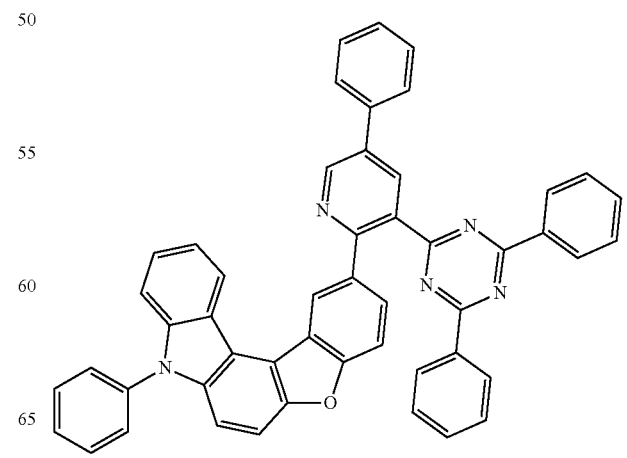

917
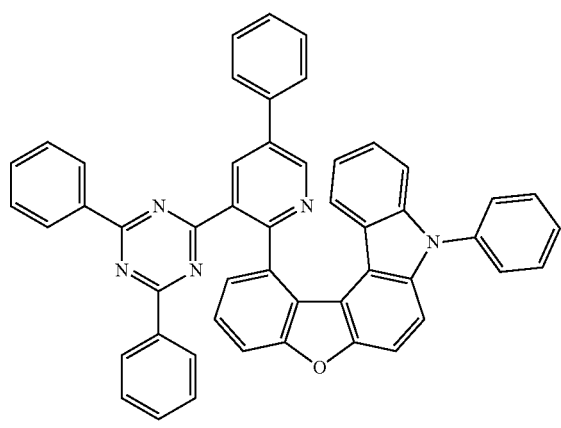
920
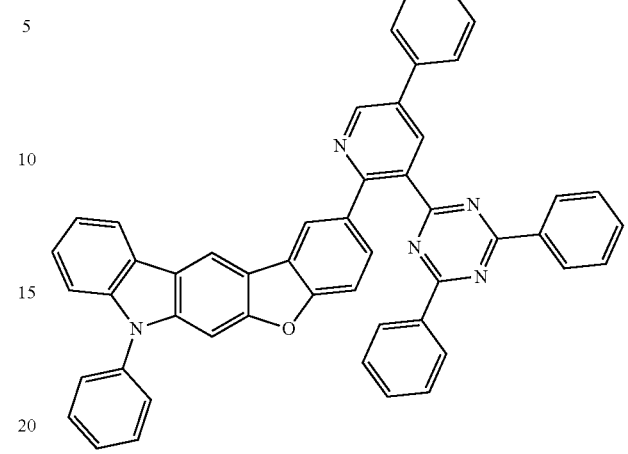
918
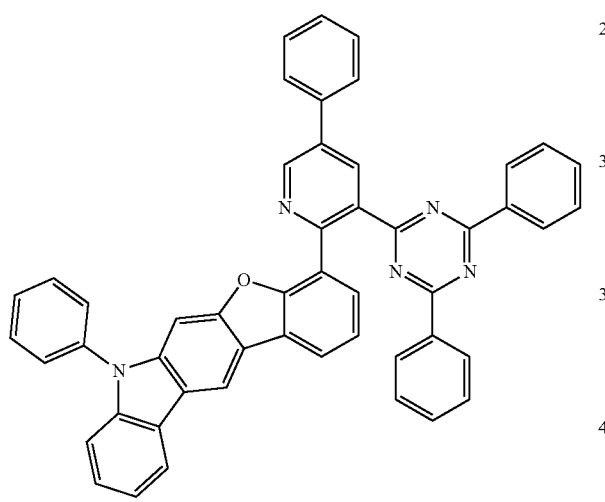
921
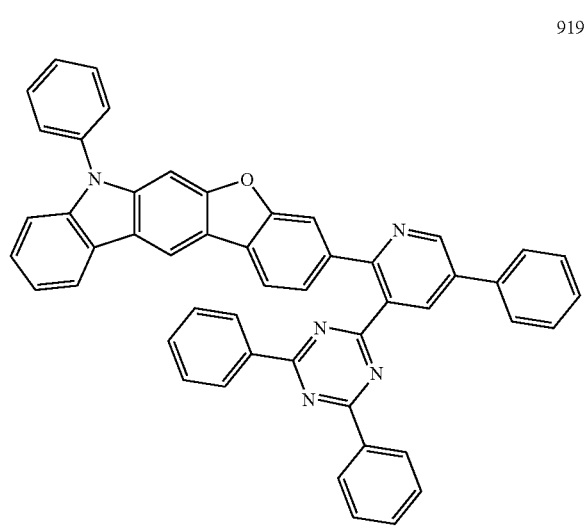
919
922
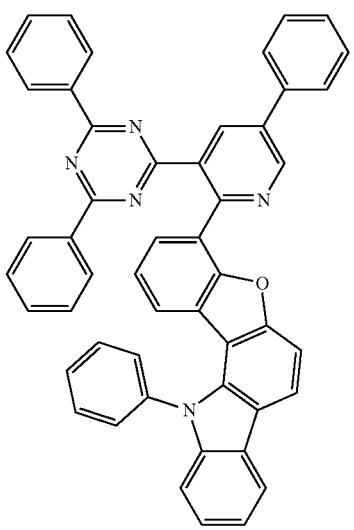

-continued
923
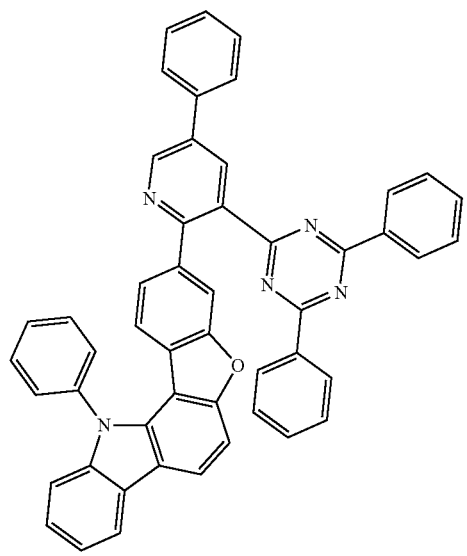
924
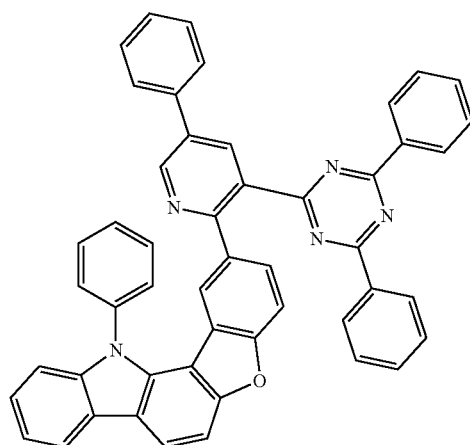
925
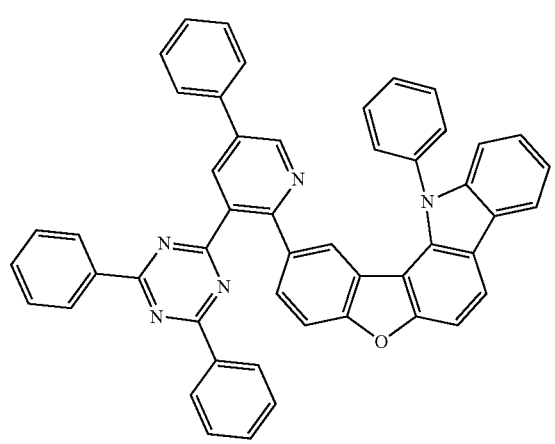
-continued
926
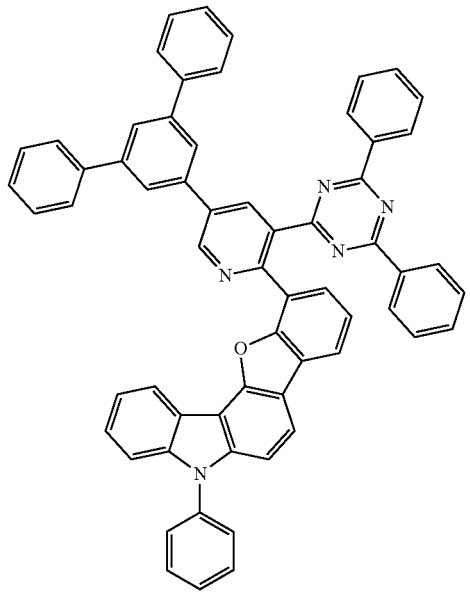
927
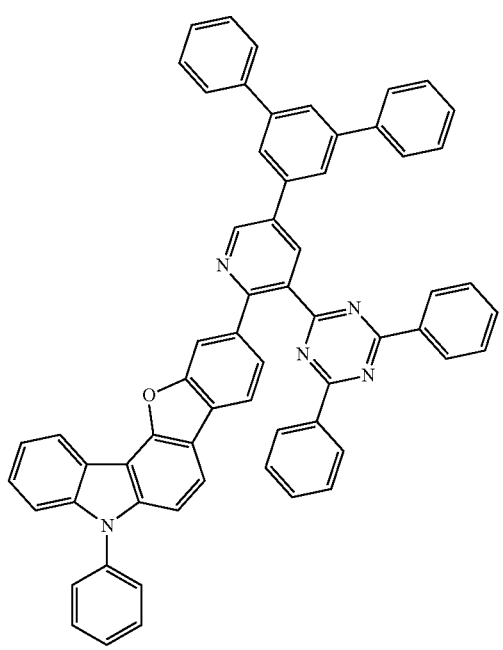

1601
-continued
928
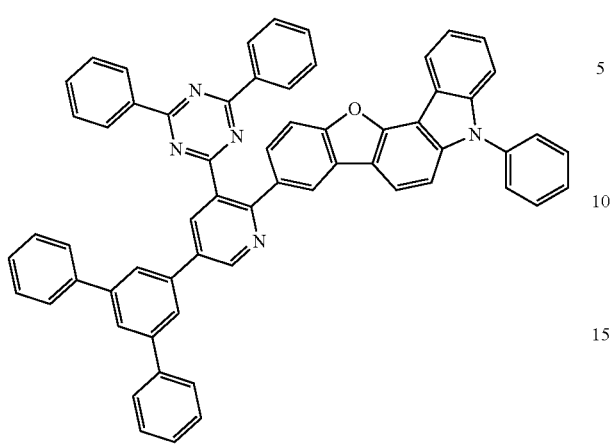
929
930
1602
-continued
931
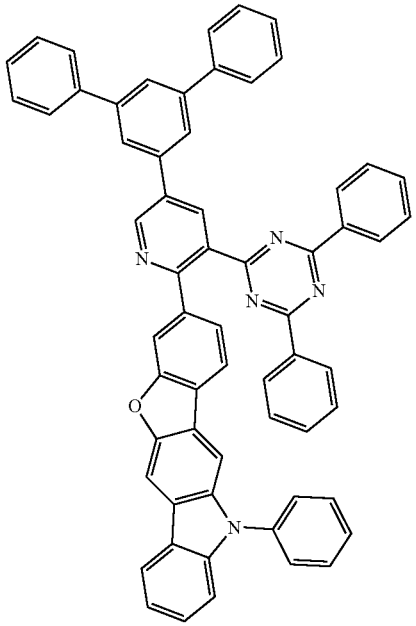
932
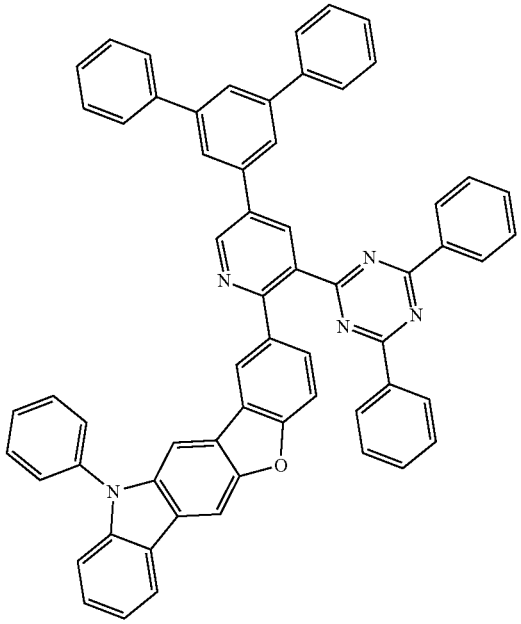

1603
-continued
933
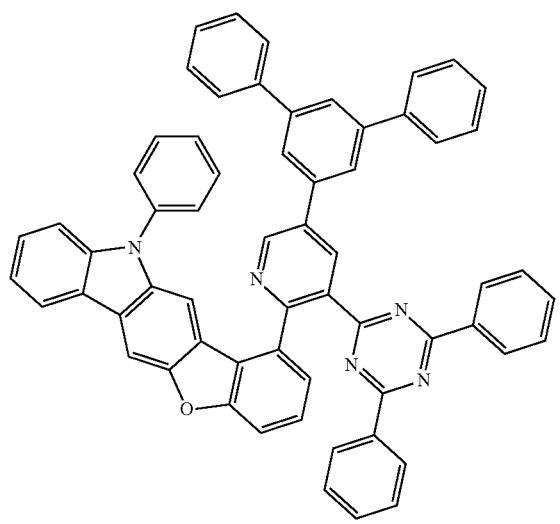
934
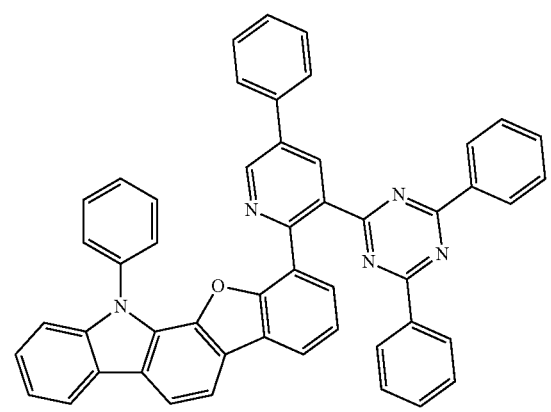
935
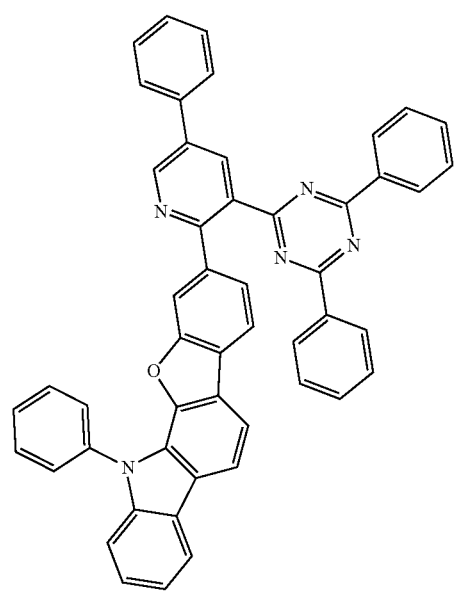
1604
-continued
936
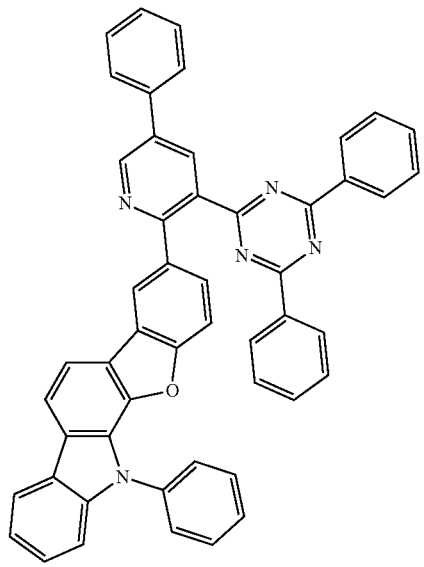
937
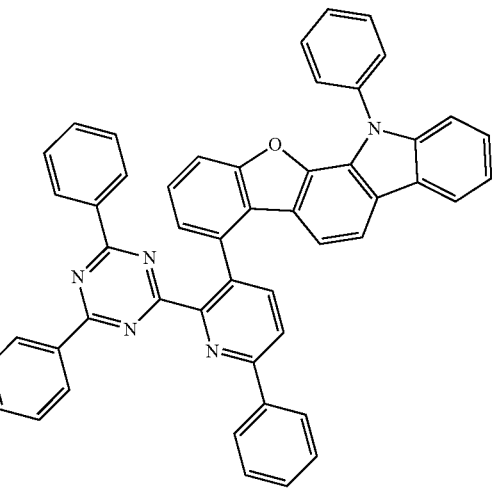
938
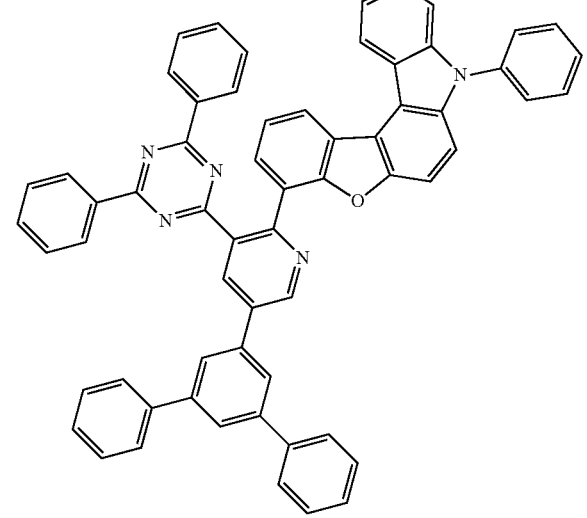

1605
-continued
939
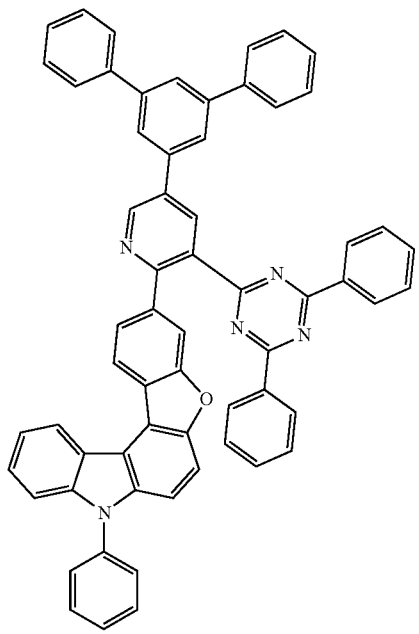
940
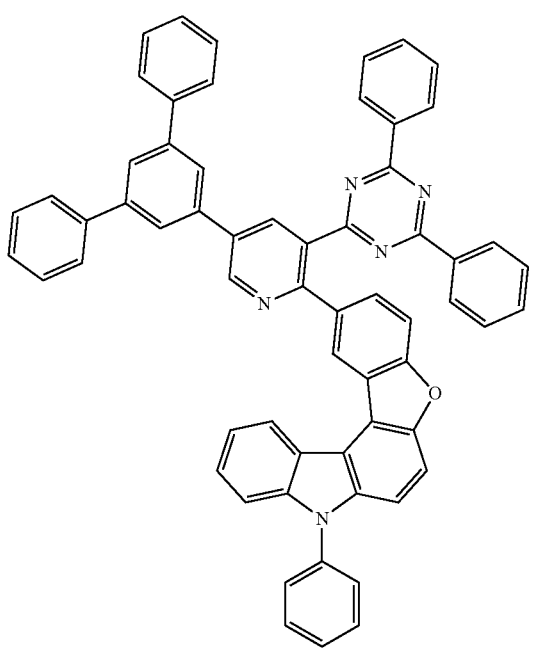
1606
-continued
941
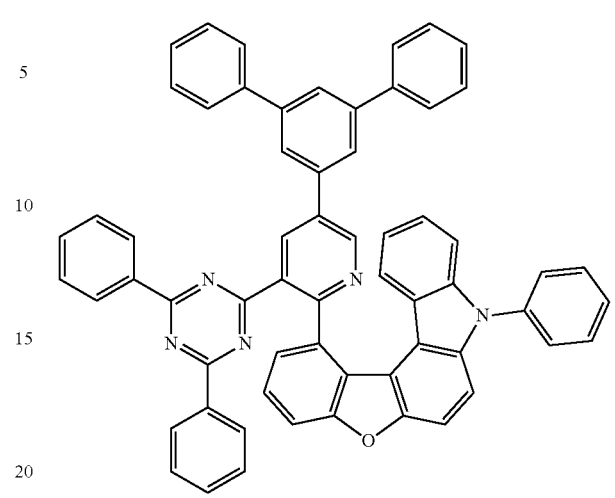
942
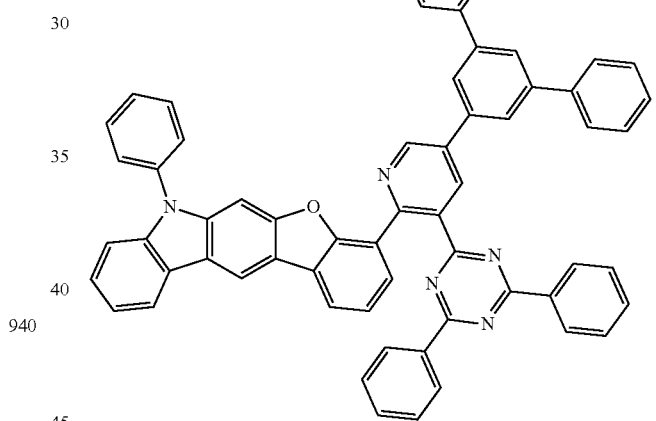
943
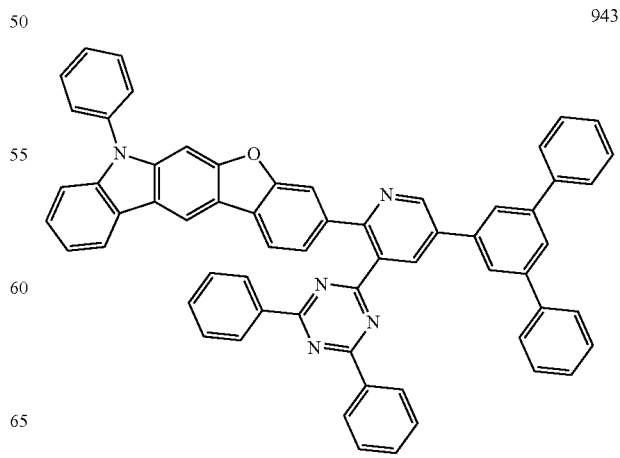

1607
-continued
944
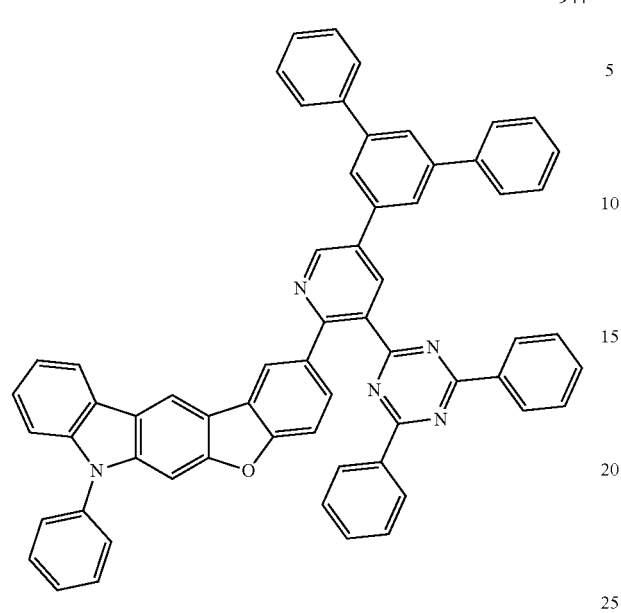
1608
-continued
946
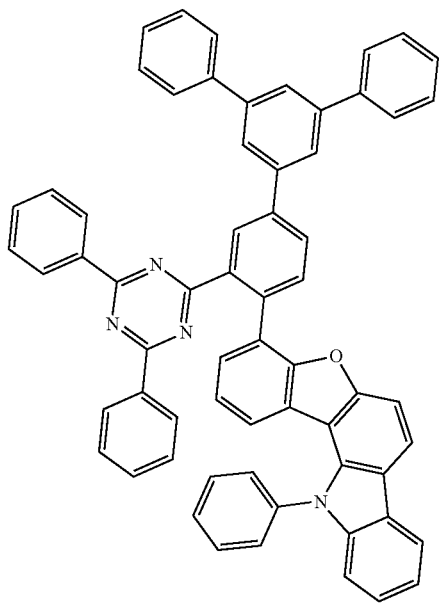
945
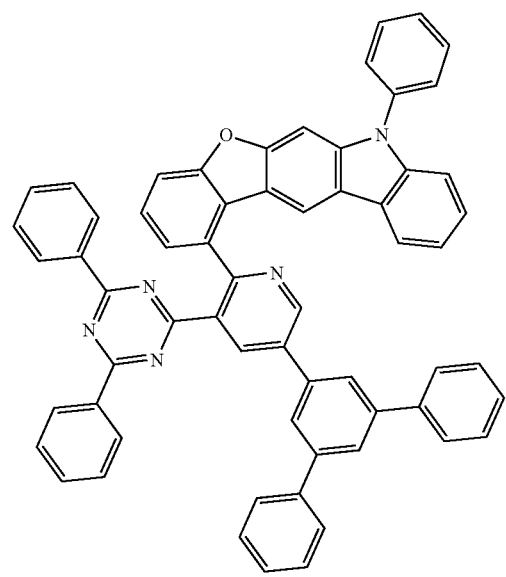
947
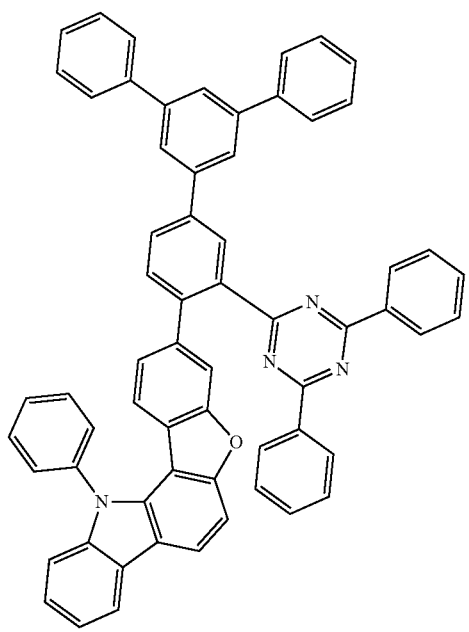

1609
-continued
948
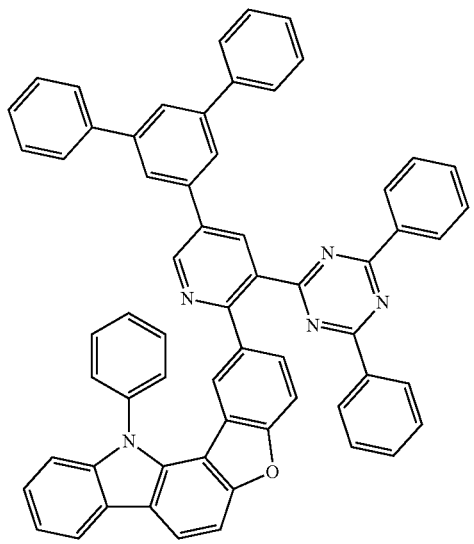
949
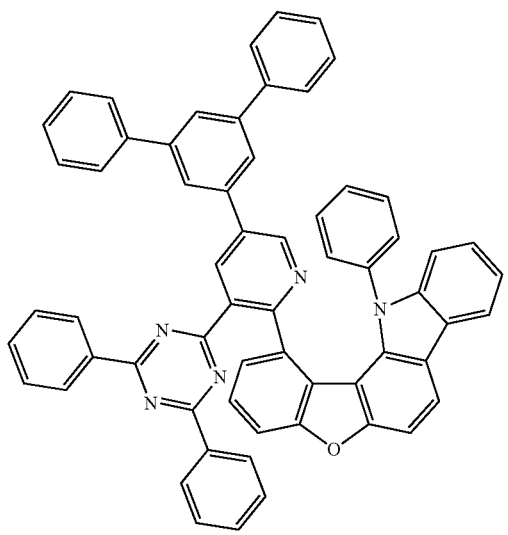
1610
-continued
950
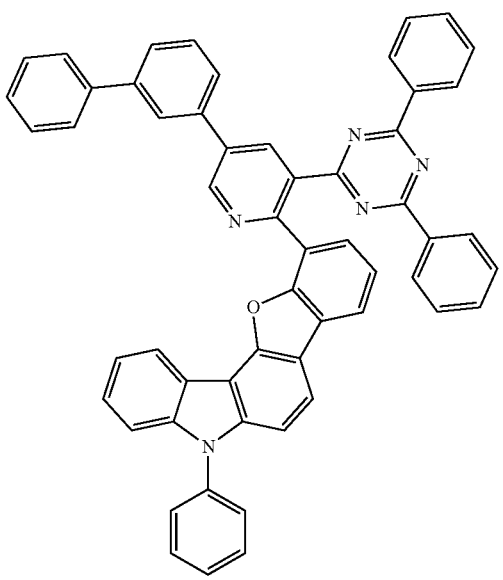
951
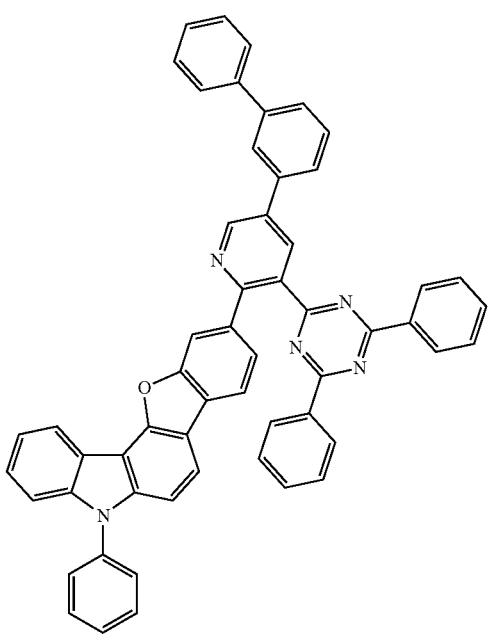

1611
-continued
952
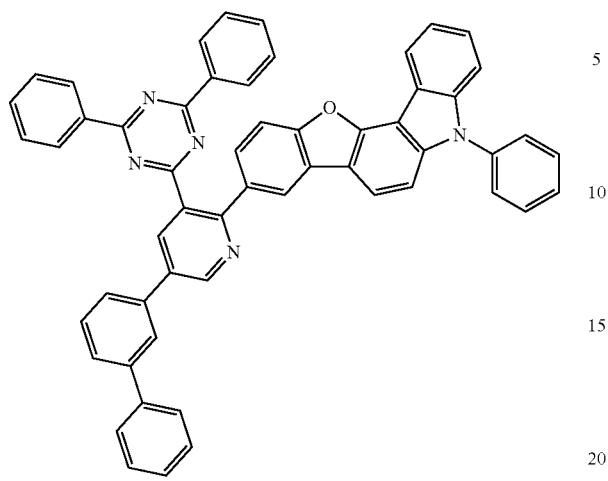
953
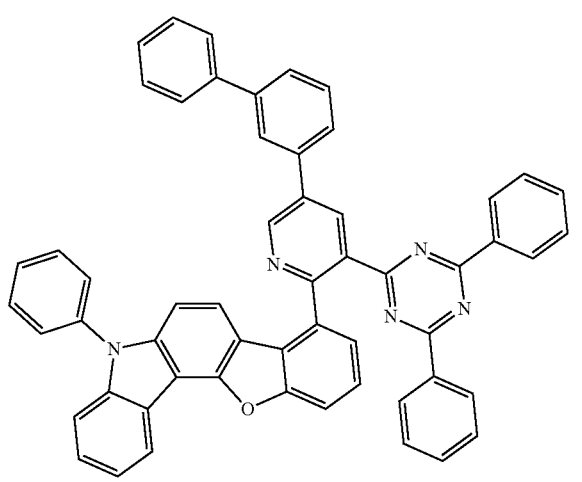
1612
-continued
955
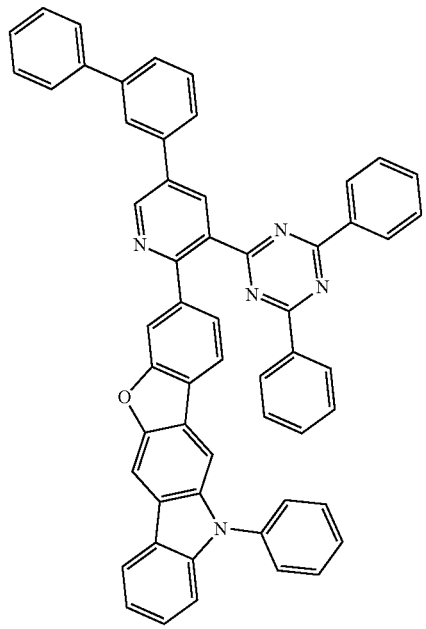
956
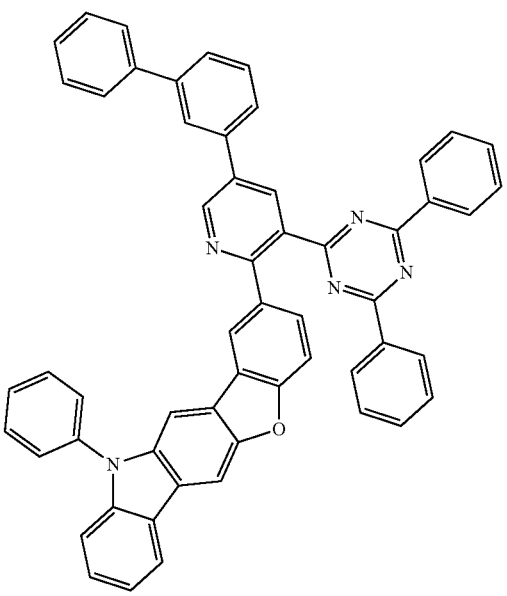
954

1613
-continued
957
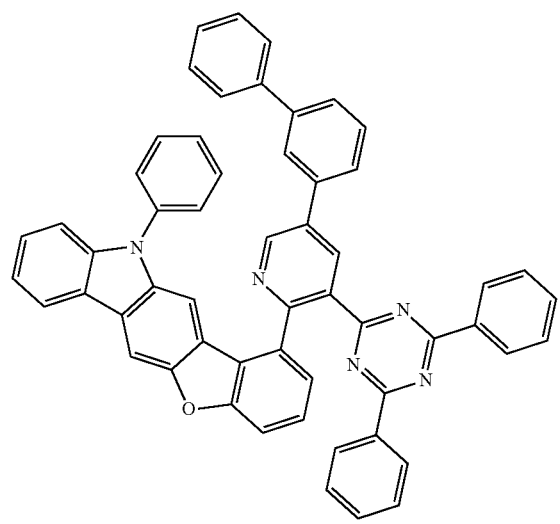
958
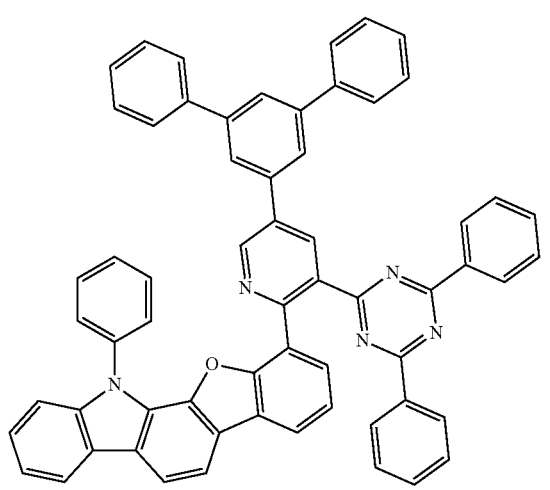
959
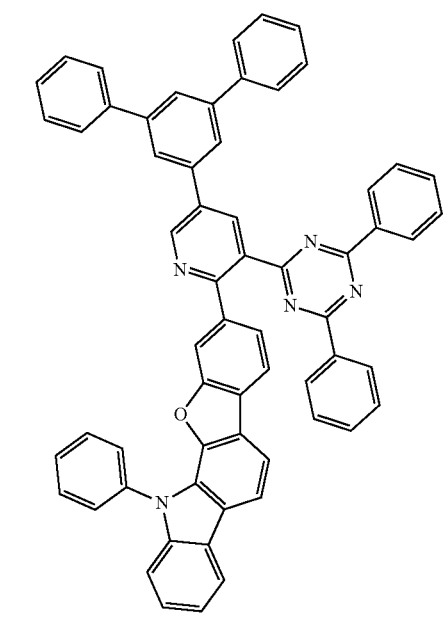
1614
-continued
960
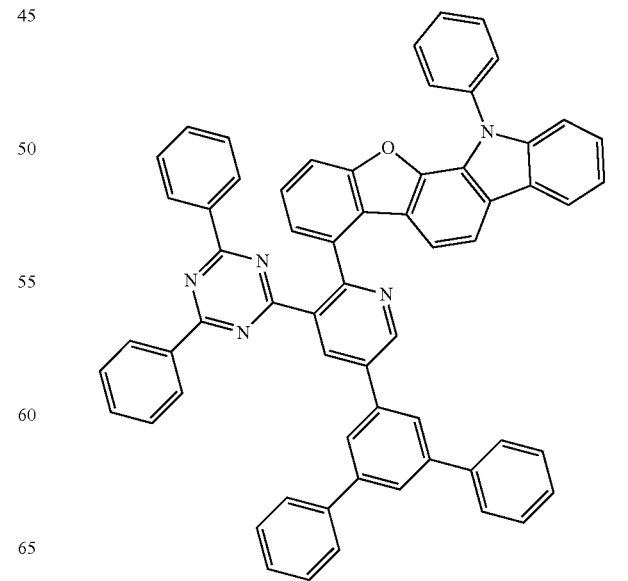
961

-continued
962
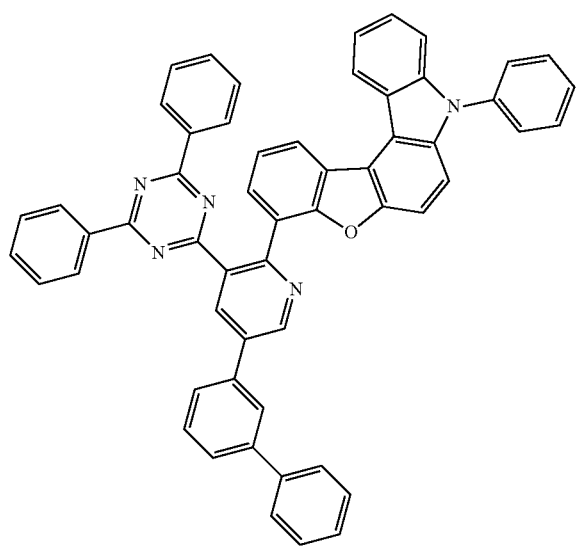
963
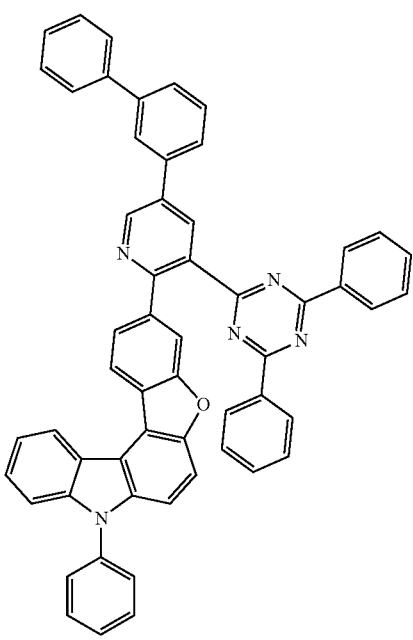
964
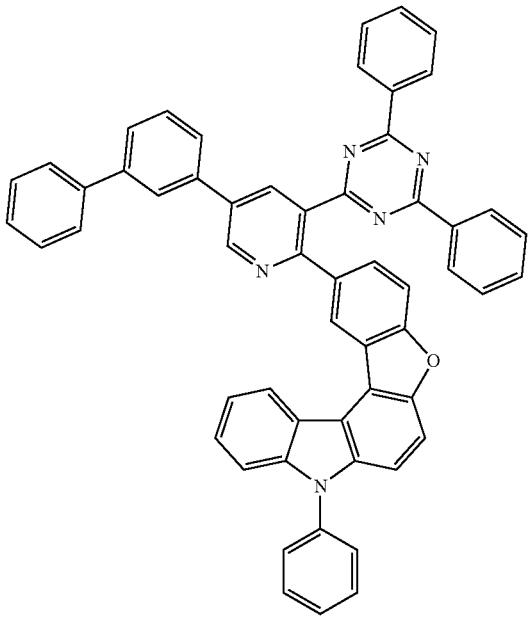
965
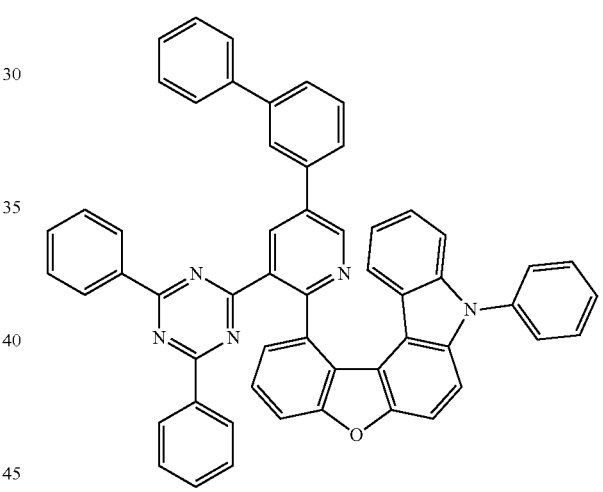
966
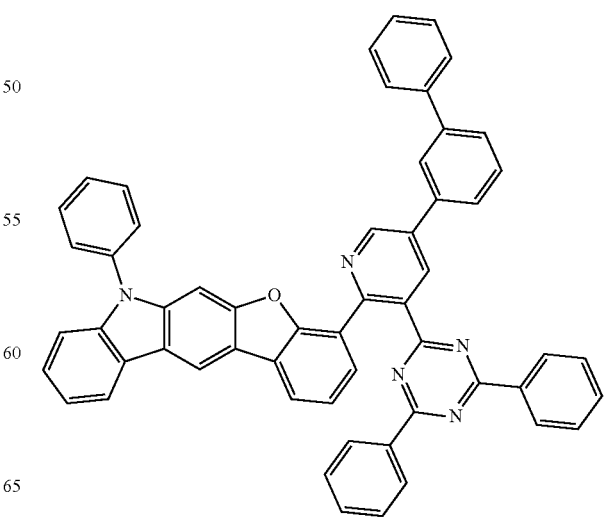

1617
-continued
967
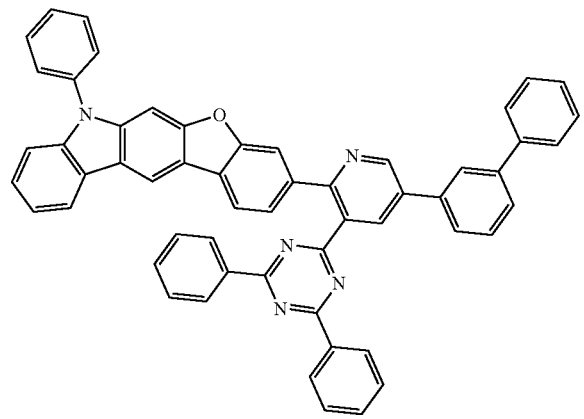
968
1618
-continued
970
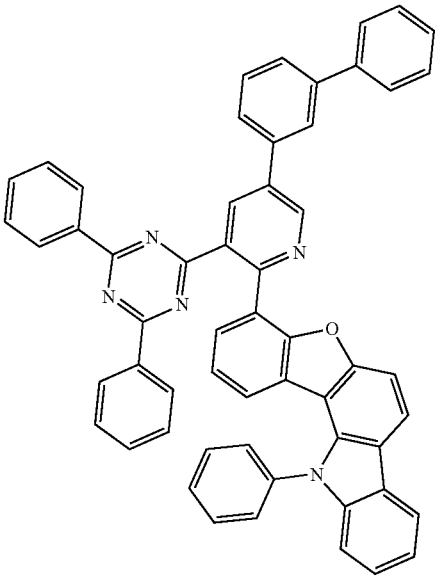
971
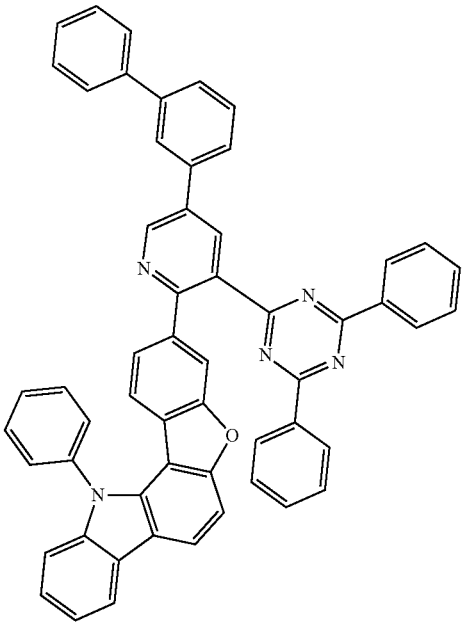
969

1619
-continued
972
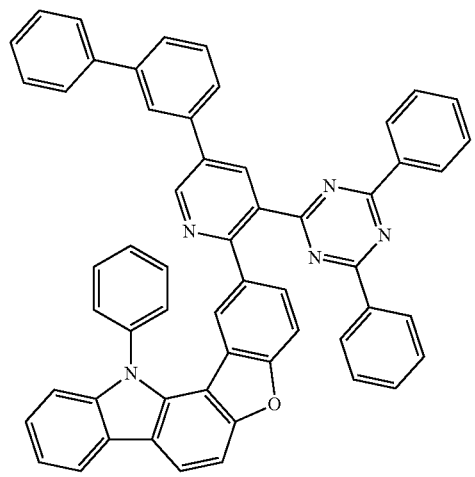
1620
-continued
974
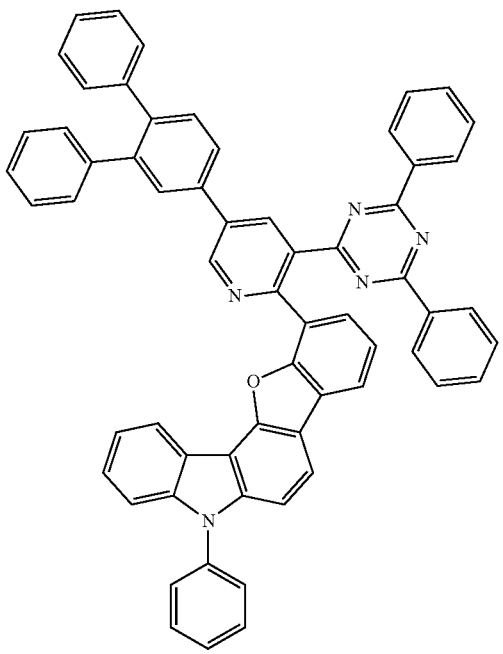
973
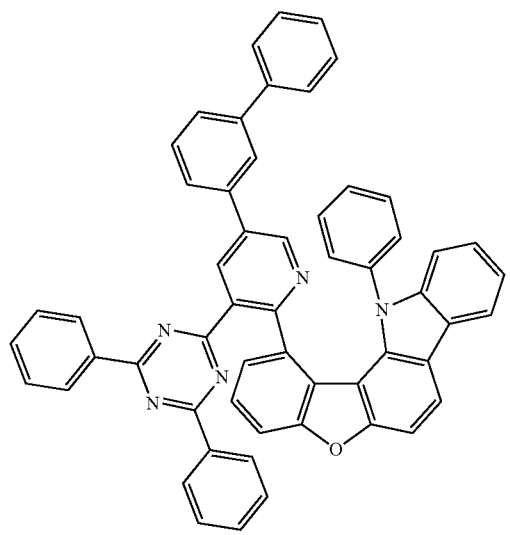
975
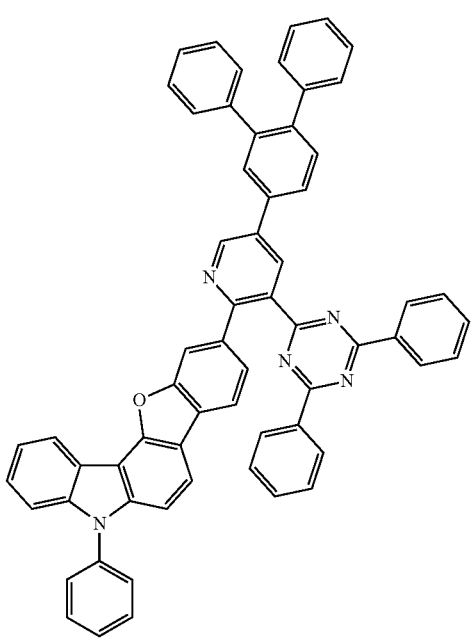

1621
-continued
1622
-continued
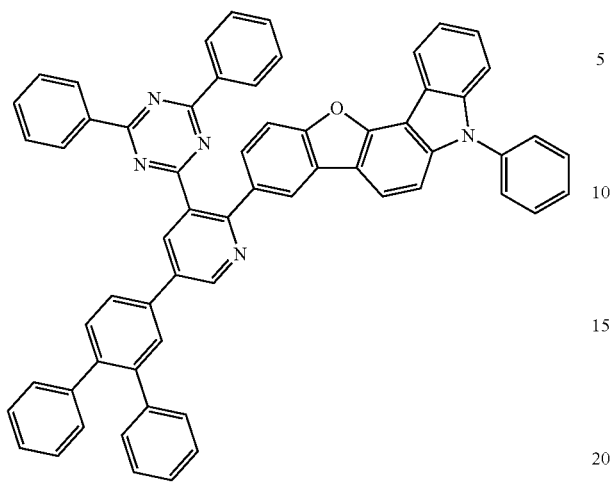
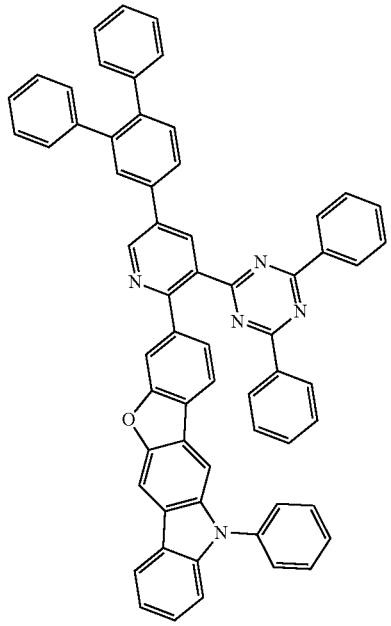
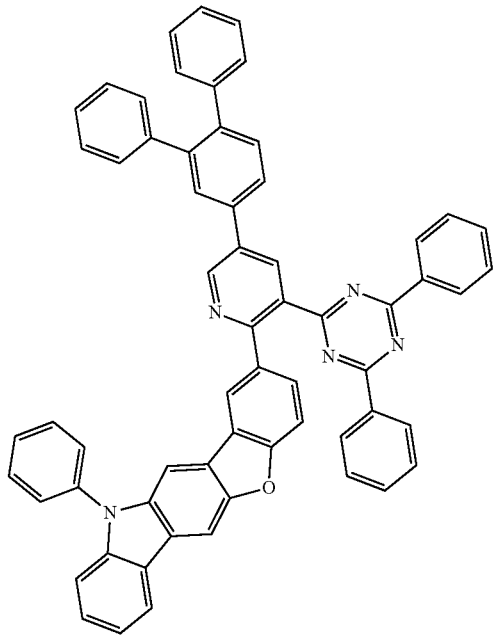

1623
-continued
981
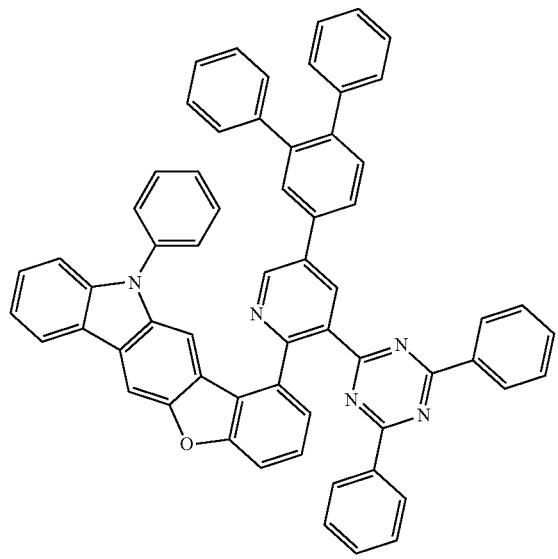
982
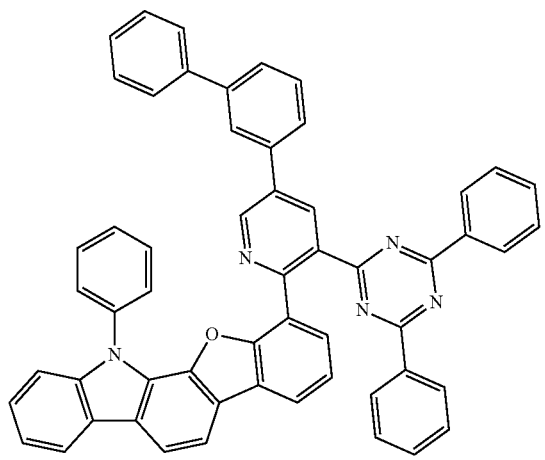
983
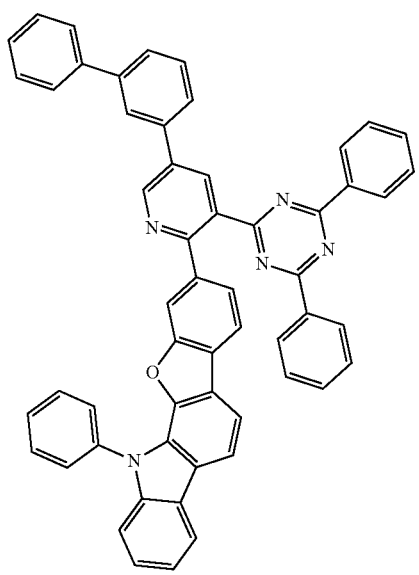
1624
-continued
984
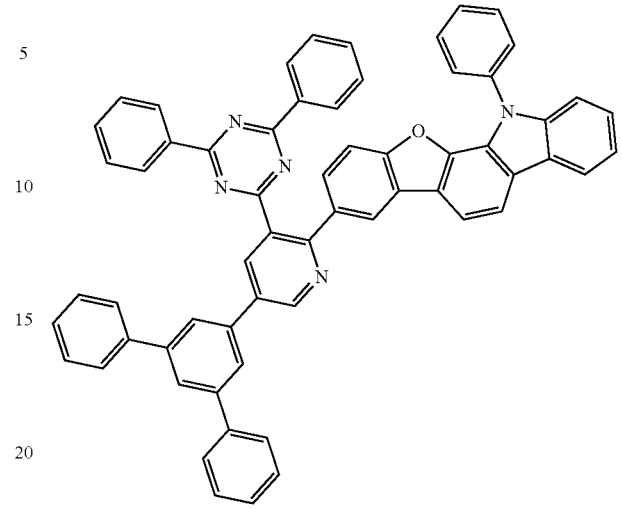
985
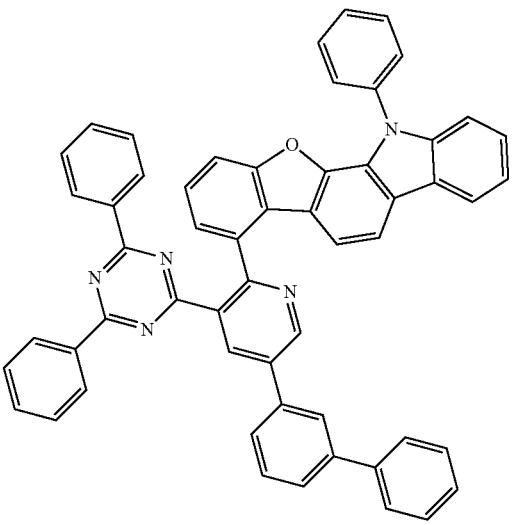
986
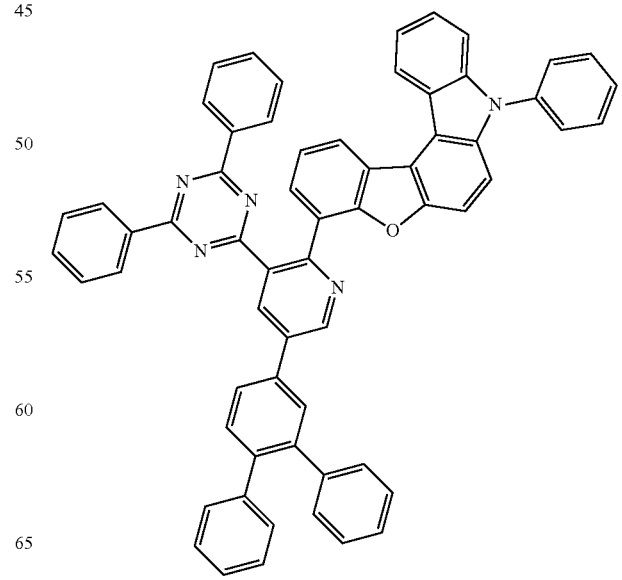

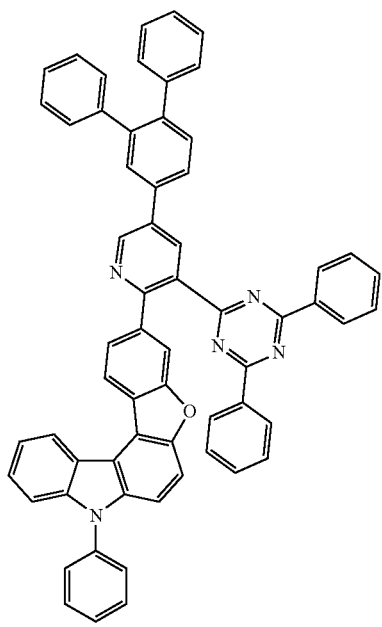
987
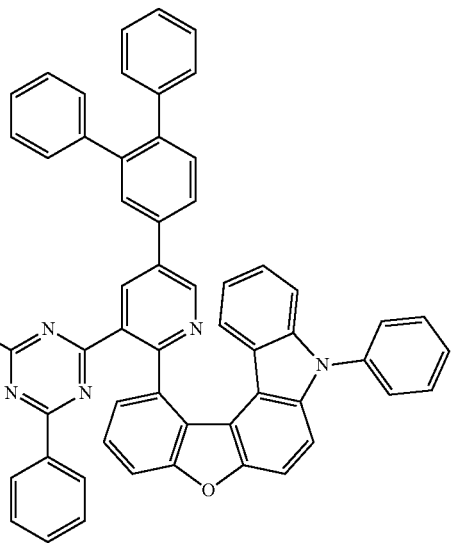
989
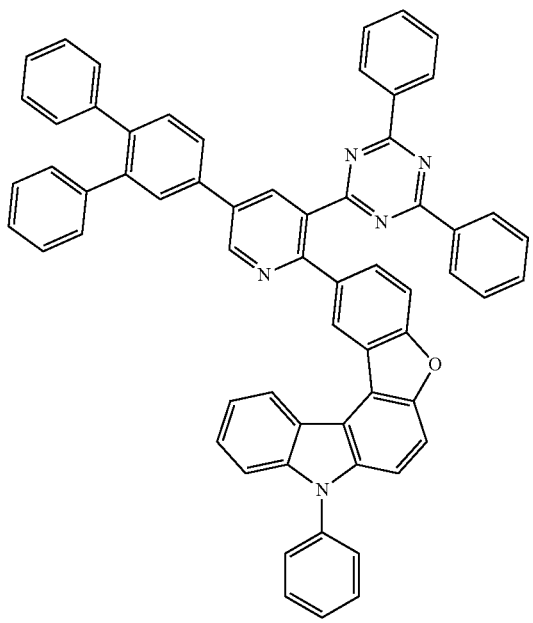
988
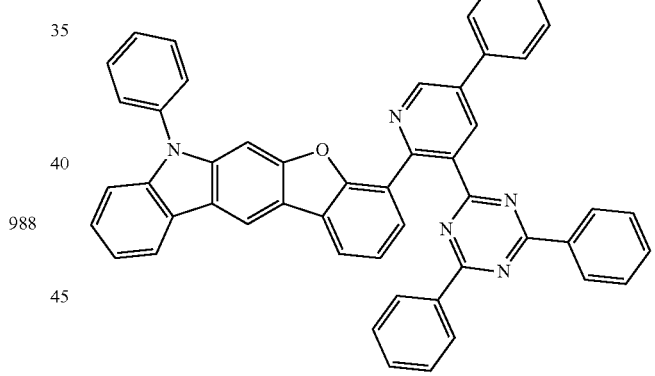
990
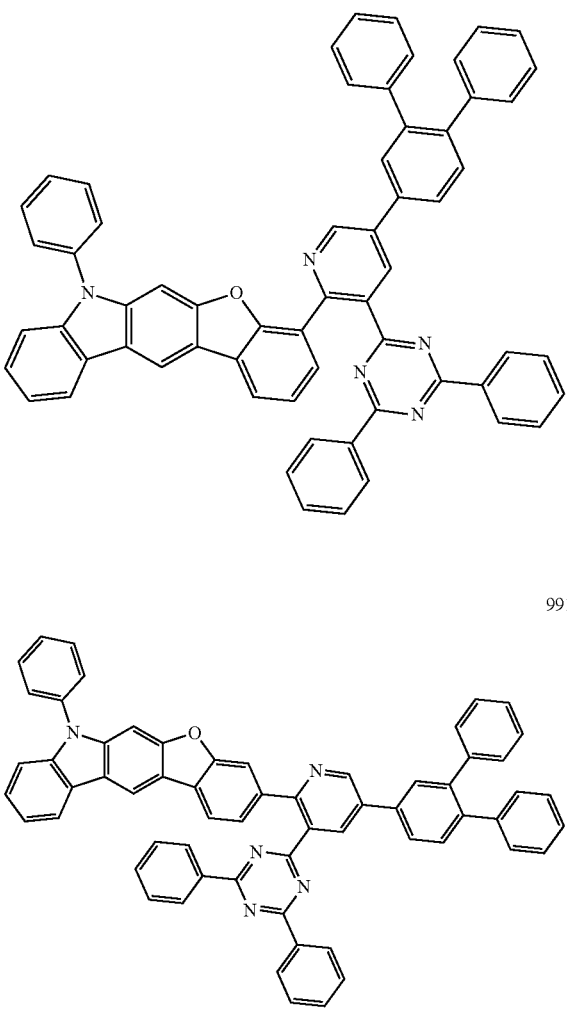
991

1627
-continued
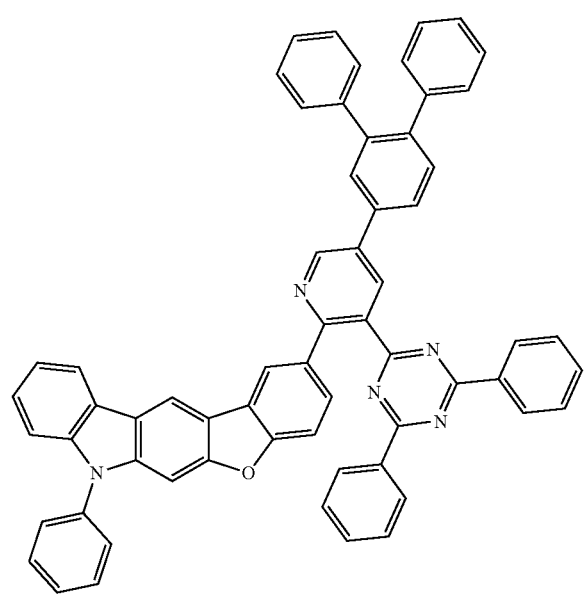
992
1628
-continued
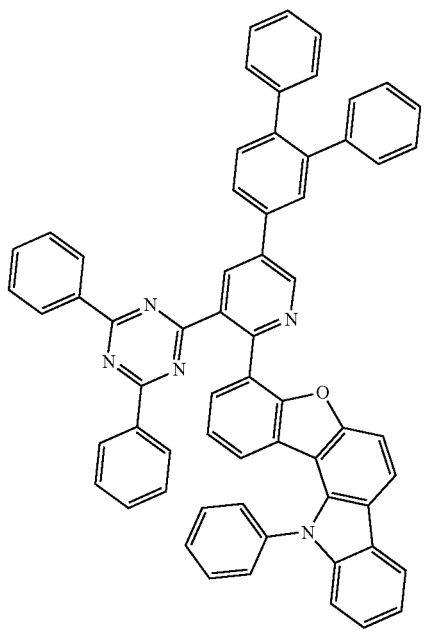
994
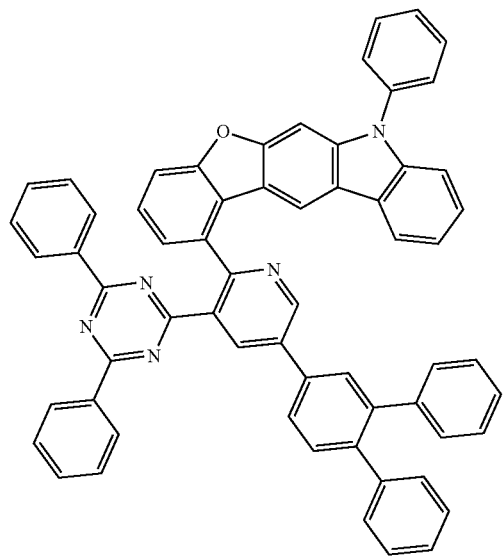
993
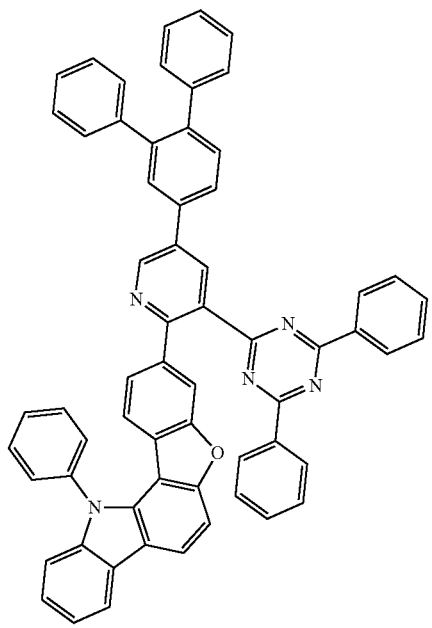
995

1629
-continued
1630
-continued
996
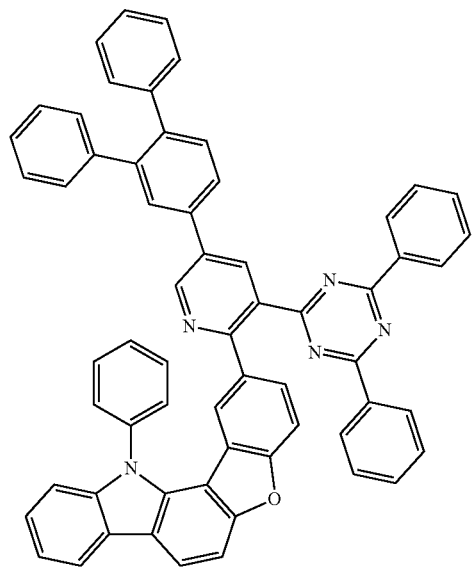
998
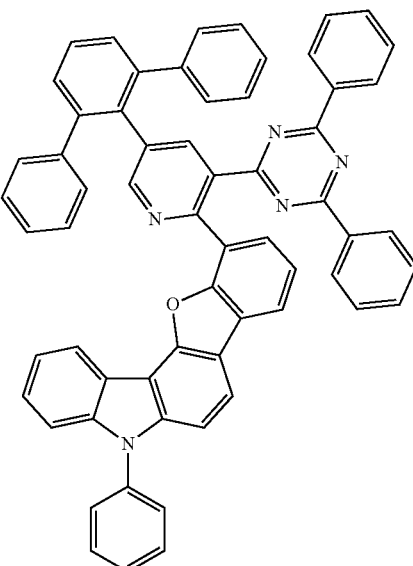
999
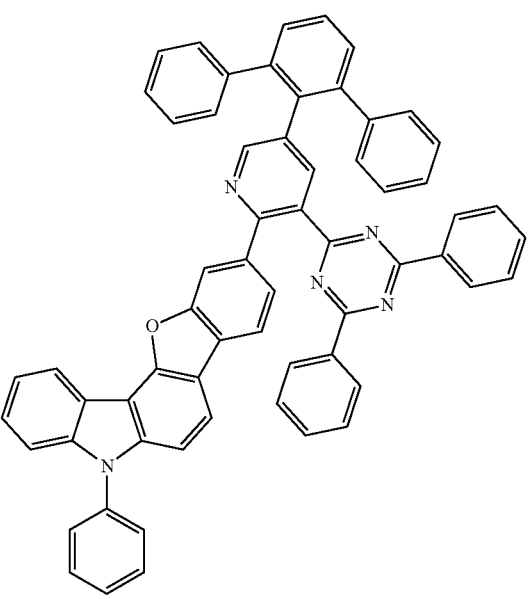
997
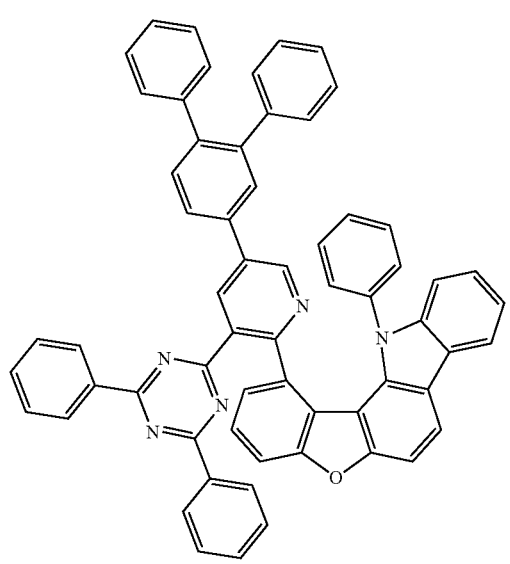
1000

1001
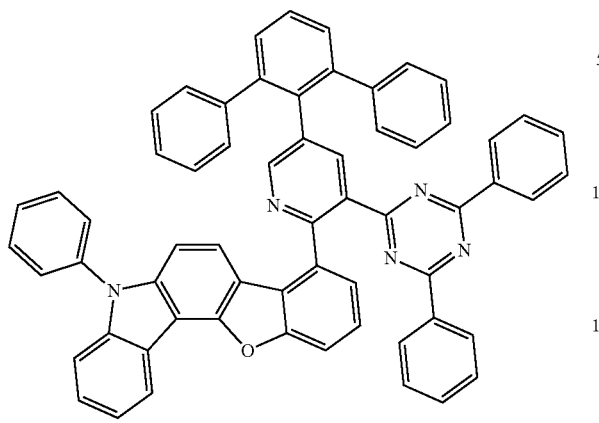
1002
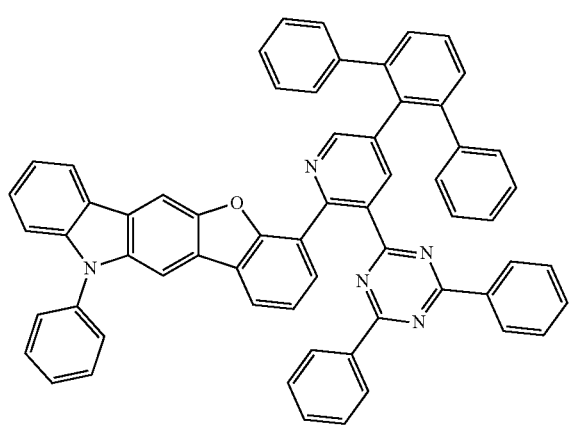
1003
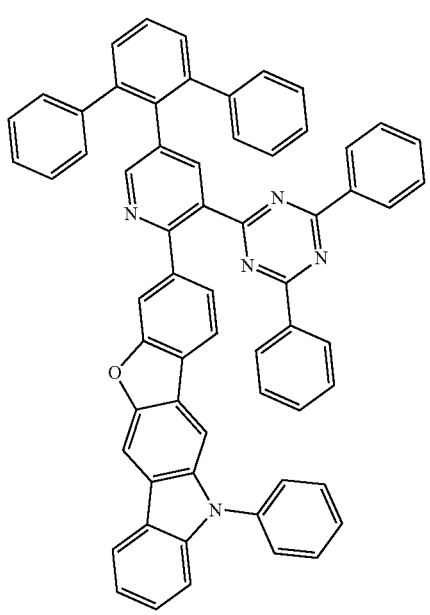
1004
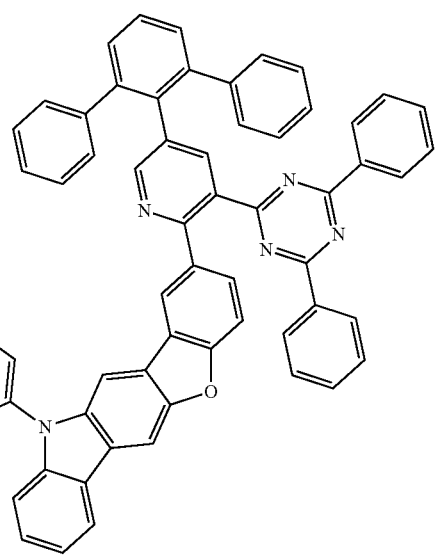
1005
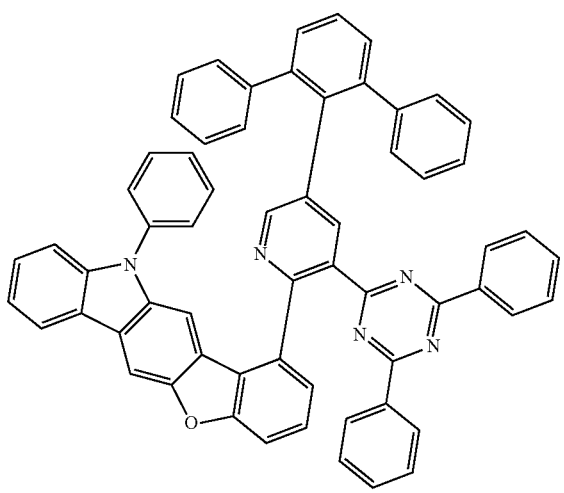
1006
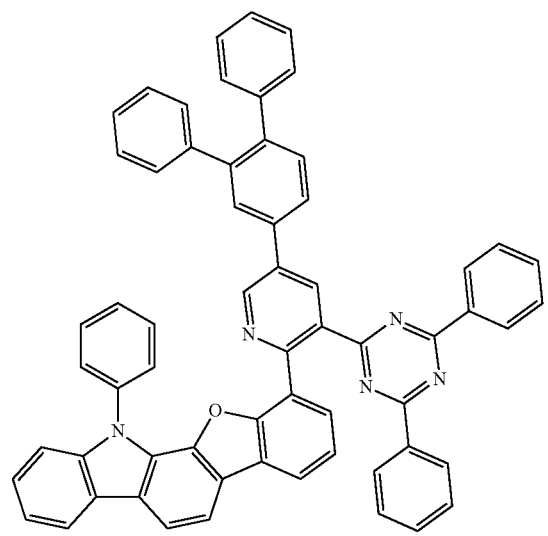

1633
-continued
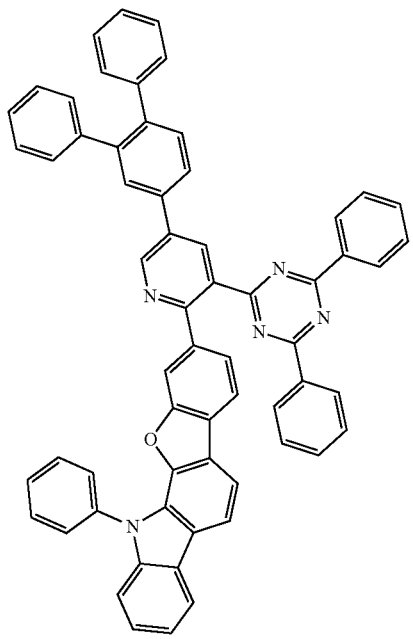
1007
1634
-continued
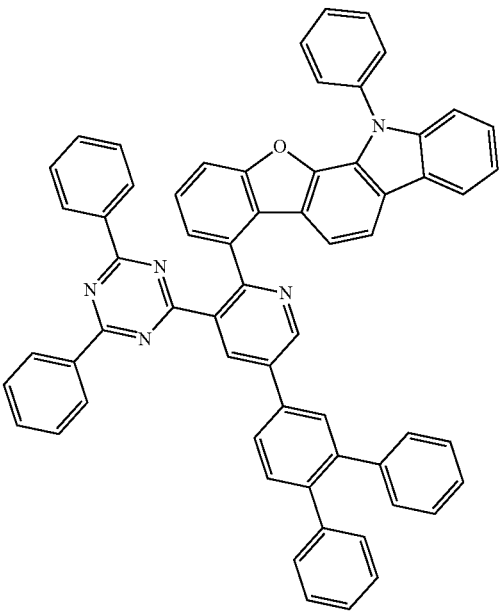
1009
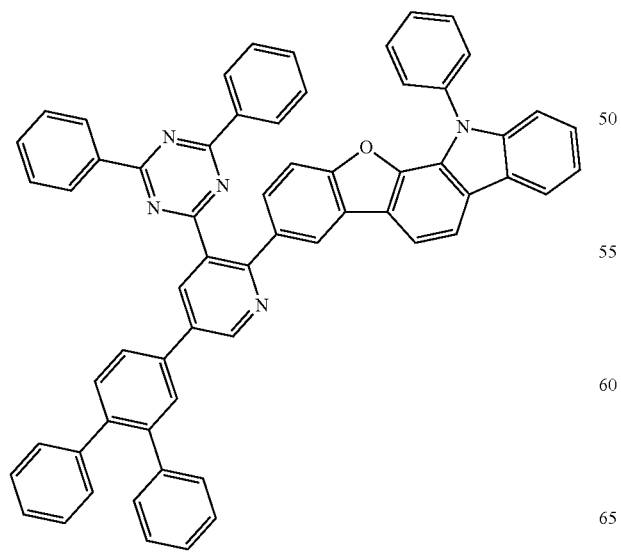
1008
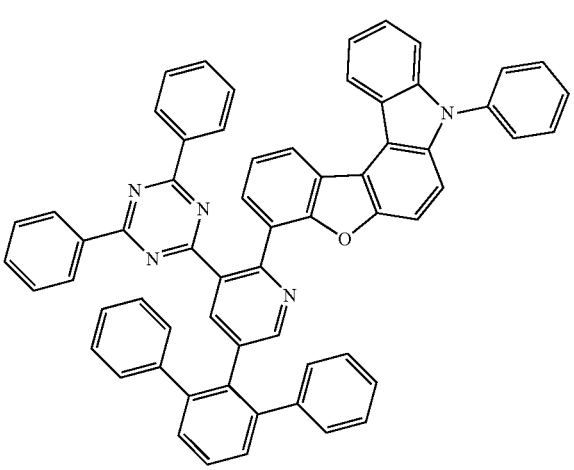
1010

1635
-continued
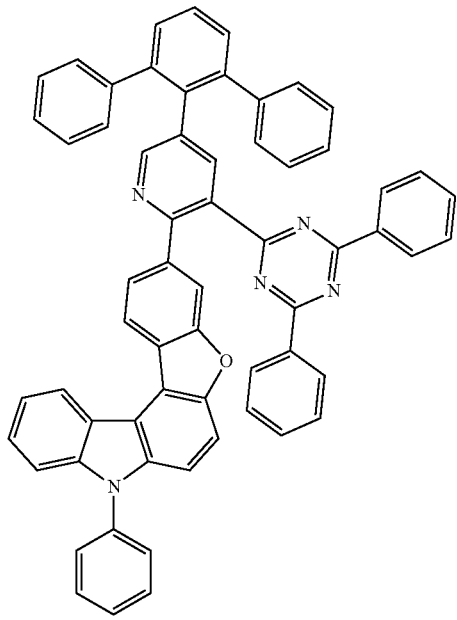
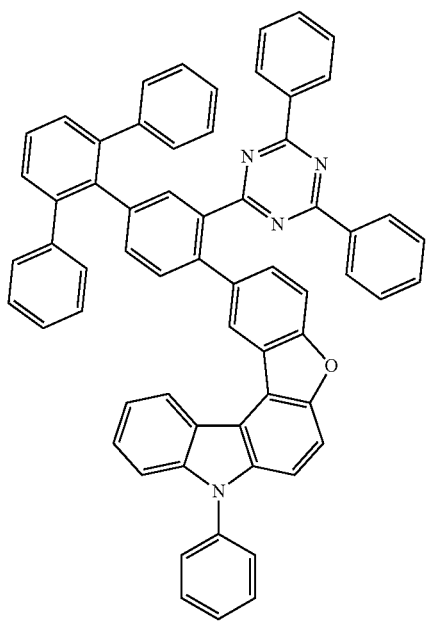
1636
-continued
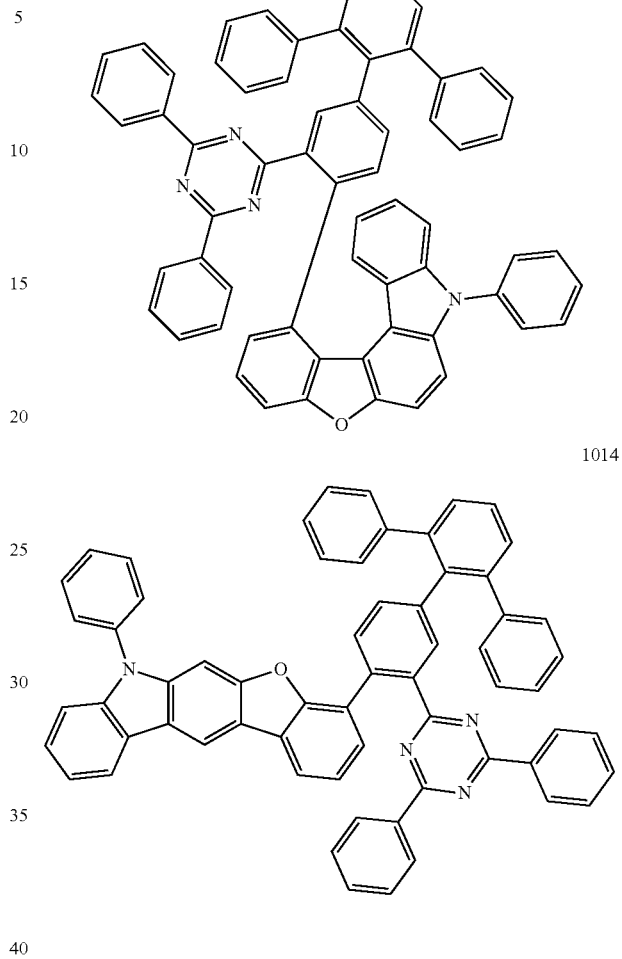
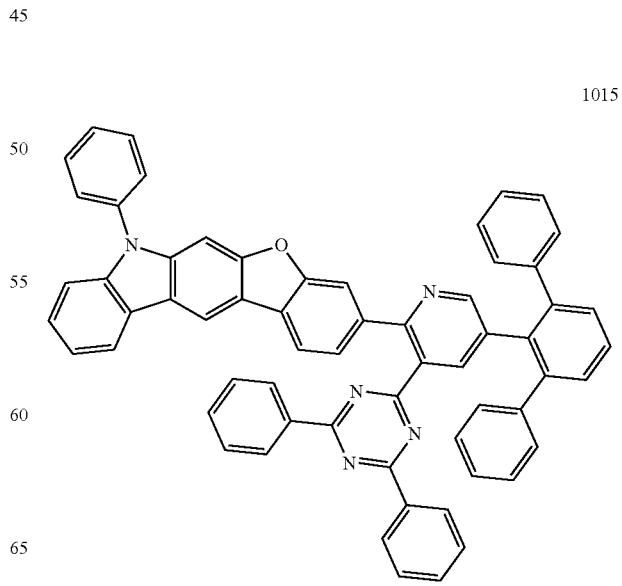

1016
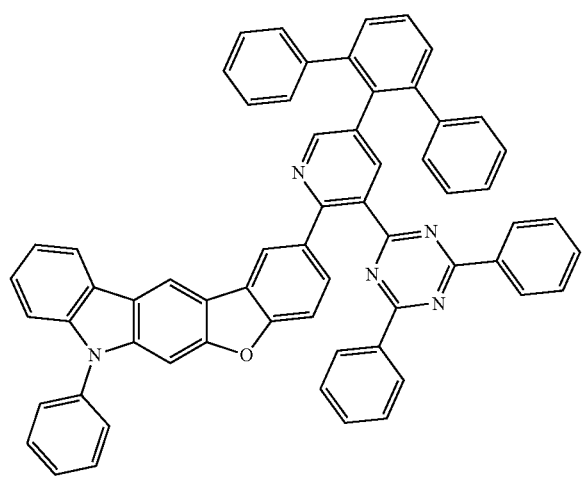
1017
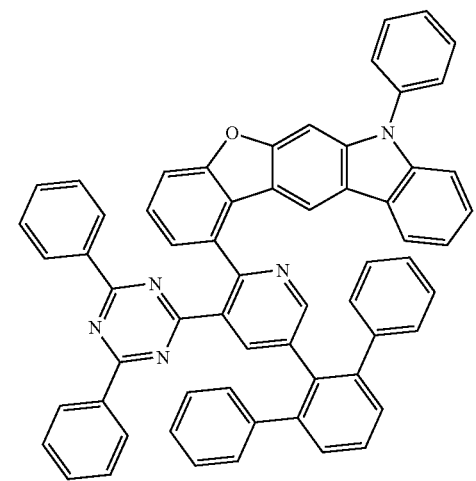
1018
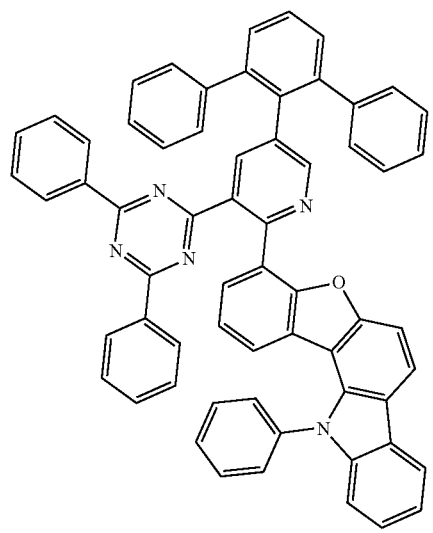
1019
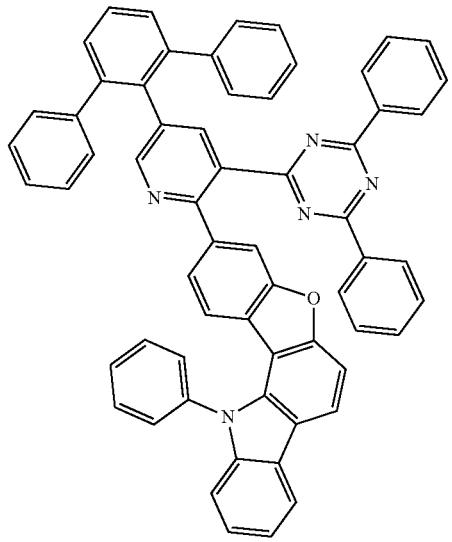
1020
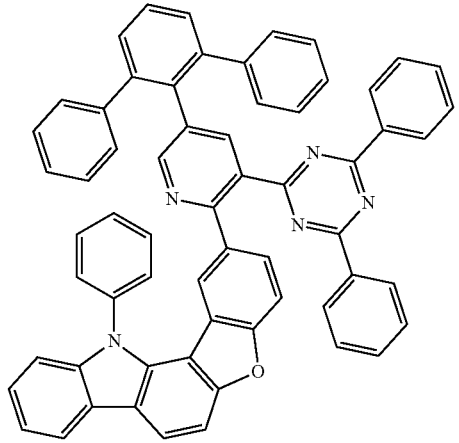
1021
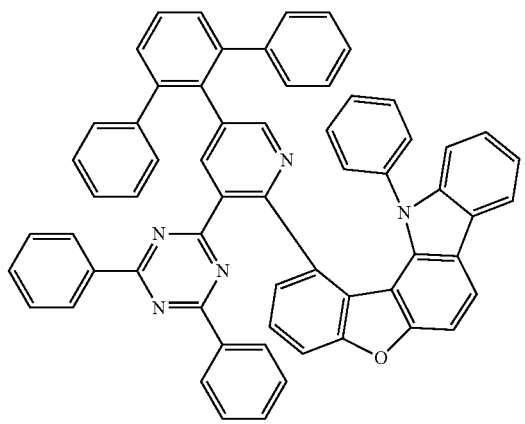

1639
-continued
1022
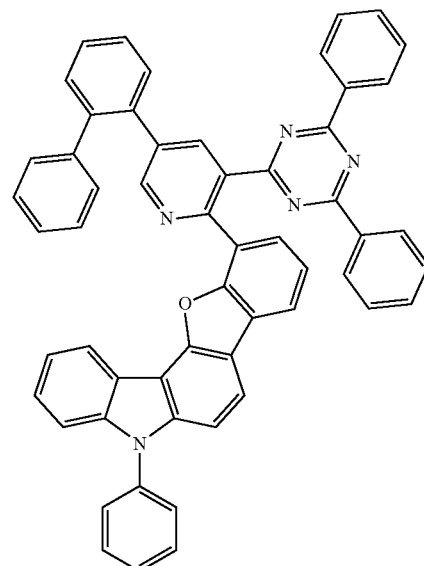
1023
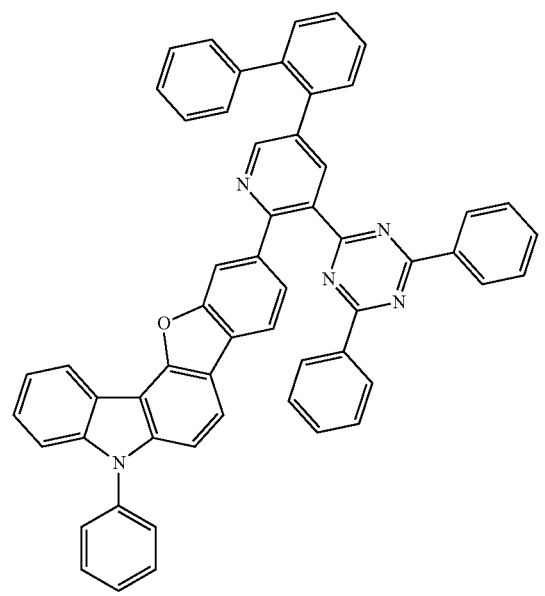
1024
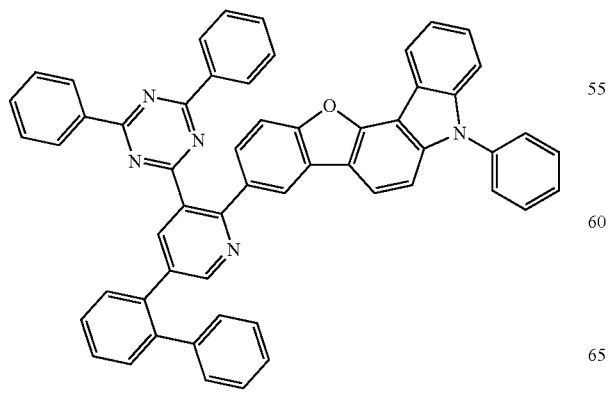
1640
-continued
1025
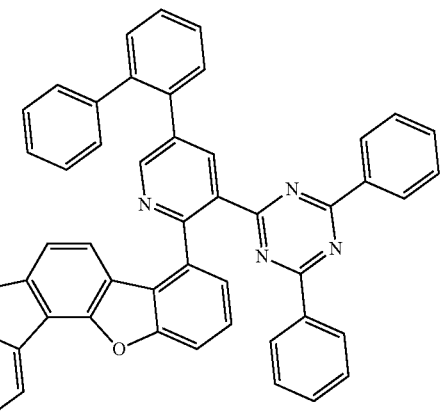
1026
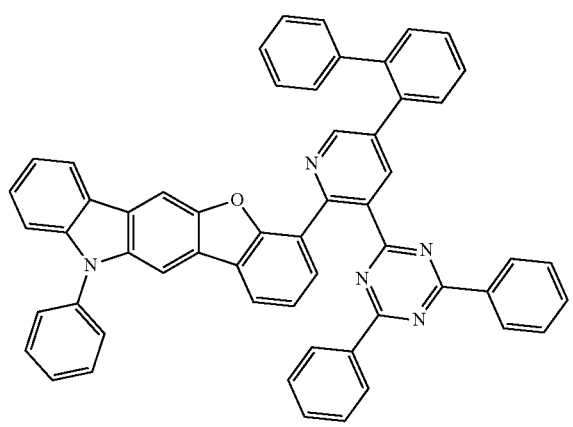
1027
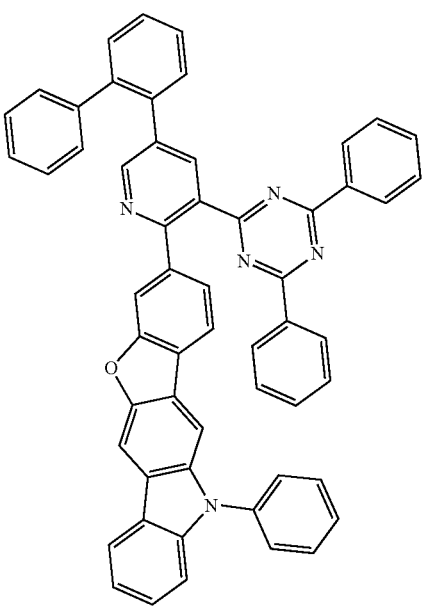

1028
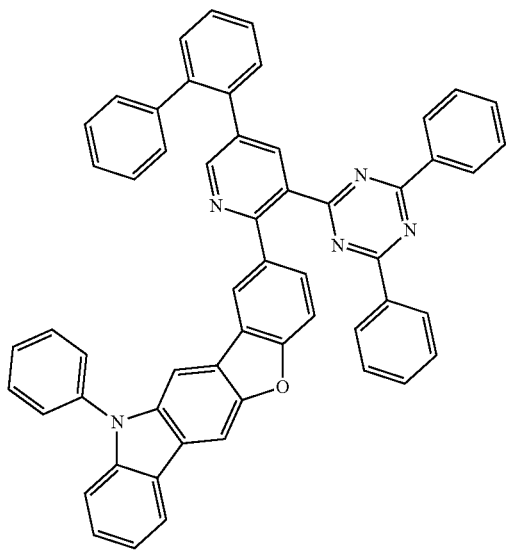
1029
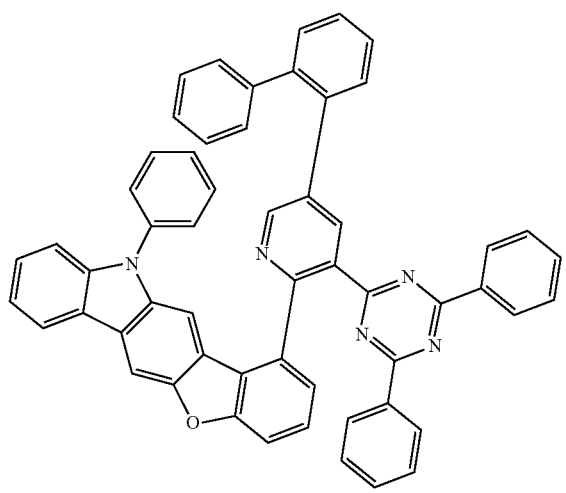
1030
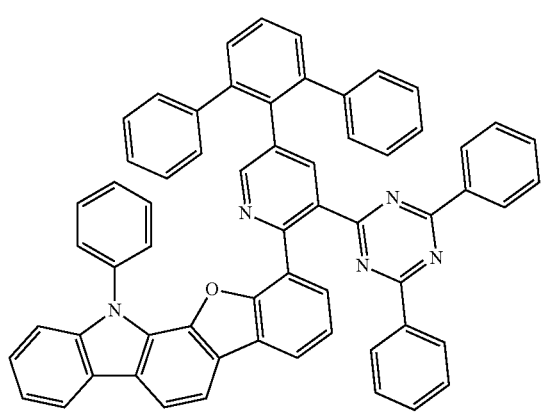
1031
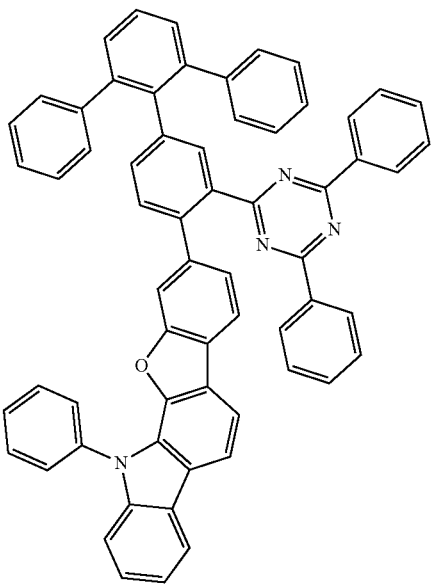
1032
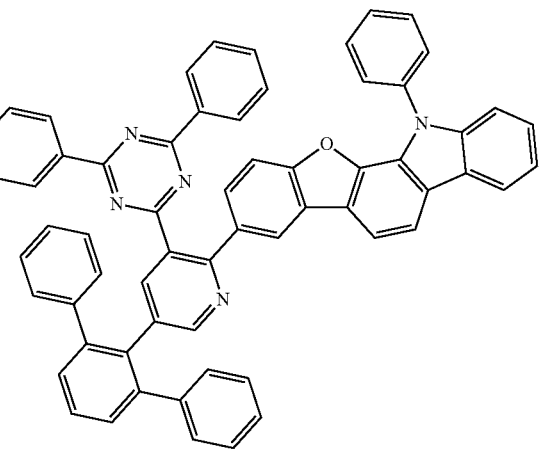
1033
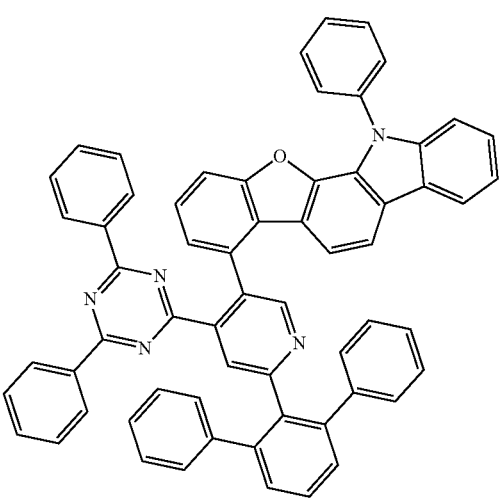

-continued
1034
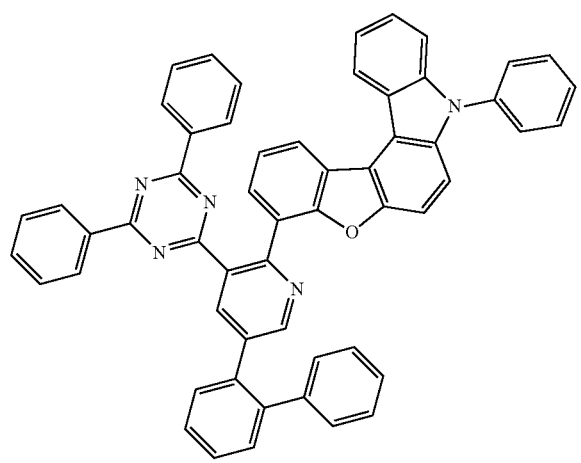
1035
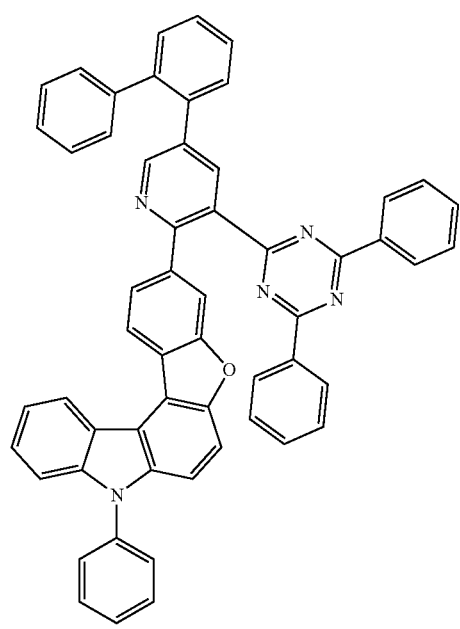
1036
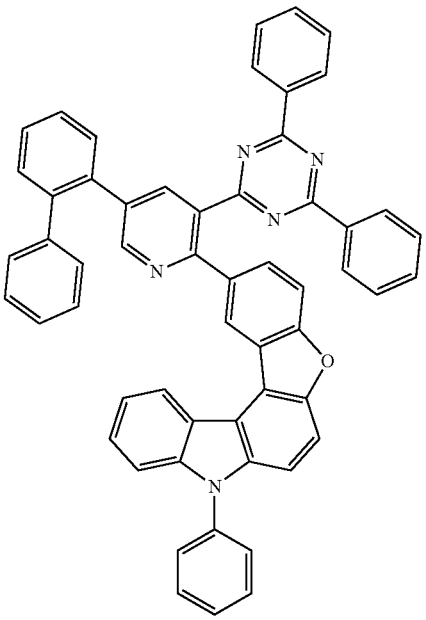
1037
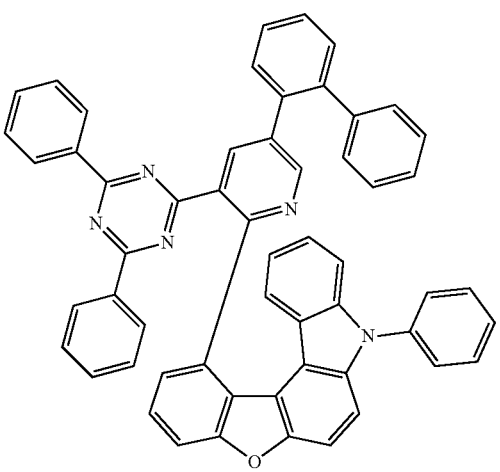
1038
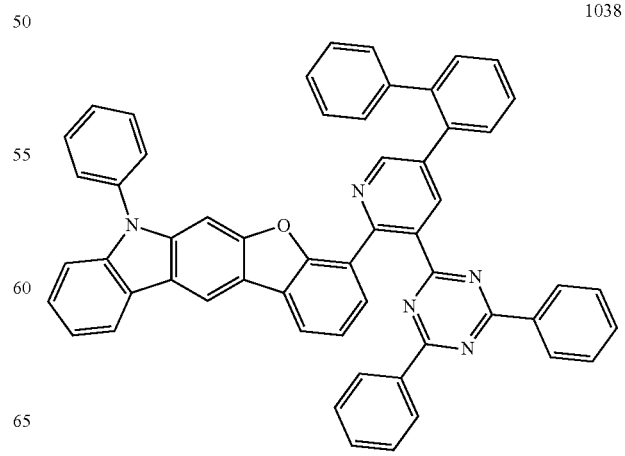

1039
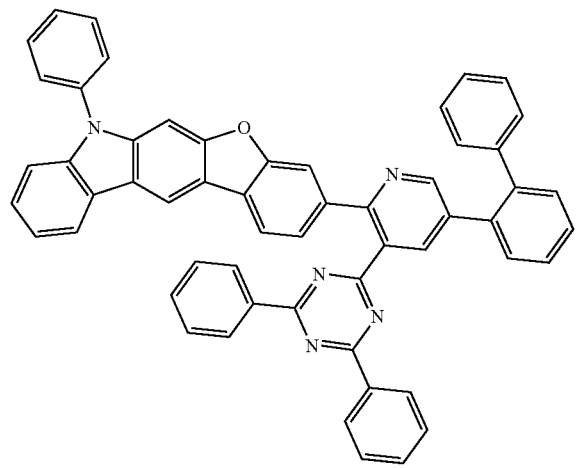
1040
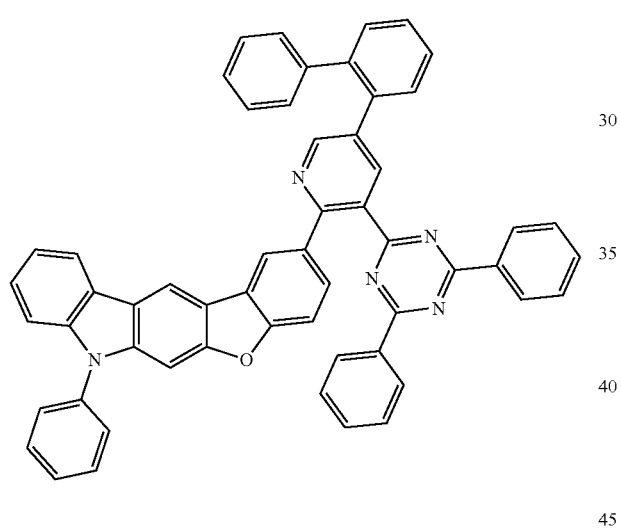
1041
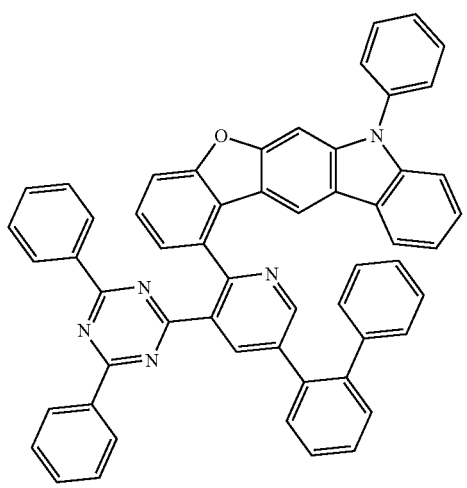
1042
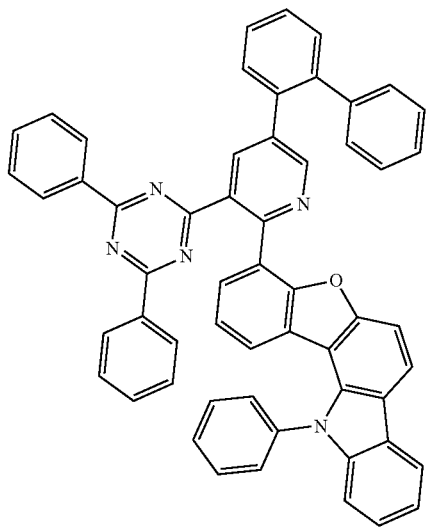
1043
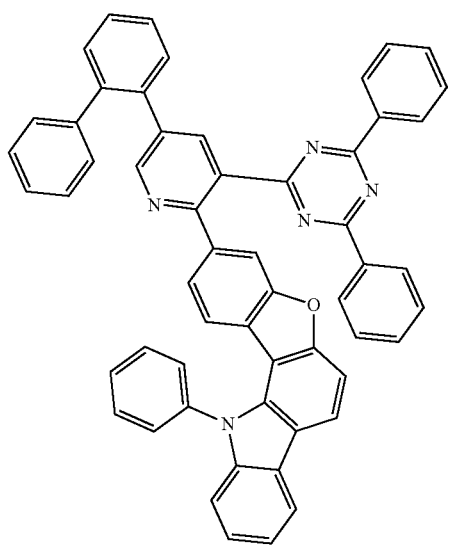
1044
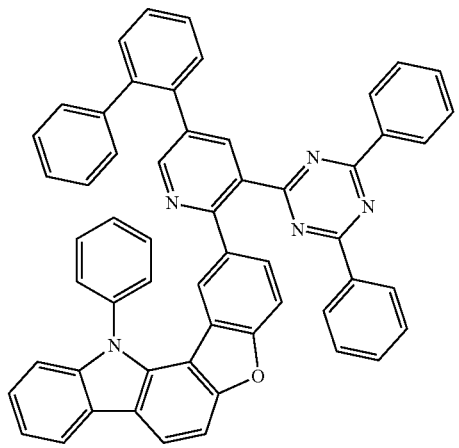

1647
-continued
1045
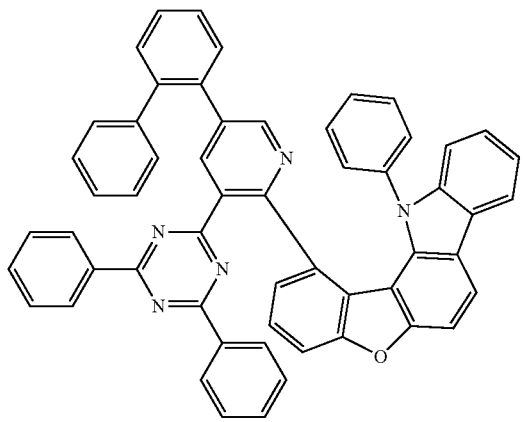
1648
-continued
1047
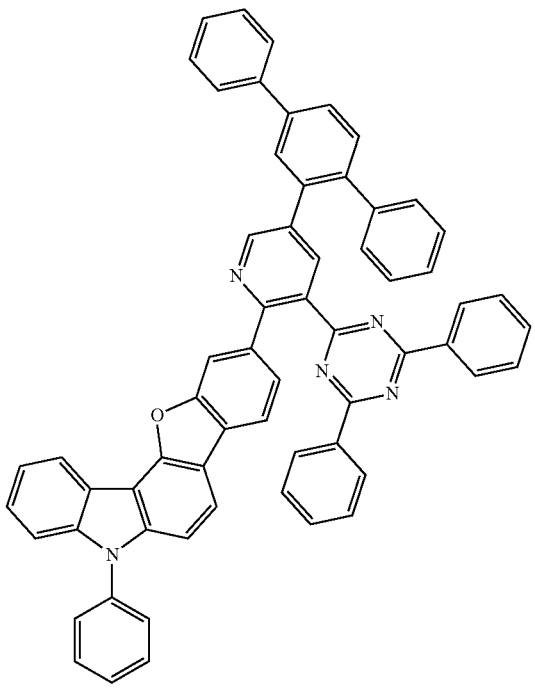
1046
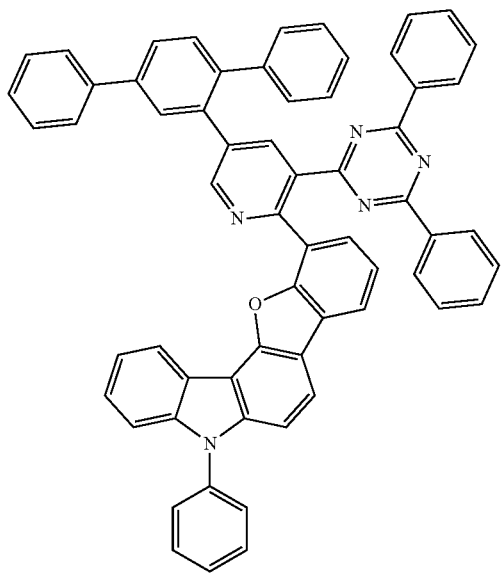
1048
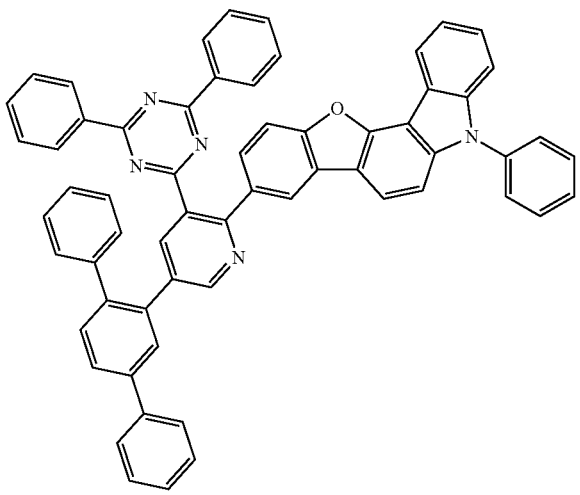

1649
-continued
1049
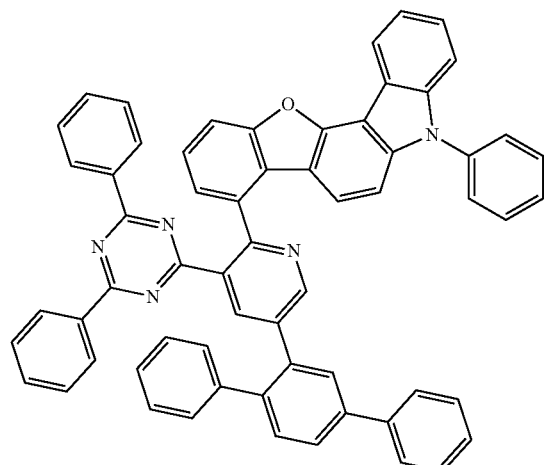
1050
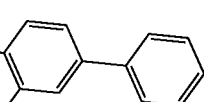
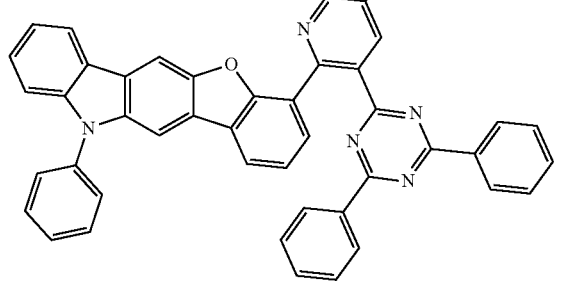
1051
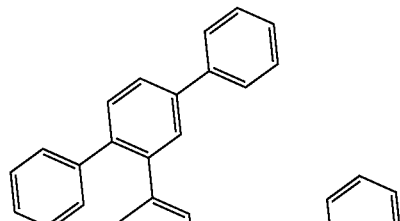
1650
-continued
1052
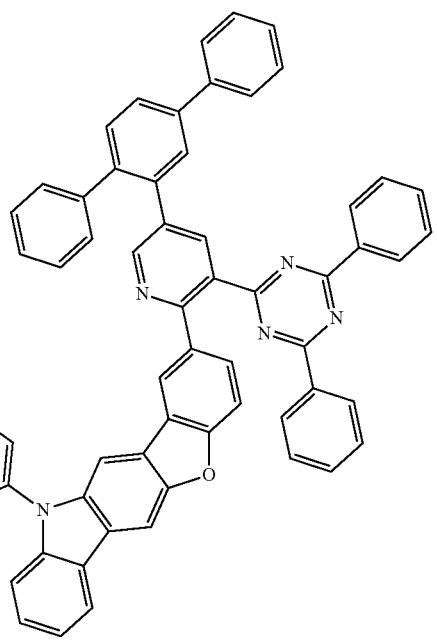
1053
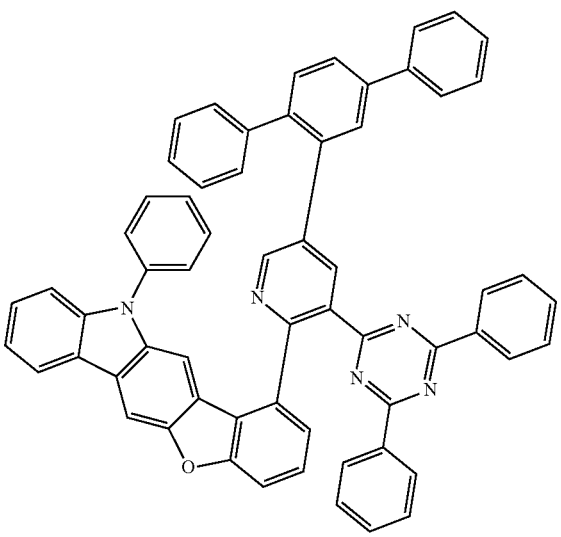
1054
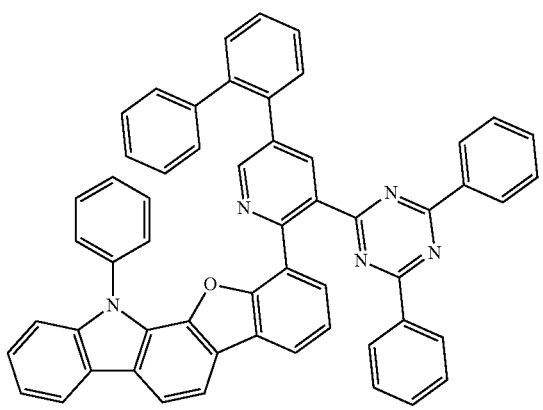

1055
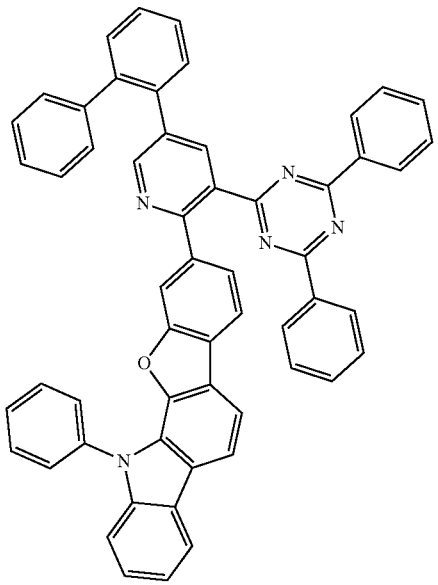
1056
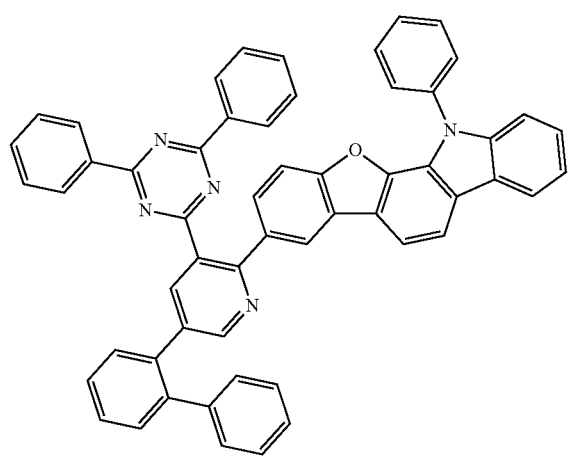
1057
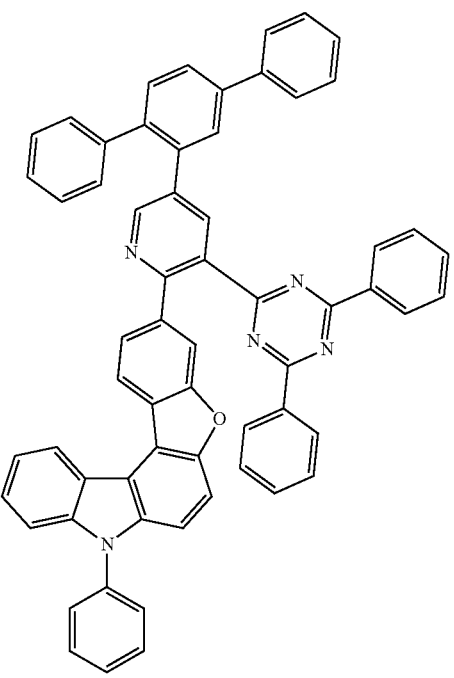
1058
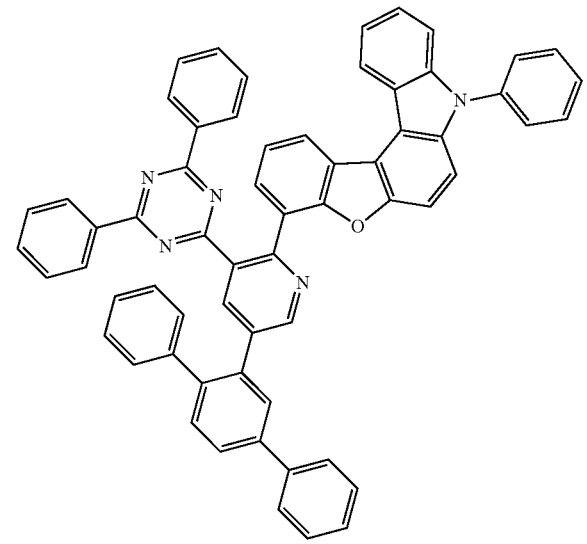
1059

1653
-continued
1060
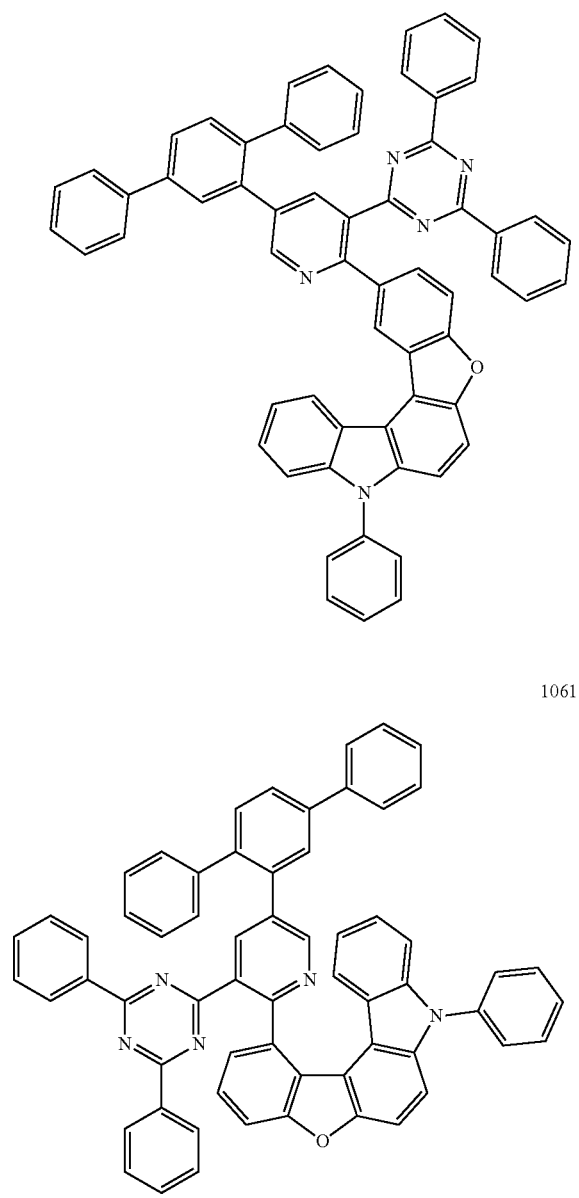
1061
1062
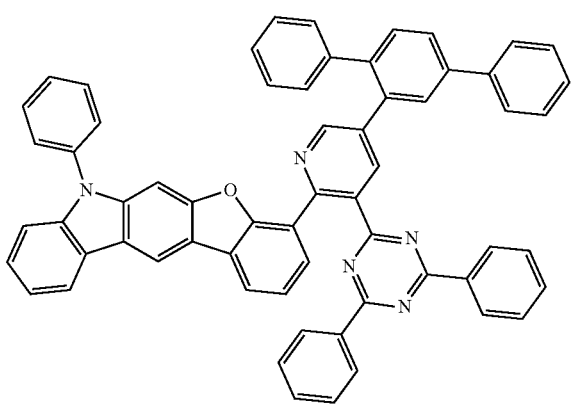
1654
-continued
1063
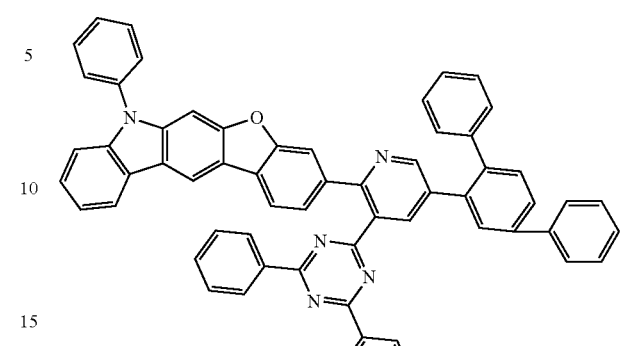
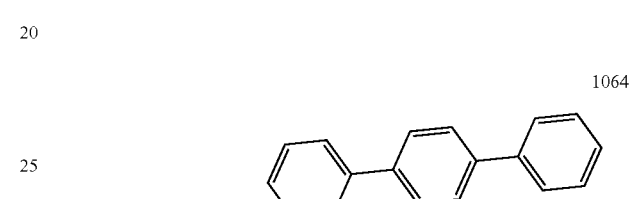
1064
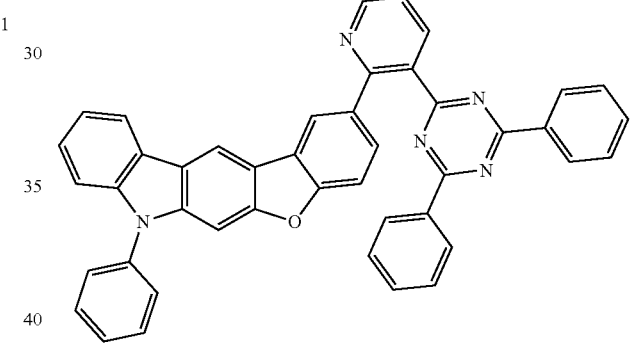
1065
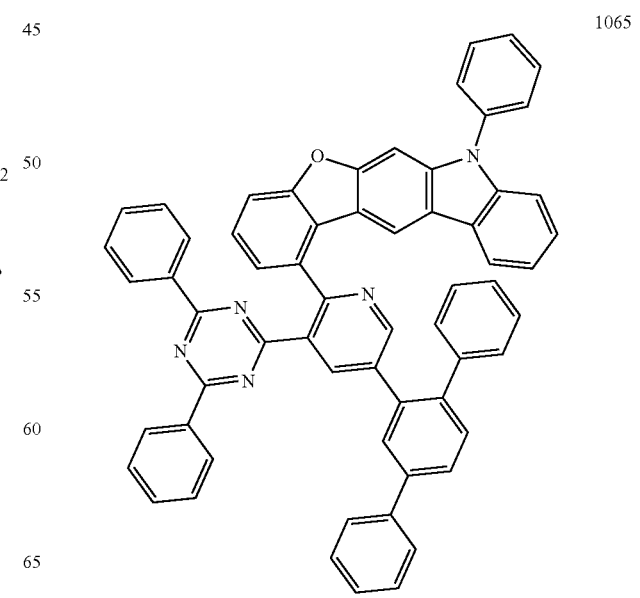

1066
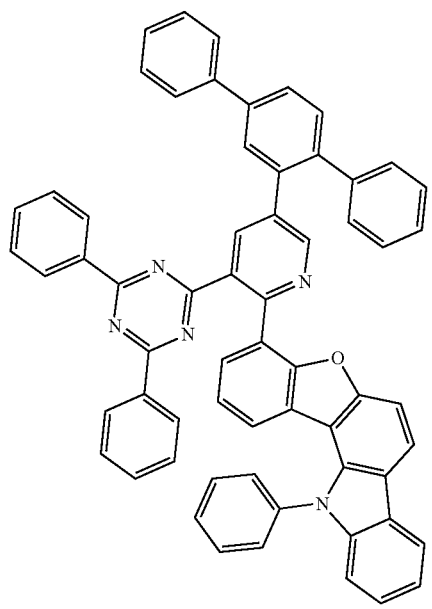
1067
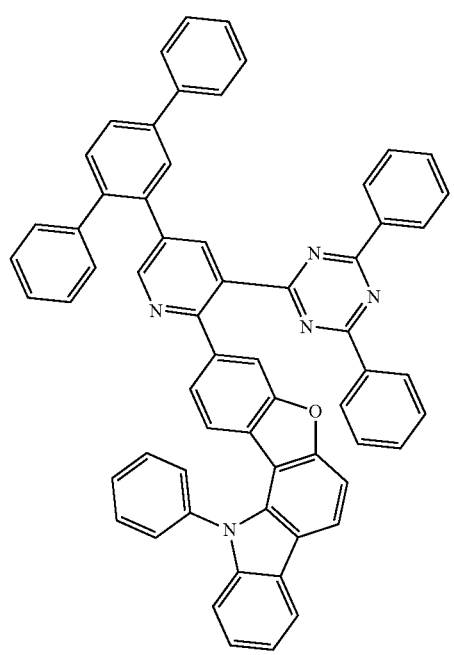
1068
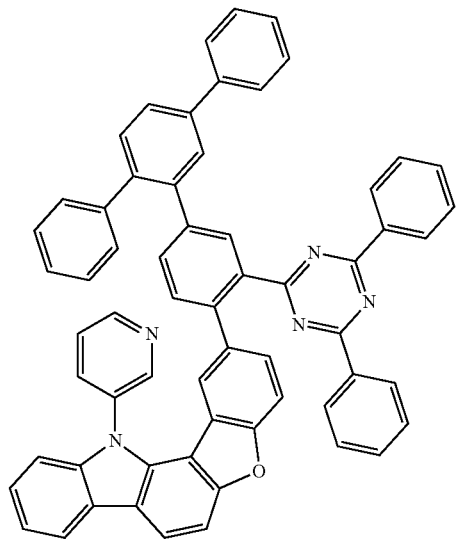
1069
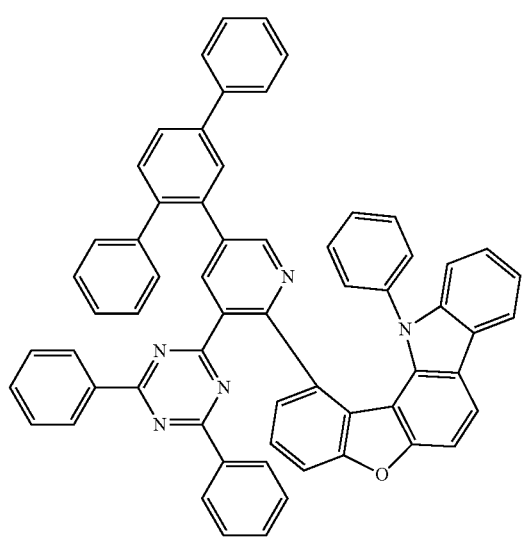
1070
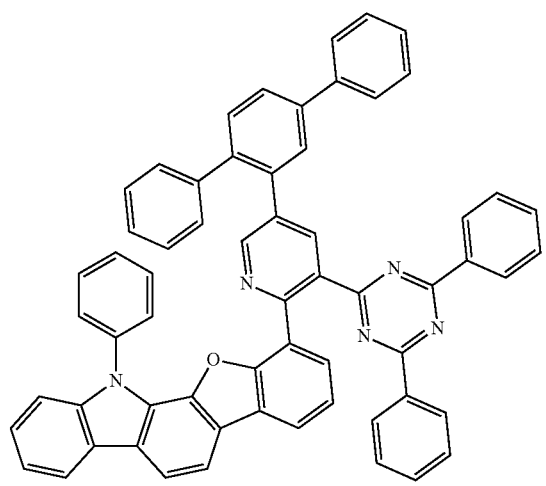

1657
-continued
1071
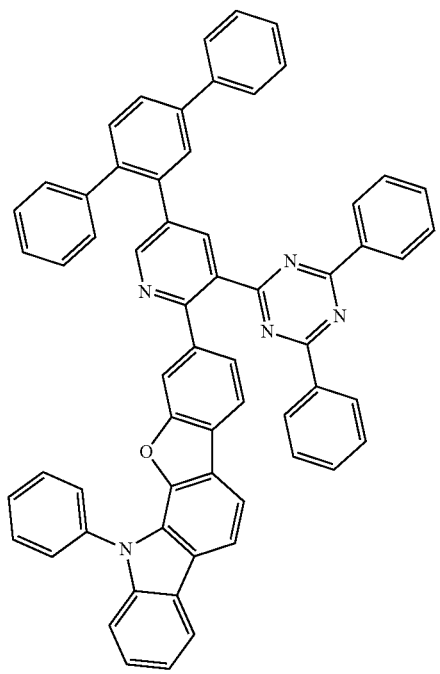
1072
1658
-continued
1073
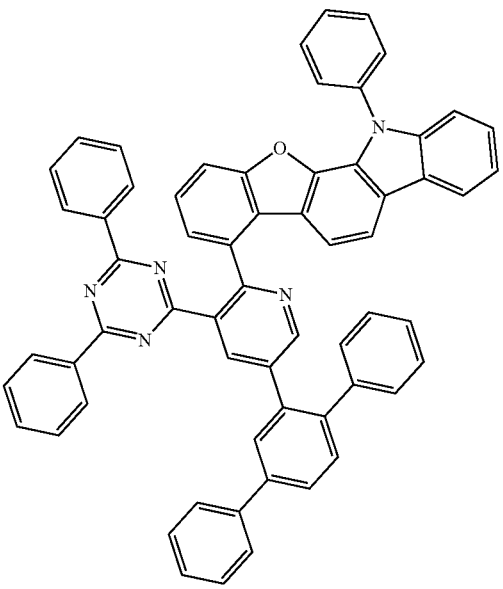
1074
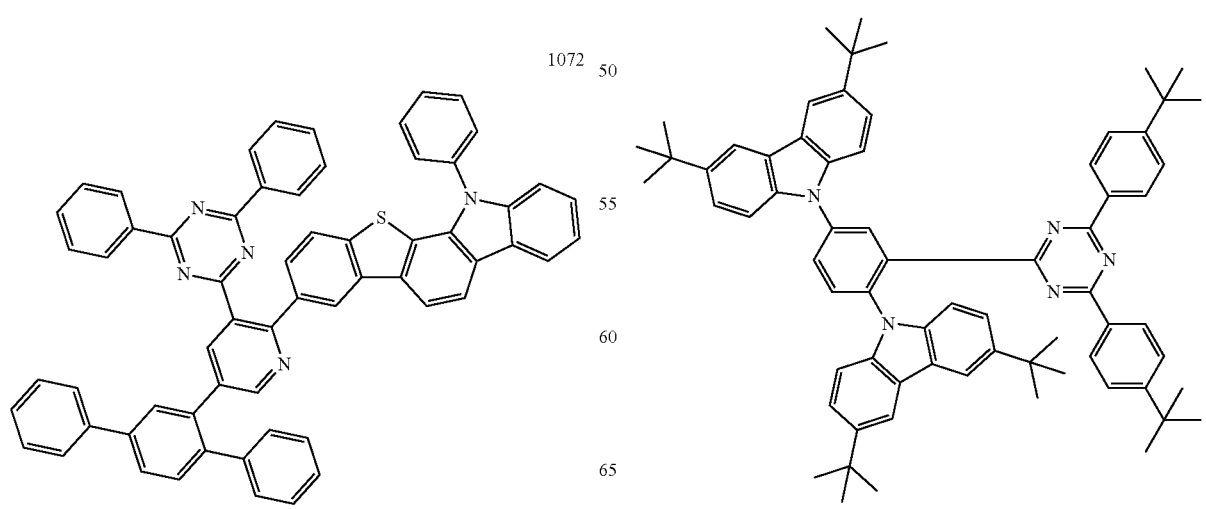

1075
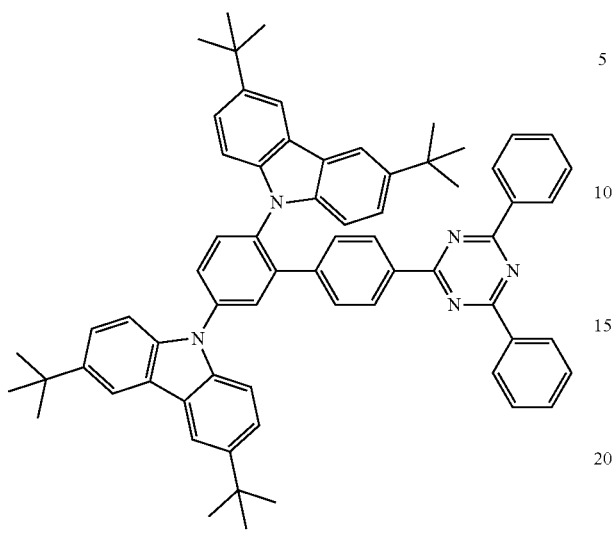
1076
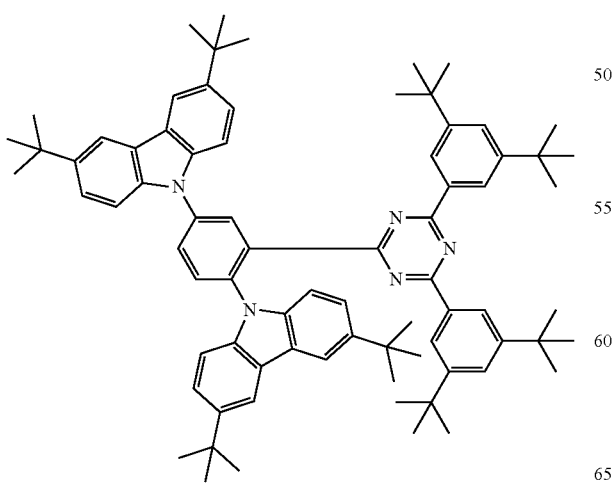
1077
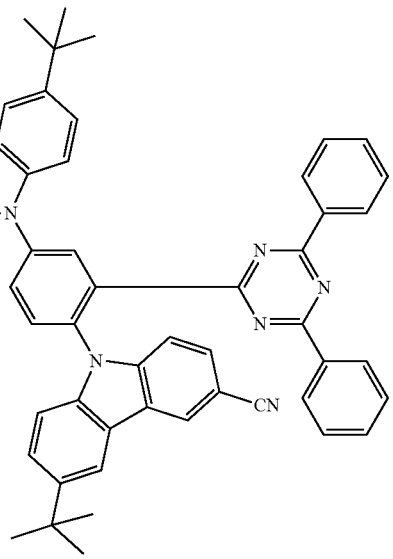
1078
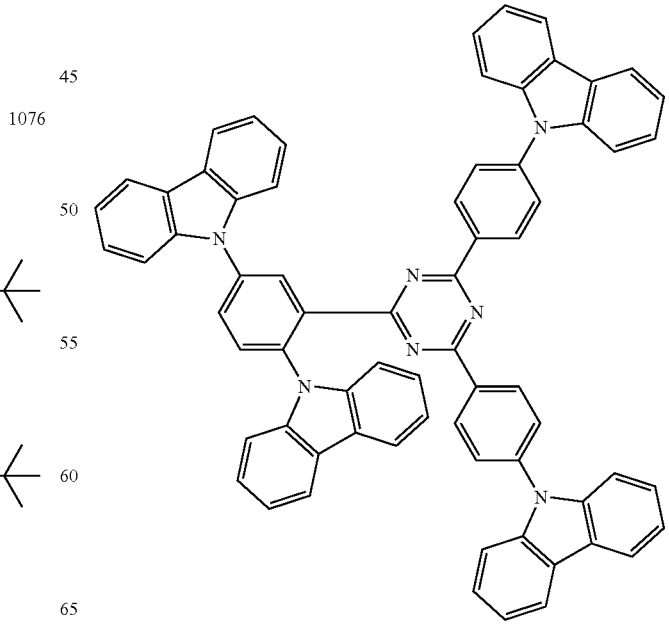

<Group XI>
1661
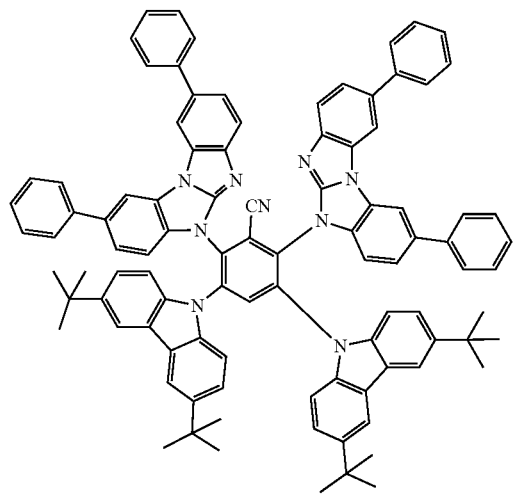
1
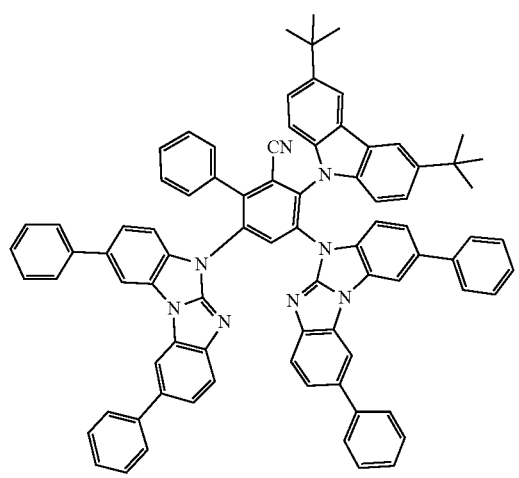
3
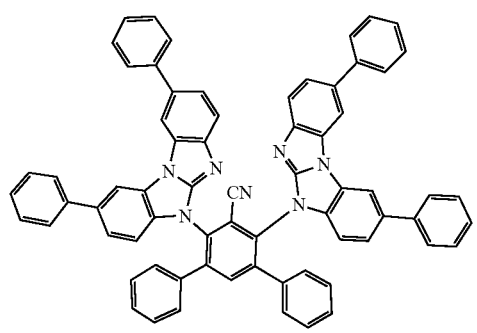
5
1662
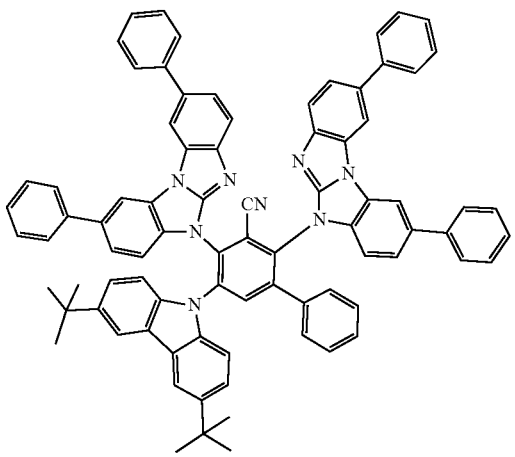
2
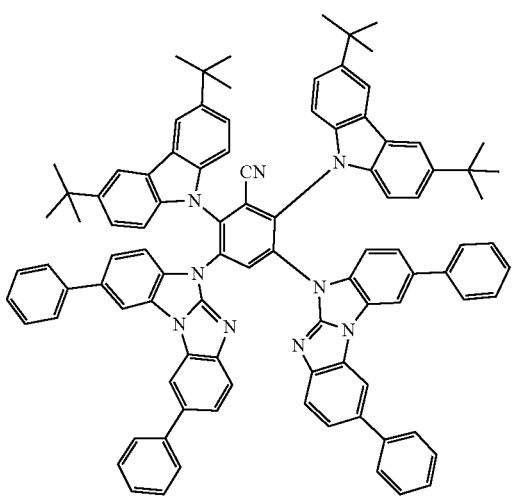
4
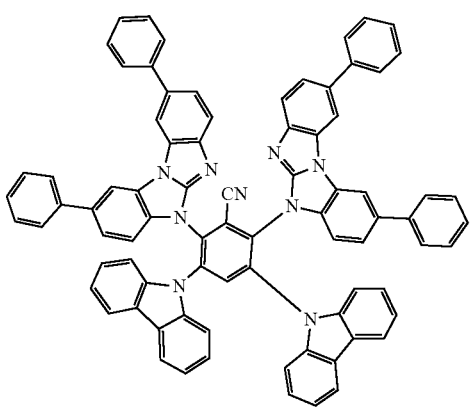
6

-continued
7
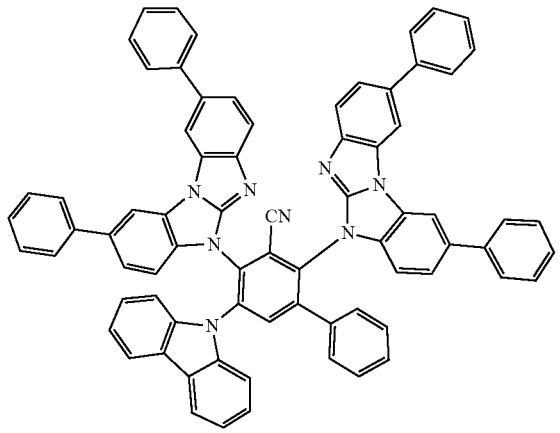
8
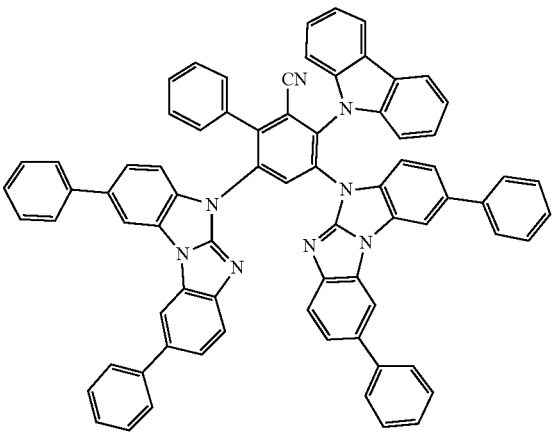
9
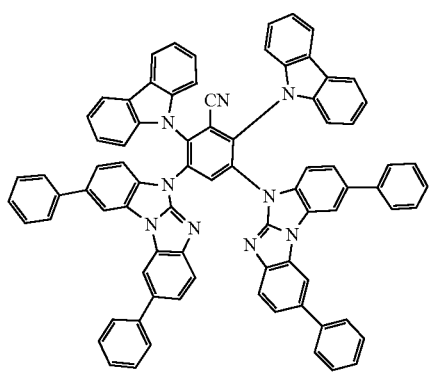
10
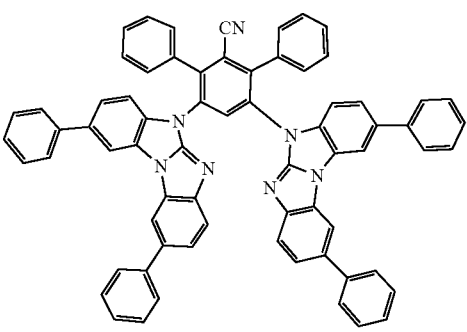
11
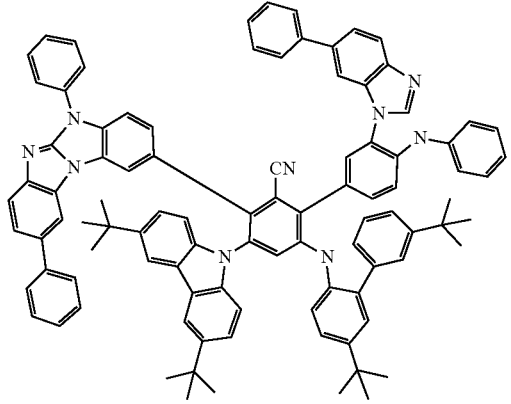
12
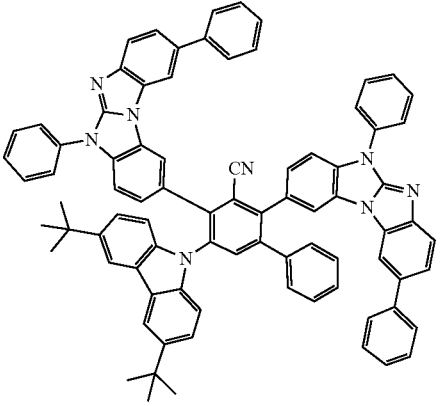
13
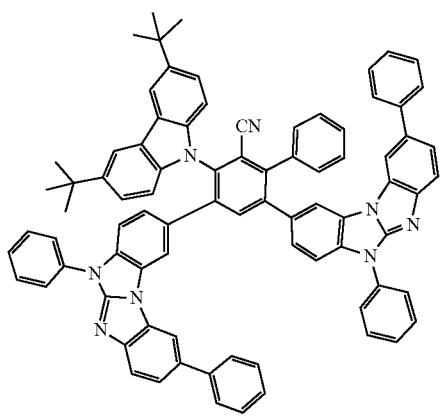
14
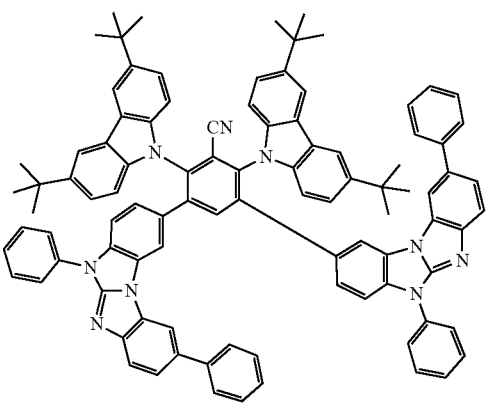

-continued
15
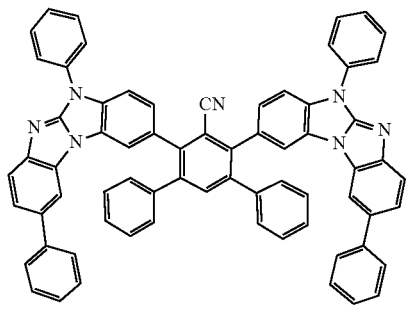
16
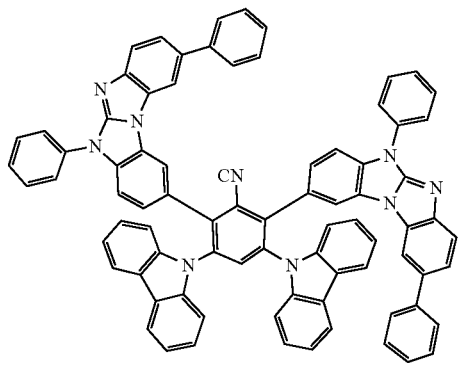
17
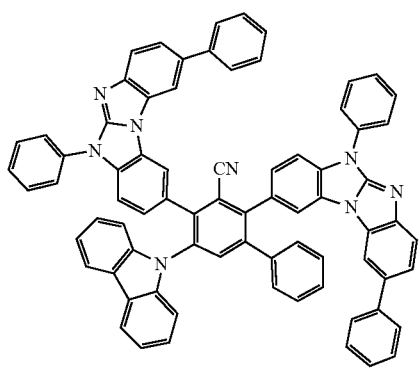
18
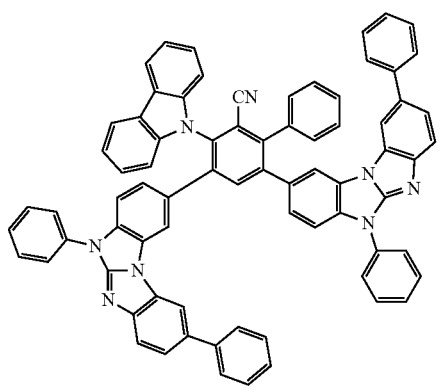
19
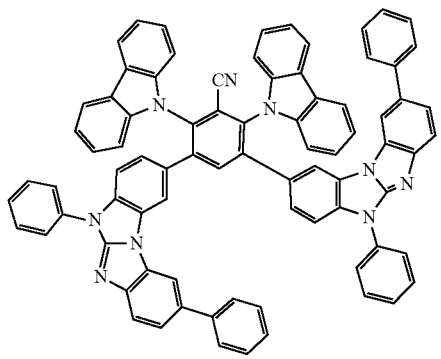
20
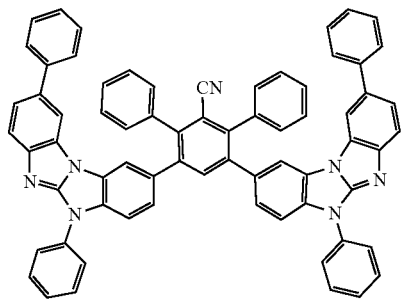
21
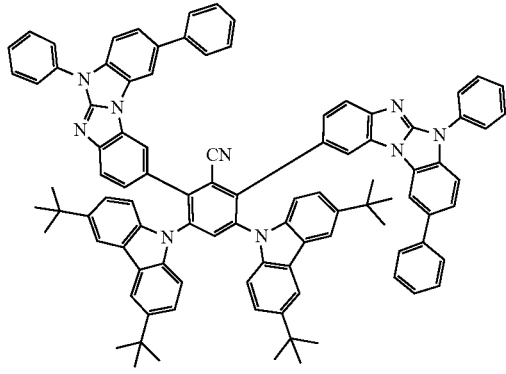
22
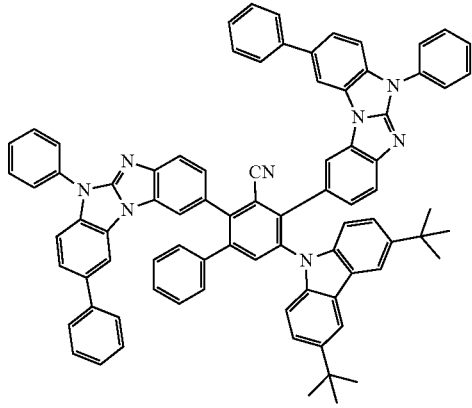

23
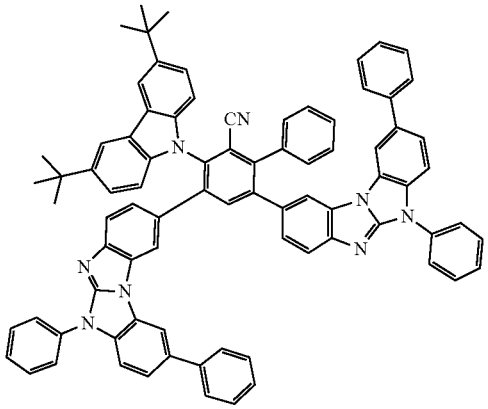
24
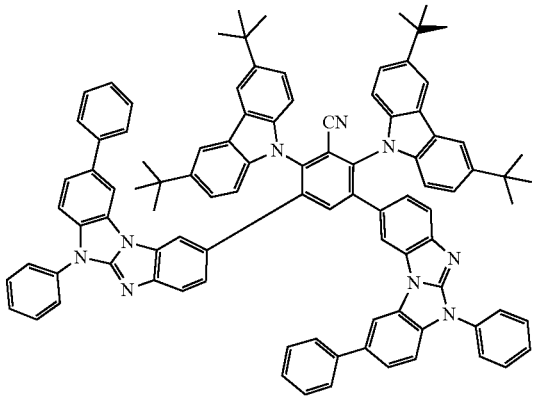
25
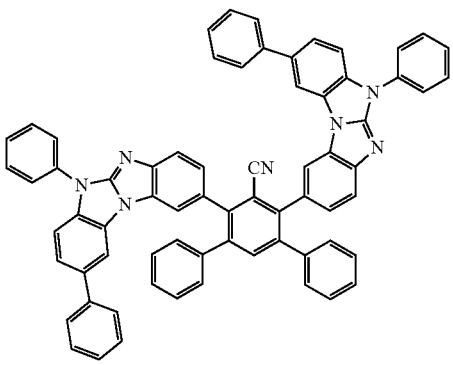
26
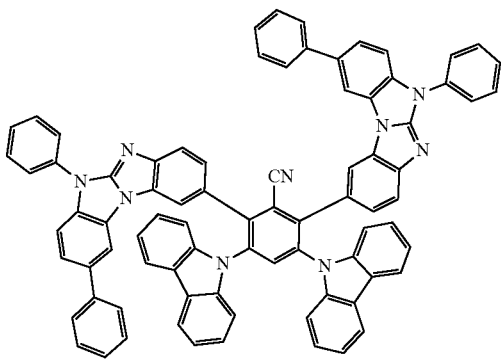
27
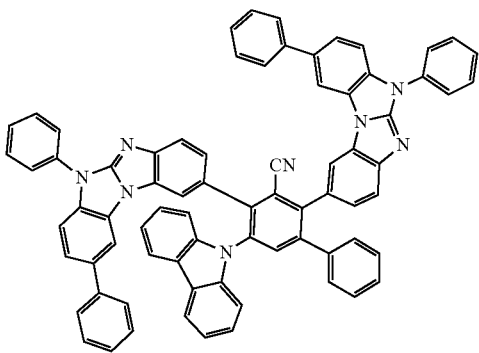
28
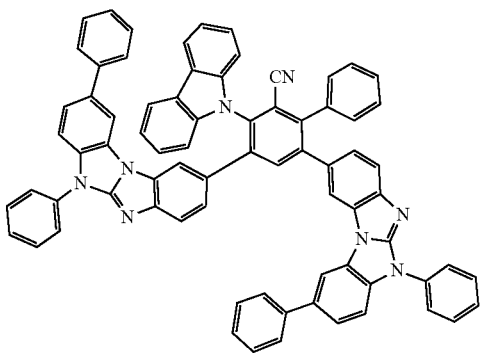
29
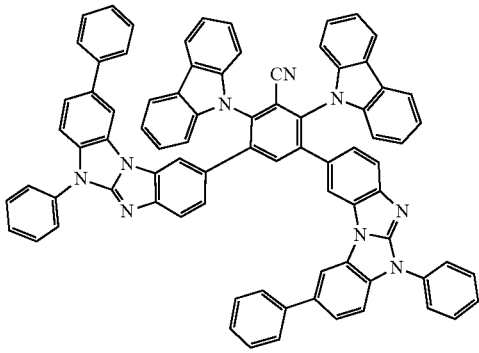
30
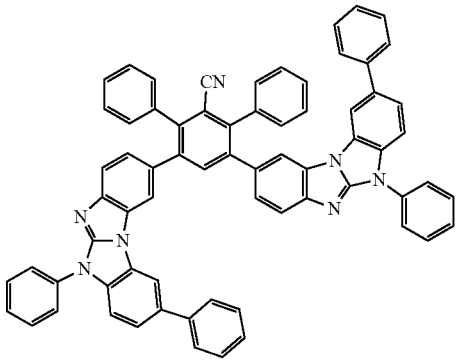

1669 1670
-continued
31
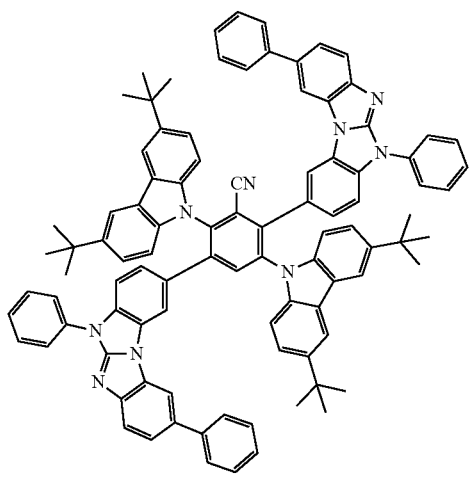
32
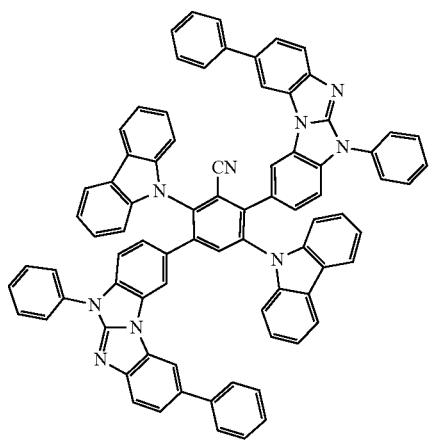
33
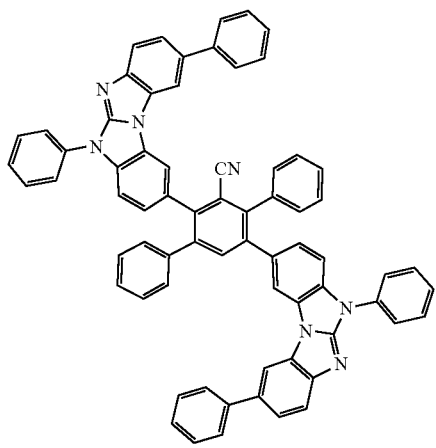
34
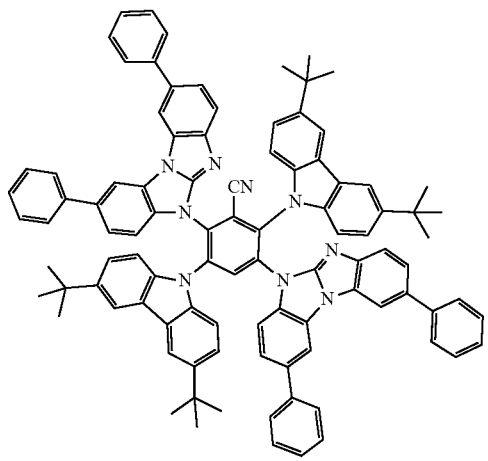
35
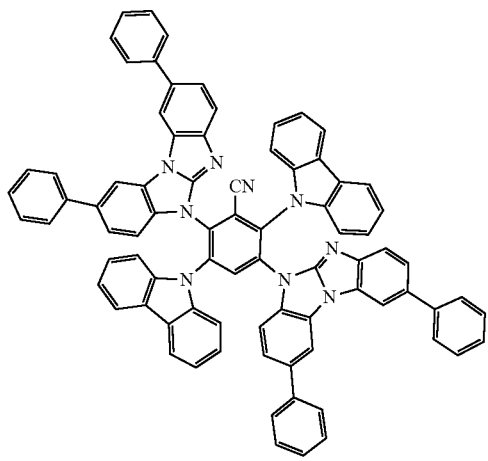
36
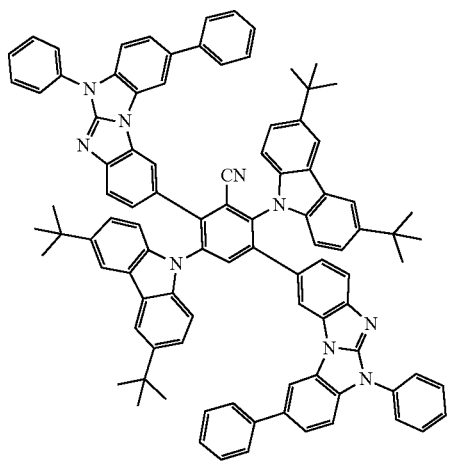

-continued
1671
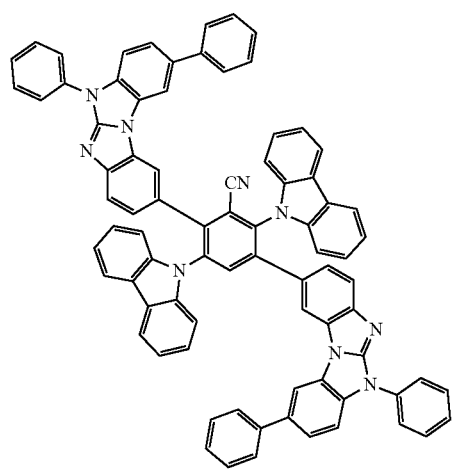
1672
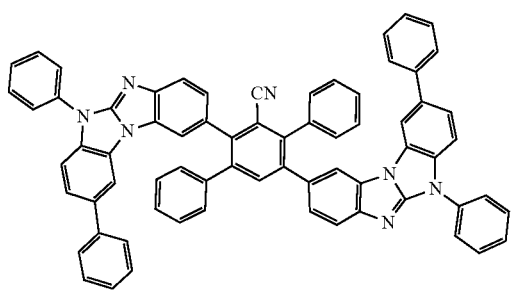
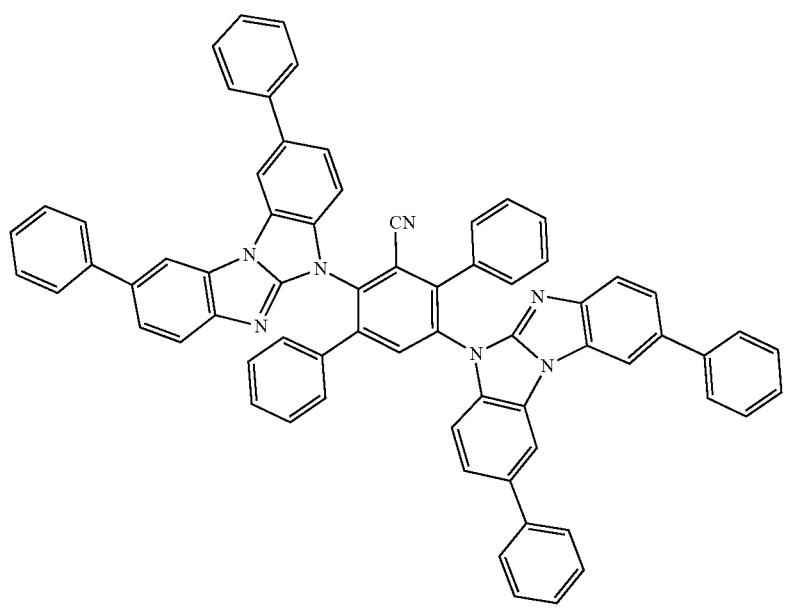

<Group XII>

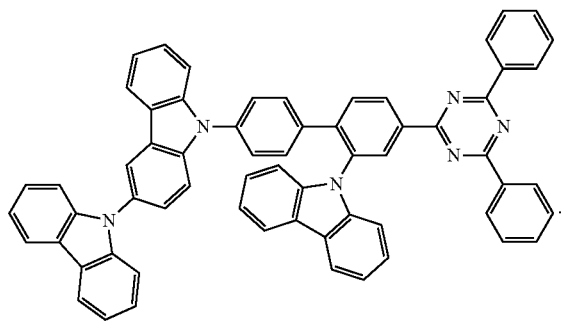 [SMILES: c1ccc(-c2nc(-c3ccccc3)nc(-c3ccc(-c4ccc(-n5c6ccccc6c6cc(-n7c8ccccc8c8ccccc87)ccc65)cc4)c(-n4c5ccccc5c5ccccc54)c3)n2)cc1]

Hole Transport Region 12

In the organic light-emitting device 10, a hole transport region 12 may be disposed between the first electrode 11 and the emission layer 15.

The hole transport region 12 may have a single-layered structure or a multi-layered structure.

For example, the hole transport region 12 may have a hole injection layer structure, a hole transport layer structure, a hole injection layer/hole transport layer structure, a hole injection layer/first hole transport layer/second hole transport layer structure, a hole transport layer/intermediate layer structure, a hole injection layer/hole transport layer/intermediate layer structure, a hole transport layer/electron blocking layer structure, or a hole injection layer/hole transport layer/electron blocking layer structure, but embodiments of the present disclosure are not limited thereto.

The hole transport region 12 may include any compound having hole transport properties.

For example, the hole transport region 12 may include an amine-based compound.

In one or more embodiments, the hole transport region 12 may include at least one compound represented by Formulae 201 to 205, but embodiments of the present disclosure are not limited thereto:

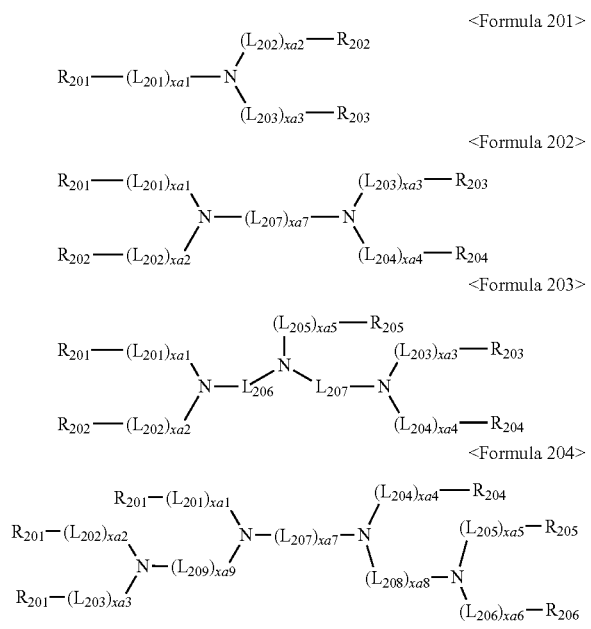

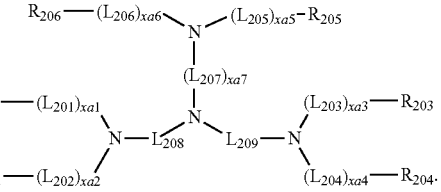

<Formula 205>

In Formulae 201 to 205, $L_{201}$ to $L_{209}$ may each independently be *—O—*', *—S—*', a substituted or unsubstituted $C_5$-$C_{60}$ carbocyclic group, or a substituted or unsubstituted $C_1$-$C_{60}$ heterocyclic group, xa1 to xa9 may each independently be an integer from 0 to 5, and $R_{201}$ to $R_{206}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, wherein two adjacent a group among $R_{201}$ to $R_{206}$ may optionally be linked to each other via a single bond, a dimethyl-methylene group, or a diphenyl-methylene group.

For example, $L_{201}$ to $L_{206}$ may each independently be a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group, each unsubstituted or substituted with at least one deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —Si($Q_{11}$)($Q_{12}$)($Q_{13}$), or any combination thereof, xa1 to xa9 may each independently be 0, 1, or 2, $R_{201}$ to $R_{206}$ may each independently be a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an indeno carbazolyl group, an indolocarbazolyl group, a benzofurocarbazolyl group, or a benzothienocarbazolyl group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), or any combination thereof, and $Q_{11}$ to $Q_{13}$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

In one or more embodiments, the hole transport region 12 may include a carbazole-containing amine-based compound.

In one or more embodiments, the hole transport region 12 may include a carbazole-containing amine-based compound and a non-carbazole-containing amine-based compound.

The carbazole-containing amine-based compound may be, for example, a compound represented by Formula 201 further including, in addition to a carbazole group, at least one of a dibenzofuran group, a dibenzothiophene group, a fluorene group, a spiro-bifluorene group, an indenocarbazole group, an indolocarbazole group, a benzofurocarbazole group, a benzothienocarbazole group, or any combination thereof.

The non-carbazole-containing amine-based compound may be, for example, a compound represented by Formula 201 not including a carbazole group, but including at least one of a dibenzofuran group, a dibenzothiophene group, a fluorene group, a spiro-bifluorene group, an indenocarbazole group, an indolocarbazole group, a benzofurocarbazole group, a benzothienocarbazole group, or any combination thereof.

In one or more embodiments, the hole transport region 12 may include at least one compound represented by Formulae 201 and 202.

In one or more embodiments, the hole transport region 12 may include at least one compound represented by Formulae 201-1, 202-1, and 201-2, but embodiments of the present disclosure are not limited thereto:

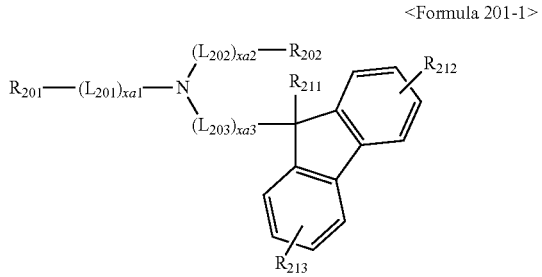

<Formula 201-1>

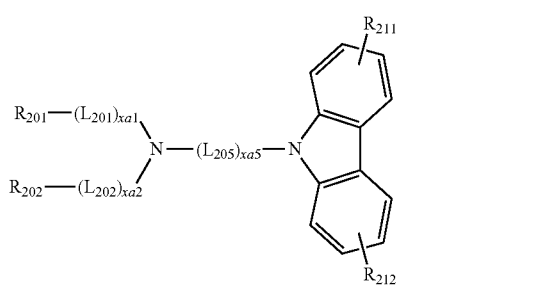

<Formula 202-1>

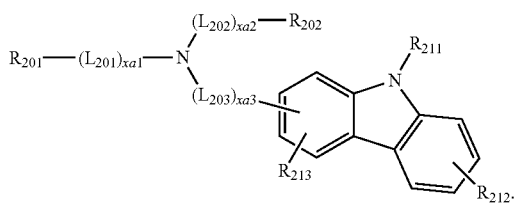

<Formula 201-2>

In Formulae 201-1, 202-1, and 201-2, $L_{201}$ to $L_{203}$, $L_{205}$, xa1 to xa3, xa5, $R_{201}$, and $R_{202}$ may each be understood by referring to the descriptions thereof presented herein, and $R_{211}$ to $R_{213}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a dimethylfluorenyl group, a diphenyla fluorenyl group, a triphenylenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.

For example, the hole transport region 12 may include at least one compound of Compounds HT1 to HT39, but embodiments of the present disclosure are not limited thereto:

1677
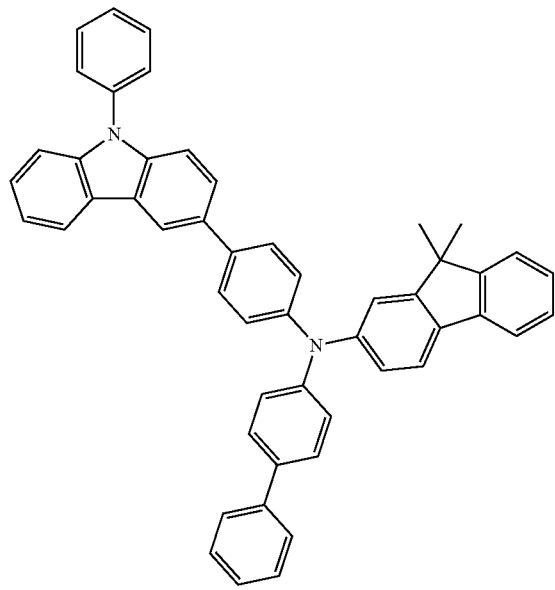
1678
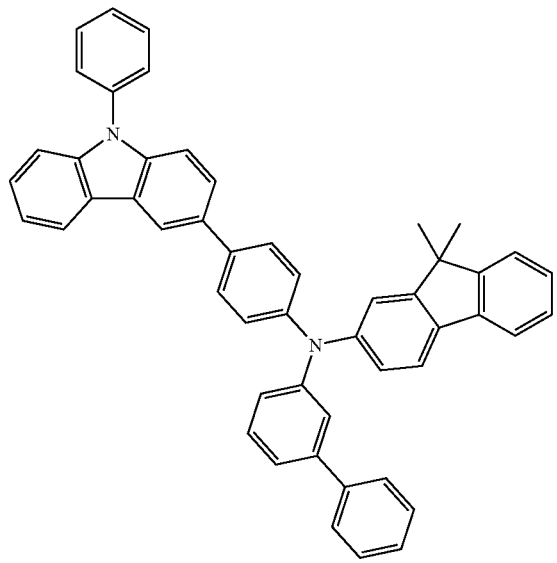
HT1
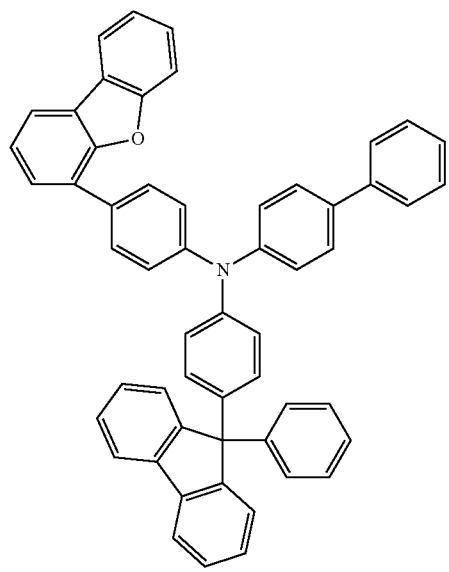
HT2
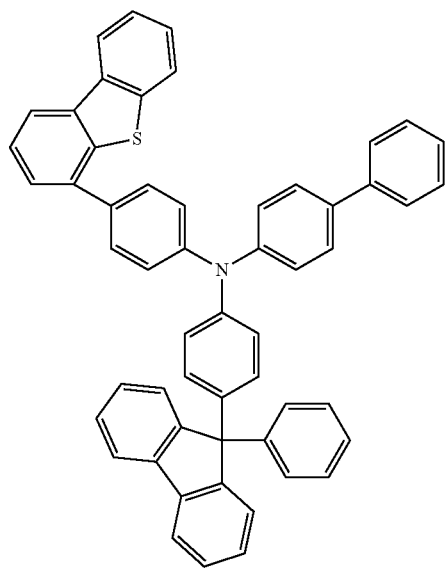
HT3
HT4

-continued
HT5
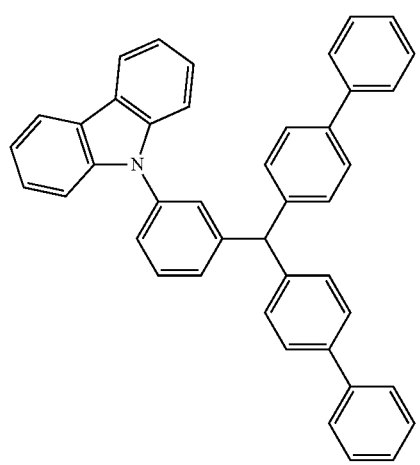
HT6
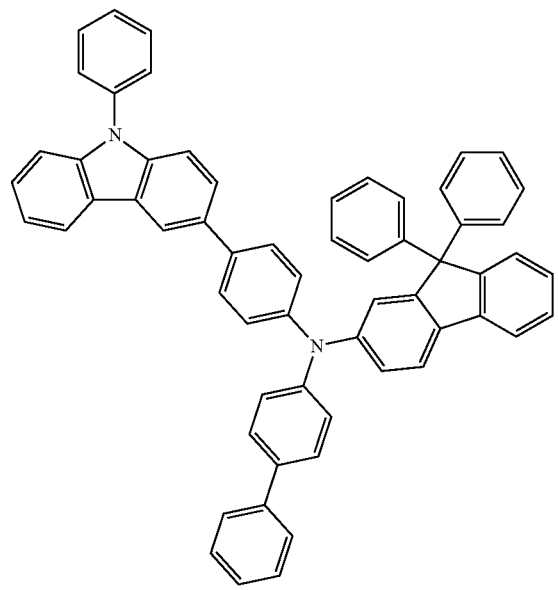
HT13
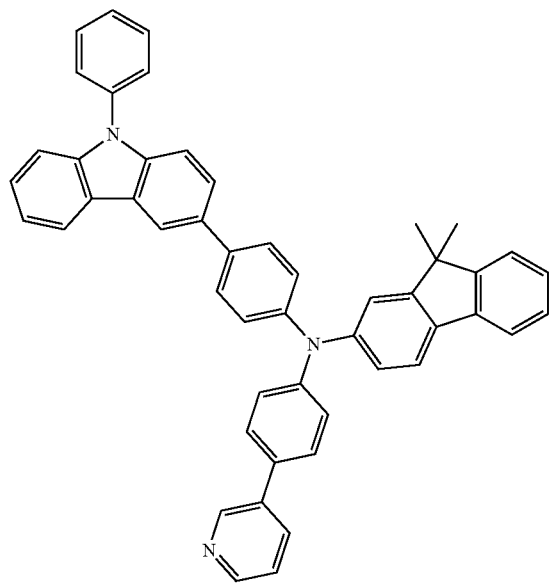
HT14
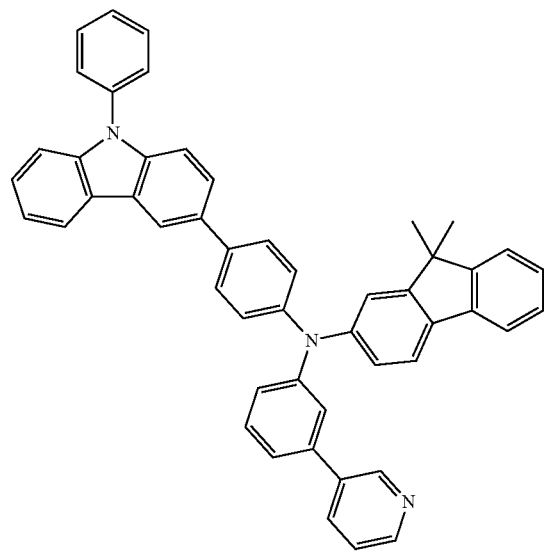

-continued
HT15
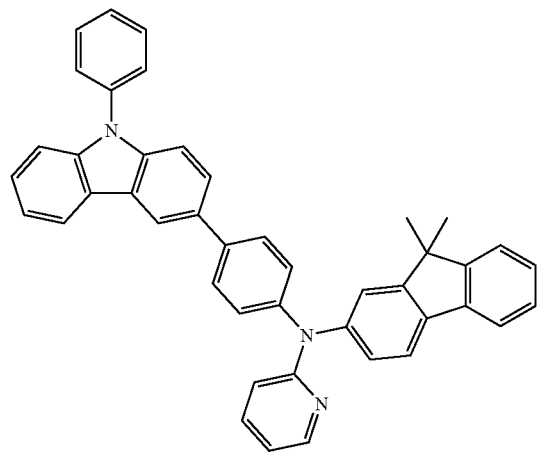
HT16
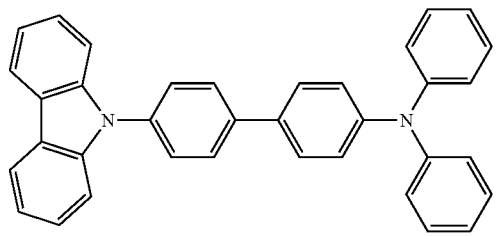
HT17
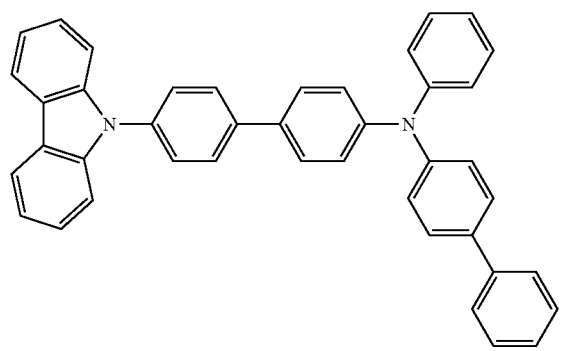
HT18
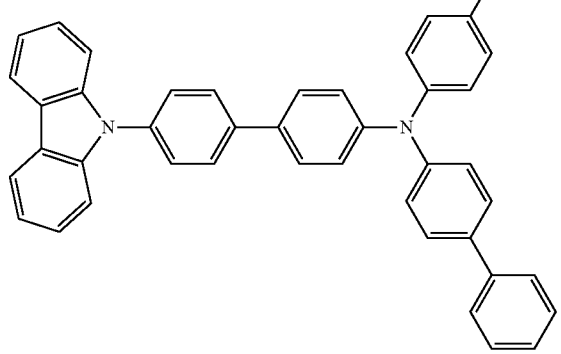
HT19
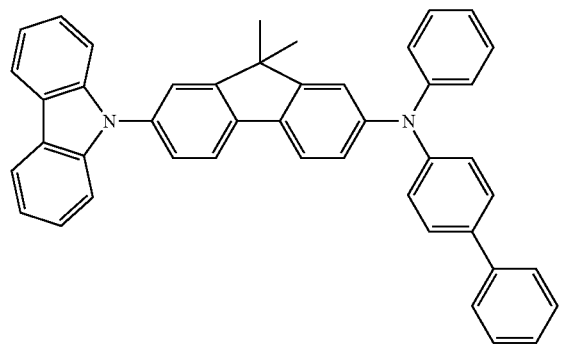
HT20
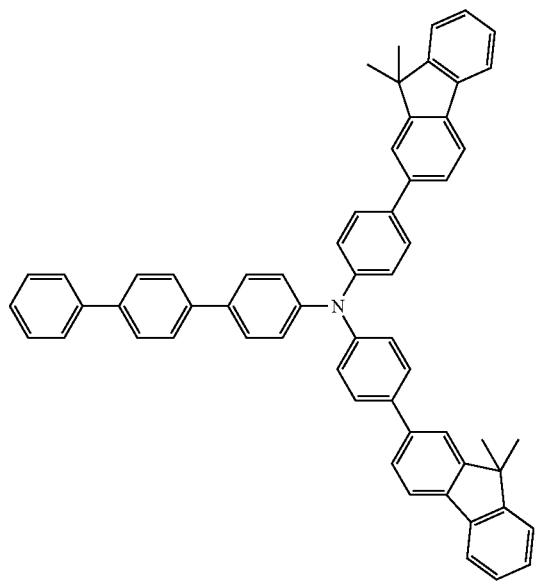

-continued
HT21
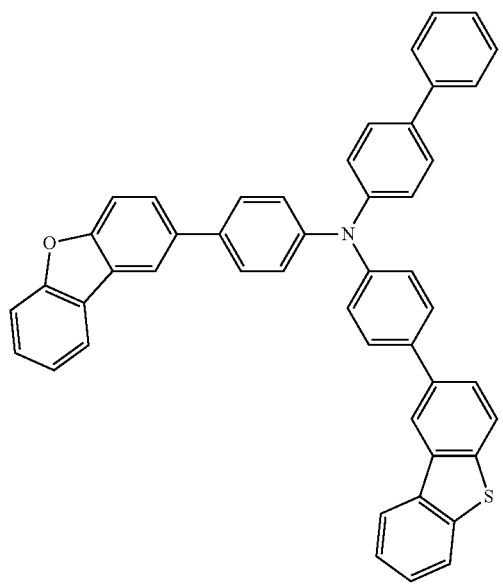
HT22
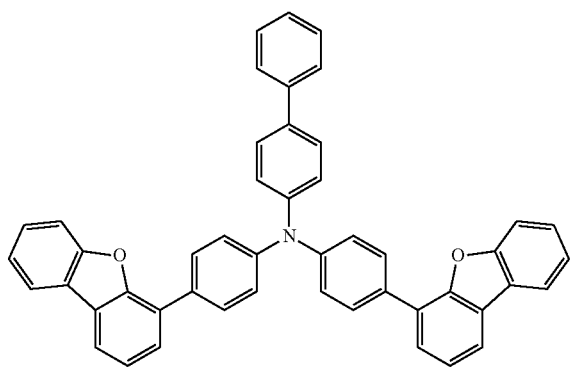
HT23
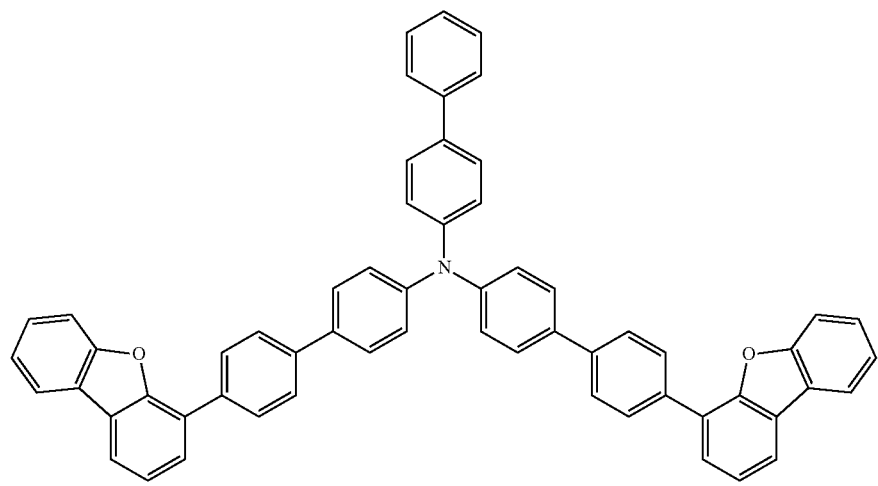

-continued
HT24
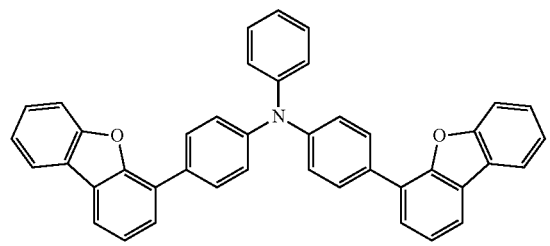
HT25
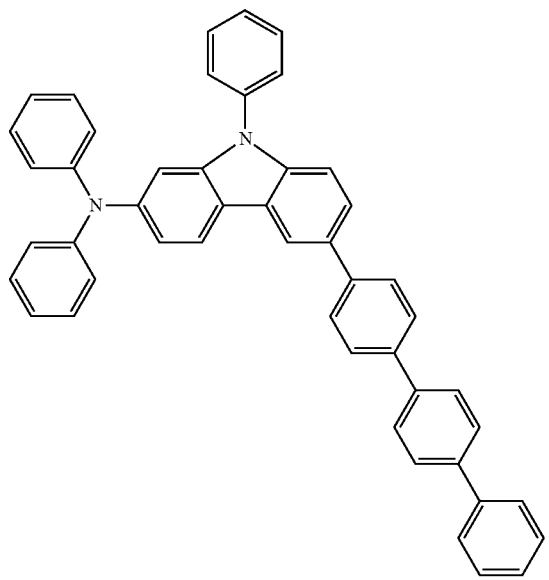
HT26
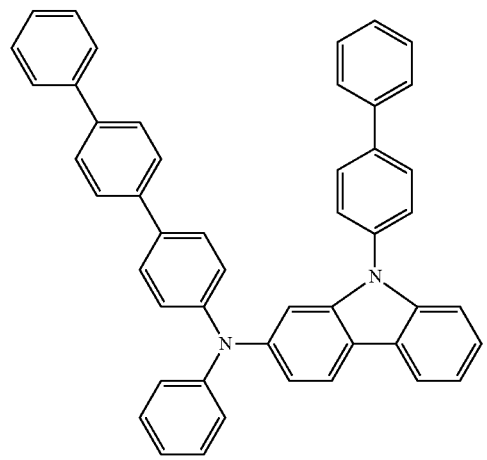
HT27
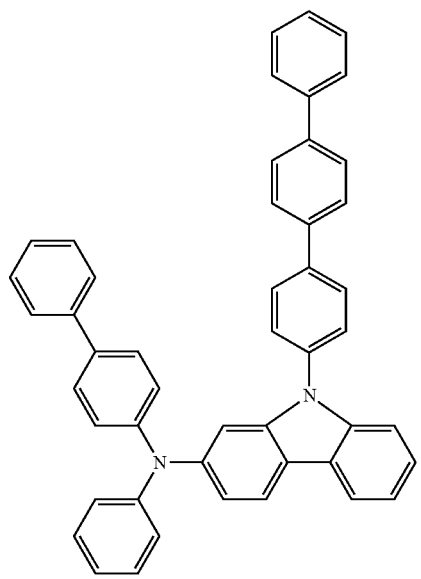
HT28
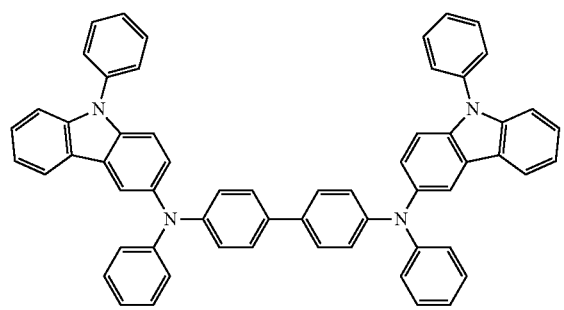
HT29
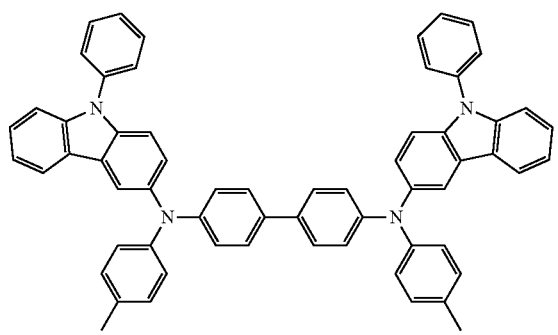

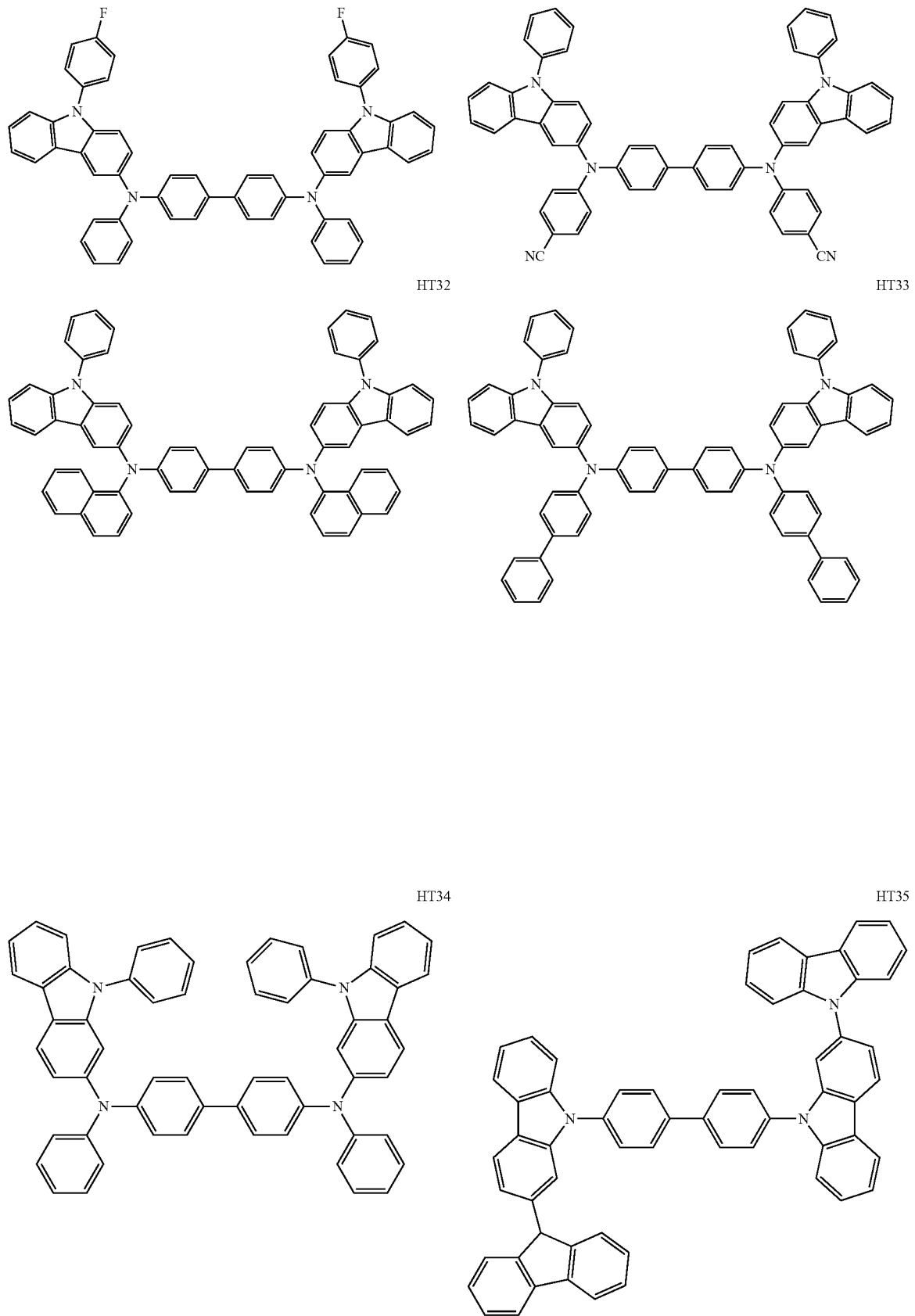

-continued

HT36
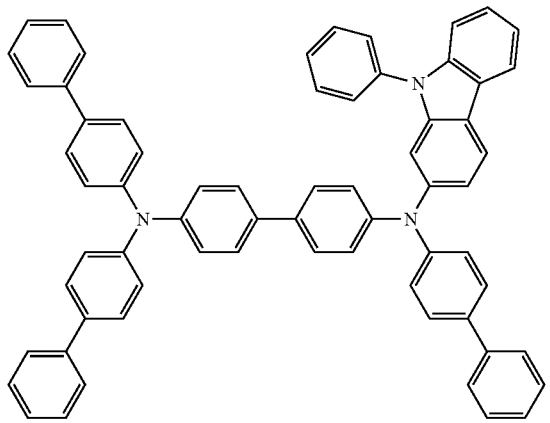

HT37
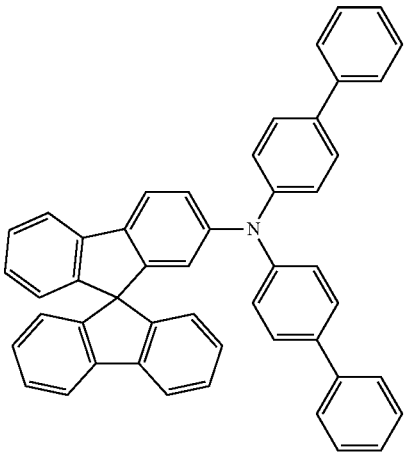

HT38
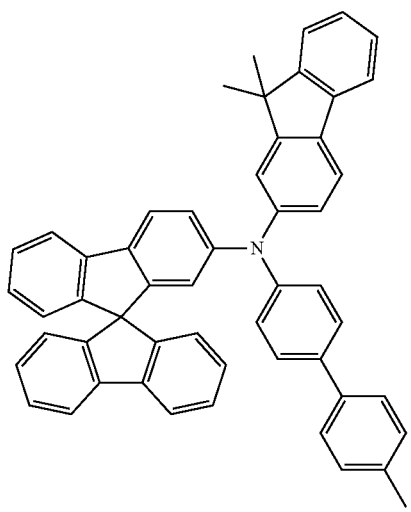

HT39
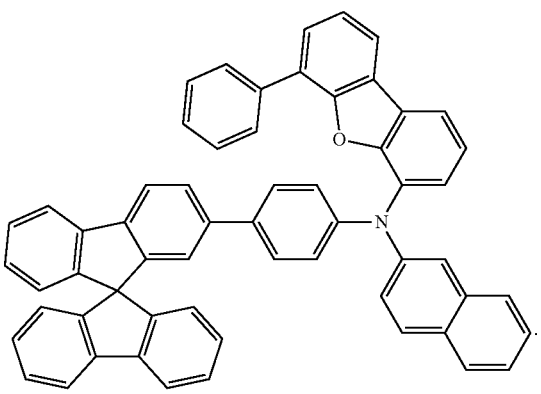

In one or more embodiments, the hole transport region 12 of the organic light-emitting device 10 may further include a p-dopant. When the hole transport region 12 further includes a p-dopant, the hole transport region 12 may have a structure including a matrix (for example, at least one of the compounds represented by Formulae 201 to 205) and a p-dopant included in the matrix. The p-dopant may be uniformly or non-uniformly doped on the hole transport region 12.

In one or more embodiments, the p-dopant may have a lowest unoccupied molecular orbital (LUMO) energy level of −3.5 eV or less.

The p-dopant may include at least one of a quinone derivative, a metal oxide, a cyano group-containing compound, or any combination thereof, but embodiments of the present disclosure are not limited thereto.

For example, the p-dopant may include at least one of:
 a quinone derivative, such as tetracyanoquinodimethane (TCNQ), 2,3,5,6-tetrafluoro-7,7,8,8-tetracyanoquinodimethane (F4-TCNQ), F6-TCNNQ, or any combination thereof;
 a metal oxide, such as a tungsten oxide and a molybdenum oxide;
 1,4,5,8,9,12-hexaazatriphenylene-hexacarbonitrile (HAT-CN); and
 a compound represented by Formula 221,
but embodiments of the present disclosure are not limited thereto:

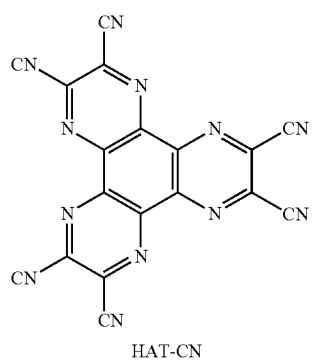

HAT-CN

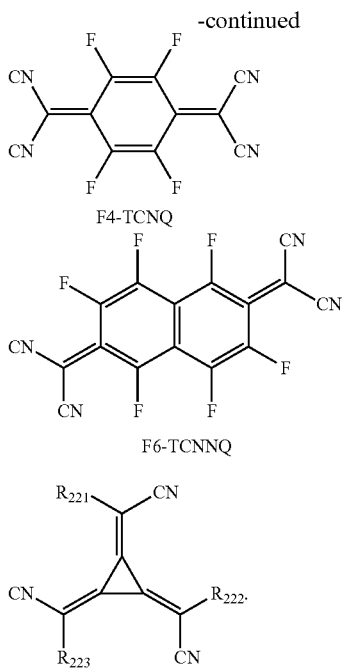

F4-TCNQ

F6-TCNNQ

<Formula 221>

In Formula 221, $R_{221}$ to $R_{223}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, wherein at least one of $R_{221}$ to $R_{223}$ may have at least one substituent of a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, a $C_1$-$C_{20}$ alkyl group substituted with —I, or any combination thereof.

A thickness of the hole transport region 12 may be in a range from about 100 Å to about 10,000 Å, for example, about 400 Å to about 2,000 Å, and a thickness of the emission layer 15 may be in a range from about 100 Å to about 3,000 Å, for example, about 300 Å to about 1,000 Å. When the thicknesses of the hole transport region 12 and the emission layer 15 are within the ranges above, satisfactory hole transport characteristics and/or emission characteristics may be obtained without a substantial increase in driving voltage.

Hole Transport Region 17

In the organic light-emitting device 10, an electron transport region 17 may be disposed between the emission layer 15 and the second electrode 19.

The electron transport region 17 may have a single-layered structure or a multi-layered structure.

For example, the electron transport region 17 may have an electron transport layer structure, an electron transport layer/electron injection layer structure, a buffer layer/electron transport layer structure, a hole blocking layer/electron transport layer structure, a buffer layer/electron transport layer/electron injection layer structure, or a hole blocking layer/electron transport layer/electron injection layer structure, but embodiments of the present disclosure are not limited thereto. The electron transport region 17 may further include an electron control layer.

The electron transport region 17 may include a known electron transport material.

The electron transport region 17 (for example, a buffer layer, a hole blocking layer, an electron control layer, or an electron transport layer in the electron transport region 17) may include at least one metal-non-containing compound including at least one TT electron-depleted nitrogen-containing cyclic group. The π electron-depleted nitrogen-containing cyclic group may be understood by referring to the description thereof presented herein.

For example, the electron transport region 17 may include a compound represented by Formula 601:

$[Ar_{501}]_{xe11}\text{-}[(L_{601})_{xe1}\text{-}R_{601}]_{xe21}.$  <Formula 601>

In Formula 601, $A_{601}$ and $L_{601}$ may each independently be a substituted or unsubstituted $C_5$-$C_{60}$ carbocyclic group or a substituted or unsubstituted $C_1$-$C_{60}$ heterocyclic group, xe11 may be 1, 2, or 3, xe1 may be an integer from 0 to 5, $R_{601}$ may be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one or more embodiments, at least one of $Ar_{601}$(s) in the number of xe11 and at least one of $R_{601}$(s) in the number of xe21 may include the electron-depleted nitrogen-containing cyclic group.

In one or more embodiments, $Ar_{601}$ and $L_{601}$ in Formula 601 may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with at least one deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), —P(=O)($Q_{31}$)($Q_{32}$), or any combination thereof, and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, a naphthyl group, or any combination thereof.

In Formula 601, when xe11 is 2 or more, two or more $Ar_{601}$(s) may be linked via a single bond.

In one or more embodiments, $A_{601}$ in Formula 601 may be an anthracene group.

In one or more embodiments, the compound represented by Formula 601 may be represented by Formula 601-1:

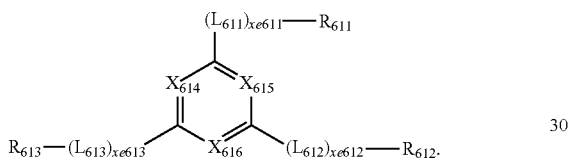

<Formula 601-1>

In Formula 601-1, $X_{614}$ may be N or C($R_{814}$), $X_{615}$ may be N or C($R_{815}$), $X_{616}$ may be N or C($R_{616}$), and at least one $X_{614}$ to $X_{616}$ may be N, $L_{611}$ to $L_{613}$ may each be understood by referring to the description presented in connection with $L_{601}$, xe611 to xe613 may each be understood by referring to the description presented in connection with xe1, $R_{611}$ to $R_{613}$ may each be understood by referring to the description presented in connection with $R_{601}$, and $R_{614}$ to $R_{616}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formulae 601 and 601-1 may each independently be:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group; or any combination thereof, or —S(=O)$_2$($Q_{601}$) or —P(=O)($Q_{601}$)($Q_{602}$), and $Q_{601}$ and $Q_{602}$ may each be understood by referring to the descriptions thereof presented herein.

The electron transport region 17 may include at least one compound of Compounds ET1 to ET36, but embodiments of the present disclosure are not limited thereto:

ET1
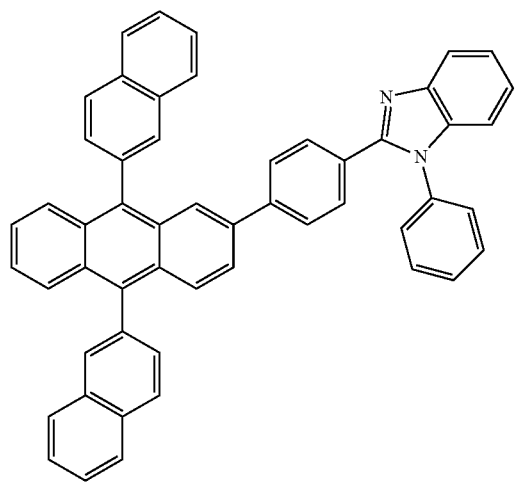
ET2
ET3
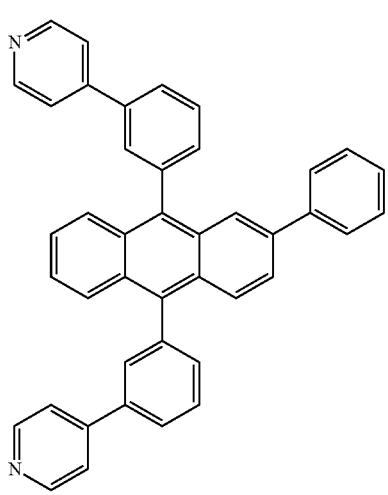
-continued
ET4
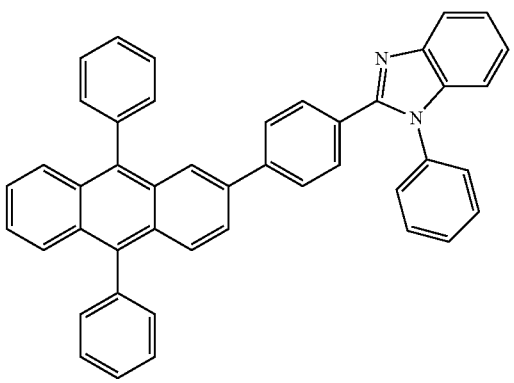
ET5
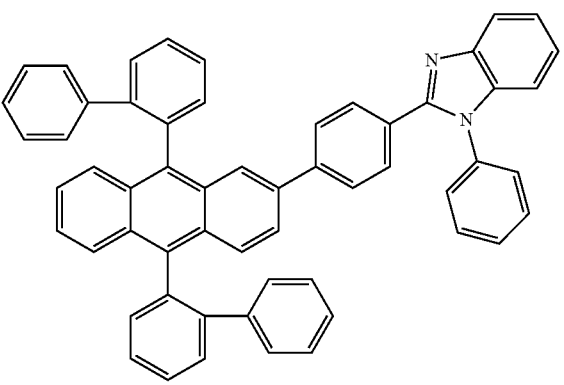
ET6

ET7
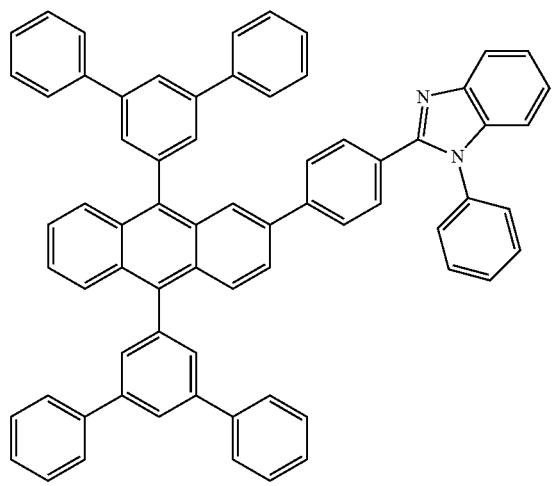
ET8
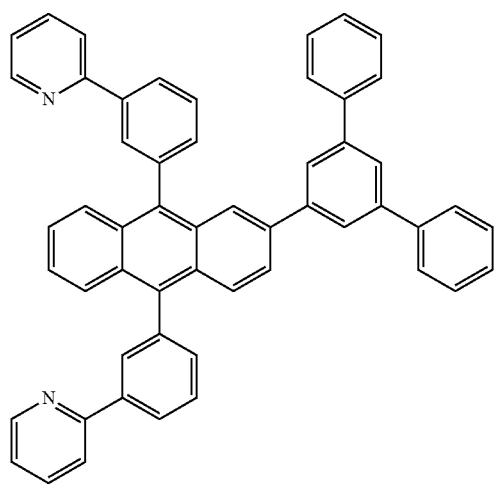
ET9
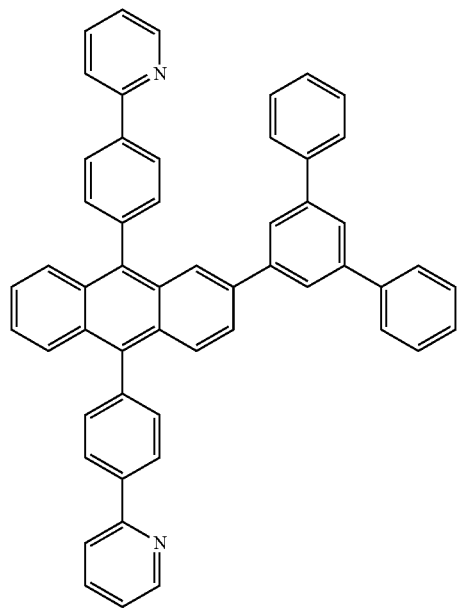
ET10
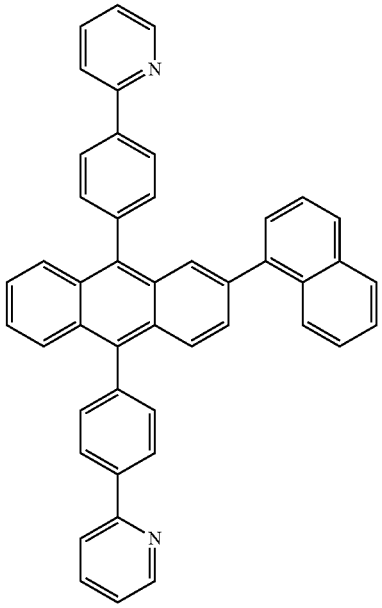
ET11
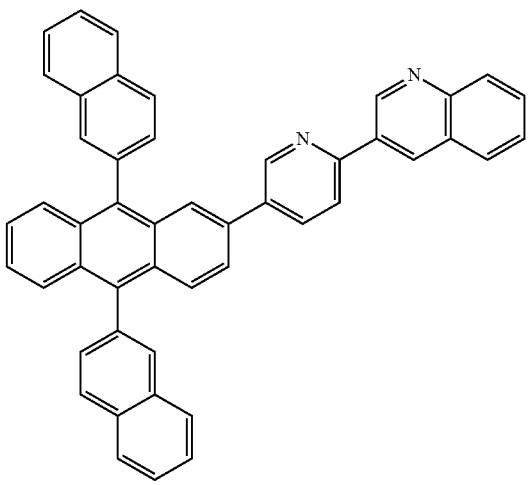
ET12
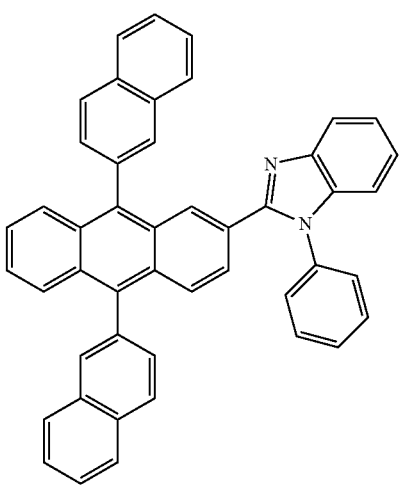

ET13
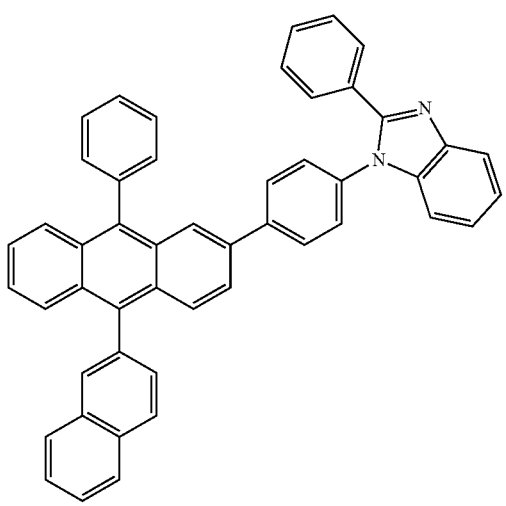
ET14
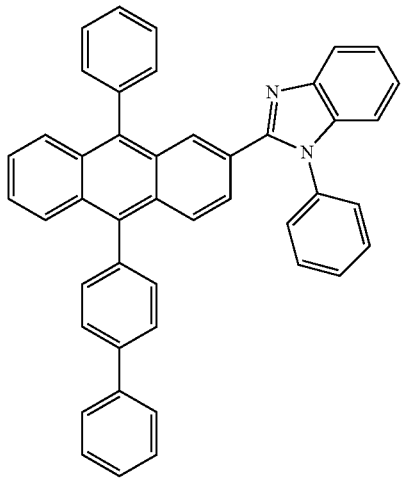
ET15
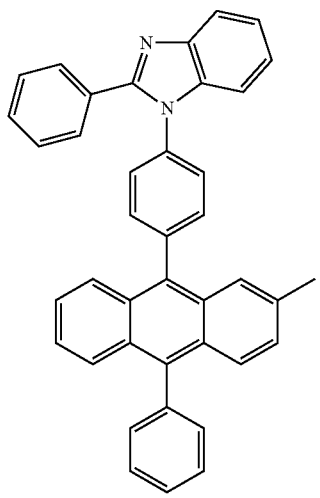
ET16
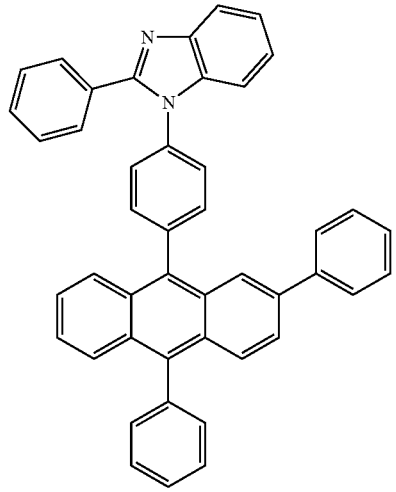
ET17
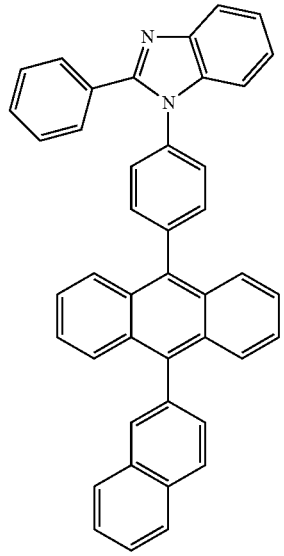
ET18
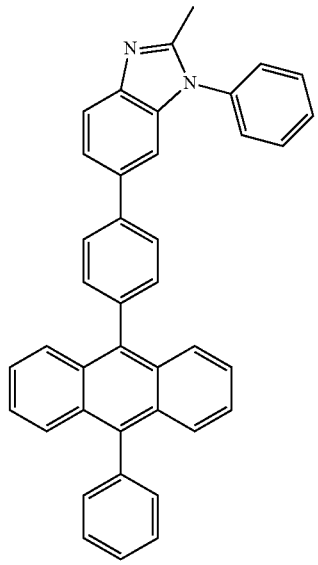

ET19
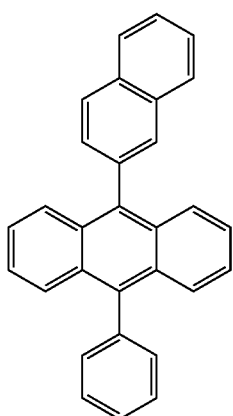
ET20
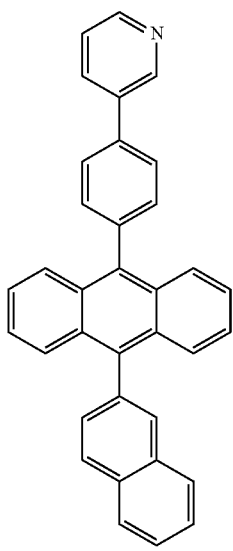
ET21
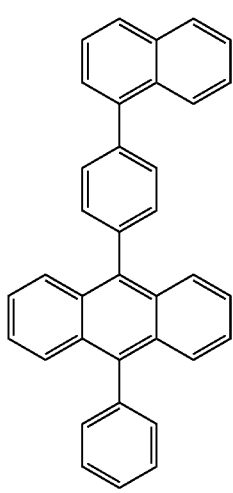
ET22
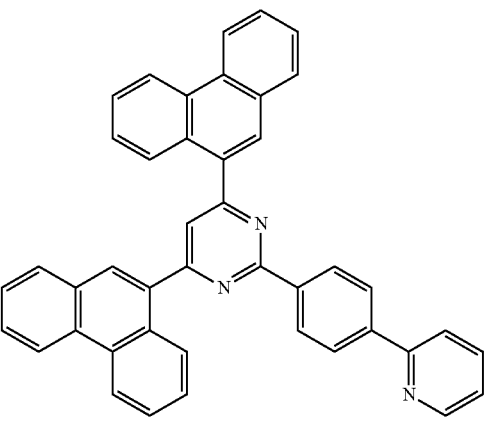
ET23
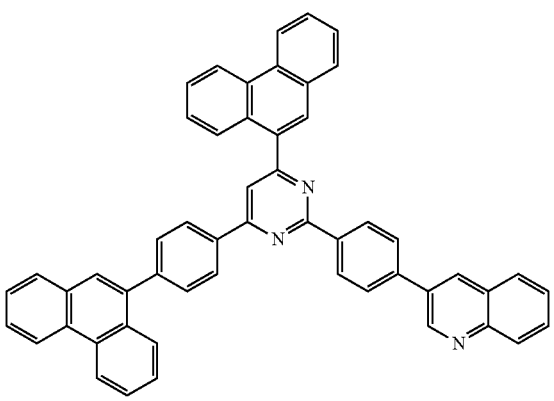
ET24
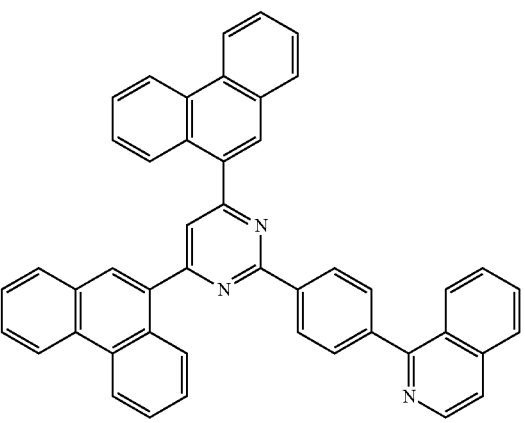

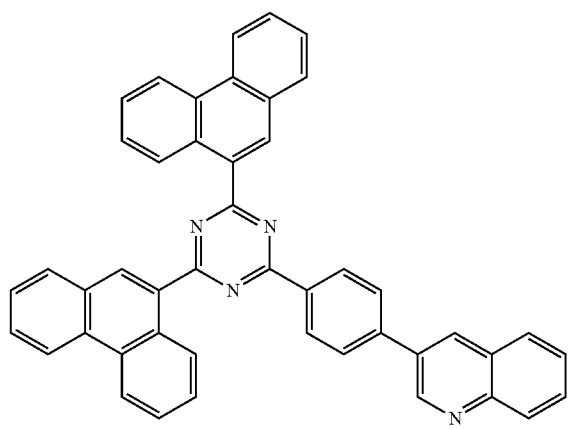
ET25
ET26
ET27
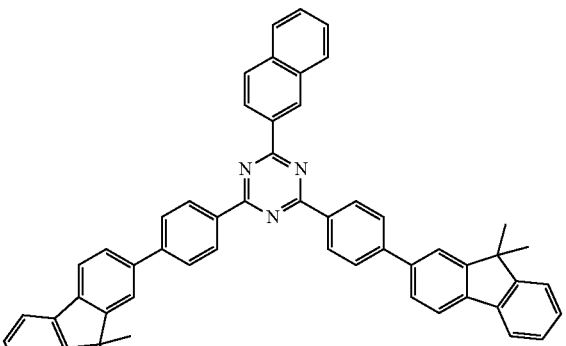
ET28
ET29
ET30
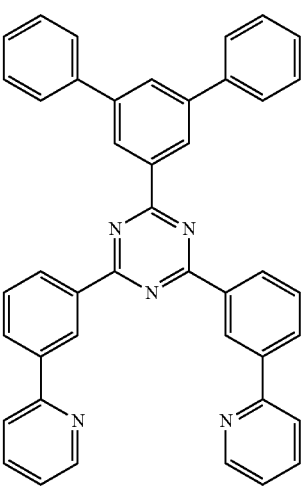

ET31
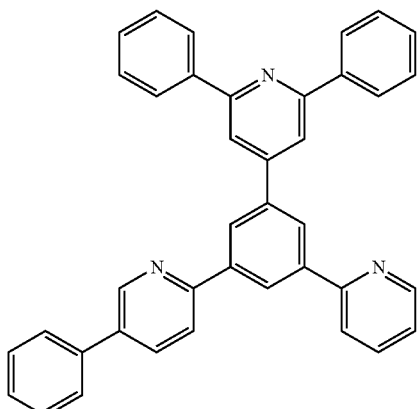
ET34
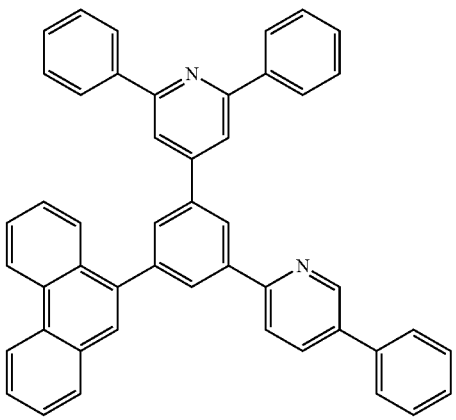
ET32
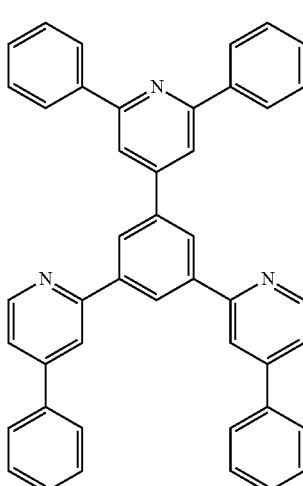
ET35
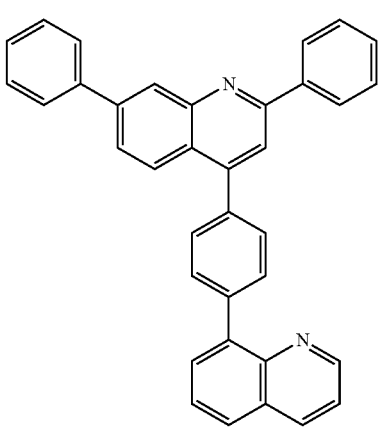
ET33
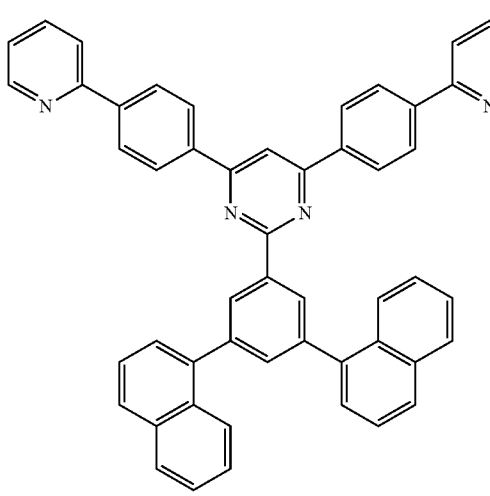
ET36
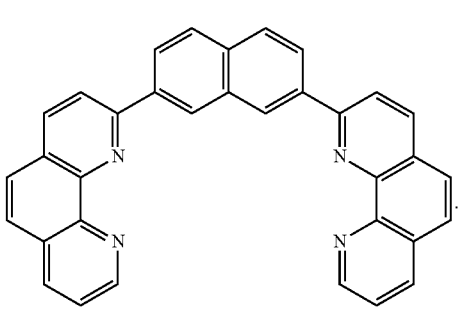
In one or more embodiments, the electron transport region 17 may include at least one compound of 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), NTAZ, or any combination thereof:

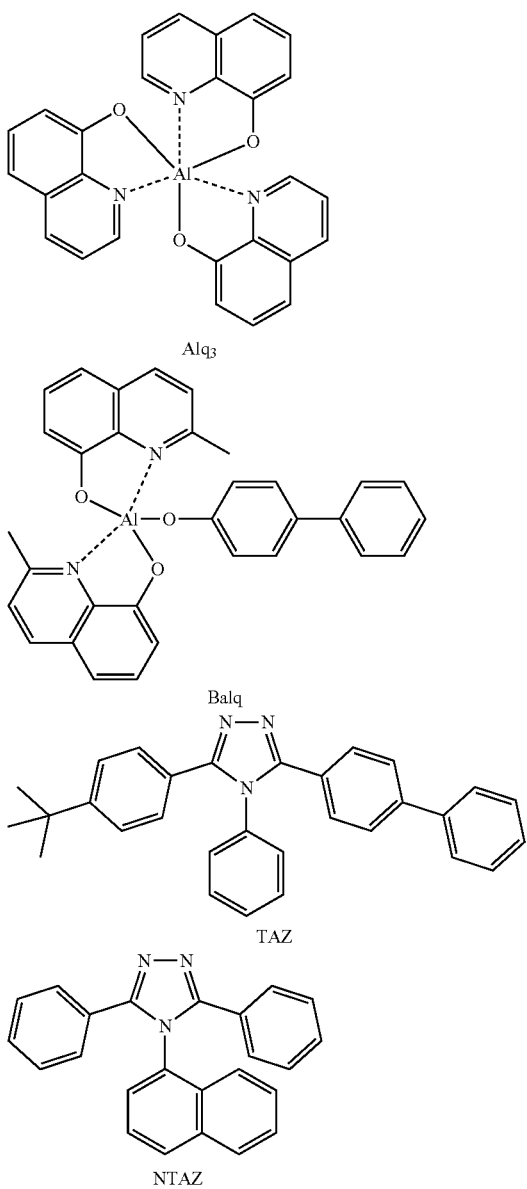

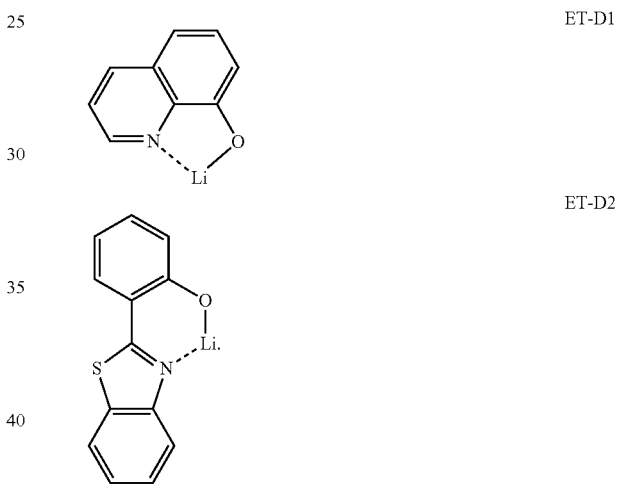

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, excellent electron blocking characteristics or electron control characteristics may be obtained without a substantial increase in driving voltage.

A thickness of the electron transport layer may be from about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region 17 (for example, the electron transport layer in the electron transport region) may further include, in addition to the materials described above, a metal-containing material.

The metal-containing material may include at least one alkali metal complex, alkaline earth-metal complex, or any combination thereof. The alkali metal complex may include a metal ion a Li ion, a Na ion, a K ion, a Rb ion, a Cs ion, or any combination thereof, and the alkaline earth-metal complex may include a metal ion a Be ion, a Mg ion, a Ca ion, a Sr ion, a Ba ion, or any combination thereof. A ligand coordinated with the metal ion of the alkali metal complex or the alkaline earth-metal complex may be a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, a cyclopentadiene, or any combination thereof, but embodiments of the present disclosure are not limited thereto.

For example, the metal-containing material may include a Li complex. The Li complex may include, for example, Compound ET-D1 (lithium quinolate, LiQ) or ET-D2:

The electron transport region 17 may include an electron injection layer that facilitates injection of electrons from the second electrode 19. The electron injection layer may be in direct contact with the second electrode 19.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof.

The alkali metal may be Li, Na, K, Rb, Cs, or any combination thereof. In one or more embodiments, the alkali metal may be Li, Na, or Cs. In one or more embodiments, the alkali metal may be Li or Cs, but embodiments of the present disclosure are not limited thereto.

The alkaline earth metal may be Mg, Ca, Sr, Ba, or any combination thereof.

The rare earth metal may be Sc, Y, Ce, Tb, Yb, Gd, or any combination thereof.

The alkali metal compound, the alkaline earth-metal compound, and the rare earth metal compound may be an oxide, a halide, or any combination thereof (for example, fluorides, chlorides, bromides, or iodides) of the alkali metal, the alkaline earth-metal, and the rare earth metal.

The alkali metal compound may be an alkali metal oxide, such as $Li_2O$, $Cs_2O$, or $K_2O$, or an alkali metal halide, such as LiF, NaF, CsF, KF, LiI, NaI, CsI, or KiIn one or more embodiments, the alkali metal compound may be LiF, $Li_2O$, NaF, LiI, NaI, CsI, or KI, but embodiments of the present disclosure are not limited thereto.

The alkaline earth-metal compound may be an alkaline earth-metal oxide, such as BaO, SrO, CaO, $Ba_xSr_{1-x}O$ (0<x<1), or $Ba_xCa_{1-x}O$ (0<x<1). In one or more embodiments, the alkaline earth-metal compound may be BaO, SrO, or CaO, but embodiments of the present disclosure are not limited thereto.

The rare earth metal compound may be $YbF_3$, $ScF_3$, $ScO_3$, $Y_2O_3$, $Ce_2O_3$, $GdF_3$, or $TbF_3$. In one or more embodiments, the rare earth metal compound may be $YbF_3$, $ScF_3$, $TbF_3$, $YbI_3$, $ScI_3$, or $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, or cyclopentadiene, but embodiments of the present disclosure are not limited thereto.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combination thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When a thickness of the electron injection layer is within these ranges, satisfactory electron injection characteristics may be obtained without substantial increase in driving voltage.

Second Electrode 19

The second electrode 19 may be disposed on the organic layer 10A having such a structure. The second electrode 19 may be a cathode which is an electron injection electrode, and in this regard, a material for forming the second electrode 19 may be metal, an alloy, an electrically conductive compound, or any combination thereof, which may have a relatively low work function.

The second electrode 19 may include at least one lithium (Li), silver (Ag), magnesium (Mg), aluminum (Al), aluminum-lithium (Al—Li), calcium (Ca), magnesium-indium (Mg—In), magnesium-silver (Mg—Ag), ITO, IZO, or any combination thereof, but embodiments of the present disclosure are not limited thereto. The second electrode 19 may be a transmissive electrode, a semi-transmissive electrode, or a reflective electrode.

The second electrode 19 may have a single-layered structure, or a multi-layered structure including two or more layers.

Hereinbefore, the organic light-emitting device according to an exemplary embodiment has been described in connection with FIG. 1.

Figure 2:
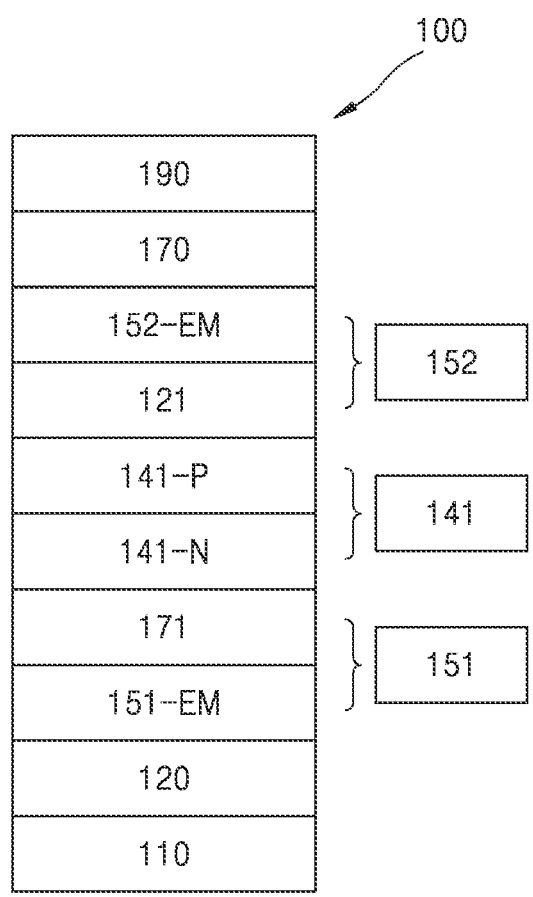
FIG. 2 is a schematic view of an organic light-emitting device 100 according to another exemplary embodiment.

Description of FIG. 2

FIG. 2 is a schematic view of an organic light-emitting device 100 according to another embodiment.

The organic light-emitting device 100 of FIG. 2 includes a first electrode 110, a second electrode 190 facing the first electrode 110, and a first light-emitting unit 151 and a second light-emitting unit 152 that are disposed between the first electrode 100 and the second electrode 190. A charge generation layer 141 may be disposed between the first light-emitting unit 151 and the second light-emitting unit 152, wherein the charge generation layer 141 may include an n-type charge generation layer 141-N and a p-type charge generation layer 141-P. The charge generation layer 141 is a layer that generates and supplies a charge to an adjacent light-emitting unit, and may include a known material.

The first light-emitting unit 151 may include a first emission layer 151-EM, and the second light-emitting unit 152 may include a second emission layer 152-EM. A maximum emission wavelength of light emitted from the first light-emitting unit 151 may be different that of light emitted from the second light-emitting unit 152. For example, mixed light of the light emitted from the first light-emitting unit 151 and the light emitted from the second light-emitting unit 152 may be white light, but embodiments of the present disclosure are not limited thereto.

A hole transport region 120 may be disposed between the first light-emitting unit 151 and the first electrode 110, and the second light-emitting unit 152 may include a first hole transport region 121 disposed on the side of the second light-emitting unit 152 facing the first electrode 110.

An electron transport region 170 may be disposed between the second light-emitting unit 152 and the second electrode 190, and the first light-emitting unit 151 may include a first electron transport region 171 disposed between the charge generation layer 141 and the first emission layer 151-EM.

The first emission layer 151-EM may include a host, a dopant, and a compound, wherein the dopant and the compound may each satisfy Conditions 1 to 4 above.

The second emission layer 152-EM may include a host, a dopant, and a compound, wherein the dopant and the compound may each satisfy Conditions 1 to 4 above.

In FIG. 2, the first electrode 110 and the second electrode 190 may each be understood by referring to the descriptions presented in connection with the first electrode 11 and the second electrode 19 in FIG. 1, respectively.

In FIG. 2, the first emission layer 151-EM and the second emission layer 152-EM may each be understood by referring to the description presented in connection with the emission layer 15 in FIG. 2.

In FIG. 2, the hole transport region 120 and the first hole transport region 121 may each be understood by referring to the description presented in connection with the hole transport region 12 in FIG. 1.

In FIG. 2, the electron transport region 170 and the first electron transport region 171 may each be understood by referring to the description presented in connection with the electron transport region 17 in FIG. 1.

Hereinbefore, referring to FIG. 2, both the first light-emitting unit 151 and the second light-emitting unit 152 are described with respect to the organic light-emitting device including the emission layer that includes the host, the dopant, and the compound. However, various modifications may be available in a way that, for example, one of the first light-emitting unit 151 and the second light-emitting unit 152 in the organic light-emitting device of FIG. 2 may be replaced with any light-emitting unit known in the art, or the organic light-emitting device may include three or more light-emitting units.

Figure 3:
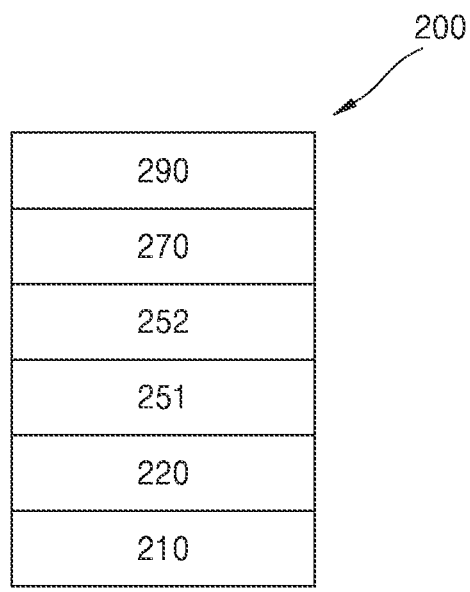
FIG. 3 is a schematic view of an organic light-emitting device 200 according to another exemplary embodiment.

Description of FIG. 3

FIG. 3 is a schematic view of an organic light-emitting device 200 according to another exemplary embodiment.

The organic light-emitting device 200 includes a first electrode 210, a second electrode 290 facing the first electrode 210, and a first emission layer 251 and a second emission layer 252 that are stacked between the first electrode 210 and the second electrode 290.

A maximum emission wavelength of light emitted from the first emission layer 251 may be different that of light emitted from the second emission layer 252. For example, mixed light of the light emitted from the first emission layer 251 and the light emitted from the second emission layer 252 may be white light, but embodiments of the present disclosure are not limited thereto.

In one or more embodiments, a hole transport region 220 may be disposed between the first emission layer 251 and the first electrode 210, and an electron transport region 270 may be disposed between the second emission layer 252 and the second electrode 290.

The first emission layer 251 may include a host, a dopant, and a compound, wherein the dopant and the compound may each satisfy Conditions 1 to 4 above.

The second emission layer 252 may include a host, a dopant, and a compound, wherein the dopant and the compound may each satisfy Conditions 1 to 4 above.

In FIG. 3, the first electrode 210, the hole transport region 220, and the second electrode 290 may each be understood by referring to the descriptions presented in connection with the first electrode 11, the hole transport region 12, and the second electrode 19 in FIG. 1, respectively.

In FIG. 3, the first emission layer 251 and the second emission layer 252 may each be understood by referring to the description presented in connection with the emission layer 15 in FIG. 1.

In FIG. 3, the electron transport region 270 may be understood by referring to the description presented in connection with the electron transport region 17 in FIG. 1.

Hereinbefore, referring to FIG. 3, both the first emission layer 251 and the second emission layer 252 are described with respect to the organic light-emitting device including the emission layer that includes the host, the dopant, and the compound. However, various modifications may be available in a way that, for example, any one of the first emission layer 251 and the second emission layer 252 in FIG. 3 may be replaced with a known layer, the organic light-emitting device may include three or more emission layers, or the organic light-emitting device may further include an intermediate layer between adjacent emission layers.

Descriptions of the Terms

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an isobutyl group, a sec-butyl group, ter-butyl group, pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one N, O, P, Si, B, Se, Ge, Te, S, or any combination thereof as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one N, O, P, Si, B, Se, Ge, Te, S, or any combination thereof as a ring-forming atom, 1 to 10 carbon atoms, and at least one double bond in its ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{10}$ heteroaryl group" as used herein refers to a monovalent group having a cyclic aromatic system that has at least one N, O, P, Si, B, Se, Ge, Te, S, or any combination thereof as a ring-forming atom, in addition to 1 to 60 carbon atoms. The term "$C_1$-$C_{10}$ heteroarylene group" as used herein refers to a divalent group having a carbocyclic aromatic system that has at least one N, O, P, Si, B, Se, Ge, Te, S, or any combination thereof as a ring-forming atom, in addition to 1 to 60 carbon atoms. Non-limiting examples of the $C_1$-$C_{10}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{10}$ heteroaryl group and the $C_1$-$C_{10}$ heteroarylene group each include two or more rings, the rings may be condensed with each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed with each other, at least one N, O, P, Si, B, Se, Ge, Te, S, or any combination thereof as ring-forming atoms, in addition to carbon atoms (for example, having 8 to 60 carbon atoms carbon), and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The term "$C_5$-$C_{30}$ carbocyclic group" as used herein refers to a monocyclic group or a polycyclic group, and, according to its chemical structure, a monovalent, divalent, trivalent, tetravalent, pentavalent, or hexavalent group.

The term "$C_1$-$C_{30}$ heterocyclic group" as used herein refers to a saturated or unsaturated cyclic group having, as a ring-forming atom, at least one heteroatom N, O, Si, P, B, Se, Ge, Te, S, or any combination thereof other than 1 to 30 carbon atoms. The term "$C_1$-$C_{30}$ heterocyclic group" as used herein refers to a monocyclic group or a polycyclic group, and, according to its chemical structure, a monovalent, divalent, trivalent, tetravalent, pentavalent, or hexavalent group.

In the present specification, at least one substituent of the substituted $C_5$-$C_{30}$ carbocyclic group, the substituted $C_1$-$C_{30}$ heterocyclic group, the substituted $C_1$-$C_{10}$ alkyl group, the substituted $C_2$-$C_{60}$ alkenyl group, the substituted $C_2$-$C_{60}$ alkynyl group, the substituted $C_1$-$C_{10}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{10}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_3$-$C_{60}$ aryloxy group, a $C_6$-$C_{60}$ arylthio group, a $C_1$-$C_{10}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_5$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), —P(=O)($Q_{28}$)($Q_{29}$), or any combination thereof; or —N($Q_{31}$)($Q_{32}$), —Si($Q_{33}$)($Q_{34}$)($Q_{35}$), —B($Q_{36}$)($Q_{37}$), or —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_2$-$C_0$ alkenyl group, a $C_2$-$C_0$ alkynyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group, a $C_6$-$C_{60}$ aryl group, or any combination thereof, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

The term "room temperature" as used herein refers to a temperature of about 25° C.

The terms "biphenyl group", "terphenyl group", and "tetraphenyl group" as used herein refer to a monovalent group in which two, three, and four phenyl a group are connected to each other via a single bond, respectively.

The terms "cyano group-containing phenyl group", "cyano group-containing biphenyl group", "cyano group-containing terphenyl group", and "cyano group-containing tetraphenyl group" as used herein refer to "phenyl group", "biphenyl group", "terphenyl group", and "tetraphenyl group", each substituted with at least one cyano group, respectively. In the "cyano group-containing phenyl group", "cyano group-containing biphenyl group", "cyano group-containing terphenyl group", and "cyano group-containing tetraphenyl group", a cyano group may be substituted at any position, and the "cyano group-containing phenyl group", "cyano group-containing biphenyl group", "cyano group-containing terphenyl group", and "cyano group-containing tetraphenyl group" may further include, in addition to a cyano group, other substituents. For example, both a phenyl group substituted with a cyano group and a phenyl group substituted with a cyano group or a methyl group belong to the "cyano group-containing phenyl group".

Hereinafter, a compound and an organic light-emitting device according to embodiments are described in detail with reference to Synthesis Example and Examples. However, the organic light-emitting device is not limited thereto. The wording "'B' was used instead of 'A'" used in describing Synthesis Examples means that a molar equivalent of 'A' was identical to a molar equivalent of 'B'.

EXAMPLES

Evaluation Example 1: Calculation of $\Delta E_{ST}$, $\Delta E_{ST2}$, and $\Delta E'_{TT}$ Regarding Compounds X, Y, and Z of the Comparative Examples and the Example, $\Delta E_{ST}$, $\Delta E_{ST2}$, and $\Delta E'_{TT}$ were calculated according to the methods described above, and it was determined whether Conditions 1 to 4 were satisfied. Results thereof are shown in Table 1.

TABLE 1

|  | Condition 1 | Condition 2 | Condition 3 | Condition 4 |
|---|---|---|---|---|
| Compound X (Comparative Example Compound 1) | Satisfied | Satisfied | Satisfied | Not satisfied |
| Compound Y (Comparative Example Compound 2) | Satisfied | Satisfied | Satisfied | Not satisfied |
| Compound Z (Example Compound 1) | Satisfied | Satisfied | Satisfied | Satisfied |

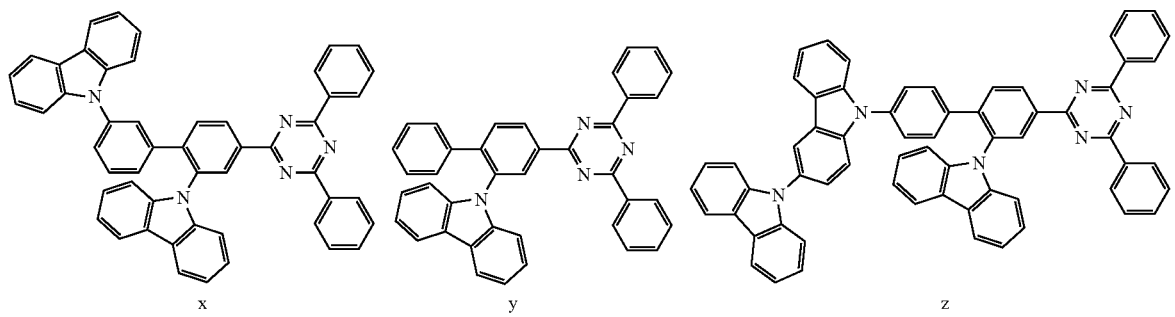

x  y  z

Evaluation Example 2: Measurement of HOMO, LUMO, $T_1$, $S_1$, and $\Delta E_{ST}$ According to methods described in Table 2, HOMO, LUMO, $T_1$, $S_1$, and $\Delta E_{ST}$ were measured, and results thereof are shown in Table 3.

TABLE 2

| | |
|---|---|
| HOMO energy level evaluation method | A potential (volts (V))-current (amperes (A)) graph of each compound was obtained by using cyclic voltammetery (CV) (electrolyte: 0.1M Bu$_4$NClO$_4$/solvent: CH$_2$Cl$_2$/electrode: 3-electrode suste, (working electrode: GC, reference electrode: Ag/AgCl, auxiliary electrode: Pt)), and from the reduction onset of the graph, a HOMO energy level of each compound was calculated. |
| LUMO energy level evaluation method | Each compound was diluted at a concentration of 1 × 10$^{-5}$M in CHCl$_3$, and a UV absorption spectrum was measured at room temperature by using a Shimadzu UV-350 spectrometer, and a LUMO energy level thereof was calculated by using an optical band gap (Eg) from an edge of the absorption spectrum. |
| $S_1$ energy level evaluation method | A photoluminence spectrum of a mixture of toluene and each compound (diluted at a concentration of 1 × 10$^{-4}$M) was measured at room temperature by using a photoluminence measuring meter, and peacks observed therefrom were analyzed to calculate an on set $S_1$ energy level. |
| $T_1$ energy level evaluation method | A photoluminence spectrum of a mixture of toluene and each compound (diluted at a concentration of 1 × 10$^{-4}$M) was added to a quartz cell, and liquid nitrogen (77K) was added thereto. A photoluminence spectrum of the resulting solution was measrued by using a photoluminence measuring meter, and the photoluminence spectrum thus obtained was compared to a normal photoluminence spectrum at room temperature to analyze peaks observed only at low temperatures to calculate an on set $T_1$ energy level. |
| $\Delta E_{ST}$ | A difference between the $S_1$ energy level and the $T_1$ energy level was calculated. |

TABLE 3

| | HOMO (eV) | LUMO (eV) | $T_1$ (eV) | $S_1$ (eV) | $\Delta E_{ST}$ (eV) |
|---|---|---|---|---|---|
| Compound X (Comparative Example Compound 1) | −5.71 | −2.167 | 2.684 | 2.78 | 0.096 |
| Compound Y (Comparative Example Compound 2) | −5.787 | −2.204 | 2.56 | 2.818 | 0.258 |
| Compound Z (Example Compound 1) | −5.5 | −2.36 | 2.48 | 2.774 | 0.294 |

Referring to Table 3, it was confirmed that Compound X had a relatively small $\Delta E_{ST}$, whereas Compounds Y and Z each had a relatively large $\Delta E_{ST}$.

Example 1

An ITO glass substrate was cut to a size of 50 mm×50 mm×0.5 mm, sonicated with isopropyl alcohol and pure water each for 15 minutes, and then, cleaned by exposure to ultraviolet rays and ozone for 30 minutes.

Then, F6-TCNNQ was deposited on the ITO electrode (i.e., an anode) of the glass substrate to form a hole injection layer having a thickness of 100 Å, and HT1 was deposited on the hole injection layer to form a hole transport layer having a thickness of 1,260 Å, thereby forming a hole transport region.

DPEPO (i.e., a first host) and Compound Z (i.e., a dopant) (wherein, an amount of the dopant was about 15 weight % based on the total weight of the first and the dopant) were co-deposited on the hole transport region to form an emission layer having a thickness of 400 Å.

Compound ET17 and LiQ were co-deposited at a weight ratio of 5:5 on the emission layer to form an electron transport layer having a thickness of 360 Å. Then, LiQ was deposited on the electron transport layer to form an electron injection layer having a thickness of 5 Å, and Ai was formed on the electron injection layer to a thickness of 1,000 Å, thereby completing the manufacture of an organic light-emitting device.

Comparative Examples 1 and 2

Organic light-emitting devices were each manufactured in the same manner as in Example 1, except that compounds shown in Table 4 were used as the dopant in forming an emission layer.

Example 2

An organic light-emitting device was manufactured in the same manner as in Example 1, except that a first host and a second host shown in Table 4 were used instead of the first host in forming an emission layer.

Comparative Examples 3 and 4

Organic light-emitting devices were each manufactured in the same manner as in Example 2, except that compounds shown in Table 4 were used as the dopant in forming an emission layer.

Example 2 and Comparative Examples 1 to 4

Organic light-emitting devices were each manufactured in the same manner as in Example 1, except that compounds shown in Table 4 were used as the compound and the dopant in forming an emission layer.

Evaluation Example 2: Measurement of OLED Lifespan and External Quantum Efficiency The external quantum efficiency (EQE) and lifespan of each of the organic light-emitting devices manufactured according to Examples 1 and 2 and Comparative Examples 1 to 4 were evaluated. Results thereof were calculated as relative values (%) and shown in Table 4. Here, a luminance meter (Minolta Cs-1000A) was used as an evaluation meter. The lifespan ($T_{95}$) was determined by evaluating the time taken to achieve 95% lyminance compared to initial luminance (100%) under the same luminance measurement conditions.

Results obtained by the evaluation were calculated as relative values (%) based on the values of Comparative Example 1 or Comparative Example 3, and shown in Table 4.

TABLE 4

| | First host | Second host | Weight ratio of first host:second host | Dopant | Lifespan (%) | EQE (%) |
|---|---|---|---|---|---|---|
| Comparative Example 1 | DPEPO | — | — | Compound X | — | 100 |
| Comparative Example 2 | DPEPO | — | — | Compound Y | — | 35.8 |
| Example 1 | DPEPO | — | — | Compound Z | — | 153.7 |
| Comparative Example 3 | mCBP-CN | o-CBP | 9:1 | Compound X | 100 | 100 |
| Comparative Example 4 | mCBP-CN | o-CBP | 9:1 | Compound Y | 82.4 | 97.2 |
| Example 2 | mCBP-CN | o-CBP | 9:1 | Compound Z | 341.2 | 850.5 |

Referring to Table 4, it was confirmed that the organic light-emitting devices Examples 1 and 2 had long lifespan and/or high efficiency compared to those of Comparative Examples 1 to 4. In particular, since Compound X of Comparative Examples 1 and 3 had a relatively small $\Delta E_{ST}$ compared to Compound Z, Compound X was generally expected to emit TADF, but was found to have low efficiency compared to the organic light-emitting devices of Examples 1 and 2. That is, in the case of using a compound that satisfies all Conditions 1 to 4 in an organic light-emitting device, delayed fluorescence characteristics were exhibited in spite of a large $\Delta E_{ST}$, and accordingly, it was confirmed that an organic light-emitting device with a relatively high efficiency was able to be provided.

According to the one or more embodiments, the organic light-emitting device may have improved efficiency and/or improved lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. An organic light-emitting device comprising:
a first electrode;
a second electrode; and
an organic layer disposed between the first electrode and the second electrode and comprising an emission layer, wherein the emission layer comprises a compound satisfying Conditions 5' and 6 below:

$0 \text{ eV} < \Delta E_{ST} \leq 0.1 \text{ eV}$      <Condition 5'>

$\Delta E_{ST} > 0.2 \text{ eV}$      <Condition 6> wherein, in Conditions 5' and 6, $\Delta E_{ST2}$ indicates the value obtained by subtracting a 2nd-lowest triplet excitation energy level calculated for a $T_2$ equilibrium structure of the compound from a lowest singlet excitation energy level calculated for an $S_1$ equilibrium structure of the compound and $\Delta E_{ST}$ indicates the value obtained by subtracting a lowest triplet excitation energy level calculated for a $T_1$ equilibrium structure of the compound from a lowest singlet excitation energy level calculated for the S1 equilibrium structure of the compound.

2. The organic light-emitting device of claim 1, wherein the emission layer further comprises a host, and
the weight of the compound in the emission layer is less than or equal to the weight of the host in the emission layer.

3. The organic light-emitting device of claim 1, wherein the emission layer further comprises a host and a dopant,
the weight of the compound in the emission layer is less than or equal to the weight of the host in the emission layer, and
the weight of the compound in the emission layer is greater than or equal to the weight of the dopant in the emission layer.

4. The organic light-emitting device of claim 1, wherein the emission layer further comprises a host and a sensitizer, and
the weight of the compound in the emission layer is less than or equal to the weight of the sensitizer in the emission layer.

5. The organic light-emitting device of claim 4, wherein the host comprises an electron transport host, a hole transport host, or any combination thereof.

6. The organic light-emitting device of claim 5, wherein the electron transport host comprises at least one π electron-depleted nitrogen-free cyclic group and at least one electron transport moiety,
the hole transport host comprises at least one π electron-depleted nitrogen-free cyclic group, but does not comprise an electron transport moiety, and
the electron transport moiety is a cyano group or a π electron-depleted nitrogen-containing cyclic group.

7. The organic light-emitting device of claim 6, wherein the π electron-depleted nitrogen-containing cyclic group is:
an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group; or
a condensed ring of two or more π electron-depleted nitrogen-containing cyclic groups, and
the at least one π electron-depleted nitrogen-free cyclic group is:

a benzene group, a heptalene group, an indene group, a naphthalene group, an azulene group, an indacene group, acenaphthylene group, a fluorene group, a spirobifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group; or a condensed ring of two or more π electron-depleted nitrogen-free cyclic groups.

8. The organic light-emitting device of claim 5, wherein the hole transport host comprises a carbazole group.

9. The organic light-emitting device of claim 5, wherein the electron transport host comprises i) at least one of a cyano group, a pyrimidine group, a pyrazine group, a triazine group, or any combination thereof, and ii) a triphenylene group.

10. The organic light-emitting device of claim 1, wherein the compound is represented by Formula 101 or 102 below:

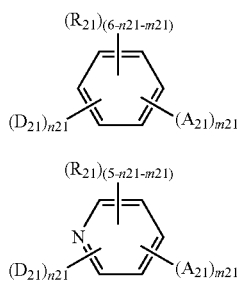

<Formula 101>

<Formula 102> wherein, in Formulae 101 and 102,
$A_{21}$ is an acceptor group,
$D_{21}$ is a donor group,
m21 is 1, 2, or 3,
n21 is 1, 2, or 3,
the sum of n21 and m21 in Formula 101 is 6 or less,
the sum of n21 and m21 in Formula 102 is 5 or less,
$R_{21}$ is hydrogen, deuterium, —F, —Cl, —Br, —I, —SF$_5$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkyl aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —B(Q$_1$)(Q$_2$), —N(Q$_1$)(Q$_2$), —P(Q$_1$)(Q$_2$), —C(=O)(Q$_1$), —S(=O)(Q$_1$), —S(=O)$_2$(Q$_1$), —P(=O)(Q$_1$)(Q$_2$), or —P(=S)(Q$_1$)(Q$_2$), wherein a plurality of R$_{21}$(s) are optionally linked to each other to form a substituted or unsubstituted $C_5$-$C_{30}$ carbocyclic group or a substituted or unsubstituted $C_1$-$C_{30}$ heterocyclic group, and $Q_1$ to $Q_3$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with at least one deuterium, —F, a cyano group, a $C_1$-$C_{60}$ alkyl group, a $C_6$-$C_{60}$ aryl group, or any combination thereof, or a $C_6$-$C_{60}$ aryl group substituted with at least one deuterium, —F, a cyano group, a $C_1$-$C_{60}$ alkyl group, a $C_6$-$C_{60}$ aryl group, or any combination thereof.

11. The organic light-emitting device of claim 10, wherein $A_{21}$ is a substituted or unsubstituted π electron-depleted nitrogen-free cyclic group, $D_{21}$ is:
—F, a cyano group, or a π electron-depleted nitrogen-containing cyclic group;
a $C_1$-$C_{60}$ alkyl group, a π electron-depleted nitrogen-containing cyclic group, or a π electron-depleted nitrogen-free cyclic group, each substituted with at least one —F, a cyano group, or any combination thereof; or
a π electron-depleted nitrogen-containing cyclic group substituted with at least one of a deuterium, a $C_1$-$C_{60}$ alkyl group, a π electron-depleted nitrogen-containing cyclic group, a π electron-depleted nitrogen-free cyclic group, or any combination thereof,
the at least one π electron-depleted nitrogen-free cyclic group is:
a benzene group, a heptalene group, an indene group, a naphthalene group, an azulene group, an indacene group, acenaphthylene group, a fluorene group, a spirobifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group; or a condensed ring of two or more π electron-depleted nitrogen-free cyclic groups, and the π electron-depleted nitrogen-containing cyclic group comprises at least one *—N=* moiety, and is:

an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, or a benzimidazolobenzimidazole group; or a condensed ring of two or more π electron-depleted nitrogen-containing cyclic groups.

12. An organic light-emitting device comprising:
a first electrode;
a second electrode; and
an organic layer disposed between the first electrode and the second electrode and comprising an emission layer,
wherein the emission layer comprises a compound satisfying Condition 2 below:

$0\ eV < \Delta E_{ST2} + E'_{TT} \leq 1.0\ eV$,  <Condition 2> wherein, in Condition 2, $\Delta E_{ST2}$ indicates the value obtained by subtracting a 2nd-lowest triplet excitation energy level calculated for a $T_2$ equilibrium structure of the compound from the lowest singlet excitation energy level calculated for an $S_1$ equilibrium structure of the compound and $\Delta E'_{TT}$ indicates the value obtained by subtracting the lowest triplet excitation energy level calculated for the $T_2$ equilibrium structure of the compound from a 2nd-lowest triplet excitation energy level calculated for the $T_2$ equilibrium structure of the compound.

13. The organic light-emitting device of claim 12, wherein the compound further satisfies Condition 4 below:

$\Delta E_{ST2} > 0\ eV$  <Condition 4> wherein, in Condition 4, $\Delta E_{ST2}$ indicates the value obtained by subtracting a 2nd-lowest triplet excitation energy level calculated for the $T_2$ equilibrium structure of the compound from the lowest singlet excitation energy level calculated for an $S_1$ equilibrium structure of the compound.

14. The organic light-emitting device of claim 12, wherein the compound further satisfies Condition 6 below:

$\Delta E_{ST} > 0.2\ eV$  <Condition 6> wherein, in Condition 6, $\Delta E_{ST}$ indicates the value obtained by subtracting the lowest triplet excitation energy level calculated for the $T_1$ equilibrium structure of the compound from the lowest singlet excitation energy level calculated for the $S_1$ equilibrium structure of the compound.

15. The organic light-emitting device of claim 12, wherein the compound further satisfies Condition 5 below:

$\Delta E_{ST2} \leq 0.1\ eV$  <Condition 5> wherein, in Condition 5, $\Delta E_{ST2}$ indicates the value obtained by subtracting 2nd-lowest triplet excitation energy level calculated for the $T_2$ equilibrium structure of the compound from the lowest singlet excitation energy level calculated for an $S_1$ equilibrium structure of the compound.

16. The organic light-emitting device of claim 12, wherein the compound further satisfies Condition 3 below:

$0\ eV < \Delta E'_{TT} \leq 0.15\ eV$  <Condition 3> wherein, in Condition 3, $\Delta E'_{TT}$ indicates the value obtained by subtracting the lowest triplet excitation energy level calculated for the $T_2$ equilibrium structure of the compound from a 2nd-lowest triplet excitation energy level calculated for a $T_2$ equilibrium structure of the compound.

17. The organic light-emitting device of claim 12, wherein the emission layer further comprises a host, and
the weight of the compound in the emission layer is less than or equal to the weight of the host in the emission layer.

18. The organic light-emitting device of claim 17, wherein the host comprises an electron transport host, a hole transport host, or any combination thereof.

19. The organic light-emitting device of claim 18, wherein the hole transport host comprises a carbazole group.

20. The organic light-emitting device of claim 18, wherein the electron transport host comprises i) at least one of a cyano group, a pyrimidine group, a pyrazine group, a triazine group, or any combination thereof, and ii) a triphenylene group.

* * * * *